US012595256B2

(12) United States Patent
Parham et al.

(10) Patent No.: US 12,595,256 B2
(45) Date of Patent: Apr. 7, 2026

(54) COMPOSITION FOR ORGANIC ELECTRONIC DEVICES

(71) Applicant: Merck Patent GmbH, Darmstadt (DE)

(72) Inventors: Amir Parham, Frankfurt am Main (DE); Jonas Kroeber, Frankfurt am Main (DE); Jens Engelhart, Darmstadt (DE); Anja Jatsch, Frankfurt am Main (DE); Christian Eickhoff, Mannheim (DE); Christian Ehrenreich, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 815 days.

(21) Appl. No.: 15/733,850

(22) PCT Filed: May 28, 2019

(86) PCT No.: PCT/EP2019/063712

§ 371 (c)(1),
(2) Date: Nov. 30, 2020

(87) PCT Pub. No.: WO2019/229011

PCT Pub. Date: Dec. 5, 2019

(65) Prior Publication Data

US 2022/0332724 A1 Oct. 20, 2022

(30) Foreign Application Priority Data

May 30, 2018 (EP) .................................... 18175234

(51) Int. Cl.

| | |
|---|---|
| ***C07D 405/04*** | (2006.01) |
| ***C07D 493/00*** | (2006.01) |
| ***H10K 50/11*** | (2023.01) |
| ***H10K 50/16*** | (2023.01) |
| ***H10K 50/17*** | (2023.01) |
| ***H10K 50/18*** | (2023.01) |
| ***H10K 85/60*** | (2023.01) |
| ***H10K 101/00*** | (2023.01) |
| ***H10K 101/10*** | (2023.01) |

(52) U.S. Cl.

CPC ......... *C07D 405/04* (2013.01); *C07D 493/00* (2013.01); *H10K 85/623* (2023.02); *H10K 85/654* (2023.02); *H10K 85/6574* (2023.02); *H10K 85/6576* (2023.02); *H10K 50/11* (2023.02); *H10K 50/16* (2023.02); *H10K 50/171* (2023.02); *H10K 50/18* (2023.02); *H10K 2101/10* (2023.02); *H10K 2101/90* (2023.02)

(58) Field of Classification Search

CPC .. C07D 493/00; C07D 405/04; H10K 85/623; H10K 85/654; H10K 85/6574; H10K 85/6576; H10K 50/11; H10K 50/16; H10K 50/171; H10K 50/18; H10K 2101/10; H10K 2101/90; H10K 85/615; H10K 85/624; C09K 2211/1007; C09K 2211/1029; C09K 2211/185; C09K 11/06; Y02E 10/549

See application file for complete search history.

(56) References Cited

U.S. PATENT DOCUMENTS

| | | | | |
|---|---|---|---|---|
| 4,539,507 | A | 9/1985 | Vanslyke et al. | |
| 5,151,629 | A | 9/1992 | Vanslyke | |
| 6,392,250 | B1 | 5/2002 | Aziz et al. | |
| 6,803,720 | B2 | 10/2004 | Kwong et al. | |
| 2010/0187977 | A1 | 7/2010 | Kai et al. | |
| 2016/0093808 | A1 | 3/2016 | Adamovich et al. | |
| 2017/0054087 | A1 | 2/2017 | Zeng et al. | |
| 2017/0186965 | A1* | 6/2017 | Parham ................ | C07D 409/14 |
| 2018/0037546 | A1 | 2/2018 | Sugino et al. | |
| 2020/0058877 | A1* | 2/2020 | Cha ........................ | C09K 11/06 |

FOREIGN PATENT DOCUMENTS

| | | | |
|---|---|---|---|
| EP | 0676461 | A2 | 10/1995 |
| EP | 3043398 | A1 | 7/2016 |
| EP | 3415512 | A2 | 12/2018 |
| JP | 5831654 | B1 | 12/2015 |
| KR | 10-2015-0074603 | A | 7/2015 |
| KR | 10-2015-0136027 | A | 12/2015 |
| KR | 10-2018-0051355 | A | 5/2018 |
| KR | 10-1856728 | B1 | 5/2018 |
| WO | 98/27136 | A1 | 6/1998 |
| WO | 2008/056746 | A1 | 5/2008 |
| WO | WO-2015099507 | A1 * | 7/2015 |

(Continued)

OTHER PUBLICATIONS

Dong, S. C. et al., (2012). New dibenzofuran/spirobifluorene hybrids as thermally stable host materials for efficient phosphorescent organic light-emitting diodes with low efficiency roll-off. Physical Chemistry Chemical Physics, 14(41), 14224-14228. (Year: 2012).*

(Continued)

*Primary Examiner* — Dawn L Garrett
(74) *Attorney, Agent, or Firm* — Faegre Drinker Biddle & Reath LLP

(57) ABSTRACT

The invention relates to a composition comprising an electron-transporting host and a hole-transporting host, to the use thereof in electronic devices and to electronic devices containing said composition. The electron-transporting host is most preferably selected from the class of triazine-dibenzofurane-fluorenyl systems or from the class of triazine-dibenzothiophene-fluorenyl systems. The hole-transporting host is preferably selected from the class of biscarbazoles.

9 Claims, No Drawings

(56) References Cited

FOREIGN PATENT DOCUMENTS

| | | | |
|---|---|---|---|
| WO | 2015/169412 | A1 | 11/2015 |
| WO | 2018/016742 | A1 | 1/2018 |

OTHER PUBLICATIONS

Baldo et al., "Very high-efficiency green organic light-emitting devices based on electrophosphorescence," Appl. Phys. Lett., vol. 75, (1999), pp. 4-6.

International Preliminary Report on Patentability received for PCT Patent Application No. PCT/EP2019/063712, mailed on Dec. 10, 2020, 23 pages. (11 pages of English Translation and 12 pages of Original Document).

International Search Report and Written Opinion received for PCT Patent Application No. PCT/EP2019/063712, mailed on Oct. 9, 2019, 29 pages. (12 pages of English Translation and 17 pages of Original Document).

* cited by examiner

COMPOSITION FOR ORGANIC ELECTRONIC DEVICES

CROSS-REFERENCE TO RELATED APPLICATIONS

This application is a national stage application (under 35 U.S.C. § 371) of PCT/EP2019/063712, filed May 28, 2019, which claims benefit of European Application No. 18175234.6, filed May 30, 2018, both of which are incorporated herein by reference in their entirety.

The present invention relates to a composition comprising an electron-transporting host and a hole-transporting host, to the use thereof in electronic devices and electronic devices comprising said composition. The electron-transporting host is more preferably selected from the class of the triazine-dibenzofuran-fluorenyl systems or the class of the triazine-dibenzothiophene-fluorenyl systems. The hole-transporting host is preferably selected from the class of biscarbazoles.

The structure of organic electroluminescent devices (e.g. OLEDs—organic light-emitting diodes or OLECs—organic light-emitting electrochemical cells) in which organic semiconductors are used as functional materials is described, for example, in U.S. Pat. Nos. 4,539,507, 5,151,629, EP 0676461 and WO 98/27136. Emitting materials used here, as well as fluorescent emitters, are increasingly organometallic complexes which exhibit phosphorescence rather than fluorescence (M. A. Baldo et al., *Appl. Phys. Lett.* 1999, 75, 4-6). For quantum-mechanical reasons, up to a fourfold increase in energy efficiency and power efficiency is possible using organometallic compounds as phosphorescent emitters. In general terms, however, there is still a need for improvement in OLEDs, especially also in OLEDs which exhibit triplet emission (phosphorescence), for example with regard to efficiency, operating voltage and lifetime.

The properties of organic electroluminescent devices are not only determined by the emitters used. Also of particular significance here are especially the other materials used, such as host and matrix materials, hole blocker materials, electron transport materials, hole transport materials and electron or exciton blocker materials, and among these especially the host or matrix materials. Improvements to these materials can lead to distinct improvements to electroluminescent devices.

Host materials for use in organic electronic devices are well known to the person skilled in the art. The term "matrix material" is also frequently used in the prior art when what is meant is a host material for phosphorescent emitters. This use of the term is also applicable to the present invention. In the meantime, a multitude of host materials has been developed both for fluorescent and for phosphorescent electronic devices.

According to the prior art, triazines are among the matrix materials used for phosphorescent emitters, for example structures as described in WO 2008/056746, KR 20150074603, KR 20150136027, WO 2015/169412, EP3043398 A1, JP5831654, US 2016/093808, US 2017/0054087 or WO 2018/016742.

A further means of improving the performance data of electronic devices, especially of organic electroluminescent devices, is to use combinations of two or more materials, especially host materials or matrix materials.

U.S. Pat. No. 6,392,250 B1 discloses the use of a mixture consisting of an electron transport material, a hole transport material and a fluorescent emitter in the emission layer of an OLED. With the aid of this mixture, it was possible to improve the lifetime of the OLED compared to the prior art.

U.S. Pat. No. 6,803,720 B1 discloses the use of a mixture comprising a phosphorescent emitter and a hole transport material and an electron transport material in the emission layer of an OLED. Both the hole transport material and the electron transport material are small organic molecules.

According to WO 2015/169412, it is likewise possible to use triazine-dibenzofuran-carbazole derivatives and triazine-dibenzothiophene-carbazole derivatives, for example, in a mixture. For example, the production of the OLED designated E34 is described, which contains, in the emitting layer, the host materials EG1, IC6 and the phosphorescent emitter TEG1. The structures of the compounds used are shown below:

EG1

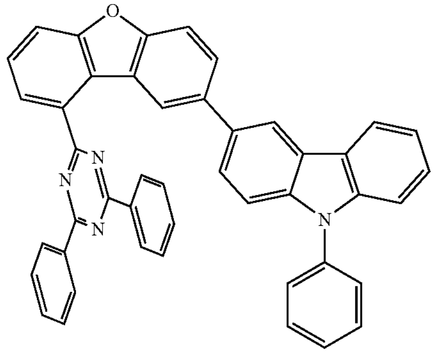

IC6

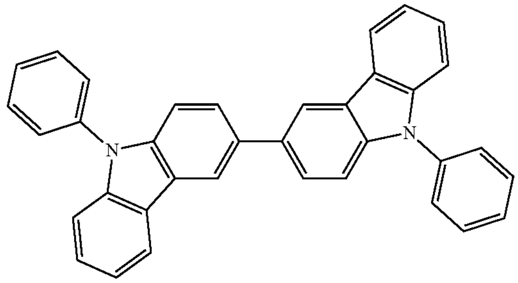

TEG1

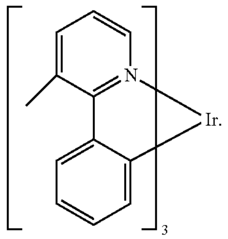

According to WO 2018/016742, it is possible to use triazine-dibenzofuran-aryl derivatives and triazine-dibenzothiophene-aryl derivatives, for example, in a mixture. For example, specific triazine-dibenzofuran-triphenylene derivatives are combined with a specific biscarbazole and an emitter in an EML. Detailed by way of example is the combination of compound 4 with the biscarbazole PH-2 and the emitter GD-1, as shown in the following table:

chemical compound 4
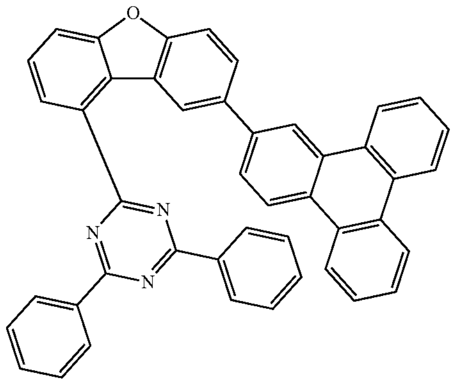 [SMILES: c1ccc(-c2nc(-c3ccccc3)nc(-c3cccc4oc5ccc(-c6ccc7c8ccccc8c8ccccc8c7c6)cc5c34)n2)cc1]
PH-2
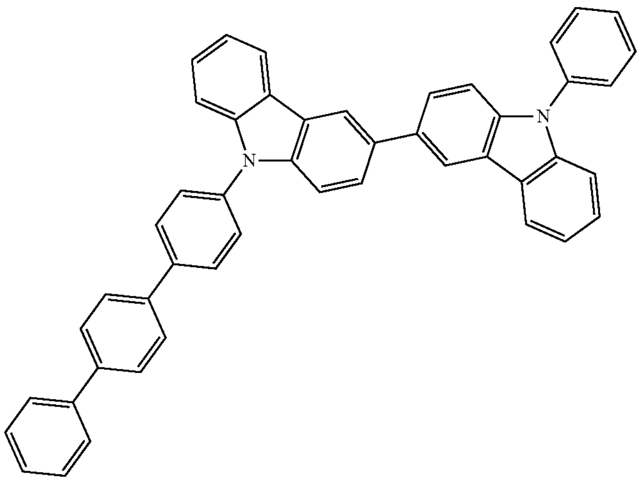 [SMILES: c1ccc(-c2ccc(-c3ccc(-n4c5ccccc5c5cc(-c6ccc7c(c6)c6ccccc6n7-c6ccccc6)ccc54)cc3)cc2)cc1]
GD-1
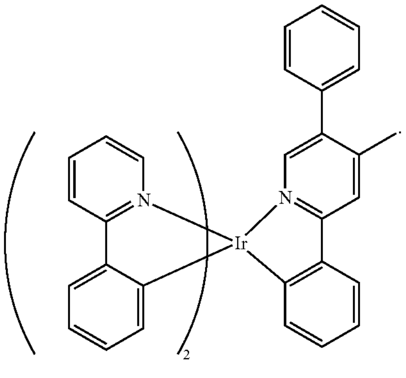

The compound H of the formula chemical compound H

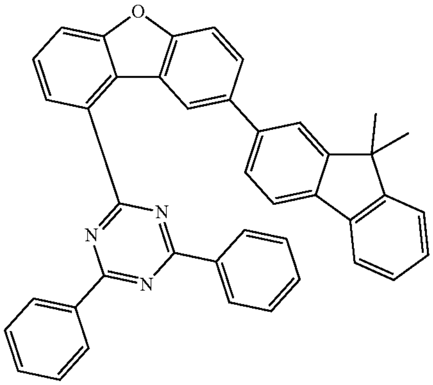

is used for comparative purposes in a single-host system.

According to US 2017/0054087, it is possible to use a combination of specific triazine-dibenzofuran-aryl derivatives or specific triazine-dibenzothiophene-aryl derivatives with specific biscarbazole derivatives in what is called a premix system, a preliminary mixture for the production of light-emitting devices. Three premixes are specified by way of example in the following table:

Compound A14

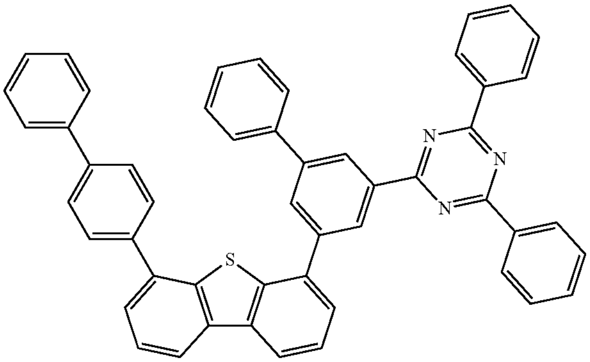 [SMILES: c1ccc(-c2ccc(-c3cccc4c3sc3c(-c5cc(-c6ccccc6)cc(-c6nc(-c7ccccc7)nc(-c7ccccc7)n6)c5)cccc34)cc2)cc1]

Compound F1

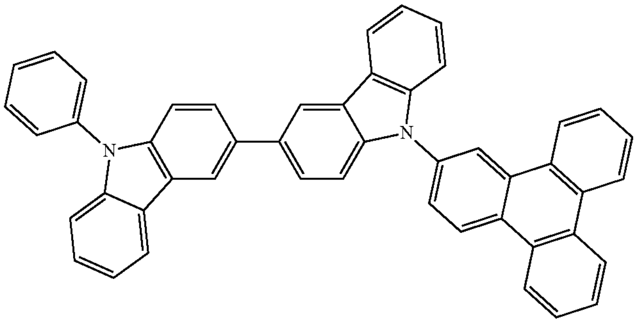 [SMILES: c1ccc(-n2c3ccccc3c3cc(-c4ccc5c(c4)c4ccccc4n5-c4ccc5c6ccccc6c6ccccc6c5c4)ccc32)cc1]

-continued
Compound A11
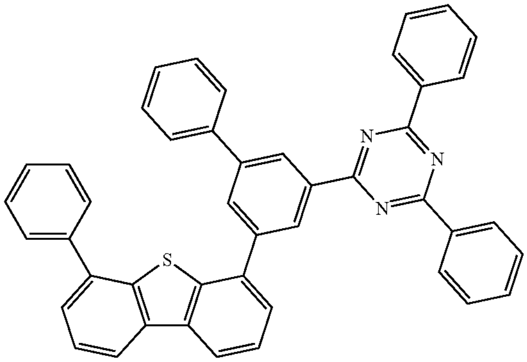 [SMILES: c1ccc(-c2cc(-c3nc(-c4ccccc4)nc(-c4ccccc4)n3)cc(-c3cccc4c3sc3c(-c5ccccc5)cccc34)c2)cc1]
Compound H3
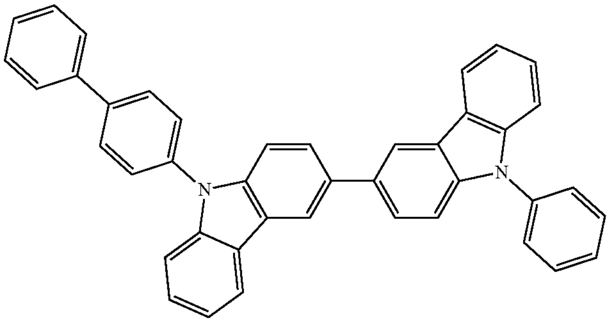 [SMILES: c1ccc(-c2ccc(-n3c4ccccc4c4cc(-c5ccc6c(c5)c5ccccc5n6-c5ccccc5)ccc43)cc2)cc1]
Compound D2
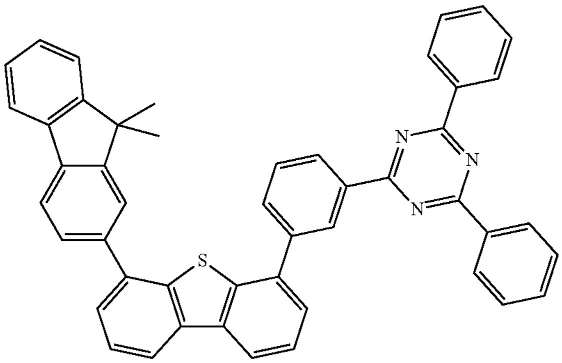 [SMILES: CC1(C)c2ccccc2-c2ccc(-c3cccc4c3sc3c(-c5cccc(-c6nc(-c7ccccc7)nc(-c7ccccc7)n6)c5)cccc34)cc21]
Compound G14
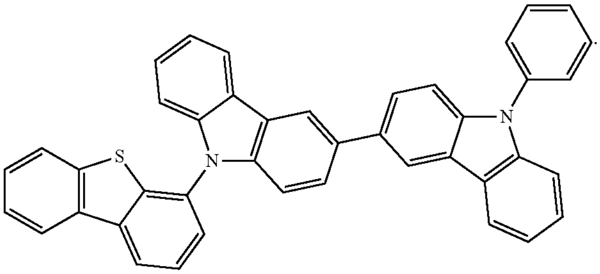 [SMILES: c1ccc(-n2c3ccccc3c3cc(-c4ccc5c(c4)c4ccccc4n5-c4cccc5c4sc4ccccc45)ccc32)cc1]

According to EP3043398 A1, it is possible to use a combination of specific triazine-dibenzofuran-aryl derivatives or specific triazine-dibenzothiophene-aryl derivatives with specific carbazole derivatives for production of light-emitting devices. Two material combinations are specified by way of example in the following table:

Compound 2

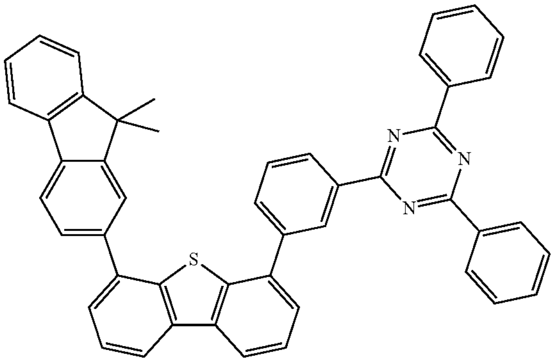 [SMILES: CC1(C)c2ccccc2-c2ccc(-c3cccc4c3sc3c(-c5cccc(-c6nc(-c7ccccc7)nc(-c7ccccc7)n6)c5)cccc34)cc21]

Compound H2

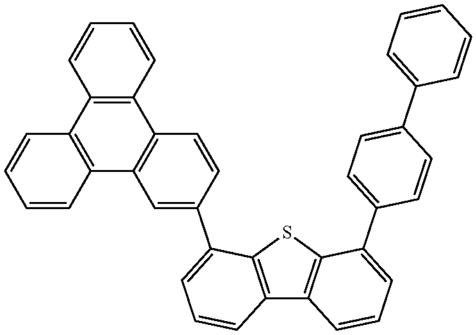 [SMILES: c1ccc(-c2ccc(-c3cccc4c3sc3c(-c5ccc6c7ccccc7c7ccccc7c6c5)cccc34)cc2)cc1]

Compound 5

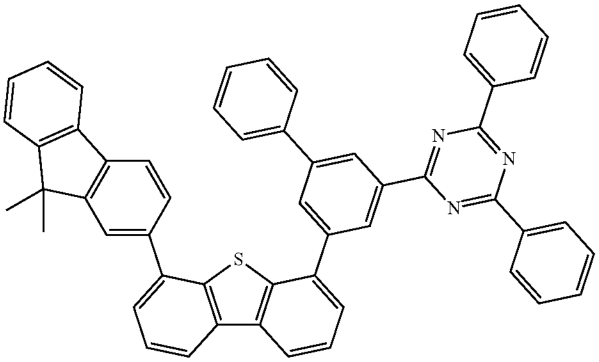 [SMILES: CC1(C)c2ccccc2-c2ccc(-c3cccc4c3sc3c(-c5cc(-c6ccccc6)cc(-c6nc(-c7ccccc7)nc(-c7ccccc7)n6)c5)cccc34)cc21]

Compound H11

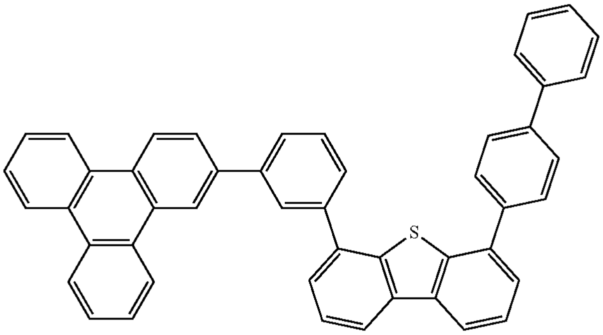 [SMILES: c1ccc(-c2ccc(-c3cccc4c3sc3c(-c5cccc(-c6ccc7c8ccccc8c8ccccc8c7c6)c5)cccc34)cc2)cc1]

According to US 2016/093808, it is possible to use a ternary mixture of specific triazine derivatives for production of organic layers for organic electronic devices, byway of example the mixture TPMI (compound H8, compound C74 and compound H17) and the mixture of compounds C83, F20 and F18. The structures are specified in the following table:
C74
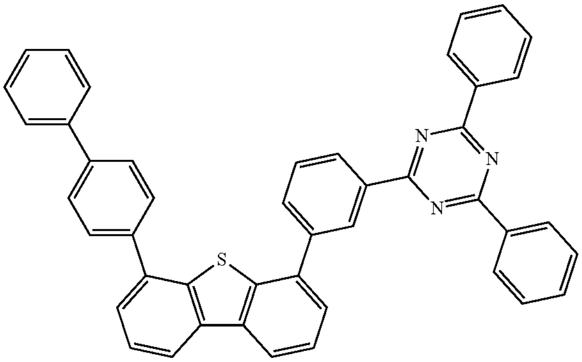 [SMILES: c1ccc(-c2ccc(-c3cccc4c3sc3c(-c5cccc(-c6nc(-c7ccccc7)nc(-c7ccccc7)n6)c5)cccc34)cc2)cc1]
H8
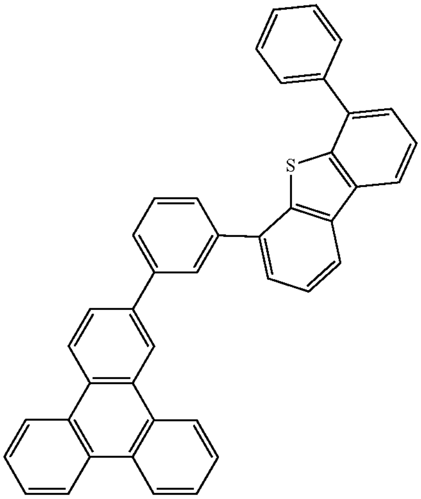 [SMILES: c1ccc(-c2cccc3c2sc2c(-c4cccc(-c5ccc6c7ccccc7c7ccccc7c6c5)c4)cccc23)cc1]
H17
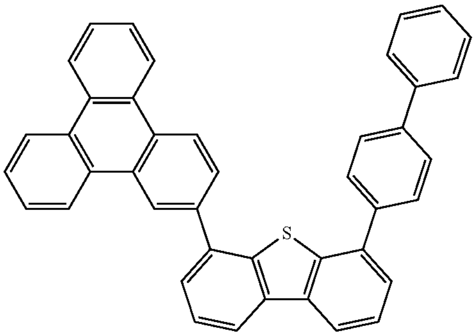 [SMILES: c1ccc(-c2ccc(-c3cccc4c3sc3c(-c5ccc6c7ccccc7c7ccccc7c6c5)cccc34)cc2)cc1]

-continued

C82

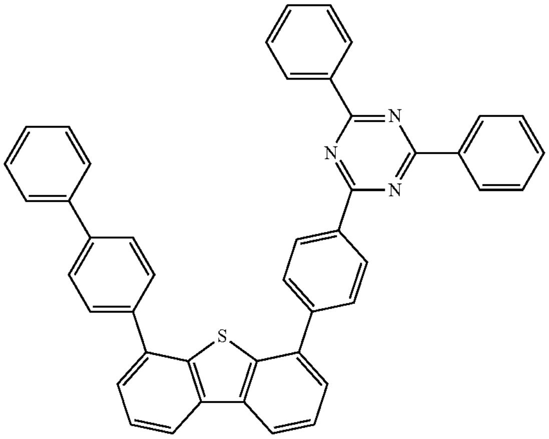 [SMILES: c1ccc(-c2ccc(-c3cccc4c3sc3c(-c5ccc(-c6nc(-c7ccccc7)nc(-c7ccccc7)n6)cc5)cccc34)cc2)cc1]

F20

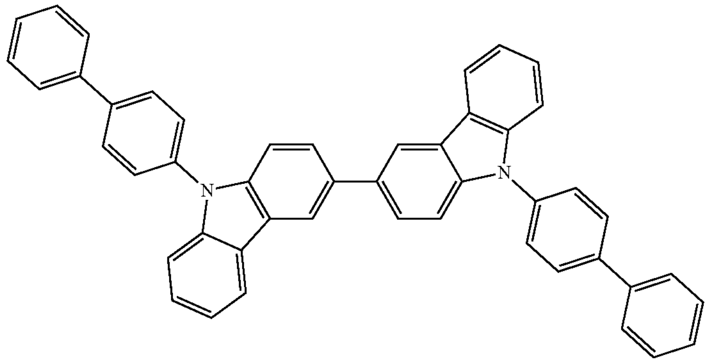 [SMILES: c1ccc(-c2ccc(-n3c4ccccc4c4cc(-c5ccc6c(c5)c5ccccc5n6-c5ccc(-c6ccccc6)cc5)ccc43)cc2)cc1]

F18

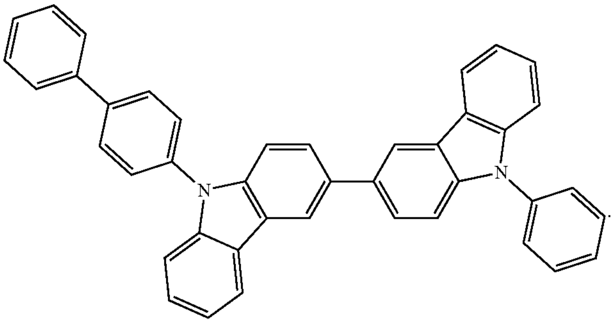 [SMILES: c1ccc(-c2ccc(-n3c4ccccc4c4cc(-c5ccc6c(c5)c5ccccc5n6-c5ccccc5)ccc43)cc2)cc1]

However, there is still need for improvement in the case of use of these materials or in the case of use of mixtures of the materials, especially in relation to efficiency, operating voltage and/or lifetime of the organic electronic device.

It is therefore an object of the present invention to provide materials that are suitable for use in an organic electronic device, especially in an organic electroluminescent device, and especially in a fluorescent or phosphorescent OLED, and lead to good device properties, especially with regard to improved efficiency, improved operating voltage and/or improved lifetime, and that of providing the corresponding electronic device.

It has now been found that this object is achieved, and the disadvantages from the prior art are eliminated, by compositions containing compounds of the formula (1), for example more preferably triazine-dibenzofuran-fluorene derivatives or triazine-benzothiophene-fluorene derivatives, and comprising a hole-transporting host of the formula (2). Such compositions lead to very good properties of organic electronic devices, especially organic electroluminescent devices, especially with regard to efficiency, operating voltage and/or lifetime, and especially also in the presence of a light-emitting component in the emission layer, at concentrations between 2% and 15% by weight.

The present invention therefore firstly provides a composition comprising at least one compound of the formula (1) and at least one compound of the formula (2)

Formula (1)

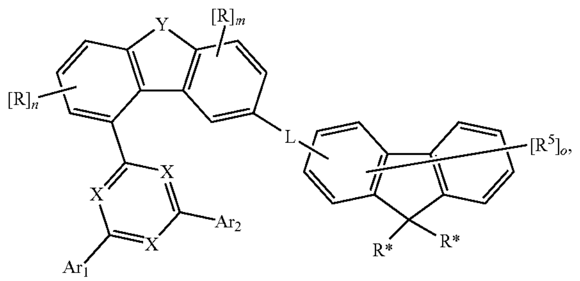

Formula (2)

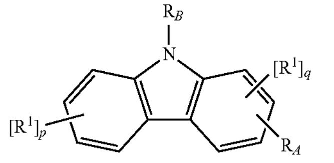

where the symbols and indices used are as follows:

X is the same or different at each instance and is $CR^0$ or N, with the proviso that at least two X groups are N;

Y is selected from O and S;

L is the same or different at each instance and is a single bond or an aromatic ring system which has 6 to 30 aromatic ring atoms and may be substituted by one or more $R^5$ radicals;

$L_1$, $L_2$ are the same or different at each instance and are a single bond or an aromatic or heteroaromatic ring system which has 5 to aromatic ring atoms and may be substituted by one or more $R^3$ radicals;

$L_3$ is a single bond or an aromatic or heteroaromatic ring system which has 5 to 30 aromatic ring atoms and may be substituted by one or more $R^3$ radicals, where one substituent $R^1$ on the carbazole may form a ring with a substituent $R^3$;

$Ar_1$, $Ar_2$ at each instance are each independently an aryl or heteroaryl group having 5 to 40 aromatic ring atoms which may be substituted by one or more $R^3$ radicals;

$R_A$ is H, $-L_3-Ar_4$, $-L_1-N(Ar)_2$;

$R_B$ is $Ar_3$ or $-L_2-N(Ar)_2$;

$Ar_3$ is an aromatic ring system having 6 to 40 aromatic ring atoms or a heteroaromatic ring system having 10 to 40 aromatic ring atoms, which may be substituted by one or more $R^3$ radicals;

$Ar_4$ is the same or different at each instance and is an unsubstituted or substituted 9-arylcarbazolyl or unsubstituted or substituted carbazol-9-yl, which may be substituted by one or more $R^4$ radicals, and where one or more instances each of two $R^4$ radicals or one $R^4$ radical together with one $R^1$ radical may independently form a monocyclic or polycyclic, aliphatic, aromatic or heteroaromatic ring, where aryl is an aromatic or heteroaromatic ring system which has 5 to 30 aromatic ring atoms and may be substituted by $R^3$;

R* is the same or different at each instance and is a straight-chain alkyl group having 1 to 10 carbon atoms or an aryl group having 6 to 12 carbon atoms, where two substituents R* together may form a monocyclic or polycyclic, aliphatic, aromatic or heteroaromatic ring system which may be substituted by one or more substituents $R^5$;

$R^0$, R, $R^1$ are the same or different at each instance and are selected from the group consisting of H, D, F, Cl, Br, I, CN, $NO_2$, $N(Ar)_2$, $N(R^2)_2$, C(=O)Ar, $C(=O)R^2$, $P(=O)(Ar)_2$, $P(Ar)_2$, $B(Ar)_2$, $Si(Ar)_3$, $Si(R^2)_3$, a straight-chain alkyl, alkoxy or thioalkyl group having 1 to carbon atoms or a branched or cyclic alkyl, alkoxy or thioalkyl group having 3 to 20 carbon atoms or an alkenyl group having 2 to carbon atoms, each of which may be substituted by one or more $R^2$ radicals, where one or more nonadjacent $CH_2$ groups may be replaced by $R^2C{=}CR^2$, $Si(R^2)_2$, C=O, C=S, $C{=}NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^2$ radicals, an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals; at the same time, it is optionally possible for two substituents $R^0$ and/or R and/or $R^1$ bonded to the same carbon atom or to adjacent carbon atoms to form a monocyclic or polycyclic, aliphatic, aromatic or heteroaromatic ring system which may be substituted by one or more $R^2$ radicals;

$R^2$ is the same or different at each instance and is selected from the group consisting of H, D, F, Cl, Br, I, CN, $NO_2$, $N(Ar)_2$, $NH_2$, $N(R^3)_2$, C(=O)Ar, C(=O)H, $C(=O)R^3$, $P(=O)(Ar)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^3$ radicals, where one or more nonadjacent $CH_2$ groups may be replaced by HC=CH, $R^3C{=}CR^3$, C≡C, $Si(R^3)_2$, $Ge(R^3)_2$, $Sn(R^3)_2$, C=O, C=S, C=Se, $C{=}NR^3$, $P(=O)(R^3)$, SO, $SO_2$, NH, $NR^3$, O, S, CONH or $CONR^3$ and where one or more hydrogen atoms may be replaced by D, F, Cl, Br, I, CN or $NO_2$, an aromatic or heteroaromatic ring system which has 5 to 60 aromatic ring atoms and may be substituted in each case by one or more $R^3$ radicals, an aryloxy or heteroaryloxy group which has 5 to 60 aromatic ring atoms and may be substituted by one or more $R^3$ radicals, or a combination of these systems; where it is optionally possible for two or more adjacent substituents $R^2$ to form a monocyclic or polycyclic, aliphatic, aromatic or heteroaromatic ring system which may be substituted by one or more $R^3$ radicals;

$R^3$ is the same or different at each instance and is selected from the group consisting of H, D, F, CN, $N(Ar)_2$, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more adjacent $R^3$ substituents together to form a mono- or polycyclic, aliphatic ring system;

$R^4$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I, a straight-chain or branched alkyl group having 1 to 4 carbon atoms or CN; at the same time, two or more adjacent $R^4$ substituents together may form a mono- or polycyclic ring system;

$R^5$ is the same or different at each instance and is selected from the group consisting of D, F, CN and an aryl group having 6 to 18 carbon atoms; at the same time, two or more adjacent substituents $R^5$ together may form a mono- or polycyclic, aliphatic ring system;

Ar is the same or different at each instance and is an aromatic or heteroaromatic ring system which has 5 to 30 aromatic ring atoms and may be substituted by one or more nonaromatic $R^3$ radicals; at the same time, two Ar radicals bonded to the same nitrogen atom, phosphorus atom or boron atom may also be bridged to one another by a single bond or a bridge selected from $N(R^3)$, $C(R^3)_2$, O and S, and n and m at each instance are independently 0, 1, 2 or 3, o at each instance is independently 0, 1, 2, 3, 4, 5, 6 or 7;

q at each instance is independently 0, 1, 2 or 3;

p at each instance is independently 0, 1, 2, 3 or 4.

The invention further provides specific material combinations, formulations comprising compositions of this kind, for the use of these compositions in an organic electronic device, organic electronic devices, preferably electroluminescent devices, comprising compositions of this kind and preferably comprising the composition in one layer, and processes for producing devices of this kind. The corresponding preferred embodiments as described hereinafter likewise form part of the subject-matter of the present invention. The surprising and advantageous effects are achieved through specific selection of known materials, especially with regard to the selection of the compounds of the formula (1).

The layer comprising the composition comprising at least one compound of the formula (1) and at least one compound of the formula (2) as described above or described as preferred hereinafter is especially an emitting layer (EML), an electron transport layer (ETL), an electron injection layer (EIL) and/or a hole blocker layer (HBL).

When the layer is an emitting layer, it is preferably a phosphorescent layer which is characterized in that it comprises, in addition to the composition comprising the matrix materials of the formula (1) and formula (2) as described above, a phosphorescent emitter.

Adjacent carbon atoms in the context of the present invention are carbon atoms bonded directly to one another.

The wording that two or more radicals together may form a ring, in the context of the present description, should be understood to mean, inter alia, that the two radicals are joined to one another by a chemical bond with formal elimination of two hydrogen atoms. This is illustrated by the following scheme:

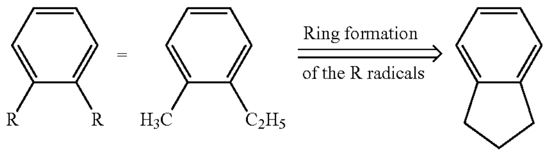

In addition, however, the abovementioned wording shall also be understood to mean that, if one of the two radicals is hydrogen, the second radical binds to the position to which the hydrogen atom was bonded, forming a ring. This shall be illustrated by the following scheme:

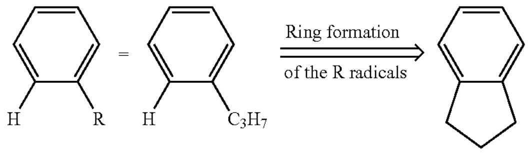

An aryl group in the context of this invention contains 6 to 40 aromatic ring atoms, preferably carbon atoms. A heteroaryl group in the context of this invention contains 5 to 40 aromatic ring atoms, where the ring atoms include carbon atoms and at least one heteroatom, with the proviso that the sum total of carbon atoms and heteroatoms adds up to at least 5. The heteroatoms are preferably selected from N, O and/or S. An aryl group or heteroaryl group is understood here to mean either a simple aromatic cycle, i.e. phenyl, derived from benzene, or a simple heteroaromatic cycle, for example derived from pyridine, pyrimidine or thiophene, or a fused aryl or heteroaryl group, for example derived from naphthalene, anthracene, phenanthrene, quinoline or isoquinoline. An aryl group having 6 to 18 carbon atoms is therefore preferably phenyl, naphthyl, phenanthryl or triphenylenyl, with no restriction in the attachment of the aryl group as substituent. An arylene group having 6 to 18 carbon atoms is therefore preferably phenylene, naphthylene, phenanthrylene or triphenylenylene, with no restriction in the linkage of the arylene group as linker.

An aromatic ring system in the context of this invention contains 6 to 40 carbon atoms in the ring system and may be substituted by one or more $R^3$ radicals, where $R^3$ has a definition described below. An aromatic ring system also contains aryl groups as described above.

An aromatic ring system having 6 to 18 carbon atoms is preferably selected from phenylene, biphenylene, naphthylene, phenanthrenylene and triphenylenylene, where the respective aromatic ring system may be substituted by one or more $R^5$ radicals.

A heteroaromatic ring system in the context of this invention contains 5 to ring atoms and at least one heteroatom and may be substituted by one or more $R^3$ radicals, where $R^3$ has a definition described below. A preferred heteroaromatic ring system has 10 to 40 ring atoms and at least one heteroatom and may be substituted by one or more $R^3$ radicals, where $R^3$ has a definition described below. A heteroaromatic ring system also contains heteroaryl groups as described above. The heteroatoms in the heteroaromatic ring system are preferably selected from N, O and/or S. An aromatic or heteroaromatic ring system in the context of this invention is understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic or heteroaromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, are likewise encompassed by the definition of the aromatic or heteroaromatic ring system.

An aromatic or heteroaromatic ring system which has 5-40 aromatic ring atoms and may also be substituted in each case by the abovementioned $R^3$ radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The abbreviation Ar is the same or different at each instance and is an aromatic or heteroaromatic ring system which has 5 to 30 aromatic ring atoms and may be substituted by one or more nonaromatic $R^3$ radicals; at the same time, two Ar radicals bonded to the same nitrogen atom, phosphorus atom or boron atom may also be bridged to one another by a single bond or a bridge selected from $N(R^3)$, $C(R^3)_2$, O and S. The substituent $R^3$ has been described above or is described with preference hereinafter.

A cyclic alkyl, alkoxy or thioalkyl group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals.

An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl.

An alkynyl group is understood to mean, for example, ethynyl, propynyl, butynyl, pentynyl, hexynyl, heptynyl or octynyl.

A $C_1$- to $C_{20}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

A $C_1$- to $C_{20}$-thioalkyl group is understood to mean, for example S-alkyl groups, for example thiomethyl, 1-thioethyl, 1-thio-i-propyl, 1-thio-n-propyl, 1-thio-i-butyl, 1-thio-n-butyl or 1-thio-t-butyl.

An aryloxy or heteroaryloxy group having 5 to 40 aromatic ring atoms means O-aryl or O-heteroaryl and means that the aryl or heteroaryl group is bonded via an oxygen atom.

An aralkyl or heteroaralkyl group having 5 to 40 aromatic ring atoms means that an alkyl group as described above is substituted by an aryl group or heteroaryl group.

A phosphorescent emitter in the context of the present invention is a compound that exhibits luminescence from an excited state with higher spin multiplicity, i.e. a spin state >1, especially from an excited triplet state. In the context of this application, all luminescent complexes with transition metals or lanthanides are to be regarded as phosphorescent emitters. A more exact definition is given further down.

When the composition comprising at least one compound of the formula (1) as described above or described as preferred hereinafter and at least one compound of the formula (2) as described above or described hereinafter is used as matrix material for a phosphorescent emitter, it is preferable when the triplet energy thereof is not significantly less than the triplet energy of the phosphorescent emitter. In respect of the triplet level, it is preferably the case that $T_1(\text{emitter})-T_1(\text{matrix}) \leq 0.2$ eV, more preferably $\leq 0.15$ eV, most preferably $\leq 0.1$ eV. $T_1(\text{matrix})$ here is the triplet level of the matrix material in the emission layer, this condition being applicable to each of the two matrix materials, and $T_1(\text{emitter})$ is the triplet level of the phosphorescent emitter. If the emission layer contains more than two matrix materials, the abovementioned relationship is preferably also applicable to every further matrix material.

In a preferred embodiment of the invention, compounds of the formula (1) in which Y is selected from O and S, preferably O, are selected.

In compounds of the formula (1), the symbol X is N in two instances and $CR^0$ at one instance, or N in three instances.

The substituent

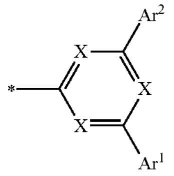

therefore has the following definitions, where * indicates the bonding site to the dibenzofuran or dibenzothiophene and $R^0$, $Ar^1$ and $Ar^2$ have a definition given above or a definition given as preferred:

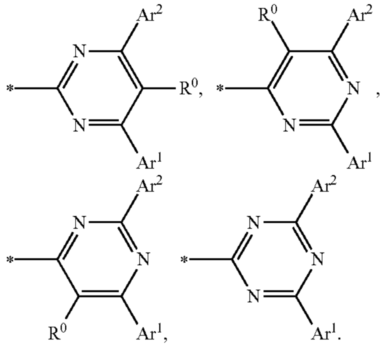

$R^0$ is the same or different at each instance and is preferably selected from the group consisting of H, D, F or an aromatic or heteroaromatic ring system having 5 to 40 aromatic ring atoms. $R^0$ at each instance is more preferably H.

Compounds of the formula (1) in which X at each instance is N are represented by the formula (1a)

Formula (1a)

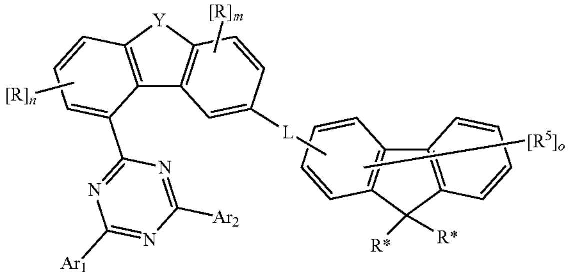

where Y, L, $Ar_1$, $Ar_2$, R, $R^5$, R*, n, m and o have a definition given above or a definition given hereinafter.

More preferably, at least one compound of the formula (1a) having substituents described above, described as preferred or described hereinafter as preferred is selected for the composition.

The invention accordingly further provides a composition as described above, where the compound of the formula (1) conforms to the formula (1a), preferably when the symbol Y is O.

In compounds of the formula (1) or (1a), or compounds of the formula (1) or (1a) described with preference, $Ar_1$ and $Ar_2$ are each independently preferably an aryl group which has 6 to 40 carbon atoms, as described above or described as preferred, and may be substituted by one or more $R^3$ radicals or are a dibenzofuranyl or dibenzothiophenyl group which may be substituted by one or more $R^3$ radicals.

The bonding of the aryl group or of the dibenzofuranyl group or dibenzothiophenyl group is not restricted here.

$Ar_1$ and $Ar_2$ may therefore preferably be selected from the following Ar-1 to Ar-12 groups, where $R^3$ has a definition specified above or specified as preferred:

Ar-1

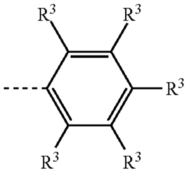

Ar-2

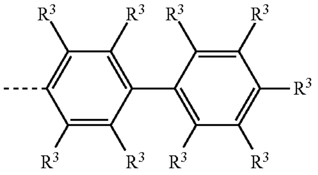

Ar-3

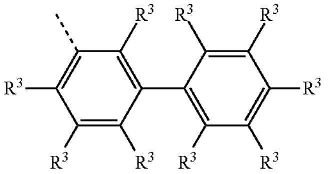

Ar-4

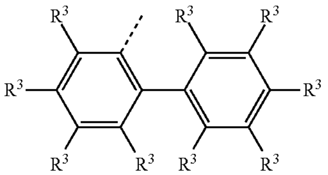

Ar-5

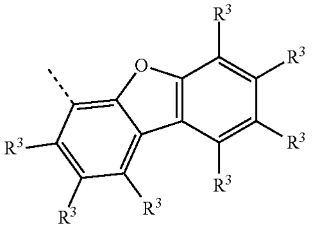

Ar-6

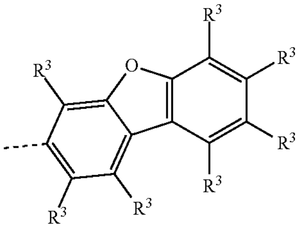

Ar-7

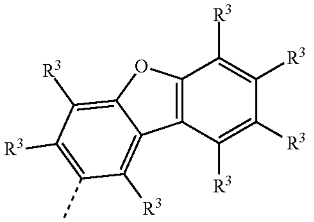

-continued

Ar-8

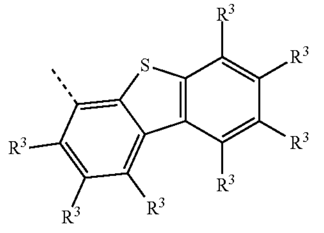

Ar-9

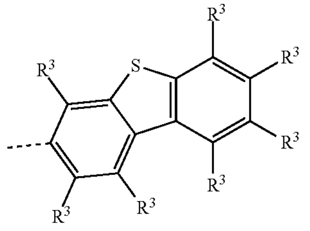

Ar-10

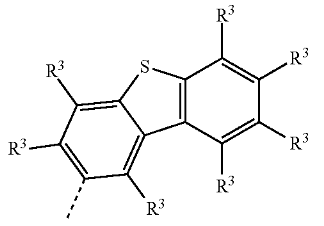

Ar-11

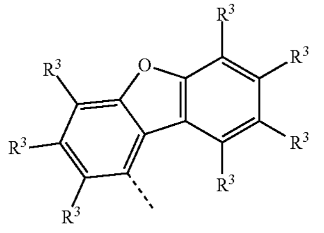

Ar-12

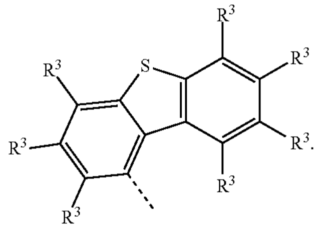

More preferably, at least one $Ar_1$ or $Ar_2$ is phenyl and the other aromatic substituent is an aryl group which has 6 to 40 carbon atoms and may be substituted by one or more $R^3$ radicals or is a dibenzofuranyl or dibenzothiophenyl group, preferably selected from Ar-1 to Ar-12. More preferably, at least one $Ar_1$ or $Ar_2$ is phenyl and the other aromatic substituent is a phenyl group which may be substituted by one or more $R^3$ radicals or is dibenzofuranyl. Most preferably, both $Ar_1$ and $Ar_2$ groups are the same. Most preferably, both $Ar_1$ and $Ar_2$ groups are phenyl or both $Ar_1$ and $Ar_2$ groups are dibenzofuranyl.

When, in compounds of the formulae (1) or (1a) or compounds of the formulae (1) or (1a) described as preferred, $Ar_1$ and $Ar_2$ are, as described above or described as preferred, an aryl or heteroaryl group substituted by one or more $R^3$ radicals, the substituent $R^3$ is the same or different at each instance and is preferably selected from the group consisting of D, F or an aromatic or heteroaromatic ring system having 5 to 40 aromatic ring atoms. The heteroaromatic ring system having 5 to 40 aromatic ring atoms in this case of $R^3$ is preferably derived from dibenzofuran or dibenzothiophene. The aromatic ring system having 6 to 40 aromatic ring atoms in this case of $R^3$ is preferably phenyl, biphenyl or terphenyl, more preferably phenyl or [1,1',2',1"]-terphenyl-5'-yl. Preferably, the aryl group or heteroaryl group in $Ar_1$ and $Ar_2$ is in each case independently substituted once by $R^3$. More preferably, the aryl group or heteroaryl group in $Ar_1$ or $Ar_2$ is substituted once by $R^3$.

The substituent $R^3$ on the dibenzofuranyl or dibenzothiophenyl is preferably H. The substituent $R^3$ on the aryl group having 6 to 40 carbon atoms, when it occurs, is preferably phenyl or H. Most preferably, the aryl group or heteroaryl group in $Ar_1$ and $Ar_2$ is unsubstituted.

In compounds of the formulae (1) or (1a), or compounds of the formulae (1) or (1a) described as preferred, the substituent R* is the same or different at each instance and is a straight-chain alkyl group having 1 to 10 carbon atoms or an aryl group having 6 to 12 carbon atoms, where the two substituents R* may together form a monocyclic or polycyclic, aliphatic, aromatic or heteroaromatic ring system that may be substituted by one or more substituents $R^5$. R* is preferably the same at each instance, or two substituents R* together form a monocyclic or polycyclic, aliphatic, aromatic or heteroaromatic ring system. More preferably, R* is selected from methyl, ethyl and phenyl. More preferably, two substituents R* together with the carbon atom to which they are bonded form a ring system selected from cyclopentyl and dibenzocyclopentyl which may be substituted by one or more substituents $R^5$. The ring system formed by two substituents R* is more preferably a spirobifluorene.

Compounds of the formula (1) in which the substituents R* have a preferred definition, as described above, are represented by the formulae (1b), (1c), (1d), (1e) and (1f)

Formula (1b)

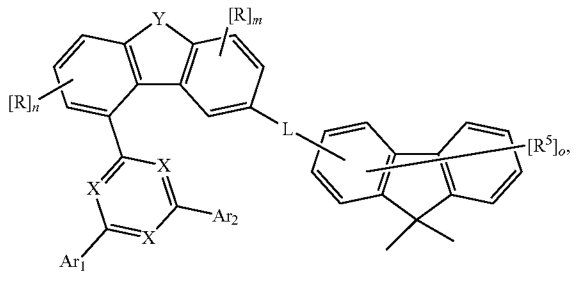

Formula (1c)

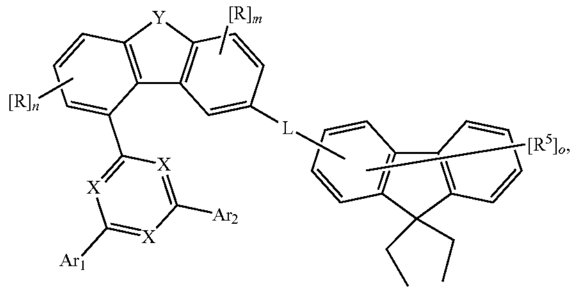

-continued

Formula (1d)

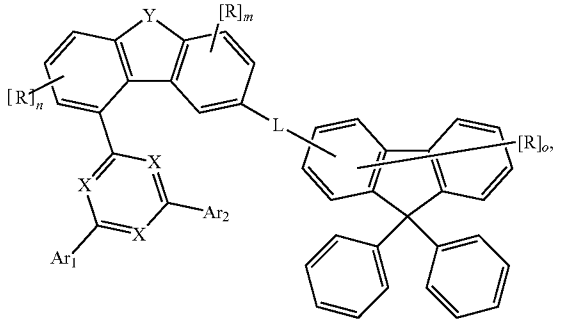

Formula (1e)

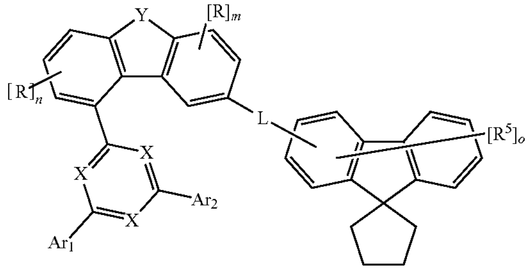 or

Formula (1f)

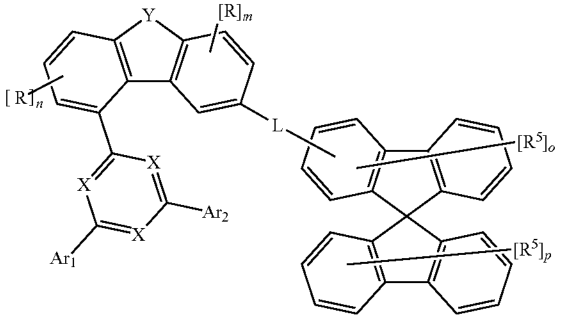

where X, Y, L, $Ar_1$, $Ar_2$, R, $R^5$, n, m and o have a definition given above or a definition given as preferred or a definition given hereinafter and p is 0, 1, 2, 3, 4, 5, 6, 7 or 8.

In compounds of the formulae (1), (1a), (1b), (1c), (1d), (1e) and (1f), or in compounds of the formulae (1), (1a), (1b), (1c), (1d), (1e) and (1f) described as preferred, n is preferably 0 or 1, where R has a definition given above or a definition given hereinafter. More preferably, n is 0.

In compounds of the formulae (1), (1a), (1b), (1c), (1d), (1e) and (1f), or in compounds of the formulae (1), (1a), (1b), (1c), (1d), (1e) and (1f) described as preferred, m is preferably 0 or 1, where R has a definition given above or a definition given hereinafter. More preferably, m is 0.

In compounds of the formulae (1), (1a), (1b), (1c), (1d), (1e) and (1f), or in compounds of the formulae (1), (1a), (1b), (1c), (1d), (1e) and (1f) described as preferred, the sum total of n and m, (n+m) for short, is preferably 0, 1 or 2, where R has a definition given above or a definition given hereinafter. More preferably, (n+m) is 0 or 1. Most preferably, (n+m) is 0.

In compounds of the formulae (1), (1a), (1b), (1c), (1d), (1e) and (1f), or in compounds of the formulae (1), (1a), (1b), (1c), (1d), (1e) and (1f) described as preferred, o is preferably 0, 1 or 2, where $R^5$ has a definition given above or a definition given hereinafter. More preferably, o is 0.

In compounds of the formula (1f) or compounds of the formula (1f) described as preferred, p is preferably 0, 1 or 2, where $R^5$ has a definition given above or a definition given hereinafter. More preferably, p is 0.

When, in compounds of the formulae (1), (1a), (1b), (1c), (1d), (1e) and (1f) or in compounds of the formulae (1), (1a), (1b), (1c), (1d), (1e) and (1f) described as preferred, n or m is greater than 0, the substituent R is the same or different at each instance and is preferably selected from the group consisting of D, F, an alkyl group having 1 to 40 carbon atoms or an aromatic or heteroaromatic ring system having 5 to 40 aromatic ring atoms. The heteroaromatic ring system having 5 to 40 aromatic ring atoms in this case of R is preferably derived from dibenzofuran or dibenzothiophene. The aromatic ring system having 6 to 40 aromatic ring atoms in this case of R is preferably phenyl, biphenyl or terphenyl, more preferably phenyl or [1,1',2',1"]-terphenyl-5'-yl. The alkyl group having 1 to 40 carbon atoms in this case of R is preferably a linear or branched alkyl group having 1 to 4 carbon atoms, more preferably methyl, ethyl, n-propyl or n-butyl, most preferably methyl.

When, in compounds of the formulae (1), (1a), (1b), (1c), (1d), (1e) and (1f) or in compounds of the formulae (1), (1a), (1b), (1c), (1d), (1e) and (1f) described as preferred, o or p is greater than 0, the substituent $R^5$ is the same or different at each instance and is preferably selected from the group consisting of D and phenyl.

In compounds of the formulae (1), (1a), (1b), (1c), (1d), (1e) and (1f) or in compounds of the formulae (1), (1a), (1b), (1c), (1d), (1e) and (1f) described as preferred, L is the same or different at each instance and is a single bond or an aromatic ring system which has 6 to 30 aromatic ring atoms and may be substituted by one or more $R^5$ radicals, where $R^5$ is defined as described above. $R^5$ here is preferably selected from the group consisting of D and phenyl. L is preferably a single bond or an aromatic ring system having 6 to 18 carbon atoms, preferably phenylene, diphenylene, naphthylene, phenanthrenylene or triphenylenylene, where the attachment to the further substituents is not restricted. Phenylene here may be bonded to the dibenzofuran/dibenzothiophene unit and the fluorenyl unit in the ortho, meta or para position for example.

L may therefore preferably be selected from the following linkers L-1 to L-20 that may be unsubstituted or substituted by $R^5$ as described above:

L-1

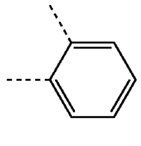

L-2

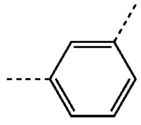

L-3

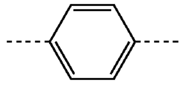

L-4

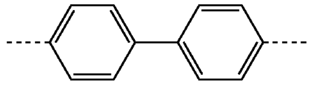

-continued

L-5

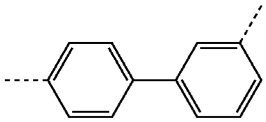

L-6

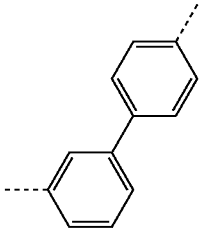

L-7

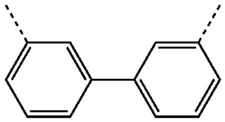

L-8

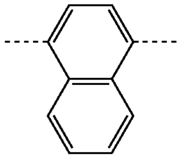

L-9

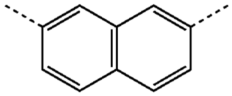

L-10

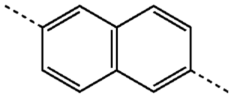

L-11

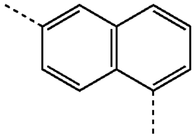

L-12

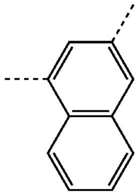

L-13

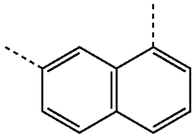

L-14

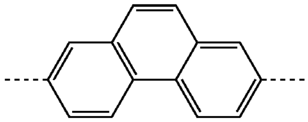

-continued

L-15

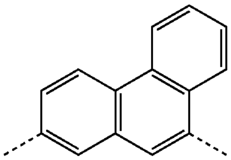

L-16

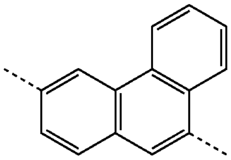

L-17

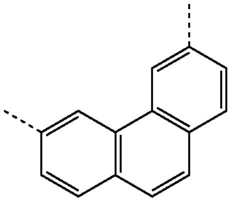

L-18

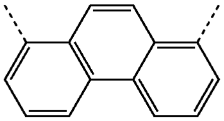

L-19

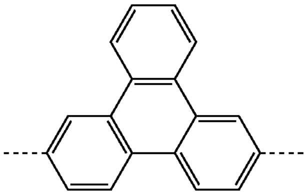

L-20

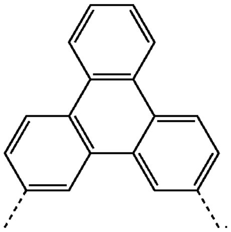

Preferably, the linkers L-1 to L-20 are unsubstituted.

Particular preference is given to using the linkers L-1 to L-7.

Preferably, L is joined as phenylene in the meta position.

In compounds of the formulae (1), (1a), (1b), (1c), (1d), (1e) and (1f) or in compounds of the formulae (1), (1a), (1b), (1c), (1d), (1e) and (1f) that are described as preferred, L may be bonded to the fluorenyl in any position. L, as described above or described as preferred, is more preferably joined in position 2 and 4 of the fluorenyl radical, most preferably in position 2 of the fluorenyl radical.

L, as described above or described as preferred, is preferably joined in position 2, 3 or 4 of the bispirofluorenyl radical, or most preferably in position 2 of the bispirofluorenyl radical.

Particularly preferred compounds of the formula (1) conform to the formulae (1d) and (1f), as described above.

The invention likewise further provides the specific compounds of the formula (1a)

Formula (1a)

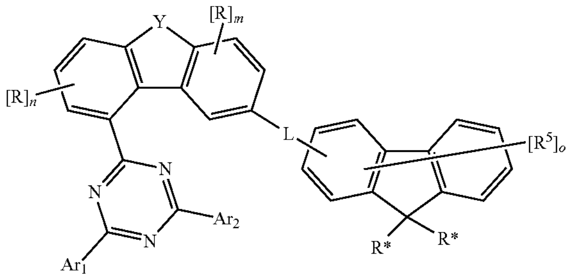

where the symbols and indices used are as follows:

Y is selected from O and S;

L is the same or different at each instance and is an aromatic ring system having 6 to 18 carbon atoms, preferably phenylene, biphenylene, naphthylene, phenanthrenylene or triphenylenylene, which may be substituted by one or more $R^5$ radicals;

$Ar_1$, $Ar_2$ at each instance are each independently an aryl or heteroaryl group having 5 to 40 aromatic ring atoms which may be substituted by one or more $R^3$ radicals;

R* is the same or different at each instance and is a straight-chain alkyl group having 1 to 10 carbon atoms or an aryl group having 6 to 12 carbon atoms, where two substituents R* together may form a monocyclic or polycyclic, aliphatic, aromatic or heteroaromatic ring system which may be substituted by one or more $R^5$ radicals;

R is the same or different at each instance and is selected from the group consisting of D, F, CN and an aryl group having 6 to 10 carbon atoms;

$R^3$ is the same or different at each instance and is selected from the group consisting of H, D, F, CN, $N(Ar)_2$, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more adjacent $R^3$ substituents together to form a mono- or polycyclic, aliphatic ring system;

$R^5$ is the same or different at each instance and is selected from the group consisting of D, F, CN and an aryl group having 6 to 18 carbon atoms; at the same time, two or more adjacent substituents $R^5$ together may form a mono- or polycyclic, aliphatic ring system;

n and m at each instance are independently 0, 1, 2 or 3 and o at each instance is independently 0, 1, 2, 3, 4, 5, 6 or 7.

The definitions of Y, L, $Ar^1$, $Ar^2$, R, $R^3$, $R^5$, R*, n, m and o that are specified as preferred are correspondingly applicable, as described above.

Accordingly, the invention likewise provides the preferred compounds of the following formulae (1g), (1h), (1i), (1j) and (1k):

Formula (1g)

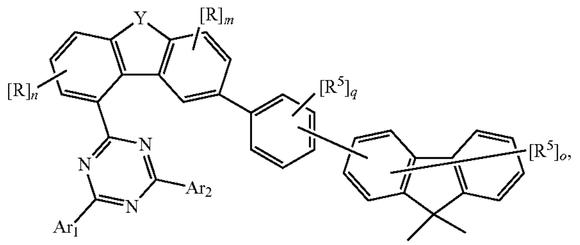

Formula (1h)

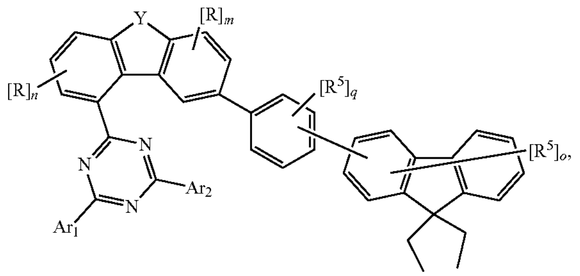

Formula (1i)

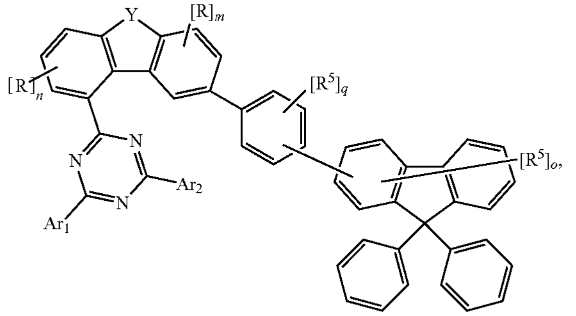

Formula (1j)

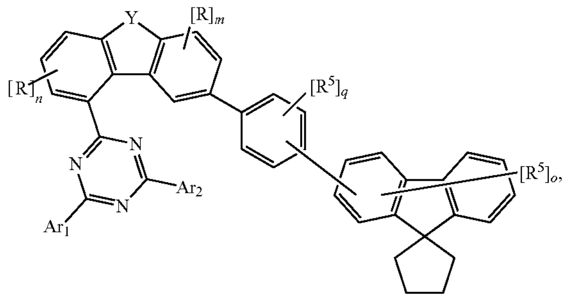

Formula (1k)

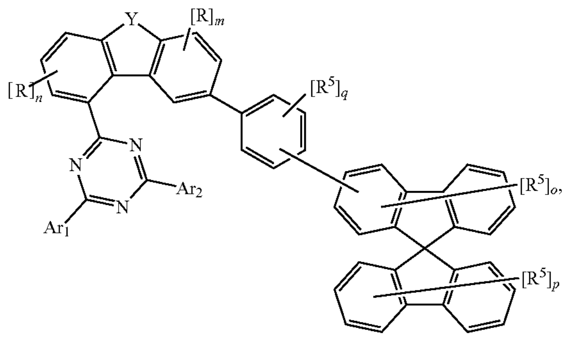

where Y, $Ar_1$, $Ar_2$, R, $R^5$, n, m, o and p have a definition given above or a definition given as preferred and q is 0, 1, 2, 3 or 4. If q is greater than 0, $R^5$ is preferably D or phenyl.

In compounds of the formulae (1), (1a), (1g), (1h), (1i), (1j) and (1k), Y is preferably O, $Ar^1$ and $Ar^2$ are preferably phenyl, dibenzofuranyl, dibenzothiophenyl and biphenyl, as described above, and n, m, o, p and q are preferably 0.

Compounds of the formulae (1g), (1h), (1i), (1j) and (1k) are preferably selected for the composition of the invention.

Compounds of the formula (1k) are preferably provided by the invention or are more preferably selected for the composition of the invention, where the symbols utilized have a definition specified or one specified as preferred.

Examples of suitable compounds of the formulae (1), (1a), (1b), (1c), (1d), (1e), (1f), (1g), (1h), (1i), (1j) and (1k) that are selected in accordance with the invention are the structures shown below in table 1.

TABLE 1

1

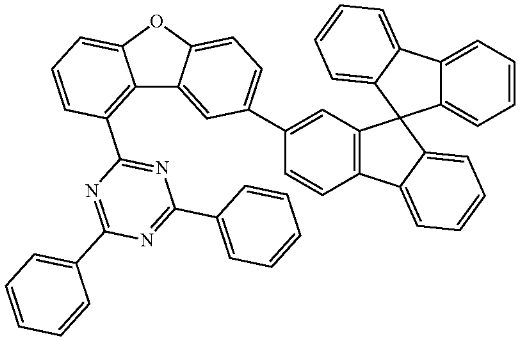 [SMILES: c1ccc(-c2nc(-c3ccccc3)nc(-c3cccc4oc5ccc(-c6ccc7c(c6)C6(c8ccccc8-c8ccccc86)c6ccccc6-7)cc5c34)n2)cc1]

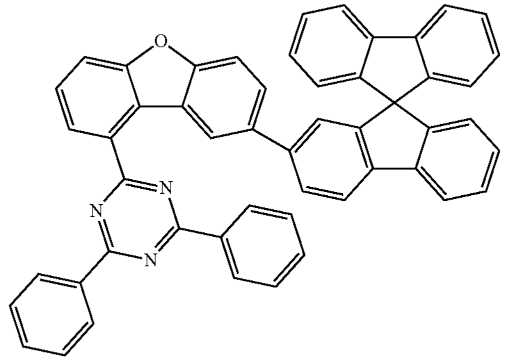 [SMILES: c1ccc(-c2nc(-c3ccccc3)nc(-c3cccc4oc5ccc(-c6ccc7c(c6)C6(c8ccccc8-c8ccccc86)c6ccccc6-7)cc5c34)n2)cc1]

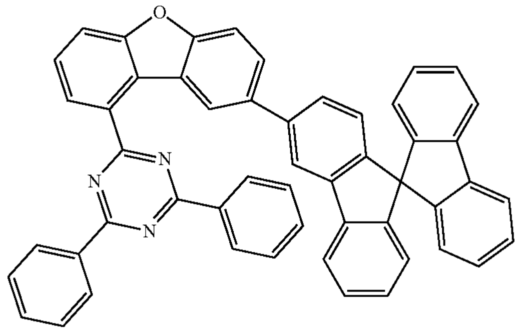 [SMILES: c1ccc(-c2nc(-c3ccccc3)nc(-c3cccc4oc5ccc(-c6ccc7c(c6)-c6ccccc6C76c7ccccc7-c7ccccc76)cc5c34)n2)cc1]

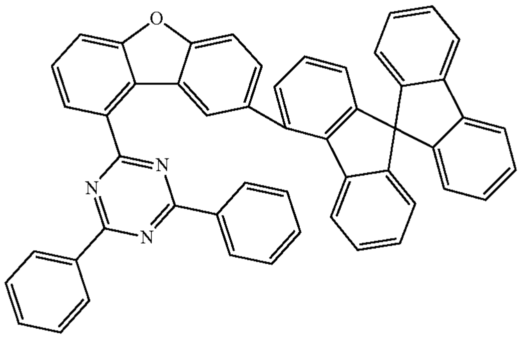 [SMILES: c1ccc(-c2nc(-c3ccccc3)nc(-c3cccc4oc5ccc(-c6cccc7c6-c6ccccc6C76c7ccccc7-c7ccccc76)cc5c34)n2)cc1]

TABLE 1-continued
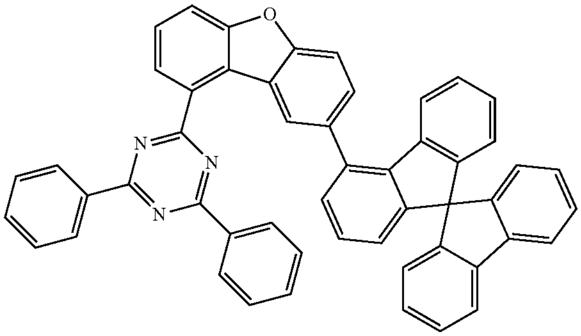 [SMILES: c1ccc(-c2nc(-c3ccccc3)nc(-c3cccc4oc5ccc(-c6cccc7c6-c6ccccc6C76c7ccccc7-c7ccccc76)cc5c34)n2)cc1]
2
3
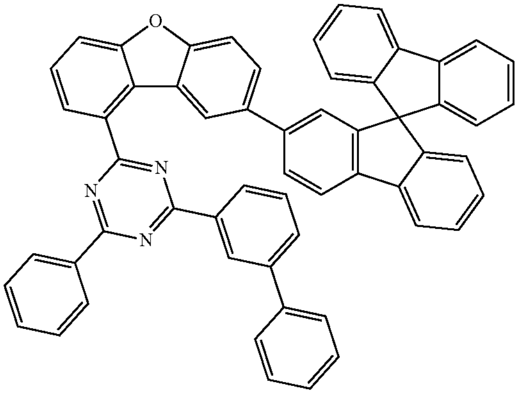 [SMILES: c1ccc(-c2cccc(-c3nc(-c4ccccc4)nc(-c4cccc5oc6ccc(-c7ccc8c(c7)C7(c9ccccc9-c9ccccc97)c7ccccc7-8)cc6c45)n3)c2)cc1]
4
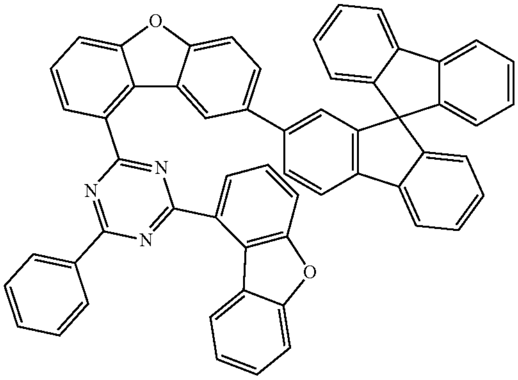 [SMILES: c1ccc(-c2nc(-c3cccc4oc5ccccc5c34)nc(-c3cccc4oc5ccc(-c6ccc7c(c6)C6(c8ccccc8-c8ccccc86)c6ccccc6-7)cc5c34)n2)cc1]
5
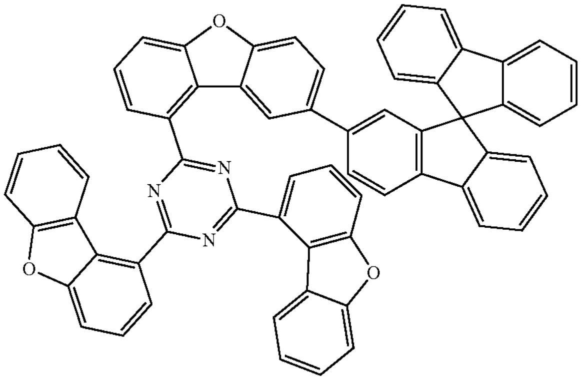 [SMILES: c1ccc2c(c1)-c1ccccc1C21c2ccccc2-c2ccc(-c3ccc4oc5cccc(-c6nc(-c7cccc8oc9ccccc9c78)nc(-c7cccc8oc9ccccc9c78)n6)c5c4c3)cc21]

TABLE 1-continued
6
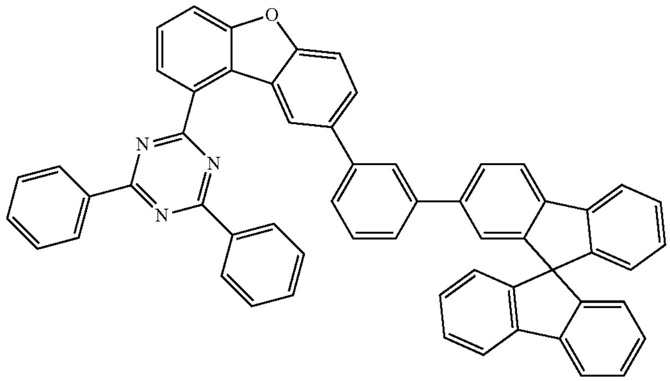 [SMILES: c1ccc(-c2nc(-c3ccccc3)nc(-c3cccc4oc5ccc(-c6cccc(-c7ccc8c(c7)C7(c9ccccc9-c9ccccc97)c7ccccc7-8)c6)cc5c34)n2)cc1]
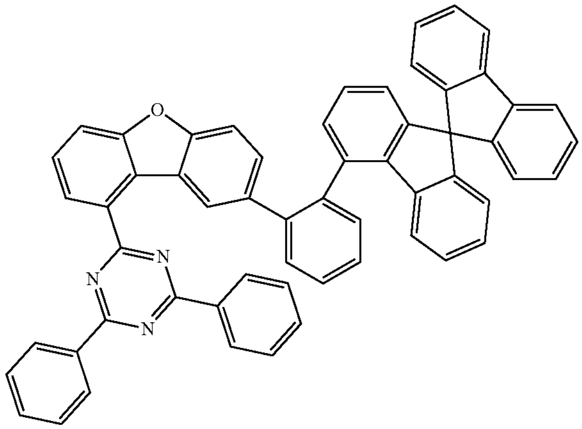 [SMILES: c1ccc(-c2nc(-c3ccccc3)nc(-c3cccc4oc5ccc(-c6ccccc6-c6cccc7c6-c6ccccc6C76c7ccccc7-c7ccccc76)cc5c34)n2)cc1]
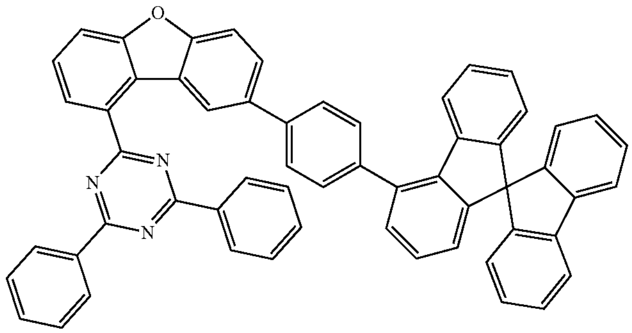 [SMILES: c1ccc(-c2nc(-c3ccccc3)nc(-c3cccc4oc5ccc(-c6ccc(-c7cccc8c7-c7ccccc7C87c8ccccc8-c8ccccc87)cc6)cc5c34)n2)cc1]

TABLE 1-continued
7
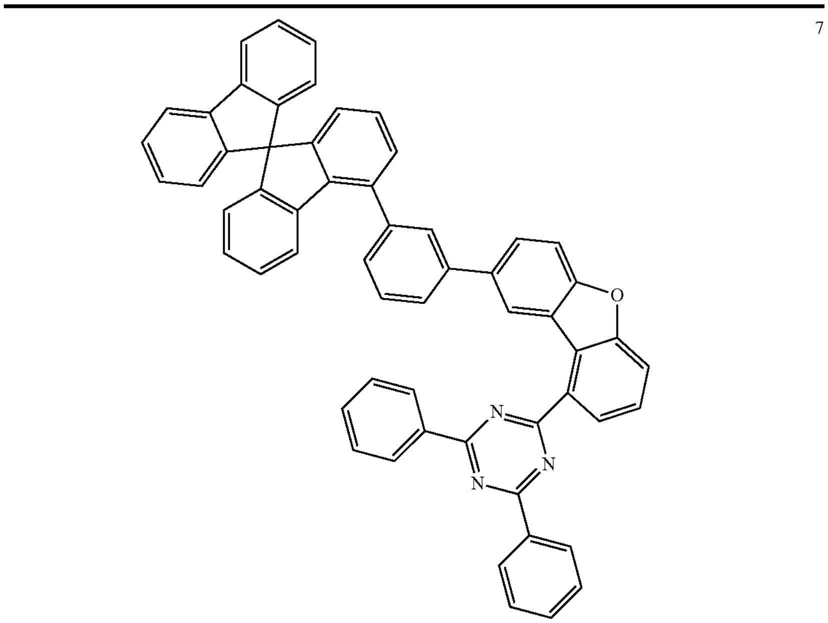
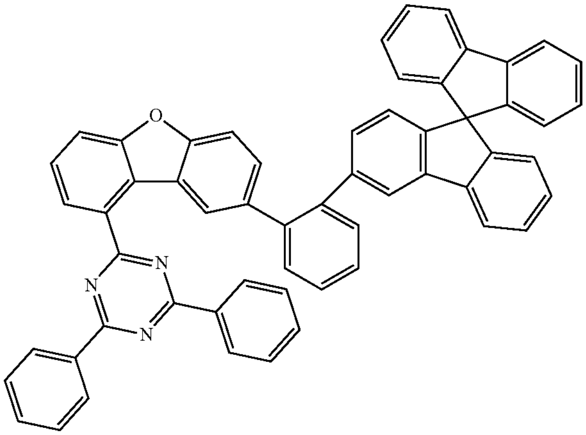 [SMILES: c1ccc(-c2nc(-c3ccccc3)nc(-c3cccc4oc5ccc(-c6ccccc6-c6ccc7c(c6)-c6ccccc6C76c7ccccc7-c7ccccc76)cc5c34)n2)cc1]
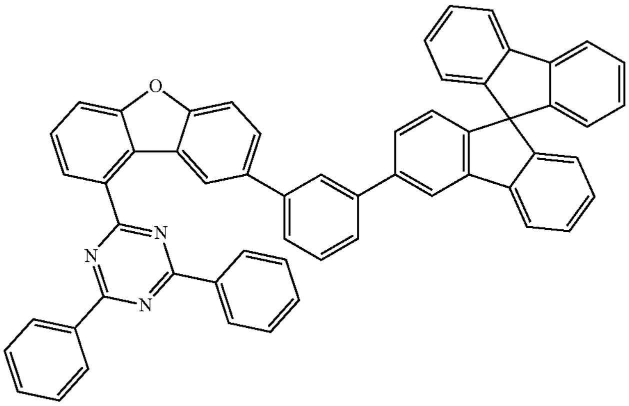 [SMILES: c1ccc(-c2nc(-c3ccccc3)nc(-c3cccc4oc5ccc(-c6cccc(-c7ccc8c(c7)-c7ccccc7C87c8ccccc8-c8ccccc87)c6)cc5c34)n2)cc1]

TABLE 1-continued
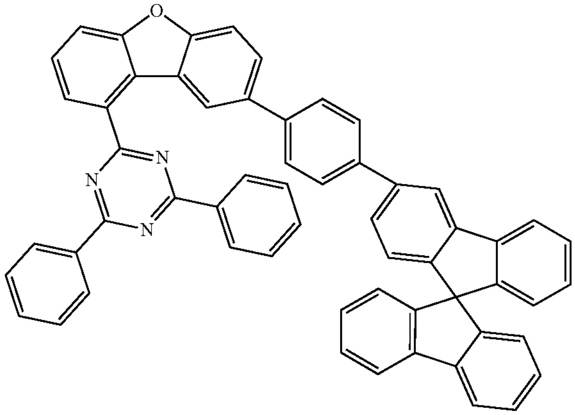 [SMILES: c1ccc(-c2nc(-c3ccccc3)nc(-c3cccc4oc5ccc(-c6ccc(-c7ccc8c(c7)-c7ccccc7C87c8ccccc8-c8ccccc87)cc6)cc5c34)n2)cc1]
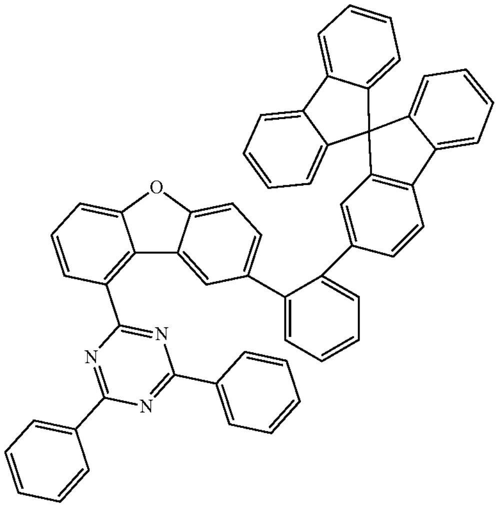 [SMILES: c1ccc(-c2nc(-c3ccccc3)nc(-c3cccc4oc5ccc(-c6ccccc6-c6ccc7c(c6)C6(c8ccccc8-c8ccccc86)c6ccccc6-7)cc5c34)n2)cc1]
8
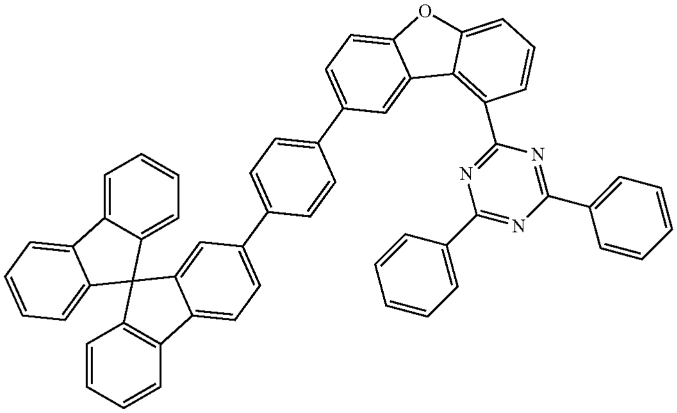 [SMILES: c1ccc(-c2nc(-c3ccccc3)nc(-c3cccc4oc5ccc(-c6ccc(-c7ccc8c(c7)C7(c9ccccc9-c9ccccc97)c7ccccc7-8)cc6)cc5c34)n2)cc1]

TABLE 1-continued
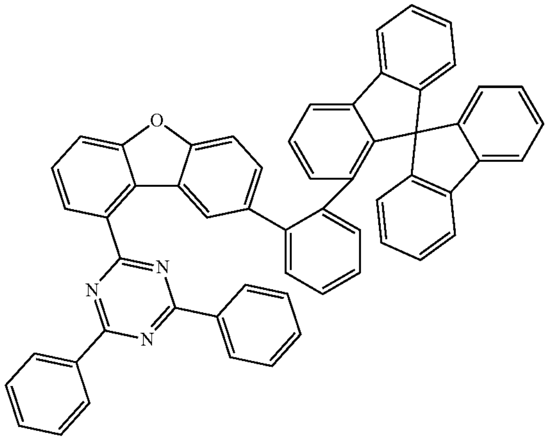 [SMILES: c1ccc(-c2nc(-c3ccccc3)nc(-c3cccc4oc5ccc(-c6ccccc6-c6cccc7c6C6(c8ccccc8-c8ccccc86)c6ccccc6-7)cc5c34)n2)cc1]
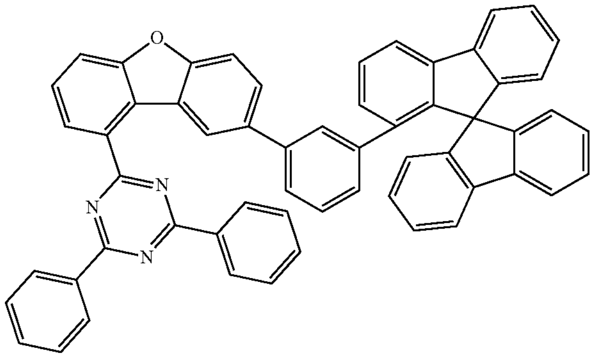 [SMILES: c1ccc(-c2nc(-c3ccccc3)nc(-c3cccc4oc5ccc(-c6cccc(-c7cccc8c7C7(c9ccccc9-c9ccccc97)c7ccccc7-8)c6)cc5c34)n2)cc1]
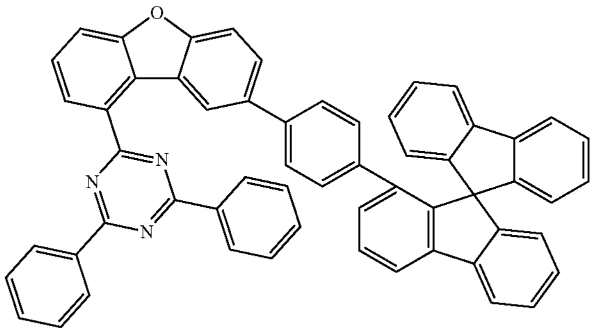 [SMILES: c1ccc(-c2nc(-c3ccccc3)nc(-c3cccc4oc5ccc(-c6ccc(-c7cccc8c7C7(c9ccccc9-c9ccccc97)c7ccccc7-8)cc6)cc5c34)n2)cc1]
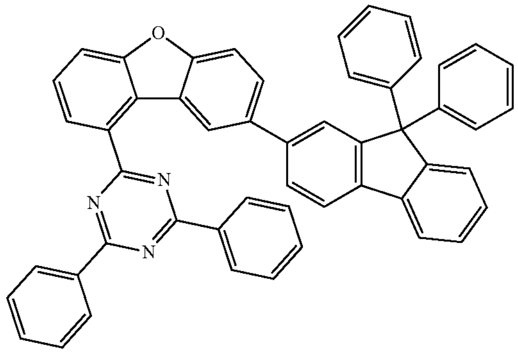 [SMILES: c1ccc(-c2nc(-c3ccccc3)nc(-c3cccc4oc5ccc(-c6ccc7c(c6)C(c6ccccc6)(c6ccccc6)c6ccccc6-7)cc5c34)n2)cc1]

TABLE 1-continued
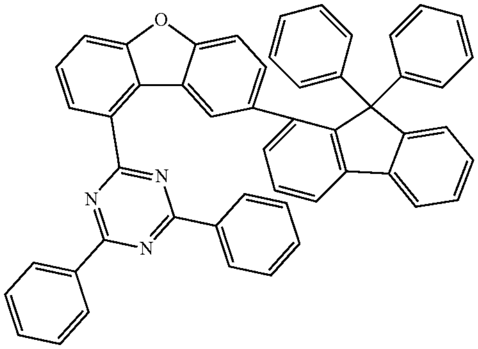 [SMILES: c1ccc(-c2nc(-c3ccccc3)nc(-c3cccc4oc5ccc(-c6cccc7c6C(c6ccccc6)(c6ccccc6)c6ccccc6-7)cc5c34)n2)cc1]
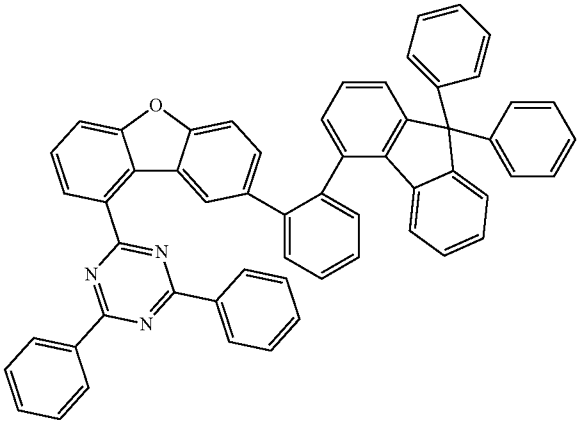 [SMILES: c1ccc(-c2nc(-c3ccccc3)nc(-c3cccc4oc5ccc(-c6ccccc6-c6cccc7c6-c6ccccc6C7(c6ccccc6)c6ccccc6)cc5c34)n2)cc1]
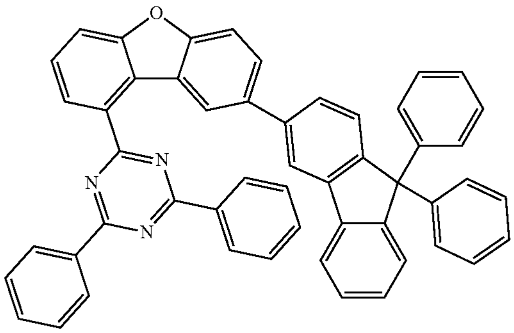 [SMILES: c1ccc(-c2nc(-c3ccccc3)nc(-c3cccc4oc5ccc(-c6ccc7c(c6)-c6ccccc6C7(c6ccccc6)c6ccccc6)cc5c34)n2)cc1]
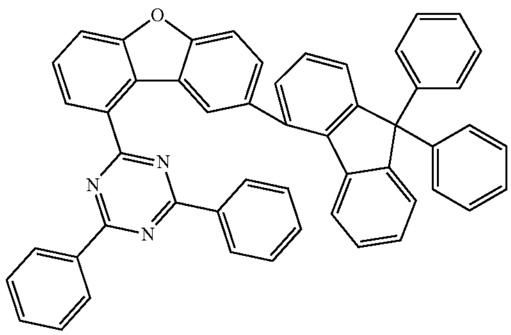 [SMILES: c1ccc(-c2nc(-c3ccccc3)nc(-c3cccc4oc5ccc(-c6cccc7c6-c6ccccc6C7(c6ccccc6)c6ccccc6)cc5c34)n2)cc1]

TABLE 1-continued
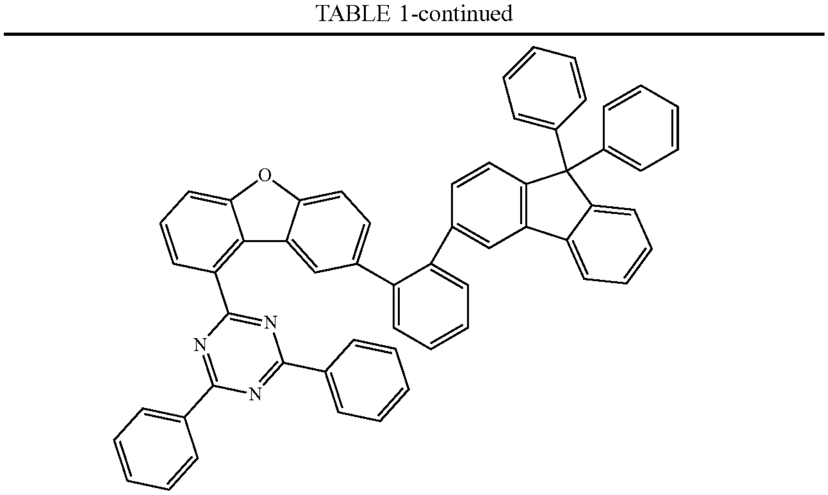
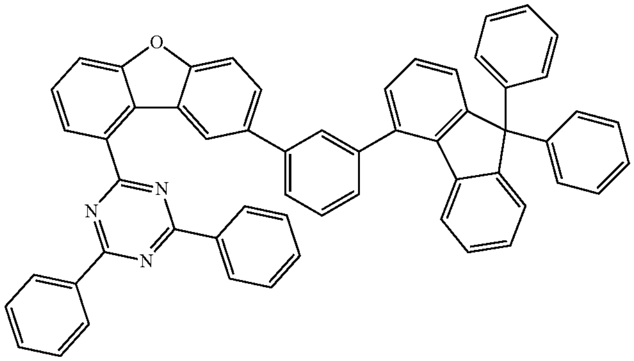 [SMILES: c1ccc(-c2nc(-c3ccccc3)nc(-c3cccc4oc5ccc(-c6cccc(-c7cccc8c7-c7ccccc7C8(c7ccccc7)c7ccccc7)c6)cc5c34)n2)cc1]
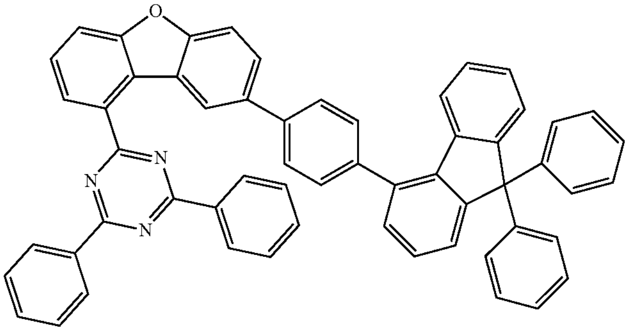 [SMILES: c1ccc(-c2nc(-c3ccccc3)nc(-c3cccc4oc5ccc(-c6ccc(-c7cccc8c7-c7ccccc7C8(c7ccccc7)c7ccccc7)cc6)cc5c34)n2)cc1]
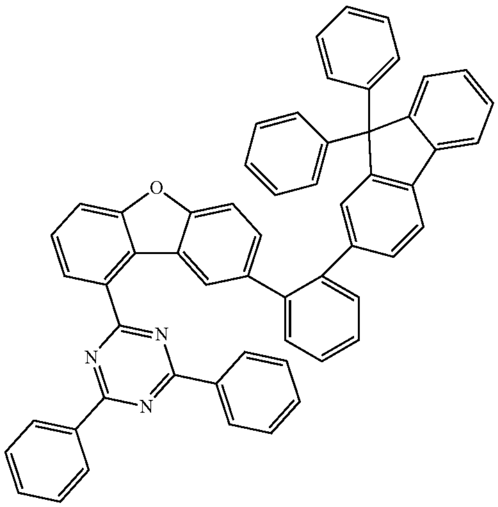 [SMILES: c1ccc(-c2nc(-c3ccccc3)nc(-c3cccc4oc5ccc(-c6ccccc6-c6ccc7c(c6)C(c6ccccc6)(c6ccccc6)c6ccccc6-7)cc5c34)n2)cc1]

TABLE 1-continued
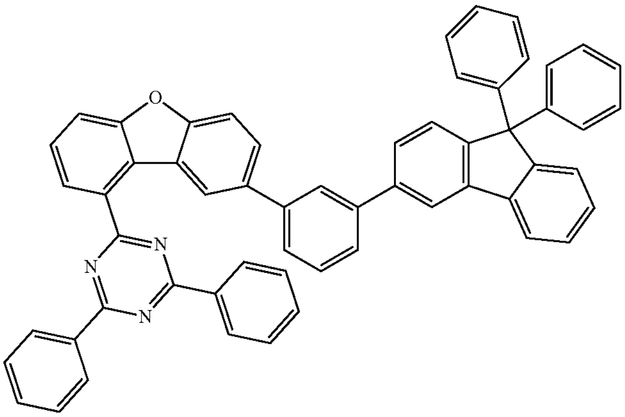 [SMILES: c1ccc(-c2nc(-c3ccccc3)nc(-c3cccc4oc5ccc(-c6cccc(-c7ccc8c(c7)-c7ccccc7C8(c7ccccc7)c7ccccc7)c6)cc5c34)n2)cc1]
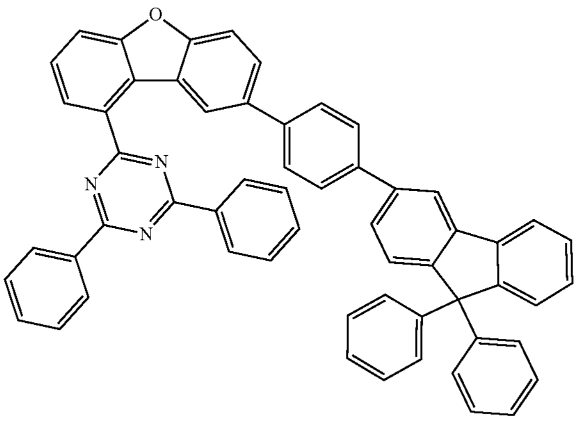 [SMILES: c1ccc(-c2nc(-c3ccccc3)nc(-c3cccc4oc5ccc(-c6ccc(-c7ccc8c(c7)-c7ccccc7C8(c7ccccc7)c7ccccc7)cc6)cc5c34)n2)cc1]
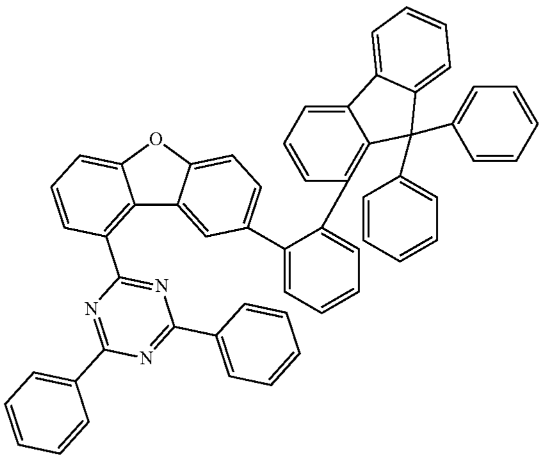 [SMILES: c1ccc(-c2nc(-c3ccccc3)nc(-c3cccc4oc5ccc(-c6ccccc6-c6cccc7c6C(c6ccccc6)(c6ccccc6)c6ccccc6-7)cc5c34)n2)cc1]

TABLE 1-continued
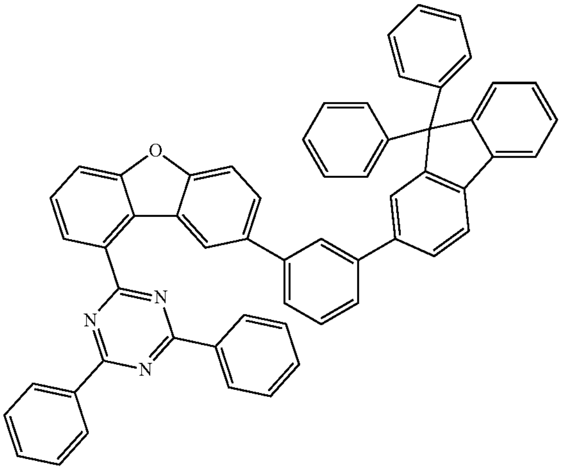 [SMILES: c1ccc(-c2nc(-c3ccccc3)nc(-c3cccc4oc5ccc(-c6cccc(-c7ccc8c(c7)C(c7ccccc7)(c7ccccc7)c7ccccc7-8)c6)cc5c34)n2)cc1]
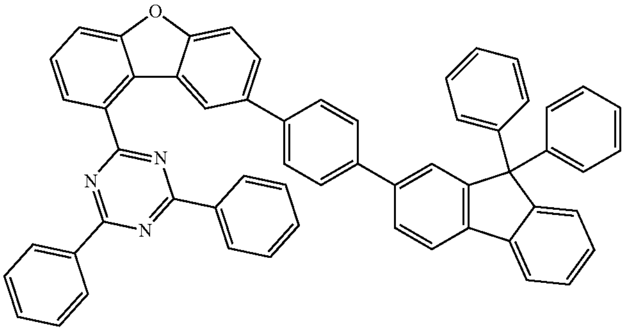 [SMILES: c1ccc(-c2nc(-c3ccccc3)nc(-c3cccc4oc5ccc(-c6ccc(-c7ccc8c(c7)C(c7ccccc7)(c7ccccc7)c7ccccc7-8)cc6)cc5c34)n2)cc1]
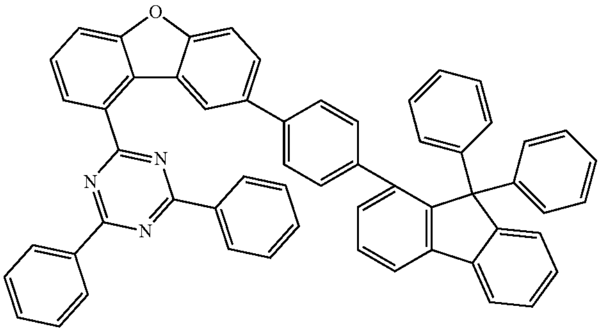 [SMILES: c1ccc(-c2nc(-c3ccccc3)nc(-c3cccc4oc5ccc(-c6ccc(-c7cccc8c7C(c7ccccc7)(c7ccccc7)c7ccccc7-8)cc6)cc5c34)n2)cc1]
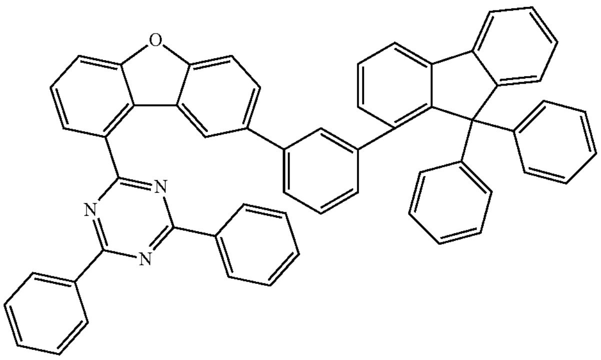 [SMILES: c1ccc(-c2nc(-c3ccccc3)nc(-c3cccc4oc5ccc(-c6cccc(-c7cccc8c7C(c7ccccc7)(c7ccccc7)c7ccccc7-8)c6)cc5c34)n2)cc1]

TABLE 1-continued
9
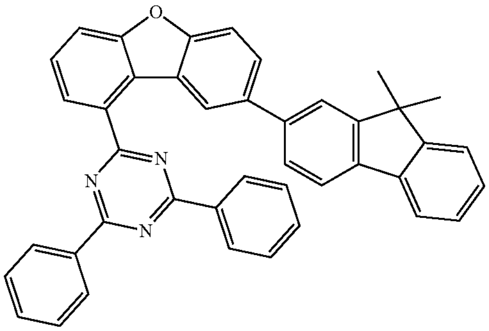 [SMILES: CC1(C)c2ccccc2-c2ccc(-c3ccc4oc5cccc(-c6nc(-c7ccccc7)nc(-c7ccccc7)n6)c5c4c3)cc21]
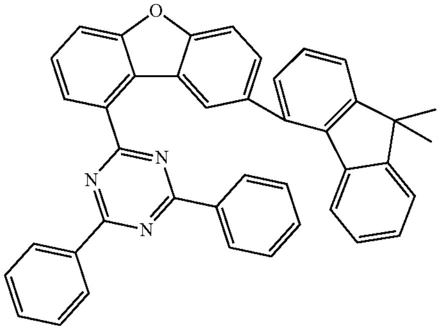 [SMILES: CC1(C)c2ccccc2-c2c(-c3ccc4oc5cccc(-c6nc(-c7ccccc7)nc(-c7ccccc7)n6)c5c4c3)cccc21]
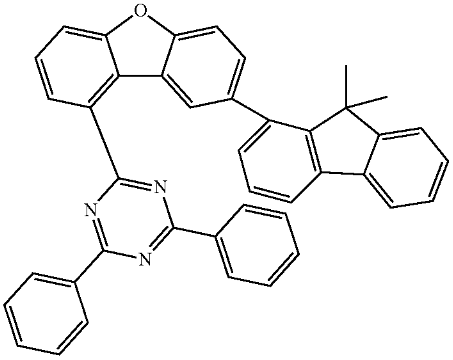 [SMILES: CC1(C)c2ccccc2-c2cccc(-c3ccc4oc5cccc(-c6nc(-c7ccccc7)nc(-c7ccccc7)n6)c5c4c3)c21]
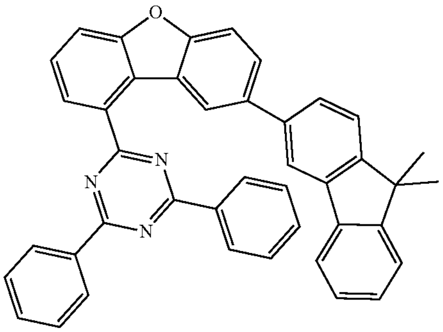 [SMILES: CC1(C)c2ccccc2-c2cc(-c3ccc4oc5cccc(-c6nc(-c7ccccc7)nc(-c7ccccc7)n6)c5c4c3)ccc21]

TABLE 1-continued
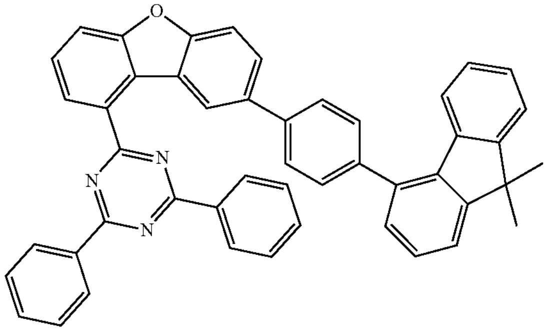 [SMILES: CC1(C)c2ccccc2-c2c(-c3ccc(-c4ccc5oc6cccc(-c7nc(-c8ccccc8)nc(-c8ccccc8)n7)c6c5c4)cc3)cccc21]
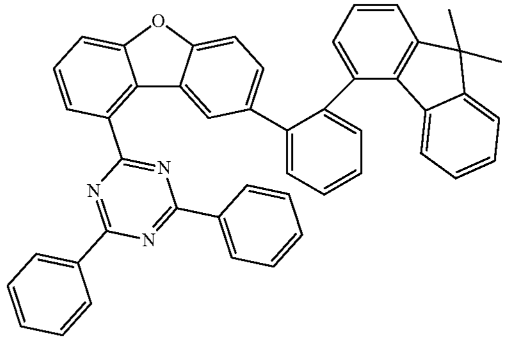 [SMILES: CC1(C)c2ccccc2-c2c(-c3ccccc3-c3ccc4oc5cccc(-c6nc(-c7ccccc7)nc(-c7ccccc7)n6)c5c4c3)cccc21]
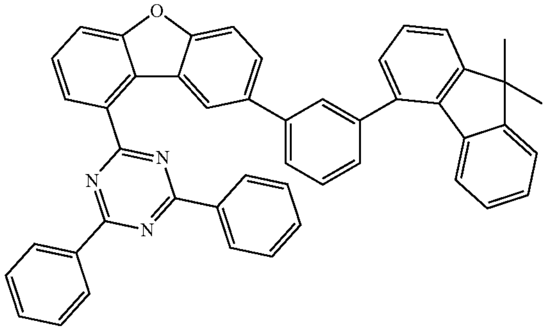 [SMILES: CC1(C)c2ccccc2-c2c(-c3cccc(-c4ccc5oc6cccc(-c7nc(-c8ccccc8)nc(-c8ccccc8)n7)c6c5c4)c3)cccc21]
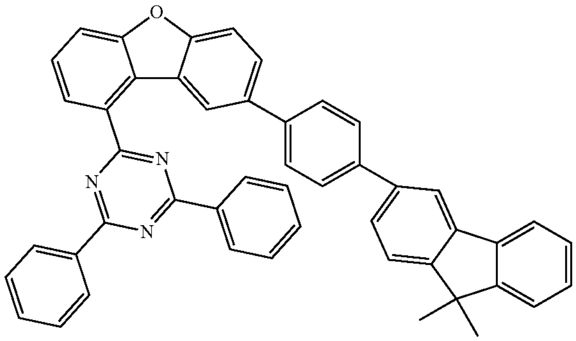 [SMILES: CC1(C)c2ccccc2-c2cc(-c3ccc(-c4ccc5oc6cccc(-c7nc(-c8ccccc8)nc(-c8ccccc8)n7)c6c5c4)cc3)ccc21]

TABLE 1-continued
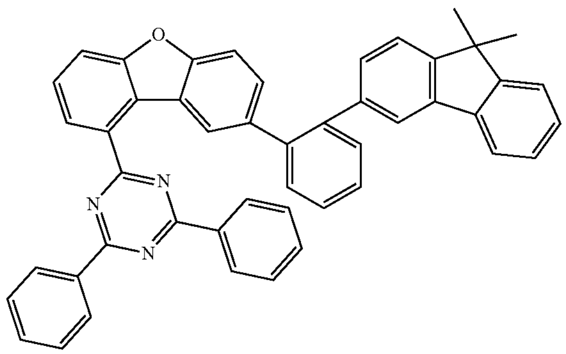 [SMILES: CC1(C)c2ccccc2-c2cc(-c3ccccc3-c3ccc4oc5cccc(-c6nc(-c7ccccc7)nc(-c7ccccc7)n6)c5c4c3)ccc21]
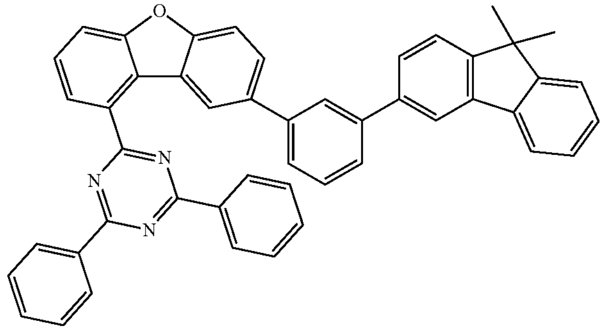 [SMILES: CC1(C)c2ccccc2-c2cc(-c3cccc(-c4ccc5oc6cccc(-c7nc(-c8ccccc8)nc(-c8ccccc8)n7)c6c5c4)c3)ccc21]
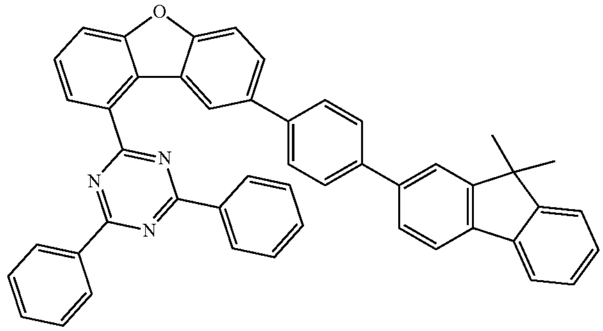 [SMILES: CC1(C)c2ccccc2-c2ccc(-c3ccc(-c4ccc5oc6cccc(-c7nc(-c8ccccc8)nc(-c8ccccc8)n7)c6c5c4)cc3)cc21]
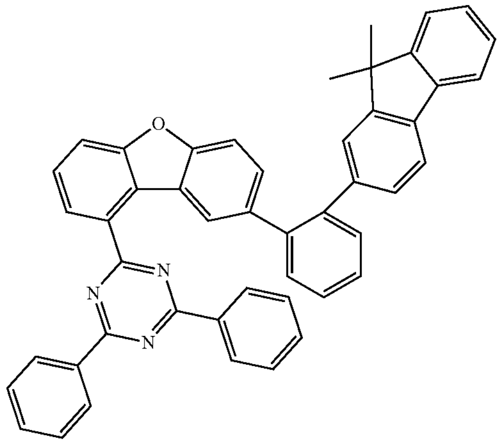 [SMILES: CC1(C)c2ccccc2-c2ccc(-c3ccccc3-c3ccc4oc5cccc(-c6nc(-c7ccccc7)nc(-c7ccccc7)n6)c5c4c3)cc21]

TABLE 1-continued
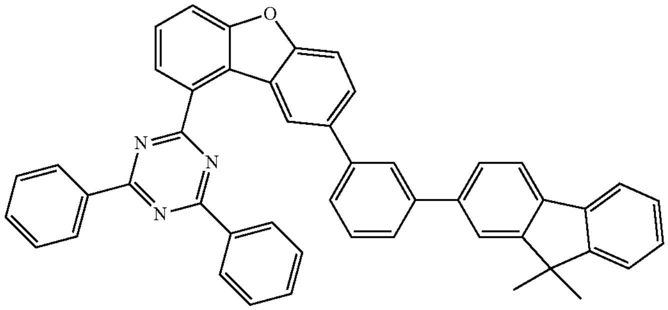 [SMILES: CC1(C)c2ccccc2-c2ccc(-c3cccc(-c4ccc5oc6cccc(-c7nc(-c8ccccc8)nc(-c8ccccc8)n7)c6c5c4)c3)cc21]
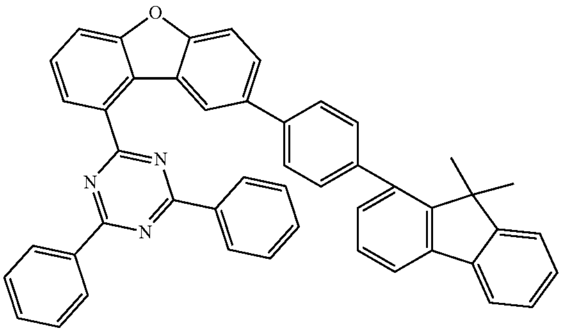 [SMILES: CC1(C)c2ccccc2-c2cccc(-c3ccc(-c4ccc5oc6cccc(-c7nc(-c8ccccc8)nc(-c8ccccc8)n7)c6c5c4)cc3)c21]
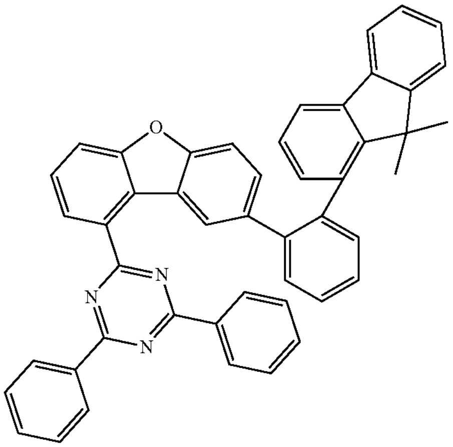 [SMILES: CC1(C)c2ccccc2-c2cccc(-c3ccccc3-c3ccc4oc5cccc(-c6nc(-c7ccccc7)nc(-c7ccccc7)n6)c5c4c3)c21]
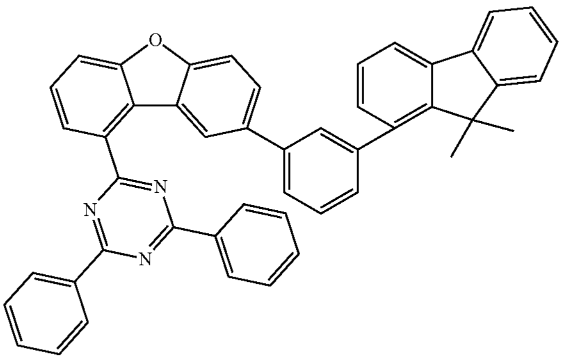 [SMILES: CC1(C)c2ccccc2-c2cccc(-c3cccc(-c4ccc5oc6cccc(-c7nc(-c8ccccc8)nc(-c8ccccc8)n7)c6c5c4)c3)c21]

TABLE 1-continued
11
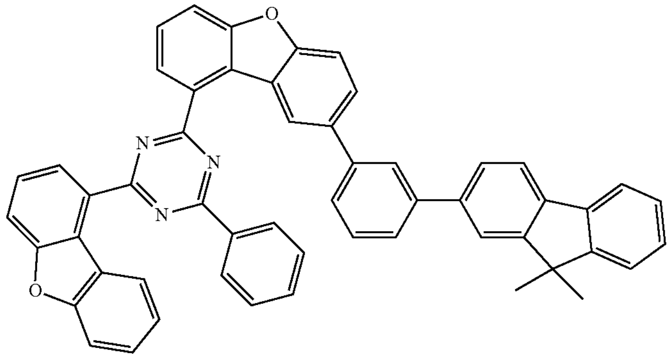 [SMILES: CC1(C)c2ccccc2-c2ccc(-c3cccc(-c4ccc5oc6cccc(-c7nc(-c8ccccc8)nc(-c8cccc9oc%10ccccc%10c89)n7)c6c5c4)c3)cc21]
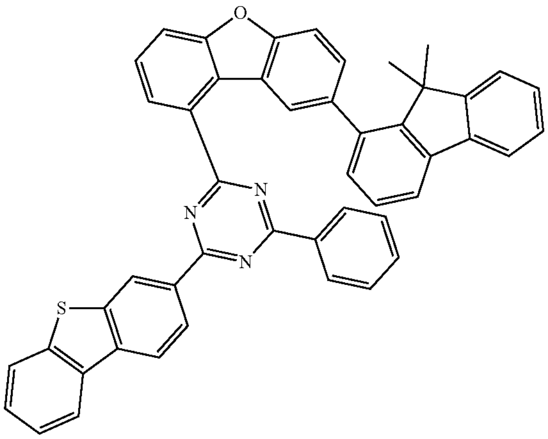 [SMILES: CC1(C)c2ccccc2-c2cccc(-c3ccc4oc5cccc(-c6nc(-c7ccccc7)nc(-c7ccc8c(c7)sc7ccccc78)n6)c5c4c3)c21]
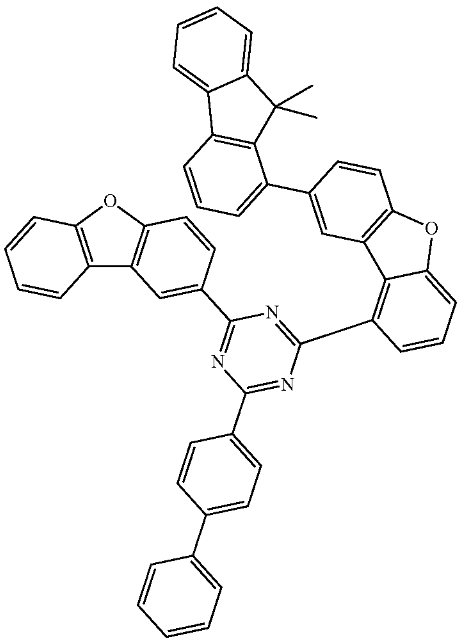 [SMILES: CC1(C)c2ccccc2-c2cccc(-c3ccc4oc5cccc(-c6nc(-c7ccc(-c8ccccc8)cc7)nc(-c7ccc8oc9ccccc9c8c7)n6)c5c4c3)c21]

TABLE 1-continued
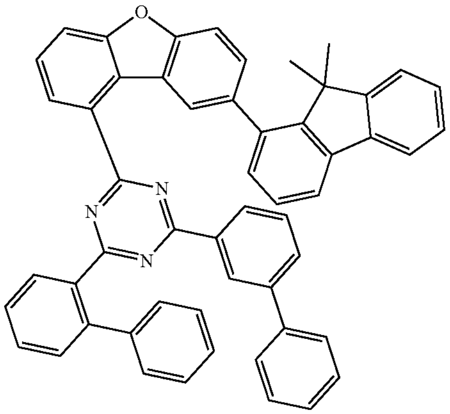 [SMILES: CC1(C)c2ccccc2-c2cccc(-c3ccc4oc5cccc(-c6nc(-c7cccc(-c8ccccc8)c7)nc(-c7ccccc7-c7ccccc7)n6)c5c4c3)c21]
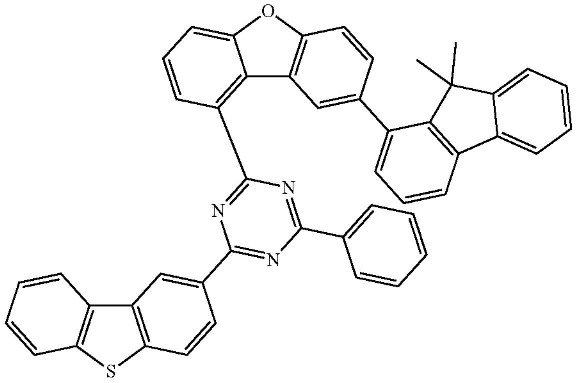 [SMILES: CC1(C)c2ccccc2-c2cccc(-c3ccc4oc5cccc(-c6nc(-c7ccccc7)nc(-c7ccc8sc9ccccc9c8c7)n6)c5c4c3)c21]
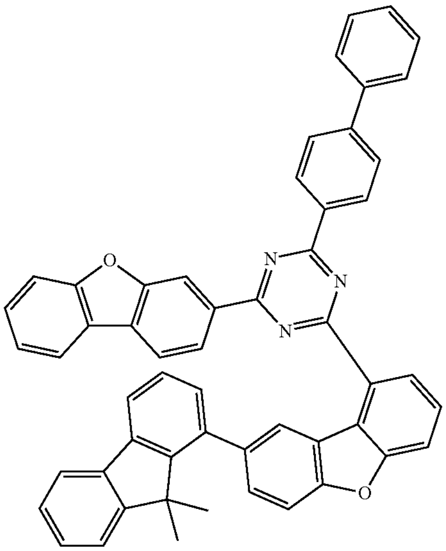 [SMILES: CC1(C)c2ccccc2-c2cccc(-c3ccc4oc5cccc(-c6nc(-c7ccc(-c8ccccc8)cc7)nc(-c7ccc8c(c7)oc7ccccc78)n6)c5c4c3)c21]

TABLE 1-continued
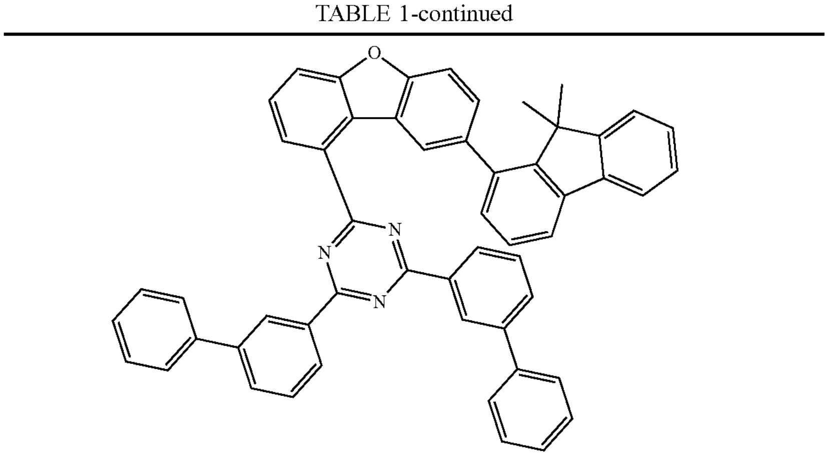
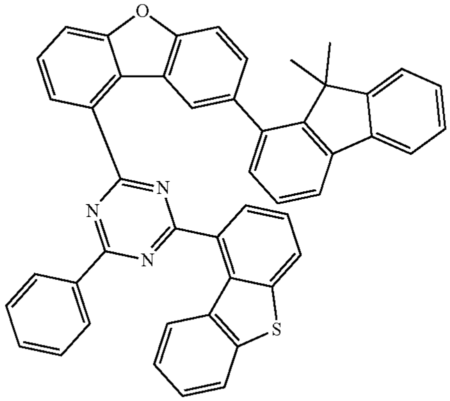 [SMILES: CC1(C)c2ccccc2-c2cccc(-c3ccc4oc5cccc(-c6nc(-c7ccccc7)nc(-c7cccc8sc9ccccc9c78)n6)c5c4c3)c21]
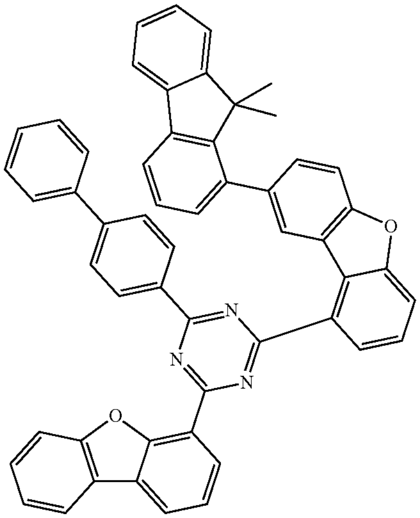 [SMILES: CC1(C)c2ccccc2-c2cccc(-c3ccc4oc5cccc(-c6nc(-c7ccc(-c8ccccc8)cc7)nc(-c7cccc8c7oc7ccccc78)n6)c5c4c3)c21]

TABLE 1-continued
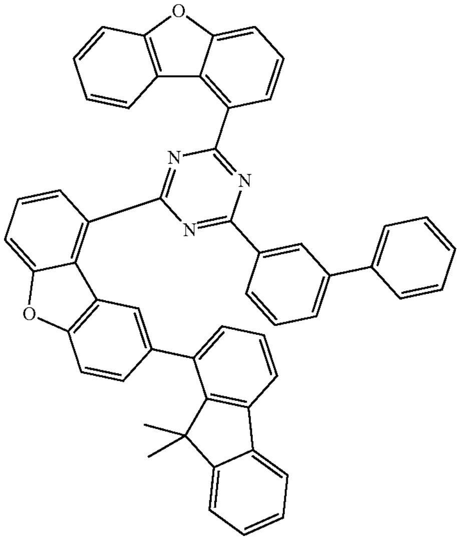 [SMILES: CC1(C)c2ccccc2-c2cccc(-c3ccc4oc5cccc(-c6nc(-c7cccc(-c8ccccc8)c7)nc(-c7cccc8oc9ccccc9c78)n6)c5c4c3)c21]
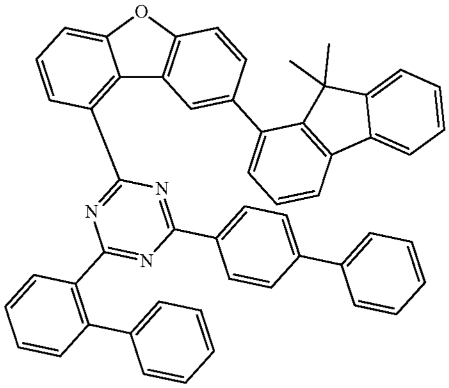 [SMILES: CC1(C)c2ccccc2-c2cccc(-c3ccc4oc5cccc(-c6nc(-c7ccc(-c8ccccc8)cc7)nc(-c7ccccc7-c7ccccc7)n6)c5c4c3)c21]
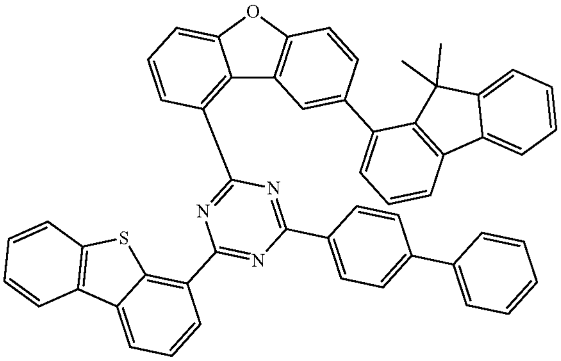 [SMILES: CC1(C)c2ccccc2-c2cccc(-c3ccc4oc5cccc(-c6nc(-c7ccc(-c8ccccc8)cc7)nc(-c7cccc8c7sc7ccccc78)n6)c5c4c3)c21]

TABLE 1-continued
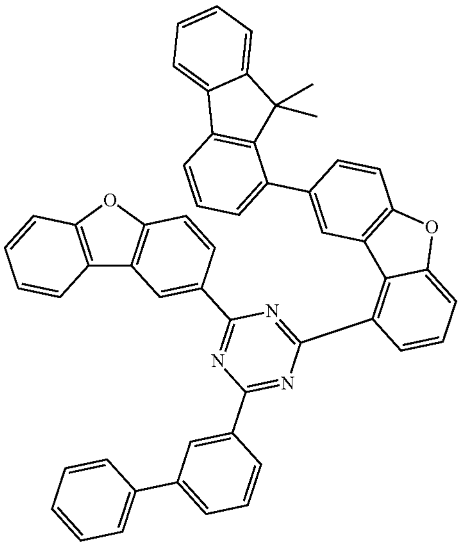 [SMILES: CC1(C)c2ccccc2-c2cccc(-c3ccc4oc5cccc(-c6nc(-c7cccc(-c8ccccc8)c7)nc(-c7ccc8oc9ccccc9c8c7)n6)c5c4c3)c21]
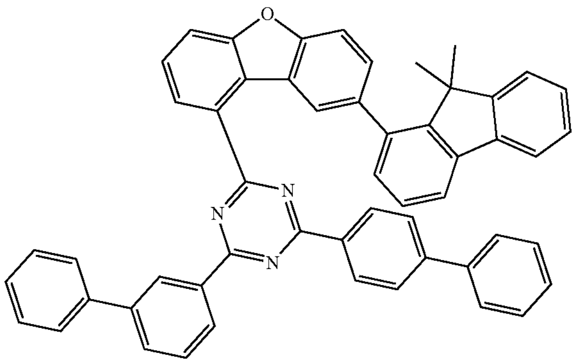 [SMILES: CC1(C)c2ccccc2-c2cccc(-c3ccc4oc5cccc(-c6nc(-c7ccc(-c8ccccc8)cc7)nc(-c7cccc(-c8ccccc8)c7)n6)c5c4c3)c21]
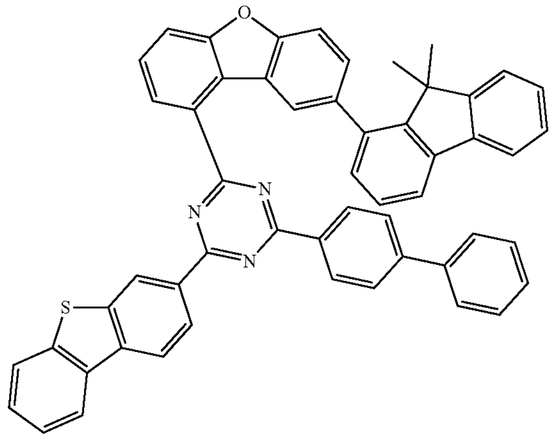 [SMILES: CC1(C)c2ccccc2-c2cccc(-c3ccc4oc5cccc(-c6nc(-c7ccc(-c8ccccc8)cc7)nc(-c7ccc8c(c7)sc7ccccc78)n6)c5c4c3)c21]

TABLE 1-continued
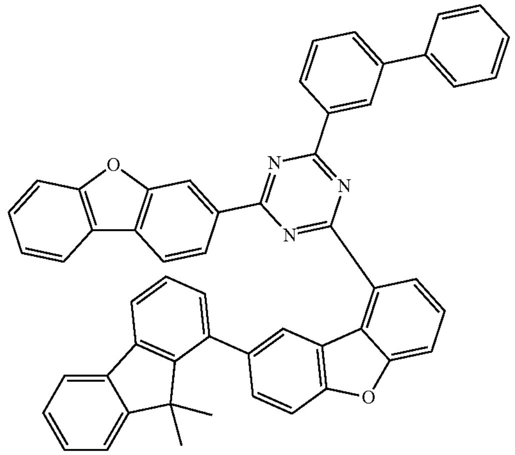 [SMILES: CC1(C)c2ccccc2-c2cccc(-c3ccc4oc5cccc(-c6nc(-c7cccc(-c8ccccc8)c7)nc(-c7ccc8c(c7)oc7ccccc78)n6)c5c4c3)c21]
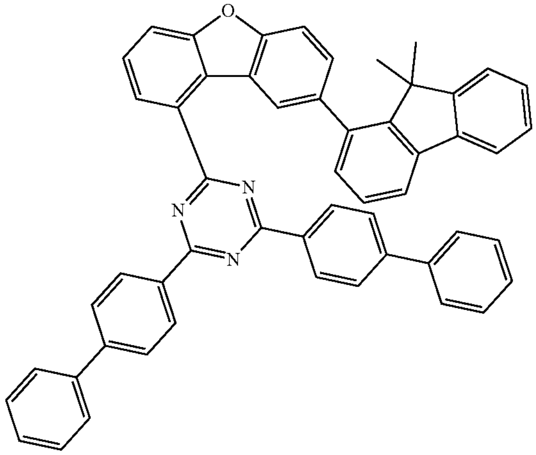 [SMILES: CC1(C)c2ccccc2-c2cccc(-c3ccc4oc5cccc(-c6nc(-c7ccc(-c8ccccc8)cc7)nc(-c7ccc(-c8ccccc8)cc7)n6)c5c4c3)c21]
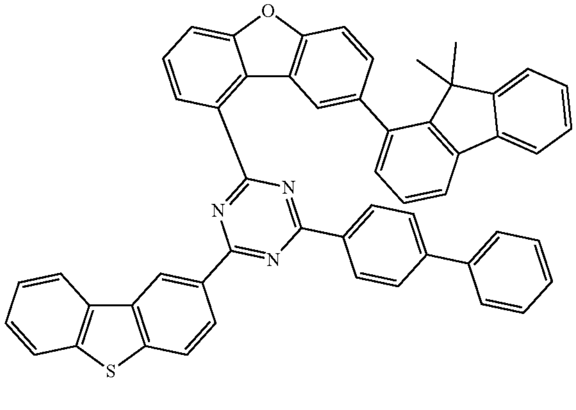 [SMILES: CC1(C)c2ccccc2-c2cccc(-c3ccc4oc5cccc(-c6nc(-c7ccc(-c8ccccc8)cc7)nc(-c7ccc8sc9ccccc9c8c7)n6)c5c4c3)c21]

TABLE 1-continued
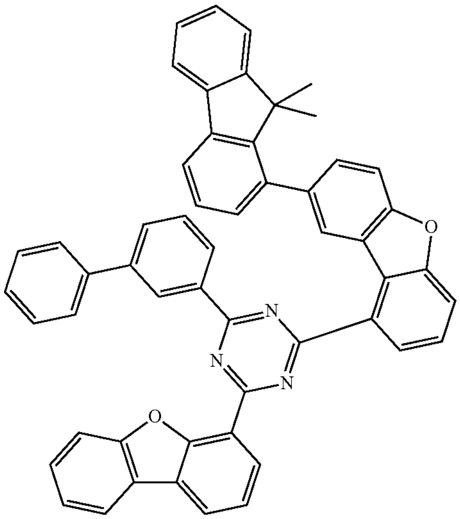 [SMILES: CC1(C)c2ccccc2-c2cccc(-c3ccc4oc5cccc(-c6nc(-c7cccc(-c8ccccc8)c7)nc(-c7cccc8c7oc7ccccc78)n6)c5c4c3)c21]
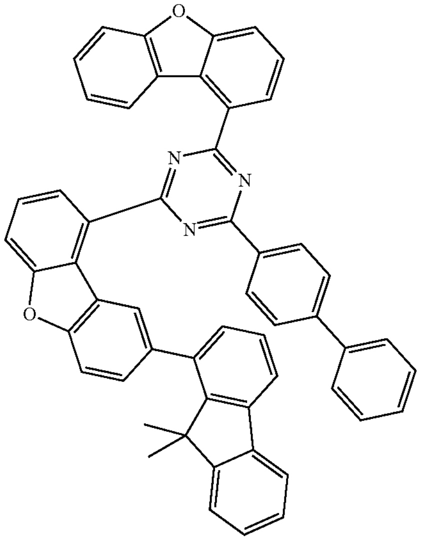 [SMILES: CC1(C)c2ccccc2-c2cccc(-c3ccc4oc5cccc(-c6nc(-c7ccc(-c8ccccc8)cc7)nc(-c7cccc8oc9ccccc9c78)n6)c5c4c3)c21]
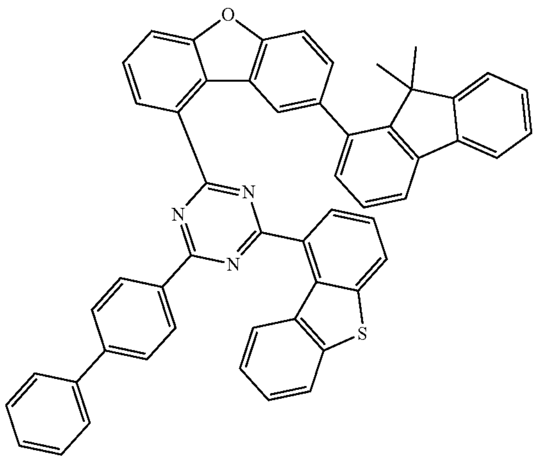 [SMILES: CC1(C)c2ccccc2-c2cccc(-c3ccc4oc5cccc(-c6nc(-c7ccc(-c8ccccc8)cc7)nc(-c7cccc8sc9ccccc9c78)n6)c5c4c3)c21]

TABLE 1-continued
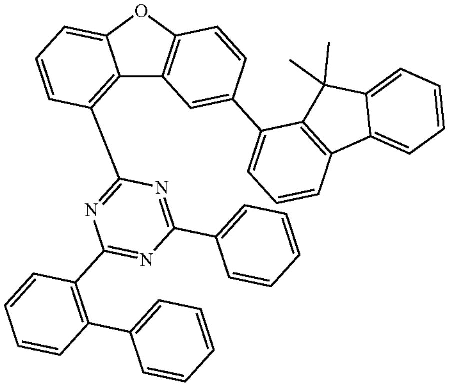 [SMILES: CC1(C)c2ccccc2-c2cccc(-c3ccc4oc5cccc(-c6nc(-c7ccccc7)nc(-c7ccccc7-c7ccccc7)n6)c5c4c3)c21]
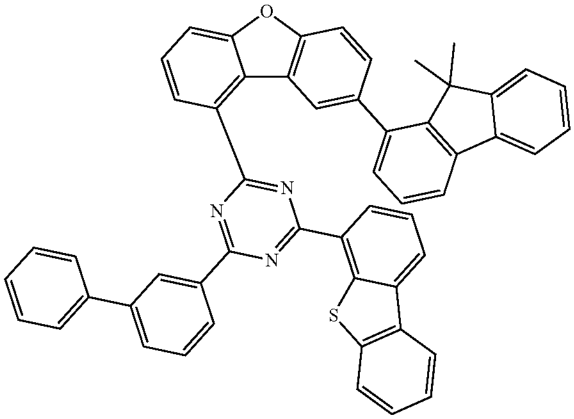 [SMILES: CC1(C)c2ccccc2-c2cccc(-c3ccc4oc5cccc(-c6nc(-c7cccc(-c8ccccc8)c7)nc(-c7cccc8c7sc7ccccc78)n6)c5c4c3)c21]
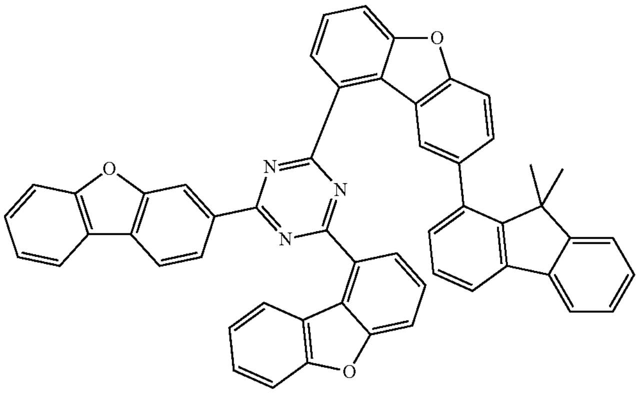 [SMILES: CC1(C)c2ccccc2-c2cccc(-c3ccc4oc5cccc(-c6nc(-c7ccc8c(c7)oc7ccccc78)nc(-c7cccc8oc9ccccc9c78)n6)c5c4c3)c21]
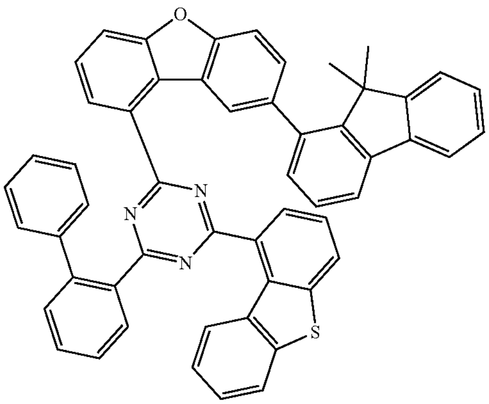 [SMILES: CC1(C)c2ccccc2-c2cccc(-c3ccc4oc5cccc(-c6nc(-c7ccccc7-c7ccccc7)nc(-c7cccc8sc9ccccc9c78)n6)c5c4c3)c21]

TABLE 1-continued
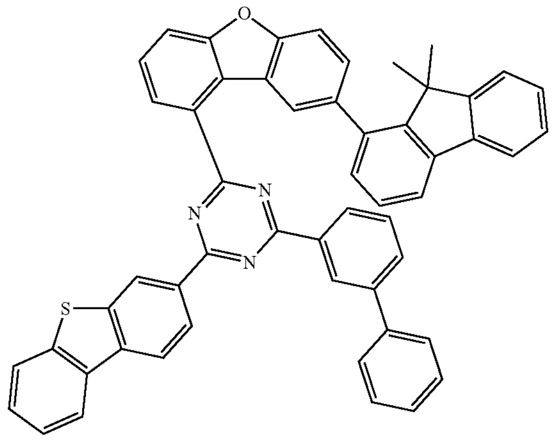 [SMILES: CC1(C)c2ccccc2-c2cccc(-c3ccc4oc5cccc(-c6nc(-c7cccc(-c8ccccc8)c7)nc(-c7ccc8c(c7)sc7ccccc78)n6)c5c4c3)c21]
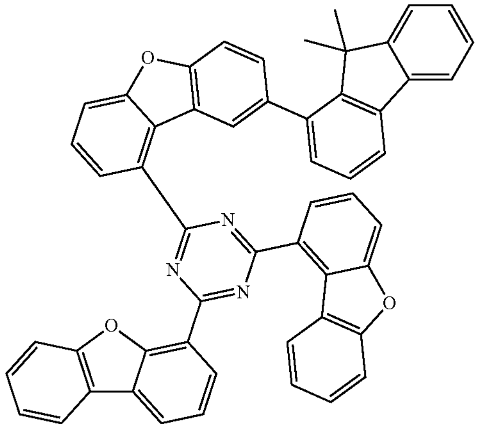 [SMILES: CC1(C)c2ccccc2-c2cccc(-c3ccc4oc5cccc(-c6nc(-c7cccc8c7oc7ccccc78)nc(-c7cccc8oc9ccccc9c78)n6)c5c4c3)c21]
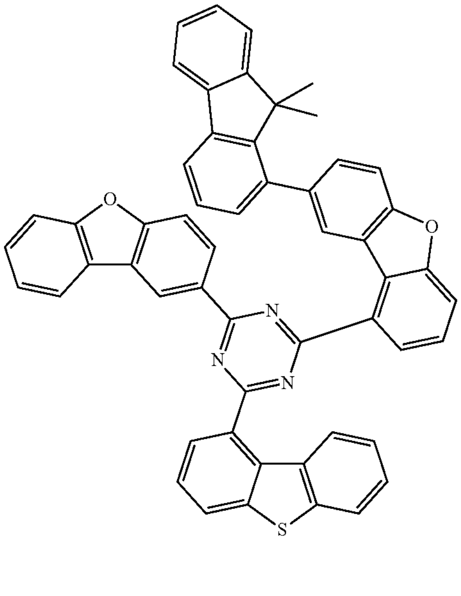 [SMILES: CC1(C)c2ccccc2-c2cccc(-c3ccc4oc5cccc(-c6nc(-c7ccc8oc9ccccc9c8c7)nc(-c7cccc8sc9ccccc9c78)n6)c5c4c3)c21]

TABLE 1-continued
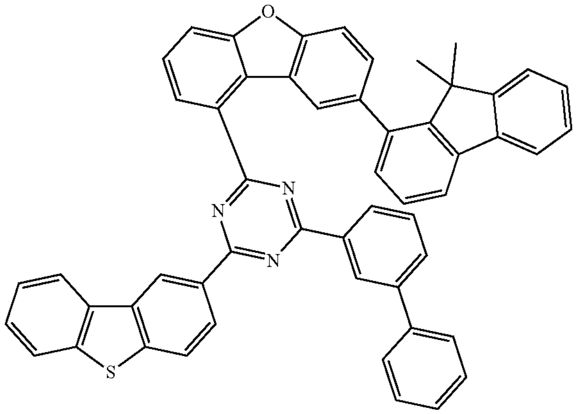 [SMILES: CC1(C)c2ccccc2-c2cccc(-c3ccc4oc5cccc(-c6nc(-c7cccc(-c8ccccc8)c7)nc(-c7ccc8sc9ccccc9c8c7)n6)c5c4c3)c21]
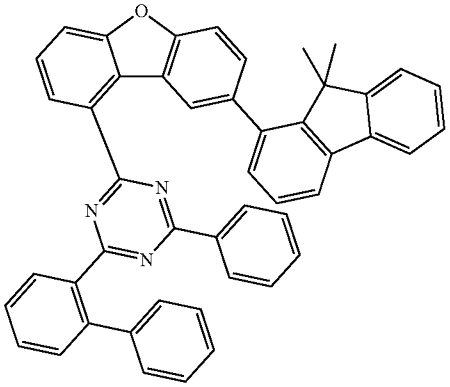 [SMILES: CC1(C)c2ccccc2-c2cccc(-c3ccc4oc5cccc(-c6nc(-c7ccccc7)nc(-c7ccccc7-c7ccccc7)n6)c5c4c3)c21]
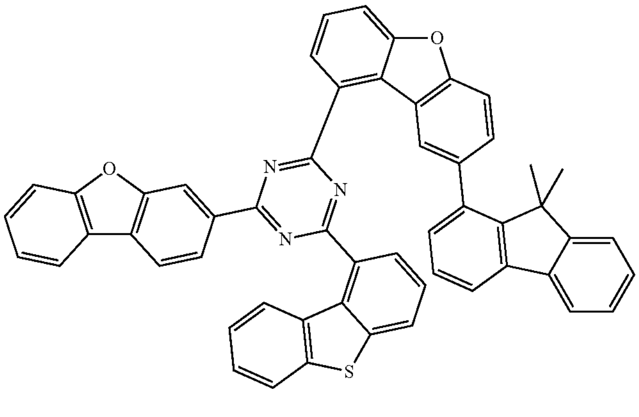 [SMILES: CC1(C)c2ccccc2-c2cccc(-c3ccc4oc5cccc(-c6nc(-c7ccc8c(c7)oc7ccccc78)nc(-c7cccc8sc9ccccc9c78)n6)c5c4c3)c21]
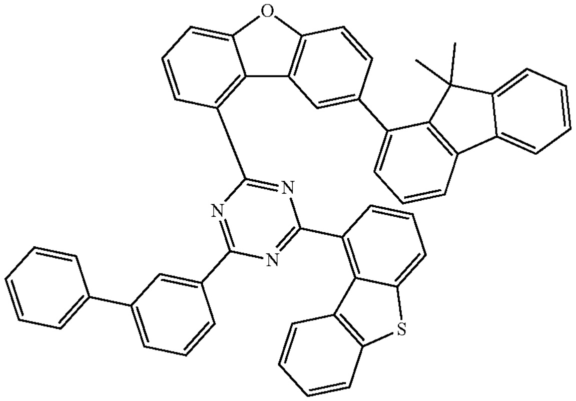 [SMILES: CC1(C)c2ccccc2-c2cccc(-c3ccc4oc5cccc(-c6nc(-c7cccc(-c8ccccc8)c7)nc(-c7cccc8sc9ccccc9c78)n6)c5c4c3)c21]

TABLE 1-continued
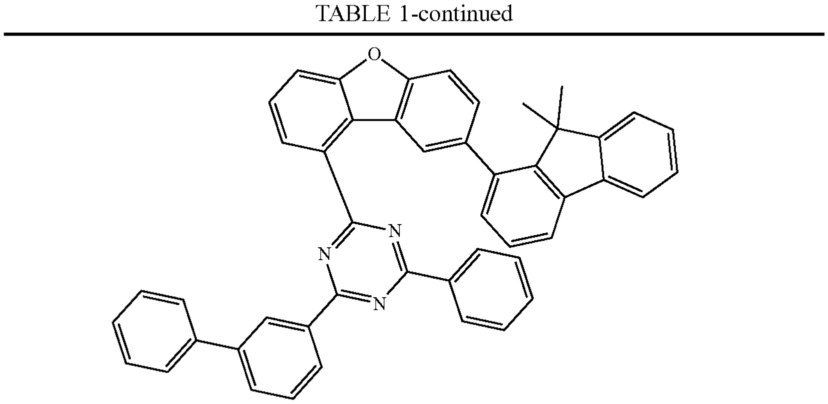
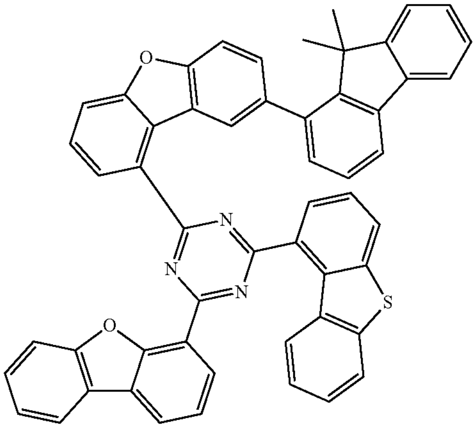 [SMILES: CC1(C)c2ccccc2-c2cccc(-c3ccc4oc5cccc(-c6nc(-c7cccc8c7oc7ccccc78)nc(-c7cccc8sc9ccccc9c78)n6)c5c4c3)c21]
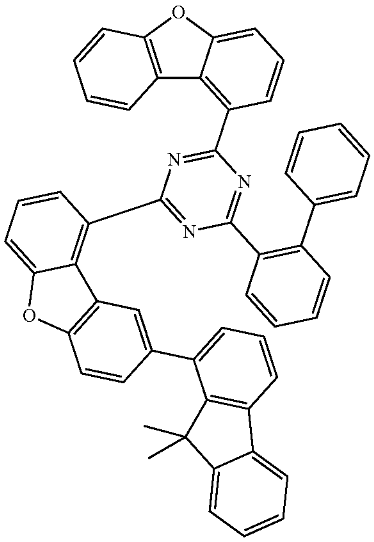 [SMILES: CC1(C)c2ccccc2-c2cccc(-c3ccc4oc5cccc(-c6nc(-c7ccccc7-c7ccccc7)nc(-c7cccc8oc9ccccc9c78)n6)c5c4c3)c21]

TABLE 1-continued
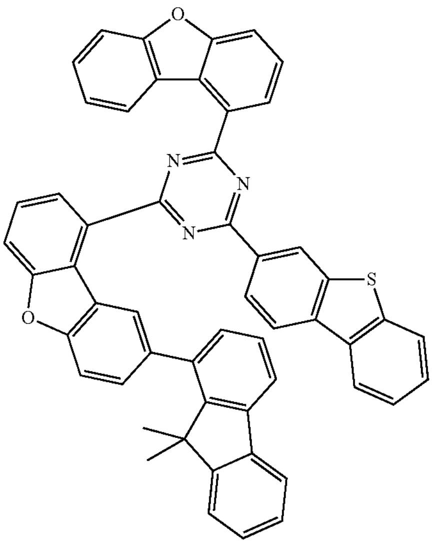 [SMILES: CC1(C)c2ccccc2-c2cccc(-c3ccc4oc5cccc(-c6nc(-c7ccc8c(c7)sc7ccccc78)nc(-c7cccc8oc9ccccc9c78)n6)c5c4c3)c21]
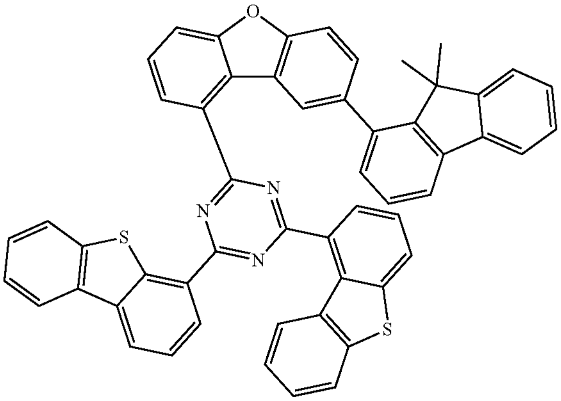 [SMILES: CC1(C)c2ccccc2-c2cccc(-c3ccc4oc5cccc(-c6nc(-c7cccc8c7sc7ccccc78)nc(-c7cccc8sc9ccccc9c78)n6)c5c4c3)c21]
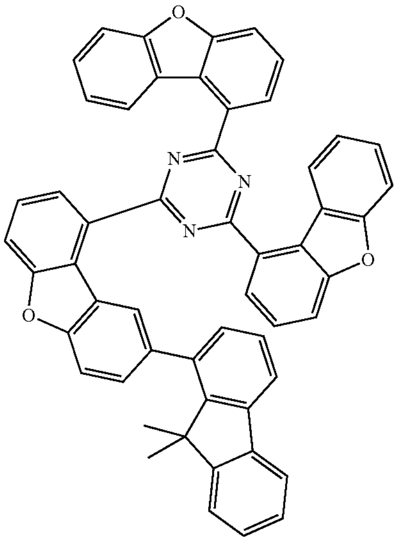 [SMILES: CC1(C)c2ccccc2-c2cccc(-c3ccc4oc5cccc(-c6nc(-c7cccc8oc9ccccc9c78)nc(-c7cccc8oc9ccccc9c78)n6)c5c4c3)c21]

TABLE 1-continued
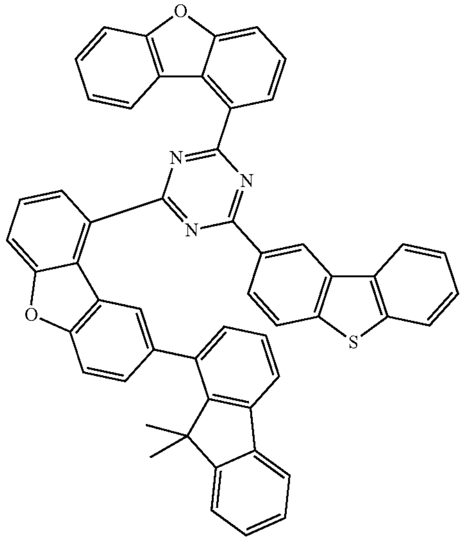 [SMILES: CC1(C)c2ccccc2-c2cccc(-c3ccc4oc5cccc(-c6nc(-c7ccc8sc9ccccc9c8c7)nc(-c7cccc8oc9ccccc9c78)n6)c5c4c3)c21]
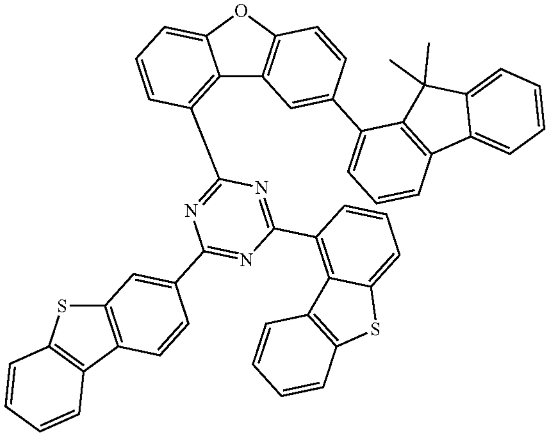 [SMILES: CC1(C)c2ccccc2-c2cccc(-c3ccc4oc5cccc(-c6nc(-c7ccc8c(c7)sc7ccccc78)nc(-c7cccc8sc9ccccc9c78)n6)c5c4c3)c21]
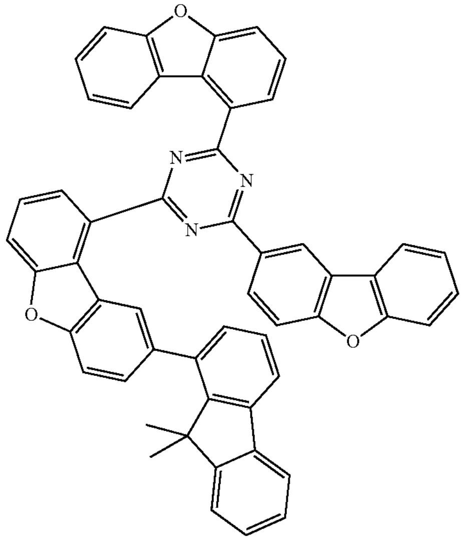 [SMILES: CC1(C)c2ccccc2-c2cccc(-c3ccc4oc5cccc(-c6nc(-c7ccc8oc9ccccc9c8c7)nc(-c7cccc8oc9ccccc9c78)n6)c5c4c3)c21]

TABLE 1-continued
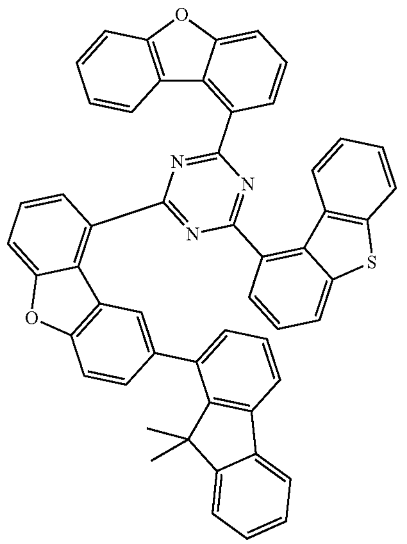 [SMILES: CC1(C)c2ccccc2-c2cccc(-c3ccc4oc5cccc(-c6nc(-c7cccc8oc9ccccc9c78)nc(-c7cccc8sc9ccccc9c78)n6)c5c4c3)c21]
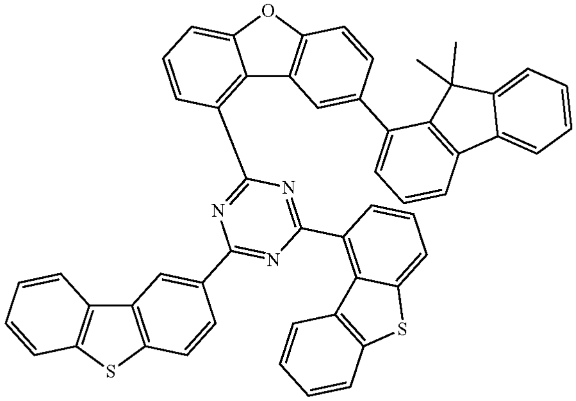 [SMILES: CC1(C)c2ccccc2-c2cccc(-c3ccc4oc5cccc(-c6nc(-c7ccc8sc9ccccc9c8c7)nc(-c7cccc8sc9ccccc9c78)n6)c5c4c3)c21]
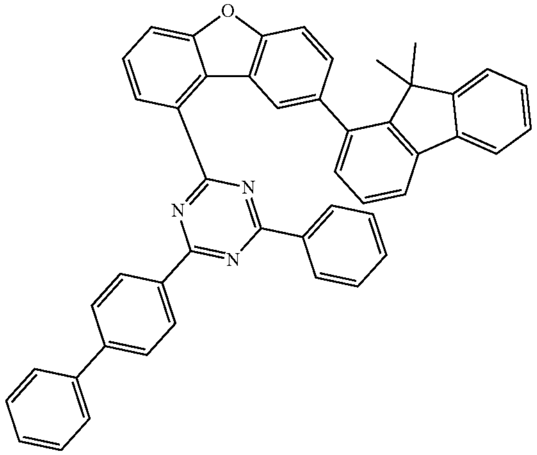 [SMILES: CC1(C)c2ccccc2-c2cccc(-c3ccc4oc5cccc(-c6nc(-c7ccccc7)nc(-c7ccc(-c8ccccc8)cc7)n6)c5c4c3)c21]

TABLE 1-continued
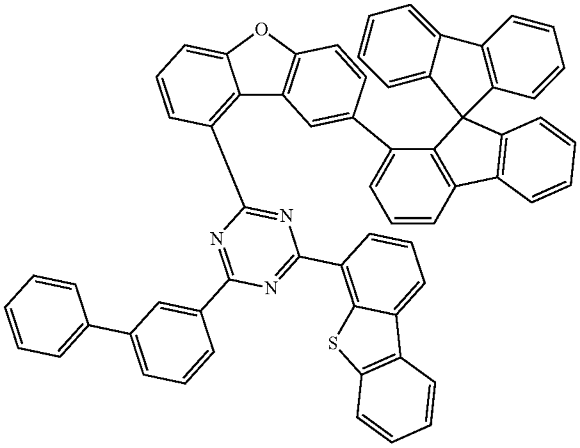 [SMILES: c1ccc(-c2cccc(-c3nc(-c4cccc5c4sc4ccccc45)nc(-c4cccc5oc6ccc(-c7cccc8c7C7(c9ccccc9-c9ccccc97)c7ccccc7-8)cc6c45)n3)c2)cc1]
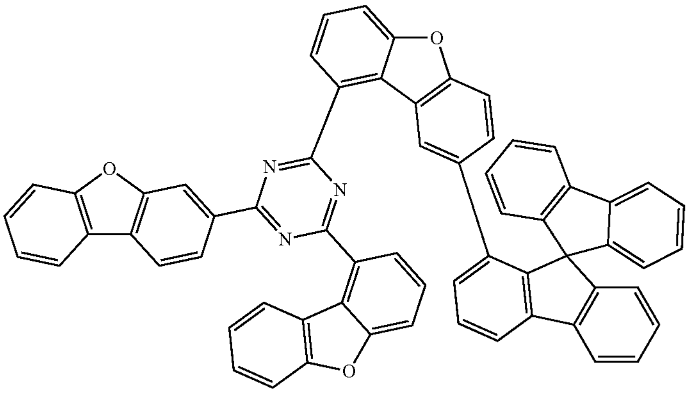 [SMILES: c1ccc2c(c1)-c1ccccc1C21c2ccccc2-c2cccc(-c3ccc4oc5cccc(-c6nc(-c7ccc8c(c7)oc7ccccc78)nc(-c7cccc8oc9ccccc9c78)n6)c5c4c3)c21]
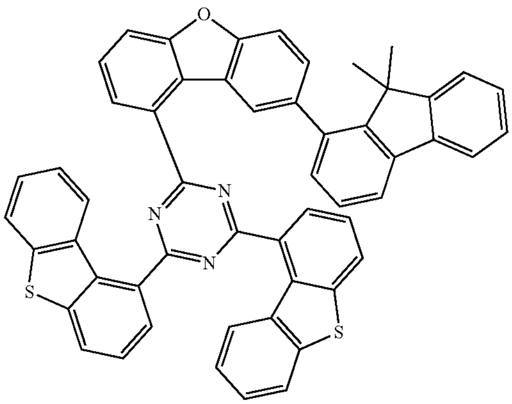 [SMILES: CC1(C)c2ccccc2-c2cccc(-c3ccc4oc5cccc(-c6nc(-c7cccc8sc9ccccc9c78)nc(-c7cccc8sc9ccccc9c78)n6)c5c4c3)c21]

TABLE 1-continued
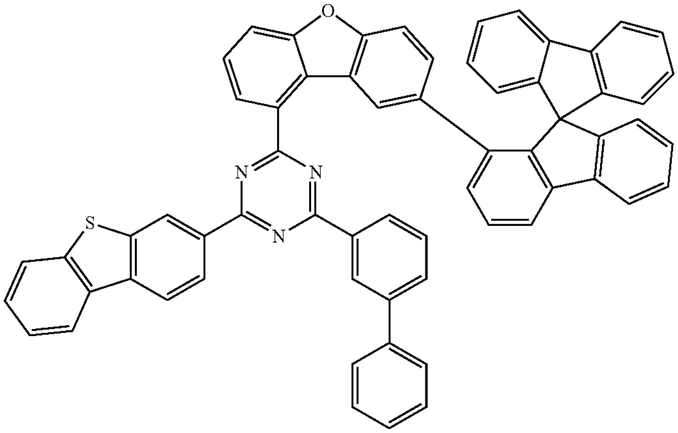 [SMILES: c1ccc(-c2cccc(-c3nc(-c4ccc5c(c4)sc4ccccc45)nc(-c4cccc5oc6ccc(-c7cccc8c7C7(c9ccccc9-c9ccccc97)c7ccccc7-8)cc6c45)n3)c2)cc1]
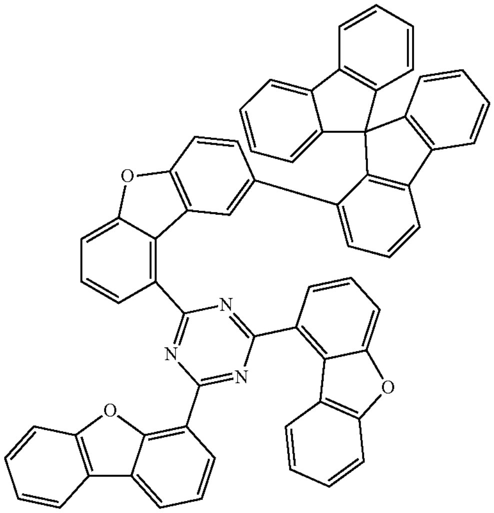 [SMILES: c1ccc2c(c1)-c1ccccc1C21c2ccccc2-c2cccc(-c3ccc4oc5cccc(-c6nc(-c7cccc8c7oc7ccccc78)nc(-c7cccc8oc9ccccc9c78)n6)c5c4c3)c21]
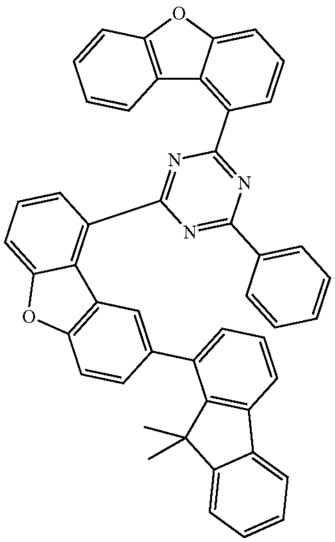 [SMILES: CC1(C)c2ccccc2-c2cccc(-c3ccc4oc5cccc(-c6nc(-c7ccccc7)nc(-c7cccc8oc9ccccc9c78)n6)c5c4c3)c21]

TABLE 1-continued
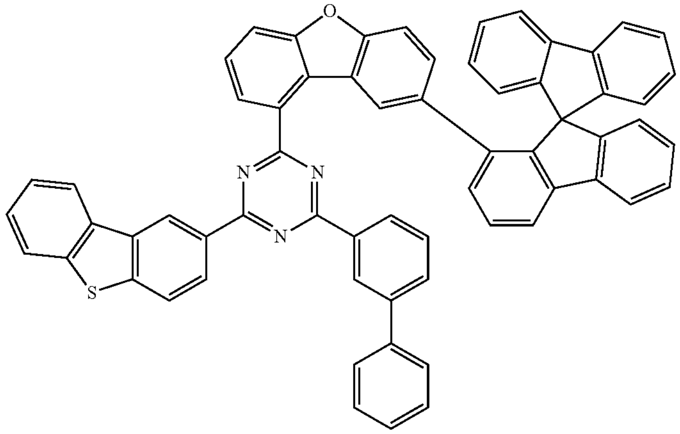 [SMILES: c1ccc(-c2cccc(-c3nc(-c4ccc5sc6ccccc6c5c4)nc(-c4cccc5oc6ccc(-c7cccc8c7C7(c9ccccc9-c9ccccc97)c7ccccc7-8)cc6c45)n3)c2)cc1]
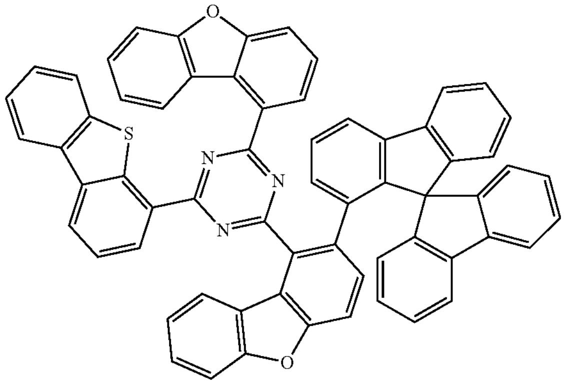 [SMILES: c1ccc2c(c1)-c1ccccc1C21c2ccccc2-c2cccc(-c3ccc4oc5ccccc5c4c3-c3nc(-c4cccc5c4sc4ccccc45)nc(-c4cccc5oc6ccccc6c45)n3)c21]
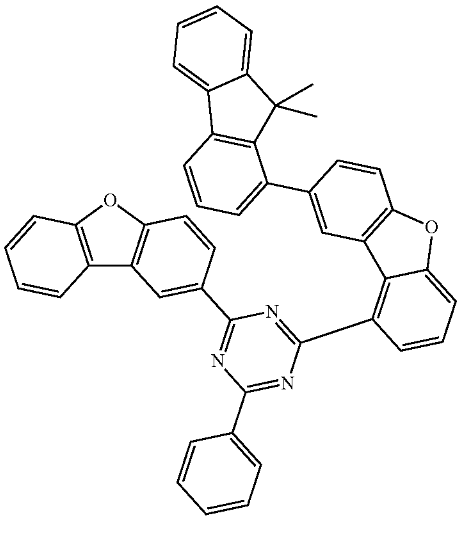 [SMILES: CC1(C)c2ccccc2-c2cccc(-c3ccc4oc5cccc(-c6nc(-c7ccccc7)nc(-c7ccc8oc9ccccc9c8c7)n6)c5c4c3)c21]

TABLE 1-continued
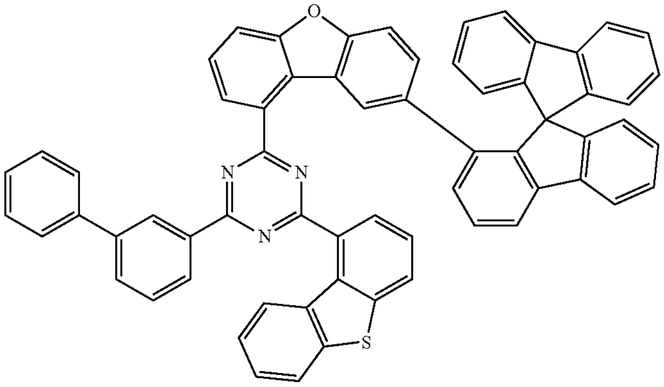 [SMILES: c1ccc(-c2cccc(-c3nc(-c4cccc5oc6ccc(-c7cccc8c7C7(c9ccccc9-c9ccccc97)c7ccccc7-8)cc6c45)nc(-c4cccc5sc6ccccc6c45)n3)c2)cc1]
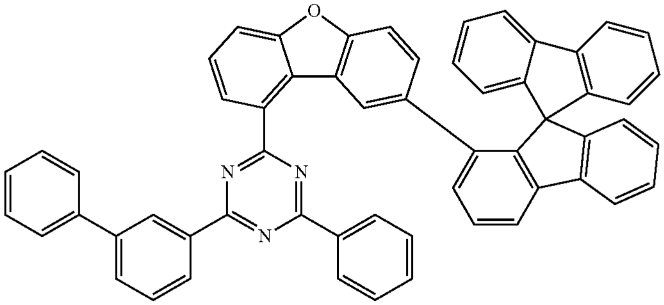 [SMILES: c1ccc(-c2cccc(-c3nc(-c4ccccc4)nc(-c4cccc5oc6ccc(-c7cccc8c7C7(c9ccccc9-c9ccccc97)c7ccccc7-8)cc6c45)n3)c2)cc1]
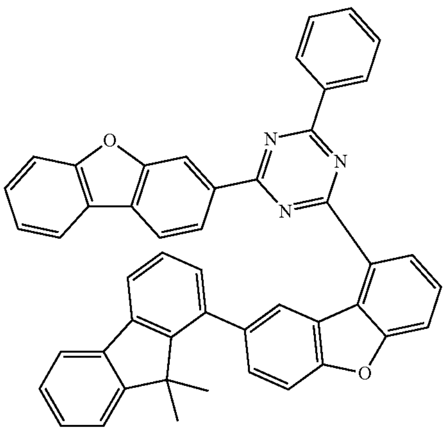 [SMILES: CC1(C)c2ccccc2-c2cccc(-c3ccc4oc5cccc(-c6nc(-c7ccccc7)nc(-c7ccc8c(c7)oc7ccccc78)n6)c5c4c3)c21]

TABLE 1-continued
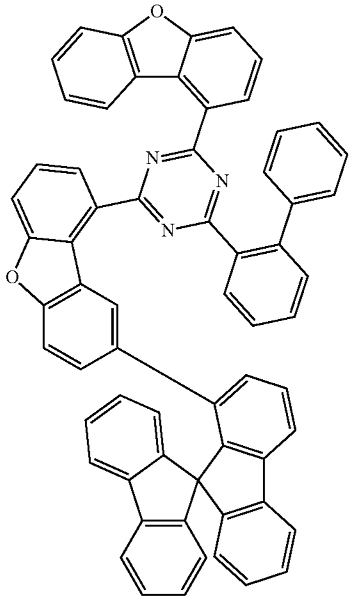 [SMILES: c1ccc(-c2ccccc2-c2nc(-c3cccc4oc5ccccc5c34)nc(-c3cccc4oc5ccc(-c6cccc7c6C6(c8ccccc8-c8ccccc86)c6ccccc6-7)cc5c34)n2)cc1]
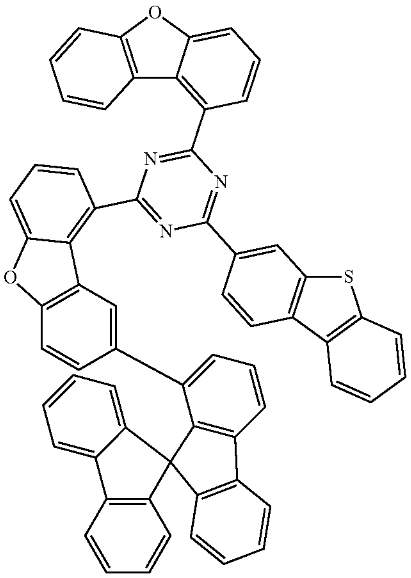 [SMILES: c1ccc2c(c1)-c1ccccc1C21c2ccccc2-c2cccc(-c3ccc4oc5cccc(-c6nc(-c7ccc8c(c7)sc7ccccc78)nc(-c7cccc8oc9ccccc9c78)n6)c5c4c3)c21]

TABLE 1-continued
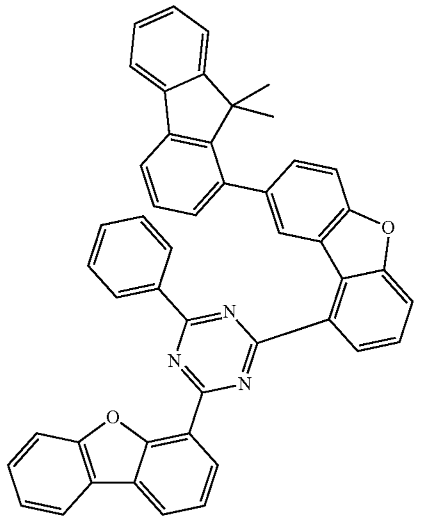 [SMILES: CC1(C)c2ccccc2-c2cccc(-c3ccc4oc5cccc(-c6nc(-c7ccccc7)nc(-c7cccc8c7oc7ccccc78)n6)c5c4c3)c21]
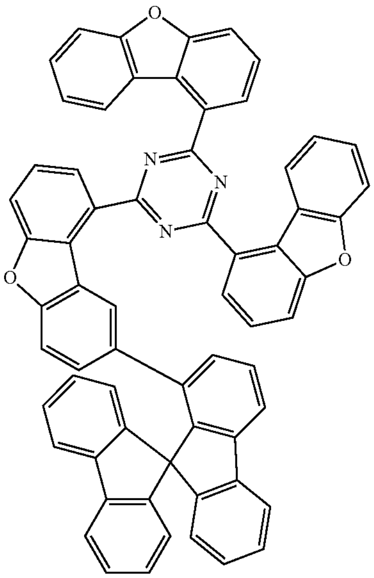 [SMILES: c1ccc2c(c1)-c1ccccc1C21c2ccccc2-c2cccc(-c3ccc4oc5cccc(-c6nc(-c7cccc8oc9ccccc9c78)nc(-c7cccc8oc9ccccc9c78)n6)c5c4c3)c21]

TABLE 1-continued
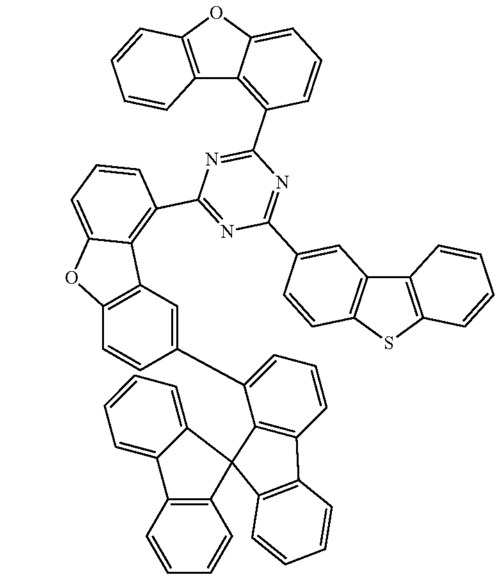 [SMILES: c1ccc2c(c1)-c1ccccc1C21c2ccccc2-c2cccc(-c3ccc4oc5cccc(-c6nc(-c7ccc8sc9ccccc9c8c7)nc(-c7cccc8oc9ccccc9c78)n6)c5c4c3)c21]
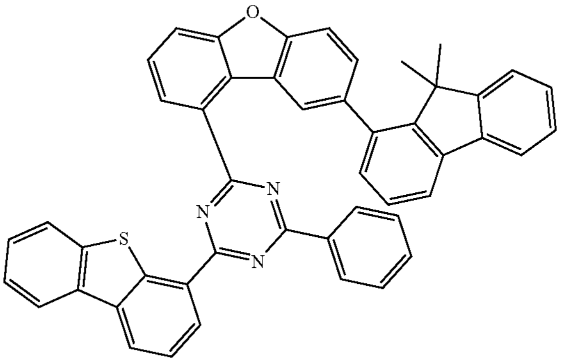 [SMILES: CC1(C)c2ccccc2-c2cccc(-c3ccc4oc5cccc(-c6nc(-c7ccccc7)nc(-c7cccc8c7sc7ccccc78)n6)c5c4c3)c21]
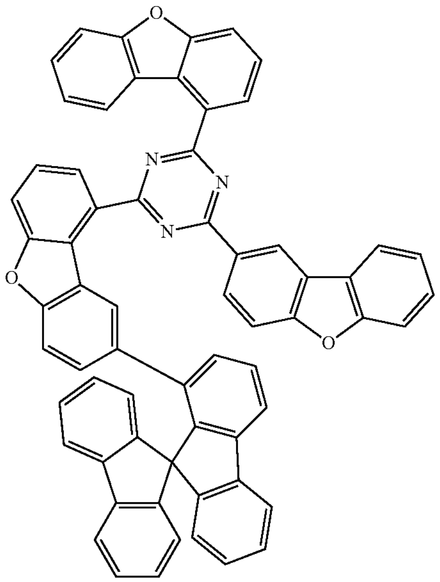 [SMILES: c1ccc2c(c1)-c1ccccc1C21c2ccccc2-c2cccc(-c3ccc4oc5cccc(-c6nc(-c7ccc8oc9ccccc9c8c7)nc(-c7cccc8oc9ccccc9c78)n6)c5c4c3)c21]

TABLE 1-continued
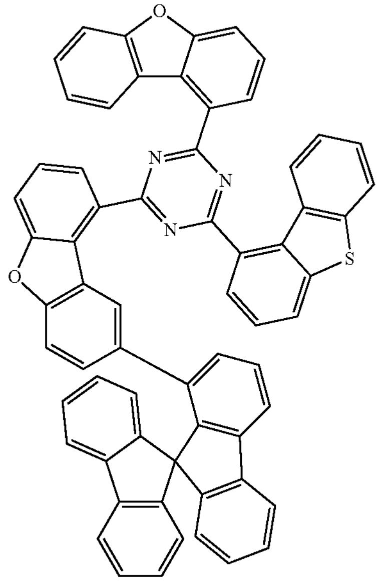
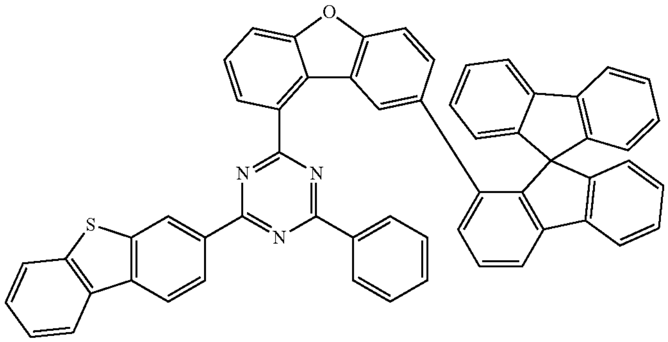 [SMILES: c1ccc(-c2nc(-c3ccc4c(c3)sc3ccccc34)nc(-c3cccc4oc5ccc(-c6cccc7c6C6(c8ccccc8-c8ccccc86)c6ccccc6-7)cc5c34)n2)cc1]
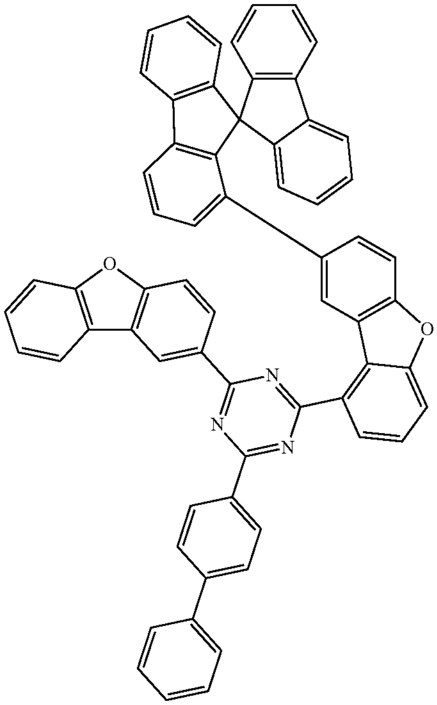 [SMILES: c1ccc(-c2ccc(-c3nc(-c4ccc5oc6ccccc6c5c4)nc(-c4cccc5oc6ccc(-c7cccc8c7C7(c9ccccc9-c9ccccc97)c7ccccc7-8)cc6c45)n3)cc2)cc1]

TABLE 1-continued
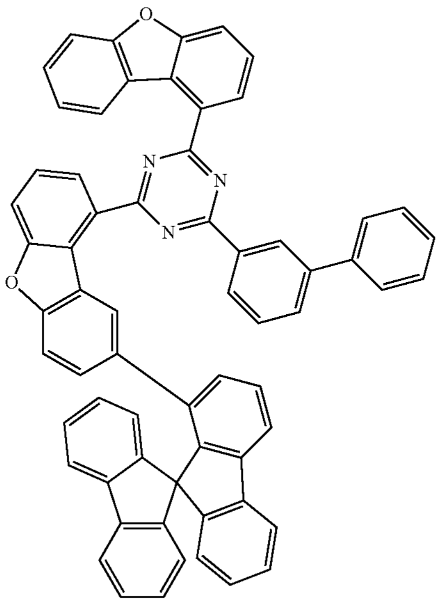 [SMILES: c1ccc(-c2cccc(-c3nc(-c4cccc5oc6ccccc6c45)nc(-c4cccc5oc6ccc(-c7cccc8c7C7(c9ccccc9-c9ccccc97)c7ccccc7-8)cc6c45)n3)c2)cc1]
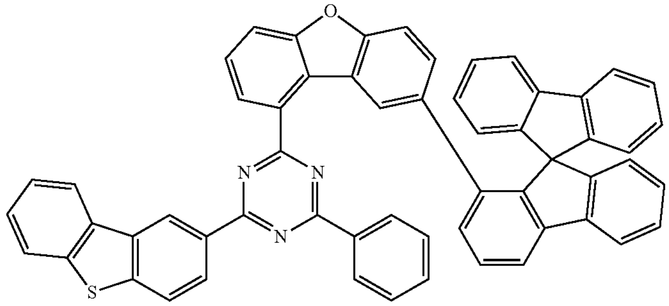 [SMILES: c1ccc(-c2nc(-c3ccc4sc5ccccc5c4c3)nc(-c3cccc4oc5ccc(-c6cccc7c6C6(c8ccccc8-c8ccccc86)c6ccccc6-7)cc5c34)n2)cc1]
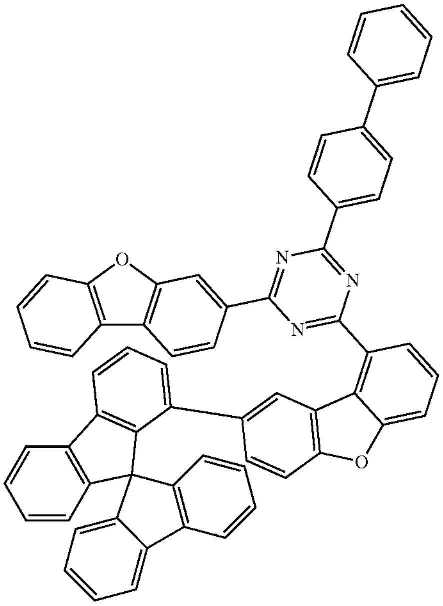 [SMILES: c1ccc(-c2ccc(-c3nc(-c4ccc5c(c4)oc4ccccc45)nc(-c4cccc5oc6ccc(-c7cccc8c7C7(c9ccccc9-c9ccccc97)c7ccccc7-8)cc6c45)n3)cc2)cc1]

TABLE 1-continued
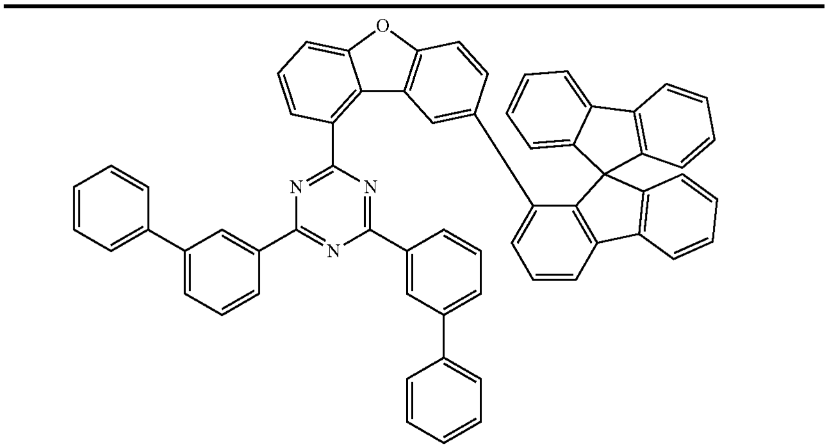
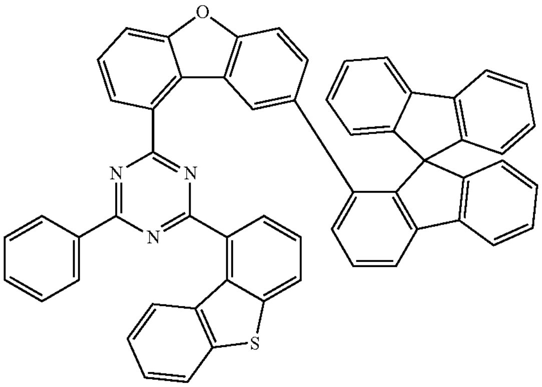 [SMILES: c1ccc(-c2nc(-c3cccc4oc5ccc(-c6cccc7c6C6(c8ccccc8-c8ccccc86)c6ccccc6-7)cc5c34)nc(-c3cccc4sc5ccccc5c34)n2)cc1]
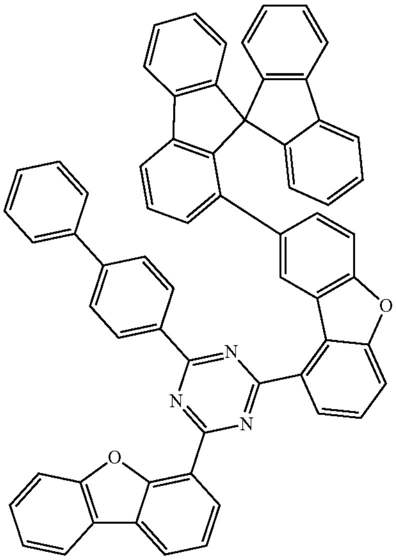 [SMILES: c1ccc(-c2ccc(-c3nc(-c4cccc5c4oc4ccccc45)nc(-c4cccc5oc6ccc(-c7cccc8c7C7(c9ccccc9-c9ccccc97)c7ccccc7-8)cc6c45)n3)cc2)cc1]

TABLE 1-continued
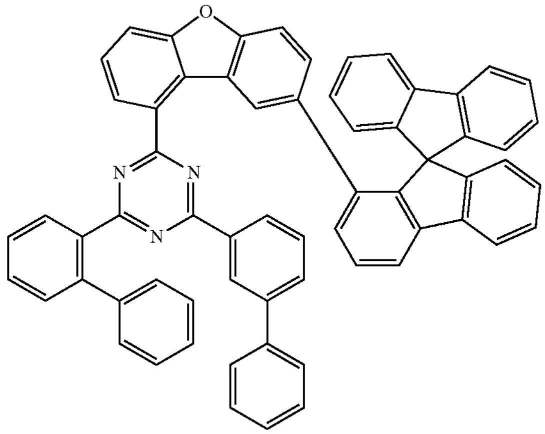 [SMILES: c1ccc(-c2cccc(-c3nc(-c4ccccc4-c4ccccc4)nc(-c4cccc5oc6ccc(-c7cccc8c7C7(c9ccccc9-c9ccccc97)c7ccccc7-8)cc6c45)n3)c2)cc1]
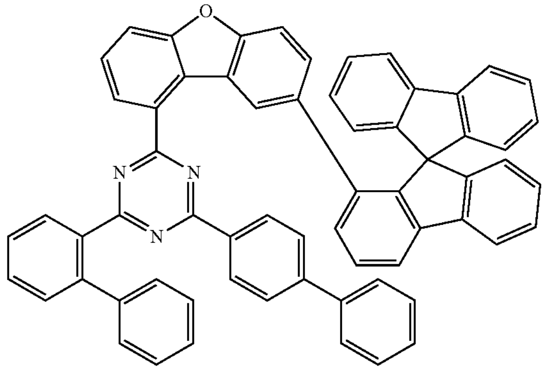 [SMILES: c1ccc(-c2ccc(-c3nc(-c4ccccc4-c4ccccc4)nc(-c4cccc5oc6ccc(-c7cccc8c7C7(c9ccccc9-c9ccccc97)c7ccccc7-8)cc6c45)n3)cc2)cc1]
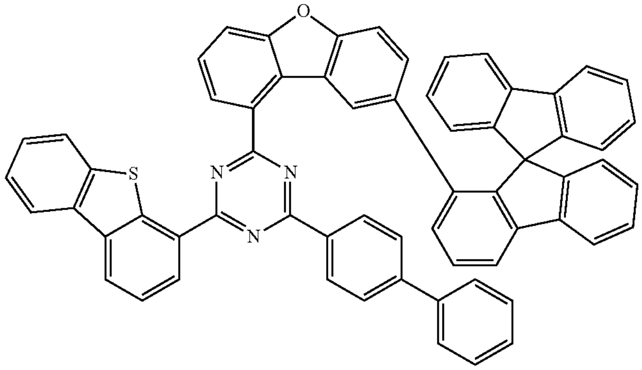 [SMILES: c1ccc(-c2ccc(-c3nc(-c4cccc5c4sc4ccccc45)nc(-c4cccc5oc6ccc(-c7cccc8c7C7(c9ccccc9-c9ccccc97)c7ccccc7-8)cc6c45)n3)cc2)cc1]

TABLE 1-continued
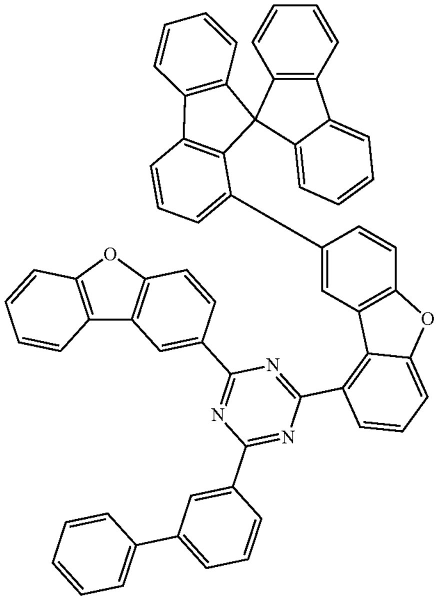 [SMILES: c1ccc(-c2cccc(-c3nc(-c4ccc5oc6ccccc6c5c4)nc(-c4cccc5oc6ccc(-c7cccc8c7C7(c9ccccc9-c9ccccc97)c7ccccc7-8)cc6c45)n3)c2)cc1]
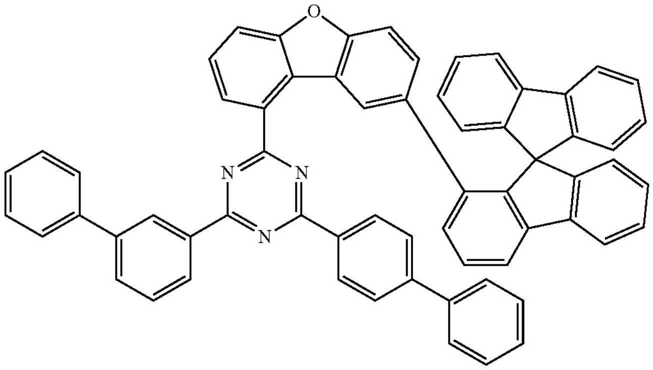 [SMILES: c1ccc(-c2ccc(-c3nc(-c4cccc(-c5ccccc5)c4)nc(-c4cccc5oc6ccc(-c7cccc8c7C7(c9ccccc9-c9ccccc97)c7ccccc7-8)cc6c45)n3)cc2)cc1]
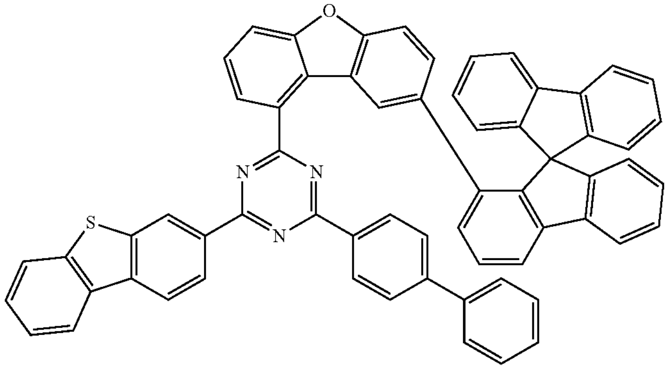 [SMILES: c1ccc(-c2ccc(-c3nc(-c4ccc5c(c4)sc4ccccc45)nc(-c4cccc5oc6ccc(-c7cccc8c7C7(c9ccccc9-c9ccccc97)c7ccccc7-8)cc6c45)n3)cc2)cc1]

TABLE 1-continued
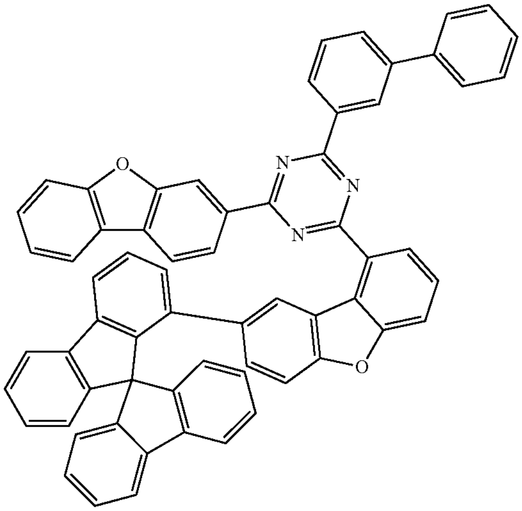 [SMILES: c1ccc(-c2cccc(-c3nc(-c4ccc5c(c4)oc4ccccc45)nc(-c4cccc5oc6ccc(-c7cccc8c7C7(c9ccccc9-c9ccccc97)c7ccccc7-8)cc6c45)n3)c2)cc1]
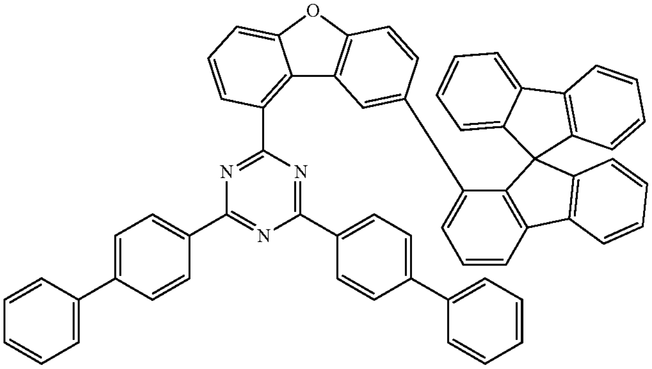 [SMILES: c1ccc(-c2ccc(-c3nc(-c4ccc(-c5ccccc5)cc4)nc(-c4cccc5oc6ccc(-c7cccc8c7C7(c9ccccc9-c9ccccc97)c7ccccc7-8)cc6c45)n3)cc2)cc1]
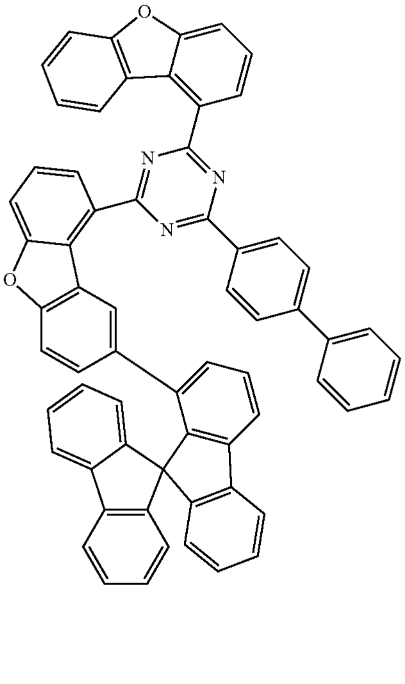 [SMILES: c1ccc(-c2ccc(-c3nc(-c4cccc5oc6ccccc6c45)nc(-c4cccc5oc6ccc(-c7cccc8c7C7(c9ccccc9-c9ccccc97)c7ccccc7-8)cc6c45)n3)cc2)cc1]

TABLE 1-continued
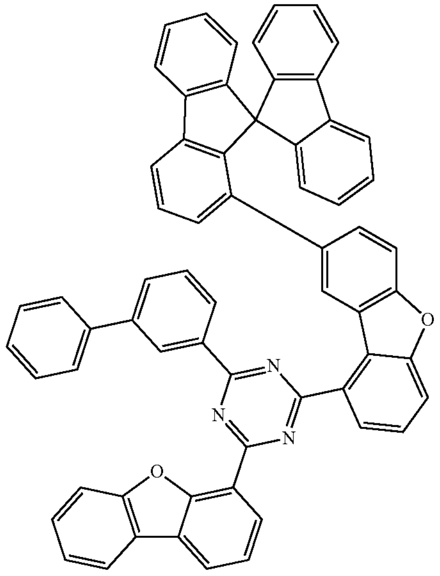 [SMILES: c1ccc(-c2cccc(-c3nc(-c4cccc5c4oc4ccccc45)nc(-c4cccc5oc6ccc(-c7cccc8c7C7(c9ccccc9-c9ccccc97)c7ccccc7-8)cc6c45)n3)c2)cc1]
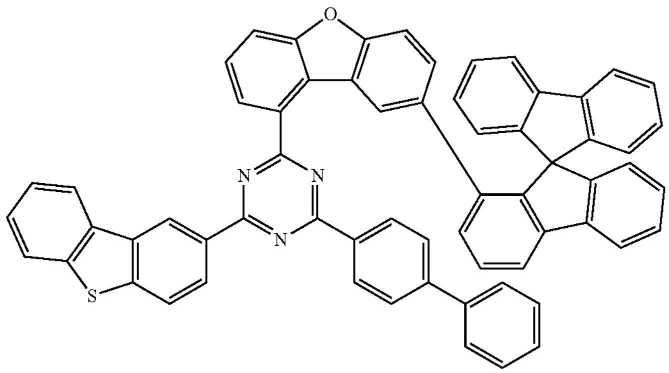 [SMILES: c1ccc(-c2ccc(-c3nc(-c4ccc5sc6ccccc6c5c4)nc(-c4cccc5oc6ccc(-c7cccc8c7C7(c9ccccc9-c9ccccc97)c7ccccc7-8)cc6c45)n3)cc2)cc1]
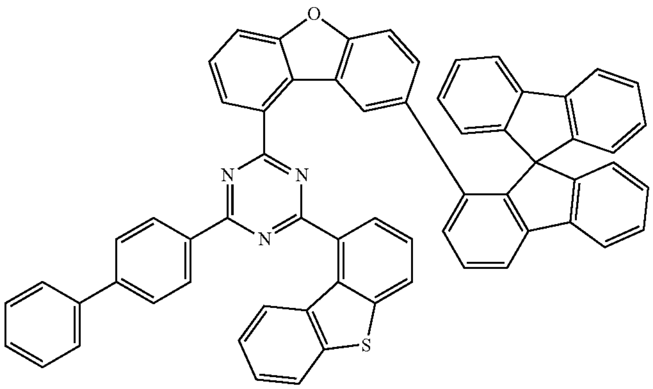 [SMILES: c1ccc(-c2ccc(-c3nc(-c4cccc5oc6ccc(-c7cccc8c7C7(c9ccccc9-c9ccccc97)c7ccccc7-8)cc6c45)nc(-c4cccc5sc6ccccc6c45)n3)cc2)cc1]

TABLE 1-continued
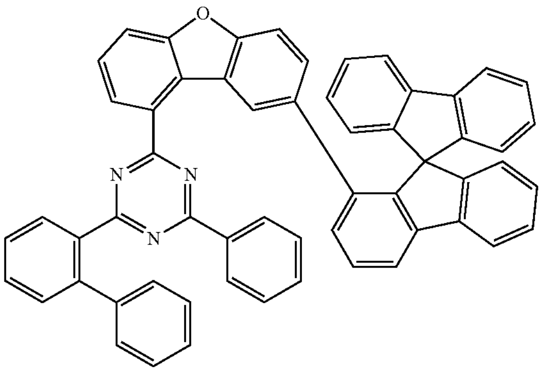 [SMILES: c1ccc(-c2nc(-c3ccccc3-c3ccccc3)nc(-c3cccc4oc5ccc(-c6cccc7c6C6(c8ccccc8-c8ccccc86)c6ccccc6-7)cc5c34)n2)cc1]
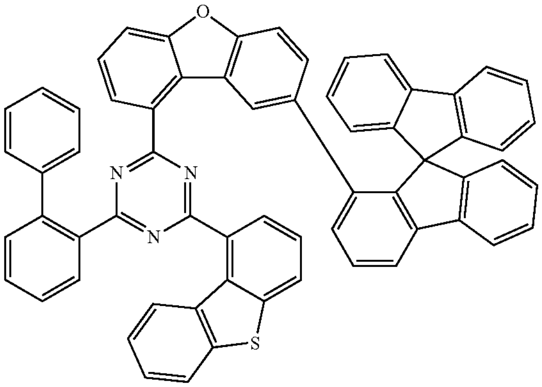 [SMILES: c1ccc(-c2ccccc2-c2nc(-c3cccc4oc5ccc(-c6cccc7c6C6(c8ccccc8-c8ccccc86)c6ccccc6-7)cc5c34)nc(-c3cccc4sc5ccccc5c34)n2)cc1]
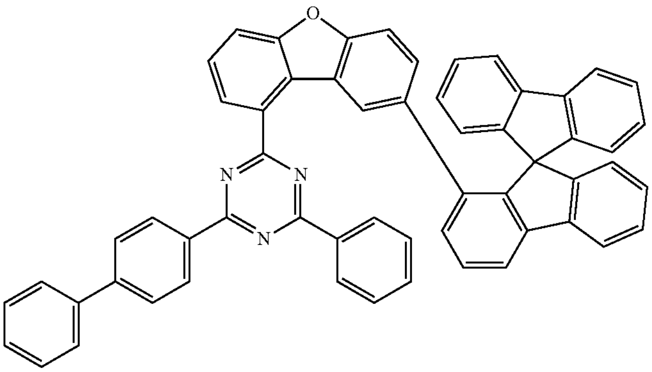 [SMILES: c1ccc(-c2ccc(-c3nc(-c4ccccc4)nc(-c4cccc5oc6ccc(-c7cccc8c7C7(c9ccccc9-c9ccccc97)c7ccccc7-8)cc6c45)n3)cc2)cc1]
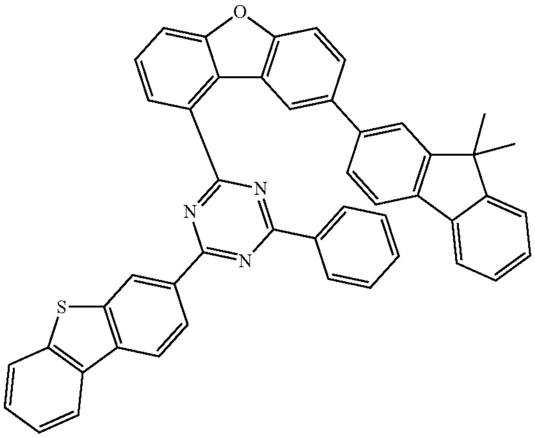 [SMILES: CC1(C)c2ccccc2-c2ccc(-c3ccc4oc5cccc(-c6nc(-c7ccccc7)nc(-c7ccc8c(c7)sc7ccccc78)n6)c5c4c3)cc21]

TABLE 1-continued
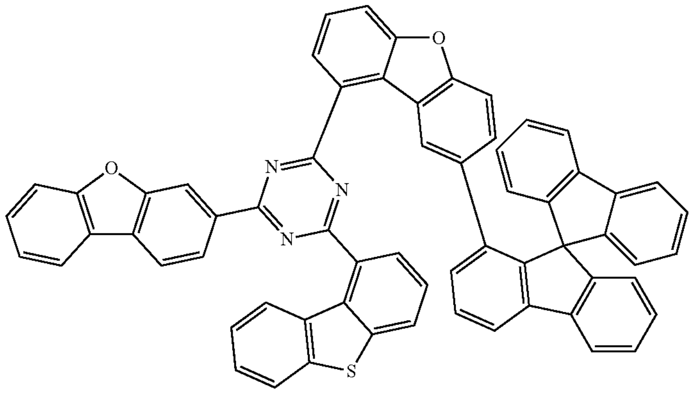 [SMILES: c1ccc2c(c1)-c1ccccc1C21c2ccccc2-c2cccc(-c3ccc4oc5cccc(-c6nc(-c7ccc8c(c7)oc7ccccc78)nc(-c7cccc8sc9ccccc9c78)n6)c5c4c3)c21]
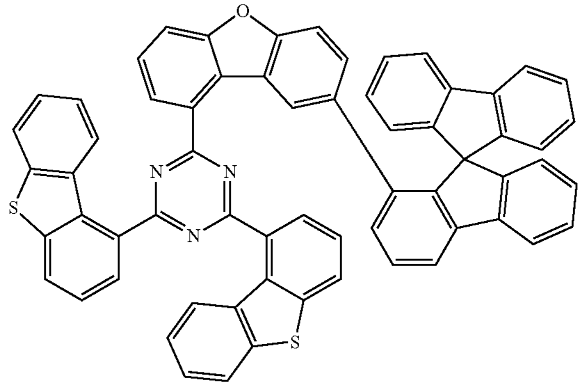 [SMILES: c1ccc2c(c1)-c1ccccc1C21c2ccccc2-c2cccc(-c3ccc4oc5cccc(-c6nc(-c7cccc8sc9ccccc9c78)nc(-c7cccc8sc9ccccc9c78)n6)c5c4c3)c21]
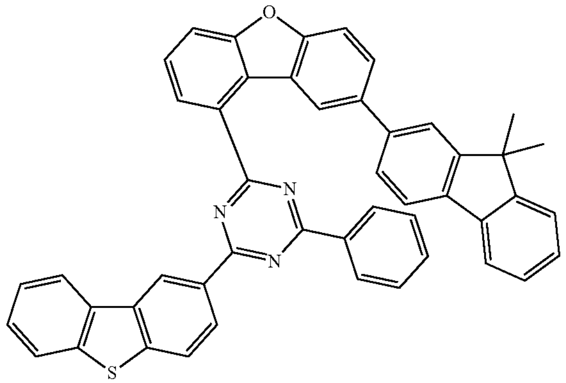 [SMILES: CC1(C)c2ccccc2-c2ccc(-c3ccc4oc5cccc(-c6nc(-c7ccccc7)nc(-c7ccc8sc9ccccc9c8c7)n6)c5c4c3)cc21]

TABLE 1-continued
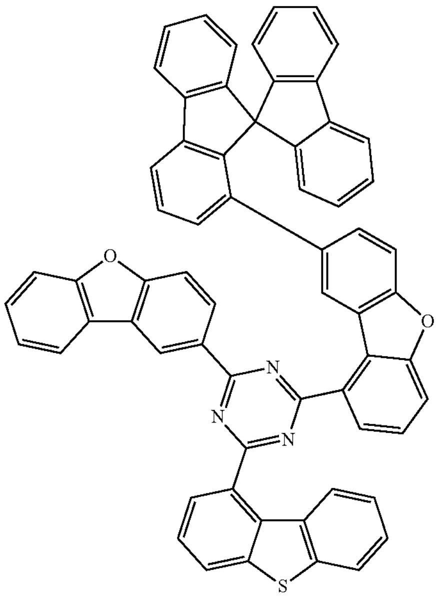 [SMILES: c1ccc2c(c1)-c1ccccc1C21c2ccccc2-c2cccc(-c3ccc4oc5cccc(-c6nc(-c7ccc8oc9ccccc9c8c7)nc(-c7cccc8sc9ccccc9c78)n6)c5c4c3)c21]
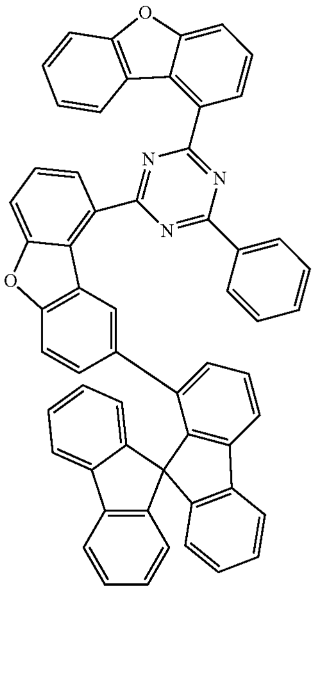 [SMILES: c1ccc(-c2nc(-c3cccc4oc5ccccc5c34)nc(-c3cccc4oc5ccc(-c6cccc7c6C6(c8ccccc8-c8ccccc86)c6ccccc6-7)cc5c34)n2)cc1]

TABLE 1-continued
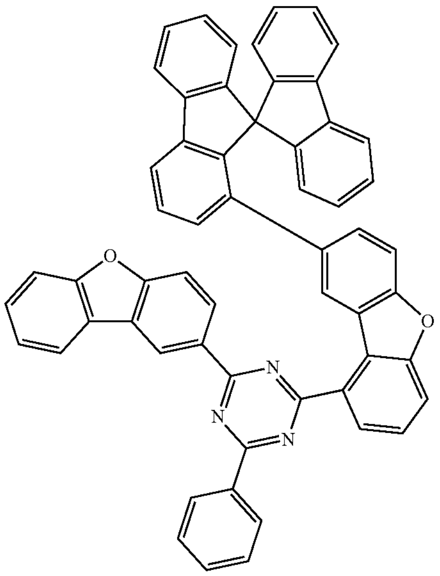 [SMILES: c1ccc(-c2nc(-c3ccc4oc5ccccc5c4c3)nc(-c3cccc4oc5ccc(-c6cccc7c6C6(c8ccccc8-c8ccccc86)c6ccccc6-7)cc5c34)n2)cc1]
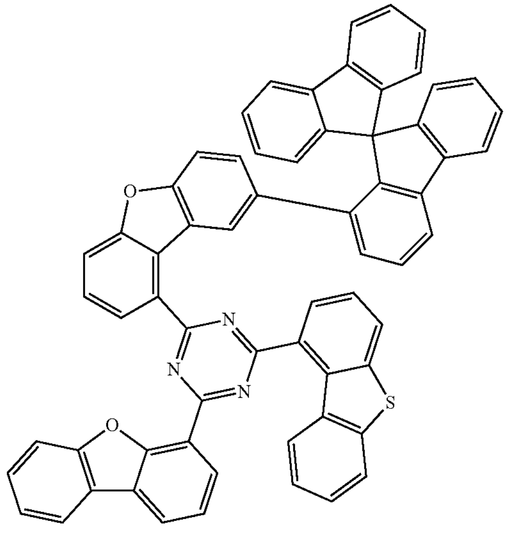 [SMILES: c1ccc2c(c1)-c1ccccc1C21c2ccccc2-c2cccc(-c3ccc4oc5cccc(-c6nc(-c7cccc8c7oc7ccccc78)nc(-c7cccc8sc9ccccc9c78)n6)c5c4c3)c21]
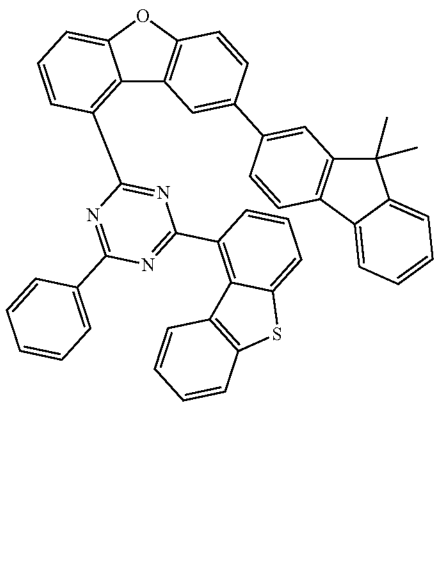 [SMILES: CC1(C)c2ccccc2-c2ccc(-c3ccc4oc5cccc(-c6nc(-c7ccccc7)nc(-c7cccc8sc9ccccc9c78)n6)c5c4c3)cc21]

TABLE 1-continued
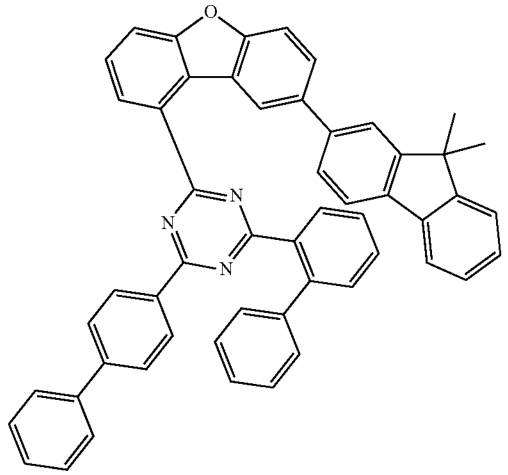 [SMILES: CC1(C)c2ccccc2-c2ccc(-c3ccc4oc5cccc(-c6nc(-c7ccc(-c8ccccc8)cc7)nc(-c7ccccc7-c7ccccc7)n6)c5c4c3)cc21]
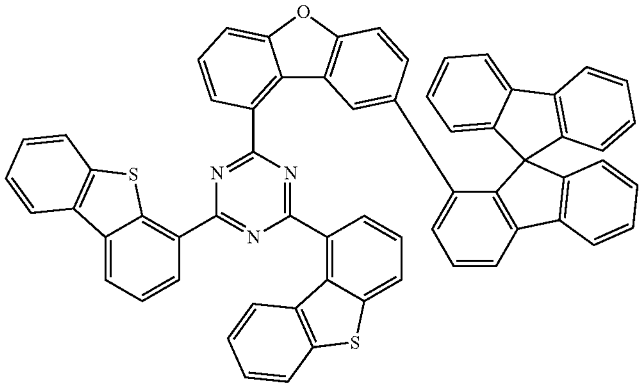 [SMILES: c1ccc2c(c1)-c1ccccc1C21c2ccccc2-c2cccc(-c3ccc4oc5cccc(-c6nc(-c7cccc8c7sc7ccccc78)nc(-c7cccc8sc9ccccc9c78)n6)c5c4c3)c21]
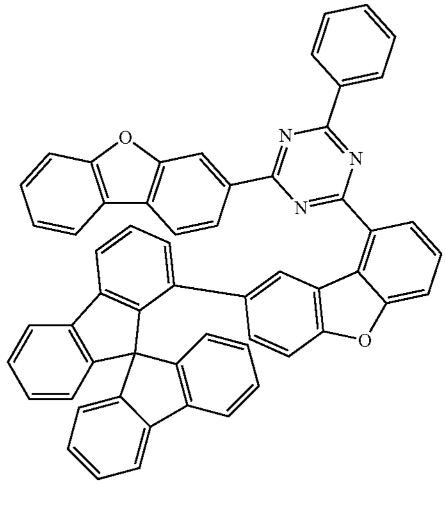 [SMILES: c1ccc(-c2nc(-c3ccc4c(c3)oc3ccccc34)nc(-c3cccc4oc5ccc(-c6cccc7c6C6(c8ccccc8-c8ccccc86)c6ccccc6-7)cc5c34)n2)cc1]

TABLE 1-continued
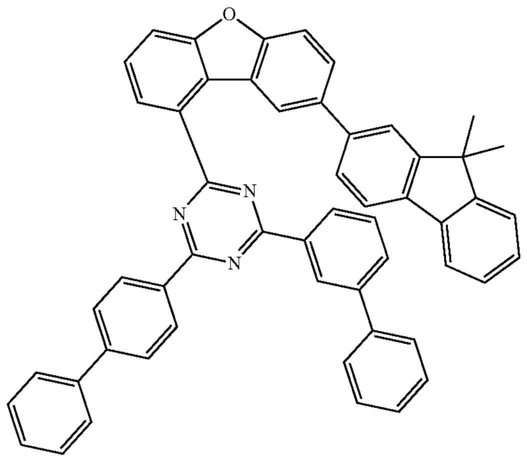 [SMILES: CC1(C)c2ccccc2-c2ccc(-c3ccc4oc5cccc(-c6nc(-c7ccc(-c8ccccc8)cc7)nc(-c7cccc(-c8ccccc8)c7)n6)c5c4c3)cc21]
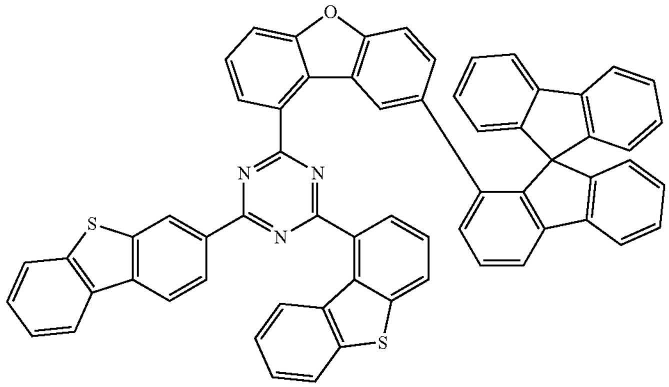 [SMILES: c1ccc2c(c1)-c1ccccc1C21c2ccccc2-c2cccc(-c3ccc4oc5cccc(-c6nc(-c7ccc8c(c7)sc7ccccc78)nc(-c7cccc8sc9ccccc9c78)n6)c5c4c3)c21]
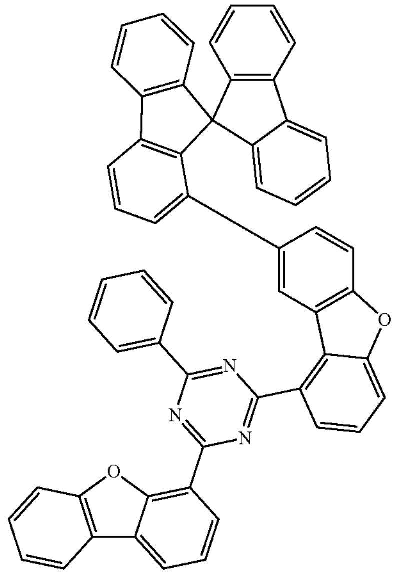 [SMILES: c1ccc(-c2nc(-c3cccc4c3oc3ccccc34)nc(-c3cccc4oc5ccc(-c6cccc7c6C6(c8ccccc8-c8ccccc86)c6ccccc6-7)cc5c34)n2)cc1]

TABLE 1-continued
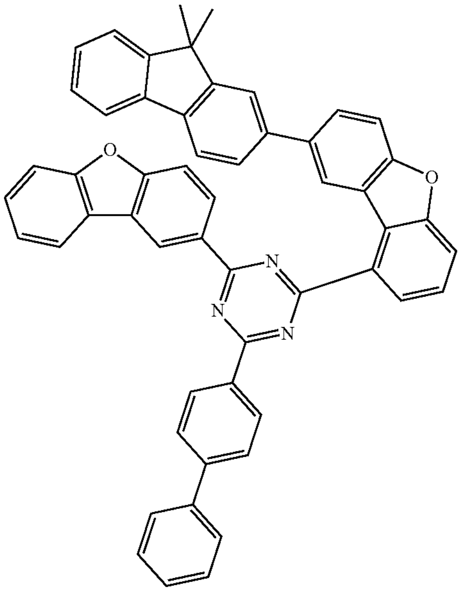 [SMILES: CC1(C)c2ccccc2-c2ccc(-c3ccc4oc5cccc(-c6nc(-c7ccc(-c8ccccc8)cc7)nc(-c7ccc8oc9ccccc9c8c7)n6)c5c4c3)cc21]
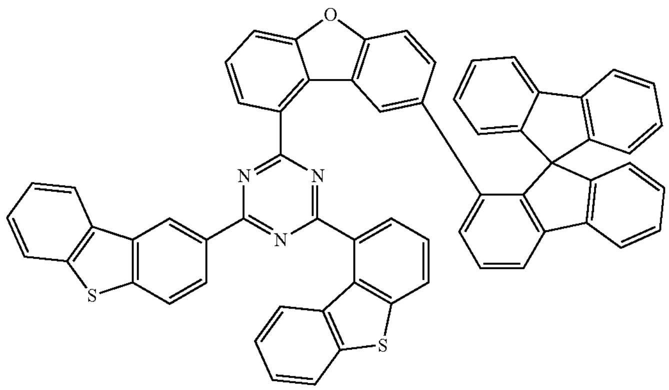 [SMILES: c1ccc2c(c1)-c1ccccc1C21c2ccccc2-c2cccc(-c3ccc4oc5cccc(-c6nc(-c7ccc8sc9ccccc9c8c7)nc(-c7cccc8sc9ccccc9c78)n6)c5c4c3)c21]
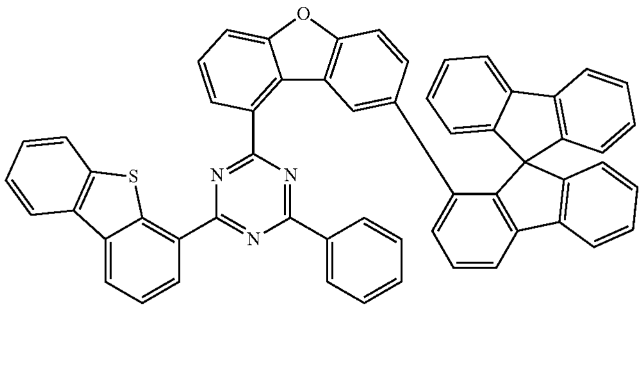 [SMILES: c1ccc(-c2nc(-c3cccc4c3sc3ccccc34)nc(-c3cccc4oc5ccc(-c6cccc7c6C6(c8ccccc8-c8ccccc86)c6ccccc6-7)cc5c34)n2)cc1]

TABLE 1-continued
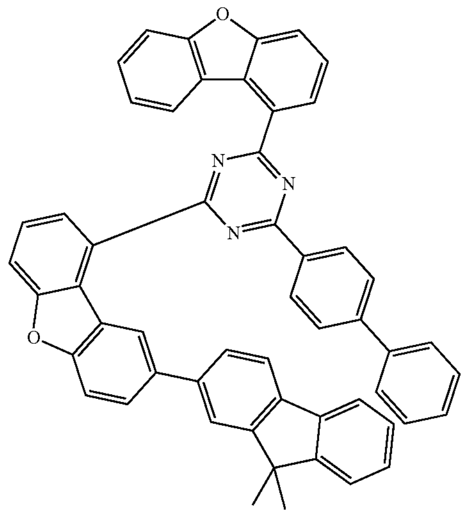 [SMILES: CC1(C)c2ccccc2-c2ccc(-c3ccc4oc5cccc(-c6nc(-c7ccc(-c8ccccc8)cc7)nc(-c7cccc8oc9ccccc9c78)n6)c5c4c3)cc21]
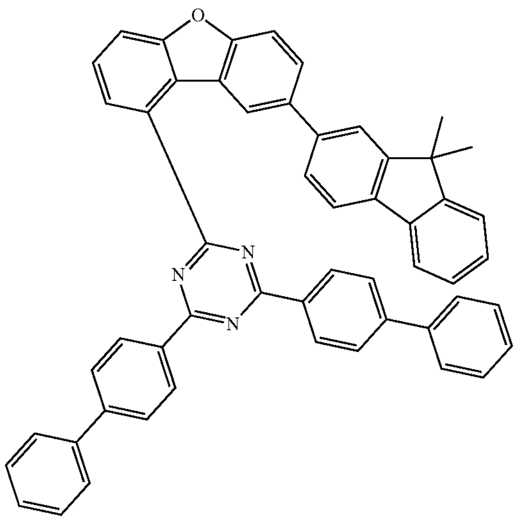 [SMILES: CC1(C)c2ccccc2-c2ccc(-c3ccc4oc5cccc(-c6nc(-c7ccc(-c8ccccc8)cc7)nc(-c7ccc(-c8ccccc8)cc7)n6)c5c4c3)cc21]
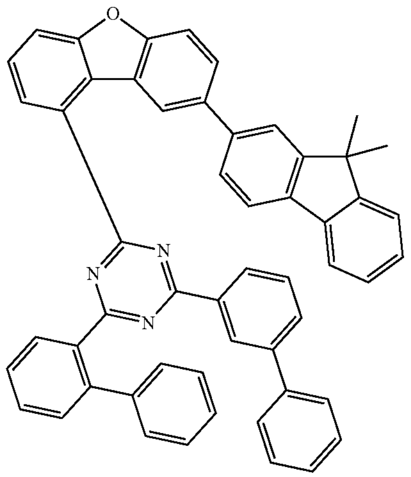 [SMILES: CC1(C)c2ccccc2-c2ccc(-c3ccc4oc5cccc(-c6nc(-c7cccc(-c8ccccc8)c7)nc(-c7ccccc7-c7ccccc7)n6)c5c4c3)cc21]

TABLE 1-continued
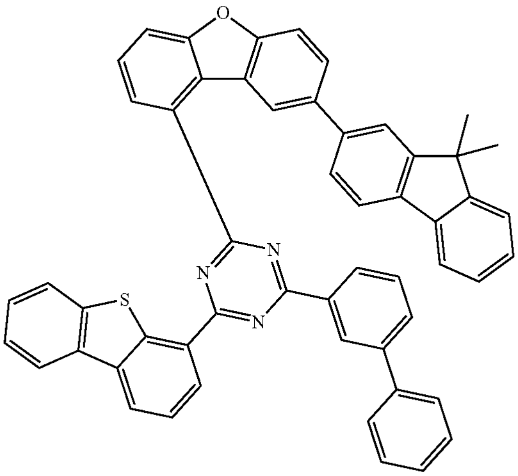 [SMILES: CC1(C)c2ccccc2-c2ccc(-c3ccc4oc5cccc(-c6nc(-c7cccc(-c8ccccc8)c7)nc(-c7cccc8c7sc7ccccc78)n6)c5c4c3)cc21]
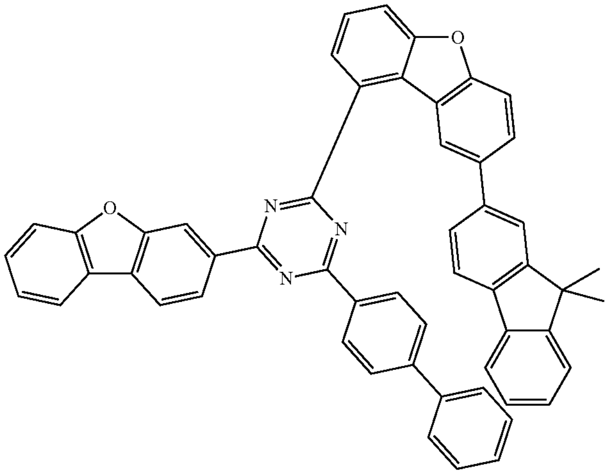 [SMILES: CC1(C)c2ccccc2-c2ccc(-c3ccc4oc5cccc(-c6nc(-c7ccc(-c8ccccc8)cc7)nc(-c7ccc8c(c7)oc7ccccc78)n6)c5c4c3)cc21]
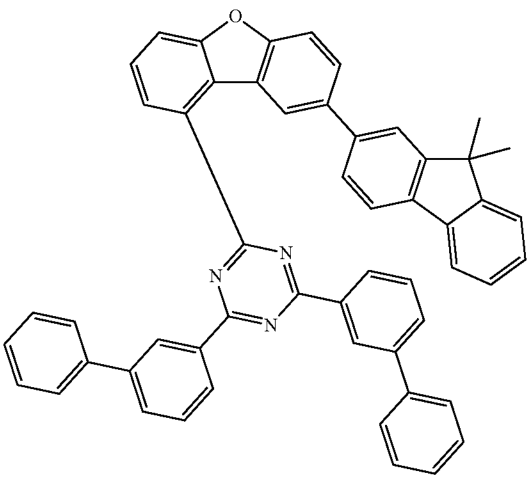 [SMILES: CC1(C)c2ccccc2-c2ccc(-c3ccc4oc5cccc(-c6nc(-c7cccc(-c8ccccc8)c7)nc(-c7cccc(-c8ccccc8)c7)n6)c5c4c3)cc21]

TABLE 1-continued
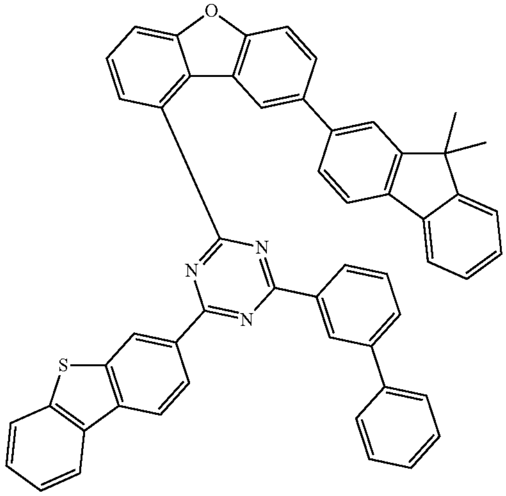 [SMILES: CC1(C)c2ccccc2-c2ccc(-c3ccc4oc5cccc(-c6nc(-c7cccc(-c8ccccc8)c7)nc(-c7ccc8c(c7)sc7ccccc78)n6)c5c4c3)cc21]
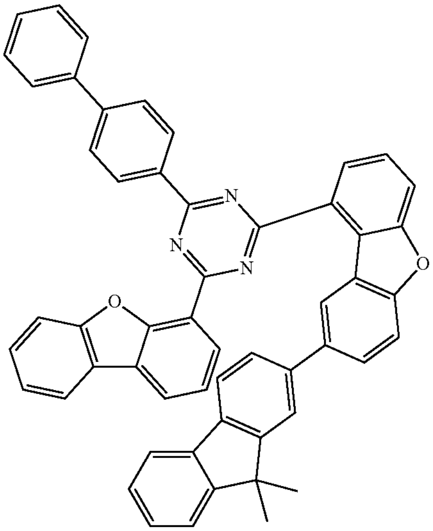 [SMILES: CC1(C)c2ccccc2-c2ccc(-c3ccc4oc5cccc(-c6nc(-c7ccc(-c8ccccc8)cc7)nc(-c7cccc8c7oc7ccccc78)n6)c5c4c3)cc21]
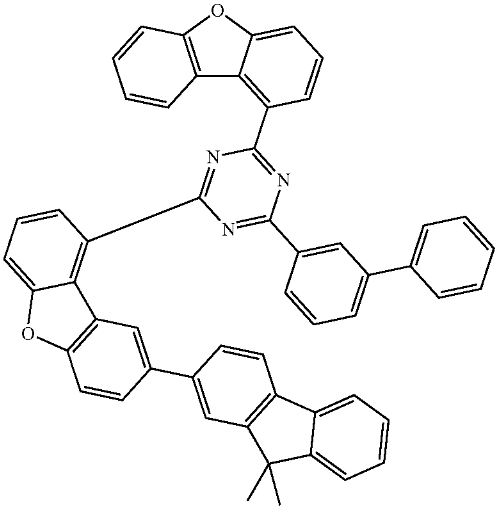 [SMILES: CC1(C)c2ccccc2-c2ccc(-c3ccc4oc5cccc(-c6nc(-c7cccc(-c8ccccc8)c7)nc(-c7cccc8oc9ccccc9c78)n6)c5c4c3)cc21]

TABLE 1-continued
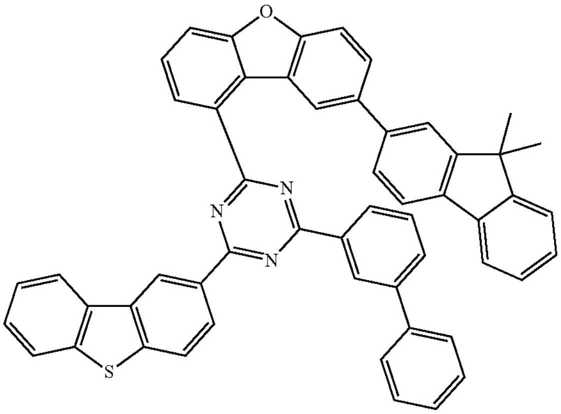 [SMILES: CC1(C)c2ccccc2-c2ccc(-c3ccc4oc5cccc(-c6nc(-c7cccc(-c8ccccc8)c7)nc(-c7ccc8sc9ccccc9c8c7)n6)c5c4c3)cc21]
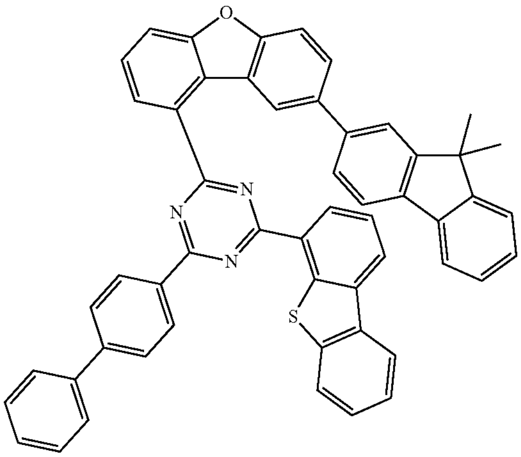 [SMILES: CC1(C)c2ccccc2-c2ccc(-c3ccc4oc5cccc(-c6nc(-c7ccc(-c8ccccc8)cc7)nc(-c7cccc8c7sc7ccccc78)n6)c5c4c3)cc21]
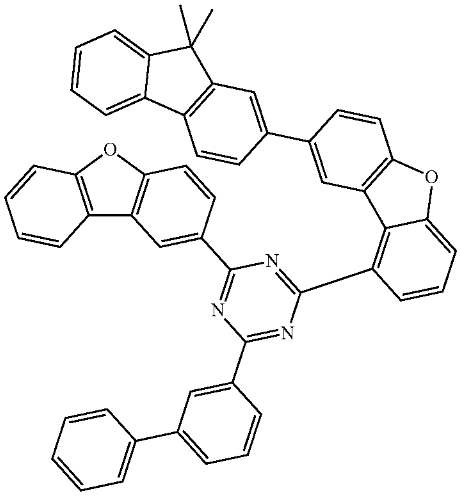 [SMILES: CC1(C)c2ccccc2-c2ccc(-c3ccc4oc5cccc(-c6nc(-c7cccc(-c8ccccc8)c7)nc(-c7ccc8oc9ccccc9c8c7)n6)c5c4c3)cc21]

TABLE 1-continued
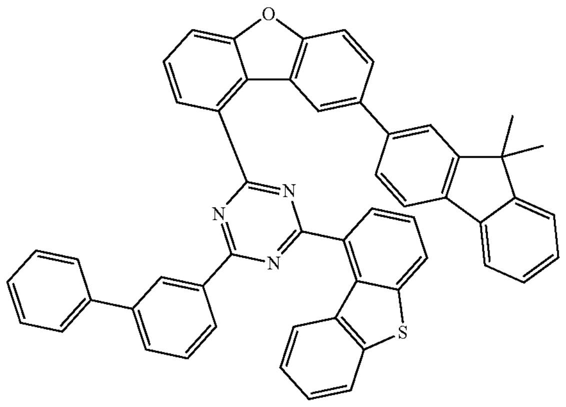 [SMILES: CC1(C)c2ccccc2-c2ccc(-c3ccc4oc5cccc(-c6nc(-c7cccc(-c8ccccc8)c7)nc(-c7cccc8sc9ccccc9c78)n6)c5c4c3)cc21]
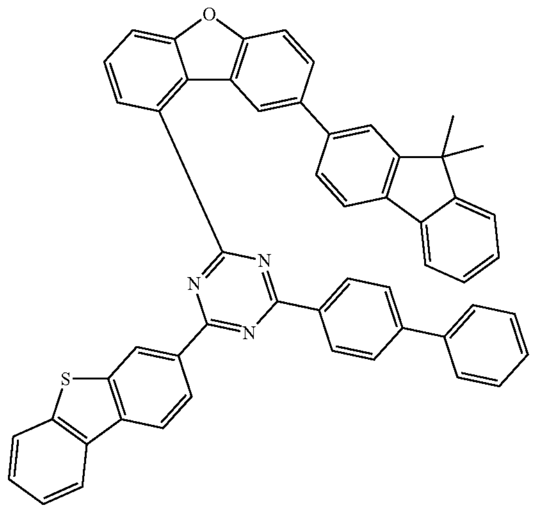 [SMILES: CC1(C)c2ccccc2-c2ccc(-c3ccc4oc5cccc(-c6nc(-c7ccc(-c8ccccc8)cc7)nc(-c7ccc8c(c7)sc7ccccc78)n6)c5c4c3)cc21]
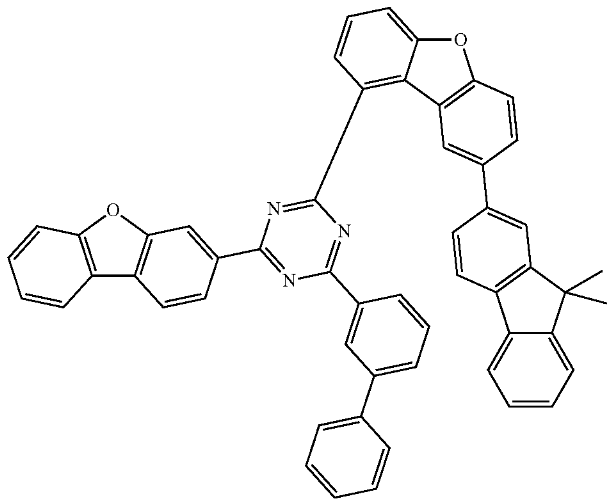 [SMILES: CC1(C)c2ccccc2-c2ccc(-c3ccc4oc5cccc(-c6nc(-c7cccc(-c8ccccc8)c7)nc(-c7ccc8c(c7)oc7ccccc78)n6)c5c4c3)cc21]

TABLE 1-continued
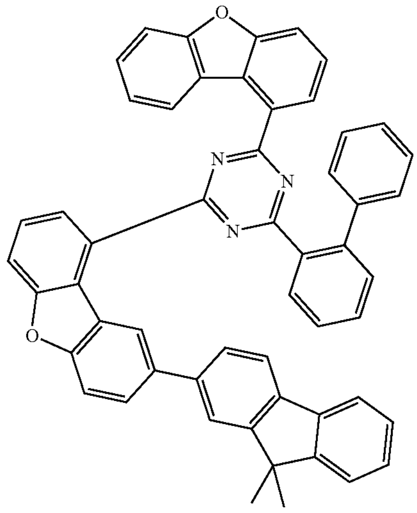 [SMILES: CC1(C)c2ccccc2-c2ccc(-c3ccc4oc5cccc(-c6nc(-c7ccccc7-c7ccccc7)nc(-c7cccc8oc9ccccc9c78)n6)c5c4c3)cc21]
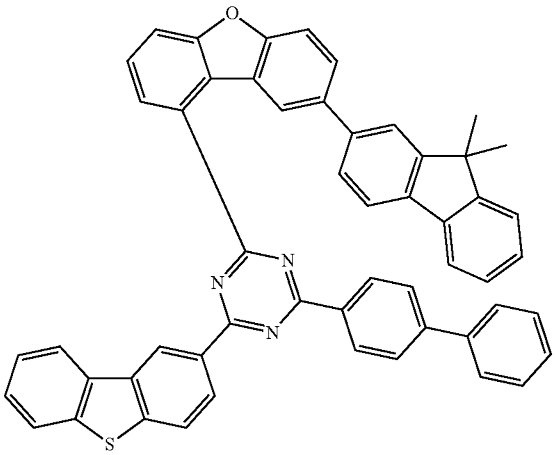 [SMILES: CC1(C)c2ccccc2-c2ccc(-c3ccc4oc5cccc(-c6nc(-c7ccc(-c8ccccc8)cc7)nc(-c7ccc8sc9ccccc9c8c7)n6)c5c4c3)cc21]
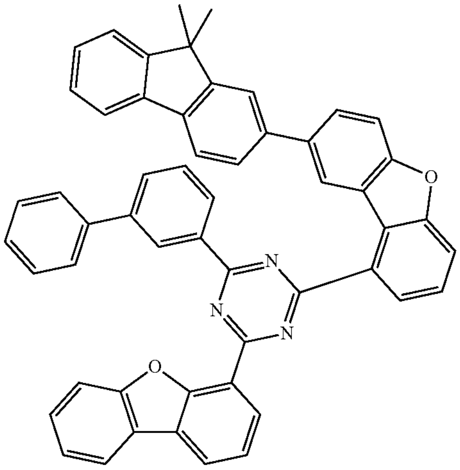 [SMILES: CC1(C)c2ccccc2-c2ccc(-c3ccc4oc5cccc(-c6nc(-c7cccc(-c8ccccc8)c7)nc(-c7cccc8c7oc7ccccc78)n6)c5c4c3)cc21]

TABLE 1-continued
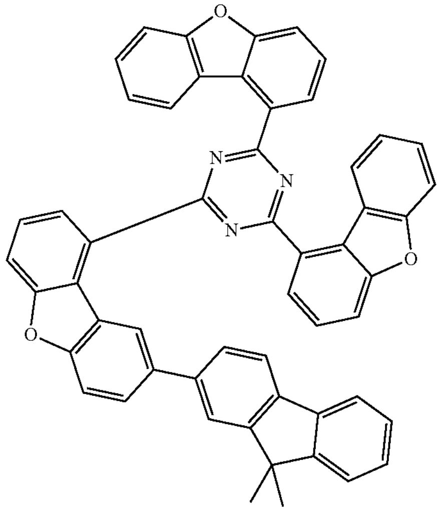 [SMILES: CC1(C)c2ccccc2-c2ccc(-c3ccc4oc5cccc(-c6nc(-c7cccc8oc9ccccc9c78)nc(-c7cccc8oc9ccccc9c78)n6)c5c4c3)cc21]
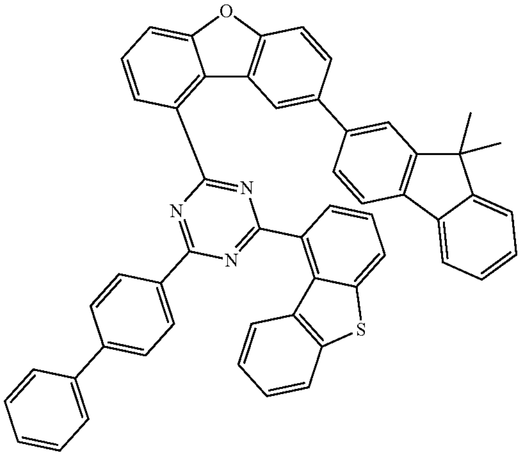 [SMILES: CC1(C)c2ccccc2-c2ccc(-c3ccc4oc5cccc(-c6nc(-c7ccc(-c8ccccc8)cc7)nc(-c7cccc8sc9ccccc9c78)n6)c5c4c3)cc21]
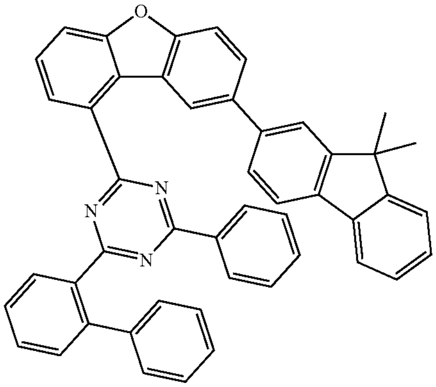 [SMILES: CC1(C)c2ccccc2-c2ccc(-c3ccc4oc5cccc(-c6nc(-c7ccccc7)nc(-c7ccccc7-c7ccccc7)n6)c5c4c3)cc21]

TABLE 1-continued
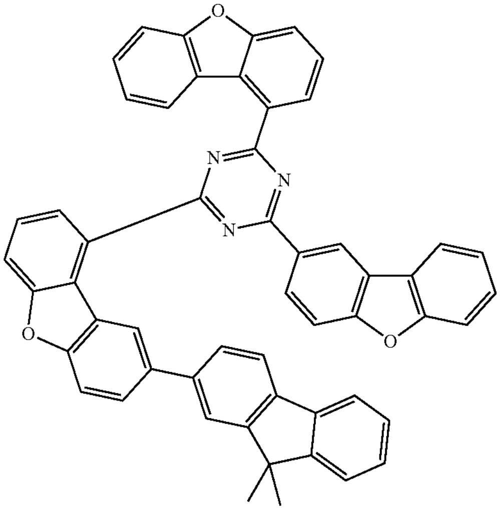 [SMILES: CC1(C)c2ccccc2-c2ccc(-c3ccc4oc5cccc(-c6nc(-c7ccc8oc9ccccc9c8c7)nc(-c7cccc8oc9ccccc9c78)n6)c5c4c3)cc21]
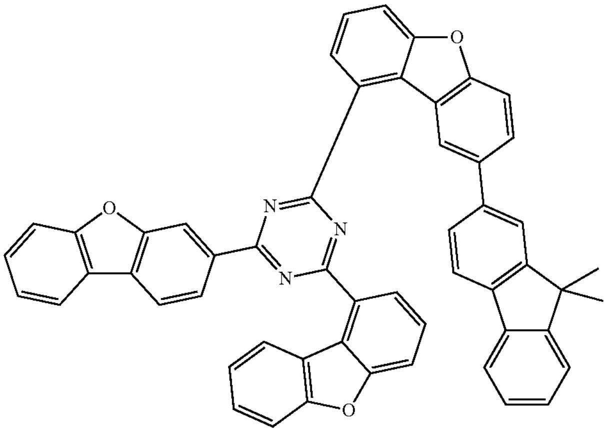 [SMILES: CC1(C)c2ccccc2-c2ccc(-c3ccc4oc5cccc(-c6nc(-c7ccc8c(c7)oc7ccccc78)nc(-c7cccc8oc9ccccc9c78)n6)c5c4c3)cc21]
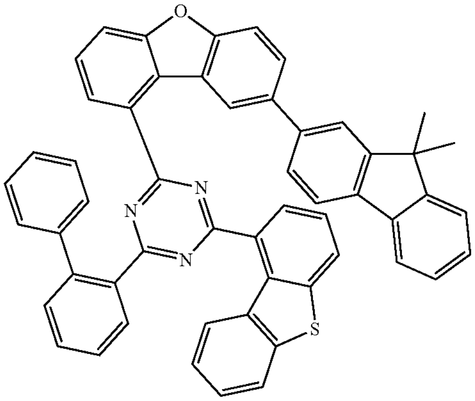 [SMILES: CC1(C)c2ccccc2-c2ccc(-c3ccc4oc5cccc(-c6nc(-c7ccccc7-c7ccccc7)nc(-c7cccc8sc9ccccc9c78)n6)c5c4c3)cc21]

TABLE 1-continued
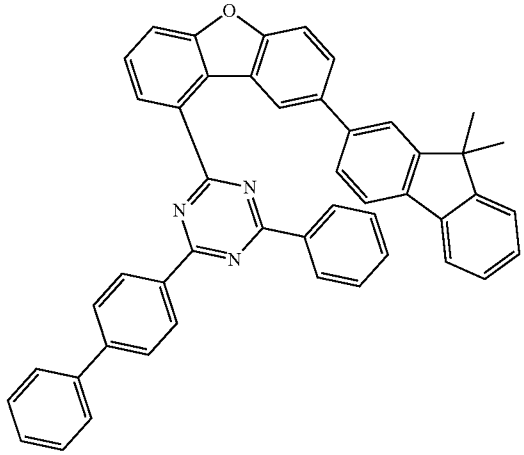 [SMILES: CC1(C)c2ccccc2-c2ccc(-c3ccc4oc5cccc(-c6nc(-c7ccccc7)nc(-c7ccc(-c8ccccc8)cc7)n6)c5c4c3)cc21]
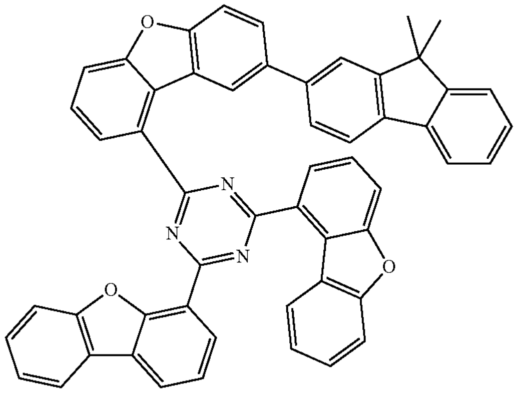 [SMILES: CC1(C)c2ccccc2-c2ccc(-c3ccc4oc5cccc(-c6nc(-c7cccc8c7oc7ccccc78)nc(-c7cccc8oc9ccccc9c78)n6)c5c4c3)cc21]
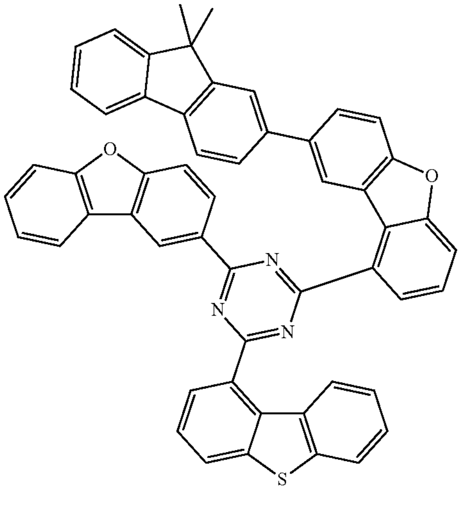 [SMILES: CC1(C)c2ccccc2-c2ccc(-c3ccc4oc5cccc(-c6nc(-c7ccc8oc9ccccc9c8c7)nc(-c7cccc8sc9ccccc9c78)n6)c5c4c3)cc21]

TABLE 1-continued
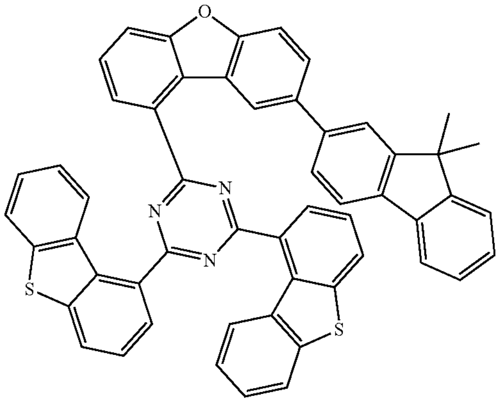 [SMILES: CC1(C)c2ccccc2-c2ccc(-c3ccc4oc5cccc(-c6nc(-c7cccc8sc9ccccc9c78)nc(-c7cccc8sc9ccccc9c78)n6)c5c4c3)cc21]
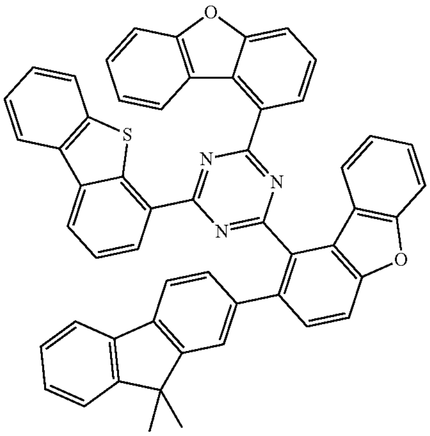 [SMILES: CC1(C)c2ccccc2-c2ccc(-c3ccc4oc5ccccc5c4c3-c3nc(-c4cccc5c4sc4ccccc45)nc(-c4cccc5oc6ccccc6c45)n3)cc21]
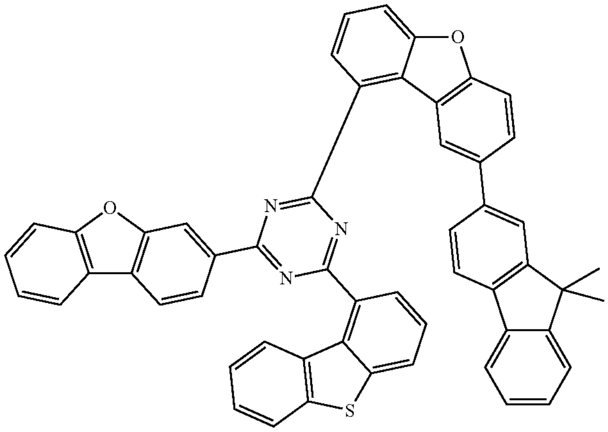 [SMILES: CC1(C)c2ccccc2-c2ccc(-c3ccc4oc5cccc(-c6nc(-c7ccc8c(c7)oc7ccccc78)nc(-c7cccc8sc9ccccc9c78)n6)c5c4c3)cc21]

TABLE 1-continued
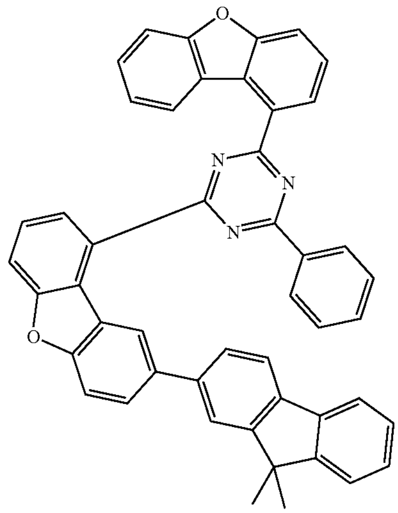 [SMILES: CC1(C)c2ccccc2-c2ccc(-c3ccc4oc5cccc(-c6nc(-c7ccccc7)nc(-c7cccc8oc9ccccc9c78)n6)c5c4c3)cc21]
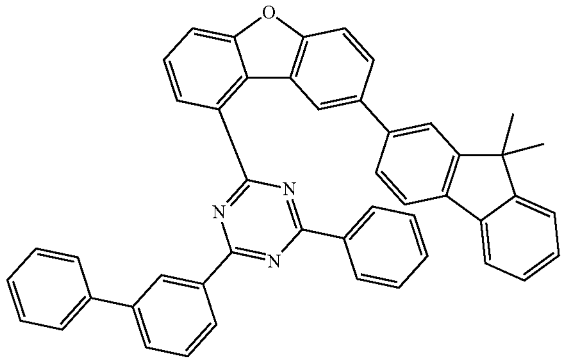 [SMILES: CC1(C)c2ccccc2-c2ccc(-c3ccc4oc5cccc(-c6nc(-c7ccccc7)nc(-c7cccc(-c8ccccc8)c7)n6)c5c4c3)cc21]
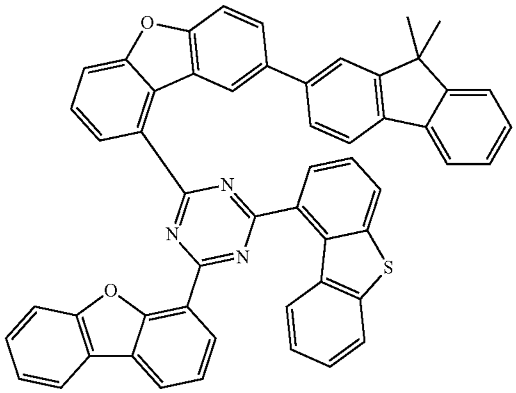 [SMILES: CC1(C)c2ccccc2-c2ccc(-c3ccc4oc5cccc(-c6nc(-c7cccc8c7oc7ccccc78)nc(-c7cccc8sc9ccccc9c78)n6)c5c4c3)cc21]

TABLE 1-continued
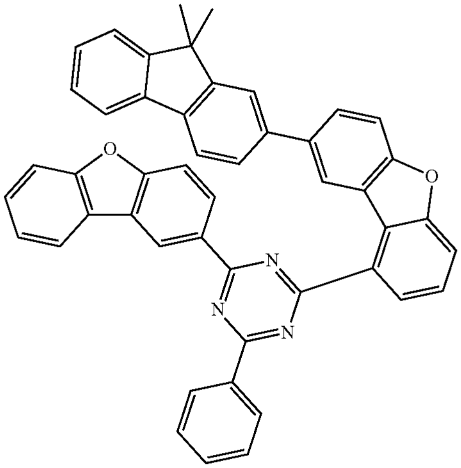 [SMILES: CC1(C)c2ccccc2-c2ccc(-c3ccc4oc5cccc(-c6nc(-c7ccccc7)nc(-c7ccc8oc9ccccc9c8c7)n6)c5c4c3)cc21]
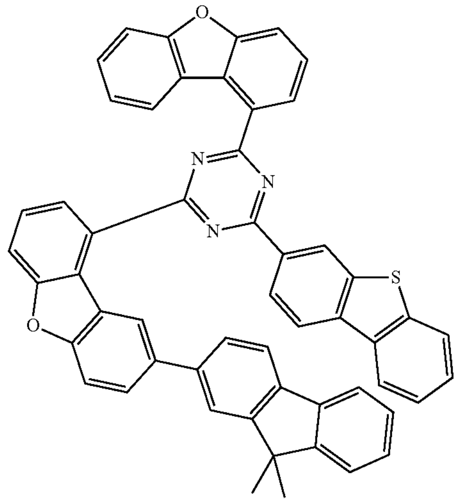 [SMILES: CC1(C)c2ccccc2-c2ccc(-c3ccc4oc5cccc(-c6nc(-c7ccc8c(c7)sc7ccccc78)nc(-c7cccc8oc9ccccc9c78)n6)c5c4c3)cc21]
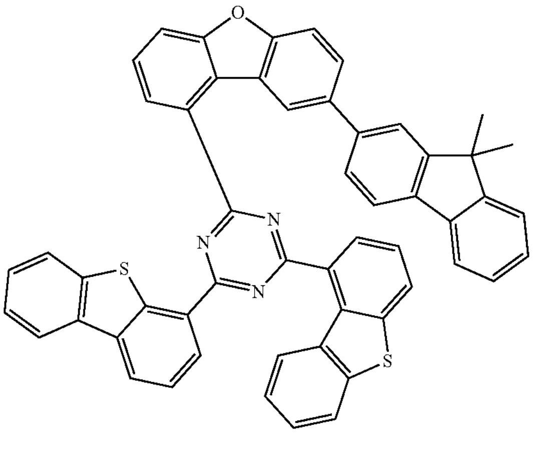 [SMILES: CC1(C)c2ccccc2-c2ccc(-c3ccc4oc5cccc(-c6nc(-c7cccc8c7sc7ccccc78)nc(-c7cccc8sc9ccccc9c78)n6)c5c4c3)cc21]

TABLE 1-continued
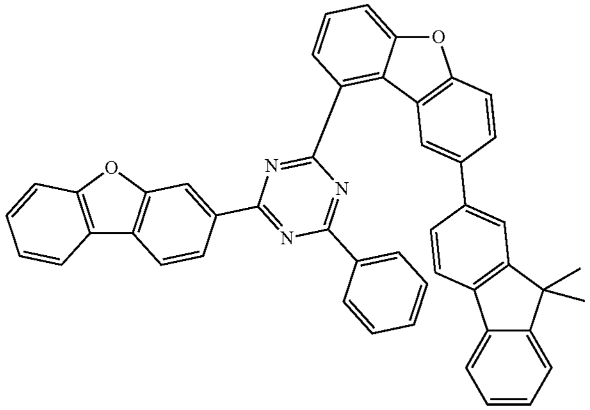 [SMILES: CC1(C)c2ccccc2-c2ccc(-c3ccc4oc5cccc(-c6nc(-c7ccccc7)nc(-c7ccc8c(c7)oc7ccccc78)n6)c5c4c3)cc21]
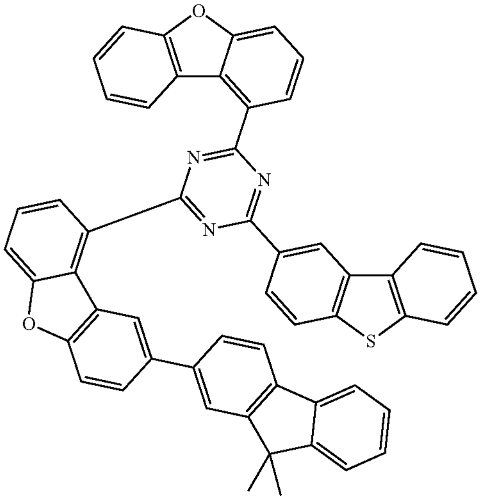 [SMILES: CC1(C)c2ccccc2-c2ccc(-c3ccc4oc5cccc(-c6nc(-c7ccc8sc9ccccc9c8c7)nc(-c7cccc8oc9ccccc9c78)n6)c5c4c3)cc21]
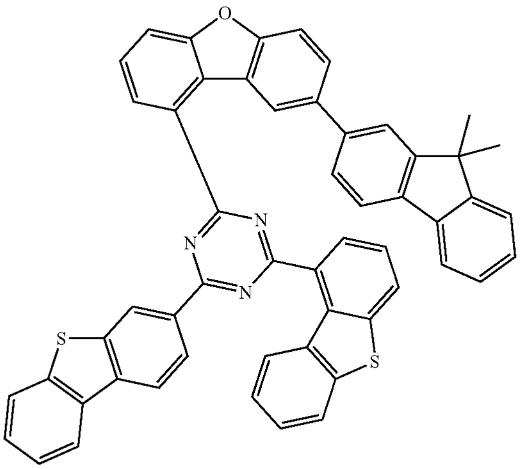 [SMILES: CC1(C)c2ccccc2-c2ccc(-c3ccc4oc5cccc(-c6nc(-c7ccc8c(c7)sc7ccccc78)nc(-c7cccc8sc9ccccc9c78)n6)c5c4c3)cc21]

TABLE 1-continued
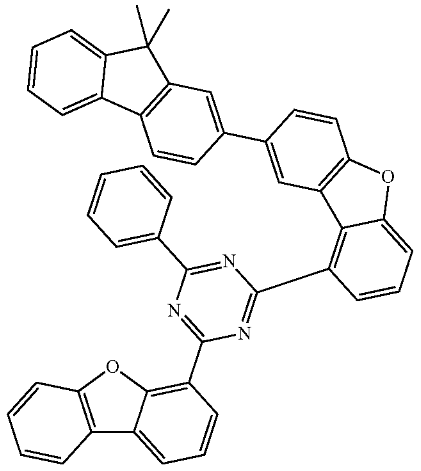 [SMILES: CC1(C)c2ccccc2-c2ccc(-c3ccc4oc5cccc(-c6nc(-c7ccccc7)nc(-c7cccc8c7oc7ccccc78)n6)c5c4c3)cc21]
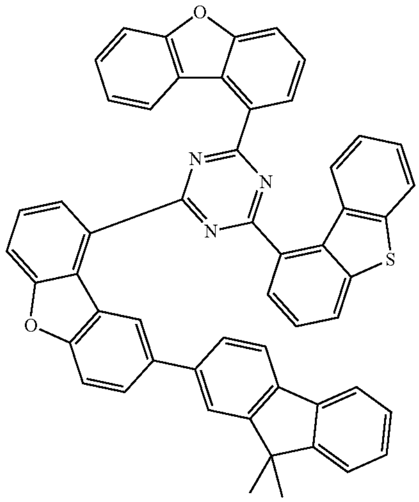 [SMILES: CC1(C)c2ccccc2-c2ccc(-c3ccc4oc5cccc(-c6nc(-c7cccc8oc9ccccc9c78)nc(-c7cccc8sc9ccccc9c78)n6)c5c4c3)cc21]
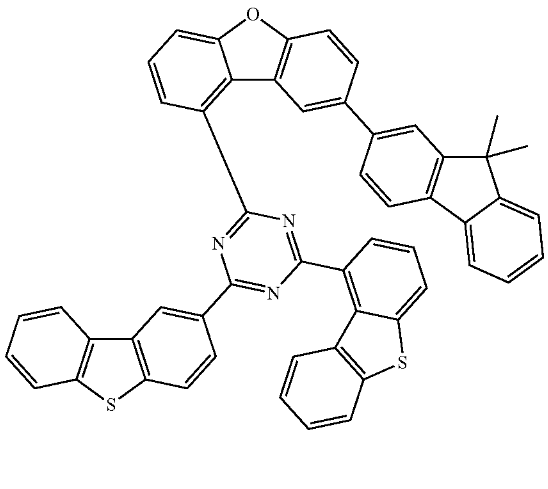 [SMILES: CC1(C)c2ccccc2-c2ccc(-c3ccc4oc5cccc(-c6nc(-c7ccc8sc9ccccc9c8c7)nc(-c7cccc8sc9ccccc9c78)n6)c5c4c3)cc21]

TABLE 1-continued
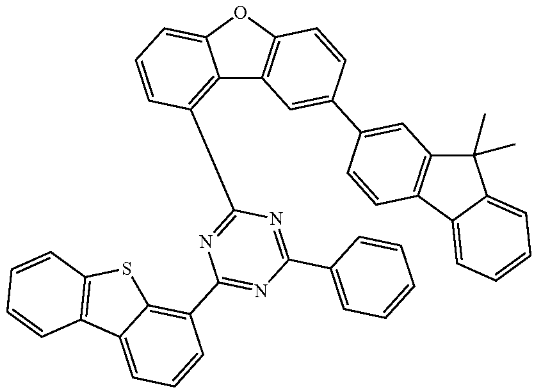 [SMILES: CC1(C)c2ccccc2-c2ccc(-c3ccc4oc5cccc(-c6nc(-c7ccccc7)nc(-c7cccc8c7sc7ccccc78)n6)c5c4c3)cc21]
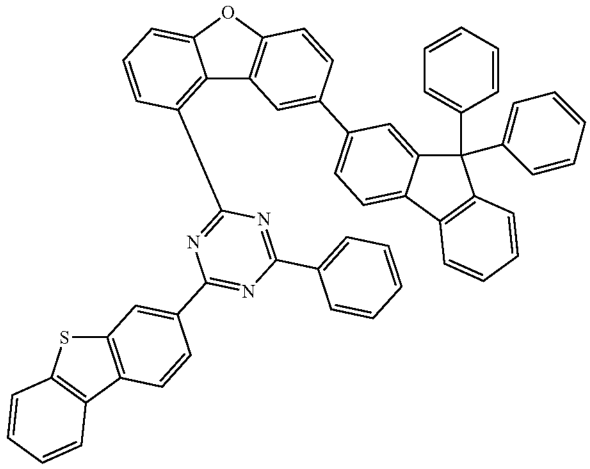 [SMILES: c1ccc(-c2nc(-c3ccc4c(c3)sc3ccccc34)nc(-c3cccc4oc5ccc(-c6ccc7c(c6)C(c6ccccc6)(c6ccccc6)c6ccccc6-7)cc5c34)n2)cc1]
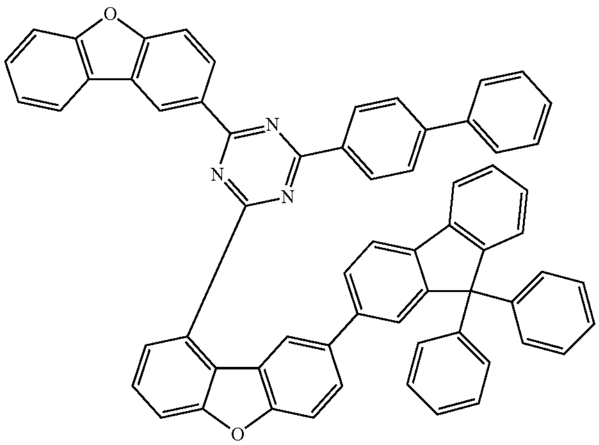 [SMILES: c1ccc(-c2ccc(-c3nc(-c4ccc5oc6ccccc6c5c4)nc(-c4cccc5oc6ccc(-c7ccc8c(c7)C(c7ccccc7)(c7ccccc7)c7ccccc7-8)cc6c45)n3)cc2)cc1]

TABLE 1-continued
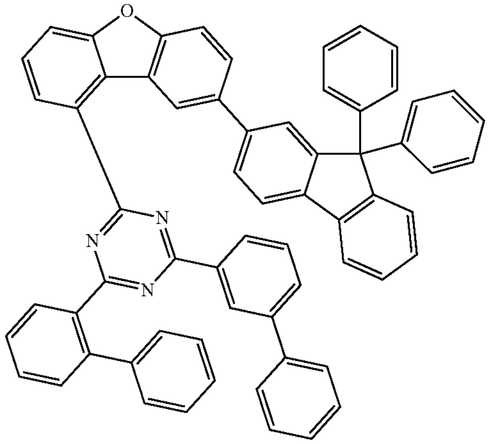 [SMILES: c1ccc(-c2cccc(-c3nc(-c4ccccc4-c4ccccc4)nc(-c4cccc5oc6ccc(-c7ccc8c(c7)C(c7ccccc7)(c7ccccc7)c7ccccc7-8)cc6c45)n3)c2)cc1]
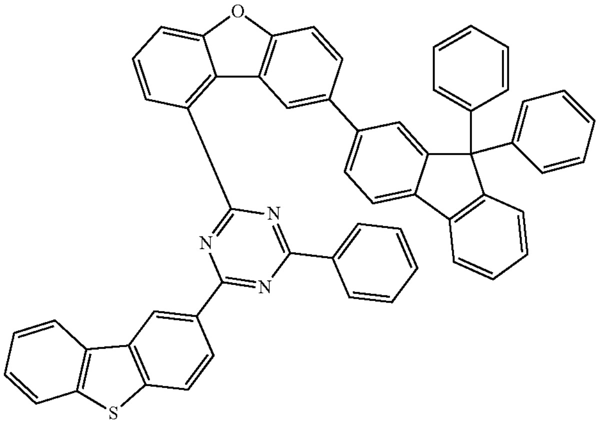 [SMILES: c1ccc(-c2nc(-c3ccc4sc5ccccc5c4c3)nc(-c3cccc4oc5ccc(-c6ccc7c(c6)C(c6ccccc6)(c6ccccc6)c6ccccc6-7)cc5c34)n2)cc1]
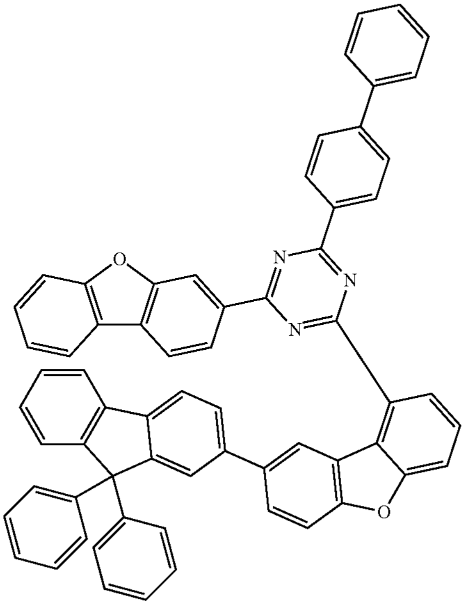 [SMILES: c1ccc(-c2ccc(-c3nc(-c4ccc5c(c4)oc4ccccc45)nc(-c4cccc5oc6ccc(-c7ccc8c(c7)C(c7ccccc7)(c7ccccc7)c7ccccc7-8)cc6c45)n3)cc2)cc1]

TABLE 1-continued
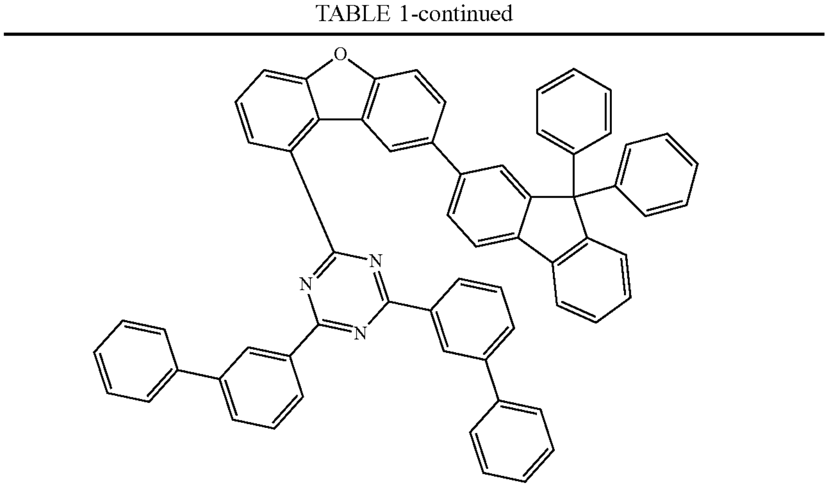
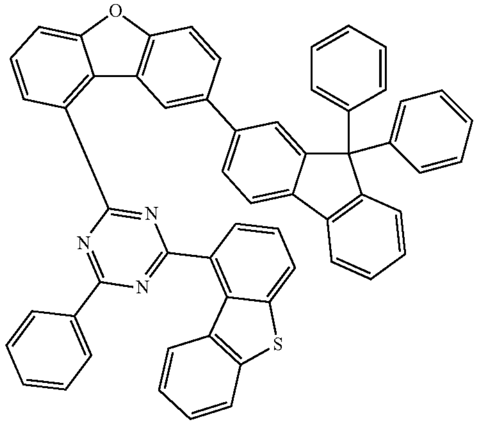 [SMILES: c1ccc(-c2nc(-c3cccc4oc5ccc(-c6ccc7c(c6)C(c6ccccc6)(c6ccccc6)c6ccccc6-7)cc5c34)nc(-c3cccc4sc5ccccc5c34)n2)cc1]
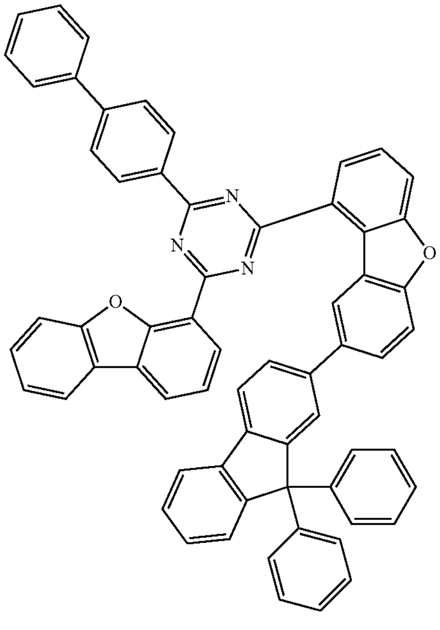 [SMILES: c1ccc(-c2ccc(-c3nc(-c4cccc5c4oc4ccccc45)nc(-c4cccc5oc6ccc(-c7ccc8c(c7)C(c7ccccc7)(c7ccccc7)c7ccccc7-8)cc6c45)n3)cc2)cc1]

TABLE 1-continued
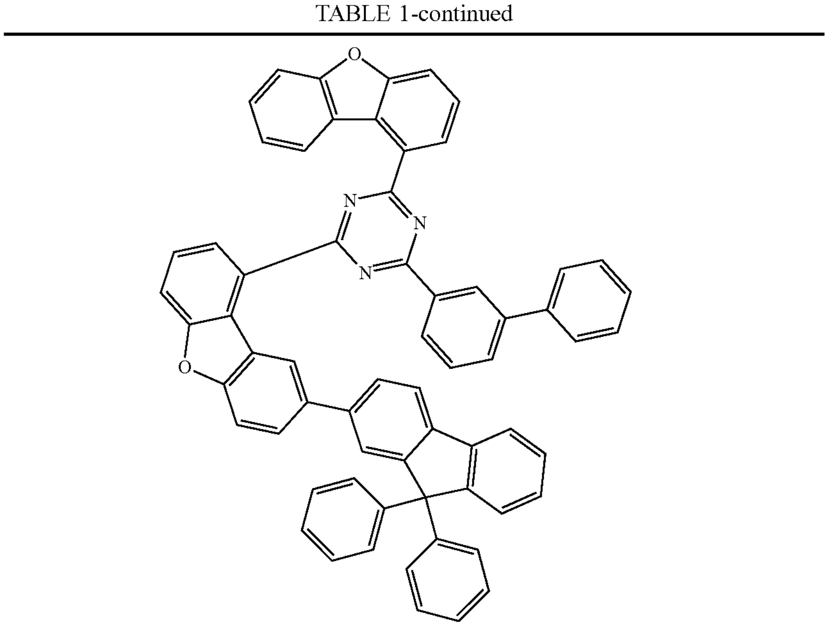
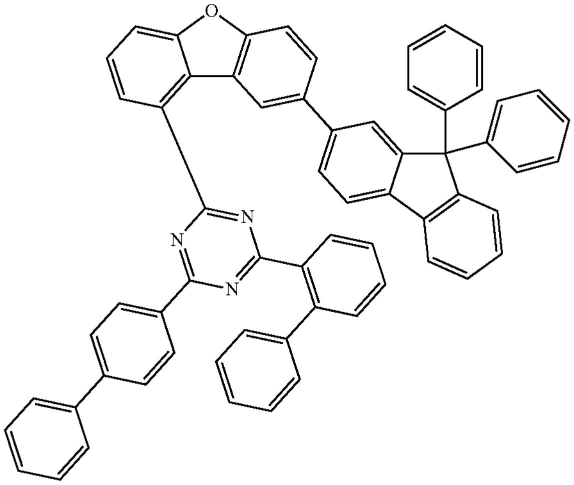 [SMILES: c1ccc(-c2ccc(-c3nc(-c4ccccc4-c4ccccc4)nc(-c4cccc5oc6ccc(-c7ccc8c(c7)C(c7ccccc7)(c7ccccc7)c7ccccc7-8)cc6c45)n3)cc2)cc1]
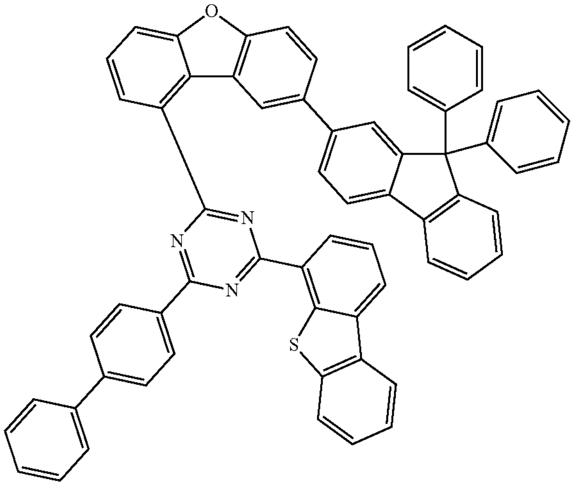 [SMILES: c1ccc(-c2ccc(-c3nc(-c4cccc5c4sc4ccccc45)nc(-c4cccc5oc6ccc(-c7ccc8c(c7)C(c7ccccc7)(c7ccccc7)c7ccccc7-8)cc6c45)n3)cc2)cc1]

TABLE 1-continued
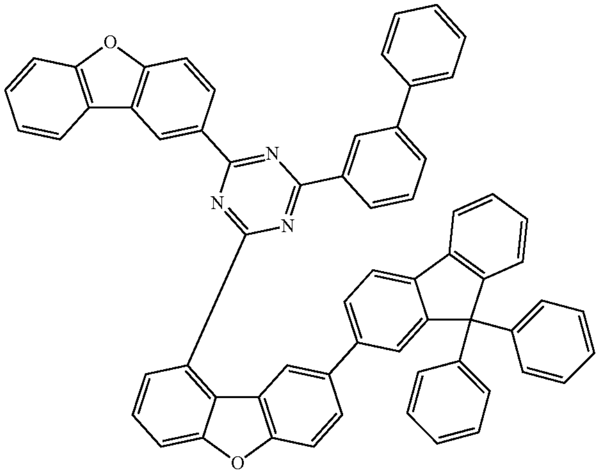 [SMILES: c1ccc(-c2cccc(-c3nc(-c4ccc5oc6ccccc6c5c4)nc(-c4cccc5oc6ccc(-c7ccc8c(c7)C(c7ccccc7)(c7ccccc7)c7ccccc7-8)cc6c45)n3)c2)cc1]
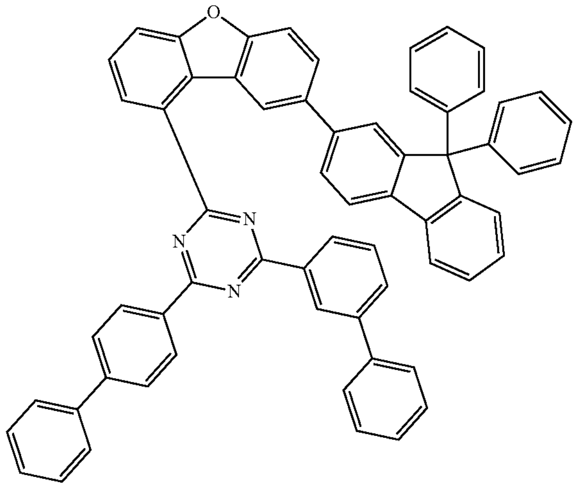 [SMILES: c1ccc(-c2ccc(-c3nc(-c4cccc(-c5ccccc5)c4)nc(-c4cccc5oc6ccc(-c7ccc8c(c7)C(c7ccccc7)(c7ccccc7)c7ccccc7-8)cc6c45)n3)cc2)cc1]
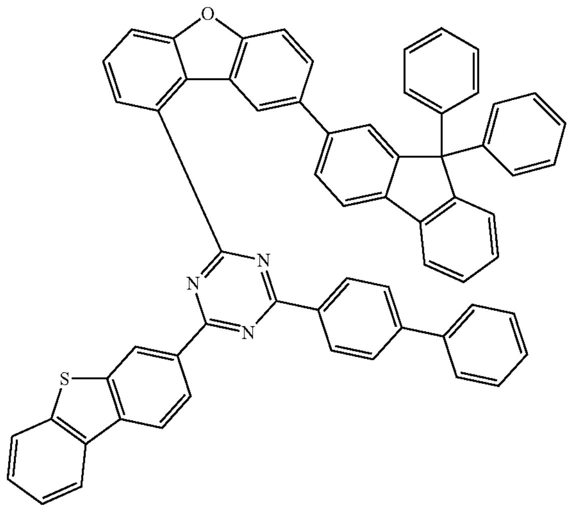 [SMILES: c1ccc(-c2ccc(-c3nc(-c4ccc5c(c4)sc4ccccc45)nc(-c4cccc5oc6ccc(-c7ccc8c(c7)C(c7ccccc7)(c7ccccc7)c7ccccc7-8)cc6c45)n3)cc2)cc1]

TABLE 1-continued
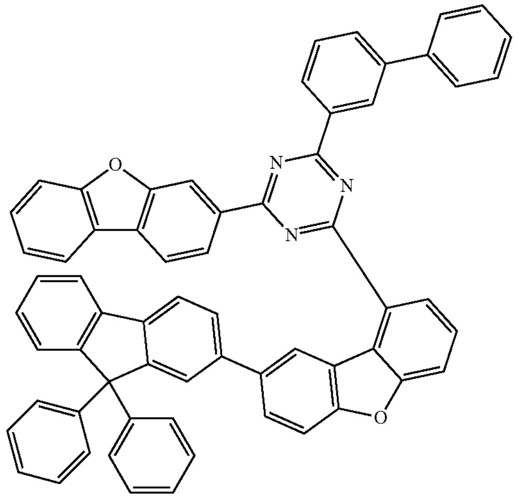 [SMILES: c1ccc(-c2cccc(-c3nc(-c4ccc5c(c4)oc4ccccc45)nc(-c4cccc5oc6ccc(-c7ccc8c(c7)C(c7ccccc7)(c7ccccc7)c7ccccc7-8)cc6c45)n3)c2)cc1]
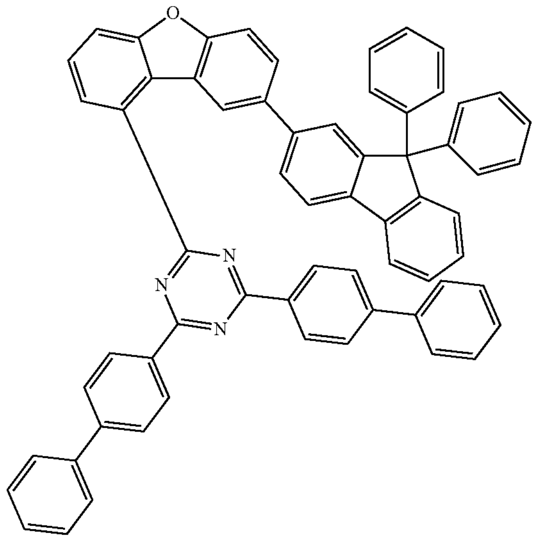 [SMILES: c1ccc(-c2ccc(-c3nc(-c4ccc(-c5ccccc5)cc4)nc(-c4cccc5oc6ccc(-c7ccc8c(c7)C(c7ccccc7)(c7ccccc7)c7ccccc7-8)cc6c45)n3)cc2)cc1]
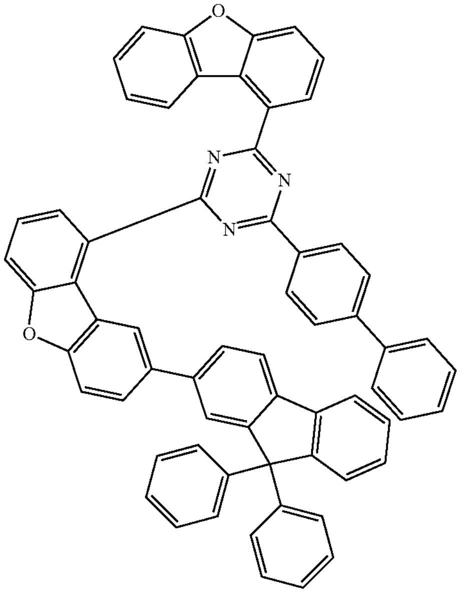 [SMILES: c1ccc(-c2ccc(-c3nc(-c4cccc5oc6ccccc6c45)nc(-c4cccc5oc6ccc(-c7ccc8c(c7)C(c7ccccc7)(c7ccccc7)c7ccccc7-8)cc6c45)n3)cc2)cc1]

TABLE 1-continued
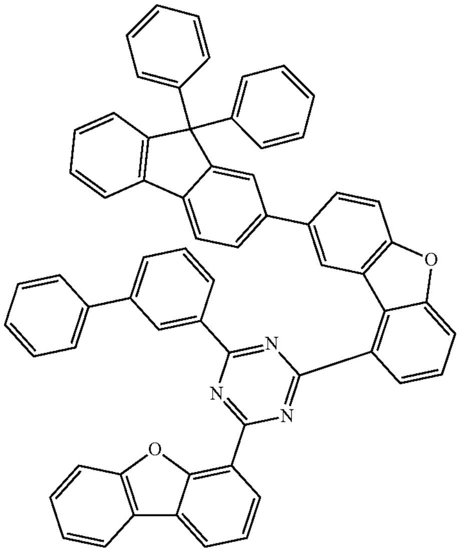 [SMILES: c1ccc(-c2cccc(-c3nc(-c4cccc5c4oc4ccccc45)nc(-c4cccc5oc6ccc(-c7ccc8c(c7)C(c7ccccc7)(c7ccccc7)c7ccccc7-8)cc6c45)n3)c2)cc1]
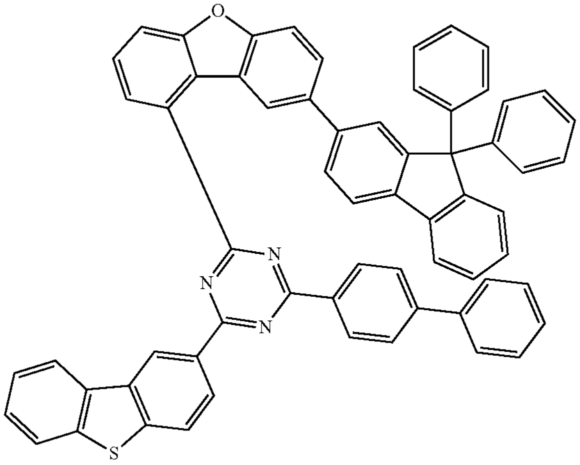 [SMILES: c1ccc(-c2ccc(-c3nc(-c4ccc5sc6ccccc6c5c4)nc(-c4cccc5oc6ccc(-c7ccc8c(c7)C(c7ccccc7)(c7ccccc7)c7ccccc7-8)cc6c45)n3)cc2)cc1]
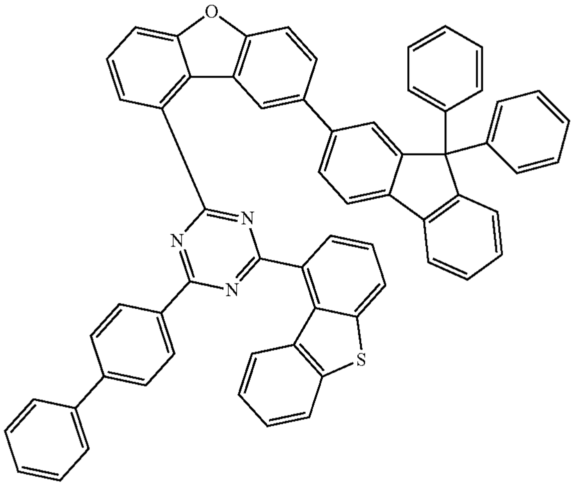 [SMILES: c1ccc(-c2ccc(-c3nc(-c4cccc5oc6ccc(-c7ccc8c(c7)C(c7ccccc7)(c7ccccc7)c7ccccc7-8)cc6c45)nc(-c4cccc5sc6ccccc6c45)n3)cc2)cc1]

TABLE 1-continued
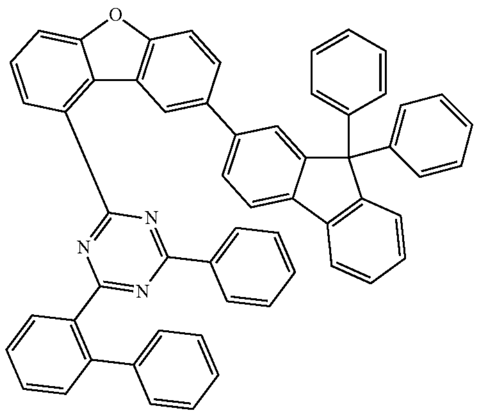 [SMILES: c1ccc(-c2nc(-c3ccccc3-c3ccccc3)nc(-c3cccc4oc5ccc(-c6ccc7c(c6)C(c6ccccc6)(c6ccccc6)c6ccccc6-7)cc5c34)n2)cc1]
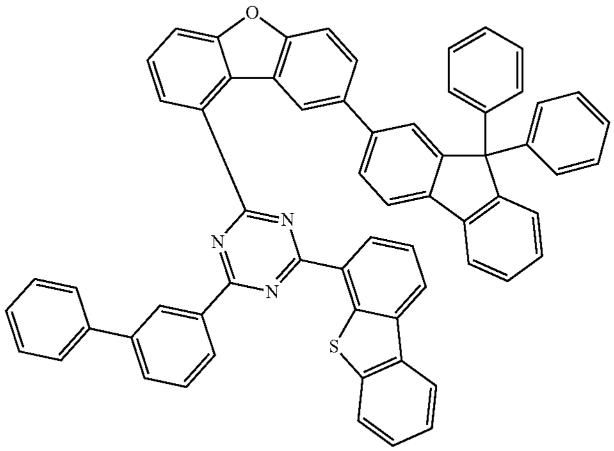 [SMILES: c1ccc(-c2cccc(-c3nc(-c4cccc5c4sc4ccccc45)nc(-c4cccc5oc6ccc(-c7ccc8c(c7)C(c7ccccc7)(c7ccccc7)c7ccccc7-8)cc6c45)n3)c2)cc1]
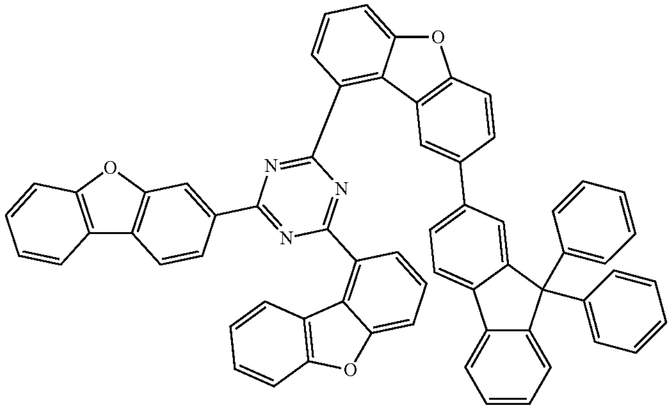 [SMILES: c1ccc(C2(c3ccccc3)c3ccccc3-c3ccc(-c4ccc5oc6cccc(-c7nc(-c8ccc9c(c8)oc8ccccc89)nc(-c8cccc9oc%10ccccc%10c89)n7)c6c5c4)cc32)cc1]

TABLE 1-continued
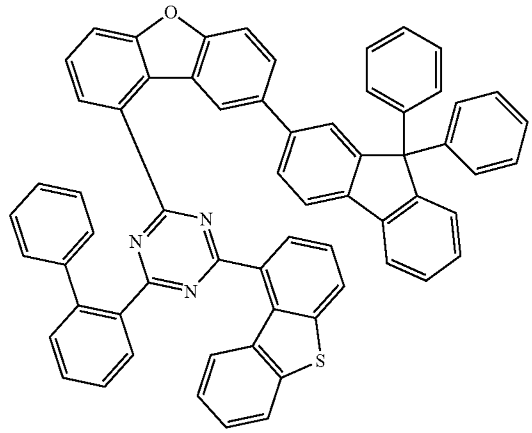 [SMILES: c1ccc(-c2ccccc2-c2nc(-c3cccc4oc5ccc(-c6ccc7c(c6)C(c6ccccc6)(c6ccccc6)c6ccccc6-7)cc5c34)nc(-c3cccc4sc5ccccc5c34)n2)cc1]
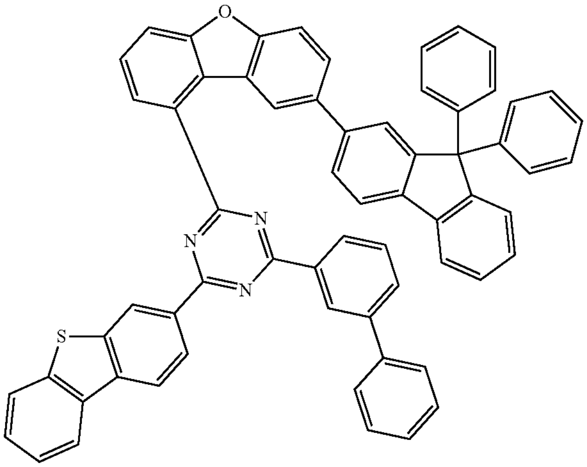 [SMILES: c1ccc(-c2cccc(-c3nc(-c4ccc5c(c4)sc4ccccc45)nc(-c4cccc5oc6ccc(-c7ccc8c(c7)C(c7ccccc7)(c7ccccc7)c7ccccc7-8)cc6c45)n3)c2)cc1]
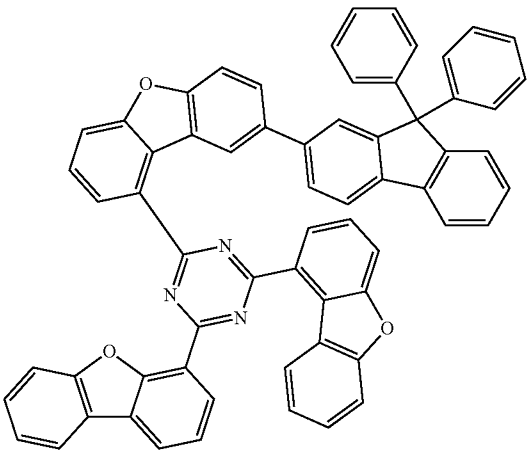 [SMILES: c1ccc(C2(c3ccccc3)c3ccccc3-c3ccc(-c4ccc5oc6cccc(-c7nc(-c8cccc9c8oc8ccccc89)nc(-c8cccc9oc%10ccccc%10c89)n7)c6c5c4)cc32)cc1]

TABLE 1-continued
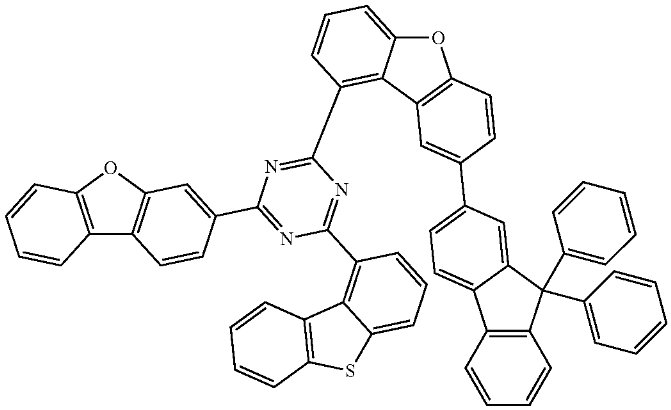 [SMILES: c1ccc(C2(c3ccccc3)c3ccccc3-c3ccc(-c4ccc5oc6cccc(-c7nc(-c8ccc9c(c8)oc8ccccc89)nc(-c8cccc9sc%10ccccc%10c89)n7)c6c5c4)cc32)cc1]
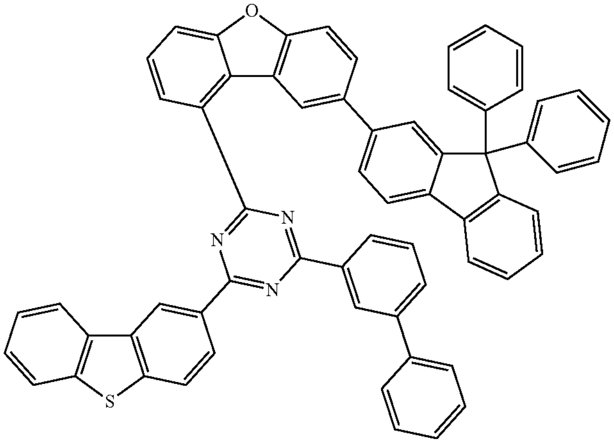 [SMILES: c1ccc(-c2cccc(-c3nc(-c4ccc5sc6ccccc6c5c4)nc(-c4cccc5oc6ccc(-c7ccc8c(c7)C(c7ccccc7)(c7ccccc7)c7ccccc7-8)cc6c45)n3)c2)cc1]
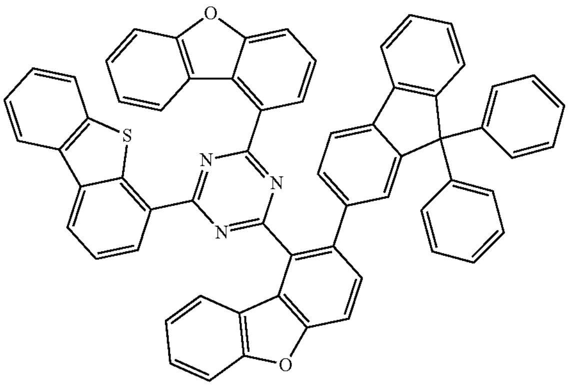 [SMILES: c1ccc(C2(c3ccccc3)c3ccccc3-c3ccc(-c4ccc5oc6ccccc6c5c4-c4nc(-c5cccc6c5sc5ccccc56)nc(-c5cccc6oc7ccccc7c56)n4)cc32)cc1]

TABLE 1-continued
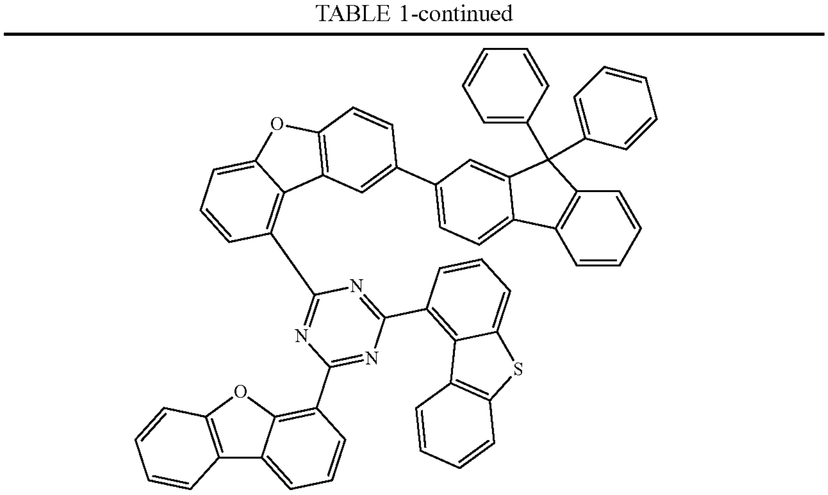
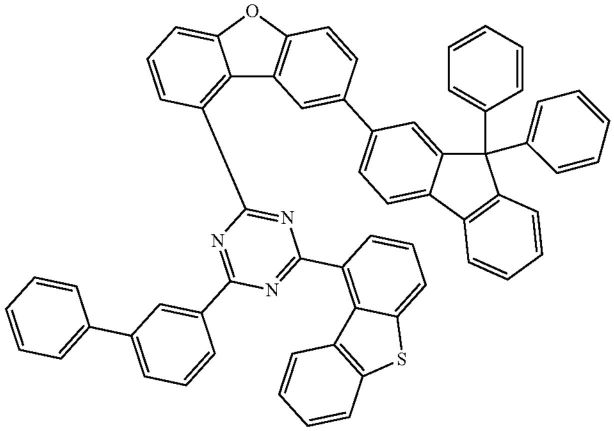 [SMILES: c1ccc(-c2cccc(-c3nc(-c4cccc5oc6ccc(-c7ccc8c(c7)C(c7ccccc7)(c7ccccc7)c7ccccc7-8)cc6c45)nc(-c4cccc5sc6ccccc6c45)n3)c2)cc1]
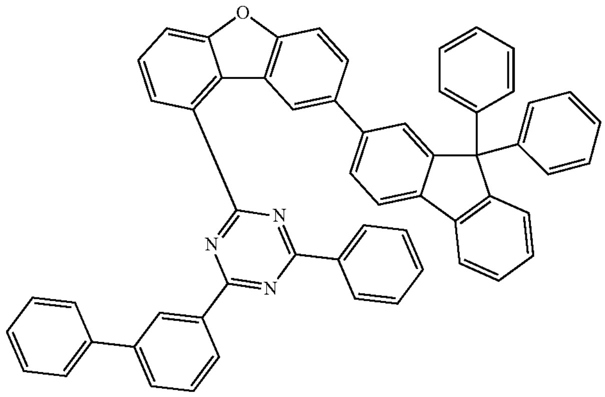 [SMILES: c1ccc(-c2cccc(-c3nc(-c4ccccc4)nc(-c4cccc5oc6ccc(-c7ccc8c(c7)C(c7ccccc7)(c7ccccc7)c7ccccc7-8)cc6c45)n3)c2)cc1]

TABLE 1-continued
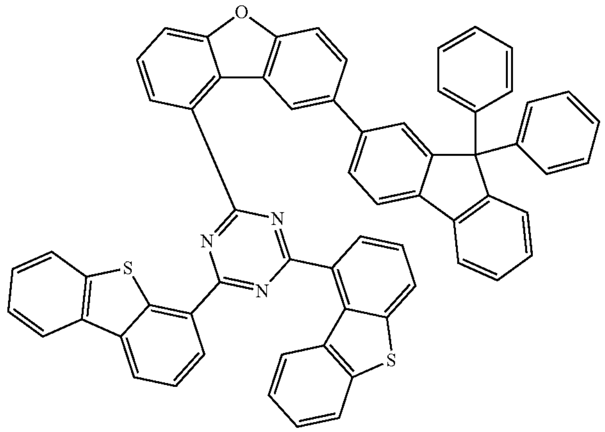 [SMILES: c1ccc(C2(c3ccccc3)c3ccccc3-c3ccc(-c4ccc5oc6cccc(-c7nc(-c8cccc9c8sc8ccccc89)nc(-c8cccc9sc%10ccccc%10c89)n7)c6c5c4)cc32)cc1]
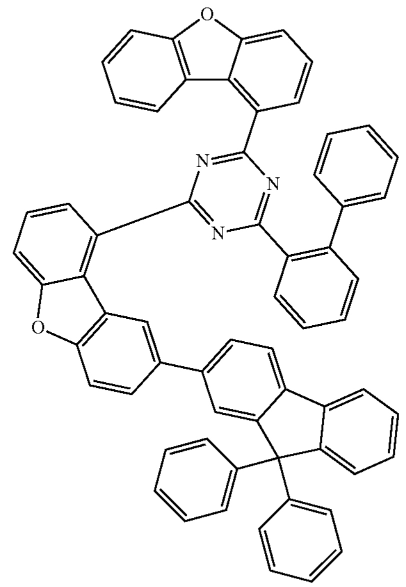 [SMILES: c1ccc(-c2ccccc2-c2nc(-c3cccc4oc5ccccc5c34)nc(-c3cccc4oc5ccc(-c6ccc7c(c6)C(c6ccccc6)(c6ccccc6)c6ccccc6-7)cc5c34)n2)cc1]
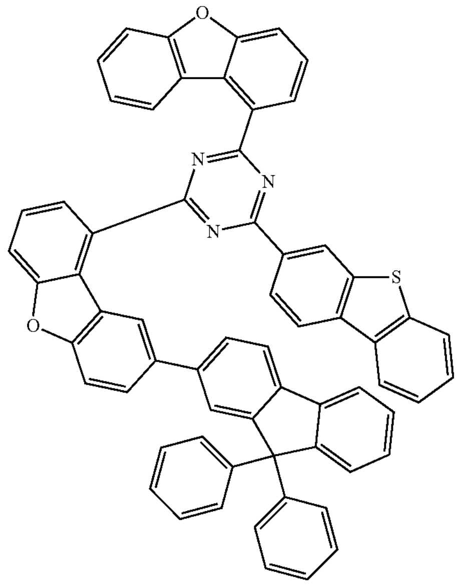 [SMILES: c1ccc(C2(c3ccccc3)c3ccccc3-c3ccc(-c4ccc5oc6cccc(-c7nc(-c8ccc9c(c8)sc8ccccc89)nc(-c8cccc9oc%10ccccc%10c89)n7)c6c5c4)cc32)cc1]

TABLE 1-continued
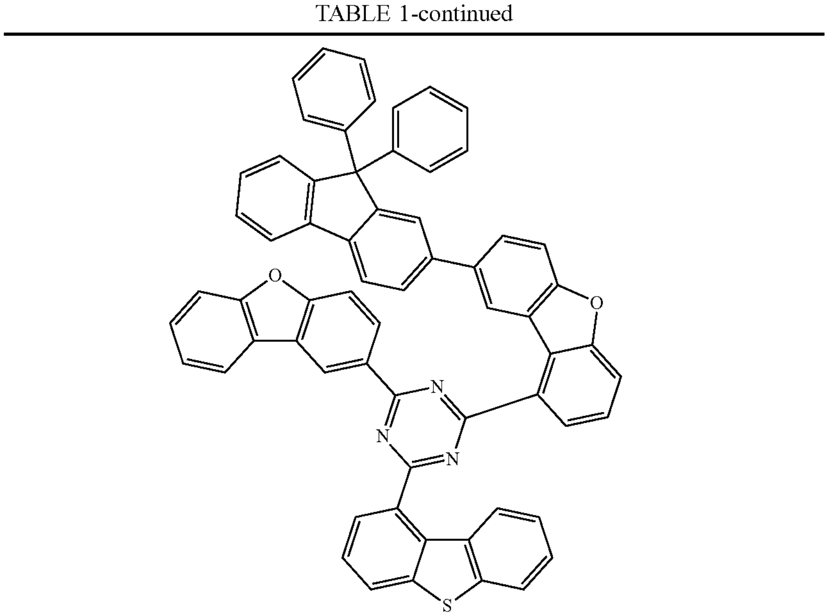
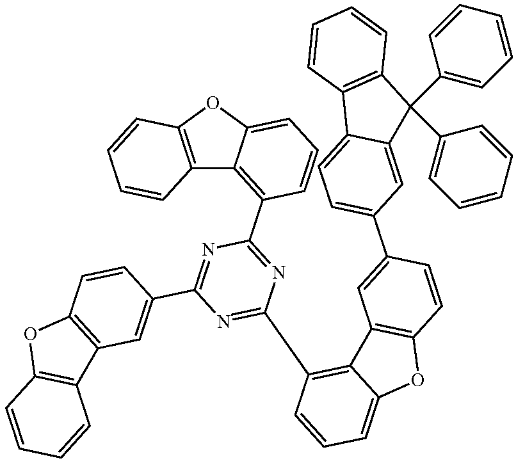 [SMILES: c1ccc(C2(c3ccccc3)c3ccccc3-c3ccc(-c4ccc5oc6cccc(-c7nc(-c8ccc9oc%10ccccc%10c9c8)nc(-c8cccc9oc%10ccccc%10c89)n7)c6c5c4)cc32)cc1]
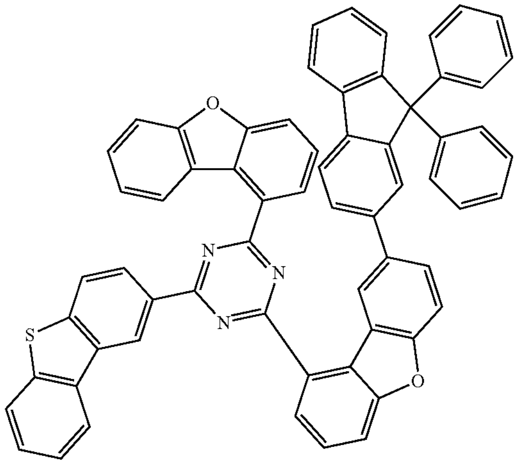 [SMILES: c1ccc(C2(c3ccccc3)c3ccccc3-c3ccc(-c4ccc5oc6cccc(-c7nc(-c8ccc9sc%10ccccc%10c9c8)nc(-c8cccc9oc%10ccccc%10c89)n7)c6c5c4)cc32)cc1]

TABLE 1-continued
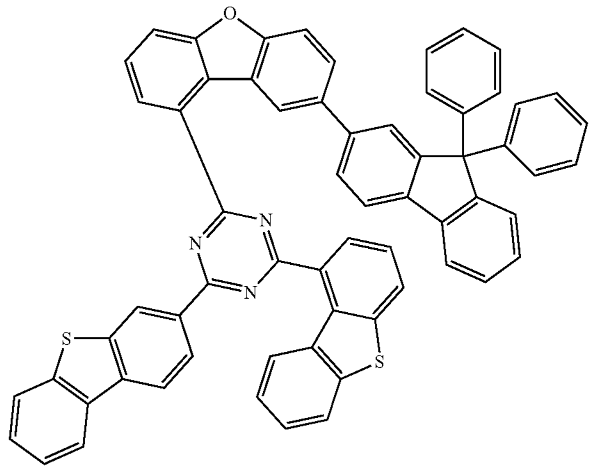 [SMILES: c1ccc(C2(c3ccccc3)c3ccccc3-c3ccc(-c4ccc5oc6cccc(-c7nc(-c8ccc9c(c8)sc8ccccc89)nc(-c8cccc9sc%10ccccc%10c89)n7)c6c5c4)cc32)cc1]
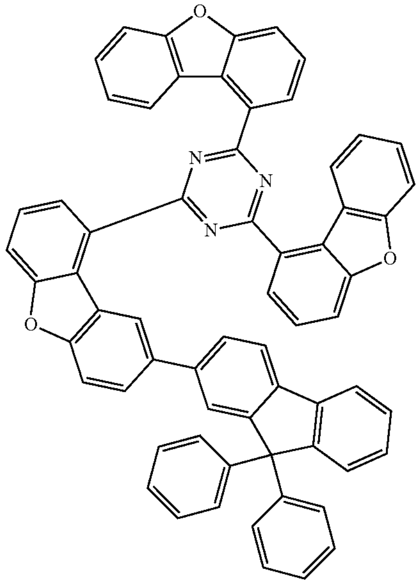 [SMILES: c1ccc(C2(c3ccccc3)c3ccccc3-c3ccc(-c4ccc5oc6cccc(-c7nc(-c8cccc9oc%10ccccc%10c89)nc(-c8cccc9oc%10ccccc%10c89)n7)c6c5c4)cc32)cc1]
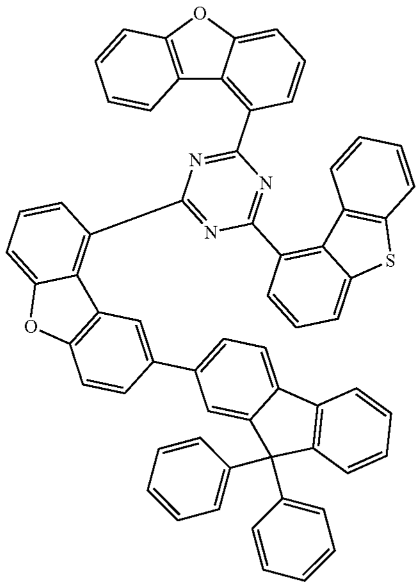 [SMILES: c1ccc(C2(c3ccccc3)c3ccccc3-c3ccc(-c4ccc5oc6cccc(-c7nc(-c8cccc9oc%10ccccc%10c89)nc(-c8cccc9sc%10ccccc%10c89)n7)c6c5c4)cc32)cc1]

TABLE 1-continued
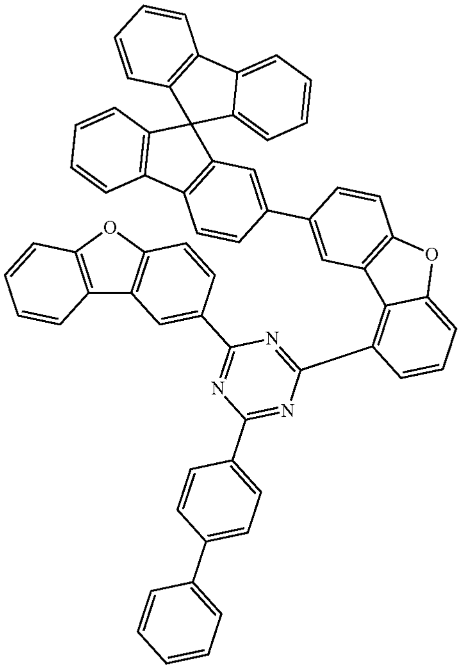 [SMILES: c1ccc(-c2ccc(-c3nc(-c4ccc5oc6ccccc6c5c4)nc(-c4cccc5oc6ccc(-c7ccc8c(c7)C7(c9ccccc9-c9ccccc97)c7ccccc7-8)cc6c45)n3)cc2)cc1]
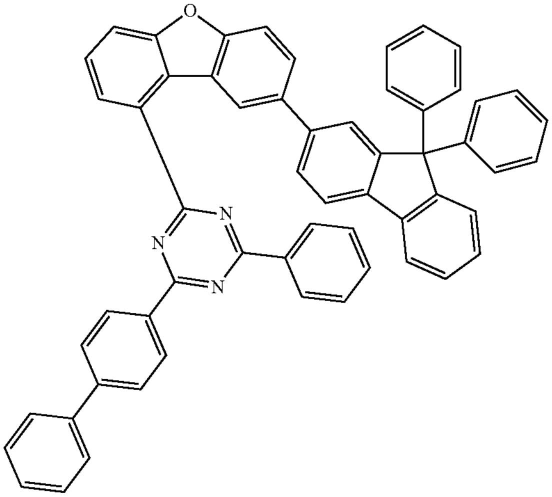 [SMILES: c1ccc(-c2ccc(-c3nc(-c4ccccc4)nc(-c4cccc5oc6ccc(-c7ccc8c(c7)C(c7ccccc7)(c7ccccc7)c7ccccc7-8)cc6c45)n3)cc2)cc1]
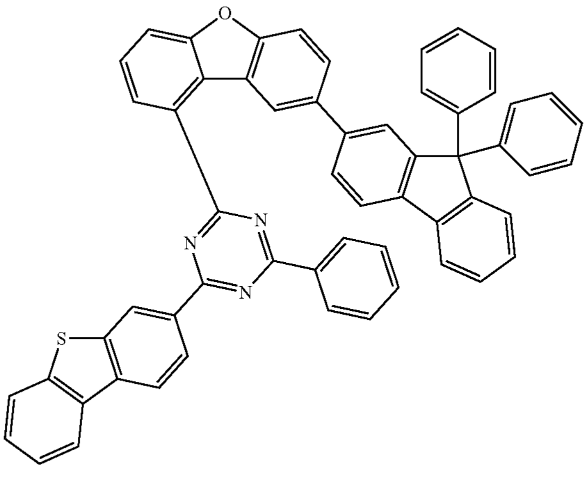 [SMILES: c1ccc(-c2nc(-c3ccc4c(c3)sc3ccccc34)nc(-c3cccc4oc5ccc(-c6ccc7c(c6)C(c6ccccc6)(c6ccccc6)c6ccccc6-7)cc5c34)n2)cc1]

TABLE 1-continued
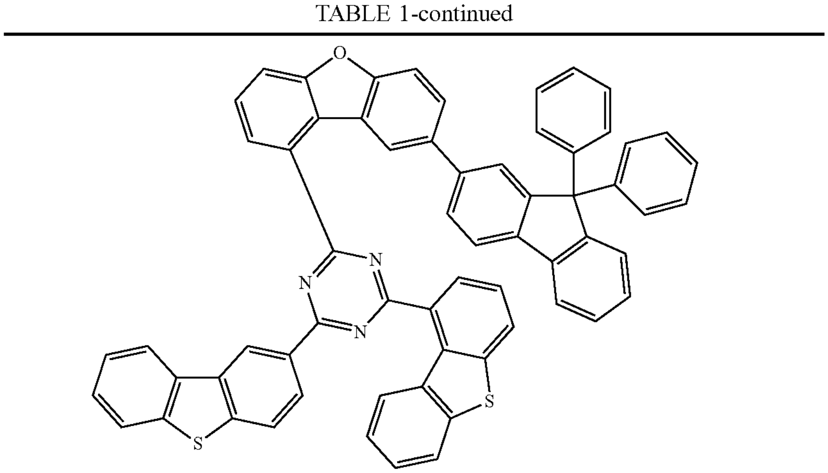
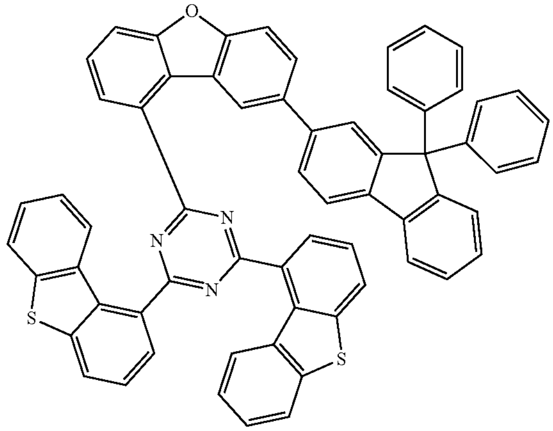 [SMILES: c1ccc(C2(c3ccccc3)c3ccccc3-c3ccc(-c4ccc5oc6cccc(-c7nc(-c8cccc9sc%10ccccc%10c89)nc(-c8cccc9sc%10ccccc%10c89)n7)c6c5c4)cc32)cc1]
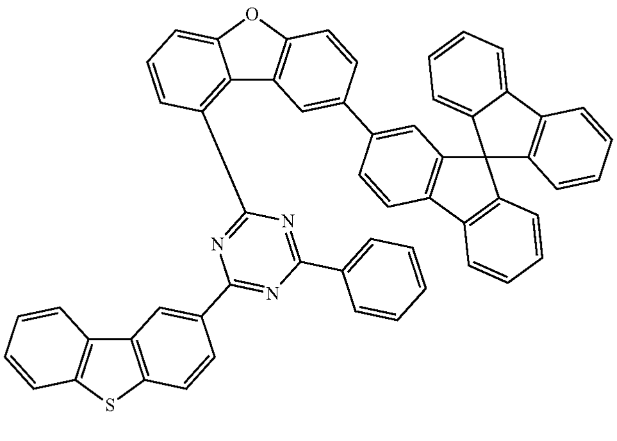 [SMILES: c1ccc(-c2nc(-c3ccc4sc5ccccc5c4c3)nc(-c3cccc4oc5ccc(-c6ccc7c(c6)C6(c8ccccc8-c8ccccc86)c6ccccc6-7)cc5c34)n2)cc1]

TABLE 1-continued
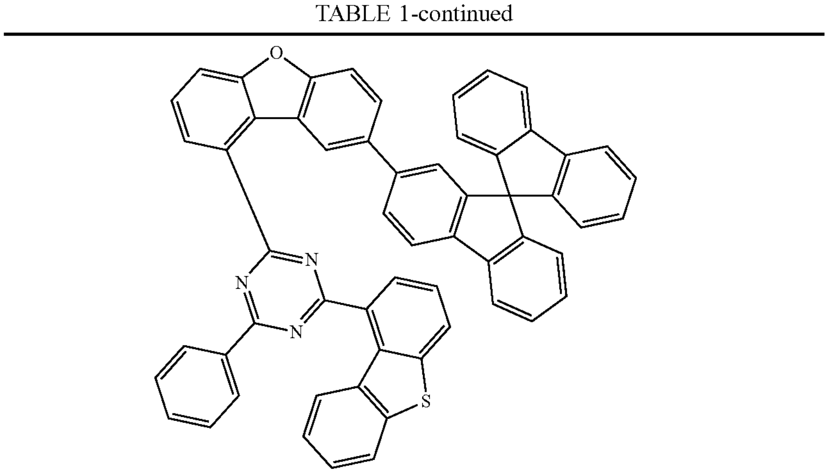
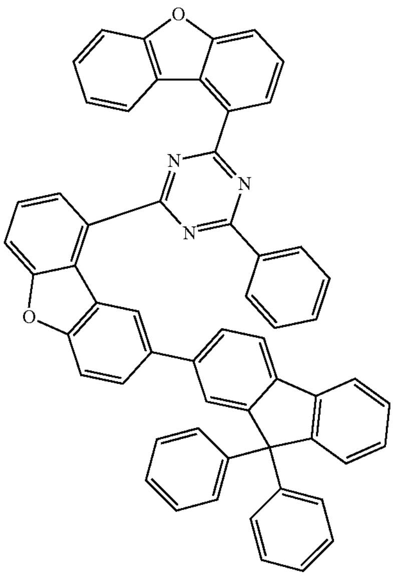 [SMILES: c1ccc(-c2nc(-c3cccc4oc5ccccc5c34)nc(-c3cccc4oc5ccc(-c6ccc7c(c6)C(c6ccccc6)(c6ccccc6)c6ccccc6-7)cc5c34)n2)cc1]
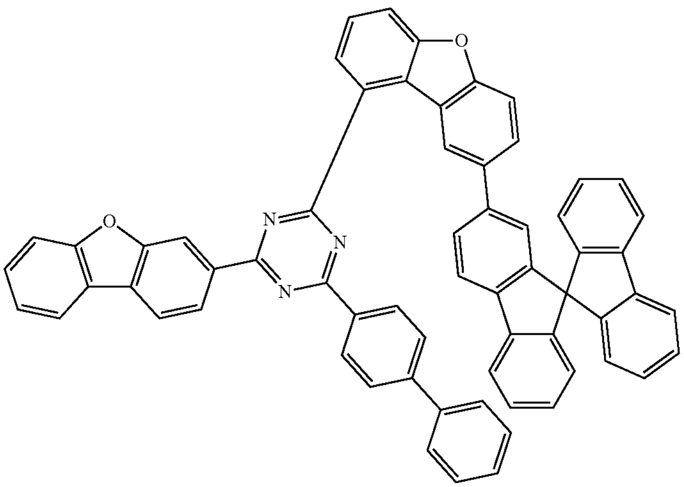 [SMILES: c1ccc(-c2ccc(-c3nc(-c4ccc5c(c4)oc4ccccc45)nc(-c4cccc5oc6ccc(-c7ccc8c(c7)C7(c9ccccc9-c9ccccc97)c7ccccc7-8)cc6c45)n3)cc2)cc1]

TABLE 1-continued
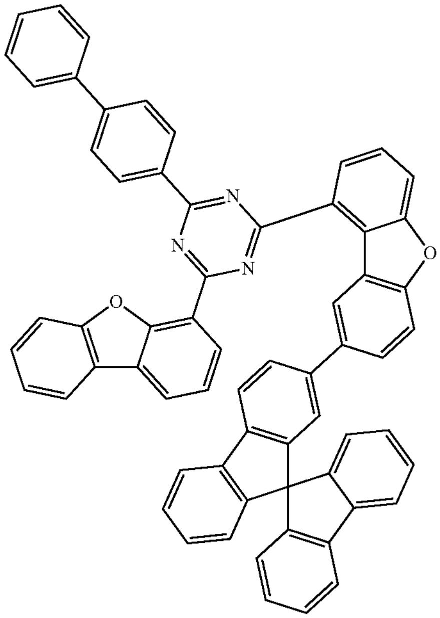 [SMILES: c1ccc(-c2ccc(-c3nc(-c4cccc5c4oc4ccccc45)nc(-c4cccc5oc6ccc(-c7ccc8c(c7)C7(c9ccccc9-c9ccccc97)c7ccccc7-8)cc6c45)n3)cc2)cc1]
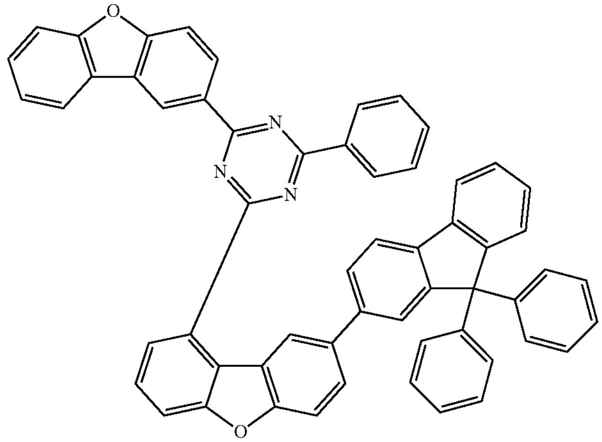 [SMILES: c1ccc(-c2nc(-c3ccc4oc5ccccc5c4c3)nc(-c3cccc4oc5ccc(-c6ccc7c(c6)C(c6ccccc6)(c6ccccc6)c6ccccc6-7)cc5c34)n2)cc1]
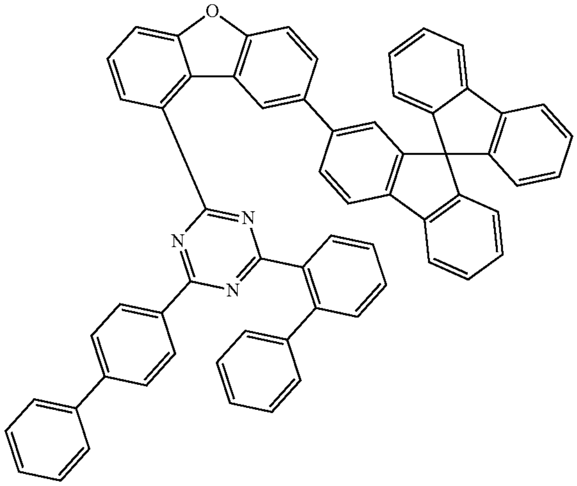 [SMILES: c1ccc(-c2ccc(-c3nc(-c4ccccc4-c4ccccc4)nc(-c4cccc5oc6ccc(-c7ccc8c(c7)C7(c9ccccc9-c9ccccc97)c7ccccc7-8)cc6c45)n3)cc2)cc1]

TABLE 1-continued
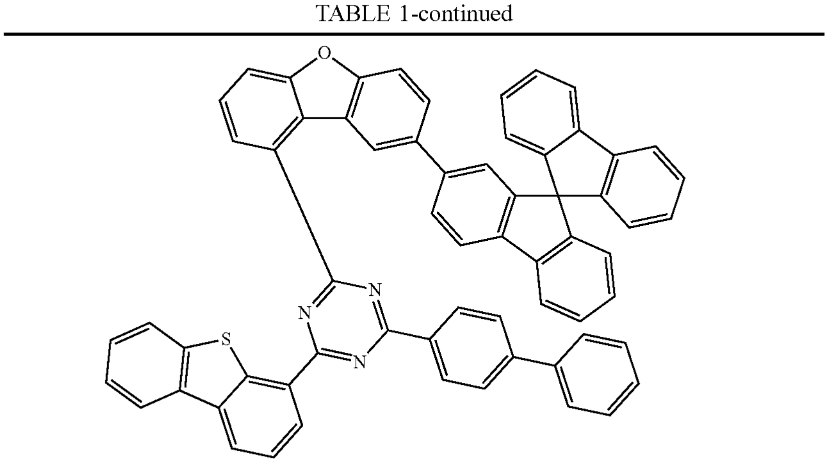
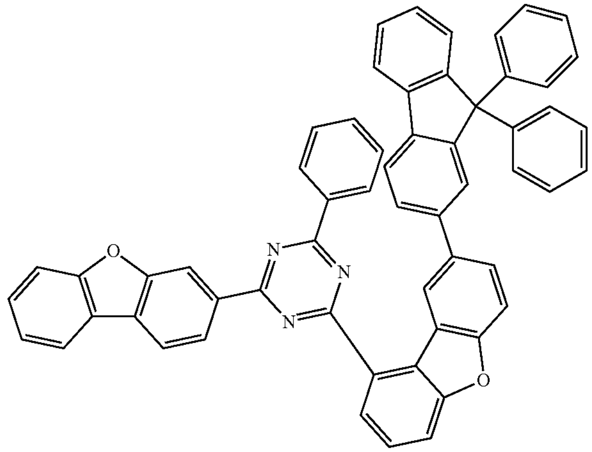 [SMILES: c1ccc(-c2nc(-c3ccc4c(c3)oc3ccccc34)nc(-c3cccc4oc5ccc(-c6ccc7c(c6)C(c6ccccc6)(c6ccccc6)c6ccccc6-7)cc5c34)n2)cc1]
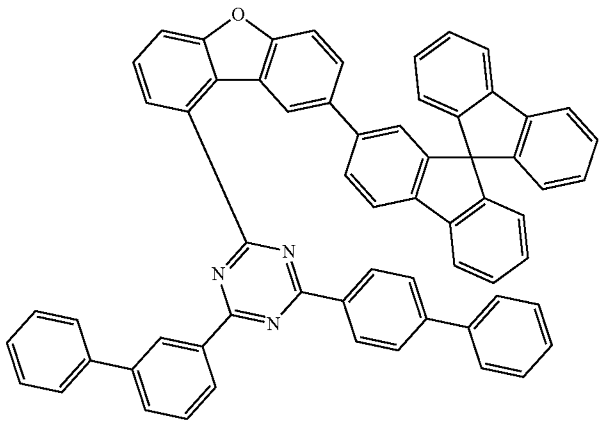 [SMILES: c1ccc(-c2ccc(-c3nc(-c4cccc(-c5ccccc5)c4)nc(-c4cccc5oc6ccc(-c7ccc8c(c7)C7(c9ccccc9-c9ccccc97)c7ccccc7-8)cc6c45)n3)cc2)cc1]

TABLE 1-continued
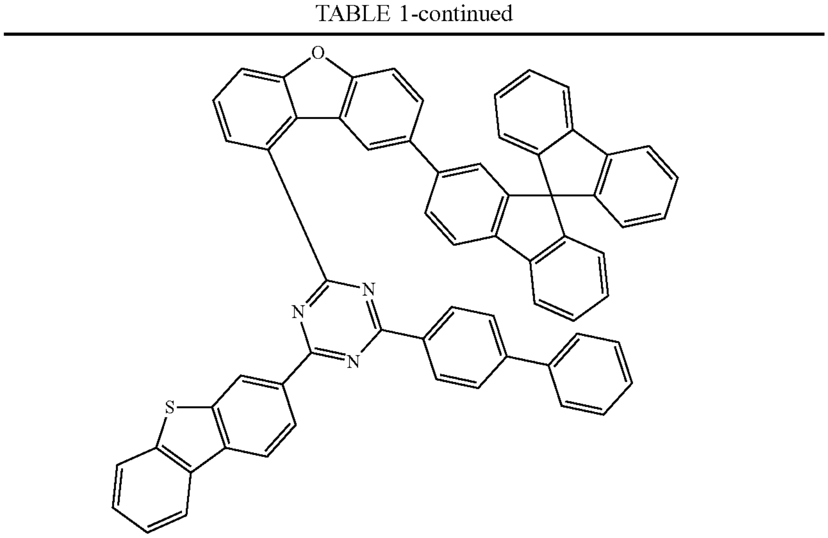
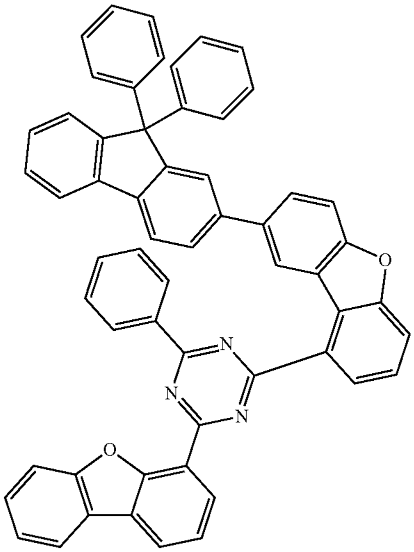 [SMILES: c1ccc(-c2nc(-c3cccc4c3oc3ccccc34)nc(-c3cccc4oc5ccc(-c6ccc7c(c6)C(c6ccccc6)(c6ccccc6)c6ccccc6-7)cc5c34)n2)cc1]
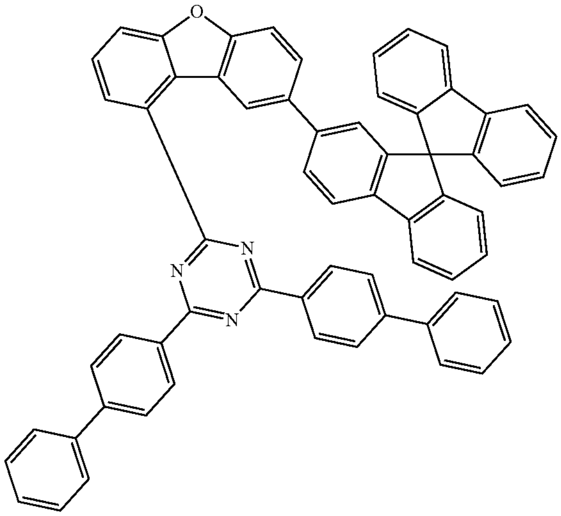 [SMILES: c1ccc(-c2ccc(-c3nc(-c4ccc(-c5ccccc5)cc4)nc(-c4cccc5oc6ccc(-c7ccc8c(c7)C7(c9ccccc9-c9ccccc97)c7ccccc7-8)cc6c45)n3)cc2)cc1]

TABLE 1-continued
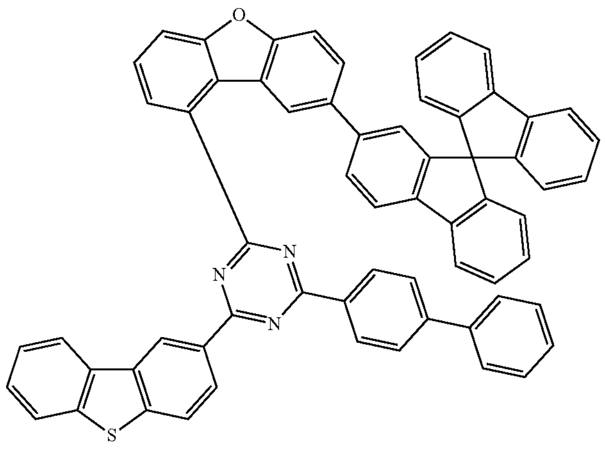 [SMILES: c1ccc(-c2ccc(-c3nc(-c4ccc5sc6ccccc6c5c4)nc(-c4cccc5oc6ccc(-c7ccc8c(c7)C7(c9ccccc9-c9ccccc97)c7ccccc7-8)cc6c45)n3)cc2)cc1]
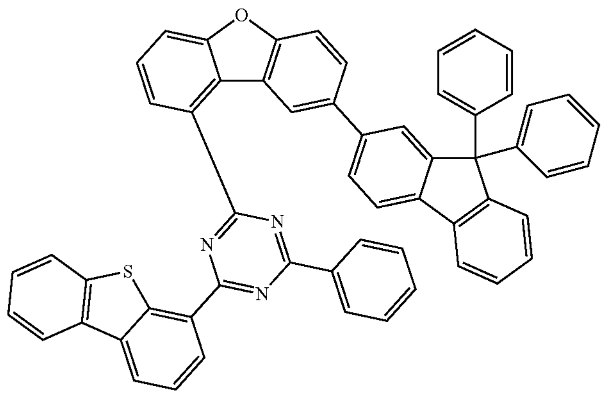 [SMILES: c1ccc(-c2nc(-c3cccc4c3sc3ccccc34)nc(-c3cccc4oc5ccc(-c6ccc7c(c6)C(c6ccccc6)(c6ccccc6)c6ccccc6-7)cc5c34)n2)cc1]
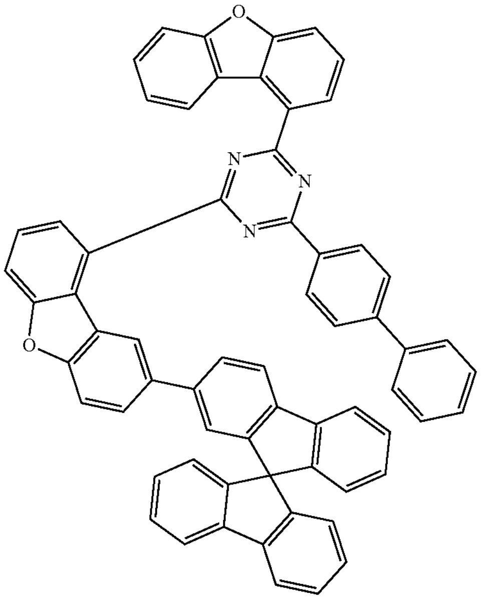 [SMILES: c1ccc(-c2ccc(-c3nc(-c4cccc5oc6ccccc6c45)nc(-c4cccc5oc6ccc(-c7ccc8c(c7)C7(c9ccccc9-c9ccccc97)c7ccccc7-8)cc6c45)n3)cc2)cc1]

TABLE 1-continued
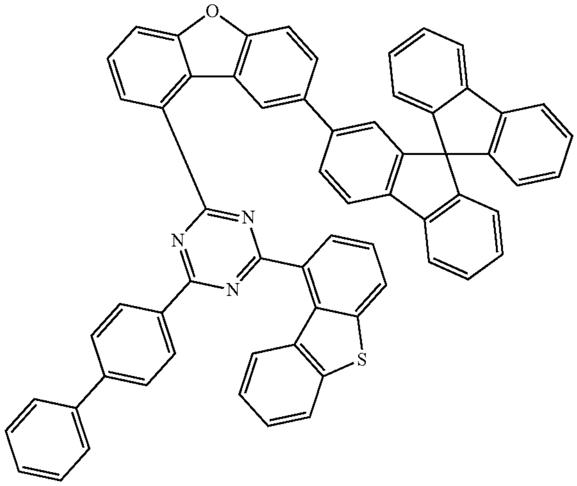 [SMILES: c1ccc(-c2ccc(-c3nc(-c4cccc5oc6ccc(-c7ccc8c(c7)C7(c9ccccc9-c9ccccc97)c7ccccc7-8)cc6c45)nc(-c4cccc5sc6ccccc6c45)n3)cc2)cc1]
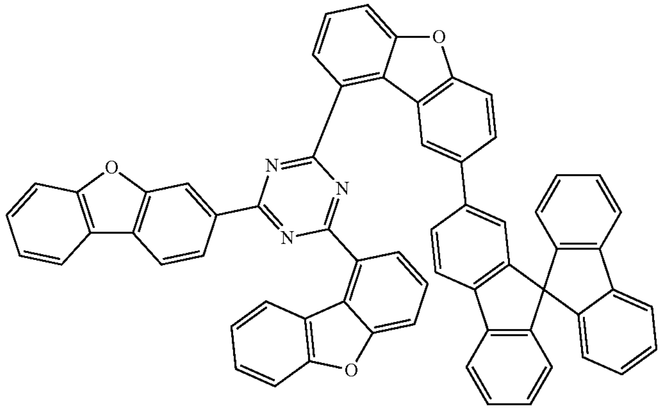 [SMILES: c1ccc2c(c1)-c1ccccc1C21c2ccccc2-c2ccc(-c3ccc4oc5cccc(-c6nc(-c7ccc8c(c7)oc7ccccc78)nc(-c7cccc8oc9ccccc9c78)n6)c5c4c3)cc21]
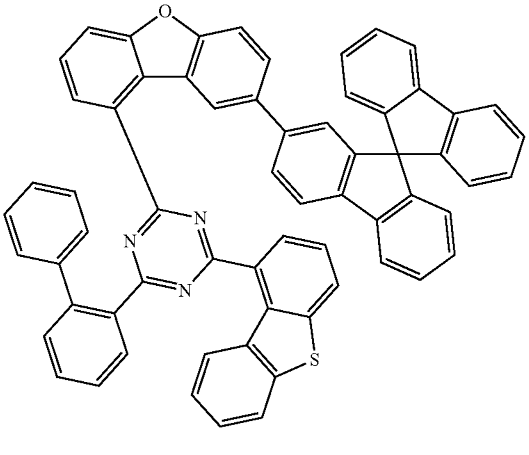 [SMILES: c1ccc(-c2ccccc2-c2nc(-c3cccc4oc5ccc(-c6ccc7c(c6)C6(c8ccccc8-c8ccccc86)c6ccccc6-7)cc5c34)nc(-c3cccc4sc5ccccc5c34)n2)cc1]

TABLE 1-continued
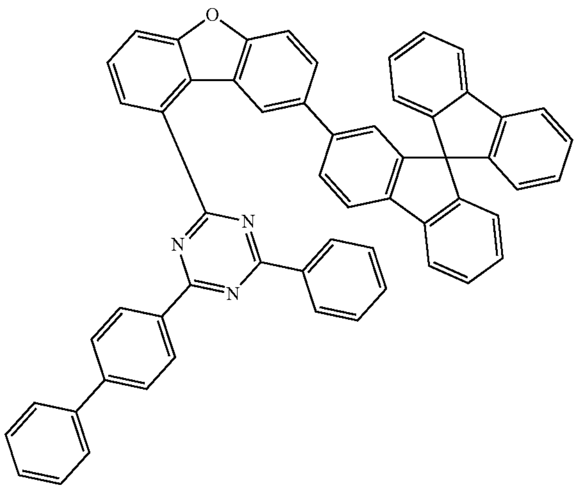 [SMILES: c1ccc(-c2ccc(-c3nc(-c4ccccc4)nc(-c4cccc5oc6ccc(-c7ccc8c(c7)C7(c9ccccc9-c9ccccc97)c7ccccc7-8)cc6c45)n3)cc2)cc1]
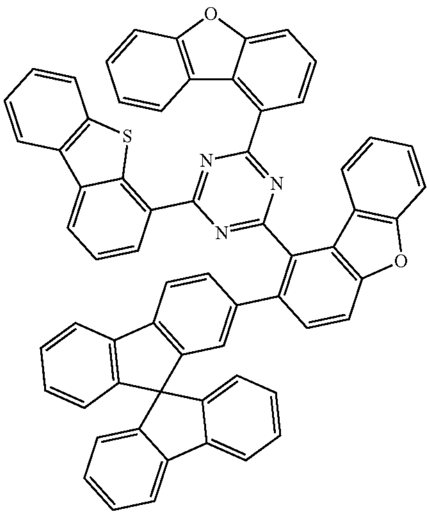 [SMILES: c1ccc2c(c1)-c1ccccc1C21c2ccccc2-c2ccc(-c3ccc4oc5ccccc5c4c3-c3nc(-c4cccc5c4sc4ccccc45)nc(-c4cccc5oc6ccccc6c45)n3)cc21]
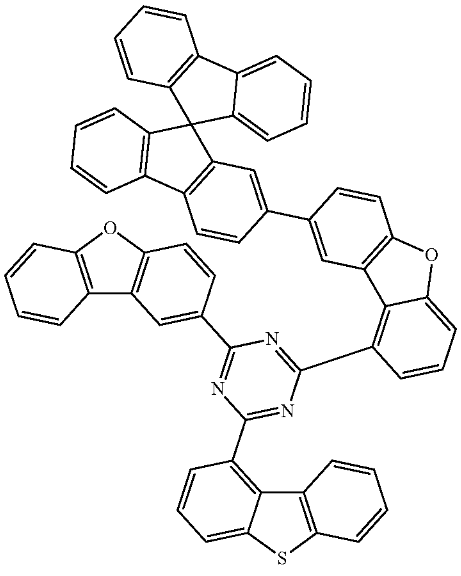 [SMILES: c1ccc2c(c1)-c1ccccc1C21c2ccccc2-c2ccc(-c3ccc4oc5cccc(-c6nc(-c7ccc8oc9ccccc9c8c7)nc(-c7cccc8sc9ccccc9c78)n6)c5c4c3)cc21]

TABLE 1-continued
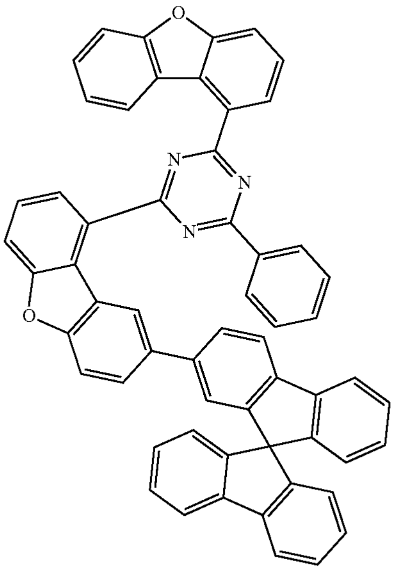 [SMILES: c1ccc(-c2nc(-c3cccc4oc5ccccc5c34)nc(-c3cccc4oc5ccc(-c6ccc7c(c6)C6(c8ccccc8-c8ccccc86)c6ccccc6-7)cc5c34)n2)cc1]
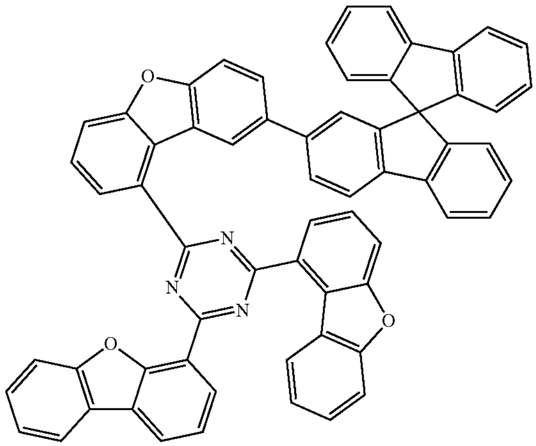 [SMILES: c1ccc2c(c1)-c1ccccc1C21c2ccccc2-c2ccc(-c3ccc4oc5cccc(-c6nc(-c7cccc8c7oc7ccccc78)nc(-c7cccc8oc9ccccc9c78)n6)c5c4c3)cc21]
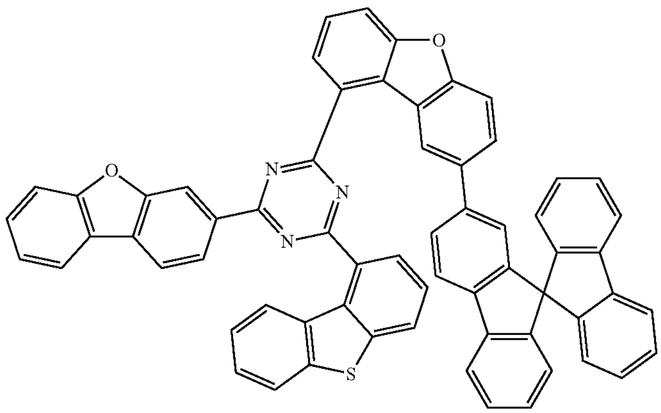

TABLE 1-continued
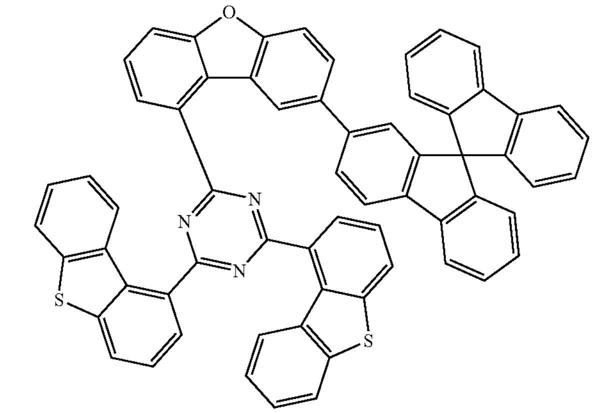 [SMILES: c1ccc2c(c1)-c1ccccc1C21c2ccccc2-c2ccc(-c3ccc4oc5cccc(-c6nc(-c7cccc8sc9ccccc9c78)nc(-c7cccc8sc9ccccc9c78)n6)c5c4c3)cc21]
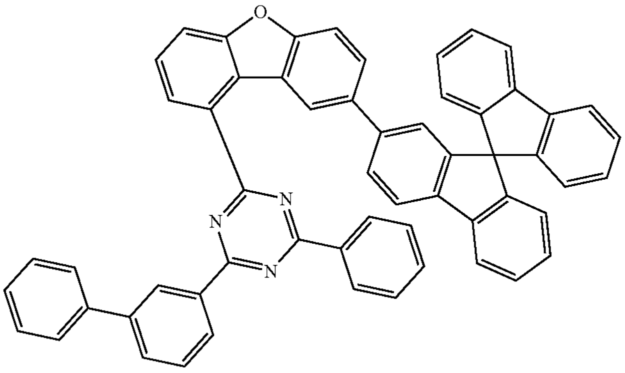 [SMILES: c1ccc(-c2cccc(-c3nc(-c4ccccc4)nc(-c4cccc5oc6ccc(-c7ccc8c(c7)C7(c9ccccc9-c9ccccc97)c7ccccc7-8)cc6c45)n3)c2)cc1]
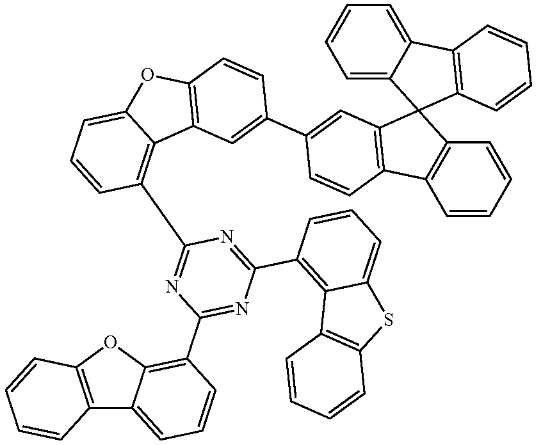

TABLE 1-continued
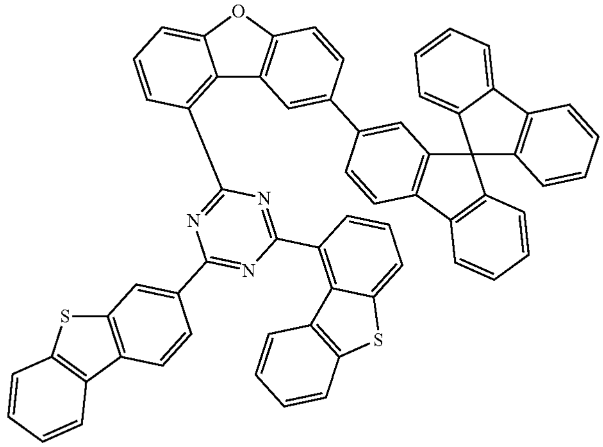 [SMILES: c1ccc2c(c1)-c1ccccc1C21c2ccccc2-c2ccc(-c3ccc4oc5cccc(-c6nc(-c7ccc8c(c7)sc7ccccc78)nc(-c7cccc8sc9ccccc9c78)n6)c5c4c3)cc21]
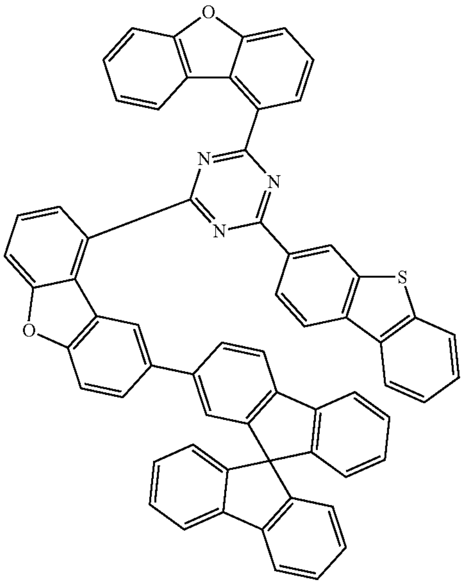 [SMILES: c1ccc2c(c1)-c1ccccc1C21c2ccccc2-c2ccc(-c3ccc4oc5cccc(-c6nc(-c7ccc8c(c7)sc7ccccc78)nc(-c7cccc8oc9ccccc9c78)n6)c5c4c3)cc21]
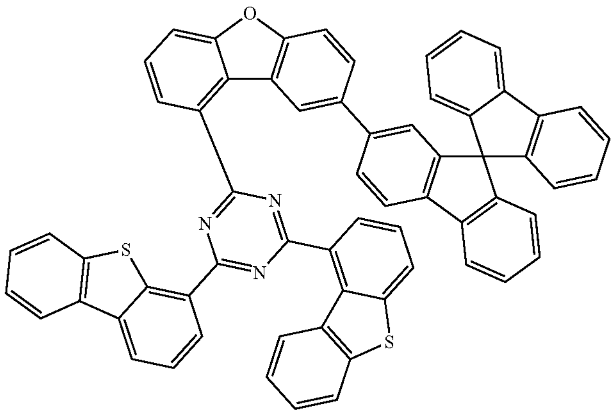 [SMILES: c1ccc2c(c1)-c1ccccc1C21c2ccccc2-c2ccc(-c3ccc4oc5cccc(-c6nc(-c7cccc8c7sc7ccccc78)nc(-c7cccc8sc9ccccc9c78)n6)c5c4c3)cc21]

TABLE 1-continued
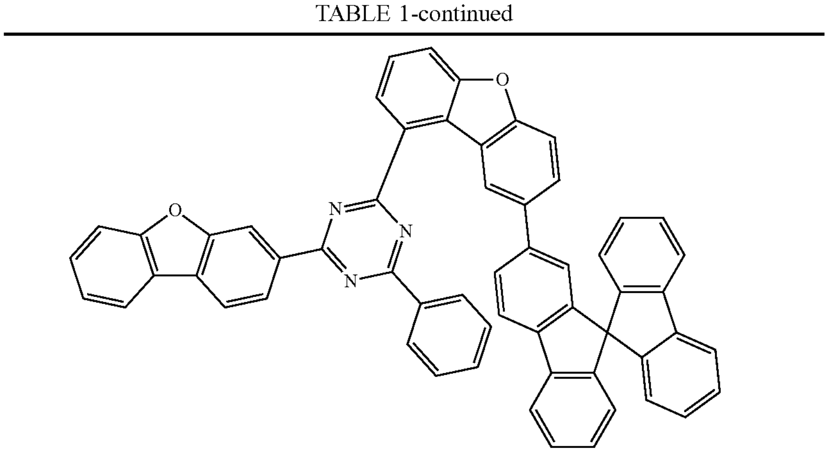
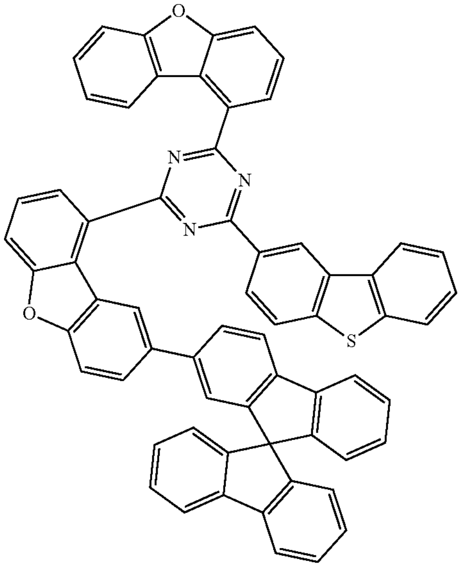
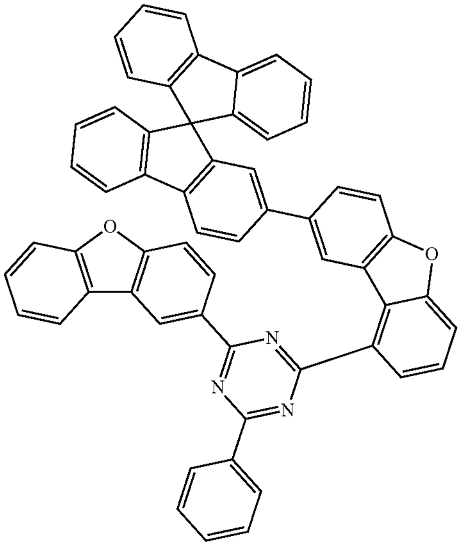 [SMILES: c1ccc(-c2nc(-c3ccc4oc5ccccc5c4c3)nc(-c3cccc4oc5ccc(-c6ccc7c(c6)C6(c8ccccc8-c8ccccc86)c6ccccc6-7)cc5c34)n2)cc1]

TABLE 1-continued
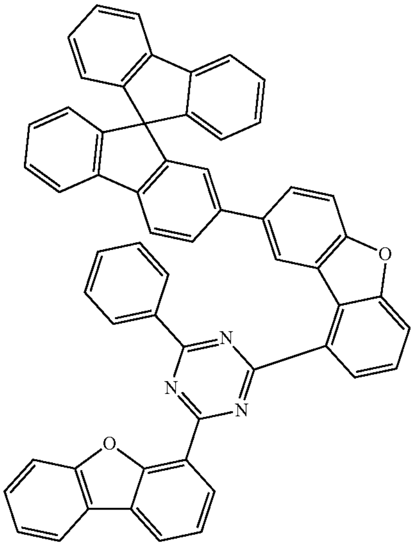 [SMILES: c1ccc(-c2nc(-c3cccc4c3oc3ccccc34)nc(-c3cccc4oc5ccc(-c6ccc7c(c6)C6(c8ccccc8-c8ccccc86)c6ccccc6-7)cc5c34)n2)cc1]
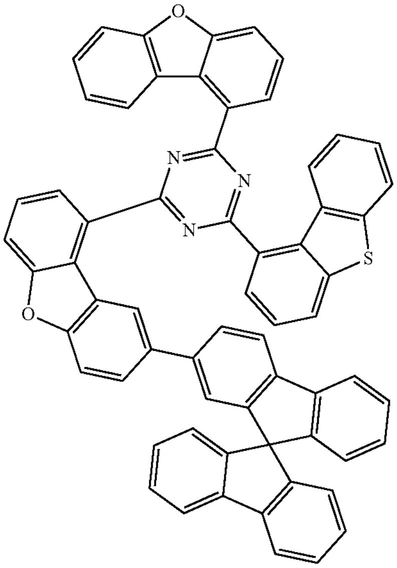

TABLE 1-continued
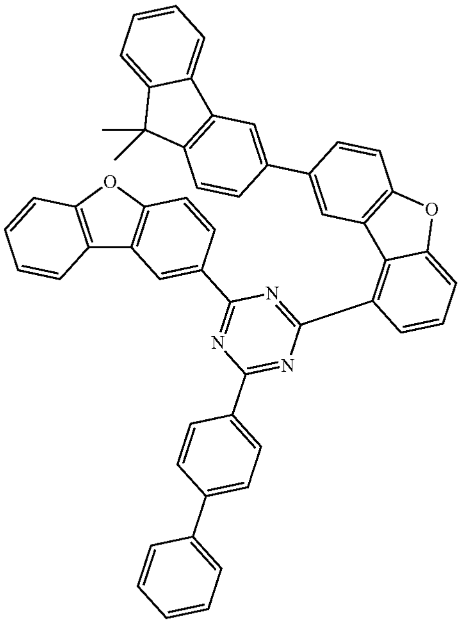 [SMILES: CC1(C)c2ccccc2-c2cc(-c3ccc4oc5cccc(-c6nc(-c7ccc(-c8ccccc8)cc7)nc(-c7ccc8oc9ccccc9c8c7)n6)c5c4c3)ccc21]
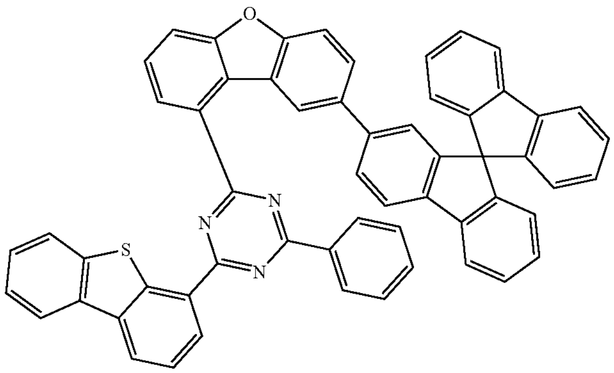 [SMILES: c1ccc(-c2nc(-c3cccc4c3sc3ccccc34)nc(-c3cccc4oc5ccc(-c6ccc7c(c6)C6(c8ccccc8-c8ccccc86)c6ccccc6-7)cc5c34)n2)cc1]
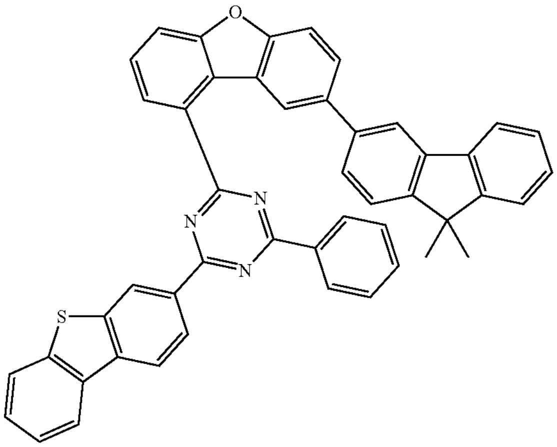 [SMILES: CC1(C)c2ccccc2-c2cc(-c3ccc4oc5cccc(-c6nc(-c7ccccc7)nc(-c7ccc8c(c7)sc7ccccc78)n6)c5c4c3)ccc21]

TABLE 1-continued
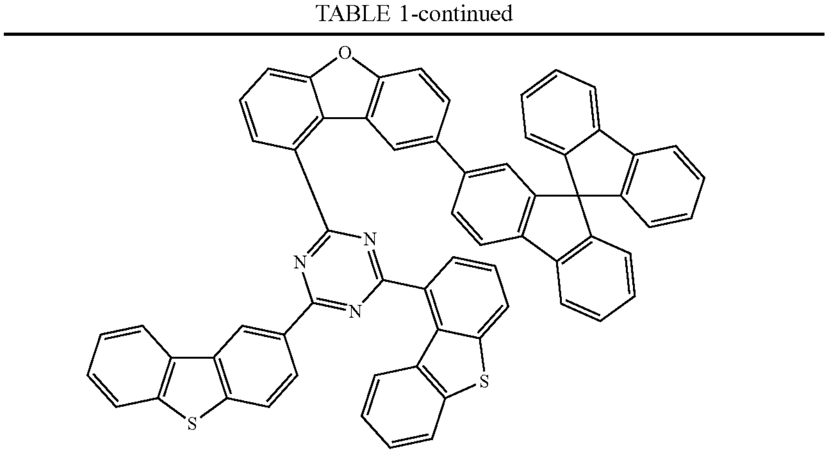
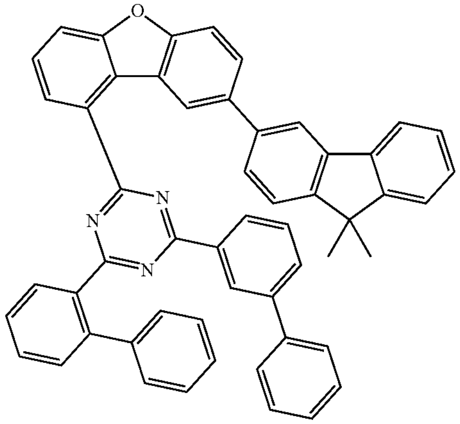 [SMILES: CC1(C)c2ccccc2-c2cc(-c3ccc4oc5cccc(-c6nc(-c7cccc(-c8ccccc8)c7)nc(-c7ccccc7-c7ccccc7)n6)c5c4c3)ccc21]
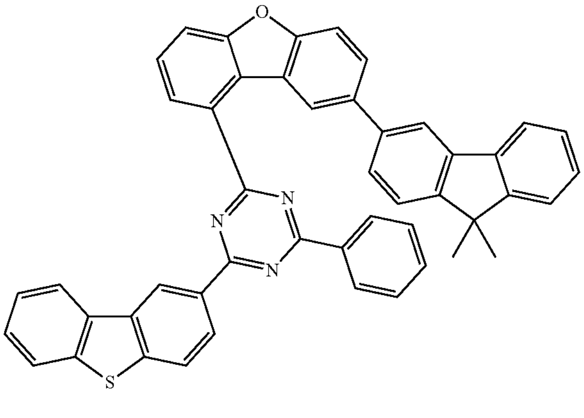 [SMILES: CC1(C)c2ccccc2-c2cc(-c3ccc4oc5cccc(-c6nc(-c7ccccc7)nc(-c7ccc8sc9ccccc9c8c7)n6)c5c4c3)ccc21]

TABLE 1-continued
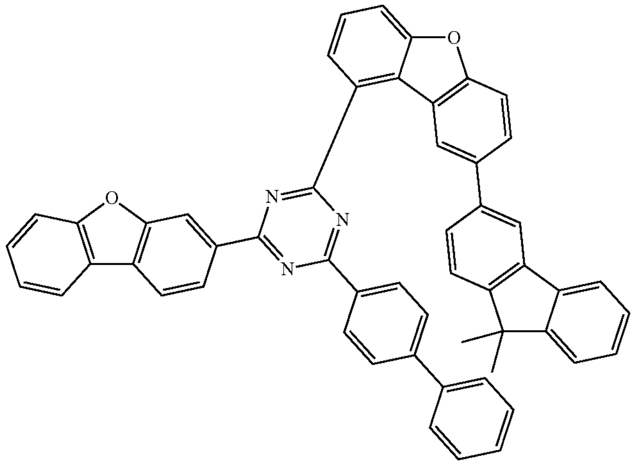 [SMILES: CC1(C)c2ccccc2-c2cc(-c3ccc4oc5cccc(-c6nc(-c7ccc(-c8ccccc8)cc7)nc(-c7ccc8c(c7)oc7ccccc78)n6)c5c4c3)ccc21]
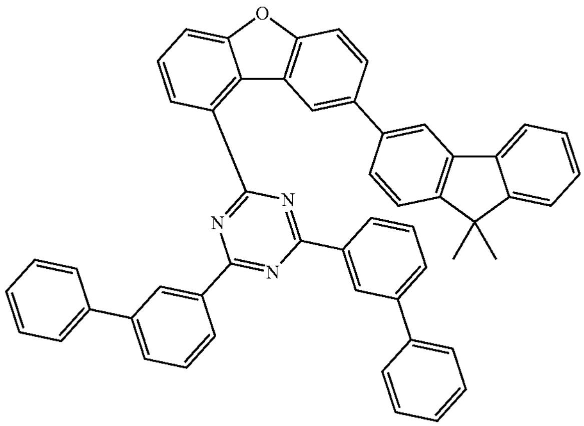 [SMILES: CC1(C)c2ccccc2-c2cc(-c3ccc4oc5cccc(-c6nc(-c7cccc(-c8ccccc8)c7)nc(-c7cccc(-c8ccccc8)c7)n6)c5c4c3)ccc21]
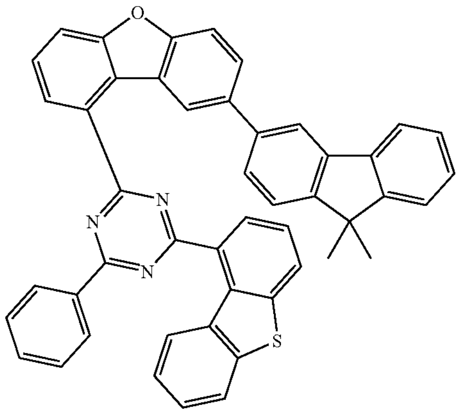 [SMILES: CC1(C)c2ccccc2-c2cc(-c3ccc4oc5cccc(-c6nc(-c7ccccc7)nc(-c7cccc8sc9ccccc9c78)n6)c5c4c3)ccc21]

TABLE 1-continued
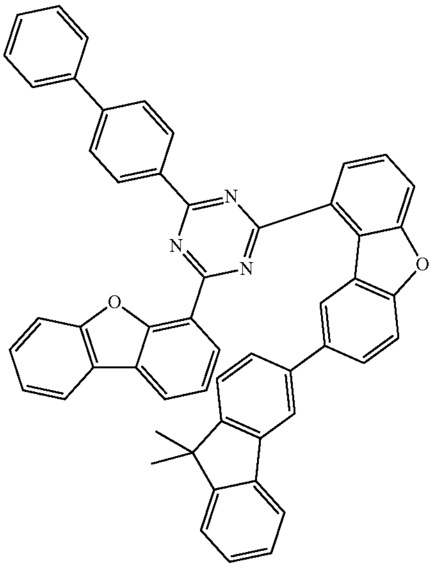 [SMILES: CC1(C)c2ccccc2-c2cc(-c3ccc4oc5cccc(-c6nc(-c7ccc(-c8ccccc8)cc7)nc(-c7cccc8c7oc7ccccc78)n6)c5c4c3)ccc21]
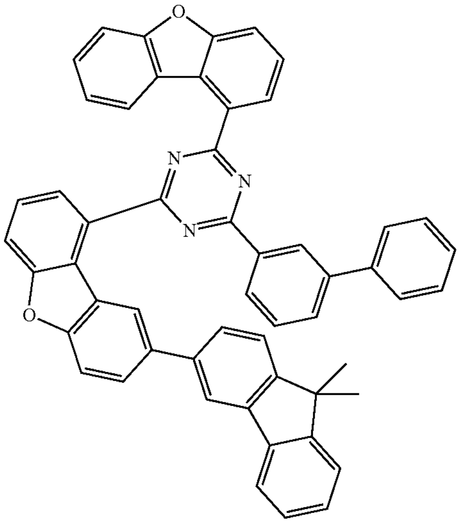 [SMILES: CC1(C)c2ccccc2-c2cc(-c3ccc4oc5cccc(-c6nc(-c7cccc(-c8ccccc8)c7)nc(-c7cccc8oc9ccccc9c78)n6)c5c4c3)ccc21]
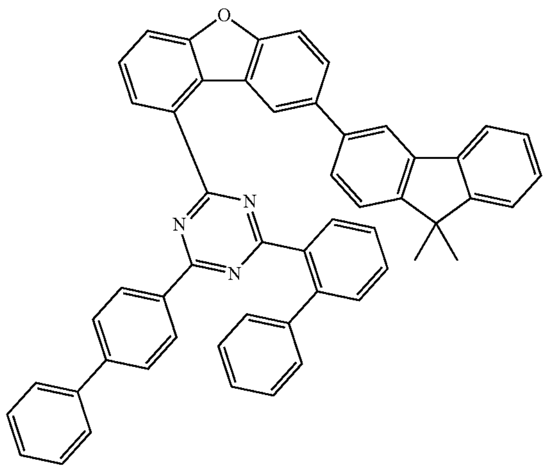 [SMILES: CC1(C)c2ccccc2-c2cc(-c3ccc4oc5cccc(-c6nc(-c7ccc(-c8ccccc8)cc7)nc(-c7ccccc7-c7ccccc7)n6)c5c4c3)ccc21]

TABLE 1-continued
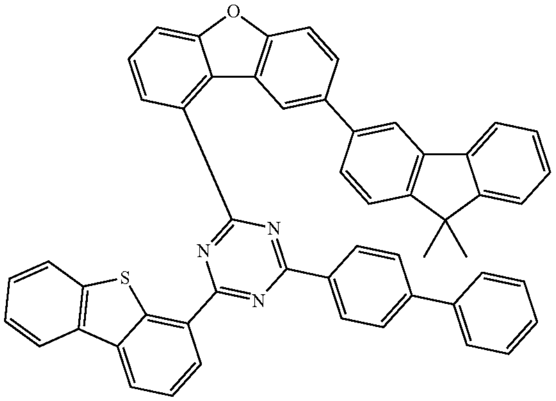 [SMILES: CC1(C)c2ccccc2-c2cc(-c3ccc4oc5cccc(-c6nc(-c7ccc(-c8ccccc8)cc7)nc(-c7cccc8c7sc7ccccc78)n6)c5c4c3)ccc21]
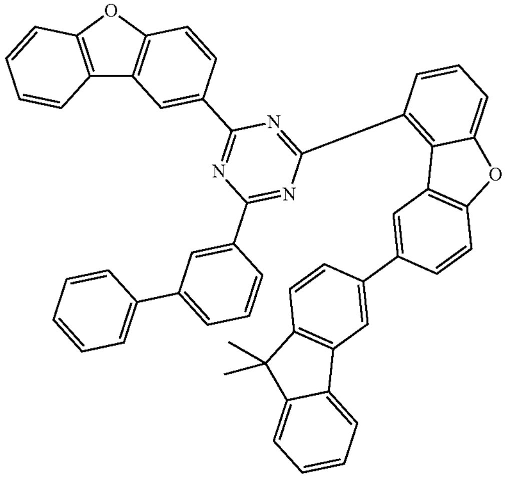 [SMILES: CC1(C)c2ccccc2-c2cc(-c3ccc4oc5cccc(-c6nc(-c7cccc(-c8ccccc8)c7)nc(-c7ccc8oc9ccccc9c8c7)n6)c5c4c3)ccc21]
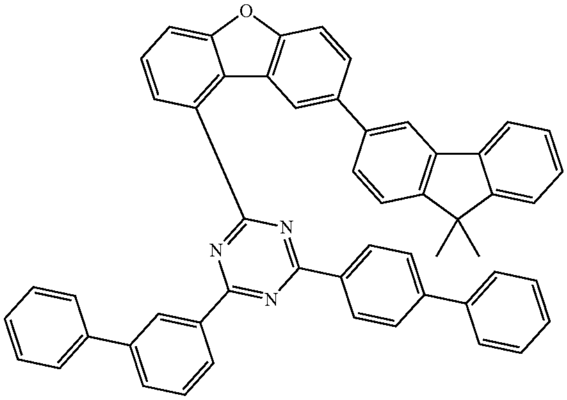 [SMILES: CC1(C)c2ccccc2-c2cc(-c3ccc4oc5cccc(-c6nc(-c7ccc(-c8ccccc8)cc7)nc(-c7cccc(-c8ccccc8)c7)n6)c5c4c3)ccc21]

TABLE 1-continued
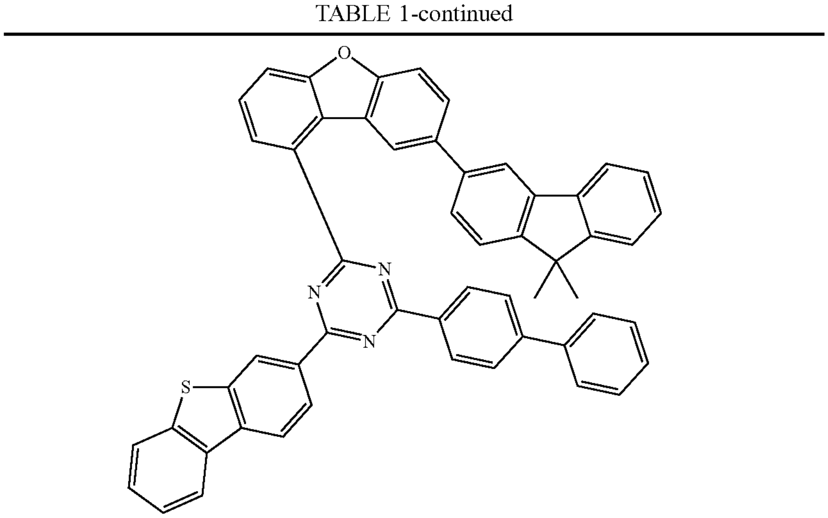
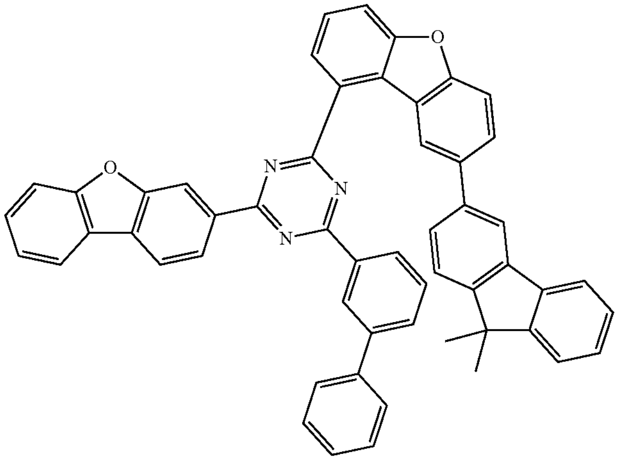 [SMILES: CC1(C)c2ccccc2-c2cc(-c3ccc4oc5cccc(-c6nc(-c7cccc(-c8ccccc8)c7)nc(-c7ccc8c(c7)oc7ccccc78)n6)c5c4c3)ccc21]
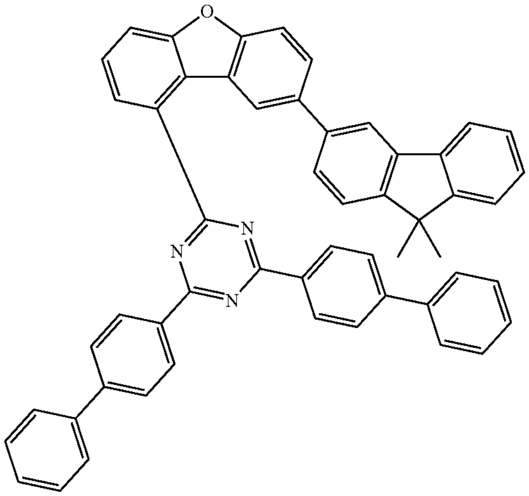 [SMILES: CC1(C)c2ccccc2-c2cc(-c3ccc4oc5cccc(-c6nc(-c7ccc(-c8ccccc8)cc7)nc(-c7ccc(-c8ccccc8)cc7)n6)c5c4c3)ccc21]

TABLE 1-continued
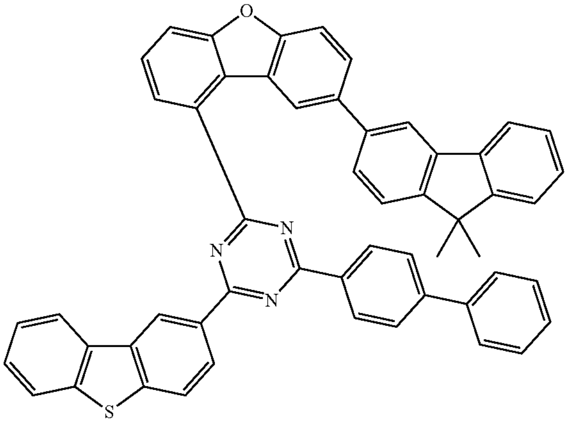 [SMILES: CC1(C)c2ccccc2-c2cc(-c3ccc4oc5cccc(-c6nc(-c7ccc(-c8ccccc8)cc7)nc(-c7ccc8sc9ccccc9c8c7)n6)c5c4c3)ccc21]
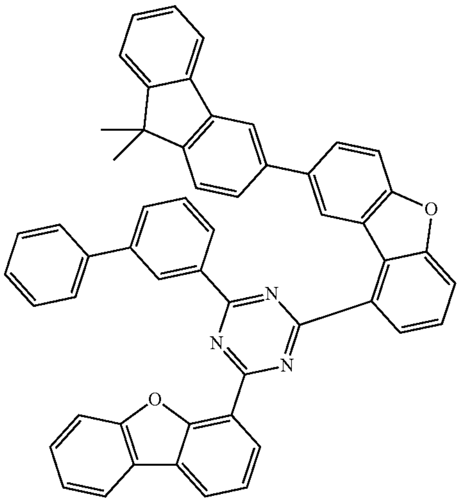 [SMILES: CC1(C)c2ccccc2-c2cc(-c3ccc4oc5cccc(-c6nc(-c7cccc(-c8ccccc8)c7)nc(-c7cccc8c7oc7ccccc78)n6)c5c4c3)ccc21]
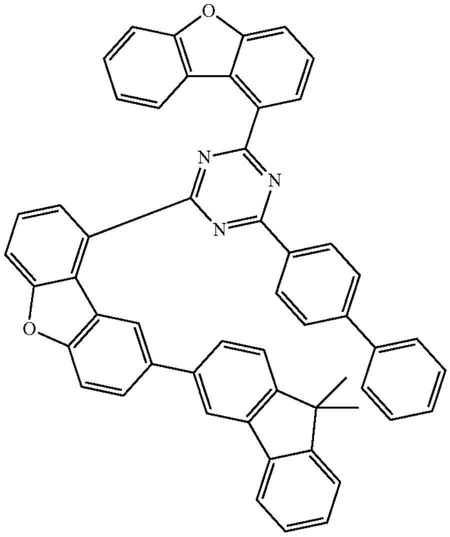 [SMILES: CC1(C)c2ccccc2-c2cc(-c3ccc4oc5cccc(-c6nc(-c7ccc(-c8ccccc8)cc7)nc(-c7cccc8oc9ccccc9c78)n6)c5c4c3)ccc21]

TABLE 1-continued
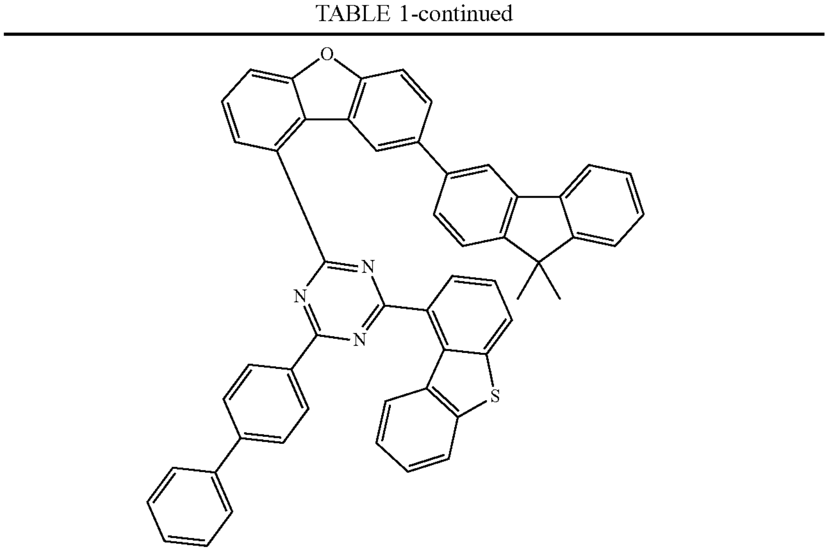
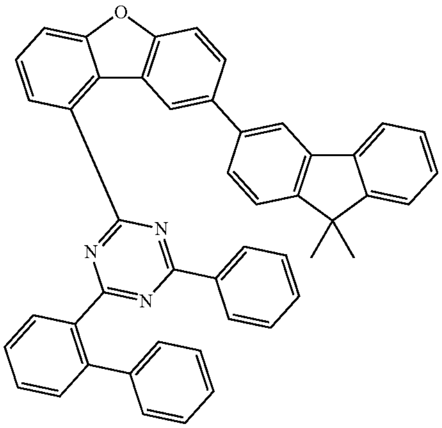 [SMILES: CC1(C)c2ccccc2-c2cc(-c3ccc4oc5cccc(-c6nc(-c7ccccc7)nc(-c7ccccc7-c7ccccc7)n6)c5c4c3)ccc21]
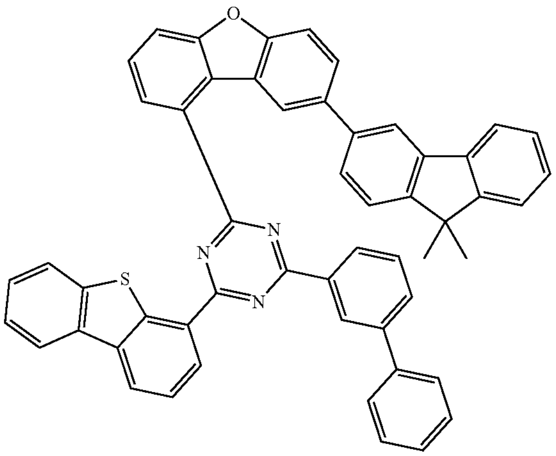 [SMILES: CC1(C)c2ccccc2-c2cc(-c3ccc4oc5cccc(-c6nc(-c7cccc(-c8ccccc8)c7)nc(-c7cccc8c7sc7ccccc78)n6)c5c4c3)ccc21]

TABLE 1-continued
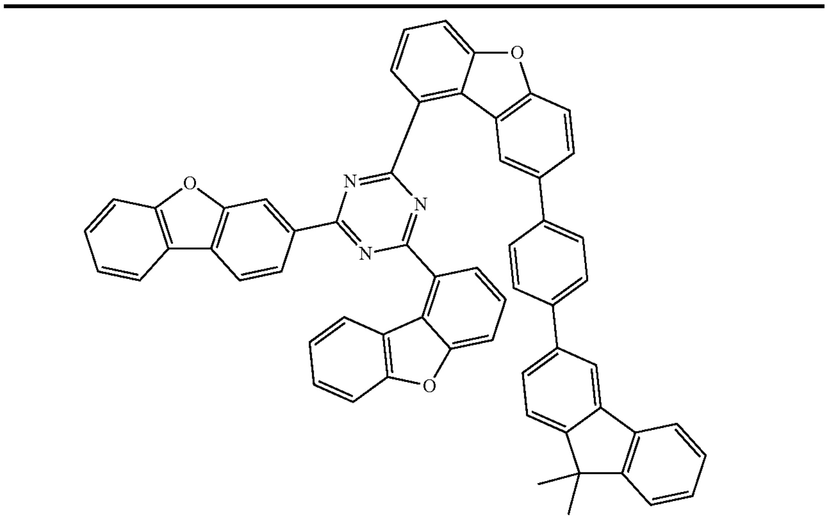
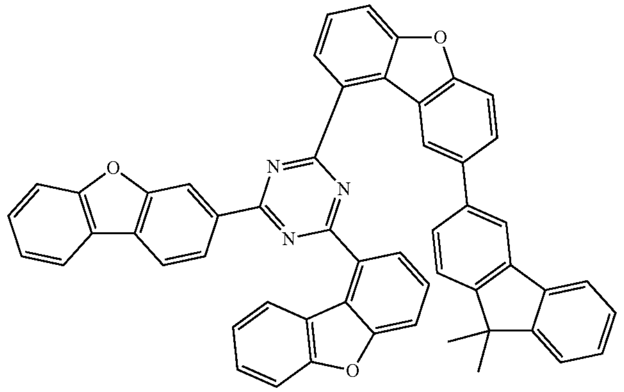 [SMILES: CC1(C)c2ccccc2-c2cc(-c3ccc4oc5cccc(-c6nc(-c7ccc8c(c7)oc7ccccc78)nc(-c7cccc8oc9ccccc9c78)n6)c5c4c3)ccc21]
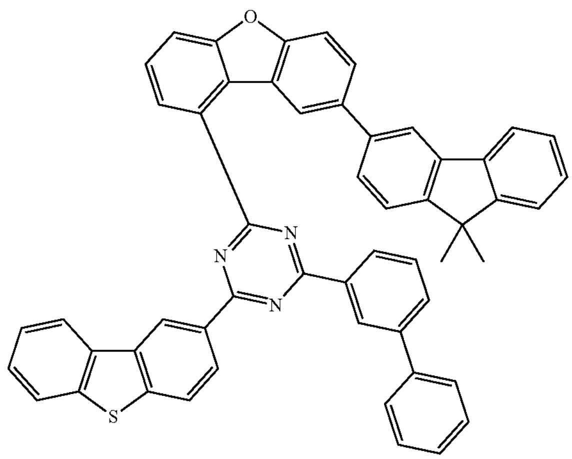 [SMILES: CC1(C)c2ccccc2-c2cc(-c3ccc4oc5cccc(-c6nc(-c7cccc(-c8ccccc8)c7)nc(-c7ccc8sc9ccccc9c8c7)n6)c5c4c3)ccc21]

TABLE 1-continued
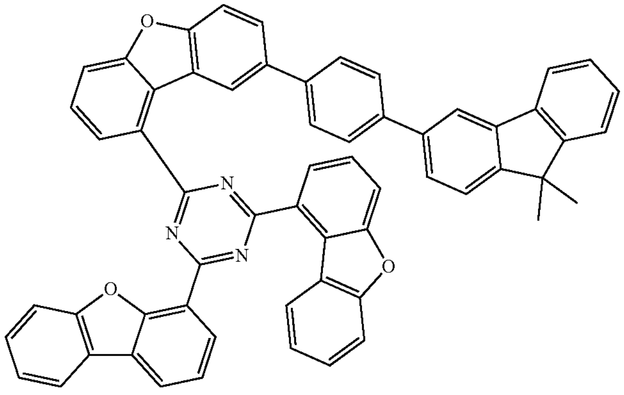 [SMILES: CC1(C)c2ccccc2-c2cc(-c3ccc(-c4ccc5oc6cccc(-c7nc(-c8cccc9c8oc8ccccc89)nc(-c8cccc9oc%10ccccc%10c89)n7)c6c5c4)cc3)ccc21]
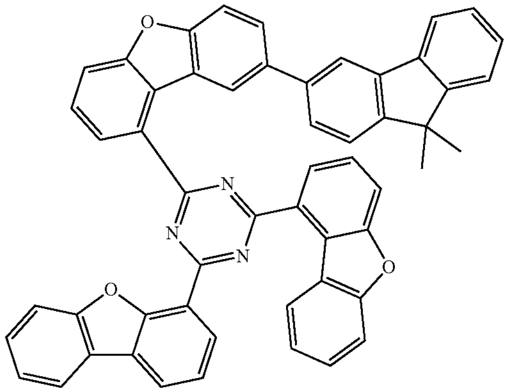 [SMILES: CC1(C)c2ccccc2-c2cc(-c3ccc4oc5cccc(-c6nc(-c7cccc8c7oc7ccccc78)nc(-c7cccc8oc9ccccc9c78)n6)c5c4c3)ccc21]
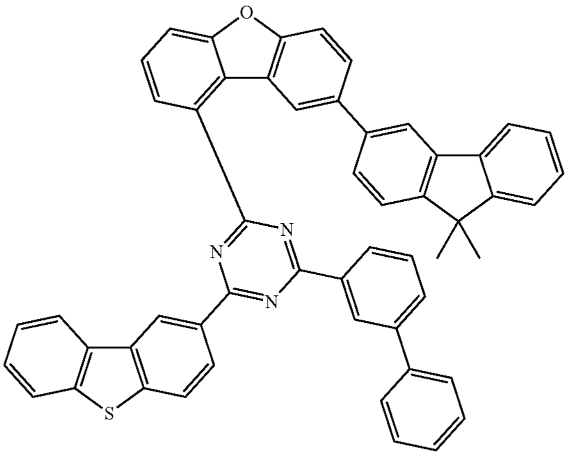 [SMILES: CC1(C)c2ccccc2-c2cc(-c3ccc4oc5cccc(-c6nc(-c7cccc(-c8ccccc8)c7)nc(-c7ccc8sc9ccccc9c8c7)n6)c5c4c3)ccc21]
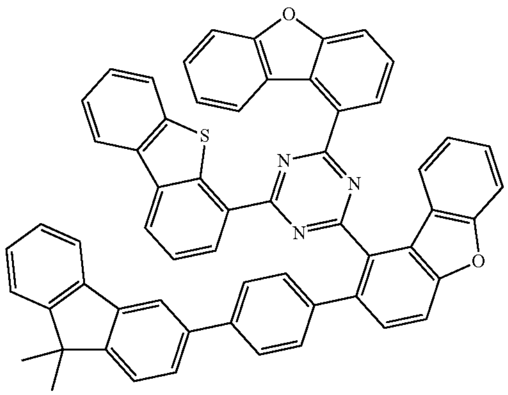 [SMILES: CC1(C)c2ccccc2-c2cc(-c3ccc(-c4ccc5oc6ccccc6c5c4-c4nc(-c5cccc6c5sc5ccccc56)nc(-c5cccc6oc7ccccc7c56)n4)cc3)ccc21]

TABLE 1-continued
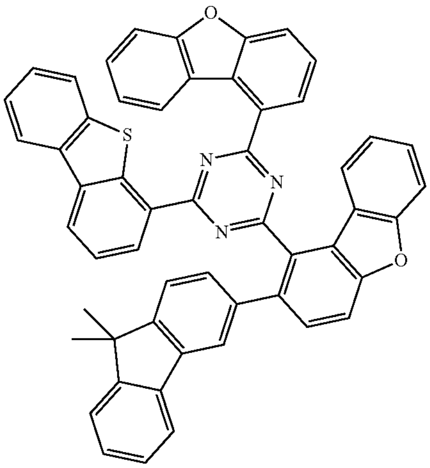 [SMILES: CC1(C)c2ccccc2-c2cc(-c3ccc4oc5ccccc5c4c3-c3nc(-c4cccc5c4sc4ccccc45)nc(-c4cccc5oc6ccccc6c45)n3)ccc21]
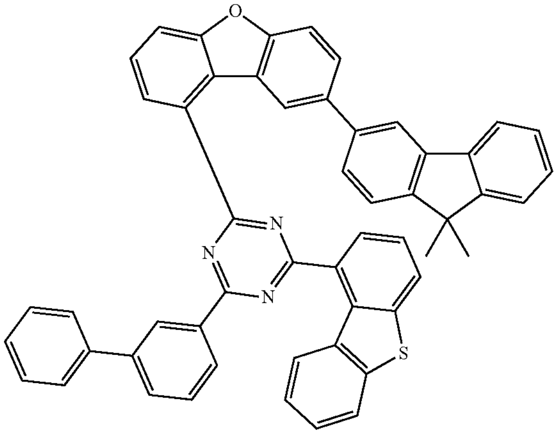 [SMILES: CC1(C)c2ccccc2-c2cc(-c3ccc4oc5cccc(-c6nc(-c7cccc(-c8ccccc8)c7)nc(-c7cccc8sc9ccccc9c78)n6)c5c4c3)ccc21]
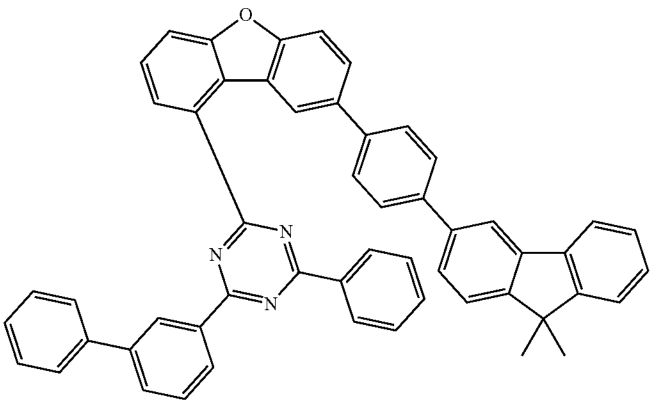 [SMILES: CC1(C)c2ccccc2-c2cc(-c3ccc(-c4ccc5oc6cccc(-c7nc(-c8ccccc8)nc(-c8cccc(-c9ccccc9)c8)n7)c6c5c4)cc3)ccc21]

TABLE 1-continued
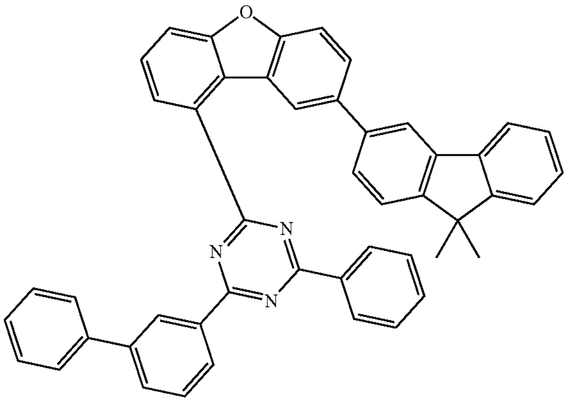 [SMILES: CC1(C)c2ccccc2-c2cc(-c3ccc4oc5cccc(-c6nc(-c7ccccc7)nc(-c7cccc(-c8ccccc8)c7)n6)c5c4c3)ccc21]
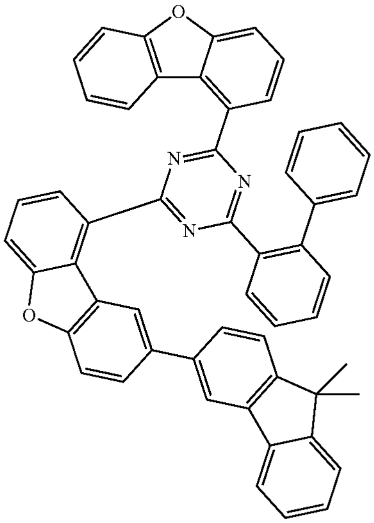 [SMILES: CC1(C)c2ccccc2-c2cc(-c3ccc4oc5cccc(-c6nc(-c7ccccc7-c7ccccc7)nc(-c7cccc8oc9ccccc9c78)n6)c5c4c3)ccc21]
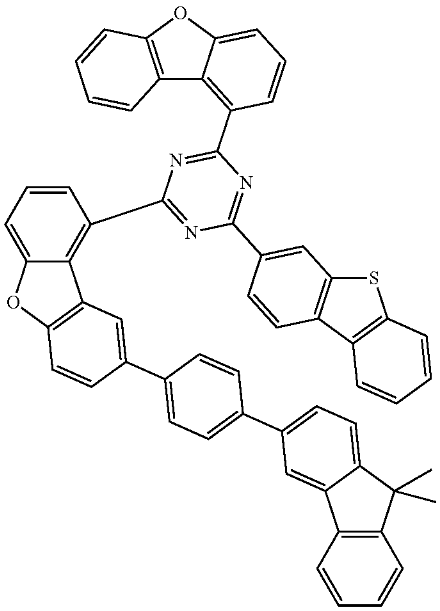 [SMILES: CC1(C)c2ccccc2-c2cc(-c3ccc(-c4ccc5oc6cccc(-c7nc(-c8ccc9c(c8)sc8ccccc89)nc(-c8cccc9oc%10ccccc%10c89)n7)c6c5c4)cc3)ccc21]

TABLE 1-continued
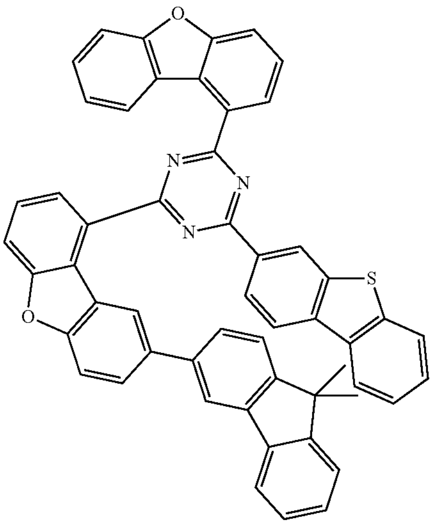 [SMILES: CC1(C)c2ccccc2-c2cc(-c3ccc4oc5cccc(-c6nc(-c7ccc8c(c7)sc7ccccc78)nc(-c7cccc8oc9ccccc9c78)n6)c5c4c3)ccc21]
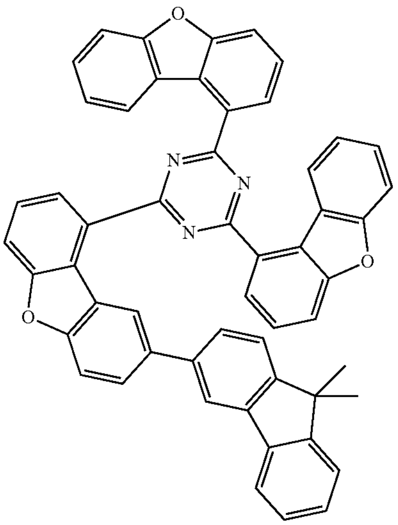 [SMILES: CC1(C)c2ccccc2-c2cc(-c3ccc4oc5cccc(-c6nc(-c7cccc8oc9ccccc9c78)nc(-c7cccc8oc9ccccc9c78)n6)c5c4c3)ccc21]
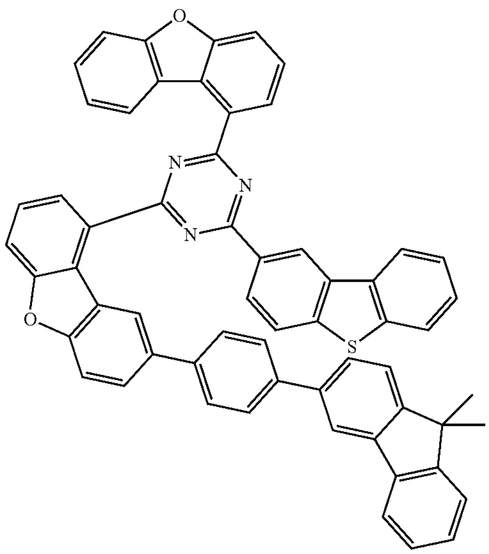 [SMILES: CC1(C)c2ccccc2-c2cc(-c3ccc(-c4ccc5oc6cccc(-c7nc(-c8ccc9sc%10ccccc%10c9c8)nc(-c8cccc9oc%10ccccc%10c89)n7)c6c5c4)cc3)ccc21]

TABLE 1-continued
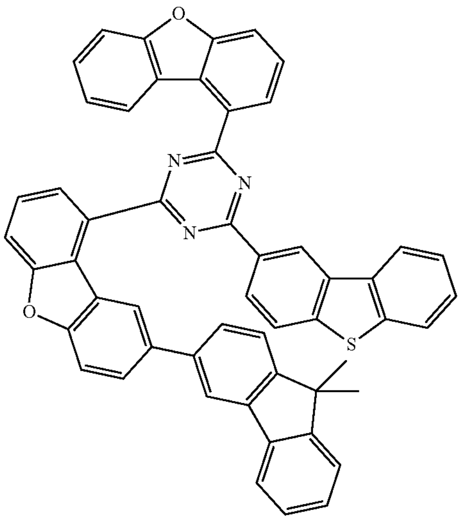 [SMILES: CC1(C)c2ccccc2-c2cc(-c3ccc4oc5cccc(-c6nc(-c7ccc8sc9ccccc9c8c7)nc(-c7cccc8oc9ccccc9c78)n6)c5c4c3)ccc21]
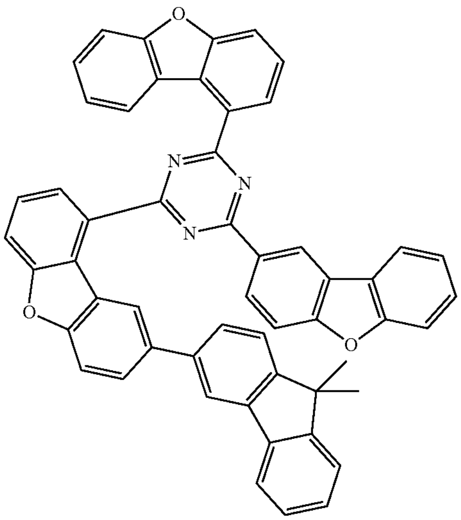 [SMILES: CC1(C)c2ccccc2-c2cc(-c3ccc4oc5cccc(-c6nc(-c7ccc8oc9ccccc9c8c7)nc(-c7cccc8oc9ccccc9c78)n6)c5c4c3)ccc21]
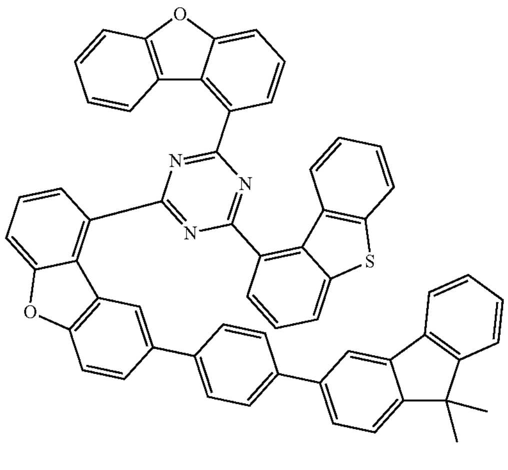 [SMILES: CC1(C)c2ccccc2-c2cc(-c3ccc(-c4ccc5oc6cccc(-c7nc(-c8cccc9oc%10ccccc%10c89)nc(-c8cccc9sc%10ccccc%10c89)n7)c6c5c4)cc3)ccc21]

TABLE 1-continued
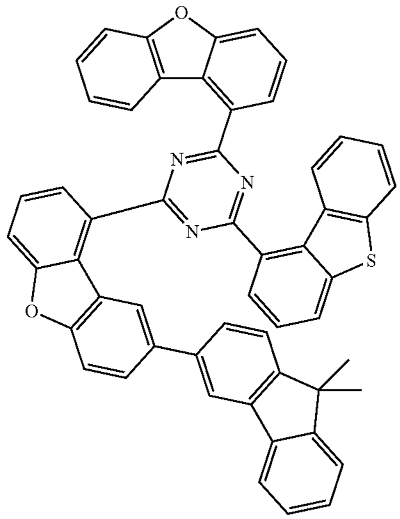 [SMILES: CC1(C)c2ccccc2-c2cc(-c3ccc4oc5cccc(-c6nc(-c7cccc8oc9ccccc9c78)nc(-c7cccc8sc9ccccc9c78)n6)c5c4c3)ccc21]
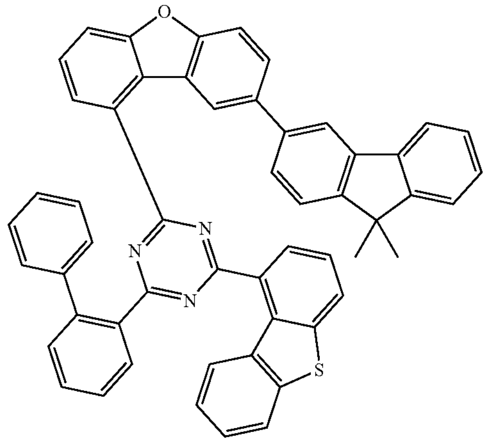 [SMILES: CC1(C)c2ccccc2-c2cc(-c3ccc4oc5cccc(-c6nc(-c7ccccc7-c7ccccc7)nc(-c7cccc8sc9ccccc9c78)n6)c5c4c3)ccc21]
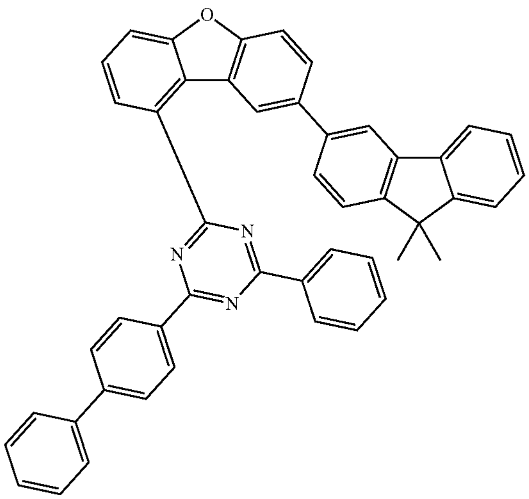 [SMILES: CC1(C)c2ccccc2-c2cc(-c3ccc4oc5cccc(-c6nc(-c7ccccc7)nc(-c7ccc(-c8ccccc8)cc7)n6)c5c4c3)ccc21]

TABLE 1-continued
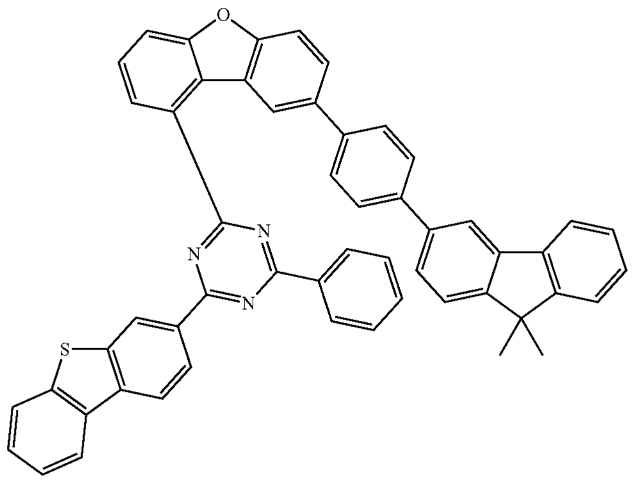 [SMILES: CC1(C)c2ccccc2-c2cc(-c3ccc(-c4ccc5oc6cccc(-c7nc(-c8ccccc8)nc(-c8ccc9c(c8)sc8ccccc89)n7)c6c5c4)cc3)ccc21]
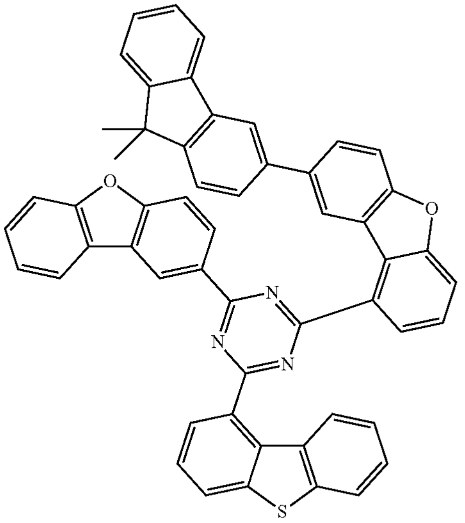 [SMILES: CC1(C)c2ccccc2-c2cc(-c3ccc4oc5cccc(-c6nc(-c7ccc8oc9ccccc9c8c7)nc(-c7cccc8sc9ccccc9c78)n6)c5c4c3)ccc21]
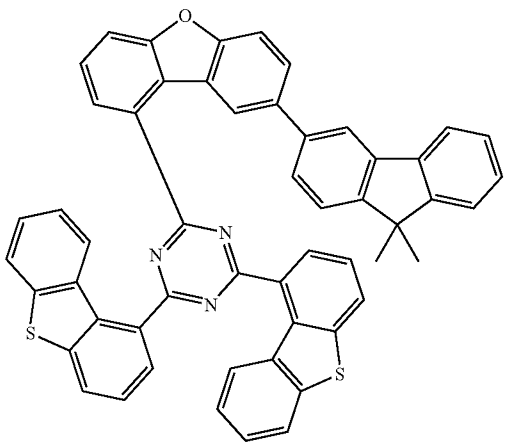 [SMILES: CC1(C)c2ccccc2-c2cc(-c3ccc4oc5cccc(-c6nc(-c7cccc8sc9ccccc9c78)nc(-c7cccc8sc9ccccc9c78)n6)c5c4c3)ccc21]

TABLE 1-continued
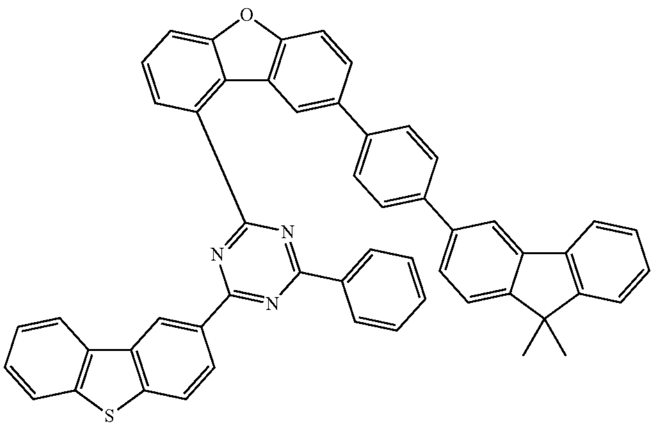 [SMILES: CC1(C)c2ccccc2-c2cc(-c3ccc(-c4ccc5oc6cccc(-c7nc(-c8ccccc8)nc(-c8ccc9sc%10ccccc%10c9c8)n7)c6c5c4)cc3)ccc21]
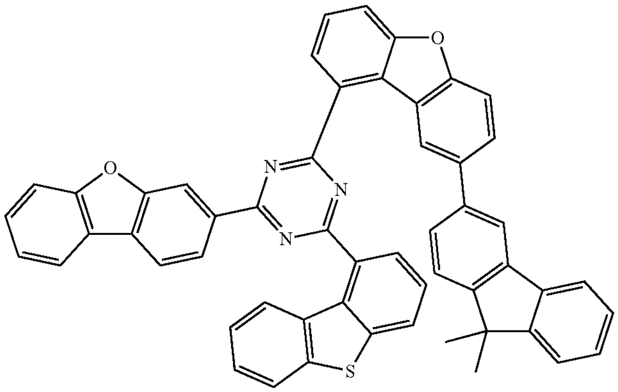 [SMILES: CC1(C)c2ccccc2-c2cc(-c3ccc4oc5cccc(-c6nc(-c7ccc8c(c7)oc7ccccc78)nc(-c7cccc8sc9ccccc9c78)n6)c5c4c3)ccc21]
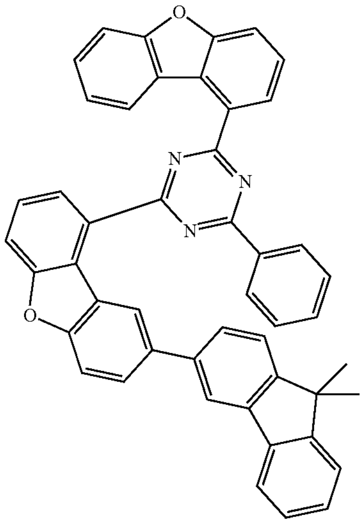 [SMILES: CC1(C)c2ccccc2-c2cc(-c3ccc4oc5cccc(-c6nc(-c7ccccc7)nc(-c7cccc8oc9ccccc9c78)n6)c5c4c3)ccc21]

TABLE 1-continued
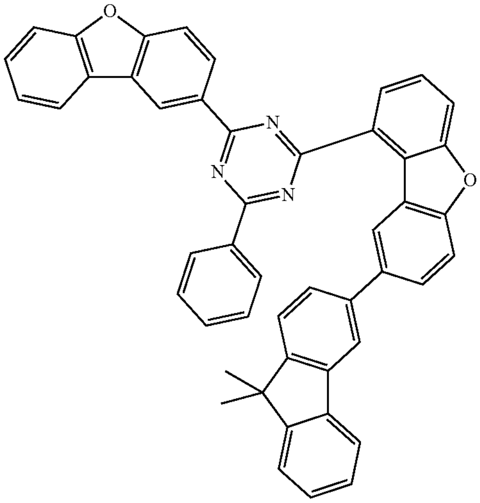 [SMILES: CC1(C)c2ccccc2-c2cc(-c3ccc4oc5cccc(-c6nc(-c7ccccc7)nc(-c7ccc8oc9ccccc9c8c7)n6)c5c4c3)ccc21]
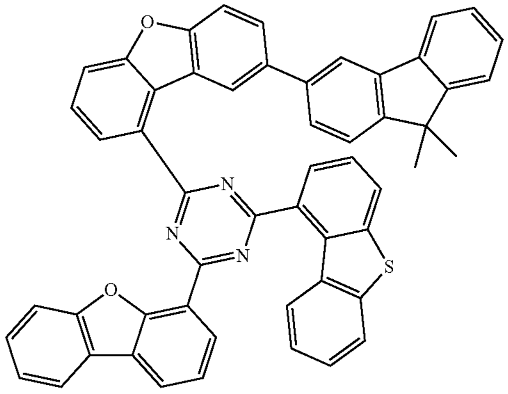 [SMILES: CC1(C)c2ccccc2-c2cc(-c3ccc4oc5cccc(-c6nc(-c7cccc8c7oc7ccccc78)nc(-c7cccc8sc9ccccc9c78)n6)c5c4c3)ccc21]
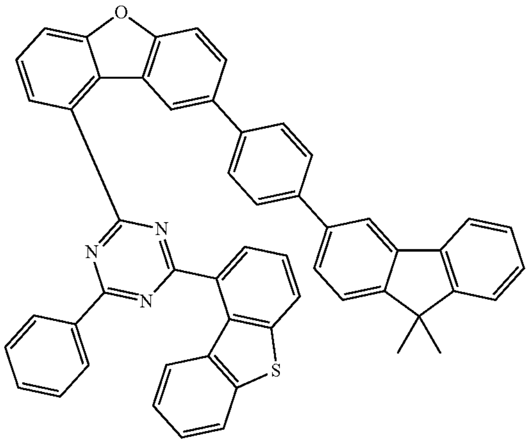 [SMILES: CC1(C)c2ccccc2-c2cc(-c3ccc(-c4ccc5oc6cccc(-c7nc(-c8ccccc8)nc(-c8cccc9sc%10ccccc%10c89)n7)c6c5c4)cc3)ccc21]

TABLE 1-continued
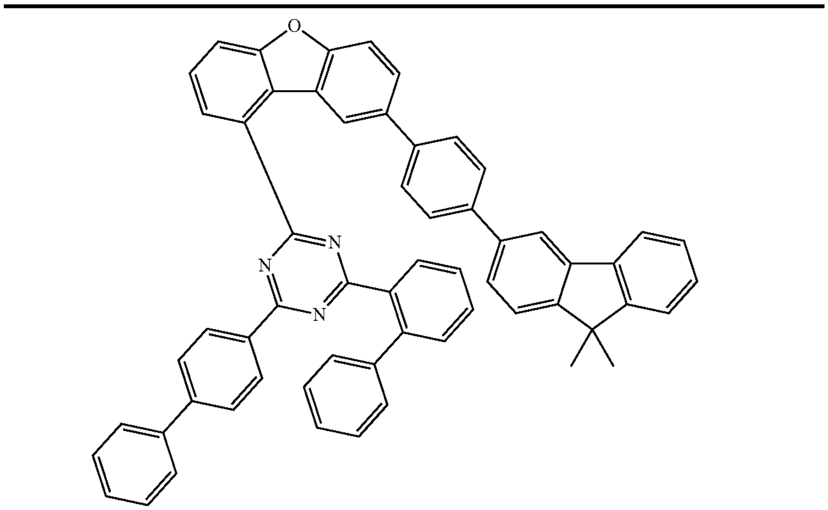
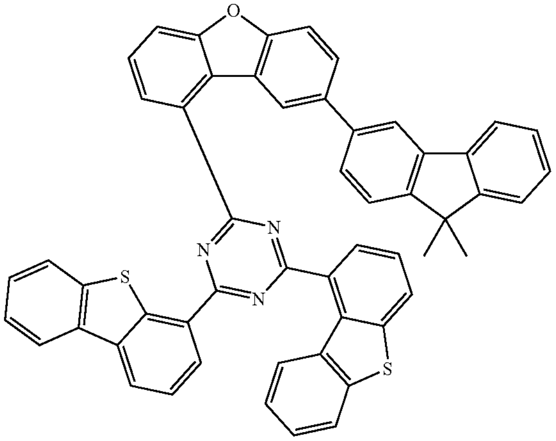 [SMILES: CC1(C)c2ccccc2-c2cc(-c3ccc4oc5cccc(-c6nc(-c7cccc8c7sc7ccccc78)nc(-c7cccc8sc9ccccc9c78)n6)c5c4c3)ccc21]
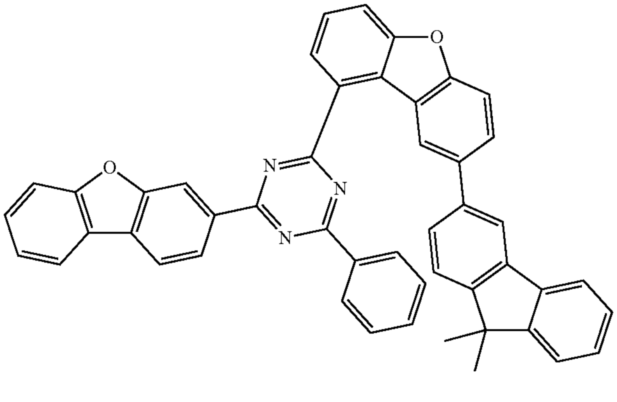 [SMILES: CC1(C)c2ccccc2-c2cc(-c3ccc4oc5cccc(-c6nc(-c7ccccc7)nc(-c7ccc8c(c7)oc7ccccc78)n6)c5c4c3)ccc21]

TABLE 1-continued
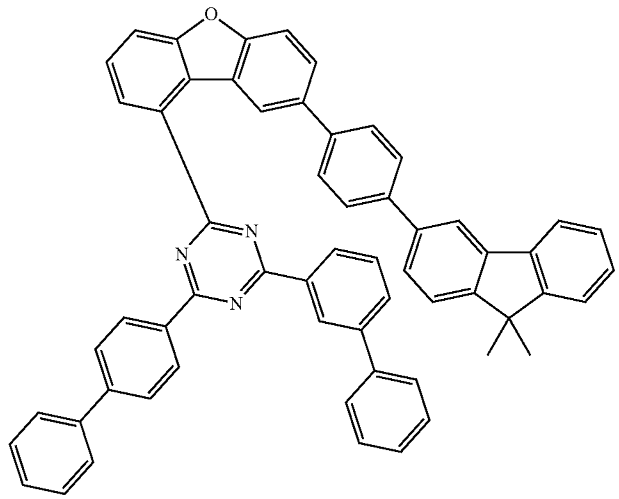 [SMILES: CC1(C)c2ccccc2-c2cc(-c3ccc(-c4ccc5oc6cccc(-c7nc(-c8ccc(-c9ccccc9)cc8)nc(-c8cccc(-c9ccccc9)c8)n7)c6c5c4)cc3)ccc21]
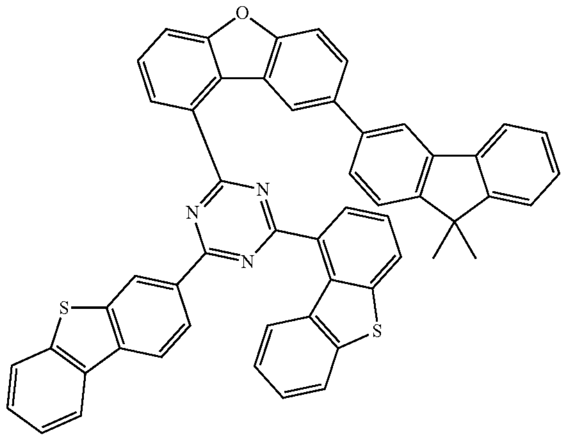 [SMILES: CC1(C)c2ccccc2-c2cc(-c3ccc4oc5cccc(-c6nc(-c7ccc8c(c7)sc7ccccc78)nc(-c7cccc8sc9ccccc9c78)n6)c5c4c3)ccc21]
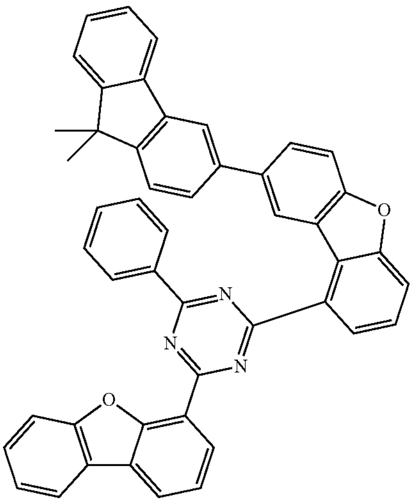 [SMILES: CC1(C)c2ccccc2-c2cc(-c3ccc4oc5cccc(-c6nc(-c7ccccc7)nc(-c7cccc8c7oc7ccccc78)n6)c5c4c3)ccc21]

TABLE 1-continued
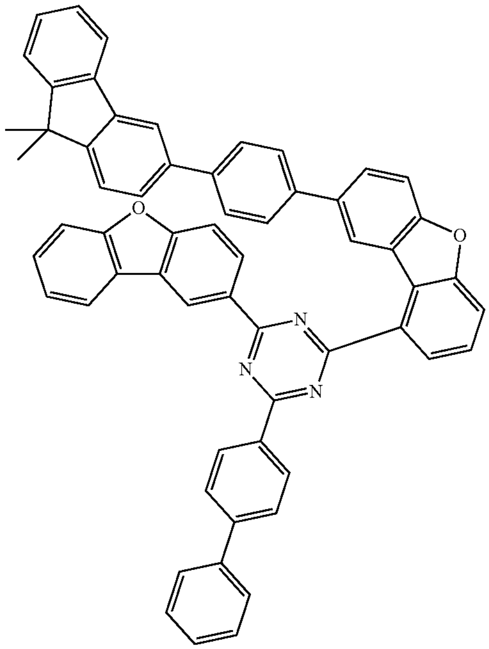 [SMILES: CC1(C)c2ccccc2-c2cc(-c3ccc(-c4ccc5oc6cccc(-c7nc(-c8ccc(-c9ccccc9)cc8)nc(-c8ccc9oc%10ccccc%10c9c8)n7)c6c5c4)cc3)ccc21]
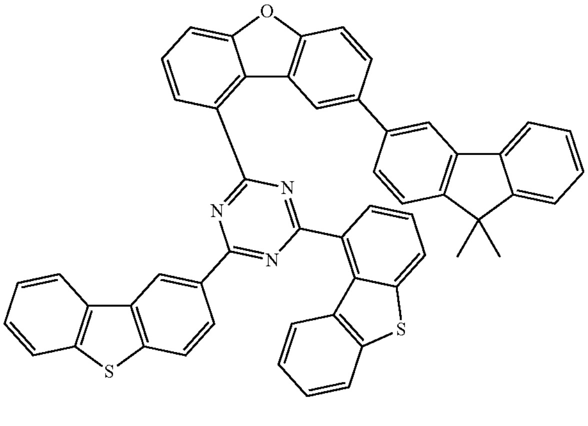 [SMILES: CC1(C)c2ccccc2-c2cc(-c3ccc4oc5cccc(-c6nc(-c7ccc8sc9ccccc9c8c7)nc(-c7cccc8sc9ccccc9c78)n6)c5c4c3)ccc21]
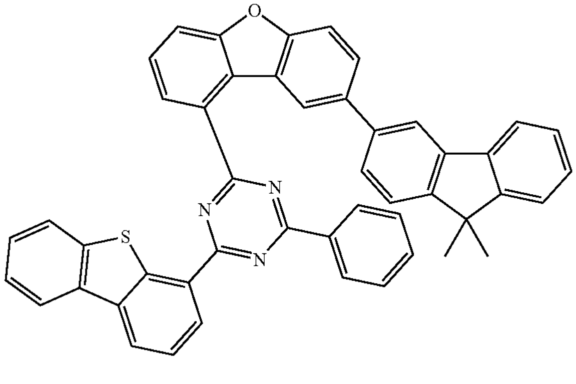 [SMILES: CC1(C)c2ccccc2-c2cc(-c3ccc4oc5cccc(-c6nc(-c7ccccc7)nc(-c7cccc8c7sc7ccccc78)n6)c5c4c3)ccc21]

TABLE 1-continued
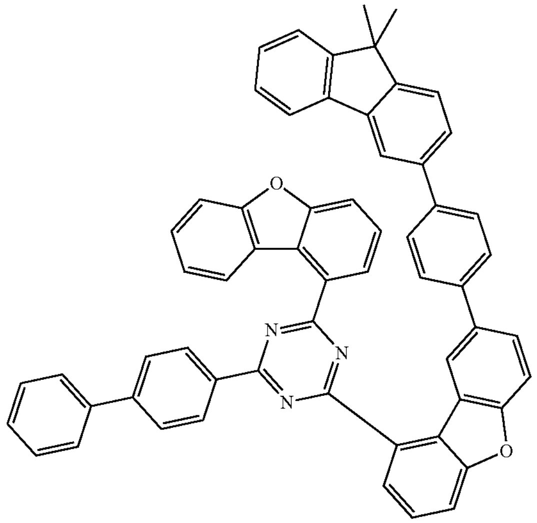 [SMILES: CC1(C)c2ccccc2-c2cc(-c3ccc(-c4ccc5oc6cccc(-c7nc(-c8ccc(-c9ccccc9)cc8)nc(-c8cccc9oc%10ccccc%10c89)n7)c6c5c4)cc3)ccc21]
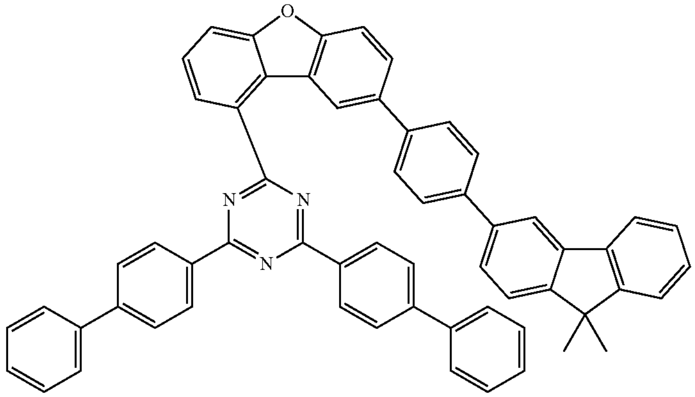 [SMILES: CC1(C)c2ccccc2-c2cc(-c3ccc(-c4ccc5oc6cccc(-c7nc(-c8ccc(-c9ccccc9)cc8)nc(-c8ccc(-c9ccccc9)cc8)n7)c6c5c4)cc3)ccc21]
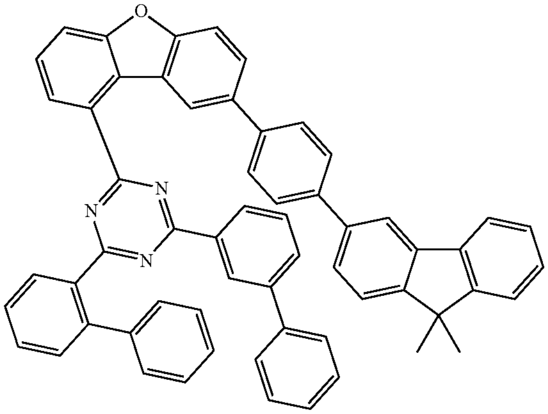 [SMILES: CC1(C)c2ccccc2-c2cc(-c3ccc(-c4ccc5oc6cccc(-c7nc(-c8cccc(-c9ccccc9)c8)nc(-c8ccccc8-c8ccccc8)n7)c6c5c4)cc3)ccc21]

TABLE 1-continued
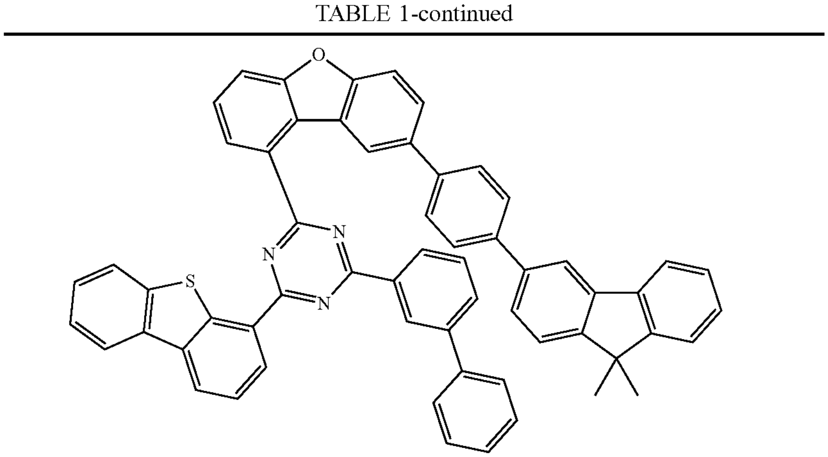
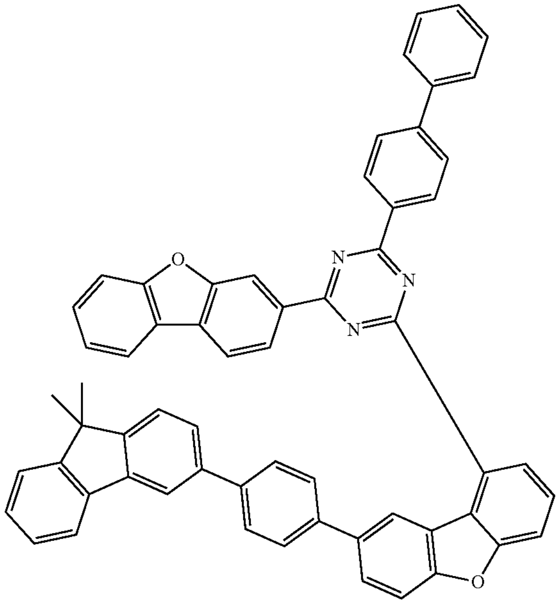 [SMILES: CC1(C)c2ccccc2-c2cc(-c3ccc(-c4ccc5oc6cccc(-c7nc(-c8ccc(-c9ccccc9)cc8)nc(-c8ccc9c(c8)oc8ccccc89)n7)c6c5c4)cc3)ccc21]
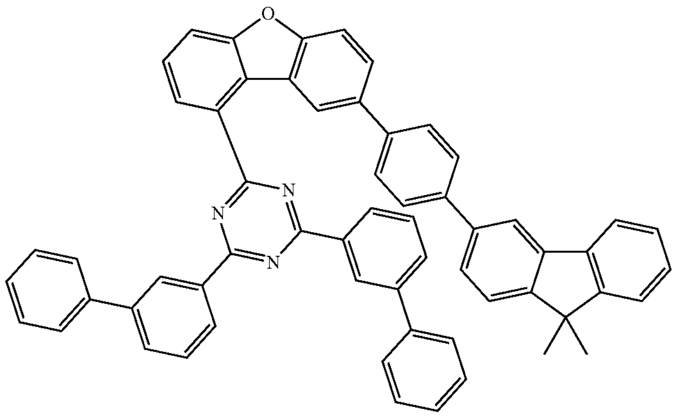 [SMILES: CC1(C)c2ccccc2-c2cc(-c3ccc(-c4ccc5oc6cccc(-c7nc(-c8cccc(-c9ccccc9)c8)nc(-c8cccc(-c9ccccc9)c8)n7)c6c5c4)cc3)ccc21]

TABLE 1-continued
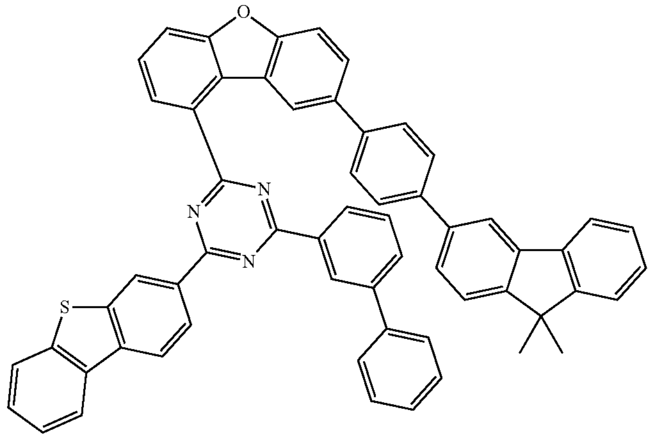 [SMILES: CC1(C)c2ccccc2-c2cc(-c3ccc(-c4ccc5oc6cccc(-c7nc(-c8cccc(-c9ccccc9)c8)nc(-c8ccc9c(c8)sc8ccccc89)n7)c6c5c4)cc3)ccc21]
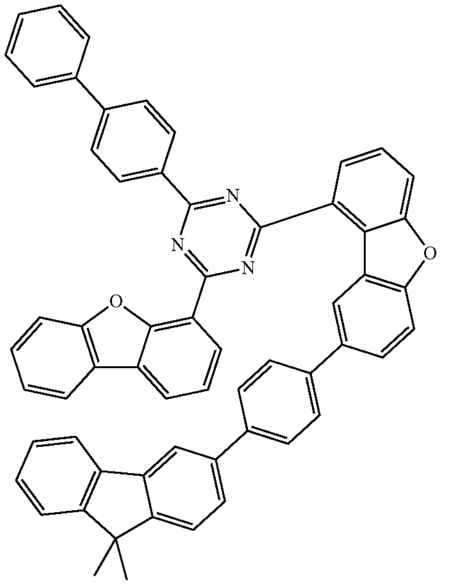 [SMILES: CC1(C)c2ccccc2-c2cc(-c3ccc(-c4ccc5oc6cccc(-c7nc(-c8ccc(-c9ccccc9)cc8)nc(-c8cccc9c8oc8ccccc89)n7)c6c5c4)cc3)ccc21]
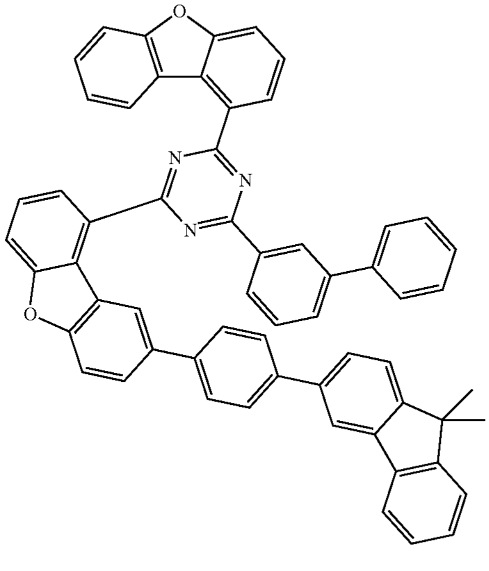 [SMILES: CC1(C)c2ccccc2-c2cc(-c3ccc(-c4ccc5oc6cccc(-c7nc(-c8cccc(-c9ccccc9)c8)nc(-c8cccc9oc%10ccccc%10c89)n7)c6c5c4)cc3)ccc21]

TABLE 1-continued
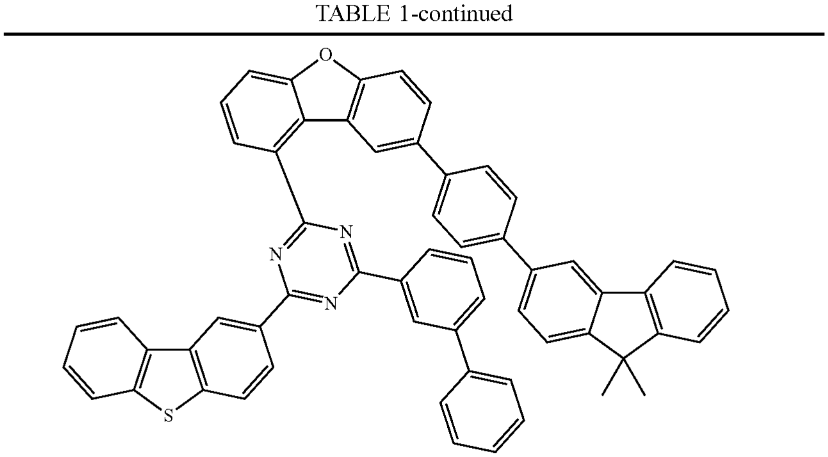
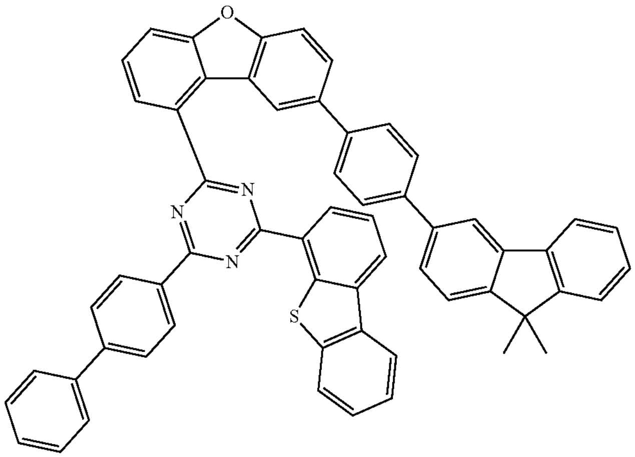 [SMILES: CC1(C)c2ccccc2-c2cc(-c3ccc(-c4ccc5oc6cccc(-c7nc(-c8ccc(-c9ccccc9)cc8)nc(-c8cccc9c8sc8ccccc89)n7)c6c5c4)cc3)ccc21]
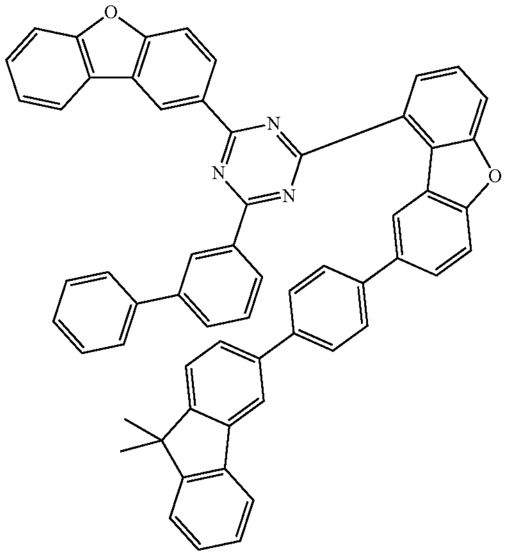 [SMILES: CC1(C)c2ccccc2-c2cc(-c3ccc(-c4ccc5oc6cccc(-c7nc(-c8cccc(-c9ccccc9)c8)nc(-c8ccc9oc%10ccccc%10c9c8)n7)c6c5c4)cc3)ccc21]

TABLE 1-continued
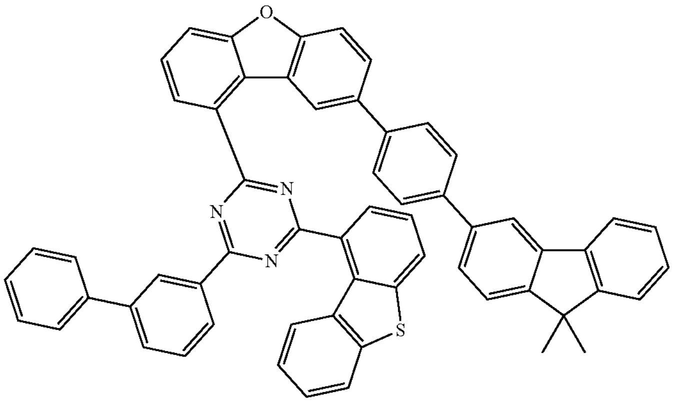 [SMILES: CC1(C)c2ccccc2-c2cc(-c3ccc(-c4ccc5oc6cccc(-c7nc(-c8cccc(-c9ccccc9)c8)nc(-c8cccc9sc%10ccccc%10c89)n7)c6c5c4)cc3)ccc21]
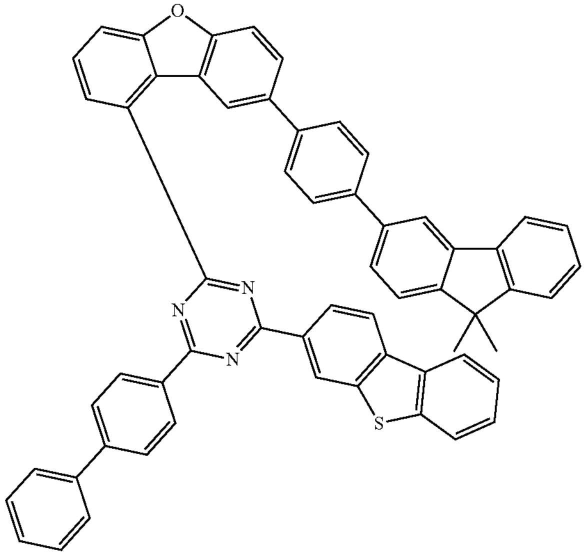 [SMILES: CC1(C)c2ccccc2-c2cc(-c3ccc(-c4ccc5oc6cccc(-c7nc(-c8ccc(-c9ccccc9)cc8)nc(-c8ccc9c(c8)sc8ccccc89)n7)c6c5c4)cc3)ccc21]
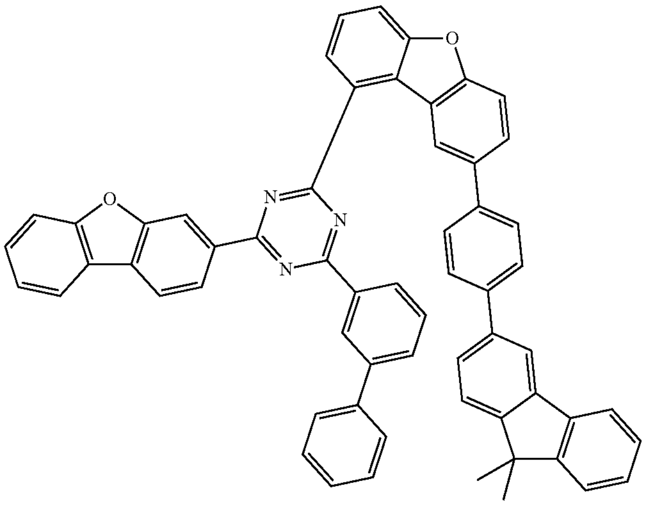 [SMILES: CC1(C)c2ccccc2-c2cc(-c3ccc(-c4ccc5oc6cccc(-c7nc(-c8cccc(-c9ccccc9)c8)nc(-c8ccc9c(c8)oc8ccccc89)n7)c6c5c4)cc3)ccc21]

TABLE 1-continued
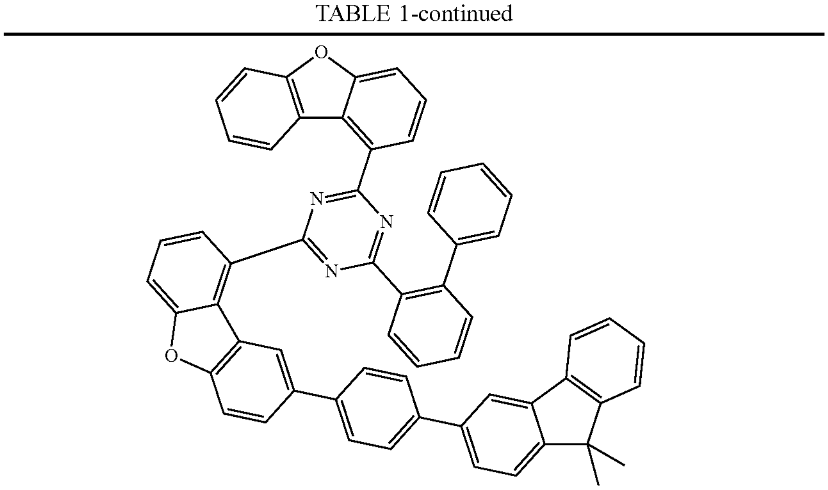
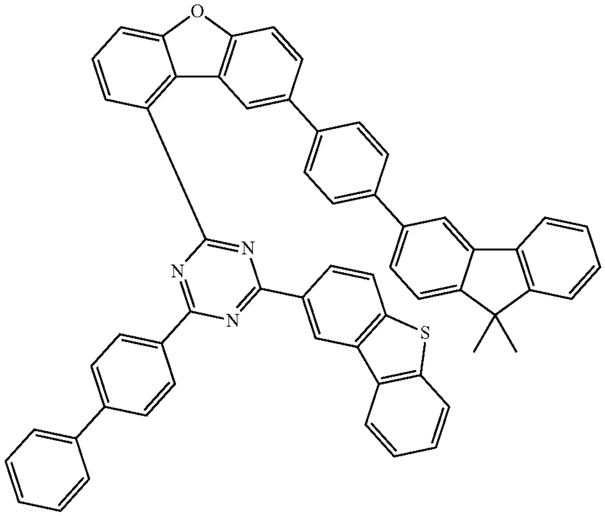 [SMILES: CC1(C)c2ccccc2-c2cc(-c3ccc(-c4ccc5oc6cccc(-c7nc(-c8ccc(-c9ccccc9)cc8)nc(-c8ccc9sc%10ccccc%10c9c8)n7)c6c5c4)cc3)ccc21]
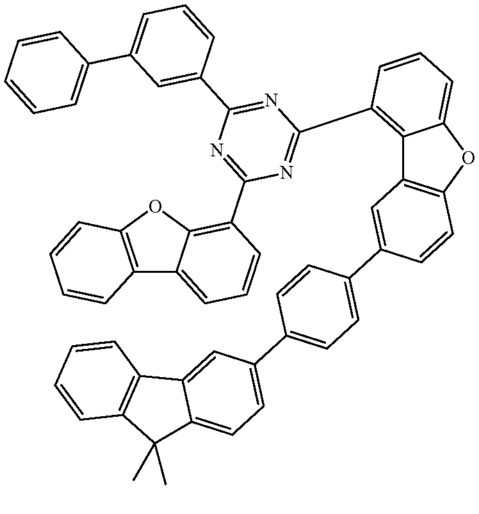 [SMILES: CC1(C)c2ccccc2-c2cc(-c3ccc(-c4ccc5oc6cccc(-c7nc(-c8cccc(-c9ccccc9)c8)nc(-c8cccc9c8oc8ccccc89)n7)c6c5c4)cc3)ccc21]

TABLE 1-continued
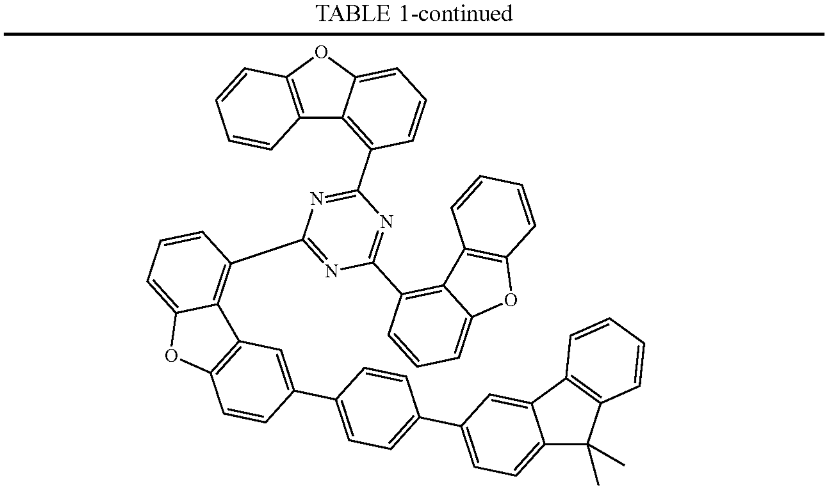
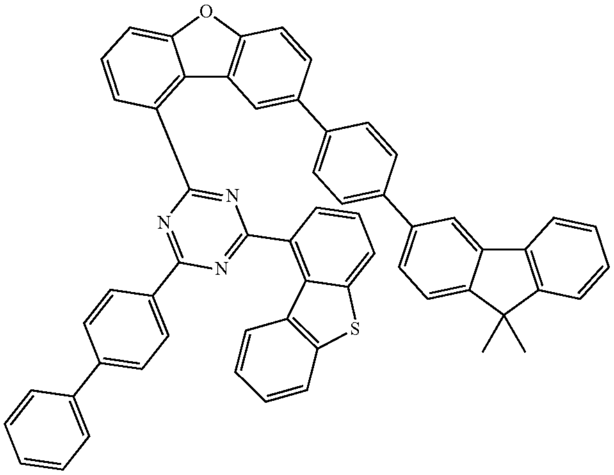 [SMILES: CC1(C)c2ccccc2-c2cc(-c3ccc(-c4ccc5oc6cccc(-c7nc(-c8ccc(-c9ccccc9)cc8)nc(-c8cccc9sc%10ccccc%10c89)n7)c6c5c4)cc3)ccc21]
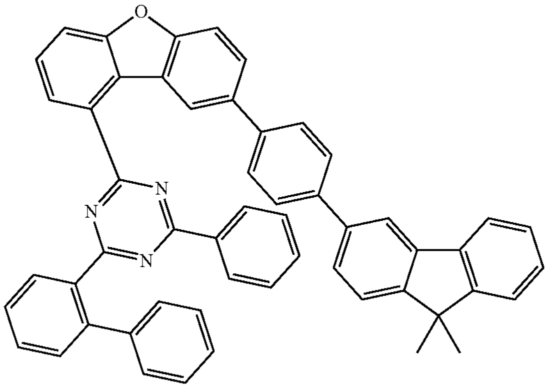 [SMILES: CC1(C)c2ccccc2-c2cc(-c3ccc(-c4ccc5oc6cccc(-c7nc(-c8ccccc8)nc(-c8ccccc8-c8ccccc8)n7)c6c5c4)cc3)ccc21]

TABLE 1-continued
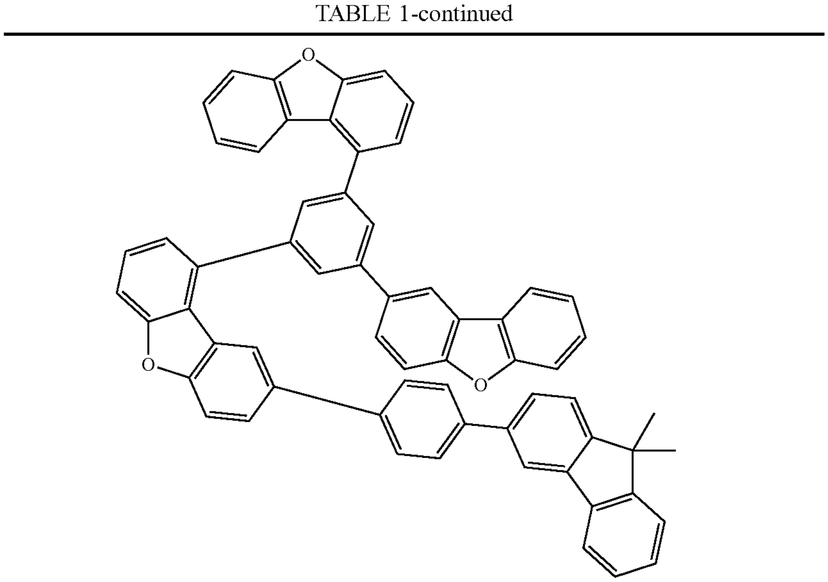
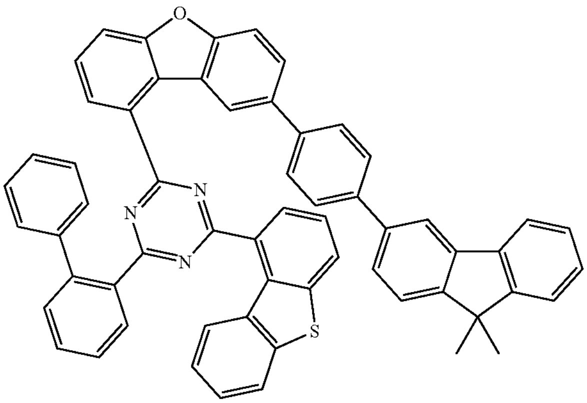 [SMILES: CC1(C)c2ccccc2-c2cc(-c3ccc(-c4ccc5oc6cccc(-c7nc(-c8ccccc8-c8ccccc8)nc(-c8cccc9sc%10ccccc%10c89)n7)c6c5c4)cc3)ccc21]
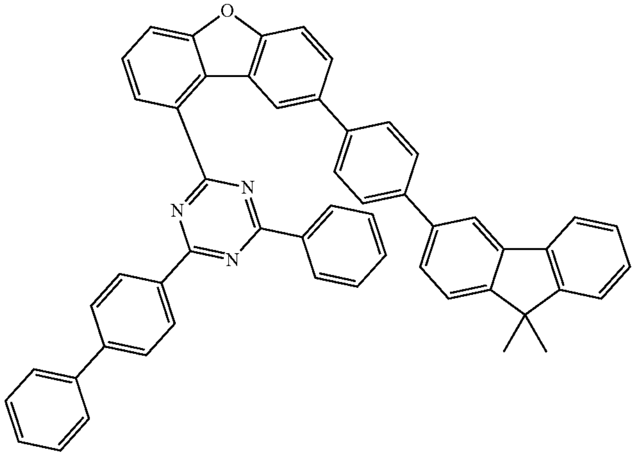 [SMILES: CC1(C)c2ccccc2-c2cc(-c3ccc(-c4ccc5oc6cccc(-c7nc(-c8ccccc8)nc(-c8ccc(-c9ccccc9)cc8)n7)c6c5c4)cc3)ccc21]

TABLE 1-continued
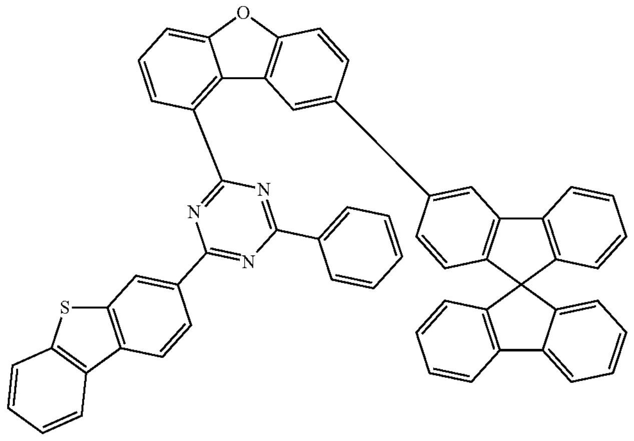 [SMILES: c1ccc(-c2nc(-c3ccc4c(c3)sc3ccccc34)nc(-c3cccc4oc5ccc(-c6ccc7c(c6)-c6ccccc6C76c7ccccc7-c7ccccc76)cc5c34)n2)cc1]
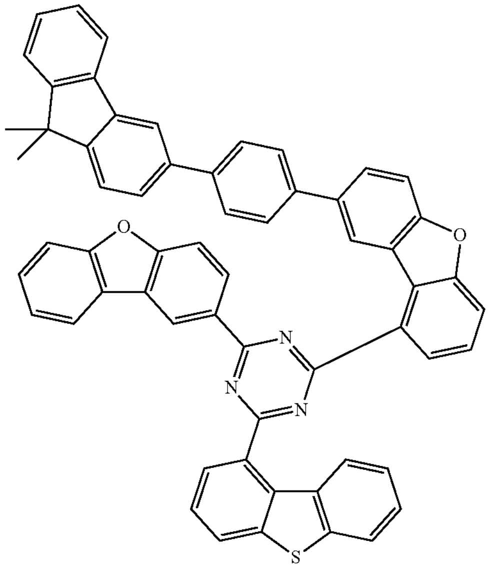 [SMILES: CC1(C)c2ccccc2-c2cc(-c3ccc(-c4ccc5oc6cccc(-c7nc(-c8ccc9oc%10ccccc%10c9c8)nc(-c8cccc9sc%10ccccc%10c89)n7)c6c5c4)cc3)ccc21]
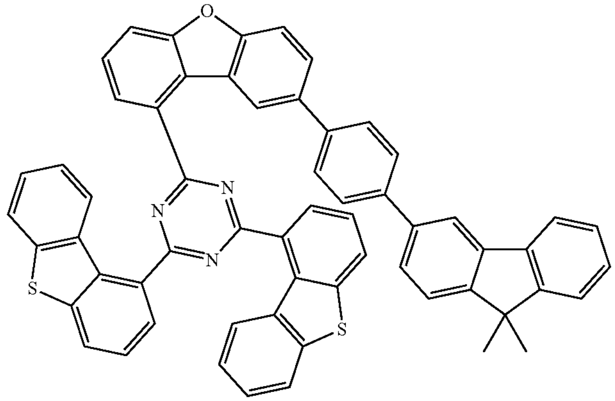 [SMILES: CC1(C)c2ccccc2-c2cc(-c3ccc(-c4ccc5oc6cccc(-c7nc(-c8cccc9sc%10ccccc%10c89)nc(-c8cccc9sc%10ccccc%10c89)n7)c6c5c4)cc3)ccc21]

TABLE 1-continued
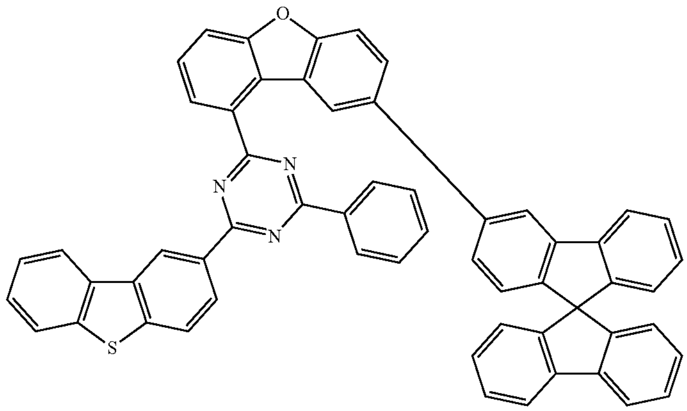 [SMILES: c1ccc(-c2nc(-c3ccc4sc5ccccc5c4c3)nc(-c3cccc4oc5ccc(-c6ccc7c(c6)-c6ccccc6C76c7ccccc7-c7ccccc76)cc5c34)n2)cc1]
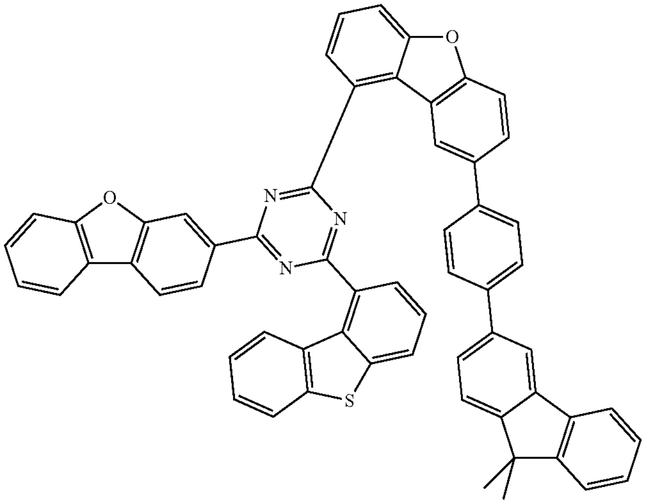 [SMILES: CC1(C)c2ccccc2-c2cc(-c3ccc(-c4ccc5oc6cccc(-c7nc(-c8ccc9c(c8)oc8ccccc89)nc(-c8cccc9sc%10ccccc%10c89)n7)c6c5c4)cc3)ccc21]
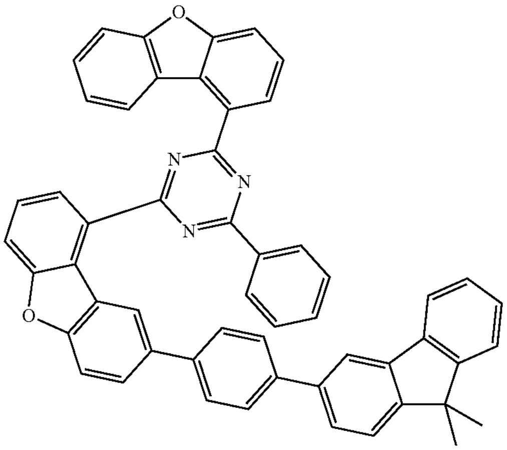 [SMILES: CC1(C)c2ccccc2-c2cc(-c3ccc(-c4ccc5oc6cccc(-c7nc(-c8ccccc8)nc(-c8cccc9oc%10ccccc%10c89)n7)c6c5c4)cc3)ccc21]

TABLE 1-continued
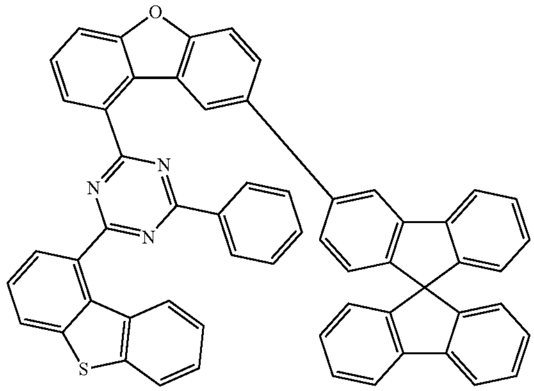 [SMILES: c1ccc(-c2nc(-c3cccc4oc5ccc(-c6ccc7c(c6)-c6ccccc6C76c7ccccc7-c7ccccc76)cc5c34)nc(-c3cccc4sc5ccccc5c34)n2)cc1]
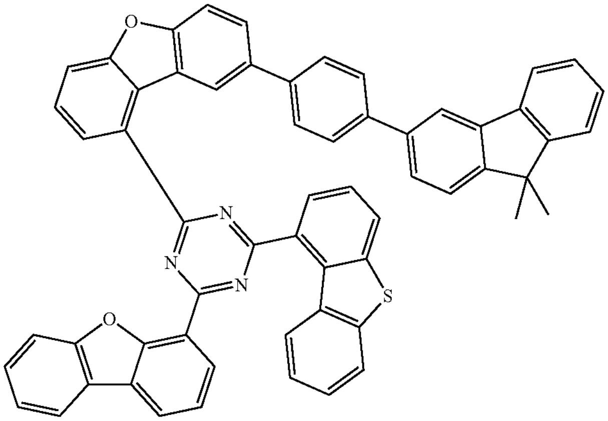 [SMILES: CC1(C)c2ccccc2-c2cc(-c3ccc(-c4ccc5oc6cccc(-c7nc(-c8cccc9c8oc8ccccc89)nc(-c8cccc9sc%10ccccc%10c89)n7)c6c5c4)cc3)ccc21]
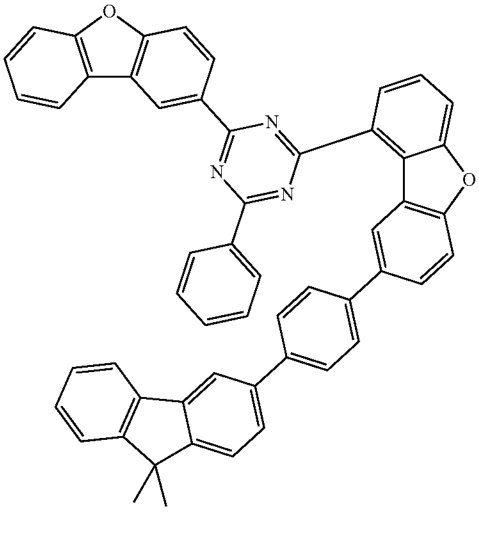 [SMILES: CC1(C)c2ccccc2-c2cc(-c3ccc(-c4ccc5oc6cccc(-c7nc(-c8ccccc8)nc(-c8ccc9oc%10ccccc%10c9c8)n7)c6c5c4)cc3)ccc21]

TABLE 1-continued
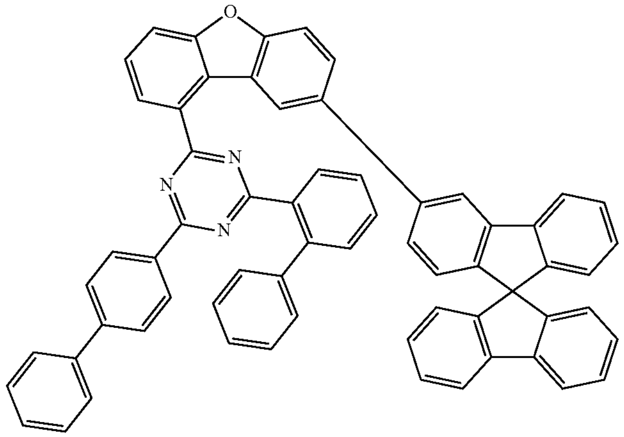 [SMILES: c1ccc(-c2ccc(-c3nc(-c4ccccc4-c4ccccc4)nc(-c4cccc5oc6ccc(-c7ccc8c(c7)-c7ccccc7C87c8ccccc8-c8ccccc87)cc6c45)n3)cc2)cc1]
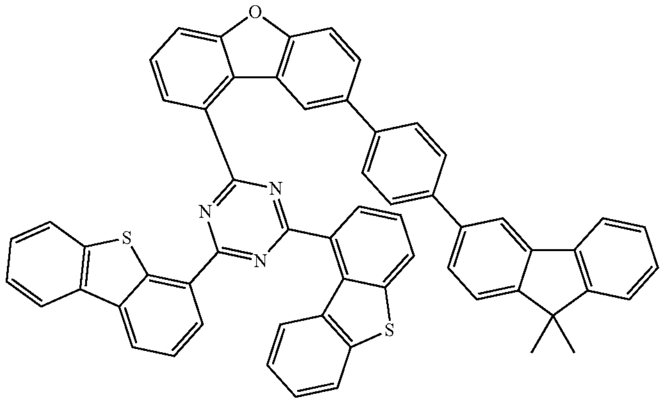 [SMILES: CC1(C)c2ccccc2-c2cc(-c3ccc(-c4ccc5oc6cccc(-c7nc(-c8cccc9c8sc8ccccc89)nc(-c8cccc9sc%10ccccc%10c89)n7)c6c5c4)cc3)ccc21]
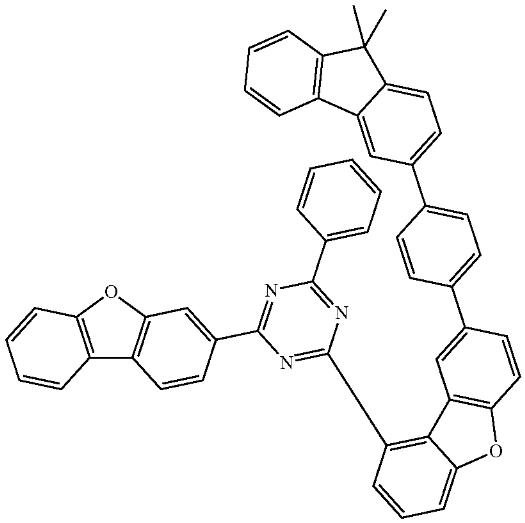 [SMILES: CC1(C)c2ccccc2-c2cc(-c3ccc(-c4ccc5oc6cccc(-c7nc(-c8ccccc8)nc(-c8ccc9c(c8)oc8ccccc89)n7)c6c5c4)cc3)ccc21]

TABLE 1-continued
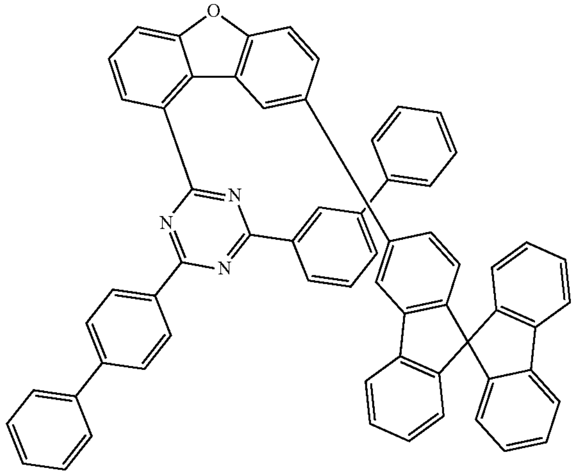 [SMILES: c1ccc(-c2ccc(-c3nc(-c4cccc(-c5ccccc5)c4)nc(-c4cccc5oc6ccc(-c7ccc8c(c7)-c7ccccc7C87c8ccccc8-c8ccccc87)cc6c45)n3)cc2)cc1]
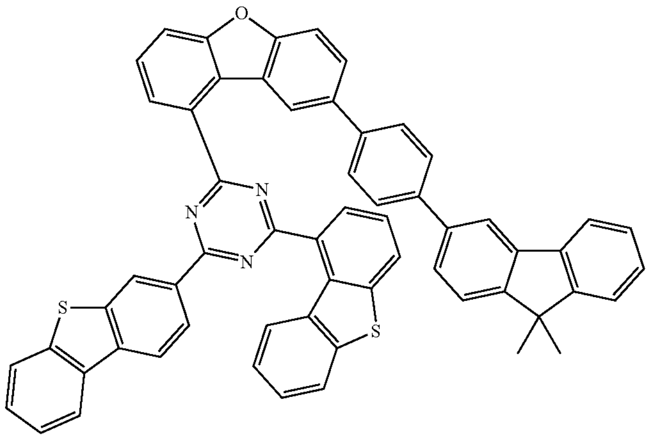 [SMILES: CC1(C)c2ccccc2-c2cc(-c3ccc(-c4ccc5oc6cccc(-c7nc(-c8ccc9c(c8)sc8ccccc89)nc(-c8cccc9sc%10ccccc%10c89)n7)c6c5c4)cc3)ccc21]
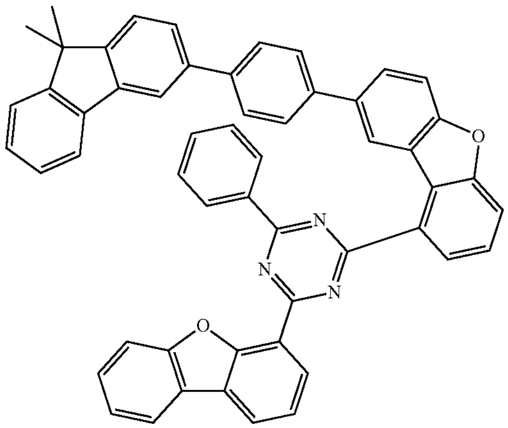 [SMILES: CC1(C)c2ccccc2-c2cc(-c3ccc(-c4ccc5oc6cccc(-c7nc(-c8ccccc8)nc(-c8cccc9c8oc8ccccc89)n7)c6c5c4)cc3)ccc21]

TABLE 1-continued
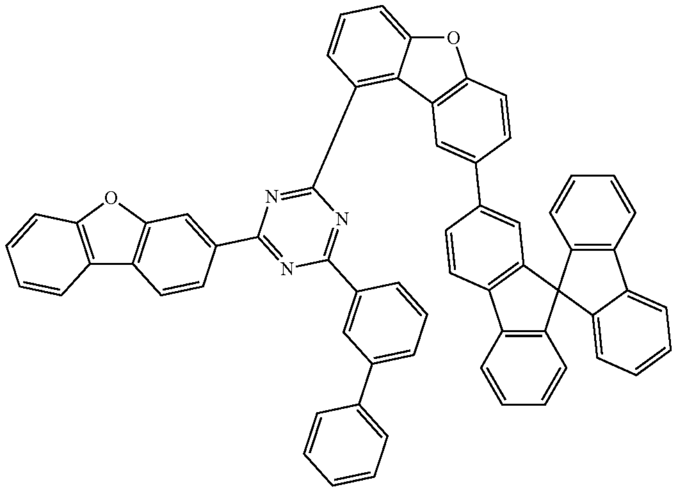 [SMILES: c1ccc(-c2cccc(-c3nc(-c4ccc5c(c4)oc4ccccc45)nc(-c4cccc5oc6ccc(-c7ccc8c(c7)C7(c9ccccc9-c9ccccc97)c7ccccc7-8)cc6c45)n3)c2)cc1]
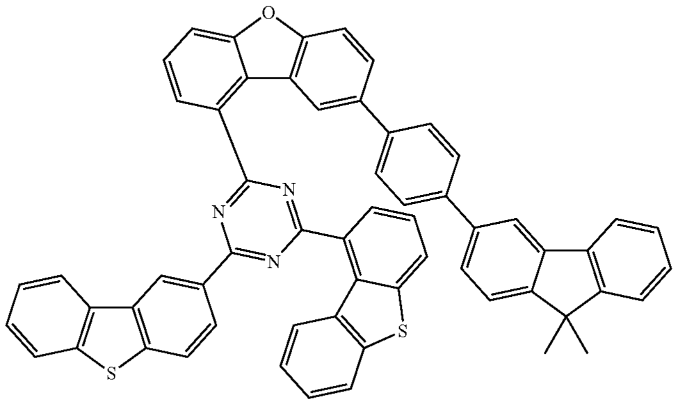 [SMILES: CC1(C)c2ccccc2-c2cc(-c3ccc(-c4ccc5oc6cccc(-c7nc(-c8ccc9sc%10ccccc%10c9c8)nc(-c8cccc9sc%10ccccc%10c89)n7)c6c5c4)cc3)ccc21]
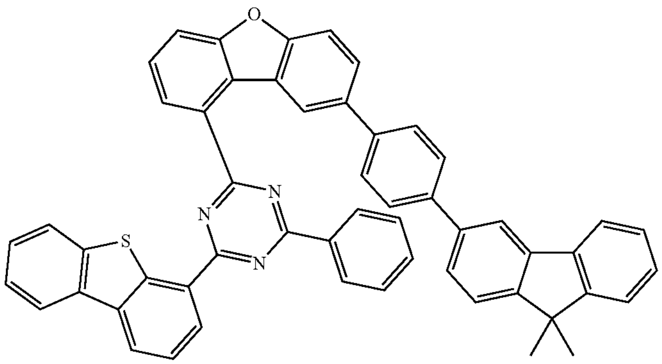 [SMILES: CC1(C)c2ccccc2-c2cc(-c3ccc(-c4ccc5oc6cccc(-c7nc(-c8ccccc8)nc(-c8cccc9c8sc8ccccc89)n7)c6c5c4)cc3)ccc21]

TABLE 1-continued
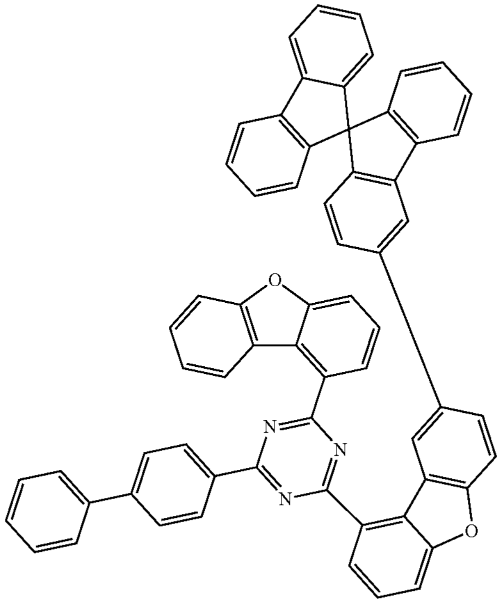 [SMILES: c1ccc(-c2ccc(-c3nc(-c4cccc5oc6ccccc6c45)nc(-c4cccc5oc6ccc(-c7ccc8c(c7)-c7ccccc7C87c8ccccc8-c8ccccc87)cc6c45)n3)cc2)cc1]
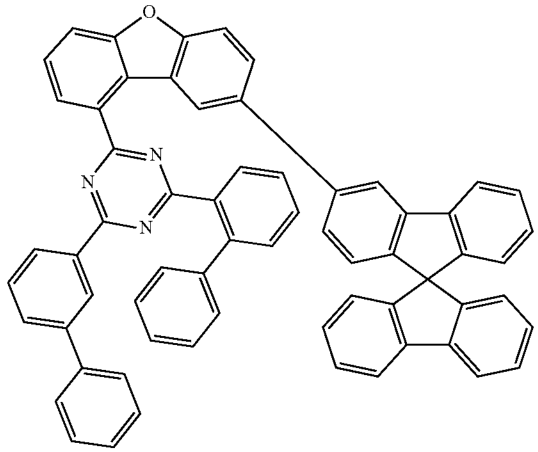 [SMILES: c1ccc(-c2cccc(-c3nc(-c4ccccc4-c4ccccc4)nc(-c4cccc5oc6ccc(-c7ccc8c(c7)-c7ccccc7C87c8ccccc8-c8ccccc87)cc6c45)n3)c2)cc1]
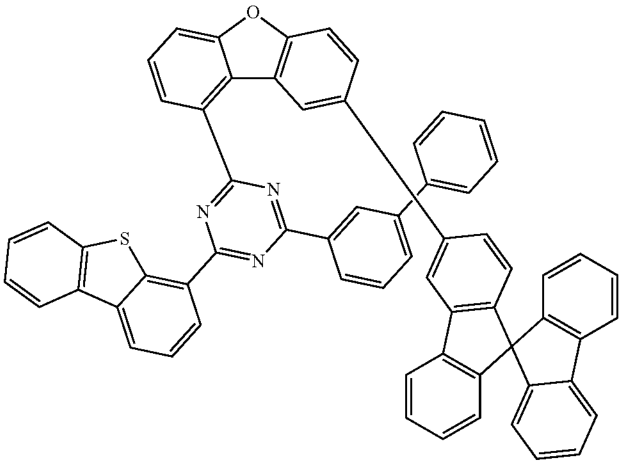 [SMILES: c1ccc(-c2cccc(-c3nc(-c4cccc5c4sc4ccccc45)nc(-c4cccc5oc6ccc(-c7ccc8c(c7)-c7ccccc7C87c8ccccc8-c8ccccc87)cc6c45)n3)c2)cc1]

TABLE 1-continued
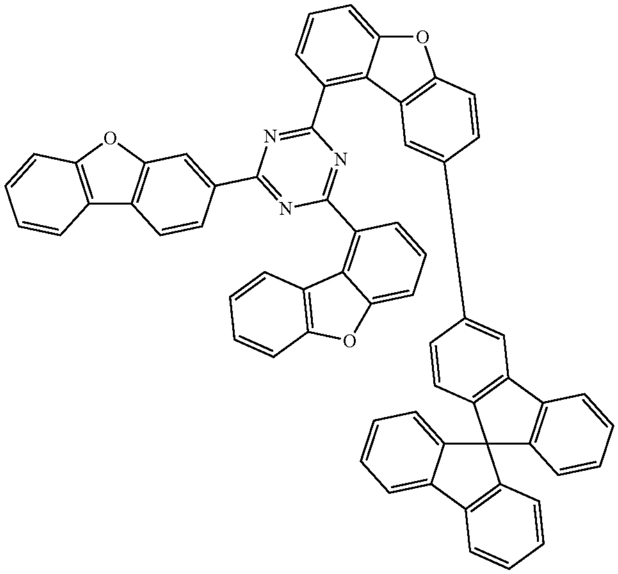 [SMILES: c1ccc2c(c1)-c1ccccc1C21c2ccccc2-c2cc(-c3ccc4oc5cccc(-c6nc(-c7ccc8c(c7)oc7ccccc78)nc(-c7cccc8oc9ccccc9c78)n6)c5c4c3)ccc21]
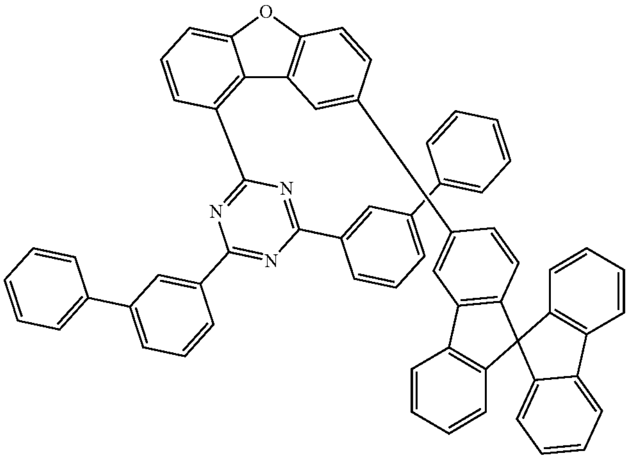 [SMILES: c1ccc(-c2cccc(-c3nc(-c4cccc(-c5ccccc5)c4)nc(-c4cccc5oc6ccc(-c7ccc8c(c7)-c7ccccc7C87c8ccccc8-c8ccccc87)cc6c45)n3)c2)cc1]
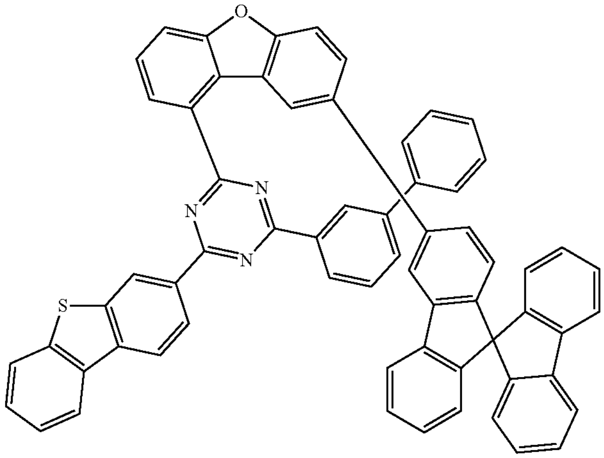 [SMILES: c1ccc(-c2cccc(-c3nc(-c4ccc5c(c4)sc4ccccc45)nc(-c4cccc5oc6ccc(-c7ccc8c(c7)-c7ccccc7C87c8ccccc8-c8ccccc87)cc6c45)n3)c2)cc1]

TABLE 1-continued
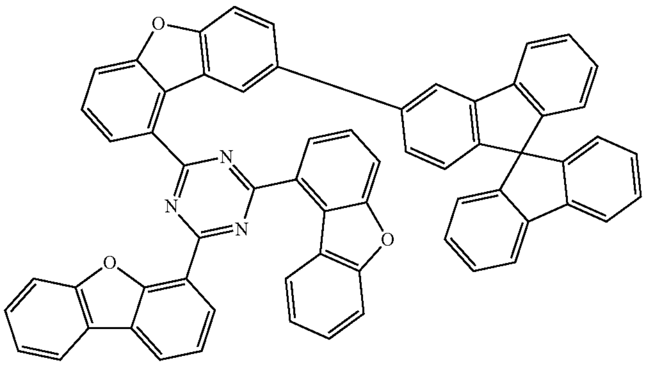 [SMILES: c1ccc2c(c1)-c1ccccc1C21c2ccccc2-c2cc(-c3ccc4oc5cccc(-c6nc(-c7cccc8c7oc7ccccc78)nc(-c7cccc8oc9ccccc9c78)n6)c5c4c3)ccc21]
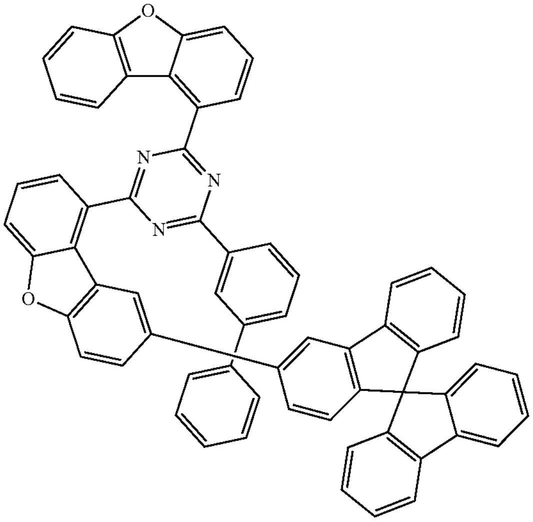 [SMILES: c1ccc(-c2cccc(-c3nc(-c4cccc5oc6ccccc6c45)nc(-c4cccc5oc6ccc(-c7ccc8c(c7)-c7ccccc7C87c8ccccc8-c8ccccc87)cc6c45)n3)c2)cc1]
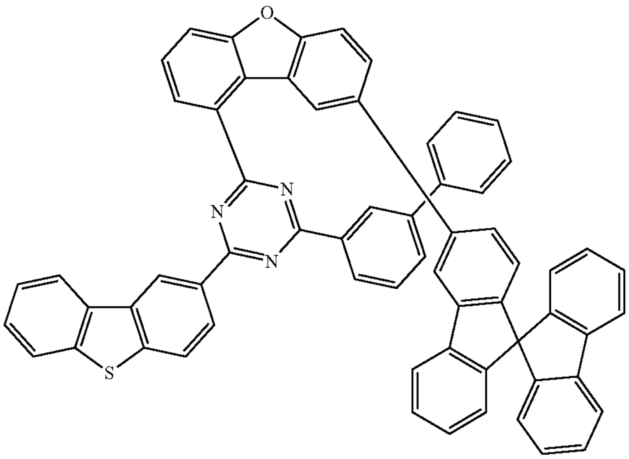 [SMILES: c1ccc(-c2cccc(-c3nc(-c4ccc5sc6ccccc6c5c4)nc(-c4cccc5oc6ccc(-c7ccc8c(c7)-c7ccccc7C87c8ccccc8-c8ccccc87)cc6c45)n3)c2)cc1]

TABLE 1-continued
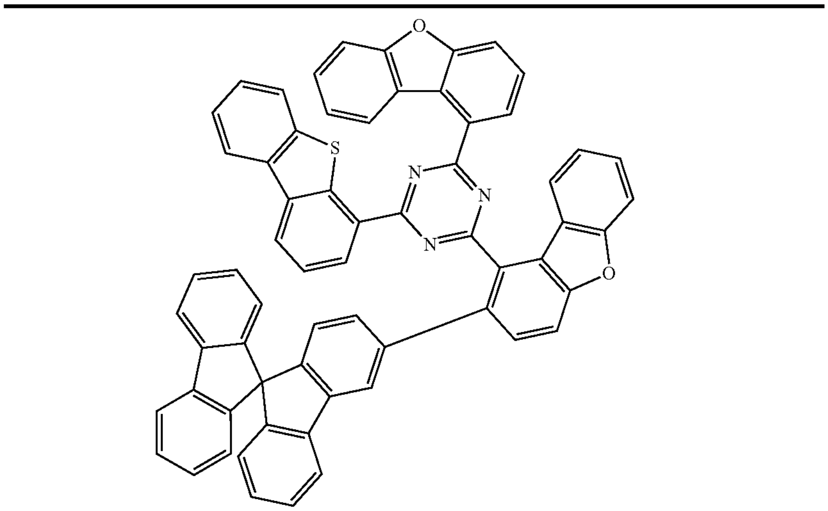
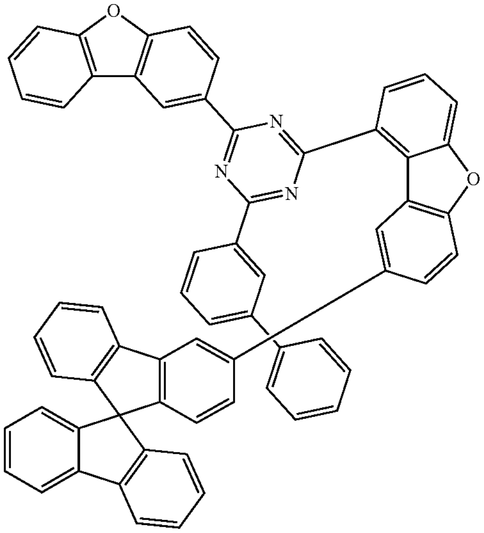 [SMILES: c1ccc(-c2cccc(-c3nc(-c4ccc5oc6ccccc6c5c4)nc(-c4cccc5oc6ccc(-c7ccc8c(c7)-c7ccccc7C87c8ccccc8-c8ccccc87)cc6c45)n3)c2)cc1]
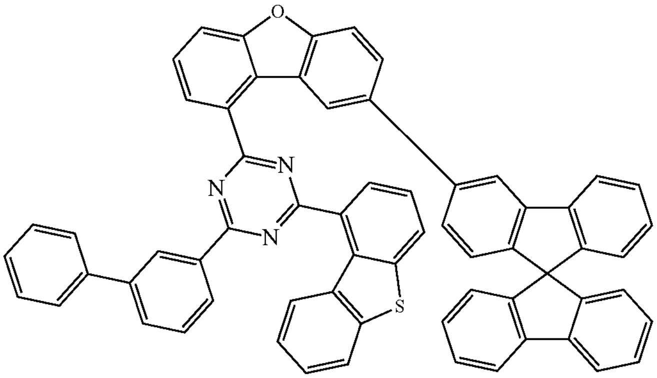 [SMILES: c1ccc(-c2cccc(-c3nc(-c4cccc5oc6ccc(-c7ccc8c(c7)-c7ccccc7C87c8ccccc8-c8ccccc87)cc6c45)nc(-c4cccc5sc6ccccc6c45)n3)c2)cc1]

TABLE 1-continued
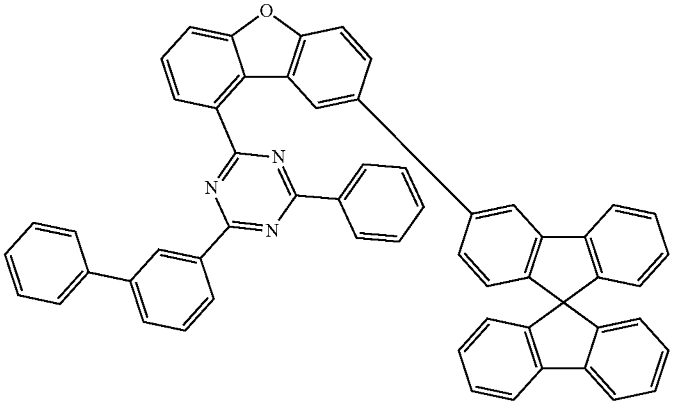 [SMILES: c1ccc(-c2cccc(-c3nc(-c4ccccc4)nc(-c4cccc5oc6ccc(-c7ccc8c(c7)-c7ccccc7C87c8ccccc8-c8ccccc87)cc6c45)n3)c2)cc1]
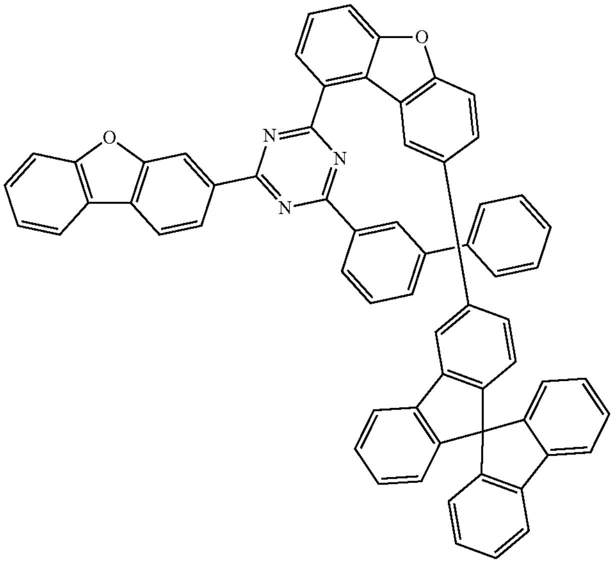 [SMILES: c1ccc(-c2cccc(-c3nc(-c4ccc5c(c4)oc4ccccc45)nc(-c4cccc5oc6ccc(-c7ccc8c(c7)-c7ccccc7C87c8ccccc8-c8ccccc87)cc6c45)n3)c2)cc1]
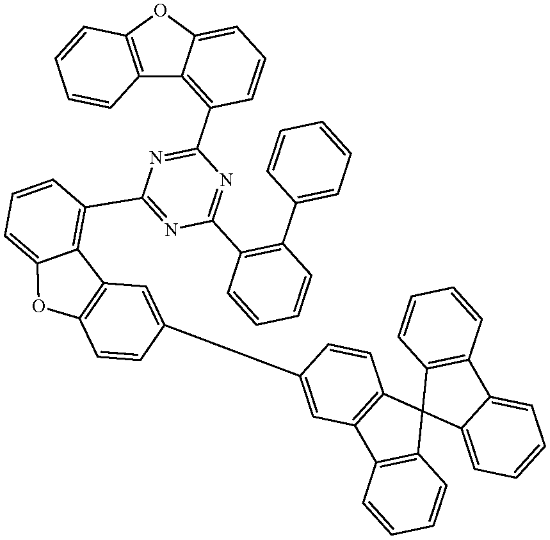 [SMILES: c1ccc(-c2ccccc2-c2nc(-c3cccc4oc5ccccc5c34)nc(-c3cccc4oc5ccc(-c6ccc7c(c6)-c6ccccc6C76c7ccccc7-c7ccccc76)cc5c34)n2)cc1]

TABLE 1-continued
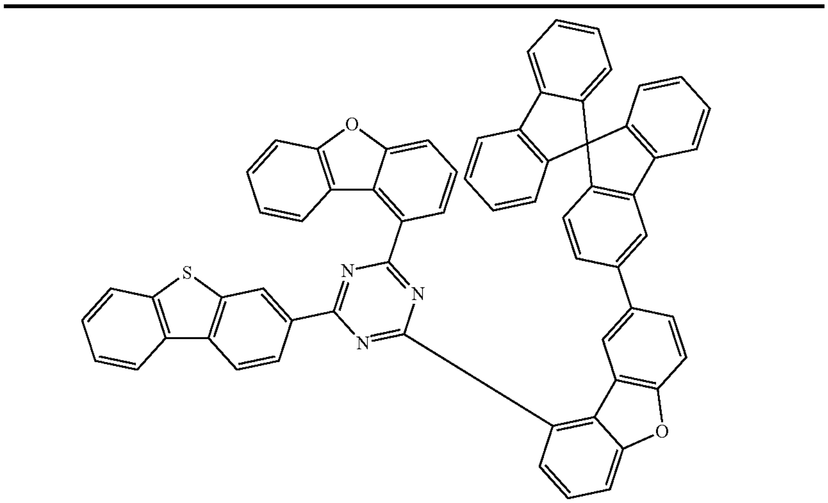
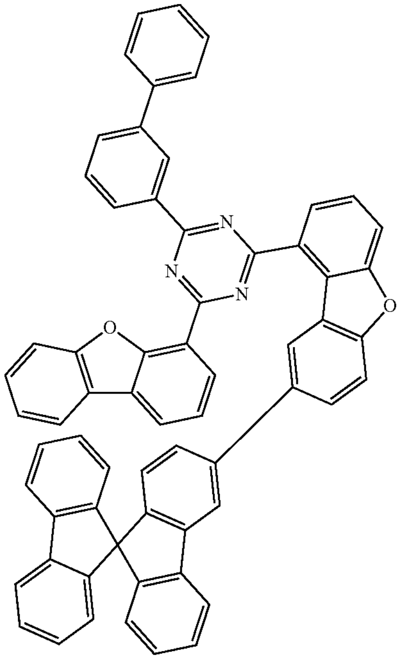 [SMILES: c1ccc(-c2cccc(-c3nc(-c4cccc5c4oc4ccccc45)nc(-c4cccc5oc6ccc(-c7ccc8c(c7)-c7ccccc7C87c8ccccc8-c8ccccc87)cc6c45)n3)c2)cc1]

TABLE 1-continued
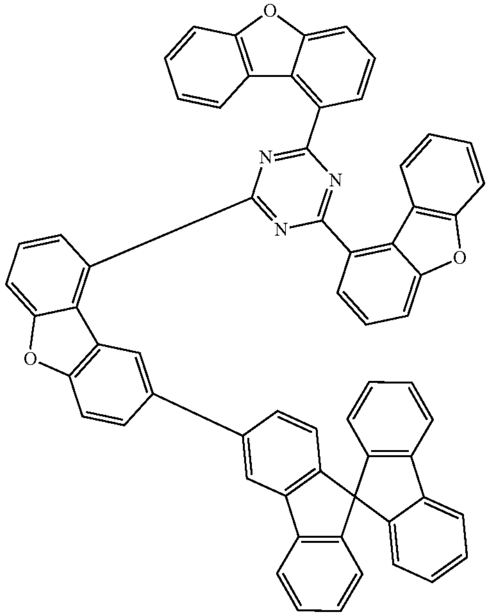 [SMILES: c1ccc2c(c1)-c1ccccc1C21c2ccccc2-c2cc(-c3ccc4oc5cccc(-c6nc(-c7cccc8oc9ccccc9c78)nc(-c7cccc8oc9ccccc9c78)n6)c5c4c3)ccc21]
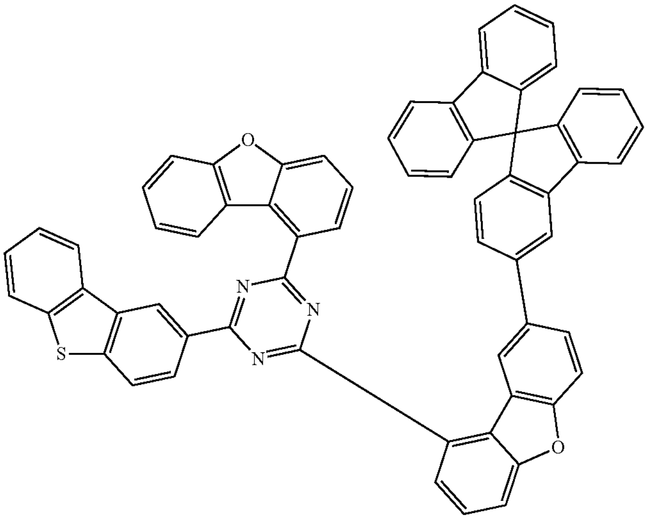 [SMILES: c1ccc2c(c1)-c1ccccc1C21c2ccccc2-c2cc(-c3ccc4oc5cccc(-c6nc(-c7ccc8sc9ccccc9c8c7)nc(-c7cccc8oc9ccccc9c78)n6)c5c4c3)ccc21]
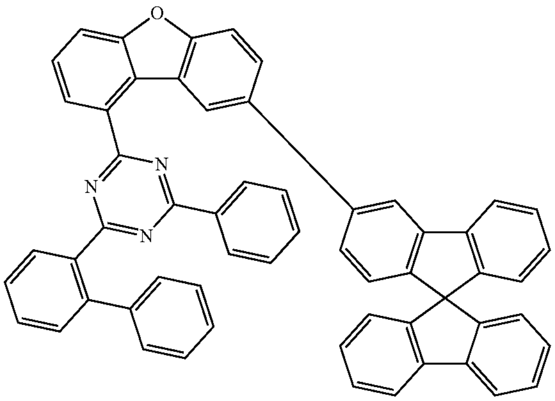 [SMILES: c1ccc(-c2nc(-c3ccccc3-c3ccccc3)nc(-c3cccc4oc5ccc(-c6ccc7c(c6)-c6ccccc6C76c7ccccc7-c7ccccc76)cc5c34)n2)cc1]

TABLE 1-continued
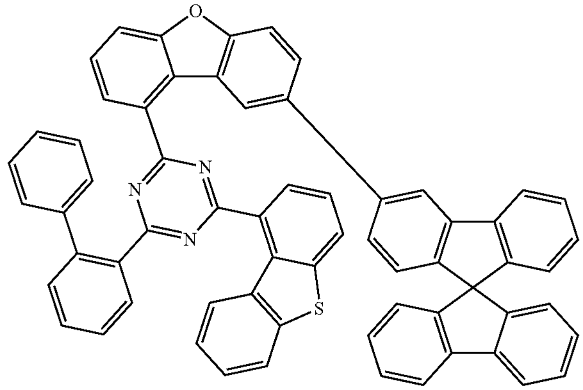 [SMILES: c1ccc(-c2ccccc2-c2nc(-c3cccc4oc5ccc(-c6ccc7c(c6)-c6ccccc6C76c7ccccc7-c7ccccc76)cc5c34)nc(-c3cccc4sc5ccccc5c34)n2)cc1]
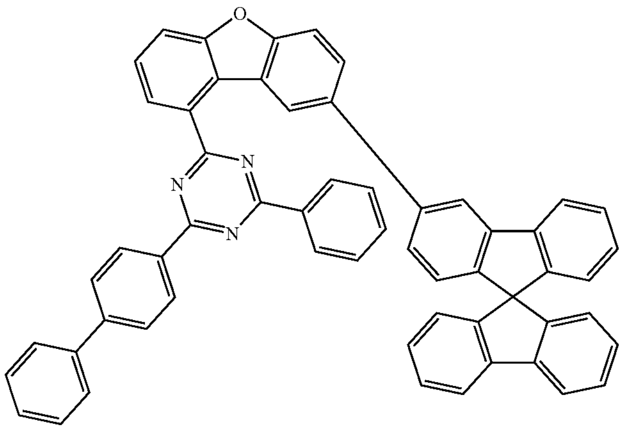 [SMILES: c1ccc(-c2ccc(-c3nc(-c4ccccc4)nc(-c4cccc5oc6ccc(-c7ccc8c(c7)-c7ccccc7C87c8ccccc8-c8ccccc87)cc6c45)n3)cc2)cc1]
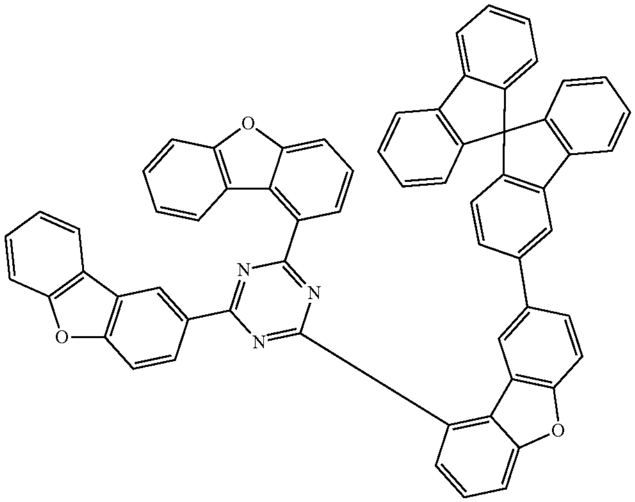 [SMILES: c1ccc2c(c1)-c1ccccc1C21c2ccccc2-c2cc(-c3ccc4oc5cccc(-c6nc(-c7ccc8oc9ccccc9c8c7)nc(-c7cccc8oc9ccccc9c78)n6)c5c4c3)ccc21]

TABLE 1-continued
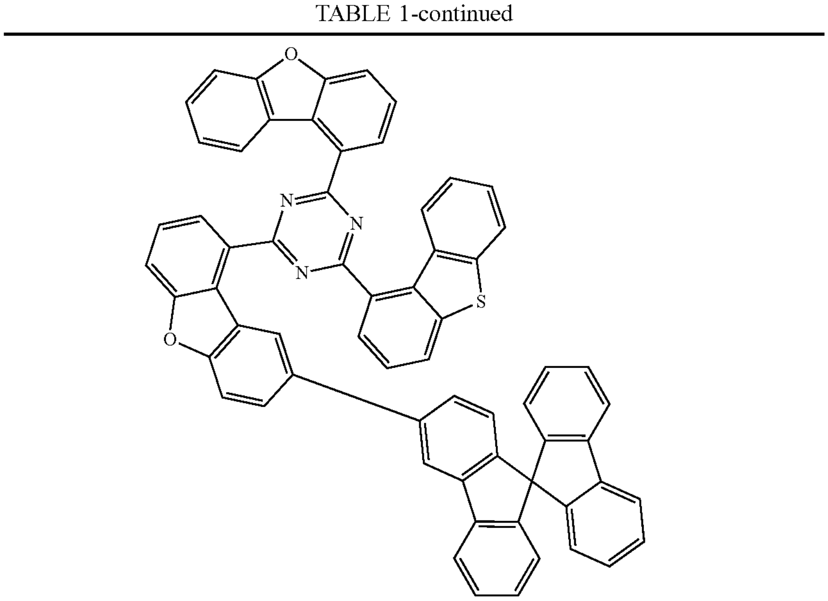
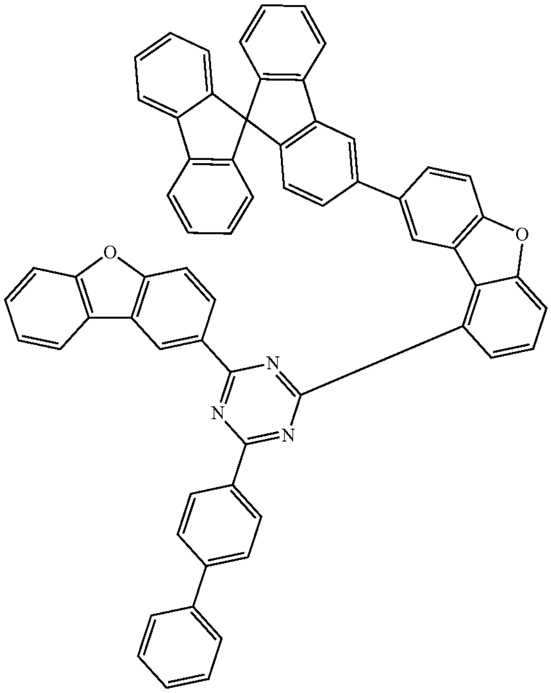 [SMILES: c1ccc(-c2ccc(-c3nc(-c4ccc5oc6ccccc6c5c4)nc(-c4cccc5oc6ccc(-c7ccc8c(c7)-c7ccccc7C87c8ccccc8-c8ccccc87)cc6c45)n3)cc2)cc1]

TABLE 1-continued
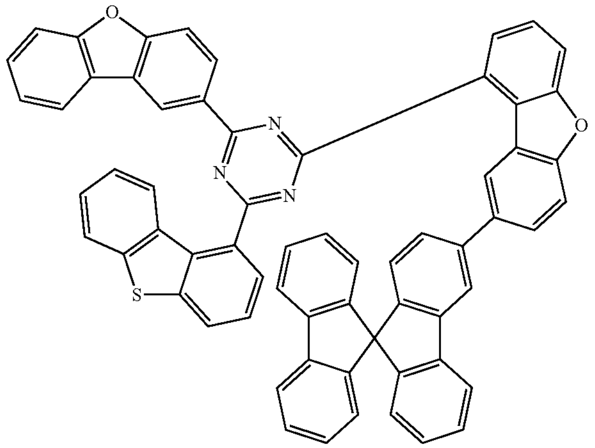 [SMILES: c1ccc2c(c1)-c1ccccc1C21c2ccccc2-c2cc(-c3ccc4oc5cccc(-c6nc(-c7ccc8oc9ccccc9c8c7)nc(-c7cccc8sc9ccccc9c78)n6)c5c4c3)ccc21]
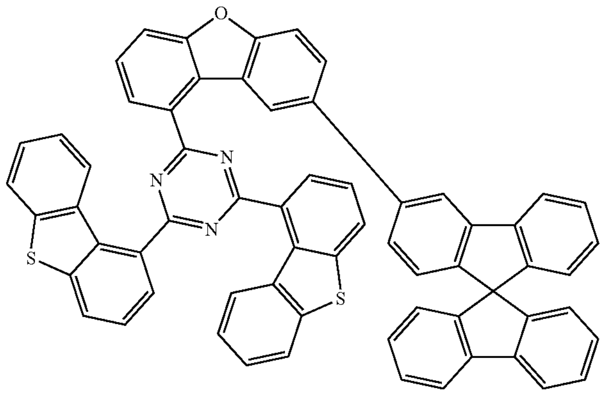 [SMILES: c1ccc2c(c1)-c1ccccc1C21c2ccccc2-c2cc(-c3ccc4oc5cccc(-c6nc(-c7cccc8sc9ccccc9c78)nc(-c7cccc8sc9ccccc9c78)n6)c5c4c3)ccc21]
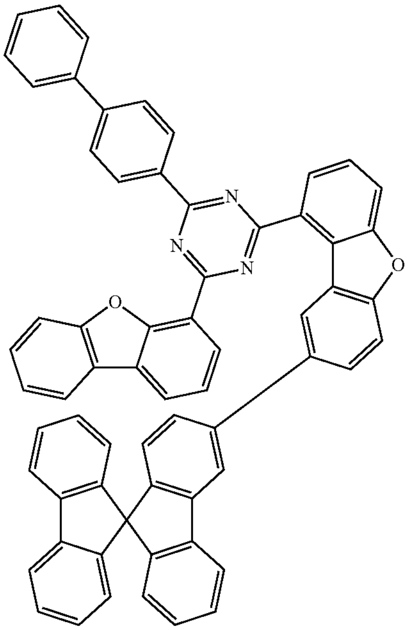 [SMILES: c1ccc(-c2ccc(-c3nc(-c4cccc5c4oc4ccccc45)nc(-c4cccc5oc6ccc(-c7ccc8c(c7)-c7ccccc7C87c8ccccc8-c8ccccc87)cc6c45)n3)cc2)cc1]

TABLE 1-continued
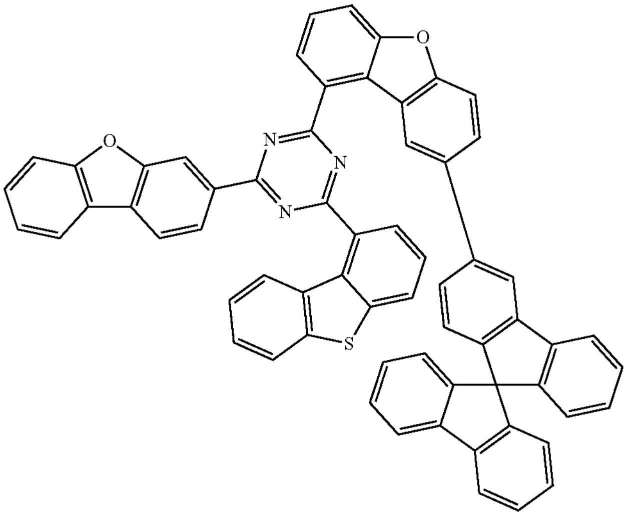 [SMILES: c1ccc2c(c1)-c1ccccc1C21c2ccccc2-c2cc(-c3ccc4oc5cccc(-c6nc(-c7ccc8c(c7)oc7ccccc78)nc(-c7cccc8sc9ccccc9c78)n6)c5c4c3)ccc21]
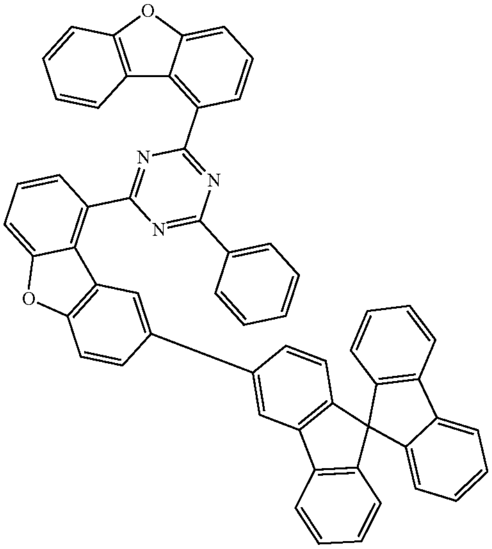 [SMILES: c1ccc(-c2nc(-c3cccc4oc5ccccc5c34)nc(-c3cccc4oc5ccc(-c6ccc7c(c6)-c6ccccc6C76c7ccccc7-c7ccccc76)cc5c34)n2)cc1]
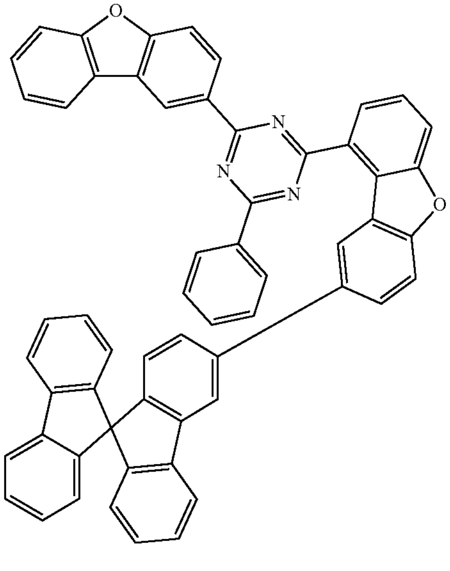 [SMILES: c1ccc(-c2nc(-c3ccc4oc5ccccc5c4c3)nc(-c3cccc4oc5ccc(-c6ccc7c(c6)-c6ccccc6C76c7ccccc7-c7ccccc76)cc5c34)n2)cc1]

TABLE 1-continued
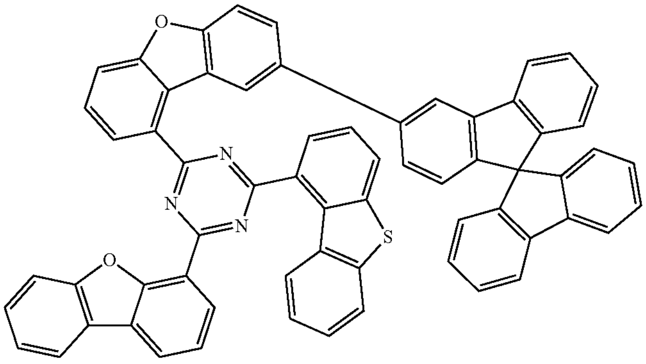 [SMILES: c1ccc2c(c1)-c1ccccc1C21c2ccccc2-c2cc(-c3ccc4oc5cccc(-c6nc(-c7cccc8c7oc7ccccc78)nc(-c7cccc8sc9ccccc9c78)n6)c5c4c3)ccc21]
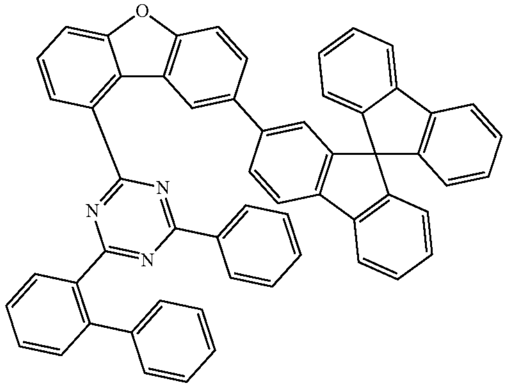 [SMILES: c1ccc(-c2nc(-c3ccccc3-c3ccccc3)nc(-c3cccc4oc5ccc(-c6ccc7c(c6)C6(c8ccccc8-c8ccccc86)c6ccccc6-7)cc5c34)n2)cc1]
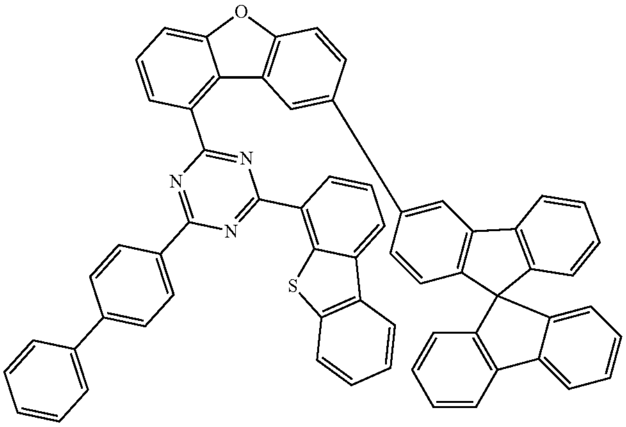 [SMILES: c1ccc(-c2ccc(-c3nc(-c4cccc5c4sc4ccccc45)nc(-c4cccc5oc6ccc(-c7ccc8c(c7)-c7ccccc7C87c8ccccc8-c8ccccc87)cc6c45)n3)cc2)cc1]
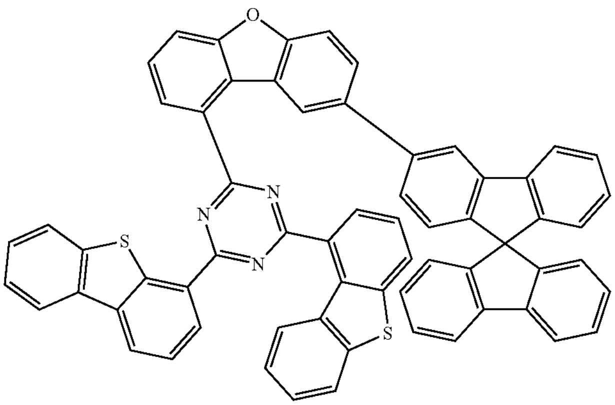 [SMILES: c1ccc2c(c1)-c1ccccc1C21c2ccccc2-c2cc(-c3ccc4oc5cccc(-c6nc(-c7cccc8c7sc7ccccc78)nc(-c7cccc8sc9ccccc9c78)n6)c5c4c3)ccc21]

TABLE 1-continued
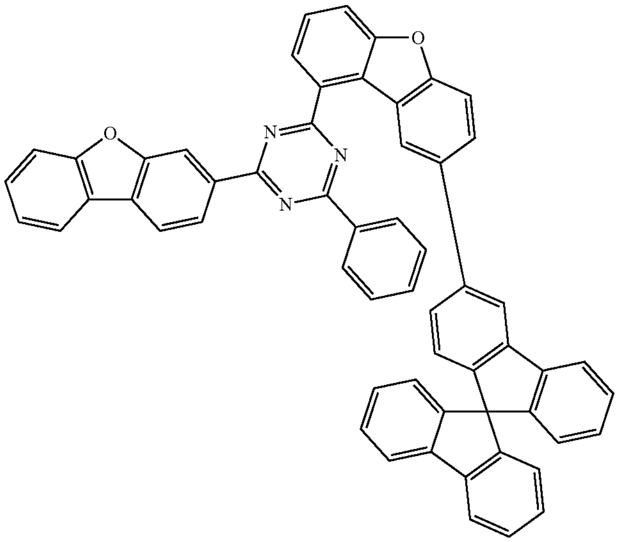 [SMILES: c1ccc(-c2nc(-c3ccc4c(c3)oc3ccccc34)nc(-c3cccc4oc5ccc(-c6ccc7c(c6)-c6ccccc6C76c7ccccc7-c7ccccc76)cc5c34)n2)cc1]
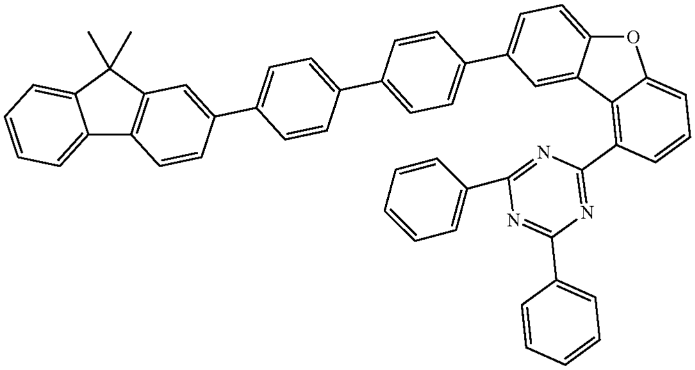 [SMILES: CC1(C)c2ccccc2-c2ccc(-c3ccc(-c4ccc(-c5ccc6oc7cccc(-c8nc(-c9ccccc9)nc(-c9ccccc9)n8)c7c6c5)cc4)cc3)cc21]
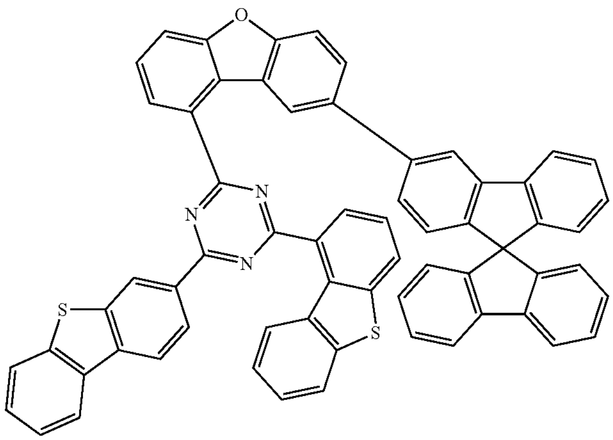 [SMILES: c1ccc2c(c1)-c1ccccc1C21c2ccccc2-c2cc(-c3ccc4oc5cccc(-c6nc(-c7ccc8c(c7)sc7ccccc78)nc(-c7cccc8sc9ccccc9c78)n6)c5c4c3)ccc21]

TABLE 1-continued
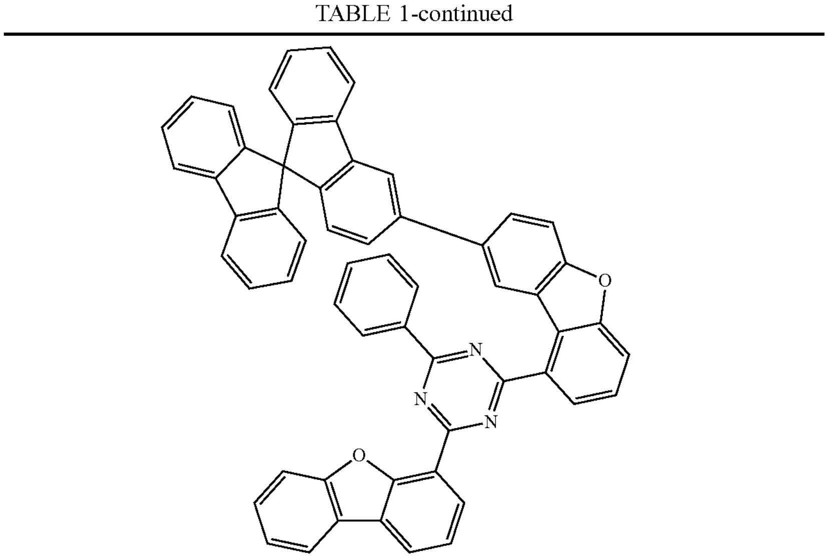
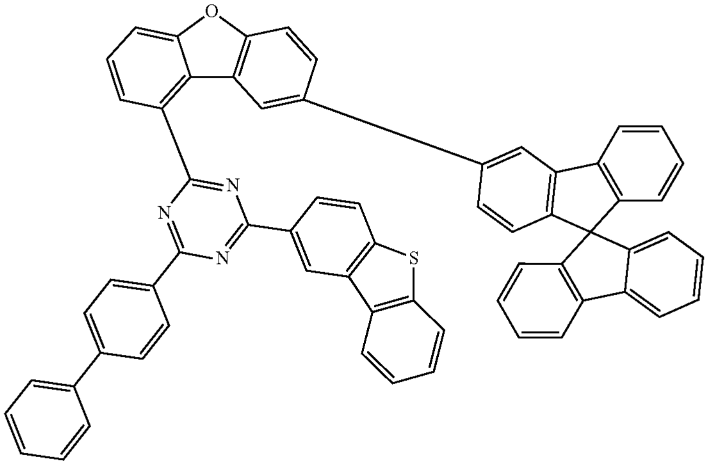 [SMILES: c1ccc(-c2ccc(-c3nc(-c4ccc5sc6ccccc6c5c4)nc(-c4cccc5oc6ccc(-c7ccc8c(c7)-c7ccccc7C87c8ccccc8-c8ccccc87)cc6c45)n3)cc2)cc1]
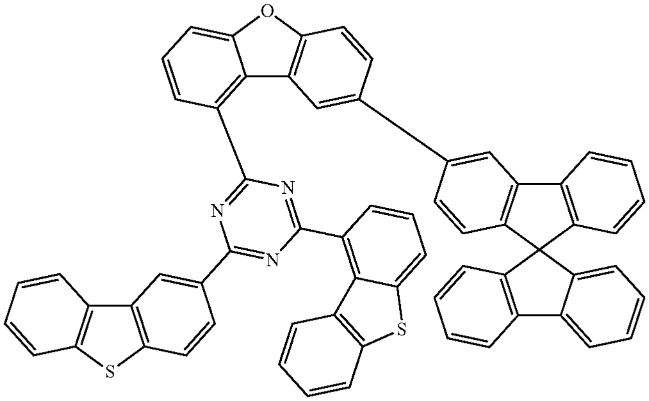 [SMILES: c1ccc2c(c1)-c1ccccc1C21c2ccccc2-c2cc(-c3ccc4oc5cccc(-c6nc(-c7ccc8sc9ccccc9c8c7)nc(-c7cccc8sc9ccccc9c78)n6)c5c4c3)ccc21]

TABLE 1-continued
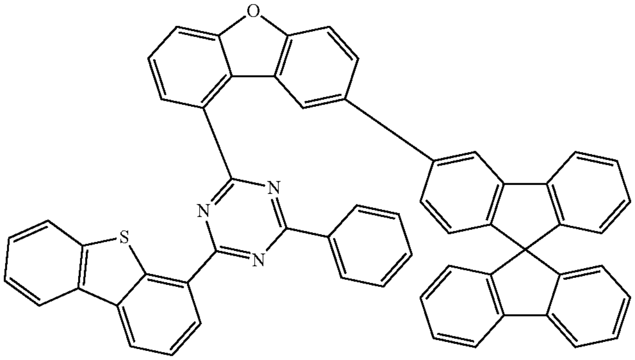 [SMILES: c1ccc(-c2nc(-c3cccc4c3sc3ccccc34)nc(-c3cccc4oc5ccc(-c6ccc7c(c6)-c6ccccc6C76c7ccccc7-c7ccccc76)cc5c34)n2)cc1]
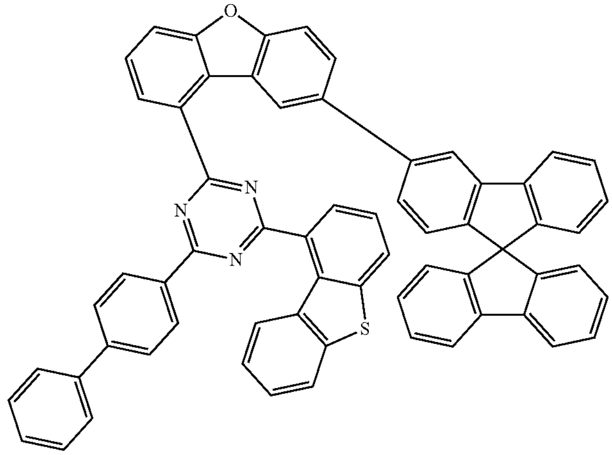 [SMILES: c1ccc(-c2ccc(-c3nc(-c4cccc5oc6ccc(-c7ccc8c(c7)-c7ccccc7C87c8ccccc8-c8ccccc87)cc6c45)nc(-c4cccc5sc6ccccc6c45)n3)cc2)cc1]
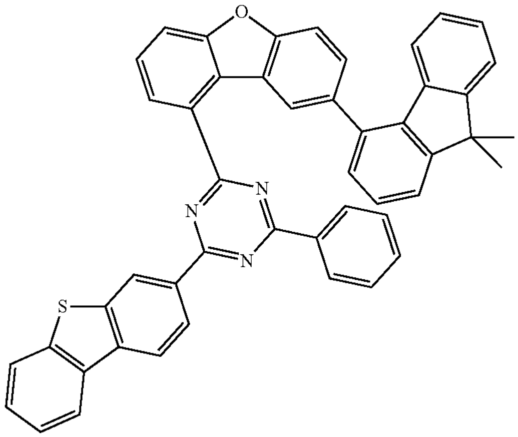 [SMILES: CC1(C)c2ccccc2-c2c(-c3ccc4oc5cccc(-c6nc(-c7ccccc7)nc(-c7ccc8c(c7)sc7ccccc78)n6)c5c4c3)cccc21]

TABLE 1-continued
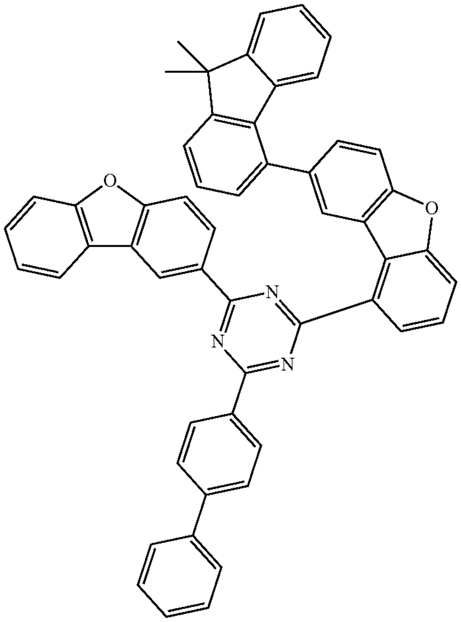 [SMILES: CC1(C)c2ccccc2-c2c(-c3ccc4oc5cccc(-c6nc(-c7ccc(-c8ccccc8)cc7)nc(-c7ccc8oc9ccccc9c8c7)n6)c5c4c3)cccc21]
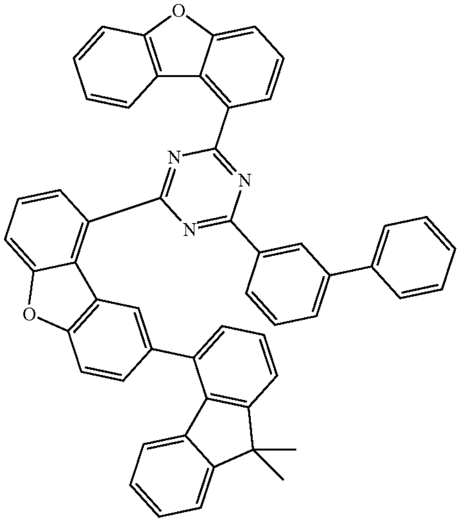 [SMILES: CC1(C)c2ccccc2-c2c(-c3ccc4oc5cccc(-c6nc(-c7cccc(-c8ccccc8)c7)nc(-c7cccc8oc9ccccc9c78)n6)c5c4c3)cccc21]
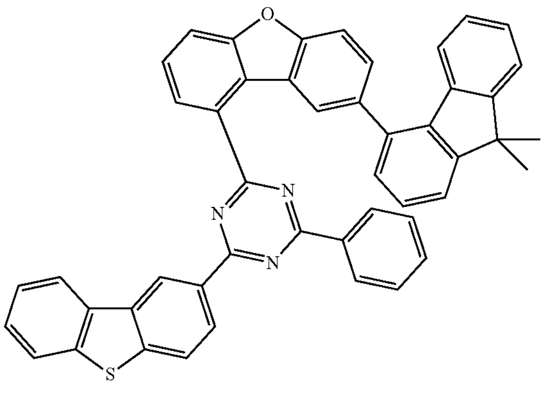 [SMILES: CC1(C)c2ccccc2-c2c(-c3ccc4oc5cccc(-c6nc(-c7ccccc7)nc(-c7ccc8sc9ccccc9c8c7)n6)c5c4c3)cccc21]

TABLE 1-continued
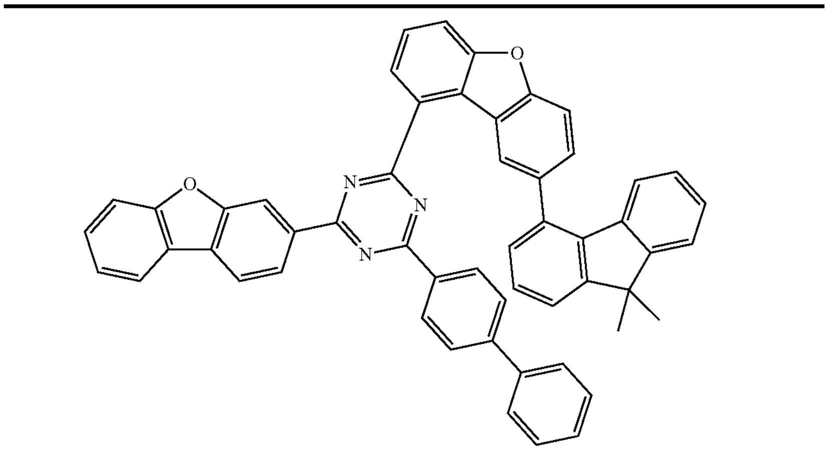
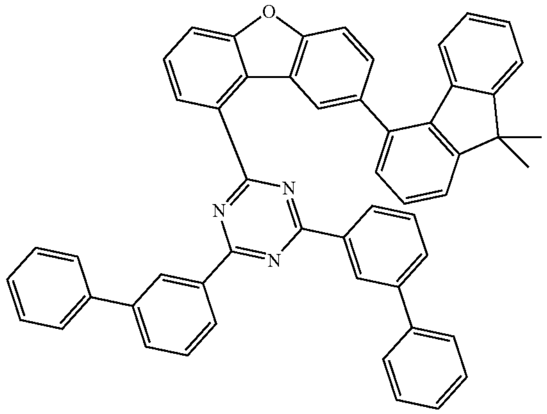 [SMILES: CC1(C)c2ccccc2-c2c(-c3ccc4oc5cccc(-c6nc(-c7cccc(-c8ccccc8)c7)nc(-c7cccc(-c8ccccc8)c7)n6)c5c4c3)cccc21]
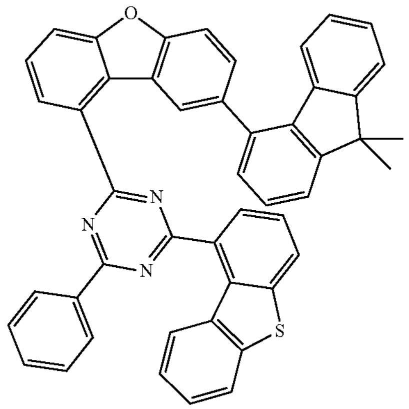 [SMILES: CC1(C)c2ccccc2-c2c(-c3ccc4oc5cccc(-c6nc(-c7ccccc7)nc(-c7cccc8sc9ccccc9c78)n6)c5c4c3)cccc21]

TABLE 1-continued
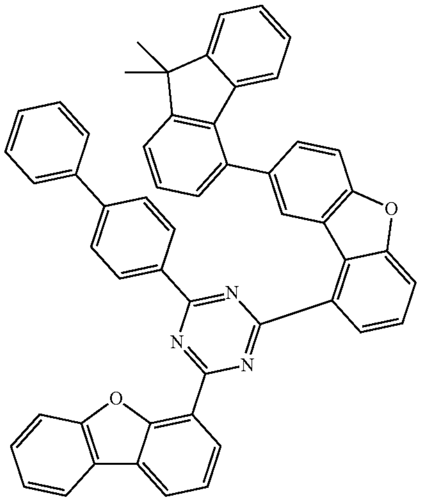 [SMILES: CC1(C)c2ccccc2-c2c(-c3ccc4oc5cccc(-c6nc(-c7ccc(-c8ccccc8)cc7)nc(-c7cccc8c7oc7ccccc78)n6)c5c4c3)cccc21]
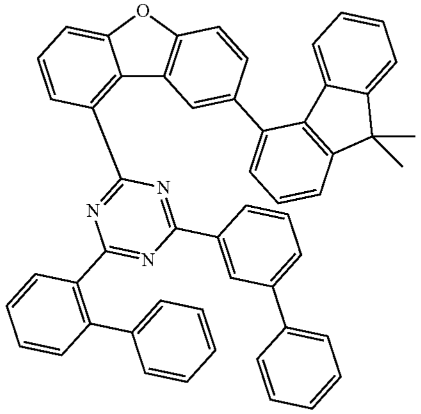 [SMILES: CC1(C)c2ccccc2-c2c(-c3ccc4oc5cccc(-c6nc(-c7cccc(-c8ccccc8)c7)nc(-c7ccccc7-c7ccccc7)n6)c5c4c3)cccc21]
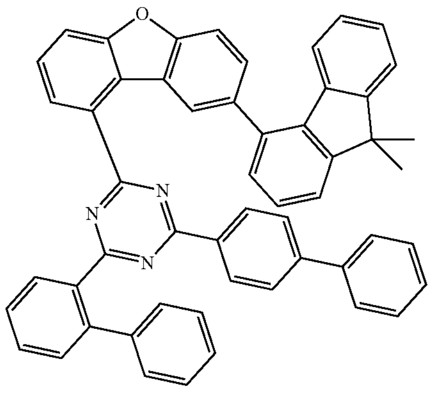 [SMILES: CC1(C)c2ccccc2-c2c(-c3ccc4oc5cccc(-c6nc(-c7ccc(-c8ccccc8)cc7)nc(-c7ccccc7-c7ccccc7)n6)c5c4c3)cccc21]

TABLE 1-continued
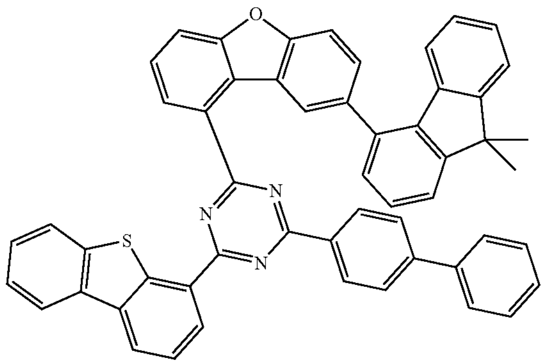 [SMILES: CC1(C)c2ccccc2-c2c(-c3ccc4oc5cccc(-c6nc(-c7ccc(-c8ccccc8)cc7)nc(-c7cccc8c7sc7ccccc78)n6)c5c4c3)cccc21]
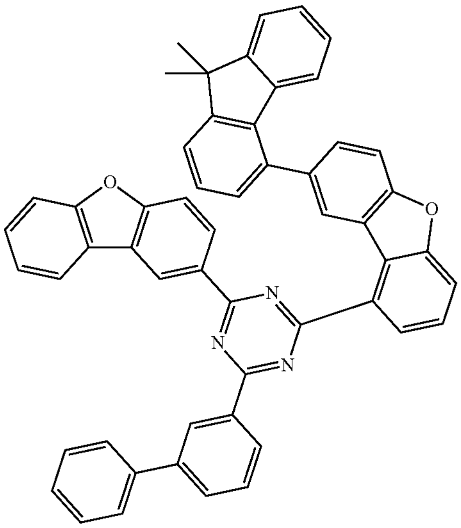 [SMILES: CC1(C)c2ccccc2-c2c(-c3ccc4oc5cccc(-c6nc(-c7cccc(-c8ccccc8)c7)nc(-c7ccc8oc9ccccc9c8c7)n6)c5c4c3)cccc21]
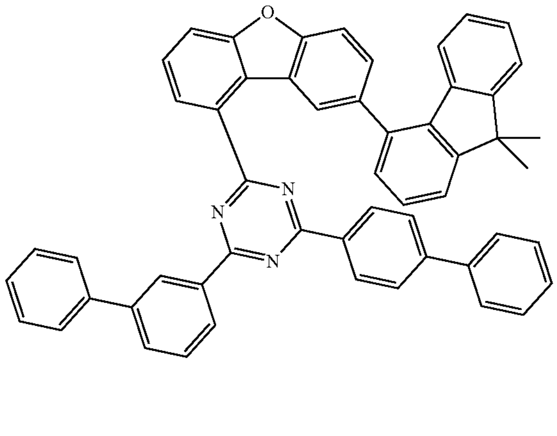 [SMILES: CC1(C)c2ccccc2-c2c(-c3ccc4oc5cccc(-c6nc(-c7ccc(-c8ccccc8)cc7)nc(-c7cccc(-c8ccccc8)c7)n6)c5c4c3)cccc21]

TABLE 1-continued
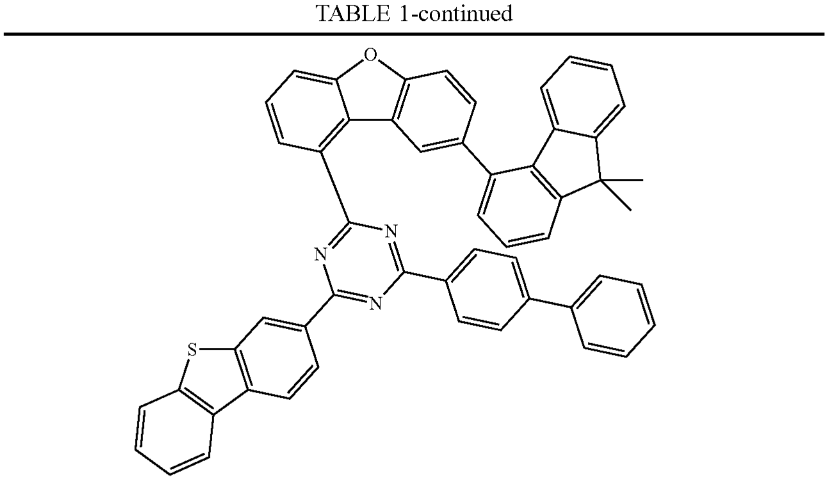
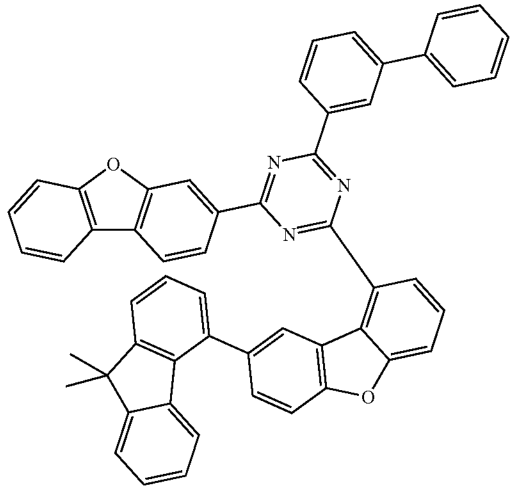 [SMILES: CC1(C)c2ccccc2-c2c(-c3ccc4oc5cccc(-c6nc(-c7cccc(-c8ccccc8)c7)nc(-c7ccc8c(c7)oc7ccccc78)n6)c5c4c3)cccc21]
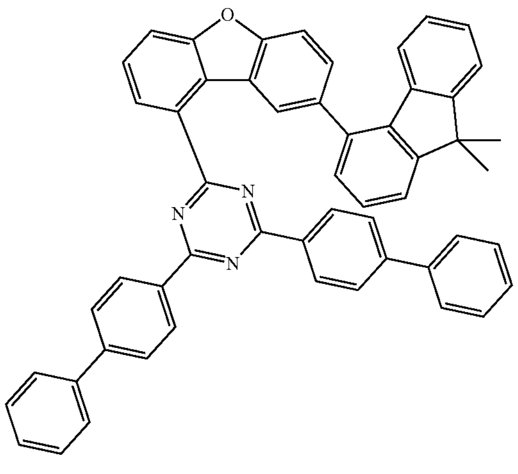 [SMILES: CC1(C)c2ccccc2-c2c(-c3ccc4oc5cccc(-c6nc(-c7ccc(-c8ccccc8)cc7)nc(-c7ccc(-c8ccccc8)cc7)n6)c5c4c3)cccc21]

TABLE 1-continued
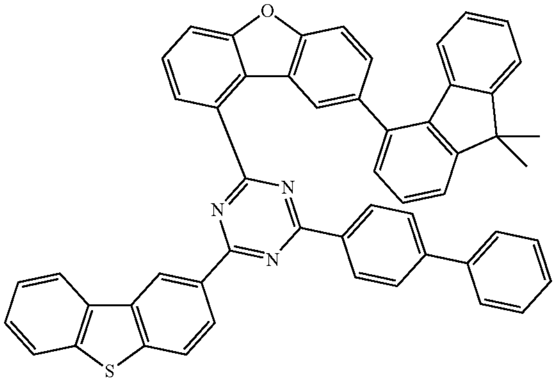 [SMILES: CC1(C)c2ccccc2-c2c(-c3ccc4oc5cccc(-c6nc(-c7ccc(-c8ccccc8)cc7)nc(-c7ccc8sc9ccccc9c8c7)n6)c5c4c3)cccc21]
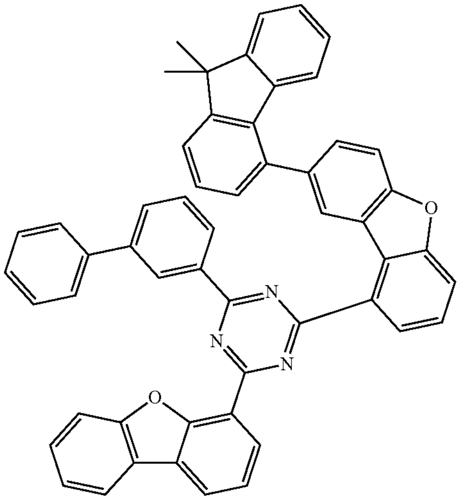 [SMILES: CC1(C)c2ccccc2-c2c(-c3ccc4oc5cccc(-c6nc(-c7cccc(-c8ccccc8)c7)nc(-c7cccc8c7oc7ccccc78)n6)c5c4c3)cccc21]
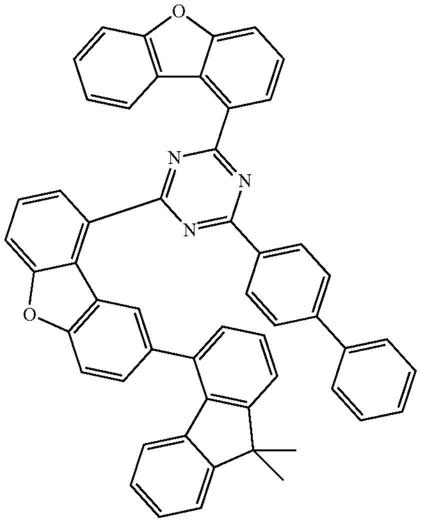 [SMILES: CC1(C)c2ccccc2-c2c(-c3ccc4oc5cccc(-c6nc(-c7ccc(-c8ccccc8)cc7)nc(-c7cccc8oc9ccccc9c78)n6)c5c4c3)cccc21]

TABLE 1-continued
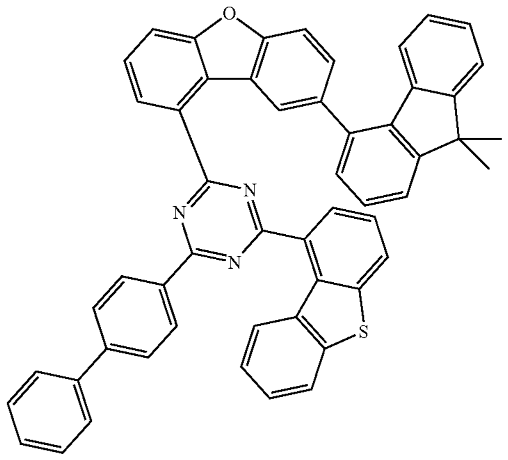 [SMILES: CC1(C)c2ccccc2-c2c(-c3ccc4oc5cccc(-c6nc(-c7ccc(-c8ccccc8)cc7)nc(-c7cccc8sc9ccccc9c78)n6)c5c4c3)cccc21]
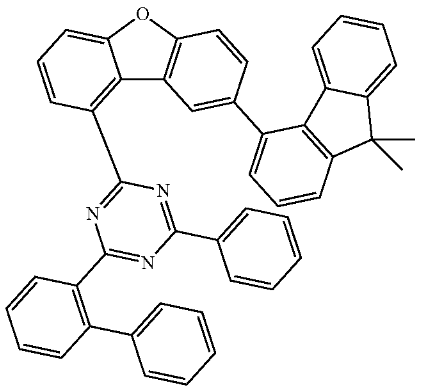 [SMILES: CC1(C)c2ccccc2-c2c(-c3ccc4oc5cccc(-c6nc(-c7ccccc7)nc(-c7ccccc7-c7ccccc7)n6)c5c4c3)cccc21]
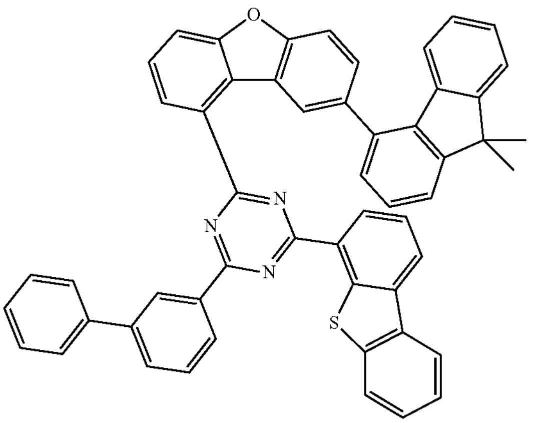 [SMILES: CC1(C)c2ccccc2-c2c(-c3ccc4oc5cccc(-c6nc(-c7cccc(-c8ccccc8)c7)nc(-c7cccc8c7sc7ccccc78)n6)c5c4c3)cccc21]

TABLE 1-continued
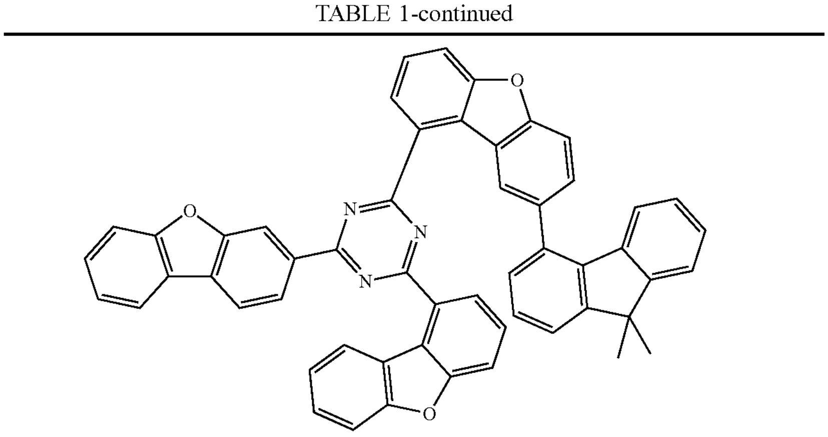
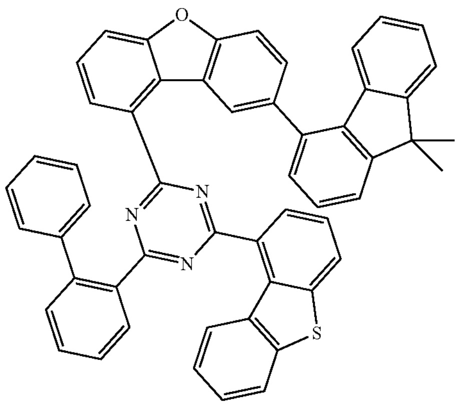 [SMILES: CC1(C)c2ccccc2-c2c(-c3ccc4oc5cccc(-c6nc(-c7ccccc7-c7ccccc7)nc(-c7cccc8sc9ccccc9c78)n6)c5c4c3)cccc21]
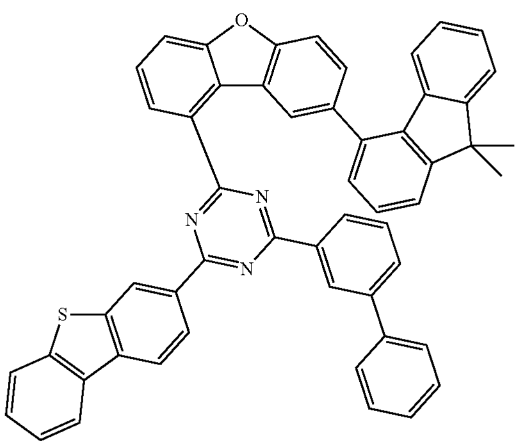 [SMILES: CC1(C)c2ccccc2-c2c(-c3ccc4oc5cccc(-c6nc(-c7cccc(-c8ccccc8)c7)nc(-c7ccc8c(c7)sc7ccccc78)n6)c5c4c3)cccc21]

TABLE 1-continued
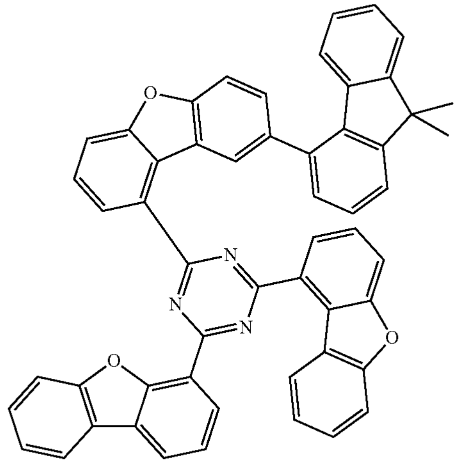 [SMILES: CC1(C)c2ccccc2-c2c(-c3ccc4oc5cccc(-c6nc(-c7cccc8c7oc7ccccc78)nc(-c7cccc8oc9ccccc9c78)n6)c5c4c3)cccc21]
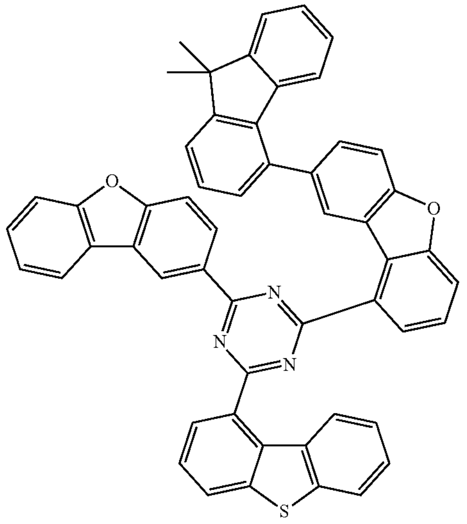 [SMILES: CC1(C)c2ccccc2-c2c(-c3ccc4oc5cccc(-c6nc(-c7ccc8oc9ccccc9c8c7)nc(-c7cccc8sc9ccccc9c78)n6)c5c4c3)cccc21]
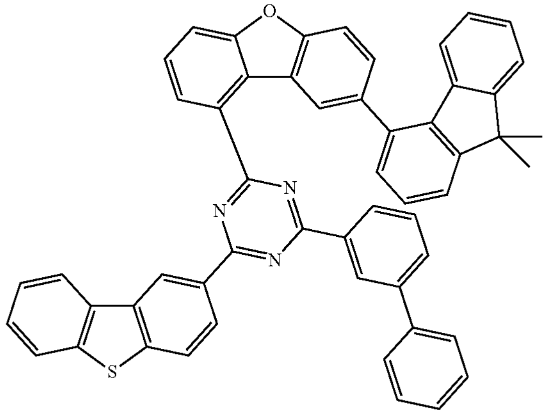 [SMILES: CC1(C)c2ccccc2-c2c(-c3ccc4oc5cccc(-c6nc(-c7cccc(-c8ccccc8)c7)nc(-c7ccc8sc9ccccc9c8c7)n6)c5c4c3)cccc21]

TABLE 1-continued
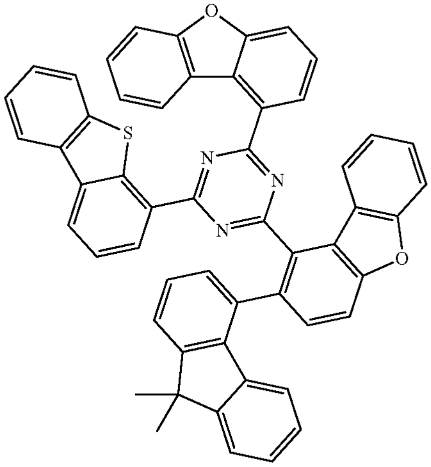 [SMILES: CC1(C)c2ccccc2-c2c(-c3ccc4oc5ccccc5c4c3-c3nc(-c4cccc5c4sc4ccccc45)nc(-c4cccc5oc6ccccc6c45)n3)cccc21]
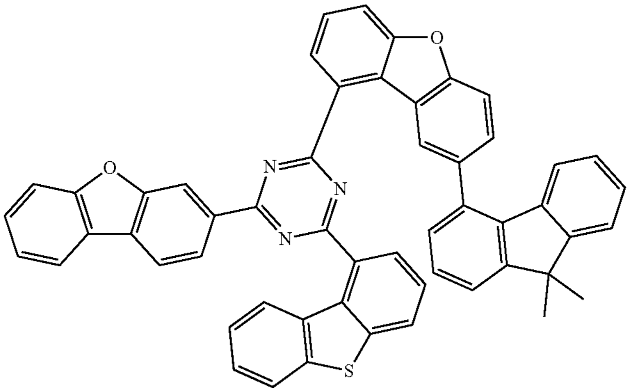 [SMILES: CC1(C)c2ccccc2-c2c(-c3ccc4oc5cccc(-c6nc(-c7ccc8c(c7)oc7ccccc78)nc(-c7cccc8sc9ccccc9c78)n6)c5c4c3)cccc21]
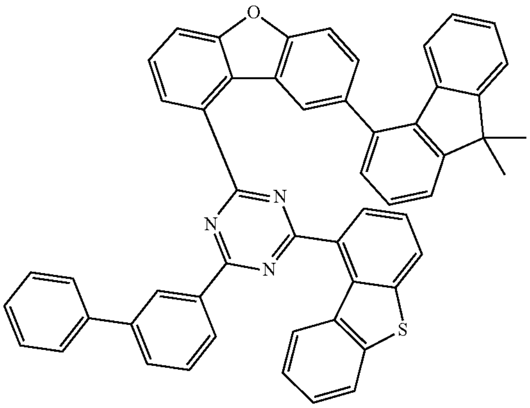 [SMILES: CC1(C)c2ccccc2-c2c(-c3ccc4oc5cccc(-c6nc(-c7cccc(-c8ccccc8)c7)nc(-c7cccc8sc9ccccc9c78)n6)c5c4c3)cccc21]
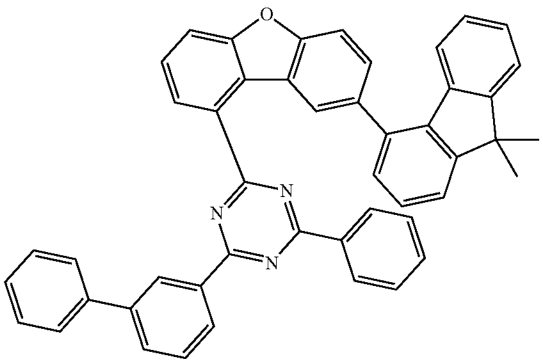 [SMILES: CC1(C)c2ccccc2-c2c(-c3ccc4oc5cccc(-c6nc(-c7ccccc7)nc(-c7cccc(-c8ccccc8)c7)n6)c5c4c3)cccc21]

TABLE 1-continued
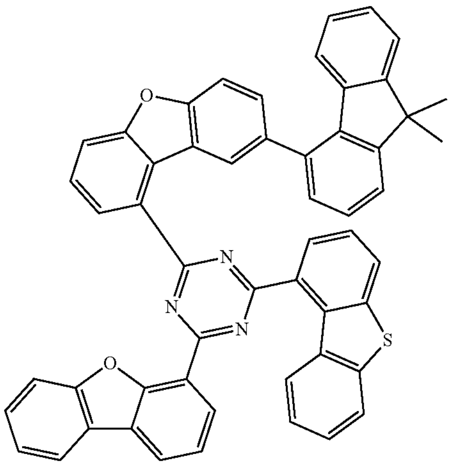 [SMILES: CC1(C)c2ccccc2-c2c(-c3ccc4oc5cccc(-c6nc(-c7cccc8c7oc7ccccc78)nc(-c7cccc8sc9ccccc9c78)n6)c5c4c3)cccc21]
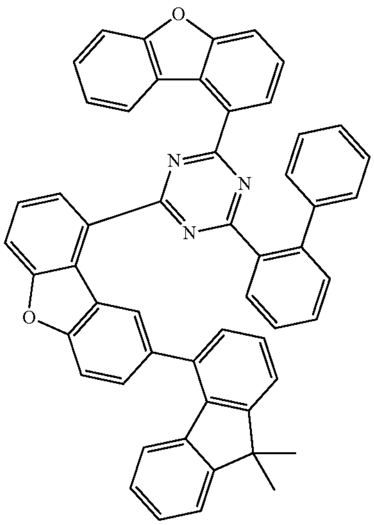 [SMILES: CC1(C)c2ccccc2-c2c(-c3ccc4oc5cccc(-c6nc(-c7ccccc7-c7ccccc7)nc(-c7cccc8oc9ccccc9c78)n6)c5c4c3)cccc21]
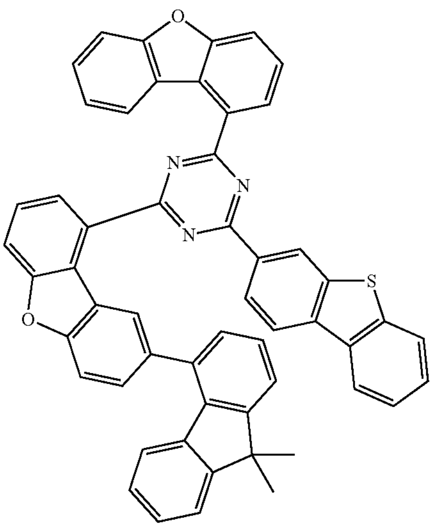 [SMILES: CC1(C)c2ccccc2-c2c(-c3ccc4oc5cccc(-c6nc(-c7ccc8c(c7)sc7ccccc78)nc(-c7cccc8oc9ccccc9c78)n6)c5c4c3)cccc21]

TABLE 1-continued
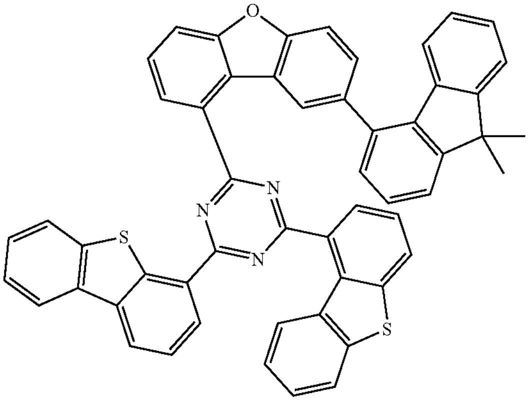 [SMILES: CC1(C)c2ccccc2-c2c(-c3ccc4oc5cccc(-c6nc(-c7cccc8c7sc7ccccc78)nc(-c7cccc8sc9ccccc9c78)n6)c5c4c3)cccc21]
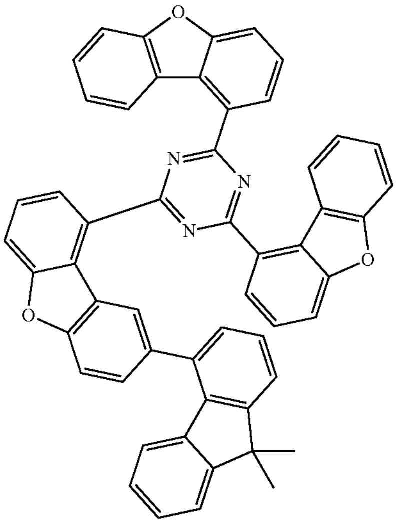 [SMILES: CC1(C)c2ccccc2-c2c(-c3ccc4oc5cccc(-c6nc(-c7cccc8oc9ccccc9c78)nc(-c7cccc8oc9ccccc9c78)n6)c5c4c3)cccc21]
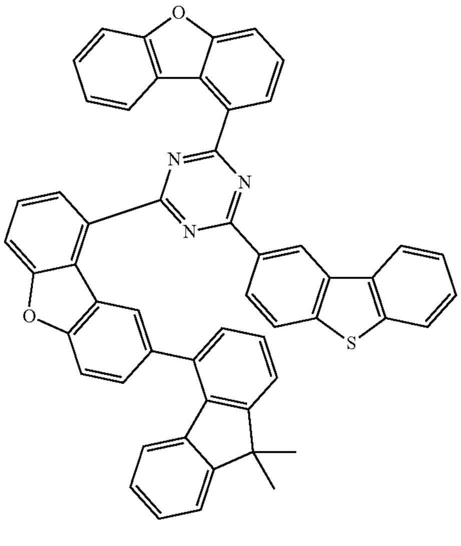 [SMILES: CC1(C)c2ccccc2-c2c(-c3ccc4oc5cccc(-c6nc(-c7ccc8sc9ccccc9c8c7)nc(-c7cccc8oc9ccccc9c78)n6)c5c4c3)cccc21]

TABLE 1-continued
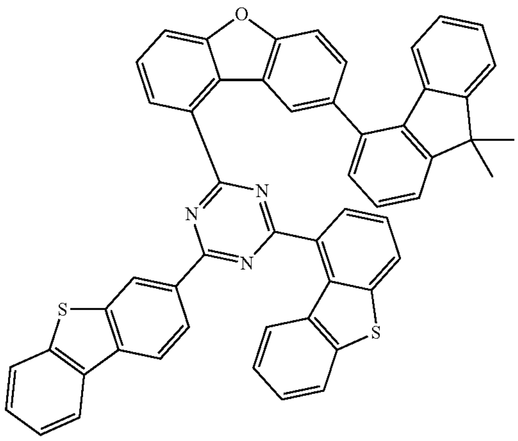 [SMILES: CC1(C)c2ccccc2-c2c(-c3ccc4oc5cccc(-c6nc(-c7ccc8c(c7)sc7ccccc78)nc(-c7cccc8sc9ccccc9c78)n6)c5c4c3)cccc21]
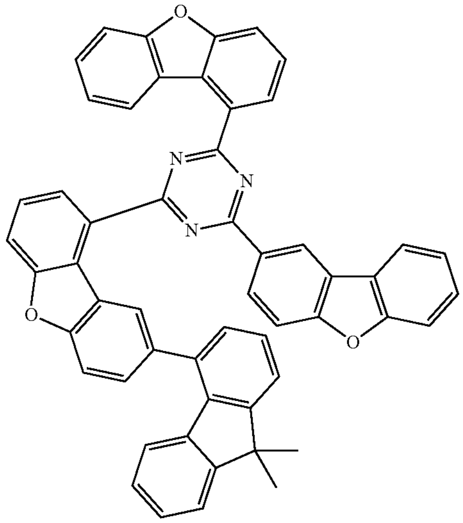 [SMILES: CC1(C)c2ccccc2-c2c(-c3ccc4oc5cccc(-c6nc(-c7ccc8oc9ccccc9c8c7)nc(-c7cccc8oc9ccccc9c78)n6)c5c4c3)cccc21]
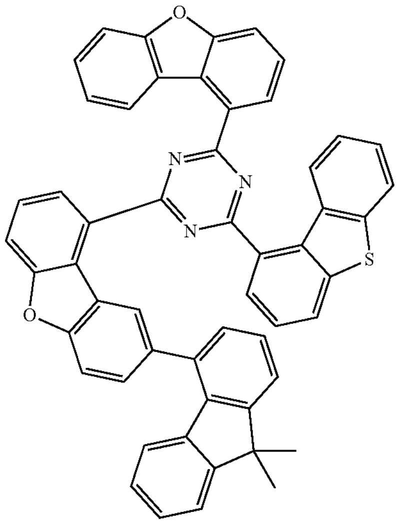 [SMILES: CC1(C)c2ccccc2-c2c(-c3ccc4oc5cccc(-c6nc(-c7cccc8oc9ccccc9c78)nc(-c7cccc8sc9ccccc9c78)n6)c5c4c3)cccc21]

TABLE 1-continued
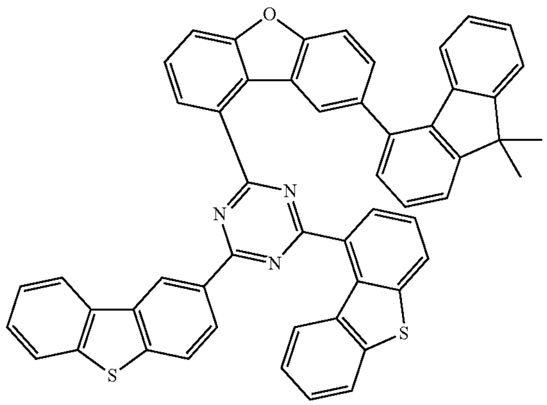 [SMILES: CC1(C)c2ccccc2-c2c(-c3ccc4oc5cccc(-c6nc(-c7ccc8sc9ccccc9c8c7)nc(-c7cccc8sc9ccccc9c78)n6)c5c4c3)cccc21]
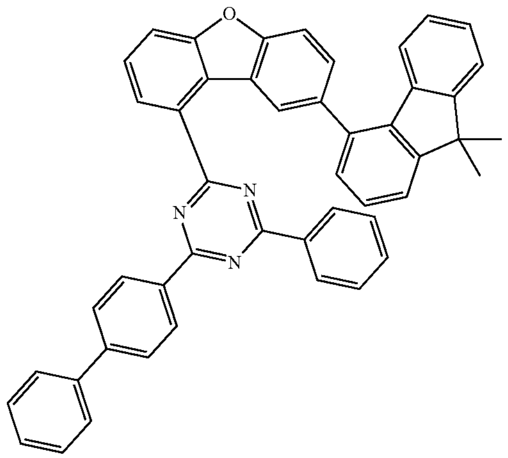 [SMILES: CC1(C)c2ccccc2-c2c(-c3ccc4oc5cccc(-c6nc(-c7ccccc7)nc(-c7ccc(-c8ccccc8)cc7)n6)c5c4c3)cccc21]
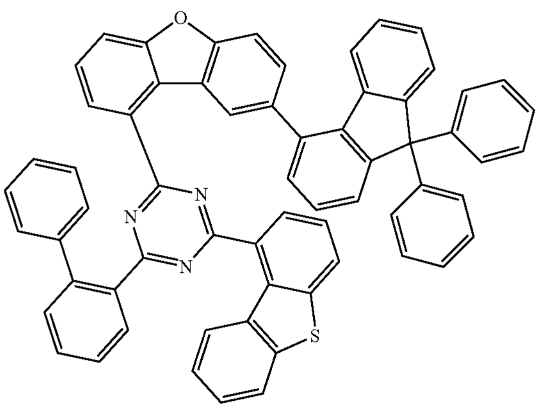 [SMILES: c1ccc(-c2ccccc2-c2nc(-c3cccc4oc5ccc(-c6cccc7c6-c6ccccc6C7(c6ccccc6)c6ccccc6)cc5c34)nc(-c3cccc4sc5ccccc5c34)n2)cc1]

TABLE 1-continued
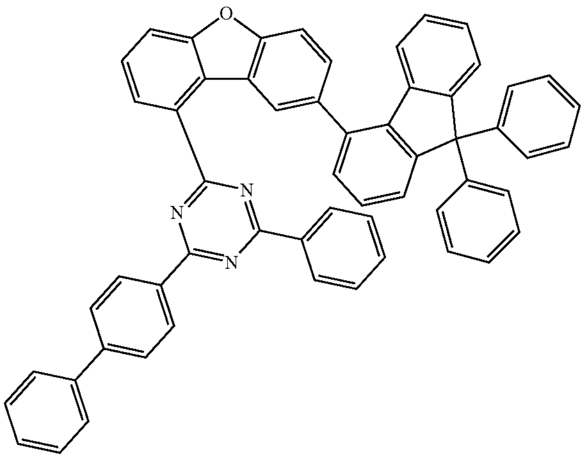 [SMILES: c1ccc(-c2ccc(-c3nc(-c4ccccc4)nc(-c4cccc5oc6ccc(-c7cccc8c7-c7ccccc7C8(c7ccccc7)c7ccccc7)cc6c45)n3)cc2)cc1]
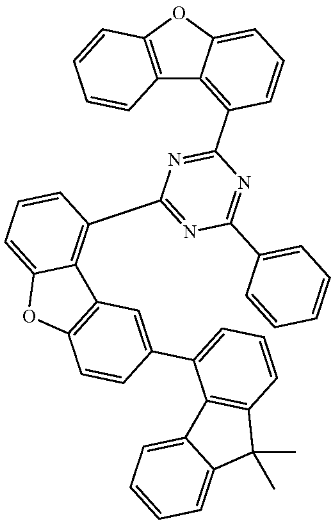 [SMILES: CC1(C)c2ccccc2-c2c(-c3ccc4oc5cccc(-c6nc(-c7ccccc7)nc(-c7cccc8oc9ccccc9c78)n6)c5c4c3)cccc21]
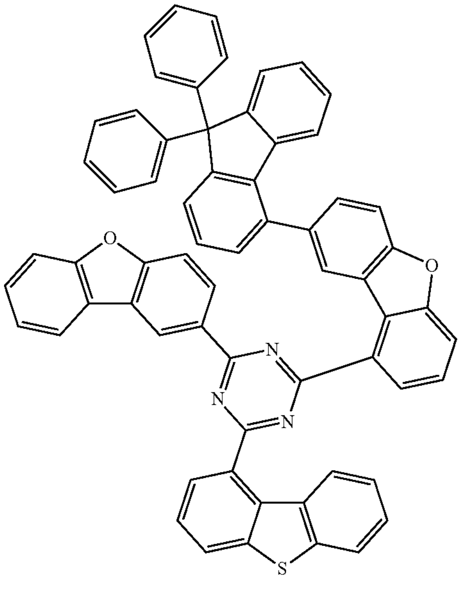 [SMILES: c1ccc(C2(c3ccccc3)c3ccccc3-c3c(-c4ccc5oc6cccc(-c7nc(-c8ccc9oc%10ccccc%10c9c8)nc(-c8cccc9sc%10ccccc%10c89)n7)c6c5c4)cccc32)cc1]

TABLE 1-continued
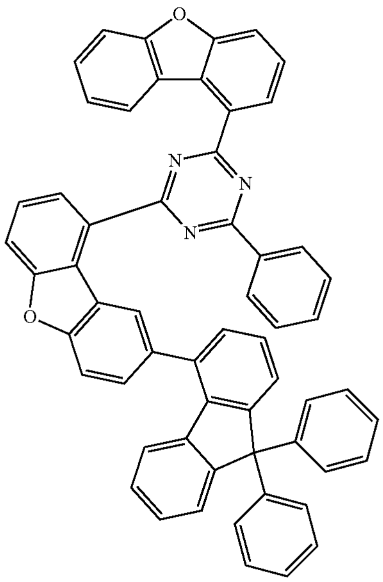 [SMILES: c1ccc(-c2nc(-c3cccc4oc5ccccc5c34)nc(-c3cccc4oc5ccc(-c6cccc7c6-c6ccccc6C7(c6ccccc6)c6ccccc6)cc5c34)n2)cc1]
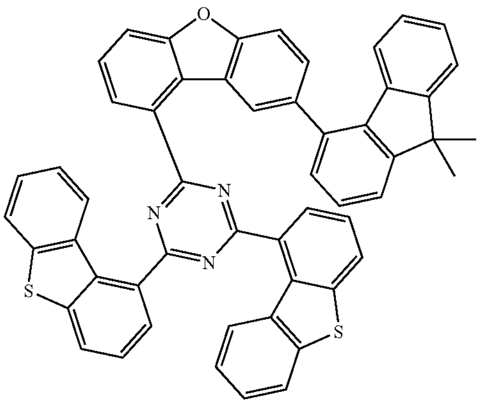 [SMILES: CC1(C)c2ccccc2-c2c(-c3ccc4oc5cccc(-c6nc(-c7cccc8sc9ccccc9c78)nc(-c7cccc8sc9ccccc9c78)n6)c5c4c3)cccc21]
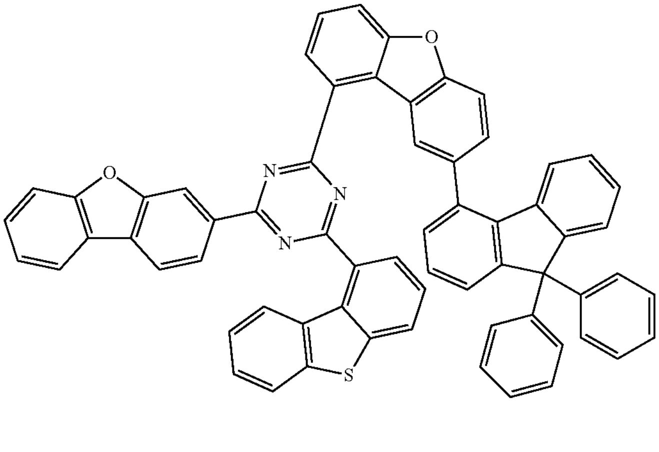 [SMILES: c1ccc(C2(c3ccccc3)c3ccccc3-c3c(-c4ccc5oc6cccc(-c7nc(-c8ccc9c(c8)oc8ccccc89)nc(-c8cccc9sc%10ccccc%10c89)n7)c6c5c4)cccc32)cc1]

TABLE 1-continued
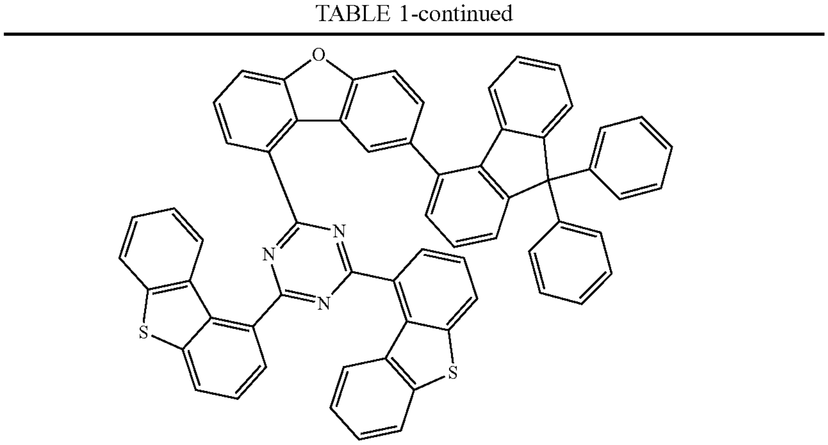
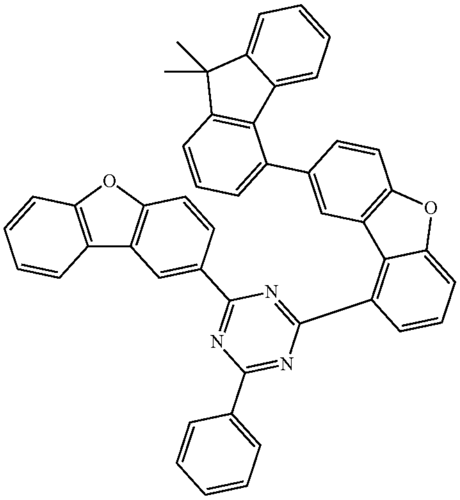 [SMILES: CC1(C)c2ccccc2-c2c(-c3ccc4oc5cccc(-c6nc(-c7ccccc7)nc(-c7ccc8oc9ccccc9c8c7)n6)c5c4c3)cccc21]
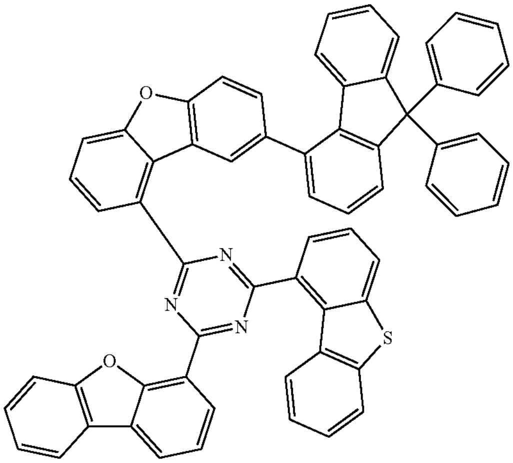 [SMILES: c1ccc(C2(c3ccccc3)c3ccccc3-c3c(-c4ccc5oc6cccc(-c7nc(-c8cccc9c8oc8ccccc89)nc(-c8cccc9sc%10ccccc%10c89)n7)c6c5c4)cccc32)cc1]

TABLE 1-continued
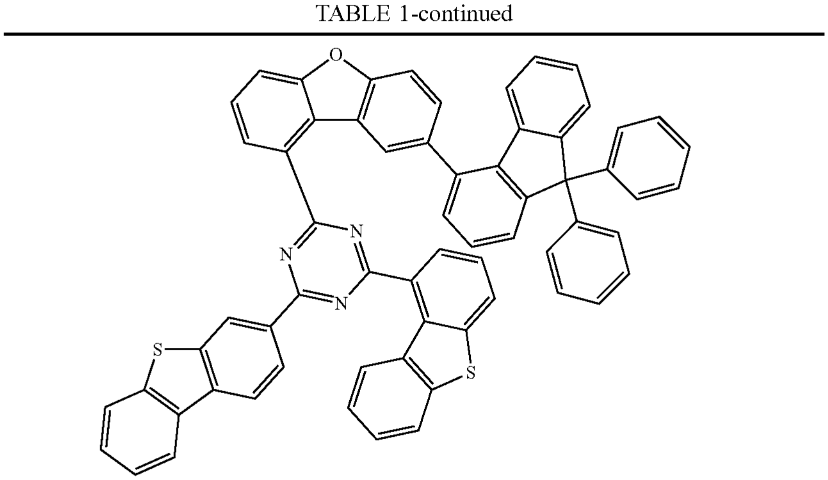
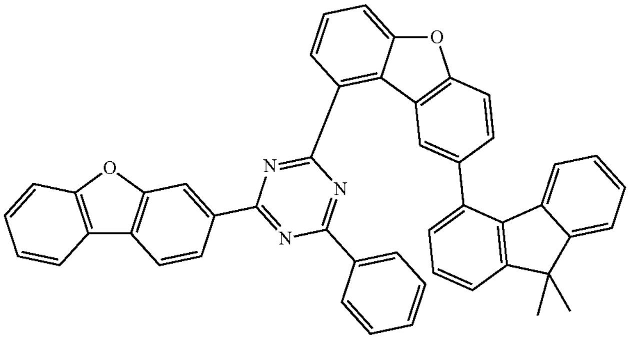 [SMILES: CC1(C)c2ccccc2-c2c(-c3ccc4oc5cccc(-c6nc(-c7ccccc7)nc(-c7ccc8c(c7)oc7ccccc78)n6)c5c4c3)cccc21]
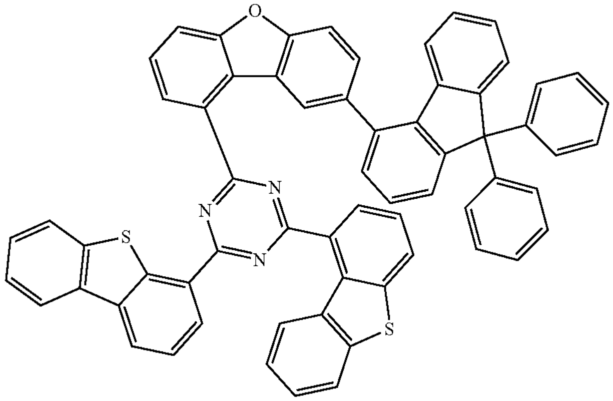 [SMILES: c1ccc(C2(c3ccccc3)c3ccccc3-c3c(-c4ccc5oc6cccc(-c7nc(-c8cccc9c8sc8ccccc89)nc(-c8cccc9sc%10ccccc%10c89)n7)c6c5c4)cccc32)cc1]
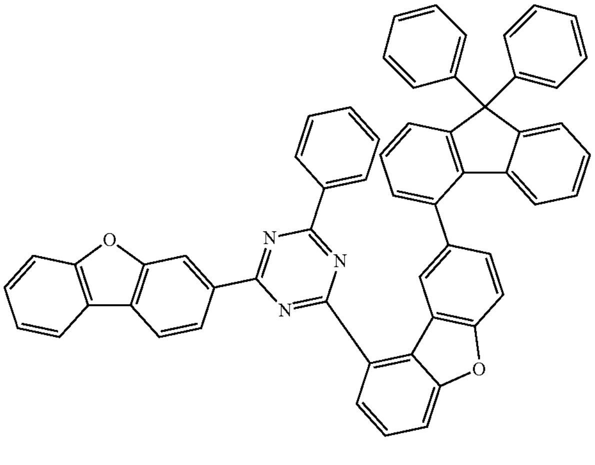 [SMILES: c1ccc(-c2nc(-c3ccc4c(c3)oc3ccccc34)nc(-c3cccc4oc5ccc(-c6cccc7c6-c6ccccc6C7(c6ccccc6)c6ccccc6)cc5c34)n2)cc1]

TABLE 1-continued
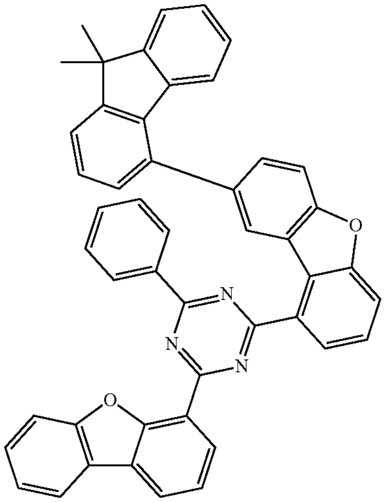 [SMILES: CC1(C)c2ccccc2-c2c(-c3ccc4oc5cccc(-c6nc(-c7ccccc7)nc(-c7cccc8c7oc7ccccc78)n6)c5c4c3)cccc21]
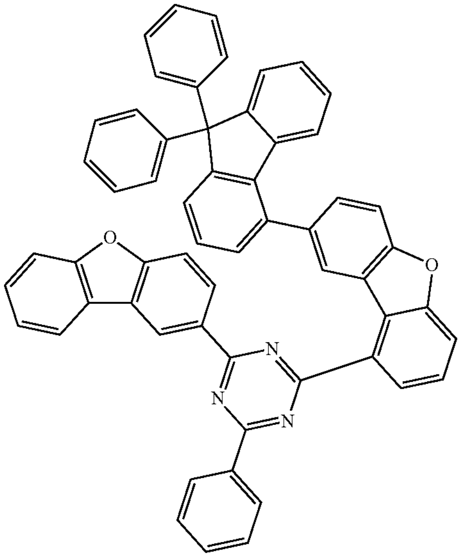 [SMILES: c1ccc(-c2nc(-c3ccc4oc5ccccc5c4c3)nc(-c3cccc4oc5ccc(-c6cccc7c6-c6ccccc6C7(c6ccccc6)c6ccccc6)cc5c34)n2)cc1]
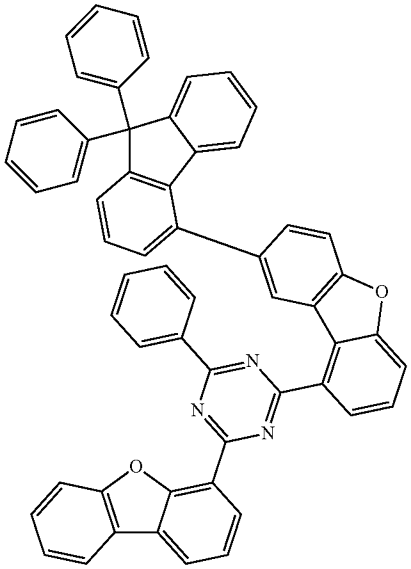 [SMILES: c1ccc(-c2nc(-c3cccc4c3oc3ccccc34)nc(-c3cccc4oc5ccc(-c6cccc7c6-c6ccccc6C7(c6ccccc6)c6ccccc6)cc5c34)n2)cc1]

TABLE 1-continued
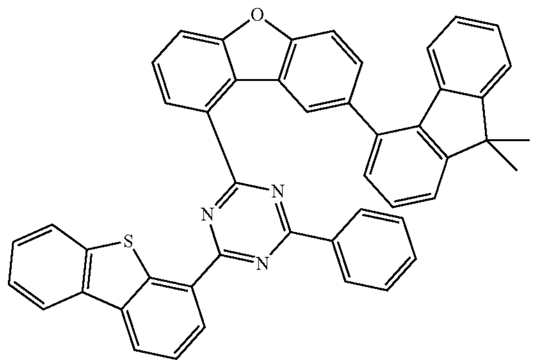 [SMILES: CC1(C)c2ccccc2-c2c(-c3ccc4oc5cccc(-c6nc(-c7ccccc7)nc(-c7cccc8c7sc7ccccc78)n6)c5c4c3)cccc21]
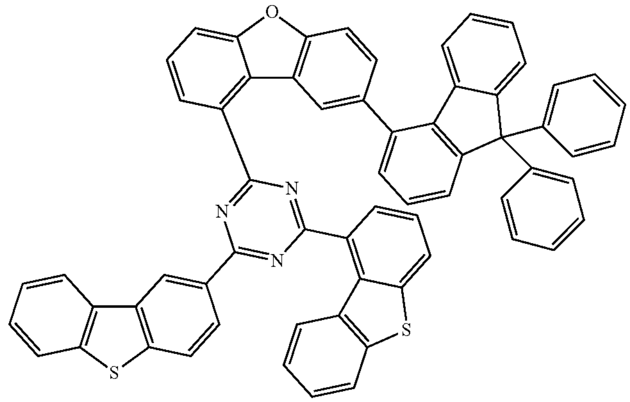 [SMILES: c1ccc(C2(c3ccccc3)c3ccccc3-c3c(-c4ccc5oc6cccc(-c7nc(-c8ccc9sc%10ccccc%10c9c8)nc(-c8cccc9sc%10ccccc%10c89)n7)c6c5c4)cccc32)cc1]
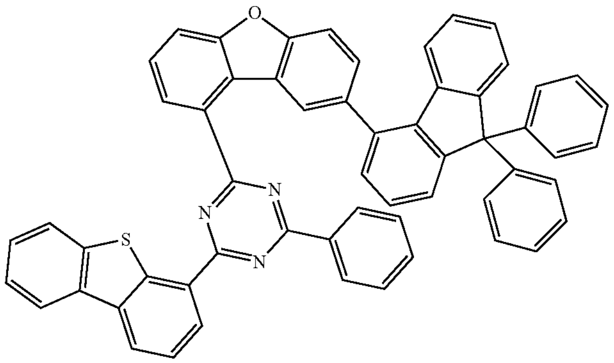 [SMILES: c1ccc(-c2nc(-c3cccc4c3sc3ccccc34)nc(-c3cccc4oc5ccc(-c6cccc7c6-c6ccccc6C7(c6ccccc6)c6ccccc6)cc5c34)n2)cc1]
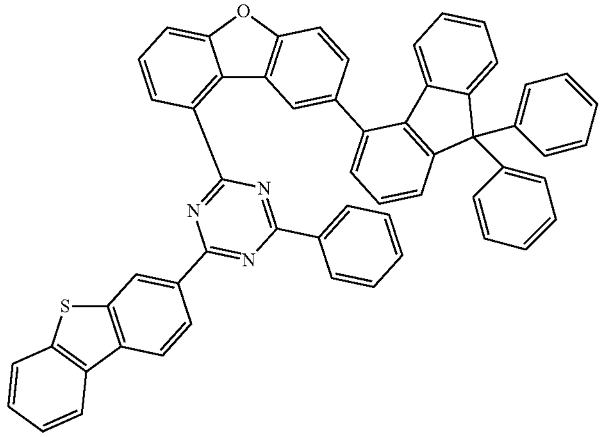 [SMILES: c1ccc(-c2nc(-c3ccc4c(c3)sc3ccccc34)nc(-c3cccc4oc5ccc(-c6cccc7c6-c6ccccc6C7(c6ccccc6)c6ccccc6)cc5c34)n2)cc1]

TABLE 1-continued
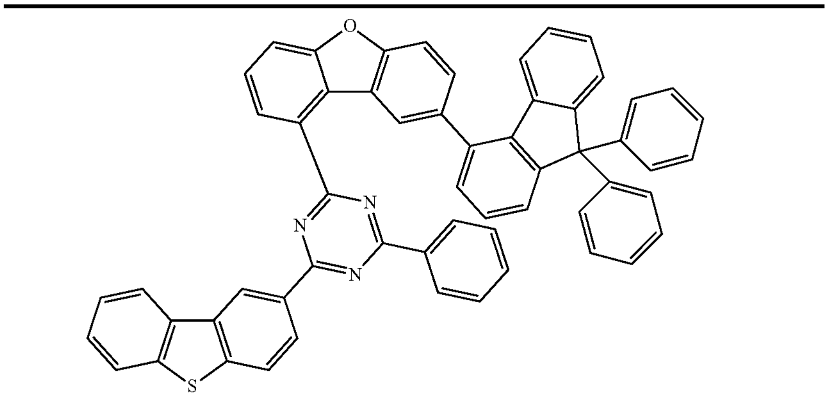
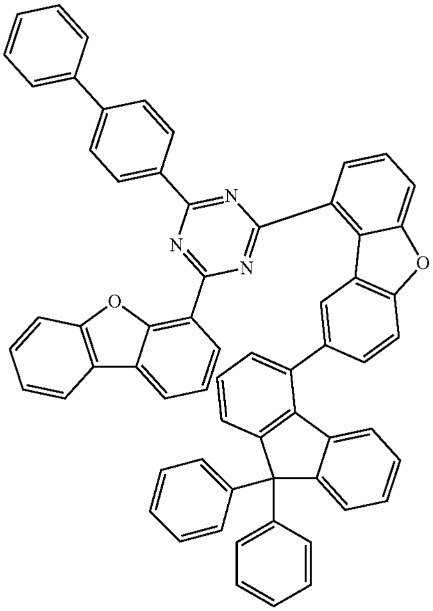 [SMILES: c1ccc(-c2ccc(-c3nc(-c4cccc5c4oc4ccccc45)nc(-c4cccc5oc6ccc(-c7cccc8c7-c7ccccc7C8(c7ccccc7)c7ccccc7)cc6c45)n3)cc2)cc1]
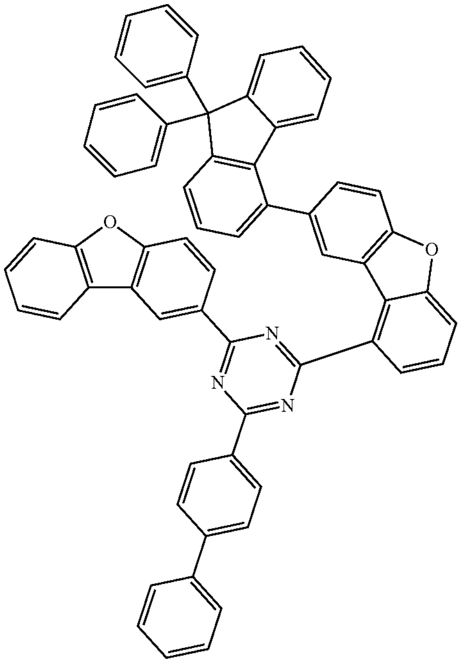 [SMILES: c1ccc(-c2ccc(-c3nc(-c4ccc5oc6ccccc6c5c4)nc(-c4cccc5oc6ccc(-c7cccc8c7-c7ccccc7C8(c7ccccc7)c7ccccc7)cc6c45)n3)cc2)cc1]

TABLE 1-continued
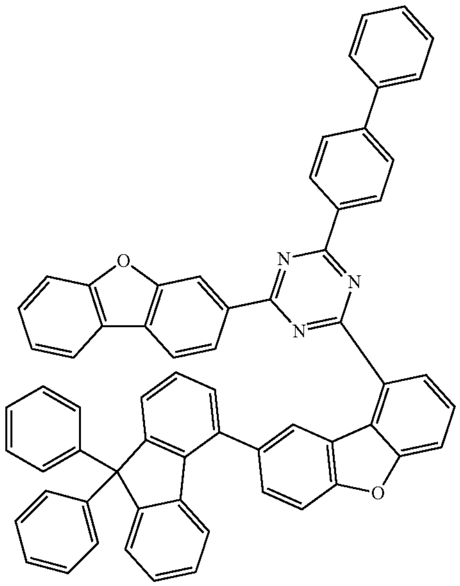 [SMILES: c1ccc(-c2ccc(-c3nc(-c4ccc5c(c4)oc4ccccc45)nc(-c4cccc5oc6ccc(-c7cccc8c7-c7ccccc7C8(c7ccccc7)c7ccccc7)cc6c45)n3)cc2)cc1]
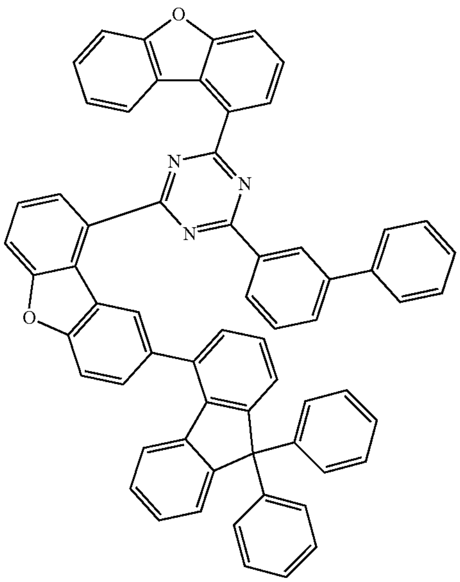 [SMILES: c1ccc(-c2cccc(-c3nc(-c4cccc5oc6ccccc6c45)nc(-c4cccc5oc6ccc(-c7cccc8c7-c7ccccc7C8(c7ccccc7)c7ccccc7)cc6c45)n3)c2)cc1]
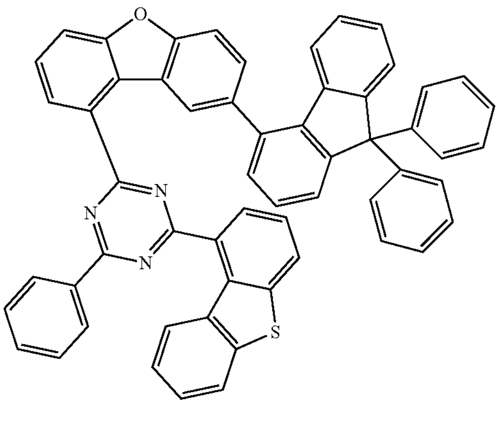 [SMILES: c1ccc(-c2nc(-c3cccc4oc5ccc(-c6cccc7c6-c6ccccc6C7(c6ccccc6)c6ccccc6)cc5c34)nc(-c3cccc4sc5ccccc5c34)n2)cc1]

TABLE 1-continued
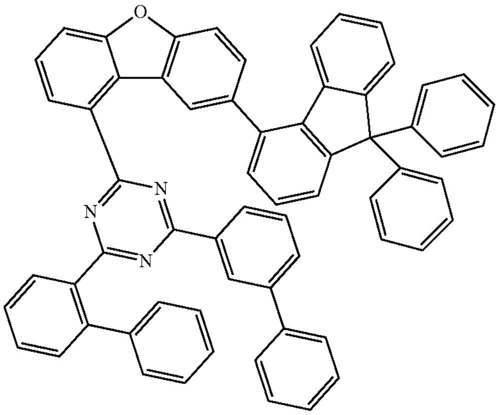 [SMILES: c1ccc(-c2cccc(-c3nc(-c4ccccc4-c4ccccc4)nc(-c4cccc5oc6ccc(-c7cccc8c7-c7ccccc7C8(c7ccccc7)c7ccccc7)cc6c45)n3)c2)cc1]
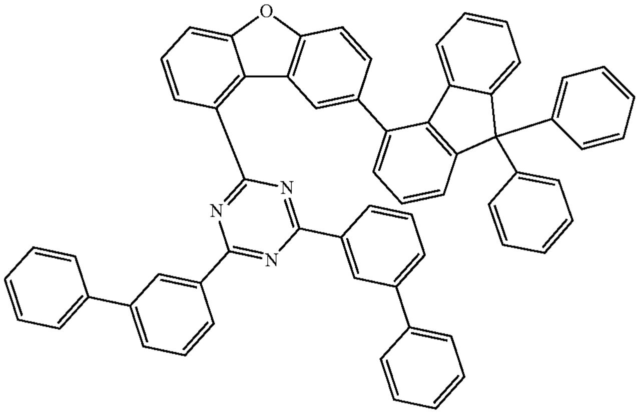 [SMILES: c1ccc(-c2cccc(-c3nc(-c4cccc(-c5ccccc5)c4)nc(-c4cccc5oc6ccc(-c7cccc8c7-c7ccccc7C8(c7ccccc7)c7ccccc7)cc6c45)n3)c2)cc1]
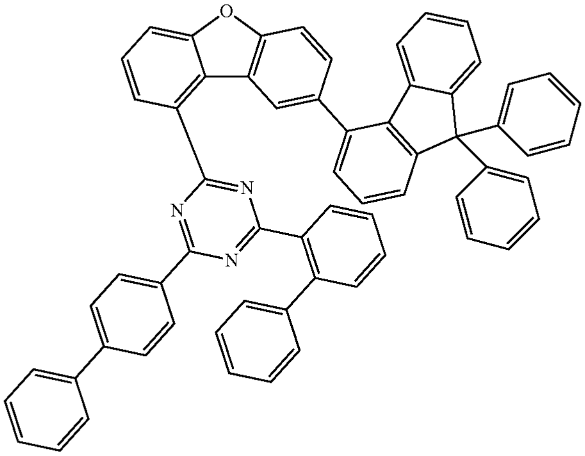 [SMILES: c1ccc(-c2ccc(-c3nc(-c4ccccc4-c4ccccc4)nc(-c4cccc5oc6ccc(-c7cccc8c7-c7ccccc7C8(c7ccccc7)c7ccccc7)cc6c45)n3)cc2)cc1]

TABLE 1-continued
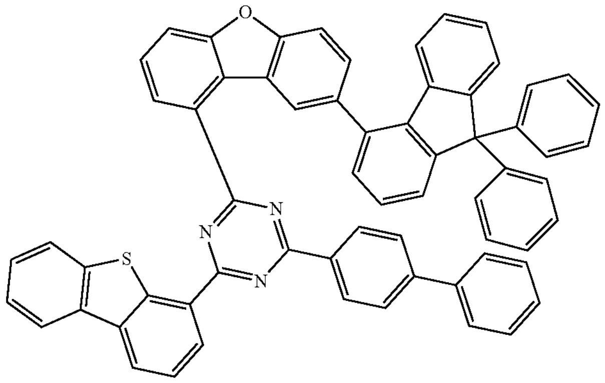 [SMILES: c1ccc(-c2ccc(-c3nc(-c4cccc5c4sc4ccccc45)nc(-c4cccc5oc6ccc(-c7cccc8c7-c7ccccc7C8(c7ccccc7)c7ccccc7)cc6c45)n3)cc2)cc1]
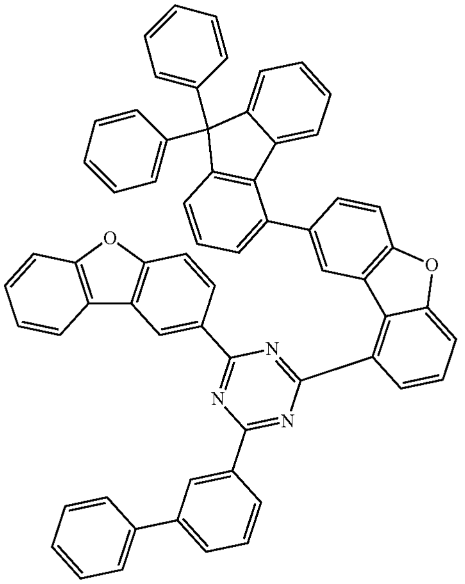 [SMILES: c1ccc(-c2cccc(-c3nc(-c4ccc5oc6ccccc6c5c4)nc(-c4cccc5oc6ccc(-c7cccc8c7-c7ccccc7C8(c7ccccc7)c7ccccc7)cc6c45)n3)c2)cc1]
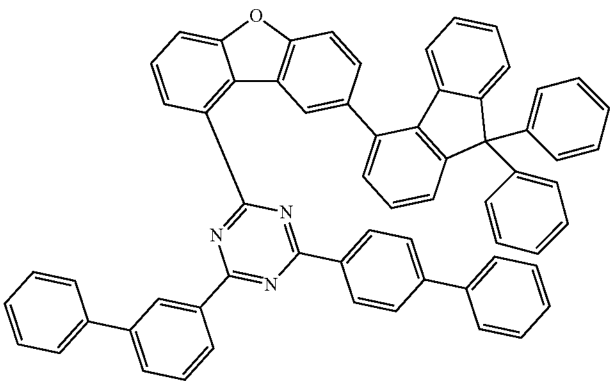 [SMILES: c1ccc(-c2ccc(-c3nc(-c4cccc(-c5ccccc5)c4)nc(-c4cccc5oc6ccc(-c7cccc8c7-c7ccccc7C8(c7ccccc7)c7ccccc7)cc6c45)n3)cc2)cc1]

TABLE 1-continued
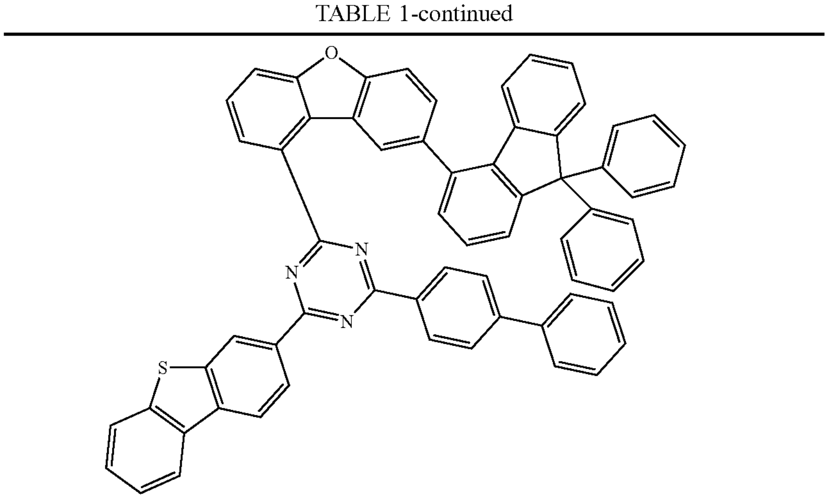
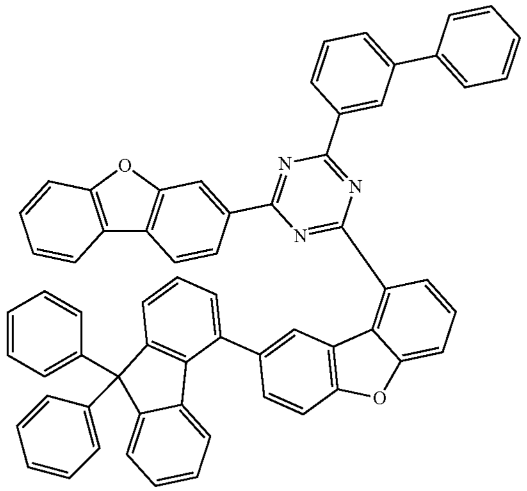 [SMILES: c1ccc(-c2cccc(-c3nc(-c4ccc5c(c4)oc4ccccc45)nc(-c4cccc5oc6ccc(-c7cccc8c7-c7ccccc7C8(c7ccccc7)c7ccccc7)cc6c45)n3)c2)cc1]
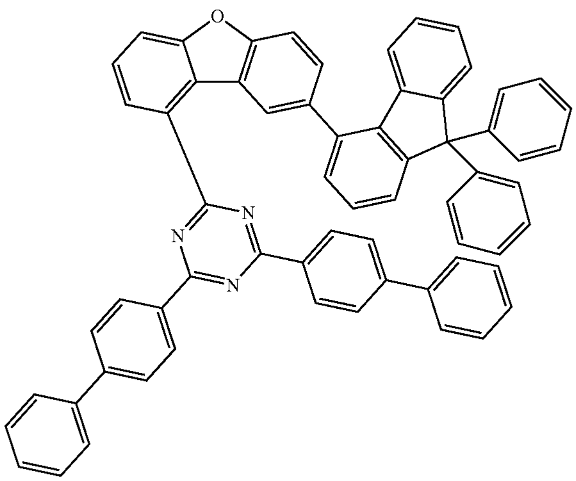 [SMILES: c1ccc(-c2ccc(-c3nc(-c4ccc(-c5ccccc5)cc4)nc(-c4cccc5oc6ccc(-c7cccc8c7-c7ccccc7C8(c7ccccc7)c7ccccc7)cc6c45)n3)cc2)cc1]

TABLE 1-continued
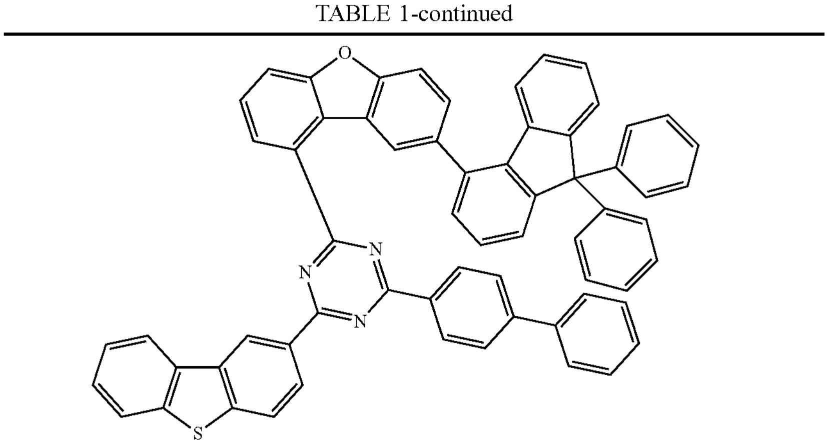
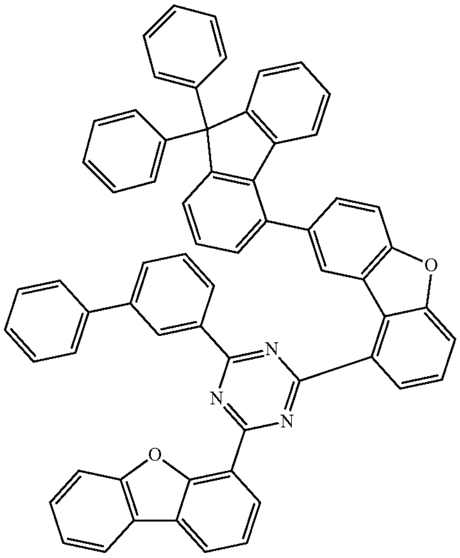 [SMILES: c1ccc(-c2cccc(-c3nc(-c4cccc5c4oc4ccccc45)nc(-c4cccc5oc6ccc(-c7cccc8c7-c7ccccc7C8(c7ccccc7)c7ccccc7)cc6c45)n3)c2)cc1]
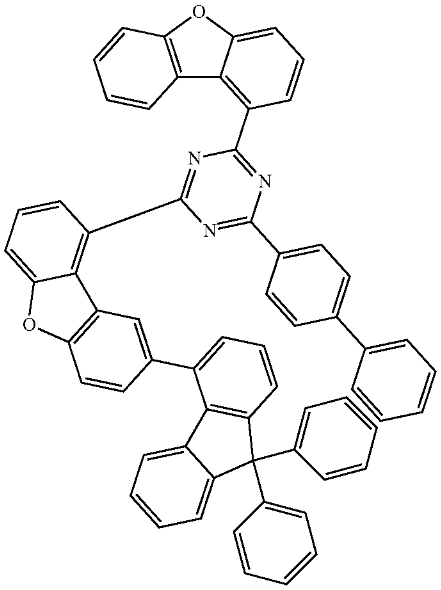 [SMILES: c1ccc(-c2ccc(-c3nc(-c4cccc5oc6ccccc6c45)nc(-c4cccc5oc6ccc(-c7cccc8c7-c7ccccc7C8(c7ccccc7)c7ccccc7)cc6c45)n3)cc2)cc1]

TABLE 1-continued
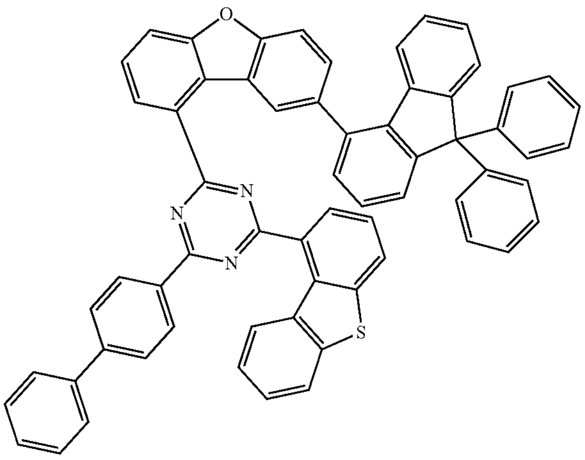 [SMILES: c1ccc(-c2ccc(-c3nc(-c4cccc5oc6ccc(-c7cccc8c7-c7ccccc7C8(c7ccccc7)c7ccccc7)cc6c45)nc(-c4cccc5sc6ccccc6c45)n3)cc2)cc1]
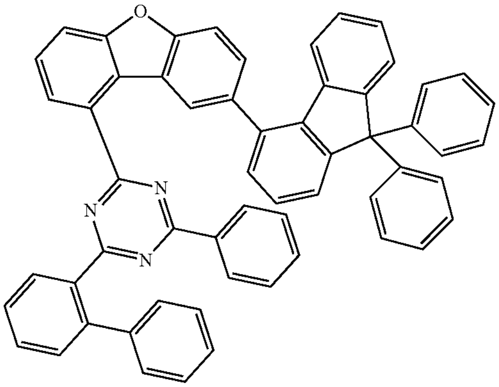 [SMILES: c1ccc(-c2nc(-c3ccccc3-c3ccccc3)nc(-c3cccc4oc5ccc(-c6cccc7c6-c6ccccc6C7(c6ccccc6)c6ccccc6)cc5c34)n2)cc1]
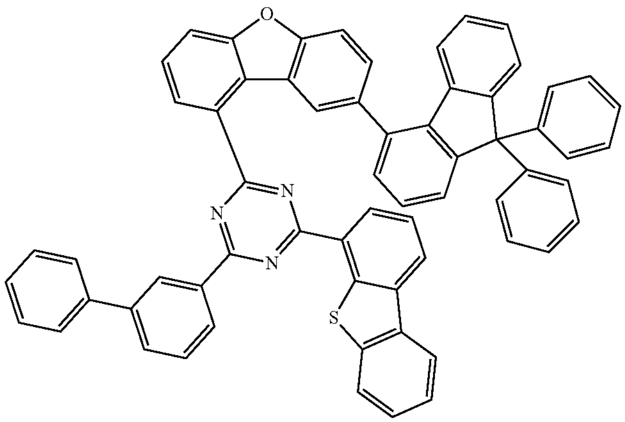 [SMILES: c1ccc(-c2cccc(-c3nc(-c4cccc5c4sc4ccccc45)nc(-c4cccc5oc6ccc(-c7cccc8c7-c7ccccc7C8(c7ccccc7)c7ccccc7)cc6c45)n3)c2)cc1]

TABLE 1-continued
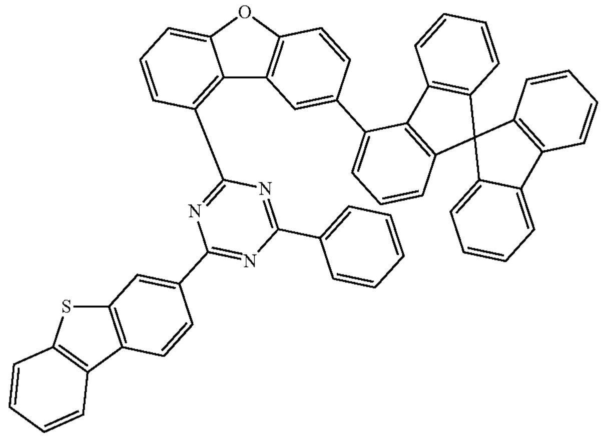 [SMILES: c1ccc(-c2nc(-c3ccc4c(c3)sc3ccccc34)nc(-c3cccc4oc5ccc(-c6cccc7c6-c6ccccc6C76c7ccccc7-c7ccccc76)cc5c34)n2)cc1]
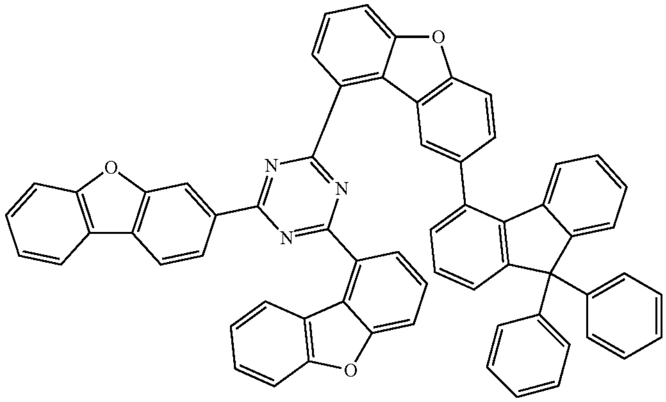 [SMILES: c1ccc(C2(c3ccccc3)c3ccccc3-c3c(-c4ccc5oc6cccc(-c7nc(-c8ccc9c(c8)oc8ccccc89)nc(-c8cccc9oc%10ccccc%10c89)n7)c6c5c4)cccc32)cc1]
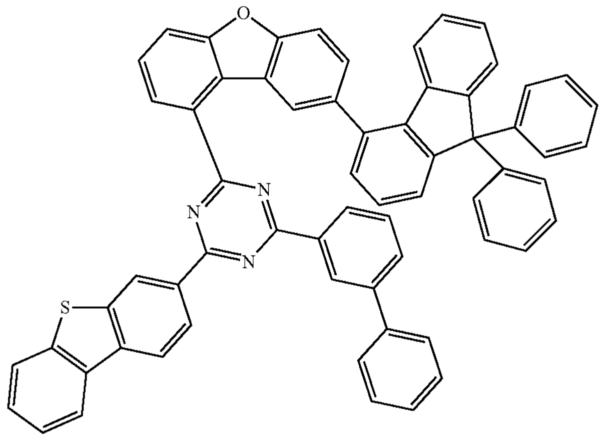 [SMILES: c1ccc(-c2cccc(-c3nc(-c4ccc5c(c4)sc4ccccc45)nc(-c4cccc5oc6ccc(-c7cccc8c7-c7ccccc7C8(c7ccccc7)c7ccccc7)cc6c45)n3)c2)cc1]

TABLE 1-continued
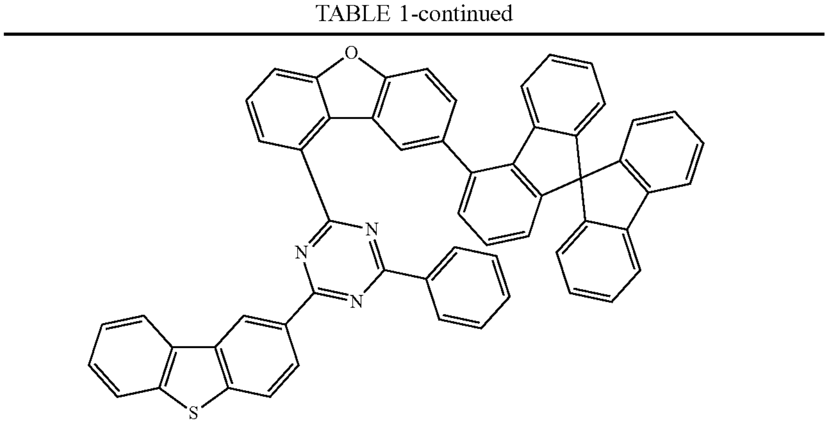
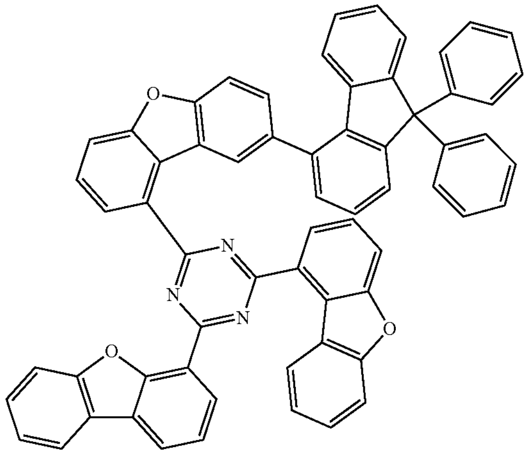 [SMILES: c1ccc(C2(c3ccccc3)c3ccccc3-c3c(-c4ccc5oc6cccc(-c7nc(-c8cccc9c8oc8ccccc89)nc(-c8cccc9oc%10ccccc%10c89)n7)c6c5c4)cccc32)cc1]
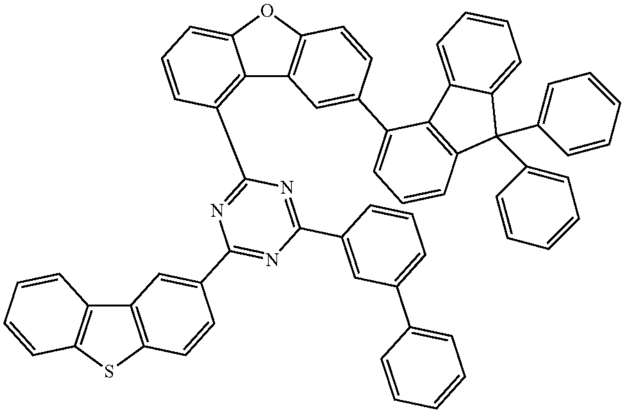 [SMILES: c1ccc(-c2cccc(-c3nc(-c4ccc5sc6ccccc6c5c4)nc(-c4cccc5oc6ccc(-c7cccc8c7-c7ccccc7C8(c7ccccc7)c7ccccc7)cc6c45)n3)c2)cc1]
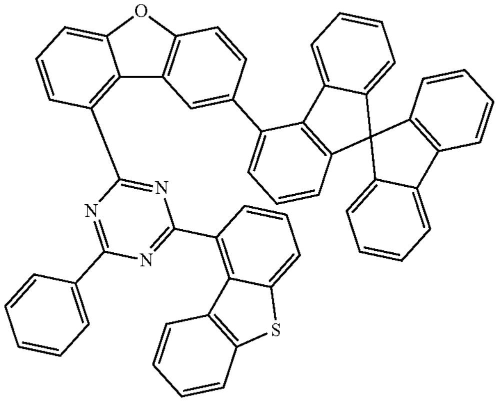 [SMILES: c1ccc(-c2nc(-c3cccc4oc5ccc(-c6cccc7c6-c6ccccc6C76c7ccccc7-c7ccccc76)cc5c34)nc(-c3cccc4sc5ccccc5c34)n2)cc1]

TABLE 1-continued
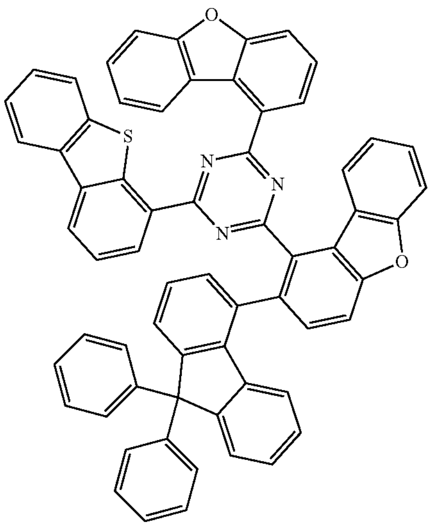 [SMILES: c1ccc(C2(c3ccccc3)c3ccccc3-c3c(-c4ccc5oc6ccccc6c5c4-c4nc(-c5cccc6c5sc5ccccc56)nc(-c5cccc6oc7ccccc7c56)n4)cccc32)cc1]
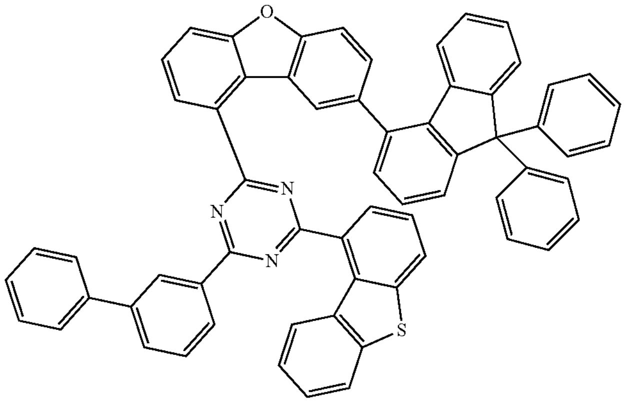 [SMILES: c1ccc(-c2cccc(-c3nc(-c4cccc5oc6ccc(-c7cccc8c7-c7ccccc7C8(c7ccccc7)c7ccccc7)cc6c45)nc(-c4cccc5sc6ccccc6c45)n3)c2)cc1]
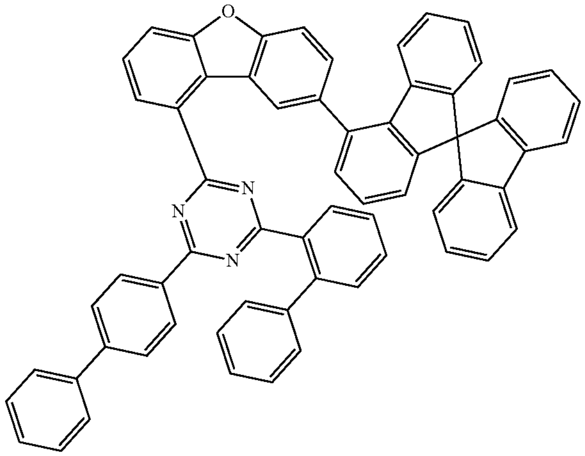 [SMILES: c1ccc(-c2ccc(-c3nc(-c4ccccc4-c4ccccc4)nc(-c4cccc5oc6ccc(-c7cccc8c7-c7ccccc7C87c8ccccc8-c8ccccc87)cc6c45)n3)cc2)cc1]

TABLE 1-continued
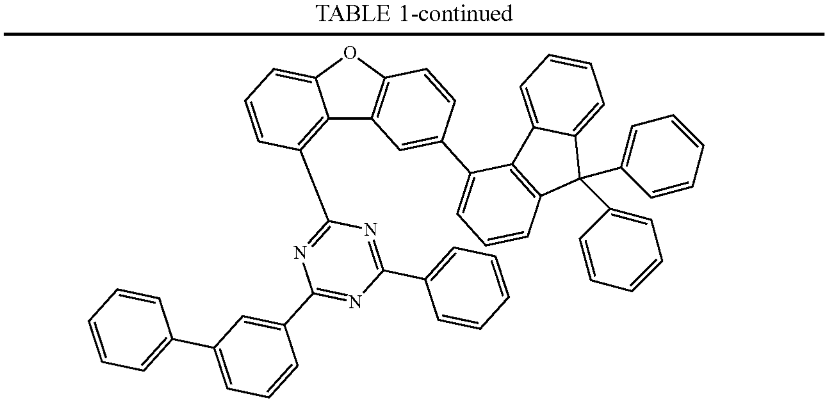
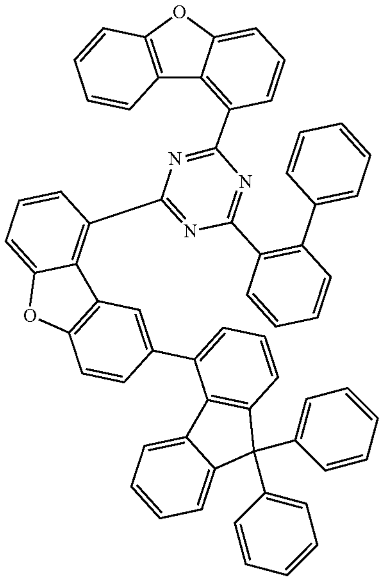 [SMILES: c1ccc(-c2ccccc2-c2nc(-c3cccc4oc5ccccc5c34)nc(-c3cccc4oc5ccc(-c6cccc7c6-c6ccccc6C7(c6ccccc6)c6ccccc6)cc5c34)n2)cc1]
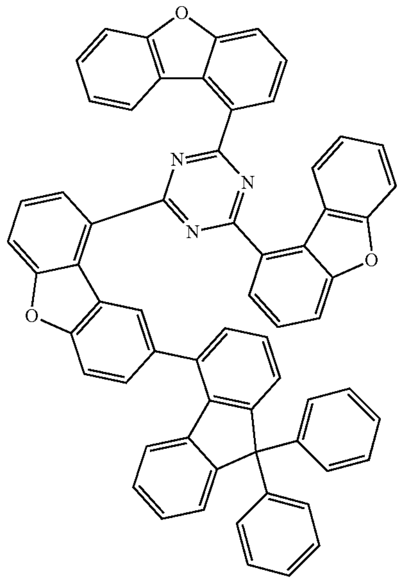 [SMILES: c1ccc(C2(c3ccccc3)c3ccccc3-c3c(-c4ccc5oc6cccc(-c7nc(-c8cccc9oc%10ccccc%10c89)nc(-c8cccc9oc%10ccccc%10c89)n7)c6c5c4)cccc32)cc1]

TABLE 1-continued
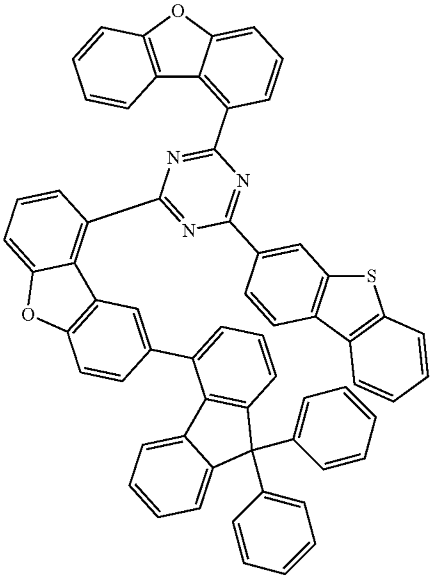 [SMILES: c1ccc(C2(c3ccccc3)c3ccccc3-c3c(-c4ccc5oc6cccc(-c7nc(-c8ccc9c(c8)sc8ccccc89)nc(-c8cccc9oc%10ccccc%10c89)n7)c6c5c4)cccc32)cc1]
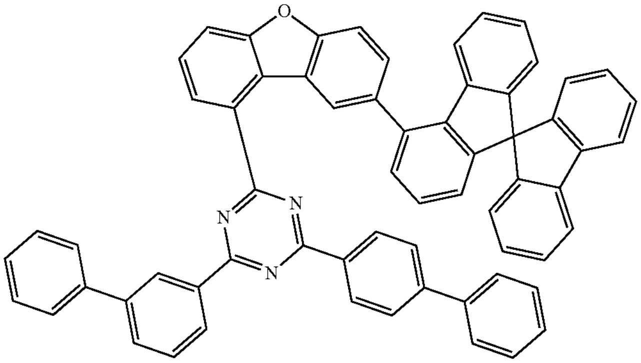 [SMILES: c1ccc(-c2ccc(-c3nc(-c4cccc(-c5ccccc5)c4)nc(-c4cccc5oc6ccc(-c7cccc8c7-c7ccccc7C87c8ccccc8-c8ccccc87)cc6c45)n3)cc2)cc1]
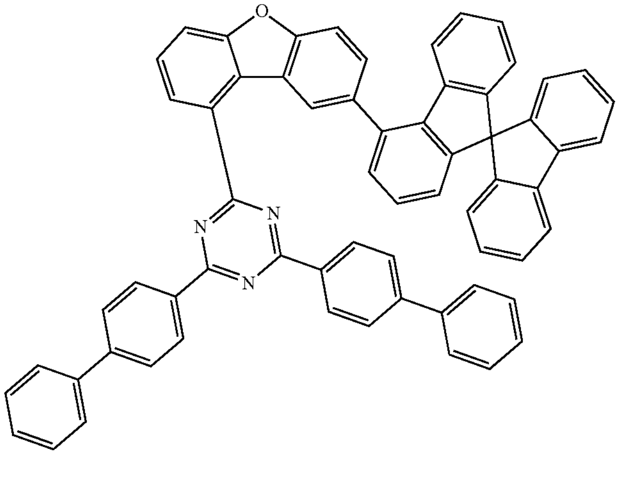 [SMILES: c1ccc(-c2ccc(-c3nc(-c4ccc(-c5ccccc5)cc4)nc(-c4cccc5oc6ccc(-c7cccc8c7-c7ccccc7C87c8ccccc8-c8ccccc87)cc6c45)n3)cc2)cc1]

TABLE 1-continued
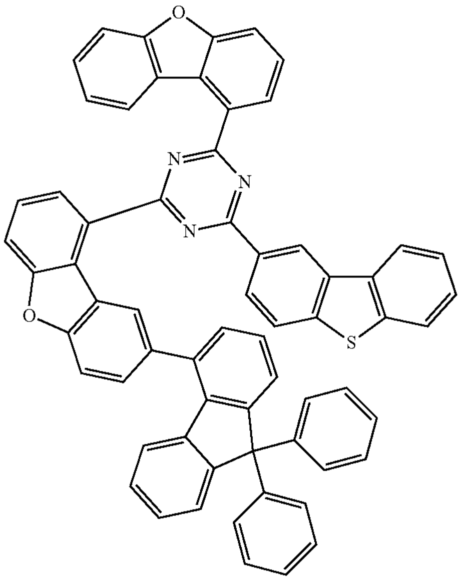 [SMILES: c1ccc(C2(c3ccccc3)c3ccccc3-c3c(-c4ccc5oc6cccc(-c7nc(-c8ccc9sc%10ccccc%10c9c8)nc(-c8cccc9oc%10ccccc%10c89)n7)c6c5c4)cccc32)cc1]
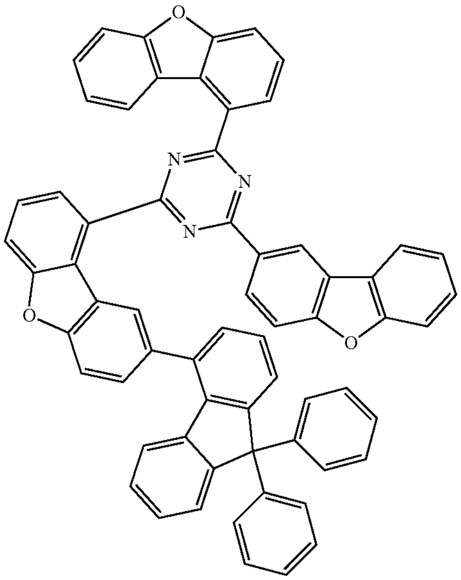 [SMILES: c1ccc(C2(c3ccccc3)c3ccccc3-c3c(-c4ccc5oc6cccc(-c7nc(-c8ccc9oc%10ccccc%10c9c8)nc(-c8cccc9oc%10ccccc%10c89)n7)c6c5c4)cccc32)cc1]

TABLE 1-continued
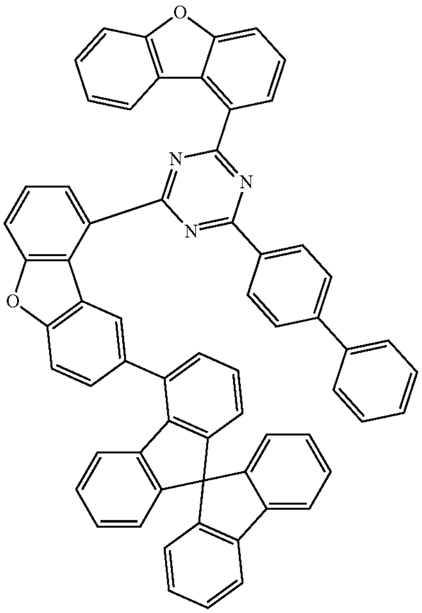 [SMILES: c1ccc(-c2ccc(-c3nc(-c4cccc5oc6ccccc6c45)nc(-c4cccc5oc6ccc(-c7cccc8c7-c7ccccc7C87c8ccccc8-c8ccccc87)cc6c45)n3)cc2)cc1]
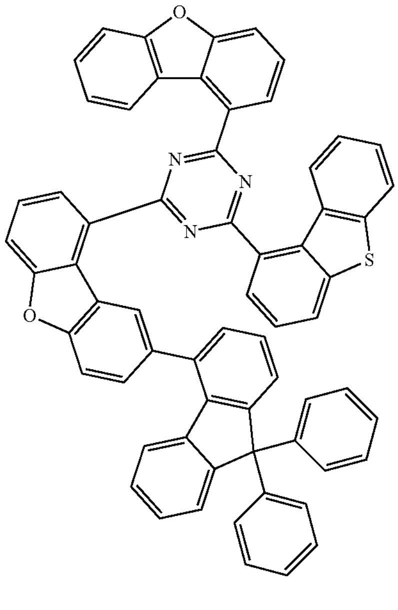 [SMILES: c1ccc(C2(c3ccccc3)c3ccccc3-c3c(-c4ccc5oc6cccc(-c7nc(-c8cccc9oc%10ccccc%10c89)nc(-c8cccc9sc%10ccccc%10c89)n7)c6c5c4)cccc32)cc1]

TABLE 1-continued
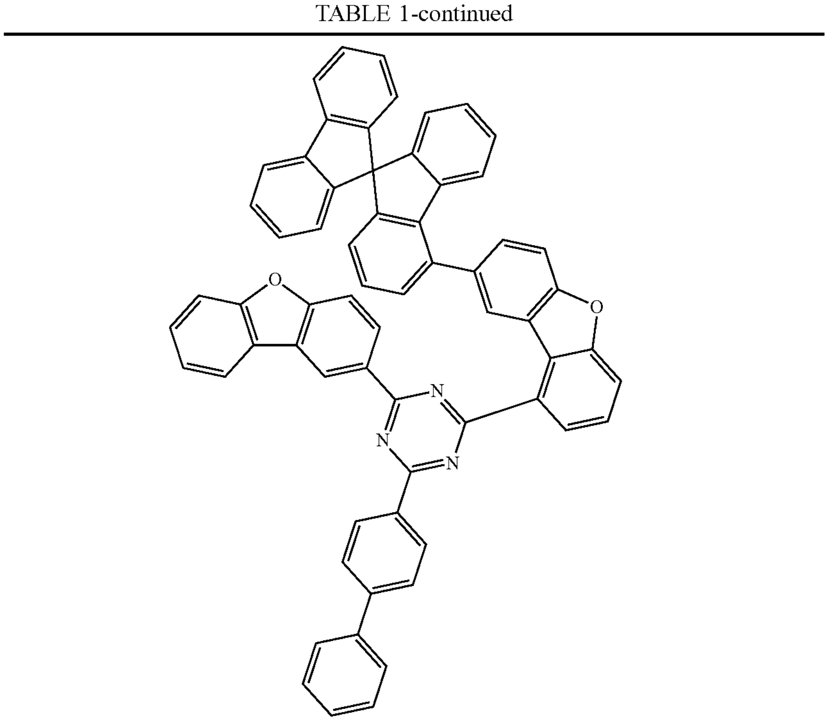
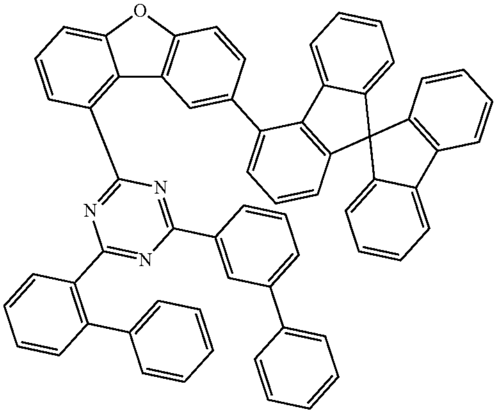 [SMILES: c1ccc(-c2cccc(-c3nc(-c4ccccc4-c4ccccc4)nc(-c4cccc5oc6ccc(-c7cccc8c7-c7ccccc7C87c8ccccc8-c8ccccc87)cc6c45)n3)c2)cc1]
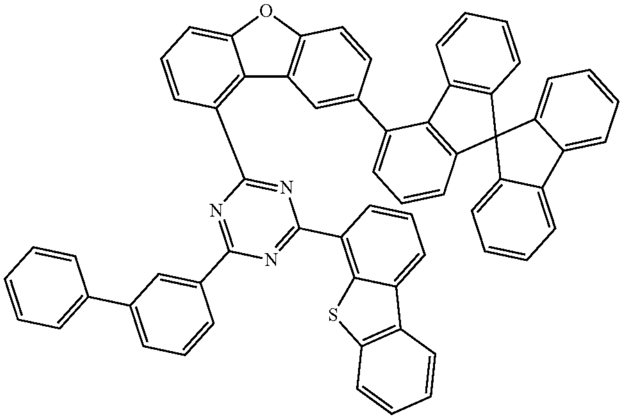 [SMILES: c1ccc(-c2cccc(-c3nc(-c4cccc5c4sc4ccccc45)nc(-c4cccc5oc6ccc(-c7cccc8c7-c7ccccc7C87c8ccccc8-c8ccccc87)cc6c45)n3)c2)cc1]

TABLE 1-continued
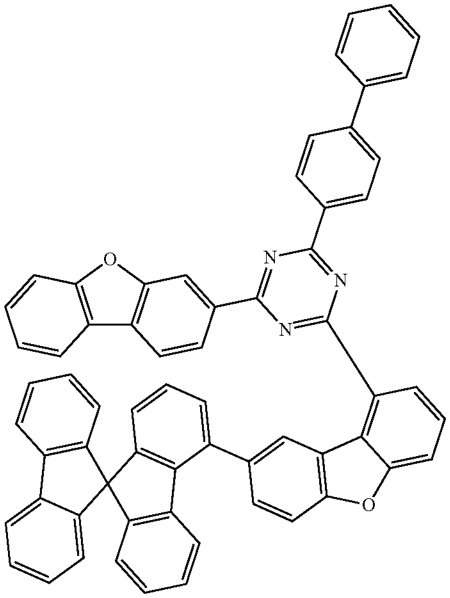 [SMILES: c1ccc(-c2ccc(-c3nc(-c4ccc5c(c4)oc4ccccc45)nc(-c4cccc5oc6ccc(-c7cccc8c7-c7ccccc7C87c8ccccc8-c8ccccc87)cc6c45)n3)cc2)cc1]
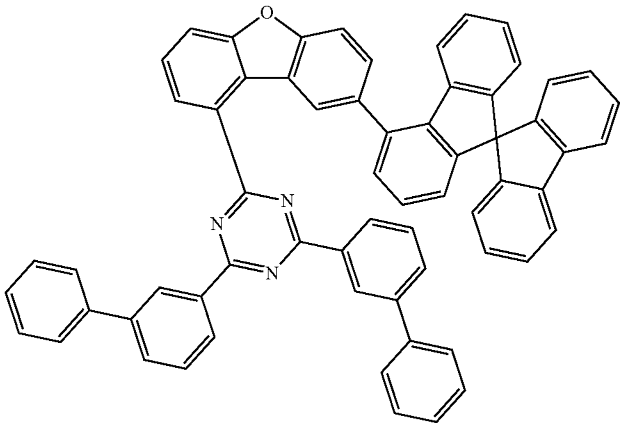 [SMILES: c1ccc(-c2cccc(-c3nc(-c4cccc(-c5ccccc5)c4)nc(-c4cccc5oc6ccc(-c7cccc8c7-c7ccccc7C87c8ccccc8-c8ccccc87)cc6c45)n3)c2)cc1]
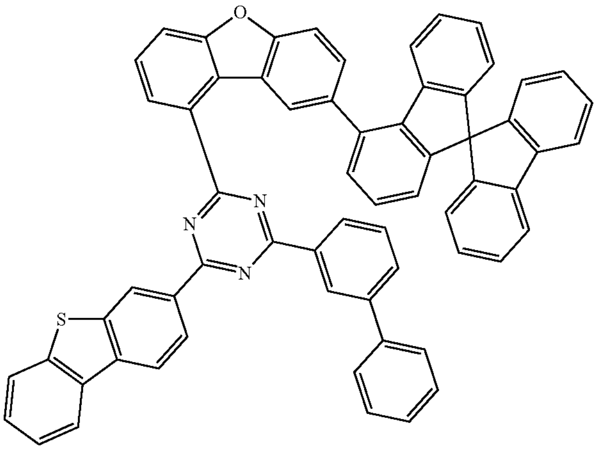 [SMILES: c1ccc(-c2cccc(-c3nc(-c4ccc5c(c4)sc4ccccc45)nc(-c4cccc5oc6ccc(-c7cccc8c7-c7ccccc7C87c8ccccc8-c8ccccc87)cc6c45)n3)c2)cc1]

TABLE 1-continued
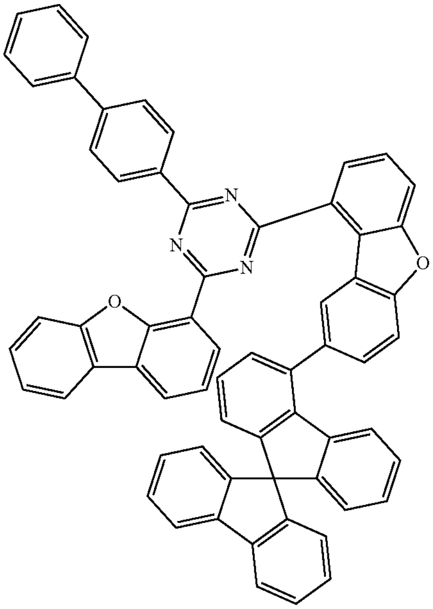 [SMILES: c1ccc(-c2ccc(-c3nc(-c4cccc5c4oc4ccccc45)nc(-c4cccc5oc6ccc(-c7cccc8c7-c7ccccc7C87c8ccccc8-c8ccccc87)cc6c45)n3)cc2)cc1]
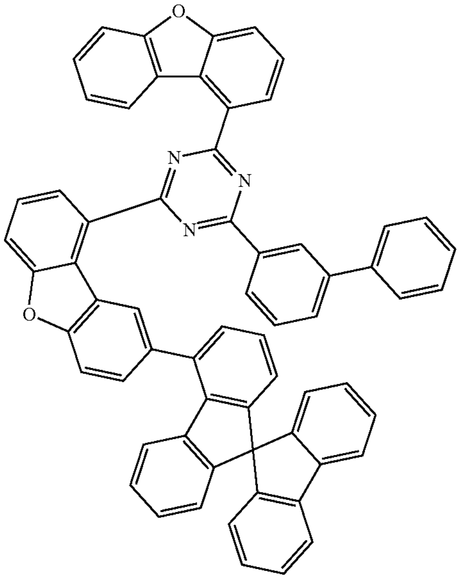 [SMILES: c1ccc(-c2cccc(-c3nc(-c4cccc5oc6ccccc6c45)nc(-c4cccc5oc6ccc(-c7cccc8c7-c7ccccc7C87c8ccccc8-c8ccccc87)cc6c45)n3)c2)cc1]
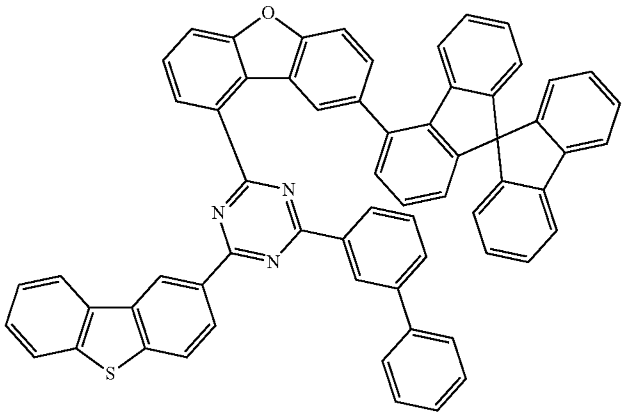 [SMILES: c1ccc(-c2cccc(-c3nc(-c4ccc5sc6ccccc6c5c4)nc(-c4cccc5oc6ccc(-c7cccc8c7-c7ccccc7C87c8ccccc8-c8ccccc87)cc6c45)n3)c2)cc1]

TABLE 1-continued
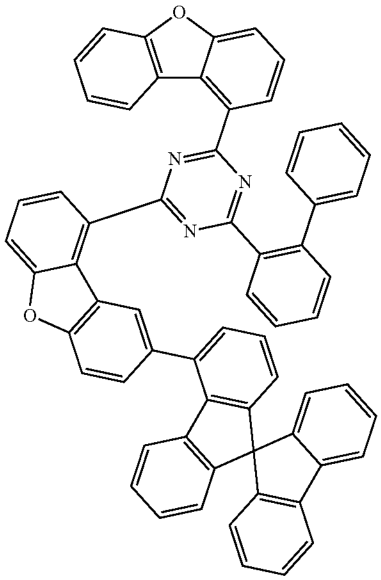 [SMILES: c1ccc(-c2ccccc2-c2nc(-c3cccc4oc5ccccc5c34)nc(-c3cccc4oc5ccc(-c6cccc7c6-c6ccccc6C76c7ccccc7-c7ccccc76)cc5c34)n2)cc1]
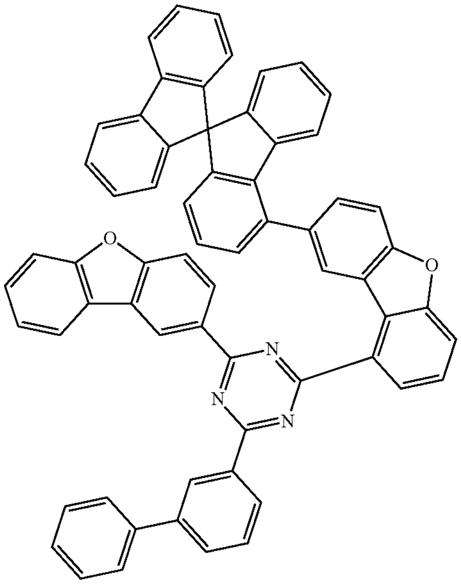 [SMILES: c1ccc(-c2cccc(-c3nc(-c4ccc5oc6ccccc6c5c4)nc(-c4cccc5oc6ccc(-c7cccc8c7-c7ccccc7C87c8ccccc8-c8ccccc87)cc6c45)n3)c2)cc1]

TABLE 1-continued
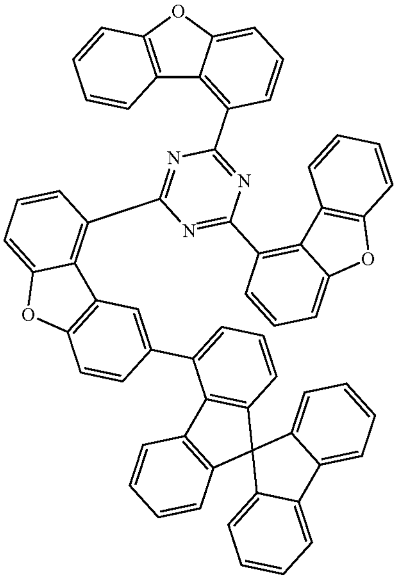 [SMILES: c1ccc2c(c1)-c1ccccc1C21c2ccccc2-c2c(-c3ccc4oc5cccc(-c6nc(-c7cccc8oc9ccccc9c78)nc(-c7cccc8oc9ccccc9c78)n6)c5c4c3)cccc21]
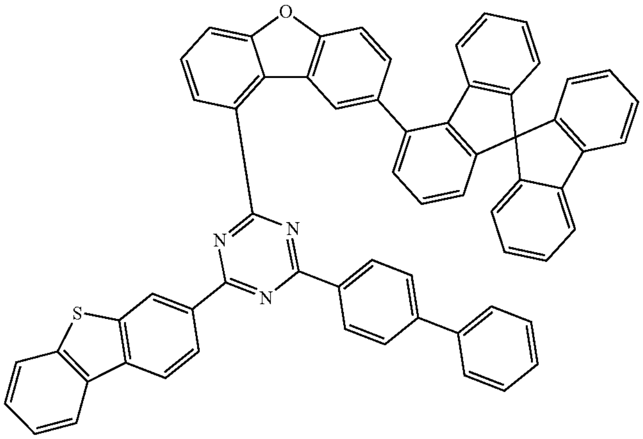 [SMILES: c1ccc(-c2ccc(-c3nc(-c4ccc5c(c4)sc4ccccc45)nc(-c4cccc5oc6ccc(-c7cccc8c7-c7ccccc7C87c8ccccc8-c8ccccc87)cc6c45)n3)cc2)cc1]
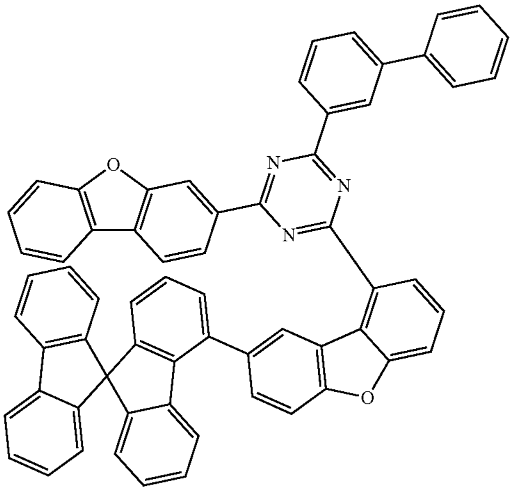 [SMILES: c1ccc(-c2cccc(-c3nc(-c4ccc5c(c4)oc4ccccc45)nc(-c4cccc5oc6ccc(-c7cccc8c7-c7ccccc7C87c8ccccc8-c8ccccc87)cc6c45)n3)c2)cc1]

TABLE 1-continued
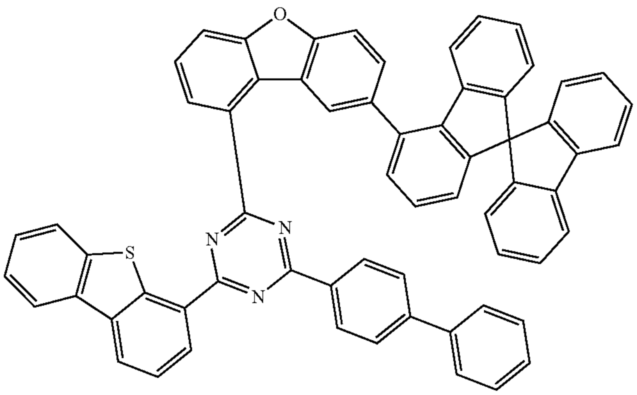 [SMILES: c1ccc(-c2ccc(-c3nc(-c4cccc5c4sc4ccccc45)nc(-c4cccc5oc6ccc(-c7cccc8c7-c7ccccc7C87c8ccccc8-c8ccccc87)cc6c45)n3)cc2)cc1]
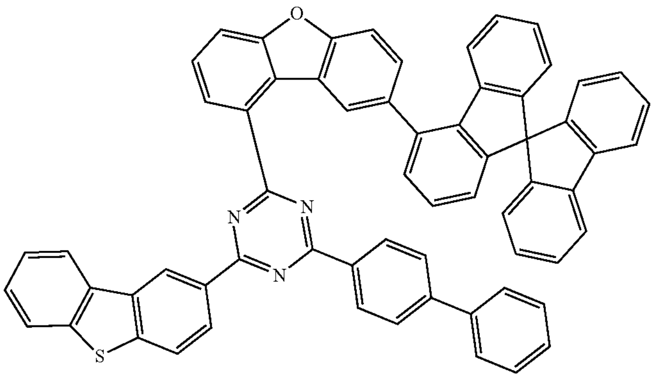 [SMILES: c1ccc(-c2ccc(-c3nc(-c4ccc5sc6ccccc6c5c4)nc(-c4cccc5oc6ccc(-c7cccc8c7-c7ccccc7C87c8ccccc8-c8ccccc87)cc6c45)n3)cc2)cc1]
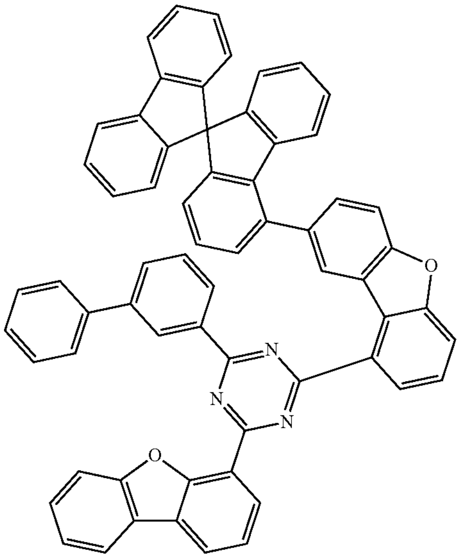 [SMILES: c1ccc(-c2cccc(-c3nc(-c4cccc5c4oc4ccccc45)nc(-c4cccc5oc6ccc(-c7cccc8c7-c7ccccc7C87c8ccccc8-c8ccccc87)cc6c45)n3)c2)cc1]

TABLE 1-continued
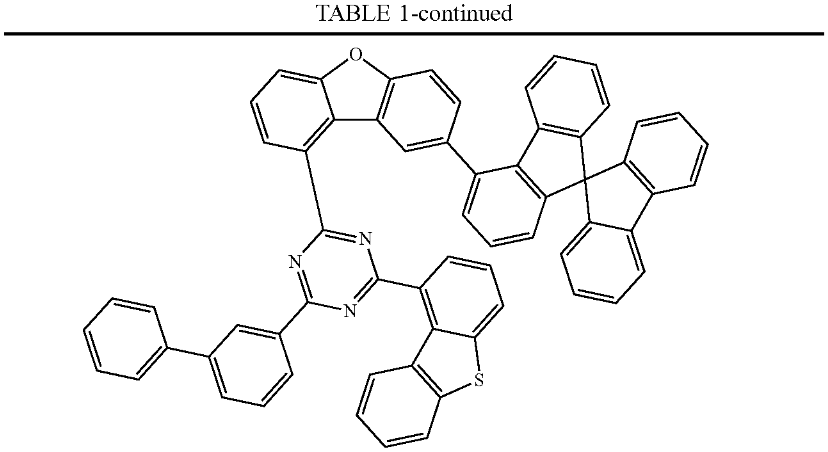
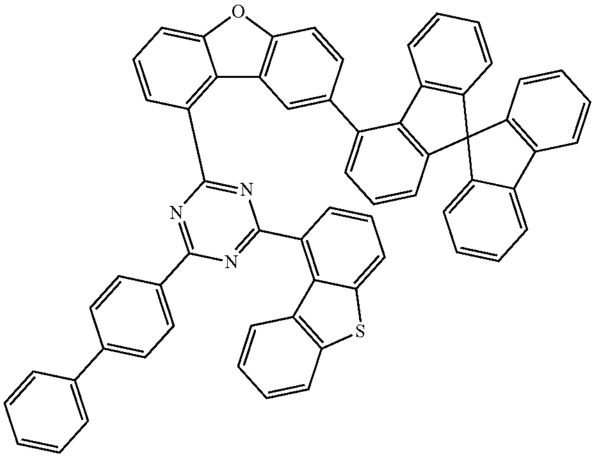 [SMILES: c1ccc(-c2ccc(-c3nc(-c4cccc5oc6ccc(-c7cccc8c7-c7ccccc7C87c8ccccc8-c8ccccc87)cc6c45)nc(-c4cccc5sc6ccccc6c45)n3)cc2)cc1]
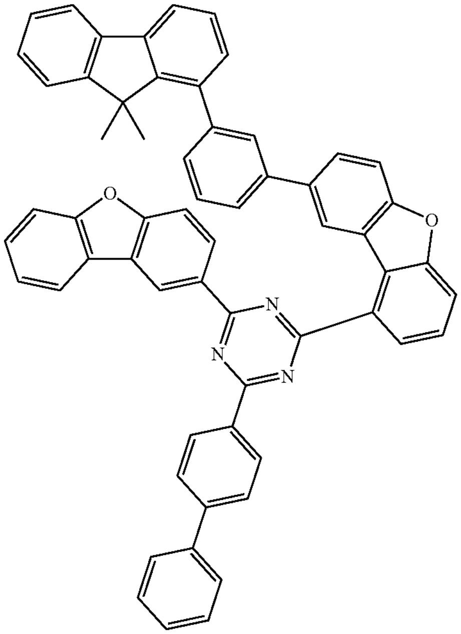 [SMILES: CC1(C)c2ccccc2-c2cccc(-c3cccc(-c4ccc5oc6cccc(-c7nc(-c8ccc(-c9ccccc9)cc8)nc(-c8ccc9oc%10ccccc%10c9c8)n7)c6c5c4)c3)c21]

TABLE 1-continued
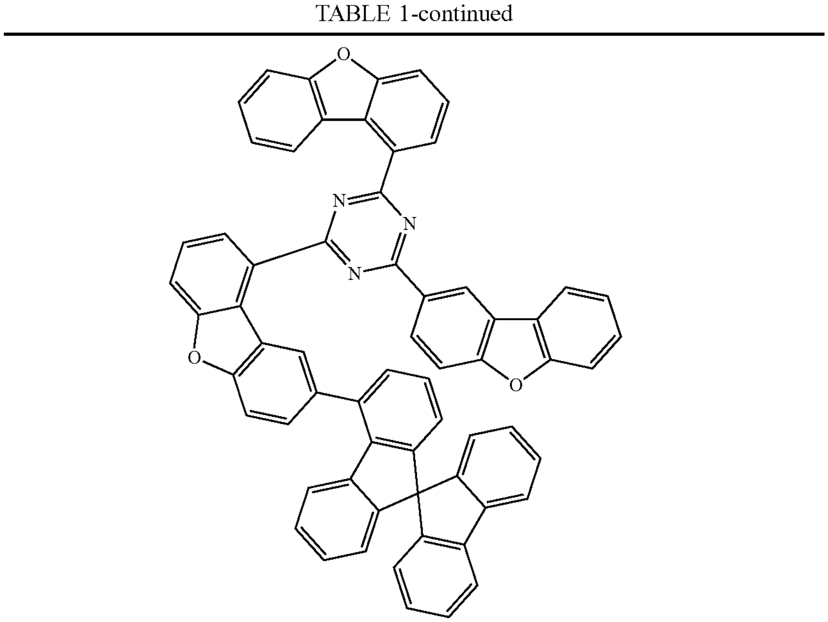
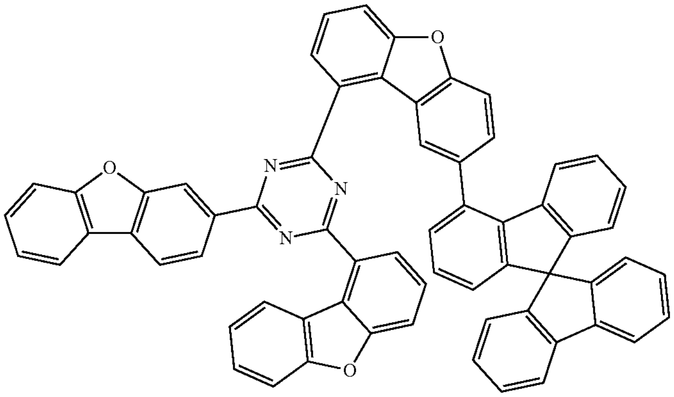 [SMILES: c1ccc2c(c1)-c1ccccc1C21c2ccccc2-c2c(-c3ccc4oc5cccc(-c6nc(-c7ccc8c(c7)oc7ccccc78)nc(-c7cccc8oc9ccccc9c78)n6)c5c4c3)cccc21]
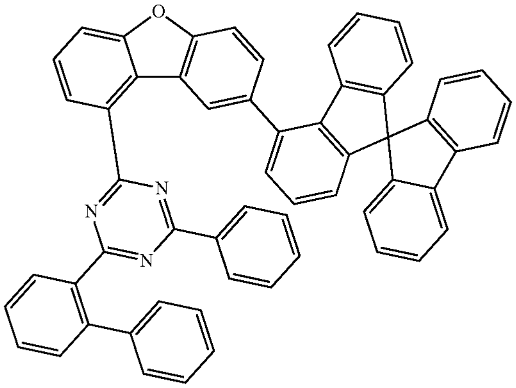 [SMILES: c1ccc(-c2nc(-c3ccccc3-c3ccccc3)nc(-c3cccc4oc5ccc(-c6cccc7c6-c6ccccc6C76c7ccccc7-c7ccccc76)cc5c34)n2)cc1]

TABLE 1-continued
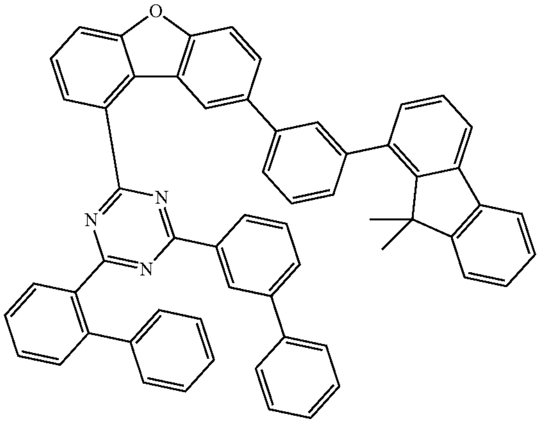 [SMILES: CC1(C)c2ccccc2-c2cccc(-c3cccc(-c4ccc5oc6cccc(-c7nc(-c8cccc(-c9ccccc9)c8)nc(-c8ccccc8-c8ccccc8)n7)c6c5c4)c3)c21]
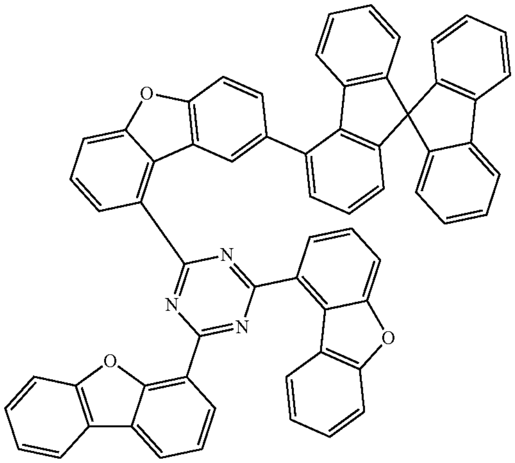 [SMILES: c1ccc2c(c1)-c1ccccc1C21c2ccccc2-c2c(-c3ccc4oc5cccc(-c6nc(-c7cccc8c7oc7ccccc78)nc(-c7cccc8oc9ccccc9c78)n6)c5c4c3)cccc21]
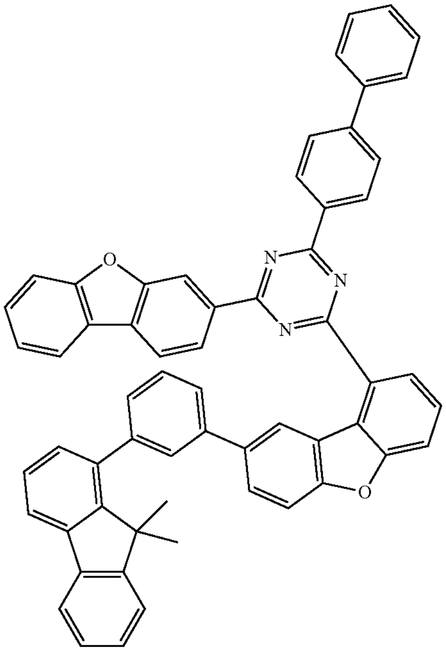 [SMILES: CC1(C)c2ccccc2-c2cccc(-c3cccc(-c4ccc5oc6cccc(-c7nc(-c8ccc(-c9ccccc9)cc8)nc(-c8ccc9c(c8)oc8ccccc89)n7)c6c5c4)c3)c21]

TABLE 1-continued
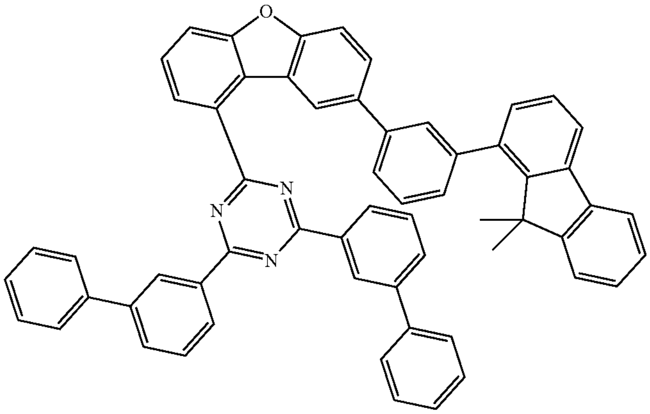 [SMILES: CC1(C)c2ccccc2-c2cccc(-c3cccc(-c4ccc5oc6cccc(-c7nc(-c8cccc(-c9ccccc9)c8)nc(-c8cccc(-c9ccccc9)c8)n7)c6c5c4)c3)c21]
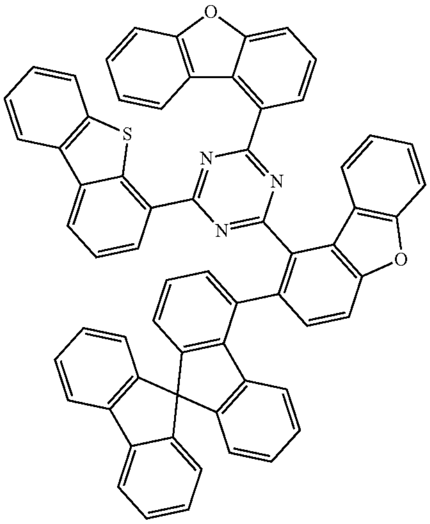 [SMILES: c1ccc2c(c1)-c1ccccc1C21c2ccccc2-c2c(-c3ccc4oc5ccccc5c4c3-c3nc(-c4cccc5c4sc4ccccc45)nc(-c4cccc5oc6ccccc6c45)n3)cccc21]
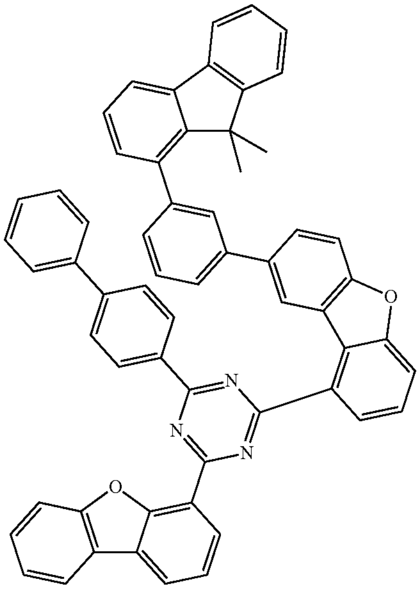 [SMILES: CC1(C)c2ccccc2-c2cccc(-c3cccc(-c4ccc5oc6cccc(-c7nc(-c8ccc(-c9ccccc9)cc8)nc(-c8cccc9c8oc8ccccc89)n7)c6c5c4)c3)c21]

TABLE 1-continued
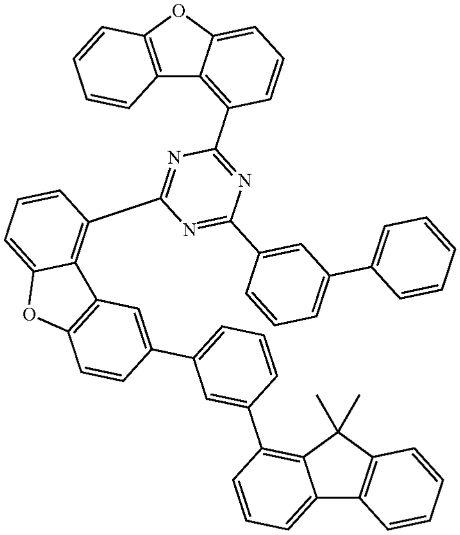 [SMILES: CC1(C)c2ccccc2-c2cccc(-c3cccc(-c4ccc5oc6cccc(-c7nc(-c8cccc(-c9ccccc9)c8)nc(-c8cccc9oc%10ccccc%10c89)n7)c6c5c4)c3)c21]
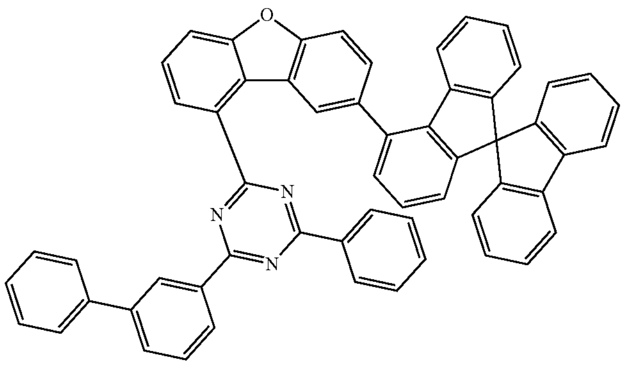 [SMILES: c1ccc(-c2cccc(-c3nc(-c4ccccc4)nc(-c4cccc5oc6ccc(-c7cccc8c7-c7ccccc7C87c8ccccc8-c8ccccc87)cc6c45)n3)c2)cc1]
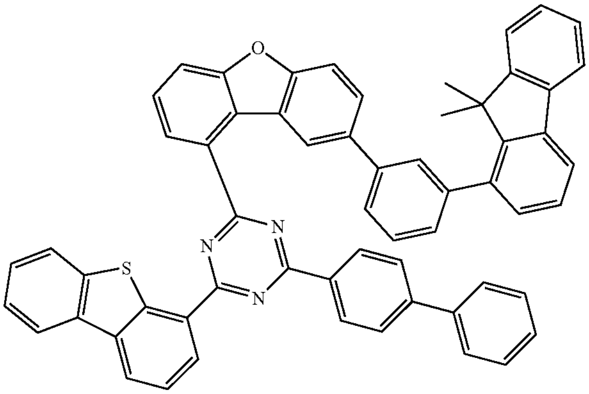 [SMILES: CC1(C)c2ccccc2-c2cccc(-c3cccc(-c4ccc5oc6cccc(-c7nc(-c8ccc(-c9ccccc9)cc8)nc(-c8cccc9c8sc8ccccc89)n7)c6c5c4)c3)c21]

TABLE 1-continued
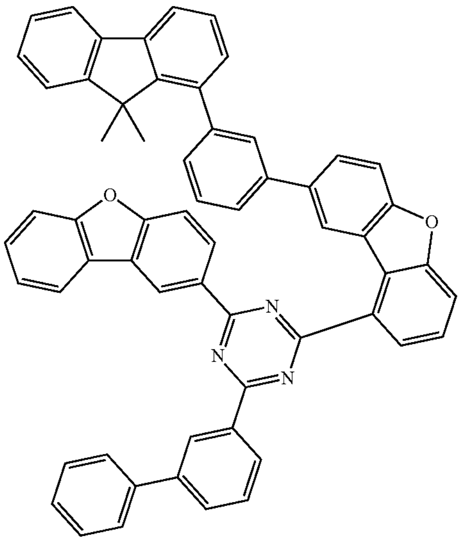 [SMILES: CC1(C)c2ccccc2-c2cccc(-c3cccc(-c4ccc5oc6cccc(-c7nc(-c8cccc(-c9ccccc9)c8)nc(-c8ccc9oc%10ccccc%10c9c8)n7)c6c5c4)c3)c21]
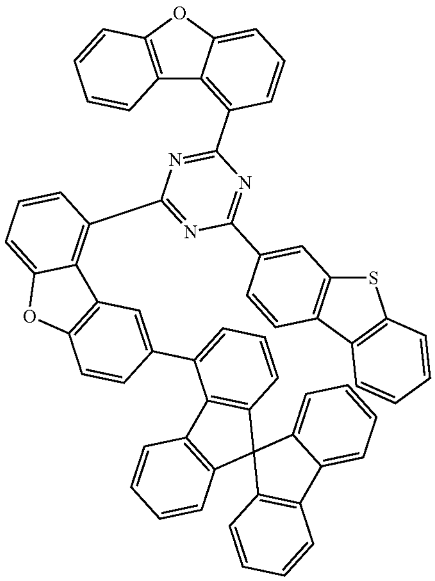 [SMILES: c1ccc2c(c1)-c1ccccc1C21c2ccccc2-c2c(-c3ccc4oc5cccc(-c6nc(-c7ccc8c(c7)sc7ccccc78)nc(-c7cccc8oc9ccccc9c78)n6)c5c4c3)cccc21]

TABLE 1-continued
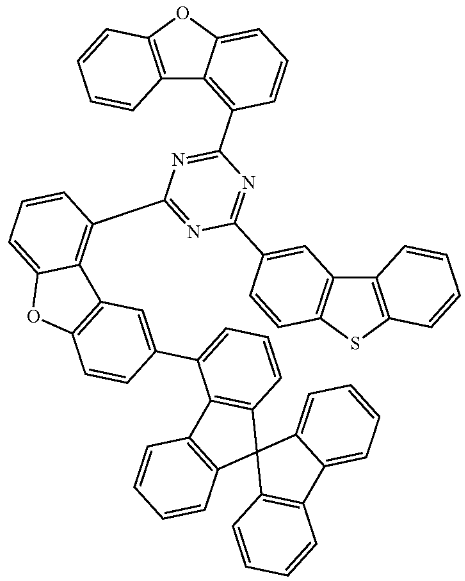 [SMILES: c1ccc2c(c1)-c1ccccc1C21c2ccccc2-c2c(-c3ccc4oc5cccc(-c6nc(-c7ccc8sc9ccccc9c8c7)nc(-c7cccc8oc9ccccc9c78)n6)c5c4c3)cccc21]
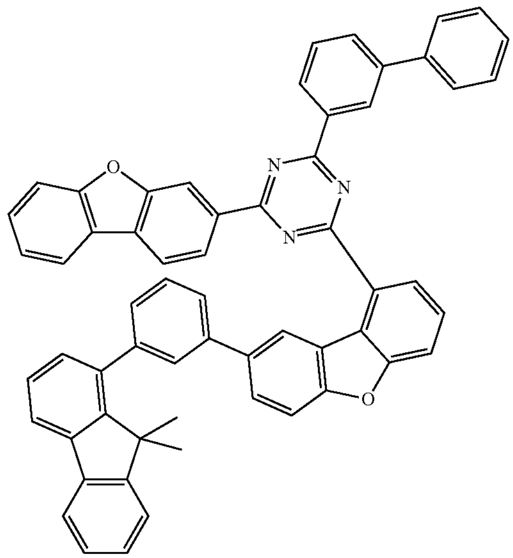 [SMILES: CC1(C)c2ccccc2-c2cccc(-c3cccc(-c4ccc5oc6cccc(-c7nc(-c8cccc(-c9ccccc9)c8)nc(-c8ccc9c(c8)oc8ccccc89)n7)c6c5c4)c3)c21]
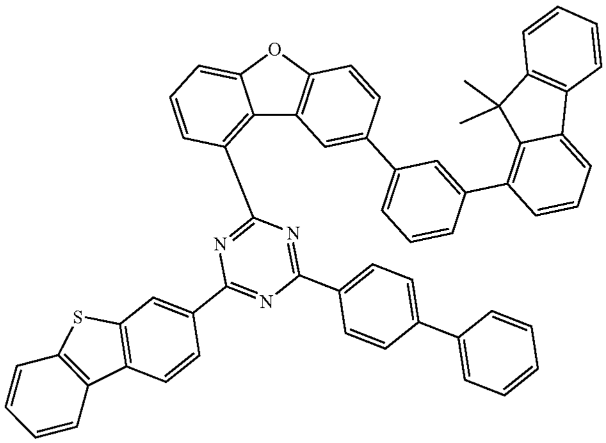 [SMILES: CC1(C)c2ccccc2-c2cccc(-c3cccc(-c4ccc5oc6cccc(-c7nc(-c8ccc(-c9ccccc9)cc8)nc(-c8ccc9c(c8)sc8ccccc89)n7)c6c5c4)c3)c21]

TABLE 1-continued
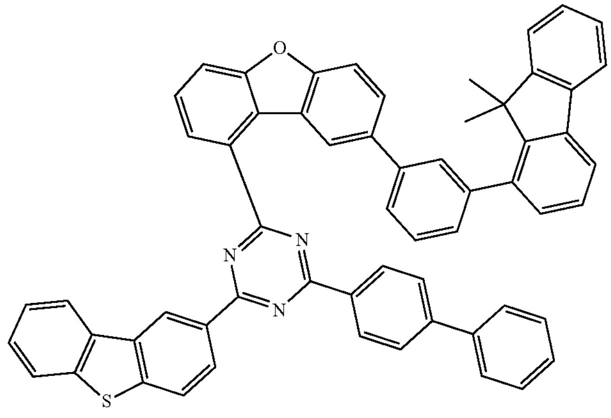 [SMILES: CC1(C)c2ccccc2-c2cccc(-c3cccc(-c4ccc5oc6cccc(-c7nc(-c8ccc(-c9ccccc9)cc8)nc(-c8ccc9sc%10ccccc%10c9c8)n7)c6c5c4)c3)c21]
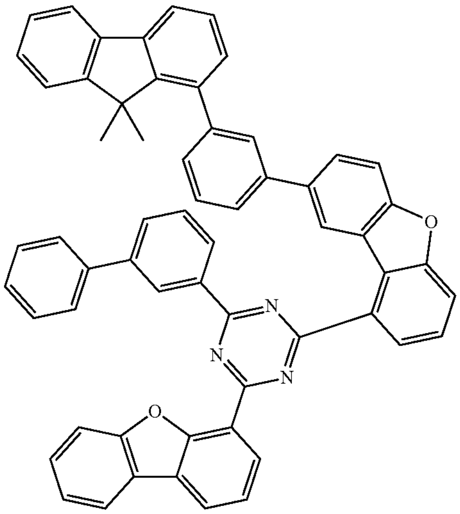 [SMILES: CC1(C)c2ccccc2-c2cccc(-c3cccc(-c4ccc5oc6cccc(-c7nc(-c8cccc(-c9ccccc9)c8)nc(-c8cccc9c8oc8ccccc89)n7)c6c5c4)c3)c21]
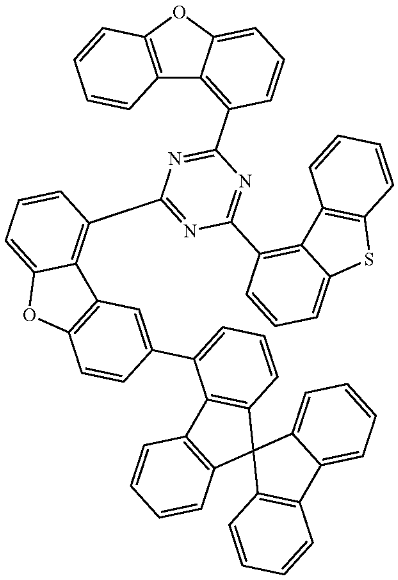 [SMILES: c1ccc2c(c1)-c1ccccc1C21c2ccccc2-c2c(-c3ccc4oc5cccc(-c6nc(-c7cccc8oc9ccccc9c78)nc(-c7cccc8sc9ccccc9c78)n6)c5c4c3)cccc21]

TABLE 1-continued
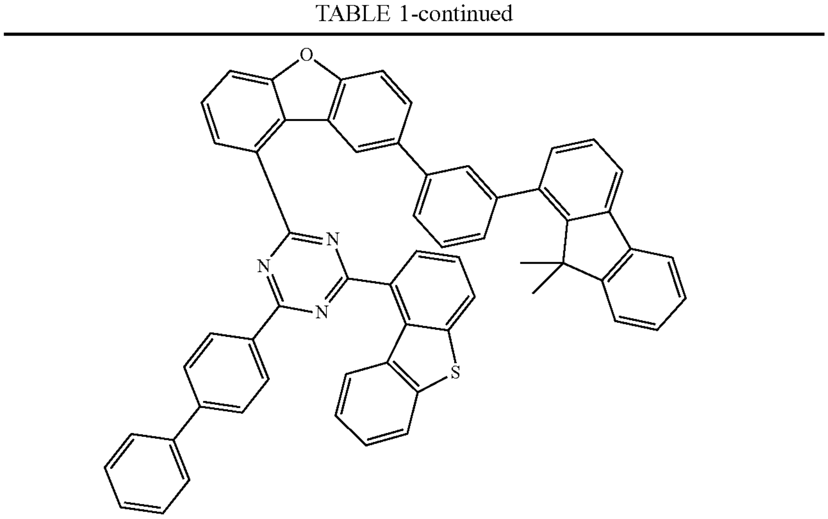
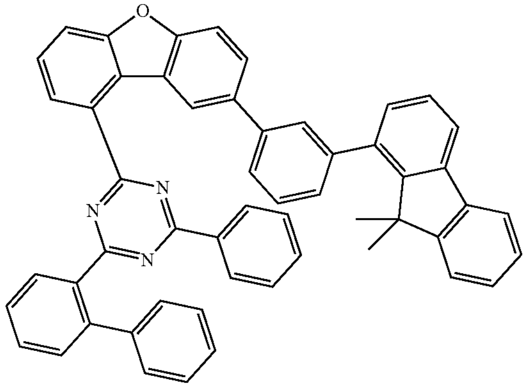 [SMILES: CC1(C)c2ccccc2-c2cccc(-c3cccc(-c4ccc5oc6cccc(-c7nc(-c8ccccc8)nc(-c8ccccc8-c8ccccc8)n7)c6c5c4)c3)c21]
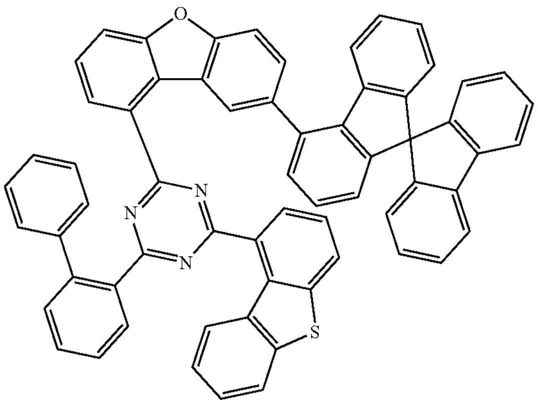 [SMILES: c1ccc(-c2ccccc2-c2nc(-c3cccc4oc5ccc(-c6cccc7c6-c6ccccc6C76c7ccccc7-c7ccccc76)cc5c34)nc(-c3cccc4sc5ccccc5c34)n2)cc1]

TABLE 1-continued
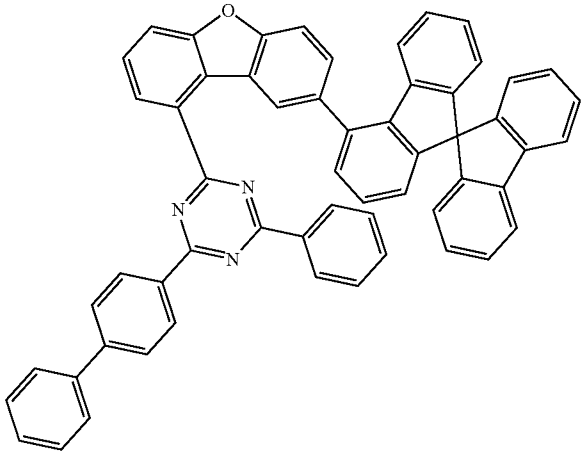 [SMILES: c1ccc(-c2ccc(-c3nc(-c4ccccc4)nc(-c4cccc5oc6ccc(-c7cccc8c7-c7ccccc7C87c8ccccc8-c8ccccc87)cc6c45)n3)cc2)cc1]
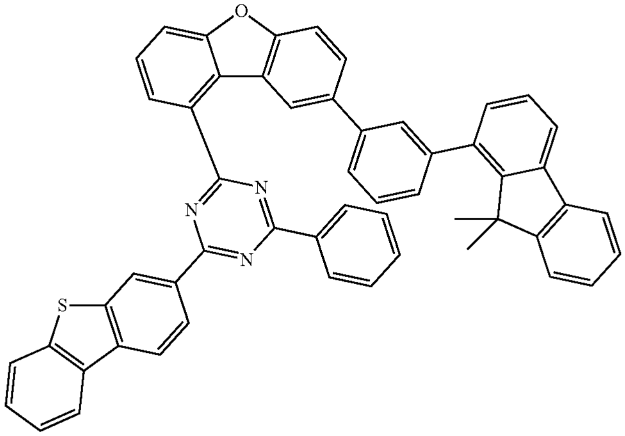 [SMILES: CC1(C)c2ccccc2-c2cccc(-c3cccc(-c4ccc5oc6cccc(-c7nc(-c8ccccc8)nc(-c8ccc9c(c8)sc8ccccc89)n7)c6c5c4)c3)c21]
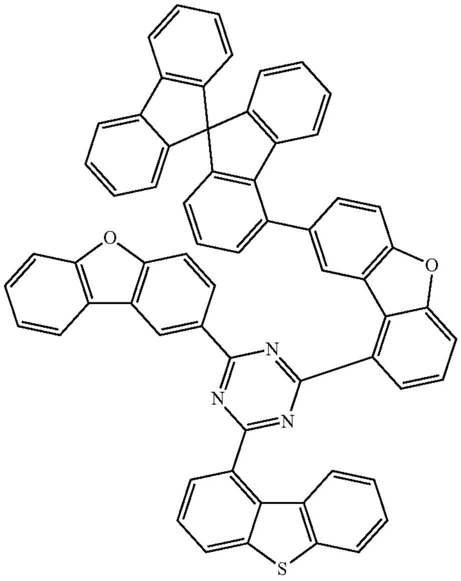 [SMILES: c1ccc2c(c1)-c1ccccc1C21c2ccccc2-c2c(-c3ccc4oc5cccc(-c6nc(-c7ccc8oc9ccccc9c8c7)nc(-c7cccc8sc9ccccc9c78)n6)c5c4c3)cccc21]

TABLE 1-continued
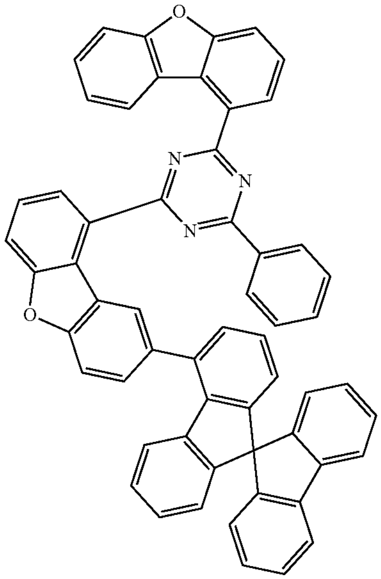 [SMILES: c1ccc(-c2nc(-c3cccc4oc5ccccc5c34)nc(-c3cccc4oc5ccc(-c6cccc7c6-c6ccccc6C76c7ccccc7-c7ccccc76)cc5c34)n2)cc1]
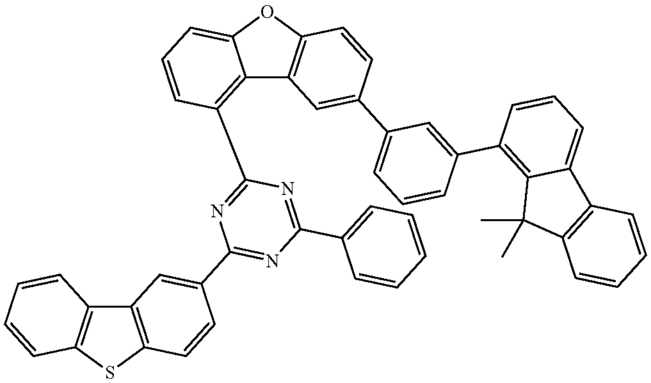 [SMILES: CC1(C)c2ccccc2-c2cccc(-c3cccc(-c4ccc5oc6cccc(-c7nc(-c8ccccc8)nc(-c8ccc9sc%10ccccc%10c9c8)n7)c6c5c4)c3)c21]
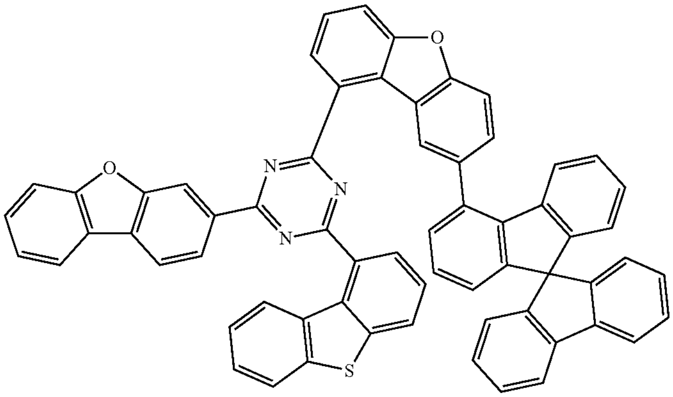 [SMILES: c1ccc2c(c1)-c1ccccc1C21c2ccccc2-c2c(-c3ccc4oc5cccc(-c6nc(-c7ccc8c(c7)oc7ccccc78)nc(-c7cccc8sc9ccccc9c78)n6)c5c4c3)cccc21]

TABLE 1-continued
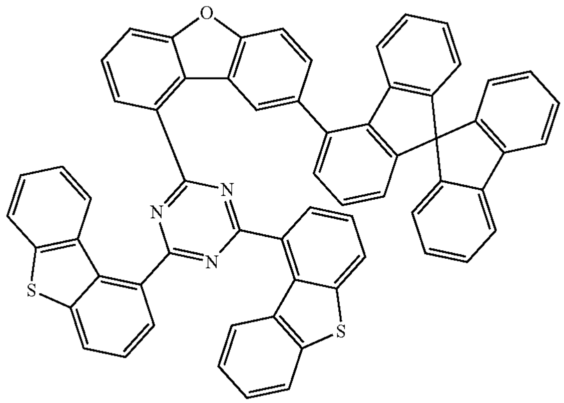 [SMILES: c1ccc2c(c1)-c1ccccc1C21c2ccccc2-c2c(-c3ccc4oc5cccc(-c6nc(-c7cccc8sc9ccccc9c78)nc(-c7cccc8sc9ccccc9c78)n6)c5c4c3)cccc21]
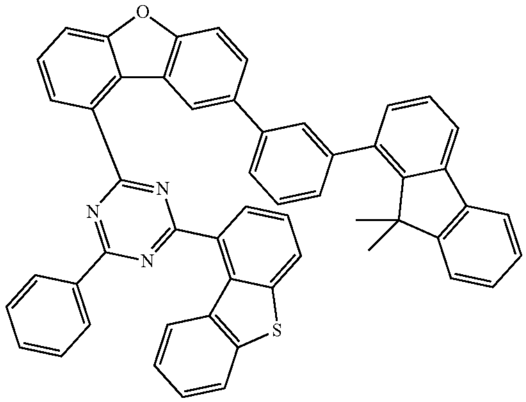 [SMILES: CC1(C)c2ccccc2-c2cccc(-c3cccc(-c4ccc5oc6cccc(-c7nc(-c8ccccc8)nc(-c8cccc9sc%10ccccc%10c89)n7)c6c5c4)c3)c21]
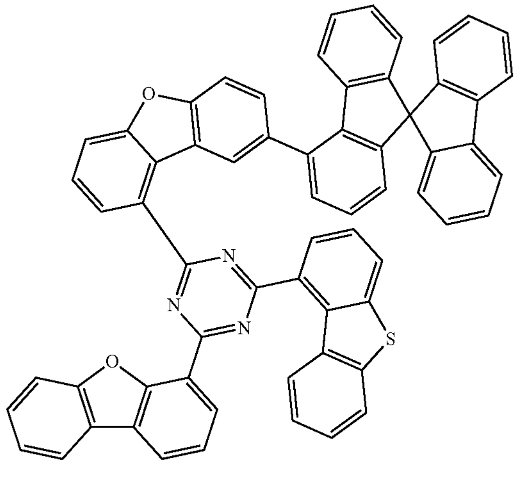 [SMILES: c1ccc2c(c1)-c1ccccc1C21c2ccccc2-c2c(-c3ccc4oc5cccc(-c6nc(-c7cccc8c7oc7ccccc78)nc(-c7cccc8sc9ccccc9c78)n6)c5c4c3)cccc21]

TABLE 1-continued
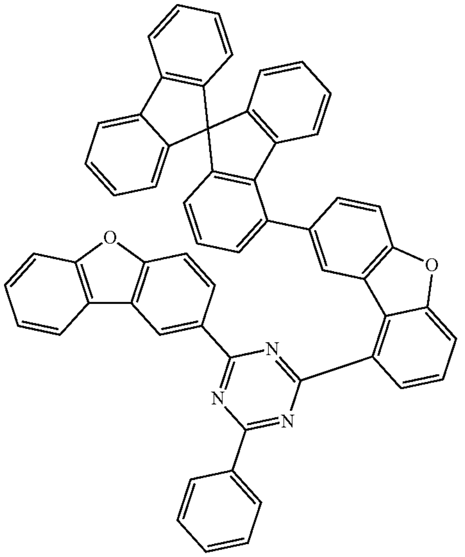 [SMILES: c1ccc(-c2nc(-c3ccc4oc5ccccc5c4c3)nc(-c3cccc4oc5ccc(-c6cccc7c6-c6ccccc6C76c7ccccc7-c7ccccc76)cc5c34)n2)cc1]
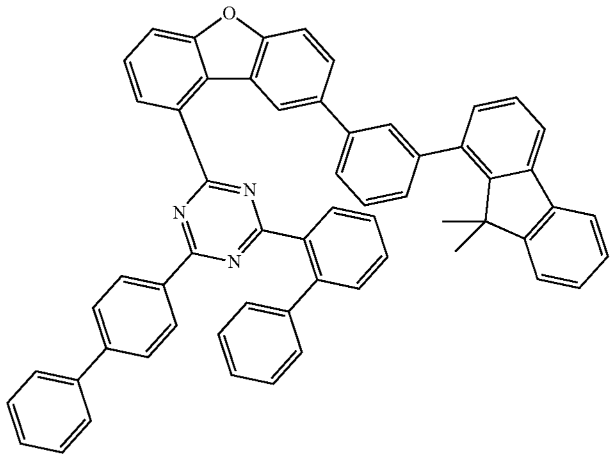 [SMILES: CC1(C)c2ccccc2-c2cccc(-c3cccc(-c4ccc5oc6cccc(-c7nc(-c8ccc(-c9ccccc9)cc8)nc(-c8ccccc8-c8ccccc8)n7)c6c5c4)c3)c21]
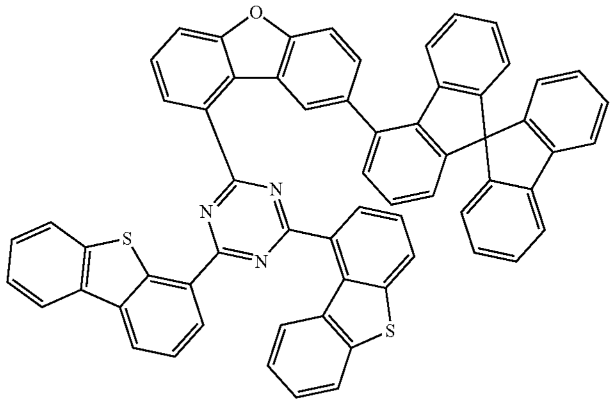 [SMILES: c1ccc2c(c1)-c1ccccc1C21c2ccccc2-c2c(-c3ccc4oc5cccc(-c6nc(-c7cccc8c7sc7ccccc78)nc(-c7cccc8sc9ccccc9c78)n6)c5c4c3)cccc21]

TABLE 1-continued
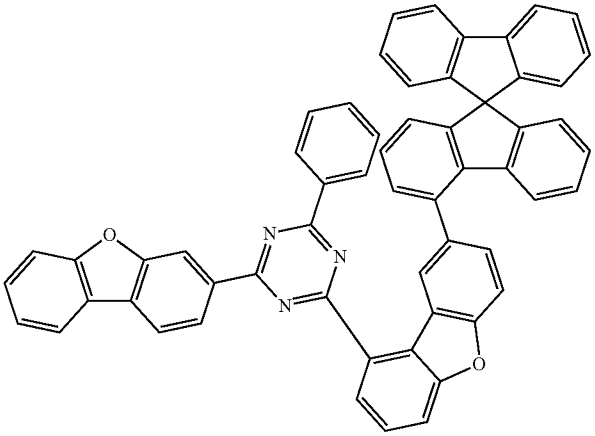 [SMILES: c1ccc(-c2nc(-c3ccc4c(c3)oc3ccccc34)nc(-c3cccc4oc5ccc(-c6cccc7c6-c6ccccc6C76c7ccccc7-c7ccccc76)cc5c34)n2)cc1]
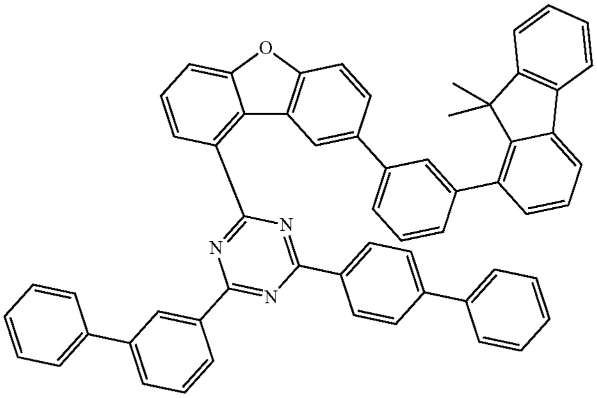 [SMILES: CC1(C)c2ccccc2-c2cccc(-c3cccc(-c4ccc5oc6cccc(-c7nc(-c8ccc(-c9ccccc9)cc8)nc(-c8cccc(-c9ccccc9)c8)n7)c6c5c4)c3)c21]
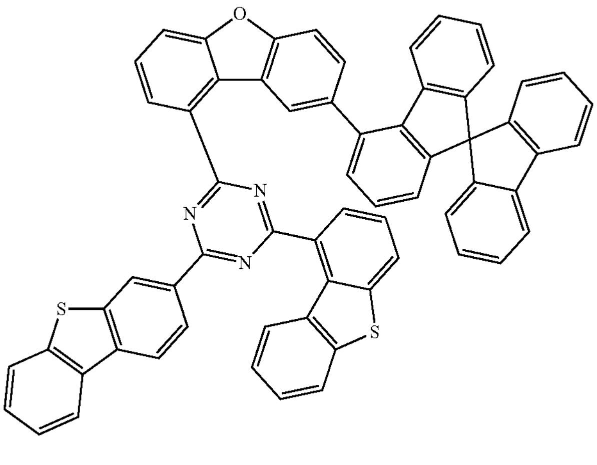 [SMILES: c1ccc2c(c1)-c1ccccc1C21c2ccccc2-c2c(-c3ccc4oc5cccc(-c6nc(-c7ccc8c(c7)sc7ccccc78)nc(-c7cccc8sc9ccccc9c78)n6)c5c4c3)cccc21]

TABLE 1-continued
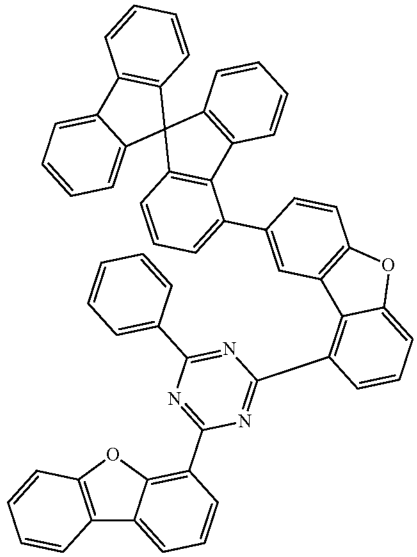 [SMILES: c1ccc(-c2nc(-c3cccc4c3oc3ccccc34)nc(-c3cccc4oc5ccc(-c6cccc7c6-c6ccccc6C76c7ccccc7-c7ccccc76)cc5c34)n2)cc1]
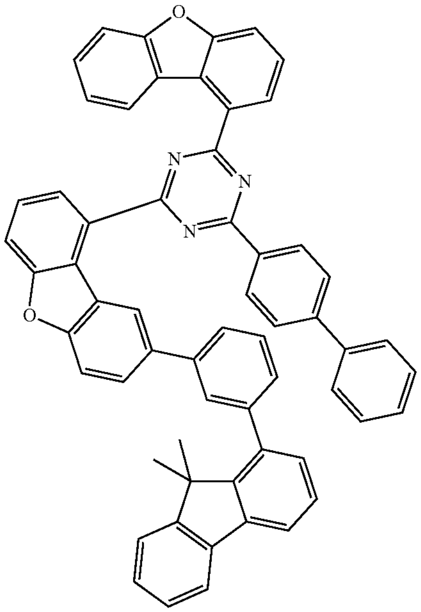 [SMILES: CC1(C)c2ccccc2-c2cccc(-c3cccc(-c4ccc5oc6cccc(-c7nc(-c8ccc(-c9ccccc9)cc8)nc(-c8cccc9oc%10ccccc%10c89)n7)c6c5c4)c3)c21]
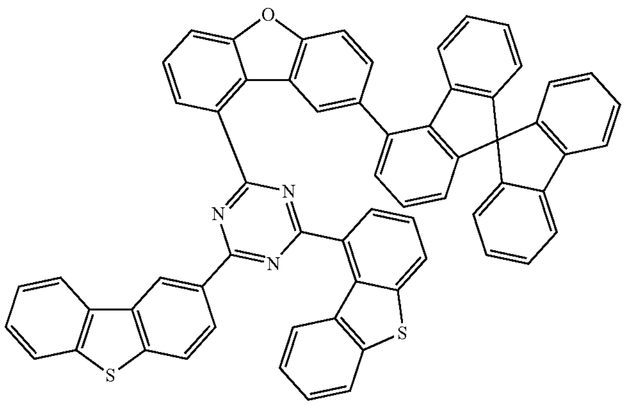 [SMILES: c1ccc2c(c1)-c1ccccc1C21c2ccccc2-c2c(-c3ccc4oc5cccc(-c6nc(-c7ccc8sc9ccccc9c8c7)nc(-c7cccc8sc9ccccc9c78)n6)c5c4c3)cccc21]

TABLE 1-continued
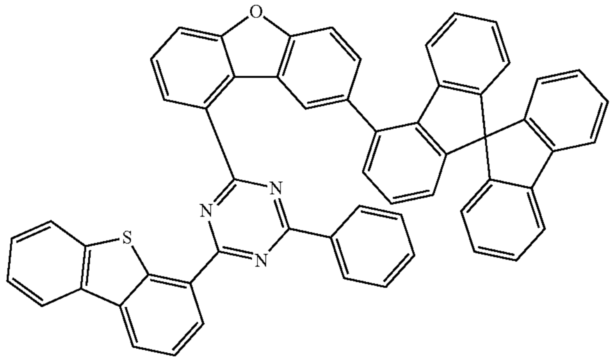 [SMILES: c1ccc(-c2nc(-c3cccc4c3sc3ccccc34)nc(-c3cccc4oc5ccc(-c6cccc7c6-c6ccccc6C76c7ccccc7-c7ccccc76)cc5c34)n2)cc1]
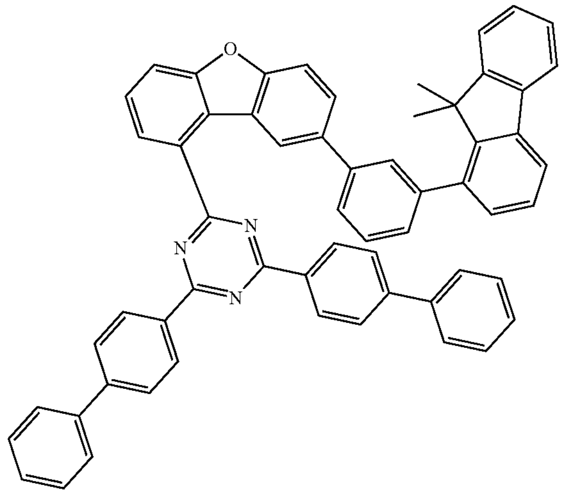 [SMILES: CC1(C)c2ccccc2-c2cccc(-c3cccc(-c4ccc5oc6cccc(-c7nc(-c8ccc(-c9ccccc9)cc8)nc(-c8ccc(-c9ccccc9)cc8)n7)c6c5c4)c3)c21]
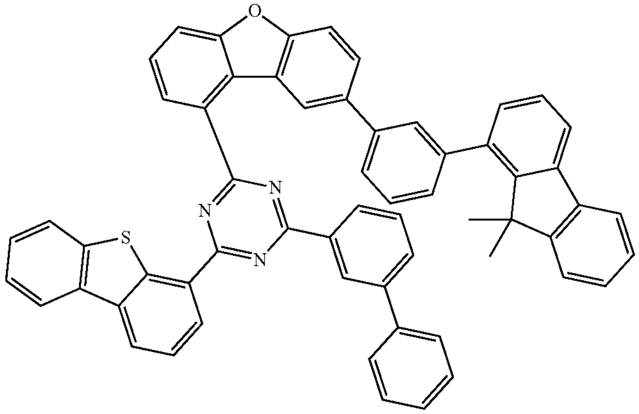 [SMILES: CC1(C)c2ccccc2-c2cccc(-c3cccc(-c4ccc5oc6cccc(-c7nc(-c8cccc(-c9ccccc9)c8)nc(-c8cccc9c8sc8ccccc89)n7)c6c5c4)c3)c21]

TABLE 1-continued
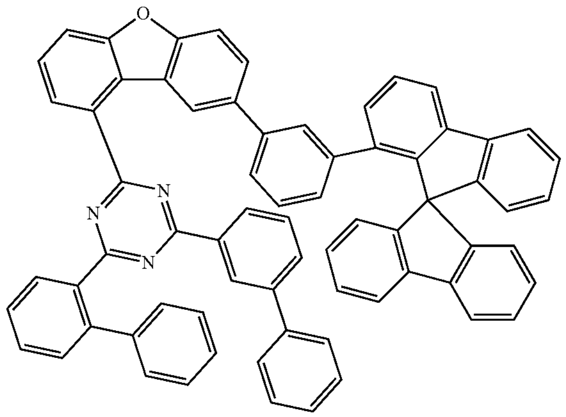 [SMILES: c1ccc(-c2cccc(-c3nc(-c4ccccc4-c4ccccc4)nc(-c4cccc5oc6ccc(-c7cccc(-c8cccc9c8C8(c%10ccccc%10-c%10ccccc%108)c8ccccc8-9)c7)cc6c45)n3)c2)cc1]
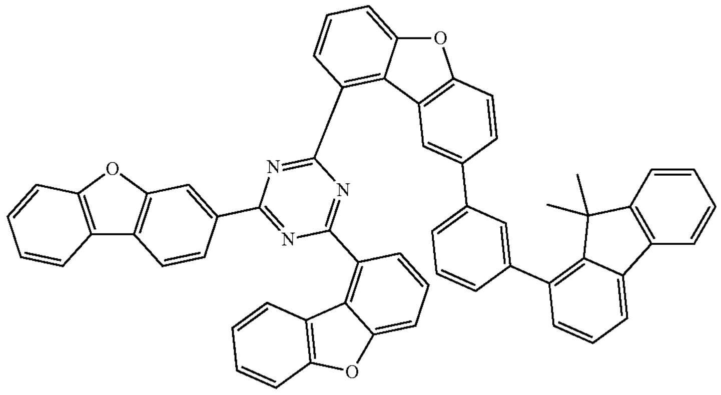 [SMILES: CC1(C)c2ccccc2-c2cccc(-c3cccc(-c4ccc5oc6cccc(-c7nc(-c8ccc9c(c8)oc8ccccc89)nc(-c8cccc9oc%10ccccc%10c89)n7)c6c5c4)c3)c21]
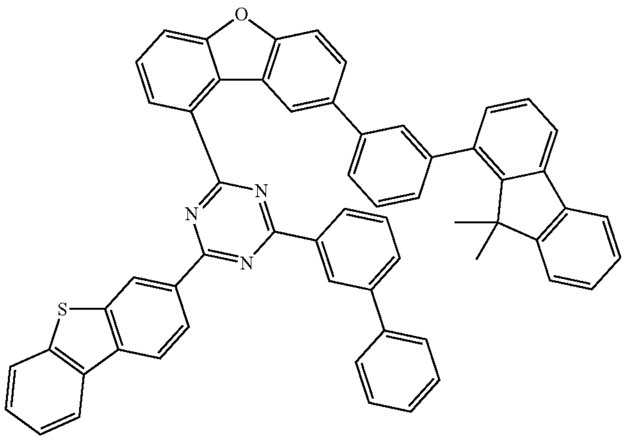 [SMILES: CC1(C)c2ccccc2-c2cccc(-c3cccc(-c4ccc5oc6cccc(-c7nc(-c8cccc(-c9ccccc9)c8)nc(-c8ccc9c(c8)sc8ccccc89)n7)c6c5c4)c3)c21]

TABLE 1-continued
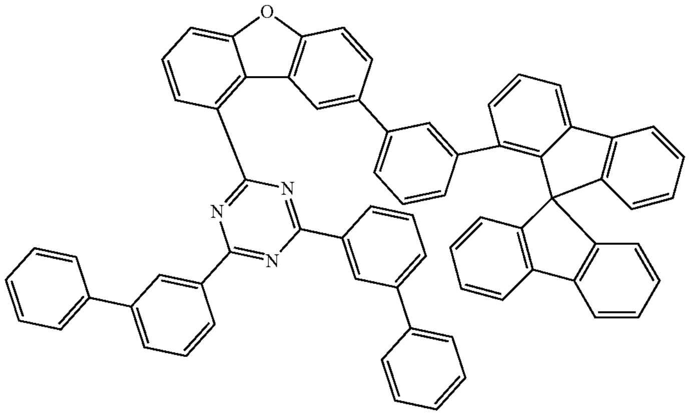 [SMILES: c1ccc(-c2cccc(-c3nc(-c4cccc(-c5ccccc5)c4)nc(-c4cccc5oc6ccc(-c7cccc(-c8cccc9c8C8(c%10ccccc%10-c%10ccccc%108)c8ccccc8-9)c7)cc6c45)n3)c2)cc1]
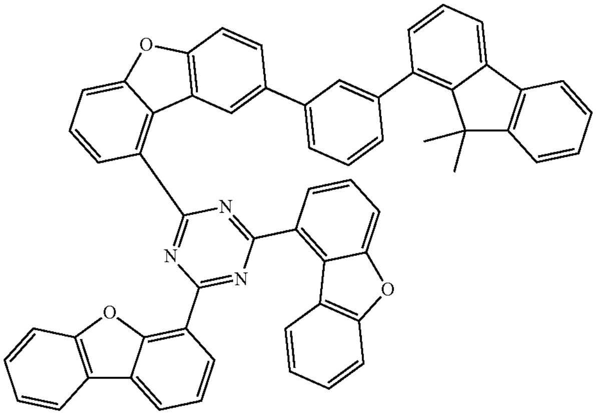 [SMILES: CC1(C)c2ccccc2-c2cccc(-c3cccc(-c4ccc5oc6cccc(-c7nc(-c8cccc9c8oc8ccccc89)nc(-c8cccc9oc%10ccccc%10c89)n7)c6c5c4)c3)c21]
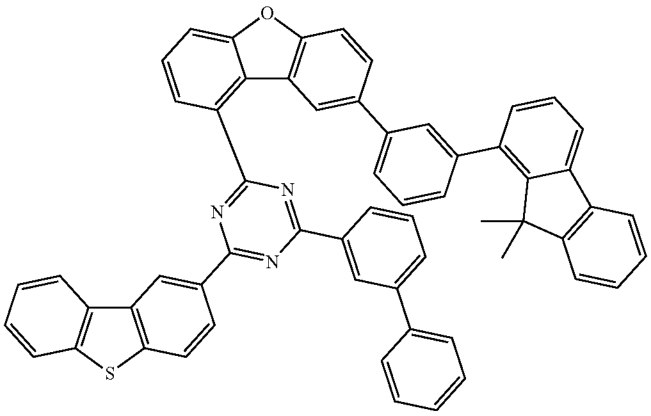 [SMILES: CC1(C)c2ccccc2-c2cccc(-c3cccc(-c4ccc5oc6cccc(-c7nc(-c8cccc(-c9ccccc9)c8)nc(-c8ccc9sc%10ccccc%10c9c8)n7)c6c5c4)c3)c21]

TABLE 1-continued
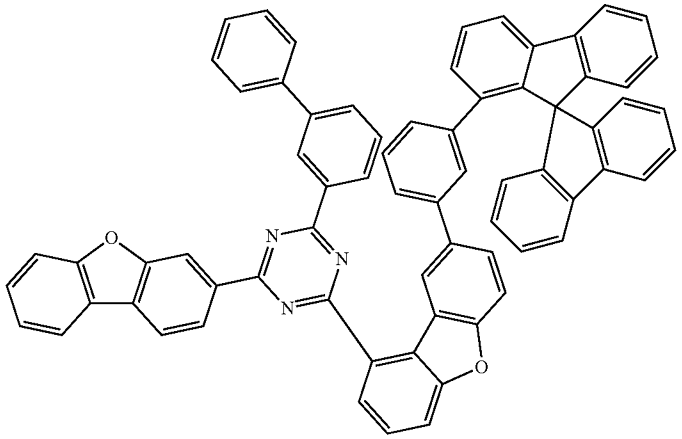 [SMILES: c1ccc(-c2cccc(-c3nc(-c4ccc5c(c4)oc4ccccc45)nc(-c4cccc5oc6ccc(-c7cccc(-c8cccc9c8C8(c%10ccccc%10-c%10ccccc%108)c8ccccc8-9)c7)cc6c45)n3)c2)cc1]
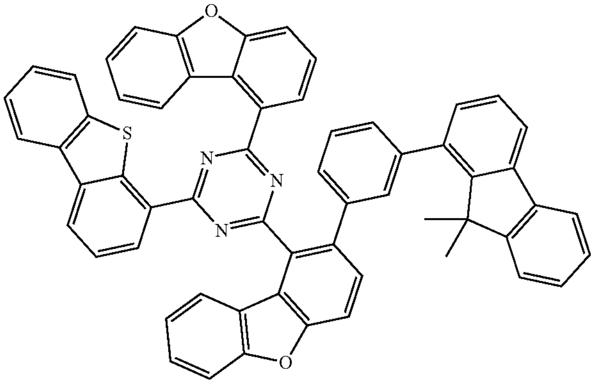 [SMILES: CC1(C)c2ccccc2-c2cccc(-c3cccc(-c4ccc5oc6ccccc6c5c4-c4nc(-c5cccc6c5sc5ccccc56)nc(-c5cccc6oc7ccccc7c56)n4)c3)c21]
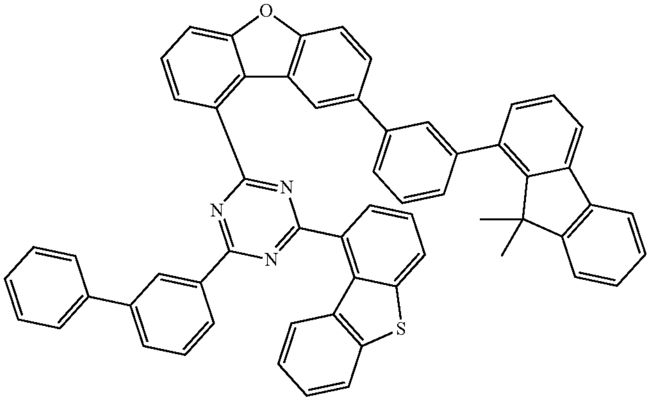 [SMILES: CC1(C)c2ccccc2-c2cccc(-c3cccc(-c4ccc5oc6cccc(-c7nc(-c8cccc(-c9ccccc9)c8)nc(-c8cccc9sc%10ccccc%10c89)n7)c6c5c4)c3)c21]

TABLE 1-continued
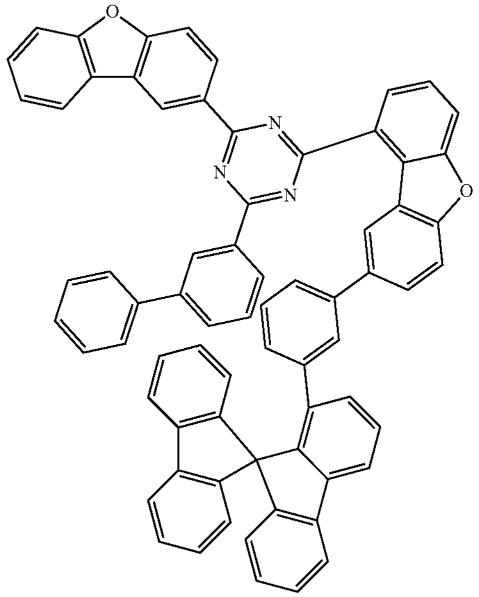 [SMILES: c1ccc(-c2cccc(-c3nc(-c4ccc5oc6ccccc6c5c4)nc(-c4cccc5oc6ccc(-c7cccc(-c8cccc9c8C8(c%10ccccc%10-c%10ccccc%108)c8ccccc8-9)c7)cc6c45)n3)c2)cc1]
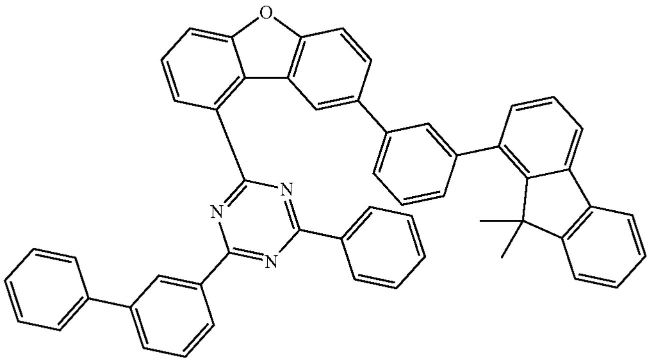 [SMILES: CC1(C)c2ccccc2-c2cccc(-c3cccc(-c4ccc5oc6cccc(-c7nc(-c8ccccc8)nc(-c8cccc(-c9ccccc9)c8)n7)c6c5c4)c3)c21]
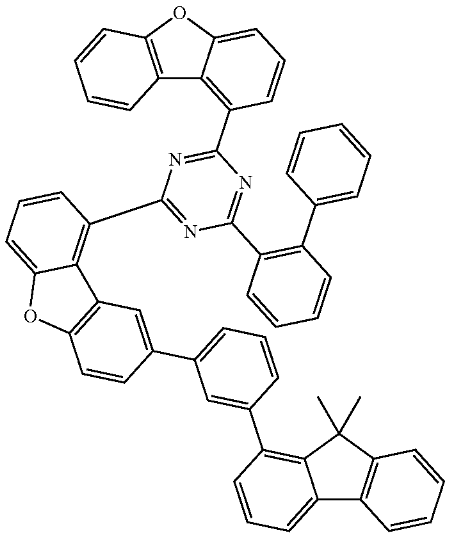 [SMILES: CC1(C)c2ccccc2-c2cccc(-c3cccc(-c4ccc5oc6cccc(-c7nc(-c8ccccc8-c8ccccc8)nc(-c8cccc9oc%10ccccc%10c89)n7)c6c5c4)c3)c21]

TABLE 1-continued
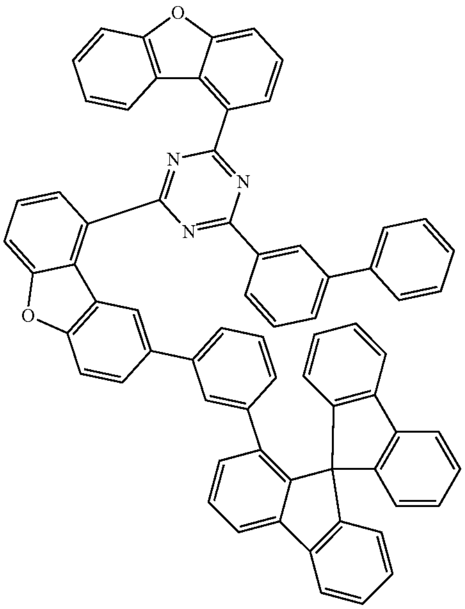 [SMILES: c1ccc(-c2cccc(-c3nc(-c4cccc5oc6ccccc6c45)nc(-c4cccc5oc6ccc(-c7cccc(-c8cccc9c8C8(c%10ccccc%10-c%10ccccc%108)c8ccccc8-9)c7)cc6c45)n3)c2)cc1]
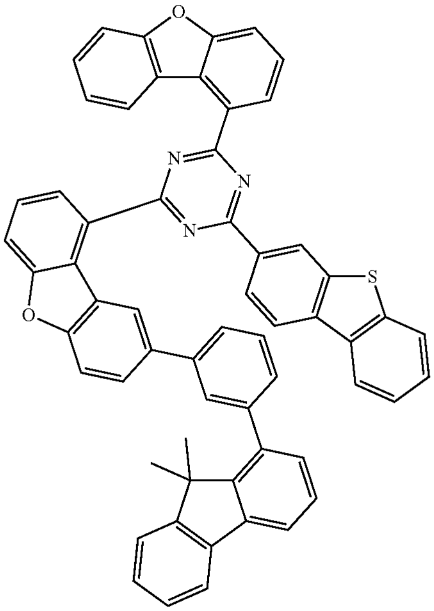 [SMILES: CC1(C)c2ccccc2-c2cccc(-c3cccc(-c4ccc5oc6cccc(-c7nc(-c8ccc9c(c8)sc8ccccc89)nc(-c8cccc9oc%10ccccc%10c89)n7)c6c5c4)c3)c21]

TABLE 1-continued
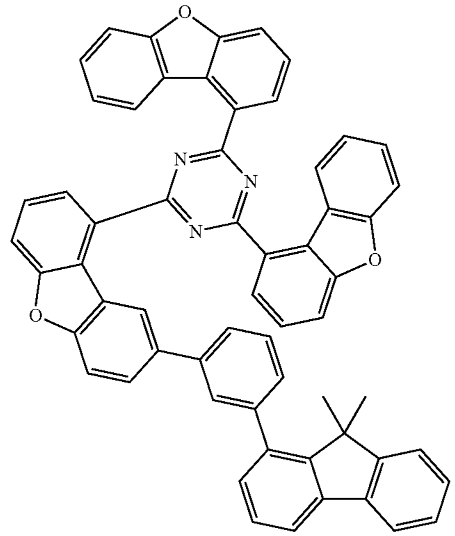 [SMILES: CC1(C)c2ccccc2-c2cccc(-c3cccc(-c4ccc5oc6cccc(-c7nc(-c8cccc9oc%10ccccc%10c89)nc(-c8cccc9oc%10ccccc%10c89)n7)c6c5c4)c3)c21]
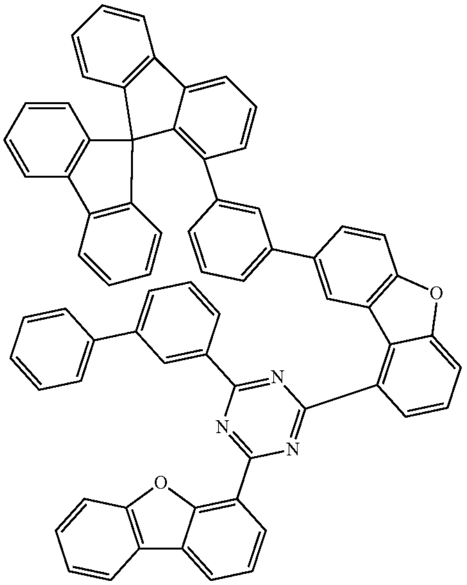 [SMILES: c1ccc(-c2cccc(-c3nc(-c4cccc5c4oc4ccccc45)nc(-c4cccc5oc6ccc(-c7cccc(-c8cccc9c8C8(c%10ccccc%10-c%10ccccc%108)c8ccccc8-9)c7)cc6c45)n3)c2)cc1]
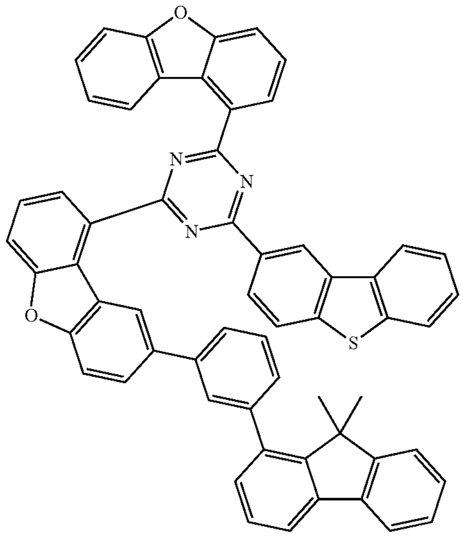 [SMILES: CC1(C)c2ccccc2-c2cccc(-c3cccc(-c4ccc5oc6cccc(-c7nc(-c8ccc9sc%10ccccc%10c9c8)nc(-c8cccc9oc%10ccccc%10c89)n7)c6c5c4)c3)c21]

TABLE 1-continued
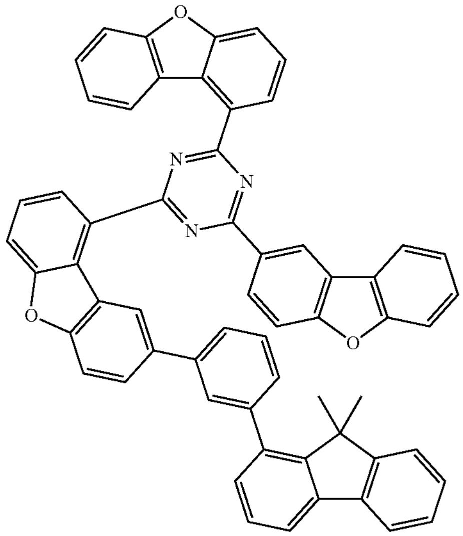 [SMILES: CC1(C)c2ccccc2-c2cccc(-c3cccc(-c4ccc5oc6cccc(-c7nc(-c8ccc9oc%10ccccc%10c9c8)nc(-c8cccc9oc%10ccccc%10c89)n7)c6c5c4)c3)c21]
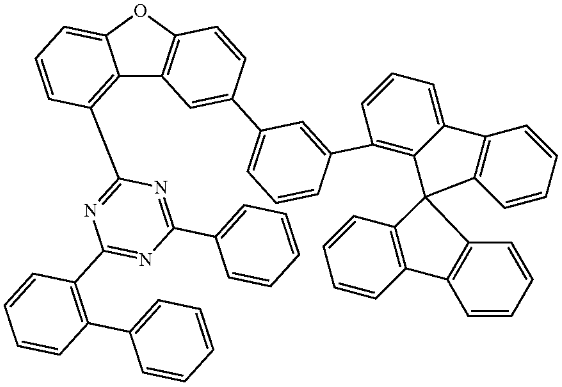 [SMILES: c1ccc(-c2nc(-c3ccccc3-c3ccccc3)nc(-c3cccc4oc5ccc(-c6cccc(-c7cccc8c7C7(c9ccccc9-c9ccccc97)c7ccccc7-8)c6)cc5c34)n2)cc1]
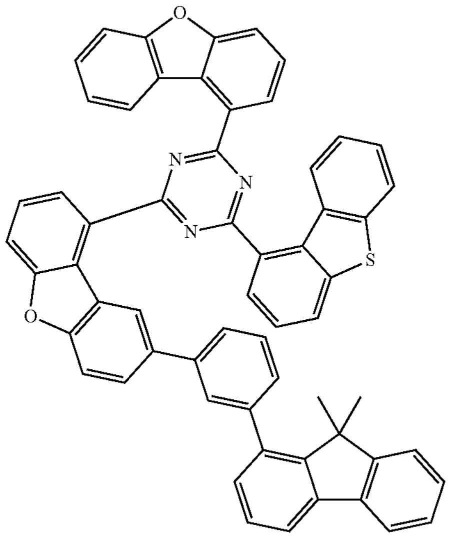 [SMILES: CC1(C)c2ccccc2-c2cccc(-c3cccc(-c4ccc5oc6cccc(-c7nc(-c8cccc9oc%10ccccc%10c89)nc(-c8cccc9sc%10ccccc%10c89)n7)c6c5c4)c3)c21]

TABLE 1-continued
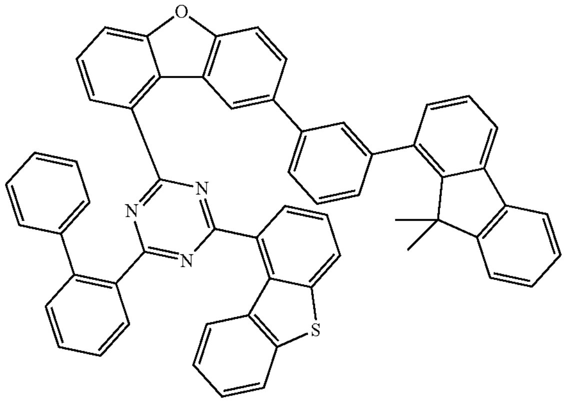 [SMILES: CC1(C)c2ccccc2-c2cccc(-c3cccc(-c4ccc5oc6cccc(-c7nc(-c8ccccc8-c8ccccc8)nc(-c8cccc9sc%10ccccc%10c89)n7)c6c5c4)c3)c21]
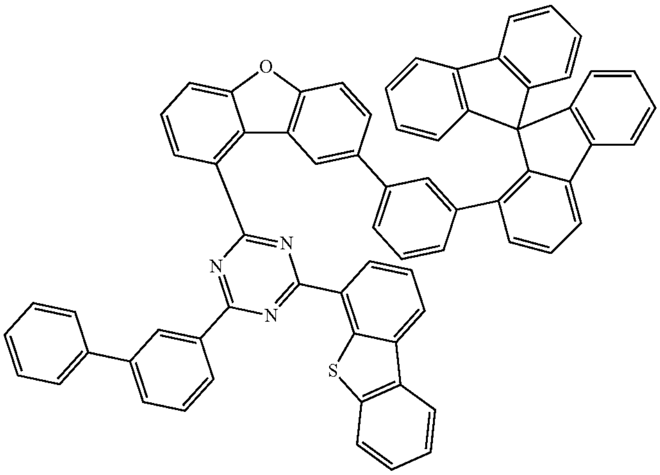 [SMILES: c1ccc(-c2cccc(-c3nc(-c4cccc5c4sc4ccccc45)nc(-c4cccc5oc6ccc(-c7cccc(-c8cccc9c8C8(c%10ccccc%10-c%10ccccc%108)c8ccccc8-9)c7)cc6c45)n3)c2)cc1]
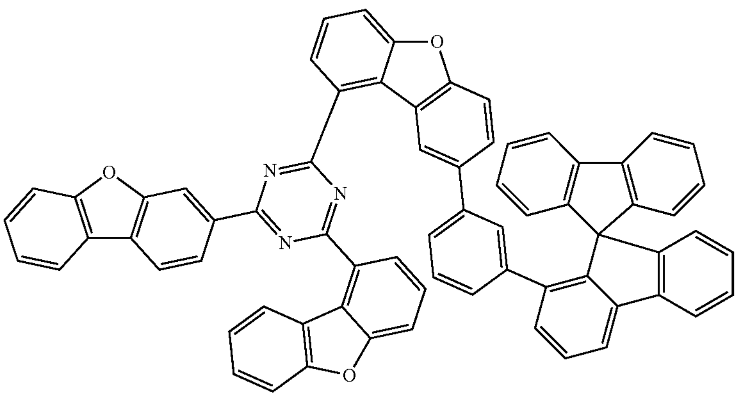 [SMILES: c1cc(-c2ccc3oc4cccc(-c5nc(-c6ccc7c(c6)oc6ccccc67)nc(-c6cccc7oc8ccccc8c67)n5)c4c3c2)cc(-c2cccc3c2C2(c4ccccc4-c4ccccc42)c2ccccc2-3)c1]

TABLE 1-continued
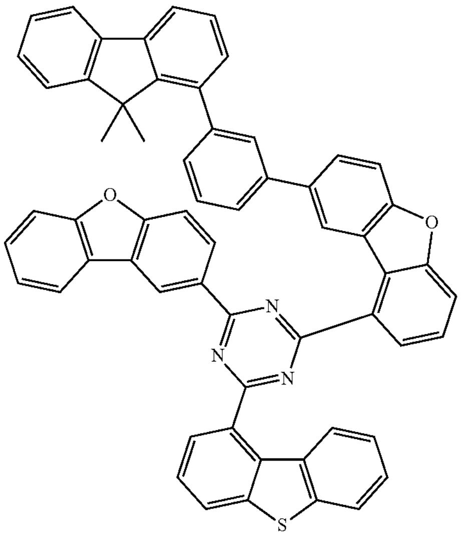 [SMILES: CC1(C)c2ccccc2-c2cccc(-c3cccc(-c4ccc5oc6cccc(-c7nc(-c8ccc9oc%10ccccc%10c9c8)nc(-c8cccc9sc%10ccccc%10c89)n7)c6c5c4)c3)c21]
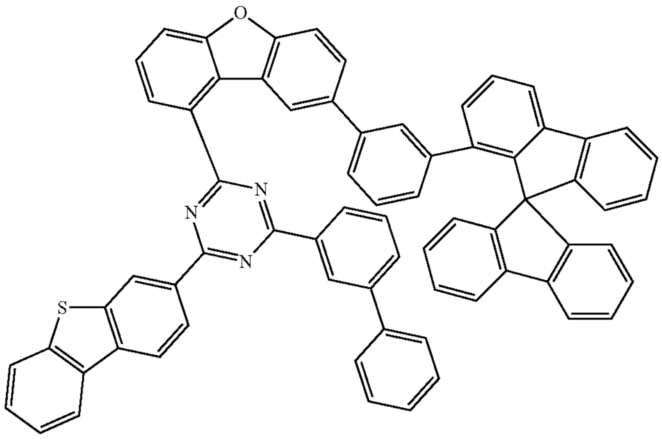 [SMILES: c1ccc(-c2cccc(-c3nc(-c4ccc5c(c4)sc4ccccc45)nc(-c4cccc5oc6ccc(-c7cccc(-c8cccc9c8C8(c%10ccccc%10-c%10ccccc%108)c8ccccc8-9)c7)cc6c45)n3)c2)cc1]
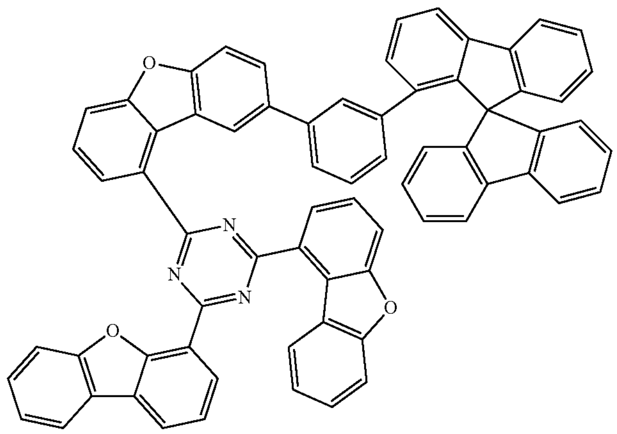 [SMILES: c1cc(-c2ccc3oc4cccc(-c5nc(-c6cccc7c6oc6ccccc67)nc(-c6cccc7oc8ccccc8c67)n5)c4c3c2)cc(-c2cccc3c2C2(c4ccccc4-c4ccccc42)c2ccccc2-3)c1]

TABLE 1-continued
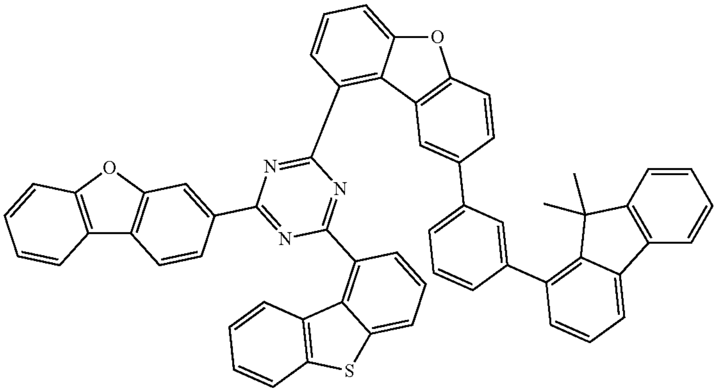 [SMILES: CC1(C)c2ccccc2-c2cccc(-c3cccc(-c4ccc5oc6cccc(-c7nc(-c8ccc9c(c8)oc8ccccc89)nc(-c8cccc9sc%10ccccc%10c89)n7)c6c5c4)c3)c21]
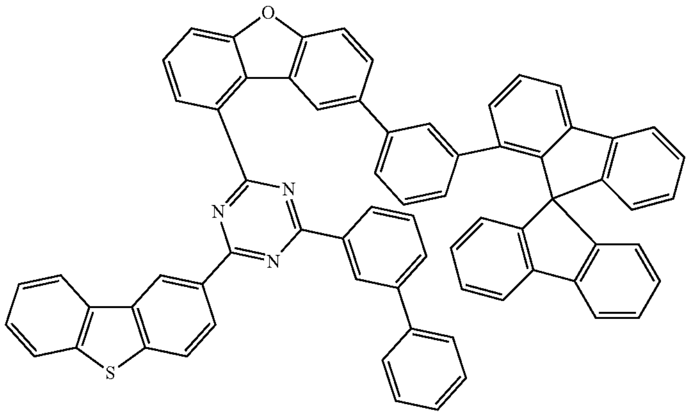 [SMILES: c1ccc(-c2cccc(-c3nc(-c4ccc5sc6ccccc6c5c4)nc(-c4cccc5oc6ccc(-c7cccc(-c8cccc9c8C8(c%10ccccc%10-c%10ccccc%108)c8ccccc8-9)c7)cc6c45)n3)c2)cc1]
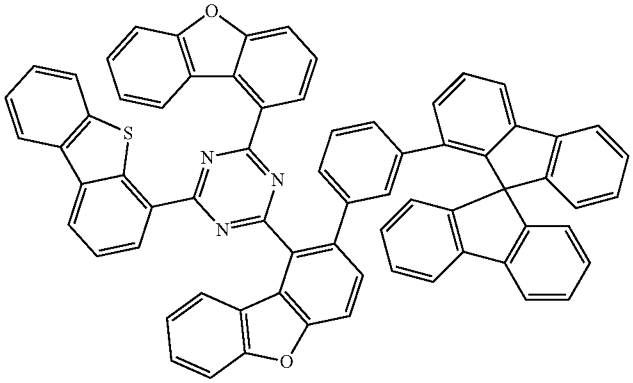 [SMILES: c1cc(-c2cccc3c2C2(c4ccccc4-c4ccccc42)c2ccccc2-3)cc(-c2ccc3oc4ccccc4c3c2-c2nc(-c3cccc4c3sc3ccccc34)nc(-c3cccc4oc5ccccc5c34)n2)c1]
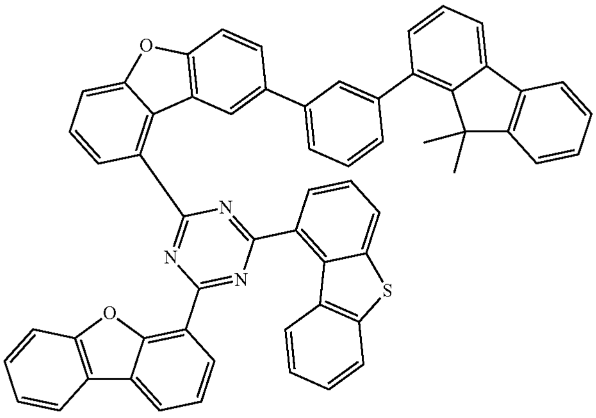 [SMILES: CC1(C)c2ccccc2-c2cccc(-c3cccc(-c4ccc5oc6cccc(-c7nc(-c8cccc9c8oc8ccccc89)nc(-c8cccc9sc%10ccccc%10c89)n7)c6c5c4)c3)c21]

TABLE 1-continued
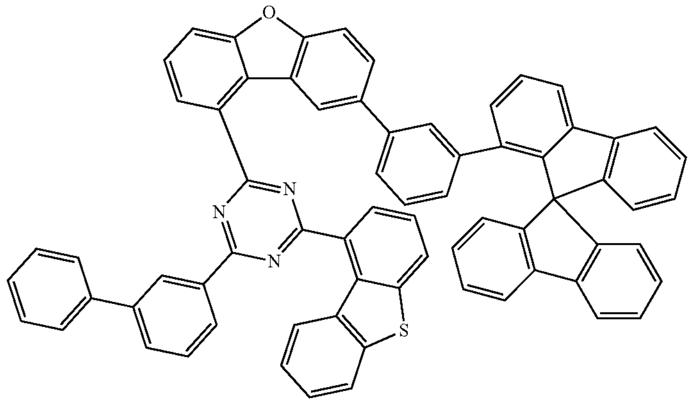 [SMILES: c1ccc(-c2cccc(-c3nc(-c4cccc5oc6ccc(-c7cccc(-c8cccc9c8C8(c%10ccccc%10-c%10ccccc%108)c8ccccc8-9)c7)cc6c45)nc(-c4cccc5sc6ccccc6c45)n3)c2)cc1]
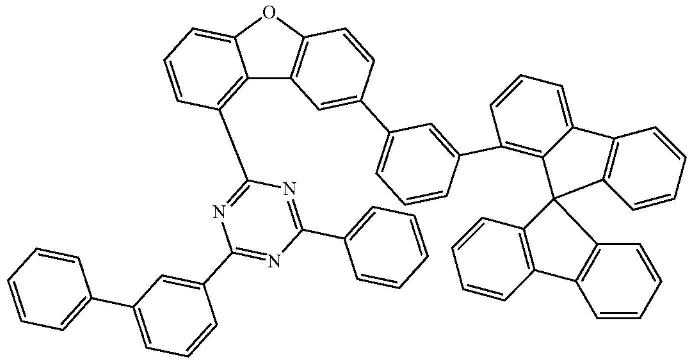 [SMILES: c1ccc(-c2cccc(-c3nc(-c4ccccc4)nc(-c4cccc5oc6ccc(-c7cccc(-c8cccc9c8C8(c%10ccccc%10-c%10ccccc%108)c8ccccc8-9)c7)cc6c45)n3)c2)cc1]
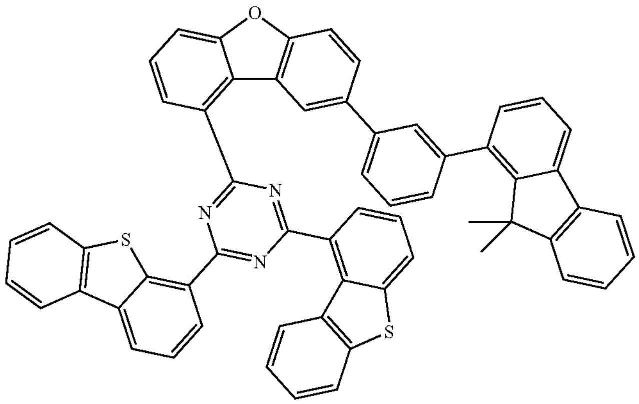 [SMILES: CC1(C)c2ccccc2-c2cccc(-c3cccc(-c4ccc5oc6cccc(-c7nc(-c8cccc9c8sc8ccccc89)nc(-c8cccc9sc%10ccccc%10c89)n7)c6c5c4)c3)c21]

TABLE 1-continued
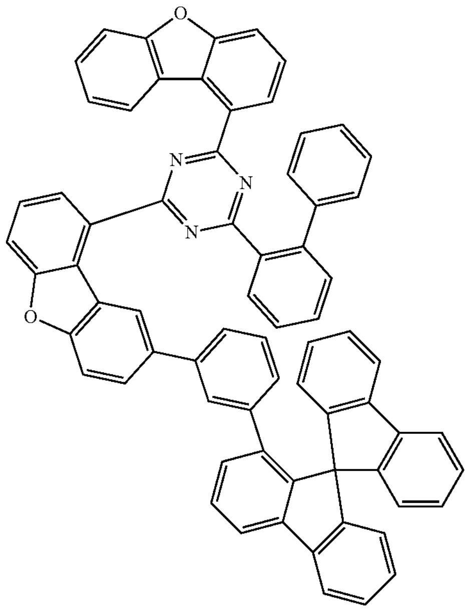 [SMILES: c1ccc(-c2ccccc2-c2nc(-c3cccc4oc5ccccc5c34)nc(-c3cccc4oc5ccc(-c6cccc(-c7cccc8c7C7(c9ccccc9-c9ccccc97)c7ccccc7-8)c6)cc5c34)n2)cc1]
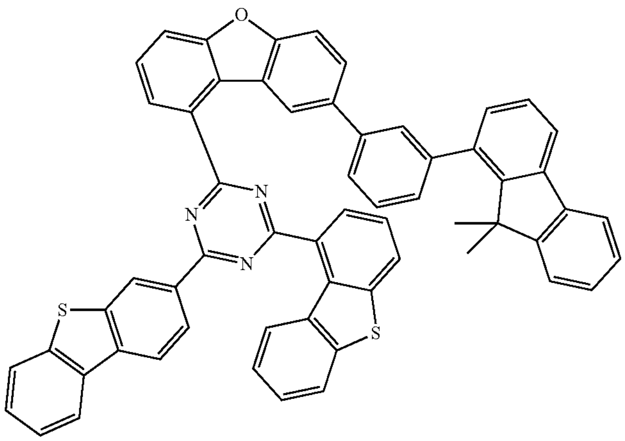 [SMILES: CC1(C)c2ccccc2-c2cccc(-c3cccc(-c4ccc5oc6cccc(-c7nc(-c8ccc9c(c8)sc8ccccc89)nc(-c8cccc9sc%10ccccc%10c89)n7)c6c5c4)c3)c21]

TABLE 1-continued
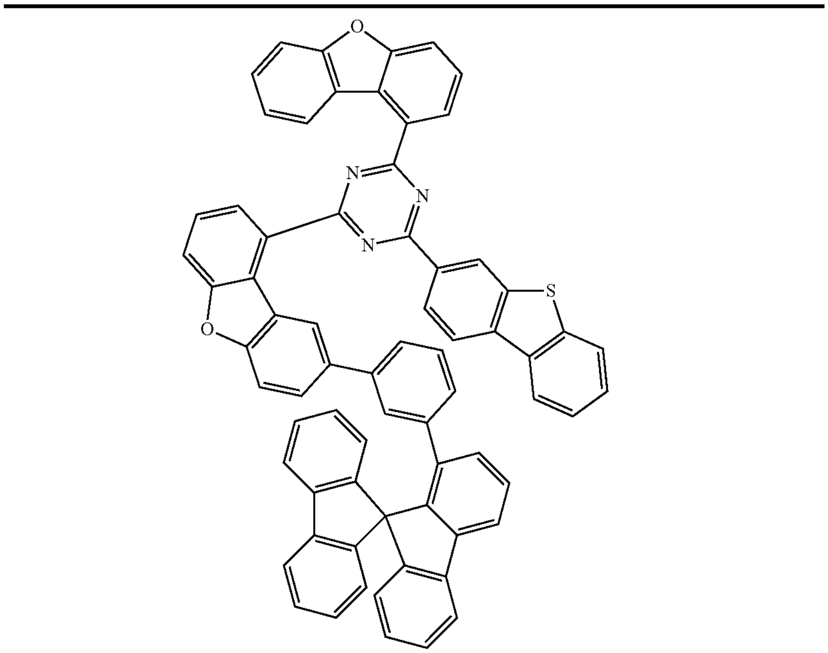
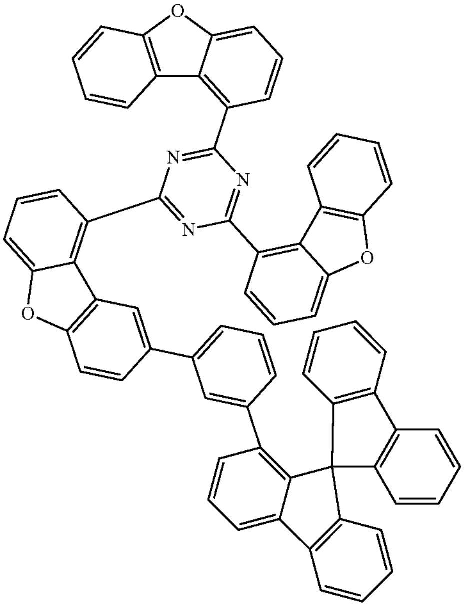 [SMILES: c1cc(-c2ccc3oc4cccc(-c5nc(-c6cccc7oc8ccccc8c67)nc(-c6cccc7oc8ccccc8c67)n5)c4c3c2)cc(-c2cccc3c2C2(c4ccccc4-c4ccccc42)c2ccccc2-3)c1]

TABLE 1-continued
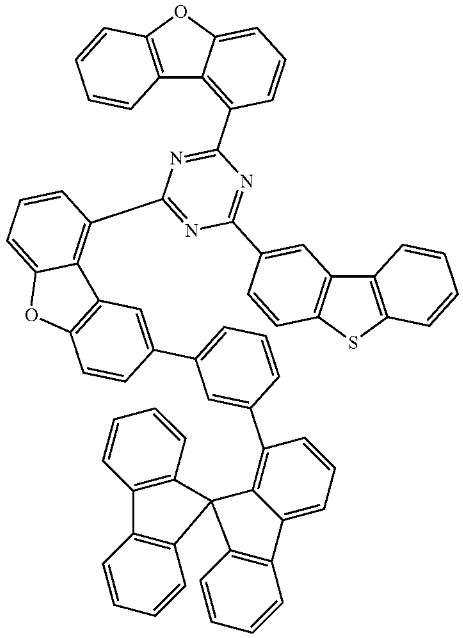 [SMILES: c1cc(-c2ccc3oc4cccc(-c5nc(-c6ccc7sc8ccccc8c7c6)nc(-c6cccc7oc8ccccc8c67)n5)c4c3c2)cc(-c2cccc3c2C2(c4ccccc4-c4ccccc42)c2ccccc2-3)c1]
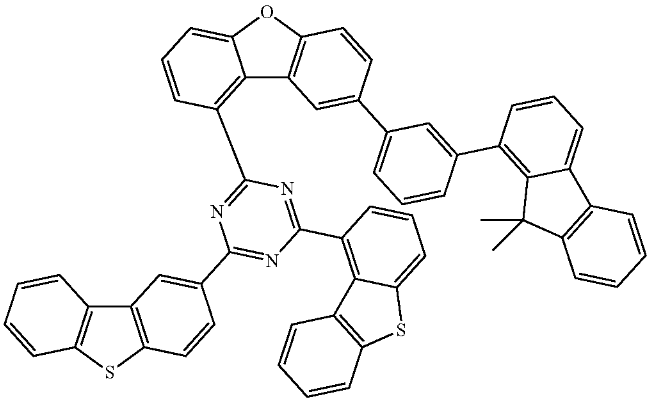 [SMILES: CC1(C)c2ccccc2-c2cccc(-c3cccc(-c4ccc5oc6cccc(-c7nc(-c8ccc9sc%10ccccc%10c9c8)nc(-c8cccc9sc%10ccccc%10c89)n7)c6c5c4)c3)c21]
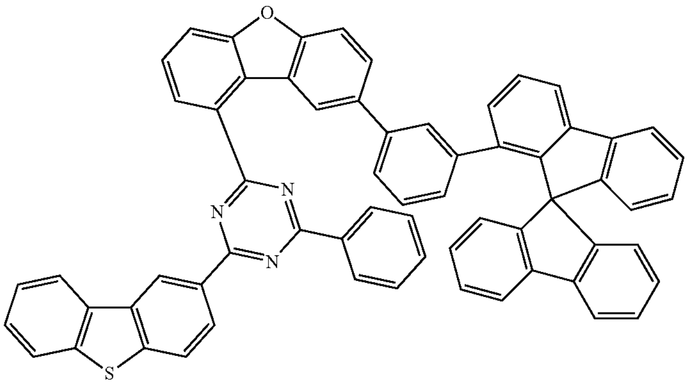 [SMILES: c1ccc(-c2nc(-c3ccc4sc5ccccc5c4c3)nc(-c3cccc4oc5ccc(-c6cccc(-c7cccc8c7C7(c9ccccc9-c9ccccc97)c7ccccc7-8)c6)cc5c34)n2)cc1]

TABLE 1-continued
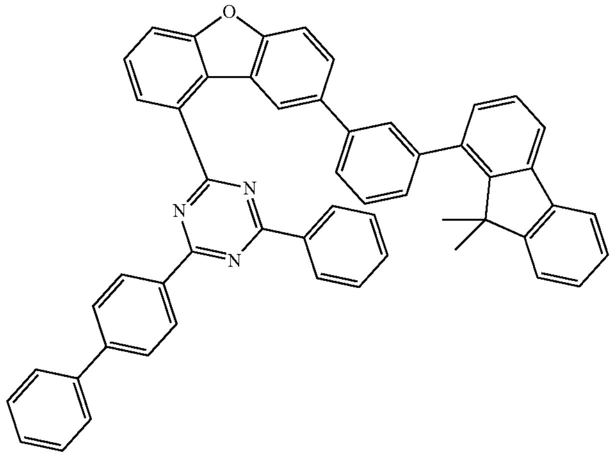 [SMILES: CC1(C)c2ccccc2-c2cccc(-c3cccc(-c4ccc5oc6cccc(-c7nc(-c8ccccc8)nc(-c8ccc(-c9ccccc9)cc8)n7)c6c5c4)c3)c21]
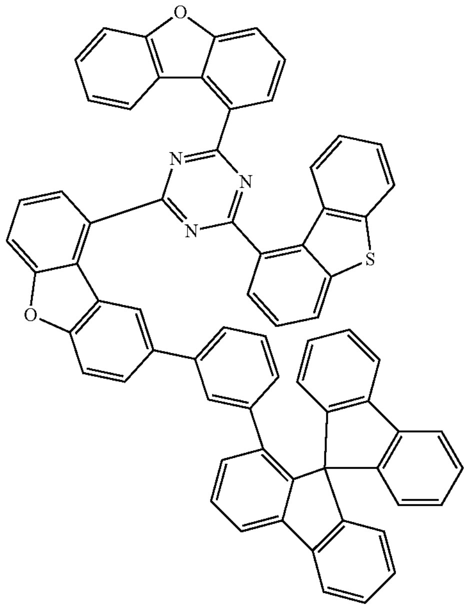 [SMILES: c1cc(-c2ccc3oc4cccc(-c5nc(-c6cccc7oc8ccccc8c67)nc(-c6cccc7sc8ccccc8c67)n5)c4c3c2)cc(-c2cccc3c2C2(c4ccccc4-c4ccccc42)c2ccccc2-3)c1]

TABLE 1-continued
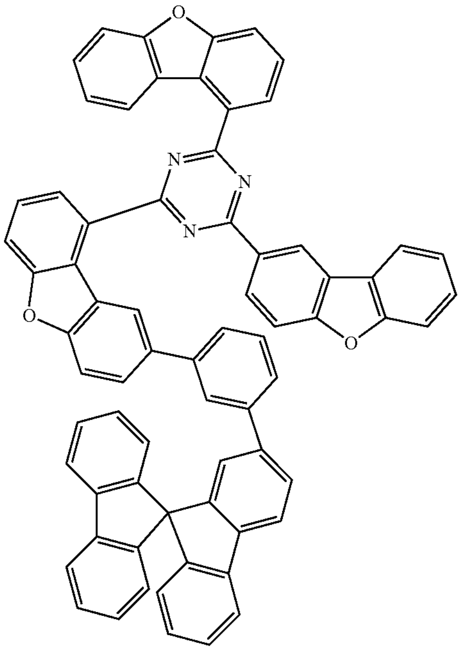 [SMILES: c1cc(-c2ccc3c(c2)C2(c4ccccc4-c4ccccc42)c2ccccc2-3)cc(-c2ccc3oc4cccc(-c5nc(-c6ccc7oc8ccccc8c7c6)nc(-c6cccc7oc8ccccc8c67)n5)c4c3c2)c1]
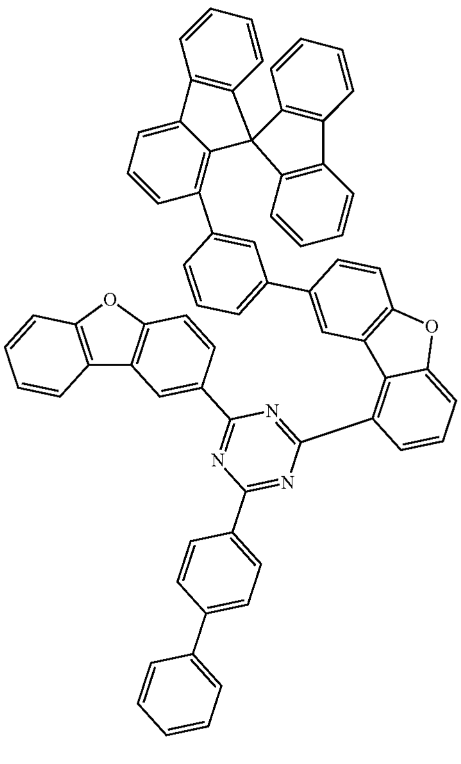 [SMILES: c1ccc(-c2ccc(-c3nc(-c4ccc5oc6ccccc6c5c4)nc(-c4cccc5oc6ccc(-c7cccc(-c8cccc9c8C8(c%10ccccc%10-c%10ccccc%108)c8ccccc8-9)c7)cc6c45)n3)cc2)cc1]

TABLE 1-continued
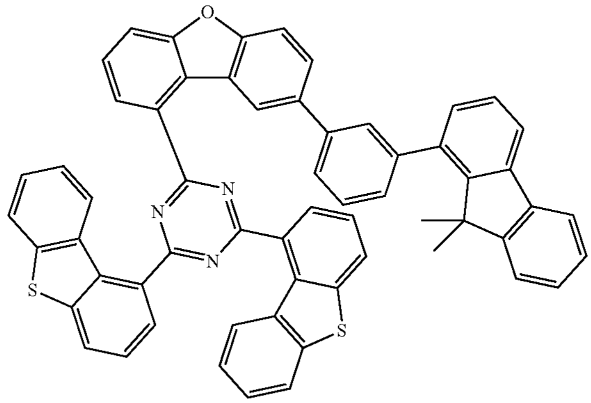 [SMILES: CC1(C)c2ccccc2-c2cccc(-c3cccc(-c4ccc5oc6cccc(-c7nc(-c8cccc9sc%10ccccc%10c89)nc(-c8cccc9sc%10ccccc%10c89)n7)c6c5c4)c3)c21]
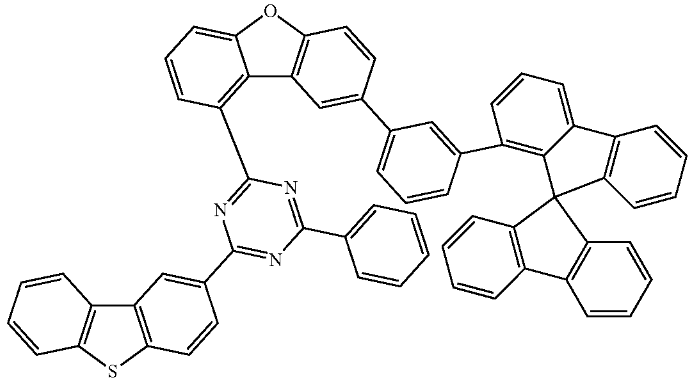 [SMILES: c1ccc(-c2nc(-c3ccc4sc5ccccc5c4c3)nc(-c3cccc4oc5ccc(-c6cccc(-c7cccc8c7C7(c9ccccc9-c9ccccc97)c7ccccc7-8)c6)cc5c34)n2)cc1]
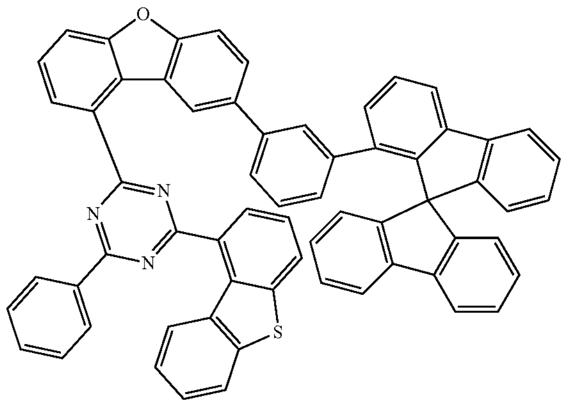 [SMILES: c1ccc(-c2nc(-c3cccc4oc5ccc(-c6cccc(-c7cccc8c7C7(c9ccccc9-c9ccccc97)c7ccccc7-8)c6)cc5c34)nc(-c3cccc4sc5ccccc5c34)n2)cc1]

TABLE 1-continued
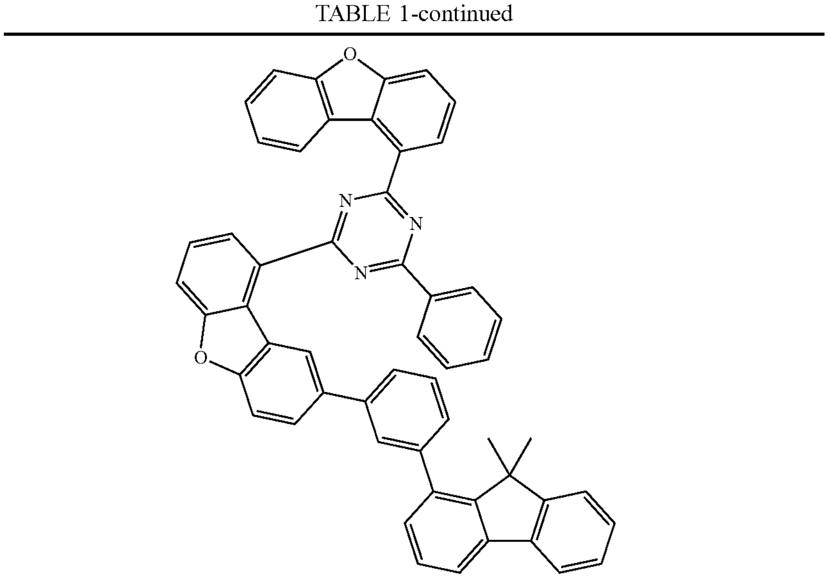
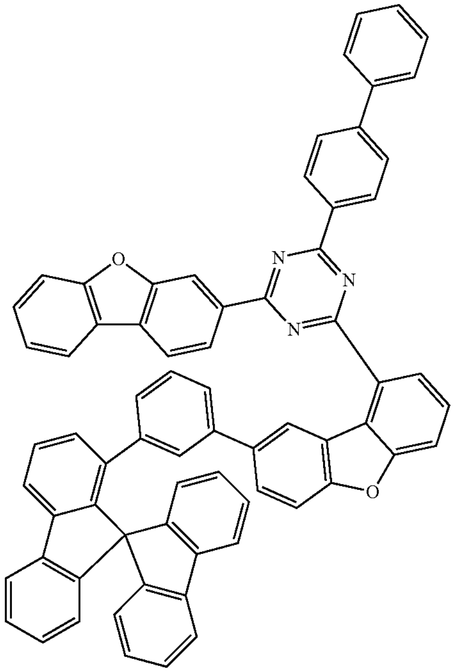 [SMILES: c1ccc(-c2ccc(-c3nc(-c4ccc5c(c4)oc4ccccc45)nc(-c4cccc5oc6ccc(-c7cccc(-c8cccc9c8C8(c%10ccccc%10-c%10ccccc%108)c8ccccc8-9)c7)cc6c45)n3)cc2)cc1]

TABLE 1-continued
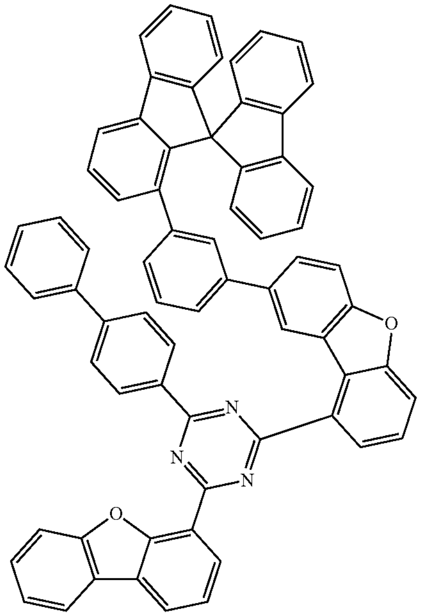 [SMILES: c1ccc(-c2ccc(-c3nc(-c4cccc5c4oc4ccccc45)nc(-c4cccc5oc6ccc(-c7cccc(-c8cccc9c8C8(c%10ccccc%10-c%10ccccc%108)c8ccccc8-9)c7)cc6c45)n3)cc2)cc1]
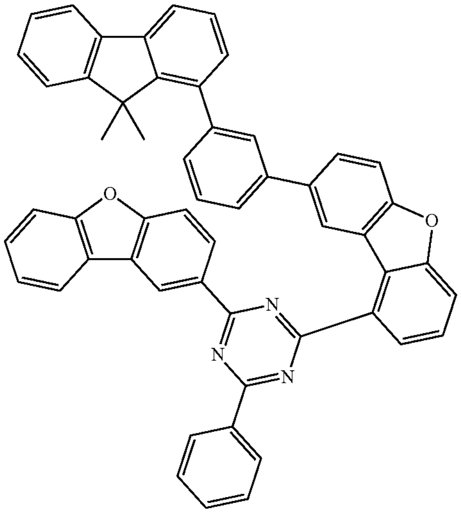 [SMILES: CC1(C)c2ccccc2-c2cccc(-c3cccc(-c4ccc5oc6cccc(-c7nc(-c8ccccc8)nc(-c8ccc9oc%10ccccc%10c9c8)n7)c6c5c4)c3)c21]
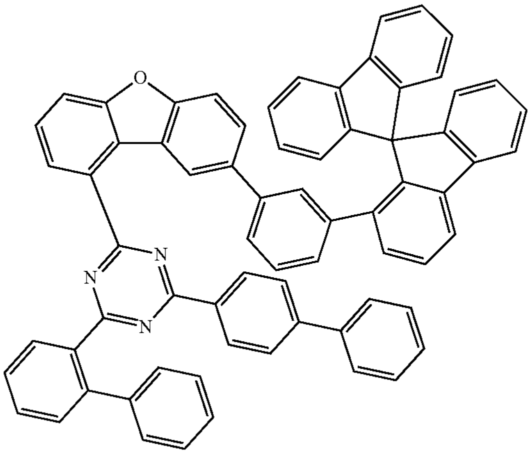 [SMILES: c1ccc(-c2ccc(-c3nc(-c4ccccc4-c4ccccc4)nc(-c4cccc5oc6ccc(-c7cccc(-c8cccc9c8C8(c%10ccccc%10-c%10ccccc%108)c8ccccc8-9)c7)cc6c45)n3)cc2)cc1]

TABLE 1-continued
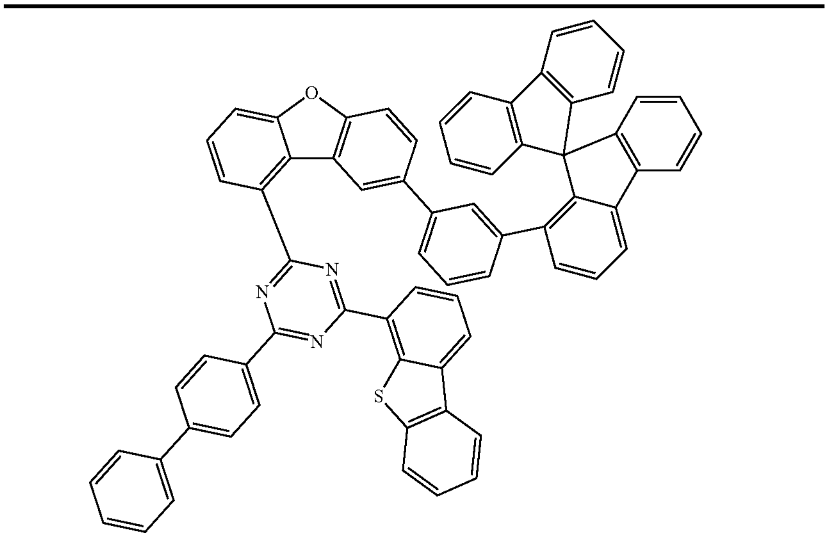
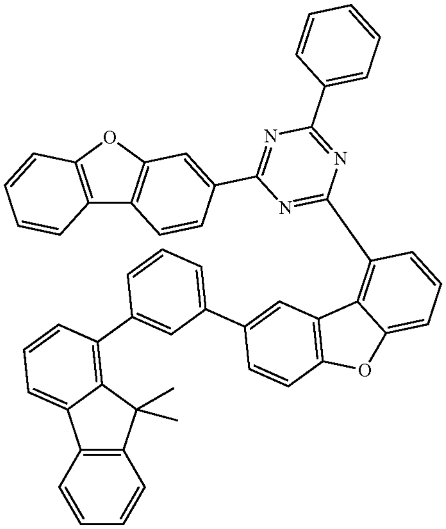 [SMILES: CC1(C)c2ccccc2-c2cccc(-c3cccc(-c4ccc5oc6cccc(-c7nc(-c8ccccc8)nc(-c8ccc9c(c8)oc8ccccc89)n7)c6c5c4)c3)c21]
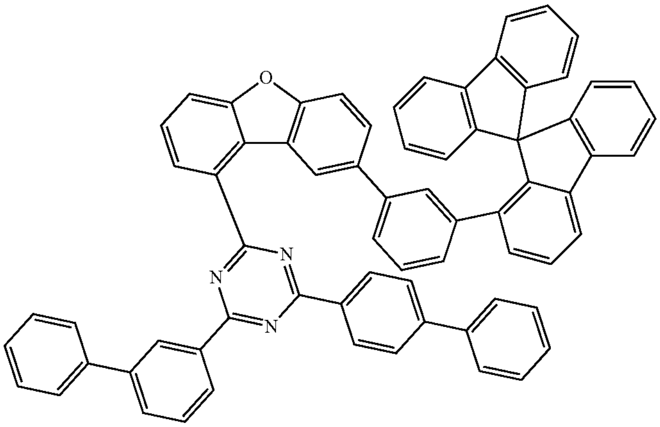 [SMILES: c1ccc(-c2ccc(-c3nc(-c4cccc(-c5ccccc5)c4)nc(-c4cccc5oc6ccc(-c7cccc(-c8cccc9c8C8(c%10ccccc%10-c%10ccccc%108)c8ccccc8-9)c7)cc6c45)n3)cc2)cc1]

TABLE 1-continued
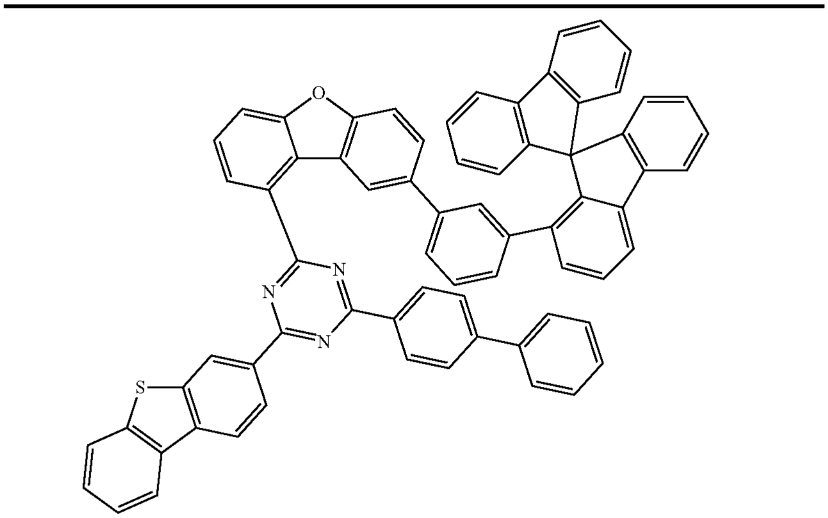
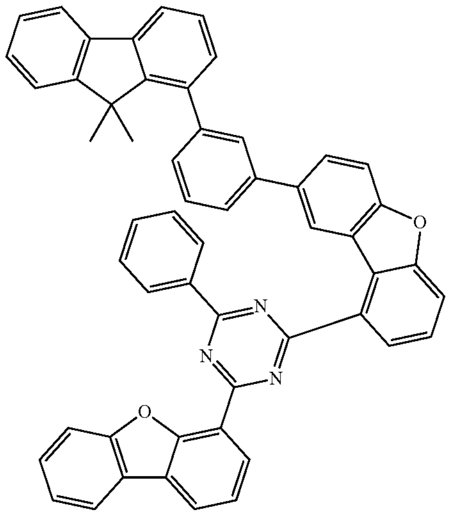 [SMILES: CC1(C)c2ccccc2-c2cccc(-c3cccc(-c4ccc5oc6cccc(-c7nc(-c8ccccc8)nc(-c8cccc9c8oc8ccccc89)n7)c6c5c4)c3)c21]
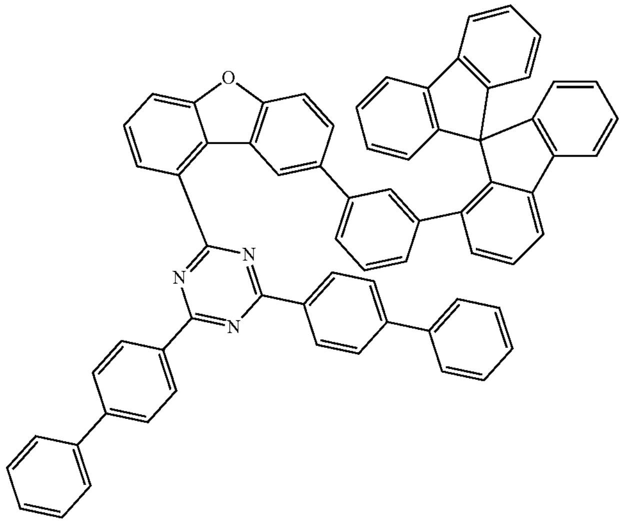 [SMILES: c1ccc(-c2ccc(-c3nc(-c4ccc(-c5ccccc5)cc4)nc(-c4cccc5oc6ccc(-c7cccc(-c8cccc9c8C8(c%10ccccc%10-c%10ccccc%108)c8ccccc8-9)c7)cc6c45)n3)cc2)cc1]

TABLE 1-continued
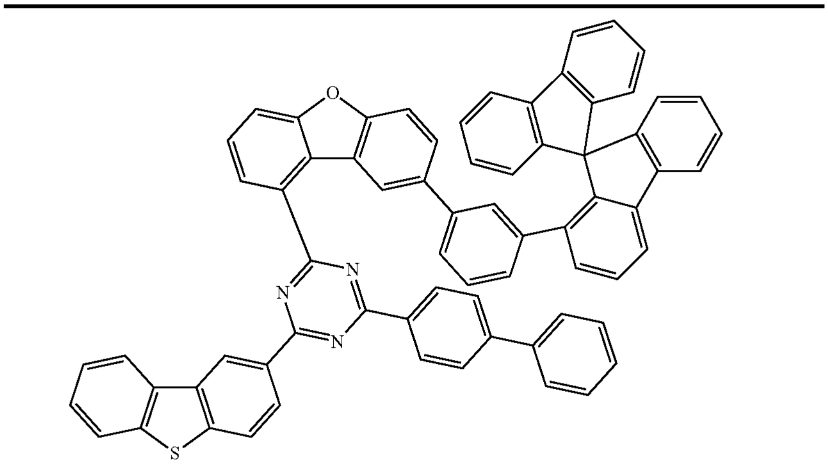
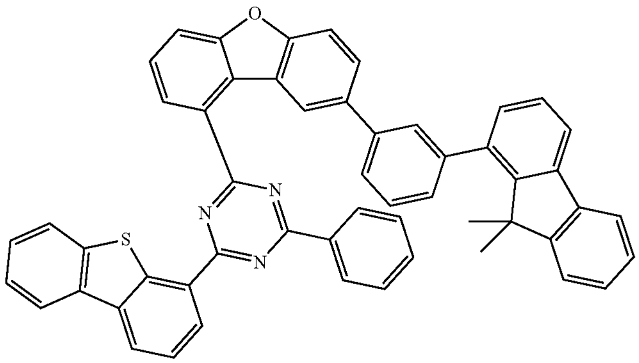 [SMILES: CC1(C)c2ccccc2-c2cccc(-c3cccc(-c4ccc5oc6cccc(-c7nc(-c8ccccc8)nc(-c8cccc9c8sc8ccccc89)n7)c6c5c4)c3)c21]
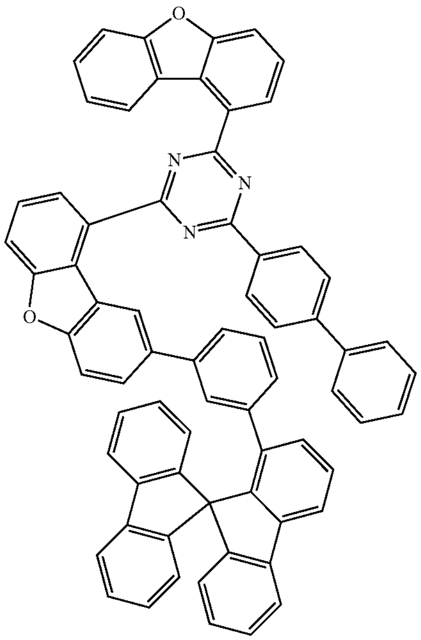 [SMILES: c1ccc(-c2ccc(-c3nc(-c4cccc5oc6ccccc6c45)nc(-c4cccc5oc6ccc(-c7cccc(-c8cccc9c8C8(c%10ccccc%10-c%10ccccc%108)c8ccccc8-9)c7)cc6c45)n3)cc2)cc1]

TABLE 1-continued
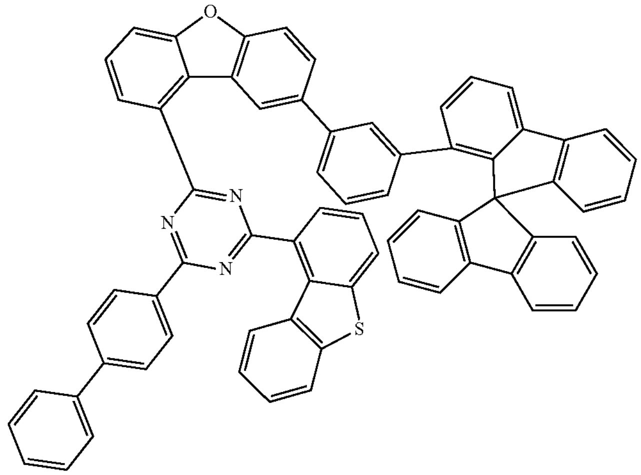 [SMILES: c1ccc(-c2ccc(-c3nc(-c4cccc5oc6ccc(-c7cccc(-c8cccc9c8C8(c%10ccccc%10-c%10ccccc%108)c8ccccc8-9)c7)cc6c45)nc(-c4cccc5sc6ccccc6c45)n3)cc2)cc1]
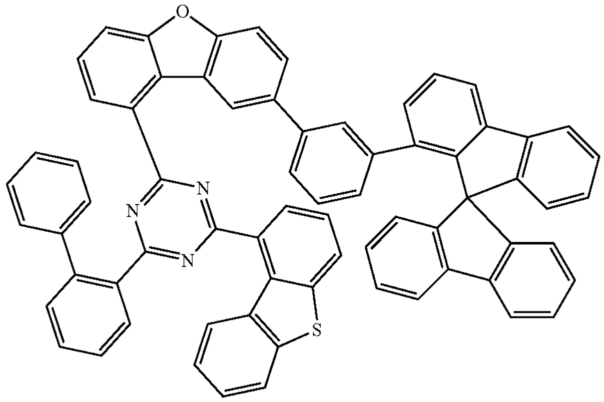 [SMILES: c1ccc(-c2ccccc2-c2nc(-c3cccc4oc5ccc(-c6cccc(-c7cccc8c7C7(c9ccccc9-c9ccccc97)c7ccccc7-8)c6)cc5c34)nc(-c3cccc4sc5ccccc5c34)n2)cc1]
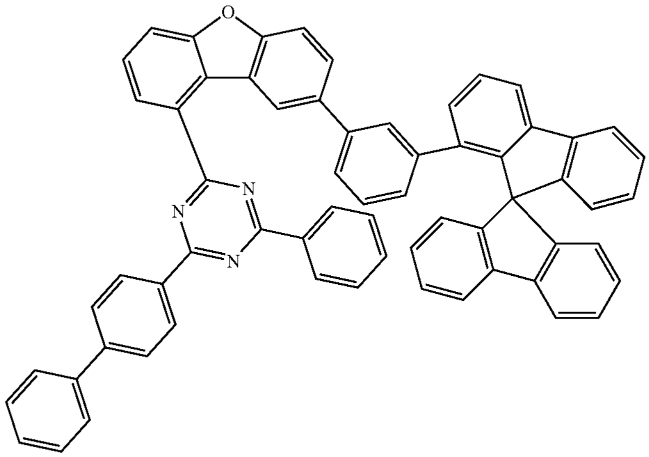 [SMILES: c1ccc(-c2ccc(-c3nc(-c4ccccc4)nc(-c4cccc5oc6ccc(-c7cccc(-c8cccc9c8C8(c%10ccccc%10-c%10ccccc%108)c8ccccc8-9)c7)cc6c45)n3)cc2)cc1]

TABLE 1-continued
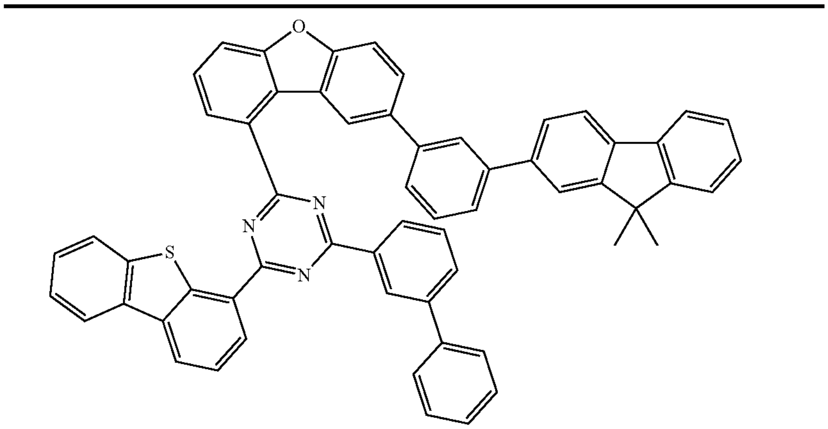
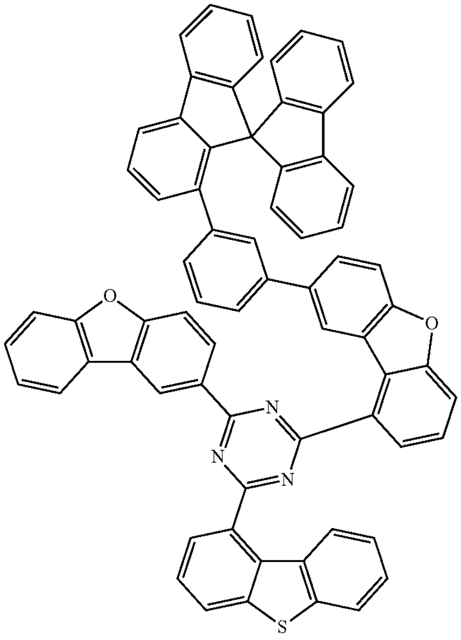 [SMILES: c1cc(-c2ccc3oc4cccc(-c5nc(-c6ccc7oc8ccccc8c7c6)nc(-c6cccc7sc8ccccc8c67)n5)c4c3c2)cc(-c2cccc3c2C2(c4ccccc4-c4ccccc42)c2ccccc2-3)c1]
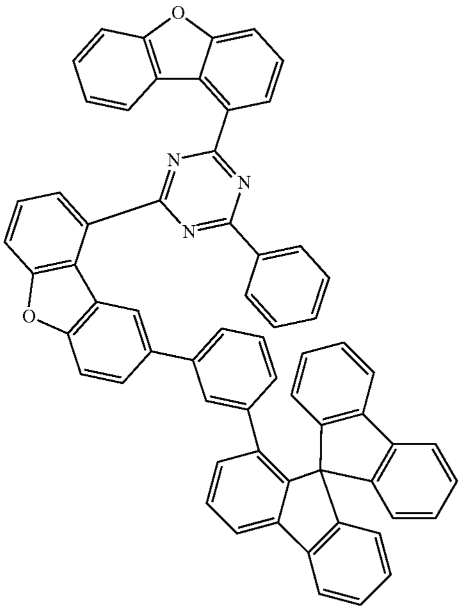 [SMILES: c1ccc(-c2nc(-c3cccc4oc5ccccc5c34)nc(-c3cccc4oc5ccc(-c6cccc(-c7cccc8c7C7(c9ccccc9-c9ccccc97)c7ccccc7-8)c6)cc5c34)n2)cc1]

TABLE 1-continued
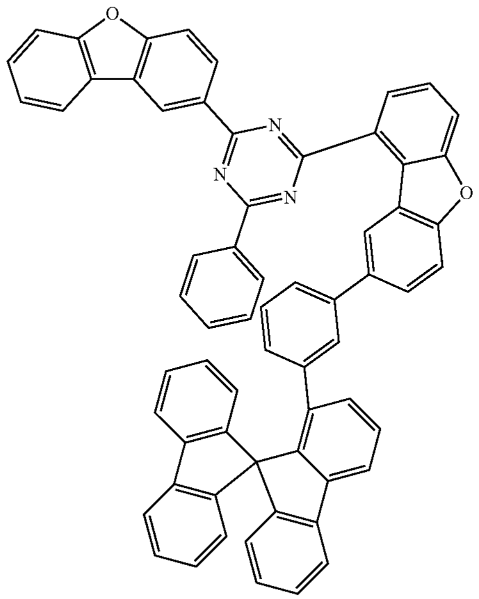 [SMILES: c1ccc(-c2nc(-c3ccc4oc5ccccc5c4c3)nc(-c3cccc4oc5ccc(-c6cccc(-c7cccc8c7C7(c9ccccc9-c9ccccc97)c7ccccc7-8)c6)cc5c34)n2)cc1]
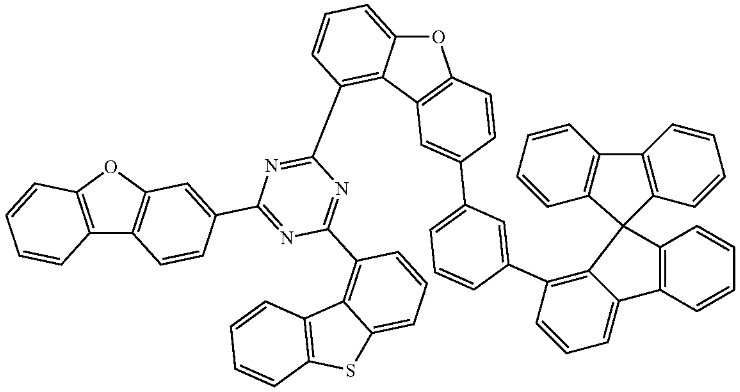 [SMILES: c1cc(-c2ccc3oc4cccc(-c5nc(-c6ccc7c(c6)oc6ccccc67)nc(-c6cccc7sc8ccccc8c67)n5)c4c3c2)cc(-c2cccc3c2C2(c4ccccc4-c4ccccc42)c2ccccc2-3)c1]
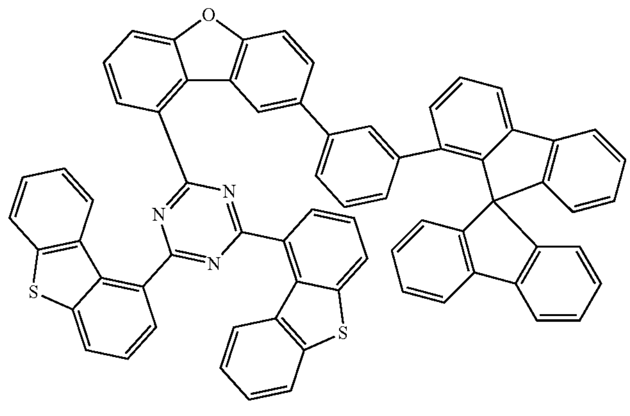 [SMILES: c1cc(-c2ccc3oc4cccc(-c5nc(-c6cccc7sc8ccccc8c67)nc(-c6cccc7sc8ccccc8c67)n5)c4c3c2)cc(-c2cccc3c2C2(c4ccccc4-c4ccccc42)c2ccccc2-3)c1]

TABLE 1-continued
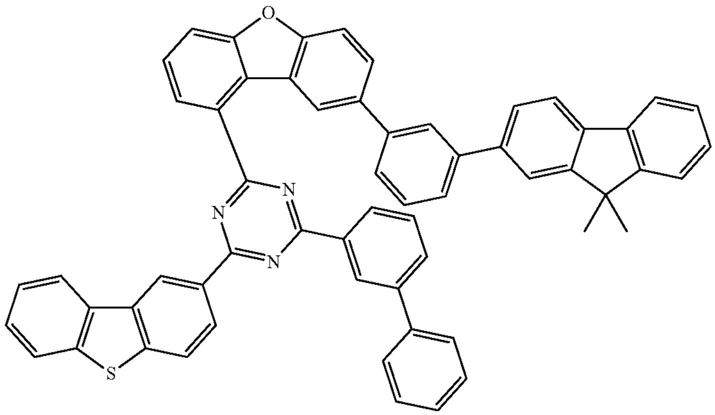 [SMILES: CC1(C)c2ccccc2-c2ccc(-c3cccc(-c4ccc5oc6cccc(-c7nc(-c8cccc(-c9ccccc9)c8)nc(-c8ccc9sc%10ccccc%10c9c8)n7)c6c5c4)c3)cc21]
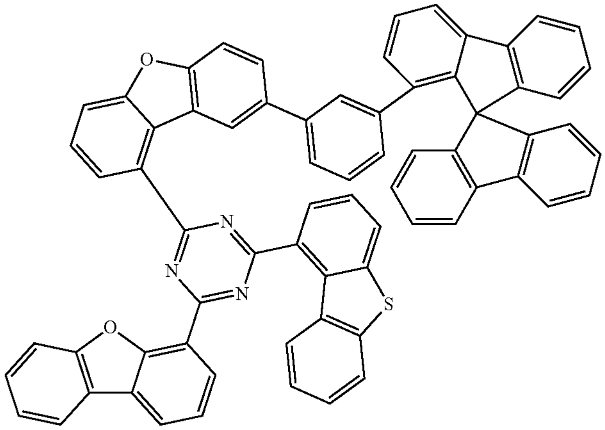 [SMILES: c1cc(-c2ccc3oc4cccc(-c5nc(-c6cccc7c6oc6ccccc67)nc(-c6cccc7sc8ccccc8c67)n5)c4c3c2)cc(-c2cccc3c2C2(c4ccccc4-c4ccccc42)c2ccccc2-3)c1]
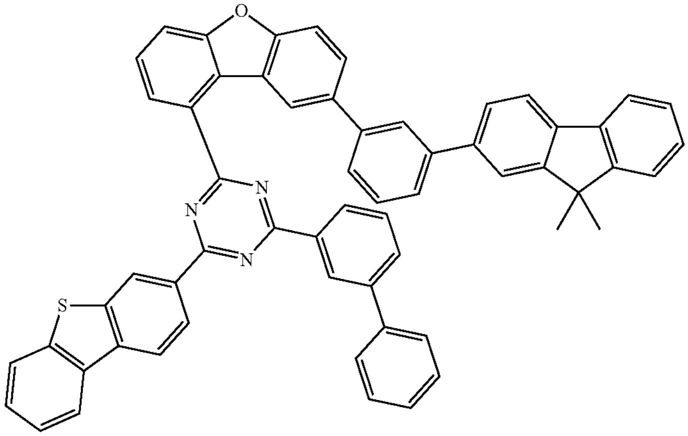 [SMILES: CC1(C)c2ccccc2-c2ccc(-c3cccc(-c4ccc5oc6cccc(-c7nc(-c8cccc(-c9ccccc9)c8)nc(-c8ccc9c(c8)sc8ccccc89)n7)c6c5c4)c3)cc21]

TABLE 1-continued
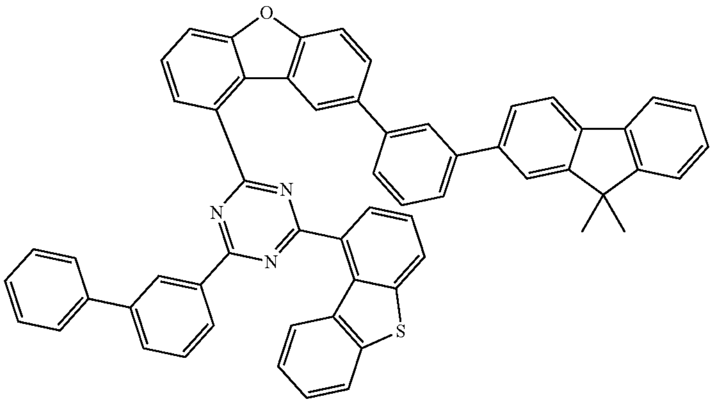 [SMILES: CC1(C)c2ccccc2-c2ccc(-c3cccc(-c4ccc5oc6cccc(-c7nc(-c8cccc(-c9ccccc9)c8)nc(-c8cccc9sc%10ccccc%10c89)n7)c6c5c4)c3)cc21]
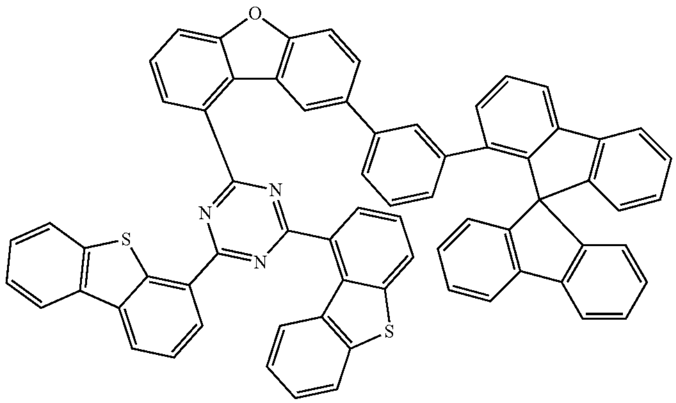 [SMILES: c1cc(-c2ccc3oc4cccc(-c5nc(-c6cccc7c6sc6ccccc67)nc(-c6cccc7sc8ccccc8c67)n5)c4c3c2)cc(-c2cccc3c2C2(c4ccccc4-c4ccccc42)c2ccccc2-3)c1]
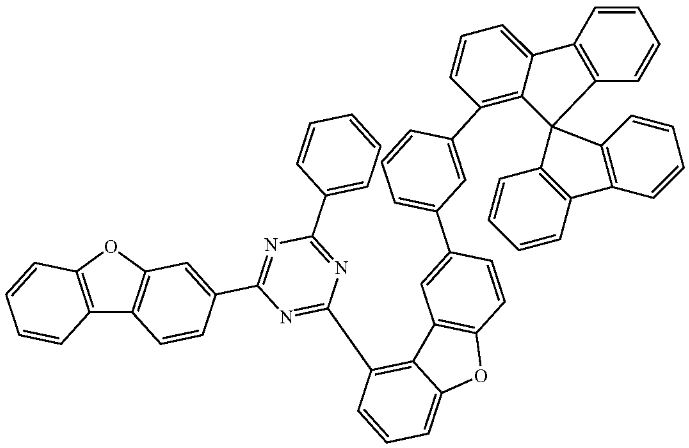 [SMILES: c1ccc(-c2nc(-c3ccc4c(c3)oc3ccccc34)nc(-c3cccc4oc5ccc(-c6cccc(-c7cccc8c7C7(c9ccccc9-c9ccccc97)c7ccccc7-8)c6)cc5c34)n2)cc1]

TABLE 1-continued
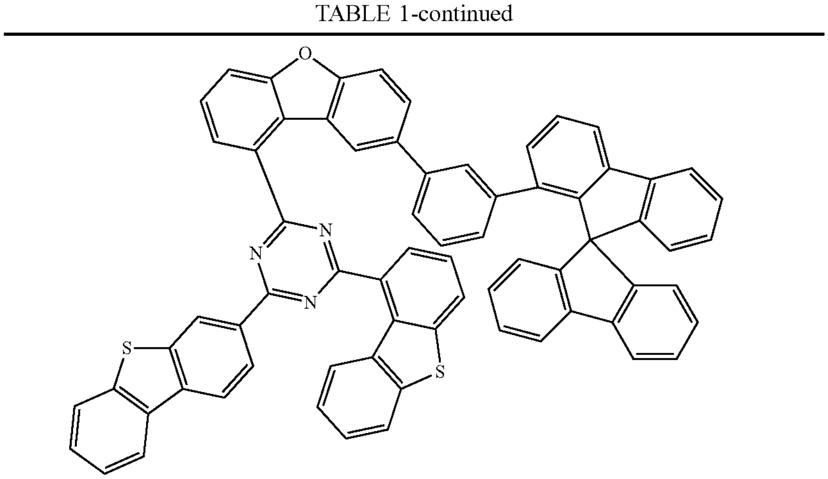
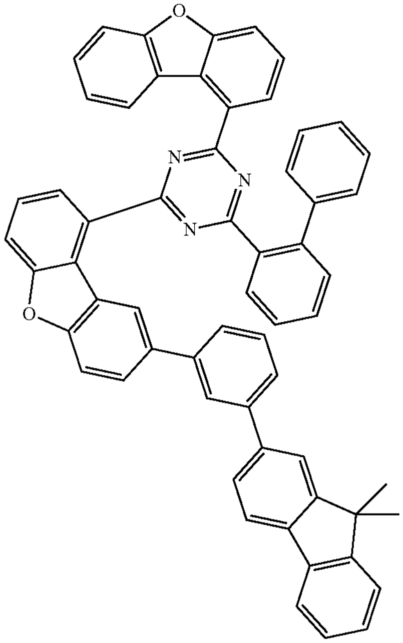 [SMILES: CC1(C)c2ccccc2-c2ccc(-c3cccc(-c4ccc5oc6cccc(-c7nc(-c8ccccc8-c8ccccc8)nc(-c8cccc9oc%10ccccc%10c89)n7)c6c5c4)c3)cc21]
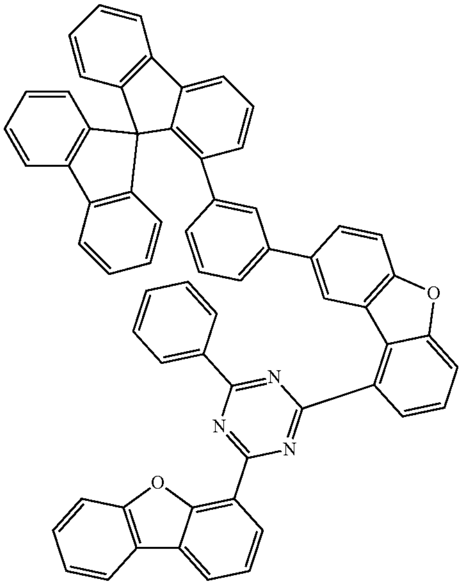 [SMILES: c1ccc(-c2nc(-c3cccc4c3oc3ccccc34)nc(-c3cccc4oc5ccc(-c6cccc(-c7cccc8c7C7(c9ccccc9-c9ccccc97)c7ccccc7-8)c6)cc5c34)n2)cc1]

TABLE 1-continued
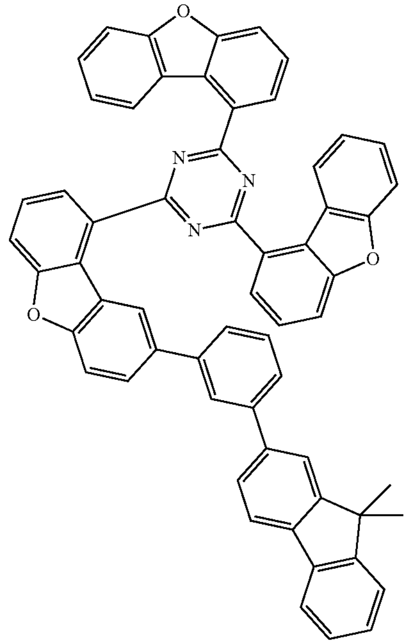 [SMILES: CC1(C)c2ccccc2-c2ccc(-c3cccc(-c4ccc5oc6cccc(-c7nc(-c8cccc9oc%10ccccc%10c89)nc(-c8cccc9oc%10ccccc%10c89)n7)c6c5c4)c3)cc21]
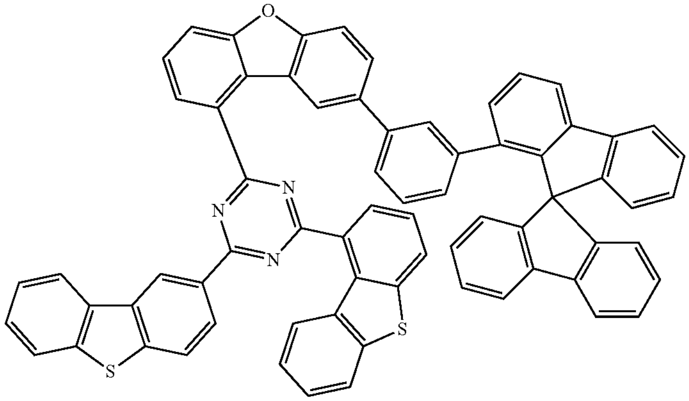 [SMILES: c1cc(-c2ccc3oc4cccc(-c5nc(-c6ccc7sc8ccccc8c7c6)nc(-c6cccc7sc8ccccc8c67)n5)c4c3c2)cc(-c2cccc3c2C2(c4ccccc4-c4ccccc42)c2ccccc2-3)c1]
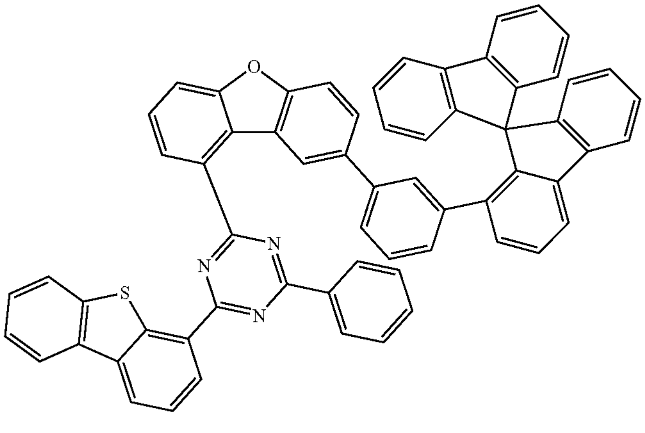 [SMILES: c1ccc(-c2nc(-c3cccc4c3sc3ccccc34)nc(-c3cccc4oc5ccc(-c6cccc(-c7cccc8c7C7(c9ccccc9-c9ccccc97)c7ccccc7-8)c6)cc5c34)n2)cc1]

TABLE 1-continued
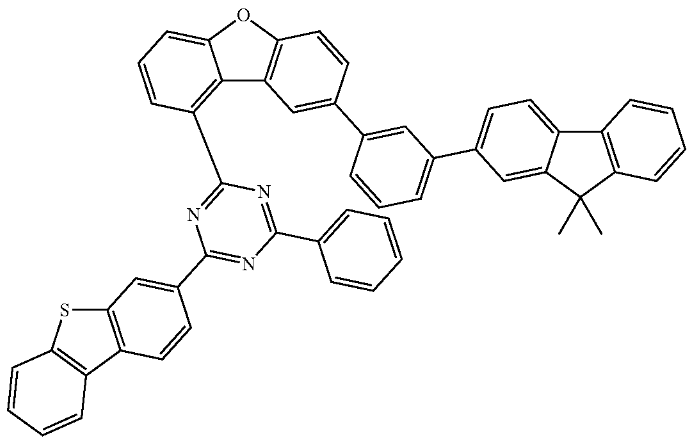 [SMILES: CC1(C)c2ccccc2-c2ccc(-c3cccc(-c4ccc5oc6cccc(-c7nc(-c8ccccc8)nc(-c8ccc9c(c8)sc8ccccc89)n7)c6c5c4)c3)cc21]
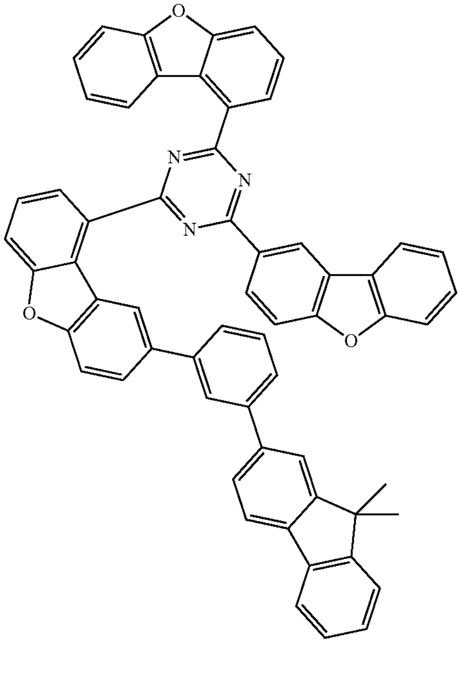 [SMILES: CC1(C)c2ccccc2-c2ccc(-c3cccc(-c4ccc5oc6cccc(-c7nc(-c8ccc9oc%10ccccc%10c9c8)nc(-c8cccc9oc%10ccccc%10c89)n7)c6c5c4)c3)cc21]

TABLE 1-continued
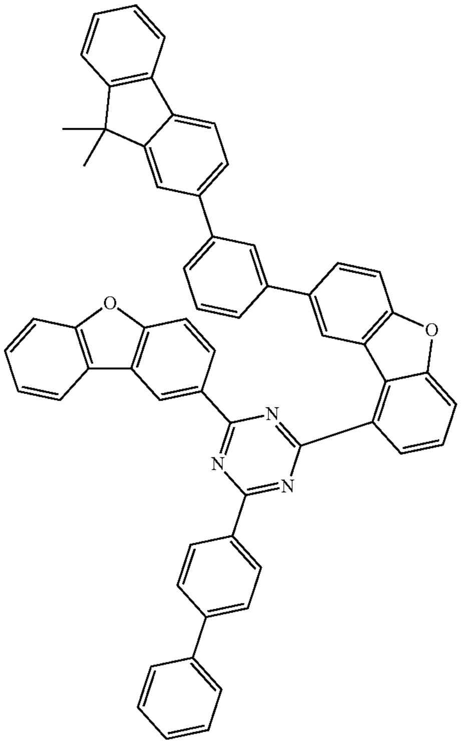 [SMILES: CC1(C)c2ccccc2-c2ccc(-c3cccc(-c4ccc5oc6cccc(-c7nc(-c8ccc(-c9ccccc9)cc8)nc(-c8ccc9oc%10ccccc%10c9c8)n7)c6c5c4)c3)cc21]
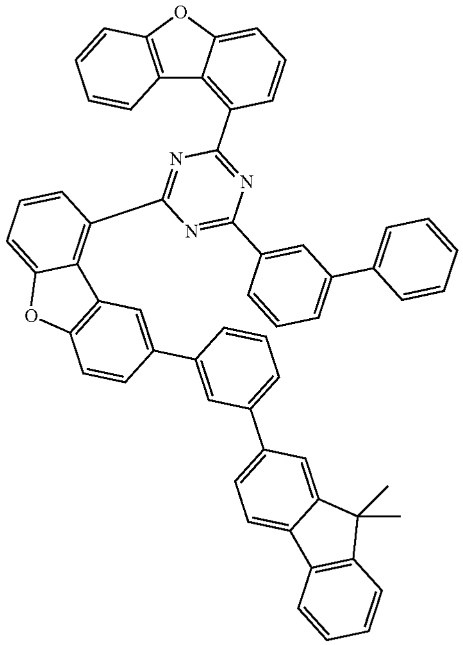 [SMILES: CC1(C)c2ccccc2-c2ccc(-c3cccc(-c4ccc5oc6cccc(-c7nc(-c8cccc(-c9ccccc9)c8)nc(-c8cccc9oc%10ccccc%10c89)n7)c6c5c4)c3)cc21]

TABLE 1-continued
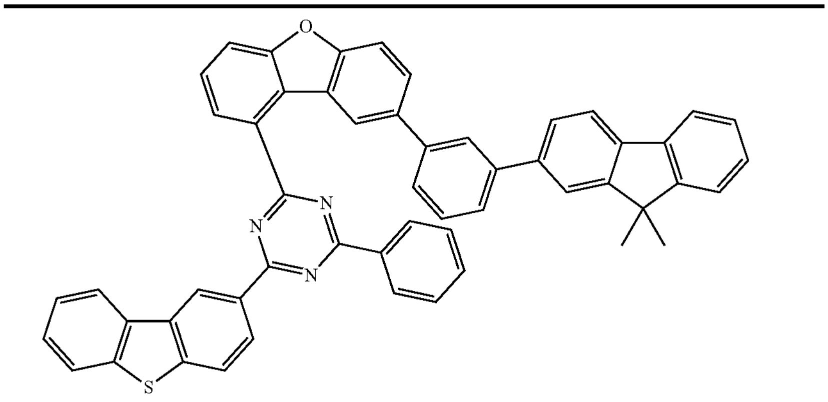
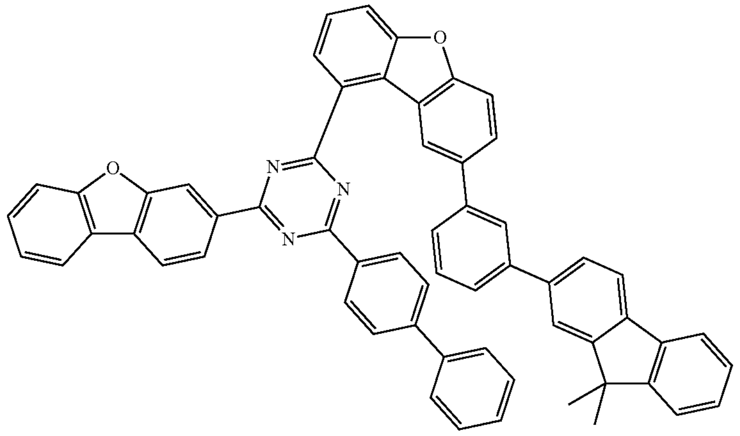 [SMILES: CC1(C)c2ccccc2-c2ccc(-c3cccc(-c4ccc5oc6cccc(-c7nc(-c8ccc(-c9ccccc9)cc8)nc(-c8ccc9c(c8)oc8ccccc89)n7)c6c5c4)c3)cc21]
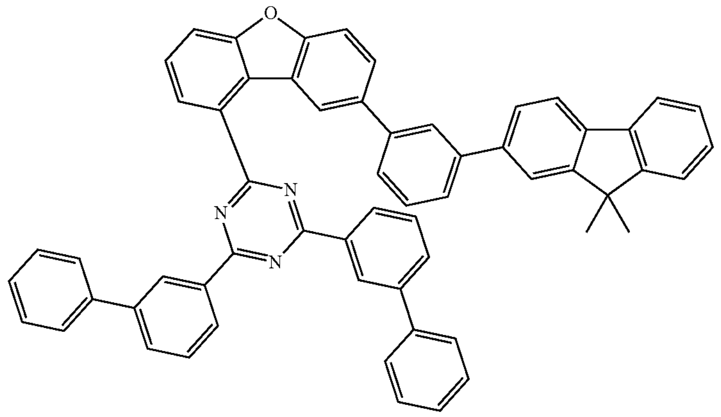 [SMILES: CC1(C)c2ccccc2-c2ccc(-c3cccc(-c4ccc5oc6cccc(-c7nc(-c8cccc(-c9ccccc9)c8)nc(-c8cccc(-c9ccccc9)c8)n7)c6c5c4)c3)cc21]
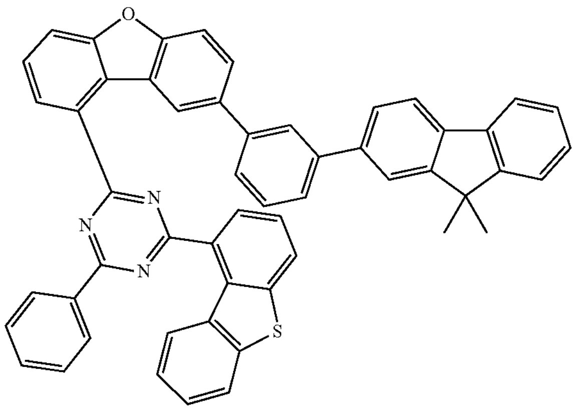 [SMILES: CC1(C)c2ccccc2-c2ccc(-c3cccc(-c4ccc5oc6cccc(-c7nc(-c8ccccc8)nc(-c8cccc9sc%10ccccc%10c89)n7)c6c5c4)c3)cc21]

TABLE 1-continued
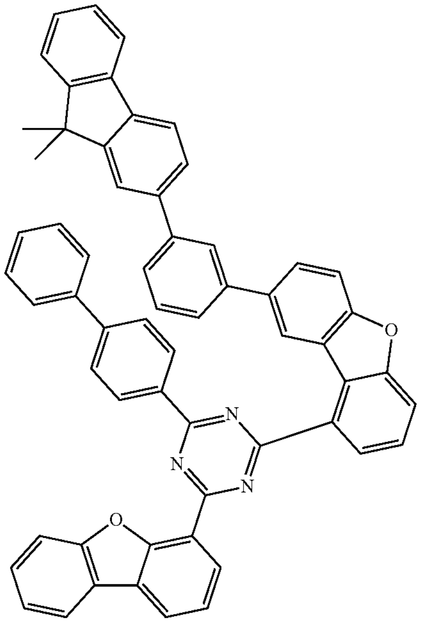 [SMILES: CC1(C)c2ccccc2-c2ccc(-c3cccc(-c4ccc5oc6cccc(-c7nc(-c8ccc(-c9ccccc9)cc8)nc(-c8cccc9c8oc8ccccc89)n7)c6c5c4)c3)cc21]
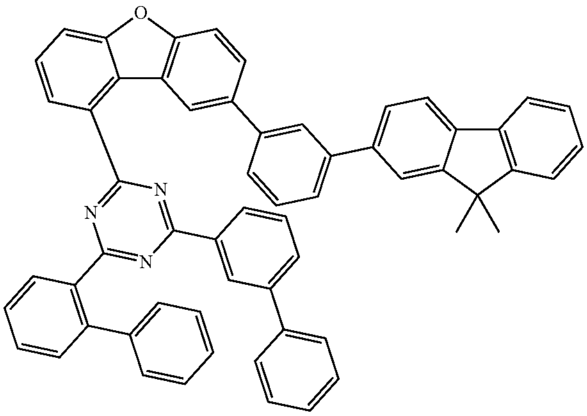 [SMILES: CC1(C)c2ccccc2-c2ccc(-c3cccc(-c4ccc5oc6cccc(-c7nc(-c8cccc(-c9ccccc9)c8)nc(-c8ccccc8-c8ccccc8)n7)c6c5c4)c3)cc21]
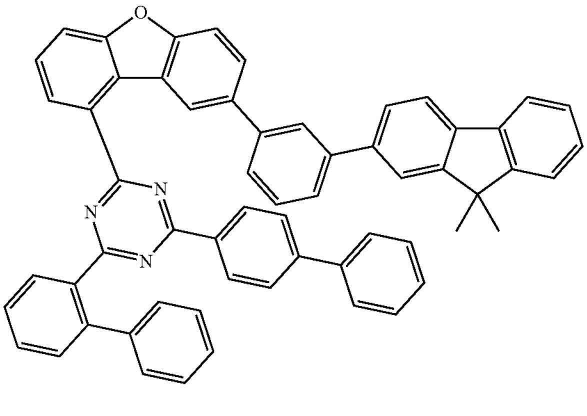 [SMILES: CC1(C)c2ccccc2-c2ccc(-c3cccc(-c4ccc5oc6cccc(-c7nc(-c8ccc(-c9ccccc9)cc8)nc(-c8ccccc8-c8ccccc8)n7)c6c5c4)c3)cc21]

TABLE 1-continued
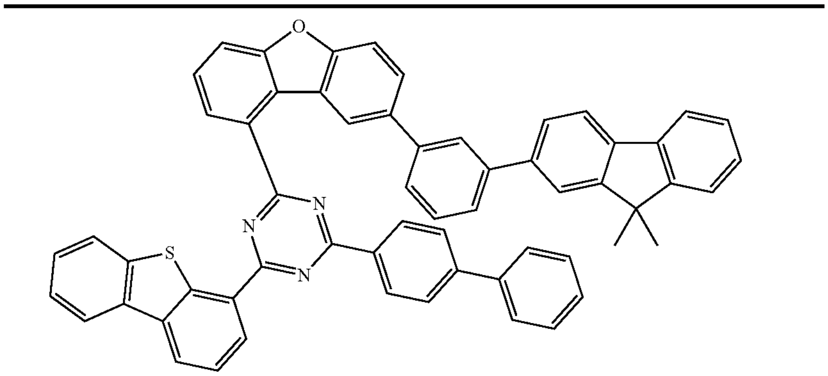
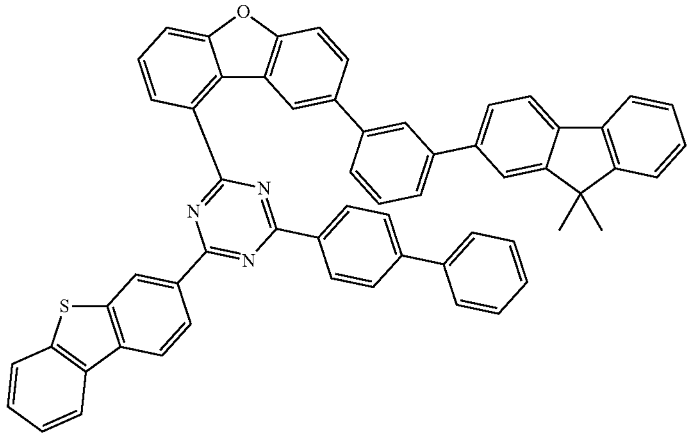 [SMILES: CC1(C)c2ccccc2-c2ccc(-c3cccc(-c4ccc5oc6cccc(-c7nc(-c8ccc(-c9ccccc9)cc8)nc(-c8ccc9c(c8)sc8ccccc89)n7)c6c5c4)c3)cc21]
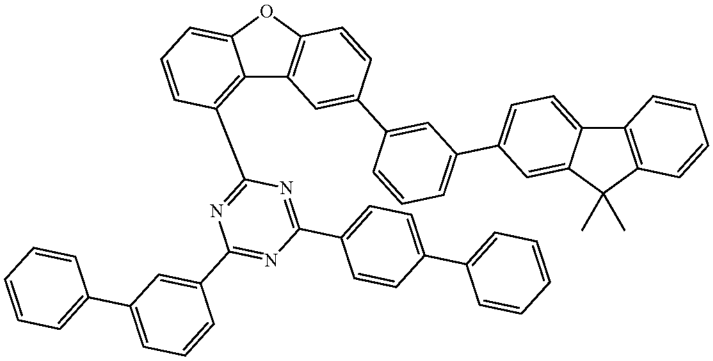 [SMILES: CC1(C)c2ccccc2-c2ccc(-c3cccc(-c4ccc5oc6cccc(-c7nc(-c8ccc(-c9ccccc9)cc8)nc(-c8cccc(-c9ccccc9)c8)n7)c6c5c4)c3)cc21]
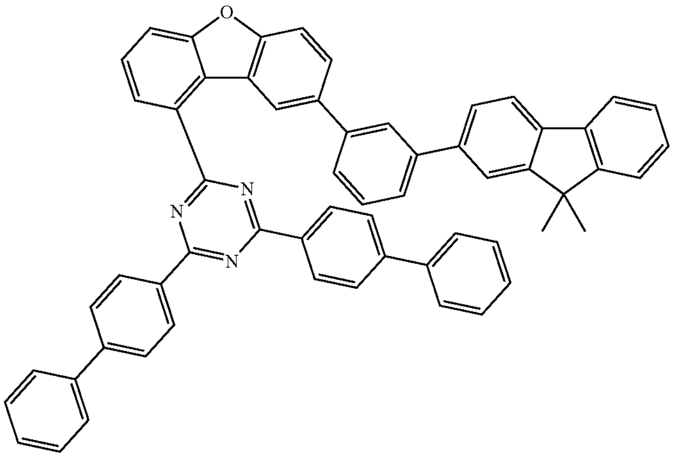 [SMILES: CC1(C)c2ccccc2-c2ccc(-c3cccc(-c4ccc5oc6cccc(-c7nc(-c8ccc(-c9ccccc9)cc8)nc(-c8ccc(-c9ccccc9)cc8)n7)c6c5c4)c3)cc21]

TABLE 1-continued
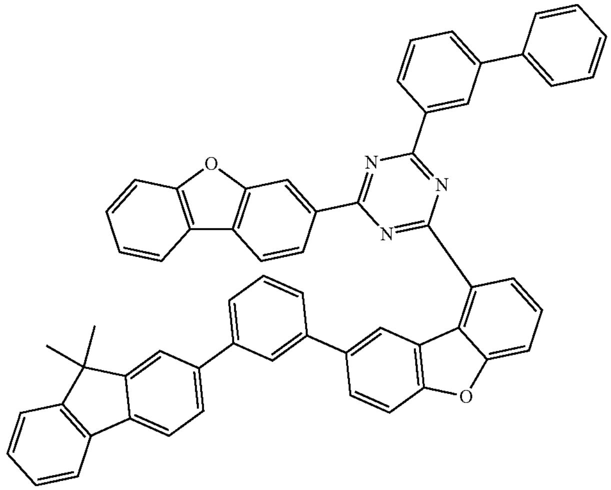 [SMILES: CC1(C)c2ccccc2-c2ccc(-c3cccc(-c4ccc5oc6cccc(-c7nc(-c8cccc(-c9ccccc9)c8)nc(-c8ccc9c(c8)oc8ccccc89)n7)c6c5c4)c3)cc21]
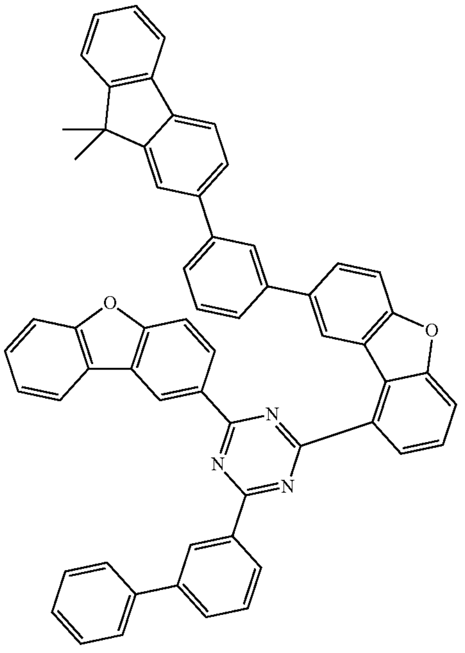 [SMILES: CC1(C)c2ccccc2-c2ccc(-c3cccc(-c4ccc5oc6cccc(-c7nc(-c8cccc(-c9ccccc9)c8)nc(-c8ccc9oc%10ccccc%10c9c8)n7)c6c5c4)c3)cc21]

TABLE 1-continued
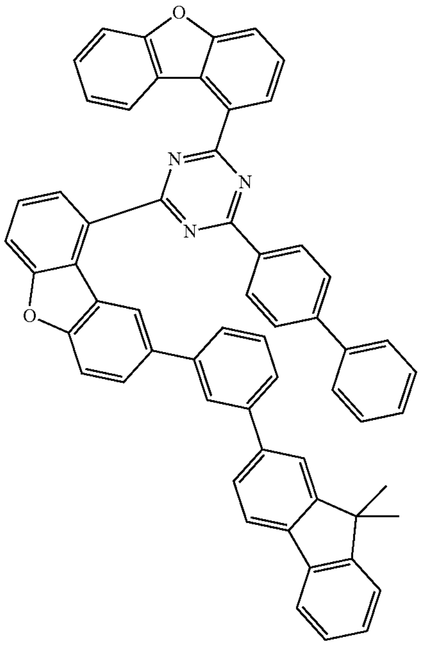 [SMILES: CC1(C)c2ccccc2-c2ccc(-c3cccc(-c4ccc5oc6cccc(-c7nc(-c8ccc(-c9ccccc9)cc8)nc(-c8cccc9oc%10ccccc%10c89)n7)c6c5c4)c3)cc21]
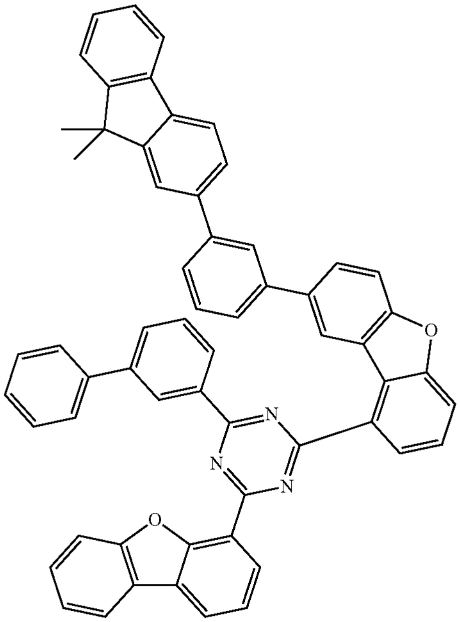 [SMILES: CC1(C)c2ccccc2-c2ccc(-c3cccc(-c4ccc5oc6cccc(-c7nc(-c8cccc(-c9ccccc9)c8)nc(-c8cccc9c8oc8ccccc89)n7)c6c5c4)c3)cc21]
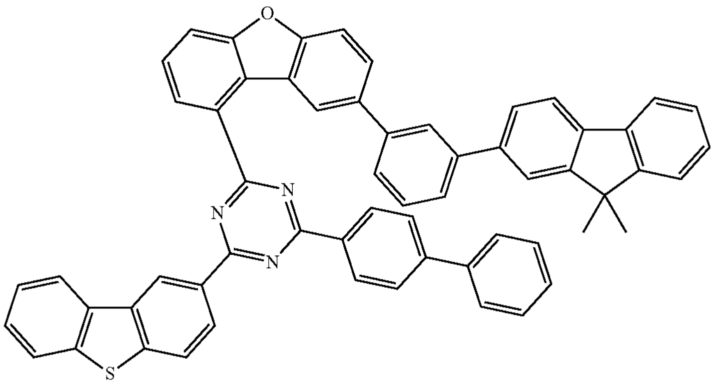 [SMILES: CC1(C)c2ccccc2-c2ccc(-c3cccc(-c4ccc5oc6cccc(-c7nc(-c8ccc(-c9ccccc9)cc8)nc(-c8ccc9sc%10ccccc%10c9c8)n7)c6c5c4)c3)cc21]

TABLE 1-continued
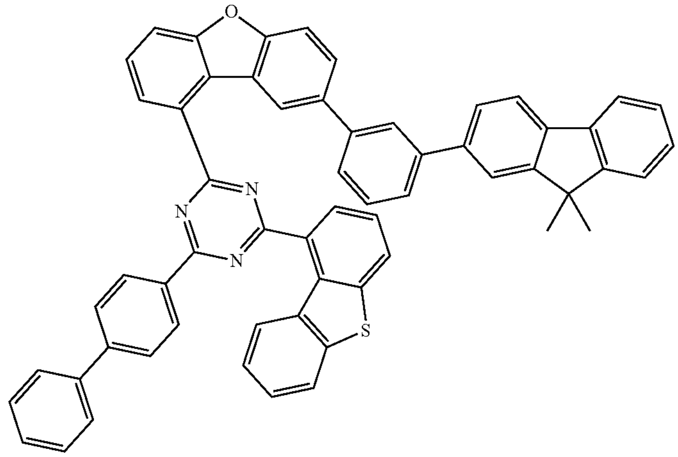 [SMILES: CC1(C)c2ccccc2-c2ccc(-c3cccc(-c4ccc5oc6cccc(-c7nc(-c8ccc(-c9ccccc9)cc8)nc(-c8cccc9sc%10ccccc%10c89)n7)c6c5c4)c3)cc21]
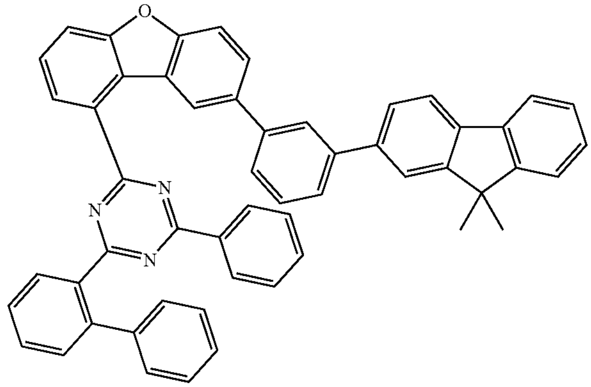 [SMILES: CC1(C)c2ccccc2-c2ccc(-c3cccc(-c4ccc5oc6cccc(-c7nc(-c8ccccc8)nc(-c8ccccc8-c8ccccc8)n7)c6c5c4)c3)cc21]
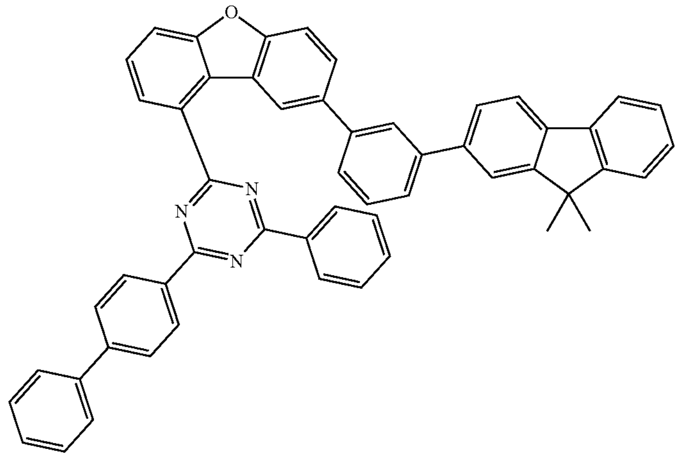 [SMILES: CC1(C)c2ccccc2-c2ccc(-c3cccc(-c4ccc5oc6cccc(-c7nc(-c8ccccc8)nc(-c8ccc(-c9ccccc9)cc8)n7)c6c5c4)c3)cc21]

TABLE 1-continued
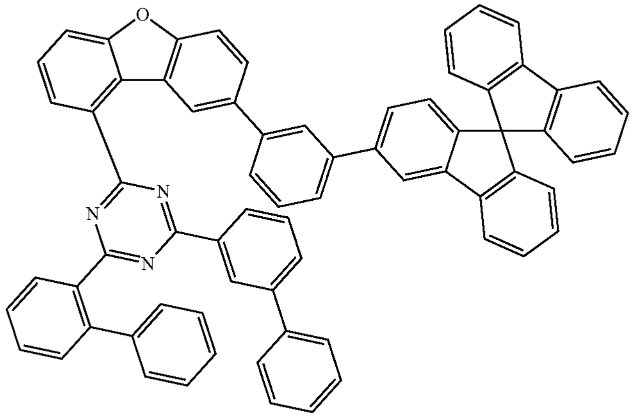 [SMILES: c1ccc(-c2cccc(-c3nc(-c4ccccc4-c4ccccc4)nc(-c4cccc5oc6ccc(-c7cccc(-c8ccc9c(c8)-c8ccccc8C98c9ccccc9-c9ccccc98)c7)cc6c45)n3)c2)cc1]
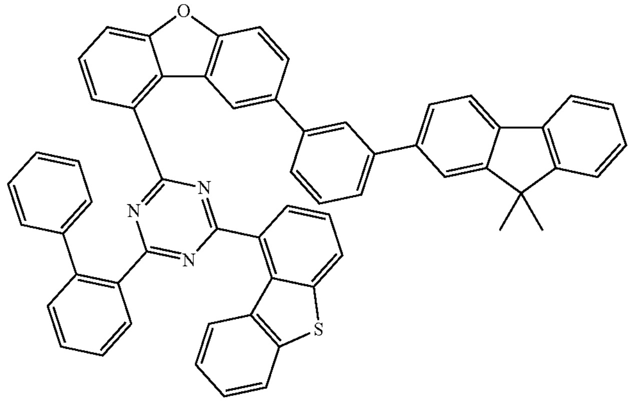 [SMILES: CC1(C)c2ccccc2-c2ccc(-c3cccc(-c4ccc5oc6cccc(-c7nc(-c8ccccc8-c8ccccc8)nc(-c8cccc9sc%10ccccc%10c89)n7)c6c5c4)c3)cc21]
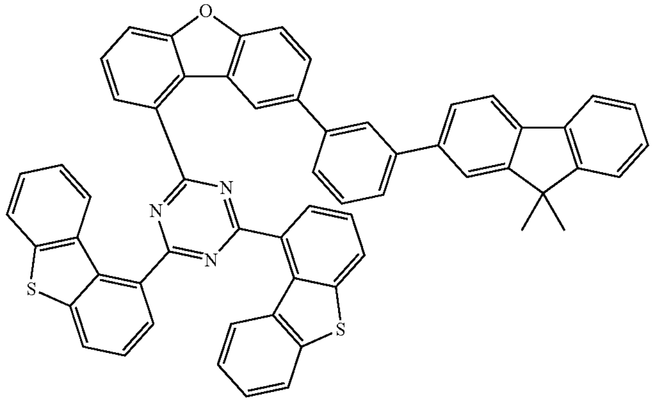 [SMILES: CC1(C)c2ccccc2-c2ccc(-c3cccc(-c4ccc5oc6cccc(-c7nc(-c8cccc9sc%10ccccc%10c89)nc(-c8cccc9sc%10ccccc%10c89)n7)c6c5c4)c3)cc21]
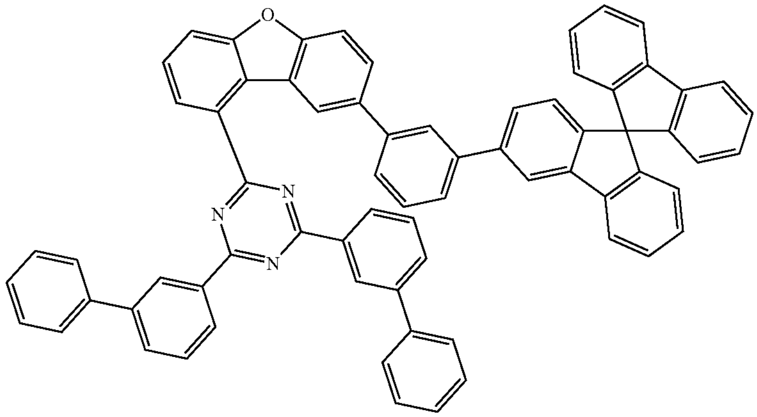 [SMILES: c1ccc(-c2cccc(-c3nc(-c4cccc(-c5ccccc5)c4)nc(-c4cccc5oc6ccc(-c7cccc(-c8ccc9c(c8)-c8ccccc8C98c9ccccc9-c9ccccc98)c7)cc6c45)n3)c2)cc1]

TABLE 1-continued
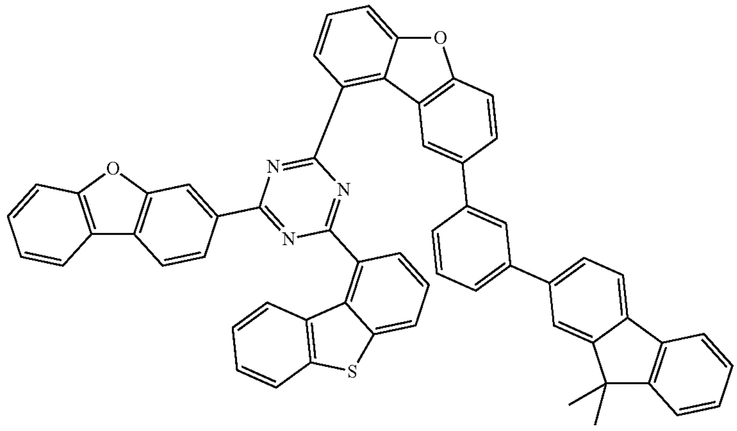
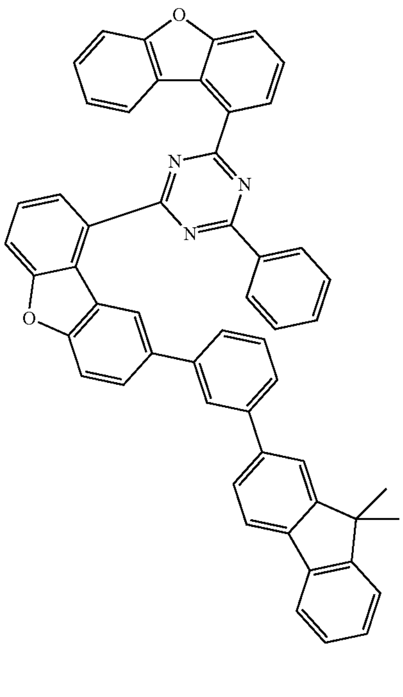 [SMILES: CC1(C)c2ccccc2-c2ccc(-c3cccc(-c4ccc5oc6cccc(-c7nc(-c8ccccc8)nc(-c8cccc9oc%10ccccc%10c89)n7)c6c5c4)c3)cc21]

TABLE 1-continued
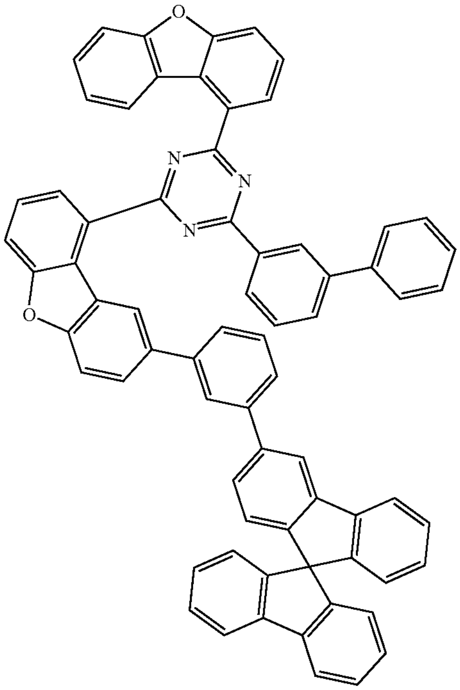 [SMILES: c1ccc(-c2cccc(-c3nc(-c4cccc5oc6ccccc6c45)nc(-c4cccc5oc6ccc(-c7cccc(-c8ccc9c(c8)-c8ccccc8C98c9ccccc9-c9ccccc98)c7)cc6c45)n3)c2)cc1]
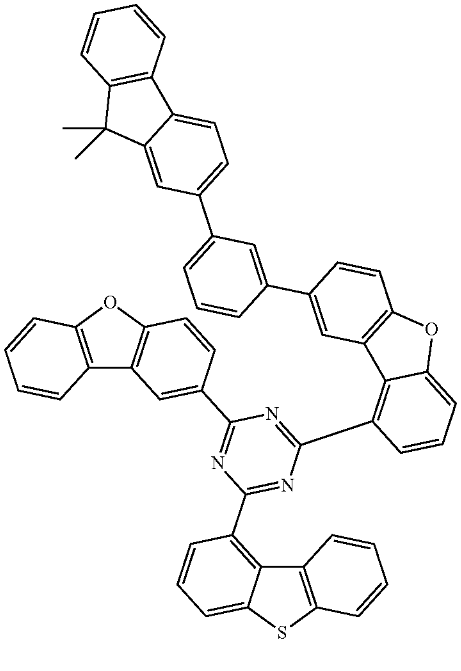 [SMILES: CC1(C)c2ccccc2-c2ccc(-c3cccc(-c4ccc5oc6cccc(-c7nc(-c8ccc9oc%10ccccc%10c9c8)nc(-c8cccc9sc%10ccccc%10c89)n7)c6c5c4)c3)cc21]

TABLE 1-continued
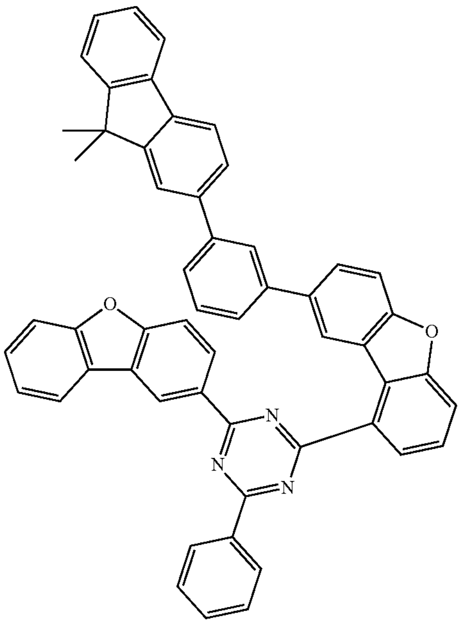 [SMILES: CC1(C)c2ccccc2-c2ccc(-c3cccc(-c4ccc5oc6cccc(-c7nc(-c8ccccc8)nc(-c8ccc9oc%10ccccc%10c9c8)n7)c6c5c4)c3)cc21]
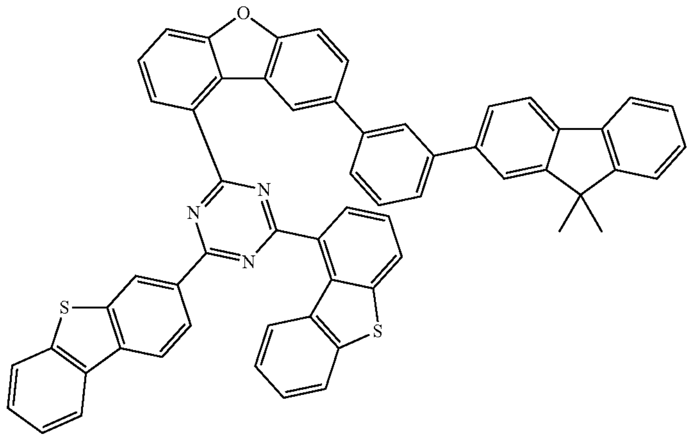 [SMILES: CC1(C)c2ccccc2-c2ccc(-c3cccc(-c4ccc5oc6cccc(-c7nc(-c8ccc9c(c8)sc8ccccc89)nc(-c8cccc9sc%10ccccc%10c89)n7)c6c5c4)c3)cc21]
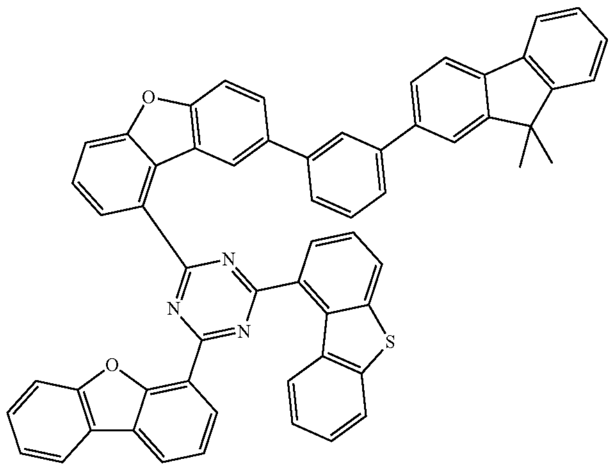 [SMILES: CC1(C)c2ccccc2-c2ccc(-c3cccc(-c4ccc5oc6cccc(-c7nc(-c8cccc9c8oc8ccccc89)nc(-c8cccc9sc%10ccccc%10c89)n7)c6c5c4)c3)cc21]

TABLE 1-continued
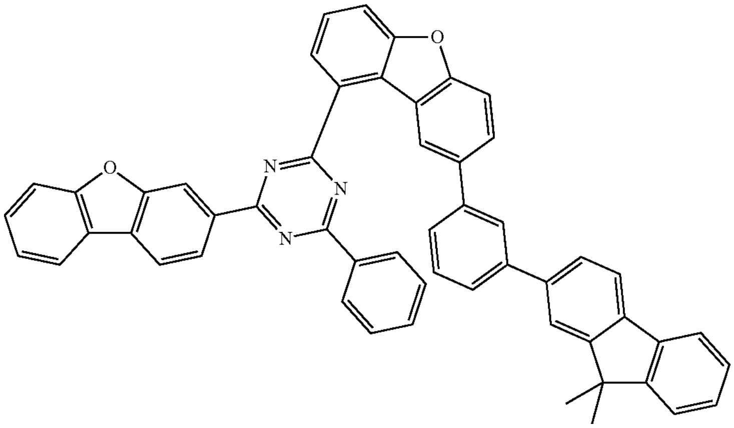 [SMILES: CC1(C)c2ccccc2-c2ccc(-c3cccc(-c4ccc5oc6cccc(-c7nc(-c8ccccc8)nc(-c8ccc9c(c8)oc8ccccc89)n7)c6c5c4)c3)cc21]
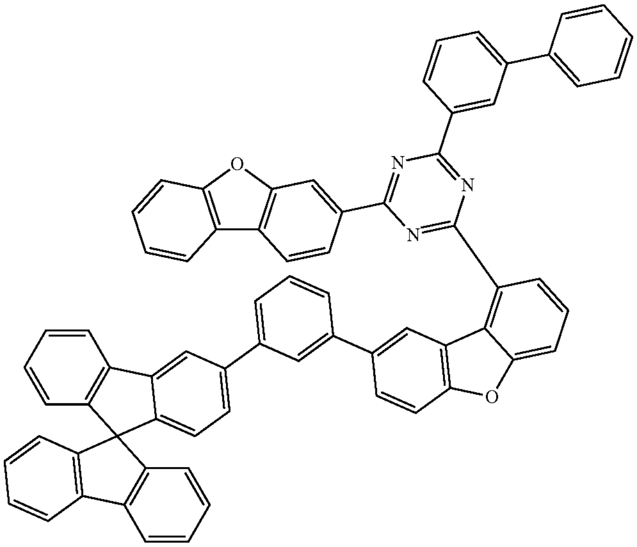 [SMILES: c1ccc(-c2cccc(-c3nc(-c4ccc5c(c4)oc4ccccc45)nc(-c4cccc5oc6ccc(-c7cccc(-c8ccc9c(c8)-c8ccccc8C98c9ccccc9-c9ccccc98)c7)cc6c45)n3)c2)cc1]
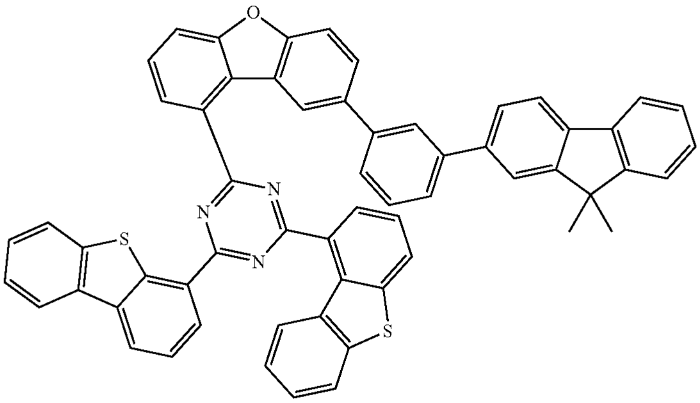 [SMILES: CC1(C)c2ccccc2-c2ccc(-c3cccc(-c4ccc5oc6cccc(-c7nc(-c8cccc9c8sc8ccccc89)nc(-c8cccc9sc%10ccccc%10c89)n7)c6c5c4)c3)cc21]

TABLE 1-continued
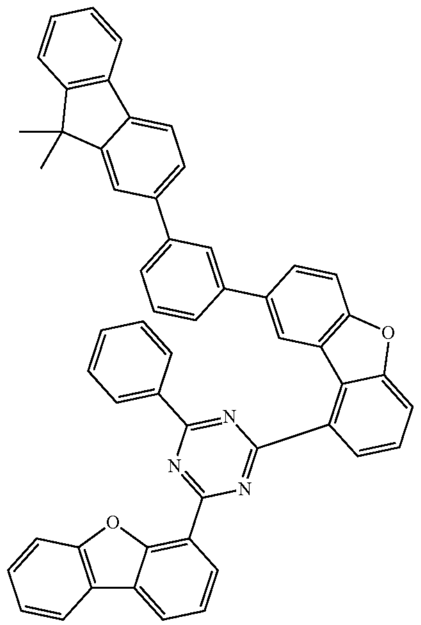 [SMILES: CC1(C)c2ccccc2-c2ccc(-c3cccc(-c4ccc5oc6cccc(-c7nc(-c8ccccc8)nc(-c8cccc9c8oc8ccccc89)n7)c6c5c4)c3)cc21]
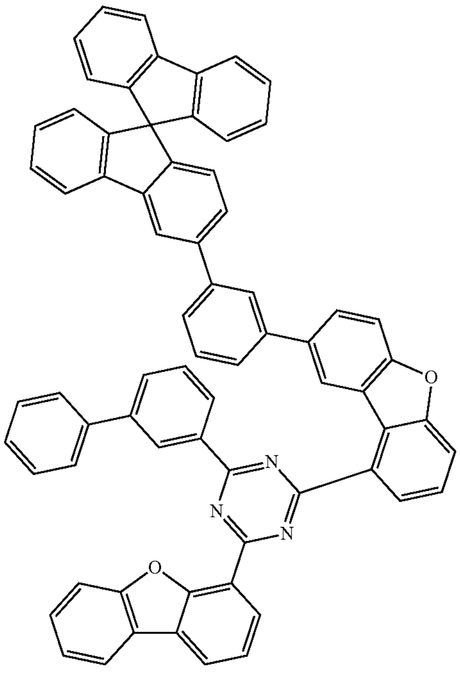 [SMILES: c1ccc(-c2cccc(-c3nc(-c4cccc5c4oc4ccccc45)nc(-c4cccc5oc6ccc(-c7cccc(-c8ccc9c(c8)-c8ccccc8C98c9ccccc9-c9ccccc98)c7)cc6c45)n3)c2)cc1]

TABLE 1-continued
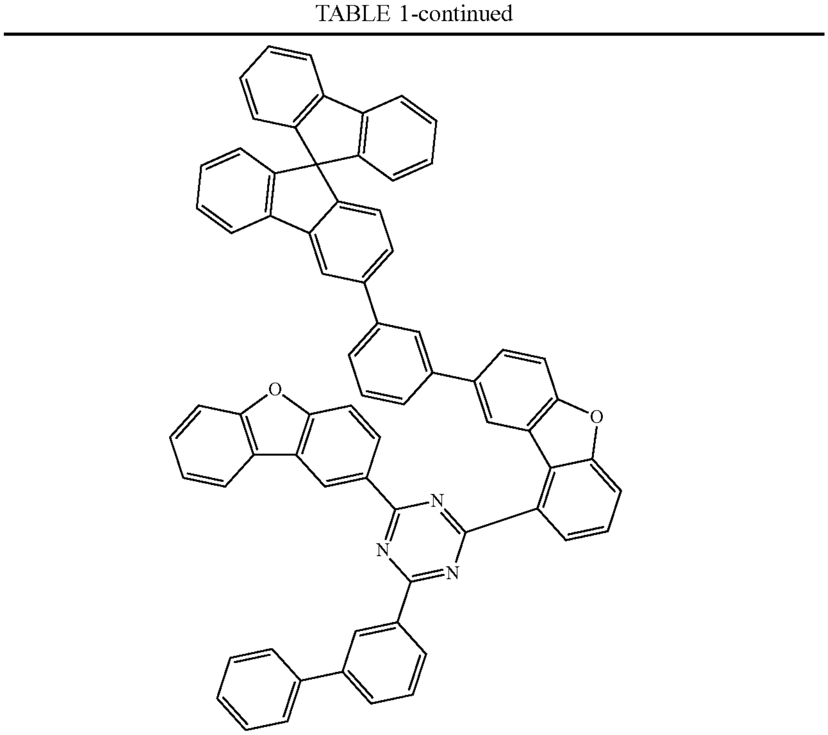
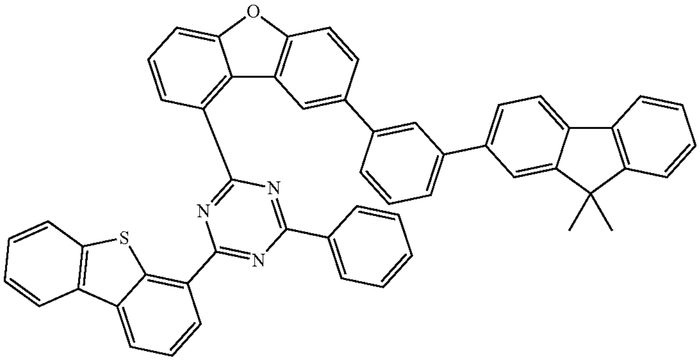 [SMILES: CC1(C)c2ccccc2-c2ccc(-c3cccc(-c4ccc5oc6cccc(-c7nc(-c8ccccc8)nc(-c8cccc9c8sc8ccccc89)n7)c6c5c4)c3)cc21]
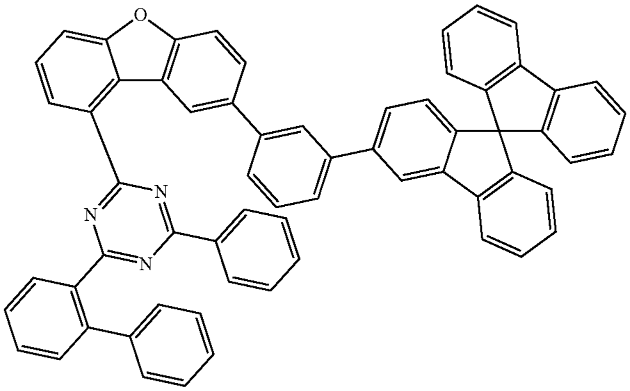 [SMILES: c1ccc(-c2nc(-c3ccccc3-c3ccccc3)nc(-c3cccc4oc5ccc(-c6cccc(-c7ccc8c(c7)-c7ccccc7C87c8ccccc8-c8ccccc87)c6)cc5c34)n2)cc1]

TABLE 1-continued
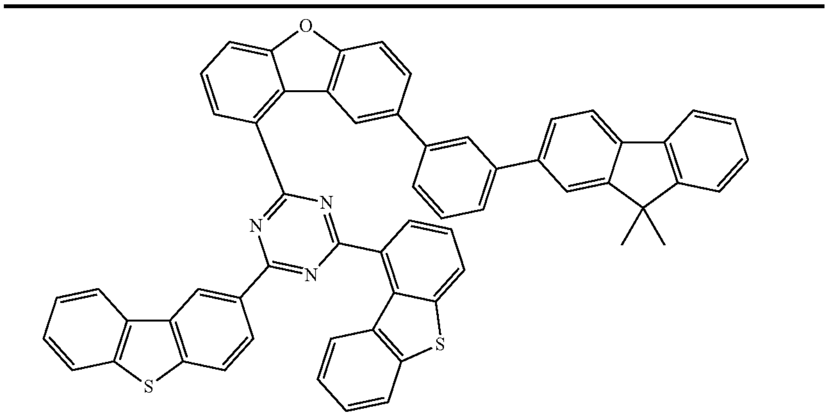
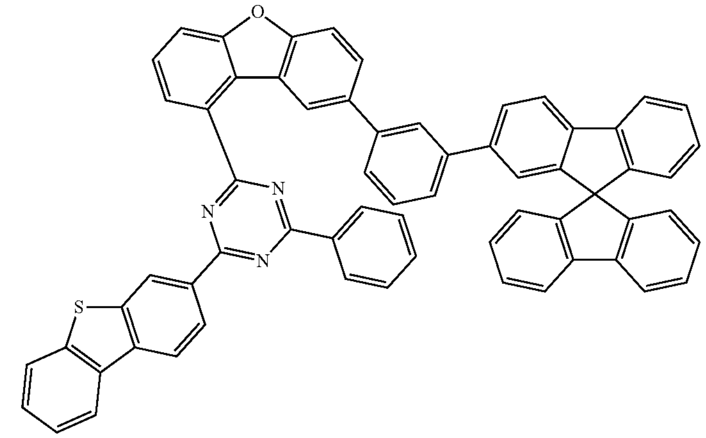 [SMILES: c1ccc(-c2nc(-c3ccc4c(c3)sc3ccccc34)nc(-c3cccc4oc5ccc(-c6cccc(-c7ccc8c(c7)C7(c9ccccc9-c9ccccc97)c7ccccc7-8)c6)cc5c34)n2)cc1]
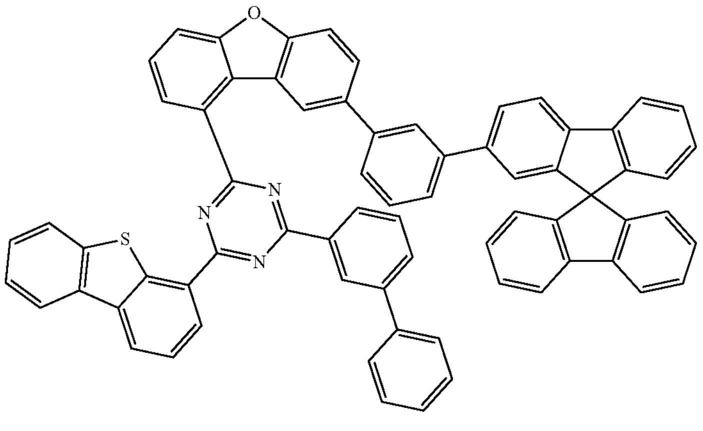 [SMILES: c1ccc(-c2cccc(-c3nc(-c4cccc5c4sc4ccccc45)nc(-c4cccc5oc6ccc(-c7cccc(-c8ccc9c(c8)C8(c%10ccccc%10-c%10ccccc%108)c8ccccc8-9)c7)cc6c45)n3)c2)cc1]

TABLE 1-continued
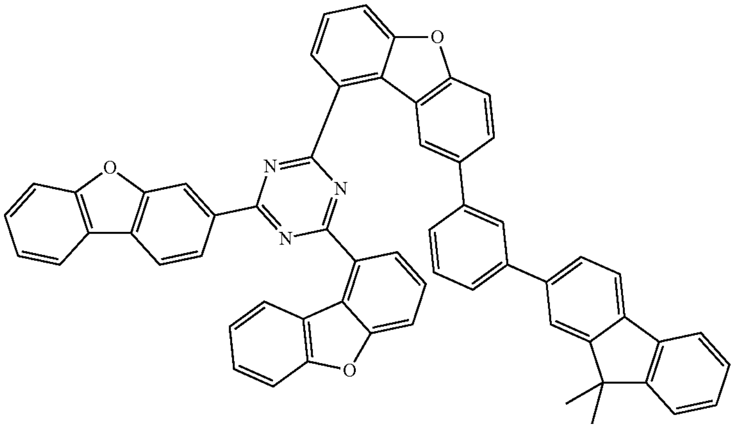 [SMILES: CC1(C)c2ccccc2-c2ccc(-c3cccc(-c4ccc5oc6cccc(-c7nc(-c8ccc9c(c8)oc8ccccc89)nc(-c8cccc9oc%10ccccc%10c89)n7)c6c5c4)c3)cc21]
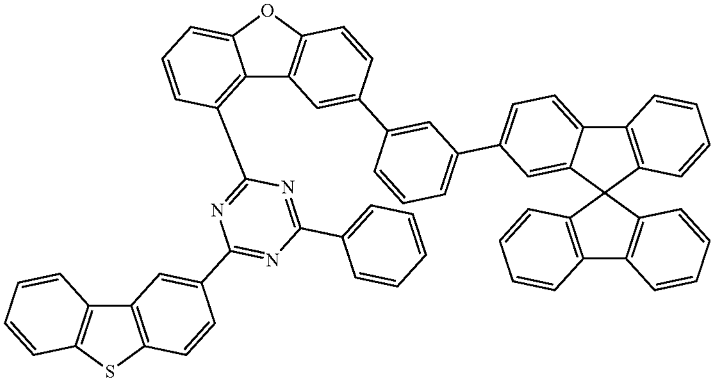 [SMILES: c1ccc(-c2nc(-c3ccc4sc5ccccc5c4c3)nc(-c3cccc4oc5ccc(-c6cccc(-c7ccc8c(c7)C7(c9ccccc9-c9ccccc97)c7ccccc7-8)c6)cc5c34)n2)cc1]
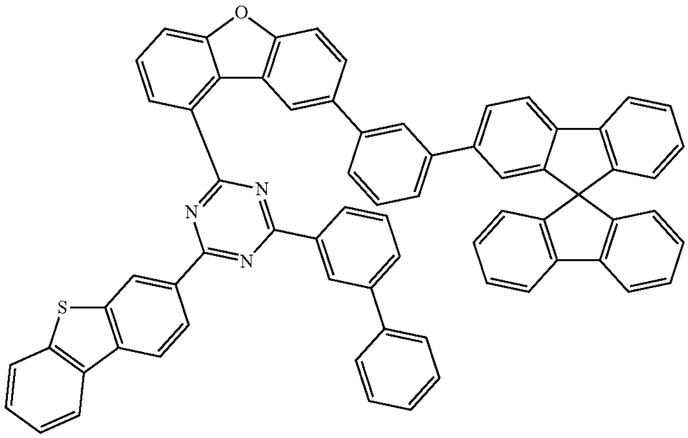 [SMILES: c1ccc(-c2cccc(-c3nc(-c4ccc5c(c4)sc4ccccc45)nc(-c4cccc5oc6ccc(-c7cccc(-c8ccc9c(c8)C8(c%10ccccc%10-c%10ccccc%108)c8ccccc8-9)c7)cc6c45)n3)c2)cc1]

TABLE 1-continued
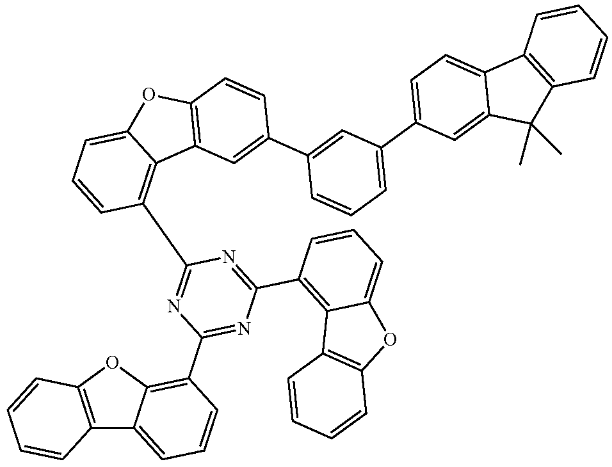 [SMILES: CC1(C)c2ccccc2-c2ccc(-c3cccc(-c4ccc5oc6cccc(-c7nc(-c8cccc9c8oc8ccccc89)nc(-c8cccc9oc%10ccccc%10c89)n7)c6c5c4)c3)cc21]
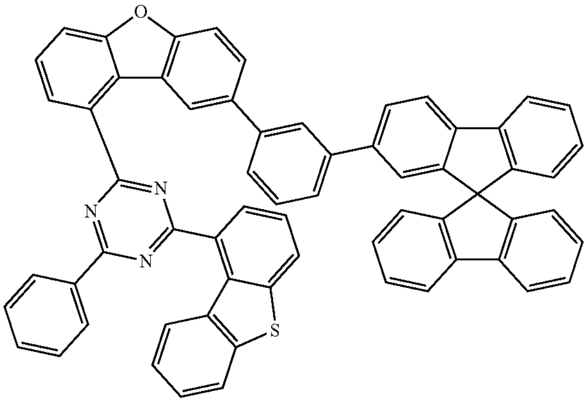 [SMILES: c1ccc(-c2nc(-c3cccc4oc5ccc(-c6cccc(-c7ccc8c(c7)C7(c9ccccc9-c9ccccc97)c7ccccc7-8)c6)cc5c34)nc(-c3cccc4sc5ccccc5c34)n2)cc1]
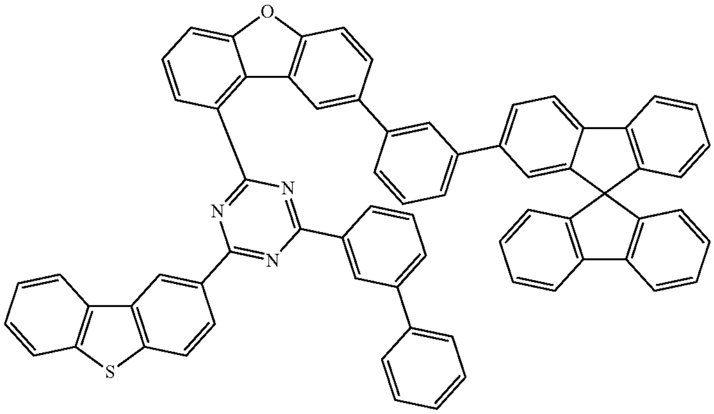 [SMILES: c1ccc(-c2cccc(-c3nc(-c4ccc5sc6ccccc6c5c4)nc(-c4cccc5oc6ccc(-c7cccc(-c8ccc9c(c8)C8(c%10ccccc%10-c%10ccccc%108)c8ccccc8-9)c7)cc6c45)n3)c2)cc1]

TABLE 1-continued
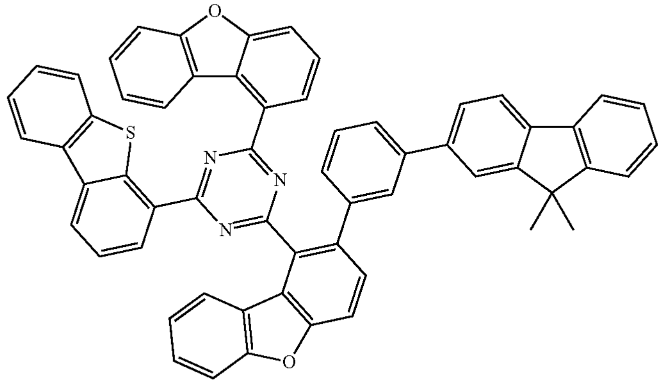 [SMILES: CC1(C)c2ccccc2-c2ccc(-c3cccc(-c4ccc5oc6ccccc6c5c4-c4nc(-c5cccc6c5sc5ccccc56)nc(-c5cccc6oc7ccccc7c56)n4)c3)cc21]
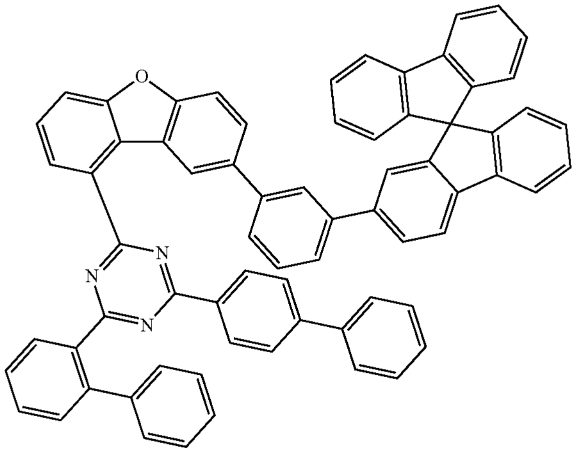 [SMILES: c1ccc(-c2ccc(-c3nc(-c4ccccc4-c4ccccc4)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
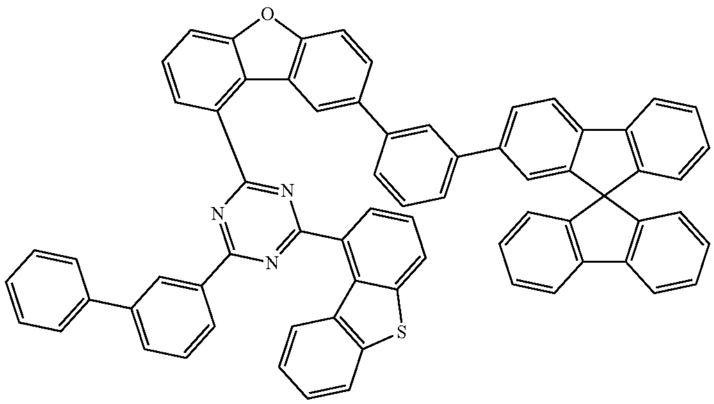 [SMILES: c1ccc(-c2cccc(-c3nc(-c4cccc5oc6ccc(-c7cccc(-c8ccc9c(c8)C8(c%10ccccc%10-c%10ccccc%108)c8ccccc8-9)c7)cc6c45)nc(-c4cccc5sc6ccccc6c45)n3)c2)cc1]
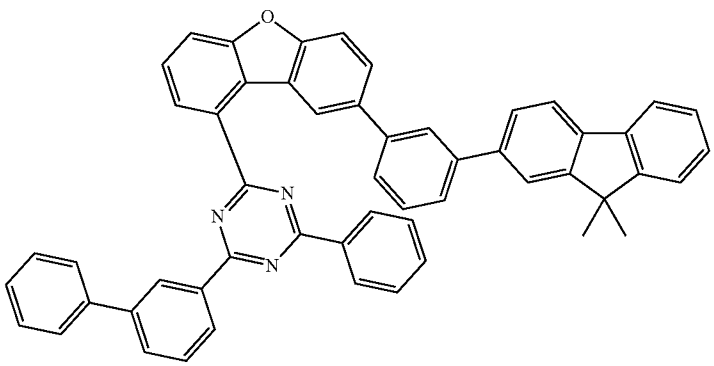 [SMILES: CC1(C)c2ccccc2-c2ccc(-c3cccc(-c4ccc5oc6cccc(-c7nc(-c8ccccc8)nc(-c8cccc(-c9ccccc9)c8)n7)c6c5c4)c3)cc21]

TABLE 1-continued
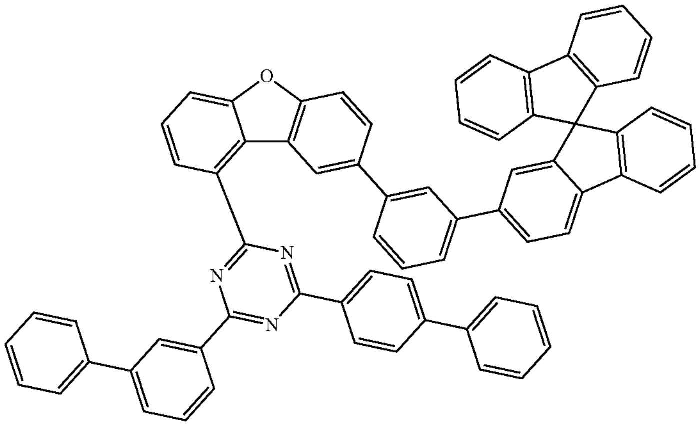 [SMILES: c1ccc(-c2ccc(-c3nc(-c4cccc(-c5ccccc5)c4)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
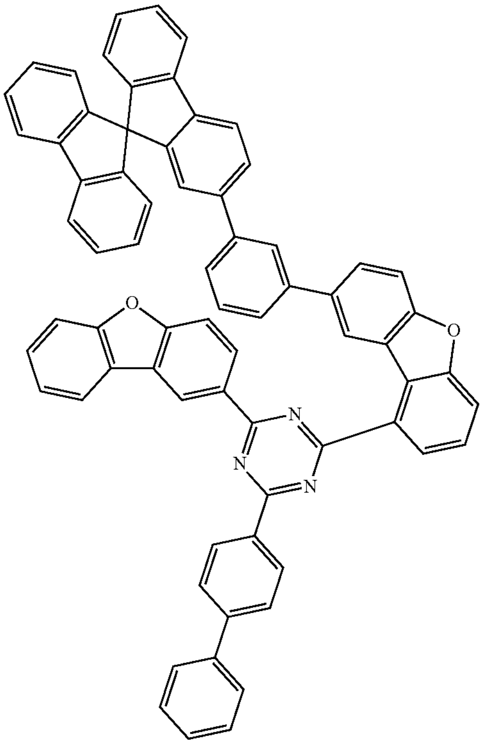 [SMILES: c1ccc(-c2ccc(-c3nc(-c4ccc5oc6ccccc6c5c4)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]

TABLE 1-continued
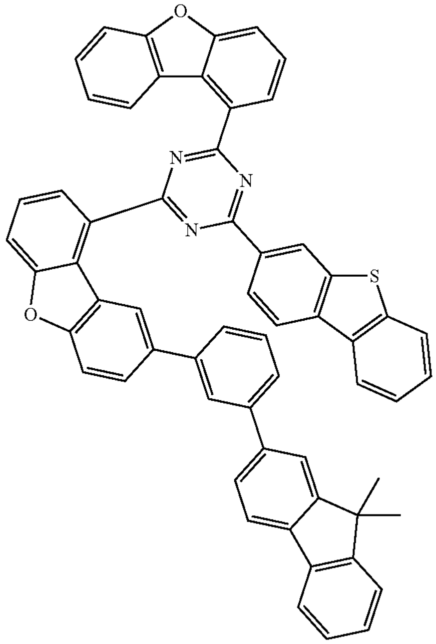 [SMILES: CC1(C)c2ccccc2-c2ccc(-c3cccc(-c4ccc5oc6cccc(-c7nc(-c8ccc9c(c8)sc8ccccc89)nc(-c8cccc9oc%10ccccc%10c89)n7)c6c5c4)c3)cc21]
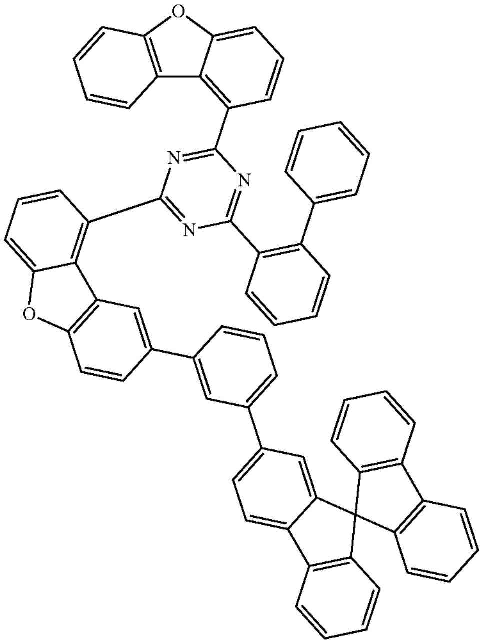 [SMILES: c1ccc(-c2ccccc2-c2nc(-c3cccc4oc5ccccc5c34)nc(-c3cccc4oc5ccc(-c6cccc(-c7ccc8c(c7)C7(c9ccccc9-c9ccccc97)c7ccccc7-8)c6)cc5c34)n2)cc1]

TABLE 1-continued
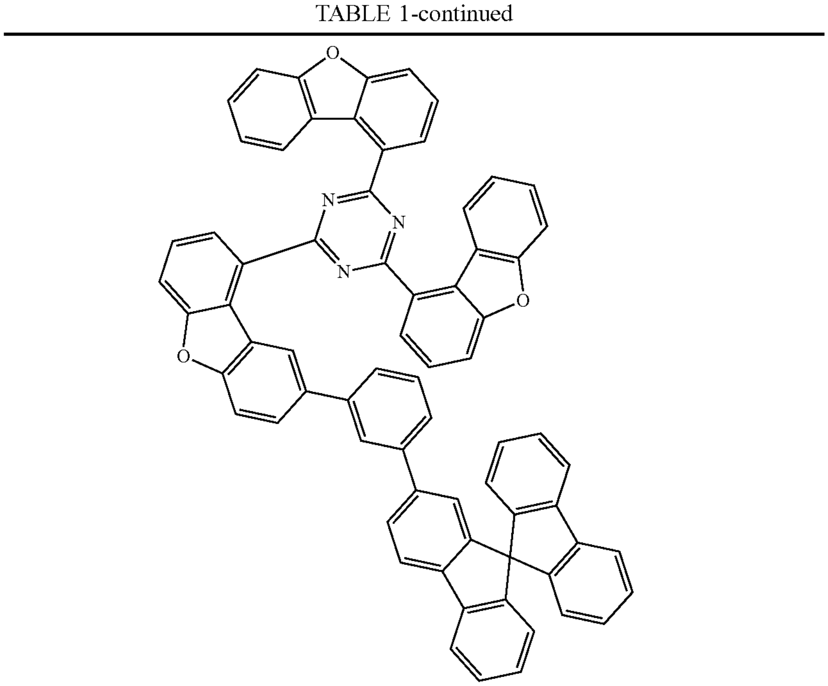
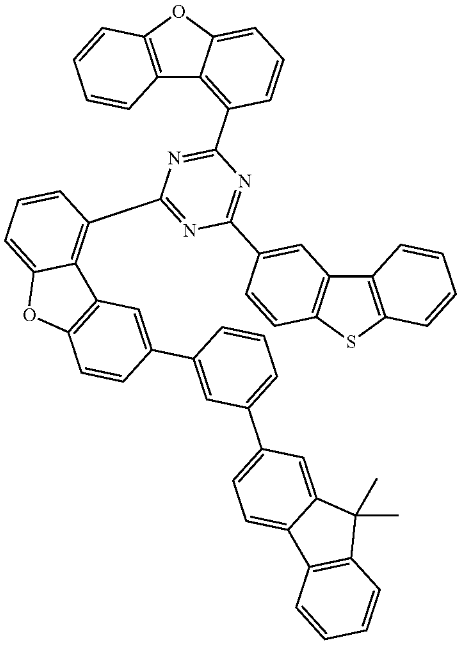 [SMILES: CC1(C)c2ccccc2-c2ccc(-c3cccc(-c4ccc5oc6cccc(-c7nc(-c8ccc9sc%10ccccc%10c9c8)nc(-c8cccc9oc%10ccccc%10c89)n7)c6c5c4)c3)cc21]

TABLE 1-continued
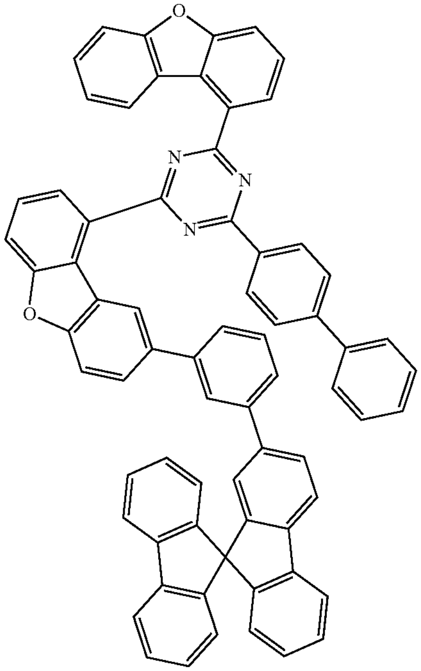 [SMILES: c1ccc(-c2ccc(-c3nc(-c4cccc5oc6ccccc6c45)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
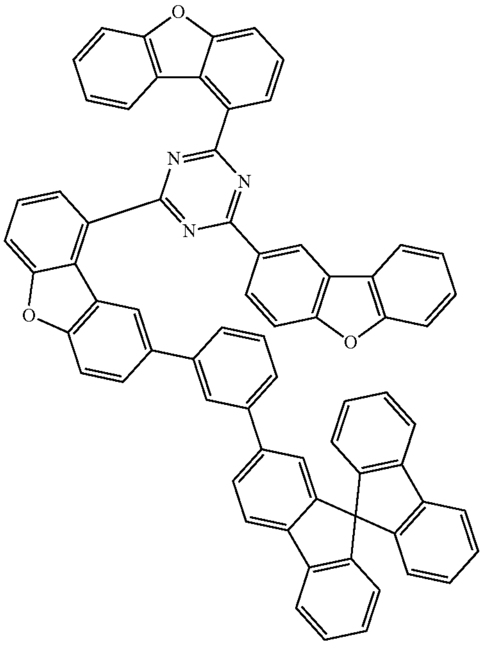 [SMILES: c1cc(-c2ccc3c(c2)C2(c4ccccc4-c4ccccc42)c2ccccc2-3)cc(-c2ccc3oc4cccc(-c5nc(-c6ccc7oc8ccccc8c7c6)nc(-c6cccc7oc8ccccc8c67)n5)c4c3c2)c1]

TABLE 1-continued
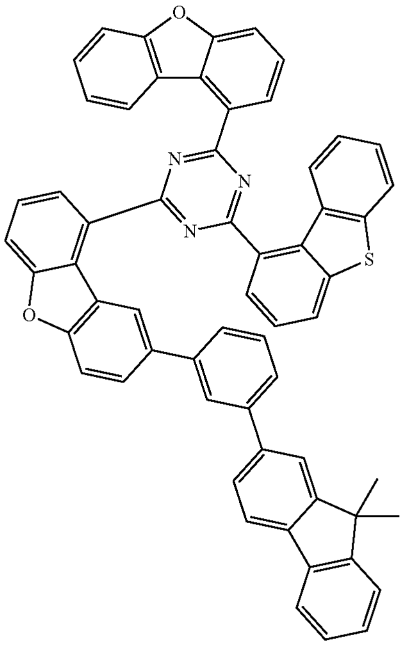 [SMILES: CC1(C)c2ccccc2-c2ccc(-c3cccc(-c4ccc5oc6cccc(-c7nc(-c8cccc9oc%10ccccc%10c89)nc(-c8cccc9sc%10ccccc%10c89)n7)c6c5c4)c3)cc21]
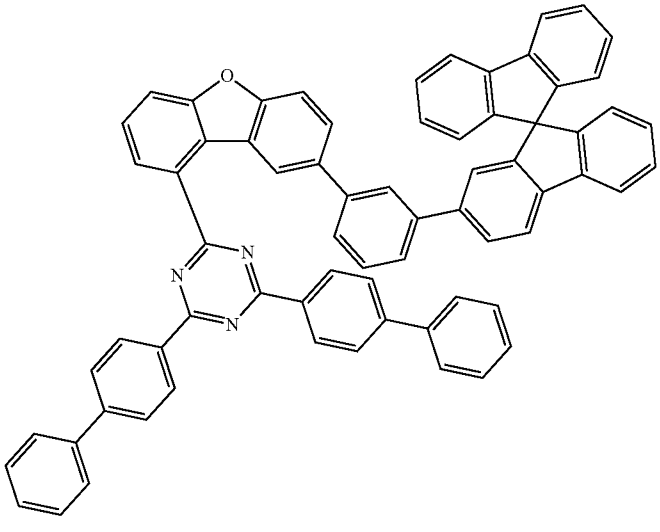 [SMILES: c1ccc(-c2ccc(-c3nc(-c4ccc(-c5ccccc5)cc4)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]

TABLE 1-continued
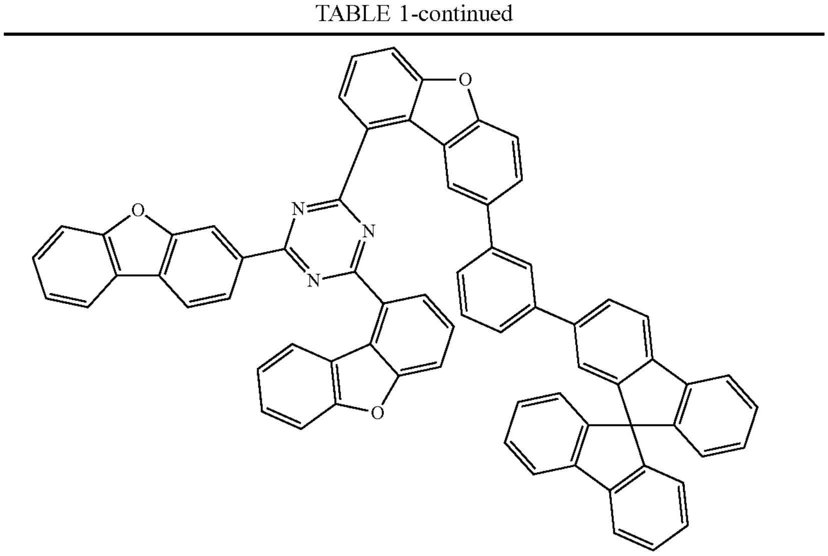
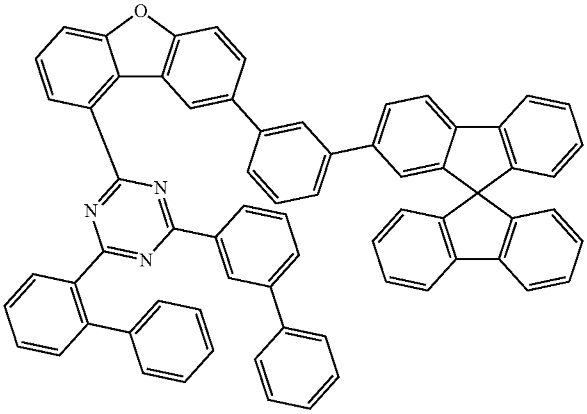 [SMILES: c1ccc(-c2cccc(-c3nc(-c4ccccc4-c4ccccc4)nc(-c4cccc5oc6ccc(-c7cccc(-c8ccc9c(c8)C8(c%10ccccc%10-c%10ccccc%108)c8ccccc8-9)c7)cc6c45)n3)c2)cc1]
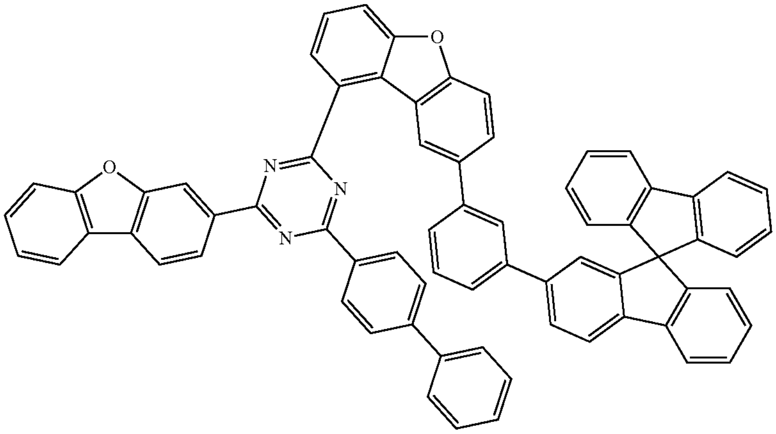 [SMILES: c1ccc(-c2ccc(-c3nc(-c4ccc5c(c4)oc4ccccc45)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]

TABLE 1-continued
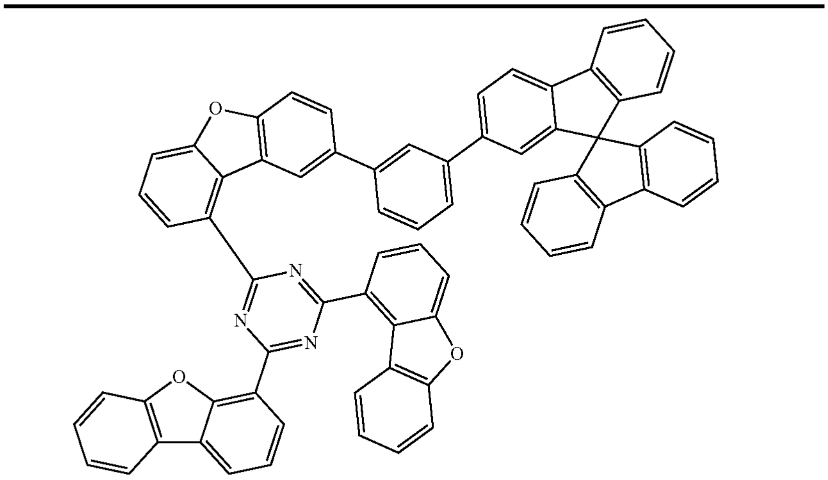
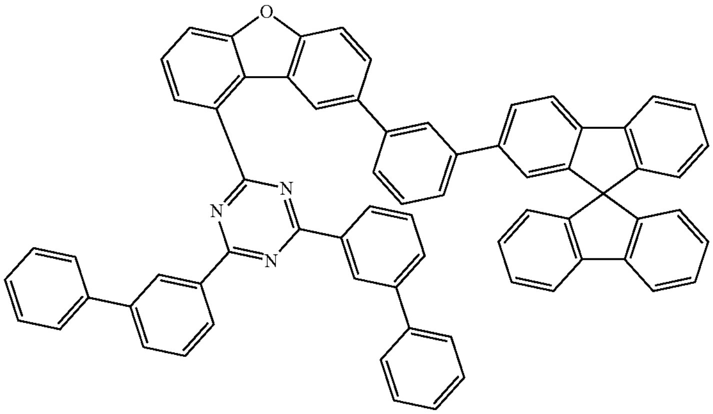 [SMILES: c1ccc(-c2cccc(-c3nc(-c4cccc(-c5ccccc5)c4)nc(-c4cccc5oc6ccc(-c7cccc(-c8ccc9c(c8)C8(c%10ccccc%10-c%10ccccc%108)c8ccccc8-9)c7)cc6c45)n3)c2)cc1]
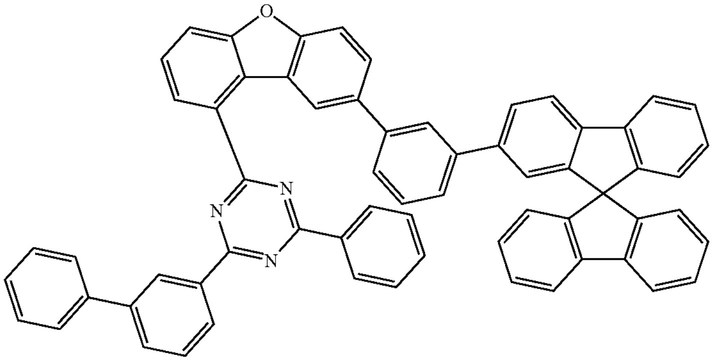 [SMILES: c1ccc(-c2cccc(-c3nc(-c4ccccc4)nc(-c4cccc5oc6ccc(-c7cccc(-c8ccc9c(c8)C8(c%10ccccc%10-c%10ccccc%108)c8ccccc8-9)c7)cc6c45)n3)c2)cc1]
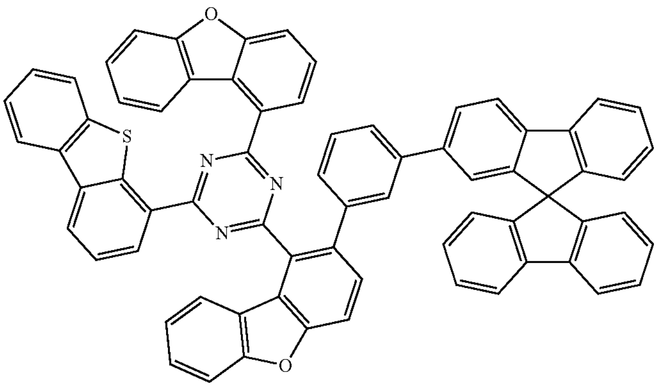 [SMILES: c1cc(-c2ccc3c(c2)C2(c4ccccc4-c4ccccc42)c2ccccc2-3)cc(-c2ccc3oc4ccccc4c3c2-c2nc(-c3cccc4c3sc3ccccc34)nc(-c3cccc4oc5ccccc5c34)n2)c1]

TABLE 1-continued
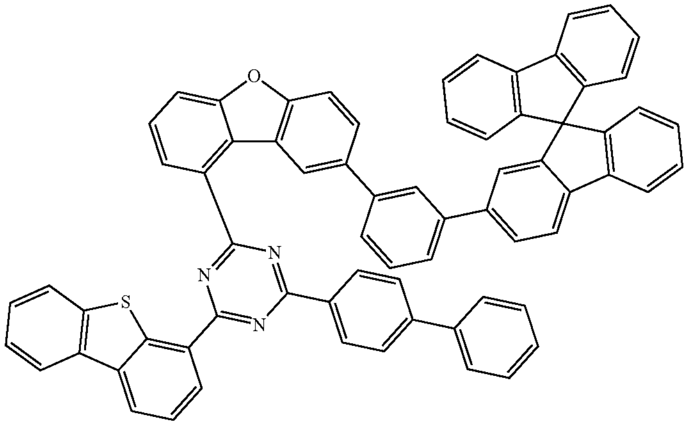 [SMILES: c1ccc(-c2ccc(-c3nc(-c4cccc5c4sc4ccccc45)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
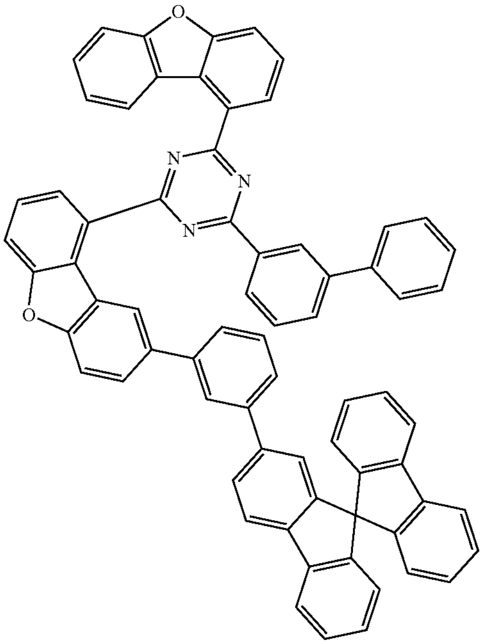 [SMILES: c1ccc(-c2cccc(-c3nc(-c4cccc5oc6ccccc6c45)nc(-c4cccc5oc6ccc(-c7cccc(-c8ccc9c(c8)C8(c%10ccccc%10-c%10ccccc%108)c8ccccc8-9)c7)cc6c45)n3)c2)cc1]

TABLE 1-continued
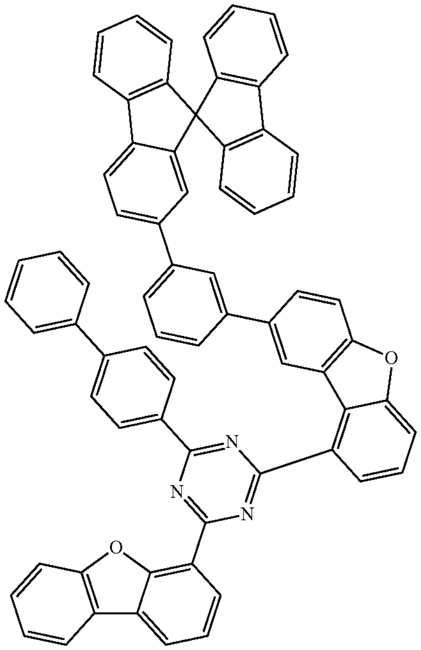 [SMILES: c1ccc(-c2ccc(-c3nc(-c4cccc5c4oc4ccccc45)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
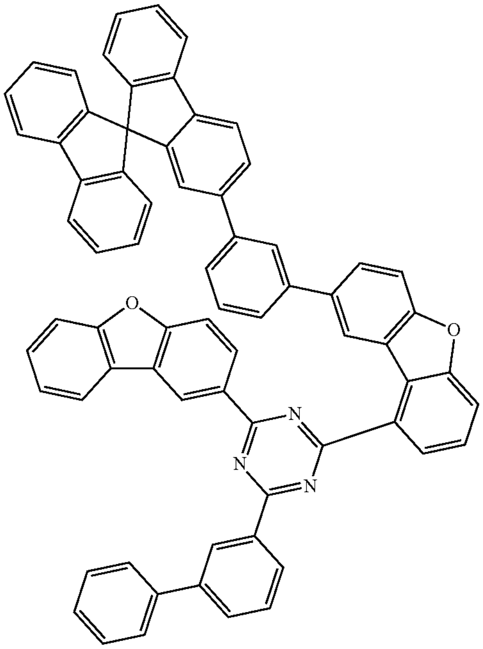 [SMILES: c1ccc(-c2cccc(-c3nc(-c4ccc5oc6ccccc6c5c4)nc(-c4cccc5oc6ccc(-c7cccc(-c8ccc9c(c8)C8(c%10ccccc%10-c%10ccccc%108)c8ccccc8-9)c7)cc6c45)n3)c2)cc1]

TABLE 1-continued
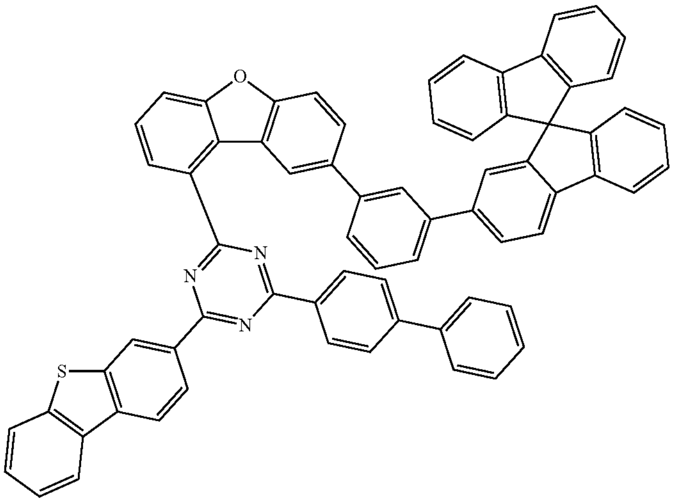 [SMILES: c1ccc(-c2ccc(-c3nc(-c4ccc5c(c4)sc4ccccc45)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
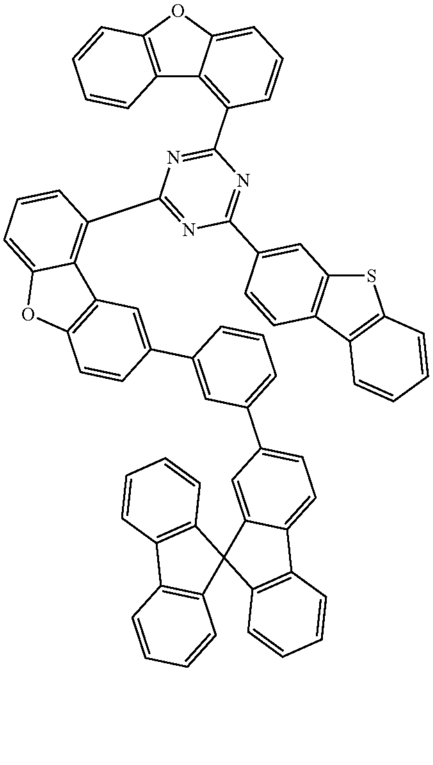 [SMILES: c1cc(-c2ccc3c(c2)C2(c4ccccc4-c4ccccc42)c2ccccc2-3)cc(-c2ccc3oc4cccc(-c5nc(-c6ccc7c(c6)sc6ccccc67)nc(-c6cccc7oc8ccccc8c67)n5)c4c3c2)c1]

TABLE 1-continued
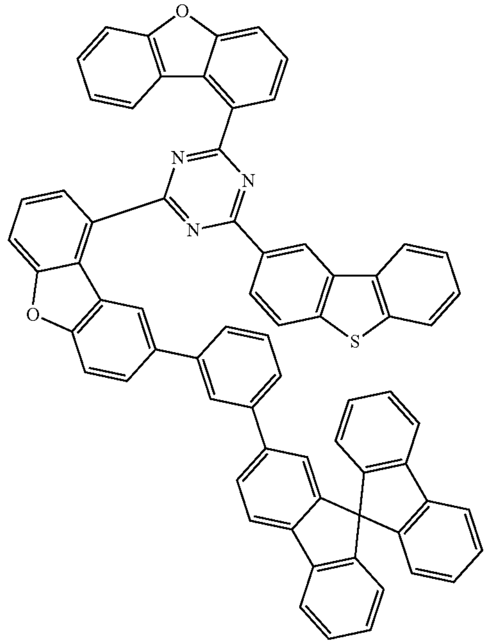
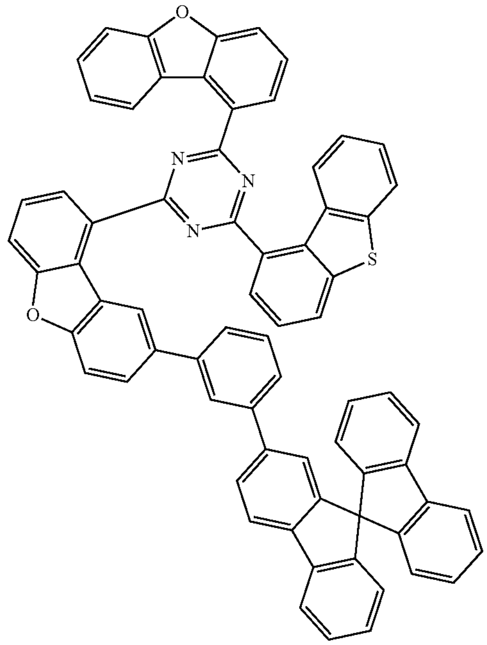 [SMILES: c1cc(-c2ccc3c(c2)C2(c4ccccc4-c4ccccc42)c2ccccc2-3)cc(-c2ccc3oc4cccc(-c5nc(-c6cccc7oc8ccccc8c67)nc(-c6cccc7sc8ccccc8c67)n5)c4c3c2)c1]

TABLE 1-continued
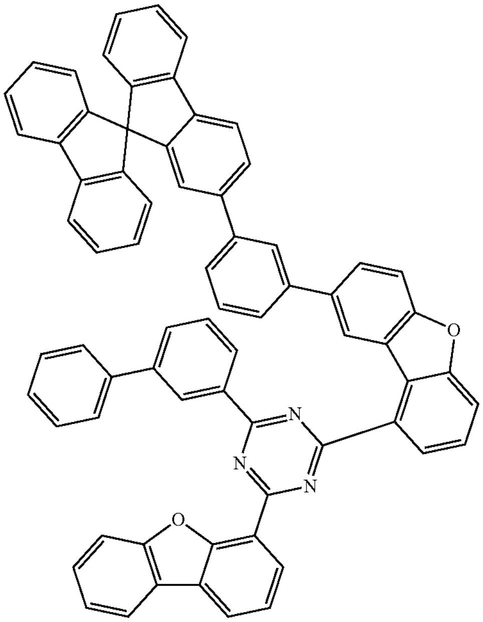 [SMILES: c1ccc(-c2cccc(-c3nc(-c4cccc5c4oc4ccccc45)nc(-c4cccc5oc6ccc(-c7cccc(-c8ccc9c(c8)C8(c%10ccccc%10-c%10ccccc%108)c8ccccc8-9)c7)cc6c45)n3)c2)cc1]
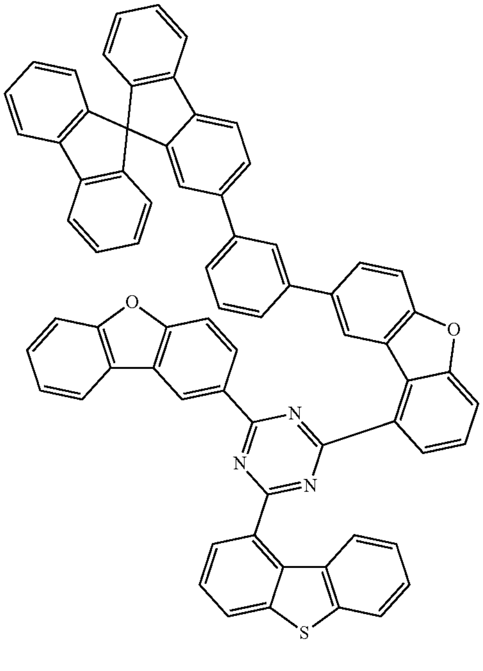 [SMILES: c1cc(-c2ccc3c(c2)C2(c4ccccc4-c4ccccc42)c2ccccc2-3)cc(-c2ccc3oc4cccc(-c5nc(-c6ccc7oc8ccccc8c7c6)nc(-c6cccc7sc8ccccc8c67)n5)c4c3c2)c1]

TABLE 1-continued
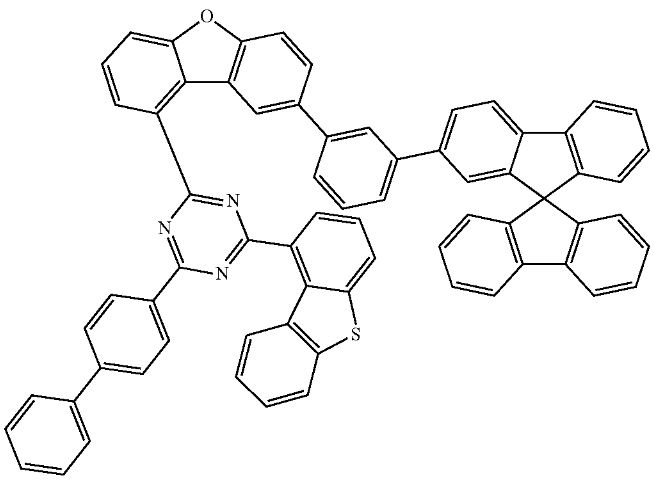 [SMILES: c1ccc(-c2ccc(-c3nc(-c4cccc5oc6ccc(-c7cccc(-c8ccc9c(c8)C8(c%10ccccc%10-c%10ccccc%108)c8ccccc8-9)c7)cc6c45)nc(-c4cccc5sc6ccccc6c45)n3)cc2)cc1]
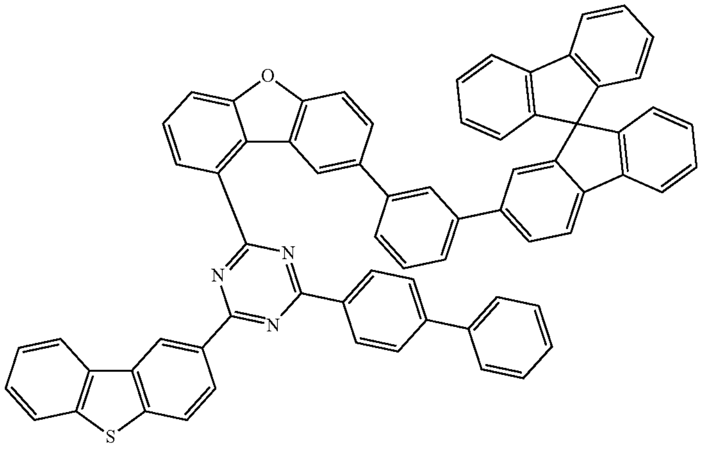 [SMILES: c1ccc(-c2ccc(-c3nc(-c4ccc5sc6ccccc6c5c4)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
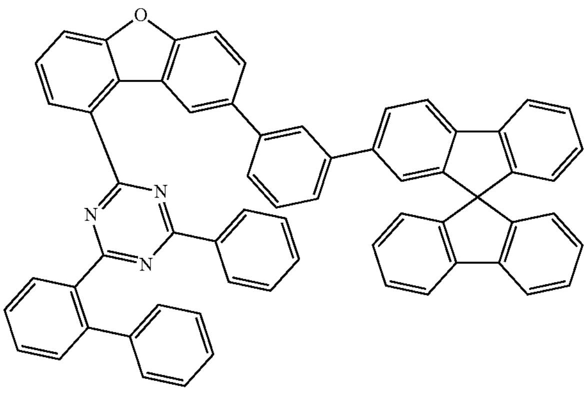 [SMILES: c1ccc(-c2nc(-c3ccccc3-c3ccccc3)nc(-c3cccc4oc5ccc(-c6cccc(-c7ccc8c(c7)C7(c9ccccc9-c9ccccc97)c7ccccc7-8)c6)cc5c34)n2)cc1]

TABLE 1-continued
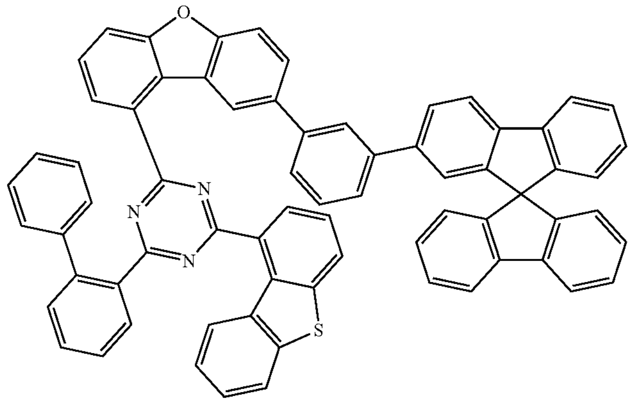 [SMILES: c1ccc(-c2ccccc2-c2nc(-c3cccc4oc5ccc(-c6cccc(-c7ccc8c(c7)C7(c9ccccc9-c9ccccc97)c7ccccc7-8)c6)cc5c34)nc(-c3cccc4sc5ccccc5c34)n2)cc1]
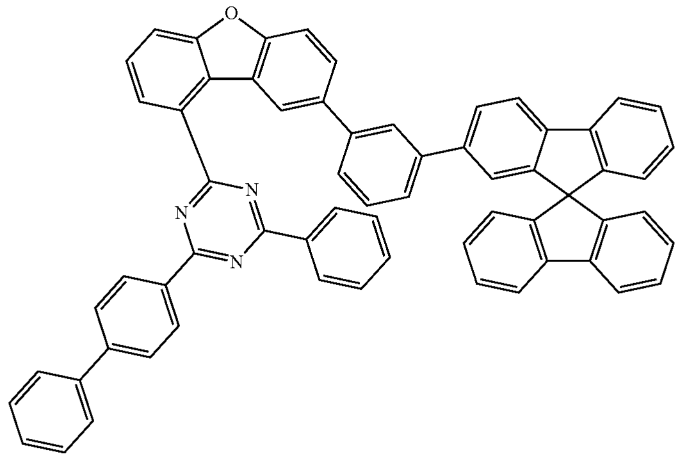 [SMILES: c1ccc(-c2ccc(-c3nc(-c4ccccc4)nc(-c4cccc5oc6ccc(-c7cccc(-c8ccc9c(c8)C8(c%10ccccc%10-c%10ccccc%108)c8ccccc8-9)c7)cc6c45)n3)cc2)cc1]
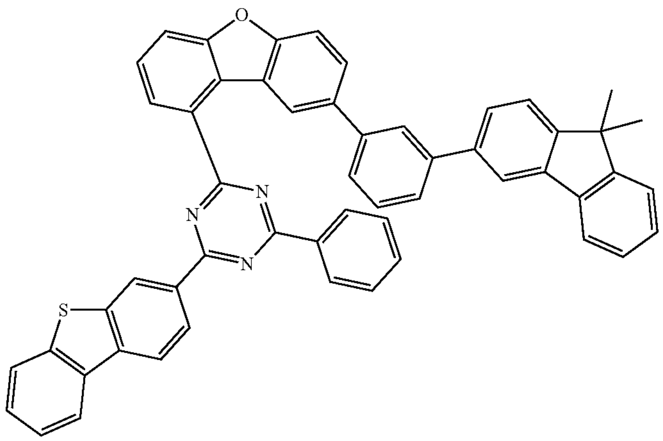 [SMILES: CC1(C)c2ccccc2-c2cc(-c3cccc(-c4ccc5oc6cccc(-c7nc(-c8ccccc8)nc(-c8ccc9c(c8)sc8ccccc89)n7)c6c5c4)c3)ccc21]

TABLE 1-continued
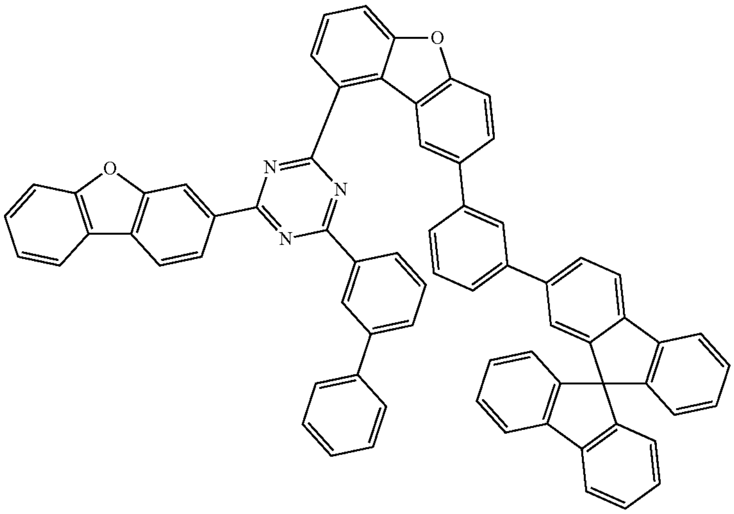 [SMILES: c1ccc(-c2cccc(-c3nc(-c4ccc5c(c4)oc4ccccc45)nc(-c4cccc5oc6ccc(-c7cccc(-c8ccc9c(c8)C8(c%10ccccc%10-c%10ccccc%108)c8ccccc8-9)c7)cc6c45)n3)c2)cc1]
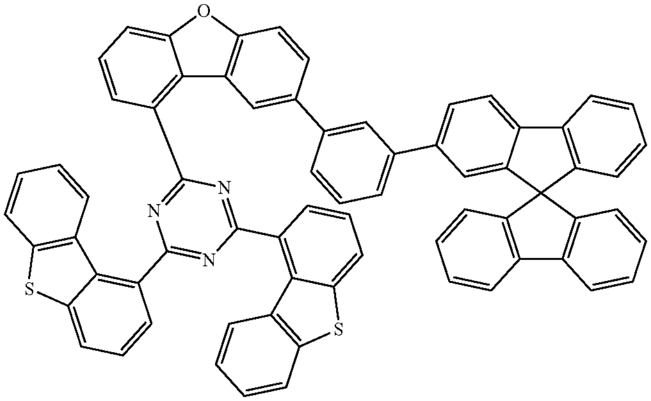 [SMILES: c1cc(-c2ccc3c(c2)C2(c4ccccc4-c4ccccc42)c2ccccc2-3)cc(-c2ccc3oc4cccc(-c5nc(-c6cccc7sc8ccccc8c67)nc(-c6cccc7sc8ccccc8c67)n5)c4c3c2)c1]
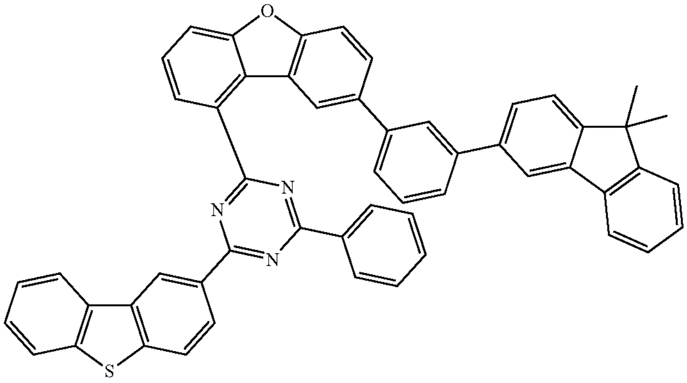 [SMILES: CC1(C)c2ccccc2-c2cc(-c3cccc(-c4ccc5oc6cccc(-c7nc(-c8ccccc8)nc(-c8ccc9sc%10ccccc%10c9c8)n7)c6c5c4)c3)ccc21]

TABLE 1-continued
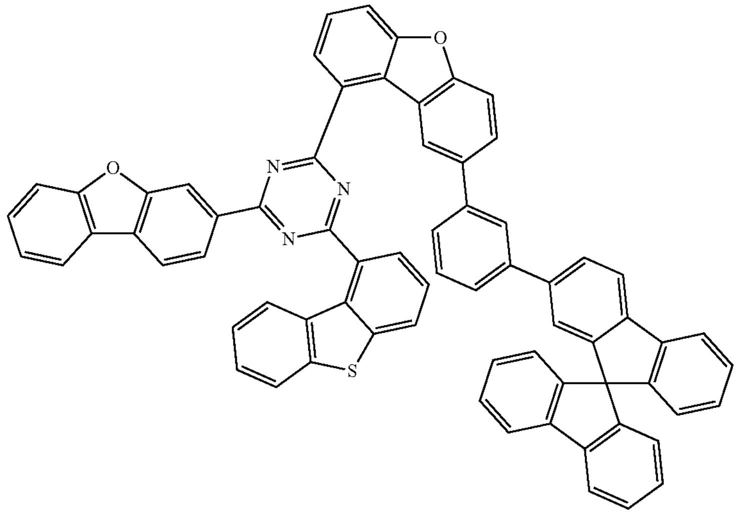 [SMILES: c1cc(-c2ccc3c(c2)C2(c4ccccc4-c4ccccc42)c2ccccc2-3)cc(-c2ccc3oc4cccc(-c5nc(-c6ccc7c(c6)oc6ccccc67)nc(-c6cccc7sc8ccccc8c67)n5)c4c3c2)c1]
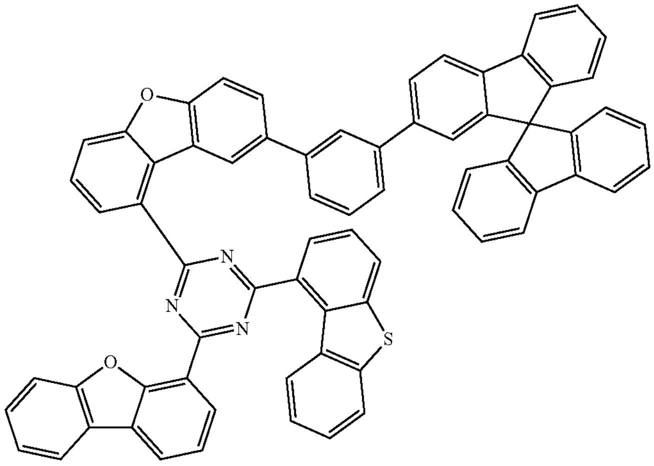 [SMILES: c1cc(-c2ccc3c(c2)C2(c4ccccc4-c4ccccc42)c2ccccc2-3)cc(-c2ccc3oc4cccc(-c5nc(-c6cccc7c6oc6ccccc67)nc(-c6cccc7sc8ccccc8c67)n5)c4c3c2)c1]
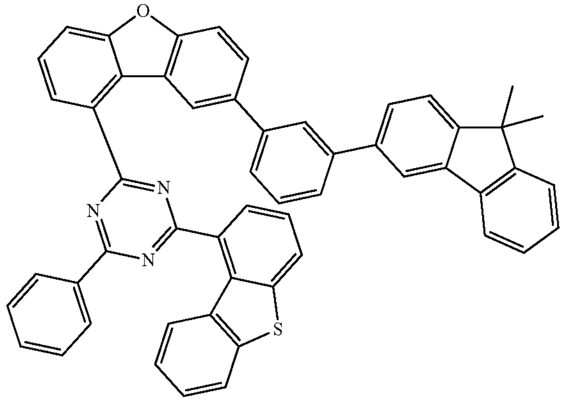 [SMILES: CC1(C)c2ccccc2-c2cc(-c3cccc(-c4ccc5oc6cccc(-c7nc(-c8ccccc8)nc(-c8cccc9sc%10ccccc%10c89)n7)c6c5c4)c3)ccc21]

TABLE 1-continued
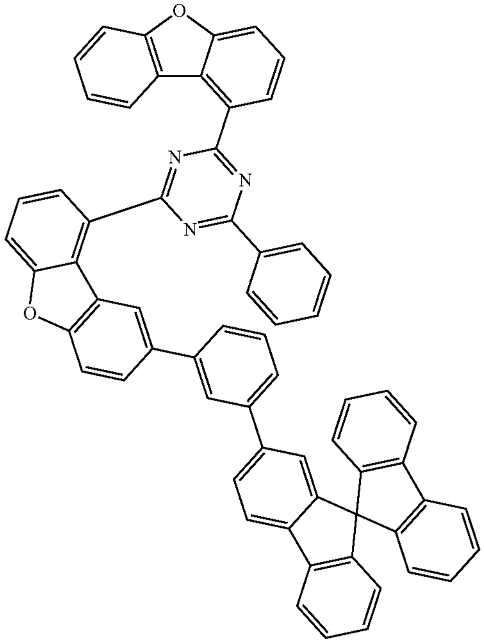 [SMILES: c1ccc(-c2nc(-c3cccc4oc5ccccc5c34)nc(-c3cccc4oc5ccc(-c6cccc(-c7ccc8c(c7)C7(c9ccccc9-c9ccccc97)c7ccccc7-8)c6)cc5c34)n2)cc1]
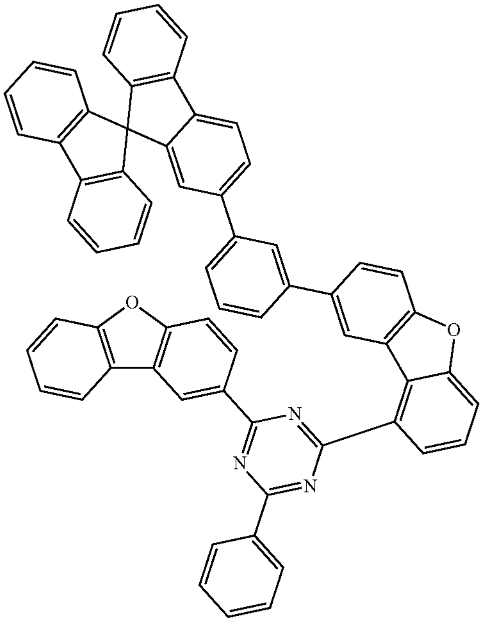 [SMILES: c1ccc(-c2nc(-c3ccc4oc5ccccc5c4c3)nc(-c3cccc4oc5ccc(-c6cccc(-c7ccc8c(c7)C7(c9ccccc9-c9ccccc97)c7ccccc7-8)c6)cc5c34)n2)cc1]

TABLE 1-continued
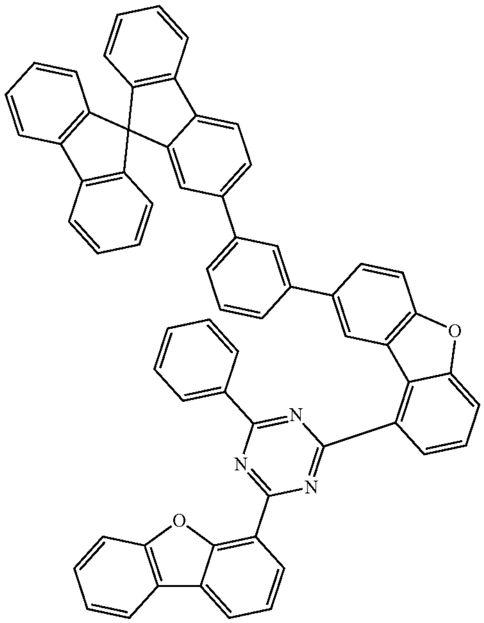 [SMILES: c1ccc(-c2nc(-c3cccc4c3oc3ccccc34)nc(-c3cccc4oc5ccc(-c6cccc(-c7ccc8c(c7)C7(c9ccccc9-c9ccccc97)c7ccccc7-8)c6)cc5c34)n2)cc1]
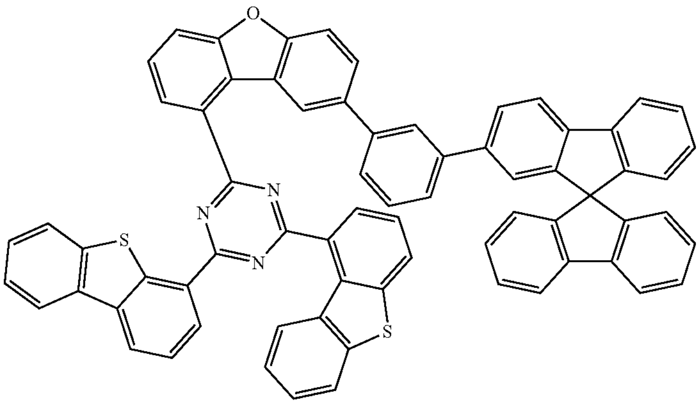 [SMILES: c1cc(-c2ccc3c(c2)C2(c4ccccc4-c4ccccc42)c2ccccc2-3)cc(-c2ccc3oc4cccc(-c5nc(-c6cccc7c6sc6ccccc67)nc(-c6cccc7sc8ccccc8c67)n5)c4c3c2)c1]
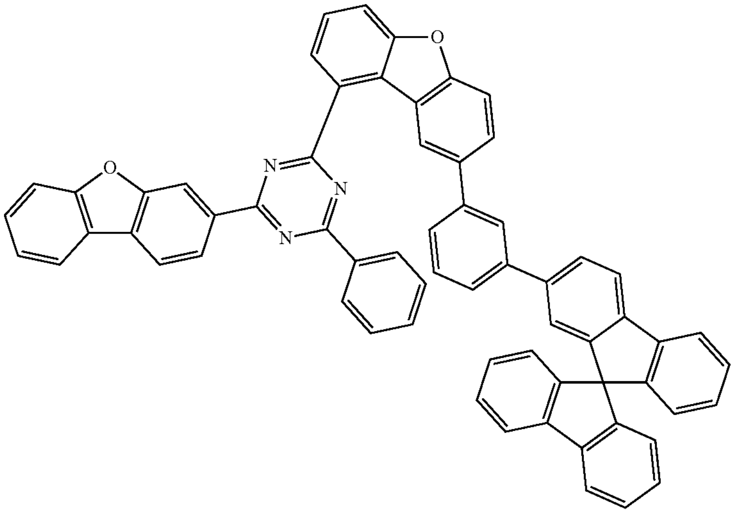 [SMILES: c1ccc(-c2nc(-c3ccc4c(c3)oc3ccccc34)nc(-c3cccc4oc5ccc(-c6cccc(-c7ccc8c(c7)C7(c9ccccc9-c9ccccc97)c7ccccc7-8)c6)cc5c34)n2)cc1]

TABLE 1-continued
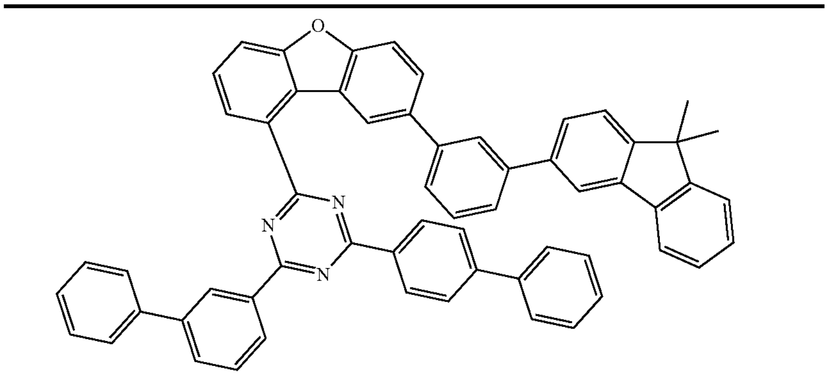
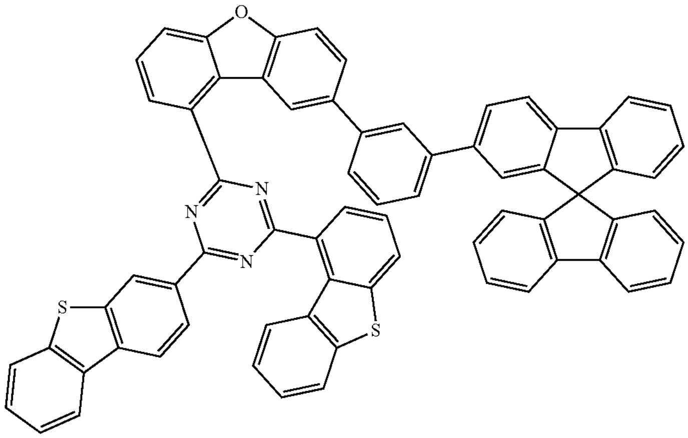 [SMILES: c1cc(-c2ccc3c(c2)C2(c4ccccc4-c4ccccc42)c2ccccc2-3)cc(-c2ccc3oc4cccc(-c5nc(-c6ccc7c(c6)sc6ccccc67)nc(-c6cccc7sc8ccccc8c67)n5)c4c3c2)c1]
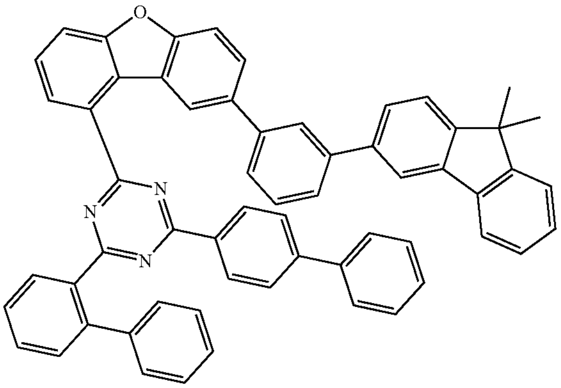 [SMILES: CC1(C)c2ccccc2-c2cc(-c3cccc(-c4ccc5oc6cccc(-c7nc(-c8ccc(-c9ccccc9)cc8)nc(-c8ccccc8-c8ccccc8)n7)c6c5c4)c3)ccc21]
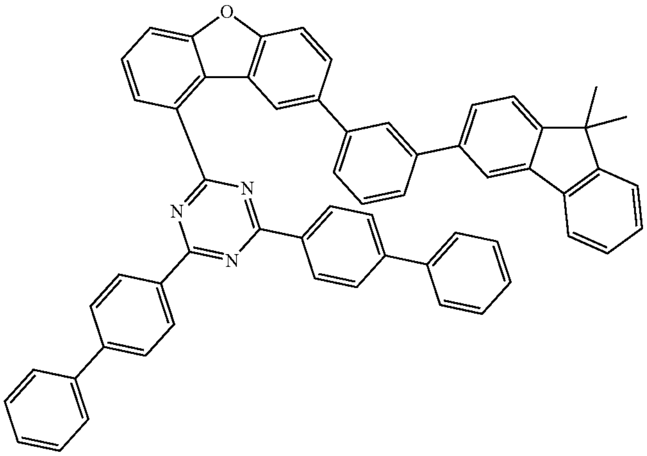 [SMILES: CC1(C)c2ccccc2-c2cc(-c3cccc(-c4ccc5oc6cccc(-c7nc(-c8ccc(-c9ccccc9)cc8)nc(-c8ccc(-c9ccccc9)cc8)n7)c6c5c4)c3)ccc21]

TABLE 1-continued
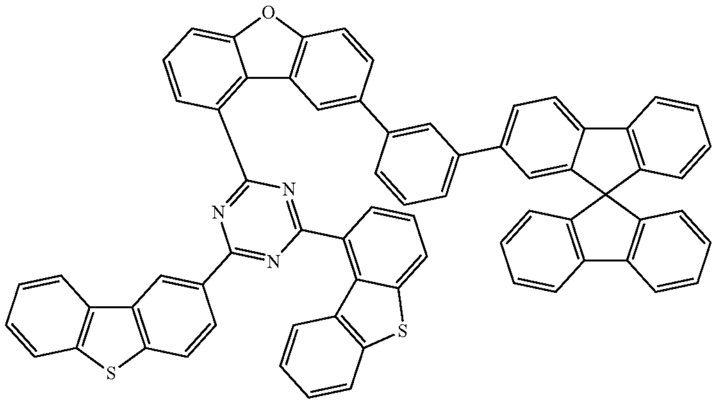 [SMILES: c1cc(-c2ccc3c(c2)C2(c4ccccc4-c4ccccc42)c2ccccc2-3)cc(-c2ccc3oc4cccc(-c5nc(-c6ccc7sc8ccccc8c7c6)nc(-c6cccc7sc8ccccc8c67)n5)c4c3c2)c1]
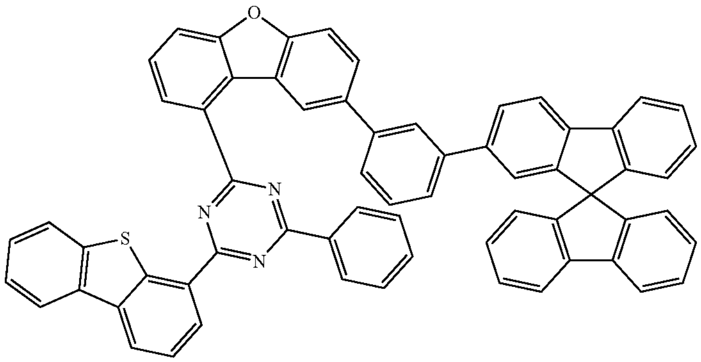 [SMILES: c1ccc(-c2nc(-c3cccc4c3sc3ccccc34)nc(-c3cccc4oc5ccc(-c6cccc(-c7ccc8c(c7)C7(c9ccccc9-c9ccccc97)c7ccccc7-8)c6)cc5c34)n2)cc1]
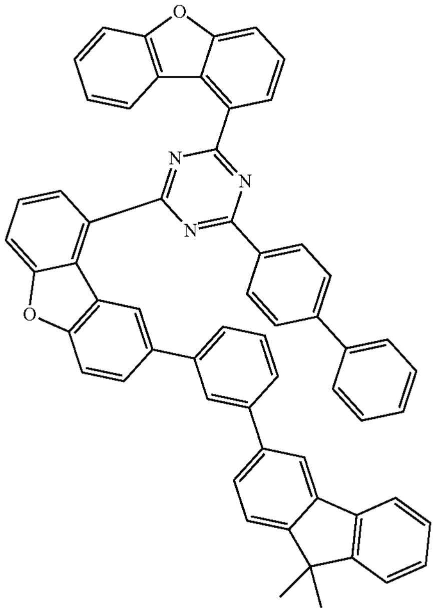 [SMILES: CC1(C)c2ccccc2-c2cc(-c3cccc(-c4ccc5oc6cccc(-c7nc(-c8ccc(-c9ccccc9)cc8)nc(-c8cccc9oc%10ccccc%10c89)n7)c6c5c4)c3)ccc21]

TABLE 1-continued
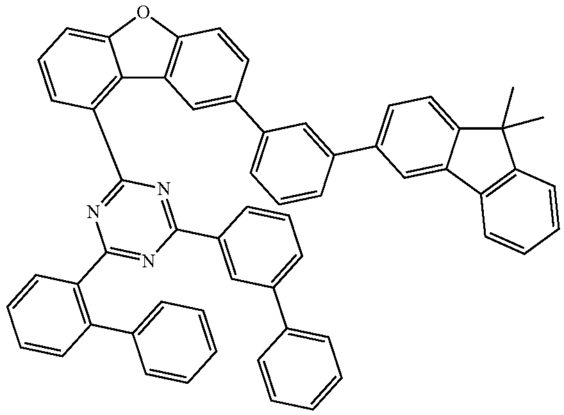 [SMILES: CC1(C)c2ccccc2-c2cc(-c3cccc(-c4ccc5oc6cccc(-c7nc(-c8cccc(-c9ccccc9)c8)nc(-c8ccccc8-c8ccccc8)n7)c6c5c4)c3)ccc21]
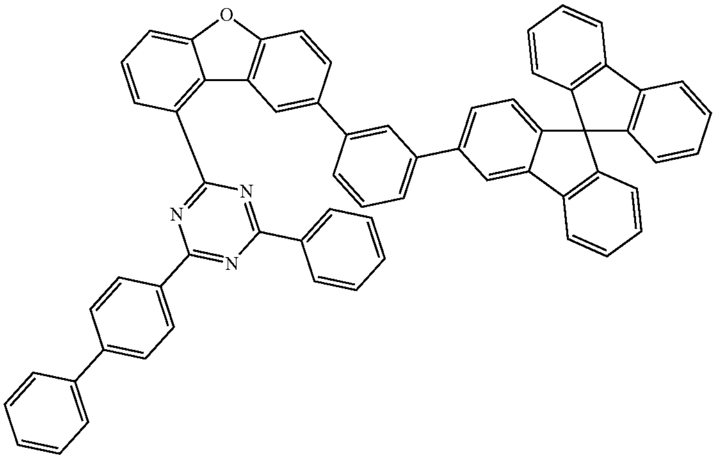 [SMILES: c1ccc(-c2ccc(-c3nc(-c4ccccc4)nc(-c4cccc5oc6ccc(-c7cccc(-c8ccc9c(c8)-c8ccccc8C98c9ccccc9-c9ccccc98)c7)cc6c45)n3)cc2)cc1]
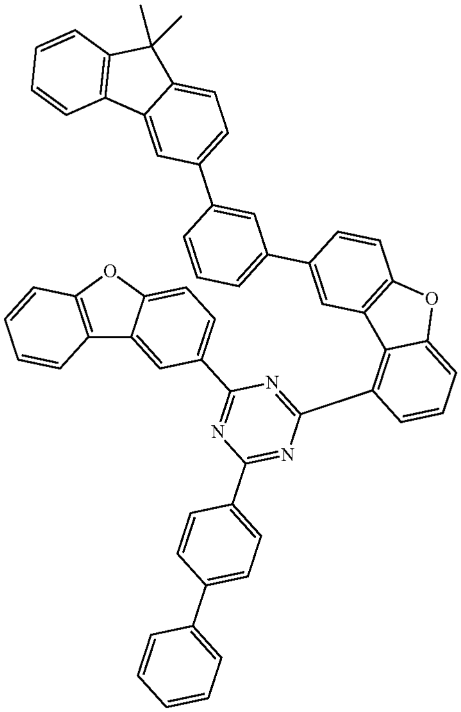 [SMILES: CC1(C)c2ccccc2-c2cc(-c3cccc(-c4ccc5oc6cccc(-c7nc(-c8ccc(-c9ccccc9)cc8)nc(-c8ccc9oc%10ccccc%10c9c8)n7)c6c5c4)c3)ccc21]

TABLE 1-continued
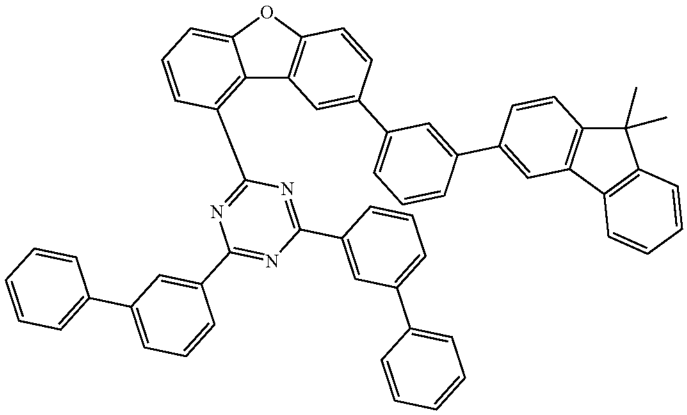 [SMILES: CC1(C)c2ccccc2-c2cc(-c3cccc(-c4ccc5oc6cccc(-c7nc(-c8cccc(-c9ccccc9)c8)nc(-c8cccc(-c9ccccc9)c8)n7)c6c5c4)c3)ccc21]
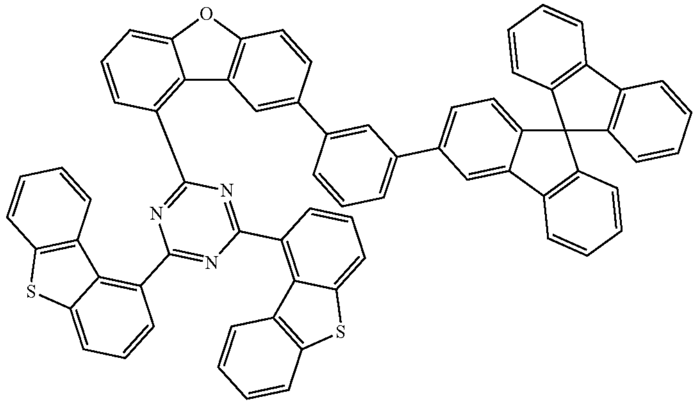 [SMILES: c1cc(-c2ccc3c(c2)-c2ccccc2C32c3ccccc3-c3ccccc32)cc(-c2ccc3oc4cccc(-c5nc(-c6cccc7sc8ccccc8c67)nc(-c6cccc7sc8ccccc8c67)n5)c4c3c2)c1]
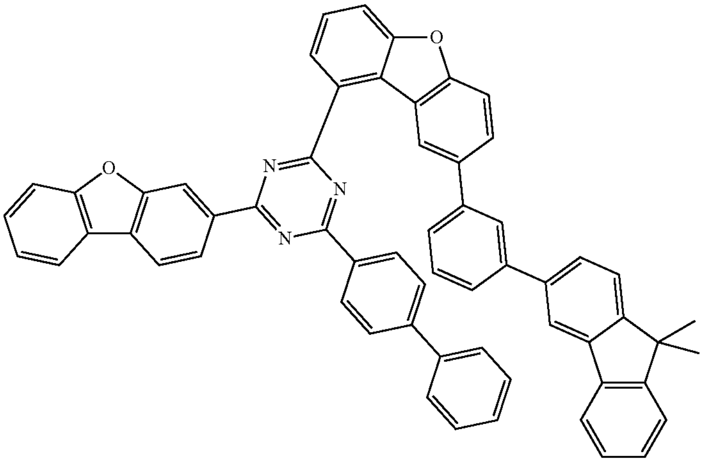 [SMILES: CC1(C)c2ccccc2-c2cc(-c3cccc(-c4ccc5oc6cccc(-c7nc(-c8ccc(-c9ccccc9)cc8)nc(-c8ccc9c(c8)oc8ccccc89)n7)c6c5c4)c3)ccc21]

TABLE 1-continued
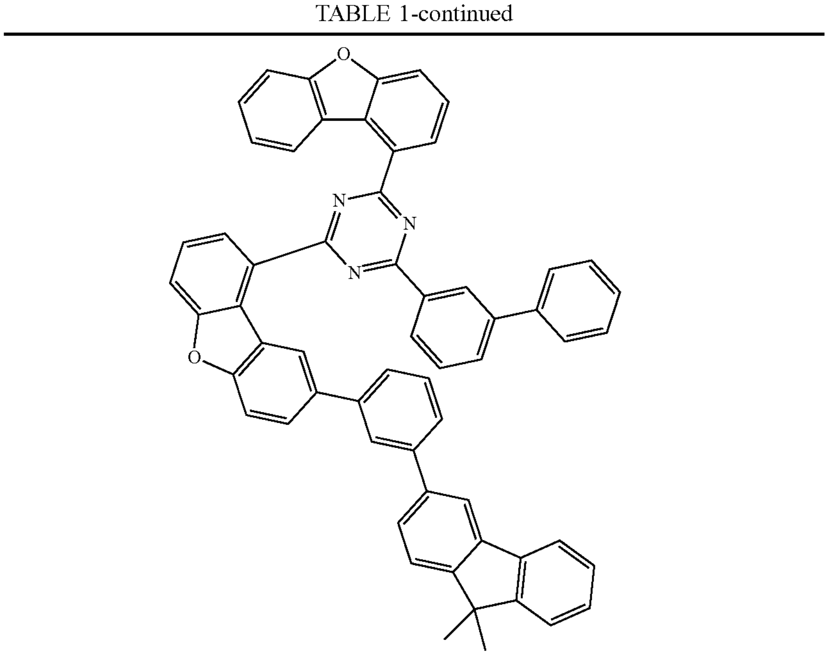
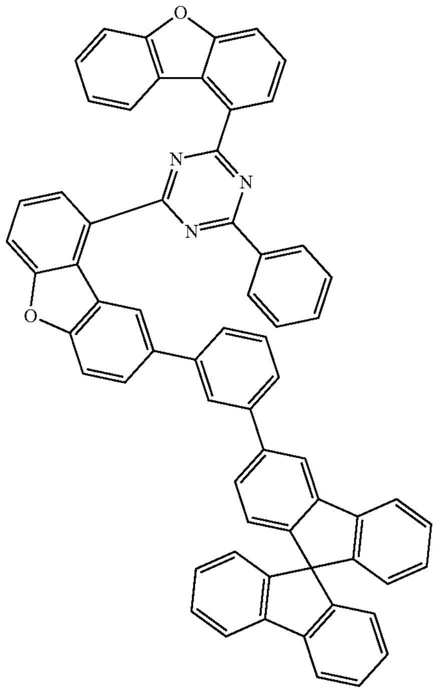 [SMILES: c1ccc(-c2nc(-c3cccc4oc5ccccc5c34)nc(-c3cccc4oc5ccc(-c6cccc(-c7ccc8c(c7)-c7ccccc7C87c8ccccc8-c8ccccc87)c6)cc5c34)n2)cc1]

TABLE 1-continued
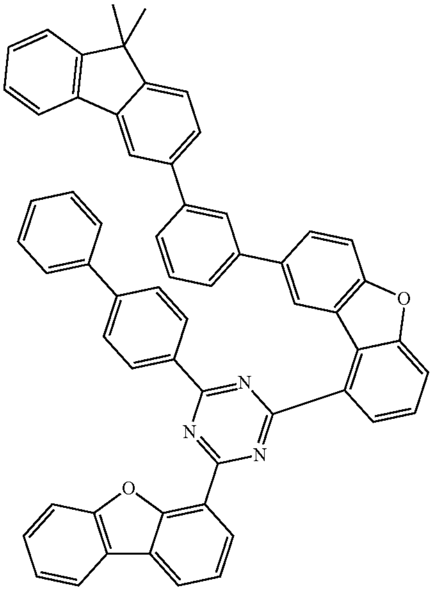 [SMILES: CC1(C)c2ccccc2-c2cc(-c3cccc(-c4ccc5oc6cccc(-c7nc(-c8ccc(-c9ccccc9)cc8)nc(-c8cccc9c8oc8ccccc89)n7)c6c5c4)c3)ccc21]
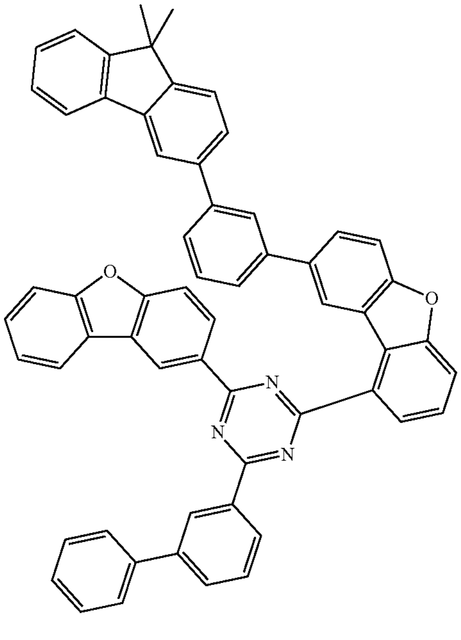 [SMILES: CC1(C)c2ccccc2-c2cc(-c3cccc(-c4ccc5oc6cccc(-c7nc(-c8cccc(-c9ccccc9)c8)nc(-c8ccc9oc%10ccccc%10c9c8)n7)c6c5c4)c3)ccc21]

TABLE 1-continued
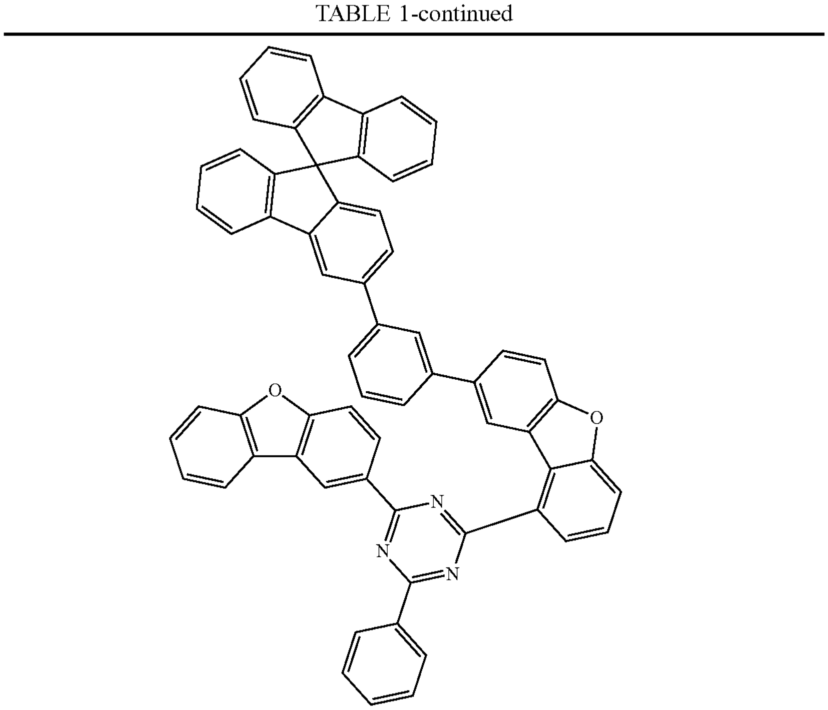
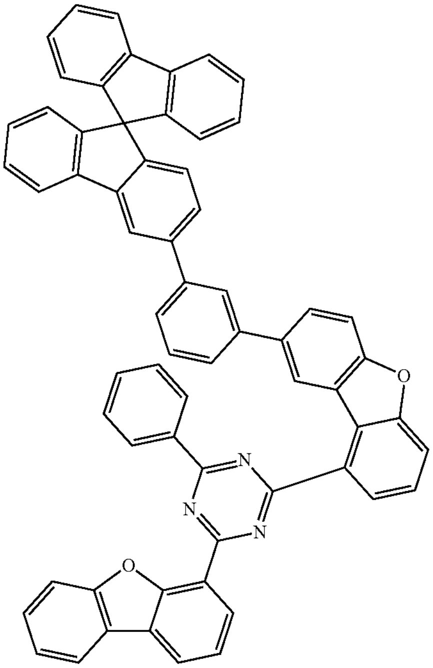 [SMILES: c1ccc(-c2nc(-c3cccc4c3oc3ccccc34)nc(-c3cccc4oc5ccc(-c6cccc(-c7ccc8c(c7)-c7ccccc7C87c8ccccc8-c8ccccc87)c6)cc5c34)n2)cc1]

TABLE 1-continued
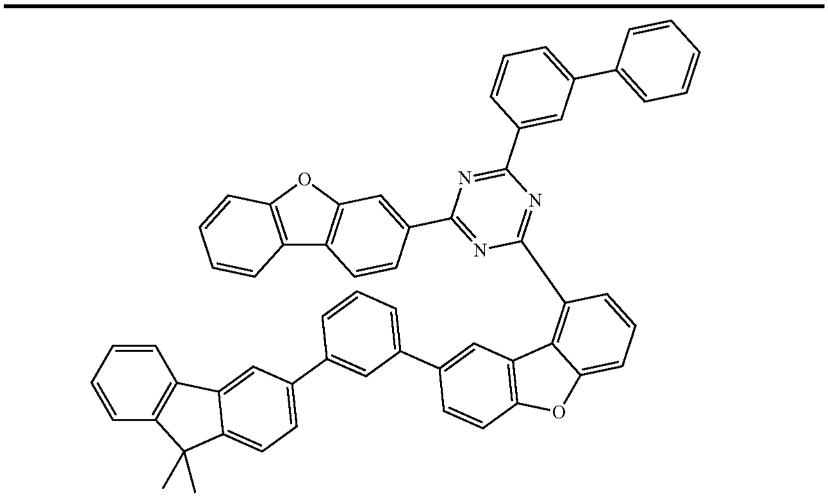
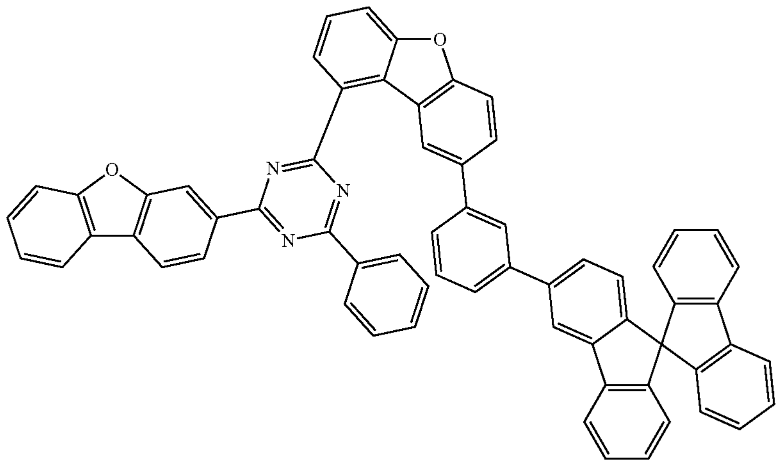 [SMILES: c1ccc(-c2nc(-c3ccc4c(c3)oc3ccccc34)nc(-c3cccc4oc5ccc(-c6cccc(-c7ccc8c(c7)-c7ccccc7C87c8ccccc8-c8ccccc87)c6)cc5c34)n2)cc1]
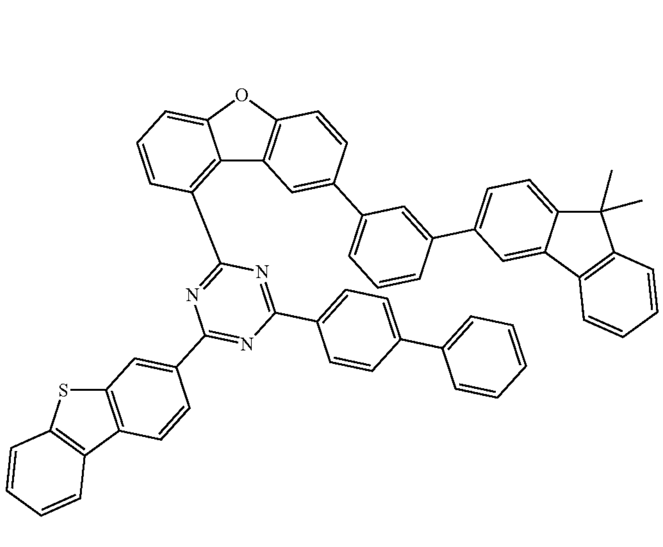 [SMILES: CC1(C)c2ccccc2-c2cc(-c3cccc(-c4ccc5oc6cccc(-c7nc(-c8ccc(-c9ccccc9)cc8)nc(-c8ccc9c(c8)sc8ccccc89)n7)c6c5c4)c3)ccc21]

TABLE 1-continued
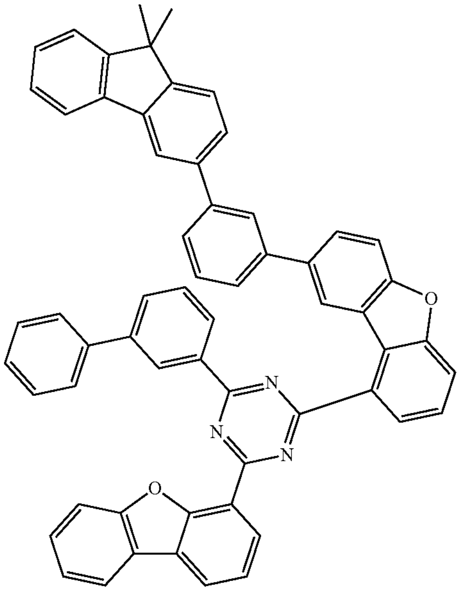 [SMILES: CC1(C)c2ccccc2-c2cc(-c3cccc(-c4ccc5oc6cccc(-c7nc(-c8cccc(-c9ccccc9)c8)nc(-c8cccc9c8oc8ccccc89)n7)c6c5c4)c3)ccc21]
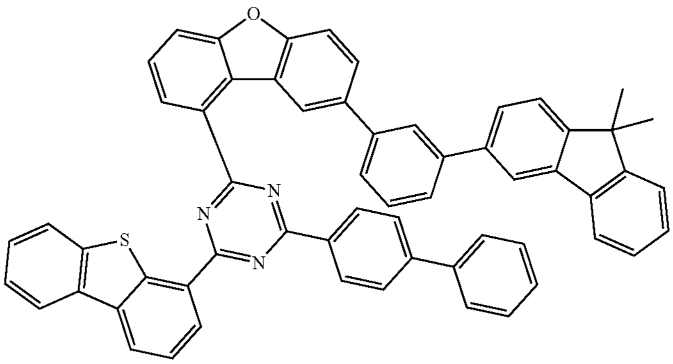 [SMILES: CC1(C)c2ccccc2-c2cc(-c3cccc(-c4ccc5oc6cccc(-c7nc(-c8ccc(-c9ccccc9)cc8)nc(-c8cccc9c8sc8ccccc89)n7)c6c5c4)c3)ccc21]
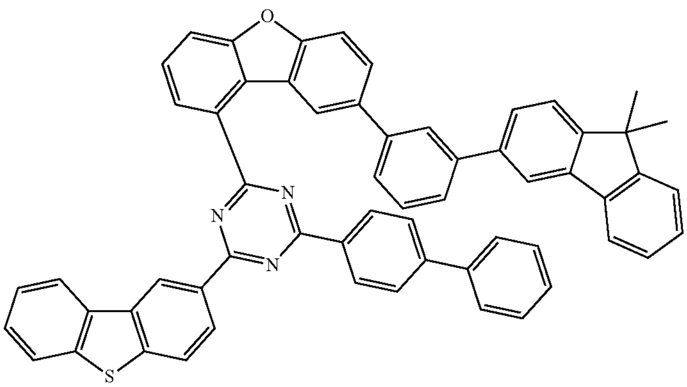 [SMILES: CC1(C)c2ccccc2-c2cc(-c3cccc(-c4ccc5oc6cccc(-c7nc(-c8ccc(-c9ccccc9)cc8)nc(-c8ccc9sc%10ccccc%10c9c8)n7)c6c5c4)c3)ccc21]

TABLE 1-continued
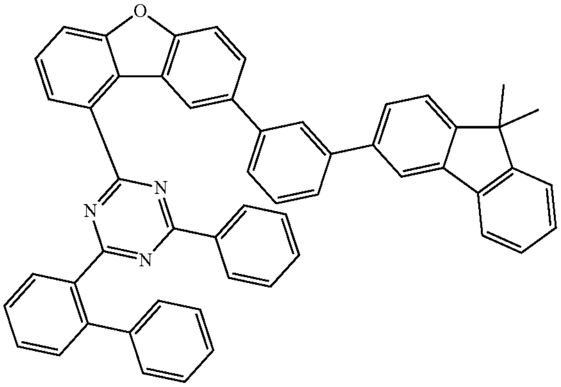 [SMILES: CC1(C)c2ccccc2-c2cc(-c3cccc(-c4ccc5oc6cccc(-c7nc(-c8ccccc8)nc(-c8ccccc8-c8ccccc8)n7)c6c5c4)c3)ccc21]
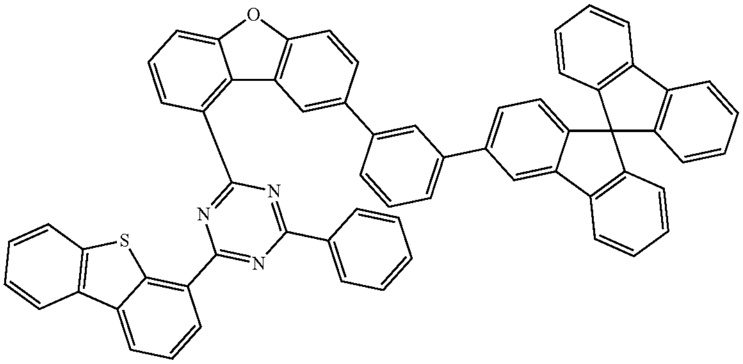 [SMILES: c1ccc(-c2nc(-c3cccc4c3sc3ccccc34)nc(-c3cccc4oc5ccc(-c6cccc(-c7ccc8c(c7)-c7ccccc7C87c8ccccc8-c8ccccc87)c6)cc5c34)n2)cc1]
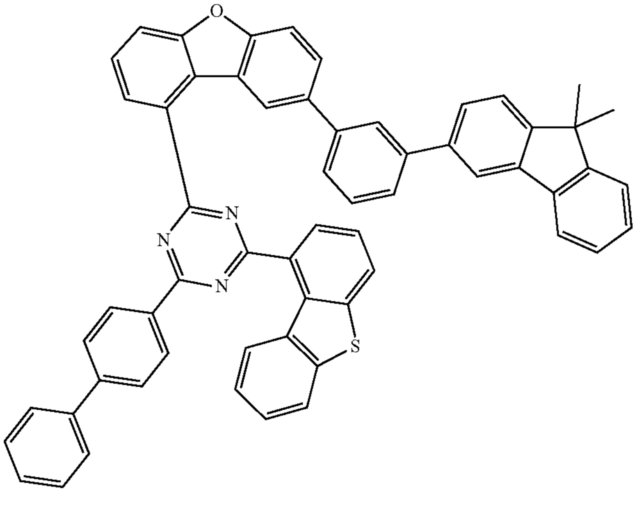 [SMILES: CC1(C)c2ccccc2-c2cc(-c3cccc(-c4ccc5oc6cccc(-c7nc(-c8ccc(-c9ccccc9)cc8)nc(-c8cccc9sc%10ccccc%10c89)n7)c6c5c4)c3)ccc21]

TABLE 1-continued
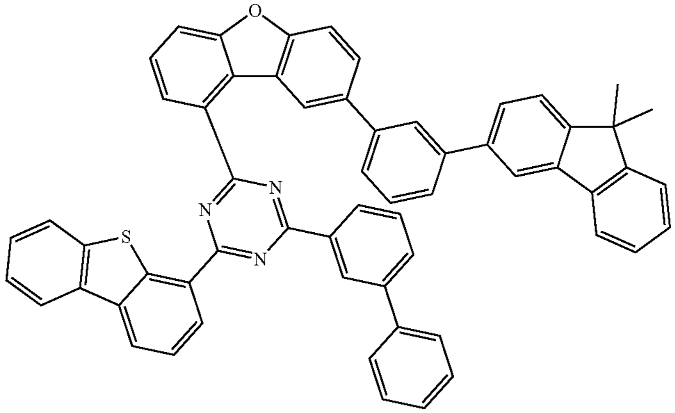 [SMILES: CC1(C)c2ccccc2-c2cc(-c3cccc(-c4ccc5oc6cccc(-c7nc(-c8cccc(-c9ccccc9)c8)nc(-c8cccc9c8sc8ccccc89)n7)c6c5c4)c3)ccc21]
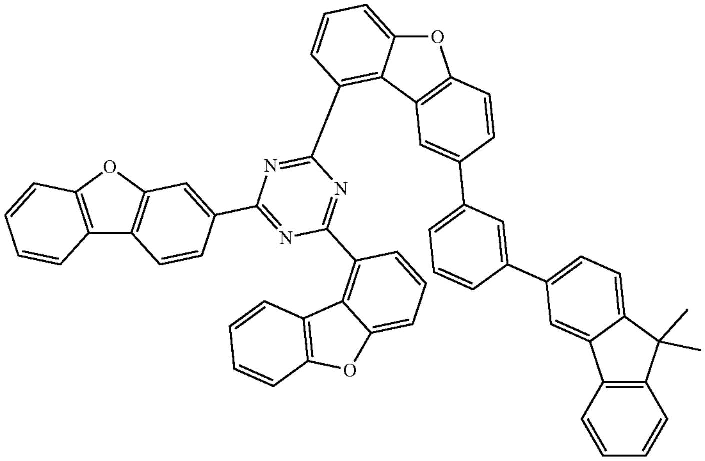 [SMILES: CC1(C)c2ccccc2-c2cc(-c3cccc(-c4ccc5oc6cccc(-c7nc(-c8ccc9c(c8)oc8ccccc89)nc(-c8cccc9oc%10ccccc%10c89)n7)c6c5c4)c3)ccc21]
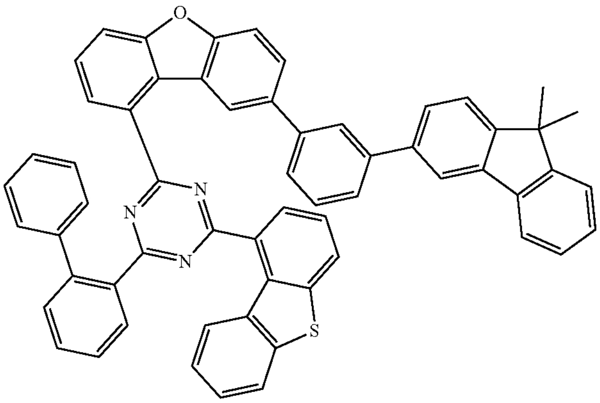 [SMILES: CC1(C)c2ccccc2-c2cc(-c3cccc(-c4ccc5oc6cccc(-c7nc(-c8ccccc8-c8ccccc8)nc(-c8cccc9sc%10ccccc%10c89)n7)c6c5c4)c3)ccc21]

TABLE 1-continued
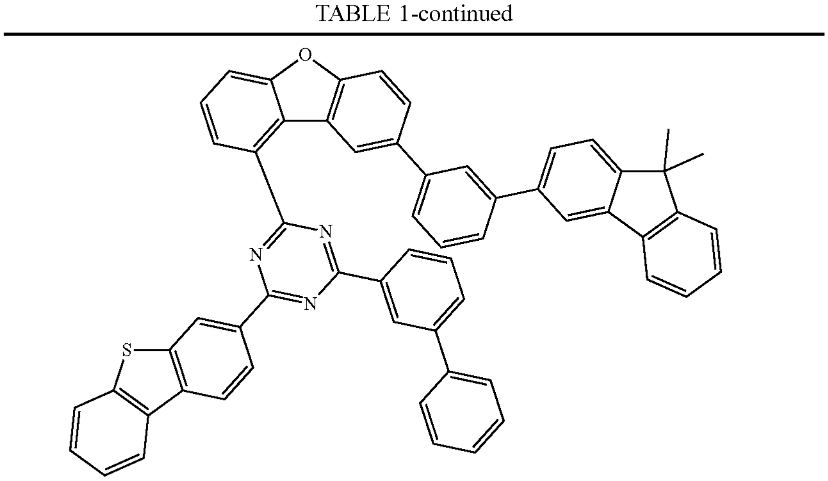
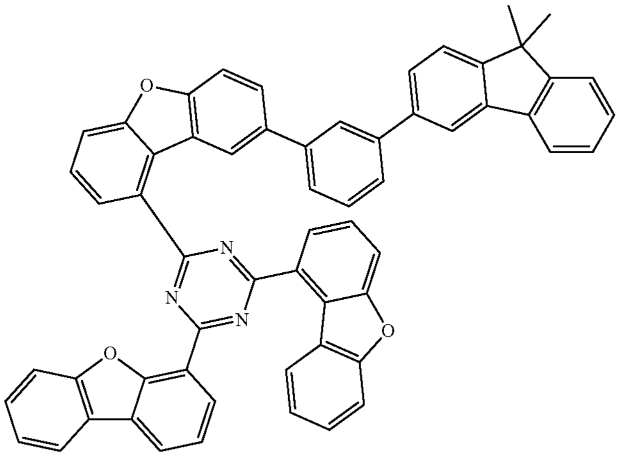 [SMILES: CC1(C)c2ccccc2-c2cc(-c3cccc(-c4ccc5oc6cccc(-c7nc(-c8cccc9c8oc8ccccc89)nc(-c8cccc9oc%10ccccc%10c89)n7)c6c5c4)c3)ccc21]
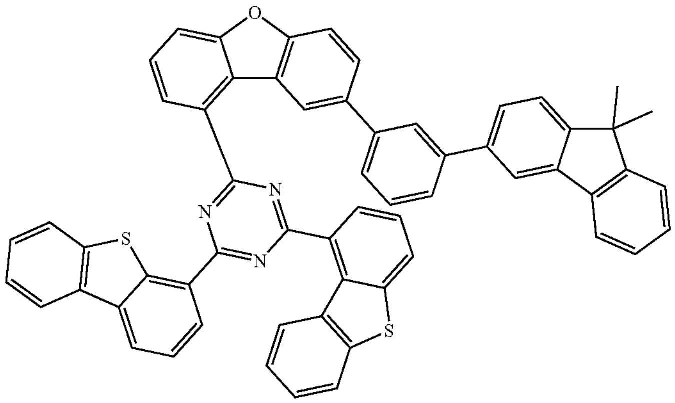 [SMILES: CC1(C)c2ccccc2-c2cc(-c3cccc(-c4ccc5oc6cccc(-c7nc(-c8cccc9c8sc8ccccc89)nc(-c8cccc9sc%10ccccc%10c89)n7)c6c5c4)c3)ccc21]

TABLE 1-continued
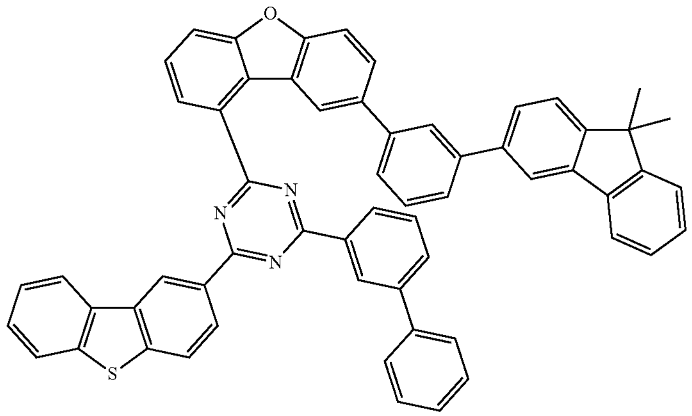 [SMILES: CC1(C)c2ccccc2-c2cc(-c3cccc(-c4ccc5oc6cccc(-c7nc(-c8cccc(-c9ccccc9)c8)nc(-c8ccc9sc%10ccccc%10c9c8)n7)c6c5c4)c3)ccc21]
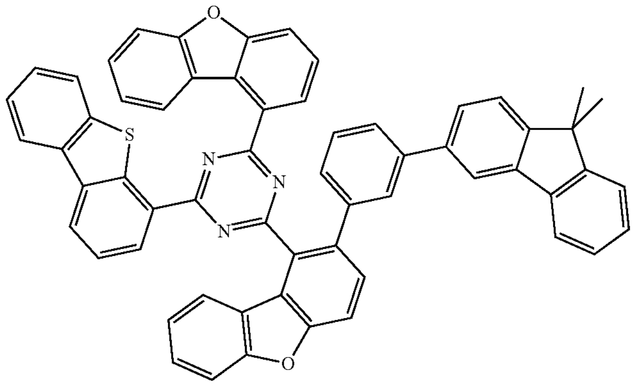 [SMILES: CC1(C)c2ccccc2-c2cc(-c3cccc(-c4ccc5oc6ccccc6c5c4-c4nc(-c5cccc6c5sc5ccccc56)nc(-c5cccc6oc7ccccc7c56)n4)c3)ccc21]
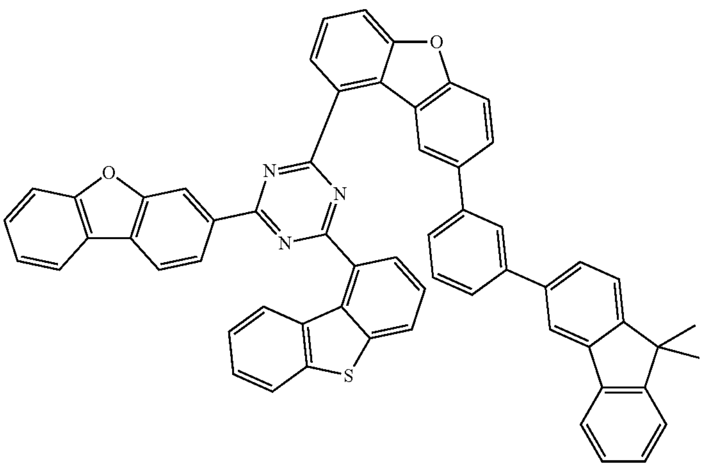 [SMILES: CC1(C)c2ccccc2-c2cc(-c3cccc(-c4ccc5oc6cccc(-c7nc(-c8ccc9c(c8)oc8ccccc89)nc(-c8cccc9sc%10ccccc%10c89)n7)c6c5c4)c3)ccc21]

TABLE 1-continued
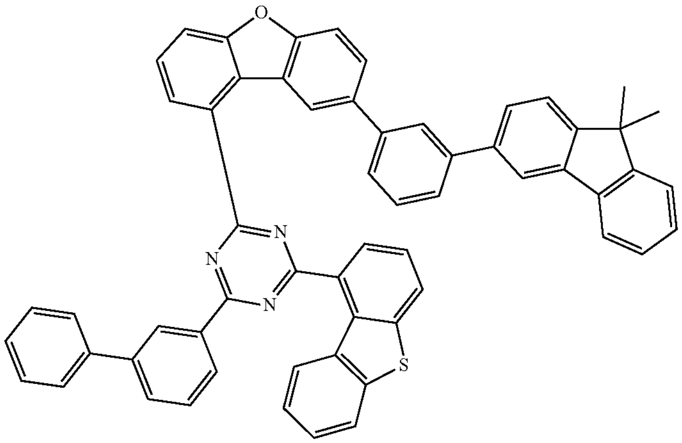 [SMILES: CC1(C)c2ccccc2-c2cc(-c3cccc(-c4ccc5oc6cccc(-c7nc(-c8cccc(-c9ccccc9)c8)nc(-c8cccc9sc%10ccccc%10c89)n7)c6c5c4)c3)ccc21]
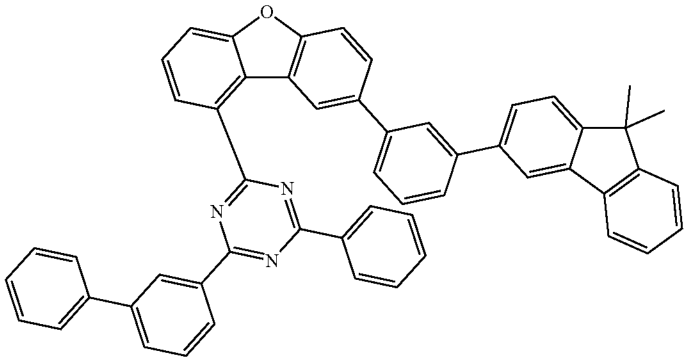 [SMILES: CC1(C)c2ccccc2-c2cc(-c3cccc(-c4ccc5oc6cccc(-c7nc(-c8ccccc8)nc(-c8cccc(-c9ccccc9)c8)n7)c6c5c4)c3)ccc21]
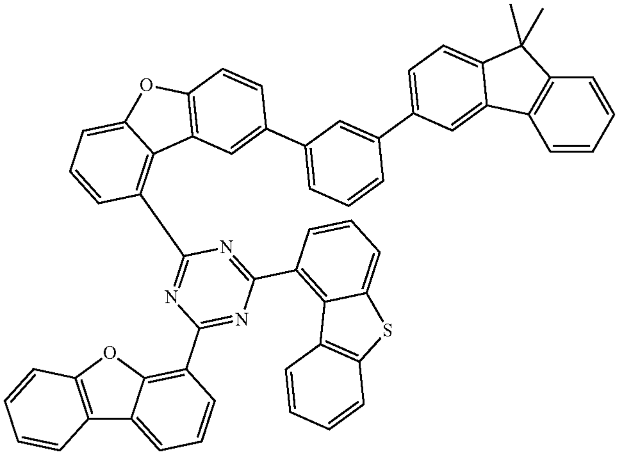 [SMILES: CC1(C)c2ccccc2-c2cc(-c3cccc(-c4ccc5oc6cccc(-c7nc(-c8cccc9c8oc8ccccc89)nc(-c8cccc9sc%10ccccc%10c89)n7)c6c5c4)c3)ccc21]

TABLE 1-continued
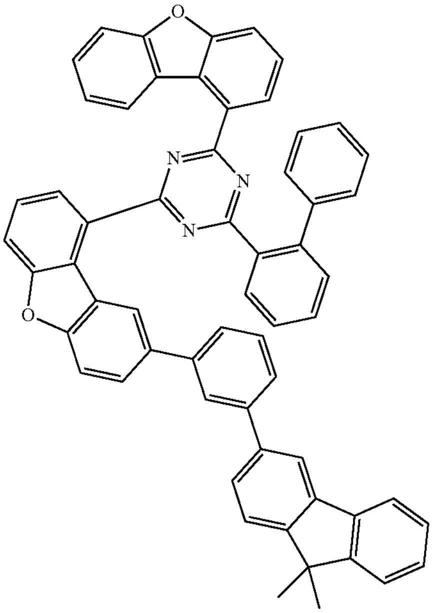 [SMILES: CC1(C)c2ccccc2-c2cc(-c3cccc(-c4ccc5oc6cccc(-c7nc(-c8ccccc8-c8ccccc8)nc(-c8cccc9oc%10ccccc%10c89)n7)c6c5c4)c3)ccc21]
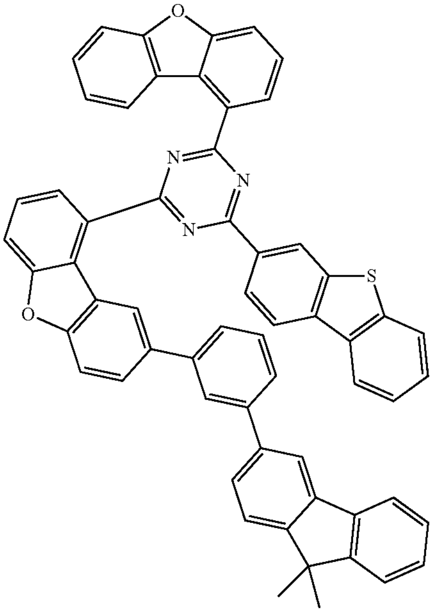 [SMILES: CC1(C)c2ccccc2-c2cc(-c3cccc(-c4ccc5oc6cccc(-c7nc(-c8ccc9c(c8)sc8ccccc89)nc(-c8cccc9oc%10ccccc%10c89)n7)c6c5c4)c3)ccc21]

TABLE 1-continued
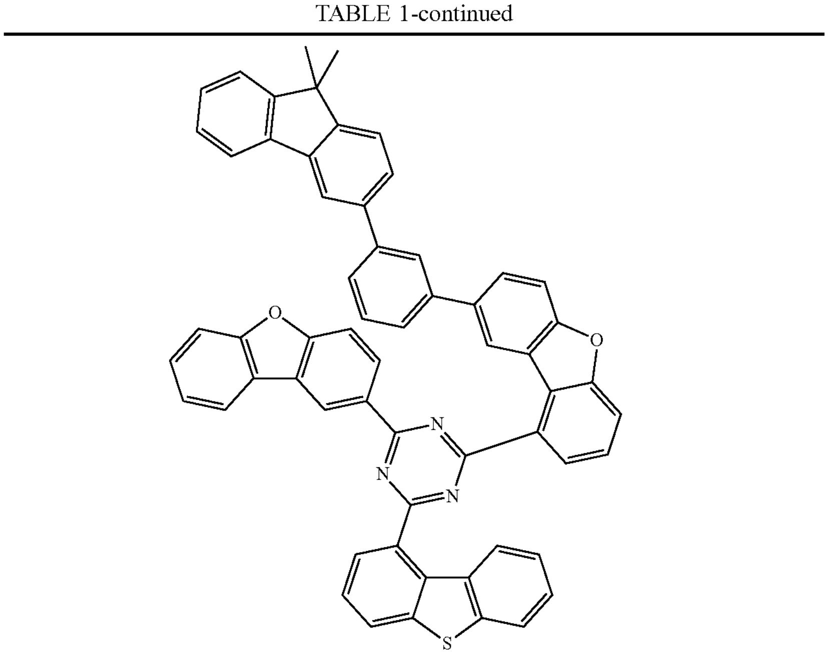
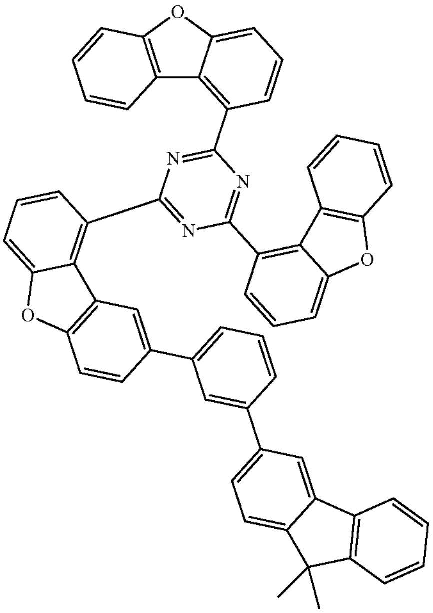 [SMILES: CC1(C)c2ccccc2-c2cc(-c3cccc(-c4ccc5oc6cccc(-c7nc(-c8cccc9oc%10ccccc%10c89)nc(-c8cccc9oc%10ccccc%10c89)n7)c6c5c4)c3)ccc21]

TABLE 1-continued
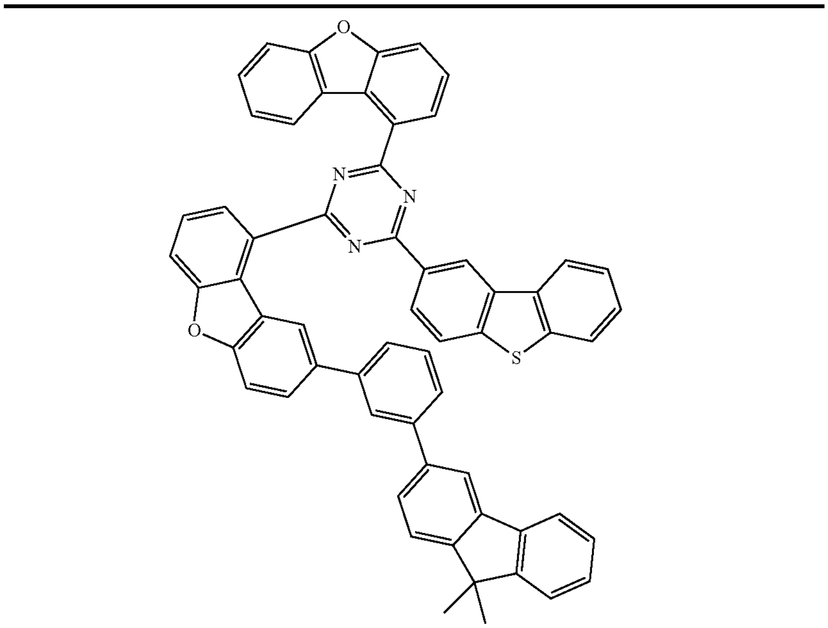
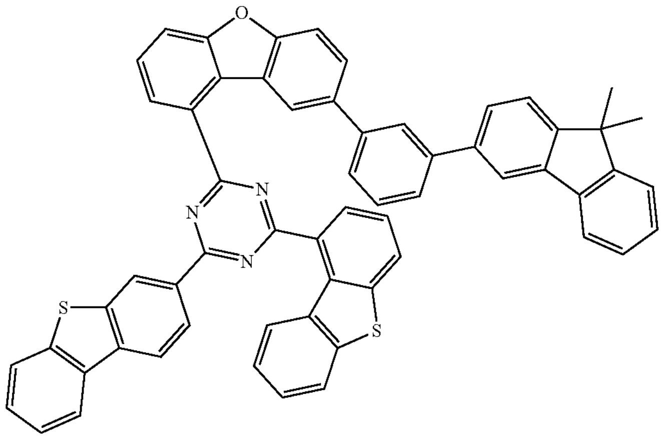 [SMILES: CC1(C)c2ccccc2-c2cc(-c3cccc(-c4ccc5oc6cccc(-c7nc(-c8ccc9c(c8)sc8ccccc89)nc(-c8cccc9sc%10ccccc%10c89)n7)c6c5c4)c3)ccc21]
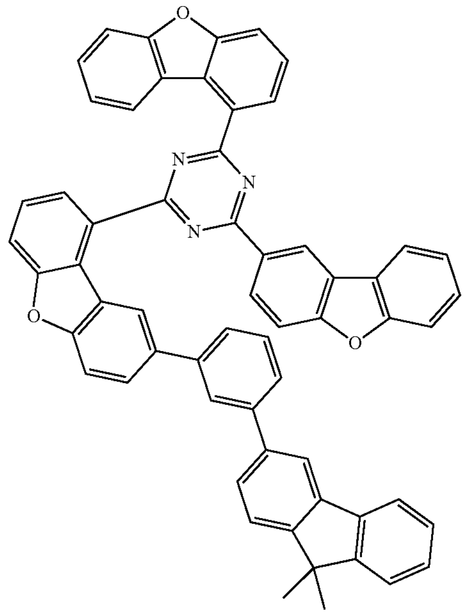 [SMILES: CC1(C)c2ccccc2-c2cc(-c3cccc(-c4ccc5oc6cccc(-c7nc(-c8ccc9oc%10ccccc%10c9c8)nc(-c8cccc9oc%10ccccc%10c89)n7)c6c5c4)c3)ccc21]

TABLE 1-continued
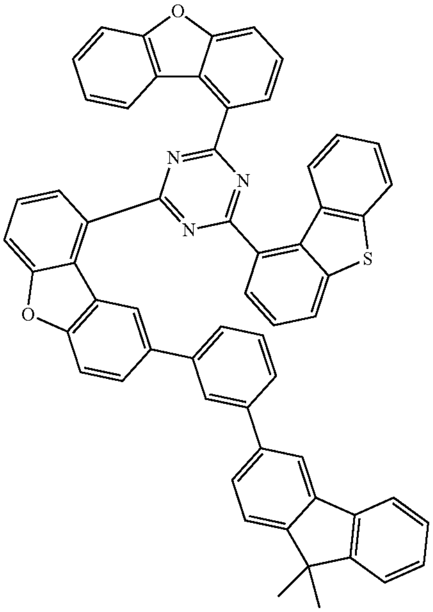 [SMILES: CC1(C)c2ccccc2-c2cc(-c3cccc(-c4ccc5oc6cccc(-c7nc(-c8cccc9oc%10ccccc%10c89)nc(-c8cccc9sc%10ccccc%10c89)n7)c6c5c4)c3)ccc21]
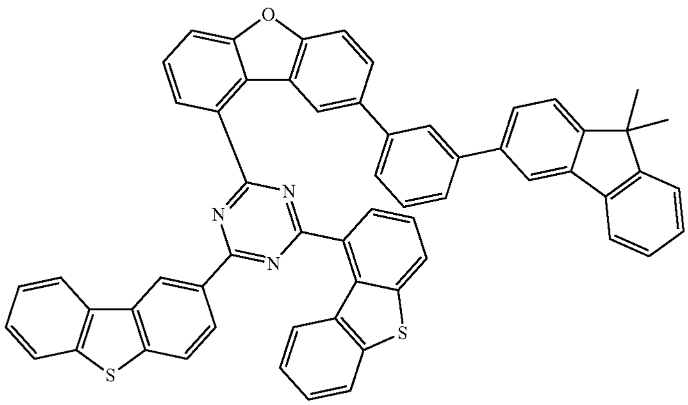 [SMILES: CC1(C)c2ccccc2-c2cc(-c3cccc(-c4ccc5oc6cccc(-c7nc(-c8ccc9sc%10ccccc%10c9c8)nc(-c8cccc9sc%10ccccc%10c89)n7)c6c5c4)c3)ccc21]
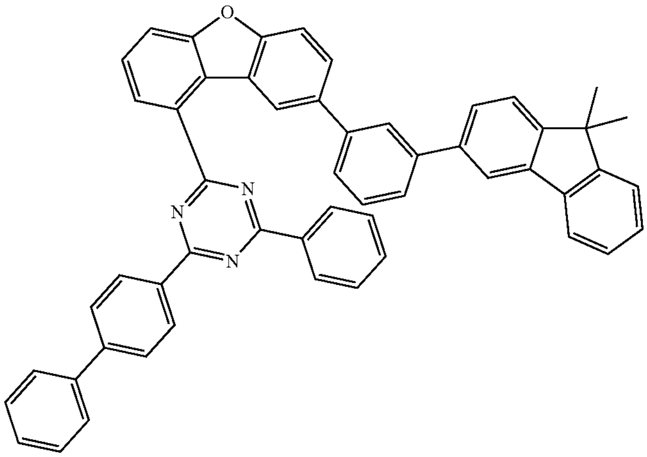 [SMILES: CC1(C)c2ccccc2-c2cc(-c3cccc(-c4ccc5oc6cccc(-c7nc(-c8ccccc8)nc(-c8ccc(-c9ccccc9)cc8)n7)c6c5c4)c3)ccc21]

TABLE 1-continued
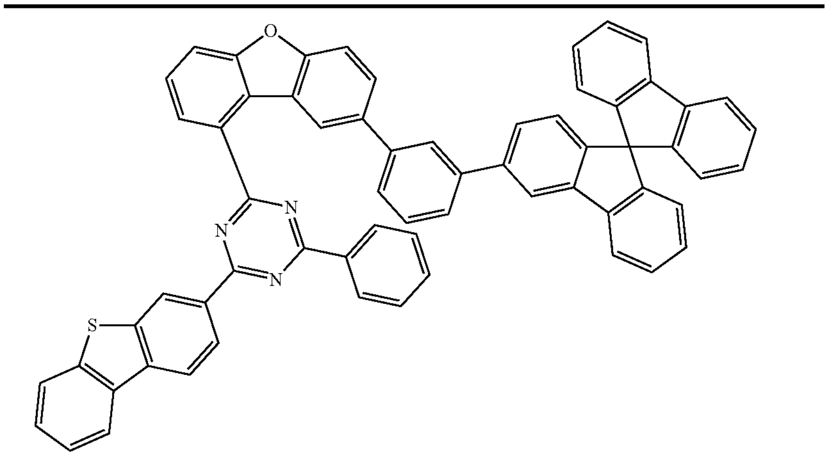
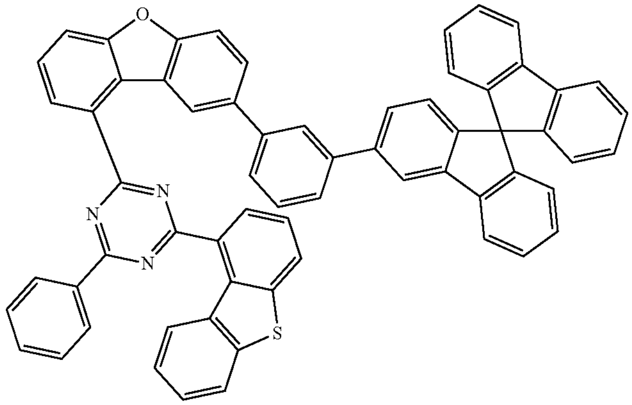 [SMILES: c1ccc(-c2nc(-c3cccc4oc5ccc(-c6cccc(-c7ccc8c(c7)-c7ccccc7C87c8ccccc8-c8ccccc87)c6)cc5c34)nc(-c3cccc4sc5ccccc5c34)n2)cc1]
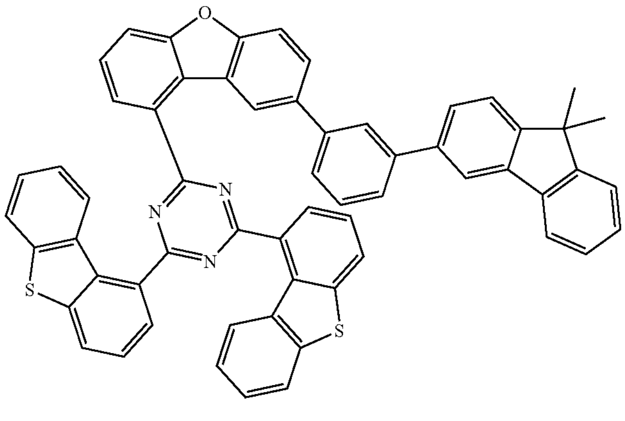 [SMILES: CC1(C)c2ccccc2-c2cc(-c3cccc(-c4ccc5oc6cccc(-c7nc(-c8cccc9sc%10ccccc%10c89)nc(-c8cccc9sc%10ccccc%10c89)n7)c6c5c4)c3)ccc21]
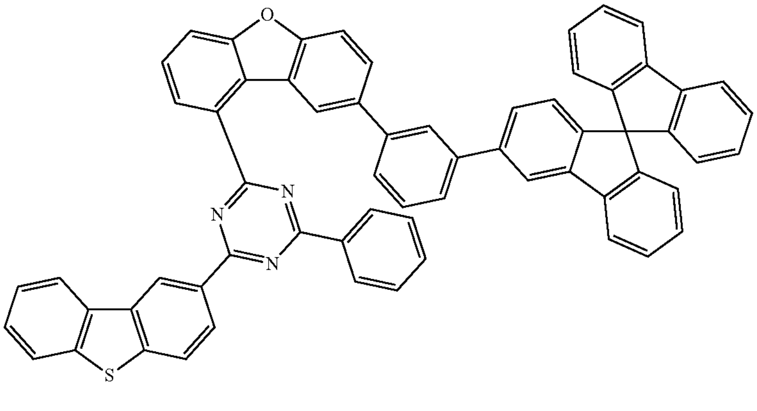 [SMILES: c1ccc(-c2nc(-c3ccc4sc5ccccc5c4c3)nc(-c3cccc4oc5ccc(-c6cccc(-c7ccc8c(c7)-c7ccccc7C87c8ccccc8-c8ccccc87)c6)cc5c34)n2)cc1]

TABLE 1-continued
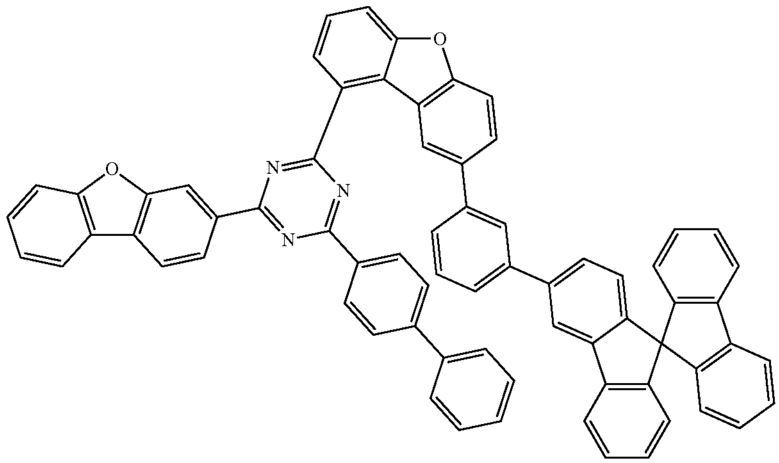 [SMILES: c1ccc(-c2ccc(-c3nc(-c4ccc5c(c4)oc4ccccc45)nc(-c4cccc5oc6ccc(-c7cccc(-c8ccc9c(c8)-c8ccccc8C98c9ccccc9-c9ccccc98)c7)cc6c45)n3)cc2)cc1]
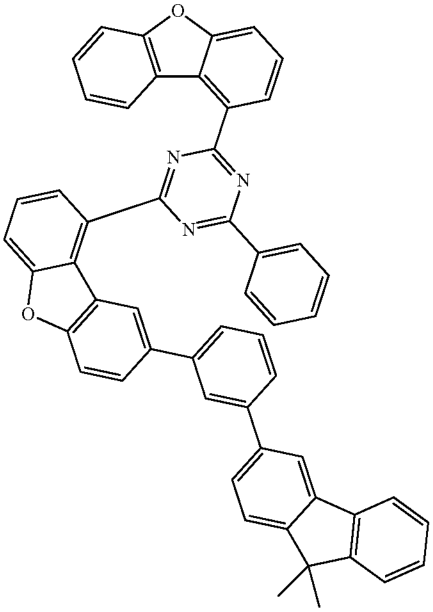 [SMILES: CC1(C)c2ccccc2-c2cc(-c3cccc(-c4ccc5oc6cccc(-c7nc(-c8ccccc8)nc(-c8cccc9oc%10ccccc%10c89)n7)c6c5c4)c3)ccc21]

TABLE 1-continued
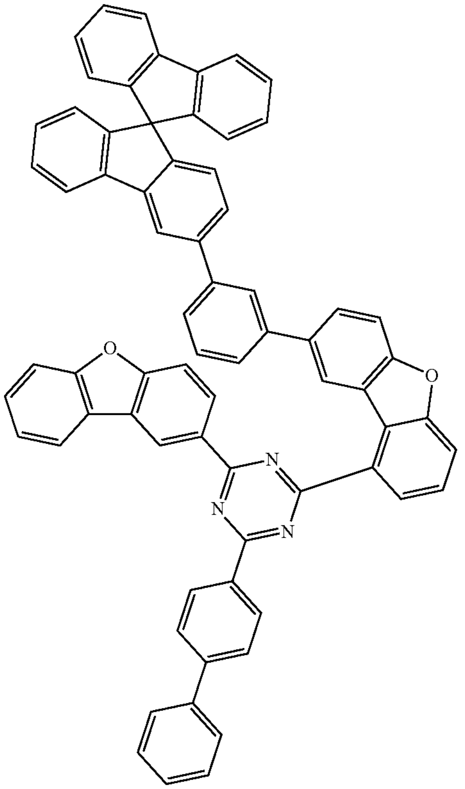 [SMILES: c1ccc(-c2ccc(-c3nc(-c4ccc5oc6ccccc6c5c4)nc(-c4cccc5oc6ccc(-c7cccc(-c8ccc9c(c8)-c8ccccc8C98c9ccccc9-c9ccccc98)c7)cc6c45)n3)cc2)cc1]
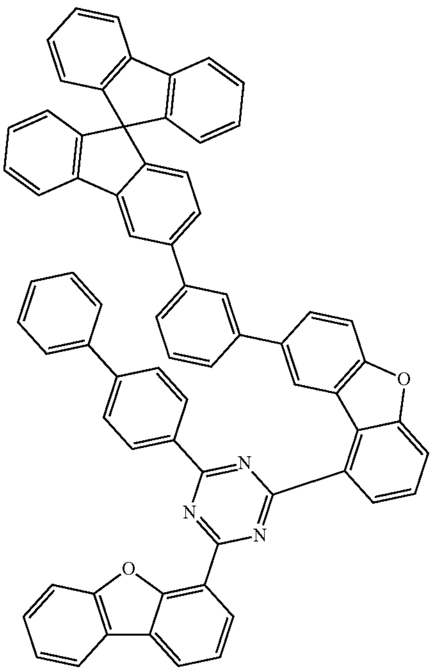 [SMILES: c1ccc(-c2ccc(-c3nc(-c4cccc5c4oc4ccccc45)nc(-c4cccc5oc6ccc(-c7cccc(-c8ccc9c(c8)-c8ccccc8C98c9ccccc9-c9ccccc98)c7)cc6c45)n3)cc2)cc1]

TABLE 1-continued
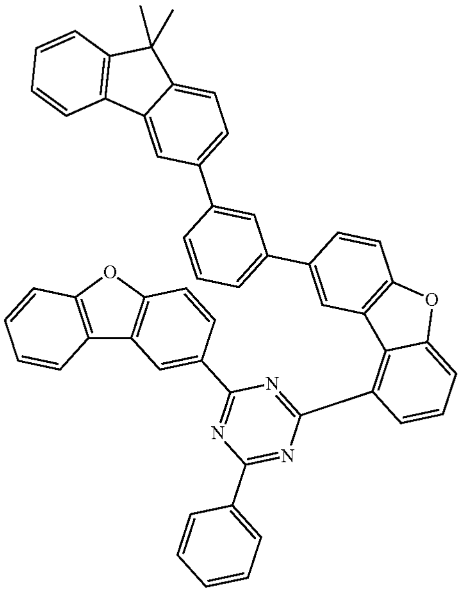 [SMILES: CC1(C)c2ccccc2-c2cc(-c3cccc(-c4ccc5oc6cccc(-c7nc(-c8ccccc8)nc(-c8ccc9oc%10ccccc%10c9c8)n7)c6c5c4)c3)ccc21]
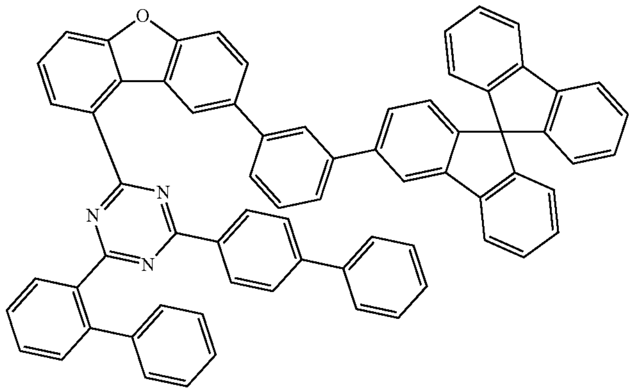 [SMILES: c1ccc(-c2ccc(-c3nc(-c4ccccc4-c4ccccc4)nc(-c4cccc5oc6ccc(-c7cccc(-c8ccc9c(c8)-c8ccccc8C98c9ccccc9-c9ccccc98)c7)cc6c45)n3)cc2)cc1]
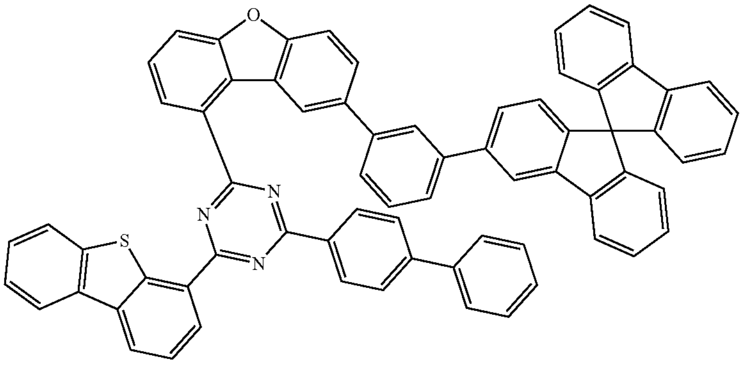 [SMILES: c1ccc(-c2ccc(-c3nc(-c4cccc5c4sc4ccccc45)nc(-c4cccc5oc6ccc(-c7cccc(-c8ccc9c(c8)-c8ccccc8C98c9ccccc9-c9ccccc98)c7)cc6c45)n3)cc2)cc1]

TABLE 1-continued
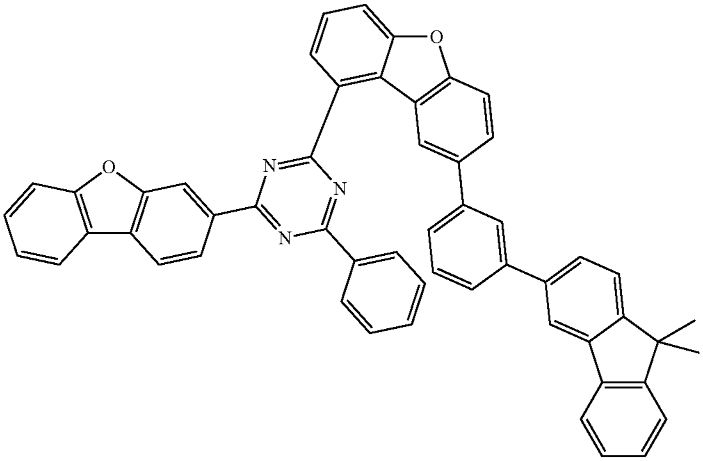 [SMILES: CC1(C)c2ccccc2-c2cc(-c3cccc(-c4ccc5oc6cccc(-c7nc(-c8ccccc8)nc(-c8ccc9c(c8)oc8ccccc89)n7)c6c5c4)c3)ccc21]
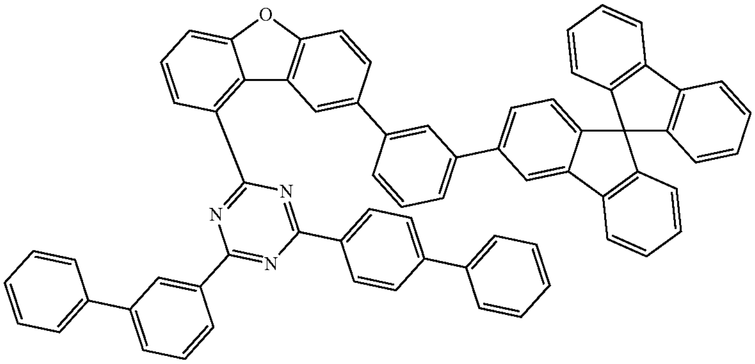 [SMILES: c1ccc(-c2ccc(-c3nc(-c4cccc(-c5ccccc5)c4)nc(-c4cccc5oc6ccc(-c7cccc(-c8ccc9c(c8)-c8ccccc8C98c9ccccc9-c9ccccc98)c7)cc6c45)n3)cc2)cc1]
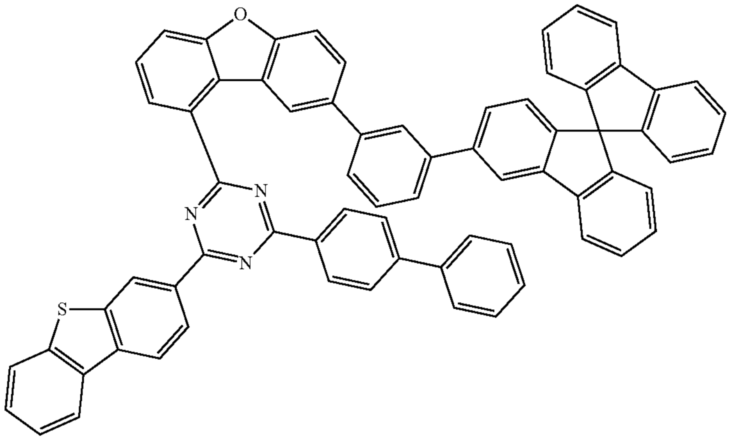 [SMILES: c1ccc(-c2ccc(-c3nc(-c4ccc5c(c4)sc4ccccc45)nc(-c4cccc5oc6ccc(-c7cccc(-c8ccc9c(c8)-c8ccccc8C98c9ccccc9-c9ccccc98)c7)cc6c45)n3)cc2)cc1]

TABLE 1-continued
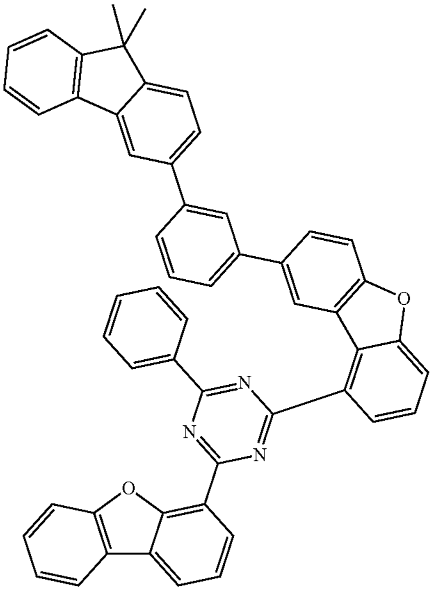 [SMILES: CC1(C)c2ccccc2-c2cc(-c3cccc(-c4ccc5oc6cccc(-c7nc(-c8ccccc8)nc(-c8cccc9c8oc8ccccc89)n7)c6c5c4)c3)ccc21]
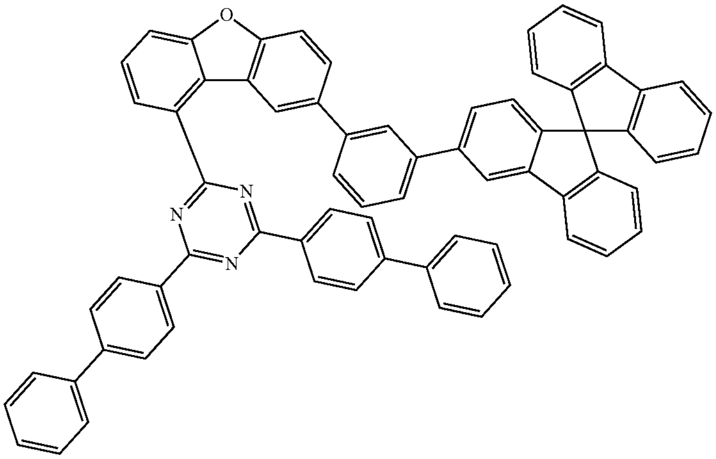 [SMILES: c1ccc(-c2ccc(-c3nc(-c4ccc(-c5ccccc5)cc4)nc(-c4cccc5oc6ccc(-c7cccc(-c8ccc9c(c8)-c8ccccc8C98c9ccccc9-c9ccccc98)c7)cc6c45)n3)cc2)cc1]
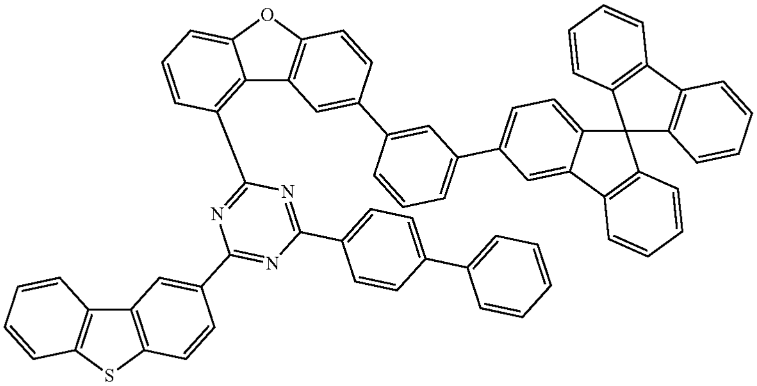 [SMILES: c1ccc(-c2ccc(-c3nc(-c4ccc5sc6ccccc6c5c4)nc(-c4cccc5oc6ccc(-c7cccc(-c8ccc9c(c8)-c8ccccc8C98c9ccccc9-c9ccccc98)c7)cc6c45)n3)cc2)cc1]

TABLE 1-continued
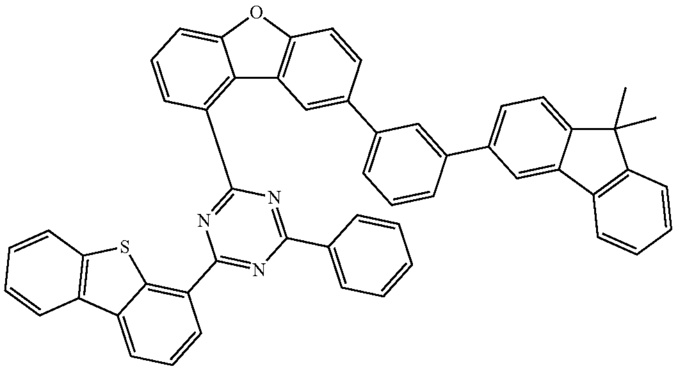 [SMILES: CC1(C)c2ccccc2-c2cc(-c3cccc(-c4ccc5oc6cccc(-c7nc(-c8ccccc8)nc(-c8cccc9c8sc8ccccc89)n7)c6c5c4)c3)ccc21]
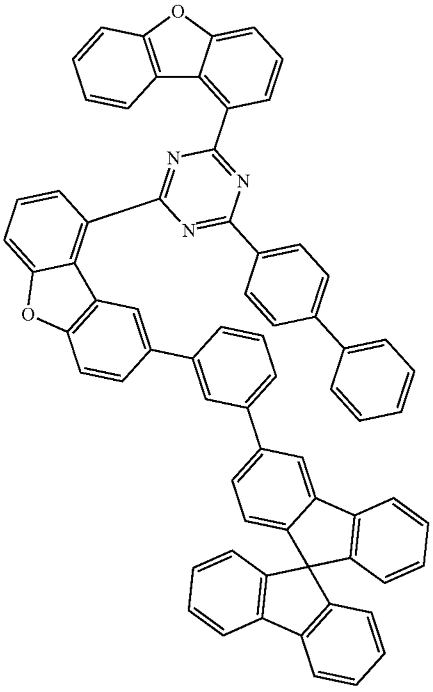 [SMILES: c1ccc(-c2ccc(-c3nc(-c4cccc5oc6ccccc6c45)nc(-c4cccc5oc6ccc(-c7cccc(-c8ccc9c(c8)-c8ccccc8C98c9ccccc9-c9ccccc98)c7)cc6c45)n3)cc2)cc1]

TABLE 1-continued
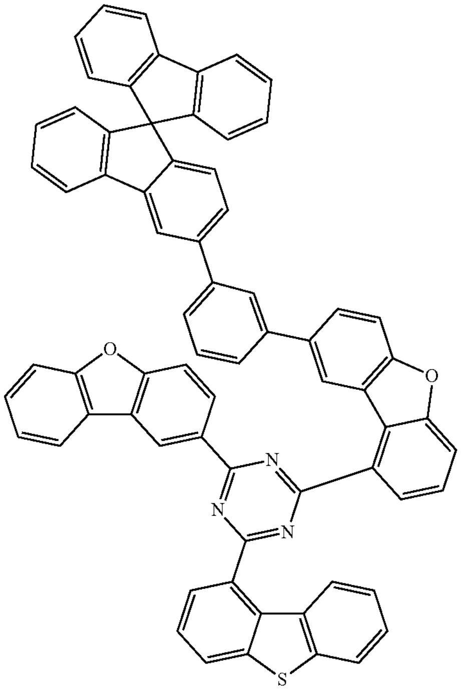 [SMILES: c1cc(-c2ccc3c(c2)-c2ccccc2C32c3ccccc3-c3ccccc32)cc(-c2ccc3oc4cccc(-c5nc(-c6ccc7oc8ccccc8c7c6)nc(-c6cccc7sc8ccccc8c67)n5)c4c3c2)c1]
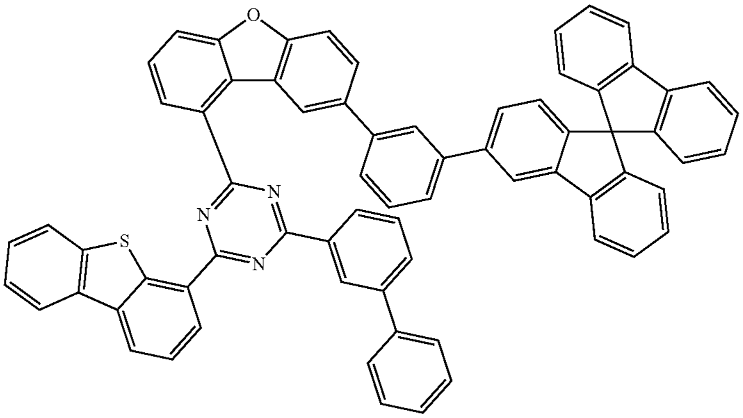 [SMILES: c1ccc(-c2cccc(-c3nc(-c4cccc5c4sc4ccccc45)nc(-c4cccc5oc6ccc(-c7cccc(-c8ccc9c(c8)-c8ccccc8C98c9ccccc9-c9ccccc98)c7)cc6c45)n3)c2)cc1]
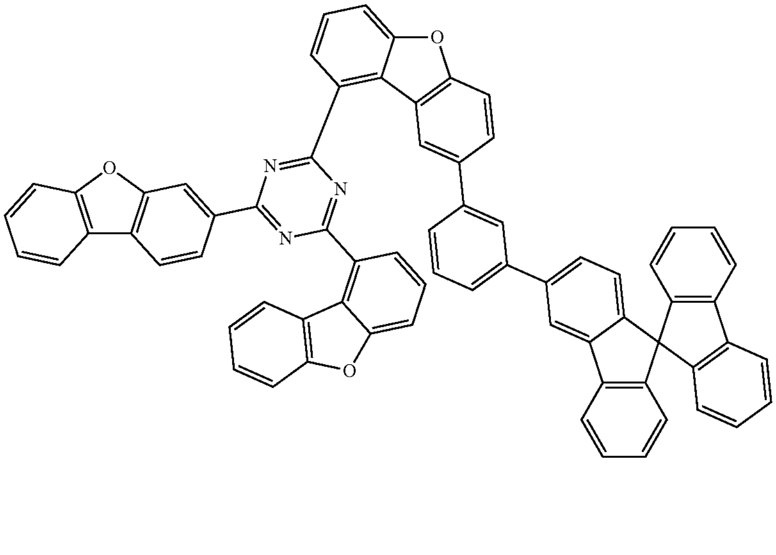 [SMILES: c1cc(-c2ccc3c(c2)-c2ccccc2C32c3ccccc3-c3ccccc32)cc(-c2ccc3oc4cccc(-c5nc(-c6ccc7c(c6)oc6ccccc67)nc(-c6cccc7oc8ccccc8c67)n5)c4c3c2)c1]

TABLE 1-continued
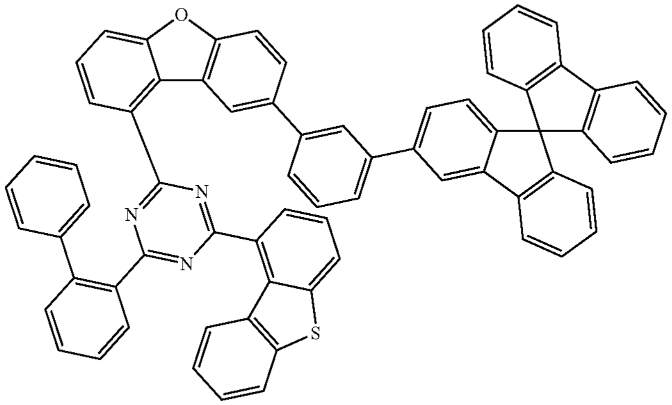 [SMILES: c1ccc(-c2ccccc2-c2nc(-c3cccc4oc5ccc(-c6cccc(-c7ccc8c(c7)-c7ccccc7C87c8ccccc8-c8ccccc87)c6)cc5c34)nc(-c3cccc4sc5ccccc5c34)n2)cc1]
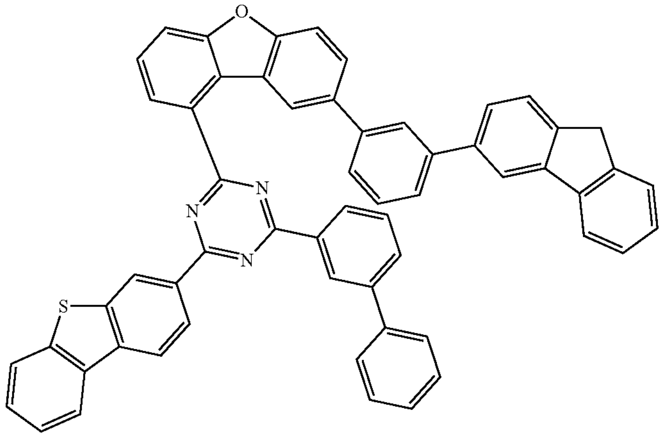 [SMILES: c1ccc(-c2cccc(-c3nc(-c4ccc5c(c4)sc4ccccc45)nc(-c4cccc5oc6ccc(-c7cccc(-c8ccc9c(c8)-c8ccccc8C9)c7)cc6c45)n3)c2)cc1]
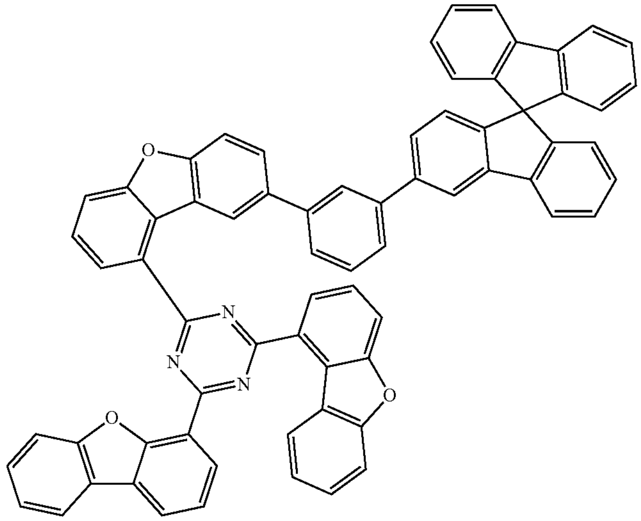 [SMILES: c1cc(-c2ccc3c(c2)-c2ccccc2C32c3ccccc3-c3ccccc32)cc(-c2ccc3oc4cccc(-c5nc(-c6cccc7c6oc6ccccc67)nc(-c6cccc7oc8ccccc8c67)n5)c4c3c2)c1]

TABLE 1-continued
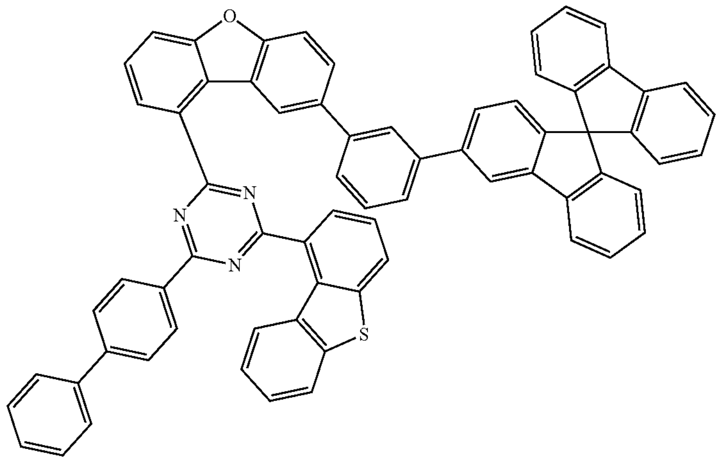 [SMILES: c1ccc(-c2ccc(-c3nc(-c4cccc5oc6ccc(-c7cccc(-c8ccc9c(c8)-c8ccccc8C98c9ccccc9-c9ccccc98)c7)cc6c45)nc(-c4cccc5sc6ccccc6c45)n3)cc2)cc1]
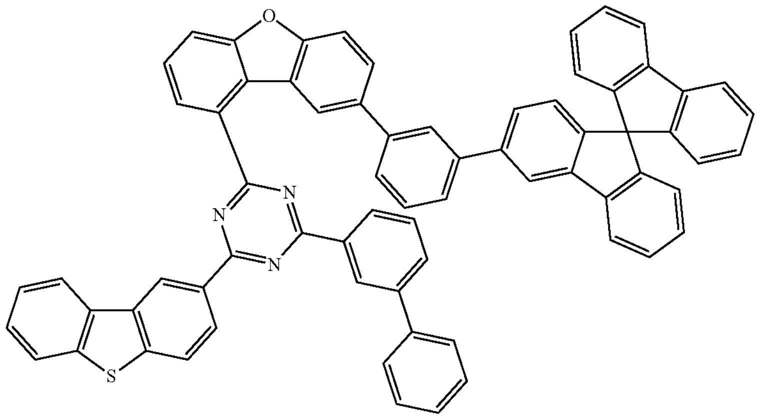 [SMILES: c1ccc(-c2cccc(-c3nc(-c4ccc5sc6ccccc6c5c4)nc(-c4cccc5oc6ccc(-c7cccc(-c8ccc9c(c8)-c8ccccc8C98c9ccccc9-c9ccccc98)c7)cc6c45)n3)c2)cc1]
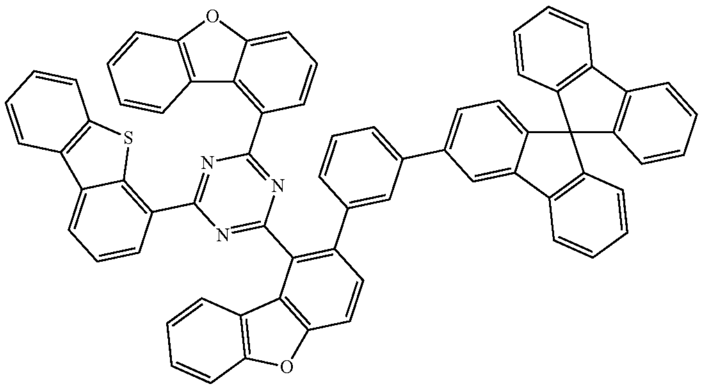 [SMILES: c1cc(-c2ccc3c(c2)-c2ccccc2C32c3ccccc3-c3ccccc32)cc(-c2ccc3oc4ccccc4c3c2-c2nc(-c3cccc4c3sc3ccccc34)nc(-c3cccc4oc5ccccc5c34)n2)c1]

TABLE 1-continued
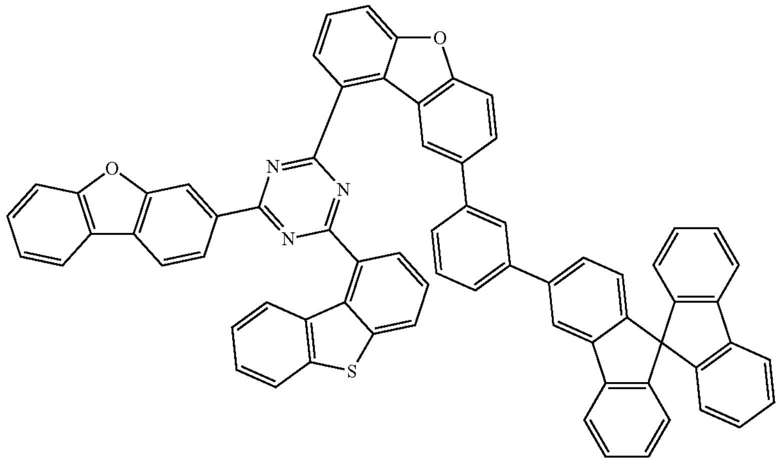
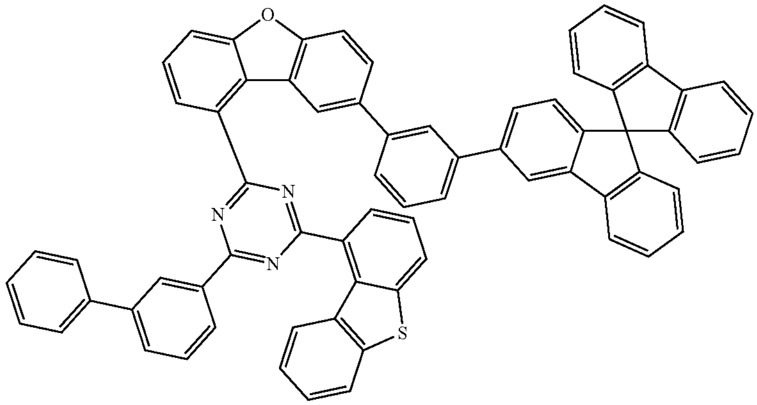 [SMILES: c1ccc(-c2cccc(-c3nc(-c4cccc5oc6ccc(-c7cccc(-c8ccc9c(c8)-c8ccccc8C98c9ccccc9-c9ccccc98)c7)cc6c45)nc(-c4cccc5sc6ccccc6c45)n3)c2)cc1]
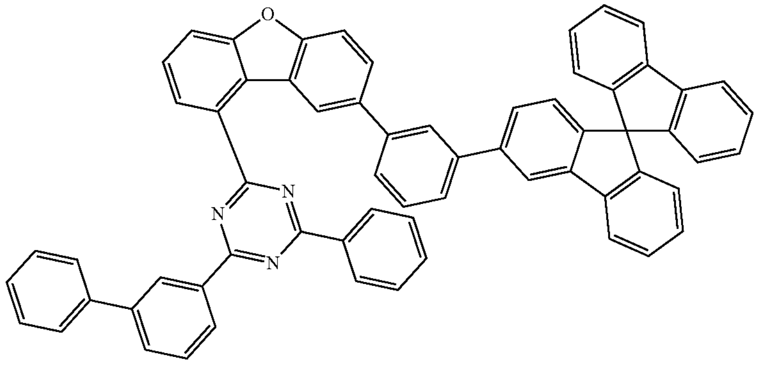 [SMILES: c1ccc(-c2cccc(-c3nc(-c4ccccc4)nc(-c4cccc5oc6ccc(-c7cccc(-c8ccc9c(c8)-c8ccccc8C98c9ccccc9-c9ccccc98)c7)cc6c45)n3)c2)cc1]

TABLE 1-continued
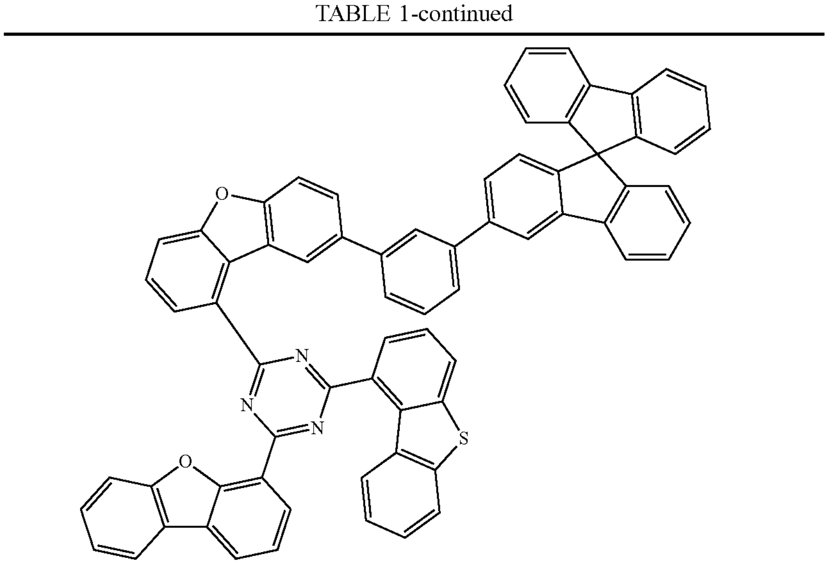
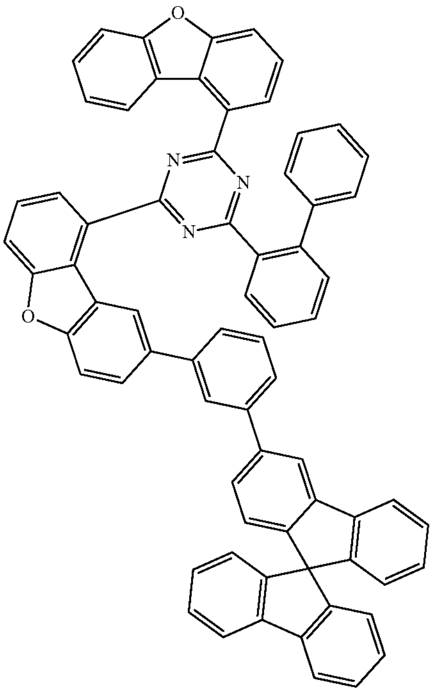 [SMILES: c1ccc(-c2ccccc2-c2nc(-c3cccc4oc5ccccc5c34)nc(-c3cccc4oc5ccc(-c6cccc(-c7ccc8c(c7)-c7ccccc7C87c8ccccc8-c8ccccc87)c6)cc5c34)n2)cc1]

TABLE 1-continued
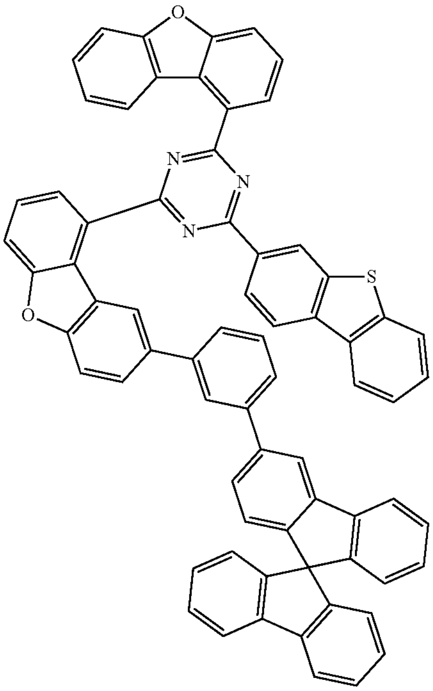 [SMILES: c1cc(-c2ccc3c(c2)-c2ccccc2C32c3ccccc3-c3ccccc32)cc(-c2ccc3oc4cccc(-c5nc(-c6ccc7c(c6)sc6ccccc67)nc(-c6cccc7oc8ccccc8c67)n5)c4c3c2)c1]
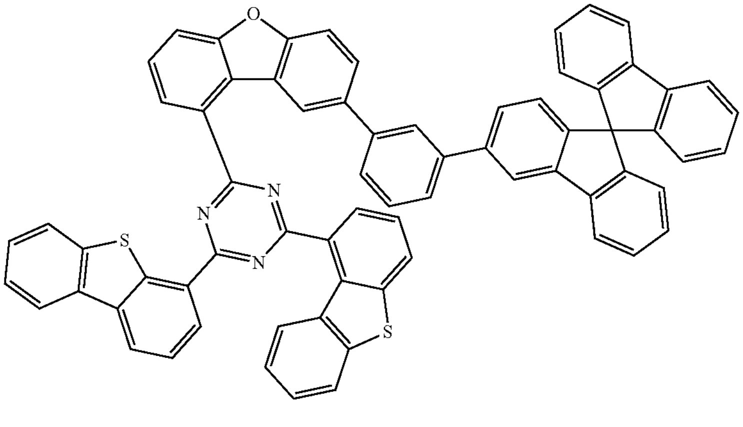 [SMILES: c1cc(-c2ccc3c(c2)-c2ccccc2C32c3ccccc3-c3ccccc32)cc(-c2ccc3oc4cccc(-c5nc(-c6cccc7c6sc6ccccc67)nc(-c6cccc7sc8ccccc8c67)n5)c4c3c2)c1]

TABLE 1-continued
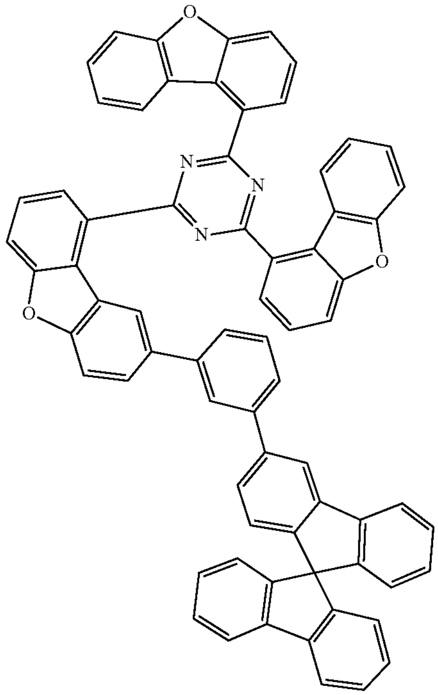 [SMILES: c1cc(-c2ccc3c(c2)-c2ccccc2C32c3ccccc3-c3ccccc32)cc(-c2ccc3oc4cccc(-c5nc(-c6cccc7oc8ccccc8c67)nc(-c6cccc7oc8ccccc8c67)n5)c4c3c2)c1]
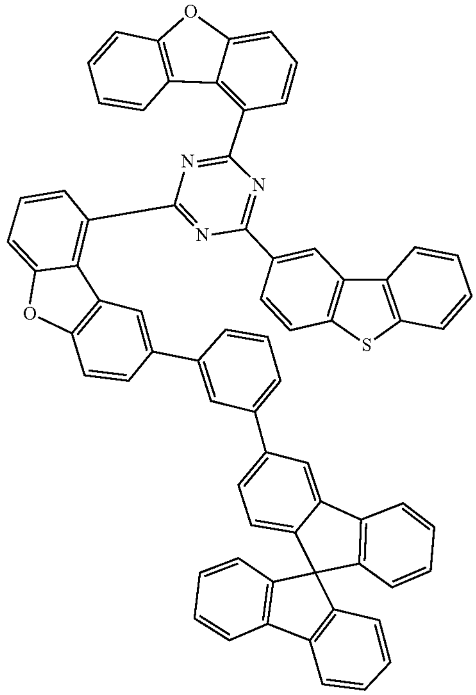 [SMILES: c1cc(-c2ccc3c(c2)-c2ccccc2C32c3ccccc3-c3ccccc32)cc(-c2ccc3oc4cccc(-c5nc(-c6ccc7sc8ccccc8c7c6)nc(-c6cccc7oc8ccccc8c67)n5)c4c3c2)c1]

TABLE 1-continued
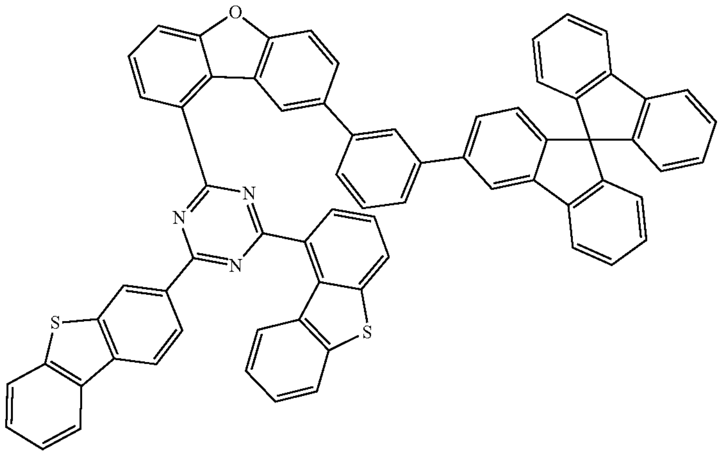 [SMILES: c1cc(-c2ccc3c(c2)-c2ccccc2C32c3ccccc3-c3ccccc32)cc(-c2ccc3oc4cccc(-c5nc(-c6ccc7c(c6)sc6ccccc67)nc(-c6cccc7sc8ccccc8c67)n5)c4c3c2)c1]
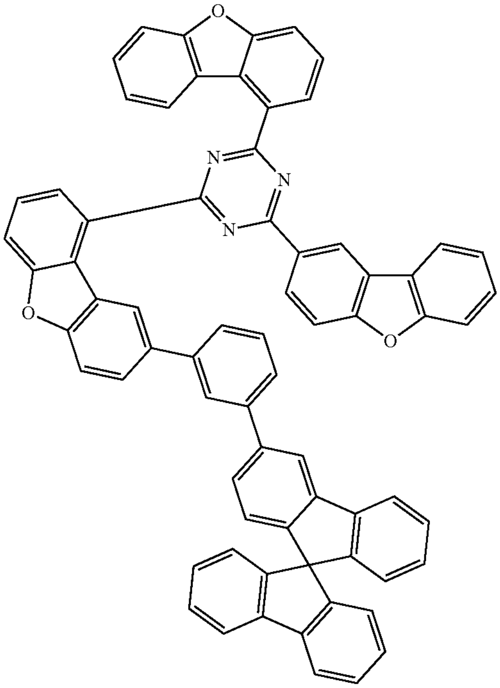 [SMILES: c1cc(-c2ccc3c(c2)-c2ccccc2C32c3ccccc3-c3ccccc32)cc(-c2ccc3oc4cccc(-c5nc(-c6ccc7oc8ccccc8c7c6)nc(-c6cccc7oc8ccccc8c67)n5)c4c3c2)c1]

TABLE 1-continued
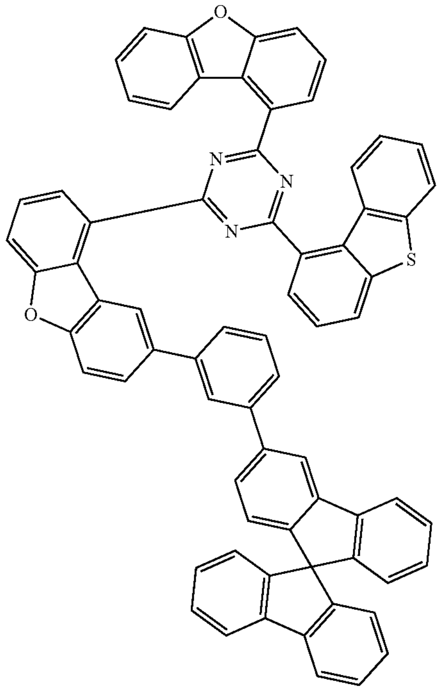 [SMILES: c1cc(-c2ccc3c(c2)-c2ccccc2C32c3ccccc3-c3ccccc32)cc(-c2ccc3oc4cccc(-c5nc(-c6cccc7oc8ccccc8c67)nc(-c6cccc7sc8ccccc8c67)n5)c4c3c2)c1]
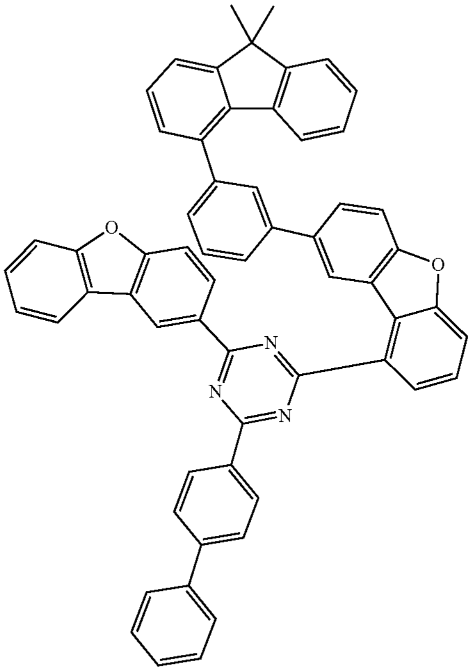 [SMILES: CC1(C)c2ccccc2-c2c(-c3cccc(-c4ccc5oc6cccc(-c7nc(-c8ccc(-c9ccccc9)cc8)nc(-c8ccc9oc%10ccccc%10c9c8)n7)c6c5c4)c3)cccc21]

TABLE 1-continued
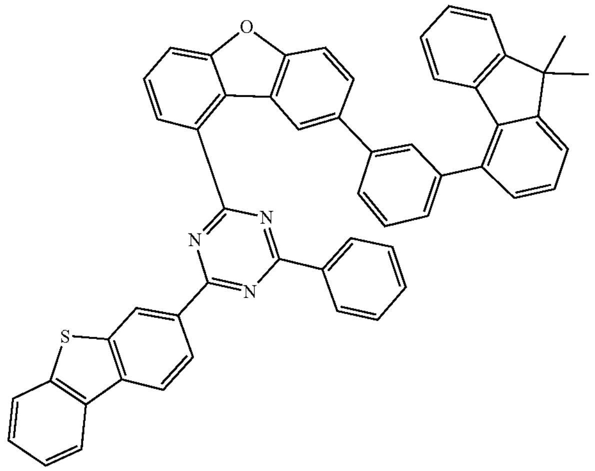 [SMILES: CC1(C)c2ccccc2-c2c(-c3cccc(-c4ccc5oc6cccc(-c7nc(-c8ccccc8)nc(-c8ccc9c(c8)sc8ccccc89)n7)c6c5c4)c3)cccc21]
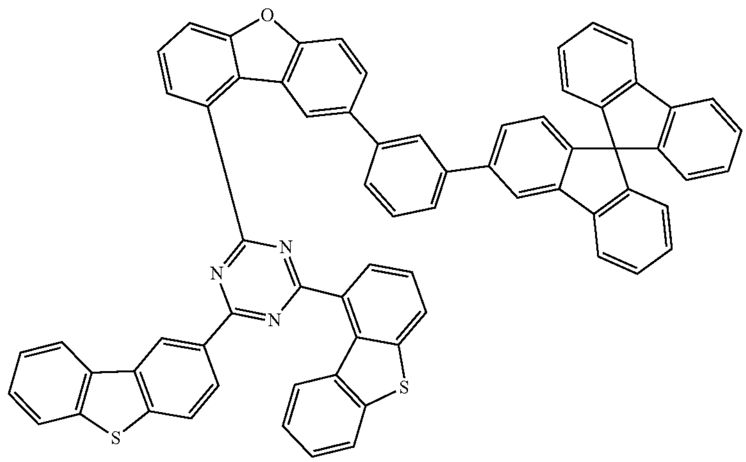 [SMILES: c1cc(-c2ccc3c(c2)-c2ccccc2C32c3ccccc3-c3ccccc32)cc(-c2ccc3oc4cccc(-c5nc(-c6ccc7sc8ccccc8c7c6)nc(-c6cccc7sc8ccccc8c67)n5)c4c3c2)c1]
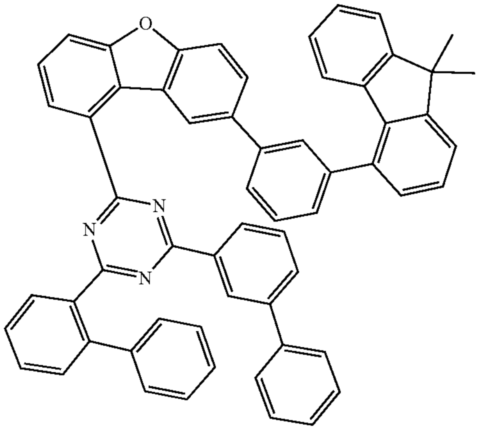 [SMILES: CC1(C)c2ccccc2-c2c(-c3cccc(-c4ccc5oc6cccc(-c7nc(-c8cccc(-c9ccccc9)c8)nc(-c8ccccc8-c8ccccc8)n7)c6c5c4)c3)cccc21]

TABLE 1-continued
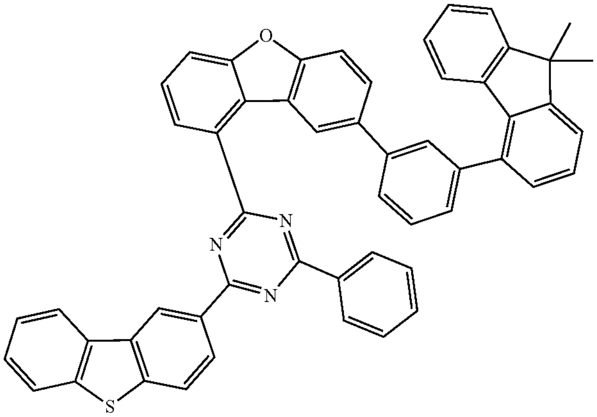 [SMILES: CC1(C)c2ccccc2-c2c(-c3cccc(-c4ccc5oc6cccc(-c7nc(-c8ccccc8)nc(-c8ccc9sc%10ccccc%10c9c8)n7)c6c5c4)c3)cccc21]
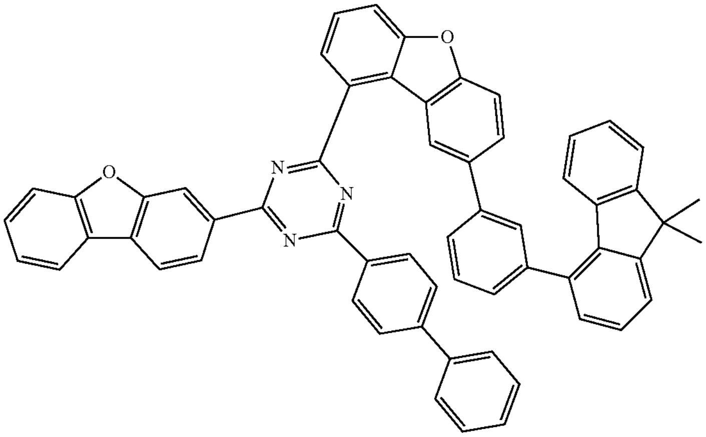 [SMILES: CC1(C)c2ccccc2-c2c(-c3cccc(-c4ccc5oc6cccc(-c7nc(-c8ccc(-c9ccccc9)cc8)nc(-c8ccc9c(c8)oc8ccccc89)n7)c6c5c4)c3)cccc21]
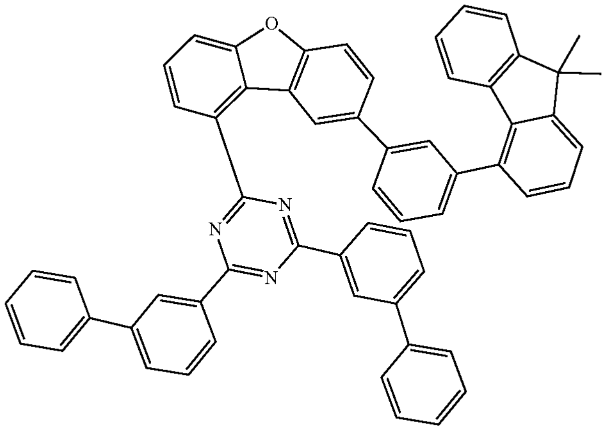 [SMILES: CC1(C)c2ccccc2-c2c(-c3cccc(-c4ccc5oc6cccc(-c7nc(-c8cccc(-c9ccccc9)c8)nc(-c8cccc(-c9ccccc9)c8)n7)c6c5c4)c3)cccc21]

TABLE 1-continued
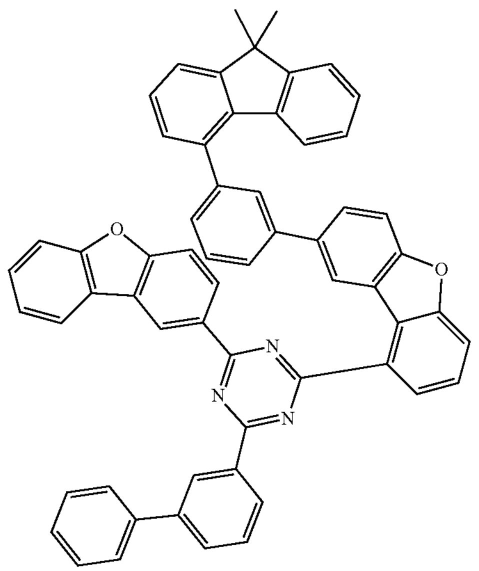 [SMILES: CC1(C)c2ccccc2-c2c(-c3cccc(-c4ccc5oc6cccc(-c7nc(-c8cccc(-c9ccccc9)c8)nc(-c8ccc9oc%10ccccc%10c9c8)n7)c6c5c4)c3)cccc21]
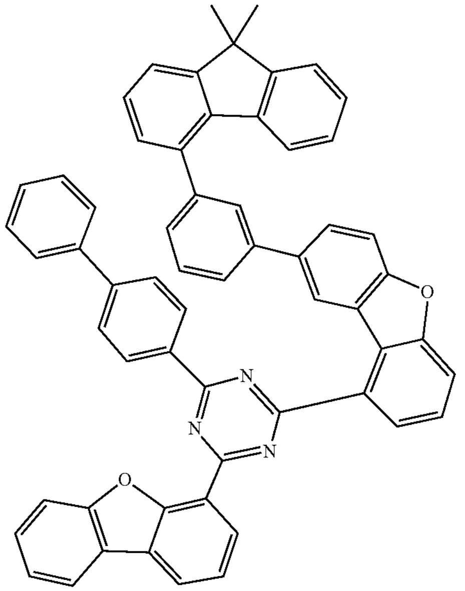 [SMILES: CC1(C)c2ccccc2-c2c(-c3cccc(-c4ccc5oc6cccc(-c7nc(-c8ccc(-c9ccccc9)cc8)nc(-c8cccc9c8oc8ccccc89)n7)c6c5c4)c3)cccc21]

TABLE 1-continued
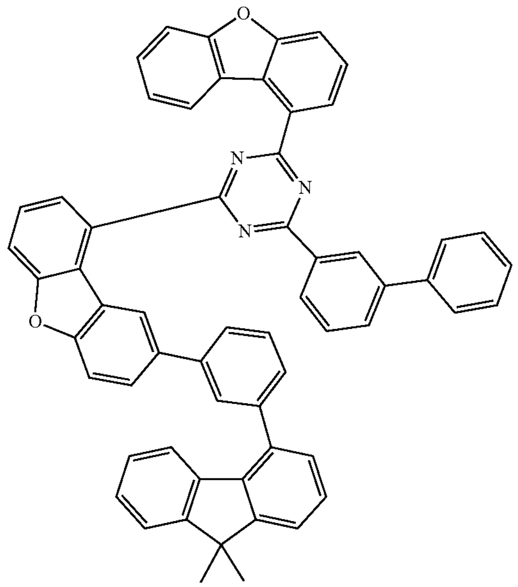 [SMILES: CC1(C)c2ccccc2-c2c(-c3cccc(-c4ccc5oc6cccc(-c7nc(-c8cccc(-c9ccccc9)c8)nc(-c8cccc9oc%10ccccc%10c89)n7)c6c5c4)c3)cccc21]
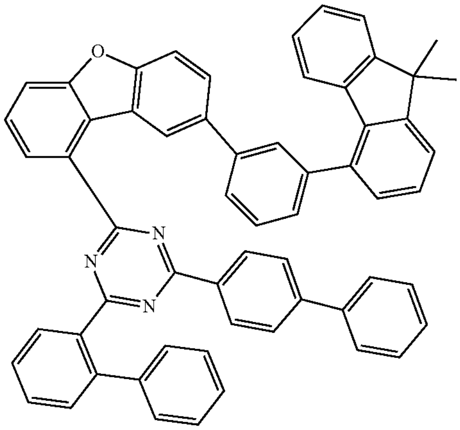 [SMILES: CC1(C)c2ccccc2-c2c(-c3cccc(-c4ccc5oc6cccc(-c7nc(-c8ccc(-c9ccccc9)cc8)nc(-c8ccccc8-c8ccccc8)n7)c6c5c4)c3)cccc21]
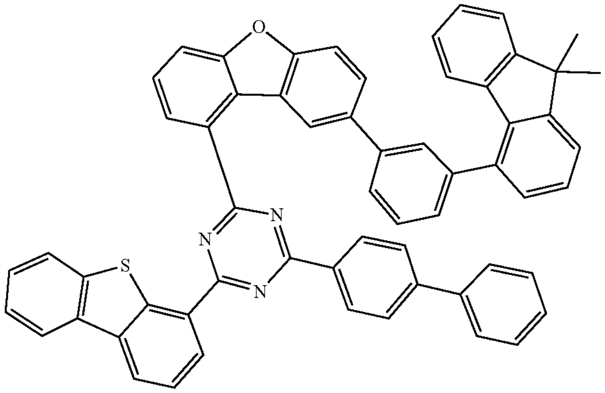 [SMILES: CC1(C)c2ccccc2-c2c(-c3cccc(-c4ccc5oc6cccc(-c7nc(-c8ccc(-c9ccccc9)cc8)nc(-c8cccc9c8sc8ccccc89)n7)c6c5c4)c3)cccc21]

TABLE 1-continued
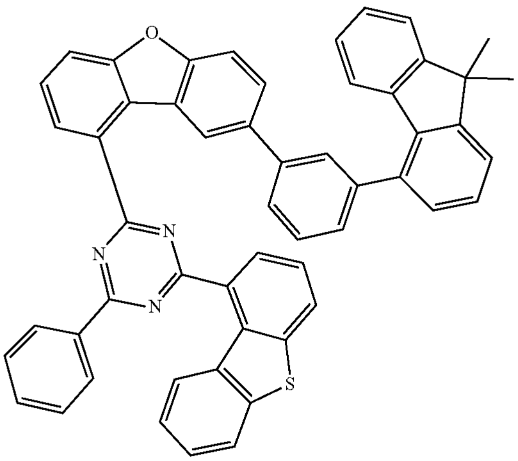 [SMILES: CC1(C)c2ccccc2-c2c(-c3cccc(-c4ccc5oc6cccc(-c7nc(-c8ccccc8)nc(-c8cccc9sc%10ccccc%10c89)n7)c6c5c4)c3)cccc21]
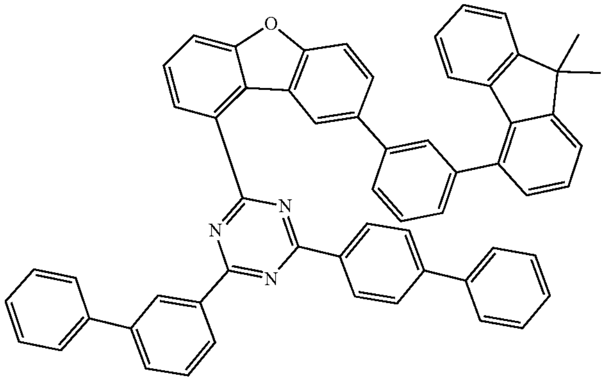 [SMILES: CC1(C)c2ccccc2-c2c(-c3cccc(-c4ccc5oc6cccc(-c7nc(-c8ccc(-c9ccccc9)cc8)nc(-c8cccc(-c9ccccc9)c8)n7)c6c5c4)c3)cccc21]
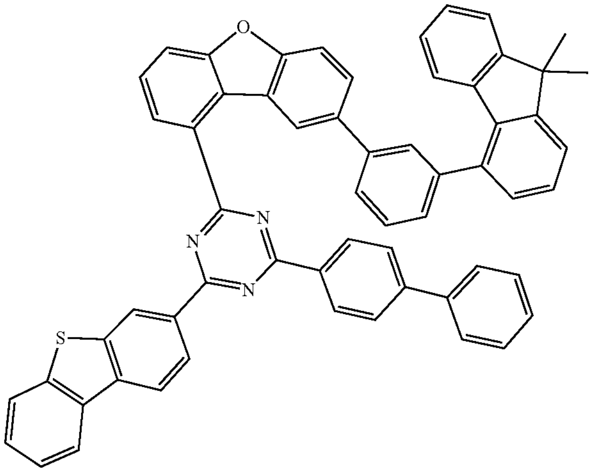 [SMILES: CC1(C)c2ccccc2-c2c(-c3cccc(-c4ccc5oc6cccc(-c7nc(-c8ccc(-c9ccccc9)cc8)nc(-c8ccc9c(c8)sc8ccccc89)n7)c6c5c4)c3)cccc21]

TABLE 1-continued
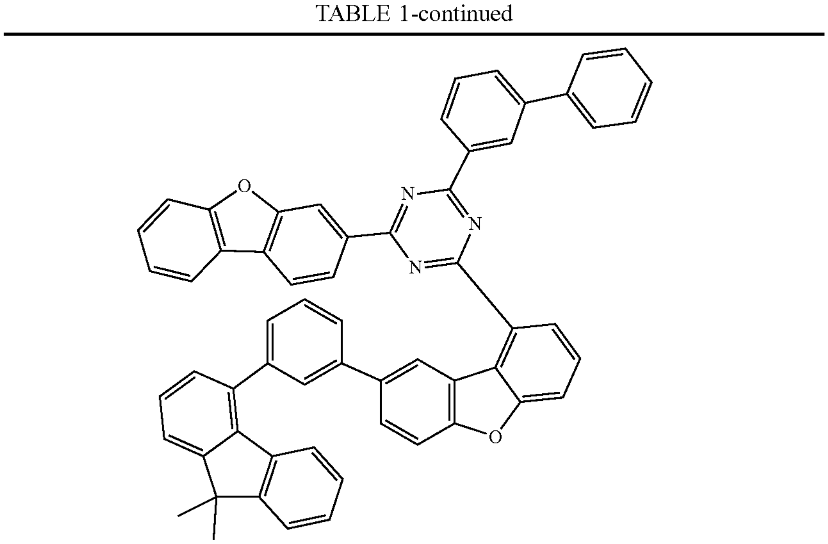
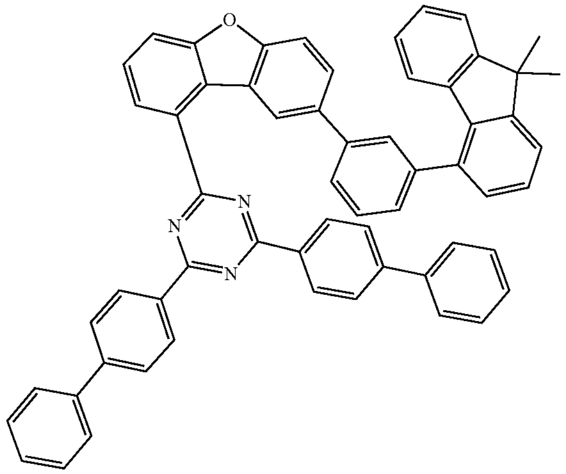 [SMILES: CC1(C)c2ccccc2-c2c(-c3cccc(-c4ccc5oc6cccc(-c7nc(-c8ccc(-c9ccccc9)cc8)nc(-c8ccc(-c9ccccc9)cc8)n7)c6c5c4)c3)cccc21]
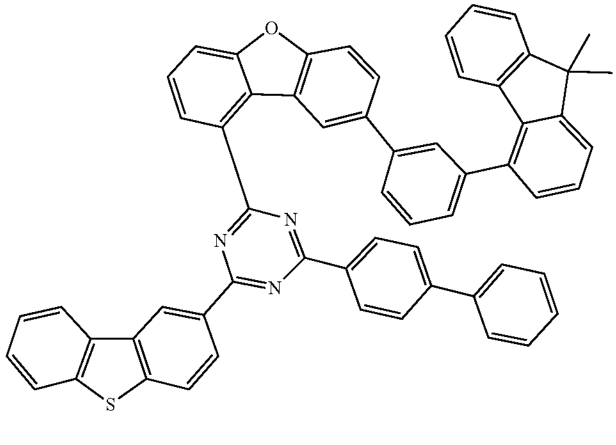 [SMILES: CC1(C)c2ccccc2-c2c(-c3cccc(-c4ccc5oc6cccc(-c7nc(-c8ccc(-c9ccccc9)cc8)nc(-c8ccc9sc%10ccccc%10c9c8)n7)c6c5c4)c3)cccc21]

TABLE 1-continued
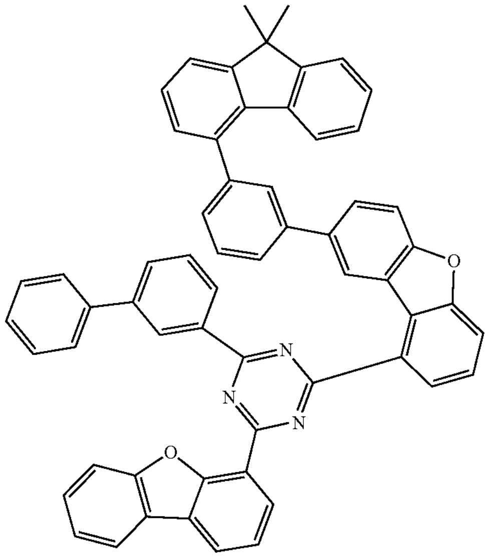 [SMILES: CC1(C)c2ccccc2-c2c(-c3cccc(-c4ccc5oc6cccc(-c7nc(-c8cccc(-c9ccccc9)c8)nc(-c8cccc9c8oc8ccccc89)n7)c6c5c4)c3)cccc21]
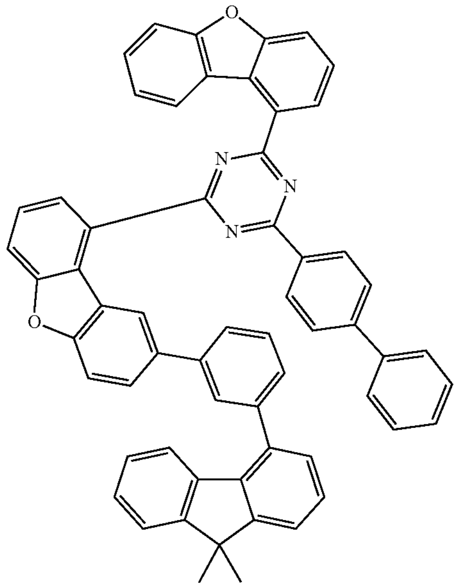 [SMILES: CC1(C)c2ccccc2-c2c(-c3cccc(-c4ccc5oc6cccc(-c7nc(-c8ccc(-c9ccccc9)cc8)nc(-c8cccc9oc%10ccccc%10c89)n7)c6c5c4)c3)cccc21]
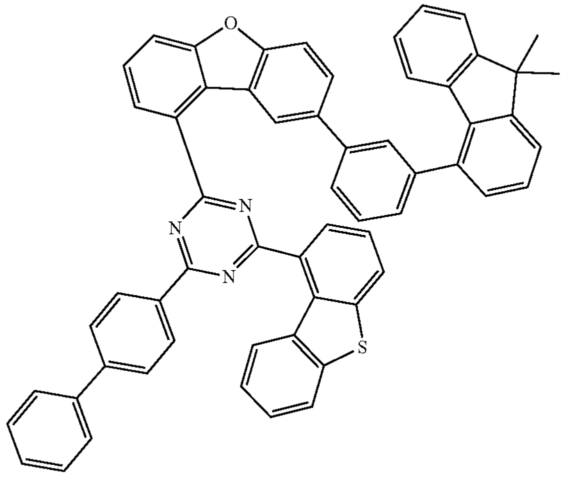 [SMILES: CC1(C)c2ccccc2-c2c(-c3cccc(-c4ccc5oc6cccc(-c7nc(-c8ccc(-c9ccccc9)cc8)nc(-c8cccc9sc%10ccccc%10c89)n7)c6c5c4)c3)cccc21]

TABLE 1-continued
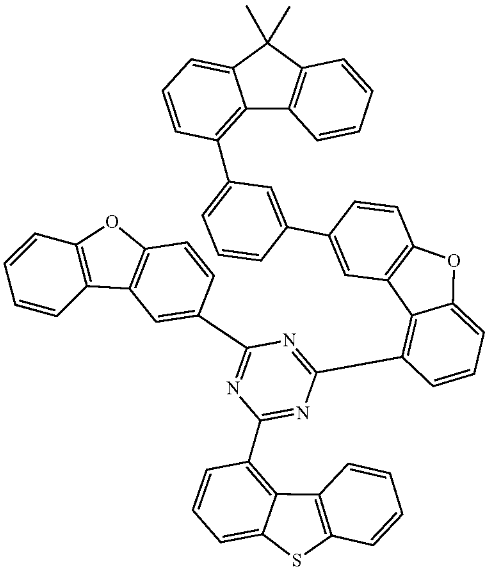 [SMILES: CC1(C)c2ccccc2-c2c(-c3cccc(-c4ccc5oc6cccc(-c7nc(-c8ccc9oc%10ccccc%10c9c8)nc(-c8cccc9sc%10ccccc%10c89)n7)c6c5c4)c3)cccc21]
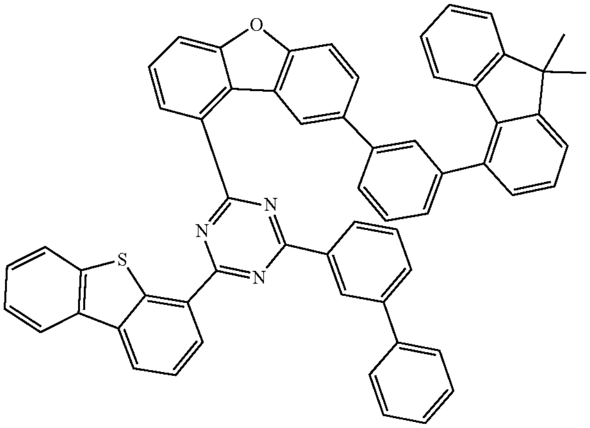 [SMILES: CC1(C)c2ccccc2-c2c(-c3cccc(-c4ccc5oc6cccc(-c7nc(-c8cccc(-c9ccccc9)c8)nc(-c8cccc9c8sc8ccccc89)n7)c6c5c4)c3)cccc21]
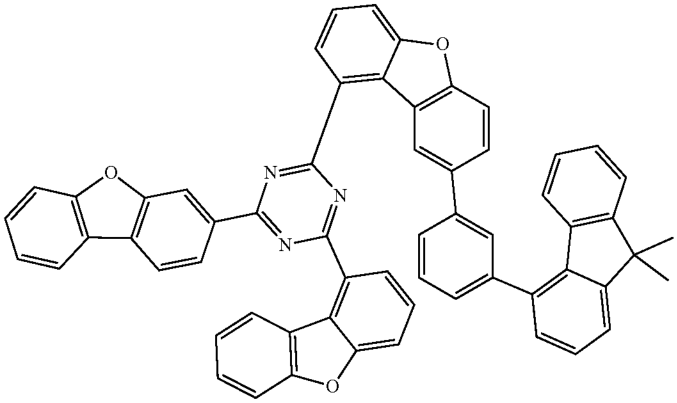 [SMILES: CC1(C)c2ccccc2-c2c(-c3cccc(-c4ccc5oc6cccc(-c7nc(-c8ccc9c(c8)oc8ccccc89)nc(-c8cccc9oc%10ccccc%10c89)n7)c6c5c4)c3)cccc21]

TABLE 1-continued
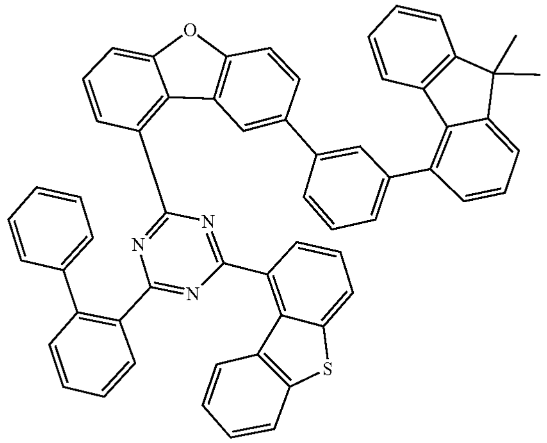 [SMILES: CC1(C)c2ccccc2-c2c(-c3cccc(-c4ccc5oc6cccc(-c7nc(-c8ccccc8-c8ccccc8)nc(-c8cccc9sc%10ccccc%10c89)n7)c6c5c4)c3)cccc21]
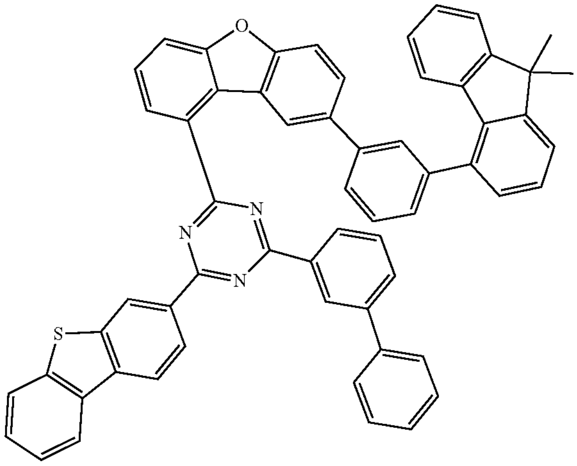 [SMILES: CC1(C)c2ccccc2-c2c(-c3cccc(-c4ccc5oc6cccc(-c7nc(-c8cccc(-c9ccccc9)c8)nc(-c8ccc9c(c8)sc8ccccc89)n7)c6c5c4)c3)cccc21]
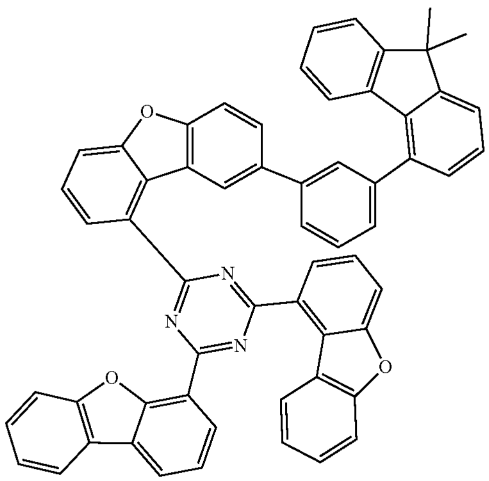 [SMILES: CC1(C)c2ccccc2-c2c(-c3cccc(-c4ccc5oc6cccc(-c7nc(-c8cccc9c8oc8ccccc89)nc(-c8cccc9oc%10ccccc%10c89)n7)c6c5c4)c3)cccc21]

TABLE 1-continued
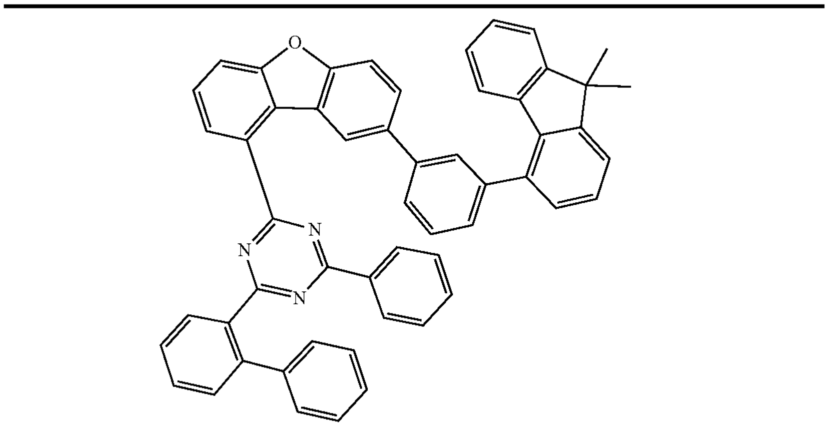
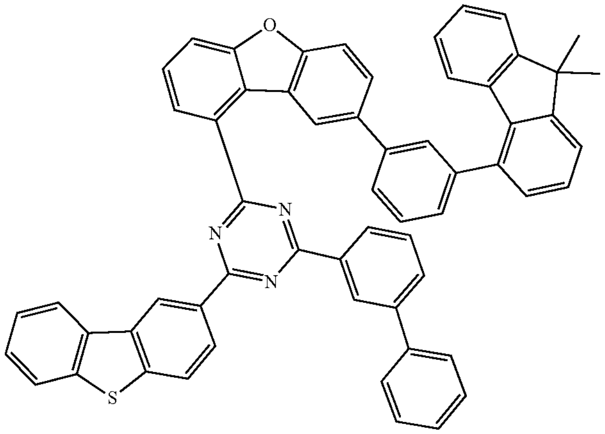 [SMILES: CC1(C)c2ccccc2-c2c(-c3cccc(-c4ccc5oc6cccc(-c7nc(-c8cccc(-c9ccccc9)c8)nc(-c8ccc9sc%10ccccc%10c9c8)n7)c6c5c4)c3)cccc21]
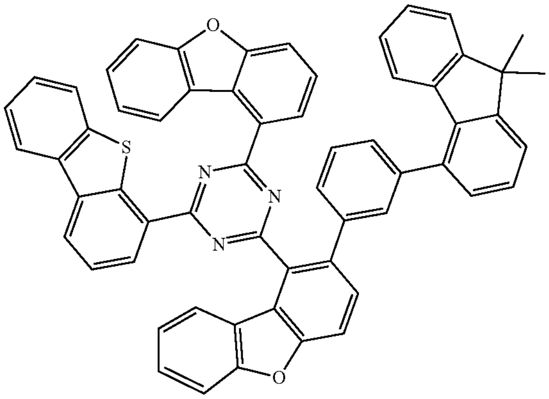 [SMILES: CC1(C)c2ccccc2-c2c(-c3cccc(-c4ccc5oc6ccccc6c5c4-c4nc(-c5cccc6c5sc5ccccc56)nc(-c5cccc6oc7ccccc7c56)n4)c3)cccc21]
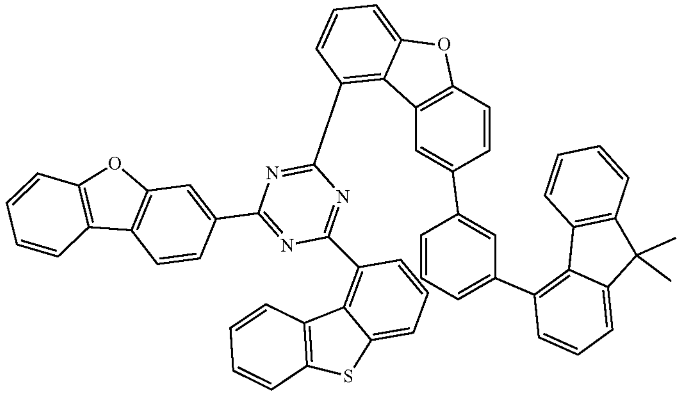 [SMILES: CC1(C)c2ccccc2-c2c(-c3cccc(-c4ccc5oc6cccc(-c7nc(-c8ccc9c(c8)oc8ccccc89)nc(-c8cccc9sc%10ccccc%10c89)n7)c6c5c4)c3)cccc21]

TABLE 1-continued
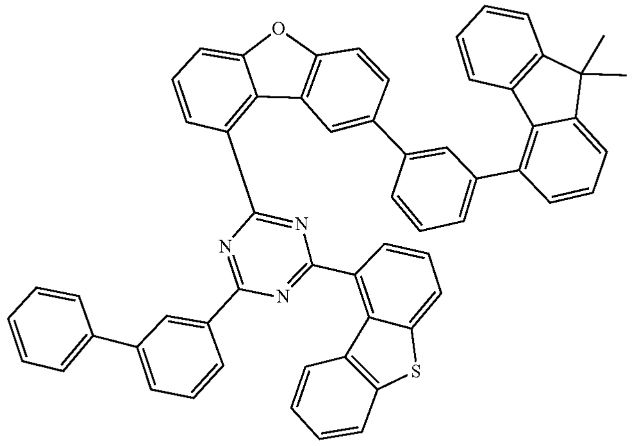 [SMILES: CC1(C)c2ccccc2-c2c(-c3cccc(-c4ccc5oc6cccc(-c7nc(-c8cccc(-c9ccccc9)c8)nc(-c8cccc9sc%10ccccc%10c89)n7)c6c5c4)c3)cccc21]
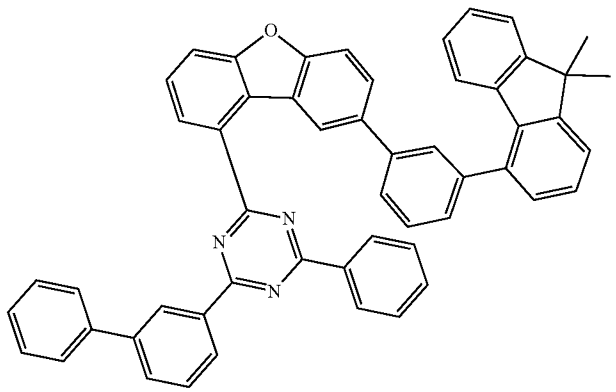 [SMILES: CC1(C)c2ccccc2-c2c(-c3cccc(-c4ccc5oc6cccc(-c7nc(-c8ccccc8)nc(-c8cccc(-c9ccccc9)c8)n7)c6c5c4)c3)cccc21]
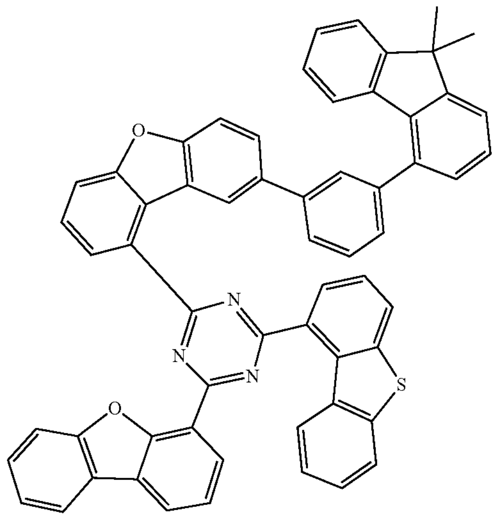 [SMILES: CC1(C)c2ccccc2-c2c(-c3cccc(-c4ccc5oc6cccc(-c7nc(-c8cccc9c8oc8ccccc89)nc(-c8cccc9sc%10ccccc%10c89)n7)c6c5c4)c3)cccc21]

TABLE 1-continued
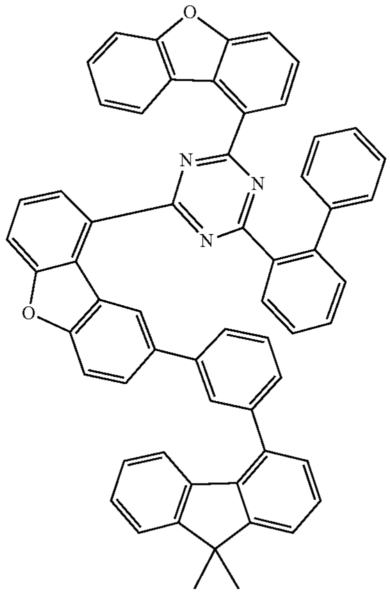 [SMILES: CC1(C)c2ccccc2-c2c(-c3cccc(-c4ccc5oc6cccc(-c7nc(-c8ccccc8-c8ccccc8)nc(-c8cccc9oc%10ccccc%10c89)n7)c6c5c4)c3)cccc21]
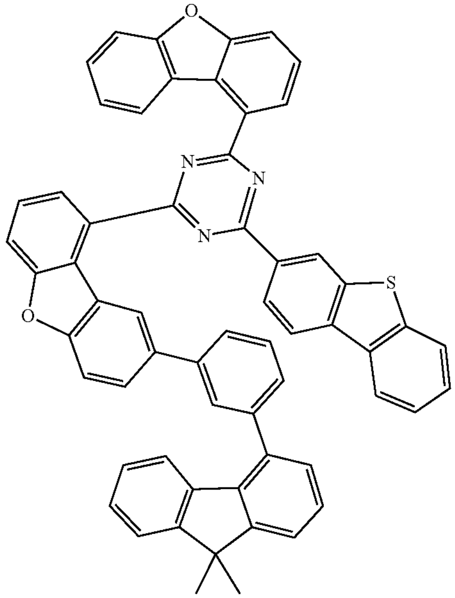 [SMILES: CC1(C)c2ccccc2-c2c(-c3cccc(-c4ccc5oc6cccc(-c7nc(-c8ccc9c(c8)sc8ccccc89)nc(-c8cccc9oc%10ccccc%10c89)n7)c6c5c4)c3)cccc21]

TABLE 1-continued
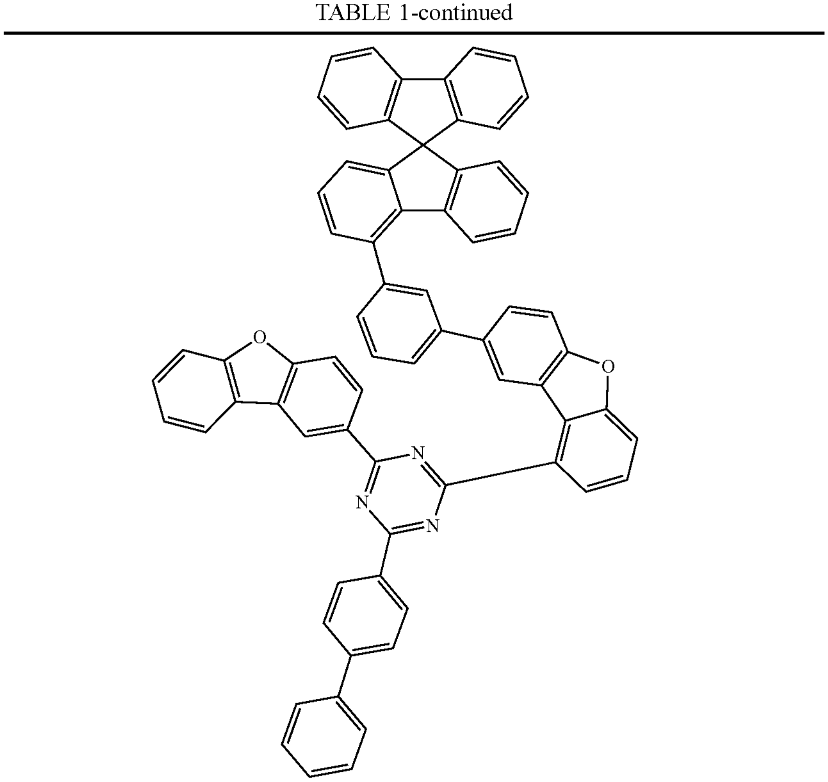
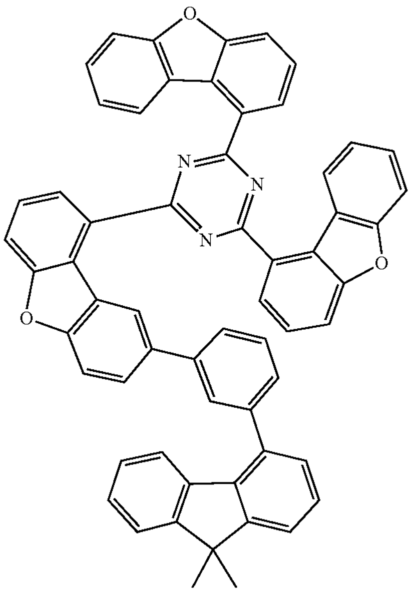

TABLE 1-continued
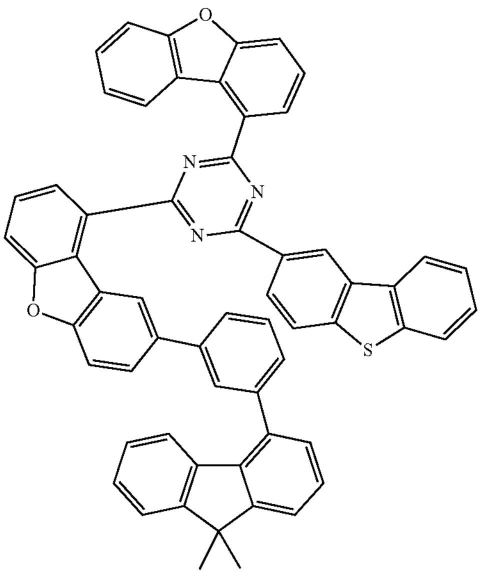 [SMILES: CC1(C)c2ccccc2-c2c(-c3cccc(-c4ccc5oc6cccc(-c7nc(-c8ccc9sc%10ccccc%10c9c8)nc(-c8cccc9oc%10ccccc%10c89)n7)c6c5c4)c3)cccc21]
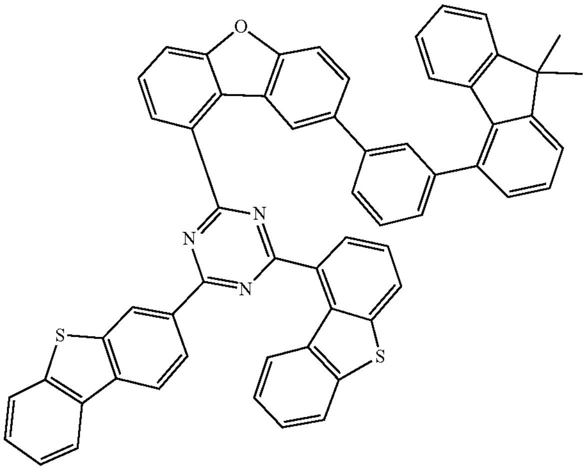 [SMILES: CC1(C)c2ccccc2-c2c(-c3cccc(-c4ccc5oc6cccc(-c7nc(-c8ccc9c(c8)sc8ccccc89)nc(-c8cccc9sc%10ccccc%10c89)n7)c6c5c4)c3)cccc21]
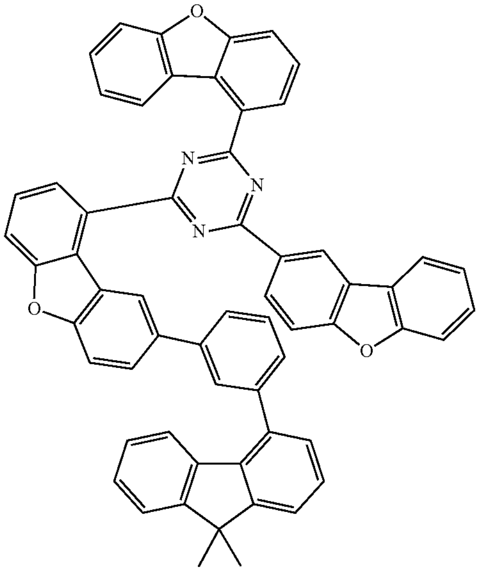 [SMILES: CC1(C)c2ccccc2-c2c(-c3cccc(-c4ccc5oc6cccc(-c7nc(-c8ccc9oc%10ccccc%10c9c8)nc(-c8cccc9oc%10ccccc%10c89)n7)c6c5c4)c3)cccc21]

TABLE 1-continued
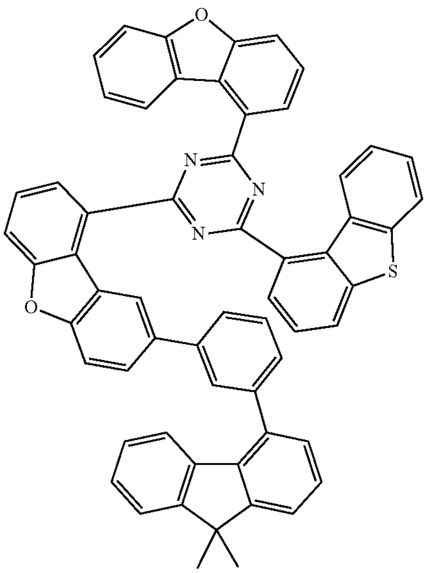 [SMILES: CC1(C)c2ccccc2-c2c(-c3cccc(-c4ccc5oc6cccc(-c7nc(-c8cccc9oc%10ccccc%10c89)nc(-c8cccc9sc%10ccccc%10c89)n7)c6c5c4)c3)cccc21]
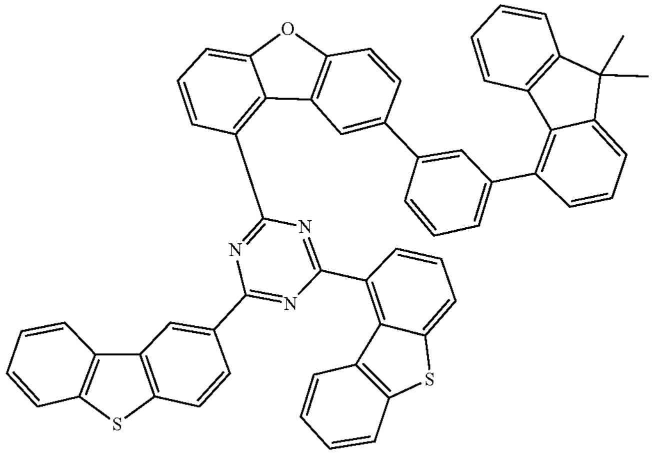 [SMILES: CC1(C)c2ccccc2-c2c(-c3cccc(-c4ccc5oc6cccc(-c7nc(-c8ccc9sc%10ccccc%10c9c8)nc(-c8cccc9sc%10ccccc%10c89)n7)c6c5c4)c3)cccc21]
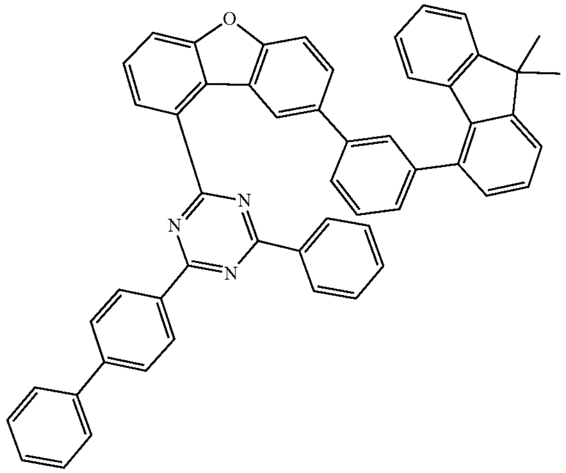 [SMILES: CC1(C)c2ccccc2-c2c(-c3cccc(-c4ccc5oc6cccc(-c7nc(-c8ccccc8)nc(-c8ccc(-c9ccccc9)cc8)n7)c6c5c4)c3)cccc21]

TABLE 1-continued
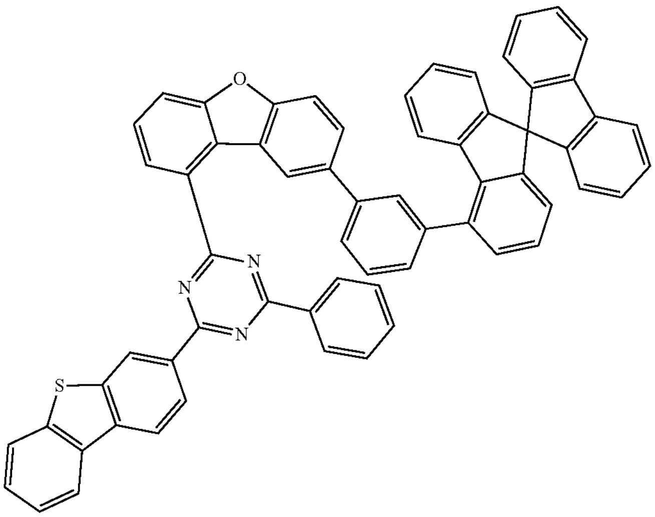 [SMILES: c1ccc(-c2nc(-c3ccc4c(c3)sc3ccccc34)nc(-c3cccc4oc5ccc(-c6cccc(-c7cccc8c7-c7ccccc7C87c8ccccc8-c8ccccc87)c6)cc5c34)n2)cc1]
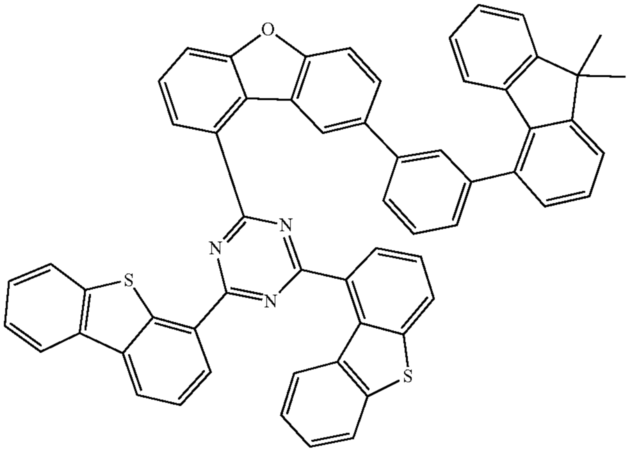 [SMILES: CC1(C)c2ccccc2-c2c(-c3cccc(-c4ccc5oc6cccc(-c7nc(-c8cccc9c8sc8ccccc89)nc(-c8cccc9sc%10ccccc%10c89)n7)c6c5c4)c3)cccc21]
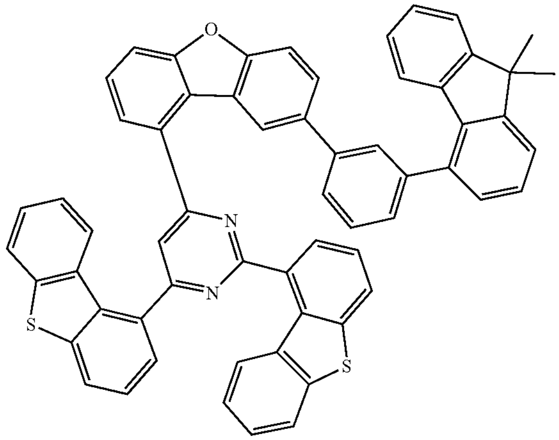 [SMILES: CC1(C)c2ccccc2-c2c(-c3cccc(-c4ccc5oc6cccc(-c7cc(-c8cccc9sc%10ccccc%10c89)nc(-c8cccc9sc%10ccccc%10c89)n7)c6c5c4)c3)cccc21]

TABLE 1-continued
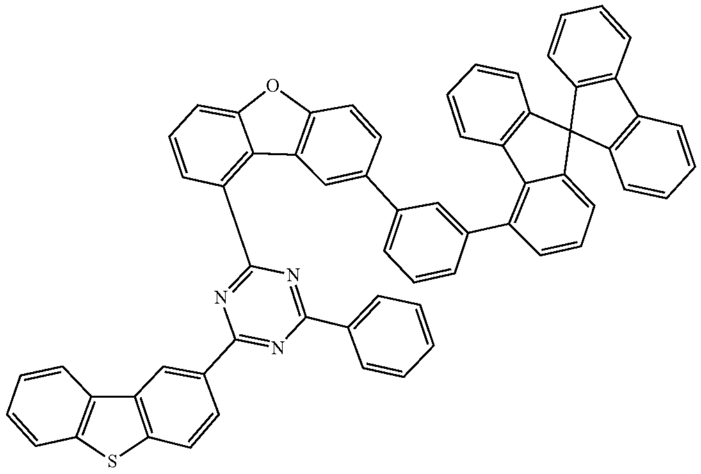 [SMILES: c1ccc(-c2nc(-c3ccc4sc5ccccc5c4c3)nc(-c3cccc4oc5ccc(-c6cccc(-c7cccc8c7-c7ccccc7C87c8ccccc8-c8ccccc87)c6)cc5c34)n2)cc1]
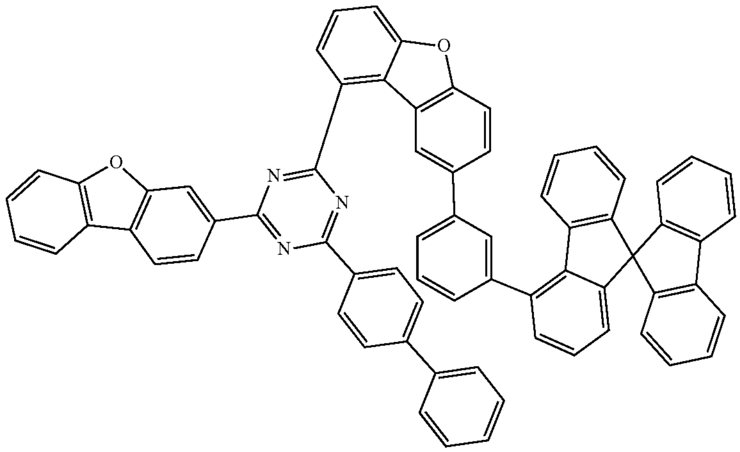 [SMILES: c1ccc(-c2ccc(-c3nc(-c4ccc5c(c4)oc4ccccc45)nc(-c4cccc5oc6ccc(-c7cccc(-c8cccc9c8-c8ccccc8C98c9ccccc9-c9ccccc98)c7)cc6c45)n3)cc2)cc1]
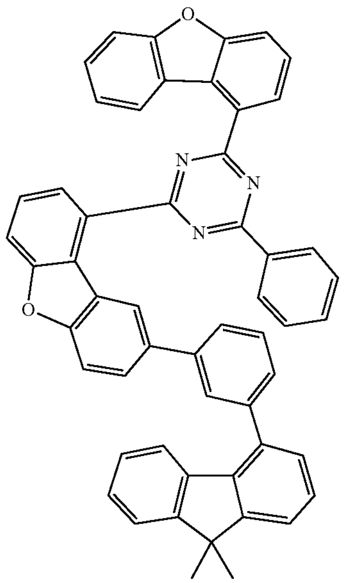 [SMILES: CC1(C)c2ccccc2-c2c(-c3cccc(-c4ccc5oc6cccc(-c7nc(-c8ccccc8)nc(-c8cccc9oc%10ccccc%10c89)n7)c6c5c4)c3)cccc21]

TABLE 1-continued
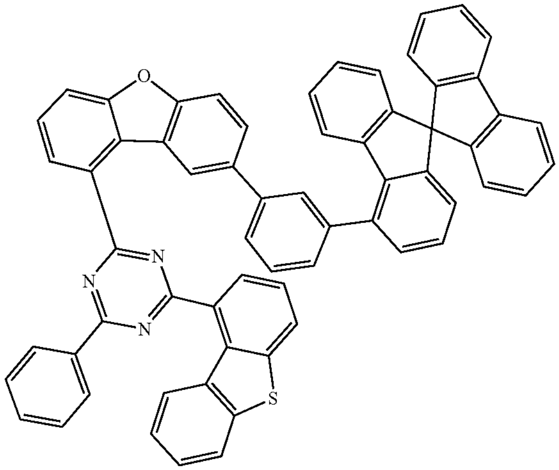 [SMILES: c1ccc(-c2nc(-c3cccc4oc5ccc(-c6cccc(-c7cccc8c7-c7ccccc7C87c8ccccc8-c8ccccc87)c6)cc5c34)nc(-c3cccc4sc5ccccc5c34)n2)cc1]
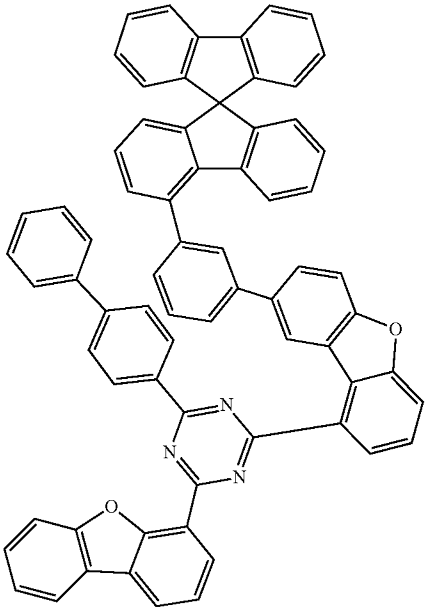 [SMILES: c1ccc(-c2ccc(-c3nc(-c4cccc5c4oc4ccccc45)nc(-c4cccc5oc6ccc(-c7cccc(-c8cccc9c8-c8ccccc8C98c9ccccc9-c9ccccc98)c7)cc6c45)n3)cc2)cc1]
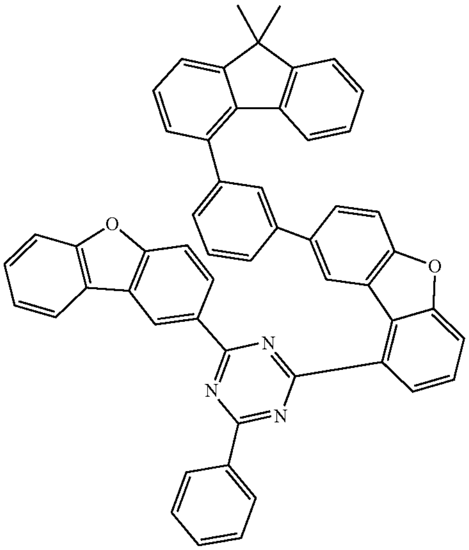 [SMILES: CC1(C)c2ccccc2-c2c(-c3cccc(-c4ccc5oc6cccc(-c7nc(-c8ccccc8)nc(-c8ccc9oc%10ccccc%10c9c8)n7)c6c5c4)c3)cccc21]

TABLE 1-continued
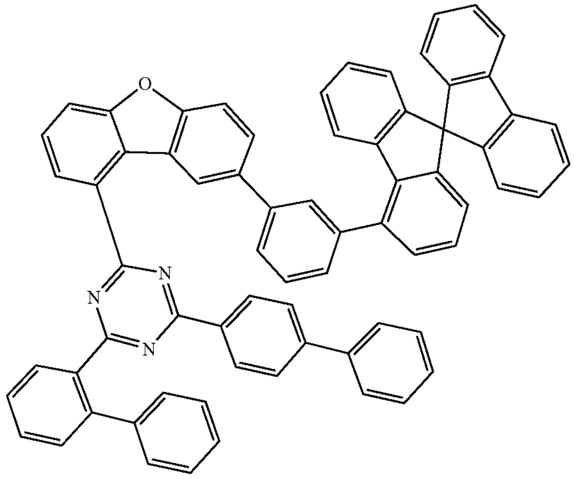 [SMILES: c1ccc(-c2ccc(-c3nc(-c4ccccc4-c4ccccc4)nc(-c4cccc5oc6ccc(-c7cccc(-c8cccc9c8-c8ccccc8C98c9ccccc9-c9ccccc98)c7)cc6c45)n3)cc2)cc1]
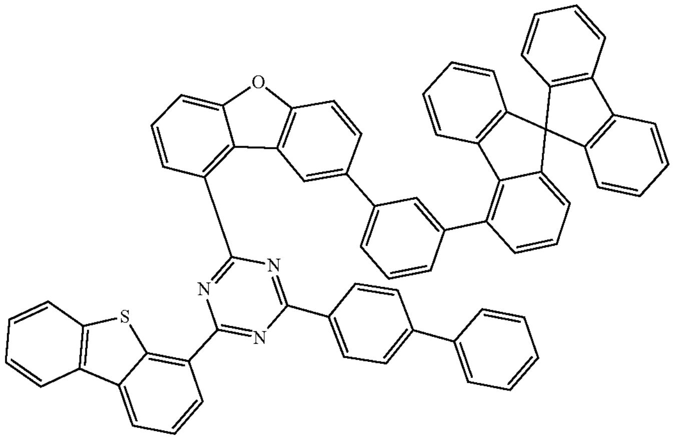 [SMILES: c1ccc(-c2ccc(-c3nc(-c4cccc5c4sc4ccccc45)nc(-c4cccc5oc6ccc(-c7cccc(-c8cccc9c8-c8ccccc8C98c9ccccc9-c9ccccc98)c7)cc6c45)n3)cc2)cc1]
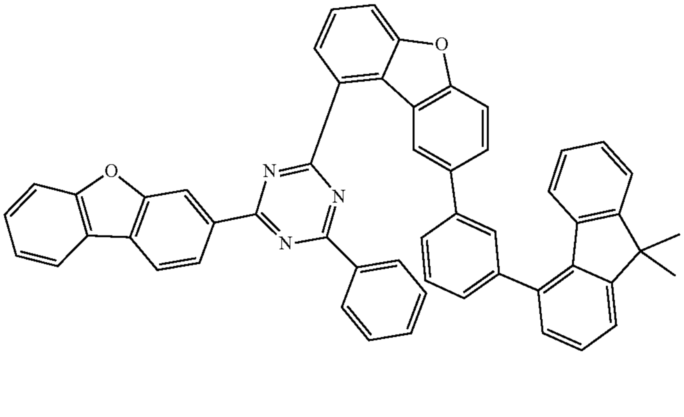 [SMILES: CC1(C)c2ccccc2-c2c(-c3cccc(-c4ccc5oc6cccc(-c7nc(-c8ccccc8)nc(-c8ccc9c(c8)oc8ccccc89)n7)c6c5c4)c3)cccc21]

TABLE 1-continued
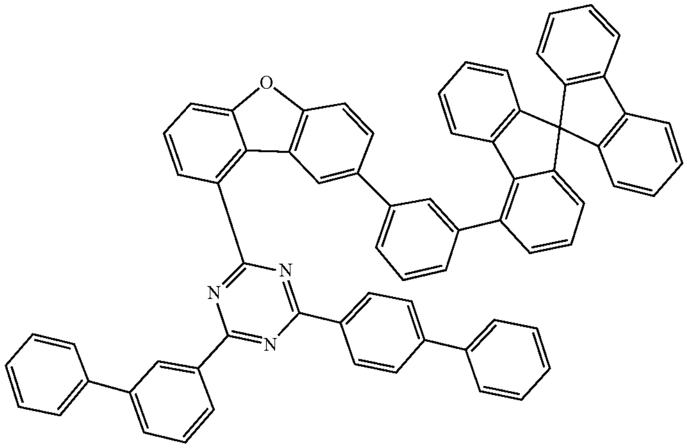 [SMILES: c1ccc(-c2ccc(-c3nc(-c4cccc(-c5ccccc5)c4)nc(-c4cccc5oc6ccc(-c7cccc(-c8cccc9c8-c8ccccc8C98c9ccccc9-c9ccccc98)c7)cc6c45)n3)cc2)cc1]
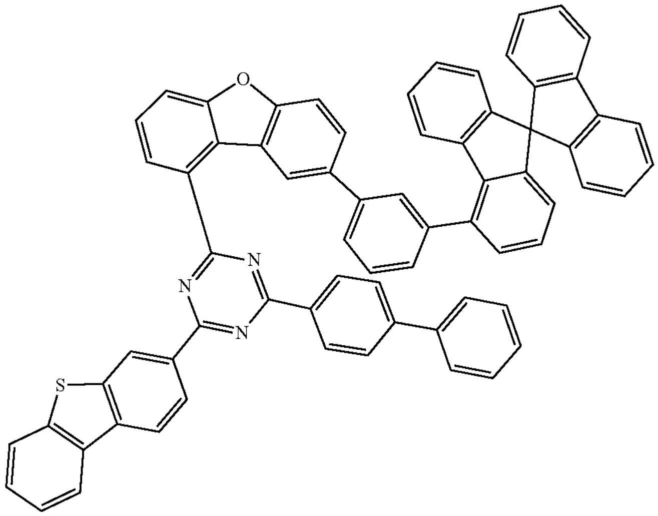 [SMILES: c1ccc(-c2ccc(-c3nc(-c4ccc5c(c4)sc4ccccc45)nc(-c4cccc5oc6ccc(-c7cccc(-c8cccc9c8-c8ccccc8C98c9ccccc9-c9ccccc98)c7)cc6c45)n3)cc2)cc1]
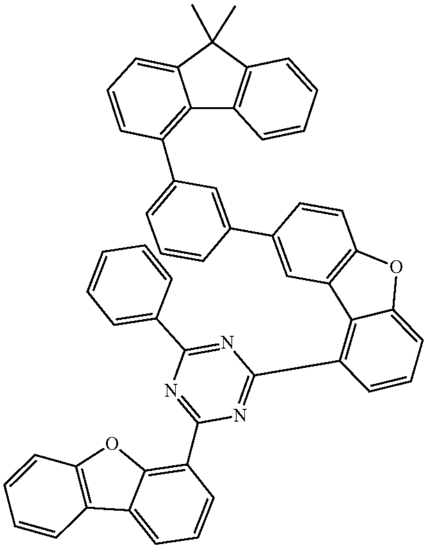 [SMILES: CC1(C)c2ccccc2-c2c(-c3cccc(-c4ccc5oc6cccc(-c7nc(-c8ccccc8)nc(-c8cccc9c8oc8ccccc89)n7)c6c5c4)c3)cccc21]

TABLE 1-continued
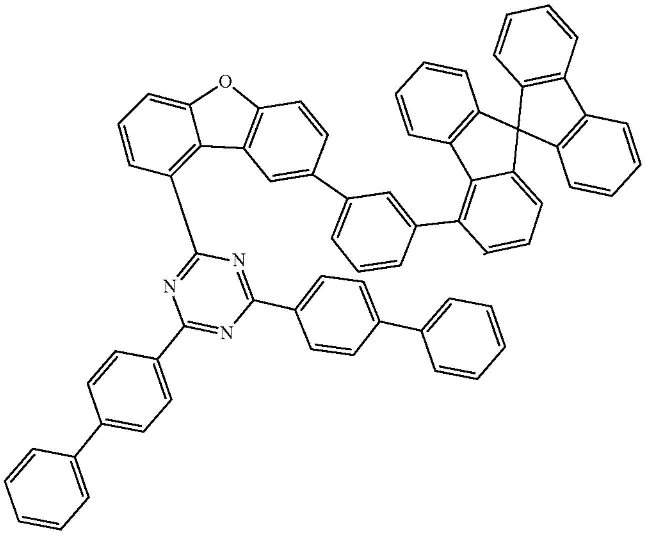 [SMILES: Cc1ccc2c(c1-c1cccc(-c3ccc4oc5cccc(-c6nc(-c7ccc(-c8ccccc8)cc7)nc(-c7ccc(-c8ccccc8)cc7)n6)c5c4c3)c1)-c1ccccc1C21c2ccccc2-c2ccccc21]
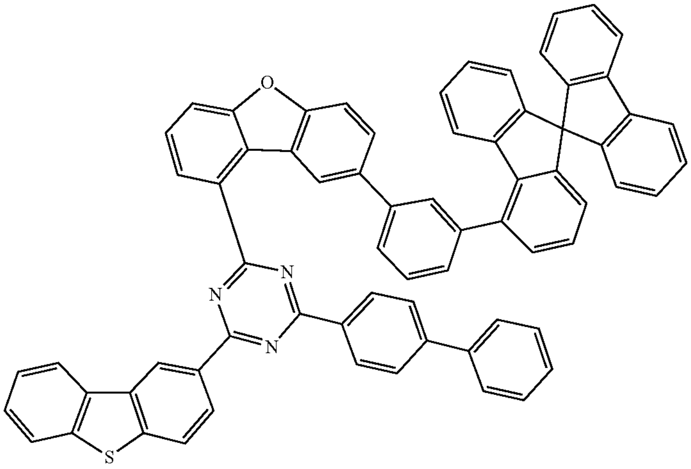 [SMILES: c1ccc(-c2ccc(-c3nc(-c4ccc5sc6ccccc6c5c4)nc(-c4cccc5oc6ccc(-c7cccc(-c8cccc9c8-c8ccccc8C98c9ccccc9-c9ccccc98)c7)cc6c45)n3)cc2)cc1]
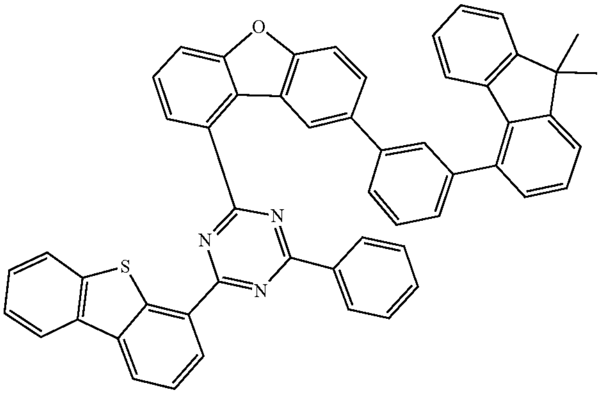 [SMILES: CC1(C)c2ccccc2-c2c(-c3cccc(-c4ccc5oc6cccc(-c7nc(-c8ccccc8)nc(-c8cccc9c8sc8ccccc89)n7)c6c5c4)c3)cccc21]

TABLE 1-continued
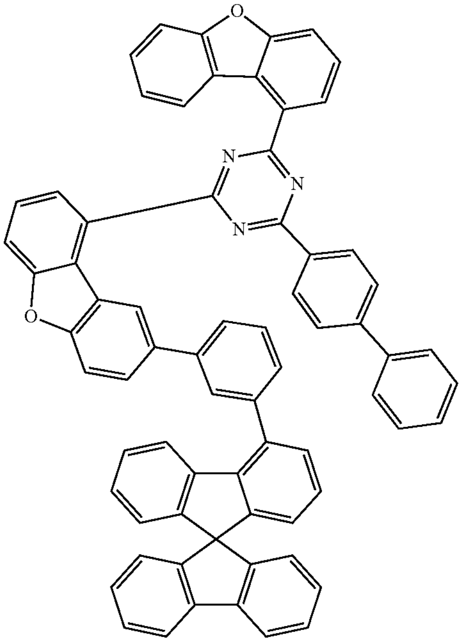 [SMILES: c1ccc(-c2ccc(-c3nc(-c4cccc5oc6ccccc6c45)nc(-c4cccc5oc6ccc(-c7cccc(-c8cccc9c8-c8ccccc8C98c9ccccc9-c9ccccc98)c7)cc6c45)n3)cc2)cc1]
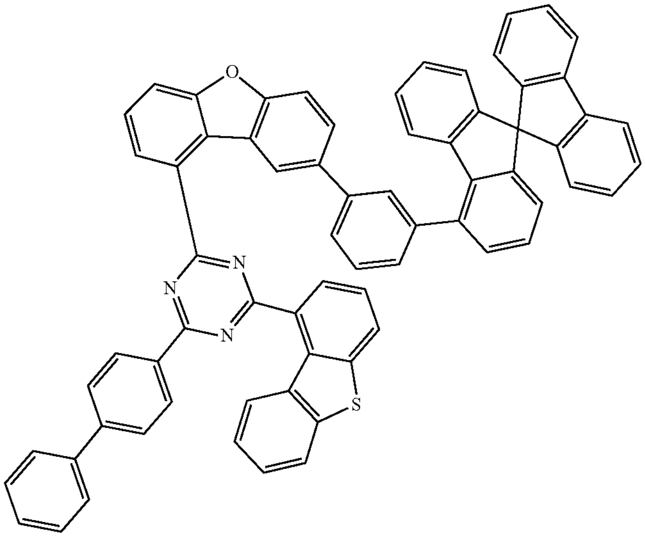 [SMILES: c1ccc(-c2ccc(-c3nc(-c4cccc5oc6ccc(-c7cccc(-c8cccc9c8-c8ccccc8C98c9ccccc9-c9ccccc98)c7)cc6c45)nc(-c4cccc5sc6ccccc6c45)n3)cc2)cc1]

TABLE 1-continued
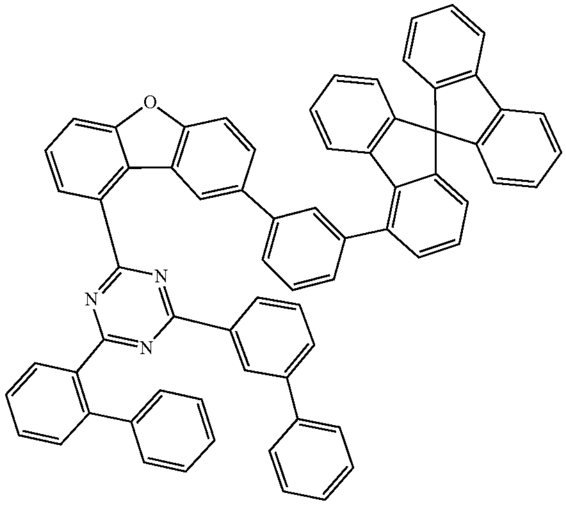 [SMILES: c1ccc(-c2cccc(-c3nc(-c4ccccc4-c4ccccc4)nc(-c4cccc5oc6ccc(-c7cccc(-c8cccc9c8-c8ccccc8C98c9ccccc9-c9ccccc98)c7)cc6c45)n3)c2)cc1]
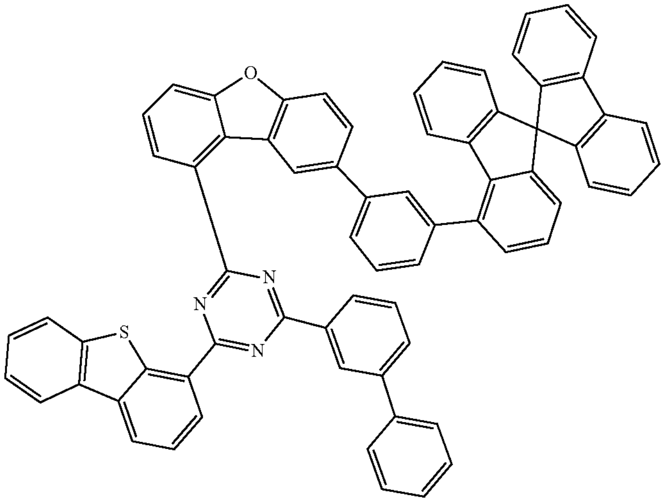 [SMILES: c1ccc(-c2cccc(-c3nc(-c4cccc5c4sc4ccccc45)nc(-c4cccc5oc6ccc(-c7cccc(-c8cccc9c8-c8ccccc8C98c9ccccc9-c9ccccc98)c7)cc6c45)n3)c2)cc1]
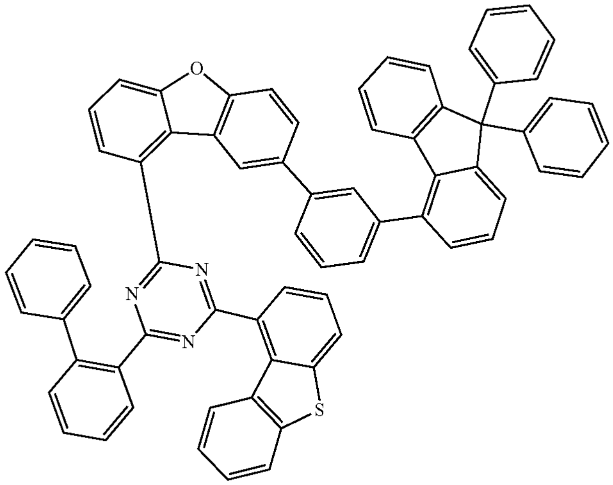 [SMILES: c1ccc(-c2ccccc2-c2nc(-c3cccc4oc5ccc(-c6cccc(-c7cccc8c7-c7ccccc7C8(c7ccccc7)c7ccccc7)c6)cc5c34)nc(-c3cccc4sc5ccccc5c34)n2)cc1]

TABLE 1-continued
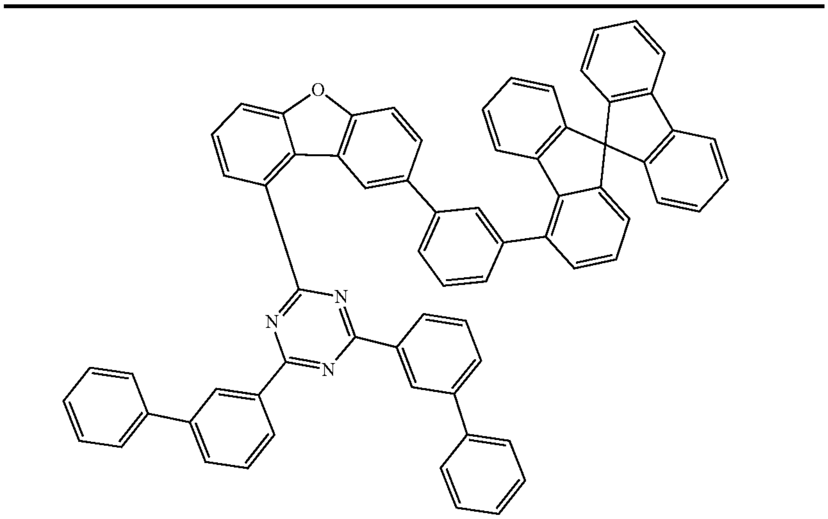
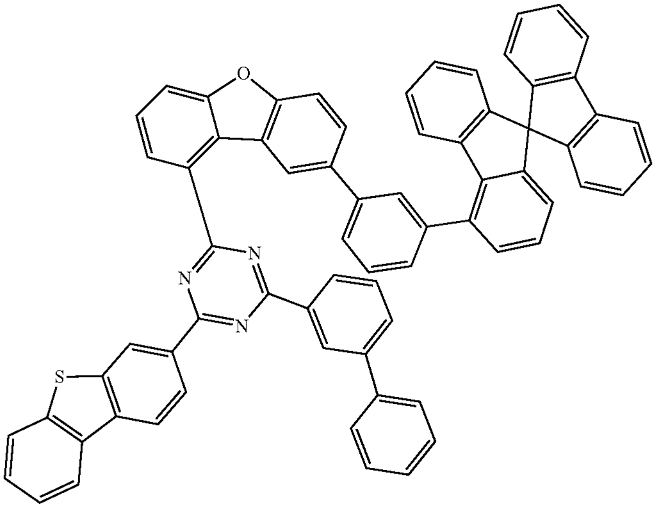 [SMILES: c1ccc(-c2cccc(-c3nc(-c4ccc5c(c4)sc4ccccc45)nc(-c4cccc5oc6ccc(-c7cccc(-c8cccc9c8-c8ccccc8C98c9ccccc9-c9ccccc98)c7)cc6c45)n3)c2)cc1]
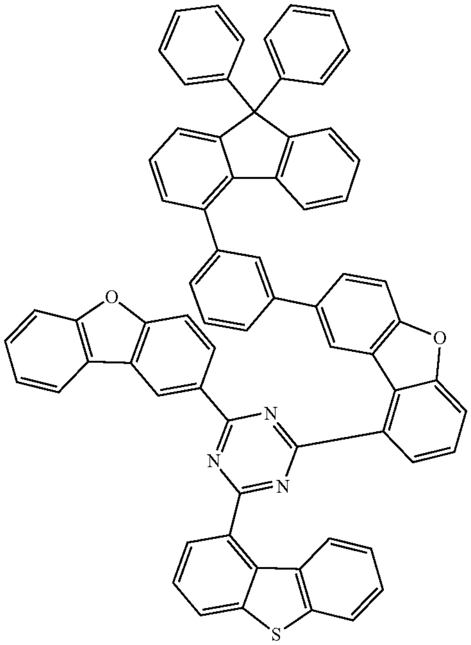 [SMILES: c1ccc(C2(c3ccccc3)c3ccccc3-c3c(-c4cccc(-c5ccc6oc7cccc(-c8nc(-c9ccc%10oc%11ccccc%11c%10c9)nc(-c9cccc%10sc%11ccccc%11c9%10)n8)c7c6c5)c4)cccc32)cc1]

TABLE 1-continued
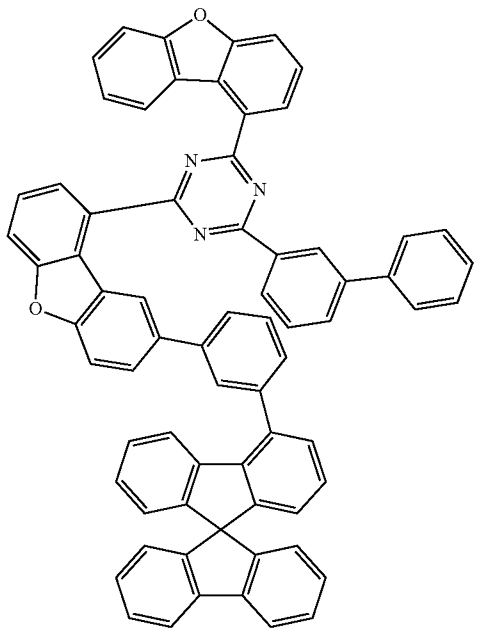 [SMILES: c1ccc(-c2cccc(-c3nc(-c4cccc5oc6ccccc6c45)nc(-c4cccc5oc6ccc(-c7cccc(-c8cccc9c8-c8ccccc8C98c9ccccc9-c9ccccc98)c7)cc6c45)n3)c2)cc1]
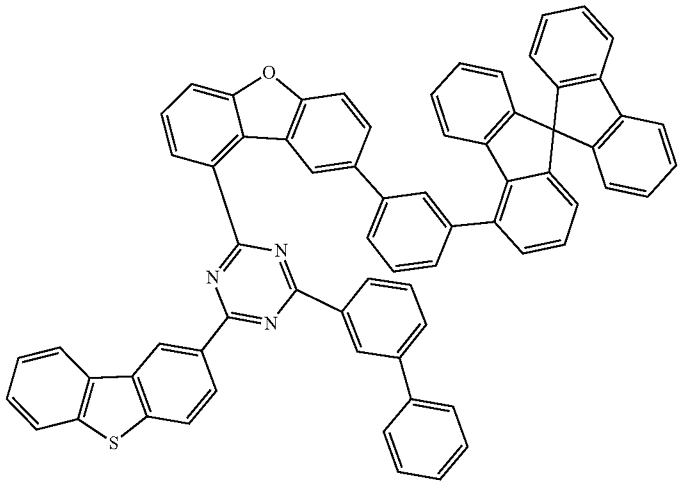 [SMILES: c1ccc(-c2cccc(-c3nc(-c4ccc5sc6ccccc6c5c4)nc(-c4cccc5oc6ccc(-c7cccc(-c8cccc9c8-c8ccccc8C98c9ccccc9-c9ccccc98)c7)cc6c45)n3)c2)cc1]
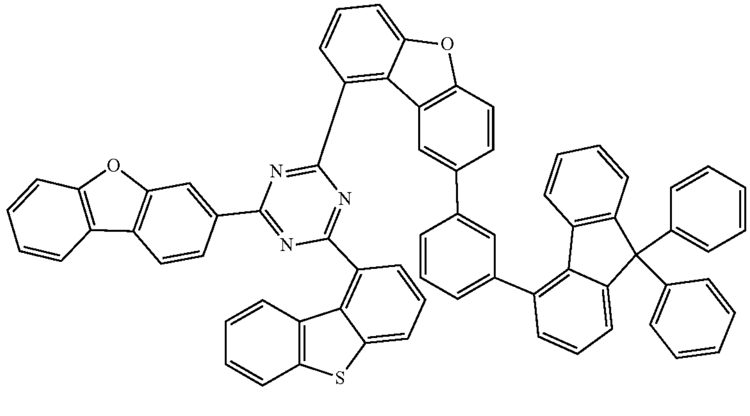 [SMILES: c1ccc(C2(c3ccccc3)c3ccccc3-c3c(-c4cccc(-c5ccc6oc7cccc(-c8nc(-c9ccc%10c(c9)oc9ccccc9%10)nc(-c9cccc%10sc%11ccccc%11c9%10)n8)c7c6c5)c4)cccc32)cc1]

TABLE 1-continued
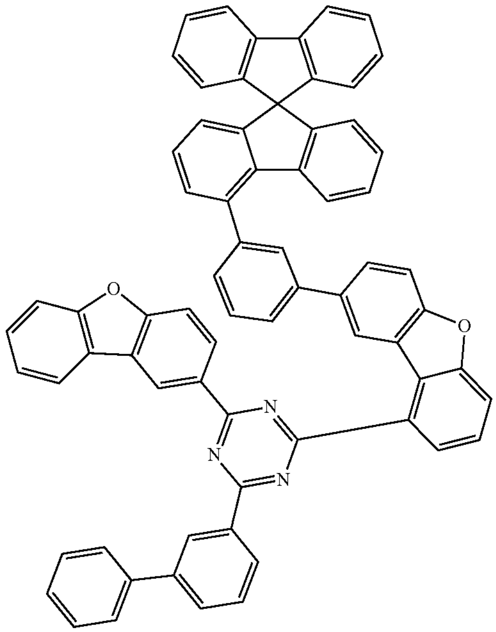 [SMILES: c1ccc(-c2cccc(-c3nc(-c4ccc5oc6ccccc6c5c4)nc(-c4cccc5oc6ccc(-c7cccc(-c8cccc9c8-c8ccccc8C98c9ccccc9-c9ccccc98)c7)cc6c45)n3)c2)cc1]
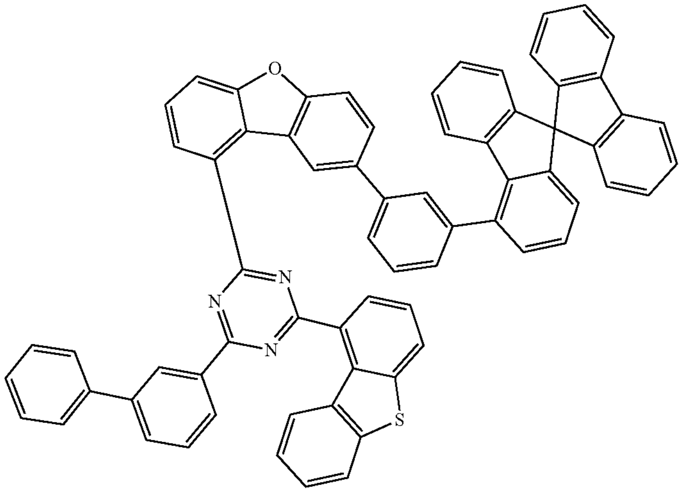 [SMILES: c1ccc(-c2cccc(-c3nc(-c4cccc5oc6ccc(-c7cccc(-c8cccc9c8-c8ccccc8C98c9ccccc9-c9ccccc98)c7)cc6c45)nc(-c4cccc5sc6ccccc6c45)n3)c2)cc1]

TABLE 1-continued
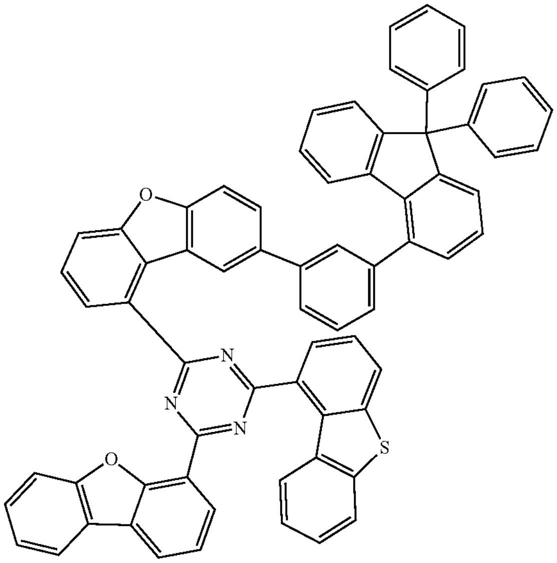 [SMILES: c1ccc(C2(c3ccccc3)c3ccccc3-c3c(-c4cccc(-c5ccc6oc7cccc(-c8nc(-c9cccc%10c9oc9ccccc9%10)nc(-c9cccc%10sc%11ccccc%11c9%10)n8)c7c6c5)c4)cccc32)cc1]
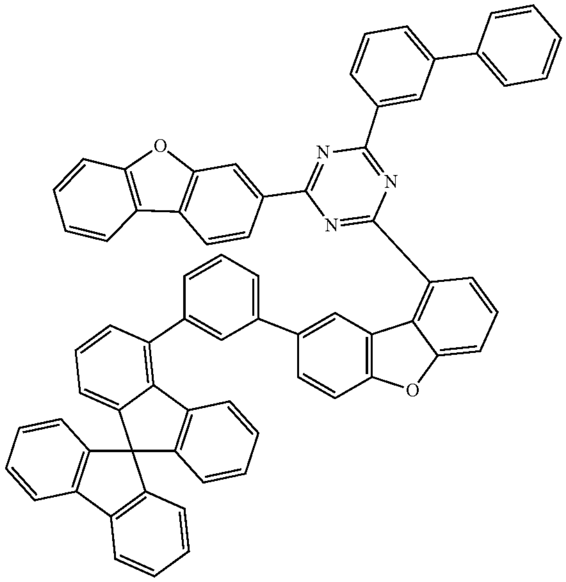 [SMILES: c1ccc(-c2cccc(-c3nc(-c4ccc5c(c4)oc4ccccc45)nc(-c4cccc5oc6ccc(-c7cccc(-c8cccc9c8-c8ccccc8C98c9ccccc9-c9ccccc98)c7)cc6c45)n3)c2)cc1]

TABLE 1-continued
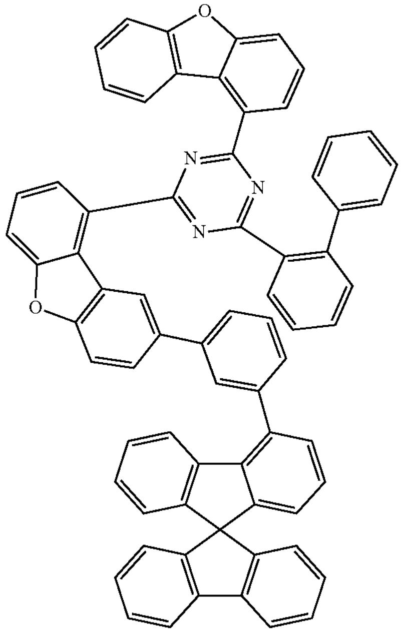 [SMILES: c1ccc(-c2ccccc2-c2nc(-c3cccc4oc5ccccc5c34)nc(-c3cccc4oc5ccc(-c6cccc(-c7cccc8c7-c7ccccc7C87c8ccccc8-c8ccccc87)c6)cc5c34)n2)cc1]
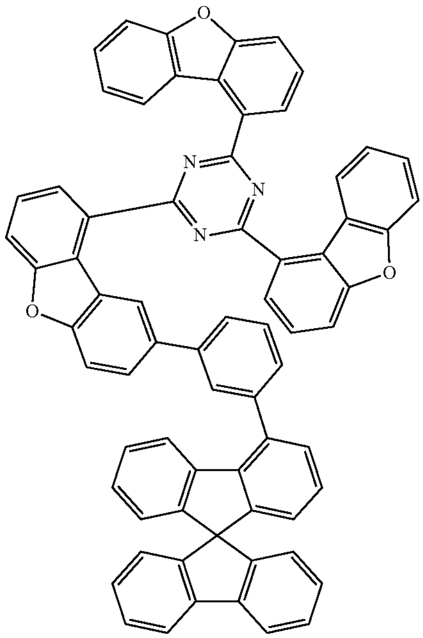 [SMILES: c1cc(-c2ccc3oc4cccc(-c5nc(-c6cccc7oc8ccccc8c67)nc(-c6cccc7oc8ccccc8c67)n5)c4c3c2)cc(-c2cccc3c2-c2ccccc2C32c3ccccc3-c3ccccc32)c1]

TABLE 1-continued
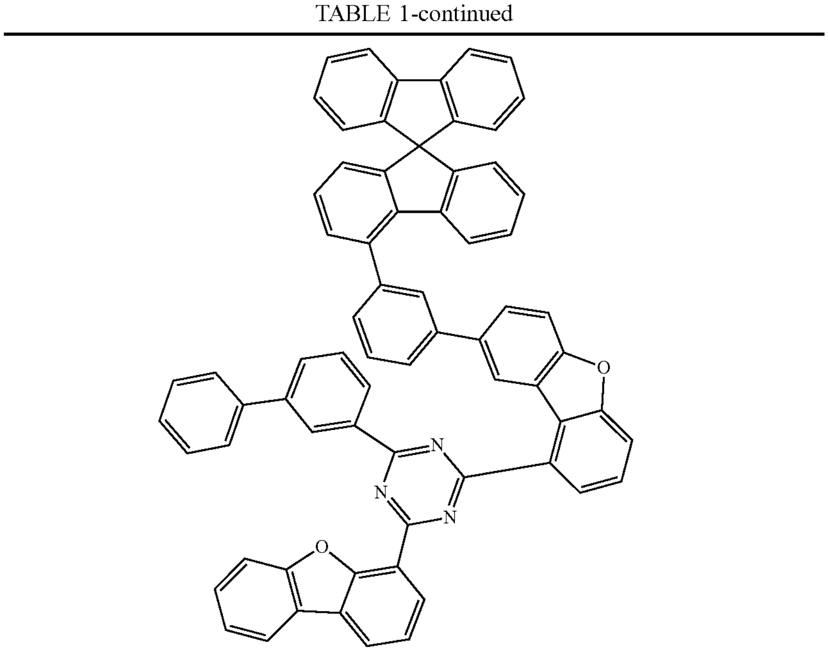
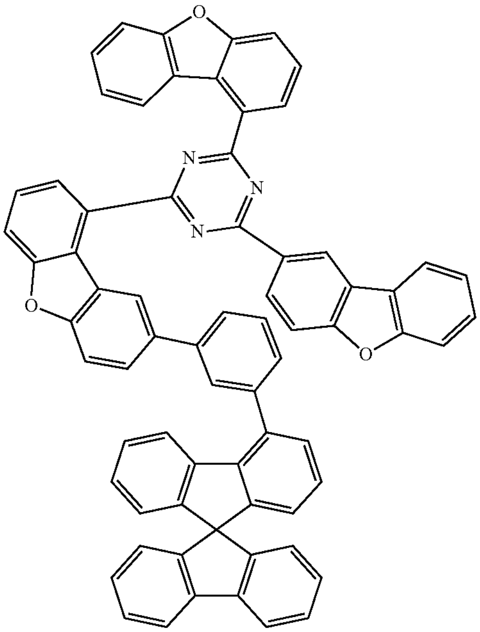 [SMILES: c1cc(-c2ccc3oc4cccc(-c5nc(-c6ccc7oc8ccccc8c7c6)nc(-c6cccc7oc8ccccc8c67)n5)c4c3c2)cc(-c2cccc3c2-c2ccccc2C32c3ccccc3-c3ccccc32)c1]

TABLE 1-continued
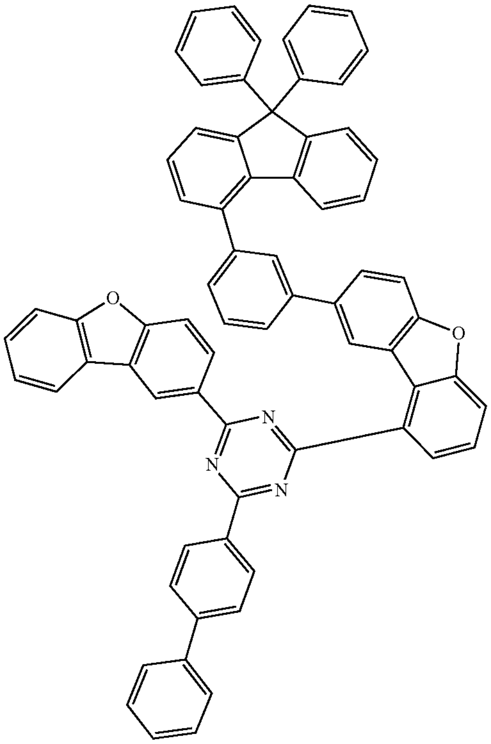 [SMILES: c1ccc(-c2ccc(-c3nc(-c4ccc5oc6ccccc6c5c4)nc(-c4cccc5oc6ccc(-c7cccc(-c8cccc9c8-c8ccccc8C9(c8ccccc8)c8ccccc8)c7)cc6c45)n3)cc2)cc1]
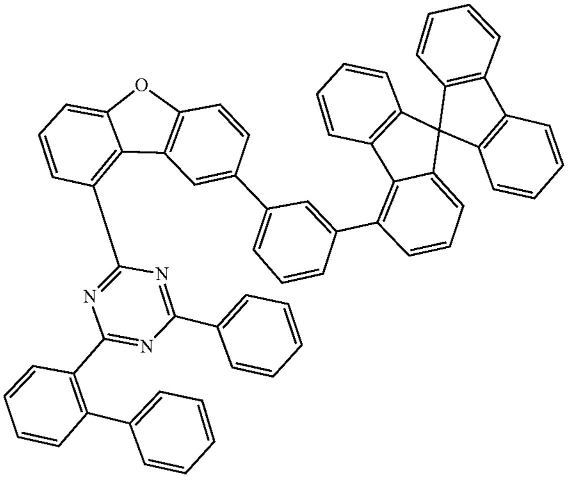 [SMILES: c1ccc(-c2nc(-c3ccccc3-c3ccccc3)nc(-c3cccc4oc5ccc(-c6cccc(-c7cccc8c7-c7ccccc7C87c8ccccc8-c8ccccc87)c6)cc5c34)n2)cc1]

TABLE 1-continued
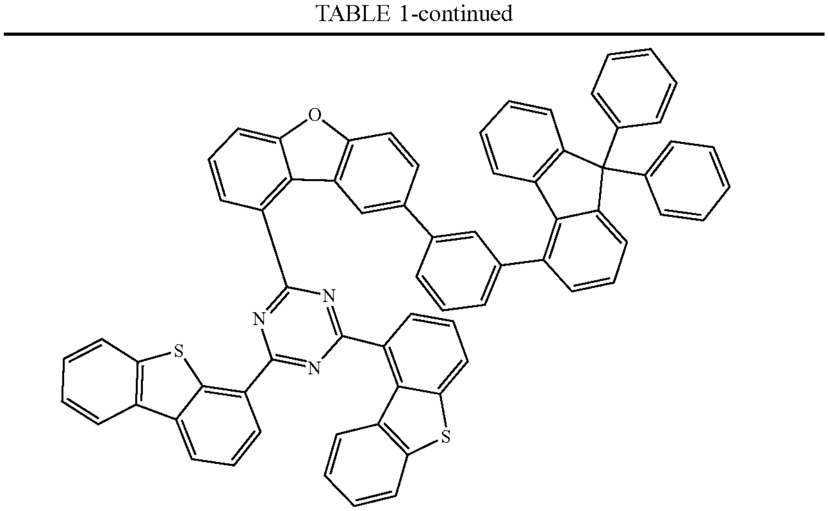
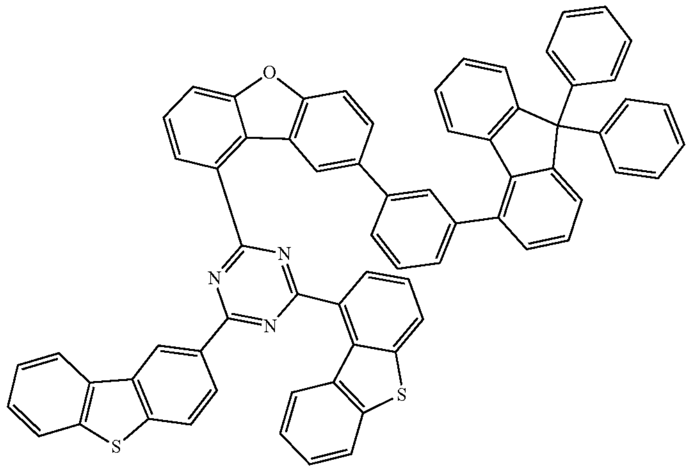 [SMILES: c1ccc(C2(c3ccccc3)c3ccccc3-c3c(-c4cccc(-c5ccc6oc7cccc(-c8nc(-c9ccc%10sc%11ccccc%11c%10c9)nc(-c9cccc%10sc%11ccccc%11c9%10)n8)c7c6c5)c4)cccc32)cc1]
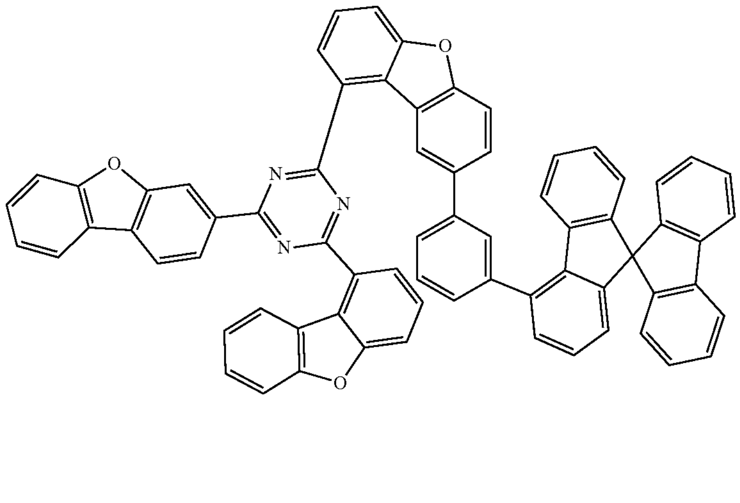 [SMILES: c1cc(-c2ccc3oc4cccc(-c5nc(-c6ccc7c(c6)oc6ccccc67)nc(-c6cccc7oc8ccccc8c67)n5)c4c3c2)cc(-c2cccc3c2-c2ccccc2C32c3ccccc3-c3ccccc32)c1]

TABLE 1-continued
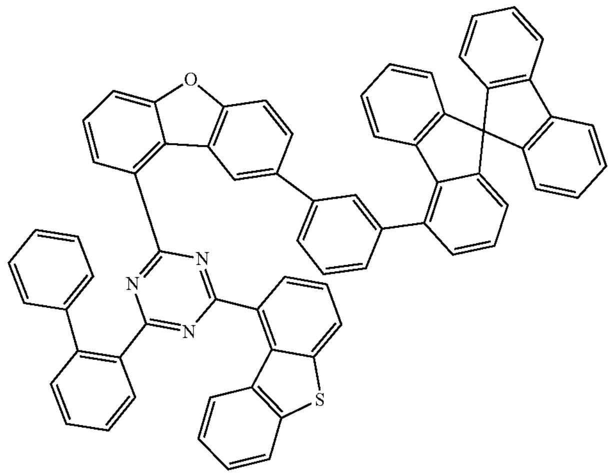 [SMILES: c1ccc(-c2ccccc2-c2nc(-c3cccc4oc5ccc(-c6cccc(-c7cccc8c7-c7ccccc7C87c8ccccc8-c8ccccc87)c6)cc5c34)nc(-c3cccc4sc5ccccc5c34)n2)cc1]
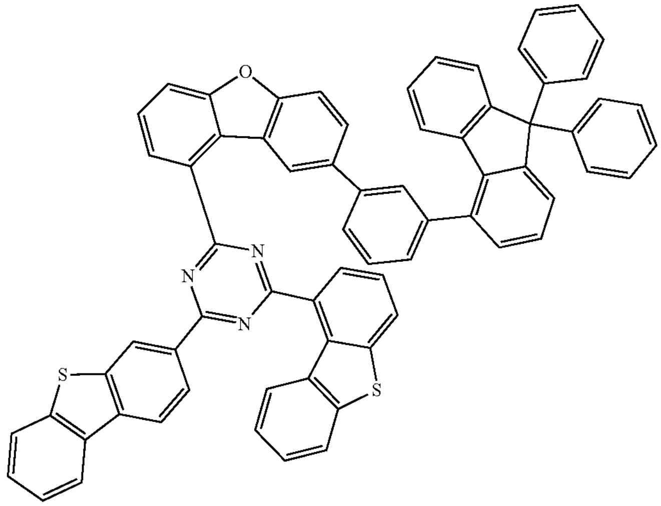 [SMILES: c1ccc(C2(c3ccccc3)c3ccccc3-c3c(-c4cccc(-c5ccc6oc7cccc(-c8nc(-c9ccc%10c(c9)sc9ccccc9%10)nc(-c9cccc%10sc%11ccccc%11c9%10)n8)c7c6c5)c4)cccc32)cc1]
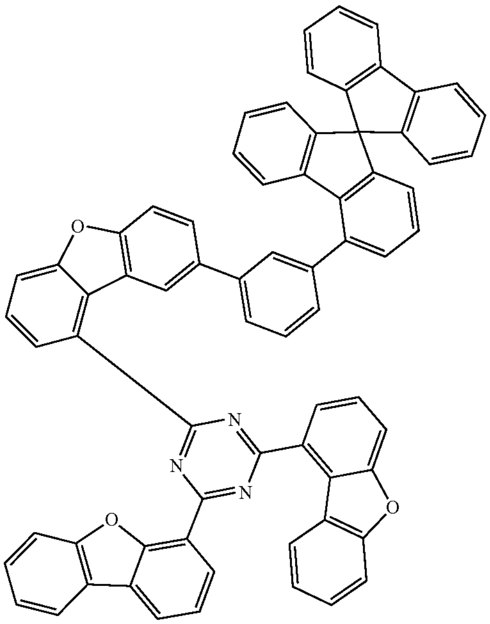 [SMILES: c1cc(-c2ccc3oc4cccc(-c5nc(-c6cccc7c6oc6ccccc67)nc(-c6cccc7oc8ccccc8c67)n5)c4c3c2)cc(-c2cccc3c2-c2ccccc2C32c3ccccc3-c3ccccc32)c1]

TABLE 1-continued
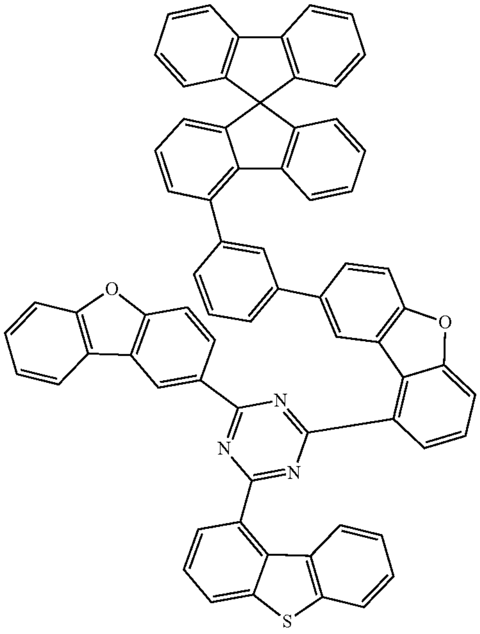 [SMILES: c1cc(-c2ccc3oc4cccc(-c5nc(-c6ccc7oc8ccccc8c7c6)nc(-c6cccc7sc8ccccc8c67)n5)c4c3c2)cc(-c2cccc3c2-c2ccccc2C32c3ccccc3-c3ccccc32)c1]
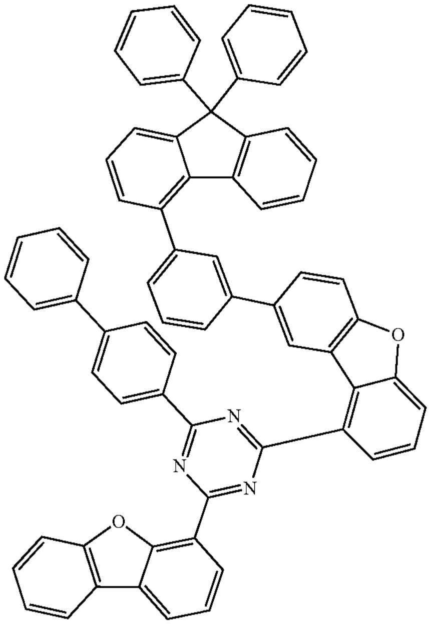 [SMILES: c1ccc(-c2ccc(-c3nc(-c4cccc5c4oc4ccccc45)nc(-c4cccc5oc6ccc(-c7cccc(-c8cccc9c8-c8ccccc8C9(c8ccccc8)c8ccccc8)c7)cc6c45)n3)cc2)cc1]
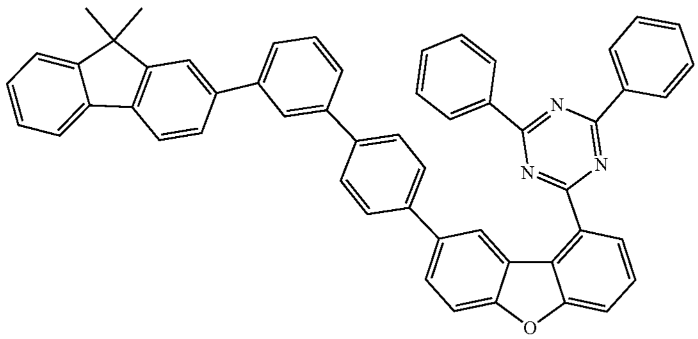 [SMILES: CC1(C)c2ccccc2-c2ccc(-c3cccc(-c4ccc(-c5ccc6oc7cccc(-c8nc(-c9ccccc9)nc(-c9ccccc9)n8)c7c6c5)cc4)c3)cc21]

TABLE 1-continued
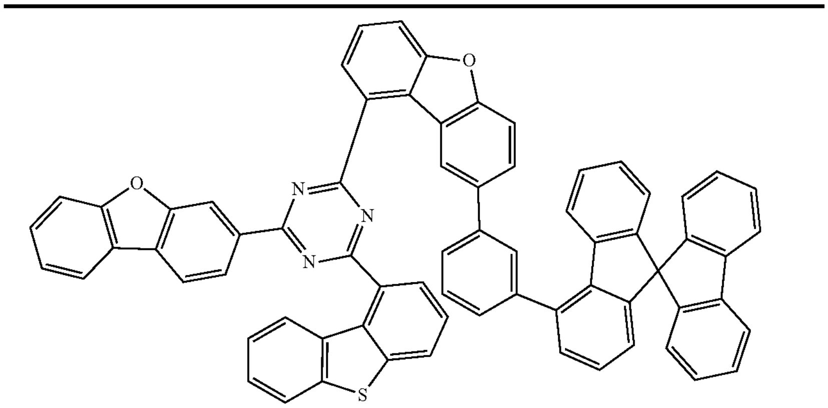
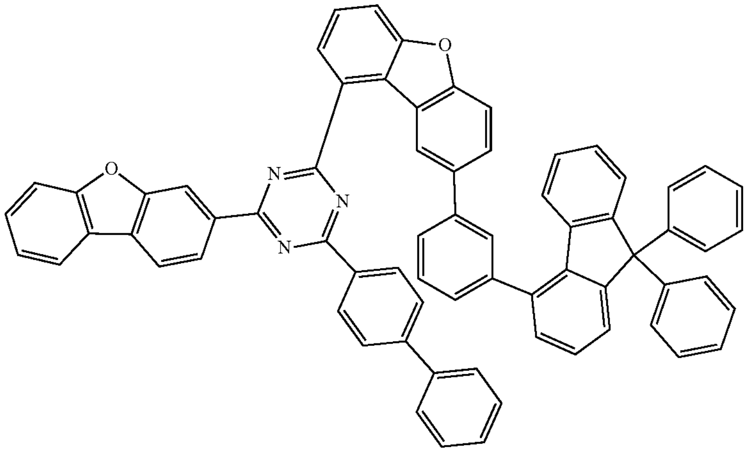 [SMILES: c1ccc(-c2ccc(-c3nc(-c4ccc5c(c4)oc4ccccc45)nc(-c4cccc5oc6ccc(-c7cccc(-c8cccc9c8-c8ccccc8C9(c8ccccc8)c8ccccc8)c7)cc6c45)n3)cc2)cc1]
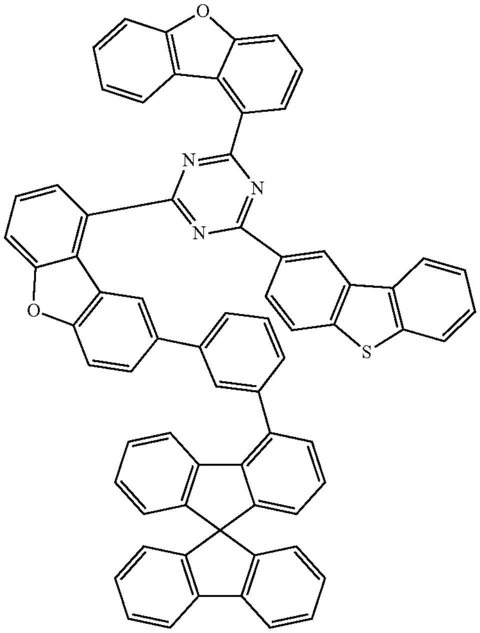 [SMILES: c1cc(-c2ccc3oc4cccc(-c5nc(-c6ccc7sc8ccccc8c7c6)nc(-c6cccc7oc8ccccc8c67)n5)c4c3c2)cc(-c2cccc3c2-c2ccccc2C32c3ccccc3-c3ccccc32)c1]

TABLE 1-continued
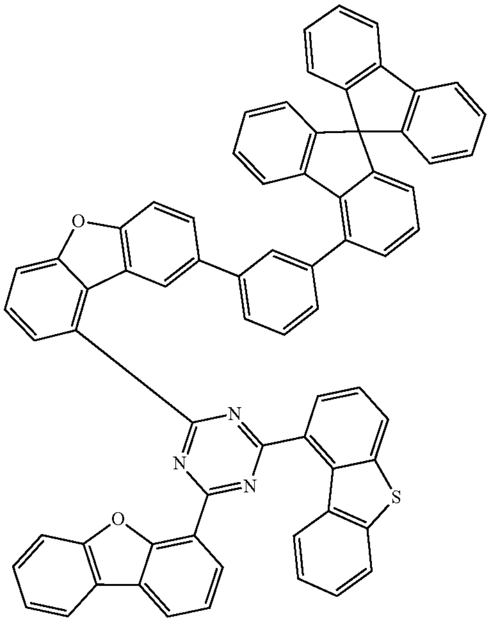 [SMILES: c1cc(-c2ccc3oc4cccc(-c5nc(-c6cccc7c6oc6ccccc67)nc(-c6cccc7sc8ccccc8c67)n5)c4c3c2)cc(-c2cccc3c2-c2ccccc2C32c3ccccc3-c3ccccc32)c1]
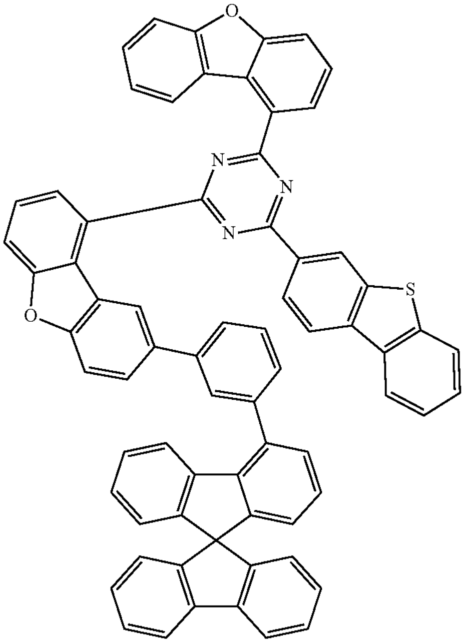 [SMILES: c1cc(-c2ccc3oc4cccc(-c5nc(-c6ccc7c(c6)sc6ccccc67)nc(-c6cccc7oc8ccccc8c67)n5)c4c3c2)cc(-c2cccc3c2-c2ccccc2C32c3ccccc3-c3ccccc32)c1]

TABLE 1-continued
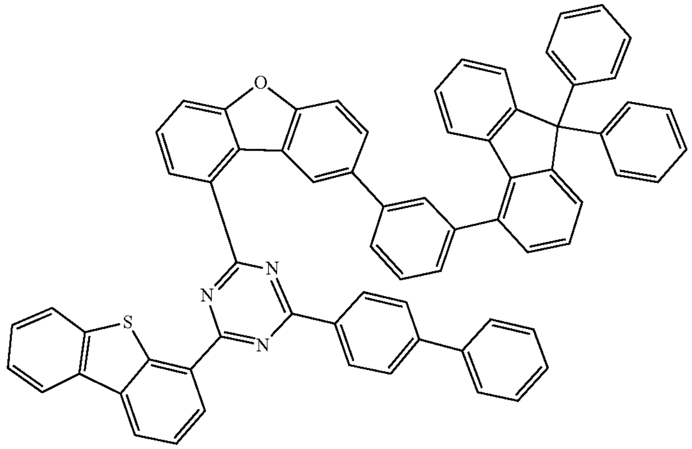
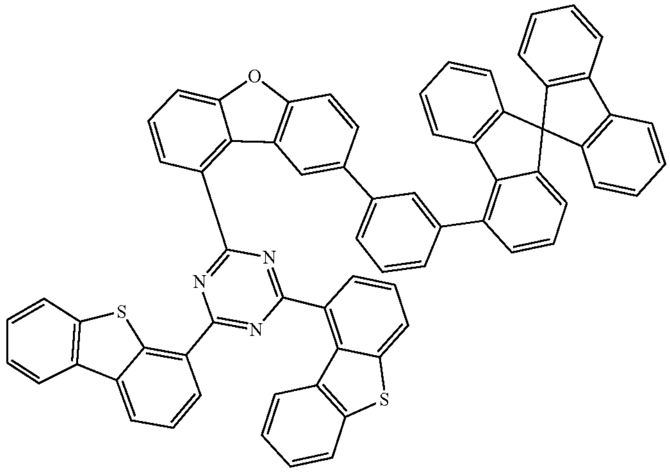 [SMILES: c1cc(-c2ccc3oc4cccc(-c5nc(-c6cccc7c6sc6ccccc67)nc(-c6cccc7sc8ccccc8c67)n5)c4c3c2)cc(-c2cccc3c2-c2ccccc2C32c3ccccc3-c3ccccc32)c1]
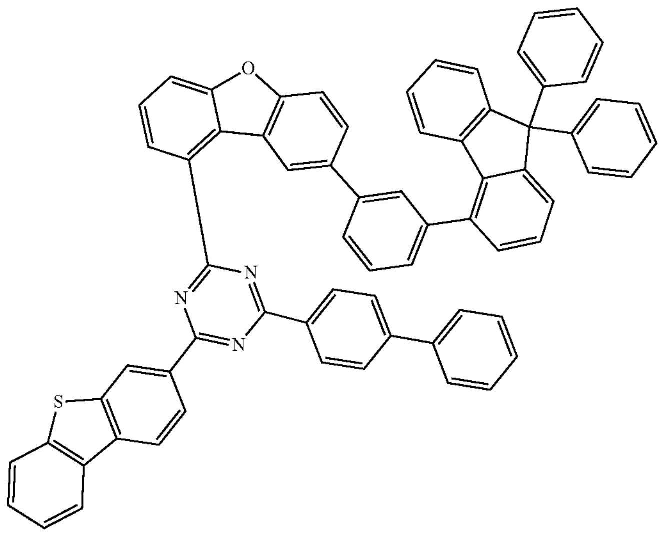 [SMILES: c1ccc(-c2ccc(-c3nc(-c4ccc5c(c4)sc4ccccc45)nc(-c4cccc5oc6ccc(-c7cccc(-c8cccc9c8-c8ccccc8C9(c8ccccc8)c8ccccc8)c7)cc6c45)n3)cc2)cc1]

TABLE 1-continued
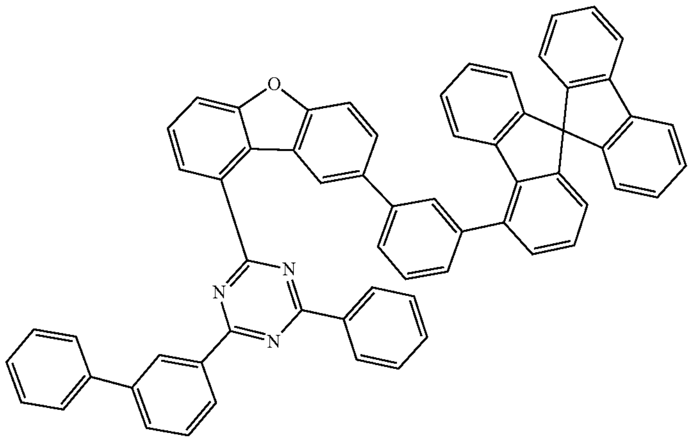 [SMILES: c1ccc(-c2cccc(-c3nc(-c4ccccc4)nc(-c4cccc5oc6ccc(-c7cccc(-c8cccc9c8-c8ccccc8C98c9ccccc9-c9ccccc98)c7)cc6c45)n3)c2)cc1]
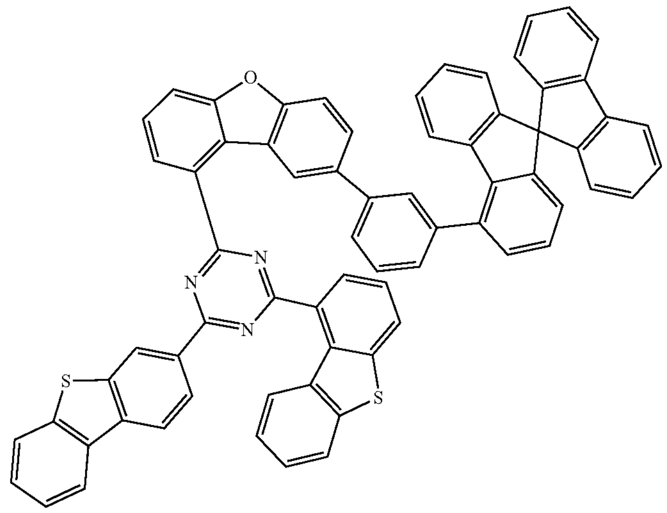 [SMILES: c1cc(-c2ccc3oc4cccc(-c5nc(-c6ccc7c(c6)sc6ccccc67)nc(-c6cccc7sc8ccccc8c67)n5)c4c3c2)cc(-c2cccc3c2-c2ccccc2C32c3ccccc3-c3ccccc32)c1]
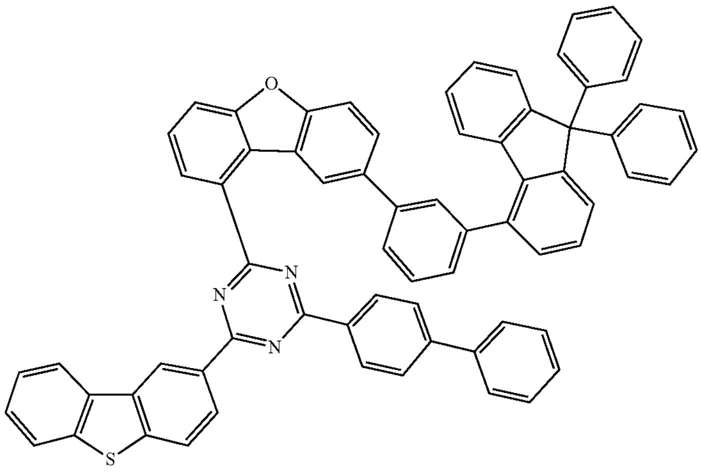 [SMILES: c1ccc(-c2ccc(-c3nc(-c4ccc5sc6ccccc6c5c4)nc(-c4cccc5oc6ccc(-c7cccc(-c8cccc9c8-c8ccccc8C9(c8ccccc8)c8ccccc8)c7)cc6c45)n3)cc2)cc1]

TABLE 1-continued
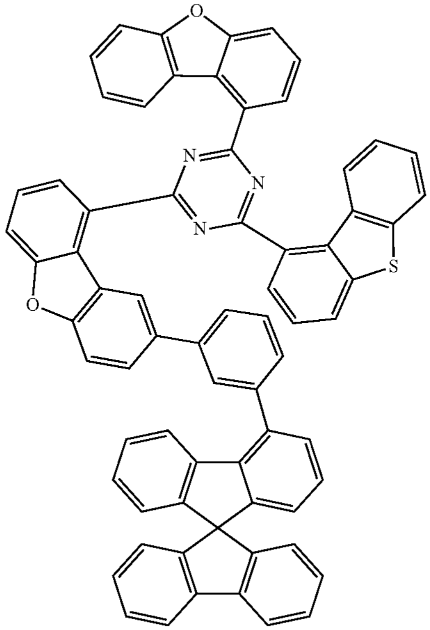 [SMILES: c1cc(-c2ccc3oc4cccc(-c5nc(-c6cccc7oc8ccccc8c67)nc(-c6cccc7sc8ccccc8c67)n5)c4c3c2)cc(-c2cccc3c2-c2ccccc2C32c3ccccc3-c3ccccc32)c1]
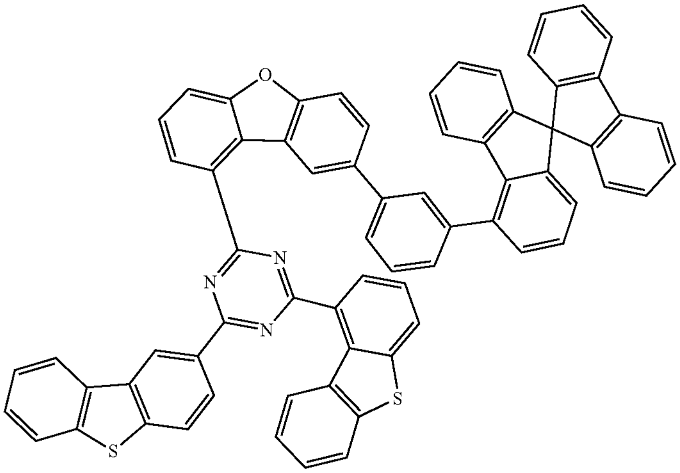 [SMILES: c1cc(-c2ccc3oc4cccc(-c5nc(-c6ccc7sc8ccccc8c7c6)nc(-c6cccc7sc8ccccc8c67)n5)c4c3c2)cc(-c2cccc3c2-c2ccccc2C32c3ccccc3-c3ccccc32)c1]
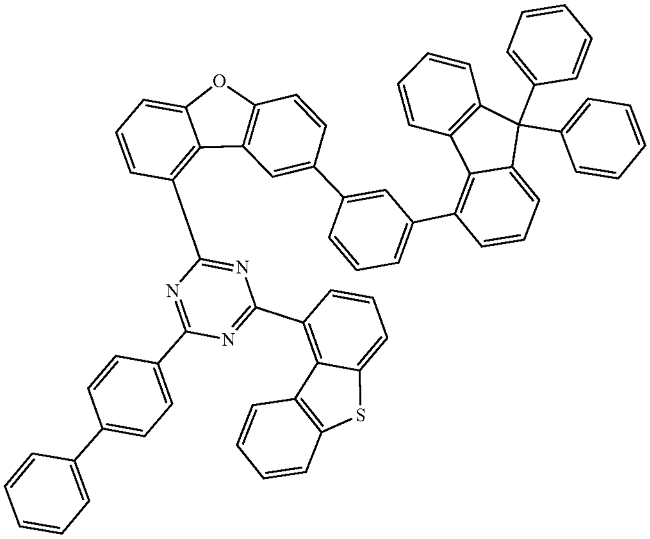 [SMILES: c1ccc(-c2ccc(-c3nc(-c4cccc5oc6ccc(-c7cccc(-c8cccc9c8-c8ccccc8C9(c8ccccc8)c8ccccc8)c7)cc6c45)nc(-c4cccc5sc6ccccc6c45)n3)cc2)cc1]

TABLE 1-continued
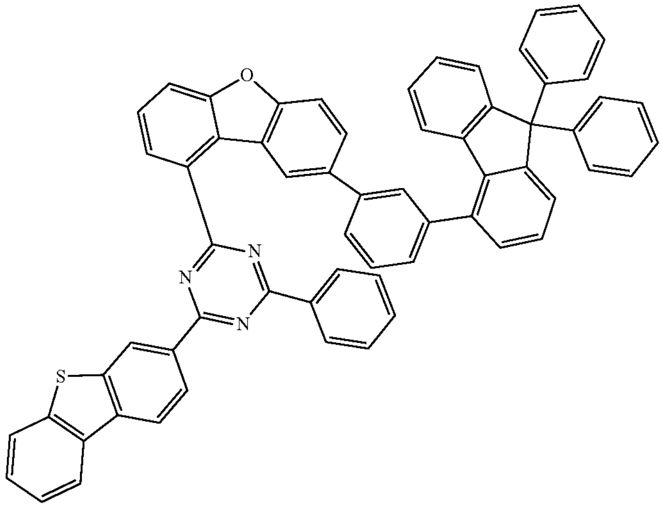 [SMILES: c1ccc(-c2nc(-c3ccc4c(c3)sc3ccccc34)nc(-c3cccc4oc5ccc(-c6cccc(-c7cccc8c7-c7ccccc7C8(c7ccccc7)c7ccccc7)c6)cc5c34)n2)cc1]
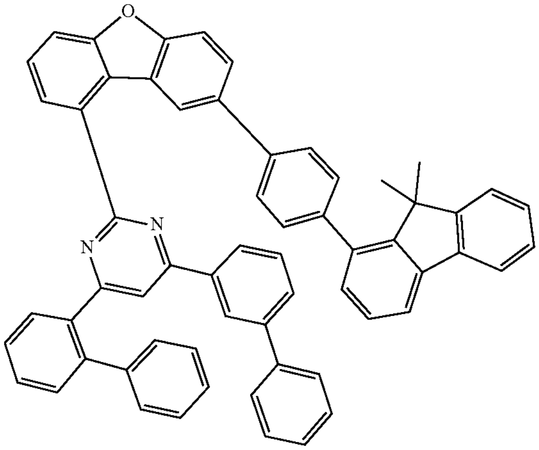 [SMILES: CC1(C)c2ccccc2-c2cccc(-c3ccc(-c4ccc5oc6cccc(-c7nc(-c8cccc(-c9ccccc9)c8)cc(-c8ccccc8-c8ccccc8)n7)c6c5c4)cc3)c21]
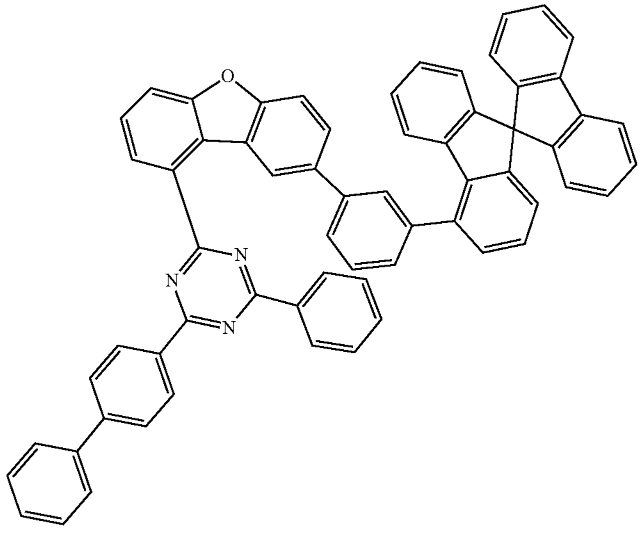 [SMILES: c1ccc(-c2ccc(-c3nc(-c4ccccc4)nc(-c4cccc5oc6ccc(-c7cccc(-c8cccc9c8-c8ccccc8C98c9ccccc9-c9ccccc98)c7)cc6c45)n3)cc2)cc1]

TABLE 1-continued
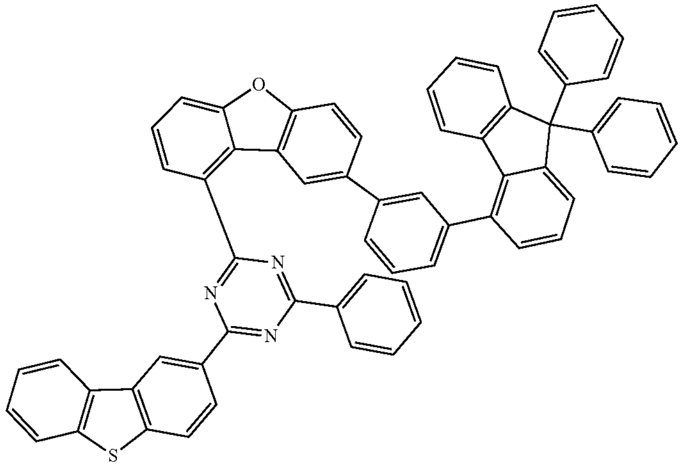 [SMILES: c1ccc(-c2nc(-c3ccc4sc5ccccc5c4c3)nc(-c3cccc4oc5ccc(-c6cccc(-c7cccc8c7-c7ccccc7C8(c7ccccc7)c7ccccc7)c6)cc5c34)n2)cc1]
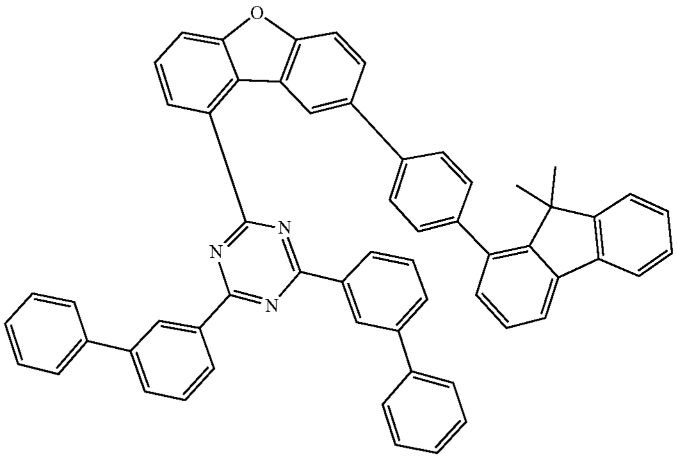 [SMILES: CC1(C)c2ccccc2-c2cccc(-c3ccc(-c4ccc5oc6cccc(-c7nc(-c8cccc(-c9ccccc9)c8)nc(-c8cccc(-c9ccccc9)c8)n7)c6c5c4)cc3)c21]
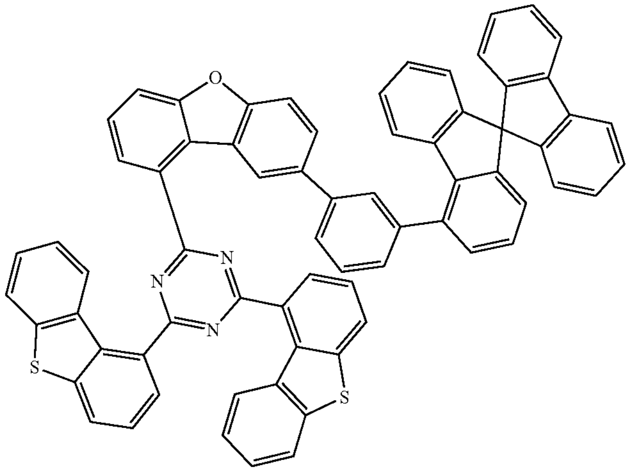 [SMILES: c1cc(-c2ccc3oc4cccc(-c5nc(-c6cccc7sc8ccccc8c67)nc(-c6cccc7sc8ccccc8c67)n5)c4c3c2)cc(-c2cccc3c2-c2ccccc2C32c3ccccc3-c3ccccc32)c1]

TABLE 1-continued
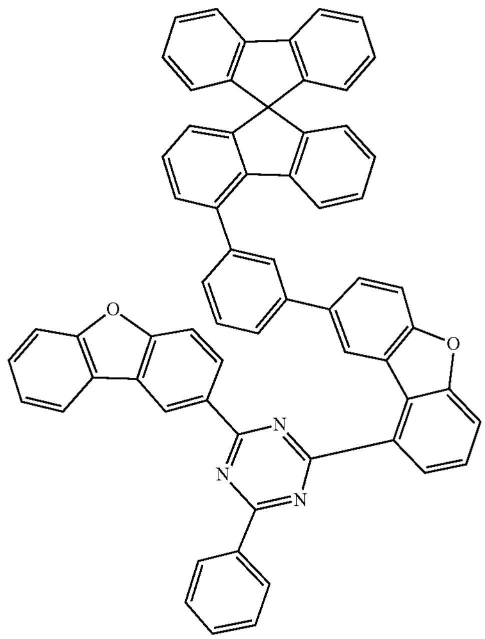 [SMILES: c1ccc(-c2nc(-c3ccc4oc5ccccc5c4c3)nc(-c3cccc4oc5ccc(-c6cccc(-c7cccc8c7-c7ccccc7C87c8ccccc8-c8ccccc87)c6)cc5c34)n2)cc1]
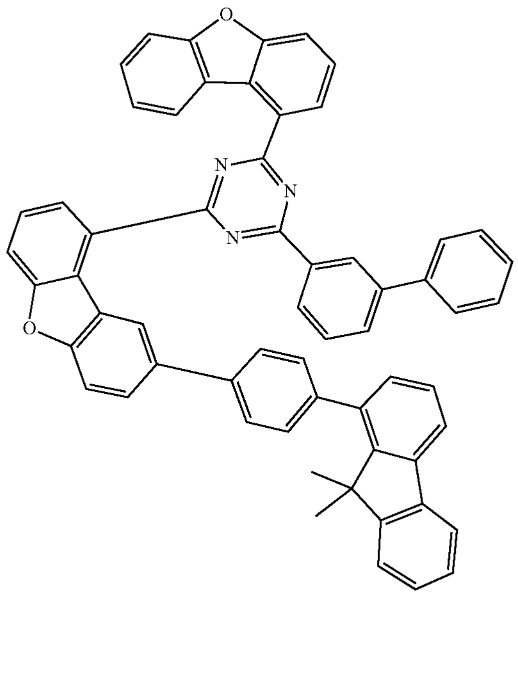 [SMILES: CC1(C)c2ccccc2-c2cccc(-c3ccc(-c4ccc5oc6cccc(-c7nc(-c8cccc(-c9ccccc9)c8)nc(-c8cccc9oc%10ccccc%10c89)n7)c6c5c4)cc3)c21]

TABLE 1-continued
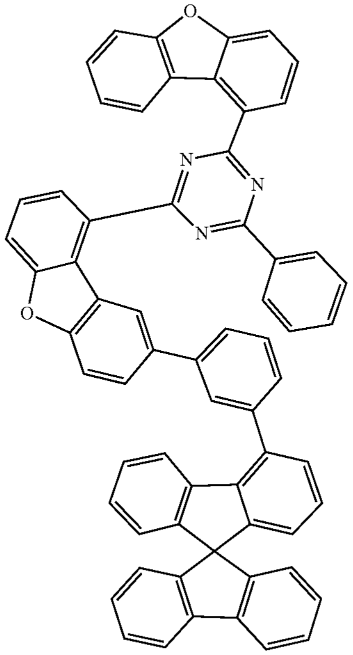 [SMILES: c1ccc(-c2nc(-c3cccc4oc5ccccc5c34)nc(-c3cccc4oc5ccc(-c6cccc(-c7cccc8c7-c7ccccc7C87c8ccccc8-c8ccccc87)c6)cc5c34)n2)cc1]
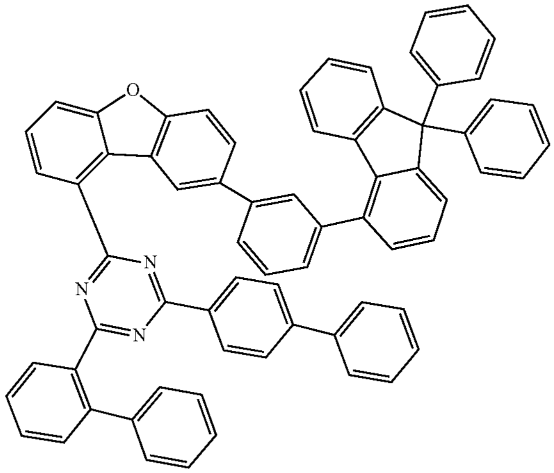 [SMILES: c1ccc(-c2ccc(-c3nc(-c4ccccc4-c4ccccc4)nc(-c4cccc5oc6ccc(-c7cccc(-c8cccc9c8-c8ccccc8C9(c8ccccc8)c8ccccc8)c7)cc6c45)n3)cc2)cc1]

TABLE 1-continued
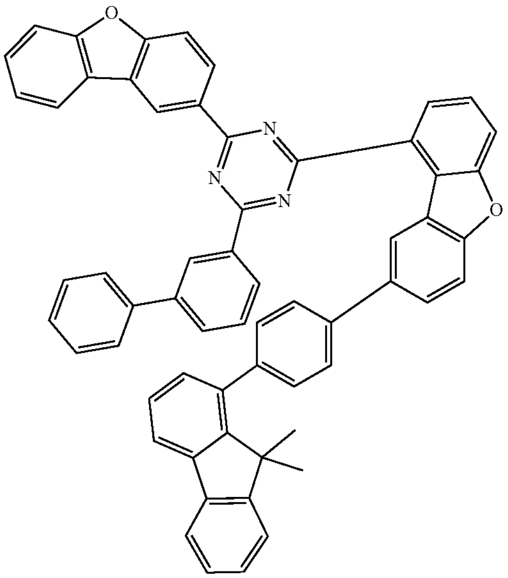 [SMILES: CC1(C)c2ccccc2-c2cccc(-c3ccc(-c4ccc5oc6cccc(-c7nc(-c8cccc(-c9ccccc9)c8)nc(-c8ccc9oc%10ccccc%10c9c8)n7)c6c5c4)cc3)c21]
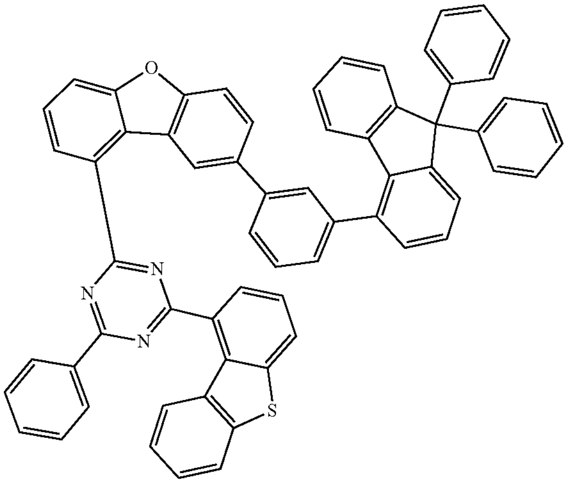 [SMILES: c1ccc(-c2nc(-c3cccc4oc5ccc(-c6cccc(-c7cccc8c7-c7ccccc7C8(c7ccccc7)c7ccccc7)c6)cc5c34)nc(-c3cccc4sc5ccccc5c34)n2)cc1]
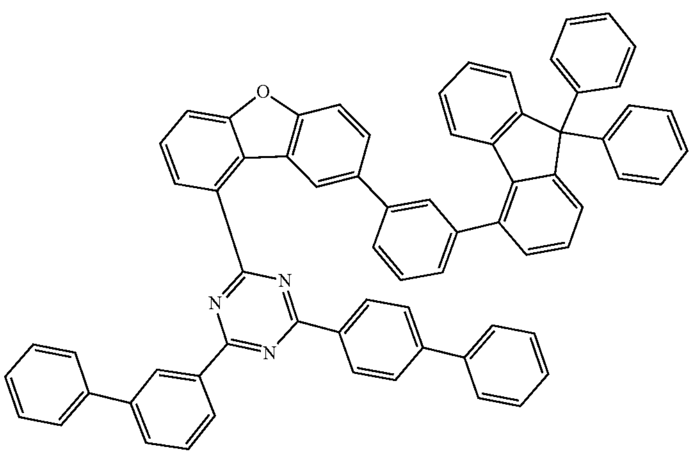 [SMILES: c1ccc(-c2ccc(-c3nc(-c4cccc(-c5ccccc5)c4)nc(-c4cccc5oc6ccc(-c7cccc(-c8cccc9c8-c8ccccc8C9(c8ccccc8)c8ccccc8)c7)cc6c45)n3)cc2)cc1]

TABLE 1-continued
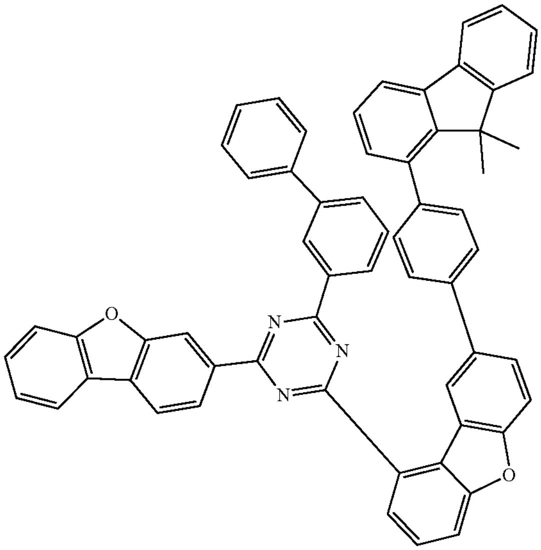 [SMILES: CC1(C)c2ccccc2-c2cccc(-c3ccc(-c4ccc5oc6cccc(-c7nc(-c8cccc(-c9ccccc9)c8)nc(-c8ccc9c(c8)oc8ccccc89)n7)c6c5c4)cc3)c21]
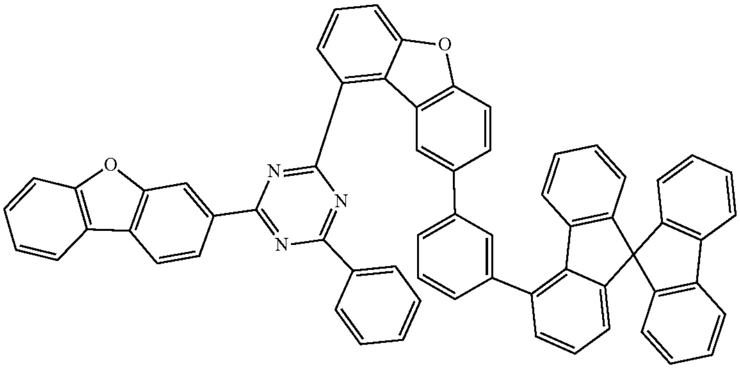 [SMILES: c1ccc(-c2nc(-c3ccc4c(c3)oc3ccccc34)nc(-c3cccc4oc5ccc(-c6cccc(-c7cccc8c7-c7ccccc7C87c8ccccc8-c8ccccc87)c6)cc5c34)n2)cc1]
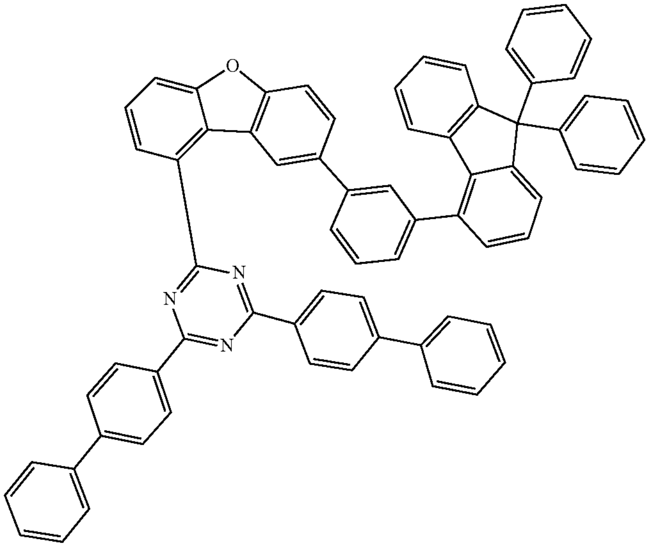 [SMILES: c1ccc(-c2ccc(-c3nc(-c4ccc(-c5ccccc5)cc4)nc(-c4cccc5oc6ccc(-c7cccc(-c8cccc9c8-c8ccccc8C9(c8ccccc8)c8ccccc8)c7)cc6c45)n3)cc2)cc1]

TABLE 1-continued
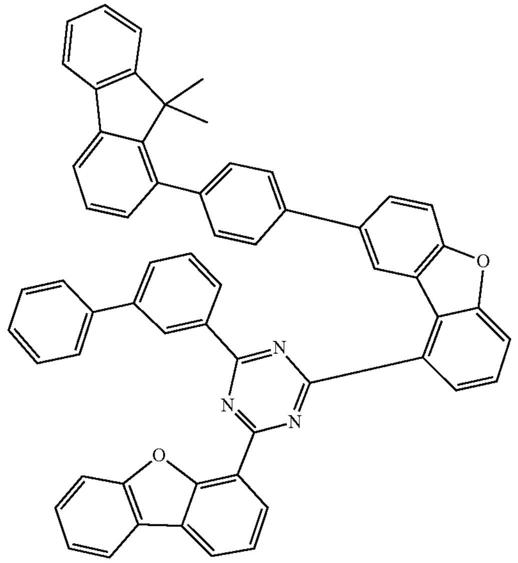 [SMILES: CC1(C)c2ccccc2-c2cccc(-c3ccc(-c4ccc5oc6cccc(-c7nc(-c8cccc(-c9ccccc9)c8)nc(-c8cccc9c8oc8ccccc89)n7)c6c5c4)cc3)c21]
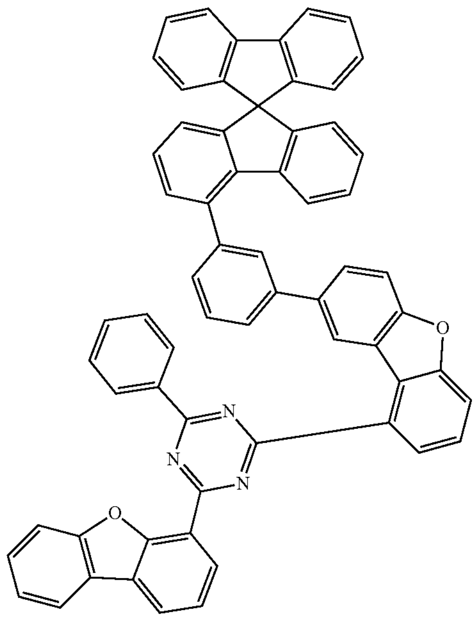 [SMILES: c1ccc(-c2nc(-c3cccc4c3oc3ccccc34)nc(-c3cccc4oc5ccc(-c6cccc(-c7cccc8c7-c7ccccc7C87c8ccccc8-c8ccccc87)c6)cc5c34)n2)cc1]

TABLE 1-continued
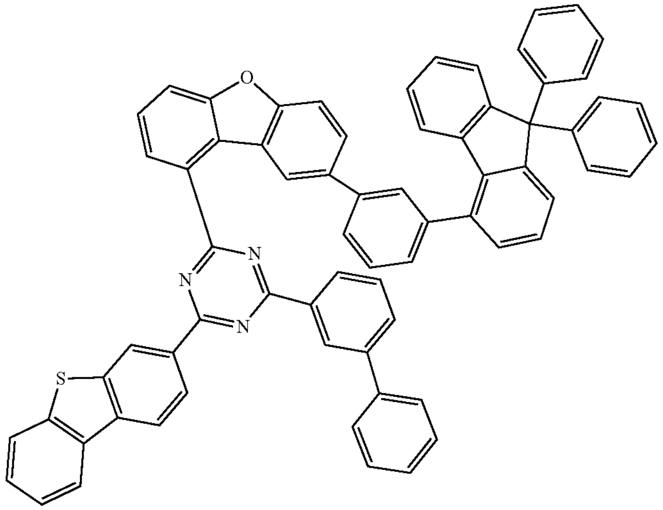 [SMILES: c1ccc(-c2cccc(-c3nc(-c4ccc5c(c4)sc4ccccc45)nc(-c4cccc5oc6ccc(-c7cccc(-c8cccc9c8-c8ccccc8C9(c8ccccc8)c8ccccc8)c7)cc6c45)n3)c2)cc1]
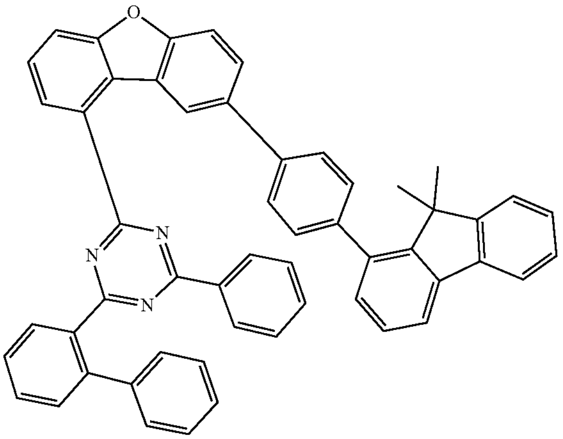 [SMILES: CC1(C)c2ccccc2-c2cccc(-c3ccc(-c4ccc5oc6cccc(-c7nc(-c8ccccc8)nc(-c8ccccc8-c8ccccc8)n7)c6c5c4)cc3)c21]
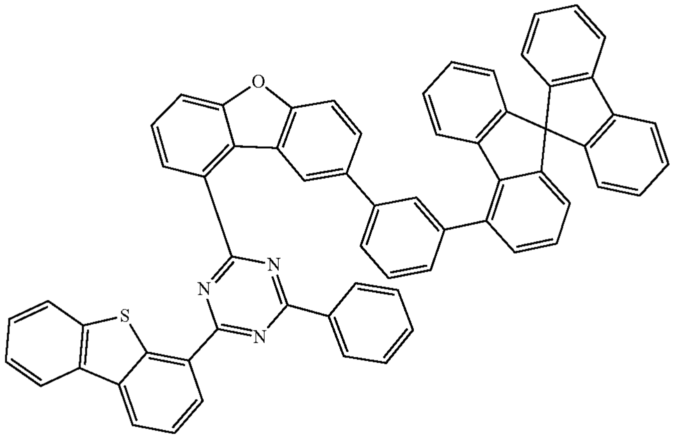 [SMILES: c1ccc(-c2nc(-c3cccc4c3sc3ccccc34)nc(-c3cccc4oc5ccc(-c6cccc(-c7cccc8c7-c7ccccc7C87c8ccccc8-c8ccccc87)c6)cc5c34)n2)cc1]

TABLE 1-continued
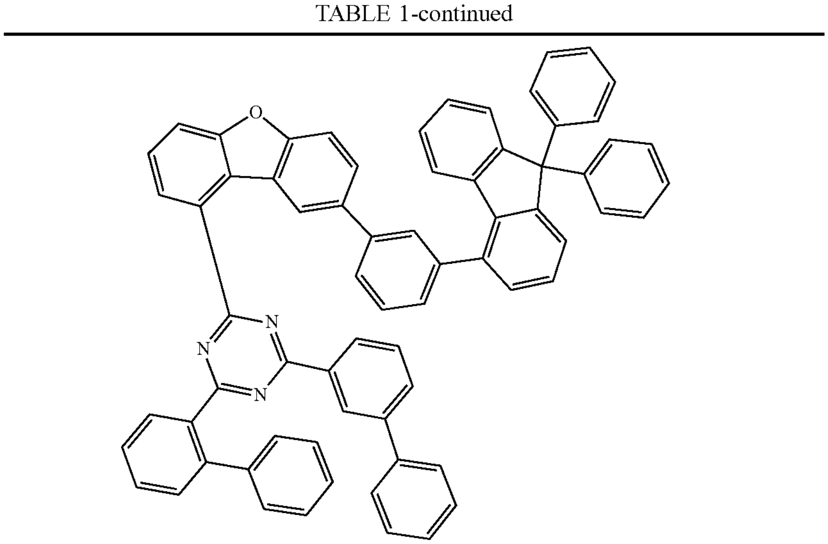
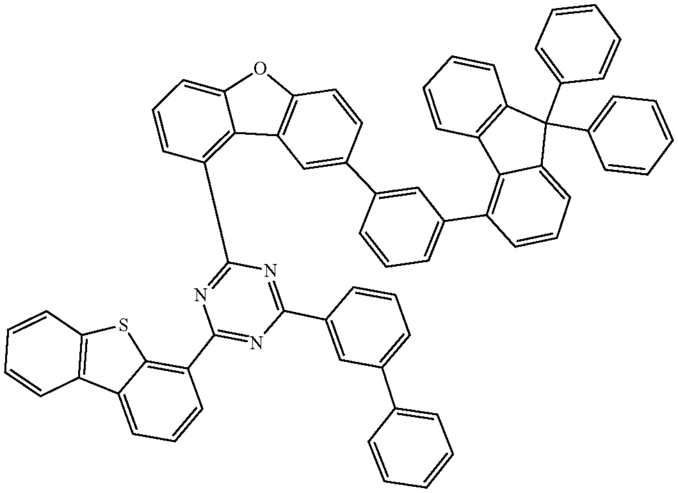 [SMILES: c1ccc(-c2cccc(-c3nc(-c4cccc5c4sc4ccccc45)nc(-c4cccc5oc6ccc(-c7cccc(-c8cccc9c8-c8ccccc8C9(c8ccccc8)c8ccccc8)c7)cc6c45)n3)c2)cc1]
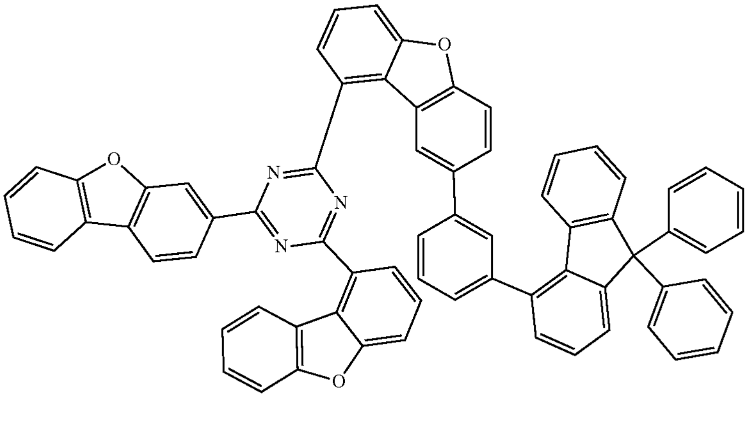 [SMILES: c1ccc(C2(c3ccccc3)c3ccccc3-c3c(-c4cccc(-c5ccc6oc7cccc(-c8nc(-c9ccc%10c(c9)oc9ccccc9%10)nc(-c9cccc%10oc%11ccccc%11c9%10)n8)c7c6c5)c4)cccc32)cc1]

TABLE 1-continued
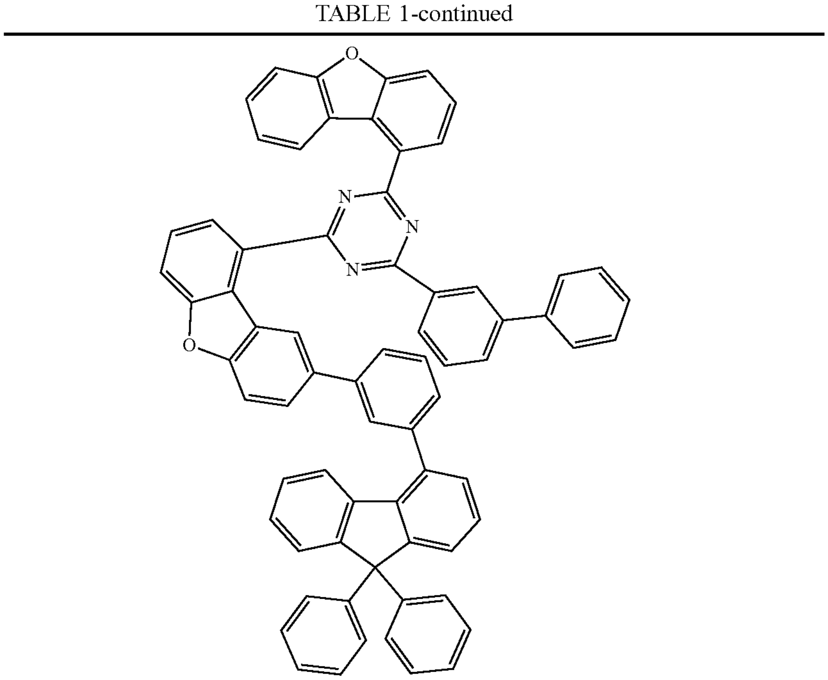
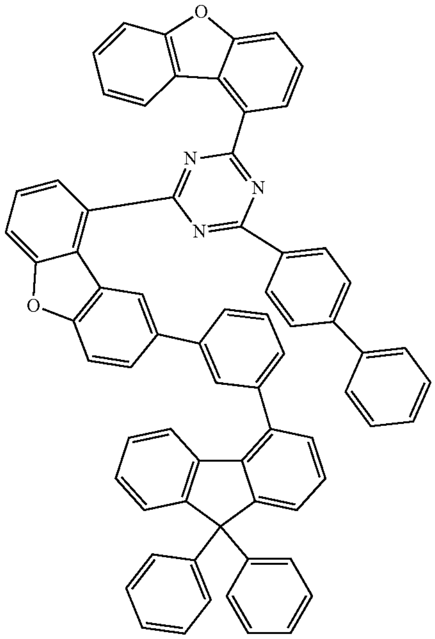 [SMILES: c1ccc(-c2ccc(-c3nc(-c4cccc5oc6ccccc6c45)nc(-c4cccc5oc6ccc(-c7cccc(-c8cccc9c8-c8ccccc8C9(c8ccccc8)c8ccccc8)c7)cc6c45)n3)cc2)cc1]

TABLE 1-continued
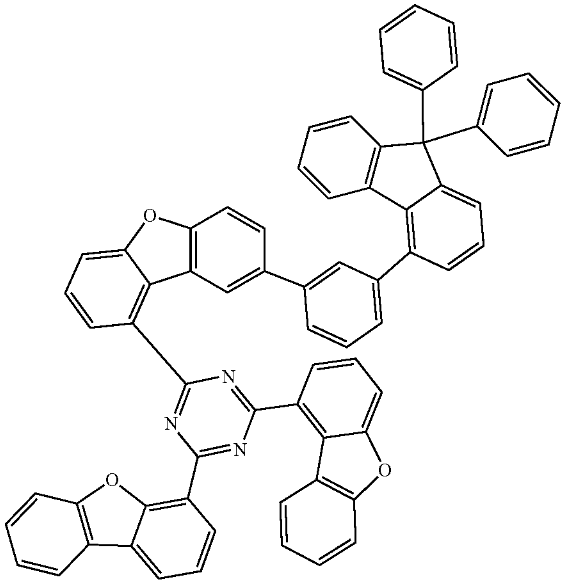 [SMILES: c1ccc(C2(c3ccccc3)c3ccccc3-c3c(-c4cccc(-c5ccc6oc7cccc(-c8nc(-c9cccc%10c9oc9ccccc9%10)nc(-c9cccc%10oc%11ccccc%11c9%10)n8)c7c6c5)c4)cccc32)cc1]
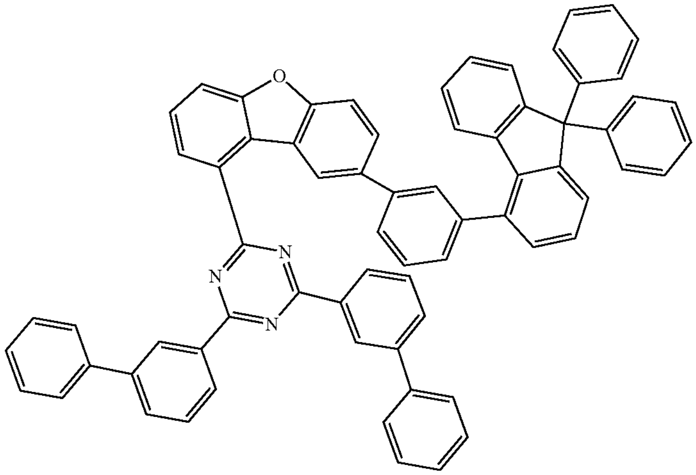 [SMILES: c1ccc(-c2cccc(-c3nc(-c4cccc(-c5ccccc5)c4)nc(-c4cccc5oc6ccc(-c7cccc(-c8cccc9c8-c8ccccc8C9(c8ccccc8)c8ccccc8)c7)cc6c45)n3)c2)cc1]
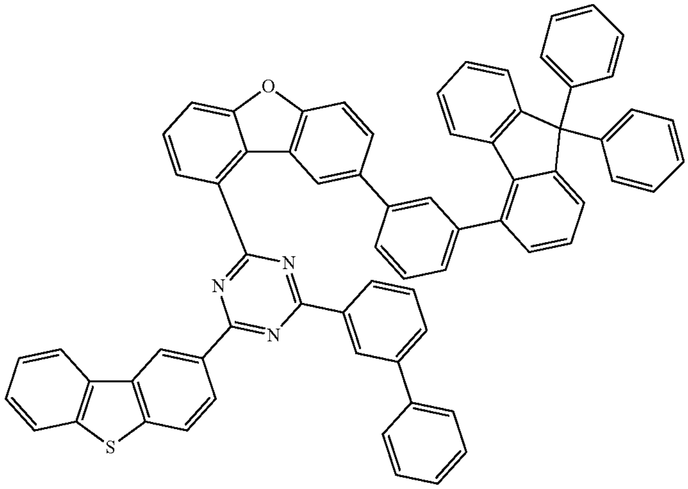 [SMILES: c1ccc(-c2cccc(-c3nc(-c4ccc5sc6ccccc6c5c4)nc(-c4cccc5oc6ccc(-c7cccc(-c8cccc9c8-c8ccccc8C9(c8ccccc8)c8ccccc8)c7)cc6c45)n3)c2)cc1]

TABLE 1-continued
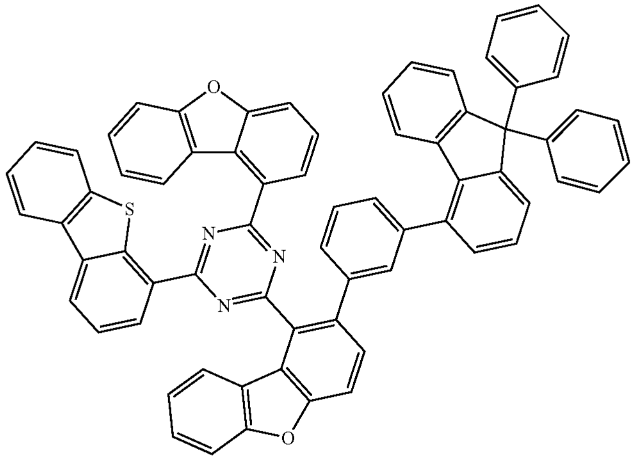 [SMILES: c1ccc(C2(c3ccccc3)c3ccccc3-c3c(-c4cccc(-c5ccc6oc7ccccc7c6c5-c5nc(-c6cccc7c6sc6ccccc67)nc(-c6cccc7oc8ccccc8c67)n5)c4)cccc32)cc1]
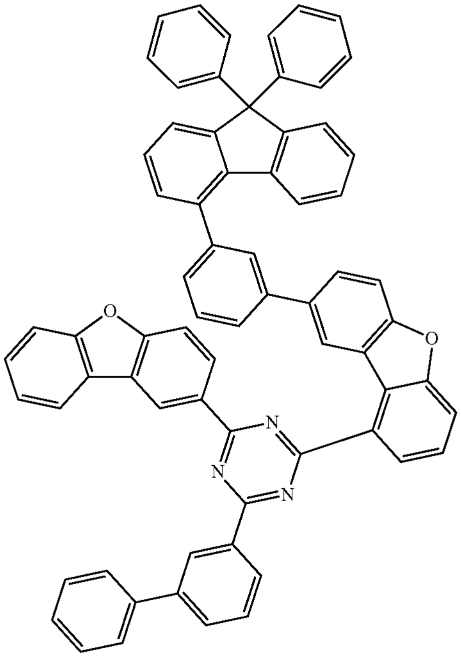 [SMILES: c1ccc(-c2cccc(-c3nc(-c4ccc5oc6ccccc6c5c4)nc(-c4cccc5oc6ccc(-c7cccc(-c8cccc9c8-c8ccccc8C9(c8ccccc8)c8ccccc8)c7)cc6c45)n3)c2)cc1]
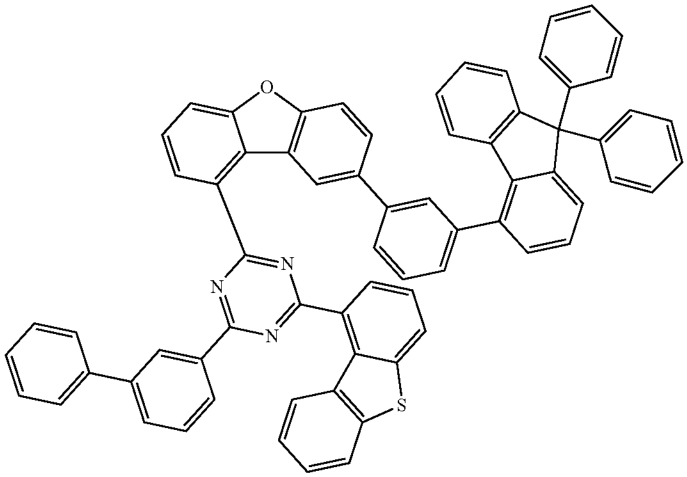 [SMILES: c1ccc(-c2cccc(-c3nc(-c4cccc5oc6ccc(-c7cccc(-c8cccc9c8-c8ccccc8C9(c8ccccc8)c8ccccc8)c7)cc6c45)nc(-c4cccc5sc6ccccc6c45)n3)c2)cc1]

TABLE 1-continued
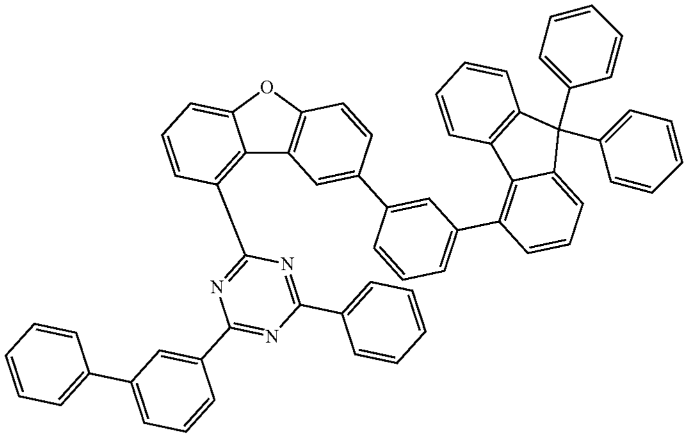 [SMILES: c1ccc(-c2cccc(-c3nc(-c4ccccc4)nc(-c4cccc5oc6ccc(-c7cccc(-c8cccc9c8-c8ccccc8C9(c8ccccc8)c8ccccc8)c7)cc6c45)n3)c2)cc1]
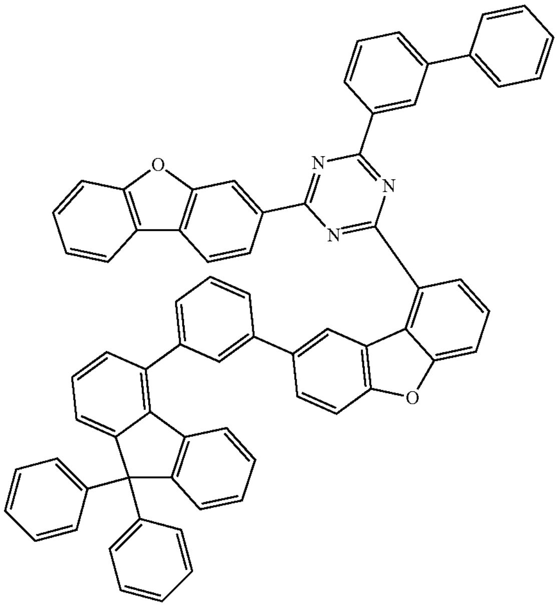 [SMILES: c1ccc(-c2cccc(-c3nc(-c4ccc5c(c4)oc4ccccc45)nc(-c4cccc5oc6ccc(-c7cccc(-c8cccc9c8-c8ccccc8C9(c8ccccc8)c8ccccc8)c7)cc6c45)n3)c2)cc1]

TABLE 1-continued
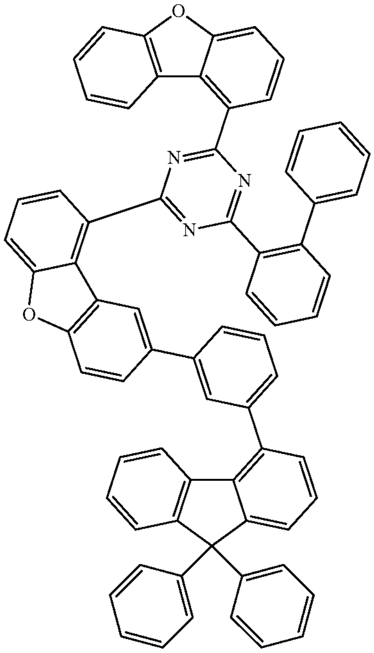 [SMILES: c1ccc(-c2ccccc2-c2nc(-c3cccc4oc5ccccc5c34)nc(-c3cccc4oc5ccc(-c6cccc(-c7cccc8c7-c7ccccc7C8(c7ccccc7)c7ccccc7)c6)cc5c34)n2)cc1]
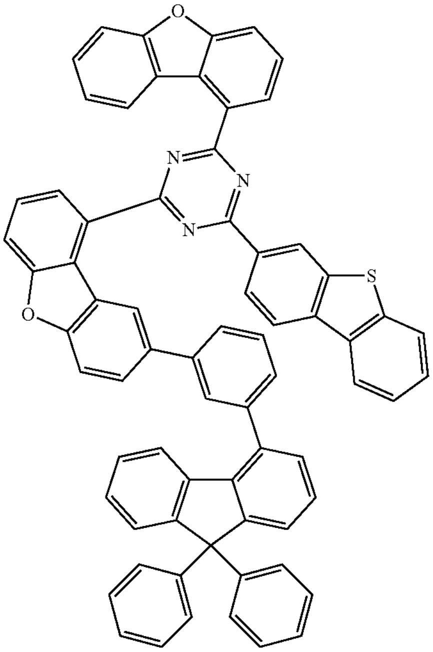 [SMILES: c1ccc(C2(c3ccccc3)c3ccccc3-c3c(-c4cccc(-c5ccc6oc7cccc(-c8nc(-c9ccc%10c(c9)sc9ccccc9%10)nc(-c9cccc%10oc%11ccccc%11c9%10)n8)c7c6c5)c4)cccc32)cc1]

TABLE 1-continued
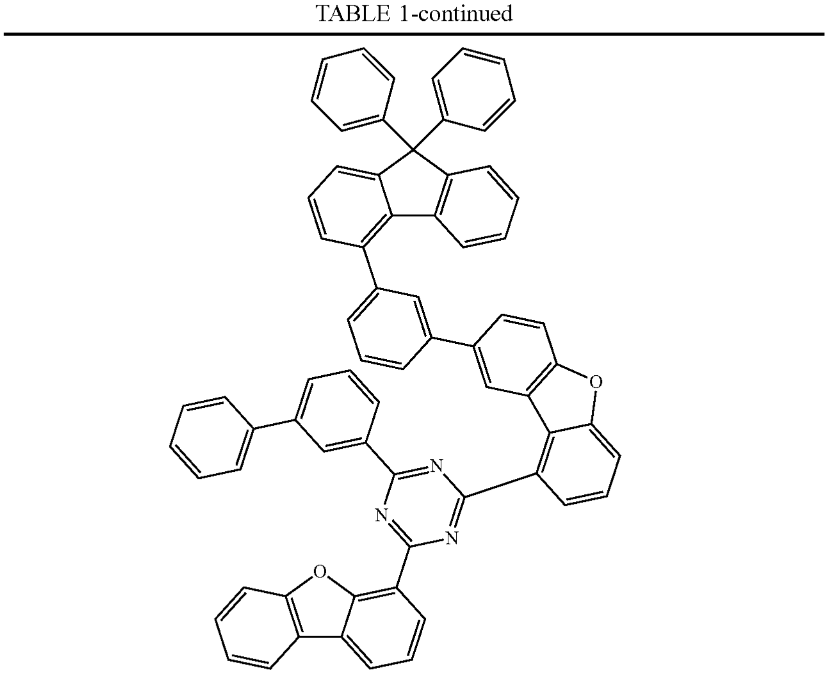
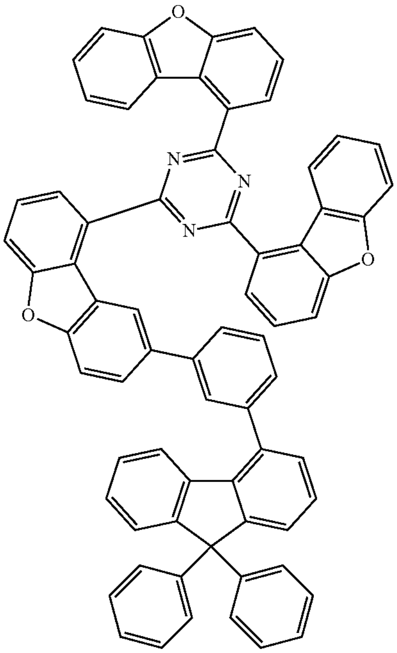 [SMILES: c1ccc(C2(c3ccccc3)c3ccccc3-c3c(-c4cccc(-c5ccc6oc7cccc(-c8nc(-c9cccc%10oc%11ccccc%11c9%10)nc(-c9cccc%10oc%11ccccc%11c9%10)n8)c7c6c5)c4)cccc32)cc1]

TABLE 1-continued
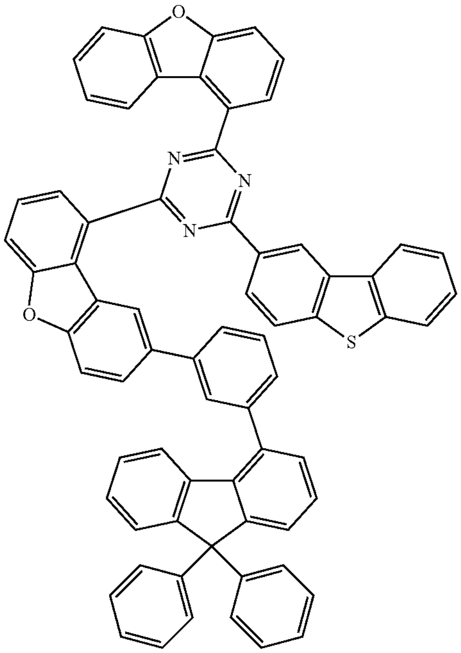 [SMILES: c1ccc(C2(c3ccccc3)c3ccccc3-c3c(-c4cccc(-c5ccc6oc7cccc(-c8nc(-c9ccc%10sc%11ccccc%11c%10c9)nc(-c9cccc%10oc%11ccccc%11c9%10)n8)c7c6c5)c4)cccc32)cc1]
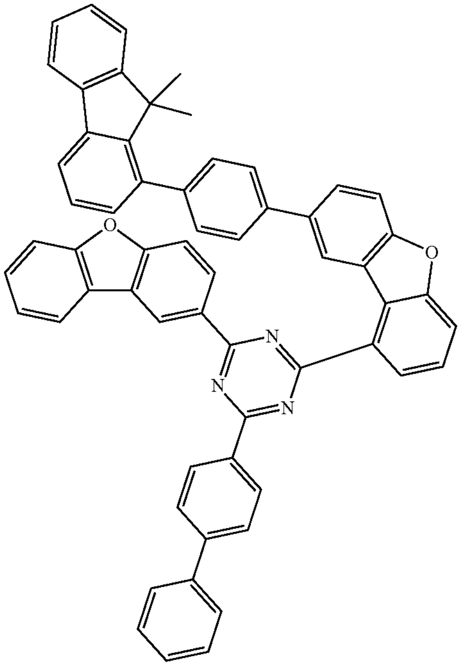 [SMILES: CC1(C)c2ccccc2-c2cccc(-c3ccc(-c4ccc5oc6cccc(-c7nc(-c8ccc(-c9ccccc9)cc8)nc(-c8ccc9oc%10ccccc%10c9c8)n7)c6c5c4)cc3)c21]

TABLE 1-continued
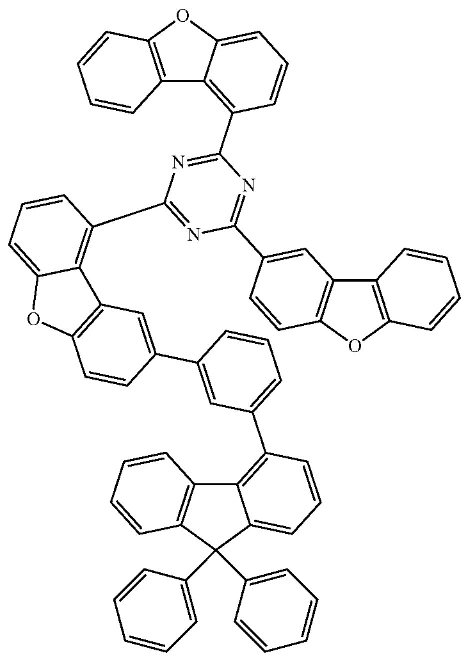 [SMILES: c1ccc(C2(c3ccccc3)c3ccccc3-c3c(-c4cccc(-c5ccc6oc7cccc(-c8nc(-c9ccc%10oc%11ccccc%11c%10c9)nc(-c9cccc%10oc%11ccccc%11c9%10)n8)c7c6c5)c4)cccc32)cc1]
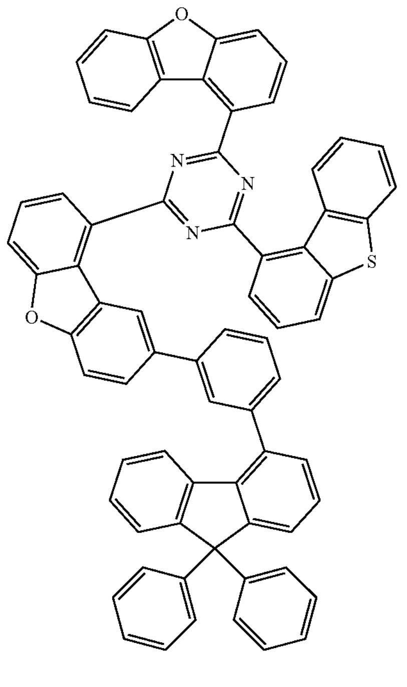 [SMILES: c1ccc(C2(c3ccccc3)c3ccccc3-c3c(-c4cccc(-c5ccc6oc7cccc(-c8nc(-c9cccc%10oc%11ccccc%11c9%10)nc(-c9cccc%10sc%11ccccc%11c9%10)n8)c7c6c5)c4)cccc32)cc1]

TABLE 1-continued
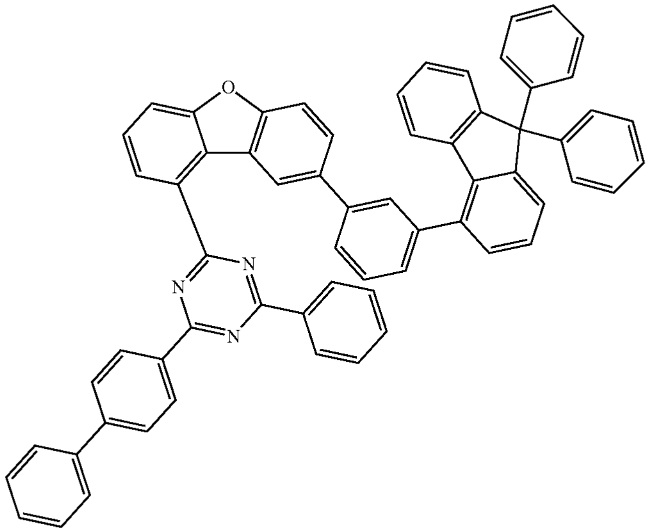 [SMILES: c1ccc(-c2ccc(-c3nc(-c4ccccc4)nc(-c4cccc5oc6ccc(-c7cccc(-c8cccc9c8-c8ccccc8C9(c8ccccc8)c8ccccc8)c7)cc6c45)n3)cc2)cc1]
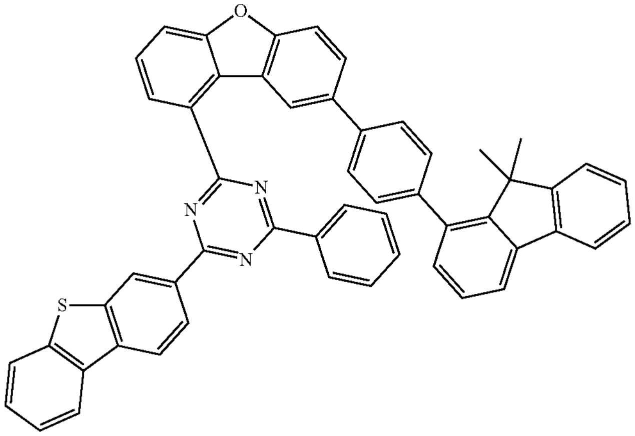 [SMILES: CC1(C)c2ccccc2-c2cccc(-c3ccc(-c4ccc5oc6cccc(-c7nc(-c8ccccc8)nc(-c8ccc9c(c8)sc8ccccc89)n7)c6c5c4)cc3)c21]
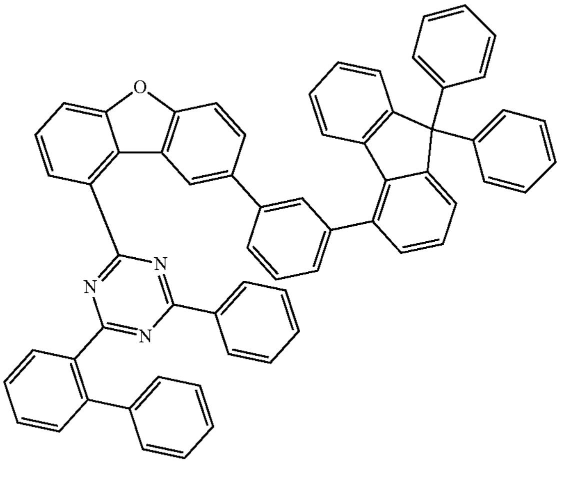 [SMILES: c1ccc(-c2nc(-c3ccccc3-c3ccccc3)nc(-c3cccc4oc5ccc(-c6cccc(-c7cccc8c7-c7ccccc7C8(c7ccccc7)c7ccccc7)c6)cc5c34)n2)cc1]

TABLE 1-continued
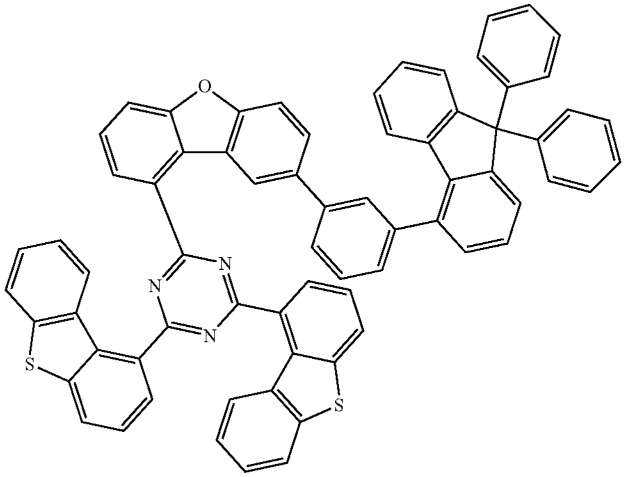 [SMILES: c1ccc(C2(c3ccccc3)c3ccccc3-c3c(-c4cccc(-c5ccc6oc7cccc(-c8nc(-c9cccc%10sc%11ccccc%11c9%10)nc(-c9cccc%10sc%11ccccc%11c9%10)n8)c7c6c5)c4)cccc32)cc1]
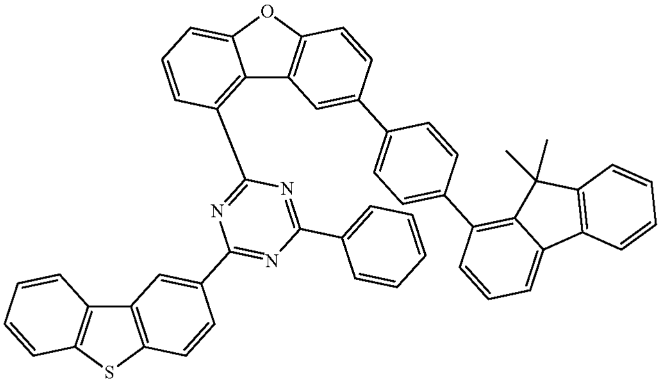 [SMILES: CC1(C)c2ccccc2-c2cccc(-c3ccc(-c4ccc5oc6cccc(-c7nc(-c8ccccc8)nc(-c8ccc9sc%10ccccc%10c9c8)n7)c6c5c4)cc3)c21]
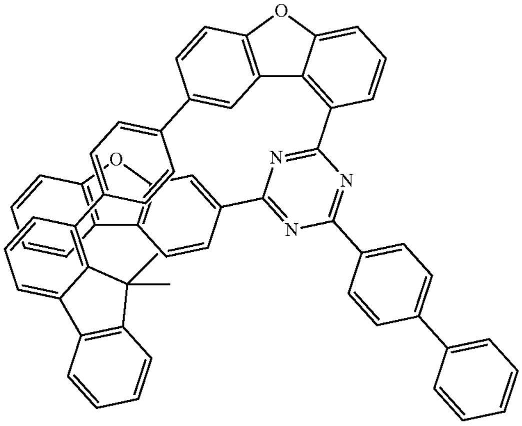 [SMILES: CC1(C)c2ccccc2-c2cccc(-c3ccc(-c4ccc5oc6cccc(-c7nc(-c8ccc(-c9ccccc9)cc8)nc(-c8ccc9c(c8)oc8ccccc89)n7)c6c5c4)cc3)c21]

TABLE 1-continued
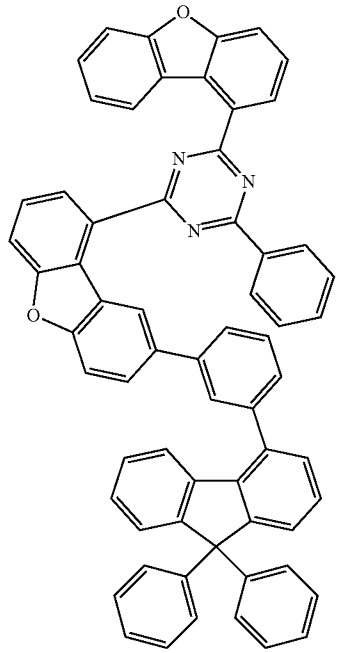 [SMILES: c1ccc(-c2nc(-c3cccc4oc5ccccc5c34)nc(-c3cccc4oc5ccc(-c6cccc(-c7cccc8c7-c7ccccc7C8(c7ccccc7)c7ccccc7)c6)cc5c34)n2)cc1]
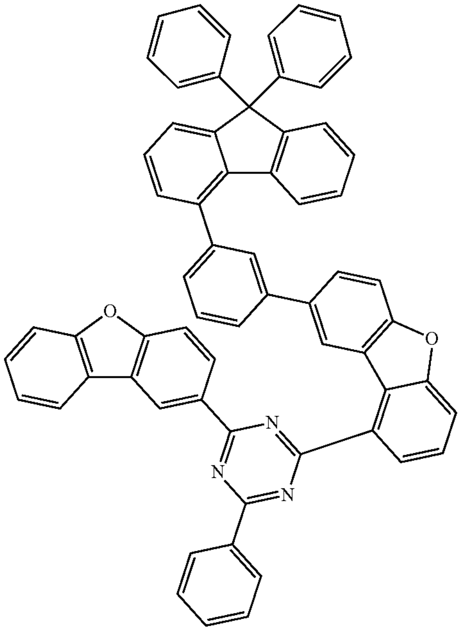 [SMILES: c1ccc(-c2nc(-c3ccc4oc5ccccc5c4c3)nc(-c3cccc4oc5ccc(-c6cccc(-c7cccc8c7-c7ccccc7C8(c7ccccc7)c7ccccc7)c6)cc5c34)n2)cc1]

TABLE 1-continued
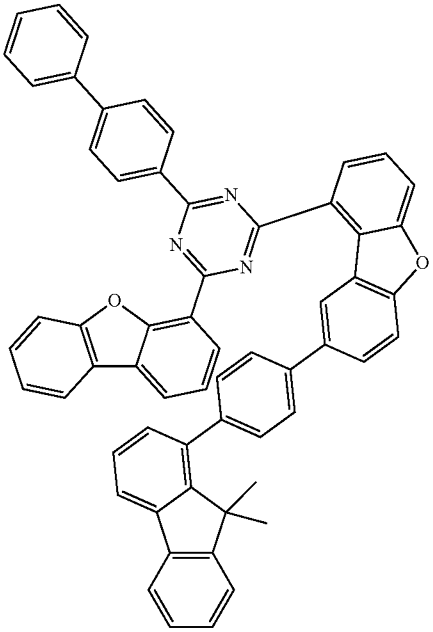 [SMILES: CC1(C)c2ccccc2-c2cccc(-c3ccc(-c4ccc5oc6cccc(-c7nc(-c8ccc(-c9ccccc9)cc8)nc(-c8cccc9c8oc8ccccc89)n7)c6c5c4)cc3)c21]
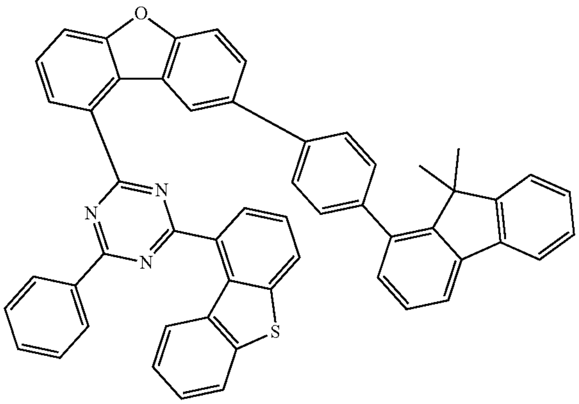 [SMILES: CC1(C)c2ccccc2-c2cccc(-c3ccc(-c4ccc5oc6cccc(-c7nc(-c8ccccc8)nc(-c8cccc9sc%10ccccc%10c89)n7)c6c5c4)cc3)c21]
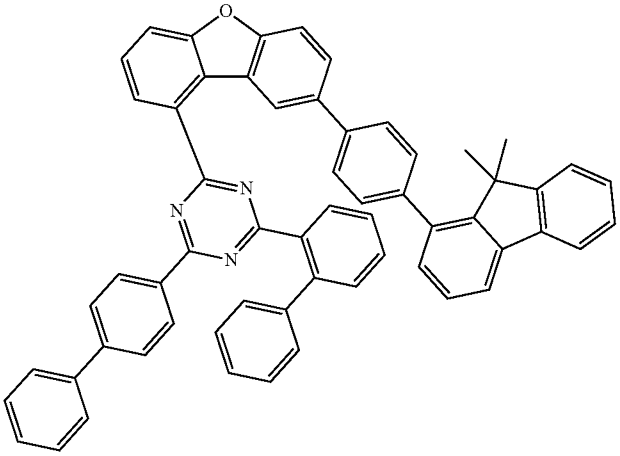 [SMILES: CC1(C)c2ccccc2-c2cccc(-c3ccc(-c4ccc5oc6cccc(-c7nc(-c8ccc(-c9ccccc9)cc8)nc(-c8ccccc8-c8ccccc8)n7)c6c5c4)cc3)c21]

TABLE 1-continued
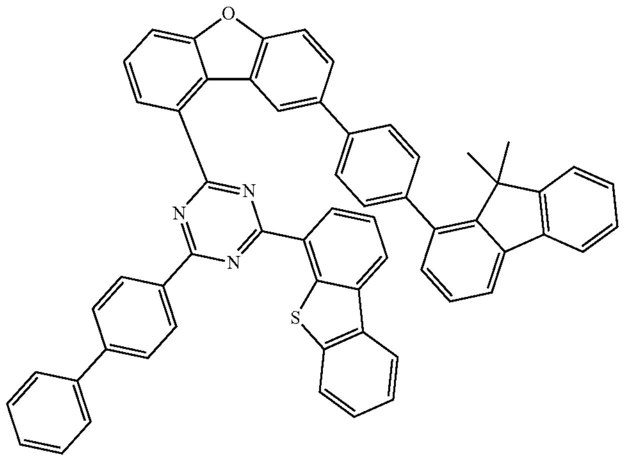 [SMILES: CC1(C)c2ccccc2-c2cccc(-c3ccc(-c4ccc5oc6cccc(-c7nc(-c8ccc(-c9ccccc9)cc8)nc(-c8cccc9c8sc8ccccc89)n7)c6c5c4)cc3)c21]
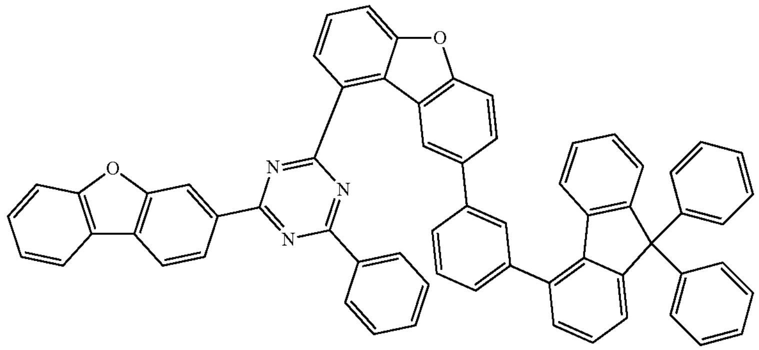 [SMILES: c1ccc(-c2nc(-c3ccc4c(c3)oc3ccccc34)nc(-c3cccc4oc5ccc(-c6cccc(-c7cccc8c7-c7ccccc7C8(c7ccccc7)c7ccccc7)c6)cc5c34)n2)cc1]
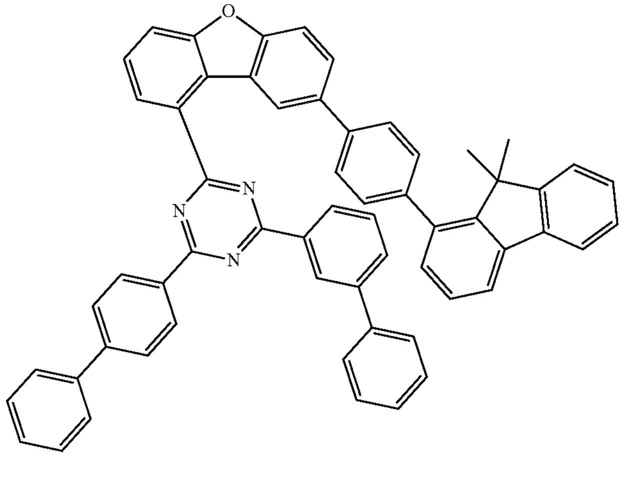 [SMILES: CC1(C)c2ccccc2-c2cccc(-c3ccc(-c4ccc5oc6cccc(-c7nc(-c8ccc(-c9ccccc9)cc8)nc(-c8cccc(-c9ccccc9)c8)n7)c6c5c4)cc3)c21]

TABLE 1-continued
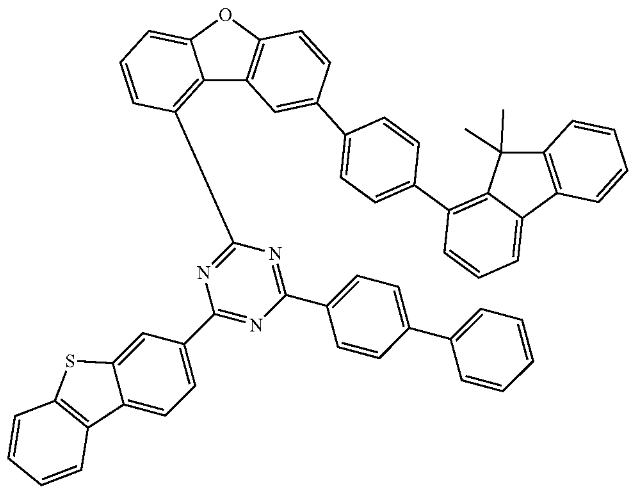 [SMILES: CC1(C)c2ccccc2-c2cccc(-c3ccc(-c4ccc5oc6cccc(-c7nc(-c8ccc(-c9ccccc9)cc8)nc(-c8ccc9c(c8)sc8ccccc89)n7)c6c5c4)cc3)c21]
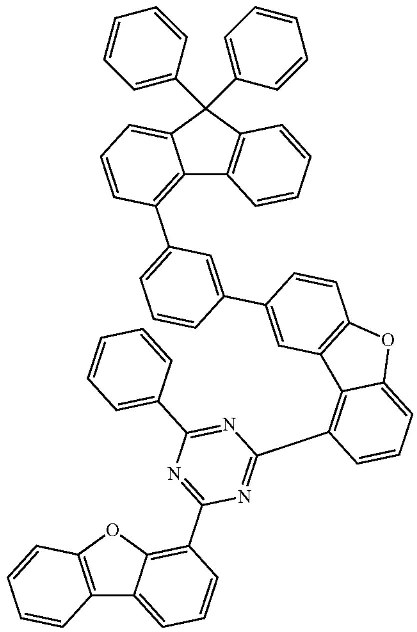 [SMILES: c1ccc(-c2nc(-c3cccc4c3oc3ccccc34)nc(-c3cccc4oc5ccc(-c6cccc(-c7cccc8c7-c7ccccc7C8(c7ccccc7)c7ccccc7)c6)cc5c34)n2)cc1]
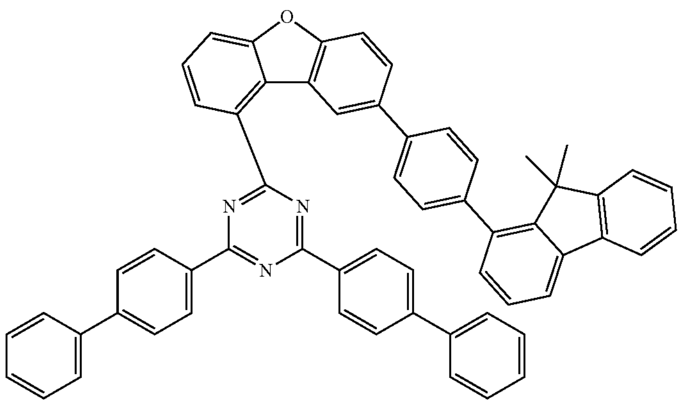 [SMILES: CC1(C)c2ccccc2-c2cccc(-c3ccc(-c4ccc5oc6cccc(-c7nc(-c8ccc(-c9ccccc9)cc8)nc(-c8ccc(-c9ccccc9)cc8)n7)c6c5c4)cc3)c21]

TABLE 1-continued
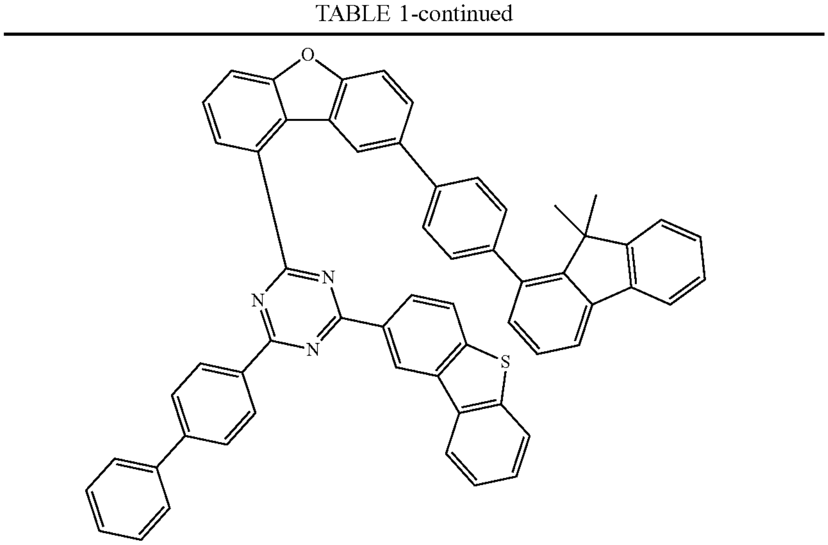
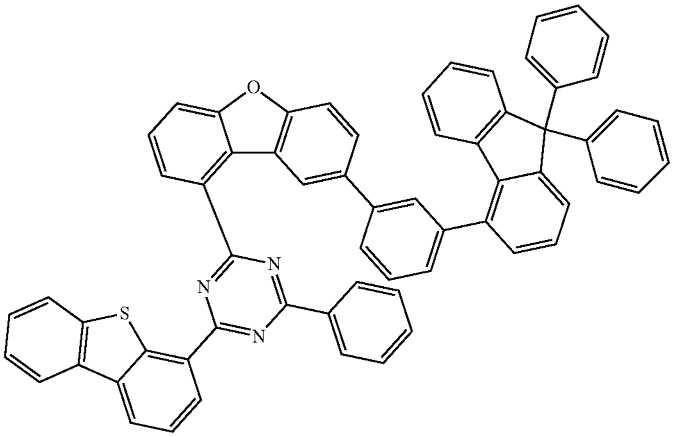 [SMILES: c1ccc(-c2nc(-c3cccc4c3sc3ccccc34)nc(-c3cccc4oc5ccc(-c6cccc(-c7cccc8c7-c7ccccc7C8(c7ccccc7)c7ccccc7)c6)cc5c34)n2)cc1]
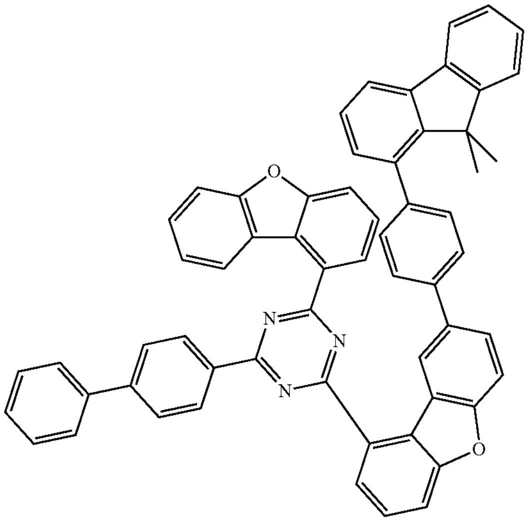 [SMILES: CC1(C)c2ccccc2-c2cccc(-c3ccc(-c4ccc5oc6cccc(-c7nc(-c8ccc(-c9ccccc9)cc8)nc(-c8cccc9oc%10ccccc%10c89)n7)c6c5c4)cc3)c21]

TABLE 1-continued
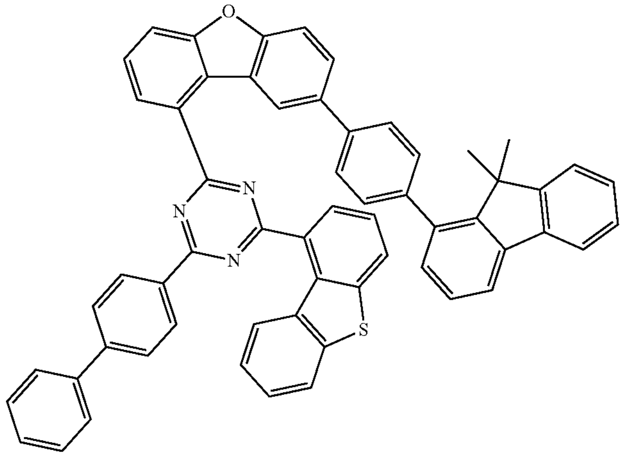 [SMILES: CC1(C)c2ccccc2-c2cccc(-c3ccc(-c4ccc5oc6cccc(-c7nc(-c8ccc(-c9ccccc9)cc8)nc(-c8cccc9sc%10ccccc%10c89)n7)c6c5c4)cc3)c21]
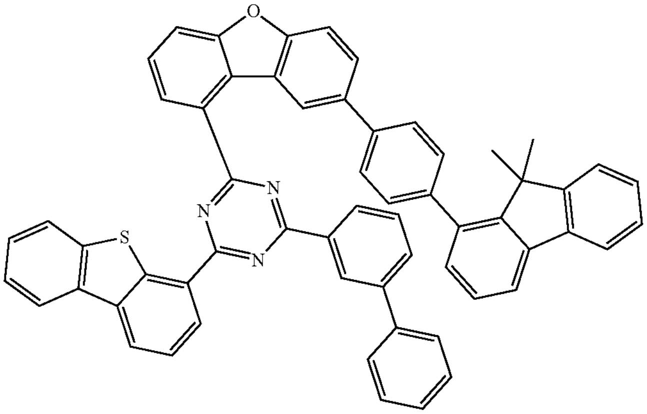 [SMILES: CC1(C)c2ccccc2-c2cccc(-c3ccc(-c4ccc5oc6cccc(-c7nc(-c8cccc(-c9ccccc9)c8)nc(-c8cccc9c8sc8ccccc89)n7)c6c5c4)cc3)c21]
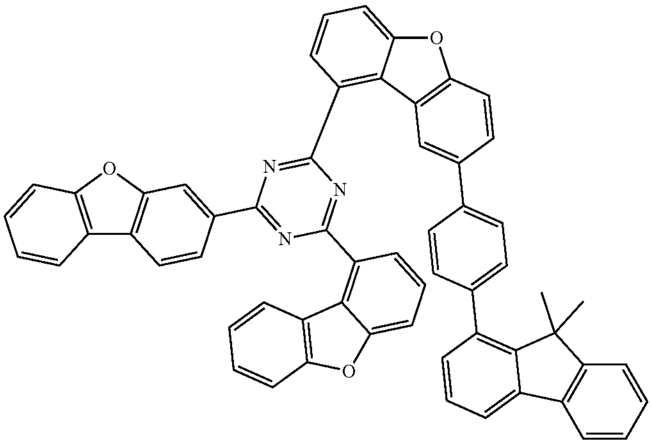 [SMILES: CC1(C)c2ccccc2-c2cccc(-c3ccc(-c4ccc5oc6cccc(-c7nc(-c8ccc9c(c8)oc8ccccc89)nc(-c8cccc9oc%10ccccc%10c89)n7)c6c5c4)cc3)c21]

TABLE 1-continued
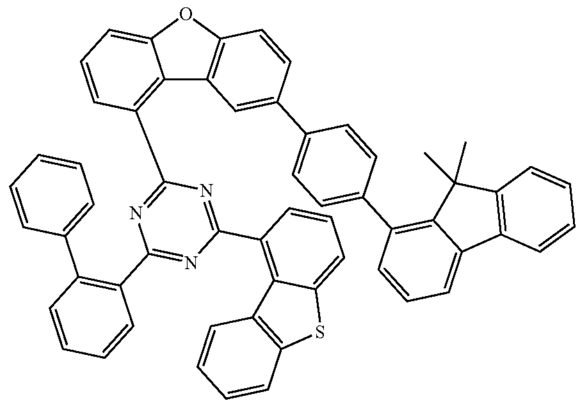 [SMILES: CC1(C)c2ccccc2-c2cccc(-c3ccc(-c4ccc5oc6cccc(-c7nc(-c8ccccc8-c8ccccc8)nc(-c8cccc9sc%10ccccc%10c89)n7)c6c5c4)cc3)c21]
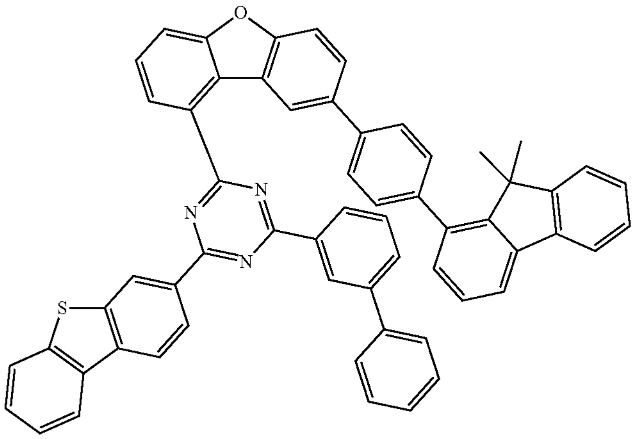 [SMILES: CC1(C)c2ccccc2-c2cccc(-c3ccc(-c4ccc5oc6cccc(-c7nc(-c8cccc(-c9ccccc9)c8)nc(-c8ccc9c(c8)sc8ccccc89)n7)c6c5c4)cc3)c21]
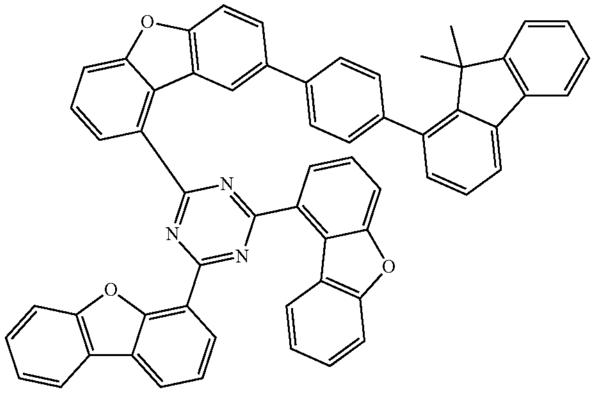 [SMILES: CC1(C)c2ccccc2-c2cccc(-c3ccc(-c4ccc5oc6cccc(-c7nc(-c8cccc9c8oc8ccccc89)nc(-c8cccc9oc%10ccccc%10c89)n7)c6c5c4)cc3)c21]

TABLE 1-continued
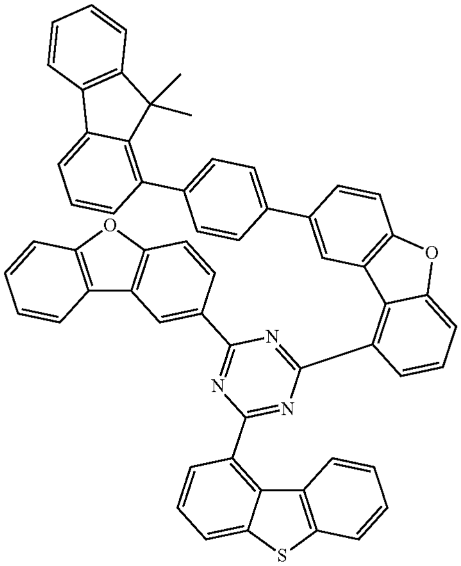 [SMILES: CC1(C)c2ccccc2-c2cccc(-c3ccc(-c4ccc5oc6cccc(-c7nc(-c8ccc9oc%10ccccc%10c9c8)nc(-c8cccc9sc%10ccccc%10c89)n7)c6c5c4)cc3)c21]
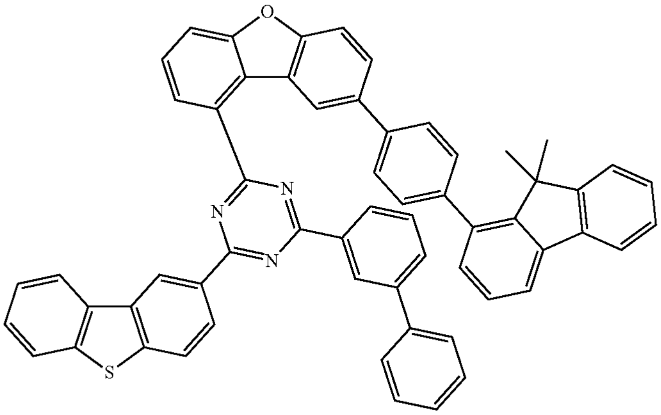 [SMILES: CC1(C)c2ccccc2-c2cccc(-c3ccc(-c4ccc5oc6cccc(-c7nc(-c8cccc(-c9ccccc9)c8)nc(-c8ccc9sc%10ccccc%10c9c8)n7)c6c5c4)cc3)c21]
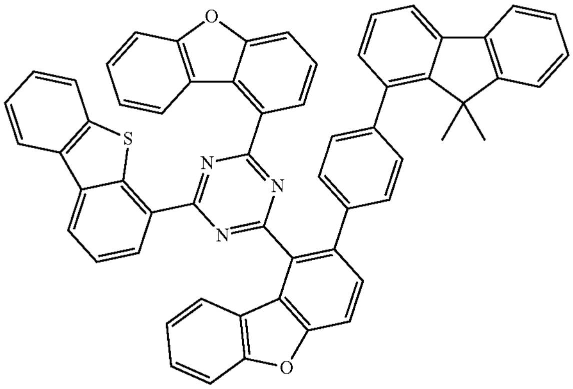 [SMILES: CC1(C)c2ccccc2-c2cccc(-c3ccc(-c4ccc5oc6ccccc6c5c4-c4nc(-c5cccc6c5sc5ccccc56)nc(-c5cccc6oc7ccccc7c56)n4)cc3)c21]

TABLE 1-continued
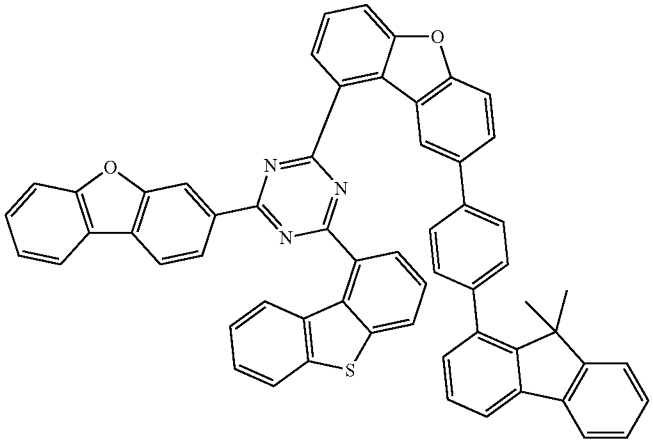 [SMILES: CC1(C)c2ccccc2-c2cccc(-c3ccc(-c4ccc5oc6cccc(-c7nc(-c8ccc9c(c8)oc8ccccc89)nc(-c8cccc9sc%10ccccc%10c89)n7)c6c5c4)cc3)c21]
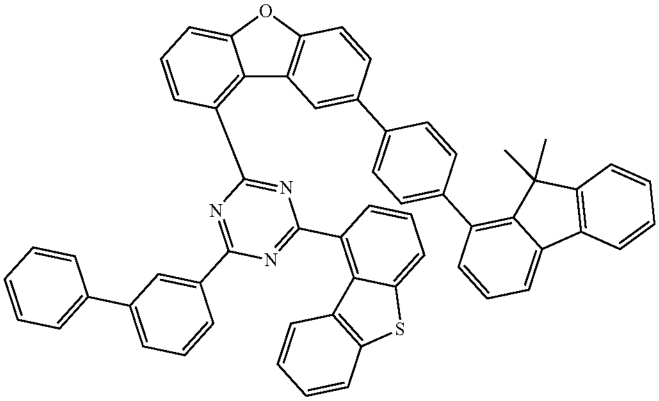 [SMILES: CC1(C)c2ccccc2-c2cccc(-c3ccc(-c4ccc5oc6cccc(-c7nc(-c8cccc(-c9ccccc9)c8)nc(-c8cccc9sc%10ccccc%10c89)n7)c6c5c4)cc3)c21]
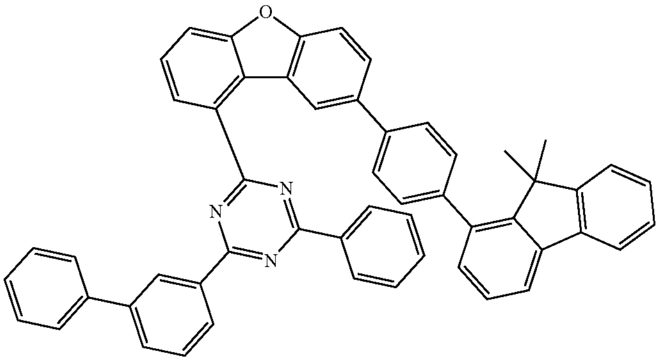 [SMILES: CC1(C)c2ccccc2-c2cccc(-c3ccc(-c4ccc5oc6cccc(-c7nc(-c8ccccc8)nc(-c8cccc(-c9ccccc9)c8)n7)c6c5c4)cc3)c21]
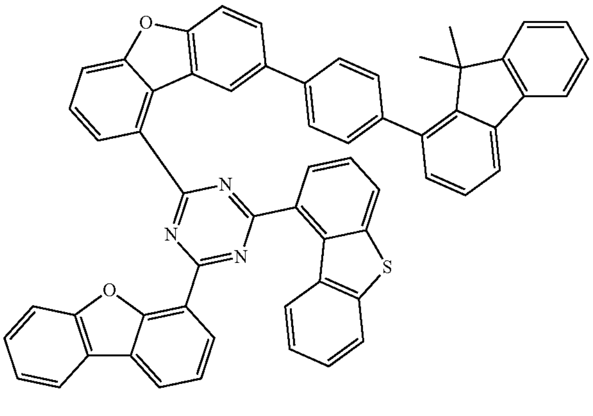

TABLE 1-continued
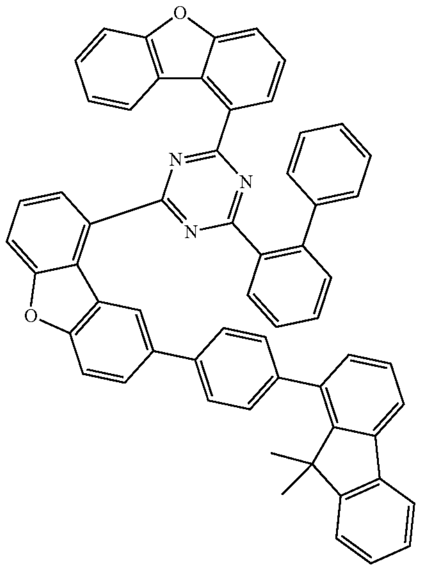 [SMILES: CC1(C)c2ccccc2-c2cccc(-c3ccc(-c4ccc5oc6cccc(-c7nc(-c8ccccc8-c8ccccc8)nc(-c8cccc9oc%10ccccc%10c89)n7)c6c5c4)cc3)c21]
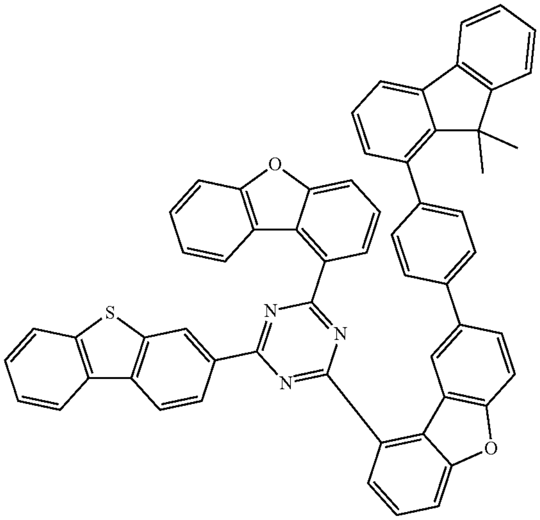 [SMILES: CC1(C)c2ccccc2-c2cccc(-c3ccc(-c4ccc5oc6cccc(-c7nc(-c8ccc9c(c8)sc8ccccc89)nc(-c8cccc9oc%10ccccc%10c89)n7)c6c5c4)cc3)c21]
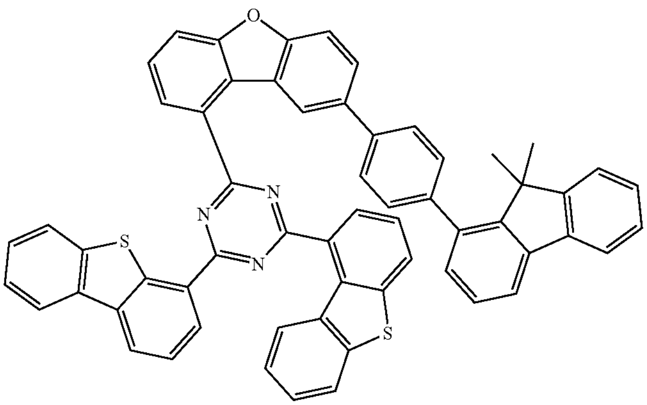 [SMILES: CC1(C)c2ccccc2-c2cccc(-c3ccc(-c4ccc5oc6cccc(-c7nc(-c8cccc9c8sc8ccccc89)nc(-c8cccc9sc%10ccccc%10c89)n7)c6c5c4)cc3)c21]

TABLE 1-continued
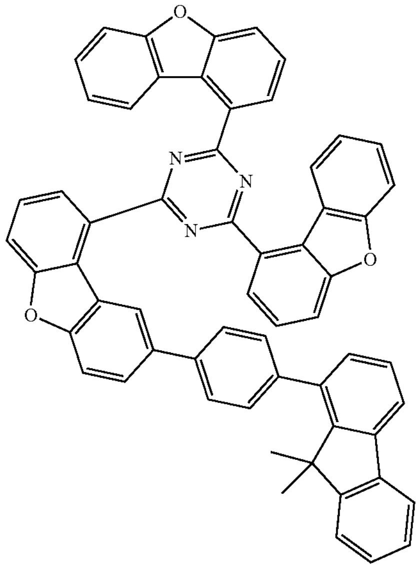 [SMILES: CC1(C)c2ccccc2-c2cccc(-c3ccc(-c4ccc5oc6cccc(-c7nc(-c8cccc9oc%10ccccc%10c89)nc(-c8cccc9oc%10ccccc%10c89)n7)c6c5c4)cc3)c21]
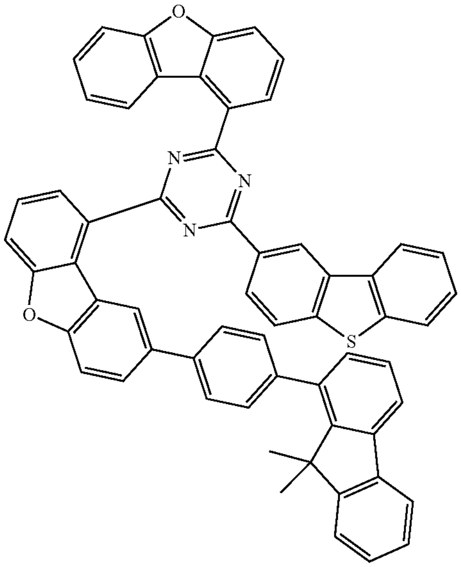 [SMILES: CC1(C)c2ccccc2-c2cccc(-c3ccc(-c4ccc5oc6cccc(-c7nc(-c8ccc9sc%10ccccc%10c9c8)nc(-c8cccc9oc%10ccccc%10c89)n7)c6c5c4)cc3)c21]
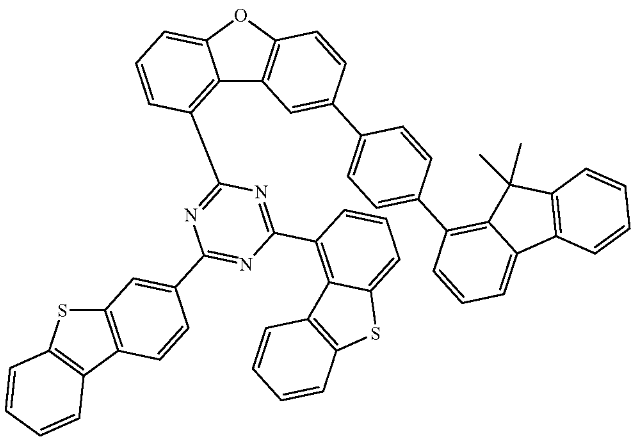 [SMILES: CC1(C)c2ccccc2-c2cccc(-c3ccc(-c4ccc5oc6cccc(-c7nc(-c8ccc9c(c8)sc8ccccc89)nc(-c8cccc9sc%10ccccc%10c89)n7)c6c5c4)cc3)c21]

TABLE 1-continued
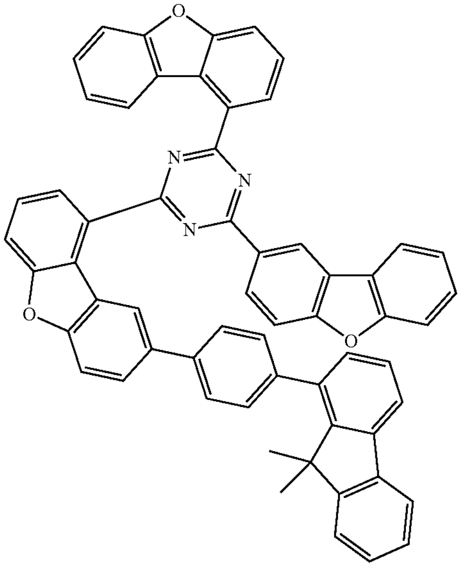
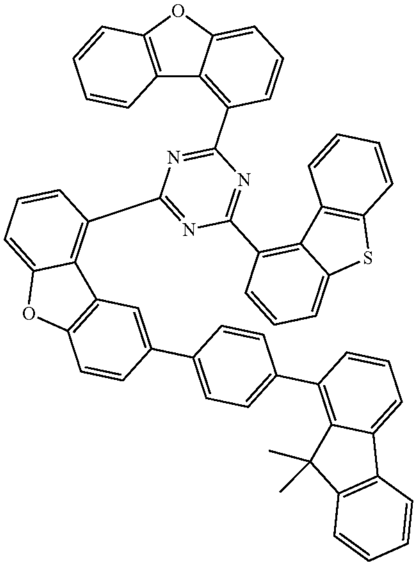 [SMILES: CC1(C)c2ccccc2-c2cccc(-c3ccc(-c4ccc5oc6cccc(-c7nc(-c8cccc9oc%10ccccc%10c89)nc(-c8cccc9sc%10ccccc%10c89)n7)c6c5c4)cc3)c21]
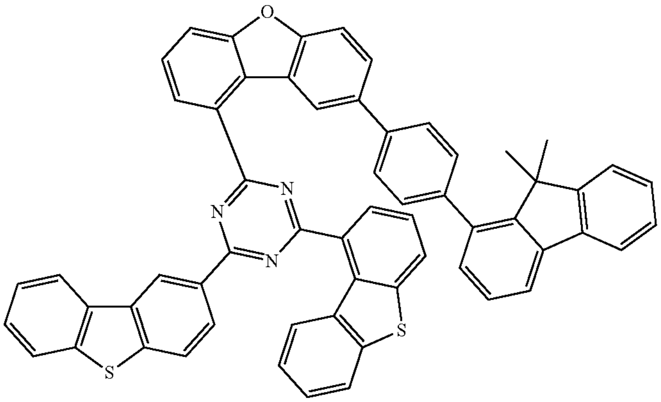 [SMILES: CC1(C)c2ccccc2-c2cccc(-c3ccc(-c4ccc5oc6cccc(-c7nc(-c8ccc9sc%10ccccc%10c9c8)nc(-c8cccc9sc%10ccccc%10c89)n7)c6c5c4)cc3)c21]

TABLE 1-continued
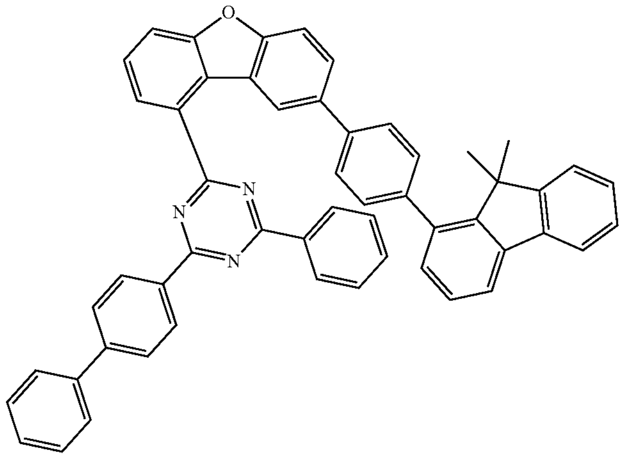 [SMILES: CC1(C)c2ccccc2-c2cccc(-c3ccc(-c4ccc5oc6cccc(-c7nc(-c8ccccc8)nc(-c8ccc(-c9ccccc9)cc8)n7)c6c5c4)cc3)c21]
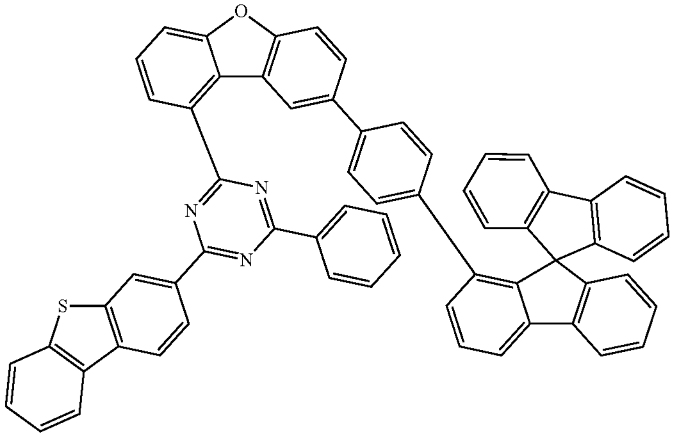 [SMILES: c1ccc(-c2nc(-c3ccc4c(c3)sc3ccccc34)nc(-c3cccc4oc5ccc(-c6ccc(-c7cccc8c7C7(c9ccccc9-c9ccccc97)c7ccccc7-8)cc6)cc5c34)n2)cc1]
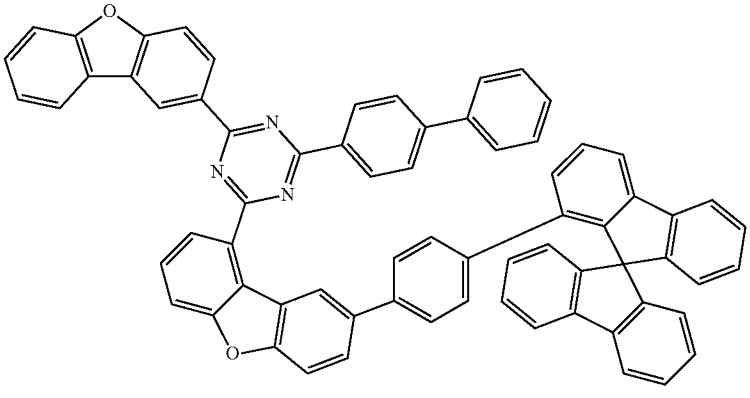 [SMILES: c1ccc(-c2ccc(-c3nc(-c4ccc5oc6ccccc6c5c4)nc(-c4cccc5oc6ccc(-c7ccc(-c8cccc9c8C8(c%10ccccc%10-c%10ccccc%108)c8ccccc8-9)cc7)cc6c45)n3)cc2)cc1]

TABLE 1-continued
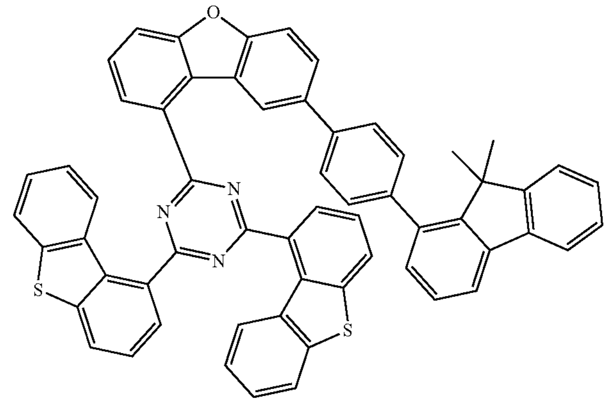 [SMILES: CC1(C)c2ccccc2-c2cccc(-c3ccc(-c4ccc5oc6cccc(-c7nc(-c8cccc9sc%10ccccc%10c89)nc(-c8cccc9sc%10ccccc%10c89)n7)c6c5c4)cc3)c21]
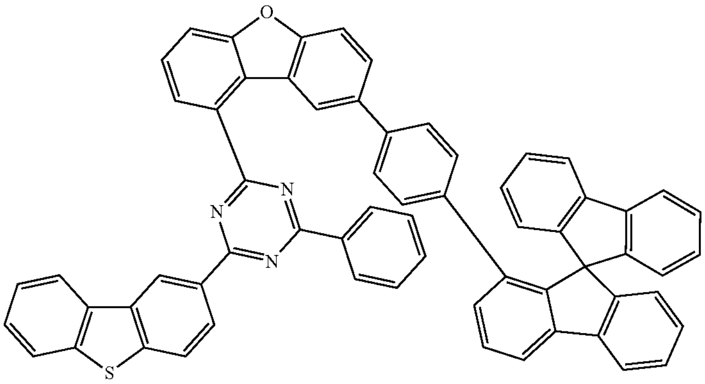 [SMILES: c1ccc(-c2nc(-c3ccc4sc5ccccc5c4c3)nc(-c3cccc4oc5ccc(-c6ccc(-c7cccc8c7C7(c9ccccc9-c9ccccc97)c7ccccc7-8)cc6)cc5c34)n2)cc1]
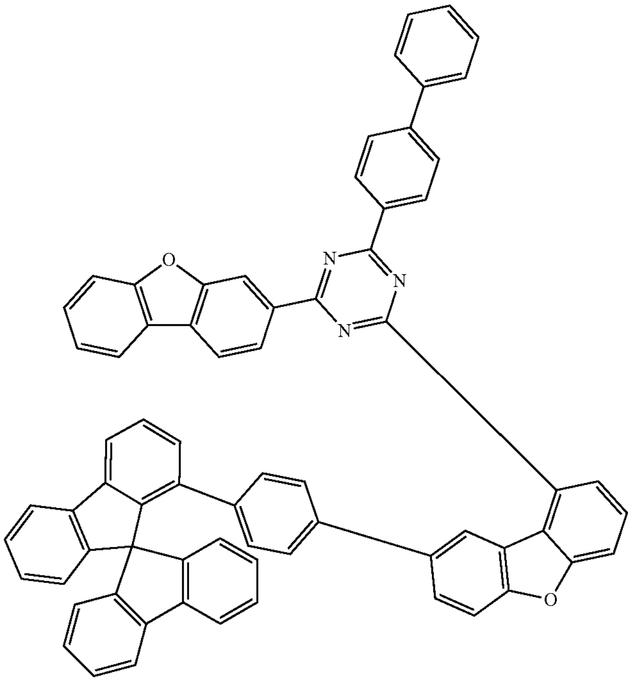 [SMILES: c1ccc(-c2ccc(-c3nc(-c4ccc5c(c4)oc4ccccc45)nc(-c4cccc5oc6ccc(-c7ccc(-c8cccc9c8C8(c%10ccccc%10-c%10ccccc%108)c8ccccc8-9)cc7)cc6c45)n3)cc2)cc1]

TABLE 1-continued
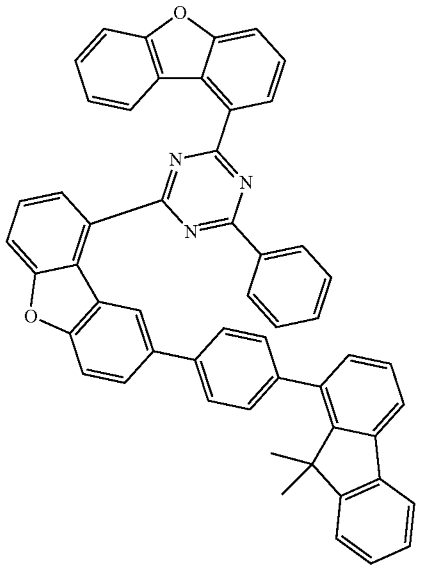 [SMILES: CC1(C)c2ccccc2-c2cccc(-c3ccc(-c4ccc5oc6cccc(-c7nc(-c8ccccc8)nc(-c8cccc9oc%10ccccc%10c89)n7)c6c5c4)cc3)c21]
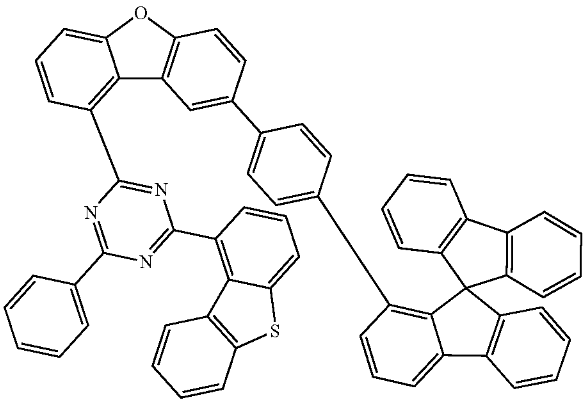 [SMILES: c1ccc(-c2nc(-c3cccc4oc5ccc(-c6ccc(-c7cccc8c7C7(c9ccccc9-c9ccccc97)c7ccccc7-8)cc6)cc5c34)nc(-c3cccc4sc5ccccc5c34)n2)cc1]
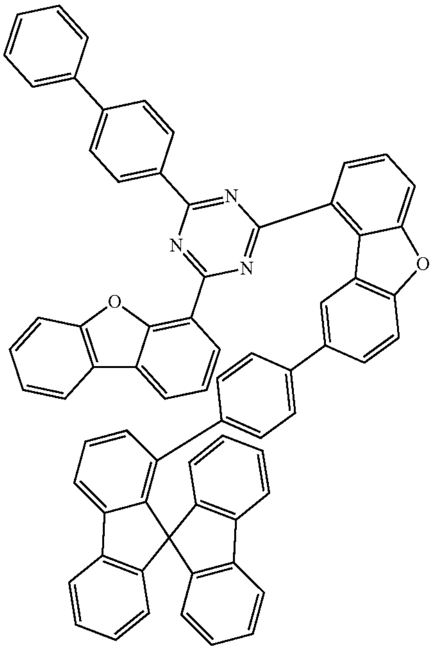 [SMILES: c1ccc(-c2ccc(-c3nc(-c4cccc5c4oc4ccccc45)nc(-c4cccc5oc6ccc(-c7ccc(-c8cccc9c8C8(c%10ccccc%10-c%10ccccc%108)c8ccccc8-9)cc7)cc6c45)n3)cc2)cc1]

TABLE 1-continued
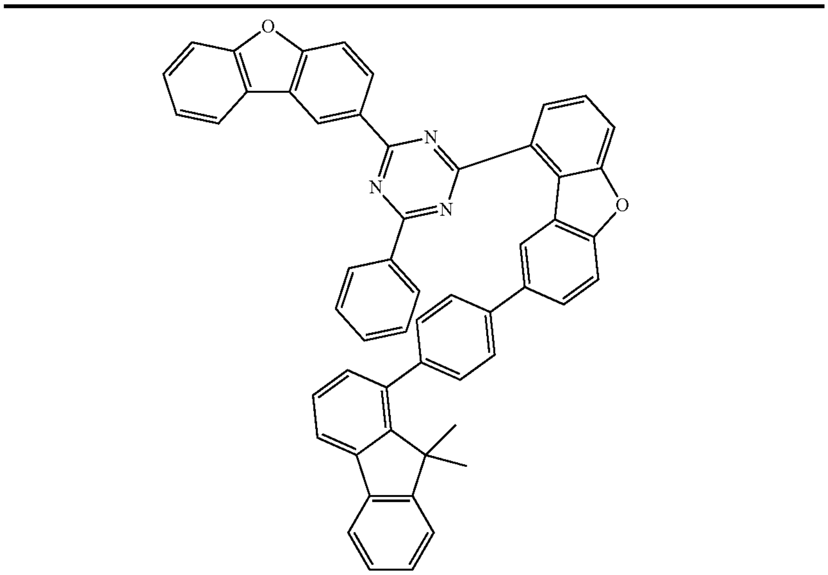
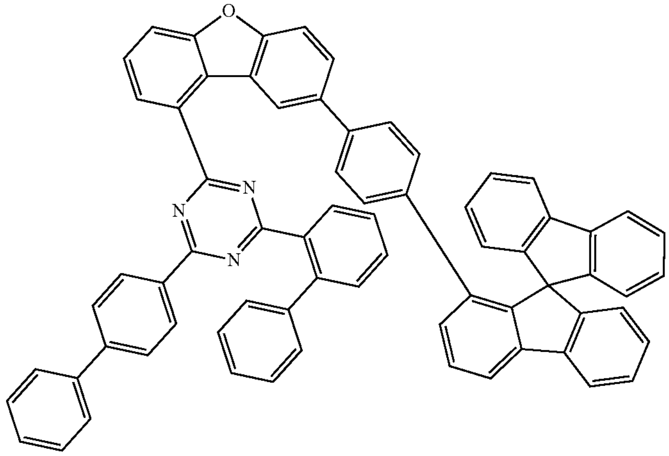 [SMILES: c1ccc(-c2ccc(-c3nc(-c4ccccc4-c4ccccc4)nc(-c4cccc5oc6ccc(-c7ccc(-c8cccc9c8C8(c%10ccccc%10-c%10ccccc%108)c8ccccc8-9)cc7)cc6c45)n3)cc2)cc1]
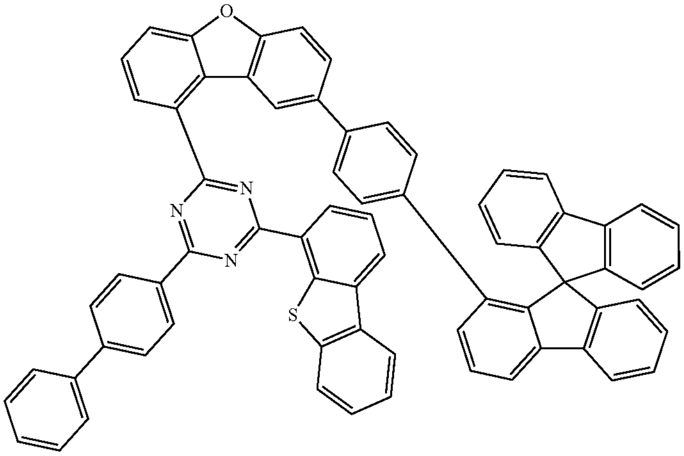 [SMILES: c1ccc(-c2ccc(-c3nc(-c4cccc5c4sc4ccccc45)nc(-c4cccc5oc6ccc(-c7ccc(-c8cccc9c8C8(c%10ccccc%10-c%10ccccc%108)c8ccccc8-9)cc7)cc6c45)n3)cc2)cc1]

TABLE 1-continued
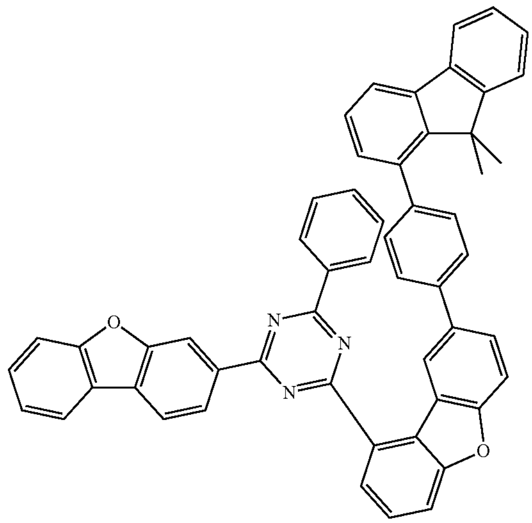 [SMILES: CC1(C)c2ccccc2-c2cccc(-c3ccc(-c4ccc5oc6cccc(-c7nc(-c8ccccc8)nc(-c8ccc9c(c8)oc8ccccc89)n7)c6c5c4)cc3)c21]
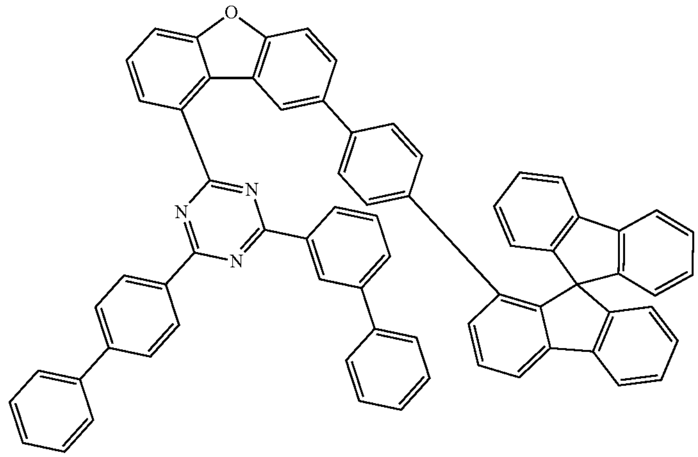 [SMILES: c1ccc(-c2ccc(-c3nc(-c4cccc(-c5ccccc5)c4)nc(-c4cccc5oc6ccc(-c7ccc(-c8cccc9c8C8(c%10ccccc%10-c%10ccccc%108)c8ccccc8-9)cc7)cc6c45)n3)cc2)cc1]
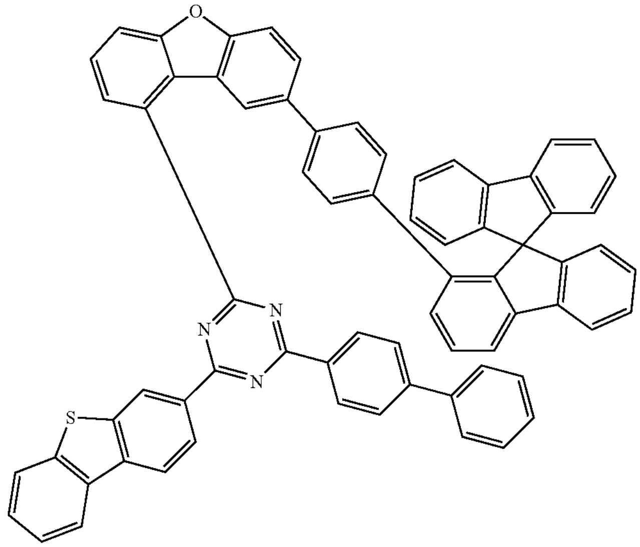 [SMILES: c1ccc(-c2ccc(-c3nc(-c4ccc5c(c4)sc4ccccc45)nc(-c4cccc5oc6ccc(-c7ccc(-c8cccc9c8C8(c%10ccccc%10-c%10ccccc%108)c8ccccc8-9)cc7)cc6c45)n3)cc2)cc1]

TABLE 1-continued
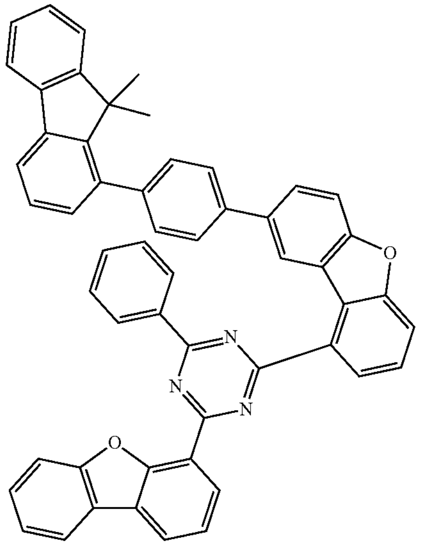 [SMILES: CC1(C)c2ccccc2-c2cccc(-c3ccc(-c4ccc5oc6cccc(-c7nc(-c8ccccc8)nc(-c8cccc9c8oc8ccccc89)n7)c6c5c4)cc3)c21]
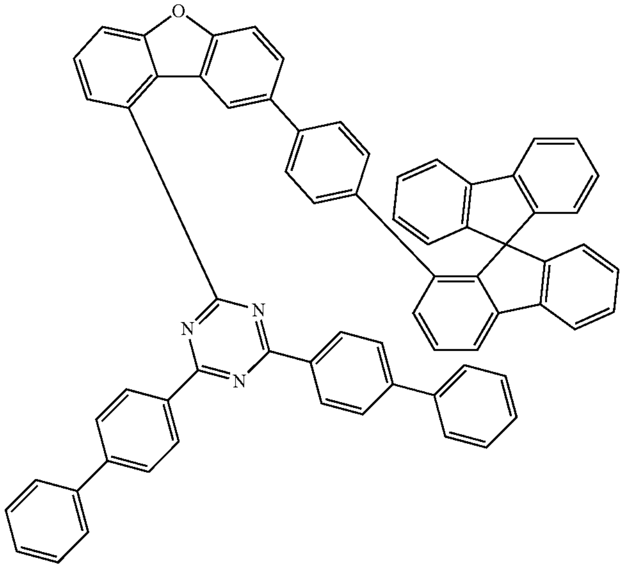 [SMILES: c1ccc(-c2ccc(-c3nc(-c4ccc(-c5ccccc5)cc4)nc(-c4cccc5oc6ccc(-c7ccc(-c8cccc9c8C8(c%10ccccc%10-c%10ccccc%108)c8ccccc8-9)cc7)cc6c45)n3)cc2)cc1]
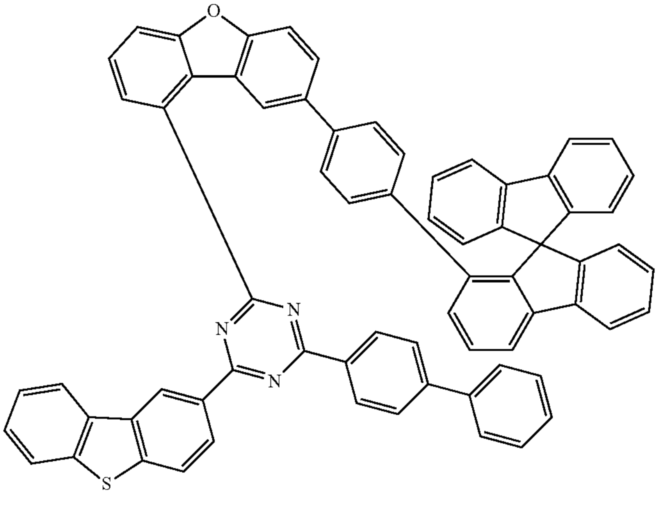 [SMILES: c1ccc(-c2ccc(-c3nc(-c4ccc5sc6ccccc6c5c4)nc(-c4cccc5oc6ccc(-c7ccc(-c8cccc9c8C8(c%10ccccc%10-c%10ccccc%108)c8ccccc8-9)cc7)cc6c45)n3)cc2)cc1]

TABLE 1-continued
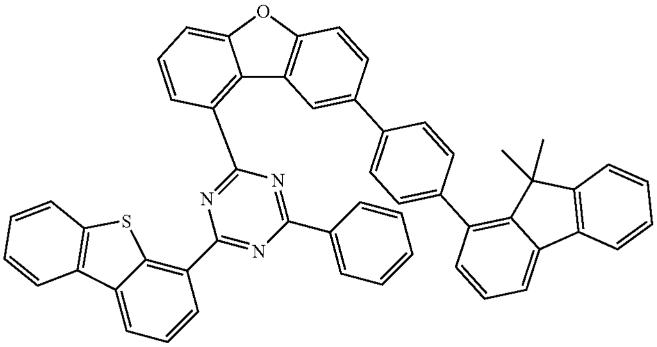 [SMILES: CC1(C)c2ccccc2-c2cccc(-c3ccc(-c4ccc5oc6cccc(-c7nc(-c8ccccc8)nc(-c8cccc9c8sc8ccccc89)n7)c6c5c4)cc3)c21]
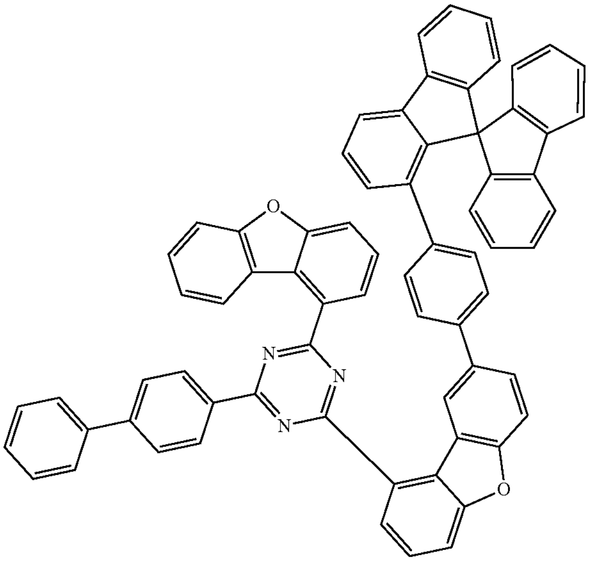 [SMILES: c1ccc(-c2ccc(-c3nc(-c4cccc5oc6ccccc6c45)nc(-c4cccc5oc6ccc(-c7ccc(-c8cccc9c8C8(c%10ccccc%10-c%10ccccc%108)c8ccccc8-9)cc7)cc6c45)n3)cc2)cc1]
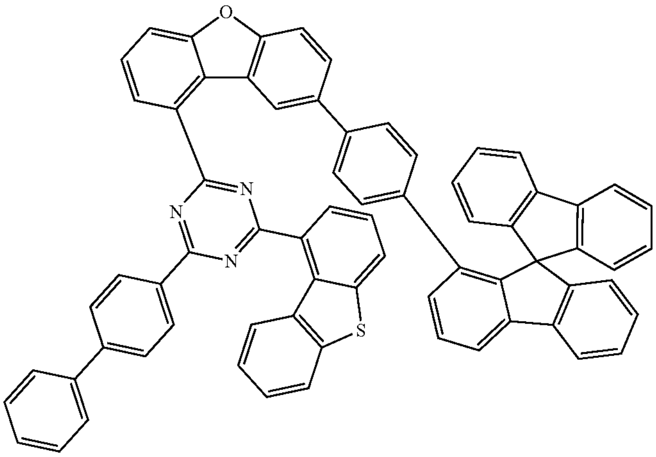 [SMILES: c1ccc(-c2ccc(-c3nc(-c4cccc5oc6ccc(-c7ccc(-c8cccc9c8C8(c%10ccccc%10-c%10ccccc%108)c8ccccc8-9)cc7)cc6c45)nc(-c4cccc5sc6ccccc6c45)n3)cc2)cc1]

TABLE 1-continued
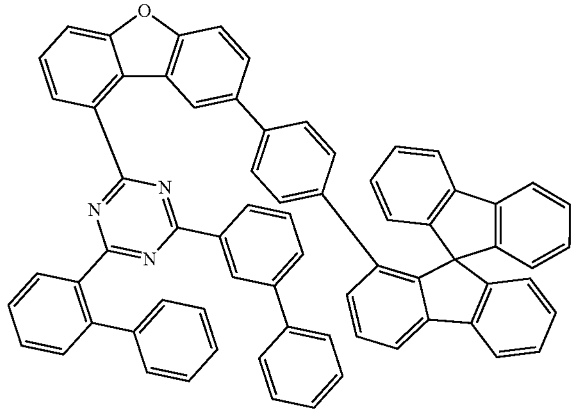 [SMILES: c1ccc(-c2cccc(-c3nc(-c4ccccc4-c4ccccc4)nc(-c4cccc5oc6ccc(-c7ccc(-c8cccc9c8C8(c%10ccccc%10-c%10ccccc%108)c8ccccc8-9)cc7)cc6c45)n3)c2)cc1]
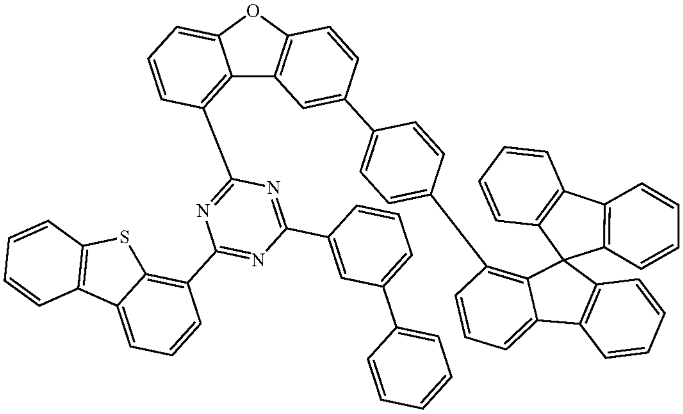 [SMILES: c1ccc(-c2cccc(-c3nc(-c4cccc5c4sc4ccccc45)nc(-c4cccc5oc6ccc(-c7ccc(-c8cccc9c8C8(c%10ccccc%10-c%10ccccc%108)c8ccccc8-9)cc7)cc6c45)n3)c2)cc1]
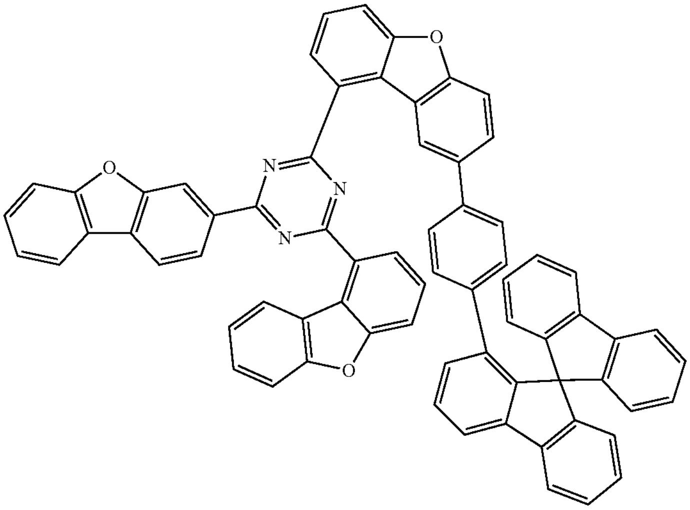 [SMILES: c1ccc2c(c1)-c1ccccc1C21c2ccccc2-c2cccc(-c3ccc(-c4ccc5oc6cccc(-c7nc(-c8ccc9c(c8)oc8ccccc89)nc(-c8cccc9oc%10ccccc%10c89)n7)c6c5c4)cc3)c21]

TABLE 1-continued
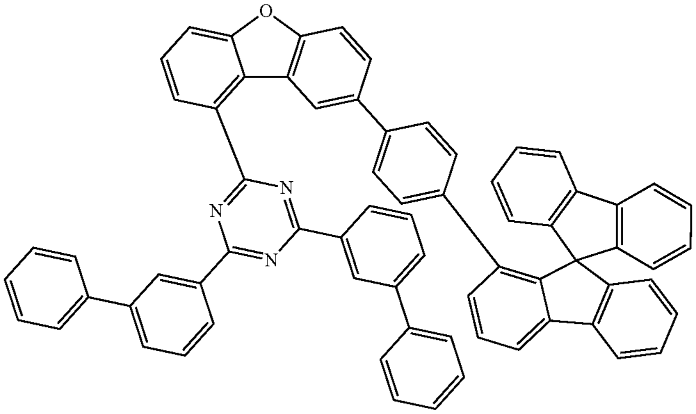 [SMILES: c1ccc(-c2cccc(-c3nc(-c4cccc(-c5ccccc5)c4)nc(-c4cccc5oc6ccc(-c7ccc(-c8cccc9c8C8(c%10ccccc%10-c%10ccccc%108)c8ccccc8-9)cc7)cc6c45)n3)c2)cc1]
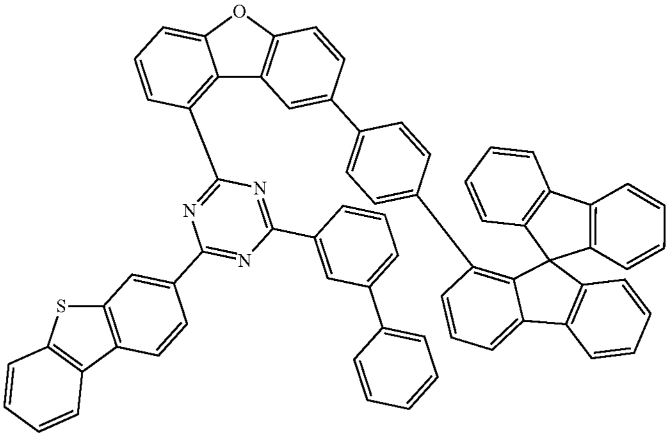 [SMILES: c1ccc(-c2cccc(-c3nc(-c4ccc5c(c4)sc4ccccc45)nc(-c4cccc5oc6ccc(-c7ccc(-c8cccc9c8C8(c%10ccccc%10-c%10ccccc%108)c8ccccc8-9)cc7)cc6c45)n3)c2)cc1]
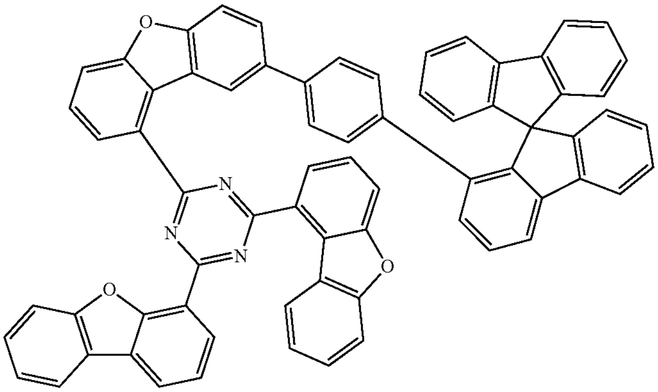 [SMILES: c1ccc2c(c1)-c1ccccc1C21c2ccccc2-c2cccc(-c3ccc(-c4ccc5oc6cccc(-c7nc(-c8cccc9c8oc8ccccc89)nc(-c8cccc9oc%10ccccc%10c89)n7)c6c5c4)cc3)c21]

TABLE 1-continued
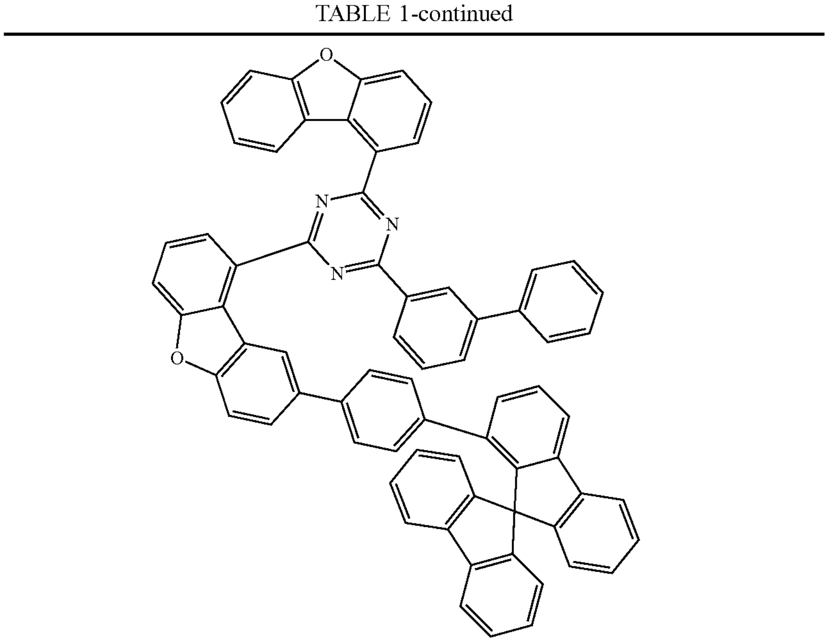
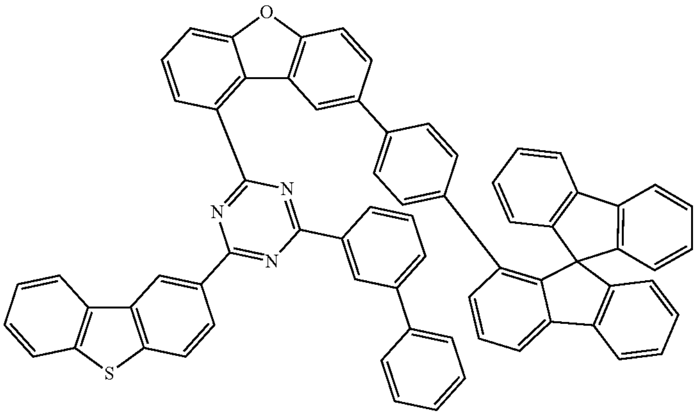 [SMILES: c1ccc(-c2cccc(-c3nc(-c4ccc5sc6ccccc6c5c4)nc(-c4cccc5oc6ccc(-c7ccc(-c8cccc9c8C8(c%10ccccc%10-c%10ccccc%108)c8ccccc8-9)cc7)cc6c45)n3)c2)cc1]
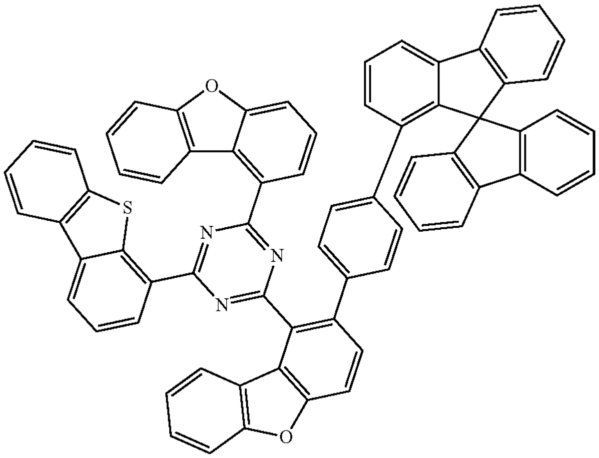 [SMILES: c1ccc2c(c1)-c1ccccc1C21c2ccccc2-c2cccc(-c3ccc(-c4ccc5oc6ccccc6c5c4-c4nc(-c5cccc6c5sc5ccccc56)nc(-c5cccc6oc7ccccc7c56)n4)cc3)c21]

TABLE 1-continued
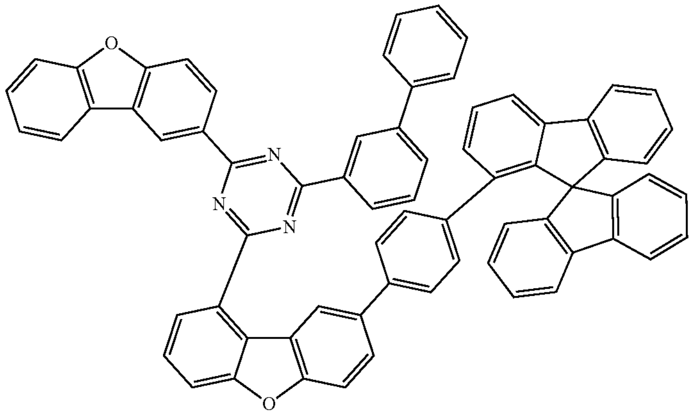 [SMILES: c1ccc(-c2cccc(-c3nc(-c4ccc5oc6ccccc6c5c4)nc(-c4cccc5oc6ccc(-c7ccc(-c8cccc9c8C8(c%10ccccc%10-c%10ccccc%108)c8ccccc8-9)cc7)cc6c45)n3)c2)cc1]
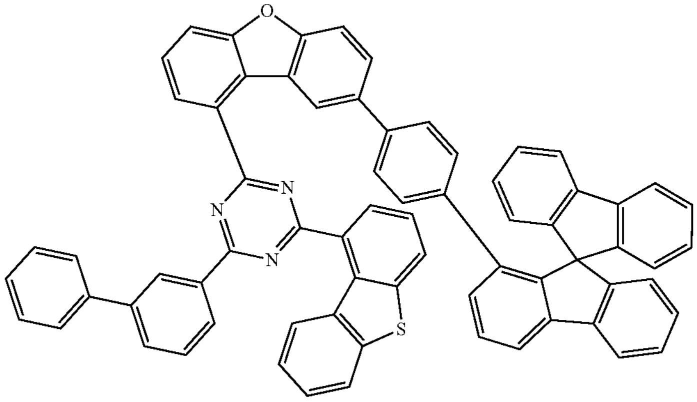 [SMILES: c1ccc(-c2cccc(-c3nc(-c4cccc5oc6ccc(-c7ccc(-c8cccc9c8C8(c%10ccccc%10-c%10ccccc%108)c8ccccc8-9)cc7)cc6c45)nc(-c4cccc5sc6ccccc6c45)n3)c2)cc1]
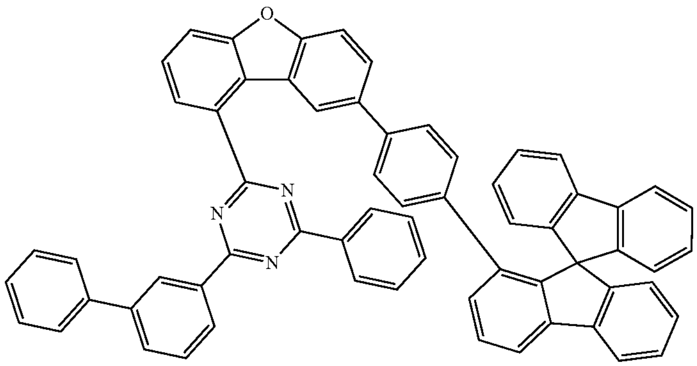 [SMILES: c1ccc(-c2cccc(-c3nc(-c4ccccc4)nc(-c4cccc5oc6ccc(-c7ccc(-c8cccc9c8C8(c%10ccccc%10-c%10ccccc%108)c8ccccc8-9)cc7)cc6c45)n3)c2)cc1]

TABLE 1-continued
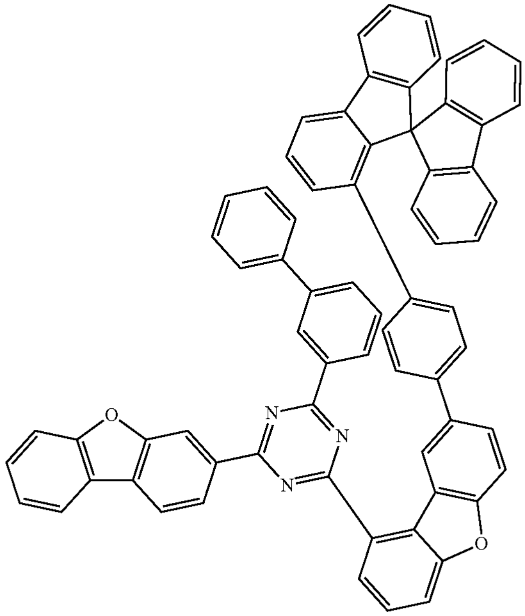 [SMILES: c1ccc(-c2cccc(-c3nc(-c4ccc5c(c4)oc4ccccc45)nc(-c4cccc5oc6ccc(-c7ccc(-c8cccc9c8C8(c%10ccccc%10-c%10ccccc%108)c8ccccc8-9)cc7)cc6c45)n3)c2)cc1]
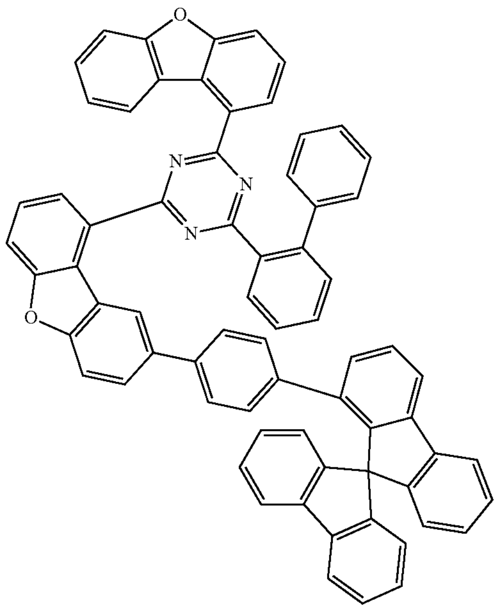 [SMILES: c1ccc(-c2ccccc2-c2nc(-c3cccc4oc5ccccc5c34)nc(-c3cccc4oc5ccc(-c6ccc(-c7cccc8c7C7(c9ccccc9-c9ccccc97)c7ccccc7-8)cc6)cc5c34)n2)cc1]

TABLE 1-continued
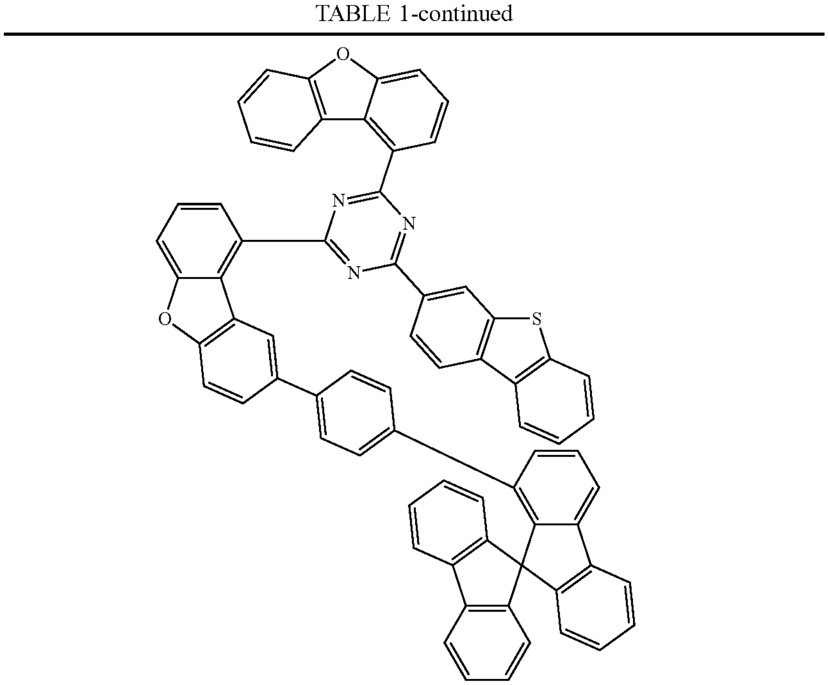
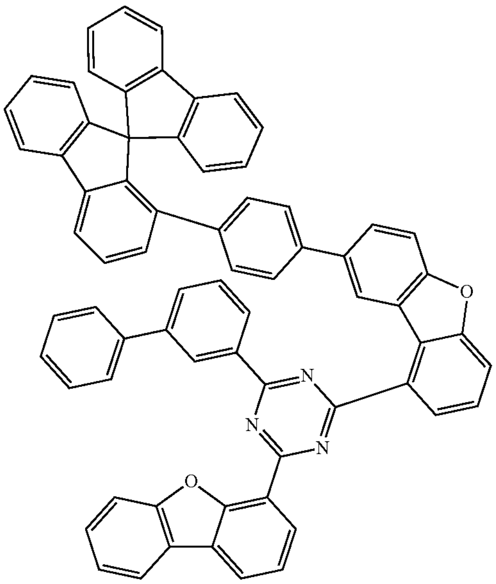 [SMILES: c1ccc(-c2cccc(-c3nc(-c4cccc5c4oc4ccccc45)nc(-c4cccc5oc6ccc(-c7ccc(-c8cccc9c8C8(c%10ccccc%10-c%10ccccc%108)c8ccccc8-9)cc7)cc6c45)n3)c2)cc1]

TABLE 1-continued
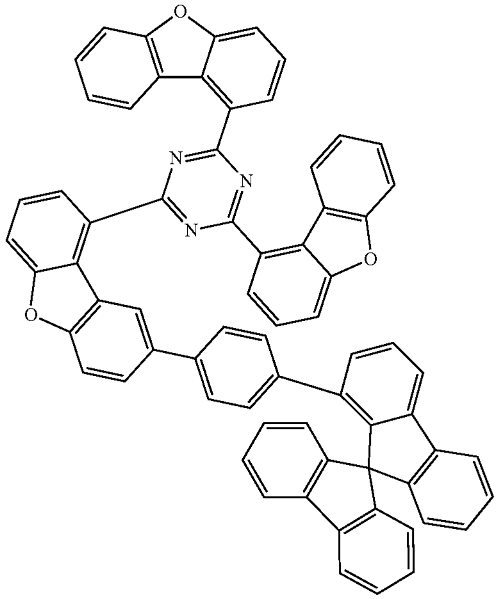 [SMILES: c1ccc2c(c1)-c1ccccc1C21c2ccccc2-c2cccc(-c3ccc(-c4ccc5oc6cccc(-c7nc(-c8cccc9oc%10ccccc%10c89)nc(-c8cccc9oc%10ccccc%10c89)n7)c6c5c4)cc3)c21]
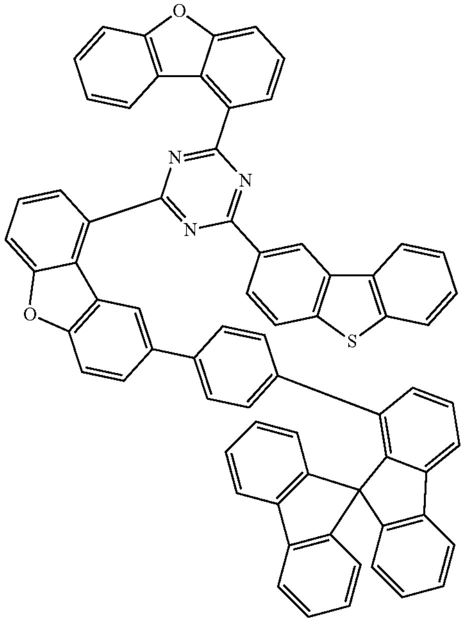 [SMILES: c1ccc2c(c1)-c1ccccc1C21c2ccccc2-c2cccc(-c3ccc(-c4ccc5oc6cccc(-c7nc(-c8ccc9sc%10ccccc%10c9c8)nc(-c8cccc9oc%10ccccc%10c89)n7)c6c5c4)cc3)c21]

TABLE 1-continued
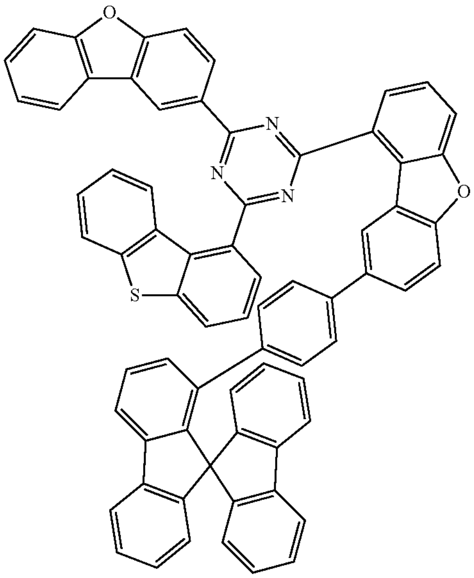 [SMILES: c1ccc2c(c1)-c1ccccc1C21c2ccccc2-c2cccc(-c3ccc(-c4ccc5oc6cccc(-c7nc(-c8ccc9oc%10ccccc%10c9c8)nc(-c8cccc9sc%10ccccc%10c89)n7)c6c5c4)cc3)c21]
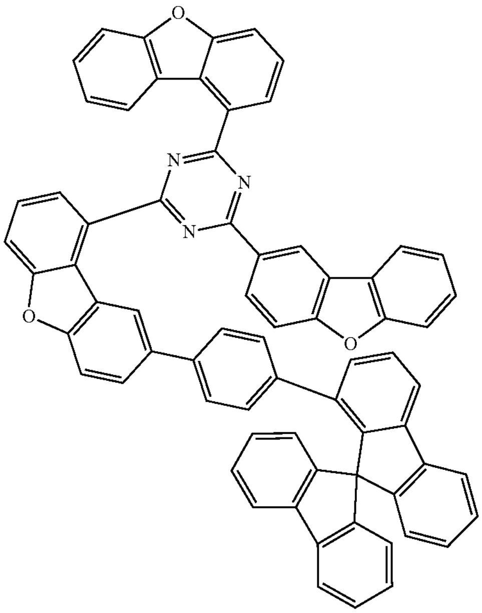 [SMILES: c1ccc2c(c1)-c1ccccc1C21c2ccccc2-c2cccc(-c3ccc(-c4ccc5oc6cccc(-c7nc(-c8ccc9oc%10ccccc%10c9c8)nc(-c8cccc9oc%10ccccc%10c89)n7)c6c5c4)cc3)c21]

TABLE 1-continued
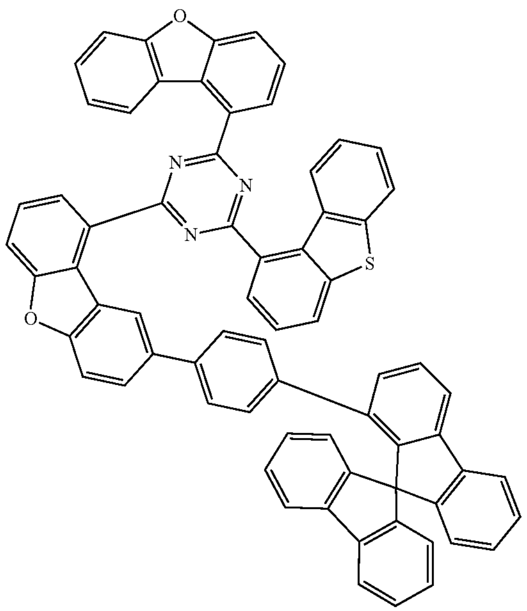 [SMILES: c1ccc2c(c1)-c1ccccc1C21c2ccccc2-c2cccc(-c3ccc(-c4ccc5oc6cccc(-c7nc(-c8cccc9oc%10ccccc%10c89)nc(-c8cccc9sc%10ccccc%10c89)n7)c6c5c4)cc3)c21]
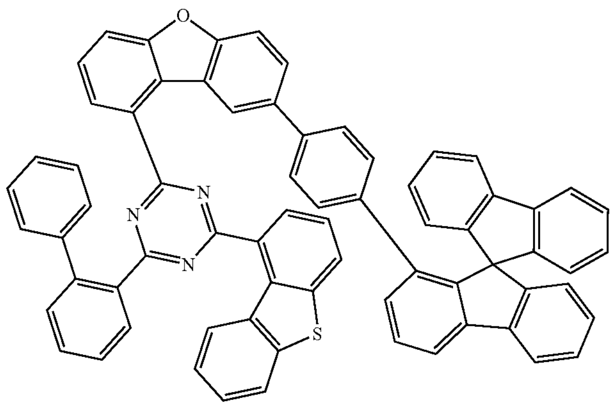 [SMILES: c1ccc(-c2ccccc2-c2nc(-c3cccc4oc5ccc(-c6ccc(-c7cccc8c7C7(c9ccccc9-c9ccccc97)c7ccccc7-8)cc6)cc5c34)nc(-c3cccc4sc5ccccc5c34)n2)cc1]
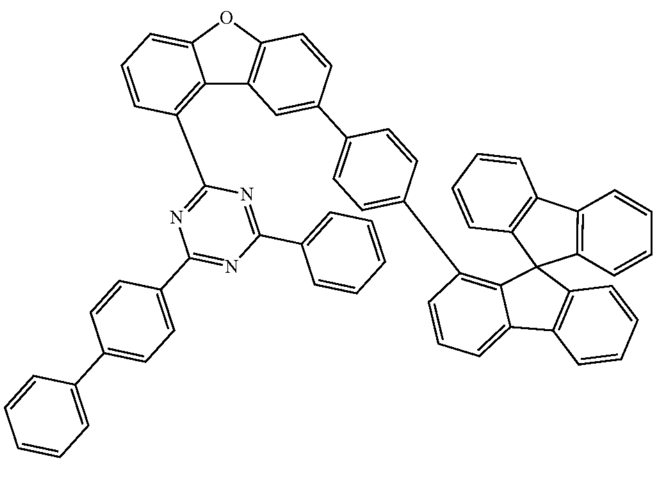 [SMILES: c1ccc(-c2ccc(-c3nc(-c4ccccc4)nc(-c4cccc5oc6ccc(-c7ccc(-c8cccc9c8C8(c%10ccccc%10-c%10ccccc%108)c8ccccc8-9)cc7)cc6c45)n3)cc2)cc1]

TABLE 1-continued
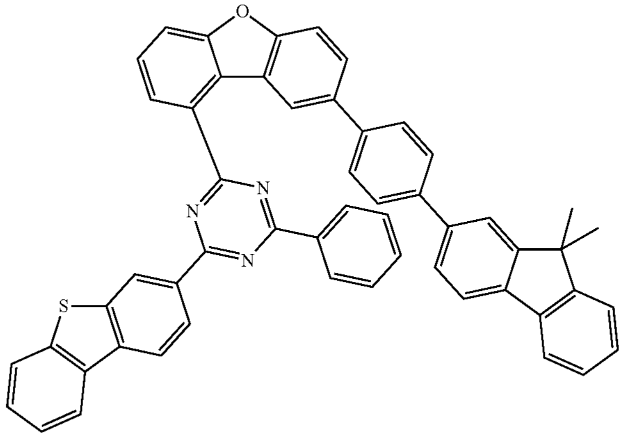 [SMILES: CC1(C)c2ccccc2-c2ccc(-c3ccc(-c4ccc5oc6cccc(-c7nc(-c8ccccc8)nc(-c8ccc9c(c8)sc8ccccc89)n7)c6c5c4)cc3)cc21]
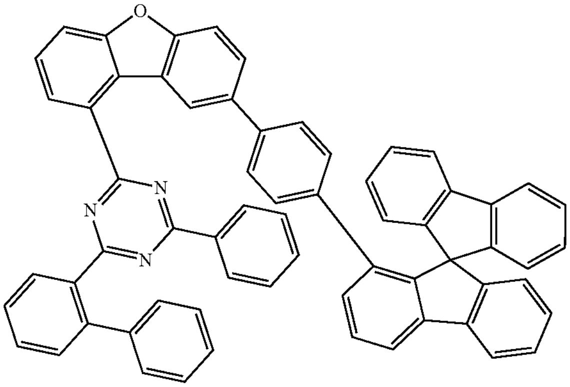 [SMILES: c1ccc(-c2nc(-c3ccccc3-c3ccccc3)nc(-c3cccc4oc5ccc(-c6ccc(-c7cccc8c7C7(c9ccccc9-c9ccccc97)c7ccccc7-8)cc6)cc5c34)n2)cc1]
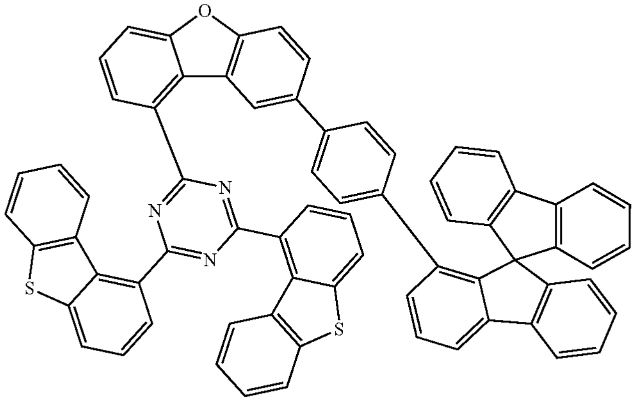 [SMILES: c1ccc2c(c1)-c1ccccc1C21c2ccccc2-c2cccc(-c3ccc(-c4ccc5oc6cccc(-c7nc(-c8cccc9sc%10ccccc%10c89)nc(-c8cccc9sc%10ccccc%10c89)n7)c6c5c4)cc3)c21]
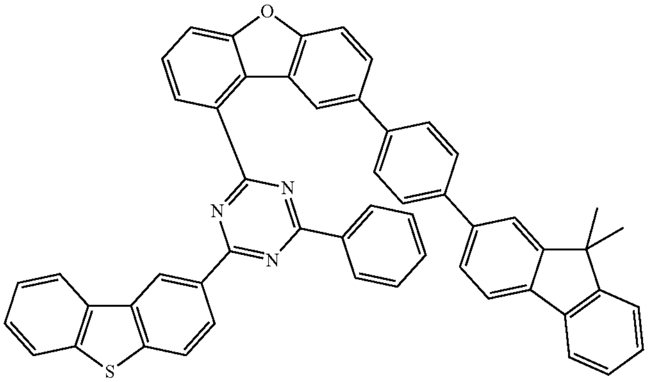 [SMILES: CC1(C)c2ccccc2-c2ccc(-c3ccc(-c4ccc5oc6cccc(-c7nc(-c8ccccc8)nc(-c8ccc9sc%10ccccc%10c9c8)n7)c6c5c4)cc3)cc21]

TABLE 1-continued
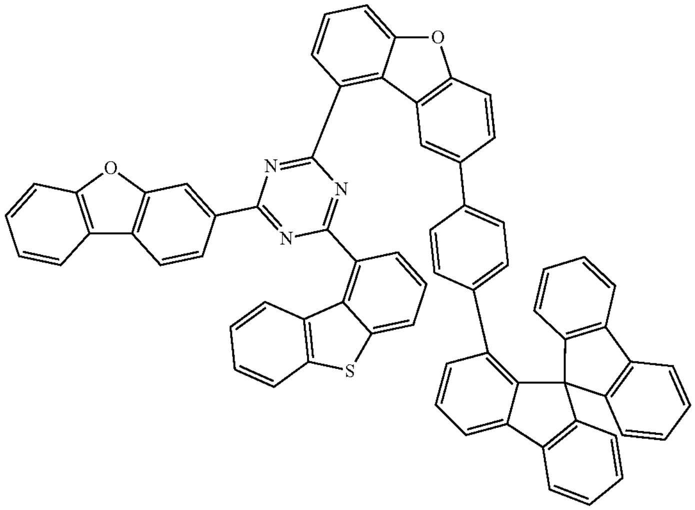 [SMILES: c1ccc2c(c1)-c1ccccc1C21c2ccccc2-c2cccc(-c3ccc(-c4ccc5oc6cccc(-c7nc(-c8ccc9c(c8)oc8ccccc89)nc(-c8cccc9sc%10ccccc%10c89)n7)c6c5c4)cc3)c21]
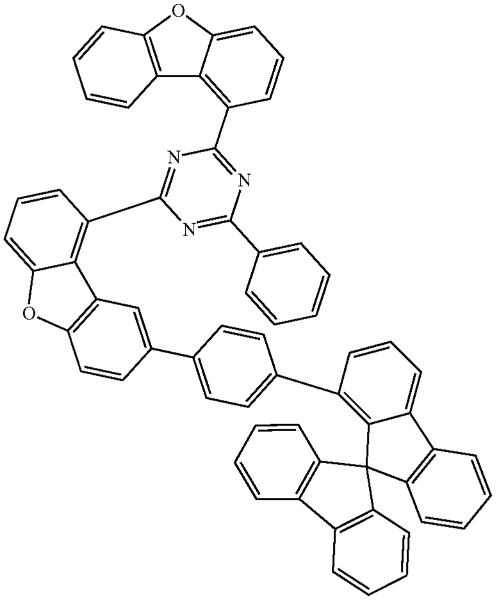 [SMILES: c1ccc(-c2nc(-c3cccc4oc5ccccc5c34)nc(-c3cccc4oc5ccc(-c6ccc(-c7cccc8c7C7(c9ccccc9-c9ccccc97)c7ccccc7-8)cc6)cc5c34)n2)cc1]

TABLE 1-continued
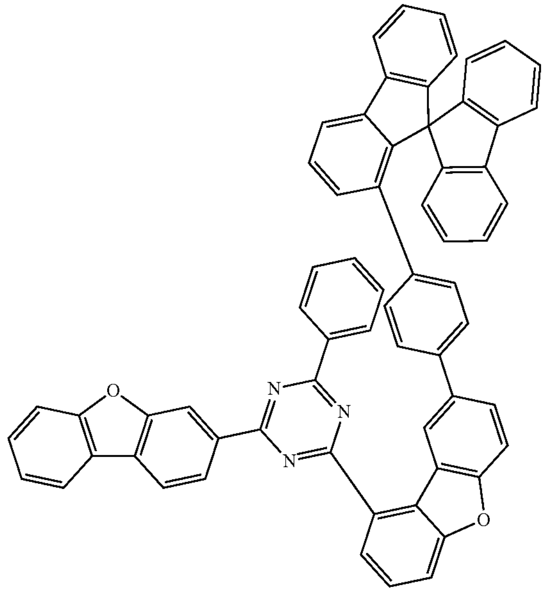 [SMILES: c1ccc(-c2nc(-c3ccc4c(c3)oc3ccccc34)nc(-c3cccc4oc5ccc(-c6ccc(-c7cccc8c7C7(c9ccccc9-c9ccccc97)c7ccccc7-8)cc6)cc5c34)n2)cc1]
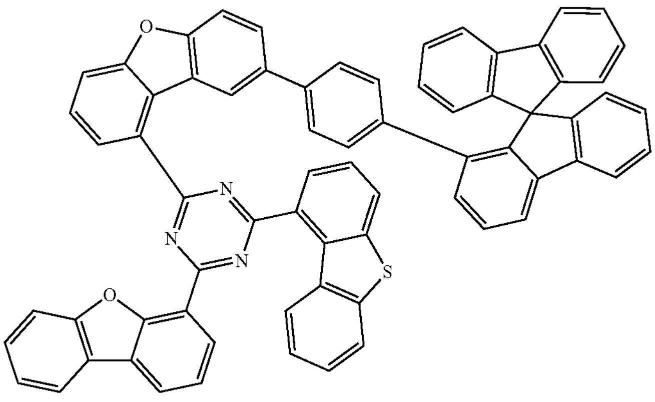 [SMILES: c1ccc2c(c1)-c1ccccc1C21c2ccccc2-c2cccc(-c3ccc(-c4ccc5oc6cccc(-c7nc(-c8cccc9c8oc8ccccc89)nc(-c8cccc9sc%10ccccc%10c89)n7)c6c5c4)cc3)c21]
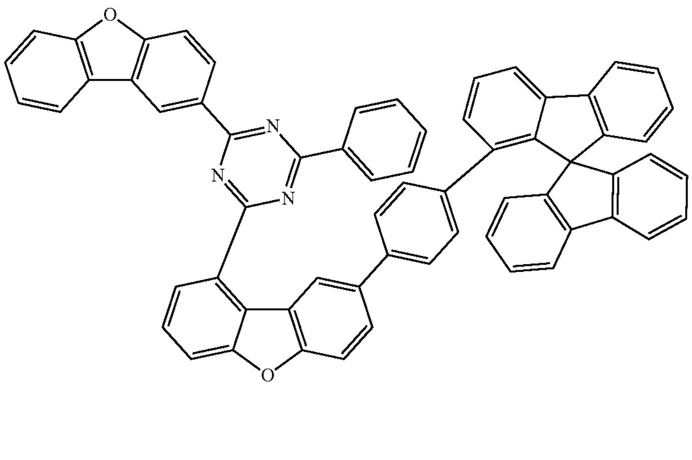 [SMILES: c1ccc(-c2nc(-c3ccc4oc5ccccc5c4c3)nc(-c3cccc4oc5ccc(-c6ccc(-c7cccc8c7C7(c9ccccc9-c9ccccc97)c7ccccc7-8)cc6)cc5c34)n2)cc1]

TABLE 1-continued
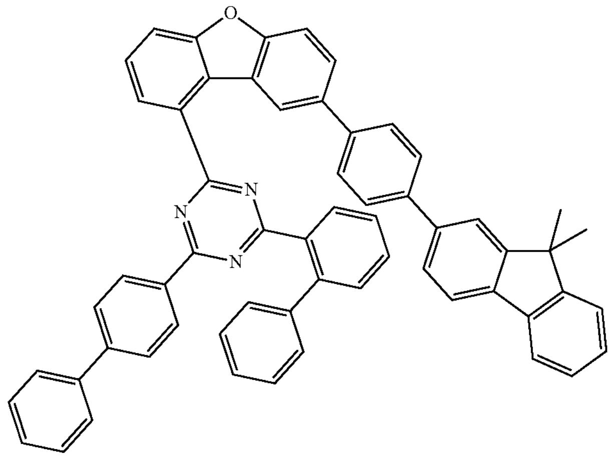 [SMILES: CC1(C)c2ccccc2-c2ccc(-c3ccc(-c4ccc5oc6cccc(-c7nc(-c8ccc(-c9ccccc9)cc8)nc(-c8ccccc8-c8ccccc8)n7)c6c5c4)cc3)cc21]
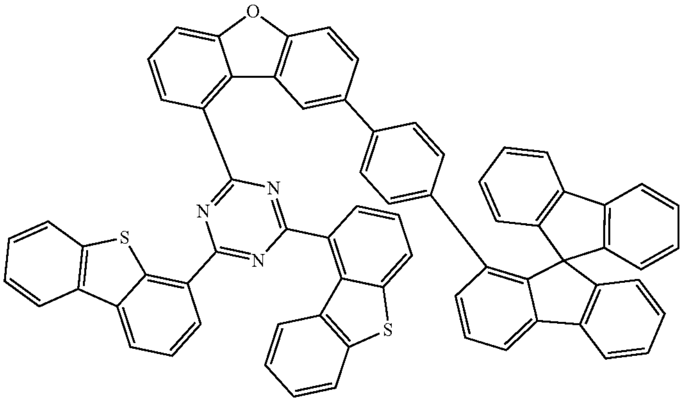 [SMILES: c1ccc2c(c1)-c1ccccc1C21c2ccccc2-c2cccc(-c3ccc(-c4ccc5oc6cccc(-c7nc(-c8cccc9c8sc8ccccc89)nc(-c8cccc9sc%10ccccc%10c89)n7)c6c5c4)cc3)c21]
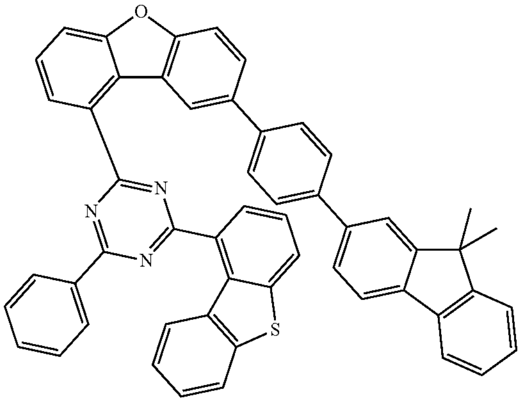 [SMILES: CC1(C)c2ccccc2-c2ccc(-c3ccc(-c4ccc5oc6cccc(-c7nc(-c8ccccc8)nc(-c8cccc9sc%10ccccc%10c89)n7)c6c5c4)cc3)cc21]

TABLE 1-continued
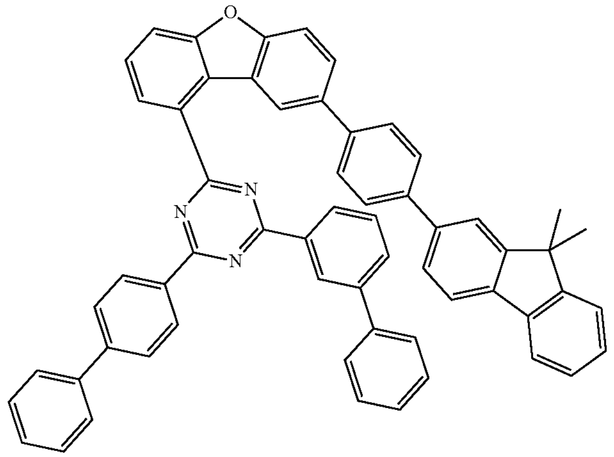 [SMILES: CC1(C)c2ccccc2-c2ccc(-c3ccc(-c4ccc5oc6cccc(-c7nc(-c8ccc(-c9ccccc9)cc8)nc(-c8cccc(-c9ccccc9)c8)n7)c6c5c4)cc3)cc21]
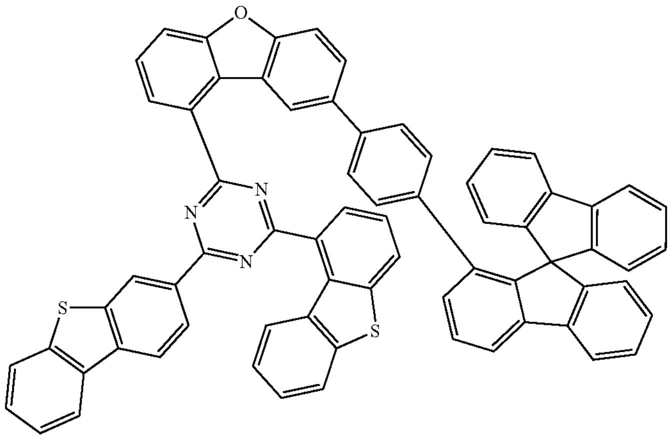 [SMILES: c1ccc2c(c1)-c1ccccc1C21c2ccccc2-c2cccc(-c3ccc(-c4ccc5oc6cccc(-c7nc(-c8ccc9c(c8)sc8ccccc89)nc(-c8cccc9sc%10ccccc%10c89)n7)c6c5c4)cc3)c21]
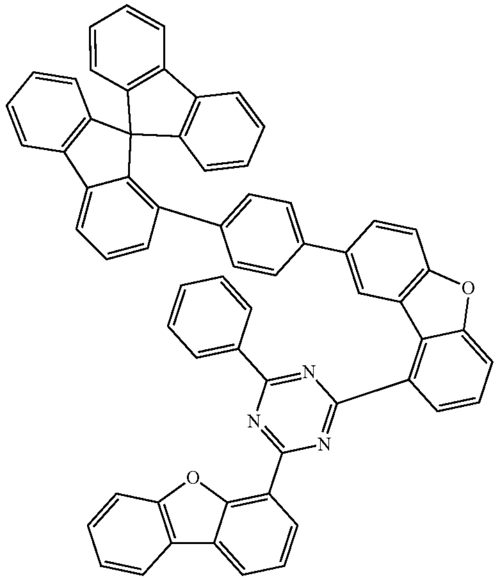 [SMILES: c1ccc(-c2nc(-c3cccc4c3oc3ccccc34)nc(-c3cccc4oc5ccc(-c6ccc(-c7cccc8c7C7(c9ccccc9-c9ccccc97)c7ccccc7-8)cc6)cc5c34)n2)cc1]

TABLE 1-continued
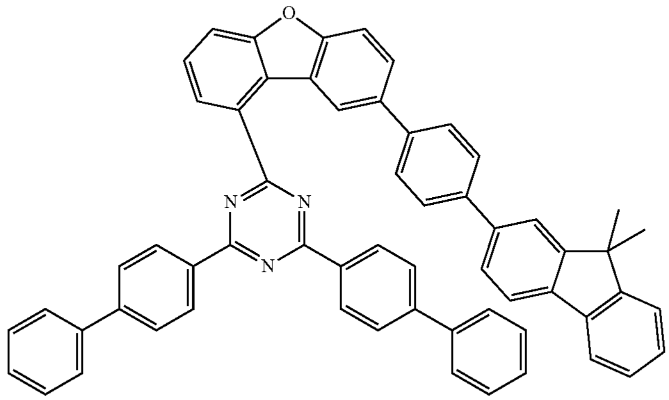 [SMILES: CC1(C)c2ccccc2-c2ccc(-c3ccc(-c4ccc5oc6cccc(-c7nc(-c8ccc(-c9ccccc9)cc8)nc(-c8ccc(-c9ccccc9)cc8)n7)c6c5c4)cc3)cc21]
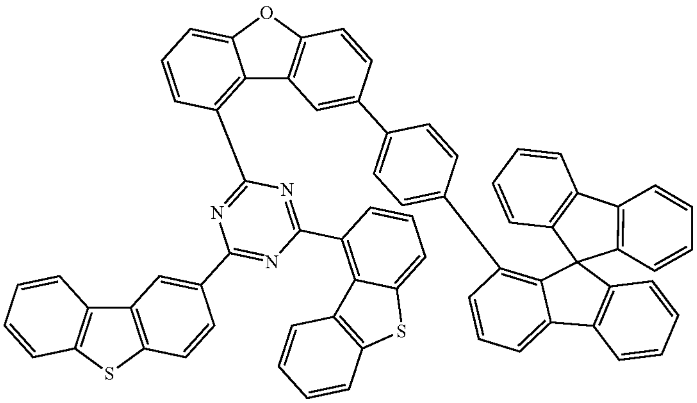 [SMILES: c1ccc2c(c1)-c1ccccc1C21c2ccccc2-c2cccc(-c3ccc(-c4ccc5oc6cccc(-c7nc(-c8ccc9sc%10ccccc%10c9c8)nc(-c8cccc9sc%10ccccc%10c89)n7)c6c5c4)cc3)c21]
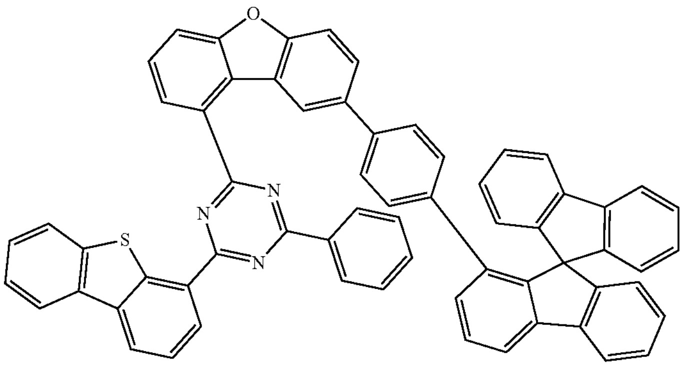 [SMILES: c1ccc(-c2nc(-c3cccc4c3sc3ccccc34)nc(-c3cccc4oc5ccc(-c6ccc(-c7cccc8c7C7(c9ccccc9-c9ccccc97)c7ccccc7-8)cc6)cc5c34)n2)cc1]

TABLE 1-continued
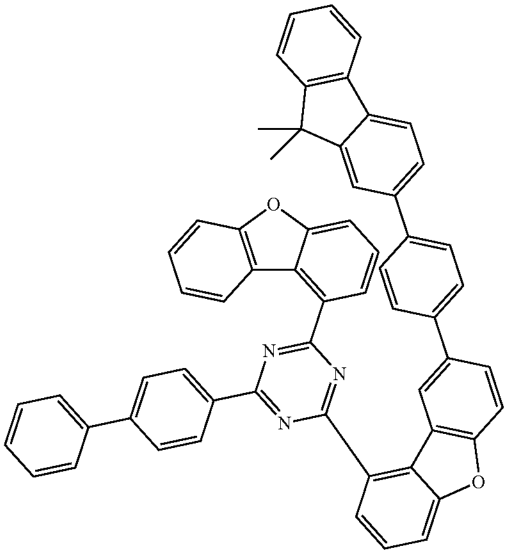 [SMILES: CC1(C)c2ccccc2-c2ccc(-c3ccc(-c4ccc5oc6cccc(-c7nc(-c8ccc(-c9ccccc9)cc8)nc(-c8cccc9oc%10ccccc%10c89)n7)c6c5c4)cc3)cc21]
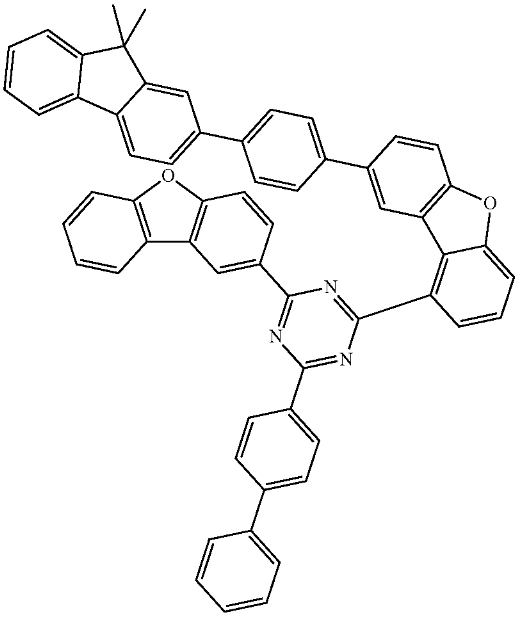 [SMILES: CC1(C)c2ccccc2-c2ccc(-c3ccc(-c4ccc5oc6cccc(-c7nc(-c8ccc(-c9ccccc9)cc8)nc(-c8ccc9oc%10ccccc%10c9c8)n7)c6c5c4)cc3)cc21]
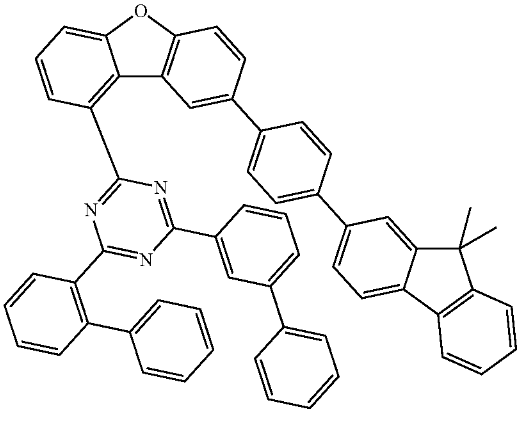 [SMILES: CC1(C)c2ccccc2-c2ccc(-c3ccc(-c4ccc5oc6cccc(-c7nc(-c8cccc(-c9ccccc9)c8)nc(-c8ccccc8-c8ccccc8)n7)c6c5c4)cc3)cc21]

TABLE 1-continued
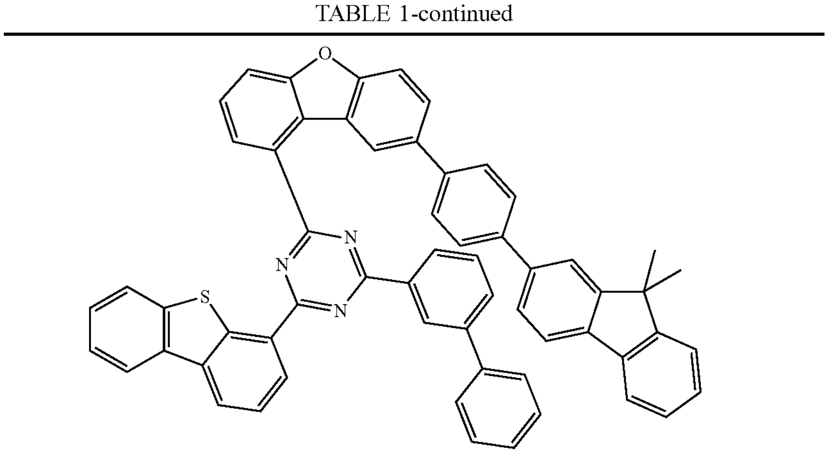
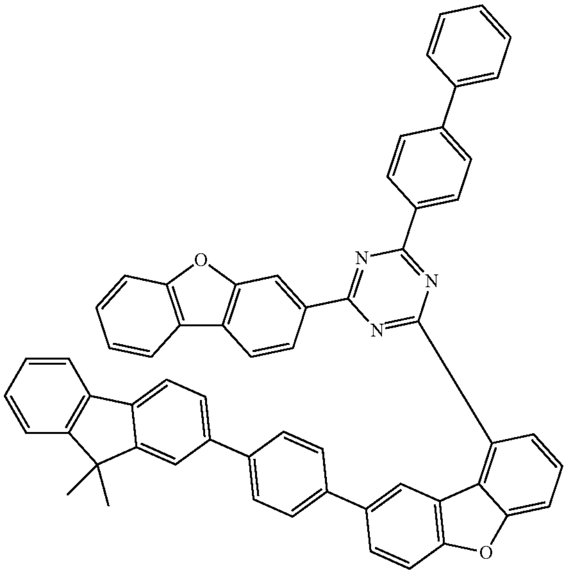 [SMILES: CC1(C)c2ccccc2-c2ccc(-c3ccc(-c4ccc5oc6cccc(-c7nc(-c8ccc(-c9ccccc9)cc8)nc(-c8ccc9c(c8)oc8ccccc89)n7)c6c5c4)cc3)cc21]
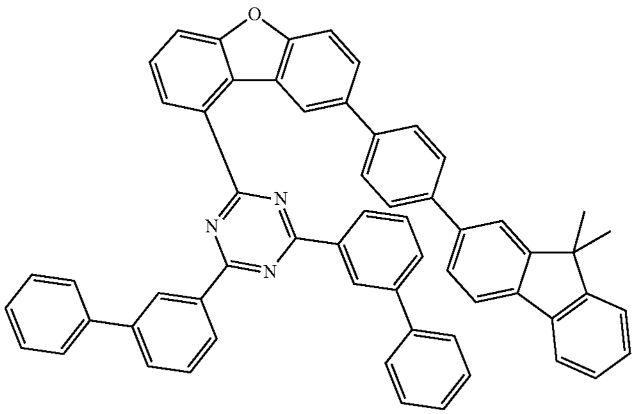 [SMILES: CC1(C)c2ccccc2-c2ccc(-c3ccc(-c4ccc5oc6cccc(-c7nc(-c8cccc(-c9ccccc9)c8)nc(-c8cccc(-c9ccccc9)c8)n7)c6c5c4)cc3)cc21]

TABLE 1-continued
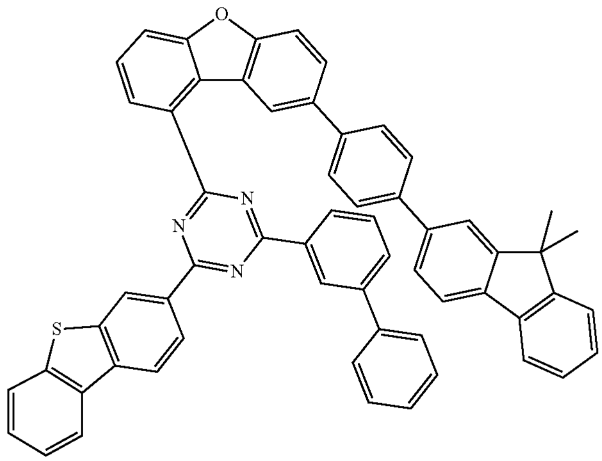 [SMILES: CC1(C)c2ccccc2-c2ccc(-c3ccc(-c4ccc5oc6cccc(-c7nc(-c8cccc(-c9ccccc9)c8)nc(-c8ccc9c(c8)sc8ccccc89)n7)c6c5c4)cc3)cc21]
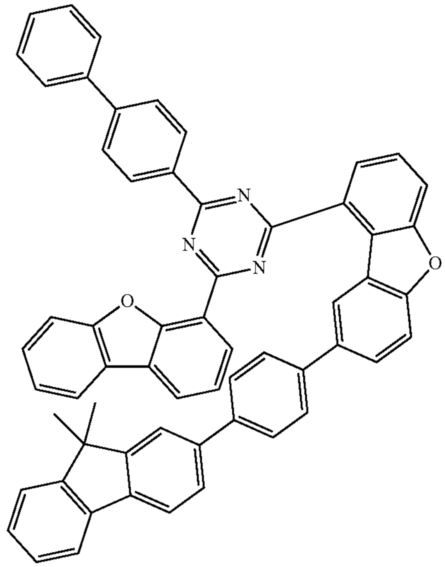 [SMILES: CC1(C)c2ccccc2-c2ccc(-c3ccc(-c4ccc5oc6cccc(-c7nc(-c8ccc(-c9ccccc9)cc8)nc(-c8cccc9c8oc8ccccc89)n7)c6c5c4)cc3)cc21]
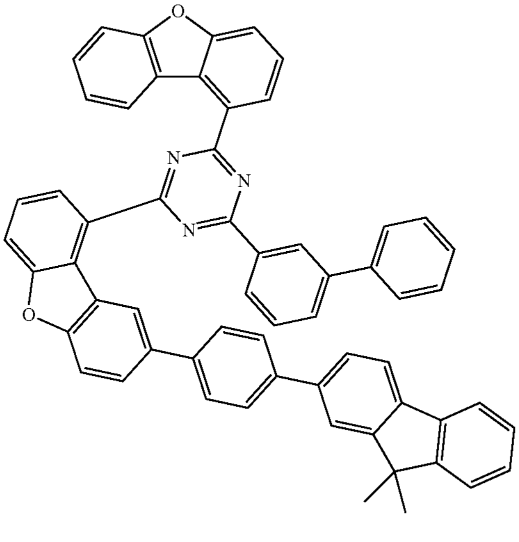 [SMILES: CC1(C)c2ccccc2-c2ccc(-c3ccc(-c4ccc5oc6cccc(-c7nc(-c8cccc(-c9ccccc9)c8)nc(-c8cccc9oc%10ccccc%10c89)n7)c6c5c4)cc3)cc21]

TABLE 1-continued
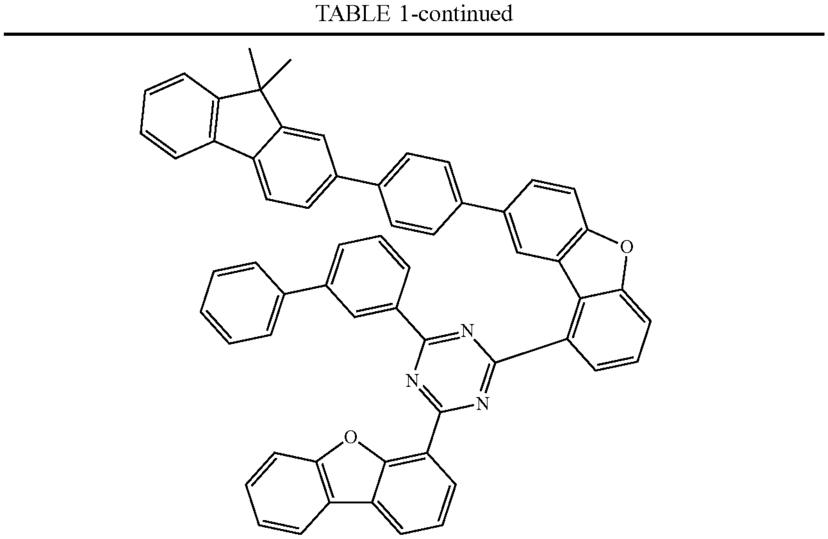
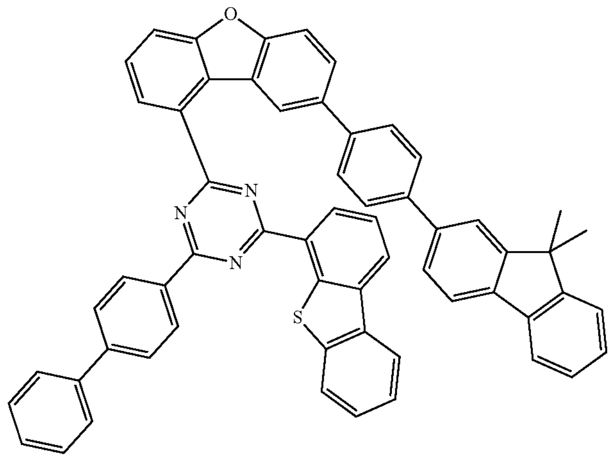 [SMILES: CC1(C)c2ccccc2-c2ccc(-c3ccc(-c4ccc5oc6cccc(-c7nc(-c8ccc(-c9ccccc9)cc8)nc(-c8cccc9c8sc8ccccc89)n7)c6c5c4)cc3)cc21]
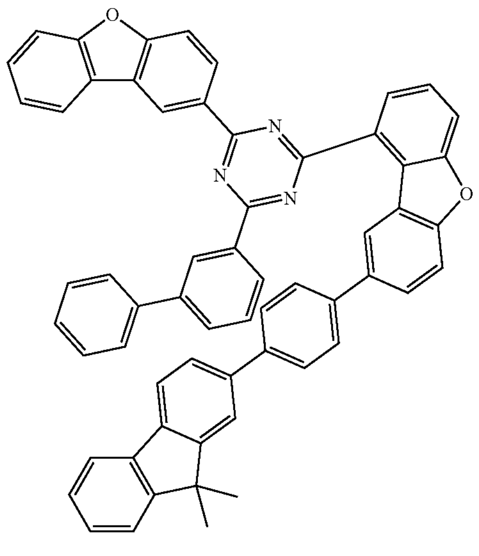 [SMILES: CC1(C)c2ccccc2-c2ccc(-c3ccc(-c4ccc5oc6cccc(-c7nc(-c8cccc(-c9ccccc9)c8)nc(-c8ccc9oc%10ccccc%10c9c8)n7)c6c5c4)cc3)cc21]

TABLE 1-continued
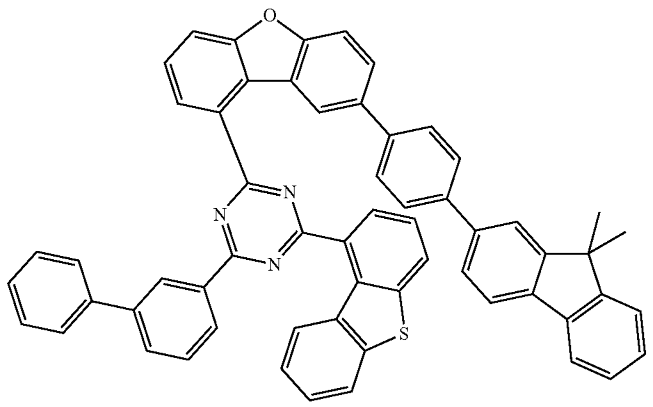 [SMILES: CC1(C)c2ccccc2-c2ccc(-c3ccc(-c4ccc5oc6cccc(-c7nc(-c8cccc(-c9ccccc9)c8)nc(-c8cccc9sc%10ccccc%10c89)n7)c6c5c4)cc3)cc21]
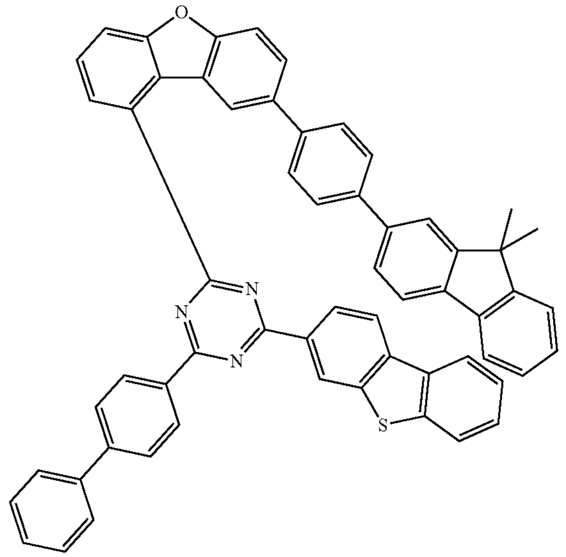 [SMILES: CC1(C)c2ccccc2-c2ccc(-c3ccc(-c4ccc5oc6cccc(-c7nc(-c8ccc(-c9ccccc9)cc8)nc(-c8ccc9c(c8)sc8ccccc89)n7)c6c5c4)cc3)cc21]
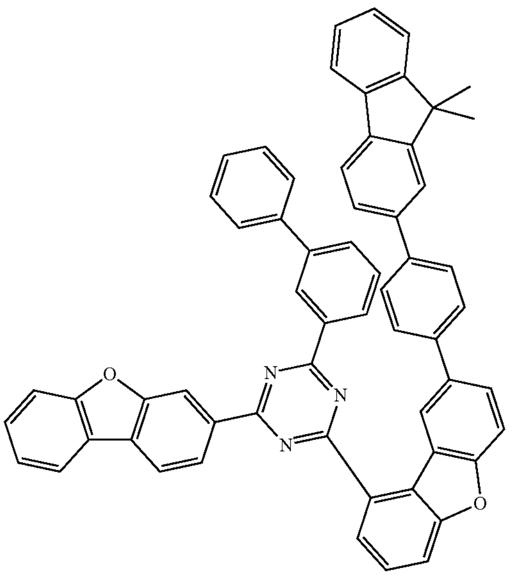 [SMILES: CC1(C)c2ccccc2-c2ccc(-c3ccc(-c4ccc5oc6cccc(-c7nc(-c8cccc(-c9ccccc9)c8)nc(-c8ccc9c(c8)oc8ccccc89)n7)c6c5c4)cc3)cc21]

TABLE 1-continued
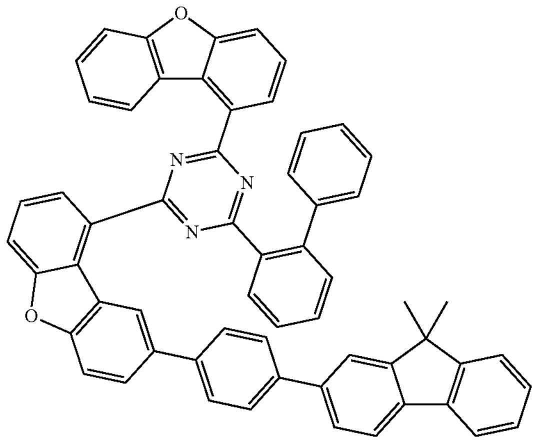 [SMILES: CC1(C)c2ccccc2-c2ccc(-c3ccc(-c4ccc5oc6cccc(-c7nc(-c8ccccc8-c8ccccc8)nc(-c8cccc9oc%10ccccc%10c89)n7)c6c5c4)cc3)cc21]
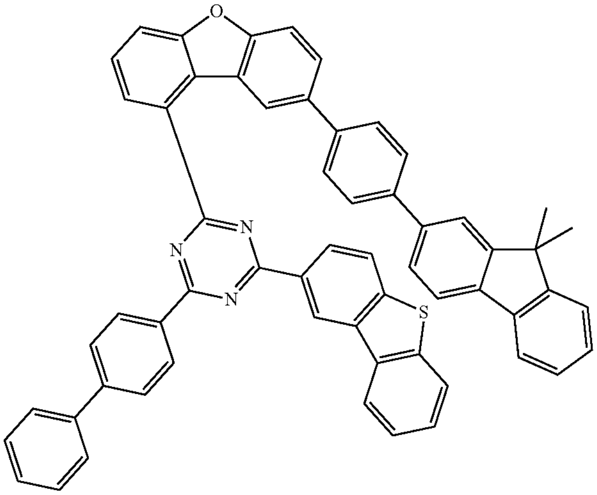 [SMILES: CC1(C)c2ccccc2-c2ccc(-c3ccc(-c4ccc5oc6cccc(-c7nc(-c8ccc(-c9ccccc9)cc8)nc(-c8ccc9sc%10ccccc%10c9c8)n7)c6c5c4)cc3)cc21]
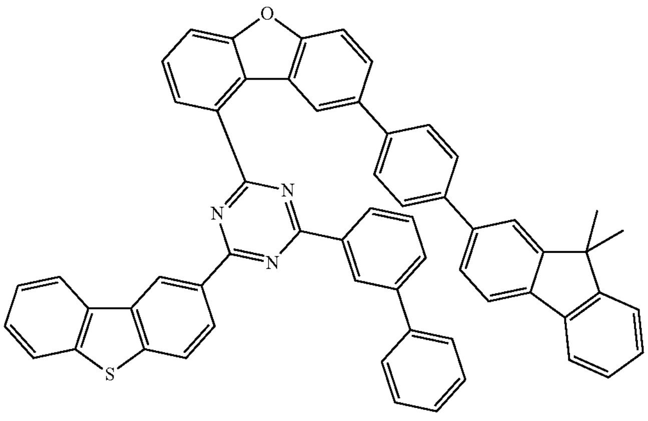 [SMILES: CC1(C)c2ccccc2-c2ccc(-c3ccc(-c4ccc5oc6cccc(-c7nc(-c8cccc(-c9ccccc9)c8)nc(-c8ccc9sc%10ccccc%10c9c8)n7)c6c5c4)cc3)cc21]

TABLE 1-continued
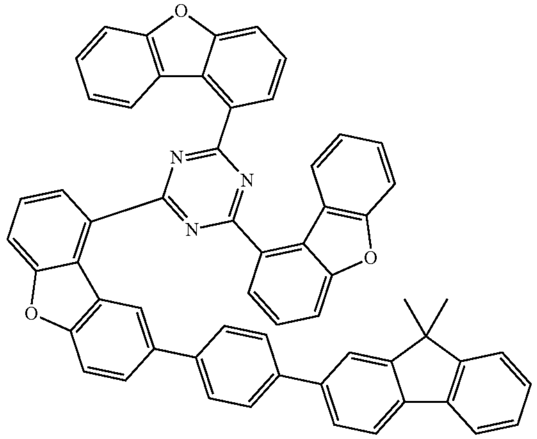
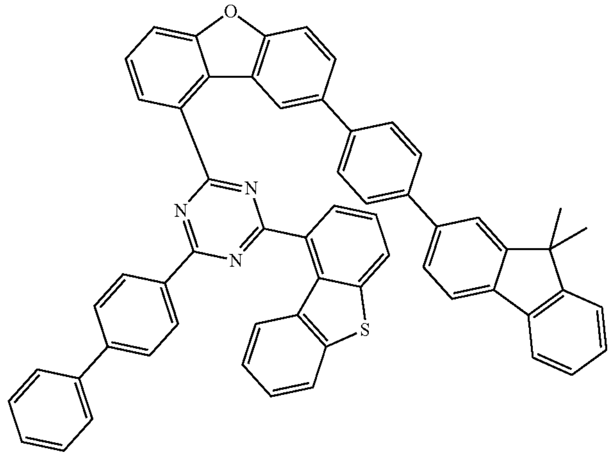 [SMILES: CC1(C)c2ccccc2-c2ccc(-c3ccc(-c4ccc5oc6cccc(-c7nc(-c8ccc(-c9ccccc9)cc8)nc(-c8cccc9sc%10ccccc%10c89)n7)c6c5c4)cc3)cc21]
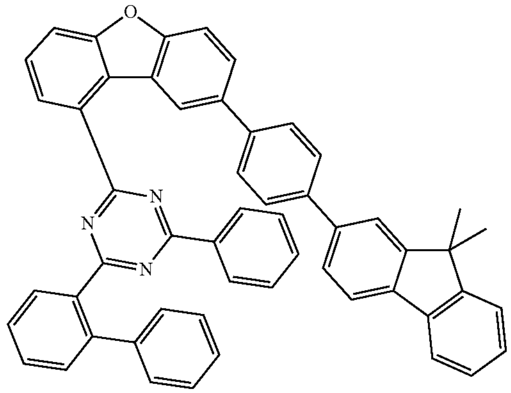 [SMILES: CC1(C)c2ccccc2-c2ccc(-c3ccc(-c4ccc5oc6cccc(-c7nc(-c8ccccc8)nc(-c8ccccc8-c8ccccc8)n7)c6c5c4)cc3)cc21]

TABLE 1-continued
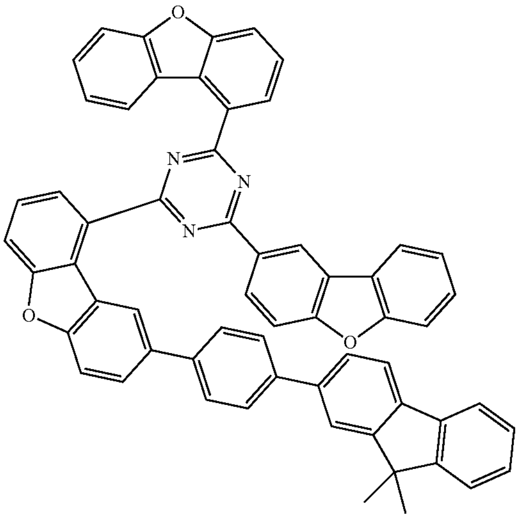 [SMILES: CC1(C)c2ccccc2-c2ccc(-c3ccc(-c4ccc5oc6cccc(-c7nc(-c8ccc9oc%10ccccc%10c9c8)nc(-c8cccc9oc%10ccccc%10c89)n7)c6c5c4)cc3)cc21]
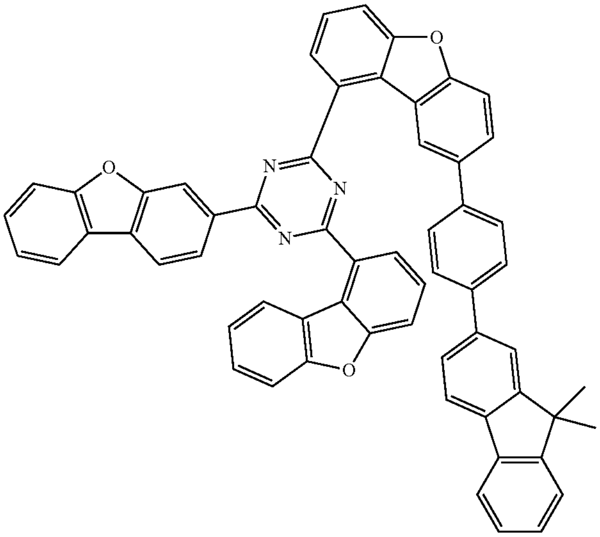
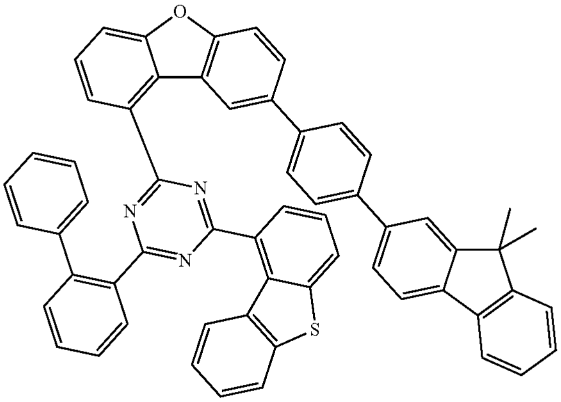 [SMILES: CC1(C)c2ccccc2-c2ccc(-c3ccc(-c4ccc5oc6cccc(-c7nc(-c8ccccc8-c8ccccc8)nc(-c8cccc9sc%10ccccc%10c89)n7)c6c5c4)cc3)cc21]

TABLE 1-continued
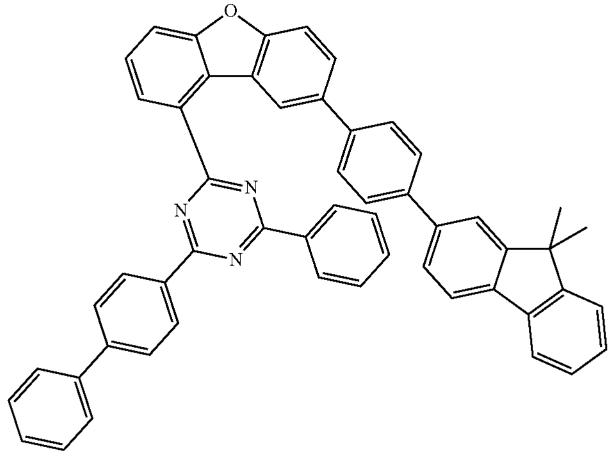 [SMILES: CC1(C)c2ccccc2-c2ccc(-c3ccc(-c4ccc5oc6cccc(-c7nc(-c8ccccc8)nc(-c8ccc(-c9ccccc9)cc8)n7)c6c5c4)cc3)cc21]
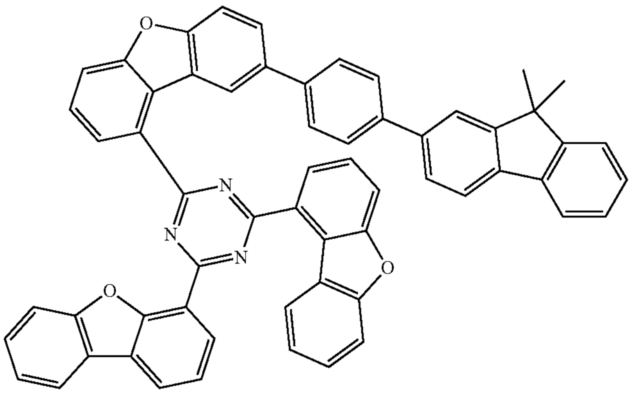 [SMILES: CC1(C)c2ccccc2-c2ccc(-c3ccc(-c4ccc5oc6cccc(-c7nc(-c8cccc9c8oc8ccccc89)nc(-c8cccc9oc%10ccccc%10c89)n7)c6c5c4)cc3)cc21]
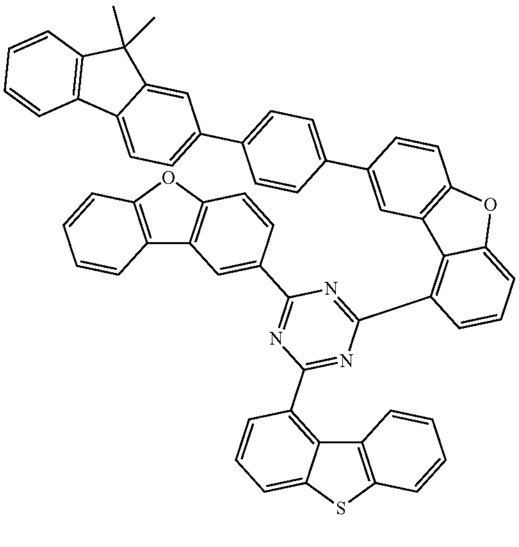 [SMILES: CC1(C)c2ccccc2-c2ccc(-c3ccc(-c4ccc5oc6cccc(-c7nc(-c8ccc9oc%10ccccc%10c9c8)nc(-c8cccc9sc%10ccccc%10c89)n7)c6c5c4)cc3)cc21]

TABLE 1-continued
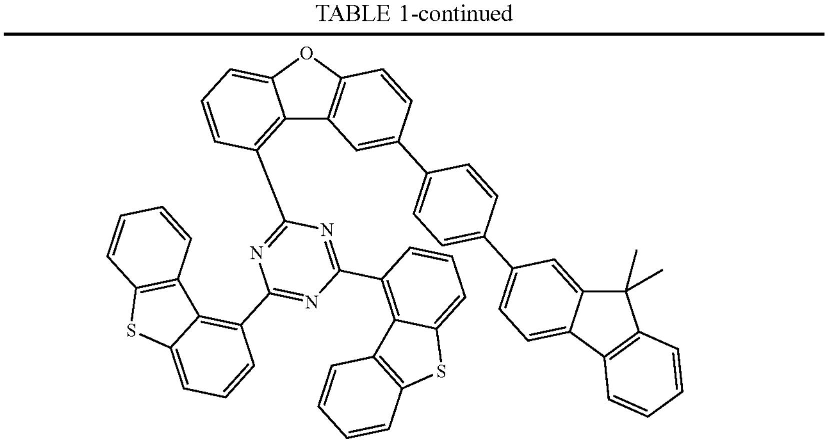
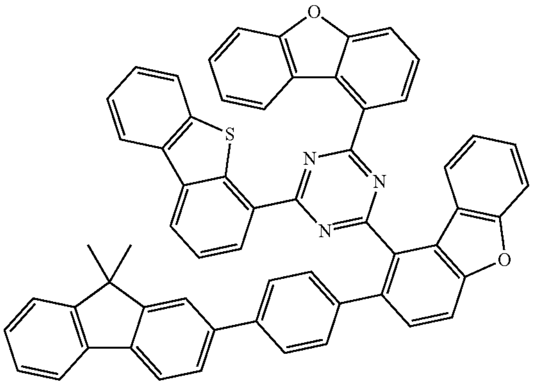 [SMILES: CC1(C)c2ccccc2-c2ccc(-c3ccc(-c4ccc5oc6ccccc6c5c4-c4nc(-c5cccc6c5sc5ccccc56)nc(-c5cccc6oc7ccccc7c56)n4)cc3)cc21]
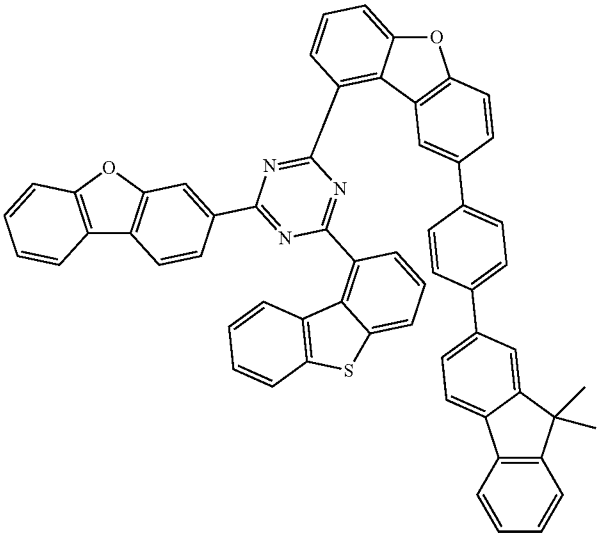 [SMILES: CC1(C)c2ccccc2-c2ccc(-c3ccc(-c4ccc5oc6cccc(-c7nc(-c8ccc9c(c8)oc8ccccc89)nc(-c8cccc9sc%10ccccc%10c89)n7)c6c5c4)cc3)cc21]

TABLE 1-continued
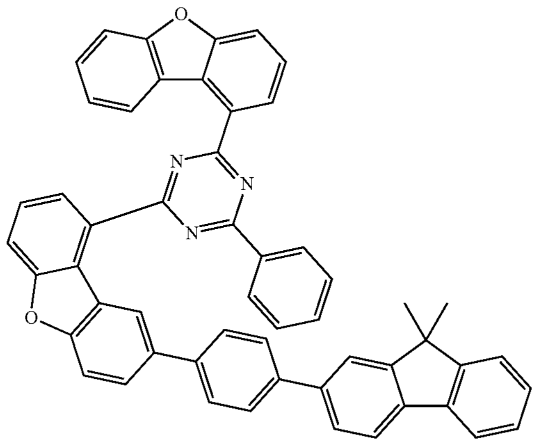 [SMILES: CC1(C)c2ccccc2-c2ccc(-c3ccc(-c4ccc5oc6cccc(-c7nc(-c8ccccc8)nc(-c8cccc9oc%10ccccc%10c89)n7)c6c5c4)cc3)cc21]
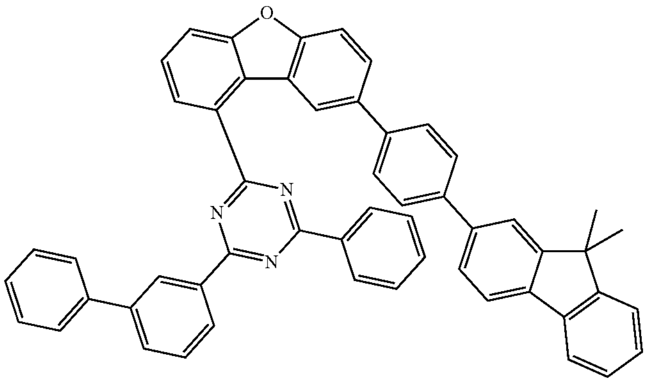 [SMILES: CC1(C)c2ccccc2-c2ccc(-c3ccc(-c4ccc5oc6cccc(-c7nc(-c8ccccc8)nc(-c8cccc(-c9ccccc9)c8)n7)c6c5c4)cc3)cc21]
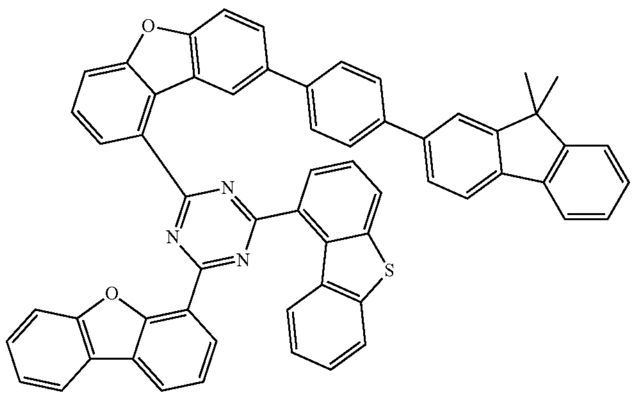 [SMILES: CC1(C)c2ccccc2-c2ccc(-c3ccc(-c4ccc5oc6cccc(-c7nc(-c8cccc9c8oc8ccccc89)nc(-c8cccc9sc%10ccccc%10c89)n7)c6c5c4)cc3)cc21]

TABLE 1-continued
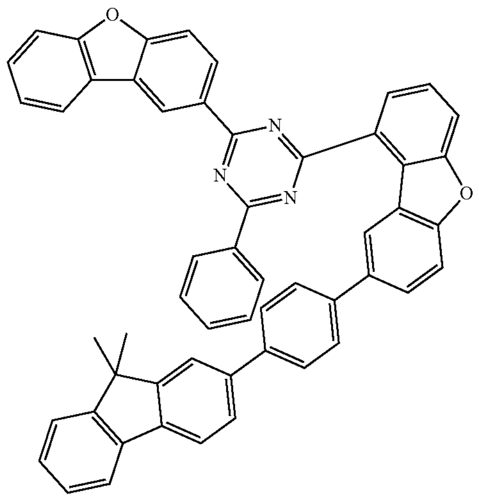 [SMILES: CC1(C)c2ccccc2-c2ccc(-c3ccc(-c4ccc5oc6cccc(-c7nc(-c8ccccc8)nc(-c8ccc9oc%10ccccc%10c9c8)n7)c6c5c4)cc3)cc21]
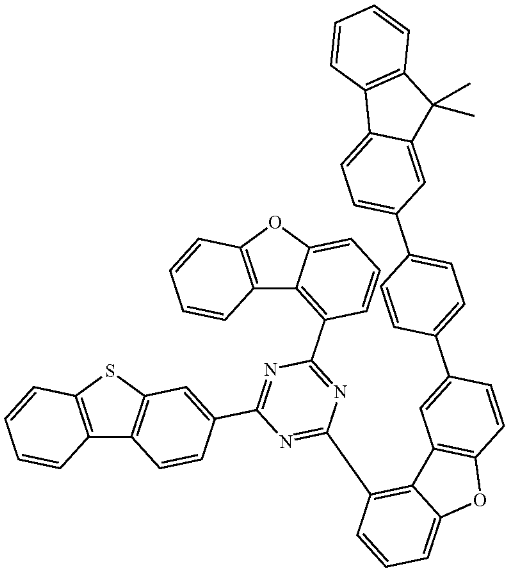 [SMILES: CC1(C)c2ccccc2-c2ccc(-c3ccc(-c4ccc5oc6cccc(-c7nc(-c8ccc9c(c8)sc8ccccc89)nc(-c8cccc9oc%10ccccc%10c89)n7)c6c5c4)cc3)cc21]
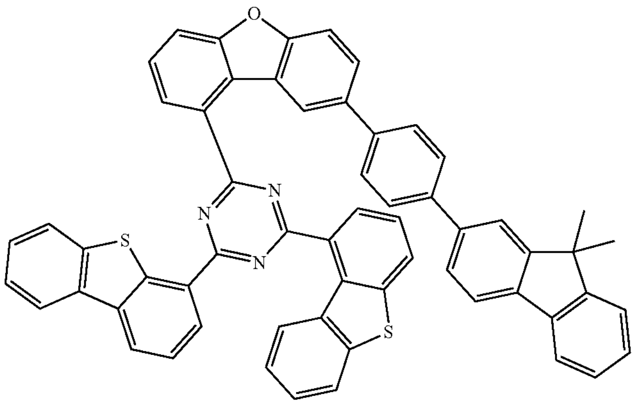 [SMILES: CC1(C)c2ccccc2-c2ccc(-c3ccc(-c4ccc5oc6cccc(-c7nc(-c8cccc9c8sc8ccccc89)nc(-c8cccc9sc%10ccccc%10c89)n7)c6c5c4)cc3)cc21]

TABLE 1-continued
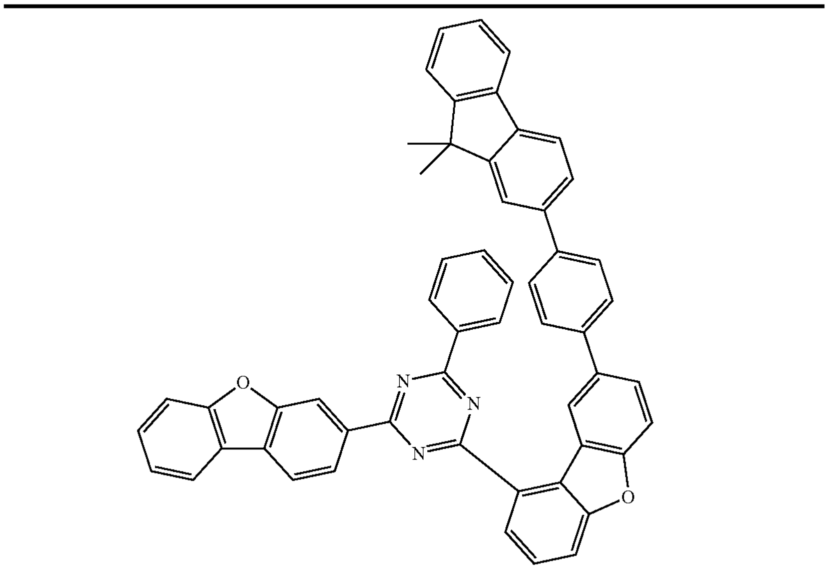
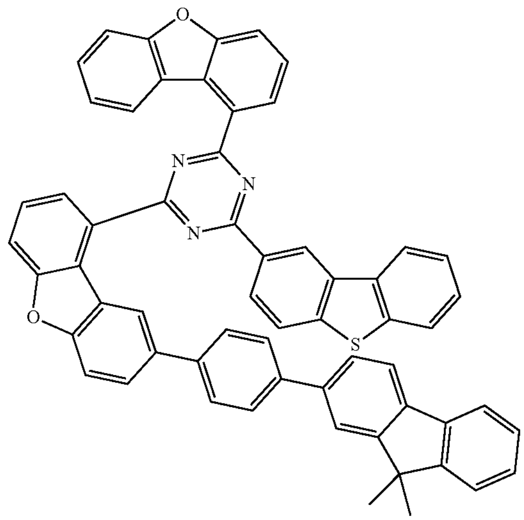 [SMILES: CC1(C)c2ccccc2-c2ccc(-c3ccc(-c4ccc5oc6cccc(-c7nc(-c8ccc9sc%10ccccc%10c9c8)nc(-c8cccc9oc%10ccccc%10c89)n7)c6c5c4)cc3)cc21]
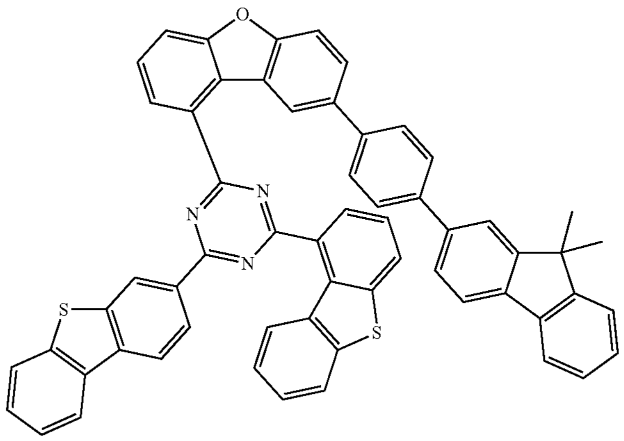 [SMILES: CC1(C)c2ccccc2-c2ccc(-c3ccc(-c4ccc5oc6cccc(-c7nc(-c8ccc9c(c8)sc8ccccc89)nc(-c8cccc9sc%10ccccc%10c89)n7)c6c5c4)cc3)cc21]

TABLE 1-continued
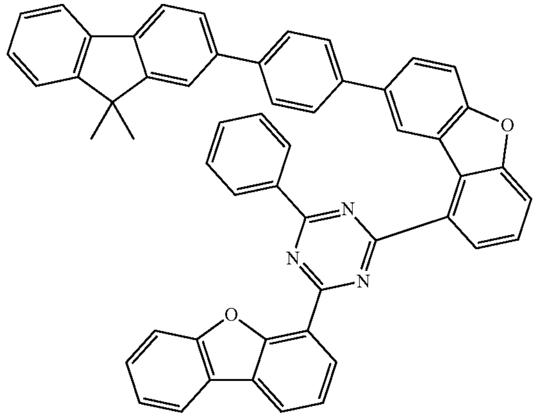 [SMILES: CC1(C)c2ccccc2-c2ccc(-c3ccc(-c4ccc5oc6cccc(-c7nc(-c8ccccc8)nc(-c8cccc9c8oc8ccccc89)n7)c6c5c4)cc3)cc21]
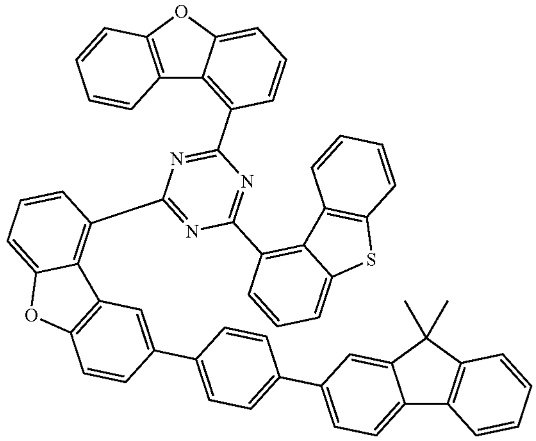
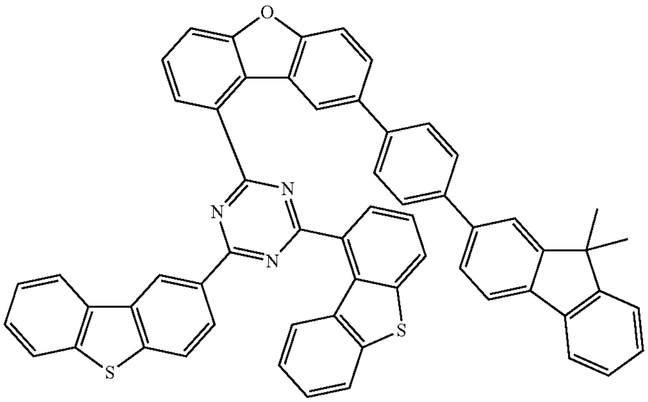 [SMILES: CC1(C)c2ccccc2-c2ccc(-c3ccc(-c4ccc5oc6cccc(-c7nc(-c8ccc9sc%10ccccc%10c9c8)nc(-c8cccc9sc%10ccccc%10c89)n7)c6c5c4)cc3)cc21]
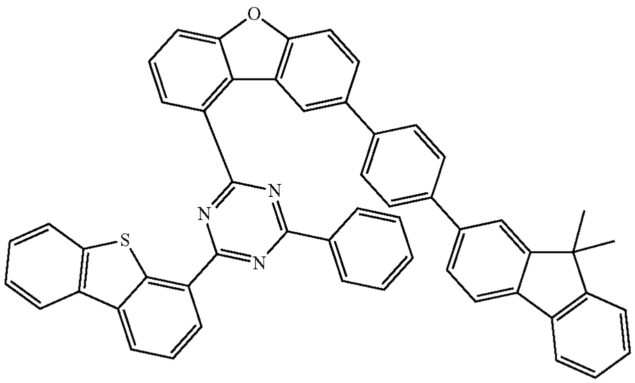 [SMILES: CC1(C)c2ccccc2-c2ccc(-c3ccc(-c4ccc5oc6cccc(-c7nc(-c8ccccc8)nc(-c8cccc9c8sc8ccccc89)n7)c6c5c4)cc3)cc21]

TABLE 1-continued
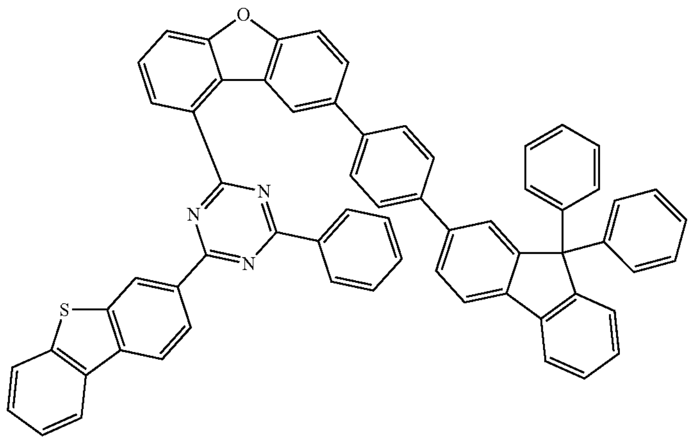 [SMILES: c1ccc(-c2nc(-c3ccc4c(c3)sc3ccccc34)nc(-c3cccc4oc5ccc(-c6ccc(-c7ccc8c(c7)C(c7ccccc7)(c7ccccc7)c7ccccc7-8)cc6)cc5c34)n2)cc1]
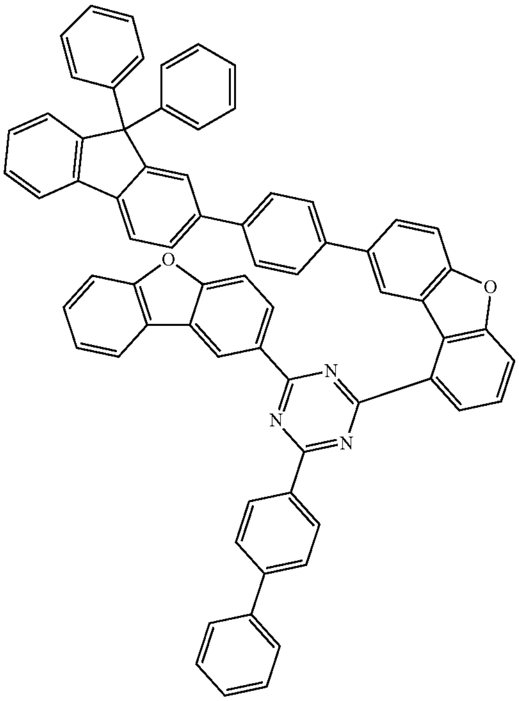 [SMILES: c1ccc(-c2ccc(-c3nc(-c4ccc5oc6ccccc6c5c4)nc(-c4cccc5oc6ccc(-c7ccc(-c8ccc9c(c8)C(c8ccccc8)(c8ccccc8)c8ccccc8-9)cc7)cc6c45)n3)cc2)cc1]
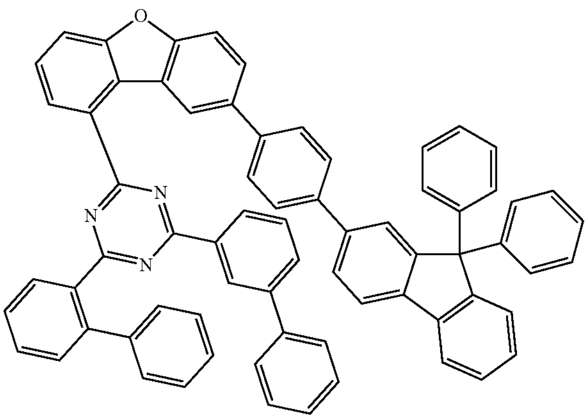 [SMILES: c1ccc(-c2cccc(-c3nc(-c4ccccc4-c4ccccc4)nc(-c4cccc5oc6ccc(-c7ccc(-c8ccc9c(c8)C(c8ccccc8)(c8ccccc8)c8ccccc8-9)cc7)cc6c45)n3)c2)cc1]

TABLE 1-continued
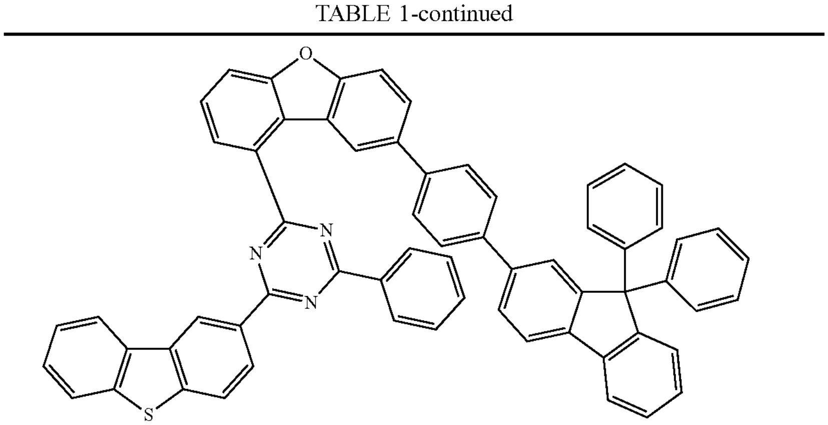
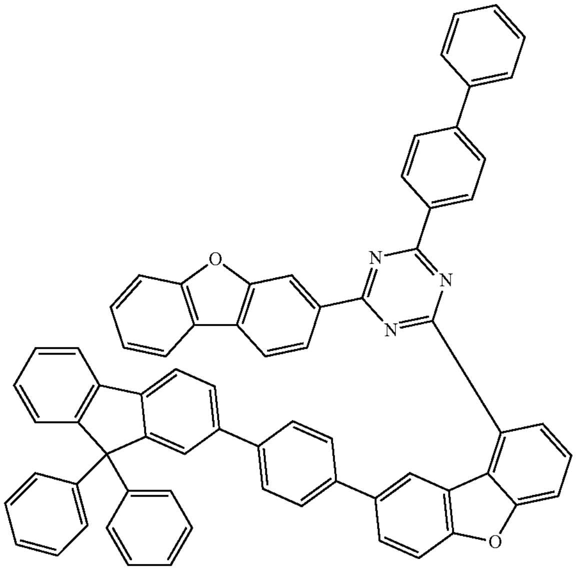 [SMILES: c1ccc(-c2ccc(-c3nc(-c4ccc5c(c4)oc4ccccc45)nc(-c4cccc5oc6ccc(-c7ccc(-c8ccc9c(c8)C(c8ccccc8)(c8ccccc8)c8ccccc8-9)cc7)cc6c45)n3)cc2)cc1]
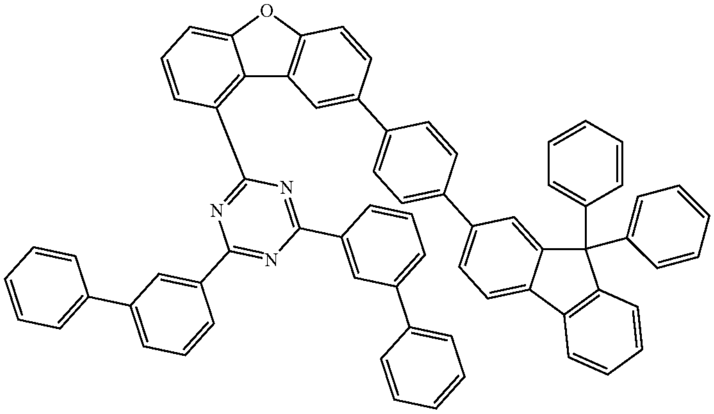 [SMILES: c1ccc(-c2cccc(-c3nc(-c4cccc(-c5ccccc5)c4)nc(-c4cccc5oc6ccc(-c7ccc(-c8ccc9c(c8)C(c8ccccc8)(c8ccccc8)c8ccccc8-9)cc7)cc6c45)n3)c2)cc1]

TABLE 1-continued
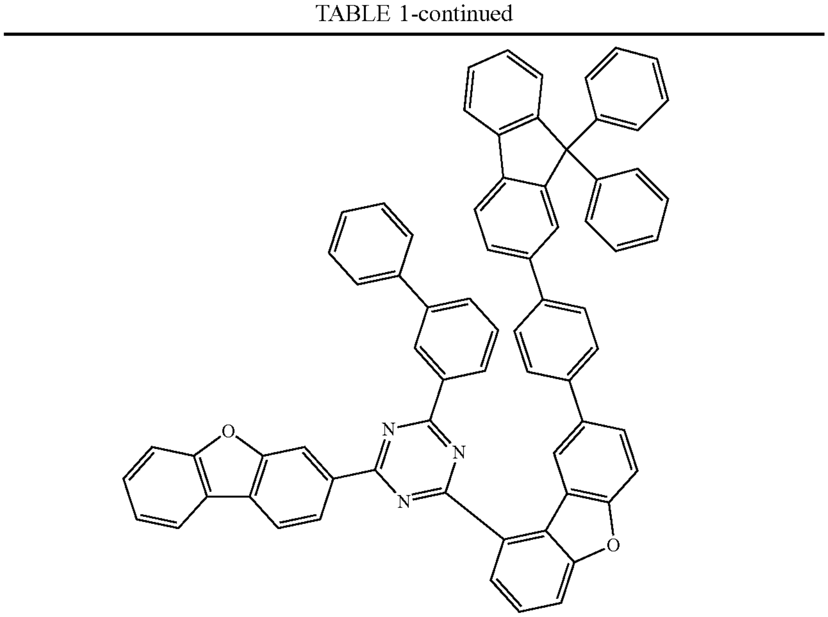
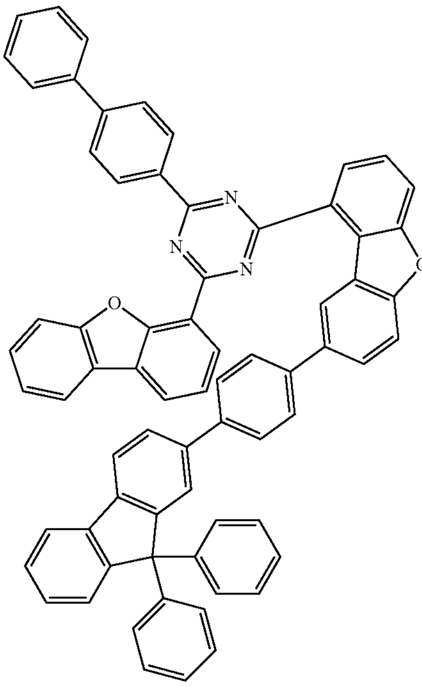 [SMILES: c1ccc(-c2ccc(-c3nc(-c4cccc5c4oc4ccccc45)nc(-c4cccc5oc6ccc(-c7ccc(-c8ccc9c(c8)C(c8ccccc8)(c8ccccc8)c8ccccc8-9)cc7)cc6c45)n3)cc2)cc1]

TABLE 1-continued
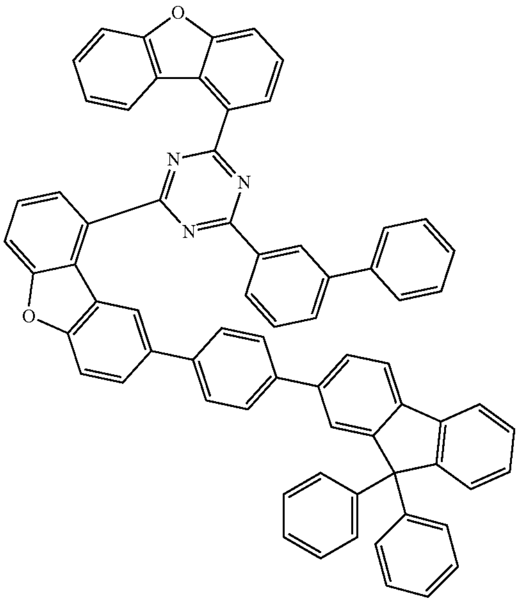 [SMILES: c1ccc(-c2cccc(-c3nc(-c4cccc5oc6ccccc6c45)nc(-c4cccc5oc6ccc(-c7ccc(-c8ccc9c(c8)C(c8ccccc8)(c8ccccc8)c8ccccc8-9)cc7)cc6c45)n3)c2)cc1]
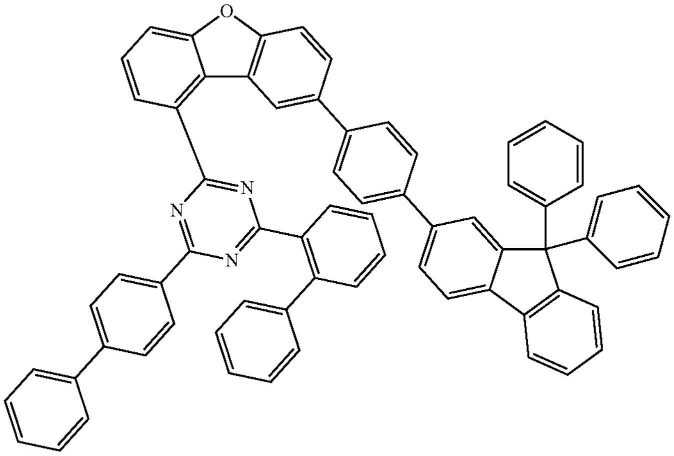 [SMILES: c1ccc(-c2ccc(-c3nc(-c4ccccc4-c4ccccc4)nc(-c4cccc5oc6ccc(-c7ccc(-c8ccc9c(c8)C(c8ccccc8)(c8ccccc8)c8ccccc8-9)cc7)cc6c45)n3)cc2)cc1]
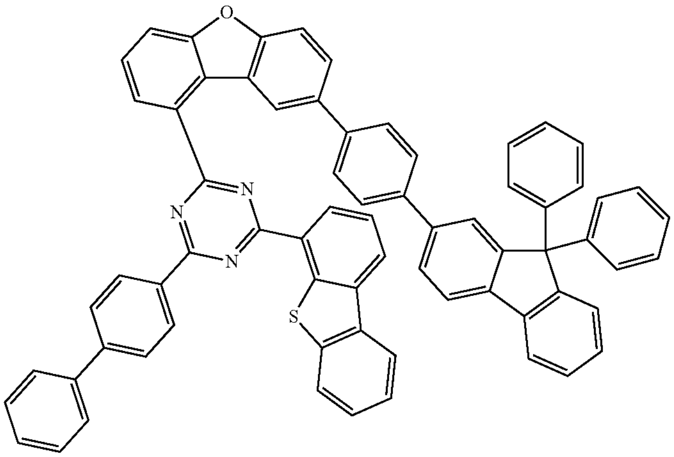 [SMILES: c1ccc(-c2ccc(-c3nc(-c4cccc5c4sc4ccccc45)nc(-c4cccc5oc6ccc(-c7ccc(-c8ccc9c(c8)C(c8ccccc8)(c8ccccc8)c8ccccc8-9)cc7)cc6c45)n3)cc2)cc1]

TABLE 1-continued
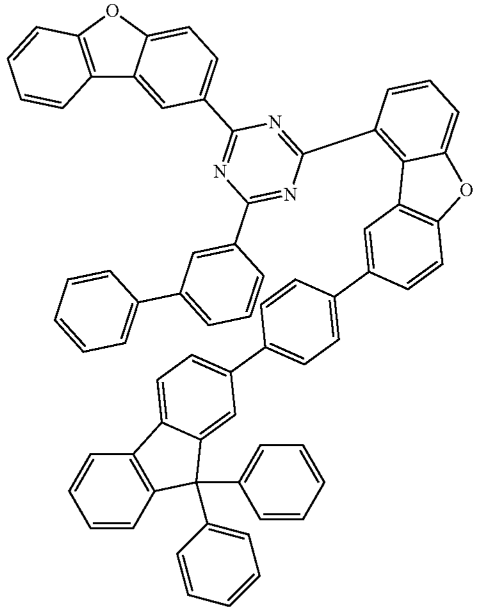 [SMILES: c1ccc(-c2cccc(-c3nc(-c4ccc5oc6ccccc6c5c4)nc(-c4cccc5oc6ccc(-c7ccc(-c8ccc9c(c8)C(c8ccccc8)(c8ccccc8)c8ccccc8-9)cc7)cc6c45)n3)c2)cc1]
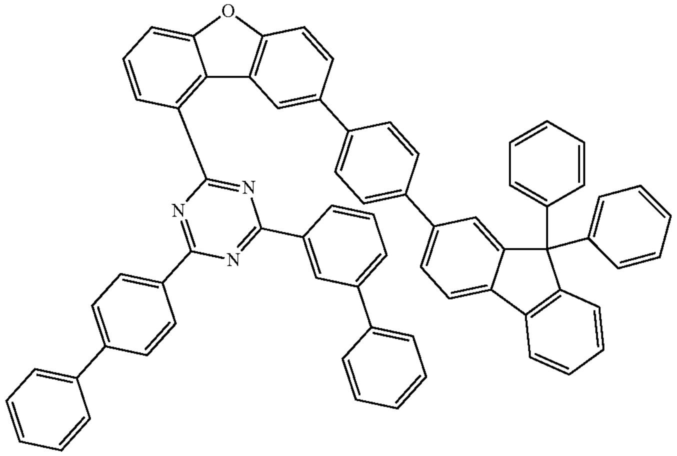 [SMILES: c1ccc(-c2ccc(-c3nc(-c4cccc(-c5ccccc5)c4)nc(-c4cccc5oc6ccc(-c7ccc(-c8ccc9c(c8)C(c8ccccc8)(c8ccccc8)c8ccccc8-9)cc7)cc6c45)n3)cc2)cc1]
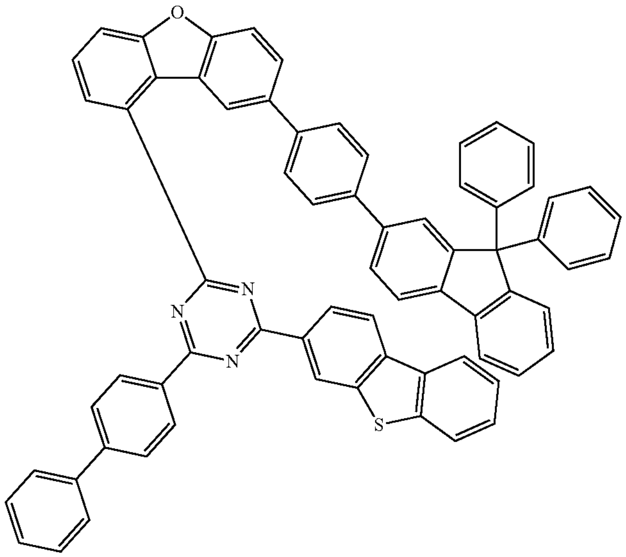 [SMILES: c1ccc(-c2ccc(-c3nc(-c4ccc5c(c4)sc4ccccc45)nc(-c4cccc5oc6ccc(-c7ccc(-c8ccc9c(c8)C(c8ccccc8)(c8ccccc8)c8ccccc8-9)cc7)cc6c45)n3)cc2)cc1]

TABLE 1-continued
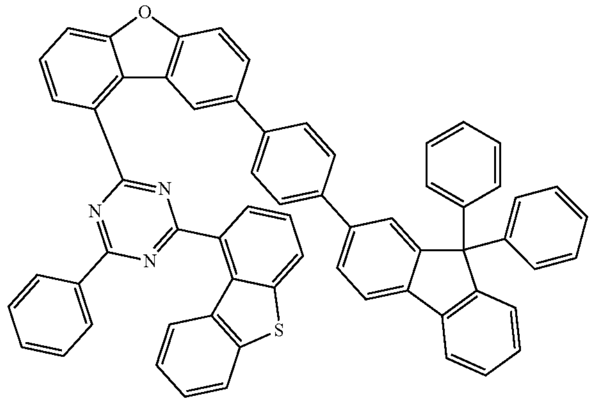 [SMILES: c1ccc(-c2nc(-c3cccc4oc5ccc(-c6ccc(-c7ccc8c(c7)C(c7ccccc7)(c7ccccc7)c7ccccc7-8)cc6)cc5c34)nc(-c3cccc4sc5ccccc5c34)n2)cc1]
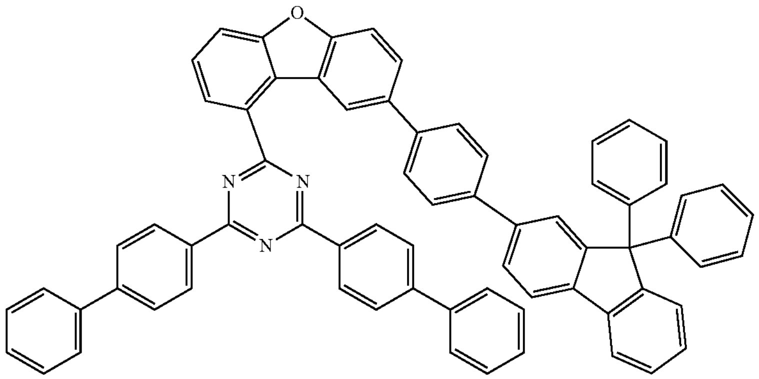 [SMILES: c1ccc(-c2ccc(-c3nc(-c4ccc(-c5ccccc5)cc4)nc(-c4cccc5oc6ccc(-c7ccc(-c8ccc9c(c8)C(c8ccccc8)(c8ccccc8)c8ccccc8-9)cc7)cc6c45)n3)cc2)cc1]
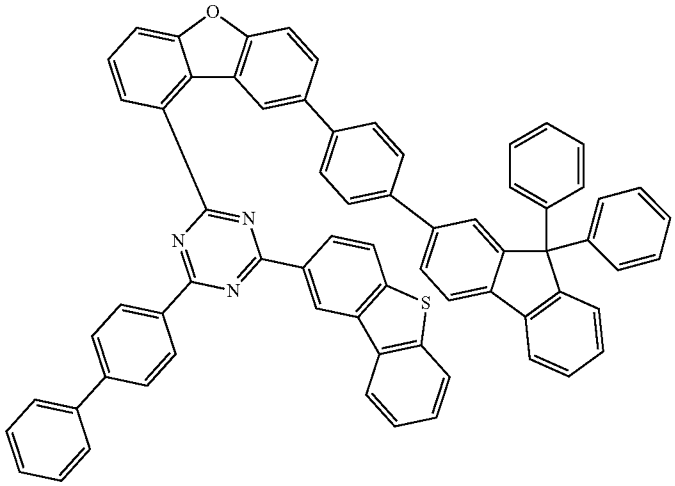 [SMILES: c1ccc(-c2ccc(-c3nc(-c4ccc5sc6ccccc6c5c4)nc(-c4cccc5oc6ccc(-c7ccc(-c8ccc9c(c8)C(c8ccccc8)(c8ccccc8)c8ccccc8-9)cc7)cc6c45)n3)cc2)cc1]

TABLE 1-continued
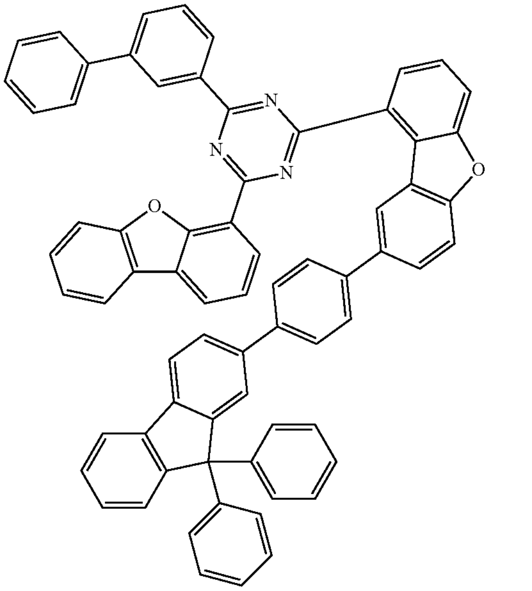 [SMILES: c1ccc(-c2cccc(-c3nc(-c4cccc5c4oc4ccccc45)nc(-c4cccc5oc6ccc(-c7ccc(-c8ccc9c(c8)C(c8ccccc8)(c8ccccc8)c8ccccc8-9)cc7)cc6c45)n3)c2)cc1]
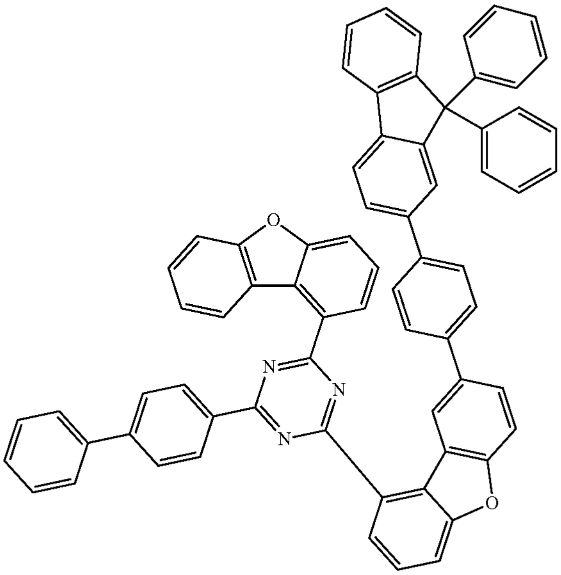 [SMILES: c1ccc(-c2ccc(-c3nc(-c4cccc5oc6ccccc6c45)nc(-c4cccc5oc6ccc(-c7ccc(-c8ccc9c(c8)C(c8ccccc8)(c8ccccc8)c8ccccc8-9)cc7)cc6c45)n3)cc2)cc1]
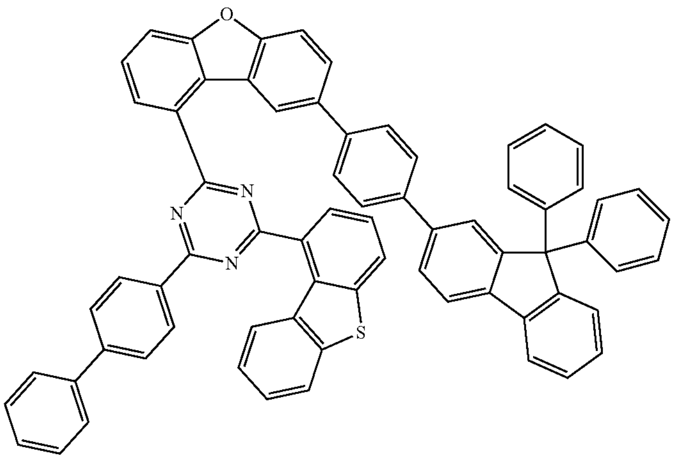 [SMILES: c1ccc(-c2ccc(-c3nc(-c4cccc5oc6ccc(-c7ccc(-c8ccc9c(c8)C(c8ccccc8)(c8ccccc8)c8ccccc8-9)cc7)cc6c45)nc(-c4cccc5sc6ccccc6c45)n3)cc2)cc1]

TABLE 1-continued
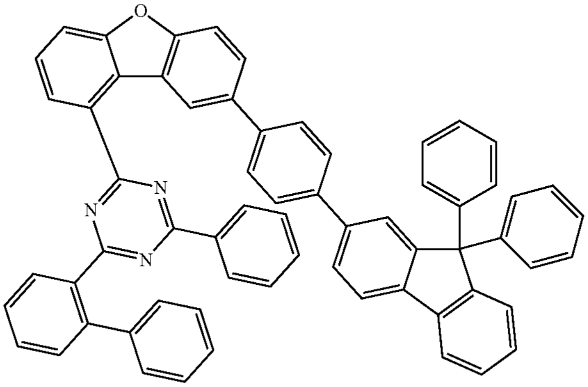 [SMILES: c1ccc(-c2nc(-c3ccccc3-c3ccccc3)nc(-c3cccc4oc5ccc(-c6ccc(-c7ccc8c(c7)C(c7ccccc7)(c7ccccc7)c7ccccc7-8)cc6)cc5c34)n2)cc1]
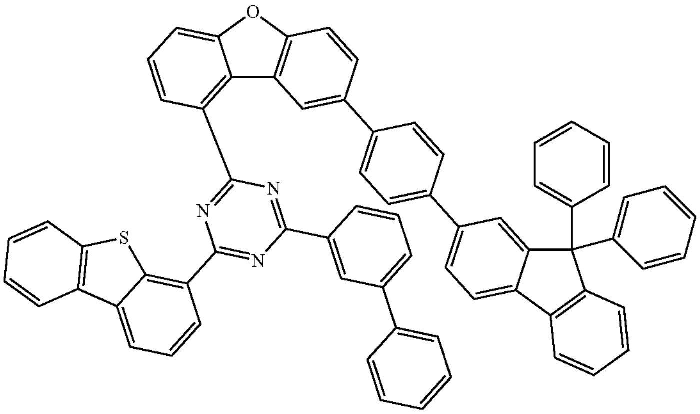 [SMILES: c1ccc(-c2cccc(-c3nc(-c4cccc5c4sc4ccccc45)nc(-c4cccc5oc6ccc(-c7ccc(-c8ccc9c(c8)C(c8ccccc8)(c8ccccc8)c8ccccc8-9)cc7)cc6c45)n3)c2)cc1]
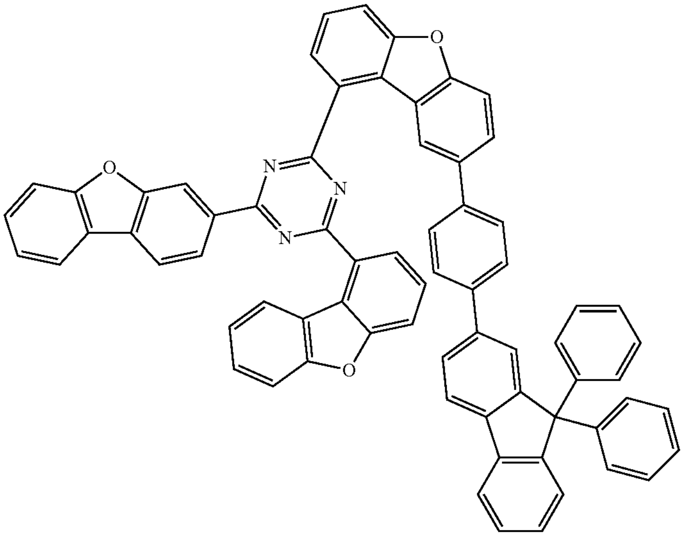 [SMILES: c1ccc(C2(c3ccccc3)c3ccccc3-c3ccc(-c4ccc(-c5ccc6oc7cccc(-c8nc(-c9ccc%10c(c9)oc9ccccc9%10)nc(-c9cccc%10oc%11ccccc%11c9%10)n8)c7c6c5)cc4)cc32)cc1]

TABLE 1-continued
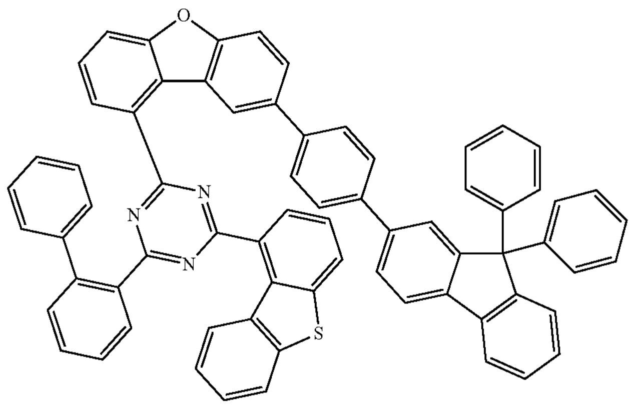 [SMILES: c1ccc(-c2ccccc2-c2nc(-c3cccc4oc5ccc(-c6ccc(-c7ccc8c(c7)C(c7ccccc7)(c7ccccc7)c7ccccc7-8)cc6)cc5c34)nc(-c3cccc4sc5ccccc5c34)n2)cc1]
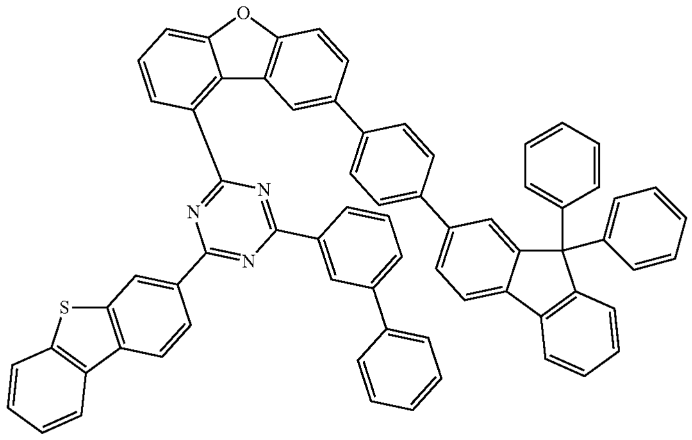 [SMILES: c1ccc(-c2cccc(-c3nc(-c4ccc5c(c4)sc4ccccc45)nc(-c4cccc5oc6ccc(-c7ccc(-c8ccc9c(c8)C(c8ccccc8)(c8ccccc8)c8ccccc8-9)cc7)cc6c45)n3)c2)cc1]
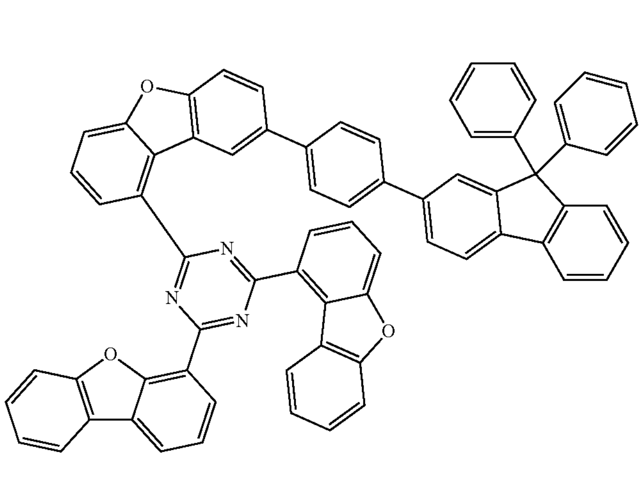

TABLE 1-continued
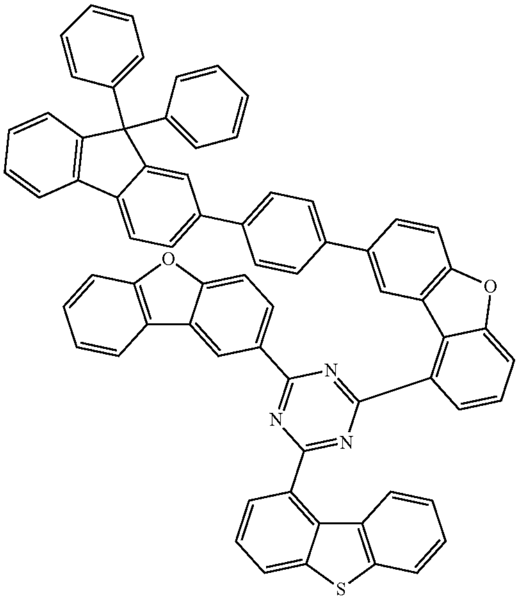 [SMILES: c1ccc(C2(c3ccccc3)c3ccccc3-c3ccc(-c4ccc(-c5ccc6oc7cccc(-c8nc(-c9ccc%10oc%11ccccc%11c%10c9)nc(-c9cccc%10sc%11ccccc%11c9%10)n8)c7c6c5)cc4)cc32)cc1]
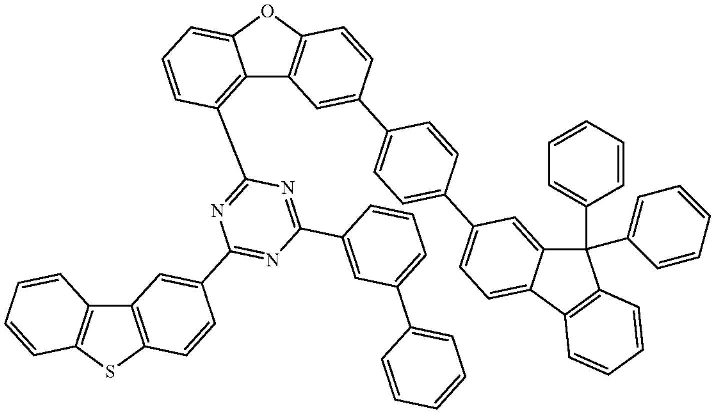 [SMILES: c1ccc(-c2cccc(-c3nc(-c4ccc5sc6ccccc6c5c4)nc(-c4cccc5oc6ccc(-c7ccc(-c8ccc9c(c8)C(c8ccccc8)(c8ccccc8)c8ccccc8-9)cc7)cc6c45)n3)c2)cc1]
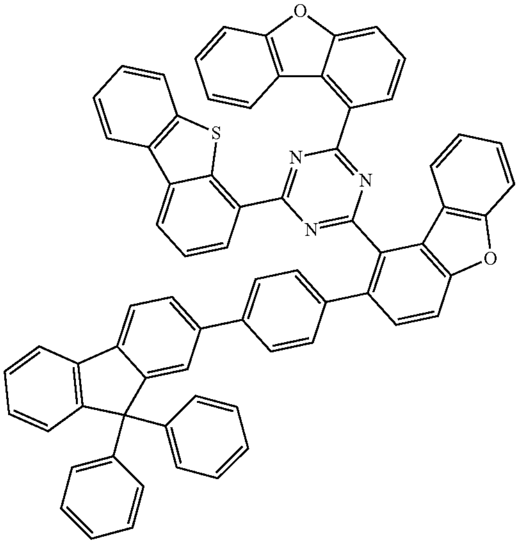 [SMILES: c1ccc(C2(c3ccccc3)c3ccccc3-c3ccc(-c4ccc(-c5ccc6oc7ccccc7c6c5-c5nc(-c6cccc7c6sc6ccccc67)nc(-c6cccc7oc8ccccc8c67)n5)cc4)cc32)cc1]

TABLE 1-continued
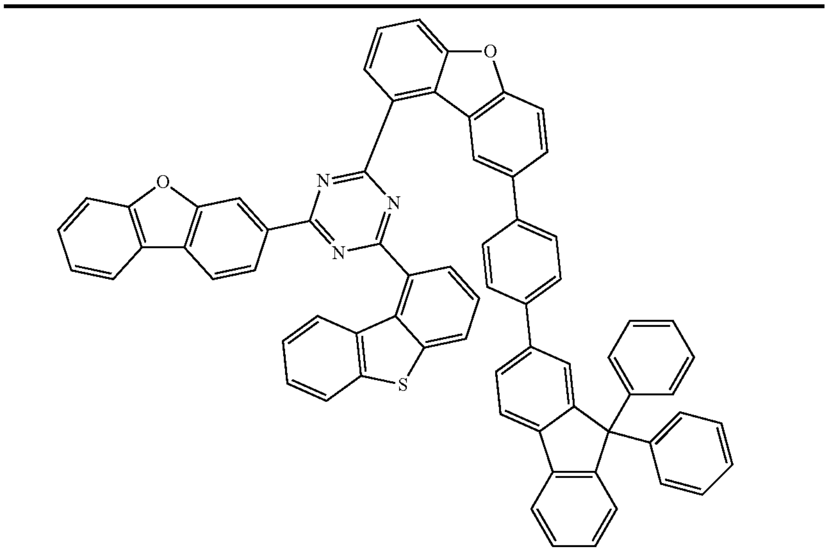
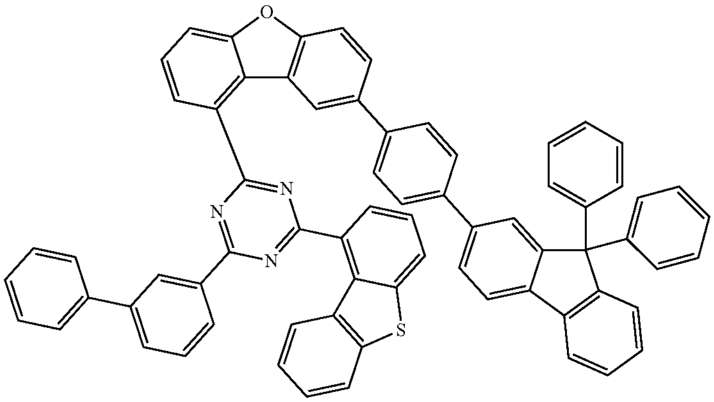 [SMILES: c1ccc(-c2cccc(-c3nc(-c4cccc5oc6ccc(-c7ccc(-c8ccc9c(c8)C(c8ccccc8)(c8ccccc8)c8ccccc8-9)cc7)cc6c45)nc(-c4cccc5sc6ccccc6c45)n3)c2)cc1]
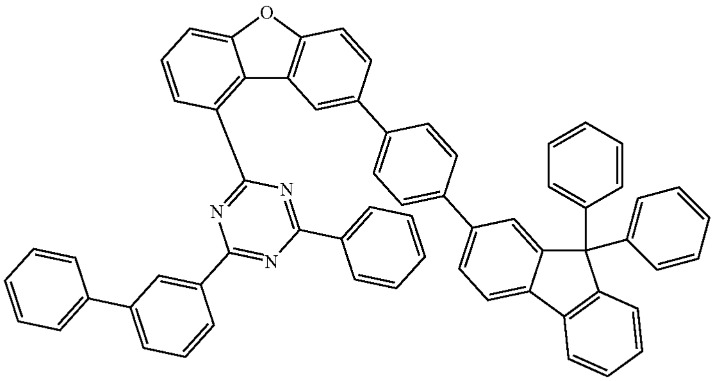 [SMILES: c1ccc(-c2cccc(-c3nc(-c4ccccc4)nc(-c4cccc5oc6ccc(-c7ccc(-c8ccc9c(c8)C(c8ccccc8)(c8ccccc8)c8ccccc8-9)cc7)cc6c45)n3)c2)cc1]

TABLE 1-continued
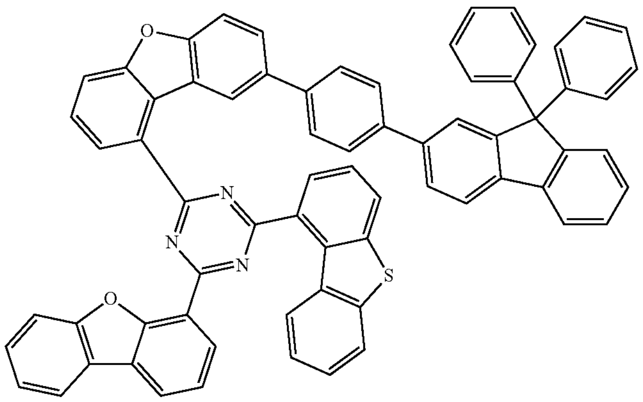 [SMILES: c1ccc(C2(c3ccccc3)c3ccccc3-c3ccc(-c4ccc(-c5ccc6oc7cccc(-c8nc(-c9cccc%10c9oc9ccccc9%10)nc(-c9cccc%10sc%11ccccc%11c9%10)n8)c7c6c5)cc4)cc32)cc1]
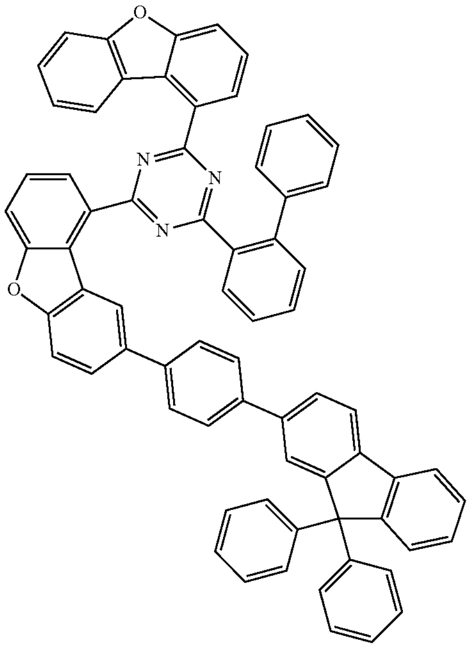 [SMILES: c1ccc(-c2ccccc2-c2nc(-c3cccc4oc5ccccc5c34)nc(-c3cccc4oc5ccc(-c6ccc(-c7ccc8c(c7)C(c7ccccc7)(c7ccccc7)c7ccccc7-8)cc6)cc5c34)n2)cc1]
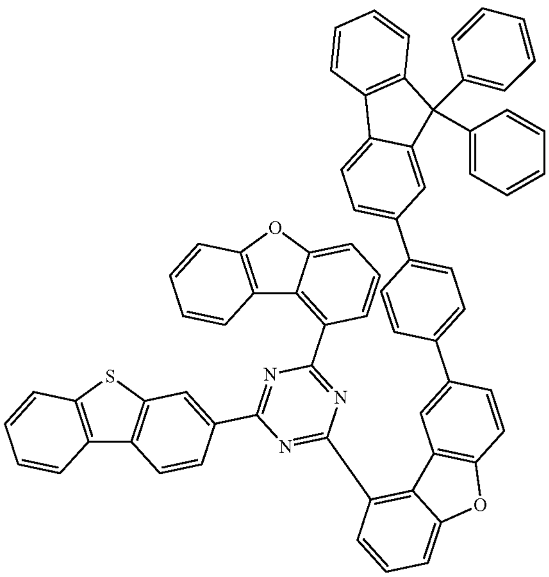 [SMILES: c1ccc(C2(c3ccccc3)c3ccccc3-c3ccc(-c4ccc(-c5ccc6oc7cccc(-c8nc(-c9ccc%10c(c9)sc9ccccc9%10)nc(-c9cccc%10oc%11ccccc%11c9%10)n8)c7c6c5)cc4)cc32)cc1]

TABLE 1-continued
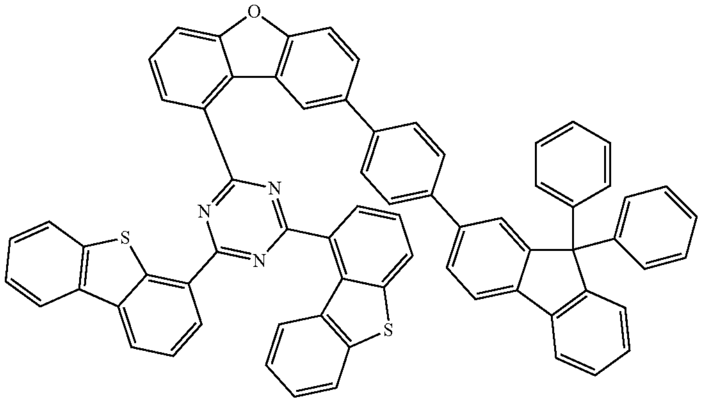 [SMILES: c1ccc(C2(c3ccccc3)c3ccccc3-c3ccc(-c4ccc(-c5ccc6oc7cccc(-c8nc(-c9cccc%10c9sc9ccccc9%10)nc(-c9cccc%10sc%11ccccc%11c9%10)n8)c7c6c5)cc4)cc32)cc1]
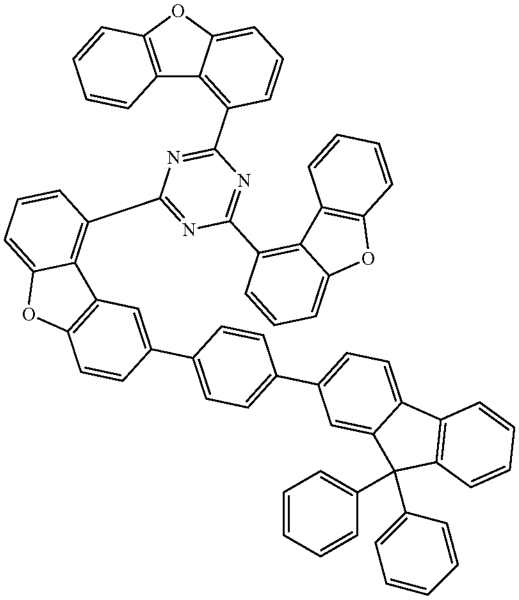 [SMILES: c1ccc(C2(c3ccccc3)c3ccccc3-c3ccc(-c4ccc(-c5ccc6oc7cccc(-c8nc(-c9cccc%10oc%11ccccc%11c9%10)nc(-c9cccc%10oc%11ccccc%11c9%10)n8)c7c6c5)cc4)cc32)cc1]
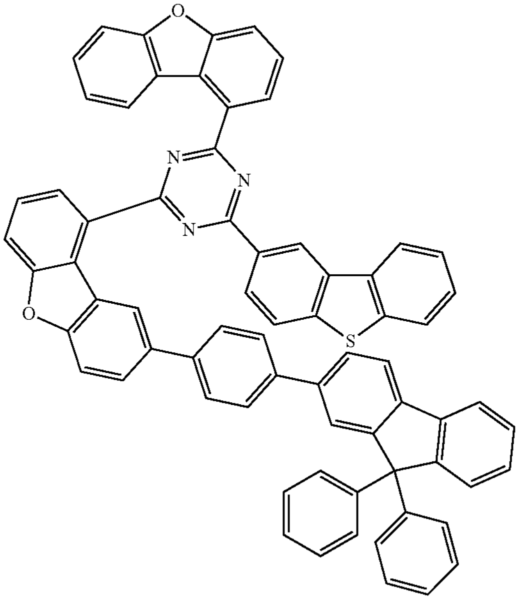

TABLE 1-continued
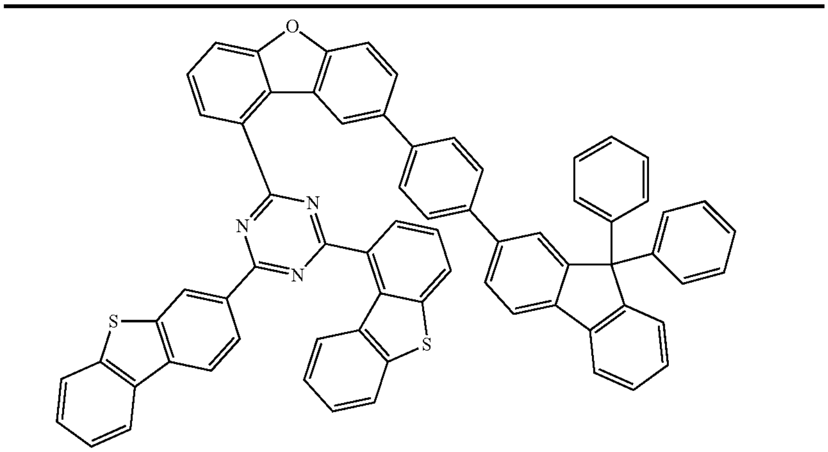
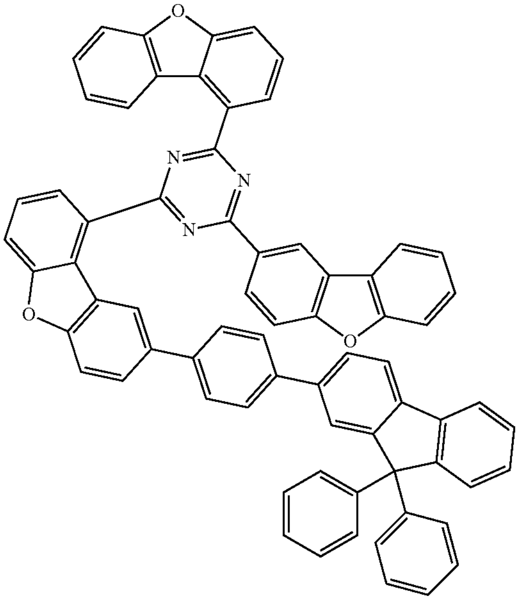 [SMILES: c1ccc(C2(c3ccccc3)c3ccccc3-c3ccc(-c4ccc(-c5ccc6oc7cccc(-c8nc(-c9ccc%10sc%11ccccc%11c%10c9)nc(-c9cccc%10oc%11ccccc%11c9%10)n8)c7c6c5)cc4)cc32)cc1]
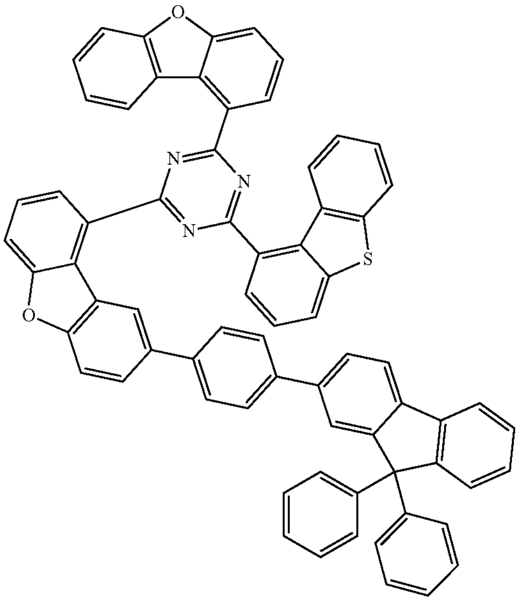 [SMILES: c1ccc(C2(c3ccccc3)c3ccccc3-c3ccc(-c4ccc(-c5ccc6oc7cccc(-c8nc(-c9cccc%10oc%11ccccc%11c9%10)nc(-c9cccc%10sc%11ccccc%11c9%10)n8)c7c6c5)cc4)cc32)cc1]

TABLE 1-continued
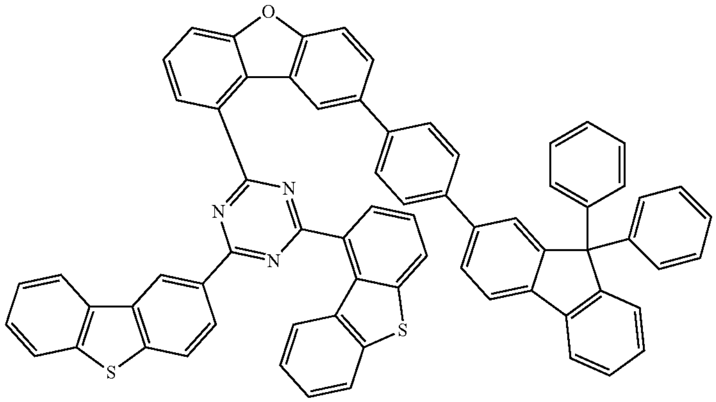 [SMILES: c1ccc(C2(c3ccccc3)c3ccccc3-c3ccc(-c4ccc(-c5ccc6oc7cccc(-c8nc(-c9ccc%10sc%11ccccc%11c%10c9)nc(-c9cccc%10sc%11ccccc%11c9%10)n8)c7c6c5)cc4)cc32)cc1]
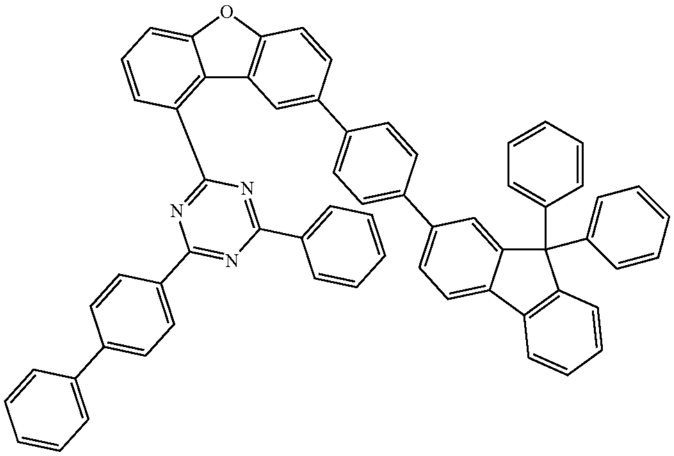 [SMILES: c1ccc(-c2ccc(-c3nc(-c4ccccc4)nc(-c4cccc5oc6ccc(-c7ccc(-c8ccc9c(c8)C(c8ccccc8)(c8ccccc8)c8ccccc8-9)cc7)cc6c45)n3)cc2)cc1]
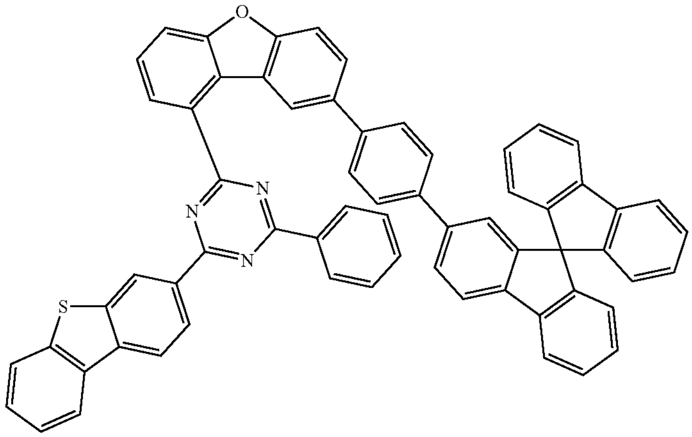 [SMILES: c1ccc(-c2nc(-c3ccc4c(c3)sc3ccccc34)nc(-c3cccc4oc5ccc(-c6ccc(-c7ccc8c(c7)C7(c9ccccc9-c9ccccc97)c7ccccc7-8)cc6)cc5c34)n2)cc1]

TABLE 1-continued
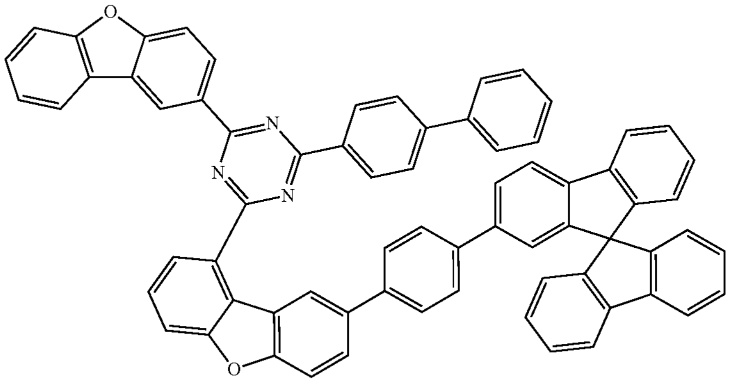 [SMILES: c1ccc(-c2ccc(-c3nc(-c4ccc5oc6ccccc6c5c4)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]
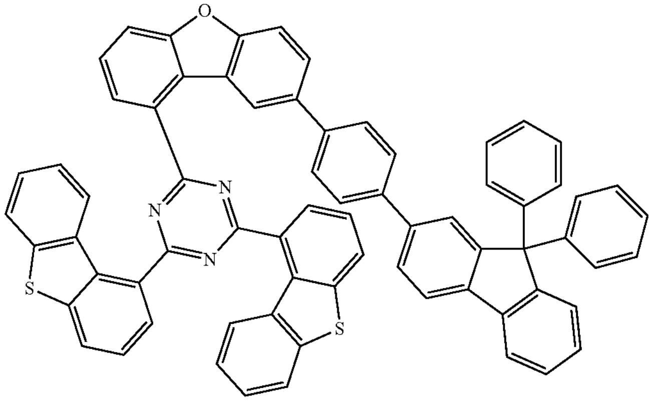 [SMILES: c1ccc(C2(c3ccccc3)c3ccccc3-c3ccc(-c4ccc(-c5ccc6oc7cccc(-c8nc(-c9cccc%10sc%11ccccc%11c9%10)nc(-c9cccc%10sc%11ccccc%11c9%10)n8)c7c6c5)cc4)cc32)cc1]
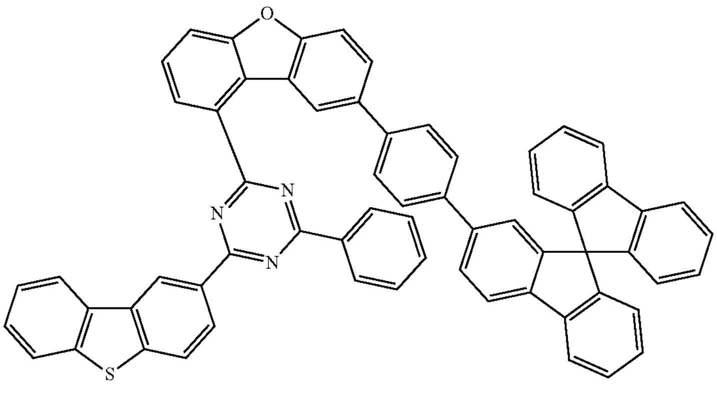 [SMILES: c1ccc(-c2nc(-c3ccc4sc5ccccc5c4c3)nc(-c3cccc4oc5ccc(-c6ccc(-c7ccc8c(c7)C7(c9ccccc9-c9ccccc97)c7ccccc7-8)cc6)cc5c34)n2)cc1]

TABLE 1-continued
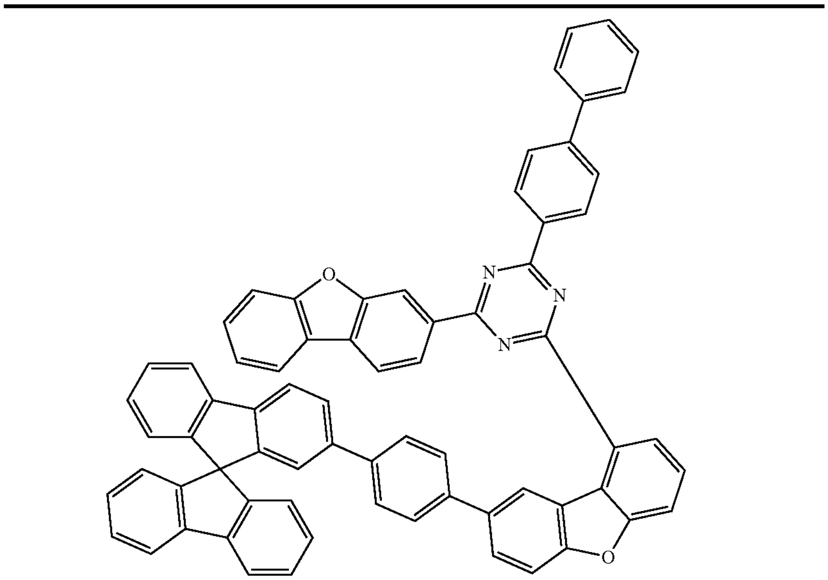
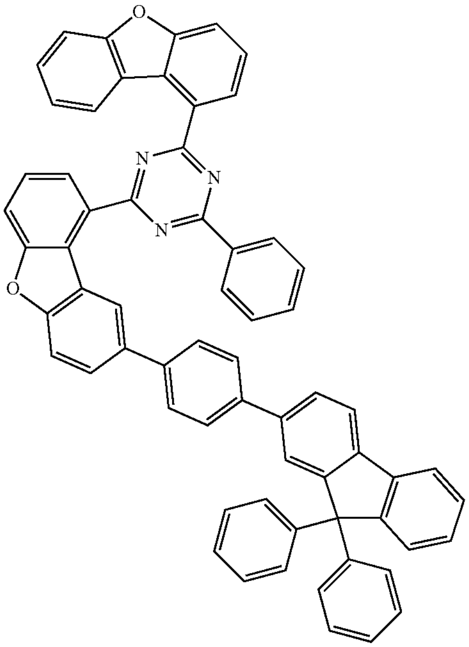 [SMILES: c1ccc(-c2nc(-c3cccc4oc5ccccc5c34)nc(-c3cccc4oc5ccc(-c6ccc(-c7ccc8c(c7)C(c7ccccc7)(c7ccccc7)c7ccccc7-8)cc6)cc5c34)n2)cc1]

TABLE 1-continued
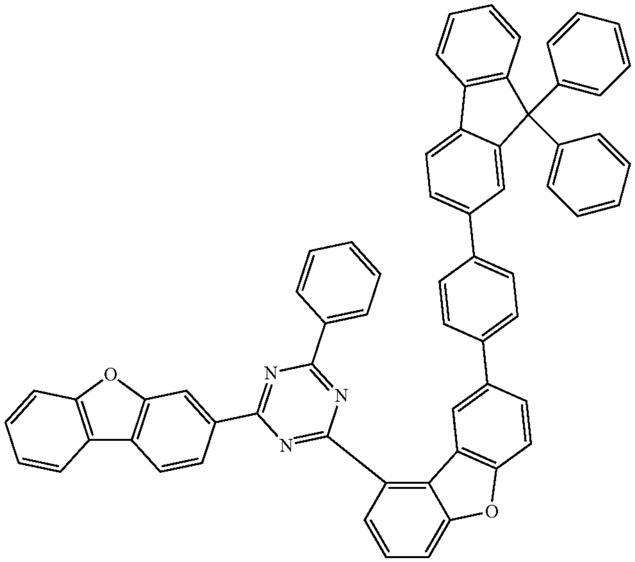 [SMILES: c1ccc(-c2nc(-c3ccc4c(c3)oc3ccccc34)nc(-c3cccc4oc5ccc(-c6ccc(-c7ccc8c(c7)C(c7ccccc7)(c7ccccc7)c7ccccc7-8)cc6)cc5c34)n2)cc1]
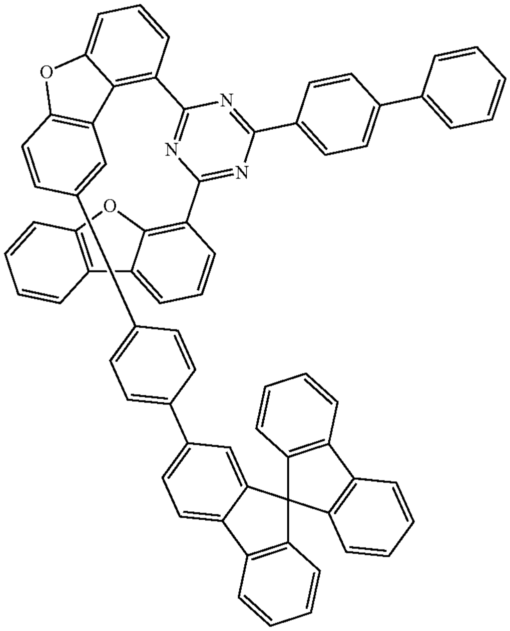 [SMILES: c1ccc(-c2ccc(-c3nc(-c4cccc5c4oc4ccccc45)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]
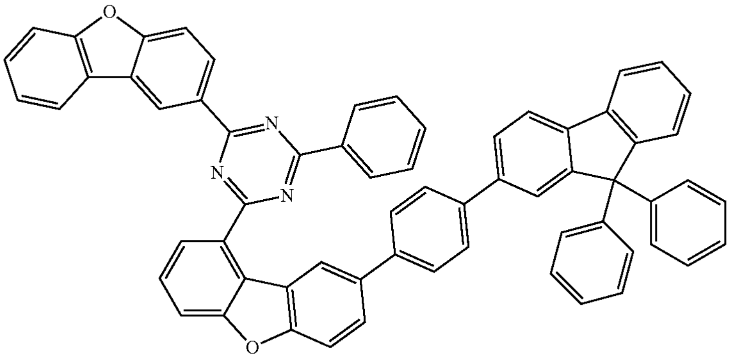 [SMILES: c1ccc(-c2nc(-c3ccc4oc5ccccc5c4c3)nc(-c3cccc4oc5ccc(-c6ccc(-c7ccc8c(c7)C(c7ccccc7)(c7ccccc7)c7ccccc7-8)cc6)cc5c34)n2)cc1]

TABLE 1-continued
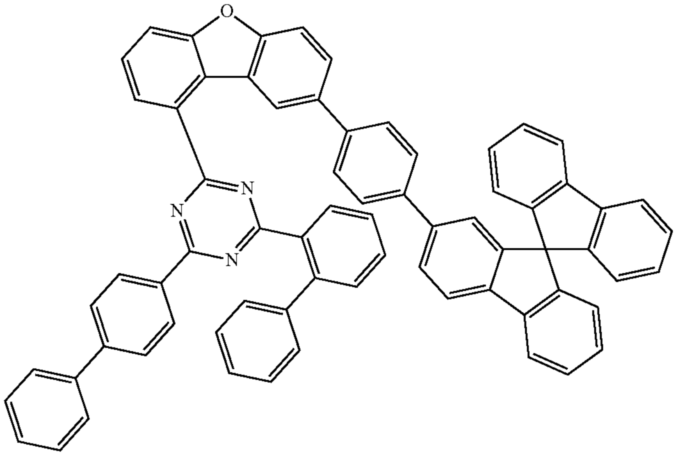 [SMILES: c1ccc(-c2ccc(-c3nc(-c4ccccc4-c4ccccc4)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]
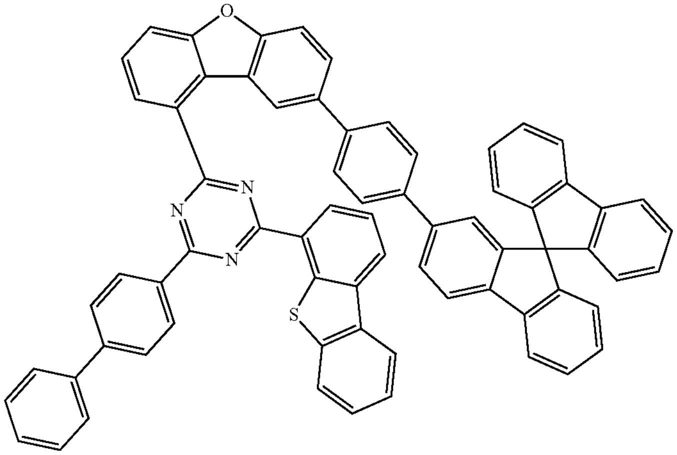 [SMILES: c1ccc(-c2ccc(-c3nc(-c4cccc5c4sc4ccccc45)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]
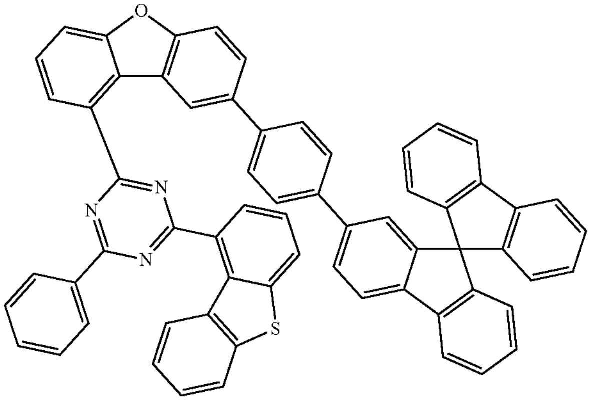 [SMILES: c1ccc(-c2nc(-c3cccc4oc5ccc(-c6ccc(-c7ccc8c(c7)C7(c9ccccc9-c9ccccc97)c7ccccc7-8)cc6)cc5c34)nc(-c3cccc4sc5ccccc5c34)n2)cc1]

TABLE 1-continued
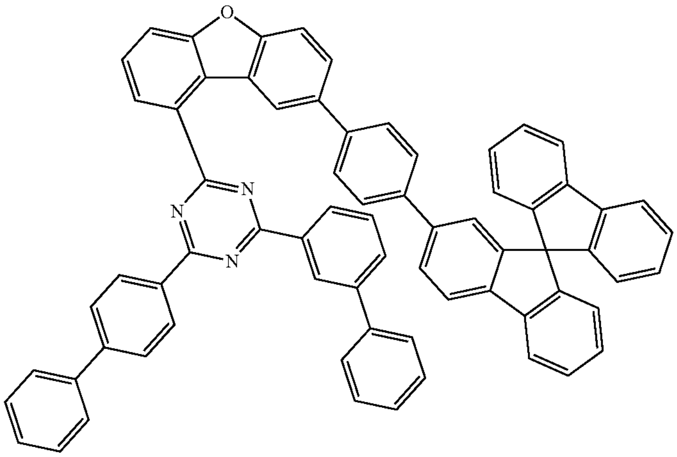 [SMILES: c1ccc(-c2ccc(-c3nc(-c4cccc(-c5ccccc5)c4)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]
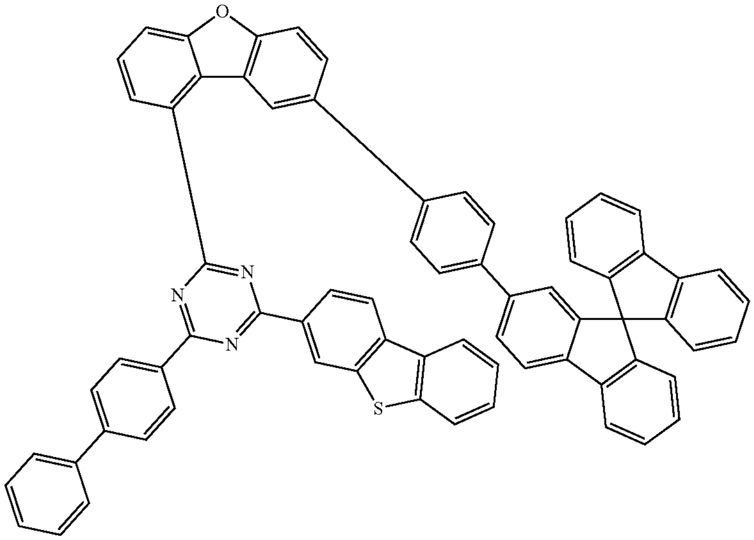 [SMILES: c1ccc(-c2ccc(-c3nc(-c4ccc5c(c4)sc4ccccc45)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]
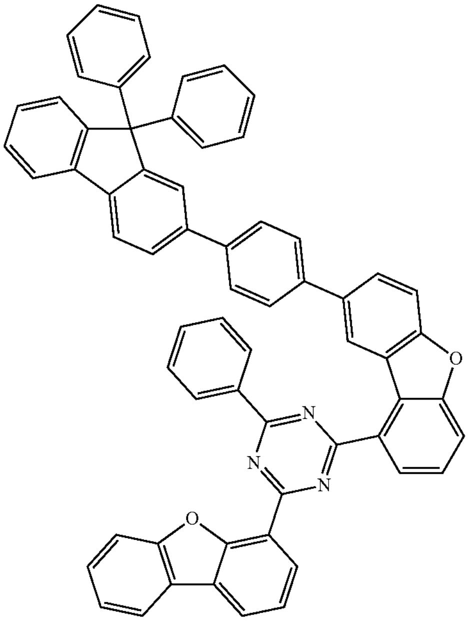 [SMILES: c1ccc(-c2nc(-c3cccc4c3oc3ccccc34)nc(-c3cccc4oc5ccc(-c6ccc(-c7ccc8c(c7)C(c7ccccc7)(c7ccccc7)c7ccccc7-8)cc6)cc5c34)n2)cc1]

TABLE 1-continued
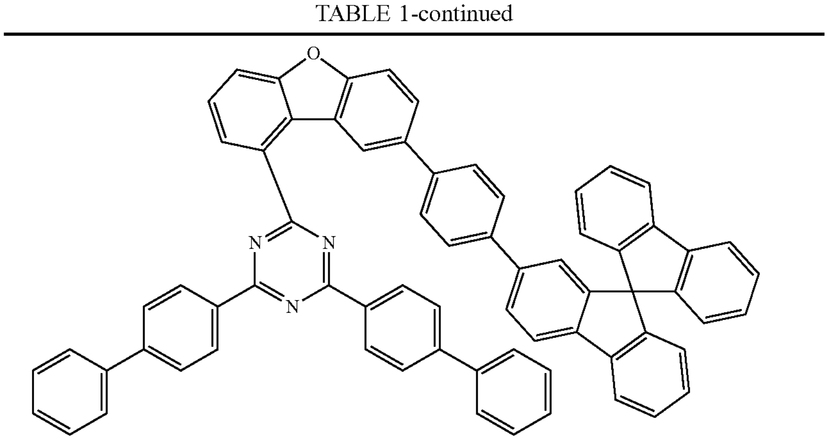
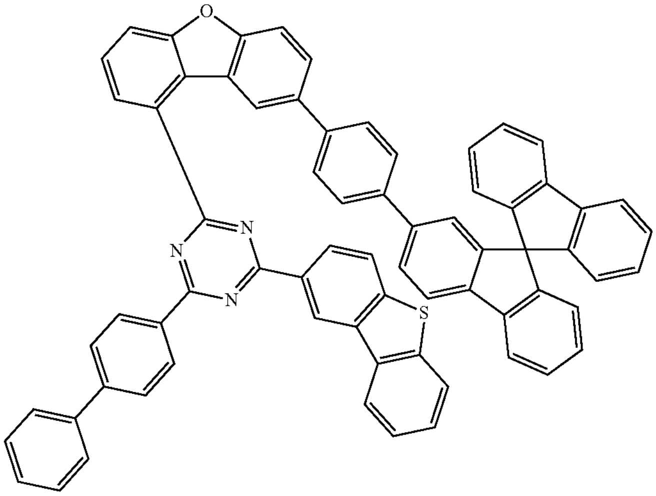 [SMILES: c1ccc(-c2ccc(-c3nc(-c4ccc5sc6ccccc6c5c4)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]
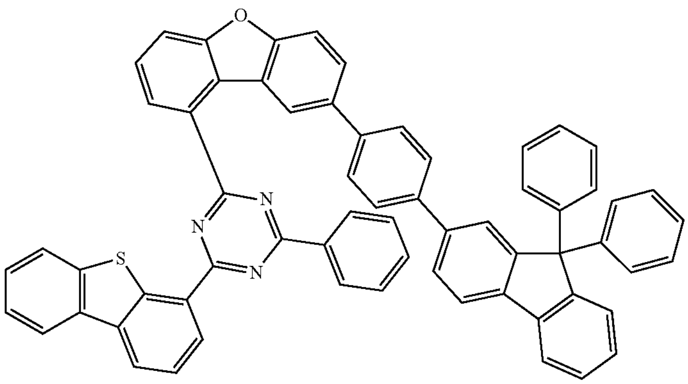 [SMILES: c1ccc(-c2nc(-c3cccc4c3sc3ccccc34)nc(-c3cccc4oc5ccc(-c6ccc(-c7ccc8c(c7)C(c7ccccc7)(c7ccccc7)c7ccccc7-8)cc6)cc5c34)n2)cc1]

TABLE 1-continued
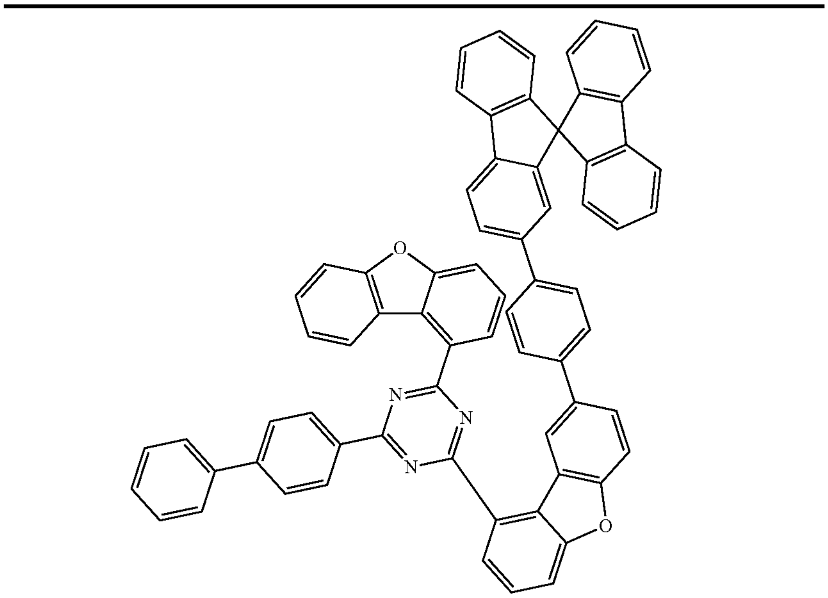
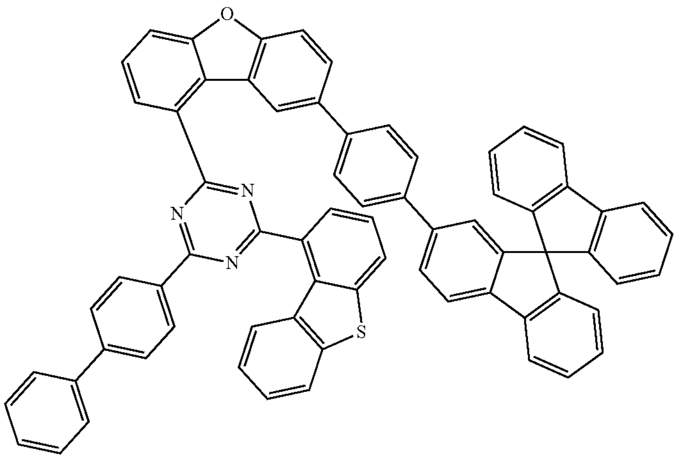 [SMILES: c1ccc(-c2ccc(-c3nc(-c4cccc5oc6ccc(-c7ccc(-c8ccc9c(c8)C8(c%10ccccc%10-c%10ccccc%108)c8ccccc8-9)cc7)cc6c45)nc(-c4cccc5sc6ccccc6c45)n3)cc2)cc1]
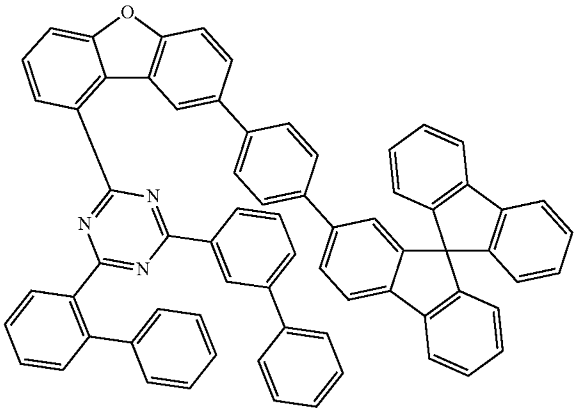 [SMILES: c1ccc(-c2cccc(-c3nc(-c4ccccc4-c4ccccc4)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]

TABLE 1-continued
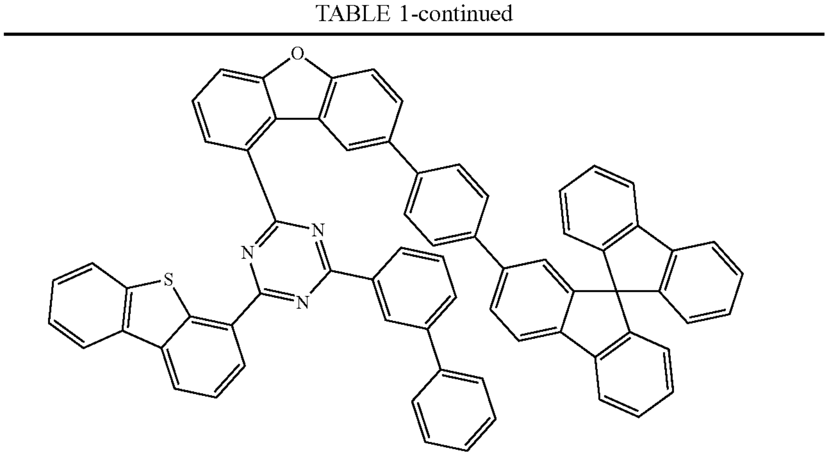
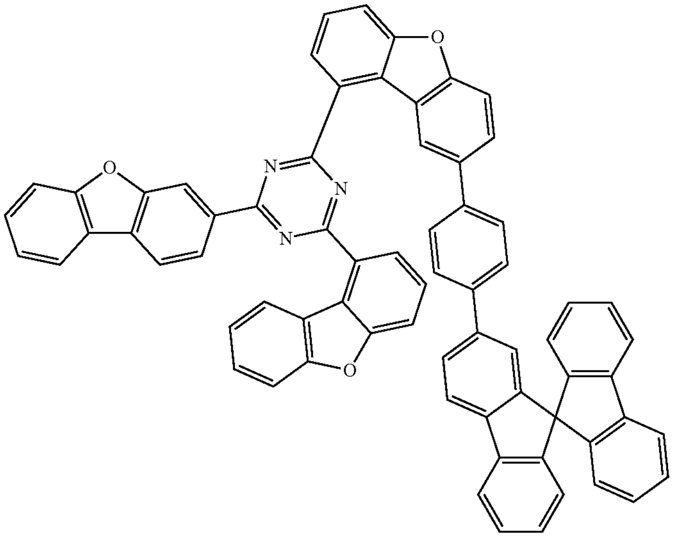 [SMILES: c1ccc2c(c1)-c1ccccc1C21c2ccccc2-c2ccc(-c3ccc(-c4ccc5oc6cccc(-c7nc(-c8ccc9c(c8)oc8ccccc89)nc(-c8cccc9oc%10ccccc%10c89)n7)c6c5c4)cc3)cc21]
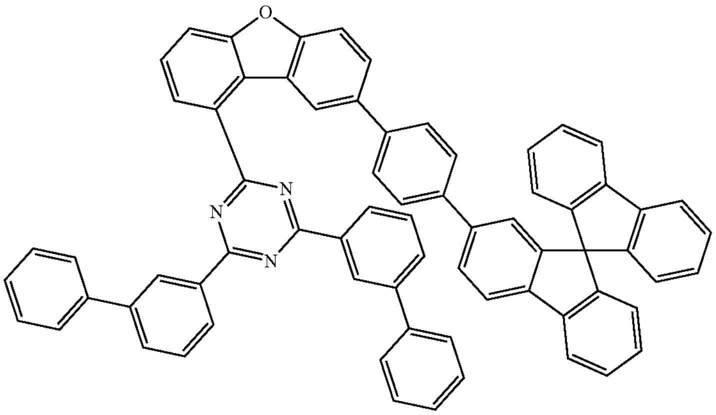 [SMILES: c1ccc(-c2cccc(-c3nc(-c4cccc(-c5ccccc5)c4)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]

TABLE 1-continued
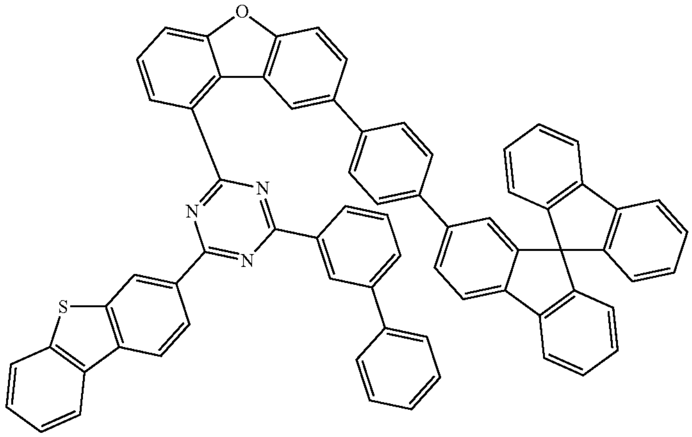 [SMILES: c1ccc(-c2cccc(-c3nc(-c4ccc5c(c4)sc4ccccc45)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]
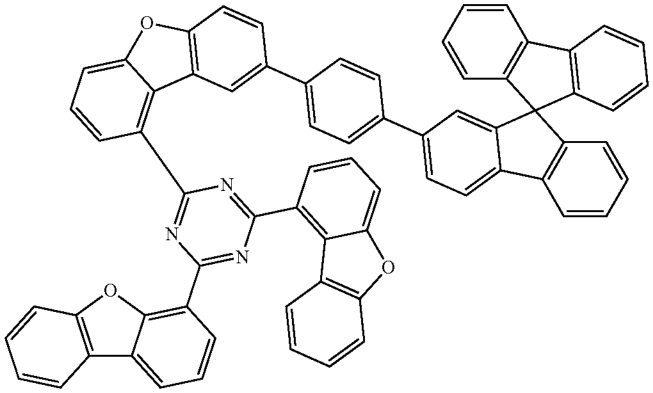 [SMILES: c1ccc2c(c1)-c1ccccc1C21c2ccccc2-c2ccc(-c3ccc(-c4ccc5oc6cccc(-c7nc(-c8cccc9c8oc8ccccc89)nc(-c8cccc9oc%10ccccc%10c89)n7)c6c5c4)cc3)cc21]
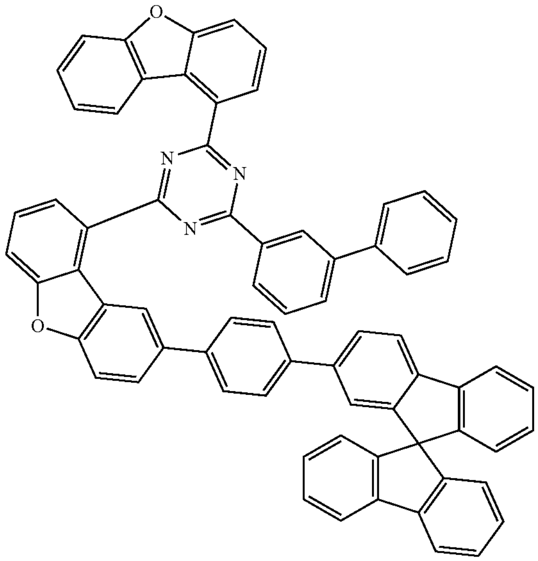 [SMILES: c1ccc(-c2cccc(-c3nc(-c4cccc5oc6ccccc6c45)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]

TABLE 1-continued
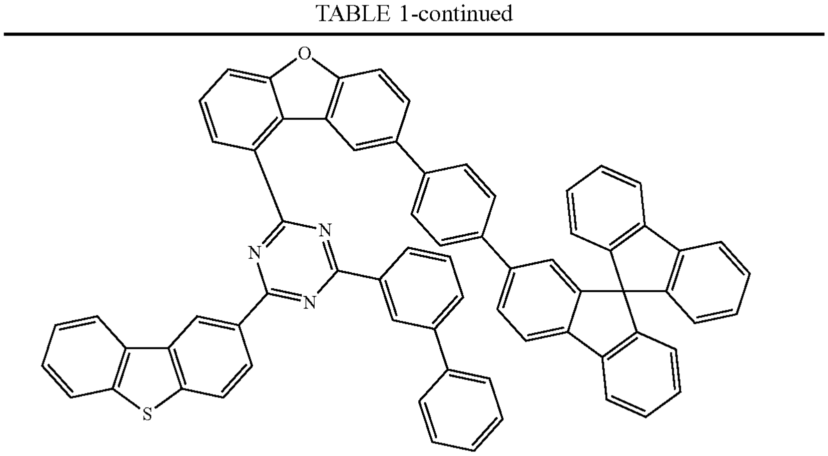
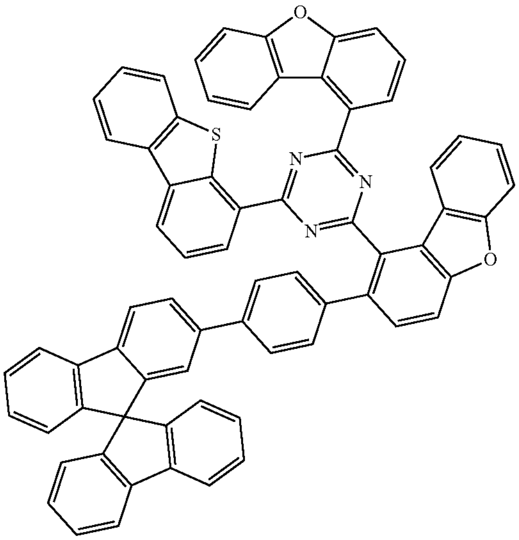 [SMILES: c1ccc2c(c1)-c1ccccc1C21c2ccccc2-c2ccc(-c3ccc(-c4ccc5oc6ccccc6c5c4-c4nc(-c5cccc6c5sc5ccccc56)nc(-c5cccc6oc7ccccc7c56)n4)cc3)cc21]
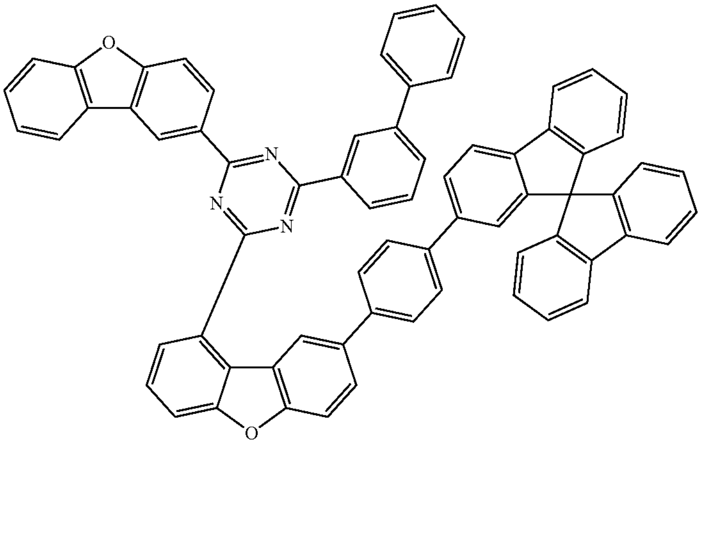 [SMILES: c1ccc(-c2cccc(-c3nc(-c4ccc5oc6ccccc6c5c4)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]

TABLE 1-continued
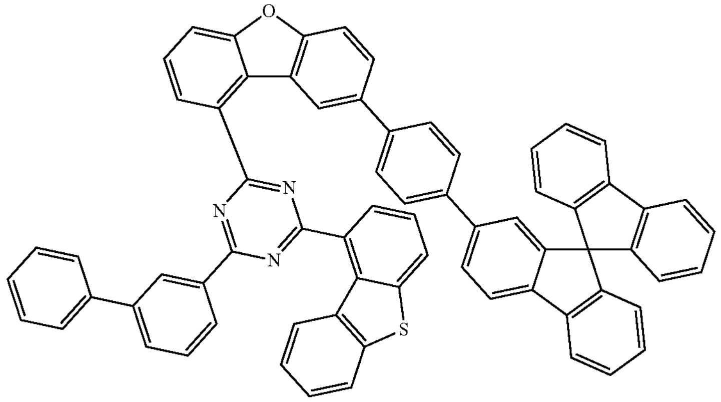 [SMILES: c1ccc(-c2cccc(-c3nc(-c4cccc5oc6ccc(-c7ccc(-c8ccc9c(c8)C8(c%10ccccc%10-c%10ccccc%108)c8ccccc8-9)cc7)cc6c45)nc(-c4cccc5sc6ccccc6c45)n3)c2)cc1]
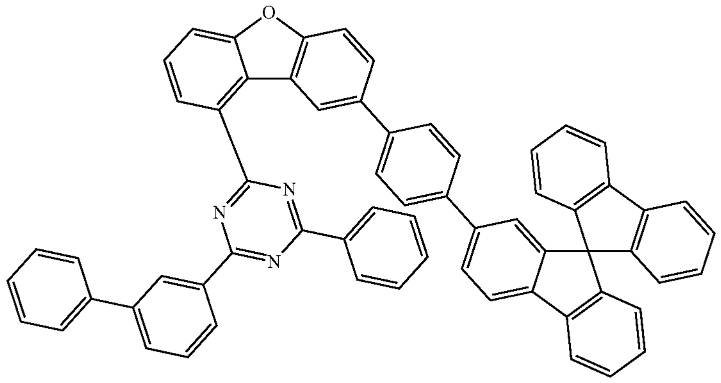 [SMILES: c1ccc(-c2cccc(-c3nc(-c4ccccc4)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]
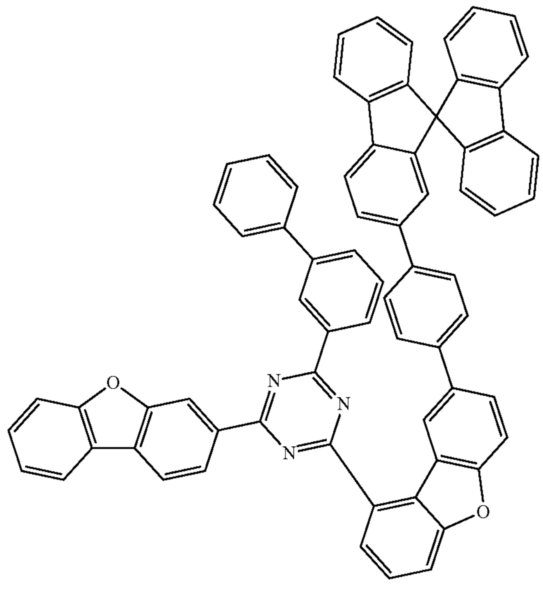 [SMILES: c1ccc(-c2cccc(-c3nc(-c4ccc5c(c4)oc4ccccc45)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]

TABLE 1-continued
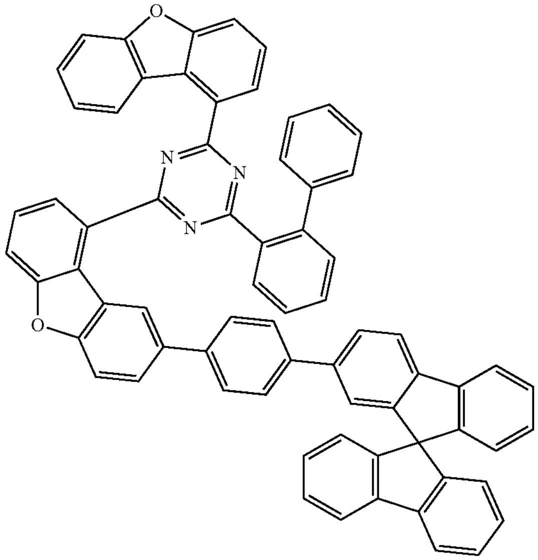 [SMILES: c1ccc(-c2ccccc2-c2nc(-c3cccc4oc5ccccc5c34)nc(-c3cccc4oc5ccc(-c6ccc(-c7ccc8c(c7)C7(c9ccccc9-c9ccccc97)c7ccccc7-8)cc6)cc5c34)n2)cc1]
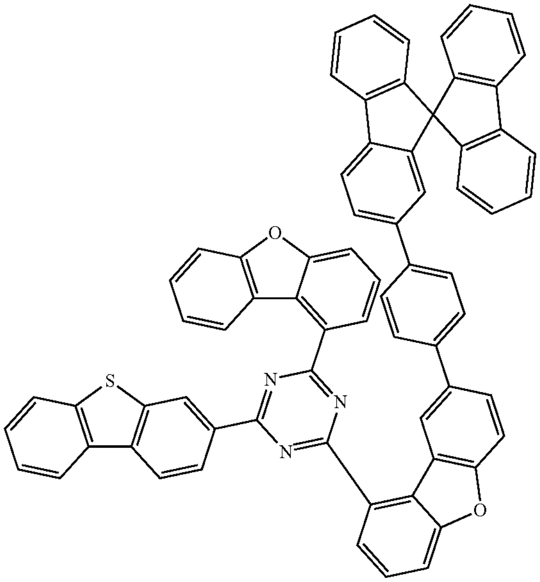 [SMILES: c1ccc2c(c1)-c1ccccc1C21c2ccccc2-c2ccc(-c3ccc(-c4ccc5oc6cccc(-c7nc(-c8ccc9c(c8)sc8ccccc89)nc(-c8cccc9oc%10ccccc%10c89)n7)c6c5c4)cc3)cc21]

TABLE 1-continued
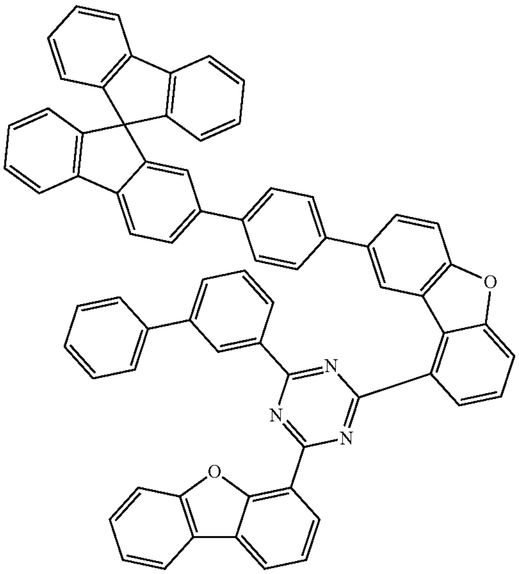 [SMILES: c1ccc(-c2cccc(-c3nc(-c4cccc5c4oc4ccccc45)nc(-c4cccc5oc6ccc(-c7ccc(-c8ccc9c(c8)C8(c%10ccccc%10-c%10ccccc%108)c8ccccc8-9)cc7)cc6c45)n3)c2)cc1]
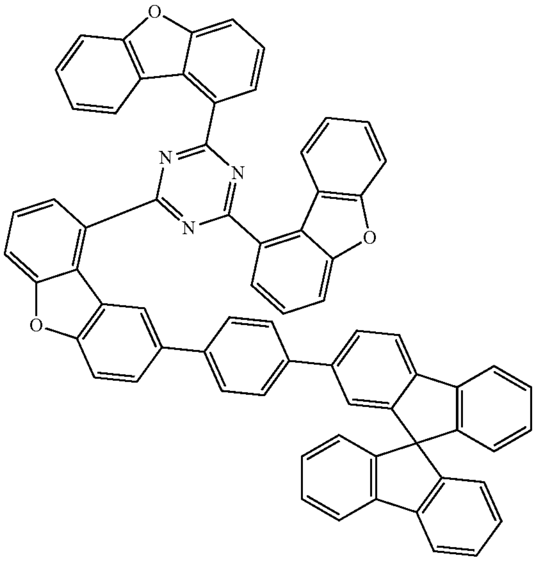 [SMILES: c1ccc2c(c1)-c1ccccc1C21c2ccccc2-c2ccc(-c3ccc(-c4ccc5oc6cccc(-c7nc(-c8cccc9oc%10ccccc%10c89)nc(-c8cccc9oc%10ccccc%10c89)n7)c6c5c4)cc3)cc21]

TABLE 1-continued
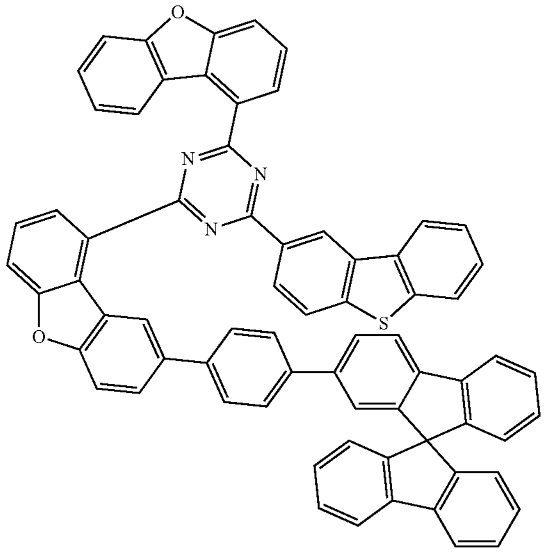 [SMILES: c1ccc2c(c1)-c1ccccc1C21c2ccccc2-c2ccc(-c3ccc(-c4ccc5oc6cccc(-c7nc(-c8ccc9sc%10ccccc%10c9c8)nc(-c8cccc9oc%10ccccc%10c89)n7)c6c5c4)cc3)cc21]
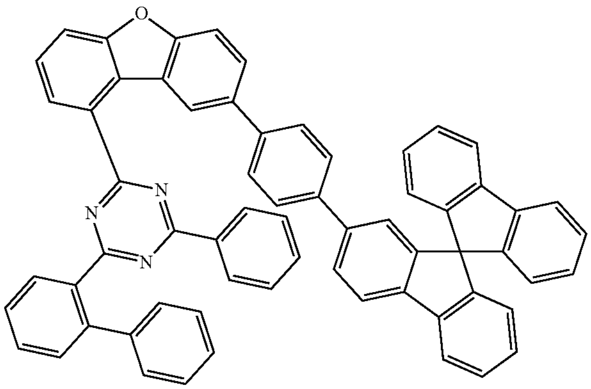 [SMILES: c1ccc(-c2nc(-c3ccccc3-c3ccccc3)nc(-c3cccc4oc5ccc(-c6ccc(-c7ccc8c(c7)C7(c9ccccc9-c9ccccc97)c7ccccc7-8)cc6)cc5c34)n2)cc1]
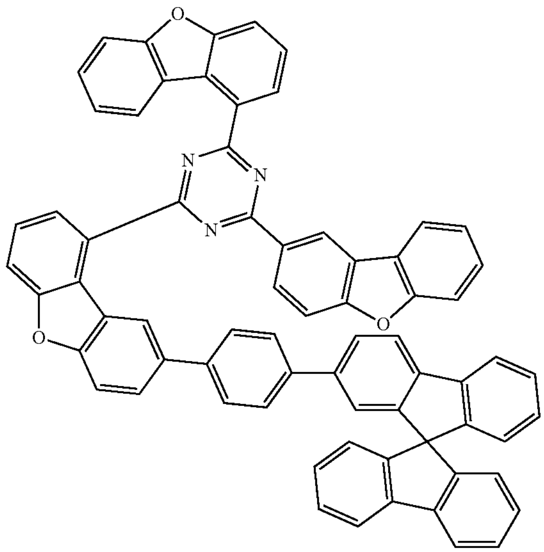 [SMILES: c1ccc2c(c1)-c1ccccc1C21c2ccccc2-c2ccc(-c3ccc(-c4ccc5oc6cccc(-c7nc(-c8ccc9oc%10ccccc%10c9c8)nc(-c8cccc9oc%10ccccc%10c89)n7)c6c5c4)cc3)cc21]

TABLE 1-continued
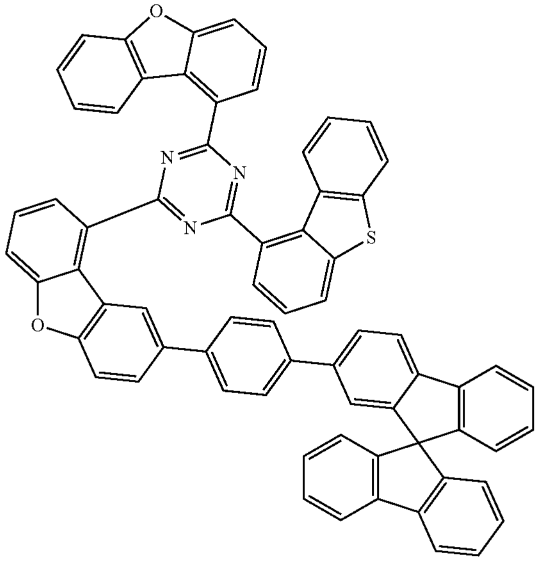 [SMILES: c1ccc2c(c1)-c1ccccc1C21c2ccccc2-c2ccc(-c3ccc(-c4ccc5oc6cccc(-c7nc(-c8cccc9oc%10ccccc%10c89)nc(-c8cccc9sc%10ccccc%10c89)n7)c6c5c4)cc3)cc21]
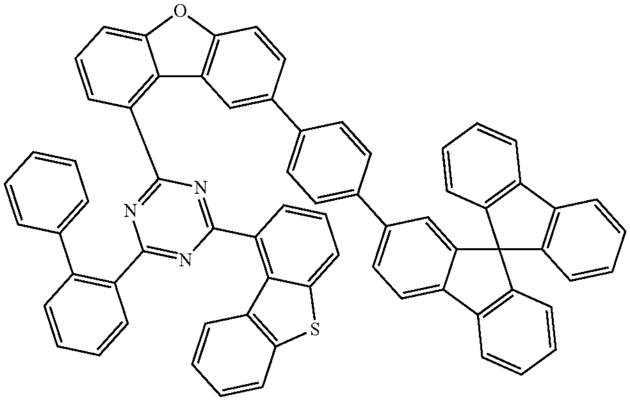 [SMILES: c1ccc(-c2ccccc2-c2nc(-c3cccc4oc5ccc(-c6ccc(-c7ccc8c(c7)C7(c9ccccc9-c9ccccc97)c7ccccc7-8)cc6)cc5c34)nc(-c3cccc4sc5ccccc5c34)n2)cc1]
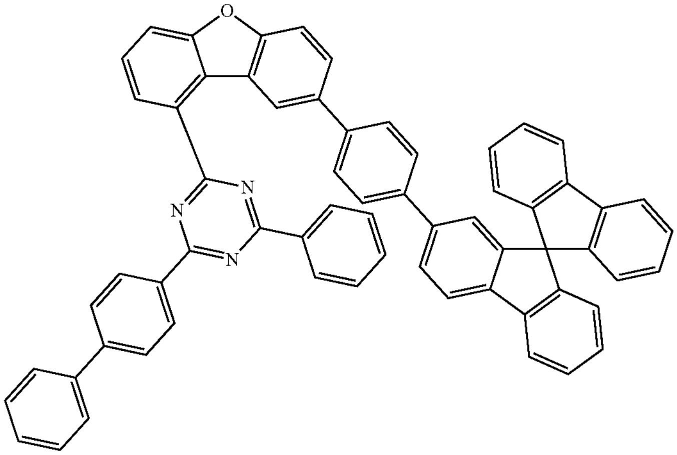 [SMILES: c1ccc(-c2ccc(-c3nc(-c4ccccc4)nc(-c4cccc5oc6ccc(-c7ccc(-c8ccc9c(c8)C8(c%10ccccc%10-c%10ccccc%108)c8ccccc8-9)cc7)cc6c45)n3)cc2)cc1]

TABLE 1-continued
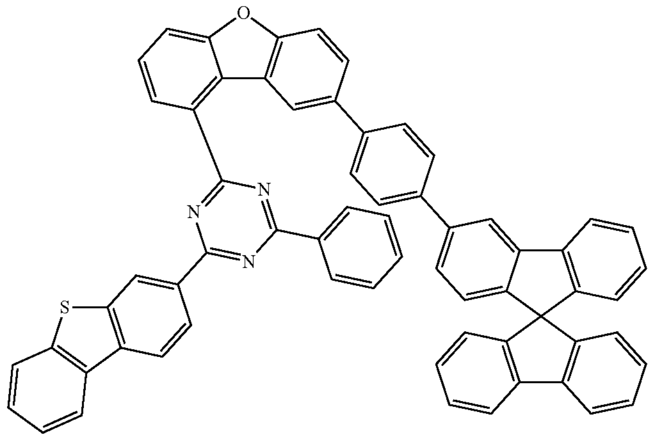 [SMILES: c1ccc(-c2nc(-c3ccc4c(c3)sc3ccccc34)nc(-c3cccc4oc5ccc(-c6ccc(-c7ccc8c(c7)-c7ccccc7C87c8ccccc8-c8ccccc87)cc6)cc5c34)n2)cc1]
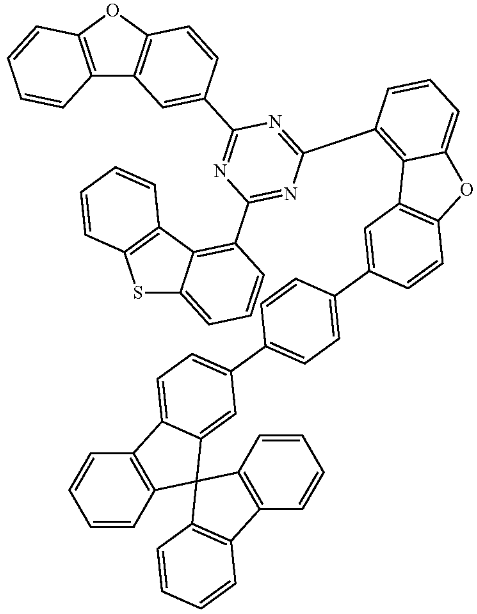 [SMILES: c1ccc2c(c1)-c1ccccc1C21c2ccccc2-c2ccc(-c3ccc(-c4ccc5oc6cccc(-c7nc(-c8ccc9oc%10ccccc%10c9c8)nc(-c8cccc9sc%10ccccc%10c89)n7)c6c5c4)cc3)cc21]
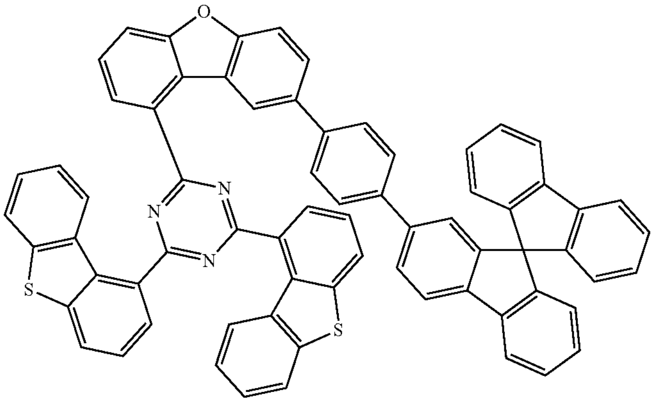 [SMILES: c1ccc2c(c1)-c1ccccc1C21c2ccccc2-c2ccc(-c3ccc(-c4ccc5oc6cccc(-c7nc(-c8cccc9sc%10ccccc%10c89)nc(-c8cccc9sc%10ccccc%10c89)n7)c6c5c4)cc3)cc21]

TABLE 1-continued
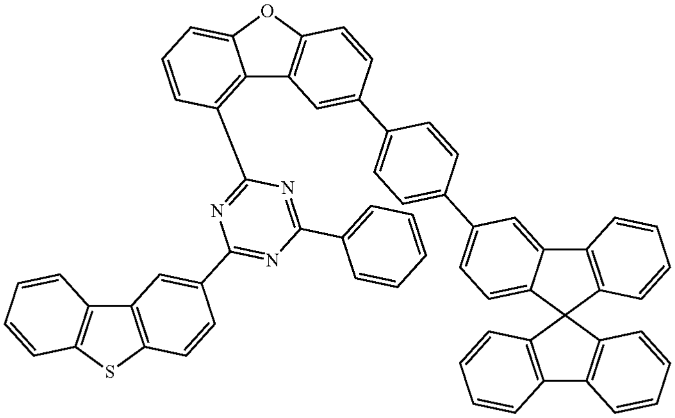 [SMILES: c1ccc(-c2nc(-c3ccc4sc5ccccc5c4c3)nc(-c3cccc4oc5ccc(-c6ccc(-c7ccc8c(c7)-c7ccccc7C87c8ccccc8-c8ccccc87)cc6)cc5c34)n2)cc1]
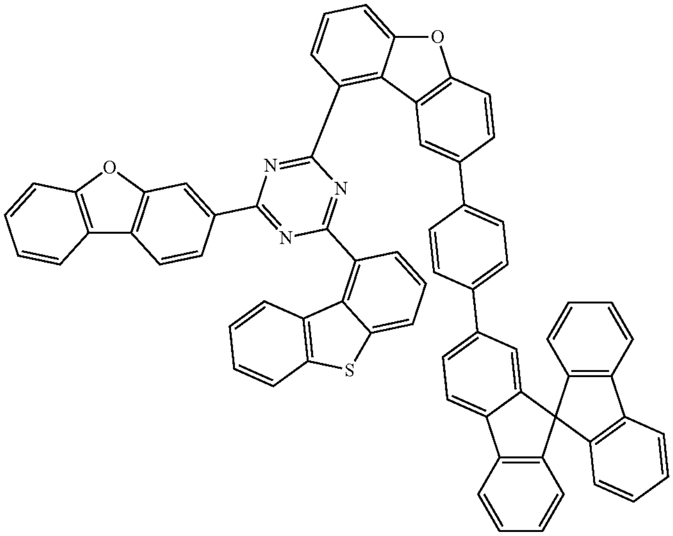 [SMILES: c1ccc2c(c1)-c1ccccc1C21c2ccccc2-c2ccc(-c3ccc(-c4ccc5oc6cccc(-c7nc(-c8ccc9c(c8)oc8ccccc89)nc(-c8cccc9sc%10ccccc%10c89)n7)c6c5c4)cc3)cc21]
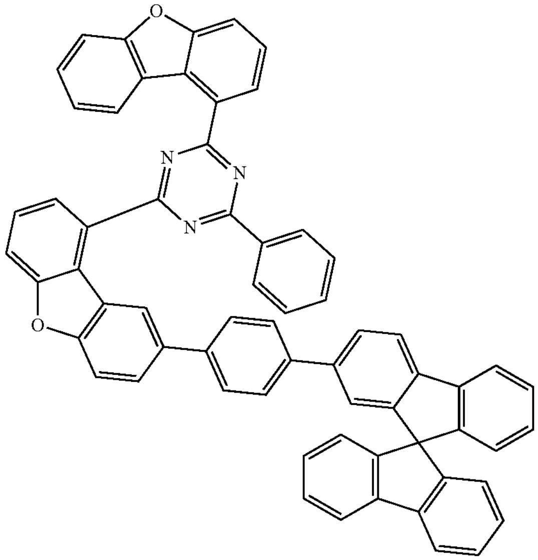 [SMILES: c1ccc(-c2nc(-c3cccc4oc5ccccc5c34)nc(-c3cccc4oc5ccc(-c6ccc(-c7ccc8c(c7)C7(c9ccccc9-c9ccccc97)c7ccccc7-8)cc6)cc5c34)n2)cc1]

TABLE 1-continued
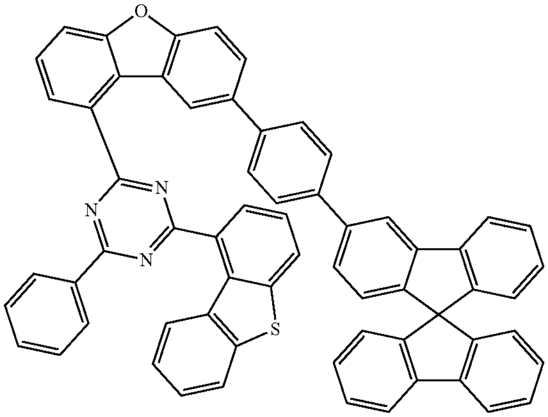 [SMILES: c1ccc(-c2nc(-c3cccc4oc5ccc(-c6ccc(-c7ccc8c(c7)-c7ccccc7C87c8ccccc8-c8ccccc87)cc6)cc5c34)nc(-c3cccc4sc5ccccc5c34)n2)cc1]
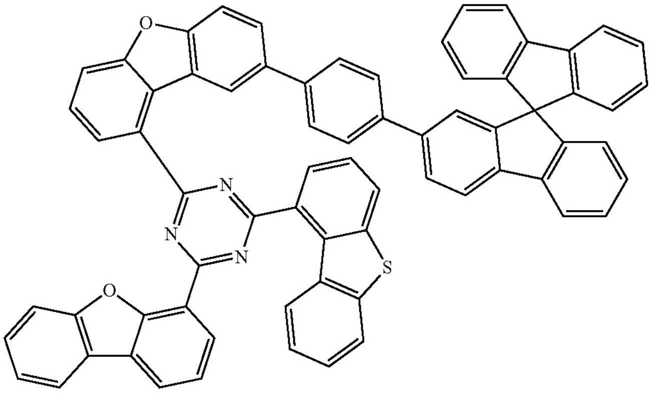 [SMILES: c1ccc2c(c1)-c1ccccc1C21c2ccccc2-c2ccc(-c3ccc(-c4ccc5oc6cccc(-c7nc(-c8cccc9c8oc8ccccc89)nc(-c8cccc9sc%10ccccc%10c89)n7)c6c5c4)cc3)cc21]
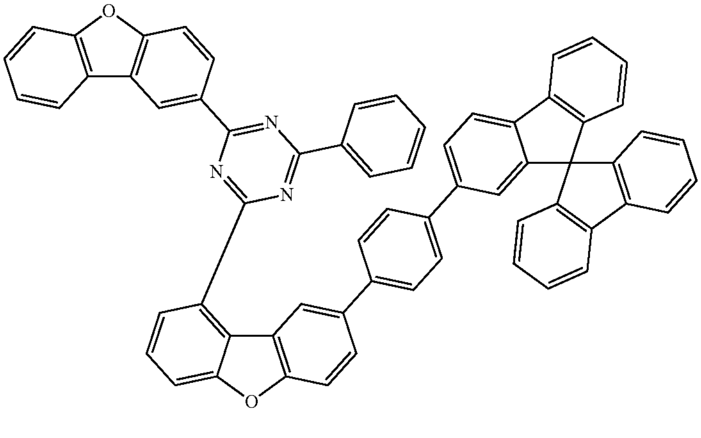 [SMILES: c1ccc(-c2nc(-c3ccc4oc5ccccc5c4c3)nc(-c3cccc4oc5ccc(-c6ccc(-c7ccc8c(c7)C7(c9ccccc9-c9ccccc97)c7ccccc7-8)cc6)cc5c34)n2)cc1]

TABLE 1-continued
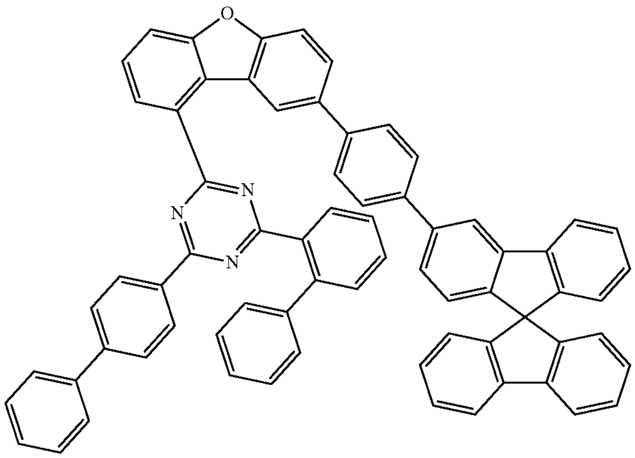 [SMILES: c1ccc(-c2ccc(-c3nc(-c4ccccc4-c4ccccc4)nc(-c4cccc5oc6ccc(-c7ccc(-c8ccc9c(c8)-c8ccccc8C98c9ccccc9-c9ccccc98)cc7)cc6c45)n3)cc2)cc1]
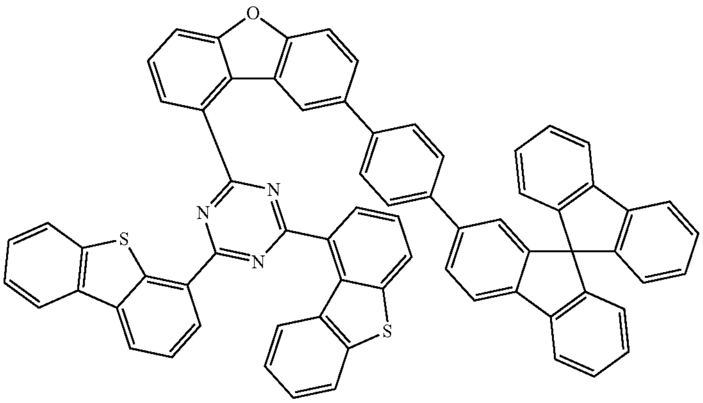 [SMILES: c1ccc2c(c1)-c1ccccc1C21c2ccccc2-c2ccc(-c3ccc(-c4ccc5oc6cccc(-c7nc(-c8cccc9c8sc8ccccc89)nc(-c8cccc9sc%10ccccc%10c89)n7)c6c5c4)cc3)cc21]
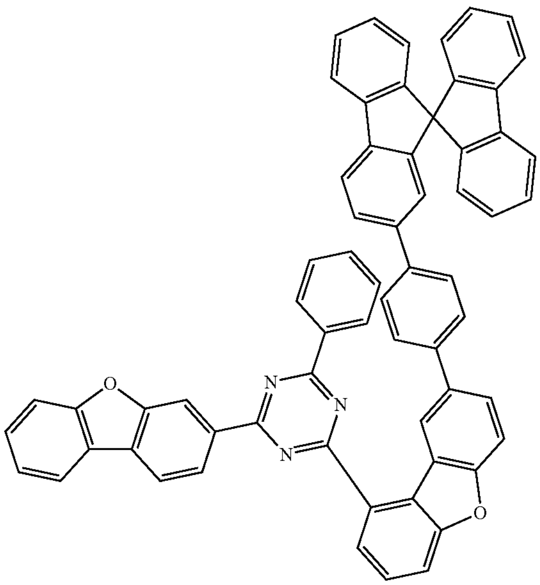 [SMILES: c1ccc(-c2nc(-c3ccc4c(c3)oc3ccccc34)nc(-c3cccc4oc5ccc(-c6ccc(-c7ccc8c(c7)C7(c9ccccc9-c9ccccc97)c7ccccc7-8)cc6)cc5c34)n2)cc1]

TABLE 1-continued
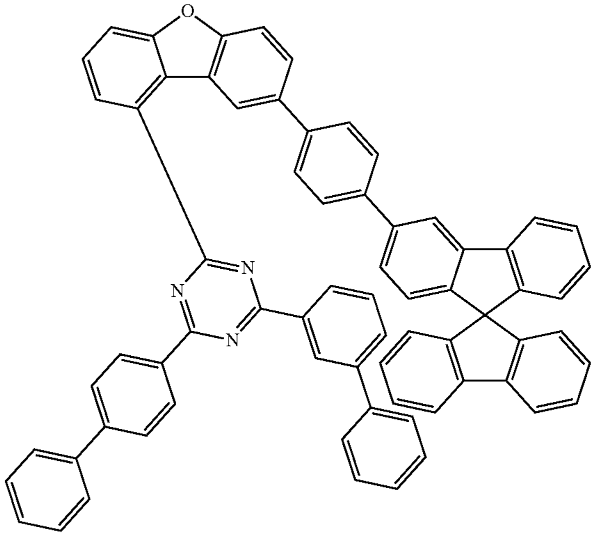 [SMILES: c1ccc(-c2ccc(-c3nc(-c4cccc(-c5ccccc5)c4)nc(-c4cccc5oc6ccc(-c7ccc(-c8ccc9c(c8)-c8ccccc8C98c9ccccc9-c9ccccc98)cc7)cc6c45)n3)cc2)cc1]
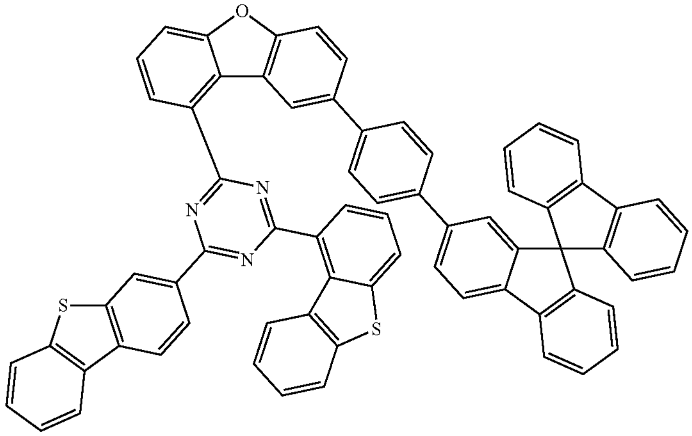 [SMILES: c1ccc2c(c1)-c1ccccc1C21c2ccccc2-c2ccc(-c3ccc(-c4ccc5oc6cccc(-c7nc(-c8ccc9c(c8)sc8ccccc89)nc(-c8cccc9sc%10ccccc%10c89)n7)c6c5c4)cc3)cc21]
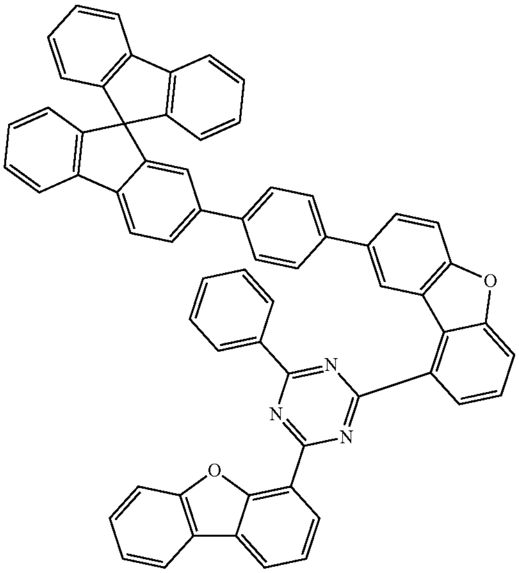 [SMILES: c1ccc(-c2nc(-c3cccc4c3oc3ccccc34)nc(-c3cccc4oc5ccc(-c6ccc(-c7ccc8c(c7)C7(c9ccccc9-c9ccccc97)c7ccccc7-8)cc6)cc5c34)n2)cc1]

TABLE 1-continued
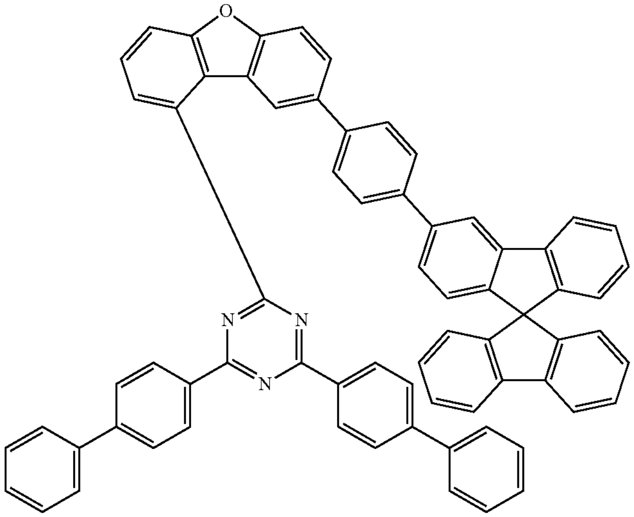 [SMILES: c1ccc(-c2ccc(-c3nc(-c4ccc(-c5ccccc5)cc4)nc(-c4cccc5oc6ccc(-c7ccc(-c8ccc9c(c8)-c8ccccc8C98c9ccccc9-c9ccccc98)cc7)cc6c45)n3)cc2)cc1]
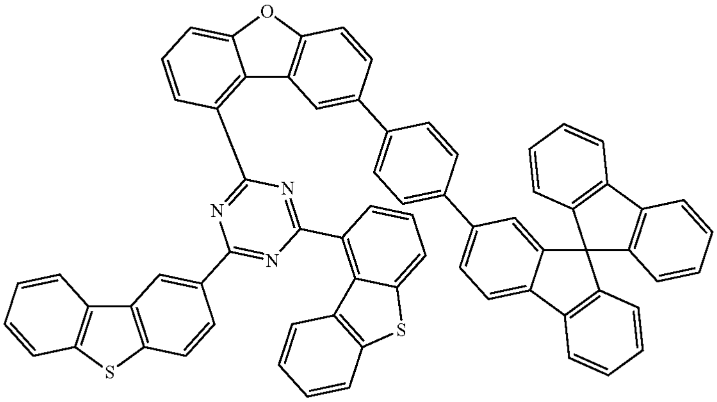 [SMILES: c1ccc2c(c1)-c1ccccc1C21c2ccccc2-c2ccc(-c3ccc(-c4ccc5oc6cccc(-c7nc(-c8ccc9sc%10ccccc%10c9c8)nc(-c8cccc9sc%10ccccc%10c89)n7)c6c5c4)cc3)cc21]
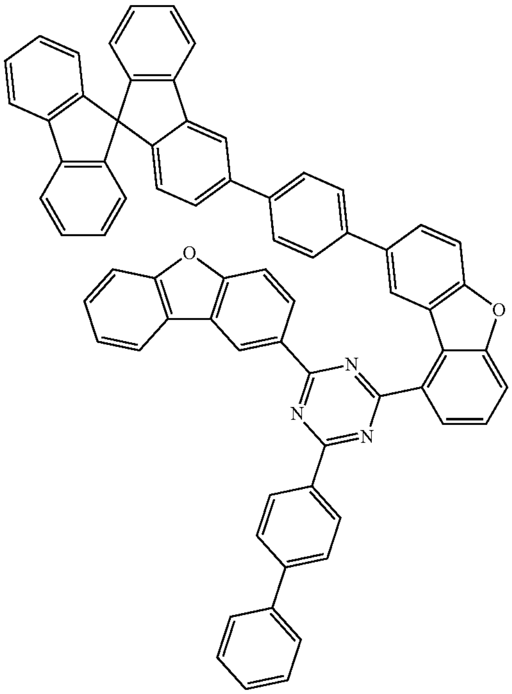 [SMILES: c1ccc(-c2ccc(-c3nc(-c4ccc5oc6ccccc6c5c4)nc(-c4cccc5oc6ccc(-c7ccc(-c8ccc9c(c8)-c8ccccc8C98c9ccccc9-c9ccccc98)cc7)cc6c45)n3)cc2)cc1]

TABLE 1-continued
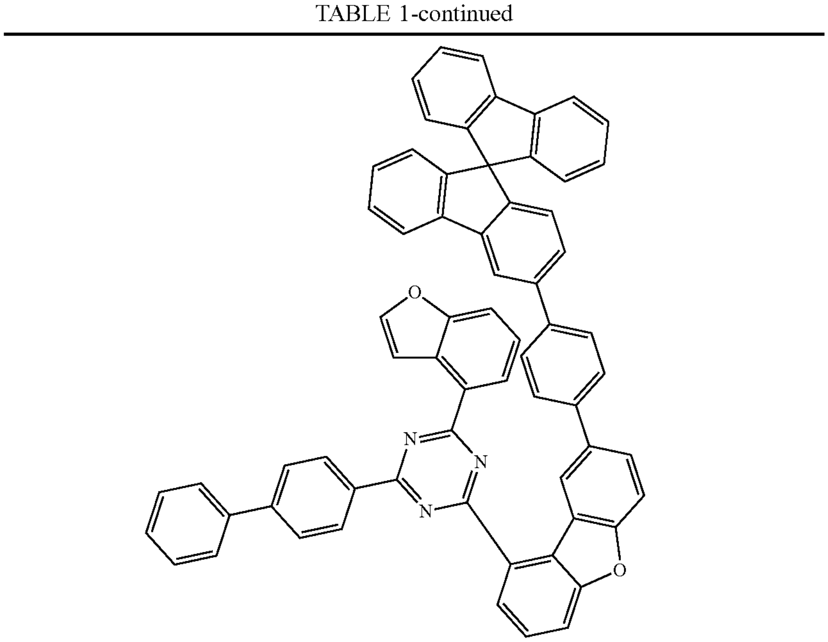
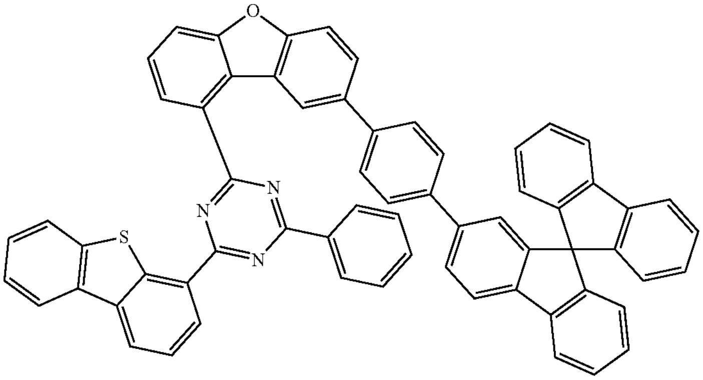 [SMILES: c1ccc(-c2nc(-c3cccc4c3sc3ccccc34)nc(-c3cccc4oc5ccc(-c6ccc(-c7ccc8c(c7)C7(c9ccccc9-c9ccccc97)c7ccccc7-8)cc6)cc5c34)n2)cc1]
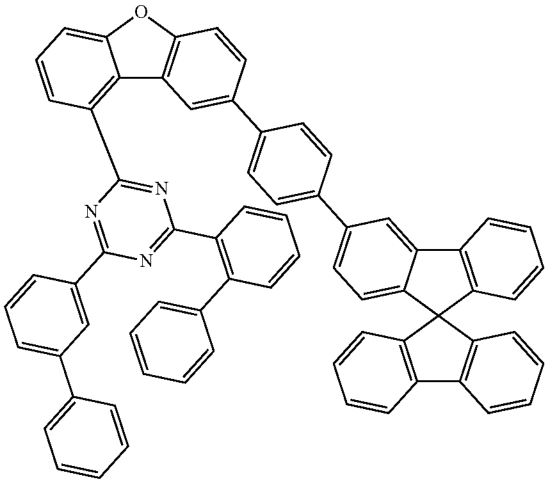 [SMILES: c1ccc(-c2cccc(-c3nc(-c4ccccc4-c4ccccc4)nc(-c4cccc5oc6ccc(-c7ccc(-c8ccc9c(c8)-c8ccccc8C98c9ccccc9-c9ccccc98)cc7)cc6c45)n3)c2)cc1]

TABLE 1-continued
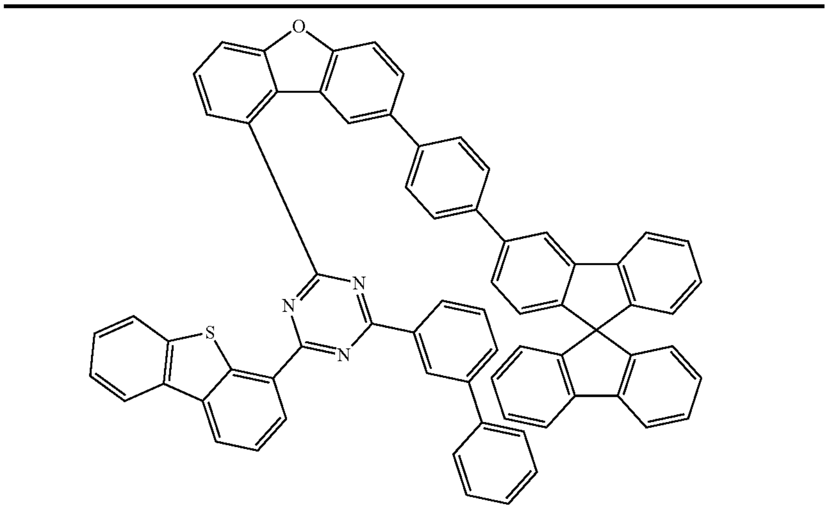
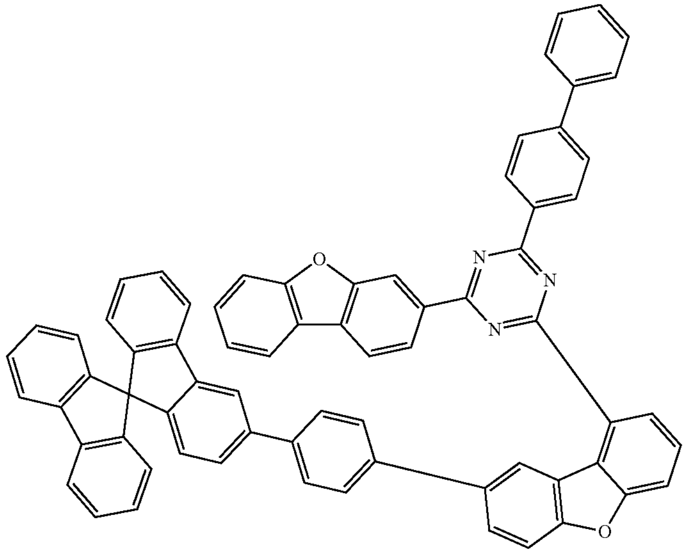 [SMILES: c1ccc(-c2ccc(-c3nc(-c4ccc5c(c4)oc4ccccc45)nc(-c4cccc5oc6ccc(-c7ccc(-c8ccc9c(c8)-c8ccccc8C98c9ccccc9-c9ccccc98)cc7)cc6c45)n3)cc2)cc1]
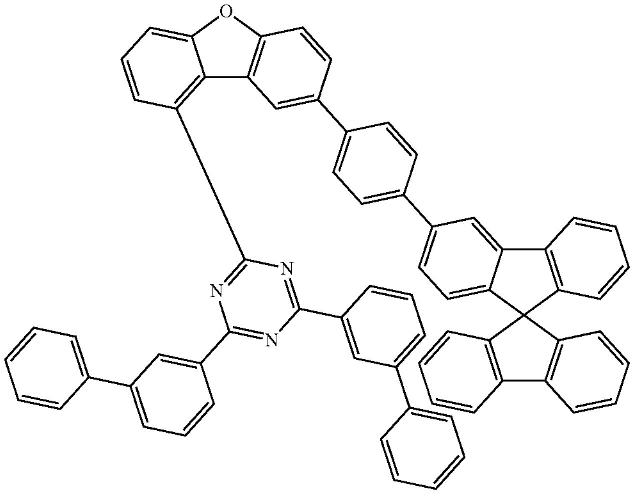 [SMILES: c1ccc(-c2cccc(-c3nc(-c4cccc(-c5ccccc5)c4)nc(-c4cccc5oc6ccc(-c7ccc(-c8ccc9c(c8)-c8ccccc8C98c9ccccc9-c9ccccc98)cc7)cc6c45)n3)c2)cc1]

TABLE 1-continued
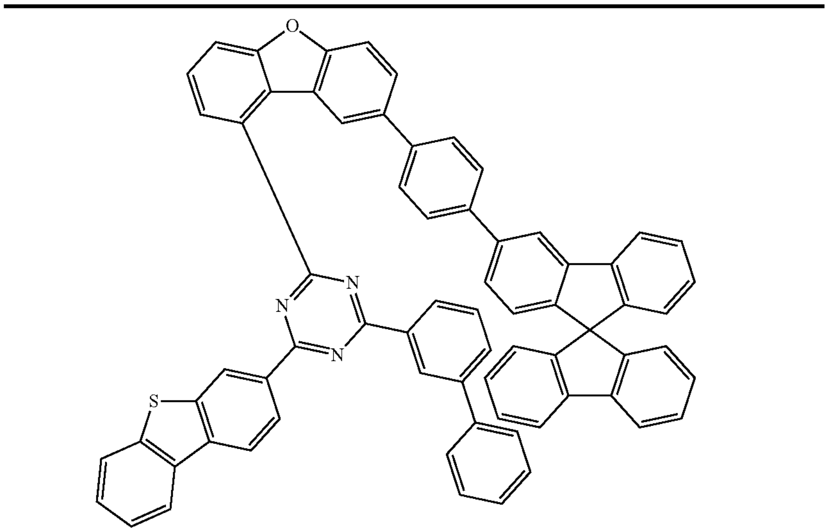
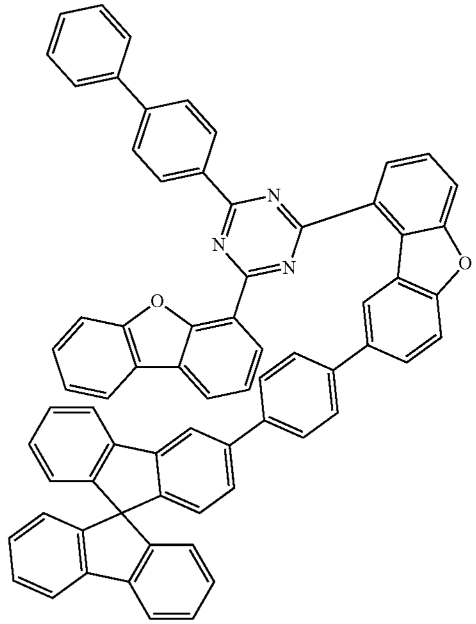 [SMILES: c1ccc(-c2ccc(-c3nc(-c4cccc5c4oc4ccccc45)nc(-c4cccc5oc6ccc(-c7ccc(-c8ccc9c(c8)-c8ccccc8C98c9ccccc9-c9ccccc98)cc7)cc6c45)n3)cc2)cc1]
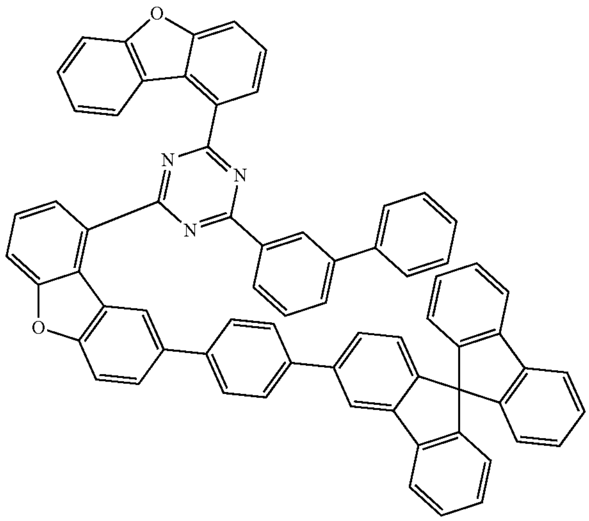 [SMILES: c1ccc(-c2cccc(-c3nc(-c4cccc5oc6ccccc6c45)nc(-c4cccc5oc6ccc(-c7ccc(-c8ccc9c(c8)-c8ccccc8C98c9ccccc9-c9ccccc98)cc7)cc6c45)n3)c2)cc1]

TABLE 1-continued
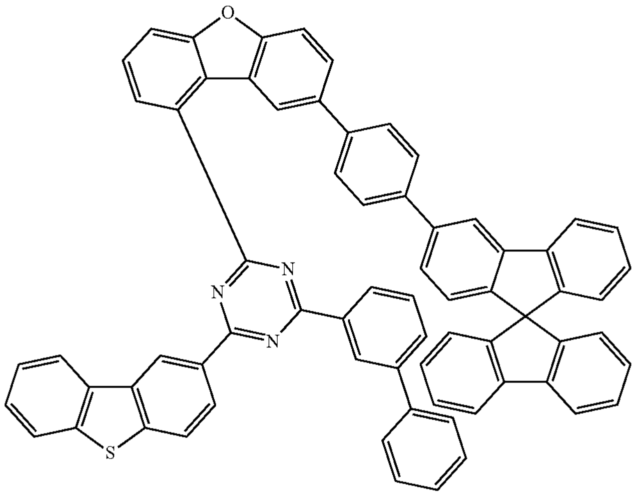 [SMILES: c1ccc(-c2cccc(-c3nc(-c4ccc5sc6ccccc6c5c4)nc(-c4cccc5oc6ccc(-c7ccc(-c8ccc9c(c8)-c8ccccc8C98c9ccccc9-c9ccccc98)cc7)cc6c45)n3)c2)cc1]
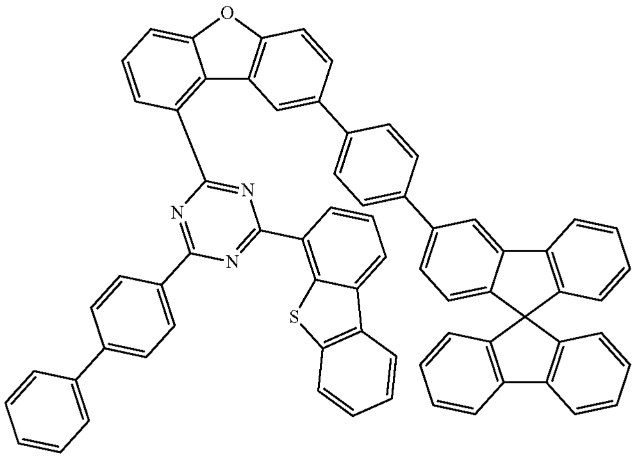 [SMILES: c1ccc(-c2ccc(-c3nc(-c4cccc5c4sc4ccccc45)nc(-c4cccc5oc6ccc(-c7ccc(-c8ccc9c(c8)-c8ccccc8C98c9ccccc9-c9ccccc98)cc7)cc6c45)n3)cc2)cc1]
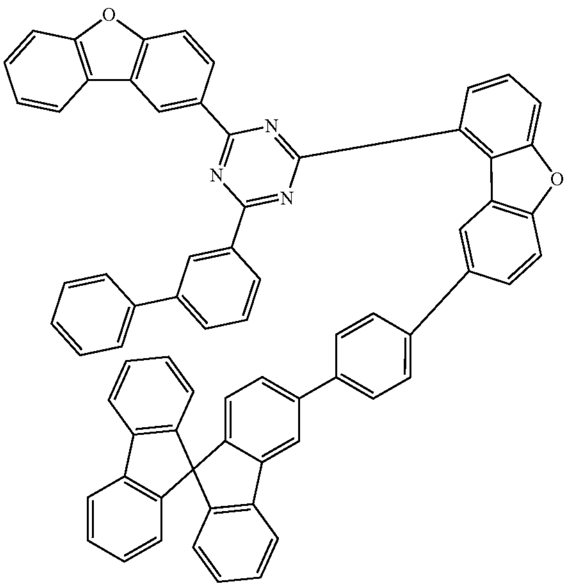 [SMILES: c1ccc(-c2cccc(-c3nc(-c4ccc5oc6ccccc6c5c4)nc(-c4cccc5oc6ccc(-c7ccc(-c8ccc9c(c8)-c8ccccc8C98c9ccccc9-c9ccccc98)cc7)cc6c45)n3)c2)cc1]

TABLE 1-continued
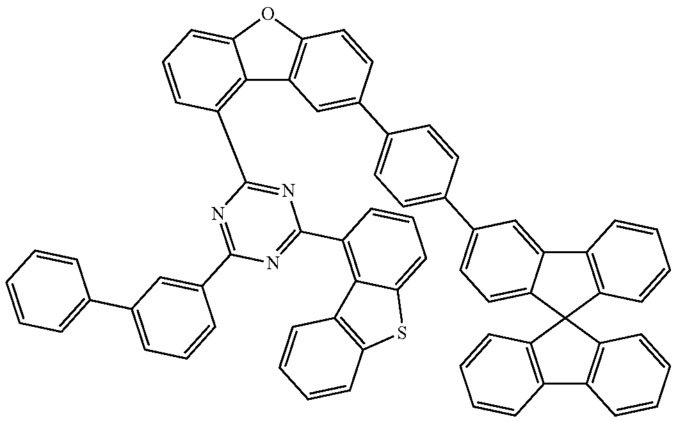 [SMILES: c1ccc(-c2cccc(-c3nc(-c4cccc5oc6ccc(-c7ccc(-c8ccc9c(c8)-c8ccccc8C98c9ccccc9-c9ccccc98)cc7)cc6c45)nc(-c4cccc5sc6ccccc6c45)n3)c2)cc1]
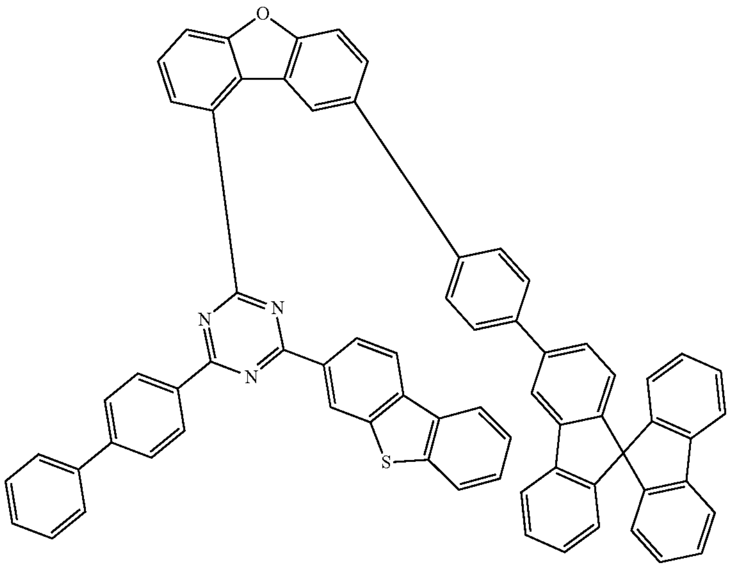 [SMILES: c1ccc(-c2ccc(-c3nc(-c4ccc5c(c4)sc4ccccc45)nc(-c4cccc5oc6ccc(-c7ccc(-c8ccc9c(c8)-c8ccccc8C98c9ccccc9-c9ccccc98)cc7)cc6c45)n3)cc2)cc1]
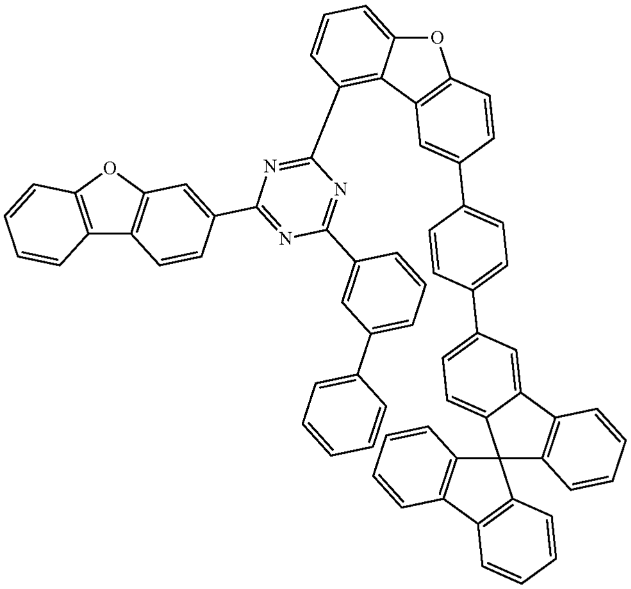 [SMILES: c1ccc(-c2cccc(-c3nc(-c4ccc5c(c4)oc4ccccc45)nc(-c4cccc5oc6ccc(-c7ccc(-c8ccc9c(c8)-c8ccccc8C98c9ccccc9-c9ccccc98)cc7)cc6c45)n3)c2)cc1]

TABLE 1-continued
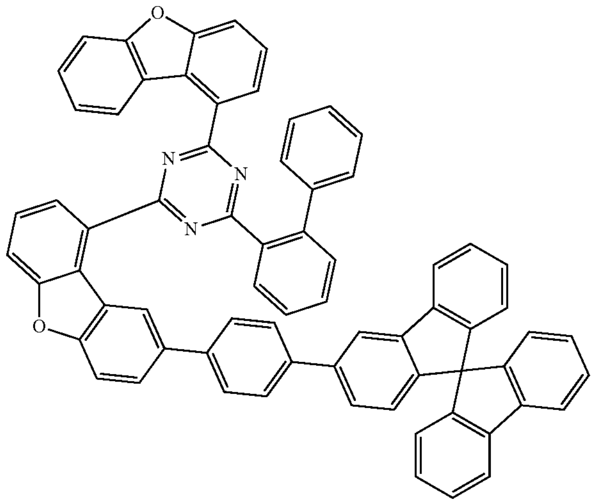 [SMILES: c1ccc(-c2ccccc2-c2nc(-c3cccc4oc5ccccc5c34)nc(-c3cccc4oc5ccc(-c6ccc(-c7ccc8c(c7)-c7ccccc7C87c8ccccc8-c8ccccc87)cc6)cc5c34)n2)cc1]
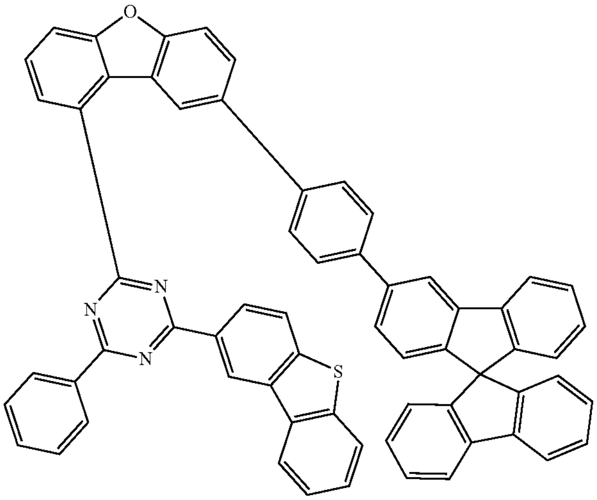 [SMILES: c1ccc(-c2nc(-c3ccc4sc5ccccc5c4c3)nc(-c3cccc4oc5ccc(-c6ccc(-c7ccc8c(c7)-c7ccccc7C87c8ccccc8-c8ccccc87)cc6)cc5c34)n2)cc1]
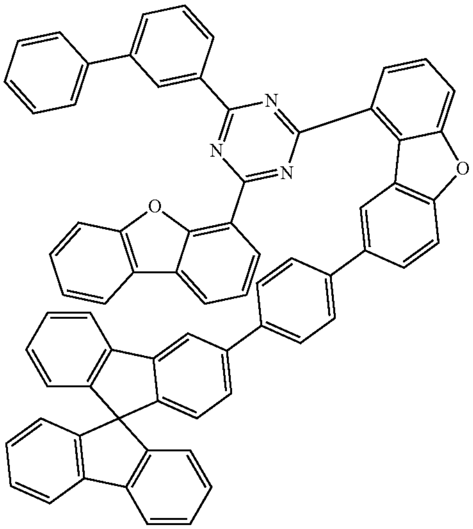 [SMILES: c1ccc(-c2cccc(-c3nc(-c4cccc5c4oc4ccccc45)nc(-c4cccc5oc6ccc(-c7ccc(-c8ccc9c(c8)-c8ccccc8C98c9ccccc9-c9ccccc98)cc7)cc6c45)n3)c2)cc1]

TABLE 1-continued
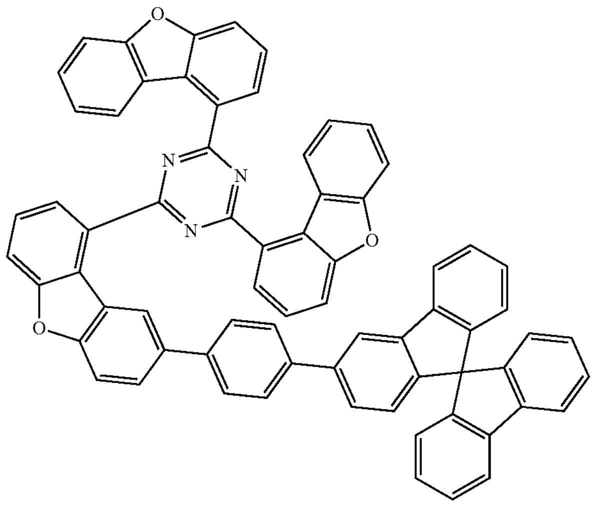 [SMILES: c1ccc2c(c1)-c1ccccc1C21c2ccccc2-c2cc(-c3ccc(-c4ccc5oc6cccc(-c7nc(-c8cccc9oc%10ccccc%10c89)nc(-c8cccc9oc%10ccccc%10c89)n7)c6c5c4)cc3)ccc21]
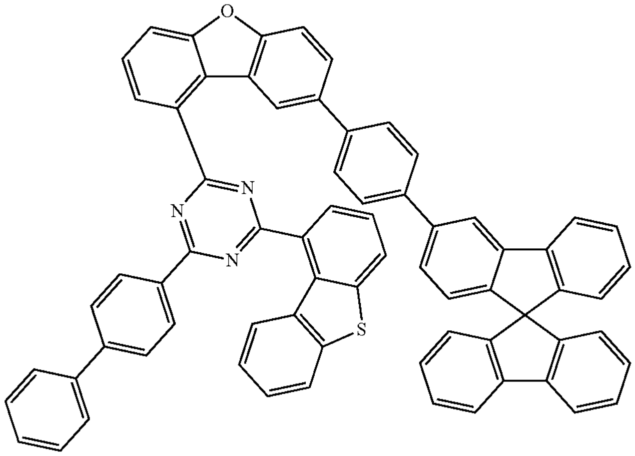 [SMILES: c1ccc(-c2ccc(-c3nc(-c4cccc5oc6ccc(-c7ccc(-c8ccc9c(c8)-c8ccccc8C98c9ccccc9-c9ccccc98)cc7)cc6c45)nc(-c4cccc5sc6ccccc6c45)n3)cc2)cc1]
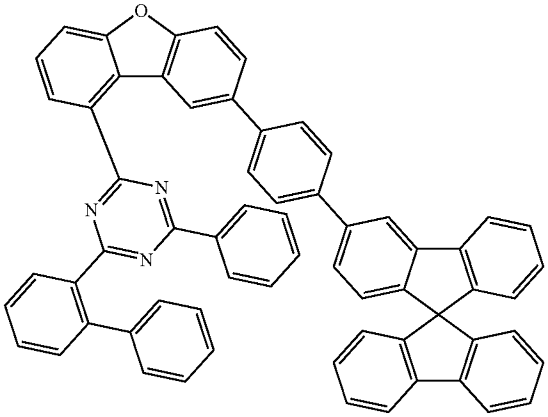 [SMILES: c1ccc(-c2nc(-c3ccccc3-c3ccccc3)nc(-c3cccc4oc5ccc(-c6ccc(-c7ccc8c(c7)-c7ccccc7C87c8ccccc8-c8ccccc87)cc6)cc5c34)n2)cc1]

TABLE 1-continued
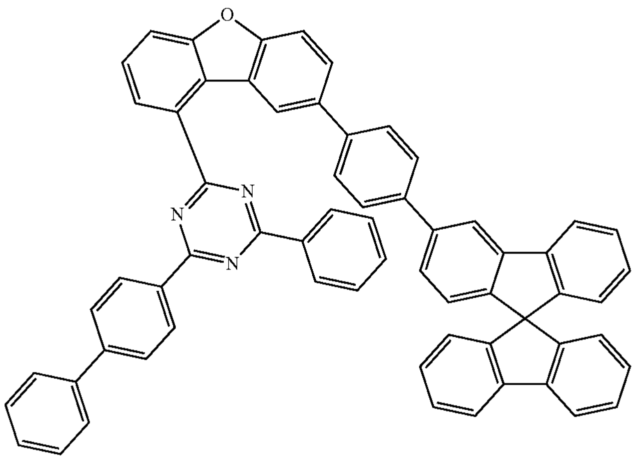 [SMILES: c1ccc(-c2ccc(-c3nc(-c4ccccc4)nc(-c4cccc5oc6ccc(-c7ccc(-c8ccc9c(c8)-c8ccccc8C98c9ccccc9-c9ccccc98)cc7)cc6c45)n3)cc2)cc1]
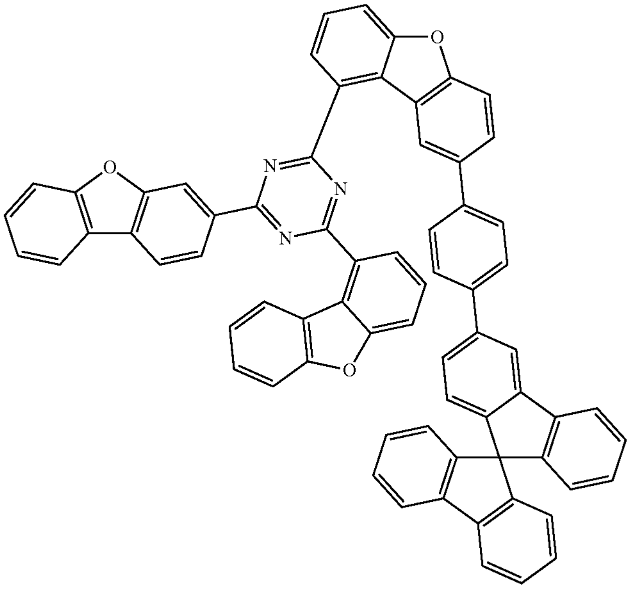 [SMILES: c1ccc2c(c1)-c1ccccc1C21c2ccccc2-c2cc(-c3ccc(-c4ccc5oc6cccc(-c7nc(-c8ccc9c(c8)oc8ccccc89)nc(-c8cccc9oc%10ccccc%10c89)n7)c6c5c4)cc3)ccc21]
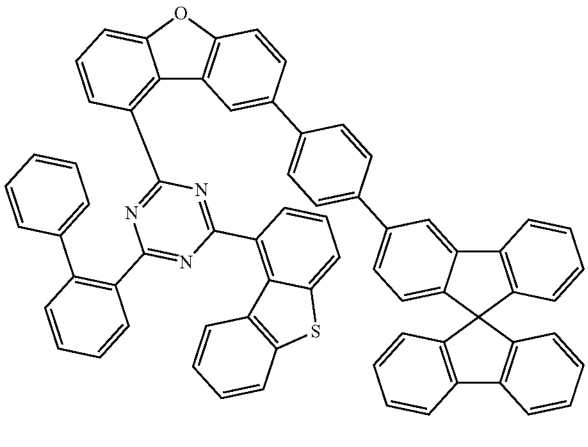 [SMILES: c1ccc(-c2ccccc2-c2nc(-c3cccc4oc5ccc(-c6ccc(-c7ccc8c(c7)-c7ccccc7C87c8ccccc8-c8ccccc87)cc6)cc5c34)nc(-c3cccc4sc5ccccc5c34)n2)cc1]

TABLE 1-continued
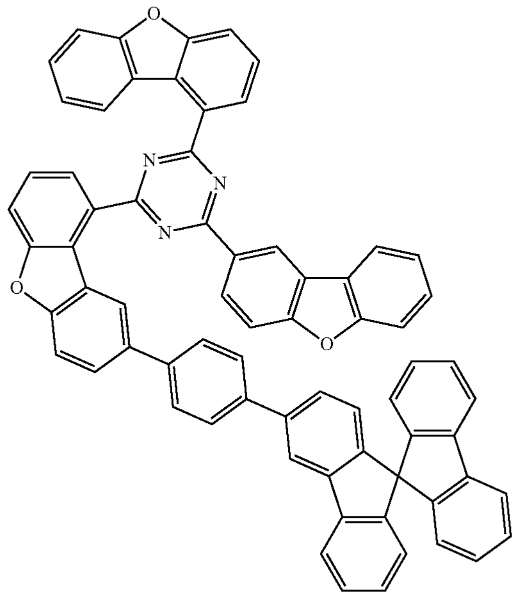
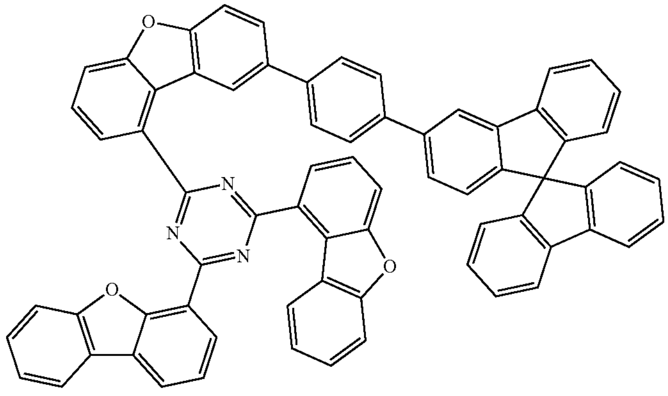
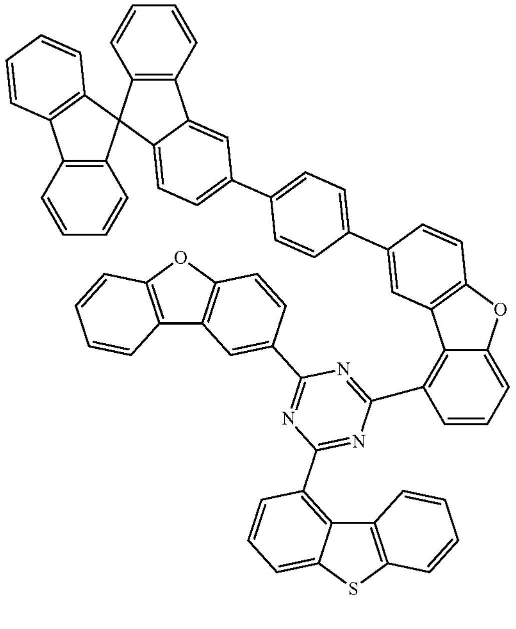 [SMILES: c1ccc2c(c1)-c1ccccc1C21c2ccccc2-c2cc(-c3ccc(-c4ccc5oc6cccc(-c7nc(-c8ccc9oc%10ccccc%10c9c8)nc(-c8cccc9sc%10ccccc%10c89)n7)c6c5c4)cc3)ccc21]

TABLE 1-continued
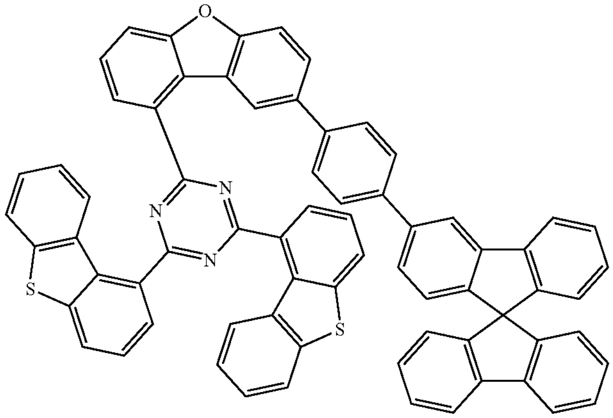 [SMILES: c1ccc2c(c1)-c1ccccc1C21c2ccccc2-c2cc(-c3ccc(-c4ccc5oc6cccc(-c7nc(-c8cccc9sc%10ccccc%10c89)nc(-c8cccc9sc%10ccccc%10c89)n7)c6c5c4)cc3)ccc21]
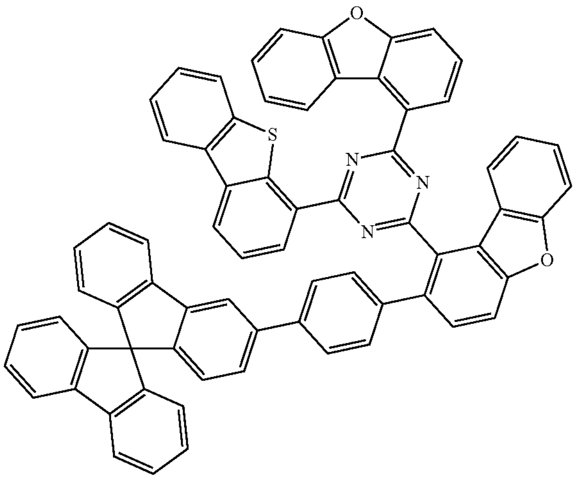 [SMILES: c1ccc2c(c1)-c1ccccc1C21c2ccccc2-c2cc(-c3ccc(-c4ccc5oc6ccccc6c5c4-c4nc(-c5cccc6c5sc5ccccc56)nc(-c5cccc6oc7ccccc7c56)n4)cc3)ccc21]
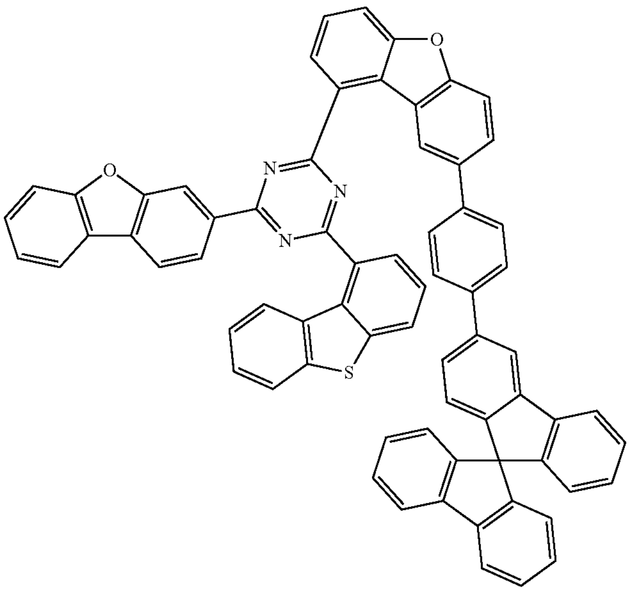

TABLE 1-continued
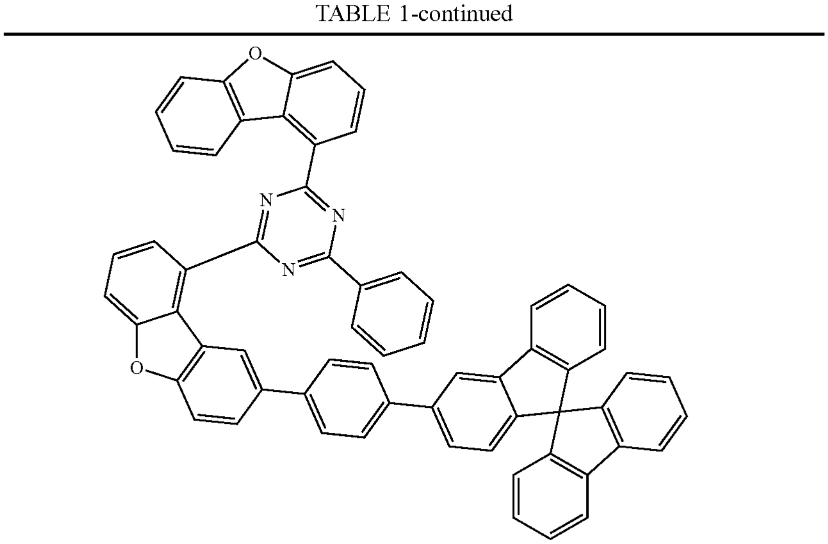
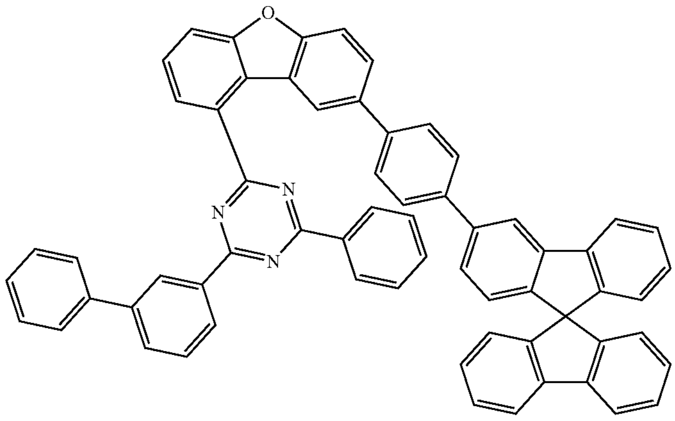 [SMILES: c1ccc(-c2cccc(-c3nc(-c4ccccc4)nc(-c4cccc5oc6ccc(-c7ccc(-c8ccc9c(c8)-c8ccccc8C98c9ccccc9-c9ccccc98)cc7)cc6c45)n3)c2)cc1]
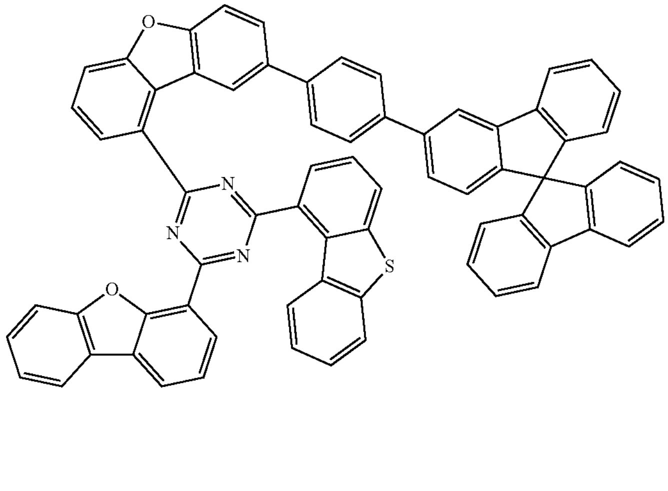 [SMILES: c1ccc2c(c1)-c1ccccc1C21c2ccccc2-c2cc(-c3ccc(-c4ccc5oc6cccc(-c7nc(-c8cccc9c8oc8ccccc89)nc(-c8cccc9sc%10ccccc%10c89)n7)c6c5c4)cc3)ccc21]

TABLE 1-continued
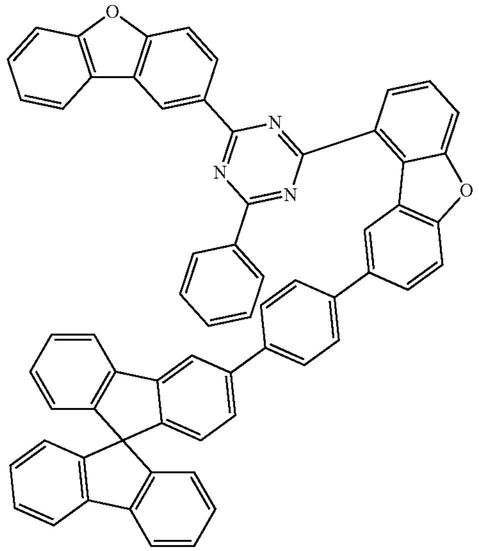 [SMILES: c1ccc(-c2nc(-c3ccc4oc5ccccc5c4c3)nc(-c3cccc4oc5ccc(-c6ccc(-c7ccc8c(c7)-c7ccccc7C87c8ccccc8-c8ccccc87)cc6)cc5c34)n2)cc1]
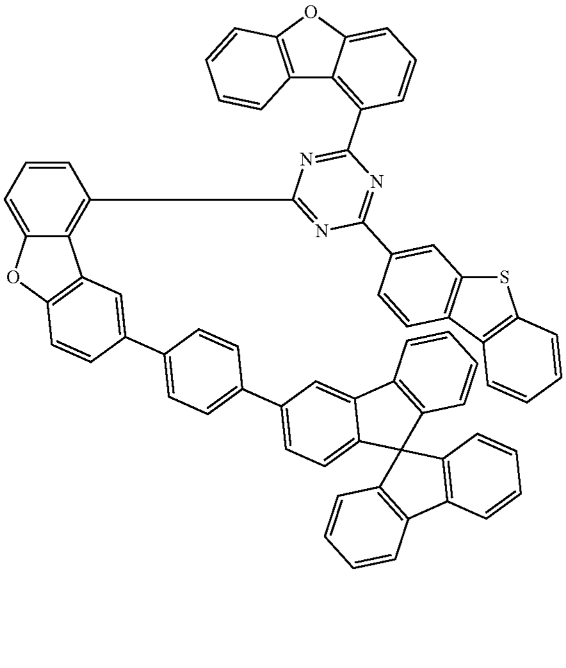 [SMILES: c1ccc2c(c1)-c1ccccc1C21c2ccccc2-c2cc(-c3ccc(-c4ccc5oc6cccc(-c7nc(-c8ccc9c(c8)sc8ccccc89)nc(-c8cccc9oc%10ccccc%10c89)n7)c6c5c4)cc3)ccc21]

TABLE 1-continued
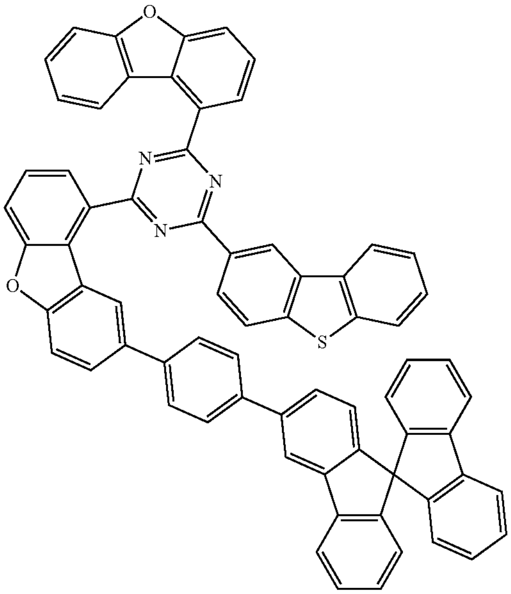
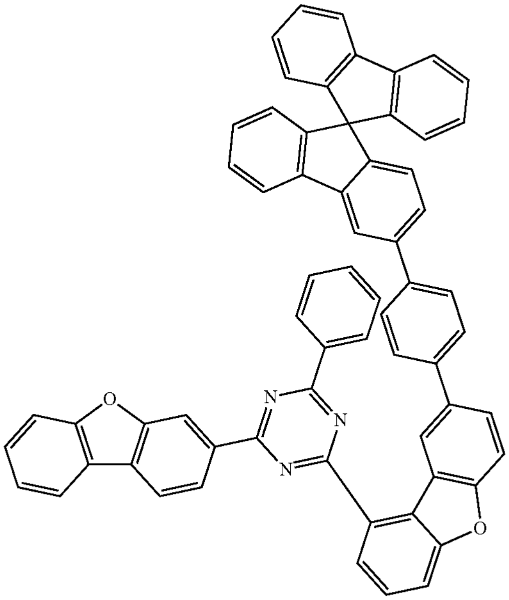 [SMILES: c1ccc(-c2nc(-c3ccc4c(c3)oc3ccccc34)nc(-c3cccc4oc5ccc(-c6ccc(-c7ccc8c(c7)-c7ccccc7C87c8ccccc8-c8ccccc87)cc6)cc5c34)n2)cc1]
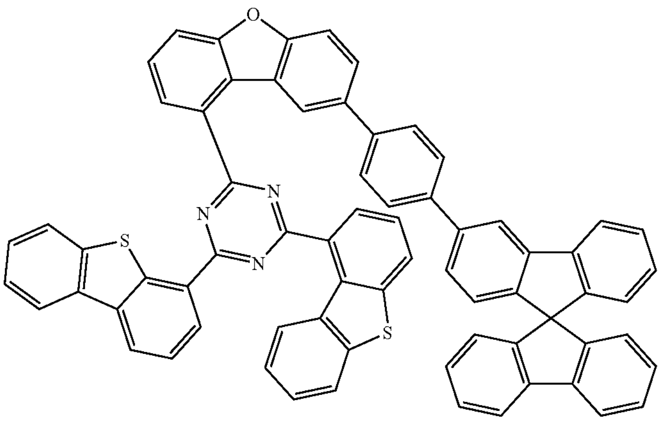 [SMILES: c1ccc2c(c1)-c1ccccc1C21c2ccccc2-c2cc(-c3ccc(-c4ccc5oc6cccc(-c7nc(-c8cccc9c8sc8ccccc89)nc(-c8cccc9sc%10ccccc%10c89)n7)c6c5c4)cc3)ccc21]

TABLE 1-continued
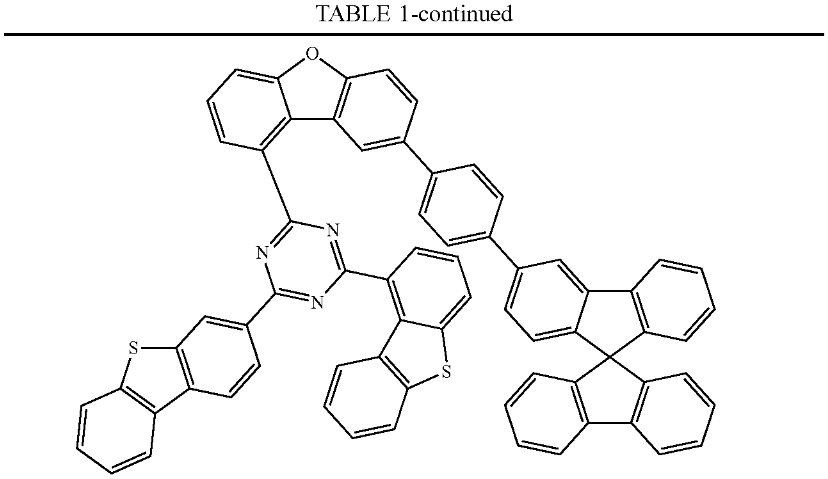
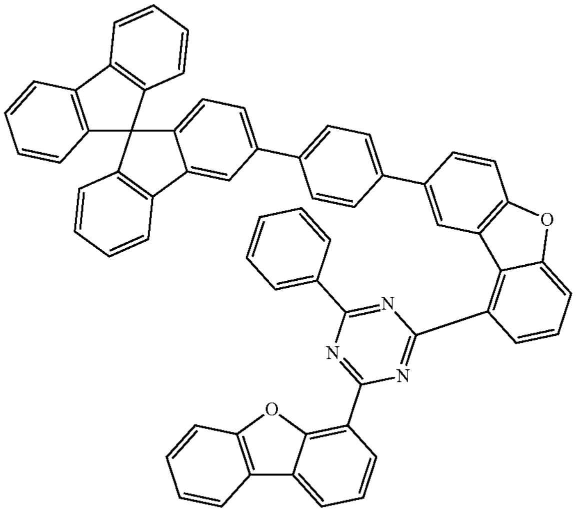 [SMILES: c1ccc(-c2nc(-c3cccc4c3oc3ccccc34)nc(-c3cccc4oc5ccc(-c6ccc(-c7ccc8c(c7)-c7ccccc7C87c8ccccc8-c8ccccc87)cc6)cc5c34)n2)cc1]
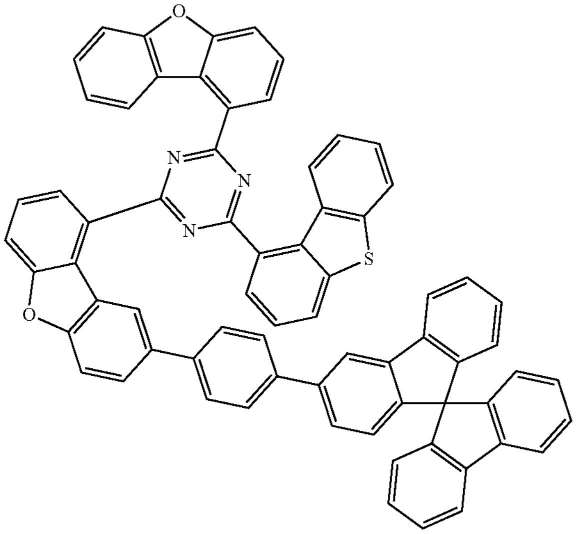 [SMILES: c1ccc2c(c1)-c1ccccc1C21c2ccccc2-c2cc(-c3ccc(-c4ccc5oc6cccc(-c7nc(-c8cccc9oc%10ccccc%10c89)nc(-c8cccc9sc%10ccccc%10c89)n7)c6c5c4)cc3)ccc21]

TABLE 1-continued
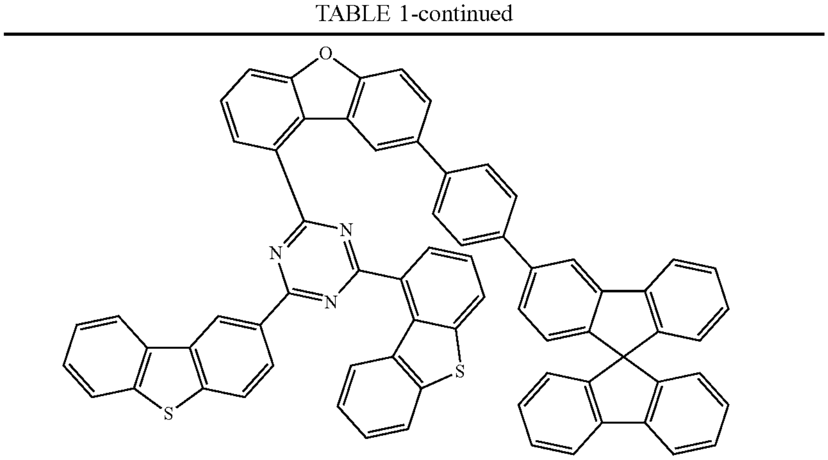
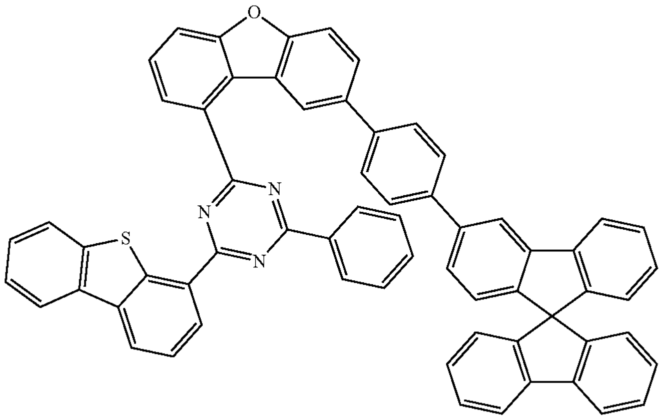 [SMILES: c1ccc(-c2nc(-c3cccc4c3sc3ccccc34)nc(-c3cccc4oc5ccc(-c6ccc(-c7ccc8c(c7)-c7ccccc7C87c8ccccc8-c8ccccc87)cc6)cc5c34)n2)cc1]
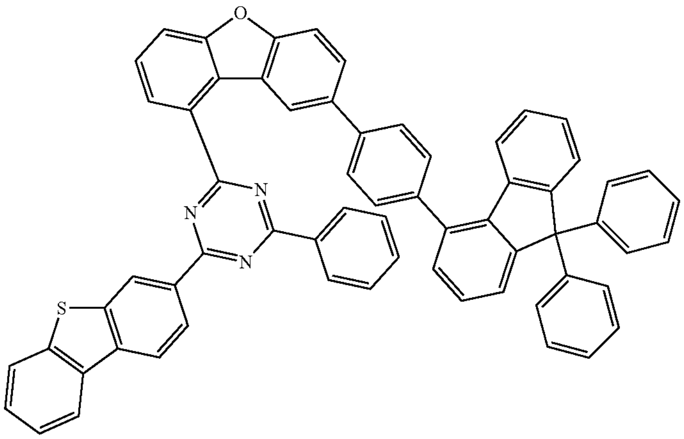 [SMILES: c1ccc(-c2nc(-c3ccc4c(c3)sc3ccccc34)nc(-c3cccc4oc5ccc(-c6ccc(-c7cccc8c7-c7ccccc7C8(c7ccccc7)c7ccccc7)cc6)cc5c34)n2)cc1]

TABLE 1-continued
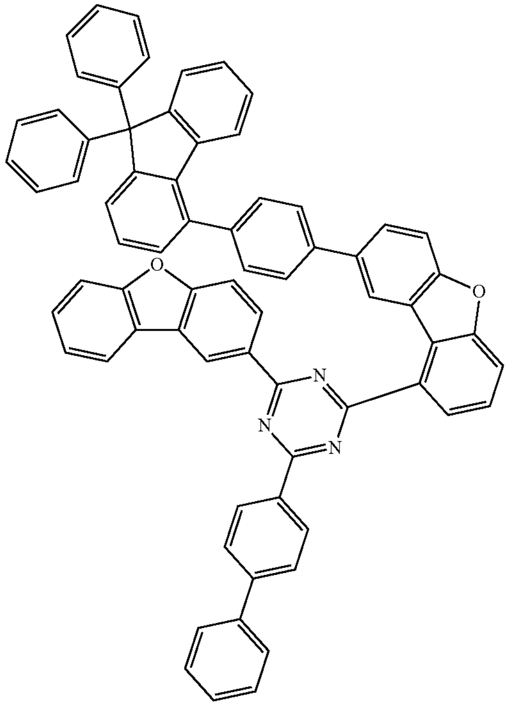 [SMILES: c1ccc(-c2ccc(-c3nc(-c4ccc5oc6ccccc6c5c4)nc(-c4cccc5oc6ccc(-c7ccc(-c8cccc9c8-c8ccccc8C9(c8ccccc8)c8ccccc8)cc7)cc6c45)n3)cc2)cc1]
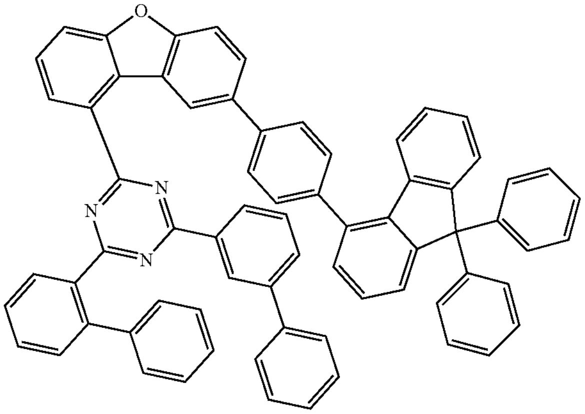 [SMILES: c1ccc(-c2cccc(-c3nc(-c4ccccc4-c4ccccc4)nc(-c4cccc5oc6ccc(-c7ccc(-c8cccc9c8-c8ccccc8C9(c8ccccc8)c8ccccc8)cc7)cc6c45)n3)c2)cc1]
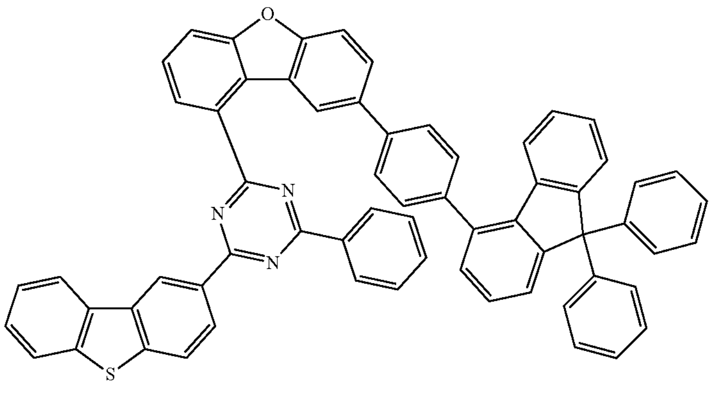 [SMILES: c1ccc(-c2nc(-c3ccc4sc5ccccc5c4c3)nc(-c3cccc4oc5ccc(-c6ccc(-c7cccc8c7-c7ccccc7C8(c7ccccc7)c7ccccc7)cc6)cc5c34)n2)cc1]

TABLE 1-continued
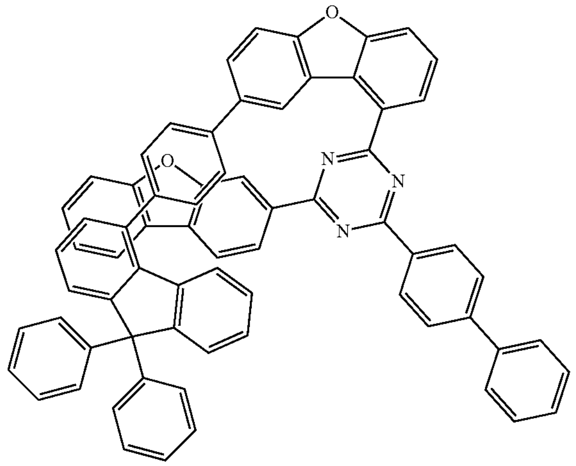 [SMILES: c1ccc(-c2ccc(-c3nc(-c4ccc5c(c4)oc4ccccc45)nc(-c4cccc5oc6ccc(-c7ccc(-c8cccc9c8-c8ccccc8C9(c8ccccc8)c8ccccc8)cc7)cc6c45)n3)cc2)cc1]
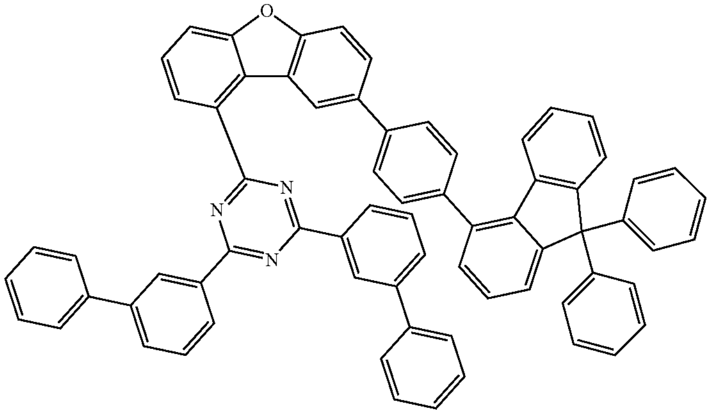 [SMILES: c1ccc(-c2cccc(-c3nc(-c4cccc(-c5ccccc5)c4)nc(-c4cccc5oc6ccc(-c7ccc(-c8cccc9c8-c8ccccc8C9(c8ccccc8)c8ccccc8)cc7)cc6c45)n3)c2)cc1]
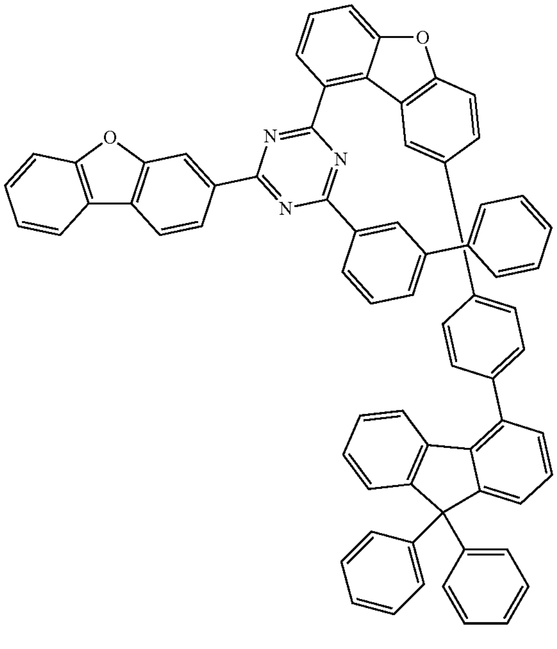 [SMILES: c1ccc(-c2cccc(-c3nc(-c4ccc5c(c4)oc4ccccc45)nc(-c4cccc5oc6ccc(-c7ccc(-c8cccc9c8-c8ccccc8C9(c8ccccc8)c8ccccc8)cc7)cc6c45)n3)c2)cc1]

TABLE 1-continued
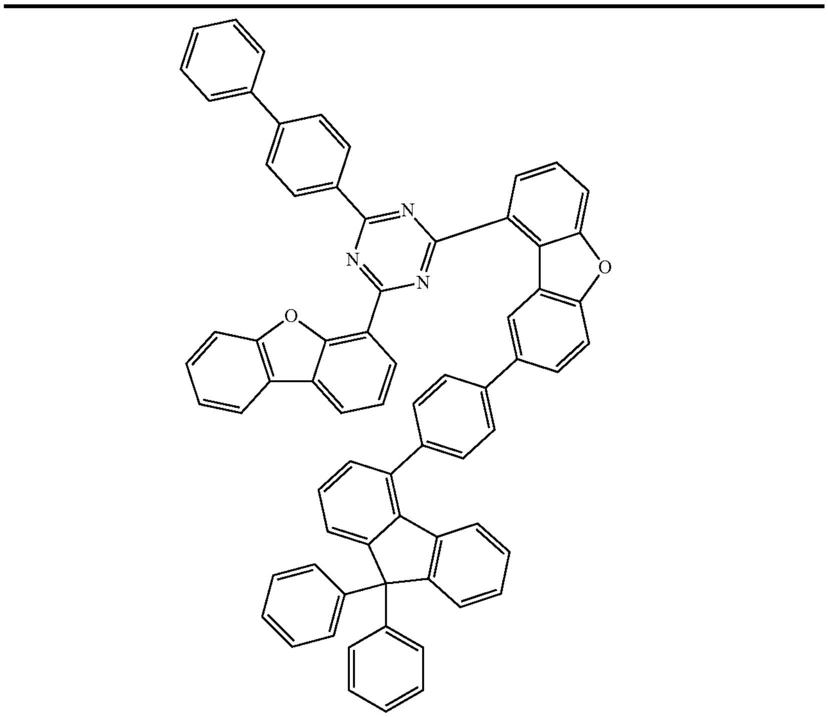
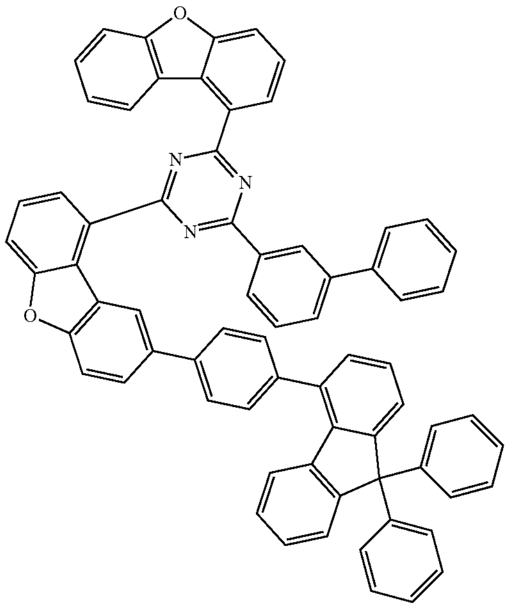 [SMILES: c1ccc(-c2cccc(-c3nc(-c4cccc5oc6ccccc6c45)nc(-c4cccc5oc6ccc(-c7ccc(-c8cccc9c8-c8ccccc8C9(c8ccccc8)c8ccccc8)cc7)cc6c45)n3)c2)cc1]

TABLE 1-continued
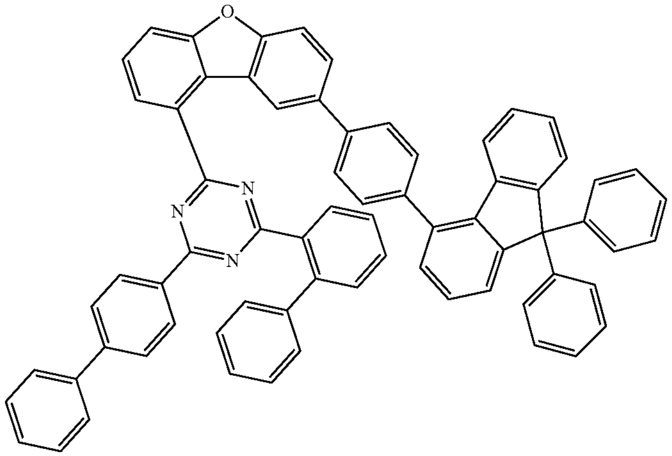 [SMILES: c1ccc(-c2ccc(-c3nc(-c4ccccc4-c4ccccc4)nc(-c4cccc5oc6ccc(-c7ccc(-c8cccc9c8-c8ccccc8C9(c8ccccc8)c8ccccc8)cc7)cc6c45)n3)cc2)cc1]
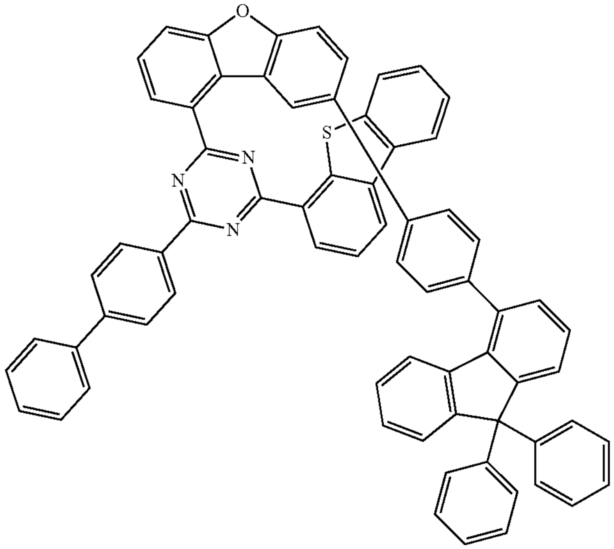 [SMILES: c1ccc(-c2ccc(-c3nc(-c4cccc5c4sc4ccccc45)nc(-c4cccc5oc6ccc(-c7ccc(-c8cccc9c8-c8ccccc8C9(c8ccccc8)c8ccccc8)cc7)cc6c45)n3)cc2)cc1]
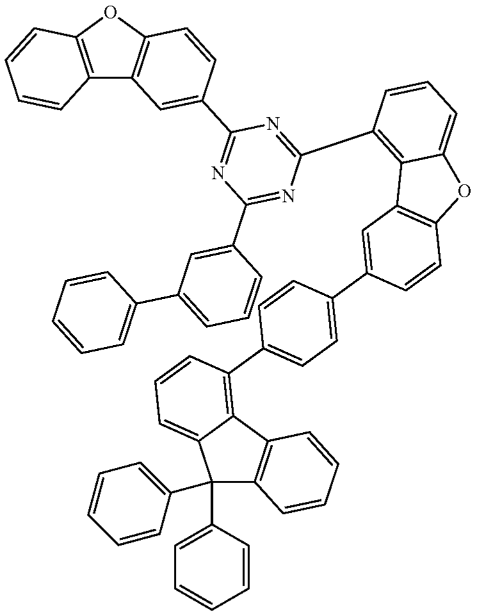 [SMILES: c1ccc(-c2cccc(-c3nc(-c4ccc5oc6ccccc6c5c4)nc(-c4cccc5oc6ccc(-c7ccc(-c8cccc9c8-c8ccccc8C9(c8ccccc8)c8ccccc8)cc7)cc6c45)n3)c2)cc1]

TABLE 1-continued
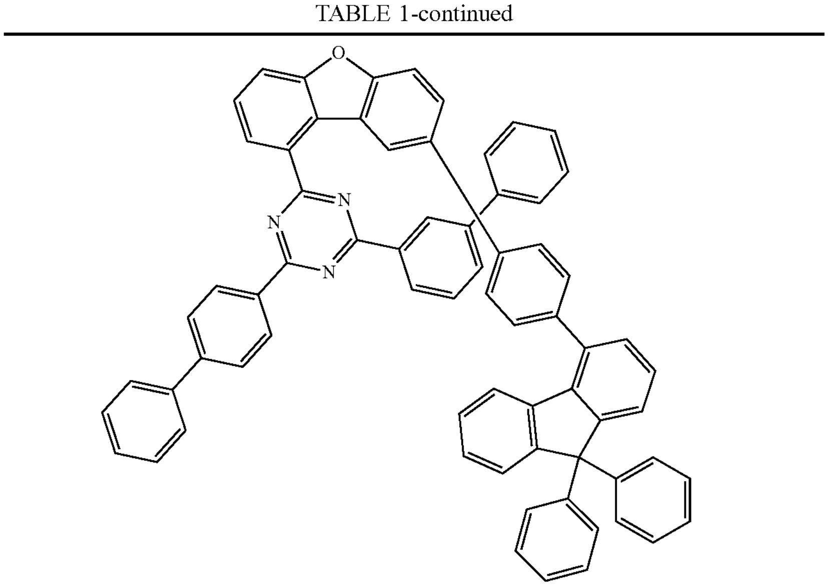
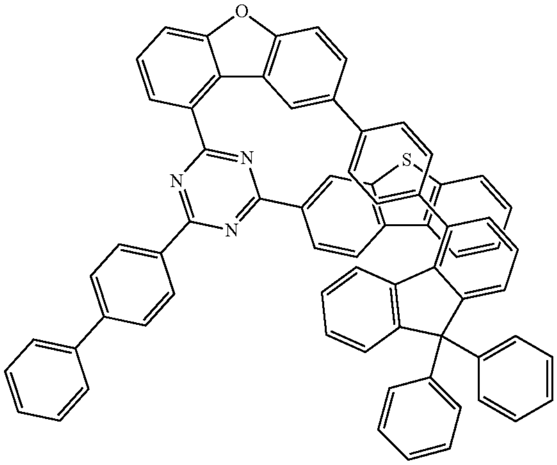 [SMILES: c1ccc(-c2ccc(-c3nc(-c4ccc5c(c4)sc4ccccc45)nc(-c4cccc5oc6ccc(-c7ccc(-c8cccc9c8-c8ccccc8C9(c8ccccc8)c8ccccc8)cc7)cc6c45)n3)cc2)cc1]
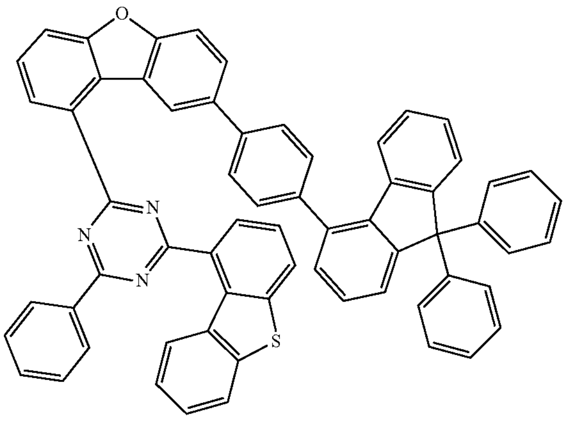 [SMILES: c1ccc(-c2nc(-c3cccc4oc5ccc(-c6ccc(-c7cccc8c7-c7ccccc7C8(c7ccccc7)c7ccccc7)cc6)cc5c34)nc(-c3cccc4sc5ccccc5c34)n2)cc1]

TABLE 1-continued
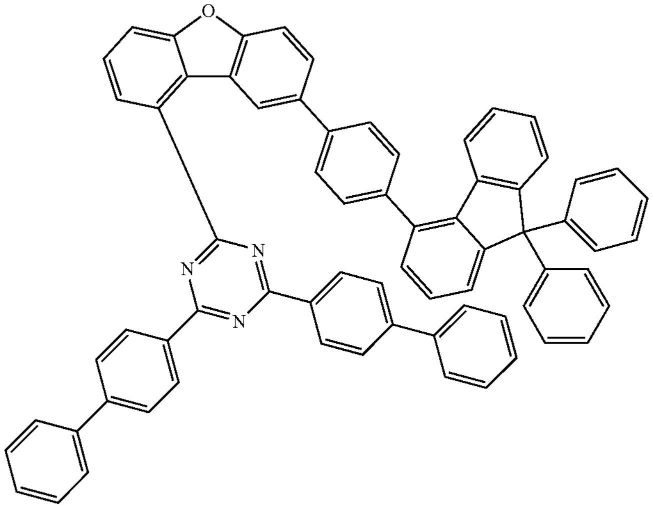 [SMILES: c1ccc(-c2ccc(-c3nc(-c4ccc(-c5ccccc5)cc4)nc(-c4cccc5oc6ccc(-c7ccc(-c8cccc9c8-c8ccccc8C9(c8ccccc8)c8ccccc8)cc7)cc6c45)n3)cc2)cc1]
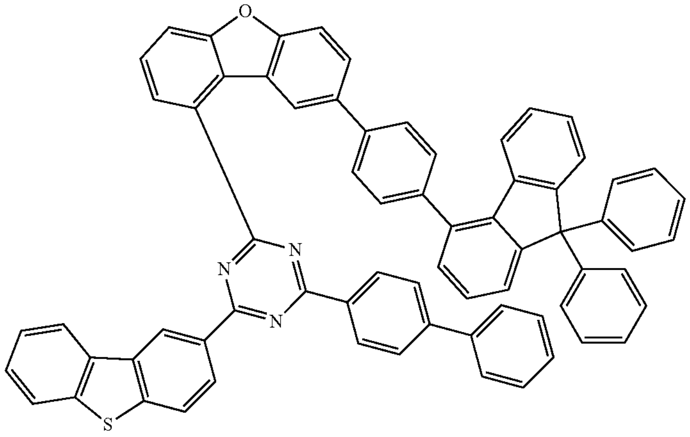 [SMILES: c1ccc(-c2ccc(-c3nc(-c4ccc5sc6ccccc6c5c4)nc(-c4cccc5oc6ccc(-c7ccc(-c8cccc9c8-c8ccccc8C9(c8ccccc8)c8ccccc8)cc7)cc6c45)n3)cc2)cc1]
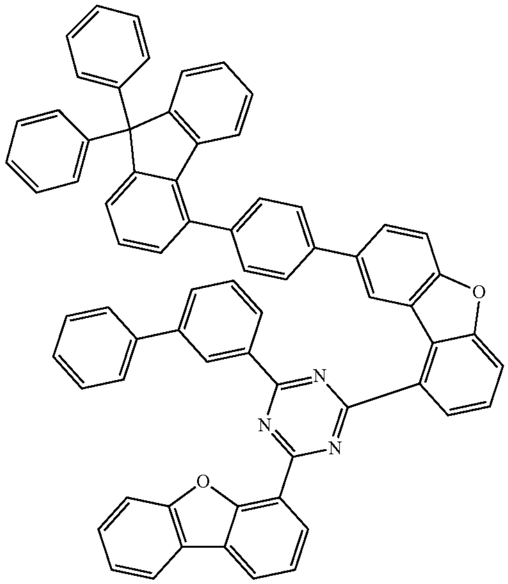 [SMILES: c1ccc(-c2cccc(-c3nc(-c4cccc5c4oc4ccccc45)nc(-c4cccc5oc6ccc(-c7ccc(-c8cccc9c8-c8ccccc8C9(c8ccccc8)c8ccccc8)cc7)cc6c45)n3)c2)cc1]

TABLE 1-continued
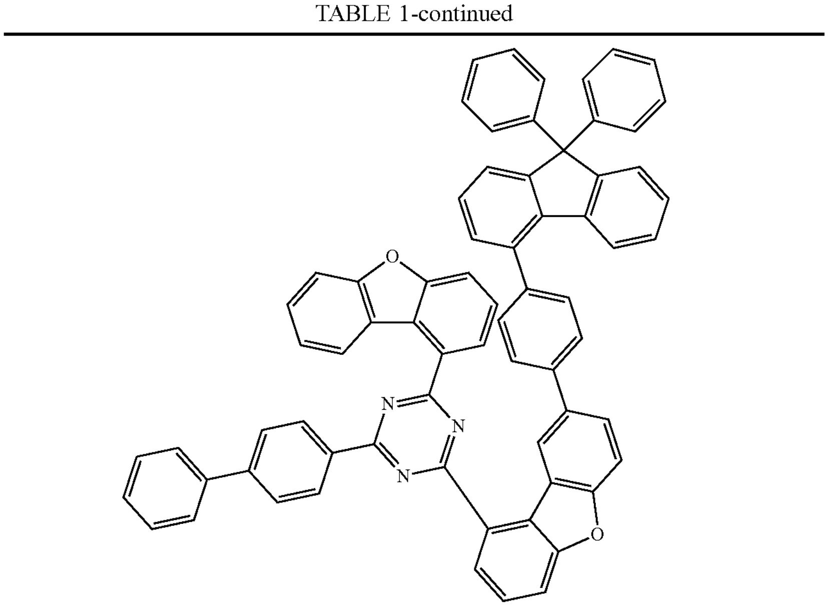
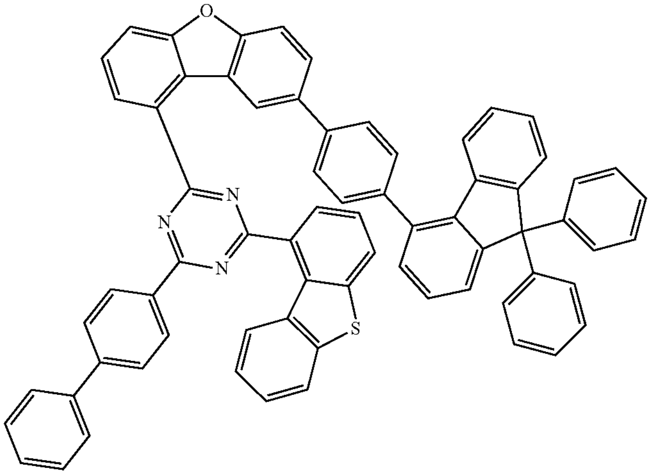 [SMILES: c1ccc(-c2ccc(-c3nc(-c4cccc5oc6ccc(-c7ccc(-c8cccc9c8-c8ccccc8C9(c8ccccc8)c8ccccc8)cc7)cc6c45)nc(-c4cccc5sc6ccccc6c45)n3)cc2)cc1]
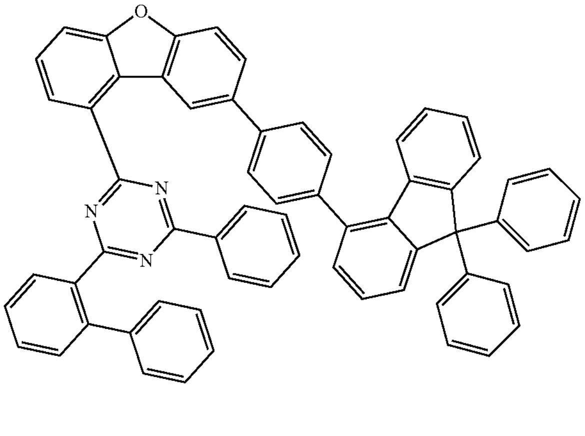 [SMILES: c1ccc(-c2nc(-c3ccccc3-c3ccccc3)nc(-c3cccc4oc5ccc(-c6ccc(-c7cccc8c7-c7ccccc7C8(c7ccccc7)c7ccccc7)cc6)cc5c34)n2)cc1]

TABLE 1-continued
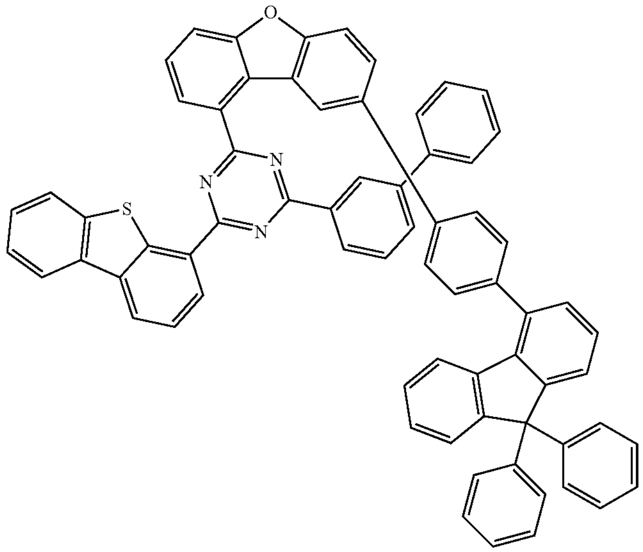 [SMILES: c1ccc(-c2cccc(-c3nc(-c4cccc5c4sc4ccccc45)nc(-c4cccc5oc6ccc(-c7ccc(-c8cccc9c8-c8ccccc8C9(c8ccccc8)c8ccccc8)cc7)cc6c45)n3)c2)cc1]
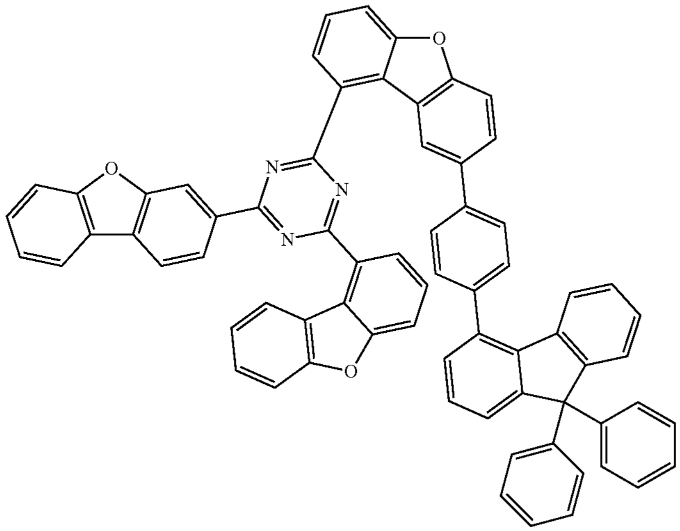 [SMILES: c1ccc(C2(c3ccccc3)c3ccccc3-c3c(-c4ccc(-c5ccc6oc7cccc(-c8nc(-c9ccc%10c(c9)oc9ccccc9%10)nc(-c9cccc%10oc%11ccccc%11c9%10)n8)c7c6c5)cc4)cccc32)cc1]
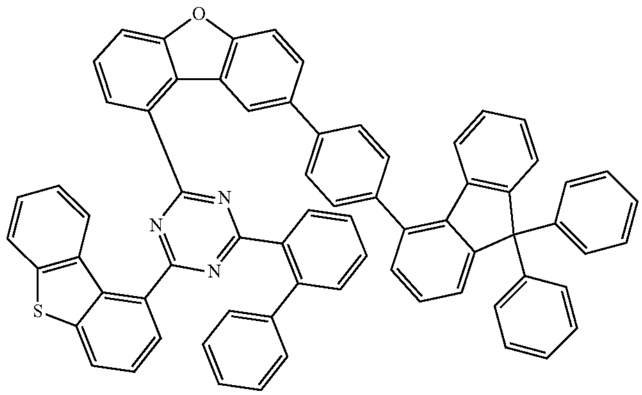 [SMILES: c1ccc(-c2ccccc2-c2nc(-c3cccc4oc5ccc(-c6ccc(-c7cccc8c7-c7ccccc7C8(c7ccccc7)c7ccccc7)cc6)cc5c34)nc(-c3cccc4sc5ccccc5c34)n2)cc1]

TABLE 1-continued
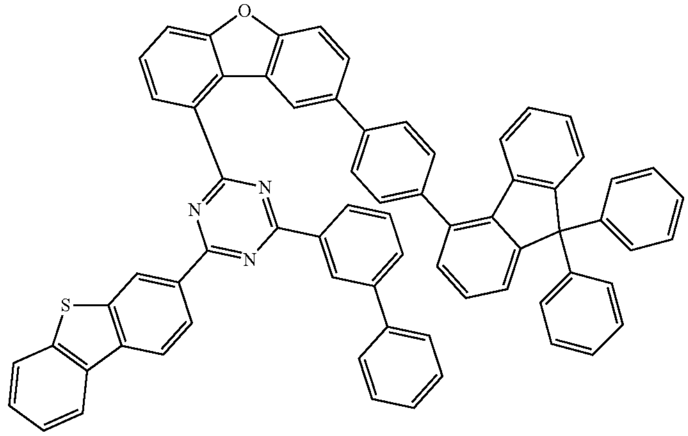 [SMILES: c1ccc(-c2cccc(-c3nc(-c4ccc5c(c4)sc4ccccc45)nc(-c4cccc5oc6ccc(-c7ccc(-c8cccc9c8-c8ccccc8C9(c8ccccc8)c8ccccc8)cc7)cc6c45)n3)c2)cc1]
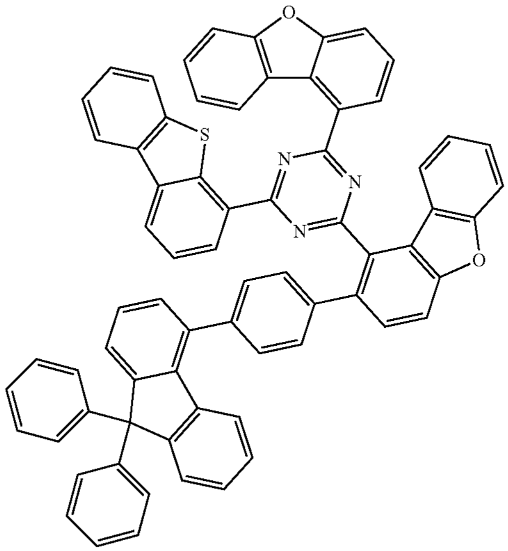 [SMILES: c1ccc(C2(c3ccccc3)c3ccccc3-c3c(-c4ccc(-c5ccc6oc7ccccc7c6c5-c5nc(-c6cccc7c6sc6ccccc67)nc(-c6cccc7oc8ccccc8c67)n5)cc4)cccc32)cc1]
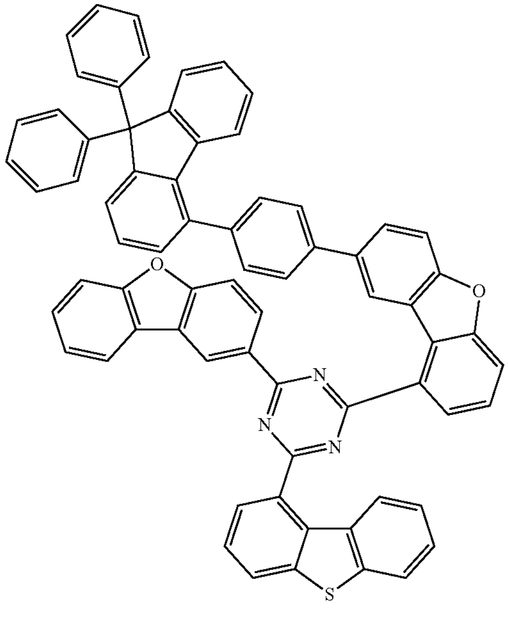 [SMILES: c1ccc(C2(c3ccccc3)c3ccccc3-c3c(-c4ccc(-c5ccc6oc7cccc(-c8nc(-c9ccc%10oc%11ccccc%11c%10c9)nc(-c9cccc%10sc%11ccccc%11c9%10)n8)c7c6c5)cc4)cccc32)cc1]

TABLE 1-continued
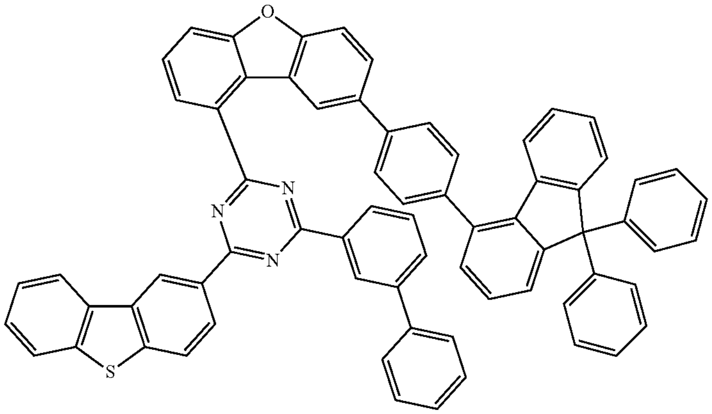 [SMILES: c1ccc(-c2cccc(-c3nc(-c4ccc5sc6ccccc6c5c4)nc(-c4cccc5oc6ccc(-c7ccc(-c8cccc9c8-c8ccccc8C9(c8ccccc8)c8ccccc8)cc7)cc6c45)n3)c2)cc1]
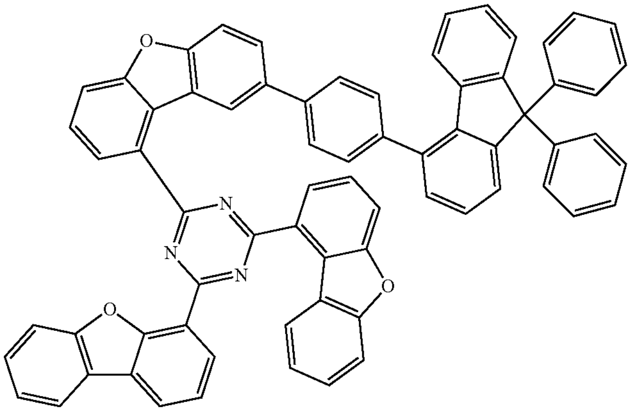 [SMILES: c1ccc(C2(c3ccccc3)c3ccccc3-c3c(-c4ccc(-c5ccc6oc7cccc(-c8nc(-c9cccc%10c9oc9ccccc9%10)nc(-c9cccc%10oc%11ccccc%11c9%10)n8)c7c6c5)cc4)cccc32)cc1]
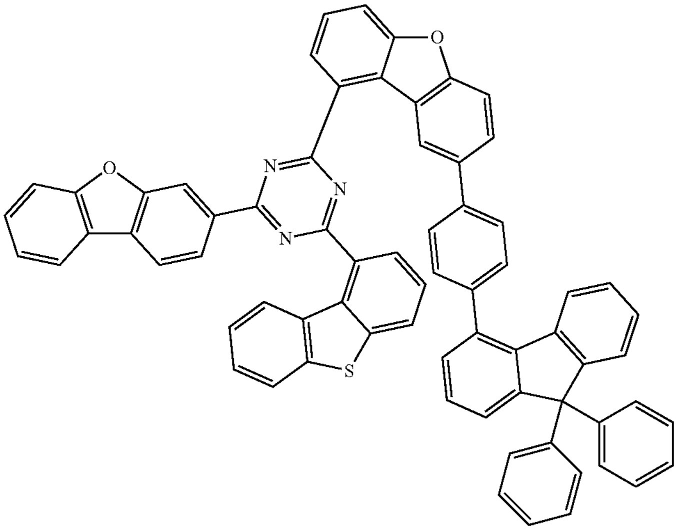 [SMILES: c1ccc(C2(c3ccccc3)c3ccccc3-c3c(-c4ccc(-c5ccc6oc7cccc(-c8nc(-c9ccc%10c(c9)oc9ccccc9%10)nc(-c9cccc%10sc%11ccccc%11c9%10)n8)c7c6c5)cc4)cccc32)cc1]

TABLE 1-continued
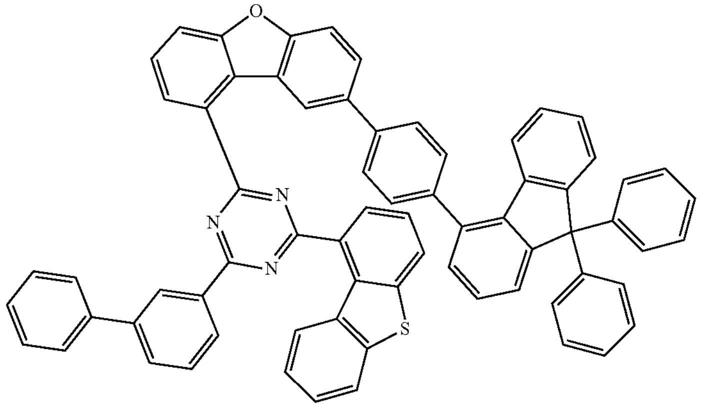 [SMILES: c1ccc(-c2cccc(-c3nc(-c4cccc5oc6ccc(-c7ccc(-c8cccc9c8-c8ccccc8C9(c8ccccc8)c8ccccc8)cc7)cc6c45)nc(-c4cccc5sc6ccccc6c45)n3)c2)cc1]
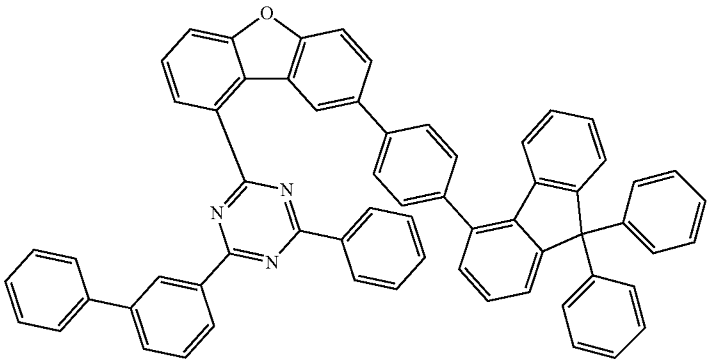 [SMILES: c1ccc(-c2cccc(-c3nc(-c4ccccc4)nc(-c4cccc5oc6ccc(-c7ccc(-c8cccc9c8-c8ccccc8C9(c8ccccc8)c8ccccc8)cc7)cc6c45)n3)c2)cc1]
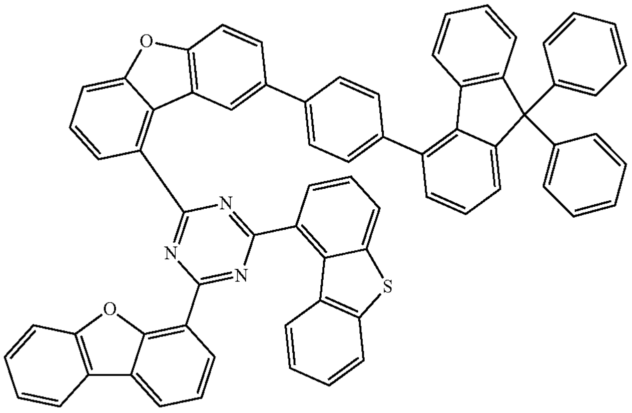 [SMILES: c1ccc(C2(c3ccccc3)c3ccccc3-c3c(-c4ccc(-c5ccc6oc7cccc(-c8nc(-c9cccc%10c9oc9ccccc9%10)nc(-c9cccc%10sc%11ccccc%11c9%10)n8)c7c6c5)cc4)cccc32)cc1]

TABLE 1-continued
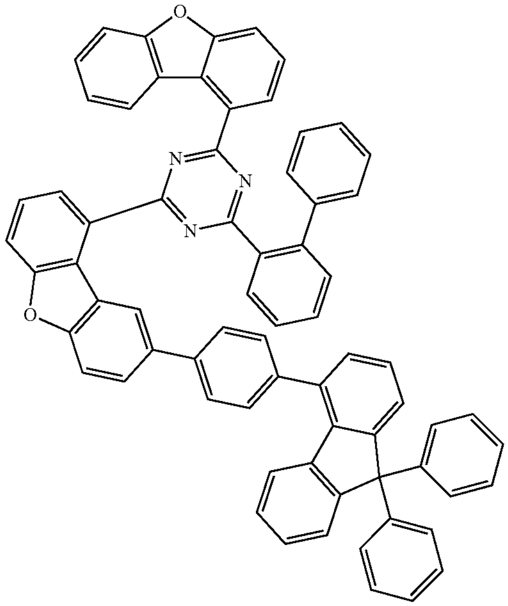 [SMILES: c1ccc(-c2ccccc2-c2nc(-c3cccc4oc5ccccc5c34)nc(-c3cccc4oc5ccc(-c6ccc(-c7cccc8c7-c7ccccc7C8(c7ccccc7)c7ccccc7)cc6)cc5c34)n2)cc1]
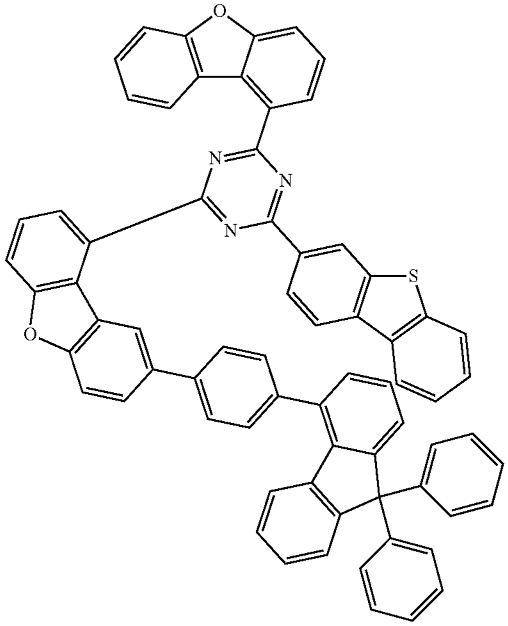 [SMILES: c1ccc(C2(c3ccccc3)c3ccccc3-c3c(-c4ccc(-c5ccc6oc7cccc(-c8nc(-c9ccc%10c(c9)sc9ccccc9%10)nc(-c9cccc%10oc%11ccccc%11c9%10)n8)c7c6c5)cc4)cccc32)cc1]

TABLE 1-continued
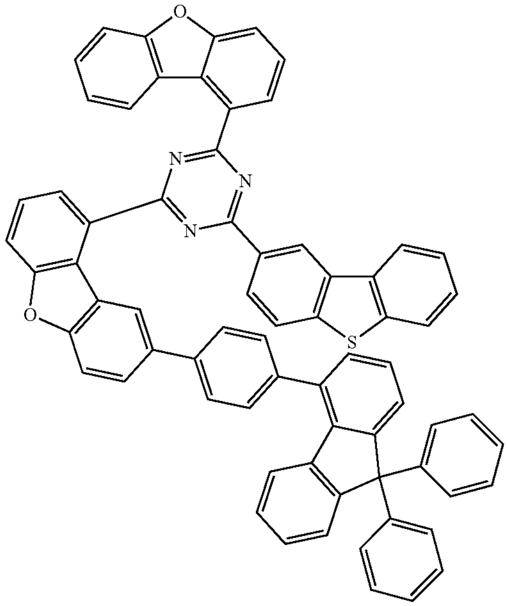
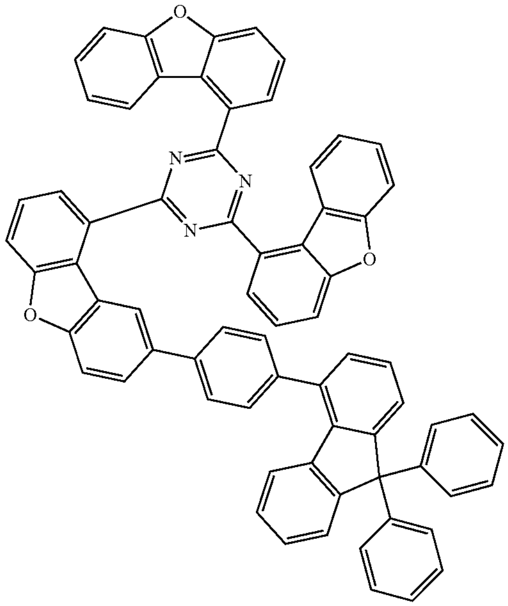 [SMILES: c1ccc(C2(c3ccccc3)c3ccccc3-c3c(-c4ccc(-c5ccc6oc7cccc(-c8nc(-c9cccc%10oc%11ccccc%11c9%10)nc(-c9cccc%10oc%11ccccc%11c9%10)n8)c7c6c5)cc4)cccc32)cc1]
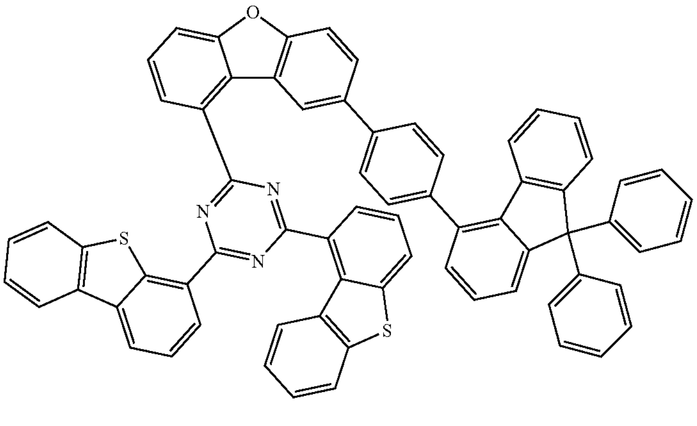 [SMILES: c1ccc(C2(c3ccccc3)c3ccccc3-c3c(-c4ccc(-c5ccc6oc7cccc(-c8nc(-c9cccc%10c9sc9ccccc9%10)nc(-c9cccc%10sc%11ccccc%11c9%10)n8)c7c6c5)cc4)cccc32)cc1]

TABLE 1-continued
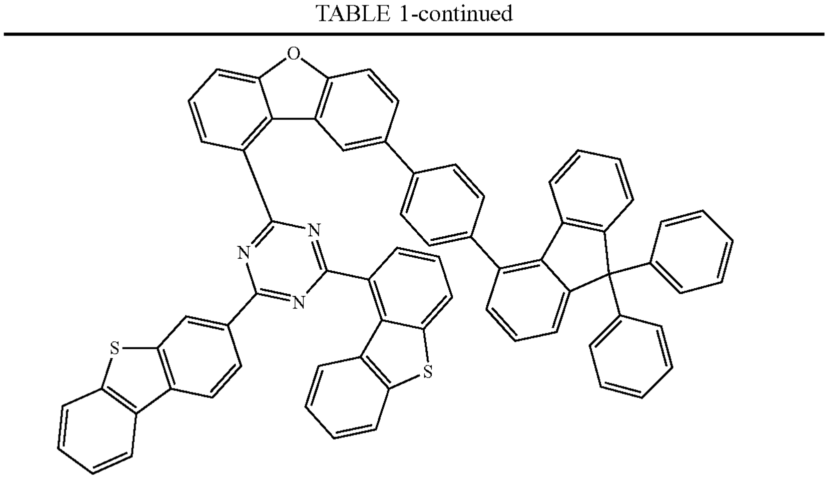
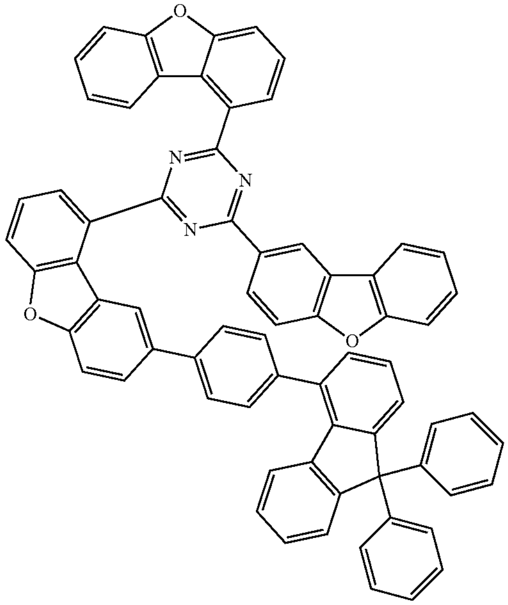 [SMILES: c1ccc(C2(c3ccccc3)c3ccccc3-c3c(-c4ccc(-c5ccc6oc7cccc(-c8nc(-c9ccc%10oc%11ccccc%11c%10c9)nc(-c9cccc%10oc%11ccccc%11c9%10)n8)c7c6c5)cc4)cccc32)cc1]
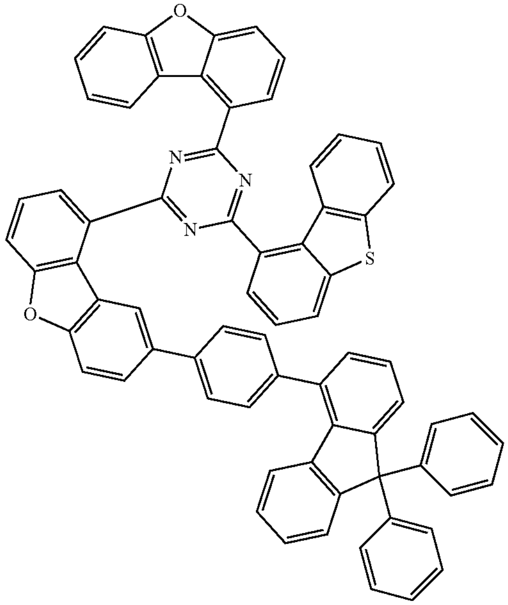

TABLE 1-continued
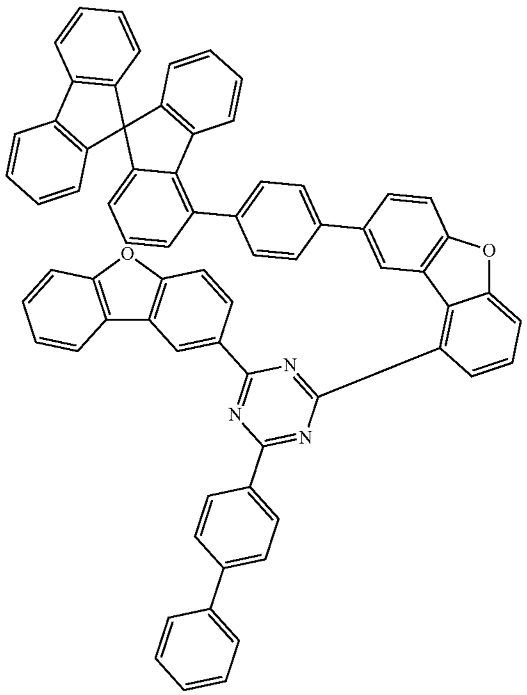 [SMILES: c1ccc(-c2ccc(-c3nc(-c4ccc5oc6ccccc6c5c4)nc(-c4cccc5oc6ccc(-c7ccc(-c8cccc9c8-c8ccccc8C98c9ccccc9-c9ccccc98)cc7)cc6c45)n3)cc2)cc1]
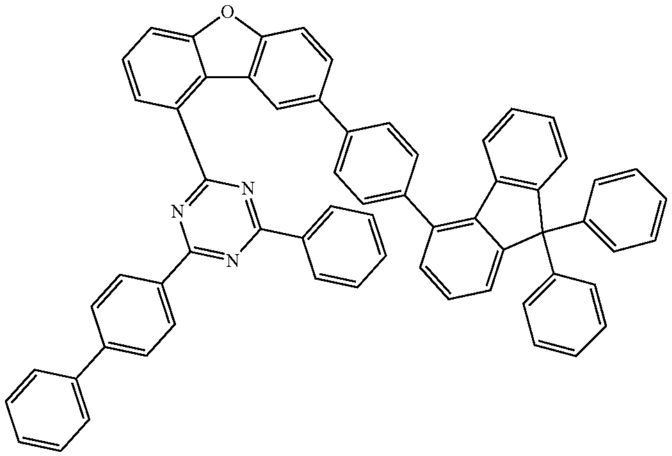 [SMILES: c1ccc(-c2ccc(-c3nc(-c4ccccc4)nc(-c4cccc5oc6ccc(-c7ccc(-c8cccc9c8-c8ccccc8C9(c8ccccc8)c8ccccc8)cc7)cc6c45)n3)cc2)cc1]
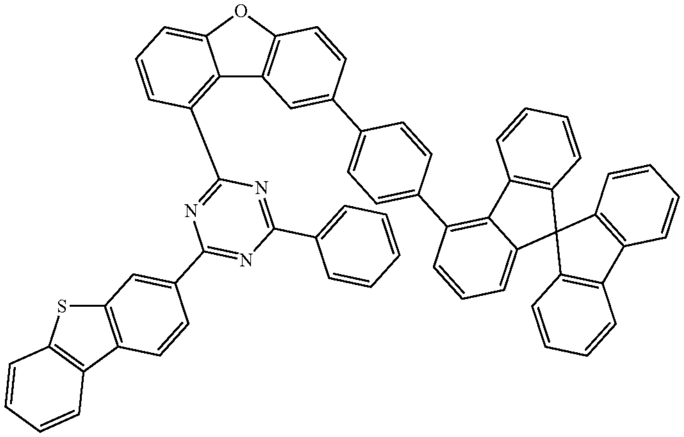 [SMILES: c1ccc(-c2nc(-c3ccc4c(c3)sc3ccccc34)nc(-c3cccc4oc5ccc(-c6ccc(-c7cccc8c7-c7ccccc7C87c8ccccc8-c8ccccc87)cc6)cc5c34)n2)cc1]

TABLE 1-continued
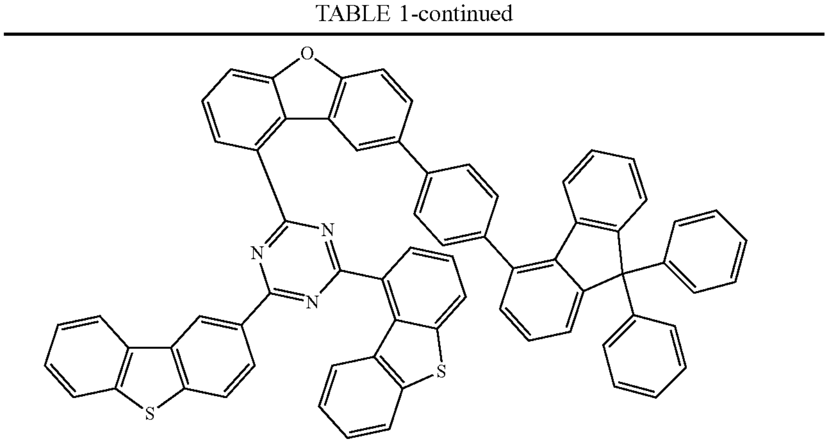
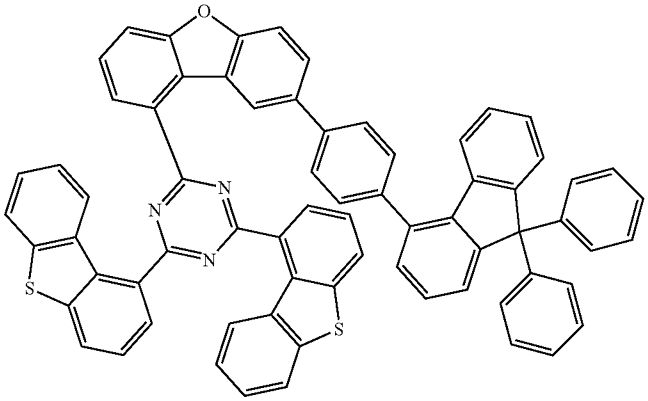 [SMILES: c1ccc(C2(c3ccccc3)c3ccccc3-c3c(-c4ccc(-c5ccc6oc7cccc(-c8nc(-c9cccc%10sc%11ccccc%11c9%10)nc(-c9cccc%10sc%11ccccc%11c9%10)n8)c7c6c5)cc4)cccc32)cc1]
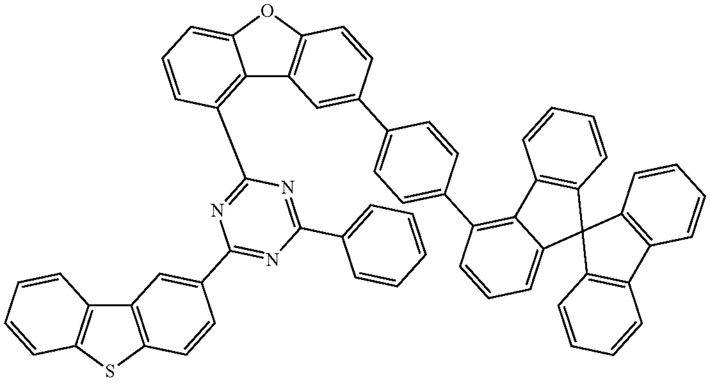 [SMILES: c1ccc(-c2nc(-c3ccc4sc5ccccc5c4c3)nc(-c3cccc4oc5ccc(-c6ccc(-c7cccc8c7-c7ccccc7C87c8ccccc8-c8ccccc87)cc6)cc5c34)n2)cc1]
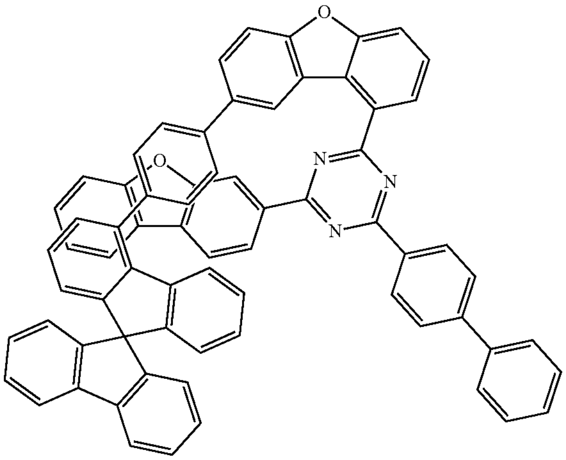 [SMILES: c1ccc(-c2ccc(-c3nc(-c4ccc5c(c4)oc4ccccc45)nc(-c4cccc5oc6ccc(-c7ccc(-c8cccc9c8-c8ccccc8C98c9ccccc9-c9ccccc98)cc7)cc6c45)n3)cc2)cc1]

TABLE 1-continued
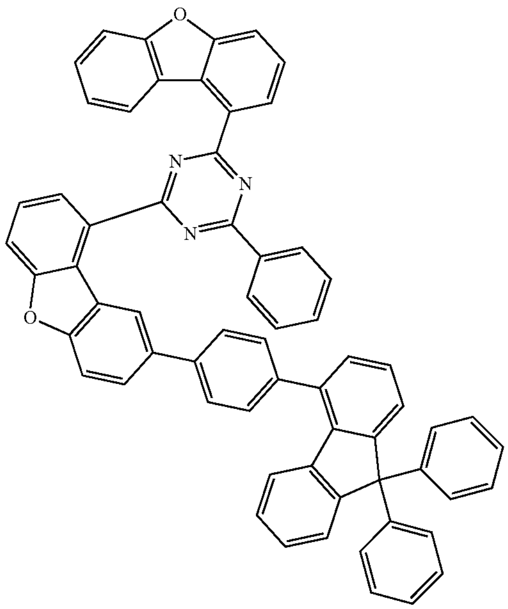 [SMILES: c1ccc(-c2nc(-c3cccc4oc5ccccc5c34)nc(-c3cccc4oc5ccc(-c6ccc(-c7cccc8c7-c7ccccc7C8(c7ccccc7)c7ccccc7)cc6)cc5c34)n2)cc1]
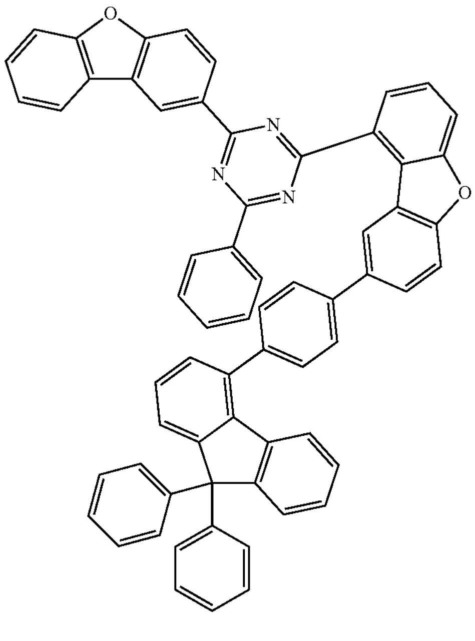 [SMILES: c1ccc(-c2nc(-c3ccc4oc5ccccc5c4c3)nc(-c3cccc4oc5ccc(-c6ccc(-c7cccc8c7-c7ccccc7C8(c7ccccc7)c7ccccc7)cc6)cc5c34)n2)cc1]

TABLE 1-continued
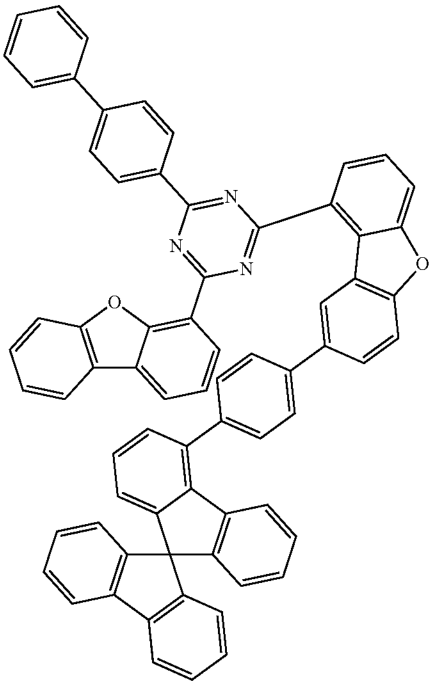 [SMILES: c1ccc(-c2ccc(-c3nc(-c4cccc5c4oc4ccccc45)nc(-c4cccc5oc6ccc(-c7ccc(-c8cccc9c8-c8ccccc8C98c9ccccc9-c9ccccc98)cc7)cc6c45)n3)cc2)cc1]
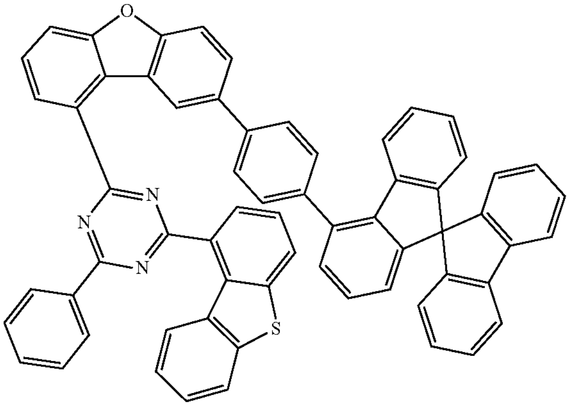 [SMILES: c1ccc(-c2nc(-c3cccc4oc5ccc(-c6ccc(-c7cccc8c7-c7ccccc7C87c8ccccc8-c8ccccc87)cc6)cc5c34)nc(-c3cccc4sc5ccccc5c34)n2)cc1]
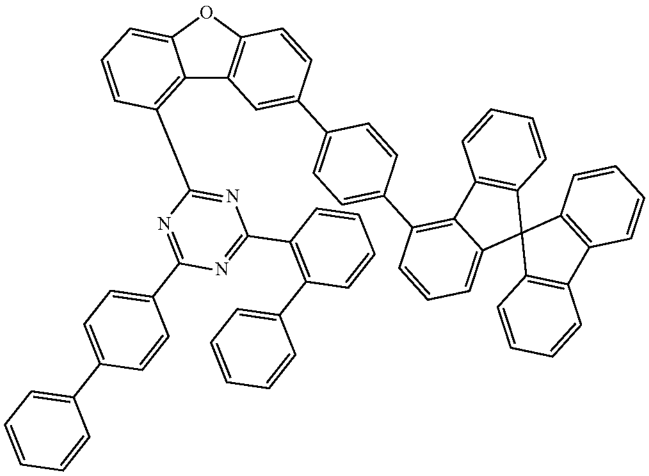 [SMILES: c1ccc(-c2ccc(-c3nc(-c4ccccc4-c4ccccc4)nc(-c4cccc5oc6ccc(-c7ccc(-c8cccc9c8-c8ccccc8C98c9ccccc9-c9ccccc98)cc7)cc6c45)n3)cc2)cc1]

TABLE 1-continued
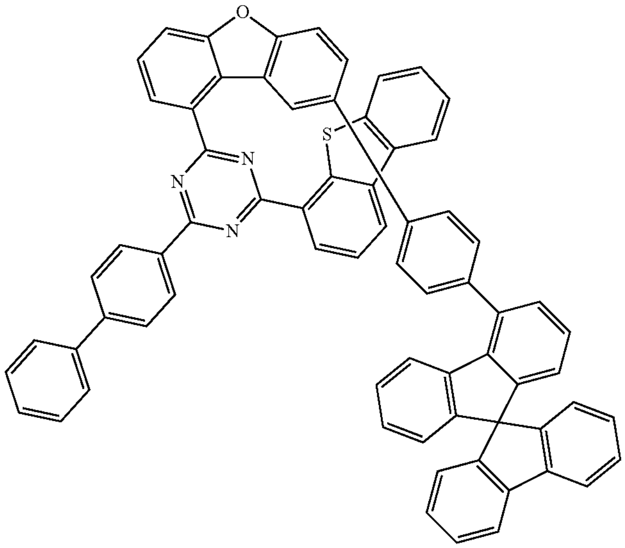 [SMILES: c1ccc(-c2ccc(-c3nc(-c4cccc5c4sc4ccccc45)nc(-c4cccc5oc6ccc(-c7ccc(-c8cccc9c8-c8ccccc8C98c9ccccc9-c9ccccc98)cc7)cc6c45)n3)cc2)cc1]
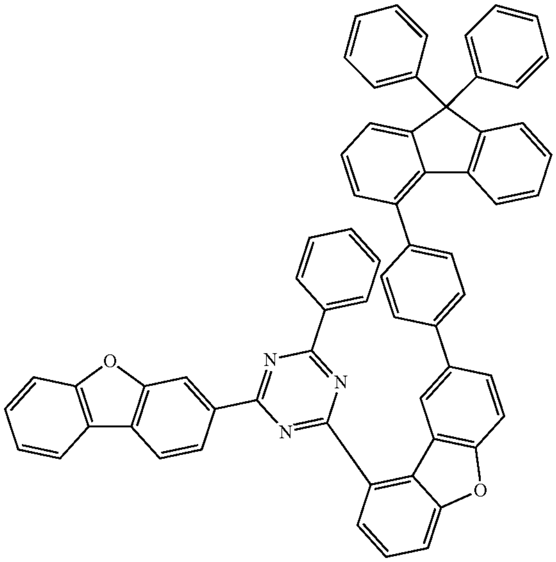 [SMILES: c1ccc(-c2nc(-c3ccc4c(c3)oc3ccccc34)nc(-c3cccc4oc5ccc(-c6ccc(-c7cccc8c7-c7ccccc7C8(c7ccccc7)c7ccccc7)cc6)cc5c34)n2)cc1]
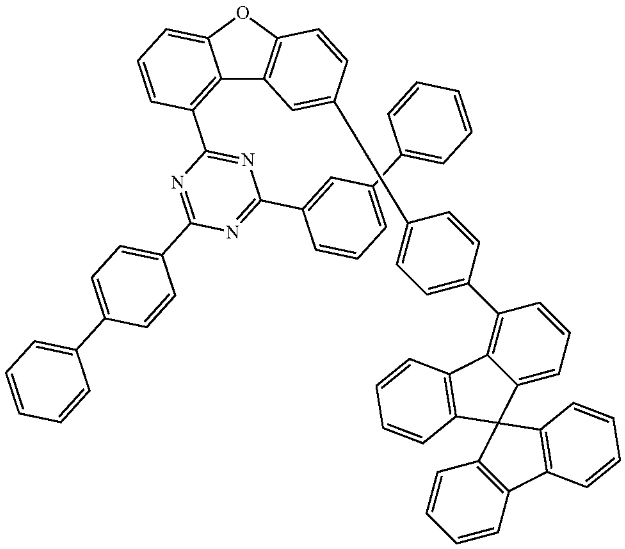 [SMILES: c1ccc(-c2ccc(-c3nc(-c4cccc(-c5ccccc5)c4)nc(-c4cccc5oc6ccc(-c7ccc(-c8cccc9c8-c8ccccc8C98c9ccccc9-c9ccccc98)cc7)cc6c45)n3)cc2)cc1]

TABLE 1-continued
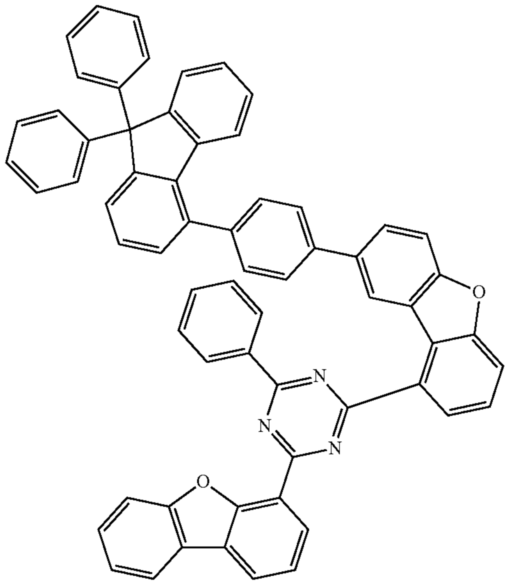 [SMILES: c1ccc(-c2nc(-c3cccc4c3oc3ccccc34)nc(-c3cccc4oc5ccc(-c6ccc(-c7cccc8c7-c7ccccc7C8(c7ccccc7)c7ccccc7)cc6)cc5c34)n2)cc1]
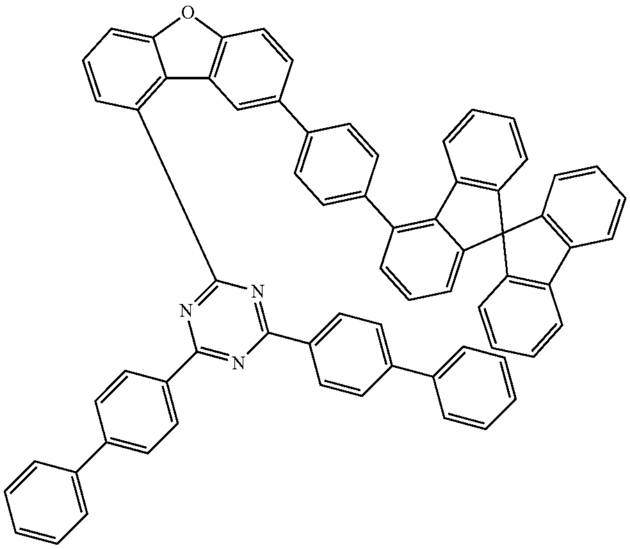 [SMILES: c1ccc(-c2ccc(-c3nc(-c4ccc(-c5ccccc5)cc4)nc(-c4cccc5oc6ccc(-c7ccc(-c8cccc9c8-c8ccccc8C98c9ccccc9-c9ccccc98)cc7)cc6c45)n3)cc2)cc1]
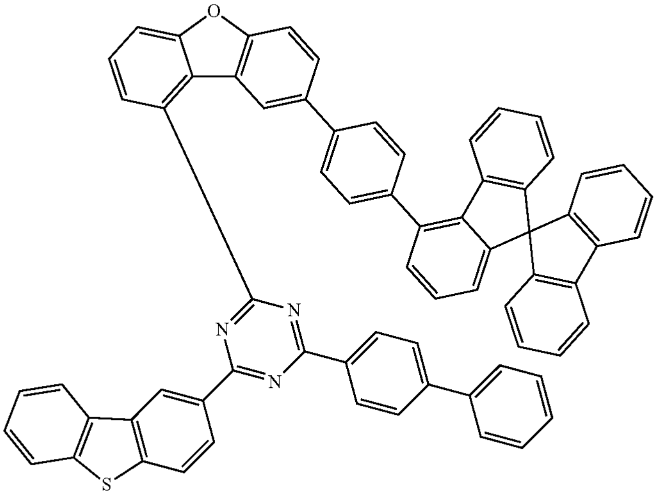 [SMILES: c1ccc(-c2ccc(-c3nc(-c4ccc5sc6ccccc6c5c4)nc(-c4cccc5oc6ccc(-c7ccc(-c8cccc9c8-c8ccccc8C98c9ccccc9-c9ccccc98)cc7)cc6c45)n3)cc2)cc1]

TABLE 1-continued
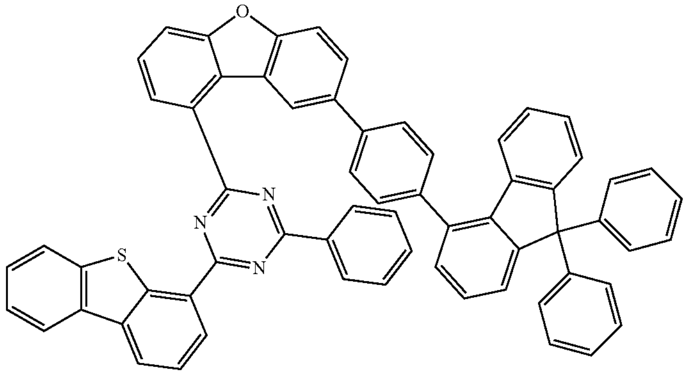 [SMILES: c1ccc(-c2nc(-c3cccc4c3sc3ccccc34)nc(-c3cccc4oc5ccc(-c6ccc(-c7cccc8c7-c7ccccc7C8(c7ccccc7)c7ccccc7)cc6)cc5c34)n2)cc1]
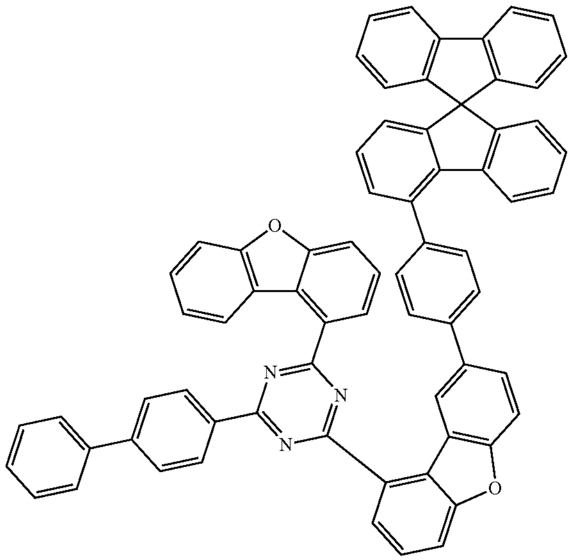 [SMILES: c1ccc(-c2ccc(-c3nc(-c4cccc5oc6ccccc6c45)nc(-c4cccc5oc6ccc(-c7ccc(-c8cccc9c8-c8ccccc8C98c9ccccc9-c9ccccc98)cc7)cc6c45)n3)cc2)cc1]
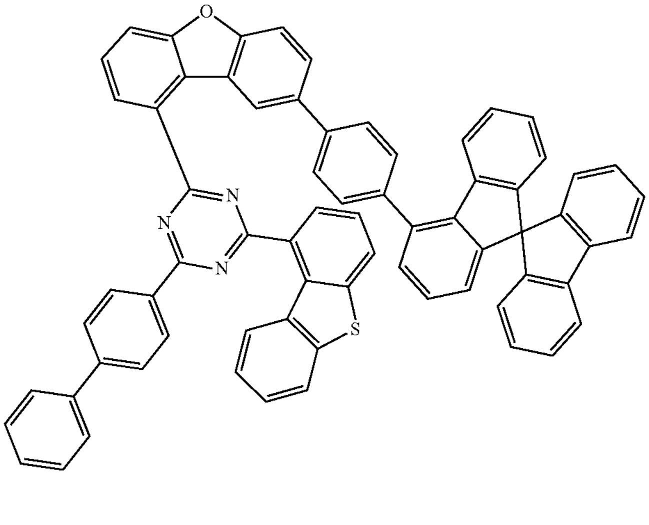 [SMILES: c1ccc(-c2ccc(-c3nc(-c4cccc5oc6ccc(-c7ccc(-c8cccc9c8-c8ccccc8C98c9ccccc9-c9ccccc98)cc7)cc6c45)nc(-c4cccc5sc6ccccc6c45)n3)cc2)cc1]

TABLE 1-continued
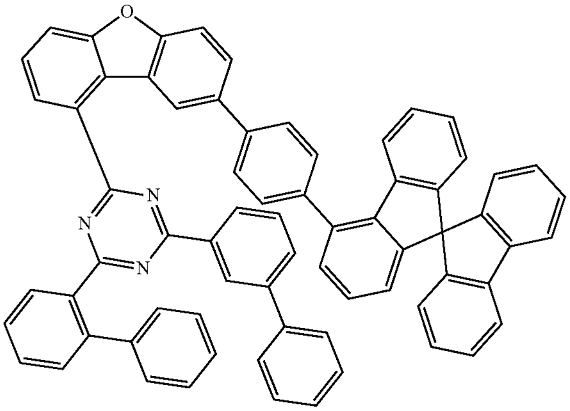 [SMILES: c1ccc(-c2cccc(-c3nc(-c4ccccc4-c4ccccc4)nc(-c4cccc5oc6ccc(-c7ccc(-c8cccc9c8-c8ccccc8C98c9ccccc9-c9ccccc98)cc7)cc6c45)n3)c2)cc1]
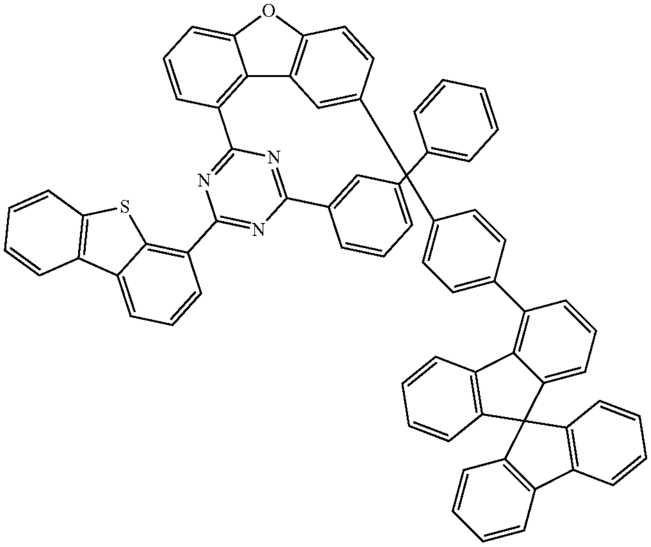 [SMILES: c1ccc(-c2cccc(-c3nc(-c4cccc5c4sc4ccccc45)nc(-c4cccc5oc6ccc(-c7ccc(-c8cccc9c8-c8ccccc8C98c9ccccc9-c9ccccc98)cc7)cc6c45)n3)c2)cc1]
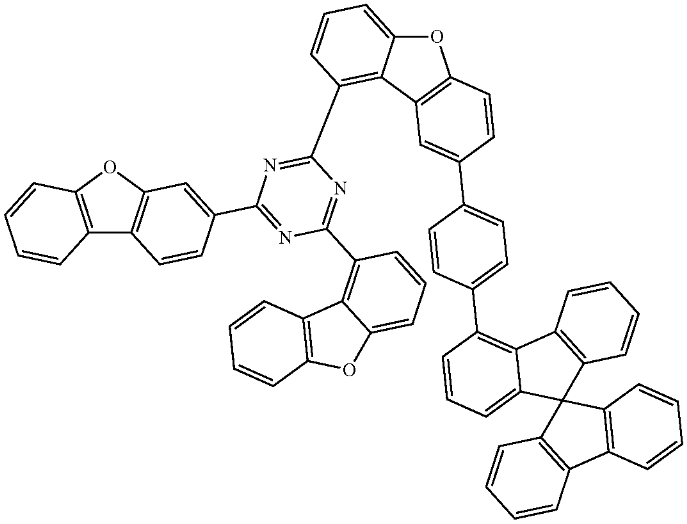 [SMILES: c1ccc2c(c1)-c1ccccc1C21c2ccccc2-c2c(-c3ccc(-c4ccc5oc6cccc(-c7nc(-c8ccc9c(c8)oc8ccccc89)nc(-c8cccc9oc%10ccccc%10c89)n7)c6c5c4)cc3)cccc21]

TABLE 1-continued
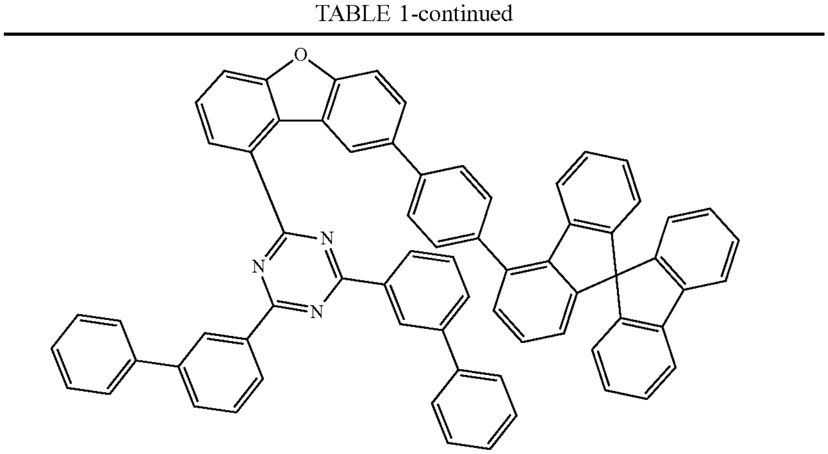
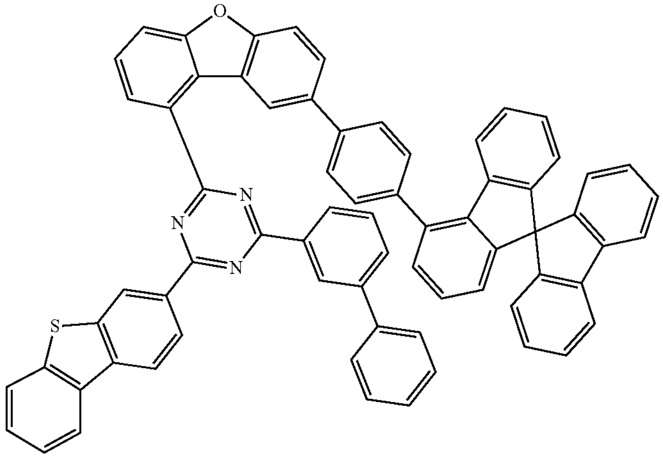 [SMILES: c1ccc(-c2cccc(-c3nc(-c4ccc5c(c4)sc4ccccc45)nc(-c4cccc5oc6ccc(-c7ccc(-c8cccc9c8-c8ccccc8C98c9ccccc9-c9ccccc98)cc7)cc6c45)n3)c2)cc1]
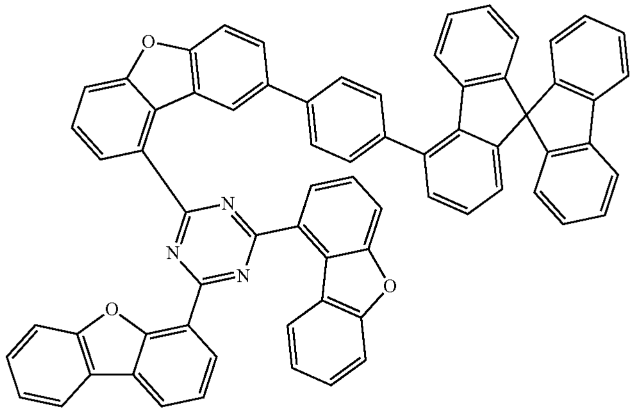 [SMILES: c1ccc2c(c1)-c1ccccc1C21c2ccccc2-c2c(-c3ccc(-c4ccc5oc6cccc(-c7nc(-c8cccc9c8oc8ccccc89)nc(-c8cccc9oc%10ccccc%10c89)n7)c6c5c4)cc3)cccc21]

TABLE 1-continued
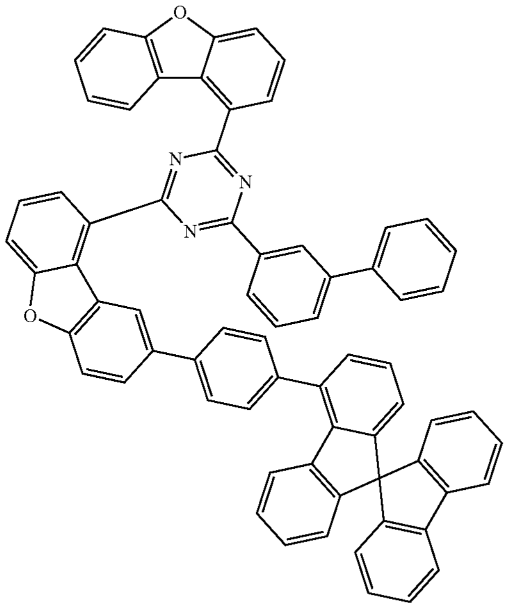 [SMILES: c1ccc(-c2cccc(-c3nc(-c4cccc5oc6ccccc6c45)nc(-c4cccc5oc6ccc(-c7ccc(-c8cccc9c8-c8ccccc8C98c9ccccc9-c9ccccc98)cc7)cc6c45)n3)c2)cc1]
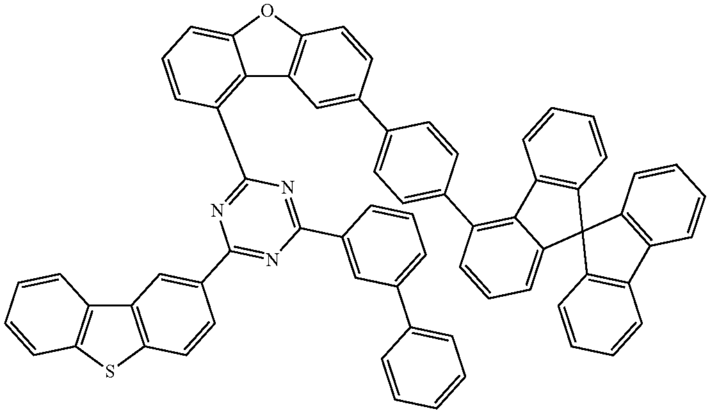 [SMILES: c1ccc(-c2cccc(-c3nc(-c4ccc5sc6ccccc6c5c4)nc(-c4cccc5oc6ccc(-c7ccc(-c8cccc9c8-c8ccccc8C98c9ccccc9-c9ccccc98)cc7)cc6c45)n3)c2)cc1]
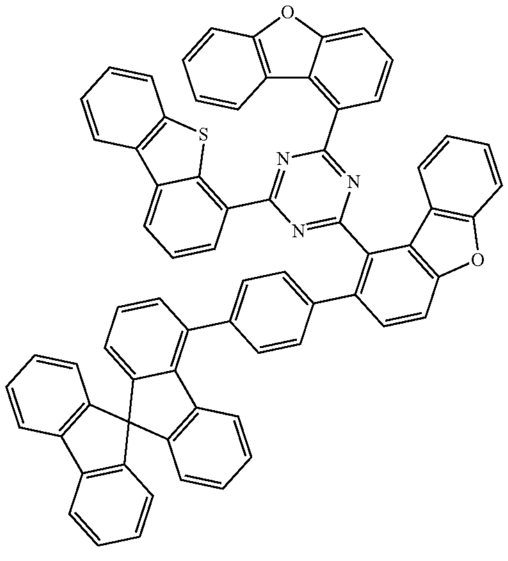 [SMILES: c1ccc2c(c1)-c1ccccc1C21c2ccccc2-c2c(-c3ccc(-c4ccc5oc6ccccc6c5c4-c4nc(-c5cccc6c5sc5ccccc56)nc(-c5cccc6oc7ccccc7c56)n4)cc3)cccc21]

TABLE 1-continued
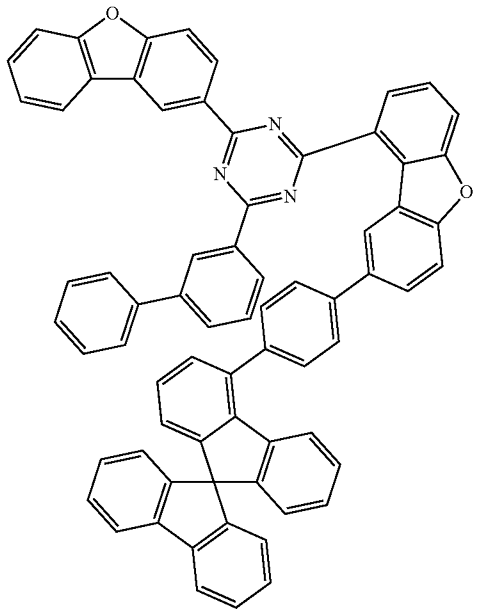 [SMILES: c1ccc(-c2cccc(-c3nc(-c4ccc5oc6ccccc6c5c4)nc(-c4cccc5oc6ccc(-c7ccc(-c8cccc9c8-c8ccccc8C98c9ccccc9-c9ccccc98)cc7)cc6c45)n3)c2)cc1]
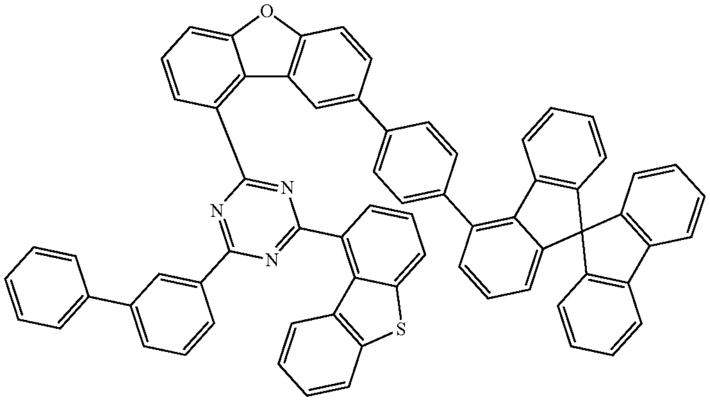 [SMILES: c1ccc(-c2cccc(-c3nc(-c4cccc5oc6ccc(-c7ccc(-c8cccc9c8-c8ccccc8C98c9ccccc9-c9ccccc98)cc7)cc6c45)nc(-c4cccc5sc6ccccc6c45)n3)c2)cc1]
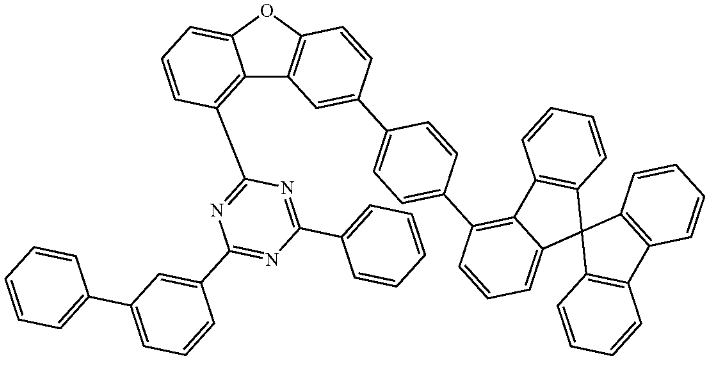 [SMILES: c1ccc(-c2cccc(-c3nc(-c4ccccc4)nc(-c4cccc5oc6ccc(-c7ccc(-c8cccc9c8-c8ccccc8C98c9ccccc9-c9ccccc98)cc7)cc6c45)n3)c2)cc1]

TABLE 1-continued
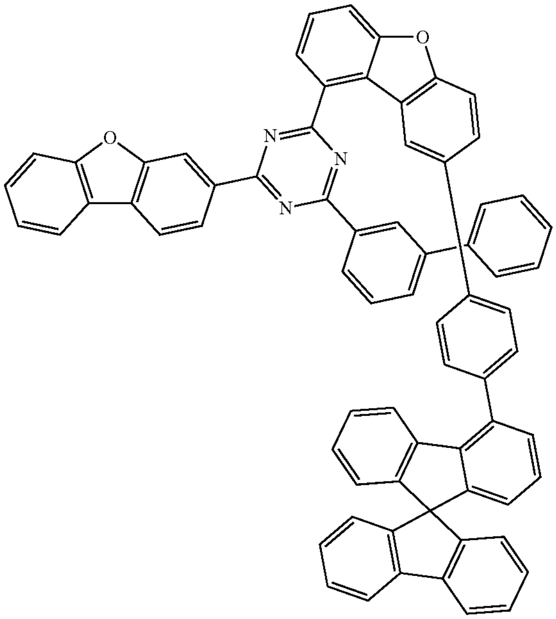 [SMILES: c1ccc(-c2cccc(-c3nc(-c4ccc5c(c4)oc4ccccc45)nc(-c4cccc5oc6ccc(-c7ccc(-c8cccc9c8-c8ccccc8C98c9ccccc9-c9ccccc98)cc7)cc6c45)n3)c2)cc1]
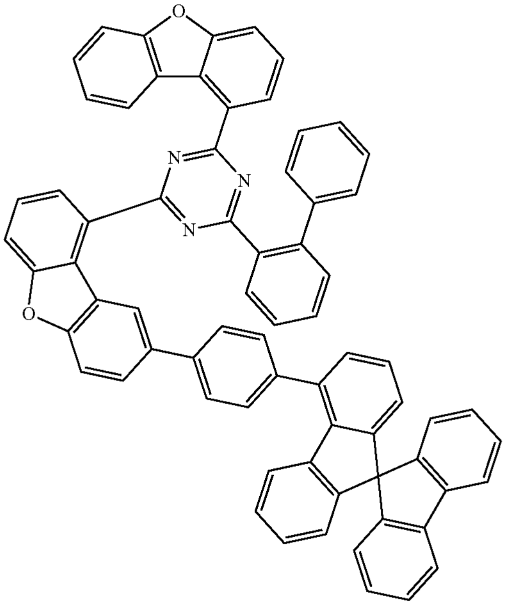 [SMILES: c1ccc(-c2ccccc2-c2nc(-c3cccc4oc5ccccc5c34)nc(-c3cccc4oc5ccc(-c6ccc(-c7cccc8c7-c7ccccc7C87c8ccccc8-c8ccccc87)cc6)cc5c34)n2)cc1]

TABLE 1-continued
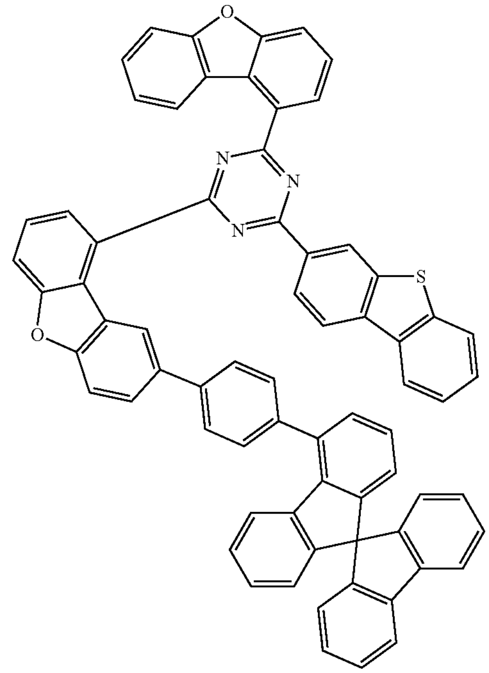 [SMILES: c1ccc2c(c1)-c1ccccc1C21c2ccccc2-c2c(-c3ccc(-c4ccc5oc6cccc(-c7nc(-c8ccc9c(c8)sc8ccccc89)nc(-c8cccc9oc%10ccccc%10c89)n7)c6c5c4)cc3)cccc21]
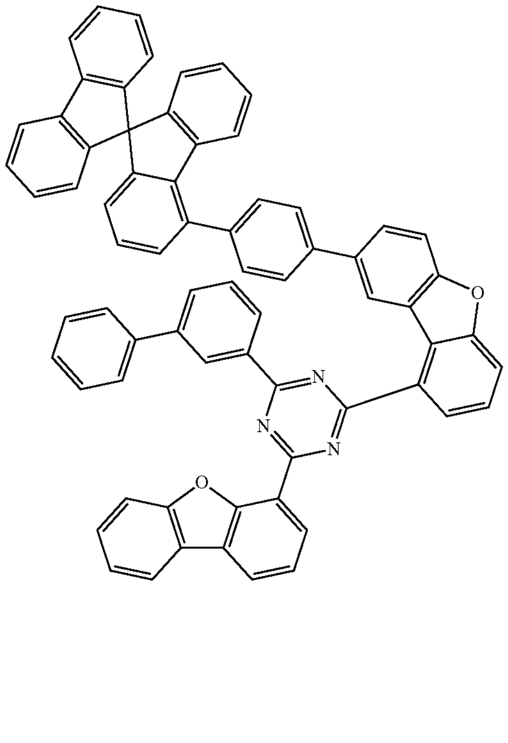 [SMILES: c1ccc(-c2cccc(-c3nc(-c4cccc5c4oc4ccccc45)nc(-c4cccc5oc6ccc(-c7ccc(-c8cccc9c8-c8ccccc8C98c9ccccc9-c9ccccc98)cc7)cc6c45)n3)c2)cc1]

TABLE 1-continued
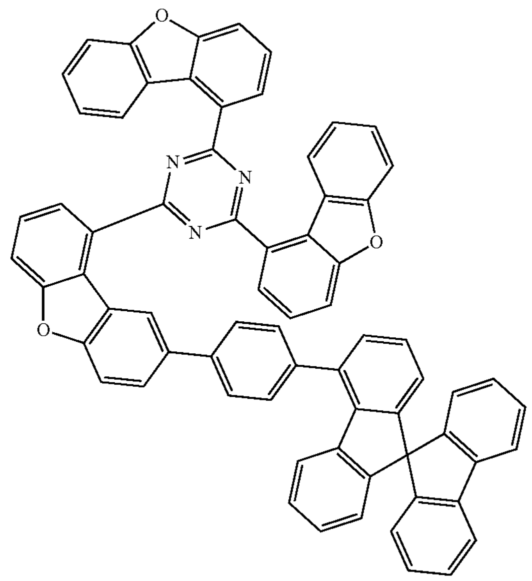 [SMILES: c1ccc2c(c1)-c1ccccc1C21c2ccccc2-c2c(-c3ccc(-c4ccc5oc6cccc(-c7nc(-c8cccc9oc%10ccccc%10c89)nc(-c8cccc9oc%10ccccc%10c89)n7)c6c5c4)cc3)cccc21]
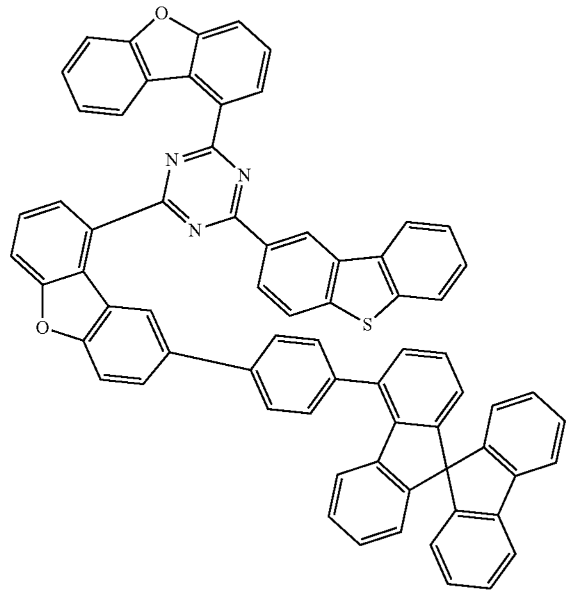 [SMILES: c1ccc2c(c1)-c1ccccc1C21c2ccccc2-c2c(-c3ccc(-c4ccc5oc6cccc(-c7nc(-c8ccc9sc%10ccccc%10c9c8)nc(-c8cccc9oc%10ccccc%10c89)n7)c6c5c4)cc3)cccc21]

TABLE 1-continued
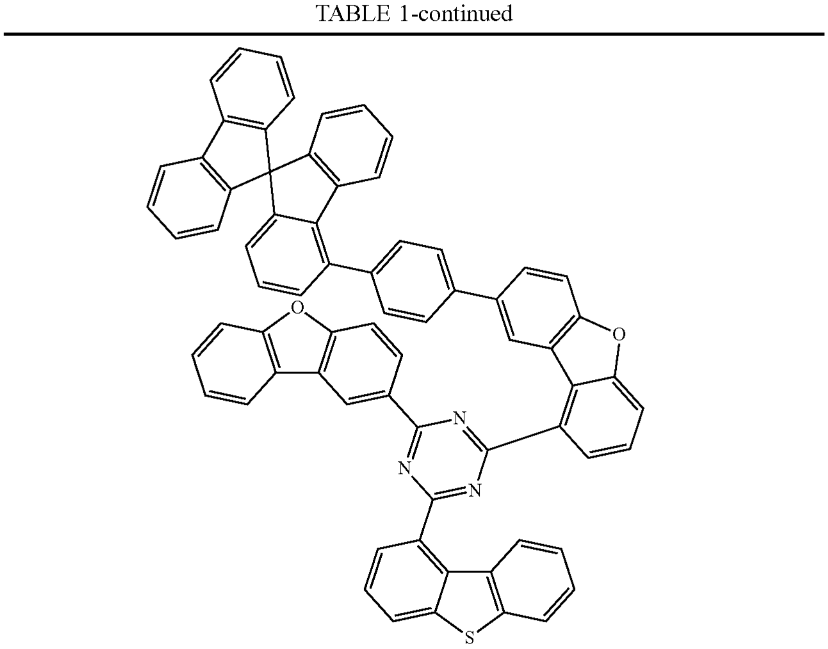
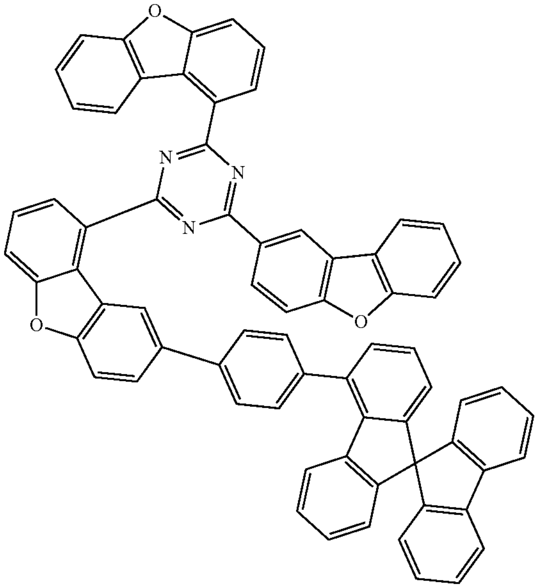 [SMILES: c1ccc2c(c1)-c1ccccc1C21c2ccccc2-c2c(-c3ccc(-c4ccc5oc6cccc(-c7nc(-c8ccc9oc%10ccccc%10c9c8)nc(-c8cccc9oc%10ccccc%10c89)n7)c6c5c4)cc3)cccc21]

TABLE 1-continued
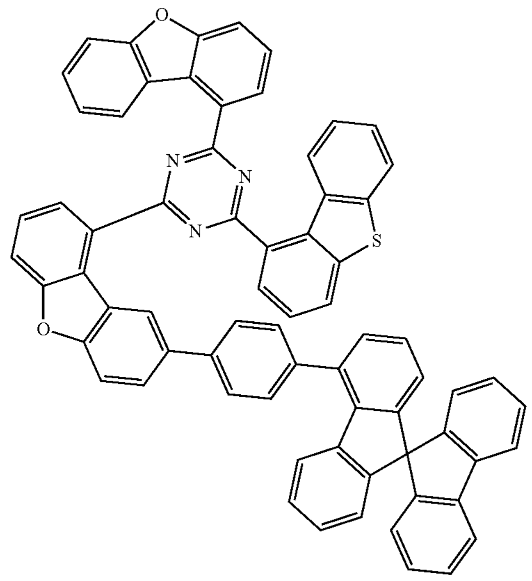 [SMILES: c1ccc2c(c1)-c1ccccc1C21c2ccccc2-c2c(-c3ccc(-c4ccc5oc6cccc(-c7nc(-c8cccc9oc%10ccccc%10c89)nc(-c8cccc9sc%10ccccc%10c89)n7)c6c5c4)cc3)cccc21]
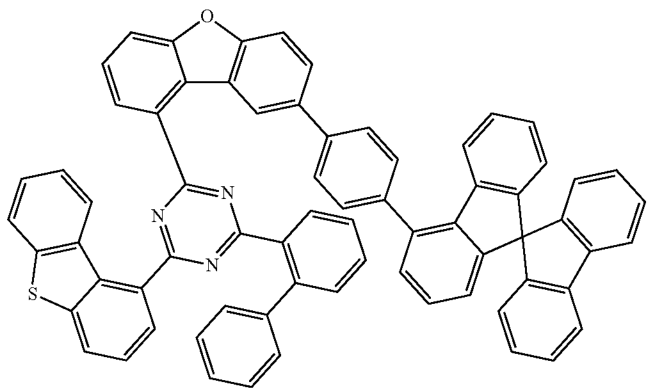 [SMILES: c1ccc(-c2ccccc2-c2nc(-c3cccc4oc5ccc(-c6ccc(-c7cccc8c7-c7ccccc7C87c8ccccc8-c8ccccc87)cc6)cc5c34)nc(-c3cccc4sc5ccccc5c34)n2)cc1]
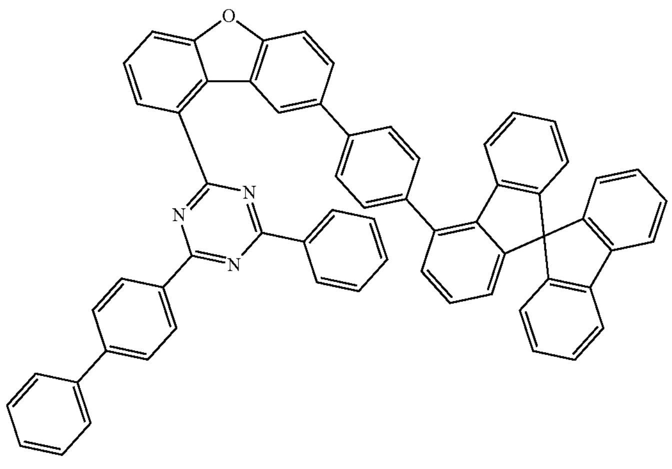 [SMILES: c1ccc(-c2ccc(-c3nc(-c4ccccc4)nc(-c4cccc5oc6ccc(-c7ccc(-c8cccc9c8-c8ccccc8C98c9ccccc9-c9ccccc98)cc7)cc6c45)n3)cc2)cc1]

TABLE 1-continued
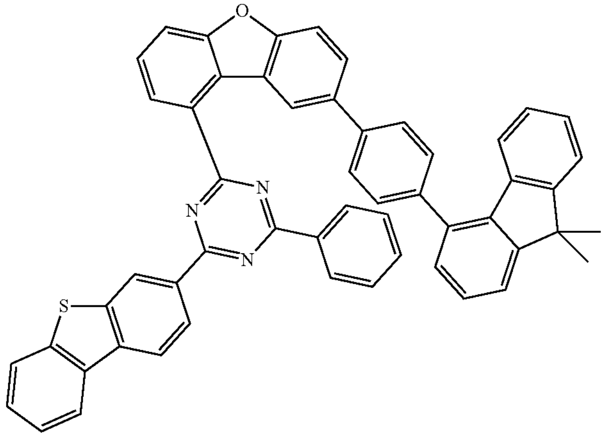 [SMILES: CC1(C)c2ccccc2-c2c(-c3ccc(-c4ccc5oc6cccc(-c7nc(-c8ccccc8)nc(-c8ccc9c(c8)sc8ccccc89)n7)c6c5c4)cc3)cccc21]
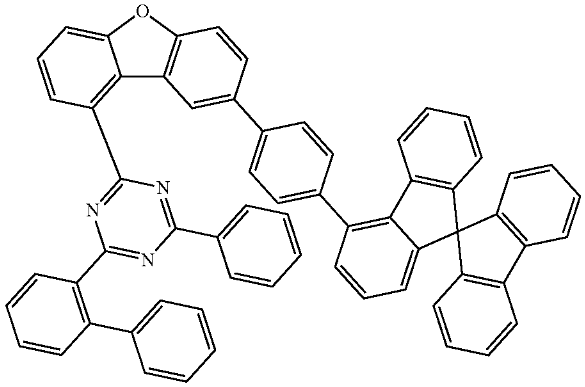 [SMILES: c1ccc(-c2nc(-c3ccccc3-c3ccccc3)nc(-c3cccc4oc5ccc(-c6ccc(-c7cccc8c7-c7ccccc7C87c8ccccc8-c8ccccc87)cc6)cc5c34)n2)cc1]
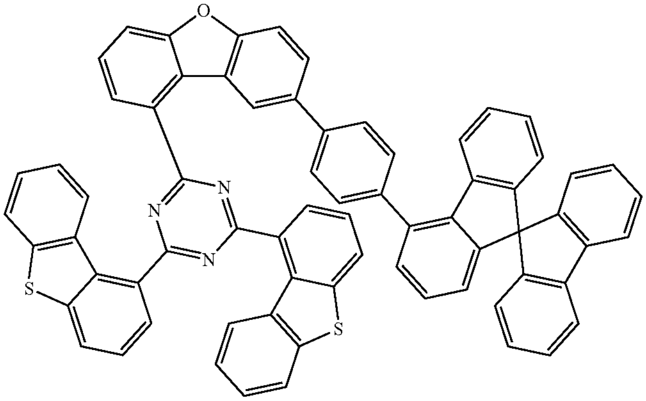 [SMILES: c1ccc2c(c1)-c1ccccc1C21c2ccccc2-c2c(-c3ccc(-c4ccc5oc6cccc(-c7nc(-c8cccc9sc%10ccccc%10c89)nc(-c8cccc9sc%10ccccc%10c89)n7)c6c5c4)cc3)cccc21]
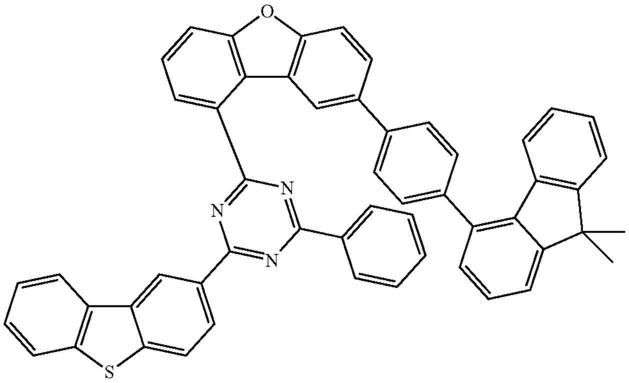 [SMILES: CC1(C)c2ccccc2-c2c(-c3ccc(-c4ccc5oc6cccc(-c7nc(-c8ccccc8)nc(-c8ccc9sc%10ccccc%10c9c8)n7)c6c5c4)cc3)cccc21]

TABLE 1-continued
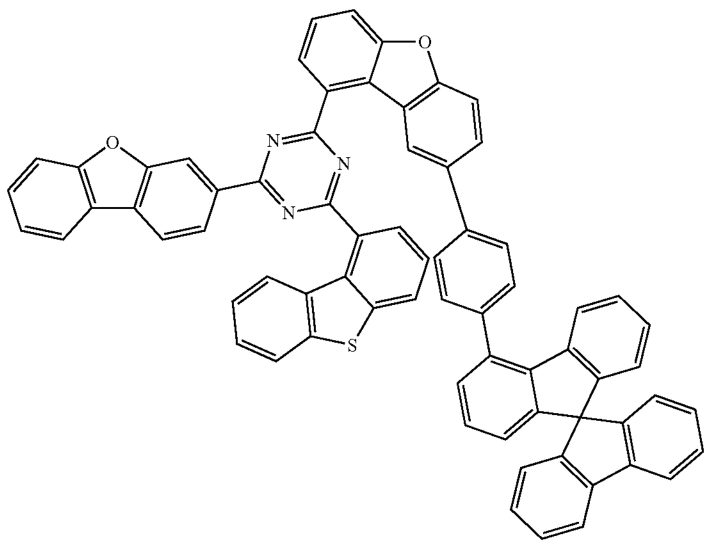 [SMILES: c1ccc2c(c1)-c1ccccc1C21c2ccccc2-c2c(-c3ccc(-c4ccc5oc6cccc(-c7nc(-c8ccc9c(c8)oc8ccccc89)nc(-c8cccc9sc%10ccccc%10c89)n7)c6c5c4)cc3)cccc21]
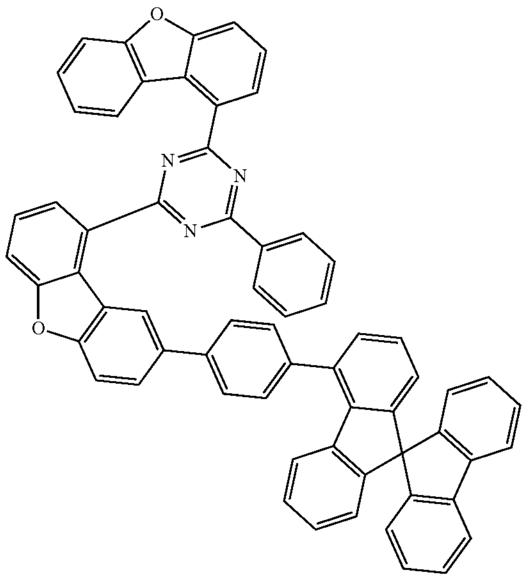 [SMILES: c1ccc(-c2nc(-c3cccc4oc5ccccc5c34)nc(-c3cccc4oc5ccc(-c6ccc(-c7cccc8c7-c7ccccc7C87c8ccccc8-c8ccccc87)cc6)cc5c34)n2)cc1]

TABLE 1-continued
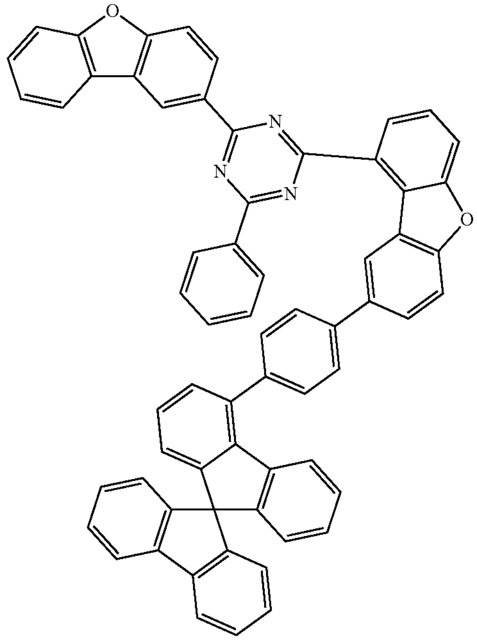 [SMILES: c1ccc(-c2nc(-c3ccc4oc5ccccc5c4c3)nc(-c3cccc4oc5ccc(-c6ccc(-c7cccc8c7-c7ccccc7C87c8ccccc8-c8ccccc87)cc6)cc5c34)n2)cc1]
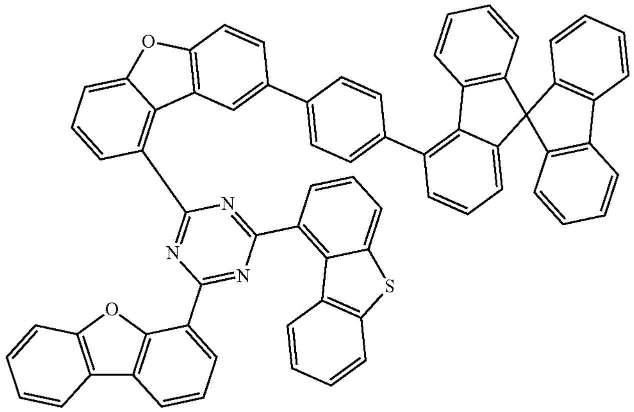 [SMILES: c1ccc2c(c1)-c1ccccc1C21c2ccccc2-c2c(-c3ccc(-c4ccc5oc6cccc(-c7nc(-c8cccc9c8oc8ccccc89)nc(-c8cccc9sc%10ccccc%10c89)n7)c6c5c4)cc3)cccc21]
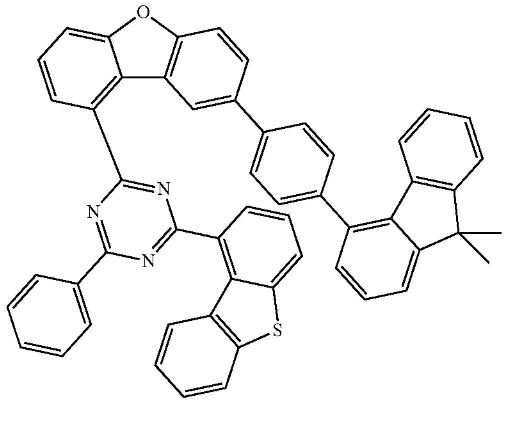 [SMILES: CC1(C)c2ccccc2-c2c(-c3ccc(-c4ccc5oc6cccc(-c7nc(-c8ccccc8)nc(-c8cccc9sc%10ccccc%10c89)n7)c6c5c4)cc3)cccc21]

TABLE 1-continued
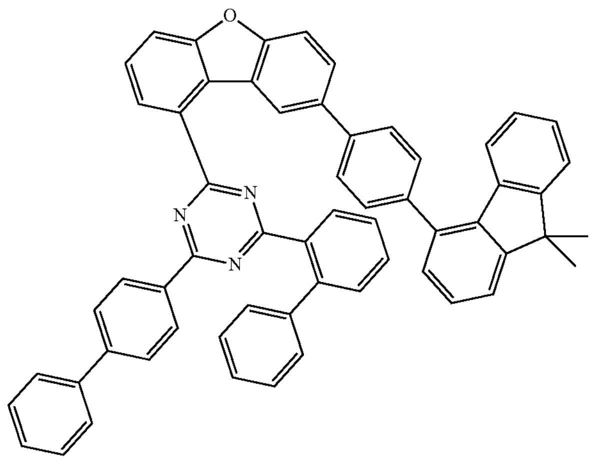 [SMILES: CC1(C)c2ccccc2-c2c(-c3ccc(-c4ccc5oc6cccc(-c7nc(-c8ccc(-c9ccccc9)cc8)nc(-c8ccccc8-c8ccccc8)n7)c6c5c4)cc3)cccc21]
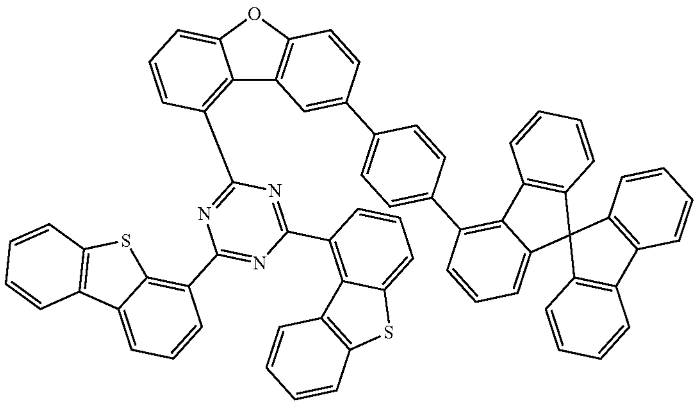 [SMILES: c1ccc2c(c1)-c1ccccc1C21c2ccccc2-c2c(-c3ccc(-c4ccc5oc6cccc(-c7nc(-c8cccc9c8sc8ccccc89)nc(-c8cccc9sc%10ccccc%10c89)n7)c6c5c4)cc3)cccc21]
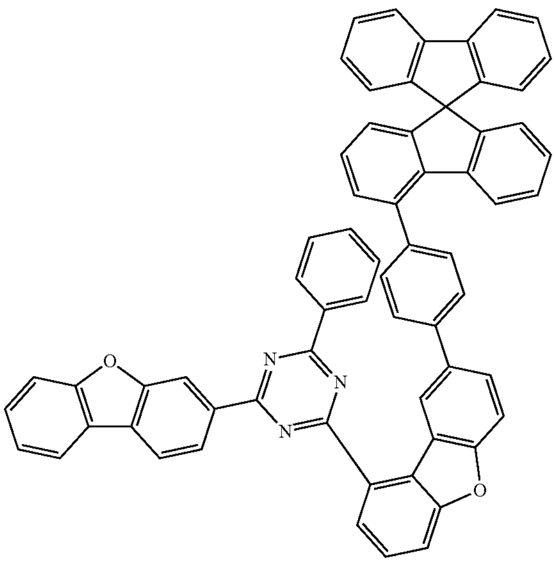 [SMILES: c1ccc(-c2nc(-c3ccc4c(c3)oc3ccccc34)nc(-c3cccc4oc5ccc(-c6ccc(-c7cccc8c7-c7ccccc7C87c8ccccc8-c8ccccc87)cc6)cc5c34)n2)cc1]

TABLE 1-continued
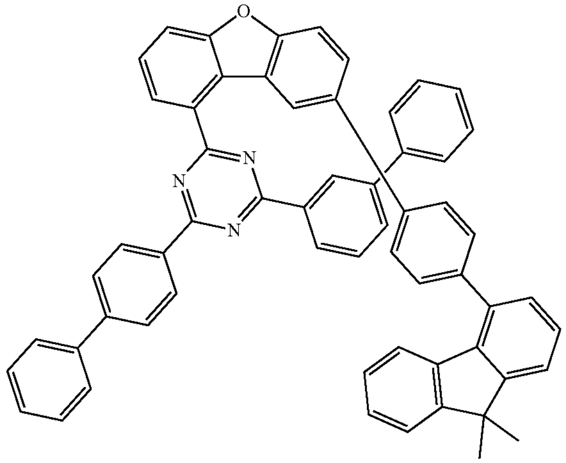 [SMILES: CC1(C)c2ccccc2-c2c(-c3ccc(-c4ccc5oc6cccc(-c7nc(-c8ccc(-c9ccccc9)cc8)nc(-c8cccc(-c9ccccc9)c8)n7)c6c5c4)cc3)cccc21]
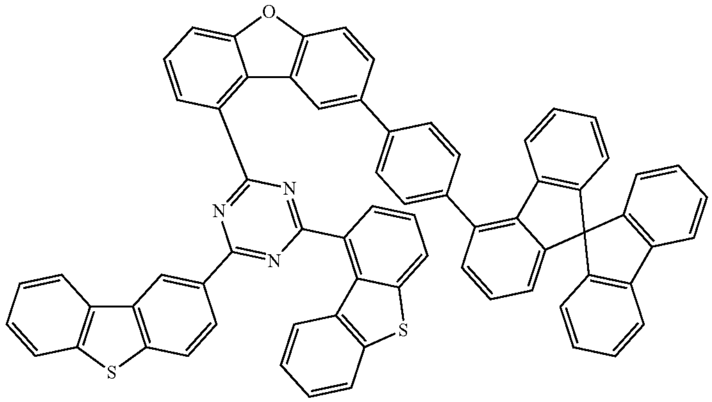 [SMILES: c1ccc2c(c1)-c1ccccc1C21c2ccccc2-c2c(-c3ccc(-c4ccc5oc6cccc(-c7nc(-c8ccc9sc%10ccccc%10c9c8)nc(-c8cccc9sc%10ccccc%10c89)n7)c6c5c4)cc3)cccc21]
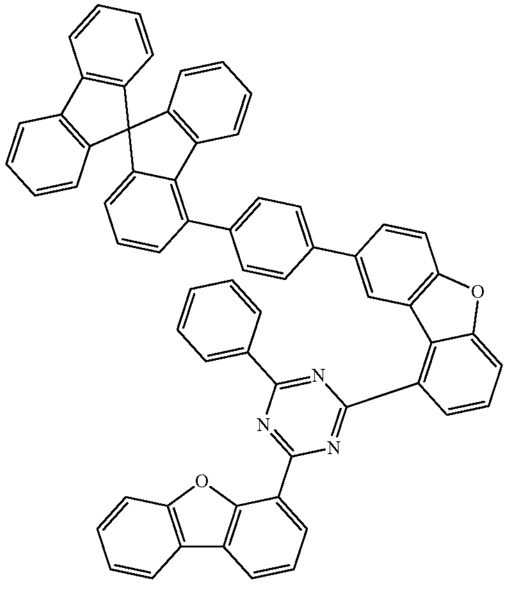 [SMILES: c1ccc(-c2nc(-c3cccc4c3oc3ccccc34)nc(-c3cccc4oc5ccc(-c6ccc(-c7cccc8c7-c7ccccc7C87c8ccccc8-c8ccccc87)cc6)cc5c34)n2)cc1]

TABLE 1-continued
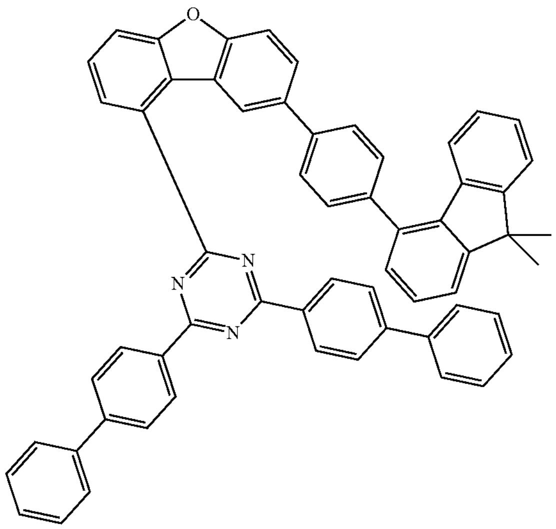 [SMILES: CC1(C)c2ccccc2-c2c(-c3ccc(-c4ccc5oc6cccc(-c7nc(-c8ccc(-c9ccccc9)cc8)nc(-c8ccc(-c9ccccc9)cc8)n7)c6c5c4)cc3)cccc21]
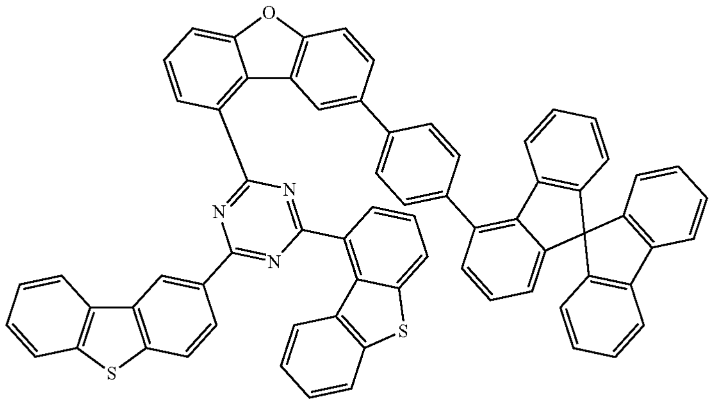 [SMILES: c1ccc2c(c1)-c1ccccc1C21c2ccccc2-c2c(-c3ccc(-c4ccc5oc6cccc(-c7nc(-c8ccc9sc%10ccccc%10c9c8)nc(-c8cccc9sc%10ccccc%10c89)n7)c6c5c4)cc3)cccc21]
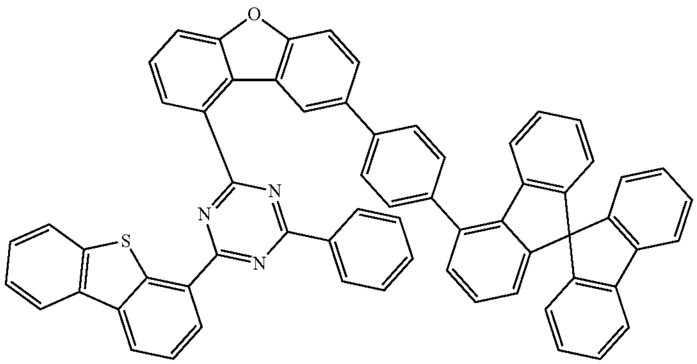 [SMILES: c1ccc(-c2nc(-c3cccc4c3sc3ccccc34)nc(-c3cccc4oc5ccc(-c6ccc(-c7cccc8c7-c7ccccc7C87c8ccccc8-c8ccccc87)cc6)cc5c34)n2)cc1]

TABLE 1-continued
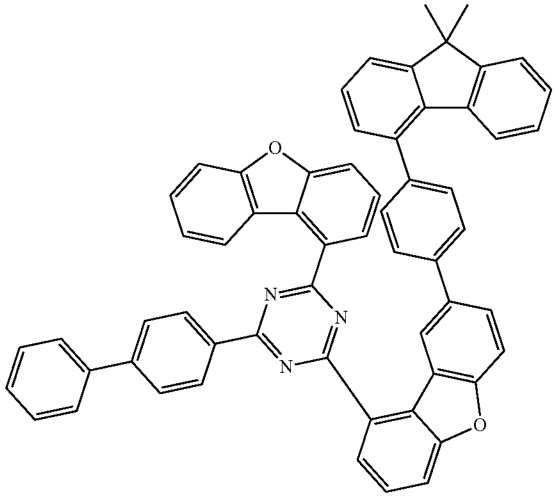 [SMILES: CC1(C)c2ccccc2-c2c(-c3ccc(-c4ccc5oc6cccc(-c7nc(-c8ccc(-c9ccccc9)cc8)nc(-c8cccc9oc%10ccccc%10c89)n7)c6c5c4)cc3)cccc21]
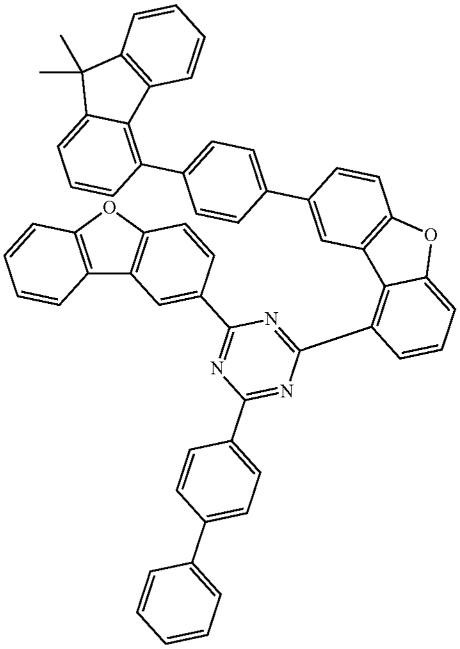 [SMILES: CC1(C)c2ccccc2-c2c(-c3ccc(-c4ccc5oc6cccc(-c7nc(-c8ccc(-c9ccccc9)cc8)nc(-c8ccc9oc%10ccccc%10c9c8)n7)c6c5c4)cc3)cccc21]
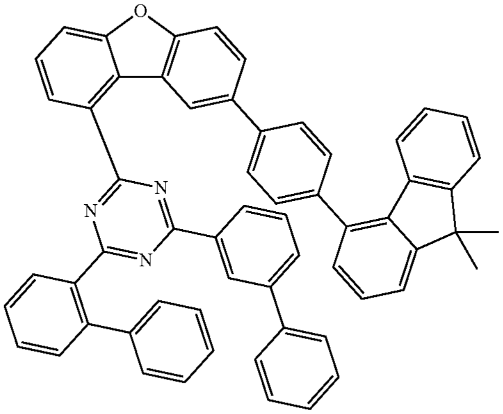 [SMILES: CC1(C)c2ccccc2-c2c(-c3ccc(-c4ccc5oc6cccc(-c7nc(-c8cccc(-c9ccccc9)c8)nc(-c8ccccc8-c8ccccc8)n7)c6c5c4)cc3)cccc21]

TABLE 1-continued
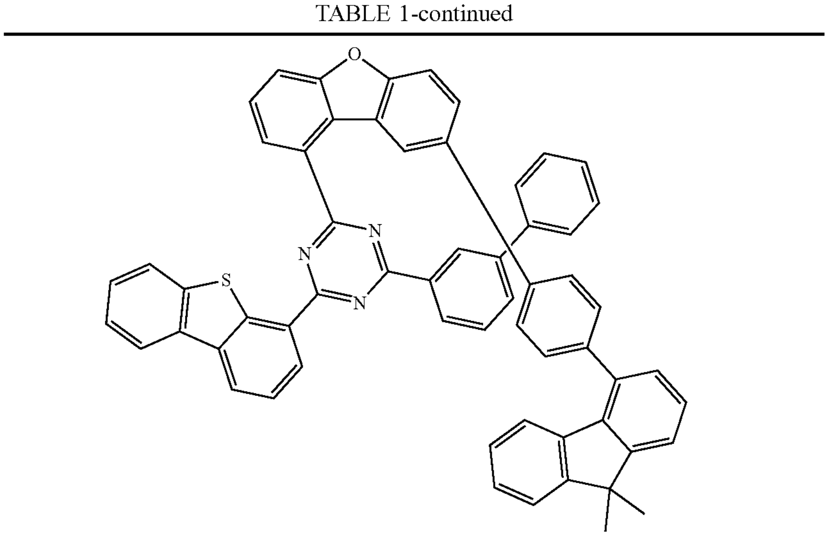
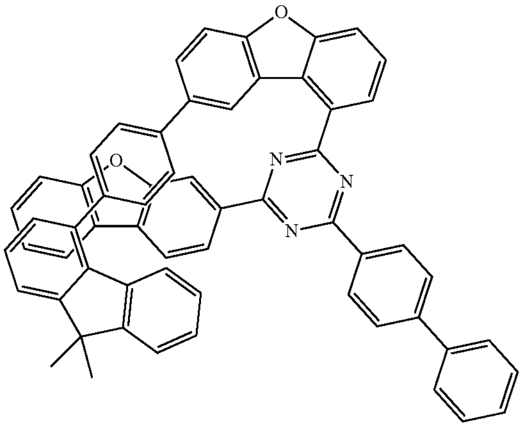 [SMILES: CC1(C)c2ccccc2-c2c(-c3ccc(-c4ccc5oc6cccc(-c7nc(-c8ccc(-c9ccccc9)cc8)nc(-c8ccc9c(c8)oc8ccccc89)n7)c6c5c4)cc3)cccc21]
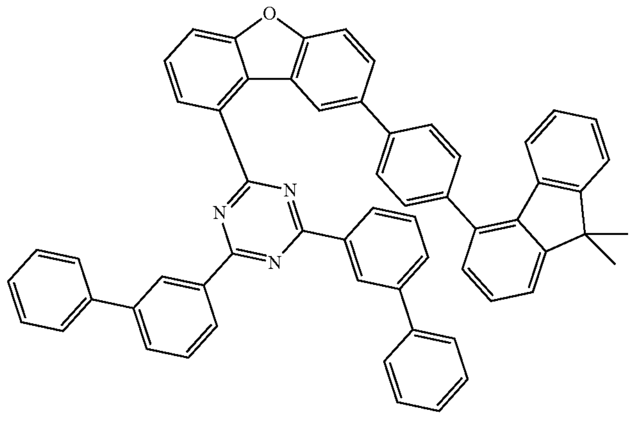 [SMILES: CC1(C)c2ccccc2-c2c(-c3ccc(-c4ccc5oc6cccc(-c7nc(-c8cccc(-c9ccccc9)c8)nc(-c8cccc(-c9ccccc9)c8)n7)c6c5c4)cc3)cccc21]

TABLE 1-continued
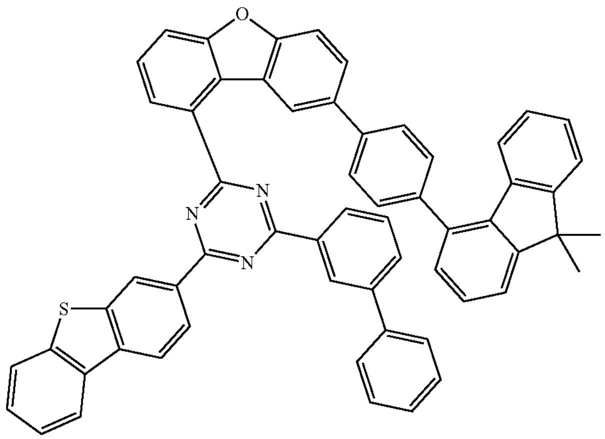 [SMILES: CC1(C)c2ccccc2-c2c(-c3ccc(-c4ccc5oc6cccc(-c7nc(-c8cccc(-c9ccccc9)c8)nc(-c8ccc9c(c8)sc8ccccc89)n7)c6c5c4)cc3)cccc21]
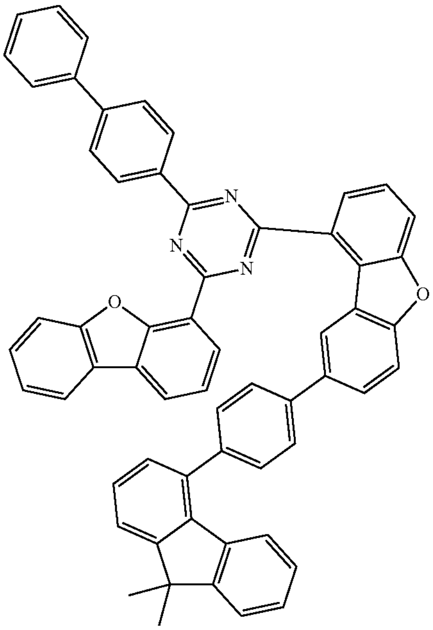 [SMILES: CC1(C)c2ccccc2-c2c(-c3ccc(-c4ccc5oc6cccc(-c7nc(-c8ccc(-c9ccccc9)cc8)nc(-c8cccc9c8oc8ccccc89)n7)c6c5c4)cc3)cccc21]
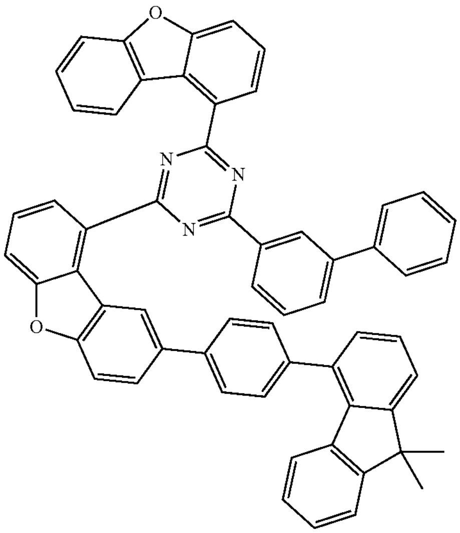 [SMILES: CC1(C)c2ccccc2-c2c(-c3ccc(-c4ccc5oc6cccc(-c7nc(-c8cccc(-c9ccccc9)c8)nc(-c8cccc9oc%10ccccc%10c89)n7)c6c5c4)cc3)cccc21]

TABLE 1-continued
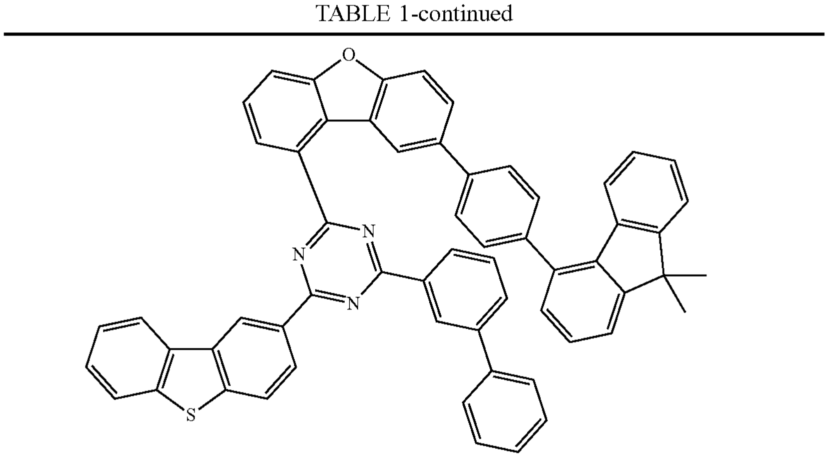
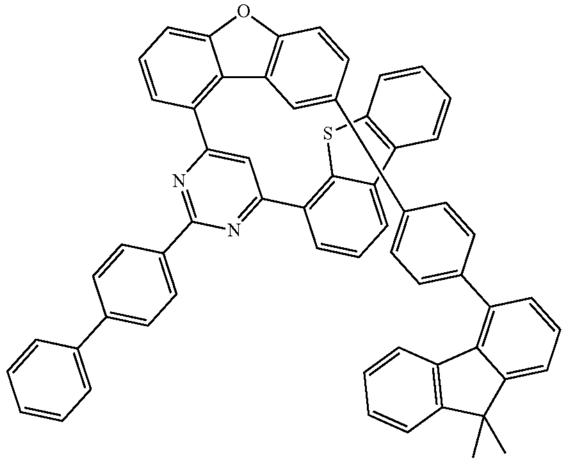 [SMILES: CC1(C)c2ccccc2-c2c(-c3ccc(-c4ccc5oc6cccc(-c7cc(-c8cccc9c8sc8ccccc89)nc(-c8ccc(-c9ccccc9)cc8)n7)c6c5c4)cc3)cccc21]
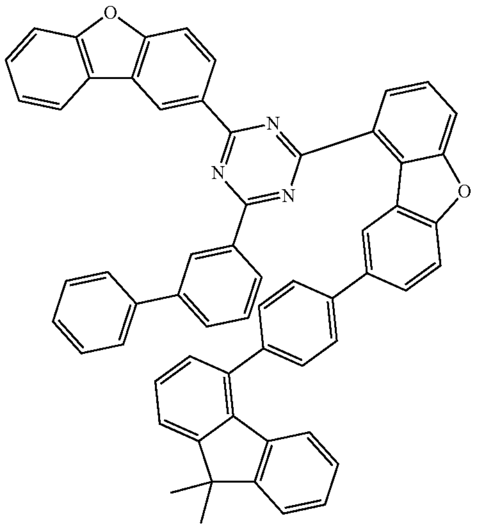 [SMILES: CC1(C)c2ccccc2-c2c(-c3ccc(-c4ccc5oc6cccc(-c7nc(-c8cccc(-c9ccccc9)c8)nc(-c8ccc9oc%10ccccc%10c9c8)n7)c6c5c4)cc3)cccc21]

TABLE 1-continued
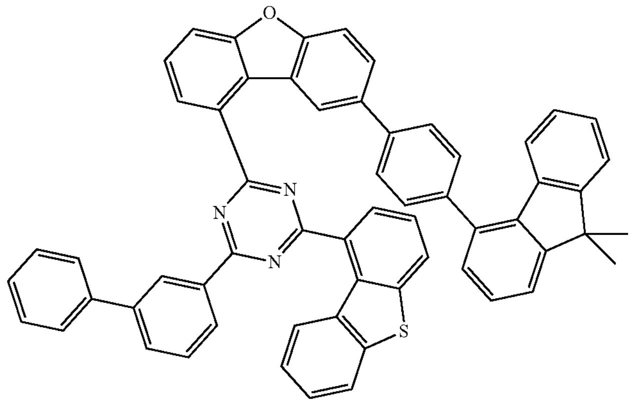 [SMILES: CC1(C)c2ccccc2-c2c(-c3ccc(-c4ccc5oc6cccc(-c7nc(-c8cccc(-c9ccccc9)c8)nc(-c8cccc9sc%10ccccc%10c89)n7)c6c5c4)cc3)cccc21]
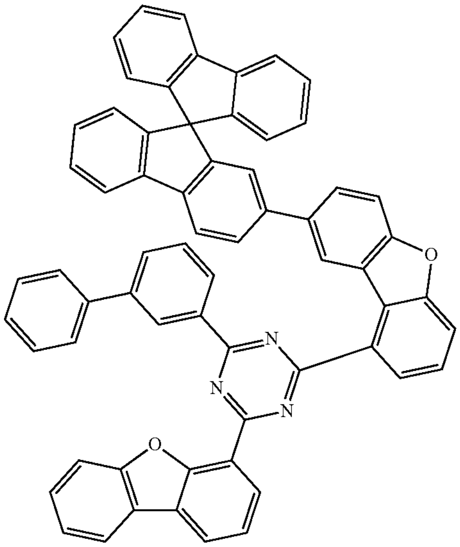 [SMILES: c1ccc(-c2cccc(-c3nc(-c4cccc5c4oc4ccccc45)nc(-c4cccc5oc6ccc(-c7ccc8c(c7)C7(c9ccccc9-c9ccccc97)c7ccccc7-8)cc6c45)n3)c2)cc1]
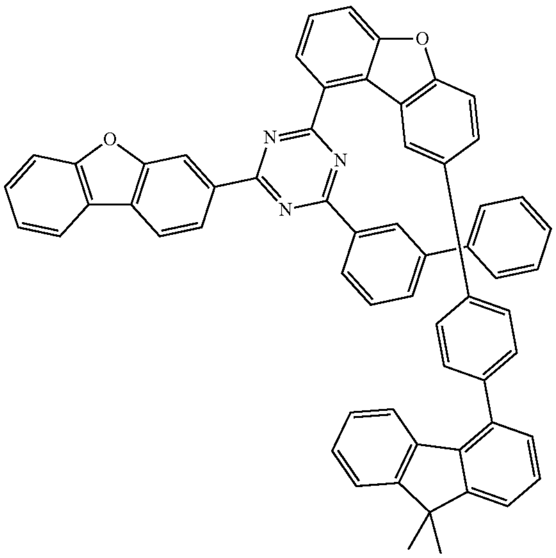 [SMILES: CC1(C)c2ccccc2-c2c(-c3ccc(-c4ccc5oc6cccc(-c7nc(-c8cccc(-c9ccccc9)c8)nc(-c8ccc9c(c8)oc8ccccc89)n7)c6c5c4)cc3)cccc21]

TABLE 1-continued
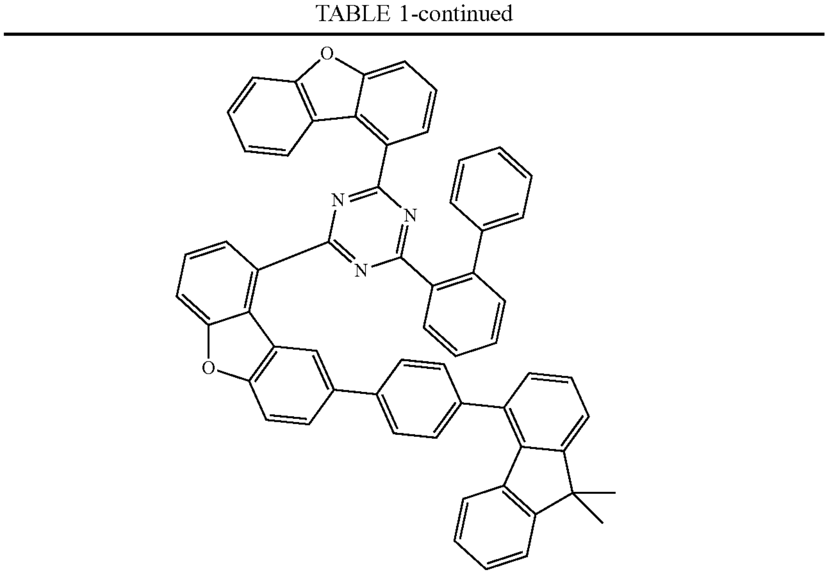
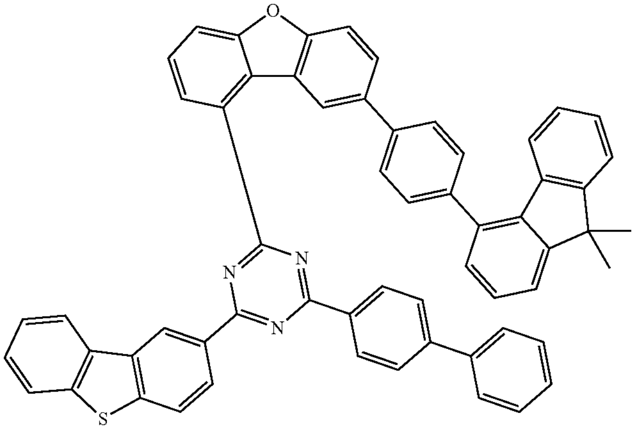 [SMILES: CC1(C)c2ccccc2-c2c(-c3ccc(-c4ccc5oc6cccc(-c7nc(-c8ccc(-c9ccccc9)cc8)nc(-c8ccc9sc%10ccccc%10c9c8)n7)c6c5c4)cc3)cccc21]
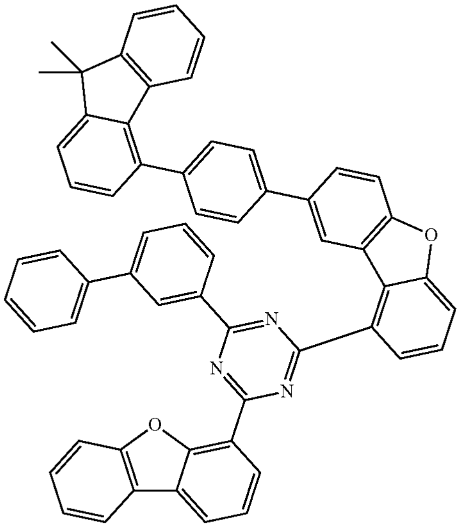 [SMILES: CC1(C)c2ccccc2-c2c(-c3ccc(-c4ccc5oc6cccc(-c7nc(-c8cccc(-c9ccccc9)c8)nc(-c8cccc9c8oc8ccccc89)n7)c6c5c4)cc3)cccc21]

TABLE 1-continued
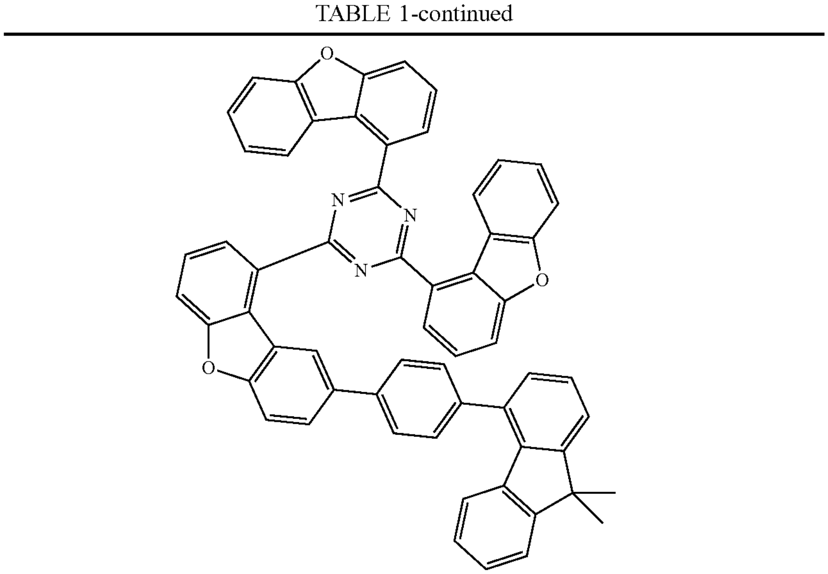
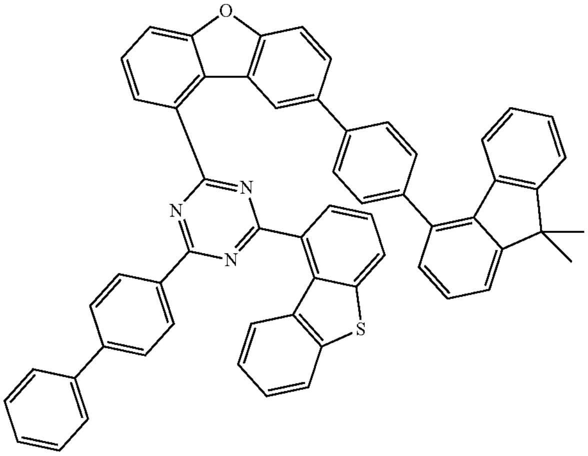 [SMILES: CC1(C)c2ccccc2-c2c(-c3ccc(-c4ccc5oc6cccc(-c7nc(-c8ccc(-c9ccccc9)cc8)nc(-c8cccc9sc%10ccccc%10c89)n7)c6c5c4)cc3)cccc21]
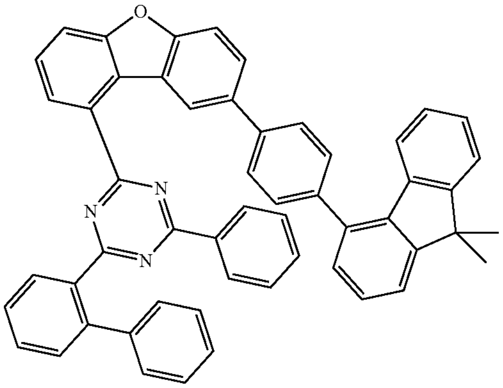 [SMILES: CC1(C)c2ccccc2-c2c(-c3ccc(-c4ccc5oc6cccc(-c7nc(-c8ccccc8)nc(-c8ccccc8-c8ccccc8)n7)c6c5c4)cc3)cccc21]

TABLE 1-continued
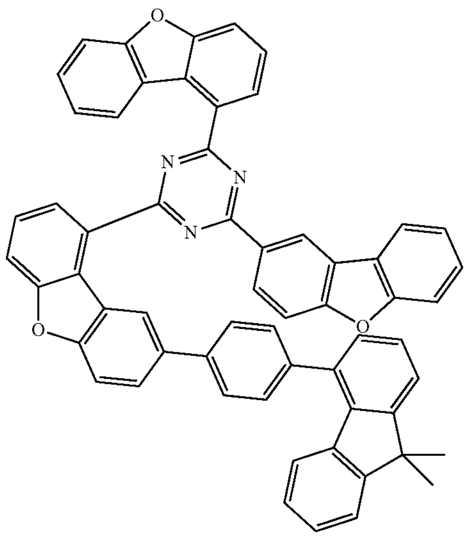 [SMILES: CC1(C)c2ccccc2-c2c(-c3ccc(-c4ccc5oc6cccc(-c7nc(-c8ccc9oc%10ccccc%10c9c8)nc(-c8cccc9oc%10ccccc%10c89)n7)c6c5c4)cc3)cccc21]
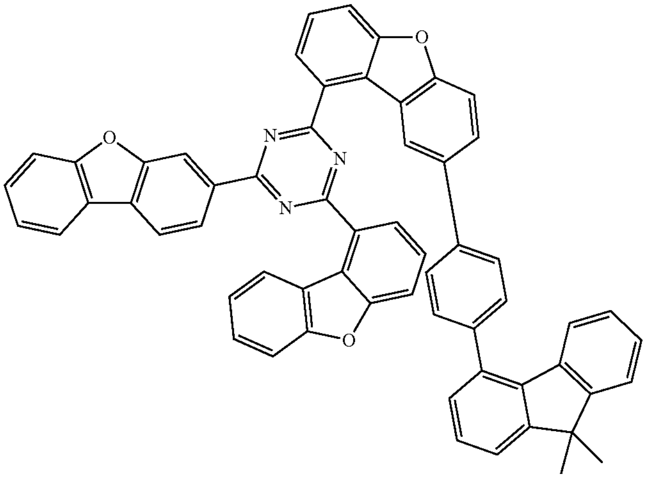 [SMILES: CC1(C)c2ccccc2-c2c(-c3ccc(-c4ccc5oc6cccc(-c7nc(-c8ccc9c(c8)oc8ccccc89)nc(-c8cccc9oc%10ccccc%10c89)n7)c6c5c4)cc3)cccc21]
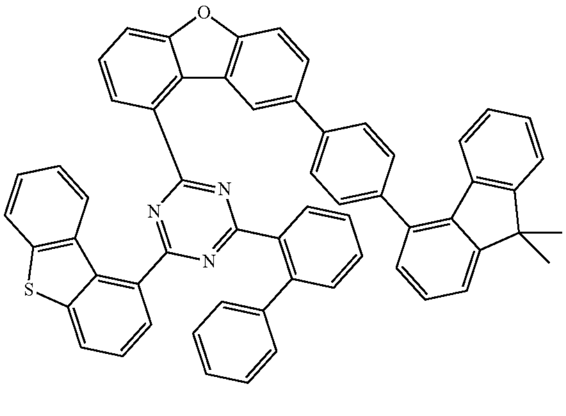 [SMILES: CC1(C)c2ccccc2-c2c(-c3ccc(-c4ccc5oc6cccc(-c7nc(-c8ccccc8-c8ccccc8)nc(-c8cccc9sc%10ccccc%10c89)n7)c6c5c4)cc3)cccc21]

TABLE 1-continued
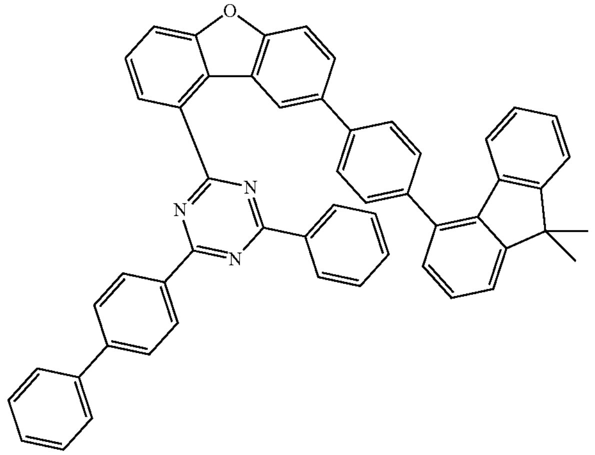 [SMILES: CC1(C)c2ccccc2-c2c(-c3ccc(-c4ccc5oc6cccc(-c7nc(-c8ccccc8)nc(-c8ccc(-c9ccccc9)cc8)n7)c6c5c4)cc3)cccc21]
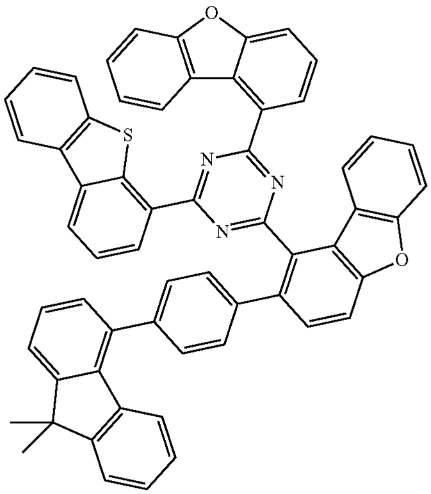 [SMILES: CC1(C)c2ccccc2-c2c(-c3ccc(-c4ccc5oc6ccccc6c5c4-c4nc(-c5cccc6c5sc5ccccc56)nc(-c5cccc6oc7ccccc7c56)n4)cc3)cccc21]
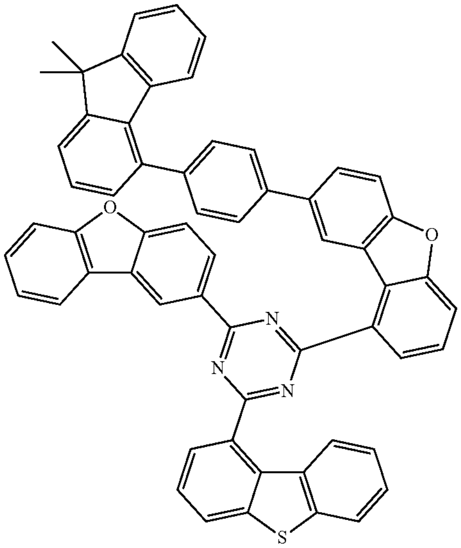 [SMILES: CC1(C)c2ccccc2-c2c(-c3ccc(-c4ccc5oc6cccc(-c7nc(-c8ccc9oc%10ccccc%10c9c8)nc(-c8cccc9sc%10ccccc%10c89)n7)c6c5c4)cc3)cccc21]

TABLE 1-continued
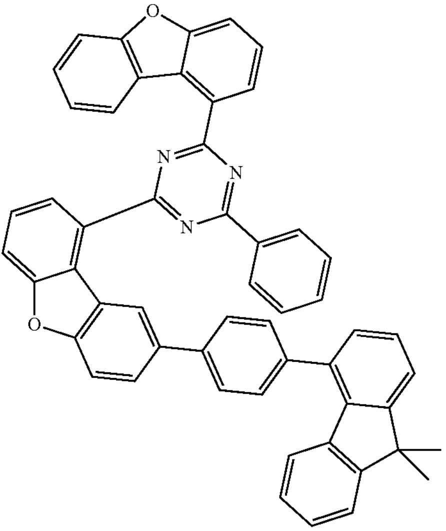 [SMILES: CC1(C)c2ccccc2-c2c(-c3ccc(-c4ccc5oc6cccc(-c7nc(-c8ccccc8)nc(-c8cccc9oc%10ccccc%10c89)n7)c6c5c4)cc3)cccc21]
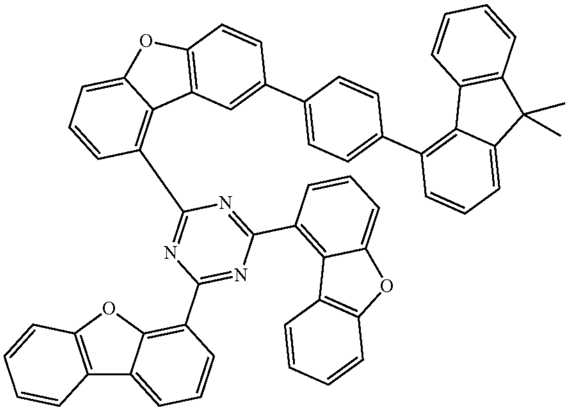 [SMILES: CC1(C)c2ccccc2-c2c(-c3ccc(-c4ccc5oc6cccc(-c7nc(-c8cccc9c8oc8ccccc89)nc(-c8cccc9oc%10ccccc%10c89)n7)c6c5c4)cc3)cccc21]
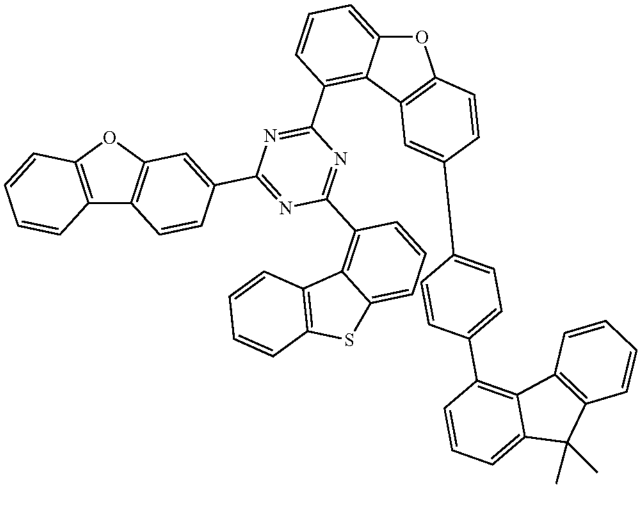 [SMILES: CC1(C)c2ccccc2-c2c(-c3ccc(-c4ccc5oc6cccc(-c7nc(-c8ccc9c(c8)oc8ccccc89)nc(-c8cccc9sc%10ccccc%10c89)n7)c6c5c4)cc3)cccc21]

TABLE 1-continued
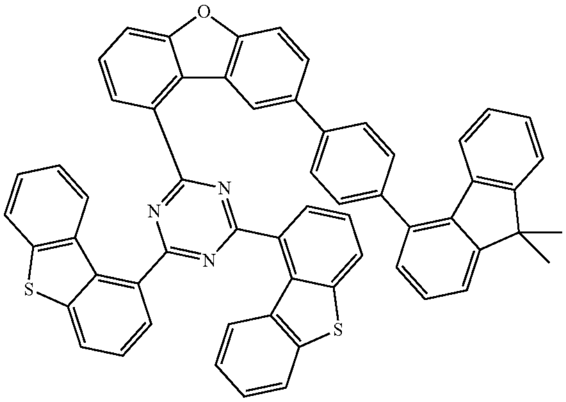 [SMILES: CC1(C)c2ccccc2-c2c(-c3ccc(-c4ccc5oc6cccc(-c7nc(-c8cccc9sc%10ccccc%10c89)nc(-c8cccc9sc%10ccccc%10c89)n7)c6c5c4)cc3)cccc21]
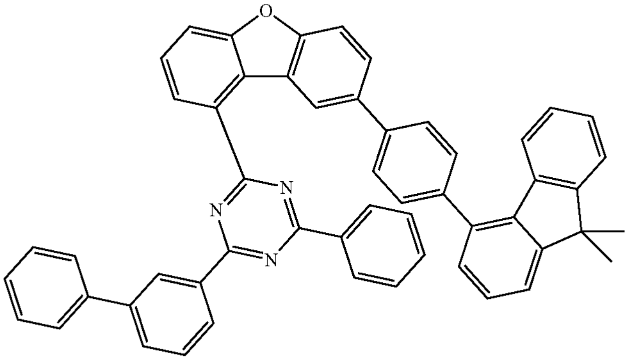 [SMILES: CC1(C)c2ccccc2-c2c(-c3ccc(-c4ccc5oc6cccc(-c7nc(-c8ccccc8)nc(-c8cccc(-c9ccccc9)c8)n7)c6c5c4)cc3)cccc21]
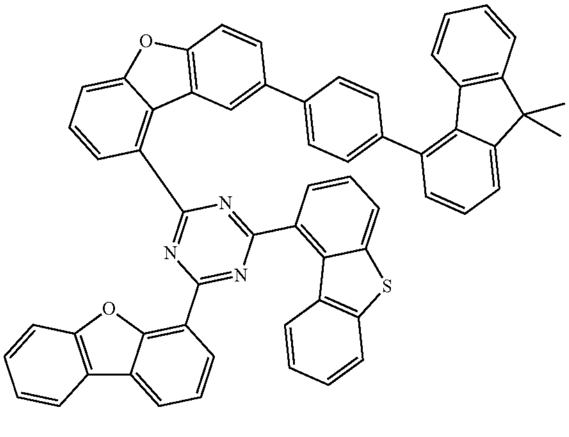 [SMILES: CC1(C)c2ccccc2-c2c(-c3ccc(-c4ccc5oc6cccc(-c7nc(-c8cccc9c8oc8ccccc89)nc(-c8cccc9sc%10ccccc%10c89)n7)c6c5c4)cc3)cccc21]

TABLE 1-continued
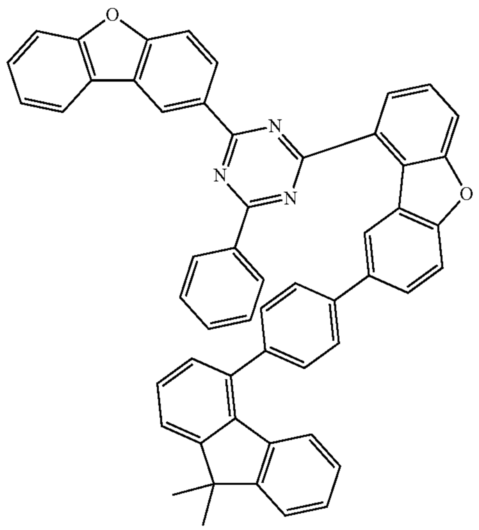 [SMILES: CC1(C)c2ccccc2-c2c(-c3ccc(-c4ccc5oc6cccc(-c7nc(-c8ccccc8)nc(-c8ccc9oc%10ccccc%10c9c8)n7)c6c5c4)cc3)cccc21]
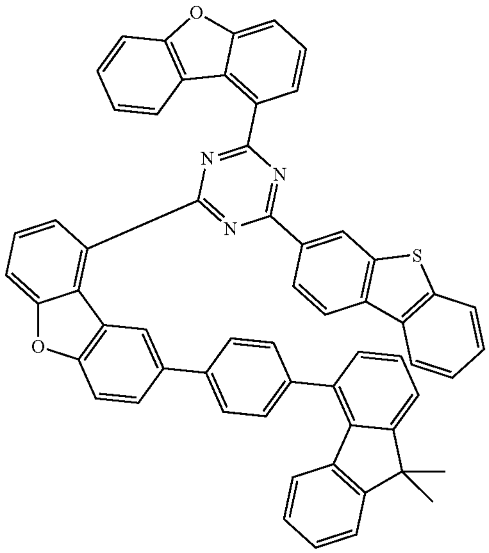 [SMILES: CC1(C)c2ccccc2-c2c(-c3ccc(-c4ccc5oc6cccc(-c7nc(-c8ccc9c(c8)sc8ccccc89)nc(-c8cccc9oc%10ccccc%10c89)n7)c6c5c4)cc3)cccc21]
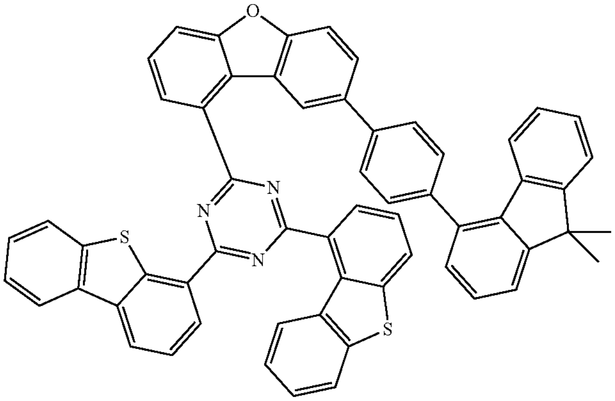 [SMILES: CC1(C)c2ccccc2-c2c(-c3ccc(-c4ccc5oc6cccc(-c7nc(-c8cccc9c8sc8ccccc89)nc(-c8cccc9sc%10ccccc%10c89)n7)c6c5c4)cc3)cccc21]

TABLE 1-continued
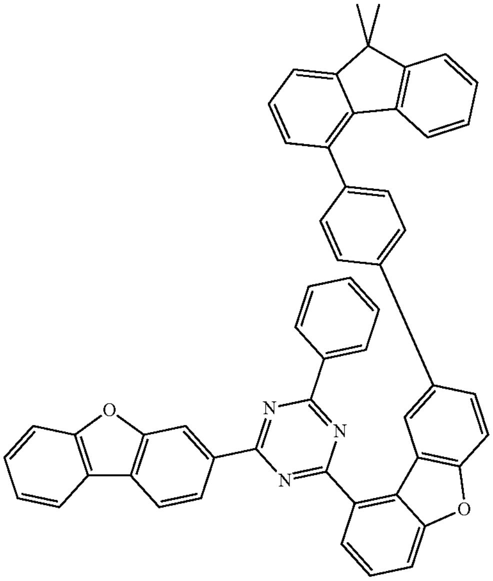 [SMILES: CC1(C)c2ccccc2-c2c(-c3ccc(-c4ccc5oc6cccc(-c7nc(-c8ccccc8)nc(-c8ccc9c(c8)oc8ccccc89)n7)c6c5c4)cc3)cccc21]
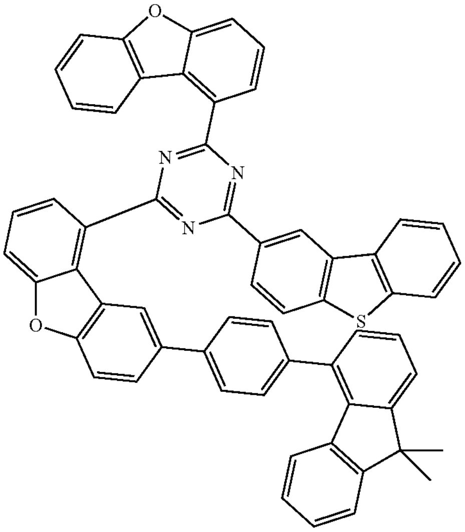
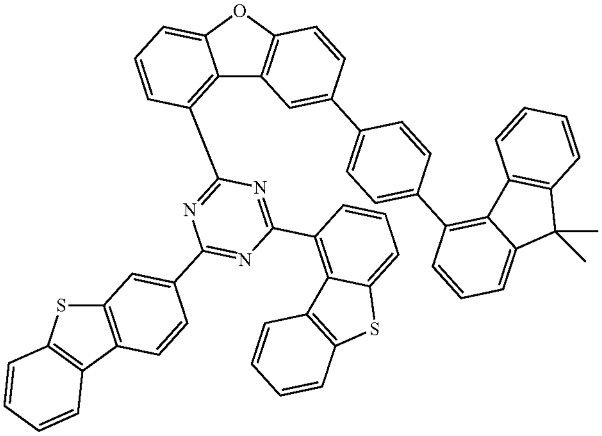 [SMILES: CC1(C)c2ccccc2-c2c(-c3ccc(-c4ccc5oc6cccc(-c7nc(-c8ccc9c(c8)sc8ccccc89)nc(-c8cccc9sc%10ccccc%10c89)n7)c6c5c4)cc3)cccc21]

TABLE 1-continued
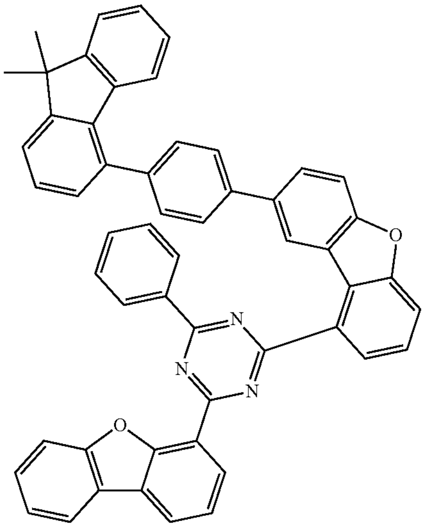 [SMILES: CC1(C)c2ccccc2-c2c(-c3ccc(-c4ccc5oc6cccc(-c7nc(-c8ccccc8)nc(-c8cccc9c8oc8ccccc89)n7)c6c5c4)cc3)cccc21]
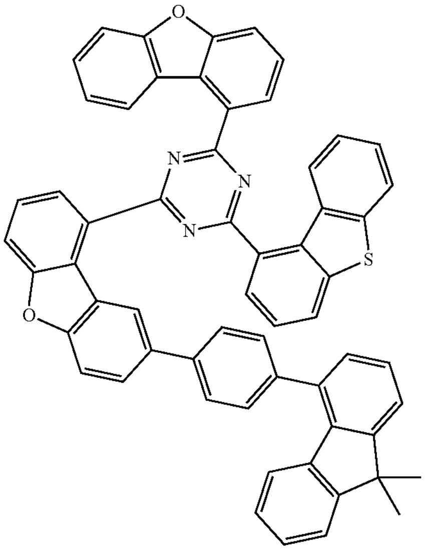 [SMILES: CC1(C)c2ccccc2-c2c(-c3ccc(-c4ccc5oc6cccc(-c7nc(-c8cccc9oc%10ccccc%10c89)nc(-c8cccc9sc%10ccccc%10c89)n7)c6c5c4)cc3)cccc21]
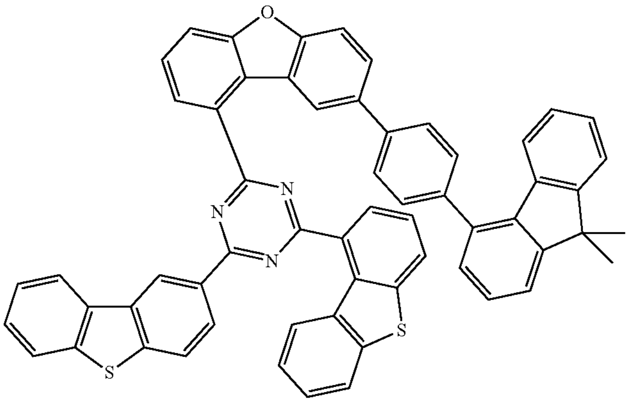 [SMILES: CC1(C)c2ccccc2-c2c(-c3ccc(-c4ccc5oc6cccc(-c7nc(-c8ccc9sc%10ccccc%10c9c8)nc(-c8cccc9sc%10ccccc%10c89)n7)c6c5c4)cc3)cccc21]

TABLE 1-continued
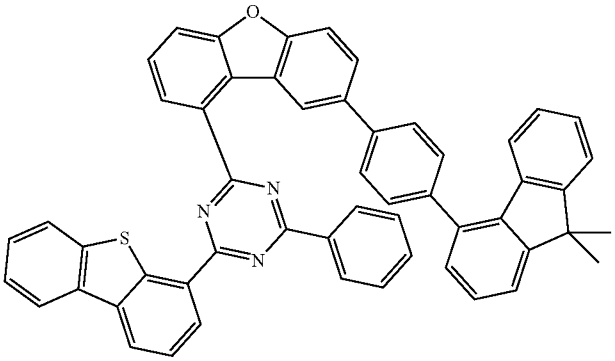 [SMILES: CC1(C)c2ccccc2-c2c(-c3ccc(-c4ccc5oc6cccc(-c7nc(-c8ccccc8)nc(-c8cccc9c8sc8ccccc89)n7)c6c5c4)cc3)cccc21]
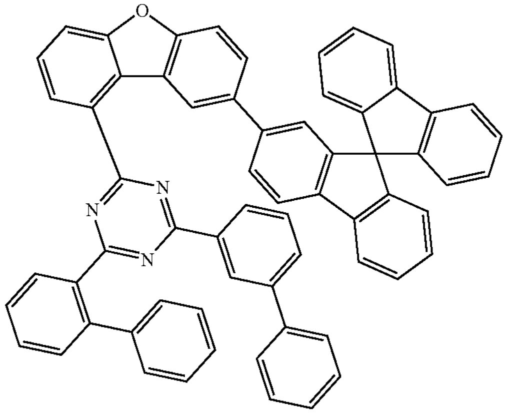 [SMILES: c1ccc(-c2cccc(-c3nc(-c4ccccc4-c4ccccc4)nc(-c4cccc5oc6ccc(-c7ccc8c(c7)C7(c9ccccc9-c9ccccc97)c7ccccc7-8)cc6c45)n3)c2)cc1]
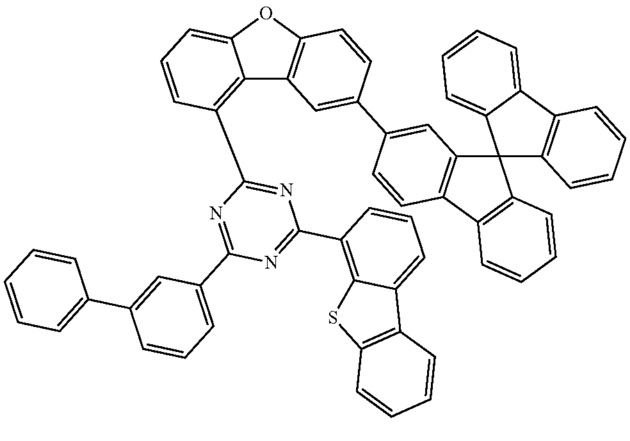 [SMILES: c1ccc(-c2cccc(-c3nc(-c4cccc5c4sc4ccccc45)nc(-c4cccc5oc6ccc(-c7ccc8c(c7)C7(c9ccccc9-c9ccccc97)c7ccccc7-8)cc6c45)n3)c2)cc1]

TABLE 1-continued
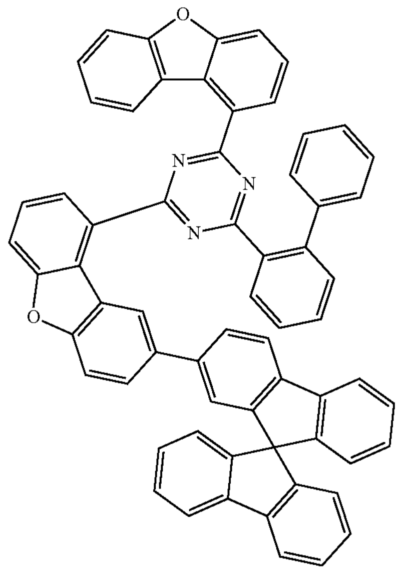 [SMILES: c1ccc(-c2ccccc2-c2nc(-c3cccc4oc5ccccc5c34)nc(-c3cccc4oc5ccc(-c6ccc7c(c6)C6(c8ccccc8-c8ccccc86)c6ccccc6-7)cc5c34)n2)cc1]
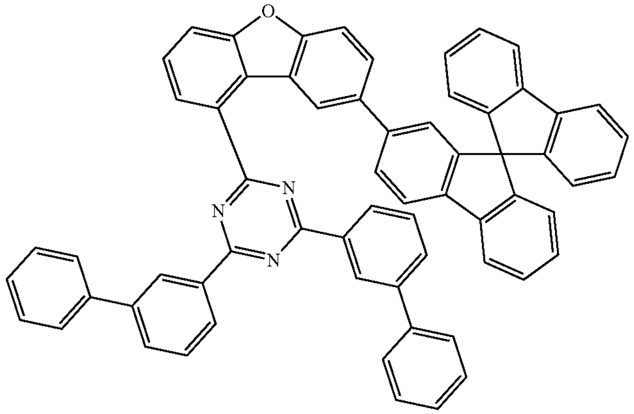 [SMILES: c1ccc(-c2cccc(-c3nc(-c4cccc(-c5ccccc5)c4)nc(-c4cccc5oc6ccc(-c7ccc8c(c7)C7(c9ccccc9-c9ccccc97)c7ccccc7-8)cc6c45)n3)c2)cc1]
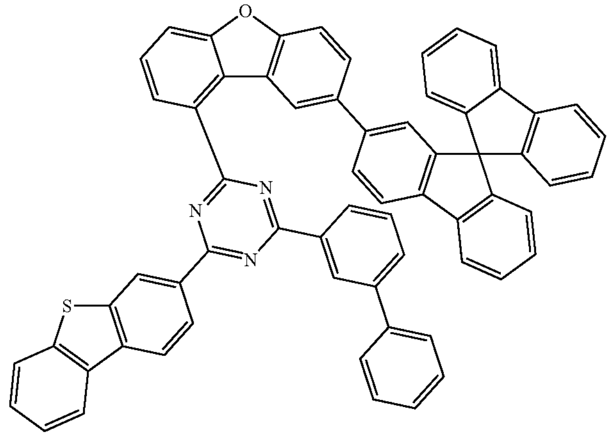 [SMILES: c1ccc(-c2cccc(-c3nc(-c4ccc5c(c4)sc4ccccc45)nc(-c4cccc5oc6ccc(-c7ccc8c(c7)C7(c9ccccc9-c9ccccc97)c7ccccc7-8)cc6c45)n3)c2)cc1]

TABLE 1-continued
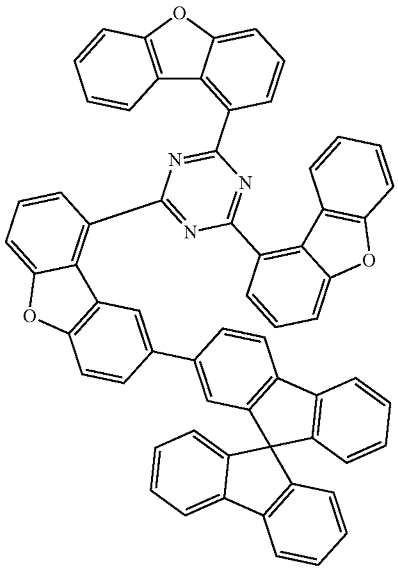 [SMILES: c1ccc2c(c1)-c1ccccc1C21c2ccccc2-c2ccc(-c3ccc4oc5cccc(-c6nc(-c7cccc8oc9ccccc9c78)nc(-c7cccc8oc9ccccc9c78)n6)c5c4c3)cc21]
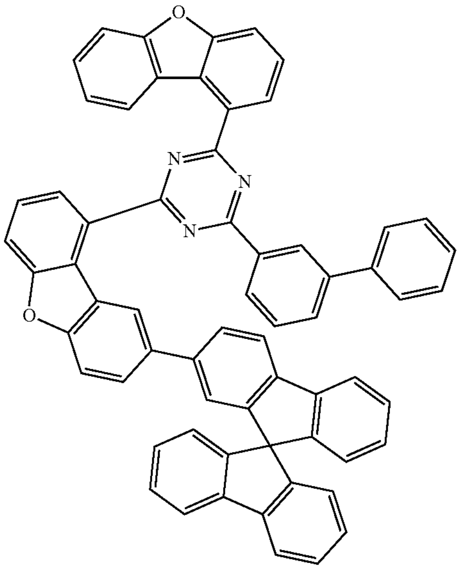 [SMILES: c1ccc(-c2cccc(-c3nc(-c4cccc5oc6ccccc6c45)nc(-c4cccc5oc6ccc(-c7ccc8c(c7)C7(c9ccccc9-c9ccccc97)c7ccccc7-8)cc6c45)n3)c2)cc1]

TABLE 1-continued
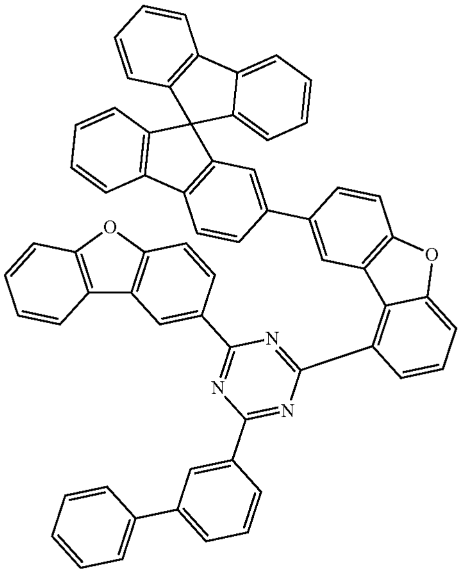 [SMILES: c1ccc(-c2cccc(-c3nc(-c4ccc5oc6ccccc6c5c4)nc(-c4cccc5oc6ccc(-c7ccc8c(c7)C7(c9ccccc9-c9ccccc97)c7ccccc7-8)cc6c45)n3)c2)cc1]
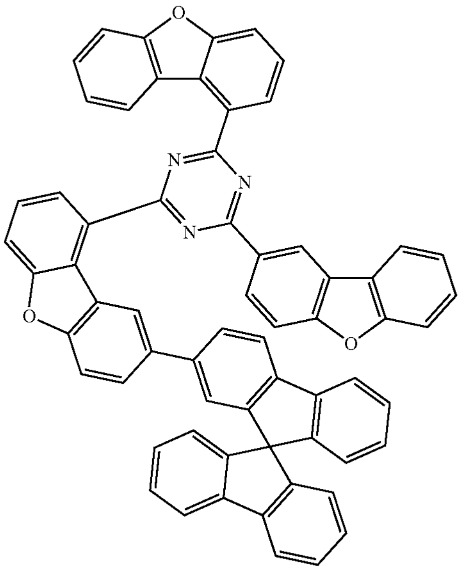 [SMILES: c1ccc2c(c1)-c1ccccc1C21c2ccccc2-c2ccc(-c3ccc4oc5cccc(-c6nc(-c7ccc8oc9ccccc9c8c7)nc(-c7cccc8oc9ccccc9c78)n6)c5c4c3)cc21]
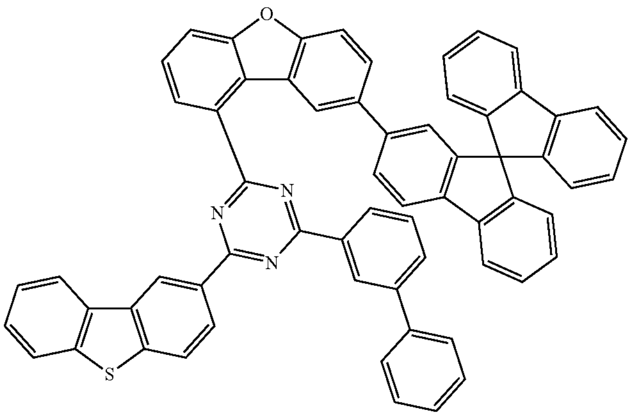 [SMILES: c1ccc(-c2cccc(-c3nc(-c4ccc5sc6ccccc6c5c4)nc(-c4cccc5oc6ccc(-c7ccc8c(c7)C7(c9ccccc9-c9ccccc97)c7ccccc7-8)cc6c45)n3)c2)cc1]

TABLE 1-continued
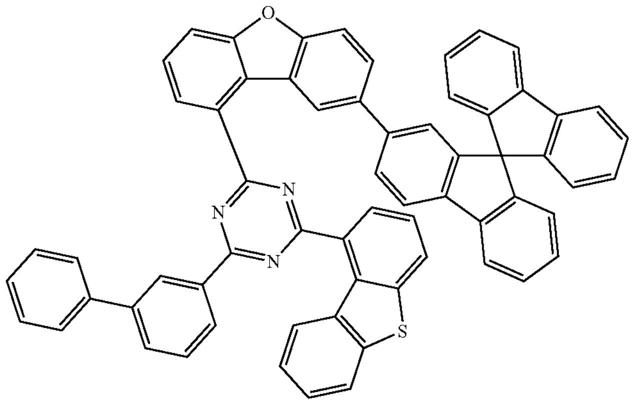 [SMILES: c1ccc(-c2cccc(-c3nc(-c4cccc5oc6ccc(-c7ccc8c(c7)C7(c9ccccc9-c9ccccc97)c7ccccc7-8)cc6c45)nc(-c4cccc5sc6ccccc6c45)n3)c2)cc1]
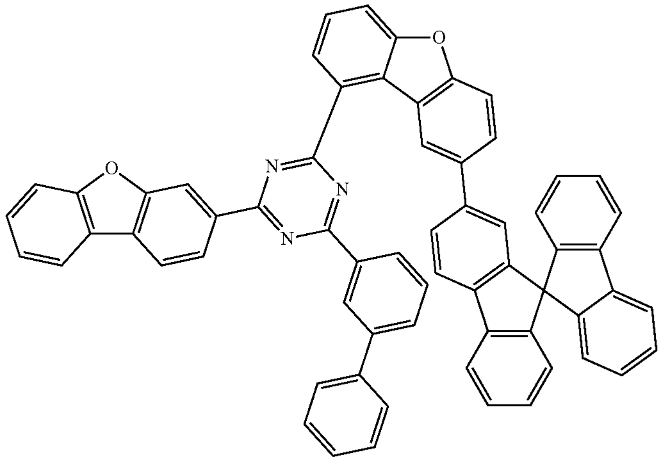 [SMILES: c1ccc(-c2cccc(-c3nc(-c4ccc5c(c4)oc4ccccc45)nc(-c4cccc5oc6ccc(-c7ccc8c(c7)C7(c9ccccc9-c9ccccc97)c7ccccc7-8)cc6c45)n3)c2)cc1]
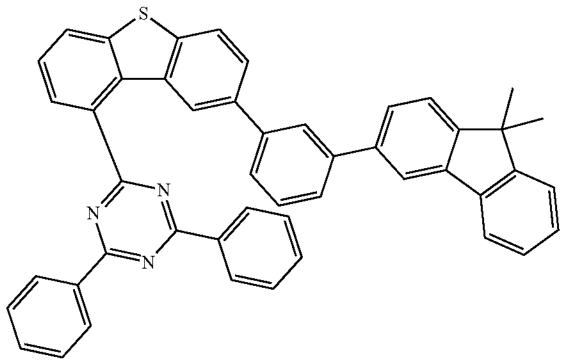 [SMILES: CC1(C)c2ccccc2-c2cc(-c3cccc(-c4ccc5sc6cccc(-c7nc(-c8ccccc8)nc(-c8ccccc8)n7)c6c5c4)c3)ccc21]
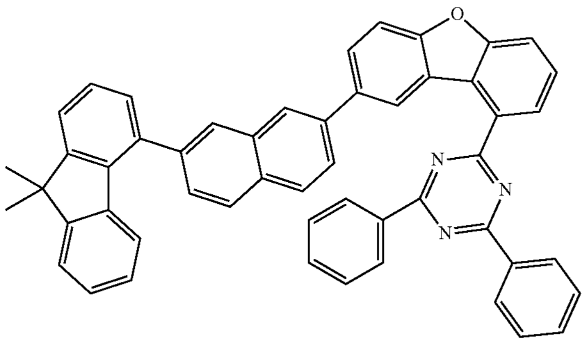 [SMILES: CC1(C)c2ccccc2-c2c(-c3ccc4ccc(-c5ccc6oc7cccc(-c8nc(-c9ccccc9)nc(-c9ccccc9)n8)c7c6c5)cc4c3)cccc21]

TABLE 1-continued
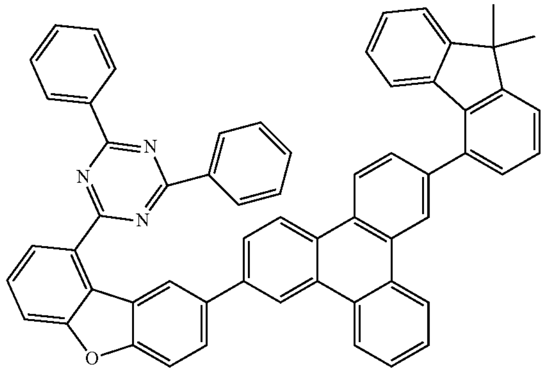 [SMILES: CC1(C)c2ccccc2-c2c(-c3ccc4c5ccc(-c6ccc7oc8cccc(-c9nc(-c%10ccccc%10)nc(-c%10ccccc%10)n9)c8c7c6)cc5c5ccccc5c4c3)cccc21]
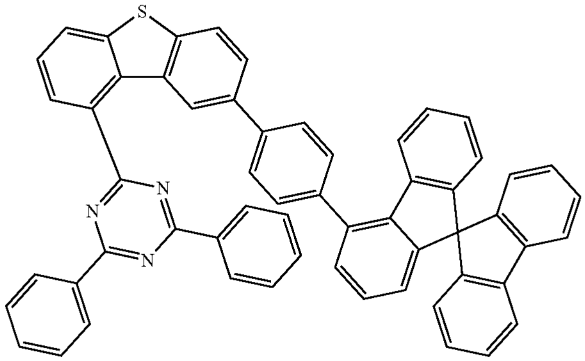 [SMILES: c1ccc(-c2nc(-c3ccccc3)nc(-c3cccc4sc5ccc(-c6ccc(-c7cccc8c7-c7ccccc7C87c8ccccc8-c8ccccc87)cc6)cc5c34)n2)cc1]
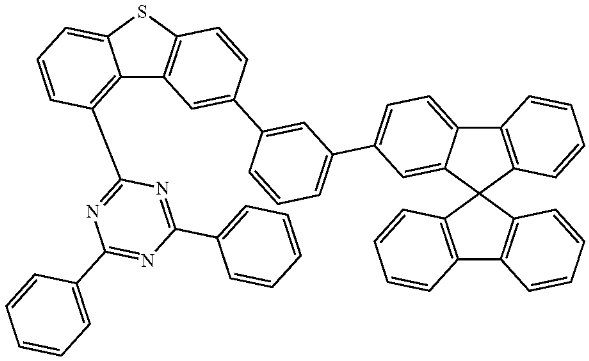 [SMILES: c1ccc(-c2nc(-c3ccccc3)nc(-c3cccc4sc5ccc(-c6cccc(-c7ccc8c(c7)C7(c9ccccc9-c9ccccc97)c7ccccc7-8)c6)cc5c34)n2)cc1]
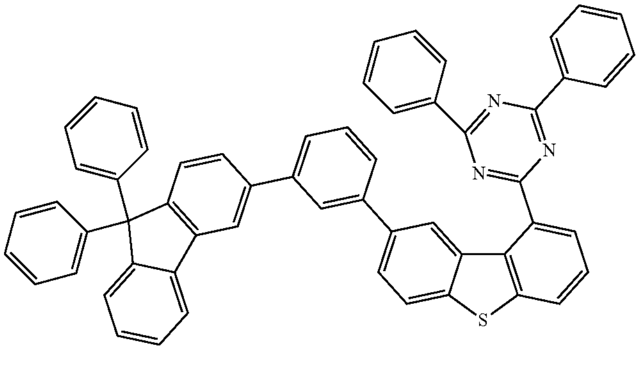 [SMILES: c1ccc(-c2nc(-c3ccccc3)nc(-c3cccc4sc5ccc(-c6cccc(-c7ccc8c(c7)-c7ccccc7C8(c7ccccc7)c7ccccc7)c6)cc5c34)n2)cc1]

TABLE 1-continued
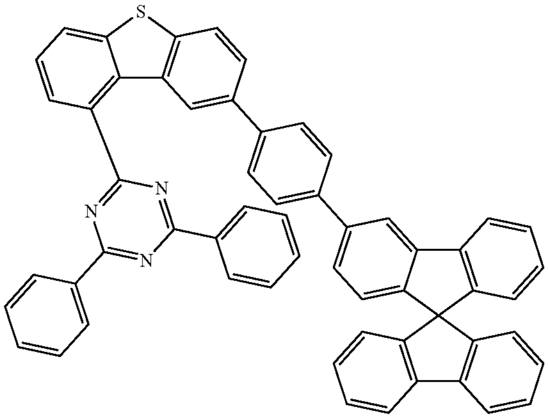 [SMILES: c1ccc(-c2nc(-c3ccccc3)nc(-c3cccc4sc5ccc(-c6ccc(-c7ccc8c(c7)-c7ccccc7C87c8ccccc8-c8ccccc87)cc6)cc5c34)n2)cc1]
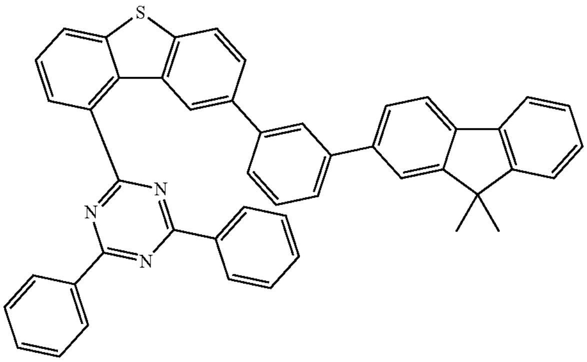 [SMILES: CC1(C)c2ccccc2-c2ccc(-c3cccc(-c4ccc5sc6cccc(-c7nc(-c8ccccc8)nc(-c8ccccc8)n7)c6c5c4)c3)cc21]
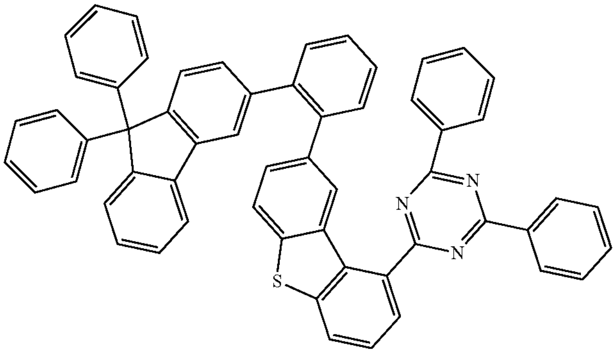 [SMILES: c1ccc(-c2nc(-c3ccccc3)nc(-c3cccc4sc5ccc(-c6ccccc6-c6ccc7c(c6)-c6ccccc6C7(c6ccccc6)c6ccccc6)cc5c34)n2)cc1]
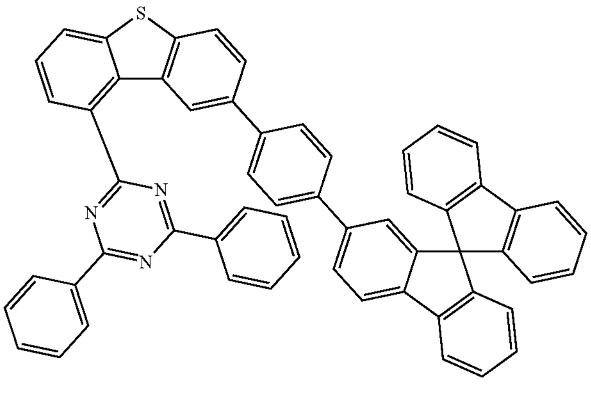 [SMILES: c1ccc(-c2nc(-c3ccccc3)nc(-c3cccc4sc5ccc(-c6ccc(-c7ccc8c(c7)C7(c9ccccc9-c9ccccc97)c7ccccc7-8)cc6)cc5c34)n2)cc1]

TABLE 1-continued
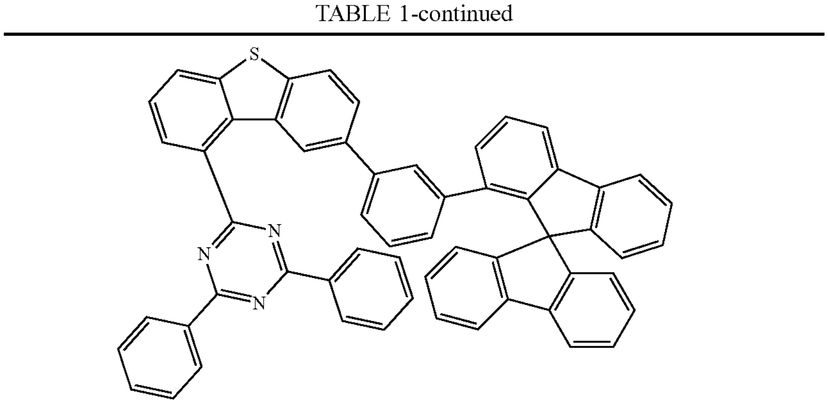
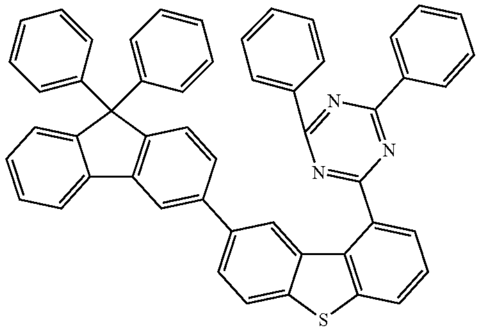 [SMILES: c1ccc(-c2nc(-c3ccccc3)nc(-c3cccc4sc5ccc(-c6ccc7c(c6)-c6ccccc6C7(c6ccccc6)c6ccccc6)cc5c34)n2)cc1]
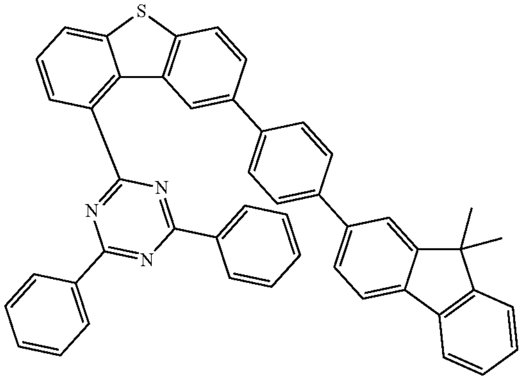 [SMILES: CC1(C)c2ccccc2-c2ccc(-c3ccc(-c4ccc5sc6cccc(-c7nc(-c8ccccc8)nc(-c8ccccc8)n7)c6c5c4)cc3)cc21]
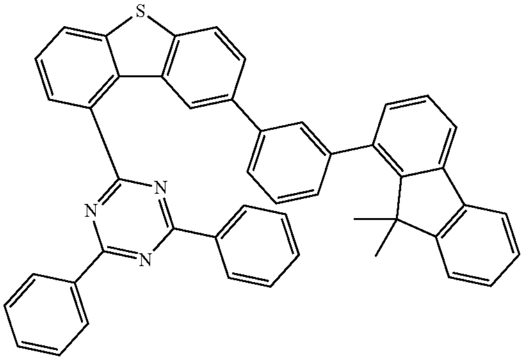 [SMILES: CC1(C)c2ccccc2-c2cccc(-c3cccc(-c4ccc5sc6cccc(-c7nc(-c8ccccc8)nc(-c8ccccc8)n7)c6c5c4)c3)c21]

TABLE 1-continued
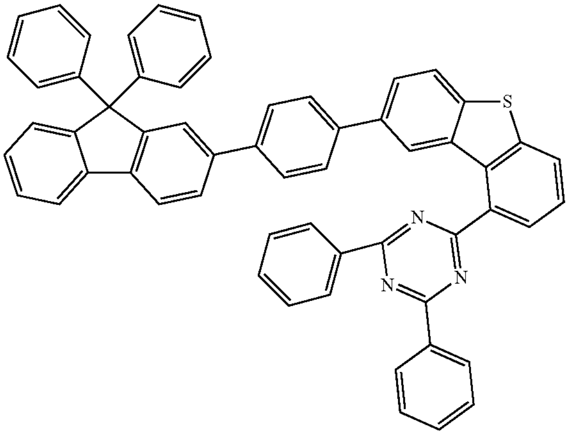 [SMILES: c1ccc(-c2nc(-c3ccccc3)nc(-c3cccc4sc5ccc(-c6ccc(-c7ccc8c(c7)C(c7ccccc7)(c7ccccc7)c7ccccc7-8)cc6)cc5c34)n2)cc1]
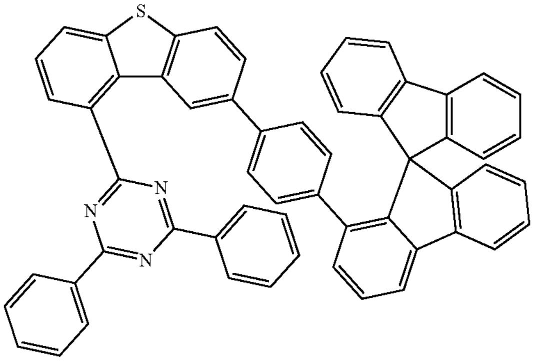 [SMILES: c1ccc(-c2nc(-c3ccccc3)nc(-c3cccc4sc5ccc(-c6ccc(-c7cccc8c7C7(c9ccccc9-c9ccccc97)c7ccccc7-8)cc6)cc5c34)n2)cc1]
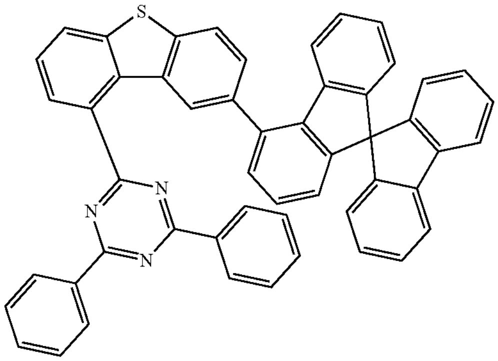 [SMILES: c1ccc(-c2nc(-c3ccccc3)nc(-c3cccc4sc5ccc(-c6cccc7c6-c6ccccc6C76c7ccccc7-c7ccccc76)cc5c34)n2)cc1]
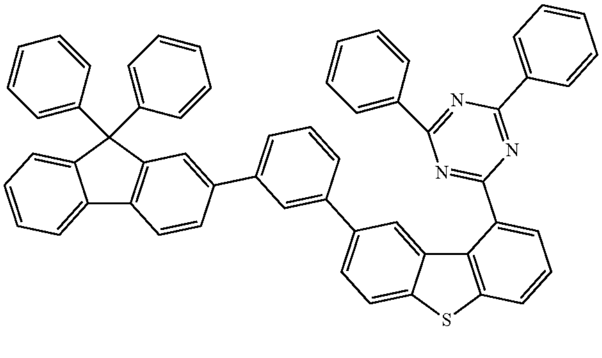 [SMILES: c1ccc(-c2nc(-c3ccccc3)nc(-c3cccc4sc5ccc(-c6cccc(-c7ccc8c(c7)C(c7ccccc7)(c7ccccc7)c7ccccc7-8)c6)cc5c34)n2)cc1]

TABLE 1-continued
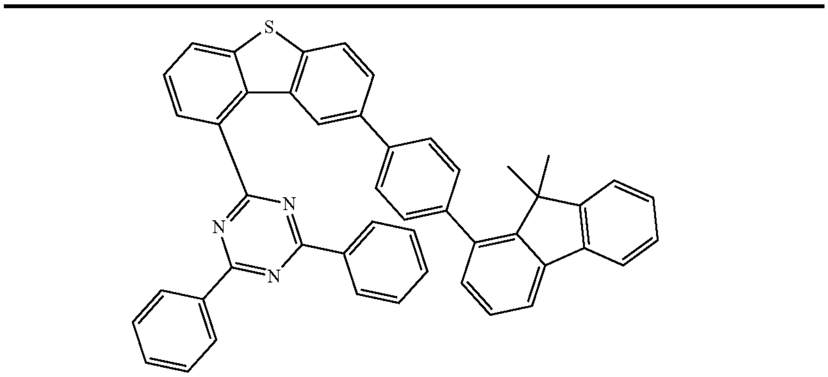
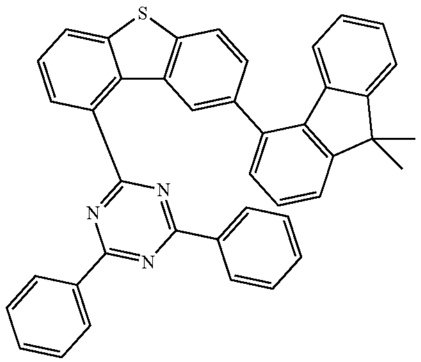 [SMILES: CC1(C)c2ccccc2-c2c(-c3ccc4sc5cccc(-c6nc(-c7ccccc7)nc(-c7ccccc7)n6)c5c4c3)cccc21]
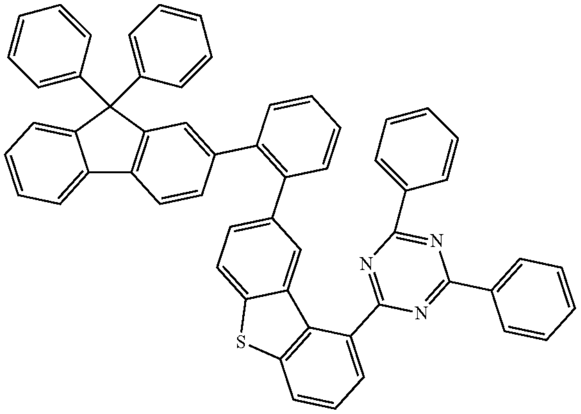 [SMILES: c1ccc(-c2nc(-c3ccccc3)nc(-c3cccc4sc5ccc(-c6ccccc6-c6ccc7c(c6)C(c6ccccc6)(c6ccccc6)c6ccccc6-7)cc5c34)n2)cc1]
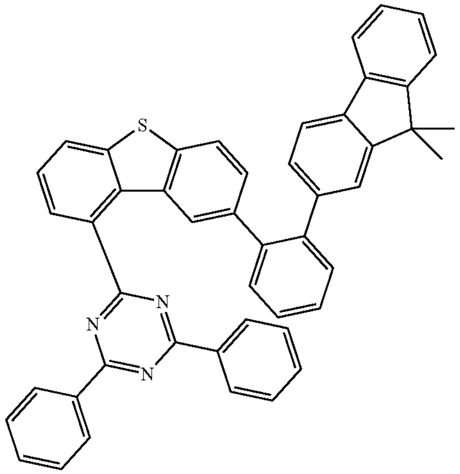 [SMILES: CC1(C)c2ccccc2-c2ccc(-c3ccccc3-c3ccc4sc5cccc(-c6nc(-c7ccccc7)nc(-c7ccccc7)n6)c5c4c3)cc21]

TABLE 1-continued
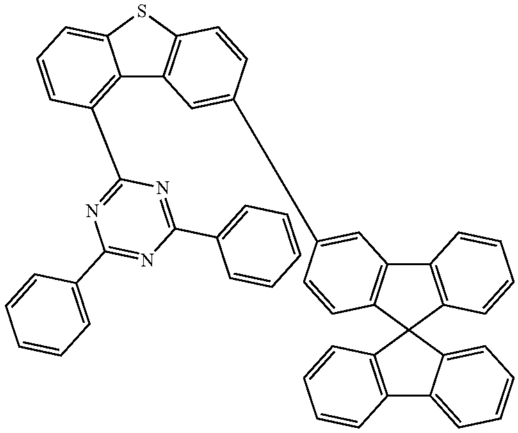 [SMILES: c1ccc(-c2nc(-c3ccccc3)nc(-c3cccc4sc5ccc(-c6ccc7c(c6)-c6ccccc6C76c7ccccc7-c7ccccc76)cc5c34)n2)cc1]
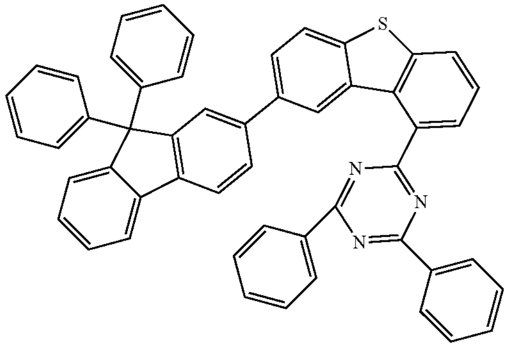 [SMILES: c1ccc(-c2nc(-c3ccccc3)nc(-c3cccc4sc5ccc(-c6ccc7c(c6)C(c6ccccc6)(c6ccccc6)c6ccccc6-7)cc5c34)n2)cc1]
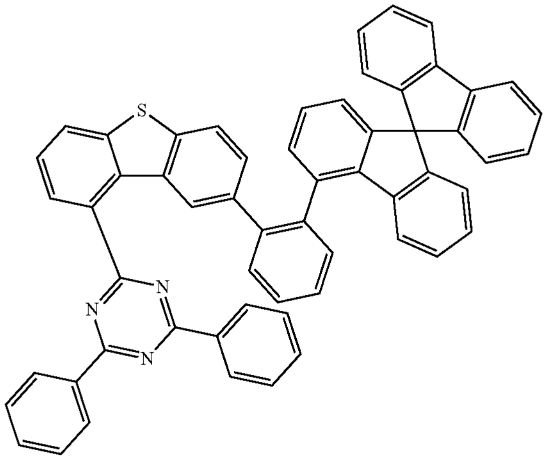 [SMILES: c1ccc(-c2nc(-c3ccccc3)nc(-c3cccc4sc5ccc(-c6ccccc6-c6cccc7c6-c6ccccc6C76c7ccccc7-c7ccccc76)cc5c34)n2)cc1]
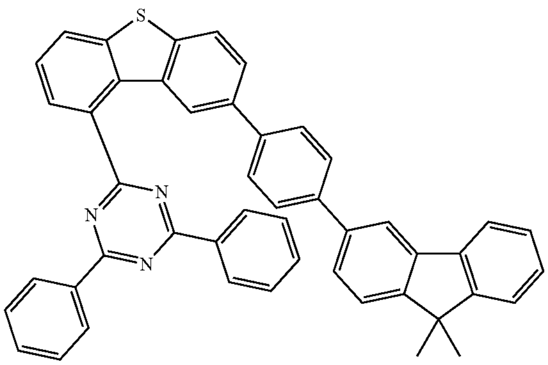 [SMILES: CC1(C)c2ccccc2-c2cc(-c3ccc(-c4ccc5sc6cccc(-c7nc(-c8ccccc8)nc(-c8ccccc8)n7)c6c5c4)cc3)ccc21]

TABLE 1-continued
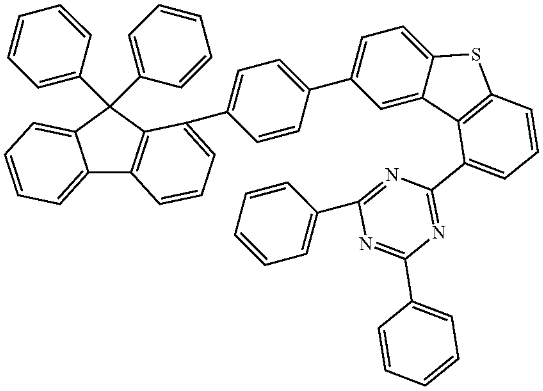 [SMILES: c1ccc(-c2nc(-c3ccccc3)nc(-c3cccc4sc5ccc(-c6ccc(-c7cccc8c7C(c7ccccc7)(c7ccccc7)c7ccccc7-8)cc6)cc5c34)n2)cc1]
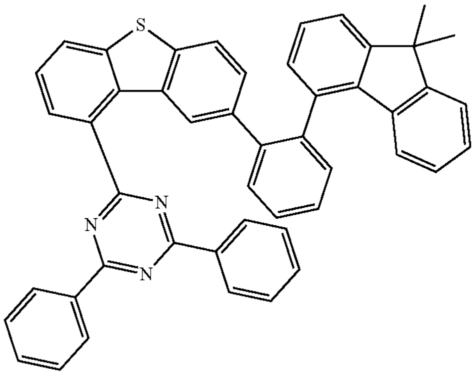 [SMILES: CC1(C)c2ccccc2-c2c(-c3ccccc3-c3ccc4sc5cccc(-c6nc(-c7ccccc7)nc(-c7ccccc7)n6)c5c4c3)cccc21]
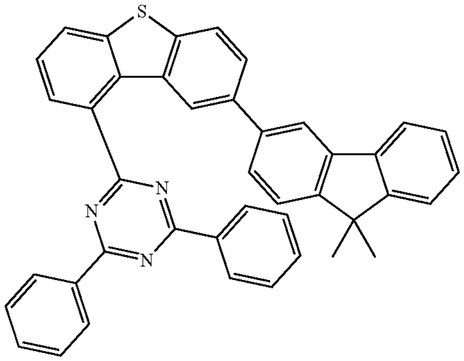 [SMILES: CC1(C)c2ccccc2-c2cc(-c3ccc4sc5cccc(-c6nc(-c7ccccc7)nc(-c7ccccc7)n6)c5c4c3)ccc21]
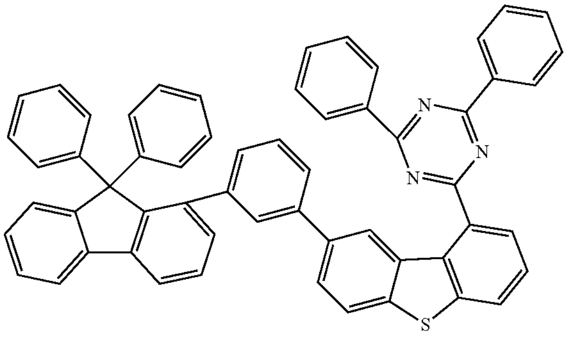 [SMILES: c1ccc(-c2nc(-c3ccccc3)nc(-c3cccc4sc5ccc(-c6cccc(-c7cccc8c7C(c7ccccc7)(c7ccccc7)c7ccccc7-8)c6)cc5c34)n2)cc1]

TABLE 1-continued
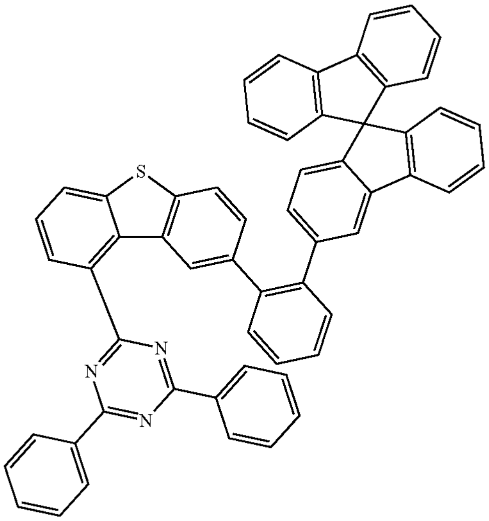 [SMILES: c1ccc(-c2nc(-c3ccccc3)nc(-c3cccc4sc5ccc(-c6ccccc6-c6ccc7c(c6)-c6ccccc6C76c7ccccc7-c7ccccc76)cc5c34)n2)cc1]
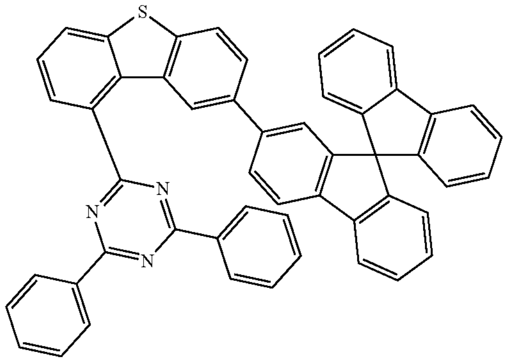 [SMILES: c1ccc(-c2nc(-c3ccccc3)nc(-c3cccc4sc5ccc(-c6ccc7c(c6)C6(c8ccccc8-c8ccccc86)c6ccccc6-7)cc5c34)n2)cc1]
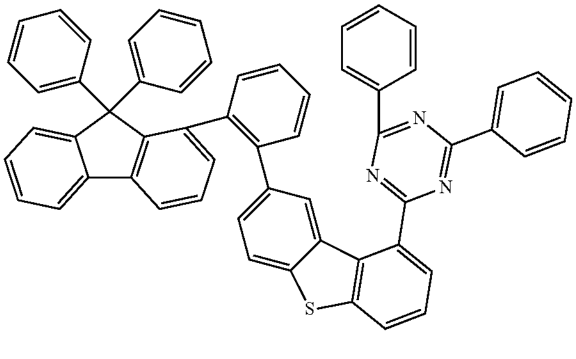 [SMILES: c1ccc(-c2nc(-c3ccccc3)nc(-c3cccc4sc5ccc(-c6ccccc6-c6cccc7c6C(c6ccccc6)(c6ccccc6)c6ccccc6-7)cc5c34)n2)cc1]

TABLE 1-continued
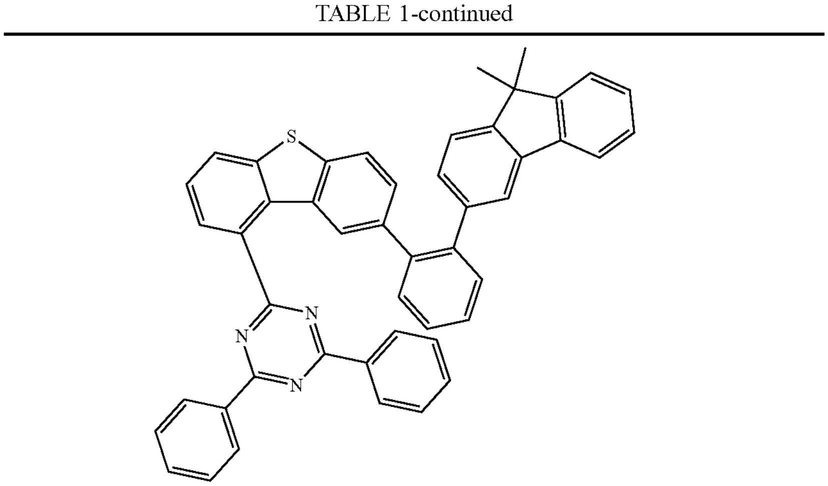
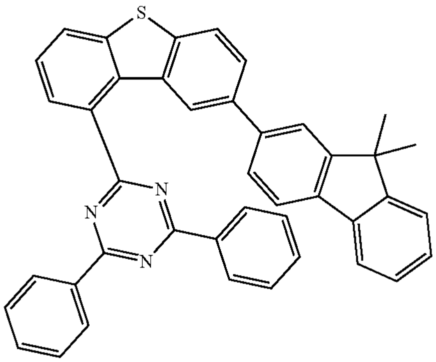 [SMILES: CC1(C)c2ccccc2-c2ccc(-c3ccc4sc5cccc(-c6nc(-c7ccccc7)nc(-c7ccccc7)n6)c5c4c3)cc21]
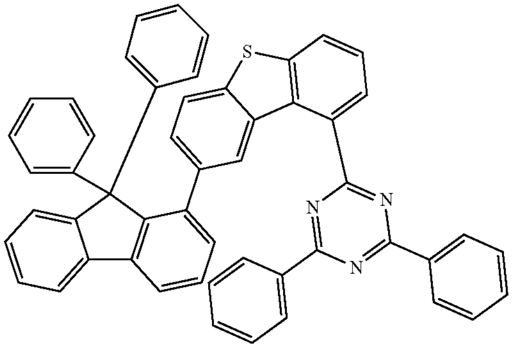 [SMILES: c1ccc(-c2nc(-c3ccccc3)nc(-c3cccc4sc5ccc(-c6cccc7c6C(c6ccccc6)(c6ccccc6)c6ccccc6-7)cc5c34)n2)cc1]
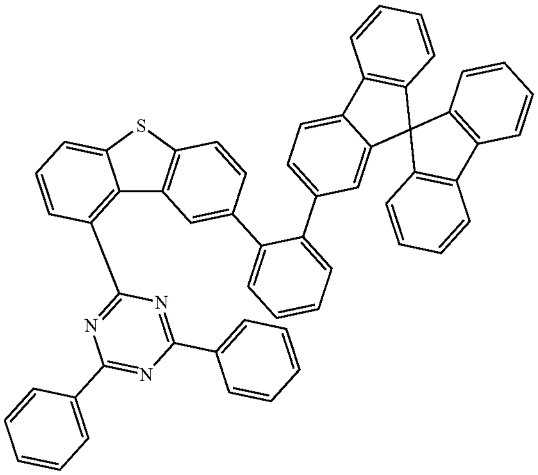 [SMILES: c1ccc(-c2nc(-c3ccccc3)nc(-c3cccc4sc5ccc(-c6ccccc6-c6ccc7c(c6)C6(c8ccccc8-c8ccccc86)c6ccccc6-7)cc5c34)n2)cc1]

TABLE 1-continued
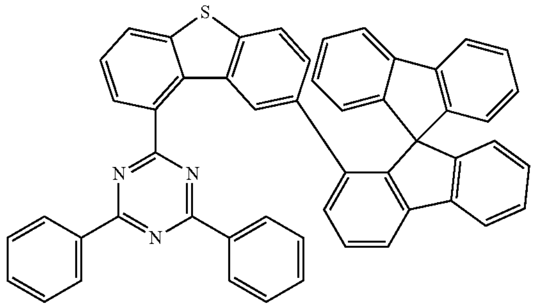 [SMILES: c1ccc(-c2nc(-c3ccccc3)nc(-c3cccc4sc5ccc(-c6cccc7c6C6(c8ccccc8-c8ccccc86)c6ccccc6-7)cc5c34)n2)cc1]
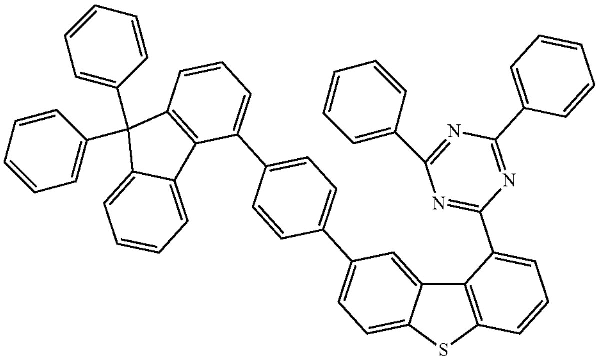 [SMILES: c1ccc(-c2nc(-c3ccccc3)nc(-c3cccc4sc5ccc(-c6ccc(-c7cccc8c7-c7ccccc7C8(c7ccccc7)c7ccccc7)cc6)cc5c34)n2)cc1]
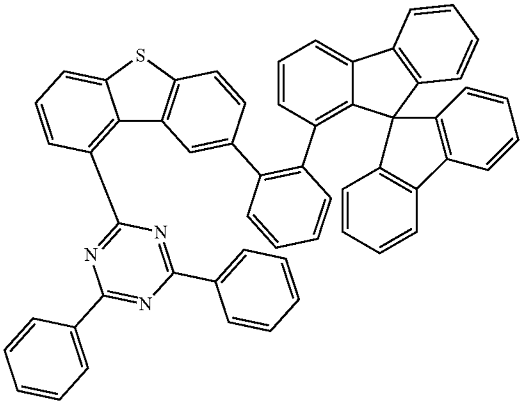 [SMILES: c1ccc(-c2nc(-c3ccccc3)nc(-c3cccc4sc5ccc(-c6ccccc6-c6cccc7c6C6(c8ccccc8-c8ccccc86)c6ccccc6-7)cc5c34)n2)cc1]
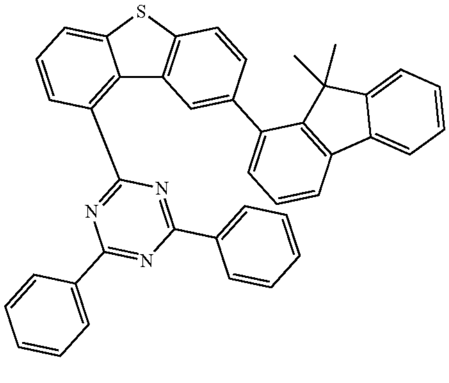 [SMILES: CC1(C)c2ccccc2-c2cccc(-c3ccc4sc5cccc(-c6nc(-c7ccccc7)nc(-c7ccccc7)n6)c5c4c3)c21]

TABLE 1-continued
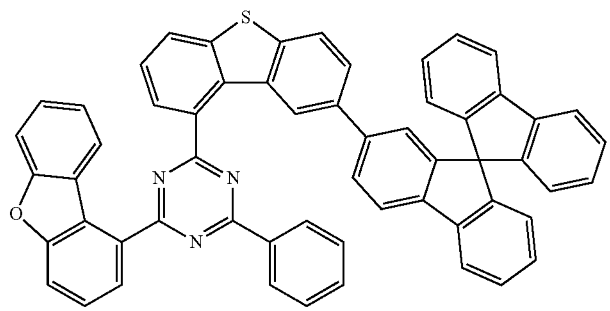 [SMILES: c1ccc(-c2nc(-c3cccc4oc5ccccc5c34)nc(-c3cccc4sc5ccc(-c6ccc7c(c6)C6(c8ccccc8-c8ccccc86)c6ccccc6-7)cc5c34)n2)cc1]
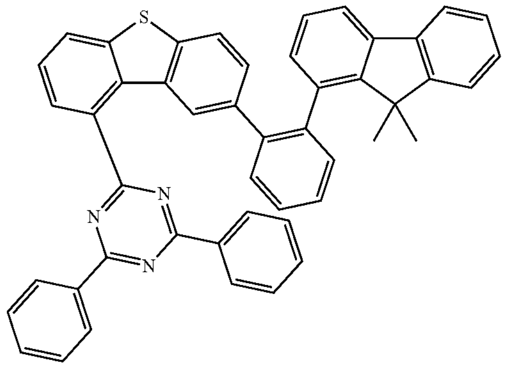 [SMILES: CC1(C)c2ccccc2-c2cccc(-c3ccccc3-c3ccc4sc5cccc(-c6nc(-c7ccccc7)nc(-c7ccccc7)n6)c5c4c3)c21]
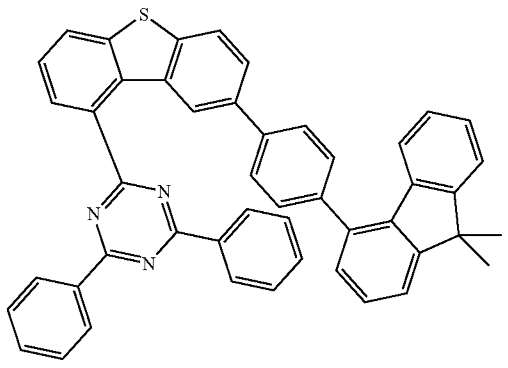 [SMILES: CC1(C)c2ccccc2-c2c(-c3ccc(-c4ccc5sc6cccc(-c7nc(-c8ccccc8)nc(-c8ccccc8)n7)c6c5c4)cc3)cccc21]
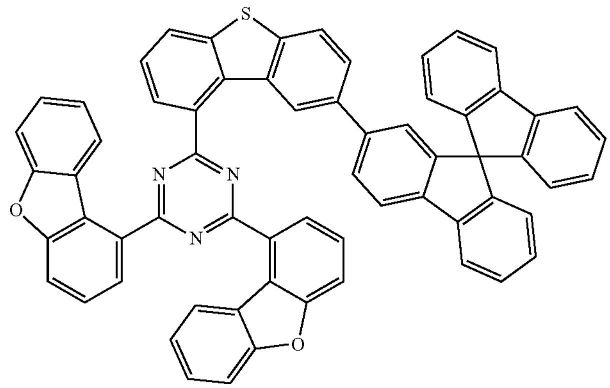 [SMILES: c1ccc2c(c1)-c1ccccc1C21c2ccccc2-c2ccc(-c3ccc4sc5cccc(-c6nc(-c7cccc8oc9ccccc9c78)nc(-c7cccc8oc9ccccc9c78)n6)c5c4c3)cc21]

TABLE 1-continued
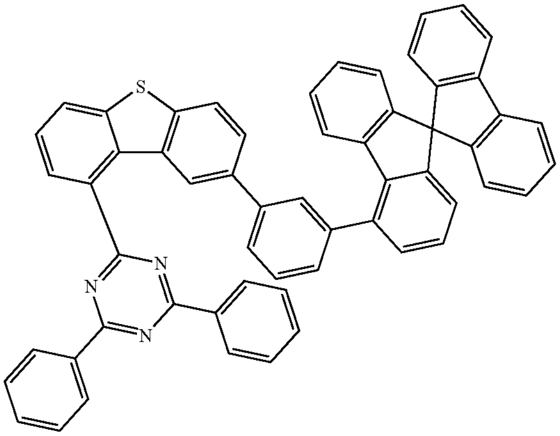 [SMILES: c1ccc(-c2nc(-c3ccccc3)nc(-c3cccc4sc5ccc(-c6cccc(-c7cccc8c7-c7ccccc7C87c8ccccc8-c8ccccc87)c6)cc5c34)n2)cc1]
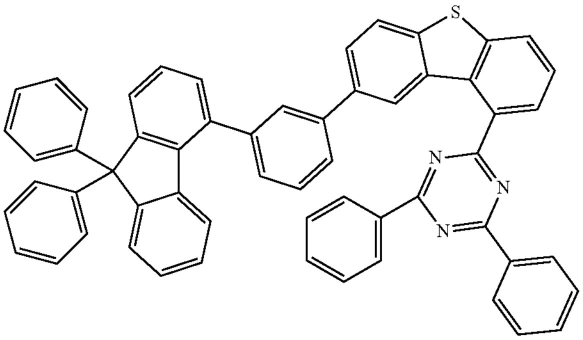 [SMILES: c1ccc(-c2nc(-c3ccccc3)nc(-c3cccc4sc5ccc(-c6cccc(-c7cccc8c7-c7ccccc7C8(c7ccccc7)c7ccccc7)c6)cc5c34)n2)cc1]
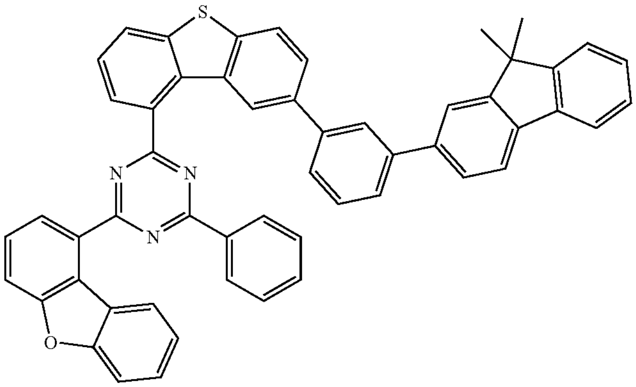 [SMILES: CC1(C)c2ccccc2-c2ccc(-c3cccc(-c4ccc5sc6cccc(-c7nc(-c8ccccc8)nc(-c8cccc9oc%10ccccc%10c89)n7)c6c5c4)c3)cc21]
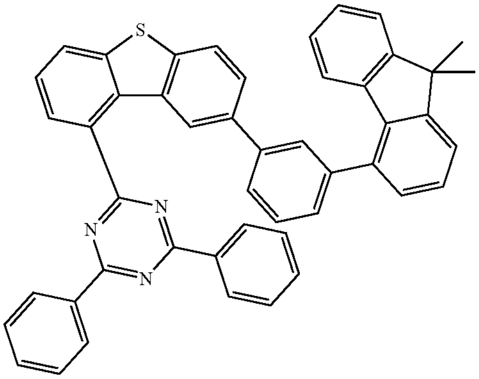 [SMILES: CC1(C)c2ccccc2-c2c(-c3cccc(-c4ccc5sc6cccc(-c7nc(-c8ccccc8)nc(-c8ccccc8)n7)c6c5c4)c3)cccc21]

TABLE 1-continued
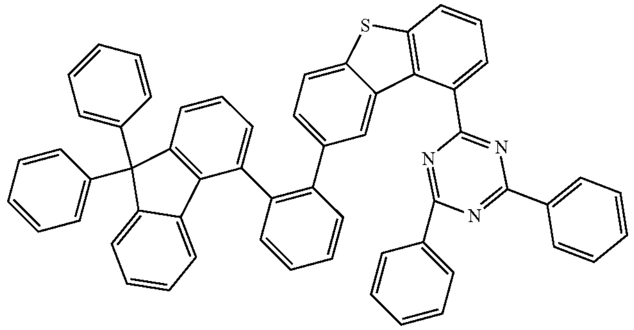 [SMILES: c1ccc(-c2nc(-c3ccccc3)nc(-c3cccc4sc5ccc(-c6ccccc6-c6cccc7c6-c6ccccc6C7(c6ccccc6)c6ccccc6)cc5c34)n2)cc1]
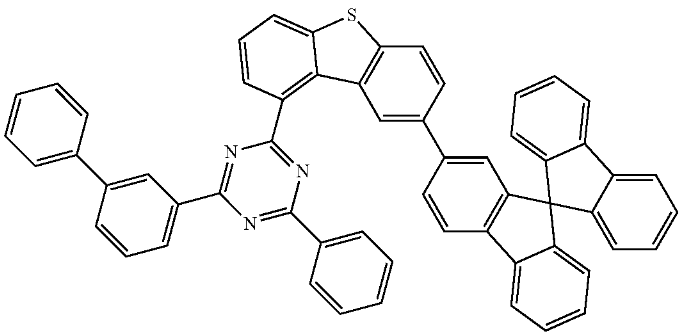 [SMILES: c1ccc(-c2cccc(-c3nc(-c4ccccc4)nc(-c4cccc5sc6ccc(-c7ccc8c(c7)C7(c9ccccc9-c9ccccc97)c7ccccc7-8)cc6c45)n3)c2)cc1]
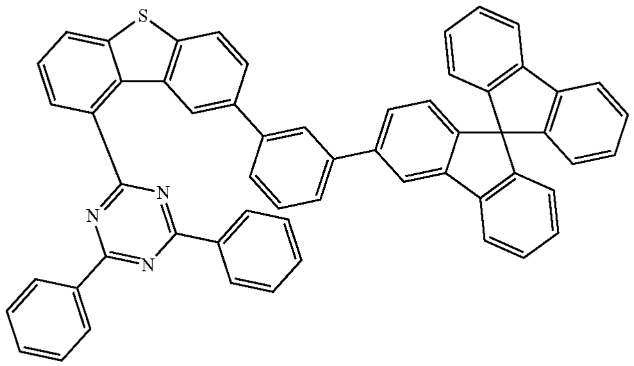 [SMILES: c1ccc(-c2nc(-c3ccccc3)nc(-c3cccc4sc5ccc(-c6cccc(-c7ccc8c(c7)-c7ccccc7C87c8ccccc8-c8ccccc87)c6)cc5c34)n2)cc1]
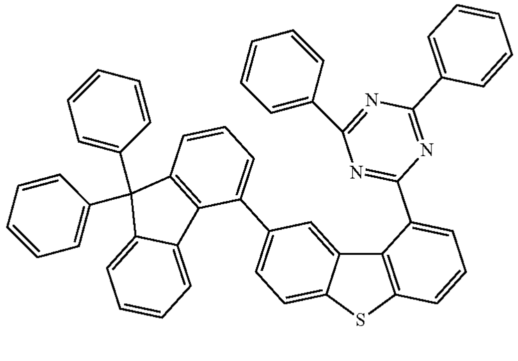 [SMILES: c1ccc(-c2nc(-c3ccccc3)nc(-c3cccc4sc5ccc(-c6cccc7c6-c6ccccc6C7(c6ccccc6)c6ccccc6)cc5c34)n2)cc1]

TABLE 1-continued
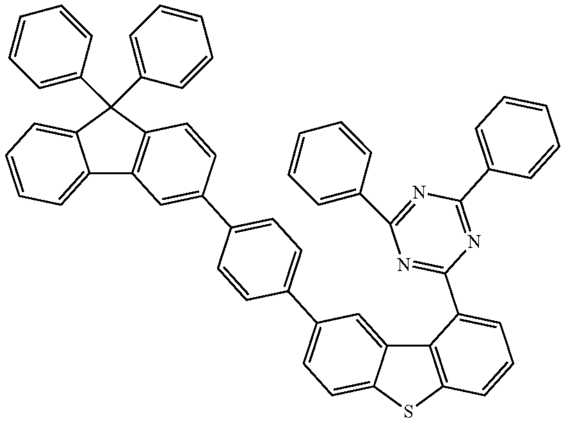 [SMILES: c1ccc(-c2nc(-c3ccccc3)nc(-c3cccc4sc5ccc(-c6ccc(-c7ccc8c(c7)-c7ccccc7C8(c7ccccc7)c7ccccc7)cc6)cc5c34)n2)cc1]
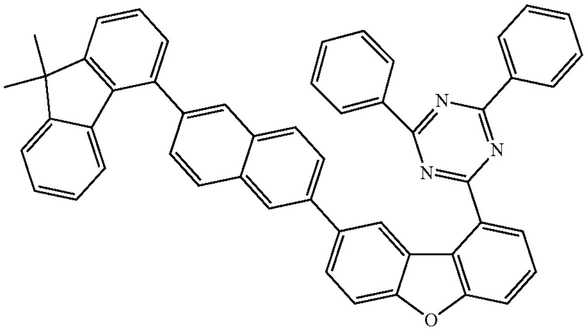 [SMILES: CC1(C)c2ccccc2-c2c(-c3ccc4cc(-c5ccc6oc7cccc(-c8nc(-c9ccccc9)nc(-c9ccccc9)n8)c7c6c5)ccc4c3)cccc21]
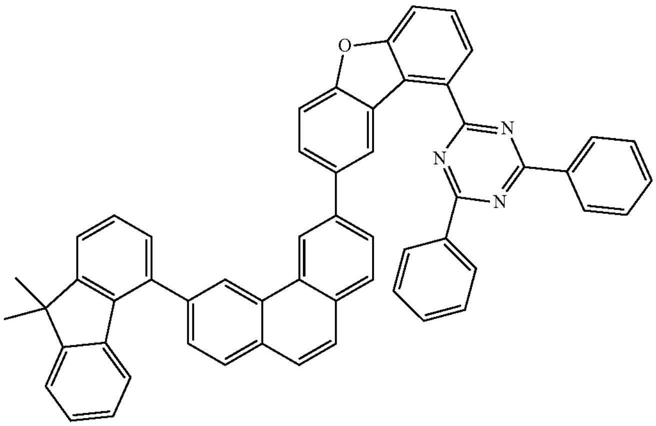 [SMILES: CC1(C)c2ccccc2-c2c(-c3ccc4ccc5ccc(-c6ccc7oc8cccc(-c9nc(-c%10ccccc%10)nc(-c%10ccccc%10)n9)c8c7c6)cc5c4c3)cccc21]
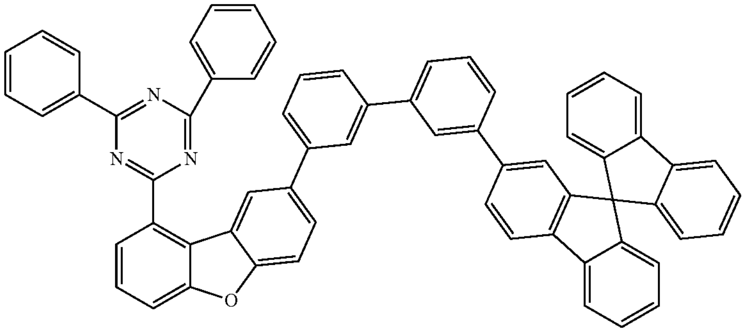 [SMILES: c1ccc(-c2nc(-c3ccccc3)nc(-c3cccc4oc5ccc(-c6cccc(-c7cccc(-c8ccc9c(c8)C8(c%10ccccc%10-c%10ccccc%108)c8ccccc8-9)c7)c6)cc5c34)n2)cc1]

TABLE 1-continued
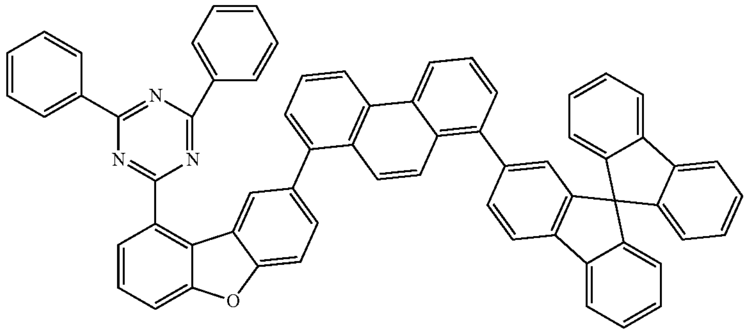 [SMILES: c1ccc(-c2nc(-c3ccccc3)nc(-c3cccc4oc5ccc(-c6cccc7c6ccc6c(-c8ccc9c(c8)C8(c%10ccccc%10-c%10ccccc%108)c8ccccc8-9)cccc67)cc5c34)n2)cc1]
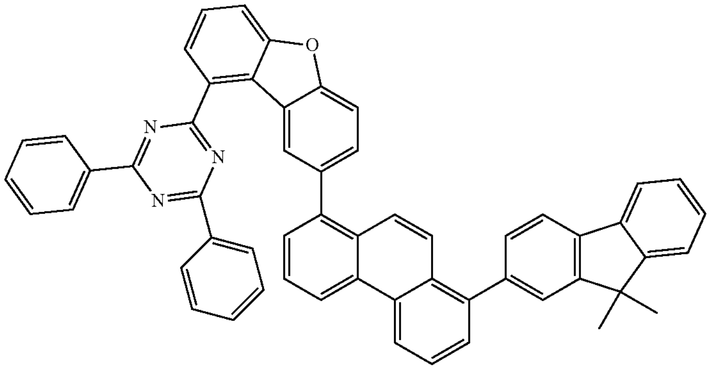 [SMILES: CC1(C)c2ccccc2-c2ccc(-c3cccc4c3ccc3c(-c5ccc6oc7cccc(-c8nc(-c9ccccc9)nc(-c9ccccc9)n8)c7c6c5)cccc34)cc21]
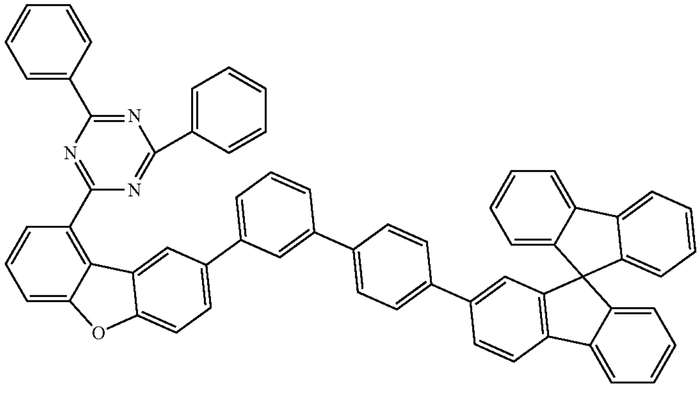 [SMILES: c1ccc(-c2nc(-c3ccccc3)nc(-c3cccc4oc5ccc(-c6cccc(-c7ccc(-c8ccc9c(c8)C8(c%10ccccc%10-c%10ccccc%108)c8ccccc8-9)cc7)c6)cc5c34)n2)cc1]
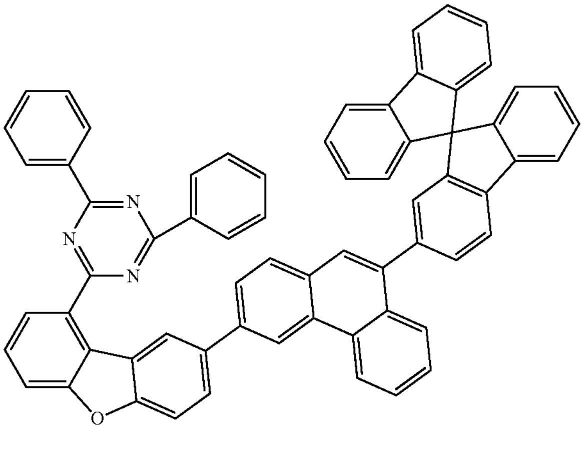 [SMILES: c1ccc(-c2nc(-c3ccccc3)nc(-c3cccc4oc5ccc(-c6ccc7cc(-c8ccc9c(c8)C8(c%10ccccc%10-c%10ccccc%108)c8ccccc8-9)c8ccccc8c7c6)cc5c34)n2)cc1]

TABLE 1-continued
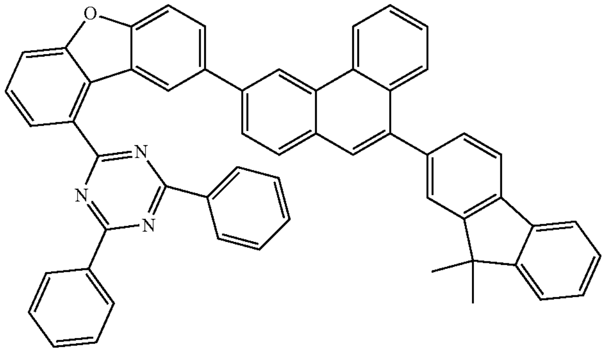 [SMILES: CC1(C)c2ccccc2-c2ccc(-c3cc4ccc(-c5ccc6oc7cccc(-c8nc(-c9ccccc9)nc(-c9ccccc9)n8)c7c6c5)cc4c4ccccc34)cc21]
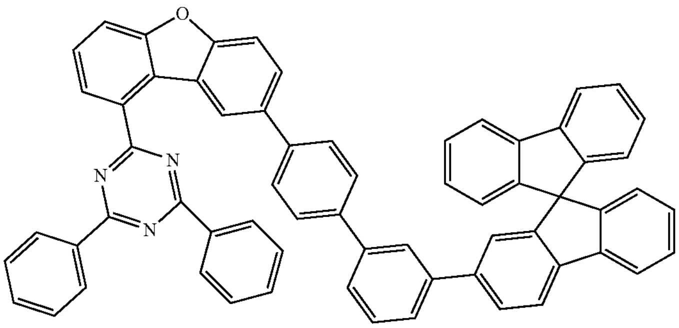 [SMILES: c1ccc(-c2nc(-c3ccccc3)nc(-c3cccc4oc5ccc(-c6ccc(-c7cccc(-c8ccc9c(c8)C8(c%10ccccc%10-c%10ccccc%108)c8ccccc8-9)c7)cc6)cc5c34)n2)cc1]
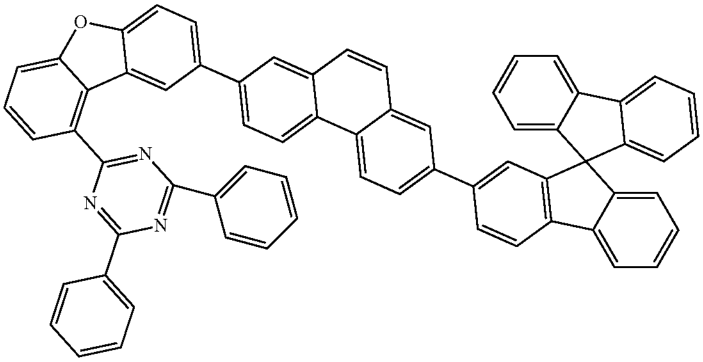 [SMILES: c1ccc(-c2nc(-c3ccccc3)nc(-c3cccc4oc5ccc(-c6ccc7c(ccc8cc(-c9ccc%10c(c9)C9(c%11ccccc%11-c%11ccccc%119)c9ccccc9-%10)ccc87)c6)cc5c34)n2)cc1]
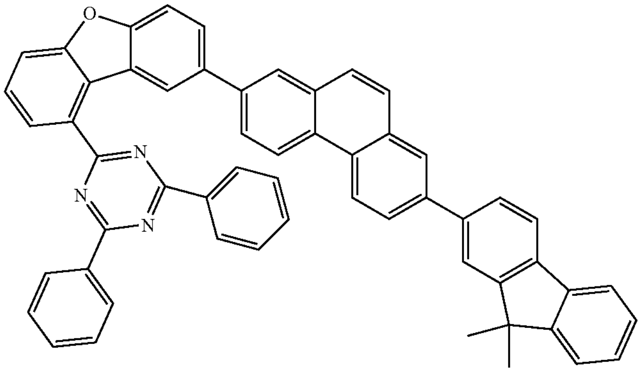 [SMILES: CC1(C)c2ccccc2-c2ccc(-c3ccc4c(ccc5cc(-c6ccc7oc8cccc(-c9nc(-c%10ccccc%10)nc(-c%10ccccc%10)n9)c8c7c6)ccc54)c3)cc21]

TABLE 1-continued
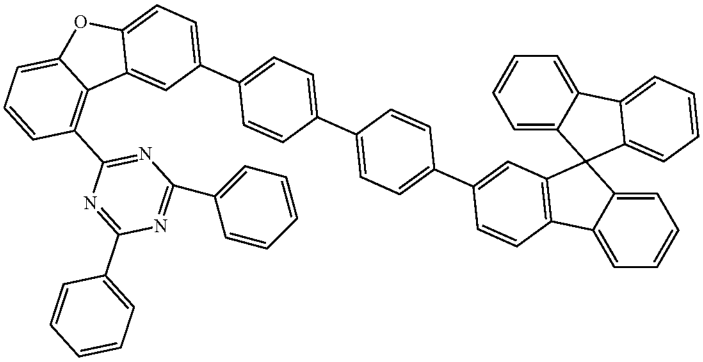 [SMILES: c1ccc(-c2nc(-c3ccccc3)nc(-c3cccc4oc5ccc(-c6ccc(-c7ccc(-c8ccc9c(c8)C8(c%10ccccc%10-c%10ccccc%108)c8ccccc8-9)cc7)cc6)cc5c34)n2)cc1]
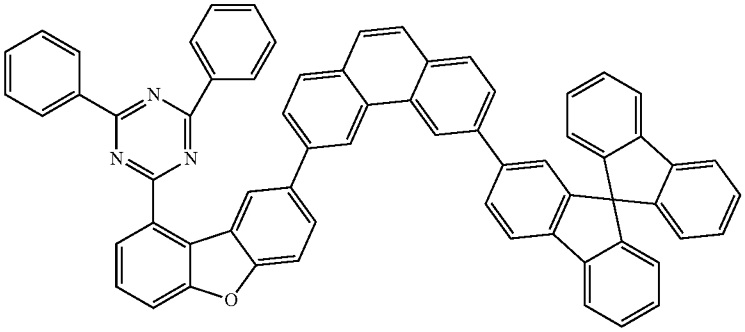 [SMILES: c1ccc(-c2nc(-c3ccccc3)nc(-c3cccc4oc5ccc(-c6ccc7ccc8ccc(-c9ccc%10c(c9)C9(c%11ccccc%11-c%11ccccc%119)c9ccccc9-%10)cc8c7c6)cc5c34)n2)cc1]
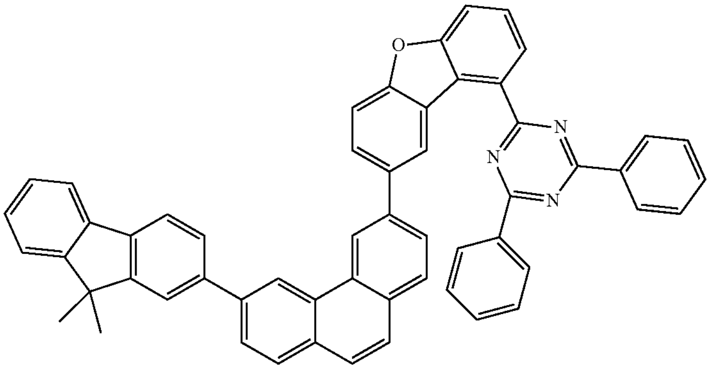 [SMILES: CC1(C)c2ccccc2-c2ccc(-c3ccc4ccc5ccc(-c6ccc7oc8cccc(-c9nc(-c%10ccccc%10)nc(-c%10ccccc%10)n9)c8c7c6)cc5c4c3)cc21]
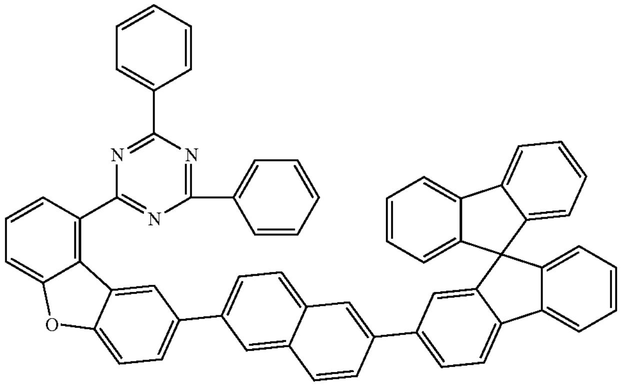 [SMILES: c1ccc(-c2nc(-c3ccccc3)nc(-c3cccc4oc5ccc(-c6ccc7cc(-c8ccc9c(c8)C8(c%10ccccc%10-c%10ccccc%108)c8ccccc8-9)ccc7c6)cc5c34)n2)cc1]

TABLE 1-continued
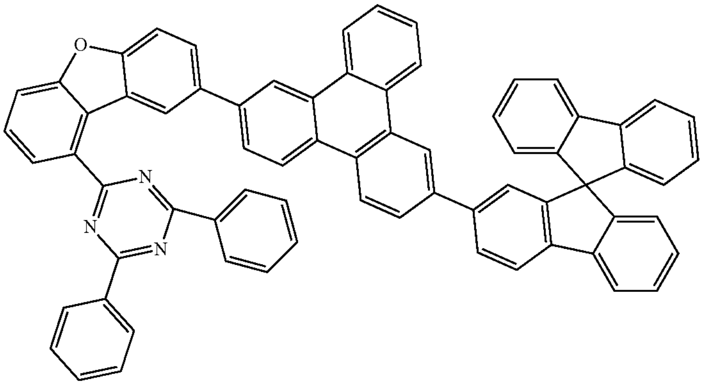 [SMILES: c1ccc(-c2nc(-c3ccccc3)nc(-c3cccc4oc5ccc(-c6ccc7c8ccc(-c9ccc%10c(c9)C9(c%11ccccc%11-c%11ccccc%119)c9ccccc9-%10)cc8c8ccccc8c7c6)cc5c34)n2)cc1]
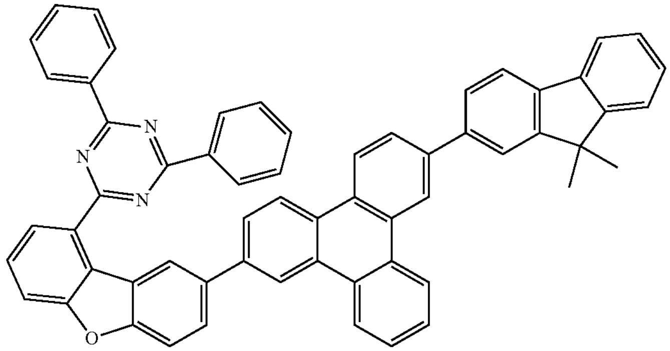 [SMILES: CC1(C)c2ccccc2-c2ccc(-c3ccc4c5ccc(-c6ccc7oc8cccc(-c9nc(-c%10ccccc%10)nc(-c%10ccccc%10)n9)c8c7c6)cc5c5ccccc5c4c3)cc21]
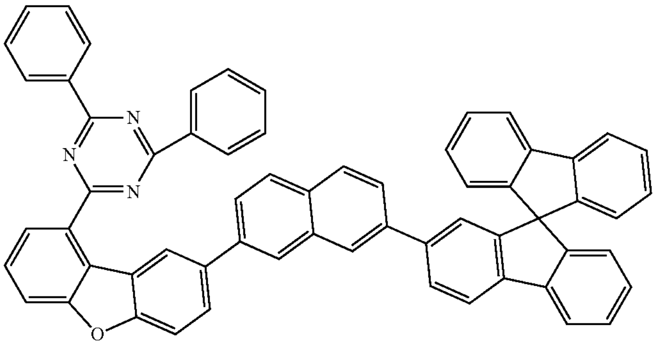 [SMILES: c1ccc(-c2nc(-c3ccccc3)nc(-c3cccc4oc5ccc(-c6ccc7ccc(-c8ccc9c(c8)C8(c%10ccccc%10-c%10ccccc%108)c8ccccc8-9)cc7c6)cc5c34)n2)cc1]
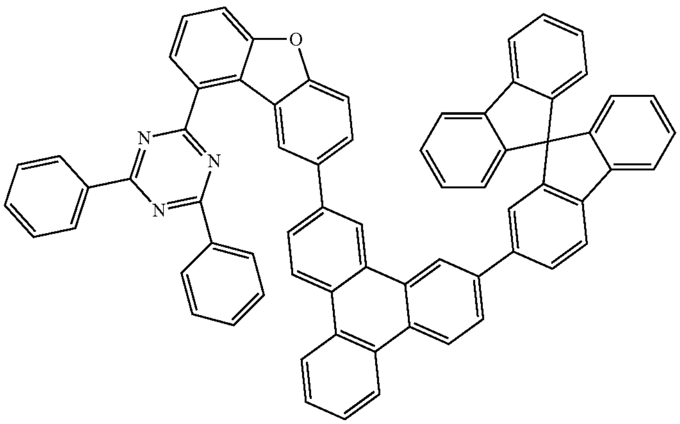 [SMILES: c1ccc(-c2nc(-c3ccccc3)nc(-c3cccc4oc5ccc(-c6ccc7c8ccccc8c8ccc(-c9ccc%10c(c9)C9(c%11ccccc%11-c%11ccccc%119)c9ccccc9-%10)cc8c7c6)cc5c34)n2)cc1]

TABLE 1-continued
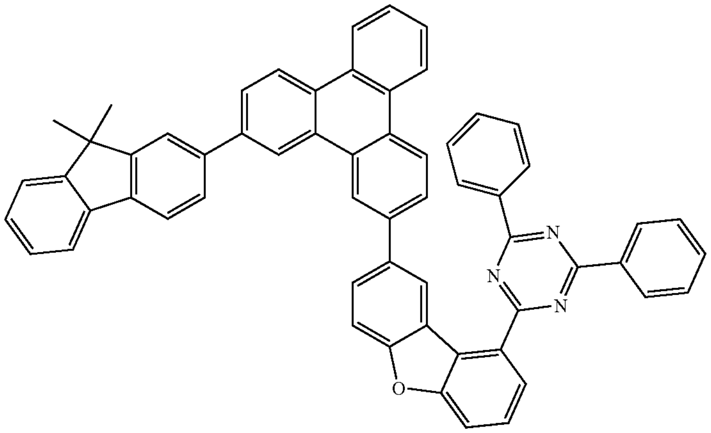 [SMILES: CC1(C)c2ccccc2-c2ccc(-c3ccc4c5ccccc5c5ccc(-c6ccc7oc8cccc(-c9nc(-c%10ccccc%10)nc(-c%10ccccc%10)n9)c8c7c6)cc5c4c3)cc21]
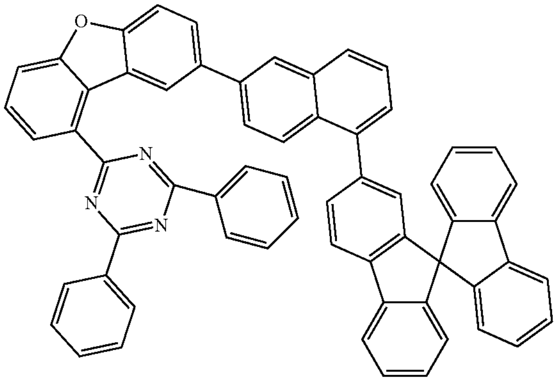 [SMILES: c1ccc(-c2nc(-c3ccccc3)nc(-c3cccc4oc5ccc(-c6ccc7c(-c8ccc9c(c8)C8(c%10ccccc%10-c%10ccccc%108)c8ccccc8-9)cccc7c6)cc5c34)n2)cc1]
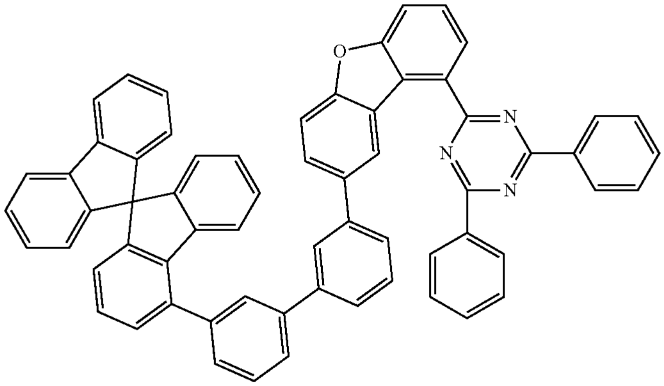 [SMILES: c1ccc(-c2nc(-c3ccccc3)nc(-c3cccc4oc5ccc(-c6cccc(-c7cccc(-c8cccc9c8-c8ccccc8C98c9ccccc9-c9ccccc98)c7)c6)cc5c34)n2)cc1]
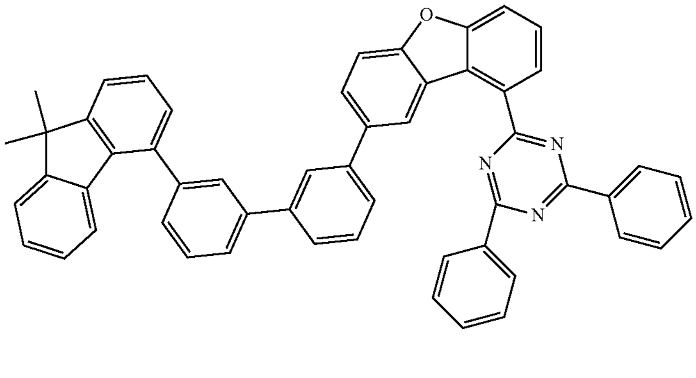 [SMILES: CC1(C)c2ccccc2-c2c(-c3cccc(-c4cccc(-c5ccc6oc7cccc(-c8nc(-c9ccccc9)nc(-c9ccccc9)n8)c7c6c5)c4)c3)cccc21]

TABLE 1-continued
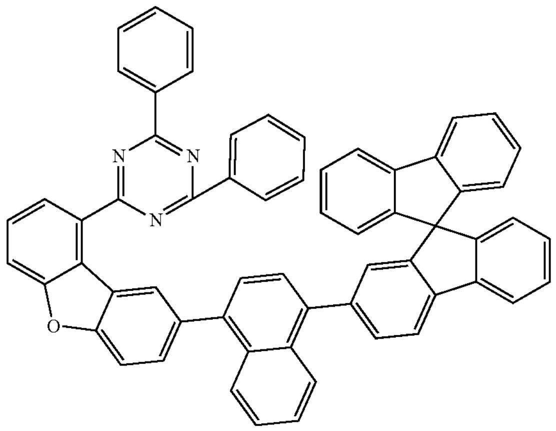 [SMILES: c1ccc(-c2nc(-c3ccccc3)nc(-c3cccc4oc5ccc(-c6ccc(-c7ccc8c(c7)C7(c9ccccc9-c9ccccc97)c7ccccc7-8)c7ccccc67)cc5c34)n2)cc1]
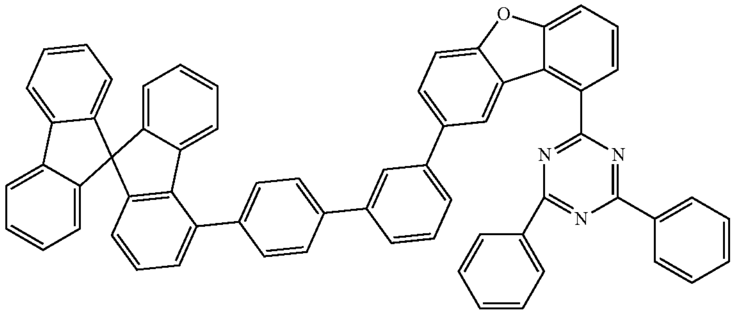 [SMILES: c1ccc(-c2nc(-c3ccccc3)nc(-c3cccc4oc5ccc(-c6cccc(-c7ccc(-c8cccc9c8-c8ccccc8C98c9ccccc9-c9ccccc98)cc7)c6)cc5c34)n2)cc1]
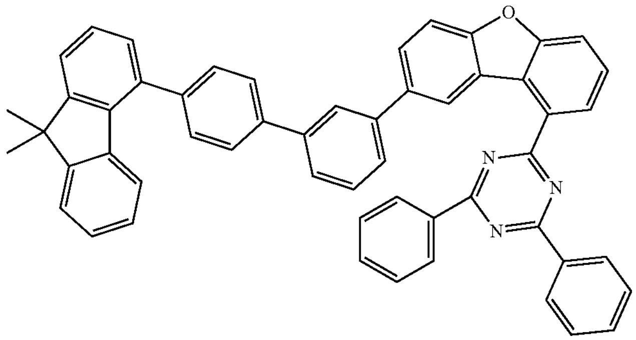 [SMILES: CC1(C)c2ccccc2-c2c(-c3ccc(-c4cccc(-c5ccc6oc7cccc(-c8nc(-c9ccccc9)nc(-c9ccccc9)n8)c7c6c5)c4)cc3)cccc21]
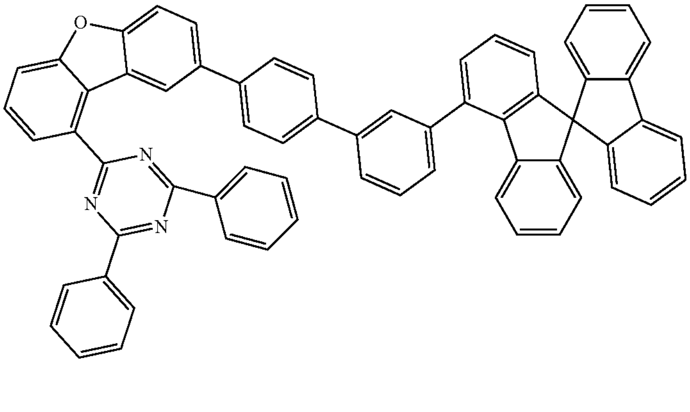 [SMILES: c1ccc(-c2nc(-c3ccccc3)nc(-c3cccc4oc5ccc(-c6ccc(-c7cccc(-c8cccc9c8-c8ccccc8C98c9ccccc9-c9ccccc98)c7)cc6)cc5c34)n2)cc1]

TABLE 1-continued
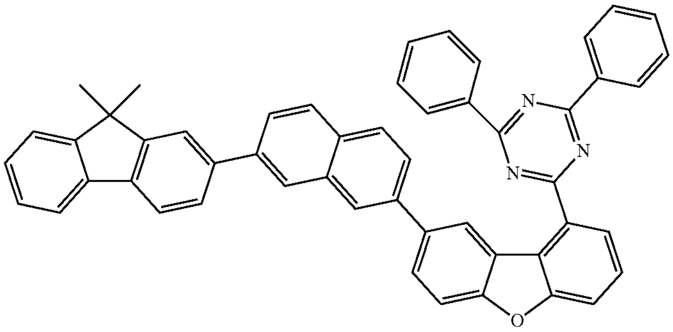 [SMILES: CC1(C)c2ccccc2-c2ccc(-c3ccc4ccc(-c5ccc6oc7cccc(-c8nc(-c9ccccc9)nc(-c9ccccc9)n8)c7c6c5)cc4c3)cc21]
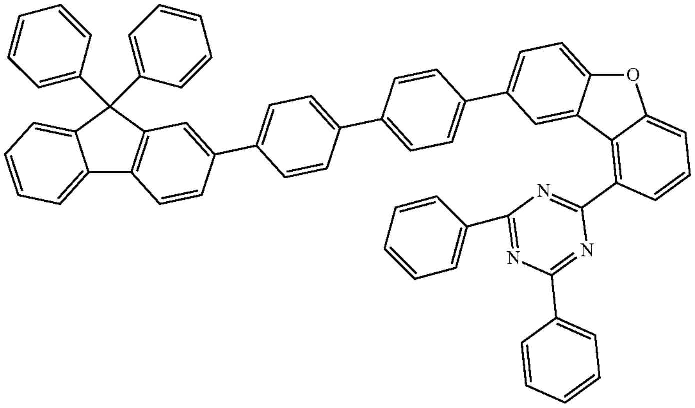 [SMILES: c1ccc(-c2nc(-c3ccccc3)nc(-c3cccc4oc5ccc(-c6ccc(-c7ccc(-c8ccc9c(c8)C(c8ccccc8)(c8ccccc8)c8ccccc8-9)cc7)cc6)cc5c34)n2)cc1]
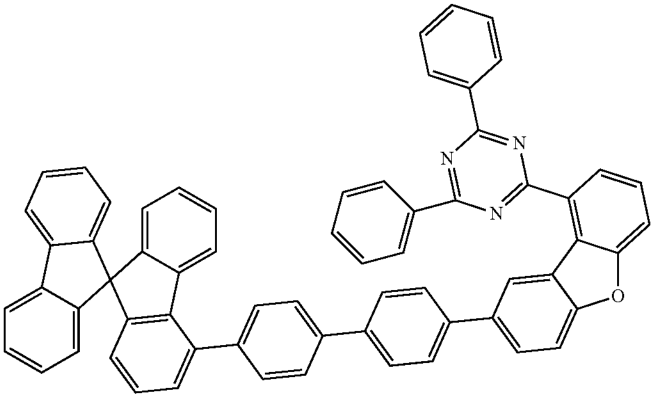 [SMILES: c1ccc(-c2nc(-c3ccccc3)nc(-c3cccc4oc5ccc(-c6ccc(-c7ccc(-c8cccc9c8-c8ccccc8C98c9ccccc9-c9ccccc98)cc7)cc6)cc5c34)n2)cc1]
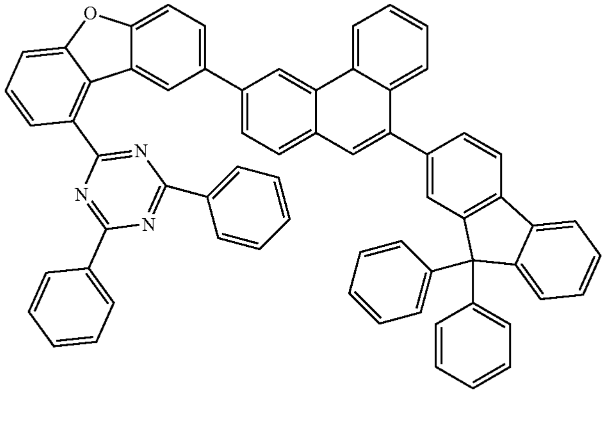 [SMILES: c1ccc(-c2nc(-c3ccccc3)nc(-c3cccc4oc5ccc(-c6ccc7cc(-c8ccc9c(c8)C(c8ccccc8)(c8ccccc8)c8ccccc8-9)c8ccccc8c7c6)cc5c34)n2)cc1]

TABLE 1-continued
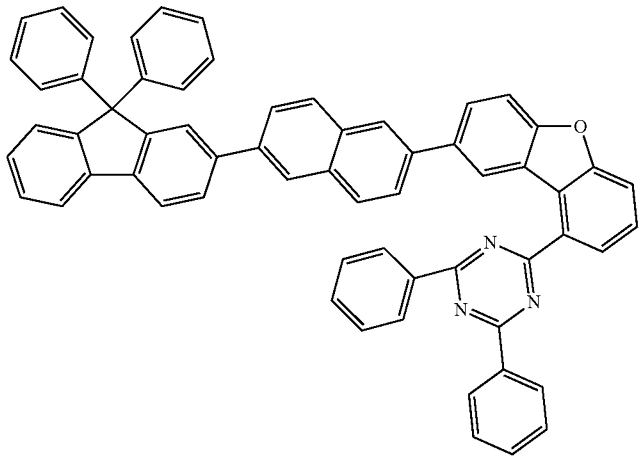 [SMILES: c1ccc(-c2nc(-c3ccccc3)nc(-c3cccc4oc5ccc(-c6ccc7cc(-c8ccc9c(c8)C(c8ccccc8)(c8ccccc8)c8ccccc8-9)ccc7c6)cc5c34)n2)cc1]
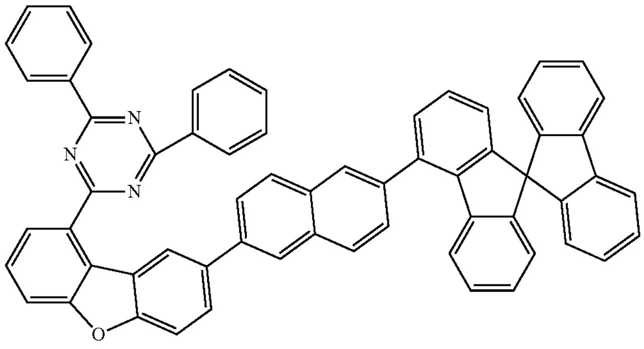 [SMILES: c1ccc(-c2nc(-c3ccccc3)nc(-c3cccc4oc5ccc(-c6ccc7cc(-c8cccc9c8-c8ccccc8C98c9ccccc9-c9ccccc98)ccc7c6)cc5c34)n2)cc1]
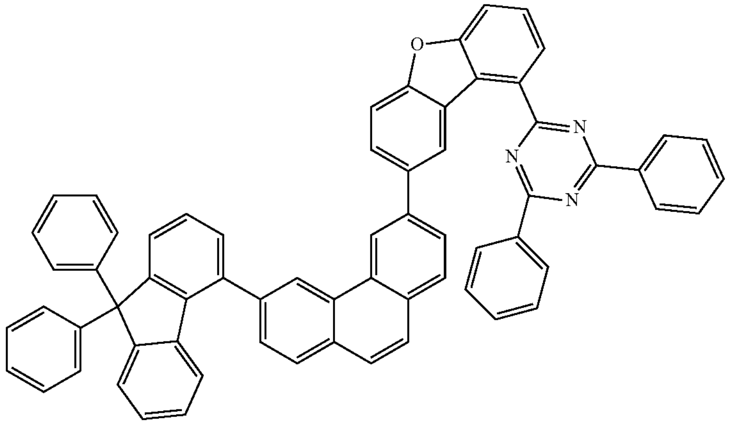 [SMILES: c1ccc(-c2nc(-c3ccccc3)nc(-c3cccc4oc5ccc(-c6ccc7ccc8ccc(-c9cccc%10c9-c9ccccc9C%10(c9ccccc9)c9ccccc9)cc8c7c6)cc5c34)n2)cc1]
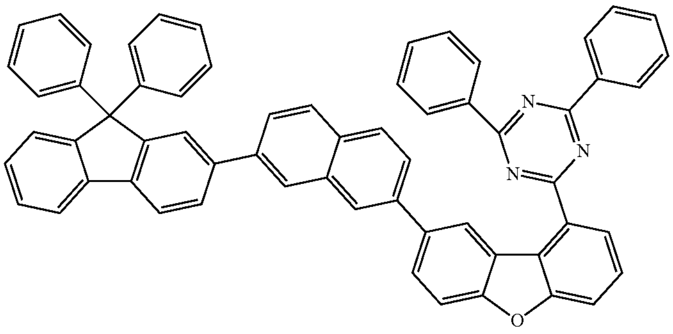 [SMILES: c1ccc(-c2nc(-c3ccccc3)nc(-c3cccc4oc5ccc(-c6ccc7ccc(-c8ccc9c(c8)C(c8ccccc8)(c8ccccc8)c8ccccc8-9)cc7c6)cc5c34)n2)cc1]

TABLE 1-continued
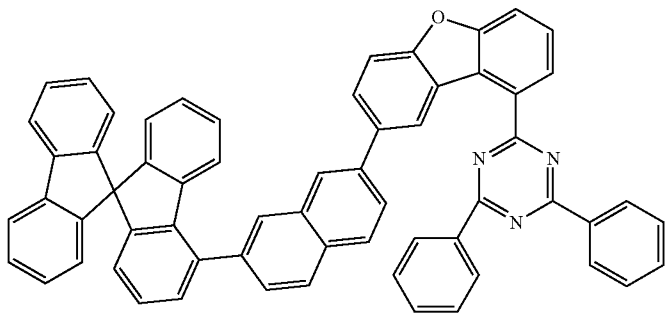 [SMILES: c1ccc(-c2nc(-c3ccccc3)nc(-c3cccc4oc5ccc(-c6ccc7ccc(-c8cccc9c8-c8ccccc8C98c9ccccc9-c9ccccc98)cc7c6)cc5c34)n2)cc1]
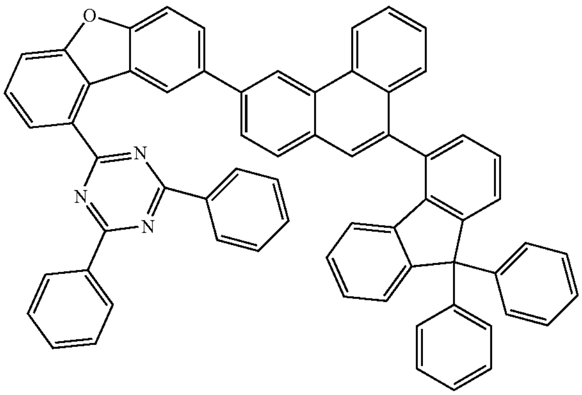 [SMILES: c1ccc(-c2nc(-c3ccccc3)nc(-c3cccc4oc5ccc(-c6ccc7cc(-c8cccc9c8-c8ccccc8C9(c8ccccc8)c8ccccc8)c8ccccc8c7c6)cc5c34)n2)cc1]
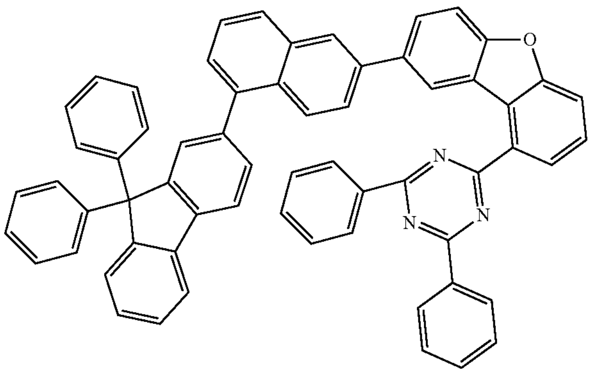 [SMILES: c1ccc(-c2nc(-c3ccccc3)nc(-c3cccc4oc5ccc(-c6ccc7c(-c8ccc9c(c8)C(c8ccccc8)(c8ccccc8)c8ccccc8-9)cccc7c6)cc5c34)n2)cc1]
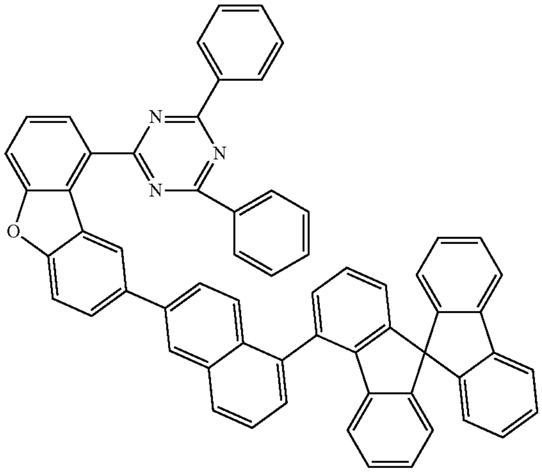 [SMILES: c1ccc(-c2nc(-c3ccccc3)nc(-c3cccc4oc5ccc(-c6ccc7c(-c8cccc9c8-c8ccccc8C98c9ccccc9-c9ccccc98)cccc7c6)cc5c34)n2)cc1]

TABLE 1-continued
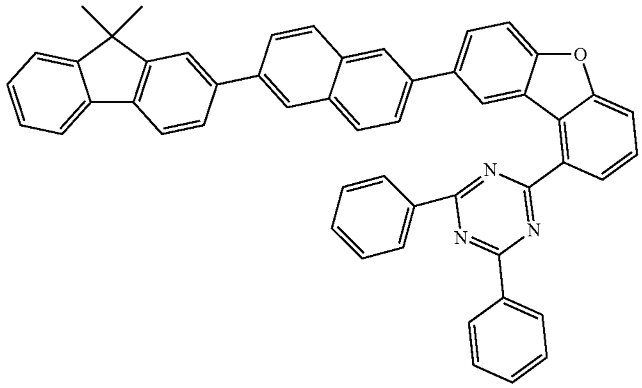 [SMILES: CC1(C)c2ccccc2-c2ccc(-c3ccc4cc(-c5ccc6oc7cccc(-c8nc(-c9ccccc9)nc(-c9ccccc9)n8)c7c6c5)ccc4c3)cc21]
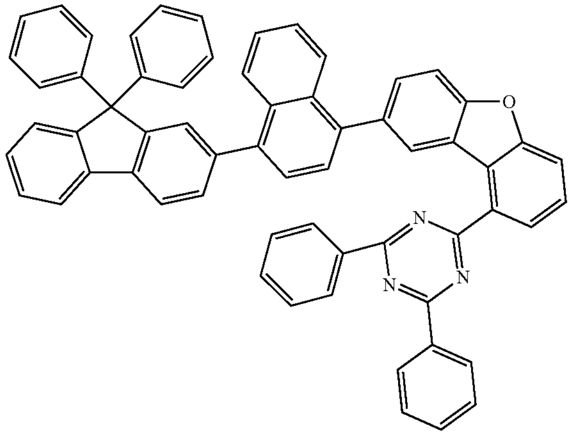 [SMILES: c1ccc(-c2nc(-c3ccccc3)nc(-c3cccc4oc5ccc(-c6ccc(-c7ccc8c(c7)C(c7ccccc7)(c7ccccc7)c7ccccc7-8)c7ccccc67)cc5c34)n2)cc1]
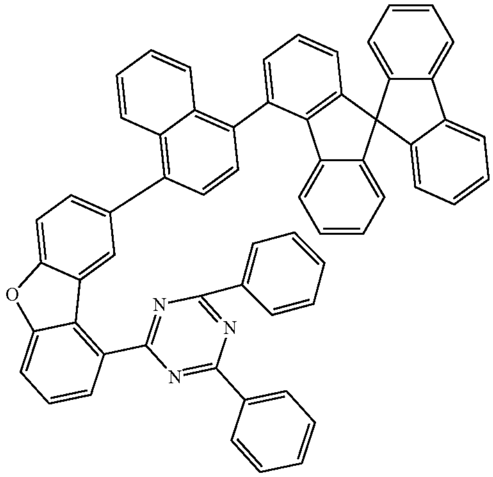 [SMILES: c1ccc(-c2nc(-c3ccccc3)nc(-c3cccc4oc5ccc(-c6ccc(-c7cccc8c7-c7ccccc7C87c8ccccc8-c8ccccc87)c7ccccc67)cc5c34)n2)cc1]

TABLE 1-continued
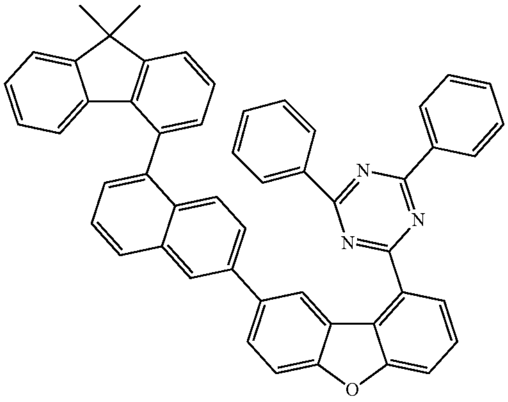 [SMILES: CC1(C)c2ccccc2-c2c(-c3cccc4cc(-c5ccc6oc7cccc(-c8nc(-c9ccccc9)nc(-c9ccccc9)n8)c7c6c5)ccc34)cccc21]
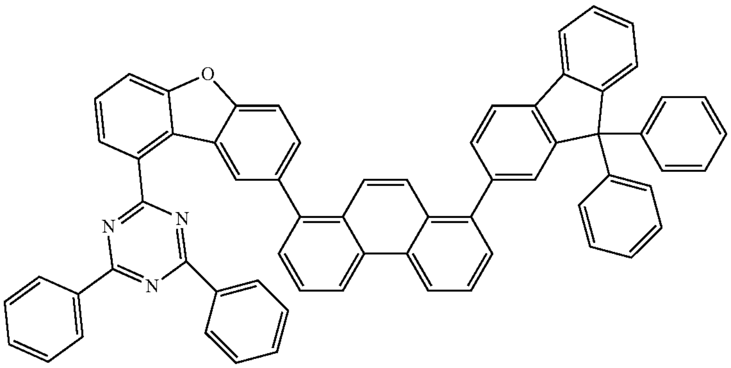 [SMILES: c1ccc(-c2nc(-c3ccccc3)nc(-c3cccc4oc5ccc(-c6cccc7c6ccc6c(-c8ccc9c(c8)C(c8ccccc8)(c8ccccc8)c8ccccc8-9)cccc67)cc5c34)n2)cc1]
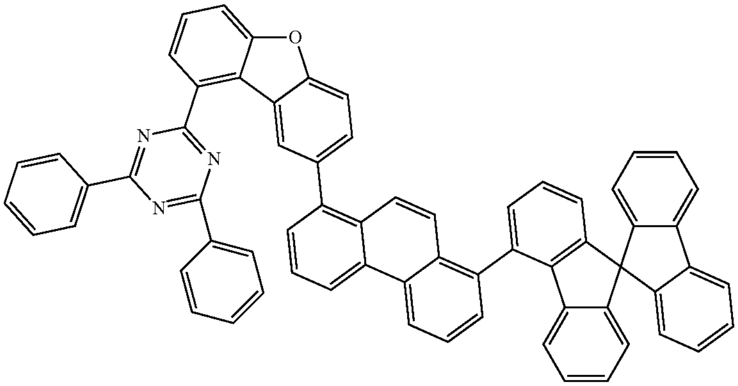 [SMILES: c1ccc(-c2nc(-c3ccccc3)nc(-c3cccc4oc5ccc(-c6cccc7c6ccc6c(-c8cccc9c8-c8ccccc8C98c9ccccc9-c9ccccc98)cccc67)cc5c34)n2)cc1]
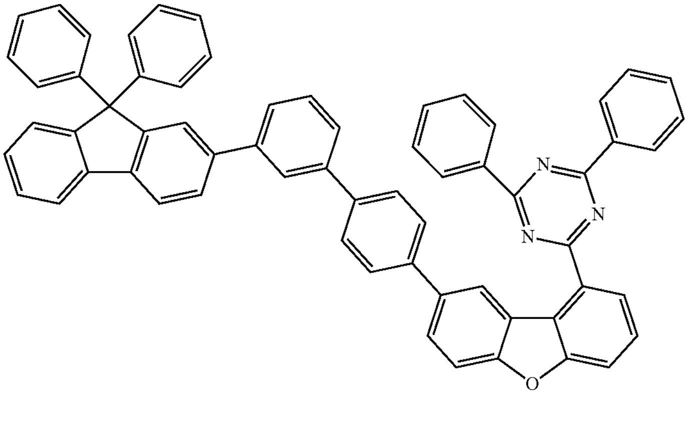 [SMILES: c1ccc(-c2nc(-c3ccccc3)nc(-c3cccc4oc5ccc(-c6ccc(-c7cccc(-c8ccc9c(c8)C(c8ccccc8)(c8ccccc8)c8ccccc8-9)c7)cc6)cc5c34)n2)cc1]

TABLE 1-continued
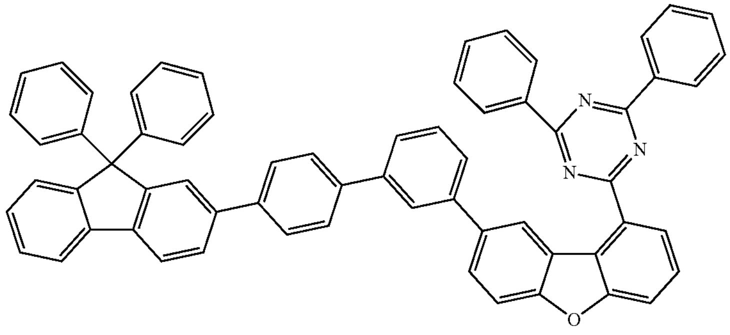 [SMILES: c1ccc(-c2nc(-c3ccccc3)nc(-c3cccc4oc5ccc(-c6cccc(-c7ccc(-c8ccc9c(c8)C(c8ccccc8)(c8ccccc8)c8ccccc8-9)cc7)c6)cc5c34)n2)cc1]
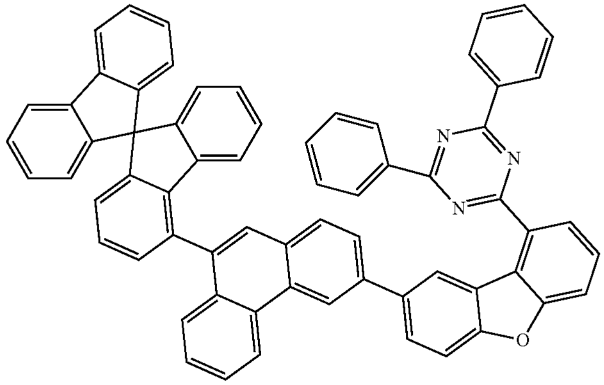 [SMILES: c1ccc(-c2nc(-c3ccccc3)nc(-c3cccc4oc5ccc(-c6ccc7cc(-c8cccc9c8-c8ccccc8C98c9ccccc9-c9ccccc98)c8ccccc8c7c6)cc5c34)n2)cc1]
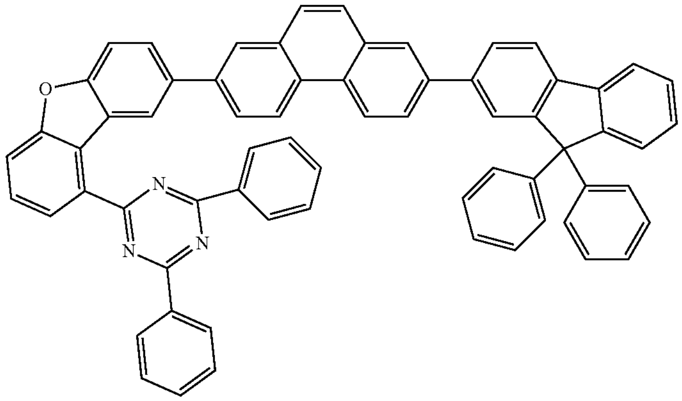 [SMILES: c1ccc(-c2nc(-c3ccccc3)nc(-c3cccc4oc5ccc(-c6ccc7c(ccc8cc(-c9ccc%10c(c9)C(c9ccccc9)(c9ccccc9)c9ccccc9-%10)ccc87)c6)cc5c34)n2)cc1]
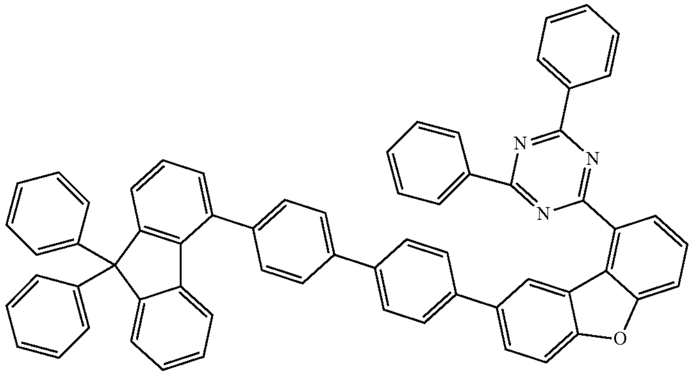 [SMILES: c1ccc(-c2nc(-c3ccccc3)nc(-c3cccc4oc5ccc(-c6ccc(-c7ccc(-c8cccc9c8-c8ccccc8C9(c8ccccc8)c8ccccc8)cc7)cc6)cc5c34)n2)cc1]

TABLE 1-continued
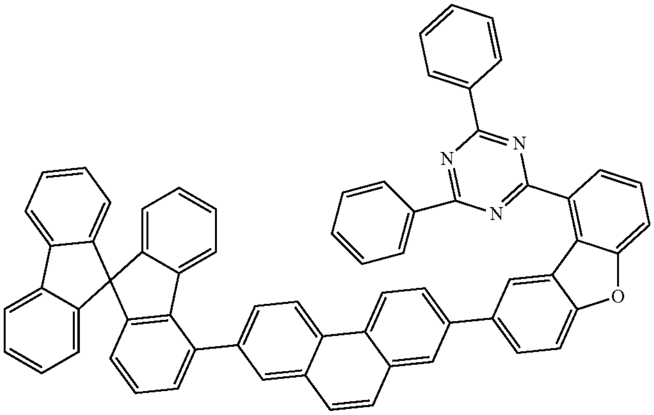 [SMILES: c1ccc(-c2nc(-c3ccccc3)nc(-c3cccc4oc5ccc(-c6ccc7c(ccc8cc(-c9cccc%10c9-c9ccccc9C%109c%10ccccc%10-c%10ccccc%109)ccc87)c6)cc5c34)n2)cc1]
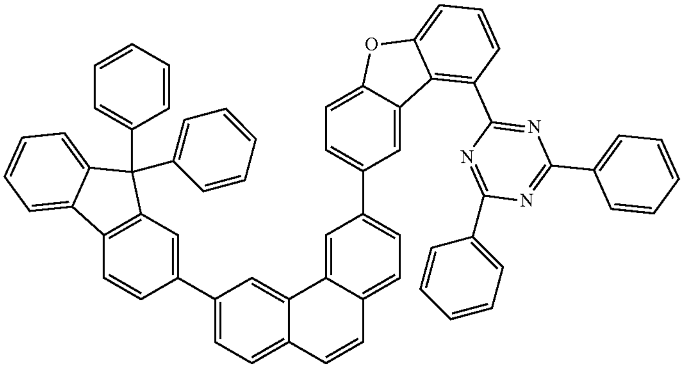 [SMILES: c1ccc(-c2nc(-c3ccccc3)nc(-c3cccc4oc5ccc(-c6ccc7ccc8ccc(-c9ccc%10c(c9)C(c9ccccc9)(c9ccccc9)c9ccccc9-%10)cc8c7c6)cc5c34)n2)cc1]
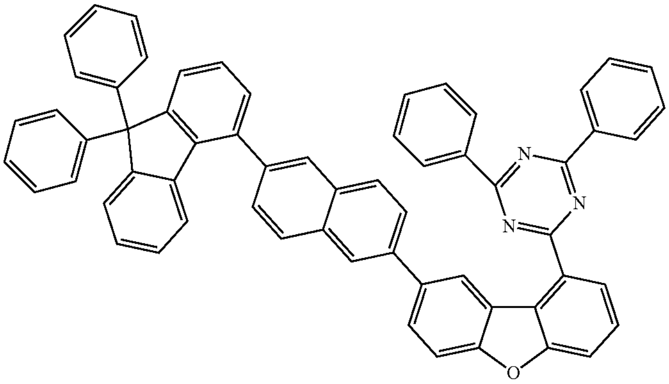 [SMILES: c1ccc(-c2nc(-c3ccccc3)nc(-c3cccc4oc5ccc(-c6ccc7cc(-c8cccc9c8-c8ccccc8C9(c8ccccc8)c8ccccc8)ccc7c6)cc5c34)n2)cc1]
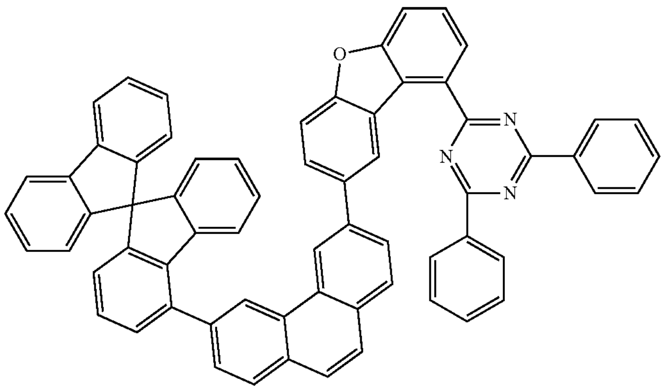 [SMILES: c1ccc(-c2nc(-c3ccccc3)nc(-c3cccc4oc5ccc(-c6ccc7ccc8ccc(-c9cccc%10c9-c9ccccc9C%109c%10ccccc%10-c%10ccccc%109)cc8c7c6)cc5c34)n2)cc1]

TABLE 1-continued
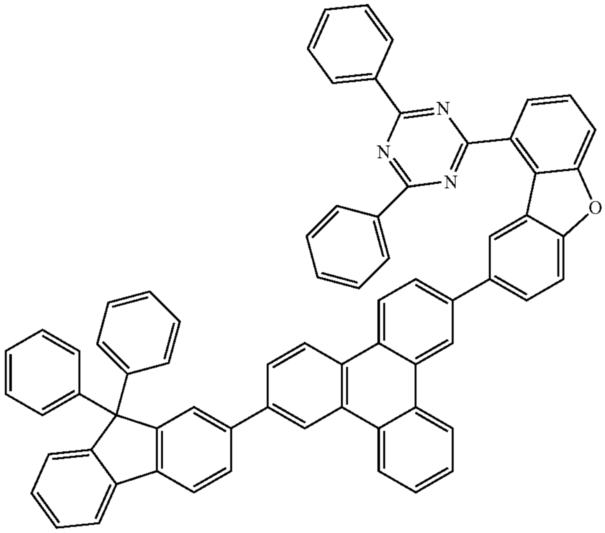 [SMILES: c1ccc(-c2nc(-c3ccccc3)nc(-c3cccc4oc5ccc(-c6ccc7c8ccc(-c9ccc%10c(c9)C(c9ccccc9)(c9ccccc9)c9ccccc9-%10)cc8c8ccccc8c7c6)cc5c34)n2)cc1]
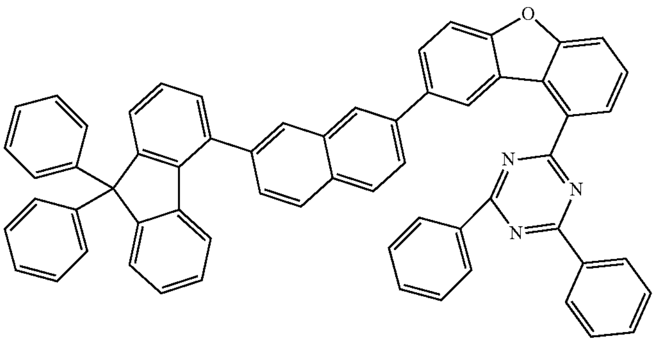 [SMILES: c1ccc(-c2nc(-c3ccccc3)nc(-c3cccc4oc5ccc(-c6ccc7ccc(-c8cccc9c8-c8ccccc8C9(c8ccccc8)c8ccccc8)cc7c6)cc5c34)n2)cc1]
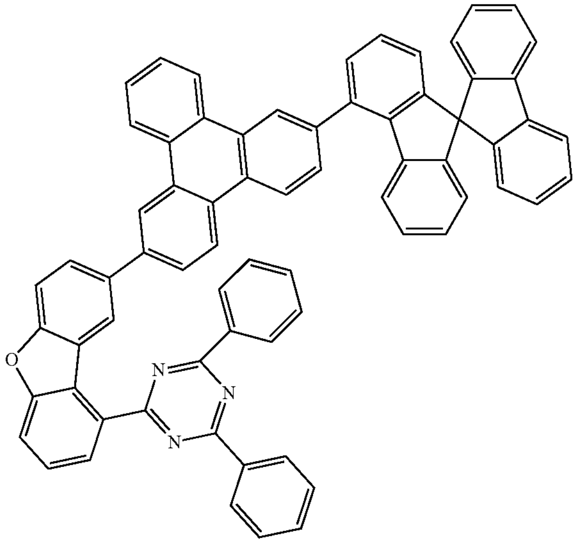 [SMILES: c1ccc(-c2nc(-c3ccccc3)nc(-c3cccc4oc5ccc(-c6ccc7c8ccc(-c9cccc%10c9-c9ccccc9C%109c%10ccccc%10-c%10ccccc%109)cc8c8ccccc8c7c6)cc5c34)n2)cc1]

TABLE 1-continued
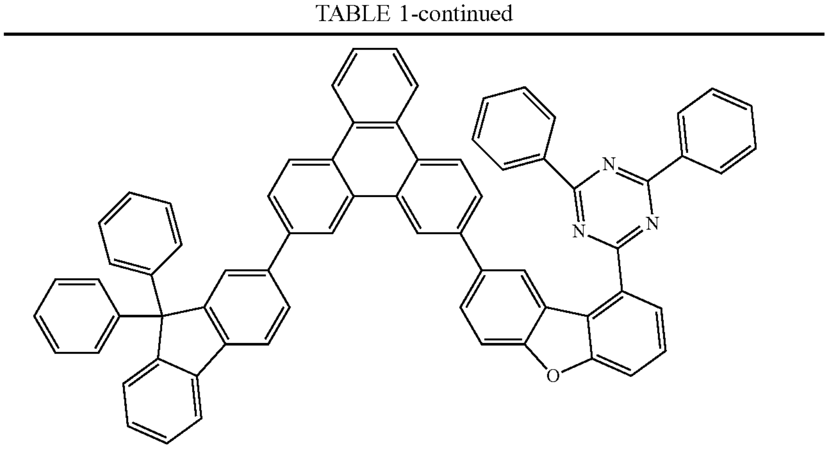
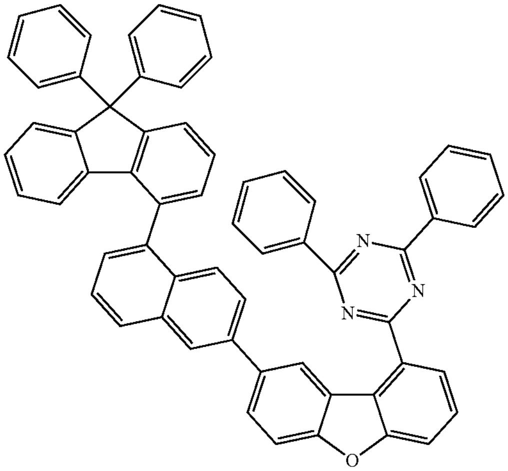 [SMILES: c1ccc(-c2nc(-c3ccccc3)nc(-c3cccc4oc5ccc(-c6ccc7c(-c8cccc9c8-c8ccccc8C9(c8ccccc8)c8ccccc8)cccc7c6)cc5c34)n2)cc1]
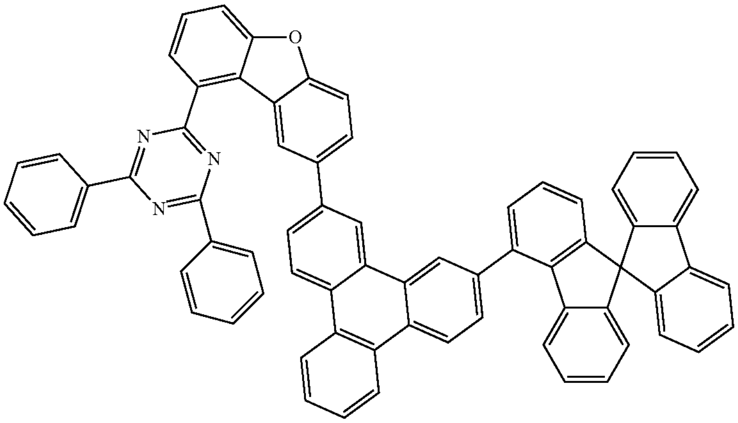 [SMILES: c1ccc(-c2nc(-c3ccccc3)nc(-c3cccc4oc5ccc(-c6ccc7c8ccccc8c8ccc(-c9cccc%10c9-c9ccccc9C%109c%10ccccc%10-c%10ccccc%109)cc8c7c6)cc5c34)n2)cc1]
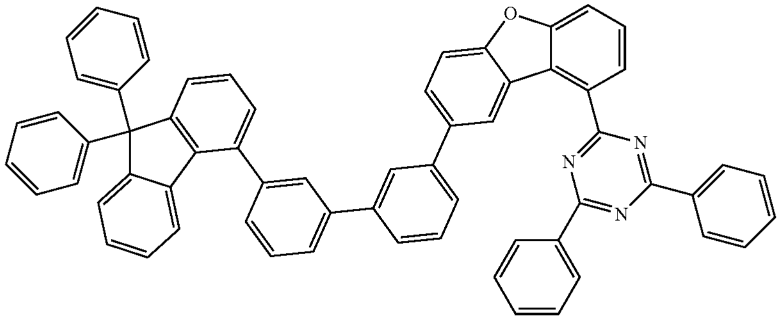 [SMILES: c1ccc(-c2nc(-c3ccccc3)nc(-c3cccc4oc5ccc(-c6cccc(-c7cccc(-c8cccc9c8-c8ccccc8C9(c8ccccc8)c8ccccc8)c7)c6)cc5c34)n2)cc1]

TABLE 1-continued
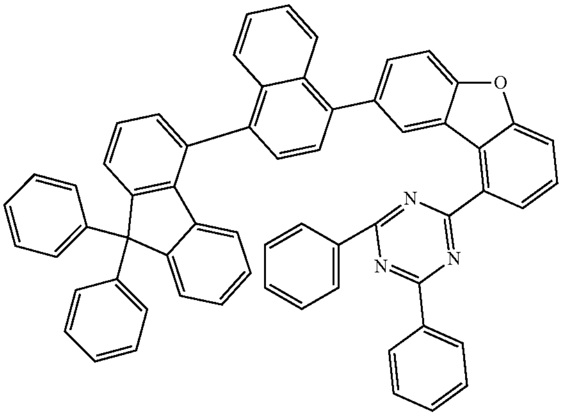 [SMILES: c1ccc(-c2nc(-c3ccccc3)nc(-c3cccc4oc5ccc(-c6ccc(-c7cccc8c7-c7ccccc7C8(c7ccccc7)c7ccccc7)c7ccccc67)cc5c34)n2)cc1]
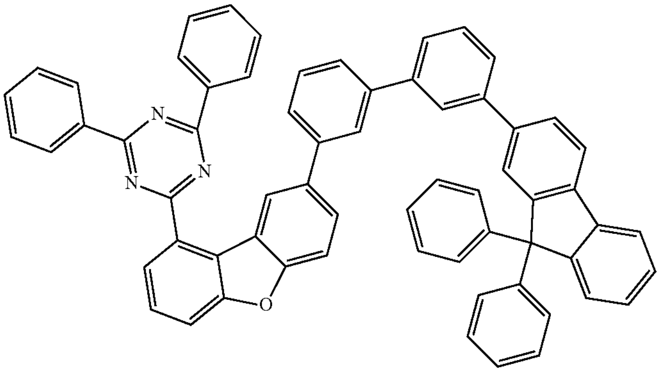 [SMILES: c1ccc(-c2nc(-c3ccccc3)nc(-c3cccc4oc5ccc(-c6cccc(-c7cccc(-c8ccc9c(c8)C(c8ccccc8)(c8ccccc8)c8ccccc8-9)c7)c6)cc5c34)n2)cc1]
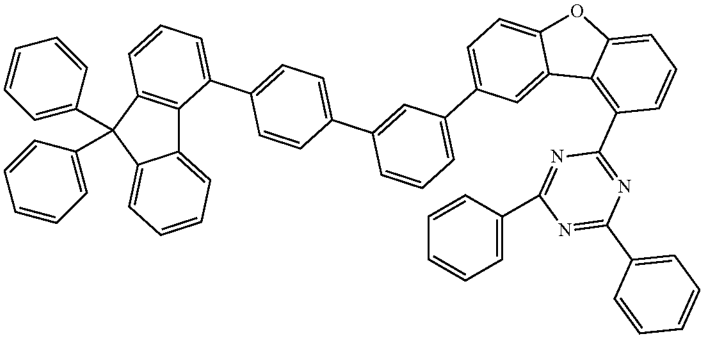 [SMILES: c1ccc(-c2nc(-c3ccccc3)nc(-c3cccc4oc5ccc(-c6cccc(-c7ccc(-c8cccc9c8-c8ccccc8C9(c8ccccc8)c8ccccc8)cc7)c6)cc5c34)n2)cc1]
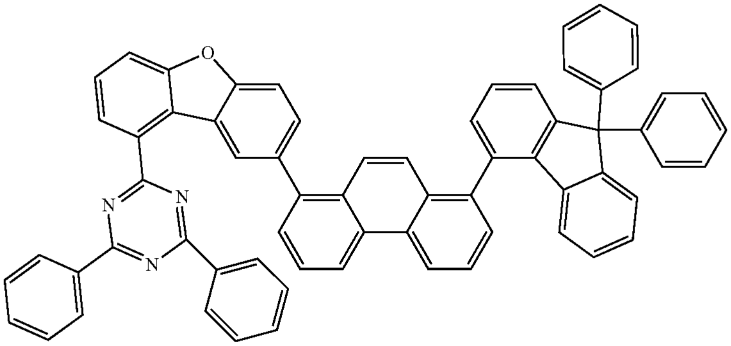 [SMILES: c1ccc(-c2nc(-c3ccccc3)nc(-c3cccc4oc5ccc(-c6cccc7c6ccc6c(-c8cccc9c8-c8ccccc8C9(c8ccccc8)c8ccccc8)cccc67)cc5c34)n2)cc1]

TABLE 1-continued
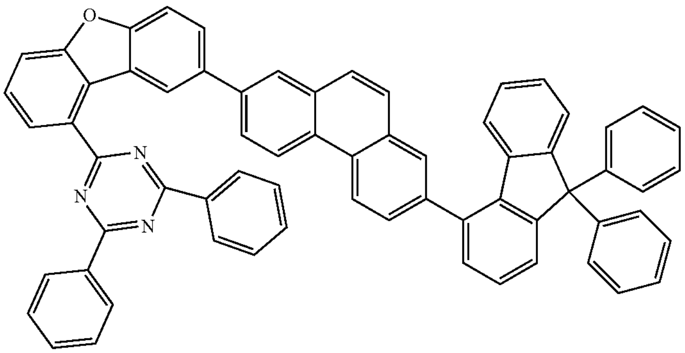 [SMILES: c1ccc(-c2nc(-c3ccccc3)nc(-c3cccc4oc5ccc(-c6ccc7c(ccc8cc(-c9cccc%10c9-c9ccccc9C%10(c9ccccc9)c9ccccc9)ccc87)c6)cc5c34)n2)cc1]
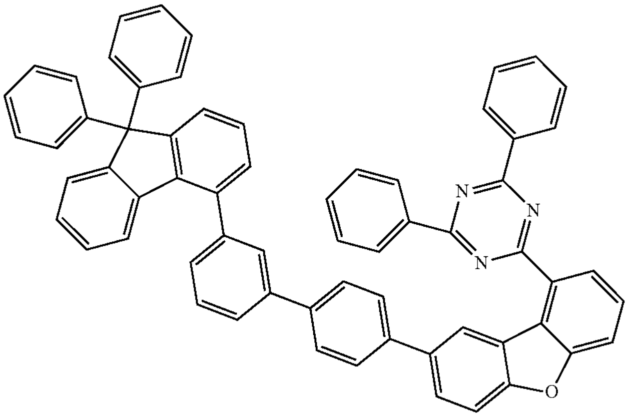 [SMILES: c1ccc(-c2nc(-c3ccccc3)nc(-c3cccc4oc5ccc(-c6ccc(-c7cccc(-c8cccc9c8-c8ccccc8C9(c8ccccc8)c8ccccc8)c7)cc6)cc5c34)n2)cc1]
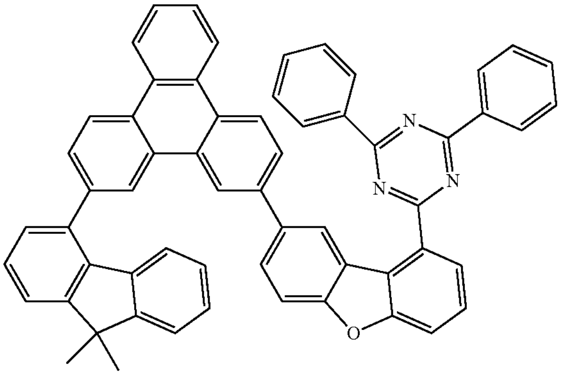 [SMILES: CC1(C)c2ccccc2-c2c(-c3ccc4c5ccccc5c5ccc(-c6ccc7oc8cccc(-c9nc(-c%10ccccc%10)nc(-c%10ccccc%10)n9)c8c7c6)cc5c4c3)cccc21]
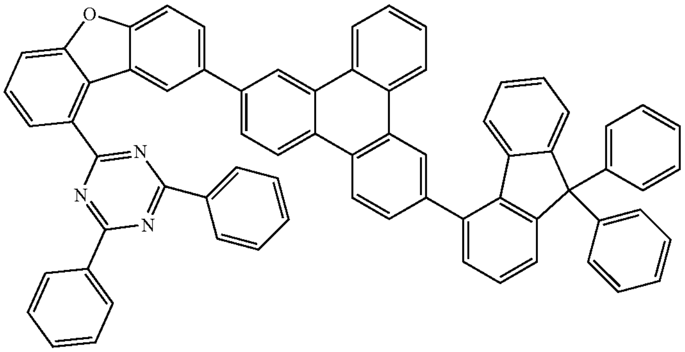 [SMILES: c1ccc(-c2nc(-c3ccccc3)nc(-c3cccc4oc5ccc(-c6ccc7c8ccc(-c9cccc%10c9-c9ccccc9C%10(c9ccccc9)c9ccccc9)cc8c8ccccc8c7c6)cc5c34)n2)cc1]

TABLE 1-continued
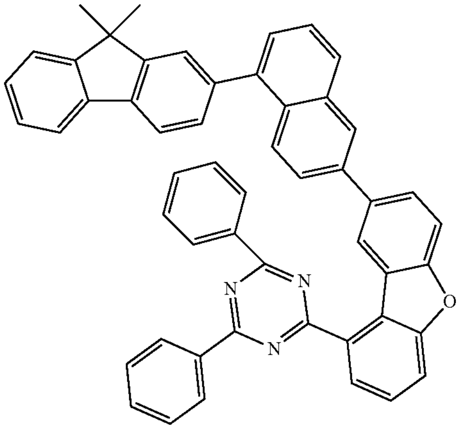 [SMILES: CC1(C)c2ccccc2-c2ccc(-c3cccc4cc(-c5ccc6oc7cccc(-c8nc(-c9ccccc9)nc(-c9ccccc9)n8)c7c6c5)ccc34)cc21]
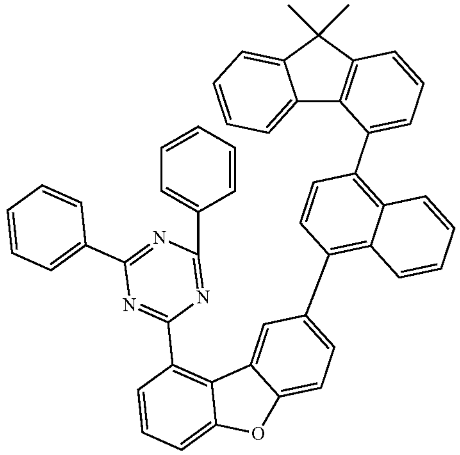 [SMILES: CC1(C)c2ccccc2-c2c(-c3ccc(-c4ccc5oc6cccc(-c7nc(-c8ccccc8)nc(-c8ccccc8)n7)c6c5c4)c4ccccc34)cccc21]
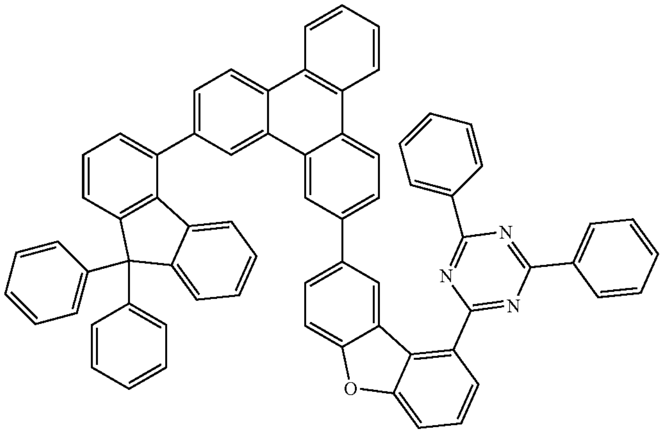 [SMILES: c1ccc(-c2nc(-c3ccccc3)nc(-c3cccc4oc5ccc(-c6ccc7c8ccccc8c8ccc(-c9cccc%10c9-c9ccccc9C%10(c9ccccc9)c9ccccc9)cc8c7c6)cc5c34)n2)cc1]

TABLE 1-continued
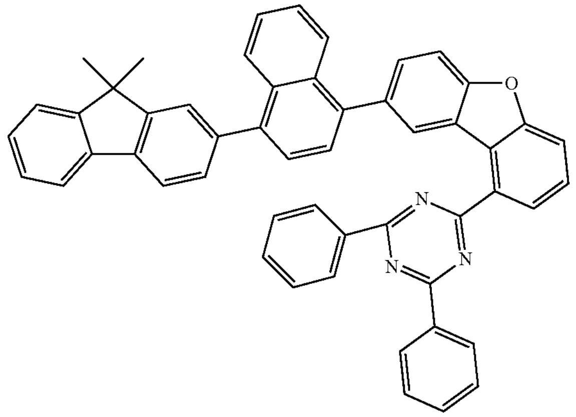 [SMILES: CC1(C)c2ccccc2-c2ccc(-c3ccc(-c4ccc5oc6cccc(-c7nc(-c8ccccc8)nc(-c8ccccc8)n7)c6c5c4)c4ccccc34)cc21]
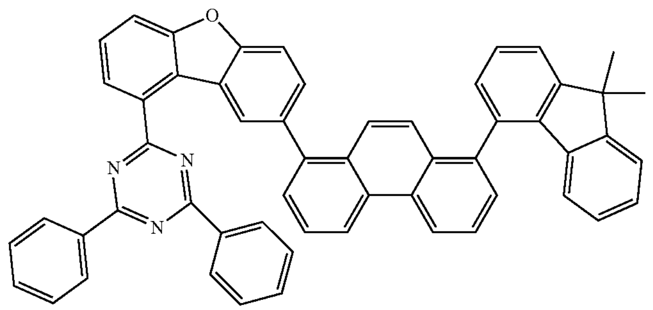 [SMILES: CC1(C)c2ccccc2-c2c(-c3cccc4c3ccc3c(-c5ccc6oc7cccc(-c8nc(-c9ccccc9)nc(-c9ccccc9)n8)c7c6c5)cccc34)cccc21]
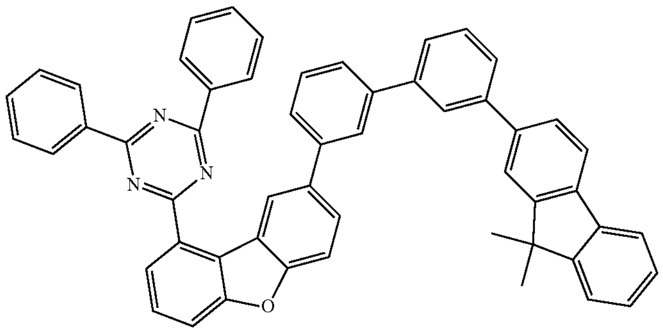 [SMILES: CC1(C)c2ccccc2-c2ccc(-c3cccc(-c4cccc(-c5ccc6oc7cccc(-c8nc(-c9ccccc9)nc(-c9ccccc9)n8)c7c6c5)c4)c3)cc21]
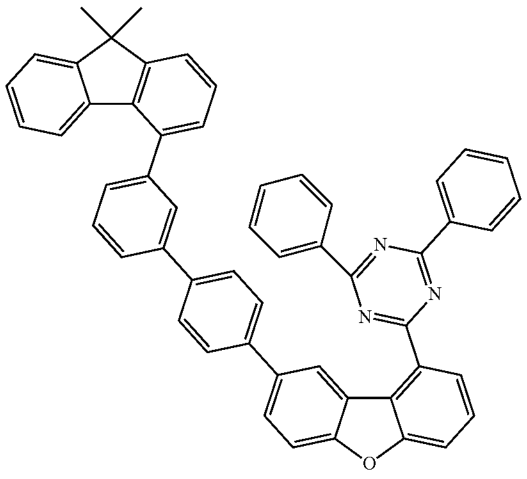 [SMILES: CC1(C)c2ccccc2-c2c(-c3cccc(-c4ccc(-c5ccc6oc7cccc(-c8nc(-c9ccccc9)nc(-c9ccccc9)n8)c7c6c5)cc4)c3)cccc21]

TABLE 1-continued
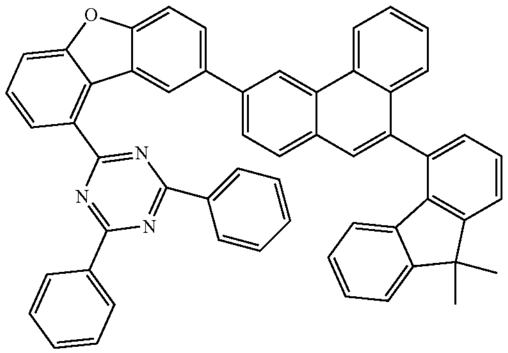 [SMILES: CC1(C)c2ccccc2-c2c(-c3cc4ccc(-c5ccc6oc7cccc(-c8nc(-c9ccccc9)nc(-c9ccccc9)n8)c7c6c5)cc4c4ccccc34)cccc21]
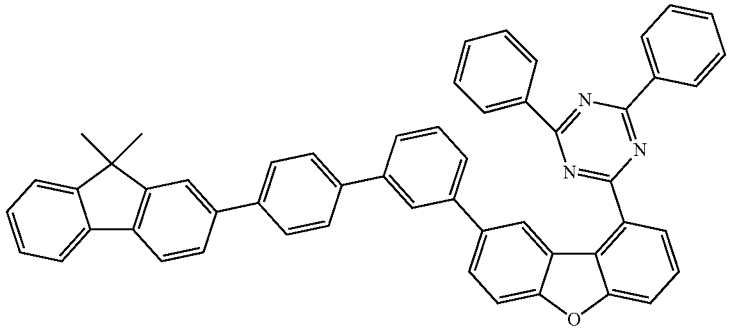 [SMILES: CC1(C)c2ccccc2-c2ccc(-c3ccc(-c4cccc(-c5ccc6oc7cccc(-c8nc(-c9ccccc9)nc(-c9ccccc9)n8)c7c6c5)c4)cc3)cc21]
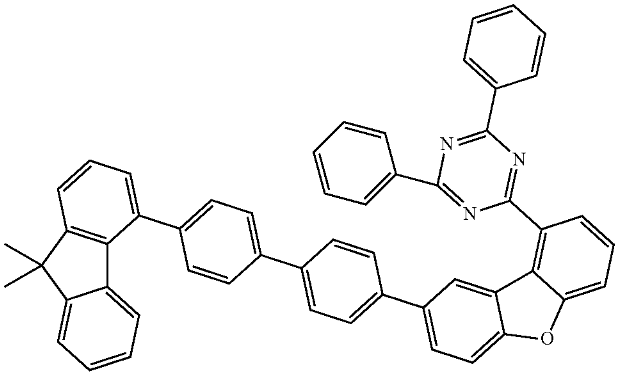 [SMILES: CC1(C)c2ccccc2-c2c(-c3ccc(-c4ccc(-c5ccc6oc7cccc(-c8nc(-c9ccccc9)nc(-c9ccccc9)n8)c7c6c5)cc4)cc3)cccc21]
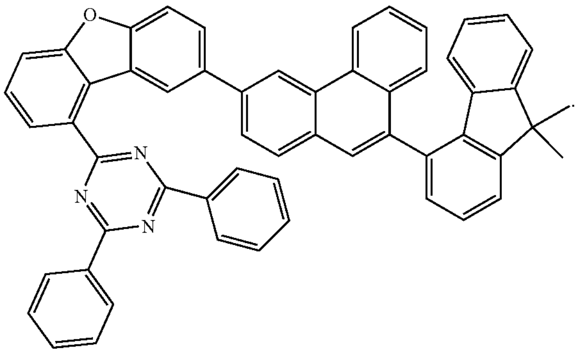 [SMILES: CC1(C)c2ccccc2-c2c(-c3cc4ccc(-c5ccc6oc7cccc(-c8nc(-c9ccccc9)nc(-c9ccccc9)n8)c7c6c5)cc4c4ccccc34)cccc21]

Particularly suitable compounds of the formula (1), (1a), (1 b), (1c), (1d), (1e), (1f), (1g), (1h), (1i), (1j) or (1k) that are selected in accordance with the invention are the compounds 1 to 11 of table 2.
TABLE 2
1
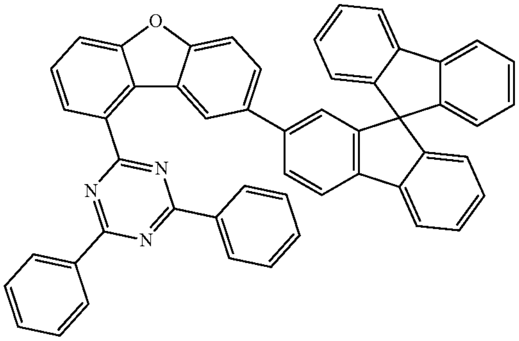 [SMILES: c1ccc(-c2nc(-c3ccccc3)nc(-c3cccc4oc5ccc(-c6ccc7c(c6)C6(c8ccccc8-c8ccccc86)c6ccccc6-7)cc5c34)n2)cc1]
2
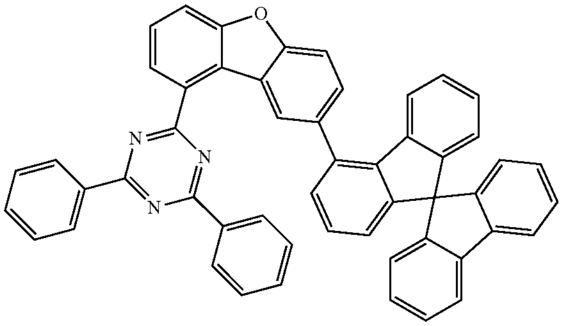 [SMILES: c1ccc(-c2nc(-c3ccccc3)nc(-c3cccc4oc5ccc(-c6cccc7c6-c6ccccc6C76c7ccccc7-c7ccccc76)cc5c34)n2)cc1]
3
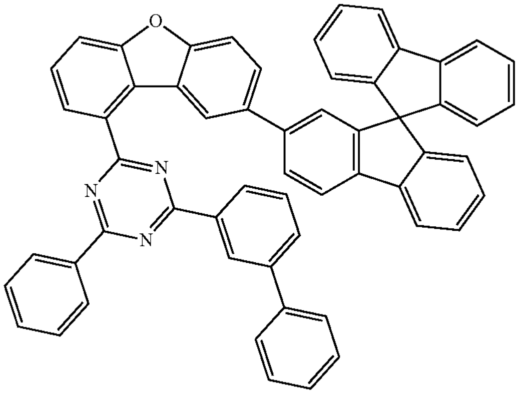 [SMILES: c1ccc(-c2cccc(-c3nc(-c4ccccc4)nc(-c4cccc5oc6ccc(-c7ccc8c(c7)C7(c9ccccc9-c9ccccc97)c7ccccc7-8)cc6c45)n3)c2)cc1]
4
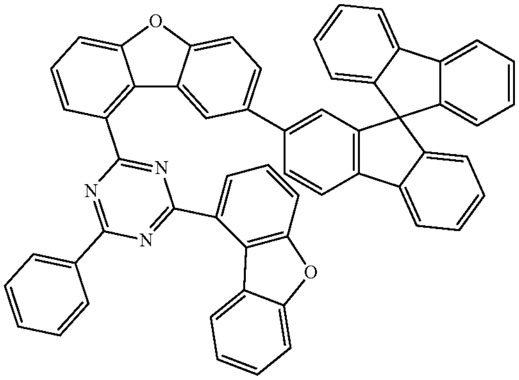 [SMILES: c1ccc(-c2nc(-c3cccc4oc5ccccc5c34)nc(-c3cccc4oc5ccc(-c6ccc7c(c6)C6(c8ccccc8-c8ccccc86)c6ccccc6-7)cc5c34)n2)cc1]
TABLE 2-continued
5
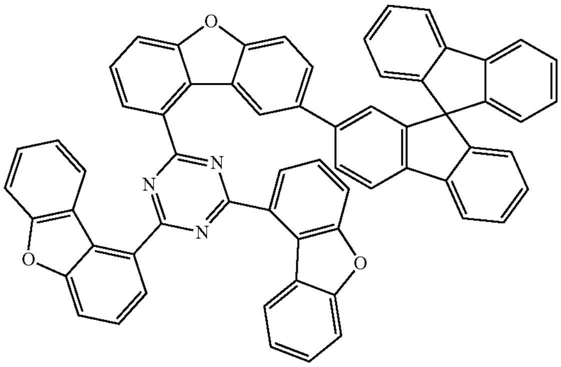 [SMILES: c1ccc2c(c1)-c1ccccc1C21c2ccccc2-c2ccc(-c3ccc4oc5cccc(-c6nc(-c7cccc8oc9ccccc9c78)nc(-c7cccc8oc9ccccc9c78)n6)c5c4c3)cc21]
6
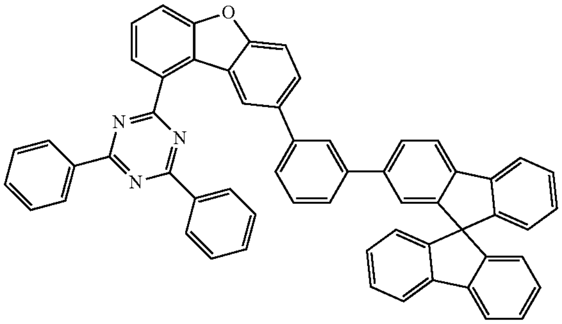 [SMILES: c1ccc(-c2nc(-c3ccccc3)nc(-c3cccc4oc5ccc(-c6cccc(-c7ccc8c(c7)C7(c9ccccc9-c9ccccc97)c7ccccc7-8)c6)cc5c34)n2)cc1]
7
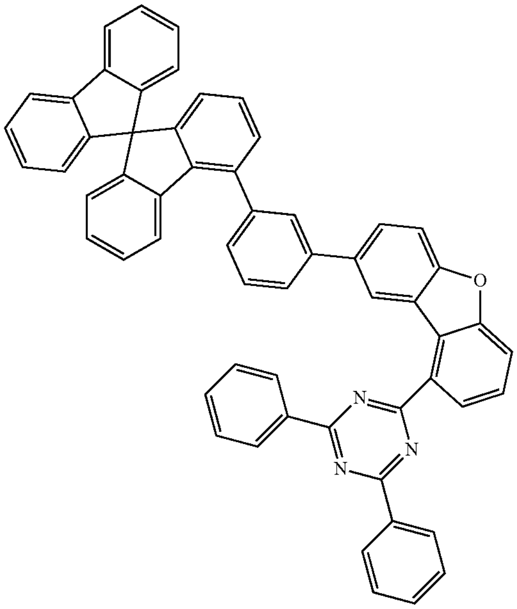 [SMILES: c1ccc(-c2nc(-c3ccccc3)nc(-c3cccc4oc5ccc(-c6cccc(-c7cccc8c7-c7ccccc7C87c8ccccc8-c8ccccc87)c6)cc5c34)n2)cc1]
8
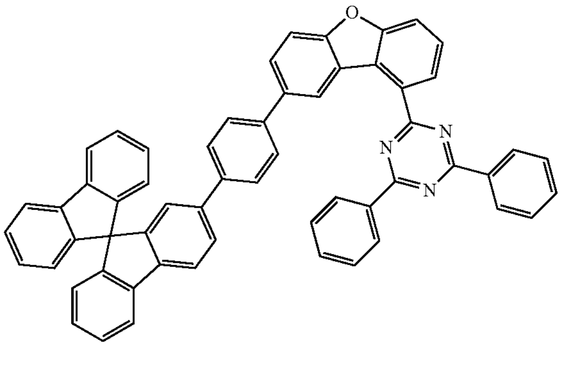 [SMILES: c1ccc(-c2nc(-c3ccccc3)nc(-c3cccc4oc5ccc(-c6ccc(-c7ccc8c(c7)C7(c9ccccc9-c9ccccc97)c7ccccc7-8)cc6)cc5c34)n2)cc1]

TABLE 2-continued

9

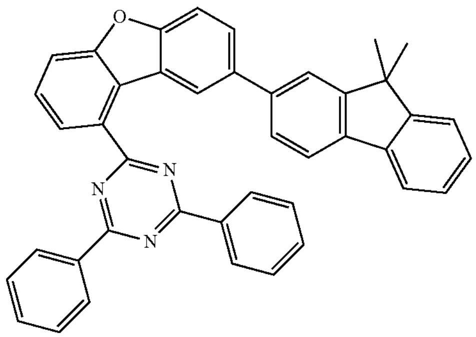 [SMILES: CC1(C)c2ccccc2-c2ccc(-c3ccc4oc5cccc(-c6nc(-c7ccccc7)nc(-c7ccccc7)n6)c5c4c3)cc21]

10

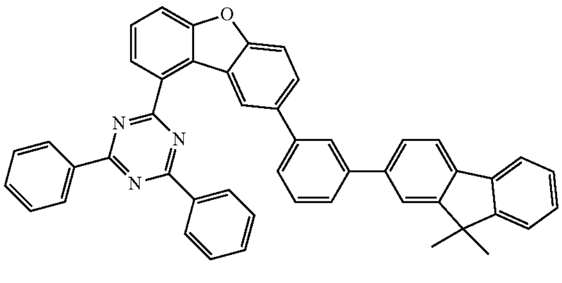 [SMILES: CC1(C)c2ccccc2-c2ccc(-c3cccc(-c4ccc5oc6cccc(-c7nc(-c8ccccc8)nc(-c8ccccc8)n7)c6c5c4)c3)cc21]

11

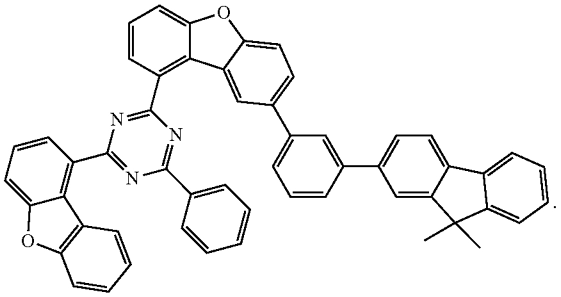 [SMILES: CC1(C)c2ccccc2-c2ccc(-c3cccc(-c4ccc5oc6cccc(-c7nc(-c8ccccc8)nc(-c8cccc9oc%10ccccc%10c89)n7)c6c5c4)c3)cc21]

The preparation of the compounds of the formula (1) or of the preferred compounds of the formulae (1a) to (1k) and of the compounds 1 to 11 is known to those skilled in the art. The compounds may be prepared by synthesis steps known to the person skilled in the art, for example halogenation, preferably bromination, and a subsequent organometallic coupling reaction, for example Suzuki coupling, Heck coupling or Hartwig-Buchwald coupling. The preparation of the compounds of the formula (1) or of the preferred compounds of the formulae (1a) to (1k) and of the compounds 1 to 11 can be inferred especially from WO 2015/169412, especially page 63 and the synthesis examples on pages 77 to 114.

The compounds of the formulae (1) to (1f) where L is a single bond can be prepared according to Scheme 1 below, where X, Y, R*, $Ar_1$, $Ar_2$ has one of the definitions given above and R in Scheme 1 is an alkyl group having 1 to 4 carbon atoms.

Scheme 1

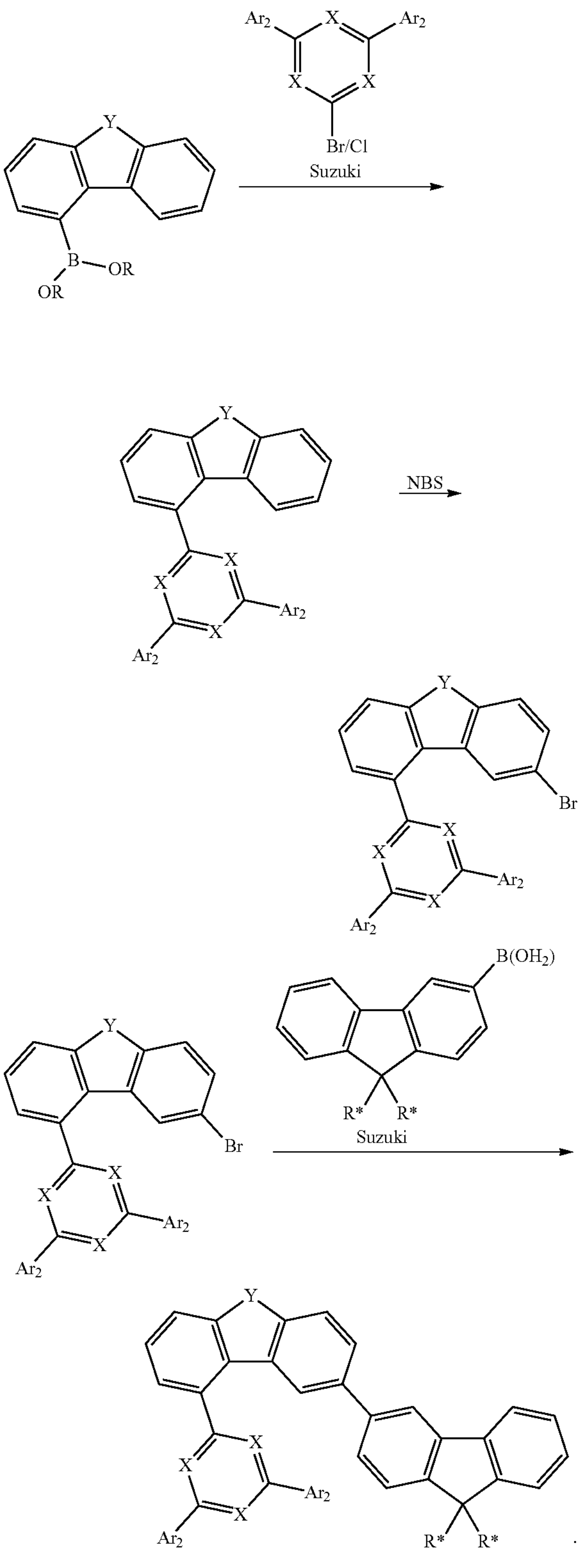

The compounds of the formulae (1) to (1k) in which L is a linker group can be prepared according to Scheme 2 below, where X, Y, R*, $Ar_1$, $Ar_2$ has one of the definitions given above.

Scheme 2

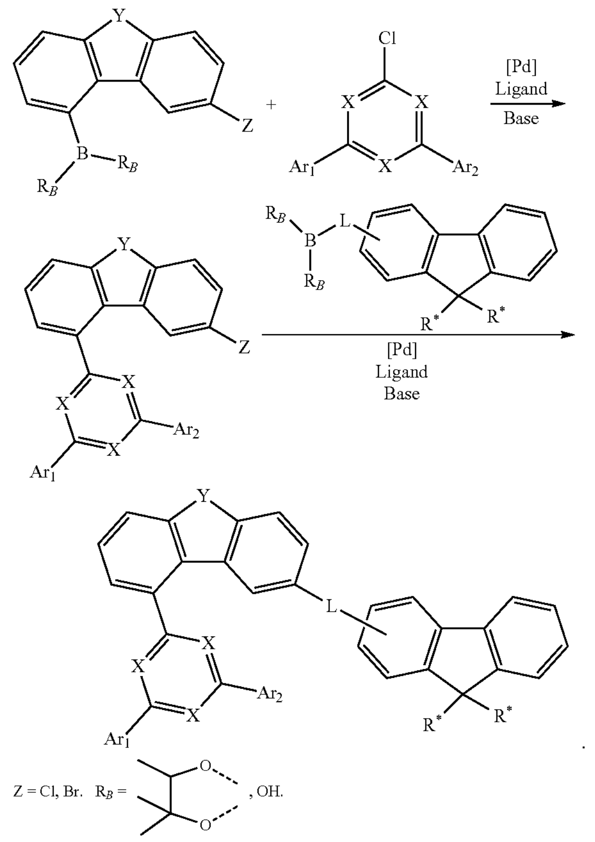

Hole-transporting hosts conform to the formula (2)

Formula (2)

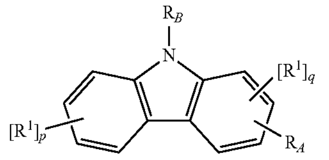

where the symbols and indices used are as follows:

$R_A$ is H, $-L_3-Ar_4$ or $-L_1-N(Ar)_2$;

$R_B$ is $Ar_3$ or $-L_2-N(Ar)_2$;

$L_1$, $L_2$ are the same or different at each instance and are a single bond or an aromatic or heteroaromatic ring system which has 5 to 30 aromatic ring atoms and may be substituted by one or more $R^3$ radicals;

$L_3$ is a single bond or an aromatic or heteroaromatic ring system which has 5 to 30 aromatic ring atoms and may be substituted by one or more $R^3$ radicals, where one substituent $R^1$ on the carbazole may form a ring with a substituent $R^3$;

$Ar_3$ is an aromatic ring system having 6 to 40 aromatic ring atoms or a heteroaromatic ring system having 10 to 40 aromatic ring atoms, which may be substituted by one or more $R^3$ radicals;

$Ar_4$ is the same or different at each instance and is an unsubstituted or substituted 9-arylcarbazolyl or unsubstituted or substituted carbazol-9-yl, which may be substituted by one or more $R^4$ radicals, and where one or more instances each of two $R^4$ radicals or one $R^4$ radical together with one $R^1$ radical may independently form a monocyclic or polycyclic, aliphatic, aromatic or heteroaromatic ring, where aryl is an aromatic or heteroaromatic ring system which has 5 to 30 aromatic ring atoms and may be substituted by $R^3$;

$R^1$ is the same or different at each instance and are selected from the group consisting of H, D, F, Cl, Br, I, CN, $NO_2$, $N(Ar)_2$, $N(R^2)_2$, C(=O)Ar, $C(=O)R^2$, $P(=O)(Ar)_2$, $P(Ar)_2$, $B(Ar)_2$, $Si(Ar)_3$, $Si(R^2)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^2$ radicals, where one or more nonadjacent $CH_2$ groups may be replaced by $R^2C{=}CR^2$, $Si(R^2)_2$, C=O, C=S, $C{=}NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^2$ radicals, an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals; at the same time, it is optionally possible for two substituents $R^0$ and/or R and/or $R^1$ bonded to the same carbon atom or to adjacent carbon atoms to form a monocyclic or polycyclic, aliphatic, aromatic or heteroaromatic ring system which may be substituted by one or more $R^2$ radicals;

$R^2$ is the same or different at each instance and is selected from the group consisting of H, D, F, Cl, Br, I, CN, $NO_2$, $N(Ar)_2$, $NH_2$, $N(R^3)_2$, C(=O)Ar, C(=O)H, $C(=O)R^3$, $P(=O)(Ar)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^3$ radicals, where one or more nonadjacent $CH_2$ groups may be replaced by HC=CH, $R^3C{=}CR^3$, C≡C, $Si(R^3)_2$, $Ge(R^3)_2$, $Sn(R^3)_2$, C=O, C=S, C=Se, $C{=}NR^3$, $P(=O)(R^3)$, SO, $SO_2$, NH, $NR^3$, O, S, CONH or $CONR^3$ and where one or more hydrogen atoms may be replaced by D, F, Cl, Br, I, CN or $NO_2$, an aromatic or heteroaromatic ring system which has 5 to 60 aromatic ring atoms and may be substituted in each case by one or more $R^3$ radicals, an aryloxy or heteroaryloxy group which has 5 to 60 aromatic ring atoms and may be substituted by one or more $R^3$ radicals, or a combination of these systems; where it is optionally possible for two or more adjacent substituents $R^2$ to form a monocyclic or polycyclic, aliphatic, aromatic or heteroaromatic ring system which may be substituted by one or more $R^3$ radicals;

$R^3$ is the same or different at each instance and is selected from the group consisting of H, D, F, CN, $N(Ar)_2$, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more adjacent $R^3$ substituents together to form a mono- or polycyclic, aliphatic ring system;

$R^4$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I, a straight-chain or branched alkyl group having 1 to 4 carbon atoms or CN; at the same time, two or more adjacent $R^4$ substituents together may form a mono- or polycyclic ring system;

Ar is the same or different at each instance and is an aromatic or heteroaromatic ring system which has 5 to 30 aromatic ring atoms and may be substituted by one or more nonaromatic $R^3$ radicals; at the same time, two Ar radicals bonded to the same nitrogen atom, phosphorus atom or boron atom may also be bridged to one another by a single bond or a bridge selected from $N(R^3)$, $C(R^3)_2$, O and S, and q at each instance is independently 0, 1, 2 or 3;

p at each instance is independently 0, 1, 2, 3 or 4.

In one embodiment of the invention, compounds of the formula (2) as described above are selected, which are used in the composition together with compounds of the formulae (1), (1a), (1b), (1c), (1d), (1e), (1f), (1g), (1h), (1i), (1j) and (1k) as described above or described as preferred, or with the compounds in table 1 or compounds 1 to 11.

Compounds of the formula (2) may be represented by the following formulae (2a), (2b), (2c) and (2d):

Formula (2a)

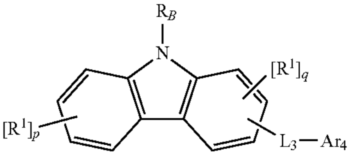

Formula (2b)

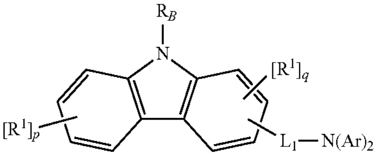

Formula (2c)

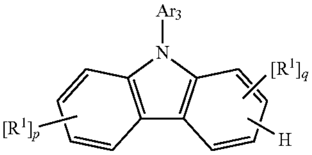

Formula (2d)

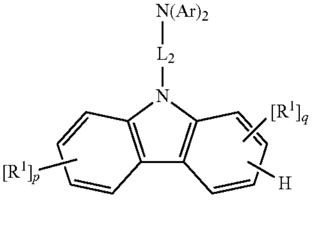

where $L_1$, $L_2$, $L_3$, Ar, $Ar_3$, $Ar_4$, $R^1$, q and p have a definition given above or definition given hereinafter.

Preferred compounds of the formula (2a) are compounds of the formulae (2e), (2f), (2g), (2h) and (2i)

Formula (2e)

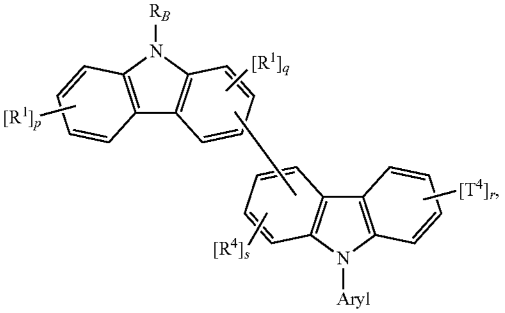

Formula (2f)

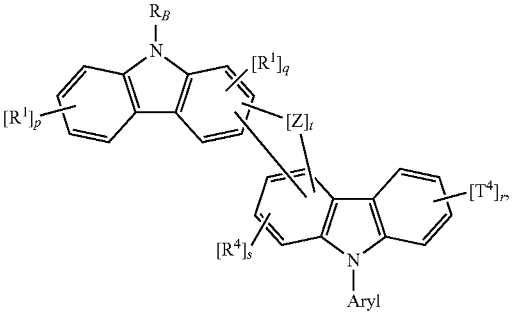

Formula (2g)

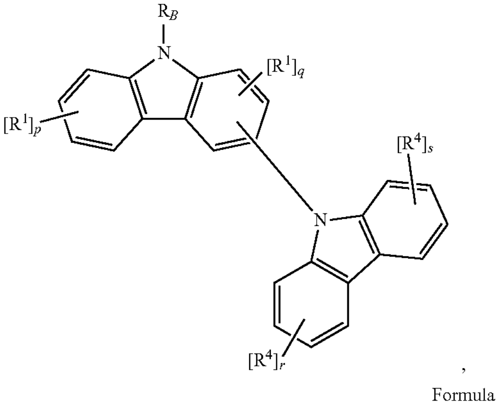

,

Formula (2h)

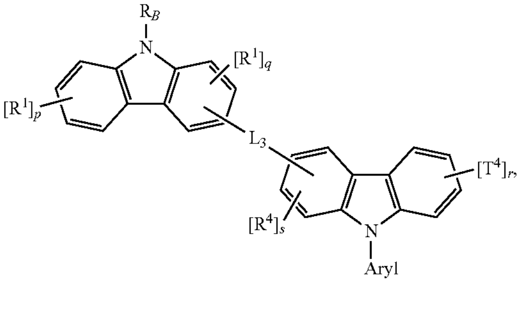

-continued

Formula (2i)

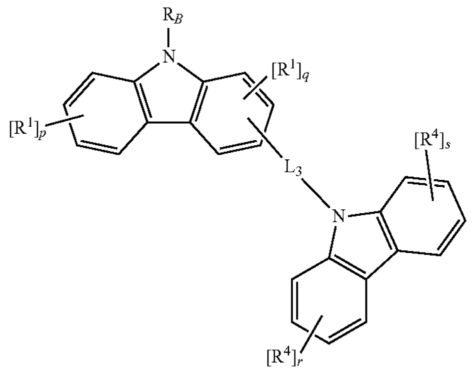

where $R_B$, Ar, $R^1$, $R^4$, q and p have a definition given above or given hereinafter, $L_3$ in the formulae (2h) and (2i) is an aromatic or heteroaromatic ring system which has 5 to 30 aromatic ring atoms and may be substituted by one or more $R^3$ radicals, where one substituent $R^1$ on the carbazole may form a ring with a substituent $R^3$, r and s are each independently 0, 1, 2, 3 or 4, Z is $C(R^1)_2$, N—Ar, O or S, and t is 0 or 1.

In compounds of the formulae (2a) to (2i), H is excluded from the definition of the substituents $R^1$ when p, q, r or s are greater than 1.

The invention accordingly further provides a composition as described above, wherein the compound of the formula (2) corresponds to one of the compounds of the formulae (2a), (2b), (2c), (2d), (2e), (2f), (2g), (2h) and (2i).

In the compounds of the formulae (2), (2a), (2b), (2c), (2d), (2e), (2f), (2g), (2h) and (2i), one substituent $R^1$ and one substituent $R^4$ may form a ring, for example also defined by $[Z]_t$ in formula (2f), preferably forming the following rings Z-1 to Z-7, and where the dotted lines in each case represent the bond to the carbazoles:

Z-1

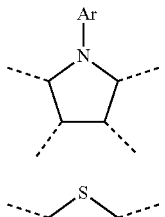

Z-2

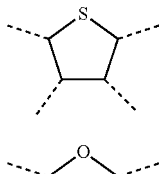

Z-3

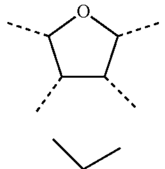

Z-4

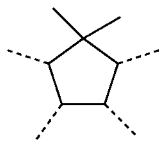

-continued

Z-5

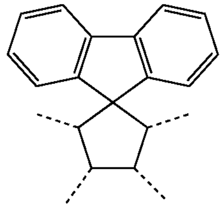

Z-6

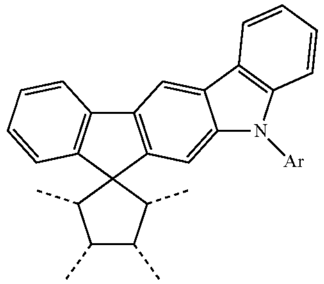

Z-7

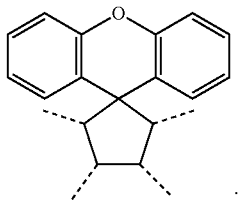

.

In the compounds of the formulae (2), (2a), (2b), (2c), (2d), (2e), (2f), (2g), (2h) and (2i), two substituents $R^1$ in one or more instances may together form a ring or two substituents $R^4$ in one or more instances may together form a ring which is preferably selected from the following structures (S1) to (S9), where # and # represent the respective bonding site to the carbon atoms and the structures may each be substituted by one or more substituents $R^2$:

(S1)

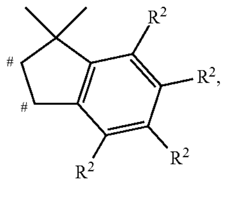

(S2)

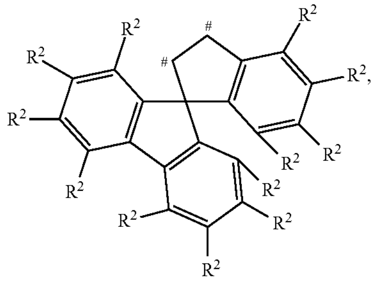

-continued (S3)

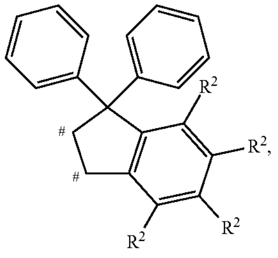

(S4)

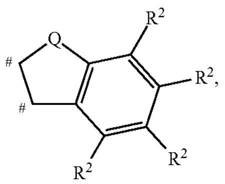

(S5)

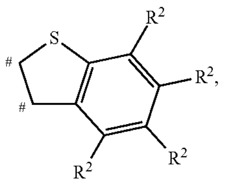

(S6)

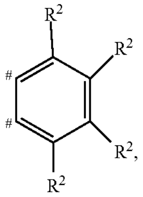

(S7)

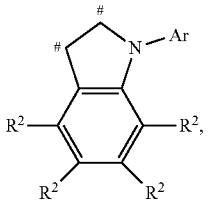

(S8)

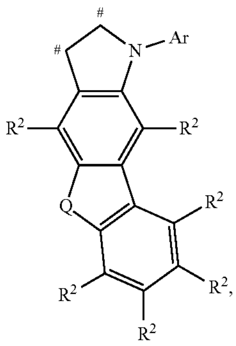

and

-continued (S9)

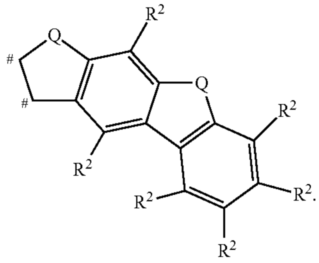

$R^2$ in the substructures (S1) to (S9) is preferably H or an aromatic or heteroaromatic ring system which has 5 to 40 ring atoms and may be substituted by $R^3$, preferably H or phenyl.

In the compounds of the formulae (2), (2a), (2b), (2c), (2d), (2e), (2f), (2g), (2h) and (2i), the linkers $L_1$, $L_2$ and $L_3$, if they are not a single bond, are each independently selected from the linkers L-2.1 to L-2.33:

L-2.1

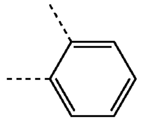

L-2.2

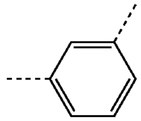

L-2.3

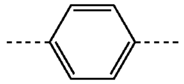

L-2.4

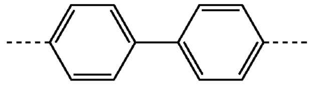

L-2.5

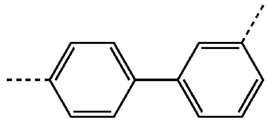

L-2.6

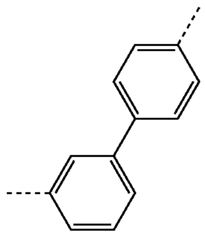

L-2.7

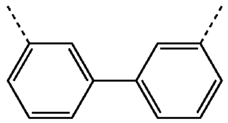

-continued
L-2.8
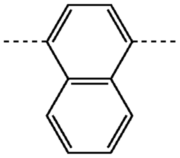
L-2.9
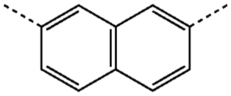
L-2.10
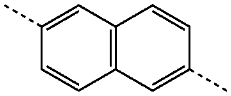
L-2.11
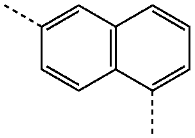
L-2.12
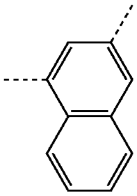
L-2.13
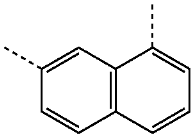
L-2.14
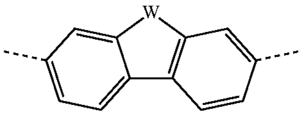
L-2.15
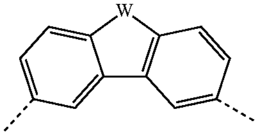
,
L-2.16
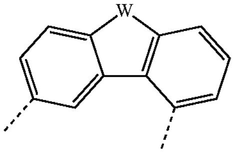
L-2.17
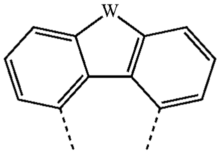
-continued
L-2.18
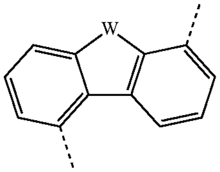
L-2.19
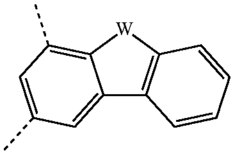
L-2.20
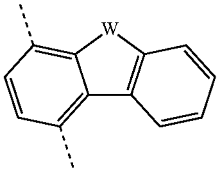
L-2.21
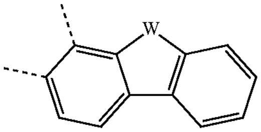
L-2.22
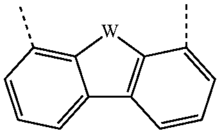
L-2.23
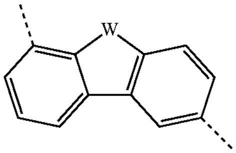
L-2.24
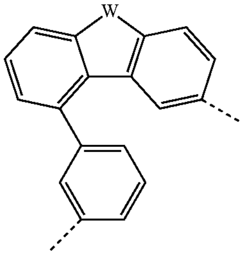
L-2.25
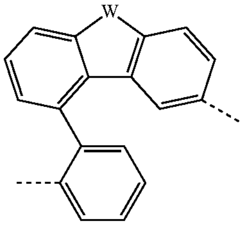

-continued

L-2.26

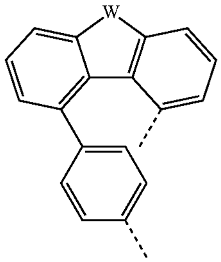

L-2.27

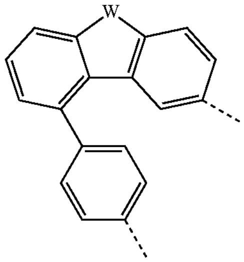

L-2.28

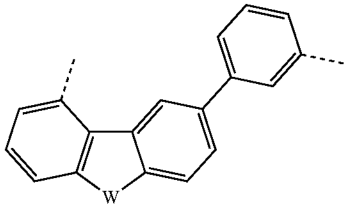

L-2.29

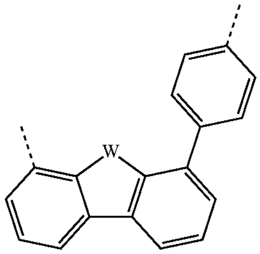

L-2.30

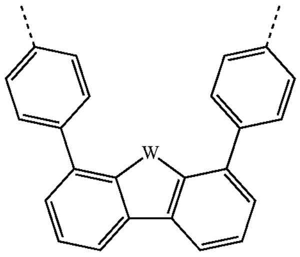

L-2.31

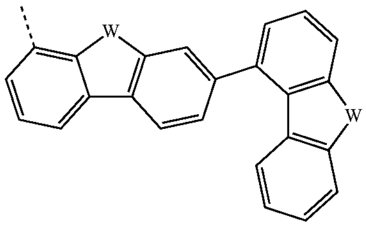

-continued

L-2.32

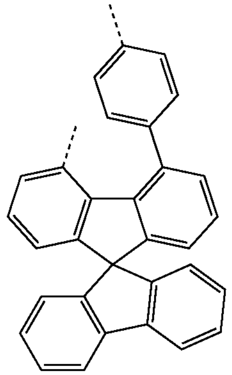

L-2.33

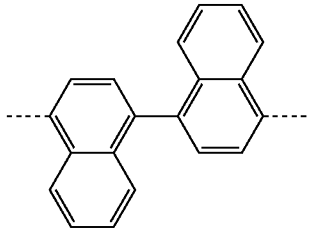

, where W denotes N—Ar, O, S or $C(CH_3)_2$, Ar has a definition given above, the linkers L-1 to L-33 may be substituted by one or more $R^3$ radicals and the dotted lines denote the attachment to the carbazoles. For the linker $L_3$, an $R^3$ radical on one of the linkers L-2.1 to L-2.33 may form a ring with an $R^1$ radical of the carbazole.

Preferably, the linkers L-2.1 to L-2.33 are unsubstituted or substituted by a phenyl.

Preferred linkers for $L_1$ are selected from the structures L-2.1 to L-2.33 in which W is defined as S or O, more preferably defined as O.

Preferred linkers for $L_3$ are selected from the structures L-2.1 to L-2.33 in which W is defined as O, S or N—Ar, more preferably defined as O or N—Ar.

In a preferred embodiment of the compounds of the formulae (2), (2a), (2b), (2c), (2d), (2e), (2f), (2g), (2h) and (2i), the two carbazoles are joined to one another, each in the 3 position.

In compounds of the formulae (2), (2a), (2b), (2c), (2d), (2e), (2f), (2g), (2h) and (2i), q is preferably 0, 1 or 2, where $R^1$ has a definition given above or a definition given below. More preferably, q is 0 or 1. Most preferably, q is 0.

When, in compounds of the formulae (2), (2a), (2b), (2c), (2d), (2e), (2f), (2g), (2h) and (2i), q is greater than 0, the substituent $R^1$ is the same or different at each instance and is preferably selected from the group consisting of D, F, an alkyl group having 1 to 40 carbon atoms or an aromatic or heteroaromatic ring system which has 5 to 40 aromatic ring atoms and may be substituted by one or more $R^2$ radicals. The aromatic or heteroaromatic ring system having 5 to 40 aromatic ring atoms in this $R^1$ is preferably derived from benzene, dibenzofuran, dibenzothiophene, 9-phenylcarbazole, biphenyl and terphenyl, which may be substituted by one or more $R^2$ radicals. The preferred position of the substituent(s) $[R^1]_q$ is position 1, 2, 3 or 4 or the combinations of positions 1 and 4 and 1 and 3, more preferably 1 and 3, 2 or 3, most preferably 3, where $R^1$ has one of the preferred definitions given above and q is greater than 0.

Particularly preferred substituents $R^1$ in $[R^1]_q$ are carbazol-9-yl, biphenyl, terphenyl and dibenzofuranyl.

In compounds of the formulae (2), (2a), (2b), (2c), (2d), (2e), (2f), (2g), (2h) and (2i), r is preferably 0, 1 or 2, where $R^4$ has a definition given above or a definition given below. More preferably, r is 0 or 1, most preferably 0.

When r is greater than 0 in compounds of the formulae (2), (2a), (2b), (2c), (2d), (2e), (2f), (2g), (2h) and (2i), the substituent $R^4$ is the same or different at each instance and is preferably selected from the group consisting of D, F, an alkyl group having 1 to 20 carbon atoms or an aromatic or heteroaromatic ring system having 5 to 30 aromatic ring atoms, in which one or more hydrogen atoms may be replaced by D, F, Cl, Br, I, a straight-chain or branched alkyl group having 1 to 4 carbon atoms or CN. It is possible here for two or more adjacent $R^4$ substituents together to form a mono- or polycyclic ring system. The aromatic or heteroaromatic ring system having 5 to 40 aromatic ring atoms in this $R^4$ is preferably derived from benzene, dibenzofuran, dibenzothiophene, 9-phenylcarbazole, biphenyl, terphenyl and triphenylene.

The preferred position of the substituent(s) $[R^4]_r$ is position 1, 2 or 3, more preferably 3, where $R^4$ has one of the preferred definitions given above and r is greater than 0.

In compounds of the formulae (2), (2a), (2b), (2c), (2d), (2e), (2f), (2g), (2h) and (2i), s is preferably 0, 1 or 2, where $R^4$ has a definition given above or a definition given below. More preferably, s is 0 or 1, most preferably 0.

When s is greater than 0 in compounds of the formulae (2), (2a), (2b), (2c), (2d), (2e), (2f), (2g), (2h) and (2i), the substituent $R^4$ is the same or different at each instance and is preferably selected as described for r.

Ar in $N(Ar)_2$ is preferably derived from benzene, dibenzofuran, fluorene, spirobifluorene, dibenzothiophene, 9-phenylcarbazole, biphenyl and terphenyl which may be substituted by one or more substituents $R^3$. Ar here is preferably unsubstituted.

The substituent $R^2$ is the same or different at each instance and is preferably selected from the group consisting of D, F, Cl, Br, I, CN, $NO_2$, $N(Ar)_2$, $NH_2$, $N(R^3)_2$, C(═O)Ar, C(═O)H, C(═O)$R^3$, P(═O)$(Ar)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^3$ radicals, an aromatic or heteroaromatic ring system which has 5 to 60 aromatic ring atoms and may in each case be substituted by one or more $R^3$ radicals, an aryloxy or heteroaryloxy group which has 5 to 60 aromatic ring atoms and may be substituted by one or more $R^3$ radicals. The substituent $R^2$ when it occurs is more preferably an aromatic or heteroaromatic ring system as described above, preferably selected from the group of carbazole, 9-phenylcarbazole, dibenzofuran, dibenzothiophene, fluorene, terphenyl or spirobifluorene, most preferably derived from a dibenzofuran.

In the case of substitution of one of the substituents $R^2$ as described above by a substituent $R^3$, the definitions of $R^3$ as described above or described as preferred are applicable.

In compounds of the formulae (2), (2a), (2b), (2c), (2d), (2e), (2f), (2g), (2h) and (2i), as described above, $Ar_3$ is in each case independently an aromatic ring system having 6 to 40 aromatic ring atoms or a heteroaromatic ring system having 10 to 40 aromatic ring atoms which may be substituted by one or more $R^3$ radicals.

$Ar_3$ is preferably derived from benzene, dibenzofuran, fluorene, spirobifluorene, dibenzothiophene, 9-phenylcarbazole, biphenyl and terphenyl, which may be substituted by one or more substituents $R^3$, where $R^3$ has a definition given above.

In the case of the heteroaromatic ring systems which have 10 to 40 carbon atoms and may be substituted by one or more of the substituents $R^3$, particular preference is given to electron-rich ring systems, where the optionally $R^3$-substituted ring system preferably contains just one nitrogen atom in its entirety or the optionally $R^3$-substituted ring system contains one or more oxygen and/or sulfur atoms in its entirety.

In compounds of the formulae (2), (2a), (2b), (2c), (2d), (2e), (2f), (2g), (2h) and (2i) or compounds of the formulae (2), (2a), (2b), (2c), (2d), (2e), (2f), (2g), (2h) and (2i) described with preference, $Ar_3$ is preferably selected from the aromatic or heteroaromatic ring systems Ar-1 to Ar-22

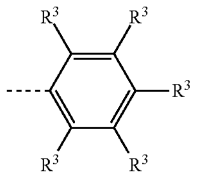

Ar-1

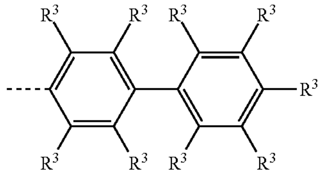

Ar-2

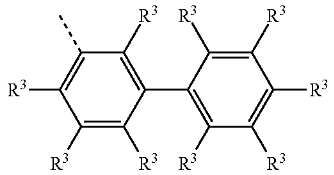

Ar-3

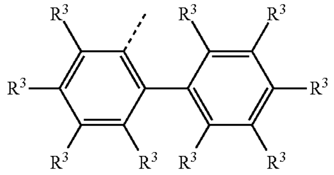

Ar-4

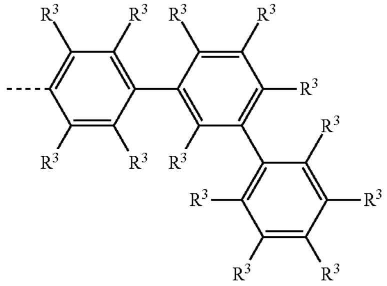

Ar-5

-continued
Ar-6
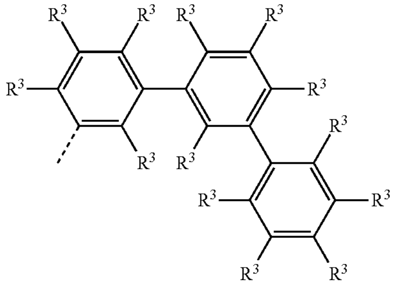
Ar-7
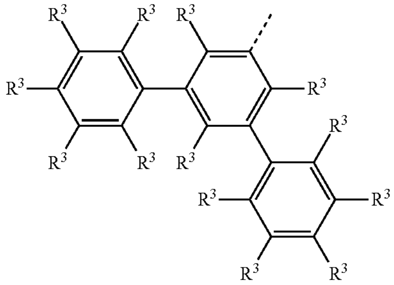
Ar-8
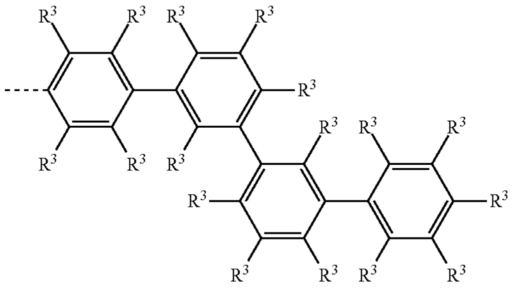
Ar-9
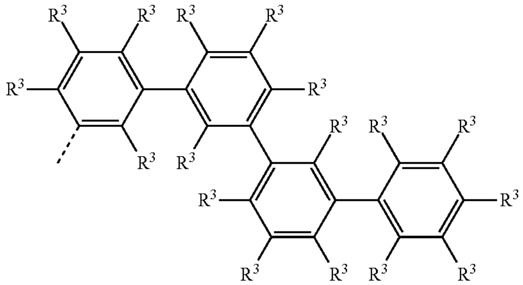
Ar-10
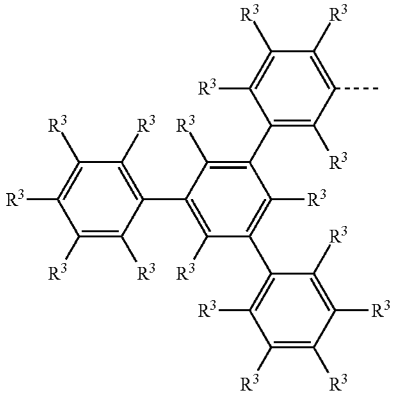
-continued
Ar-11
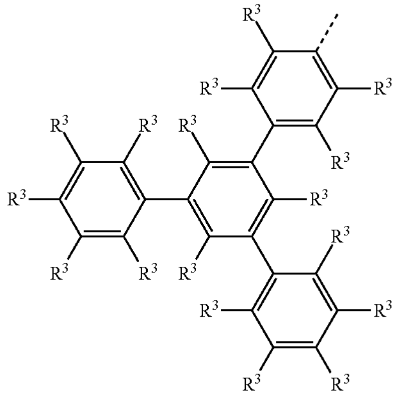
Ar-12
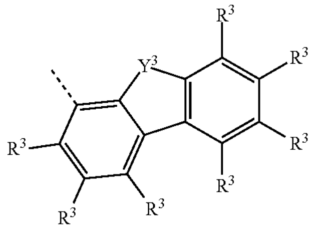
Ar-13
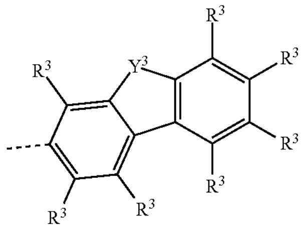
Ar-14
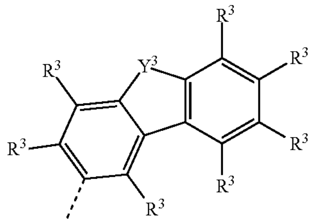
Ar-15
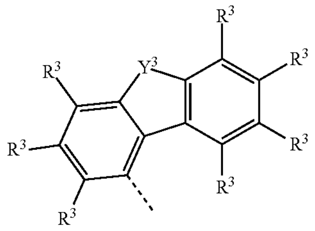
Ar-16
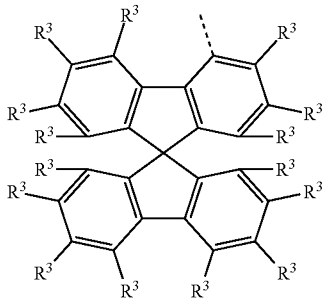

-continued

Ar-17

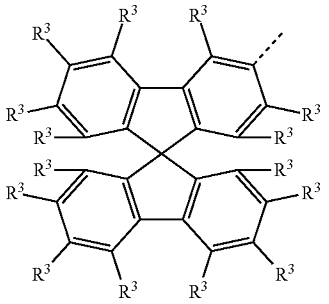

Ar-18

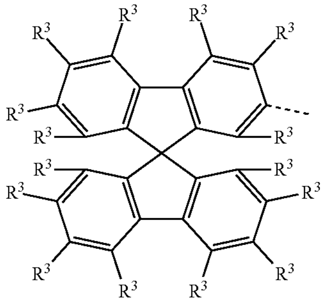

Ar-19

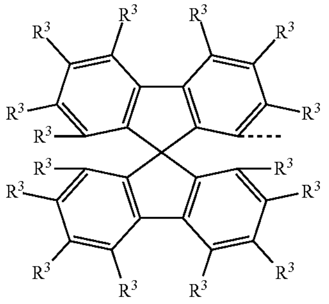

Ar-20

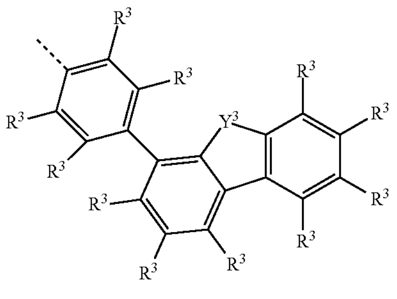

Ar-21

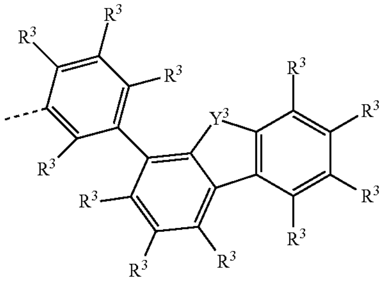

-continued

Ar-22

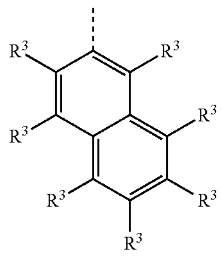

where $Y^3$ at each instance is the same or different and is O, $NR^{\#}$, S or $C(R^{\#})_2$ where the $R^{\#}$ radical bonded to N is not H, and $R^3$ has the aforementioned definition or a preferred definition below and the dotted bond represents the bond to the nitrogen atom.

The $R^{\#}$ radical is the same or different at each instance and is H, D, F, Cl, Br, I, CN, $NO_2$, $N(Ar)_2$, $N(R^2)_2$, C(=O)Ar, $C(=O)R^2$, $P(=O)(Ar)_2$, $P(Ar)_2$, $B(Ar)_2$, $Si(Ar)_3$, $Si(R^2)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to carbon atoms, each of which may be substituted by one or more $R^2$ radicals, where one or more nonadjacent $CH_2$ groups may be replaced by $R^2C{=}CR^2$, $Si(R^2)_2$, C=O, C=S, $C{=}NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^2$ radicals, an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals; at the same time, it is optionally possible for two substituents $R^{\#}$ bonded to the same carbon atom or to adjacent carbon atoms to form a monocyclic or polycyclic, aliphatic, aromatic or heteroaromatic ring system which may be substituted by one or more $R^2$ radicals.

$Y^3$ is preferably O, S or $C(CH_3)_2$. $Y^3$ is most preferably O.

In the structures Ar-1 to Ar-22, the substituent $R^3$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more adjacent substituents $R^3$ together to form a mono- or polycyclic, aliphatic ring system. In the structures Ar-1 to Ar-22, the substituent $R^3$ is the same or different at each instance and is preferably selected from the group consisting of H, F, CN, an aliphatic hydrocarbyl radical having 1 to 10 carbon atoms or an aromatic or heteroaromatic ring system having 5 to 30 aromatic ring atoms. In the structures Ar-1 to Ar-22, the substituent $R^3$ is the same or different at each instance and is preferably selected from the group consisting of H or an aromatic or heteroaromatic ring system having 5 to 30 aromatic ring atoms, as described above, but preferably dibenzofuran, dibenzothiophene, 9-phenylcarbazole or spirobifluorene. In the structures Ar-1 to Ar-22, the substituent $R^3$ at each instance is more preferably H.

Examples of suitable compounds of the formulae (2), (2a), (2b), (2c), (2d), (2e), (2f), (2g), (2h) and (2i) that are selected in accordance with the invention are the structures shown below in table 3.
TABLE 3
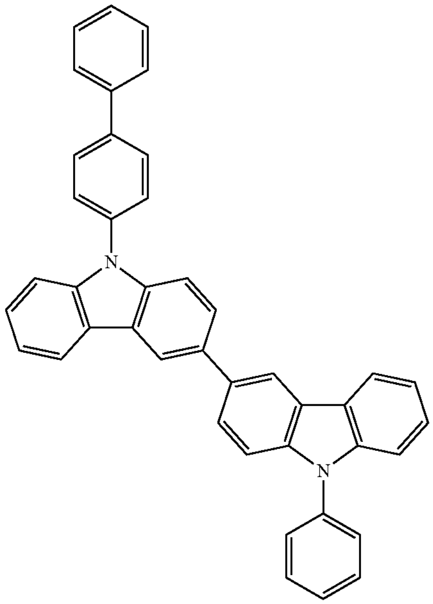 [SMILES: c1ccc(-c2ccc(-n3c4ccccc4c4cc(-c5ccc6c(c5)c5ccccc5n6-c5ccccc5)ccc43)cc2)cc1]
12
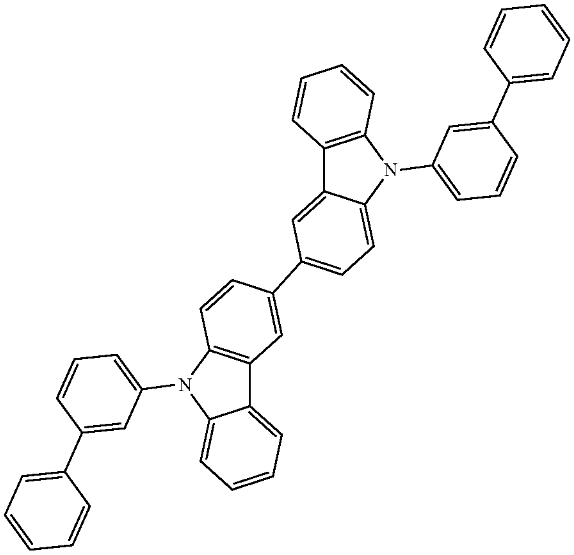 [SMILES: c1ccc(-c2cccc(-n3c4ccccc4c4cc(-c5ccc6c(c5)c5ccccc5n6-c5cccc(-c6ccccc6)c5)ccc43)c2)cc1]
13

TABLE 3-continued
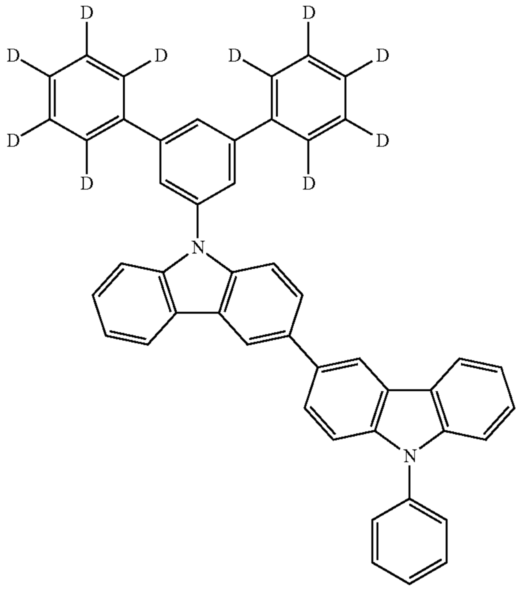 [SMILES: [2H]c1c([2H])c([2H])c(-c2cc(-c3c([2H])c([2H])c([2H])c([2H])c3[2H])cc(-n3c4ccccc4c4cc(-c5ccc6c(c5)c5ccccc5n6-c5ccccc5)ccc43)c2)c([2H])c1[2H]]
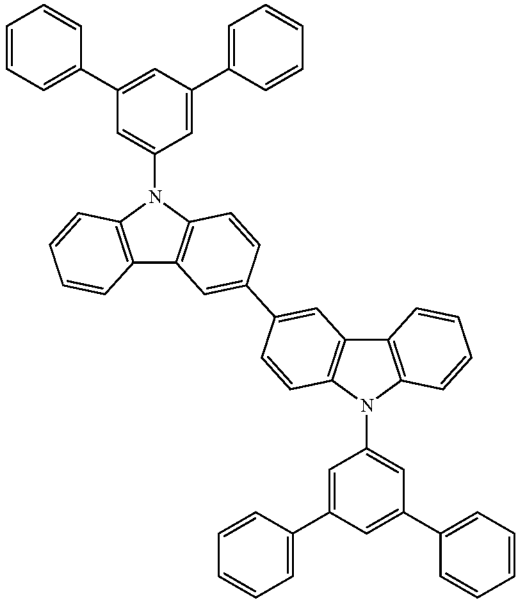 [SMILES: c1ccc(-c2cc(-c3ccccc3)cc(-n3c4ccccc4c4cc(-c5ccc6c(c5)c5ccccc5n6-c5cc(-c6ccccc6)cc(-c6ccccc6)c5)ccc43)c2)cc1]

TABLE 3-continued
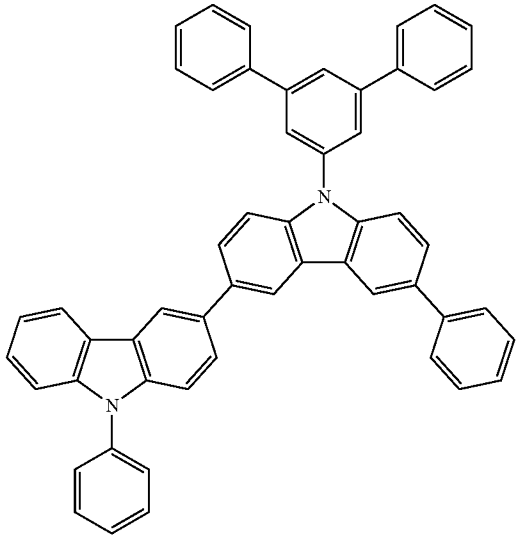 [SMILES: c1ccc(-c2cc(-c3ccccc3)cc(-n3c4ccc(-c5ccccc5)cc4c4cc(-c5ccc6c(c5)c5ccccc5n6-c5ccccc5)ccc43)c2)cc1]
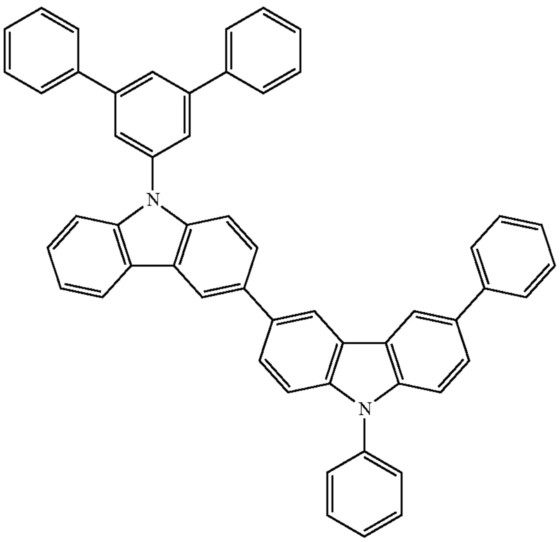 [SMILES: c1ccc(-c2cc(-c3ccccc3)cc(-n3c4ccccc4c4cc(-c5ccc6c(c5)c5cc(-c7ccccc7)ccc5n6-c5ccccc5)ccc43)c2)cc1]

TABLE 3-continued
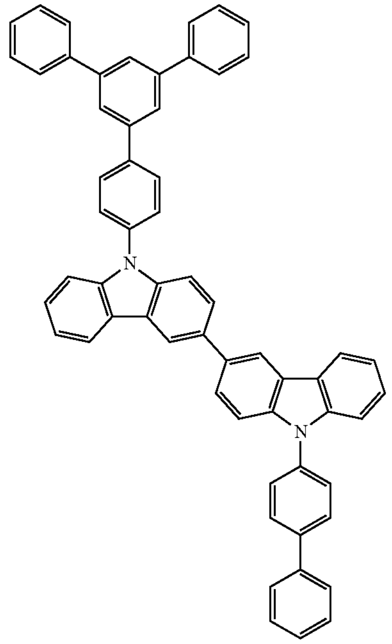 [SMILES: c1ccc(-c2ccc(-n3c4ccccc4c4cc(-c5ccc6c(c5)c5ccccc5n6-c5ccc(-c6cc(-c7ccccc7)cc(-c7ccccc7)c6)cc5)ccc43)cc2)cc1]
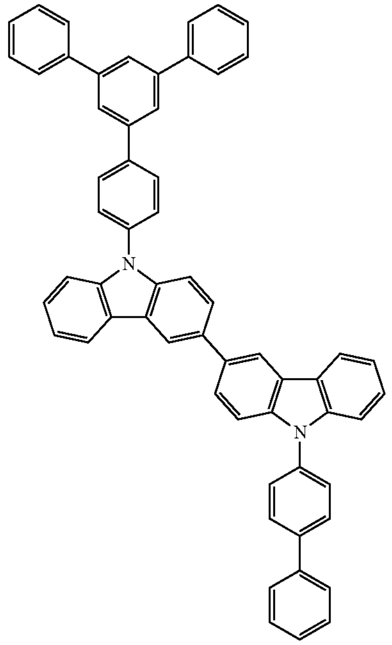 [SMILES: c1ccc(-c2ccc(-n3c4ccccc4c4cc(-c5ccc6c(c5)c5ccccc5n6-c5ccc(-c6cc(-c7ccccc7)cc(-c7ccccc7)c6)cc5)ccc43)cc2)cc1]

TABLE 3-continued
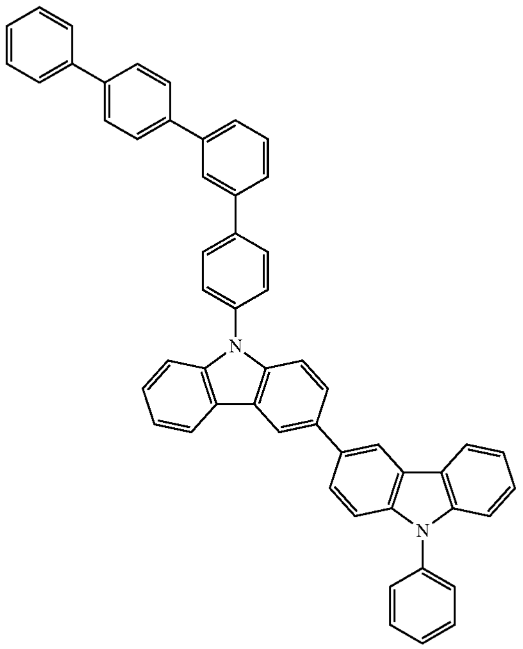 [SMILES: c1ccc(-c2ccc(-c3cccc(-c4ccc(-n5c6ccccc6c6cc(-c7ccc8c(c7)c7ccccc7n8-c7ccccc7)ccc65)cc4)c3)cc2)cc1]
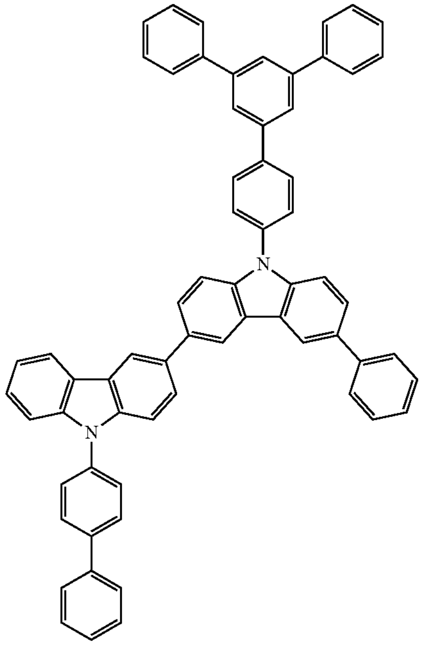 [SMILES: c1ccc(-c2ccc(-n3c4ccccc4c4cc(-c5ccc6c(c5)c5cc(-c7ccccc7)ccc5n6-c5ccc(-c6cc(-c7ccccc7)cc(-c7ccccc7)c6)cc5)ccc43)cc2)cc1]

TABLE 3-continued
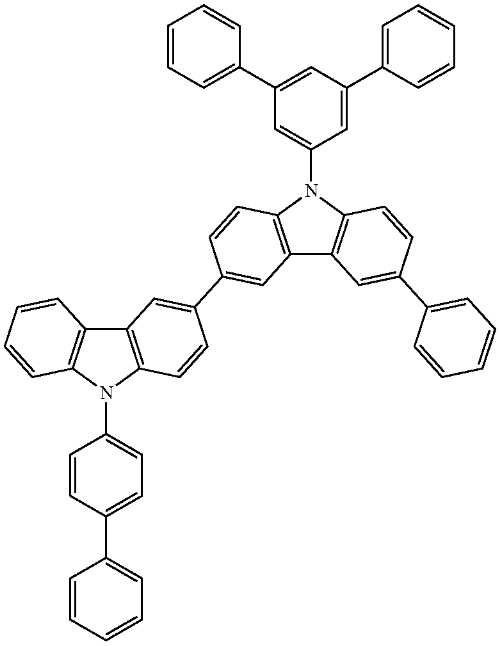 [SMILES: c1ccc(-c2ccc(-n3c4ccccc4c4cc(-c5ccc6c(c5)c5cc(-c7ccccc7)ccc5n6-c5cc(-c6ccccc6)cc(-c6ccccc6)c5)ccc43)cc2)cc1]
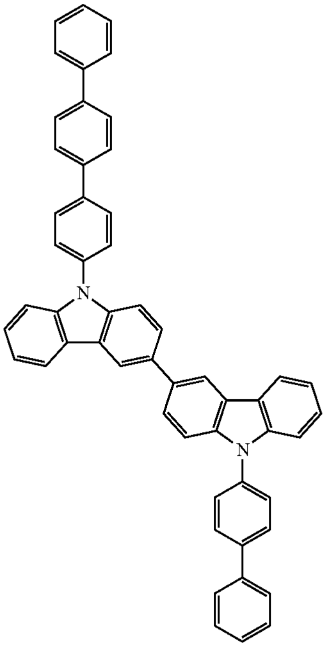 [SMILES: c1ccc(-c2ccc(-c3ccc(-n4c5ccccc5c5cc(-c6ccc7c(c6)c6ccccc6n7-c6ccc(-c7ccccc7)cc6)ccc54)cc3)cc2)cc1]

TABLE 3-continued
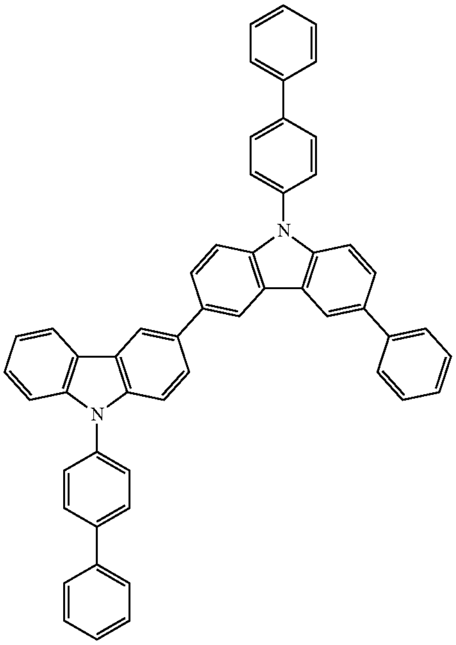 [SMILES: c1ccc(-c2ccc(-n3c4ccccc4c4cc(-c5ccc6c(c5)c5cc(-c7ccccc7)ccc5n6-c5ccc(-c6ccccc6)cc5)ccc43)cc2)cc1]
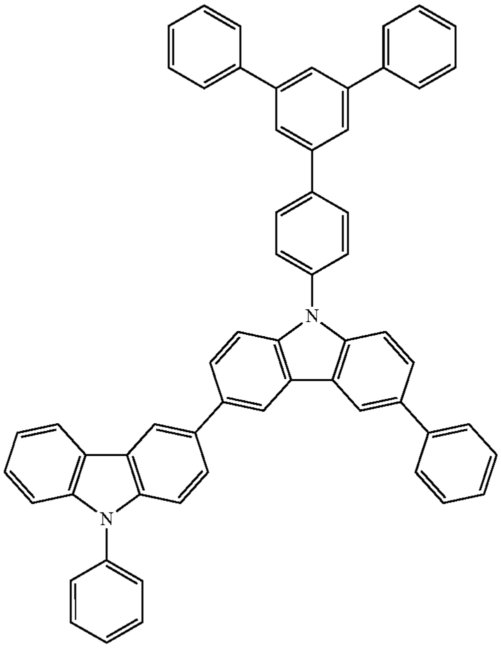 [SMILES: c1ccc(-c2cc(-c3ccccc3)cc(-c3ccc(-n4c5ccc(-c6ccccc6)cc5c5cc(-c6ccc7c(c6)c6ccccc6n7-c6ccccc6)ccc54)cc3)c2)cc1]

TABLE 3-continued
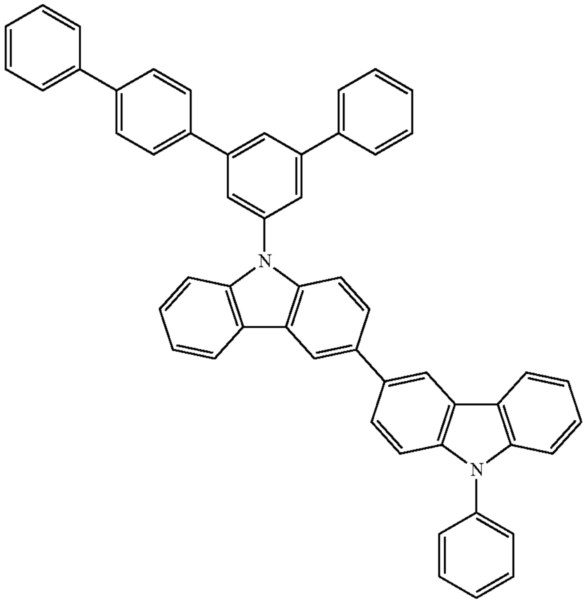 [SMILES: c1ccc(-c2ccc(-c3cc(-c4ccccc4)cc(-n4c5ccccc5c5cc(-c6ccc7c(c6)c6ccccc6n7-c6ccccc6)ccc54)c3)cc2)cc1]
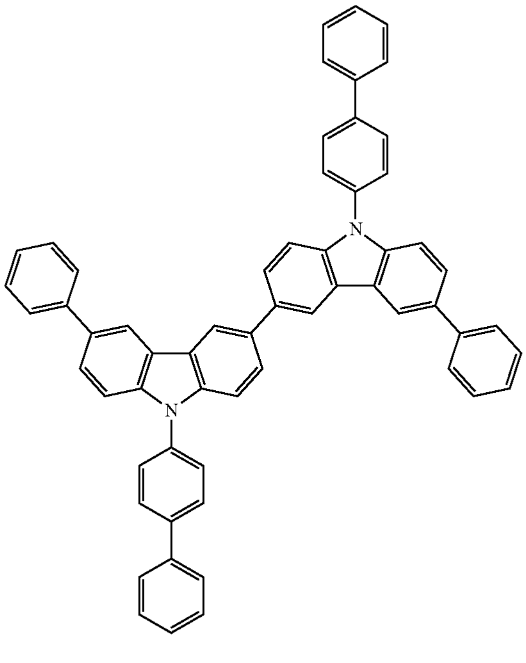 [SMILES: c1ccc(-c2ccc(-n3c4ccc(-c5ccccc5)cc4c4cc(-c5ccc6c(c5)c5cc(-c7ccccc7)ccc5n6-c5ccc(-c6ccccc6)cc5)ccc43)cc2)cc1]

TABLE 3-continued
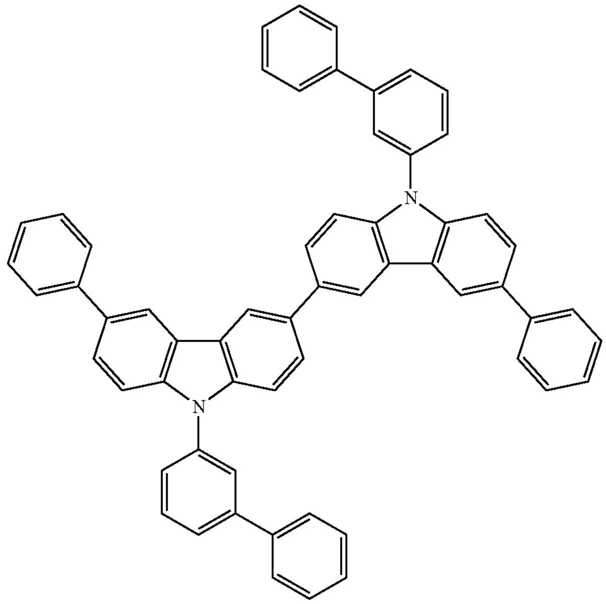 [SMILES: c1ccc(-c2cccc(-n3c4ccc(-c5ccccc5)cc4c4cc(-c5ccc6c(c5)c5cc(-c7ccccc7)ccc5n6-c5cccc(-c6ccccc6)c5)ccc43)c2)cc1]
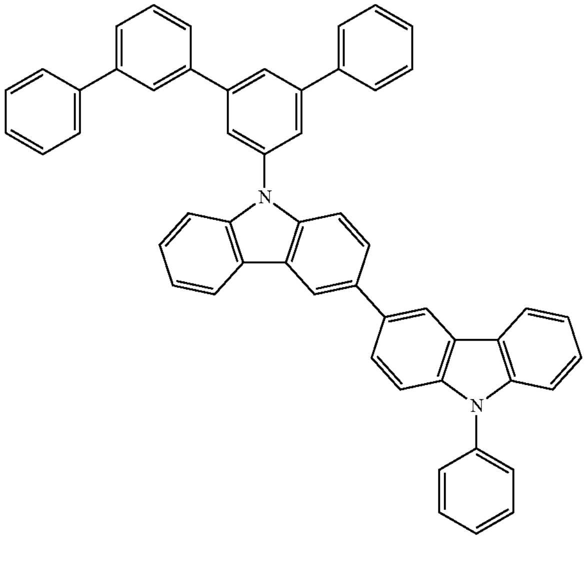 [SMILES: c1ccc(-c2cccc(-c3cc(-c4ccccc4)cc(-n4c5ccccc5c5cc(-c6ccc7c(c6)c6ccccc6n7-c6ccccc6)ccc54)c3)c2)cc1]

TABLE 3-continued
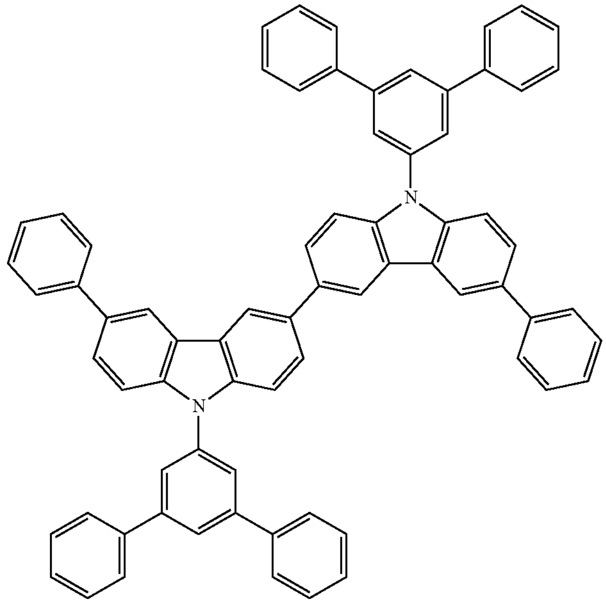 [SMILES: c1ccc(-c2cc(-c3ccccc3)cc(-n3c4ccc(-c5ccccc5)cc4c4cc(-c5ccc6c(c5)c5cc(-c7ccccc7)ccc5n6-c5cc(-c6ccccc6)cc(-c6ccccc6)c5)ccc43)c2)cc1]
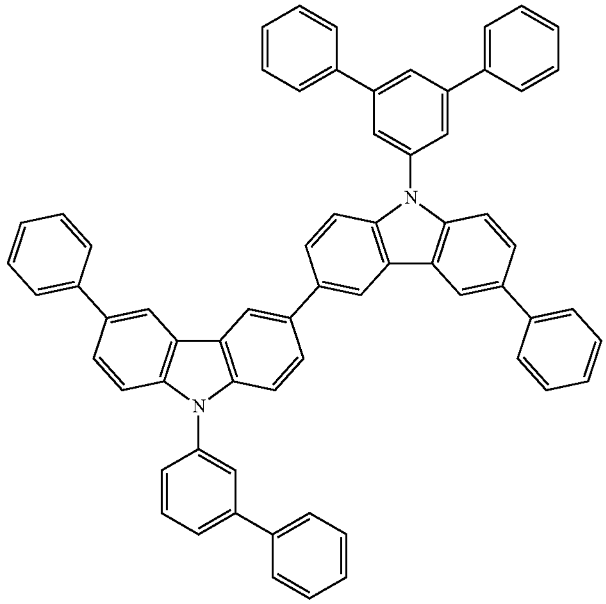 [SMILES: c1ccc(-c2cccc(-n3c4ccc(-c5ccccc5)cc4c4cc(-c5ccc6c(c5)c5cc(-c7ccccc7)ccc5n6-c5cc(-c6ccccc6)cc(-c6ccccc6)c5)ccc43)c2)cc1]

TABLE 3-continued
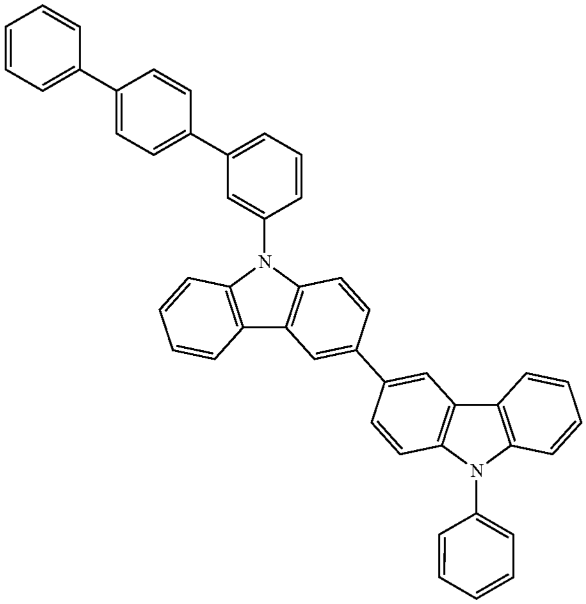 [SMILES: c1ccc(-c2ccc(-c3cccc(-n4c5ccccc5c5cc(-c6ccc7c(c6)c6ccccc6n7-c6ccccc6)ccc54)c3)cc2)cc1]
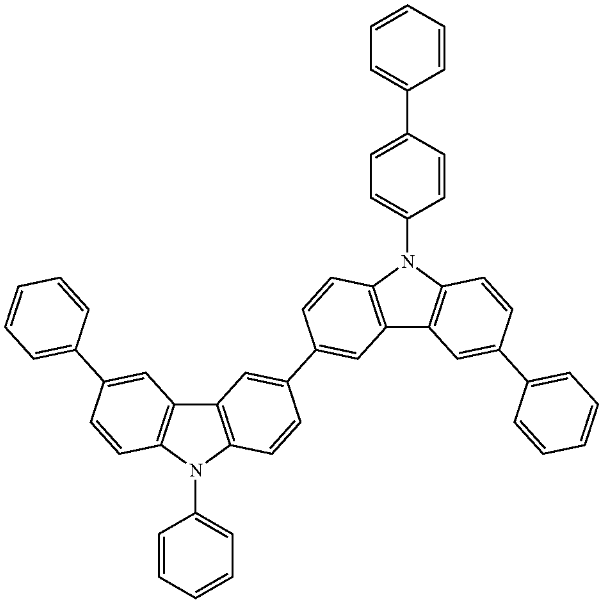 [SMILES: c1ccc(-c2ccc(-n3c4ccc(-c5ccccc5)cc4c4cc(-c5ccc6c(c5)c5cc(-c7ccccc7)ccc5n6-c5ccccc5)ccc43)cc2)cc1]

TABLE 3-continued
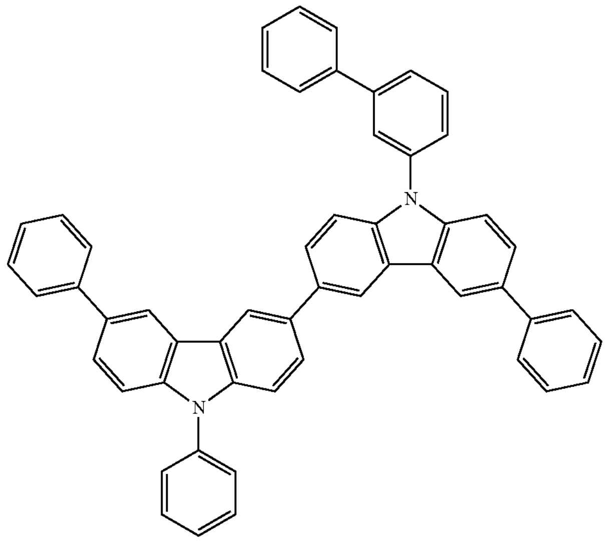 [SMILES: c1ccc(-c2cccc(-n3c4ccc(-c5ccccc5)cc4c4cc(-c5ccc6c(c5)c5cc(-c7ccccc7)ccc5n6-c5ccccc5)ccc43)c2)cc1]
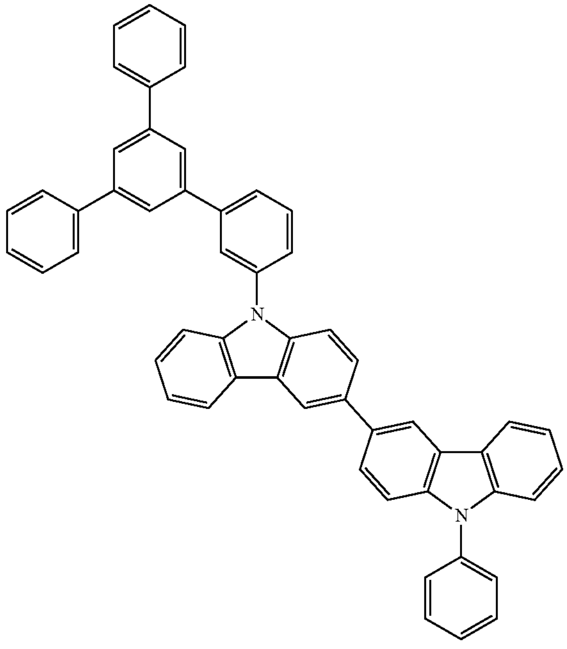 [SMILES: c1ccc(-c2cc(-c3ccccc3)cc(-c3cccc(-n4c5ccccc5c5cc(-c6ccc7c(c6)c6ccccc6n7-c6ccccc6)ccc54)c3)c2)cc1]

TABLE 3-continued
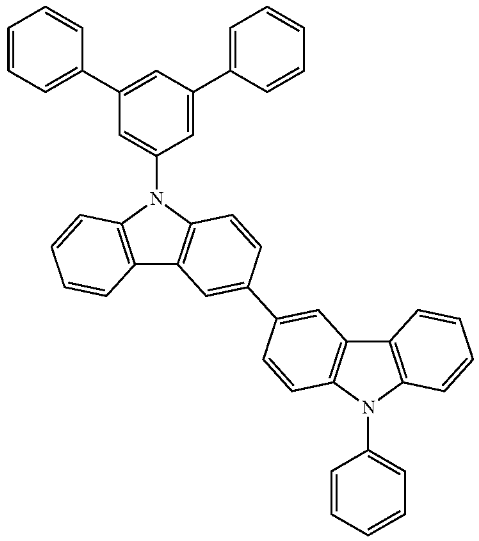 [SMILES: c1ccc(-c2cc(-c3ccccc3)cc(-n3c4ccccc4c4cc(-c5ccc6c(c5)c5ccccc5n6-c5ccccc5)ccc43)c2)cc1]
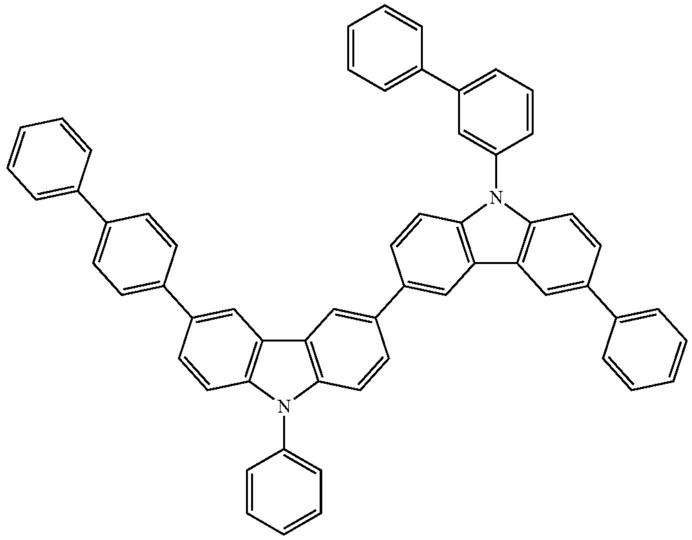 [SMILES: c1ccc(-c2ccc(-c3ccc4c(c3)c3cc(-c5ccc6c(c5)c5cc(-c7ccccc7)ccc5n6-c5cccc(-c6ccccc6)c5)ccc3n4-c3ccccc3)cc2)cc1]

TABLE 3-continued
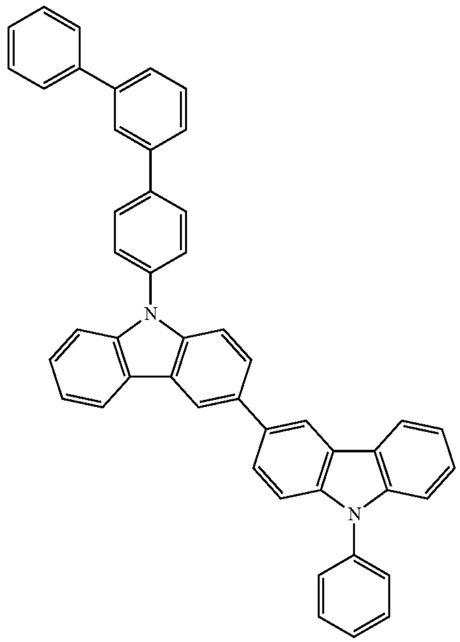 [SMILES: c1ccc(-c2cccc(-c3ccc(-n4c5ccccc5c5cc(-c6ccc7c(c6)c6ccccc6n7-c6ccccc6)ccc54)cc3)c2)cc1]
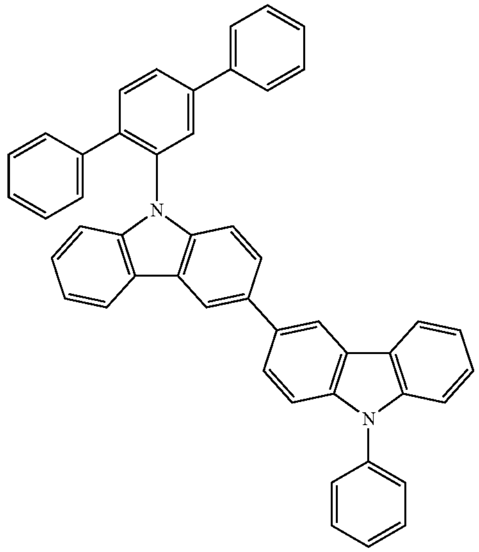 [SMILES: c1ccc(-c2ccc(-c3ccccc3)c(-n3c4ccccc4c4cc(-c5ccc6c(c5)c5ccccc5n6-c5ccccc5)ccc43)c2)cc1]

TABLE 3-continued
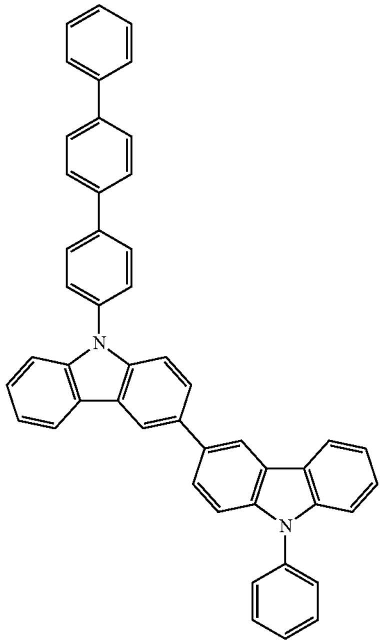 [SMILES: c1ccc(-c2ccc(-c3ccc(-n4c5ccccc5c5cc(-c6ccc7c(c6)c6ccccc6n7-c6ccccc6)ccc54)cc3)cc2)cc1]
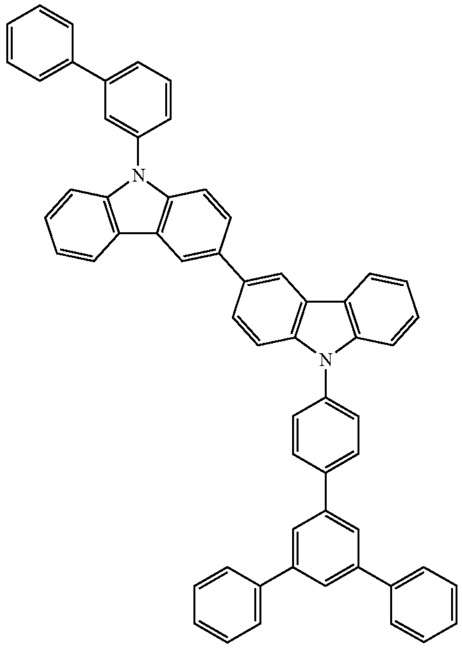 [SMILES: c1ccc(-c2cc(-c3ccccc3)cc(-c3ccc(-n4c5ccccc5c5cc(-c6ccc7c(c6)c6ccccc6n7-c6cccc(-c7ccccc7)c6)ccc54)cc3)c2)cc1]

TABLE 3-continued
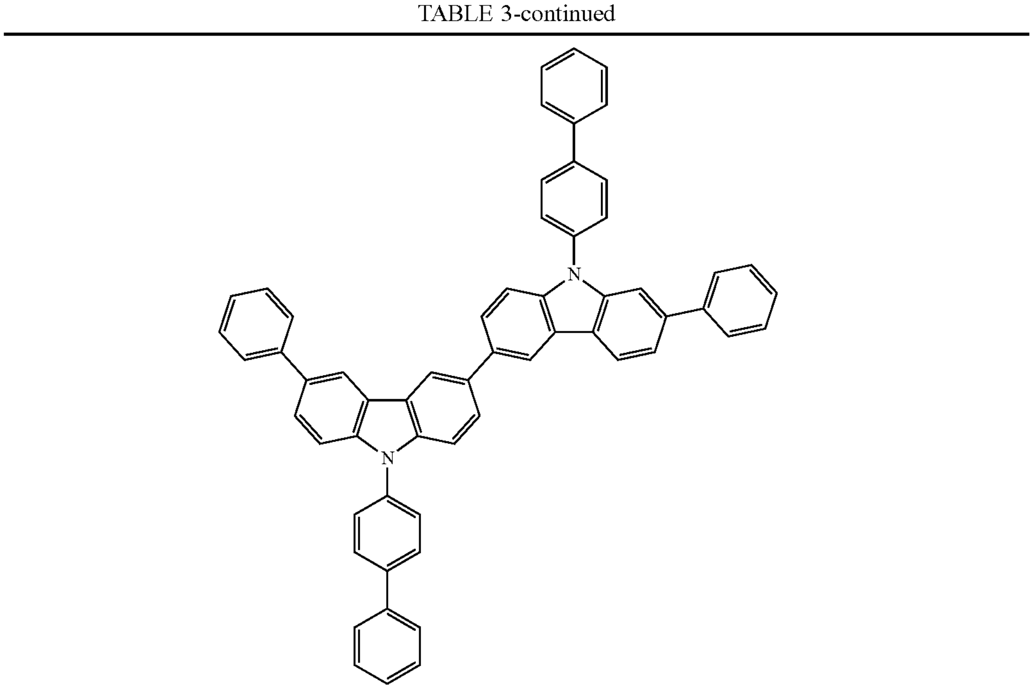
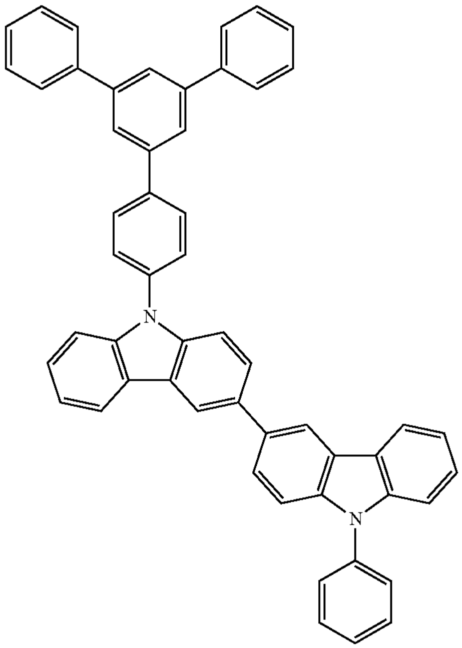 [SMILES: c1ccc(-c2cc(-c3ccccc3)cc(-c3ccc(-n4c5ccccc5c5cc(-c6ccc7c(c6)c6ccccc6n7-c6ccccc6)ccc54)cc3)c2)cc1]

TABLE 3-continued
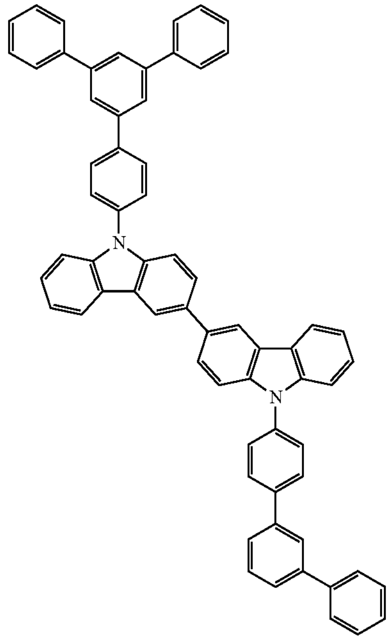 [SMILES: c1ccc(-c2cccc(-c3ccc(-n4c5ccccc5c5cc(-c6ccc7c(c6)c6ccccc6n7-c6ccc(-c7cc(-c8ccccc8)cc(-c8ccccc8)c7)cc6)ccc54)cc3)c2)cc1]
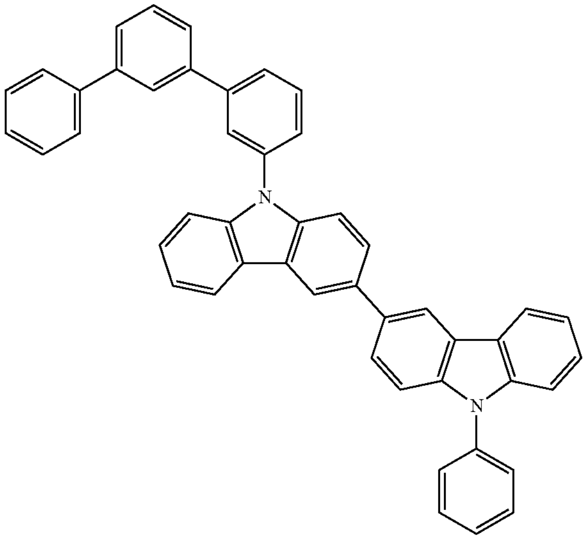 [SMILES: c1ccc(-c2cccc(-c3cccc(-n4c5ccccc5c5cc(-c6ccc7c(c6)c6ccccc6n7-c6ccccc6)ccc54)c3)c2)cc1]
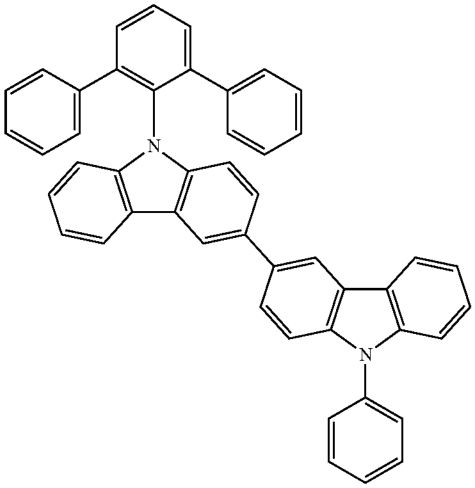 [SMILES: c1ccc(-c2cccc(-c3ccccc3)c2-n2c3ccccc3c3cc(-c4ccc5c(c4)c4ccccc4n5-c4ccccc4)ccc32)cc1]

TABLE 3-continued
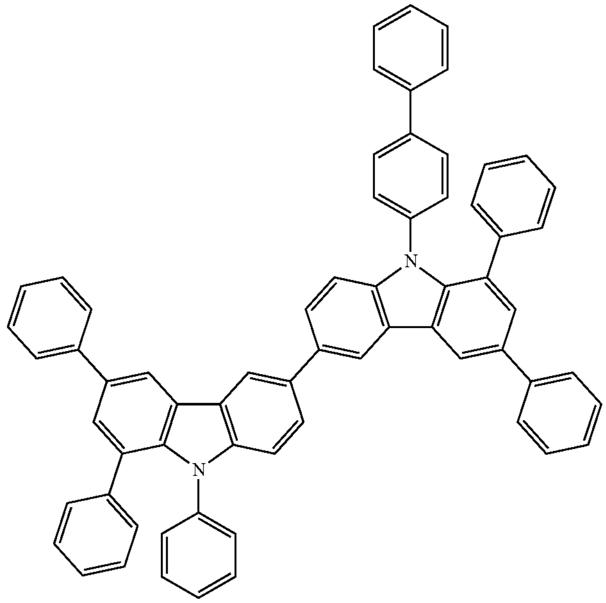 [SMILES: c1ccc(-c2ccc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)cc2)cc1]
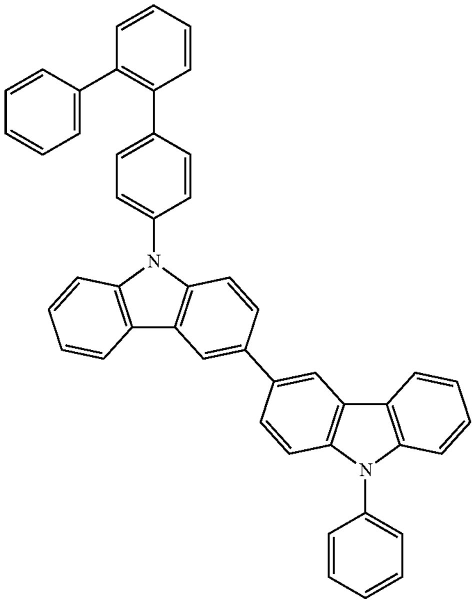 [SMILES: c1ccc(-c2ccccc2-c2ccc(-n3c4ccccc4c4cc(-c5ccc6c(c5)c5ccccc5n6-c5ccccc5)ccc43)cc2)cc1]

TABLE 3-continued
14
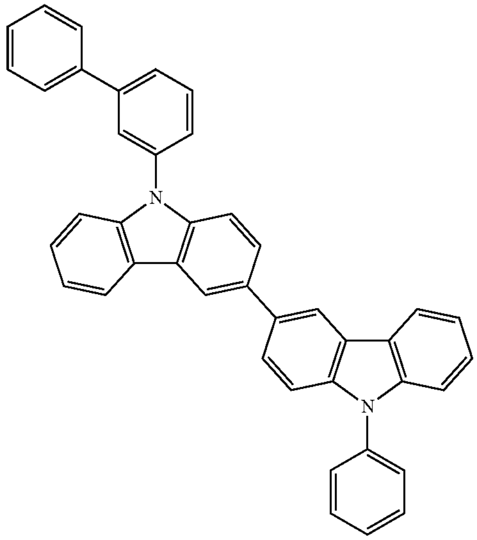 [SMILES: c1ccc(-c2cccc(-n3c4ccccc4c4cc(-c5ccc6c(c5)c5ccccc5n6-c5ccccc5)ccc43)c2)cc1]
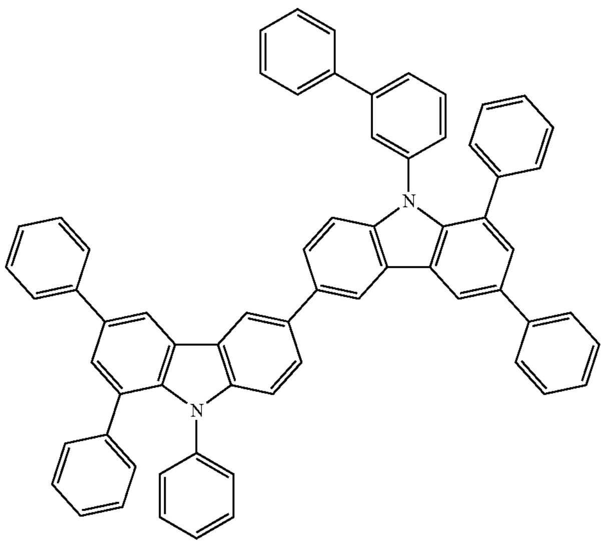 [SMILES: c1ccc(-c2cccc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)c2)cc1]

TABLE 3-continued
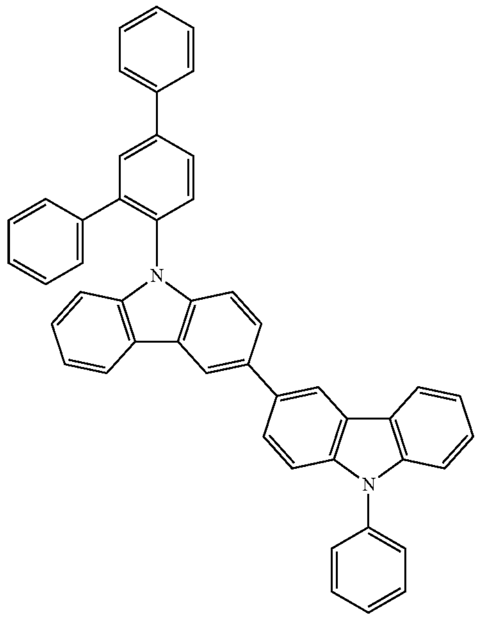 [SMILES: c1ccc(-c2ccc(-n3c4ccccc4c4cc(-c5ccc6c(c5)c5ccccc5n6-c5ccccc5)ccc43)c(-c3ccccc3)c2)cc1]
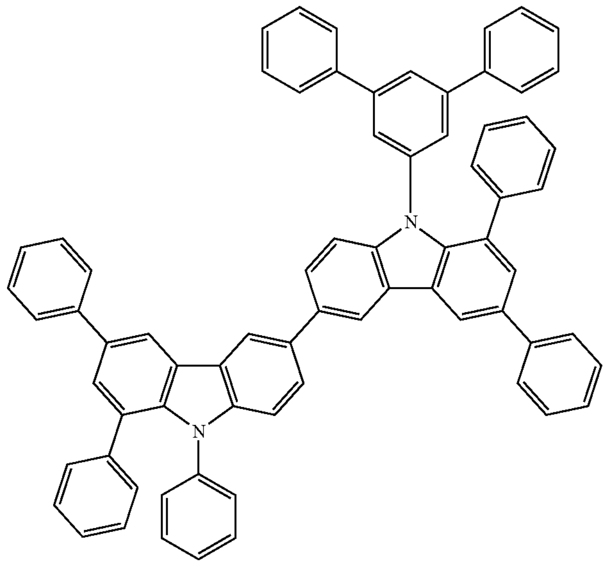 [SMILES: c1ccc(-c2cc(-c3ccccc3)cc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)c2)cc1]

TABLE 3-continued
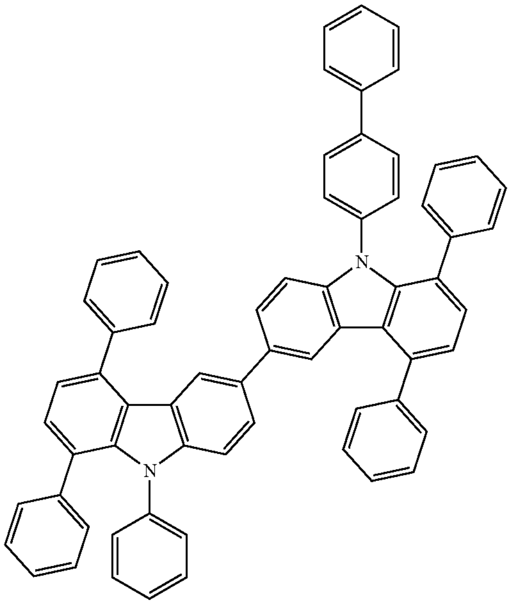 [SMILES: c1ccc(-c2ccc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)cc2)cc1]
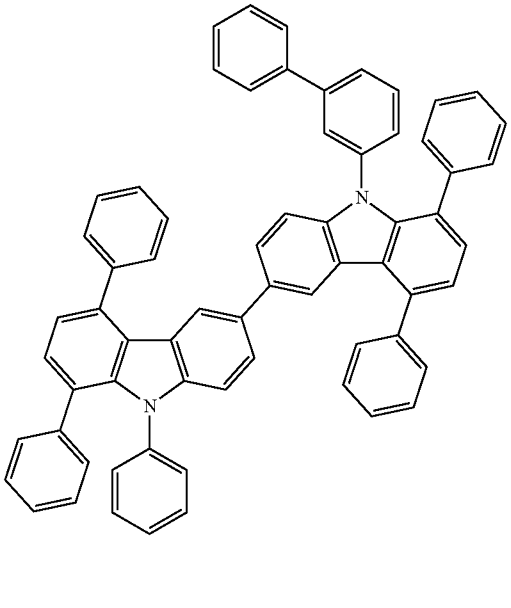 [SMILES: c1ccc(-c2cccc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)c2)cc1]

TABLE 3-continued
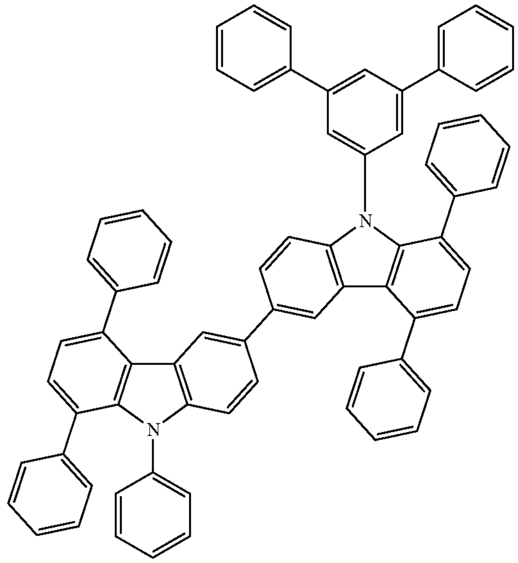 [SMILES: c1ccc(-c2cc(-c3ccccc3)cc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)c2)cc1]
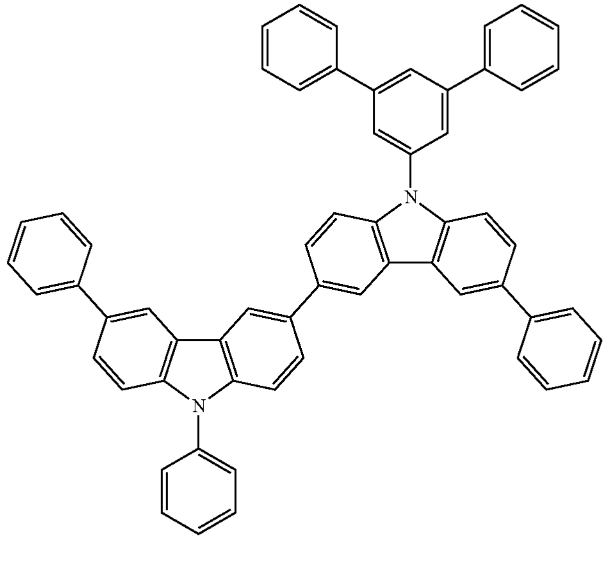 [SMILES: c1ccc(-c2cc(-c3ccccc3)cc(-n3c4ccc(-c5ccccc5)cc4c4cc(-c5ccc6c(c5)c5cc(-c7ccccc7)ccc5n6-c5ccccc5)ccc43)c2)cc1]

TABLE 3-continued
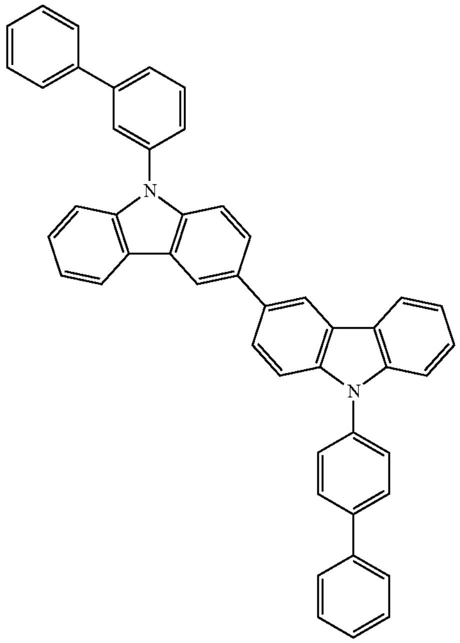 [SMILES: c1ccc(-c2ccc(-n3c4ccccc4c4cc(-c5ccc6c(c5)c5ccccc5n6-c5cccc(-c6ccccc6)c5)ccc43)cc2)cc1]
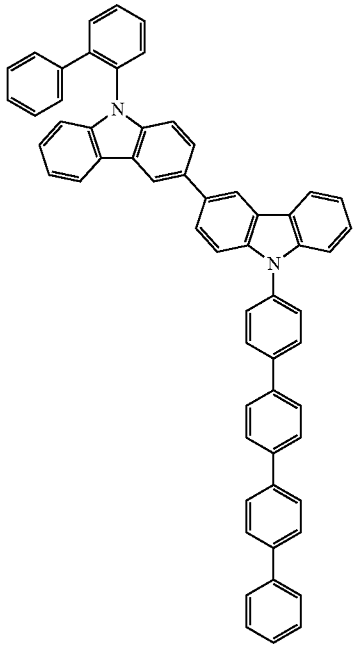 [SMILES: c1ccc(-c2ccc(-c3ccc(-c4ccc(-n5c6ccccc6c6cc(-c7ccc8c(c7)c7ccccc7n8-c7ccccc7-c7ccccc7)ccc65)cc4)cc3)cc2)cc1]

TABLE 3-continued
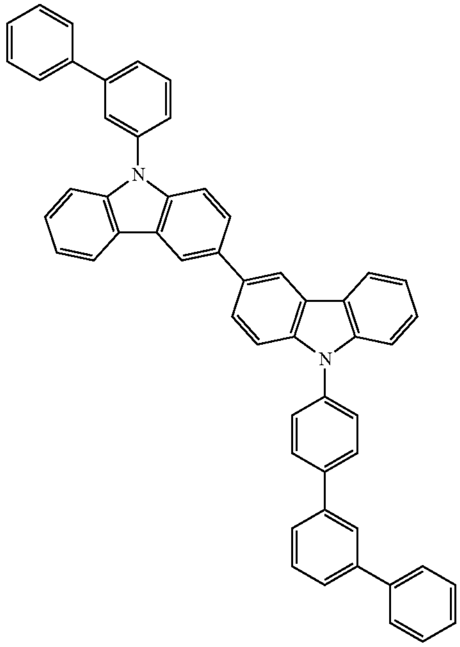 [SMILES: c1ccc(-c2cccc(-c3ccc(-n4c5ccccc5c5cc(-c6ccc7c(c6)c6ccccc6n7-c6cccc(-c7ccccc7)c6)ccc54)cc3)c2)cc1]
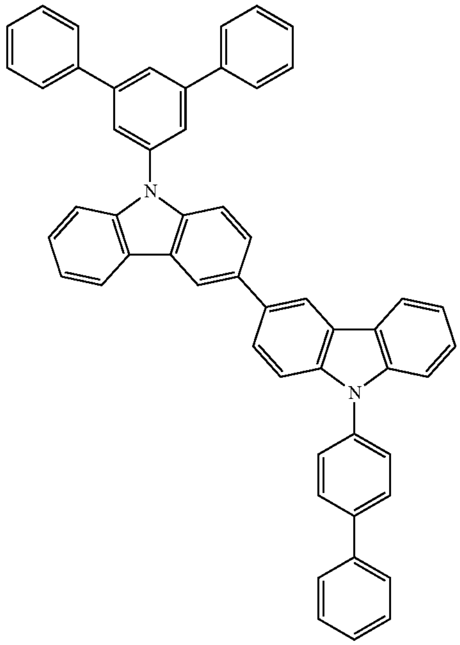 [SMILES: c1ccc(-c2ccc(-n3c4ccccc4c4cc(-c5ccc6c(c5)c5ccccc5n6-c5cc(-c6ccccc6)cc(-c6ccccc6)c5)ccc43)cc2)cc1]

TABLE 3-continued
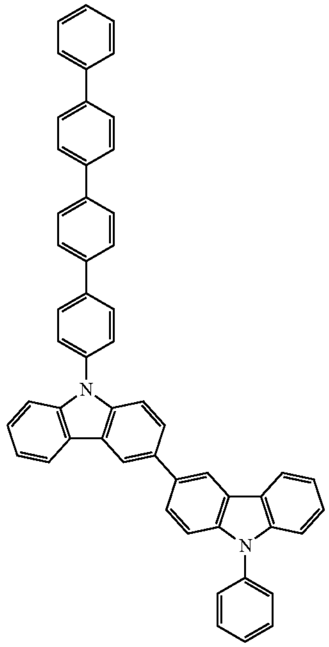 [SMILES: c1ccc(-c2ccc(-c3ccc(-c4ccc(-n5c6ccccc6c6cc(-c7ccc8c(c7)c7ccccc7n8-c7ccccc7)ccc65)cc4)cc3)cc2)cc1]
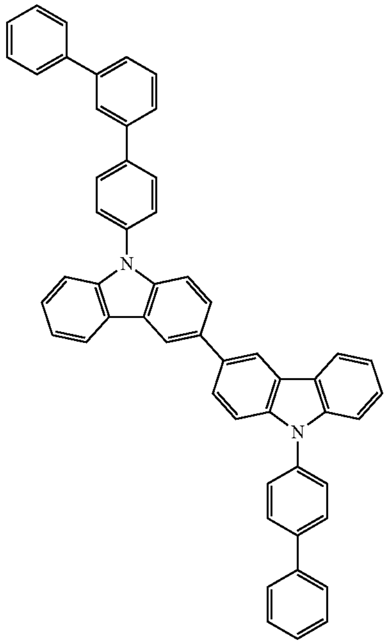 [SMILES: c1ccc(-c2ccc(-n3c4ccccc4c4cc(-c5ccc6c(c5)c5ccccc5n6-c5ccc(-c6cccc(-c7ccccc7)c6)cc5)ccc43)cc2)cc1]

TABLE 3-continued
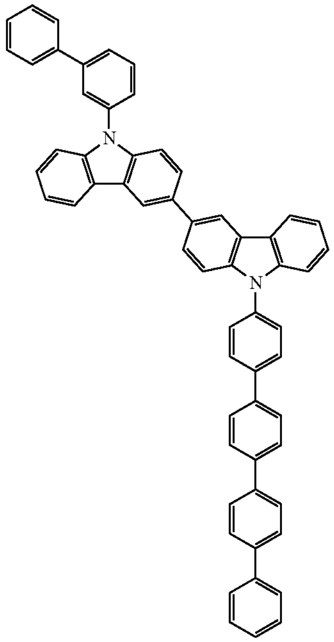 [SMILES: c1ccc(-c2ccc(-c3ccc(-c4ccc(-n5c6ccccc6c6cc(-c7ccc8c(c7)c7ccccc7n8-c7cccc(-c8ccccc8)c7)ccc65)cc4)cc3)cc2)cc1]
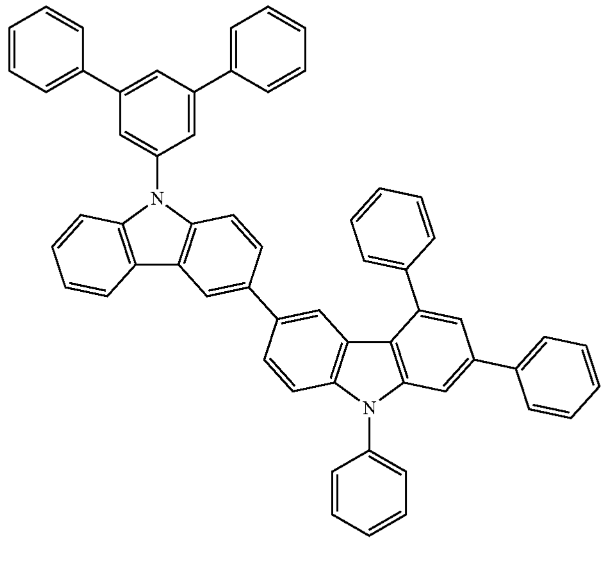 [SMILES: c1ccc(-c2cc(-c3ccccc3)cc(-n3c4ccccc4c4cc(-c5ccc6c(c5)c5c(-c7ccccc7)cc(-c7ccccc7)cc5n6-c5ccccc5)ccc43)c2)cc1]

TABLE 3-continued
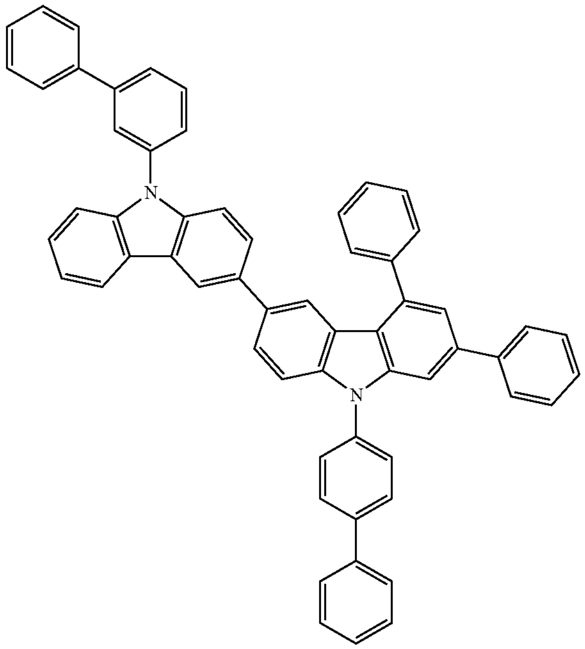 [SMILES: c1ccc(-c2ccc(-n3c4ccc(-c5ccc6c(c5)c5ccccc5n6-c5cccc(-c6ccccc6)c5)cc4c4c(-c5ccccc5)cc(-c5ccccc5)cc43)cc2)cc1]
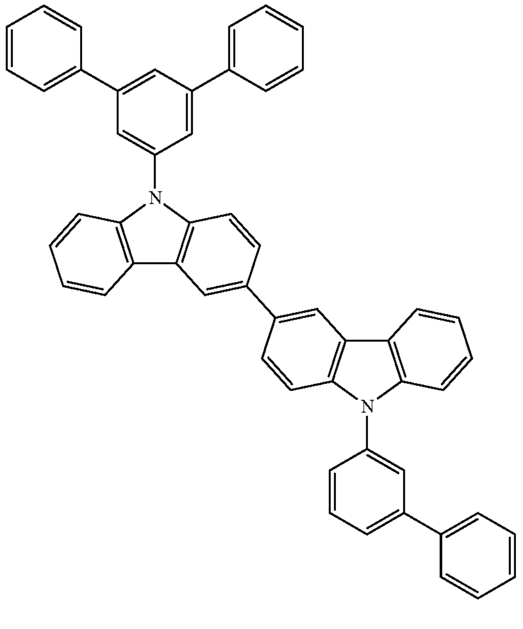 [SMILES: c1ccc(-c2cccc(-n3c4ccccc4c4cc(-c5ccc6c(c5)c5ccccc5n6-c5cc(-c6ccccc6)cc(-c6ccccc6)c5)ccc43)c2)cc1]

TABLE 3-continued
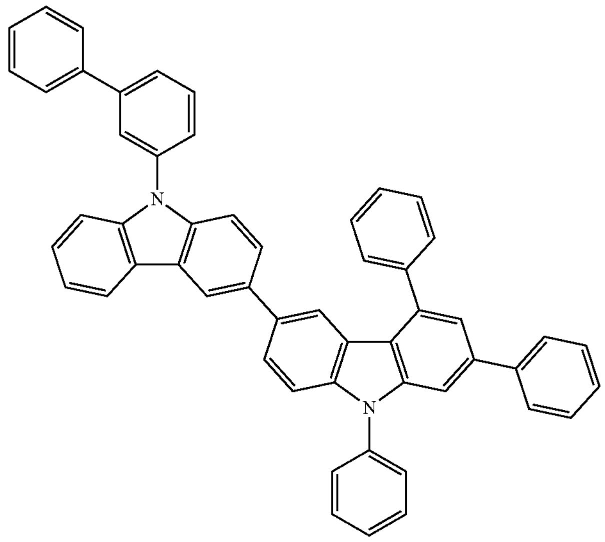 [SMILES: c1ccc(-c2cccc(-n3c4ccccc4c4cc(-c5ccc6c(c5)c5c(-c7ccccc7)cc(-c7ccccc7)cc5n6-c5ccccc5)ccc43)c2)cc1]
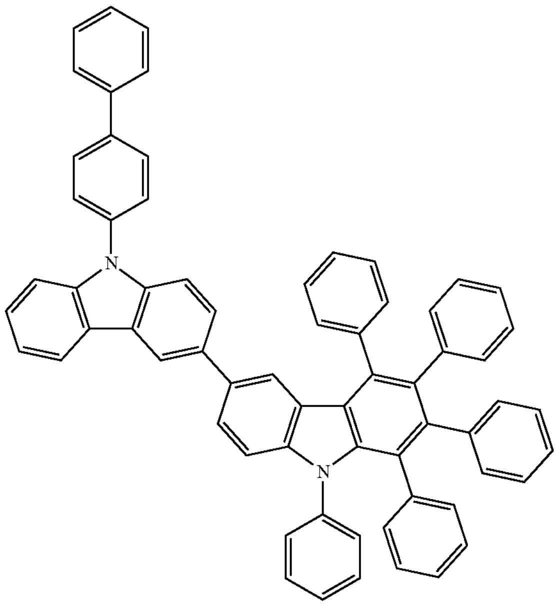 [SMILES: c1ccc(-c2ccc(-n3c4ccccc4c4cc(-c5ccc6c(c5)c5c(-c7ccccc7)c(-c7ccccc7)c(-c7ccccc7)c(-c7ccccc7)c5n6-c5ccccc5)ccc43)cc2)cc1]

TABLE 3-continued
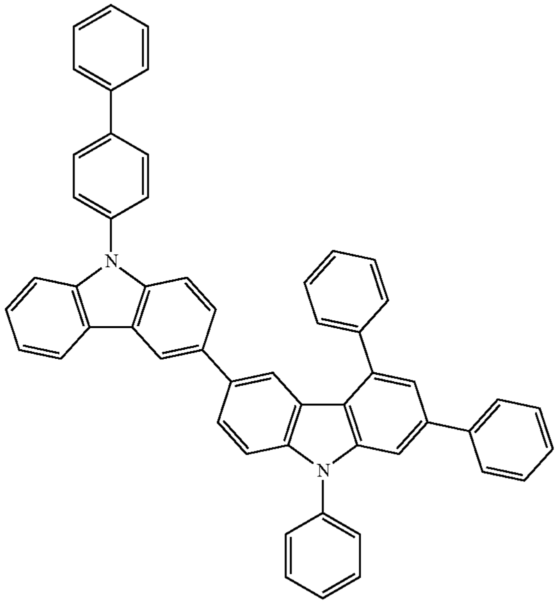 [SMILES: c1ccc(-c2ccc(-n3c4ccccc4c4cc(-c5ccc6c(c5)c5c(-c7ccccc7)cc(-c7ccccc7)cc5n6-c5ccccc5)ccc43)cc2)cc1]
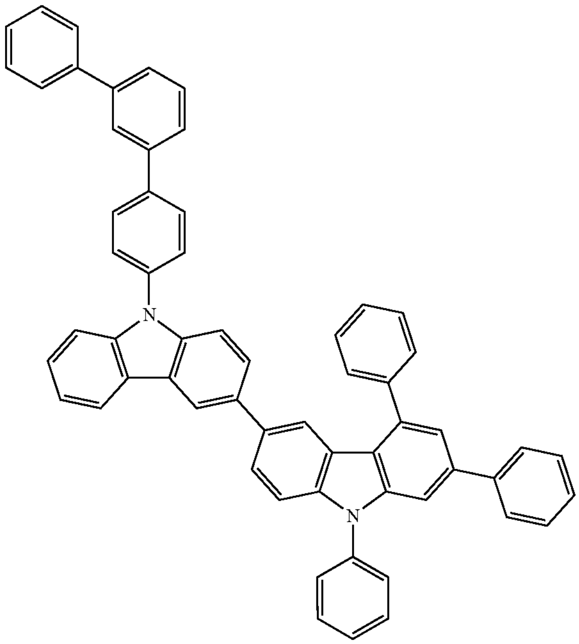 [SMILES: c1ccc(-c2cccc(-c3ccc(-n4c5ccccc5c5cc(-c6ccc7c(c6)c6c(-c8ccccc8)cc(-c8ccccc8)cc6n7-c6ccccc6)ccc54)cc3)c2)cc1]

TABLE 3-continued
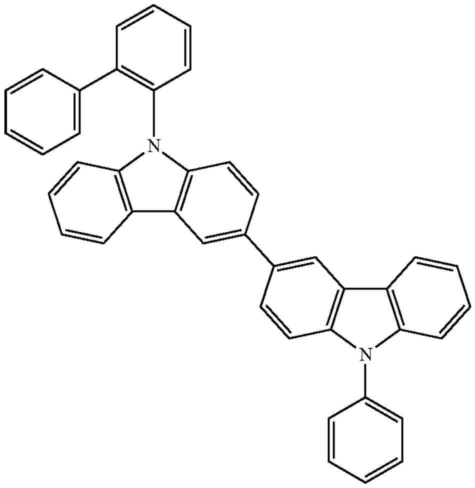 [SMILES: c1ccc(-c2ccccc2-n2c3ccccc3c3cc(-c4ccc5c(c4)c4ccccc4n5-c4ccccc4)ccc32)cc1]
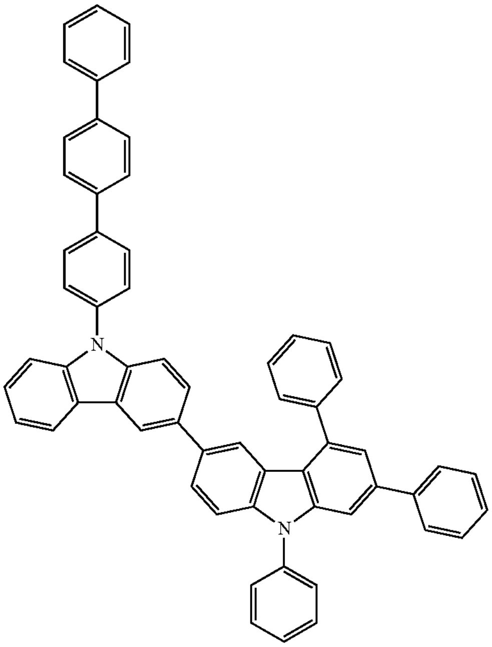 [SMILES: c1ccc(-c2ccc(-c3ccc(-n4c5ccccc5c5cc(-c6ccc7c(c6)c6c(-c8ccccc8)cc(-c8ccccc8)cc6n7-c6ccccc6)ccc54)cc3)cc2)cc1]

TABLE 3-continued
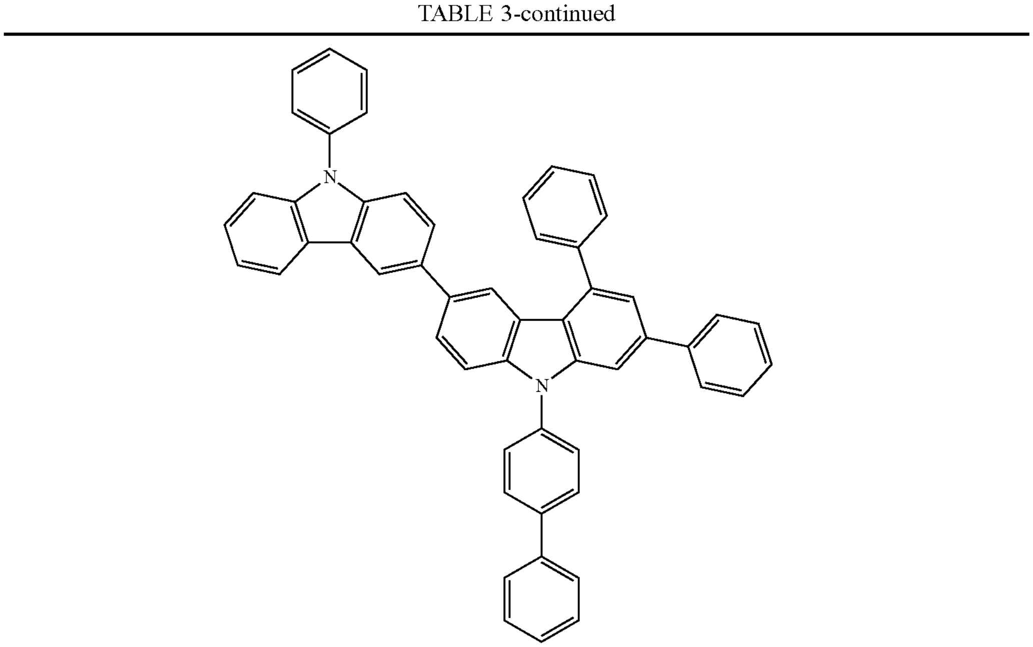
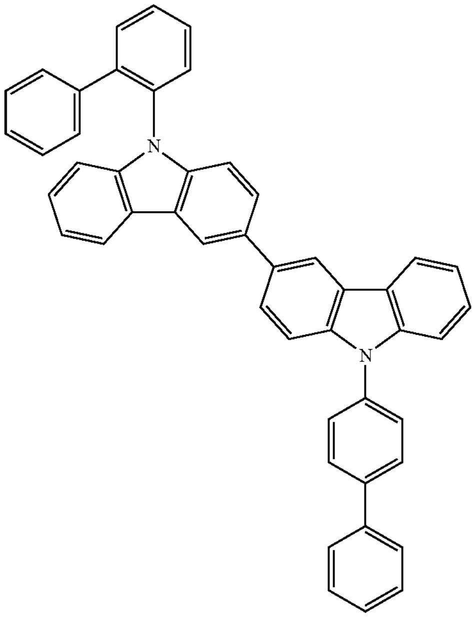 [SMILES: c1ccc(-c2ccc(-n3c4ccccc4c4cc(-c5ccc6c(c5)c5ccccc5n6-c5ccccc5-c5ccccc5)ccc43)cc2)cc1]

TABLE 3-continued
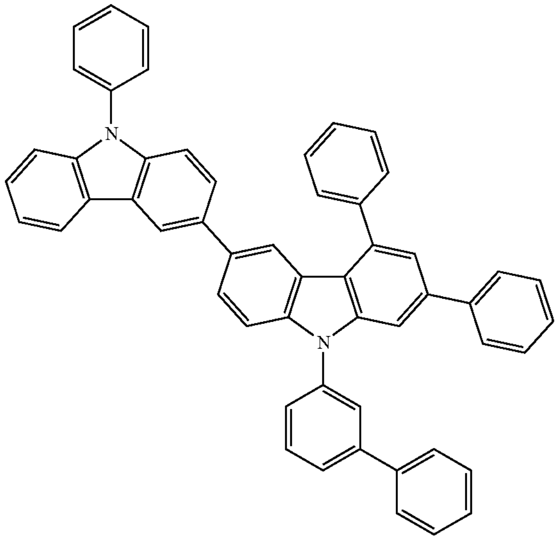 [SMILES: c1ccc(-c2cccc(-n3c4ccc(-c5ccc6c(c5)c5ccccc5n6-c5ccccc5)cc4c4c(-c5ccccc5)cc(-c5ccccc5)cc43)c2)cc1]
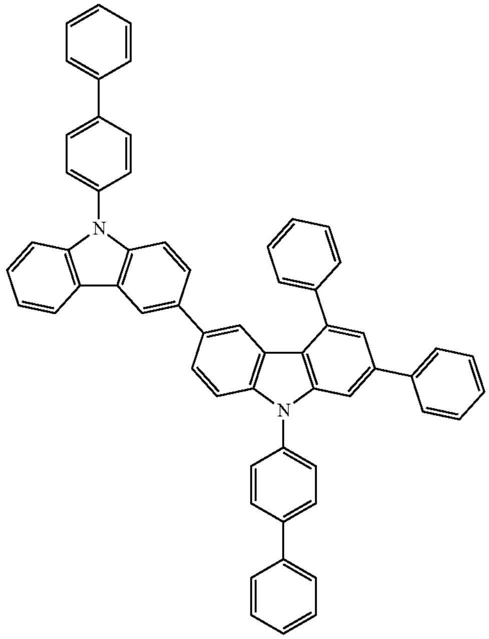 [SMILES: c1ccc(-c2ccc(-n3c4ccccc4c4cc(-c5ccc6c(c5)c5c(-c7ccccc7)cc(-c7ccccc7)cc5n6-c5ccc(-c6ccccc6)cc5)ccc43)cc2)cc1]

TABLE 3-continued
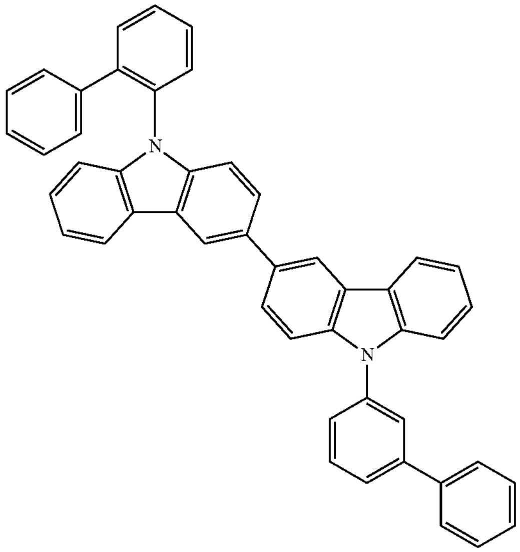 [SMILES: c1ccc(-c2cccc(-n3c4ccccc4c4cc(-c5ccc6c(c5)c5ccccc5n6-c5ccccc5-c5ccccc5)ccc43)c2)cc1]
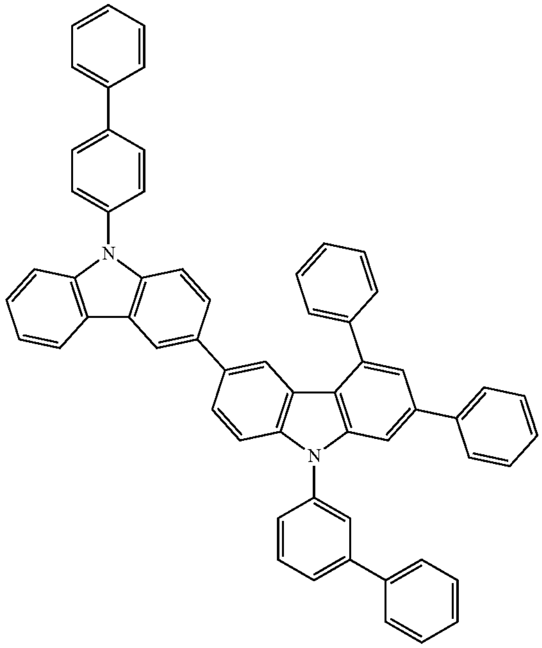 [SMILES: c1ccc(-c2ccc(-n3c4ccccc4c4cc(-c5ccc6c(c5)c5c(-c7ccccc7)cc(-c7ccccc7)cc5n6-c5cccc(-c6ccccc6)c5)ccc43)cc2)cc1]

TABLE 3-continued
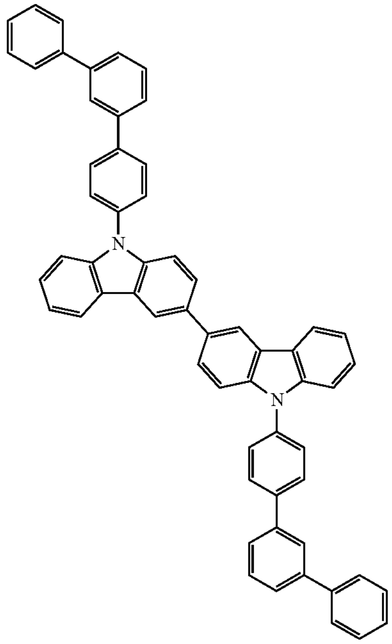 [SMILES: c1ccc(-c2cccc(-c3ccc(-n4c5ccccc5c5cc(-c6ccc7c(c6)c6ccccc6n7-c6ccc(-c7cccc(-c8ccccc8)c7)cc6)ccc54)cc3)c2)cc1]
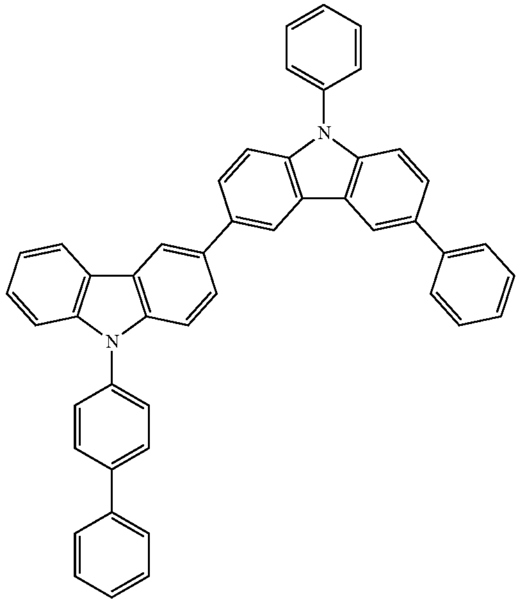 [SMILES: c1ccc(-c2ccc(-n3c4ccccc4c4cc(-c5ccc6c(c5)c5cc(-c7ccccc7)ccc5n6-c5ccccc5)ccc43)cc2)cc1]

TABLE 3-continued
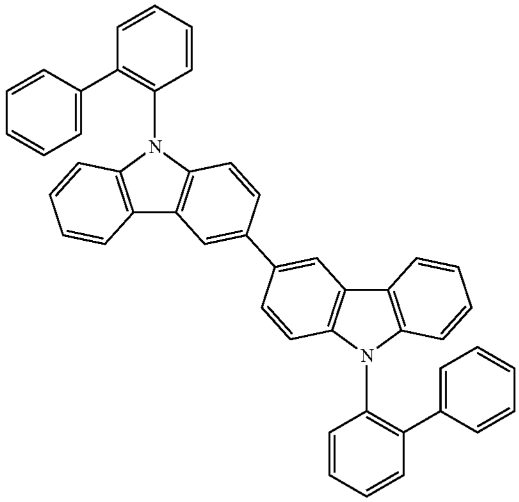 [SMILES: c1ccc(-c2ccccc2-n2c3ccccc3c3cc(-c4ccc5c(c4)c4ccccc4n5-c4ccccc4-c4ccccc4)ccc32)cc1]
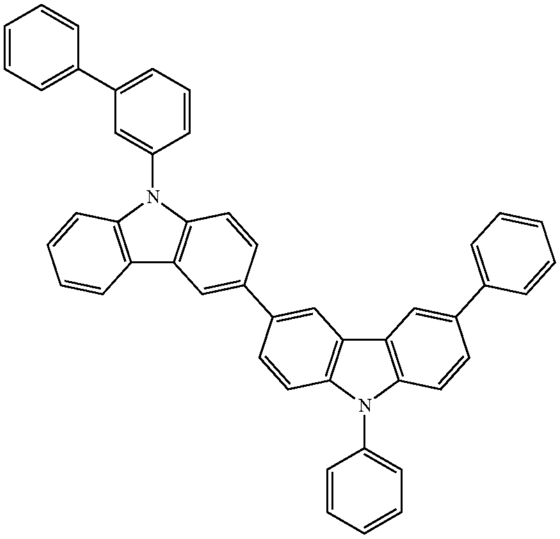 [SMILES: c1ccc(-c2cccc(-n3c4ccccc4c4cc(-c5ccc6c(c5)c5cc(-c7ccccc7)ccc5n6-c5ccccc5)ccc43)c2)cc1]
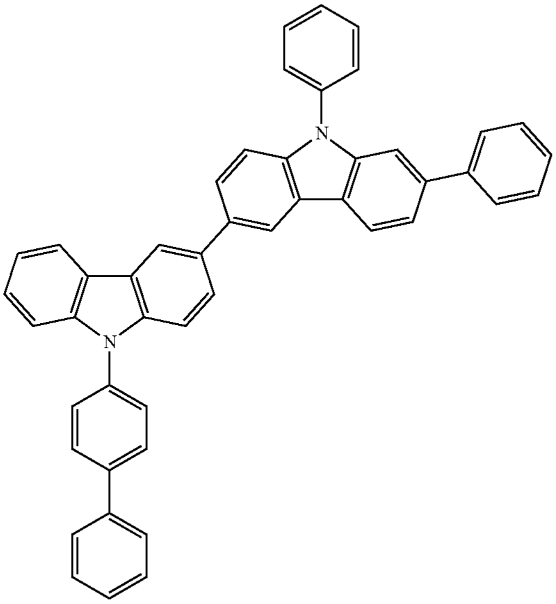 [SMILES: c1ccc(-c2ccc(-n3c4ccccc4c4cc(-c5ccc6c(c5)c5ccc(-c7ccccc7)cc5n6-c5ccccc5)ccc43)cc2)cc1]

TABLE 3-continued
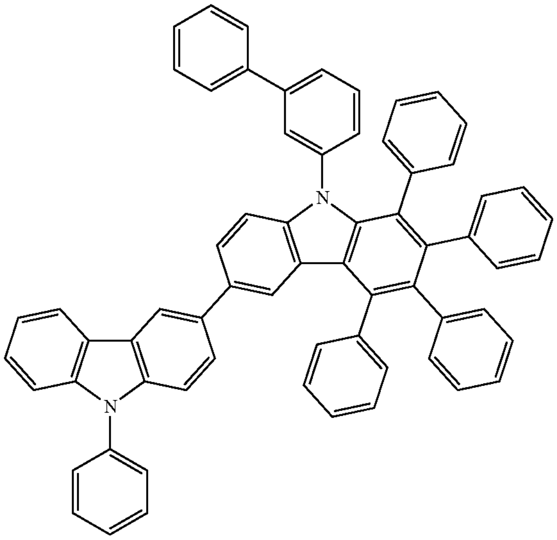 [SMILES: c1ccc(-c2cccc(-n3c4ccc(-c5ccc6c(c5)c5ccccc5n6-c5ccccc5)cc4c4c(-c5ccccc5)c(-c5ccccc5)c(-c5ccccc5)c(-c5ccccc5)c43)c2)cc1]
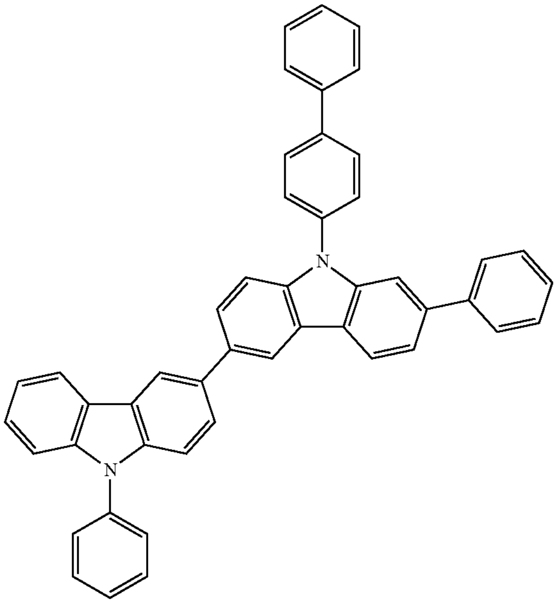 [SMILES: c1ccc(-c2ccc(-n3c4ccc(-c5ccc6c(c5)c5ccccc5n6-c5ccccc5)cc4c4ccc(-c5ccccc5)cc43)cc2)cc1]

TABLE 3-continued
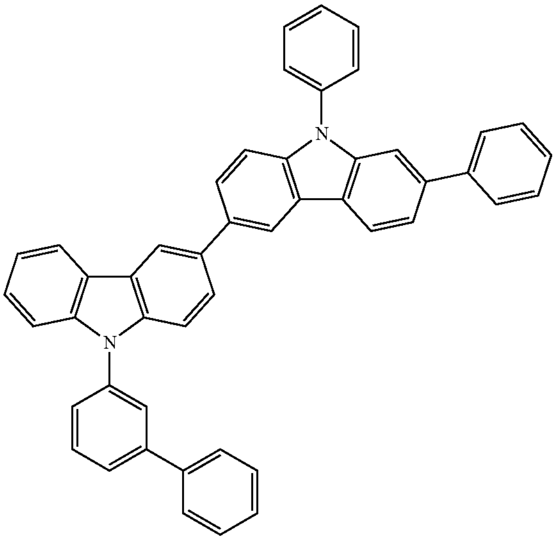 [SMILES: c1ccc(-c2cccc(-n3c4ccccc4c4cc(-c5ccc6c(c5)c5ccc(-c7ccccc7)cc5n6-c5ccccc5)ccc43)c2)cc1]
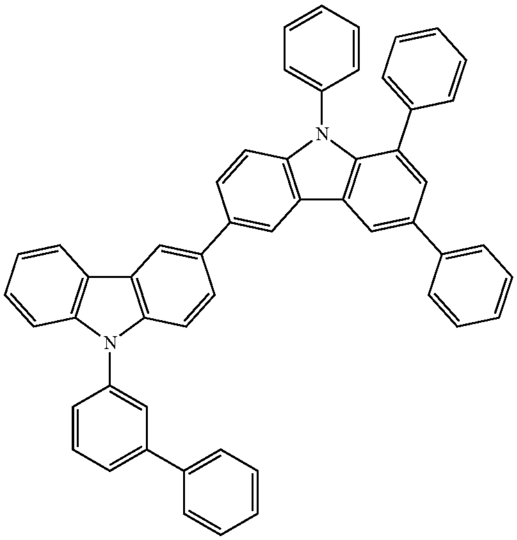 [SMILES: c1ccc(-c2cccc(-n3c4ccccc4c4cc(-c5ccc6c(c5)c5cc(-c7ccccc7)cc(-c7ccccc7)c5n6-c5ccccc5)ccc43)c2)cc1]
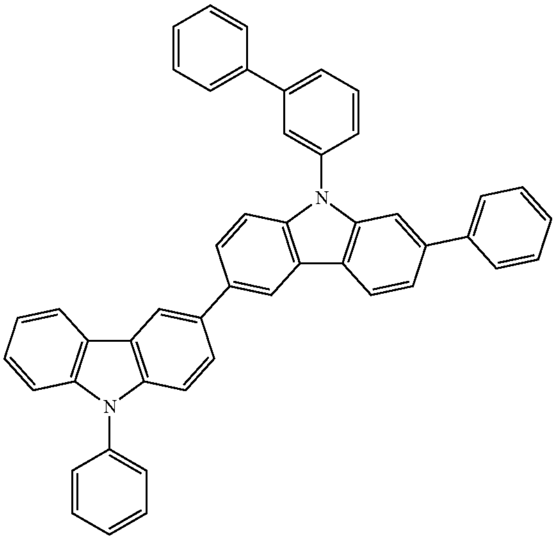 [SMILES: c1ccc(-c2cccc(-n3c4ccc(-c5ccc6c(c5)c5ccccc5n6-c5ccccc5)cc4c4ccc(-c5ccccc5)cc43)c2)cc1]

TABLE 3-continued
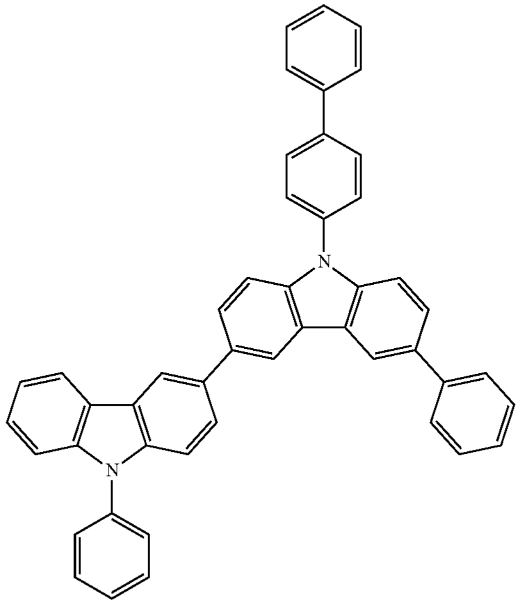 [SMILES: c1ccc(-c2ccc(-n3c4ccc(-c5ccccc5)cc4c4cc(-c5ccc6c(c5)c5ccccc5n6-c5ccccc5)ccc43)cc2)cc1]
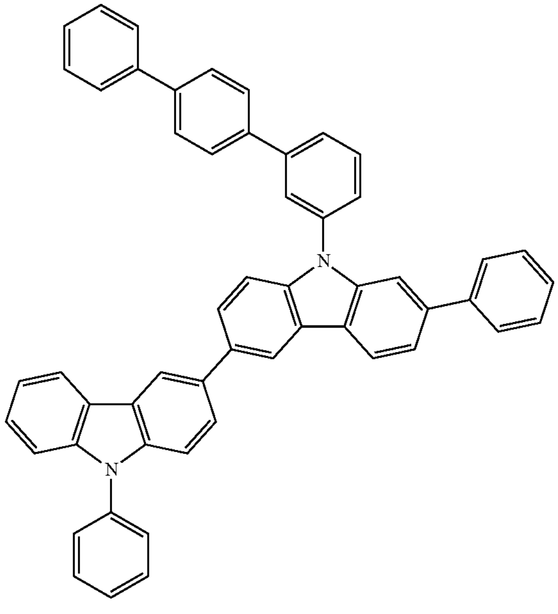 [SMILES: c1ccc(-c2ccc(-c3cccc(-n4c5ccc(-c6ccc7c(c6)c6ccccc6n7-c6ccccc6)cc5c5ccc(-c6ccccc6)cc54)c3)cc2)cc1]

TABLE 3-continued
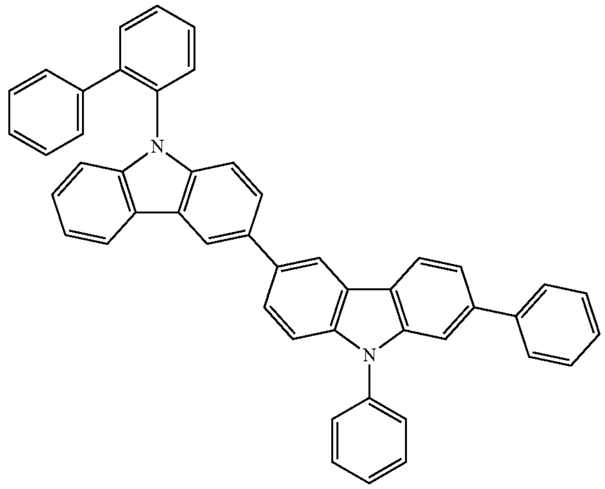 [SMILES: c1ccc(-c2ccc3c4cc(-c5ccc6c(c5)c5ccccc5n6-c5ccccc5-c5ccccc5)ccc4n(-c4ccccc4)c3c2)cc1]
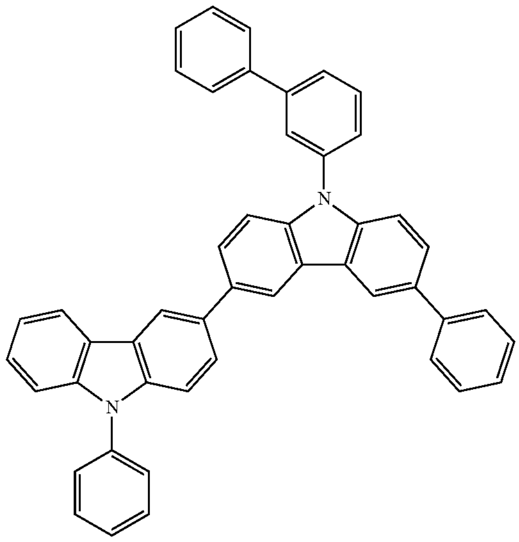 [SMILES: c1ccc(-c2cccc(-n3c4ccc(-c5ccccc5)cc4c4cc(-c5ccc6c(c5)c5ccccc5n6-c5ccccc5)ccc43)c2)cc1]
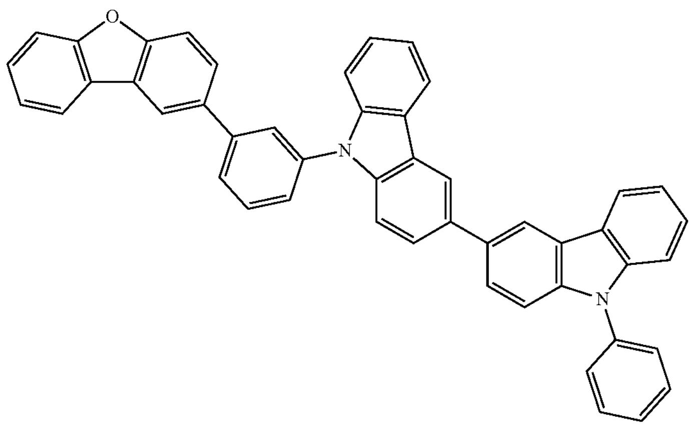 [SMILES: c1ccc(-n2c3ccccc3c3cc(-c4ccc5c(c4)c4ccccc4n5-c4cccc(-c5ccc6oc7ccccc7c6c5)c4)ccc32)cc1]

TABLE 3-continued
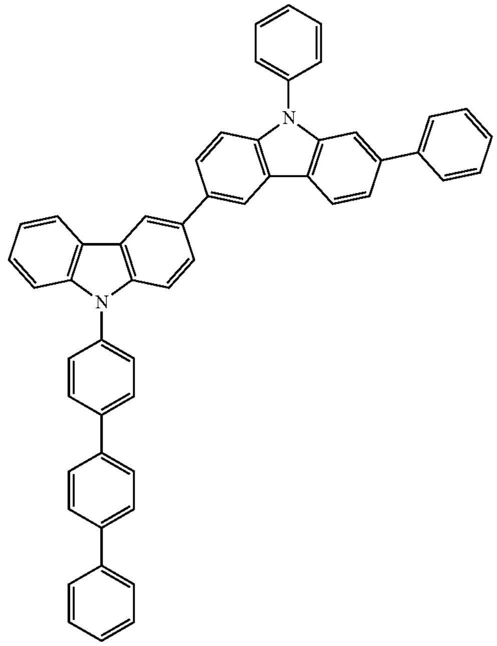 [SMILES: c1ccc(-c2ccc(-c3ccc(-n4c5ccccc5c5cc(-c6ccc7c(c6)c6ccc(-c8ccccc8)cc6n7-c6ccccc6)ccc54)cc3)cc2)cc1]
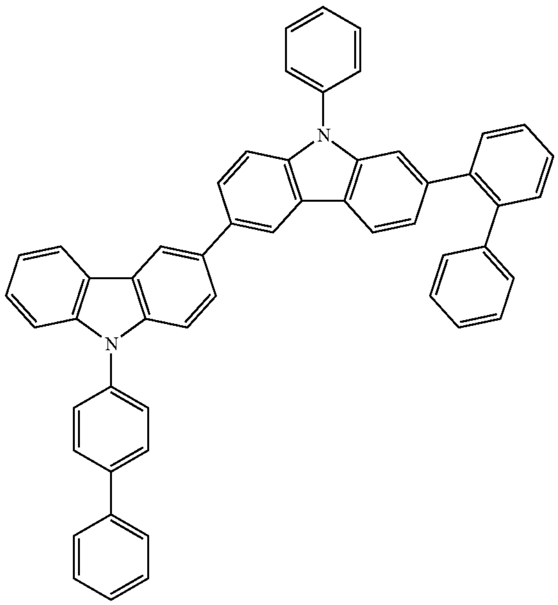 [SMILES: c1ccc(-c2ccc(-n3c4ccccc4c4cc(-c5ccc6c(c5)c5ccc(-c7ccccc7-c7ccccc7)cc5n6-c5ccccc5)ccc43)cc2)cc1]

TABLE 3-continued
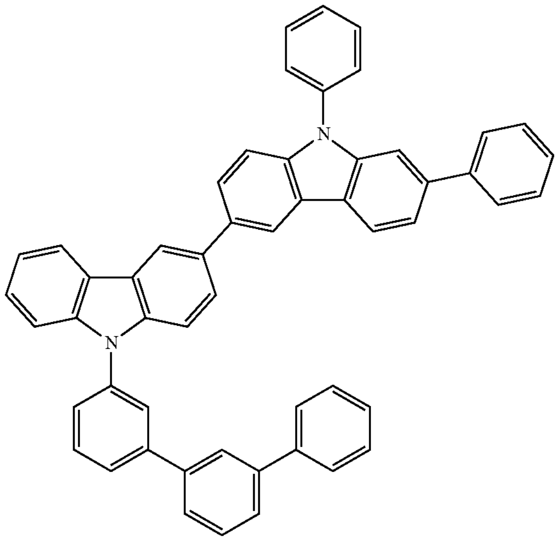 [SMILES: c1ccc(-c2cccc(-c3cccc(-n4c5ccccc5c5cc(-c6ccc7c(c6)c6ccc(-c8ccccc8)cc6n7-c6ccccc6)ccc54)c3)c2)cc1]
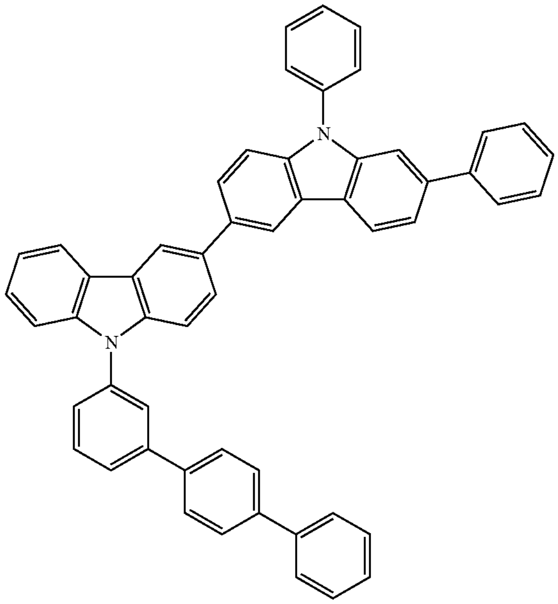 [SMILES: c1ccc(-c2ccc(-c3cccc(-n4c5ccccc5c5cc(-c6ccc7c(c6)c6ccc(-c8ccccc8)cc6n7-c6ccccc6)ccc54)c3)cc2)cc1]

TABLE 3-continued
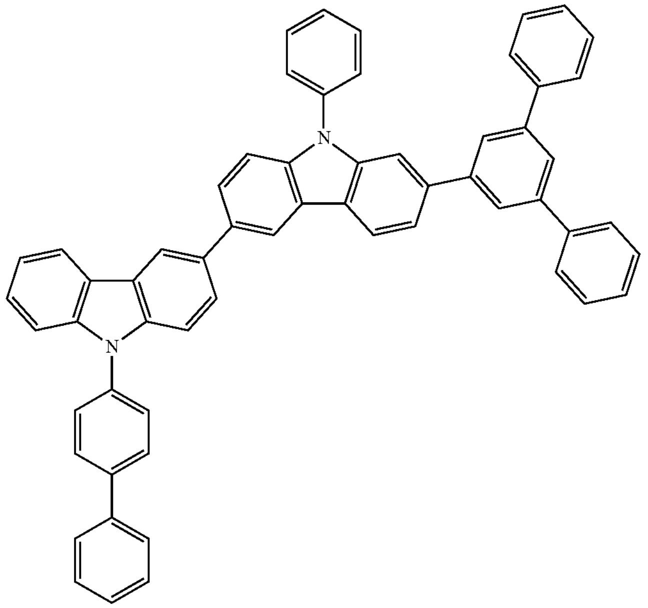 [SMILES: c1ccc(-c2ccc(-n3c4ccccc4c4cc(-c5ccc6c(c5)c5ccc(-c7cc(-c8ccccc8)cc(-c8ccccc8)c7)cc5n6-c5ccccc5)ccc43)cc2)cc1]
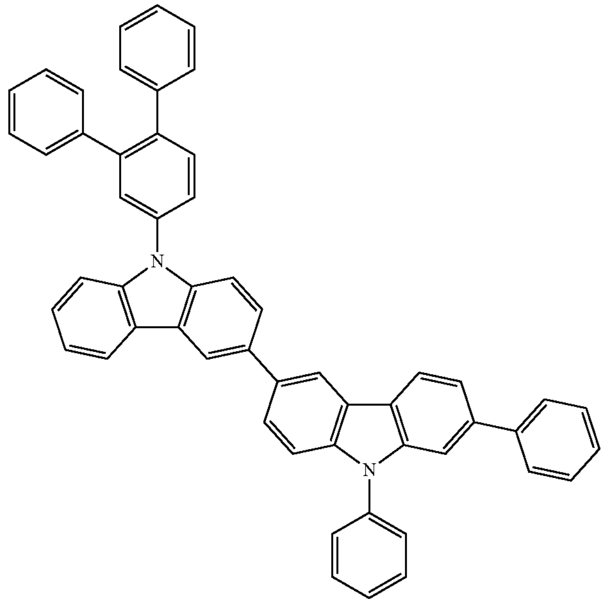 [SMILES: c1ccc(-c2ccc3c4cc(-c5ccc6c(c5)c5ccccc5n6-c5ccc(-c6ccccc6)c(-c6ccccc6)c5)ccc4n(-c4ccccc4)c3c2)cc1]

TABLE 3-continued
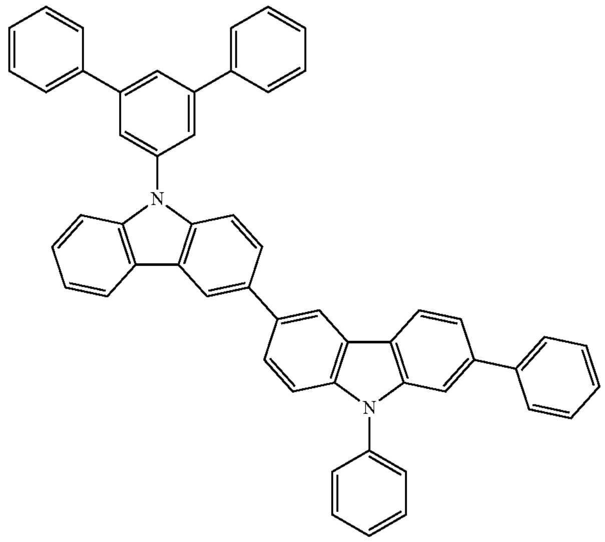 [SMILES: c1ccc(-c2cc(-c3ccccc3)cc(-n3c4ccccc4c4cc(-c5ccc6c(c5)c5ccc(-c7ccccc7)cc5n6-c5ccccc5)ccc43)c2)cc1]
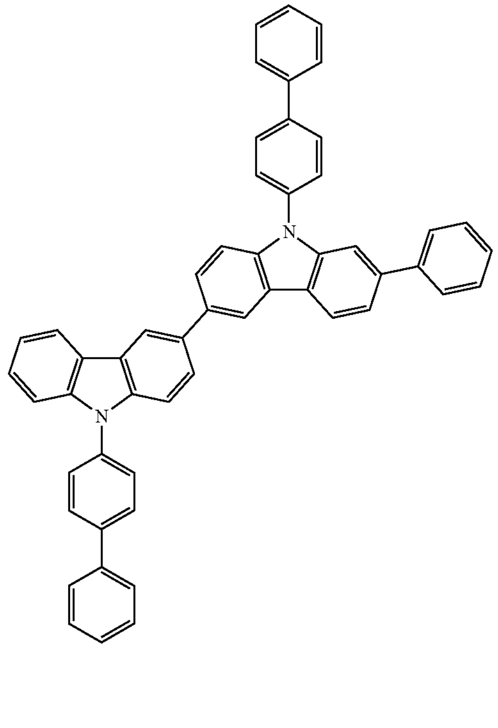 [SMILES: c1ccc(-c2ccc(-n3c4ccccc4c4cc(-c5ccc6c(c5)c5ccc(-c7ccccc7)cc5n6-c5ccc(-c6ccccc6)cc5)ccc43)cc2)cc1]

TABLE 3-continued
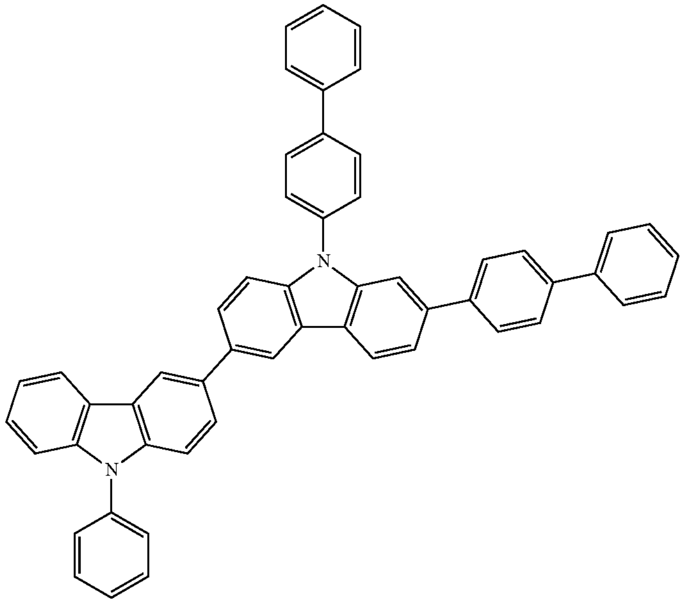 [SMILES: c1ccc(-c2ccc(-c3ccc4c5cc(-c6ccc7c(c6)c6ccccc6n7-c6ccccc6)ccc5n(-c5ccc(-c6ccccc6)cc5)c4c3)cc2)cc1]
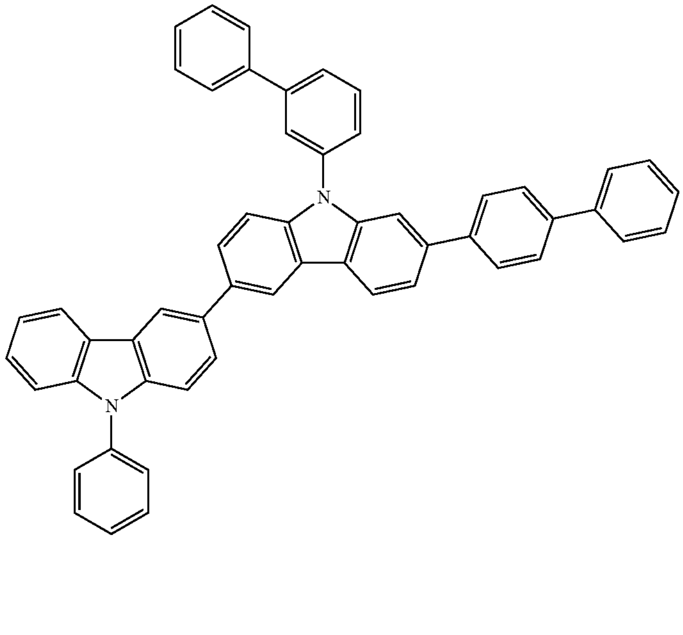 [SMILES: c1ccc(-c2ccc(-c3ccc4c5cc(-c6ccc7c(c6)c6ccccc6n7-c6ccccc6)ccc5n(-c5cccc(-c6ccccc6)c5)c4c3)cc2)cc1]

TABLE 3-continued
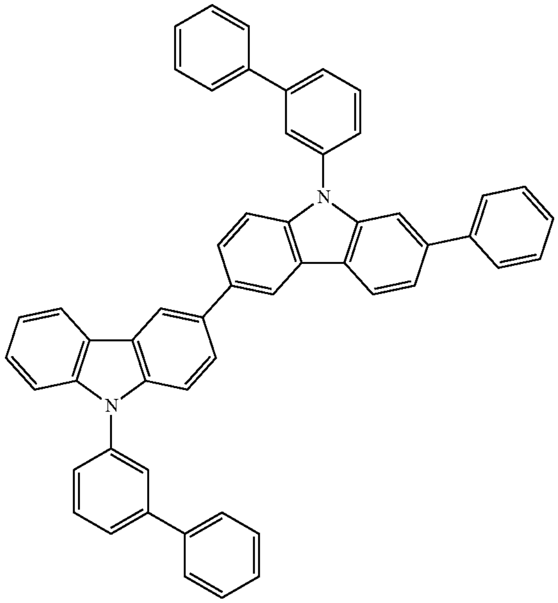 [SMILES: c1ccc(-c2cccc(-n3c4ccccc4c4cc(-c5ccc6c(c5)c5ccc(-c7ccccc7)cc5n6-c5cccc(-c6ccccc6)c5)ccc43)c2)cc1]
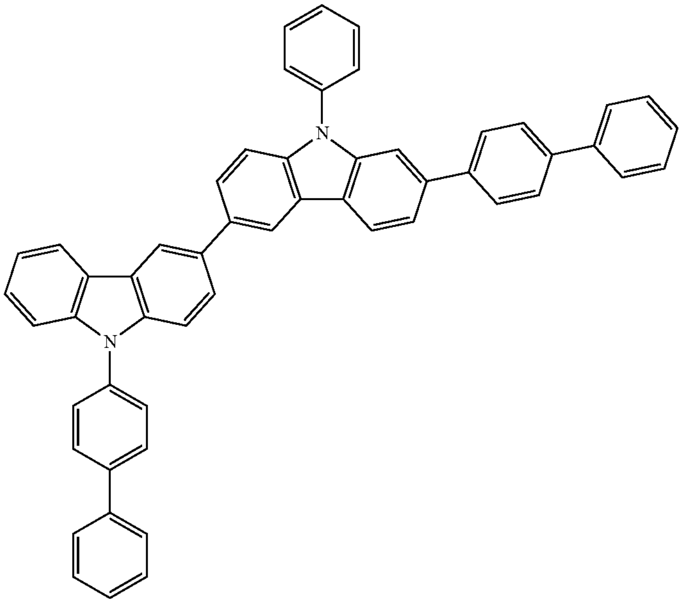 [SMILES: c1ccc(-c2ccc(-c3ccc4c5cc(-c6ccc7c(c6)c6ccccc6n7-c6ccc(-c7ccccc7)cc6)ccc5n(-c5ccccc5)c4c3)cc2)cc1]

TABLE 3-continued
16
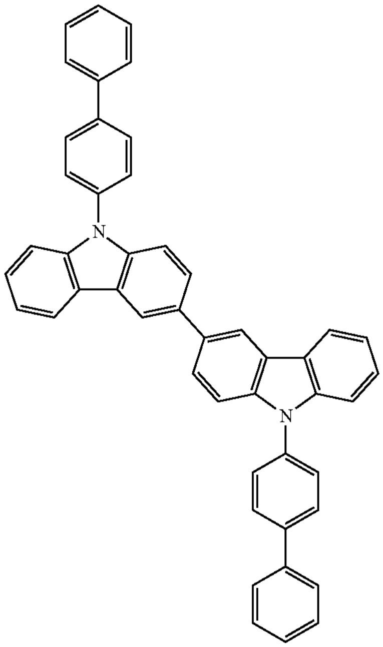 [SMILES: c1ccc(-c2ccc(-n3c4ccccc4c4cc(-c5ccc6c(c5)c5ccccc5n6-c5ccc(-c6ccccc6)cc5)ccc43)cc2)cc1]
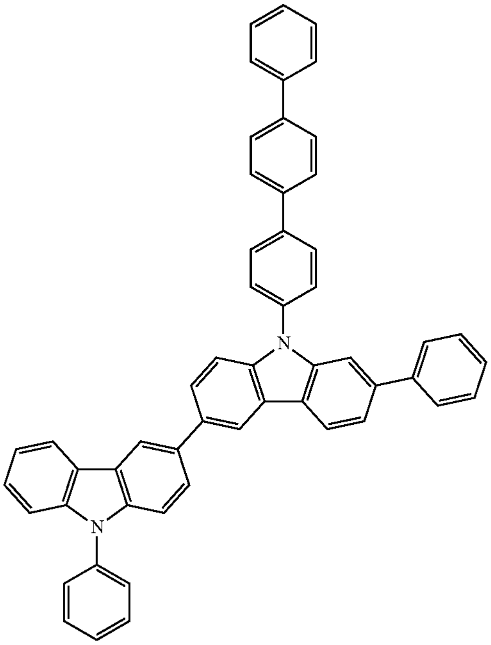 [SMILES: c1ccc(-c2ccc(-c3ccc(-n4c5ccc(-c6ccc7c(c6)c6ccccc6n7-c6ccccc6)cc5c5ccc(-c6ccccc6)cc54)cc3)cc2)cc1]

TABLE 3-continued
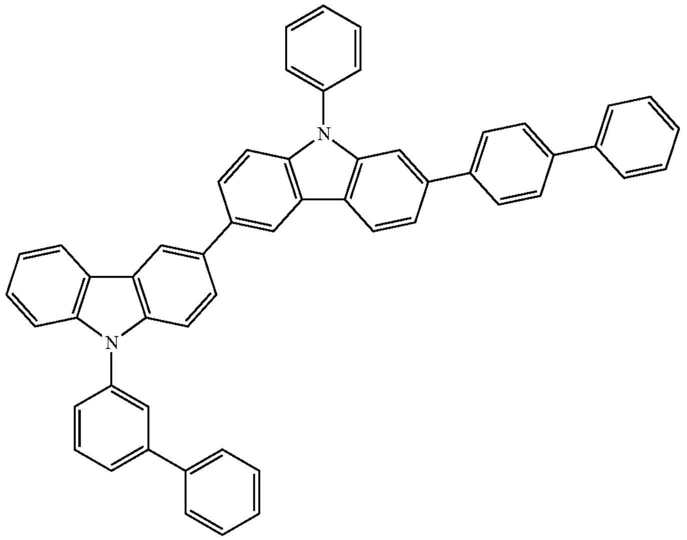 [SMILES: c1ccc(-c2ccc(-c3ccc4c5cc(-c6ccc7c(c6)c6ccccc6n7-c6cccc(-c7ccccc7)c6)ccc5n(-c5ccccc5)c4c3)cc2)cc1]
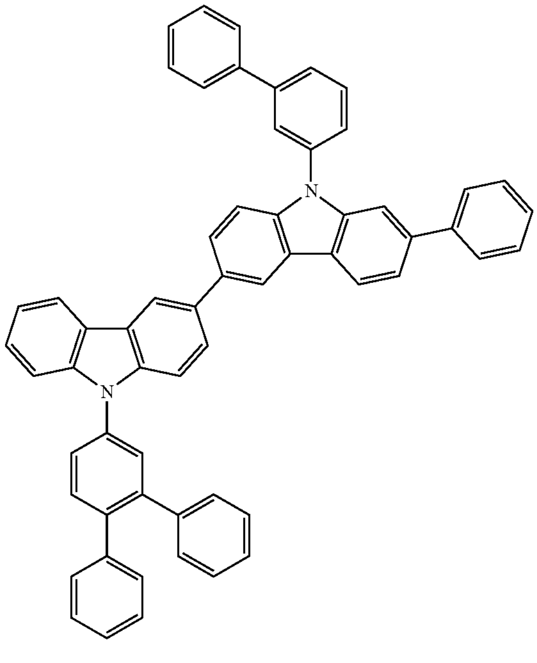 [SMILES: c1ccc(-c2cccc(-n3c4ccc(-c5ccc6c(c5)c5ccccc5n6-c5ccc(-c6ccccc6)c(-c6ccccc6)c5)cc4c4ccc(-c5ccccc5)cc43)c2)cc1]

TABLE 3-continued
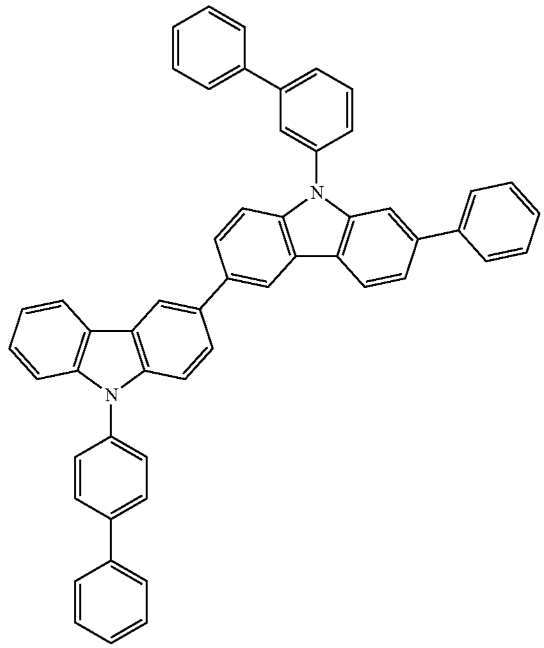 [SMILES: c1ccc(-c2ccc(-n3c4ccccc4c4cc(-c5ccc6c(c5)c5ccc(-c7ccccc7)cc5n6-c5cccc(-c6ccccc6)c5)ccc43)cc2)cc1]
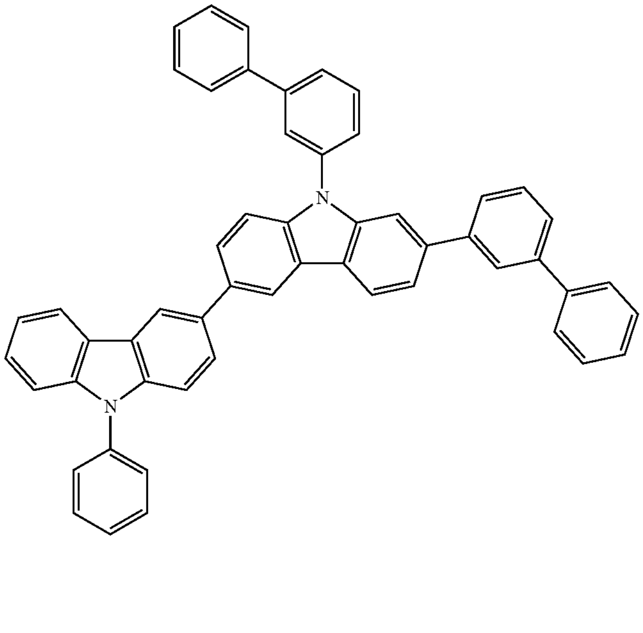 [SMILES: c1ccc(-c2cccc(-c3ccc4c5cc(-c6ccc7c(c6)c6ccccc6n7-c6ccccc6)ccc5n(-c5cccc(-c6ccccc6)c5)c4c3)c2)cc1]

TABLE 3-continued
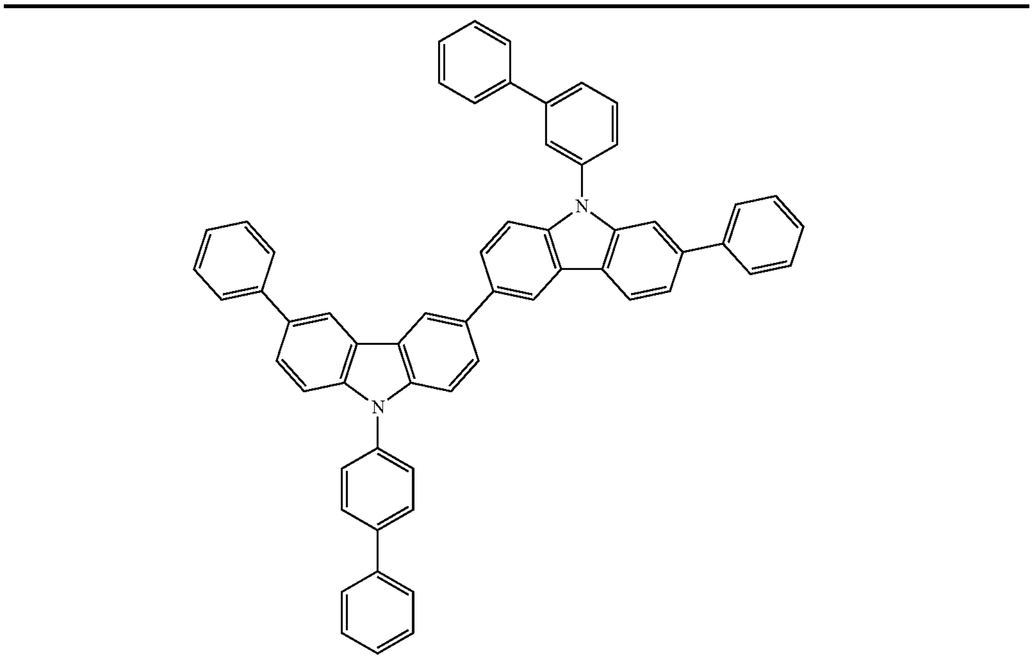
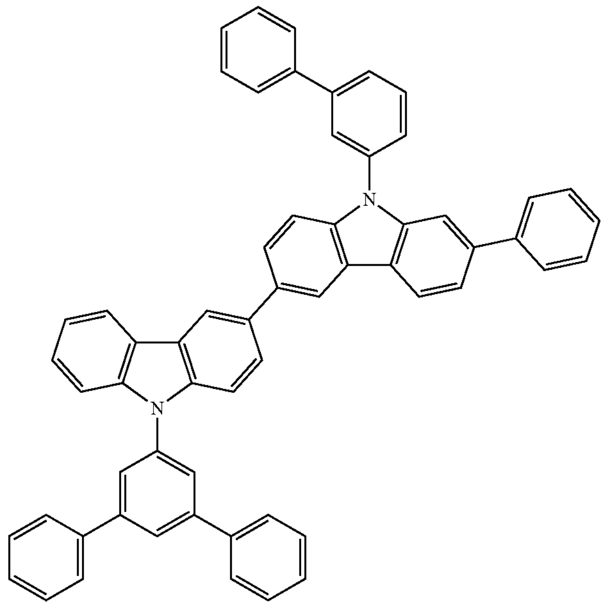 [SMILES: c1ccc(-c2cccc(-n3c4ccc(-c5ccc6c(c5)c5ccccc5n6-c5cc(-c6ccccc6)cc(-c6ccccc6)c5)cc4c4ccc(-c5ccccc5)cc43)c2)cc1]

TABLE 3-continued
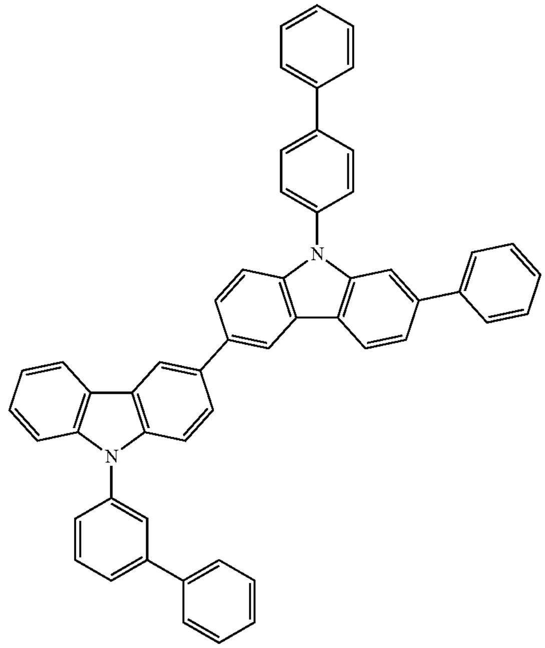 [SMILES: c1ccc(-c2ccc(-n3c4ccc(-c5ccc6c(c5)c5ccccc5n6-c5cccc(-c6ccccc6)c5)cc4c4ccc(-c5ccccc5)cc43)cc2)cc1]
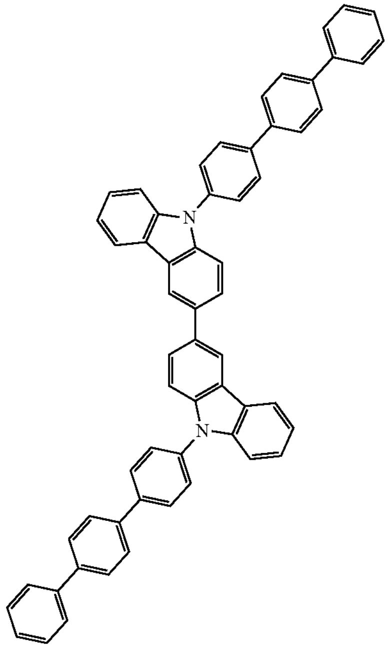 [SMILES: c1ccc(-c2ccc(-c3ccc(-n4c5ccccc5c5cc(-c6ccc7c(c6)c6ccccc6n7-c6ccc(-c7ccc(-c8ccccc8)cc7)cc6)ccc54)cc3)cc2)cc1]

TABLE 3-continued
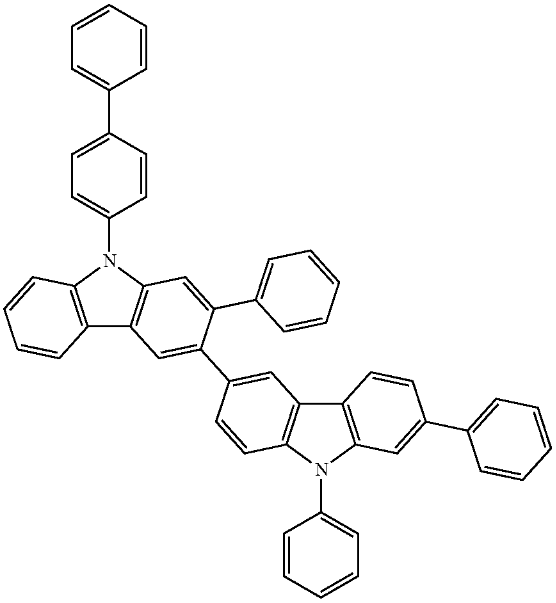 [SMILES: c1ccc(-c2ccc(-n3c4ccccc4c4cc(-c5ccc6c(c5)c5ccc(-c7ccccc7)cc5n6-c5ccccc5)c(-c5ccccc5)cc43)cc2)cc1]
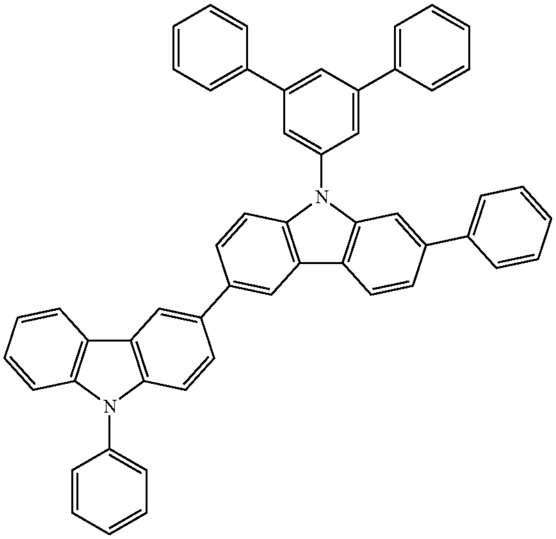 [SMILES: c1ccc(-c2cc(-c3ccccc3)cc(-n3c4ccc(-c5ccc6c(c5)c5ccccc5n6-c5ccccc5)cc4c4ccc(-c5ccccc5)cc43)c2)cc1]
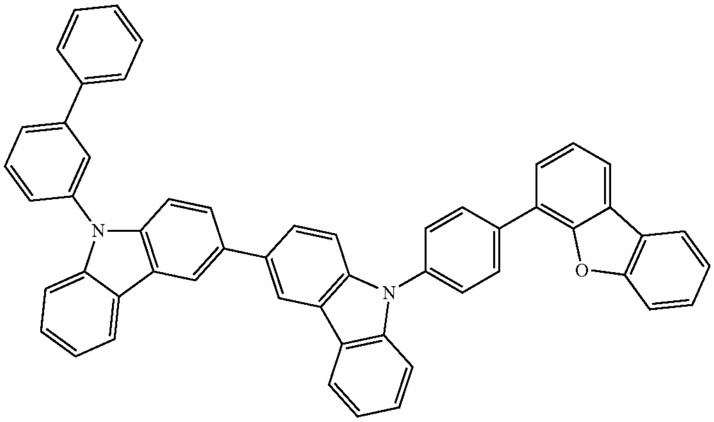 [SMILES: c1ccc(-c2cccc(-n3c4ccccc4c4cc(-c5ccc6c(c5)c5ccccc5n6-c5ccc(-c6cccc7c6oc6ccccc67)cc5)ccc43)c2)cc1]

TABLE 3-continued
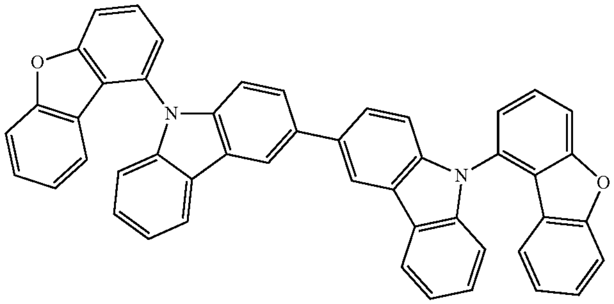 [SMILES: c1ccc2c(c1)oc1cccc(-n3c4ccccc4c4cc(-c5ccc6c(c5)c5ccccc5n6-c5cccc6oc7ccccc7c56)ccc43)c12]
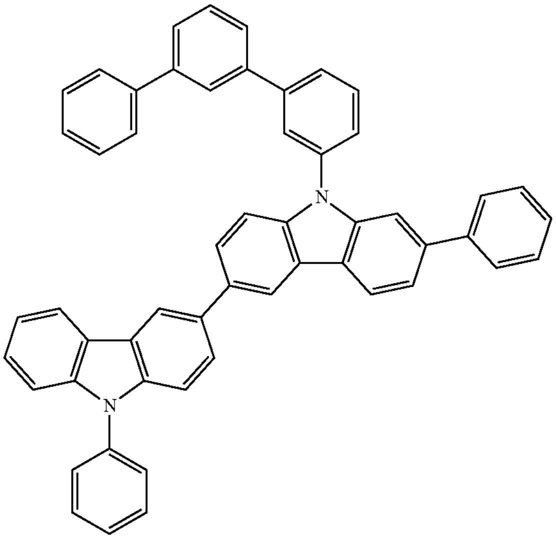 [SMILES: c1ccc(-c2cccc(-c3cccc(-n4c5ccc(-c6ccc7c(c6)c6ccccc6n7-c6ccccc6)cc5c5ccc(-c6ccccc6)cc54)c3)c2)cc1]
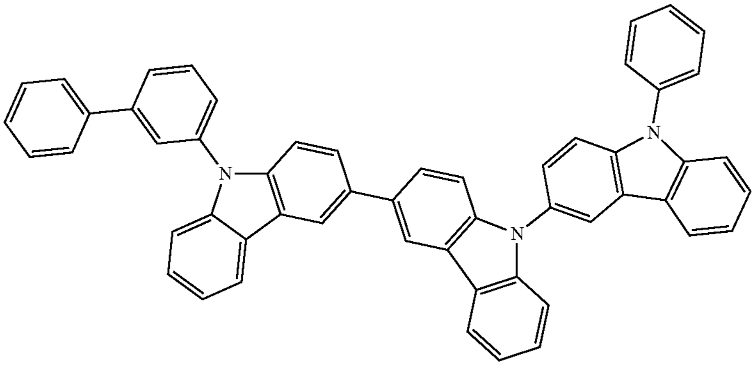 [SMILES: c1ccc(-c2cccc(-n3c4ccccc4c4cc(-c5ccc6c(c5)c5ccccc5n6-c5ccc6c(c5)c5ccccc5n6-c5ccccc5)ccc43)c2)cc1]
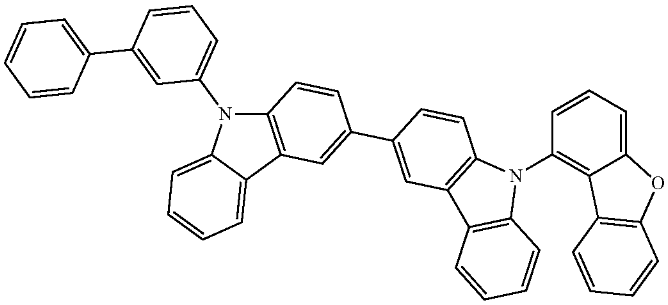 [SMILES: c1ccc(-c2cccc(-n3c4ccccc4c4cc(-c5ccc6c(c5)c5ccccc5n6-c5cccc6oc7ccccc7c56)ccc43)c2)cc1]

TABLE 3-continued
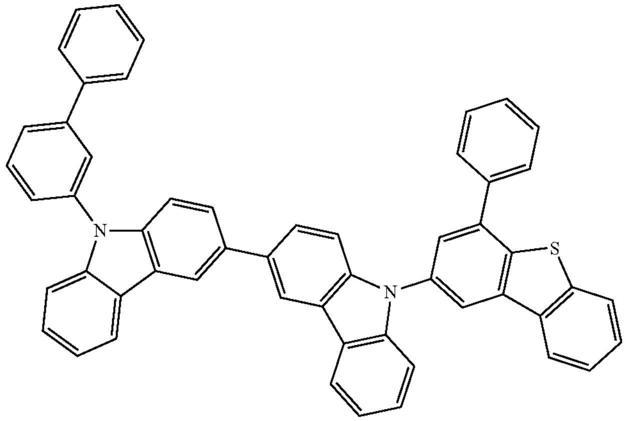 [SMILES: c1ccc(-c2cccc(-n3c4ccccc4c4cc(-c5ccc6c(c5)c5ccccc5n6-c5cc(-c6ccccc6)c6sc7ccccc7c6c5)ccc43)c2)cc1]
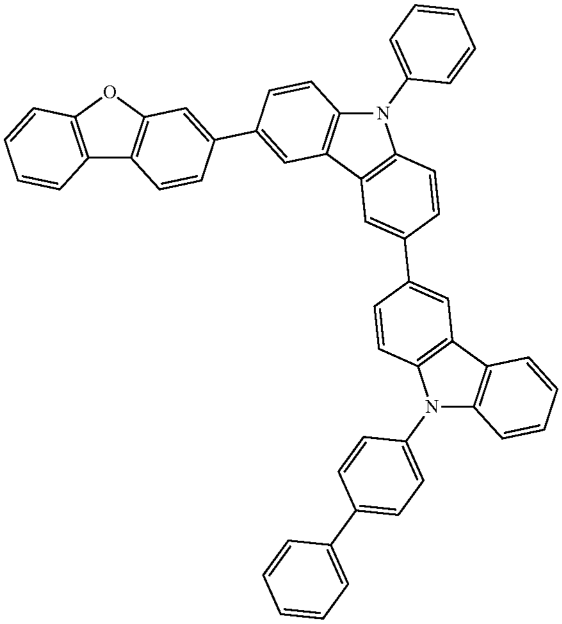

TABLE 3-continued
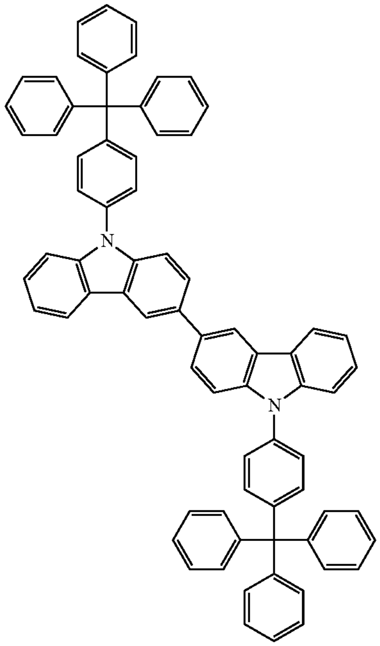 [SMILES: c1ccc(C(c2ccccc2)(c2ccccc2)c2ccc(-n3c4ccccc4c4cc(-c5ccc6c(c5)c5ccccc5n6-c5ccc(C(c6ccccc6)(c6ccccc6)c6ccccc6)cc5)ccc43)cc2)cc1]
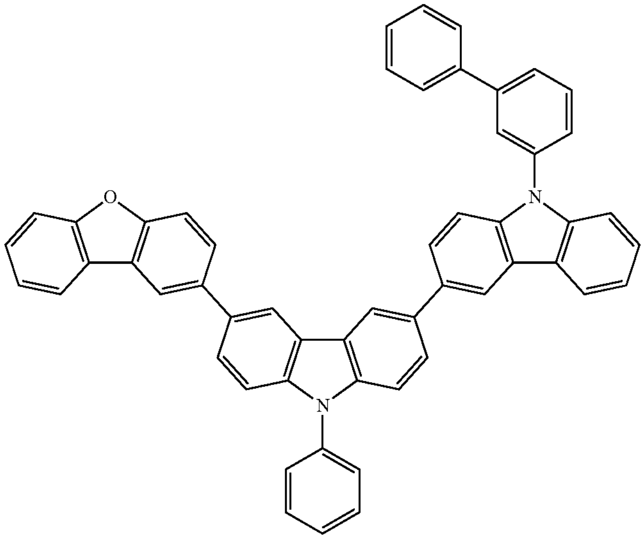
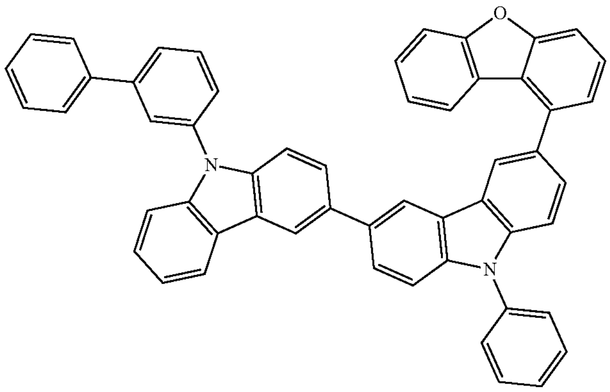 [SMILES: c1ccc(-c2cccc(-n3c4ccccc4c4cc(-c5ccc6c(c5)c5cc(-c7cccc8oc9ccccc9c78)ccc5n6-c5ccccc5)ccc43)c2)cc1]

TABLE 3-continued
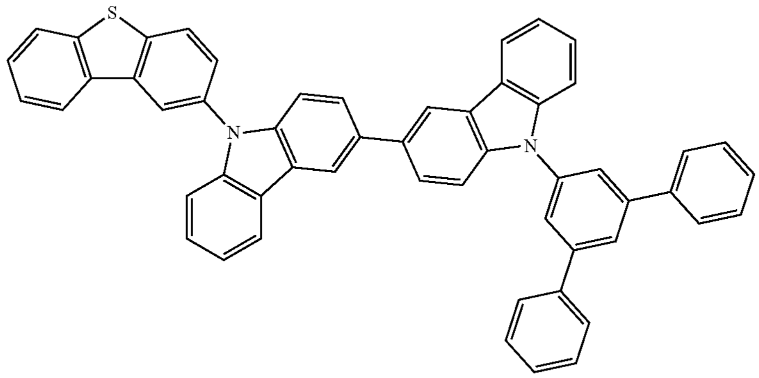
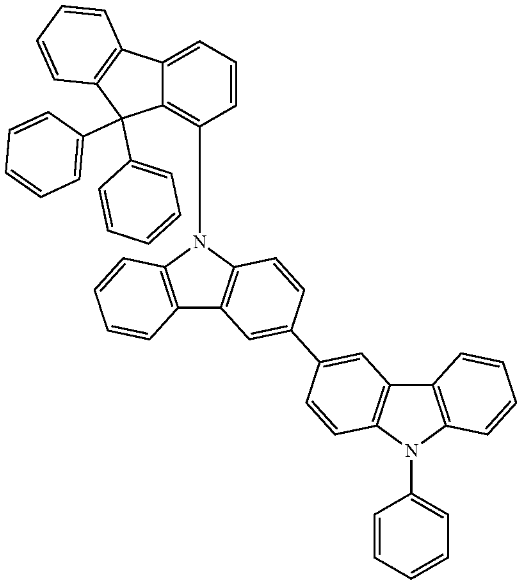 [SMILES: c1ccc(-n2c3ccccc3c3cc(-c4ccc5c(c4)c4ccccc4n5-c4cccc5c4C(c4ccccc4)(c4ccccc4)c4ccccc4-5)ccc32)cc1]
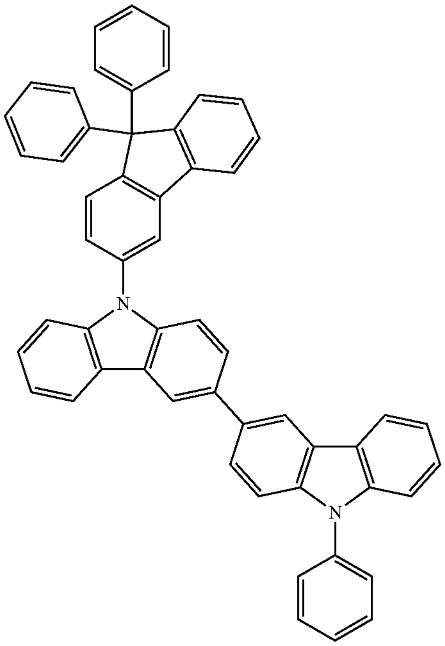 [SMILES: c1ccc(-n2c3ccccc3c3cc(-c4ccc5c(c4)c4ccccc4n5-c4ccc5c(c4)-c4ccccc4C5(c4ccccc4)c4ccccc4)ccc32)cc1]

TABLE 3-continued
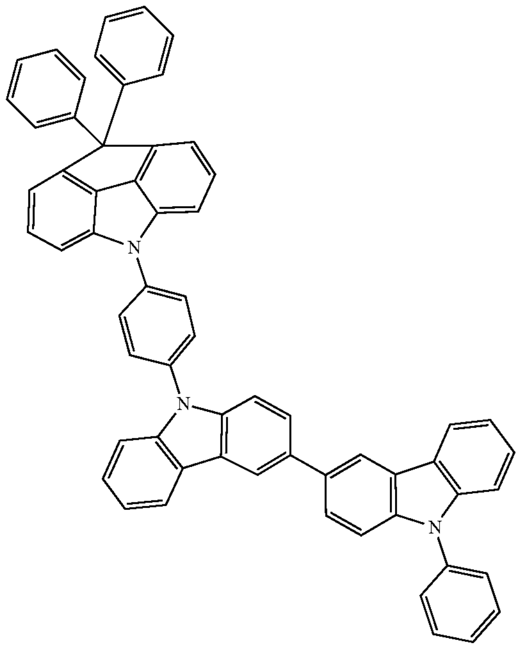 [SMILES: c1ccc(-n2c3ccccc3c3cc(-c4ccc5c(c4)c4ccccc4n5-c4ccc(-n5c6cccc7c6c6c(cccc65)C7(c5ccccc5)c5ccccc5)cc4)ccc32)cc1]
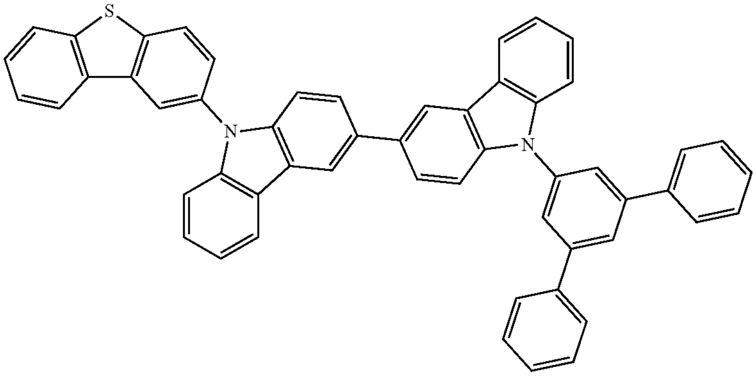 [SMILES: c1ccc(-c2cc(-c3ccccc3)cc(-n3c4ccccc4c4cc(-c5ccc6c(c5)c5ccccc5n6-c5ccc6sc7ccccc7c6c5)ccc43)c2)cc1]
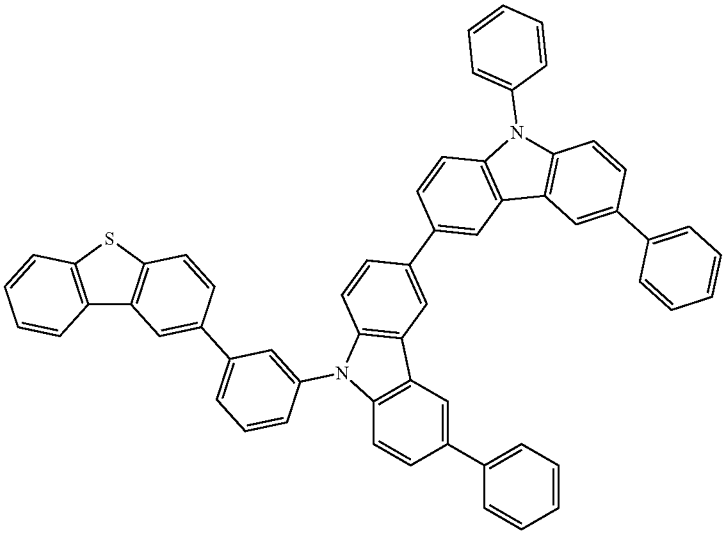 [SMILES: c1ccc(-c2ccc3c(c2)c2cc(-c4ccc5c(c4)c4cc(-c6ccccc6)ccc4n5-c4cccc(-c5ccc6sc7ccccc7c6c5)c4)ccc2n3-c2ccccc2)cc1]

TABLE 3-continued
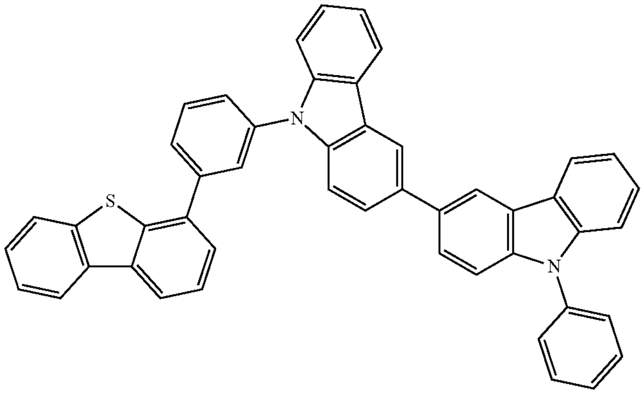
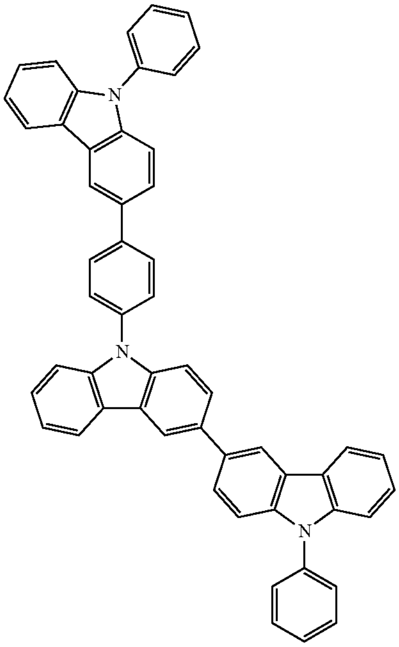 [SMILES: c1ccc(-n2c3ccccc3c3cc(-c4ccc(-n5c6ccccc6c6cc(-c7ccc8c(c7)c7ccccc7n8-c7ccccc7)ccc65)cc4)ccc32)cc1]

TABLE 3-continued
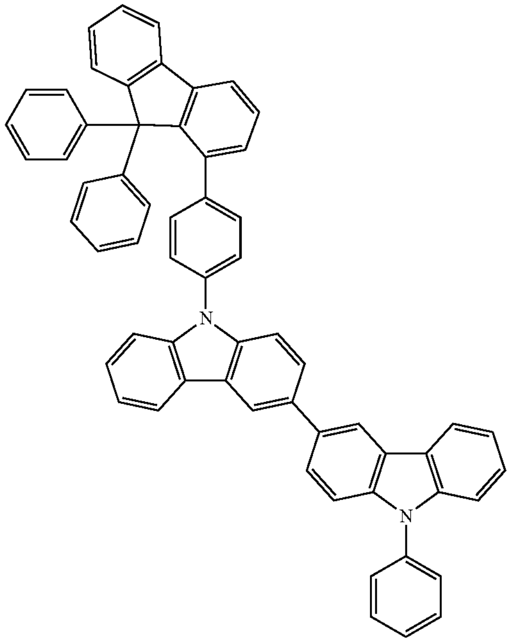 [SMILES: c1ccc(-n2c3ccccc3c3cc(-c4ccc5c(c4)c4ccccc4n5-c4ccc(-c5cccc6c5C(c5ccccc5)(c5ccccc5)c5ccccc5-6)cc4)ccc32)cc1]
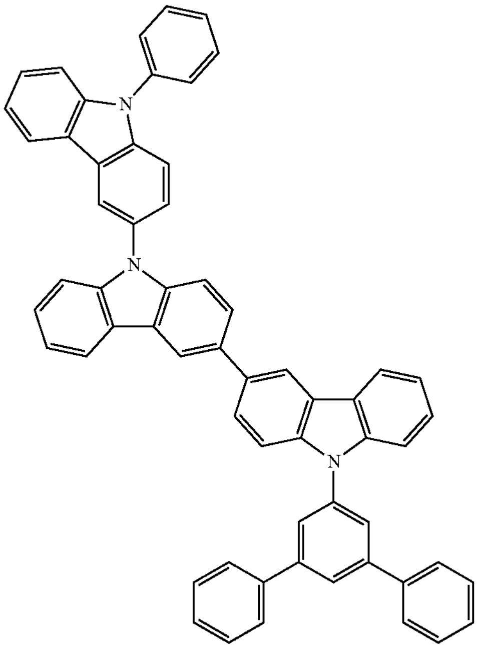 [SMILES: c1ccc(-c2cc(-c3ccccc3)cc(-n3c4ccccc4c4cc(-c5ccc6c(c5)c5ccccc5n6-c5ccc6c(c5)c5ccccc5n6-c5ccccc5)ccc43)c2)cc1]

TABLE 3-continued
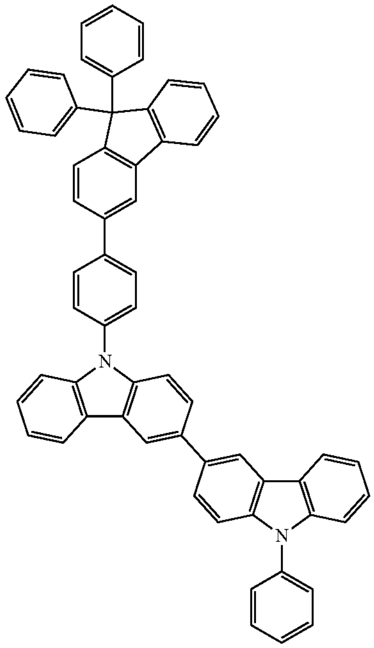 [SMILES: c1ccc(-n2c3ccccc3c3cc(-c4ccc5c(c4)c4ccccc4n5-c4ccc(-c5ccc6c(c5)-c5ccccc5C6(c5ccccc5)c5ccccc5)cc4)ccc32)cc1]
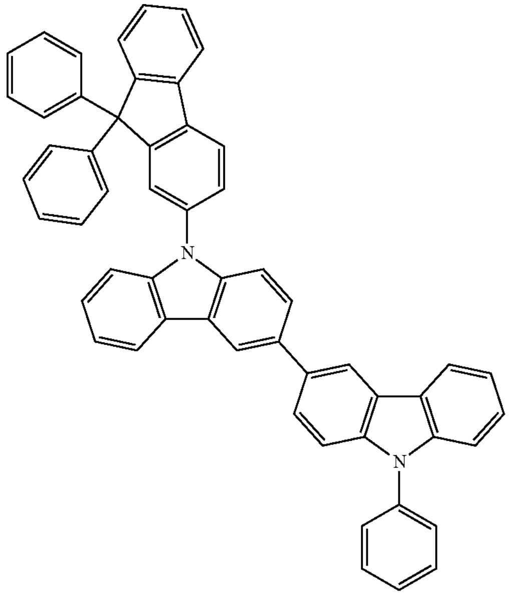 [SMILES: c1ccc(-n2c3ccccc3c3cc(-c4ccc5c(c4)c4ccccc4n5-c4ccc5c(c4)C(c4ccccc4)(c4ccccc4)c4ccccc4-5)ccc32)cc1]

TABLE 3-continued
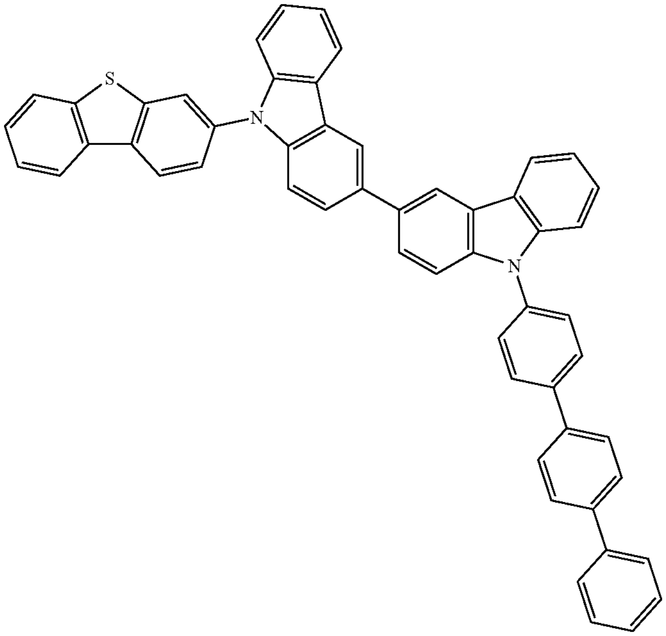
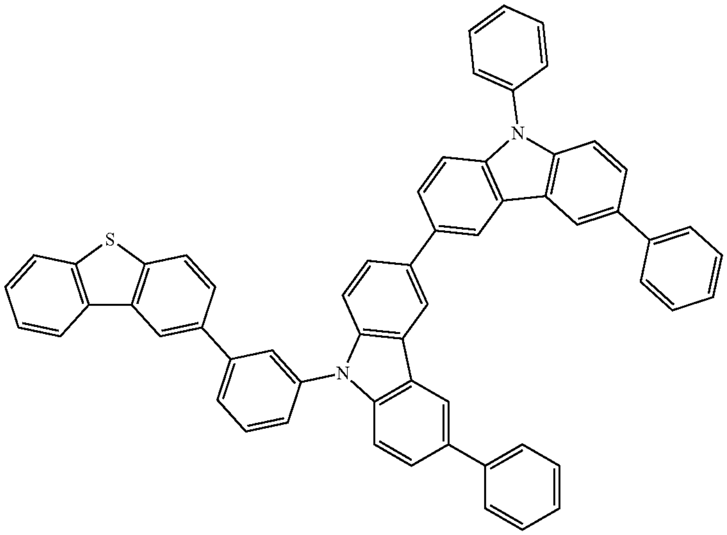 [SMILES: c1ccc(-c2ccc3c(c2)c2cc(-c4ccc5c(c4)c4cc(-c6ccccc6)ccc4n5-c4cccc(-c5ccc6sc7ccccc7c6c5)c4)ccc2n3-c2ccccc2)cc1]
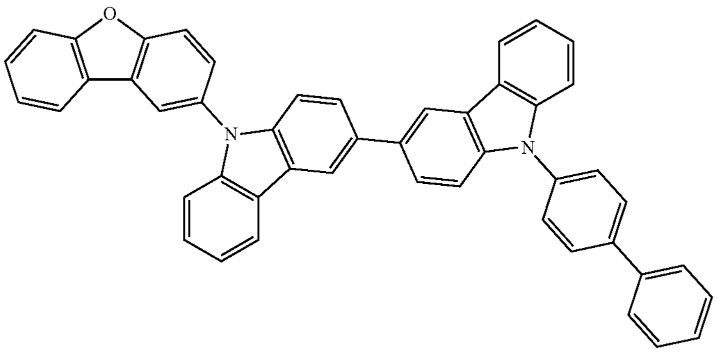

TABLE 3-continued
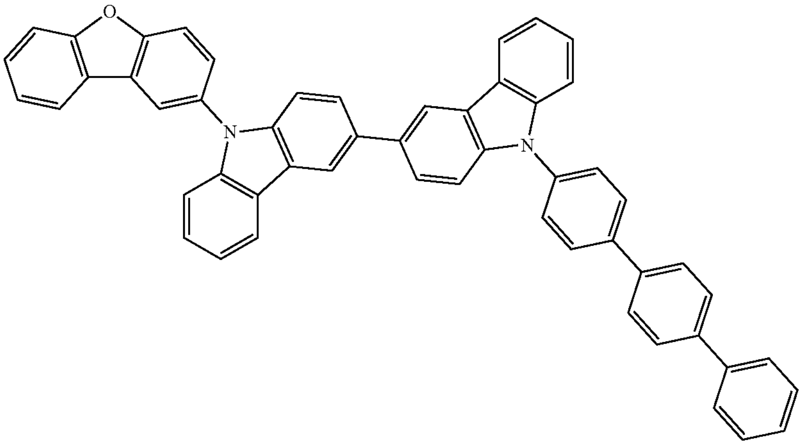 [SMILES: c1ccc(-c2ccc(-c3ccc(-n4c5ccccc5c5cc(-c6ccc7c(c6)c6ccccc6n7-c6ccc7oc8ccccc8c7c6)ccc54)cc3)cc2)cc1]
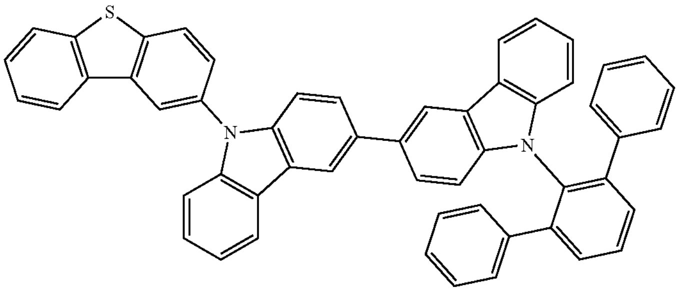 [SMILES: c1ccc(-c2cccc(-c3ccccc3)c2-n2c3ccccc3c3cc(-c4ccc5c(c4)c4ccccc4n5-c4ccc5sc6ccccc6c5c4)ccc32)cc1]
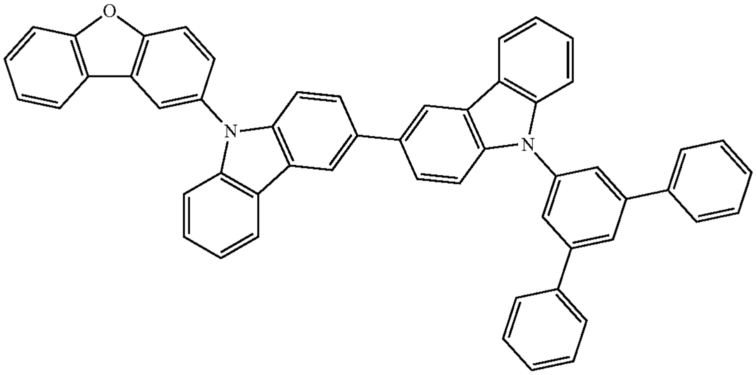
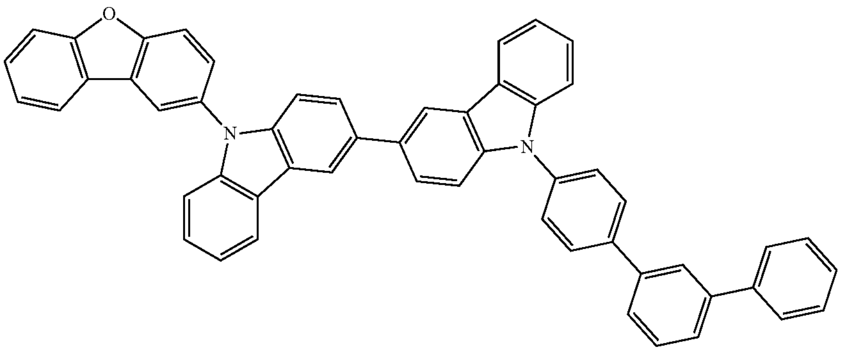 [SMILES: c1ccc(-c2cccc(-c3ccc(-n4c5ccccc5c5cc(-c6ccc7c(c6)c6ccccc6n7-c6ccc7oc8ccccc8c7c6)ccc54)cc3)c2)cc1]

TABLE 3-continued
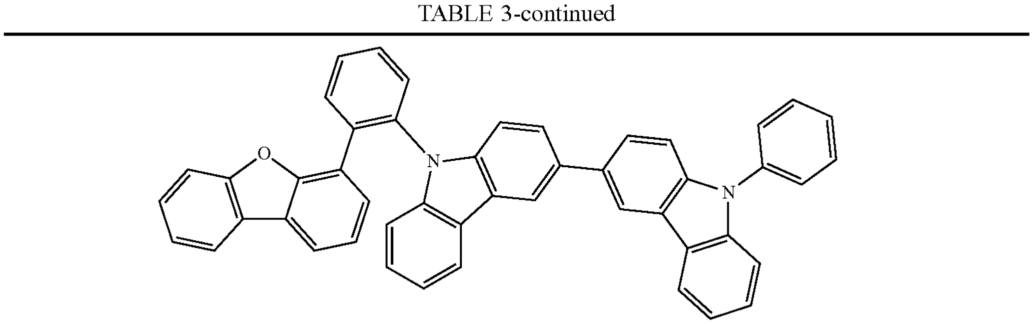
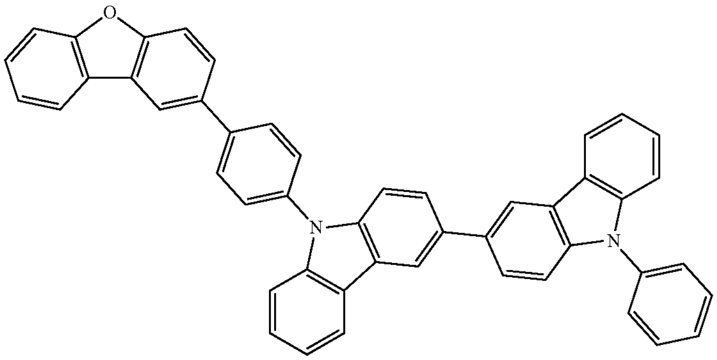 [SMILES: c1ccc(-n2c3ccccc3c3cc(-c4ccc5c(c4)c4ccccc4n5-c4ccc(-c5ccc6oc7ccccc7c6c5)cc4)ccc32)cc1]
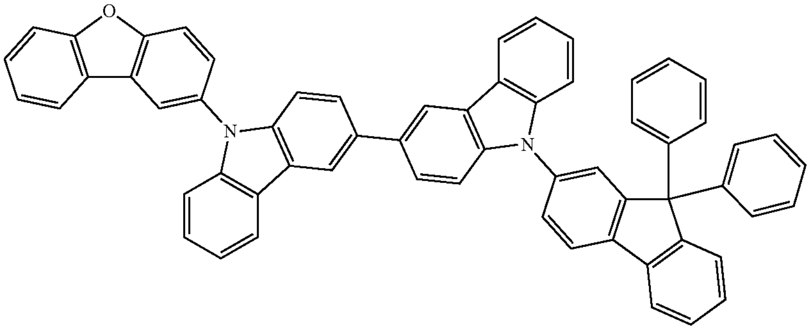 [SMILES: c1ccc(C2(c3ccccc3)c3ccccc3-c3ccc(-n4c5ccccc5c5cc(-c6ccc7c(c6)c6ccccc6n7-c6ccc7oc8ccccc8c7c6)ccc54)cc32)cc1]
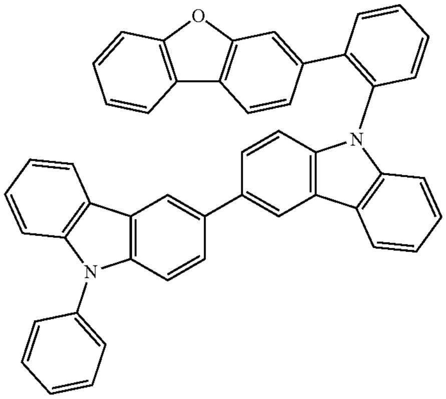 [SMILES: c1ccc(-n2c3ccccc3c3cc(-c4ccc5c(c4)c4ccccc4n5-c4ccccc4-c4ccc5c(c4)oc4ccccc45)ccc32)cc1]

TABLE 3-continued
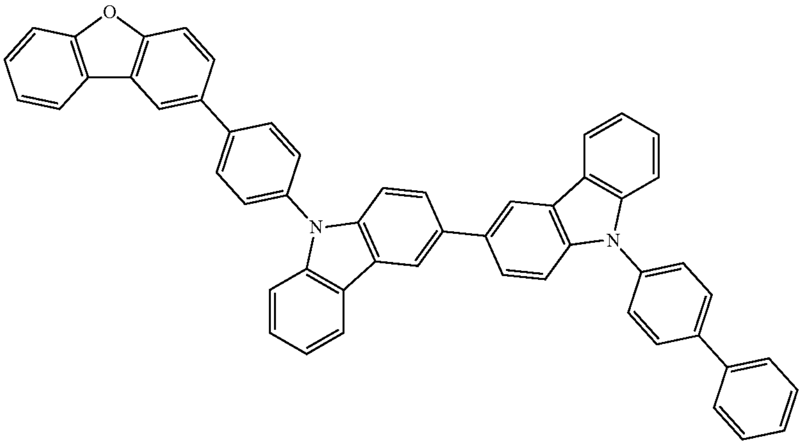 [SMILES: c1ccc(-c2ccc(-n3c4ccccc4c4cc(-c5ccc6c(c5)c5ccccc5n6-c5ccc(-c6ccc7oc8ccccc8c7c6)cc5)ccc43)cc2)cc1]
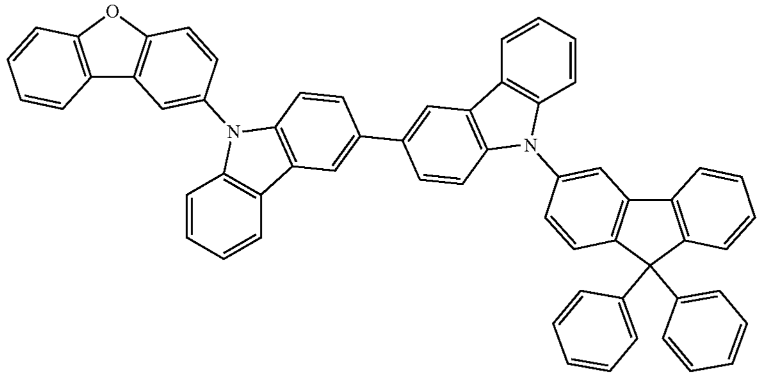 [SMILES: c1ccc(C2(c3ccccc3)c3ccccc3-c3cc(-n4c5ccccc5c5cc(-c6ccc7c(c6)c6ccccc6n7-c6ccc7oc8ccccc8c7c6)ccc54)ccc32)cc1]
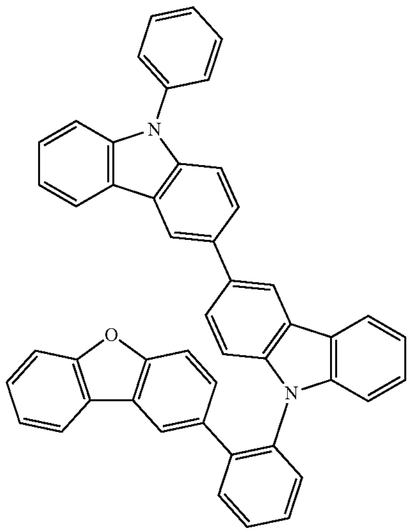 [SMILES: c1ccc(-n2c3ccccc3c3cc(-c4ccc5c(c4)c4ccccc4n5-c4ccccc4-c4ccc5oc6ccccc6c5c4)ccc32)cc1]

TABLE 3-continued
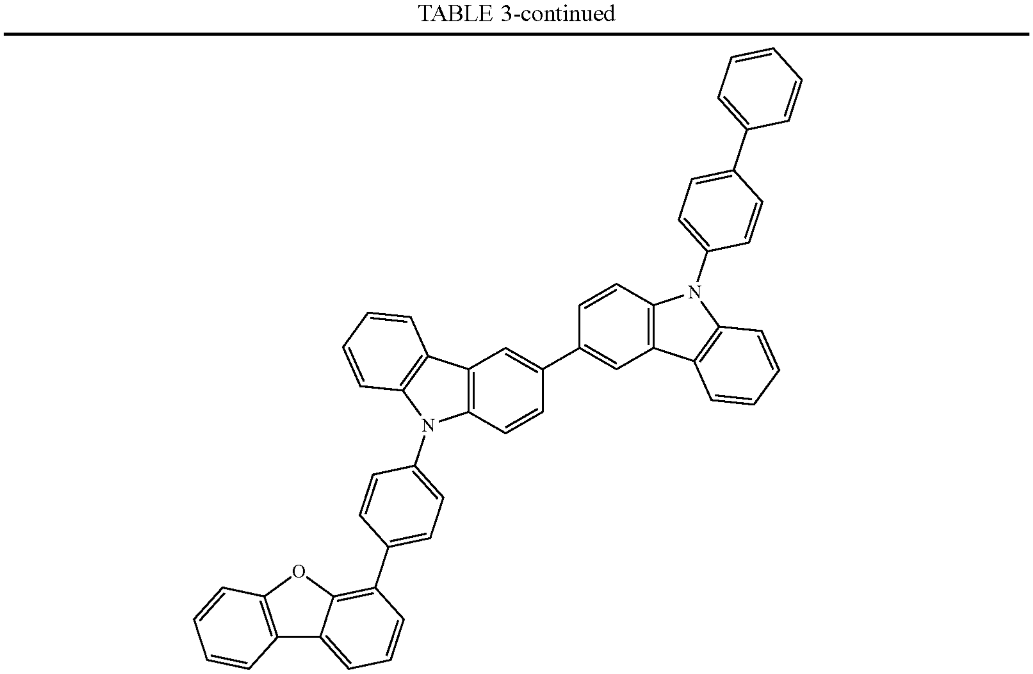
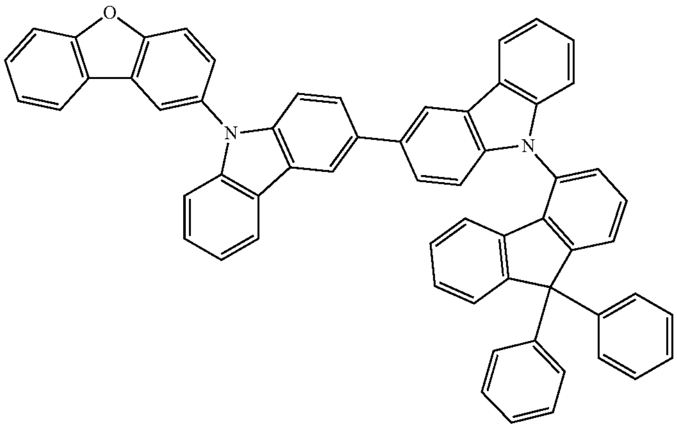 [SMILES: c1ccc(C2(c3ccccc3)c3ccccc3-c3c(-n4c5ccccc5c5cc(-c6ccc7c(c6)c6ccccc6n7-c6ccc7oc8ccccc8c7c6)ccc54)cccc32)cc1]

TABLE 3-continued
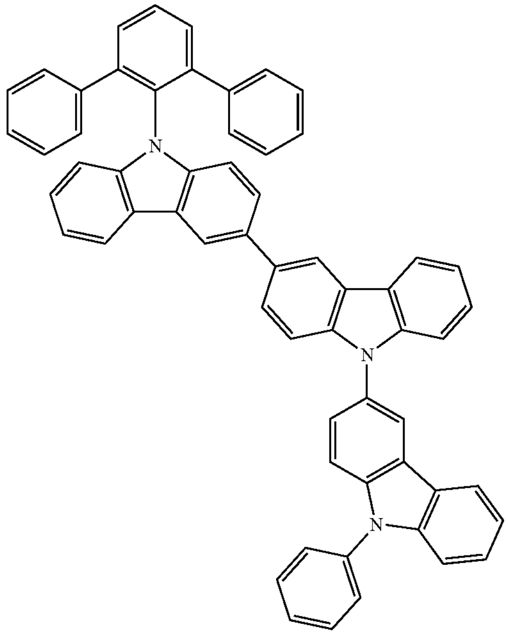 [SMILES: c1ccc(-c2cccc(-c3ccccc3)c2-n2c3ccccc3c3cc(-c4ccc5c(c4)c4ccccc4n5-c4ccc5c(c4)c4ccccc4n5-c4ccccc4)ccc32)cc1]
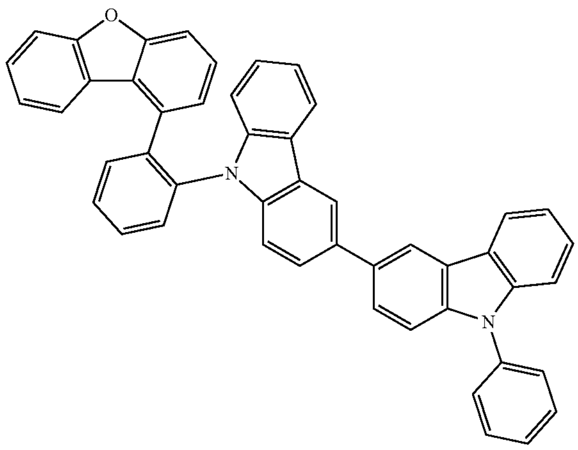 [SMILES: c1ccc(-n2c3ccccc3c3cc(-c4ccc5c(c4)c4ccccc4n5-c4ccccc4-c4cccc5oc6ccccc6c45)ccc32)cc1]

TABLE 3-continued
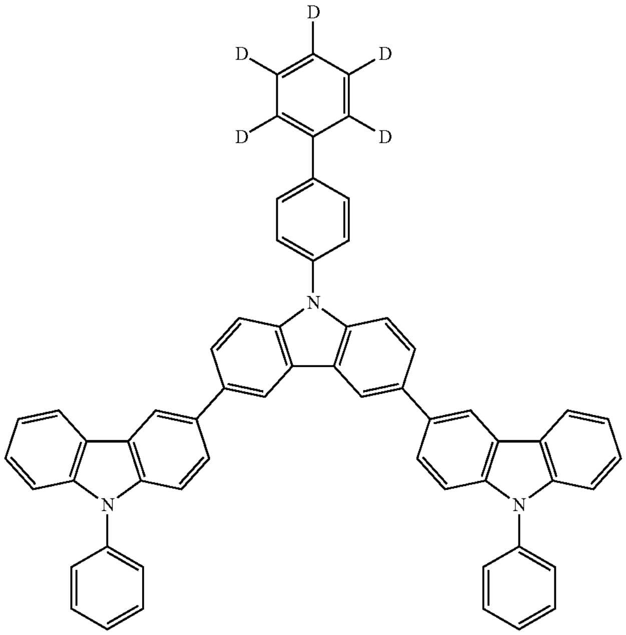 [SMILES: [2H]c1c([2H])c([2H])c(-c2ccc(-n3c4ccc(-c5ccc6c(c5)c5ccccc5n6-c5ccccc5)cc4c4cc(-c5ccc6c(c5)c5ccccc5n6-c5ccccc5)ccc43)cc2)c([2H])c1[2H]]
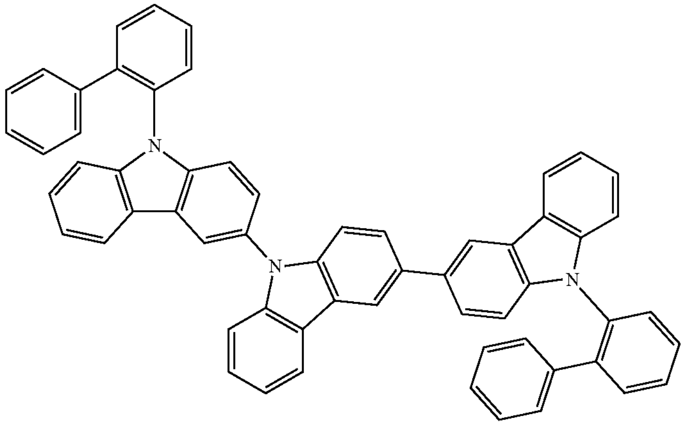 [SMILES: c1ccc(-c2ccccc2-n2c3ccccc3c3cc(-c4ccc5c(c4)c4ccccc4n5-c4ccc5c(c4)c4ccccc4n5-c4ccccc4-c4ccccc4)ccc32)cc1]
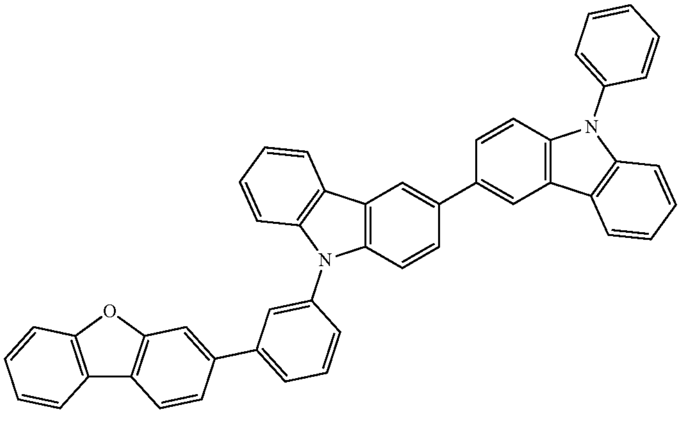

TABLE 3-continued
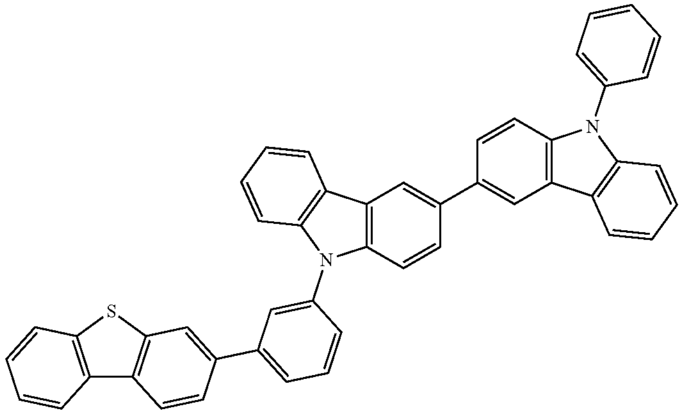 [SMILES: c1ccc(-n2c3ccccc3c3cc(-c4ccc5c(c4)c4ccccc4n5-c4cccc(-c5ccc6c(c5)oc5ccccc56)c4)ccc32)cc1]
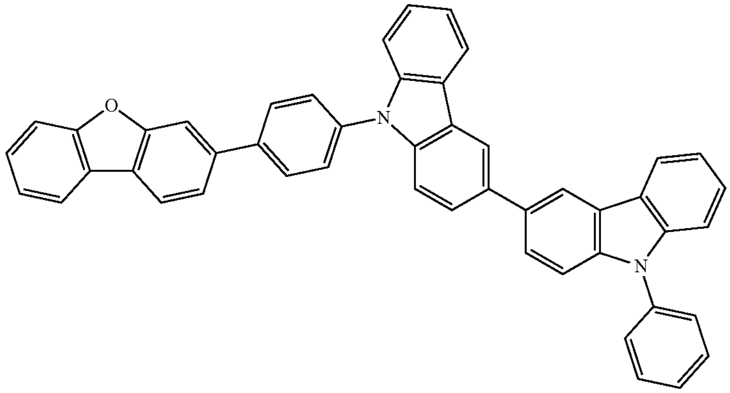
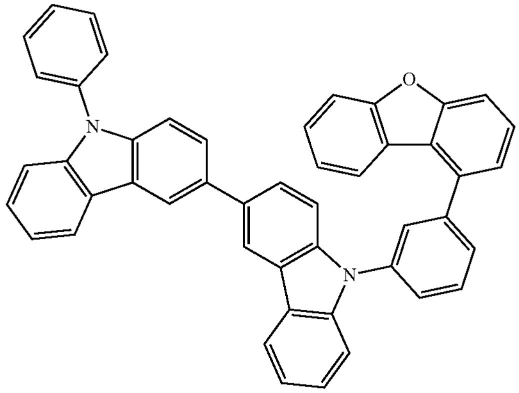 [SMILES: c1ccc(-n2c3ccccc3c3cc(-c4ccc5c(c4)c4ccccc4n5-c4cccc(-c5cccc6oc7ccccc7c56)c4)ccc32)cc1]
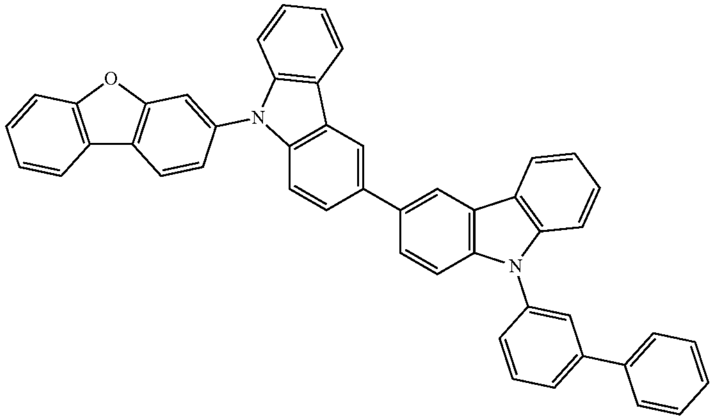 [SMILES: c1ccc(-c2cccc(-n3c4ccccc4c4cc(-c5ccc6c(c5)c5ccccc5n6-c5ccc6c(c5)oc5ccccc56)ccc43)c2)cc1]

TABLE 3-continued
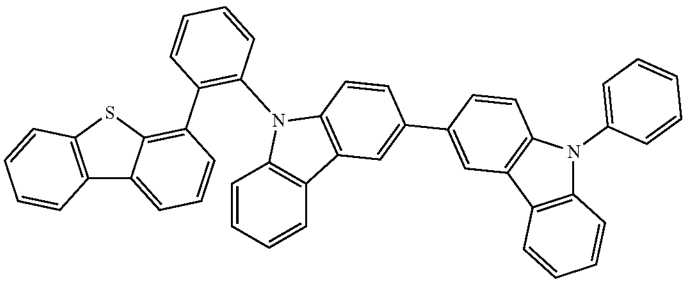 [SMILES: c1ccc(-n2c3ccccc3c3cc(-c4ccc5c(c4)c4ccccc4n5-c4ccccc4-c4cccc5c4sc4ccccc45)ccc32)cc1]
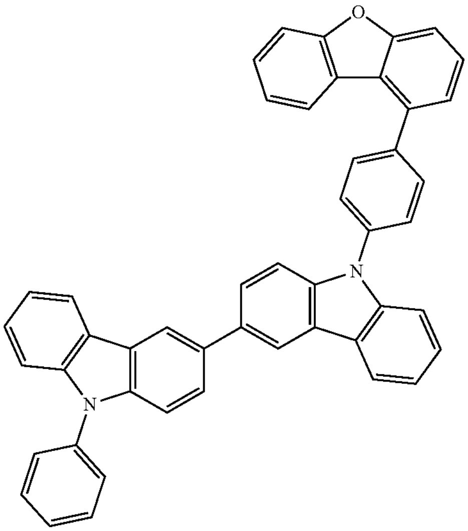
17
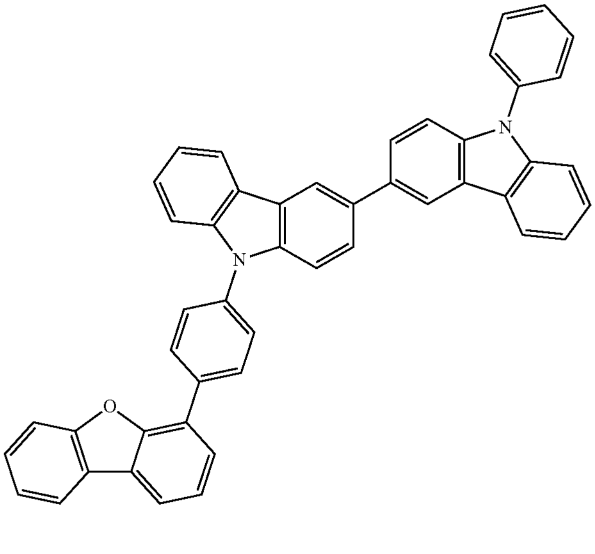

TABLE 3-continued
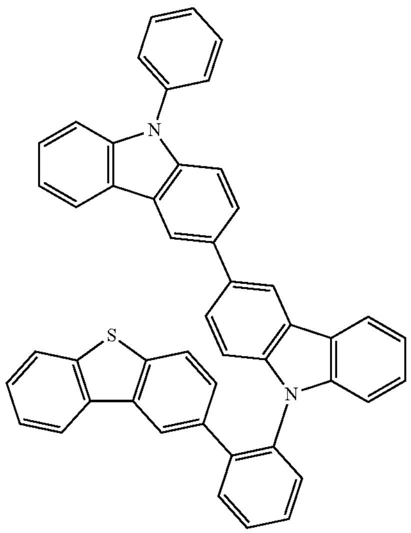
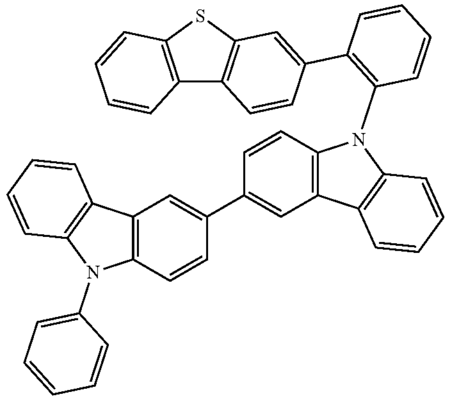 [SMILES: c1ccc(-n2c3ccccc3c3cc(-c4ccc5c(c4)c4ccccc4n5-c4ccccc4-c4ccc5c(c4)sc4ccccc45)ccc32)cc1]
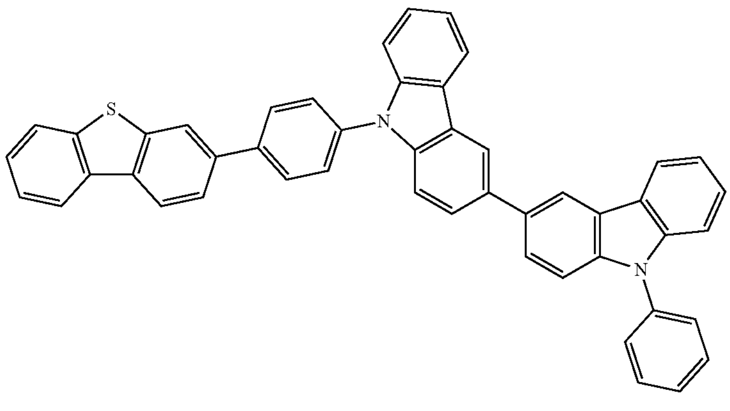

TABLE 3-continued
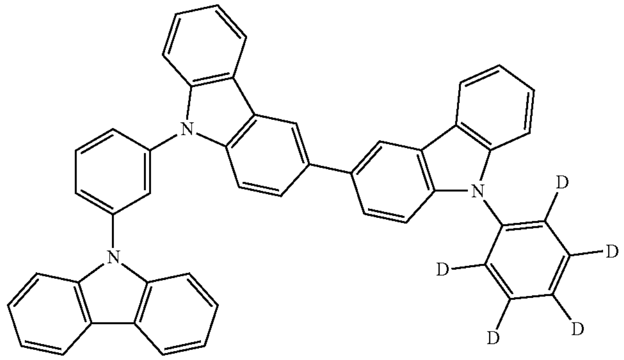 [SMILES: [2H]c1c([2H])c([2H])c(-n2c3ccccc3c3cc(-c4ccc5c(c4)c4ccccc4n5-c4cccc(-n5c6ccccc6c6ccccc65)c4)ccc32)c([2H])c1[2H]]
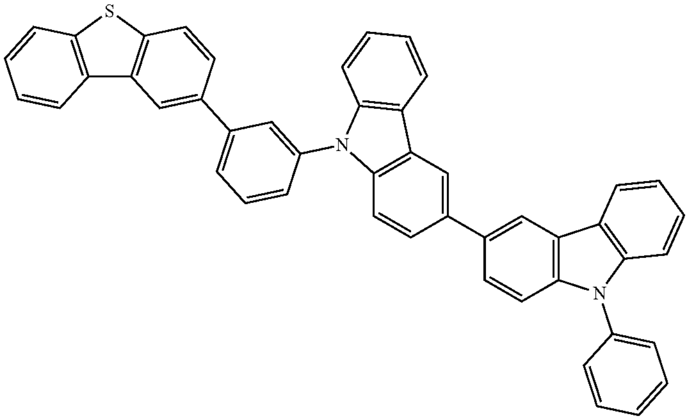
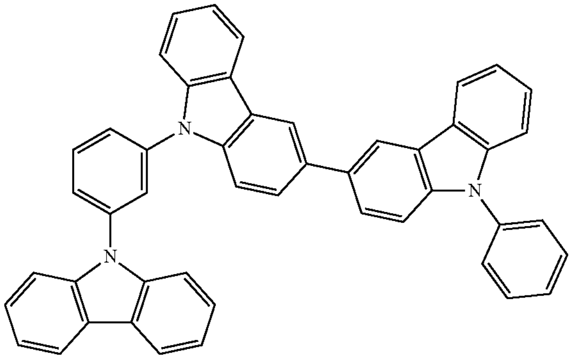 [SMILES: c1ccc(-n2c3ccccc3c3cc(-c4ccc5c(c4)c4ccccc4n5-c4cccc(-n5c6ccccc6c6ccccc65)c4)ccc32)cc1]
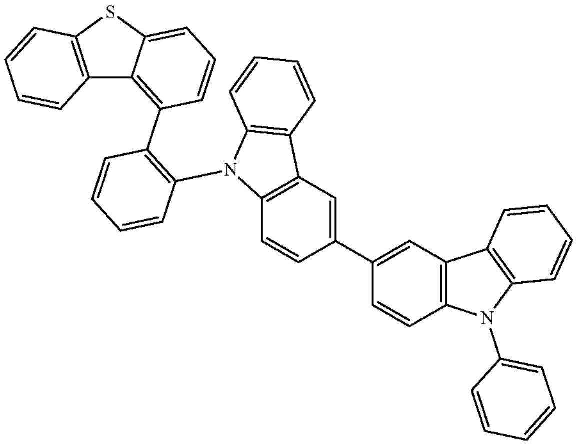

TABLE 3-continued
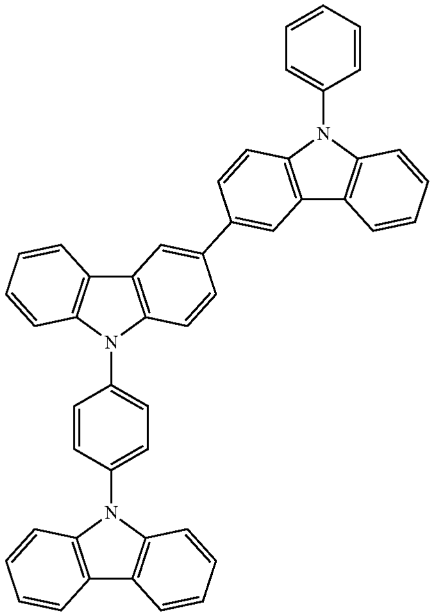 [SMILES: c1ccc(-n2c3ccccc3c3cc(-c4ccc5c(c4)c4ccccc4n5-c4ccc(-n5c6ccccc6c6ccccc65)cc4)ccc32)cc1]
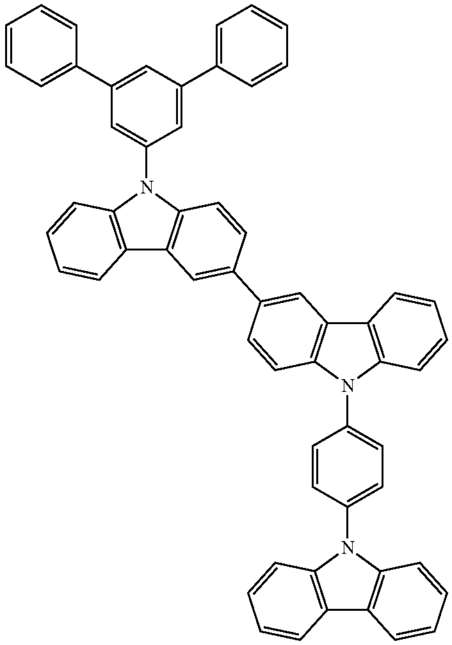 [SMILES: c1ccc(-c2cc(-c3ccccc3)cc(-n3c4ccccc4c4cc(-c5ccc6c(c5)c5ccccc5n6-c5ccc(-n6c7ccccc7c7ccccc76)cc5)ccc43)c2)cc1]

TABLE 3-continued
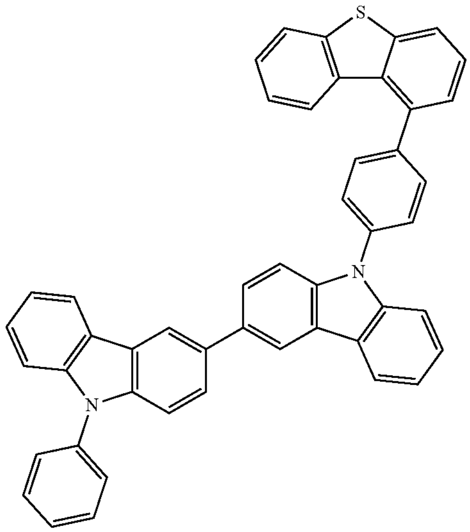 [SMILES: c1ccc(-n2c3ccccc3c3cc(-c4ccc5c(c4)c4ccccc4n5-c4ccc(-c5cccc6sc7ccccc7c56)cc4)ccc32)cc1]
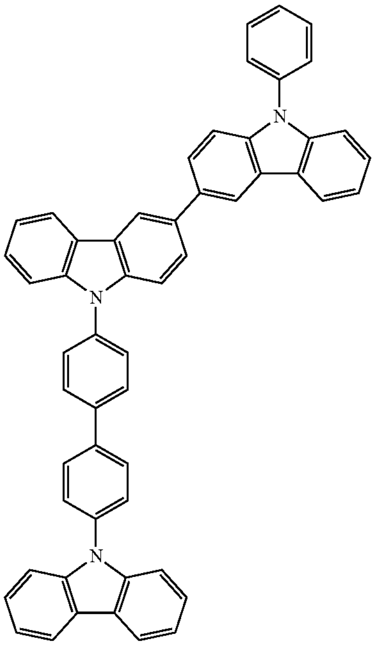 [SMILES: c1ccc(-n2c3ccccc3c3cc(-c4ccc5c(c4)c4ccccc4n5-c4ccc(-c5ccc(-n6c7ccccc7c7ccccc76)cc5)cc4)ccc32)cc1]
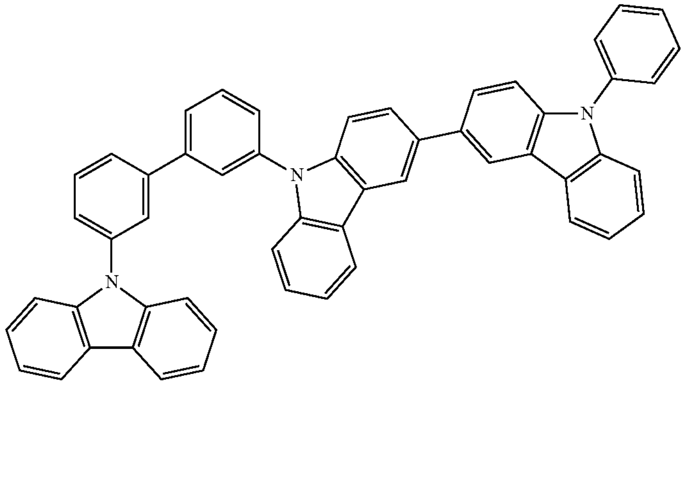 [SMILES: c1ccc(-n2c3ccccc3c3cc(-c4ccc5c(c4)c4ccccc4n5-c4cccc(-c5cccc(-n6c7ccccc7c7ccccc76)c5)c4)ccc32)cc1]

TABLE 3-continued
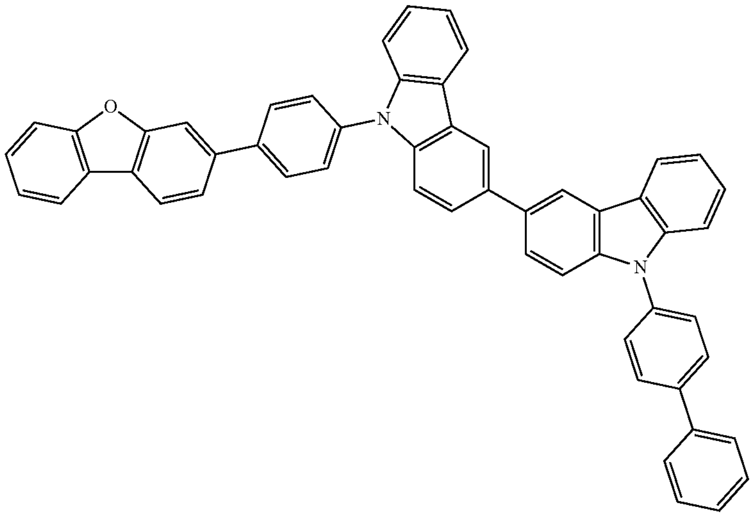 [SMILES: c1ccc(-c2ccc(-n3c4ccccc4c4cc(-c5ccc6c(c5)c5ccccc5n6-c5ccc(-c6ccc7c(c6)oc6ccccc67)cc5)ccc43)cc2)cc1]
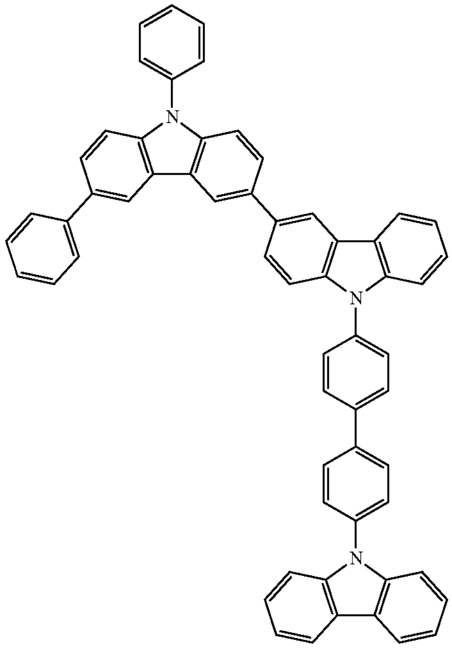 [SMILES: c1ccc(-c2ccc3c(c2)c2cc(-c4ccc5c(c4)c4ccccc4n5-c4ccc(-c5ccc(-n6c7ccccc7c7ccccc76)cc5)cc4)ccc2n3-c2ccccc2)cc1]

TABLE 3-continued
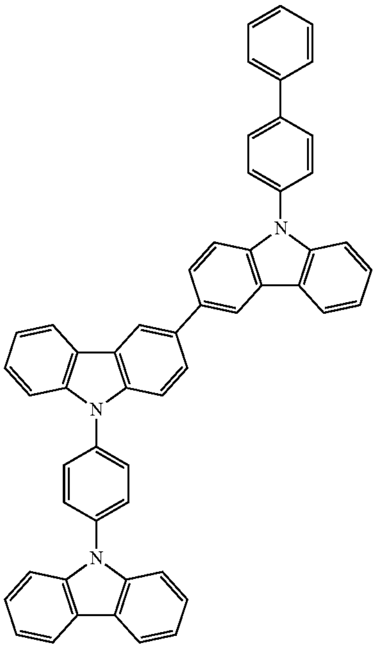 [SMILES: c1ccc(-c2ccc(-n3c4ccccc4c4cc(-c5ccc6c(c5)c5ccccc5n6-c5ccc(-n6c7ccccc7c7ccccc76)cc5)ccc43)cc2)cc1]
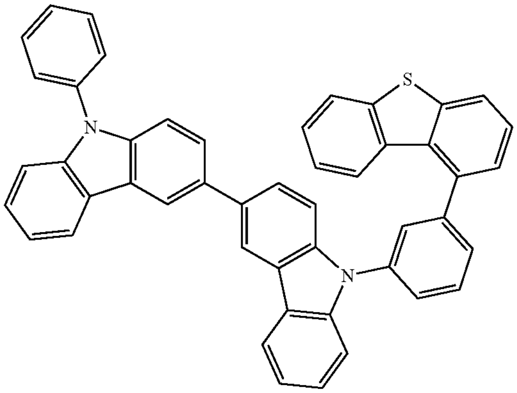 [SMILES: c1ccc(-n2c3ccccc3c3cc(-c4ccc5c(c4)c4ccccc4n5-c4cccc(-c5cccc6sc7ccccc7c56)c4)ccc32)cc1]
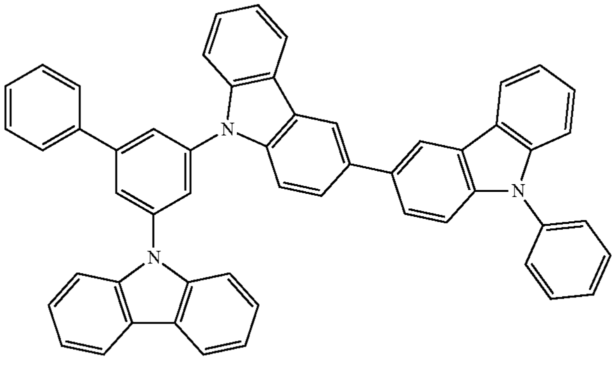 [SMILES: c1ccc(-c2cc(-n3c4ccccc4c4ccccc43)cc(-n3c4ccccc4c4cc(-c5ccc6c(c5)c5ccccc5n6-c5ccccc5)ccc43)c2)cc1]

TABLE 3-continued
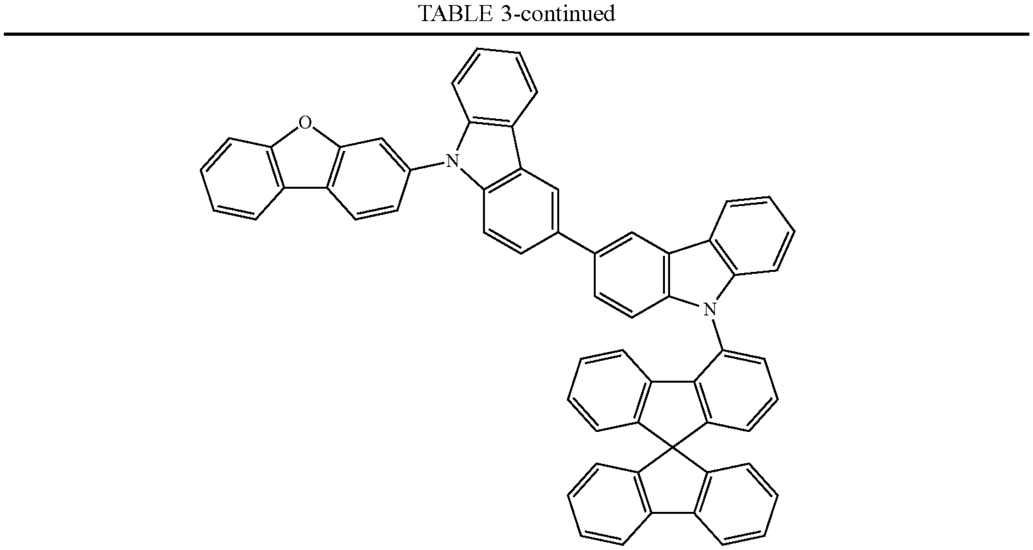
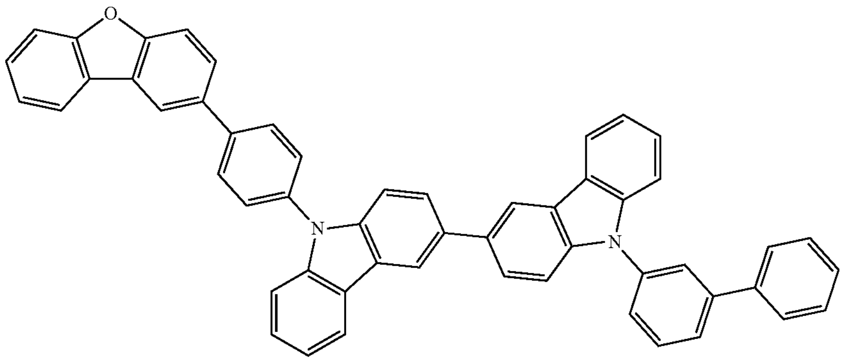 [SMILES: c1ccc(-c2cccc(-n3c4ccccc4c4cc(-c5ccc6c(c5)c5ccccc5n6-c5ccc(-c6ccc7oc8ccccc8c7c6)cc5)ccc43)c2)cc1]
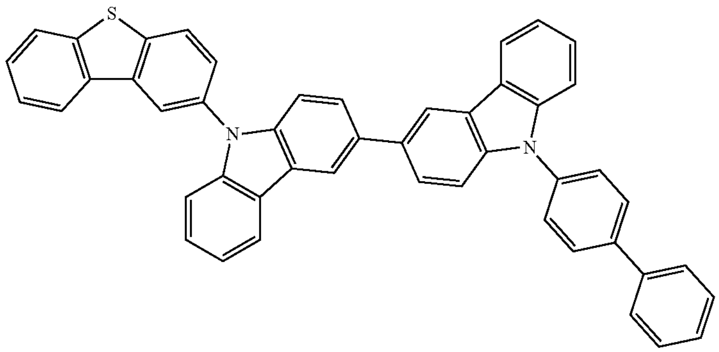 [SMILES: c1ccc(-c2ccc(-n3c4ccccc4c4cc(-c5ccc6c(c5)c5ccccc5n6-c5ccc6sc7ccccc7c6c5)ccc43)cc2)cc1]
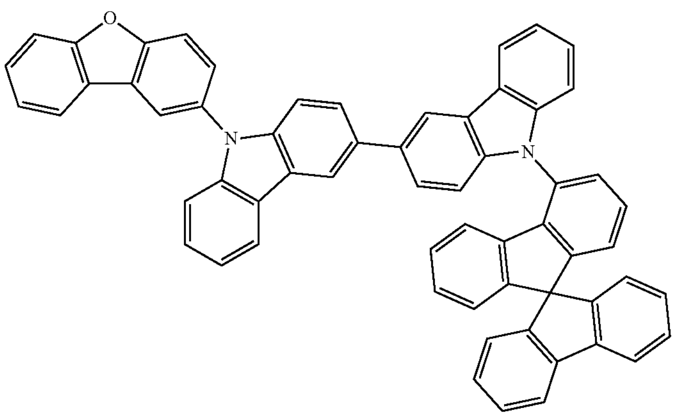 [SMILES: c1ccc2c(c1)-c1ccccc1C21c2ccccc2-c2c(-n3c4ccccc4c4cc(-c5ccc6c(c5)c5ccccc5n6-c5ccc6oc7ccccc7c6c5)ccc43)cccc21]

TABLE 3-continued
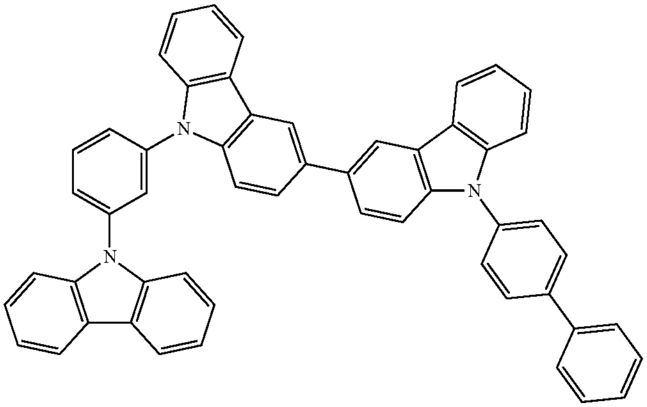 [SMILES: c1ccc(-c2ccc(-n3c4ccccc4c4cc(-c5ccc6c(c5)c5ccccc5n6-c5cccc(-n6c7ccccc7c7ccccc76)c5)ccc43)cc2)cc1]
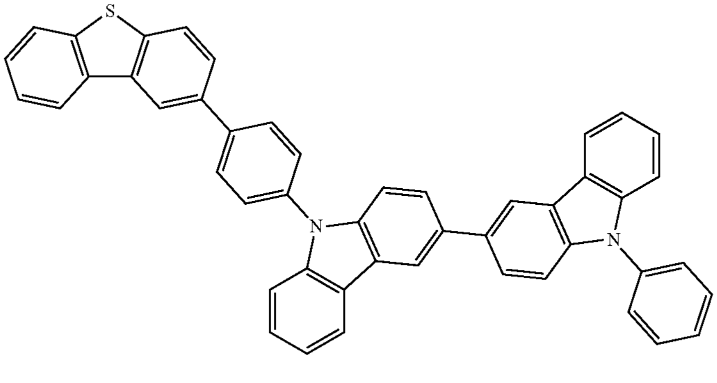
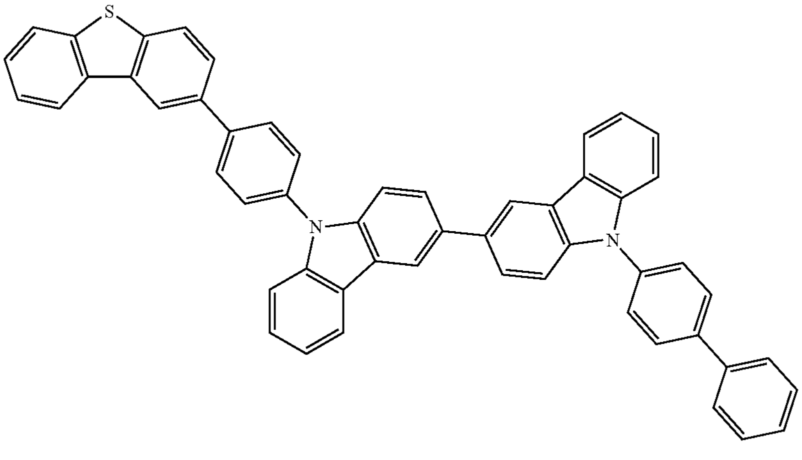 [SMILES: c1ccc(-c2ccc(-n3c4ccccc4c4cc(-c5ccc6c(c5)c5ccccc5n6-c5ccc(-c6ccc7sc8ccccc8c7c6)cc5)ccc43)cc2)cc1]

TABLE 3-continued
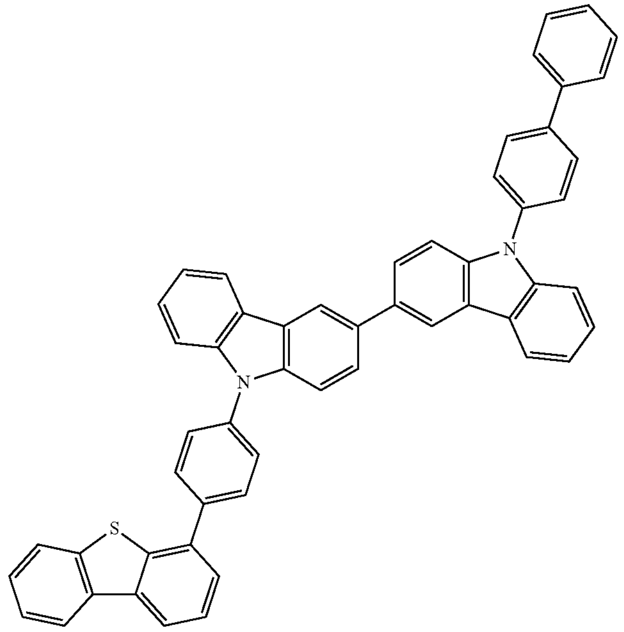 [SMILES: c1ccc(-c2ccc(-n3c4ccccc4c4cc(-c5ccc6c(c5)c5ccccc5n6-c5ccc(-c6cccc7c6sc6ccccc67)cc5)ccc43)cc2)cc1]
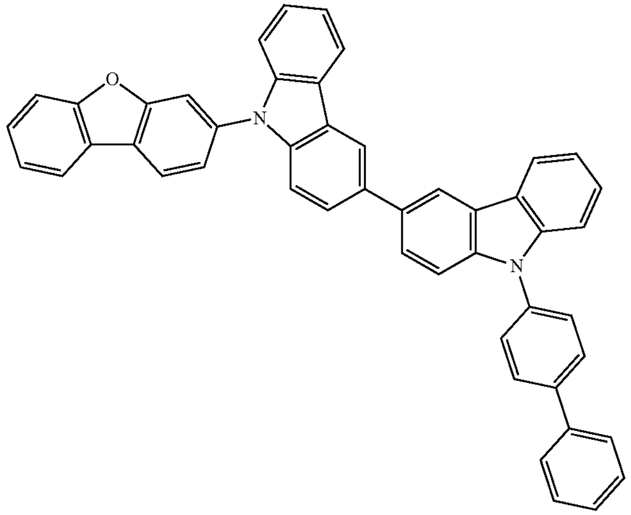 [SMILES: c1ccc(-c2ccc(-n3c4ccccc4c4cc(-c5ccc6c(c5)c5ccccc5n6-c5ccc6c(c5)oc5ccccc56)ccc43)cc2)cc1]

TABLE 3-continued
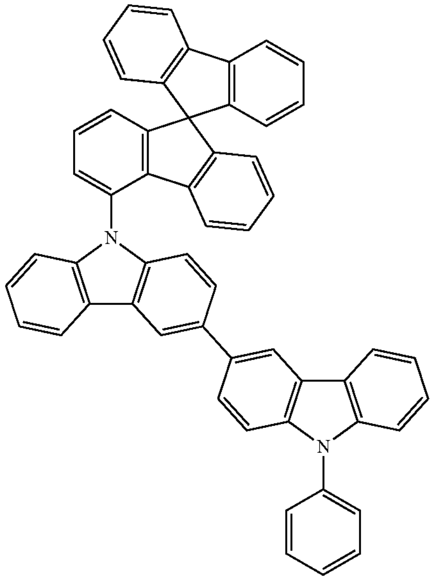 [SMILES: c1ccc(-n2c3ccccc3c3cc(-c4ccc5c(c4)c4ccccc4n5-c4cccc5c4-c4ccccc4C54c5ccccc5-c5ccccc54)ccc32)cc1]
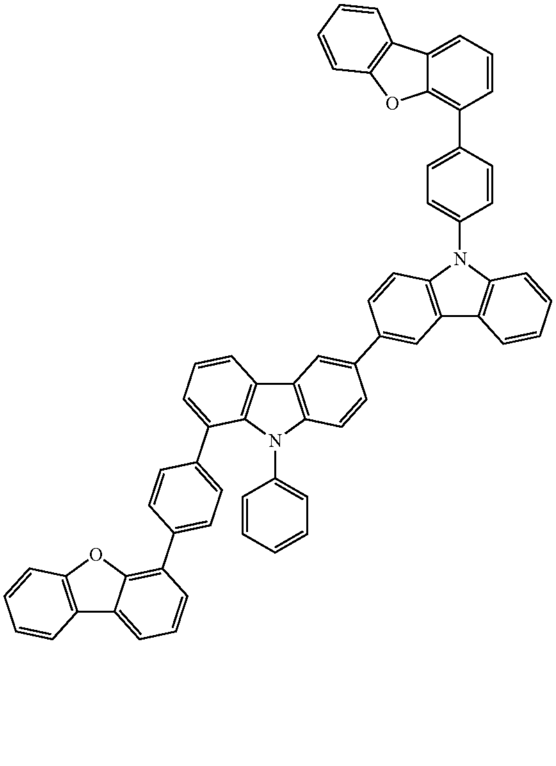 [SMILES: c1ccc(-n2c3ccc(-c4ccc5c(c4)c4ccccc4n5-c4ccc(-c5cccc6c5oc5ccccc56)cc4)cc3c3cccc(-c4ccc(-c5cccc6c5oc5ccccc56)cc4)c32)cc1]

TABLE 3-continued
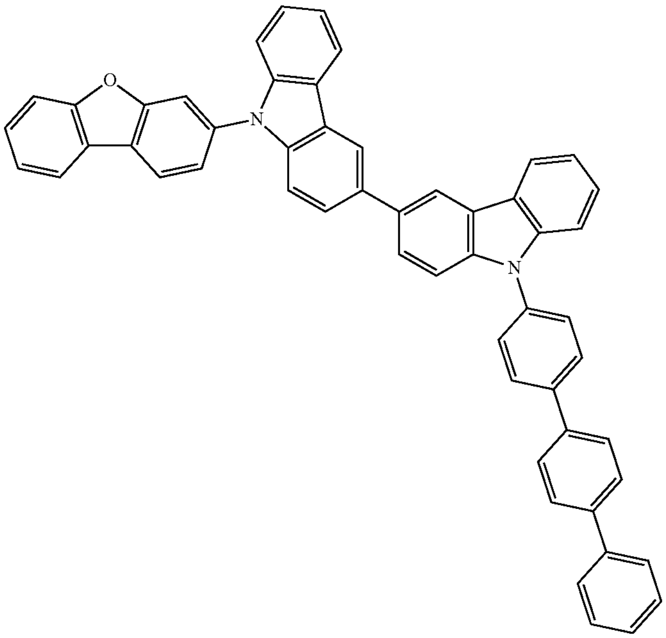 [SMILES: c1ccc(-c2ccc(-c3ccc(-n4c5ccccc5c5cc(-c6ccc7c(c6)c6ccccc6n7-c6ccc7c(c6)oc6ccccc67)ccc54)cc3)cc2)cc1]
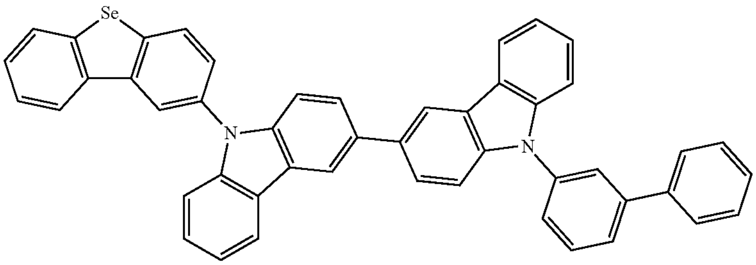
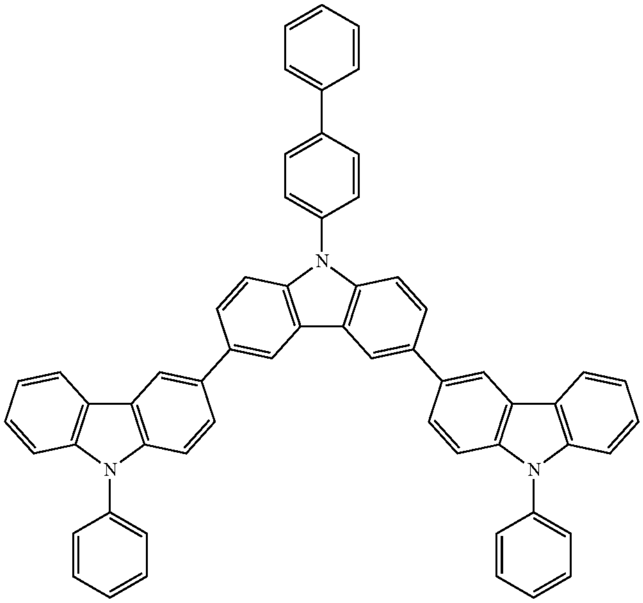 [SMILES: c1ccc(-c2ccc(-n3c4ccc(-c5ccc6c(c5)c5ccccc5n6-c5ccccc5)cc4c4cc(-c5ccc6c(c5)c5ccccc5n6-c5ccccc5)ccc43)cc2)cc1]

TABLE 3-continued
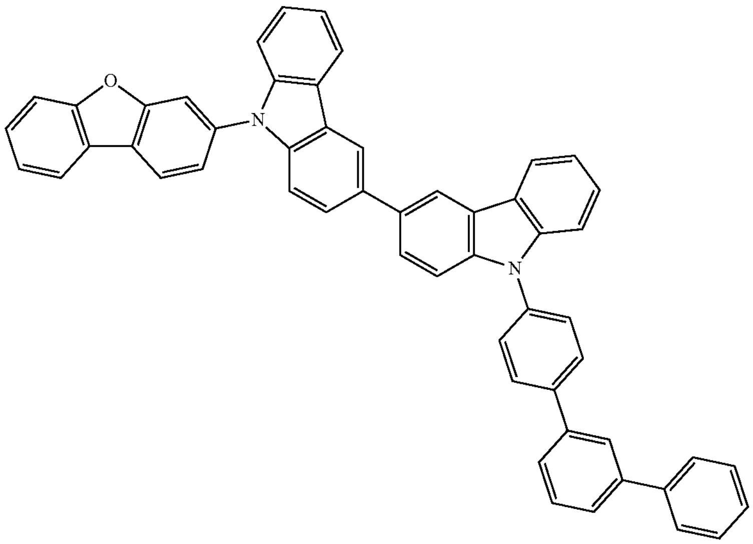 [SMILES: c1ccc(-c2cccc(-c3ccc(-n4c5ccccc5c5cc(-c6ccc7c(c6)c6ccccc6n7-c6ccc7c(c6)oc6ccccc67)ccc54)cc3)c2)cc1]
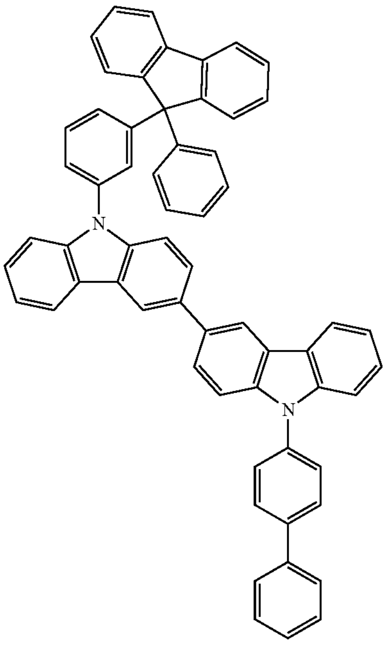 [SMILES: c1ccc(-c2ccc(-n3c4ccccc4c4cc(-c5ccc6c(c5)c5ccccc5n6-c5cccc(C6(c7ccccc7)c7ccccc7-c7ccccc76)c5)ccc43)cc2)cc1]

TABLE 3-continued
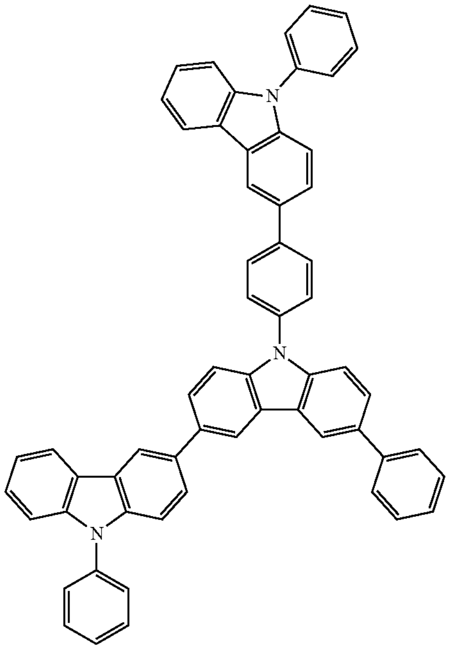 [SMILES: c1ccc(-c2ccc3c(c2)c2cc(-c4ccc5c(c4)c4ccccc4n5-c4ccccc4)ccc2n3-c2ccc(-c3ccc4c(c3)c3ccccc3n4-c3ccccc3)cc2)cc1]
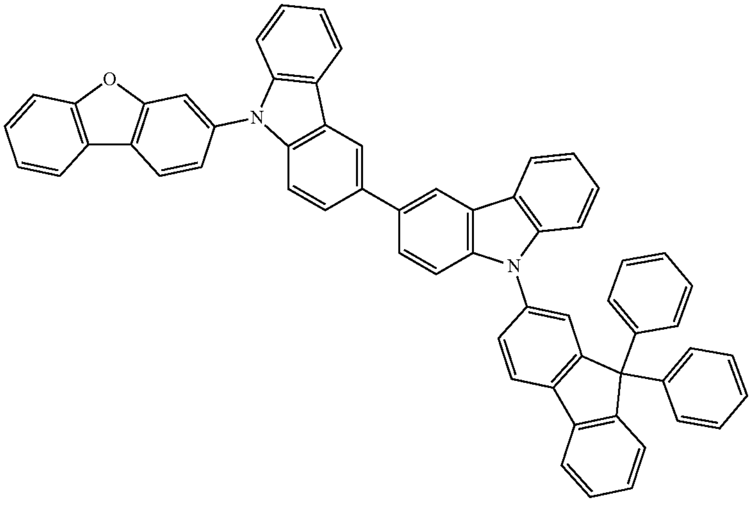 [SMILES: c1ccc(C2(c3ccccc3)c3ccccc3-c3ccc(-n4c5ccccc5c5cc(-c6ccc7c(c6)c6ccccc6n7-c6ccc7c(c6)oc6ccccc67)ccc54)cc32)cc1]

TABLE 3-continued
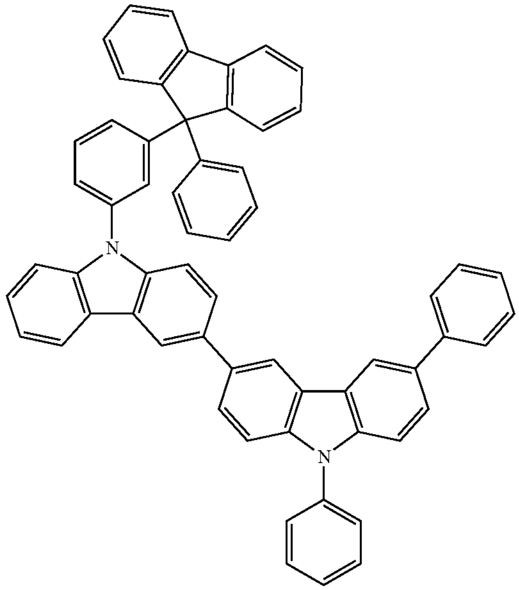 [SMILES: c1ccc(-c2ccc3c(c2)c2cc(-c4ccc5c(c4)c4ccccc4n5-c4cccc(C5(c6ccccc6)c6ccccc6-c6ccccc65)c4)ccc2n3-c2ccccc2)cc1]
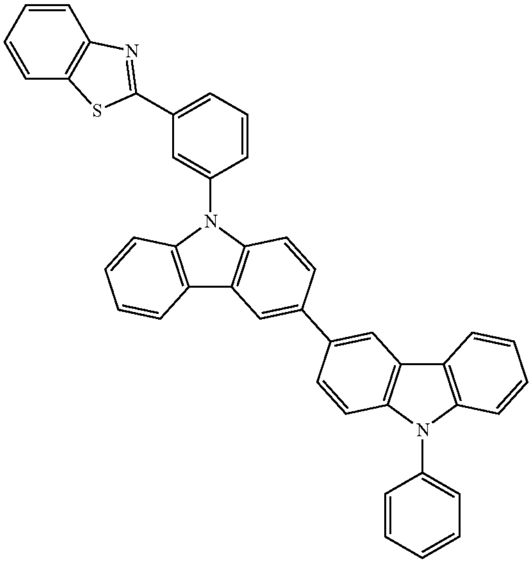 [SMILES: c1ccc(-n2c3ccccc3c3cc(-c4ccc5c(c4)c4ccccc4n5-c4cccc(-c5nc6ccccc6s5)c4)ccc32)cc1]

TABLE 3-continued
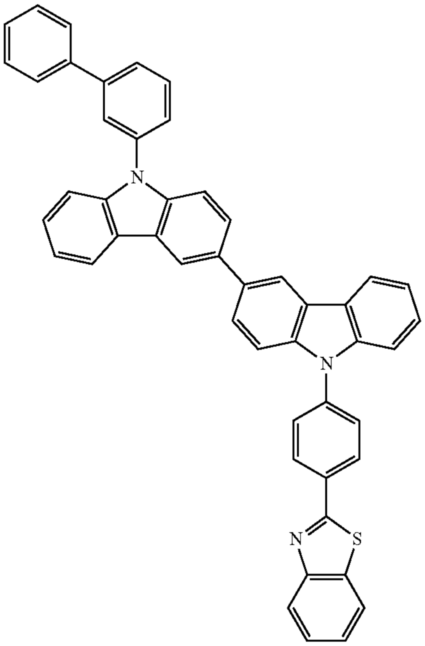 [SMILES: c1ccc(-c2cccc(-n3c4ccccc4c4cc(-c5ccc6c(c5)c5ccccc5n6-c5ccc(-c6nc7ccccc7s6)cc5)ccc43)c2)cc1]
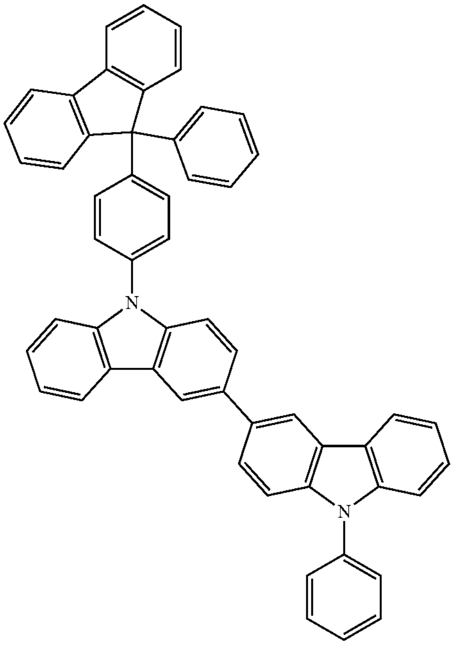 [SMILES: c1ccc(-n2c3ccccc3c3cc(-c4ccc5c(c4)c4ccccc4n5-c4ccc(C5(c6ccccc6)c6ccccc6-c6ccccc65)cc4)ccc32)cc1]
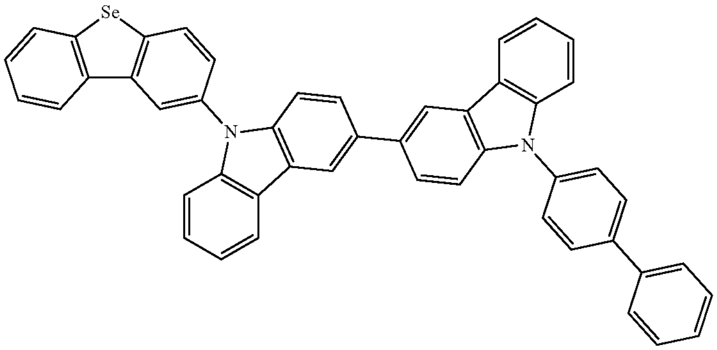

TABLE 3-continued
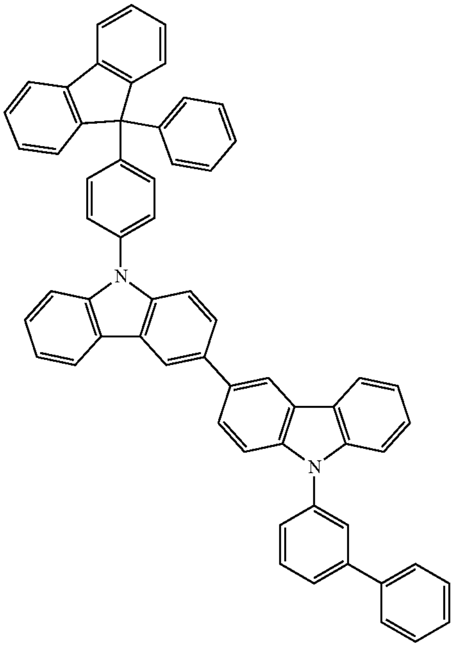 [SMILES: c1ccc(-c2cccc(-n3c4ccccc4c4cc(-c5ccc6c(c5)c5ccccc5n6-c5ccc(C6(c7ccccc7)c7ccccc7-c7ccccc76)cc5)ccc43)c2)cc1]
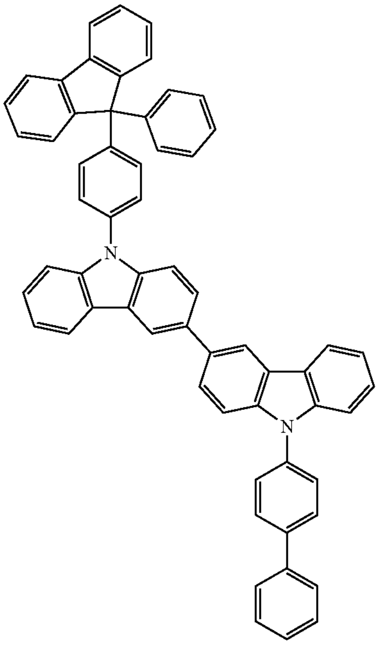 [SMILES: c1ccc(-c2ccc(-n3c4ccccc4c4cc(-c5ccc6c(c5)c5ccccc5n6-c5ccc(C6(c7ccccc7)c7ccccc7-c7ccccc76)cc5)ccc43)cc2)cc1]

TABLE 3-continued
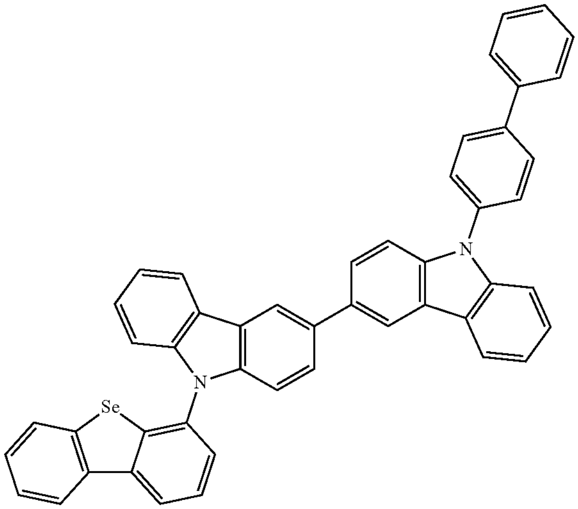
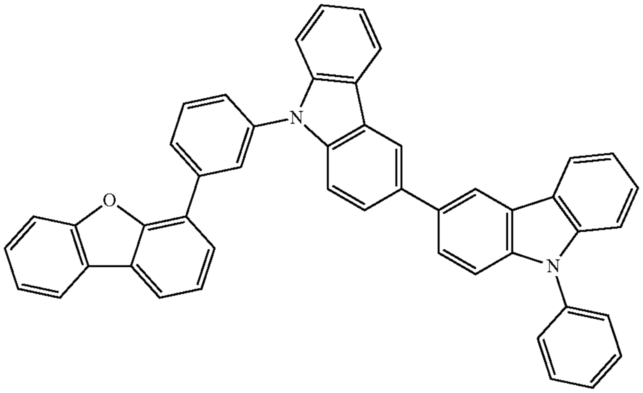
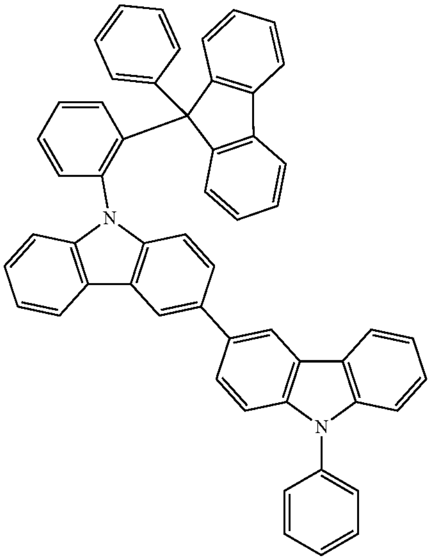 [SMILES: c1ccc(-n2c3ccccc3c3cc(-c4ccc5c(c4)c4ccccc4n5-c4ccccc4C4(c5ccccc5)c5ccccc5-c5ccccc54)ccc32)cc1]

TABLE 3-continued
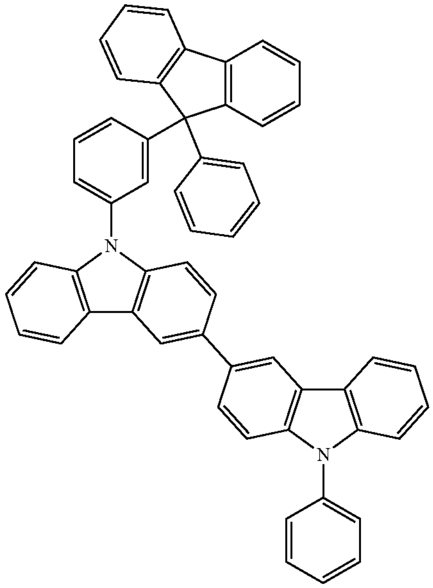 [SMILES: c1ccc(-n2c3ccccc3c3cc(-c4ccc5c(c4)c4ccccc4n5-c4cccc(C5(c6ccccc6)c6ccccc6-c6ccccc65)c4)ccc32)cc1]
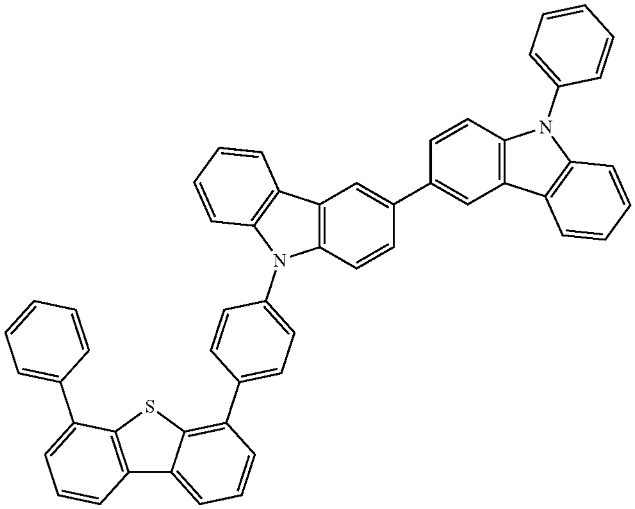 [SMILES: c1ccc(-c2cccc3c2sc2c(-c4ccc(-n5c6ccccc6c6cc(-c7ccc8c(c7)c7ccccc7n8-c7ccccc7)ccc65)cc4)cccc23)cc1]
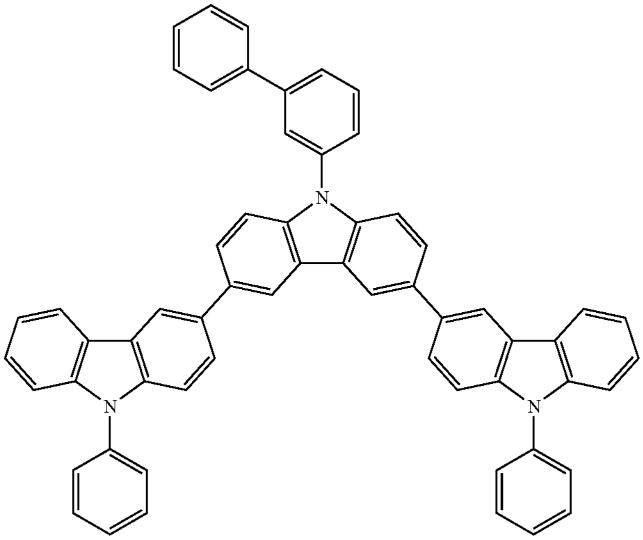 [SMILES: c1ccc(-c2cccc(-n3c4ccc(-c5ccc6c(c5)c5ccccc5n6-c5ccccc5)cc4c4cc(-c5ccc6c(c5)c5ccccc5n6-c5ccccc5)ccc43)c2)cc1]

TABLE 3-continued
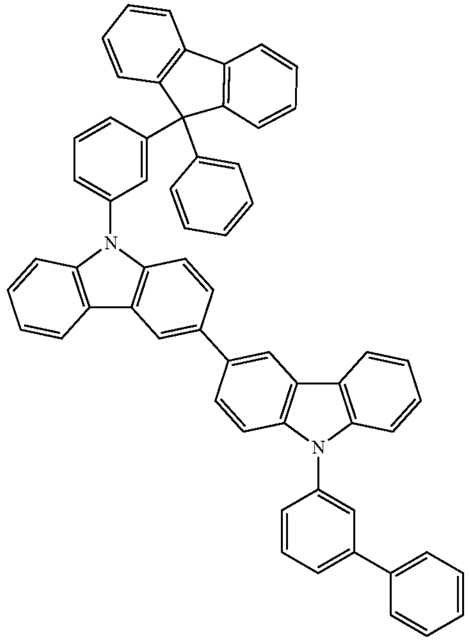 [SMILES: c1ccc(-c2cccc(-n3c4ccccc4c4cc(-c5ccc6c(c5)c5ccccc5n6-c5cccc(C6(c7ccccc7)c7ccccc7-c7ccccc76)c5)ccc43)c2)cc1]
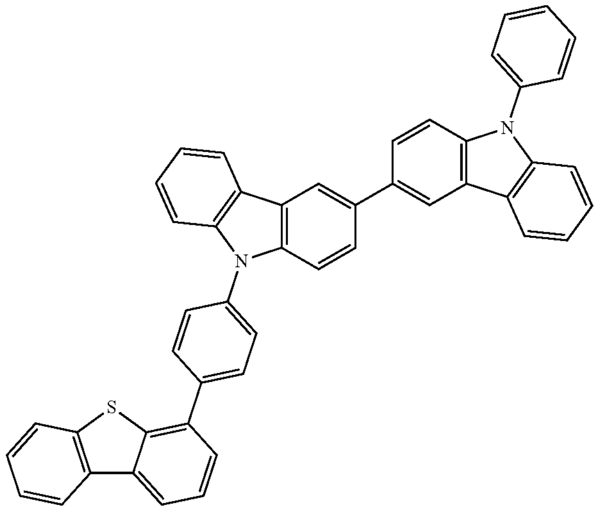 [SMILES: c1ccc(-n2c3ccccc3c3cc(-c4ccc5c(c4)c4ccccc4n5-c4ccc(-c5cccc6c5sc5ccccc56)cc4)ccc32)cc1]
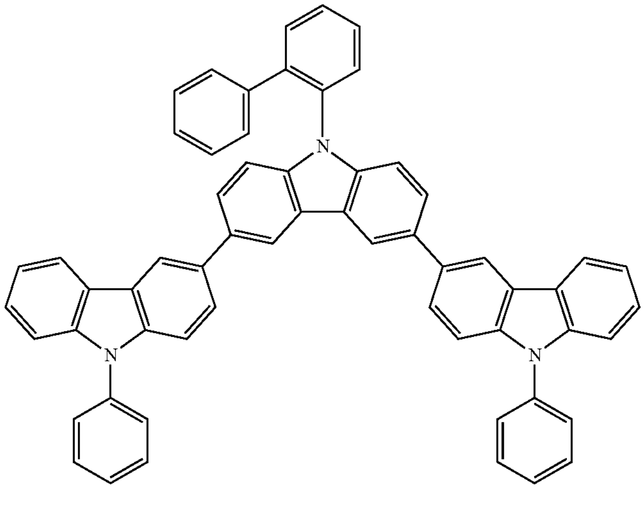 [SMILES: c1ccc(-c2ccccc2-n2c3ccc(-c4ccc5c(c4)c4ccccc4n5-c4ccccc4)cc3c3cc(-c4ccc5c(c4)c4ccccc4n5-c4ccccc4)ccc32)cc1]

TABLE 3-continued
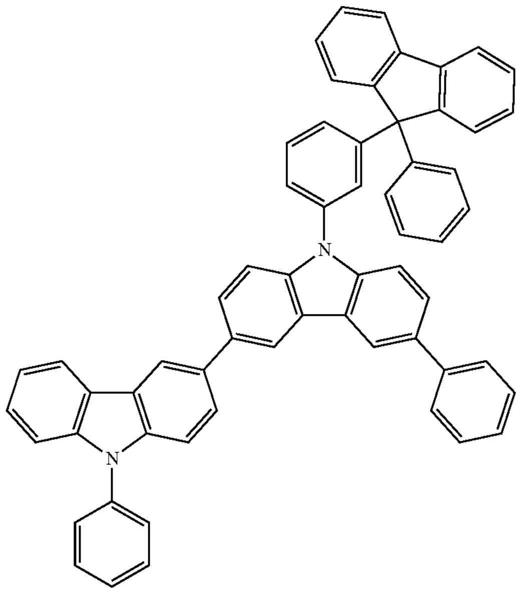 [SMILES: c1ccc(-c2ccc3c(c2)c2cc(-c4ccc5c(c4)c4ccccc4n5-c4ccccc4)ccc2n3-c2cccc(C3(c4ccccc4)c4ccccc4-c4ccccc43)c2)cc1]
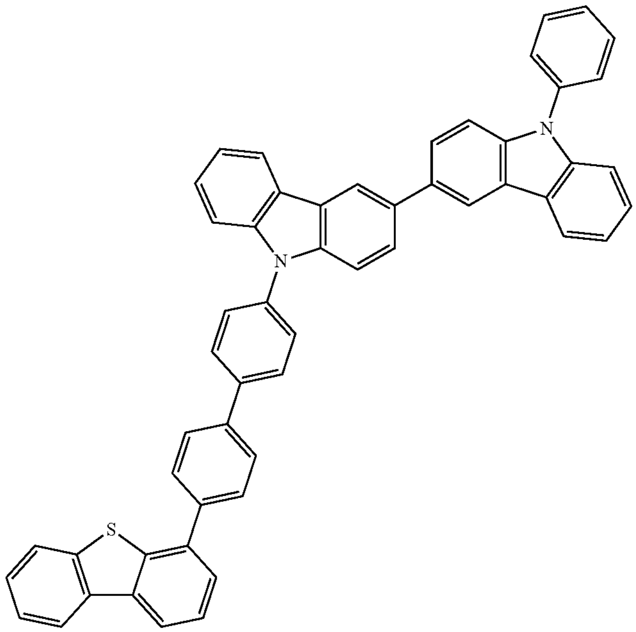 [SMILES: c1ccc(-n2c3ccccc3c3cc(-c4ccc5c(c4)c4ccccc4n5-c4ccc(-c5ccc(-c6cccc7c6sc6ccccc67)cc5)cc4)ccc32)cc1]

TABLE 3-continued
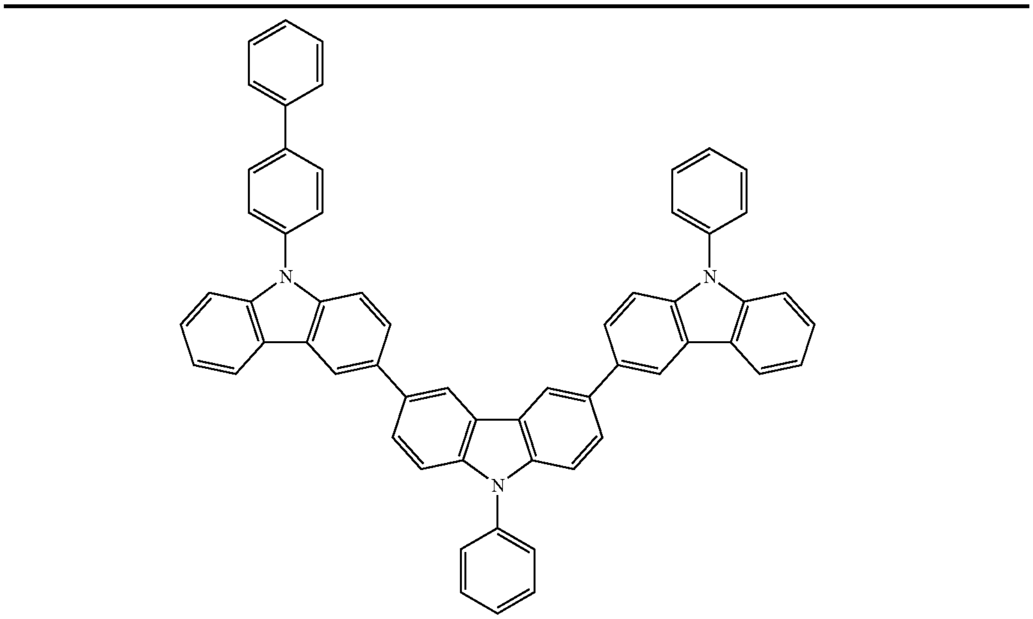
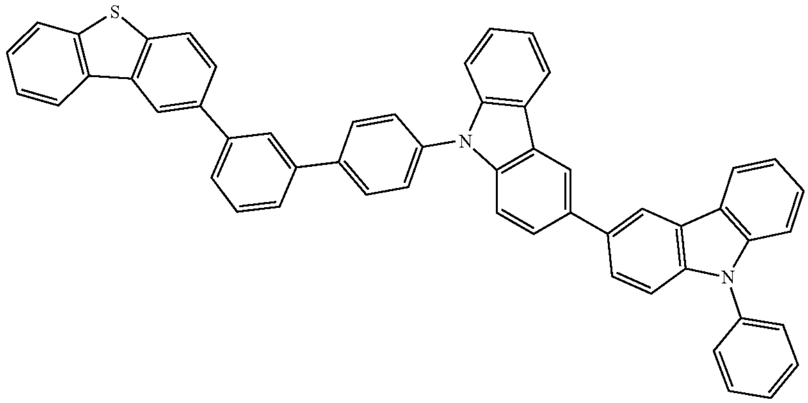 [SMILES: c1ccc(-n2c3ccccc3c3cc(-c4ccc5c(c4)c4ccccc4n5-c4ccc(-c5cccc(-c6ccc7sc8ccccc8c7c6)c5)cc4)ccc32)cc1]
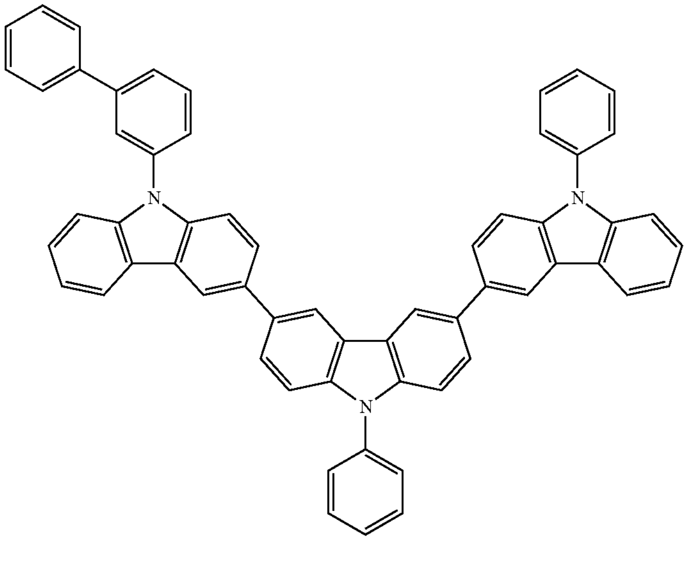 [SMILES: c1ccc(-c2cccc(-n3c4ccccc4c4cc(-c5ccc6c(c5)c5cc(-c7ccc8c(c7)c7ccccc7n8-c7ccccc7)ccc5n6-c5ccccc5)ccc43)c2)cc1]

TABLE 3-continued
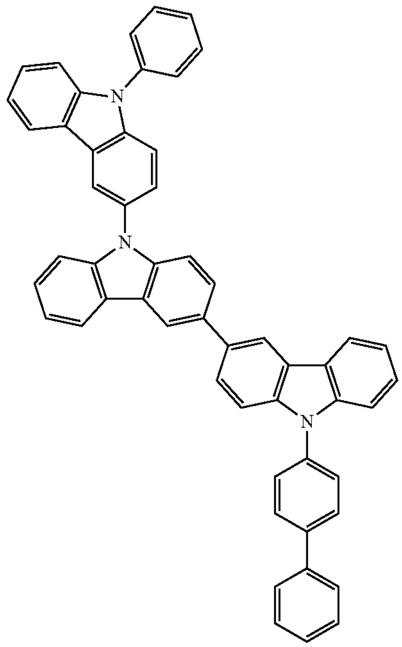 [SMILES: c1ccc(-c2ccc(-n3c4ccccc4c4cc(-c5ccc6c(c5)c5ccccc5n6-c5ccc6c(c5)c5ccccc5n6-c5ccccc5)ccc43)cc2)cc1]
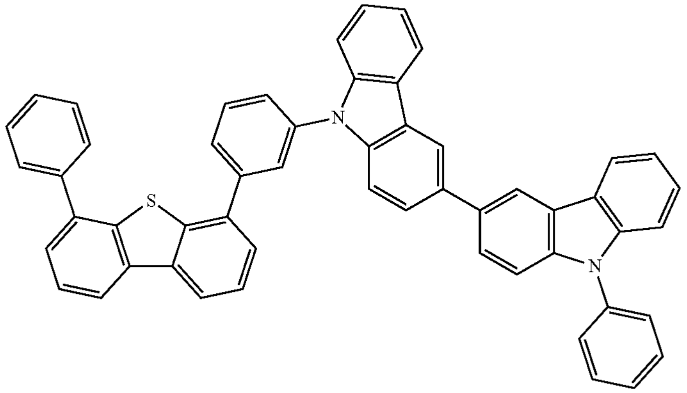

TABLE 3-continued
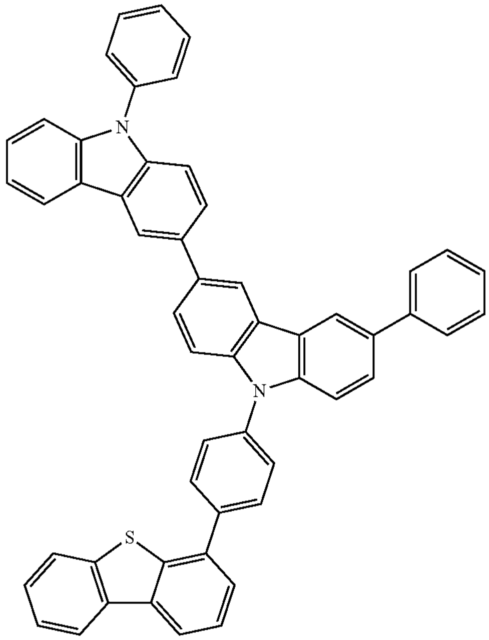 [SMILES: c1ccc(-c2ccc3c(c2)c2cc(-c4ccc5c(c4)c4ccccc4n5-c4ccccc4)ccc2n3-c2ccc(-c3cccc4c3sc3ccccc34)cc2)cc1]
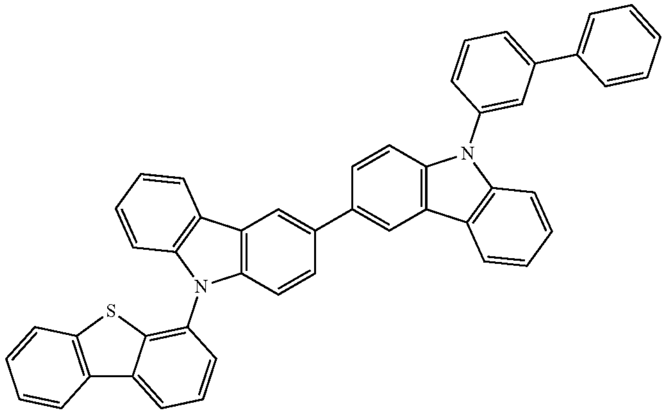 [SMILES: c1ccc(-c2cccc(-n3c4ccccc4c4cc(-c5ccc6c(c5)c5ccccc5n6-c5cccc6c5sc5ccccc56)ccc43)c2)cc1]
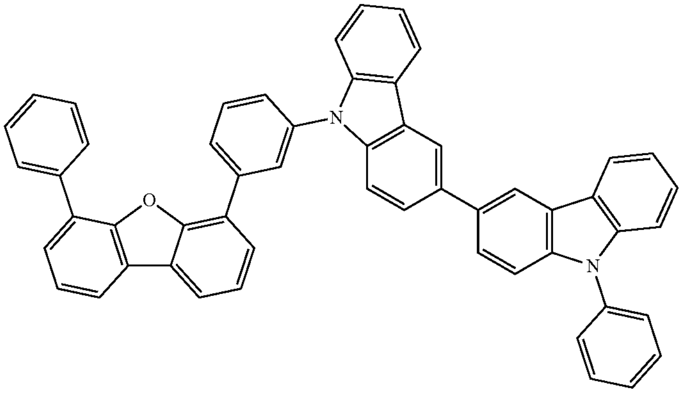

TABLE 3-continued
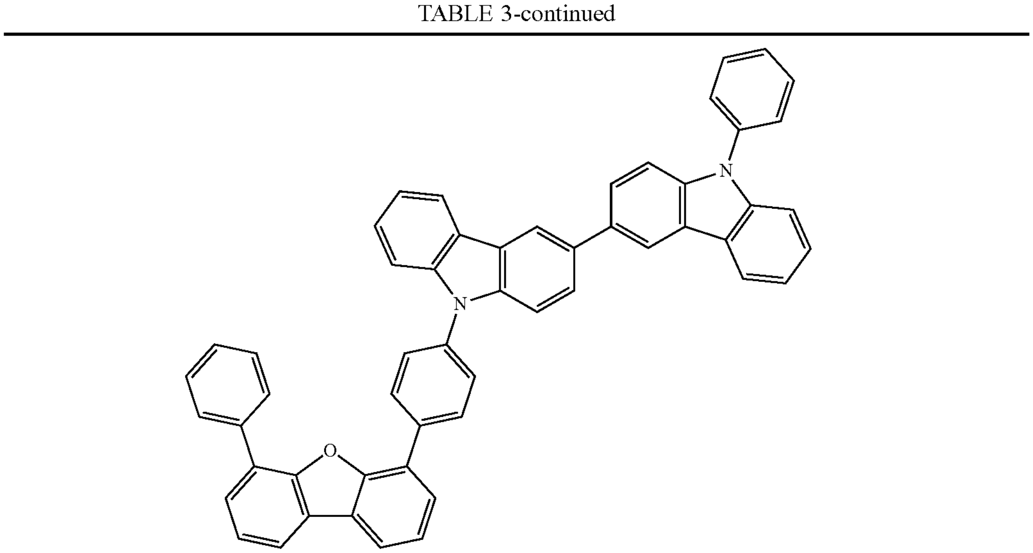
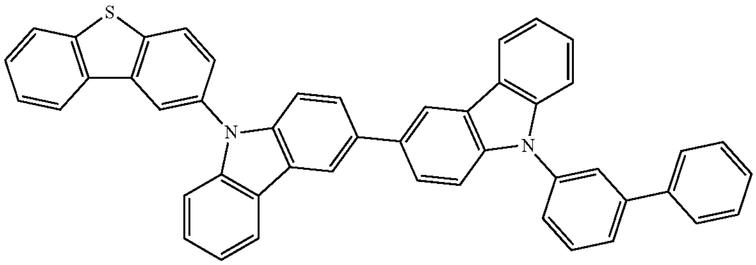
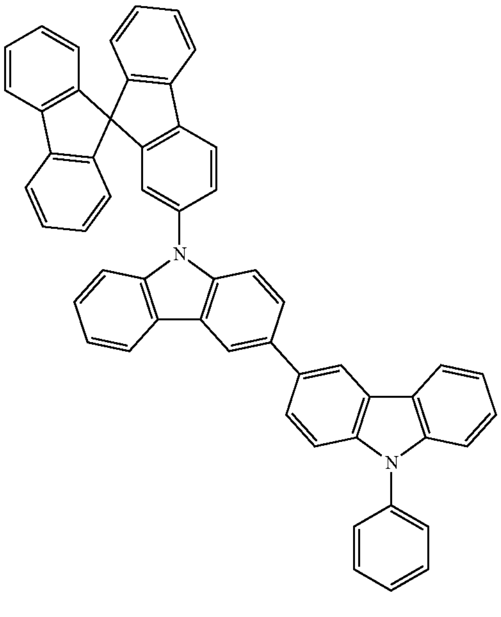 [SMILES: c1ccc(-n2c3ccccc3c3cc(-c4ccc5c(c4)c4ccccc4n5-c4ccc5c(c4)C4(c6ccccc6-c6ccccc64)c4ccccc4-5)ccc32)cc1]

TABLE 3-continued
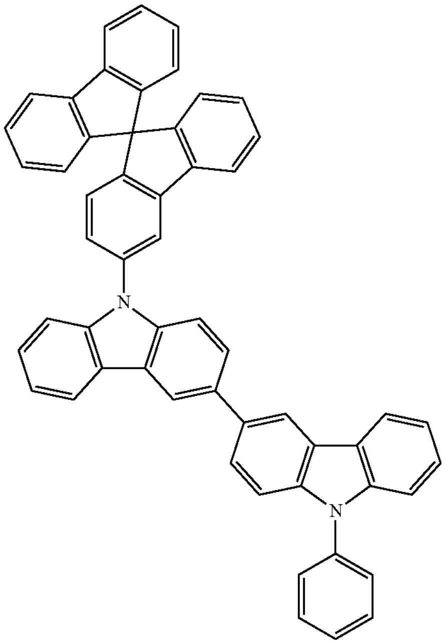 [SMILES: c1ccc(-n2c3ccccc3c3cc(-c4ccc5c(c4)c4ccccc4n5-c4ccc5c(c4)-c4ccccc4C54c5ccccc5-c5ccccc54)ccc32)cc1]
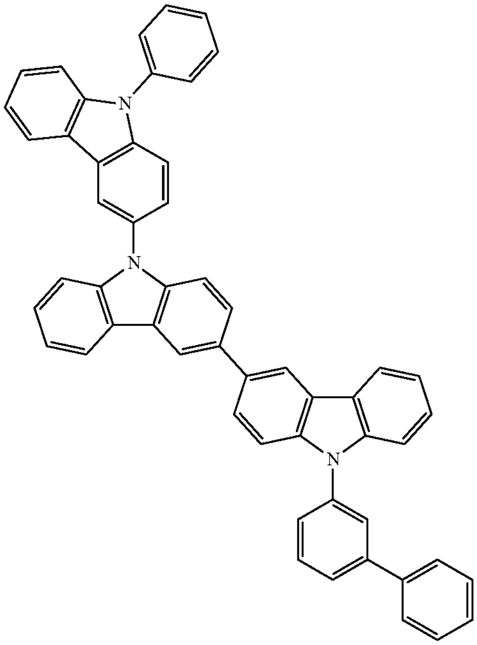 [SMILES: c1ccc(-c2cccc(-n3c4ccccc4c4cc(-c5ccc6c(c5)c5ccccc5n6-c5ccc6c(c5)c5ccccc5n6-c5ccccc5)ccc43)c2)cc1]

TABLE 3-continued
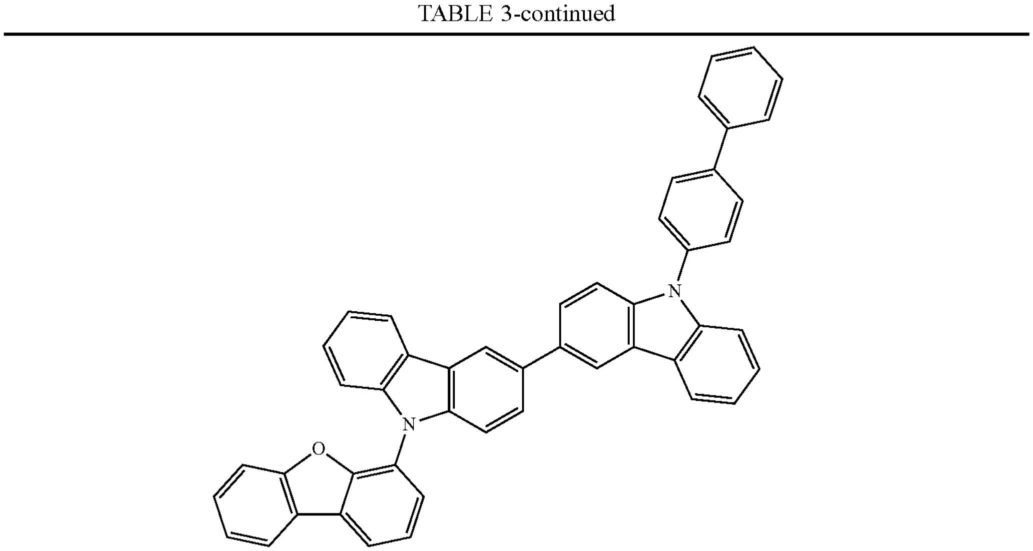
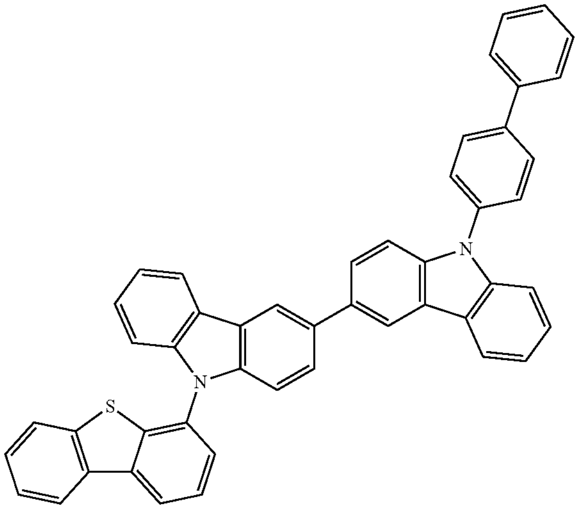 [SMILES: c1ccc(-c2ccc(-n3c4ccccc4c4cc(-c5ccc6c(c5)c5ccccc5n6-c5cccc6c5oc5ccccc56)ccc43)cc2)cc1]
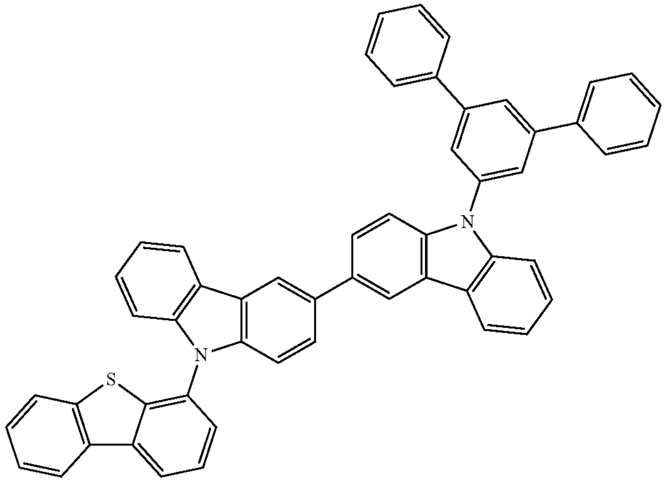

TABLE 3-continued
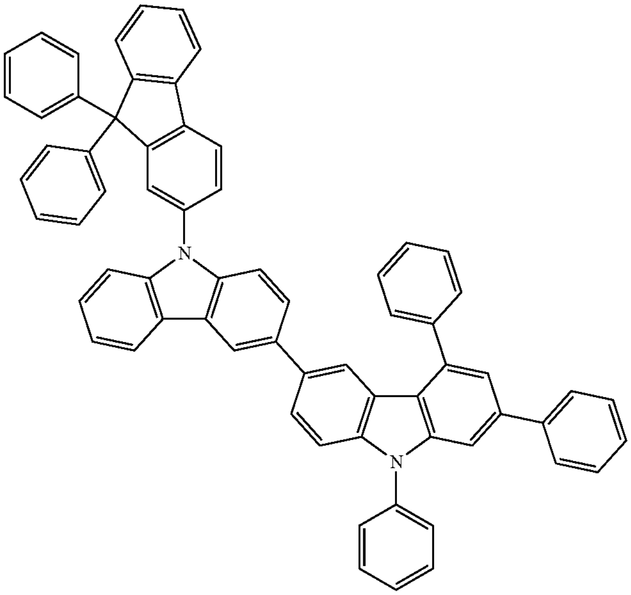 [SMILES: c1ccc(-c2cc(-c3ccccc3)c3c4cc(-c5ccc6c(c5)c5ccccc5n6-c5ccc6c(c5)C(c5ccccc5)(c5ccccc5)c5ccccc5-6)ccc4n(-c4ccccc4)c3c2)cc1]
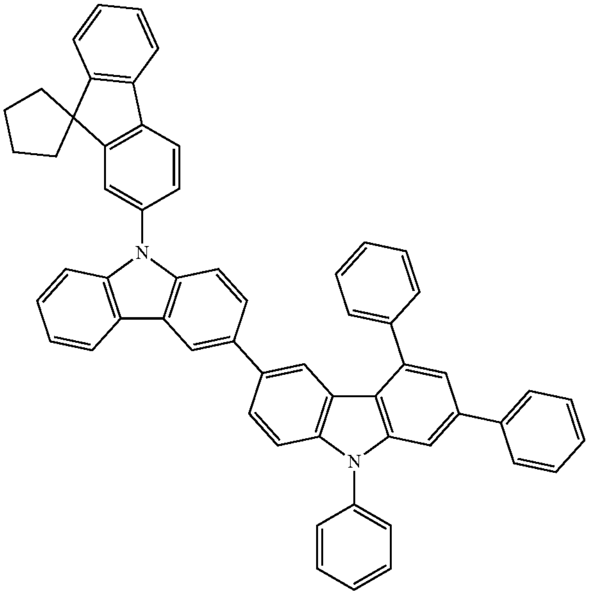 [SMILES: c1ccc(-c2cc(-c3ccccc3)c3c4cc(-c5ccc6c(c5)c5ccccc5n6-c5ccc6c(c5)C5(CCCC5)c5ccccc5-6)ccc4n(-c4ccccc4)c3c2)cc1]

TABLE 3-continued
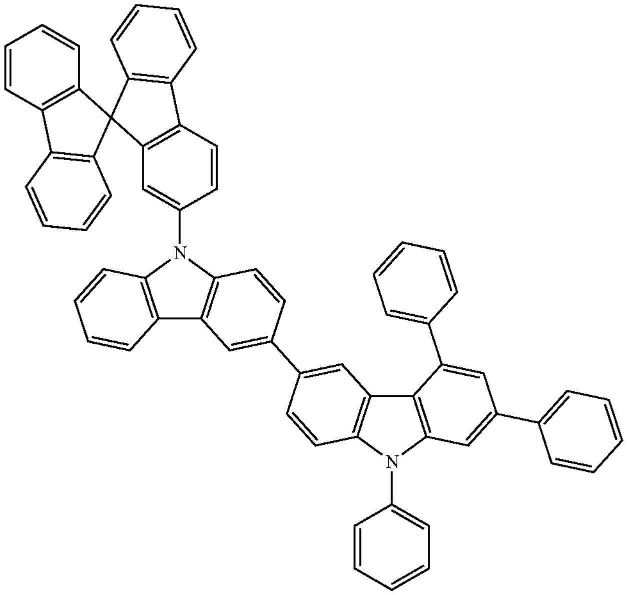 [SMILES: c1ccc(-c2cc(-c3ccccc3)c3c4cc(-c5ccc6c(c5)c5ccccc5n6-c5ccc6c(c5)C5(c7ccccc7-c7ccccc75)c5ccccc5-6)ccc4n(-c4ccccc4)c3c2)cc1]
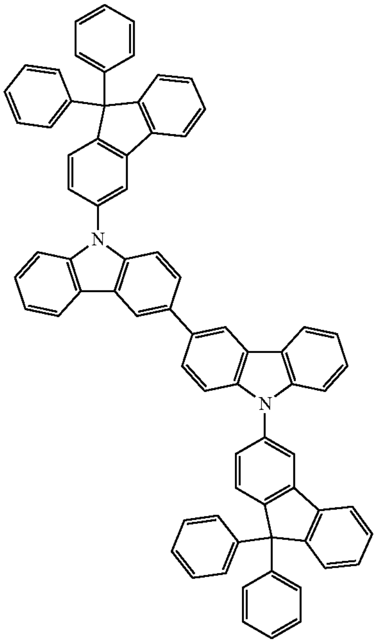 [SMILES: c1ccc(C2(c3ccccc3)c3ccccc3-c3cc(-n4c5ccccc5c5cc(-c6ccc7c(c6)c6ccccc6n7-c6ccc7c(c6)-c6ccccc6C7(c6ccccc6)c6ccccc6)ccc54)ccc32)cc1]

TABLE 3-continued
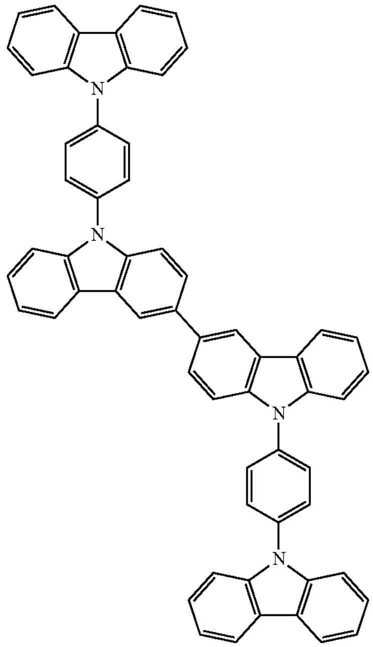 [SMILES: c1ccc2c(c1)c1ccccc1n2-c1ccc(-n2c3ccccc3c3cc(-c4ccc5c(c4)c4ccccc4n5-c4ccc(-n5c6ccccc6c6ccccc65)cc4)ccc32)cc1]
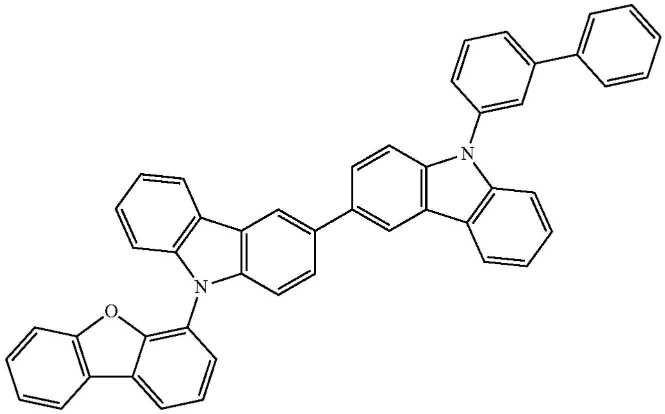
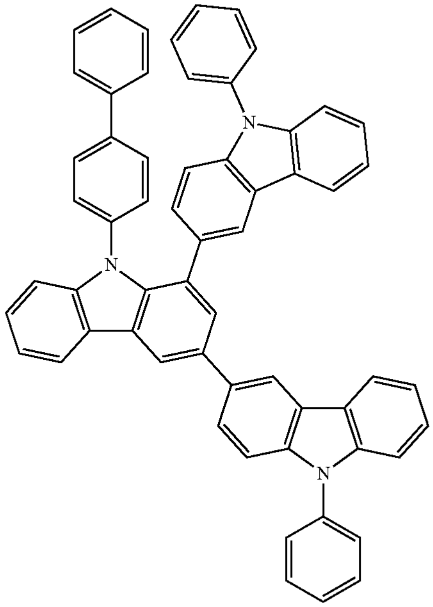 [SMILES: c1ccc(-c2ccc(-n3c4ccccc4c4cc(-c5ccc6c(c5)c5ccccc5n6-c5ccccc5)cc(-c5ccc6c(c5)c5ccccc5n6-c5ccccc5)c43)cc2)cc1]

TABLE 3-continued
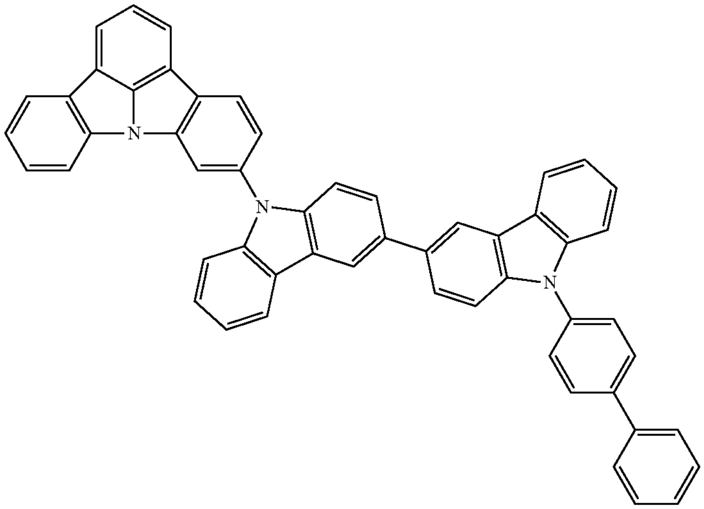 [SMILES: c1ccc(-c2ccc(-n3c4ccccc4c4cc(-c5ccc6c(c5)c5ccccc5n6-c5ccc6c7cccc8c9ccccc9n(c6c5)c87)ccc43)cc2)cc1]
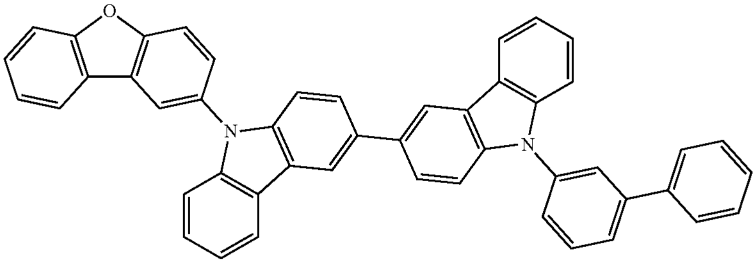
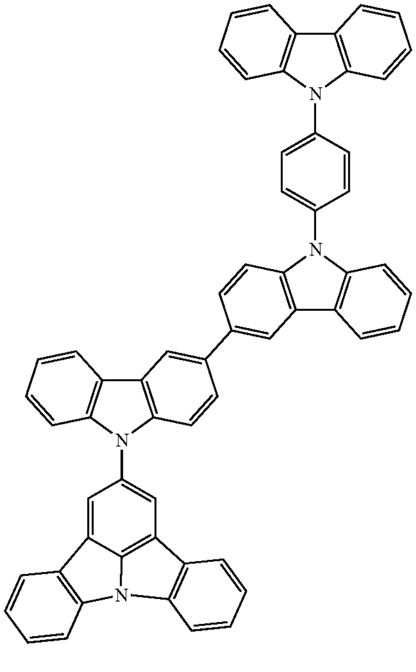 [SMILES: c1ccc2c(c1)c1ccccc1n2-c1ccc(-n2c3ccccc3c3cc(-c4ccc5c(c4)c4ccccc4n5-c4cc5c6ccccc6n6c7ccccc7c(c4)c56)ccc32)cc1]

TABLE 3-continued
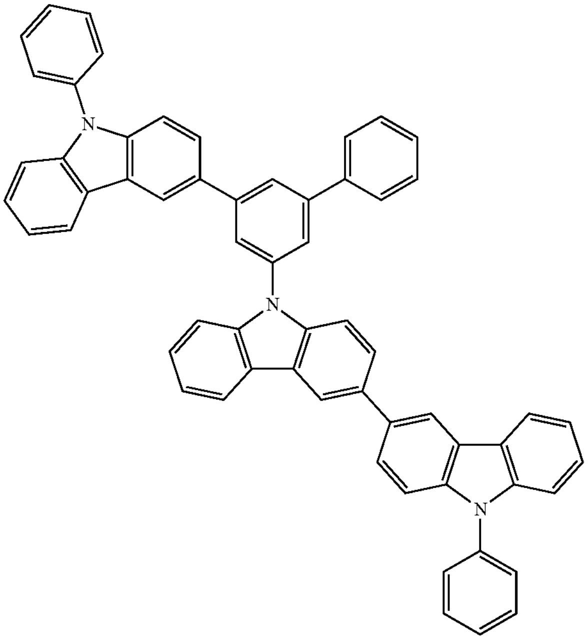 [SMILES: c1ccc(-c2cc(-c3ccc4c(c3)c3ccccc3n4-c3ccccc3)cc(-n3c4ccccc4c4cc(-c5ccc6c(c5)c5ccccc5n6-c5ccccc5)ccc43)c2)cc1]
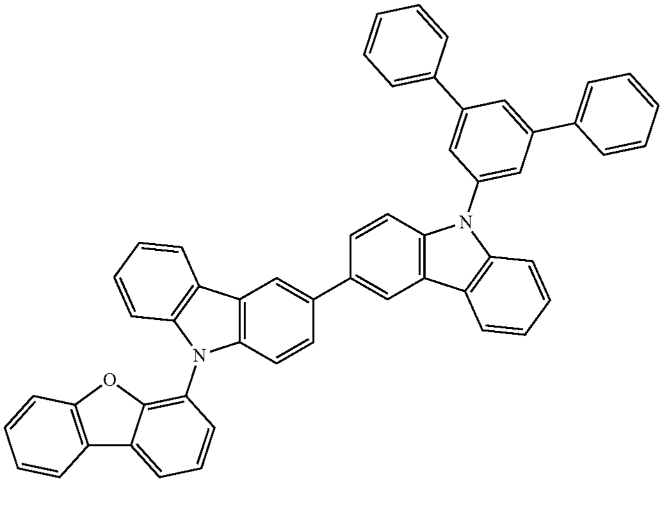 [SMILES: c1ccc(-c2cc(-c3ccccc3)cc(-n3c4ccccc4c4cc(-c5ccc6c(c5)c5ccccc5n6-c5cccc6c5oc5ccccc56)ccc43)c2)cc1]

TABLE 3-continued
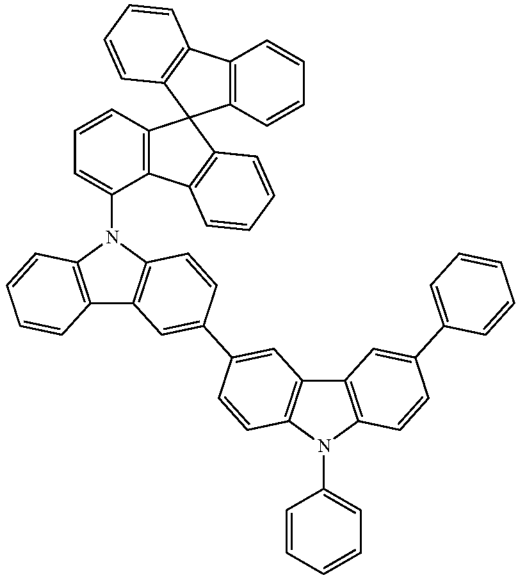 [SMILES: c1ccc(-c2ccc3c(c2)c2cc(-c4ccc5c(c4)c4ccccc4n5-c4cccc5c4-c4ccccc4C54c5ccccc5-c5ccccc54)ccc2n3-c2ccccc2)cc1]
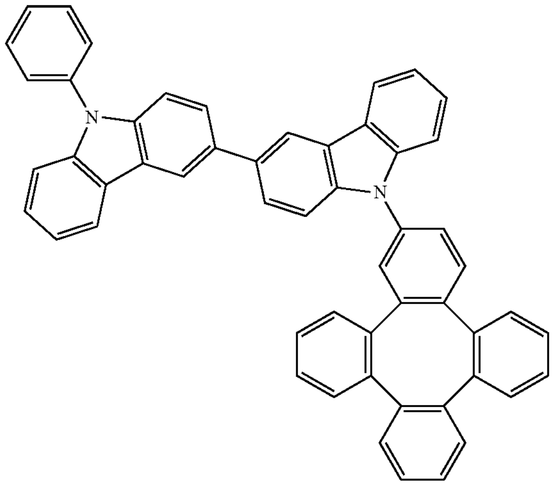 [SMILES: c1ccc(-n2c3ccccc3c3cc(-c4ccc5c(c4)c4ccccc4n5-c4ccc5c(c4)-c4ccccc4-c4ccccc4-c4ccccc4-5)ccc32)cc1]
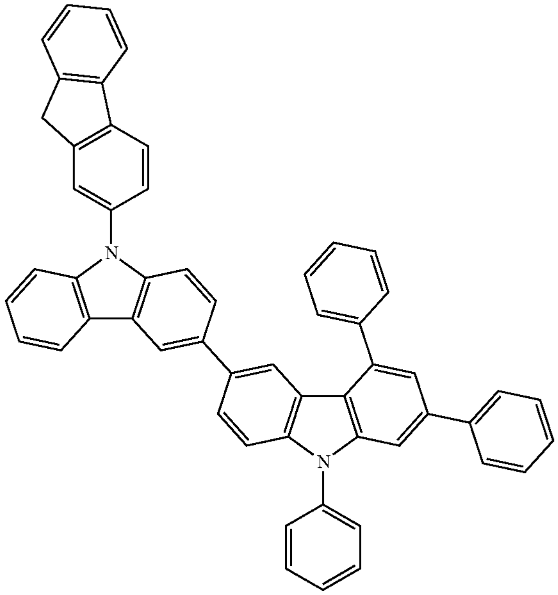 [SMILES: c1ccc(-c2cc(-c3ccccc3)c3c4cc(-c5ccc6c(c5)c5ccccc5n6-c5ccc6c(c5)Cc5ccccc5-6)ccc4n(-c4ccccc4)c3c2)cc1]

TABLE 3-continued
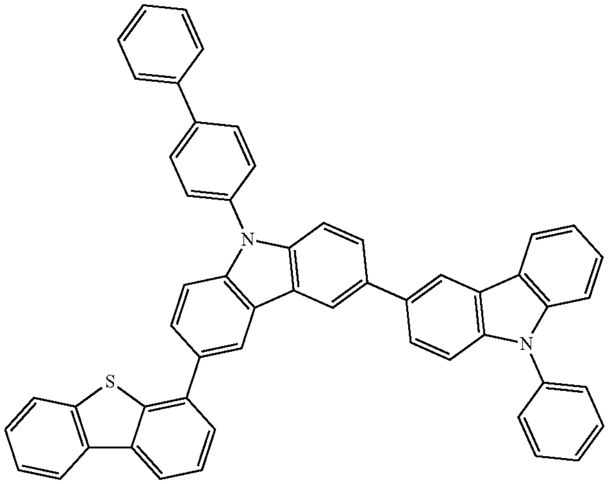
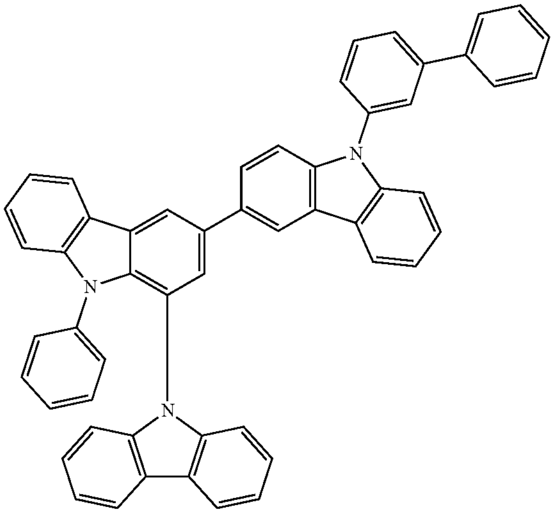 [SMILES: c1ccc(-c2cccc(-n3c4ccccc4c4cc(-c5cc(-n6c7ccccc7c7ccccc76)c6c(c5)c5ccccc5n6-c5ccccc5)ccc43)c2)cc1]
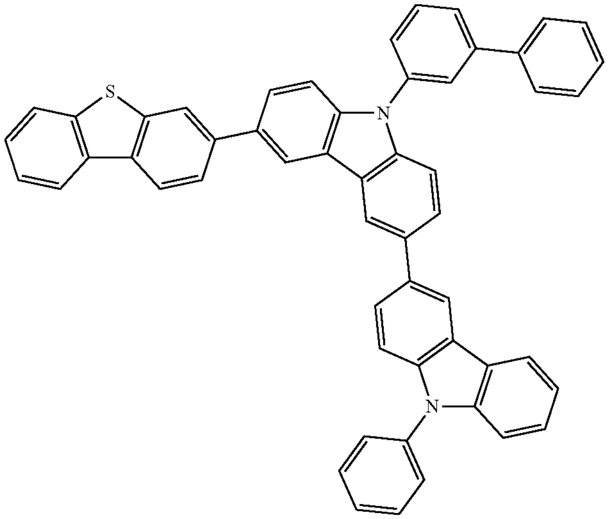 [SMILES: c1ccc(-c2cccc(-n3c4ccc(-c5ccc6c(c5)sc5ccccc56)cc4c4cc(-c5ccc6c(c5)c5ccccc5n6-c5ccccc5)ccc43)c2)cc1]

TABLE 3-continued
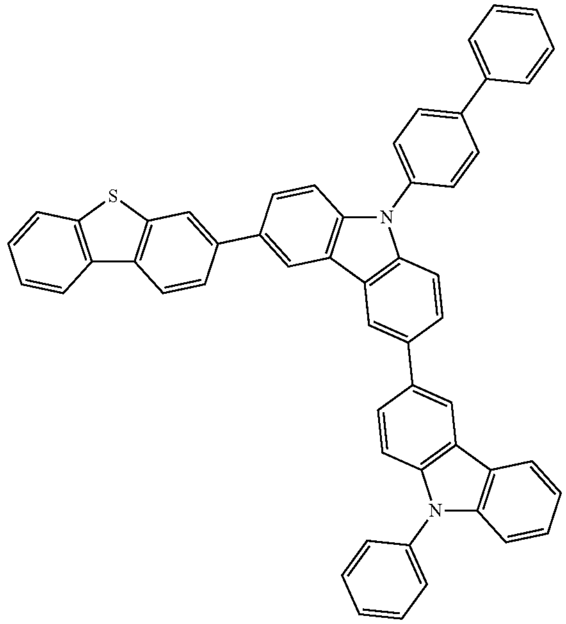
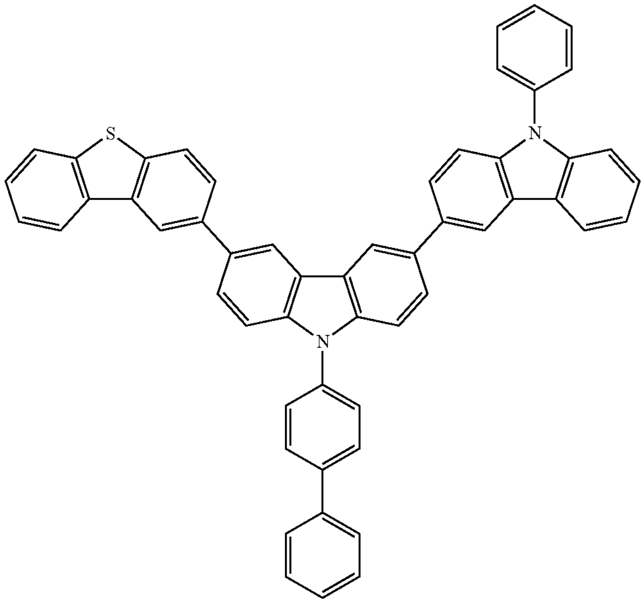 [SMILES: c1ccc(-c2ccc(-n3c4ccc(-c5ccc6sc7ccccc7c6c5)cc4c4cc(-c5ccc6c(c5)c5ccccc5n6-c5ccccc5)ccc43)cc2)cc1]
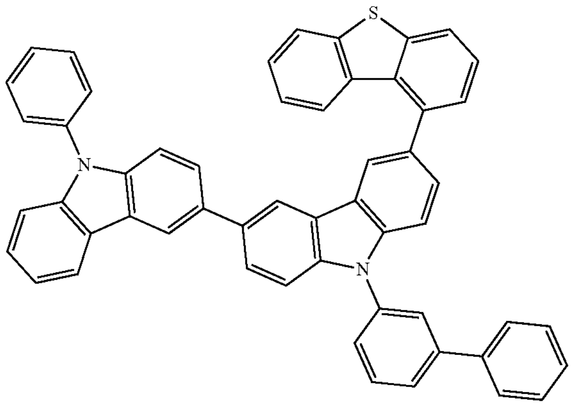 [SMILES: c1ccc(-c2cccc(-n3c4ccc(-c5ccc6c(c5)c5ccccc5n6-c5ccccc5)cc4c4cc(-c5cccc6sc7ccccc7c56)ccc43)c2)cc1]

TABLE 3-continued
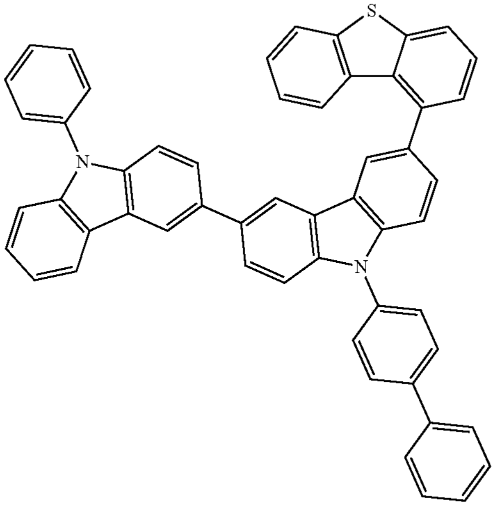 [SMILES: c1ccc(-c2ccc(-n3c4ccc(-c5ccc6c(c5)c5ccccc5n6-c5ccccc5)cc4c4cc(-c5cccc6sc7ccccc7c56)ccc43)cc2)cc1]
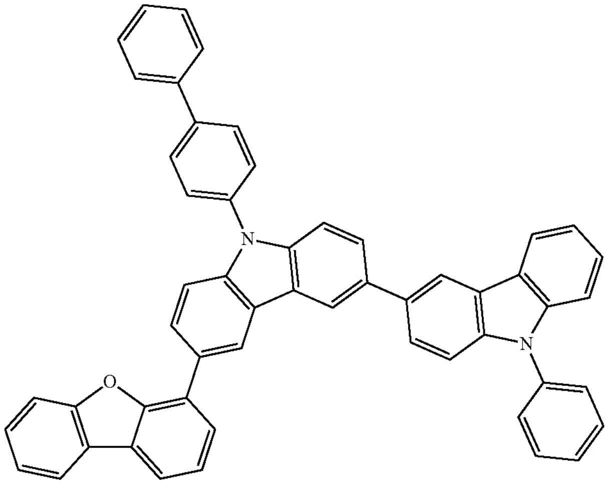 [SMILES: c1ccc(-c2ccc(-n3c4ccc(-c5ccc6c(c5)c5ccccc5n6-c5ccccc5)cc4c4cc(-c5cccc6c5oc5ccccc56)ccc43)cc2)cc1]
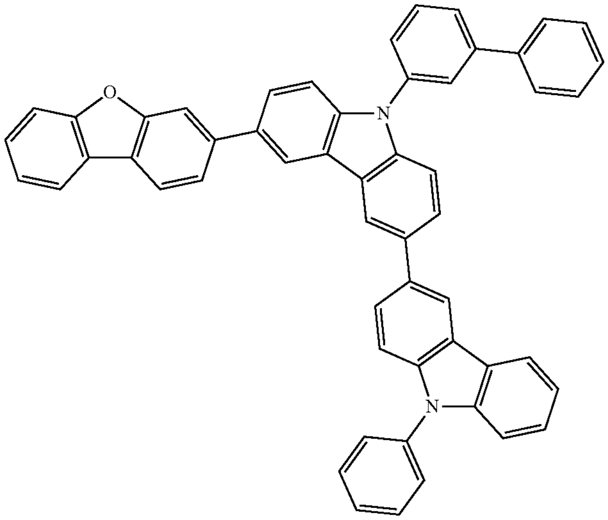

TABLE 3-continued
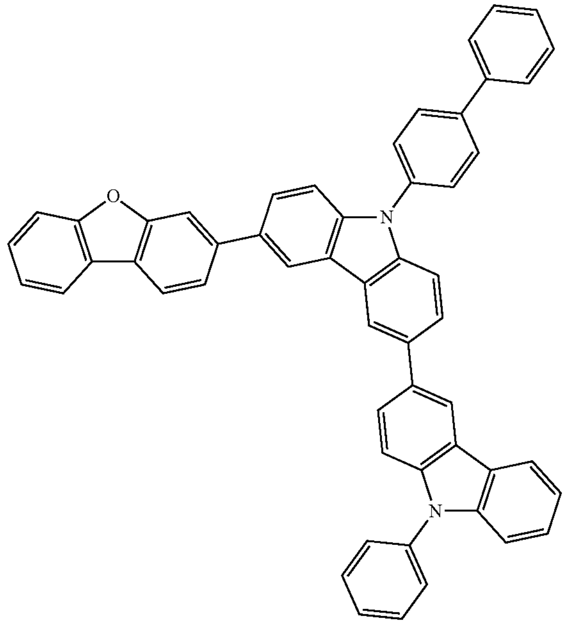 [SMILES: c1ccc(-c2ccc(-n3c4ccc(-c5ccc6c(c5)oc5ccccc56)cc4c4cc(-c5ccc6c(c5)c5ccccc5n6-c5ccccc5)ccc43)cc2)cc1]
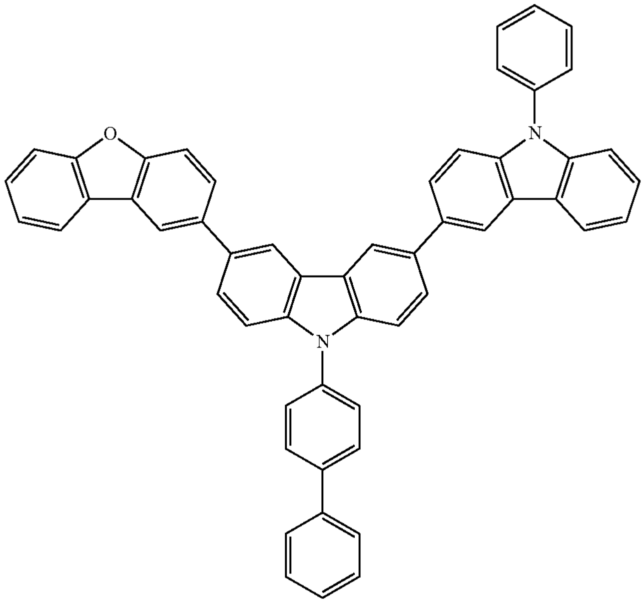 [SMILES: c1ccc(-c2ccc(-n3c4ccc(-c5ccc6oc7ccccc7c6c5)cc4c4cc(-c5ccc6c(c5)c5ccccc5n6-c5ccccc5)ccc43)cc2)cc1]
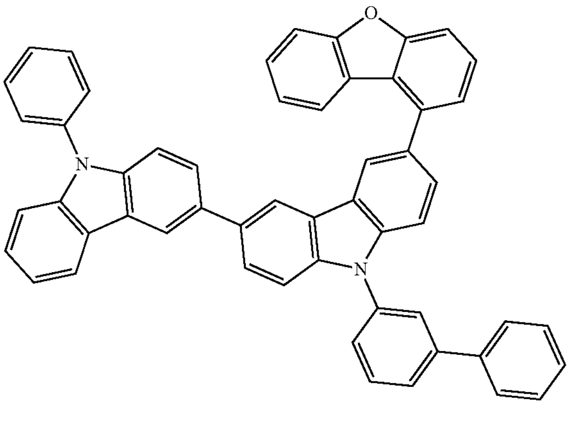 [SMILES: c1ccc(-c2cccc(-n3c4ccc(-c5ccc6c(c5)c5ccccc5n6-c5ccccc5)cc4c4cc(-c5cccc6oc7ccccc7c56)ccc43)c2)cc1]

TABLE 3-continued
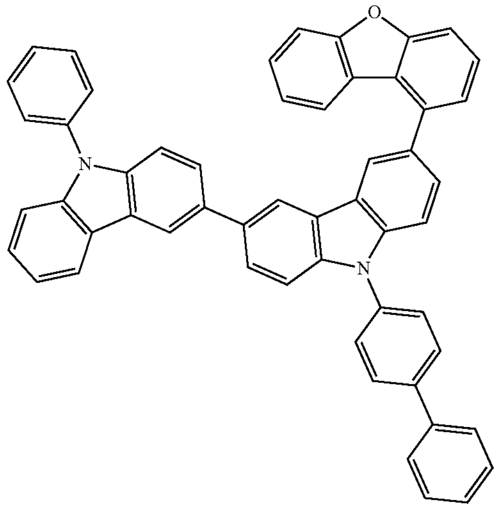
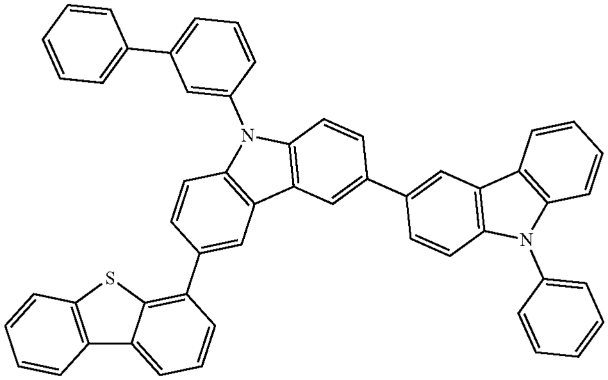
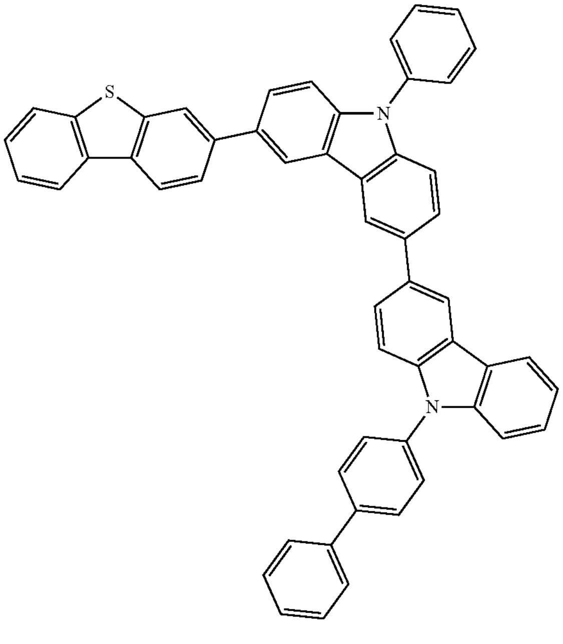 [SMILES: c1ccc(-c2ccc(-n3c4ccccc4c4cc(-c5ccc6c(c5)c5cc(-c7ccc8c(c7)sc7ccccc78)ccc5n6-c5ccccc5)ccc43)cc2)cc1]

TABLE 3-continued
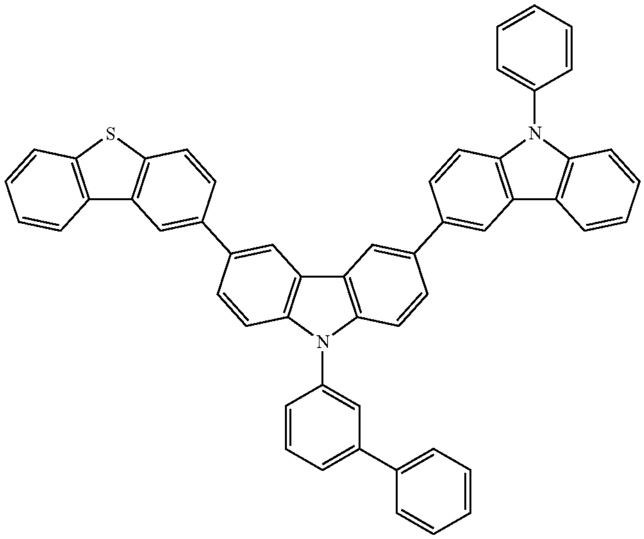 [SMILES: c1ccc(-c2cccc(-n3c4ccc(-c5ccc6sc7ccccc7c6c5)cc4c4cc(-c5ccc6c(c5)c5ccccc5n6-c5ccccc5)ccc43)c2)cc1]
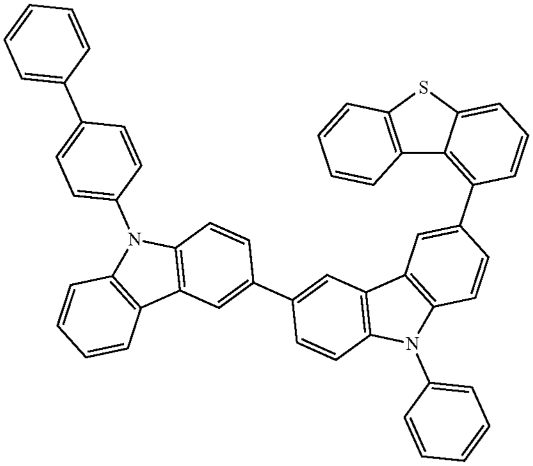 [SMILES: c1ccc(-c2ccc(-n3c4ccccc4c4cc(-c5ccc6c(c5)c5cc(-c7cccc8sc9ccccc9c78)ccc5n6-c5ccccc5)ccc43)cc2)cc1]
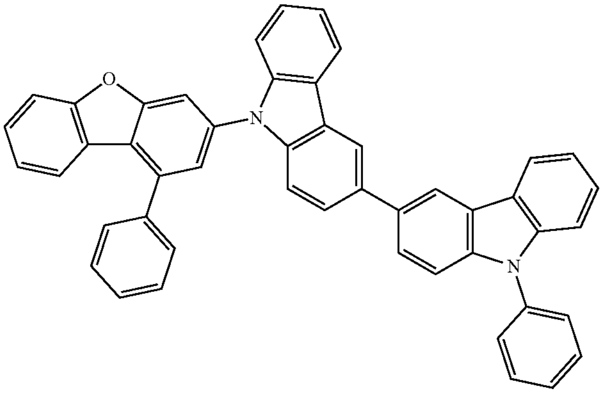 [SMILES: c1ccc(-c2cc(-n3c4ccccc4c4cc(-c5ccc6c(c5)c5ccccc5n6-c5ccccc5)ccc43)cc3oc4ccccc4c23)cc1]

TABLE 3-continued
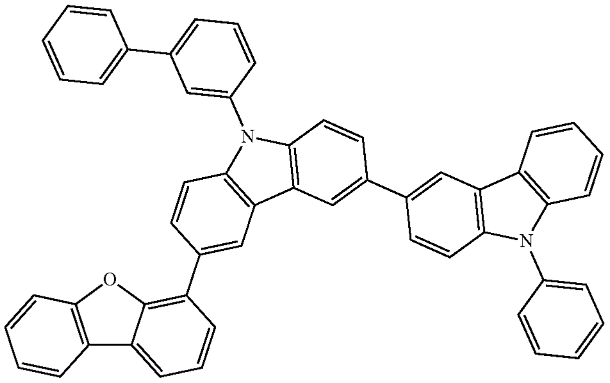 [SMILES: c1ccc(-c2cccc(-n3c4ccc(-c5ccc6c(c5)c5ccccc5n6-c5ccccc5)cc4c4cc(-c5cccc6c5oc5ccccc56)ccc43)c2)cc1]
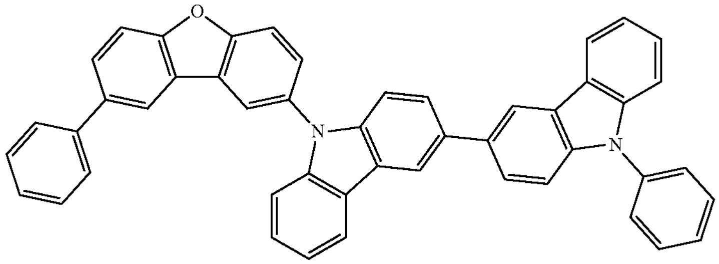 [SMILES: c1ccc(-c2ccc3oc4ccc(-n5c6ccccc6c6cc(-c7ccc8c(c7)c7ccccc7n8-c7ccccc7)ccc65)cc4c3c2)cc1]
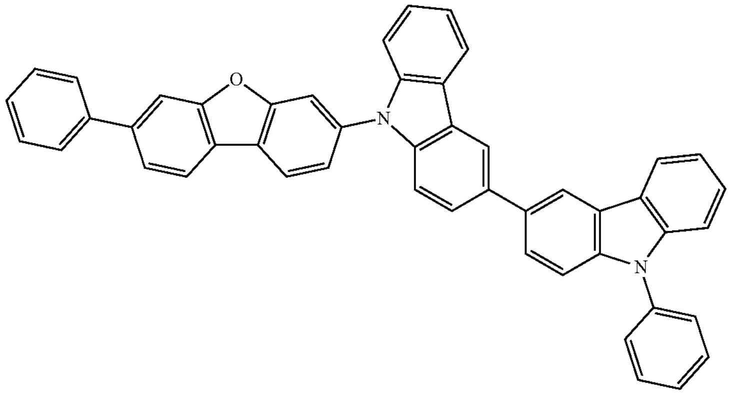 [SMILES: c1ccc(-c2ccc3c(c2)oc2cc(-n4c5ccccc5c5cc(-c6ccc7c(c6)c6ccccc6n7-c6ccccc6)ccc54)ccc23)cc1]
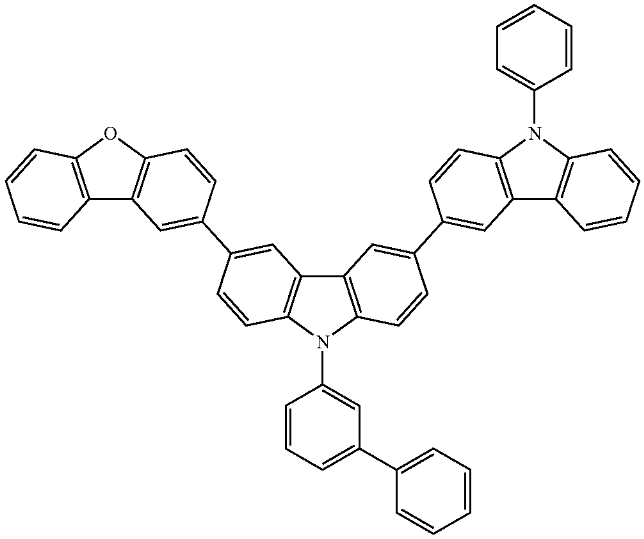

TABLE 3-continued
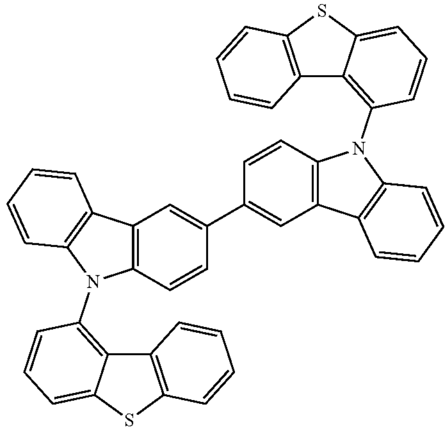 [SMILES: c1ccc2c(c1)sc1cccc(-n3c4ccccc4c4cc(-c5ccc6c(c5)c5ccccc5n6-c5cccc6sc7ccccc7c56)ccc43)c12]
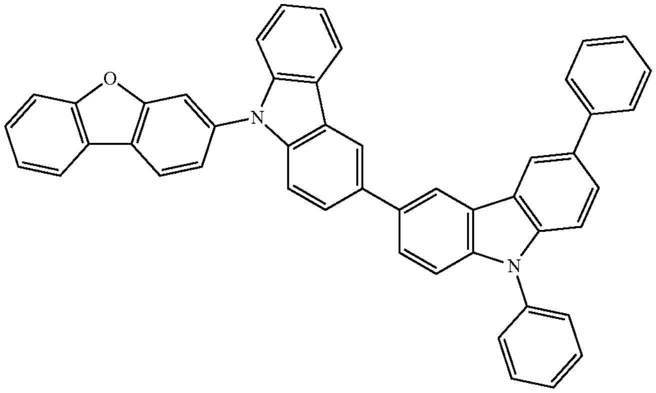 [SMILES: c1ccc(-c2ccc3c(c2)c2cc(-c4ccc5c(c4)c4ccccc4n5-c4ccc5c(c4)oc4ccccc45)ccc2n3-c2ccccc2)cc1]
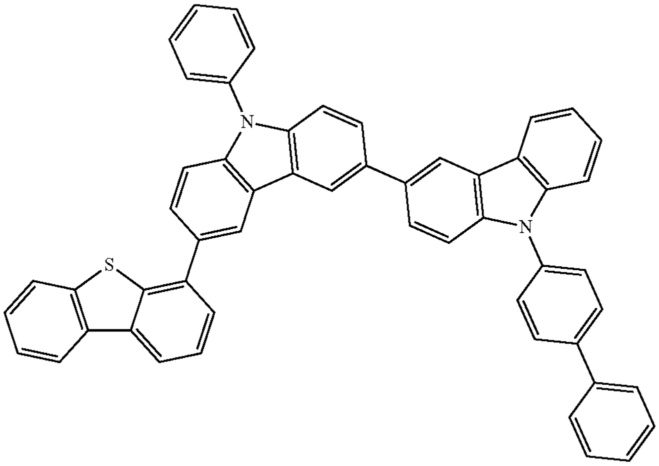 [SMILES: c1ccc(-c2ccc(-n3c4ccccc4c4cc(-c5ccc6c(c5)c5cc(-c7cccc8c7sc7ccccc78)ccc5n6-c5ccccc5)ccc43)cc2)cc1]

TABLE 3-continued
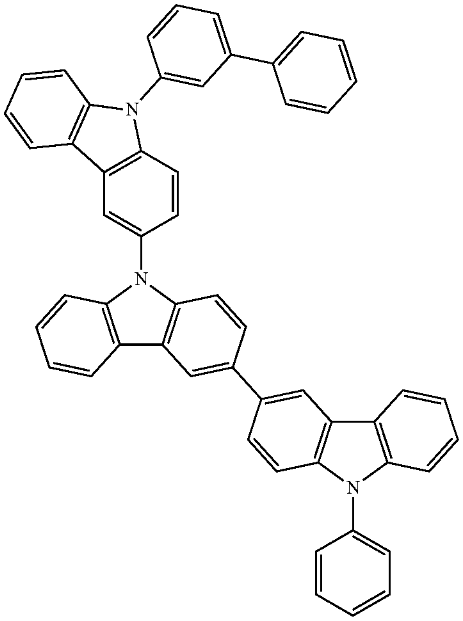 [SMILES: c1ccc(-c2cccc(-n3c4ccccc4c4cc(-n5c6ccccc6c6cc(-c7ccc8c(c7)c7ccccc7n8-c7ccccc7)ccc65)ccc43)c2)cc1]
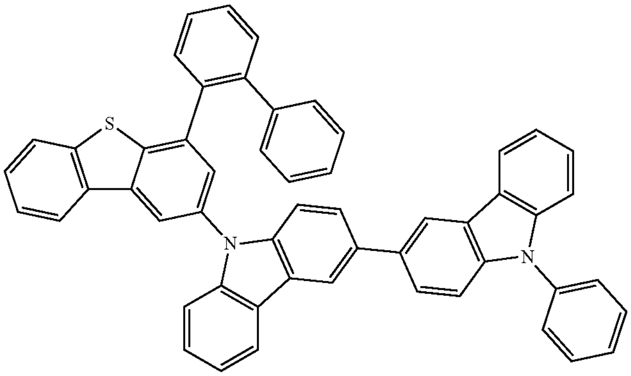 [SMILES: c1ccc(-c2ccccc2-c2cc(-n3c4ccccc4c4cc(-c5ccc6c(c5)c5ccccc5n6-c5ccccc5)ccc43)cc3c2sc2ccccc23)cc1]
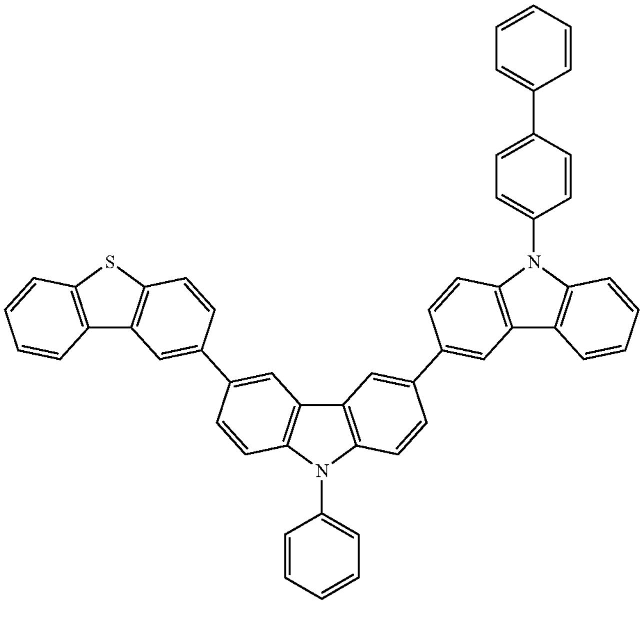

TABLE 3-continued
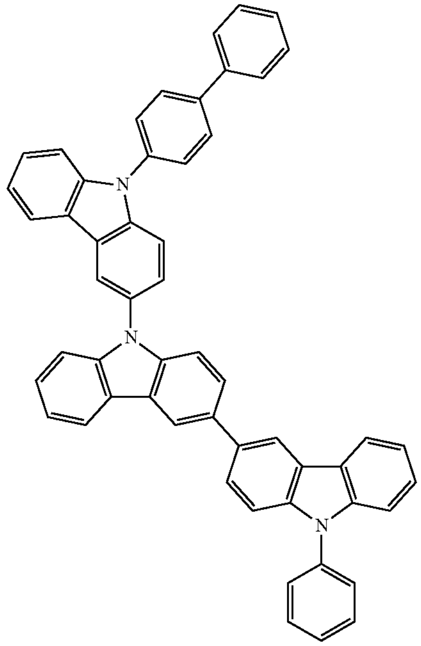 [SMILES: c1ccc(-c2ccc(-n3c4ccccc4c4cc(-n5c6ccccc6c6cc(-c7ccc8c(c7)c7ccccc7n8-c7ccccc7)ccc65)ccc43)cc2)cc1]
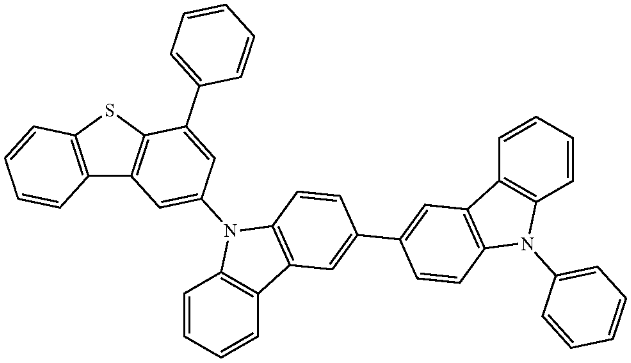
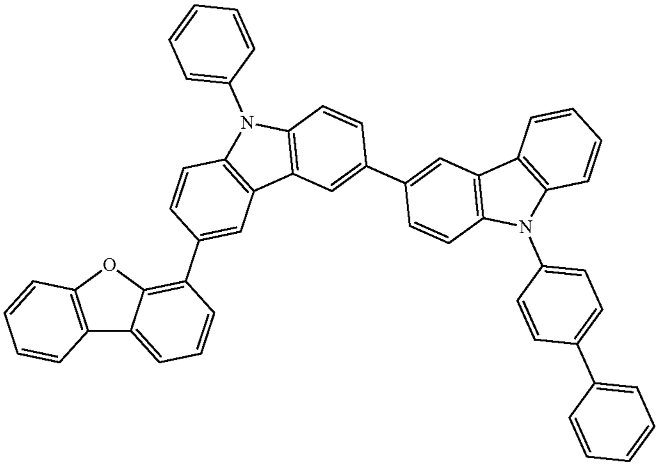 [SMILES: c1ccc(-c2ccc(-n3c4ccccc4c4cc(-c5ccc6c(c5)c5cc(-c7cccc8c7oc7ccccc78)ccc5n6-c5ccccc5)ccc43)cc2)cc1]

TABLE 3-continued
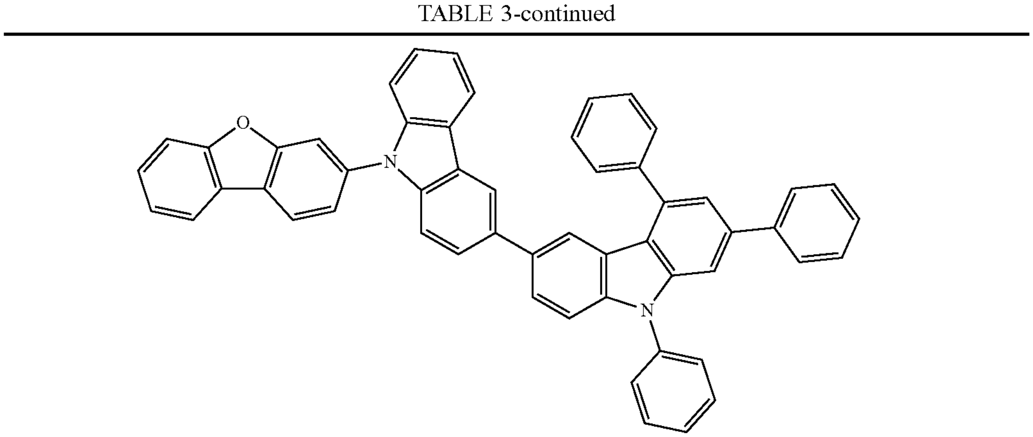
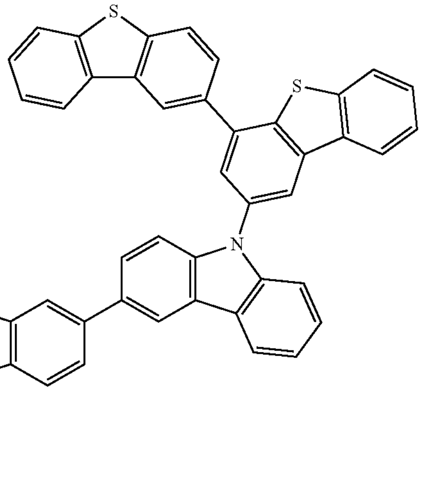
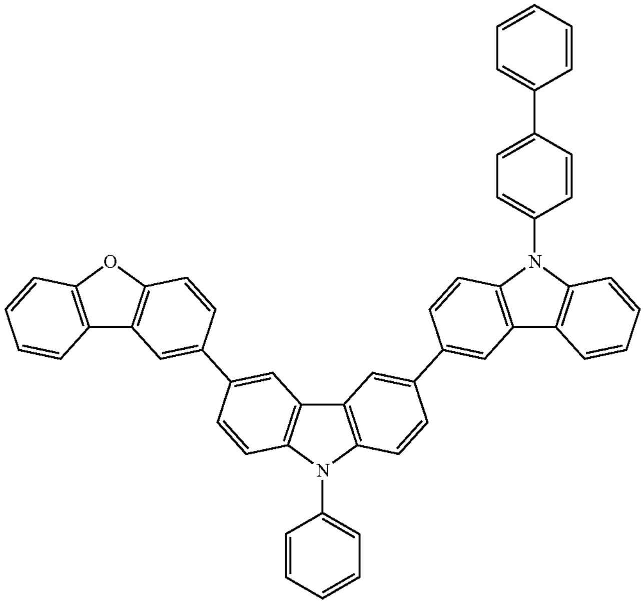 [SMILES: c1ccc(-c2ccc(-n3c4ccccc4c4cc(-c5ccc6c(c5)c5cc(-c7ccc8oc9ccccc9c8c7)ccc5n6-c5ccccc5)ccc43)cc2)cc1]

TABLE 3-continued
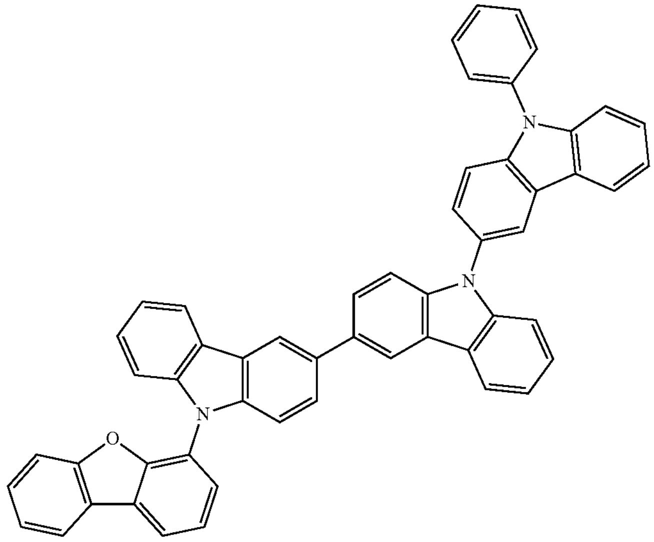 [SMILES: c1ccc(-n2c3ccccc3c3cc(-n4c5ccccc5c5cc(-c6ccc7c(c6)c6ccccc6n7-c6cccc7c6oc6ccccc67)ccc54)ccc32)cc1]
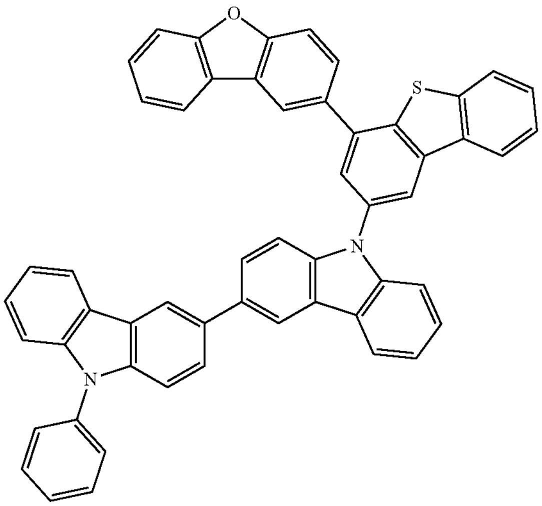 [SMILES: c1ccc(-n2c3ccccc3c3cc(-c4ccc5c(c4)c4ccccc4n5-c4cc(-c5ccc6oc7ccccc7c6c5)c5sc6ccccc6c5c4)ccc32)cc1]
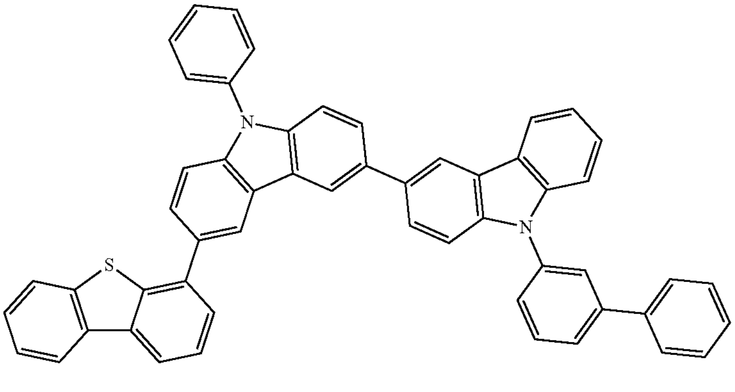

TABLE 3-continued
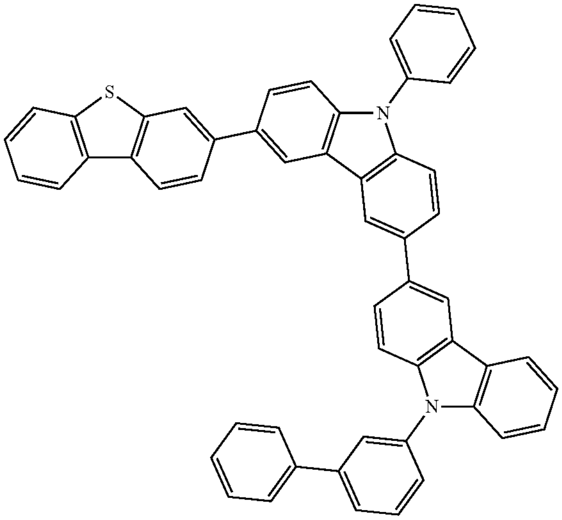 [SMILES: c1ccc(-c2cccc(-n3c4ccccc4c4cc(-c5ccc6c(c5)c5cc(-c7ccc8c(c7)sc7ccccc78)ccc5n6-c5ccccc5)ccc43)c2)cc1]
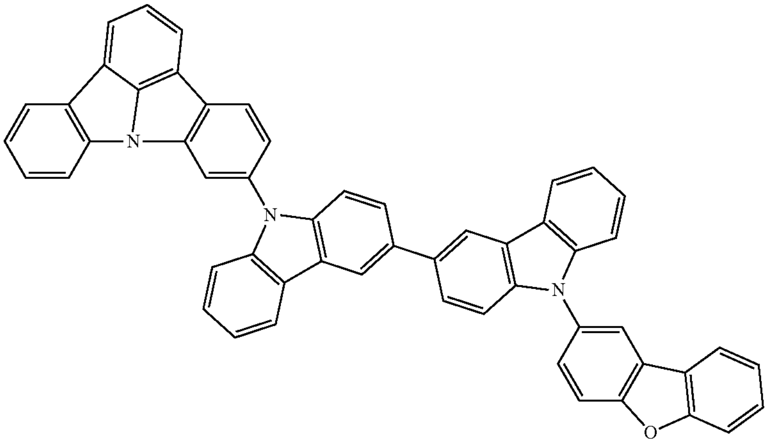 [SMILES: c1ccc2c(c1)oc1ccc(-n3c4ccccc4c4cc(-c5ccc6c(c5)c5ccccc5n6-c5ccc6c7cccc8c9ccccc9n(c6c5)c87)ccc43)cc12]
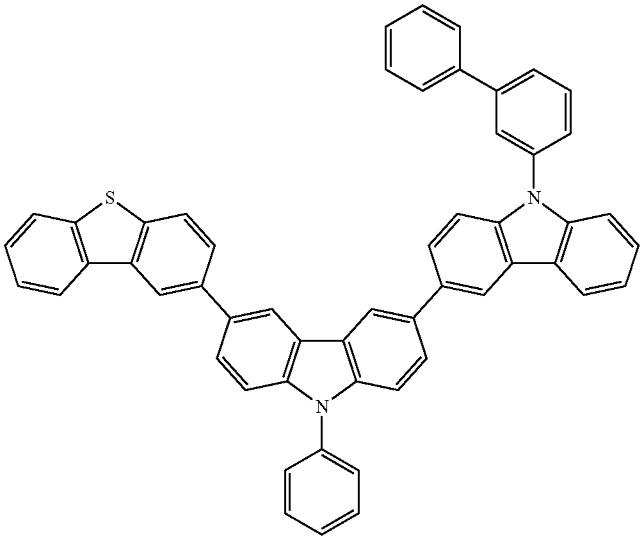 [SMILES: c1ccc(-c2cccc(-n3c4ccccc4c4cc(-c5ccc6c(c5)c5cc(-c7ccc8sc9ccccc9c8c7)ccc5n6-c5ccccc5)ccc43)c2)cc1]

TABLE 3-continued
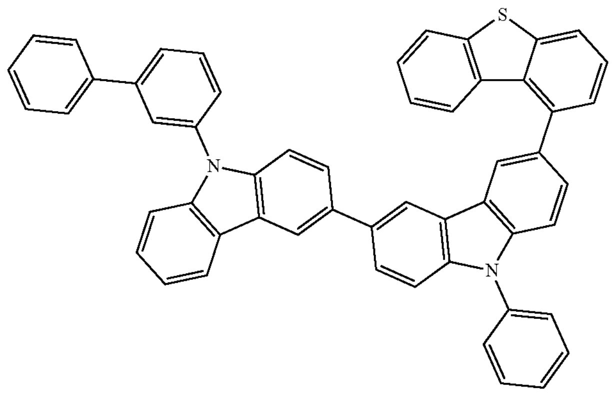 [SMILES: c1ccc(-c2cccc(-n3c4ccccc4c4cc(-c5ccc6c(c5)c5cc(-c7cccc8sc9ccccc9c78)ccc5n6-c5ccccc5)ccc43)c2)cc1]
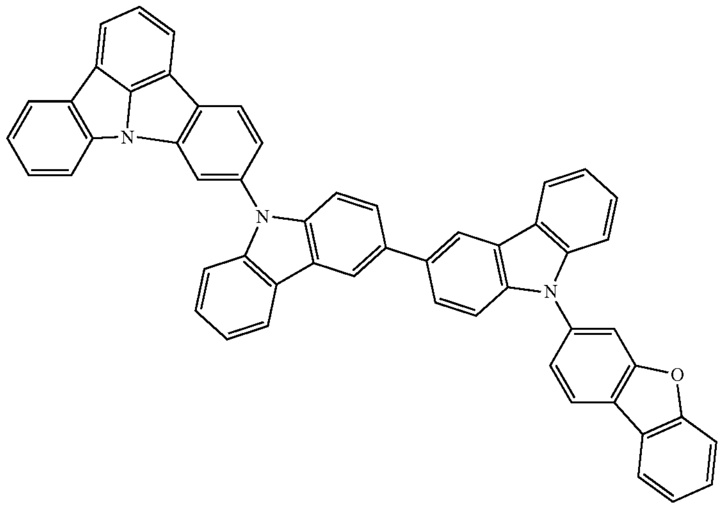 [SMILES: c1ccc2c(c1)oc1cc(-n3c4ccccc4c4cc(-c5ccc6c(c5)c5ccccc5n6-c5ccc6c7cccc8c9ccccc9n(c6c5)c87)ccc43)ccc12]
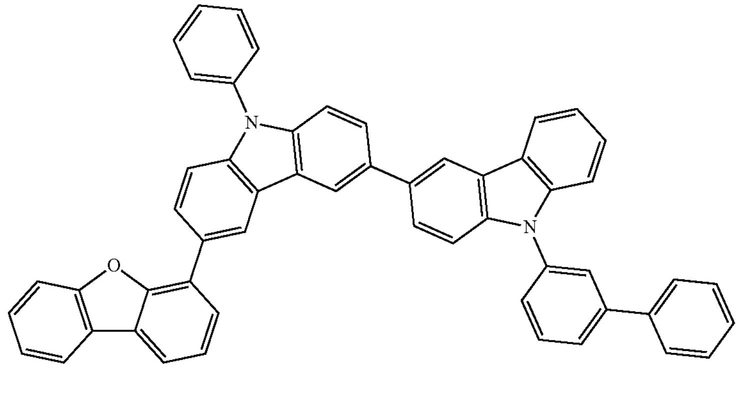

TABLE 3-continued
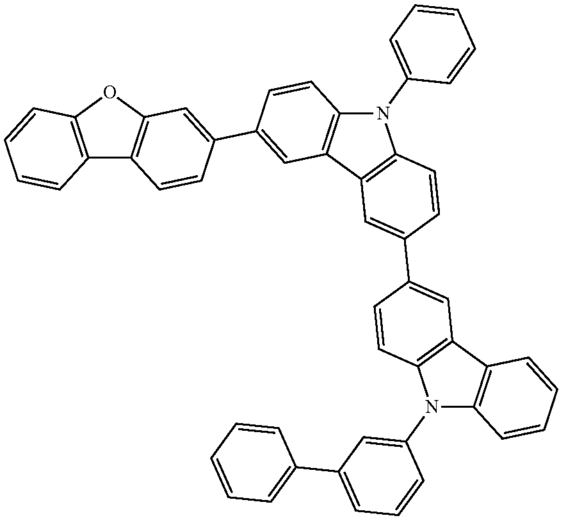 [SMILES: c1ccc(-c2cccc(-n3c4ccccc4c4cc(-c5ccc6c(c5)c5cc(-c7ccc8c(c7)oc7ccccc78)ccc5n6-c5ccccc5)ccc43)c2)cc1]
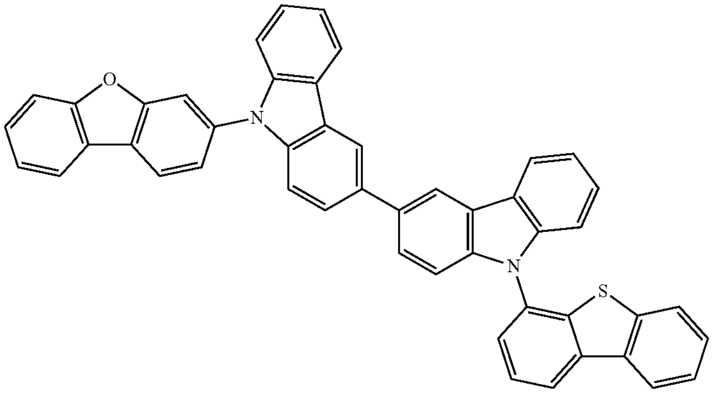 [SMILES: c1ccc2c(c1)oc1cc(-n3c4ccccc4c4cc(-c5ccc6c(c5)c5ccccc5n6-c5cccc6c5sc5ccccc56)ccc43)ccc12]
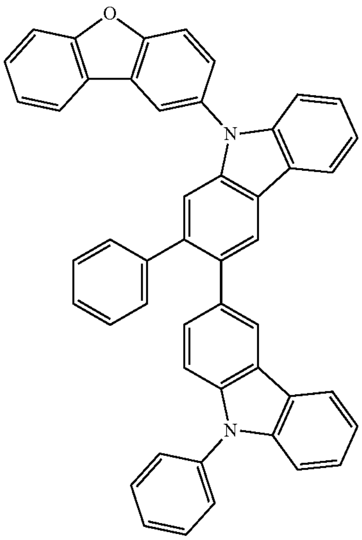 [SMILES: c1ccc(-c2cc3c(cc2-c2ccc4c(c2)c2ccccc2n4-c2ccccc2)c2ccccc2n3-c2ccc3oc4ccccc4c3c2)cc1]

TABLE 3-continued
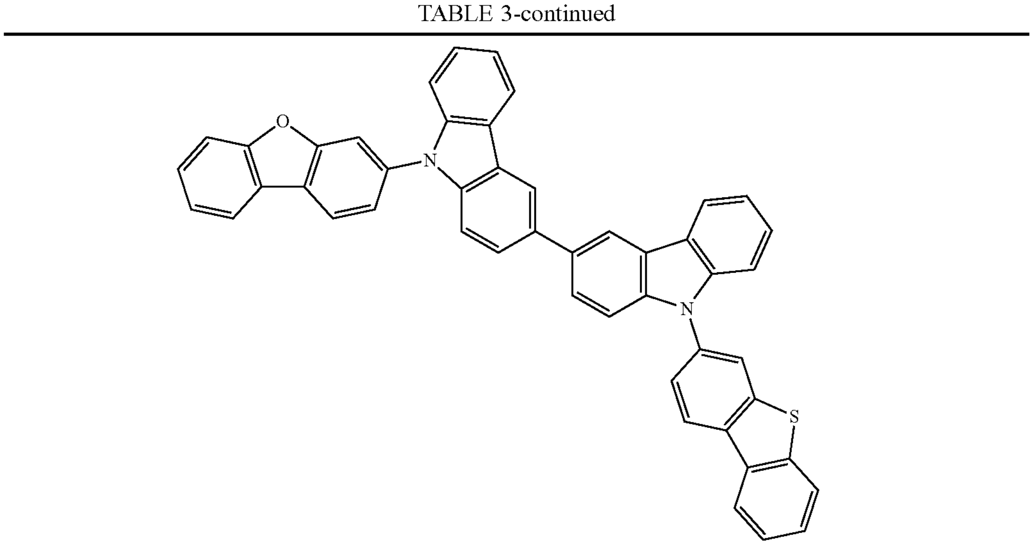
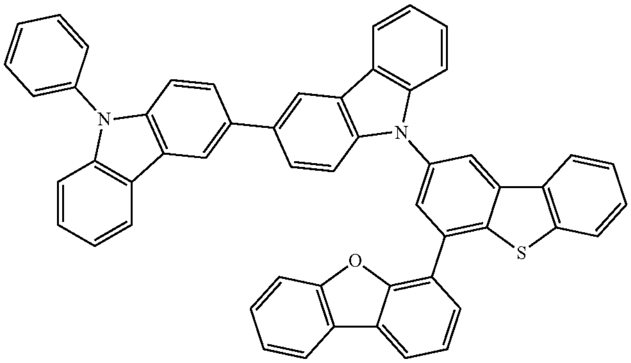
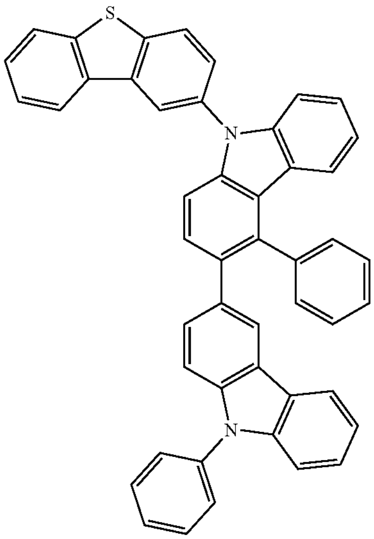 [SMILES: c1ccc(-c2c(-c3ccc4c(c3)c3ccccc3n4-c3ccccc3)ccc3c2c2ccccc2n3-c2ccc3sc4ccccc4c3c2)cc1]

TABLE 3-continued
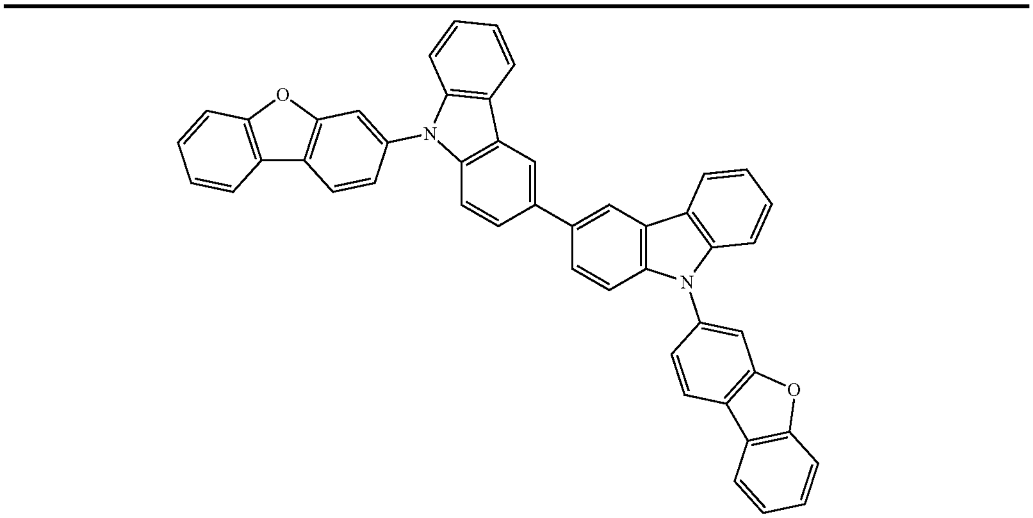
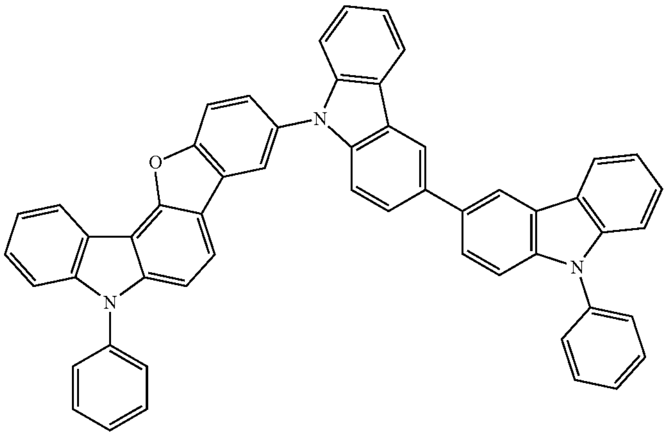 [SMILES: c1ccc(-n2c3ccccc3c3cc(-c4ccc5c(c4)c4ccccc4n5-c4ccc5oc6c(ccc7c6c6ccccc6n7-c6ccccc6)c5c4)ccc32)cc1]
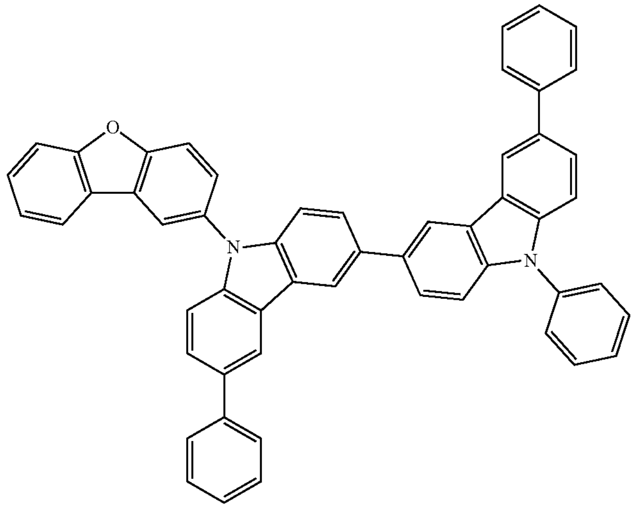 [SMILES: c1ccc(-c2ccc3c(c2)c2cc(-c4ccc5c(c4)c4cc(-c6ccccc6)ccc4n5-c4ccc5oc6ccccc6c5c4)ccc2n3-c2ccccc2)cc1]

TABLE 3-continued
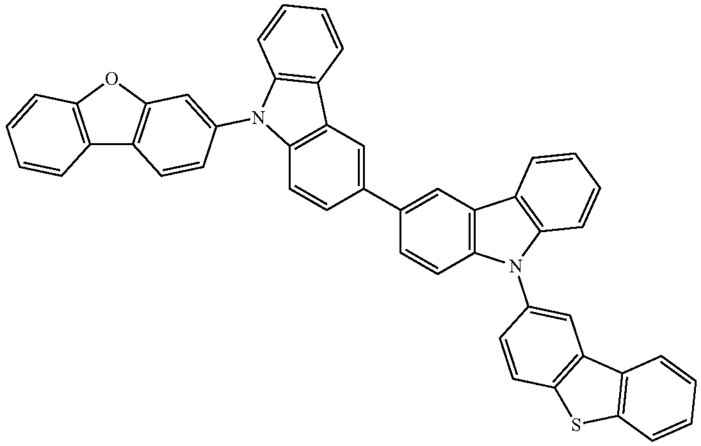 [SMILES: c1ccc2c(c1)oc1cc(-n3c4ccccc4c4cc(-c5ccc6c(c5)c5ccccc5n6-c5ccc6sc7ccccc7c6c5)ccc43)ccc12]
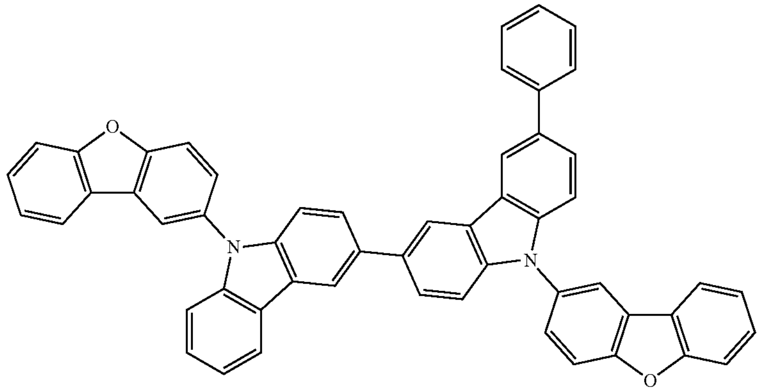 [SMILES: c1ccc(-c2ccc3c(c2)c2cc(-c4ccc5c(c4)c4ccccc4n5-c4ccc5oc6ccccc6c5c4)ccc2n3-c2ccc3oc4ccccc4c3c2)cc1]
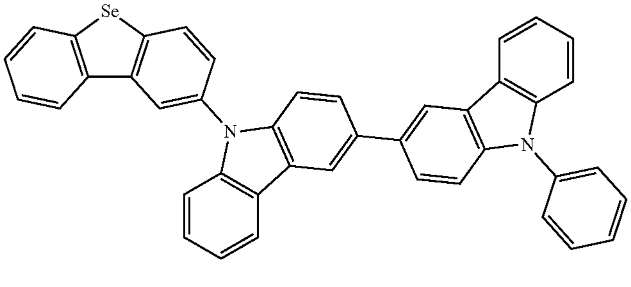 [SMILES: c1ccc(-n2c3ccccc3c3cc(-c4ccc5c(c4)c4ccccc4n5-c4ccc5[se]c6ccccc6c5c4)ccc32)cc1]

TABLE 3-continued
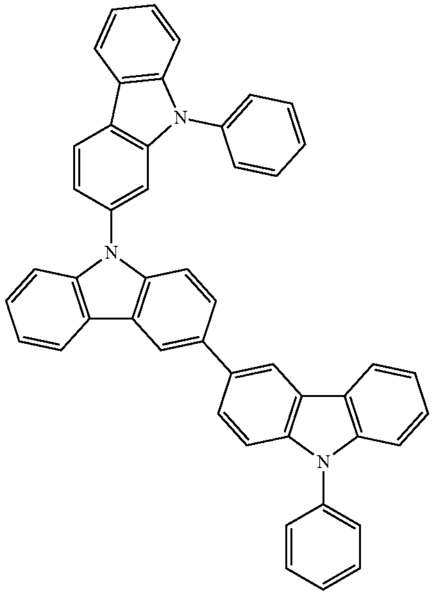 [SMILES: c1ccc(-n2c3ccccc3c3cc(-c4ccc5c(c4)c4ccccc4n5-c4ccc5c6ccccc6n(-c6ccccc6)c5c4)ccc32)cc1]
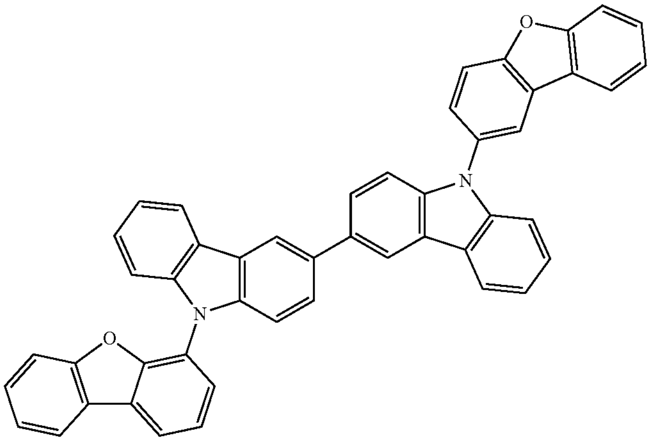 [SMILES: c1ccc2c(c1)oc1ccc(-n3c4ccccc4c4cc(-c5ccc6c(c5)c5ccccc5n6-c5cccc6c5oc5ccccc56)ccc43)cc12]
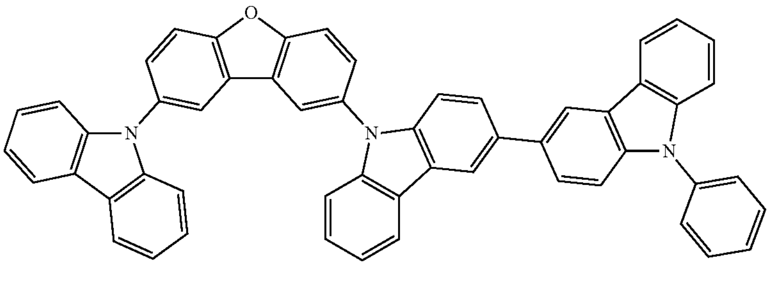 [SMILES: c1ccc(-n2c3ccccc3c3cc(-c4ccc5c(c4)c4ccccc4n5-c4ccc5oc6ccc(-n7c8ccccc8c8ccccc87)cc6c5c4)ccc32)cc1]

TABLE 3-continued
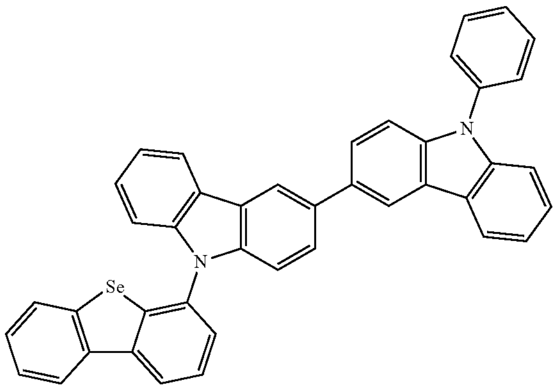 [SMILES: c1ccc(-n2c3ccccc3c3cc(-c4ccc5c(c4)c4ccccc4n5-c4cccc5c4[se]c4ccccc45)ccc32)cc1]
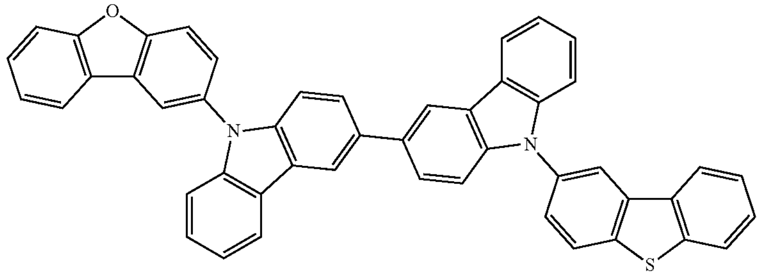 [SMILES: c1ccc2c(c1)oc1ccc(-n3c4ccccc4c4cc(-c5ccc6c(c5)c5ccccc5n6-c5ccc6sc7ccccc7c6c5)ccc43)cc12]
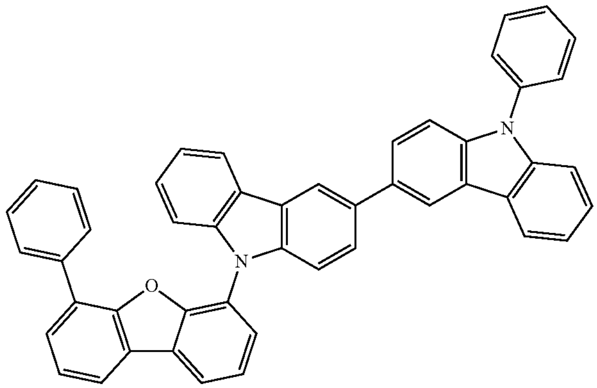
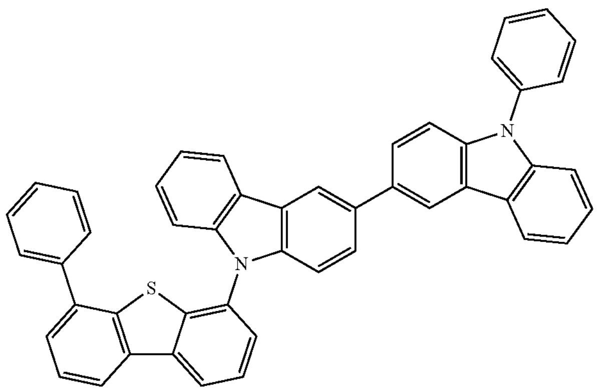 [SMILES: c1ccc(-c2cccc3c2sc2c(-n4c5ccccc5c5cc(-c6ccc7c(c6)c6ccccc6n7-c6ccccc6)ccc54)cccc23)cc1]

TABLE 3-continued
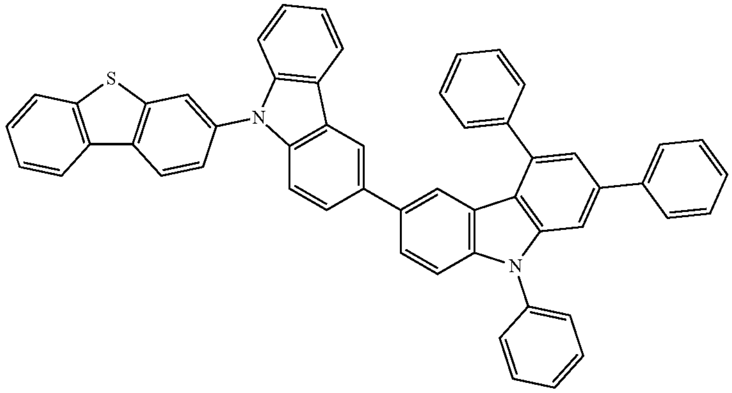
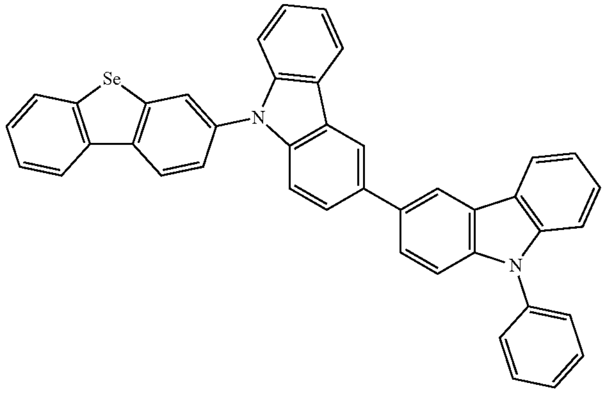 [SMILES: c1ccc(-n2c3ccccc3c3cc(-c4ccc5c(c4)c4ccccc4n5-c4ccc5c(c4)[se]c4ccccc45)ccc32)cc1]
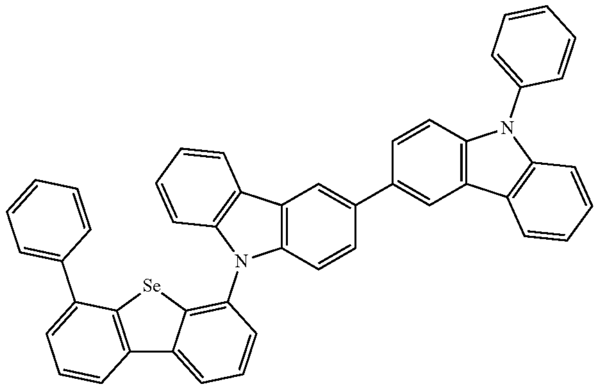
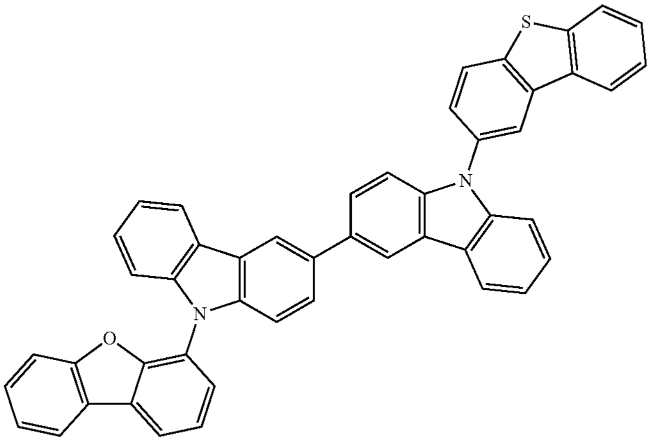 [SMILES: c1ccc2c(c1)oc1c(-n3c4ccccc4c4cc(-c5ccc6c(c5)c5ccccc5n6-c5ccc6sc7ccccc7c6c5)ccc43)cccc12]

TABLE 3-continued
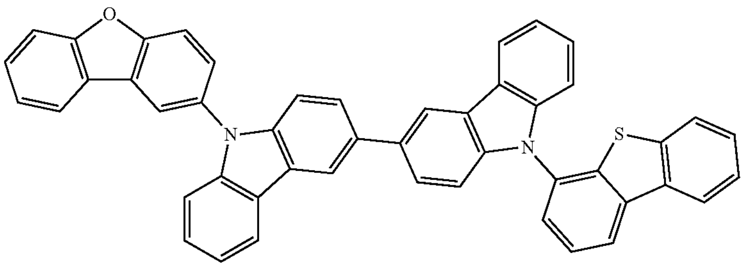 [SMILES: c1ccc2c(c1)oc1ccc(-n3c4ccccc4c4cc(-c5ccc6c(c5)c5ccccc5n6-c5cccc6c5sc5ccccc56)ccc43)cc12]
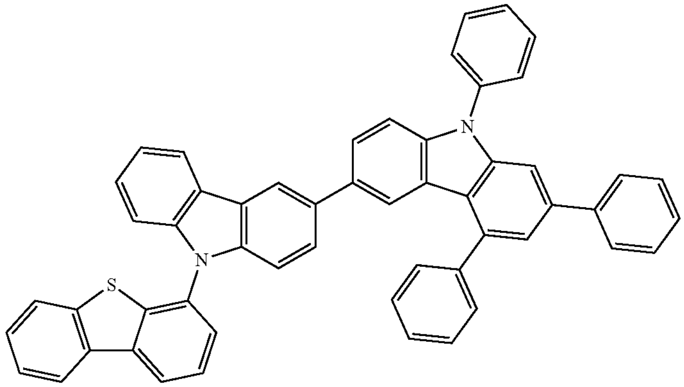 [SMILES: c1ccc(-c2cc(-c3ccccc3)c3c4cc(-c5ccc6c(c5)c5ccccc5n6-c5cccc6c5sc5ccccc56)ccc4n(-c4ccccc4)c3c2)cc1]
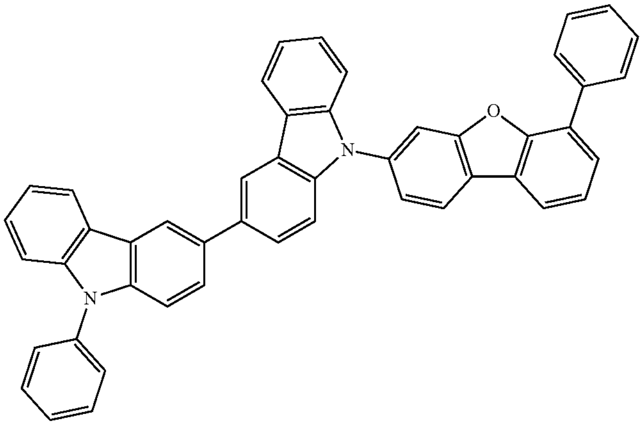 [SMILES: c1ccc(-c2cccc3c2oc2cc(-n4c5ccccc5c5cc(-c6ccc7c(c6)c6ccccc6n7-c6ccccc6)ccc54)ccc23)cc1]
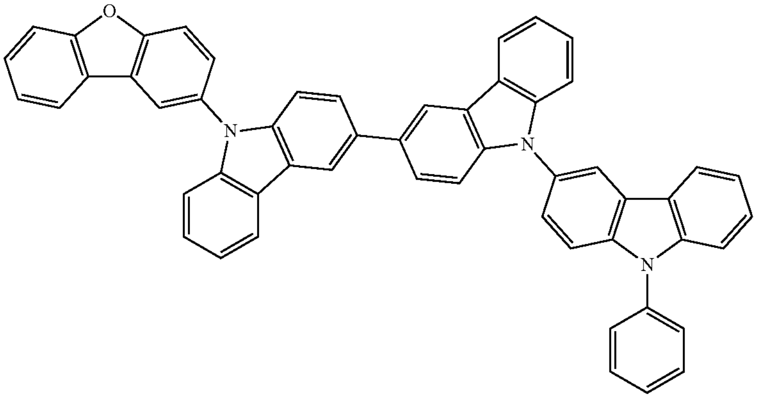 [SMILES: c1ccc(-n2c3ccccc3c3cc(-n4c5ccccc5c5cc(-c6ccc7c(c6)c6ccccc6n7-c6ccc7oc8ccccc8c7c6)ccc54)ccc32)cc1]

TABLE 3-continued
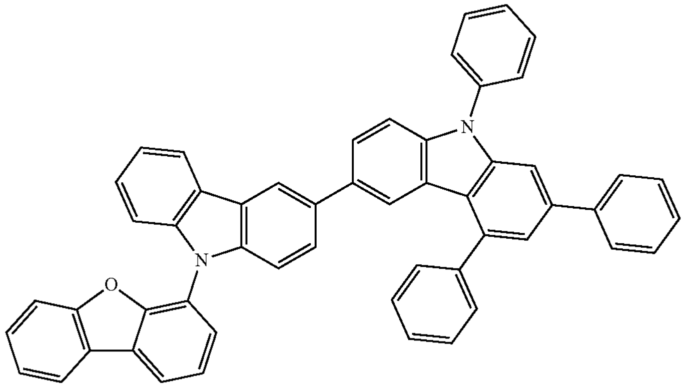
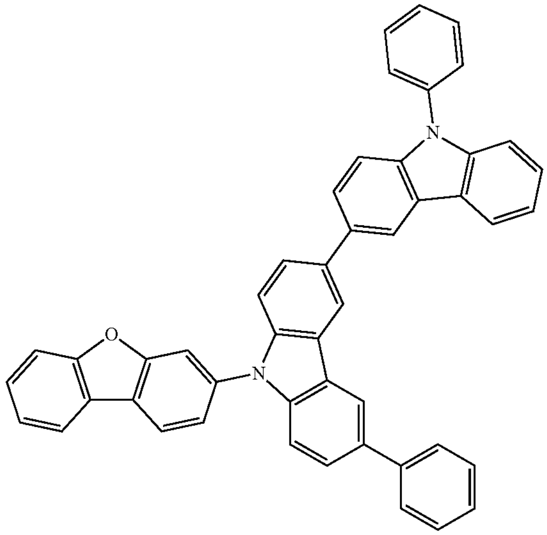 [SMILES: c1ccc(-c2ccc3c(c2)c2cc(-c4ccc5c(c4)c4ccccc4n5-c4ccccc4)ccc2n3-c2ccc3c(c2)oc2ccccc23)cc1]
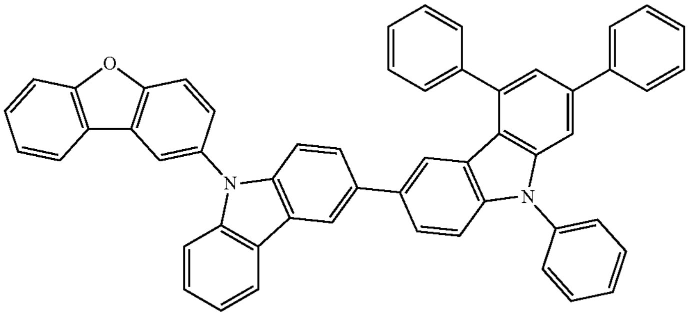 [SMILES: c1ccc(-c2cc(-c3ccccc3)c3c4cc(-c5ccc6c(c5)c5ccccc5n6-c5ccc6oc7ccccc7c6c5)ccc4n(-c4ccccc4)c3c2)cc1]
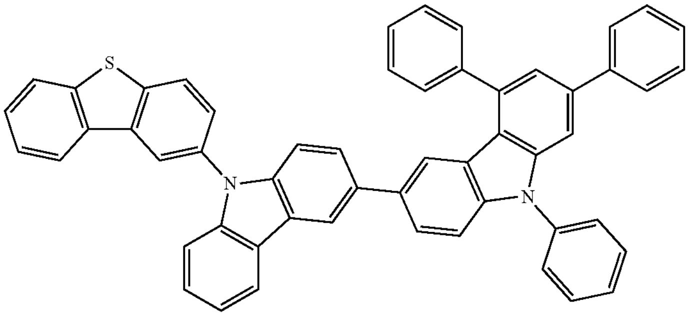 [SMILES: c1ccc(-c2cc(-c3ccccc3)c3c4cc(-c5ccc6c(c5)c5ccccc5n6-c5ccc6sc7ccccc7c6c5)ccc4n(-c4ccccc4)c3c2)cc1]

TABLE 3-continued
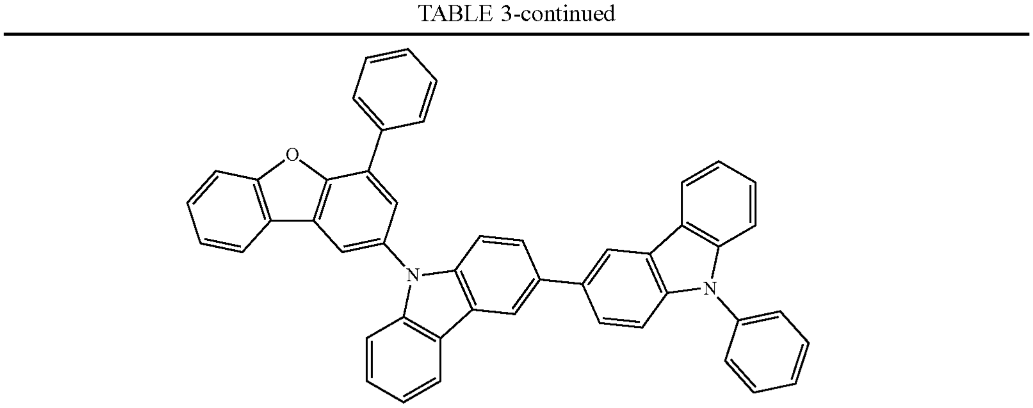
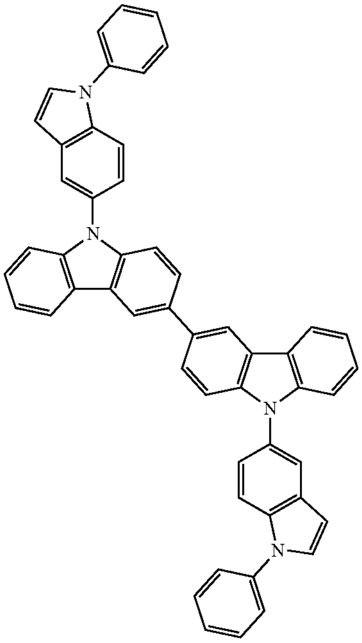 [SMILES: c1ccc(-n2ccc3cc(-n4c5ccccc5c5cc(-c6ccc7c(c6)c6ccccc6n7-c6ccc7c(ccn7-c7ccccc7)c6)ccc54)ccc32)cc1]
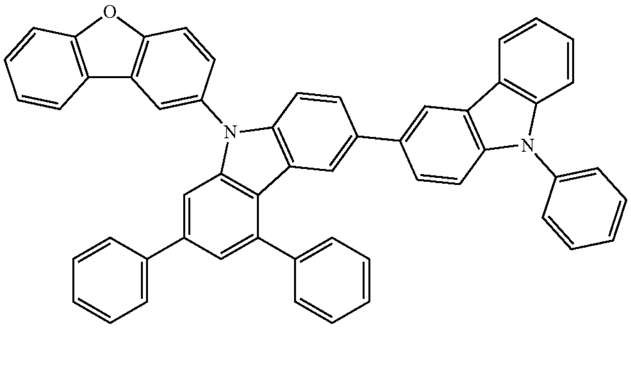 [SMILES: c1ccc(-c2cc(-c3ccccc3)c3c4cc(-c5ccc6c(c5)c5ccccc5n6-c5ccccc5)ccc4n(-c4ccc5oc6ccccc6c5c4)c3c2)cc1]

TABLE 3-continued
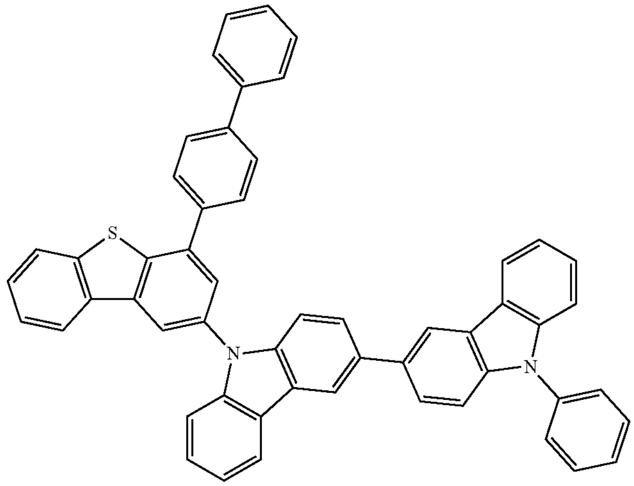 [SMILES: c1ccc(-c2ccc(-c3cc(-n4c5ccccc5c5cc(-c6ccc7c(c6)c6ccccc6n7-c6ccccc6)ccc54)cc4c3sc3ccccc34)cc2)cc1]
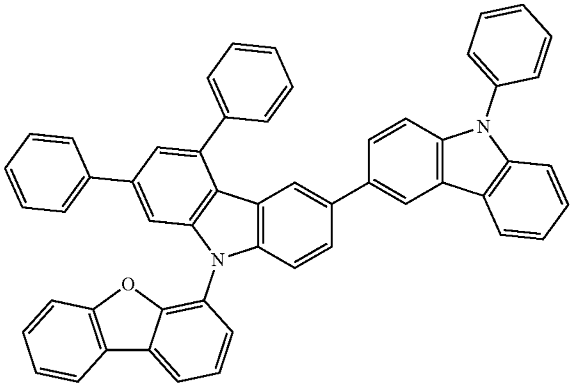 [SMILES: c1ccc(-c2cc(-c3ccccc3)c3c4cc(-c5ccc6c(c5)c5ccccc5n6-c5ccccc5)ccc4n(-c4cccc5c4oc4ccccc45)c3c2)cc1]
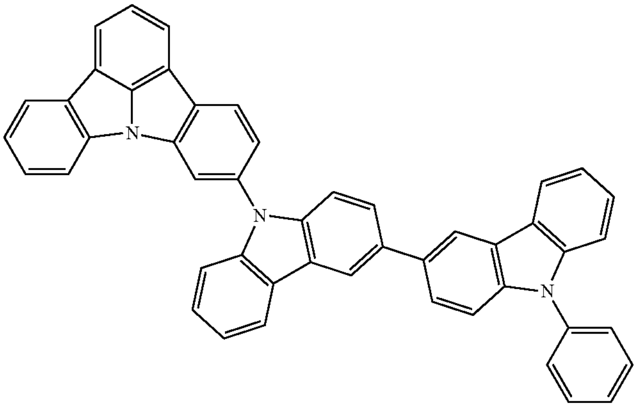 [SMILES: c1ccc(-n2c3ccccc3c3cc(-c4ccc5c(c4)c4ccccc4n5-c4ccc5c6cccc7c8ccccc8n(c5c4)c76)ccc32)cc1]

TABLE 3-continued
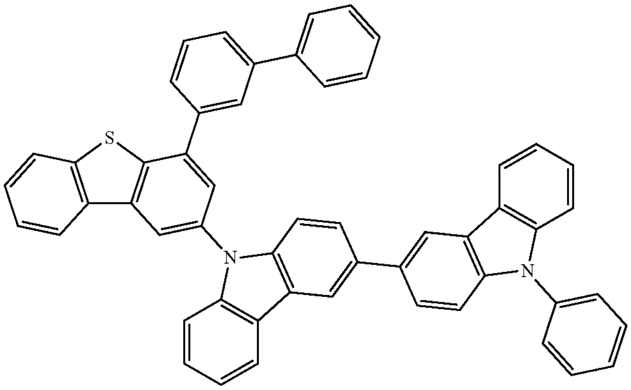 [SMILES: c1ccc(-c2cccc(-c3cc(-n4c5ccccc5c5cc(-c6ccc7c(c6)c6ccccc6n7-c6ccccc6)ccc54)cc4c3sc3ccccc34)c2)cc1]
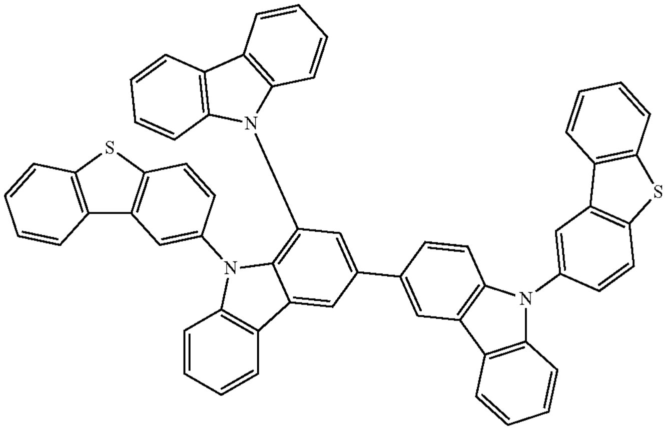 [SMILES: c1ccc2c(c1)sc1ccc(-n3c4ccccc4c4cc(-c5cc(-n6c7ccccc7c7ccccc76)c6c(c5)c5ccccc5n6-c5ccc6sc7ccccc7c6c5)ccc43)cc12]
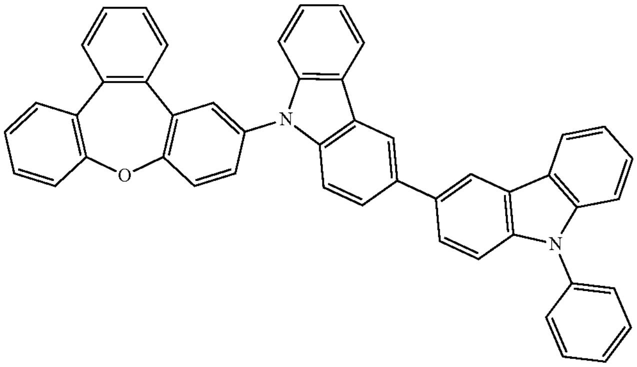 [SMILES: c1ccc(-n2c3ccccc3c3cc(-c4ccc5c(c4)c4ccccc4n5-c4ccc5c(c4)-c4ccccc4-c4ccccc4O5)ccc32)cc1]
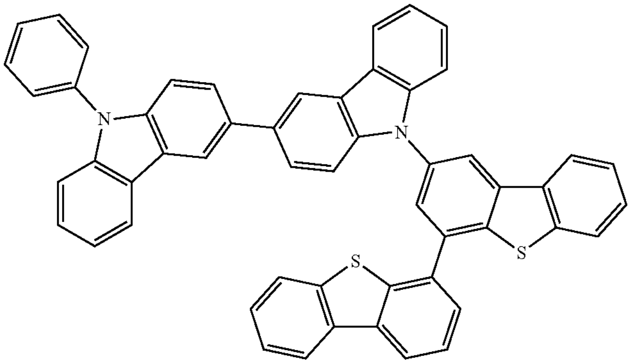 [SMILES: c1ccc(-n2c3ccccc3c3cc(-c4ccc5c(c4)c4ccccc4n5-c4cc(-c5cccc6c5sc5ccccc56)c5sc6ccccc6c5c4)ccc32)cc1]

TABLE 3-continued
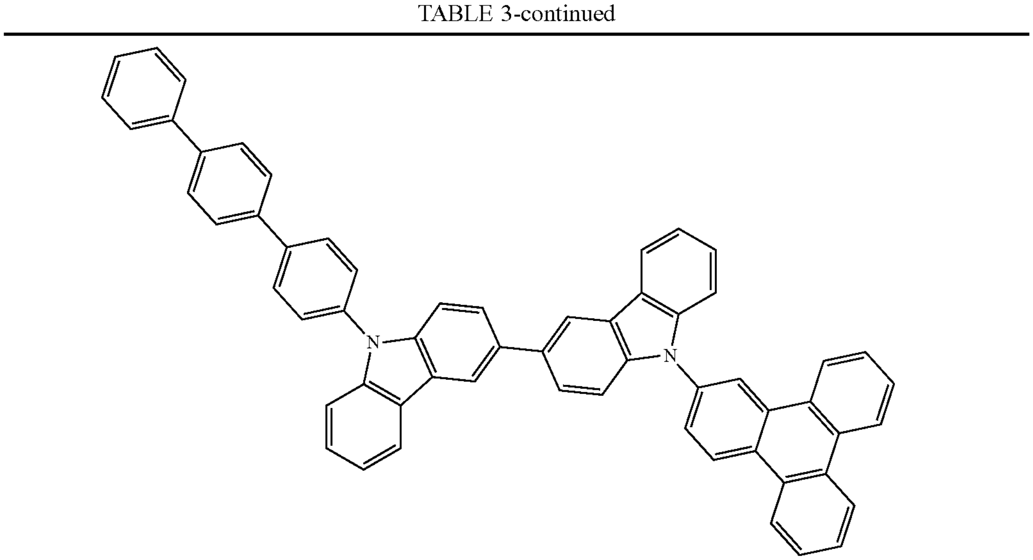
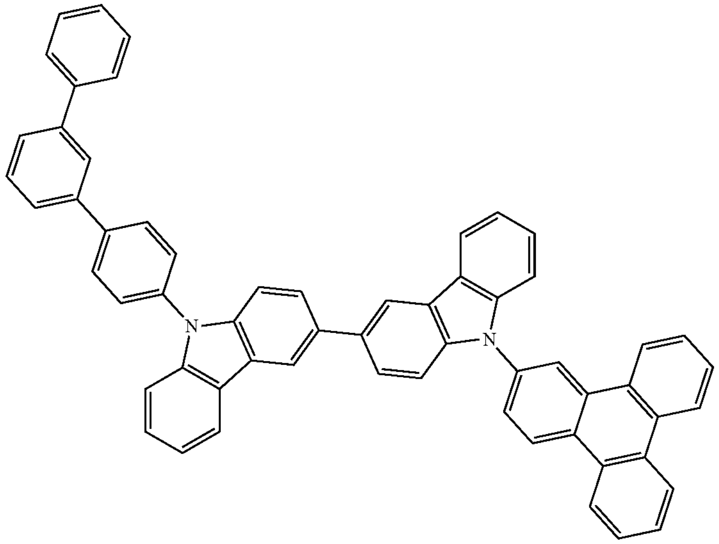 [SMILES: c1ccc(-c2cccc(-c3ccc(-n4c5ccccc5c5cc(-c6ccc7c(c6)c6ccccc6n7-c6ccc7c8ccccc8c8ccccc8c7c6)ccc54)cc3)c2)cc1]
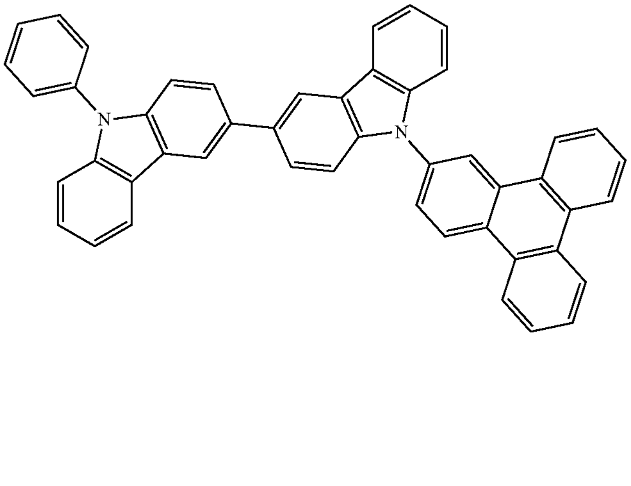 [SMILES: c1ccc(-n2c3ccccc3c3cc(-c4ccc5c(c4)c4ccccc4n5-c4ccc5c6ccccc6c6ccccc6c5c4)ccc32)cc1]

TABLE 3-continued
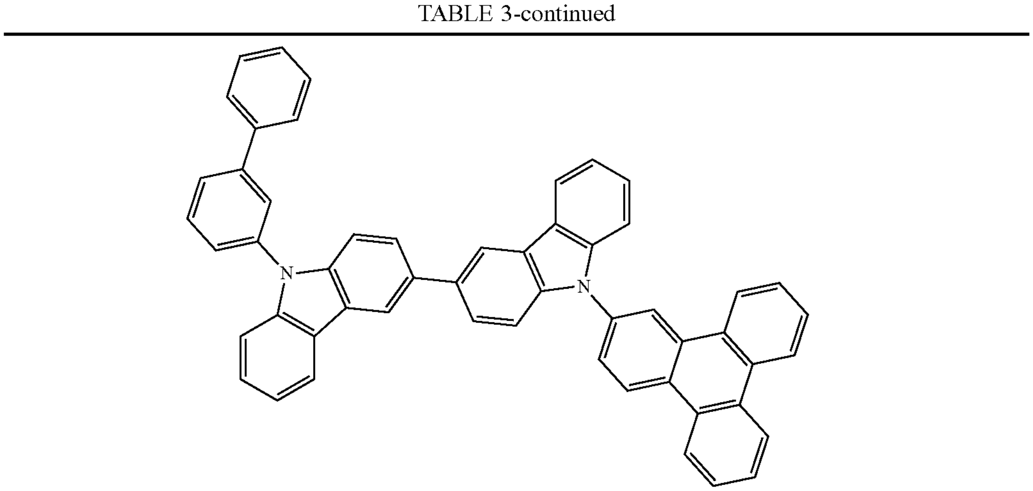
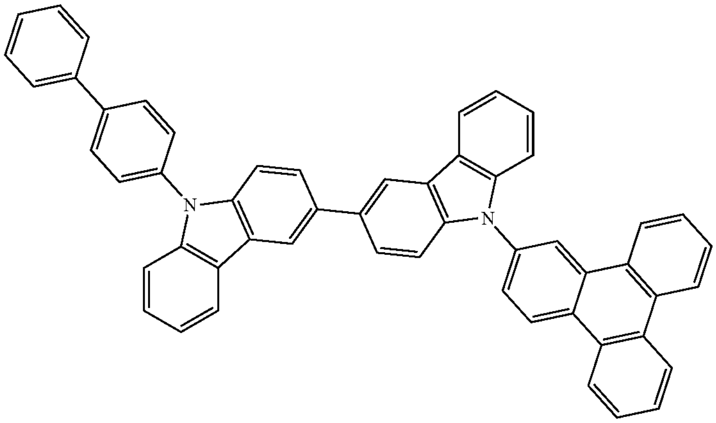 [SMILES: c1ccc(-c2ccc(-n3c4ccccc4c4cc(-c5ccc6c(c5)c5ccccc5n6-c5ccc6c7ccccc7c7ccccc7c6c5)ccc43)cc2)cc1]
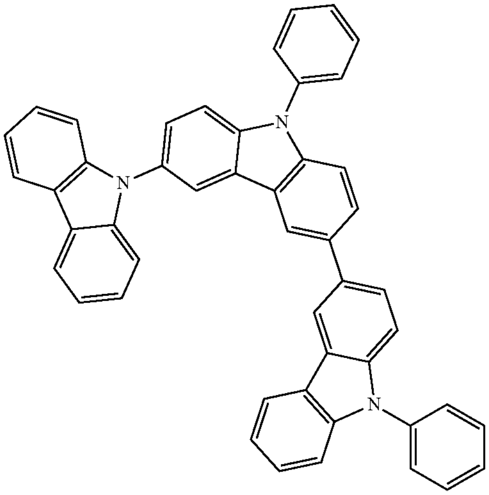 [SMILES: c1ccc(-n2c3ccccc3c3cc(-c4ccc5c(c4)c4cc(-n6c7ccccc7c7ccccc76)ccc4n5-c4ccccc4)ccc32)cc1]
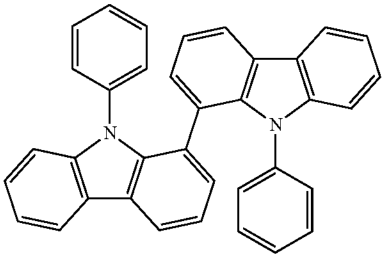 [SMILES: c1ccc(-n2c3ccccc3c3cccc(-c4cccc5c6ccccc6n(-c6ccccc6)c45)c32)cc1]

TABLE 3-continued
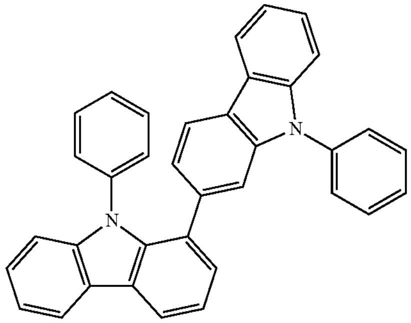 [SMILES: c1ccc(-n2c3ccccc3c3ccc(-c4cccc5c6ccccc6n(-c6ccccc6)c45)cc32)cc1]
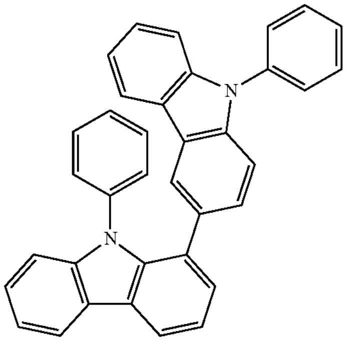 [SMILES: c1ccc(-n2c3ccccc3c3cc(-c4cccc5c6ccccc6n(-c6ccccc6)c45)ccc32)cc1]
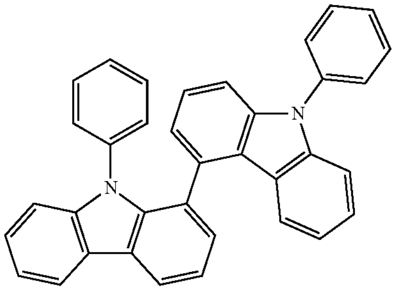 [SMILES: c1ccc(-n2c3ccccc3c3c(-c4cccc5c6ccccc6n(-c6ccccc6)c45)cccc32)cc1]
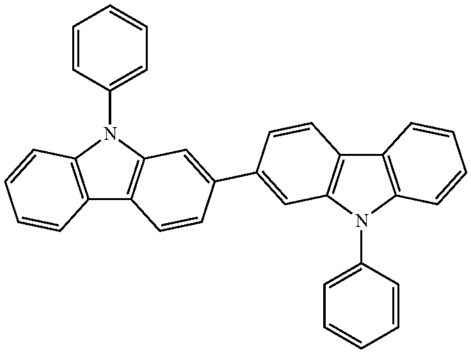 [SMILES: c1ccc(-n2c3ccccc3c3ccc(-c4ccc5c6ccccc6n(-c6ccccc6)c5c4)cc32)cc1]
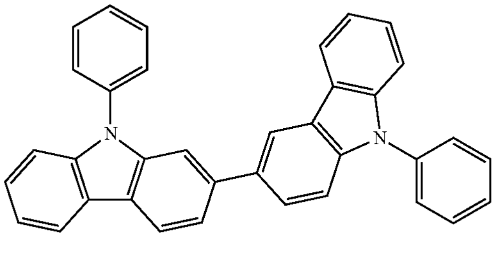 [SMILES: c1ccc(-n2c3ccccc3c3cc(-c4ccc5c6ccccc6n(-c6ccccc6)c5c4)ccc32)cc1]

TABLE 3-continued
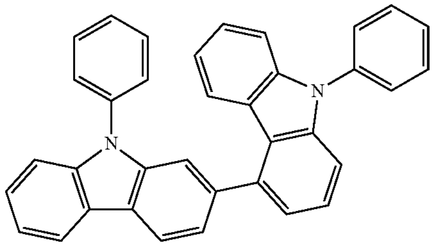 [SMILES: c1ccc(-n2c3ccccc3c3ccc(-c4cccc5c4c4ccccc4n5-c4ccccc4)cc32)cc1]
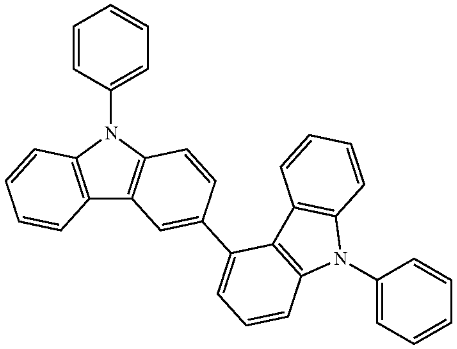 [SMILES: c1ccc(-n2c3ccccc3c3cc(-c4cccc5c4c4ccccc4n5-c4ccccc4)ccc32)cc1]
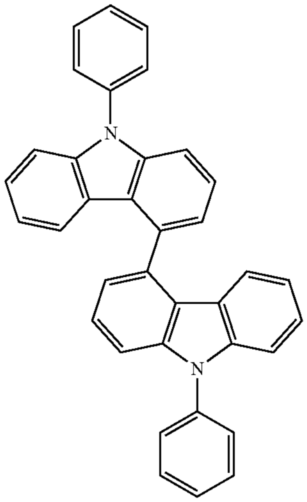 [SMILES: c1ccc(-n2c3ccccc3c3c(-c4cccc5c4c4ccccc4n5-c4ccccc4)cccc32)cc1]
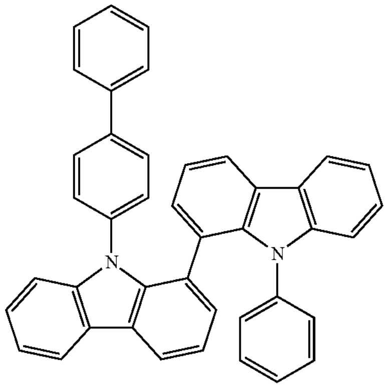 [SMILES: c1ccc(-c2ccc(-n3c4ccccc4c4cccc(-c5cccc6c7ccccc7n(-c7ccccc7)c56)c43)cc2)cc1]

TABLE 3-continued
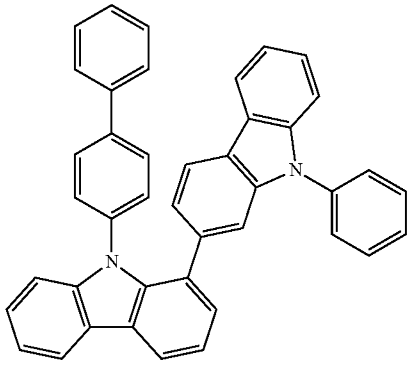 [SMILES: c1ccc(-c2ccc(-n3c4ccccc4c4cccc(-c5ccc6c7ccccc7n(-c7ccccc7)c6c5)c43)cc2)cc1]
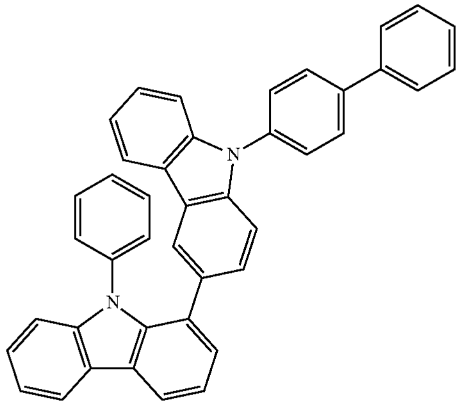 [SMILES: c1ccc(-c2ccc(-n3c4ccccc4c4cc(-c5cccc6c7ccccc7n(-c7ccccc7)c56)ccc43)cc2)cc1]
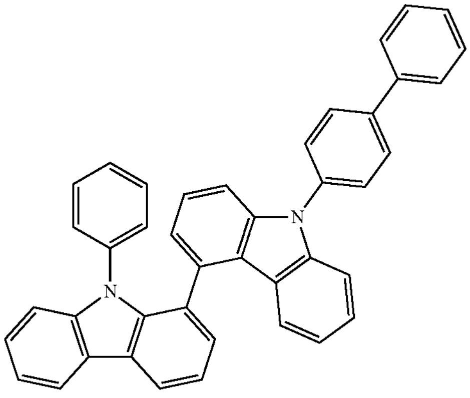 [SMILES: c1ccc(-c2ccc(-n3c4ccccc4c4c(-c5cccc6c7ccccc7n(-c7ccccc7)c56)cccc43)cc2)cc1]
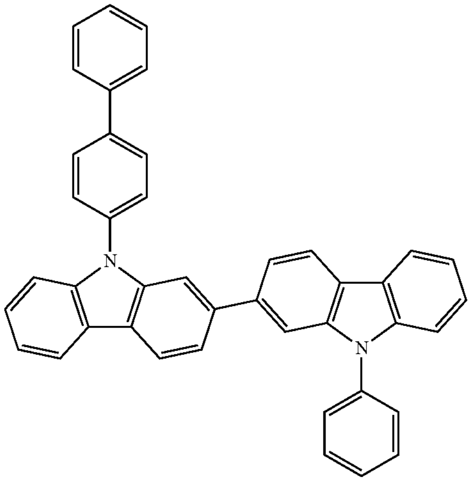 [SMILES: c1ccc(-c2ccc(-n3c4ccccc4c4ccc(-c5ccc6c7ccccc7n(-c7ccccc7)c6c5)cc43)cc2)cc1]

TABLE 3-continued
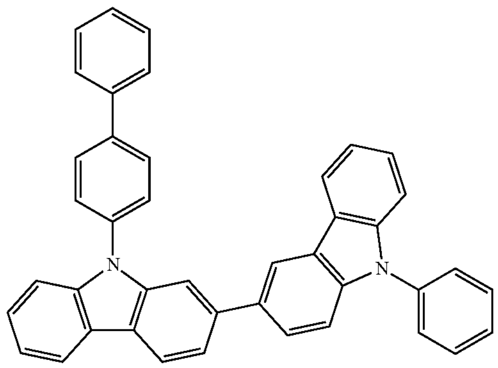 [SMILES: c1ccc(-c2ccc(-n3c4ccccc4c4ccc(-c5ccc6c(c5)c5ccccc5n6-c5ccccc5)cc43)cc2)cc1]
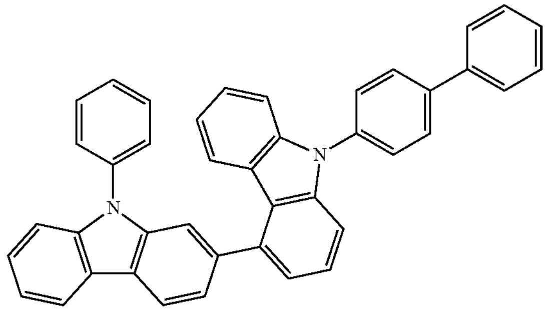 [SMILES: c1ccc(-c2ccc(-n3c4ccccc4c4c(-c5ccc6c7ccccc7n(-c7ccccc7)c6c5)cccc43)cc2)cc1]
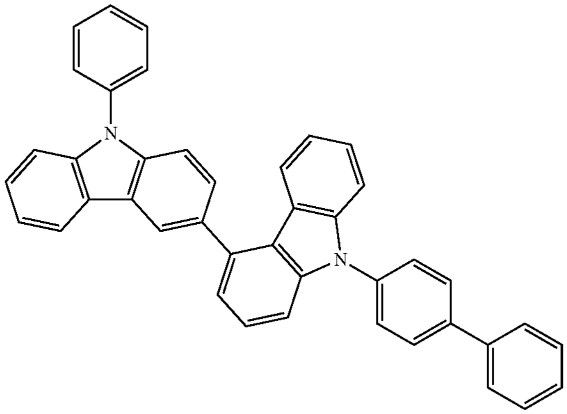 [SMILES: c1ccc(-c2ccc(-n3c4ccccc4c4c(-c5ccc6c(c5)c5ccccc5n6-c5ccccc5)cccc43)cc2)cc1]

TABLE 3-continued
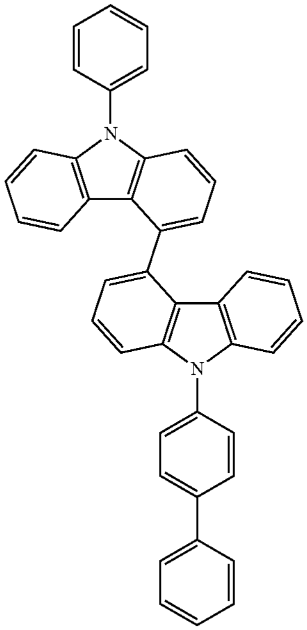 [SMILES: c1ccc(-c2ccc(-n3c4ccccc4c4c(-c5cccc6c5c5ccccc5n6-c5ccccc5)cccc43)cc2)cc1]
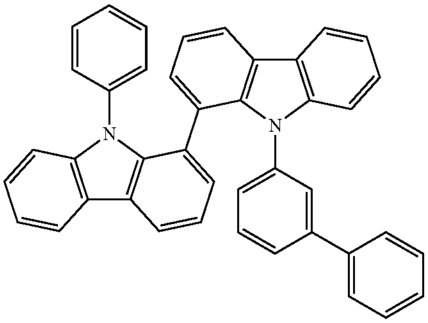 [SMILES: c1ccc(-c2cccc(-n3c4ccccc4c4cccc(-c5cccc6c7ccccc7n(-c7ccccc7)c56)c43)c2)cc1]
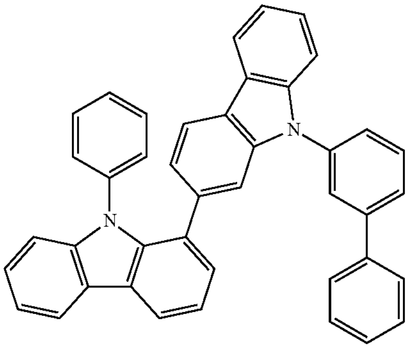 [SMILES: c1ccc(-c2cccc(-n3c4ccccc4c4ccc(-c5cccc6c7ccccc7n(-c7ccccc7)c56)cc43)c2)cc1]
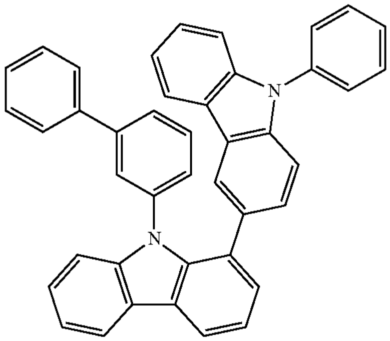 [SMILES: c1ccc(-c2cccc(-n3c4ccccc4c4cccc(-c5ccc6c(c5)c5ccccc5n6-c5ccccc5)c43)c2)cc1]

TABLE 3-continued
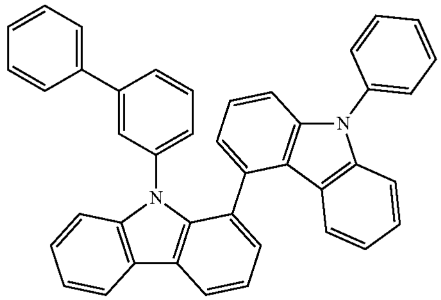 [SMILES: c1ccc(-c2cccc(-n3c4ccccc4c4cccc(-c5cccc6c5c5ccccc5n6-c5ccccc5)c43)c2)cc1]
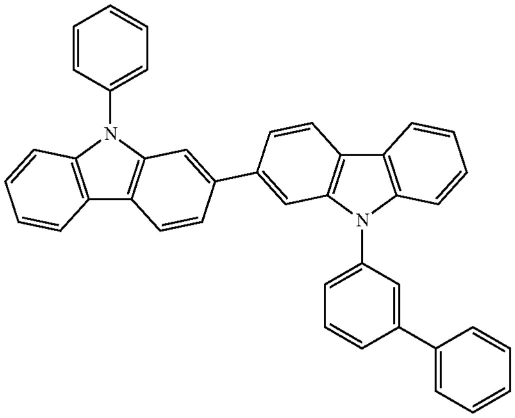 [SMILES: c1ccc(-c2cccc(-n3c4ccccc4c4ccc(-c5ccc6c7ccccc7n(-c7ccccc7)c6c5)cc43)c2)cc1]
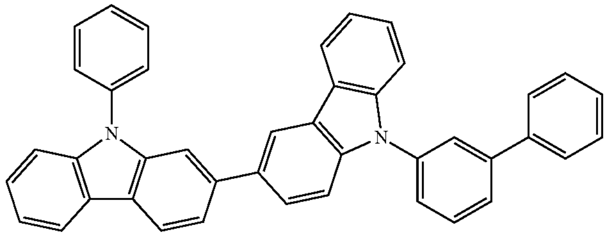 [SMILES: c1ccc(-c2cccc(-n3c4ccccc4c4cc(-c5ccc6c7ccccc7n(-c7ccccc7)c6c5)ccc43)c2)cc1]
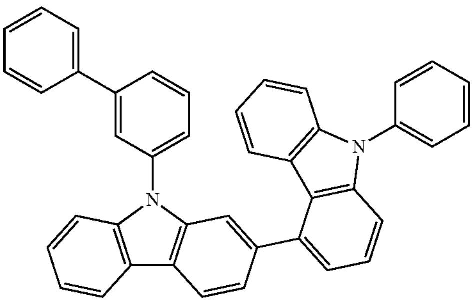 [SMILES: c1ccc(-c2cccc(-n3c4ccccc4c4ccc(-c5cccc6c5c5ccccc5n6-c5ccccc5)cc43)c2)cc1]

TABLE 3-continued
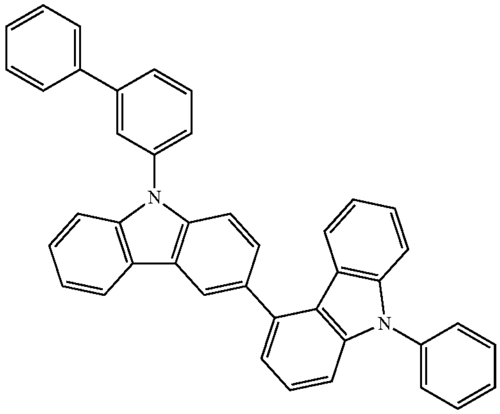 [SMILES: c1ccc(-c2cccc(-n3c4ccccc4c4cc(-c5cccc6c5c5ccccc5n6-c5ccccc5)ccc43)c2)cc1]
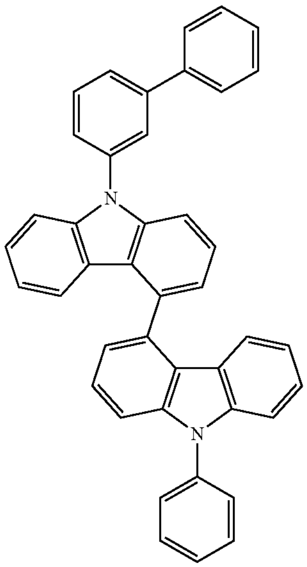 [SMILES: c1ccc(-c2cccc(-n3c4ccccc4c4c(-c5cccc6c5c5ccccc5n6-c5ccccc5)cccc43)c2)cc1]
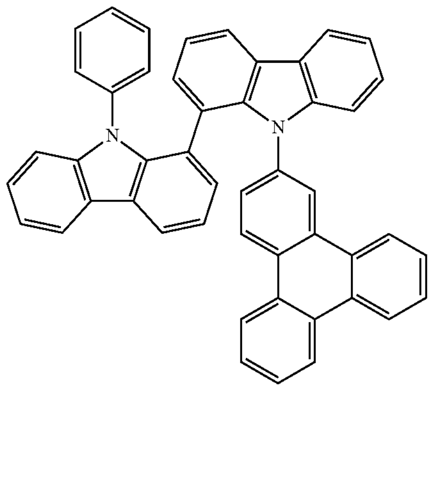 [SMILES: c1ccc(-n2c3ccccc3c3cccc(-c4cccc5c6ccccc6n(-c6ccc7c8ccccc8c8ccccc8c7c6)c45)c32)cc1]

TABLE 3-continued
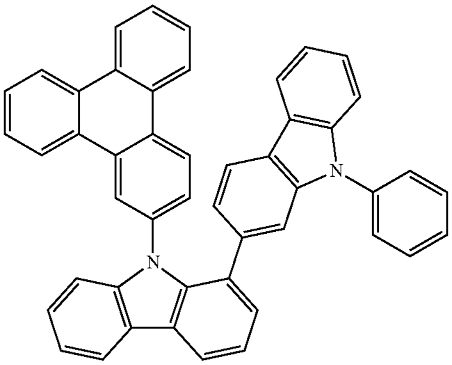 [SMILES: c1ccc(-n2c3ccccc3c3ccc(-c4cccc5c6ccccc6n(-c6ccc7c8ccccc8c8ccccc8c7c6)c45)cc32)cc1]
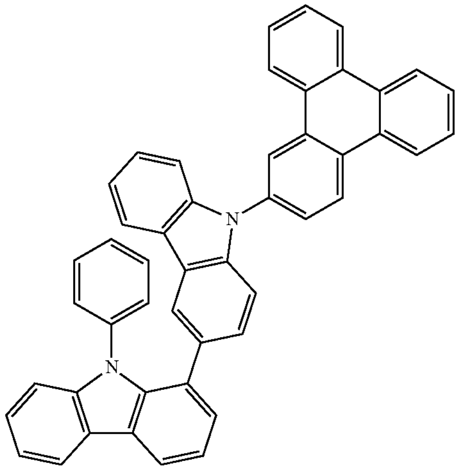 [SMILES: c1ccc(-n2c3ccccc3c3cccc(-c4ccc5c(c4)c4ccccc4n5-c4ccc5c6ccccc6c6ccccc6c5c4)c32)cc1]
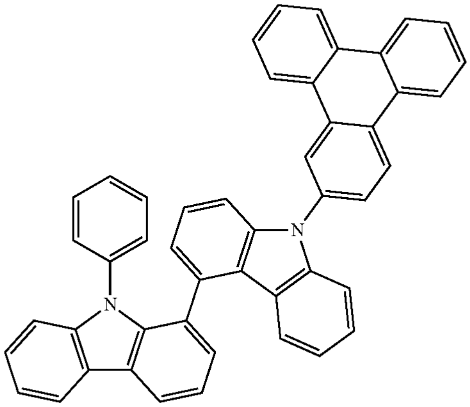 [SMILES: c1ccc(-n2c3ccccc3c3cccc(-c4cccc5c4c4ccccc4n5-c4ccc5c6ccccc6c6ccccc6c5c4)c32)cc1]

TABLE 3-continued
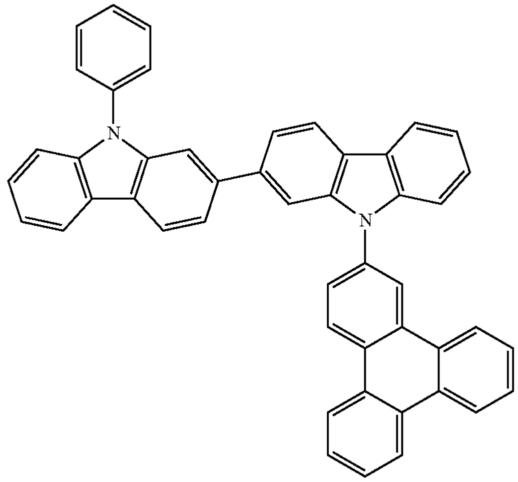 [SMILES: c1ccc(-n2c3ccccc3c3ccc(-c4ccc5c6ccccc6n(-c6ccc7c8ccccc8c8ccccc8c7c6)c5c4)cc32)cc1]
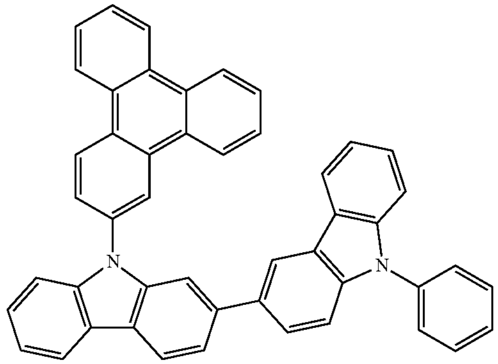 [SMILES: c1ccc(-n2c3ccccc3c3cc(-c4ccc5c6ccccc6n(-c6ccc7c8ccccc8c8ccccc8c7c6)c5c4)ccc32)cc1]
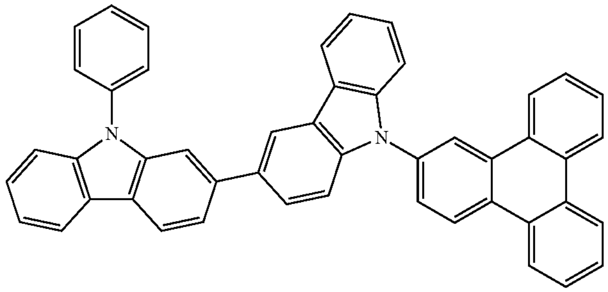 [SMILES: c1ccc(-n2c3ccccc3c3ccc(-c4ccc5c(c4)c4ccccc4n5-c4ccc5c6ccccc6c6ccccc6c5c4)cc32)cc1]
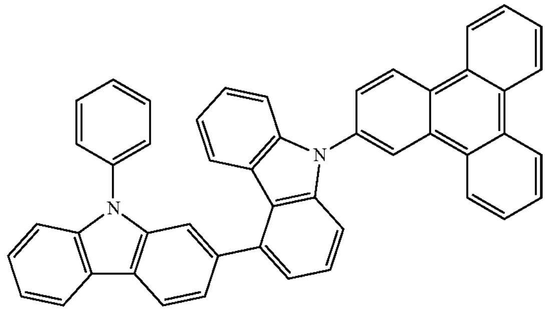 [SMILES: c1ccc(-n2c3ccccc3c3ccc(-c4cccc5c4c4ccccc4n5-c4ccc5c6ccccc6c6ccccc6c5c4)cc32)cc1]

TABLE 3-continued
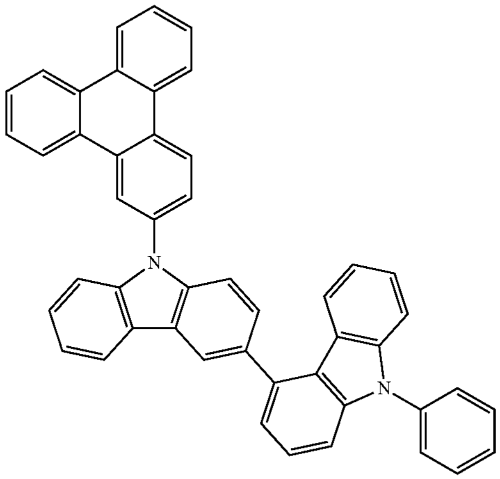 [SMILES: c1ccc(-n2c3ccccc3c3c(-c4ccc5c(c4)c4ccccc4n5-c4ccc5c6ccccc6c6ccccc6c5c4)cccc32)cc1]
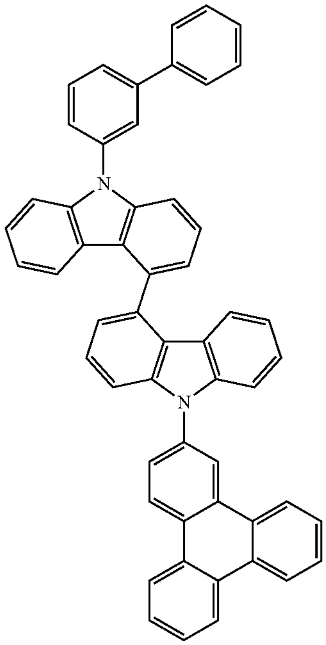 [SMILES: c1ccc(-c2cccc(-n3c4ccccc4c4c(-c5cccc6c5c5ccccc5n6-c5ccc6c7ccccc7c7ccccc7c6c5)cccc43)c2)cc1]
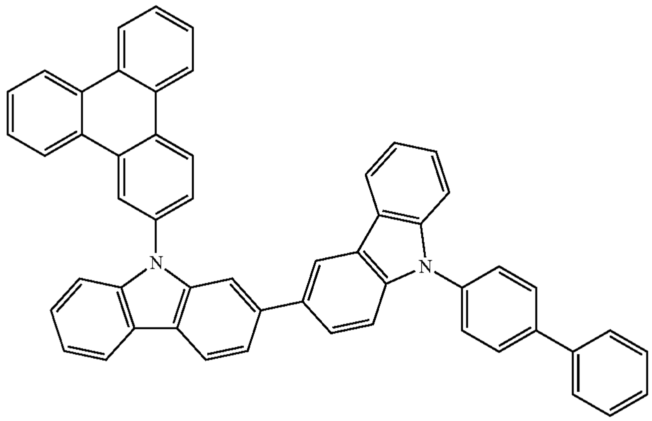 [SMILES: c1ccc(-c2ccc(-n3c4ccccc4c4cc(-c5ccc6c7ccccc7n(-c7ccc8c9ccccc9c9ccccc9c8c7)c6c5)ccc43)cc2)cc1]

TABLE 3-continued
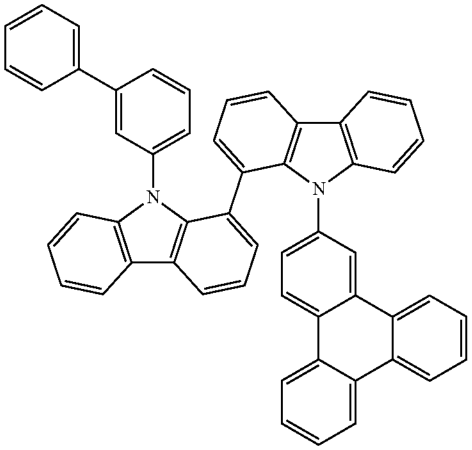 [SMILES: c1ccc(-c2cccc(-n3c4ccccc4c4cccc(-c5cccc6c7ccccc7n(-c7ccc8c9ccccc9c9ccccc9c8c7)c56)c43)c2)cc1]
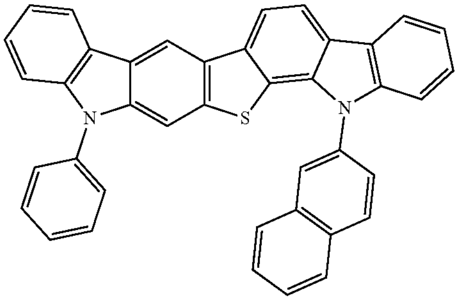 [SMILES: c1ccc(-n2c3ccccc3c3cc4c(cc32)sc2c4ccc3c4ccccc4n(-c4ccc5ccccc5c4)c32)cc1]
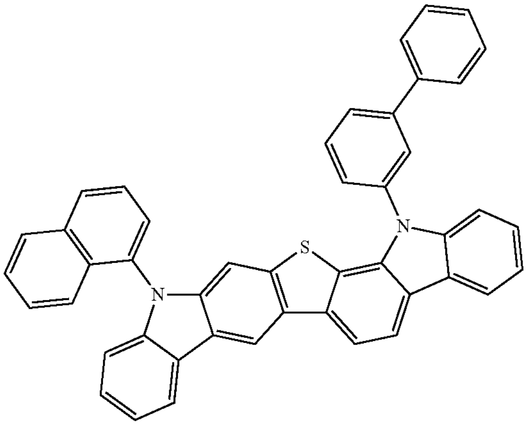 [SMILES: c1ccc(-c2cccc(-n3c4ccccc4c4ccc5c6cc7c8ccccc8n(-c8cccc9ccccc89)c7cc6sc5c43)c2)cc1]

TABLE 3-continued
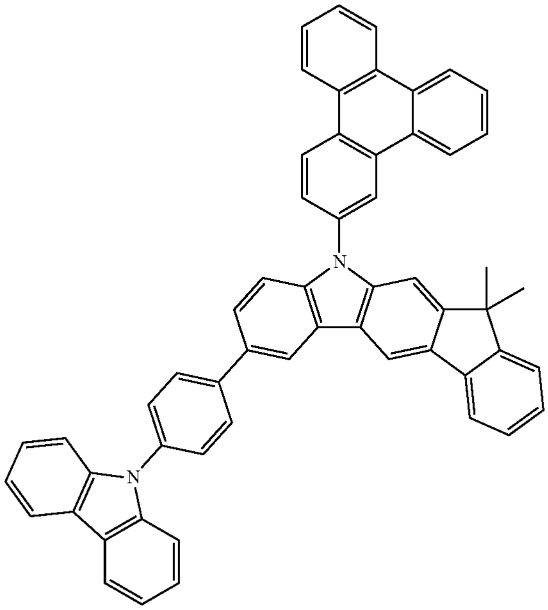 [SMILES: CC1(C)c2ccccc2-c2cc3c4cc(-c5ccc(-n6c7ccccc7c7ccccc76)cc5)ccc4n(-c4ccc5c6ccccc6c6ccccc6c5c4)c3cc21]
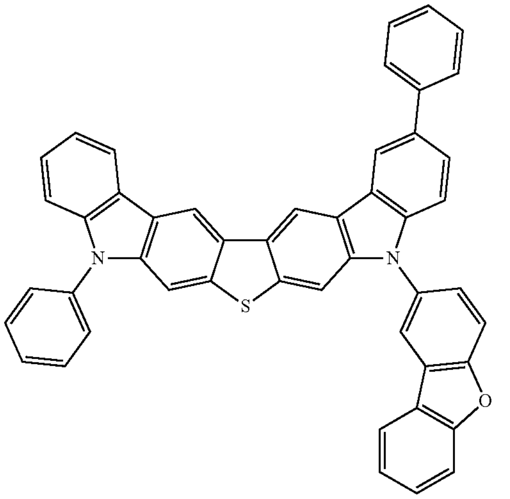 [SMILES: c1ccc(-c2ccc3c(c2)c2cc4c(cc2n3-c2ccc3oc5ccccc5c3c2)sc2cc3c(cc24)c2ccccc2n3-c2ccccc2)cc1]
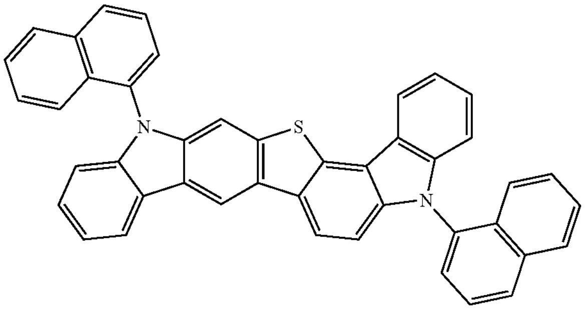 [SMILES: c1ccc2c(-n3c4ccccc4c4cc5c(cc43)sc3c5ccc4c3c3ccccc3n4-c3cccc4ccccc34)cccc2c1]

TABLE 3-continued
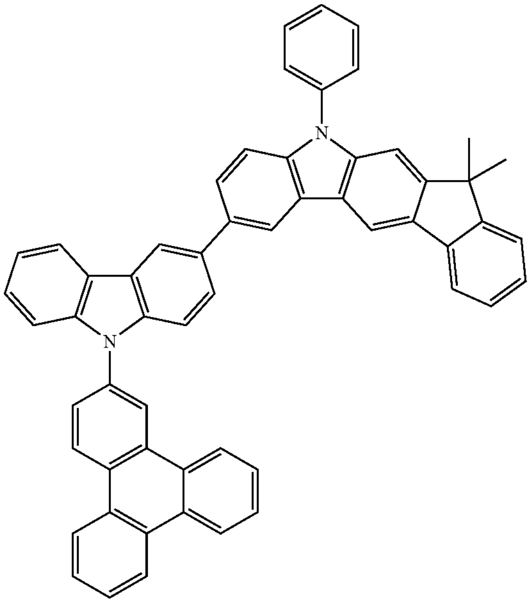 [SMILES: CC1(C)c2ccccc2-c2cc3c4cc(-c5ccc6c(c5)c5ccccc5n6-c5ccc6c7ccccc7c7ccccc7c6c5)ccc4n(-c4ccccc4)c3cc21]
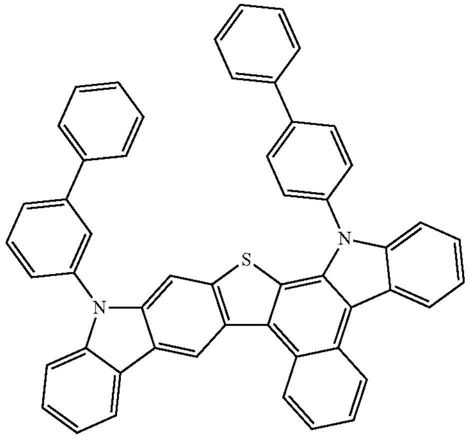 [SMILES: c1ccc(-c2ccc(-n3c4ccccc4c4c5ccccc5c5c6cc7c8ccccc8n(-c8cccc(-c9ccccc9)c8)c7cc6sc5c43)cc2)cc1]
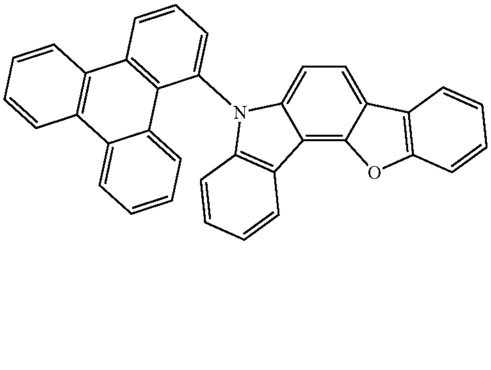 [SMILES: c1ccc2c(c1)oc1c2ccc2c1c1ccccc1n2-c1cccc2c3ccccc3c3ccccc3c12]

TABLE 3-continued
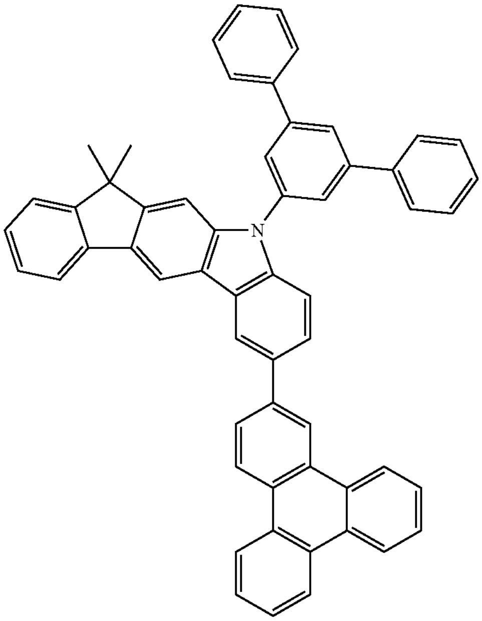 [SMILES: CC1(C)c2ccccc2-c2cc3c4cc(-c5ccc6c7ccccc7c7ccccc7c6c5)ccc4n(-c4cc(-c5ccccc5)cc(-c5ccccc5)c4)c3cc21]
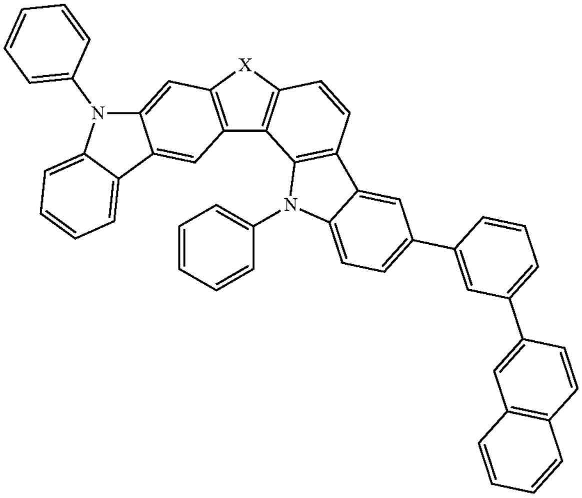
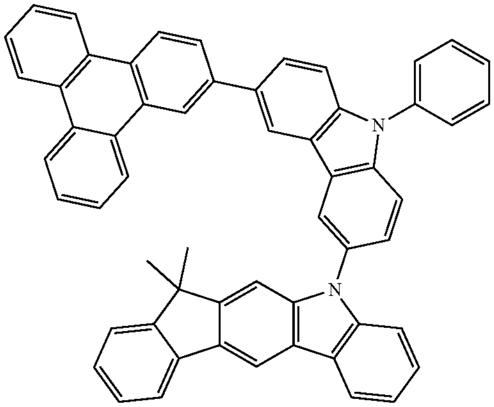 [SMILES: CC1(C)c2ccccc2-c2cc3c4ccccc4n(-c4ccc5c(c4)c4cc(-c6ccc7c8ccccc8c8ccccc8c7c6)ccc4n5-c4ccccc4)c3cc21]

TABLE 3-continued
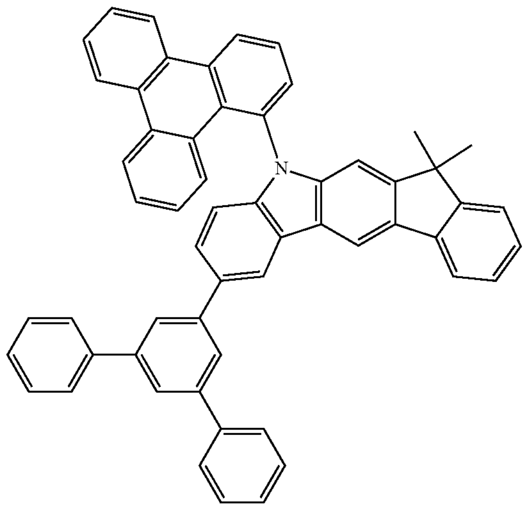 [SMILES: CC1(C)c2ccccc2-c2cc3c4cc(-c5cc(-c6ccccc6)cc(-c6ccccc6)c5)ccc4n(-c4cccc5c6ccccc6c6ccccc6c45)c3cc21]
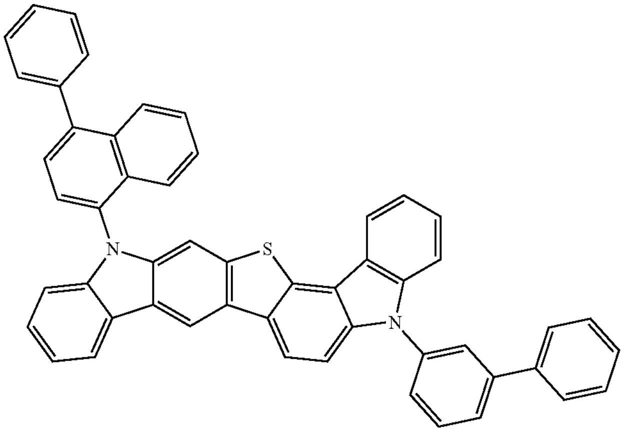 [SMILES: c1ccc(-c2cccc(-n3c4ccccc4c4c5sc6cc7c(cc6c5ccc43)c3ccccc3n7-c3ccc(-c4ccccc4)c4ccccc34)c2)cc1]
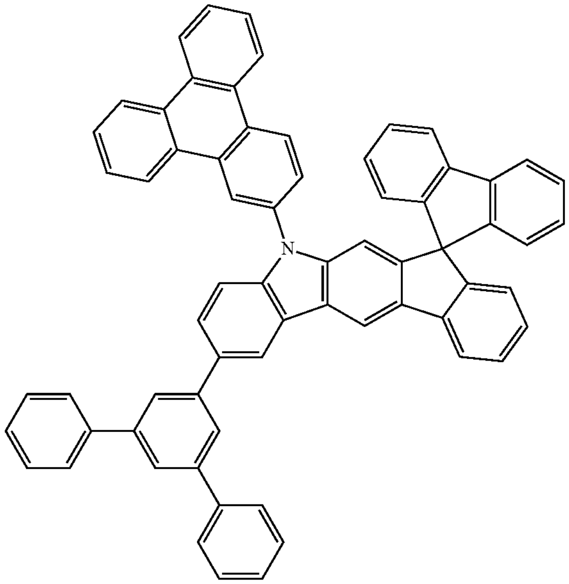 [SMILES: c1ccc(-c2cc(-c3ccccc3)cc(-c3ccc4c(c3)c3cc5c(cc3n4-c3ccc4c6ccccc6c6ccccc6c4c3)C3(c4ccccc4-c4ccccc43)c3ccccc3-5)c2)cc1]

TABLE 3-continued
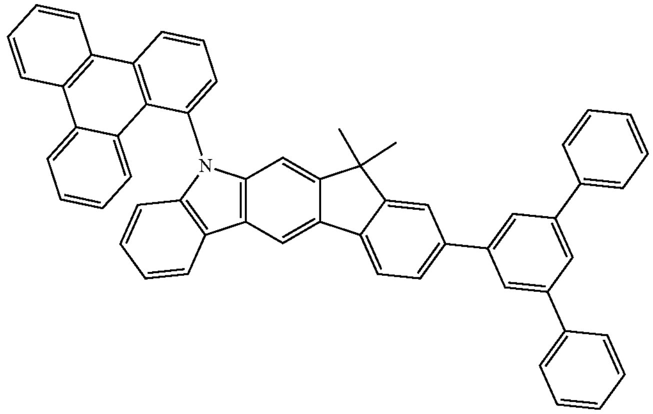 [SMILES: CC1(C)c2cc(-c3cc(-c4ccccc4)cc(-c4ccccc4)c3)ccc2-c2cc3c4ccccc4n(-c4cccc5c6ccccc6c6ccccc6c45)c3cc21]
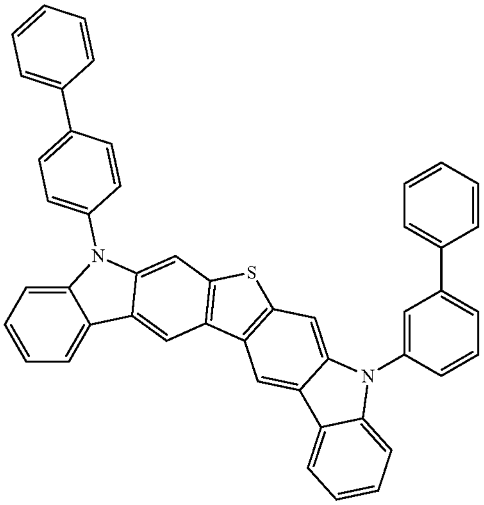 [SMILES: c1ccc(-c2ccc(-n3c4ccccc4c4cc5c(cc43)sc3cc4c(cc35)c3ccccc3n4-c3cccc(-c4ccccc4)c3)cc2)cc1]
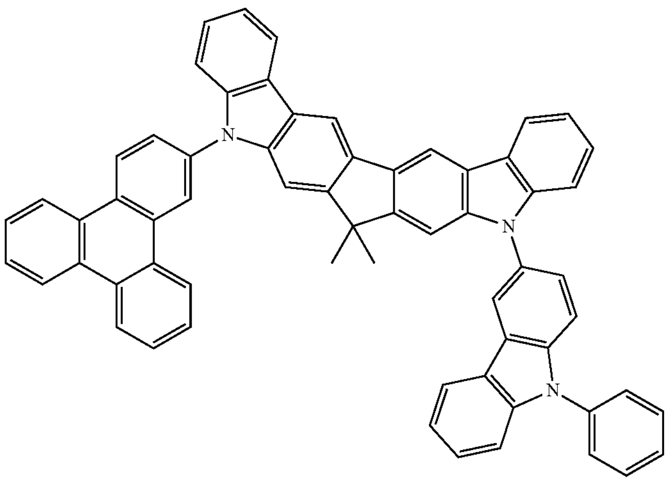 [SMILES: CC1(C)c2cc3c(cc2-c2cc4c5ccccc5n(-c5ccc6c(c5)c5ccccc5n6-c5ccccc5)c4cc21)c1ccccc1n3-c1ccc2c3ccccc3c3ccccc3c2c1]

TABLE 3-continued
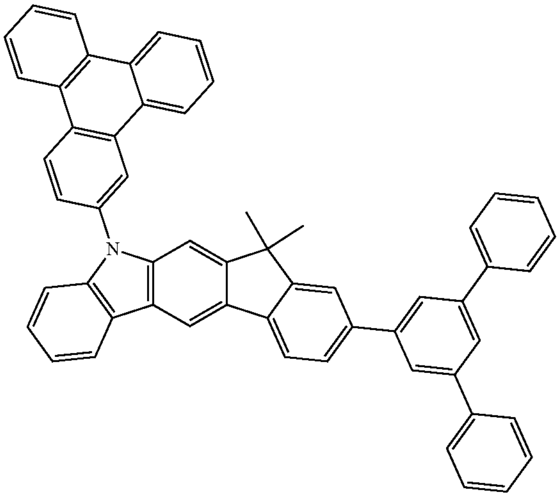 [SMILES: CC1(C)c2cc(-c3cc(-c4ccccc4)cc(-c4ccccc4)c3)ccc2-c2cc3c4ccccc4n(-c4ccc5c6ccccc6c6ccccc6c5c4)c3cc21]
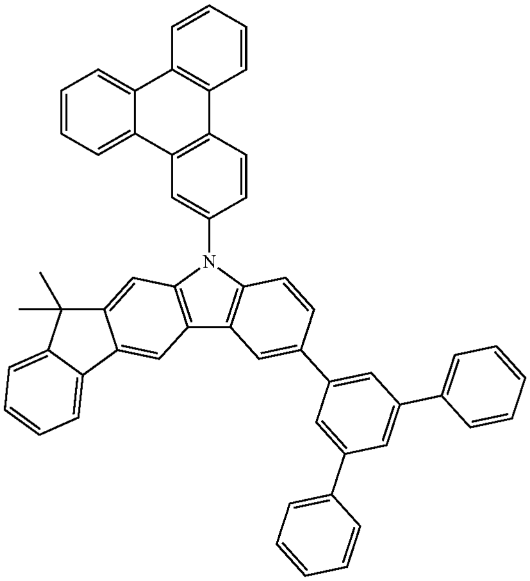 [SMILES: CC1(C)c2ccccc2-c2cc3c4cc(-c5cc(-c6ccccc6)cc(-c6ccccc6)c5)ccc4n(-c4ccc5c6ccccc6c6ccccc6c5c4)c3cc21]
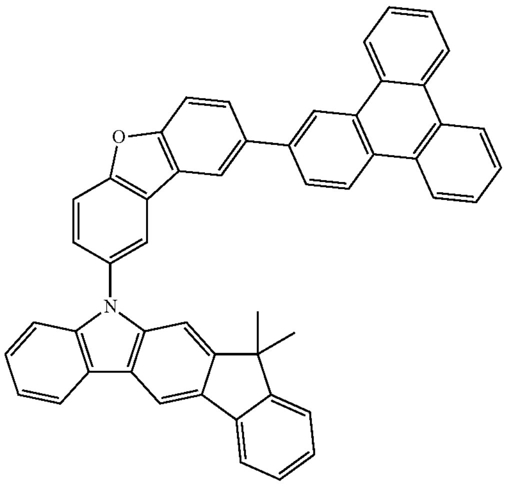 [SMILES: CC1(C)c2ccccc2-c2cc3c4ccccc4n(-c4ccc5oc6ccc(-c7ccc8c9ccccc9c9ccccc9c8c7)cc6c5c4)c3cc21]

TABLE 3-continued
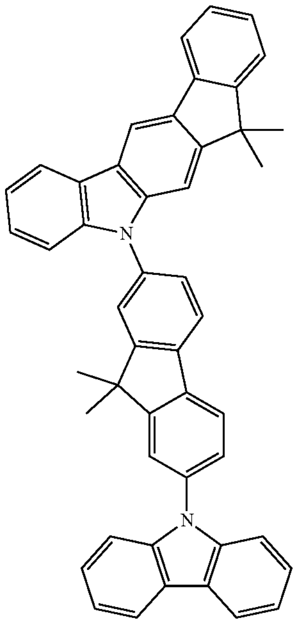 [SMILES: CC1(C)c2cc(-n3c4ccccc4c4ccccc43)ccc2-c2ccc(-n3c4ccccc4c4cc5c(cc43)C(C)(C)c3ccccc3-5)cc21]
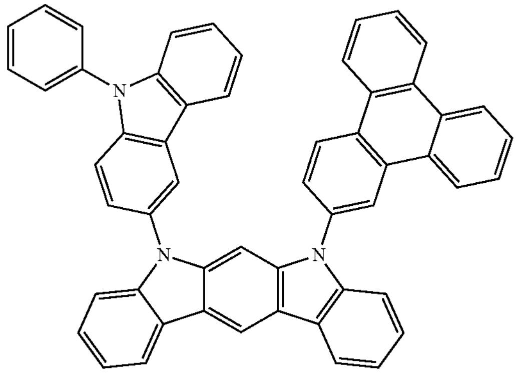 [SMILES: c1ccc(-n2c3ccccc3c3cc(-n4c5ccccc5c5cc6c7ccccc7n(-c7ccc8c9ccccc9c9ccccc9c8c7)c6cc54)ccc32)cc1]
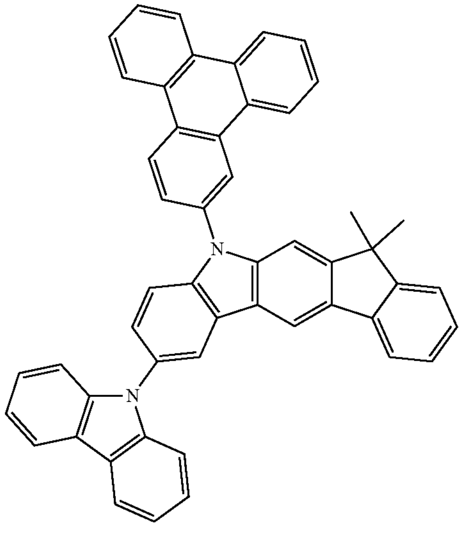 [SMILES: CC1(C)c2ccccc2-c2cc3c4cc(-n5c6ccccc6c6ccccc65)ccc4n(-c4ccc5c6ccccc6c6ccccc6c5c4)c3cc21]

TABLE 3-continued
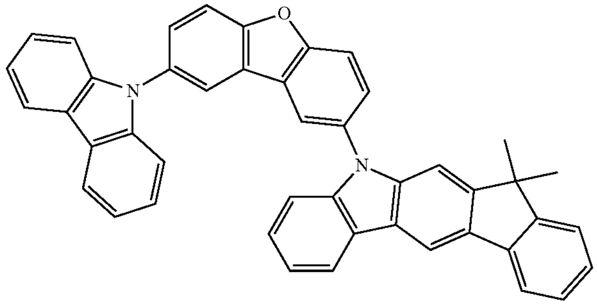 [SMILES: CC1(C)c2ccccc2-c2cc3c4ccccc4n(-c4ccc5oc6ccc(-n7c8ccccc8c8ccccc87)cc6c5c4)c3cc21]
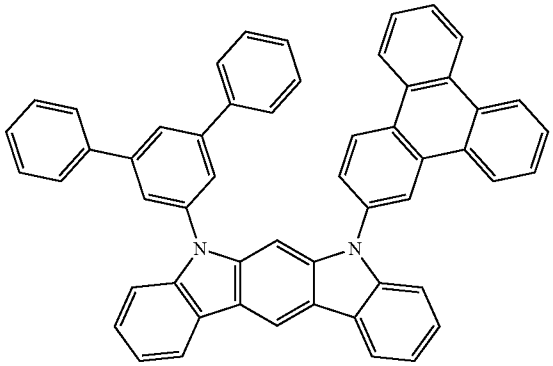 [SMILES: c1ccc(-c2cc(-c3ccccc3)cc(-n3c4ccccc4c4cc5c6ccccc6n(-c6ccc7c8ccccc8c8ccccc8c7c6)c5cc43)c2)cc1]
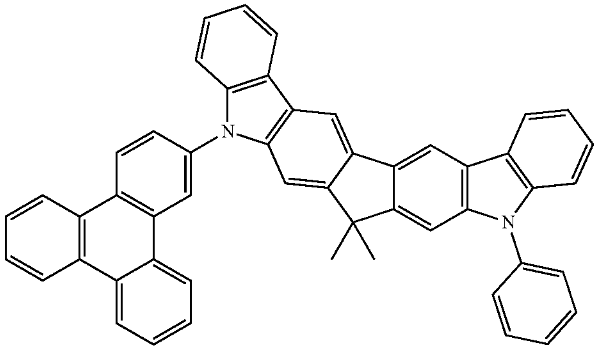 [SMILES: CC1(C)c2cc3c(cc2-c2cc4c5ccccc5n(-c5ccc6c7ccccc7c7ccccc7c6c5)c4cc21)c1ccccc1n3-c1ccccc1]
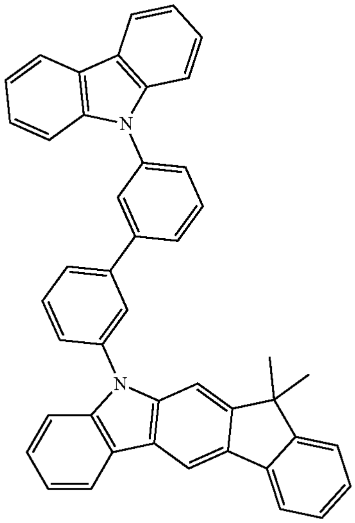 [SMILES: CC1(C)c2ccccc2-c2cc3c4ccccc4n(-c4cccc(-c5cccc(-n6c7ccccc7c7ccccc76)c5)c4)c3cc21]

TABLE 3-continued
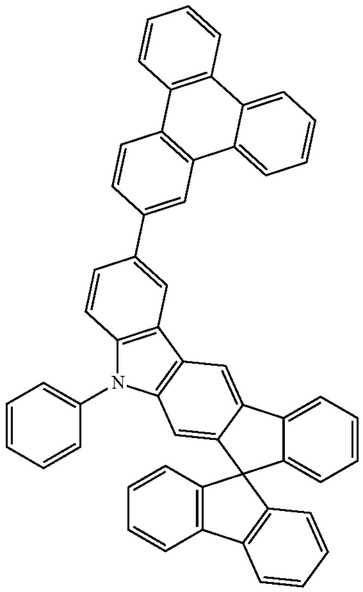 [SMILES: c1ccc(-n2c3ccc(-c4ccc5c6ccccc6c6ccccc6c5c4)cc3c3cc4c(cc32)C2(c3ccccc3-c3ccccc32)c2ccccc2-4)cc1]
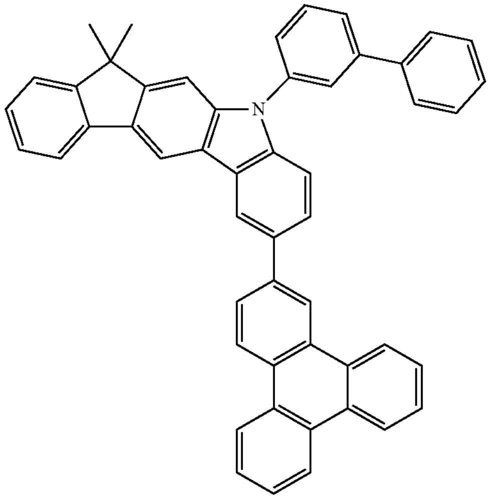 [SMILES: CC1(C)c2ccccc2-c2cc3c4cc(-c5ccc6c7ccccc7c7ccccc7c6c5)ccc4n(-c4cccc(-c5ccccc5)c4)c3cc21]

TABLE 3-continued
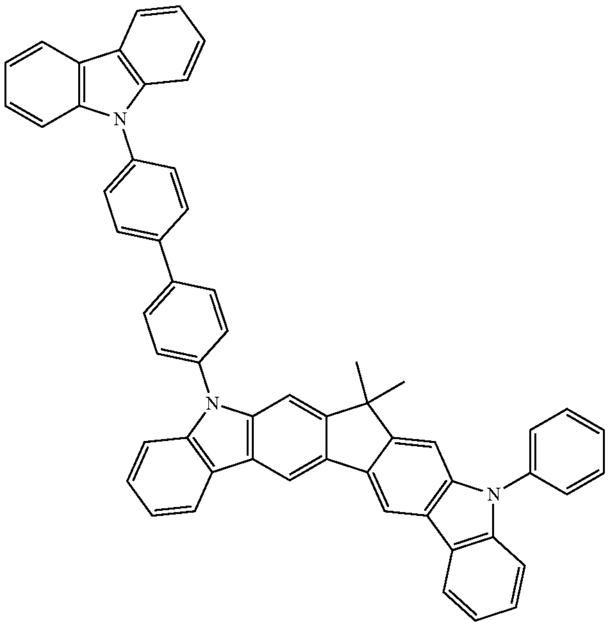 [SMILES: CC1(C)c2cc3c(cc2-c2cc4c5ccccc5n(-c5ccc(-c6ccc(-n7c8ccccc8c8ccccc87)cc6)cc5)c4cc21)c1ccccc1n3-c1ccccc1]
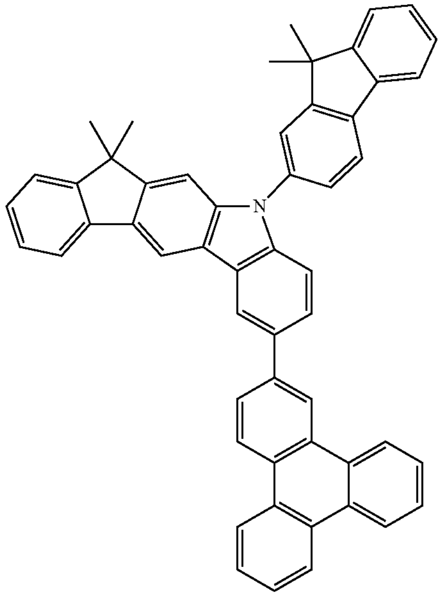 [SMILES: CC1(C)c2ccccc2-c2ccc(-n3c4ccc(-c5ccc6c7ccccc7c7ccccc7c6c5)cc4c4cc5c(cc43)C(C)(C)c3ccccc3-5)cc21]

TABLE 3-continued
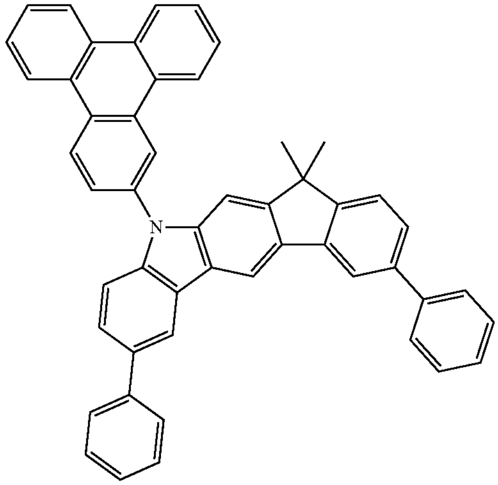 [SMILES: CC1(C)c2ccc(-c3ccccc3)cc2-c2cc3c4cc(-c5ccccc5)ccc4n(-c4ccc5c6ccccc6c6ccccc6c5c4)c3cc21]
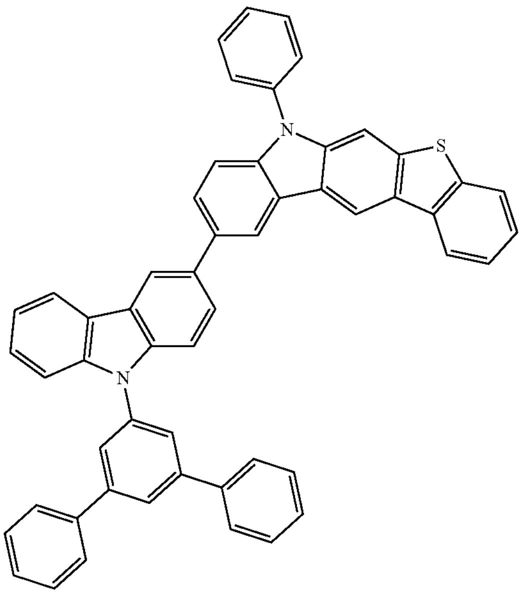 [SMILES: c1ccc(-c2cc(-c3ccccc3)cc(-n3c4ccccc4c4cc(-c5ccc6c(c5)c5cc7c(cc5n6-c5ccccc5)sc5ccccc57)ccc43)c2)cc1]

TABLE 3-continued
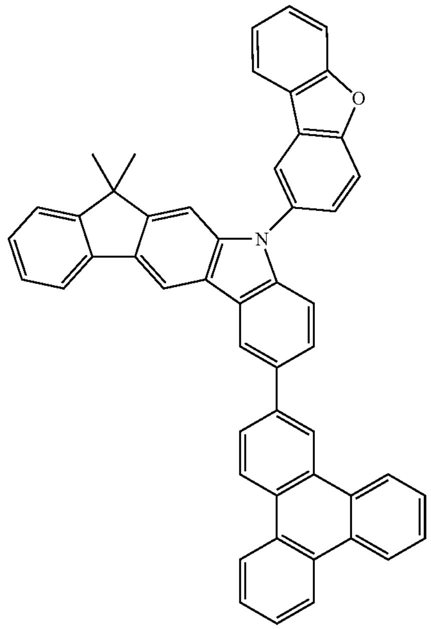 [SMILES: CC1(C)c2ccccc2-c2cc3c4cc(-c5ccc6c7ccccc7c7ccccc7c6c5)ccc4n(-c4ccc5oc6ccccc6c5c4)c3cc21]
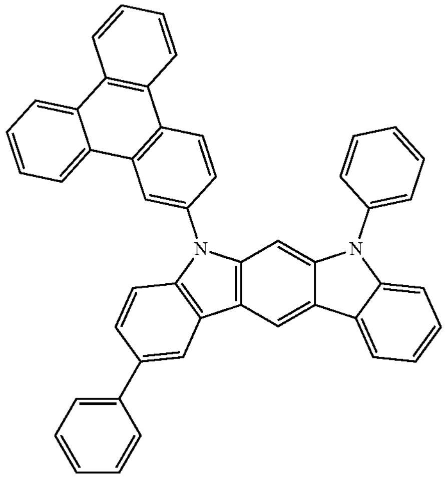 [SMILES: c1ccc(-c2ccc3c(c2)c2cc4c5ccccc5n(-c5ccccc5)c4cc2n3-c2ccc3c4ccccc4c4ccccc4c3c2)cc1]

TABLE 3-continued
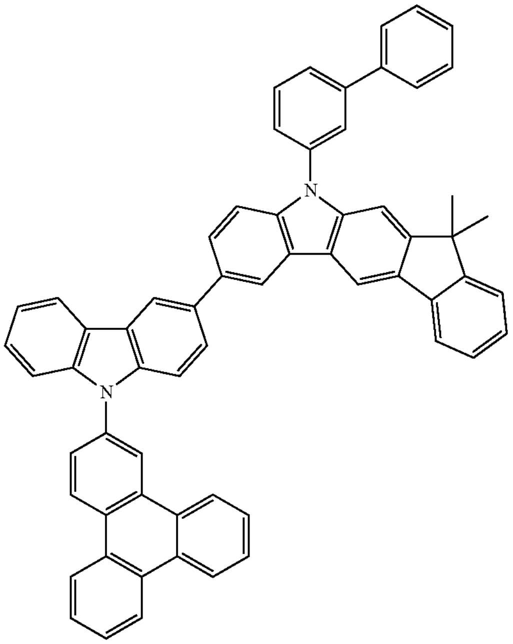 [SMILES: CC1(C)c2ccccc2-c2cc3c4cc(-c5ccc6c(c5)c5ccccc5n6-c5ccc6c7ccccc7c7ccccc7c6c5)ccc4n(-c4cccc(-c5ccccc5)c4)c3cc21]
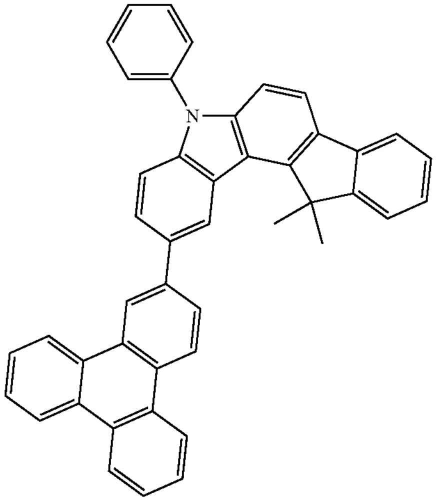 [SMILES: CC1(C)c2ccccc2-c2ccc3c(c21)c1cc(-c2ccc4c5ccccc5c5ccccc5c4c2)ccc1n3-c1ccccc1]
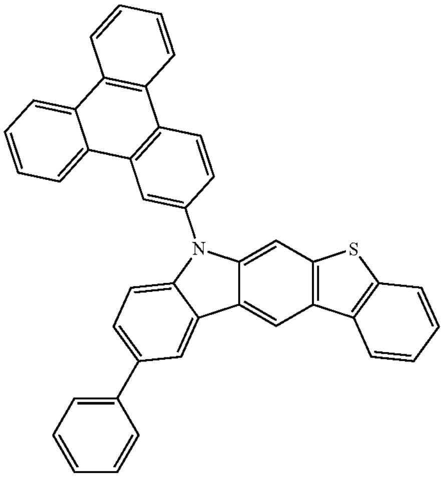 [SMILES: c1ccc(-c2ccc3c(c2)c2cc4c(cc2n3-c2ccc3c5ccccc5c5ccccc5c3c2)sc2ccccc24)cc1]

TABLE 3-continued
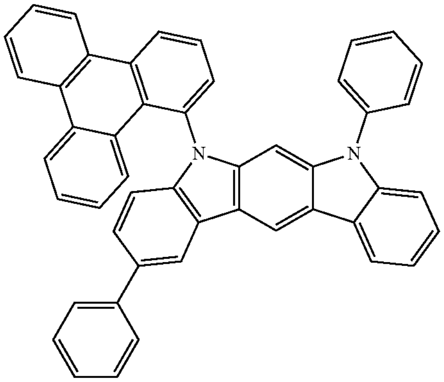 [SMILES: c1ccc(-c2ccc3c(c2)c2cc4c5ccccc5n(-c5ccccc5)c4cc2n3-c2cccc3c4ccccc4c4ccccc4c23)cc1]
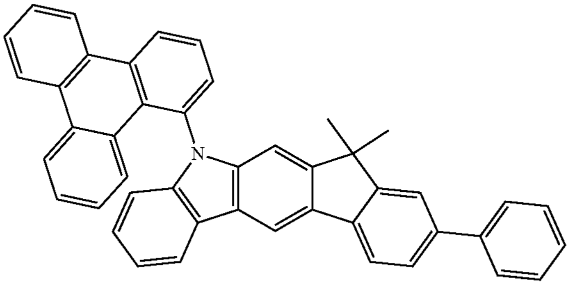 [SMILES: CC1(C)c2cc(-c3ccccc3)ccc2-c2cc3c4ccccc4n(-c4cccc5c6ccccc6c6ccccc6c45)c3cc21]
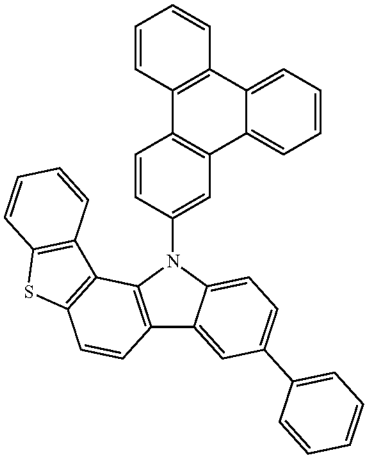 [SMILES: c1ccc(-c2ccc3c(c2)c2ccc4sc5ccccc5c4c2n3-c2ccc3c4ccccc4c4ccccc4c3c2)cc1]
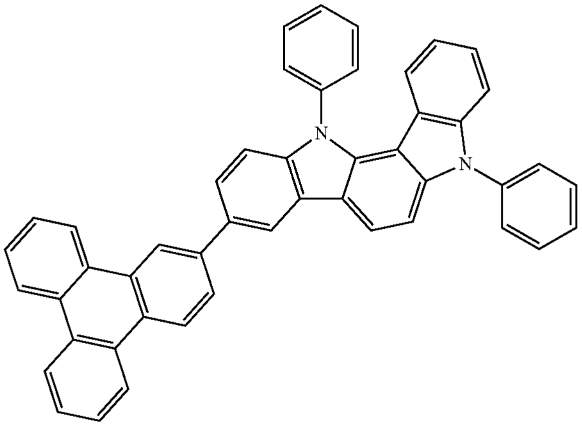 [SMILES: c1ccc(-n2c3ccccc3c3c2ccc2c4cc(-c5ccc6c7ccccc7c7ccccc7c6c5)ccc4n(-c4ccccc4)c23)cc1]

TABLE 3-continued
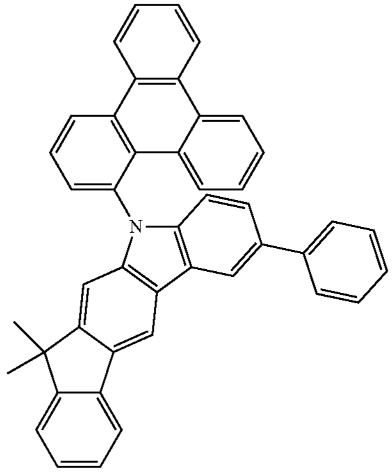 [SMILES: CC1(C)c2ccccc2-c2cc3c4cc(-c5ccccc5)ccc4n(-c4cccc5c6ccccc6c6ccccc6c45)c3cc21]
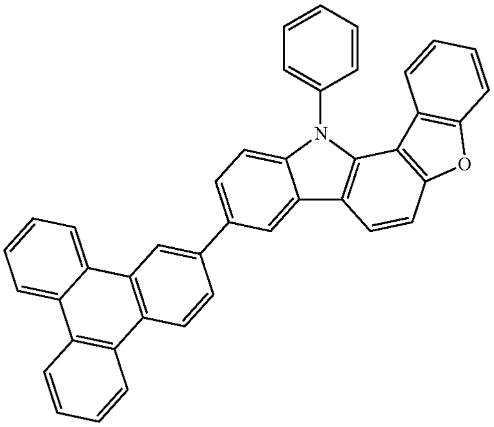 [SMILES: c1ccc(-n2c3ccc(-c4ccc5c6ccccc6c6ccccc6c5c4)cc3c3ccc4oc5ccccc5c4c32)cc1]
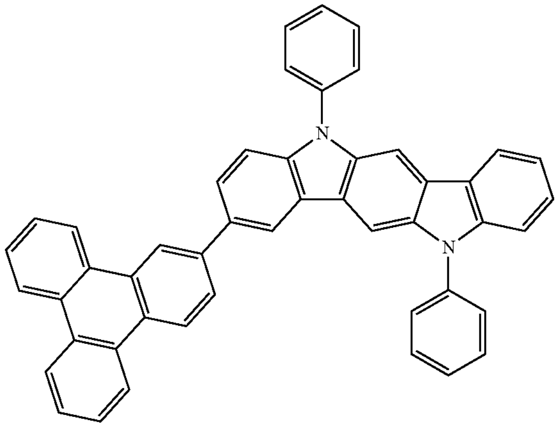 [SMILES: c1ccc(-n2c3ccccc3c3cc4c(cc32)c2cc(-c3ccc5c6ccccc6c6ccccc6c5c3)ccc2n4-c2ccccc2)cc1]

TABLE 3-continued
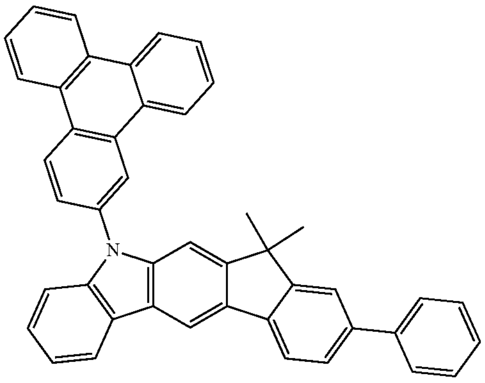 [SMILES: CC1(C)c2cc(-c3ccccc3)ccc2-c2cc3c4ccccc4n(-c4ccc5c6ccccc6c6ccccc6c5c4)c3cc21]
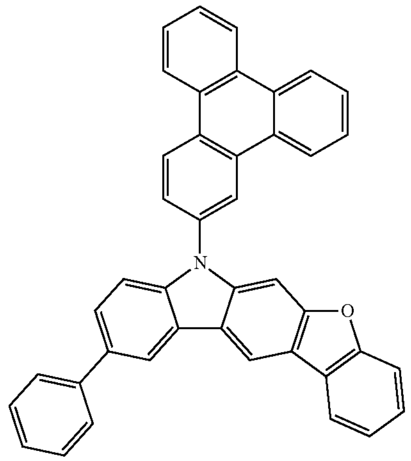 [SMILES: c1ccc(-c2ccc3c(c2)c2cc4c(cc2n3-c2ccc3c5ccccc5c5ccccc5c3c2)oc2ccccc24)cc1]
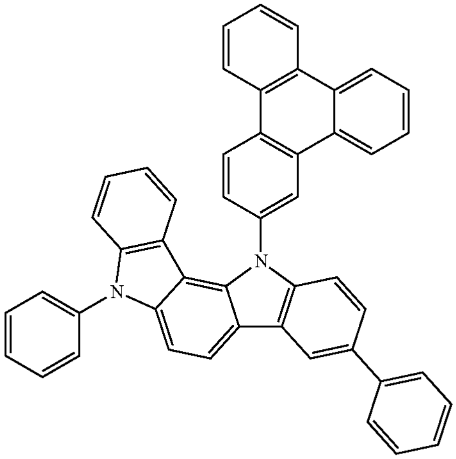 [SMILES: c1ccc(-c2ccc3c(c2)c2ccc4c(c5ccccc5n4-c4ccccc4)c2n3-c2ccc3c4ccccc4c4ccccc4c3c2)cc1]

TABLE 3-continued
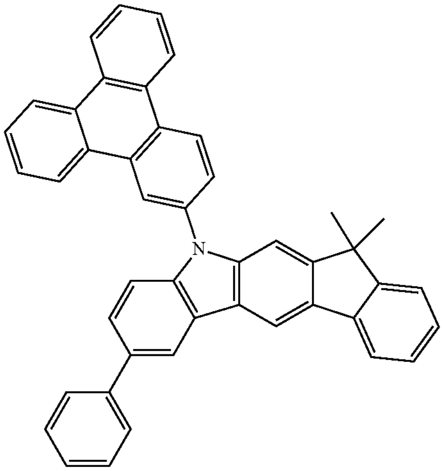 [SMILES: CC1(C)c2ccccc2-c2cc3c4cc(-c5ccccc5)ccc4n(-c4ccc5c6ccccc6c6ccccc6c5c4)c3cc21]
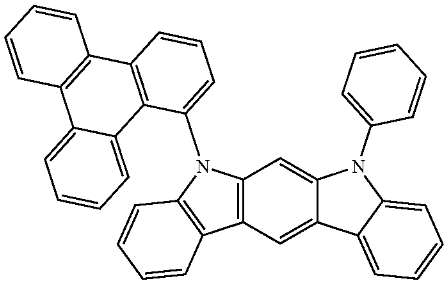 [SMILES: c1ccc(-n2c3ccccc3c3cc4c5ccccc5n(-c5cccc6c7ccccc7c7ccccc7c56)c4cc32)cc1]
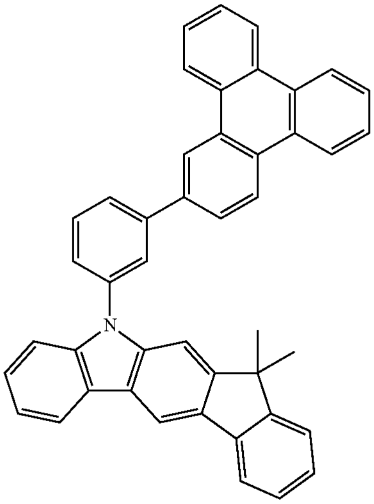 [SMILES: CC1(C)c2ccccc2-c2cc3c4ccccc4n(-c4cccc(-c5ccc6c7ccccc7c7ccccc7c6c5)c4)c3cc21]

TABLE 3-continued
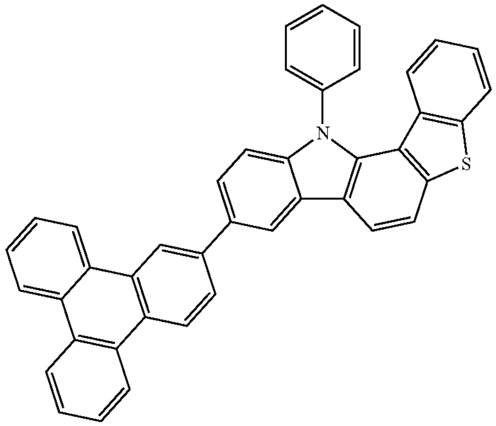
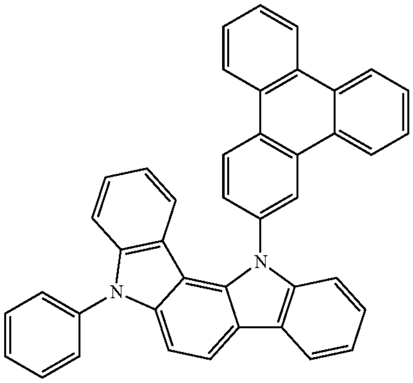 [SMILES: c1ccc(-n2c3ccccc3c3c2ccc2c4ccccc4n(-c4ccc5c6ccccc6c6ccccc6c5c4)c23)cc1]
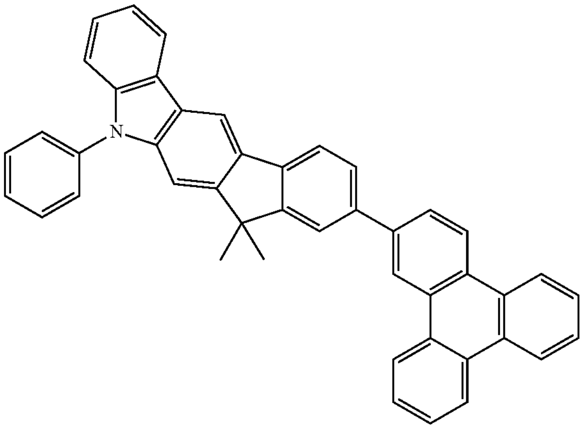 [SMILES: CC1(C)c2cc(-c3ccc4c5ccccc5c5ccccc5c4c3)ccc2-c2cc3c4ccccc4n(-c4ccccc4)c3cc21]

TABLE 3-continued
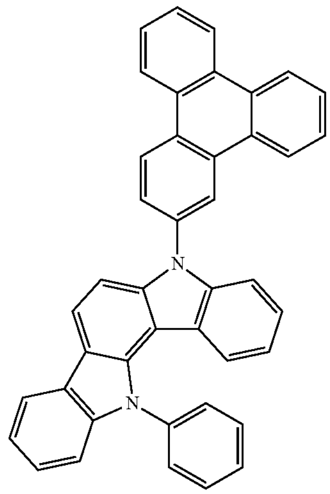 [SMILES: c1ccc(-n2c3ccccc3c3ccc4c(c5ccccc5n4-c4ccc5c6ccccc6c6ccccc6c5c4)c32)cc1]
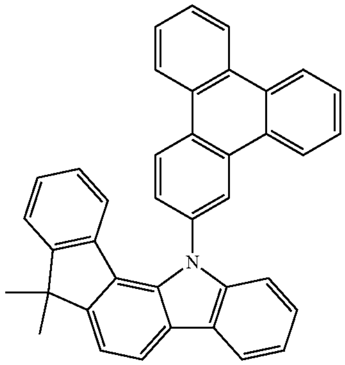 [SMILES: CC1(C)c2ccccc2-c2c1ccc1c3ccccc3n(-c3ccc4c5ccccc5c5ccccc5c4c3)c21]
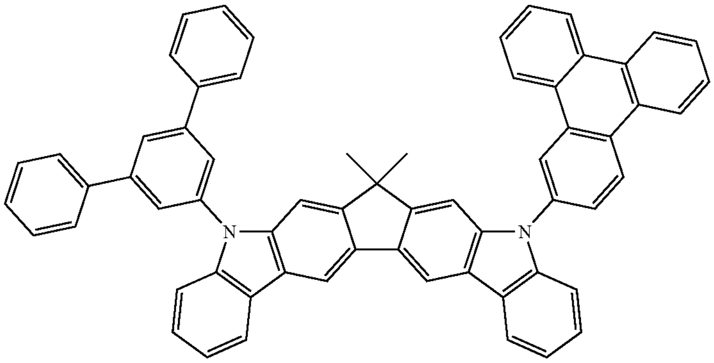 [SMILES: CC1(C)c2cc3c(cc2-c2cc4c5ccccc5n(-c5ccc6c7ccccc7c7ccccc7c6c5)c4cc21)c1ccccc1n3-c1cc(-c2ccccc2)cc(-c2ccccc2)c1]

TABLE 3-continued
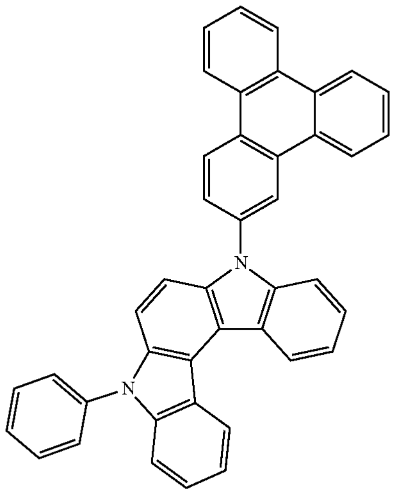 [SMILES: c1ccc(-n2c3ccccc3c3c4c5ccccc5n(-c5ccc6c7ccccc7c7ccccc7c6c5)c4ccc32)cc1]
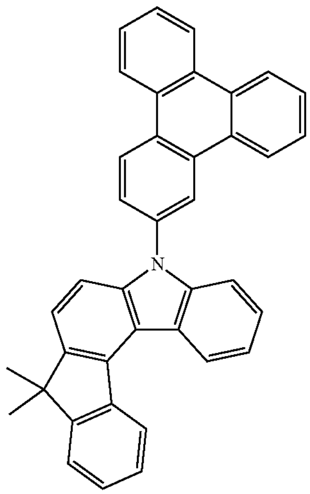 [SMILES: CC1(C)c2ccccc2-c2c1ccc1c2c2ccccc2n1-c1ccc2c3ccccc3c3ccccc3c2c1]
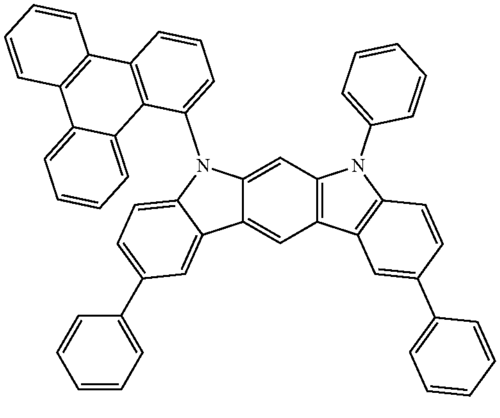 [SMILES: c1ccc(-c2ccc3c(c2)c2cc4c5cc(-c6ccccc6)ccc5n(-c5cccc6c7ccccc7c7ccccc7c56)c4cc2n3-c2ccccc2)cc1]

TABLE 3-continued
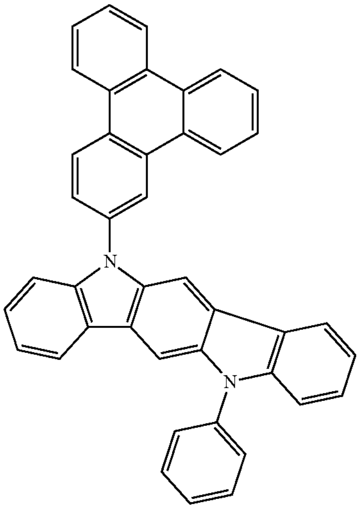 [SMILES: c1ccc(-n2c3ccccc3c3cc4c(cc32)c2ccccc2n4-c2ccc3c4ccccc4c4ccccc4c3c2)cc1]
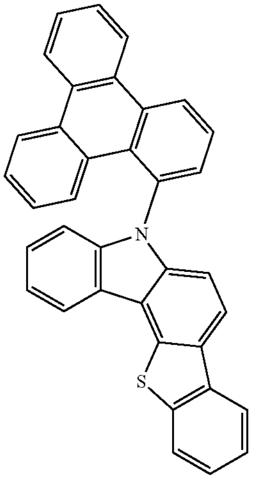 [SMILES: c1ccc2c(c1)sc1c2ccc2c1c1ccccc1n2-c1cccc2c3ccccc3c3ccccc3c12]
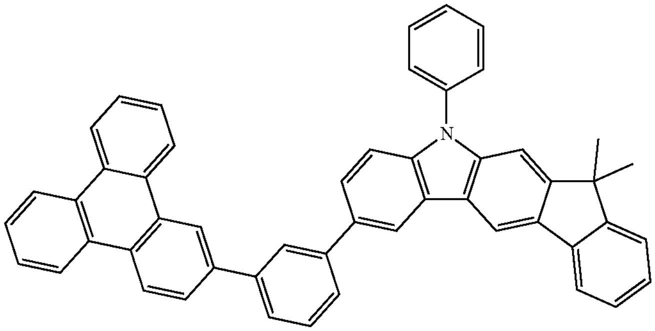 [SMILES: CC1(C)c2ccccc2-c2cc3c4cc(-c5cccc(-c6ccc7c8ccccc8c8ccccc8c7c6)c5)ccc4n(-c4ccccc4)c3cc21]

TABLE 3-continued
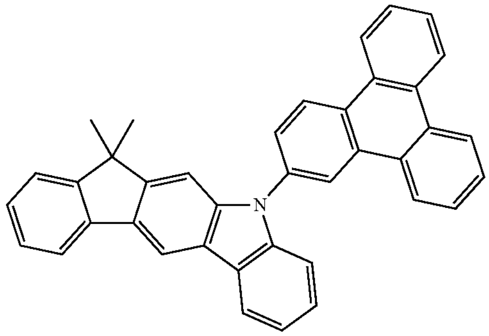 [SMILES: CC1(C)c2ccccc2-c2cc3c4ccccc4n(-c4ccc5c6ccccc6c6ccccc6c5c4)c3cc21]
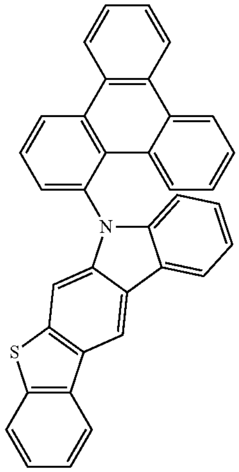 [SMILES: c1ccc2c(c1)sc1cc3c(cc12)c1ccccc1n3-c1cccc2c3ccccc3c3ccccc3c12]
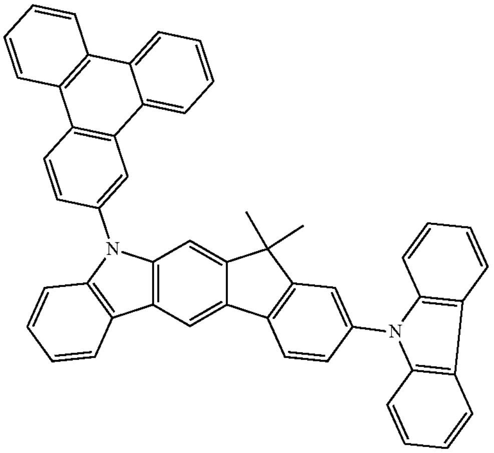 [SMILES: CC1(C)c2cc(-n3c4ccccc4c4ccccc43)ccc2-c2cc3c4ccccc4n(-c4ccc5c6ccccc6c6ccccc6c5c4)c3cc21]
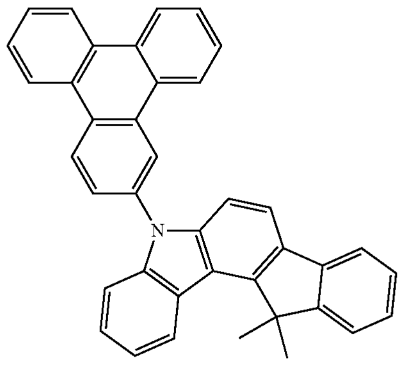 [SMILES: CC1(C)c2ccccc2-c2ccc3c(c21)c1ccccc1n3-c1ccc2c3ccccc3c3ccccc3c2c1]

TABLE 3-continued
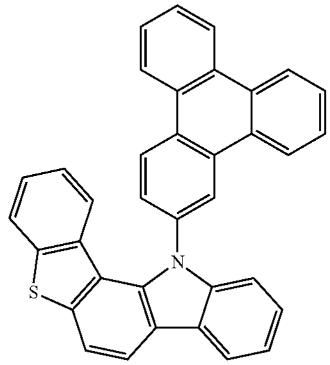 [SMILES: c1ccc2c(c1)sc1ccc3c4ccccc4n(-c4ccc5c6ccccc6c6ccccc6c5c4)c3c12]
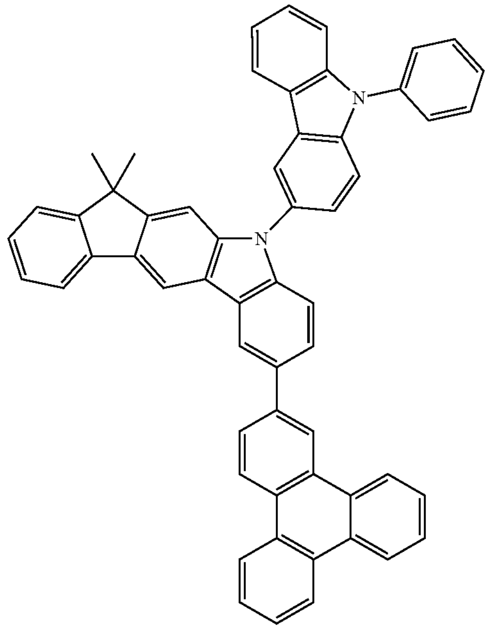 [SMILES: CC1(C)c2ccccc2-c2cc3c4cc(-c5ccc6c7ccccc7c7ccccc7c6c5)ccc4n(-c4ccc5c(c4)c4ccccc4n5-c4ccccc4)c3cc21]
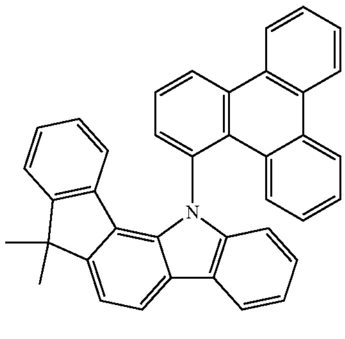 [SMILES: CC1(C)c2ccccc2-c2c1ccc1c3ccccc3n(-c3cccc4c5ccccc5c5ccccc5c34)c21]

TABLE 3-continued
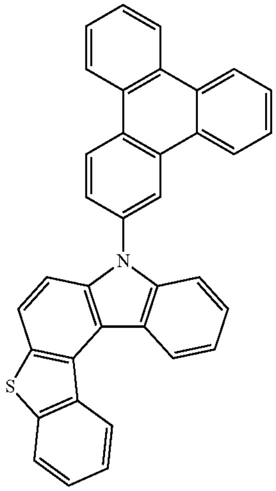 [SMILES: c1ccc2c(c1)sc1ccc3c(c4ccccc4n3-c3ccc4c5ccccc5c5ccccc5c4c3)c12]
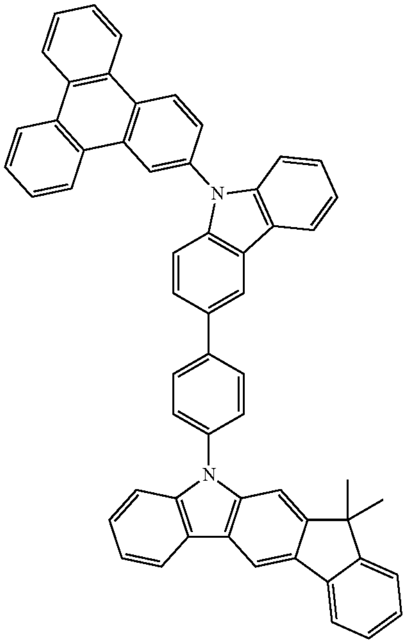 [SMILES: CC1(C)c2ccccc2-c2cc3c4ccccc4n(-c4ccc(-c5ccc6c(c5)c5ccccc5n6-c5ccc6c7ccccc7c7ccccc7c6c5)cc4)c3cc21]
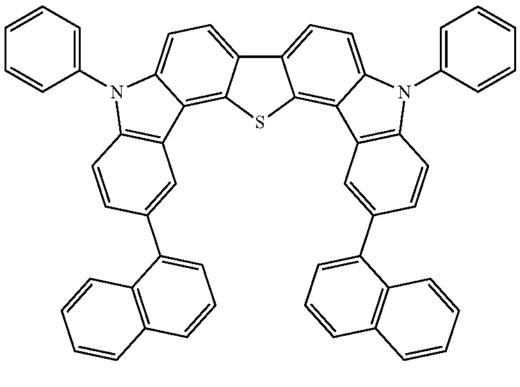 [SMILES: c1ccc(-n2c3ccc(-c4cccc5ccccc45)cc3c3c4sc5c(ccc6c5c5cc(-c7cccc8ccccc78)ccc5n6-c5ccccc5)c4ccc32)cc1]

TABLE 3-continued
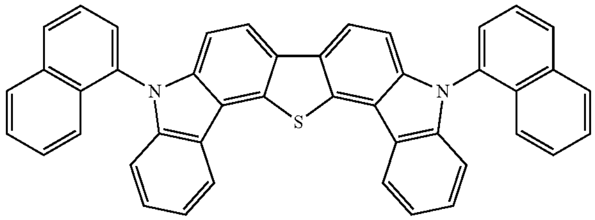
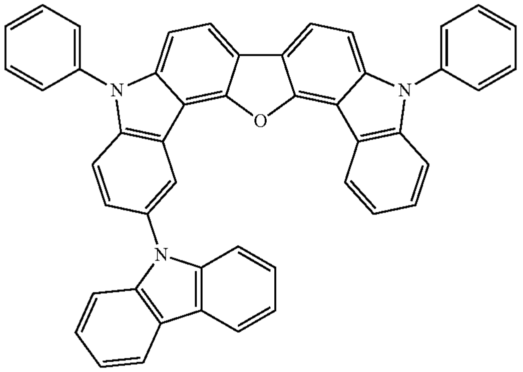 [SMILES: c1ccc(-n2c3ccccc3c3c4oc5c(ccc6c5c5cc(-n7c8ccccc8c8ccccc87)ccc5n6-c5ccccc5)c4ccc32)cc1]
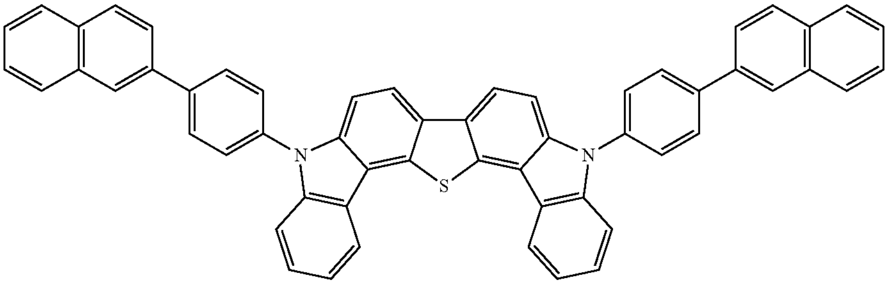 [SMILES: c1ccc2cc(-c3ccc(-n4c5ccccc5c5c6sc7c(ccc8c7c7ccccc7n8-c7ccc(-c8ccc9ccccc9c8)cc7)c6ccc54)cc3)ccc2c1]
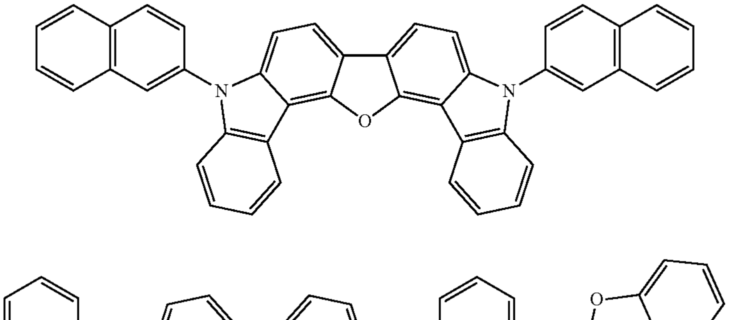
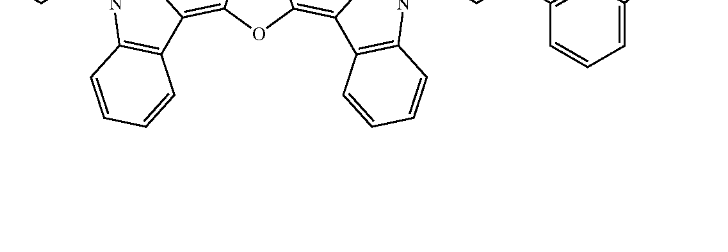

TABLE 3-continued
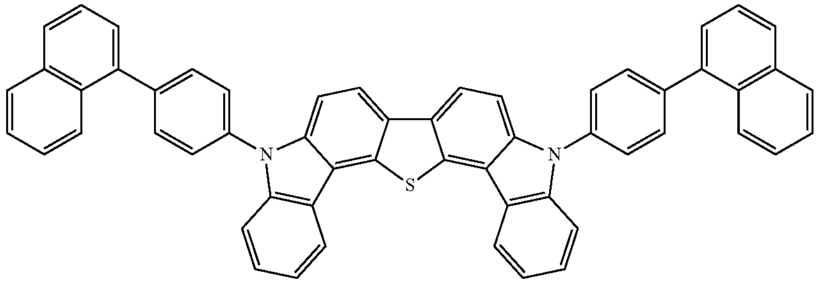 [SMILES: c1ccc2c(-c3ccc(-n4c5ccccc5c5c6sc7c(ccc8c7c7ccccc7n8-c7ccc(-c8cccc9ccccc89)cc7)c6ccc54)cc3)cccc2c1]
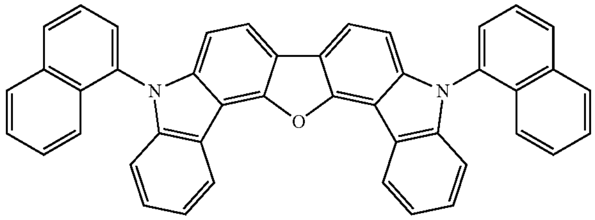 [SMILES: c1ccc2c(-n3c4ccccc4c4c5oc6c(ccc7c6c6ccccc6n7-c6cccc7ccccc67)c5ccc43)cccc2c1]
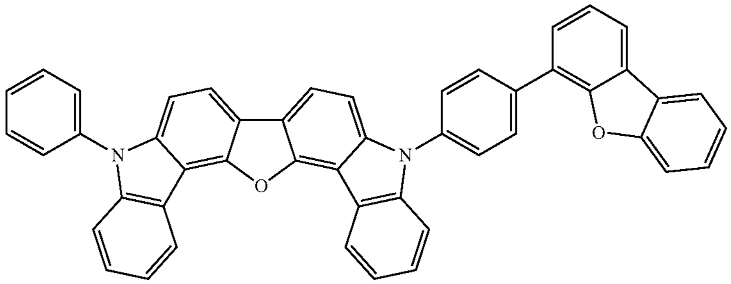 [SMILES: c1ccc(-n2c3ccccc3c3c4oc5c(ccc6c5c5ccccc5n6-c5ccc(-c6cccc7c6oc6ccccc67)cc5)c4ccc32)cc1]
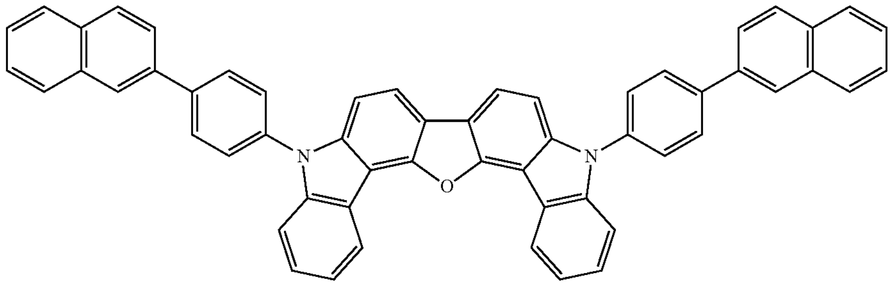 [SMILES: c1ccc2cc(-c3ccc(-n4c5ccccc5c5c6oc7c(ccc8c7c7ccccc7n8-c7ccc(-c8ccc9ccccc9c8)cc7)c6ccc54)cc3)ccc2c1]
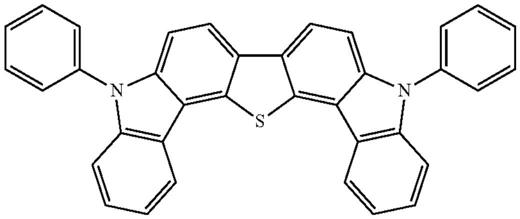 [SMILES: c1ccc(-n2c3ccccc3c3c4sc5c(ccc6c5c5ccccc5n6-c5ccccc5)c4ccc32)cc1]
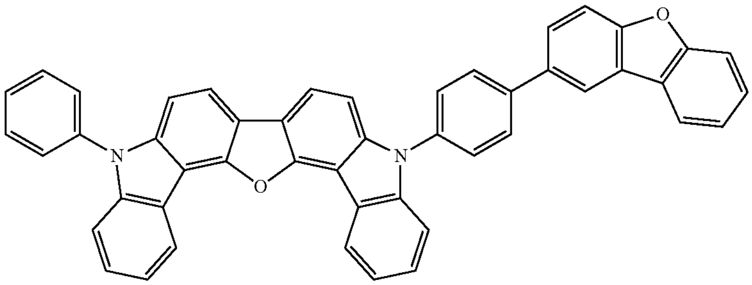 [SMILES: c1ccc(-n2c3ccccc3c3c4oc5c(ccc6c5c5ccccc5n6-c5ccc(-c6ccc7oc8ccccc8c7c6)cc5)c4ccc32)cc1]

TABLE 3-continued
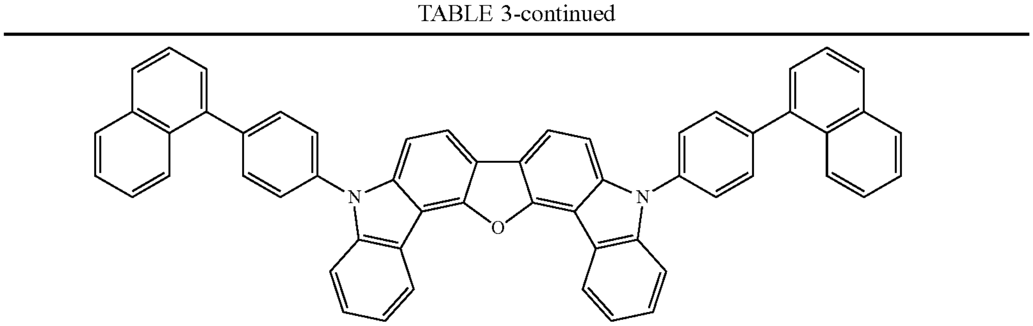
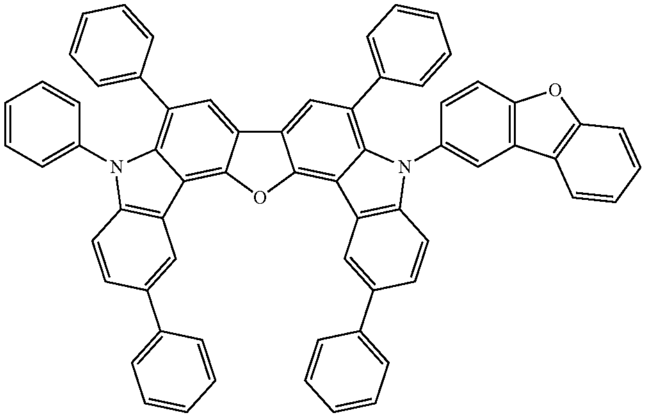 [SMILES: c1ccc(-c2ccc3c(c2)c2c4oc5c(cc(-c6ccccc6)c6c5c5cc(-c7ccccc7)ccc5n6-c5ccc6oc7ccccc7c6c5)c4cc(-c4ccccc4)c2n3-c2ccccc2)cc1]
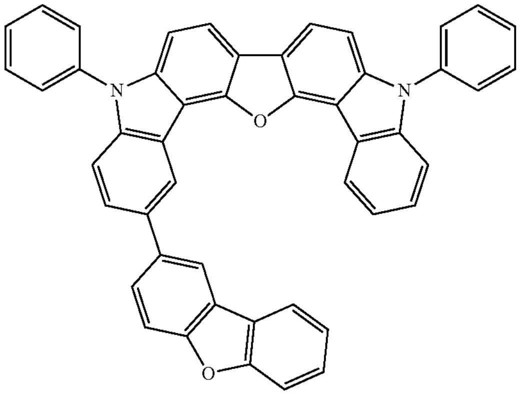 [SMILES: c1ccc(-n2c3ccccc3c3c4oc5c(ccc6c5c5cc(-c7ccc8oc9ccccc9c8c7)ccc5n6-c5ccccc5)c4ccc32)cc1]
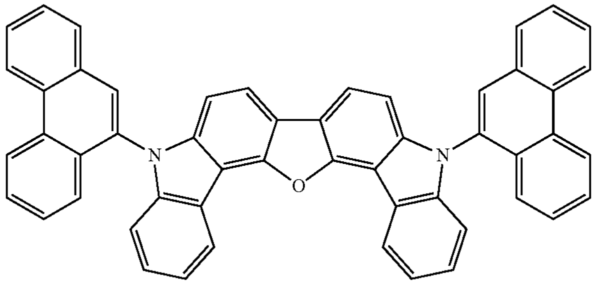 [SMILES: c1ccc2c(c1)cc(-n1c3ccccc3c3c4oc5c(ccc6c5c5ccccc5n6-c5cc6ccccc6c6ccccc56)c4ccc31)c1ccccc12]
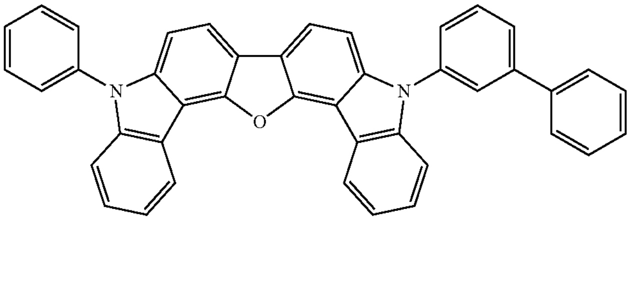 [SMILES: c1ccc(-c2cccc(-n3c4ccccc4c4c5oc6c(ccc7c6c6ccccc6n7-c6ccccc6)c5ccc43)c2)cc1]

TABLE 3-continued
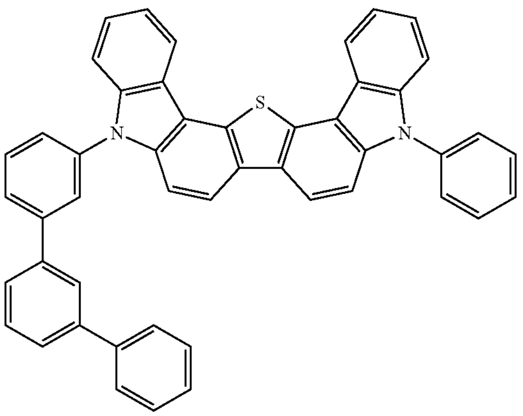 [SMILES: c1ccc(-c2cccc(-c3cccc(-n4c5ccccc5c5c6sc7c(ccc8c7c7ccccc7n8-c7ccccc7)c6ccc54)c3)c2)cc1]
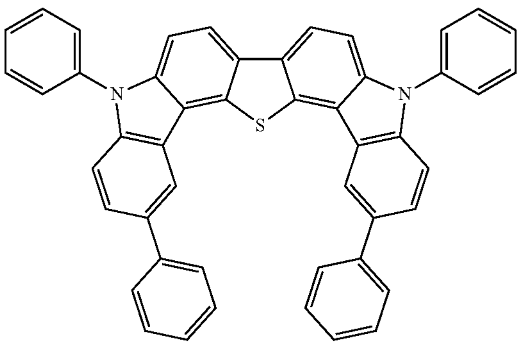
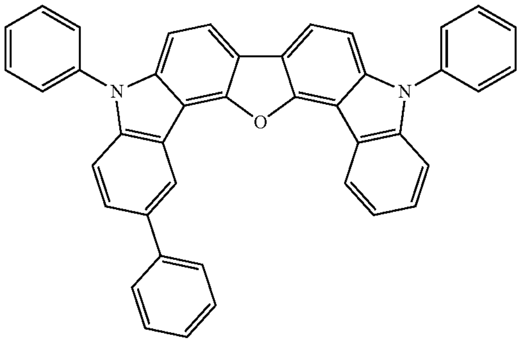 [SMILES: c1ccc(-c2ccc3c(c2)c2c4oc5c(ccc6c5c5ccccc5n6-c5ccccc5)c4ccc2n3-c2ccccc2)cc1]
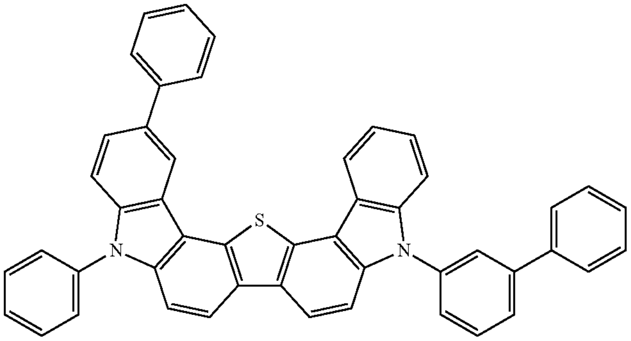 [SMILES: c1ccc(-c2cccc(-n3c4ccccc4c4c5sc6c(ccc7c6c6cc(-c8ccccc8)ccc6n7-c6ccccc6)c5ccc43)c2)cc1]

TABLE 3-continued
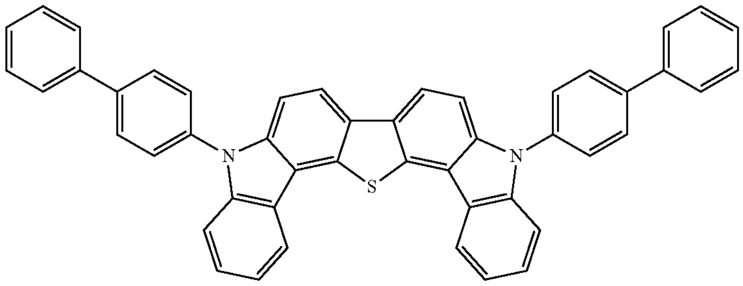 [SMILES: c1ccc(-c2ccc(-n3c4ccccc4c4c5sc6c(ccc7c6c6ccccc6n7-c6ccc(-c7ccccc7)cc6)c5ccc43)cc2)cc1]
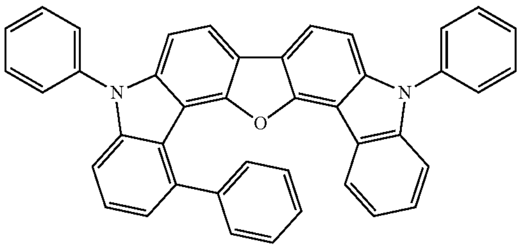 [SMILES: c1ccc(-c2cccc3c2c2c4oc5c(ccc6c5c5ccccc5n6-c5ccccc5)c4ccc2n3-c2ccccc2)cc1]
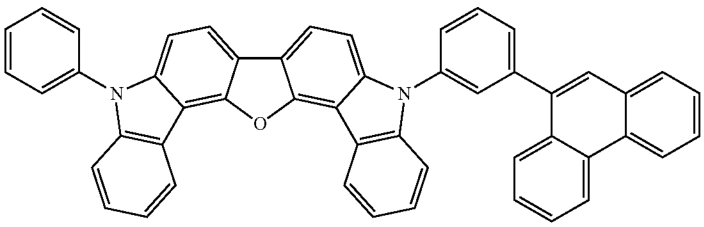 [SMILES: c1ccc(-n2c3ccccc3c3c4oc5c(ccc6c5c5ccccc5n6-c5cccc(-c6cc7ccccc7c7ccccc67)c5)c4ccc32)cc1]
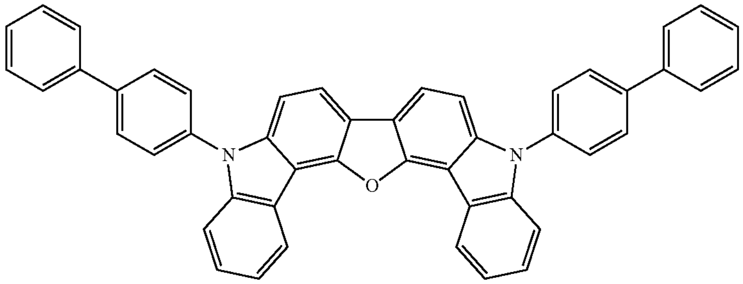 [SMILES: c1ccc(-c2ccc(-n3c4ccccc4c4c5oc6c(ccc7c6c6ccccc6n7-c6ccc(-c7ccccc7)cc6)c5ccc43)cc2)cc1]
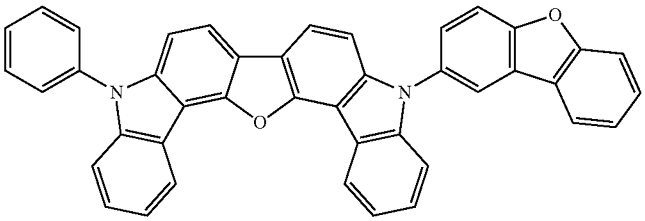 [SMILES: c1ccc(-n2c3ccccc3c3c4oc5c(ccc6c5c5ccccc5n6-c5ccc6oc7ccccc7c6c5)c4ccc32)cc1]
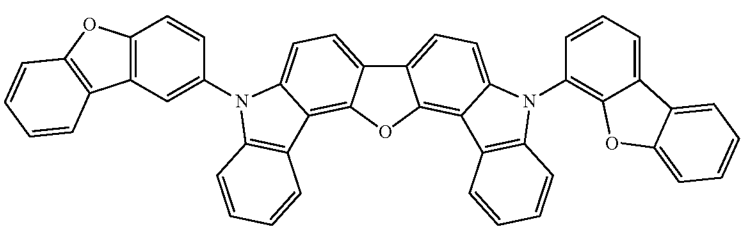 [SMILES: c1ccc2c(c1)oc1ccc(-n3c4ccccc4c4c5oc6c(ccc7c6c6ccccc6n7-c6cccc7c6oc6ccccc67)c5ccc43)cc12]

TABLE 3-continued
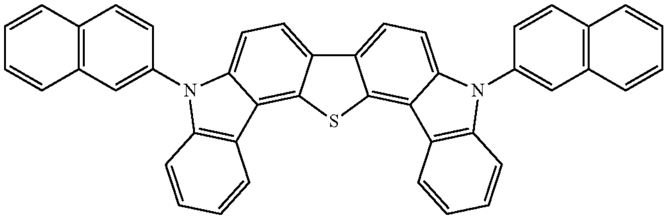
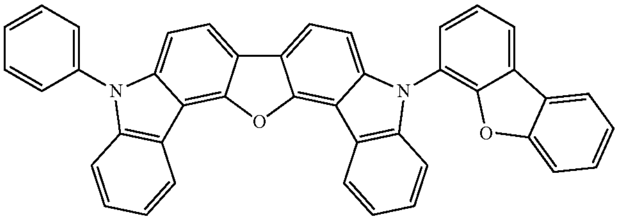 [SMILES: c1ccc(-n2c3ccccc3c3c4oc5c(ccc6c5c5ccccc5n6-c5cccc6c5oc5ccccc56)c4ccc32)cc1]
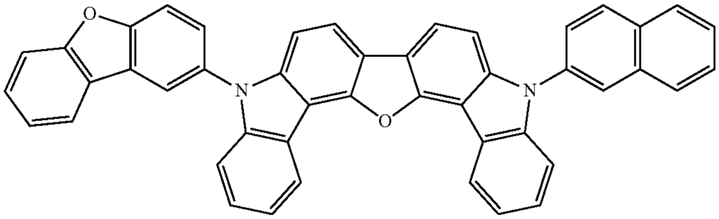 [SMILES: c1ccc2cc(-n3c4ccccc4c4c5oc6c(ccc7c6c6ccccc6n7-c6ccc7oc8ccccc8c7c6)c5ccc43)ccc2c1]
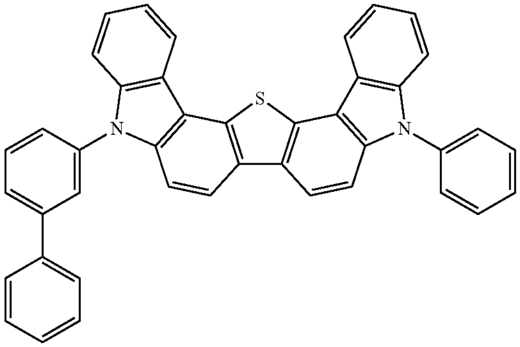 [SMILES: c1ccc(-c2cccc(-n3c4ccccc4c4c5sc6c(ccc7c6c6ccccc6n7-c6ccccc6)c5ccc43)c2)cc1]
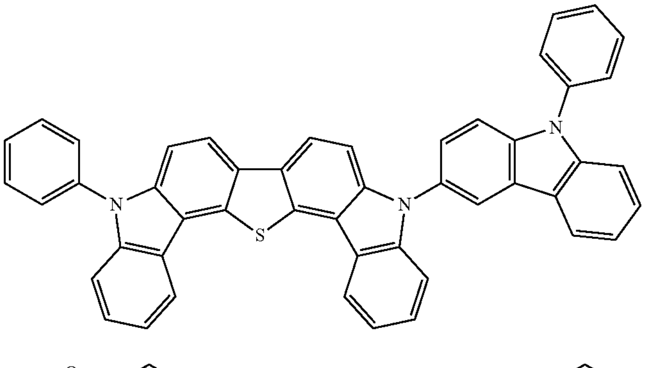
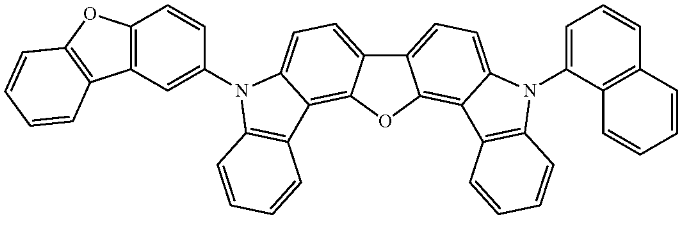 [SMILES: c1ccc2c(-n3c4ccccc4c4c5oc6c(ccc7c6c6ccccc6n7-c6ccc7oc8ccccc8c7c6)c5ccc43)cccc2c1]

TABLE 3-continued
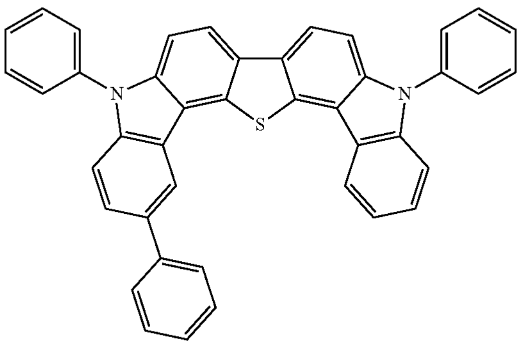 [SMILES: c1ccc(-c2ccc3c(c2)c2c4sc5c(ccc6c5c5ccccc5n6-c5ccccc5)c4ccc2n3-c2ccccc2)cc1]
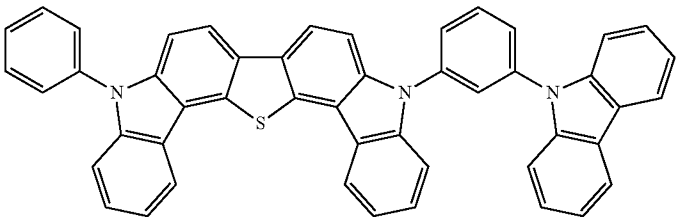 [SMILES: c1ccc(-n2c3ccccc3c3c4sc5c(ccc6c5c5ccccc5n6-c5cccc(-n6c7ccccc7c7ccccc76)c5)c4ccc32)cc1]
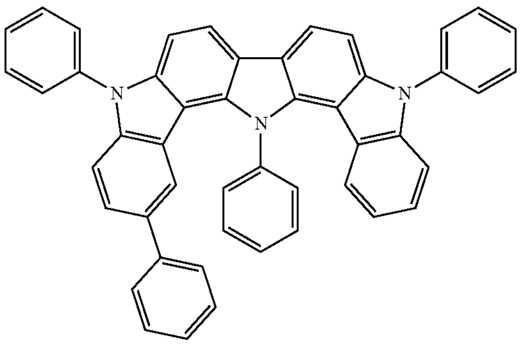 [SMILES: c1ccc(-c2ccc3c(c2)c2c(ccc4c5ccc6c(c7ccccc7n6-c6ccccc6)c5n(-c5ccccc5)c42)n3-c2ccccc2)cc1]
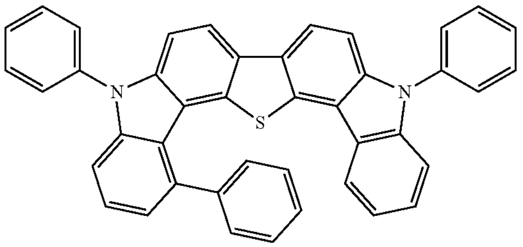 [SMILES: c1ccc(-c2cccc3c2c2c4sc5c(ccc6c5c5ccccc5n6-c5ccccc5)c4ccc2n3-c2ccccc2)cc1]
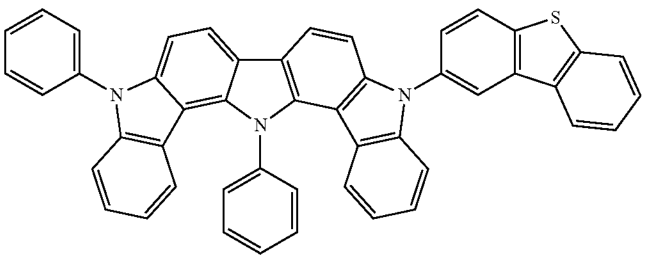

TABLE 3-continued
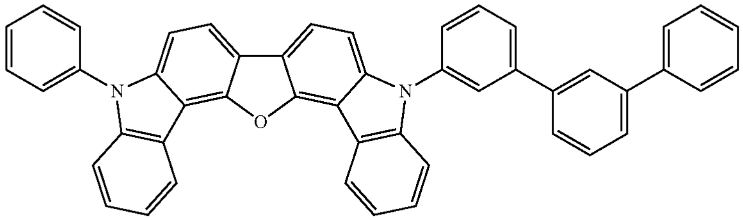 [SMILES: c1ccc(-c2cccc(-c3cccc(-n4c5ccccc5c5c6oc7c(ccc8c7c7ccccc7n8-c7ccccc7)c6ccc54)c3)c2)cc1]
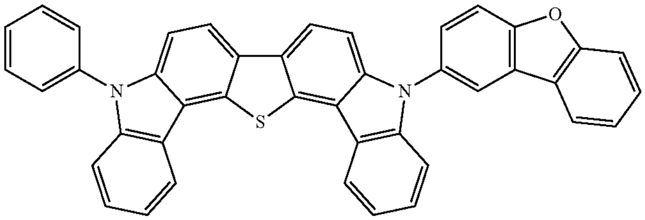 [SMILES: c1ccc(-n2c3ccccc3c3c4sc5c(ccc6c5c5ccccc5n6-c5ccc6oc7ccccc7c6c5)c4ccc32)cc1]
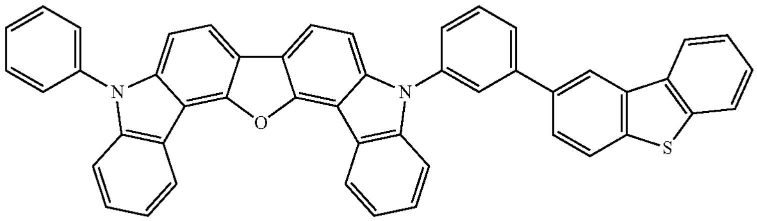 [SMILES: c1ccc(-n2c3ccccc3c3c4oc5c(ccc6c5c5ccccc5n6-c5cccc(-c6ccc7sc8ccccc8c7c6)c5)c4ccc32)cc1]
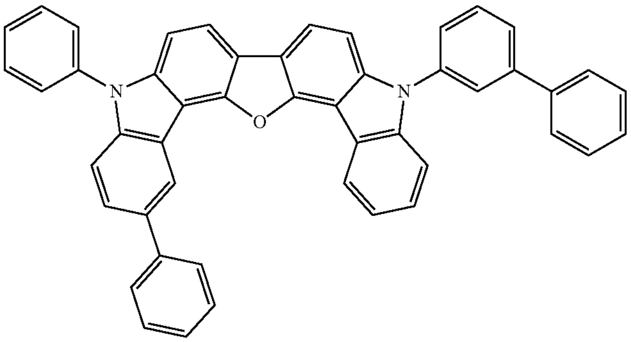 [SMILES: c1ccc(-c2cccc(-n3c4ccccc4c4c5oc6c(ccc7c6c6cc(-c8ccccc8)ccc6n7-c6ccccc6)c5ccc43)c2)cc1]
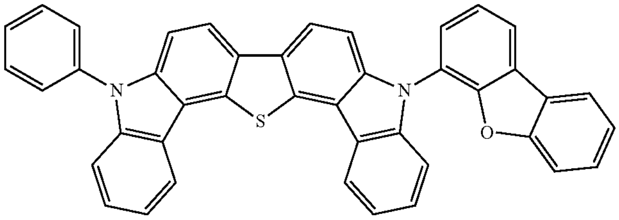
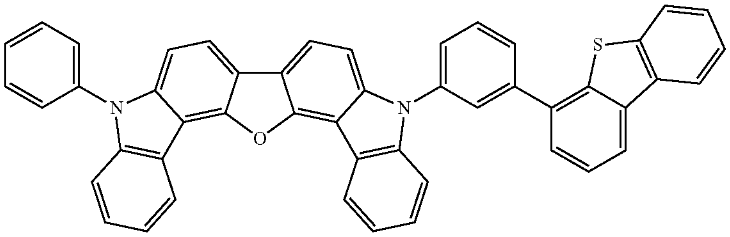 [SMILES: c1ccc(-n2c3ccccc3c3c4oc5c(ccc6c5c5ccccc5n6-c5cccc(-c6cccc7c6sc6ccccc67)c5)c4ccc32)cc1]

TABLE 3-continued
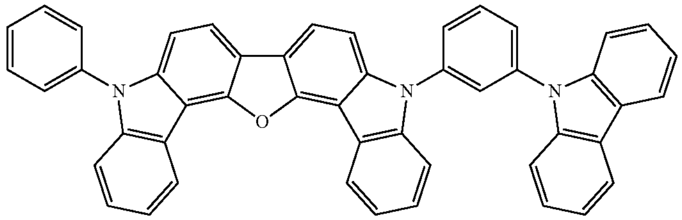 [SMILES: c1ccc(-n2c3ccccc3c3c4oc5c(ccc6c5c5ccccc5n6-c5cccc(-n6c7ccccc7c7ccccc76)c5)c4ccc32)cc1]
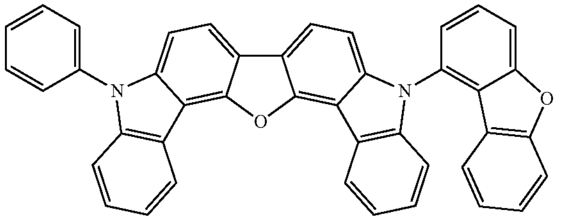 [SMILES: c1ccc(-n2c3ccccc3c3c4oc5c(ccc6c5c5ccccc5n6-c5cccc6oc7ccccc7c56)c4ccc32)cc1]
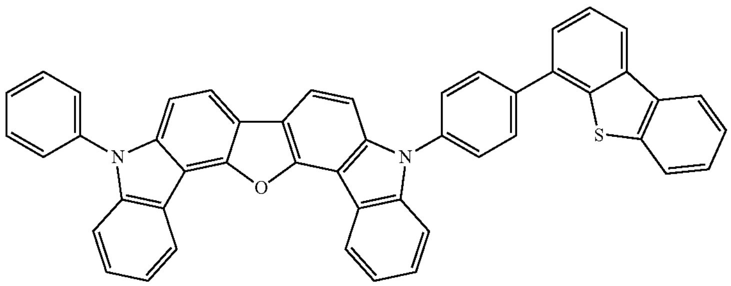 [SMILES: c1ccc(-n2c3ccccc3c3c4oc5c(ccc6c5c5ccccc5n6-c5ccc(-c6cccc7c6sc6ccccc67)cc5)c4ccc32)cc1]
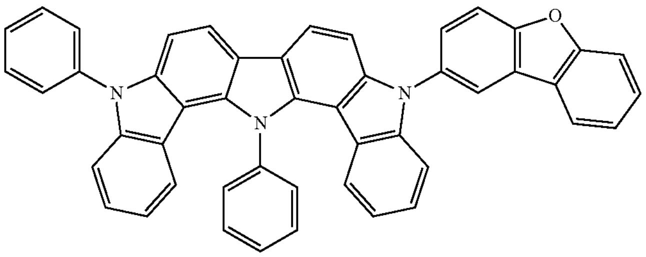 [SMILES: c1ccc(-n2c3ccccc3c3c2ccc2c4ccc5c(c6ccccc6n5-c5ccc6oc7ccccc7c6c5)c4n(-c4ccccc4)c23)cc1]
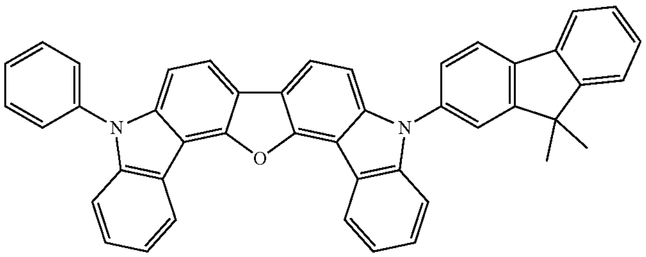 [SMILES: CC1(C)c2ccccc2-c2ccc(-n3c4ccccc4c4c5oc6c(ccc7c6c6ccccc6n7-c6ccccc6)c5ccc43)cc21]
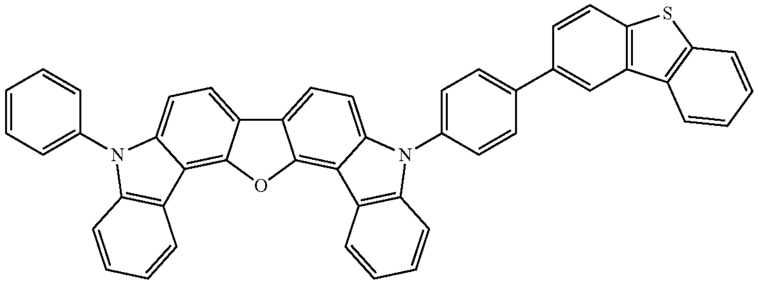 [SMILES: c1ccc(-n2c3ccccc3c3c4oc5c(ccc6c5c5ccccc5n6-c5ccc(-c6ccc7sc8ccccc8c7c6)cc5)c4ccc32)cc1]

TABLE 3-continued
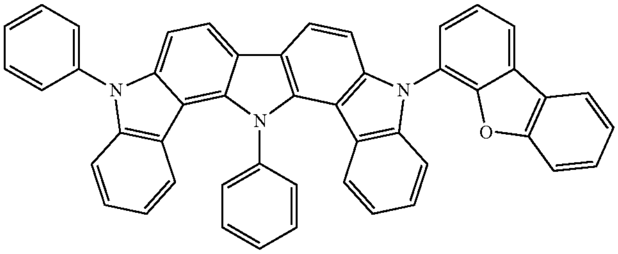 [SMILES: c1ccc(-n2c3ccccc3c3c2ccc2c4ccc5c(c6ccccc6n5-c5cccc6c5oc5ccccc56)c4n(-c4ccccc4)c23)cc1]
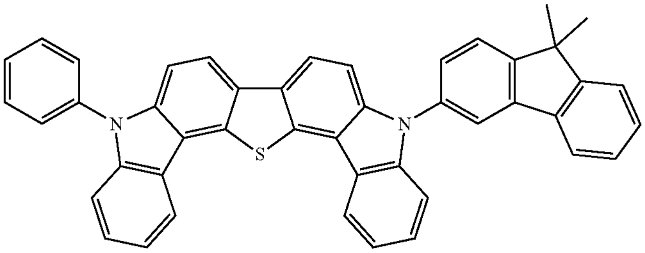 [SMILES: CC1(C)c2ccccc2-c2cc(-n3c4ccccc4c4c5sc6c(ccc7c6c6ccccc6n7-c6ccccc6)c5ccc43)ccc21]
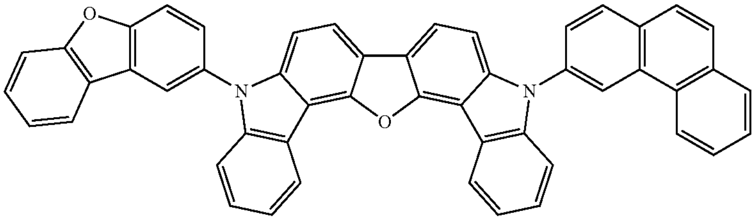 [SMILES: c1ccc2c(c1)ccc1ccc(-n3c4ccccc4c4c5oc6c(ccc7c6c6ccccc6n7-c6ccc7oc8ccccc8c7c6)c5ccc43)cc12]
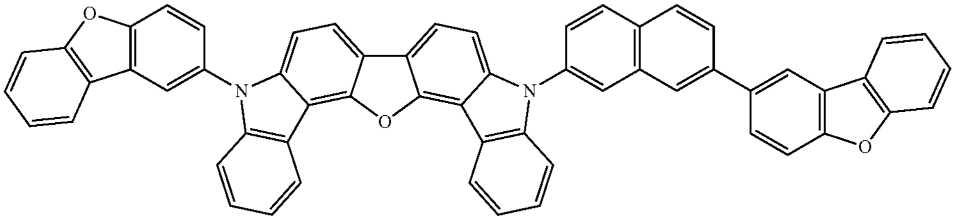 [SMILES: c1ccc2c(c1)oc1ccc(-c3ccc4ccc(-n5c6ccccc6c6c7oc8c(ccc9c8c8ccccc8n9-c8ccc9oc%10ccccc%10c9c8)c7ccc65)cc4c3)cc12]
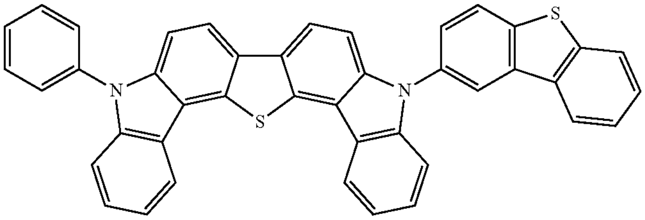
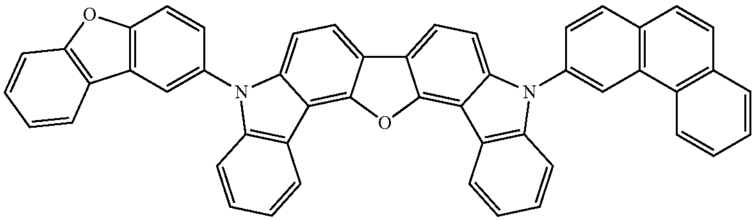 [SMILES: c1ccc2c(c1)ccc1ccc(-n3c4ccccc4c4c5oc6c(ccc7c6c6ccccc6n7-c6ccc7oc8ccccc8c7c6)c5ccc43)cc12]

TABLE 3-continued
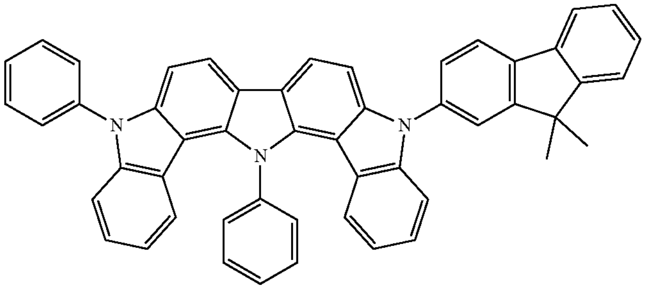 [SMILES: CC1(C)c2ccccc2-c2ccc(-n3c4ccccc4c4c3ccc3c5ccc6c(c7ccccc7n6-c6ccccc6)c5n(-c5ccccc5)c34)cc21]
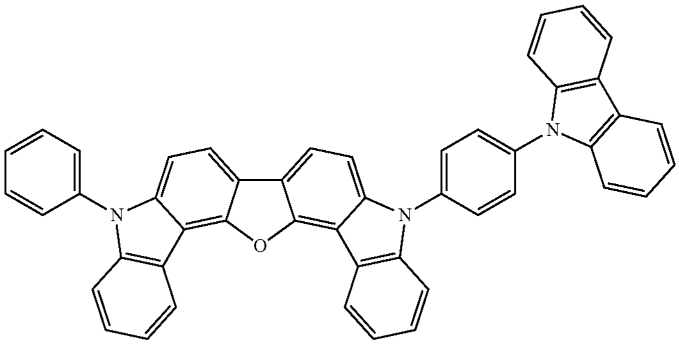 [SMILES: c1ccc(-n2c3ccccc3c3c4oc5c(ccc6c5c5ccccc5n6-c5ccc(-n6c7ccccc7c7ccccc76)cc5)c4ccc32)cc1]
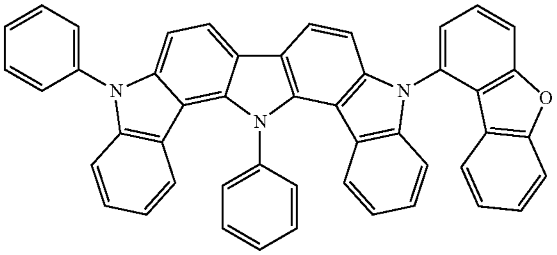 [SMILES: c1ccc(-n2c3ccccc3c3c2ccc2c4ccc5c(c6ccccc6n5-c5cccc6oc7ccccc7c56)c4n(-c4ccccc4)c23)cc1]
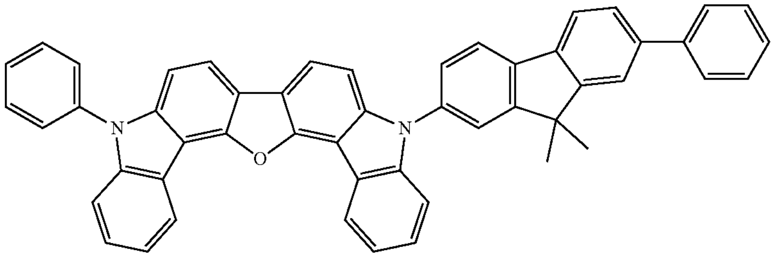 [SMILES: CC1(C)c2cc(-c3ccccc3)ccc2-c2ccc(-n3c4ccccc4c4c5oc6c(ccc7c6c6ccccc6n7-c6ccccc6)c5ccc43)cc21]
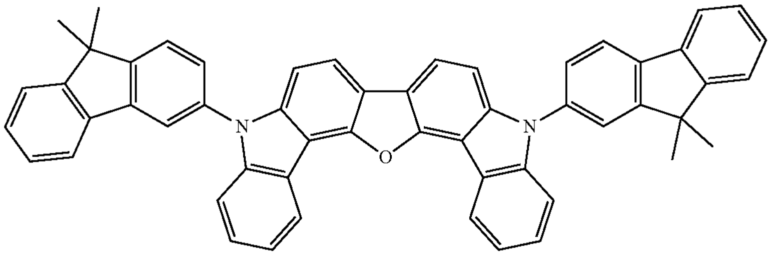 [SMILES: CC1(C)c2ccccc2-c2cc(-n3c4ccccc4c4c5oc6c(ccc7c6c6ccccc6n7-c6ccc7c(c6)C(C)(C)c6ccccc6-7)c5ccc43)ccc21]

TABLE 3-continued
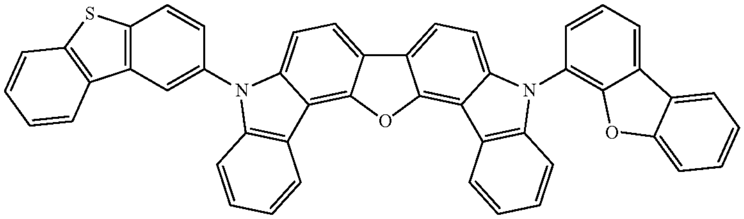 [SMILES: c1ccc2c(c1)oc1c(-n3c4ccccc4c4c5oc6c(ccc7c6c6ccccc6n7-c6ccc7sc8ccccc8c7c6)c5ccc43)cccc12]
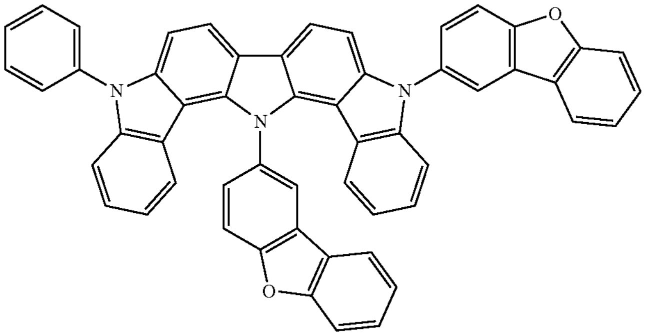 [SMILES: c1ccc(-n2c3ccccc3c3c2ccc2c4ccc5c(c6ccccc6n5-c5ccc6oc7ccccc7c6c5)c4n(-c4ccc5oc6ccccc6c5c4)c23)cc1]
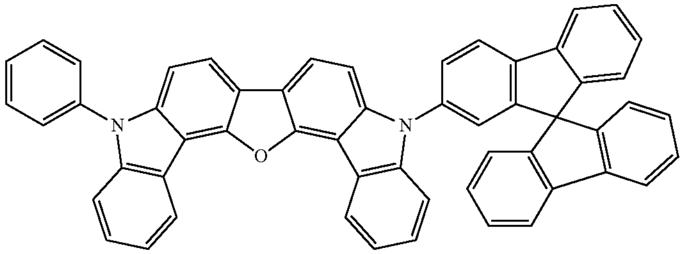 [SMILES: c1ccc(-n2c3ccccc3c3c4oc5c(ccc6c5c5ccccc5n6-c5ccc6c(c5)C5(c7ccccc7-c7ccccc75)c5ccccc5-6)c4ccc32)cc1]
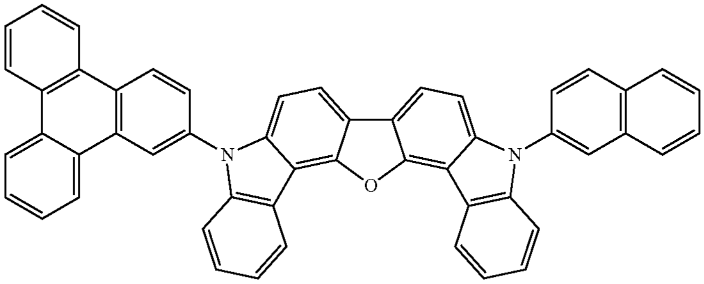 [SMILES: c1ccc2cc(-n3c4ccccc4c4c5oc6c(ccc7c6c6ccccc6n7-c6ccc7c8ccccc8c8ccccc8c7c6)c5ccc43)ccc2c1]
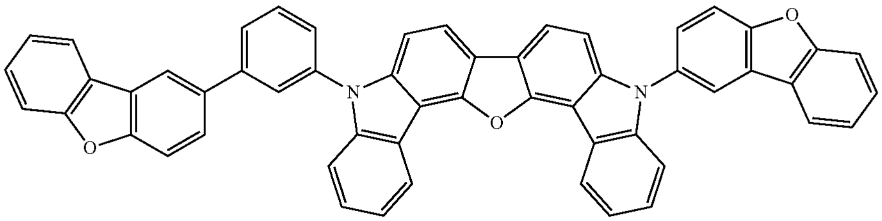 [SMILES: c1cc(-c2ccc3oc4ccccc4c3c2)cc(-n2c3ccccc3c3c4oc5c(ccc6c5c5ccccc5n6-c5ccc6oc7ccccc7c6c5)c4ccc32)c1]
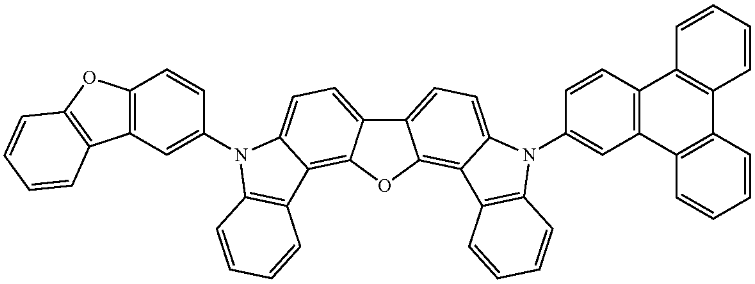 [SMILES: c1ccc2c(c1)oc1ccc(-n3c4ccccc4c4c5oc6c(ccc7c6c6ccccc6n7-c6ccc7c8ccccc8c8ccccc8c7c6)c5ccc43)cc12]

TABLE 3-continued
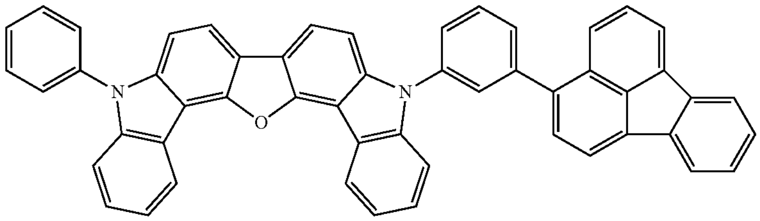 [SMILES: c1ccc(-n2c3ccccc3c3c4oc5c(ccc6c5c5ccccc5n6-c5cccc(-c6ccc7c8c(cccc68)-c6ccccc6-7)c5)c4ccc32)cc1]
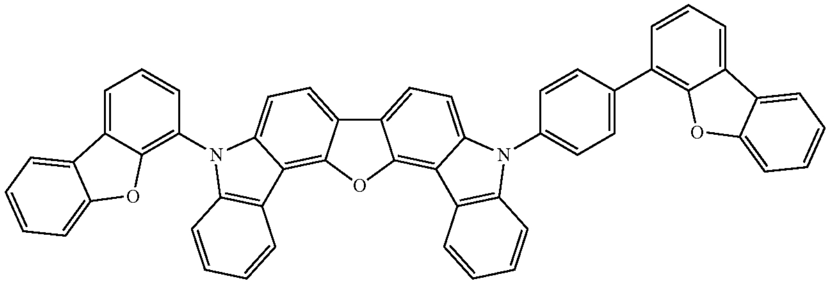 [SMILES: c1ccc2c(c1)oc1c(-c3ccc(-n4c5ccccc5c5c6oc7c(ccc8c7c7ccccc7n8-c7cccc8c7oc7ccccc78)c6ccc54)cc3)cccc12]
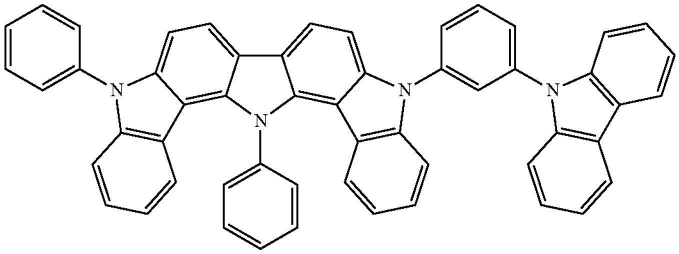 [SMILES: c1ccc(-n2c3ccccc3c3c2ccc2c4ccc5c(c6ccccc6n5-c5cccc(-n6c7ccccc7c7ccccc76)c5)c4n(-c4ccccc4)c23)cc1]
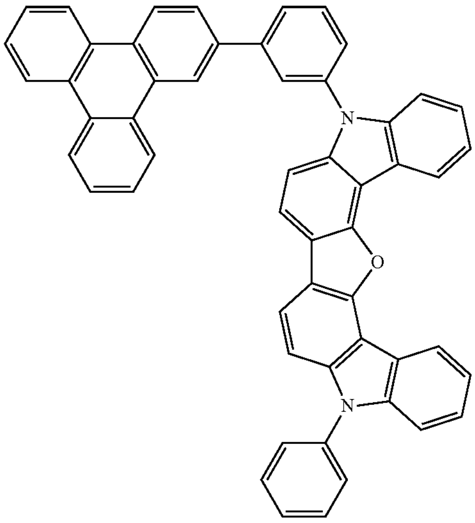 [SMILES: c1ccc(-n2c3ccccc3c3c4oc5c(ccc6c5c5ccccc5n6-c5cccc(-c6ccc7c8ccccc8c8ccccc8c7c6)c5)c4ccc32)cc1]

TABLE 3-continued
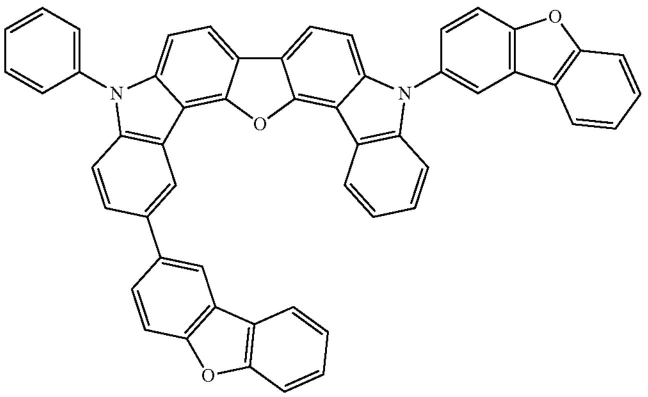 [SMILES: c1ccc(-n2c3ccc(-c4ccc5oc6ccccc6c5c4)cc3c3c4oc5c(ccc6c5c5ccccc5n6-c5ccc6oc7ccccc7c6c5)c4ccc32)cc1]
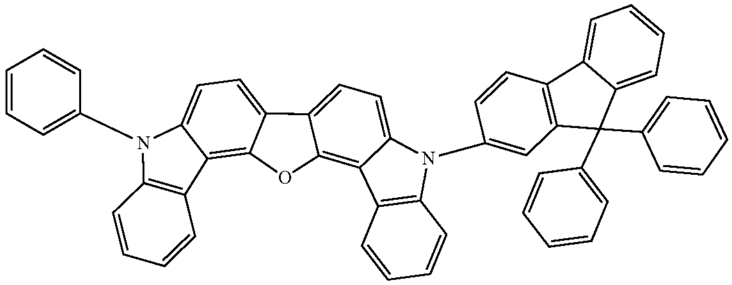 [SMILES: c1ccc(-n2c3ccccc3c3c4oc5c(ccc6c5c5ccccc5n6-c5ccc6c(c5)C(c5ccccc5)(c5ccccc5)c5ccccc5-6)c4ccc32)cc1]
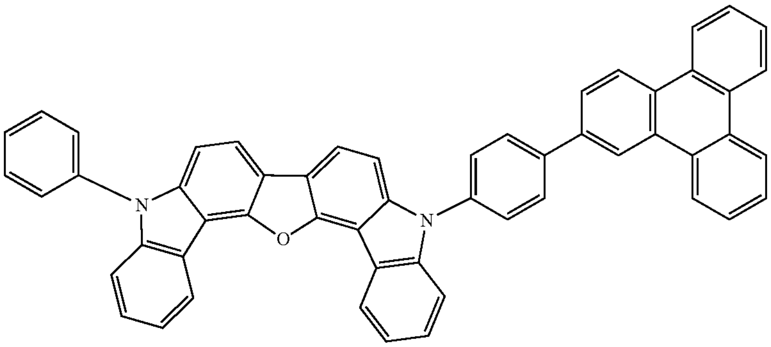 [SMILES: c1ccc(-n2c3ccccc3c3c4oc5c(ccc6c5c5ccccc5n6-c5ccc(-c6ccc7c8ccccc8c8ccccc8c7c6)cc5)c4ccc32)cc1]
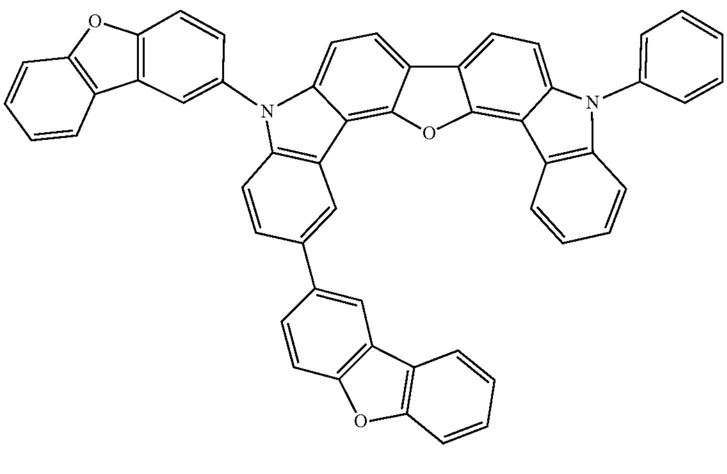 [SMILES: c1ccc(-n2c3ccccc3c3c4oc5c(ccc6c5c5cc(-c7ccc8oc9ccccc9c8c7)ccc5n6-c5ccc6oc7ccccc7c6c5)c4ccc32)cc1]

TABLE 3-continued
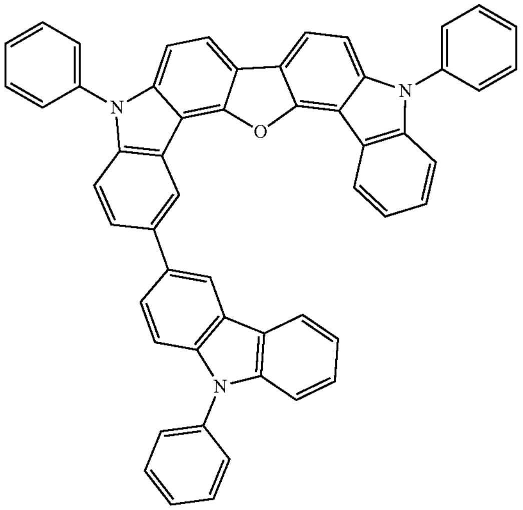 [SMILES: c1ccc(-n2c3ccccc3c3cc(-c4ccc5c(c4)c4c6oc7c(ccc8c7c7ccccc7n8-c7ccccc7)c6ccc4n5-c4ccccc4)ccc32)cc1]
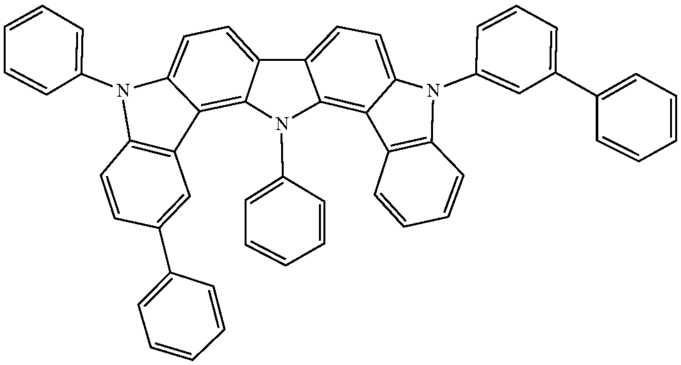 [SMILES: c1ccc(-c2cccc(-n3c4ccccc4c4c3ccc3c5ccc6c(c7cc(-c8ccccc8)ccc7n6-c6ccccc6)c5n(-c5ccccc5)c34)c2)cc1]
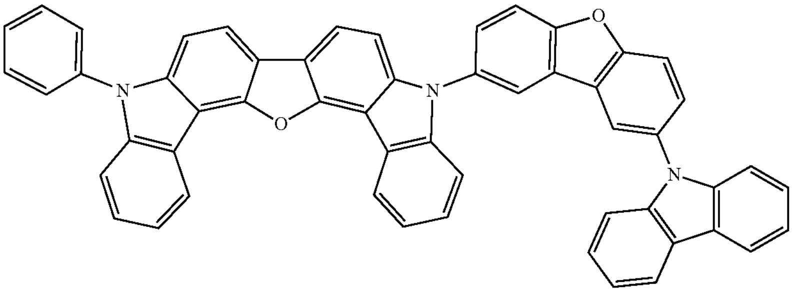 [SMILES: c1ccc(-n2c3ccccc3c3c4oc5c(ccc6c5c5ccccc5n6-c5ccc6oc7ccc(-n8c9ccccc9c9ccccc98)cc7c6c5)c4ccc32)cc1]
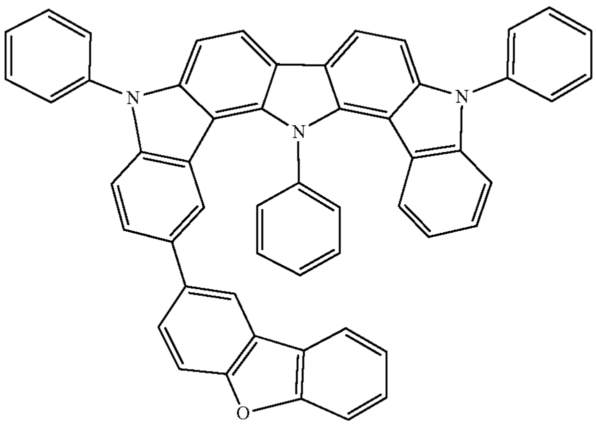 [SMILES: c1ccc(N2Cc3ccc(-c4ccc5oc6ccccc6c5c4)cc3-c3c2ccc2c4ccc5c(c6ccccc6n5-c5ccccc5)c4n(-c4ccccc4)c32)cc1]

TABLE 3-continued
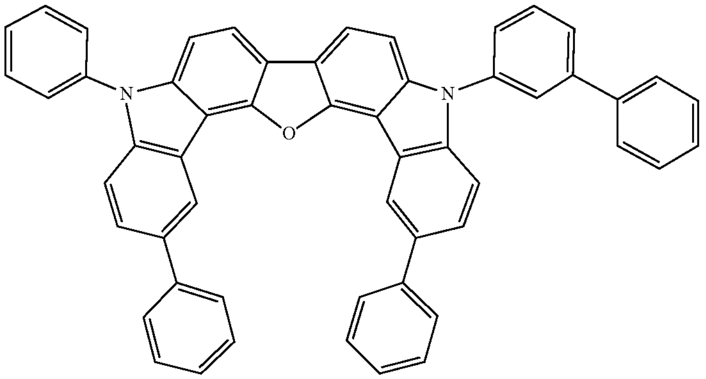 [SMILES: c1ccc(-c2cccc(-n3c4ccc(-c5ccccc5)cc4c4c5oc6c(ccc7c6c6cc(-c8ccccc8)ccc6n7-c6ccccc6)c5ccc43)c2)cc1]
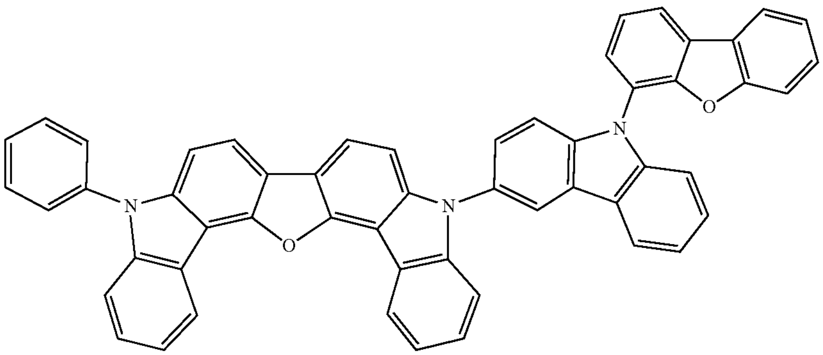 [SMILES: c1ccc(-n2c3ccccc3c3c4oc5c(ccc6c5c5ccccc5n6-c5ccc6c(c5)c5ccccc5n6-c5cccc6c5oc5ccccc56)c4ccc32)cc1]
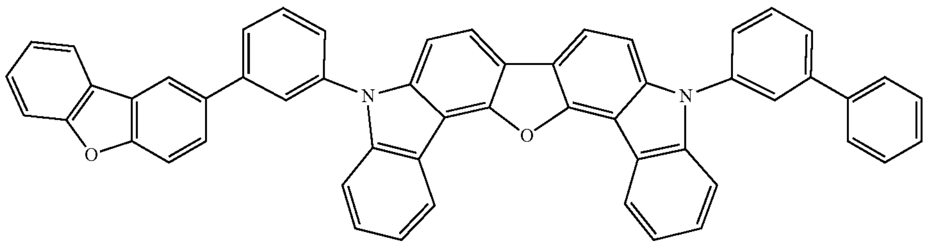 [SMILES: c1ccc(-c2cccc(-n3c4ccccc4c4c5oc6c(ccc7c6c6ccccc6n7-c6cccc(-c7ccc8oc9ccccc9c8c7)c6)c5ccc43)c2)cc1]
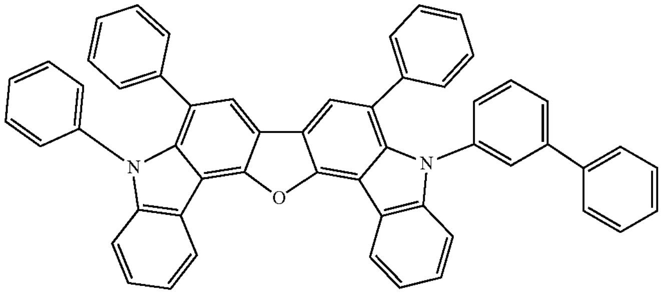 [SMILES: c1ccc(-c2cccc(-n3c4ccccc4c4c5oc6c(cc(-c7ccccc7)c7c6c6ccccc6n7-c6ccccc6)c5cc(-c5ccccc5)c43)c2)cc1]

TABLE 3-continued
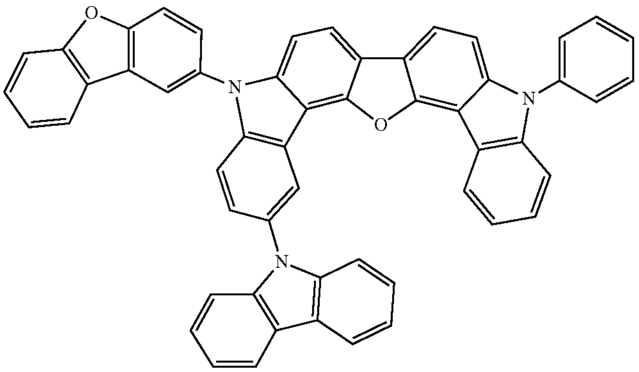 [SMILES: c1ccc(-n2c3ccccc3c3c4oc5c(ccc6c5c5cc(-n7c8ccccc8c8ccccc87)ccc5n6-c5ccc6oc7ccccc7c6c5)c4ccc32)cc1]
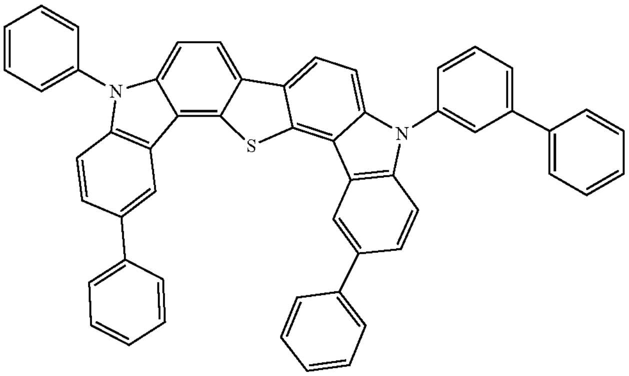 [SMILES: c1ccc(-c2cccc(-n3c4ccc(-c5ccccc5)cc4c4c5sc6c(ccc7c6c6cc(-c8ccccc8)ccc6n7-c6ccccc6)c5ccc43)c2)cc1]
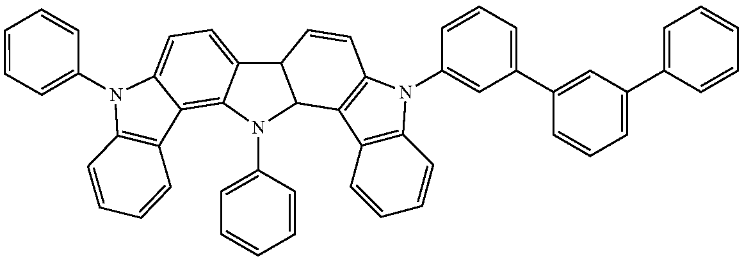 [SMILES: C1=CC2c3ccc4c(c3N(c3ccccc3)C2c2c1n(-c1cccc(-c3cccc(-c5ccccc5)c3)c1)c1ccccc21)c1ccccc1n4-c1ccccc1]
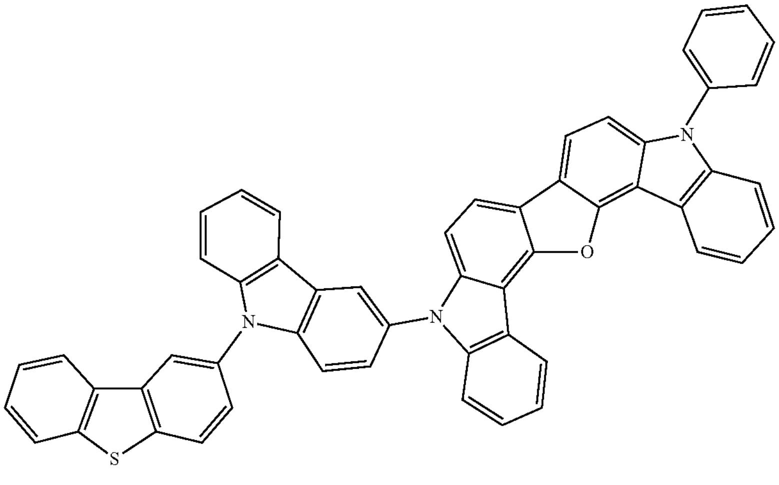

TABLE 3-continued
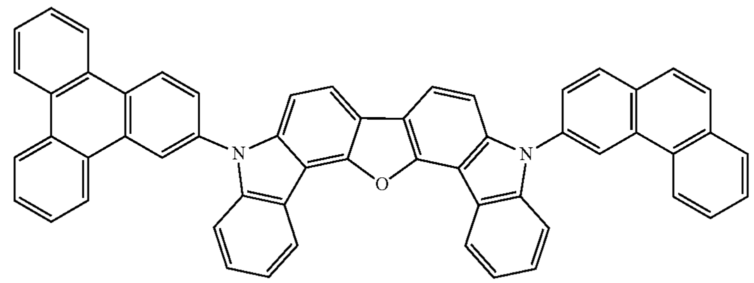 [SMILES: c1ccc2c(c1)ccc1ccc(-n3c4ccccc4c4c5oc6c(ccc7c6c6ccccc6n7-c6ccc7c8ccccc8c8ccccc8c7c6)c5ccc43)cc12]
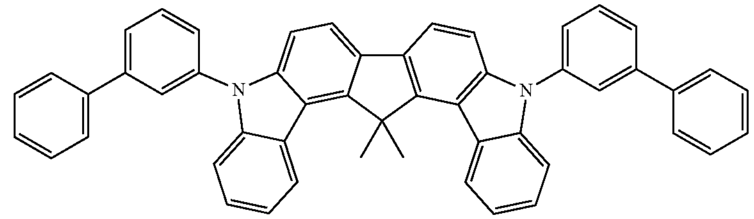 [SMILES: CC1(C)c2c(ccc3c2c2ccccc2n3-c2cccc(-c3ccccc3)c2)-c2ccc3c(c21)c1ccccc1n3-c1cccc(-c2ccccc2)c1]
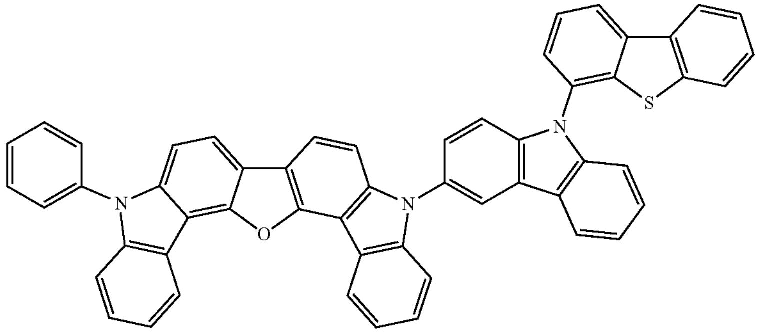 [SMILES: c1ccc(-n2c3ccccc3c3c4oc5c(ccc6c5c5ccccc5n6-c5ccc6c(c5)c5ccccc5n6-c5cccc6c5sc5ccccc56)c4ccc32)cc1]
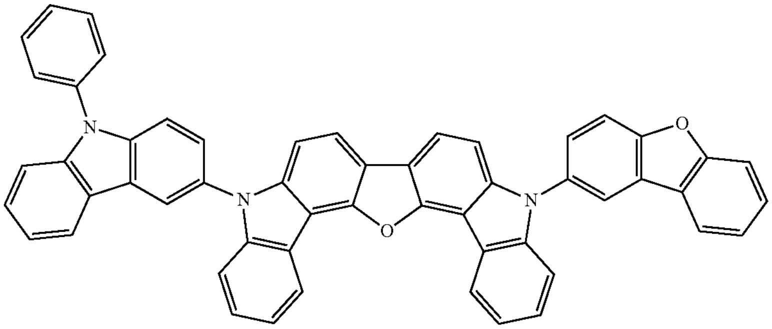 [SMILES: c1ccc(-n2c3ccccc3c3cc(-n4c5ccccc5c5c6oc7c(ccc8c7c7ccccc7n8-c7ccc8oc9ccccc9c8c7)c6ccc54)ccc32)cc1]
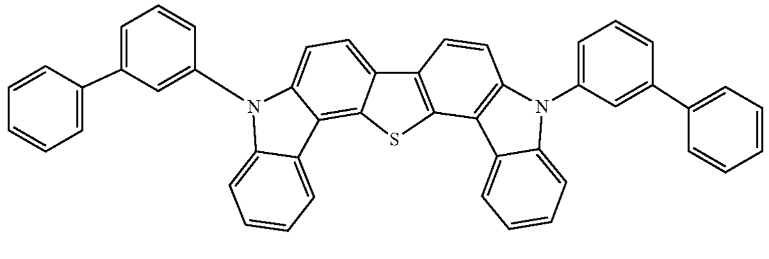 [SMILES: c1ccc(-c2cccc(-n3c4ccccc4c4c5sc6c(ccc7c6c6ccccc6n7-c6cccc(-c7ccccc7)c6)c5ccc43)c2)cc1]

TABLE 3-continued
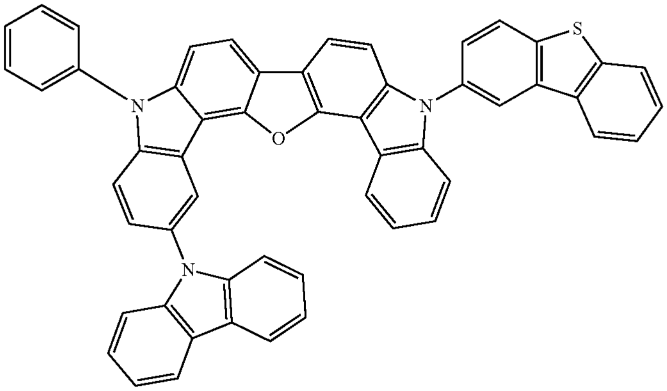 [SMILES: c1ccc(-n2c3ccc(-n4c5ccccc5c5ccccc54)cc3c3c4oc5c(ccc6c5c5ccccc5n6-c5ccc6sc7ccccc7c6c5)c4ccc32)cc1]
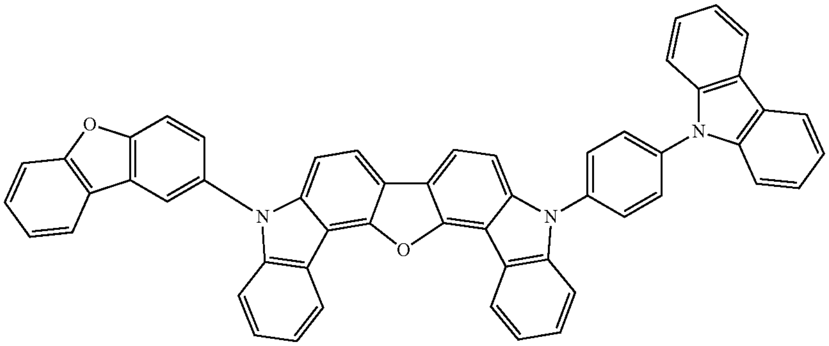 [SMILES: c1ccc2c(c1)oc1ccc(-n3c4ccccc4c4c5oc6c(ccc7c6c6ccccc6n7-c6ccc(-n7c8ccccc8c8ccccc87)cc6)c5ccc43)cc12]
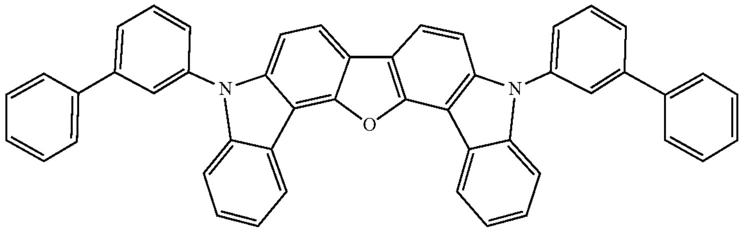 [SMILES: c1ccc(-c2cccc(-n3c4ccccc4c4c5oc6c(ccc7c6c6ccccc6n7-c6cccc(-c7ccccc7)c6)c5ccc43)c2)cc1]
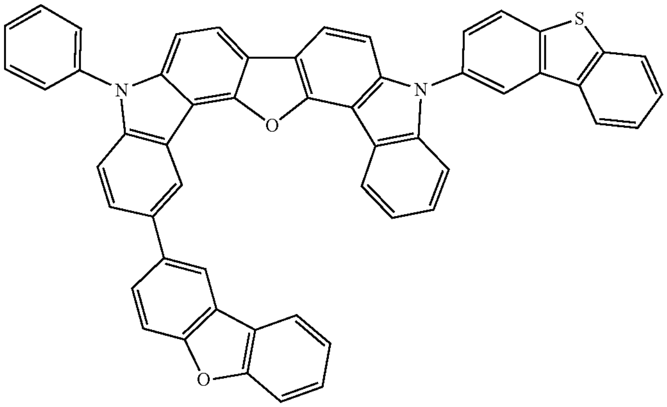 [SMILES: c1ccc(-n2c3ccc(-c4ccc5oc6ccccc6c5c4)cc3c3c4oc5c(ccc6c5c5ccccc5n6-c5ccc6sc7ccccc7c6c5)c4ccc32)cc1]
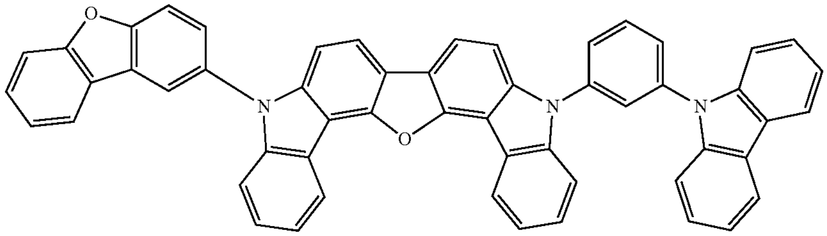 [SMILES: c1cc(-n2c3ccccc3c3ccccc32)cc(-n2c3ccccc3c3c4oc5c(ccc6c5c5ccccc5n6-c5ccc6oc7ccccc7c6c5)c4ccc32)c1]

TABLE 3-continued
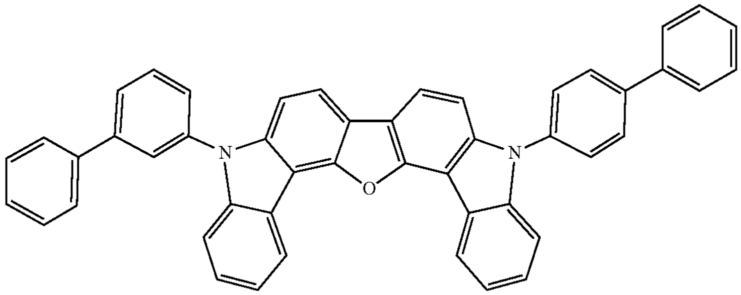 [SMILES: c1ccc(-c2ccc(-n3c4ccccc4c4c5oc6c(ccc7c6c6ccccc6n7-c6cccc(-c7ccccc7)c6)c5ccc43)cc2)cc1]
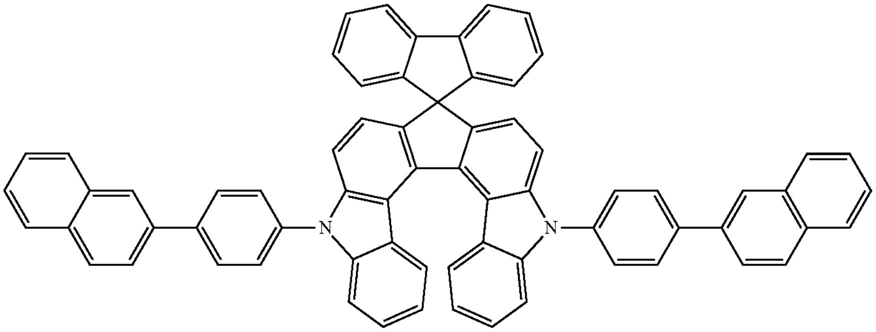 [SMILES: c1ccc2c(c1)-c1ccccc1C21c2ccc3c(c2-c2c1ccc1c2c2ccccc2n1-c1ccc(-c2ccc4ccccc4c2)cc1)c1ccccc1n3-c1ccc(-c2ccc3ccccc3c2)cc1]
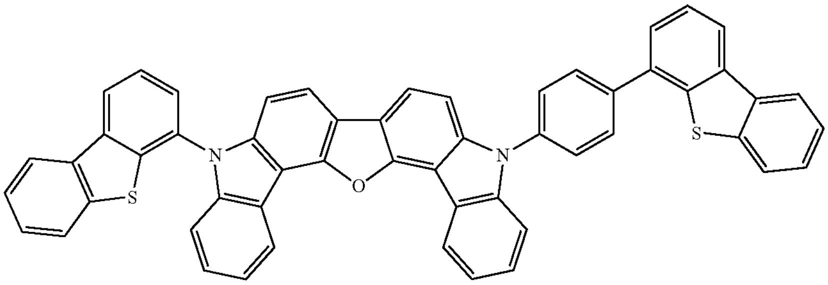 [SMILES: c1ccc2c(c1)sc1c(-c3ccc(-n4c5ccccc5c5c6oc7c(ccc8c7c7ccccc7n8-c7cccc8c7sc7ccccc78)c6ccc54)cc3)cccc12]
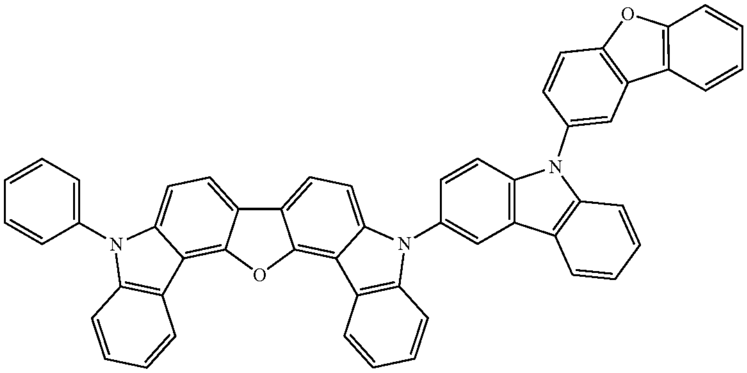 [SMILES: c1ccc(-n2c3ccccc3c3c4oc5c(ccc6c5c5ccccc5n6-c5ccc6c(c5)c5ccccc5n6-c5ccc6oc7ccccc7c6c5)c4ccc32)cc1]
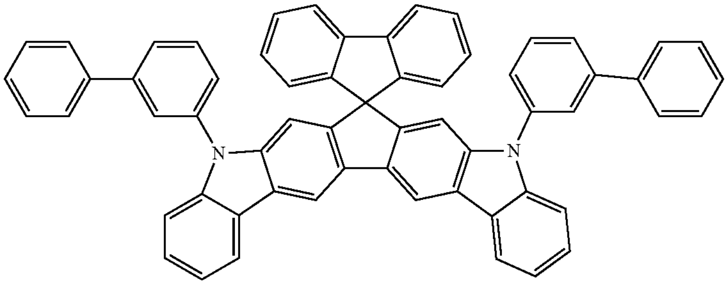 [SMILES: c1ccc(-c2cccc(-n3c4ccccc4c4cc5c(cc43)C3(c4ccccc4-c4ccccc43)c3cc4c(cc3-5)c3ccccc3n4-c3cccc(-c4ccccc4)c3)c2)cc1]

TABLE 3-continued
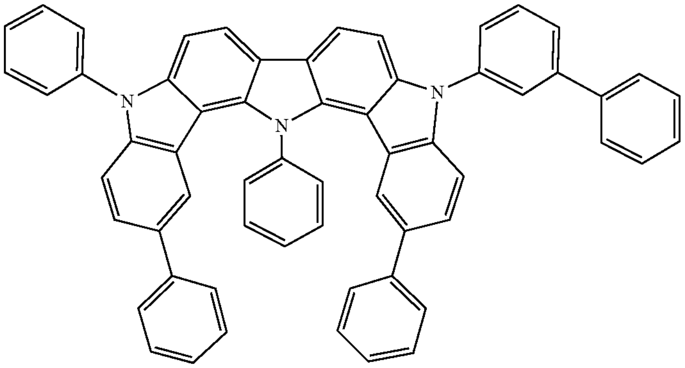 [SMILES: c1ccc(-c2cccc(-n3c4ccc(-c5ccccc5)cc4c4c3ccc3c5ccc6c(c7cc(-c8ccccc8)ccc7n6-c6ccccc6)c5n(-c5ccccc5)c34)c2)cc1]
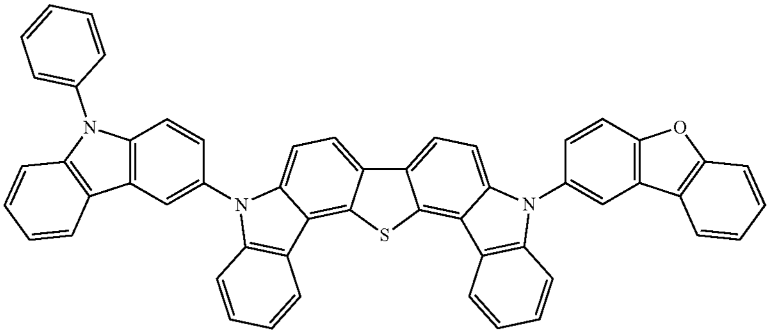 [SMILES: c1ccc(-n2c3ccccc3c3cc(-n4c5ccccc5c5c6sc7c(ccc8c7c7ccccc7n8-c7ccc8oc9ccccc9c8c7)c6ccc54)ccc32)cc1]
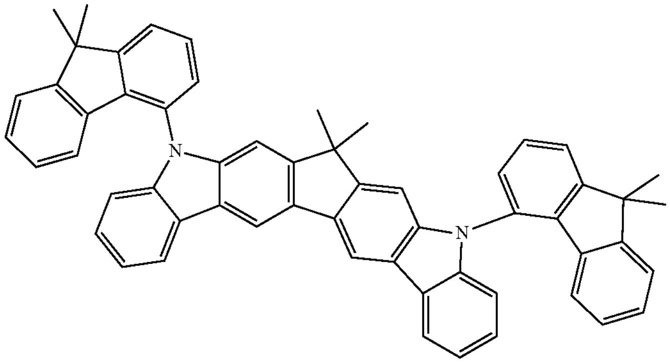 [SMILES: CC1(C)c2cc3c(cc2-c2cc4c5ccccc5n(-c5cccc6c5-c5ccccc5C6(C)C)c4cc21)c1ccccc1n3-c1cccc2c1-c1ccccc1C2(C)C]
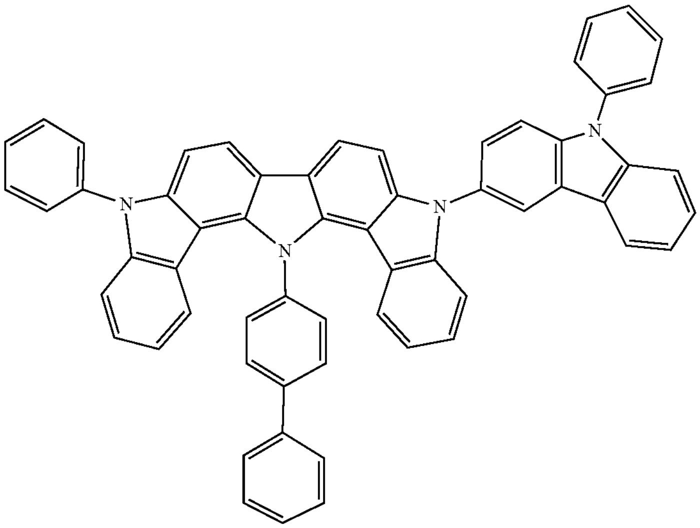 [SMILES: c1ccc(-c2ccc(-n3c4c(ccc5c4c4ccccc4n5-c4ccccc4)c4ccc5c(c6ccccc6n5-c5ccc6c(c5)c5ccccc5n6-c5ccccc5)c43)cc2)cc1]

TABLE 3-continued
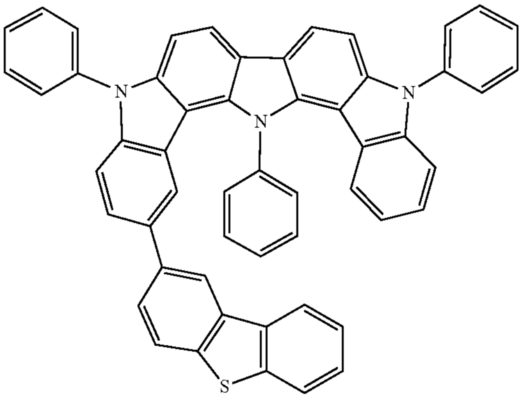 [SMILES: c1ccc(-n2c3ccccc3c3c2ccc2c4ccc5c(c6cc(-c7ccc8sc9ccccc9c8c7)ccc6n5-c5ccccc5)c4n(-c4ccccc4)c23)cc1]
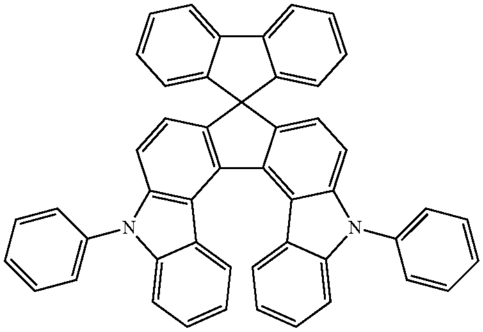 [SMILES: c1ccc(-n2c3ccccc3c3c4c(ccc32)C2(c3ccccc3-c3ccccc32)c2ccc3c(c2-4)c2ccccc2n3-c2ccccc2)cc1]
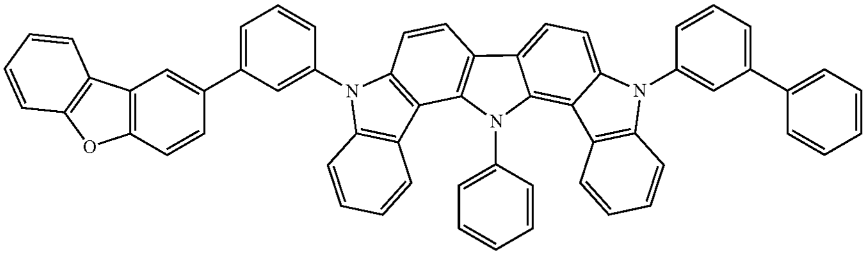 [SMILES: c1ccc(-c2cccc(-n3c4ccccc4c4c3ccc3c5ccc6c(c7ccccc7n6-c6cccc(-c7ccc8oc9ccccc9c8c7)c6)c5n(-c5ccccc5)c34)c2)cc1]
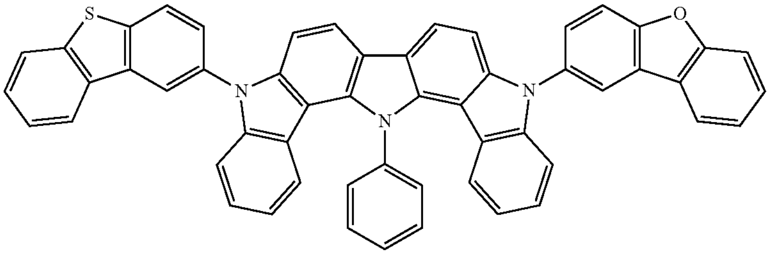 [SMILES: c1ccc(-n2c3c(ccc4c3c3ccccc3n4-c3ccc4oc5ccccc5c4c3)c3ccc4c(c5ccccc5n4-c4ccc5sc6ccccc6c5c4)c32)cc1]
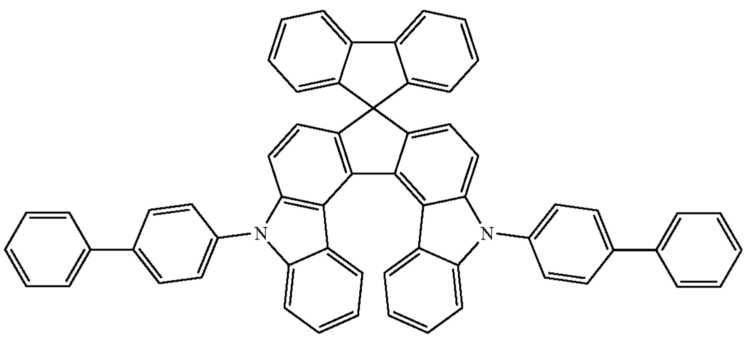 [SMILES: c1ccc(-c2ccc(-n3c4ccccc4c4c5c(ccc43)C3(c4ccccc4-c4ccccc43)c3ccc4c(c3-5)c3ccccc3n4-c3ccc(-c4ccccc4)cc3)cc2)cc1]

TABLE 3-continued
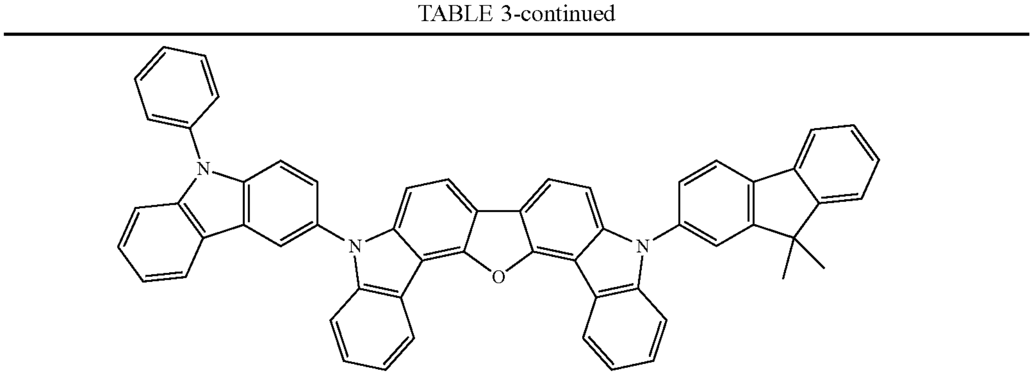
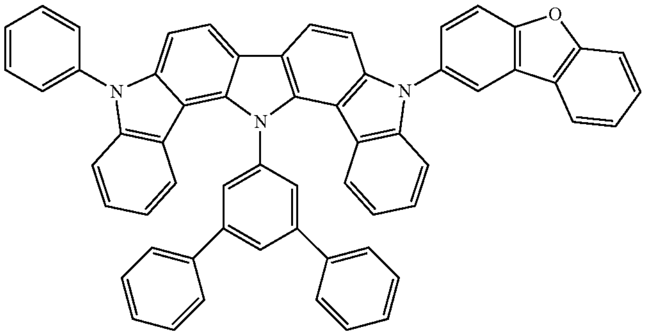 [SMILES: c1ccc(-c2cc(-c3ccccc3)cc(-n3c4c(ccc5c4c4ccccc4n5-c4ccccc4)c4ccc5c(c6ccccc6n5-c5ccc6oc7ccccc7c6c5)c43)c2)cc1]
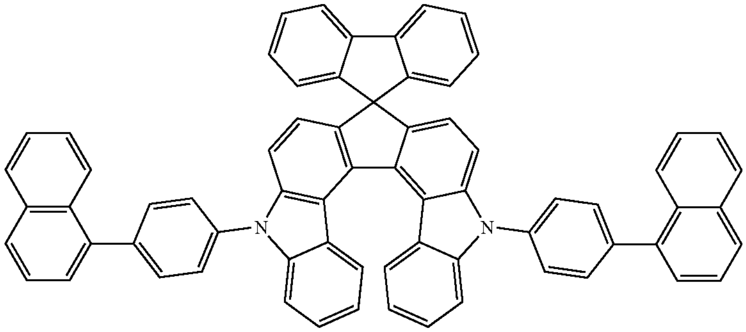 [SMILES: c1ccc2c(c1)-c1ccccc1C21c2ccc3c(c2-c2c1ccc1c2c2ccccc2n1-c1ccc(-c2cccc4ccccc24)cc1)c1ccccc1n3-c1ccc(-c2cccc3ccccc23)cc1]
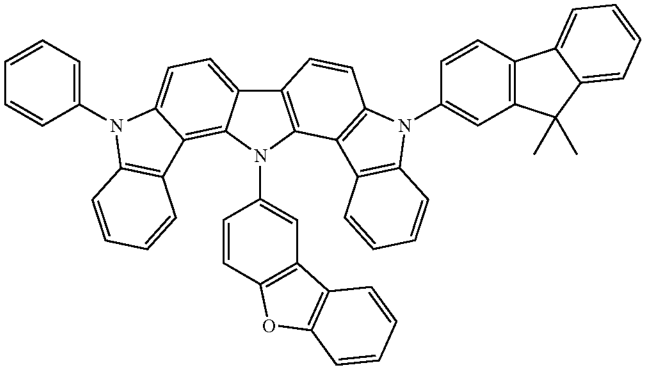 [SMILES: CC1(C)c2ccccc2-c2ccc(-n3c4ccccc4c4c3ccc3c5ccc6c(c7ccccc7n6-c6ccccc6)c5n(-c5ccc6oc7ccccc7c6c5)c34)cc21]
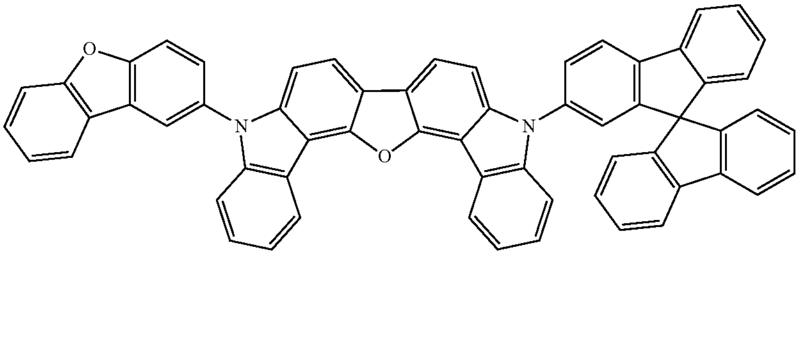 [SMILES: c1ccc2c(c1)-c1ccccc1C21c2ccccc2-c2ccc(-n3c4ccccc4c4c5oc6c(ccc7c6c6ccccc6n7-c6ccc7oc8ccccc8c7c6)c5ccc43)cc21]

TABLE 3-continued
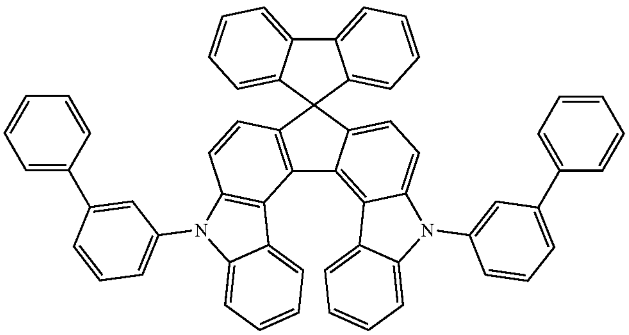 [SMILES: c1ccc(-c2cccc(-n3c4ccccc4c4c5c(ccc43)C3(c4ccccc4-c4ccccc43)c3ccc4c(c3-5)c3ccccc3n4-c3cccc(-c4ccccc4)c3)c2)cc1]
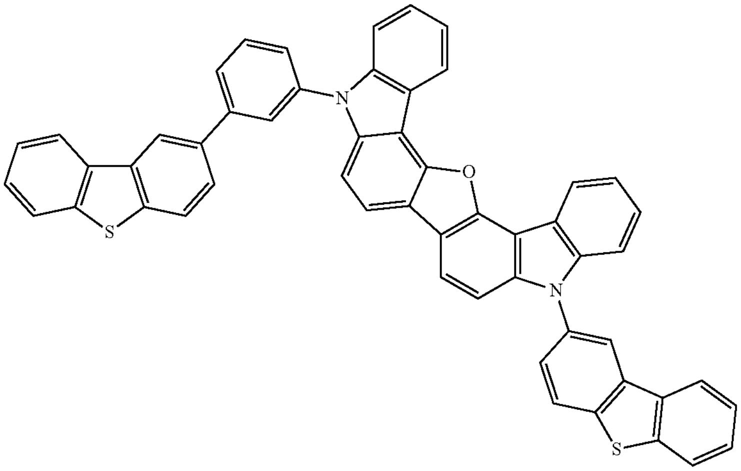 [SMILES: c1cc(-c2ccc3sc4ccccc4c3c2)cc(-n2c3ccccc3c3c4oc5c(ccc6c5c5ccccc5n6-c5ccc6sc7ccccc7c6c5)c4ccc32)c1]
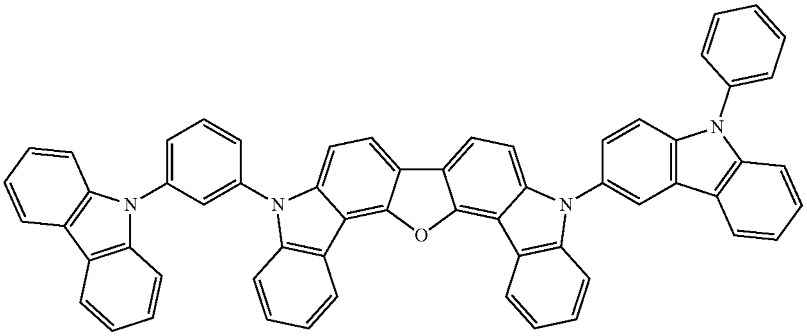 [SMILES: c1ccc(-n2c3ccccc3c3cc(-n4c5ccccc5c5c6oc7c(ccc8c7c7ccccc7n8-c7cccc(-n8c9ccccc9c9ccccc98)c7)c6ccc54)ccc32)cc1]
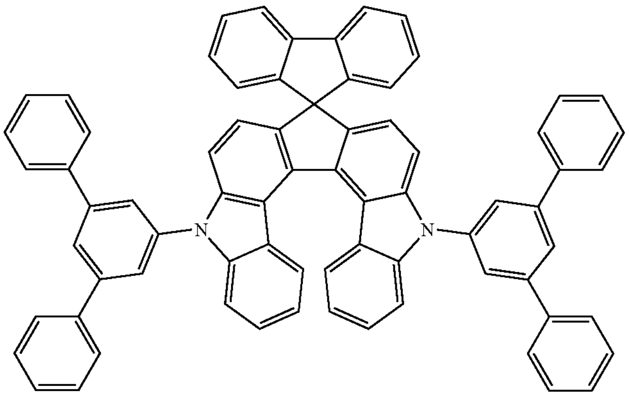 [SMILES: c1ccc(-c2cc(-c3ccccc3)cc(-n3c4ccccc4c4c5c(ccc43)C3(c4ccccc4-c4ccccc43)c3ccc4c(c3-5)c3ccccc3n4-c3cc(-c4ccccc4)cc(-c4ccccc4)c3)c2)cc1]

TABLE 3-continued
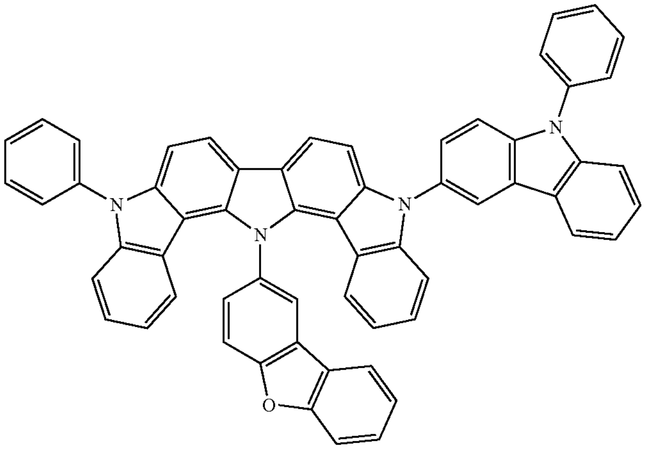 [SMILES: c1ccc(-n2c3ccccc3c3cc(-n4c5ccccc5c5c4ccc4c6ccc7c(c8ccccc8n7-c7ccccc7)c6n(-c6ccc7oc8ccccc8c7c6)c45)ccc32)cc1]
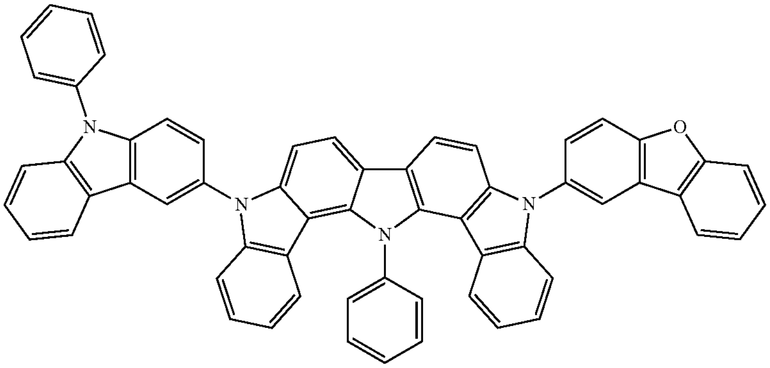 [SMILES: c1ccc(-n2c3ccccc3c3cc(-n4c5ccccc5c5c4ccc4c6ccc7c(c8ccccc8n7-c7ccc8oc9ccccc9c8c7)c6n(-c6ccccc6)c45)ccc32)cc1]
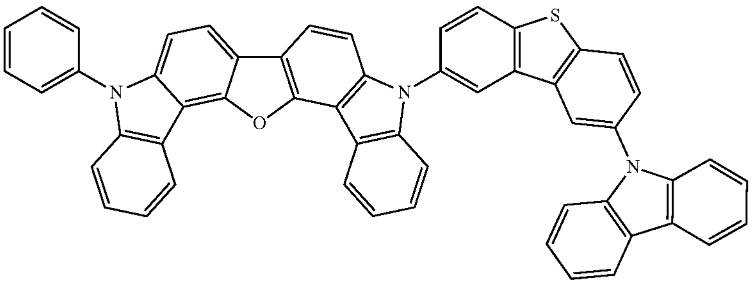 [SMILES: c1ccc(-n2c3ccccc3c3c4oc5c(ccc6c5c5ccccc5n6-c5ccc6sc7ccc(-n8c9ccccc9c9ccccc98)cc7c6c5)c4ccc32)cc1]
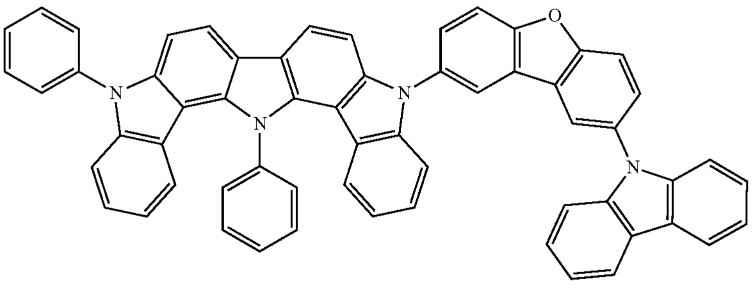 [SMILES: c1ccc(-n2c3ccccc3c3c2ccc2c4ccc5c(c6ccccc6n5-c5ccc6oc7ccc(-n8c9ccccc9c9ccccc98)cc7c6c5)c4n(-c4ccccc4)c23)cc1]

TABLE 3-continued
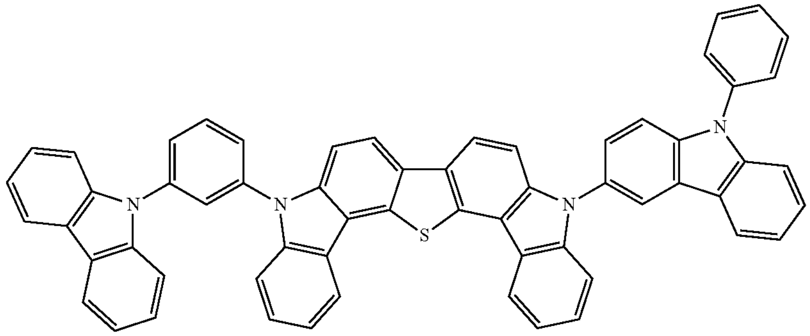 [SMILES: c1ccc(-n2c3ccccc3c3cc(-n4c5ccccc5c5c6sc7c(ccc8c7c7ccccc7n8-c7cccc(-n8c9ccccc9c9ccccc98)c7)c6ccc54)ccc32)cc1]
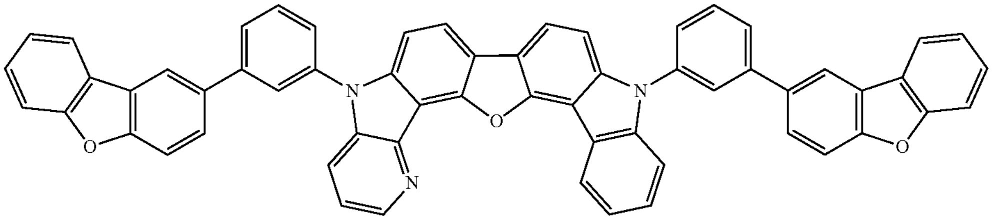 [SMILES: c1cc(-c2ccc3oc4ccccc4c3c2)cc(-n2c3ccccc3c3c4oc5c(ccc6c5c5ncccc5n6-c5cccc(-c6ccc7oc8ccccc8c7c6)c5)c4ccc32)c1]
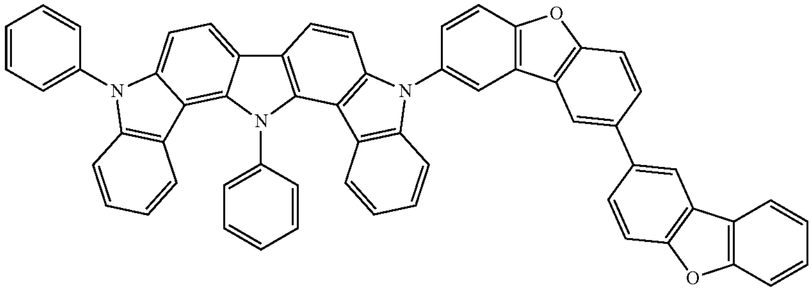 [SMILES: c1ccc(-n2c3ccccc3c3c2ccc2c4ccc5c(c6ccccc6n5-c5ccc6oc7ccc(-c8ccc9oc%10ccccc%10c9c8)cc7c6c5)c4n(-c4ccccc4)c23)cc1]
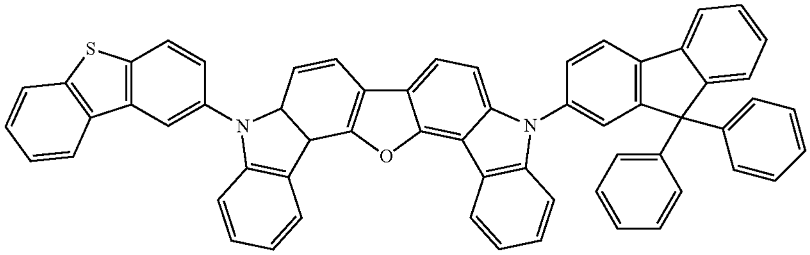 [SMILES: C1=CC2C(c3ccccc3N2c2ccc3sc4ccccc4c3c2)c2oc3c(ccc4c3c3ccccc3n4-c3ccc4c(c3)C(c3ccccc3)(c3ccccc3)c3ccccc3-4)c21]
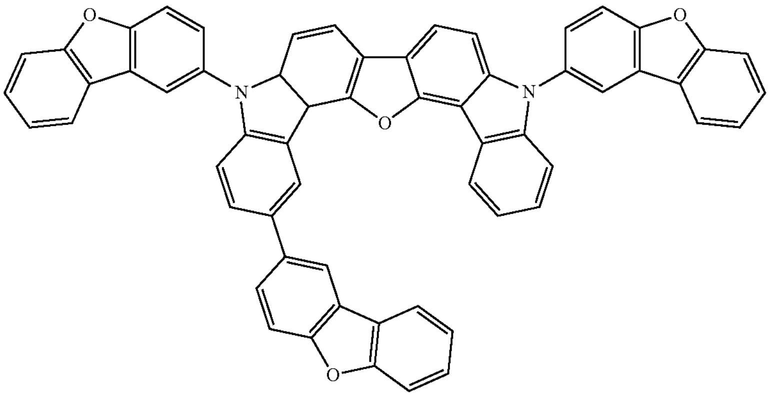 [SMILES: C1=CC2C(c3cc(-c4ccc5oc6ccccc6c5c4)ccc3N2c2ccc3oc4ccccc4c3c2)c2oc3c(ccc4c3c3ccccc3n4-c3ccc4oc5ccccc5c4c3)c21]

TABLE 3-continued
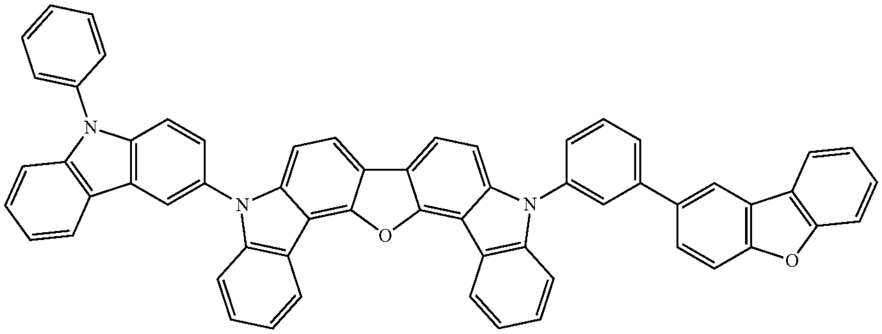 [SMILES: c1ccc(-n2c3ccccc3c3cc(-n4c5ccccc5c5c6oc7c(ccc8c7c7ccccc7n8-c7cccc(-c8ccc9oc%10ccccc%10c9c8)c7)c6ccc54)ccc32)cc1]
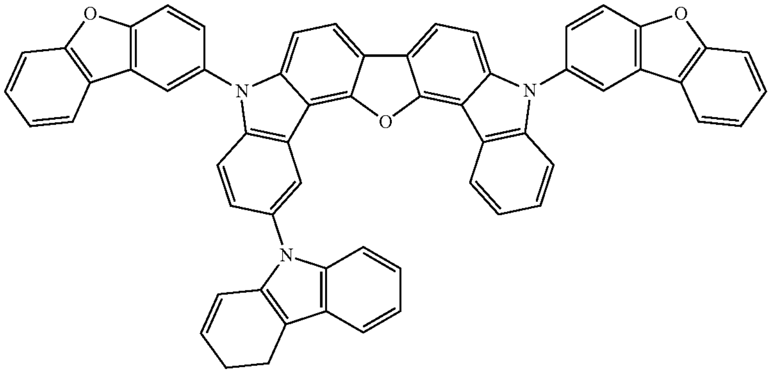 [SMILES: C1=Cc2c(c3ccccc3n2-c2ccc3c(c2)c2c4oc5c(ccc6c5c5ccccc5n6-c5ccc6oc7ccccc7c6c5)c4ccc2n3-c2ccc3oc4ccccc4c3c2)CC1]
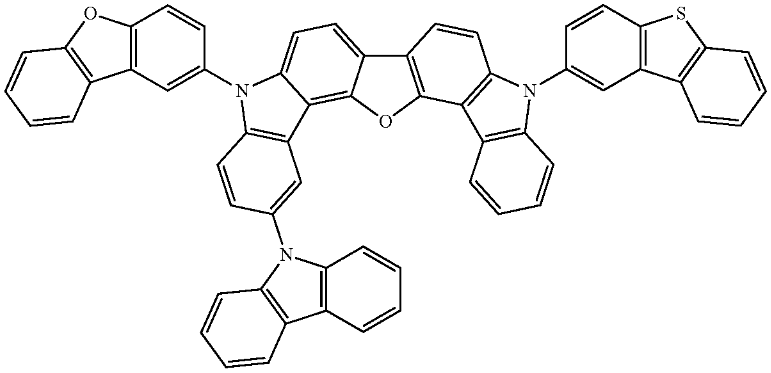 [SMILES: c1ccc2c(c1)oc1ccc(-n3c4ccc(-n5c6ccccc6c6ccccc65)cc4c4c5oc6c(ccc7c6c6ccccc6n7-c6ccc7sc8ccccc8c7c6)c5ccc43)cc12]
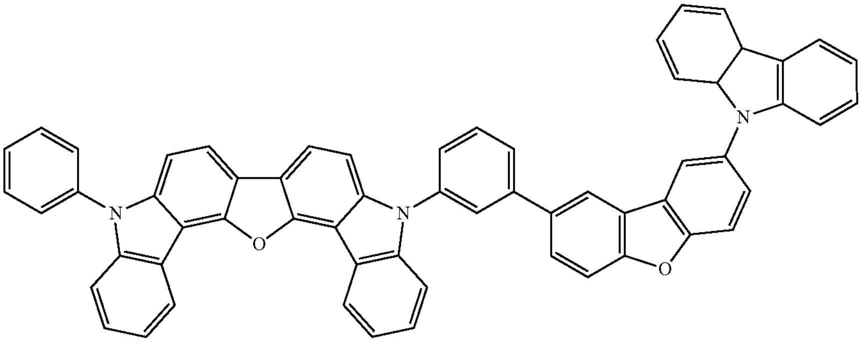 [SMILES: C1=CC2c3ccccc3N(c3ccc4oc5ccc(-c6cccc(-n7c8ccccc8c8c9oc%10c(ccc%11c%10c%10ccccc%10n%11-c%10ccccc%10)c9ccc87)c6)cc5c4c3)C2C=C1]

TABLE 3-continued
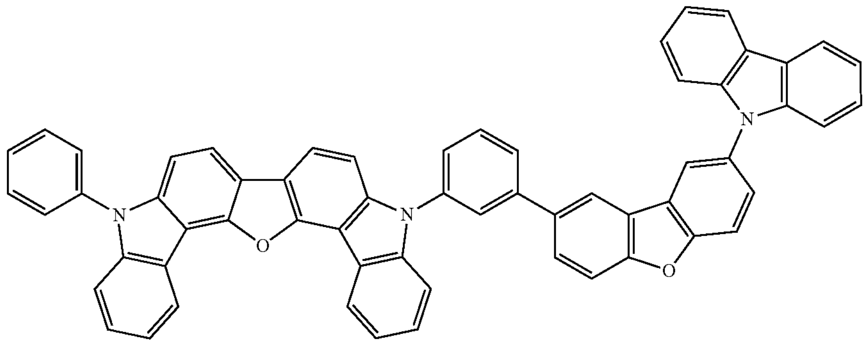 [SMILES: c1ccc(-n2c3ccccc3c3c4oc5c(ccc6c5c5ccccc5n6-c5cccc(-c6ccc7oc8ccc(-n9c%10ccccc%10c%10ccccc%109)cc8c7c6)c5)c4ccc32)cc1]
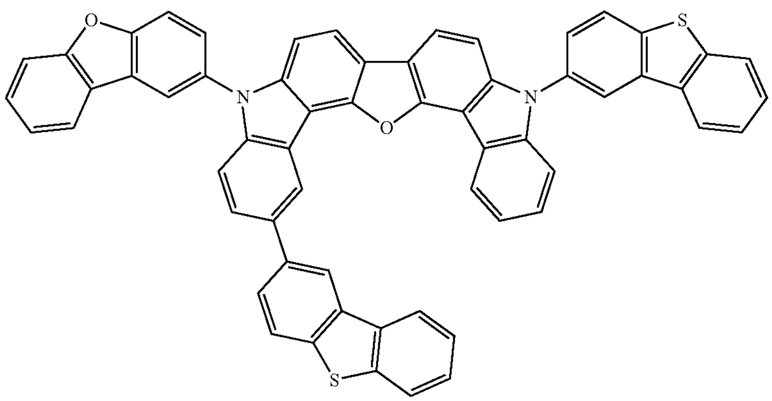 [SMILES: c1ccc2c(c1)oc1ccc(-n3c4ccc(-c5ccc6sc7ccccc7c6c5)cc4c4c5oc6c(ccc7c6c6ccccc6n7-c6ccc7sc8ccccc8c7c6)c5ccc43)cc12]
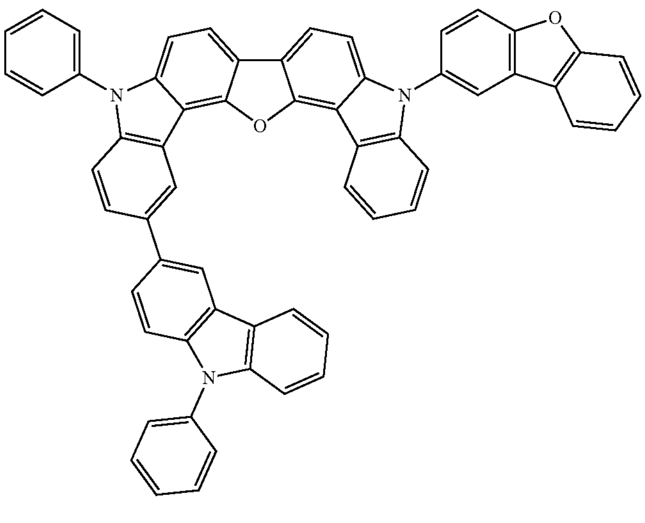 [SMILES: c1ccc(-n2c3ccccc3c3cc(-c4ccc5c(c4)c4c6oc7c(ccc8c7c7ccccc7n8-c7ccc8oc9ccccc9c8c7)c6ccc4n5-c4ccccc4)ccc32)cc1]

TABLE 3-continued
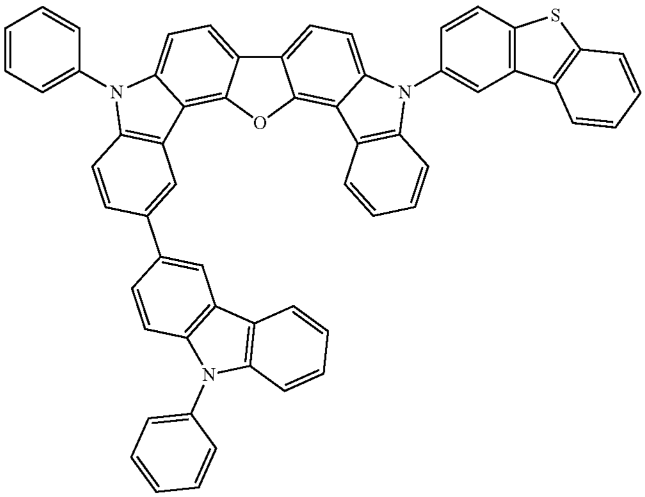 [SMILES: c1ccc(-n2c3ccccc3c3cc(-c4ccc5c(c4)c4c6oc7c(ccc8c7c7ccccc7n8-c7ccc8sc9ccccc9c8c7)c6ccc4n5-c4ccccc4)ccc32)cc1]
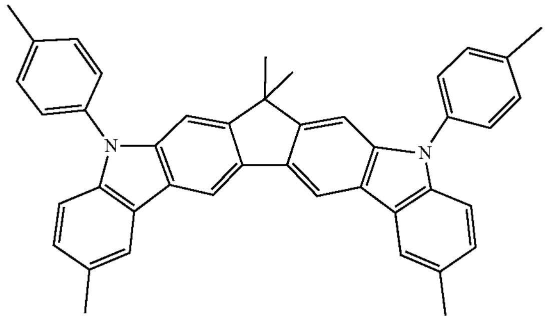
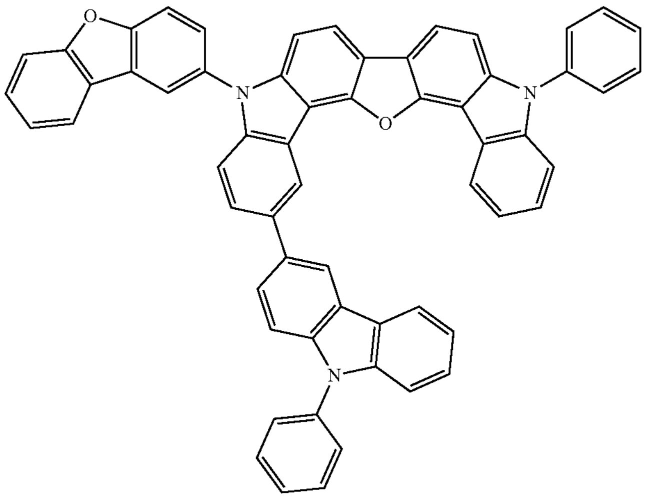 [SMILES: c1ccc(-n2c3ccccc3c3cc(-c4ccc5c(c4)c4c6oc7c(ccc8c7c7ccccc7n8-c7ccccc7)c6ccc4n5-c4ccc5oc6ccccc6c5c4)ccc32)cc1]

TABLE 3-continued
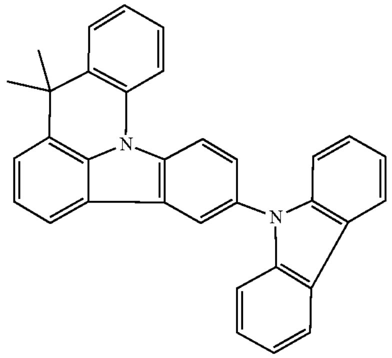 [SMILES: CC1(C)c2ccccc2-n2c3ccc(-n4c5ccccc5c5ccccc54)cc3c3cccc1c32]
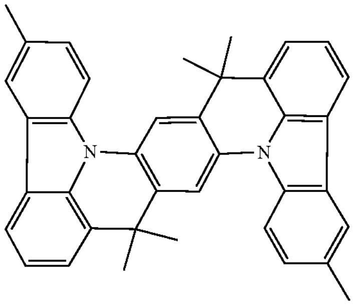 [SMILES: Cc1ccc2c(c1)c1cccc3c1n2-c1cc2c(cc1C3(C)C)-n1c3ccc(C)cc3c3cccc(c31)C2(C)C]
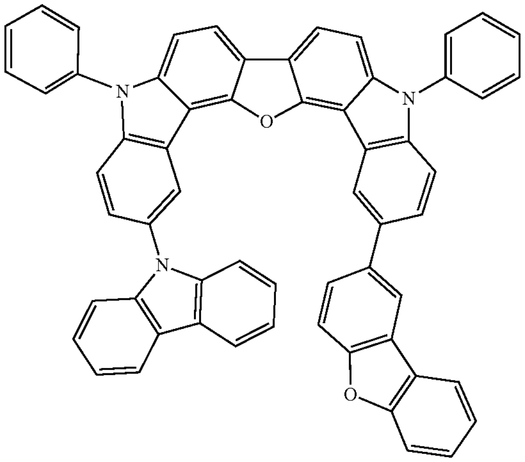 [SMILES: c1ccc(-n2c3ccc(-c4ccc5oc6ccccc6c5c4)cc3c3c4oc5c(ccc6c5c5cc(-n7c8ccccc8c8ccccc87)ccc5n6-c5ccccc5)c4ccc32)cc1]
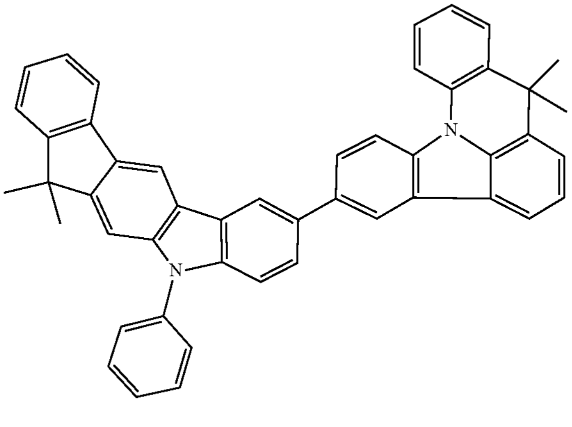

TABLE 3-continued
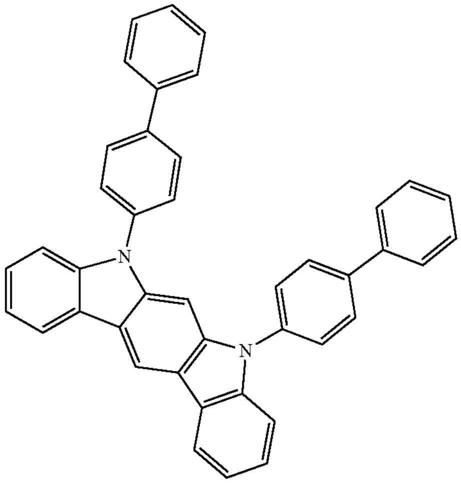 [SMILES: c1ccc(-c2ccc(-n3c4ccccc4c4cc5c6ccccc6n(-c6ccc(-c7ccccc7)cc6)c5cc43)cc2)cc1]
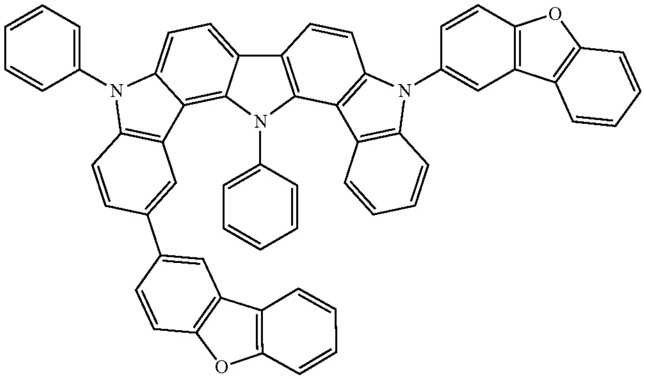 [SMILES: c1ccc(-n2c3ccc(-c4ccc5oc6ccccc6c5c4)cc3c3c2ccc2c4ccc5c(c6ccccc6n5-c5ccc6oc7ccccc7c6c5)c4n(-c4ccccc4)c23)cc1]
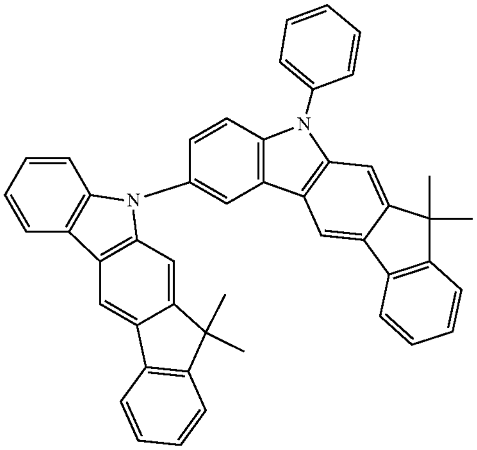 [SMILES: CC1(C)c2ccccc2-c2cc3c4ccccc4n(-c4ccc5c(c4)c4cc6c(cc4n5-c4ccccc4)C(C)(C)c4ccccc4-6)c3cc21]

TABLE 3-continued
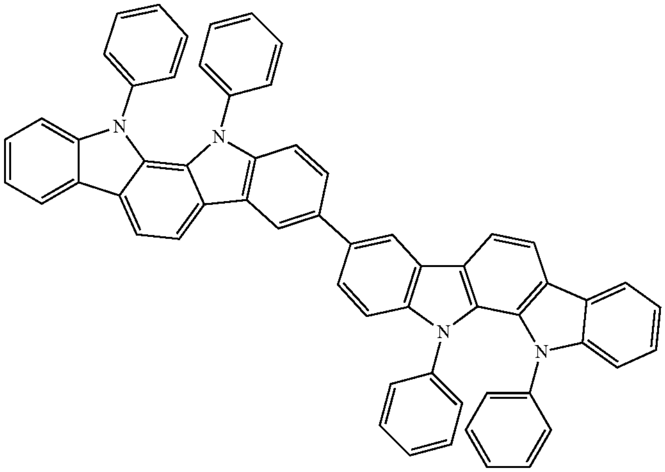 [SMILES: c1ccc(-n2c3ccccc3c3ccc4c5cc(-c6ccc7c(c6)c6ccc8c9ccccc9n(-c9ccccc9)c8c6n7-c6ccccc6)ccc5n(-c5ccccc5)c4c32)cc1]
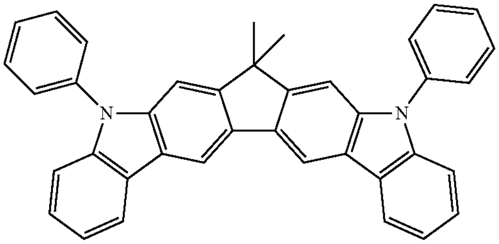 [SMILES: CC1(C)c2cc3c(cc2-c2cc4c5ccccc5n(-c5ccccc5)c4cc21)c1ccccc1n3-c1ccccc1]
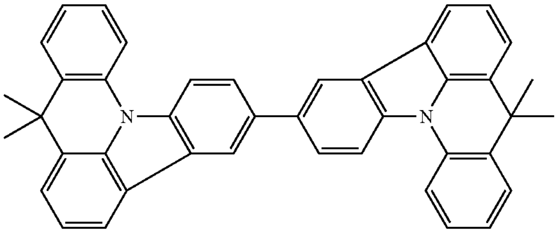
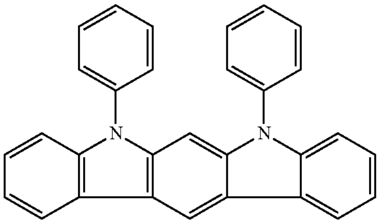 [SMILES: c1ccc(-n2c3ccccc3c3cc4c5ccccc5n(-c5ccccc5)c4cc32)cc1]
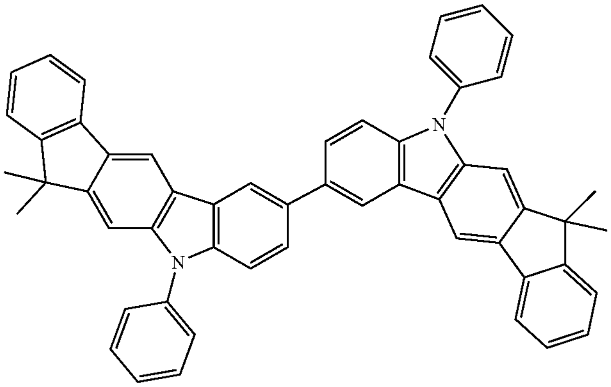

TABLE 3-continued
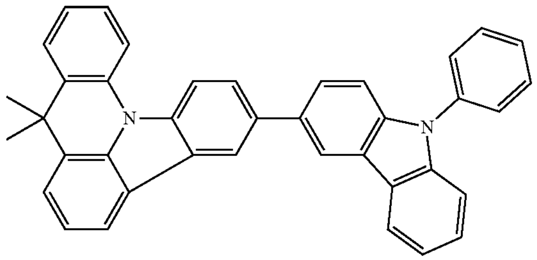 [SMILES: CC1(C)c2ccccc2-n2c3ccc(-c4ccc5c(c4)c4ccccc4n5-c4ccccc4)cc3c3cccc1c32]
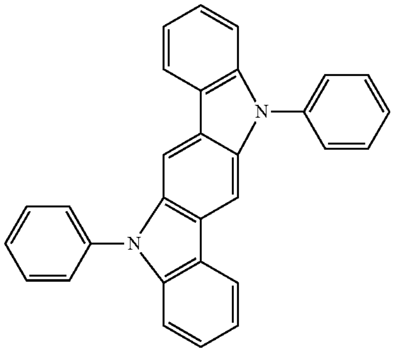 [SMILES: c1ccc(-n2c3ccccc3c3cc4c(cc32)c2ccccc2n4-c2ccccc2)cc1]
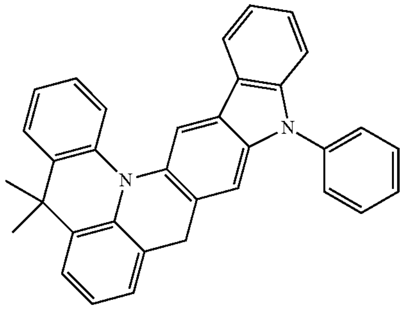 [SMILES: CC1(C)c2ccccc2N2c3cc4c5ccccc5n(-c5ccccc5)c4cc3Cc3cccc1c32]
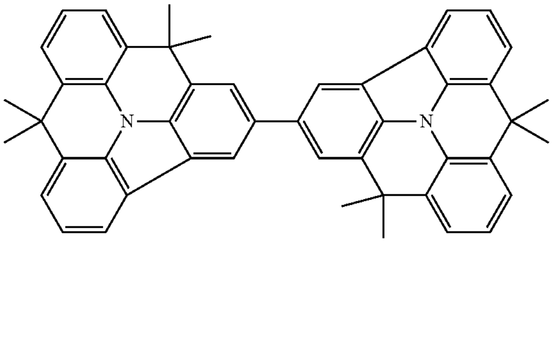

TABLE 3-continued
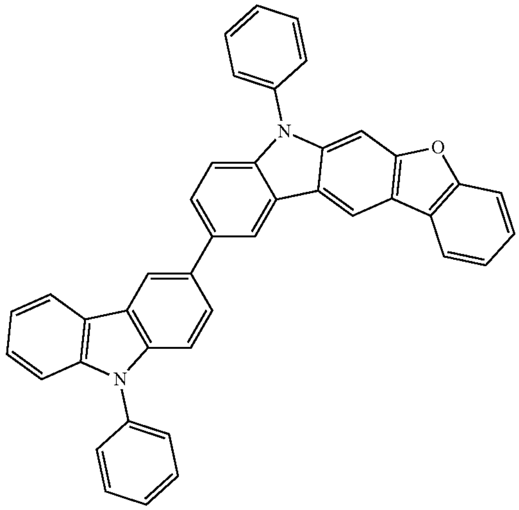 [SMILES: c1ccc(-n2c3ccccc3c3cc(-c4ccc5c(c4)c4cc6c(cc4n5-c4ccccc4)oc4ccccc46)ccc32)cc1]
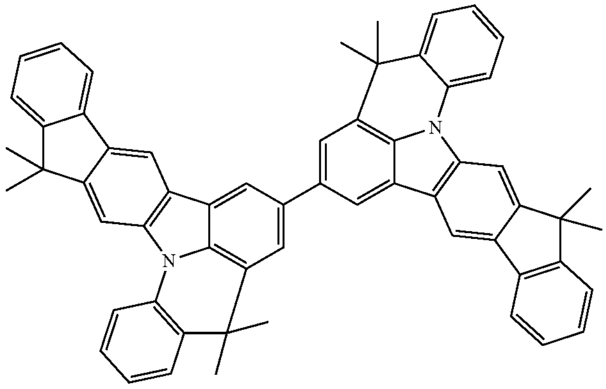
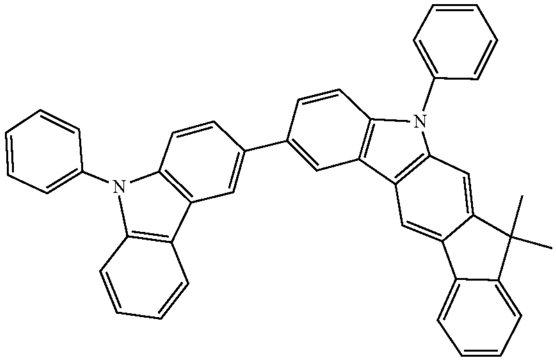 [SMILES: CC1(C)c2ccccc2-c2cc3c4cc(-c5ccc6c(c5)c5ccccc5n6-c5ccccc5)ccc4n(-c4ccccc4)c3cc21]

TABLE 3-continued
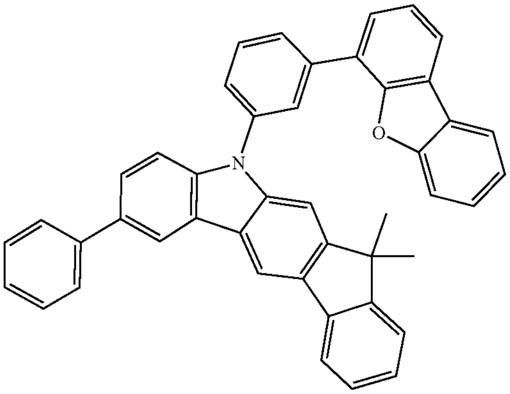 [SMILES: CC1(C)c2ccccc2-c2cc3c4cc(-c5ccccc5)ccc4n(-c4cccc(-c5cccc6c5oc5ccccc56)c4)c3cc21]
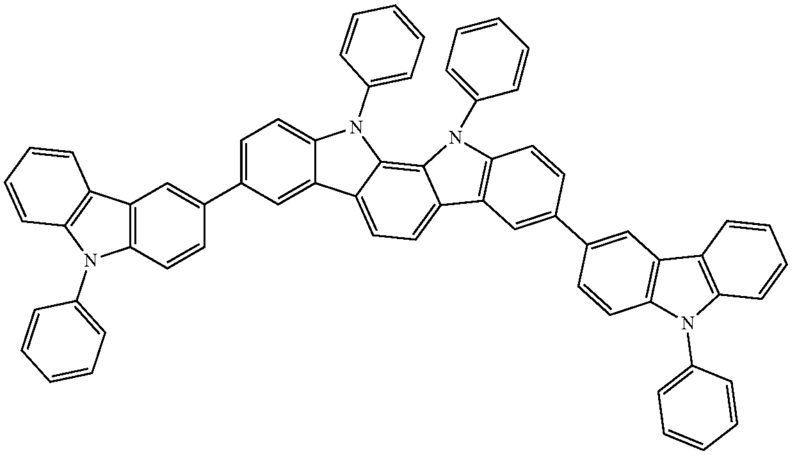 [SMILES: c1ccc(-n2c3ccccc3c3cc(-c4ccc5c(c4)c4ccc6c7cc(-c8ccc9c(c8)c8ccccc8n9-c8ccccc8)ccc7n(-c7ccccc7)c6c4n5-c4ccccc4)ccc32)cc1]
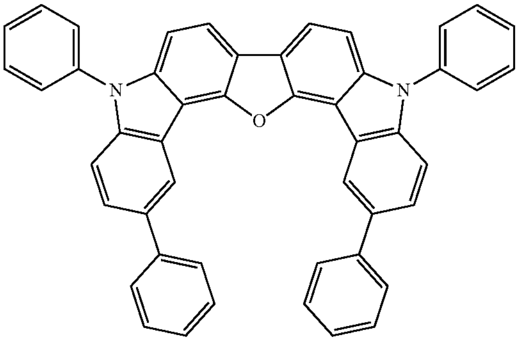 [SMILES: c1ccc(-c2ccc3c(c2)c2c4oc5c(ccc6c5c5cc(-c7ccccc7)ccc5n6-c5ccccc5)c4ccc2n3-c2ccccc2)cc1]
21
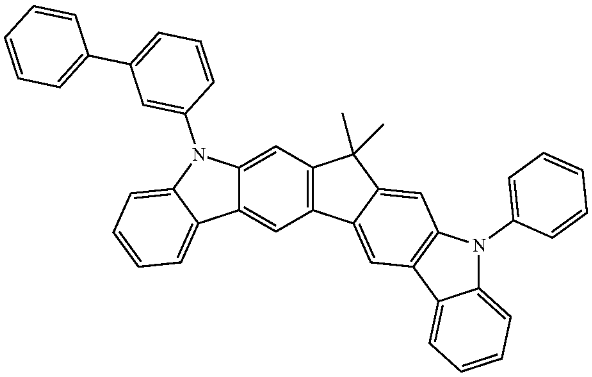 [SMILES: CC1(C)c2cc3c(cc2-c2cc4c5ccccc5n(-c5cccc(-c6ccccc6)c5)c4cc21)c1ccccc1n3-c1ccccc1]

TABLE 3-continued
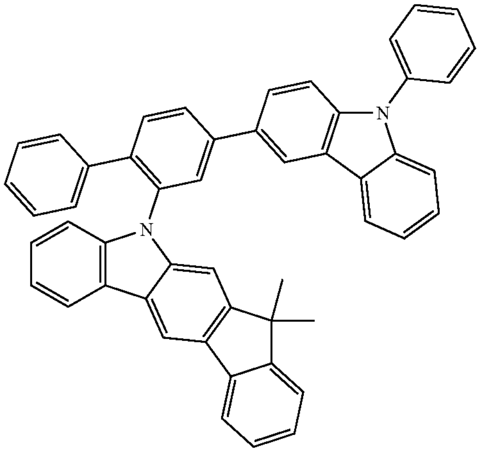 [SMILES: CC1(C)c2ccccc2-c2cc3c4ccccc4n(-c4cc(-c5ccc6c(c5)c5ccccc5n6-c5ccccc5)ccc4-c4ccccc4)c3cc21]
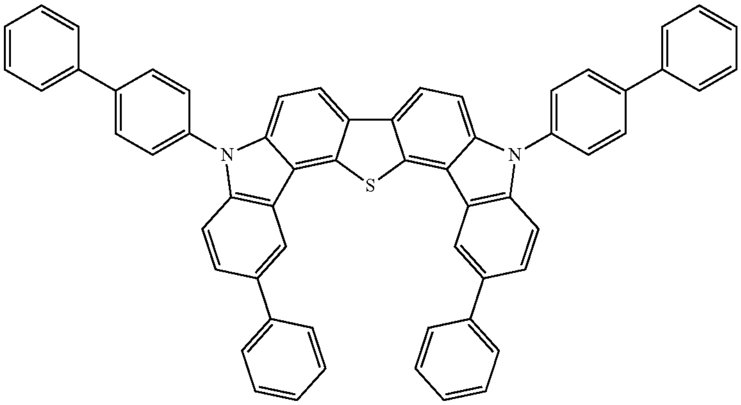 [SMILES: c1ccc(-c2ccc(-n3c4ccc(-c5ccccc5)cc4c4c5sc6c(ccc7c6c6cc(-c8ccccc8)ccc6n7-c6ccc(-c7ccccc7)cc6)c5ccc43)cc2)cc1]
34
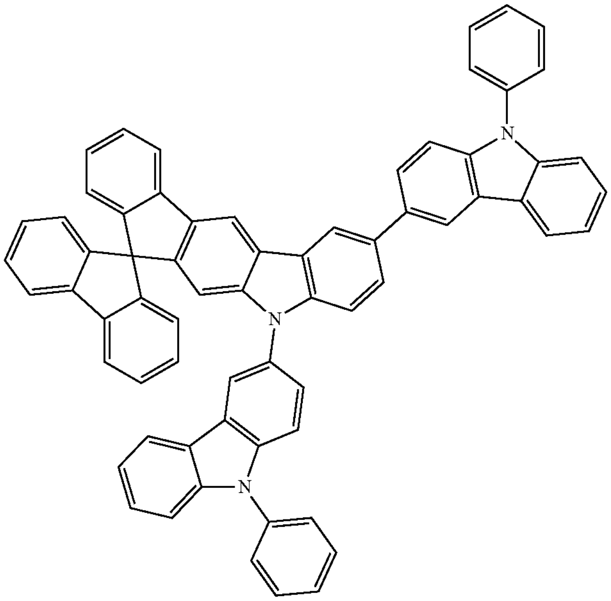 [SMILES: c1ccc(-n2c3ccccc3c3cc(-c4ccc5c(c4)c4cc6c(cc4n5-c4ccc5c(c4)c4ccccc4n5-c4ccccc4)C4(c5ccccc5-c5ccccc54)c4ccccc4-6)ccc32)cc1]

TABLE 3-continued
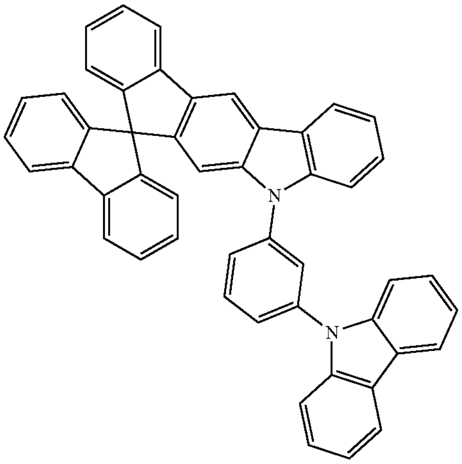 [SMILES: c1cc(-n2c3ccccc3c3ccccc32)cc(-n2c3ccccc3c3cc4c(cc32)C2(c3ccccc3-c3ccccc32)c2ccccc2-4)c1]
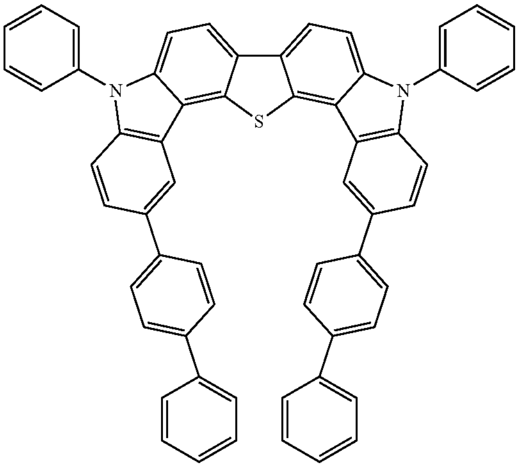 [SMILES: c1ccc(-c2ccc(-c3ccc4c(c3)c3c5sc6c(ccc7c6c6cc(-c8ccc(-c9ccccc9)cc8)ccc6n7-c6ccccc6)c5ccc3n4-c3ccccc3)cc2)cc1]
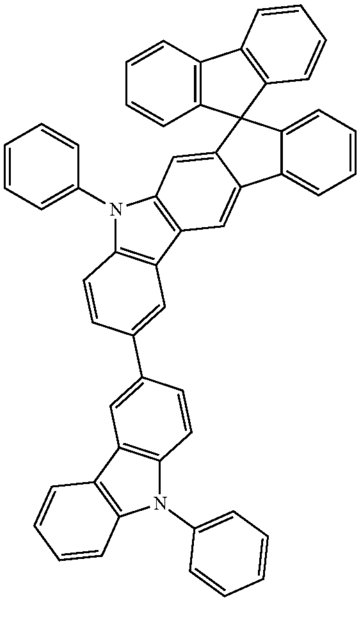 [SMILES: c1ccc(-n2c3ccccc3c3cc(-c4ccc5c(c4)c4cc6c(cc4n5-c4ccccc4)C4(c5ccccc5-c5ccccc54)c4ccccc4-6)ccc32)cc1]

TABLE 3-continued
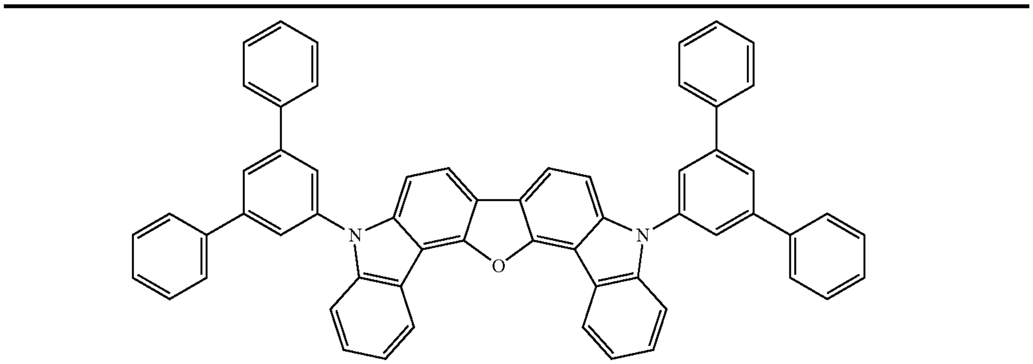
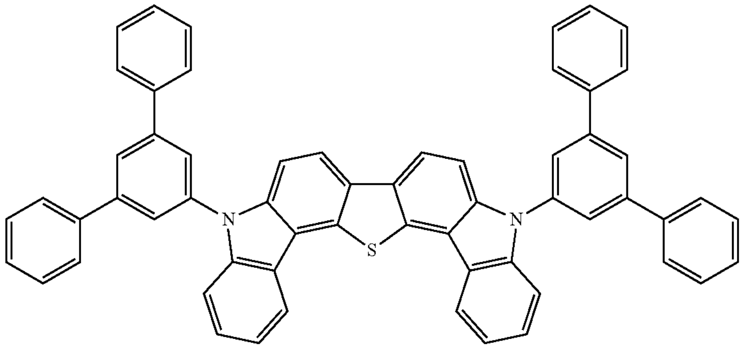 [SMILES: c1ccc(-c2cc(-c3ccccc3)cc(-n3c4ccccc4c4c5sc6c(ccc7c6c6ccccc6n7-c6cc(-c7ccccc7)cc(-c7ccccc7)c6)c5ccc43)c2)cc1]
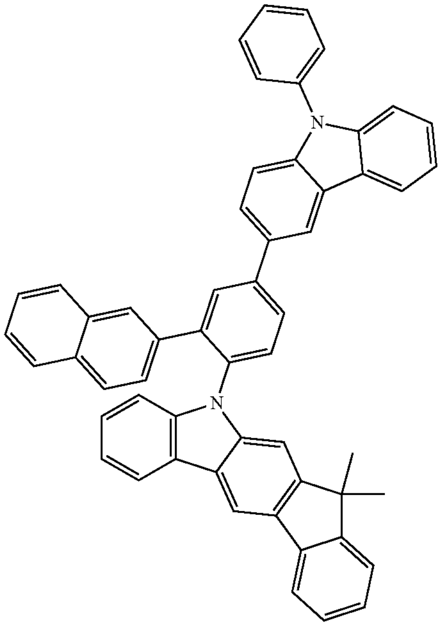 [SMILES: CC1(C)c2ccccc2-c2cc3c4ccccc4n(-c4ccc(-c5ccc6c(c5)c5ccccc5n6-c5ccccc5)cc4-c4ccc5ccccc5c4)c3cc21]

TABLE 3-continued
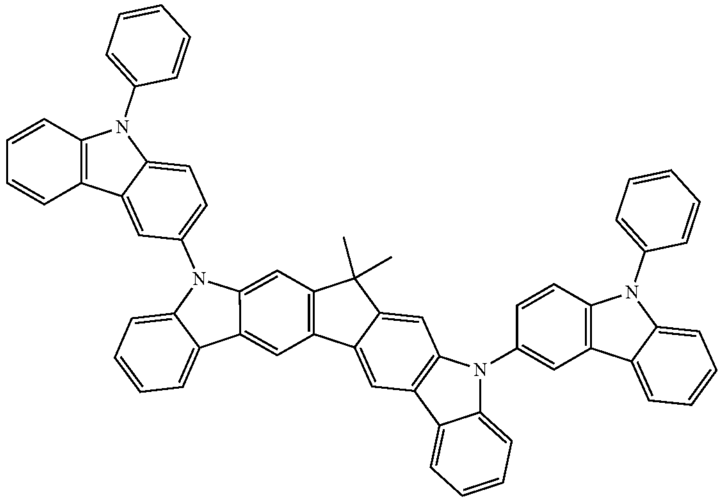 [SMILES: CC1(C)c2cc3c(cc2-c2cc4c5ccccc5n(-c5ccc6c(c5)c5ccccc5n6-c5ccccc5)c4cc21)c1ccccc1n3-c1ccc2c(c1)c1ccccc1n2-c1ccccc1]
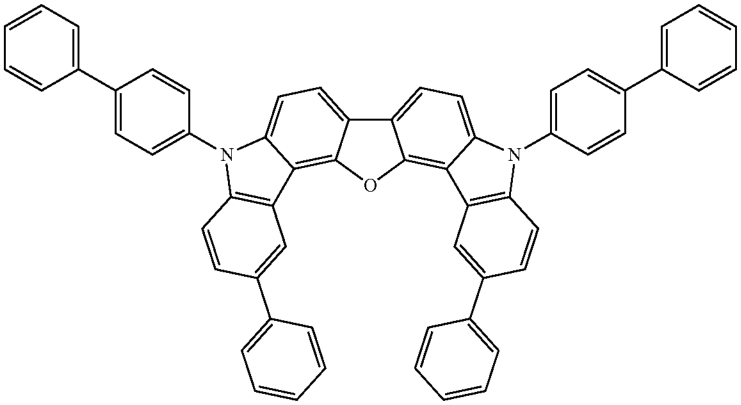 [SMILES: c1ccc(-c2ccc(-n3c4ccc(-c5ccccc5)cc4c4c5oc6c(ccc7c6c6cc(-c8ccccc8)ccc6n7-c6ccc(-c7ccccc7)cc6)c5ccc43)cc2)cc1]
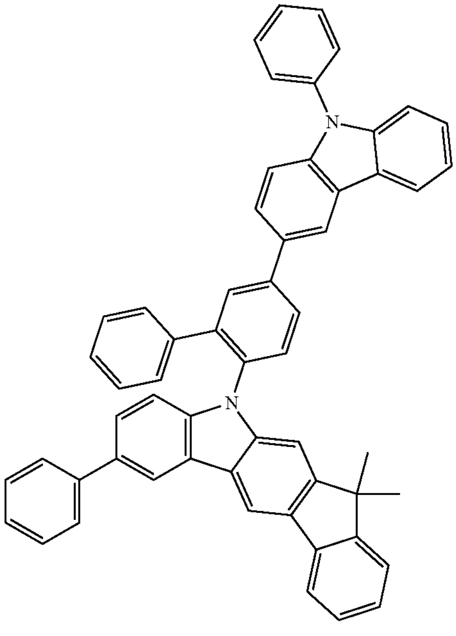 [SMILES: CC1(C)c2ccccc2-c2cc3c4cc(-c5ccccc5)ccc4n(-c4ccc(-c5ccc6c(c5)c5ccccc5n6-c5ccccc5)cc4-c4ccccc4)c3cc21]

TABLE 3-continued
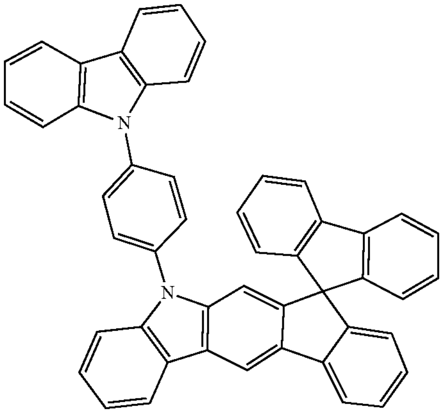 [SMILES: c1ccc2c(c1)-c1ccccc1C21c2ccccc2-c2cc3c4ccccc4n(-c4ccc(-n5c6ccccc6c6ccccc65)cc4)c3cc21]
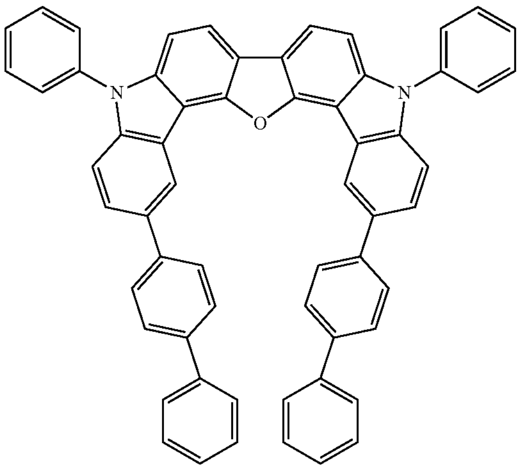 [SMILES: c1ccc(-c2ccc(-c3ccc4c(c3)c3c5oc6c(ccc7c6c6cc(-c8ccc(-c9ccccc9)cc8)ccc6n7-c6ccccc6)c5ccc3n4-c3ccccc3)cc2)cc1]
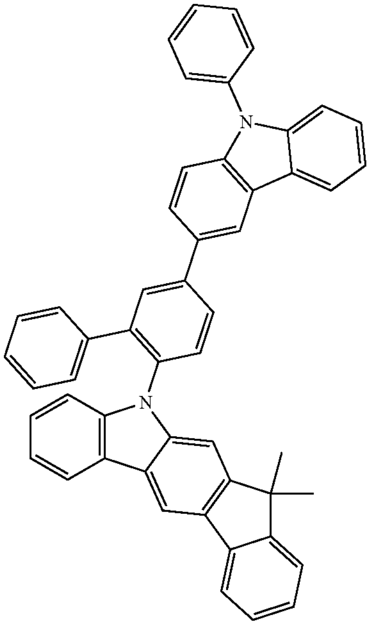 [SMILES: CC1(C)c2ccccc2-c2cc3c4ccccc4n(-c4ccc(-c5ccc6c(c5)c5ccccc5n6-c5ccccc5)cc4-c4ccccc4)c3cc21]

TABLE 3-continued
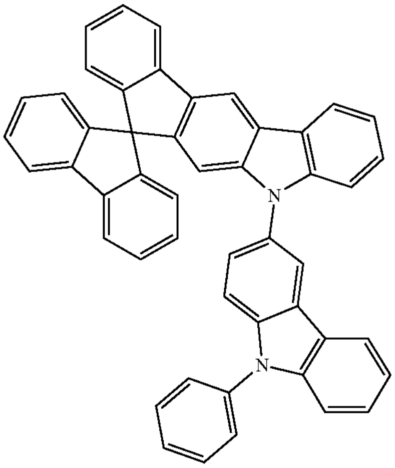 [SMILES: c1ccc(-n2c3ccccc3c3cc(-n4c5ccccc5c5cc6c(cc54)C4(c5ccccc5-c5ccccc54)c4ccccc4-6)ccc32)cc1]
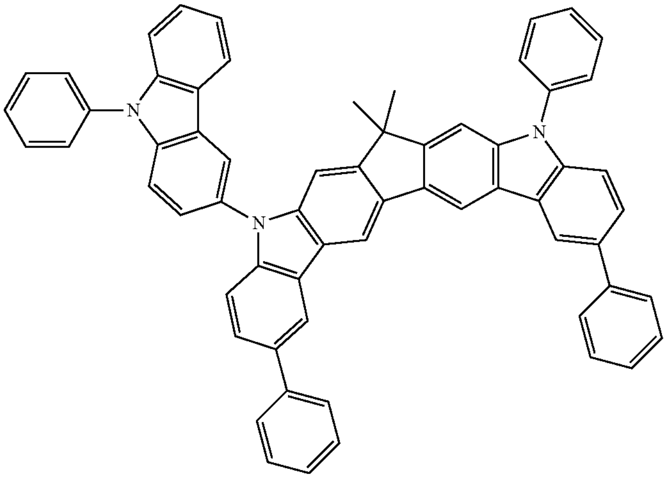 [SMILES: CC1(C)c2cc3c(cc2-c2cc4c5cc(-c6ccccc6)ccc5n(-c5ccc6c(c5)c5ccccc5n6-c5ccccc5)c4cc21)c1cc(-c2ccccc2)ccc1n3-c1ccccc1]
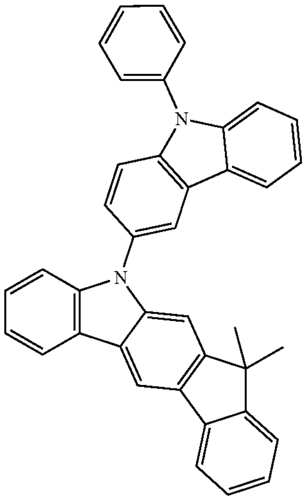 [SMILES: CC1(C)c2ccccc2-c2cc3c4ccccc4n(-c4ccc5c(c4)c4ccccc4n5-c4ccccc4)c3cc21]

TABLE 3-continued
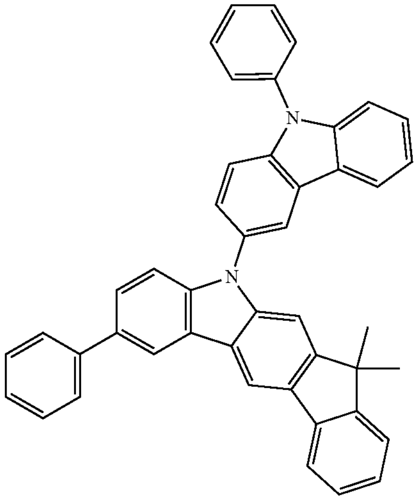 [SMILES: CC1(C)c2ccccc2-c2cc3c4cc(-c5ccccc5)ccc4n(-c4ccc5c(c4)c4ccccc4n5-c4ccccc4)c3cc21]
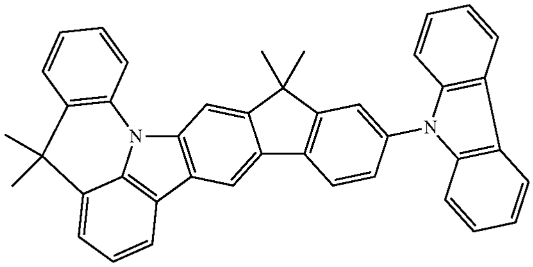 [SMILES: CC1(C)c2cc(-n3c4ccccc4c4ccccc43)ccc2-c2cc3c4cccc5c4n(c3cc21)-c1ccccc1C5(C)C]
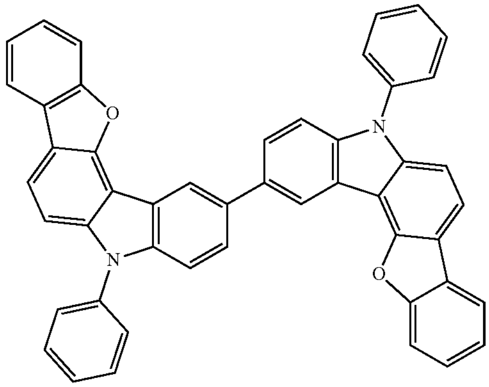 [SMILES: c1ccc(-n2c3ccc(-c4ccc5c(c4)c4c6oc7ccccc7c6ccc4n5-c4ccccc4)cc3c3c4oc5ccccc5c4ccc32)cc1]
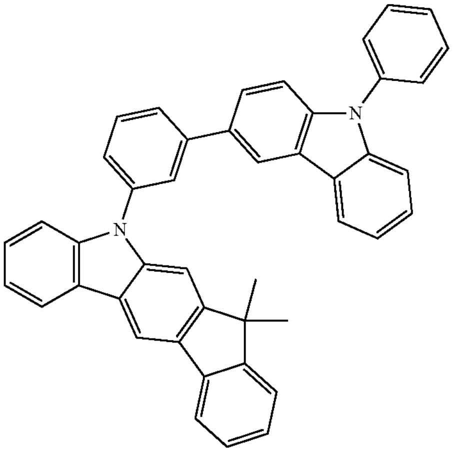 [SMILES: CC1(C)c2ccccc2-c2cc3c4ccccc4n(-c4cccc(-c5ccc6c(c5)c5ccccc5n6-c5ccccc5)c4)c3cc21]

TABLE 3-continued
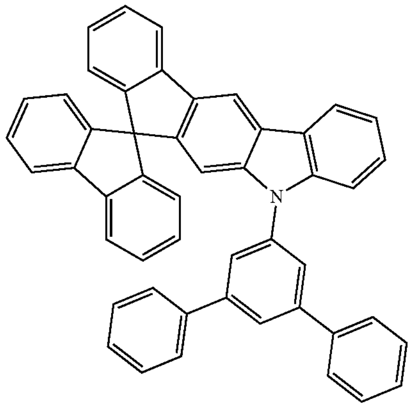 [SMILES: c1ccc(-c2cc(-c3ccccc3)cc(-n3c4ccccc4c4cc5c(cc43)C3(c4ccccc4-c4ccccc43)c3ccccc3-5)c2)cc1]
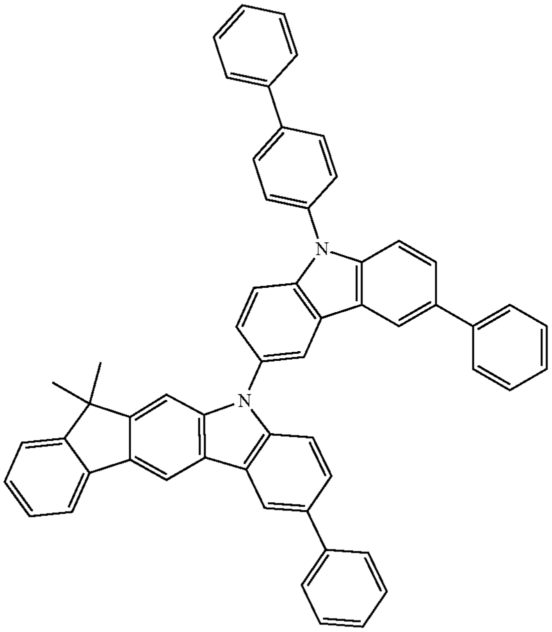 [SMILES: CC1(C)c2ccccc2-c2cc3c4cc(-c5ccccc5)ccc4n(-c4ccc5c(c4)c4cc(-c6ccccc6)ccc4n5-c4ccc(-c5ccccc5)cc4)c3cc21]
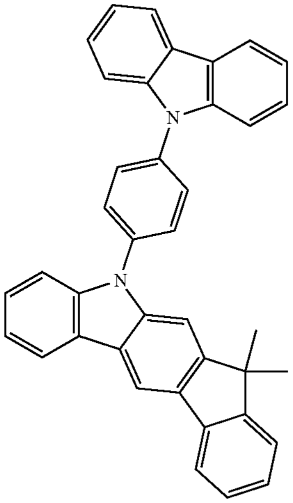 [SMILES: CC1(C)c2ccccc2-c2cc3c4ccccc4n(-c4ccc(-n5c6ccccc6c6ccccc65)cc4)c3cc21]

TABLE 3-continued
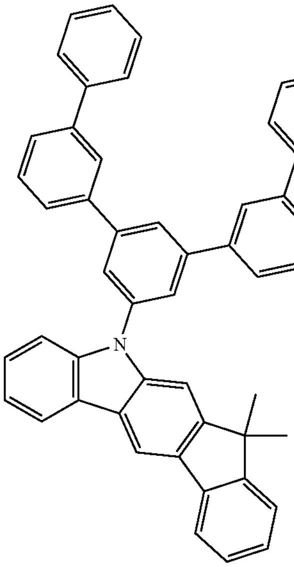
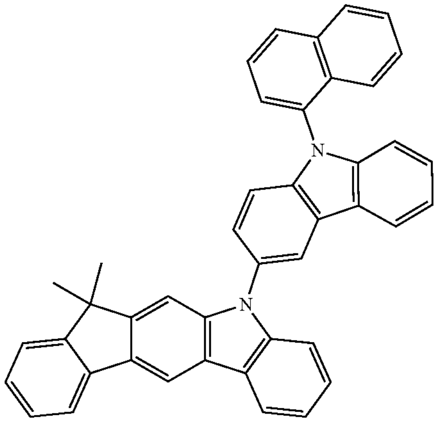 [SMILES: CC1(C)c2ccccc2-c2cc3c4ccccc4n(-c4ccc5c(c4)c4ccccc4n5-c4cccc5ccccc45)c3cc21]
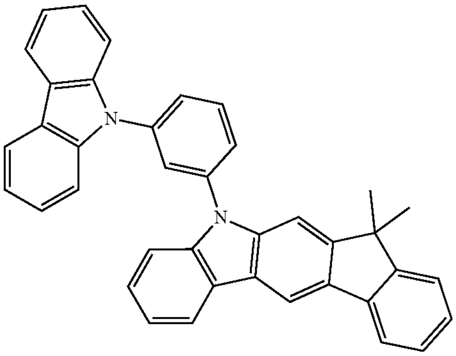 [SMILES: CC1(C)c2ccccc2-c2cc3c4ccccc4n(-c4cccc(-n5c6ccccc6c6ccccc65)c4)c3cc21]

TABLE 3-continued
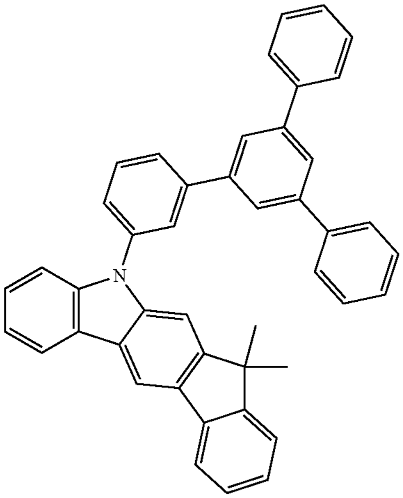 [SMILES: CC1(C)c2ccccc2-c2cc3c4ccccc4n(-c4cccc(-c5cc(-c6ccccc6)cc(-c6ccccc6)c5)c4)c3cc21]
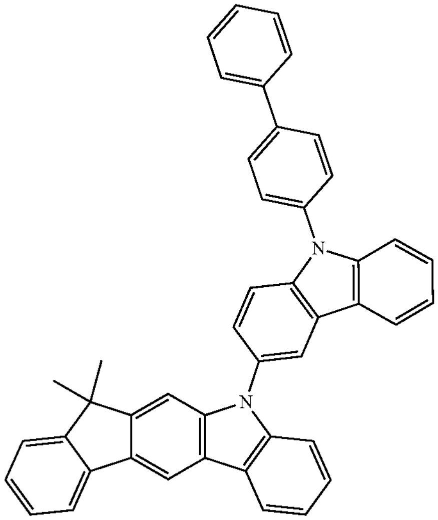 [SMILES: CC1(C)c2ccccc2-c2cc3c4ccccc4n(-c4ccc5c(c4)c4ccccc4n5-c4ccc(-c5ccccc5)cc4)c3cc21]
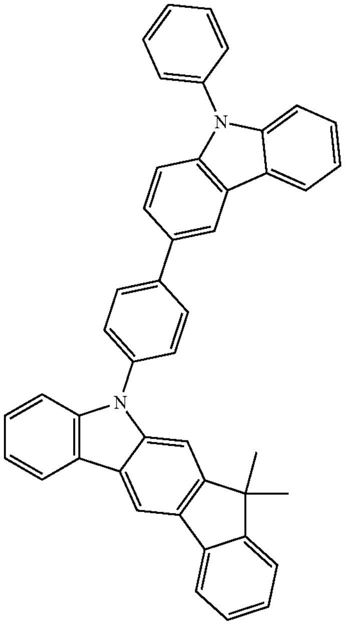 [SMILES: CC1(C)c2ccccc2-c2cc3c4ccccc4n(-c4ccc(-c5ccc6c(c5)c5ccccc5n6-c5ccccc5)cc4)c3cc21]

TABLE 3-continued
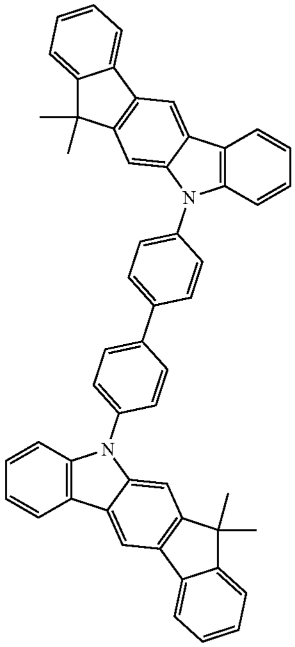 [SMILES: CC1(C)c2ccccc2-c2cc3c4ccccc4n(-c4ccc(-c5ccc(-n6c7ccccc7c7cc8c(cc76)C(C)(C)c6ccccc6-8)cc5)cc4)c3cc21]
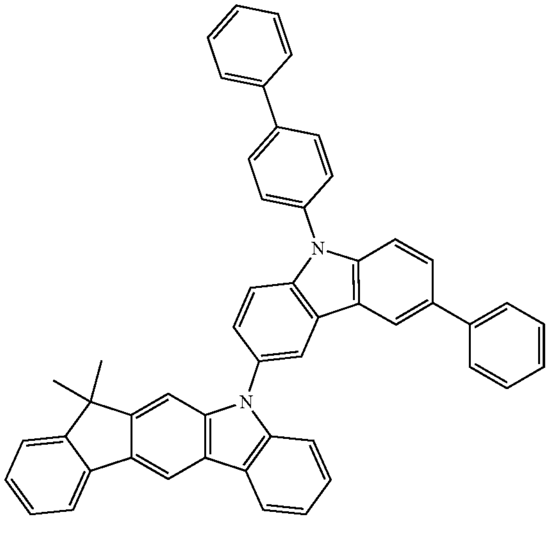 [SMILES: CC1(C)c2ccccc2-c2cc3c4ccccc4n(-c4ccc5c(c4)c4cc(-c6ccccc6)ccc4n5-c4ccc(-c5ccccc5)cc4)c3cc21]

TABLE 3-continued
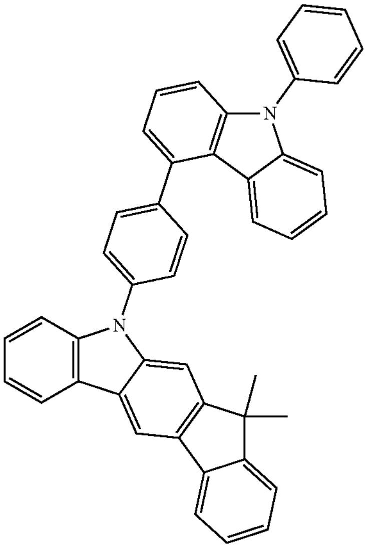 [SMILES: CC1(C)c2ccccc2-c2cc3c4ccccc4n(-c4ccc(-c5cccc6c5c5ccccc5n6-c5ccccc5)cc4)c3cc21]
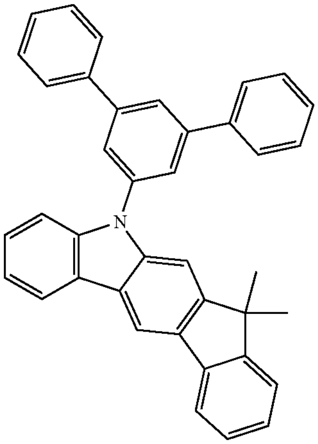 [SMILES: CC1(C)c2ccccc2-c2cc3c4ccccc4n(-c4cc(-c5ccccc5)cc(-c5ccccc5)c4)c3cc21]
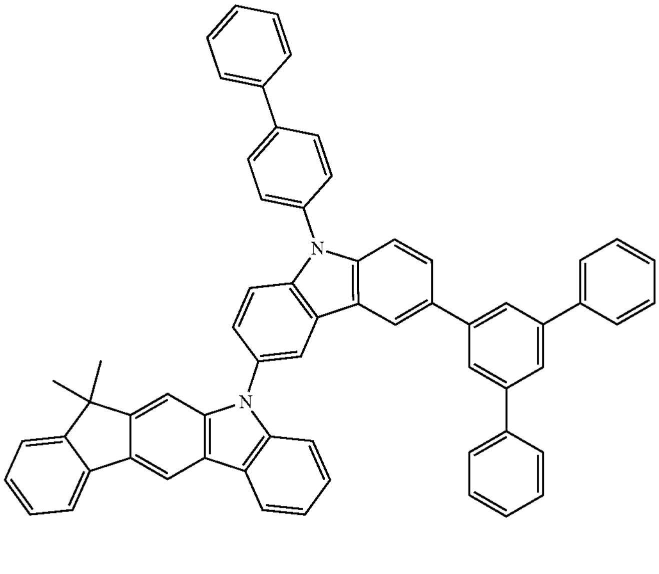 [SMILES: CC1(C)c2ccccc2-c2cc3c4ccccc4n(-c4ccc5c(c4)c4cc(-c6cc(-c7ccccc7)cc(-c7ccccc7)c6)ccc4n5-c4ccc(-c5ccccc5)cc4)c3cc21]

TABLE 3-continued
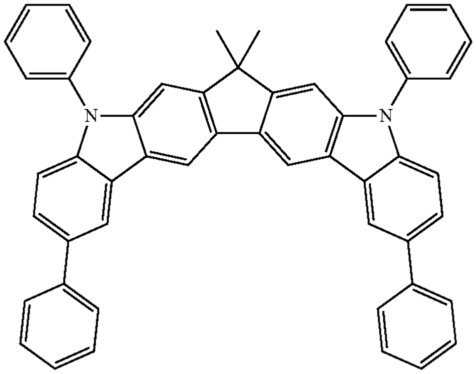 [SMILES: CC1(C)c2cc3c(cc2-c2cc4c5cc(-c6ccccc6)ccc5n(-c5ccccc5)c4cc21)c1cc(-c2ccccc2)ccc1n3-c1ccccc1]
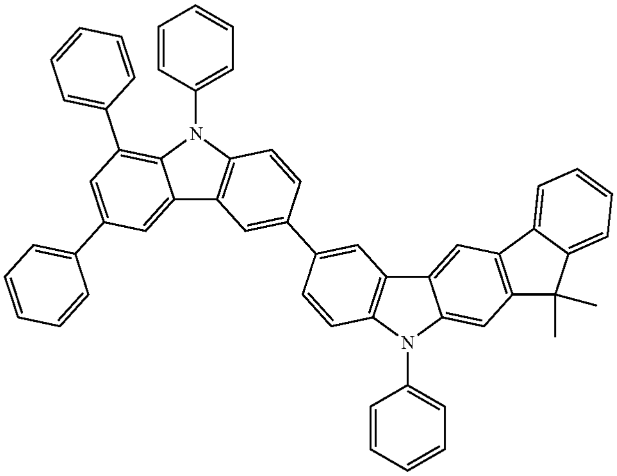 [SMILES: CC1(C)c2ccccc2-c2cc3c4cc(-c5ccc6c(c5)c5cc(-c7ccccc7)cc(-c7ccccc7)c5n6-c5ccccc5)ccc4n(-c4ccccc4)c3cc21]
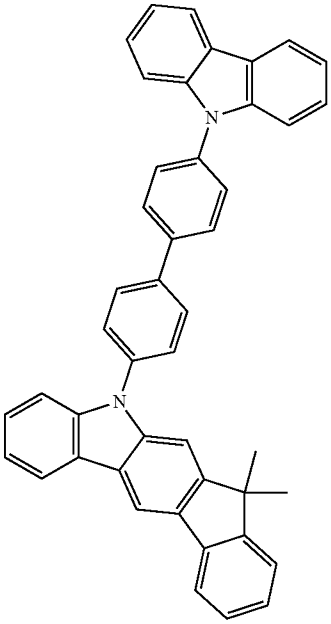 [SMILES: CC1(C)c2ccccc2-c2cc3c4ccccc4n(-c4ccc(-c5ccc(-n6c7ccccc7c7ccccc76)cc5)cc4)c3cc21]

TABLE 3-continued
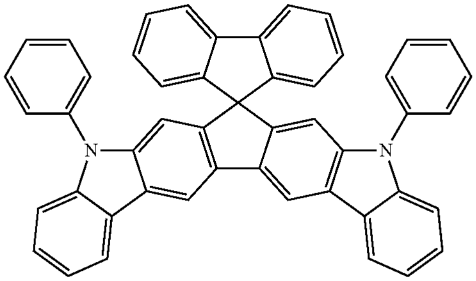 [SMILES: c1ccc(-n2c3ccccc3c3cc4c(cc32)C2(c3ccccc3-c3ccccc32)c2cc3c(cc2-4)c2ccccc2n3-c2ccccc2)cc1]
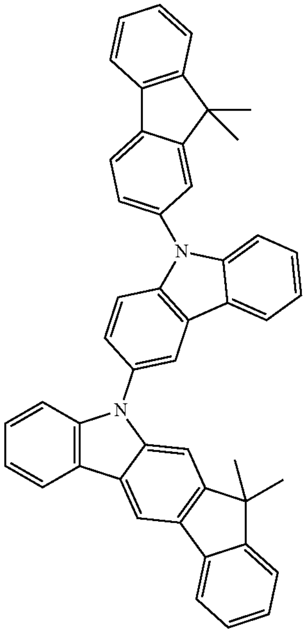 [SMILES: CC1(C)c2ccccc2-c2ccc(-n3c4ccccc4c4cc(-n5c6ccccc6c6cc7c(cc65)C(C)(C)c5ccccc5-7)ccc43)cc21]
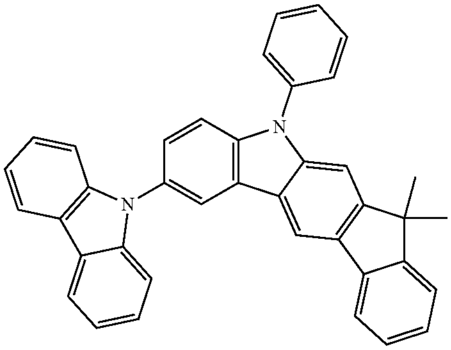 [SMILES: CC1(C)c2ccccc2-c2cc3c4cc(-n5c6ccccc6c6ccccc65)ccc4n(-c4ccccc4)c3cc21]

TABLE 3-continued
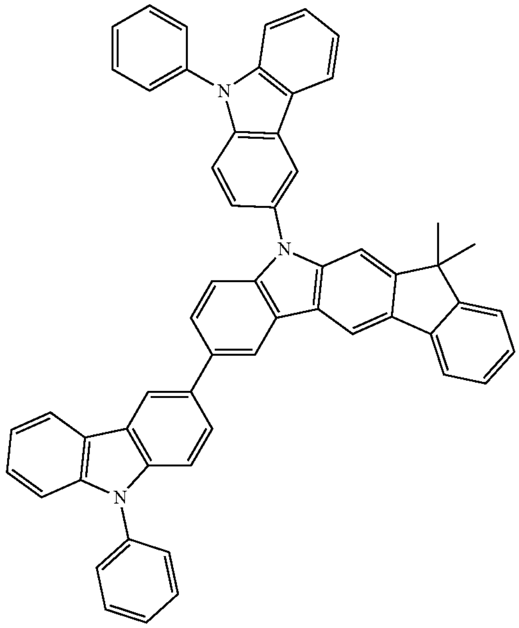 [SMILES: CC1(C)c2ccccc2-c2cc3c4cc(-c5ccc6c(c5)c5ccccc5n6-c5ccccc5)ccc4n(-c4ccc5c(c4)c4ccccc4n5-c4ccccc4)c3cc21]
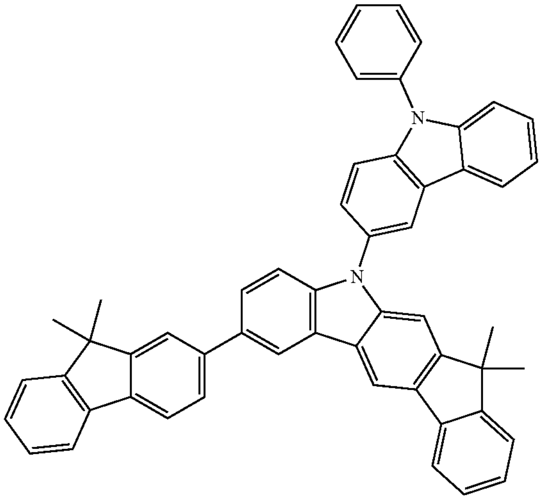 [SMILES: CC1(C)c2ccccc2-c2ccc(-c3ccc4c(c3)c3cc5c(cc3n4-c3ccc4c(c3)c3ccccc3n4-c3ccccc3)C(C)(C)c3ccccc3-5)cc21]
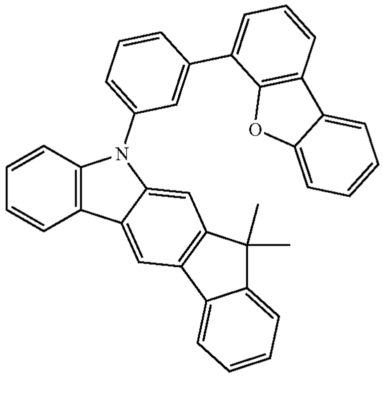 [SMILES: CC1(C)c2ccccc2-c2cc3c4ccccc4n(-c4cccc(-c5cccc6c5oc5ccccc56)c4)c3cc21]

TABLE 3-continued
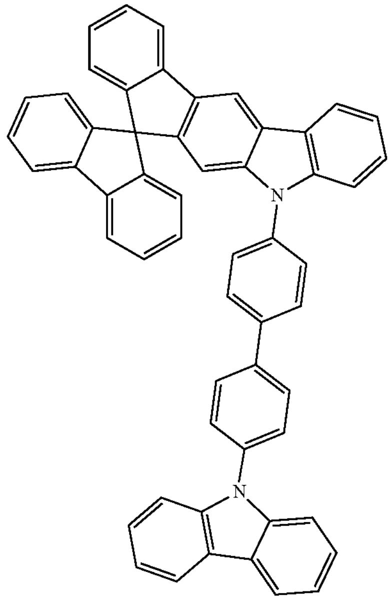 [SMILES: c1ccc2c(c1)-c1ccccc1C21c2ccccc2-c2cc3c4ccccc4n(-c4ccc(-c5ccc(-n6c7ccccc7c7ccccc76)cc5)cc4)c3cc21]
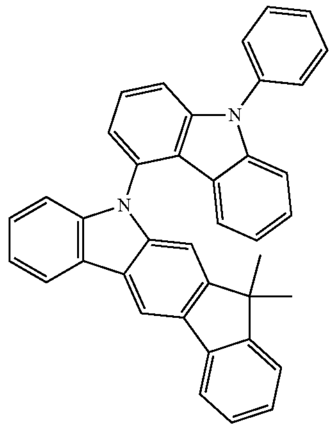 [SMILES: CC1(C)c2ccccc2-c2cc3c4ccccc4n(-c4cccc5c4c4ccccc4n5-c4ccccc4)c3cc21]
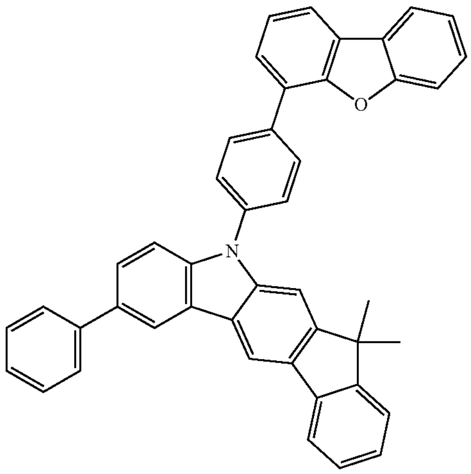 [SMILES: CC1(C)c2ccccc2-c2cc3c4cc(-c5ccccc5)ccc4n(-c4ccc(-c5cccc6c5oc5ccccc56)cc4)c3cc21]

TABLE 3-continued
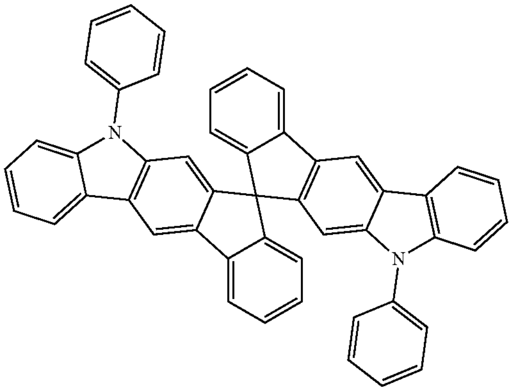 [SMILES: c1ccc(-n2c3ccccc3c3cc4c(cc32)C2(c3ccccc3-4)c3ccccc3-c3cc4c5ccccc5n(-c5ccccc5)c4cc32)cc1]
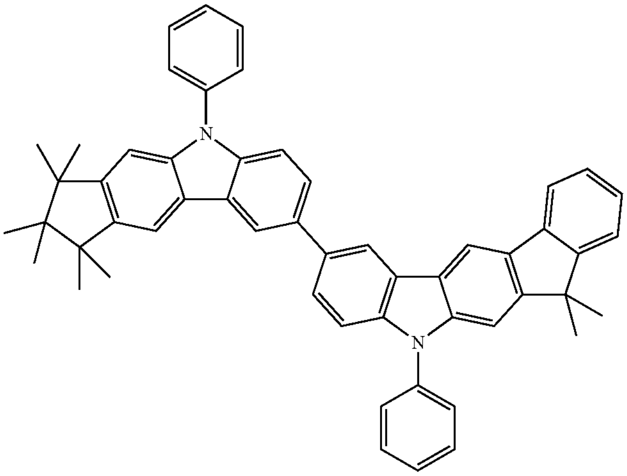 [SMILES: CC1(C)c2ccccc2-c2cc3c4cc(-c5ccc6c(c5)c5cc7c(cc5n6-c5ccccc5)C(C)(C)C(C)(C)C7(C)C)ccc4n(-c4ccccc4)c3cc21]
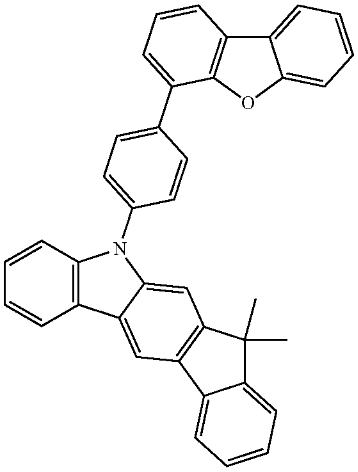 [SMILES: CC1(C)c2ccccc2-c2cc3c4ccccc4n(-c4ccc(-c5cccc6c5oc5ccccc56)cc4)c3cc21]

TABLE 3-continued
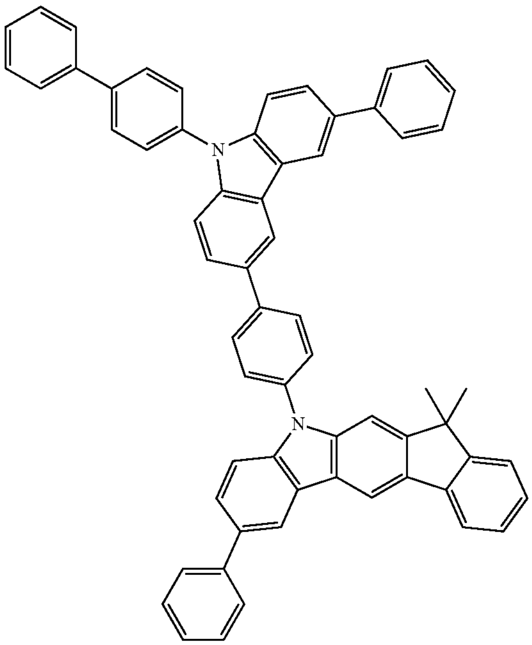 [SMILES: CC1(C)c2ccccc2-c2cc3c4cc(-c5ccccc5)ccc4n(-c4ccc(-c5ccc6c(c5)c5cc(-c7ccccc7)ccc5n6-c5ccc(-c6ccccc6)cc5)cc4)c3cc21]
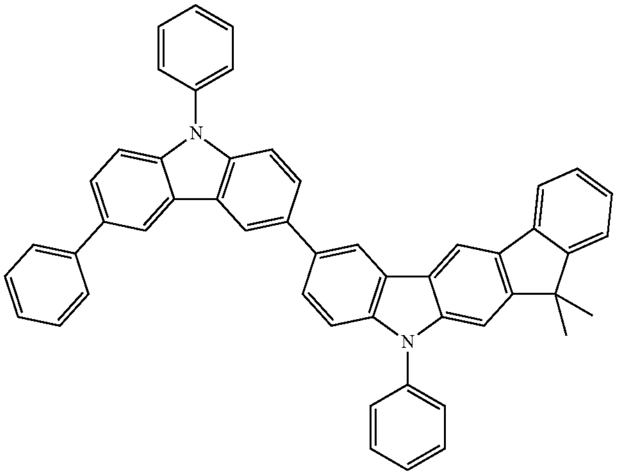 [SMILES: CC1(C)c2ccccc2-c2cc3c4cc(-c5ccc6c(c5)c5cc(-c7ccccc7)ccc5n6-c5ccccc5)ccc4n(-c4ccccc4)c3cc21]
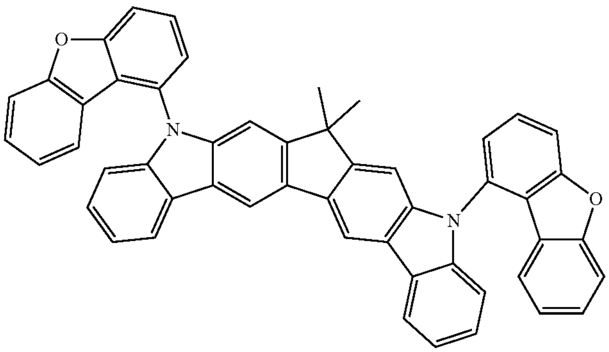 [SMILES: CC1(C)c2cc3c(cc2-c2cc4c5ccccc5n(-c5cccc6oc7ccccc7c56)c4cc21)c1ccccc1n3-c1cccc2oc3ccccc3c12]

TABLE 3-continued
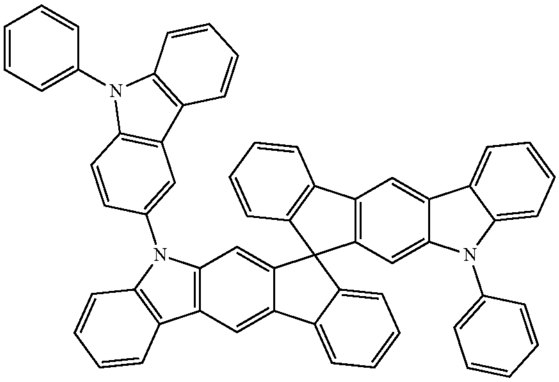 [SMILES: c1ccc(-n2c3ccccc3c3cc(-n4c5ccccc5c5cc6c(cc54)C4(c5ccccc5-c5cc7c8ccccc8n(-c8ccccc8)c7cc54)c4ccccc4-6)ccc32)cc1]
22
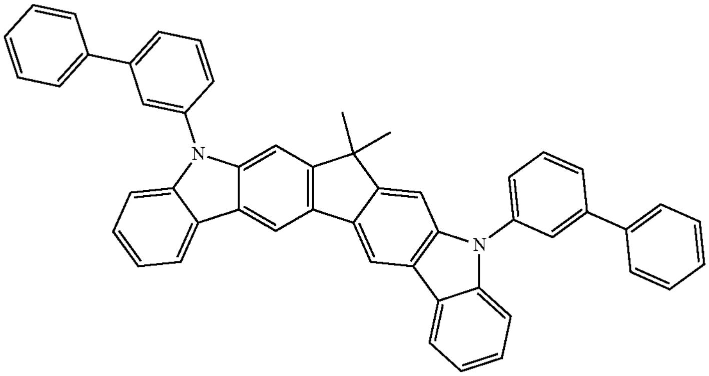 [SMILES: CC1(C)c2cc3c(cc2-c2cc4c5ccccc5n(-c5cccc(-c6ccccc6)c5)c4cc21)c1ccccc1n3-c1cccc(-c2ccccc2)c1]
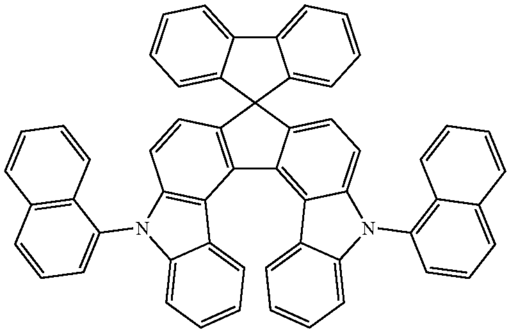 [SMILES: c1ccc2c(c1)-c1ccccc1C21c2ccc3c(c2-c2c1ccc1c2c2ccccc2n1-c1cccc2ccccc12)c1ccccc1n3-c1cccc2ccccc12]
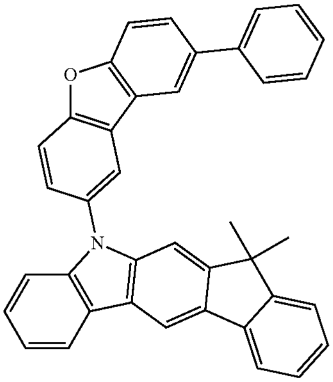 [SMILES: CC1(C)c2ccccc2-c2cc3c4ccccc4n(-c4ccc5oc6ccc(-c7ccccc7)cc6c5c4)c3cc21]

TABLE 3-continued
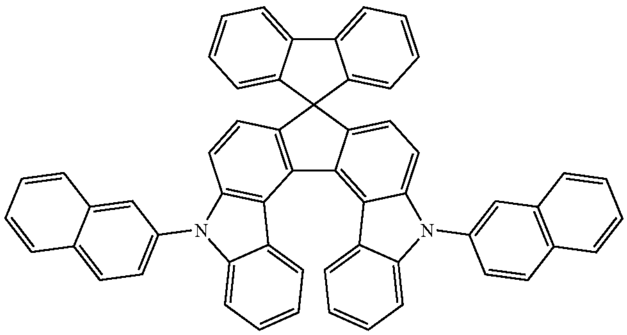 [SMILES: c1ccc2c(c1)-c1ccccc1C21c2ccc3c(c2-c2c1ccc1c2c2ccccc2n1-c1ccc2ccccc2c1)c1ccccc1n3-c1ccc2ccccc2c1]
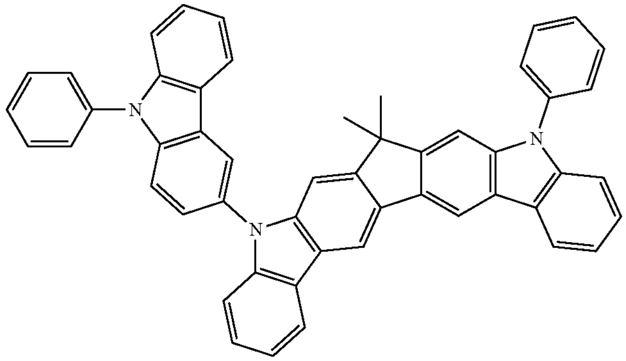 [SMILES: CC1(C)c2cc3c(cc2-c2cc4c5ccccc5n(-c5ccc6c(c5)c5ccccc5n6-c5ccccc5)c4cc21)c1ccccc1n3-c1ccccc1]
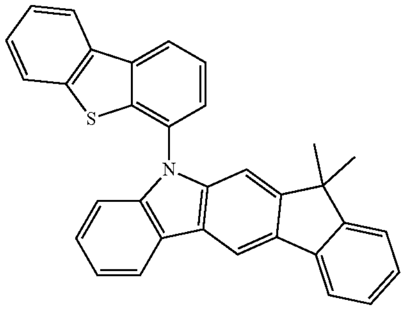 [SMILES: CC1(C)c2ccccc2-c2cc3c4ccccc4n(-c4cccc5c4sc4ccccc45)c3cc21]
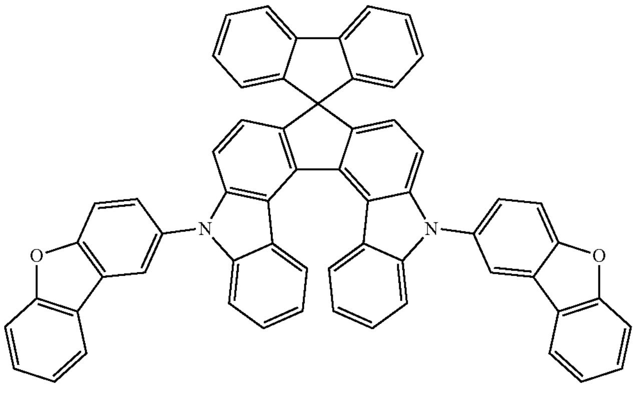 [SMILES: c1ccc2c(c1)-c1ccccc1C21c2ccc3c(c2-c2c1ccc1c2c2ccccc2n1-c1ccc2oc4ccccc4c2c1)c1ccccc1n3-c1ccc2oc3ccccc3c2c1]

TABLE 3-continued
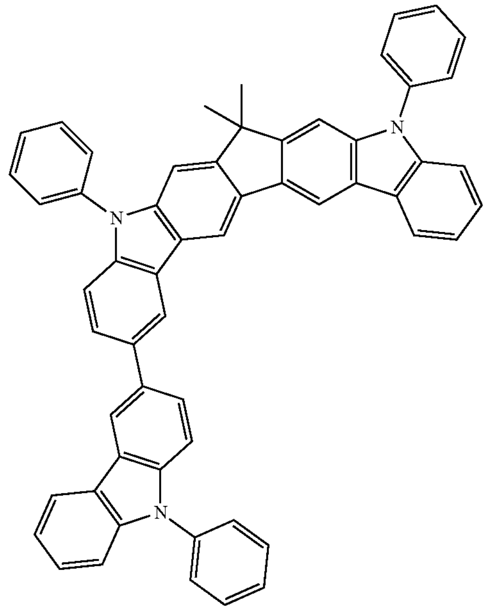 [SMILES: CC1(C)c2cc3c(cc2-c2cc4c5cc(-c6ccc7c(c6)c6ccccc6n7-c6ccccc6)ccc5n(-c5ccccc5)c4cc21)c1ccccc1n3-c1ccccc1]
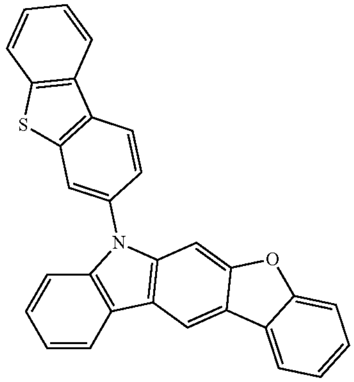 [SMILES: c1ccc2c(c1)oc1cc3c(cc12)c1ccccc1n3-c1ccc2c(c1)sc1ccccc12]
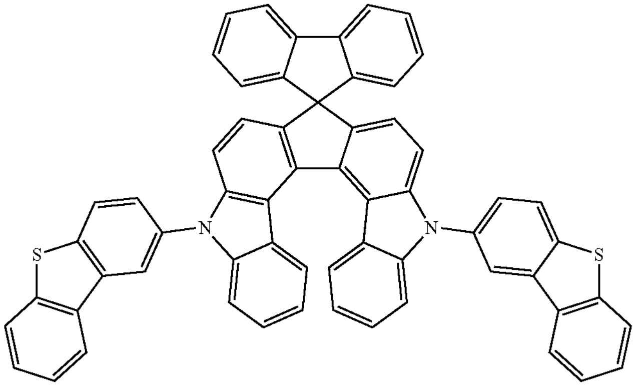 [SMILES: c1ccc2c(c1)-c1ccccc1C21c2ccc3c(c2-c2c1ccc1c2c2ccccc2n1-c1ccc2sc4ccccc4c2c1)c1ccccc1n3-c1ccc2sc3ccccc3c2c1]

TABLE 3-continued
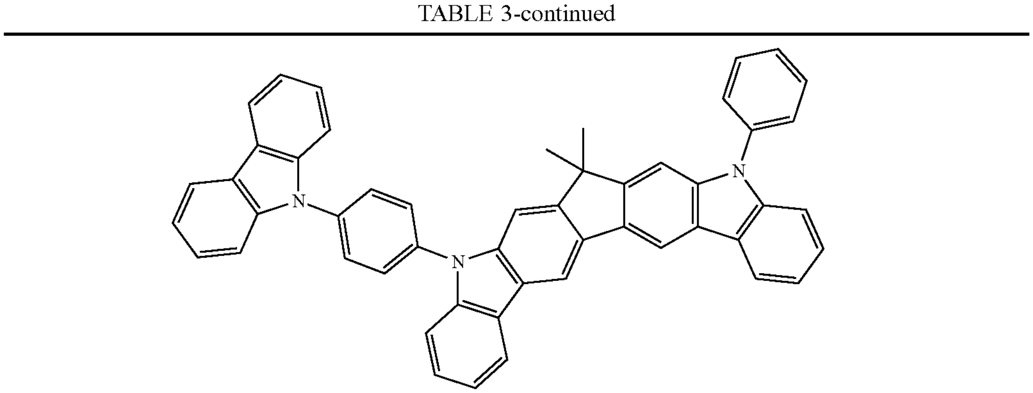
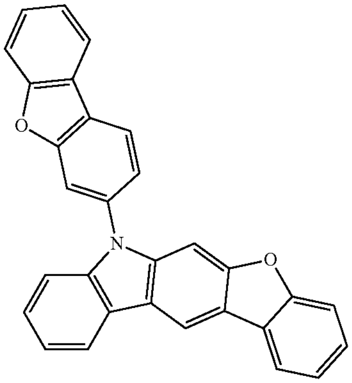 [SMILES: c1ccc2c(c1)oc1cc(-n3c4ccccc4c4cc5c(cc43)oc3ccccc35)ccc12]
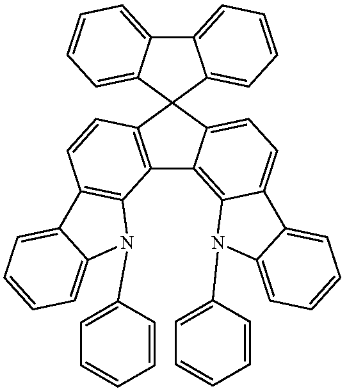 [SMILES: c1ccc(-n2c3ccccc3c3ccc4c(c32)-c2c(ccc3c5ccccc5n(-c5ccccc5)c23)C42c3ccccc3-c3ccccc32)cc1]
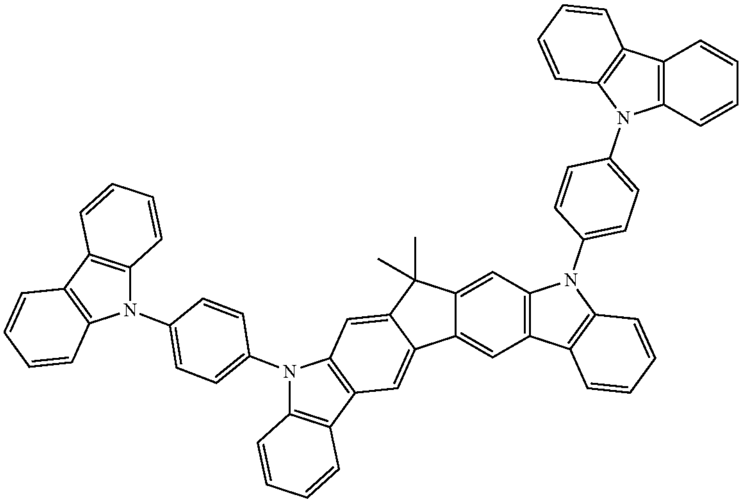 [SMILES: CC1(C)c2cc3c(cc2-c2cc4c5ccccc5n(-c5ccc(-n6c7ccccc7c7ccccc76)cc5)c4cc21)c1ccccc1n3-c1ccc(-n2c3ccccc3c3ccccc32)cc1]

TABLE 3-continued
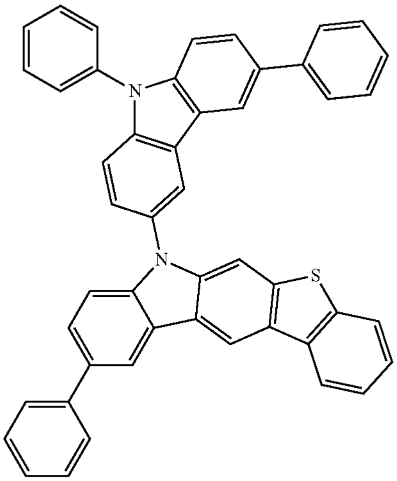 [SMILES: c1ccc(-c2ccc3c(c2)c2cc(-n4c5ccc(-c6ccccc6)cc5c5cc6c(cc54)sc4ccccc46)ccc2n3-c2ccccc2)cc1]
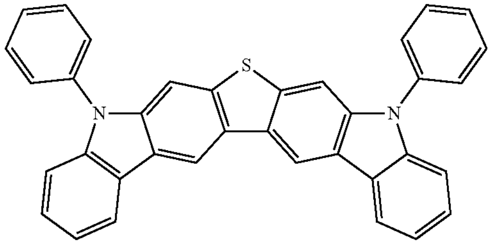 [SMILES: c1ccc(-n2c3ccccc3c3cc4c(cc32)sc2cc3c(cc24)c2ccccc2n3-c2ccccc2)cc1]
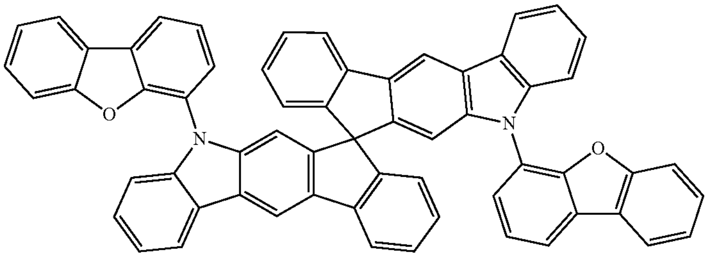 [SMILES: c1ccc2c(c1)-c1cc3c4ccccc4n(-c4cccc5c4oc4ccccc45)c3cc1C21c2ccccc2-c2cc3c4ccccc4n(-c4cccc5c4oc4ccccc45)c3cc21]
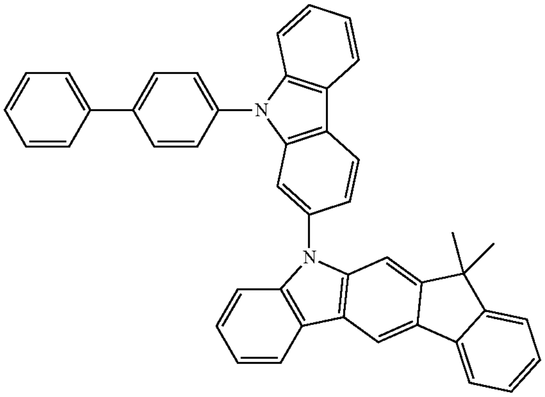 [SMILES: CC1(C)c2ccccc2-c2cc3c4ccccc4n(-c4ccc5c6ccccc6n(-c6ccc(-c7ccccc7)cc6)c5c4)c3cc21]

TABLE 3-continued
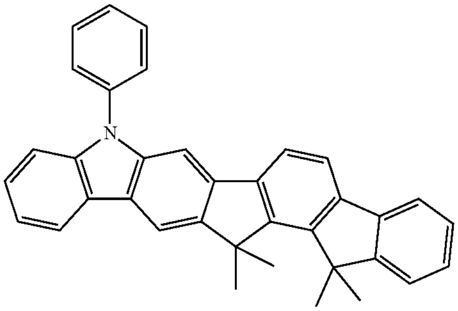 [SMILES: CC1(C)c2ccccc2-c2ccc3c(c21)C(C)(C)c1cc2c4ccccc4n(-c4ccccc4)c2cc1-3]
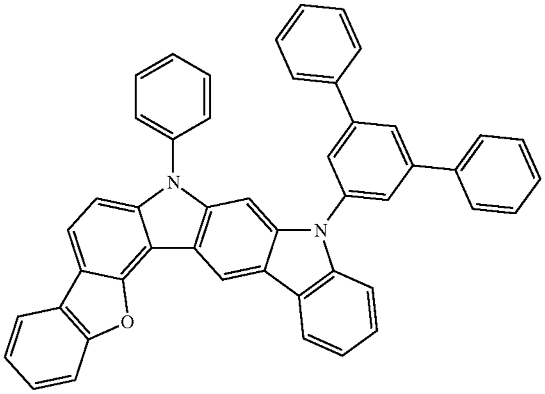 [SMILES: c1ccc(-c2cc(-c3ccccc3)cc(-n3c4ccccc4c4cc5c6c7oc8ccccc8c7ccc6n(-c6ccccc6)c5cc43)c2)cc1]
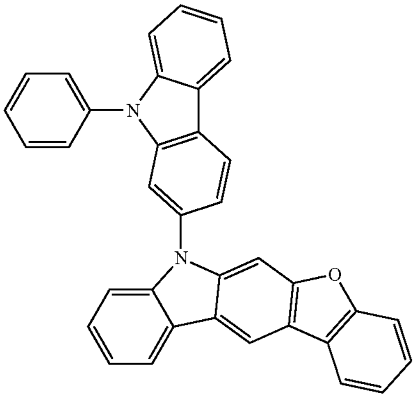 [SMILES: c1ccc(-n2c3ccccc3c3ccc(-n4c5ccccc5c5cc6c(cc54)oc4ccccc46)cc32)cc1]

TABLE 3-continued
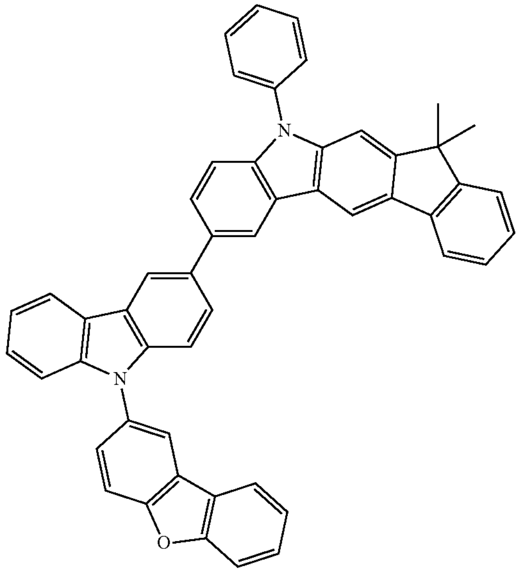 [SMILES: CC1(C)c2ccccc2-c2cc3c4cc(-c5ccc6c(c5)c5ccccc5n6-c5ccc6oc7ccccc7c6c5)ccc4n(-c4ccccc4)c3cc21]
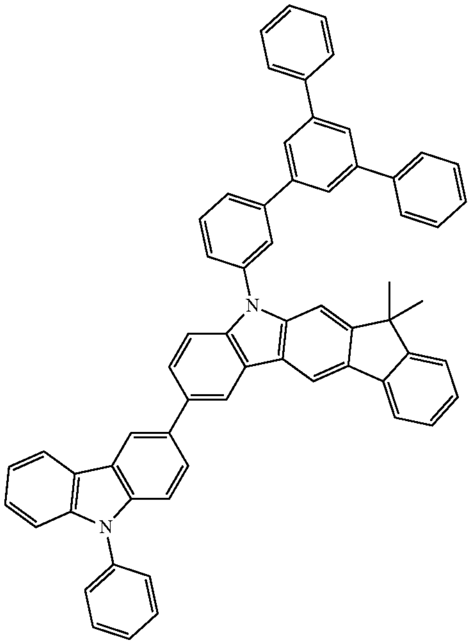 [SMILES: CC1(C)c2ccccc2-c2cc3c4cc(-c5ccc6c(c5)c5ccccc5n6-c5ccccc5)ccc4n(-c4cccc(-c5cc(-c6ccccc6)cc(-c6ccccc6)c5)c4)c3cc21]
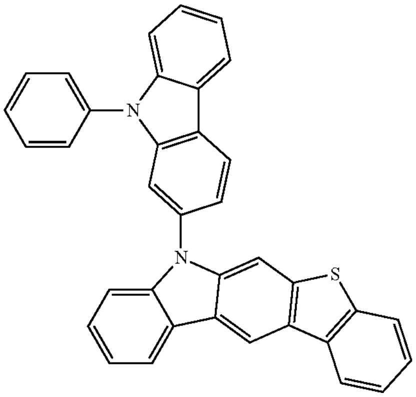 [SMILES: c1ccc(-n2c3ccccc3c3ccc(-n4c5ccccc5c5cc6c(cc54)sc4ccccc46)cc32)cc1]

TABLE 3-continued
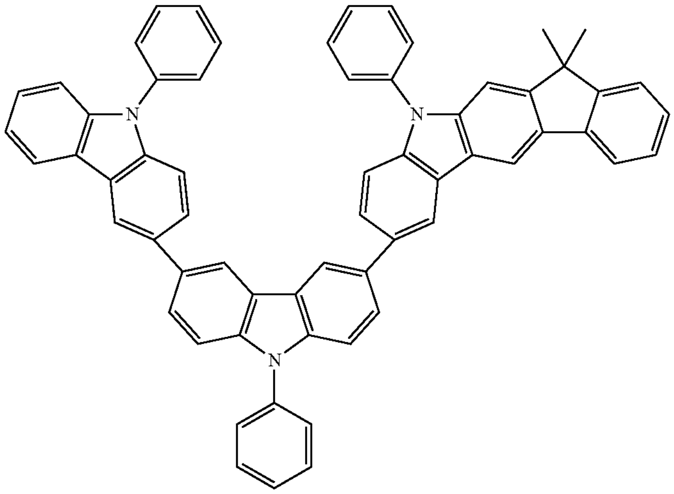 [SMILES: CC1(C)c2ccccc2-c2cc3c4cc(-c5ccc6c(c5)c5cc(-c7ccc8c(c7)c7ccccc7n8-c7ccccc7)ccc5n6-c5ccccc5)ccc4n(-c4ccccc4)c3cc21]
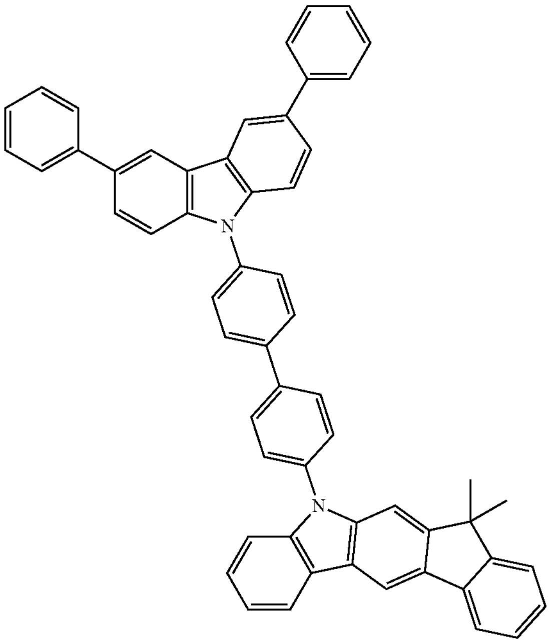 [SMILES: CC1(C)c2ccccc2-c2cc3c4ccccc4n(-c4ccc(-c5ccc(-n6c7ccc(-c8ccccc8)cc7c7cc(-c8ccccc8)ccc76)cc5)cc4)c3cc21]

TABLE 3-continued
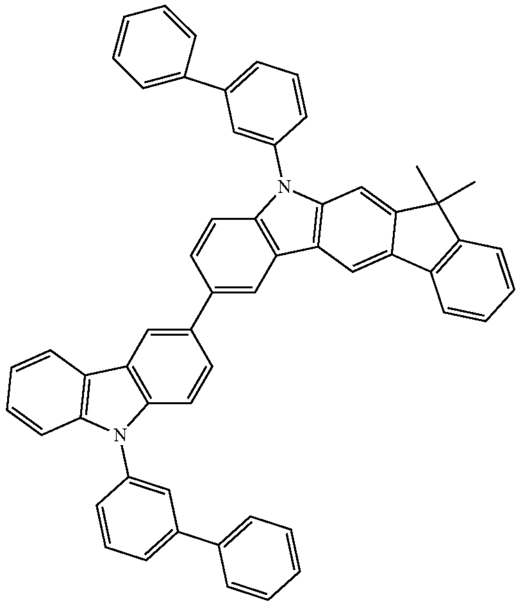 [SMILES: CC1(C)c2ccccc2-c2cc3c4cc(-c5ccc6c(c5)c5ccccc5n6-c5cccc(-c6ccccc6)c5)ccc4n(-c4cccc(-c5ccccc5)c4)c3cc21]
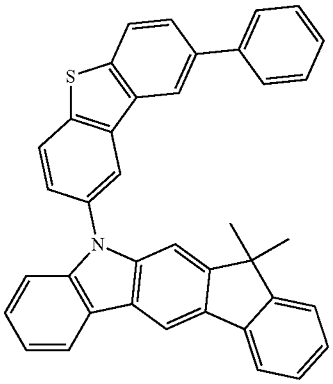 [SMILES: CC1(C)c2ccccc2-c2cc3c4ccccc4n(-c4ccc5sc6ccc(-c7ccccc7)cc6c5c4)c3cc21]
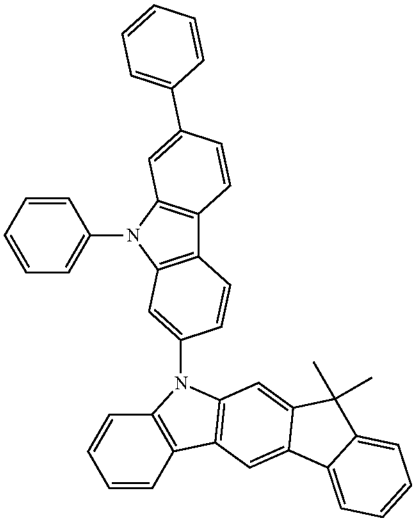 [SMILES: CC1(C)c2ccccc2-c2cc3c4ccccc4n(-c4ccc5c6ccc(-c7ccccc7)cc6n(-c6ccccc6)c5c4)c3cc21]

TABLE 3-continued
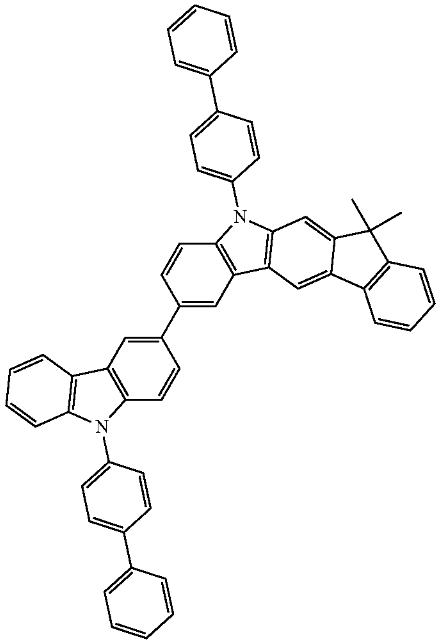 [SMILES: CC1(C)c2ccccc2-c2cc3c4cc(-c5ccc6c(c5)c5ccccc5n6-c5ccc(-c6ccccc6)cc5)ccc4n(-c4ccc(-c5ccccc5)cc4)c3cc21]
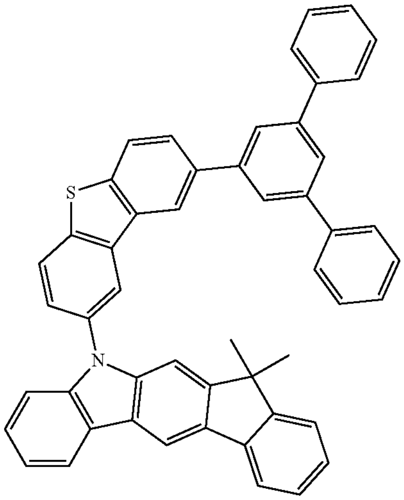 [SMILES: CC1(C)c2ccccc2-c2cc3c4ccccc4n(-c4ccc5sc6ccc(-c7cc(-c8ccccc8)cc(-c8ccccc8)c7)cc6c5c4)c3cc21]

TABLE 3-continued
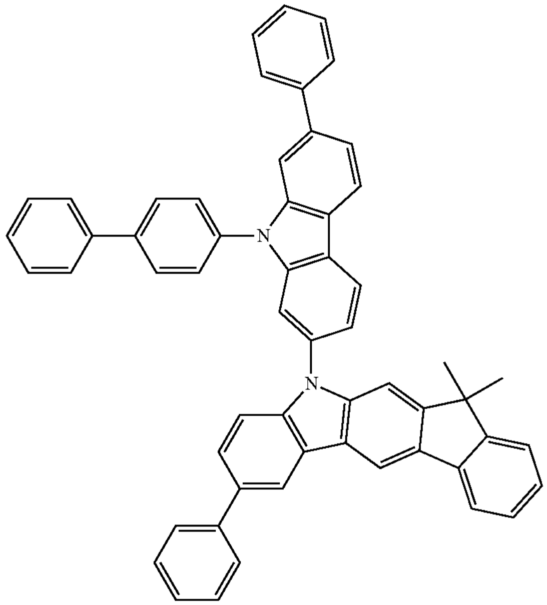 [SMILES: CC1(C)c2ccccc2-c2cc3c4cc(-c5ccccc5)ccc4n(-c4ccc5c6ccc(-c7ccccc7)cc6n(-c6ccc(-c7ccccc7)cc6)c5c4)c3cc21]
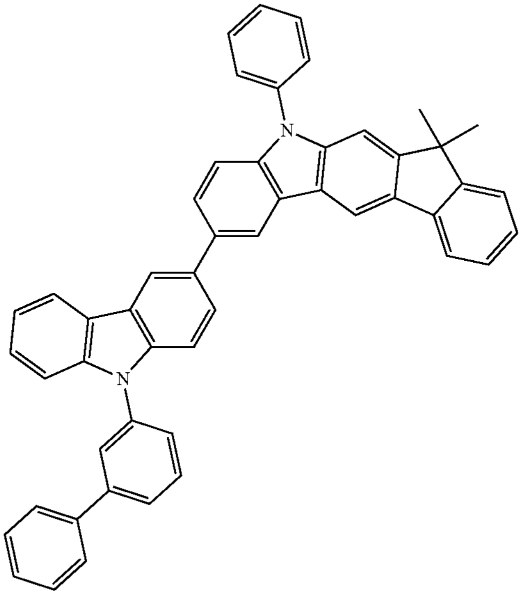 [SMILES: CC1(C)c2ccccc2-c2cc3c4cc(-c5ccc6c(c5)c5ccccc5n6-c5cccc(-c6ccccc6)c5)ccc4n(-c4ccccc4)c3cc21]

TABLE 3-continued
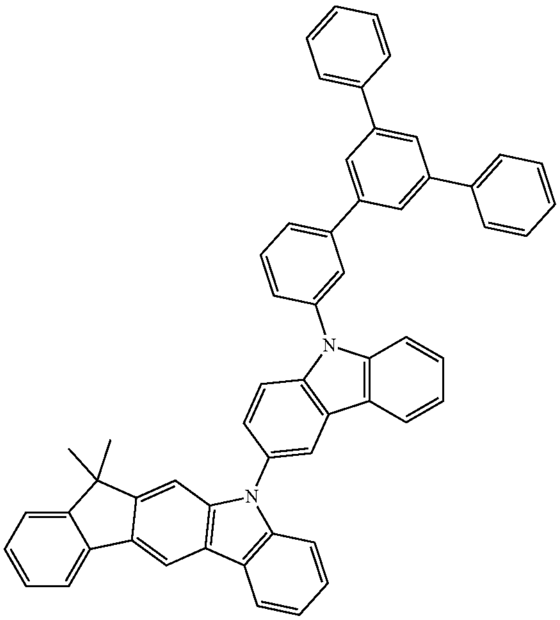 [SMILES: CC1(C)c2ccccc2-c2cc3c4ccccc4n(-c4ccc5c(c4)c4ccccc4n5-c4cccc(-c5cc(-c6ccccc6)cc(-c6ccccc6)c5)c4)c3cc21]
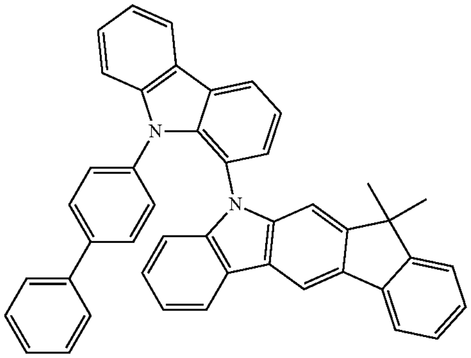 [SMILES: CC1(C)c2ccccc2-c2cc3c4ccccc4n(-c4cccc5c6ccccc6n(-c6ccc(-c7ccccc7)cc6)c45)c3cc21]
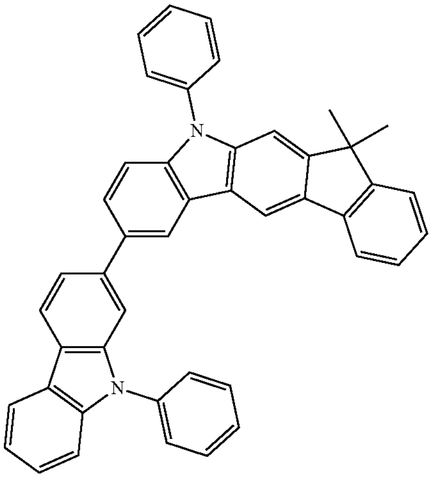 [SMILES: CC1(C)c2ccccc2-c2cc3c4cc(-c5ccc6c7ccccc7n(-c7ccccc7)c6c5)ccc4n(-c4ccccc4)c3cc21]

TABLE 3-continued
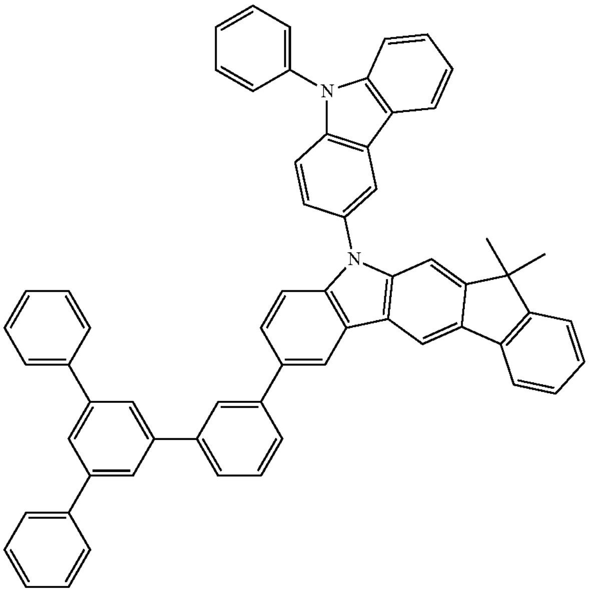 [SMILES: CC1(C)c2ccccc2-c2cc3c4cc(-c5cccc(-c6cc(-c7ccccc7)cc(-c7ccccc7)c6)c5)ccc4n(-c4ccc5c(c4)c4ccccc4n5-c4ccccc4)c3cc21]
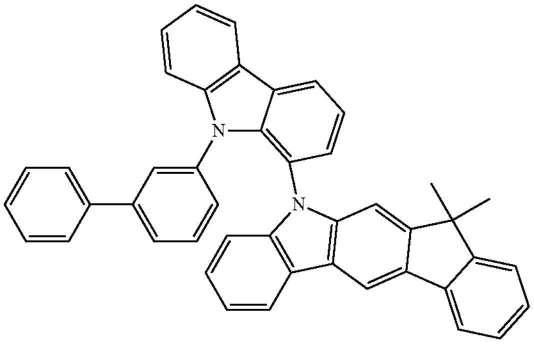 [SMILES: CC1(C)c2ccccc2-c2cc3c4ccccc4n(-c4cccc5c6ccccc6n(-c6cccc(-c7ccccc7)c6)c45)c3cc21]
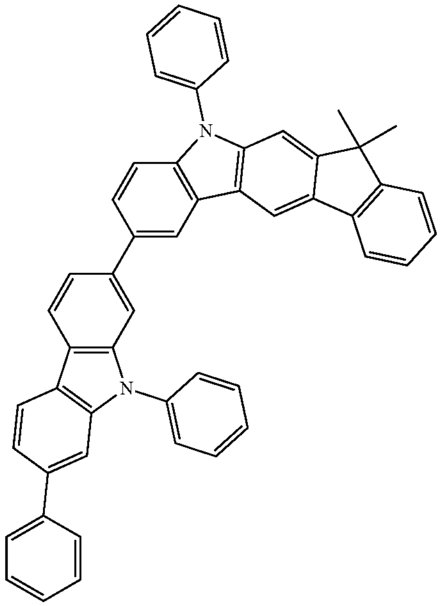 [SMILES: CC1(C)c2ccccc2-c2cc3c4cc(-c5ccc6c7ccc(-c8ccccc8)cc7n(-c7ccccc7)c6c5)ccc4n(-c4ccccc4)c3cc21]

TABLE 3-continued
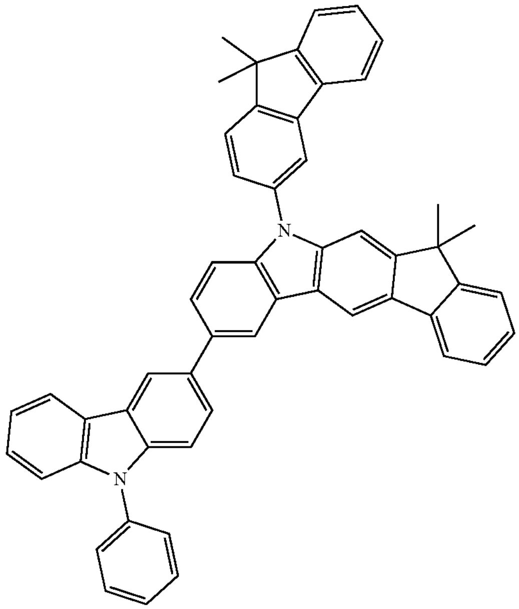 [SMILES: CC1(C)c2ccccc2-c2cc(-n3c4ccc(-c5ccc6c(c5)c5ccccc5n6-c5ccccc5)cc4c4cc5c(cc43)C(C)(C)c3ccccc3-5)ccc21]
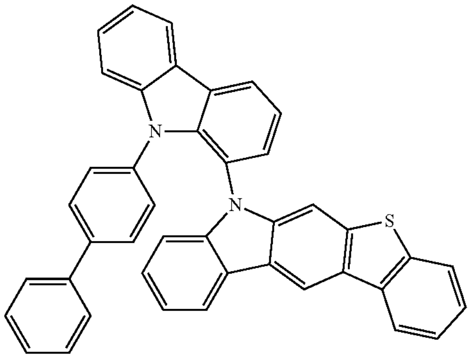 [SMILES: c1ccc(-c2ccc(-n3c4ccccc4c4cccc(-n5c6ccccc6c6cc7c(cc65)sc5ccccc57)c43)cc2)cc1]
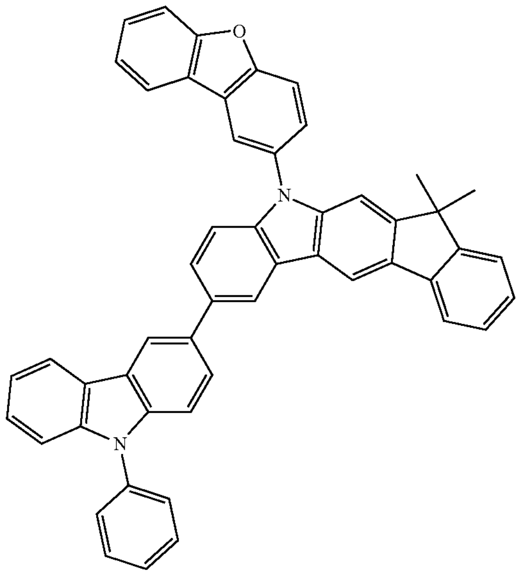 [SMILES: CC1(C)c2ccccc2-c2cc3c4cc(-c5ccc6c(c5)c5ccccc5n6-c5ccccc5)ccc4n(-c4ccc5oc6ccccc6c5c4)c3cc21]

TABLE 3-continued
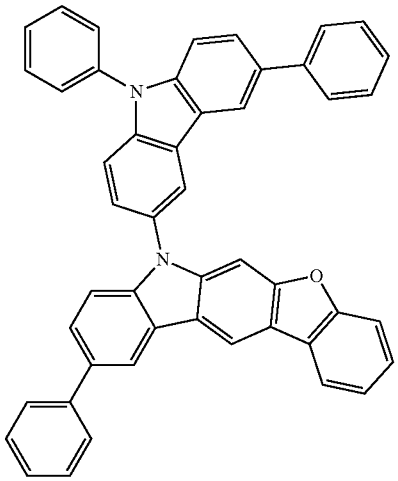 [SMILES: c1ccc(-c2ccc3c(c2)c2cc(-n4c5ccc(-c6ccccc6)cc5c5cc6c(cc54)oc4ccccc46)ccc2n3-c2ccccc2)cc1]
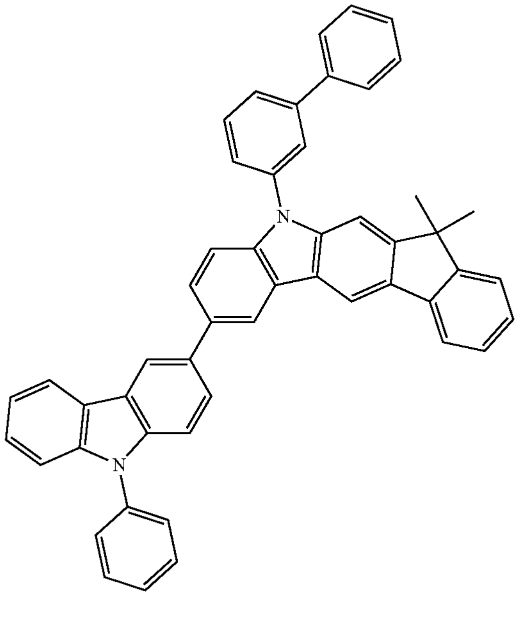 [SMILES: CC1(C)c2ccccc2-c2cc3c4cc(-c5ccc6c(c5)c5ccccc5n6-c5ccccc5)ccc4n(-c4cccc(-c5ccccc5)c4)c3cc21]

TABLE 3-continued
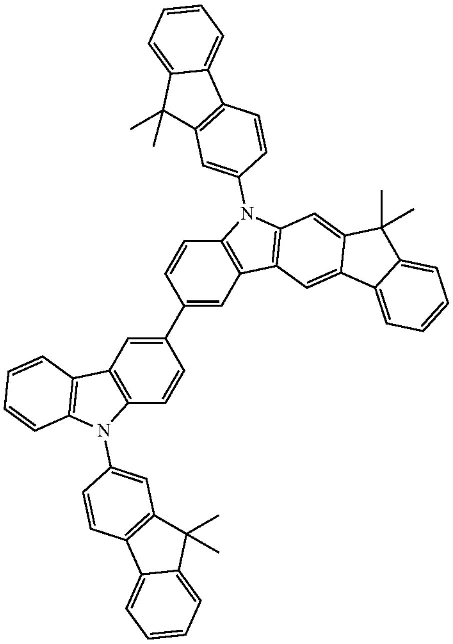 [SMILES: CC1(C)c2ccccc2-c2ccc(-n3c4ccccc4c4cc(-c5ccc6c(c5)c5cc7c(cc5n6-c5ccc6c(c5)C(C)(C)c5ccccc5-6)C(C)(C)c5ccccc5-7)ccc43)cc21]
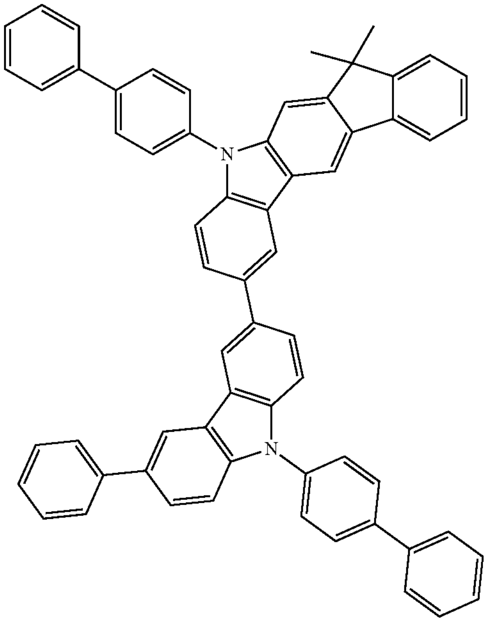 [SMILES: CC1(C)c2ccccc2-c2cc3c4cc(-c5ccc6c(c5)c5cc(-c7ccccc7)ccc5n6-c5ccc(-c6ccccc6)cc5)ccc4n(-c4ccc(-c5ccccc5)cc4)c3cc21]
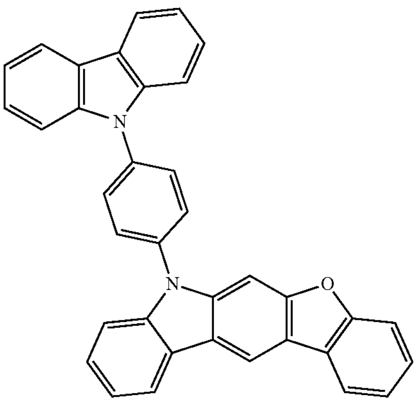 [SMILES: c1ccc2c(c1)oc1cc3c(cc12)c1ccccc1n3-c1ccc(-n2c3ccccc3c3ccccc32)cc1]

TABLE 3-continued
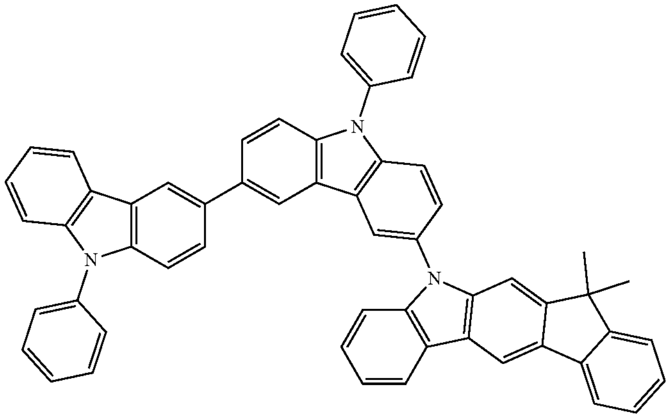 [SMILES: CC1(C)c2ccccc2-c2cc3c4ccccc4n(-c4ccc5c(c4)c4cc(-c6ccc7c(c6)c6ccccc6n7-c6ccccc6)ccc4n5-c4ccccc4)c3cc21]
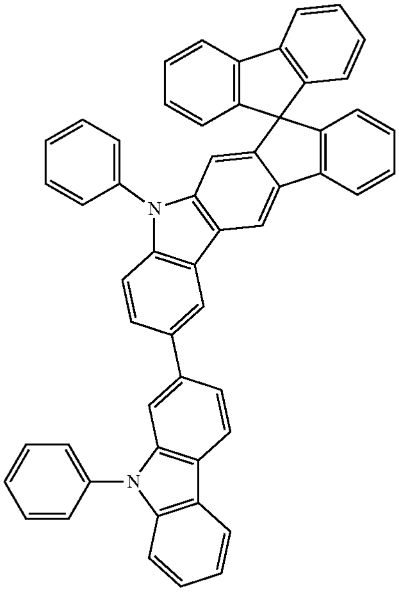 [SMILES: c1ccc(-n2c3ccccc3c3ccc(-c4ccc5c(c4)c4cc6c(cc4n5-c4ccccc4)C4(c5ccccc5-c5ccccc54)c4ccccc4-6)cc32)cc1]
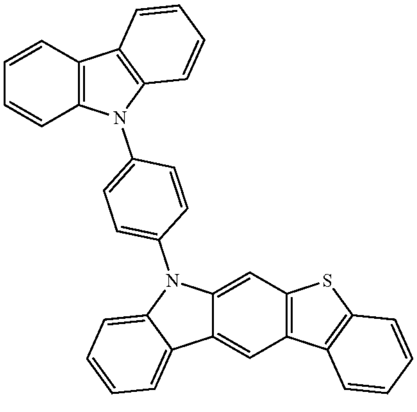 [SMILES: c1ccc2c(c1)sc1cc3c(cc12)c1ccccc1n3-c1ccc(-n2c3ccccc3c3ccccc32)cc1]

TABLE 3-continued
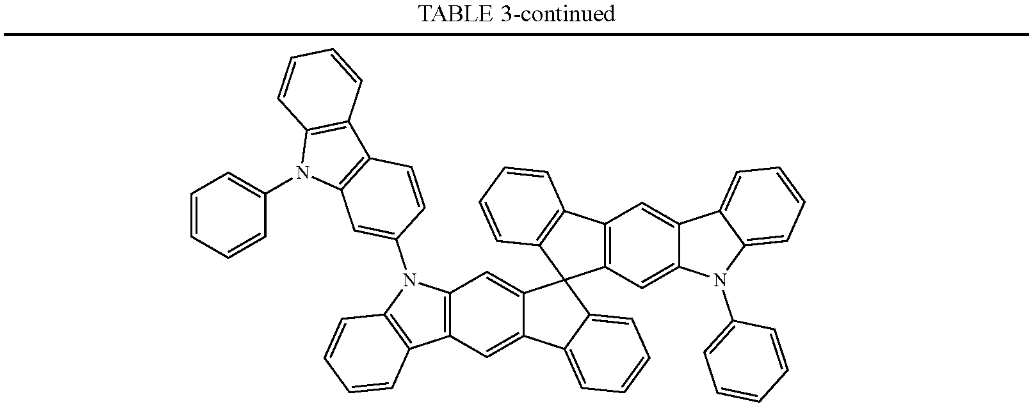
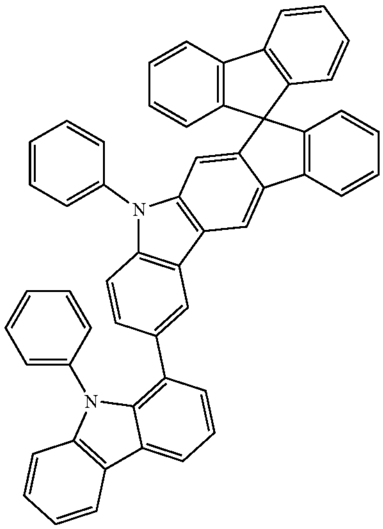 [SMILES: c1ccc(-n2c3ccc(-c4cccc5c6ccccc6n(-c6ccccc6)c45)cc3c3cc4c(cc32)C2(c3ccccc3-c3ccccc32)c2ccccc2-4)cc1]
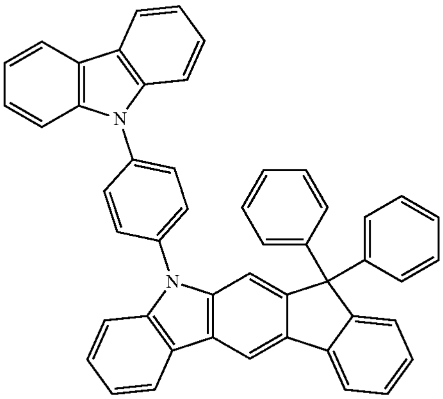 [SMILES: c1ccc(C2(c3ccccc3)c3ccccc3-c3cc4c5ccccc5n(-c5ccc(-n6c7ccccc7c7ccccc76)cc5)c4cc32)cc1]

TABLE 3-continued
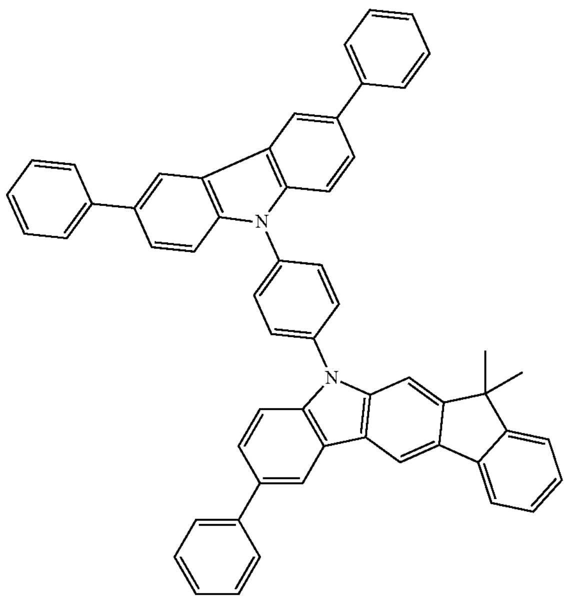 [SMILES: CC1(C)c2ccccc2-c2cc3c4cc(-c5ccccc5)ccc4n(-c4ccc(-n5c6ccc(-c7ccccc7)cc6c6cc(-c7ccccc7)ccc65)cc4)c3cc21]
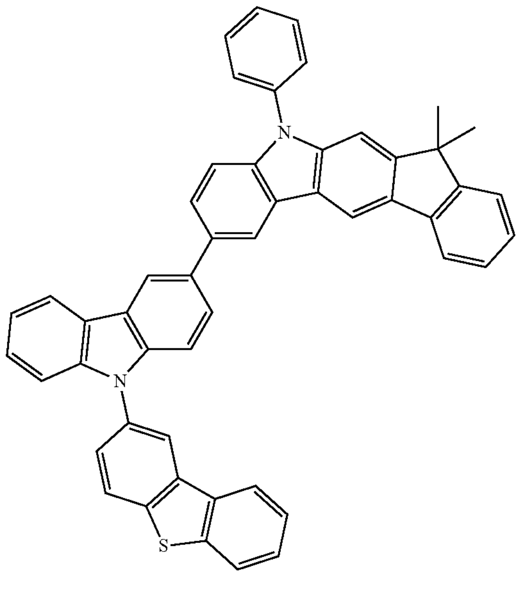

TABLE 3-continued
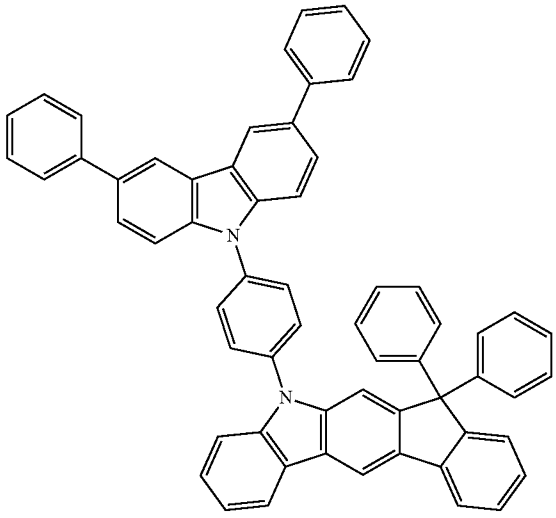 [SMILES: c1ccc(-c2ccc3c(c2)c2cc(-c4ccccc4)ccc2n3-c2ccc(-n3c4ccccc4c4cc5c(cc43)C(c3ccccc3)(c3ccccc3)c3ccccc3-5)cc2)cc1]
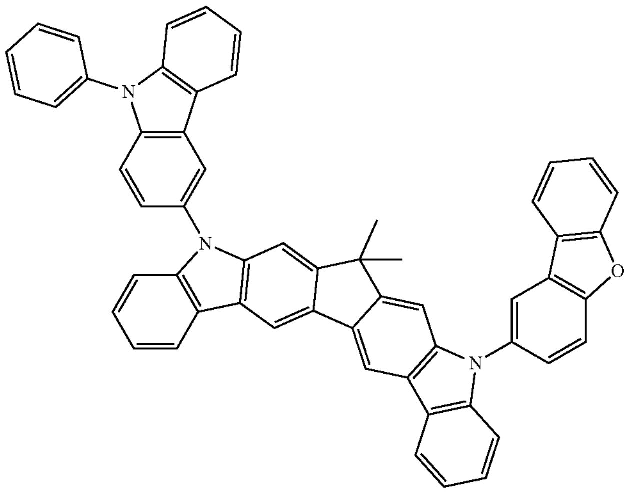 [SMILES: CC1(C)c2cc3c(cc2-c2cc4c5ccccc5n(-c5ccc6c(c5)c5ccccc5n6-c5ccccc5)c4cc21)c1ccccc1n3-c1ccc2oc3ccccc3c2c1]
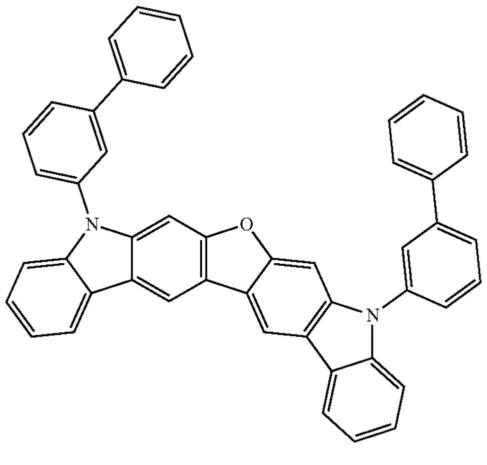 [SMILES: c1ccc(-c2cccc(-n3c4ccccc4c4cc5c(cc43)oc3cc4c(cc35)c3ccccc3n4-c3cccc(-c4ccccc4)c3)c2)cc1]

TABLE 3-continued
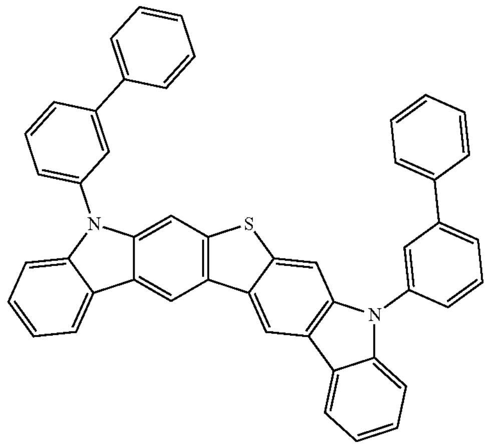 [SMILES: c1ccc(-c2cccc(-n3c4ccccc4c4cc5c(cc43)sc3cc4c(cc35)c3ccccc3n4-c3cccc(-c4ccccc4)c3)c2)cc1]
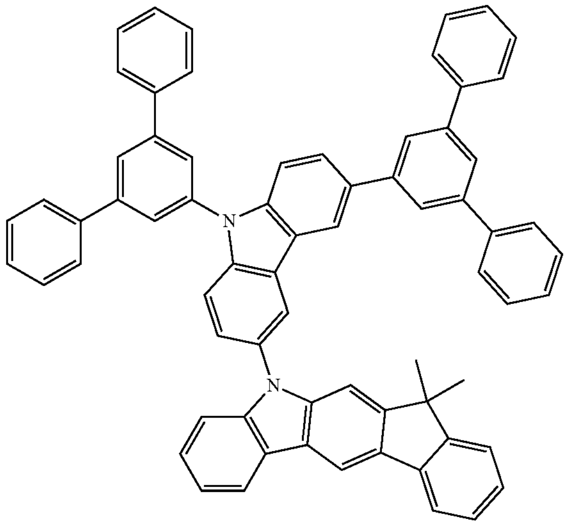 [SMILES: CC1(C)c2ccccc2-c2cc3c4ccccc4n(-c4ccc5c(c4)c4cc(-c6cc(-c7ccccc7)cc(-c7ccccc7)c6)ccc4n5-c4cc(-c5ccccc5)cc(-c5ccccc5)c4)c3cc21]
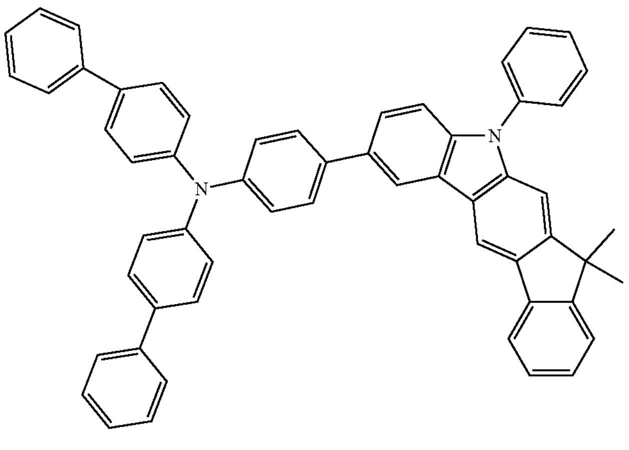 [SMILES: CC1(C)c2ccccc2-c2cc3c4cc(-c5ccc(N(c6ccc(-c7ccccc7)cc6)c6ccc(-c7ccccc7)cc6)cc5)ccc4n(-c4ccccc4)c3cc21]

TABLE 3-continued
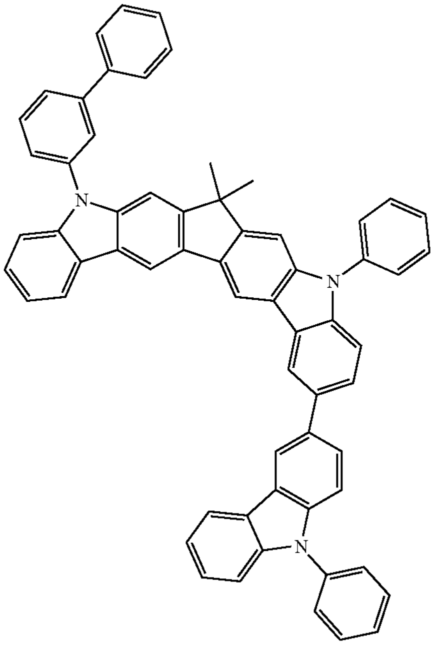 [SMILES: CC1(C)c2cc3c(cc2-c2cc4c5cc(-c6ccc7c(c6)c6ccccc6n7-c6ccccc6)ccc5n(-c5ccccc5)c4cc21)c1ccccc1n3-c1cccc(-c2ccccc2)c1]
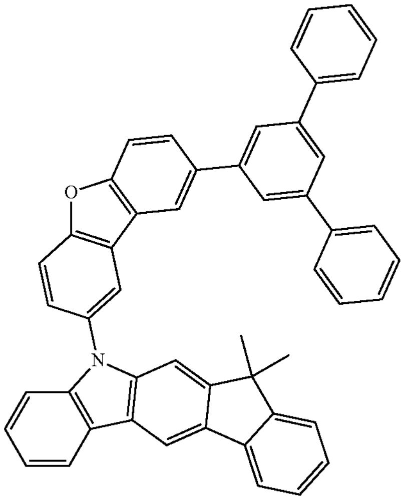 [SMILES: CC1(C)c2ccccc2-c2cc3c4ccccc4n(-c4ccc5oc6ccc(-c7cc(-c8ccccc8)cc(-c8ccccc8)c7)cc6c5c4)c3cc21]
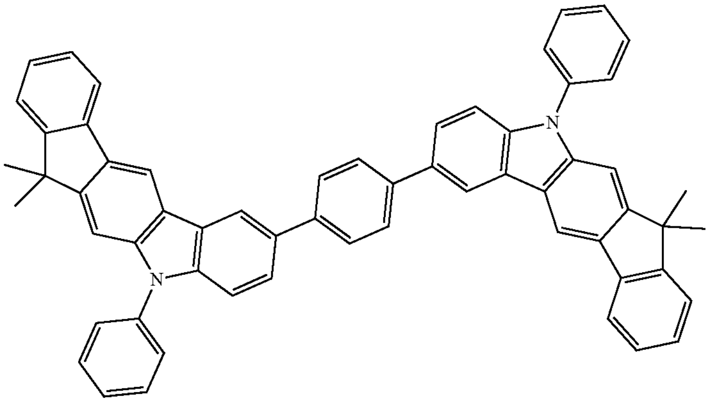

TABLE 3-continued
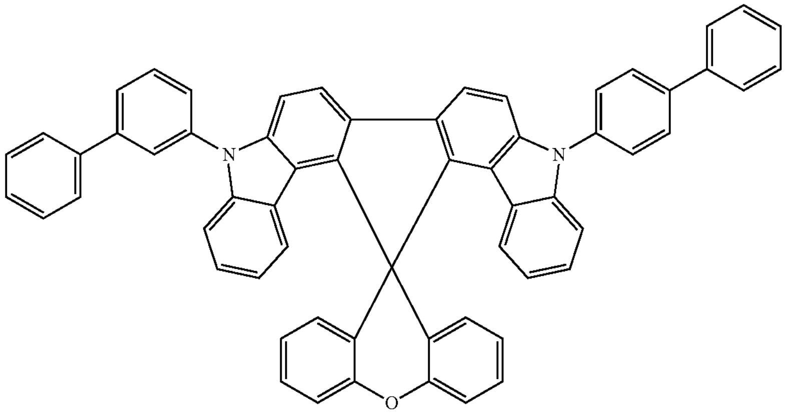 [SMILES: c1ccc(-c2ccc(-n3c4ccccc4c4c5c(ccc43)-c3ccc4c(c3C53c5ccccc5Oc5ccccc53)c3ccccc3n4-c3cccc(-c4ccccc4)c3)cc2)cc1]
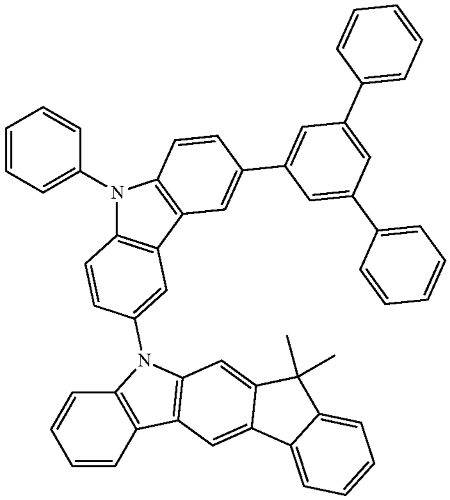 [SMILES: CC1(C)c2ccccc2-c2cc3c4ccccc4n(-c4ccc5c(c4)c4cc(-c6cc(-c7ccccc7)cc(-c7ccccc7)c6)ccc4n5-c4ccccc4)c3cc21]
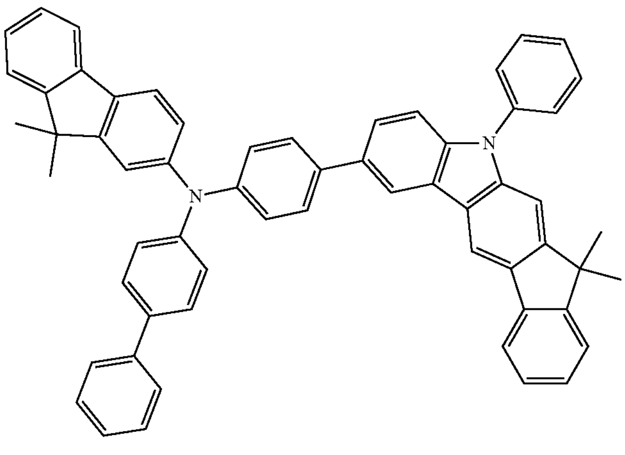 [SMILES: CC1(C)c2ccccc2-c2ccc(N(c3ccc(-c4ccccc4)cc3)c3ccc(-c4ccc5c(c4)c4cc6c(cc4n5-c4ccccc4)C(C)(C)c4ccccc4-6)cc3)cc21]

TABLE 3-continued
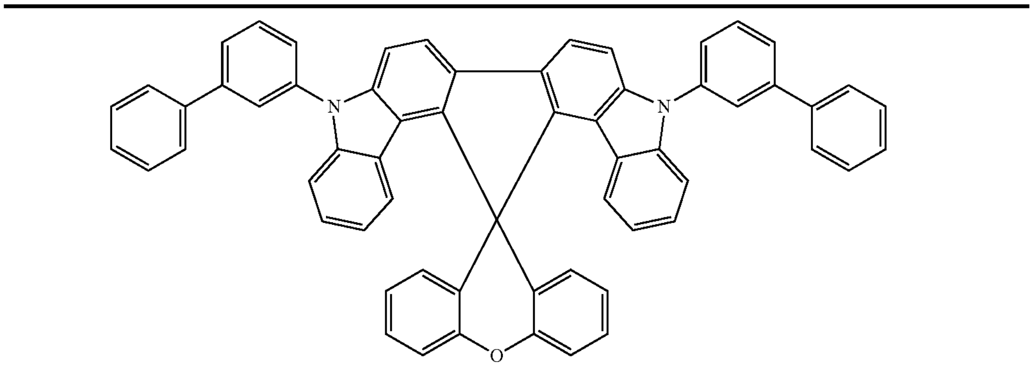
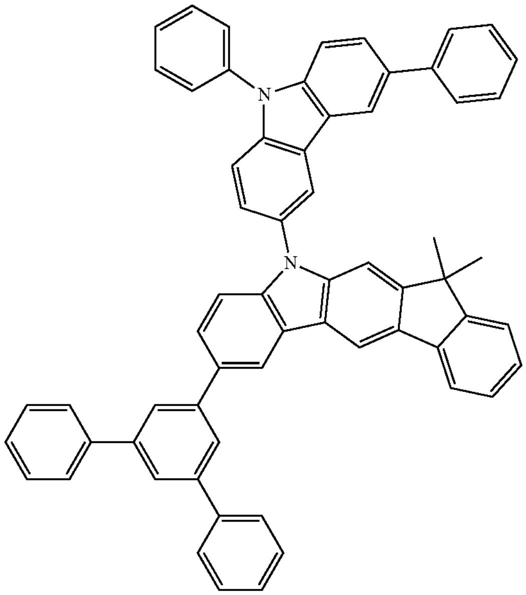 [SMILES: CC1(C)c2ccccc2-c2cc3c4cc(-c5cc(-c6ccccc6)cc(-c6ccccc6)c5)ccc4n(-c4ccc5c(c4)c4cc(-c6ccccc6)ccc4n5-c4ccccc4)c3cc21]
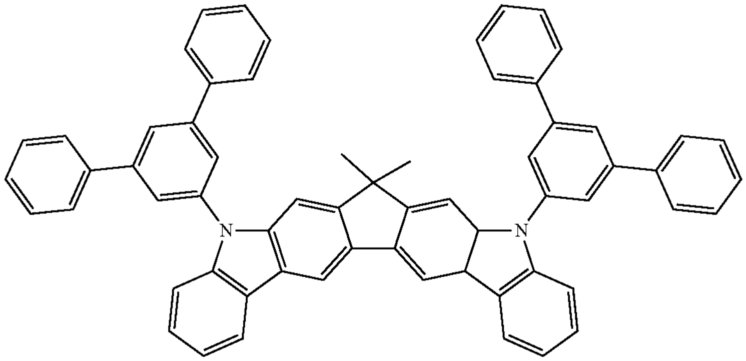 [SMILES: CC1(C)C2=CC3C(C=C2c2cc4c5ccccc5n(-c5cc(-c6ccccc6)cc(-c6ccccc6)c5)c4cc21)c1ccccc1N3c1cc(-c2ccccc2)cc(-c2ccccc2)c1]
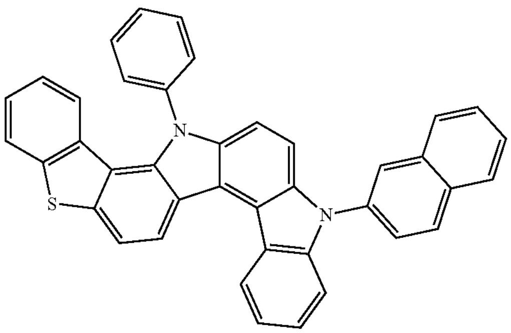 [SMILES: c1ccc(-n2c3ccc4c(c5ccccc5n4-c4ccc5ccccc5c4)c3c3ccc4sc5ccccc5c4c32)cc1]

TABLE 3-continued
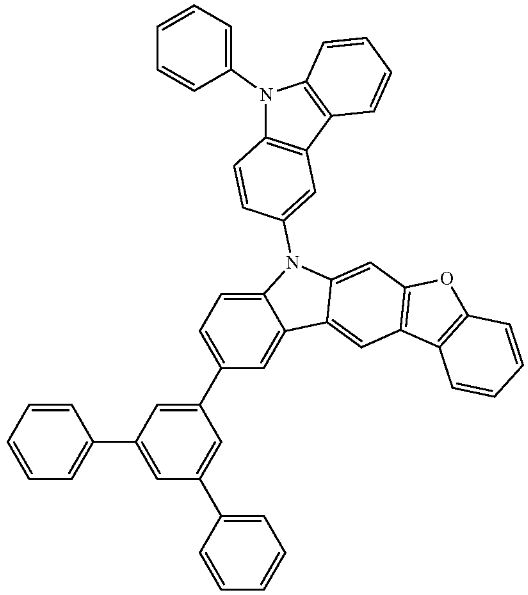 [SMILES: c1ccc(-c2cc(-c3ccccc3)cc(-c3ccc4c(c3)c3cc5c(cc3n4-c3ccc4c(c3)c3ccccc3n4-c3ccccc3)oc3ccccc35)c2)cc1]
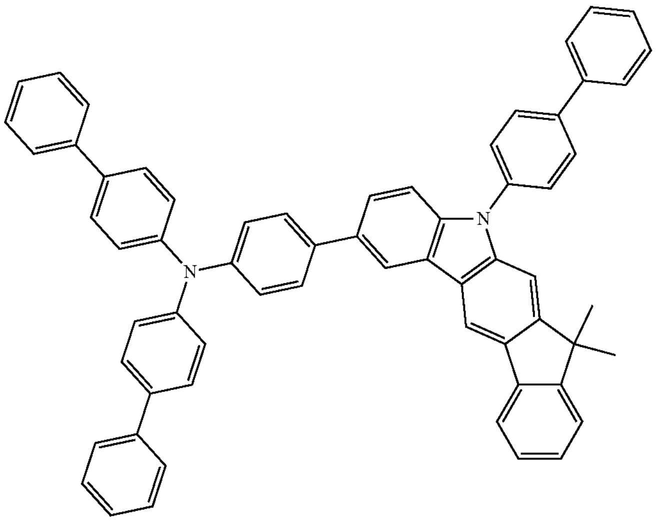 [SMILES: CC1(C)c2ccccc2-c2cc3c4cc(-c5ccc(N(c6ccc(-c7ccccc7)cc6)c6ccc(-c7ccccc7)cc6)cc5)ccc4n(-c4ccc(-c5ccccc5)cc4)c3cc21]
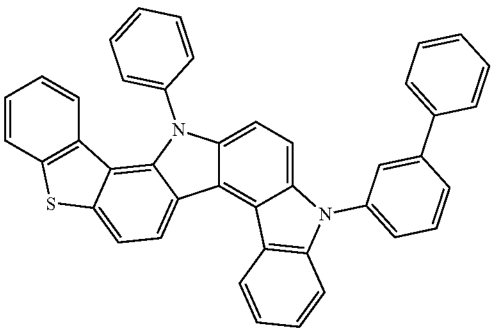 [SMILES: c1ccc(-c2cccc(-n3c4ccccc4c4c5c6ccc7sc8ccccc8c7c6n(-c6ccccc6)c5ccc43)c2)cc1]

TABLE 3-continued
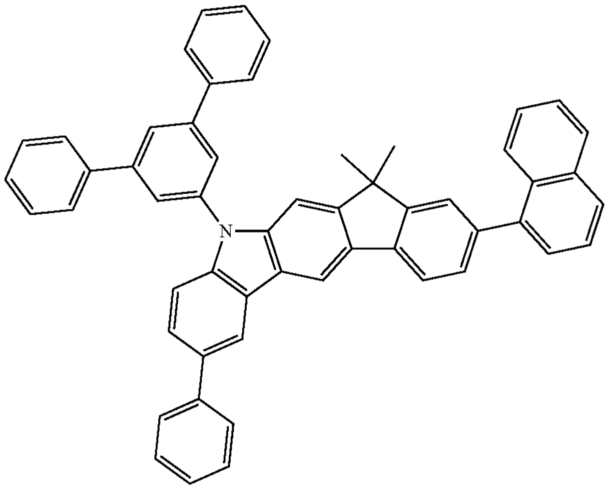 [SMILES: CC1(C)c2cc(-c3cccc4ccccc34)ccc2-c2cc3c4cc(-c5ccccc5)ccc4n(-c4cc(-c5ccccc5)cc(-c5ccccc5)c4)c3cc21]
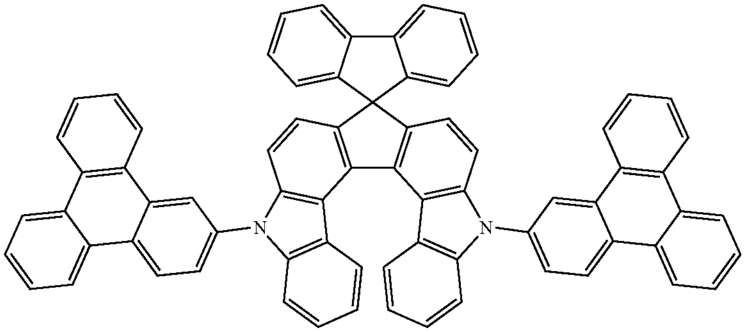 [SMILES: c1ccc2c(c1)-c1ccccc1C21c2ccc3c(c2-c2c1ccc1c2c2ccccc2n1-c1ccc2c4ccccc4c4ccccc4c2c1)c1ccccc1n3-c1ccc2c3ccccc3c3ccccc3c2c1]
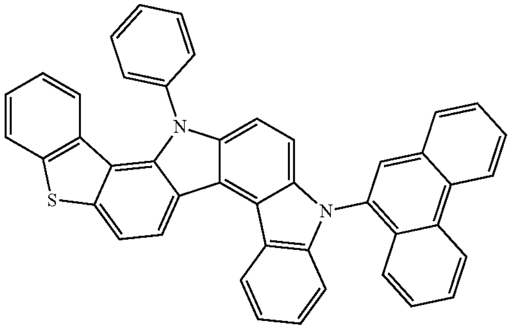 [SMILES: c1ccc(-n2c3ccc4c(c5ccccc5n4-c4cc5ccccc5c5ccccc45)c3c3ccc4sc5ccccc5c4c32)cc1]
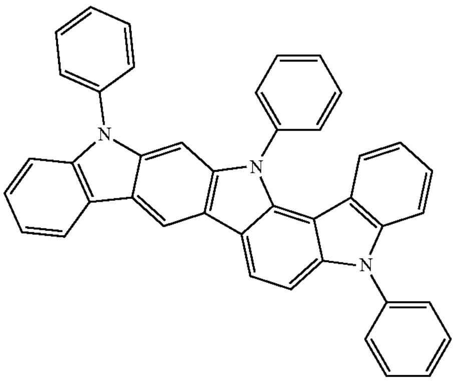 [SMILES: c1ccc(-n2c3ccccc3c3cc4c5ccc6c(c7ccccc7n6-c6ccccc6)c5n(-c5ccccc5)c4cc32)cc1]

TABLE 3-continued
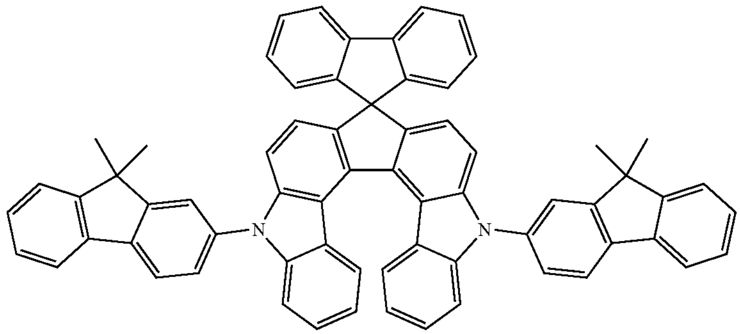 [SMILES: CC1(C)c2ccccc2-c2ccc(-n3c4ccccc4c4c5c(ccc43)C3(c4ccccc4-c4ccccc43)c3ccc4c(c3-5)c3ccccc3n4-c3ccc4c(c3)C(C)(C)c3ccccc3-4)cc21]
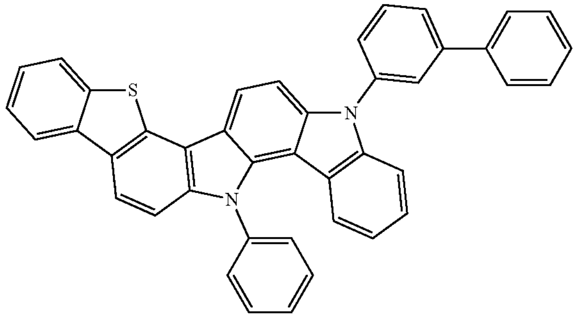 [SMILES: c1ccc(-c2cccc(-n3c4ccccc4c4c3ccc3c5c6sc7ccccc7c6ccc5n(-c5ccccc5)c34)c2)cc1]
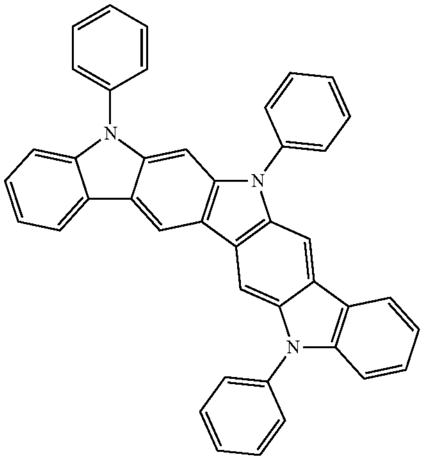 [SMILES: c1ccc(-n2c3ccccc3c3cc4c(cc32)c2cc3c5ccccc5n(-c5ccccc5)c3cc2n4-c2ccccc2)cc1]
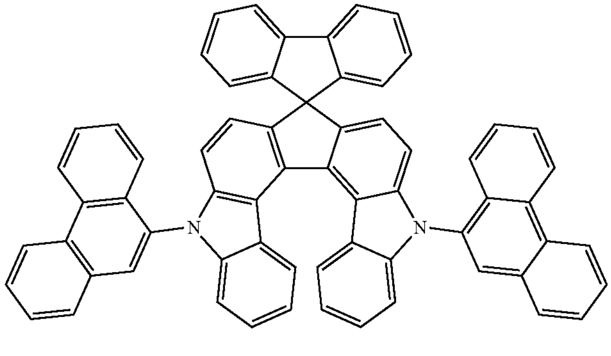 [SMILES: c1ccc2c(c1)-c1ccccc1C21c2ccc3c(c2-c2c1ccc1c2c2ccccc2n1-c1cc2ccccc2c2ccccc12)c1ccccc1n3-c1cc2ccccc2c2ccccc12]

TABLE 3-continued
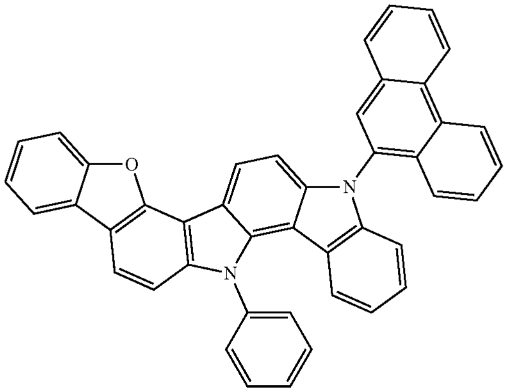 [SMILES: c1ccc(-n2c3ccc4c5ccccc5oc4c3c3ccc4c(c5ccccc5n4-c4cc5ccccc5c5ccccc45)c32)cc1]
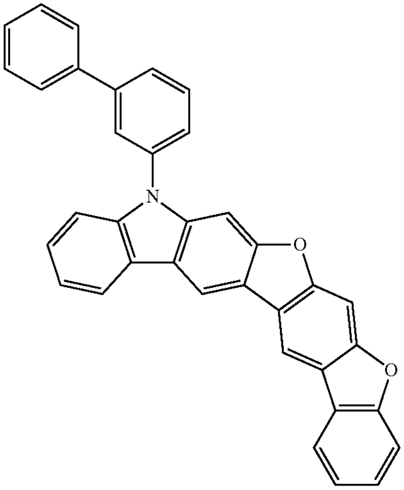 [SMILES: c1ccc(-c2cccc(-n3c4ccccc4c4cc5c(cc43)oc3cc4oc6ccccc6c4cc35)c2)cc1]
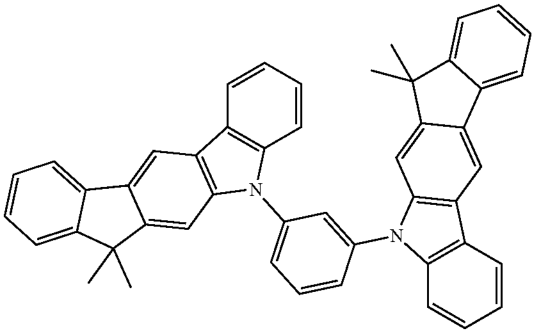 [SMILES: CC1(C)c2ccccc2-c2cc3c4ccccc4n(-c4cccc(-n5c6ccccc6c6cc7c(cc65)C(C)(C)c5ccccc5-7)c4)c3cc21]
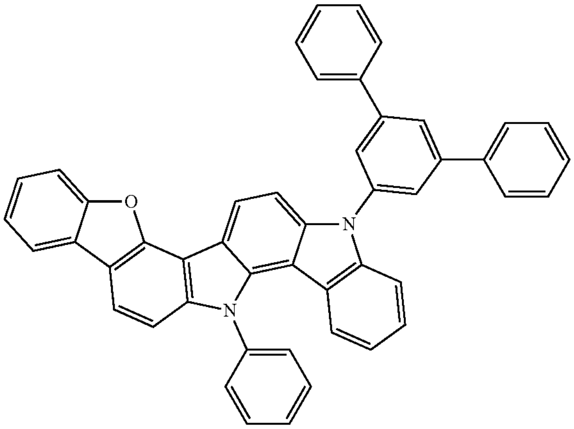 [SMILES: c1ccc(-c2cc(-c3ccccc3)cc(-n3c4ccccc4c4c3ccc3c5c6oc7ccccc7c6ccc5n(-c5ccccc5)c34)c2)cc1]

TABLE 3-continued
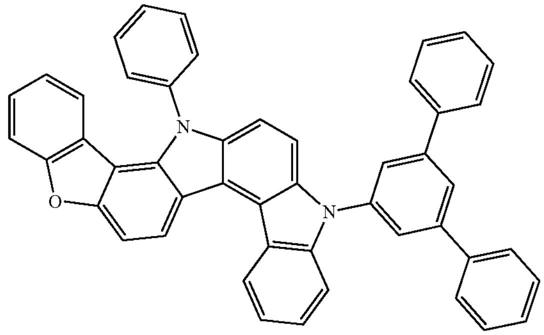 [SMILES: c1ccc(-c2cc(-c3ccccc3)cc(-n3c4ccccc4c4c5c6ccc7oc8ccccc8c7c6n(-c6ccccc6)c5ccc43)c2)cc1]
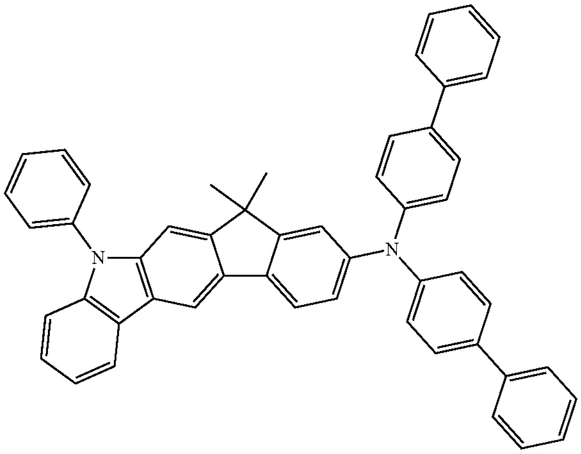 [SMILES: CC1(C)c2cc(N(c3ccc(-c4ccccc4)cc3)c3ccc(-c4ccccc4)cc3)ccc2-c2cc3c4ccccc4n(-c4ccccc4)c3cc21]
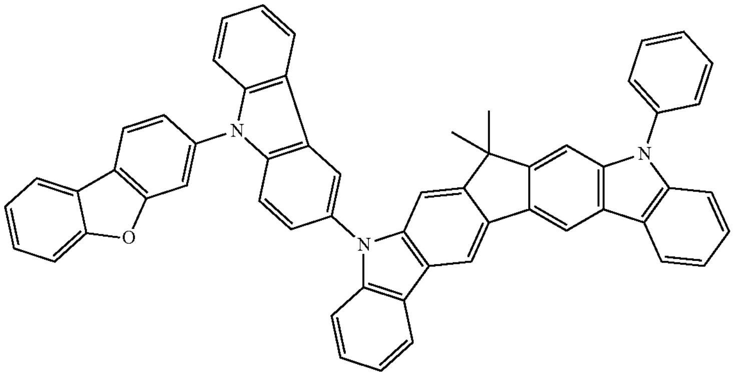 [SMILES: CC1(C)c2cc3c(cc2-c2cc4c5ccccc5n(-c5ccc6c(c5)c5ccccc5n6-c5ccc6c(c5)oc5ccccc56)c4cc21)c1ccccc1n3-c1ccccc1]
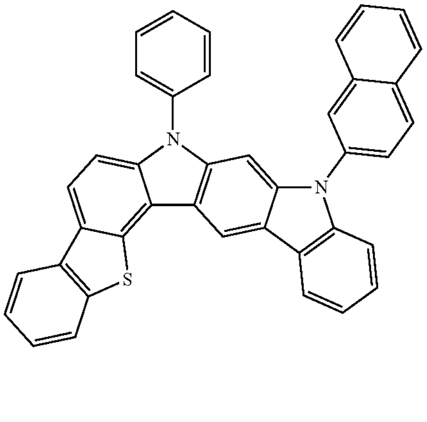 [SMILES: c1ccc(-n2c3cc4c(cc3c3c5sc6ccccc6c5ccc32)c2ccccc2n4-c2ccc3ccccc3c2)cc1]

TABLE 3-continued
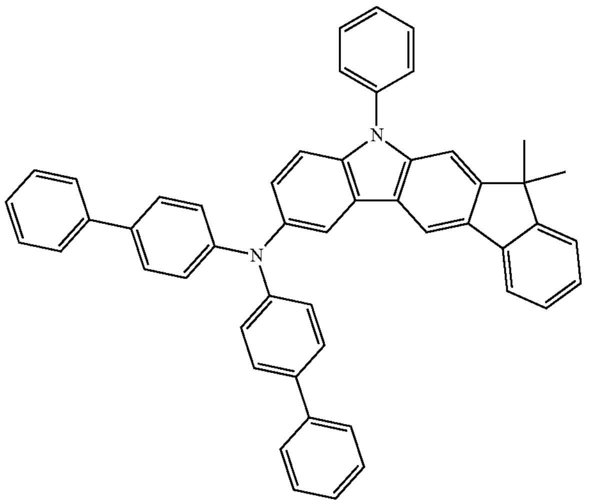 [SMILES: CC1(C)c2ccccc2-c2cc3c4cc(N(c5ccc(-c6ccccc6)cc5)c5ccc(-c6ccccc6)cc5)ccc4n(-c4ccccc4)c3cc21]
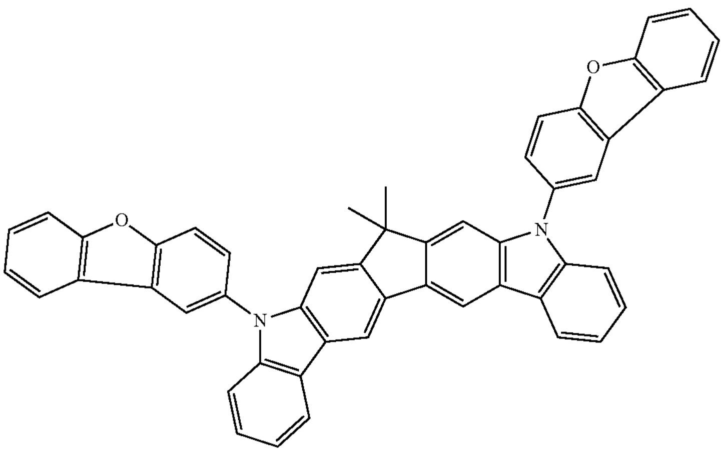 [SMILES: CC1(C)c2cc3c(cc2-c2cc4c5ccccc5n(-c5ccc6oc7ccccc7c6c5)c4cc21)c1ccccc1n3-c1ccc2oc3ccccc3c2c1]
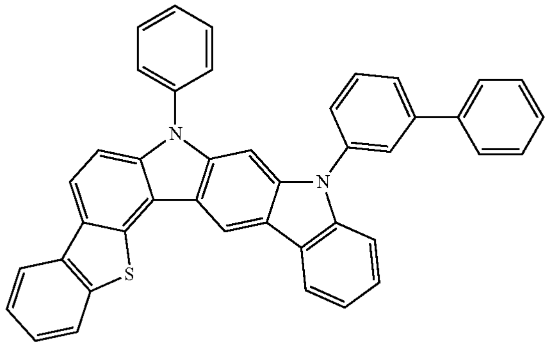 [SMILES: c1ccc(-c2cccc(-n3c4ccccc4c4cc5c6c7sc8ccccc8c7ccc6n(-c6ccccc6)c5cc43)c2)cc1]
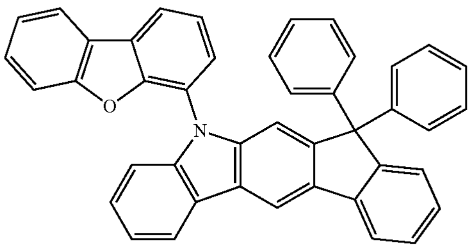 [SMILES: c1ccc(C2(c3ccccc3)c3ccccc3-c3cc4c5ccccc5n(-c5cccc6c5oc5ccccc56)c4cc32)cc1]

TABLE 3-continued
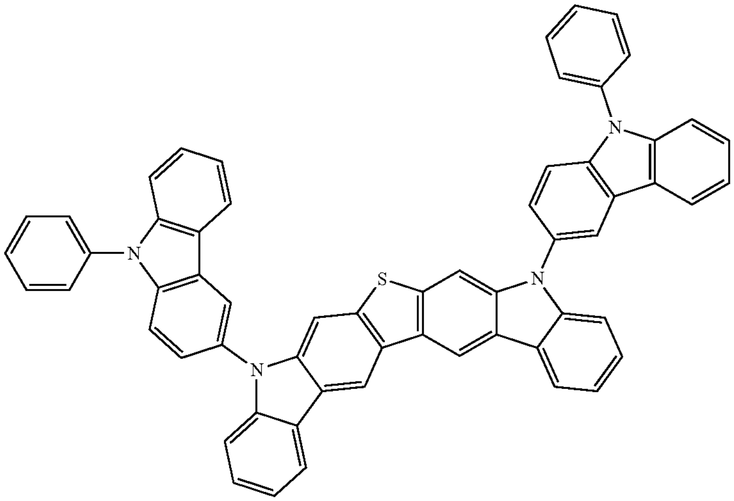 [SMILES: c1ccc(-n2c3ccccc3c3cc(-n4c5ccccc5c5cc6c(cc54)sc4cc5c(cc46)c4ccccc4n5-c4ccc5c(c4)c4ccccc4n5-c4ccccc4)ccc32)cc1]
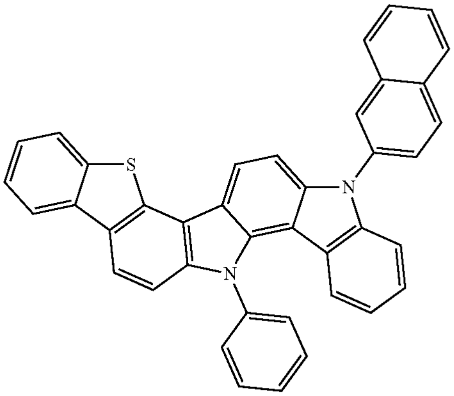 [SMILES: c1ccc(-n2c3ccc4c5ccccc5sc4c3c3ccc4c(c5ccccc5n4-c4ccc5ccccc5c4)c32)cc1]
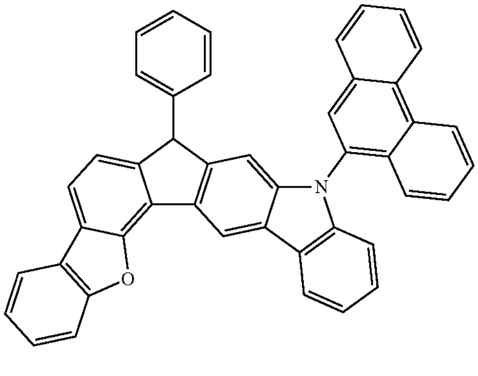 [SMILES: c1ccc(C2c3cc4c(cc3-c3c2ccc2c3oc3ccccc32)c2ccccc2n4-c2cc3ccccc3c3ccccc23)cc1]

TABLE 3-continued
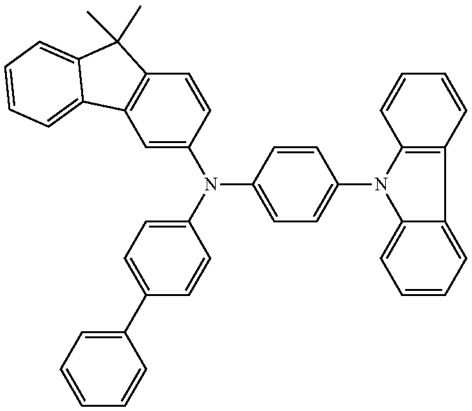 [SMILES: CC1(C)c2ccccc2-c2cc(N(c3ccc(-c4ccccc4)cc3)c3ccc(-n4c5ccccc5c5ccccc54)cc3)ccc21]
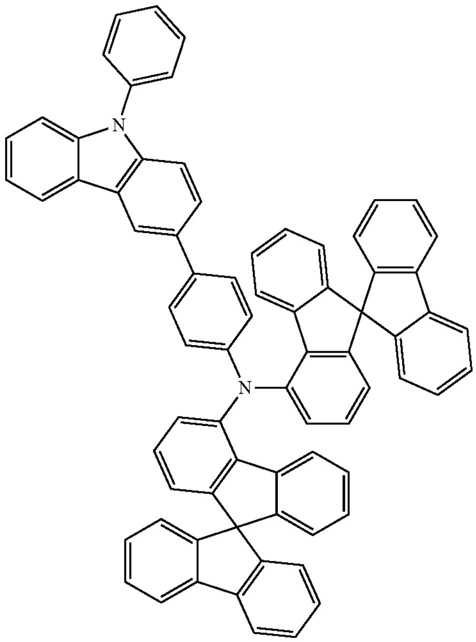 [SMILES: c1ccc(-n2c3ccccc3c3cc(-c4ccc(N(c5cccc6c5-c5ccccc5C65c6ccccc6-c6ccccc65)c5cccc6c5-c5ccccc5C65c6ccccc6-c6ccccc65)cc4)ccc32)cc1]
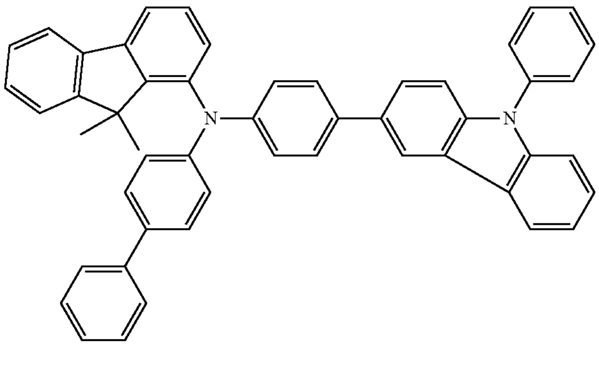 [SMILES: CC1(C)c2ccccc2-c2cccc(N(c3ccc(-c4ccccc4)cc3)c3ccc(-c4ccc5c(c4)c4ccccc4n5-c4ccccc4)cc3)c21]

TABLE 3-continued
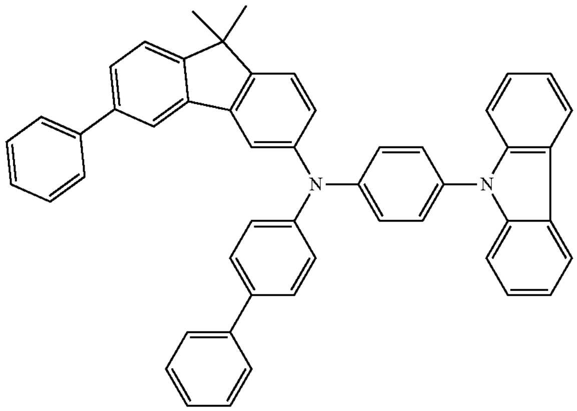 [SMILES: CC1(C)c2ccc(-c3ccccc3)cc2-c2cc(N(c3ccc(-c4ccccc4)cc3)c3ccc(-n4c5ccccc5c5ccccc54)cc3)ccc21]
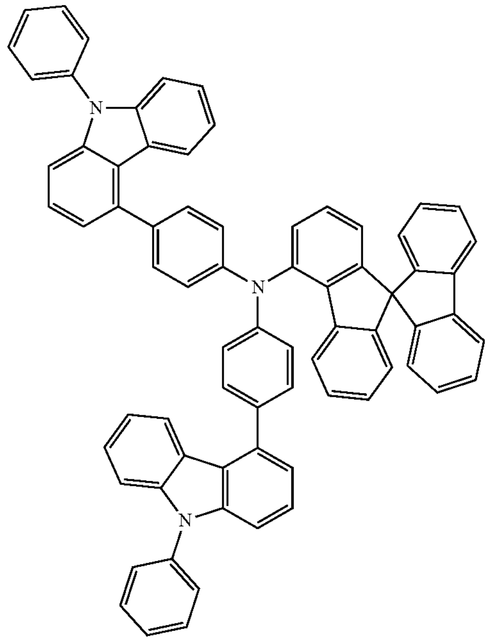 [SMILES: c1ccc(-n2c3ccccc3c3c(-c4ccc(N(c5ccc(-c6cccc7c6c6ccccc6n7-c6ccccc6)cc5)c5cccc6c5-c5ccccc5C65c6ccccc6-c6ccccc65)cc4)cccc32)cc1]
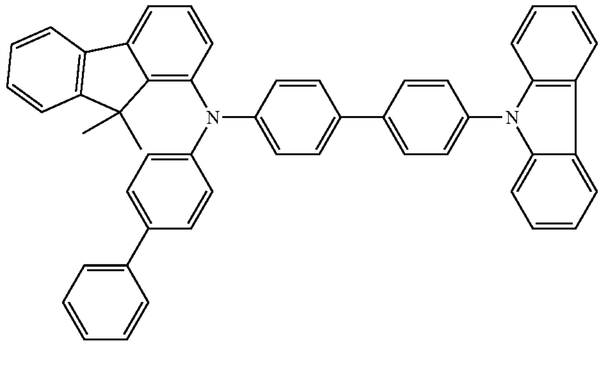 [SMILES: CC1(C)c2ccccc2-c2cccc(N(c3ccc(-c4ccccc4)cc3)c3ccc(-c4ccc(-n5c6ccccc6c6ccccc65)cc4)cc3)c21]

TABLE 3-continued
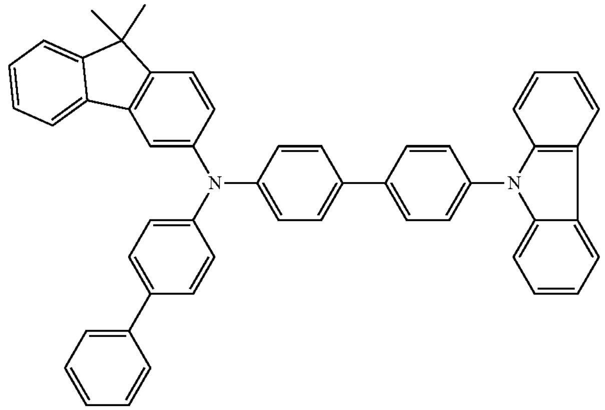 [SMILES: CC1(C)c2ccccc2-c2cc(N(c3ccc(-c4ccccc4)cc3)c3ccc(-c4ccc(-n5c6ccccc6c6ccccc65)cc4)cc3)ccc21]
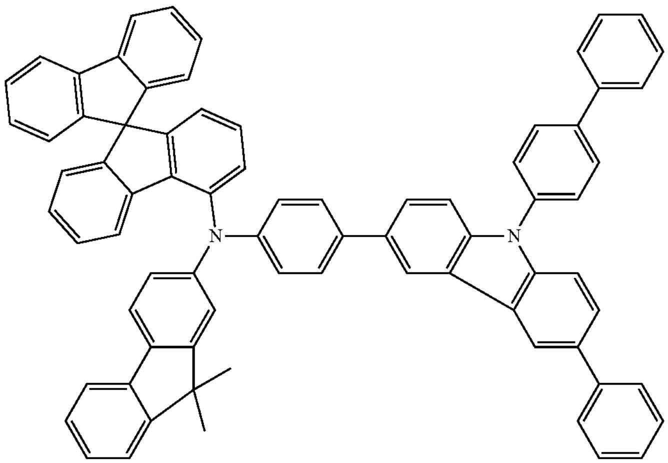 [SMILES: CC1(C)c2ccccc2-c2ccc(N(c3ccc(-c4ccc5c(c4)c4cc(-c6ccccc6)ccc4n5-c4ccc(-c5ccccc5)cc4)cc3)c3cccc4c3-c3ccccc3C43c4ccccc4-c4ccccc43)cc21]
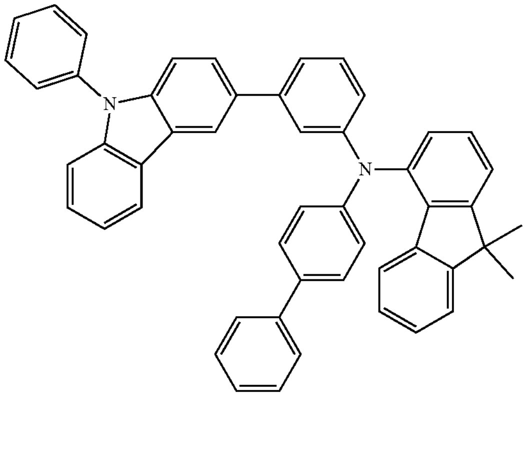 [SMILES: CC1(C)c2ccccc2-c2c(N(c3ccc(-c4ccccc4)cc3)c3cccc(-c4ccc5c(c4)c4ccccc4n5-c4ccccc4)c3)cccc21]

TABLE 3-continued
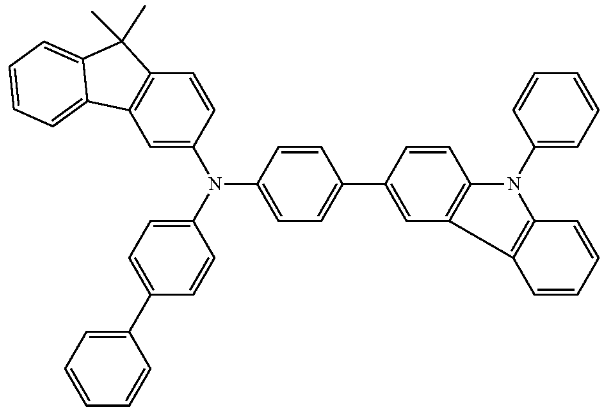 [SMILES: CC1(C)c2ccccc2-c2cc(N(c3ccc(-c4ccccc4)cc3)c3ccc(-c4ccc5c(c4)c4ccccc4n5-c4ccccc4)cc3)ccc21]
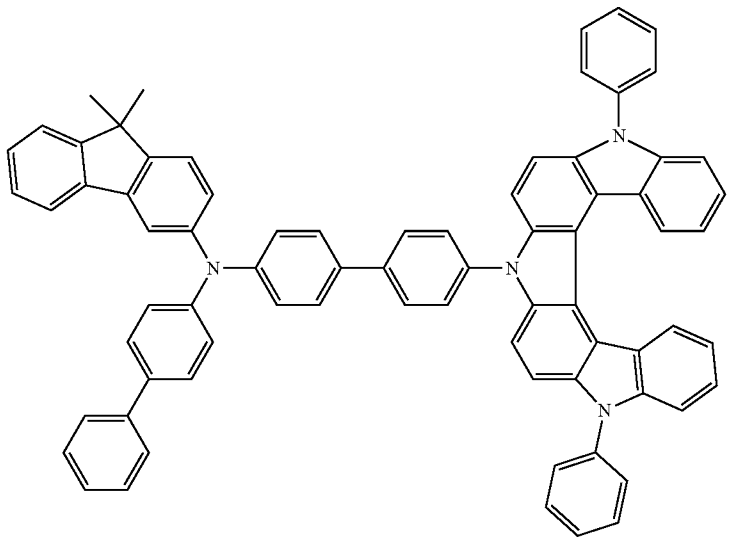 [SMILES: CC1(C)c2ccccc2-c2cc(N(c3ccc(-c4ccccc4)cc3)c3ccc(-c4ccc(-n5c6ccc7c(c8ccccc8n7-c7ccccc7)c6c6c7c8ccccc8n(-c8ccccc8)c7ccc65)cc4)cc3)ccc21]
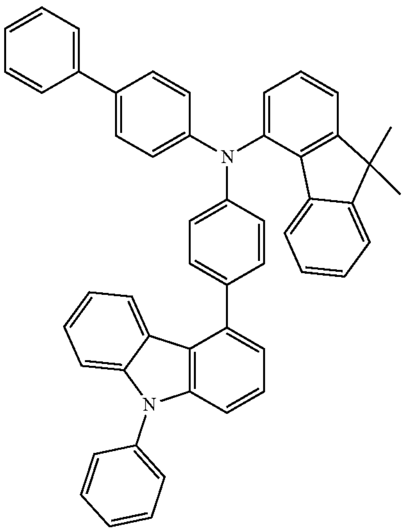 [SMILES: CC1(C)c2ccccc2-c2c(N(c3ccc(-c4ccccc4)cc3)c3ccc(-c4cccc5c4c4ccccc4n5-c4ccccc4)cc3)cccc21]

TABLE 3-continued
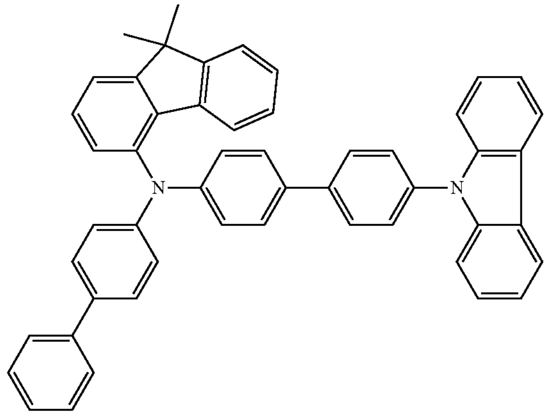 [SMILES: CC1(C)c2ccccc2-c2c(N(c3ccc(-c4ccccc4)cc3)c3ccc(-c4ccc(-n5c6ccccc6c6ccccc65)cc4)cc3)cccc21]
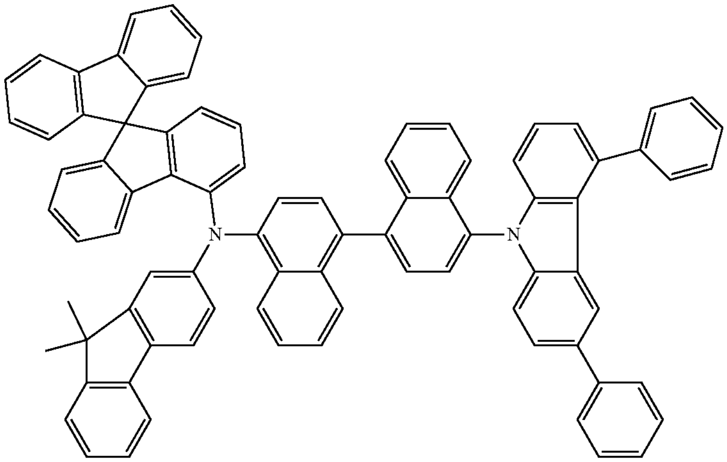 [SMILES: CC1(C)c2ccccc2-c2ccc(N(c3cccc4c3-c3ccccc3C43c4ccccc4-c4ccccc43)c3ccc(-c4ccc(-n5c6ccc(-c7ccccc7)cc6c6c(-c7ccccc7)cccc65)c5ccccc45)c4ccccc34)cc21]
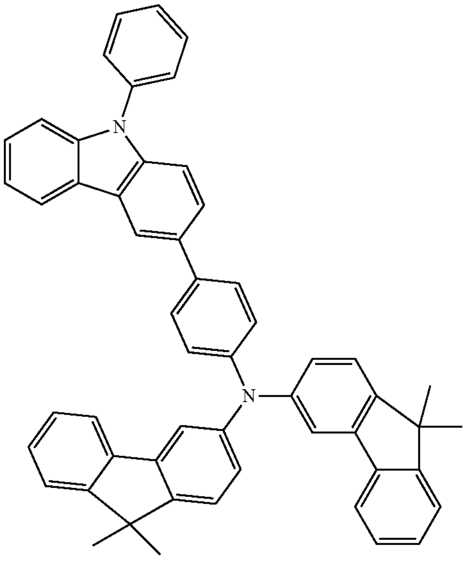 [SMILES: CC1(C)c2ccccc2-c2cc(N(c3ccc(-c4ccc5c(c4)c4ccccc4n5-c4ccccc4)cc3)c3ccc4c(c3)-c3ccccc3C4(C)C)ccc21]

TABLE 3-continued
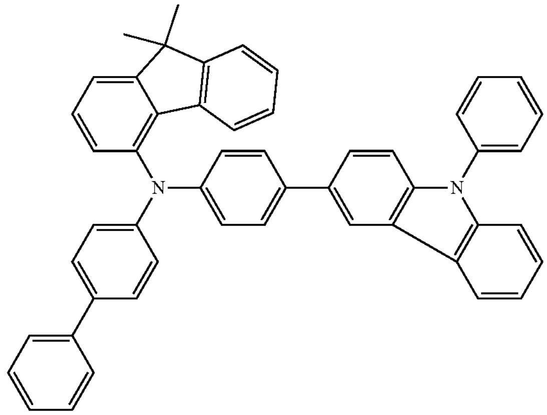 [SMILES: CC1(C)c2ccccc2-c2c(N(c3ccc(-c4ccccc4)cc3)c3ccc(-c4ccc5c(c4)c4ccccc4n5-c4ccccc4)cc3)cccc21]
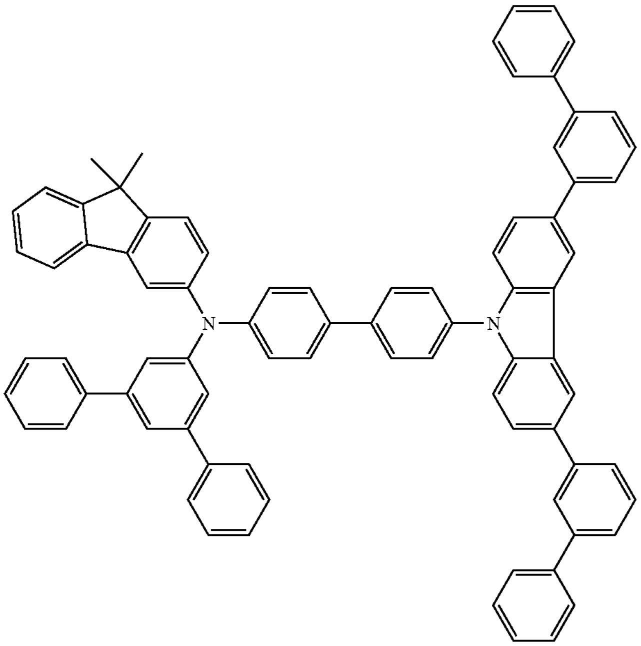 [SMILES: CC1(C)c2ccccc2-c2cc(N(c3ccc(-c4ccc(-n5c6ccc(-c7cccc(-c8ccccc8)c7)cc6c6cc(-c7cccc(-c8ccccc8)c7)ccc65)cc4)cc3)c3cc(-c4ccccc4)cc(-c4ccccc4)c3)ccc21]
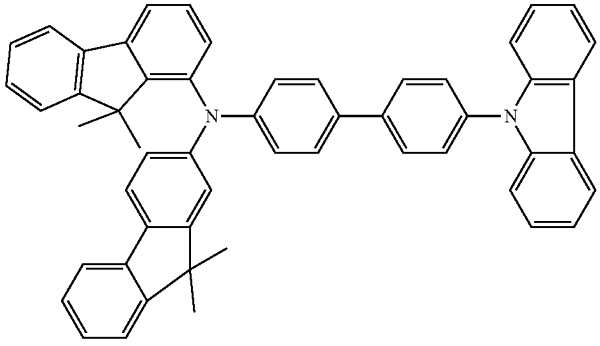 [SMILES: CC1(C)c2ccccc2-c2ccc(N(c3ccc(-c4ccc(-n5c6ccccc6c6ccccc65)cc4)cc3)c3cccc4c3C(C)(C)c3ccccc3-4)cc21]

TABLE 3-continued
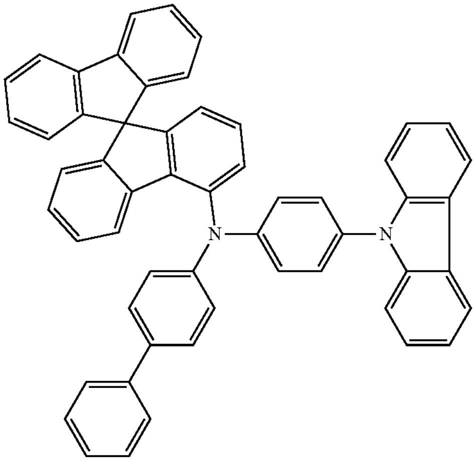 [SMILES: c1ccc(-c2ccc(N(c3ccc(-n4c5ccccc5c5ccccc54)cc3)c3cccc4c3-c3ccccc3C43c4ccccc4-c4ccccc43)cc2)cc1]
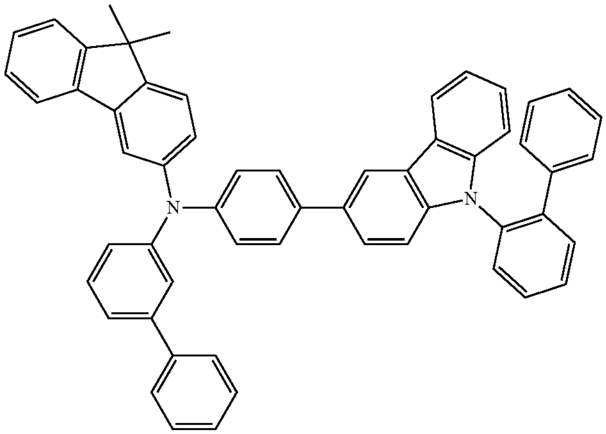 [SMILES: CC1(C)c2ccccc2-c2cc(N(c3ccc(-c4ccc5c(c4)c4ccccc4n5-c4ccccc4-c4ccccc4)cc3)c3cccc(-c4ccccc4)c3)ccc21]
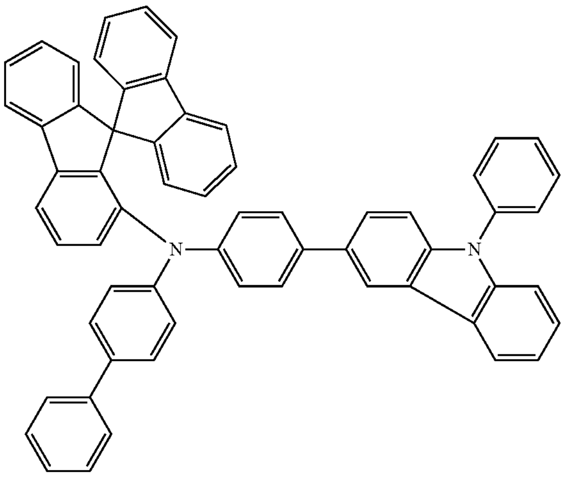 [SMILES: c1ccc(-c2ccc(N(c3ccc(-c4ccc5c(c4)c4ccccc4n5-c4ccccc4)cc3)c3cccc4c3C3(c5ccccc5-c5ccccc53)c3ccccc3-4)cc2)cc1]

TABLE 3-continued
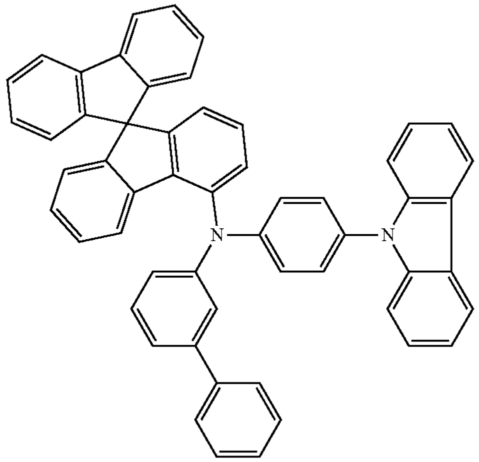 [SMILES: c1ccc(-c2cccc(N(c3ccc(-n4c5ccccc5c5ccccc54)cc3)c3cccc4c3-c3ccccc3C43c4ccccc4-c4ccccc43)c2)cc1]
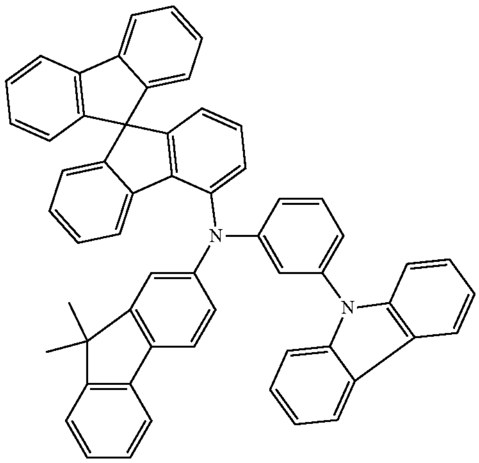 [SMILES: CC1(C)c2ccccc2-c2ccc(N(c3cccc(-n4c5ccccc5c5ccccc54)c3)c3cccc4c3-c3ccccc3C43c4ccccc4-c4ccccc43)cc21]
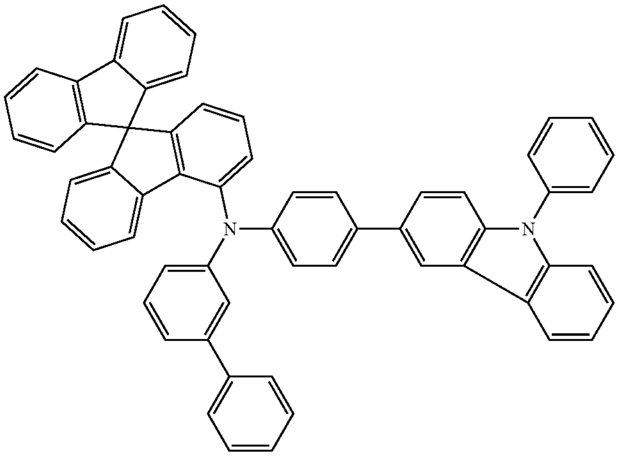 [SMILES: c1ccc(-c2cccc(N(c3ccc(-c4ccc5c(c4)c4ccccc4n5-c4ccccc4)cc3)c3cccc4c3-c3ccccc3C43c4ccccc4-c4ccccc43)c2)cc1]

TABLE 3-continued
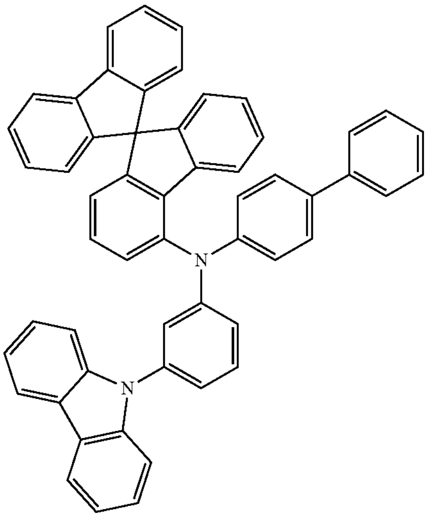 [SMILES: c1ccc(-c2ccc(N(c3cccc(-n4c5ccccc5c5ccccc54)c3)c3cccc4c3-c3ccccc3C43c4ccccc4-c4ccccc43)cc2)cc1]
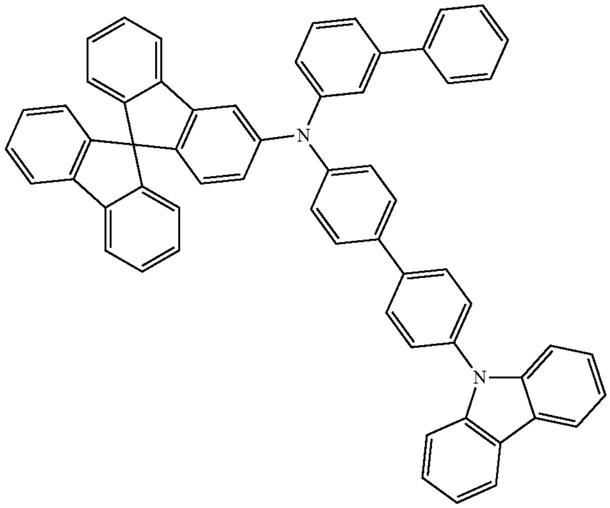 [SMILES: c1ccc(-c2cccc(N(c3ccc(-c4ccc(-n5c6ccccc6c6ccccc65)cc4)cc3)c3ccc4c(c3)-c3ccccc3C43c4ccccc4-c4ccccc43)c2)cc1]
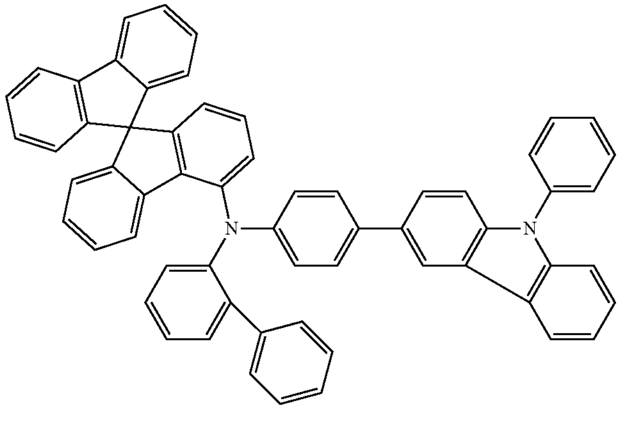 [SMILES: c1ccc(-c2ccccc2N(c2ccc(-c3ccc4c(c3)c3ccccc3n4-c3ccccc3)cc2)c2cccc3c2-c2ccccc2C32c3ccccc3-c3ccccc32)cc1]

TABLE 3-continued
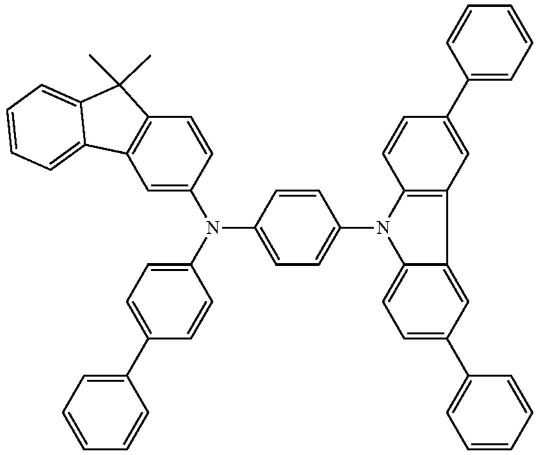 [SMILES: CC1(C)c2ccccc2-c2cc(N(c3ccc(-c4ccccc4)cc3)c3ccc(-n4c5ccc(-c6ccccc6)cc5c5cc(-c6ccccc6)ccc54)cc3)ccc21]
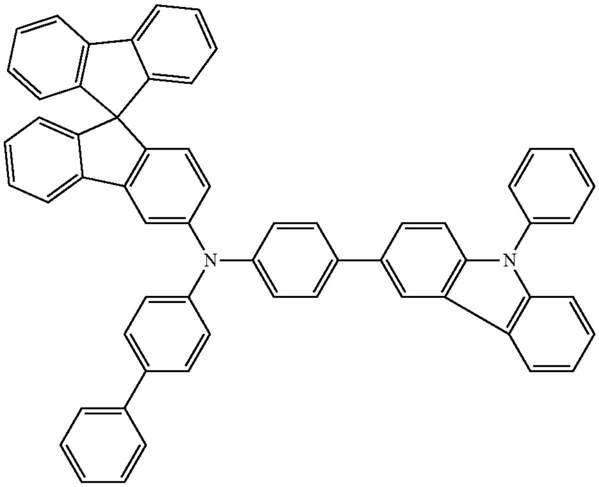 [SMILES: c1ccc(-c2ccc(N(c3ccc(-c4ccc5c(c4)c4ccccc4n5-c4ccccc4)cc3)c3ccc4c(c3)-c3ccccc3C43c4ccccc4-c4ccccc43)cc2)cc1]
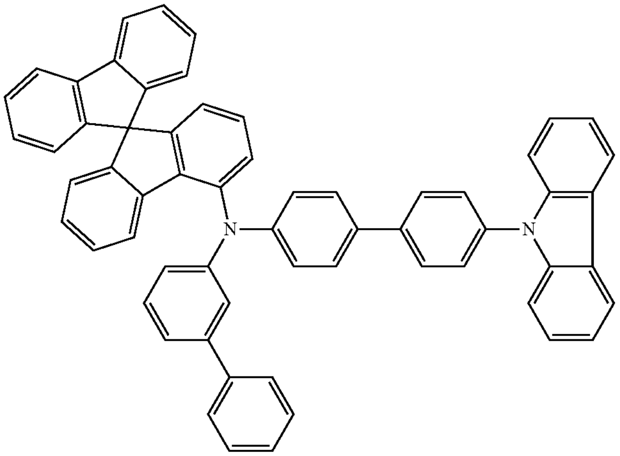 [SMILES: c1ccc(-c2cccc(N(c3ccc(-c4ccc(-n5c6ccccc6c6ccccc65)cc4)cc3)c3cccc4c3-c3ccccc3C43c4ccccc4-c4ccccc43)c2)cc1]

TABLE 3-continued
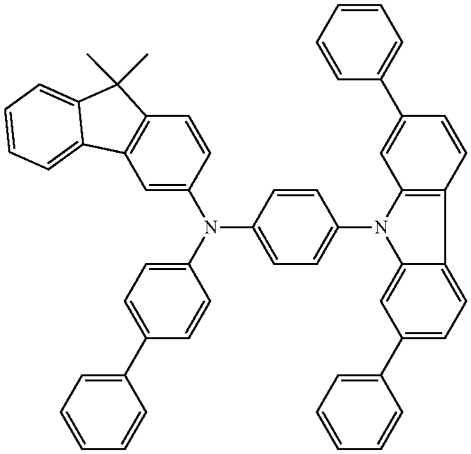 [SMILES: CC1(C)c2ccccc2-c2cc(N(c3ccc(-c4ccccc4)cc3)c3ccc(-n4c5cc(-c6ccccc6)ccc5c5ccc(-c6ccccc6)cc54)cc3)ccc21]
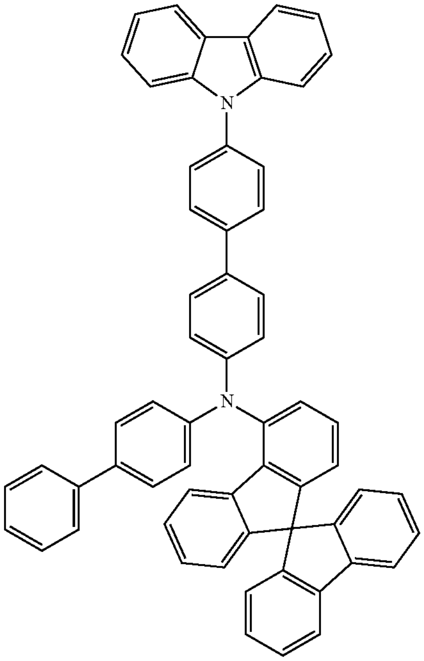 [SMILES: c1ccc(-c2ccc(N(c3ccc(-c4ccc(-n5c6ccccc6c6ccccc65)cc4)cc3)c3cccc4c3-c3ccccc3C43c4ccccc4-c4ccccc43)cc2)cc1]
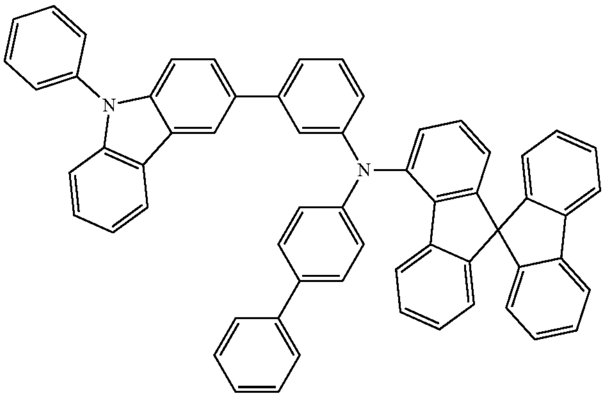 [SMILES: c1ccc(-c2ccc(N(c3cccc(-c4ccc5c(c4)c4ccccc4n5-c4ccccc4)c3)c3cccc4c3-c3ccccc3C43c4ccccc4-c4ccccc43)cc2)cc1]

TABLE 3-continued
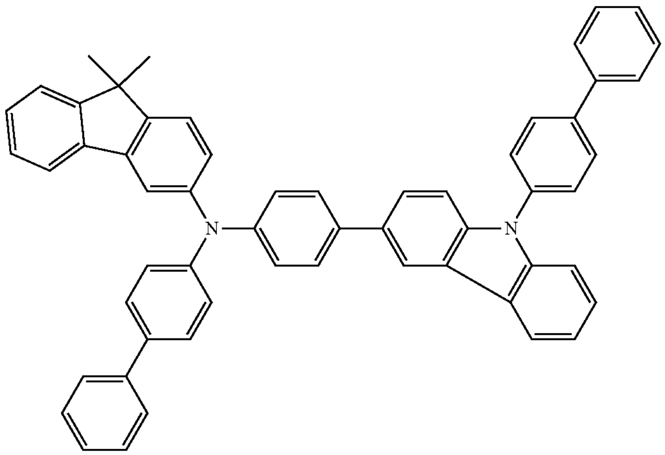 [SMILES: CC1(C)c2ccccc2-c2cc(N(c3ccc(-c4ccccc4)cc3)c3ccc(-c4ccc5c(c4)c4ccccc4n5-c4ccc(-c5ccccc5)cc4)cc3)ccc21]
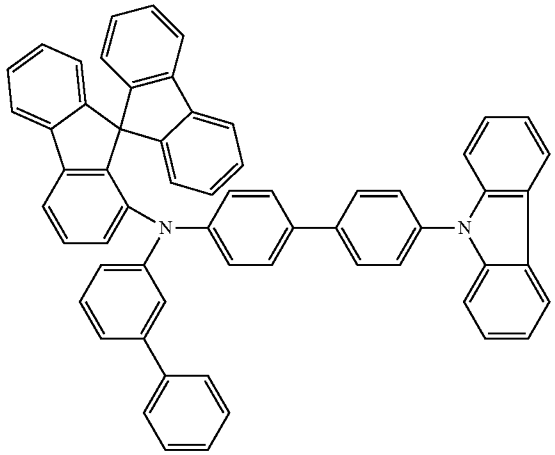 [SMILES: c1ccc(-c2cccc(N(c3ccc(-c4ccc(-n5c6ccccc6c6ccccc65)cc4)cc3)c3cccc4c3C3(c5ccccc5-c5ccccc53)c3ccccc3-4)c2)cc1]
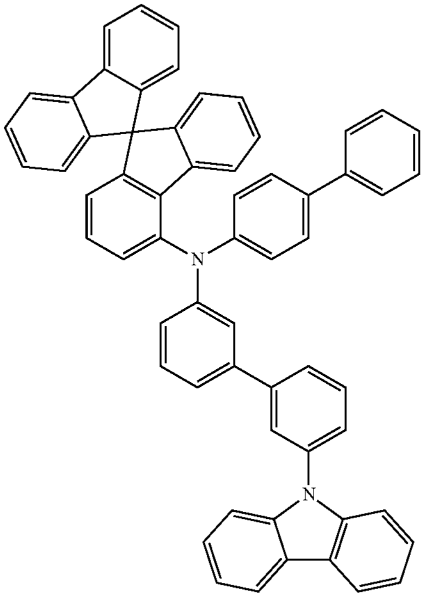 [SMILES: c1ccc(-c2ccc(N(c3cccc(-c4cccc(-n5c6ccccc6c6ccccc65)c4)c3)c3cccc4c3-c3ccccc3C43c4ccccc4-c4ccccc43)cc2)cc1]

TABLE 3-continued
27
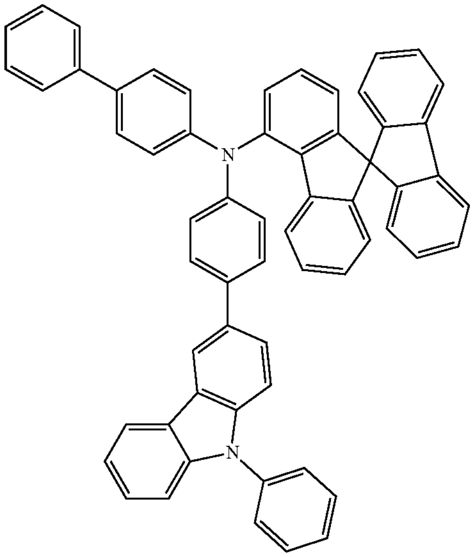 [SMILES: c1ccc(-c2ccc(N(c3ccc(-c4ccc5c(c4)c4ccccc4n5-c4ccccc4)cc3)c3cccc4c3-c3ccccc3C43c4ccccc4-c4ccccc43)cc2)cc1]
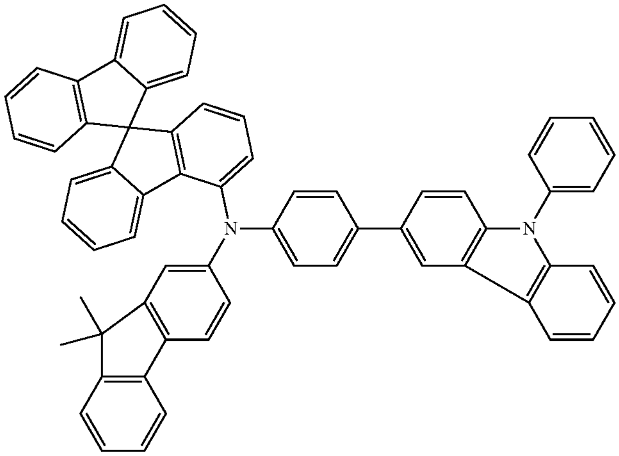 [SMILES: CC1(C)c2ccccc2-c2ccc(N(c3ccc(-c4ccc5c(c4)c4ccccc4n5-c4ccccc4)cc3)c3cccc4c3-c3ccccc3C43c4ccccc4-c4ccccc43)cc21]
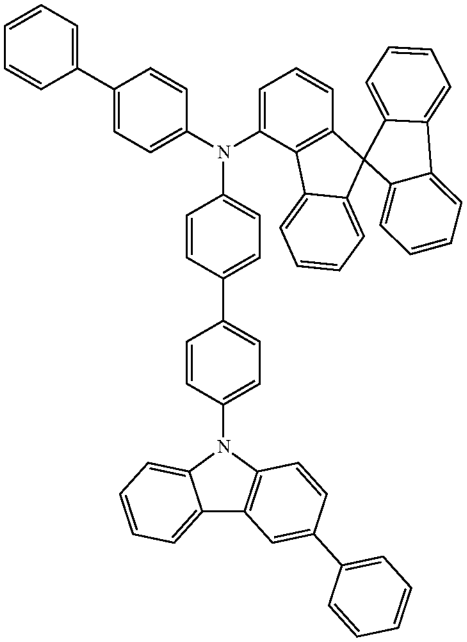 [SMILES: c1ccc(-c2ccc(N(c3ccc(-c4ccc(-n5c6ccccc6c6cc(-c7ccccc7)ccc65)cc4)cc3)c3cccc4c3-c3ccccc3C43c4ccccc4-c4ccccc43)cc2)cc1]

TABLE 3-continued
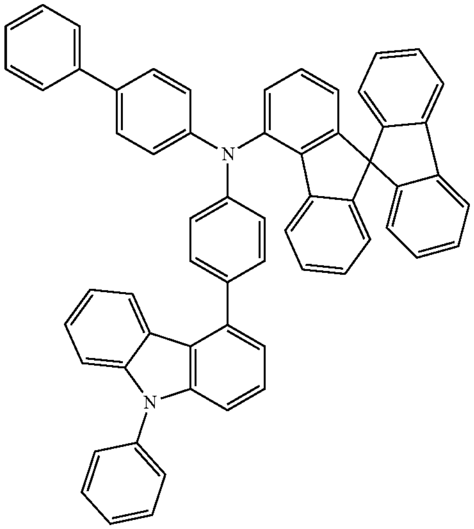 [SMILES: c1ccc(-c2ccc(N(c3ccc(-c4cccc5c4c4ccccc4n5-c4ccccc4)cc3)c3cccc4c3-c3ccccc3C43c4ccccc4-c4ccccc43)cc2)cc1]
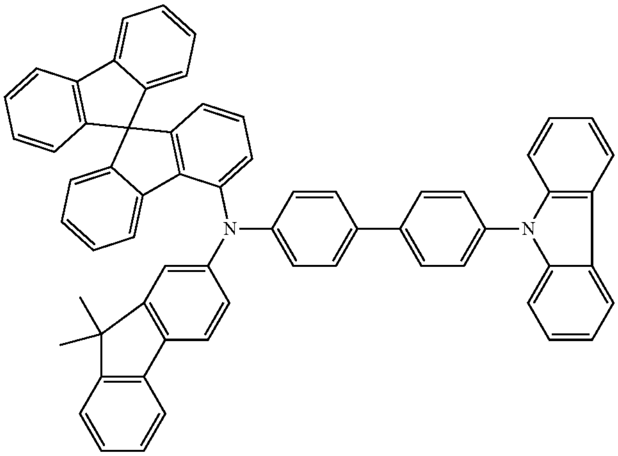 [SMILES: CC1(C)c2ccccc2-c2ccc(N(c3ccc(-c4ccc(-n5c6ccccc6c6ccccc65)cc4)cc3)c3cccc4c3-c3ccccc3C43c4ccccc4-c4ccccc43)cc21]
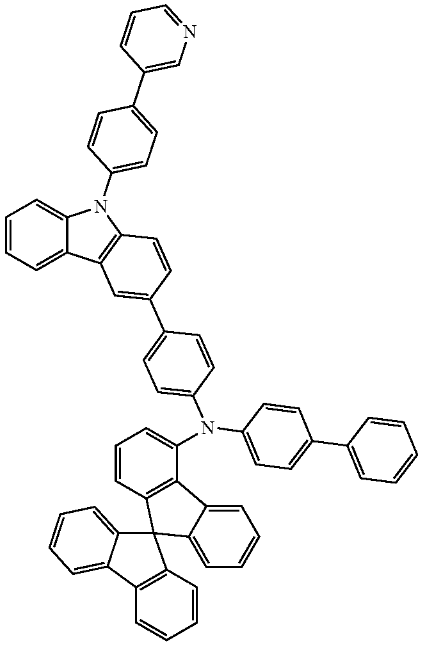 [SMILES: c1ccc(-c2ccc(N(c3ccc(-c4ccc5c(c4)c4ccccc4n5-c4ccc(-c5cccnc5)cc4)cc3)c3cccc4c3-c3ccccc3C43c4ccccc4-c4ccccc43)cc2)cc1]

TABLE 3-continued
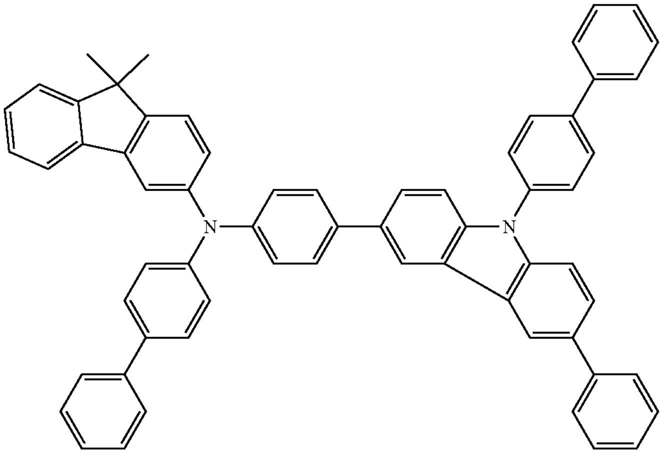 [SMILES: CC1(C)c2ccccc2-c2cc(N(c3ccc(-c4ccccc4)cc3)c3ccc(-c4ccc5c(c4)c4cc(-c6ccccc6)ccc4n5-c4ccc(-c5ccccc5)cc4)cc3)ccc21]
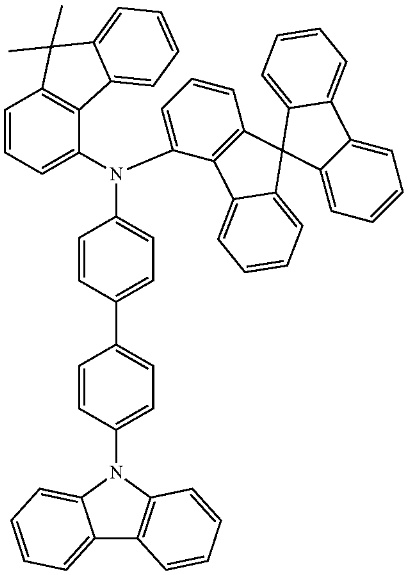 [SMILES: CC1(C)c2ccccc2-c2c(N(c3ccc(-c4ccc(-n5c6ccccc6c6ccccc65)cc4)cc3)c3cccc4c3-c3ccccc3C43c4ccccc4-c4ccccc43)cccc21]
28
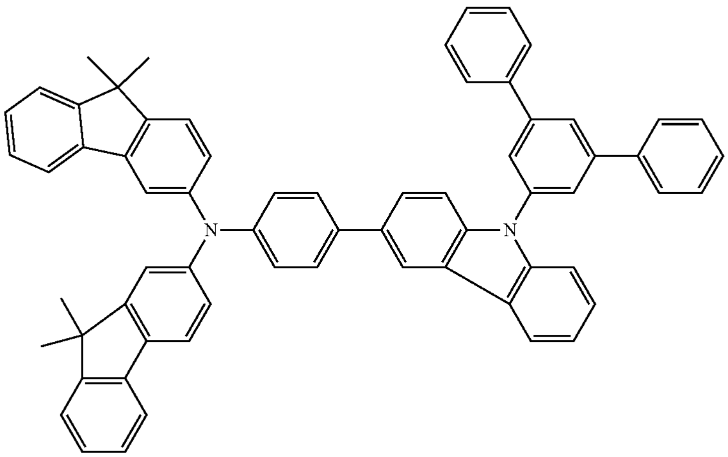 [SMILES: CC1(C)c2ccccc2-c2cc(N(c3ccc(-c4ccc5c(c4)c4ccccc4n5-c4cc(-c5ccccc5)cc(-c5ccccc5)c4)cc3)c3ccc4c(c3)C(C)(C)c3ccccc3-4)ccc21]

TABLE 3-continued
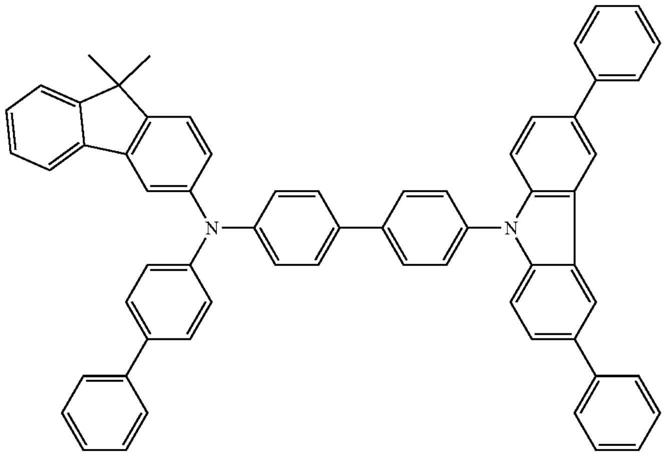 [SMILES: CC1(C)c2ccccc2-c2cc(N(c3ccc(-c4ccccc4)cc3)c3ccc(-c4ccc(-n5c6ccc(-c7ccccc7)cc6c6cc(-c7ccccc7)ccc65)cc4)cc3)ccc21]
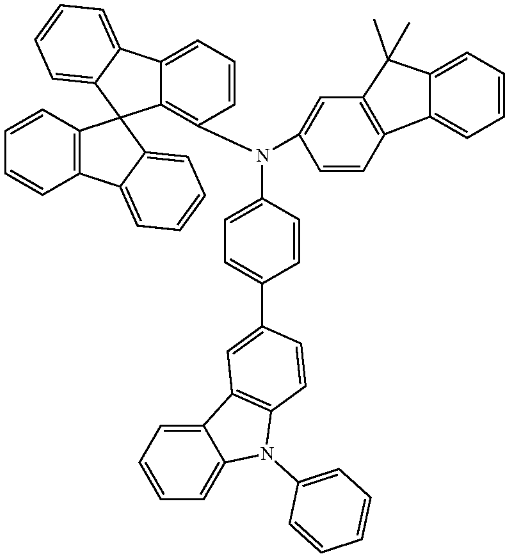 [SMILES: CC1(C)c2ccccc2-c2ccc(N(c3ccc(-c4ccc5c(c4)c4ccccc4n5-c4ccccc4)cc3)c3cccc4c3C3(c5ccccc5-c5ccccc53)c3ccccc3-4)cc21]
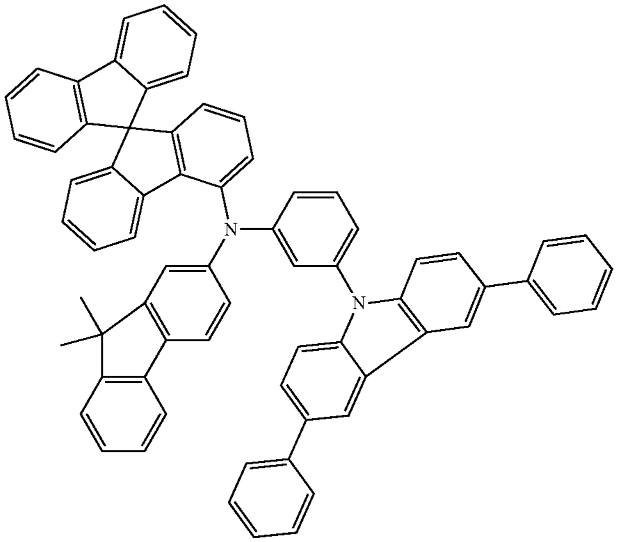 [SMILES: CC1(C)c2ccccc2-c2ccc(N(c3cccc(-n4c5ccc(-c6ccccc6)cc5c5cc(-c6ccccc6)ccc54)c3)c3cccc4c3-c3ccccc3C43c4ccccc4-c4ccccc43)cc21]

TABLE 3-continued
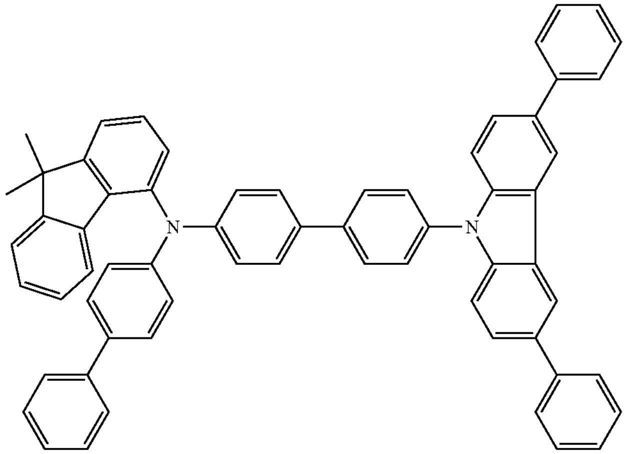 [SMILES: CC1(C)c2ccccc2-c2c(N(c3ccc(-c4ccccc4)cc3)c3ccc(-c4ccc(-n5c6ccc(-c7ccccc7)cc6c6cc(-c7ccccc7)ccc65)cc4)cc3)cccc21]
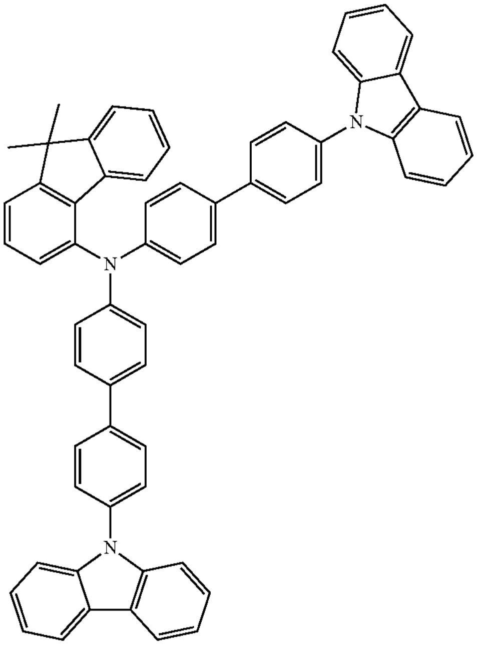 [SMILES: CC1(C)c2ccccc2-c2c(N(c3ccc(-c4ccc(-n5c6ccccc6c6ccccc65)cc4)cc3)c3ccc(-c4ccc(-n5c6ccccc6c6ccccc65)cc4)cc3)cccc21]
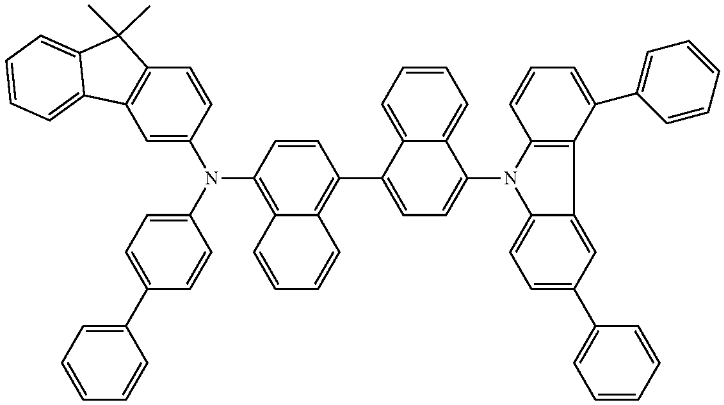 [SMILES: CC1(C)c2ccccc2-c2cc(N(c3ccc(-c4ccccc4)cc3)c3ccc(-c4ccc(-n5c6ccc(-c7ccccc7)cc6c6c(-c7ccccc7)cccc65)c5ccccc45)c4ccccc34)ccc21]

TABLE 3-continued
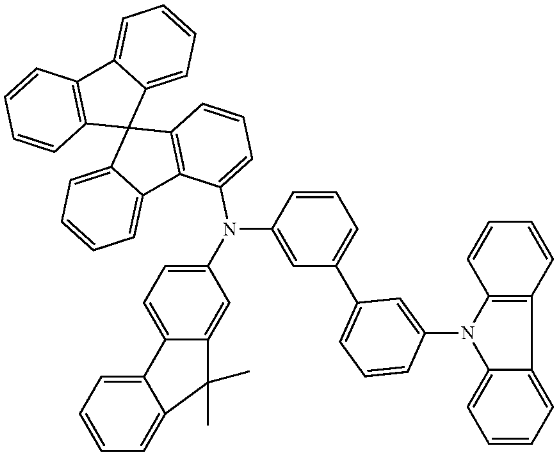 [SMILES: CC1(C)c2ccccc2-c2ccc(N(c3cccc(-c4cccc(-n5c6ccccc6c6ccccc65)c4)c3)c3cccc4c3-c3ccccc3C43c4ccccc4-c4ccccc43)cc21]
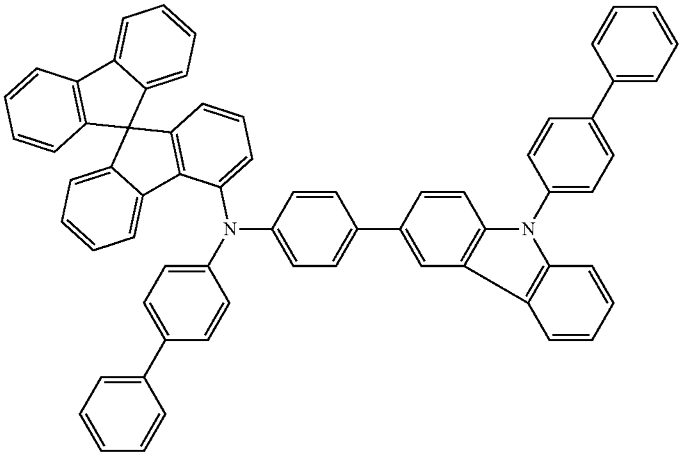 [SMILES: c1ccc(-c2ccc(N(c3ccc(-c4ccc5c(c4)c4ccccc4n5-c4ccc(-c5ccccc5)cc4)cc3)c3cccc4c3-c3ccccc3C43c4ccccc4-c4ccccc43)cc2)cc1]
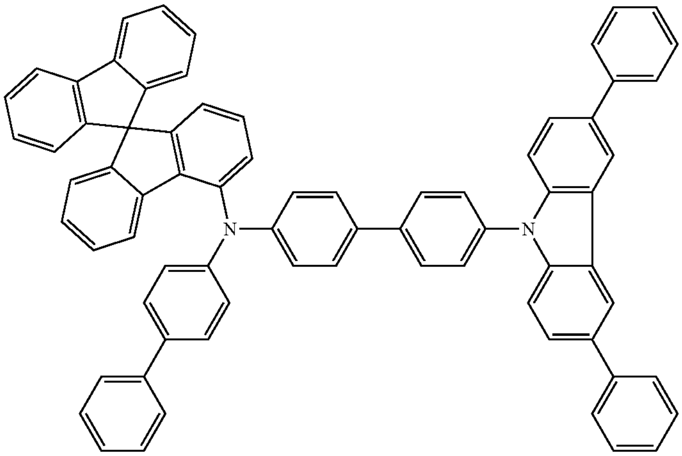 [SMILES: c1ccc(-c2ccc(N(c3ccc(-c4ccc(-n5c6ccc(-c7ccccc7)cc6c6cc(-c7ccccc7)ccc65)cc4)cc3)c3cccc4c3-c3ccccc3C43c4ccccc4-c4ccccc43)cc2)cc1]
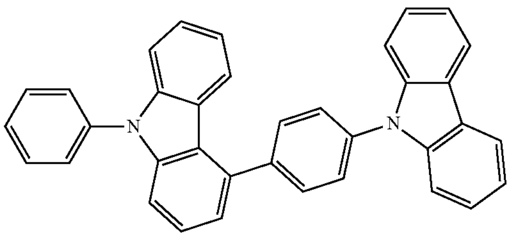 [SMILES: c1ccc(-n2c3ccccc3c3c(-c4ccc(-n5c6ccccc6c6ccccc65)cc4)cccc32)cc1]

TABLE 3-continued
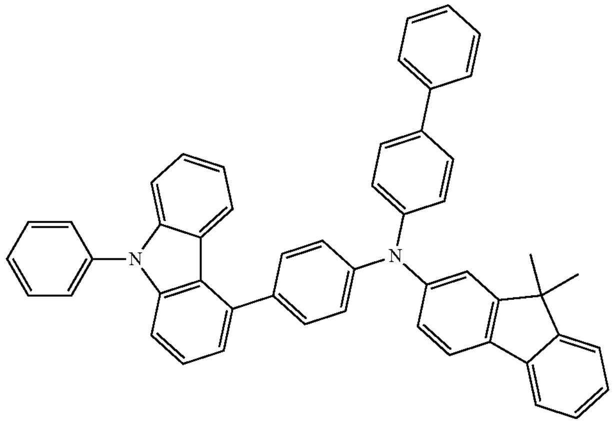 [SMILES: CC1(C)c2ccccc2-c2ccc(N(c3ccc(-c4ccccc4)cc3)c3ccc(-c4cccc5c4c4ccccc4n5-c4ccccc4)cc3)cc21]
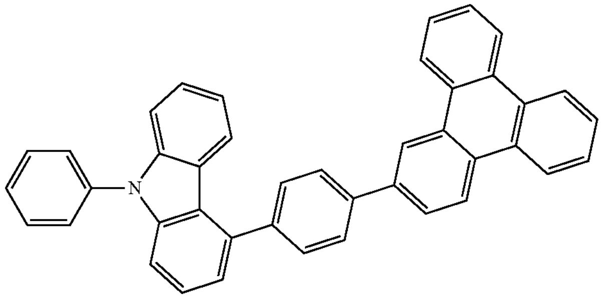 [SMILES: c1ccc(-n2c3ccccc3c3c(-c4ccc(-c5ccc6c7ccccc7c7ccccc7c6c5)cc4)cccc32)cc1]
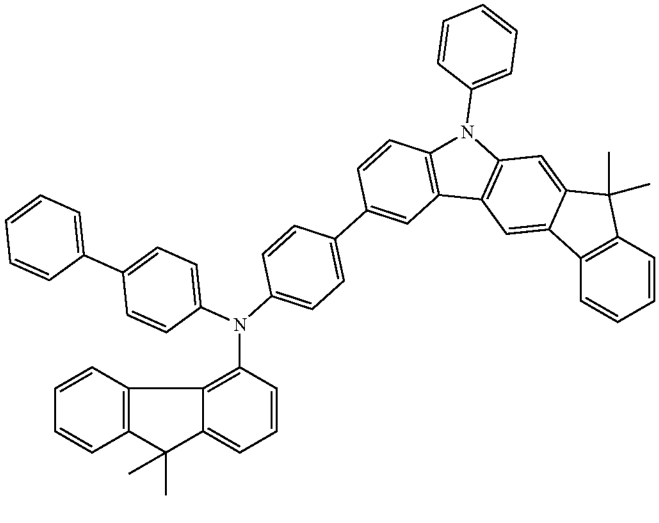 [SMILES: CC1(C)c2ccccc2-c2cc3c4cc(-c5ccc(N(c6ccc(-c7ccccc7)cc6)c6cccc7c6-c6ccccc6C7(C)C)cc5)ccc4n(-c4ccccc4)c3cc21]

TABLE 3-continued
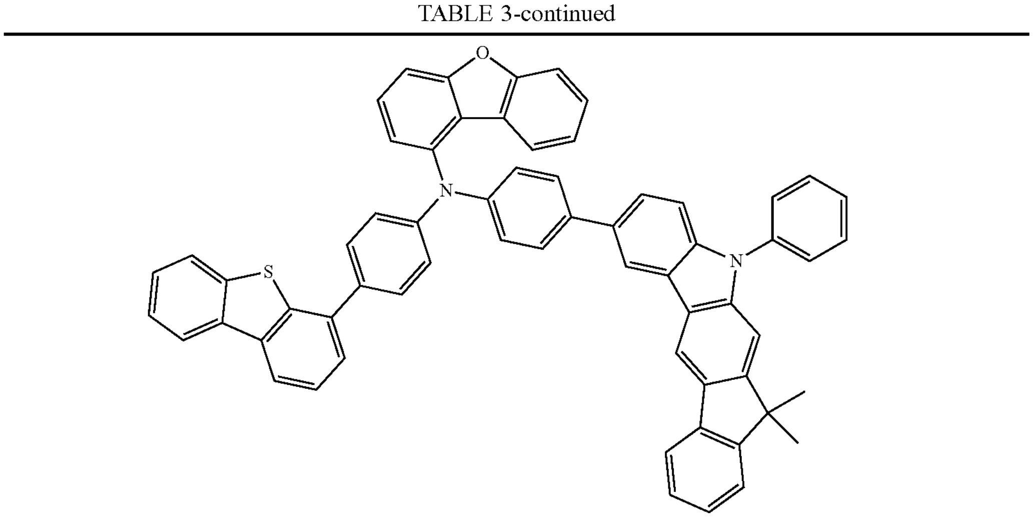
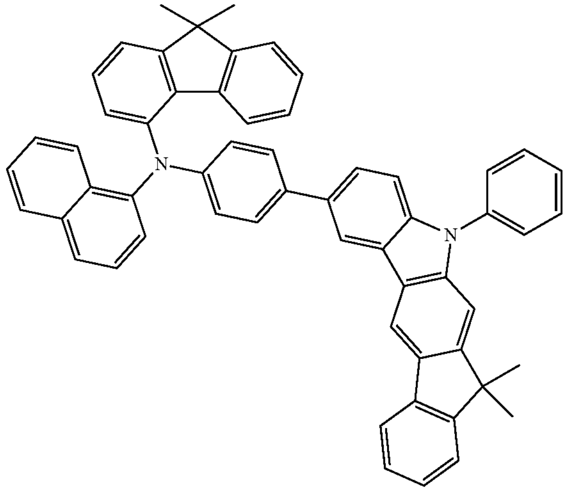 [SMILES: CC1(C)c2ccccc2-c2cc3c4cc(-c5ccc(N(c6cccc7c6-c6ccccc6C7(C)C)c6cccc7ccccc67)cc5)ccc4n(-c4ccccc4)c3cc21]
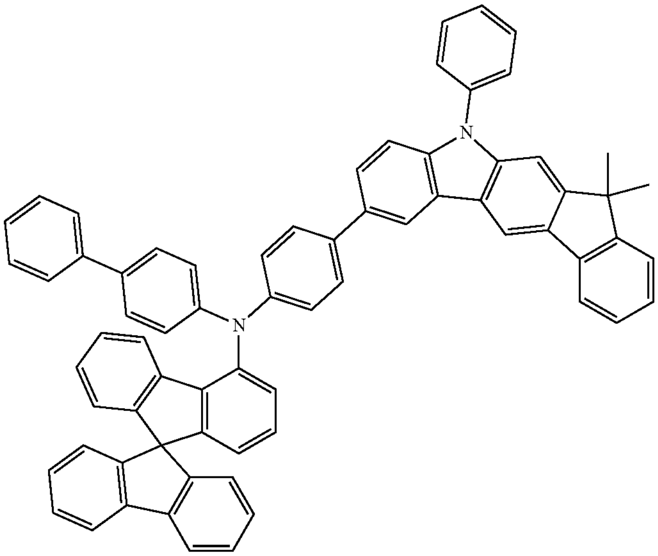 [SMILES: CC1(C)c2ccccc2-c2cc3c4cc(-c5ccc(N(c6ccc(-c7ccccc7)cc6)c6cccc7c6-c6ccccc6C76c7ccccc7-c7ccccc76)cc5)ccc4n(-c4ccccc4)c3cc21]

TABLE 3-continued
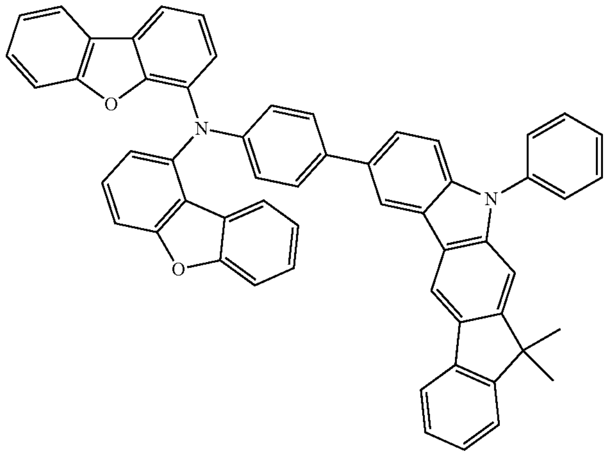 [SMILES: CC1(C)c2ccccc2-c2cc3c4cc(-c5ccc(N(c6cccc7c6oc6ccccc67)c6cccc7oc8ccccc8c67)cc5)ccc4n(-c4ccccc4)c3cc21]
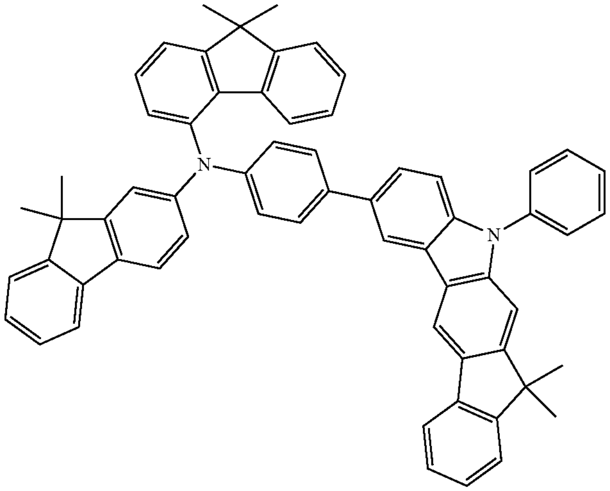 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3-c3ccccc3C4(C)C)cc21]
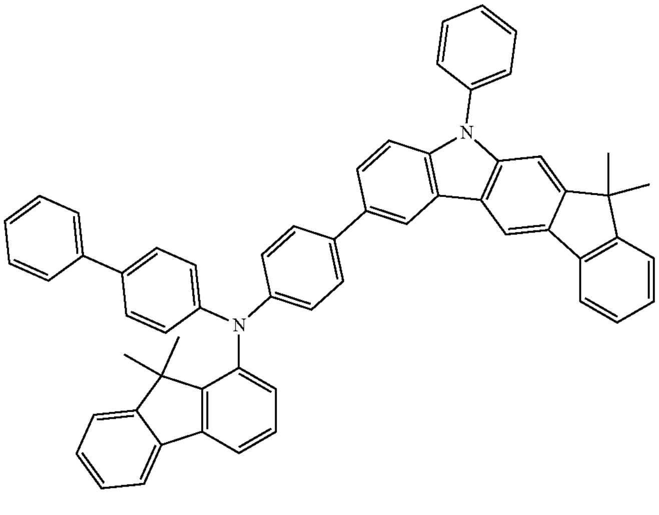 [SMILES: CC1(C)c2ccccc2-c2cc3c4cc(-c5ccc(N(c6ccc(-c7ccccc7)cc6)c6cccc7c6C(C)(C)c6ccccc6-7)cc5)ccc4n(-c4ccccc4)c3cc21]

TABLE 3-continued
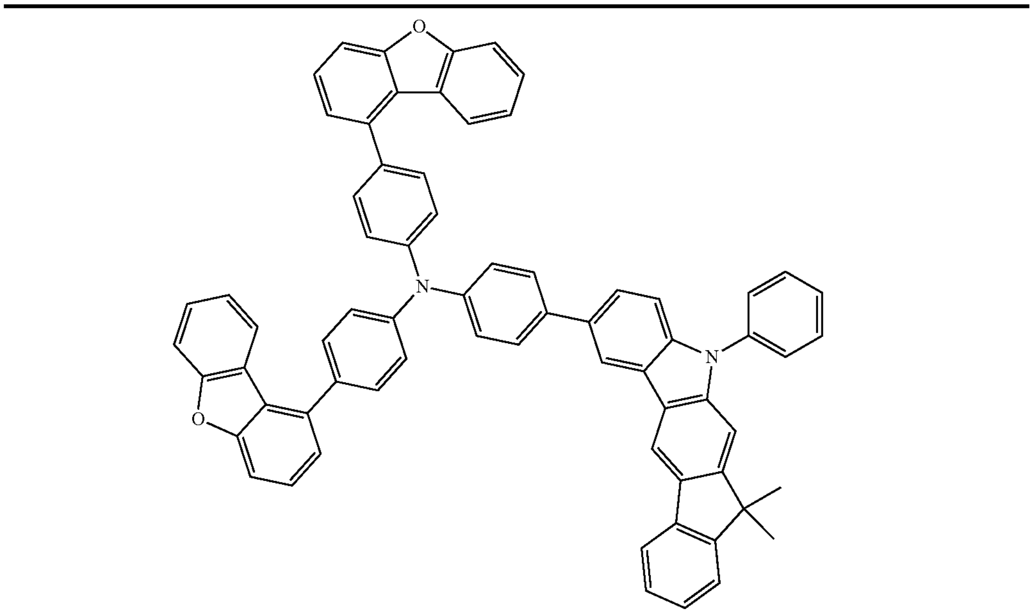
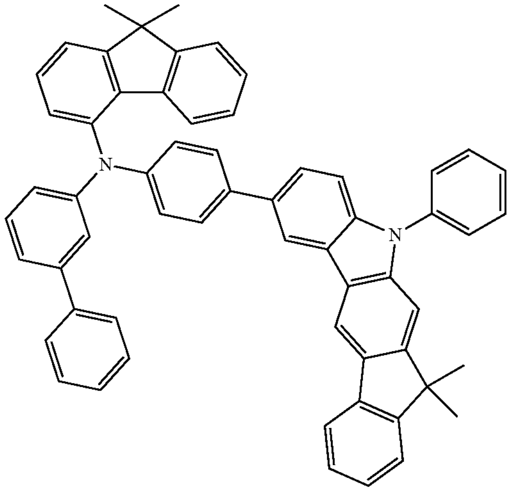 [SMILES: CC1(C)c2ccccc2-c2cc3c4cc(-c5ccc(N(c6cccc(-c7ccccc7)c6)c6cccc7c6-c6ccccc6C7(C)C)cc5)ccc4n(-c4ccccc4)c3cc21]
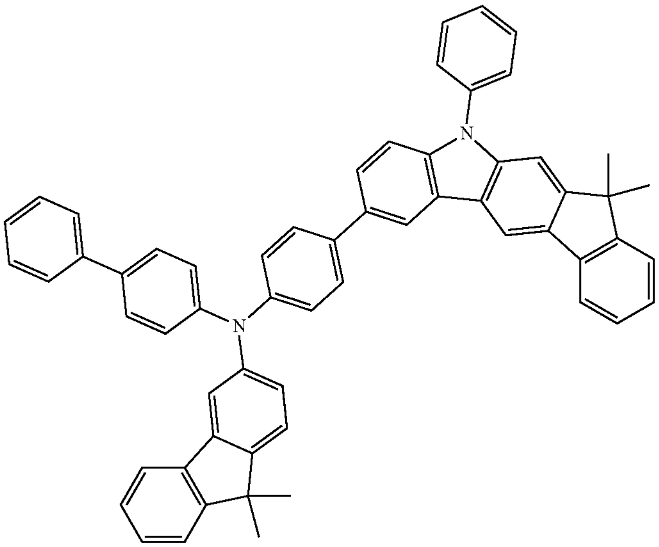 [SMILES: CC1(C)c2ccccc2-c2cc(N(c3ccc(-c4ccccc4)cc3)c3ccc(-c4ccc5c(c4)c4cc6c(cc4n5-c4ccccc4)C(C)(C)c4ccccc4-6)cc3)ccc21]

TABLE 3-continued
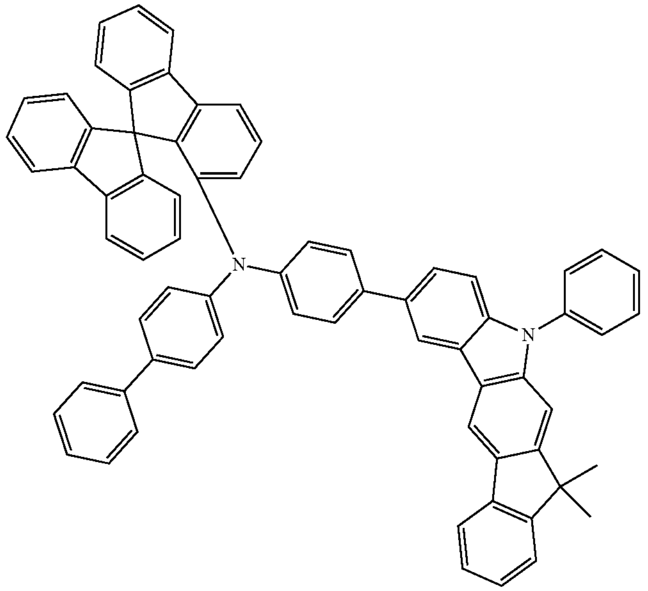 [SMILES: CC1(C)c2ccccc2-c2cc3c4cc(-c5ccc(N(c6ccc(-c7ccccc7)cc6)c6cccc7c6C6(c8ccccc8-c8ccccc86)c6ccccc6-7)cc5)ccc4n(-c4ccccc4)c3cc21]
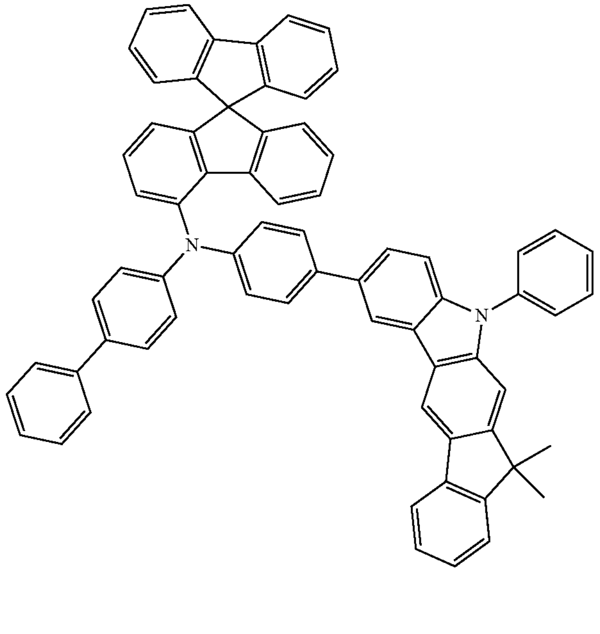 [SMILES: CC1(C)c2ccccc2-c2cc3c4cc(-c5ccc(N(c6ccc(-c7ccccc7)cc6)c6cccc7c6-c6ccccc6C76c7ccccc7-c7ccccc76)cc5)ccc4n(-c4ccccc4)c3cc21]

TABLE 3-continued
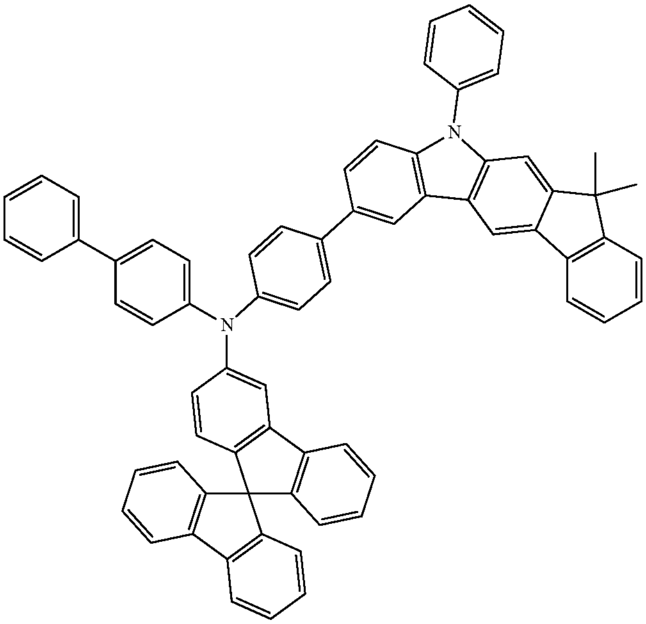 [SMILES: CC1(C)c2ccccc2-c2cc3c4cc(-c5ccc(N(c6ccc(-c7ccccc7)cc6)c6ccc7c(c6)-c6ccccc6C76c7ccccc7-c7ccccc76)cc5)ccc4n(-c4ccccc4)c3cc21]
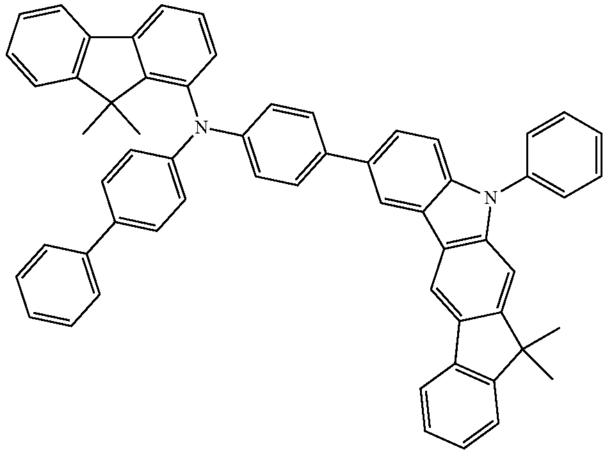 [SMILES: CC1(C)c2ccccc2-c2cc3c4cc(-c5ccc(N(c6ccc(-c7ccccc7)cc6)c6cccc7c6C(C)(C)c6ccccc6-7)cc5)ccc4n(-c4ccccc4)c3cc21]
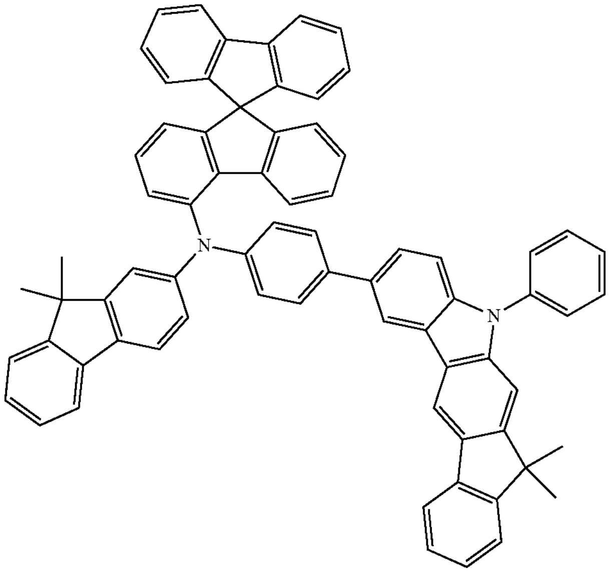 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3-c3ccccc3C43c4ccccc4-c4ccccc43)cc21]

TABLE 3-continued
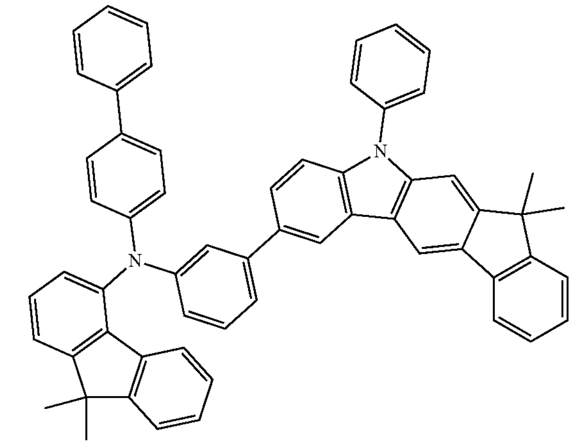 [SMILES: CC1(C)c2ccccc2-c2cc3c4cc(-c5cccc(N(c6ccc(-c7ccccc7)cc6)c6cccc7c6-c6ccccc6C7(C)C)c5)ccc4n(-c4ccccc4)c3cc21]
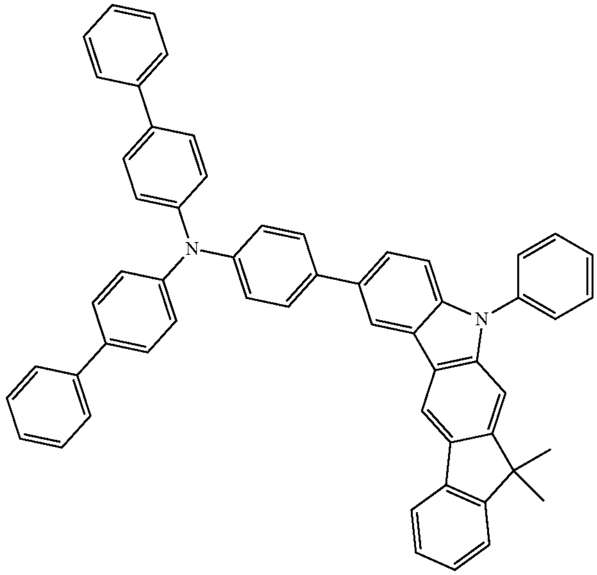 [SMILES: CC1(C)c2ccccc2-c2cc3c4cc(-c5ccc(N(c6ccc(-c7ccccc7)cc6)c6ccc(-c7ccccc7)cc6)cc5)ccc4n(-c4ccccc4)c3cc21]
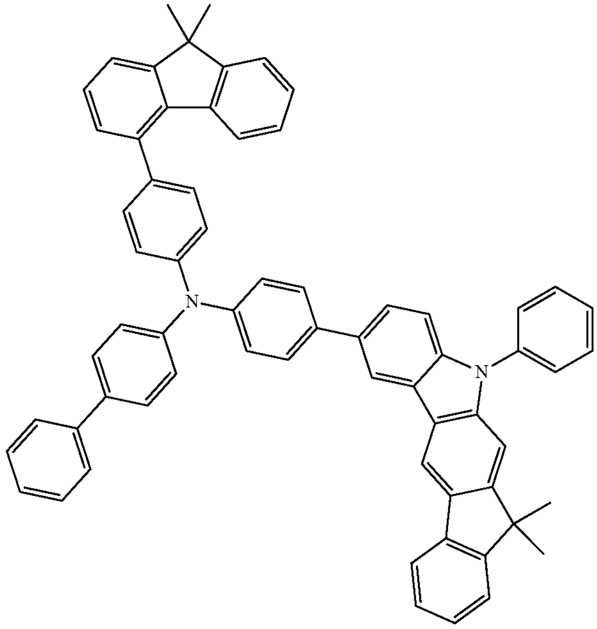 [SMILES: CC1(C)c2ccccc2-c2cc3c4cc(-c5ccc(N(c6ccc(-c7ccccc7)cc6)c6ccc(-c7cccc8c7-c7ccccc7C8(C)C)cc6)cc5)ccc4n(-c4ccccc4)c3cc21]

TABLE 3-continued
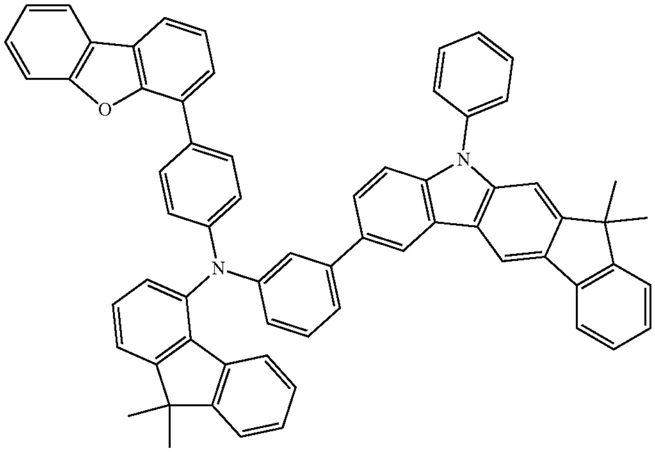 [SMILES: CC1(C)c2ccccc2-c2cc3c4cc(-c5cccc(N(c6ccc(-c7cccc8c7oc7ccccc78)cc6)c6cccc7c6-c6ccccc6C7(C)C)c5)ccc4n(-c4ccccc4)c3cc21]
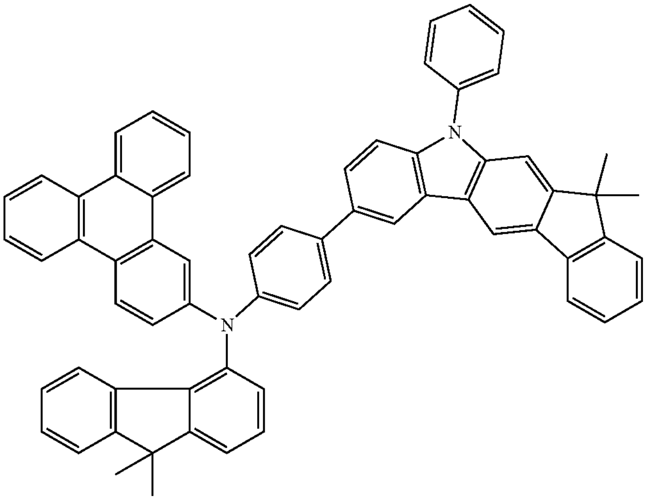 [SMILES: CC1(C)c2ccccc2-c2cc3c4cc(-c5ccc(N(c6ccc7c8ccccc8c8ccccc8c7c6)c6cccc7c6-c6ccccc6C7(C)C)cc5)ccc4n(-c4ccccc4)c3cc21]
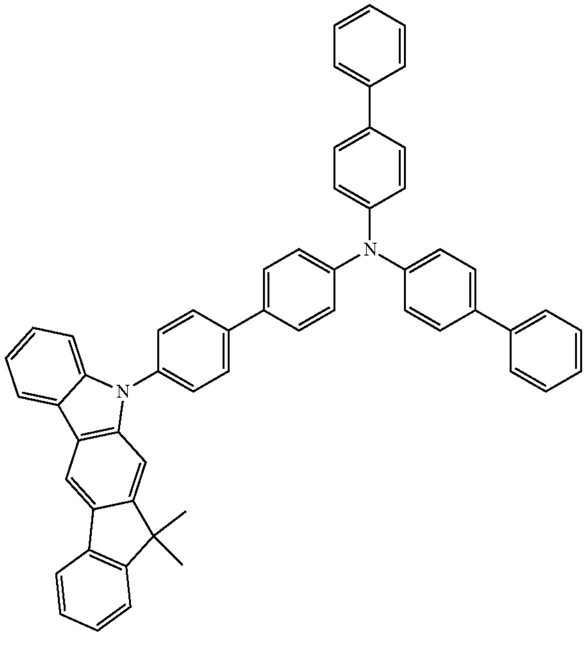 [SMILES: CC1(C)c2ccccc2-c2cc3c4ccccc4n(-c4ccc(-c5ccc(N(c6ccc(-c7ccccc7)cc6)c6ccc(-c7ccccc7)cc6)cc5)cc4)c3cc21]

TABLE 3-continued
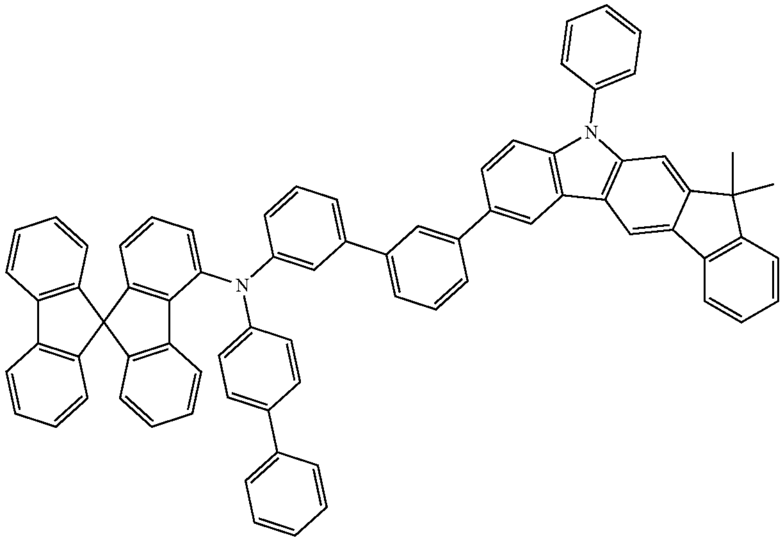 [SMILES: CC1(C)c2ccccc2-c2cc3c4cc(-c5cccc(-c6cccc(N(c7ccc(-c8ccccc8)cc7)c7cccc8c7-c7ccccc7C87c8ccccc8-c8ccccc87)c6)c5)ccc4n(-c4ccccc4)c3cc21]
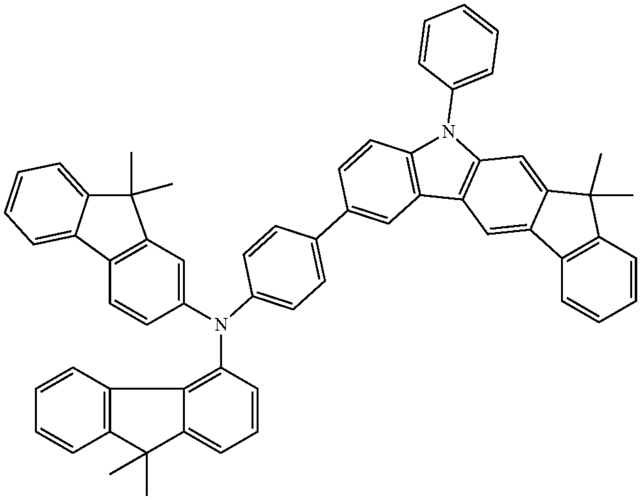 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3-c3ccccc3C4(C)C)cc21]
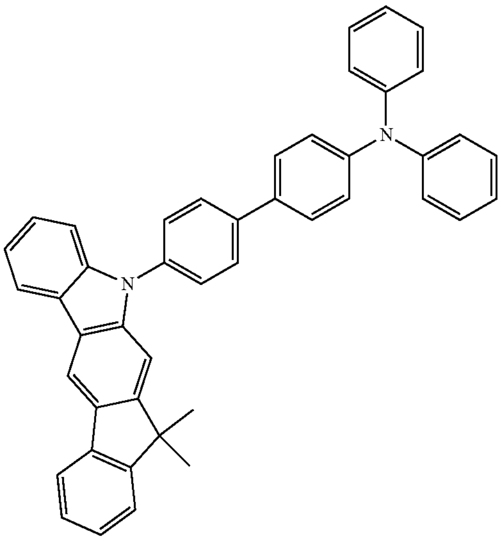 [SMILES: CC1(C)c2ccccc2-c2cc3c4ccccc4n(-c4ccc(-c5ccc(N(c6ccccc6)c6ccccc6)cc5)cc4)c3cc21]

TABLE 3-continued
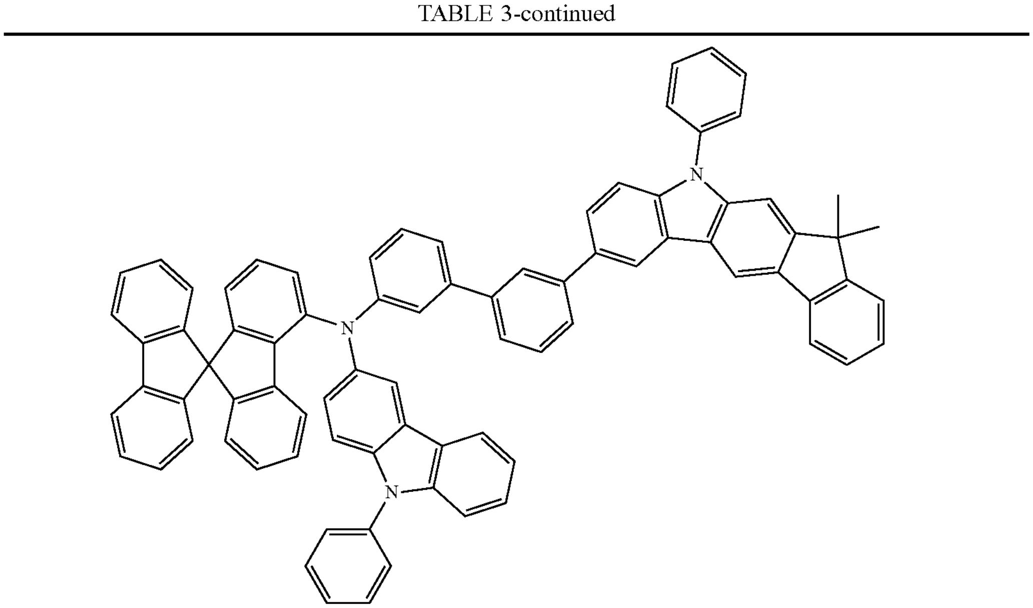
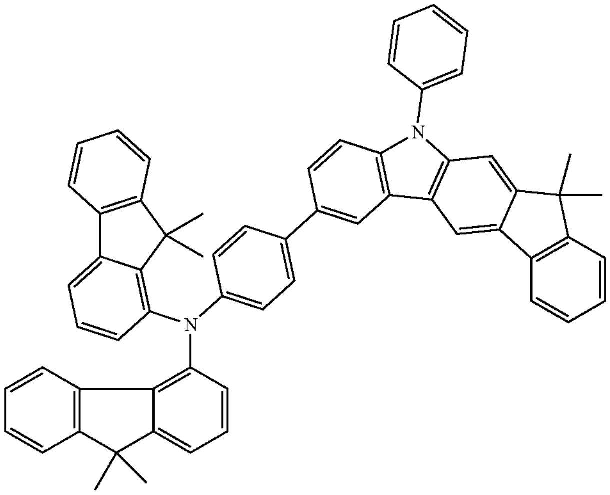 [SMILES: CC1(C)c2ccccc2-c2cc3c4cc(-c5ccc(N(c6cccc7c6-c6ccccc6C7(C)C)c6cccc7c6C(C)(C)c6ccccc6-7)cc5)ccc4n(-c4ccccc4)c3cc21]
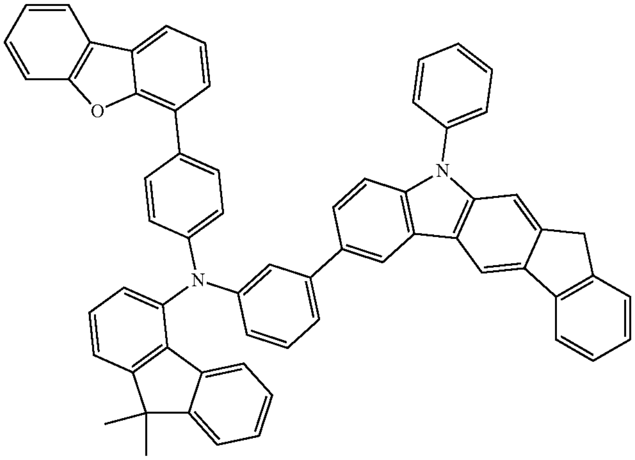 [SMILES: CC1(C)c2ccccc2-c2c(N(c3ccc(-c4cccc5c4oc4ccccc45)cc3)c3cccc(-c4ccc5c(c4)c4cc6c(cc4n5-c4ccccc4)Cc4ccccc4-6)c3)cccc21]

TABLE 3-continued
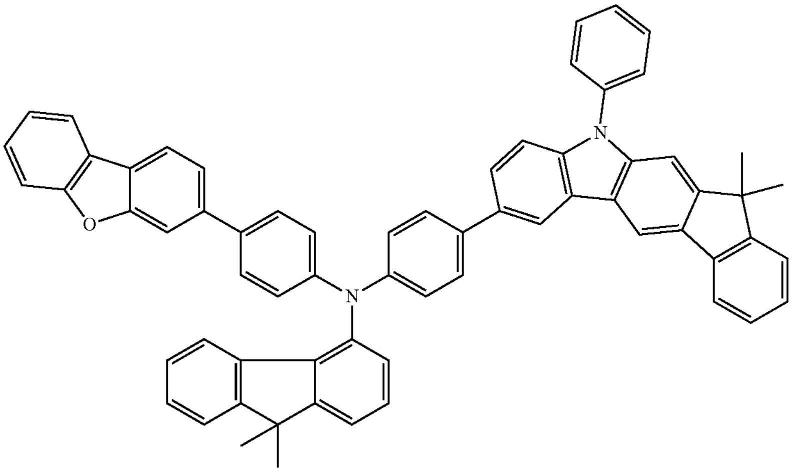 [SMILES: CC1(C)c2ccccc2-c2cc3c4cc(-c5ccc(N(c6ccc(-c7ccc8c(c7)oc7ccccc78)cc6)c6cccc7c6-c6ccccc6C7(C)C)cc5)ccc4n(-c4ccccc4)c3cc21]
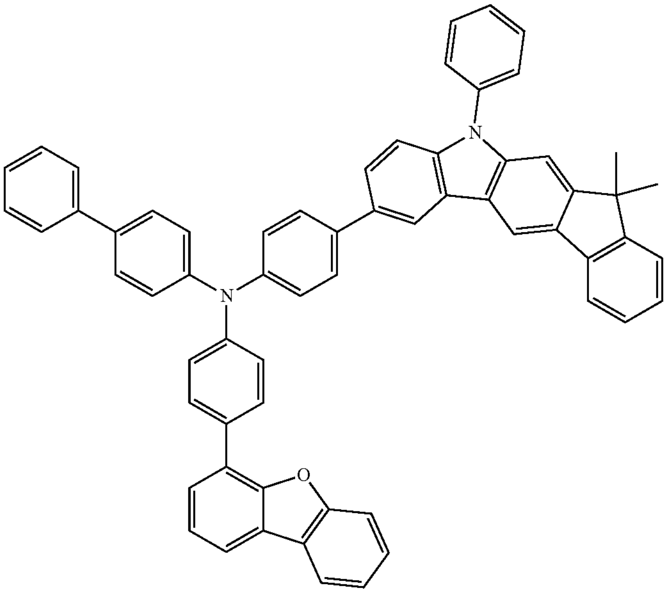 [SMILES: CC1(C)c2ccccc2-c2cc3c4cc(-c5ccc(N(c6ccc(-c7ccccc7)cc6)c6ccc(-c7cccc8c7oc7ccccc78)cc6)cc5)ccc4n(-c4ccccc4)c3cc21]
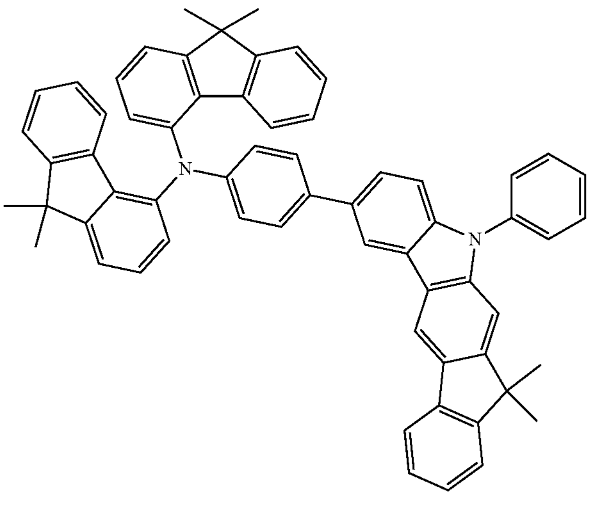 [SMILES: CC1(C)c2ccccc2-c2cc3c4cc(-c5ccc(N(c6cccc7c6-c6ccccc6C7(C)C)c6cccc7c6-c6ccccc6C7(C)C)cc5)ccc4n(-c4ccccc4)c3cc21]

TABLE 3-continued
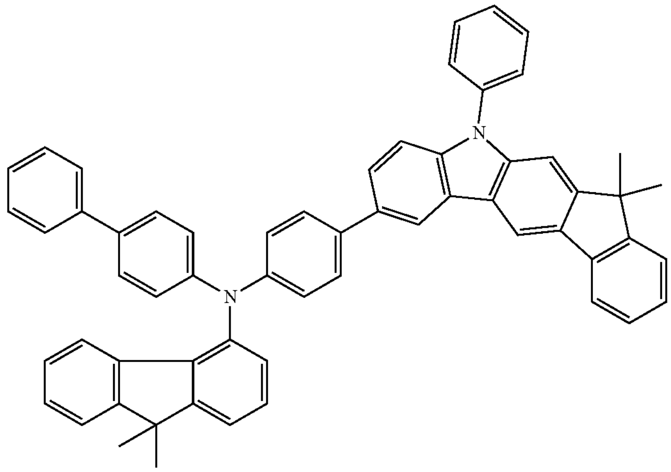 [SMILES: CC1(C)c2ccccc2-c2cc3c4cc(-c5ccc(N(c6ccc(-c7ccccc7)cc6)c6cccc7c6-c6ccccc6C7(C)C)cc5)ccc4n(-c4ccccc4)c3cc21]
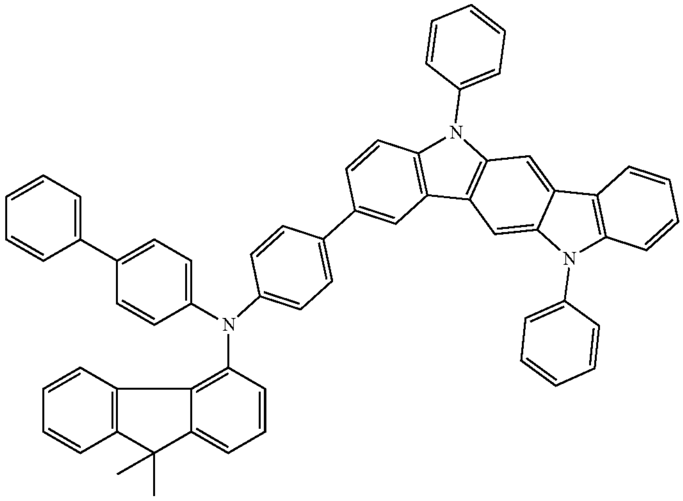 [SMILES: CC1(C)c2ccccc2-c2c(N(c3ccc(-c4ccccc4)cc3)c3ccc(-c4ccc5c(c4)c4cc6c(cc4n5-c4ccccc4)c4ccccc4n6-c4ccccc4)cc3)cccc21]
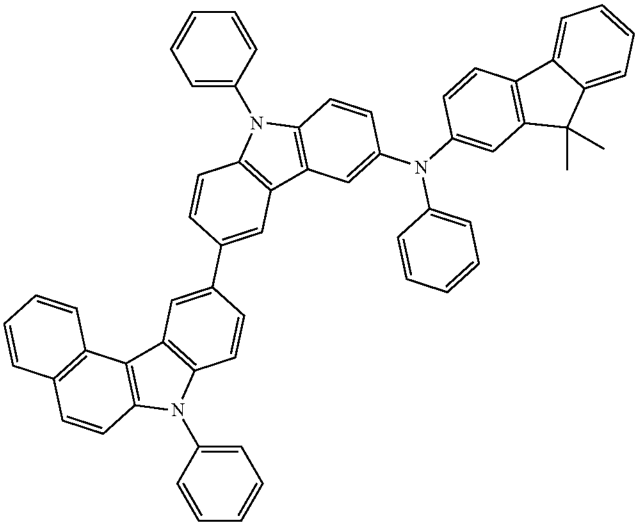 [SMILES: CC1(C)c2ccccc2-c2ccc(N(c3ccccc3)c3ccc4c(c3)c3cc(-c5ccc6c(c5)c5c7ccccc7ccc5n6-c5ccccc5)ccc3n4-c3ccccc3)cc21]

TABLE 3-continued
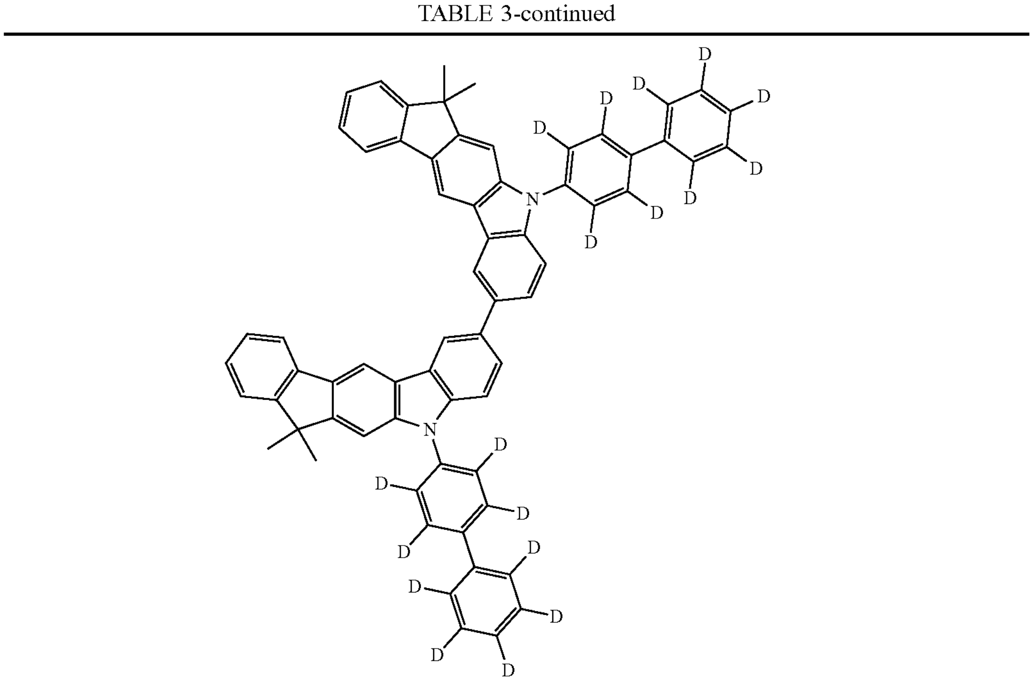
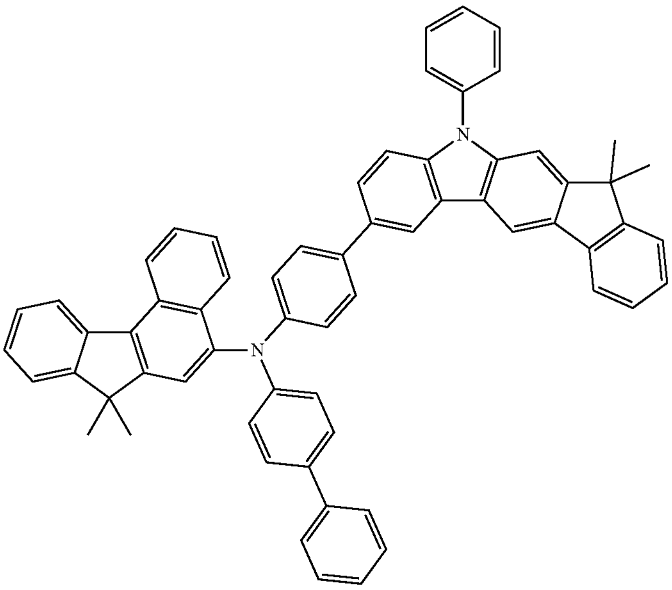 [SMILES: CC1(C)c2ccccc2-c2cc3c4cc(-c5ccc(N(c6ccc(-c7ccccc7)cc6)c6cc7c(c8ccccc68)-c6ccccc6C7(C)C)cc5)ccc4n(-c4ccccc4)c3cc21]

TABLE 3-continued
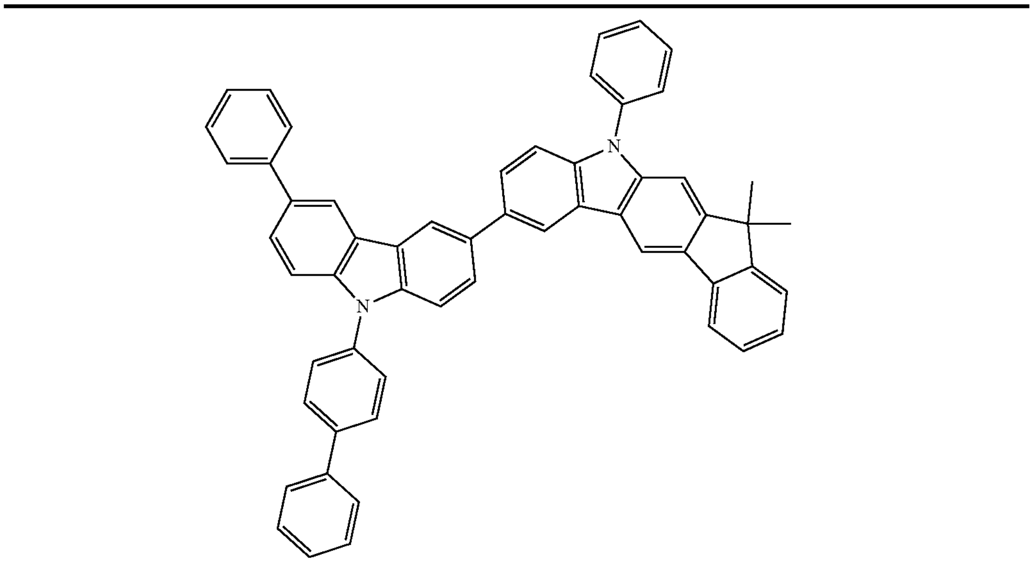
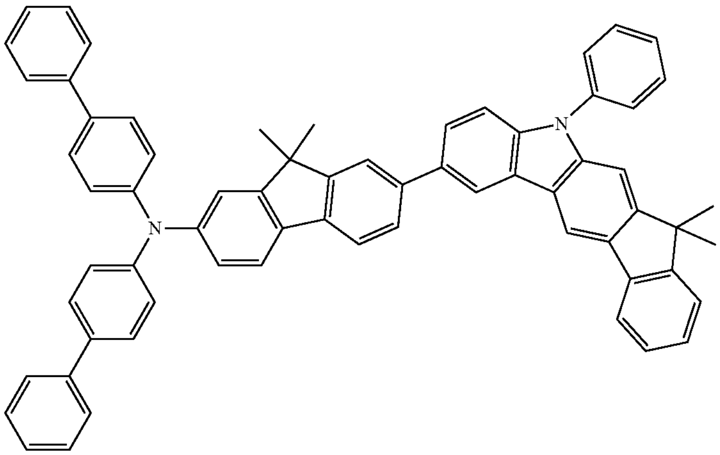 [SMILES: CC1(C)c2cc(-c3ccc4c(c3)c3cc5c(cc3n4-c3ccccc3)C(C)(C)c3ccccc3-5)ccc2-c2ccc(N(c3ccc(-c4ccccc4)cc3)c3ccc(-c4ccccc4)cc3)cc21]
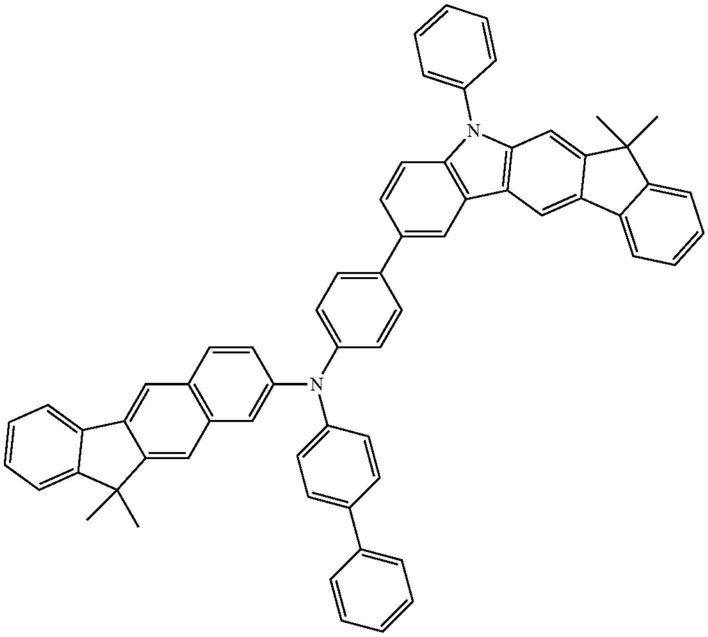 [SMILES: CC1(C)c2ccccc2-c2cc3ccc(N(c4ccc(-c5ccccc5)cc4)c4ccc(-c5ccc6c(c5)c5cc7c(cc5n6-c5ccccc5)C(C)(C)c5ccccc5-7)cc4)cc3cc21]

TABLE 3-continued
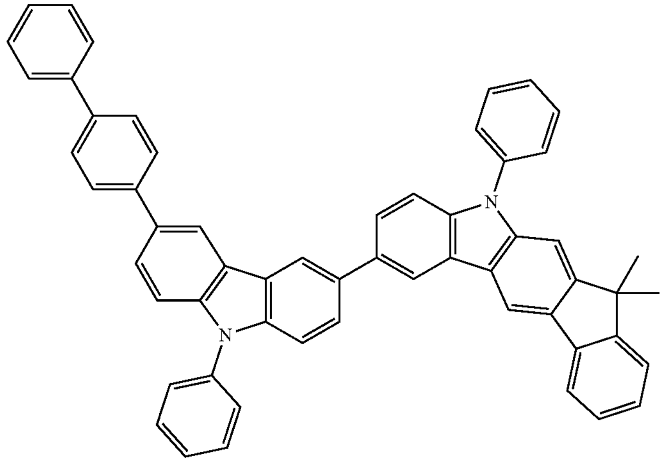 [SMILES: CC1(C)c2ccccc2-c2cc3c4cc(-c5ccc6c(c5)c5cc(-c7ccc(-c8ccccc8)cc7)ccc5n6-c5ccccc5)ccc4n(-c4ccccc4)c3cc21]
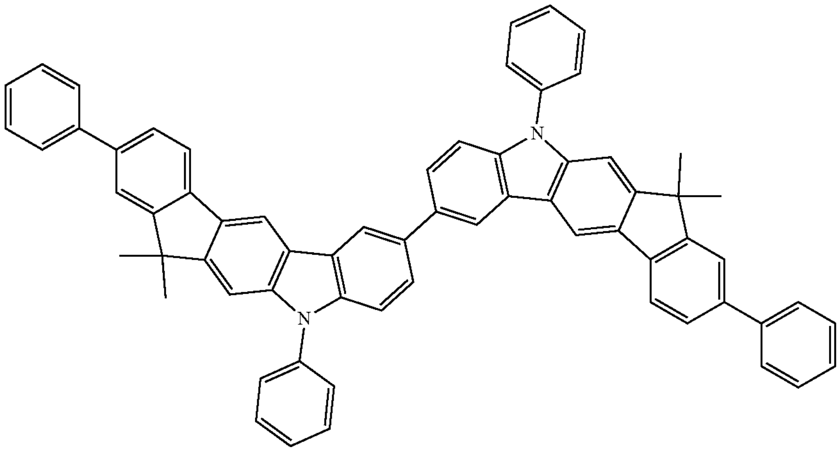 [SMILES: CC1(C)c2cc(-c3ccccc3)ccc2-c2cc3c4cc(-c5ccc6c(c5)c5cc7c(cc5n6-c5ccccc5)C(C)(C)c5cc(-c6ccccc6)ccc5-7)ccc4n(-c4ccccc4)c3cc21]
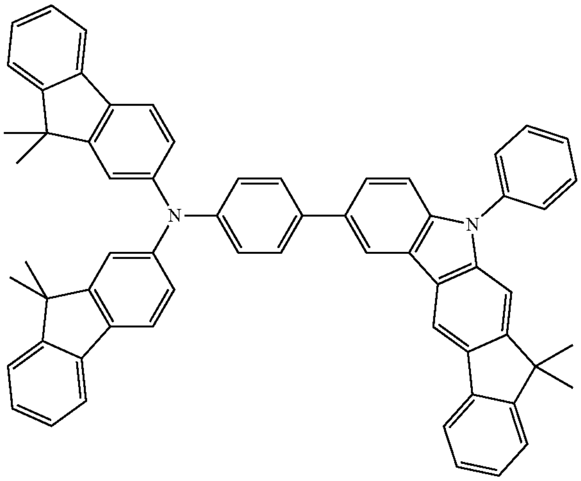 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3ccc4c(c3)C(C)(C)c3ccccc3-4)cc21]

TABLE 3-continued
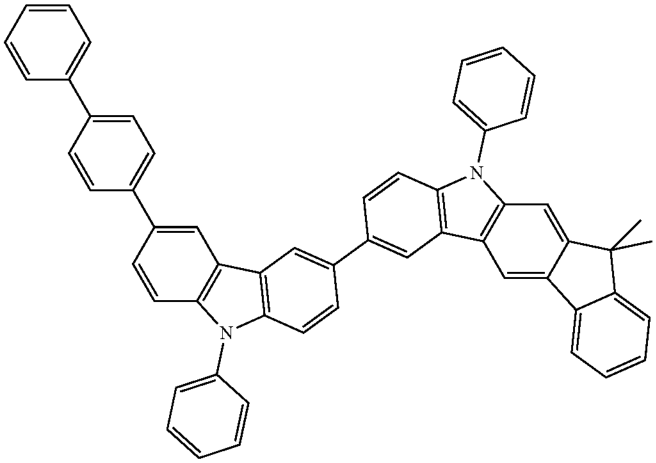 [SMILES: CC1(C)c2ccccc2-c2cc3c4cc(-c5ccc6c(c5)c5cc(-c7ccc(-c8ccccc8)cc7)ccc5n6-c5ccccc5)ccc4n(-c4ccccc4)c3cc21]
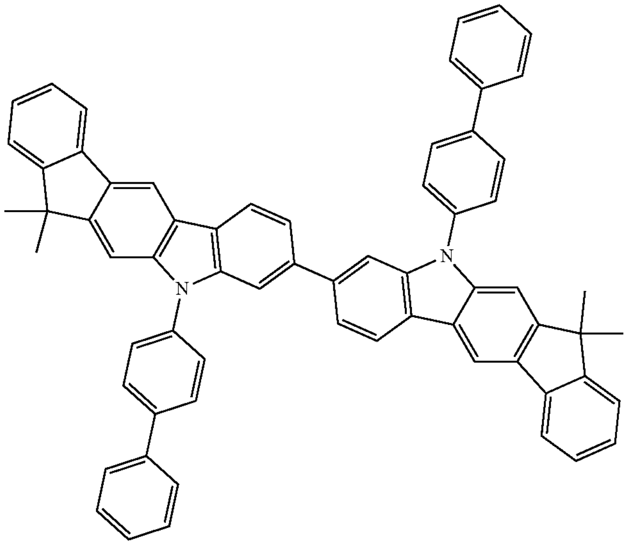
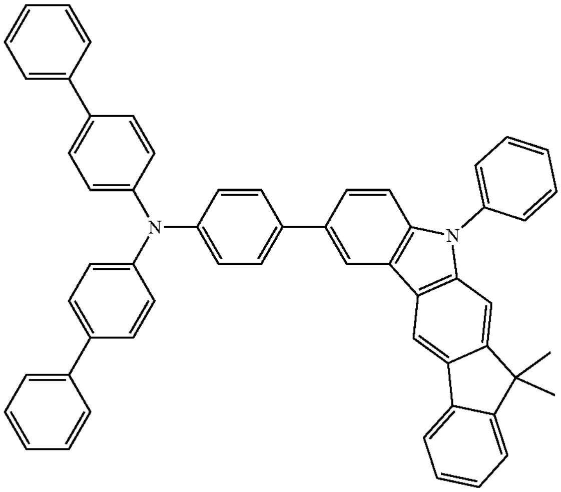 [SMILES: CC1(C)c2ccccc2-c2cc3c4cc(-c5ccc(N(c6ccc(-c7ccccc7)cc6)c6ccc(-c7ccccc7)cc6)cc5)ccc4n(-c4ccccc4)c3cc21]

TABLE 3-continued
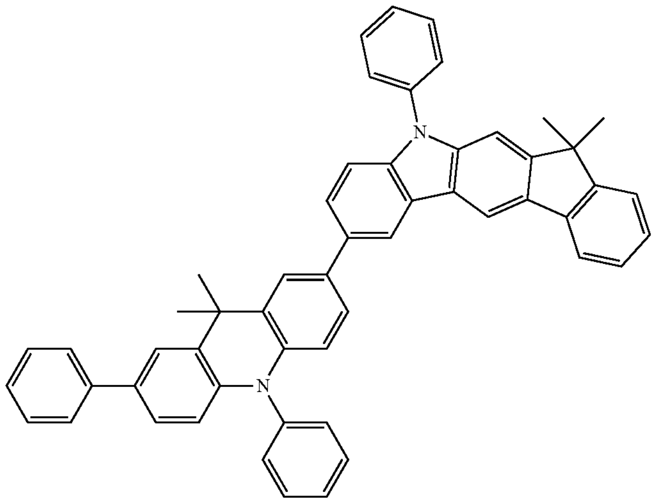 [SMILES: CC1(C)c2ccccc2-c2cc3c4cc(-c5ccc6c(c5)C(C)(C)c5cc(-c7ccccc7)ccc5N6c5ccccc5)ccc4n(-c4ccccc4)c3cc21]
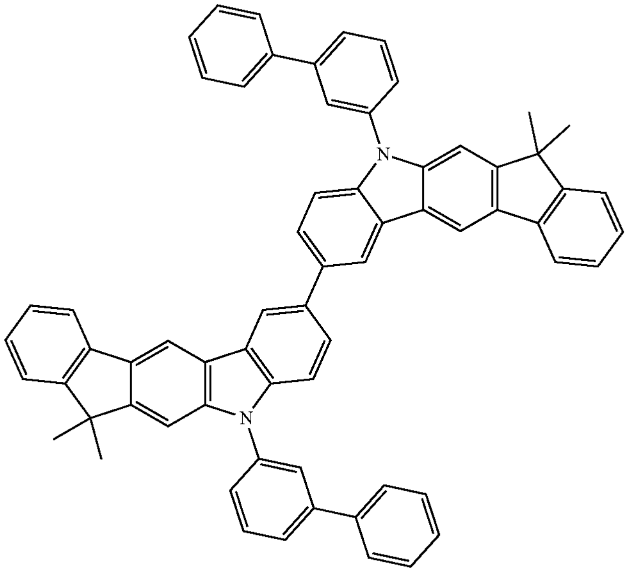 [SMILES: CC1(C)c2ccccc2-c2cc3c4cc(-c5ccc6c(c5)c5cc7c(cc5n6-c5cccc(-c6ccccc6)c5)C(C)(C)c5ccccc5-7)ccc4n(-c4cccc(-c5ccccc5)c4)c3cc21]
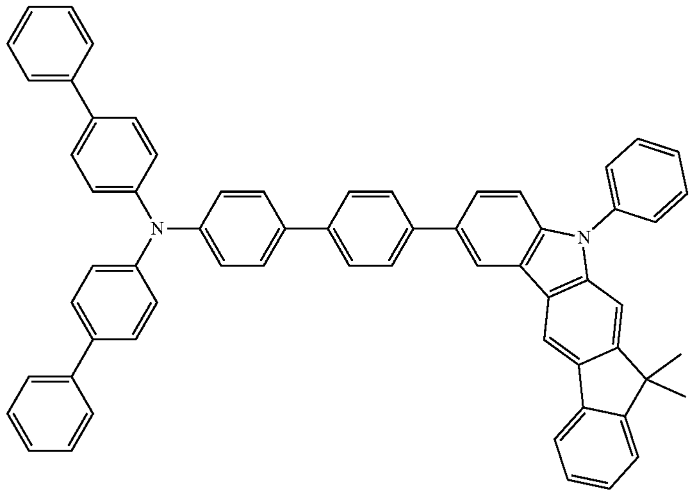 [SMILES: CC1(C)c2ccccc2-c2cc3c4cc(-c5ccc(-c6ccc(N(c7ccc(-c8ccccc8)cc7)c7ccc(-c8ccccc8)cc7)cc6)cc5)ccc4n(-c4ccccc4)c3cc21]

TABLE 3-continued
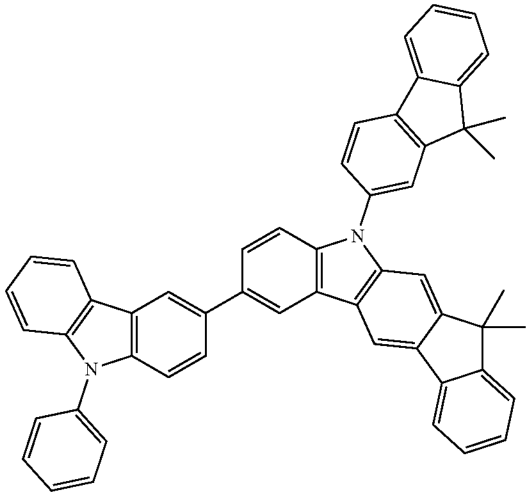 [SMILES: CC1(C)c2ccccc2-c2ccc(-n3c4ccc(-c5ccc6c(c5)c5ccccc5n6-c5ccccc5)cc4c4cc5c(cc43)C(C)(C)c3ccccc3-5)cc21]
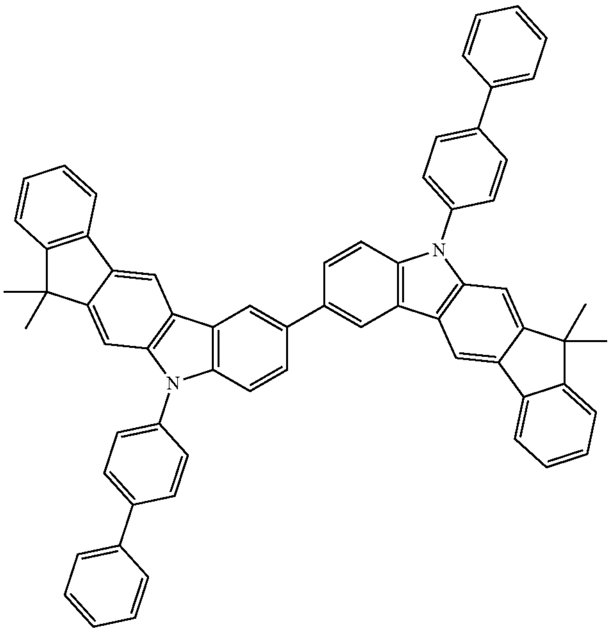
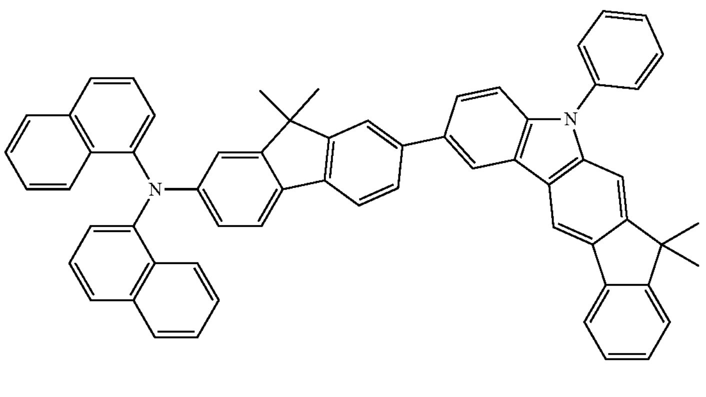 [SMILES: CC1(C)c2cc(-c3ccc4c(c3)c3cc5c(cc3n4-c3ccccc3)C(C)(C)c3ccccc3-5)ccc2-c2ccc(N(c3cccc4ccccc34)c3cccc4ccccc34)cc21]

TABLE 3-continued
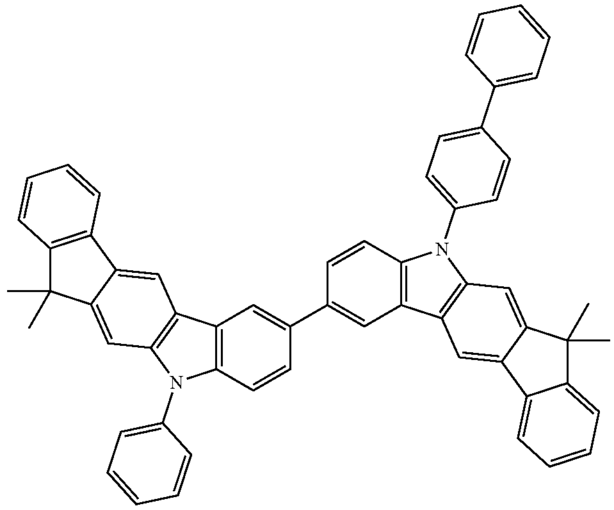
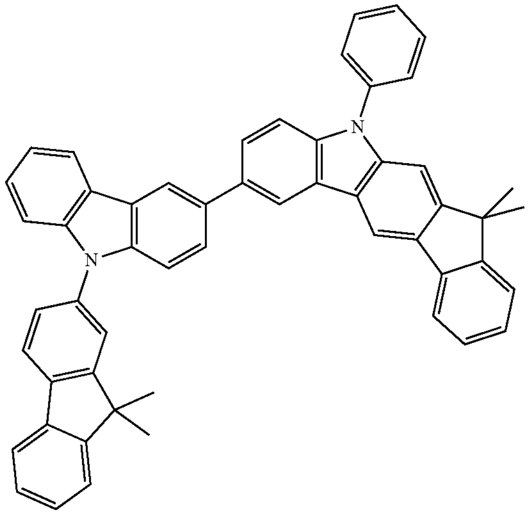 [SMILES: CC1(C)c2ccccc2-c2ccc(-n3c4ccccc4c4cc(-c5ccc6c(c5)c5cc7c(cc5n6-c5ccccc5)C(C)(C)c5ccccc5-7)ccc43)cc21]
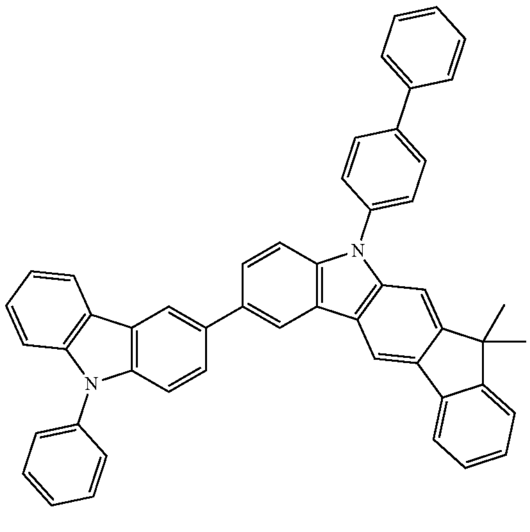 [SMILES: CC1(C)c2ccccc2-c2cc3c4cc(-c5ccc6c(c5)c5ccccc5n6-c5ccccc5)ccc4n(-c4ccc(-c5ccccc5)cc4)c3cc21]

TABLE 3-continued
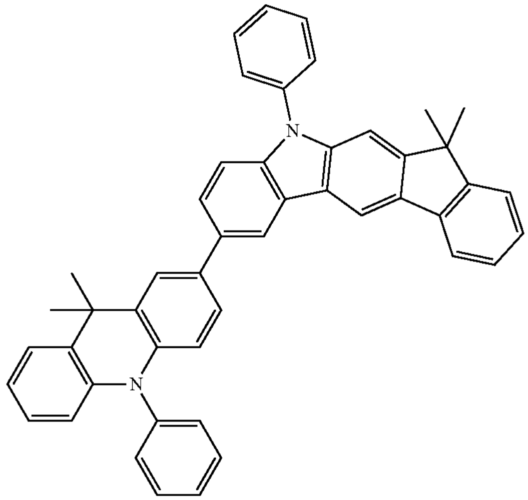 [SMILES: CC1(C)c2ccccc2-c2cc3c4cc(-c5ccc6c(c5)C(C)(C)c5ccccc5N6c5ccccc5)ccc4n(-c4ccccc4)c3cc21]
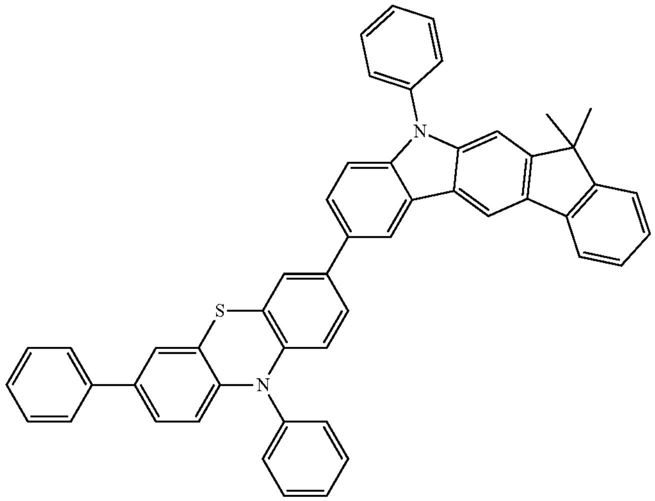 [SMILES: CC1(C)c2ccccc2-c2cc3c4cc(-c5ccc6c(c5)Sc5cc(-c7ccccc7)ccc5N6c5ccccc5)ccc4n(-c4ccccc4)c3cc21]
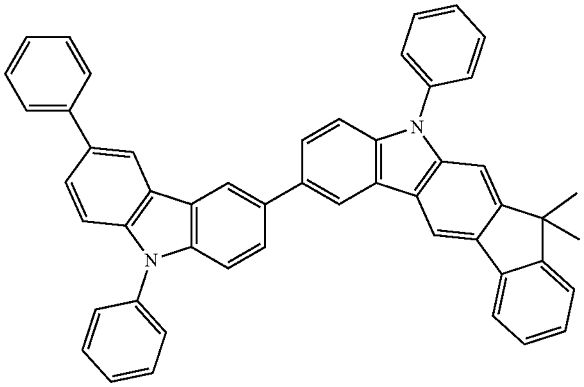 [SMILES: CC1(C)c2ccccc2-c2cc3c4cc(-c5ccc6c(c5)c5cc(-c7ccccc7)ccc5n6-c5ccccc5)ccc4n(-c4ccccc4)c3cc21]

TABLE 3-continued
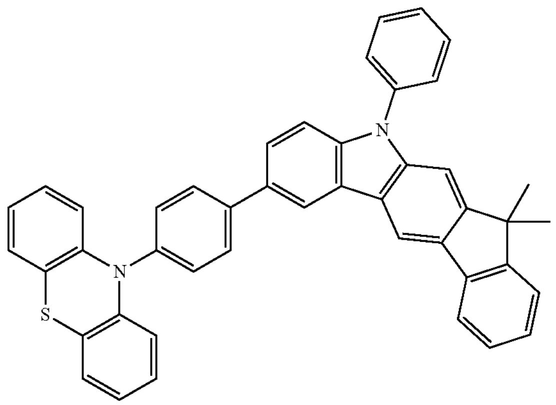 [SMILES: CC1(C)c2ccccc2-c2cc3c4cc(-c5ccc(N6c7ccccc7Sc7ccccc76)cc5)ccc4n(-c4ccccc4)c3cc21]
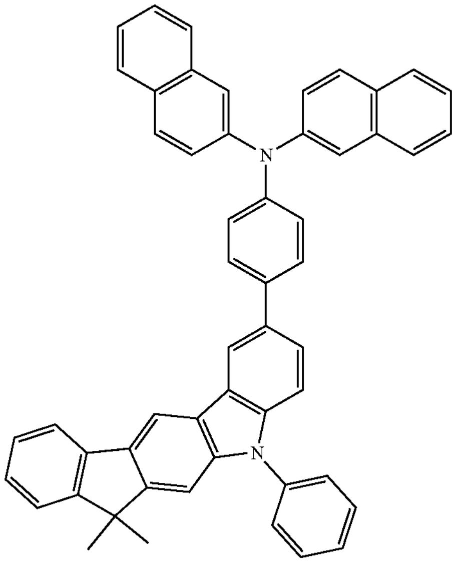 [SMILES: CC1(C)c2ccccc2-c2cc3c4cc(-c5ccc(N(c6ccc7ccccc7c6)c6ccc7ccccc7c6)cc5)ccc4n(-c4ccccc4)c3cc21]
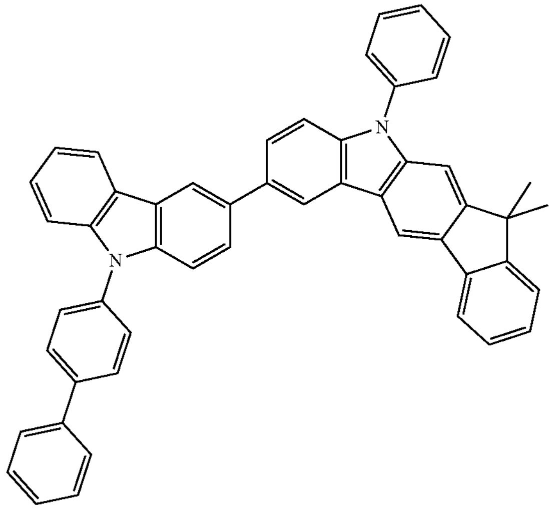 [SMILES: CC1(C)c2ccccc2-c2cc3c4cc(-c5ccc6c(c5)c5ccccc5n6-c5ccc(-c6ccccc6)cc5)ccc4n(-c4ccccc4)c3cc21]

TABLE 3-continued
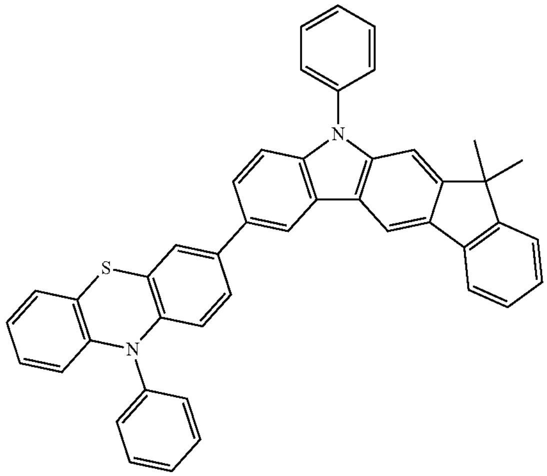 [SMILES: CC1(C)c2ccccc2-c2cc3c4cc(-c5ccc6c(c5)Sc5ccccc5N6c5ccccc5)ccc4n(-c4ccccc4)c3cc21]
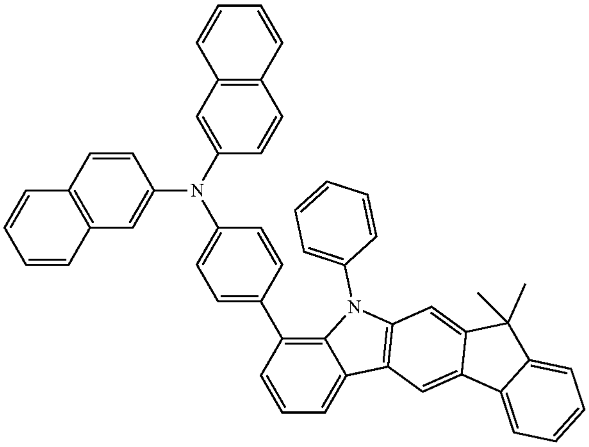 [SMILES: CC1(C)c2ccccc2-c2cc3c4cccc(-c5ccc(N(c6ccc7ccccc7c6)c6ccc7ccccc7c6)cc5)c4n(-c4ccccc4)c3cc21]
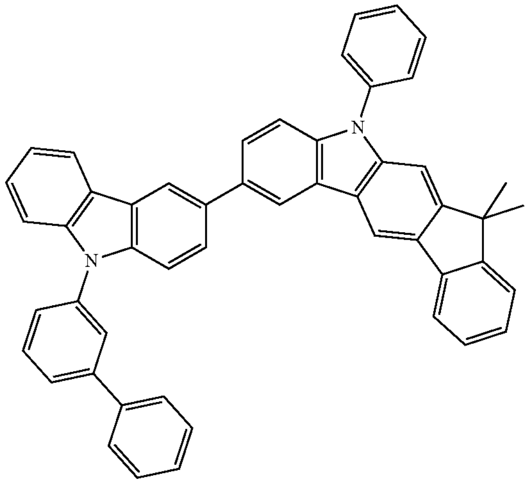 [SMILES: CC1(C)c2ccccc2-c2cc3c4cc(-c5ccc6c(c5)c5ccccc5n6-c5cccc(-c6ccccc6)c5)ccc4n(-c4ccccc4)c3cc21]

TABLE 3-continued
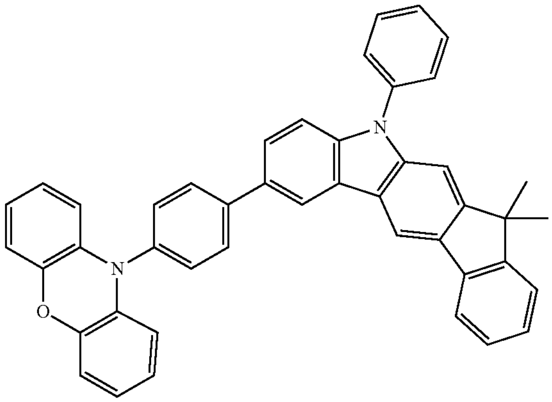 [SMILES: CC1(C)c2ccccc2-c2cc3c4cc(-c5ccc(N6c7ccccc7Oc7ccccc76)cc5)ccc4n(-c4ccccc4)c3cc21]
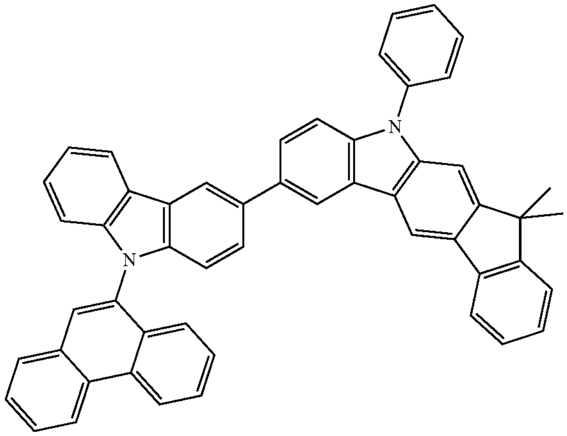 [SMILES: CC1(C)c2ccccc2-c2cc3c4cc(-c5ccc6c(c5)c5ccccc5n6-c5cc6ccccc6c6ccccc56)ccc4n(-c4ccccc4)c3cc21]
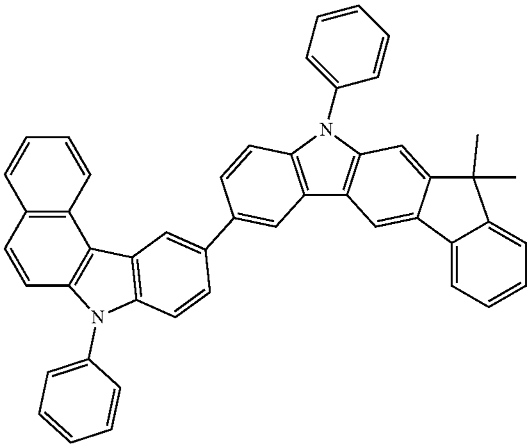 [SMILES: CC1(C)c2ccccc2-c2cc3c4cc(-c5ccc6c(c5)c5c7ccccc7ccc5n6-c5ccccc5)ccc4n(-c4ccccc4)c3cc21]

TABLE 3-continued
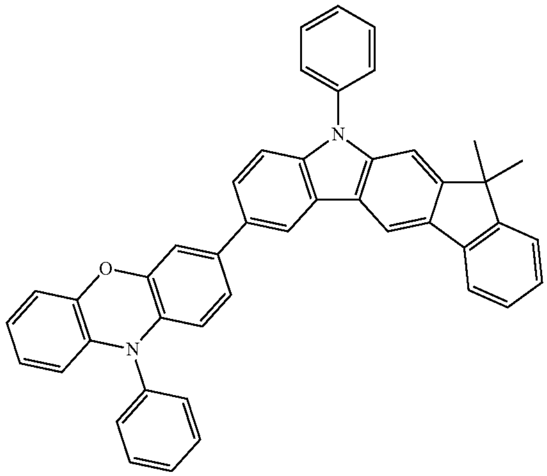 [SMILES: CC1(C)c2ccccc2-c2cc3c4cc(-c5ccc6c(c5)Oc5ccccc5N6c5ccccc5)ccc4n(-c4ccccc4)c3cc21]
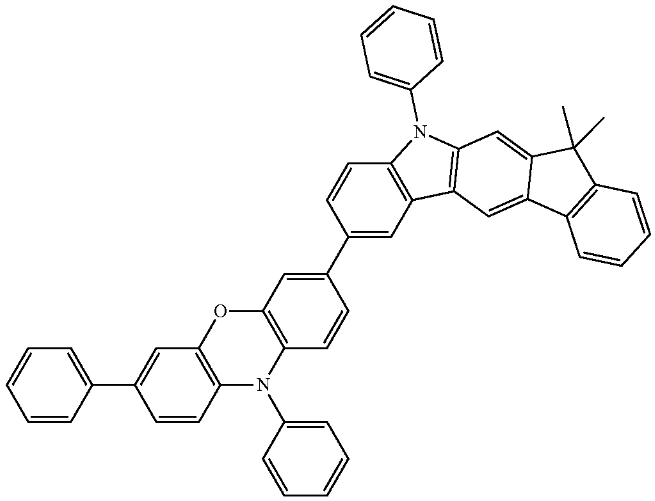 [SMILES: CC1(C)c2ccccc2-c2cc3c4cc(-c5ccc6c(c5)Oc5cc(-c7ccccc7)ccc5N6c5ccccc5)ccc4n(-c4ccccc4)c3cc21]
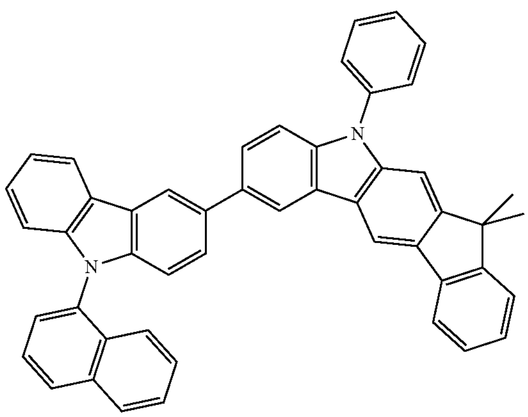 [SMILES: CC1(C)c2ccccc2-c2cc3c4cc(-c5ccc6c(c5)c5ccccc5n6-c5cccc6ccccc56)ccc4n(-c4ccccc4)c3cc21]

TABLE 3-continued
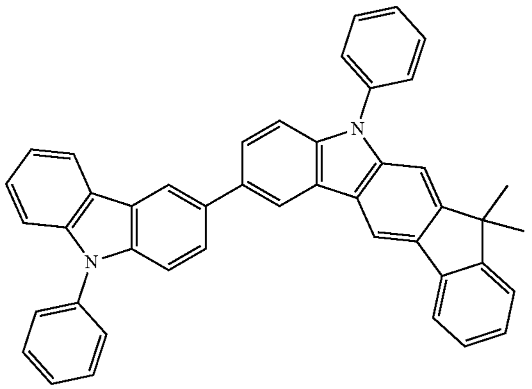 [SMILES: CC1(C)c2ccccc2-c2cc3c4cc(-c5ccc6c(c5)c5ccccc5n6-c5ccccc5)ccc4n(-c4ccccc4)c3cc21]
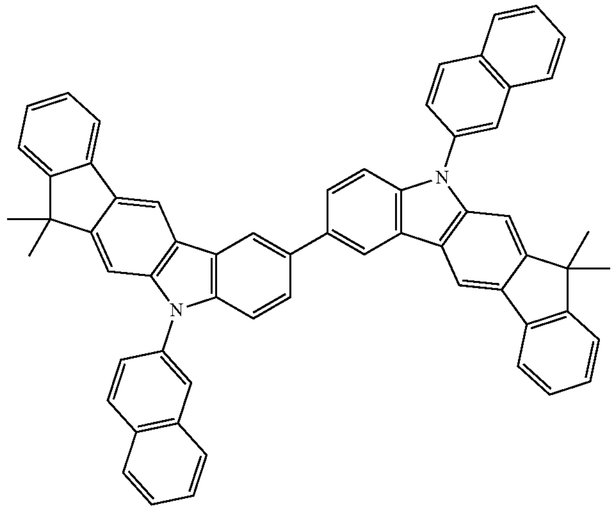
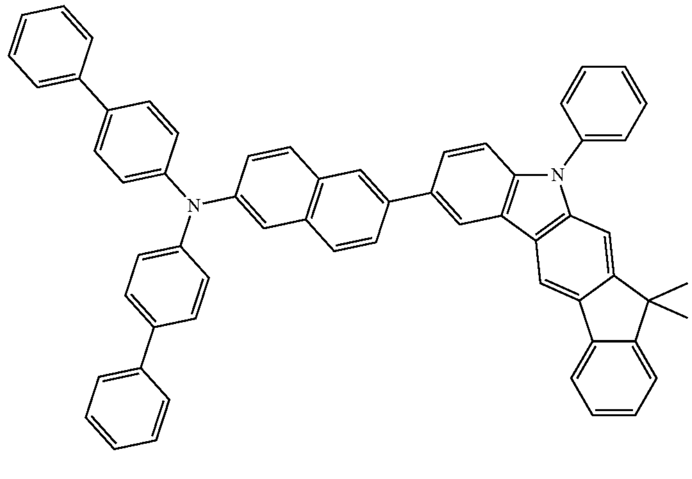 [SMILES: CC1(C)c2ccccc2-c2cc3c4cc(-c5ccc6cc(N(c7ccc(-c8ccccc8)cc7)c7ccc(-c8ccccc8)cc7)ccc6c5)ccc4n(-c4ccccc4)c3cc21]

TABLE 3-continued
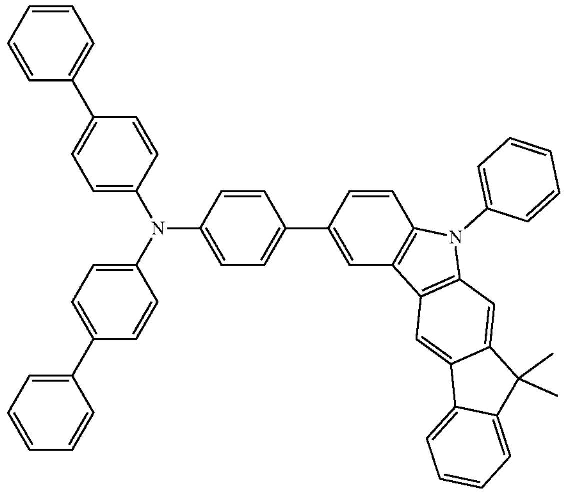 [SMILES: CC1(C)c2ccccc2-c2cc3c4cc(-c5ccc(N(c6ccc(-c7ccccc7)cc6)c6ccc(-c7ccccc7)cc6)cc5)ccc4n(-c4ccccc4)c3cc21]
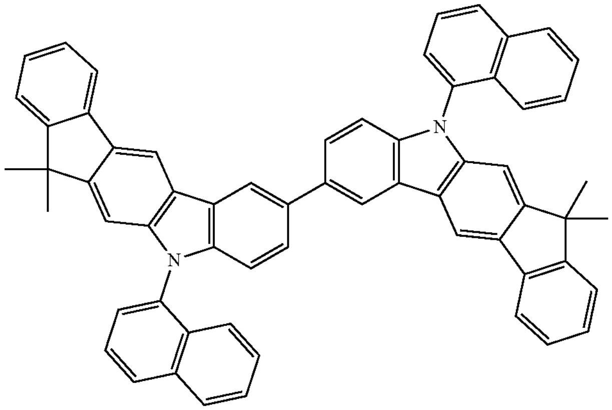
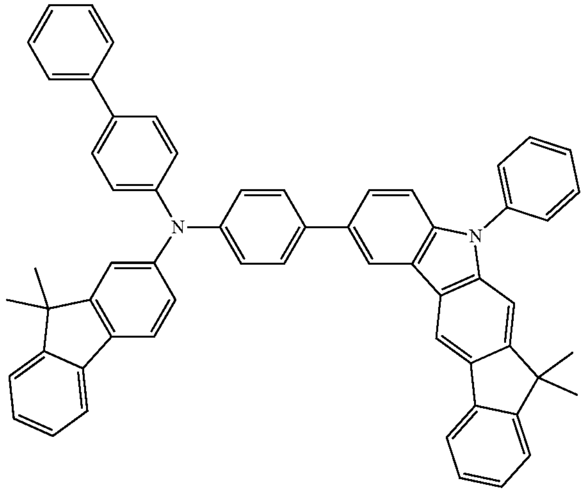 [SMILES: CC1(C)c2ccccc2-c2ccc(N(c3ccc(-c4ccccc4)cc3)c3ccc(-c4ccc5c(c4)c4cc6c(cc4n5-c4ccccc4)C(C)(C)c4ccccc4-6)cc3)cc21]

TABLE 3-continued
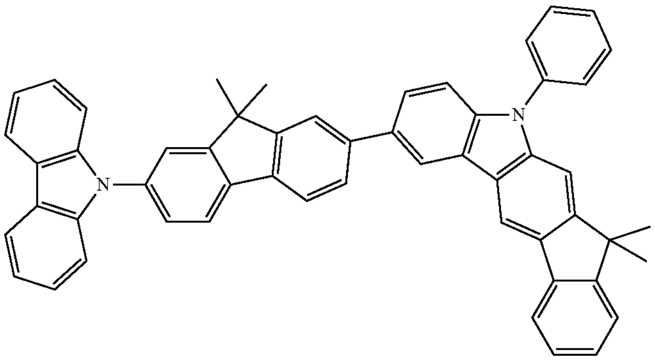 [SMILES: CC1(C)c2cc(-c3ccc4c(c3)c3cc5c(cc3n4-c3ccccc3)C(C)(C)c3ccccc3-5)ccc2-c2ccc(-n3c4ccccc4c4ccccc43)cc21]
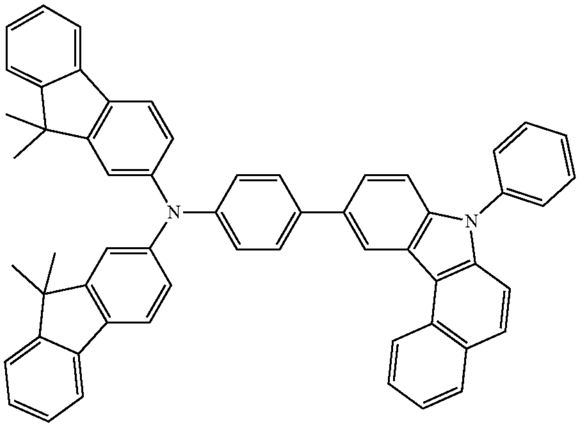 [SMILES: CC1(C)c2ccccc2-c2ccc(N(c3ccc(-c4ccc5c(c4)c4c6ccccc6ccc4n5-c4ccccc4)cc3)c3ccc4c(c3)C(C)(C)c3ccccc3-4)cc21]
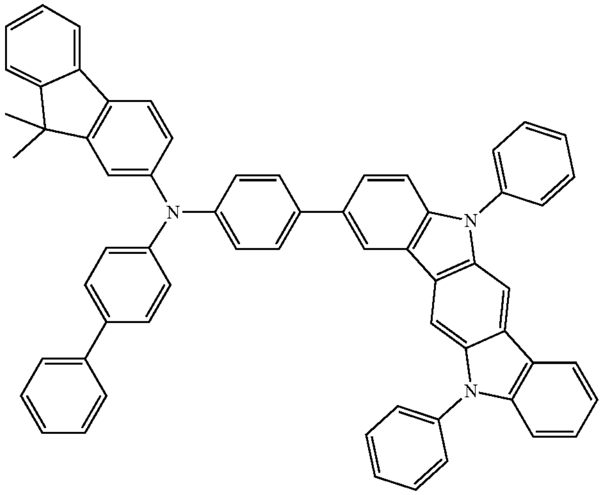 [SMILES: CC1(C)c2ccccc2-c2ccc(N(c3ccc(-c4ccccc4)cc3)c3ccc(-c4ccc5c(c4)c4cc6c(cc4n5-c4ccccc4)c4ccccc4n6-c4ccccc4)cc3)cc21]

TABLE 3-continued
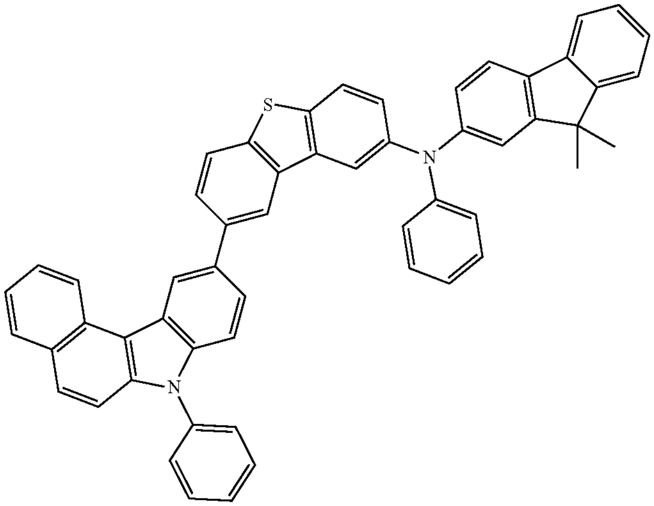 [SMILES: CC1(C)c2ccccc2-c2ccc(N(c3ccccc3)c3ccc4sc5ccc(-c6ccc7c(c6)c6c8ccccc8ccc6n7-c6ccccc6)cc5c4c3)cc21]
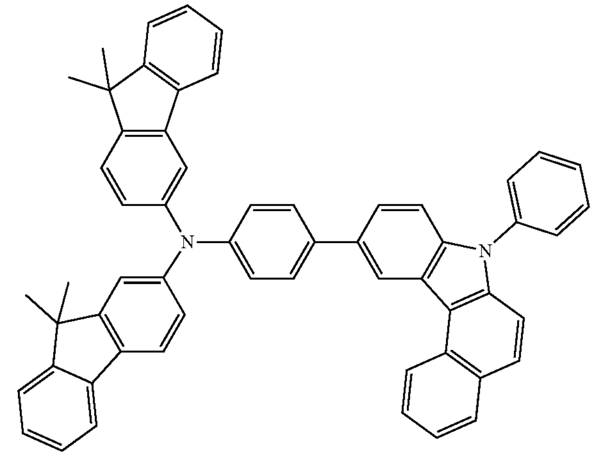 [SMILES: CC1(C)c2ccccc2-c2cc(N(c3ccc(-c4ccc5c(c4)c4c6ccccc6ccc4n5-c4ccccc4)cc3)c3ccc4c(c3)C(C)(C)c3ccccc3-4)ccc21]
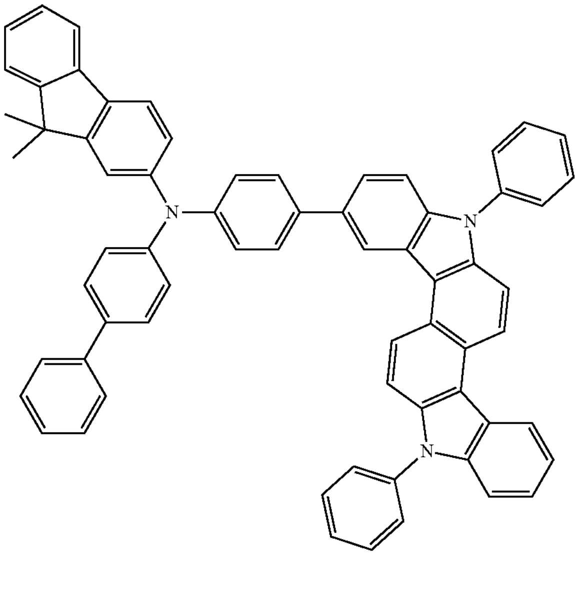 [SMILES: CC1(C)c2ccccc2-c2ccc(N(c3ccc(-c4ccccc4)cc3)c3ccc(-c4ccc5c(c4)c4c6ccc7c(c6ccc4n5-c4ccccc4)c4ccccc4n7-c4ccccc4)cc3)cc21]

TABLE 3-continued
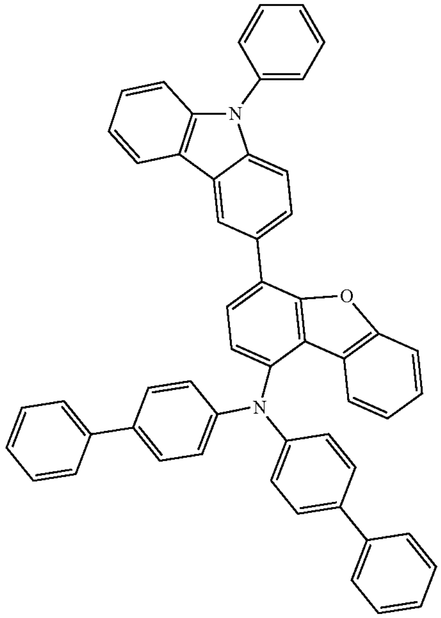 [SMILES: c1ccc(-c2ccc(N(c3ccc(-c4ccccc4)cc3)c3ccc(-c4ccc5c(c4)c4ccccc4n5-c4ccccc4)c4oc5ccccc5c34)cc2)cc1]
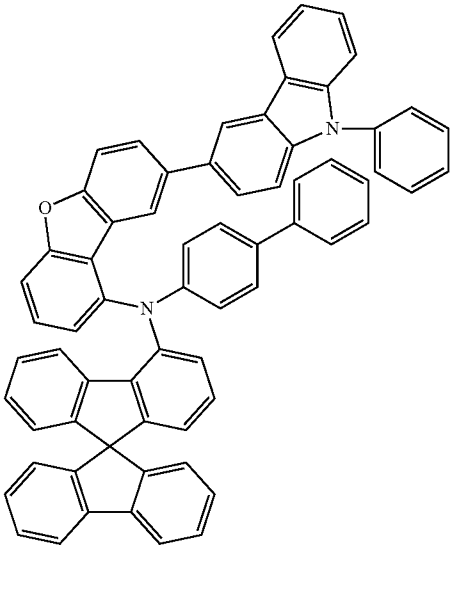 [SMILES: c1ccc(-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc2)cc1]

TABLE 3-continued
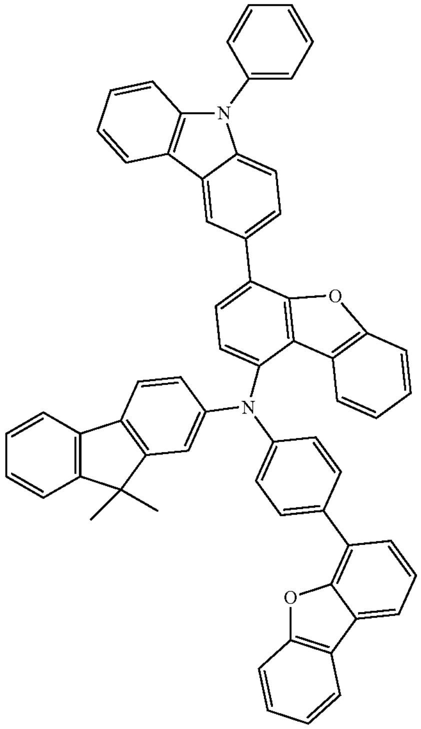 [SMILES: CC1(C)c2ccccc2-c2ccc(N(c3ccc(-c4cccc5c4oc4ccccc45)cc3)c3ccc(-c4ccc5c(c4)c4ccccc4n5-c4ccccc4)c4oc5ccccc5c34)cc21]
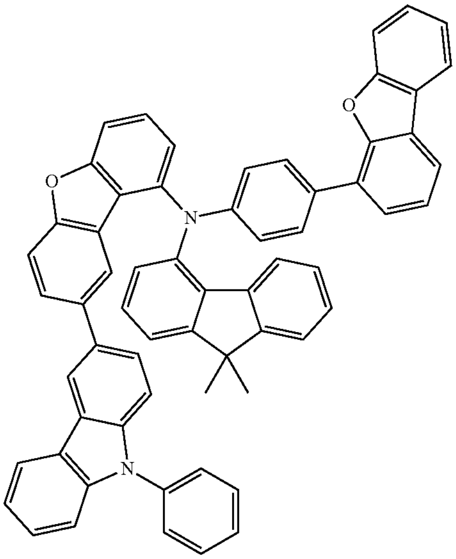 [SMILES: CC1(C)c2ccccc2-c2c(N(c3ccc(-c4cccc5c4oc4ccccc45)cc3)c3cccc4oc5ccc(-c6ccc7c(c6)c6ccccc6n7-c6ccccc6)cc5c34)cccc21]
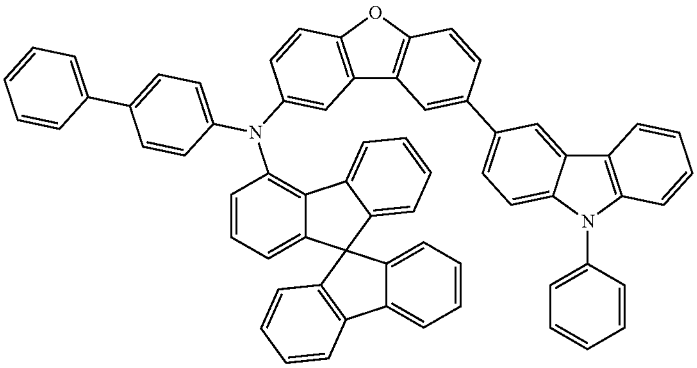 [SMILES: c1ccc(-c2ccc(N(c3ccc4oc5ccc(-c6ccc7c(c6)c6ccccc6n7-c6ccccc6)cc5c4c3)c3cccc4c3-c3ccccc3C43c4ccccc4-c4ccccc43)cc2)cc1]

TABLE 3-continued
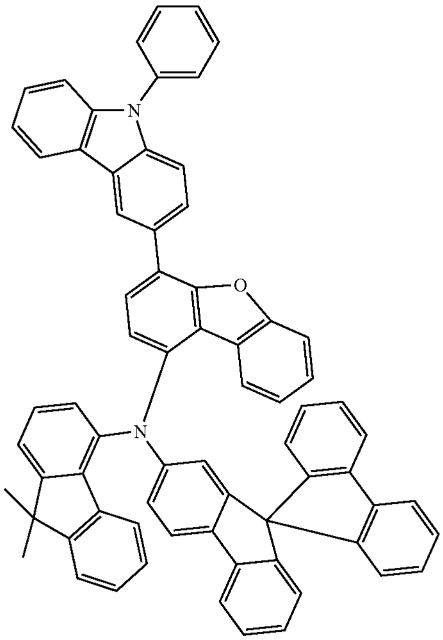
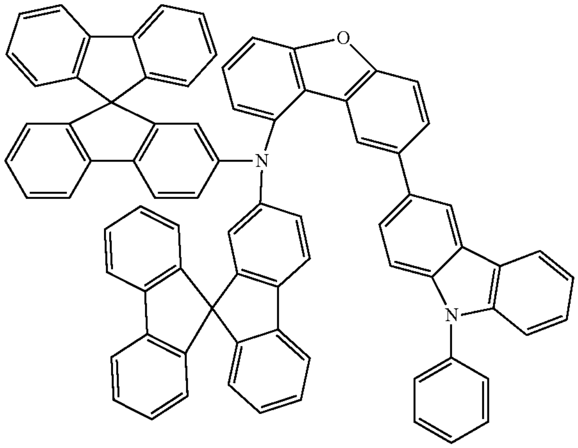 [SMILES: c1ccc(-n2c3ccccc3c3cc(-c4ccc5oc6cccc(N(c7ccc8c(c7)C7(c9ccccc9-c9ccccc97)c7ccccc7-8)c7ccc8c(c7)C7(c9ccccc9-c9ccccc97)c7ccccc7-8)c6c5c4)ccc32)cc1]
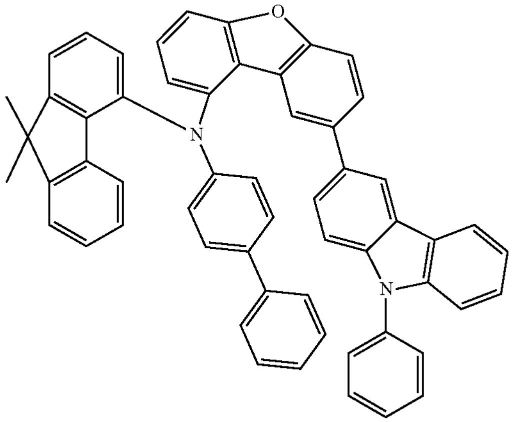 [SMILES: CC1(C)c2ccccc2-c2c(N(c3ccc(-c4ccccc4)cc3)c3cccc4oc5ccc(-c6ccc7c(c6)c6ccccc6n7-c6ccccc6)cc5c34)cccc21]

TABLE 3-continued
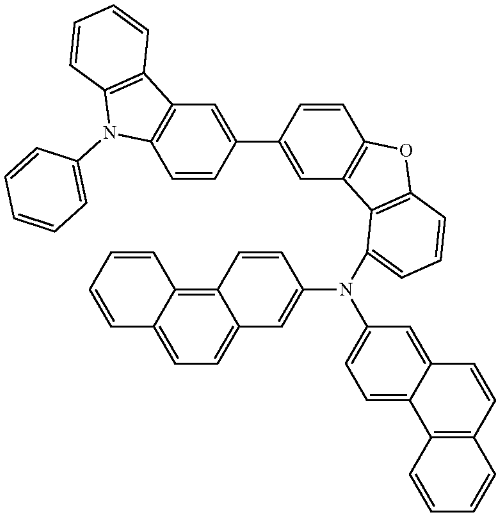 [SMILES: c1ccc(-n2c3ccccc3c3cc(-c4ccc5oc6cccc(N(c7ccc8c(ccc9ccccc98)c7)c7ccc8c(ccc9ccccc98)c7)c6c5c4)ccc32)cc1]
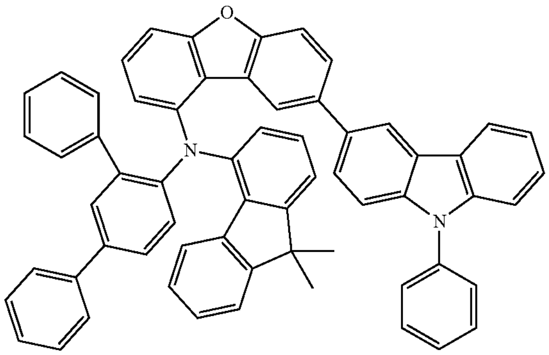 [SMILES: CC1(C)c2ccccc2-c2c(N(c3ccc(-c4ccccc4)cc3-c3ccccc3)c3cccc4oc5ccc(-c6ccc7c(c6)c6ccccc6n7-c6ccccc6)cc5c34)cccc21]
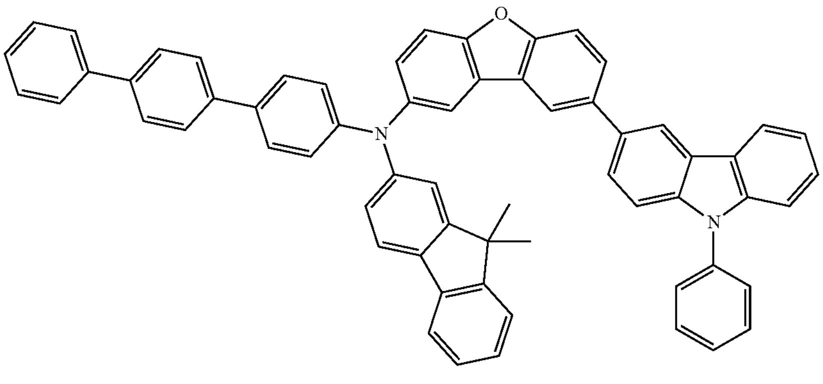 [SMILES: CC1(C)c2ccccc2-c2ccc(N(c3ccc(-c4ccc(-c5ccccc5)cc4)cc3)c3ccc4oc5ccc(-c6ccc7c(c6)c6ccccc6n7-c6ccccc6)cc5c4c3)cc21]

TABLE 3-continued
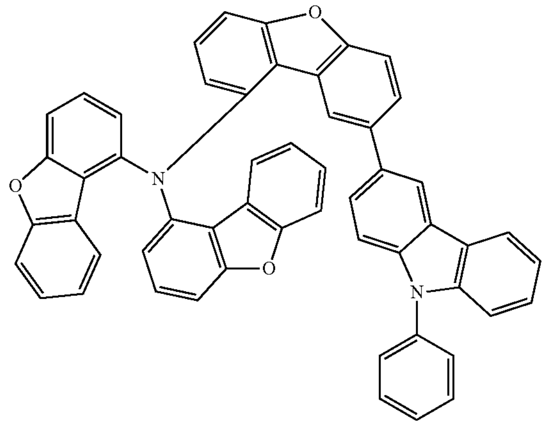 [SMILES: c1ccc(-n2c3ccccc3c3cc(-c4ccc5oc6cccc(N(c7cccc8oc9ccccc9c78)c7cccc8oc9ccccc9c78)c6c5c4)ccc32)cc1]
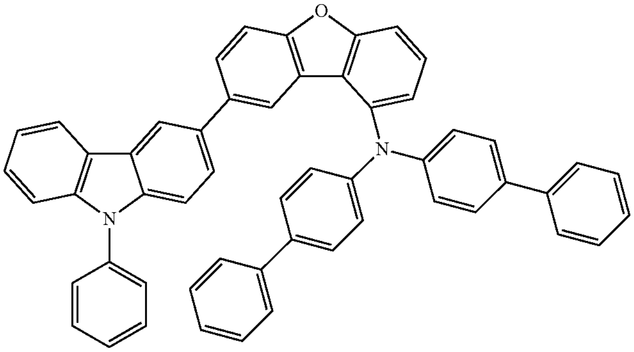 [SMILES: c1ccc(-c2ccc(N(c3ccc(-c4ccccc4)cc3)c3cccc4oc5ccc(-c6ccc7c(c6)c6ccccc6n7-c6ccccc6)cc5c34)cc2)cc1]
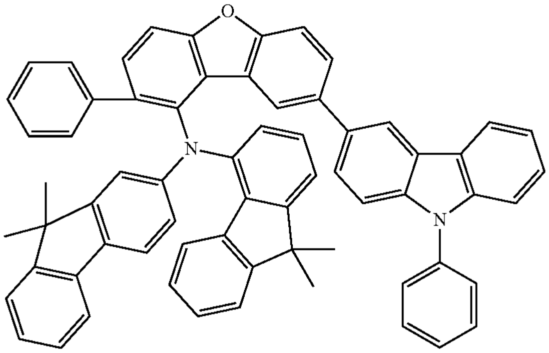 [SMILES: CC1(C)c2ccccc2-c2ccc(N(c3cccc4c3-c3ccccc3C4(C)C)c3c(-c4ccccc4)ccc4oc5ccc(-c6ccc7c(c6)c6ccccc6n7-c6ccccc6)cc5c34)cc21]
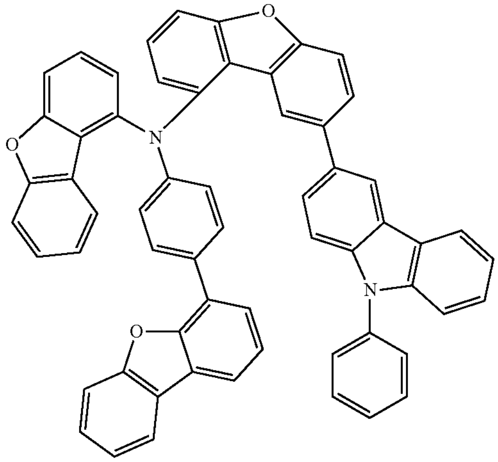 [SMILES: c1ccc(-n2c3ccccc3c3cc(-c4ccc5oc6cccc(N(c7ccc(-c8cccc9c8oc8ccccc89)cc7)c7cccc8oc9ccccc9c78)c6c5c4)ccc32)cc1]

TABLE 3-continued
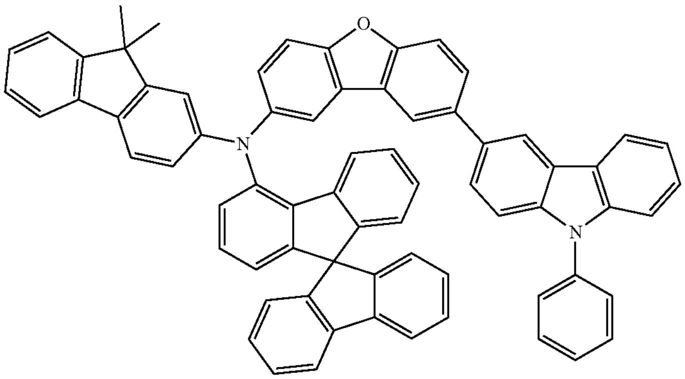 [SMILES: CC1(C)c2ccccc2-c2ccc(N(c3ccc4oc5ccc(-c6ccc7c(c6)c6ccccc6n7-c6ccccc6)cc5c4c3)c3cccc4c3-c3ccccc3C43c4ccccc4-c4ccccc43)cc21]
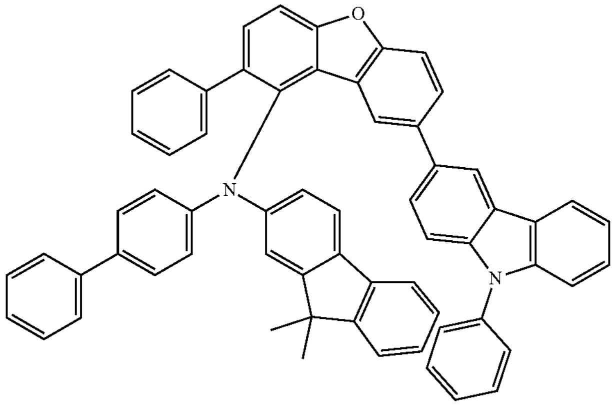 [SMILES: CC1(C)c2ccccc2-c2ccc(N(c3ccc(-c4ccccc4)cc3)c3c(-c4ccccc4)ccc4oc5ccc(-c6ccc7c(c6)c6ccccc6n7-c6ccccc6)cc5c34)cc21]
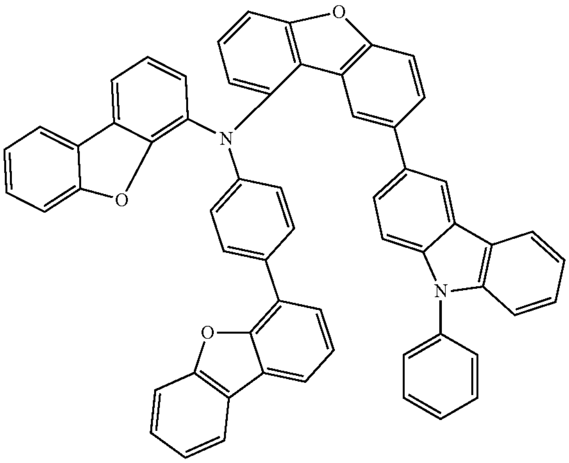 [SMILES: c1ccc(-n2c3ccccc3c3cc(-c4ccc5oc6cccc(N(c7ccc(-c8cccc9c8oc8ccccc89)cc7)c7cccc8c7oc7ccccc78)c6c5c4)ccc32)cc1]

TABLE 3-continued
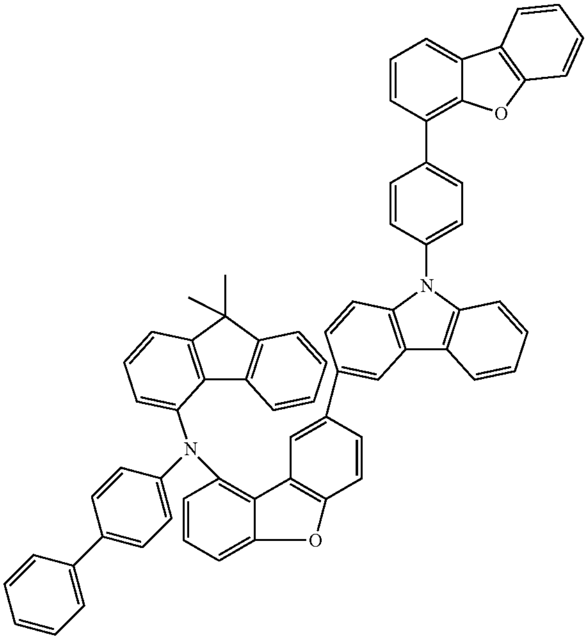 [SMILES: CC1(C)c2ccccc2-c2c(N(c3ccc(-c4ccccc4)cc3)c3cccc4oc5ccc(-c6ccc7c(c6)c6ccccc6n7-c6ccc(-c7cccc8c7oc7ccccc78)cc6)cc5c34)cccc21]
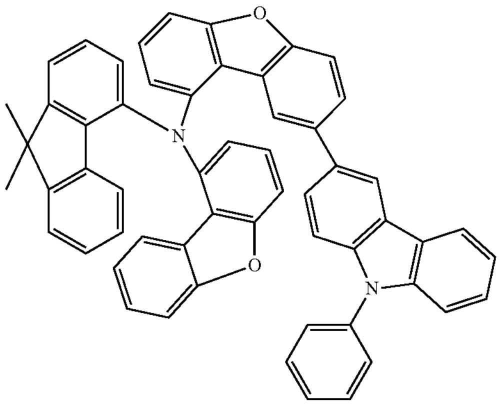 [SMILES: CC1(C)c2ccccc2-c2c(N(c3cccc4oc5ccccc5c34)c3cccc4oc5ccc(-c6ccc7c(c6)c6ccccc6n7-c6ccccc6)cc5c34)cccc21]
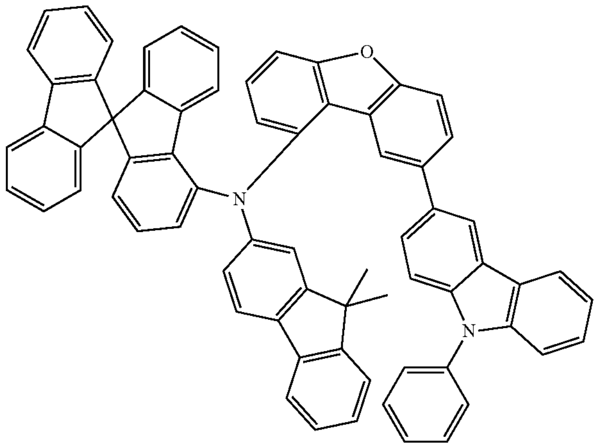 [SMILES: CC1(C)c2ccccc2-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc21]

TABLE 3-continued
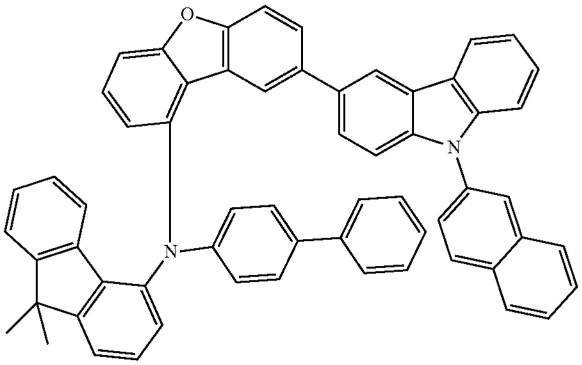 [SMILES: CC1(C)c2ccccc2-c2c(N(c3ccc(-c4ccccc4)cc3)c3cccc4oc5ccc(-c6ccc7c(c6)c6ccccc6n7-c6ccc7ccccc7c6)cc5c34)cccc21]
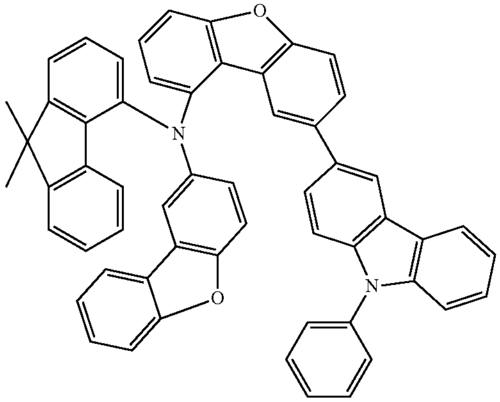 [SMILES: CC1(C)c2ccccc2-c2c(N(c3ccc4oc5ccccc5c4c3)c3cccc4oc5ccc(-c6ccc7c(c6)c6ccccc6n7-c6ccccc6)cc5c34)cccc21]
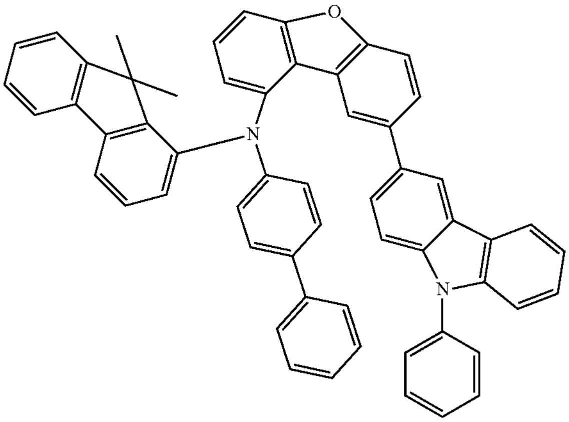 [SMILES: CC1(C)c2ccccc2-c2cccc(N(c3ccc(-c4ccccc4)cc3)c3cccc4oc5ccc(-c6ccc7c(c6)c6ccccc6n7-c6ccccc6)cc5c34)c21]
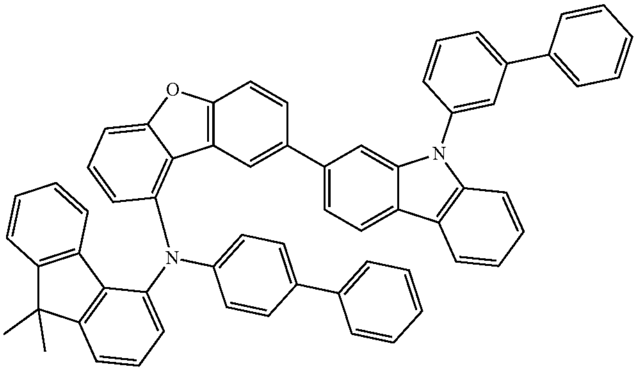 [SMILES: CC1(C)c2ccccc2-c2c(N(c3ccc(-c4ccccc4)cc3)c3cccc4oc5ccc(-c6ccc7c8ccccc8n(-c8cccc(-c9ccccc9)c8)c7c6)cc5c34)cccc21]

TABLE 3-continued
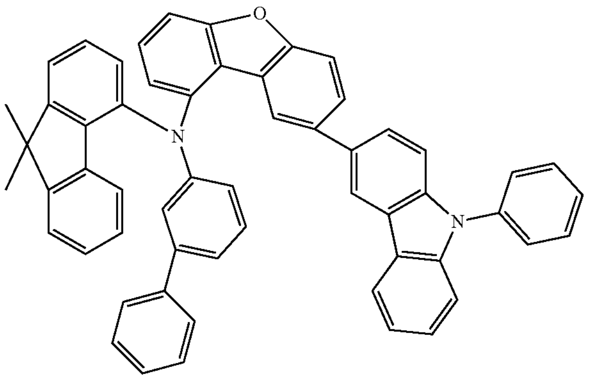 [SMILES: CC1(C)c2ccccc2-c2c(N(c3cccc(-c4ccccc4)c3)c3cccc4oc5ccc(-c6ccc7c(c6)c6ccccc6n7-c6ccccc6)cc5c34)cccc21]
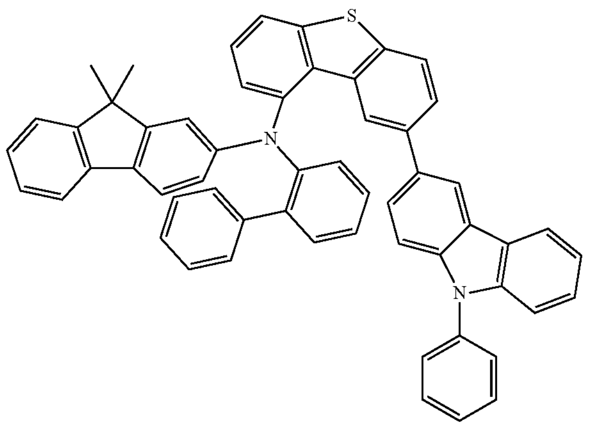 [SMILES: CC1(C)c2ccccc2-c2ccc(N(c3ccccc3-c3ccccc3)c3cccc4sc5ccc(-c6ccc7c(c6)c6ccccc6n7-c6ccccc6)cc5c34)cc21]
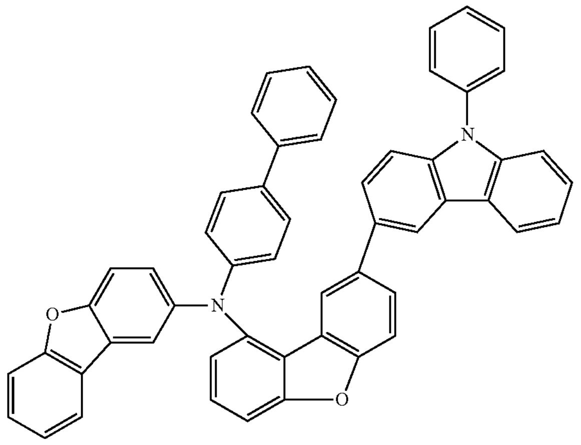 [SMILES: c1ccc(-c2ccc(N(c3ccc4oc5ccccc5c4c3)c3cccc4oc5ccc(-c6ccc7c(c6)c6ccccc6n7-c6ccccc6)cc5c34)cc2)cc1]

TABLE 3-continued
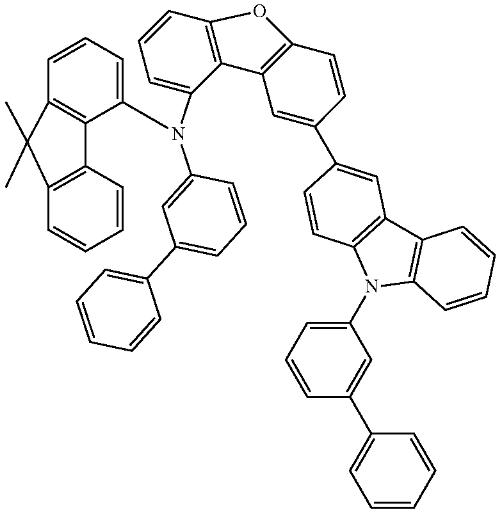 [SMILES: CC1(C)c2ccccc2-c2c(N(c3cccc(-c4ccccc4)c3)c3cccc4oc5ccc(-c6ccc7c(c6)c6ccccc6n7-c6cccc(-c7ccccc7)c6)cc5c34)cccc21]
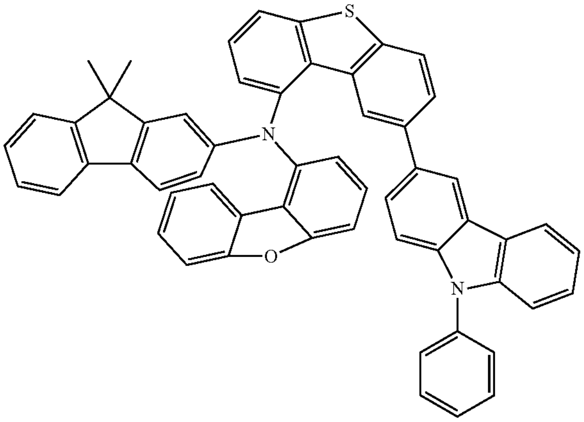 [SMILES: CC1(C)c2ccccc2-c2ccc(N(c3cccc4oc5ccccc5c34)c3cccc4sc5ccc(-c6ccc7c(c6)c6ccccc6n7-c6ccccc6)cc5c34)cc21]
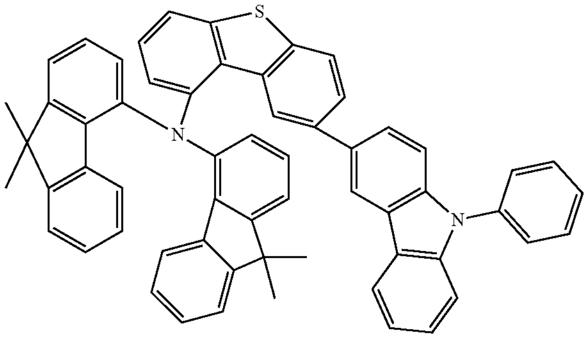 [SMILES: CC1(C)c2ccccc2-c2c(N(c3cccc4c3-c3ccccc3C4(C)C)c3cccc4sc5ccc(-c6ccc7c(c6)c6ccccc6n7-c6ccccc6)cc5c34)cccc21]
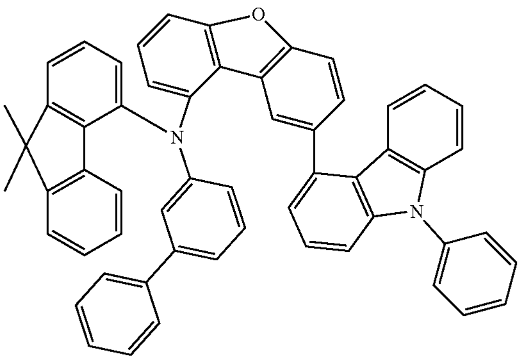 [SMILES: CC1(C)c2ccccc2-c2c(N(c3cccc(-c4ccccc4)c3)c3cccc4oc5ccc(-c6cccc7c6c6ccccc6n7-c6ccccc6)cc5c34)cccc21]

TABLE 3-continued
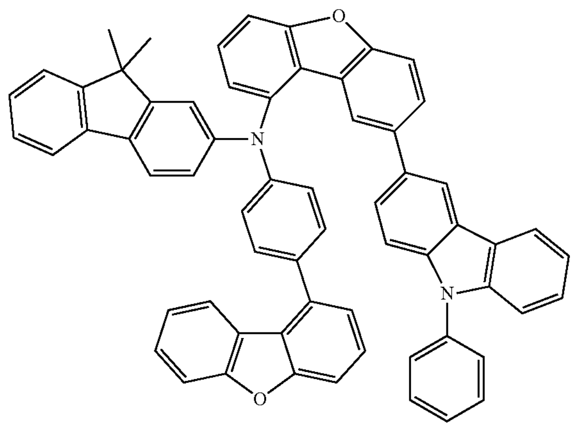 [SMILES: CC1(C)c2ccccc2-c2ccc(N(c3ccc(-c4cccc5oc6ccccc6c45)cc3)c3cccc4oc5ccc(-c6ccc7c(c6)c6ccccc6n7-c6ccccc6)cc5c34)cc21]
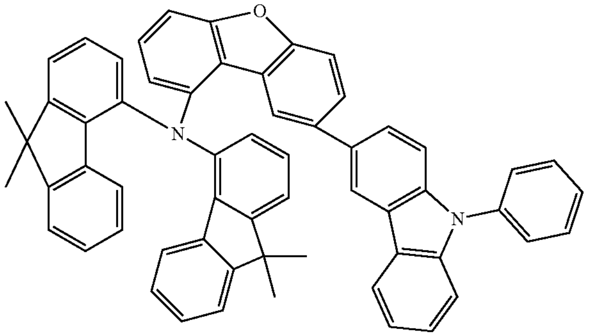 [SMILES: CC1(C)c2ccccc2-c2c(N(c3cccc4c3-c3ccccc3C4(C)C)c3cccc4oc5ccc(-c6ccc7c(c6)c6ccccc6n7-c6ccccc6)cc5c34)cccc21]
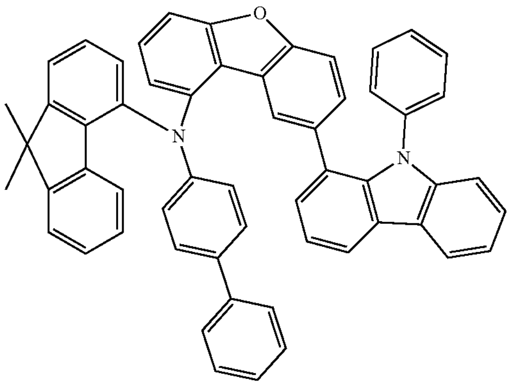 [SMILES: CC1(C)c2ccccc2-c2c(N(c3ccc(-c4ccccc4)cc3)c3cccc4oc5ccc(-c6cccc7c8ccccc8n(-c8ccccc8)c67)cc5c34)cccc21]

TABLE 3-continued
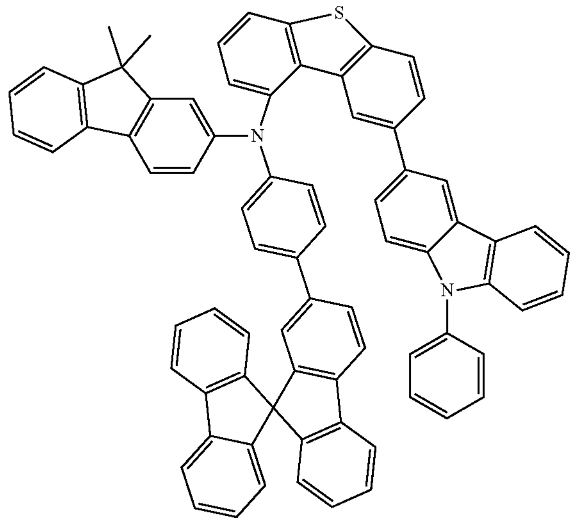 [SMILES: CC1(C)c2ccccc2-c2ccc(N(c3ccc(-c4ccc5c(c4)C4(c6ccccc6-c6ccccc64)c4ccccc4-5)cc3)c3cccc4sc5ccc(-c6ccc7c(c6)c6ccccc6n7-c6ccccc6)cc5c34)cc21]
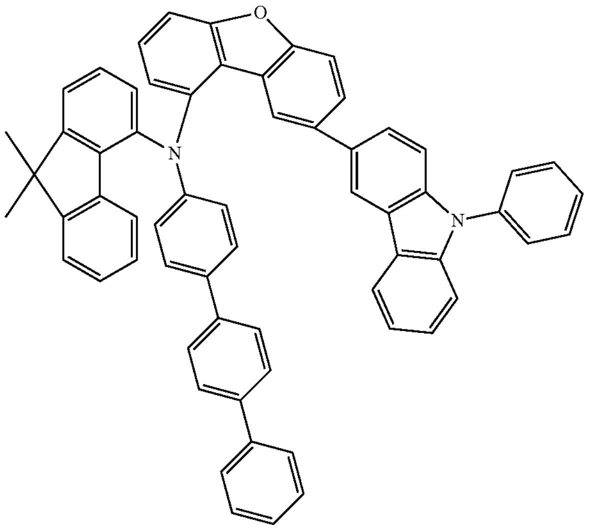 [SMILES: CC1(C)c2ccccc2-c2c(N(c3ccc(-c4ccc(-c5ccccc5)cc4)cc3)c3cccc4oc5ccc(-c6ccc7c(c6)c6ccccc6n7-c6ccccc6)cc5c34)cccc21]
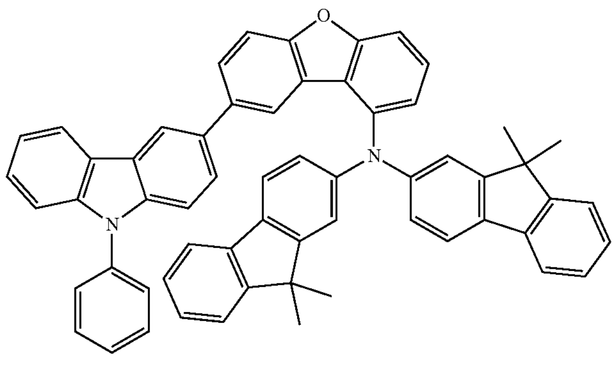 [SMILES: CC1(C)c2ccccc2-c2ccc(N(c3ccc4c(c3)C(C)(C)c3ccccc3-4)c3cccc4oc5ccc(-c6ccc7c(c6)c6ccccc6n7-c6ccccc6)cc5c34)cc21]

TABLE 3-continued
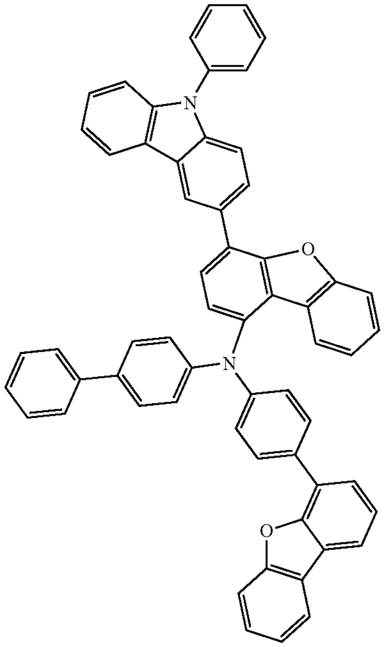 [SMILES: c1ccc(-c2ccc(N(c3ccc(-c4cccc5c4oc4ccccc45)cc3)c3ccc(-c4ccc5c(c4)c4ccccc4n5-c4ccccc4)c4oc5ccccc5c34)cc2)cc1]
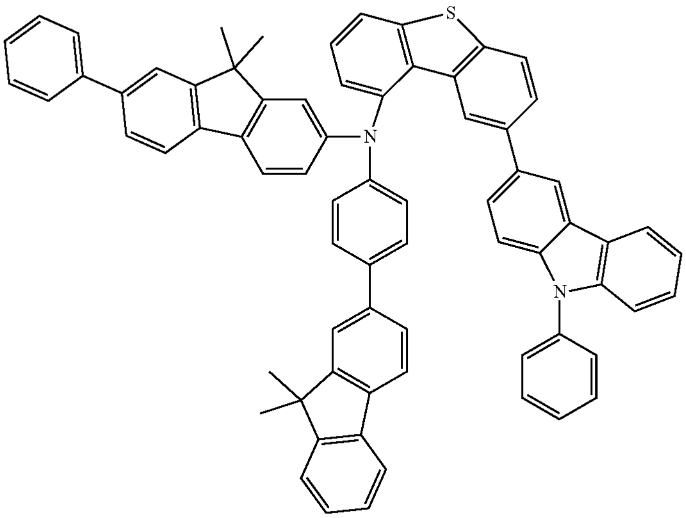 [SMILES: CC1(C)c2ccccc2-c2ccc(-c3ccc(N(c4ccc5c(c4)C(C)(C)c4cc(-c6ccccc6)ccc4-5)c4cccc5sc6ccc(-c7ccc8c(c7)c7ccccc7n8-c7ccccc7)cc6c45)cc3)cc21]
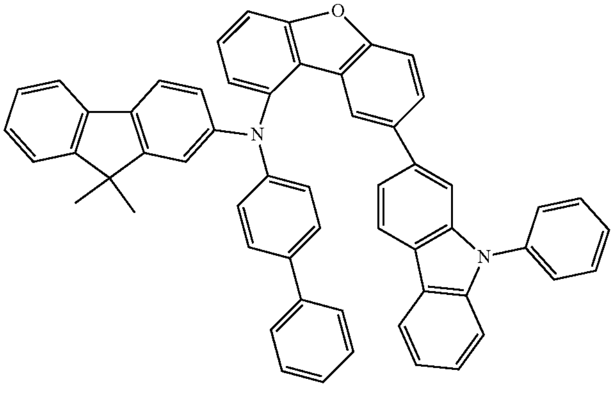 [SMILES: CC1(C)c2ccccc2-c2ccc(N(c3ccc(-c4ccccc4)cc3)c3cccc4oc5ccc(-c6ccc7c8ccccc8n(-c8ccccc8)c7c6)cc5c34)cc21]

TABLE 3-continued
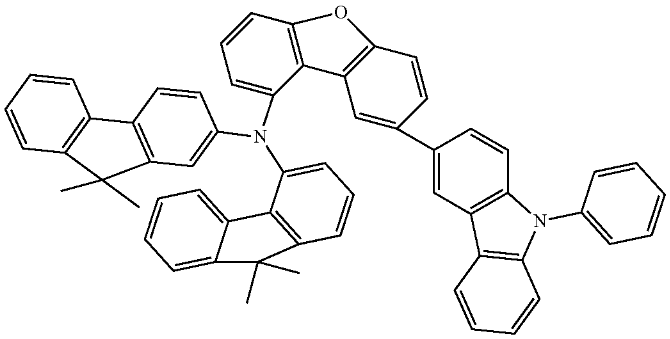 [SMILES: CC1(C)c2ccccc2-c2ccc(N(c3cccc4c3-c3ccccc3C4(C)C)c3cccc4oc5ccc(-c6ccc7c(c6)c6ccccc6n7-c6ccccc6)cc5c34)cc21]
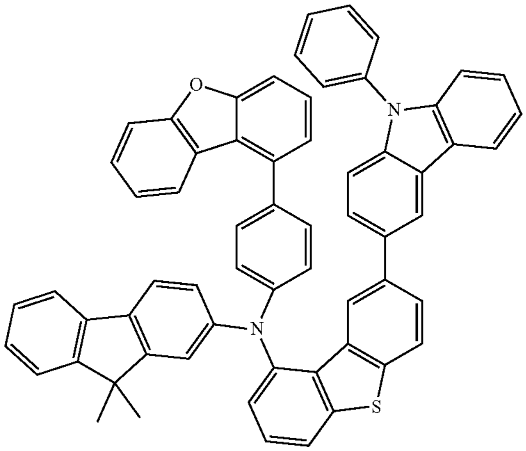 [SMILES: CC1(C)c2ccccc2-c2ccc(N(c3ccc(-c4cccc5oc6ccccc6c45)cc3)c3cccc4sc5ccc(-c6ccc7c(c6)c6ccccc6n7-c6ccccc6)cc5c34)cc21]
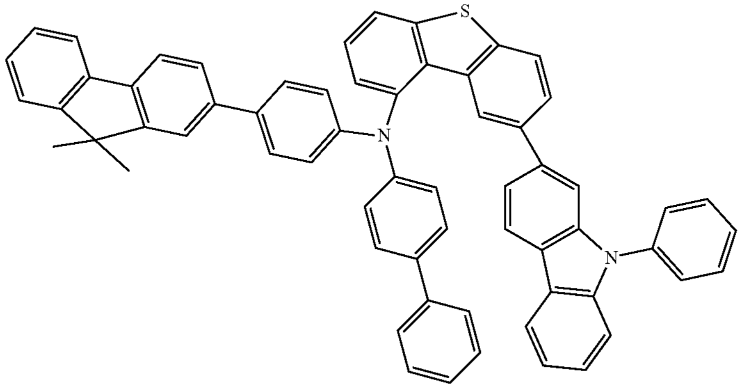 [SMILES: CC1(C)c2ccccc2-c2ccc(-c3ccc(N(c4ccc(-c5ccccc5)cc4)c4cccc5sc6ccc(-c7ccc8c9ccccc9n(-c9ccccc9)c8c7)cc6c45)cc3)cc21]
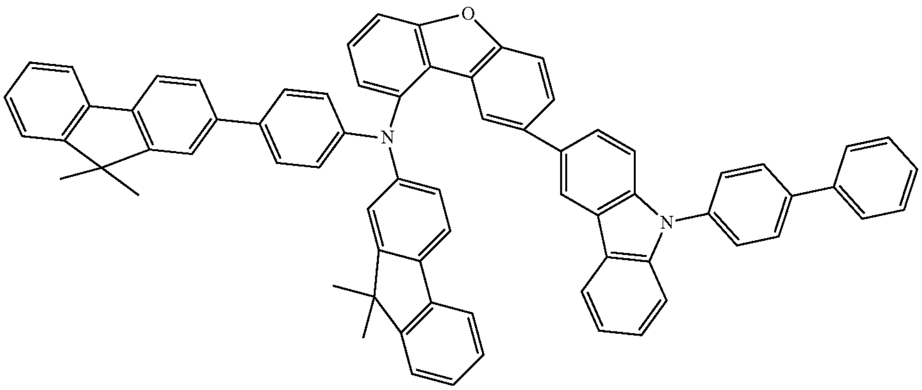 [SMILES: CC1(C)c2ccccc2-c2ccc(-c3ccc(N(c4ccc5c(c4)C(C)(C)c4ccccc4-5)c4cccc5oc6ccc(-c7ccc8c(c7)c7ccccc7n8-c7ccc(-c8ccccc8)cc7)cc6c45)cc3)cc21]

TABLE 3-continued
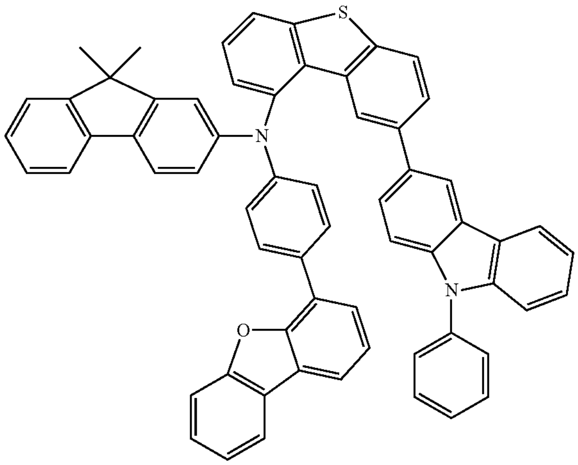 [SMILES: CC1(C)c2ccccc2-c2ccc(N(c3ccc(-c4cccc5c4oc4ccccc45)cc3)c3cccc4sc5ccc(-c6ccc7c(c6)c6ccccc6n7-c6ccccc6)cc5c34)cc21]
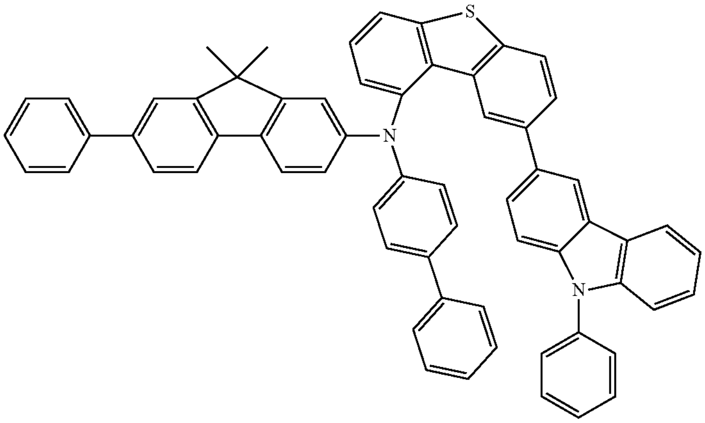 [SMILES: CC1(C)c2cc(-c3ccccc3)ccc2-c2ccc(N(c3ccc(-c4ccccc4)cc3)c3cccc4sc5ccc(-c6ccc7c(c6)c6ccccc6n7-c6ccccc6)cc5c34)cc21]
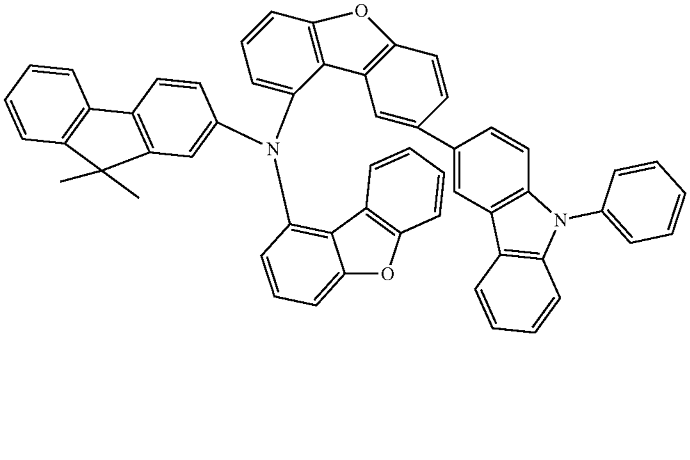 [SMILES: CC1(C)c2ccccc2-c2ccc(N(c3cccc4oc5ccccc5c34)c3cccc4oc5ccc(-c6ccc7c(c6)c6ccccc6n7-c6ccccc6)cc5c34)cc21]

TABLE 3-continued
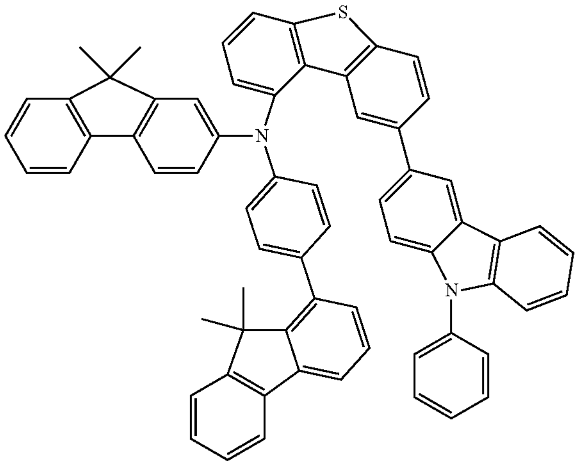 [SMILES: CC1(C)c2ccccc2-c2ccc(N(c3ccc(-c4cccc5c4C(C)(C)c4ccccc4-5)cc3)c3cccc4sc5ccc(-c6ccc7c(c6)c6ccccc6n7-c6ccccc6)cc5c34)cc21]
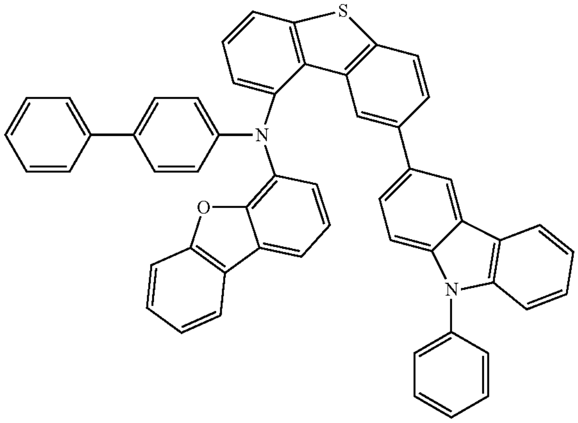 [SMILES: c1ccc(-c2ccc(N(c3cccc4c3oc3ccccc34)c3cccc4sc5ccc(-c6ccc7c(c6)c6ccccc6n7-c6ccccc6)cc5c34)cc2)cc1]
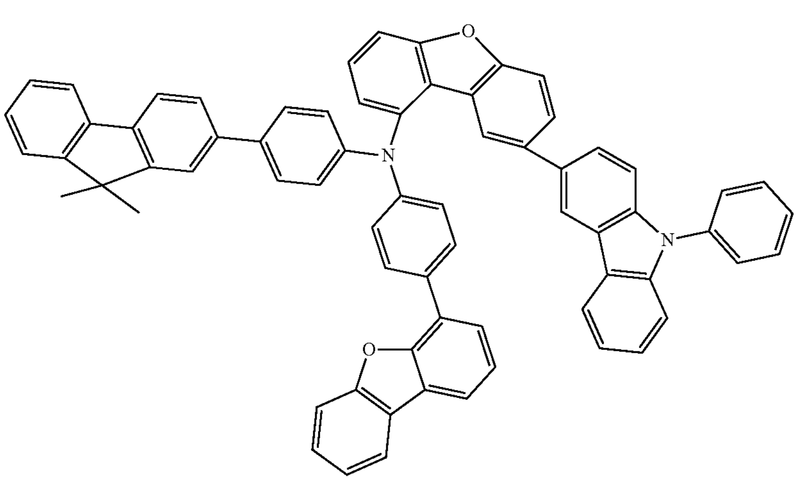 [SMILES: CC1(C)c2ccccc2-c2ccc(-c3ccc(N(c4ccc(-c5cccc6c5oc5ccccc56)cc4)c4cccc5oc6ccc(-c7ccc8c(c7)c7ccccc7n8-c7ccccc7)cc6c45)cc3)cc21]

TABLE 3-continued
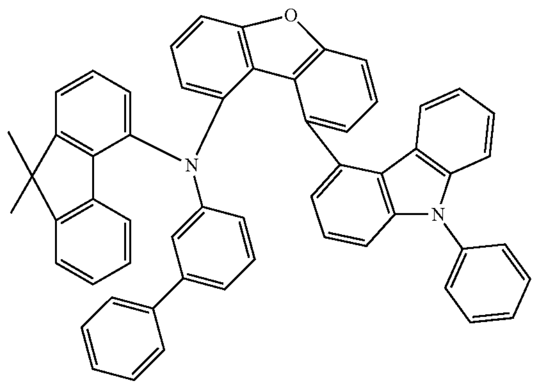 [SMILES: CC1(C)c2ccccc2-c2c(N(c3cccc(-c4ccccc4)c3)c3cccc4oc5cccc(-c6cccc7c6c6ccccc6n7-c6ccccc6)c5c34)cccc21]
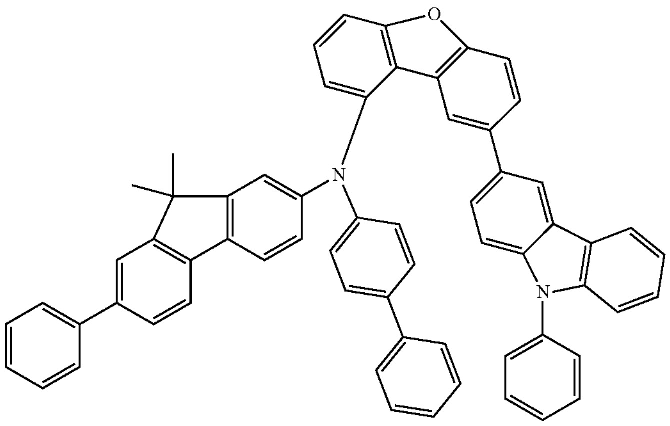 [SMILES: CC1(C)c2cc(-c3ccccc3)ccc2-c2ccc(N(c3ccc(-c4ccccc4)cc3)c3cccc4oc5ccc(-c6ccc7c(c6)c6ccccc6n7-c6ccccc6)cc5c34)cc21]
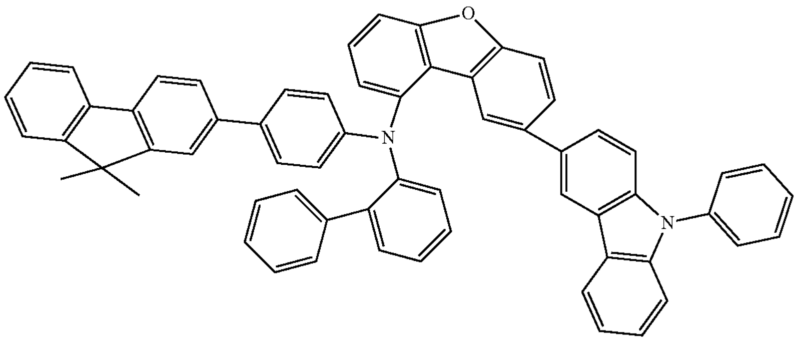 [SMILES: CC1(C)c2ccccc2-c2ccc(-c3ccc(N(c4ccccc4-c4ccccc4)c4cccc5oc6ccc(-c7ccc8c(c7)c7ccccc7n8-c7ccccc7)cc6c45)cc3)cc21]

TABLE 3-continued
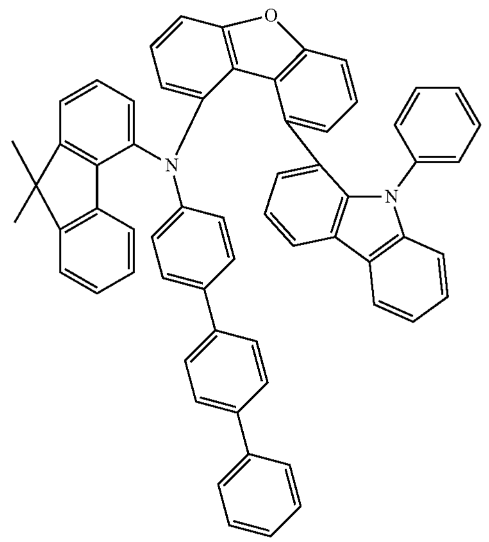 [SMILES: CC1(C)c2ccccc2-c2c(N(c3ccc(-c4ccc(-c5ccccc5)cc4)cc3)c3cccc4oc5cccc(-c6cccc7c8ccccc8n(-c8ccccc8)c67)c5c34)cccc21]
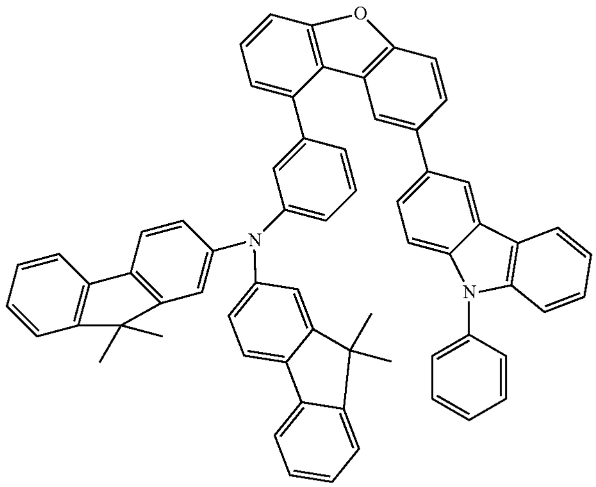 [SMILES: CC1(C)c2ccccc2-c2ccc(N(c3cccc(-c4cccc5oc6ccc(-c7ccc8c(c7)c7ccccc7n8-c7ccccc7)cc6c45)c3)c3ccc4c(c3)C(C)(C)c3ccccc3-4)cc21]
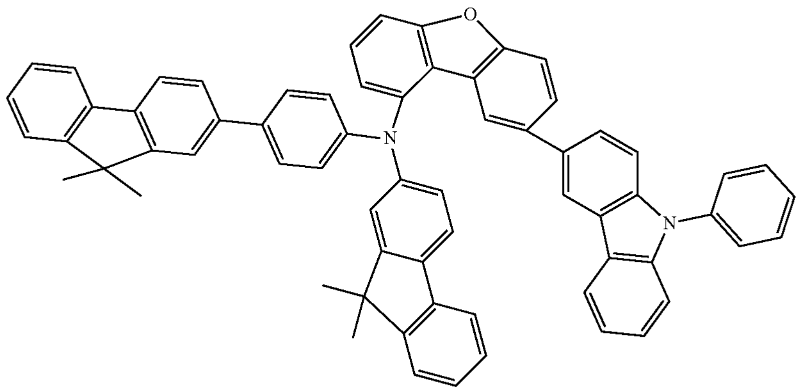 [SMILES: CC1(C)c2ccccc2-c2ccc(-c3ccc(N(c4ccc5c(c4)C(C)(C)c4ccccc4-5)c4cccc5oc6ccc(-c7ccc8c(c7)c7ccccc7n8-c7ccccc7)cc6c45)cc3)cc21]

TABLE 3-continued
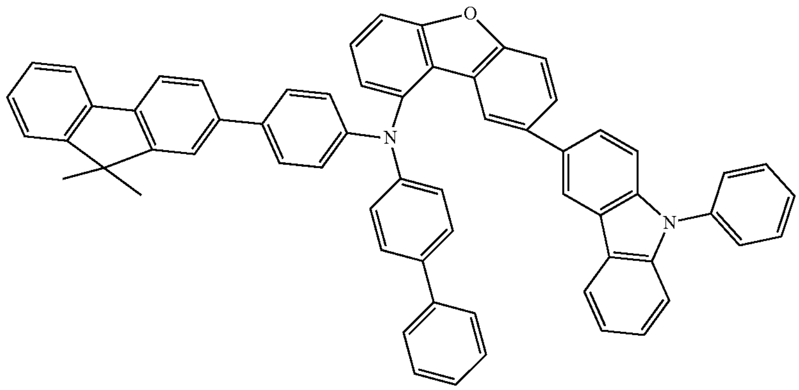 [SMILES: CC1(C)c2ccccc2-c2ccc(-c3ccc(N(c4ccc(-c5ccccc5)cc4)c4cccc5oc6ccc(-c7ccc8c(c7)c7ccccc7n8-c7ccccc7)cc6c45)cc3)cc21]
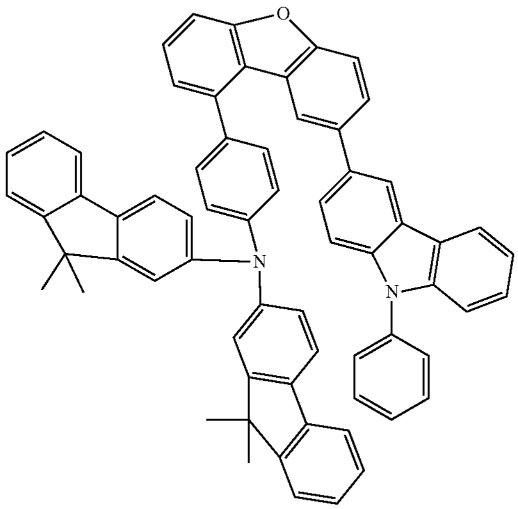 [SMILES: CC1(C)c2ccccc2-c2ccc(N(c3ccc(-c4cccc5oc6ccc(-c7ccc8c(c7)c7ccccc7n8-c7ccccc7)cc6c45)cc3)c3ccc4c(c3)C(C)(C)c3ccccc3-4)cc21]
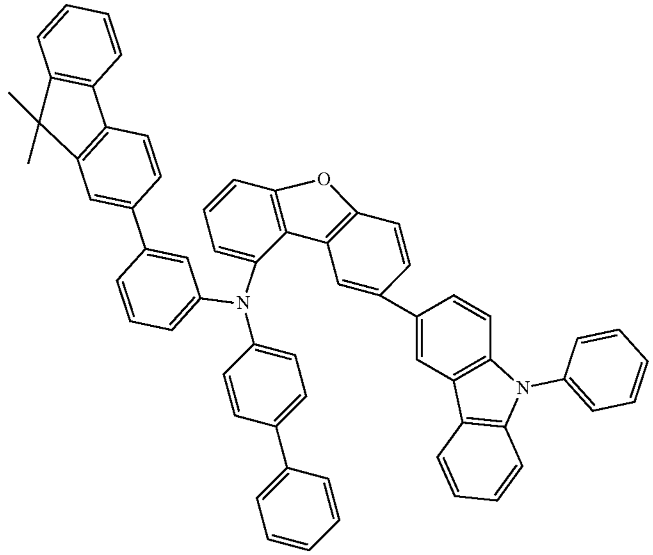 [SMILES: CC1(C)c2ccccc2-c2ccc(-c3cccc(N(c4ccc(-c5ccccc5)cc4)c4cccc5oc6ccc(-c7ccc8c(c7)c7ccccc7n8-c7ccccc7)cc6c45)c3)cc21]

TABLE 3-continued
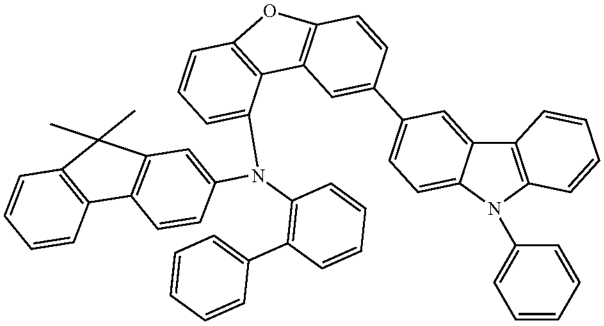 [SMILES: CC1(C)c2ccccc2-c2ccc(N(c3ccccc3-c3ccccc3)c3cccc4oc5ccc(-c6ccc7c(c6)c6ccccc6n7-c6ccccc6)cc5c34)cc21]
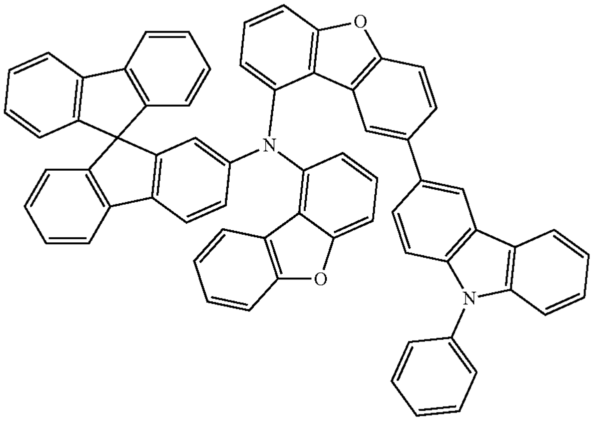 [SMILES: c1ccc(-n2c3ccccc3c3cc(-c4ccc5oc6cccc(N(c7ccc8c(c7)C7(c9ccccc9-c9ccccc97)c7ccccc7-8)c7cccc8oc9ccccc9c78)c6c5c4)ccc32)cc1]
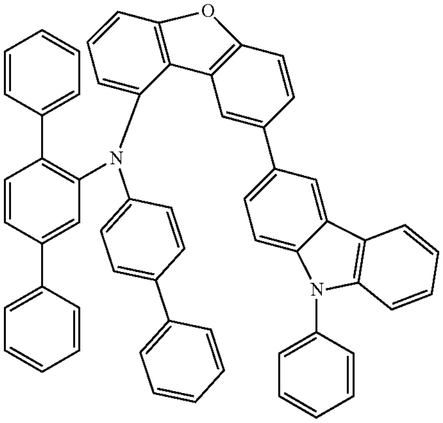 [SMILES: c1ccc(-c2ccc(N(c3cc(-c4ccccc4)ccc3-c3ccccc3)c3cccc4oc5ccc(-c6ccc7c(c6)c6ccccc6n7-c6ccccc6)cc5c34)cc2)cc1]
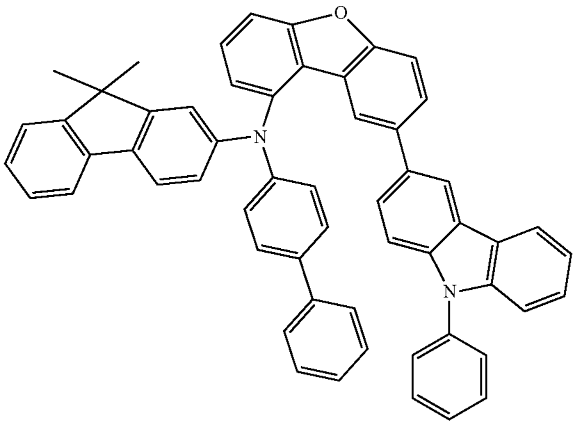 [SMILES: CC1(C)c2ccccc2-c2ccc(N(c3ccc(-c4ccccc4)cc3)c3cccc4oc5ccc(-c6ccc7c(c6)c6ccccc6n7-c6ccccc6)cc5c34)cc21]

TABLE 3-continued
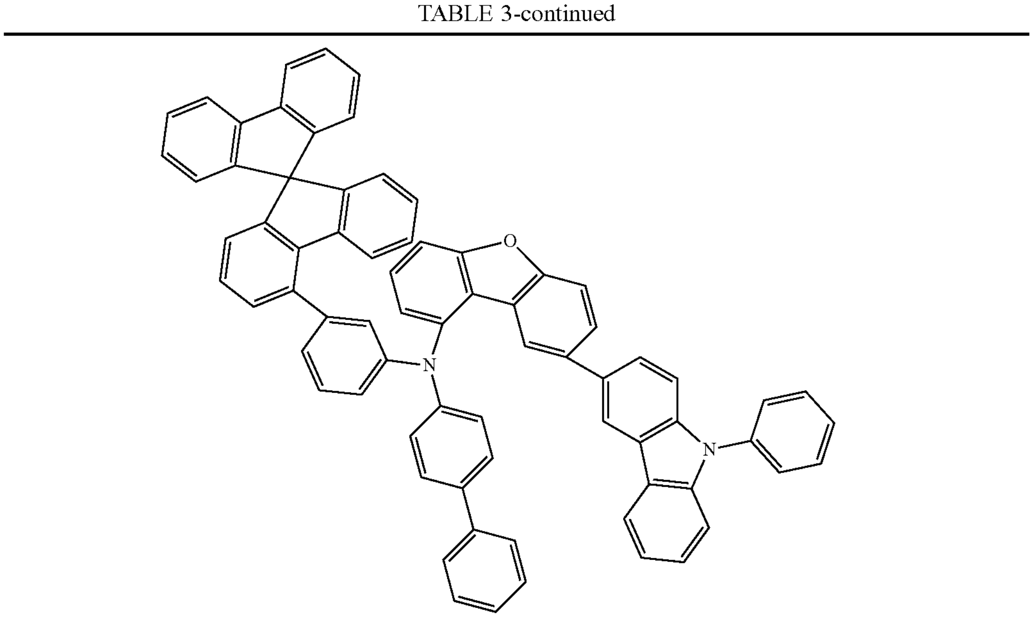
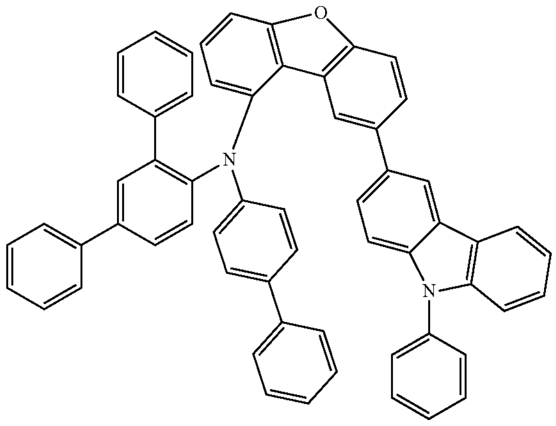 [SMILES: c1ccc(-c2ccc(N(c3ccc(-c4ccccc4)cc3-c3ccccc3)c3cccc4oc5ccc(-c6ccc7c(c6)c6ccccc6n7-c6ccccc6)cc5c34)cc2)cc1]
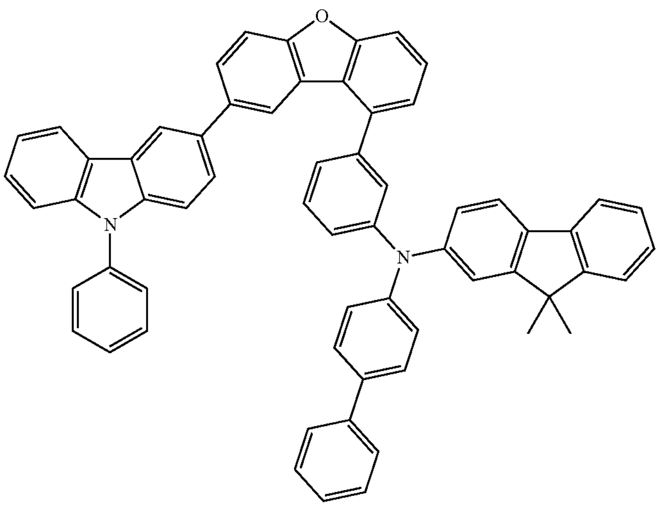 [SMILES: CC1(C)c2ccccc2-c2ccc(N(c3ccc(-c4ccccc4)cc3)c3cccc(-c4cccc5oc6ccc(-c7ccc8c(c7)c7ccccc7n8-c7ccccc7)cc6c45)c3)cc21]

TABLE 3-continued
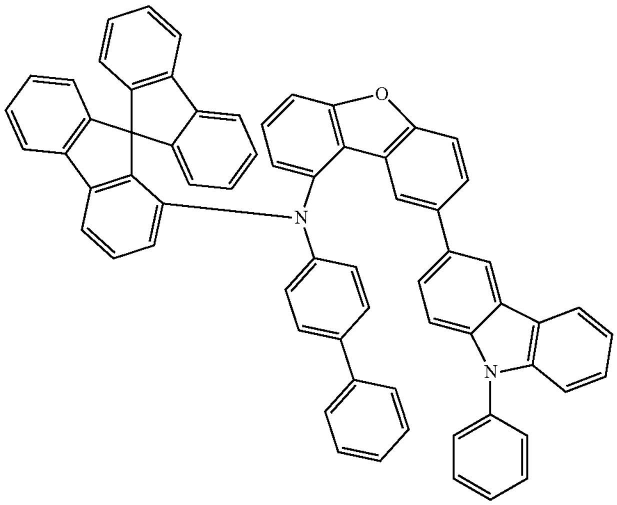 [SMILES: c1ccc(-c2ccc(N(c3cccc4c3C3(c5ccccc5-c5ccccc53)c3ccccc3-4)c3cccc4oc5ccc(-c6ccc7c(c6)c6ccccc6n7-c6ccccc6)cc5c34)cc2)cc1]
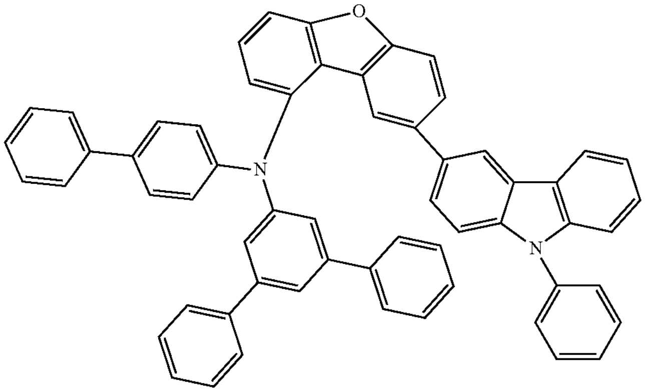 [SMILES: c1ccc(-c2ccc(N(c3cc(-c4ccccc4)cc(-c4ccccc4)c3)c3cccc4oc5ccc(-c6ccc7c(c6)c6ccccc6n7-c6ccccc6)cc5c34)cc2)cc1]
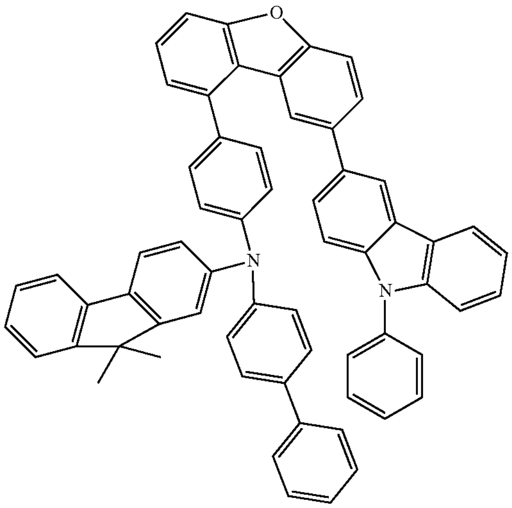 [SMILES: CC1(C)c2ccccc2-c2ccc(N(c3ccc(-c4ccccc4)cc3)c3ccc(-c4cccc5oc6ccc(-c7ccc8c(c7)c7ccccc7n8-c7ccccc7)cc6c45)cc3)cc21]

TABLE 3-continued
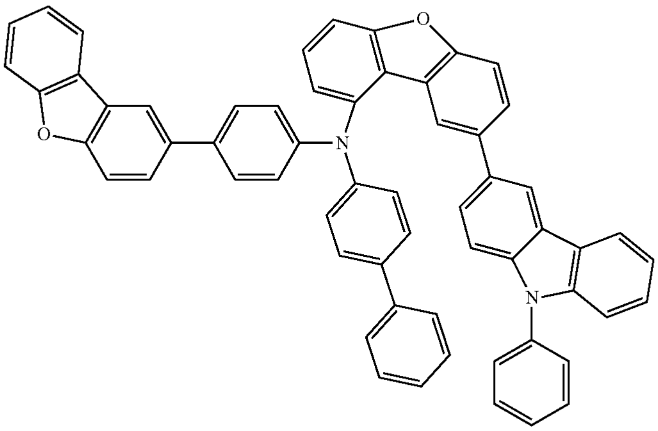 [SMILES: c1ccc(-c2ccc(N(c3ccc(-c4ccc5oc6ccccc6c5c4)cc3)c3cccc4oc5ccc(-c6ccc7c(c6)c6ccccc6n7-c6ccccc6)cc5c34)cc2)cc1]
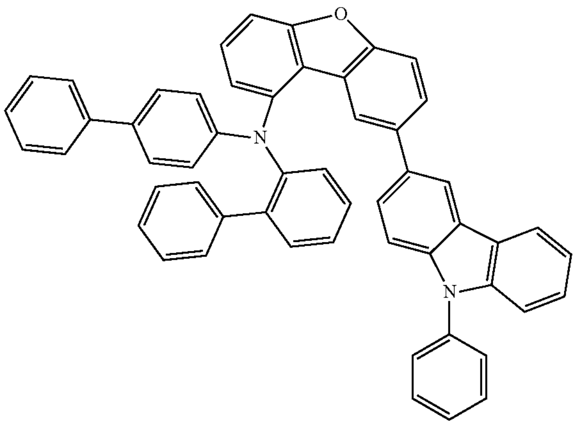 [SMILES: c1ccc(-c2ccc(N(c3ccccc3-c3ccccc3)c3cccc4oc5ccc(-c6ccc7c(c6)c6ccccc6n7-c6ccccc6)cc5c34)cc2)cc1]
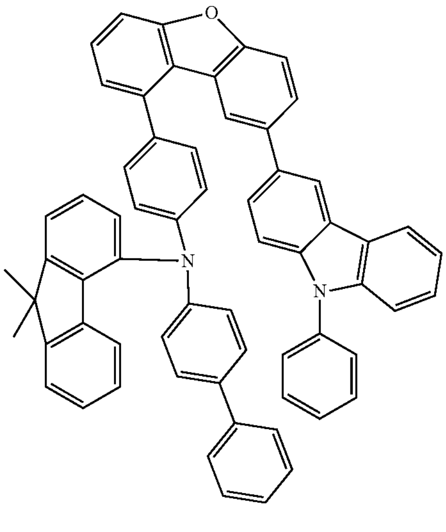 [SMILES: CC1(C)c2ccccc2-c2c(N(c3ccc(-c4ccccc4)cc3)c3ccc(-c4cccc5oc6ccc(-c7ccc8c(c7)c7ccccc7n8-c7ccccc7)cc6c45)cc3)cccc21]

TABLE 3-continued
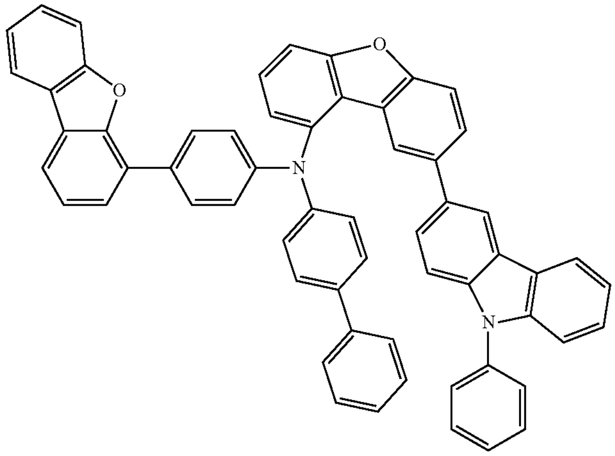 [SMILES: c1ccc(-c2ccc(N(c3ccc(-c4cccc5c4oc4ccccc45)cc3)c3cccc4oc5ccc(-c6ccc7c(c6)c6ccccc6n7-c6ccccc6)cc5c34)cc2)cc1]
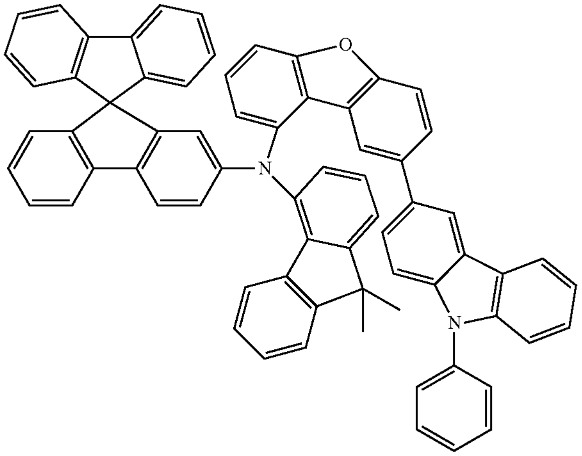 [SMILES: CC1(C)c2ccccc2-c2c(N(c3ccc4c(c3)C3(c5ccccc5-c5ccccc53)c3ccccc3-4)c3cccc4oc5ccc(-c6ccc7c(c6)c6ccccc6n7-c6ccccc6)cc5c34)cccc21]
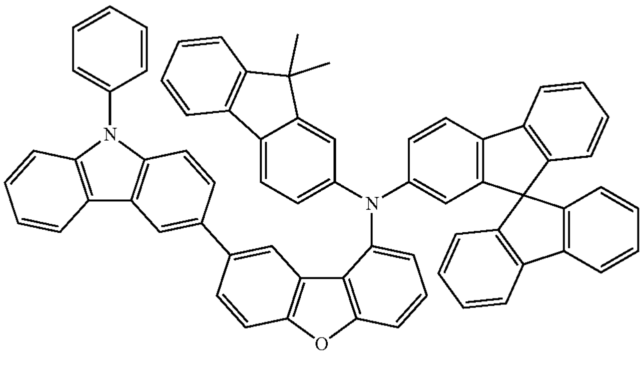 [SMILES: CC1(C)c2ccccc2-c2ccc(N(c3ccc4c(c3)C3(c5ccccc5-c5ccccc53)c3ccccc3-4)c3cccc4oc5ccc(-c6ccc7c(c6)c6ccccc6n7-c6ccccc6)cc5c34)cc21]

TABLE 3-continued
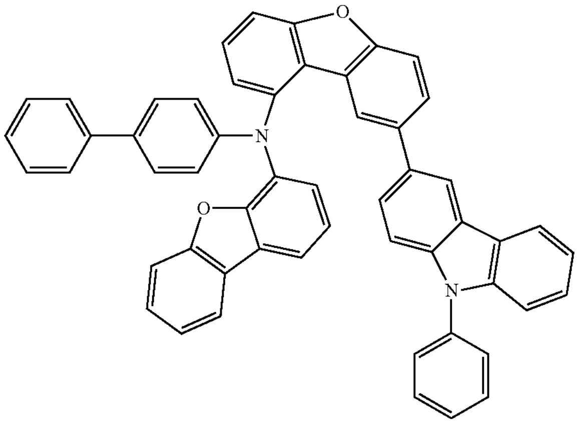 [SMILES: c1ccc(-c2ccc(N(c3cccc4c3oc3ccccc34)c3cccc4oc5ccc(-c6ccc7c(c6)c6ccccc6n7-c6ccccc6)cc5c34)cc2)cc1]
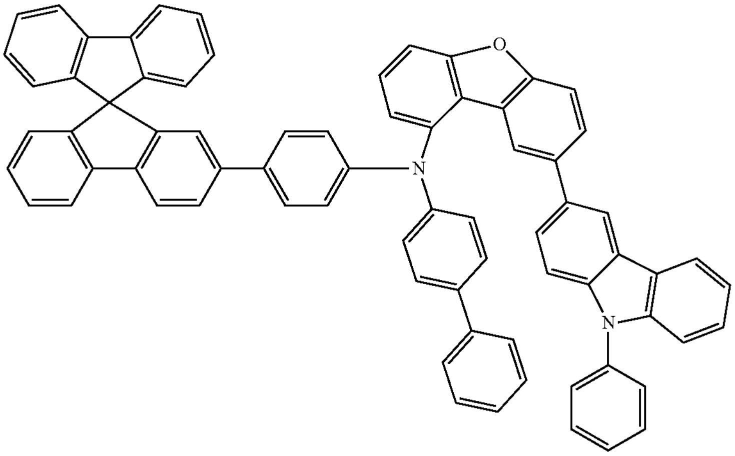 [SMILES: c1ccc(-c2ccc(N(c3ccc(-c4ccc5c(c4)C4(c6ccccc6-c6ccccc64)c4ccccc4-5)cc3)c3cccc4oc5ccc(-c6ccc7c(c6)c6ccccc6n7-c6ccccc6)cc5c34)cc2)cc1]
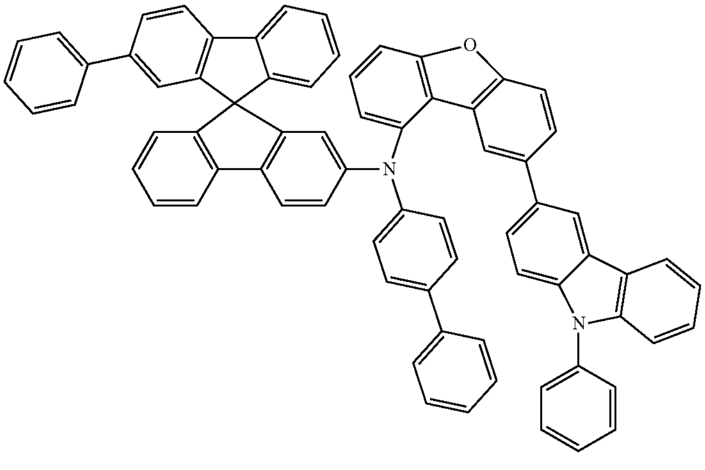 [SMILES: c1ccc(-c2ccc(N(c3ccc4c(c3)C3(c5ccccc5-c5ccc(-c6ccccc6)cc53)c3ccccc3-4)c3cccc4oc5ccc(-c6ccc7c(c6)c6ccccc6n7-c6ccccc6)cc5c34)cc2)cc1]

TABLE 3-continued
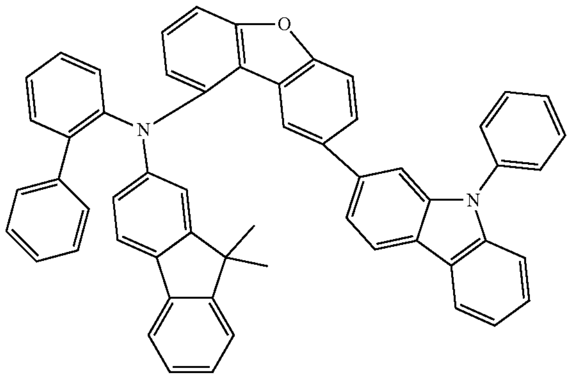 [SMILES: CC1(C)c2ccccc2-c2ccc(N(c3ccccc3-c3ccccc3)c3cccc4oc5ccc(-c6ccc7c8ccccc8n(-c8ccccc8)c7c6)cc5c34)cc21]
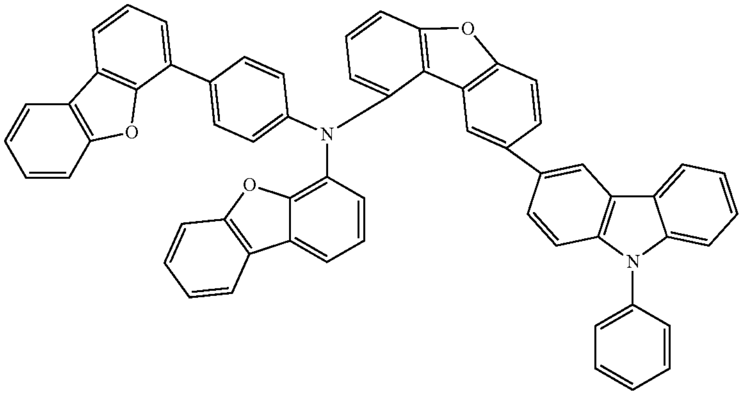 [SMILES: c1ccc(-n2c3ccccc3c3cc(-c4ccc5oc6cccc(N(c7ccc(-c8cccc9c8oc8ccccc89)cc7)c7cccc8c7oc7ccccc78)c6c5c4)ccc32)cc1]
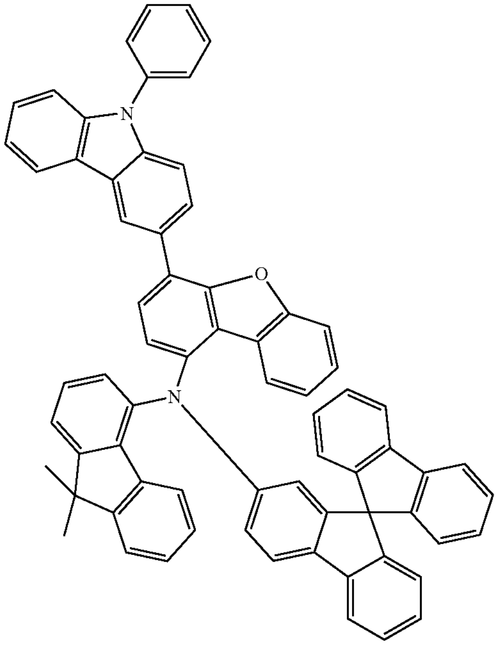 [SMILES: CC1(C)c2ccccc2-c2c(N(c3ccc4c(c3)C3(c5ccccc5-c5ccccc53)c3ccccc3-4)c3ccc(-c4ccc5c(c4)c4ccccc4n5-c4ccccc4)c4oc5ccccc5c34)cccc21]

TABLE 3-continued
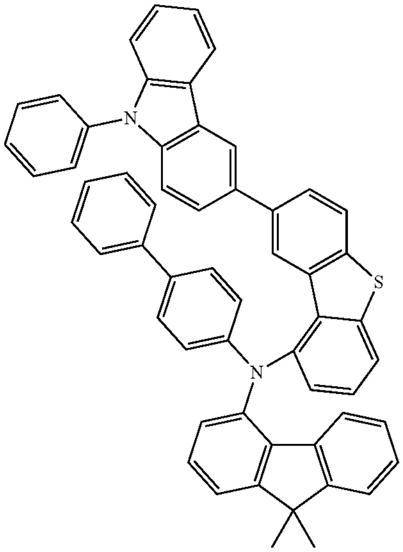 [SMILES: CC1(C)c2ccccc2-c2c(N(c3ccc(-c4ccccc4)cc3)c3cccc4sc5ccc(-c6ccc7c(c6)c6ccccc6n7-c6ccccc6)cc5c34)cccc21]
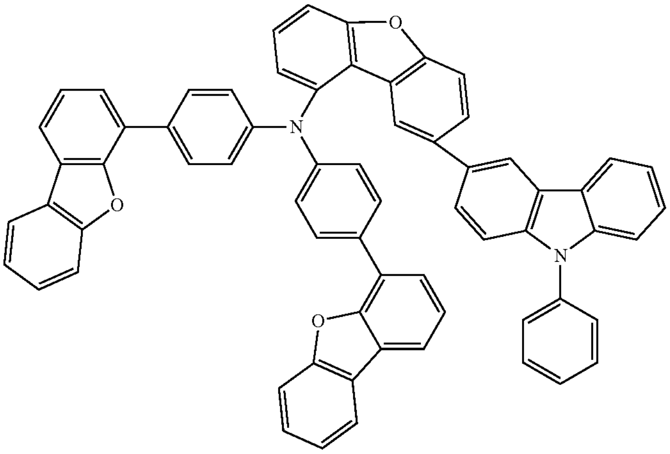 [SMILES: c1ccc(-n2c3ccccc3c3cc(-c4ccc5oc6cccc(N(c7ccc(-c8cccc9c8oc8ccccc89)cc7)c7ccc(-c8cccc9c8oc8ccccc89)cc7)c6c5c4)ccc32)cc1]
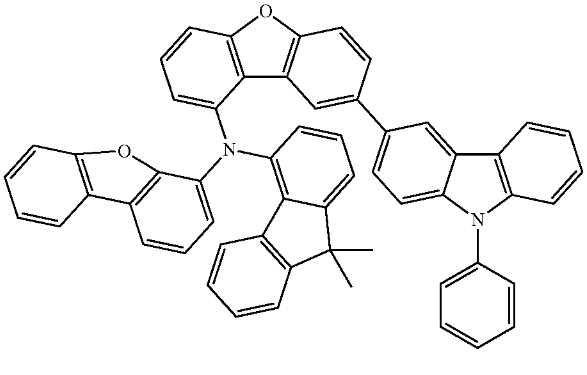 [SMILES: CC1(C)c2ccccc2-c2c(N(c3cccc4c3oc3ccccc34)c3cccc4oc5ccc(-c6ccc7c(c6)c6ccccc6n7-c6ccccc6)cc5c34)cccc21]

TABLE 3-continued
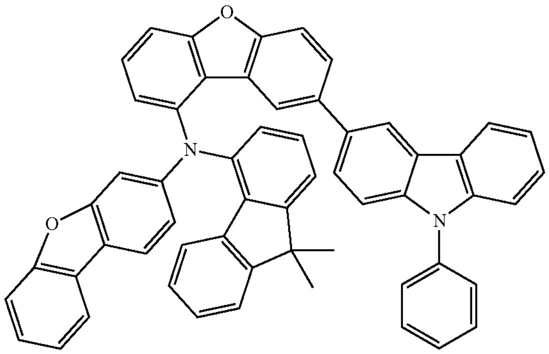 [SMILES: CC1(C)c2ccccc2-c2c(N(c3ccc4c(c3)oc3ccccc34)c3cccc4oc5ccc(-c6ccc7c(c6)c6ccccc6n7-c6ccccc6)cc5c34)cccc21]
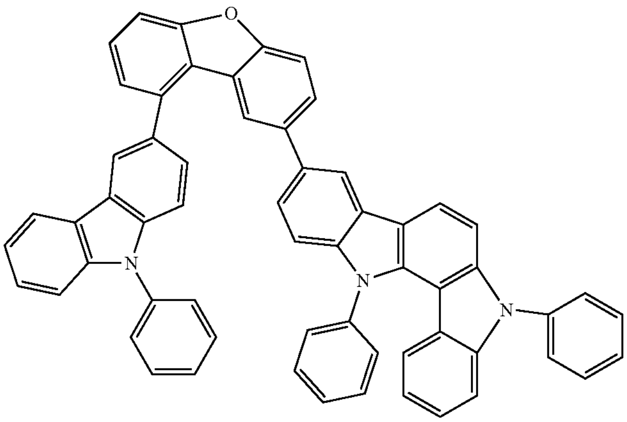 [SMILES: c1ccc(-n2c3ccccc3c3cc(-c4cccc5oc6ccc(-c7ccc8c(c7)c7ccc9c(c%10ccccc%10n9-c9ccccc9)c7n8-c7ccccc7)cc6c45)ccc32)cc1]
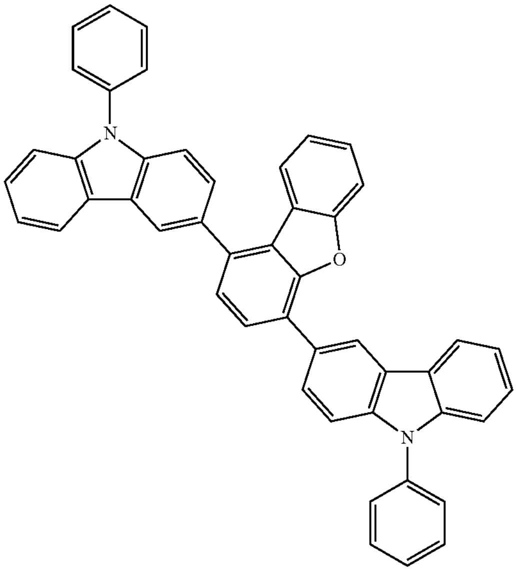 [SMILES: c1ccc(-n2c3ccccc3c3cc(-c4ccc(-c5ccc6c(c5)c5ccccc5n6-c5ccccc5)c5c4oc4ccccc45)ccc32)cc1]

TABLE 3-continued
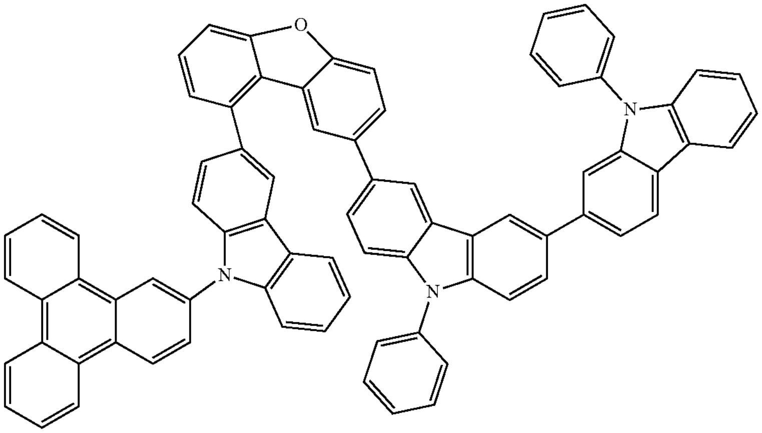 [SMILES: c1ccc(-n2c3ccc(-c4ccc5oc6cccc(-c7ccc8c(c7)c7ccccc7n8-c7ccc8c9ccccc9c9ccccc9c8c7)c6c5c4)cc3c3cc(-c4ccc5c6ccccc6n(-c6ccccc6)c5c4)ccc32)cc1]
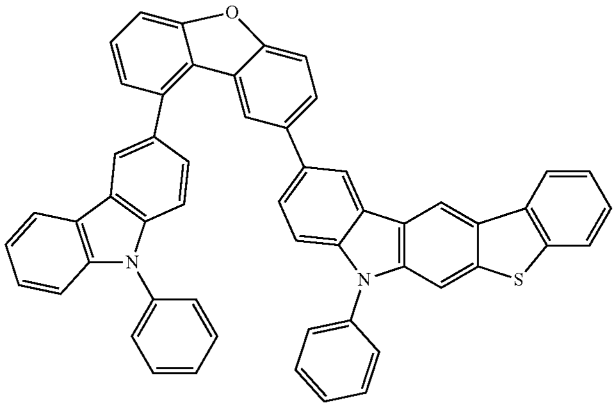 [SMILES: c1ccc(-n2c3ccccc3c3cc(-c4cccc5oc6ccc(-c7ccc8c(c7)c7cc9c(cc7n8-c7ccccc7)sc7ccccc79)cc6c45)ccc32)cc1]
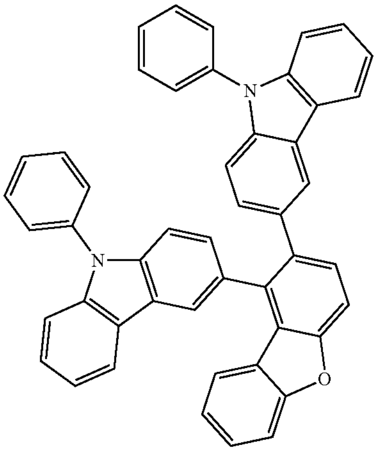 [SMILES: c1ccc(-n2c3ccccc3c3cc(-c4ccc5oc6ccccc6c5c4-c4ccc5c(c4)c4ccccc4n5-c4ccccc4)ccc32)cc1]

TABLE 3-continued
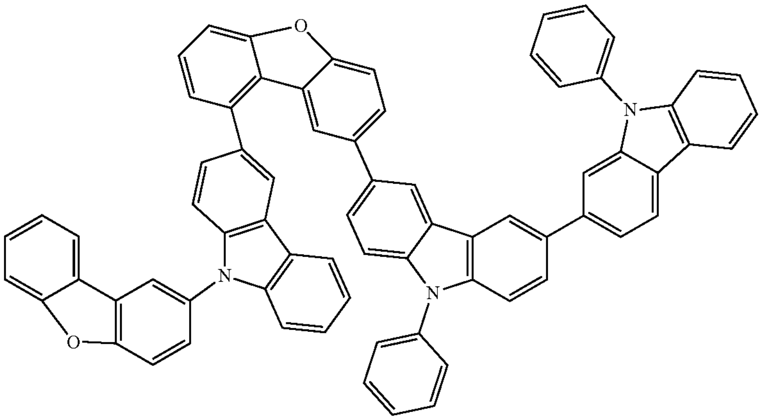 [SMILES: c1ccc(-n2c3ccc(-c4ccc5oc6cccc(-c7ccc8c(c7)c7ccccc7n8-c7ccc8oc9ccccc9c8c7)c6c5c4)cc3c3cc(-c4ccc5c6ccccc6n(-c6ccccc6)c5c4)ccc32)cc1]
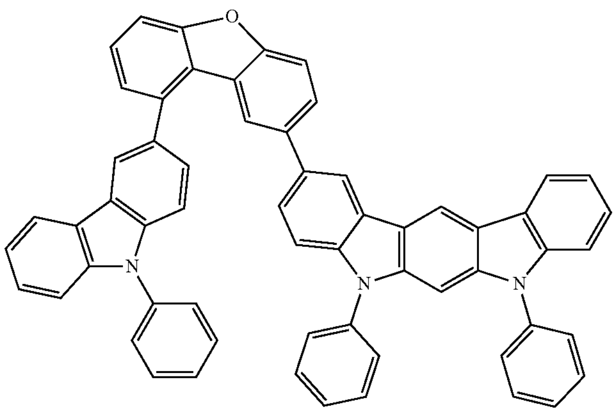 [SMILES: c1ccc(-n2c3ccccc3c3cc(-c4cccc5oc6ccc(-c7ccc8c(c7)c7cc9c%10ccccc%10n(-c%10ccccc%10)c9cc7n8-c7ccccc7)cc6c45)ccc32)cc1]
31
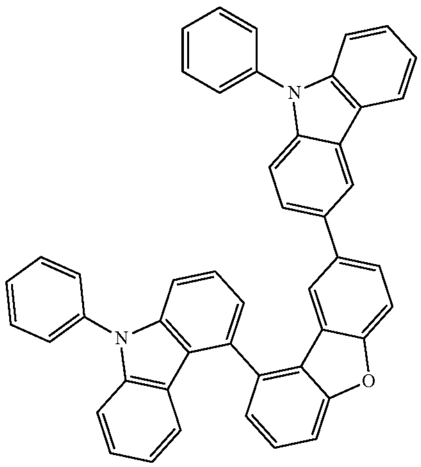 [SMILES: c1ccc(-n2c3ccccc3c3cc(-c4ccc5oc6cccc(-c7cccc8c7c7ccccc7n8-c7ccccc7)c6c5c4)ccc32)cc1]

TABLE 3-continued
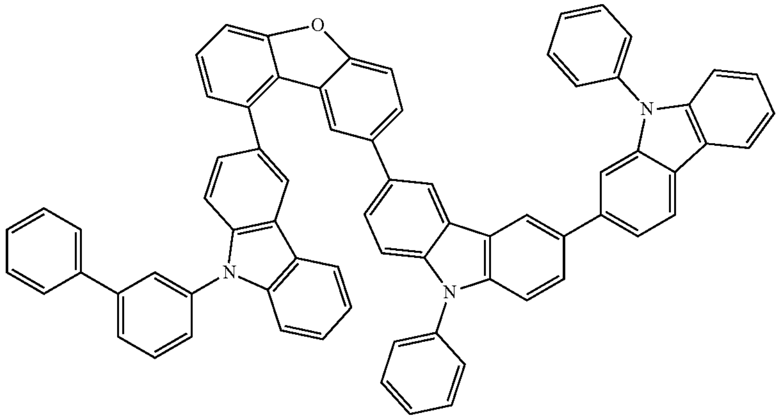 [SMILES: c1ccc(-c2cccc(-n3c4ccccc4c4cc(-c5cccc6oc7ccc(-c8ccc9c(c8)c8cc(-c%10ccc%11c%12ccccc%12n(-c%12ccccc%12)c%11c%10)ccc8n9-c8ccccc8)cc7c56)ccc43)c2)cc1]
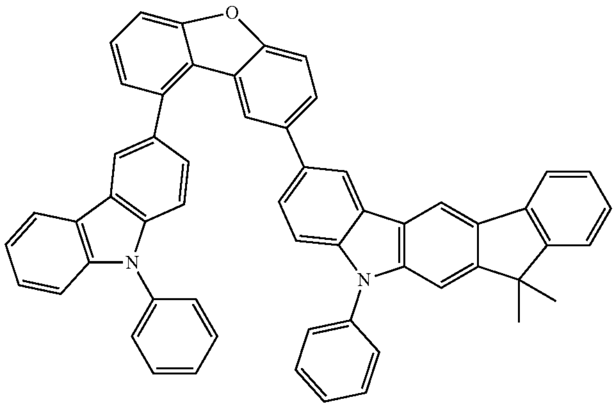 [SMILES: CC1(C)c2ccccc2-c2cc3c4cc(-c5ccc6oc7cccc(-c8ccc9c(c8)c8ccccc8n9-c8ccccc8)c7c6c5)ccc4n(-c4ccccc4)c3cc21]
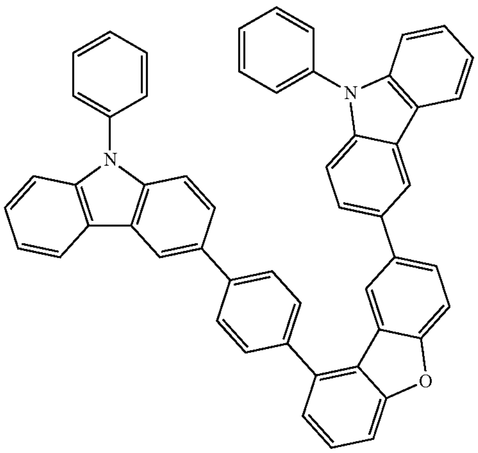 [SMILES: c1ccc(-n2c3ccccc3c3cc(-c4ccc(-c5cccc6oc7ccc(-c8ccc9c(c8)c8ccccc8n9-c8ccccc8)cc7c56)cc4)ccc32)cc1]

TABLE 3-continued
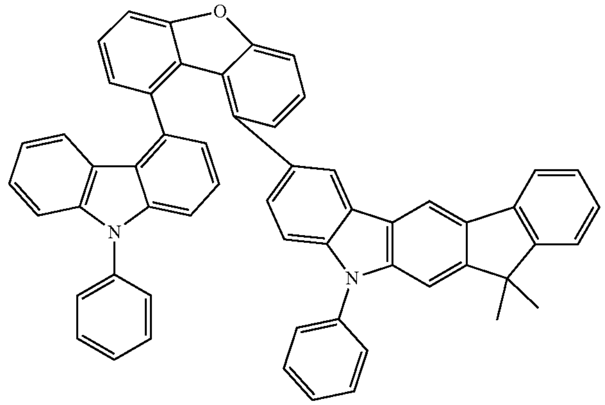 [SMILES: CC1(C)c2ccccc2-c2cc3c4cc(-c5cccc6oc7cccc(-c8cccc9c8c8ccccc8n9-c8ccccc8)c7c56)ccc4n(-c4ccccc4)c3cc21]
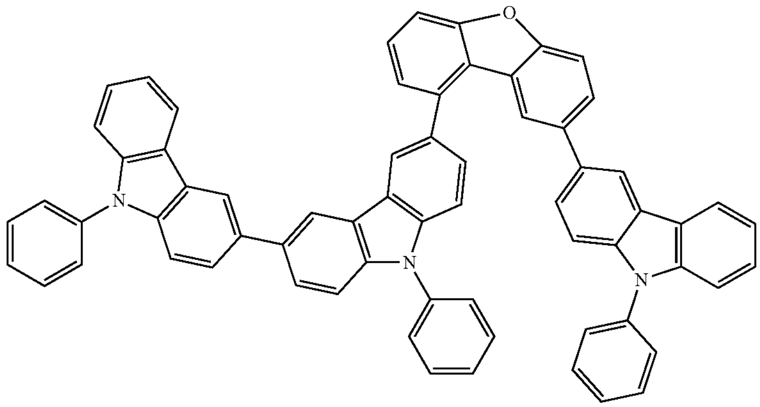 [SMILES: c1ccc(-n2c3ccccc3c3cc(-c4ccc5oc6cccc(-c7ccc8c(c7)c7cc(-c9ccc%10c(c9)c9ccccc9n%10-c9ccccc9)ccc7n8-c7ccccc7)c6c5c4)ccc32)cc1]
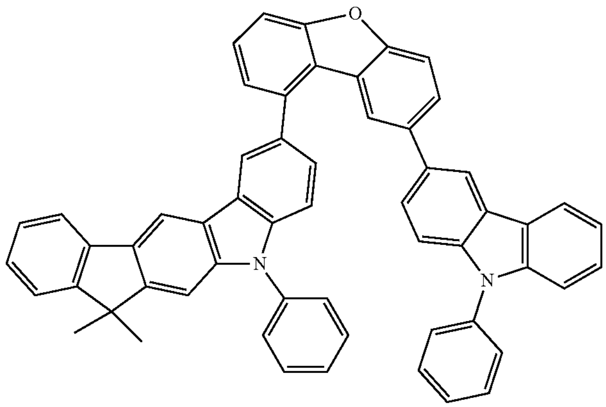 [SMILES: CC1(C)c2ccccc2-c2cc3c4cc(-c5cccc6oc7ccc(-c8ccc9c(c8)c8ccccc8n9-c8ccccc8)cc7c56)ccc4n(-c4ccccc4)c3cc21]
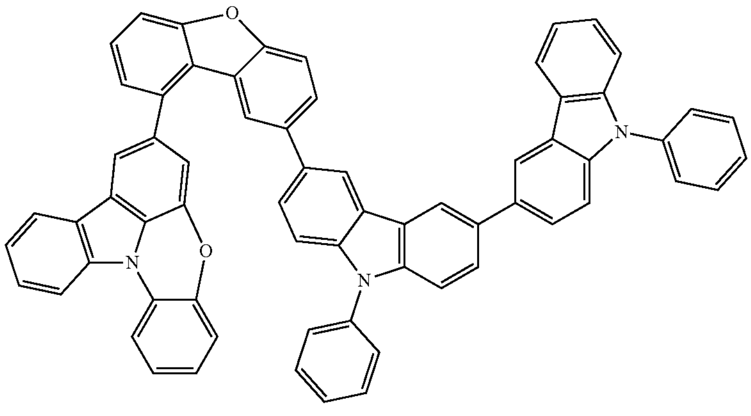 [SMILES: c1ccc(-n2c3ccccc3c3cc(-c4ccc5c(c4)c4cc(-c6ccc7oc8cccc(-c9cc%10c%11c(c9)c9ccccc9n%11-c9ccccc9O%10)c8c7c6)ccc4n5-c4ccccc4)ccc32)cc1]

TABLE 3-continued
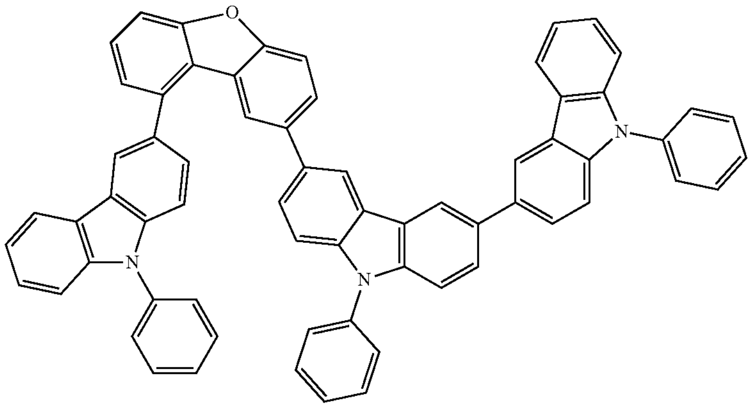 [SMILES: c1ccc(-n2c3ccccc3c3cc(-c4ccc5c(c4)c4cc(-c6ccc7oc8cccc(-c9ccc%10c(c9)c9ccccc9n%10-c9ccccc9)c8c7c6)ccc4n5-c4ccccc4)ccc32)cc1]
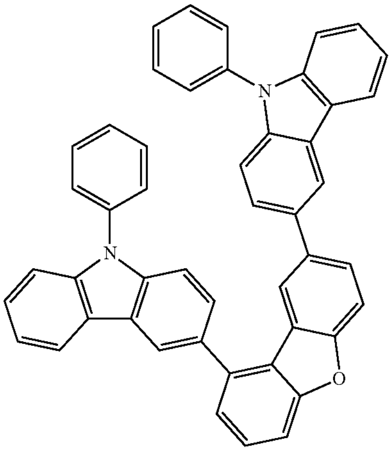 [SMILES: c1ccc(-n2c3ccccc3c3cc(-c4ccc5oc6cccc(-c7ccc8c(c7)c7ccccc7n8-c7ccccc7)c6c5c4)ccc32)cc1]
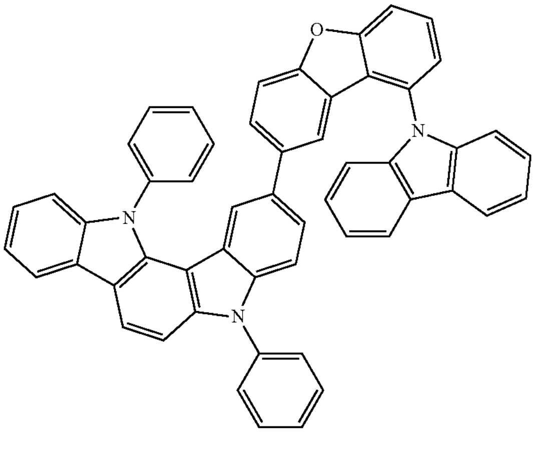 [SMILES: c1ccc(-n2c3ccc(-c4ccc5oc6cccc(-n7c8ccccc8c8ccccc87)c6c5c4)cc3c3c2ccc2c4ccccc4n(-c4ccccc4)c23)cc1]

TABLE 3-continued
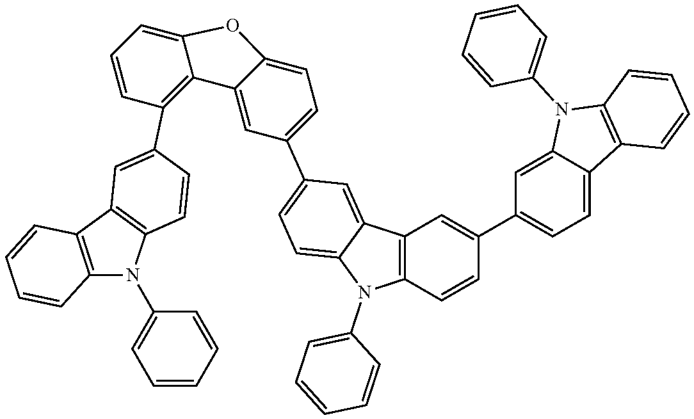 [SMILES: c1ccc(-n2c3ccc(-c4ccc5oc6cccc(-c7ccc8c(c7)c7ccccc7n8-c7ccccc7)c6c5c4)cc3c3cc(-c4ccc5c6ccccc6n(-c6ccccc6)c5c4)ccc32)cc1]
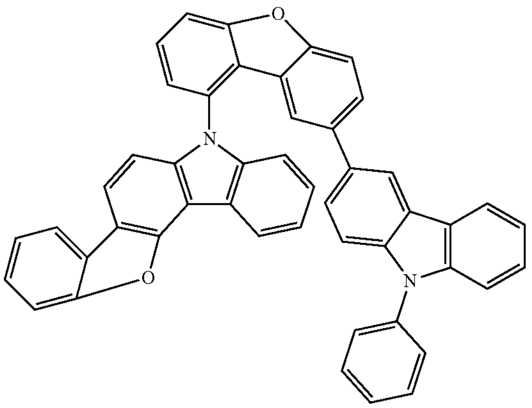 [SMILES: c1ccc(-n2c3ccccc3c3cc(-c4ccc5oc6cccc(-n7c8ccccc8c8c9oc%10ccccc%10c9ccc87)c6c5c4)ccc32)cc1]
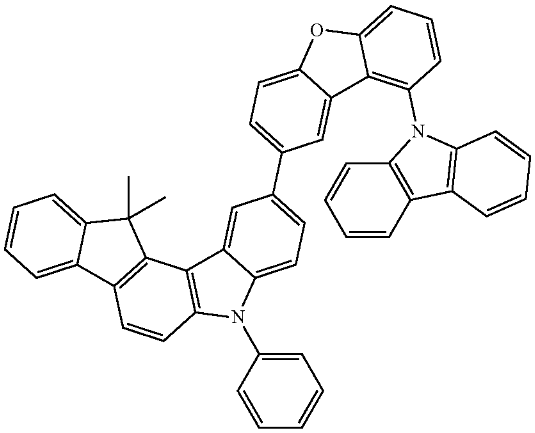 [SMILES: CC1(C)c2ccccc2-c2ccc3c(c21)c1cc(-c2ccc4oc5cccc(-n6c7ccccc7c7ccccc76)c5c4c2)ccc1n3-c1ccccc1]
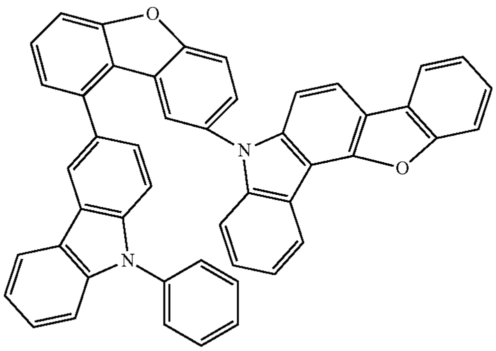 [SMILES: c1ccc(-n2c3ccccc3c3cc(-c4cccc5oc6ccc(-n7c8ccccc8c8c9oc%10ccccc%10c9ccc87)cc6c45)ccc32)cc1]

TABLE 3-continued
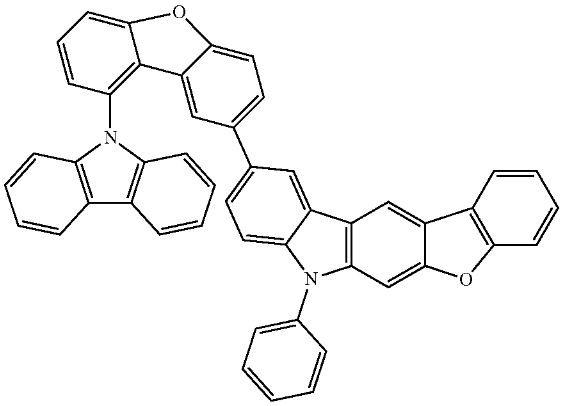 [SMILES: c1ccc(-n2c3ccc(-c4ccc5oc6cccc(-n7c8ccccc8c8ccccc87)c6c5c4)cc3c3cc4c(cc32)oc2ccccc24)cc1]
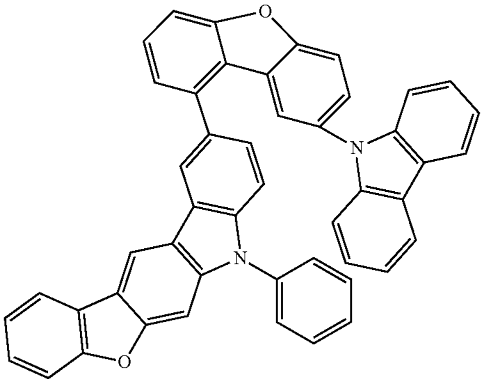 [SMILES: c1ccc(-n2c3ccc(-c4cccc5oc6ccc(-n7c8ccccc8c8ccccc87)cc6c45)cc3c3cc4c(cc32)oc2ccccc24)cc1]
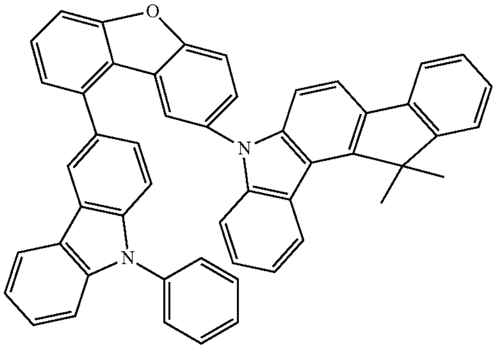 [SMILES: CC1(C)c2ccccc2-c2ccc3c(c21)c1ccccc1n3-c1ccc2oc3cccc(-c4ccc5c(c4)c4ccccc4n5-c4ccccc4)c3c2c1]
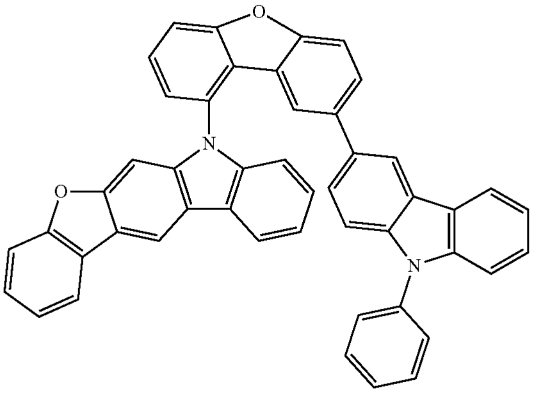 [SMILES: c1ccc(-n2c3ccccc3c3cc(-c4ccc5oc6cccc(-n7c8ccccc8c8cc9c(cc87)oc7ccccc79)c6c5c4)ccc32)cc1]

TABLE 3-continued
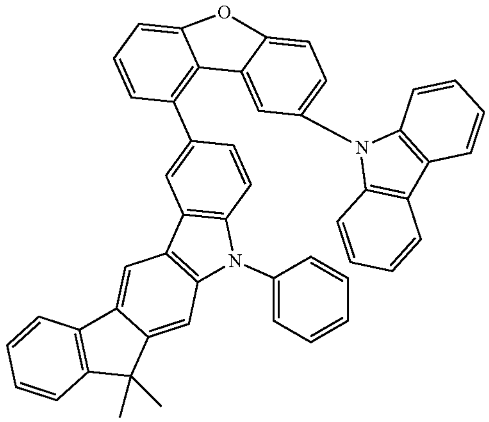 [SMILES: CC1(C)c2ccccc2-c2cc3c4cc(-c5cccc6oc7ccc(-n8c9ccccc9c9ccccc98)cc7c56)ccc4n(-c4ccccc4)c3cc21]
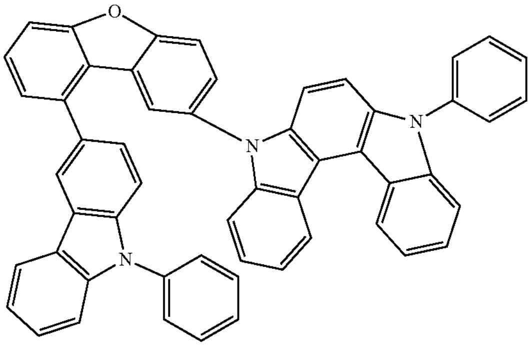 [SMILES: c1ccc(-n2c3ccccc3c3cc(-c4cccc5oc6ccc(-n7c8ccccc8c8c9c%10ccccc%10n(-c%10ccccc%10)c9ccc87)cc6c45)ccc32)cc1]
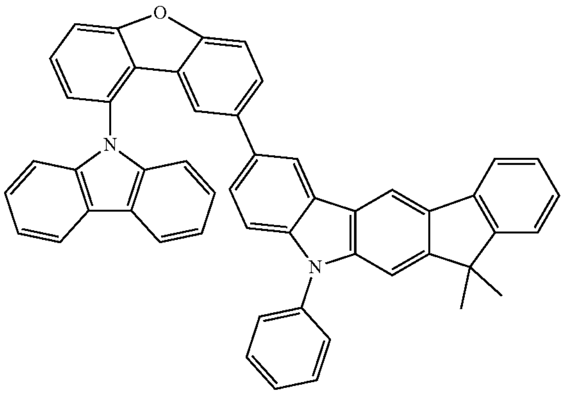 [SMILES: CC1(C)c2ccccc2-c2cc3c4cc(-c5ccc6oc7cccc(-n8c9ccccc9c9ccccc98)c7c6c5)ccc4n(-c4ccccc4)c3cc21]
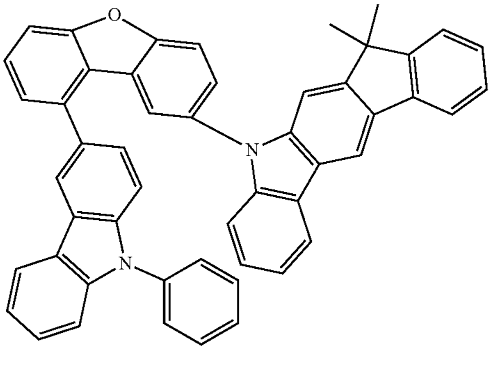 [SMILES: CC1(C)c2ccccc2-c2cc3c4ccccc4n(-c4ccc5oc6cccc(-c7ccc8c(c7)c7ccccc7n8-c7ccccc7)c6c5c4)c3cc21]

TABLE 3-continued
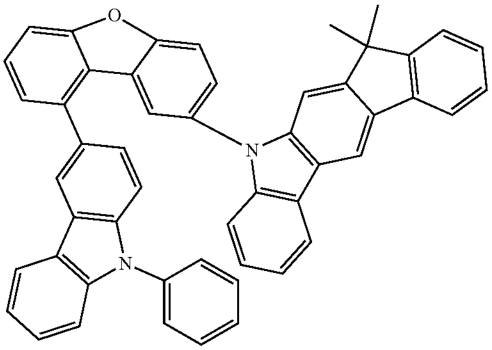 [SMILES: CC1(C)c2ccccc2-c2cc3c4ccccc4n(-c4ccc5oc6cccc(-c7ccc8c(c7)c7ccccc7n8-c7ccccc7)c6c5c4)c3cc21]
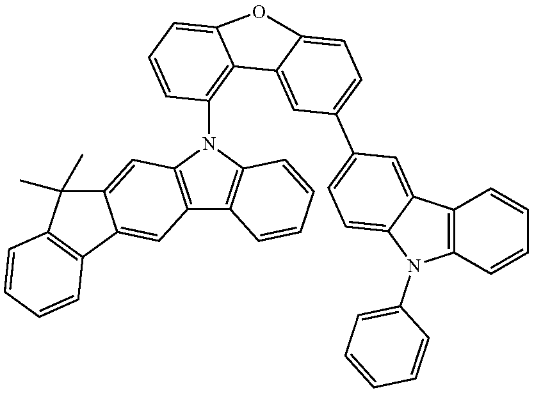 [SMILES: CC1(C)c2ccccc2-c2cc3c4ccccc4n(-c4cccc5oc6ccc(-c7ccc8c(c7)c7ccccc7n8-c7ccccc7)cc6c45)c3cc21]
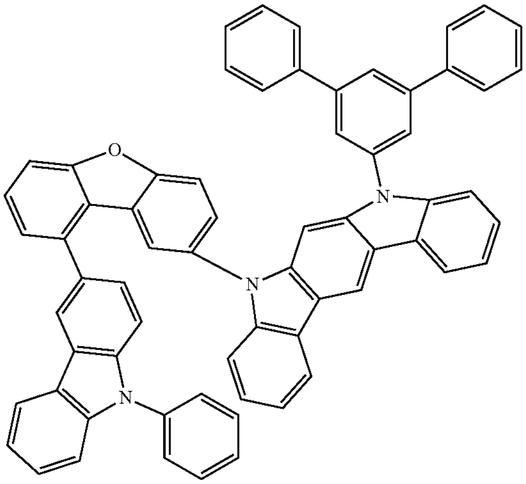 [SMILES: c1ccc(-c2cc(-c3ccccc3)cc(-n3c4ccccc4c4cc5c6ccccc6n(-c6ccc7oc8cccc(-c9ccc%10c(c9)c9ccccc9n%10-c9ccccc9)c8c7c6)c5cc43)c2)cc1]
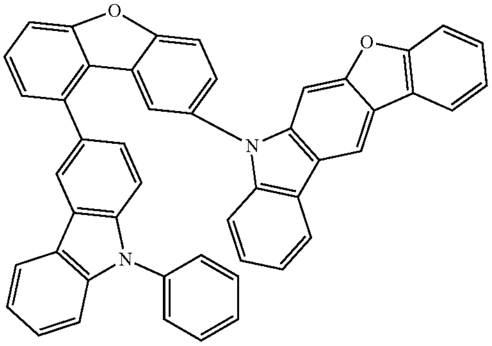 [SMILES: c1ccc(-n2c3ccccc3c3cc(-c4cccc5oc6ccc(-n7c8ccccc8c8cc9c(cc87)oc7ccccc79)cc6c45)ccc32)cc1]

TABLE 3-continued
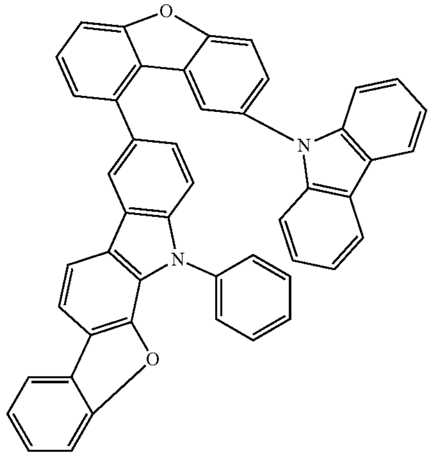 [SMILES: c1ccc(-n2c3ccc(-c4cccc5oc6ccc(-n7c8ccccc8c8ccccc87)cc6c45)cc3c3ccc4c5ccccc5oc4c32)cc1]
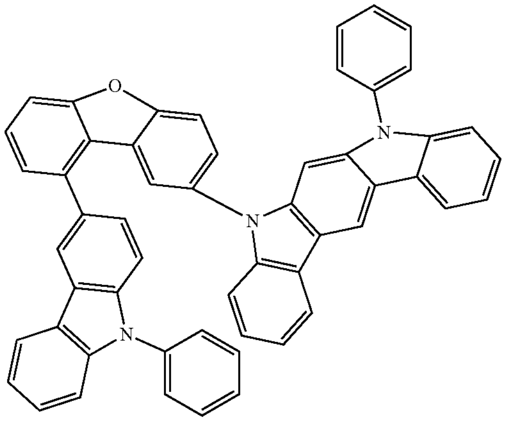 [SMILES: c1ccc(-n2c3ccccc3c3cc(-c4cccc5oc6ccc(-n7c8ccccc8c8cc9c%10ccccc%10n(-c%10ccccc%10)c9cc87)cc6c45)ccc32)cc1]
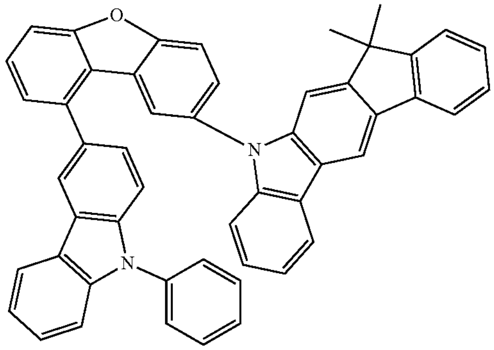 [SMILES: CC1(C)c2ccccc2-c2cc3c4ccccc4n(-c4ccc5oc6cccc(-c7ccc8c(c7)c7ccccc7n8-c7ccccc7)c6c5c4)c3cc21]
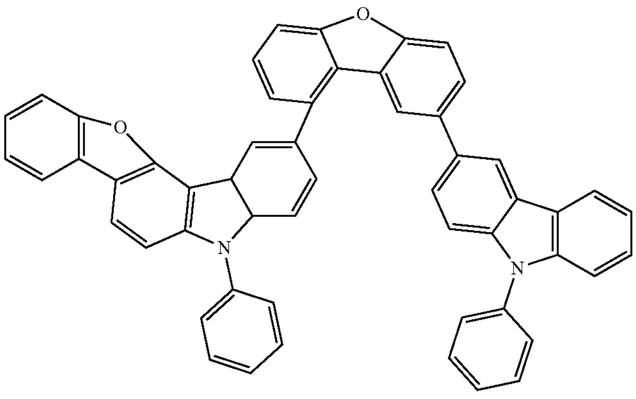 [SMILES: C1=CC2C(C=C1c1cccc3oc4ccc(-c5ccc6c(c5)c5ccccc5n6-c5ccccc5)cc4c13)c1c(ccc3c1oc1ccccc13)N2c1ccccc1]

TABLE 3-continued
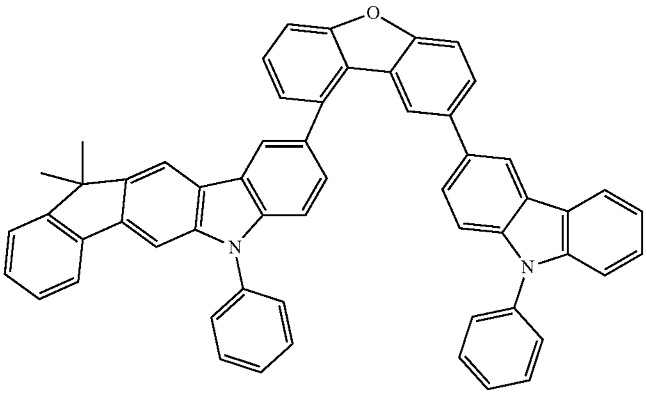 [SMILES: CC1(C)c2ccccc2-c2cc3c(cc21)c1cc(-c2cccc4oc5ccc(-c6ccc7c(c6)c6ccccc6n7-c6ccccc6)cc5c24)ccc1n3-c1ccccc1]
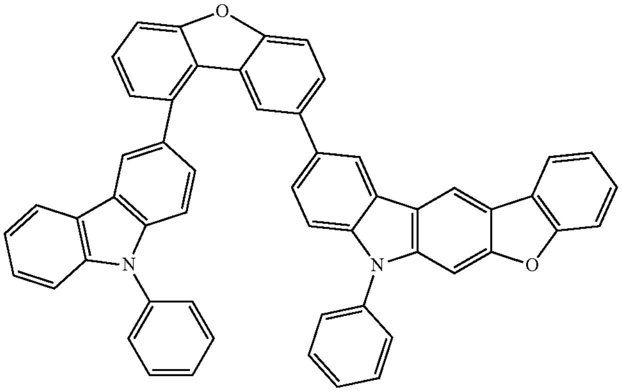 [SMILES: c1ccc(-n2c3ccccc3c3cc(-c4cccc5oc6ccc(-c7ccc8c(c7)c7cc9c(cc7n8-c7ccccc7)oc7ccccc79)cc6c45)ccc32)cc1]
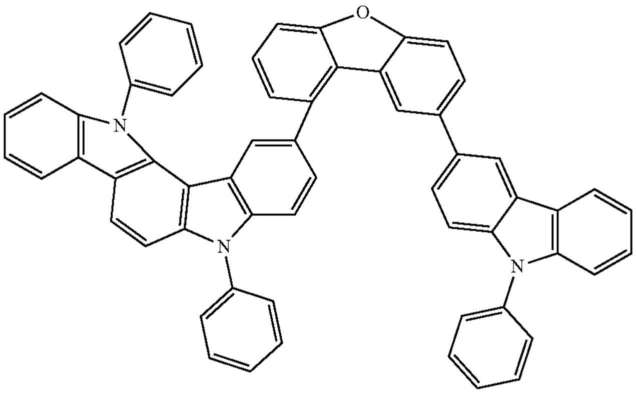 [SMILES: c1ccc(-n2c3ccccc3c3cc(-c4ccc5oc6cccc(-c7ccc8c(c7)c7c(ccc9c%10ccccc%10n(-c%10ccccc%10)c97)n8-c7ccccc7)c6c5c4)ccc32)cc1]
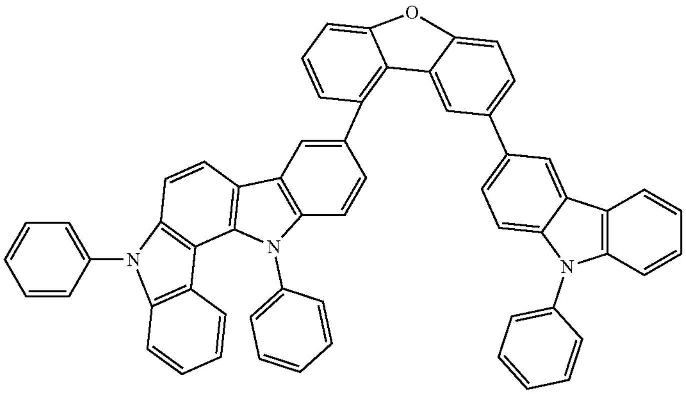 [SMILES: c1ccc(-n2c3ccccc3c3cc(-c4ccc5oc6cccc(-c7ccc8c(c7)c7ccc9c(c%10ccccc%10n9-c9ccccc9)c7n8-c7ccccc7)c6c5c4)ccc32)cc1]

TABLE 3-continued
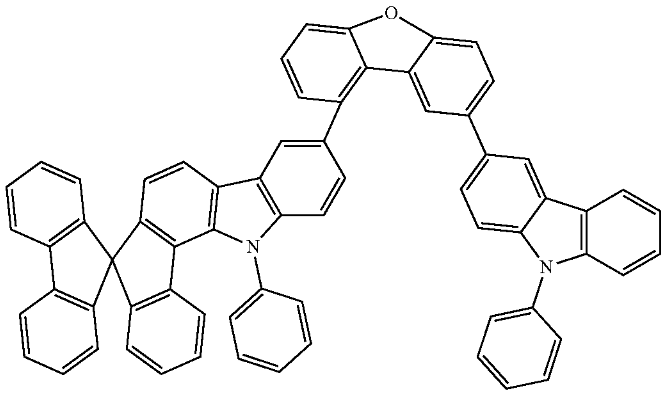 [SMILES: c1ccc(-n2c3ccccc3c3cc(-c4ccc5oc6cccc(-c7ccc8c(c7)c7ccc9c(c7n8-c7ccccc7)-c7ccccc7C97c8ccccc8-c8ccccc87)c6c5c4)ccc32)cc1]
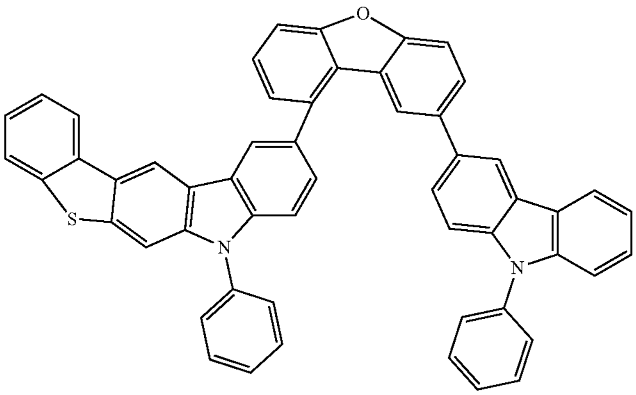 [SMILES: c1ccc(-n2c3ccccc3c3cc(-c4ccc5oc6cccc(-c7ccc8c(c7)c7cc9c(cc7n8-c7ccccc7)sc7ccccc79)c6c5c4)ccc32)cc1]
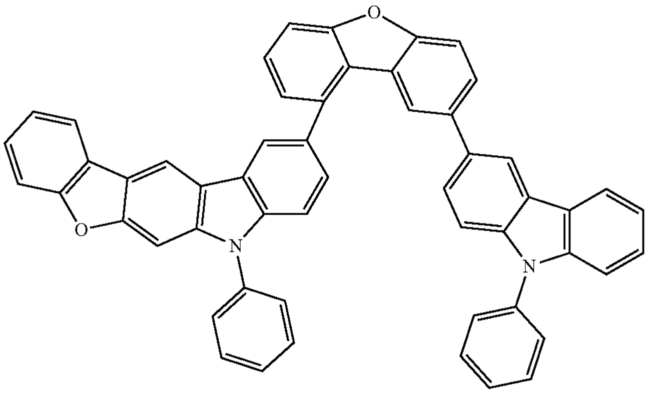 [SMILES: c1ccc(-n2c3ccccc3c3cc(-c4ccc5oc6cccc(-c7ccc8c(c7)c7cc9c(cc7n8-c7ccccc7)oc7ccccc79)c6c5c4)ccc32)cc1]
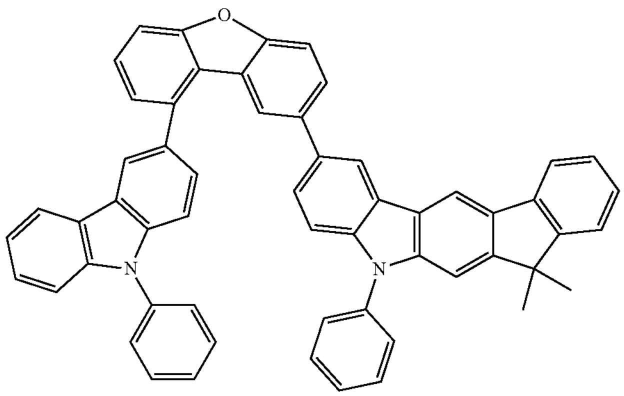 [SMILES: CC1(C)c2ccccc2-c2cc3c4cc(-c5ccc6oc7cccc(-c8ccc9c(c8)c8ccccc8n9-c8ccccc8)c7c6c5)ccc4n(-c4ccccc4)c3cc21]

TABLE 3-continued
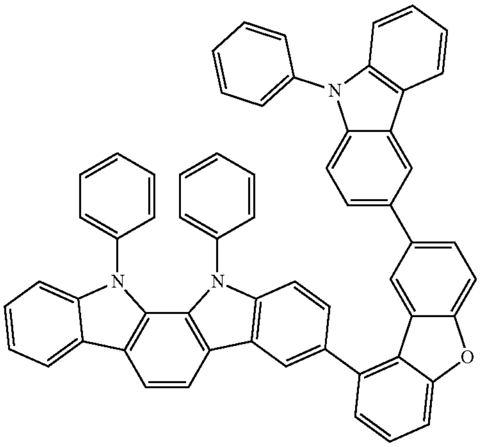 [SMILES: c1ccc(-n2c3ccccc3c3cc(-c4ccc5oc6cccc(-c7ccc8c(c7)c7ccc9c%10ccccc%10n(-c%10ccccc%10)c9c7n8-c7ccccc7)c6c5c4)ccc32)cc1]
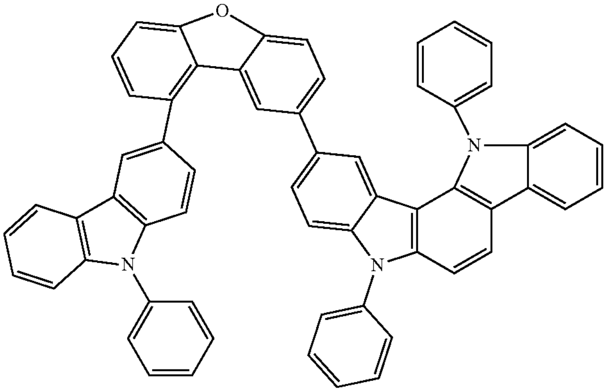 [SMILES: c1ccc(-n2c3ccccc3c3cc(-c4cccc5oc6ccc(-c7ccc8c(c7)c7c(ccc9c%10ccccc%10n(-c%10ccccc%10)c97)n8-c7ccccc7)cc6c45)ccc32)cc1]
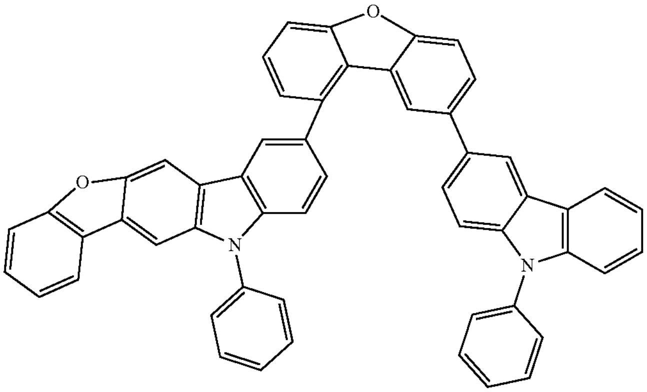 [SMILES: c1ccc(-n2c3ccccc3c3cc(-c4ccc5oc6cccc(-c7ccc8c(c7)c7cc9oc%10ccccc%10c9cc7n8-c7ccccc7)c6c5c4)ccc32)cc1]
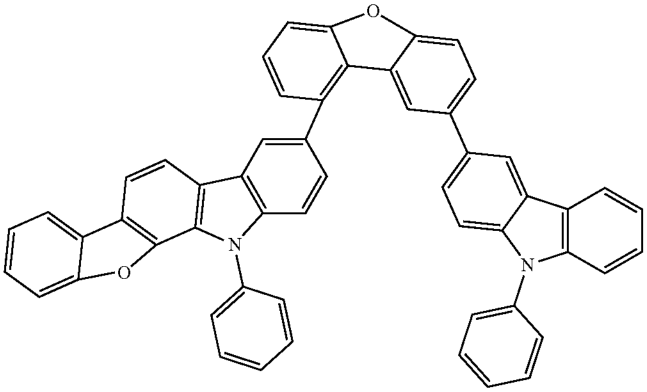 [SMILES: c1ccc(-n2c3ccccc3c3cc(-c4ccc5oc6cccc(-c7ccc8c(c7)c7ccc9c%10ccccc%10oc9c7n8-c7ccccc7)c6c5c4)ccc32)cc1]

TABLE 3-continued
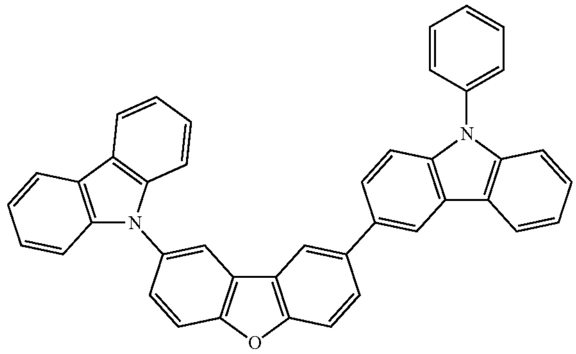 [SMILES: c1ccc(-n2c3ccccc3c3cc(-c4ccc5oc6ccc(-n7c8ccccc8c8ccccc87)cc6c5c4)ccc32)cc1]
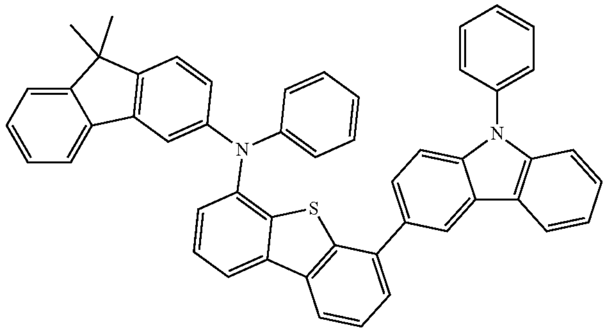 [SMILES: CC1(C)c2ccccc2-c2cc(N(c3ccccc3)c3cccc4c3sc3c(-c5ccc6c(c5)c5ccccc5n6-c5ccccc5)cccc34)ccc21]
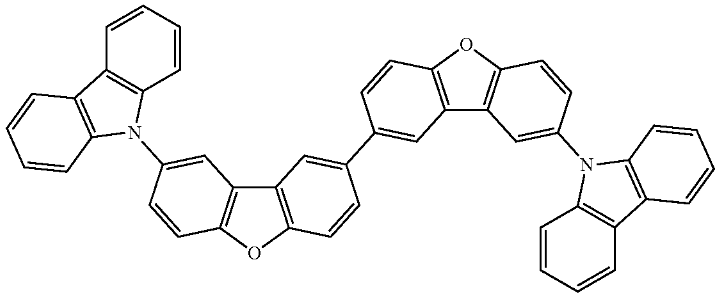 [SMILES: c1ccc2c(c1)c1ccccc1n2-c1ccc2oc3ccc(-c4ccc5oc6ccc(-n7c8ccccc8c8ccccc87)cc6c5c4)cc3c2c1]
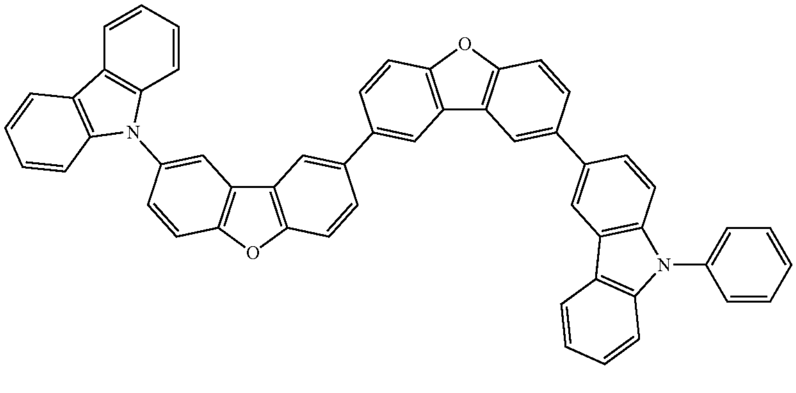 [SMILES: c1ccc(-n2c3ccccc3c3cc(-c4ccc5oc6ccc(-c7ccc8oc9ccc(-n%10c%11ccccc%11c%11ccccc%11%10)cc9c8c7)cc6c5c4)ccc32)cc1]

TABLE 3-continued
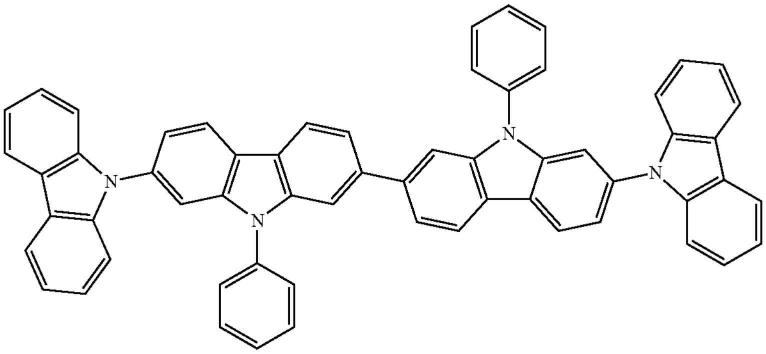 [SMILES: c1ccc(-n2c3cc(-c4ccc5c6ccc(-n7c8ccccc8c8ccccc87)cc6n(-c6ccccc6)c5c4)ccc3c3ccc(-n4c5ccccc5c5ccccc54)cc32)cc1]
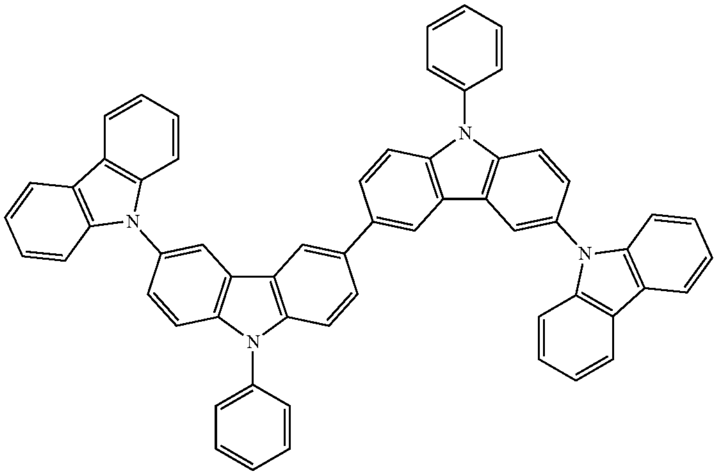 [SMILES: c1ccc(-n2c3ccc(-c4ccc5c(c4)c4cc(-n6c7ccccc7c7ccccc76)ccc4n5-c4ccccc4)cc3c3cc(-n4c5ccccc5c5ccccc54)ccc32)cc1]
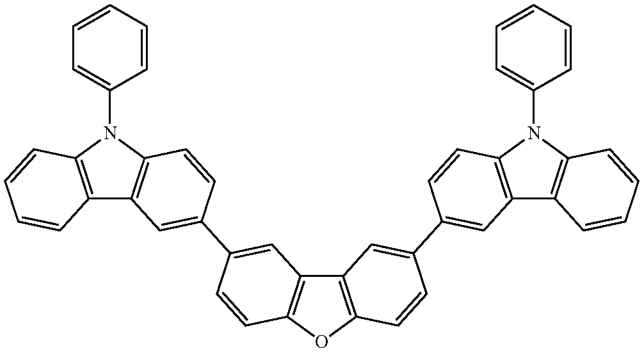 [SMILES: c1ccc(-n2c3ccccc3c3cc(-c4ccc5oc6ccc(-c7ccc8c(c7)c7ccccc7n8-c7ccccc7)cc6c5c4)ccc32)cc1]

TABLE 3-continued
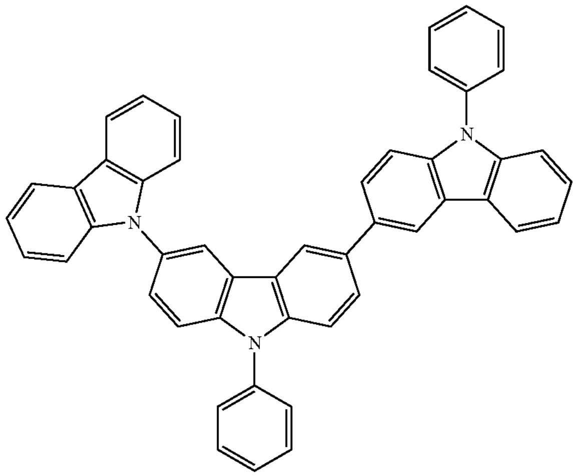 [SMILES: c1ccc(-n2c3ccccc3c3cc(-c4ccc5c(c4)c4cc(-n6c7ccccc7c7ccccc76)ccc4n5-c4ccccc4)ccc32)cc1]
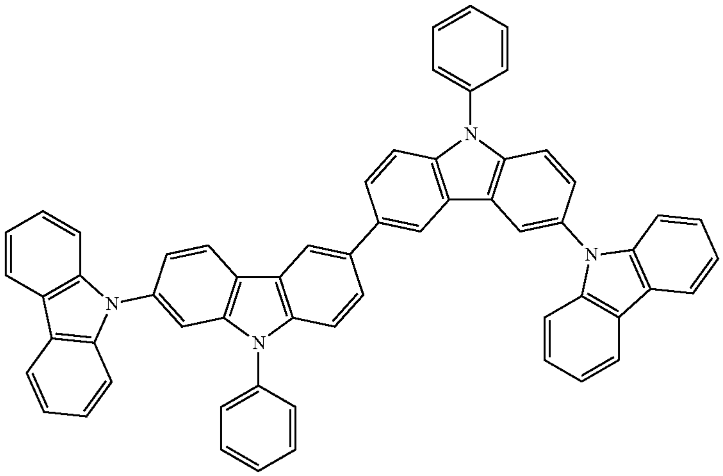 [SMILES: c1ccc(-n2c3ccc(-c4ccc5c(c4)c4ccc(-n6c7ccccc7c7ccccc76)cc4n5-c4ccccc4)cc3c3cc(-n4c5ccccc5c5ccccc54)ccc32)cc1]
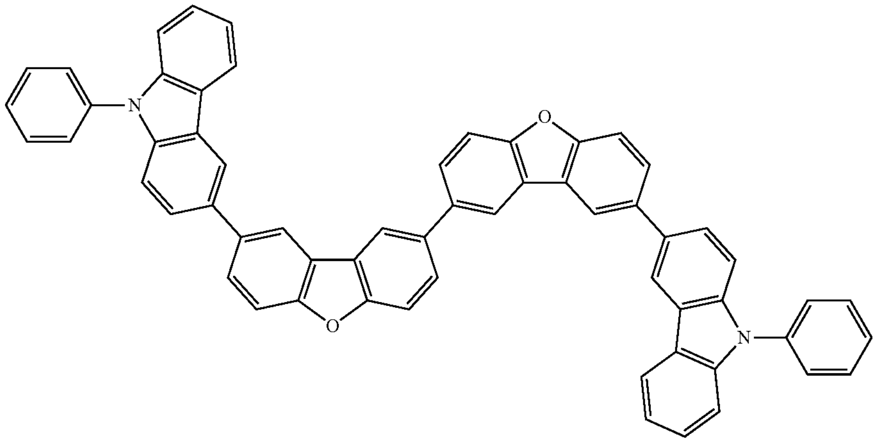 [SMILES: c1ccc(-n2c3ccccc3c3cc(-c4ccc5oc6ccc(-c7ccc8oc9ccc(-c%10ccc%11c(c%10)c%10ccccc%10n%11-c%10ccccc%10)cc9c8c7)cc6c5c4)ccc32)cc1]

TABLE 3-continued
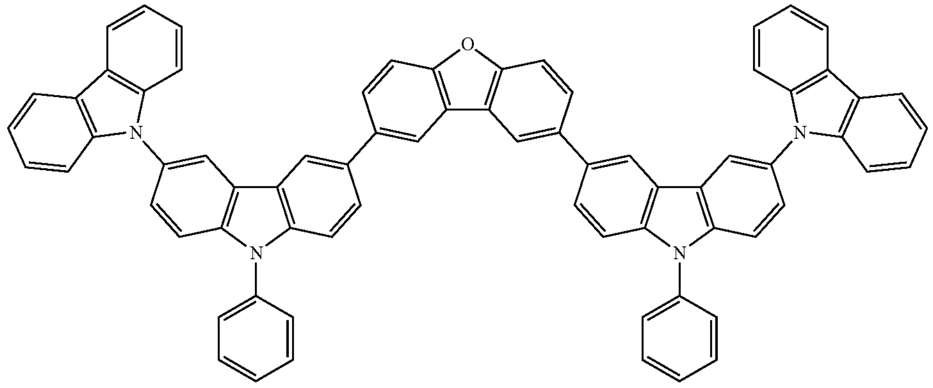 [SMILES: c1ccc(-n2c3ccc(-c4ccc5oc6ccc(-c7ccc8c(c7)c7cc(-n9c%10ccccc%10c%10ccccc%109)ccc7n8-c7ccccc7)cc6c5c4)cc3c3cc(-n4c5ccccc5c5ccccc54)ccc32)cc1]
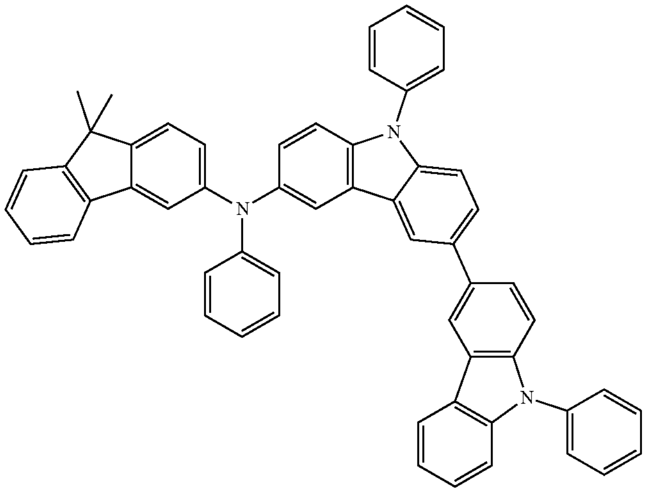 [SMILES: CC1(C)c2ccccc2-c2cc(N(c3ccccc3)c3ccc4c(c3)c3cc(-c5ccc6c(c5)c5ccccc5n6-c5ccccc5)ccc3n4-c3ccccc3)ccc21]
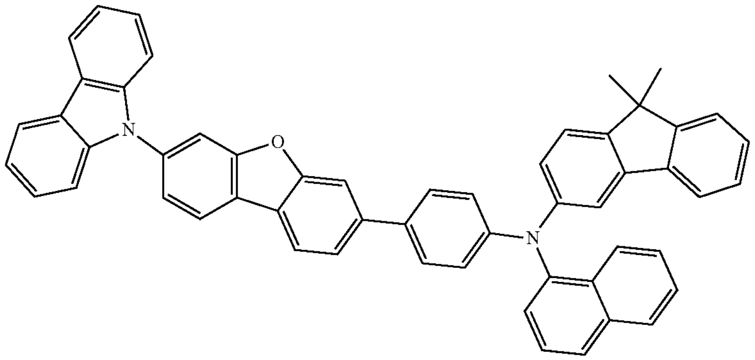 [SMILES: CC1(C)c2ccccc2-c2cc(N(c3ccc(-c4ccc5c(c4)oc4cc(-n6c7ccccc7c7ccccc76)ccc45)cc3)c3cccc4ccccc34)ccc21]
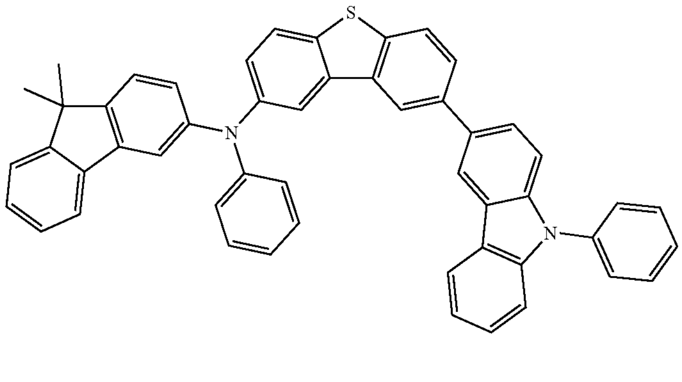 [SMILES: CC1(C)c2ccccc2-c2cc(N(c3ccccc3)c3ccc4sc5ccc(-c6ccc7c(c6)c6ccccc6n7-c6ccccc6)cc5c4c3)ccc21]

TABLE 3-continued
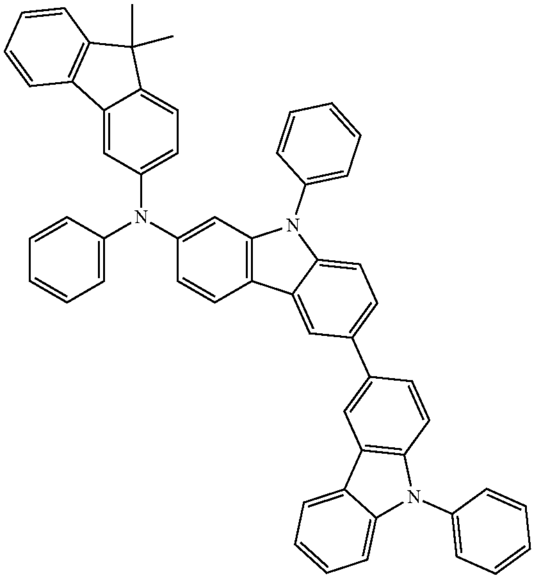 [SMILES: CC1(C)c2ccccc2-c2cc(N(c3ccccc3)c3ccc4c5cc(-c6ccc7c(c6)c6ccccc6n7-c6ccccc6)ccc5n(-c5ccccc5)c4c3)ccc21]
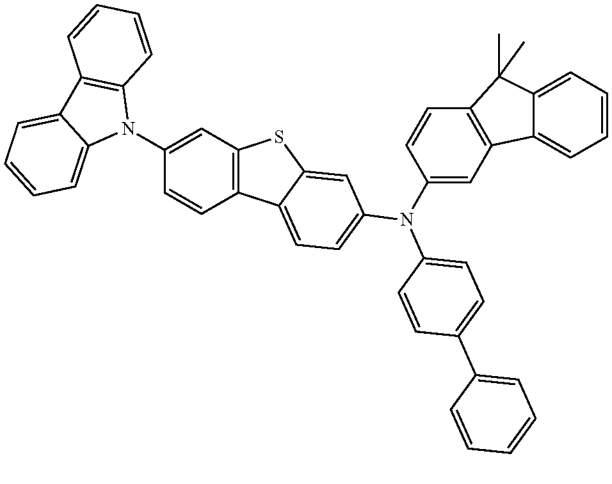 [SMILES: CC1(C)c2ccccc2-c2cc(N(c3ccc(-c4ccccc4)cc3)c3ccc4c(c3)sc3cc(-n5c6ccccc6c6ccccc65)ccc34)ccc21]
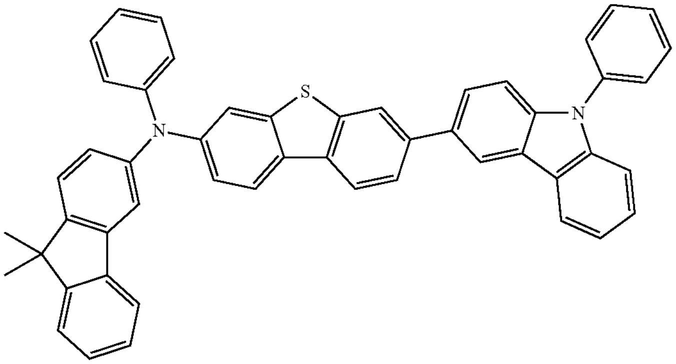 [SMILES: CC1(C)c2ccccc2-c2cc(N(c3ccccc3)c3ccc4c(c3)sc3cc(-c5ccc6c(c5)c5ccccc5n6-c5ccccc5)ccc34)ccc21]

TABLE 3-continued
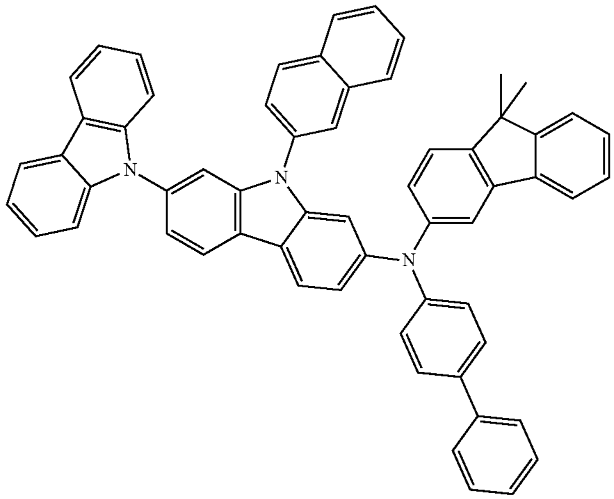 [SMILES: CC1(C)c2ccccc2-c2cc(N(c3ccc(-c4ccccc4)cc3)c3ccc4c5ccc(-n6c7ccccc7c7ccccc76)cc5n(-c5ccc6ccccc6c5)c4c3)ccc21]
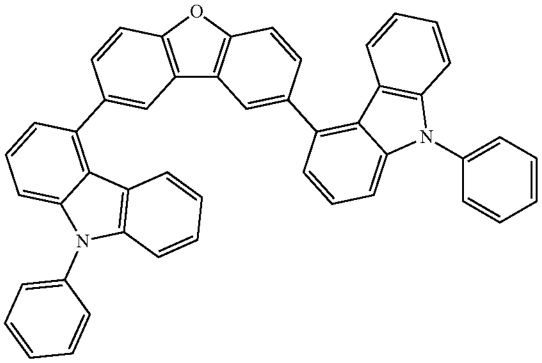 [SMILES: c1ccc(-n2c3ccccc3c3c(-c4ccc5oc6ccc(-c7cccc8c7c7ccccc7n8-c7ccccc7)cc6c5c4)cccc32)cc1]
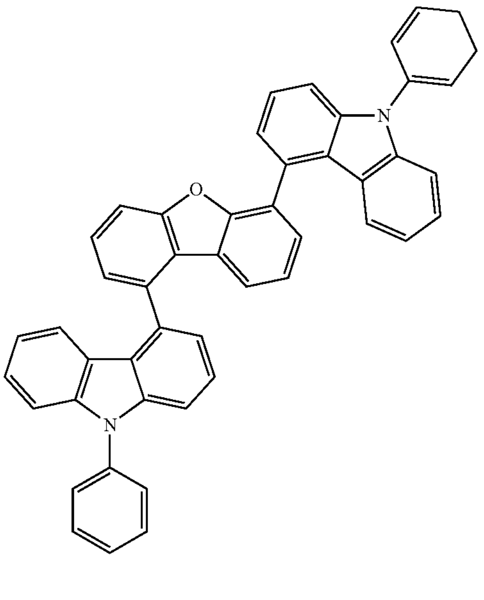 [SMILES: C1=CC(n2c3ccccc3c3c(-c4cccc5c4oc4cccc(-c6cccc7c6c6ccccc6n7-c6ccccc6)c45)cccc32)=CCC1]

TABLE 3-continued
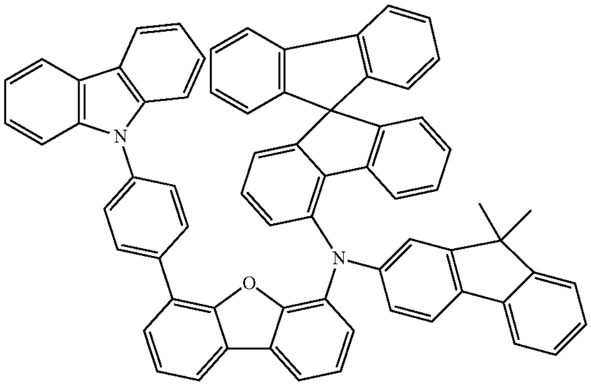 [SMILES: CC1(C)c2ccccc2-c2ccc(N(c3cccc4c3-c3ccccc3C43c4ccccc4-c4ccccc43)c3cccc4c3oc3c(-c5ccc(-n6c7ccccc7c7ccccc76)cc5)cccc34)cc21]
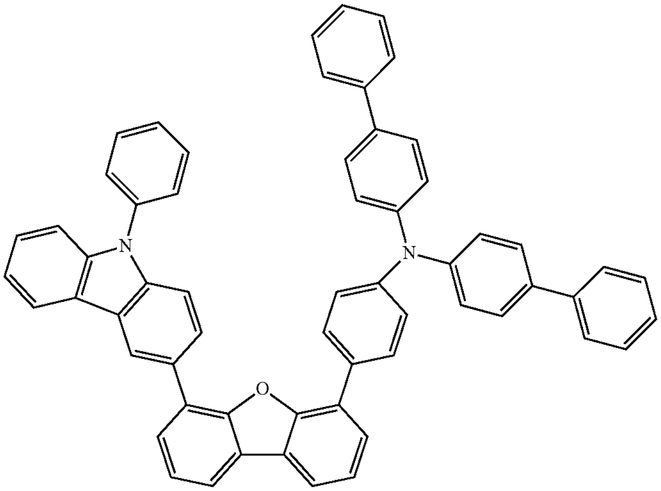 [SMILES: c1ccc(-c2ccc(N(c3ccc(-c4ccccc4)cc3)c3ccc(-c4cccc5c4oc4c(-c6ccc7c(c6)c6ccccc6n7-c6ccccc6)cccc45)cc3)cc2)cc1]
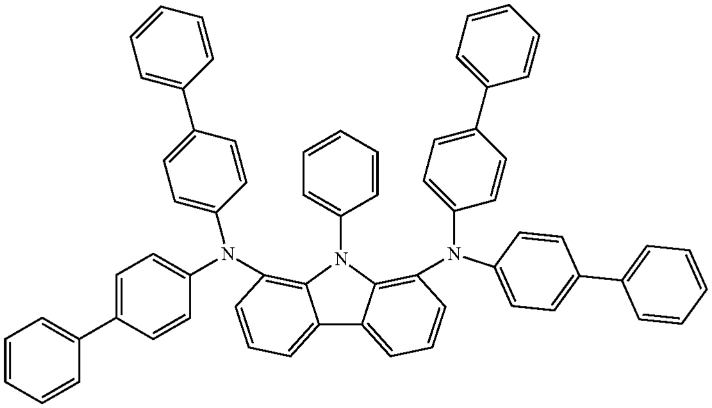 [SMILES: c1ccc(-c2ccc(N(c3ccc(-c4ccccc4)cc3)c3cccc4c5cccc(N(c6ccc(-c7ccccc7)cc6)c6ccc(-c7ccccc7)cc6)c5n(-c5ccccc5)c34)cc2)cc1]

TABLE 3-continued
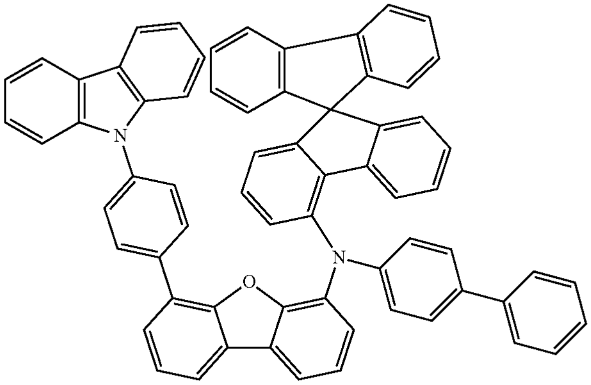 [SMILES: c1ccc(-c2ccc(N(c3cccc4c3-c3ccccc3C43c4ccccc4-c4ccccc43)c3cccc4c3oc3c(-c5ccc(-n6c7ccccc7c7ccccc76)cc5)cccc34)cc2)cc1]
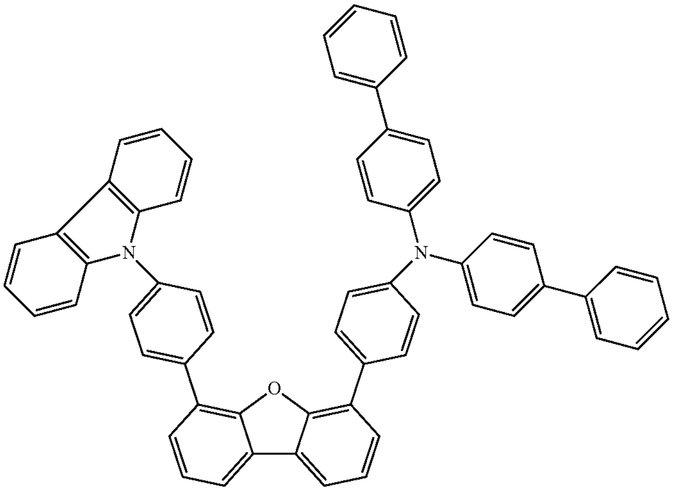 [SMILES: c1ccc(-c2ccc(N(c3ccc(-c4ccccc4)cc3)c3ccc(-c4cccc5c4oc4c(-c6ccc(-n7c8ccccc8c8ccccc87)cc6)cccc45)cc3)cc2)cc1]
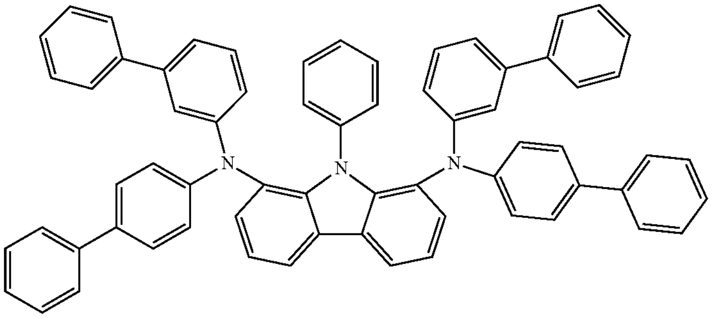 [SMILES: c1ccc(-c2ccc(N(c3cccc(-c4ccccc4)c3)c3cccc4c5cccc(N(c6ccc(-c7ccccc7)cc6)c6cccc(-c7ccccc7)c6)c5n(-c5ccccc5)c34)cc2)cc1]
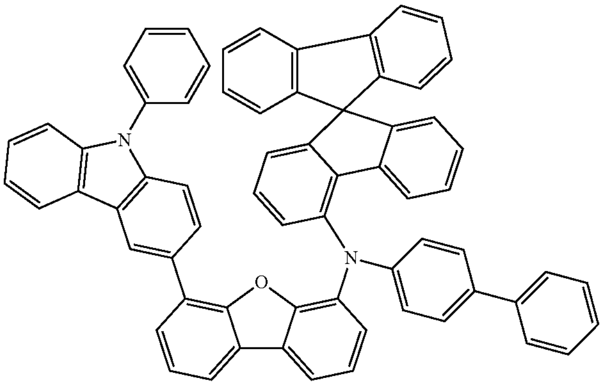 [SMILES: c1ccc(-c2ccc(N(c3cccc4c3-c3ccccc3C43c4ccccc4-c4ccccc43)c3cccc4c3oc3c(-c5ccc6c(c5)c5ccccc5n6-c5ccccc5)cccc34)cc2)cc1]

TABLE 3-continued
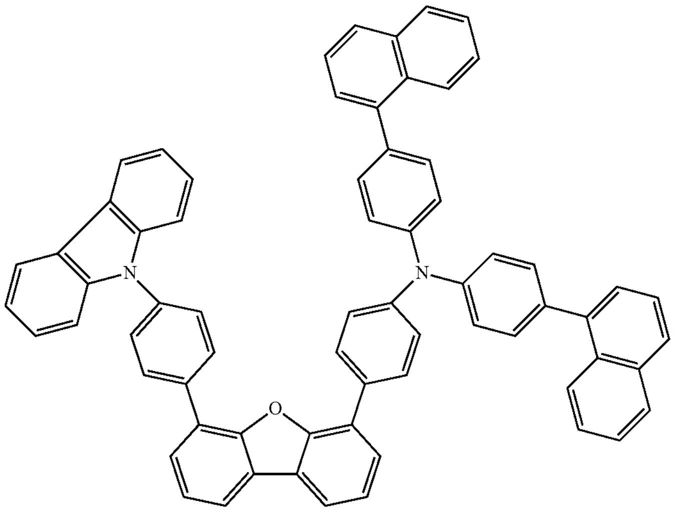 [SMILES: c1ccc2c(-c3ccc(N(c4ccc(-c5cccc6ccccc56)cc4)c4ccc(-c5cccc6c5oc5c(-c7ccc(-n8c9ccccc9c9ccccc98)cc7)cccc56)cc4)cc3)cccc2c1]
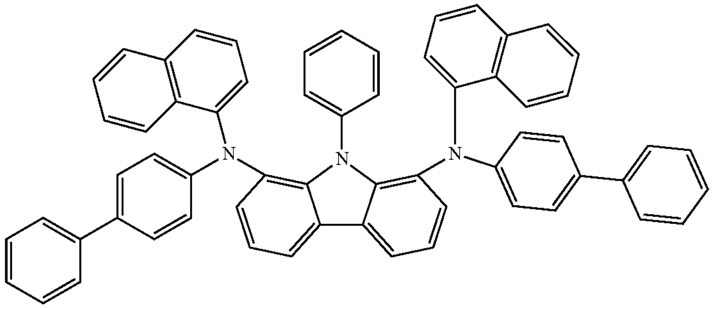 [SMILES: c1ccc(-c2ccc(N(c3cccc4ccccc34)c3cccc4c5cccc(N(c6ccc(-c7ccccc7)cc6)c6cccc7ccccc67)c5n(-c5ccccc5)c34)cc2)cc1]
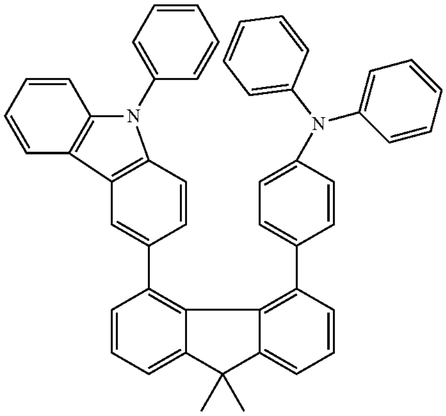 [SMILES: CC1(C)c2cccc(-c3ccc(N(c4ccccc4)c4ccccc4)cc3)c2-c2c(-c3ccc4c(c3)c3ccccc3n4-c3ccccc3)cccc21]

TABLE 3-continued
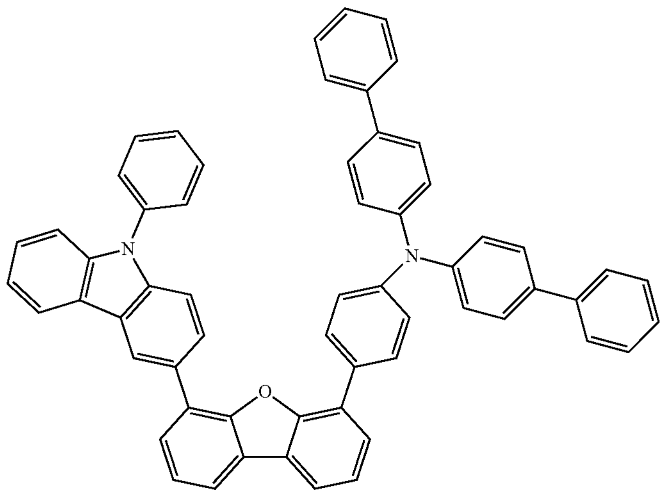 [SMILES: c1ccc(-c2ccc(N(c3ccc(-c4ccccc4)cc3)c3ccc(-c4cccc5c4oc4c(-c6ccc7c(c6)c6ccccc6n7-c6ccccc6)cccc45)cc3)cc2)cc1]
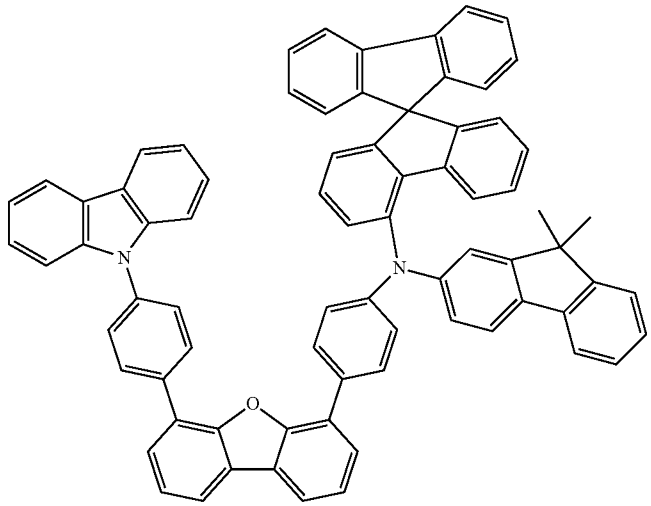 [SMILES: CC1(C)c2ccccc2-c2ccc(N(c3ccc(-c4cccc5c4oc4c(-c6ccc(-n7c8ccccc8c8ccccc87)cc6)cccc45)cc3)c3cccc4c3-c3ccccc3C43c4ccccc4-c4ccccc43)cc21]
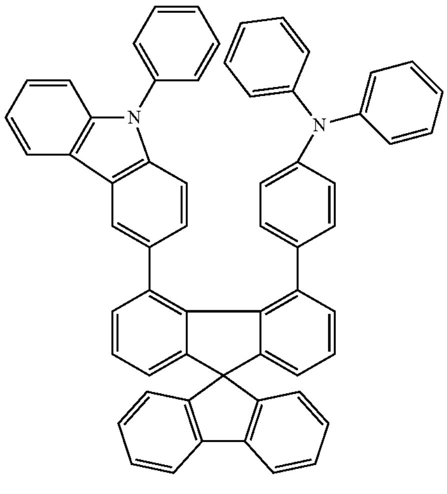 [SMILES: c1ccc(N(c2ccccc2)c2ccc(-c3cccc4c3-c3c(-c5ccc6c(c5)c5ccccc5n6-c5ccccc5)cccc3C43c4ccccc4-c4ccccc43)cc2)cc1]

TABLE 3-continued
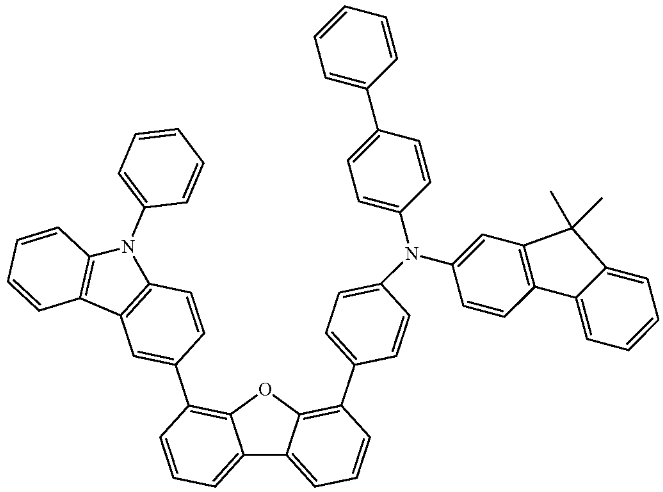 [SMILES: CC1(C)c2ccccc2-c2ccc(N(c3ccc(-c4ccccc4)cc3)c3ccc(-c4cccc5c4oc4c(-c6ccc7c(c6)c6ccccc6n7-c6ccccc6)cccc45)cc3)cc21]
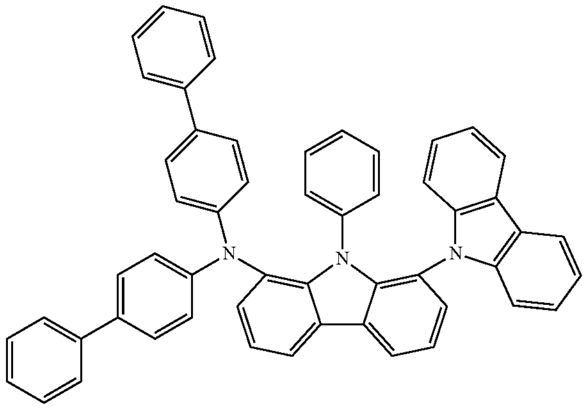 [SMILES: c1ccc(-c2ccc(N(c3ccc(-c4ccccc4)cc3)c3cccc4c5cccc(-n6c7ccccc7c7ccccc76)c5n(-c5ccccc5)c34)cc2)cc1]
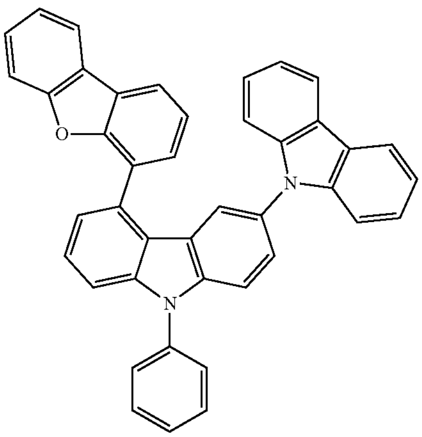 [SMILES: c1ccc(-n2c3ccc(-n4c5ccccc5c5ccccc54)cc3c3c(-c4cccc5c4oc4ccccc45)cccc32)cc1]

TABLE 3-continued
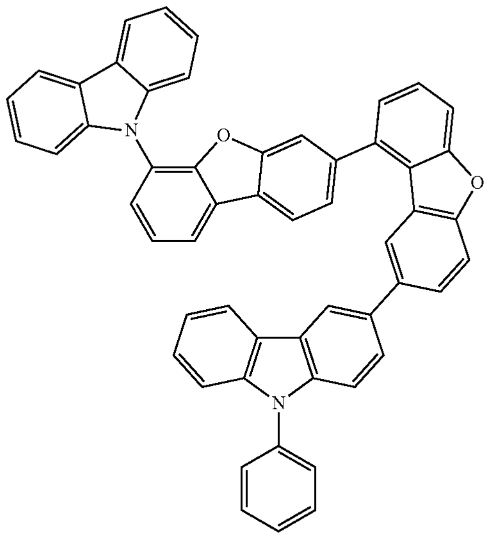 [SMILES: c1ccc(-n2c3ccccc3c3cc(-c4ccc5oc6cccc(-c7ccc8c(c7)oc7c(-n9c%10ccccc%10c%10ccccc%109)cccc78)c6c5c4)ccc32)cc1]
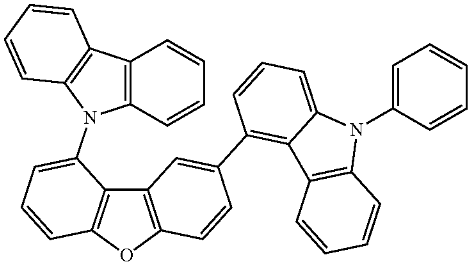 [SMILES: c1ccc(-n2c3ccccc3c3c(-c4ccc5oc6cccc(-n7c8ccccc8c8ccccc87)c6c5c4)cccc32)cc1]
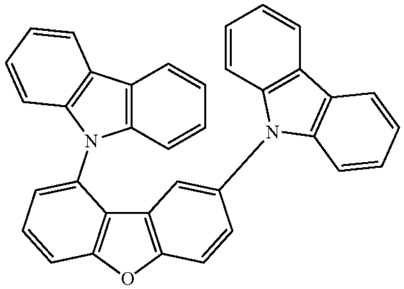 [SMILES: c1cc(-n2c3ccccc3c3ccccc32)c2c(c1)oc1ccc(-n3c4ccccc4c4ccccc43)cc12]
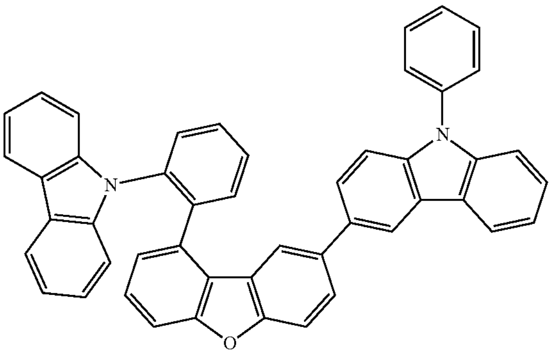 [SMILES: c1ccc(-n2c3ccccc3c3cc(-c4ccc5oc6cccc(-c7ccccc7-n7c8ccccc8c8ccccc87)c6c5c4)ccc32)cc1]

TABLE 3-continued
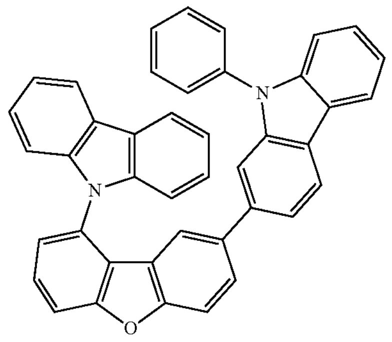 [SMILES: c1ccc(-n2c3ccccc3c3ccc(-c4ccc5oc6cccc(-n7c8ccccc8c8ccccc87)c6c5c4)cc32)cc1]
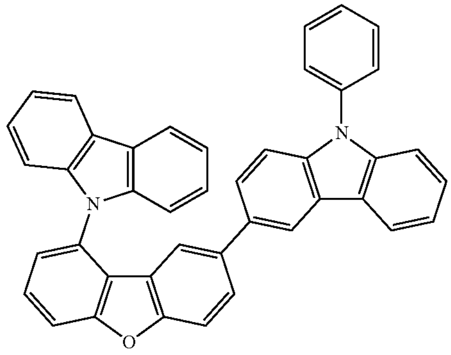 [SMILES: c1ccc(-n2c3ccccc3c3cc(-c4ccc5oc6cccc(-n7c8ccccc8c8ccccc87)c6c5c4)ccc32)cc1]
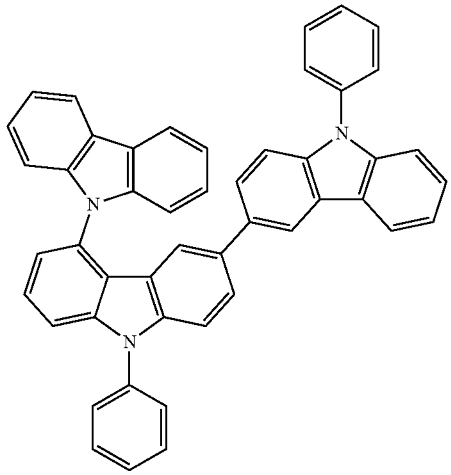 [SMILES: c1ccc(-n2c3ccccc3c3cc(-c4ccc5c(c4)c4c(-n6c7ccccc7c7ccccc76)cccc4n5-c4ccccc4)ccc32)cc1]

TABLE 3-continued
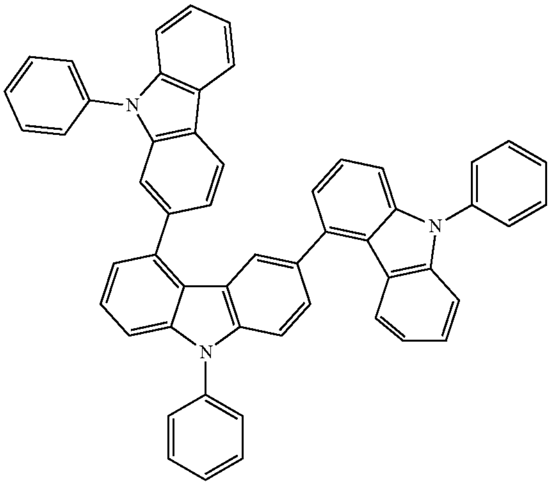 [SMILES: c1ccc(-n2c3ccccc3c3ccc(-c4cccc5c4c4cc(-c6cccc7c6c6ccccc6n7-c6ccccc6)ccc4n5-c4ccccc4)cc32)cc1]
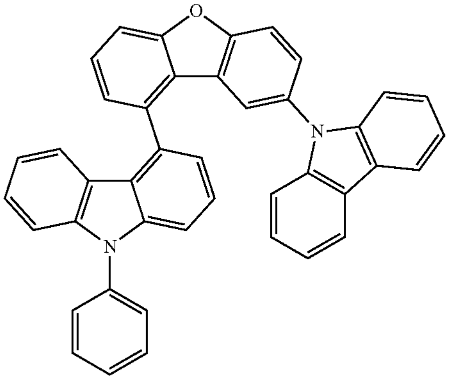 [SMILES: c1ccc(-n2c3ccccc3c3c(-c4cccc5oc6ccc(-n7c8ccccc8c8ccccc87)cc6c45)cccc32)cc1]
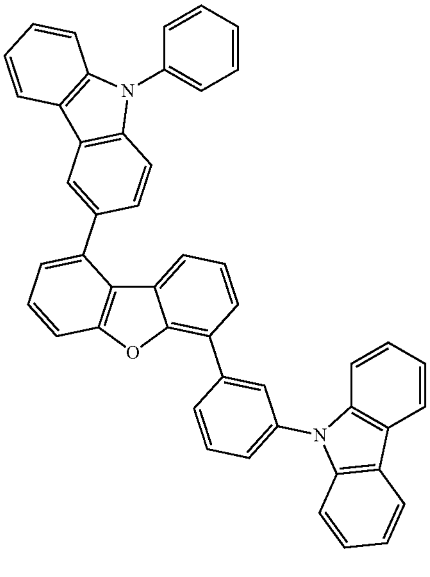 [SMILES: c1ccc(-n2c3ccccc3c3cc(-c4cccc5oc6c(-c7cccc(-n8c9ccccc9c9ccccc98)c7)cccc6c45)ccc32)cc1]

TABLE 3-continued
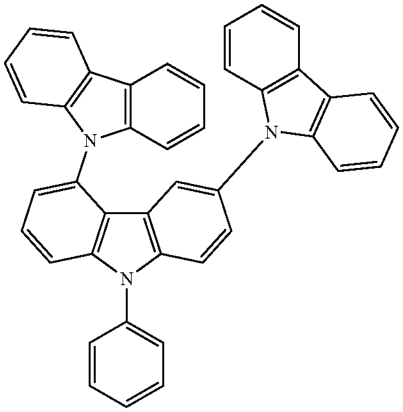 [SMILES: c1ccc(-n2c3ccc(-n4c5ccccc5c5ccccc54)cc3c3c(-n4c5ccccc5c5ccccc54)cccc32)cc1]
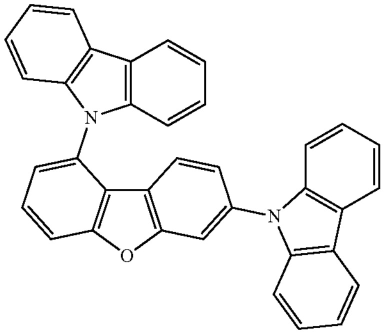 [SMILES: c1cc(-n2c3ccccc3c3ccccc32)c2c(c1)oc1cc(-n3c4ccccc4c4ccccc43)ccc12]
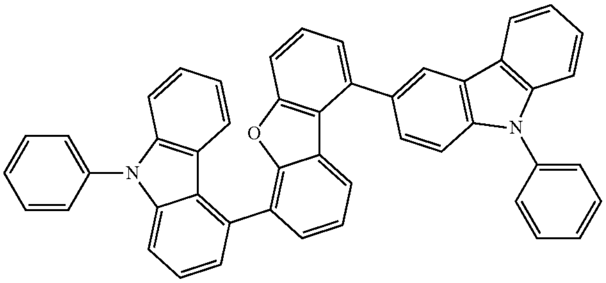 [SMILES: c1ccc(-n2c3ccccc3c3cc(-c4cccc5oc6c(-c7cccc8c7c7ccccc7n8-c7ccccc7)cccc6c45)ccc32)cc1]
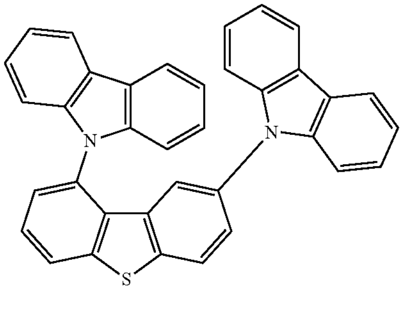 [SMILES: c1cc(-n2c3ccccc3c3ccccc32)c2c(c1)sc1ccc(-n3c4ccccc4c4ccccc43)cc12]

TABLE 3-continued
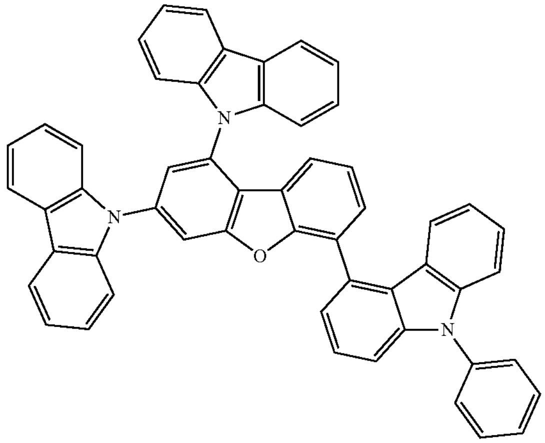 [SMILES: c1ccc(-n2c3ccccc3c3c(-c4cccc5c4oc4cc(-n6c7ccccc7c7ccccc76)cc(-n6c7ccccc7c7ccccc76)c45)cccc32)cc1]
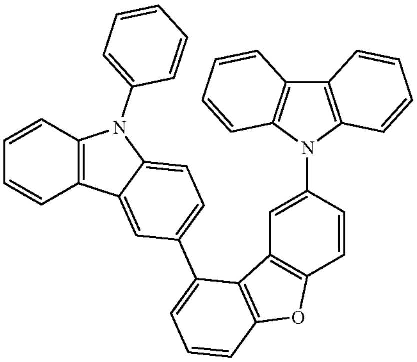 [SMILES: c1ccc(-n2c3ccccc3c3cc(-c4cccc5oc6ccc(-n7c8ccccc8c8ccccc87)cc6c45)ccc32)cc1]
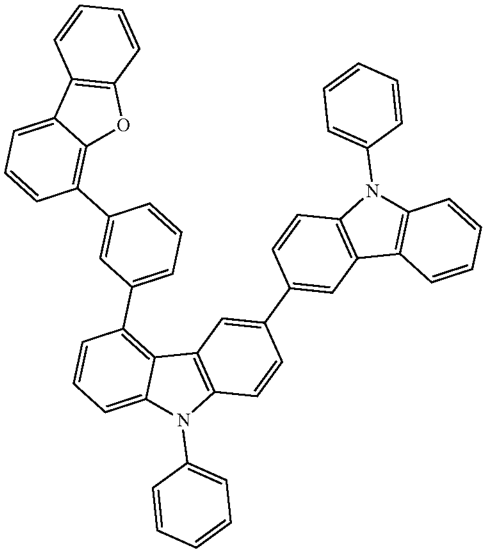 [SMILES: c1ccc(-n2c3ccccc3c3cc(-c4ccc5c(c4)c4c(-c6cccc(-c7cccc8c7oc7ccccc78)c6)cccc4n5-c4ccccc4)ccc32)cc1]

TABLE 3-continued
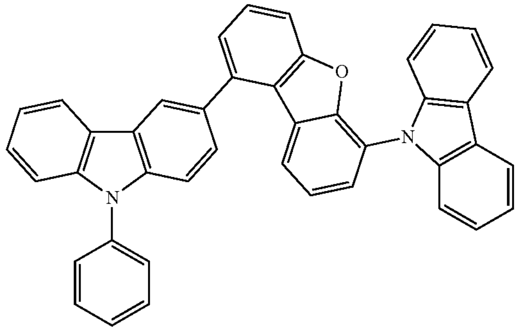 [SMILES: c1ccc(-n2c3ccccc3c3cc(-c4cccc5oc6c(-n7c8ccccc8c8ccccc87)cccc6c45)ccc32)cc1]
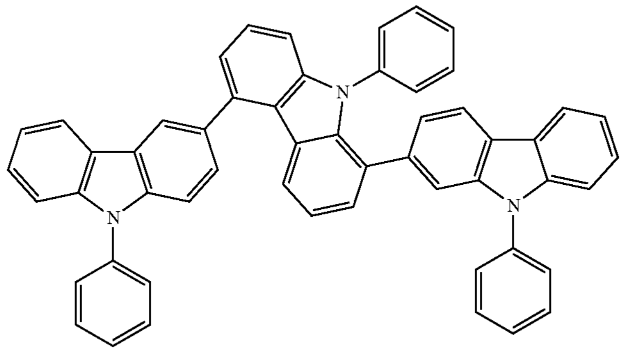 [SMILES: c1ccc(-n2c3ccccc3c3cc(-c4cccc5c4c4cccc(-c6ccc7c8ccccc8n(-c8ccccc8)c7c6)c4n5-c4ccccc4)ccc32)cc1]
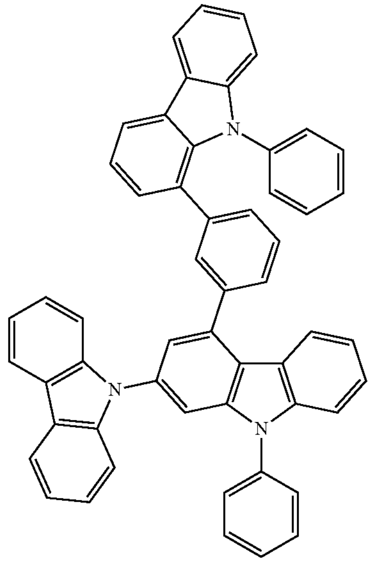 [SMILES: c1ccc(-n2c3ccccc3c3c(-c4cccc(-c5cccc6c7ccccc7n(-c7ccccc7)c56)c4)cc(-n4c5ccccc5c5ccccc54)cc32)cc1]

TABLE 3-continued
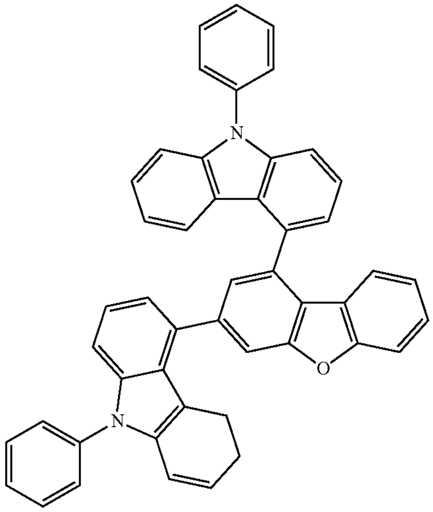 [SMILES: C1=Cc2c(c3c(-c4cc(-c5cccc6c5c5ccccc5n6-c5ccccc5)c5c(c4)oc4ccccc45)cccc3n2-c2ccccc2)CC1]
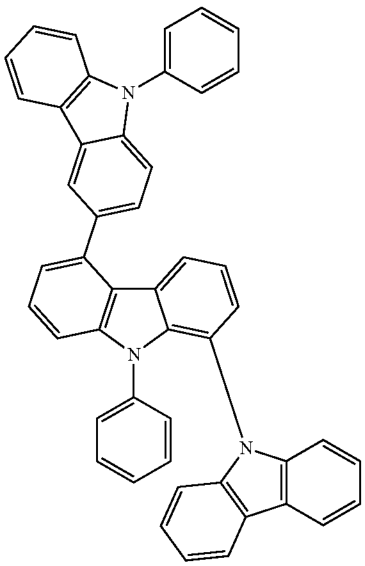 [SMILES: c1ccc(-n2c3ccccc3c3cc(-c4cccc5c4c4cccc(-n6c7ccccc7c7ccccc76)c4n5-c4ccccc4)ccc32)cc1]
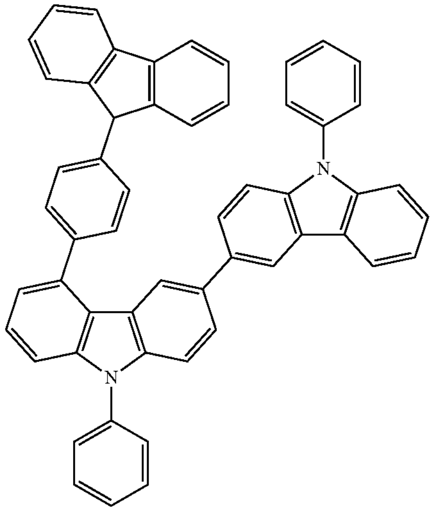 [SMILES: c1ccc(-n2c3ccccc3c3cc(-c4ccc5c(c4)c4c(-c6ccc(C7c8ccccc8-c8ccccc87)cc6)cccc4n5-c4ccccc4)ccc32)cc1]

TABLE 3-continued
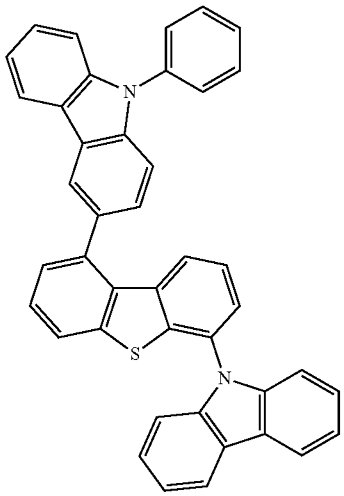 [SMILES: c1ccc(-n2c3ccccc3c3cc(-c4cccc5sc6c(-n7c8ccccc8c8ccccc87)cccc6c45)ccc32)cc1]
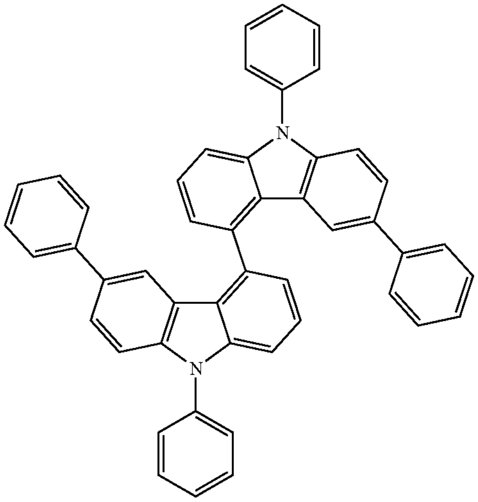 [SMILES: c1ccc(-c2ccc3c(c2)c2c(-c4cccc5c4c4cc(-c6ccccc6)ccc4n5-c4ccccc4)cccc2n3-c2ccccc2)cc1]
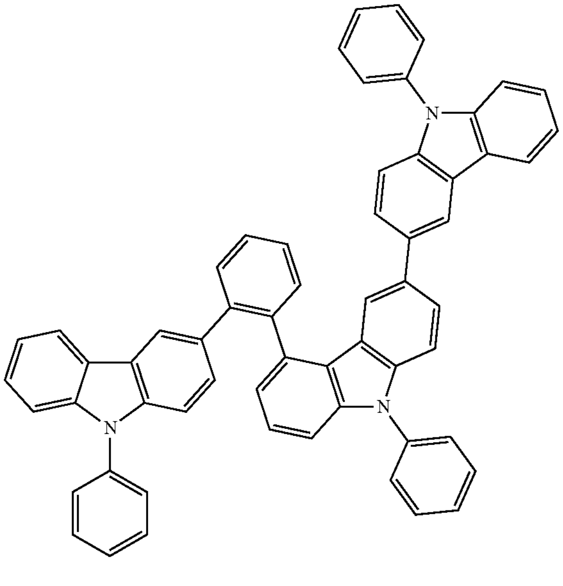 [SMILES: c1ccc(-n2c3ccccc3c3cc(-c4ccc5c(c4)c4c(-c6ccccc6-c6ccc7c(c6)c6ccccc6n7-c6ccccc6)cccc4n5-c4ccccc4)ccc32)cc1]

TABLE 3-continued
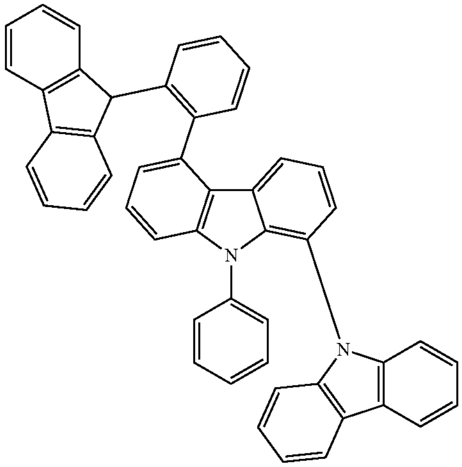 [SMILES: c1ccc(-n2c3cccc(-c4ccccc4C4c5ccccc5-c5ccccc54)c3c3cccc(-n4c5ccccc5c5ccccc54)c32)cc1]
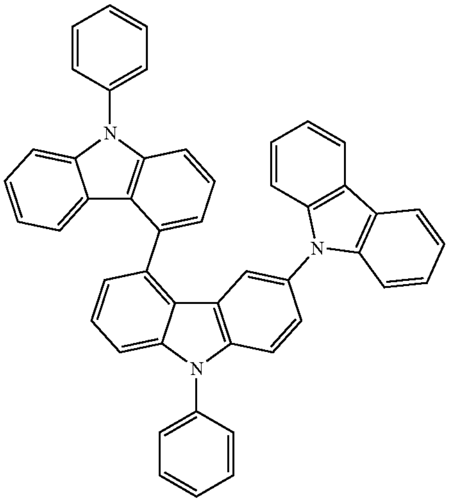 [SMILES: c1ccc(-n2c3ccccc3c3c(-c4cccc5c4c4cc(-n6c7ccccc7c7ccccc76)ccc4n5-c4ccccc4)cccc32)cc1]
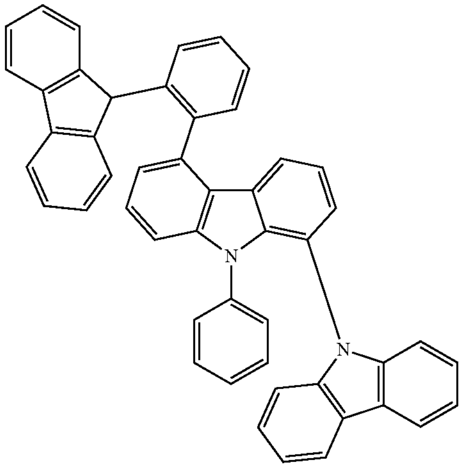 [SMILES: c1ccc(-n2c3cccc(-c4ccccc4C4c5ccccc5-c5ccccc54)c3c3cccc(-n4c5ccccc5c5ccccc54)c32)cc1]

TABLE 3-continued
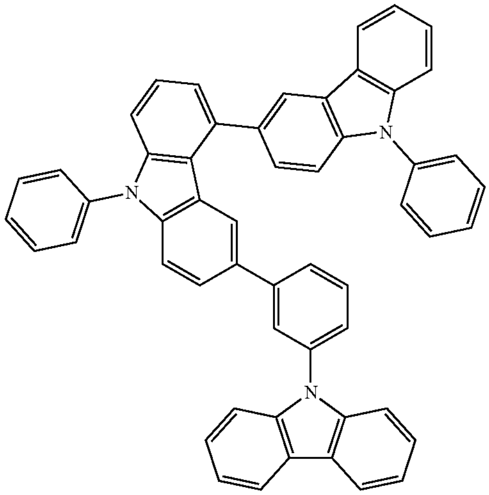 [SMILES: c1ccc(-n2c3ccccc3c3cc(-c4cccc5c4c4cc(-c6cccc(-n7c8ccccc8c8ccccc87)c6)ccc4n5-c4ccccc4)ccc32)cc1]
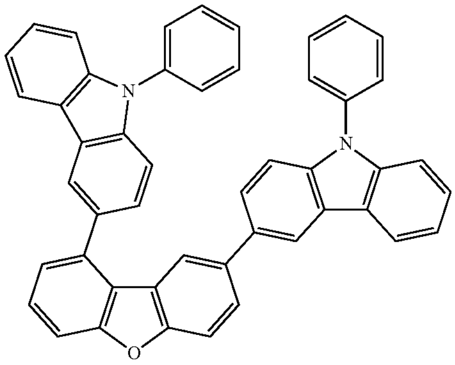 [SMILES: c1ccc(-n2c3ccccc3c3cc(-c4ccc5oc6cccc(-c7ccc8c(c7)c7ccccc7n8-c7ccccc7)c6c5c4)ccc32)cc1]
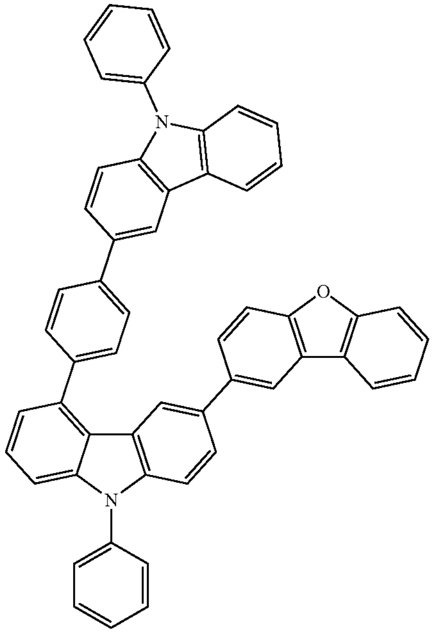 [SMILES: c1ccc(-n2c3ccccc3c3cc(-c4ccc(-c5cccc6c5c5cc(-c7ccc8oc9ccccc9c8c7)ccc5n6-c5ccccc5)cc4)ccc32)cc1]

TABLE 3-continued
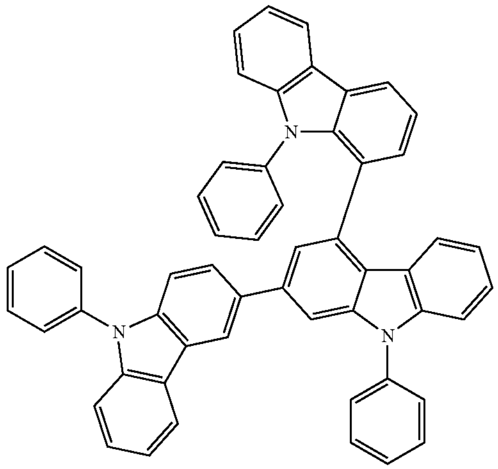 [SMILES: c1ccc(-n2c3ccccc3c3cc(-c4cc(-c5cccc6c7ccccc7n(-c7ccccc7)c56)c5c6ccccc6n(-c6ccccc6)c5c4)ccc32)cc1]
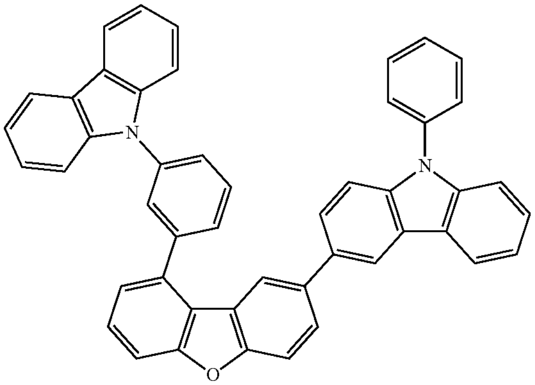 [SMILES: c1ccc(-n2c3ccccc3c3cc(-c4ccc5oc6cccc(-c7cccc(-n8c9ccccc9c9ccccc98)c7)c6c5c4)ccc32)cc1]
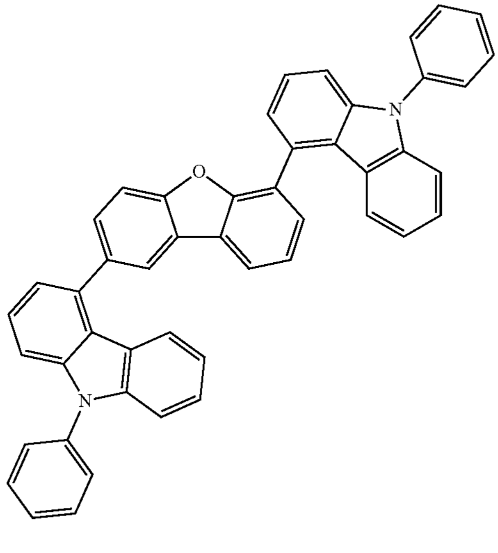 [SMILES: c1ccc(-n2c3ccccc3c3c(-c4ccc5oc6c(-c7cccc8c7c7ccccc7n8-c7ccccc7)cccc6c5c4)cccc32)cc1]

TABLE 3-continued
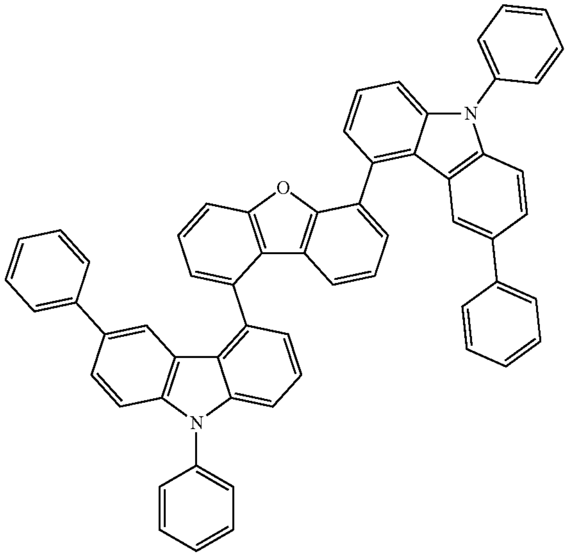 [SMILES: c1ccc(-c2ccc3c(c2)c2c(-c4cccc5c4oc4cccc(-c6cccc7c6c6cc(-c8ccccc8)ccc6n7-c6ccccc6)c45)cccc2n3-c2ccccc2)cc1]
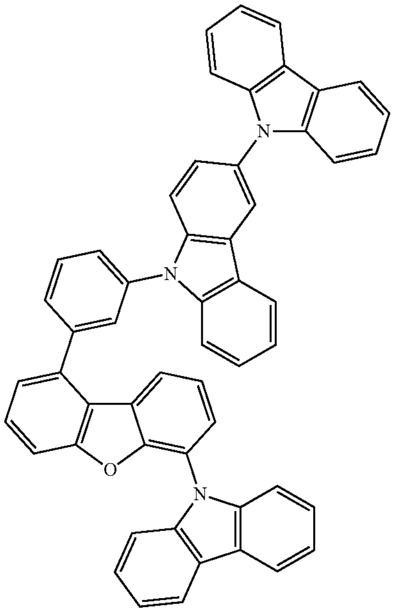 [SMILES: c1cc(-c2cccc3oc4c(-n5c6ccccc6c6ccccc65)cccc4c23)cc(-n2c3ccccc3c3cc(-n4c5ccccc5c5ccccc54)ccc32)c1]
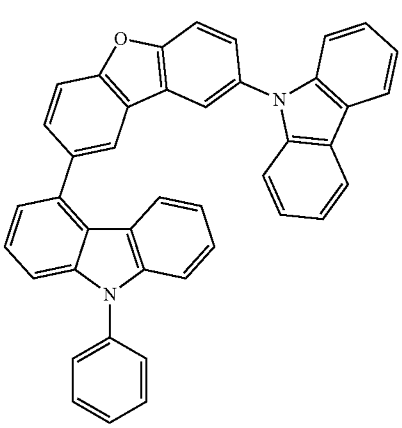 [SMILES: c1ccc(-n2c3ccccc3c3c(-c4ccc5oc6ccc(-n7c8ccccc8c8ccccc87)cc6c5c4)cccc32)cc1]

TABLE 3-continued
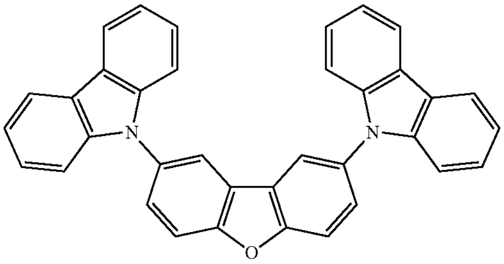 [SMILES: c1ccc2c(c1)c1ccccc1n2-c1ccc2oc3ccc(-n4c5ccccc5c5ccccc54)cc3c2c1]
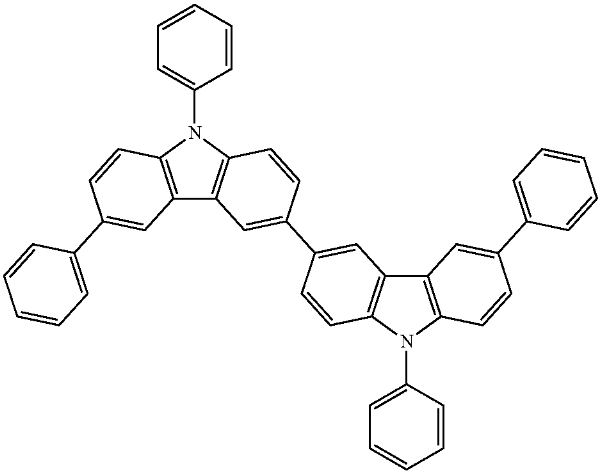 [SMILES: c1ccc(-c2ccc3c(c2)c2cc(-c4ccc5c(c4)c4cc(-c6ccccc6)ccc4n5-c4ccccc4)ccc2n3-c2ccccc2)cc1]
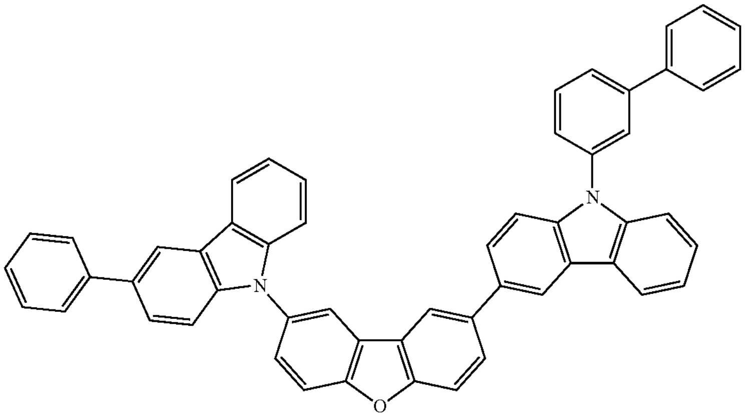 [SMILES: c1ccc(-c2cccc(-n3c4ccccc4c4cc(-c5ccc6oc7ccc(-n8c9ccccc9c9cc(-c%10ccccc%10)ccc98)cc7c6c5)ccc43)c2)cc1]
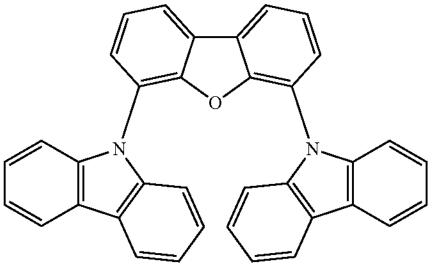 [SMILES: c1cc(-n2c3ccccc3c3ccccc32)c2oc3c(-n4c5ccccc5c5ccccc54)cccc3c2c1]

TABLE 3-continued
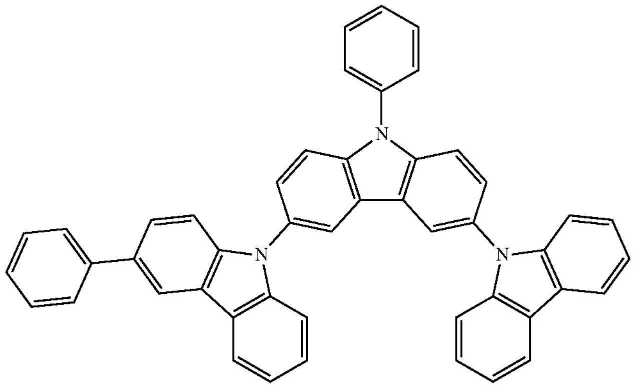 [SMILES: c1ccc(-c2ccc3c(c2)c2ccccc2n3-c2ccc3c(c2)c2cc(-n4c5ccccc5c5ccccc54)ccc2n3-c2ccccc2)cc1]
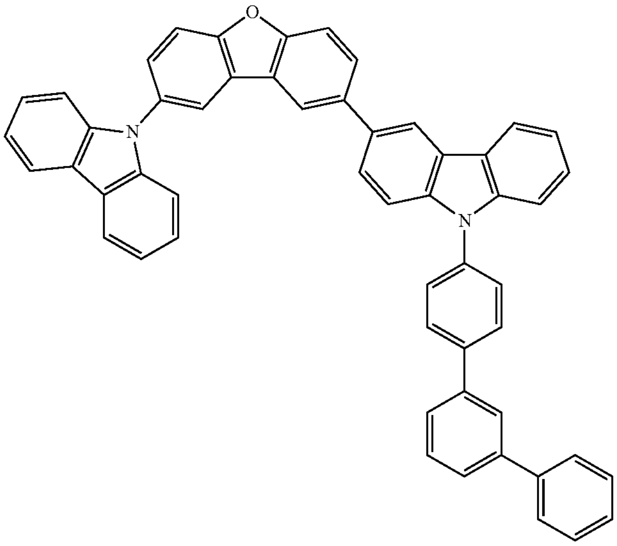 [SMILES: c1ccc(-c2cccc(-c3ccc(-n4c5ccccc5c5cc(-c6ccc7oc8ccc(-n9c%10ccccc%10c%10ccccc%109)cc8c7c6)ccc54)cc3)c2)cc1]
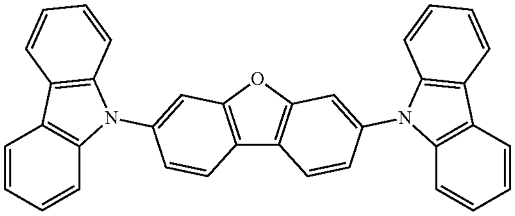 [SMILES: c1ccc2c(c1)c1ccccc1n2-c1ccc2c(c1)oc1cc(-n3c4ccccc4c4ccccc43)ccc12]
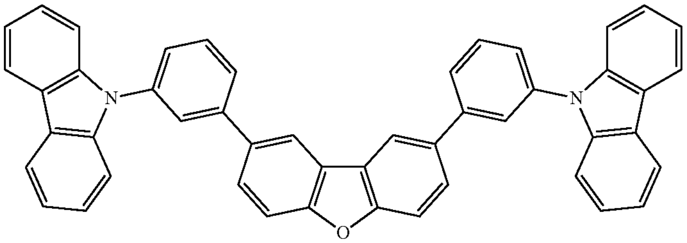 [SMILES: c1cc(-c2ccc3oc4ccc(-c5cccc(-n6c7ccccc7c7ccccc76)c5)cc4c3c2)cc(-n2c3ccccc3c3ccccc32)c1]

TABLE 3-continued
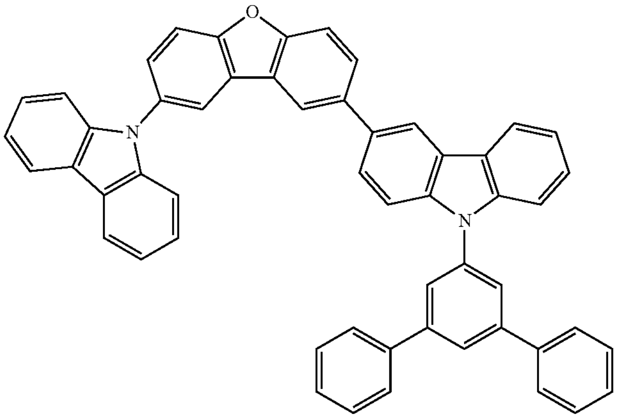 [SMILES: c1ccc(-c2cc(-c3ccccc3)cc(-n3c4ccccc4c4cc(-c5ccc6oc7ccc(-n8c9ccccc9c9ccccc98)cc7c6c5)ccc43)c2)cc1]
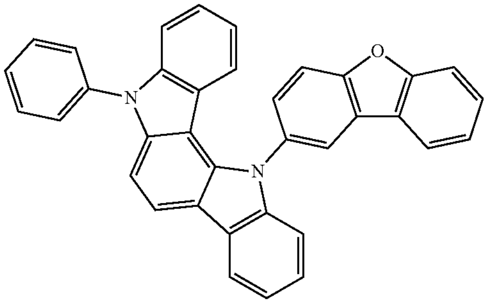 [SMILES: c1ccc(-n2c3ccccc3c3c2ccc2c4ccccc4n(-c4ccc5oc6ccccc6c5c4)c23)cc1]
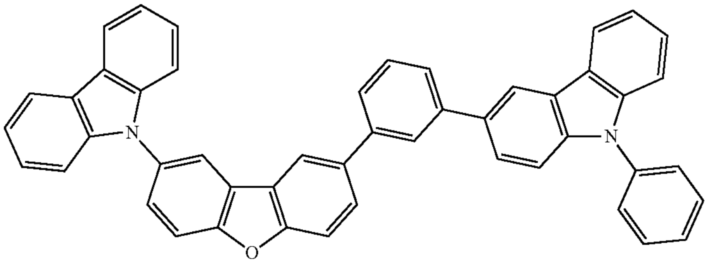 [SMILES: c1ccc(-n2c3ccccc3c3cc(-c4cccc(-c5ccc6oc7ccc(-n8c9ccccc9c9ccccc98)cc7c6c5)c4)ccc32)cc1]
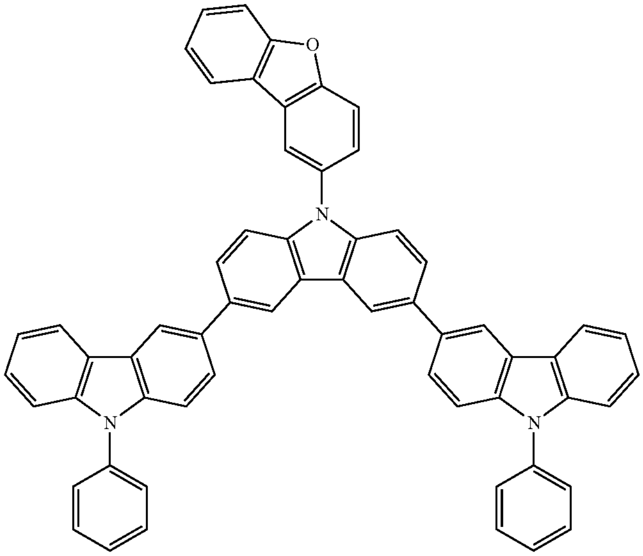 [SMILES: c1ccc(-n2c3ccccc3c3cc(-c4ccc5c(c4)c4cc(-c6ccc7c(c6)c6ccccc6n7-c6ccccc6)ccc4n5-c4ccc5oc6ccccc6c5c4)ccc32)cc1]

TABLE 3-continued
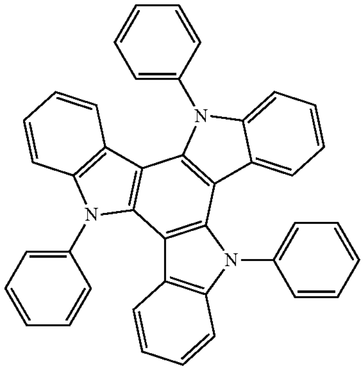 [SMILES: c1ccc(-n2c3ccccc3c3c2c2c4ccccc4n(-c4ccccc4)c2c2c4ccccc4n(-c4ccccc4)c32)cc1]
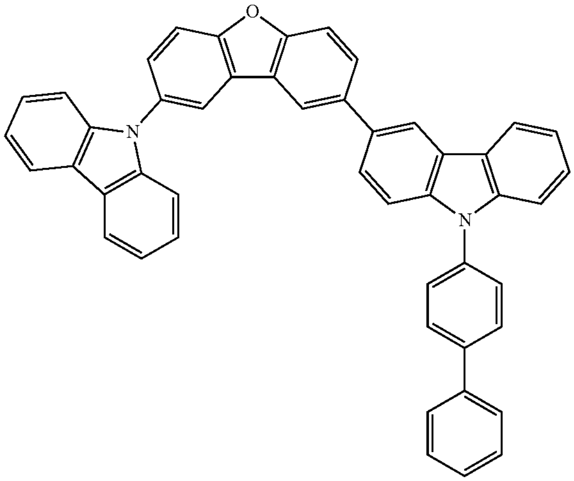 [SMILES: c1ccc(-c2ccc(-n3c4ccccc4c4cc(-c5ccc6oc7ccc(-n8c9ccccc9c9ccccc98)cc7c6c5)ccc43)cc2)cc1]
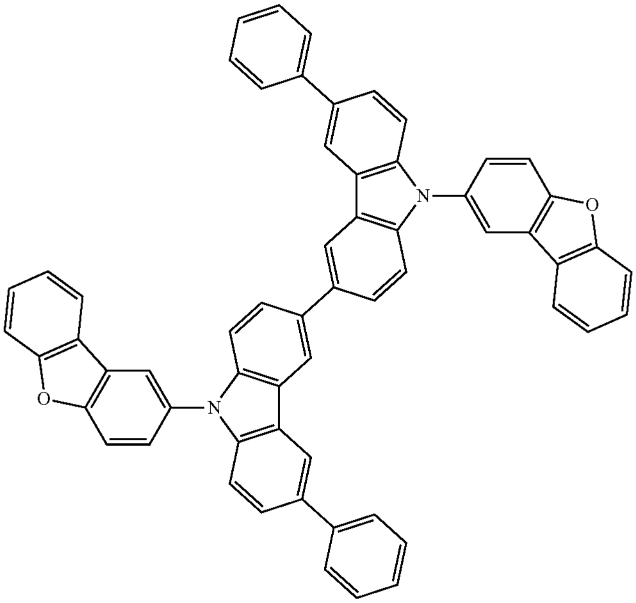 [SMILES: c1ccc(-c2ccc3c(c2)c2cc(-c4ccc5c(c4)c4cc(-c6ccccc6)ccc4n5-c4ccc5oc6ccccc6c5c4)ccc2n3-c2ccc3oc4ccccc4c3c2)cc1]

TABLE 3-continued
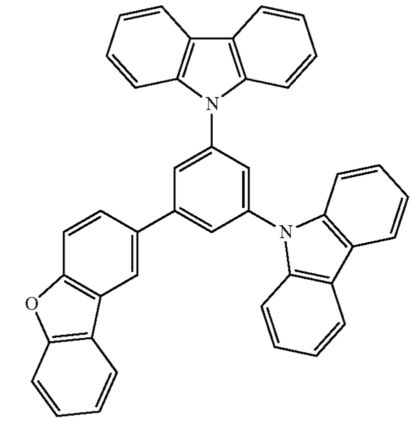 [SMILES: c1ccc2c(c1)oc1ccc(-c3cc(-n4c5ccccc5c5ccccc54)cc(-n4c5ccccc5c5ccccc54)c3)cc12]
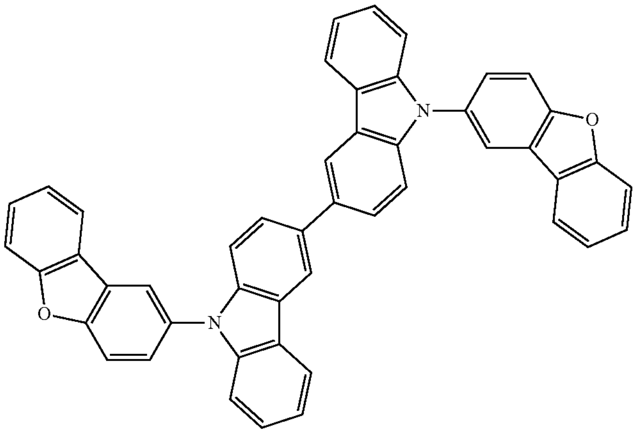 [SMILES: c1ccc2c(c1)oc1ccc(-n3c4ccccc4c4cc(-c5ccc6c(c5)c5ccccc5n6-c5ccc6oc7ccccc7c6c5)ccc43)cc12]
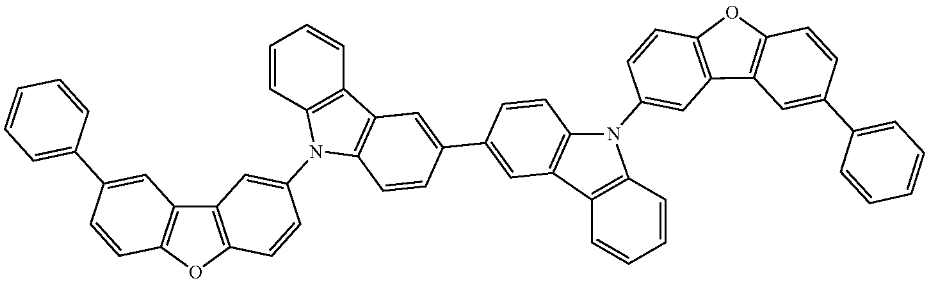 [SMILES: c1ccc(-c2ccc3oc4ccc(-n5c6ccccc6c6cc(-c7ccc8c(c7)c7ccccc7n8-c7ccc8oc9ccc(-c%10ccccc%10)cc9c8c7)ccc65)cc4c3c2)cc1]
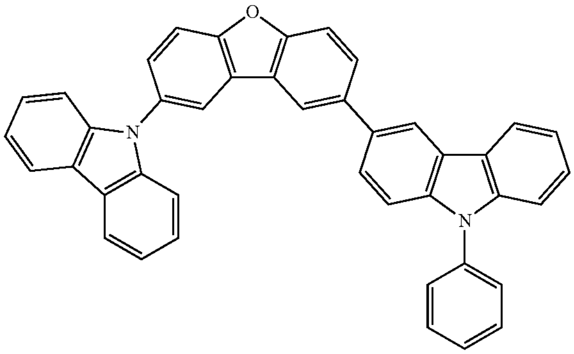 [SMILES: c1ccc(-n2c3ccccc3c3cc(-c4ccc5oc6ccc(-n7c8ccccc8c8ccccc87)cc6c5c4)ccc32)cc1]

TABLE 3-continued
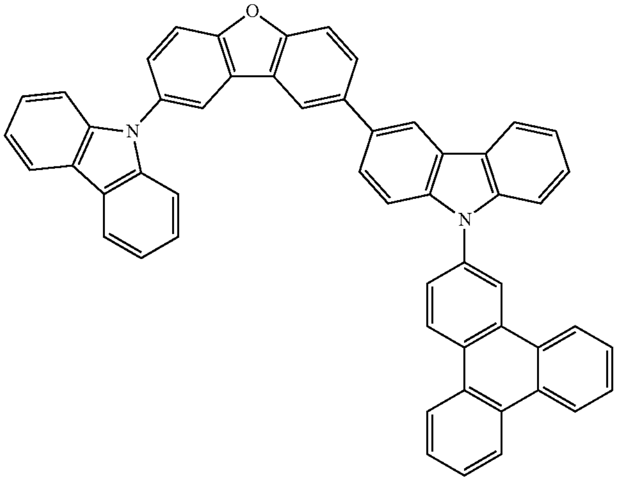 [SMILES: c1ccc2c(c1)c1ccccc1c1cc(-n3c4ccccc4c4cc(-c5ccc6oc7ccc(-n8c9ccccc9c9ccccc98)cc7c6c5)ccc43)ccc21]
32
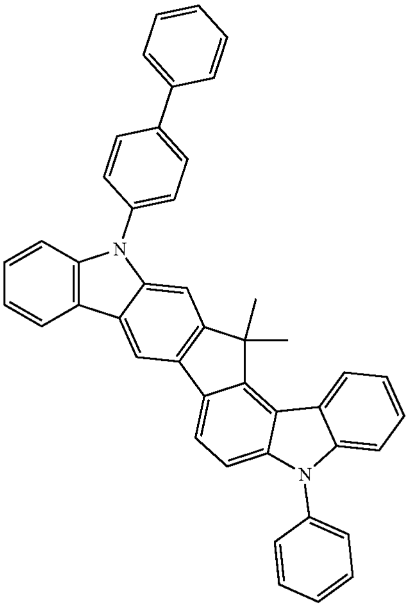 [SMILES: CC1(C)c2cc3c(cc2-c2ccc4c(c21)c1ccccc1n4-c1ccccc1)c1ccccc1n3-c1ccc(-c2ccccc2)cc1]
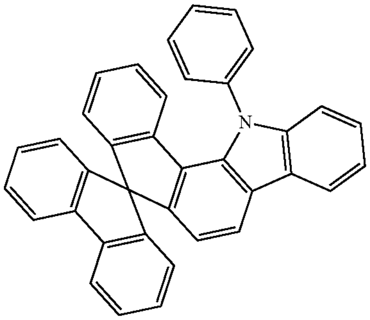 [SMILES: c1ccc(-n2c3ccccc3c3ccc4c(c32)-c2ccccc2C42c3ccccc3-c3ccccc32)cc1]

TABLE 3-continued
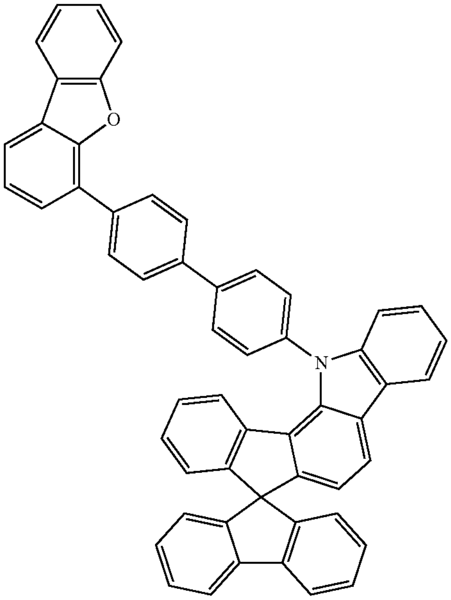 [SMILES: c1ccc2c(c1)-c1ccccc1C21c2ccccc2-c2c1ccc1c3ccccc3n(-c3ccc(-c4ccc(-c5cccc6c5oc5ccccc56)cc4)cc3)c21]
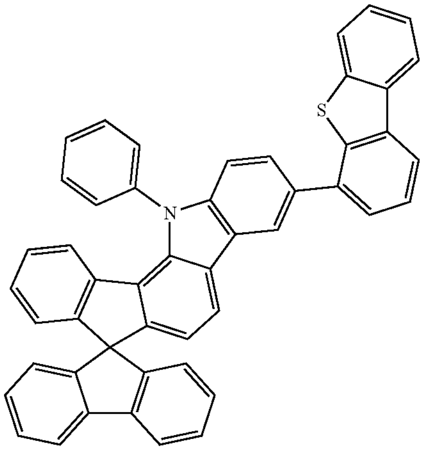 [SMILES: c1ccc(-n2c3ccc(-c4cccc5c4sc4ccccc45)cc3c3ccc4c(c32)-c2ccccc2C42c3ccccc3-c3ccccc32)cc1]
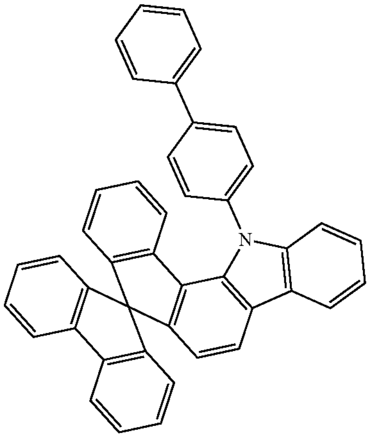 [SMILES: c1ccc(-c2ccc(-n3c4ccccc4c4ccc5c(c43)-c3ccccc3C53c4ccccc4-c4ccccc43)cc2)cc1]

TABLE 3-continued
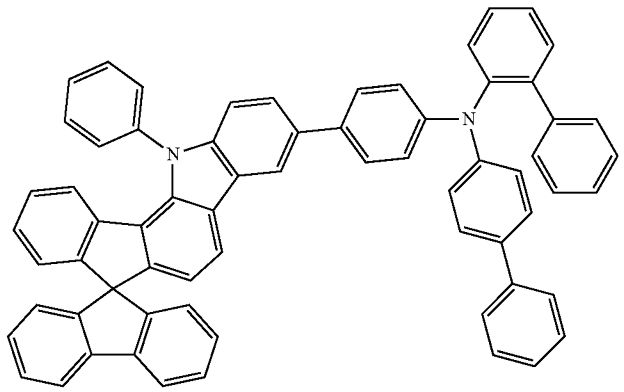 [SMILES: c1ccc(-c2ccc(N(c3ccc(-c4ccc5c(c4)c4ccc6c(c4n5-c4ccccc4)-c4ccccc4C64c5ccccc5-c5ccccc54)cc3)c3ccccc3-c3ccccc3)cc2)cc1]
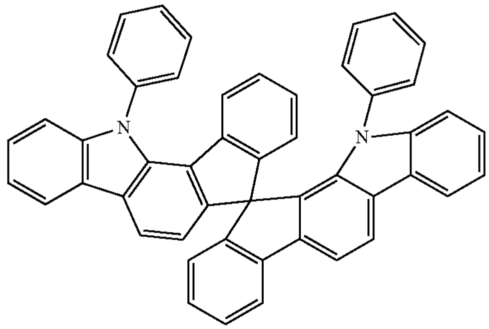 [SMILES: c1ccc(-n2c3ccccc3c3ccc4c(c32)-c2ccccc2C42c3ccccc3-c3ccc4c5ccccc5n(-c5ccccc5)c4c32)cc1]
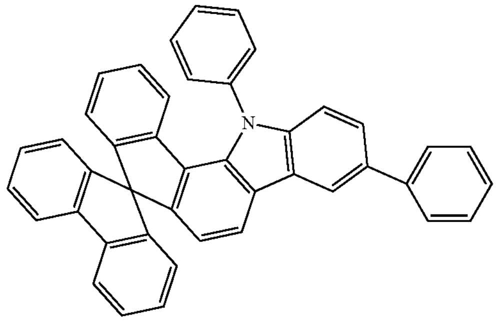 [SMILES: c1ccc(-c2ccc3c(c2)c2ccc4c(c2n3-c2ccccc2)-c2ccccc2C42c3ccccc3-c3ccccc32)cc1]
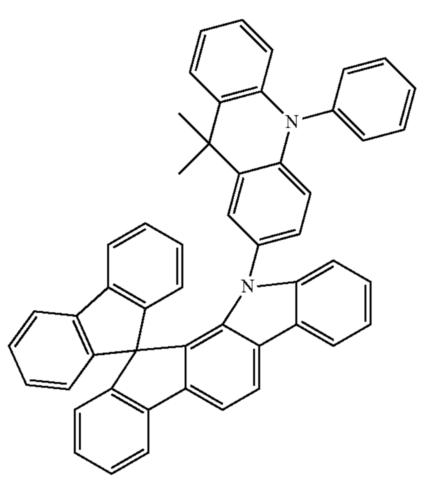 [SMILES: CC1(C)c2ccccc2N(c2ccccc2)c2ccc(-n3c4ccccc4c4ccc5c(c43)C3(c4ccccc4-c4ccccc43)c3ccccc3-5)cc21]

TABLE 3-continued
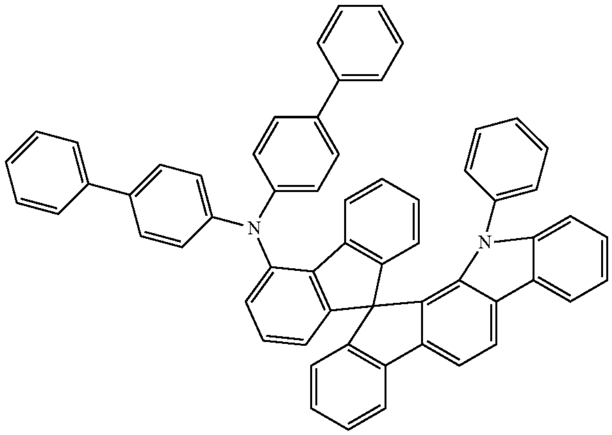 [SMILES: c1ccc(-c2ccc(N(c3ccc(-c4ccccc4)cc3)c3cccc4c3-c3ccccc3C43c4ccccc4-c4ccc5c6ccccc6n(-c6ccccc6)c5c43)cc2)cc1]
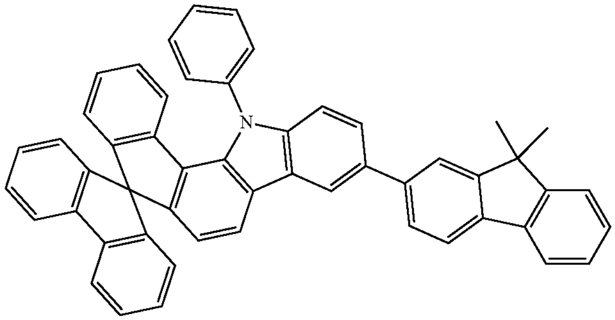 [SMILES: CC1(C)c2ccccc2-c2ccc(-c3ccc4c(c3)c3ccc5c(c3n4-c3ccccc3)-c3ccccc3C53c4ccccc4-c4ccccc43)cc21]
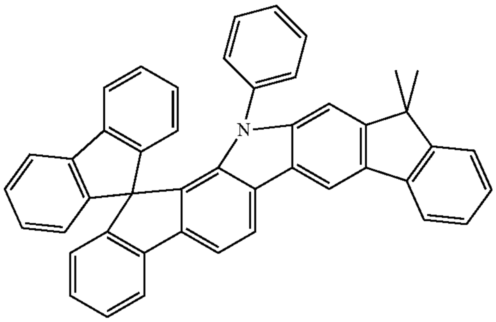 [SMILES: CC1(C)c2ccccc2-c2cc3c4ccc5c(c4n(-c4ccccc4)c3cc21)C1(c2ccccc2-c2ccccc21)c1ccccc1-5]
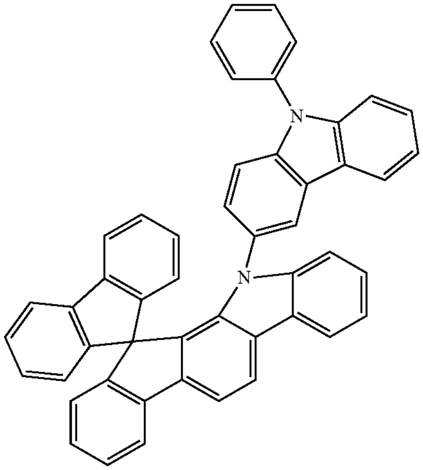 [SMILES: c1ccc(-n2c3ccccc3c3cc(-n4c5ccccc5c5ccc6c(c54)C4(c5ccccc5-c5ccccc54)c4ccccc4-6)ccc32)cc1]

TABLE 3-continued
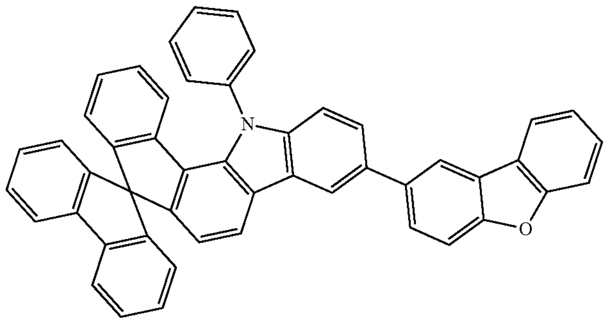 [SMILES: c1ccc(-n2c3ccc(-c4ccc5oc6ccccc6c5c4)cc3c3ccc4c(c32)-c2ccccc2C42c3ccccc3-c3ccccc32)cc1]
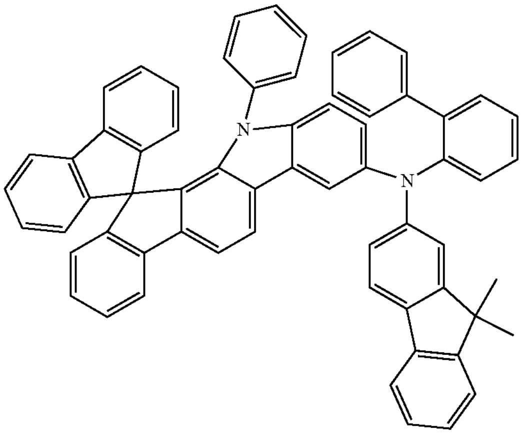 [SMILES: CC1(C)c2ccccc2-c2ccc(N(c3ccc4c(c3)c3ccc5c(c3n4-c3ccccc3)C3(c4ccccc4-c4ccccc43)c3ccccc3-5)c3ccccc3-c3ccccc3)cc21]
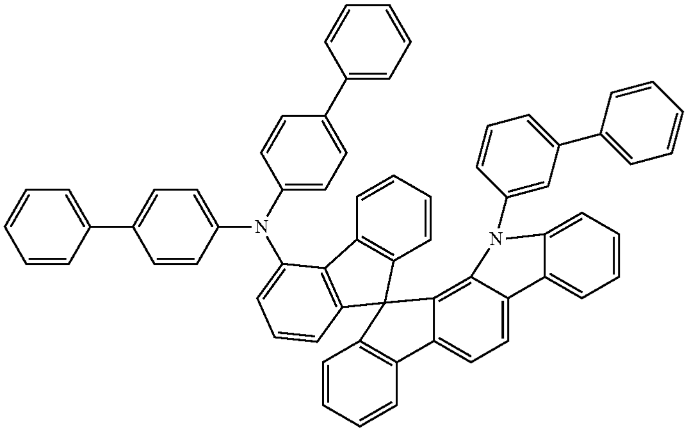 [SMILES: c1ccc(-c2ccc(N(c3ccc(-c4ccccc4)cc3)c3cccc4c3-c3ccccc3C43c4ccccc4-c4ccc5c6ccccc6n(-c6cccc(-c7ccccc7)c6)c5c43)cc2)cc1]
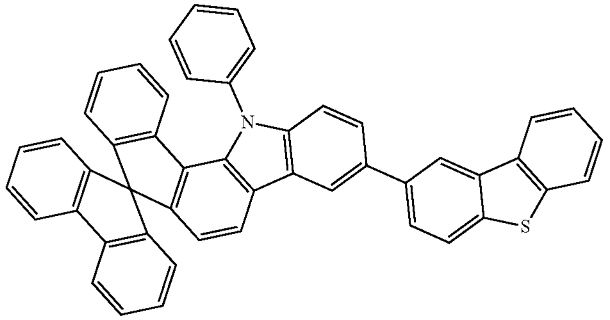 [SMILES: c1ccc(-n2c3ccc(-c4ccc5sc6ccccc6c5c4)cc3c3ccc4c(c32)-c2ccccc2C42c3ccccc3-c3ccccc32)cc1]

TABLE 3-continued
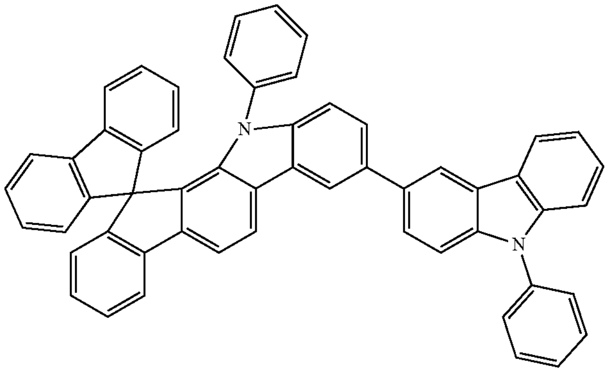 [SMILES: c1ccc(-n2c3ccccc3c3cc(-c4ccc5c(c4)c4ccc6c(c4n5-c4ccccc4)C4(c5ccccc5-c5ccccc54)c4ccccc4-6)ccc32)cc1]
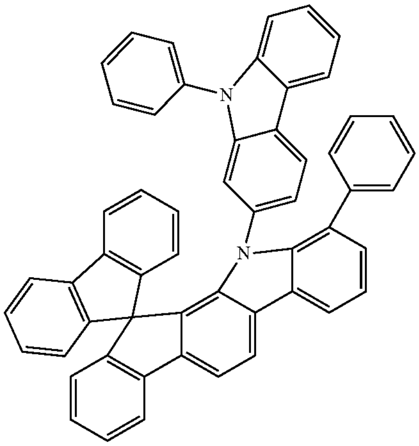 [SMILES: c1ccc(-c2cccc3c4ccc5c(c4n(-c4ccc6c7ccccc7n(-c7ccccc7)c6c4)c23)C2(c3ccccc3-c3ccccc32)c2ccccc2-5)cc1]
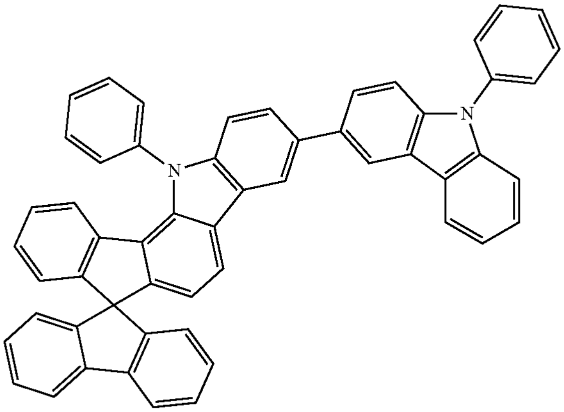 [SMILES: c1ccc(-n2c3ccccc3c3cc(-c4ccc5c(c4)c4ccc6c(c4n5-c4ccccc4)-c4ccccc4C64c5ccccc5-c5ccccc54)ccc32)cc1]
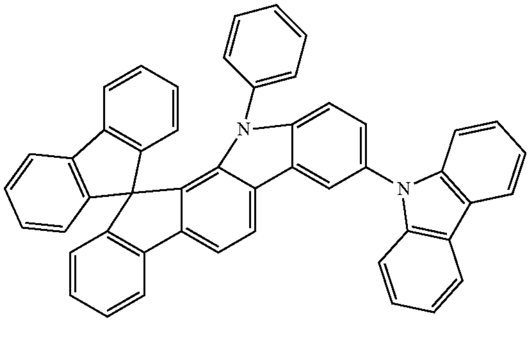 [SMILES: c1ccc(-n2c3ccc(-n4c5ccccc5c5ccccc54)cc3c3ccc4c(c32)C2(c3ccccc3-c3ccccc32)c2ccccc2-4)cc1]

TABLE 3-continued
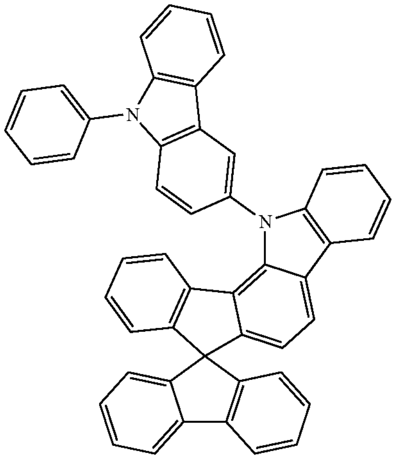 [SMILES: c1ccc(-n2c3ccccc3c3cc(-n4c5ccccc5c5ccc6c(c54)-c4ccccc4C64c5ccccc5-c5ccccc54)ccc32)cc1]
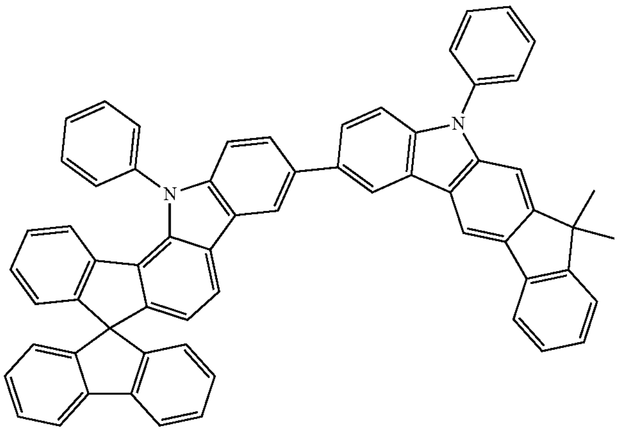 [SMILES: CC1(C)c2ccccc2-c2cc3c4cc(-c5ccc6c(c5)c5ccc7c(c5n6-c5ccccc5)-c5ccccc5C75c6ccccc6-c6ccccc65)ccc4n(-c4ccccc4)c3cc21]
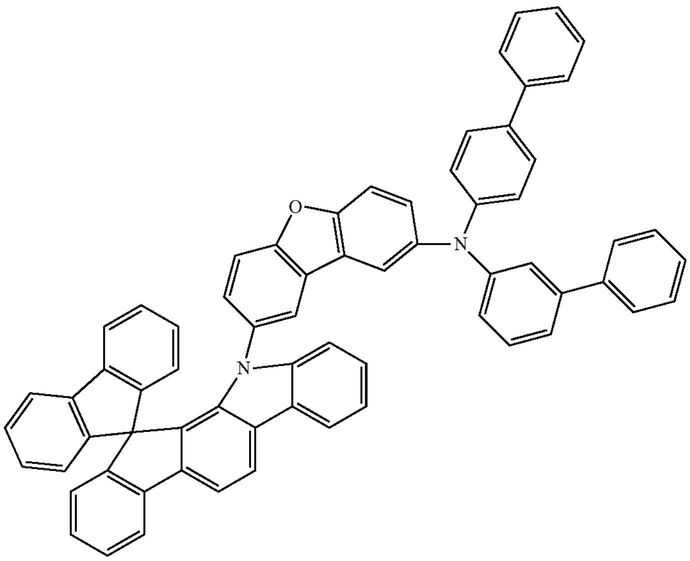 [SMILES: c1ccc(-c2ccc(N(c3cccc(-c4ccccc4)c3)c3ccc4oc5ccc(-n6c7ccccc7c7ccc8c(c76)C6(c7ccccc7-c7ccccc76)c6ccccc6-8)cc5c4c3)cc2)cc1]

TABLE 3-continued
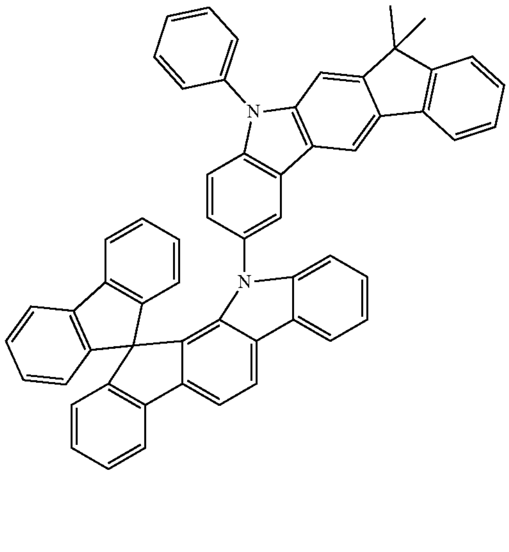 [SMILES: CC1(C)c2ccccc2-c2cc3c4cc(-n5c6ccccc6c6ccc7c(c65)C5(c6ccccc6-c6ccccc65)c5ccccc5-7)ccc4n(-c4ccccc4)c3cc21]
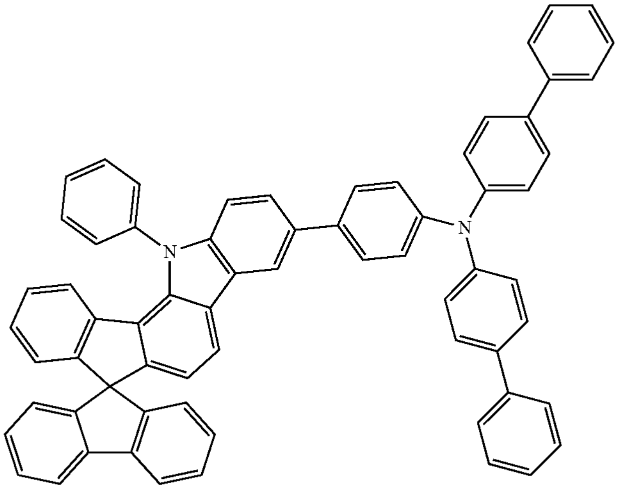 [SMILES: c1ccc(-c2ccc(N(c3ccc(-c4ccccc4)cc3)c3ccc(-c4ccc5c(c4)c4ccc6c(c4n5-c4ccccc4)-c4ccccc4C64c5ccccc5-c5ccccc54)cc3)cc2)cc1]
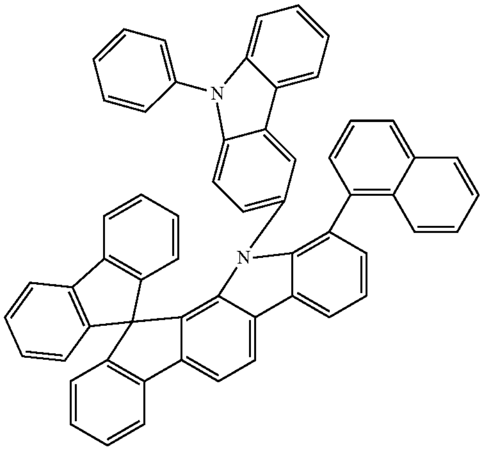 [SMILES: c1ccc(-n2c3ccccc3c3cc(-n4c5c(-c6cccc7ccccc67)cccc5c5ccc6c(c54)C4(c5ccccc5-c5ccccc54)c4ccccc4-6)ccc32)cc1]

TABLE 3-continued
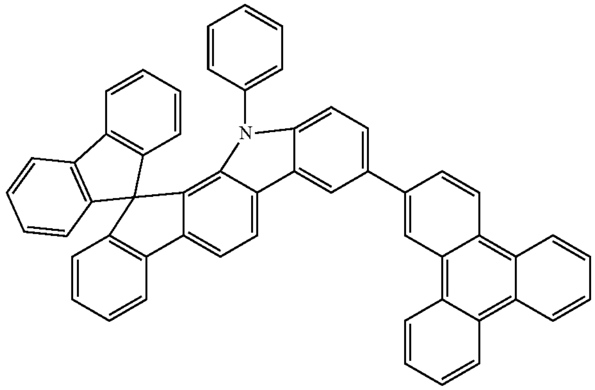 [SMILES: c1ccc(-n2c3ccc(-c4ccc5c6ccccc6c6ccccc6c5c4)cc3c3ccc4c(c32)C2(c3ccccc3-c3ccccc32)c2ccccc2-4)cc1]
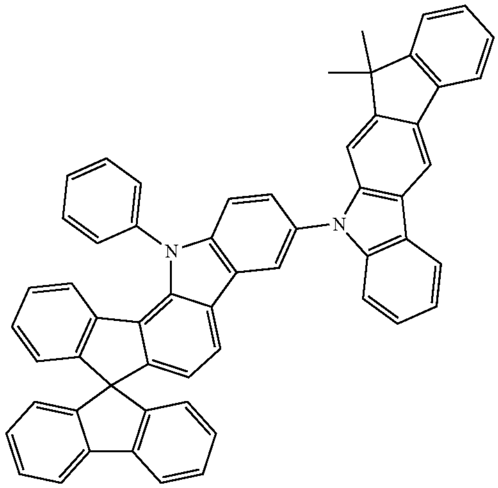 [SMILES: CC1(C)c2ccccc2-c2cc3c4ccccc4n(-c4ccc5c(c4)c4ccc6c(c4n5-c4ccccc4)-c4ccccc4C64c5ccccc5-c5ccccc54)c3cc21]
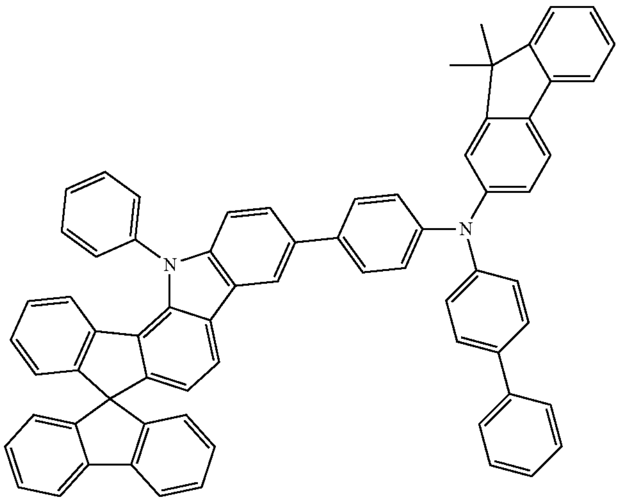 [SMILES: CC1(C)c2ccccc2-c2ccc(N(c3ccc(-c4ccccc4)cc3)c3ccc(-c4ccc5c(c4)c4ccc6c(c4n5-c4ccccc4)-c4ccccc4C64c5ccccc5-c5ccccc54)cc3)cc21]

TABLE 3-continued
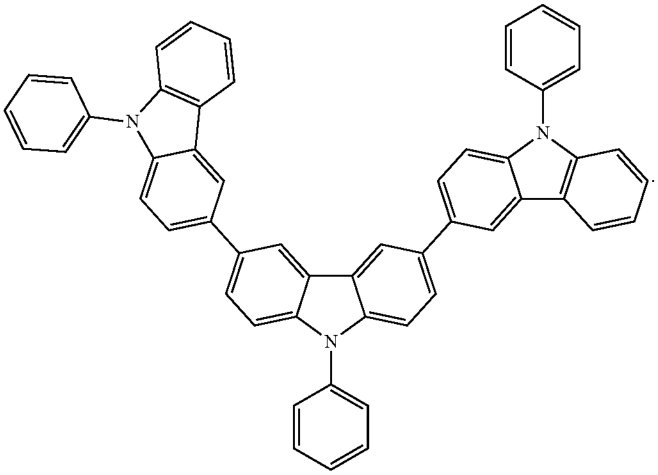 [SMILES: c1ccc(-n2c3ccccc3c3cc(-c4ccc5c(c4)c4cc(-c6ccc7c(c6)c6ccccc6n7-c6ccccc6)ccc4n5-c4ccccc4)ccc32)cc1 ; "."]
33
Particularly suitable examples of compounds of the formulae (2), (2a), (2b), (2c), (2d), (2e), (2f), (2g), (2h) and (2i) that are selected in accordance with the invention are the compounds 12 to 34, as described in table 4:
TABLE 4
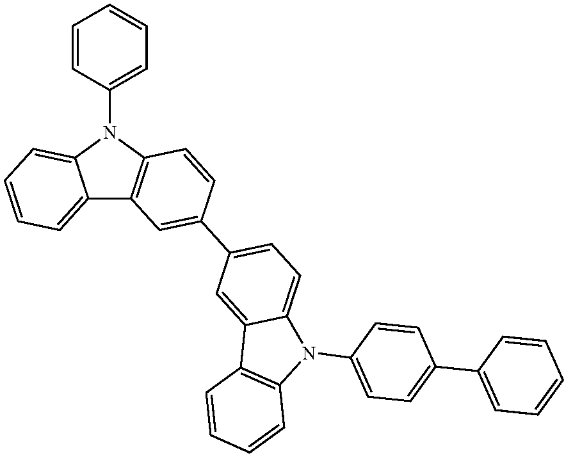 [SMILES: c1ccc(-c2ccc(-n3c4ccccc4c4cc(-c5ccc6c(c5)c5ccccc5n6-c5ccccc5)ccc43)cc2)cc1]
12
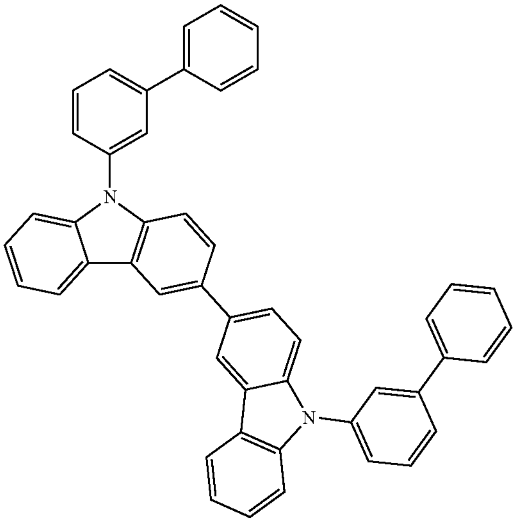 [SMILES: c1ccc(-c2cccc(-n3c4ccccc4c4cc(-c5ccc6c(c5)c5ccccc5n6-c5cccc(-c6ccccc6)c5)ccc43)c2)cc1]
13

TABLE 4-continued
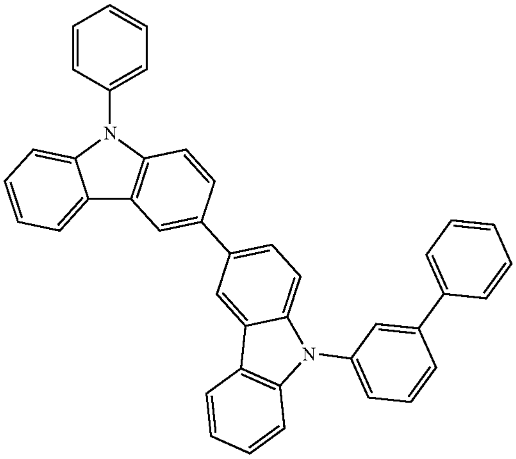 [SMILES: c1ccc(-c2cccc(-n3c4ccccc4c4cc(-c5ccc6c(c5)c5ccccc5n6-c5ccccc5)ccc43)c2)cc1]
14
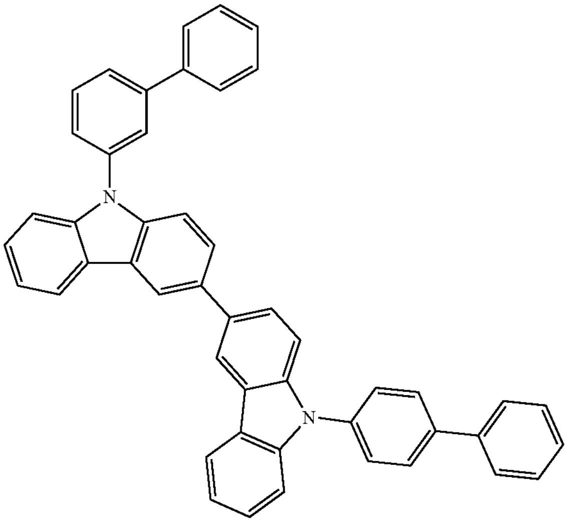 [SMILES: c1ccc(-c2ccc(-n3c4ccccc4c4cc(-c5ccc6c(c5)c5ccccc5n6-c5cccc(-c6ccccc6)c5)ccc43)cc2)cc1]
15
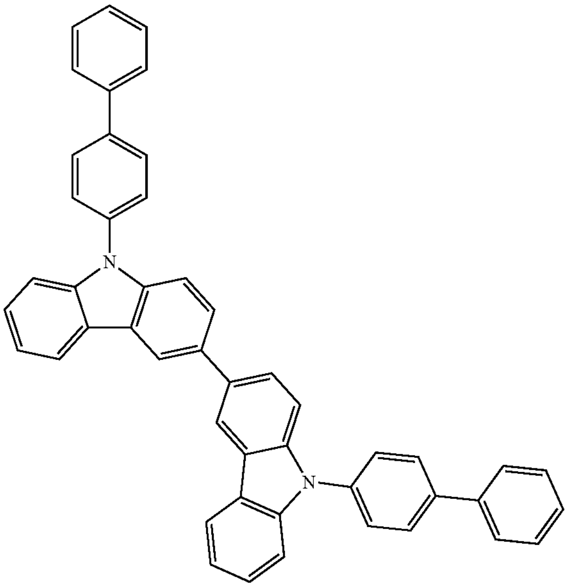 [SMILES: c1ccc(-c2ccc(-n3c4ccccc4c4cc(-c5ccc6c(c5)c5ccccc5n6-c5ccc(-c6ccccc6)cc5)ccc43)cc2)cc1]
16

TABLE 4-continued
17
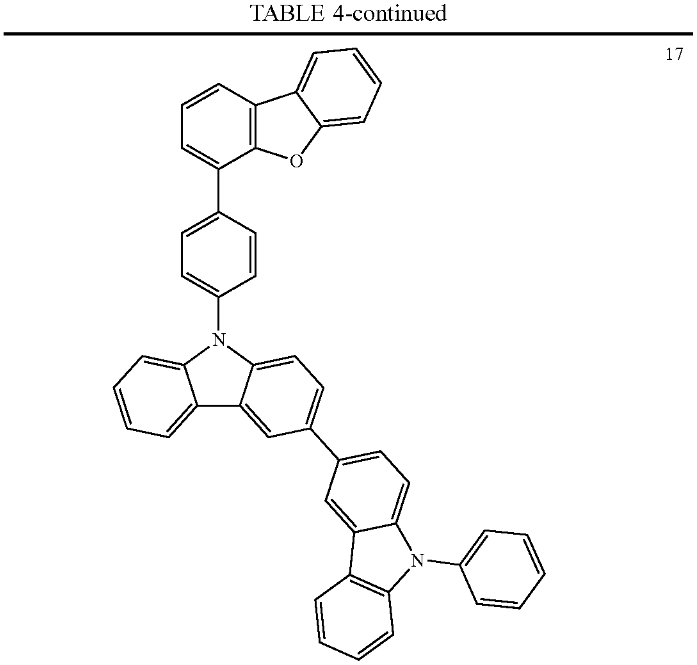
18
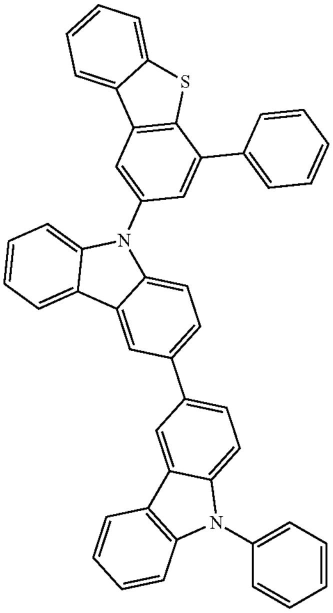 [SMILES: c1ccc(-c2cc(-n3c4ccccc4c4cc(-c5ccc6c(c5)c5ccccc5n6-c5ccccc5)ccc43)cc3c2sc2ccccc23)cc1]

TABLE 4-continued
19
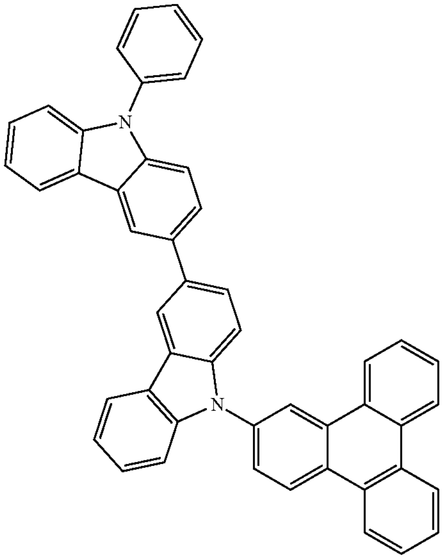 [SMILES: c1ccc(-n2c3ccccc3c3cc(-c4ccc5c(c4)c4ccccc4n5-c4ccc5c6ccccc6c6ccccc6c5c4)ccc32)cc1]
20
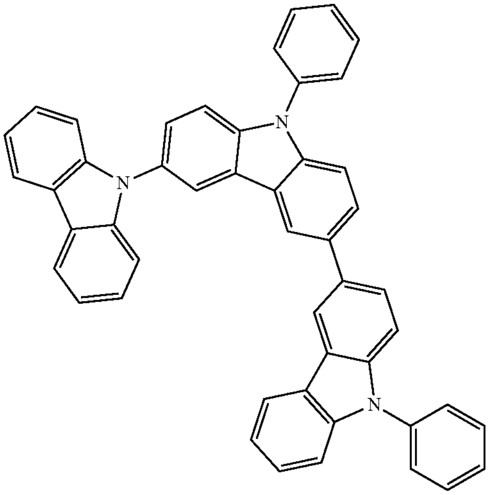 [SMILES: c1ccc(-n2c3ccccc3c3cc(-c4ccc5c(c4)c4cc(-n6c7ccccc7c7ccccc76)ccc4n5-c4ccccc4)ccc32)cc1]
21
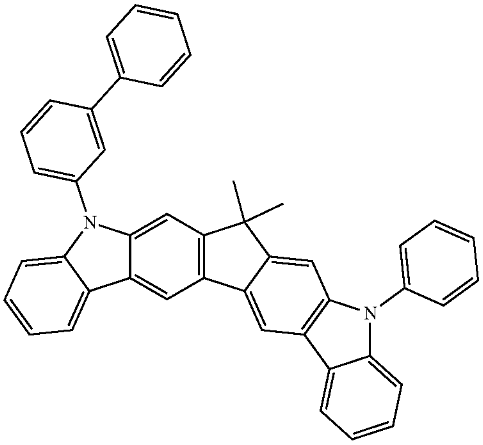 [SMILES: CC1(C)c2cc3c(cc2-c2cc4c5ccccc5n(-c5cccc(-c6ccccc6)c5)c4cc21)c1ccccc1n3-c1ccccc1]

TABLE 4-continued
22
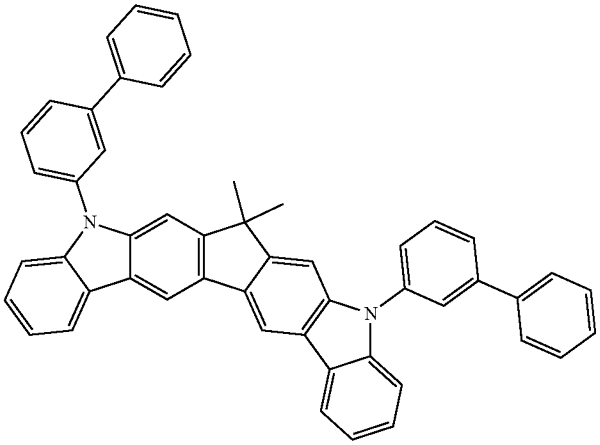 [SMILES: CC1(C)c2cc3c(cc2-c2cc4c5ccccc5n(-c5cccc(-c6ccccc6)c5)c4cc21)c1ccccc1n3-c1cccc(-c2ccccc2)c1]
23
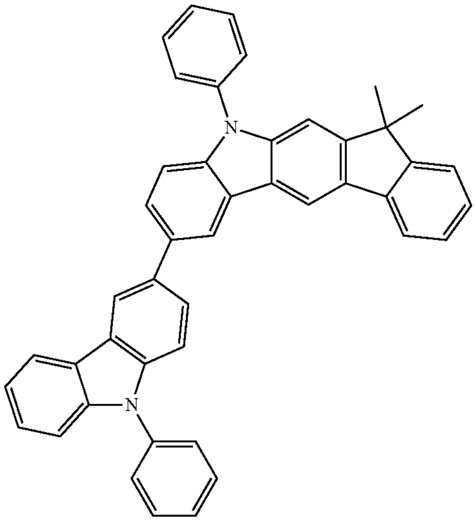 [SMILES: CC1(C)c2ccccc2-c2cc3c4cc(-c5ccc6c(c5)c5ccccc5n6-c5ccccc5)ccc4n(-c4ccccc4)c3cc21]
24
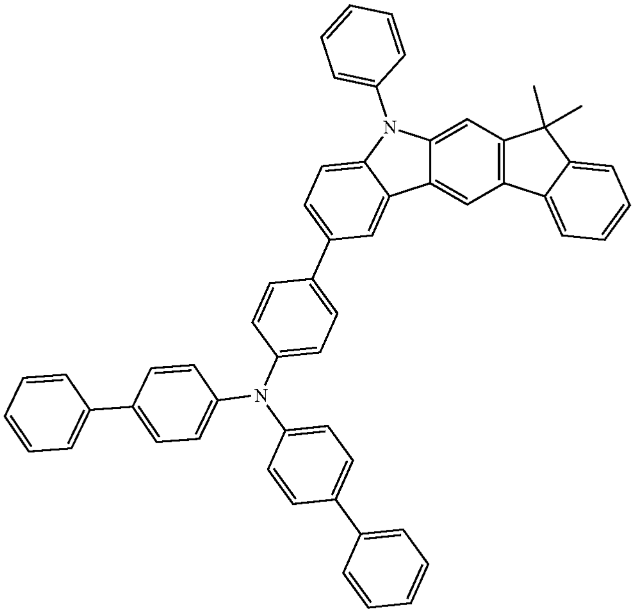 [SMILES: CC1(C)c2ccccc2-c2cc3c4cc(-c5ccc(N(c6ccc(-c7ccccc7)cc6)c6ccc(-c7ccccc7)cc6)cc5)ccc4n(-c4ccccc4)c3cc21]

TABLE 4-continued
25
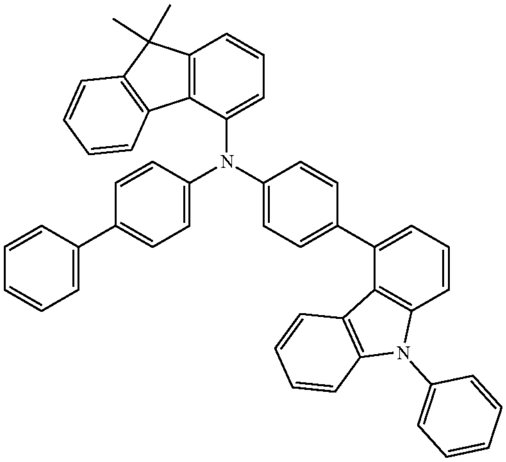 [SMILES: CC1(C)c2ccccc2-c2c(N(c3ccc(-c4ccccc4)cc3)c3ccc(-c4cccc5c4c4ccccc4n5-c4ccccc4)cc3)cccc21]
26
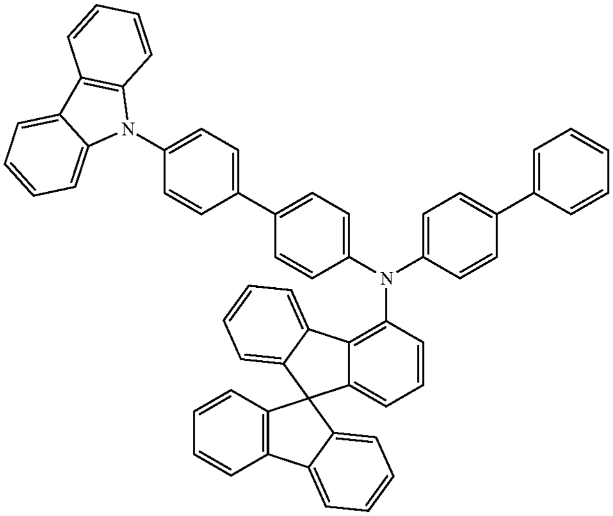 [SMILES: c1ccc(-c2ccc(N(c3ccc(-c4ccc(-n5c6ccccc6c6ccccc65)cc4)cc3)c3cccc4c3-c3ccccc3C43c4ccccc4-c4ccccc43)cc2)cc1]
27
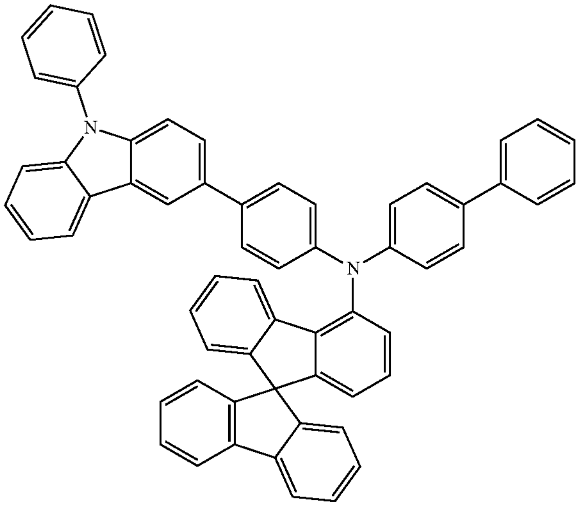 [SMILES: c1ccc(-c2ccc(N(c3ccc(-c4ccc5c(c4)c4ccccc4n5-c4ccccc4)cc3)c3cccc4c3-c3ccccc3C43c4ccccc4-c4ccccc43)cc2)cc1]

TABLE 4-continued
28
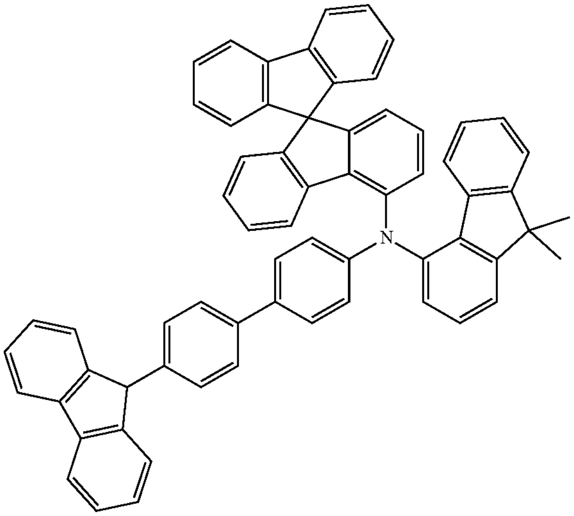 [SMILES: CC1(C)c2ccccc2-c2c(N(c3ccc(-c4ccc(C5c6ccccc6-c6ccccc65)cc4)cc3)c3cccc4c3-c3ccccc3C43c4ccccc4-c4ccccc43)cccc21]
29
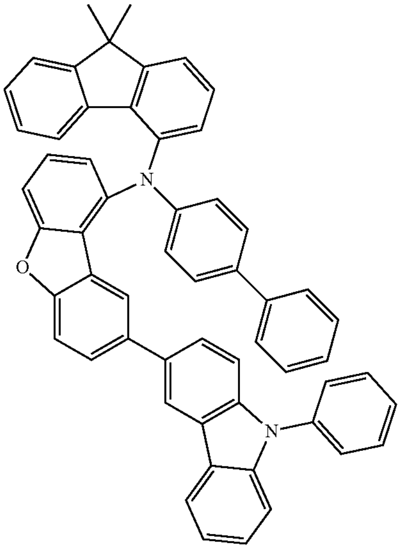 [SMILES: CC1(C)c2ccccc2-c2c(N(c3ccc(-c4ccccc4)cc3)c3cccc4oc5ccc(-c6ccc7c(c6)c6ccccc6n7-c6ccccc6)cc5c34)cccc21]
30
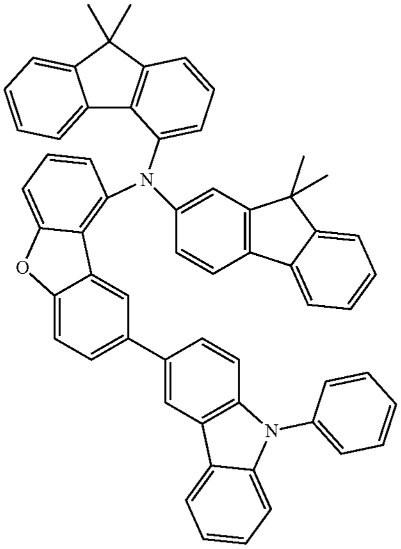 [SMILES: CC1(C)c2ccccc2-c2ccc(N(c3cccc4c3-c3ccccc3C4(C)C)c3cccc4oc5ccc(-c6ccc7c(c6)c6ccccc6n7-c6ccccc6)cc5c34)cc21]

TABLE 4-continued
31
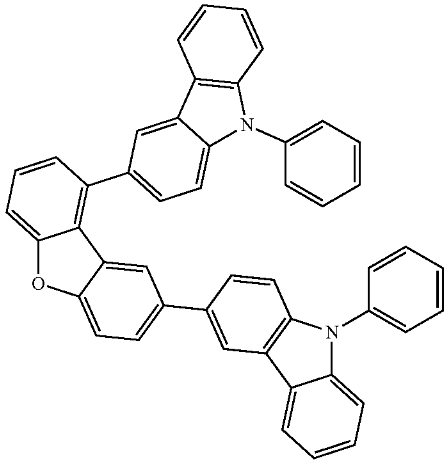 [SMILES: c1ccc(-n2c3ccccc3c3cc(-c4ccc5oc6cccc(-c7ccc8c(c7)c7ccccc7n8-c7ccccc7)c6c5c4)ccc32)cc1]
32
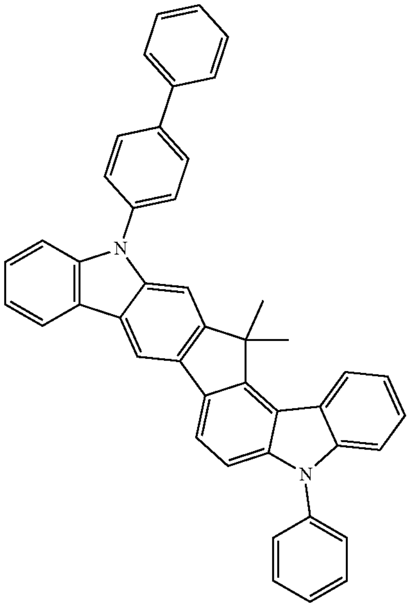 [SMILES: CC1(C)c2cc3c(cc2-c2ccc4c(c21)c1ccccc1n4-c1ccccc1)c1ccccc1n3-c1ccc(-c2ccccc2)cc1]
33
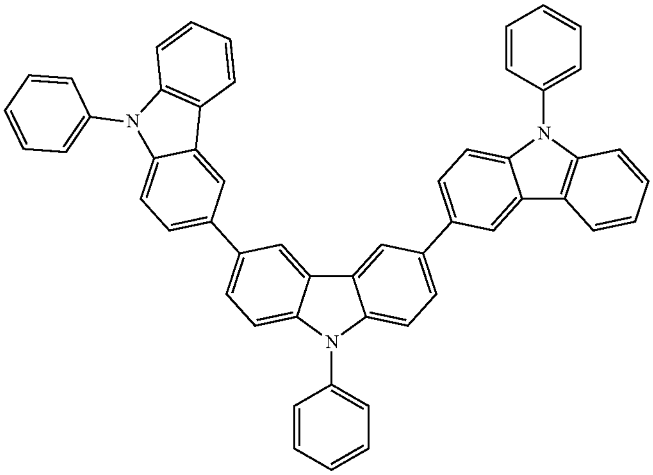 [SMILES: c1ccc(-n2c3ccccc3c3cc(-c4ccc5c(c4)c4cc(-c6ccc7c(c6)c6ccccc6n7-c6ccccc6)ccc4n5-c4ccccc4)ccc32)cc1]

TABLE 4-continued

34

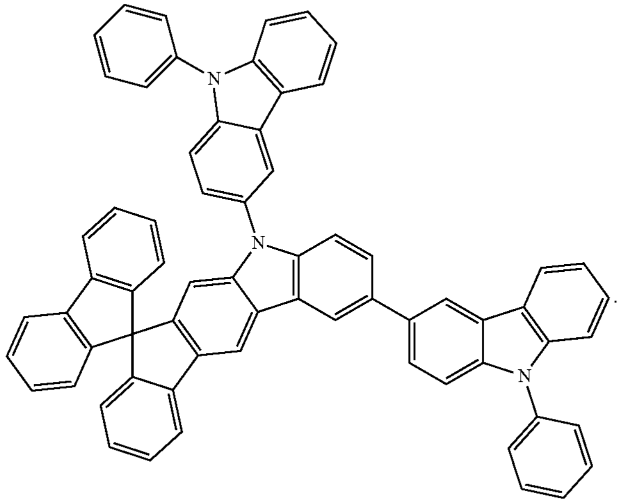 [SMILES: c1ccc(-n2c3ccccc3c3cc(-c4ccc5c(c4)c4cc6c(cc4n5-c4ccc5c(c4)c4ccccc4n5-c4ccccc4)C4(c5ccccc5-c5ccccc54)c4ccccc4-6)ccc32)cc1 ; "."]

The preparation of the compounds of the formula (2) or preferred compounds of the formulae (2), (2a), (2b), (2c), (2d), (2e), (2f), (2g), (2h) and (2i) and of the compounds from tables 3 and 4 is known to the person skilled in the art. The compounds may be prepared by synthesis steps known to the person skilled in the art, for example halogenation, preferably bromination, and a subsequent organometallic coupling reaction, for example Suzuki coupling, Heck coupling or Hartwig-Buchwald coupling. Some of the compounds of the formula (2) are commercially available.

The aforementioned host materials of the formulae (1), (1a), (1b), (1c), (1d), (1e), (1f), (1g), (1h), (1i), (1j) or (1k) and the embodiments thereof described as preferred or the compounds from table 1 and table 2 can be combined as desired in accordance with the invention with the specified host materials of the formulae (2), (2a), (2b), (2c), (2d), (2e), (2f), (2g), (2h) and (2i) and the embodiments thereof that are described as preferred or the compounds from table 3 or 4.

Particularly preferred mixtures of the host materials of the formula (1) with the host materials of the formula (2) for the composition of the invention are obtained by combination of the compounds 1 to 11 from table 2 with the compounds from table 3.

Very particularly preferred mixtures of the host materials of the formula (1) with the host materials of the formula (2) for the composition of the invention are obtained by combination of the compounds 1 to 11 from table 2 with the compounds 12 to 34 from table 4, as shown hereinafter in table 5.

TABLE 5

| | | | | | | | | |
|---|---|---|---|---|---|---|---|---|
| M1 | 1 | 12 | M2 | 1 | 13 | M3 | 1 | 14 |
| M4 | 1 | 15 | M5 | 1 | 16 | M6 | 1 | 17 |
| M7 | 1 | 18 | M8 | 1 | 19 | M9 | 1 | 20 |
| M10 | 1 | 21 | M11 | 1 | 22 | M12 | 1 | 23 |
| M13 | 1 | 24 | M14 | 1 | 25 | M15 | 1 | 26 |
| M16 | 1 | 27 | M17 | 1 | 28 | M18 | 1 | 29 |
| M19 | 1 | 30 | M20 | 1 | 31 | M21 | 1 | 32 |
| M22 | 1 | 33 | M23 | 1 | 34 | | | |
| M24 | 2 | 12 | M25 | 2 | 13 | M26 | 2 | 14 |
| M27 | 2 | 15 | M28 | 2 | 16 | M29 | 2 | 17 |
| M30 | 2 | 18 | M31 | 2 | 19 | M32 | 2 | 20 |
| M33 | 2 | 21 | M34 | 2 | 22 | M35 | 2 | 23 |
| M36 | 2 | 24 | M37 | 2 | 25 | M38 | 2 | 26 |

TABLE 5-continued

| | | | | | | | | |
|---|---|---|---|---|---|---|---|---|
| M39 | 2 | 27 | M40 | 2 | 28 | M41 | 2 | 29 |
| M42 | 2 | 30 | M43 | 2 | 31 | M44 | 2 | 32 |
| M45 | 2 | 33 | M46 | 2 | 34 | | | |
| M47 | 3 | 12 | M48 | 3 | 13 | M49 | 3 | 14 |
| M50 | 3 | 15 | M51 | 3 | 16 | M52 | 3 | 17 |
| M53 | 3 | 18 | M54 | 3 | 19 | M55 | 3 | 20 |
| M56 | 3 | 21 | M57 | 3 | 22 | M58 | 3 | 23 |
| M59 | 3 | 24 | M60 | 3 | 25 | M61 | 3 | 26 |
| M62 | 3 | 27 | M63 | 3 | 28 | M64 | 3 | 29 |
| M65 | 3 | 30 | M66 | 3 | 31 | M67 | 3 | 32 |
| M68 | 3 | 33 | M69 | 3 | 34 | | | |
| M70 | 4 | 12 | M71 | 4 | 13 | M72 | 4 | 14 |
| M73 | 4 | 15 | M74 | 4 | 16 | M75 | 4 | 17 |
| M76 | 4 | 18 | M77 | 4 | 19 | M78 | 4 | 20 |
| M79 | 4 | 21 | M80 | 4 | 22 | M81 | 4 | 23 |
| M82 | 4 | 24 | M83 | 4 | 25 | M84 | 4 | 26 |
| M85 | 4 | 27 | M86 | 4 | 28 | M87 | 4 | 29 |
| M88 | 4 | 30 | M89 | 4 | 31 | M90 | 4 | 32 |
| M91 | 4 | 33 | M92 | 4 | 34 | | | |
| M93 | 5 | 12 | M94 | 5 | 13 | M95 | 5 | 14 |
| M96 | 5 | 15 | M97 | 5 | 16 | M98 | 5 | 17 |
| M99 | 5 | 18 | M100 | 5 | 19 | M101 | 5 | 20 |
| M102 | 5 | 21 | M103 | 5 | 22 | M104 | 5 | 23 |
| M105 | 5 | 24 | M106 | 5 | 25 | M107 | 5 | 26 |
| M108 | 5 | 27 | M109 | 5 | 28 | M110 | 5 | 29 |
| M111 | 5 | 30 | M112 | 5 | 31 | M113 | 5 | 32 |
| M114 | 5 | 33 | M115 | 5 | 34 | | | |
| M116 | 6 | 12 | M117 | 6 | 13 | M118 | 6 | 14 |
| M119 | 6 | 15 | M120 | 6 | 16 | M121 | 6 | 17 |
| M122 | 6 | 18 | M123 | 6 | 19 | M124 | 6 | 20 |
| M125 | 6 | 21 | M126 | 6 | 22 | M127 | 6 | 23 |
| M128 | 6 | 24 | M129 | 6 | 25 | M130 | 6 | 26 |
| M131 | 6 | 27 | M132 | 6 | 28 | M133 | 6 | 29 |
| M134 | 6 | 30 | M135 | 6 | 31 | M136 | 6 | 32 |
| M137 | 6 | 33 | M138 | 6 | 34 | | | |
| M139 | 7 | 12 | M140 | 7 | 13 | M141 | 7 | 14 |
| M142 | 7 | 15 | M143 | 7 | 16 | M144 | 7 | 17 |
| M145 | 7 | 18 | M146 | 7 | 19 | M147 | 7 | 20 |
| M148 | 7 | 21 | M149 | 7 | 22 | M150 | 7 | 23 |
| M151 | 7 | 24 | M152 | 7 | 25 | M153 | 7 | 26 |
| M154 | 7 | 27 | M155 | 7 | 28 | M156 | 7 | 29 |
| M157 | 7 | 30 | M158 | 7 | 31 | M159 | 7 | 32 |
| M160 | 7 | 33 | M161 | 7 | 34 | | | |
| M162 | 8 | 12 | M163 | 8 | 13 | M164 | 8 | 14 |
| M165 | 8 | 15 | M166 | 8 | 16 | M167 | 8 | 17 |
| M168 | 8 | 18 | M169 | 8 | 19 | M170 | 8 | 20 |
| M171 | 8 | 21 | M172 | 8 | 22 | M173 | 8 | 23 |
| M174 | 8 | 24 | M175 | 8 | 25 | M176 | 8 | 26 |
| M177 | 8 | 27 | M178 | 8 | 28 | M179 | 8 | 29 |
| M180 | 8 | 30 | M181 | 8 | 31 | M182 | 8 | 32 |
| M183 | 8 | 33 | M184 | 8 | 34 | | | |

TABLE 5-continued

| | | | | | | | | |
|---|---|---|---|---|---|---|---|---|
| M185 | 9 | 12 | M186 | 9 | 13 | M187 | 9 | 14 |
| M188 | 9 | 15 | M189 | 9 | 16 | M190 | 9 | 17 |
| M191 | 9 | 18 | M192 | 9 | 19 | M193 | 9 | 20 |
| M194 | 9 | 21 | M195 | 9 | 22 | M196 | 9 | 23 |
| M197 | 9 | 24 | M198 | 9 | 25 | M199 | 9 | 26 |
| M200 | 9 | 27 | M201 | 9 | 28 | M202 | 9 | 29 |
| M203 | 9 | 30 | M204 | 9 | 31 | M205 | 9 | 32 |
| M206 | 9 | 33 | M207 | 9 | 34 | | | |
| M208 | 10 | 12 | M209 | 10 | 13 | M210 | 10 | 14 |
| M211 | 10 | 15 | M212 | 10 | 16 | M213 | 10 | 17 |
| M214 | 10 | 18 | M215 | 10 | 19 | M216 | 10 | 20 |
| M217 | 10 | 21 | M218 | 10 | 22 | M219 | 10 | 23 |
| M220 | 10 | 24 | M221 | 10 | 25 | M222 | 10 | 26 |
| M223 | 10 | 27 | M224 | 10 | 28 | M225 | 10 | 29 |
| M226 | 10 | 30 | M227 | 10 | 31 | M228 | 10 | 32 |
| M229 | 10 | 33 | M230 | 10 | 34 | | | |
| M231 | 11 | 12 | M232 | 11 | 13 | M233 | 11 | 14 |
| M234 | 11 | 15 | M235 | 11 | 16 | M236 | 11 | 17 |
| M237 | 11 | 18 | M238 | 11 | 19 | M239 | 11 | 20 |
| M240 | 11 | 21 | M241 | 11 | 22 | M242 | 11 | 23 |
| M243 | 11 | 24 | M244 | 11 | 25 | M245 | 11 | 26 |
| M246 | 11 | 27 | M247 | 11 | 28 | M248 | 11 | 29 |
| M249 | 11 | 30 | M250 | 11 | 31 | M251 | 11 | 32 |
| M252 | 11 | 33 | M253 | 11 | 34. | | | |

The concentration of the electron-transporting host of the formula (1) as described above or described as preferred in the composition of the invention is in the range from 5% by weight to 90% by weight, preferably in the range from 10% by weight to 85% by weight, more preferably in the range from 20% by weight to 85% by weight, even more preferably in the range from 30% by weight to 80% by weight, very especially preferably in the range from 20% by weight to 60% by weight and most preferably in the range from 30% by weight to 50% by weight, based on the overall composition.

The concentration of the hole-transporting host of the formula (2) as described above or described as preferred in the composition is in the range from 10% by weight to 95% by weight, preferably in the range from 15% by weight to 90% by weight, more preferably in the range from 15% by weight to 80% by weight, even more preferably in the range from 20% by weight to 70% by weight, very especially preferably in the range from 40% by weight to 80% by weight and most preferably in the range from 50% by weight to 70% by weight, based on the overall composition.

In a further preferred embodiment, the composition of the invention may comprise, as well as at least one compound of the formula (1) as described above or described as preferred as electron-transporting host or electron-transporting matrix material, and at least one compound of the formula (2) as described above or described as preferred as hole-transporting host or hole-transporting matrix material, further compounds as well, especially organic functional materials. In this embodiment, the composition preferably forms an organic layer in an electronic device as described hereinafter.

The present invention therefore also relates to a composition which, as well as the aforementioned materials, also comprises at least one further compound selected from the group consisting of hole injection materials, hole transport materials, hole blocker materials, wide band gap materials, fluorescent emitters, phosphorescent emitters, host materials, electron blocker materials, electron transport materials and electron injection materials, n-dopants and p-dopants. It does not present any difficulties at all to the person skilled in the art to select these from a multitude of materials that are known to such a person.

n-Dopants are understood herein to mean reducing agents, i.e. electron donors. Preferred examples of n-dopants are $W(hpp)_4$ and further electron-rich metal complexes according to WO 2005/086251 A2, P=N compounds (e.g. WO 2012/175535 A1, WO 2012/175219 A1), naphthylenecarbodiimides (e.g. WO 2012/168358 A1), fluorenes (e.g. WO 2012/031735 A1), radicals and diradicals (e.g. EP 1837926 A1, WO 2007/107306 A1), pyridines (e.g. EP 2452946 A1, EP 2463927 A1), N-heterocyclic compounds (e.g. WO 2009/000237 A1) and acridines and phenazines (e.g. US 2007/145355 A1).

p-Dopants are understood herein to mean oxidizing agents, i.e. electron acceptors. Preferred examples of p-dopants are $F_4$-TCNQ, $F_6$-TNAP, NDP-2 (from Novaled), NDP-9 (from Novaled), quinones (e.g. EP 1538684 A1, WO 2006/081780 A1, WO 2009/003455 A1, WO 2010/097433 A1), radialenes (e.g. EP 1988587 A1, US 2010/102709 A1, EP 2180029 A1, WO 2011/131185 A1, WO 2011134458 A1, US 2012/223296 A1), S-containing transition metal complexes (e.g. WO 2007/134873 A1, WO 2008/061517 A2, WO 2008/061518 A2, DE 102008051737 A1, WO 2009/089821 A1, US 2010/096600 A1), bisimidazoles (e.g. WO 2008/138580 A1), phthalocyanines (e.g. WO 2008/058525 A2), bora-tetraazapentalenes (e.g. WO 2007/115540 A1), fullerenes (e.g. DE 102010046040 A1) and main group halides (e.g. WO 2008/128519 A2).

A wide band gap material is understood herein to mean a material within the scope of the disclosure of U.S. Pat. No. 7,294,849 which is characterized by a band gap of at least 3.5 eV, the band gap being understood to mean the gap between the HOMO and LUMO energy of a material.

It is preferable when the composition of the invention comprising a bipolar host and an electron-transporting host additionally comprises at least one light-emitting compound or an emitter, particular preference being given to phosphorescent emitters.

The term "phosphorescent emitters" typically encompasses compounds where the light is emitted through a spin-forbidden transition from an excited state having higher spin multiplicity, i.e. a spin state >1, for example through a transition from a triplet state or a state having an even higher spin quantum number, for example a quintet state. This is preferably understood to mean a transition from a triplet state.

Suitable phosphorescent emitters (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the above-mentioned metals are regarded as phosphorescent emitters.

In general, all phosphorescent complexes as used for phosphorescent OLEDs according to the prior art and as known to those skilled in the art in the field of organic electroluminescent devices are suitable.

Examples of the above-described emitters can be found in applications WO 2016/015815, WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2015/036074, WO 2015/117718 and WO 2016/015815.
Preferred examples of phosphorescent emitters are listed in table 6 below.
TABLE 6
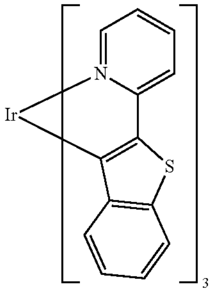
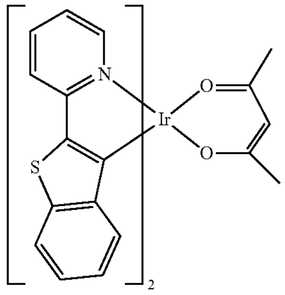
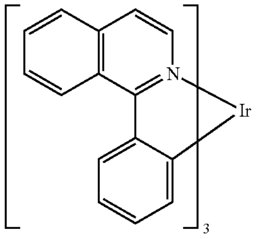
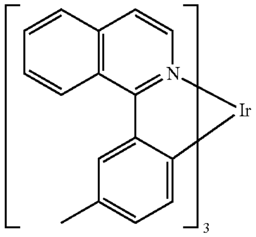
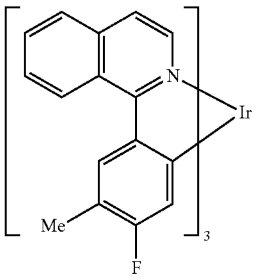
TABLE 6-continued
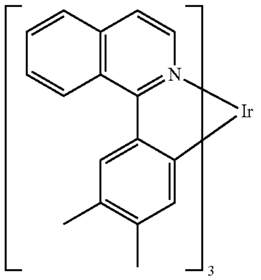
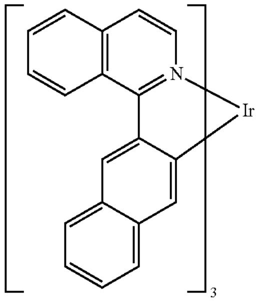
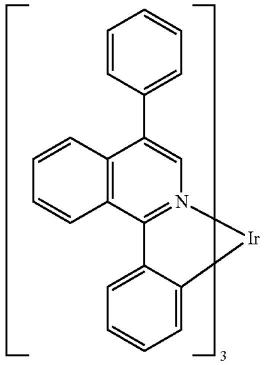
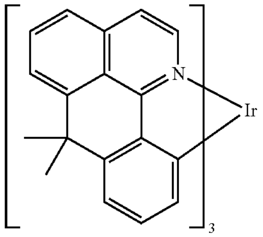
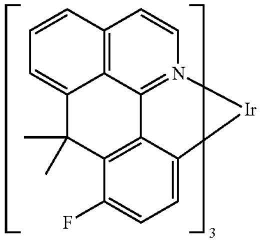

TABLE 6-continued
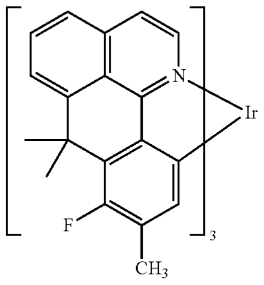
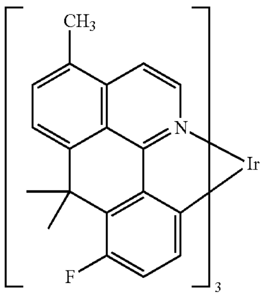
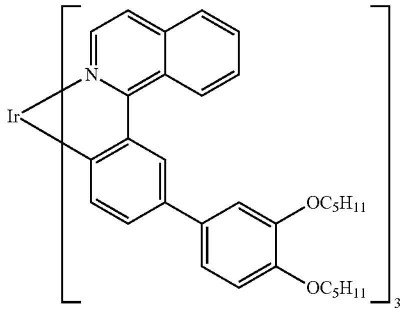
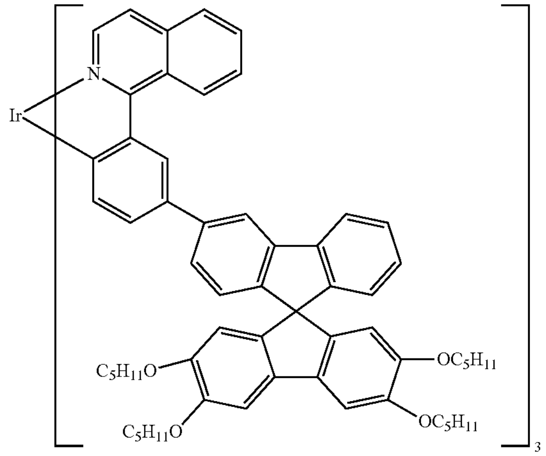
TABLE 6-continued
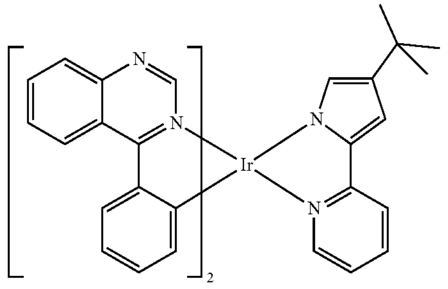
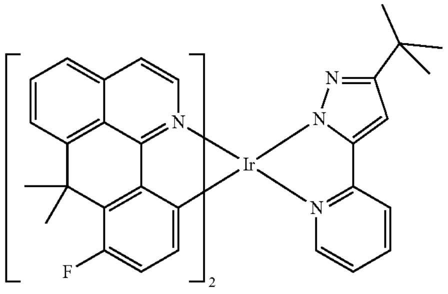
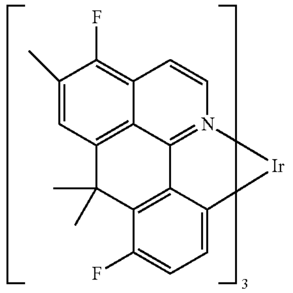
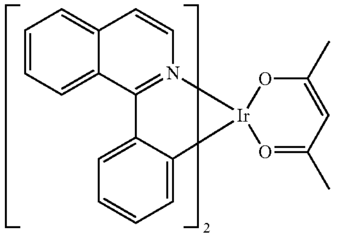
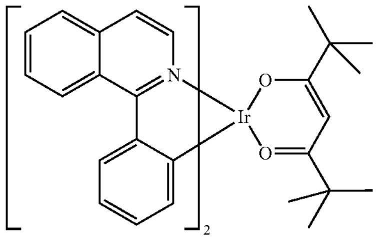
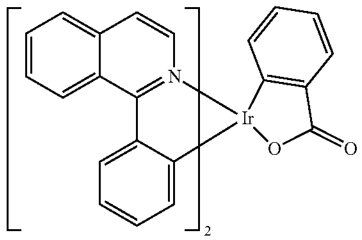

TABLE 6-continued
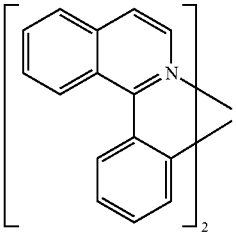
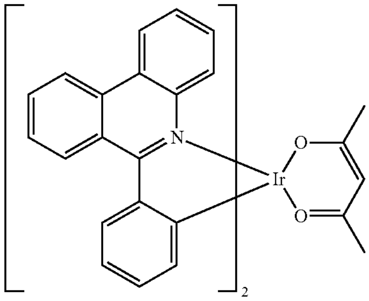
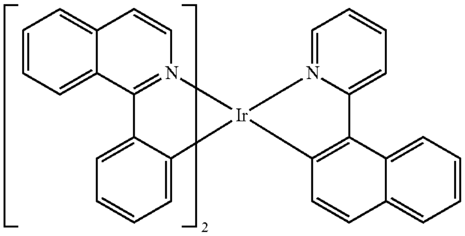
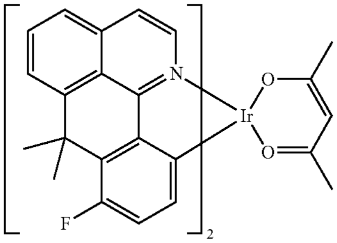
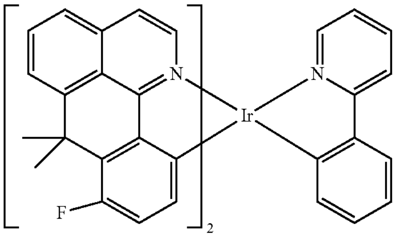
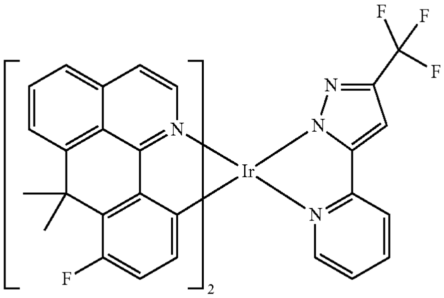
TABLE 6-continued
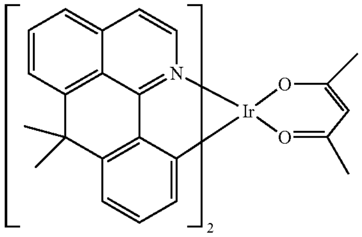
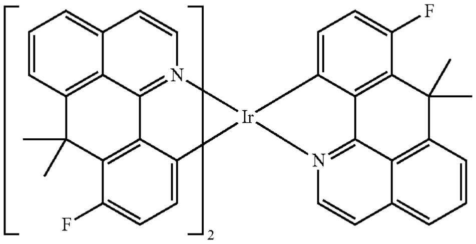
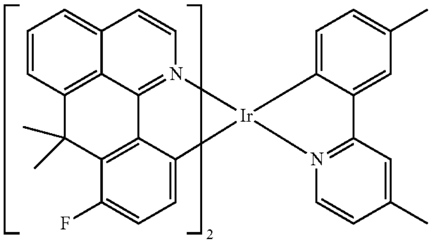
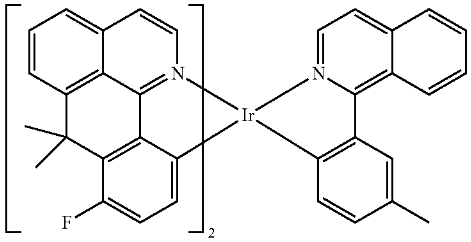
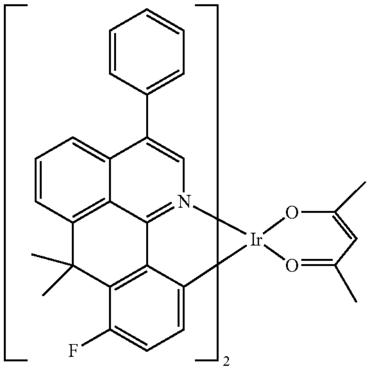
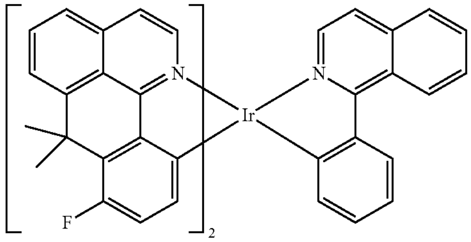

TABLE 6-continued
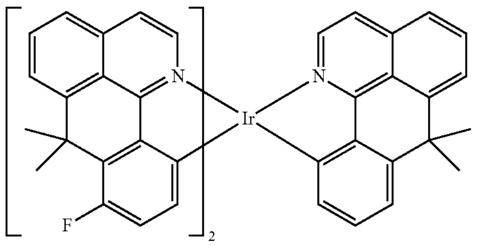
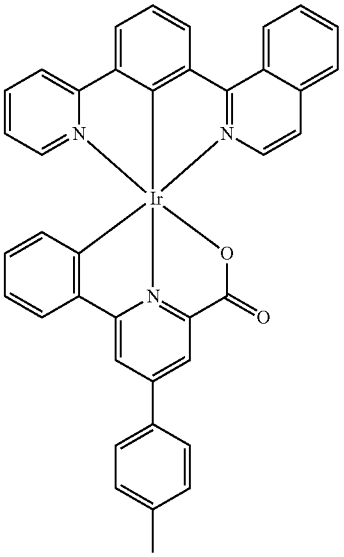
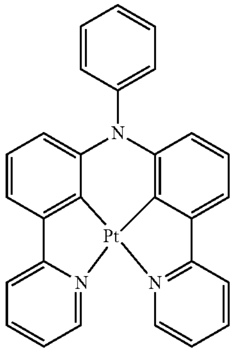
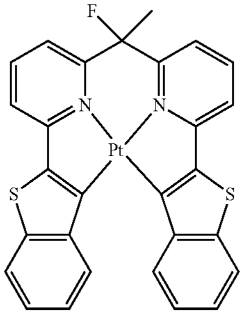
TABLE 6-continued
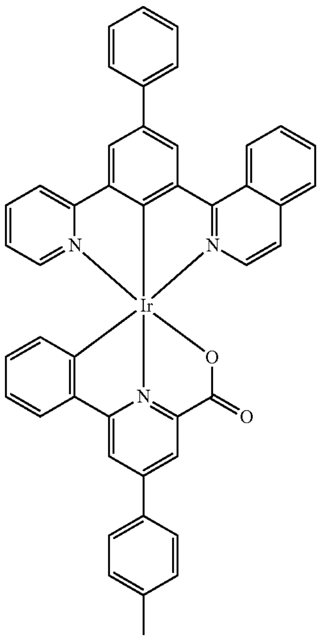
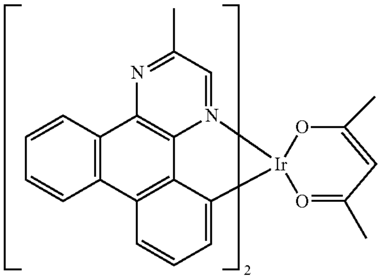
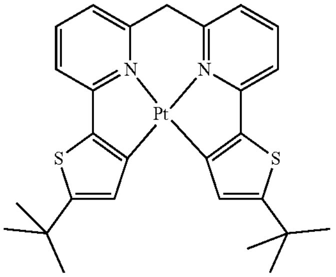
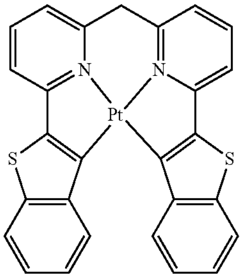

TABLE 6-continued
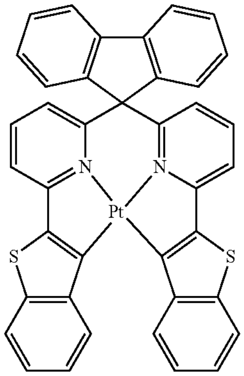
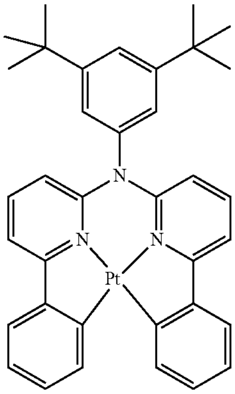
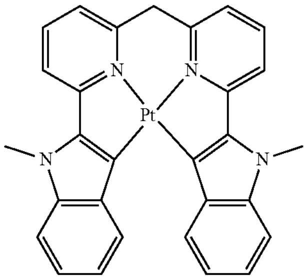
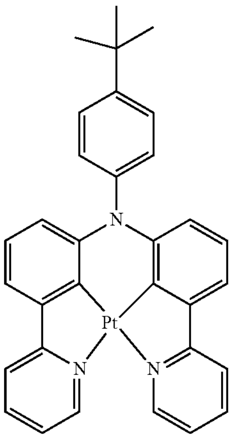
TABLE 6-continued
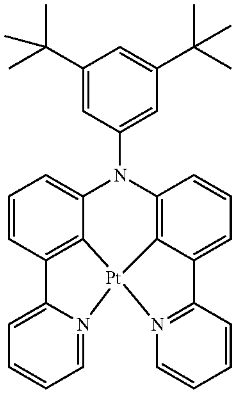
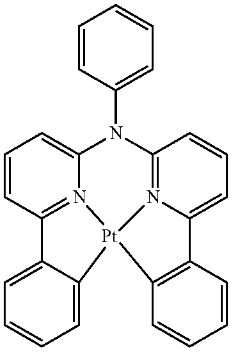
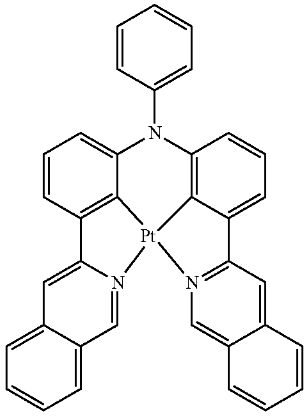
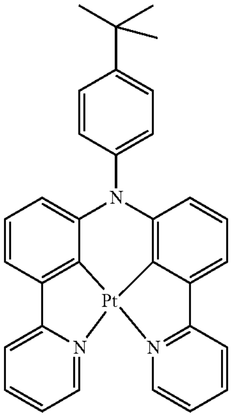

TABLE 6-continued
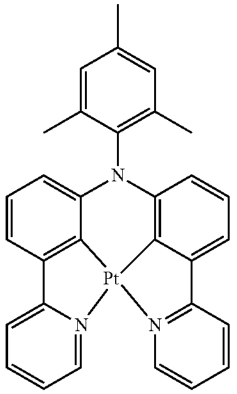
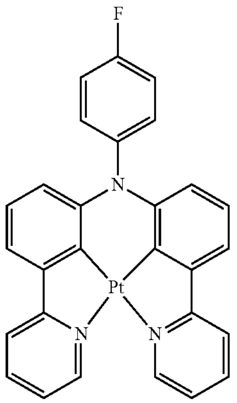
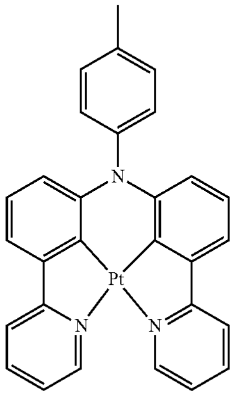
TABLE 6-continued
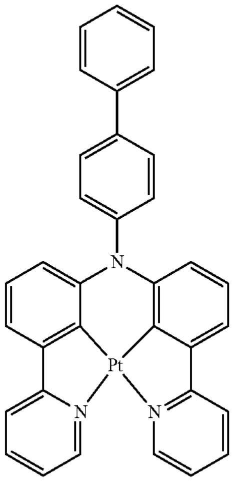
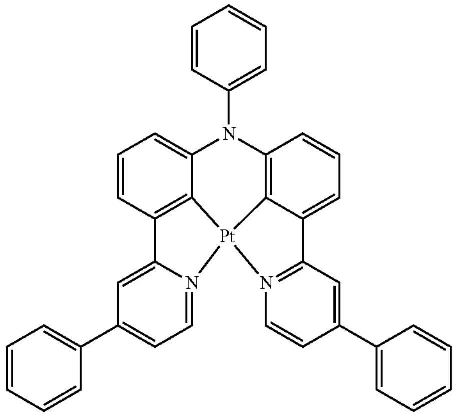
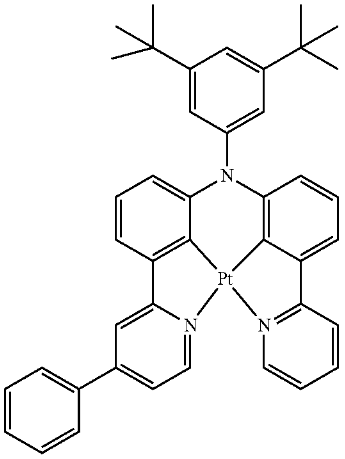

TABLE 6-continued
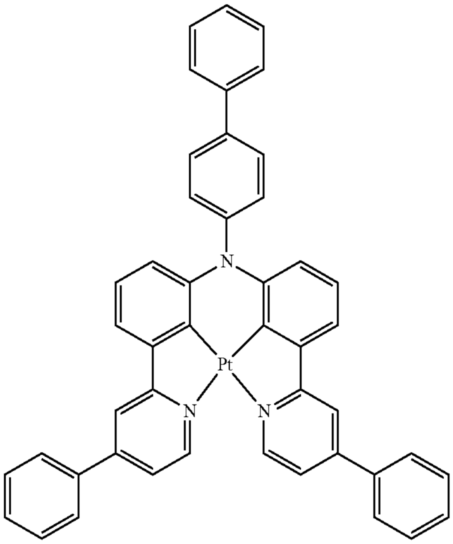
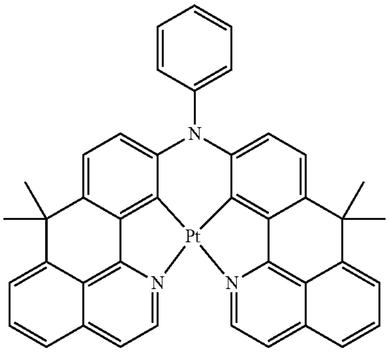
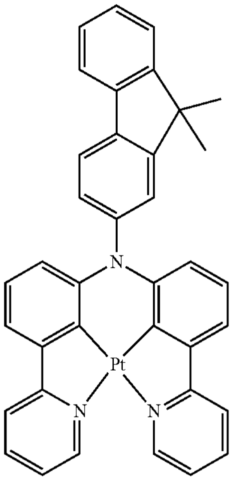
TABLE 6-continued
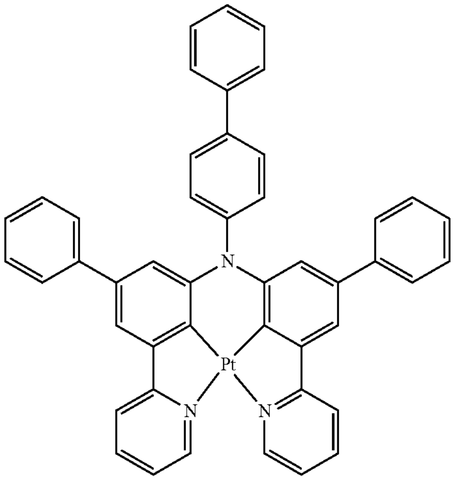
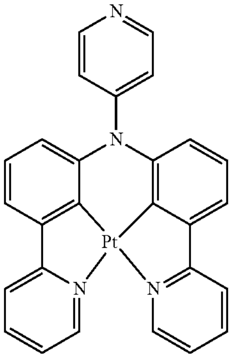
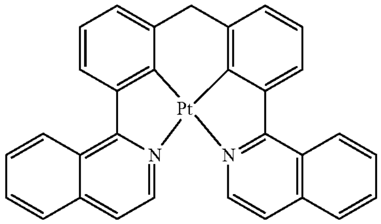
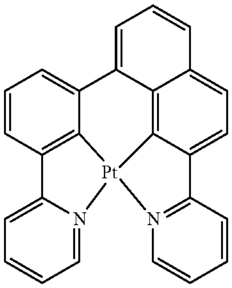

TABLE 6-continued
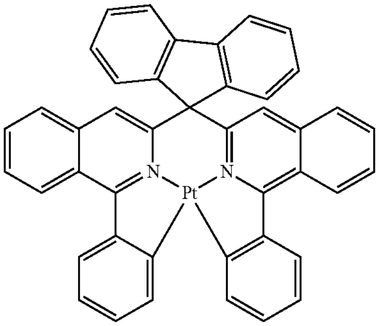
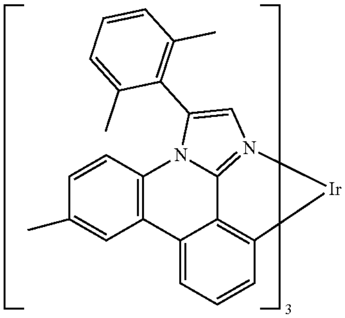
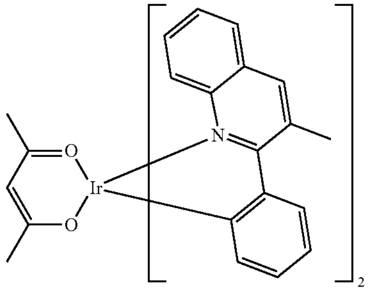
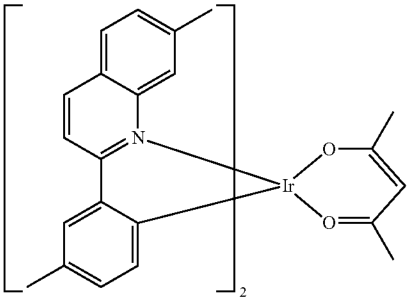
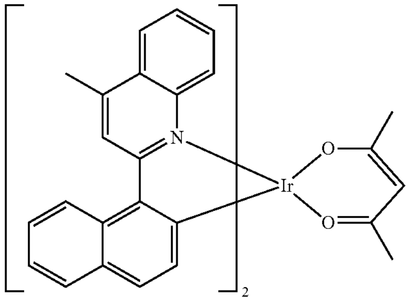
TABLE 6-continued
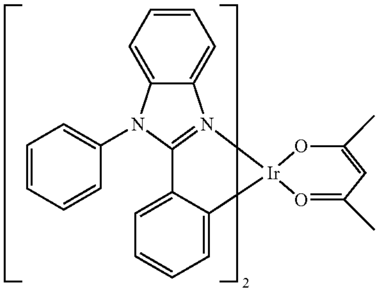
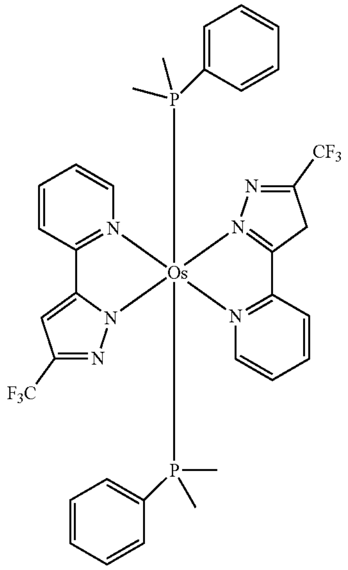
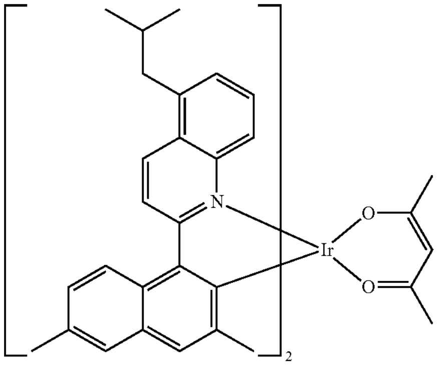
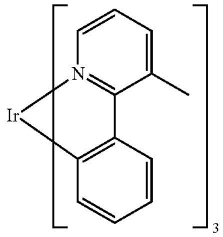

TABLE 6-continued
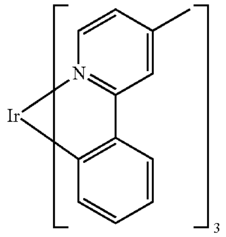
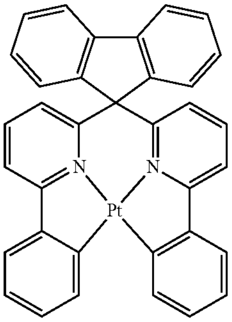
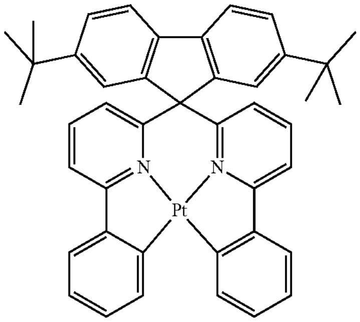
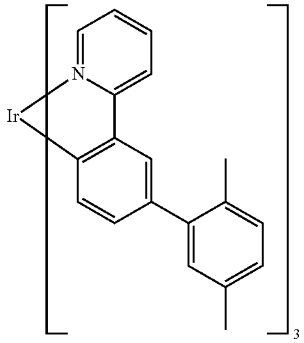
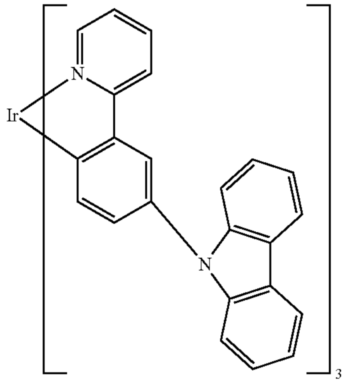
TABLE 6-continued
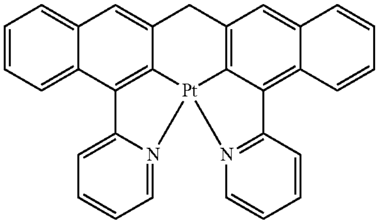
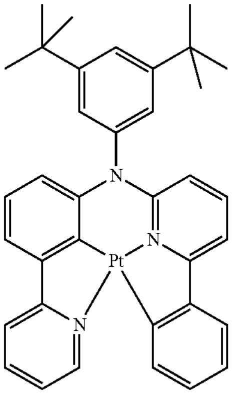
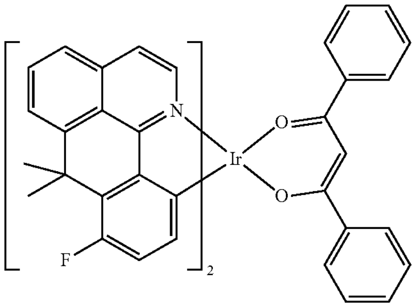
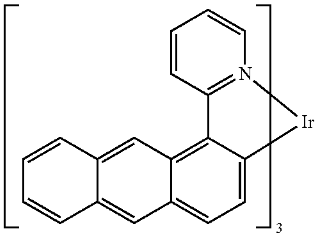
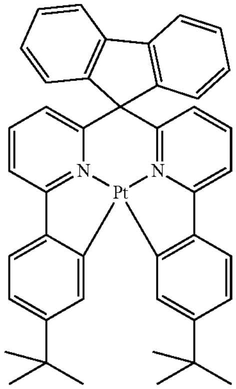

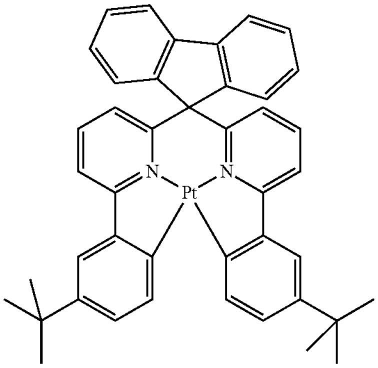
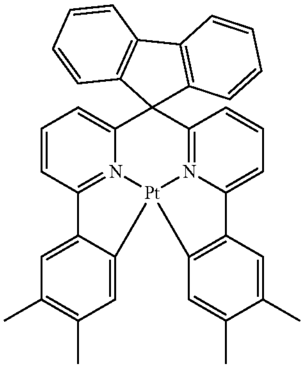
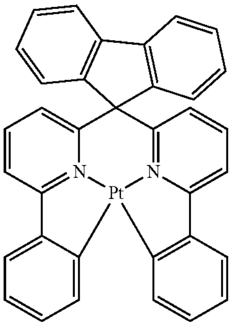
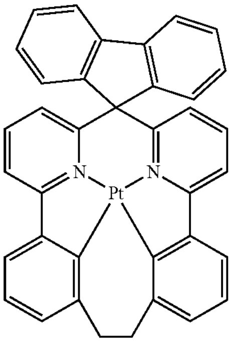
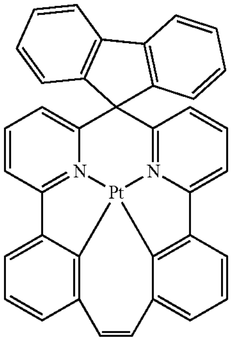
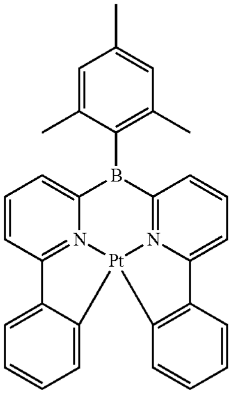
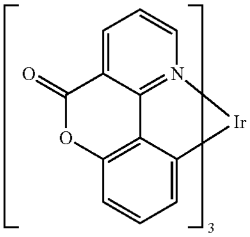
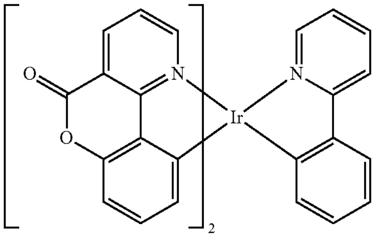
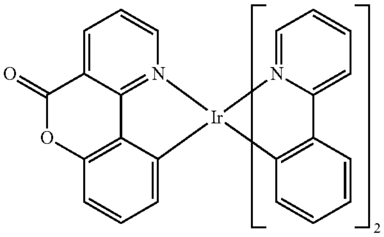

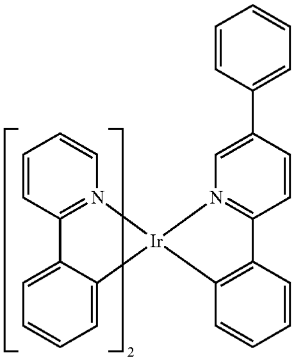
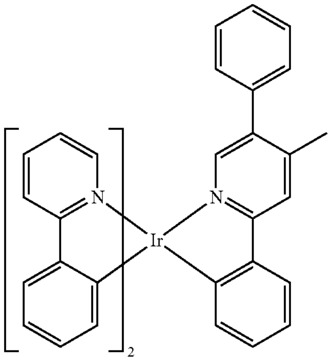
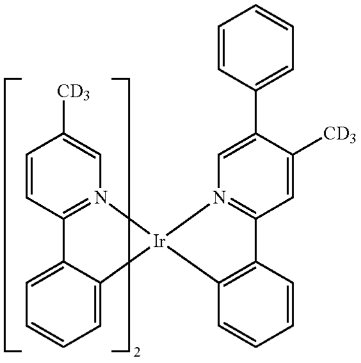
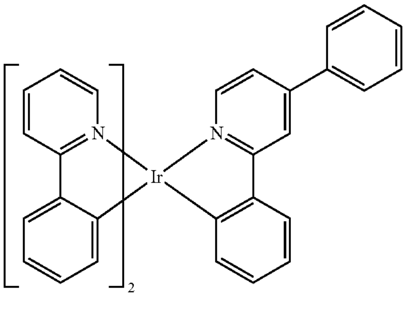
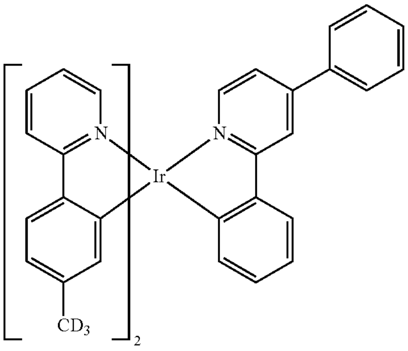
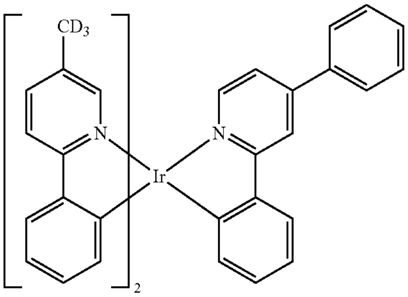
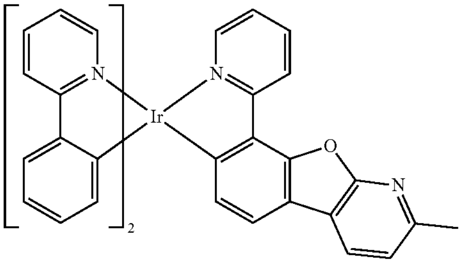
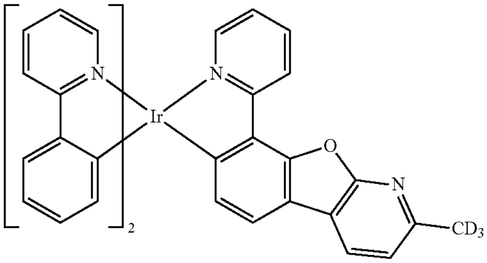
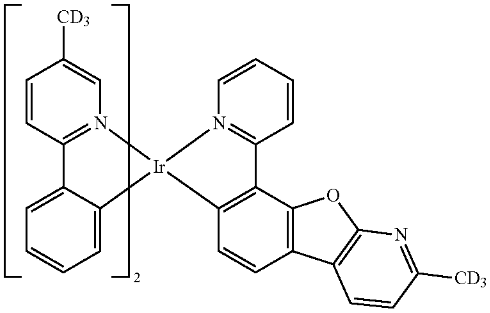

TABLE 6-continued
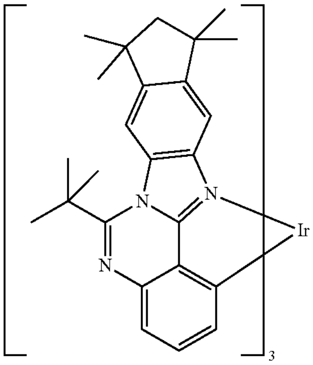
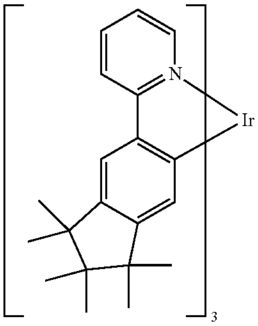
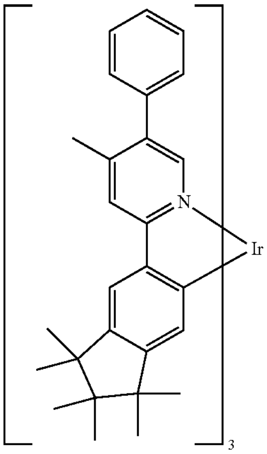
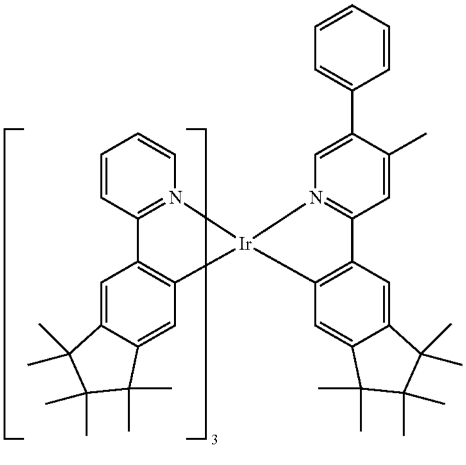
TABLE 6-continued
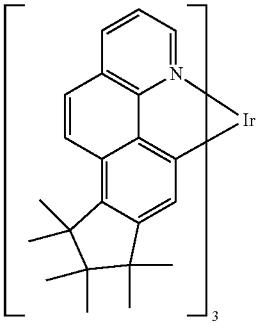
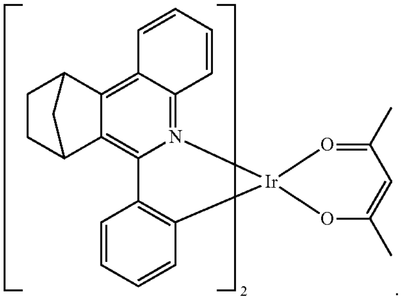
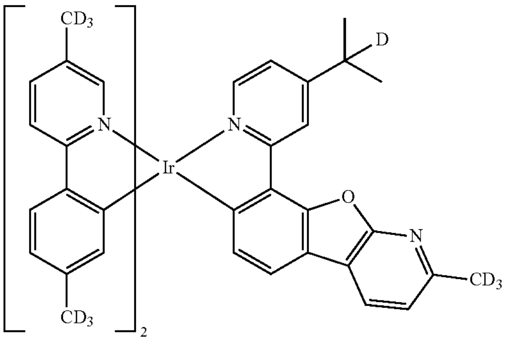
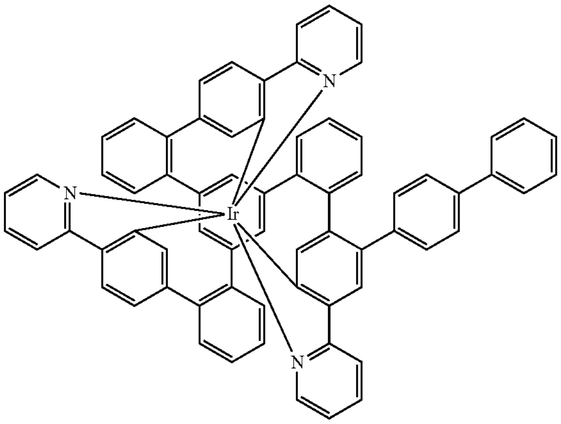

TABLE 6-continued
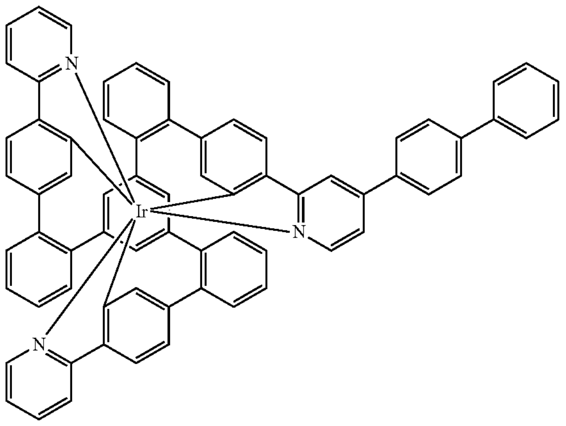
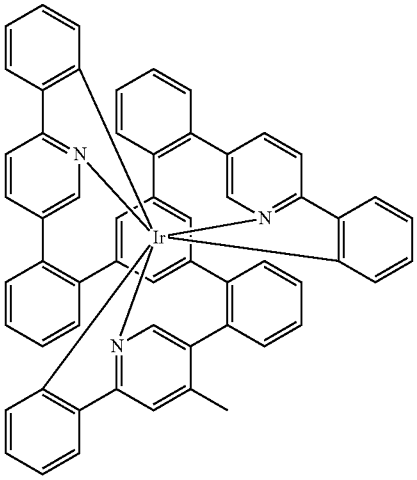
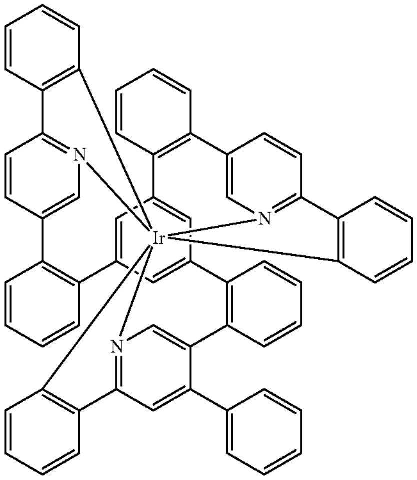
TABLE 6-continued
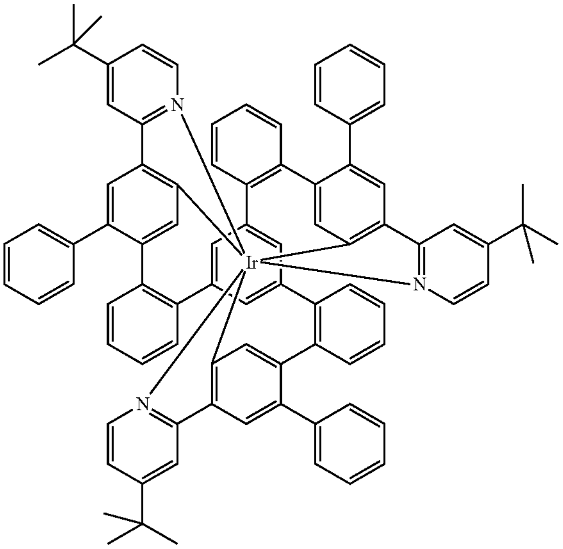
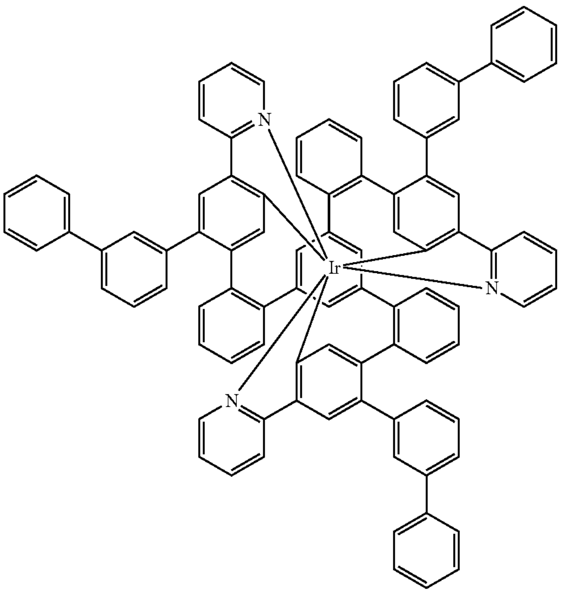

TABLE 6-continued

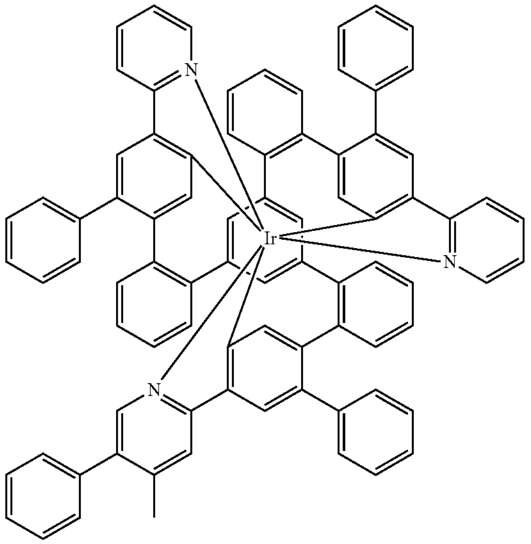

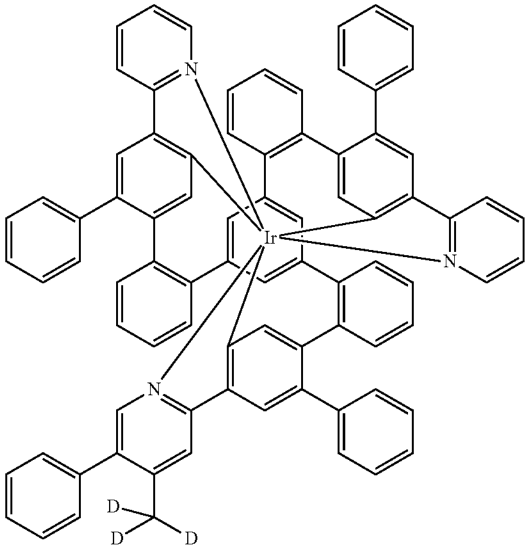

Preferred examples of phosphorescent polypodal emitters are listed in table 7 below.

TABLE 7

| |
|---|
| CAS-1269508-30-6 |
| CAS-1215692-34-4 |
| CAS-1370364-40-1 |
| CAS-1370364-42-3 |
| CAS-1989600-74-9 |
| CAS-1989600-75-0 |
| CAS-1989600-77-2 |
| CAS-1989600-78-3 |
| CAS-1989600-79-4 |
| CAS-1989600-82-9 |
| CAS-1989600-83-0 |
| CAS-1989600-84-1 |
| CAS-1989600-85-2 |
| CAS-1989600-86-3 |
| CAS-1989600-87-4 |
| CAS-1989600-88-5 |
| CAS-1989600-89-6 |
| CAS-1989601-11-7 |
| CAS-1989601-23-1 |
| CAS-1989601-26-4 |

TABLE 7-continued

| |
|---|
| CAS-1989601-28-6 |
| CAS-1989601-29-7 |
| CAS-1989601-33-3 |
| CAS-1989601-40-2 |
| CAS-1989601-41-3 |
| CAS-1989601-42-4 |
| CAS-1989601-43-5 |
| CAS-1989601-44-6 |
| CAS-1989601-45-7 |
| CAS-1989601-46-8 |
| CAS-1989601-47-9 |
| CAS-1989601-48-0 |
| CAS-1989601-49-1 |
| CAS-1989601-50-4 |
| CAS-1989601-51-5 |
| CAS-1989601-52-6 |
| CAS-1989601-53-7 |
| CAS-1989601-54-8 |
| CAS-1989601-55-9 |
| CAS-1989601-56-0 |
| CAS-1989601-57-1 |
| CAS-1989601-58-2 |
| CAS-1989601-59-3 |
| CAS-1989601-60-6 |
| CAS-1989601-61-7 |
| CAS-1989601-62-8 |
| CAS-1989601-63-9 |
| CAS-1989601-64-0 |
| CAS-1989601-65-1 |
| CAS-1989601-66-2 |
| CAS-1989601-67-3 |
| CAS-1989604-35-4 |
| CAS-1989604-36-5 |
| CAS-1989604-37-6 |
| CAS-1989604-38-7 |
| CAS-1989604-39-8 |
| CAS-1989604-40-1 |
| CAS-1989604-41-2 |
| CAS-1989604-42-3 |
| CAS-1989604-43-4 |
| CAS-1989604-45-6 |
| CAS-1989604-46-7 |
| CAS-1989604-47-8 |
| CAS-1989604-48-9 |
| CAS-1989604-49-0 |
| CAS-1989604-50-3 |
| CAS-1989604-52-5 |
| CAS-1989604-53-6 |
| CAS-1989604-54-7 |
| CAS-1989604-55-8 |
| CAS-1989604-56-9 |
| CAS-1989604-57-0 |
| CAS-1989604-58-1 |
| CAS-1989604-59-2 |
| CAS-1989604-60-5 |
| CAS-1989604-61-6 |
| CAS-1989604-62-7 |
| CAS-1989604-63-8 |
| CAS-1989604-64-9 |
| CAS-1989604-65-0 |
| CAS-1989604-66-1 |
| CAS-1989604-67-2 |
| CAS-1989604-68-3 |
| CAS-1989604-69-4 |
| CAS-1989604-70-7 |
| CAS-1989604-71-8 |
| CAS-1989604-72-9 |
| CAS-1989604-73-0 |
| CAS-1989604-74-1 |
| CAS-1989604-75-2 |
| CAS-1989604-76-3 |
| CAS-1989604-77-4 |
| CAS-1989604-78-5 |
| CAS-1989604-79-6 |
| CAS-1989604-80-9 |
| CAS-1989604-81-0 |
| CAS-1989604-82-1 |
| CAS-1989604-83-2 |
| CAS-1989604-84-3 |
| CAS-1989604-85-4 |

TABLE 7-continued

| |
|---|
| CAS-1989604-86-5 |
| CAS-1989604-87-6 |
| CAS-1989658-39-0 |
| CAS-1989658-41-4 |
| CAS-1989658-43-6 |
| CAS-1989658-47-0 |
| CAS-1989658-49-2 |
| CAS-2088184-07-8 |
| CAS-2088184-08-9 |
| CAS-2088184-09-0 |
| CAS-2088184-10-3 |
| CAS-2088184-11-4 |
| CAS-2088184-13-6 |
| CAS-2088184-14-7 |
| CAS-2088184-15-8 |
| CAS-2088184-16-9 |
| CAS-2088184-17-0 |
| CAS-2088184-18-1 |
| CAS-2088184-19-2 |
| CAS-2088184-20-5 |
| CAS-2088184-21-6 |
| CAS-2088184-22-7 |
| CAS-2088184-23-8 |
| CAS-2088184-24-9 |
| CAS-2088184-25-0 |
| CAS-2088184-26-1 |
| CAS-2088184-27-2 |
| CAS-2088184-28-3 |
| CAS-2088184-29-4 |
| CAS-2088184-30-7 |
| CAS-2088184-32-9 |
| CAS-2088184-34-1 |
| CAS-2088184-35-2 |
| CAS-2088184-36-3 |
| CAS-2088184-37-4 |
| CAS-2088184-38-5 |
| CAS-2088184-39-6 |
| CAS-2088184-40-9 |
| CAS-2088184-41-0 |
| CAS-2088184-42-1 |
| CAS-2088184-43-2 |
| CAS-2088184-44-3 |
| CAS-2088184-45-4 |
| CAS-2088184-46-5 |
| CAS-2088184-47-6 |
| CAS-2088184-48-7 |
| CAS-2088184-49-8 |
| CAS-2088184-50-1 |
| CAS-2088184-51-2 |
| CAS-2088184-52-3 |
| CAS-2088184-53-4 |
| CAS-2088184-54-5 |
| CAS-2088184-55-6 |
| CAS-1989601-68-4 |
| CAS-1989601-69-5 |
| CAS-1989601-70-8 |
| CAS-1989601-71-9 |
| CAS-1989601-72-0 |
| CAS-1989601-73-1 |
| CAS-1989601-74-2 |
| CAS-1989601-75-3 |
| CAS-1989601-76-4 |
| CAS-1989601-77-5 |
| CAS-1989601-78-6 |
| CAS-1989601-79-7 |
| CAS-1989601-80-0 |
| CAS-1989601-81-1 |
| CAS-1989601-82-2 |
| CAS-1989601-83-3 |
| CAS-1989601-84-4 |
| CAS-1989601-85-5 |
| CAS-1989601-86-6 |
| CAS-1989601-87-7 |
| CAS-1989601-88-8 |
| CAS-1989601-89-9 |
| CAS-1989601-90-2 |
| CAS-1989601-91-3 |
| CAS-1989601-92-4 |
| CAS-1989601-93-5 |
| CAS-1989601-94-6 |

TABLE 7-continued

| |
|---|
| CAS-1989601-95-7 |
| CAS-1989601-96-8 |
| CAS-1989601-97-9 |
| CAS-1989601-98-0 |
| CAS-1989601-99-1 |
| CAS-1989602-00-7 |
| CAS-1989602-01-8 |
| CAS-1989602-02-9 |
| CAS-1989602-03-0 |
| CAS-1989602-04-1 |
| CAS-1989602-05-2 |
| CAS-1989602-06-3 |
| CAS-1989602-07-4 |
| CAS-1989602-08-5 |
| CAS-1989602-09-6 |
| CAS-1989602-10-9 |
| CAS-1989602-11-0 |
| CAS-1989602-12-1 |
| CAS-1989602-13-2 |
| CAS-1989602-14-3 |
| CAS-1989602-15-4 |
| CAS-1989602-16-5 |
| CAS-1989602-17-6 |
| CAS-1989602-18-7 |
| CAS-1989604-88-7 |
| CAS-1989604-89-8 |
| CAS-1989604-90-1 |
| CAS-1989604-92-3 |
| CAS-1989604-93-4 |
| CAS-1989604-94-5 |
| CAS-1989604-95-6 |
| CAS-1989604-96-7 |
| CAS-1989604-97-8 |
| CAS-1989605-09-5 |
| CAS-1989605-10-8 |
| CAS-1989605-11-9 |
| CAS-1989605-13-1 |
| CAS-1989605-14-2 |
| CAS-1989605-15-3 |
| CAS-1989605-16-4 |
| CAS-1989605-17-5 |
| CAS-1989605-18-6 |
| CAS-1989605-19-7 |
| CAS-1989605-20-0 |
| CAS-1989605-21-1 |
| CAS-1989605-22-2 |
| CAS-1989605-23-3 |
| CAS-1989605-24-4 |
| CAS-1989605-25-5 |
| CAS-1989605-26-6 |
| CAS-1989605-27-7 |
| CAS-1989605-28-8 |
| CAS-1989605-29-9 |
| CAS-1989605-30-2 |
| CAS-1989605-31-3 |
| CAS-1989605-32-4 |
| CAS-1989605-33-5 |
| CAS-1989605-34-6 |
| CAS-1989605-35-7 |
| CAS-1989605-36-8 |
| CAS-1989605-37-9 |
| CAS-1989605-38-0 |
| CAS-1989605-39-1 |
| CAS-1989605-40-4 |
| CAS-1989605-41-5 |
| CAS-1989605-42-6 |
| CAS-1989605-43-7 |
| CAS-1989605-44-8 |
| CAS-1989605-45-9 |
| CAS-1989605-46-0 |
| CAS-1989605-47-1 |
| CAS-1989605-48-2 |
| CAS-1989605-49-3 |
| CAS-1989605-50-6 |
| CAS-1989605-51-7 |
| CAS-2088184-56-7 |
| CAS-2088184-57-8 |
| CAS-2088184-58-9 |
| CAS-2088184-59-0 |
| CAS-2088184-60-3 |

TABLE 7-continued

| |
|---|
| CAS-2088184-61-4 |
| CAS-2088184-62-5 |
| CAS-2088184-63-6 |
| CAS-2088184-64-7 |
| CAS-2088184-65-8 |
| CAS-2088184-66-9 |
| CAS-2088184-67-0 |
| CAS-2088184-68-1 |
| CAS-2088184-69-2 |
| CAS-2088184-70-5 |
| CAS-2088184-71-6 |
| CAS-2088184-72-7 |
| CAS-2088184-73-8 |
| CAS-2088184-74-9 |
| CAS-2088184-75-0 |
| CAS-2088184-76-1 |
| CAS-2088184-77-2 |
| CAS-2088184-78-3 |
| CAS-2088184-79-4 |
| CAS-2088184-80-7 |
| CAS-2088184-81-8 |
| CAS-2088184-82-9 |
| CAS-2088184-83-0 |
| CAS-2088184-84-1 |
| CAS-2088184-85-2 |
| CAS-2088184-86-3 |
| CAS-2088184-87-4 |
| CAS-2088184-88-5 |
| CAS-2088184-89-6 |
| CAS-2088184-90-9 |
| CAS-2088184-91-0 |
| CAS-2088184-92-1 |
| CAS-2088184-93-2 |
| CAS-2088184-94-3 |
| CAS-2088184-95-4 |
| CAS-2088184-96-5 |
| CAS-2088184-97-6 |
| CAS-2088184-98-7 |
| CAS-2088184-99-8 |
| CAS-2088185-00-4 |
| CAS-2088185-01-5 |
| CAS-2088185-02-6 |
| CAS-2088185-03-7 |
| CAS-2088185-04-8 |
| CAS-2088185-05-9 |
| CAS-2088185-06-0 |
| CAS-1989602-19-8 |
| CAS-1989602-20-1 |
| CAS-1989602-21-2 |
| CAS-1989602-22-3 |
| CAS-1989602-23-4 |
| CAS-1989602-24-5 |
| CAS-1989602-25-6 |
| CAS-1989602-26-7 |
| CAS-1989602-27-8 |
| CAS-1989602-28-9 |
| CAS-1989602-29-0 |
| CAS-1989602-30-3 |
| CAS-1989602-31-4 |
| CAS-1989602-32-5 |
| CAS-1989602-33-6 |
| CAS-1989602-34-7 |
| CAS-1989602-35-8 |
| CAS-1989602-36-9 |
| CAS-1989602-37-0 |
| CAS-1989602-38-1 |
| CAS-1989602-39-2 |
| CAS-1989602-40-5 |
| CAS-1989602-41-6 |
| CAS-1989602-42-7 |
| CAS-1989602-43-8 |
| CAS-1989602-44-9 |
| CAS-1989602-45-0 |
| CAS-1989602-46-1 |
| CAS-1989602-47-2 |
| CAS-1989602-48-3 |
| CAS-1989602-49-4 |
| CAS-1989602-50-7 |
| CAS-1989602-51-8 |
| CAS-1989602-52-9 |

TABLE 7-continued

| |
|---|
| CAS-1989602-53-0 |
| CAS-1989602-54-1 |
| CAS-1989602-55-2 |
| CAS-1989602-56-3 |
| CAS-1989602-57-4 |
| CAS-1989602-58-5 |
| CAS-1989602-59-6 |
| CAS-1989602-60-9 |
| CAS-1989602-61-0 |
| CAS-1989602-62-1 |
| CAS-1989602-63-2 |
| CAS-1989602-64-3 |
| CAS-1989602-65-4 |
| CAS-1989602-66-5 |
| CAS-1989602-67-6 |
| CAS-1989602-68-7 |
| CAS-1989602-69-8 |
| CAS-1989605-52-8 |
| CAS-1989605-53-9 |
| CAS-1989605-54-0 |
| CAS-1989605-55-1 |
| CAS-1989605-56-2 |
| CAS-1989605-57-3 |
| CAS-1989605-58-4 |
| CAS-1989605-59-5 |
| CAS-1989605-61-9 |
| CAS-1989605-62-0 |
| CAS-1989605-63-1 |
| CAS-1989605-64-2 |
| CAS-1989605-65-3 |
| CAS-1989605-66-4 |
| CAS-1989605-67-5 |
| CAS-1989605-68-6 |
| CAS-1989605-69-7 |
| CAS-1989605-70-0 |
| CAS-1989605-71-1 |
| CAS-1989605-72-2 |
| CAS-1989605-73-3 |
| CAS-1989605-74-4 |
| CAS-1989605-75-5 |
| CAS-1989605-76-6 |
| CAS-1989605-77-7 |
| CAS-1989605-78-8 |
| CAS-1989605-79-9 |
| CAS-1989605-81-3 |
| CAS-1989605-82-4 |
| CAS-1989605-83-5 |
| CAS-1989605-84-6 |
| CAS-1989605-85-7 |
| CAS-1989605-86-8 |
| CAS-1989605-87-9 |
| CAS-1989605-88-0 |
| CAS-1989605-89-1 |
| CAS-1989605-90-4 |
| CAS-1989605-91-5 |
| CAS-1989605-92-6 |
| CAS-1989605-93-7 |
| CAS-1989605-94-8 |
| CAS-1989605-95-9 |
| CAS-1989605-96-0 |
| CAS-1989605-97-1 |
| CAS-1989605-98-2 |
| CAS-1989605-99-3 |
| CAS-1989606-00-9 |
| CAS-1989606-01-0 |
| CAS-1989606-04-3 |
| CAS-1989606-05-4 |
| CAS-1989606-06-5 |
| CAS-2088185-07-1 |
| CAS-2088185-08-2 |
| CAS-2088185-09-3 |
| CAS-2088185-10-6 |
| CAS-2088185-11-7 |
| CAS-2088185-12-8 |
| CAS-2088185-13-9 |
| CAS-2088185-14-0 |
| CAS-2088185-15-1 |
| CAS-2088185-16-2 |
| CAS-2088185-17-3 |
| CAS-2088185-18-4 |

TABLE 7-continued

| |
|---|
| CAS-2088185-19-5 |
| CAS-2088185-20-8 |
| CAS-2088185-21-9 |
| CAS-2088185-22-0 |
| CAS-2088185-23-1 |
| CAS-2088185-32-2 |
| CAS-2088185-33-3 |
| CAS-2088185-34-4 |
| CAS-2088185-35-5 |
| CAS-2088185-36-6 |
| CAS-2088185-37-7 |
| CAS-2088185-38-8 |
| CAS-2088185-39-9 |
| CAS-2088185-40-2 |
| CAS-2088185-41-3 |
| CAS-2088185-42-4 |
| CAS-2088185-43-5 |
| CAS-2088185-44-6 |
| CAS-2088185-45-7 |
| CAS-2088185-46-8 |
| CAS-2088185-47-9 |
| CAS-2088185-48-0 |
| CAS-2088185-49-1 |
| CAS-2088185-50-4 |
| CAS-2088185-51-5 |
| CAS-2088185-52-6 |
| CAS-2088185-53-7 |
| CAS-2088185-54-8 |
| CAS-2088185-55-9 |
| CAS-2088185-56-0 |
| CAS-2088185-57-1 |
| CAS-2088185-58-2 |
| CAS-2088185-59-3 |
| CAS-2088185-60-6 |
| CAS-2088185-61-7 |
| CAS-2088185-62-8 |
| CAS-2088185-63-9 |
| CAS-2088185-64-0 |
| CAS-2088185-65-1 |
| CAS-1989602-70-1 |
| CAS-1989602-71-2 |
| CAS-1989602-72-3 |
| CAS-1989602-73-4 |
| CAS-1989602-74-5 |
| CAS-1989602-75-6 |
| CAS-1989602-76-7 |
| CAS-1989602-77-8 |
| CAS-1989602-78-9 |
| CAS-1989602-79-0 |
| CAS-1989602-80-3 |
| CAS-1989602-82-5 |
| CAS-1989602-84-7 |
| CAS-1989602-85-8 |
| CAS-1989602-86-9 |
| CAS-1989602-87-0 |
| CAS-1989602-88-1 |
| CAS-1989604-00-3 |
| CAS-1989604-01-4 |
| CAS-1989604-02-5 |
| CAS-1989604-03-6 |
| CAS-1989604-04-7 |
| CAS-1989604-05-8 |
| CAS-1989604-06-9 |
| CAS-1989604-07-0 |
| CAS-1989604-08-1 |
| CAS-1989604-09-2 |
| CAS-1989604-10-5 |
| CAS-1989604-11-6 |
| CAS-1989604-13-8 |
| CAS-1989604-14-9 |
| CAS-1989604-15-0 |
| CAS-1989604-16-1 |
| CAS-1989604-17-2 |
| CAS-1989604-18-3 |
| CAS-1989604-19-4 |
| CAS-1989604-20-7 |
| CAS-1989604-21-8 |
| CAS-1989604-22-9 |
| CAS-1989604-23-0 |
| CAS-1989604-24-1 |

TABLE 7-continued

| |
|---|
| CAS-1989604-25-2 |
| CAS-1989604-26-3 |
| CAS-1989604-27-4 |
| CAS-1989604-28-5 |
| CAS-1989604-29-6 |
| CAS-1989604-30-9 |
| CAS-1989604-31-0 |
| CAS-1989604-32-1 |
| CAS-1989604-33-2 |
| CAS-1989604-34-3 |
| CAS-1989606-07-6 |
| CAS-1989606-08-7 |
| CAS-1989606-09-8 |
| CAS-1989606-10-1 |
| CAS-1989606-11-2 |
| CAS-1989606-12-3 |
| CAS-1989606-13-4 |
| CAS-1989606-14-5 |
| CAS-1989606-15-6 |
| CAS-1989606-16-7 |
| CAS-1989606-17-8 |
| CAS-1989606-18-9 |
| CAS-1989606-19-0 |
| CAS-1989606-20-3 |
| CAS-1989606-21-4 |
| CAS-1989606-22-5 |
| CAS-1989606-23-6 |
| CAS-1989606-24-7 |
| CAS-1989606-26-9 |
| CAS-1989606-27-0 |
| CAS-1989606-28-1 |
| CAS-1989606-29-2 |
| CAS-1989606-30-5 |
| CAS-1989606-31-6 |
| CAS-1989606-32-7 |
| CAS-1989606-33-8 |
| CAS-1989606-34-9 |
| CAS-1989606-35-0 |
| CAS-1989606-36-1 |
| CAS-1989606-37-2 |
| CAS-1989606-38-3 |
| CAS-1989606-39-4 |
| CAS-1989606-40-7 |
| CAS-1989606-41-8 |
| CAS-1989606-42-9 |
| CAS-1989606-43-0 |
| CAS-1989606-44-1 |
| CAS-1989606-45-2 |
| CAS-1989606-46-3 |
| CAS-1989606-48-5 |
| CAS-1989606-49-6 |
| CAS-1989606-53-2 |
| CAS-1989606-55-4 |
| CAS-1989606-56-5 |
| CAS-1989606-61-2 |
| CAS-1989606-62-3 |
| CAS-1989606-63-4 |
| CAS-1989606-67-8 |
| CAS-1989606-69-0 |
| CAS-1989606-70-3 |
| CAS-1989606-74-7 |
| CAS-2088185-66-2 |
| CAS-2088185-67-3 |
| CAS-2088185-68-4 |
| CAS-2088185-69-5 |
| CAS-2088185-70-8 |
| CAS-2088185-71-9 |
| CAS-2088185-72-0 |
| CAS-2088185-73-1 |
| CAS-2088185-74-2 |
| CAS-2088185-75-3 |
| CAS-2088185-76-4 |
| CAS-2088185-77-5 |
| CAS-2088185-78-6 |
| CAS-2088185-79-7 |
| CAS-2088185-80-0 |
| CAS-2088185-81-1 |
| CAS-2088185-82-2 |
| CAS-2088185-83-3 |
| CAS-2088185-84-4 |

TABLE 7-continued

| |
|---|
| CAS-2088185-85-5 |
| CAS-2088185-86-6 |
| CAS-2088185-87-7 |
| CAS-2088185-88-8 |
| CAS-2088185-89-9 |
| CAS-2088185-90-2 |
| CAS-2088185-91-3 |
| CAS-2088185-92-4 |
| CAS-2088185-93-5 |
| CAS-2088185-94-6 |
| CAS-2088185-95-7 |
| CAS-2088185-96-8 |
| CAS-2088185-97-9 |
| CAS-2088185-98-0 |
| CAS-2088185-99-1 |
| CAS-2088186-00-7 |
| CAS-2088186-01-8 |
| CAS-2088186-02-9 |
| CAS-2088195-88-2 |
| CAS-2088195-89-3 |
| CAS-2088195-90-6 |
| CAS-2088195-91-7 |
| CAS-861806-70-4 |
| CAS-1269508-30-6 |

In the composition of the invention, preferably any mixture M1, M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, M33, M34, M35, M36, M37, M38, M39, M40, M41, M42, M43, M44, M45, M46, M47, M48, M49, M50, M51, M52, M53, M54, M55, M56, M57, M58, M59, M60, M61, M62, M63, M64, M65, M66, M67, M68, M69, M70, M71, M72, M73, M74, M75, M76, M77, M78, M79, M80, M81, M82, M83, M84, M85, M86, M87, M88, M89, M90, M91, M92, M93, M94, M95, M96, M97, M98, M99, M100, M101, M102, M103, M104, M105, M106, M107, M108, M109, M110, M111, M112, M113, M114, M115, M116, M117, M118, M119, M120, M121, M122, M123, M124, M125, M126, M127, M128, M129, M130, M131, M132, M133, M134, M135, M136, M137, M138, M139, M140, M141, M142, M143, M144, M145, M146, M147, M148, M149, M150, M151, M152, M153, M154, M155, M156, M157, M158, M159, M160, M161, M162, M163, M164, M165, M166, M167, M168, M169, M170, M171, M172, M173, M174, M175, M176, M177, M178, M179, M180, M181, M182, M183, M184, M185, M186, M187, M188, M189, M190, M191, M192, M193, M194, M195, M196, M197, M198, M199, M200, M201, M202, M203, M204, M205, M206, M207, M208, M209, M210, M211, M212, M213, M214, M215, M216, M217, M218, M219, M220, M221, M222, M223, M224, M225, M226, M227, M228, M229, M230, M231, M232, M233, M234, M235, M236, M237, M238, M239, M240, M241, M242, M243, M244, M245, M246, M247, M248, M249, M250, M251, M252 or M253 is combined with a compound from table 6 or 7.

The composition of the invention, comprising at least one phosphorescent emitter, preferably forms an infrared-emitting or yellow-, orange-, red-, green-, blue- or ultraviolet-emitting layer, more preferably a yellow- or green-emitting layer and most preferably a green-emitting layer.

A yellow-emitting layer is understood here to mean a layer having a photoluminescence maximum within the range from 540 to 570 nm. An orange-emitting layer is understood to mean a layer having a photoluminescence maximum within the range from 570 to 600 nm. A red-emitting layer is understood to mean a layer having a photoluminescence maximum within the range from 600 to 750 nm. A green-emitting layer is understood to mean a layer having a photoluminescence maximum within the range from 490 to 540 nm. A blue-emitting layer is understood to mean a layer having a photoluminescence maximum within the range from 440 to 490 nm. The photoluminescence maximum of the layer is determined here by measuring the photoluminescence spectrum of the layer having a layer thickness of 50 nm at room temperature, said layer having the composition of the invention, i.e. comprising emitter and matrix.

The photoluminescence spectrum of the layer is recorded, for example, with a commercial photoluminescence spectrometer.

The photoluminescence spectrum of the emitter chosen is generally measured in oxygen-free solution, $10^{-5}$ molar, at room temperature, a suitable solvent being any in which the chosen emitter dissolves in the concentration mentioned. Particularly suitable solvents are typically toluene or 2-methyl-THF, but also dichloromethane. Measurement is effected with a commercial photoluminescence spectrometer. The triplet energy T1 in eV is determined from the photoluminescence spectra of the emitters. Firstly, the peak maximum Plmax. (in nm) of the photoluminescence spectrum is determined. The peak maximum Plmax. (in nm) is then converted to eV by: E(T1 in eV)=1240/E(T1 in nm)=1240/PLmax. (in nm).

Preferred phosphorescent emitters are accordingly infrared emitters, preferably from table 5 or 6, the triplet energy $T_1$ of which is preferably ~1.9 eV to ~1.0 eV.

Preferred phosphorescent emitters are accordingly red emitters, preferably from table 5 or 6, the triplet energy $T_1$ of which is preferably ~2.1 eV to ~1.9 eV.

Preferred phosphorescent emitters are accordingly yellow emitters, preferably from table 5 or 6, the triplet energy $T_1$ of which is preferably ~2.3 eV to ~2.1 eV.

Preferred phosphorescent emitters are accordingly green emitters, preferably from table 5 or 6, the triplet energy $T_1$ of which is preferably ~2.5 eV to ~2.3 eV.

Preferred phosphorescent emitters are accordingly blue emitters, preferably from table 5 or 6, the triplet energy $T_1$ of which is preferably ~3.1 eV to ~2.5 eV.

Preferred phosphorescent emitters are accordingly ultraviolet emitters, preferably from table 5 or 6, the triplet energy $T_1$ of which is preferably ~4.0 eV to ~3.1 eV.

Particularly preferred phosphorescent emitters are accordingly green or yellow emitters, preferably from table 6 or 7 as described above.

Very particularly preferred phosphorescent emitters are accordingly green emitters, preferably from table 6 or 7, the triplet energy $T_1$ of which is preferably ~2.5 eV to ~2.3 eV.

Most preferably, green emitters, preferably from table 6 or 7, as described above, are selected for the composition of the invention or emitting layer of the invention.

Preferred fluorescent emitters are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred fluorescent emitters are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328.

In a further preferred embodiment of the invention, the composition of the invention is used as a component of mixed matrix systems. The mixed matrix systems preferably comprise three or four different matrix materials, more preferably three different matrix materials (in other words, one further matrix component in addition to the composition of the invention). Examples of suitable matrix materials which can be used in combination with the composition of the invention as matrix components in a mixed matrix system are selected from wide band gap materials, electron transport materials (ETM) and hole transport materials (HTM).

Preference is given to using mixed matrix systems in phosphorescent organic electroluminescent devices. One source of more detailed information about mixed matrix systems is the application WO 2010/108579. Particularly suitable matrix materials which can be used in combination with the composition of the invention as matrix components of a mixed matrix system in phosphorescent or fluorescent organic electroluminescent devices are selected from the preferred matrix materials specified below for phosphorescent emitters or the preferred matrix materials for fluorescent emitters, according to what type of emitter is used. Preferably, the mixed matrix system is optimized for an emitter from table 6 or 7.

Various substance classes are useful as further host materials, preferably for fluorescent emitters, as well as the composition of the invention as described above, more preferably comprising a mixture of materials selected from M1 to M253. Preferred further host materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred host materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Various substance classes are useful as further matrix materials, preferably for phosphorescent emitters, as well as the composition of the invention as described above, more preferably comprising a mixture of materials selected from M1 to M253. Preferred further matrix materials are selected from the classes of the aromatic amines, especially triarylamines, for example according to US 2005/0069729, carbazole derivatives (e.g. CBP, N,N-biscarbazolylbiphenyl) or compounds according to WO 2005/039246, US 2005/0069729, JP 2004/288381, EP 1205527 or WO 2008/086851, bridged carbazole derivatives, for example according to WO 2011/088877 and WO 2011/128017, indenocarbazole derivatives, for example according to WO 2010/136109 and WO 2011/000455, azacarbazole derivatives, for example according to EP 1617710, EP 1617711, EP 1731584, JP 2005/347160, indolocarbazole derivatives, for example according to WO 2007/063754 or WO 2008/056746, ketones, for example according to WO 2004/093207 or WO 2010/006680, phosphine oxides, sulfoxides and sulfones, for example according to WO 2005/003253, oligophenylenes, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, aluminum complexes, e.g. BAlq, diazasilole derivatives and tetraazasilole derivatives, for example according to WO 2010/054729, diazaphosphole derivatives, for example according to WO 2010/054730, and aluminum complexes, e.g. BAIQ.

In an alternative embodiment of the present invention, the composition, aside from the constituents of electron-transporting host and hole-transporting host, does not contain any further constituents, i.e. any functional materials. This embodiment concerns material mixtures that are used as such for production of the organic layer. These systems are also referred to as premix systems that are used as the sole material source in the vapor deposition. In this way, it is possible in a simple and rapid manner to achieve the vapor deposition of a layer with homogeneous distribution of the components without the need for precise actuation of a multitude of material sources.

The invention accordingly further provides a composition consisting of a compound of the formula (1), (1a) to (1k) or a compound selected from 1 to 11 and a compound of the formula (2), (2a) to (2i) or a compound selected from 12 to 34.

The composition of the invention as described above or described as preferred is suitable for use in an organic electronic device. An organic electronic device is understood here to mean a device containing at least one layer containing at least one organic compound. However, the device may also comprise inorganic materials or else layers formed entirely from inorganic materials.

The invention accordingly further provides for the use of a composition as described above or described as preferred, especially of a mixture selected from M1 to M253, in an organic electronic device.

The components or constituents of the compositions may be processed by vapor deposition or from solution. If the compositions are applied from solution, formulations of the composition of the invention comprising at least one further solvent are required. These formulations may, for example, be solutions, dispersions or emulsions. For this purpose, it may be preferable to use mixtures of two or more solvents.

The present invention therefore further provides a formulation comprising a composition of the invention and at least one solvent.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The formulation may also comprise at least one further organic or inorganic compound which is likewise used in the electronic device, especially an emitting compound, especially a phosphorescent emitter and/or a further matrix material. Suitable emitting compounds and further matrix materials have already been detailed above.

The present invention also provides for the use of the composition of the invention in an organic electronic device, preferably in an electron-transporting layer and/or in an emitting layer.

The organic electronic device is preferably selected from organic integrated circuits (OICs), organic field-effect transistors (OFETs), organic thin-film transistors (OTFTs), organic electroluminescent devices, organic solar cells (OSCs), organic optical detectors and organic photoreceptors, particular preference being given to organic electroluminescent devices.

Very particularly preferred organic electroluminescent devices for the use of the composition of the invention are organic light-emitting transistors (OLETs), organic field-quench devices (OFQDs), organic light-emitting electrochemical cells (OLECs, LECs, LEECs), organic laser diodes (O-lasers) and organic light-emitting diodes (OLEDs); OLECs and OLEDs are especially preferred and OLEDs are most preferred.

Preferably, the composition of the invention as described above or described as preferred is used in a layer having an electron-transporting function in an electronic device. The layer is preferably an electron injection layer (EIL), an electron transport layer (ETL), a hole blocker layer (HBL) and/or an emission layer (EML), more preferably an ETL, EIL and/or an EML. Most preferably, the composition of the invention is used in an EML, especially as matrix material.

Therefore, the present invention still further provides an organic electronic device which is especially selected from one of the aforementioned electronic devices and which comprises the composition of the invention, as described above or described as preferred, preferably in an emission layer (EML), in an electron transport layer (ETL), in an electron injection layer (EIL) and/or in a hole blocker layer (HBL), very preferably in an EML, EIL and/or ETL and most preferably in an EML.

When the layer is an emitting layer, it is especially preferably a phosphorescent layer which is characterized in that it comprises, in addition to the composition as described above or described as preferred, a phosphorescent emitter, especially together with an emitter from table 6 or 7 or a preferred emitter as described above.

In a particularly preferred embodiment of the present invention, therefore, the electronic device is an organic electroluminescent device, most preferably an organic light-emitting diode (OLED), containing the composition of the invention as described above or described as preferred together with a phosphorescent emitter in the emission layer (EML).

The composition of the invention in the preferred embodiments and of the emitting compound contains preferably between 99.9% and 1% by volume, further preferably between 99% and 10% by volume, especially preferably between 98% and 60% by volume, very especially preferably between 97% and 80% by volume, of matrix material composed of at least one compound of the formula (1) and at least one compound of the formula (2) according to the preferred embodiments, based on the overall composition of emitter and matrix material. Correspondingly, the composition preferably contains between 0.1% and 99% by volume, further preferably between 1% and 90% by volume, more preferably between 2% and 40% by volume, most preferably between 3% and 20% by volume, of the emitter based on the overall composition of emitter and matrix material. If the compounds are processed from solution, preference is given to using the corresponding amounts in % by weight rather than the above-specified amounts in % by volume.

Apart from the cathode, anode and the layer comprising the composition of the invention, an electronic device may comprise further layers. These are selected, for example, from in each case one or more hole injection layers, hole transport layers, hole blocker layers, emitting layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that not necessarily every one of these layers need be present.

The sequence of layers in an organic electroluminescent device is preferably as follows:

anode/hole injection layer/hole transport layer/emitting layer/electron transport layer/electron injection layer/cathode.

This sequence of the layers is a preferred sequence.

At the same time, it should be pointed out again that not all the layers mentioned need be present and/or that further layers may additionally be present.

An organic electroluminescent device comprising the composition of the invention may comprise multiple emitting layers. More preferably, these emission layers in this case have several emission maxima between 380 nm and 750 nm overall, such that the overall result is white emission; in other words, various emitting compounds which may fluoresce or phosphoresce and which emit blue or yellow or orange or red light are used in the emitting layers. Especially preferred are three-layer systems, i.e. systems having three emitting layers, where the three layers show blue, green and orange or red emission (for the basic construction see, for example, WO 2005/011013). It should be noted that, for the production of white light, rather than a plurality of color-emitting emitter compounds, an emitter compound used individually which emits over a broad wavelength range may also be suitable.

Suitable charge transport materials as usable in the hole injection or hole transport layer or electron blocker layer or in the electron transport layer of the organic electroluminescent device of the invention are, for example, the compounds disclosed in Y. Shirota et al., Chem. Rev. 2007, 107(4), 953-1010, or other materials as used in these layers according to the prior art.

Materials used for the electron transport layer may be any materials as used according to the prior art as electron transport materials in the electron transport layer. Especially suitable are aluminum complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the abovementioned compounds as disclosed in JP 2000/053957, WO 2003/060956, WO 2004/028217, WO 2004/080975 and WO 2010/072300.

Preferred hole transport materials are especially materials which can be used in a hole transport, hole injection or electron blocker layer, such as indenofluoreneamine derivatives (for example according to WO 06/122630 or WO 06/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or the as yet unpublished EP 12000929.5), fluoreneamines (for example according to WO 2014/015937, WO 2014/015938 and WO 2014/015935), spirodibenzopyranamines (for example according to WO 2013/083216) and dihydroacridine derivatives (for example WO 2012/150001).

Preferred cathodes of electronic devices are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The organic electronic device, in the course of production, is appropriately (according to the application) structured, contact-connected and finally sealed, since the lifetime of the devices of the invention is shortened in the presence of water and/or air.

In a further preferred embodiment, the organic electronic device comprising the composition of the invention is characterized in that one or more organic layers comprising the composition of the invention are coated by a sublimation method. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., Appl. Phys. Lett. 2008, 92, 053301).

Preference is additionally given to an organic electroluminescent device, characterized in that one or more organic layers comprising the composition of the invention are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of the components of the composition of the invention are needed. High solubility can be achieved by suitable substitution of the corresponding compounds. Processing from solution has the advantage that the layer comprising the composition of the invention can be applied in a very simple and inexpensive manner. This technique is especially suitable for the mass production of organic electronic devices.

In addition, hybrid methods are possible, in which, for example, one or more layers are applied from solution and one or more further layers are applied by vapor deposition. These methods are known in general terms to those skilled in the art and can be applied to organic electroluminescent devices.

The invention therefore further provides a process for producing an organic electronic device comprising a composition of the invention as described above or described as preferred, characterized in that at least one organic layer comprising a composition of the invention is applied by gas phase deposition, especially by a sublimation method and/or by an OVPD (organic vapor phase deposition) method and/or with the aid of carrier gas sublimation, or from solution, especially by spin-coating or by a printing method.

In the production of an organic electronic device by means of gas phase deposition, there are two methods in principle by which an organic layer which is to comprise the composition of the invention and which may comprise multiple different constituents can be applied, or applied by vapor deposition, to any substrate. Firstly, the materials used can each be initially charged in a material source and ultimately evaporated from the different material sources ("co-evaporation"). Secondly, the various materials can be premixed and the mixture can be initially charged in a single material source from which it is ultimately evaporated ("premix evaporation"). In this way, it is possible in a simple and rapid manner to achieve the vapor deposition of a layer with homogeneous distribution of the components without the need for precise actuation of a multitude of material sources.

The invention accordingly further provides a process characterized in that the at least one compound of the formula (1) as described above or described as preferred and the at least one compound of the formula (2) as described above or described as preferred are deposited from the gas phase successively or simultaneously from at least two material sources, optionally with other materials as described above or described as preferred, and form the organic layer.

In a preferred embodiment of the present invention, the at least one organic layer is applied by means of gas phase deposition, wherein the constituents of the composition are premixed and evaporated from a single material source.

The invention accordingly further provides a process characterized in that the composition of the invention as described above or described as preferred is utilized as material source for the gas phase deposition of the host system and, optionally together with further materials, forms the organic layer.

The invention further provides a process for producing an organic electronic device comprising a composition of the invention as described above or described as preferred, characterized in that the formulation of the invention as described above is used to apply the organic layer.

The compositions of the invention and the devices of the invention feature the following surprising advantages over the prior art:

The use of the compositions of the invention in organic electronic devices, especially in an organic electroluminescent device, and especially in an OLED or OLEC, leads to distinct increases in the lifetime of the devices.

The use of the compositions of the invention in organic electronic devices, especially in an organic electroluminescent device, and especially in an OLED or OLEC, likewise leads to a distinct increase in the efficiency and/or operating voltage of the devices.

As apparent in example 1 adduced below, it is possible through the use of prior art compounds, for example the compound SoA1, to achieve good voltages and efficiencies at low emitter concentrations in the EML of 12%. However, the lifetime of the components is short.

An improvement in lifetime by 10% to 40%, for example of 12% to 37% as representative figures from the examples of table 10, with a comparable increase in operating voltage and comparable or improved current efficiency can be achieved by the inventive combination of compounds of the formula (1), as described above, with compounds of the formula (2), as described above.

This improvement in lifetime with comparable operating voltage and comparable or improved current efficiency can preferably be achieved by virtue of the inventive combination of the compounds of the formula (1) as described above with compounds of the formula (2) as described above at emitter concentrations of 2% to 15% by weight in the emission layer.

The difference from the comparative example lies in the electronic structure of the electron-transporting host of compounds 1 and 6 from the comparative compound SoA1, as shown in table 9.

In a manner unforeseeable to the person skilled in the art, the exchange of the carbazole for a spirobifluorenyl bonded directly or via a linker to the dibenzofuran/dibenzothiophene results in an improvement in the lifetime of electronic devices, especially of OLEDs, of about 10% to 40%.

In a manner unforeseeable to the person skilled in the art, the linkage in positions 1 and 8 of the dibenzofuran or dibenzothiophene, compared to linkage in position 4 or 6 of the dibenzofuran or dibenzothiophene, results in an improvement in the lifetime of electronic devices.

The compositions of the invention are of very good suitability for use in an emission layer and exhibit improved performance data, especially in respect of lifetime, operating voltage and/or current efficiency, over compounds from the prior art as described above.

The compositions of the invention can easily be processed and are therefore of very good suitability for mass production in commercial use.

The compositions of the invention can be premixed and vapor-deposited from a single material source, and so it is possible in a simple and rapid manner to produce an organic layer with homogeneous distribution of the components used.

These abovementioned advantages are not accompanied by a deterioration in the further electronic properties of an electronic device.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Any feature disclosed in the present invention, unless stated otherwise, should therefore be considered as an example from a generic series or as an equivalent or similar feature.

All features of the present invention may be combined with one another in any manner, unless particular features and/or steps are mutually exclusive. This is especially true of preferred features of the present invention.

Equally, features of non-essential combinations may be used separately (and not in combination).

The technical teaching disclosed with the present invention may be abstracted and combined with other examples.

The invention is illustrated in more detail by the examples which follow, without any intention of restricting it thereby.

General Methods

Determination of Orbital Energies and Electronic States

The HOMO and LUMO energies and the triplet level and the singlet levels of the materials are determined via quantum-chemical calculations. For this purpose, in the present case, the "Gaussian09, Revision D.01" software package (Gaussian Inc.) is used. For calculation of organic substances without metals (referred to as the "org." method), a geometry optimization is first conducted by the semi-empirical method AM1 (Gaussian input line "#AM1 opt") with charge 0 and multiplicity 1. Subsequently, on the basis of the optimized geometry, a (single-point) energy calculation is effected for the electronic ground state and the triplet level. This is done using the TDDFT (time dependent density functional theory) method B3PW91 with the 6-31 G(d) basis set (Gaussian input line "#B3PW91/6-31G(d) td=(50-50, nstates=4)") (charge 0, multiplicity 1). For organometallic compounds (referred to as the "M-org." method), the geometry is optimized by the Hartree-Fock method and the LanL2 MB basis set (Gaussian input line "#HF/LanL2 MB opt") (charge 0, multiplicity 1). The energy calculation is effected, as described above, analogously to that for the organic substances, except that the "LanL2DZ" basis set is used for the metal atom and the "6-31 G(d)" basis set for the ligands (Gaussian input line "#B3PW91/gen pseudo=lanl2 td=(50-50,nstates=4)"). From the energy calculation, the HOMO is obtained as the last orbital occupied by two electrons (alpha occ. eigenvalues) and LUMO as the first unoccupied orbital (alpha virt. eigenvalues) in Hartree units, where HEh and LEh represent the HOMO energy in Hartree units and the LUMO energy in Hartree units respectively. This is used to determine the HOMO and LUMO value in electron volts, calibrated by cyclic voltammetry measurements, as follows:

$$HOMO\ (eV)=(HEh*27.212)*0.8308-1.118;$$

$$LUMO\ (eV)=(LEh*27.212)*1.0658-0.5049.$$

The triplet level T1 of a material is defined as the relative excitation energy (in eV) of the triplet state having the lowest energy which is found by the quantum-chemical energy calculation.

The singlet level S1 of a material is defined as the relative excitation energy (in eV) of the singlet state having the second-lowest energy which is found by the quantum-chemical energy calculation.

The energetically lowest singlet state is referred to as S0.

The method described herein is independent of the software package used and always gives the same results. Examples of frequently utilized programs for this purpose are "Gaussian09" (Gaussian Inc.) and Q-Chem 4.1 (Q-Chem, Inc.). In the present case, the energies are calculated using the software package "Gaussian09, Revision D.01".

EXAMPLE 1: PRODUCTION OF THE OLEDS

Examples C1 to I10 which follow (see table 8) present the use of the material combinations of the invention in OLEDs.

Pretreatment for examples C1 to I10: Glass plaques coated with structured ITO (indium tin oxide) of thickness 50 nm are treated prior to coating, first with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in table 8. The materials required for production of the OLEDs are shown in table 9. The data of the OLEDs are listed in table 10. Examples C1-C8 are comparative examples according to the prior art; examples I1 to I10 show data of OLEDs of the invention.

All materials are applied by thermal vapor deposition in a vacuum chamber. In this case, the emission layer always consists of at least one matrix material (host material), for the purposes of the invention at least two matrix materials, and an emitting dopant (emitter) which is added to the matrix material(s) in a particular proportion by volume by co-evaporation. Details given in such a form as SoA1:CoH1:TEG1 (45%:45%:10%) mean here that the material SoA1 is present in the layer in a proportion by volume of 45%, CoH1 in a proportion of 45% and TEG1 in a proportion of 10%.

Analogously, the electron transport layer may also consist of a mixture of two materials.

The OLEDs are characterized in a standard manner. For this purpose, the electroluminescence spectra and the current efficiency (CE, measured in cd/A) as a function of luminance, calculated from current-voltage-luminance characteristics assuming Lambertian emission characteristics, and the lifetime are measured. The electroluminescence spectra are determined at a current density of 10 $mA/cm^2$, and the CIE 1931 x and y color coordinates are calculated therefrom. The parameter U10 in table 10 refers to the voltage which is required for a current density of 10 $mA/cm^2$. CE10 refers to the current efficiency attained at a current density of 10 $mA/cm^2$.

The lifetime LT is defined as the time after which the luminance drops from the starting luminance to a certain proportion L1 in the course of operation with constant current density $j_0$. A figure of L1=80% in table 10 means that the lifetime reported in the LT column corresponds to the time after which the luminance falls to 80% of its starting value.

Use of Mixtures of the Invention in OLEDs

The material combinations of the invention can be used in the emission layer in phosphorescent green OLEDs. The inventive combinations of compounds 1 and 6 with compound 15, 19, 23, 26 or 27 are used in examples 11 to 110 as matrix material in the emission layer.

TABLE 8

Structure of the OLEDs

| Ex. | HIL thickness | HTL thickness | EBL thickness | EML thickness | HBL thickness | ETL thickness | EIL thickness |
|---|---|---|---|---|---|---|---|
| C1 | HATCN 5 nm | SpMA1 230 nm | SpMA2 20 nm | SoA1:15:TEG1 (44%:44%:12%) 30 nm | ST2 10 nm | ST2:LiQ (50%:50%) 30 nm | LiQ 1nm |
| C2 | HATCN 5 nm | SpMA1 230 nm | SpMA2 20 nm | SoA1:19:TEG1 (44%:44%:12%) 30 nm | ST2 10 nm | ST2:LiQ (50%:50%) 30 nm | LiQ 1 nm |

TABLE 8-continued

| Structure of the OLEDs | | | | | | | |
|---|---|---|---|---|---|---|---|
| Ex. | HIL thickness | HTL thickness | EBL thickness | EML thickness | HBL thickness | ETL thickness | EIL thickness |
| C3 | HATCN 5 nm | SpMA1 230 nm | SpMA2 20 nm | SoA1:23:TEG1 (44%:44%:12%) 30 nm | ST2 10 nm | ST2:LiQ (50%:50%) 30 nm | LiQ 1 nm |
| C4 | HATCN 5 nm | SpMA1 230 nm | SpMA2 20 nm | SoA1:26:TEG1 (44%:44%:12%) 30 nm | ST2 10 nm | ST2:LiQ (50%:50%) 30 nm | LiQ 1nm |
| C5 | HATCN 5 nm | SpMA1 230 nm | SpMA2 20 nm | SoA1:27:TEG1 (44%:44%:12%) 30 nm | ST2 10 nm | ST2:LiQ (50%:50%) 30 nm | LiQ 1 nm |
| C6 | HATCN 5 nm | SpMA1 230 nm | SpMA2 20 nm | SoA2:23:TEG1 (44%:44%:12%) 30 nm | ST2 10 nm | ST2:LiQ (50%:50%) 30 nm | LiQ 1 nm |
| C7 | HATCN 5 nm | SpMA1 230 nm | SpMA2 20 nm | SoA3:15:TEG1 (44%:44%:12%) 30 nm | ST2 10 nm | ST2:LiQ (50%:50%) 30 nm | LiQ 1 nm |
| C8 | HATCN 5 nm | SpMA1 230 nm | SpMA2 20 nm | SoA3:23:TEG1 (44%:44%:12%) 30 nm | ST2 10 nm | ST2:LiQ (50%:50%) 30 nm | LiQ 1 nm |
| I1 | HATCN 5 nm | SpMA1 230 nm | SpMA2 20 nm | 6:15:TEG1 (44%:44%:12%) 30 nm | ST2 10 nm | ST2:LiQ (50%:50%) 30 nm | LiQ 1 nm |
| I2 | HATCN 5 nm | SpMA1 230 nm | SpMA2 20 nm | 6:19:TEG1 (44%:44%:12%) 30 nm | ST2 10 nm | ST2:LiQ (50%:50%) 30 nm | LiQ 1 nm |
| I3 | HATCN 5 nm | SpMA1 230 nm | SpMA2 20 nm | 6:23:TEG1 (44%:44%:12%) 30 nm | ST2 10 nm | ST2:LiQ (50%:50%) 30 nm | LiQ 1 nm |
| I4 | HATCN 5 nm | SpMA1 230 nm | SpMA2 20 nm | 6:26:TEG1 (44%:44%:12%) 30 nm | ST2 10 nm | ST2:LiQ (50%:50%) 30 nm | LiQ 1 nm |
| I5 | HATCN 5 nm | SpMA1 230 nm | SpMA2 20 nm | 6:27:TEG1 (44%:44%:12%) 30 nm | ST2 10 nm | ST2:LiQ (50%:50%) 30 nm | LiQ 1 nm |
| I6 | HATCN 5 nm | SpMA1 230 nm | SpMA2 20 nm | 1:15:TEG1 (44%:44%:12%) 30 nm | ST2 10 nm | ST2:LiQ (50%:50%) 30 nm | LiQ 1 nm |
| I7 | HATCN 5 nm | SpMA1 230 nm | SpMA2 20 nm | 1:19:TEG1 (44%:44%:12%) 30 nm | ST2 10 nm | ST2:LiQ (50%:50%) 30 nm | LiQ 1 nm |
| I8 | HATCN 5 nm | SpMA1 230 nm | SpMA2 20 nm | 1:23:TEG1 (44%:44%:12%) 30 nm | ST2 10 nm | ST2:LiQ (50%:50%) 30 nm | LiQ 1 nm |
| I9 | HATCN 5 nm | SpMA1 230 nm | SpMA2 20 nm | 1:26:TEG1 (44%:44%:12%) 30 nm | ST2 10 nm | ST2:LiQ (50%:50%) 30 nm | LiQ 1 nm |
| I10 | HATCN 5 nm | SpMA1 230 nm | SpMA2 20 nm | 1:27:TEG1 (44%:44%:12%) 30 nm | ST2 10 nm | ST2:LiQ (50%:50%) 30 nm | LiQ 1 nm |

TABLE 9
| Structural formulae of the materials for OLEDs |
| --- |
| 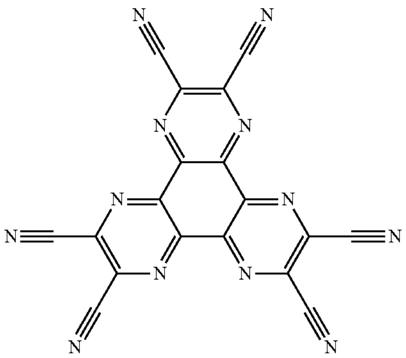 |
| HATCN |
| 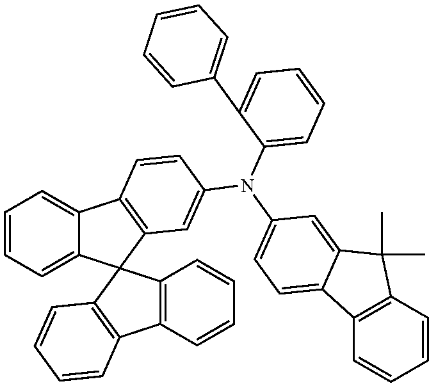 |
| SpMA1 |
| 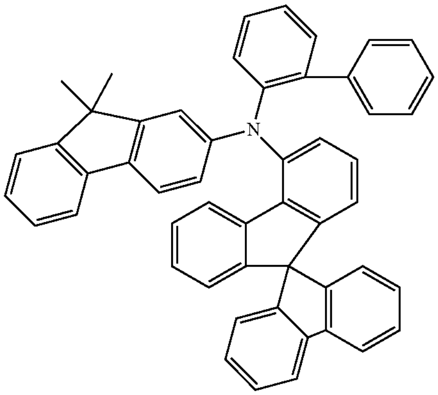 |
| SpMA2 |
TABLE 9-continued
| Structural formulae of the materials for OLEDs |
| --- |
| 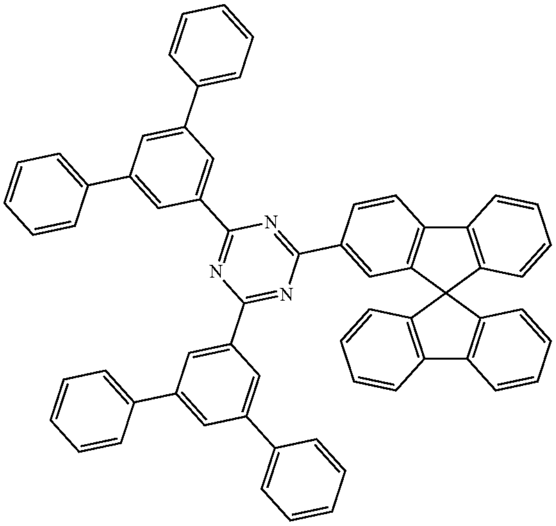 |
| ST2 |
| 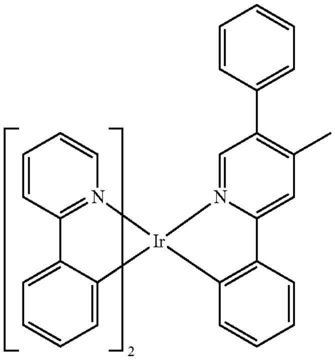 |
| TEG1 |
| 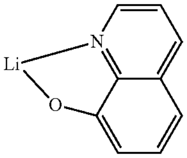 |
| LiQ |
| 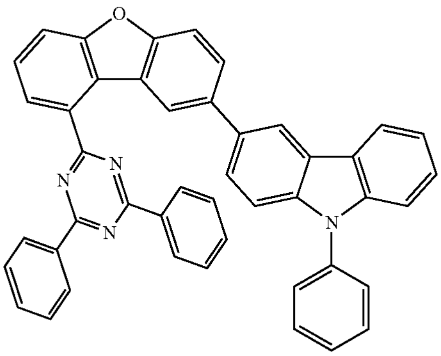 |
| SoA1 |

TABLE 9-continued

Structural formulae of the materials for OLEDs

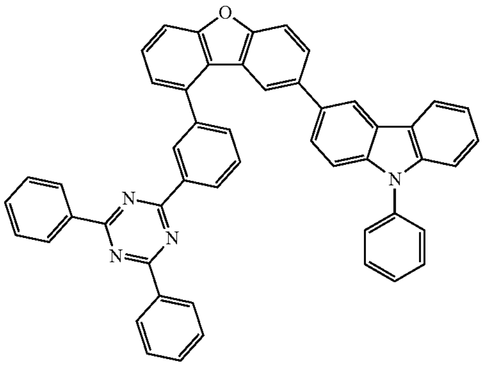

SoA2

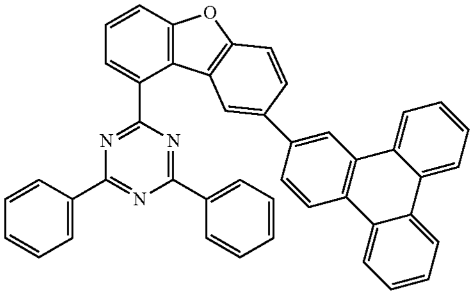

SoA3

TABLE 10

Data of the OLEDs

| Ex. | U10 (V) | CE10 (cd/A) | CIE x/y at 10 mA/cm$^2$ | $j_0$ (mA/cm$^2$) | L1 (%) | LT (h) |
|---|---|---|---|---|---|---|
| C1 | 4.1 | 59 | 0.33/0.63 | 40 | 80 | 410 |
| C7 | 4.3 | 63 | 0.33/0.63 | 40 | 80 | 470 |
| I1 | 4.1 | 65 | 0.33/0.63 | 40 | 80 | 560 |
| I6 | 4.0 | 65 | 0.33/0.63 | 40 | 80 | 490 |
| C2 | 4.1 | 58 | 0.33/0.63 | 40 | 80 | 460 |
| I2 | 4.0 | 64 | 0.33/0.63 | 40 | 80 | 610 |
| I7 | 4.0 | 63 | 0.33/0.63 | 40 | 80 | 550 |
| C3 | 4.0 | 57 | 0.32/0.64 | 40 | 80 | 320 |
| C6 | 4.0 | 62 | 0.33/0.63 | 40 | 80 | 200 |
| C8 | 4.3 | 62 | 0.33/0.63 | 40 | 80 | 350 |
| I3 | 4.0 | 62 | 0.32/0.64 | 40 | 80 | 400 |
| I8 | 4.0 | 61 | 0.32/0.64 | 40 | 80 | 380 |
| C4 | 3.9 | 60 | 0.32/0.63 | 40 | 80 | 240 |
| I4 | 3.9 | 65 | 0.32/0.63 | 40 | 80 | 310 |
| I9 | 3.9 | 59 | 0.32/0.63 | 40 | 80 | 270 |
| C5 | 3.9 | 60 | 0.33/0.63 | 40 | 80 | 280 |
| I5 | 3.9 | 64 | 0.33/0.63 | 40 | 80 | 360 |
| I10 | 3.9 | 60 | 0.33/0.63 | 40 | 80 | 330 |

EXAMPLE 2: SYNTHESIS OF COMPOUNDS OF THE INVENTION a) 2-{12-chloro-8-oxatricyclo[7.4.0.0$^{2,7}$]trideca-1(13),2(7),3,5,9,11-hexaen-3-yl}-4-{8-oxatricyclo[7.4.0.0$^{2,7}$]trideca-1(9),2,4,6,10,12-hexaen-3-yl}-6-phenyl-1,3,5-triazine

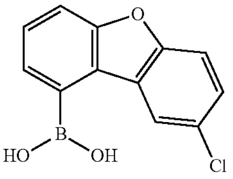

+

[CAS 2173554-84-0]

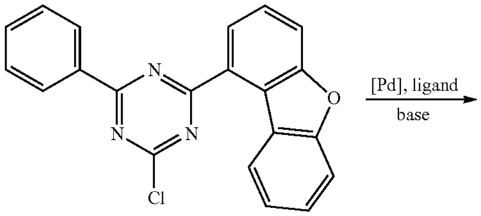

[CAS 1883265-32]

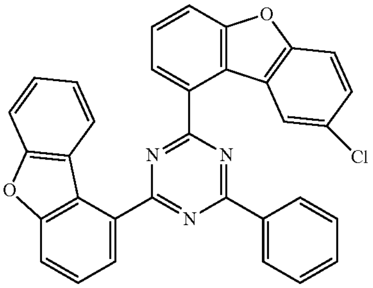

58 g (210 mmol; 1.00 eq.) of 1-boronyl-8-chlorodibenzofuran [CAS 162667-19-4], 90.2 g (252 mmol; 1.20 eq.) of 2-chloro-4-{8-oxatricyclo[7.4.0.0$^{2,7}$]trideca-1(9),2(7),3,5,10,12-hexaen-3-yl}-6-phenyl-1,3,5-triazine [CAS 1883265-32-4] and 44.5 g (420 mmol, 2.00 eq.) of sodium carbonate [CAS 497-19-8] are suspended in a mixture of 1000 ml of dioxane [CAS 123-91-1], 1000 ml of toluene [CAS 108-88-3] and 400 ml of water. To this suspension is added 4.85 g (4.20 mmol; 0.02 eq.) of tetrakis(triphenylphosphine)palladium(0) [CAS 14221-01-3], and the reaction mixture is heated under reflux for 16 h. After cooling, the organic phase is removed, filtered through silica gel, washed three times with 200 ml of water and then concentrated to dryness. The yield is 79.1 g (151 mmol; 72% of theory).

In an analogous manner, it is possible to obtain the following compounds;
| No. | Reactant 1 | Product | Yield |
| --- | --- | --- | --- |
| 1a | 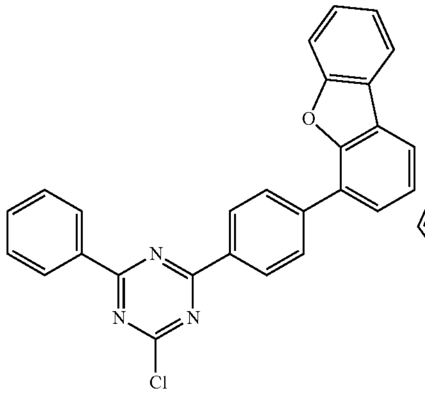 [CAS 2074632-09-8] | 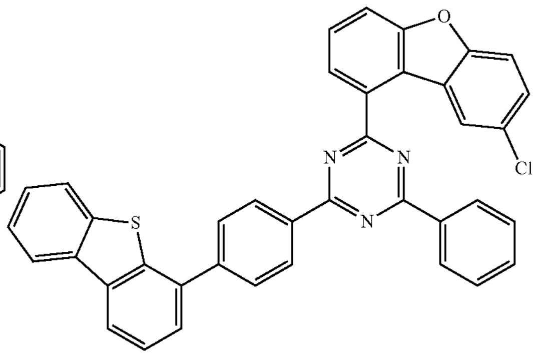 | 80% |
| 2a | 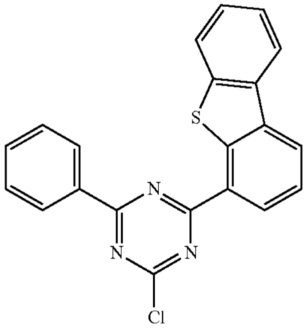 [CAS 1476735-48-4] | 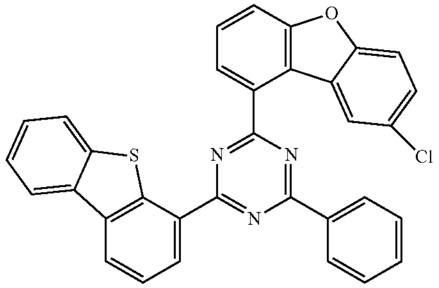 [SMILES: Clc1ccc2oc3cccc(-c4nc(-c5ccccc5)nc(-c5cccc6c5sc5ccccc56)n4)c3c2c1] | 65% |
| 3a | 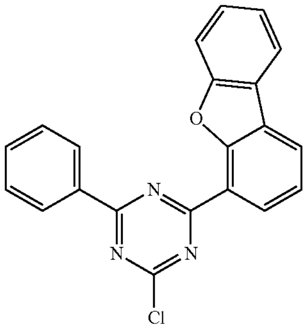 [CAS 1472729-25-1] | 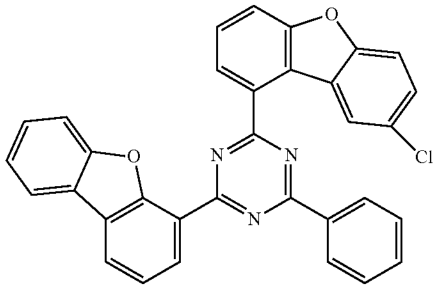 [SMILES: Clc1ccc2oc3cccc(-c4nc(-c5ccccc5)nc(-c5cccc6c5oc5ccccc56)n4)c3c2c1] | 67% |

-continued

| No. | Reactant 1 | Product | Yield |
| --- | --- | --- | --- |
| 4a | 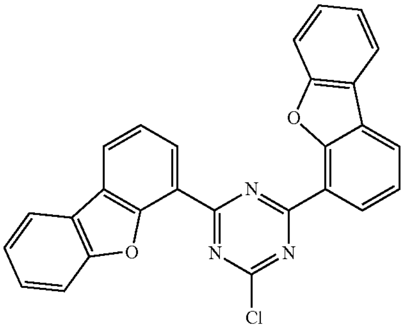 [CAS 1699739-83-7] | 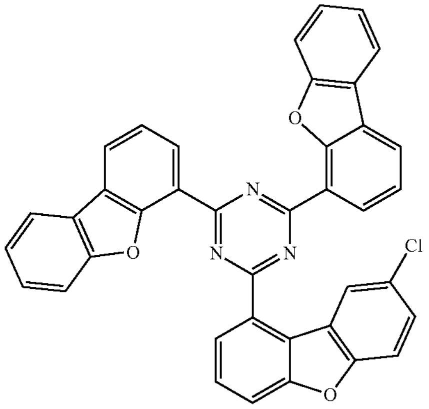 [SMILES: Clc1ccc2oc3cccc(-c4nc(-c5cccc6c5oc5ccccc56)nc(-c5cccc6c5oc5ccccc56)n4)c3c2c1] | 75% |

b) 2,4-Diphenyl-6-[12-(3-{9,9'-spirobi[fluoren]-7-yl}phenyl)-8-oxatricyclo[7.4.0.$0^{2,7}$]trideca-1(9),2(7),3,5,10,12-hexaen-3-yl]-1,3,5-triazine

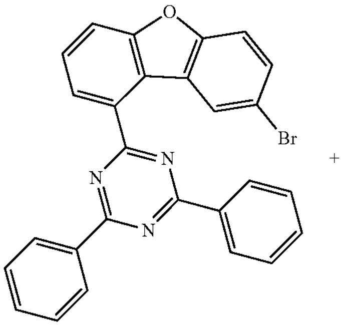

[CAS 1822310-63-3]

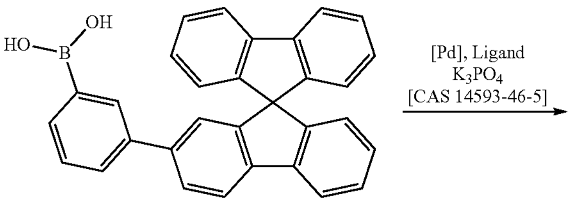

[CAS 1365812-76-5]

-continued

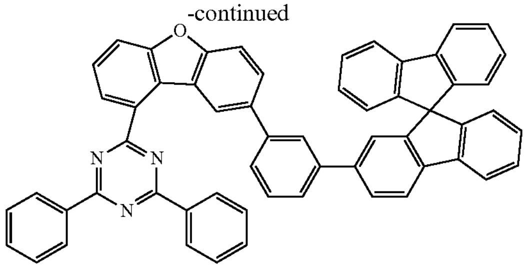

100 g (209 mmol; 1.00 eq.) of 2□{12□bromo□8□oxatricyclo[7.4.0.$0^{2,7}$]trideca□1(9),2(7),3,5, 10,12□hexaen□3□yl}□4,6□diphenyl□1,3,5□triazine [CAS 1160861-53-9], 114 g (220 mmol; 1.05 eq.) of (3□{9,9'□spirobi[fluoren]□2□yl}phenyl)boronic acid [CAS 1365812-76-5] and 133 g (627 mmol; 3.00 eq.) of tripotassium phosphate [CAS 14593-46-5] suspended in a mixture of 800 ml of dioxane [CAS 123-91-1], 800 ml of toluene [CAS 108-88-3] and 800 ml of water. To this suspension are added 3.86 g (4.80 mmol; 4.5 mol %) of dicyclohexyl(2',6'-dimethoxybiphenyl-2-yl)phosphine (SPhos) [CAS 657408-07-6] and 2.87 g (3.14 mmol; 1.5 mol %) of tris(dibenzylideneacetone)dipalladium [CAS 51364-51-3], and the reaction mixture is heated under reflux for 16 h. The reaction mixture is cooled down to room temperature and phases are separated. After the aqueous phase has been extracted, the combined organic phases are washed with saline solution and dried over sodium sulfate. After filtration through alox, the solvent is removed. The resultant solid is recrystallized twice from ethyl acetate. After final sublimation under high vacuum, the purified product is obtained as a colorless solid, 96.3 g (122 mmol; 58%).

In an analogous manner, it is possible to obtain the following compounds:

| No. | Reactant 1 | Reactant 2 | Product | Yield |
|---|---|---|---|---|
| 1b | 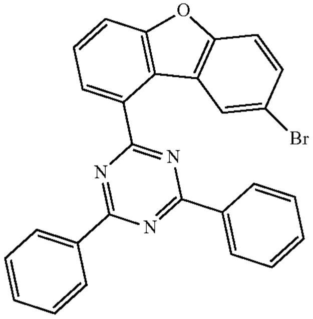 [CAS 1822310-63-3] | 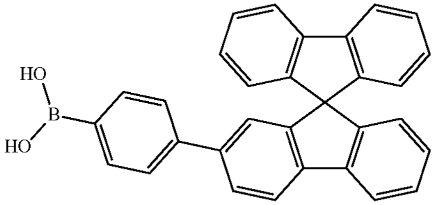 [CAS 1365812-76-5] | 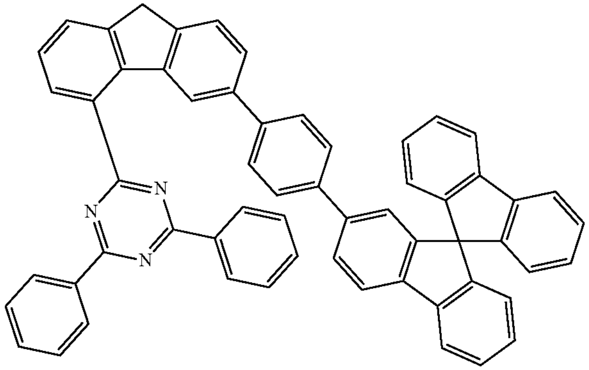 [SMILES: c1ccc(-c2nc(-c3ccccc3)nc(-c3cccc4c3-c3cc(-c5ccc(-c6ccc7c(c6)C6(c8ccccc8-c8ccccc86)c6ccccc6-7)cc5)ccc3C4)n2)cc1] | 42% |
| 2b | 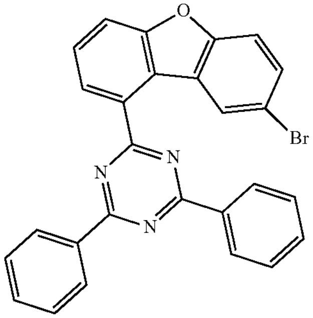 [CAS 1822310-63-3] | 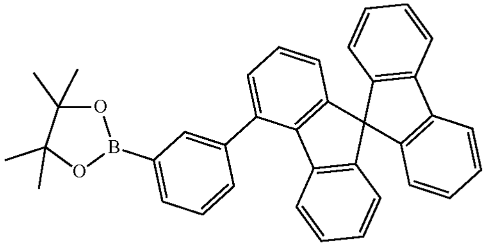 [CAS 2112854-30-3] | 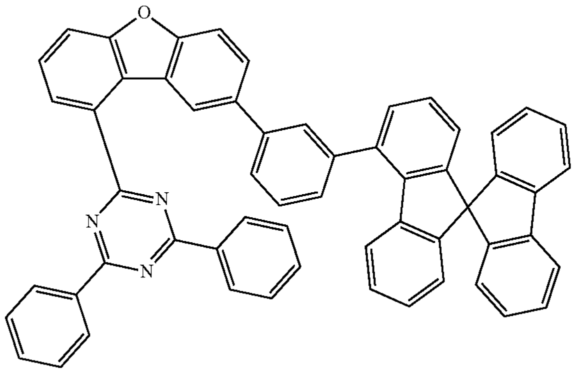 [SMILES: c1ccc(-c2nc(-c3ccccc3)nc(-c3cccc4oc5ccc(-c6cccc(-c7cccc8c7-c7ccccc7C87c8ccccc8-c8ccccc87)c6)cc5c34)n2)cc1] | 45% |

-continued
| No. | Reactant 1 | Reactant 2 | Product | Yield |
|---|---|---|---|---|
| 3b | 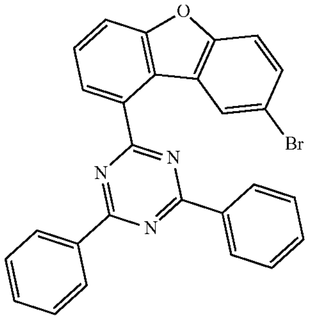 [CAS 1822310-63-3] | 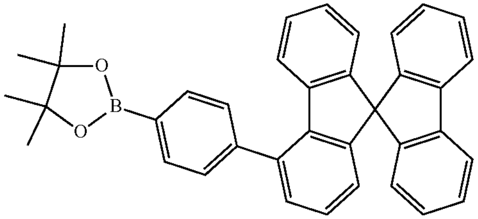 [CAS 1813574-89-8] | 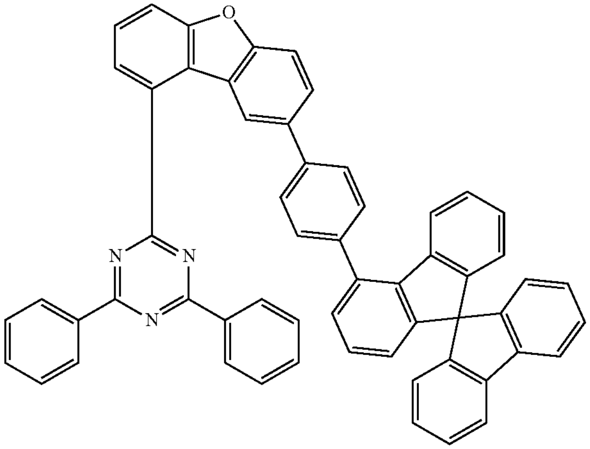 [SMILES: c1ccc(-c2nc(-c3ccccc3)nc(-c3cccc4oc5ccc(-c6ccc(-c7cccc8c7-c7ccccc7C87c8ccccc8-c8ccccc87)cc6)cc5c34)n2)cc1] | 55% |
| 4b | 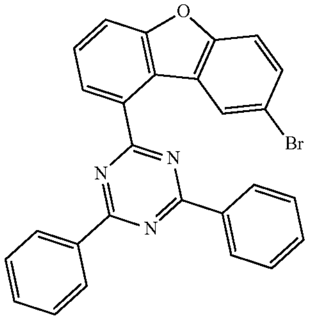 [CAS 1822310-63-3] | 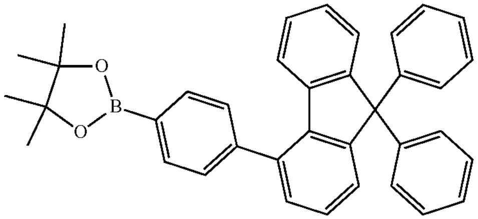 [CAS 1813574-77-4] | 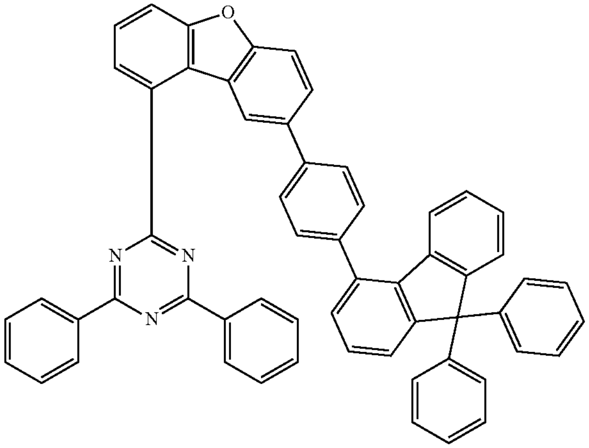 [SMILES: c1ccc(-c2nc(-c3ccccc3)nc(-c3cccc4oc5ccc(-c6ccc(-c7cccc8c7-c7ccccc7C8(c7ccccc7)c7ccccc7)cc6)cc5c34)n2)cc1] | 50% |

-continued
| No. | Reactant 1 | Reactant 2 | Product | Yield |
|---|---|---|---|---|
| 5b | 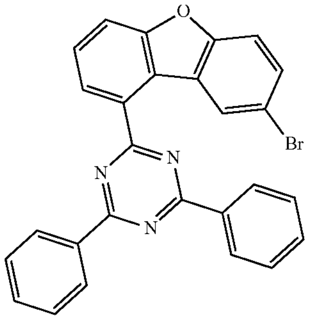 [CAS 1822310-63-3] | 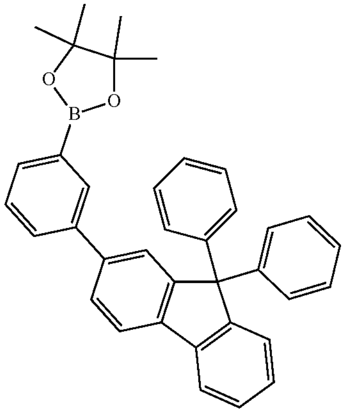 [CAS 1813574-80-9] | 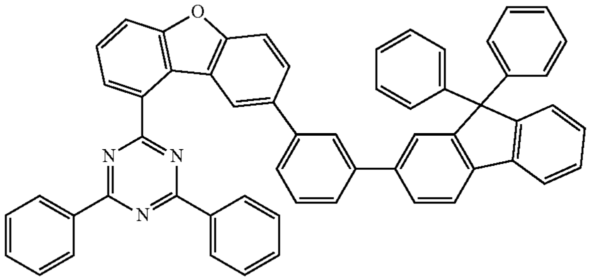 [SMILES: c1ccc(-c2nc(-c3ccccc3)nc(-c3cccc4oc5ccc(-c6cccc(-c7ccc8c(c7)C(c7ccccc7)(c7ccccc7)c7ccccc7-8)c6)cc5c34)n2)cc1] | 60% |
| 6b | 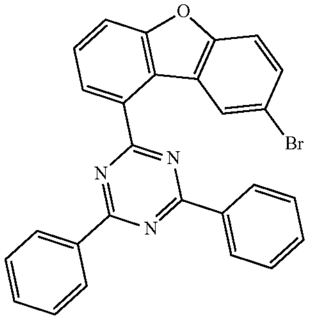 [CAS 1822310-63-3] | 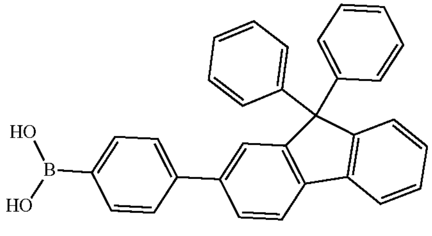 [CAS 736928-24-8] | 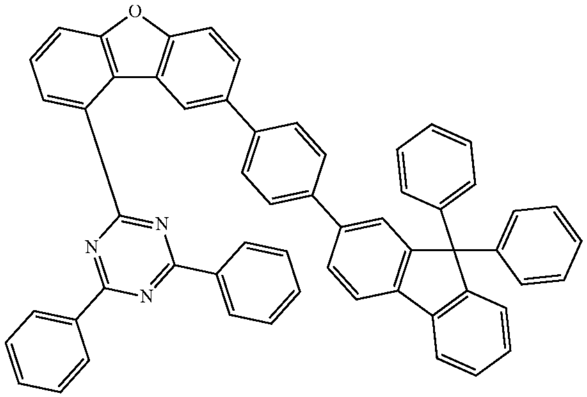 [SMILES: c1ccc(-c2nc(-c3ccccc3)nc(-c3cccc4oc5ccc(-c6ccc(-c7ccc8c(c7)C(c7ccccc7)(c7ccccc7)c7ccccc7-8)cc6)cc5c34)n2)cc1] | 53% |

-continued
| No. | Reactant 1 | Reactant 2 | Product | Yield |
|---|---|---|---|---|
| 7b | 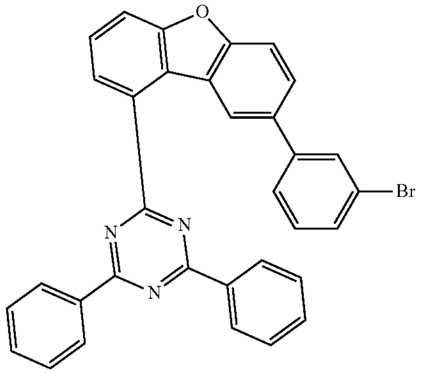 [CAS 2178703-69-1] | 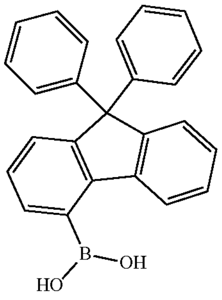 [CAS 1224976-40-2] | 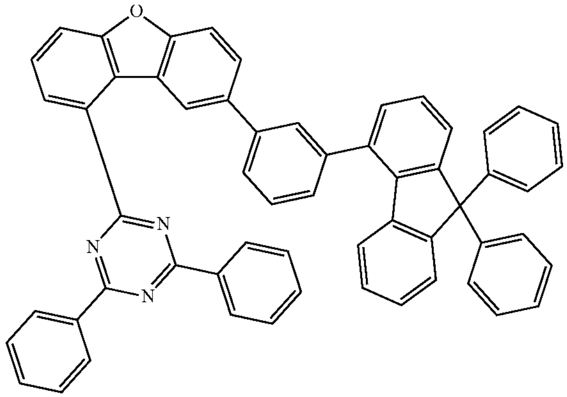 [SMILES: c1ccc(-c2nc(-c3ccccc3)nc(-c3cccc4oc5ccc(-c6cccc(-c7cccc8c7-c7ccccc7C8(c7ccccc7)c7ccccc7)c6)cc5c34)n2)cc1] | 49% |
| 8b | 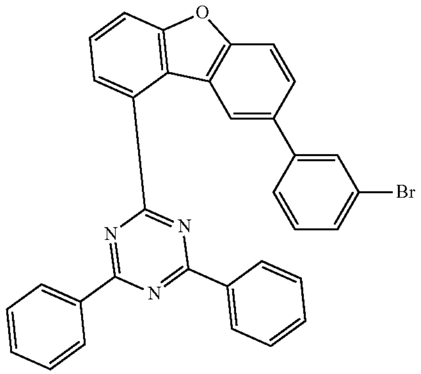 [CAS 2178703-69-1] | 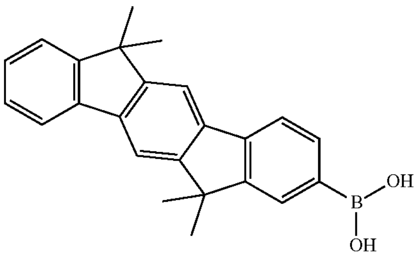 [CAS 1207559-33-8] | 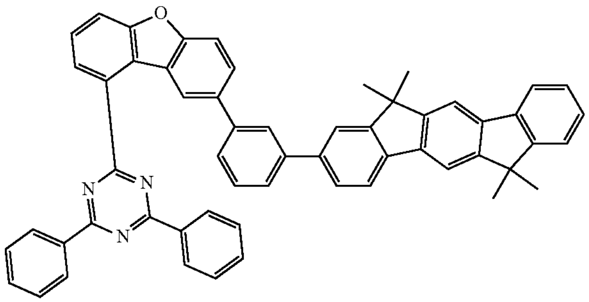 [SMILES: CC1(C)c2ccccc2-c2cc3c(cc21)-c1ccc(-c2cccc(-c4ccc5oc6cccc(-c7nc(-c8ccccc8)nc(-c8ccccc8)n7)c6c5c4)c2)cc1C3(C)C] | 28% |

-continued
| No. | Reactant 1 | Reactant 2 | Product | Yield |
| --- | --- | --- | --- | --- |
| 9b | 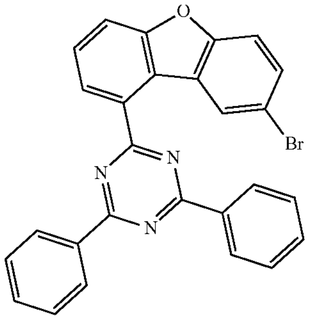 [CAS 1822310-63-3] | 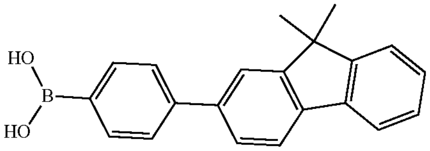 [CAS 736928-21-5] | 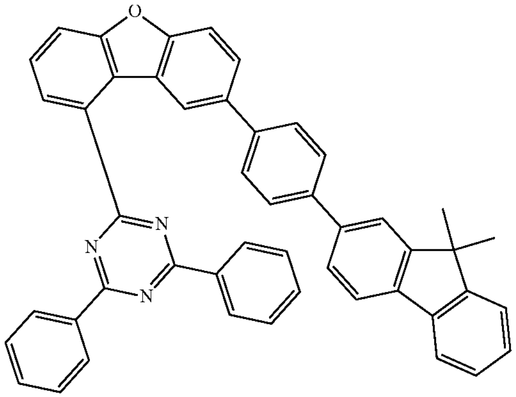 [SMILES: CC1(C)c2ccccc2-c2ccc(-c3ccc(-c4ccc5oc6cccc(-c7nc(-c8ccccc8)nc(-c8ccccc8)n7)c6c5c4)cc3)cc21] | 15% |
| 10b | 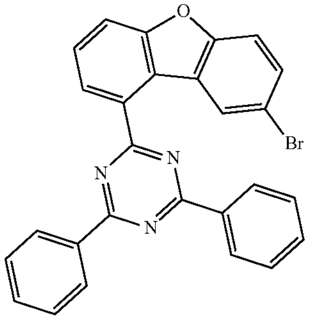 [CAS 1822310-63-3] | 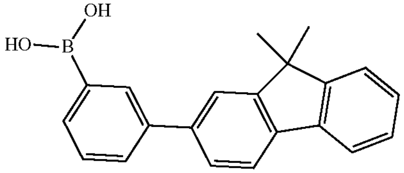 [CAS 1092840-71-5] | 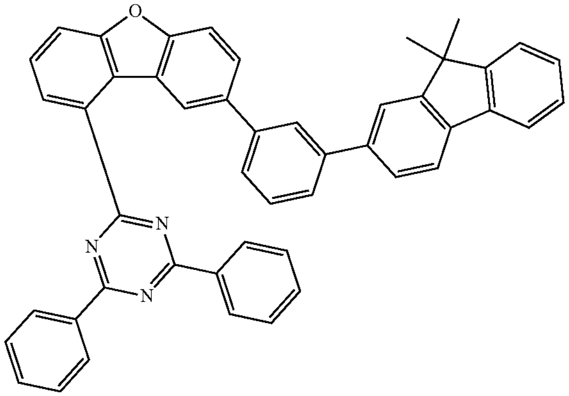 [SMILES: CC1(C)c2ccccc2-c2ccc(-c3cccc(-c4ccc5oc6cccc(-c7nc(-c8ccccc8)nc(-c8ccccc8)n7)c6c5c4)c3)cc21] | 55% |

-continued
| No. | Reactant 1 | Reactant 2 | Product | Yield |
| --- | --- | --- | --- | --- |
| 11b | 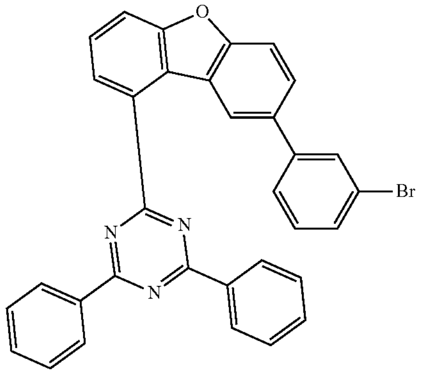 [CAS 2178703-69-1] | 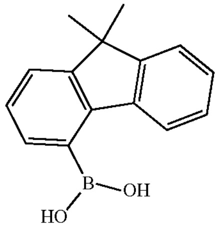 [CAS 1246022-50-3] | 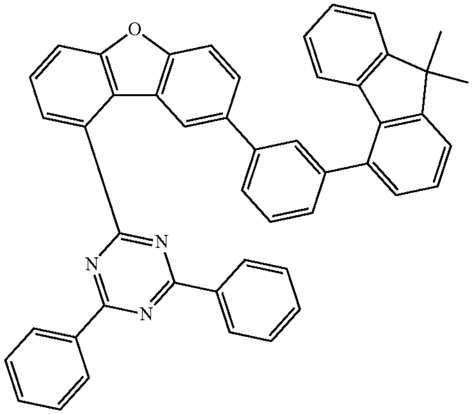 [SMILES: CC1(C)c2ccccc2-c2c(-c3cccc(-c4ccc5oc6cccc(-c7nc(-c8ccccc8)nc(-c8ccccc8)n7)c6c5c4)c3)cccc21] | 61% |
| 12b | 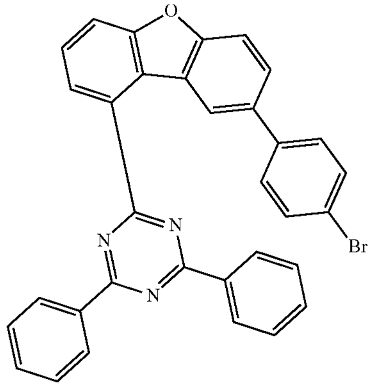 [CAS 2178073-68-0] | 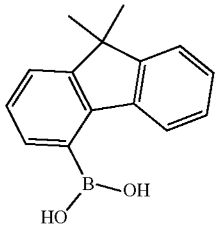 [CAS 1246022-50-3] | 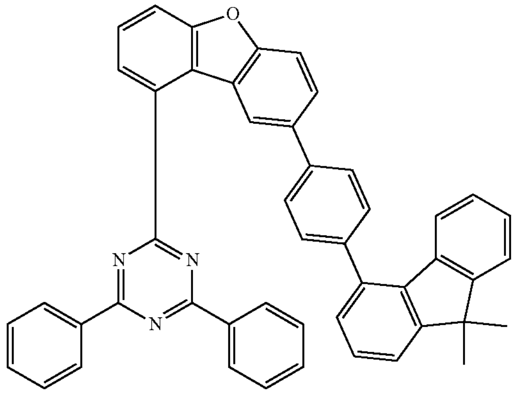 [SMILES: CC1(C)c2ccccc2-c2c(-c3ccc(-c4ccc5oc6cccc(-c7nc(-c8ccccc8)nc(-c8ccccc8)n7)c6c5c4)cc3)cccc21] | 51% |

-continued
| No. | Reactant 1 | Reactant 2 | Product | Yield |
|---|---|---|---|---|
| 13b | 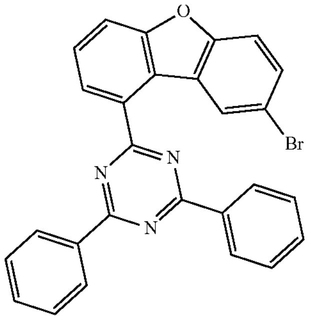 [CAS 1822310-63-3] | 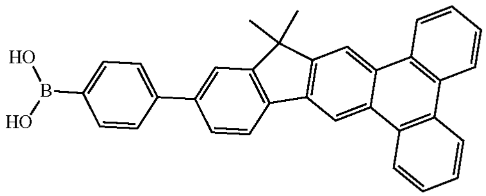 [CAS 1612245-56-3] | 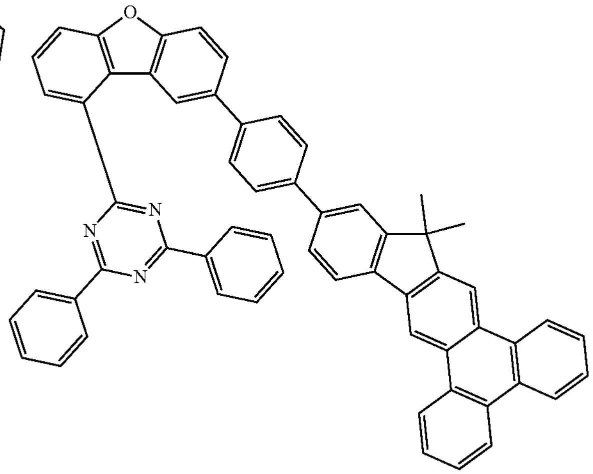 | 38% |
| 14b | 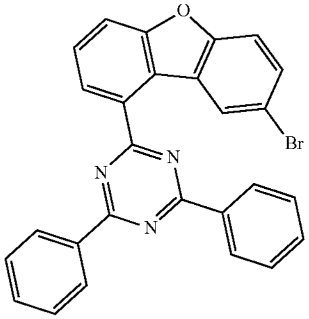 [CAS 1822310-63-3] | 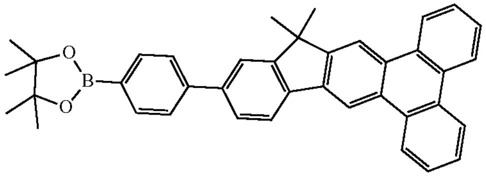 [CAS 2101632-14-6] | 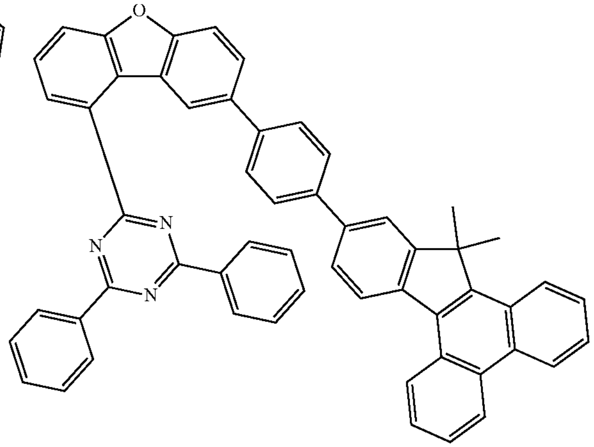 | 42% |

-continued
| No. | Reactant 1 | Reactant 2 | Product | Yield |
| --- | --- | --- | --- | --- |
| 15b | 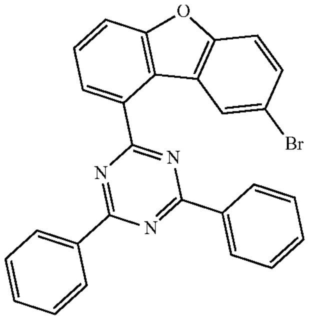 [CAS 1822310-63-3] | 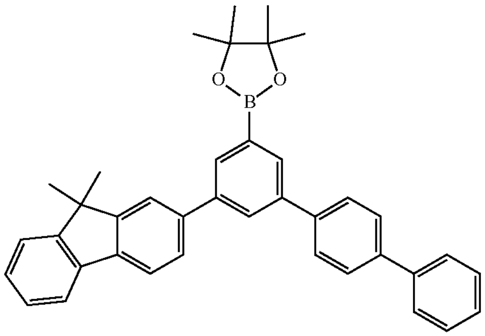 [CAS 1858289-69-6] | 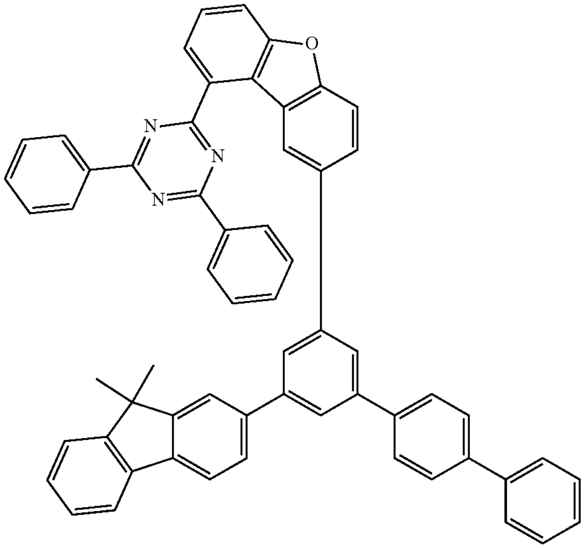 [SMILES: CC1(C)c2ccccc2-c2ccc(-c3cc(-c4ccc(-c5ccccc5)cc4)cc(-c4ccc5oc6cccc(-c7nc(-c8ccccc8)nc(-c8ccccc8)n7)c6c5c4)c3)cc21] | 48% |
| 16b | 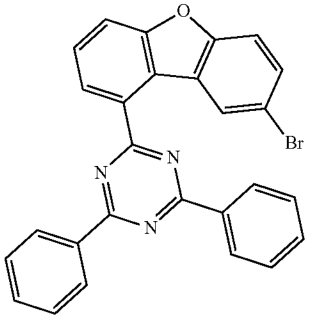 [CAS 1822310-63-3] | 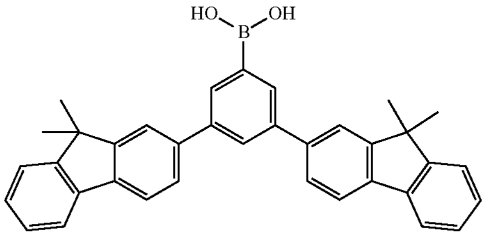 [CAS 881913-13-9] | 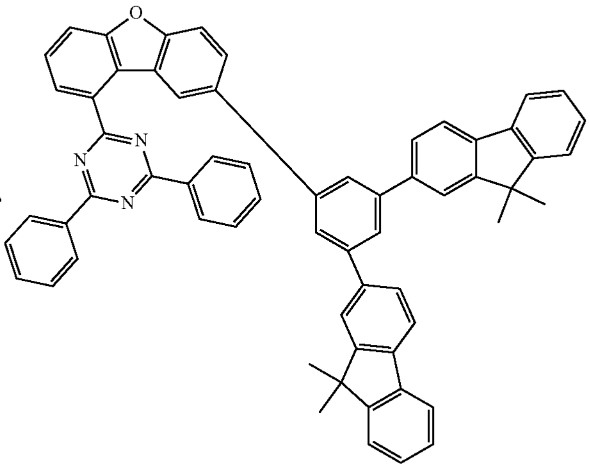 [SMILES: CC1(C)c2ccccc2-c2ccc(-c3cc(-c4ccc5c(c4)C(C)(C)c4ccccc4-5)cc(-c4ccc5oc6cccc(-c7nc(-c8ccccc8)nc(-c8ccccc8)n7)c6c5c4)c3)cc21] | 44% |

-continued
| No. | Reactant 1 | Reactant 2 | Product | Yield |
| --- | --- | --- | --- | --- |
| 17b | 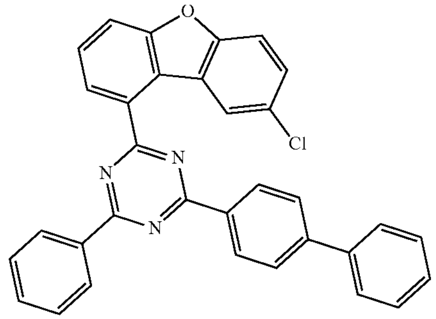 [CAS 2173554-68-2] | 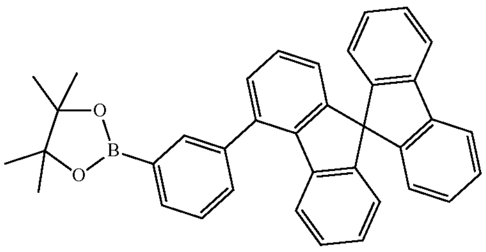 [CAS 2112854-30-3] | 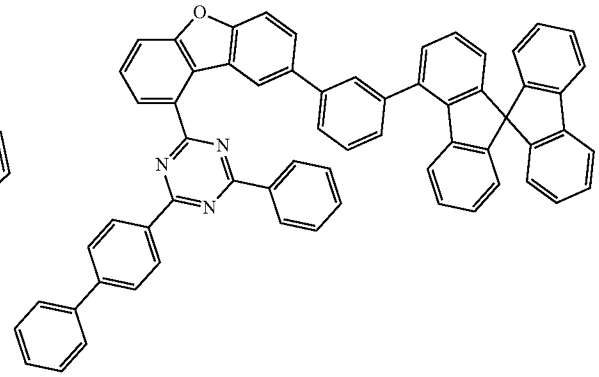 | 62% |
| 18b | 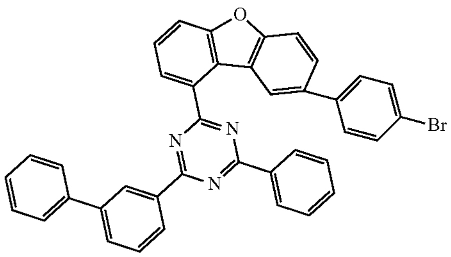 [CAS 2178073-71-5] | 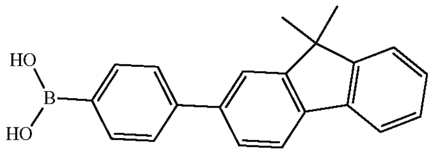 [CAS 736928-21-5] | 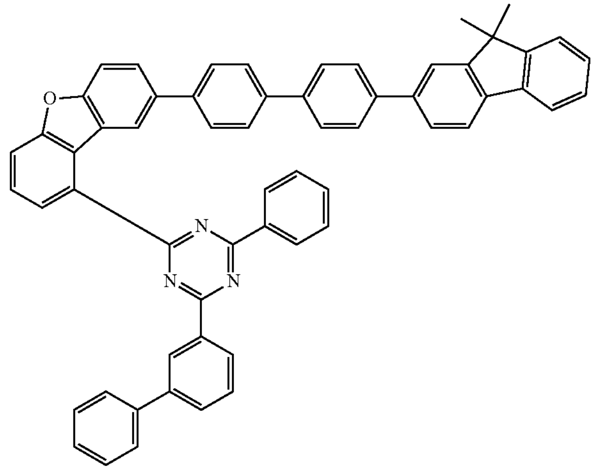 [SMILES: CC1(C)c2ccccc2-c2ccc(-c3ccc(-c4ccc(-c5ccc6oc7cccc(-c8nc(-c9ccccc9)nc(-c9cccc(-c%10ccccc%10)c9)n8)c7c6c5)cc4)cc3)cc21] | 48% |

-continued
| No. | Reactant 1 | Reactant 2 | Product | Yield |
| --- | --- | --- | --- | --- |
| 19b | 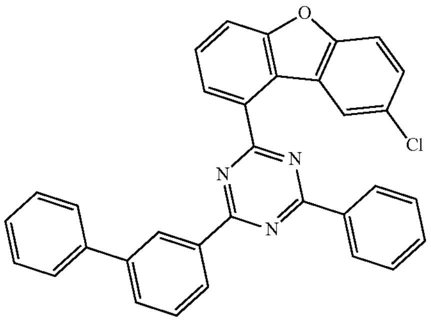 [CAS 2173554-89-5] | 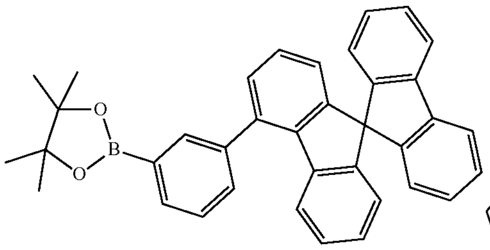 [CAS 2112854-30-3] | 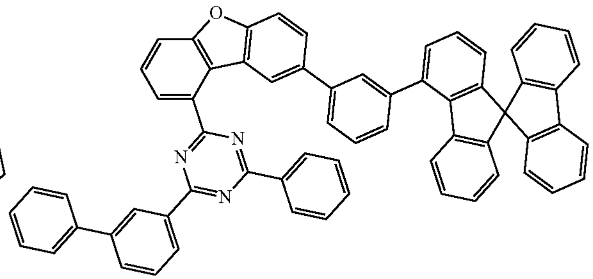 | 55% |
| 20b | 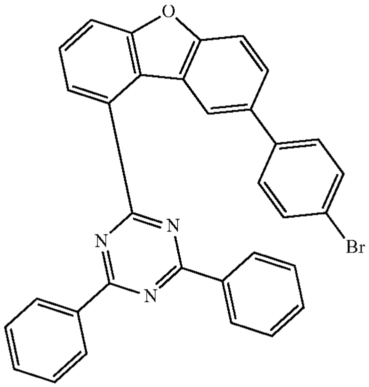 [CAS 2178073-68-0] | 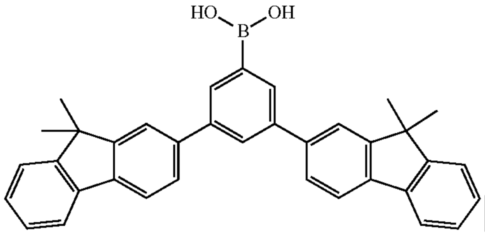 [CAS 881913-13-9] | 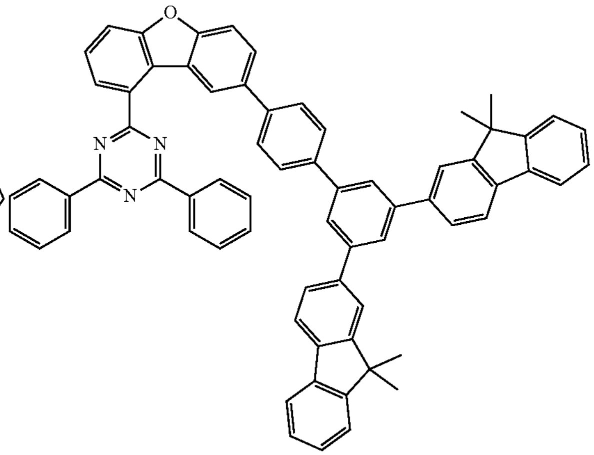 | 49% |

-continued
| No. | Reactant 1 | Reactant 2 | Product | Yield |
| --- | --- | --- | --- | --- |
| 21b | 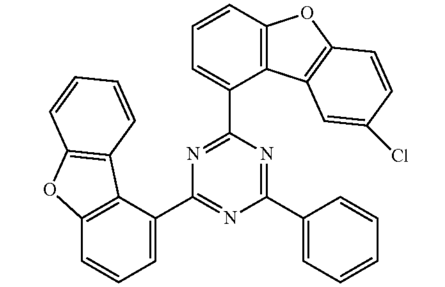 [SMILES: Clc1ccc2oc3cccc(-c4nc(-c5ccccc5)nc(-c5cccc6oc7ccccc7c56)n4)c3c2c1] | 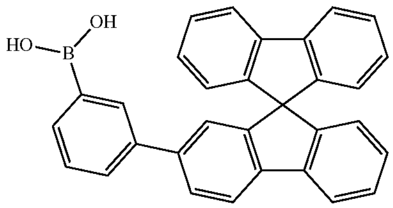 [CAS 1365812-76-5] | 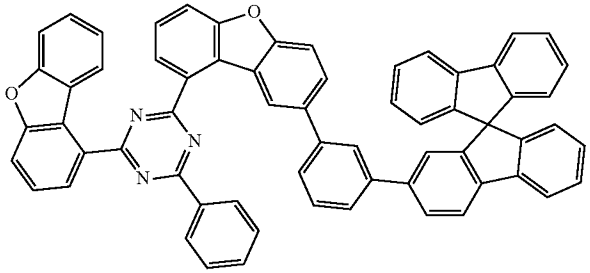 [SMILES: c1ccc(-c2nc(-c3cccc4oc5ccccc5c34)nc(-c3cccc4oc5ccc(-c6cccc(-c7ccc8c(c7)C7(c9ccccc9-c9ccccc97)c7ccccc7-8)c6)cc5c34)n2)cc1] | 53% |
| 22b | 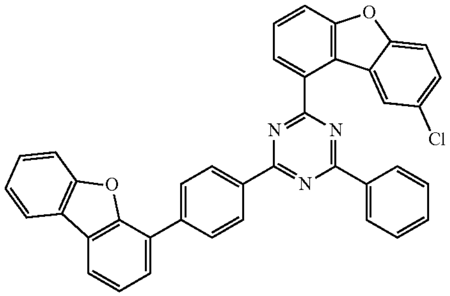 | 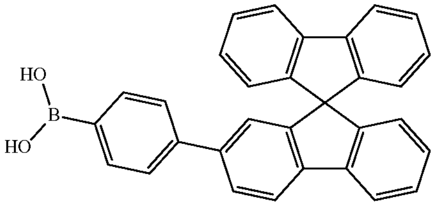 [CAS 1365812-76-5] | 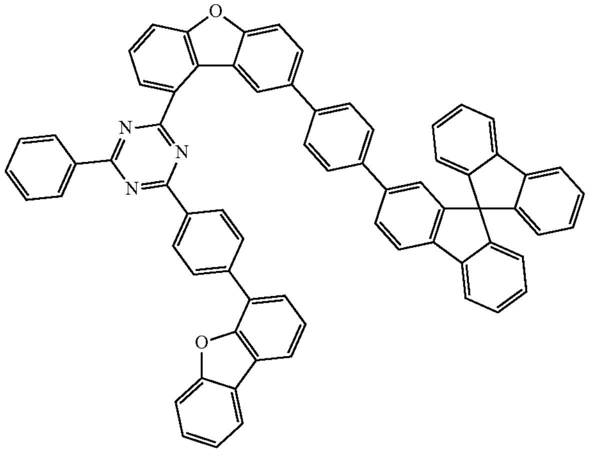 [SMILES: c1ccc(-c2nc(-c3ccc(-c4cccc5c4oc4ccccc45)cc3)nc(-c3cccc4oc5ccc(-c6ccc(-c7ccc8c(c7)C7(c9ccccc9-c9ccccc97)c7ccccc7-8)cc6)cc5c34)n2)cc1] | 59% |

-continued
| No. | Reactant 1 | Reactant 2 | Product | Yield |
|---|---|---|---|---|
| 23b | 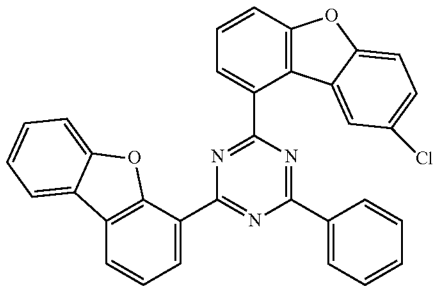 [SMILES: Clc1ccc2oc3cccc(-c4nc(-c5ccccc5)nc(-c5cccc6c5oc5ccccc56)n4)c3c2c1] | 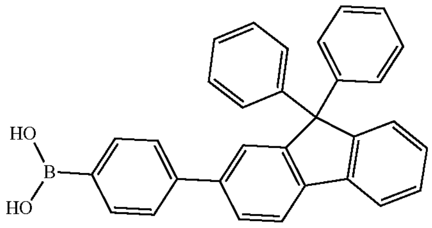 [CAS 736928-24-8] | 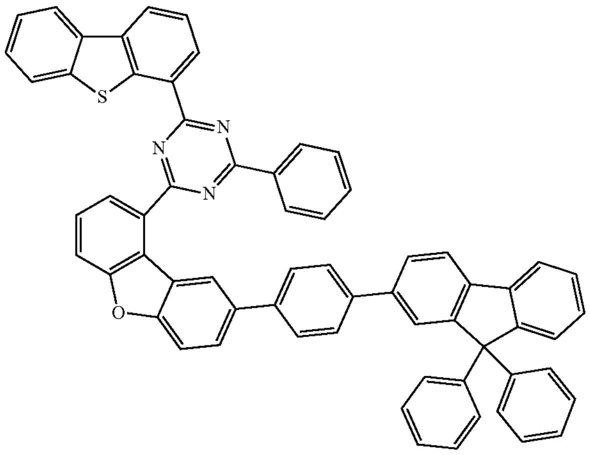 [SMILES: c1ccc(-c2nc(-c3cccc4c3sc3ccccc34)nc(-c3cccc4oc5ccc(-c6ccc(-c7ccc8c(c7)C(c7ccccc7)(c7ccccc7)c7ccccc7-8)cc6)cc5c34)n2)cc1] | 65% |
| 24b | 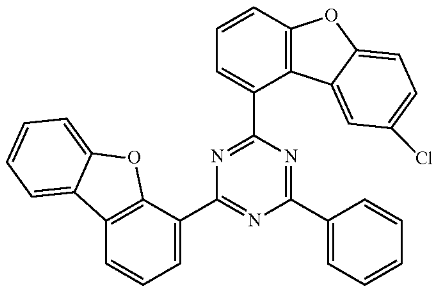 [SMILES: Clc1ccc2oc3cccc(-c4nc(-c5ccccc5)nc(-c5cccc6c5oc5ccccc56)n4)c3c2c1] | 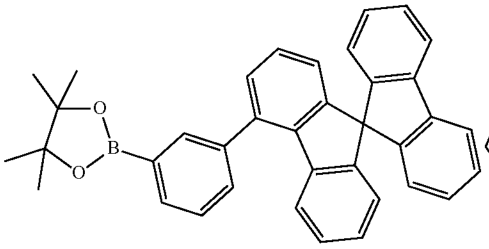 | 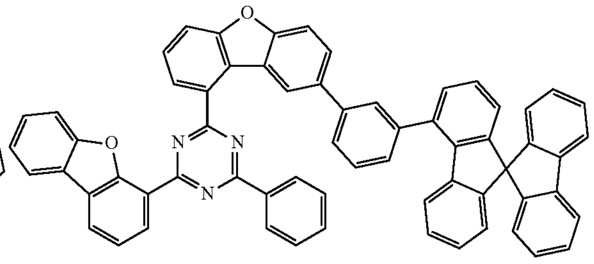 | 57% |

-continued
| No. | Reactant 1 | Reactant 2 | Product | Yield |
| --- | --- | --- | --- | --- |
| 25b | 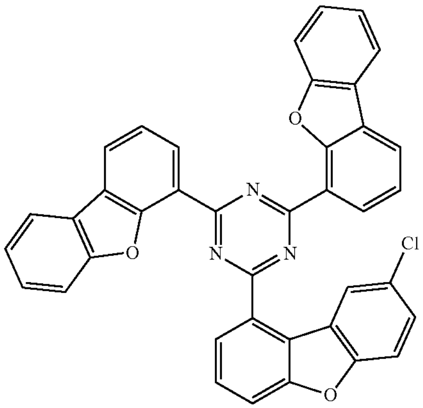 [SMILES: Clc1ccc2oc3cccc(-c4nc(-c5cccc6c5oc5ccccc56)nc(-c5cccc6c5oc5ccccc56)n4)c3c2c1] | 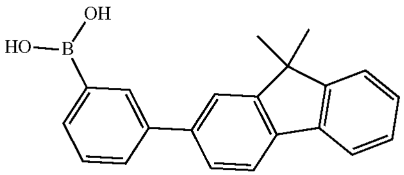 [CAS 1092840-71-5] | 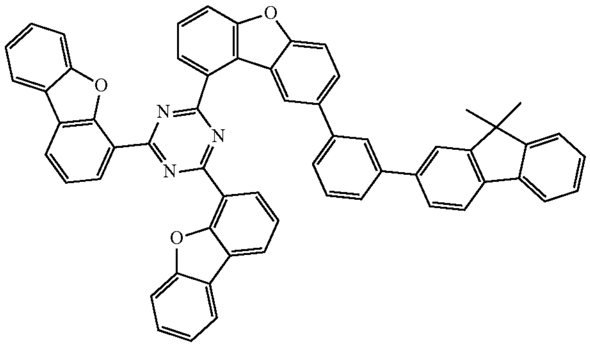 [SMILES: CC1(C)c2ccccc2-c2ccc(-c3cccc(-c4ccc5oc6cccc(-c7nc(-c8cccc9c8oc8ccccc89)nc(-c8cccc9c8oc8ccccc89)n7)c6c5c4)c3)cc21] | 57% |
| 26b | 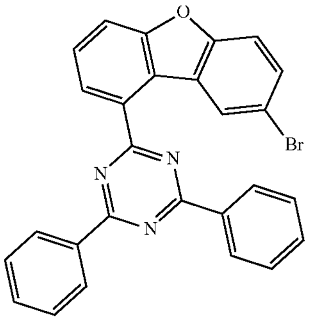 [CAS 1822310-63-3] | 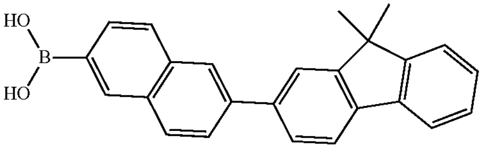 [CAS 1233141-52-0] | 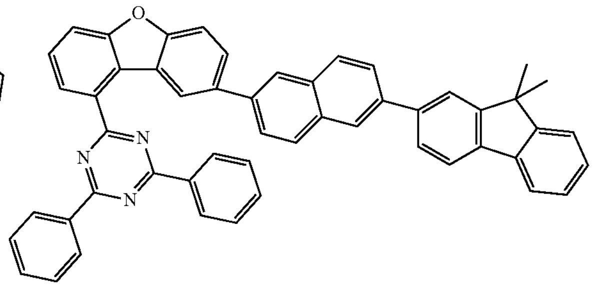 | 53% |

-continued
| No. | Reactant 1 | Reactant 2 | Product | Yield |
|---|---|---|---|---|
| 27b | 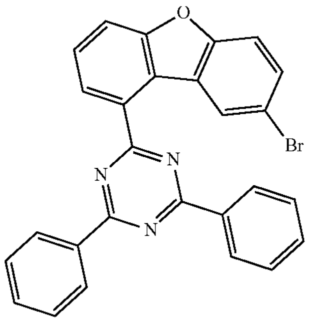 [CAS 1822310-63-3] | 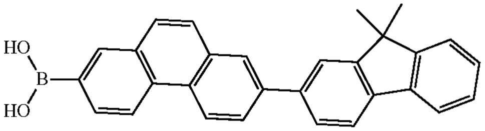 [CAS 1246021-88-4] | 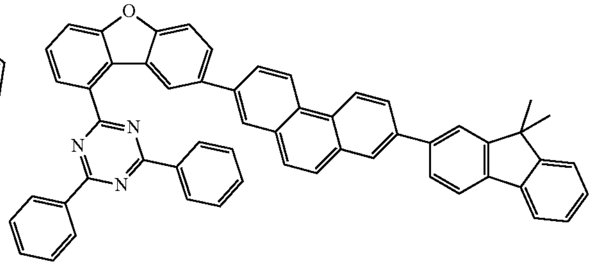 | 49% |

The invention claimed is:

1. An emitting layer, an electron transport layer, an electron injection layer or a hole blocker layer comprising a composition comprising at least one compound of the formula (1k) and at least one compound of the formula (2e)

Formula (1k)

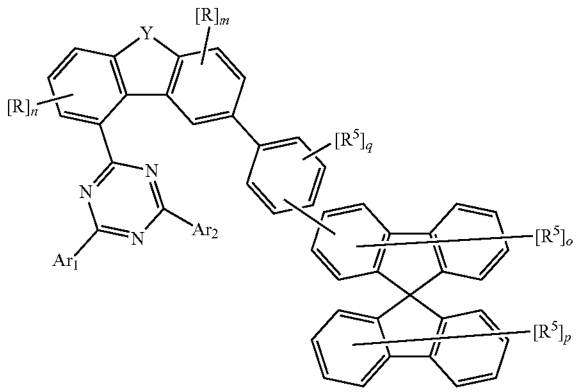

Formula (2e)

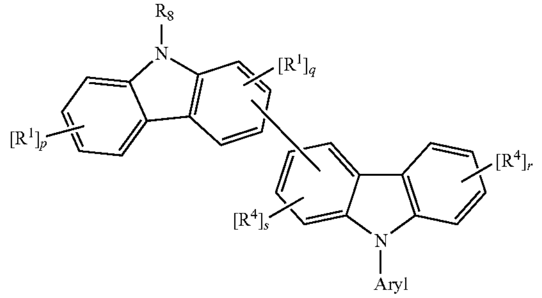

where the symbols and indices used are as follows:

Y is selected from O and S;

$R_B$ is $Ar_3$;

$Ar_1$, $Ar_2$ at each instance are each independently are selected from Ar-1 to Ar-12

Ar-1

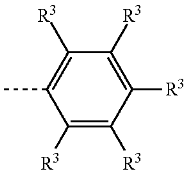

Ar-2

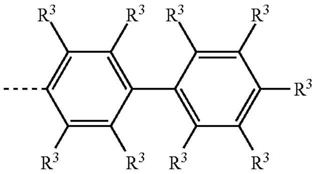

Ar-3

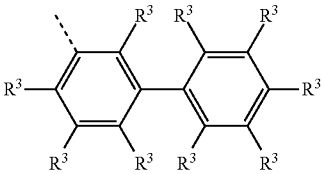

-continued

Ar-4

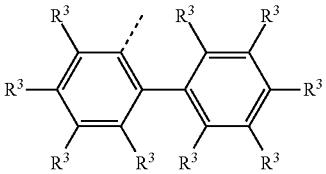

Ar-5

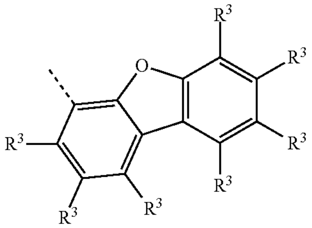

Ar-6

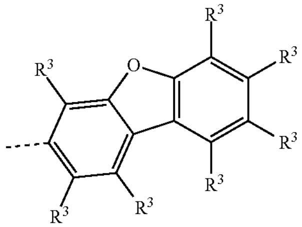

Ar-7

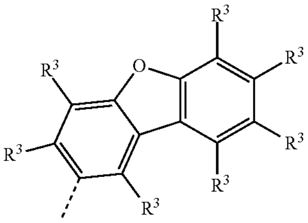

Ar-8

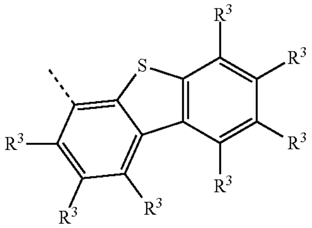

Ar-9

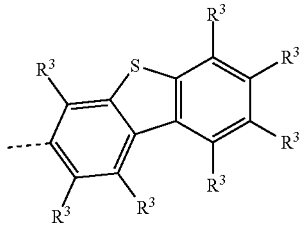

Ar-10

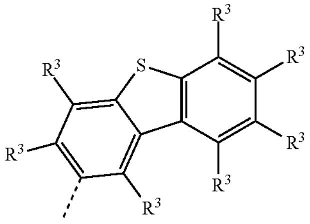

-continued

Ar-11

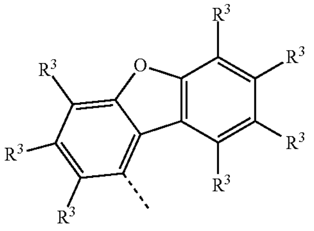

Ar-12

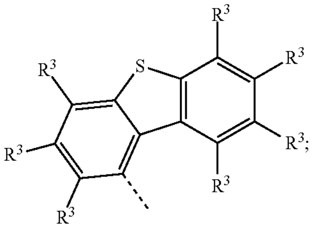

$Ar_3$ is an aromatic ring system having 6 to 40 aromatic ring atoms selected from Ar-2 to Ar-7

Ar-2

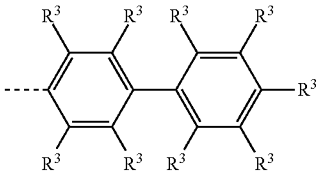

Ar-3

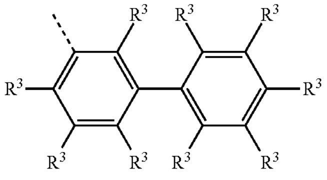

Ar-4

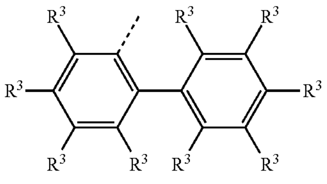

Ar-5

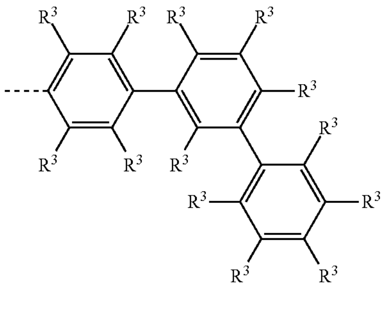

-continued

Ar-6

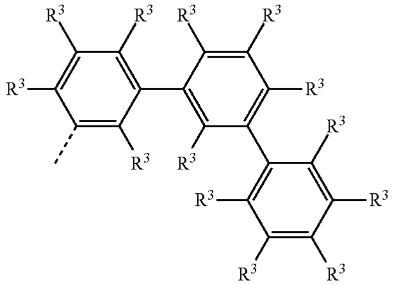

Ar-7

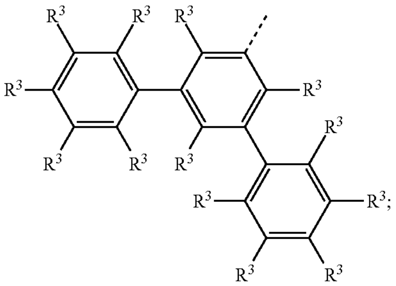

R is the same or different at each instance and is selected from the group consisting of D, F, CN and an aryl group having 6 to 10 carbon atoms;

$R^1$ is the same or different at each instance and is selected from the group consisting of D, F, an alkyl group having 1 to 40 carbon atoms or an aromatic or heteroaromatic ring system which has 5 to 40 aromatic ring atoms;

$R^3$ is the same or different at each instance and is selected from the group consisting of H or D;

$R^4$ is D;

$R^5$ is the same or different at each instance and is D or phenyl; and

Aryl is an aryl group containing 6 to 40 carbon atoms n and m at each instance are independently 0, 1, 2 or 3, o at each instance is independently 0, 1, 2, 3, 4, 5, 6 or 7;

q at each instance is independently 0, 1, 2 or 3;

p at each instance is independently 0, 1, 2, 3 or 4 r and s are each independently 0, 1, 2, 3 or 4.

2. The emitting layer, the electron transport layer, the electron injection layer or the hole blocker layer as claimed in claim 1, wherein Y in formula (1k) is O.

3. The emitting layer, the electron transport layer, the electron injection layer or the hole blocker layer as claimed in claim 1, wherein the composition further comprises at least one compound selected from the group consisting of hole injection materials, hole transport materials, hole blocker materials, wide band gap materials, fluorescent emitters, phosphorescent emitters, host materials, matrix materials, electron blocker materials, electron transport materials and electron injection materials, n-dopants and p-dopants.

4. An organic electronic device comprising the emitting layer, the electron transport layer, the electron injection layer or the hole blocker layer as claimed in claim 1.

5. The device as claimed in claim 4, wherein the organic electronic device is selected from the group of organic integrated circuits (OICs), organic field-effect transistors (OFETs), organic thin-film transistors (OTFTs), organic electroluminescent devices, organic solar cells (OSCs), organic optical detectors and organic photoreceptors.

6. The device as claimed in claim 5, wherein the device is an electroluminescent device selected from organic light-emitting transistors (OLETs), organic field quench devices (OFQDs), organic light-emitting electrochemical cells (OLECs), organic laser diodes (O-lasers) and organic light-emitting diodes (OLEDs).

7. An organic electronic device which comprises the emitting layer, electron transport layer, electron injection layer, or hole blocker layer as claimed in claim 1 together with a phosphorescent emitter.

8. A process for producing an organic electronic device, which comprises applying at least one emitting layer, electron transport layer, electron injection layer or hole blocker layer as claimed in claim 1 by gas phase deposition or from solution.

9. The emitting layer, the electron transport layer, the electron injection layer or the hole blocker layer as claimed in claim 1 wherein the compound of formula (1k) is selected from the following compounds:

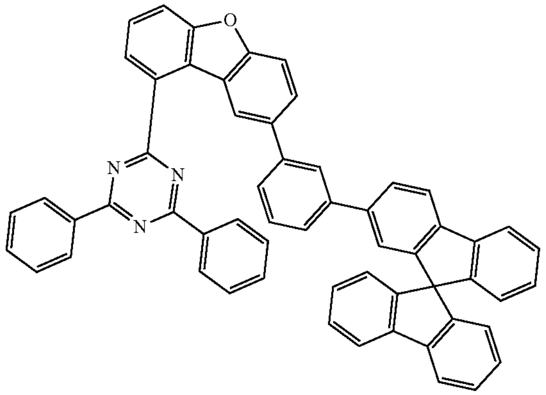

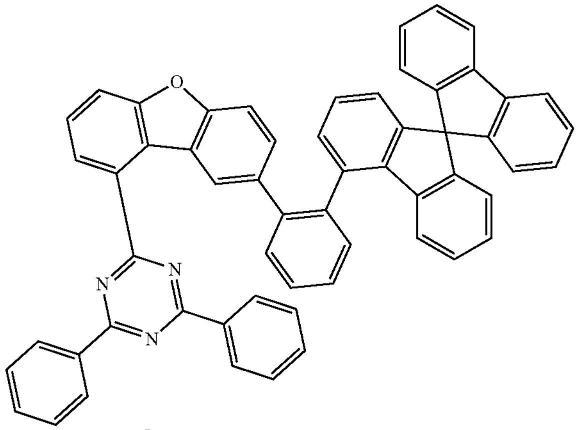

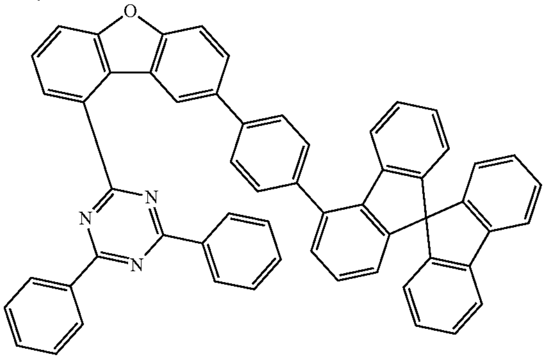

-continued

7

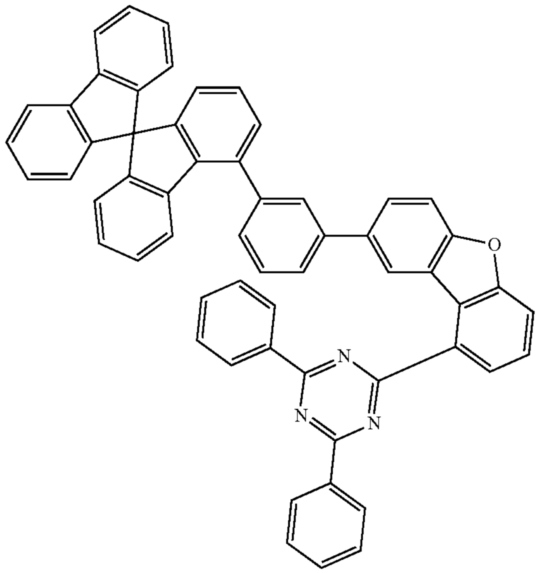

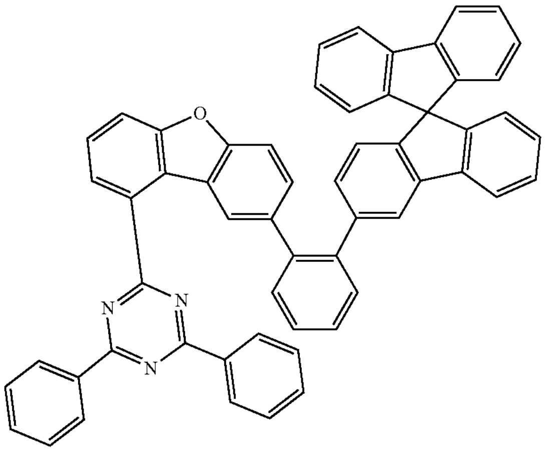

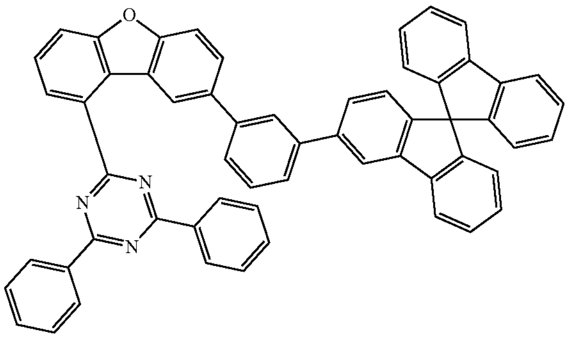

-continued
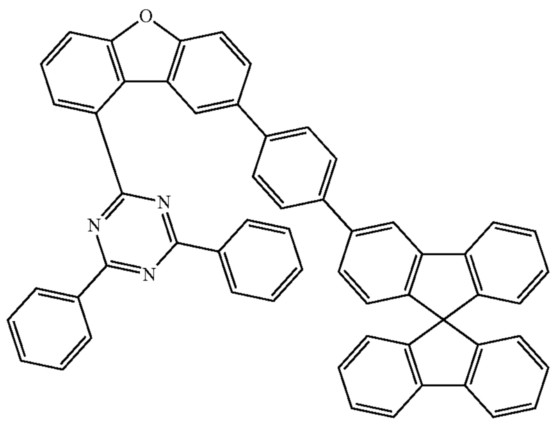
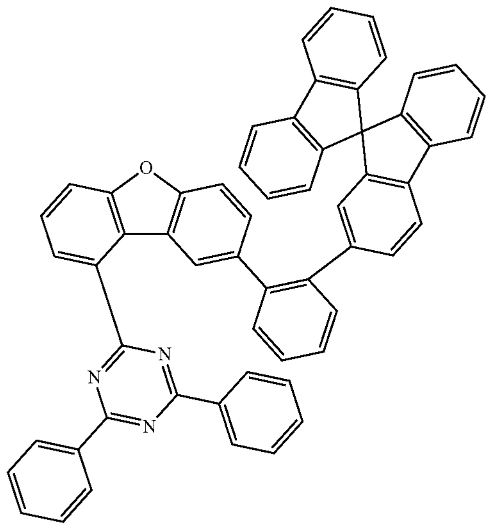
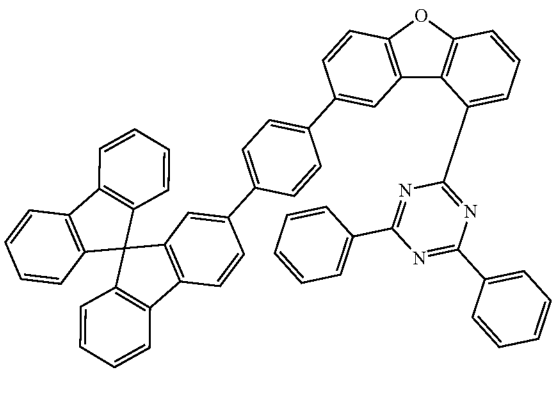
-continued
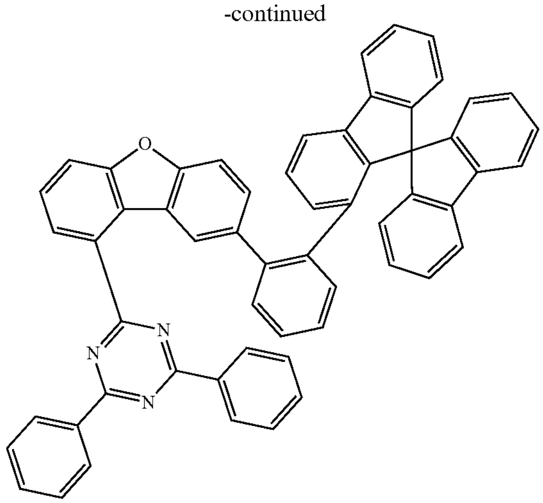
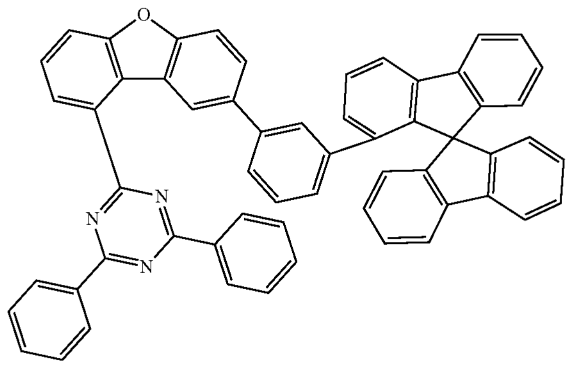
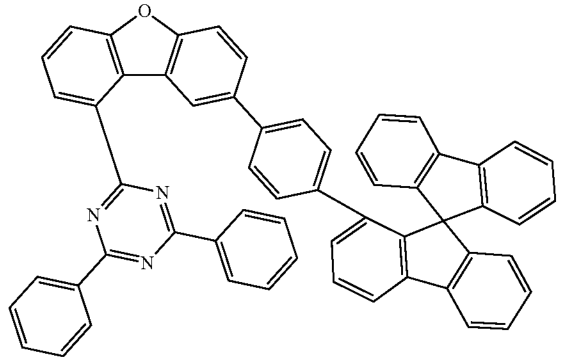
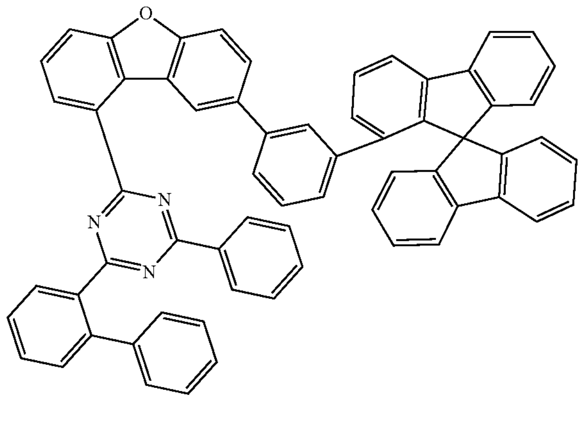

-continued
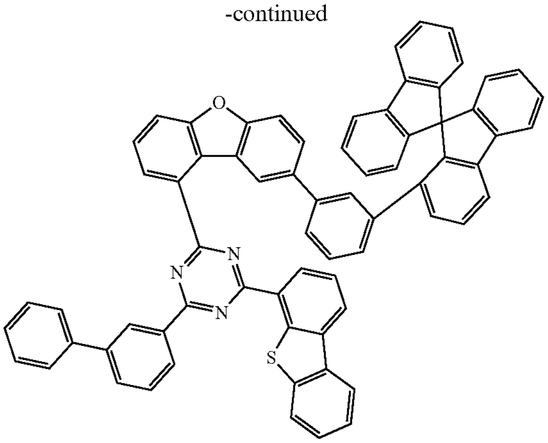
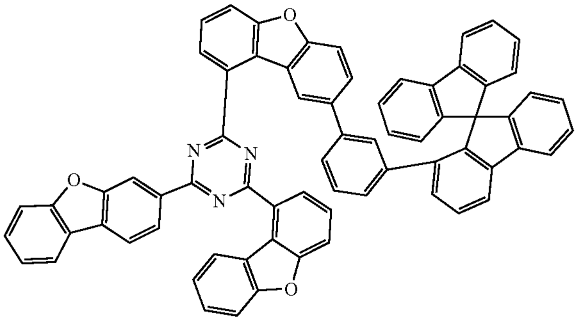
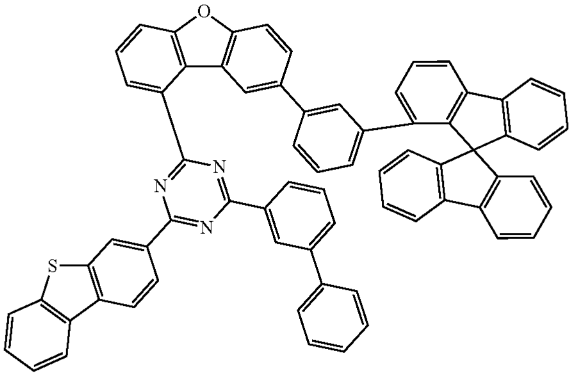
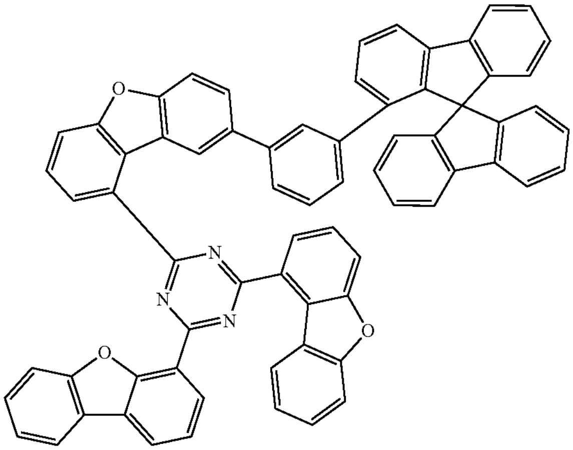
-continued
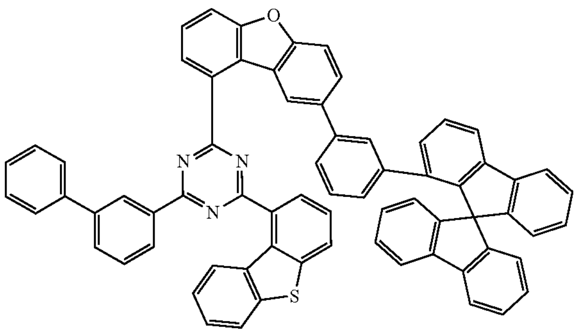
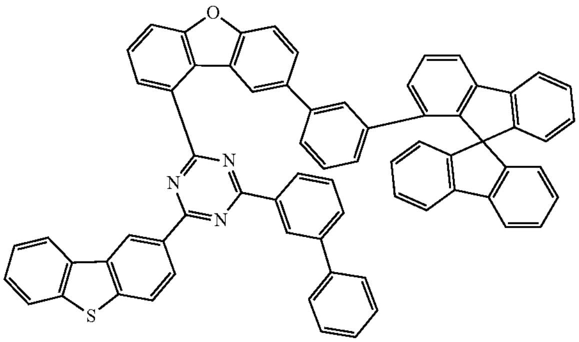
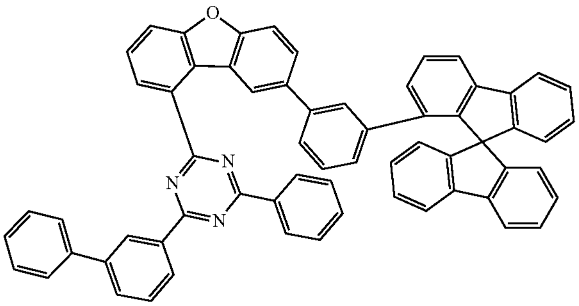
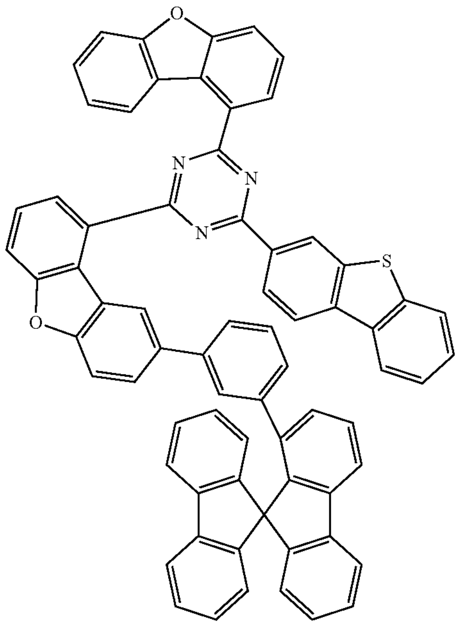

-continued
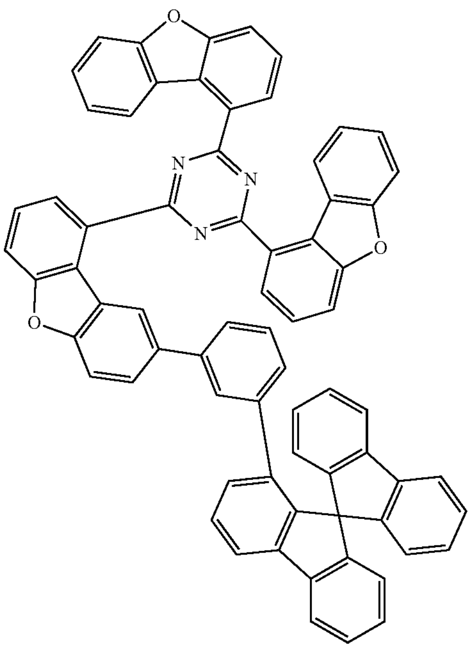
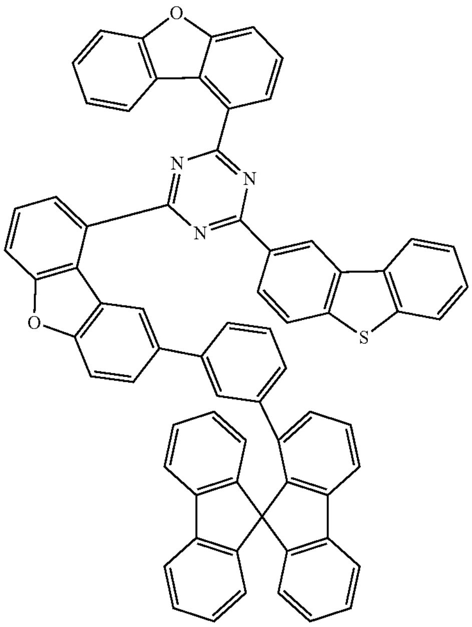
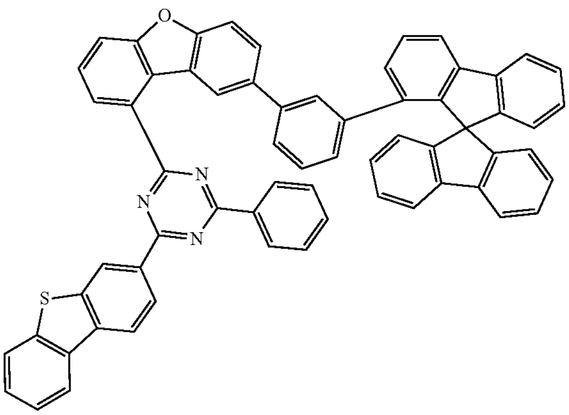
-continued
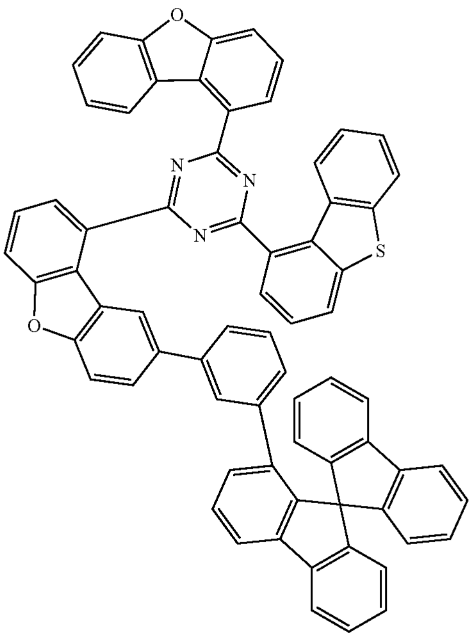
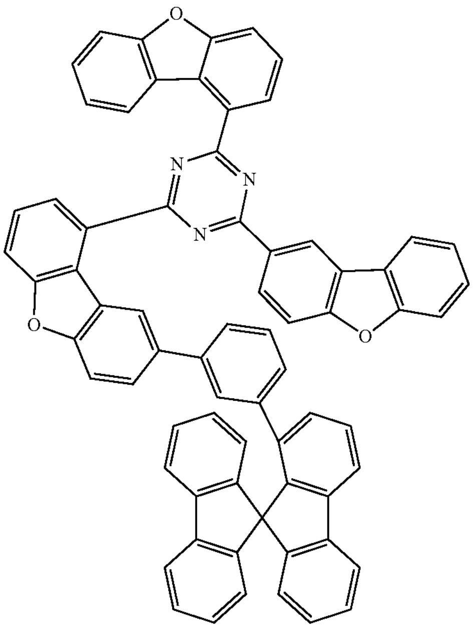

-continued
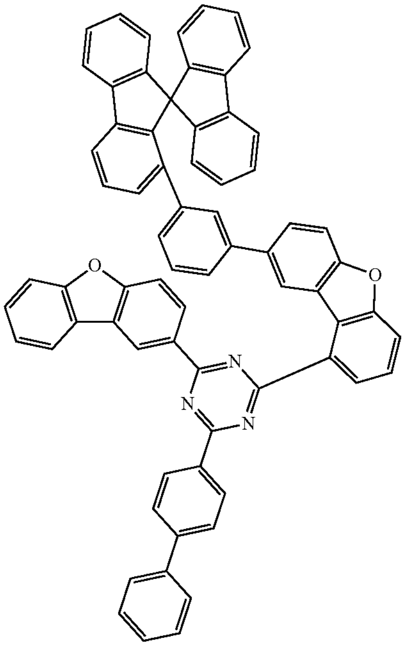
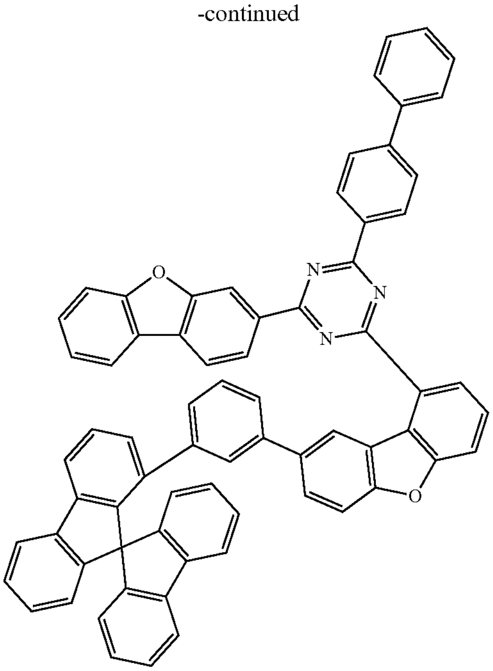
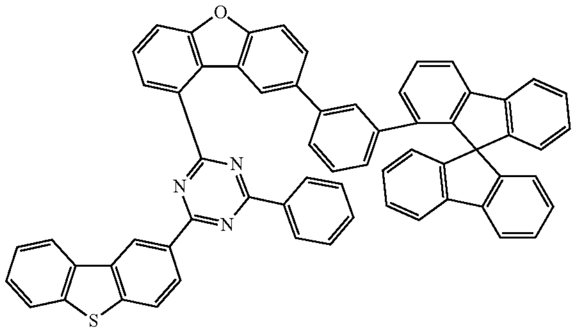
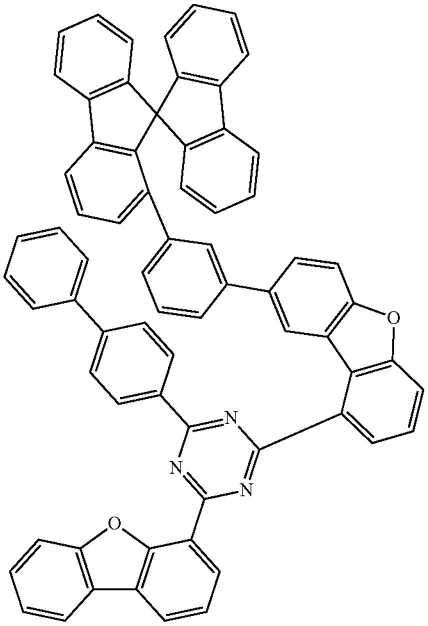
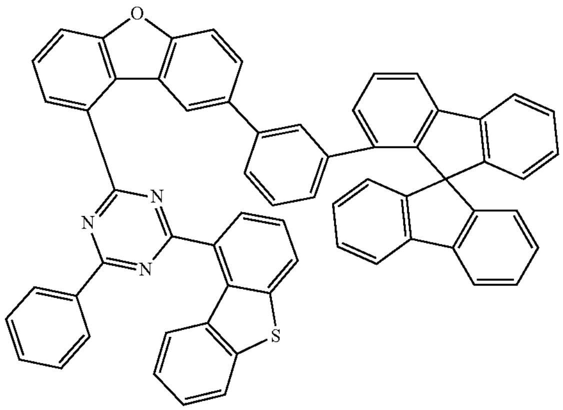
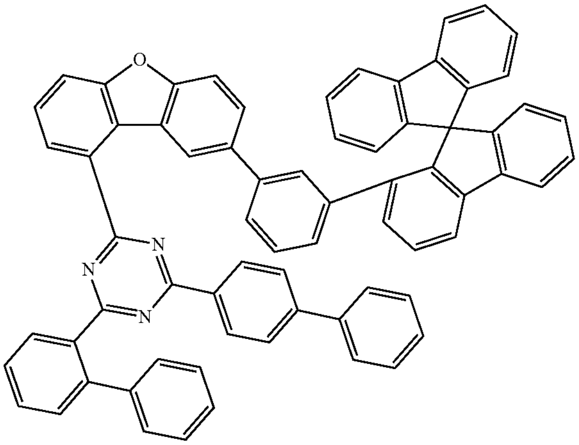

-continued
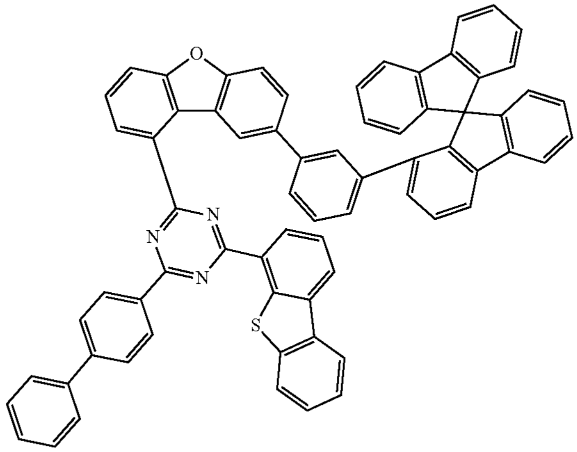
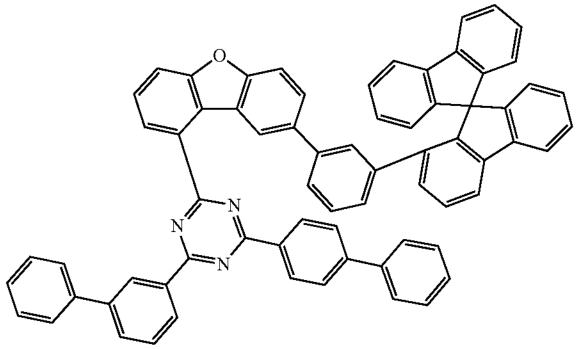
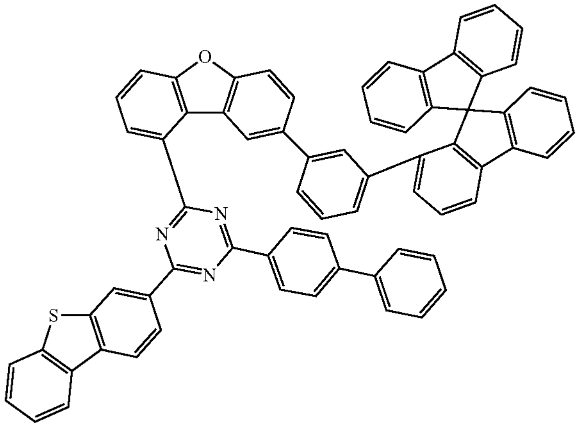
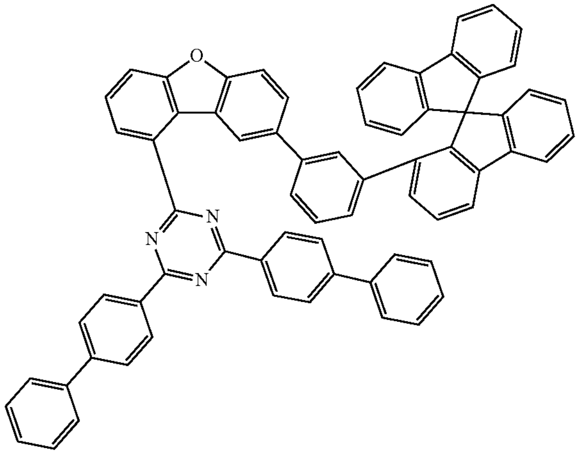
-continued
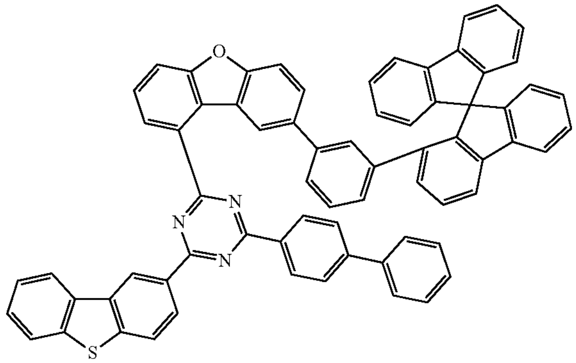
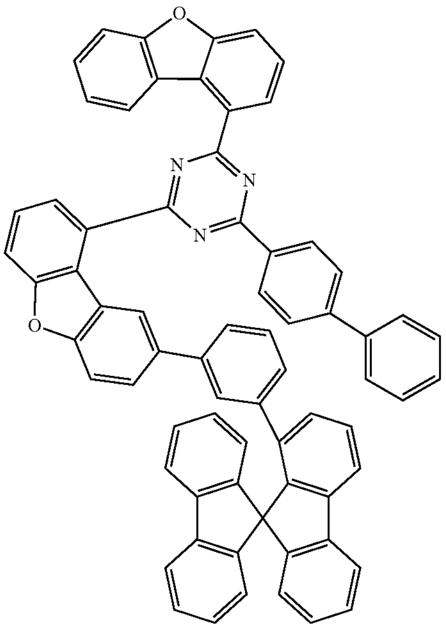
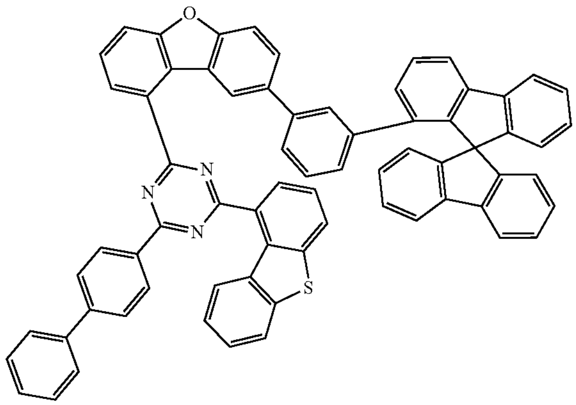

-continued
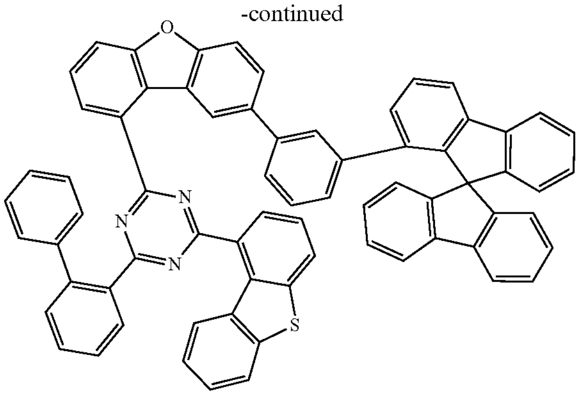
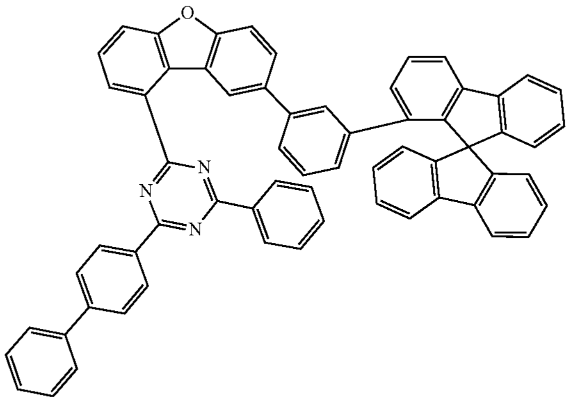
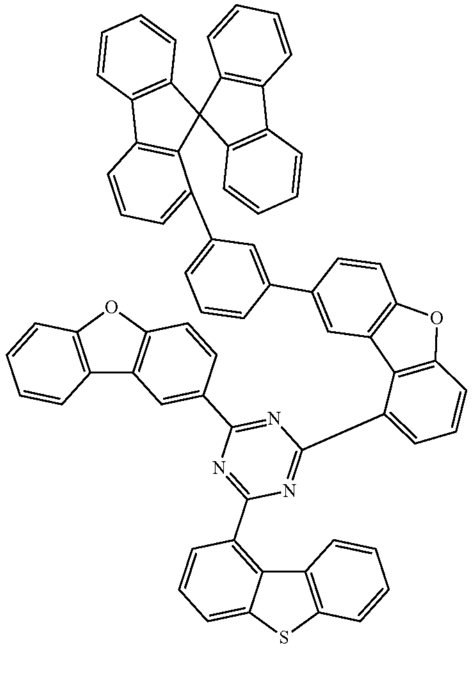
-continued
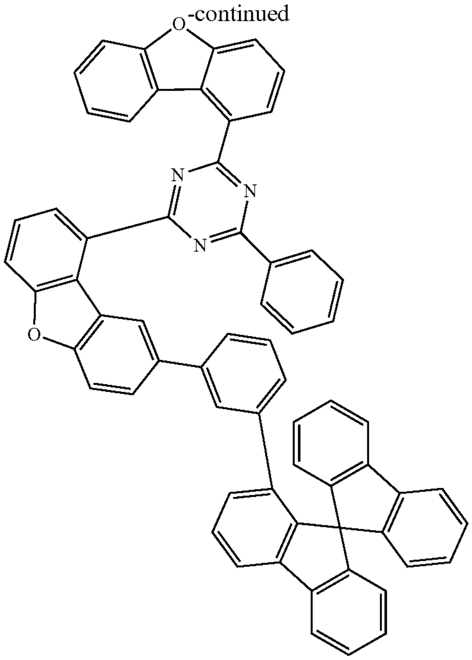
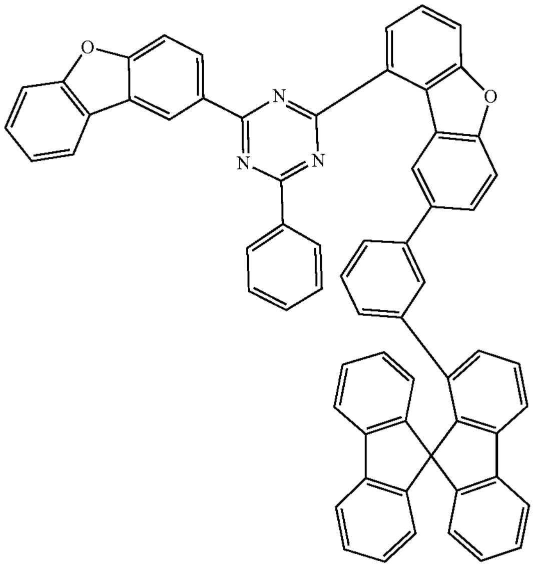
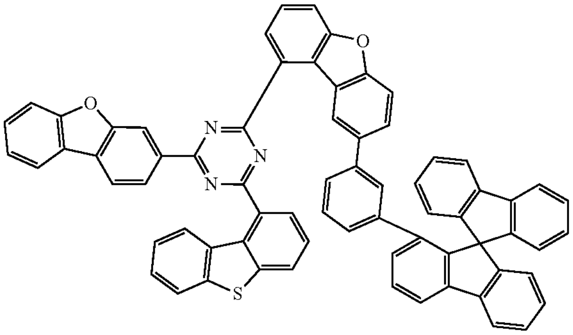

-continued
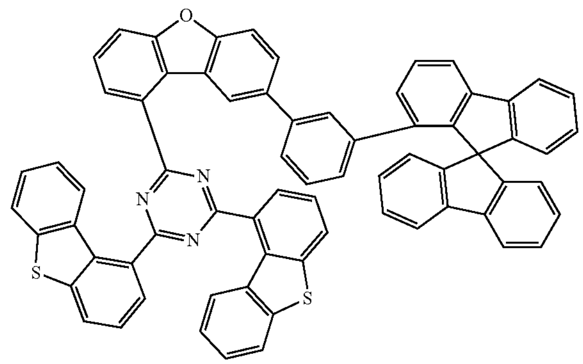
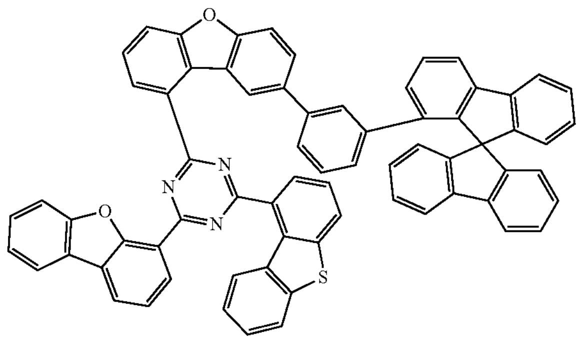
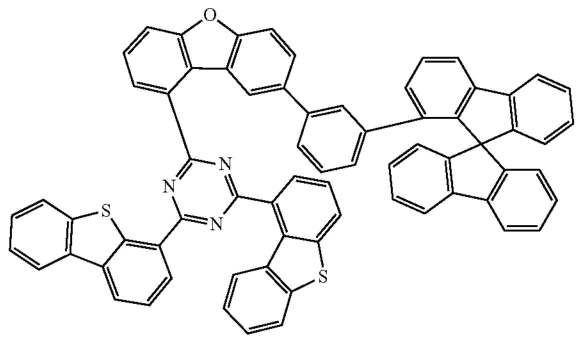
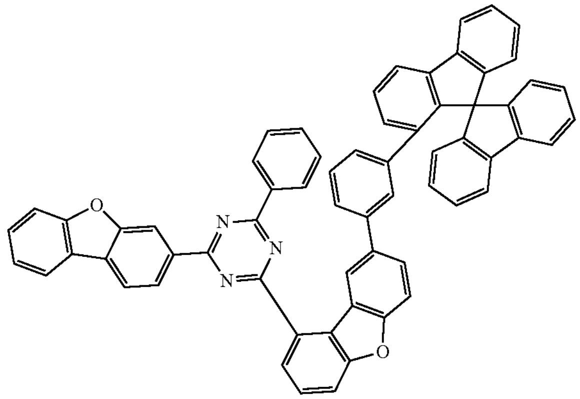
-continued
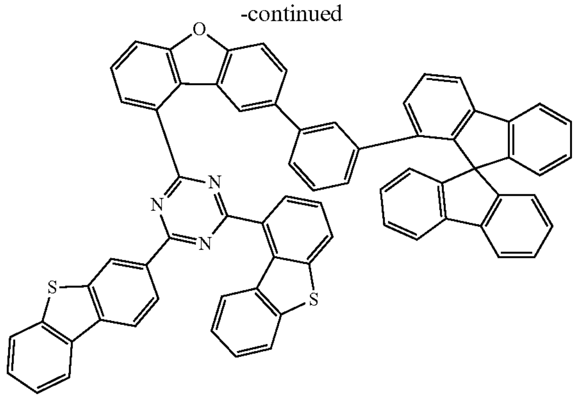
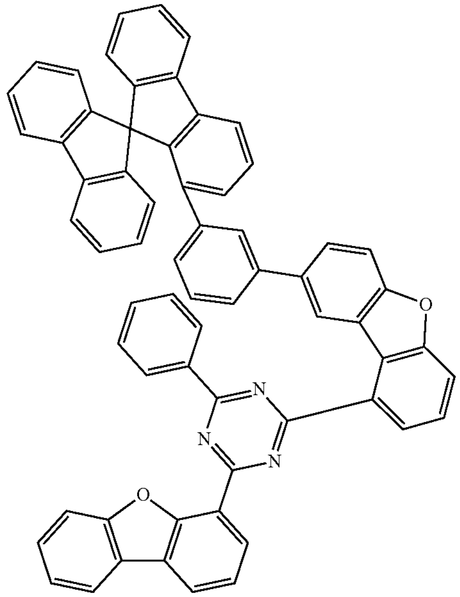
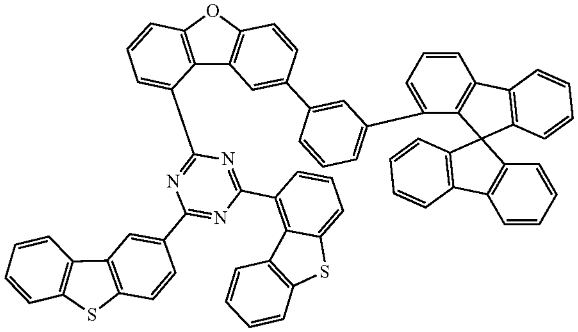
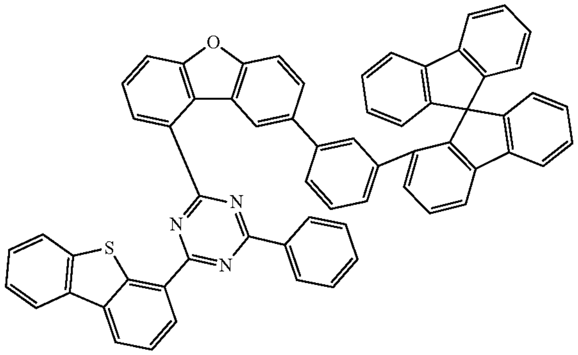

-continued
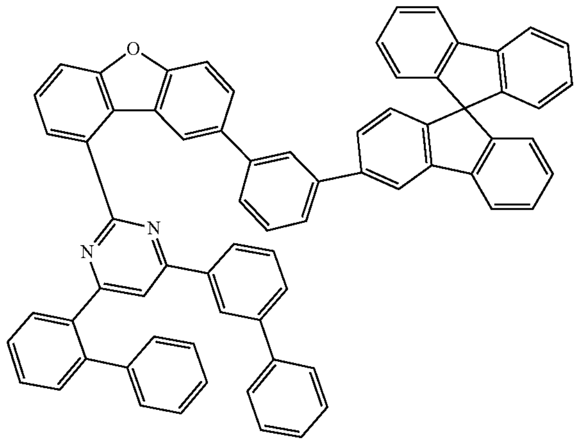
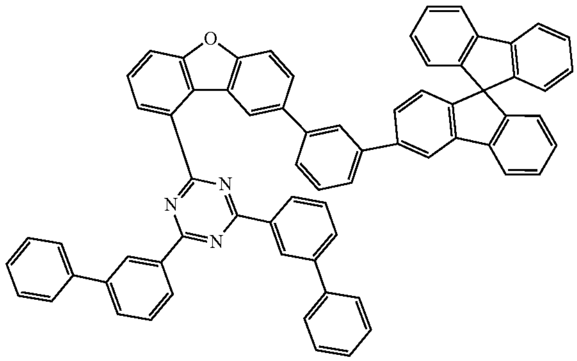
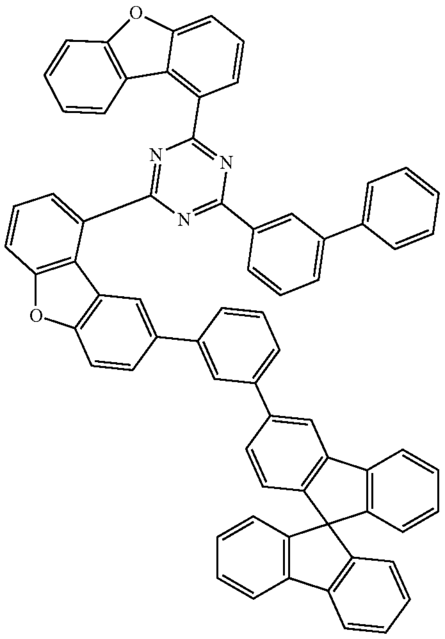
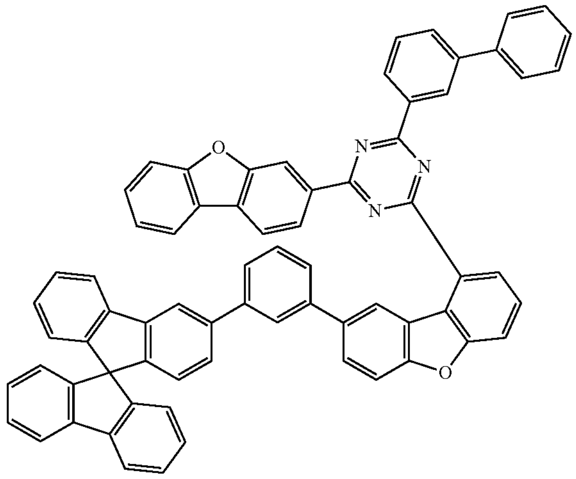
-continued
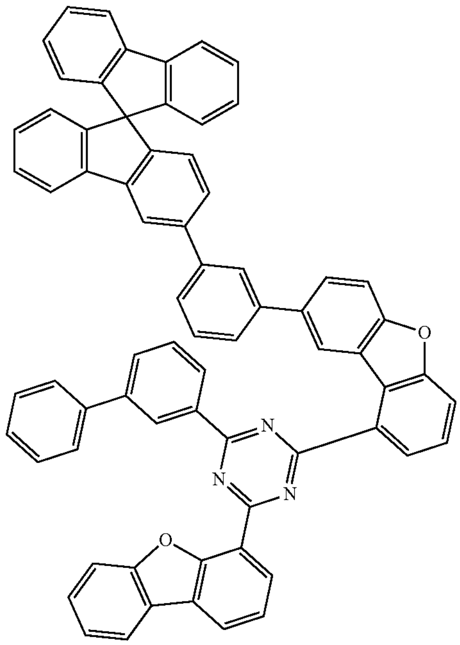

-continued
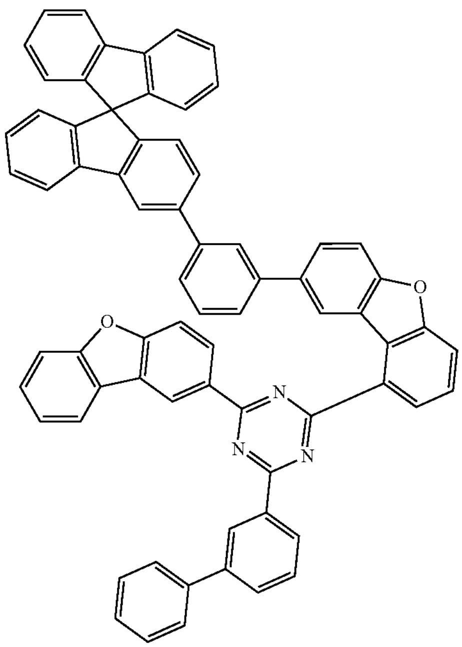
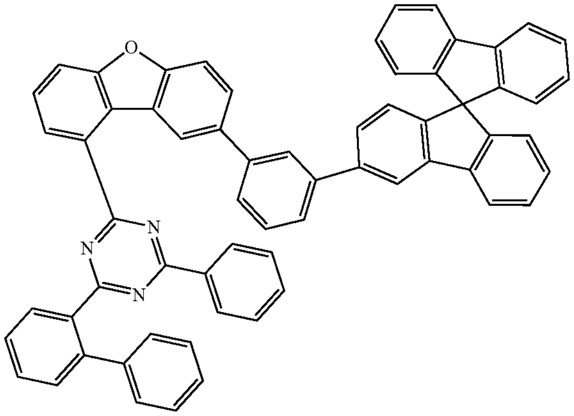
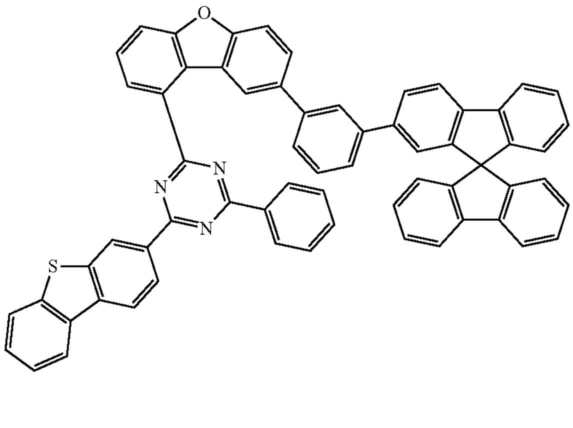
-continued
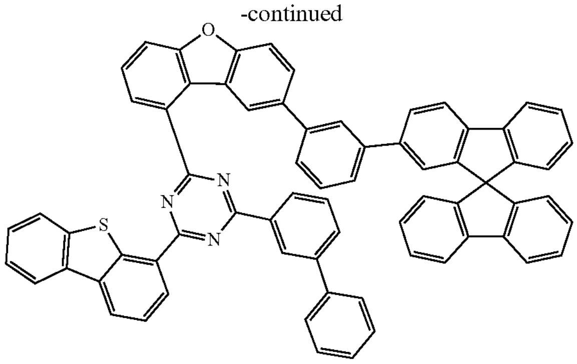
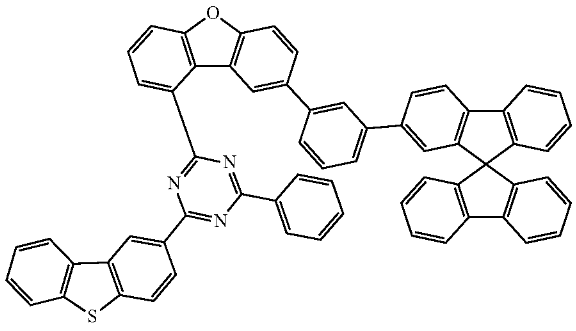
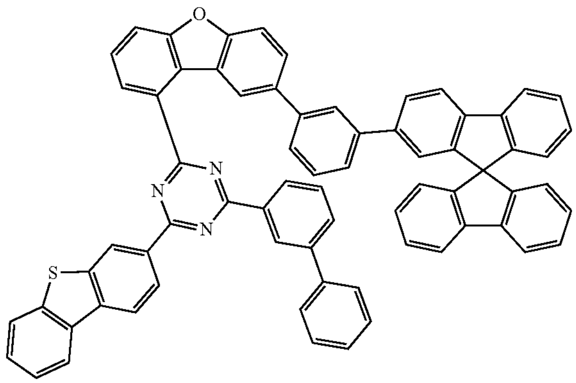
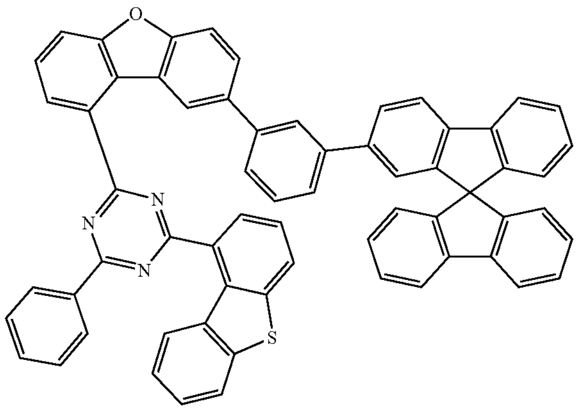

-continued
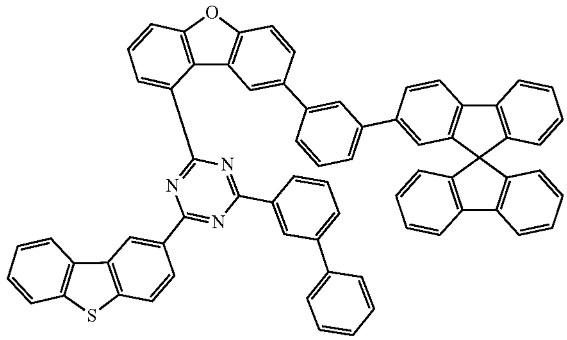
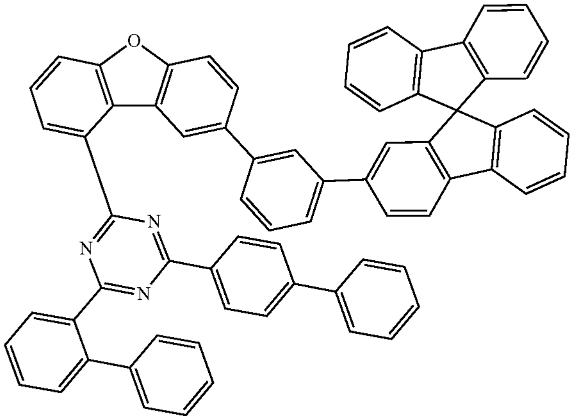
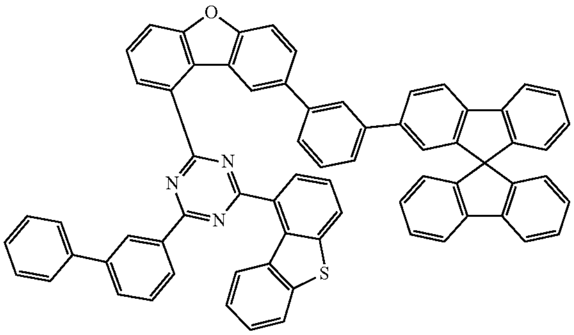
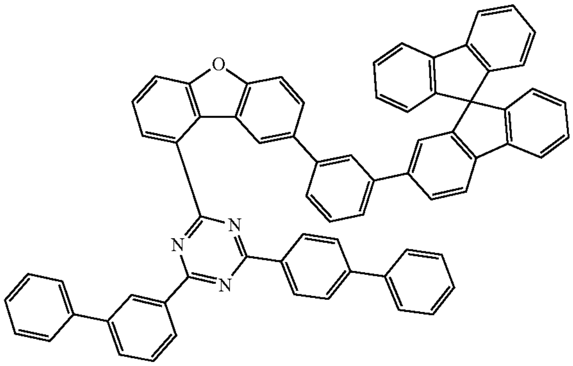
-continued
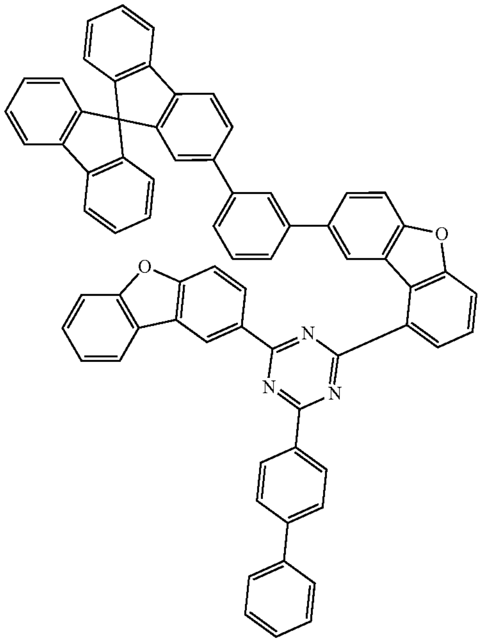
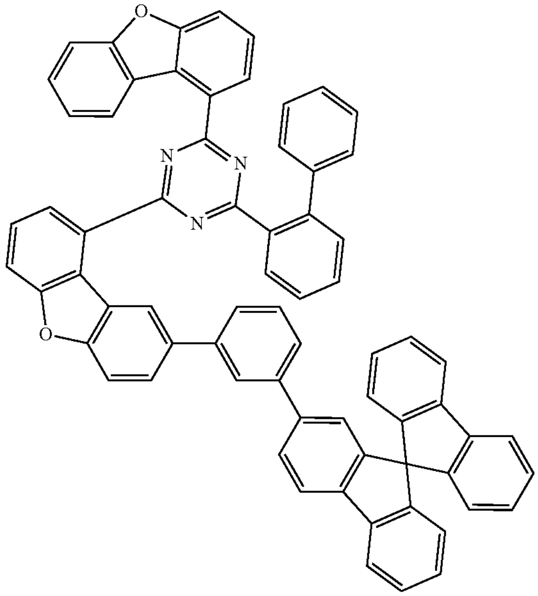

-continued
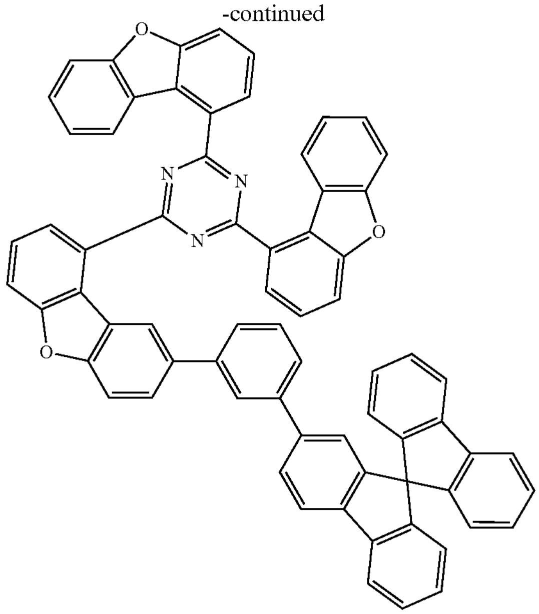
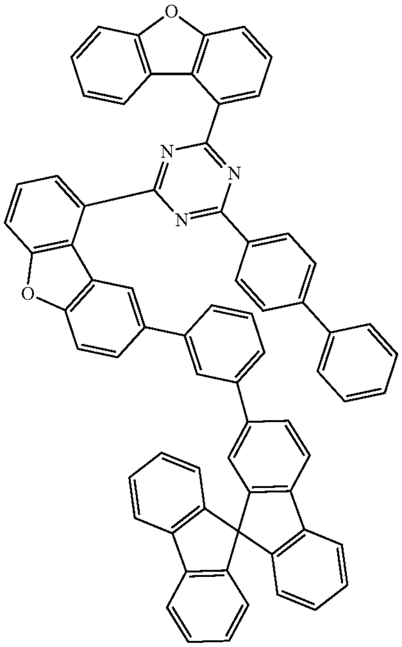
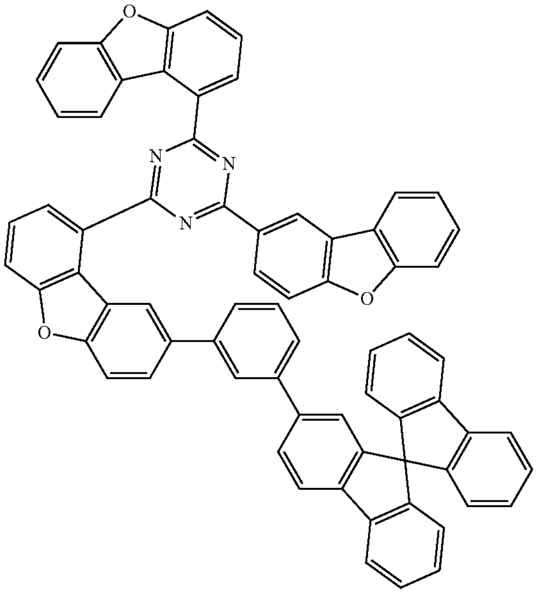

-continued
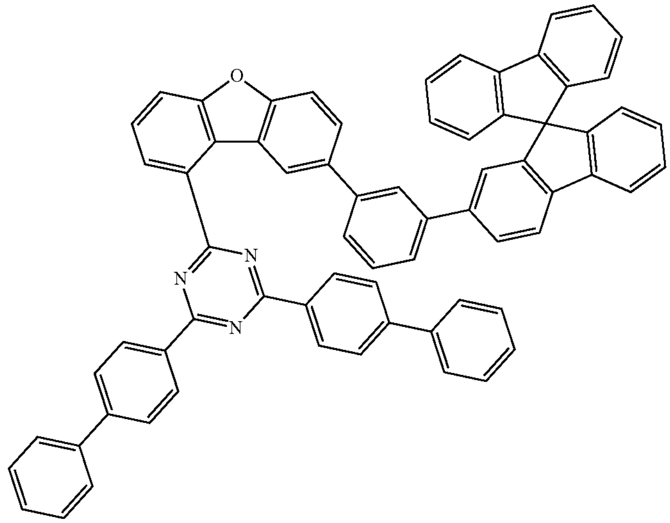
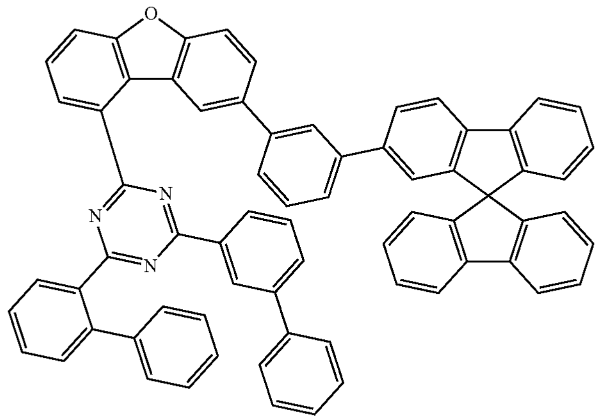
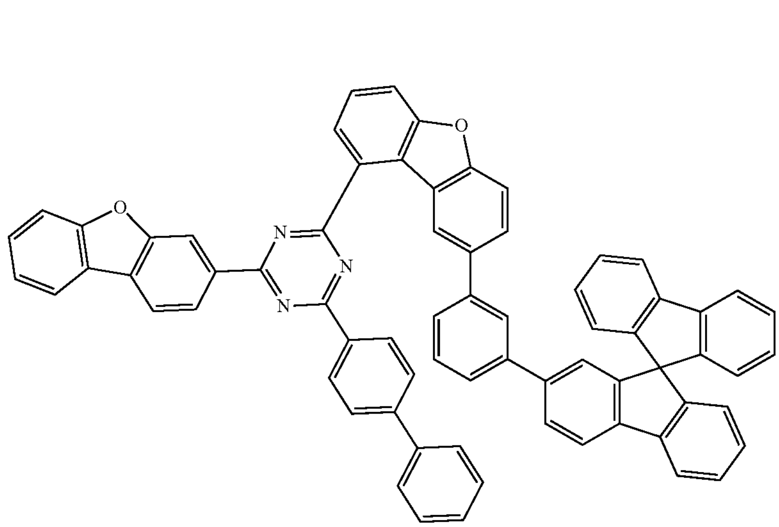

-continued
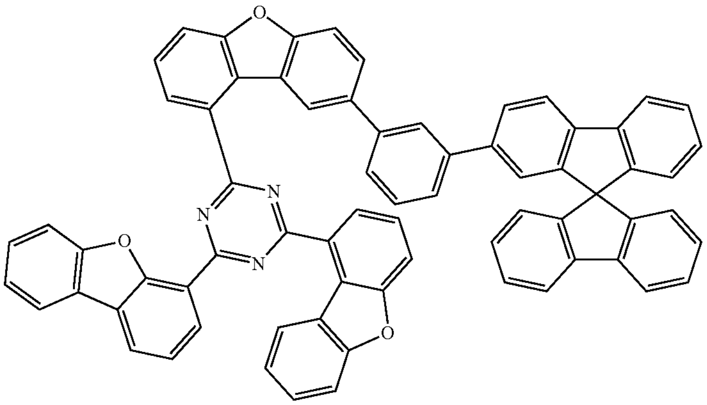
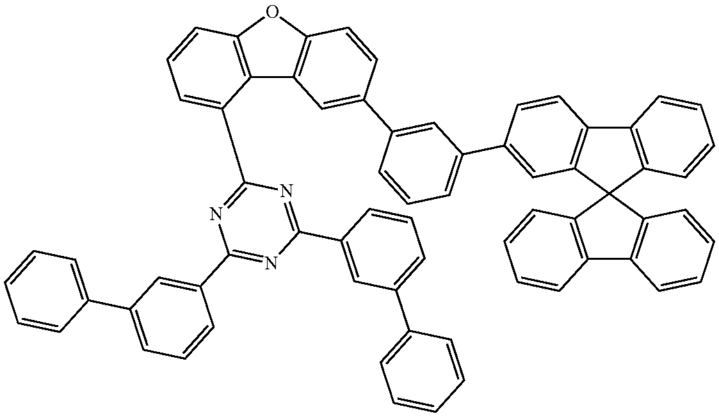
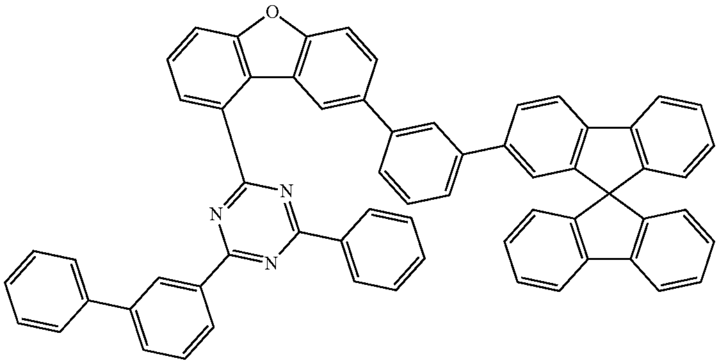
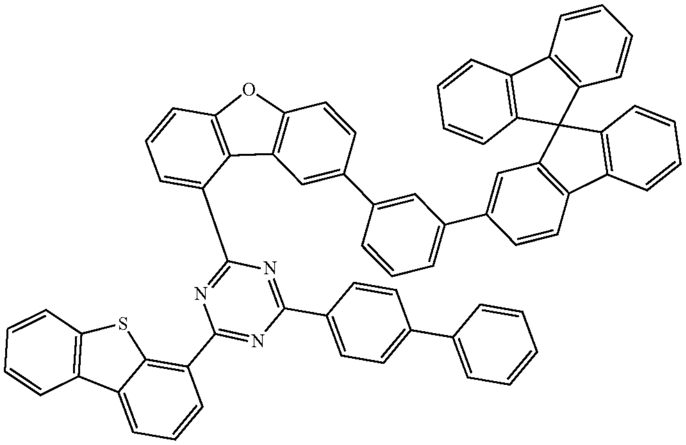

-continued
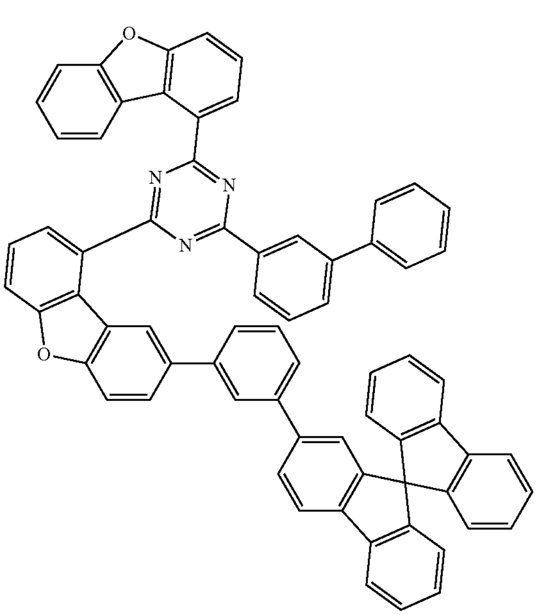
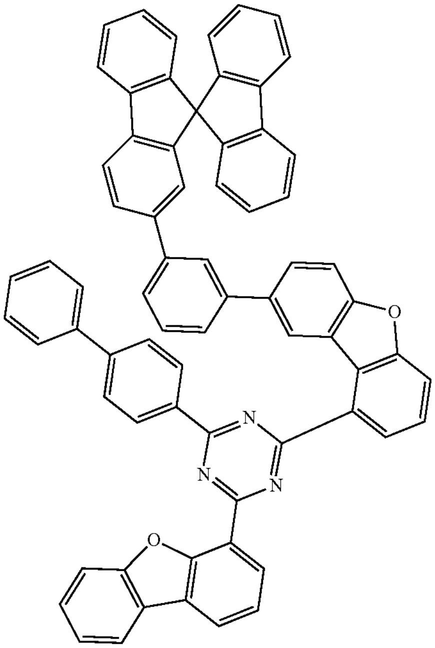
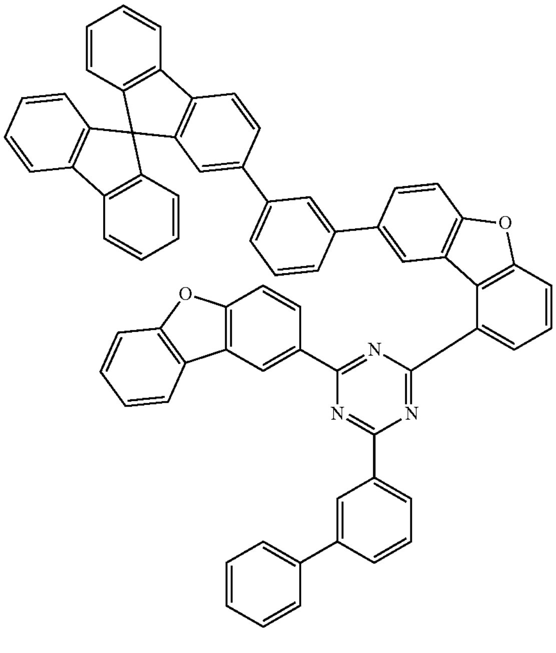

-continued
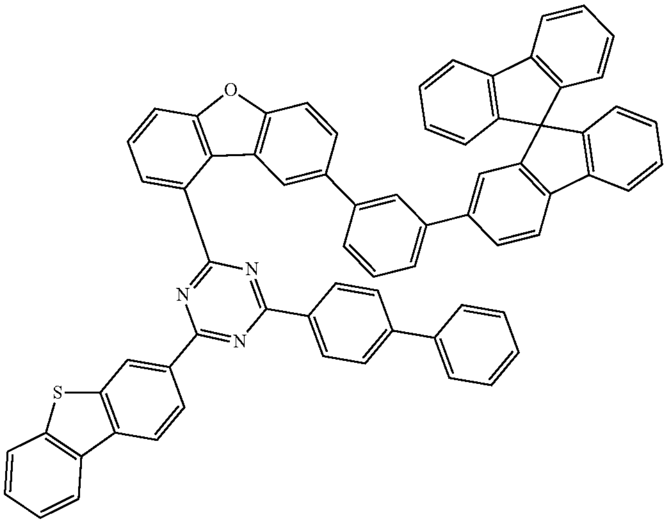
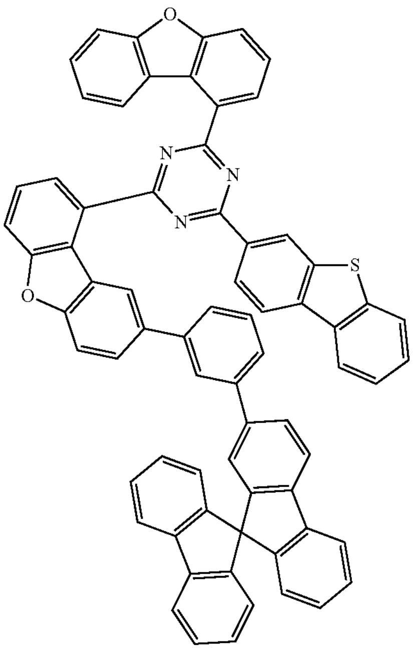
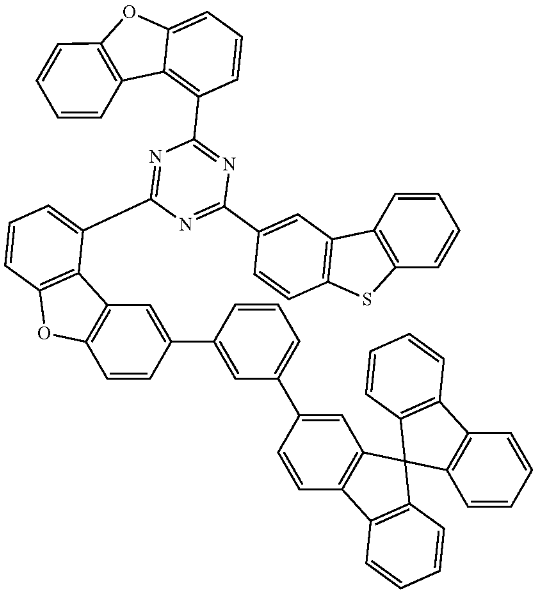
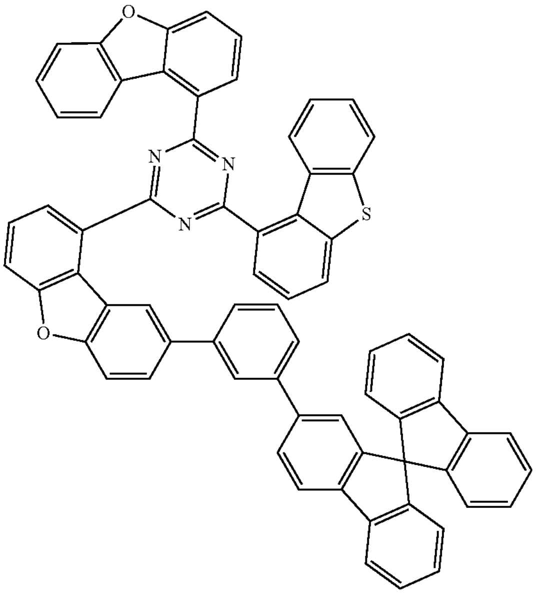

-continued
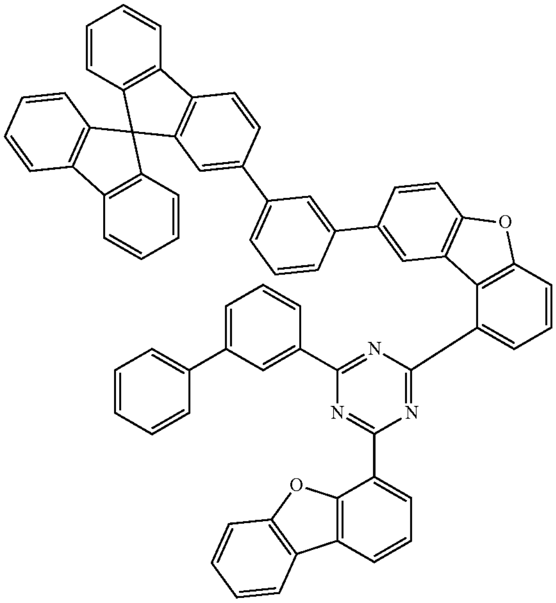
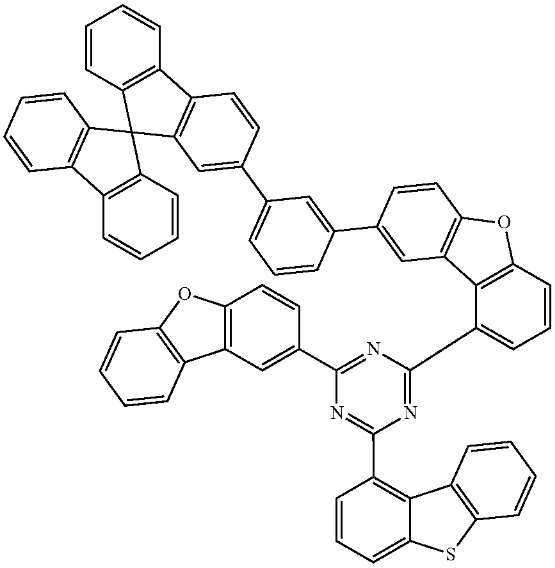
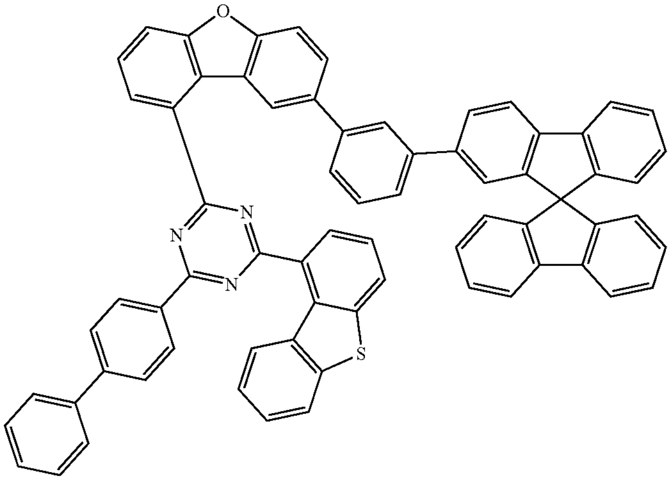
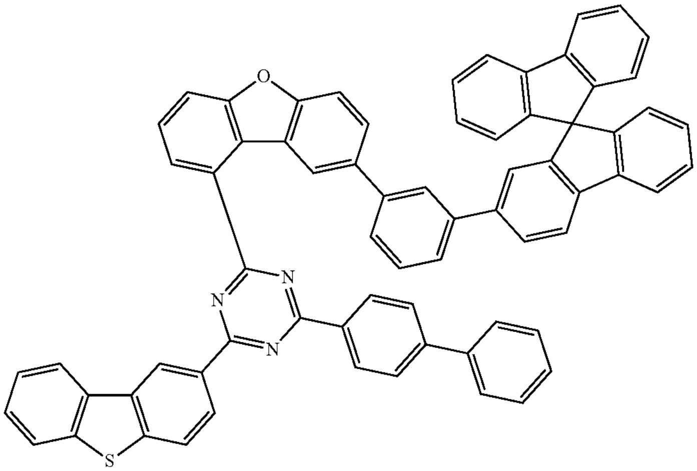

-continued
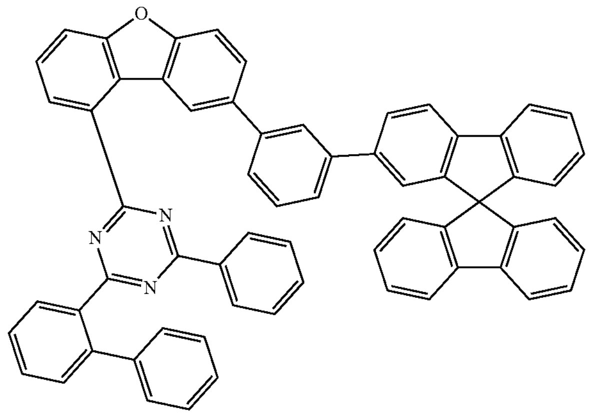
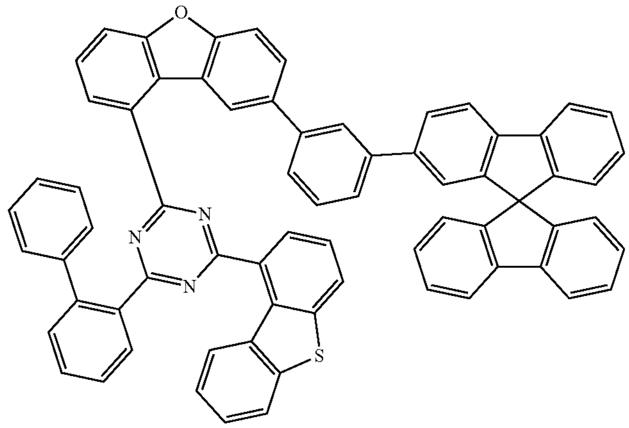
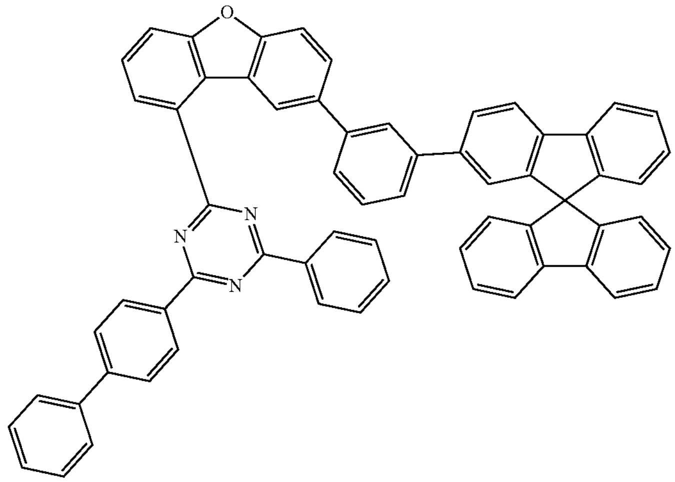

-continued
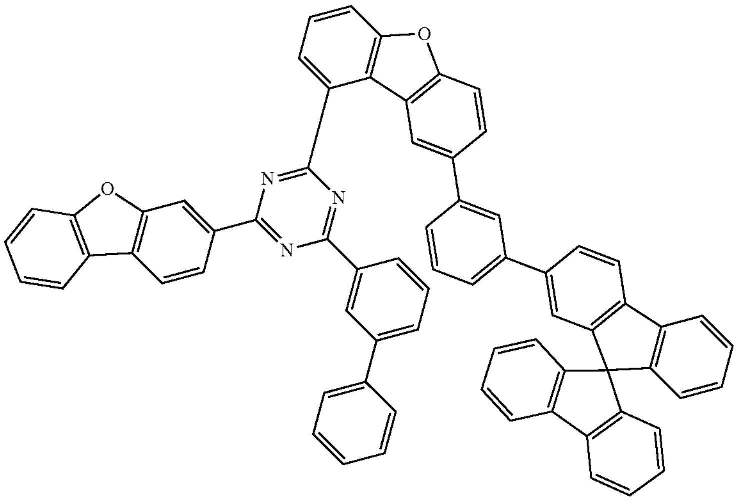
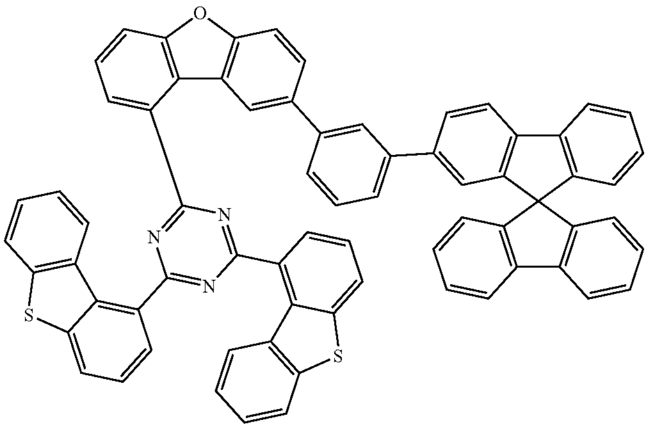
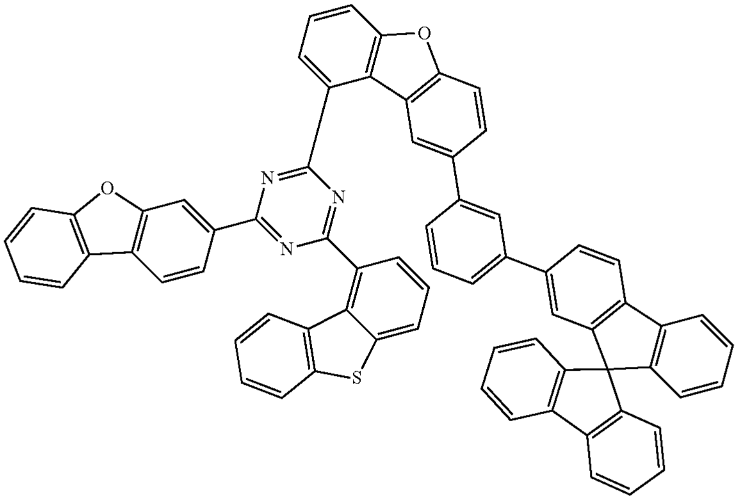

-continued
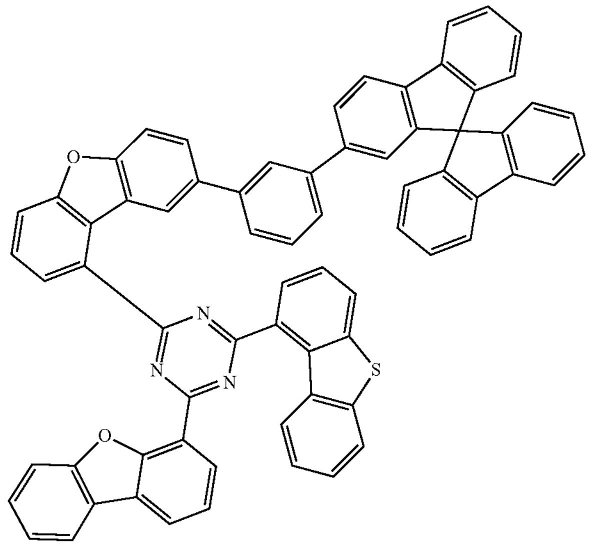
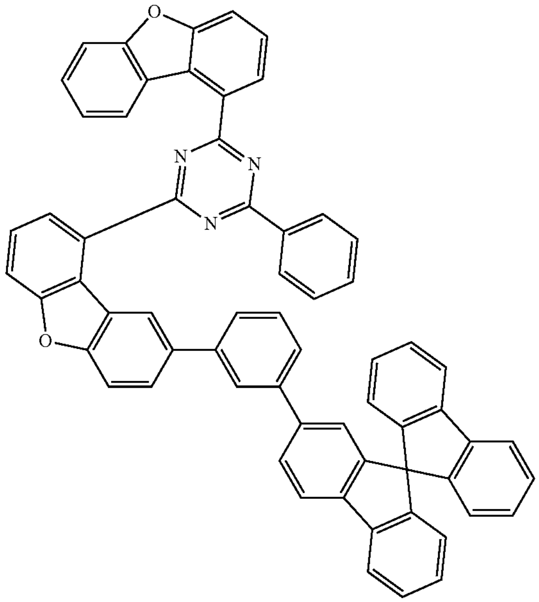
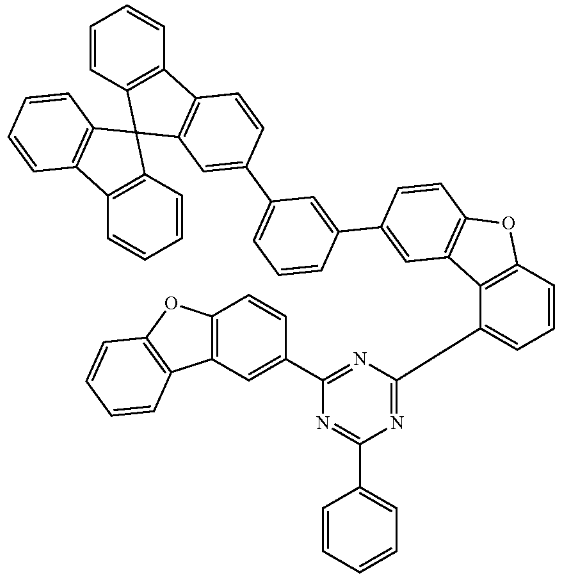
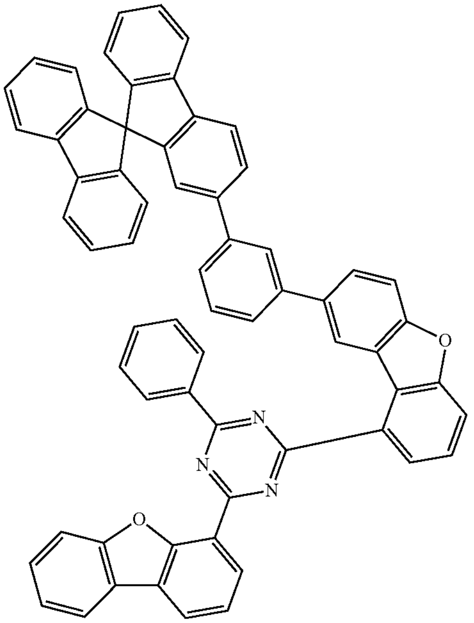
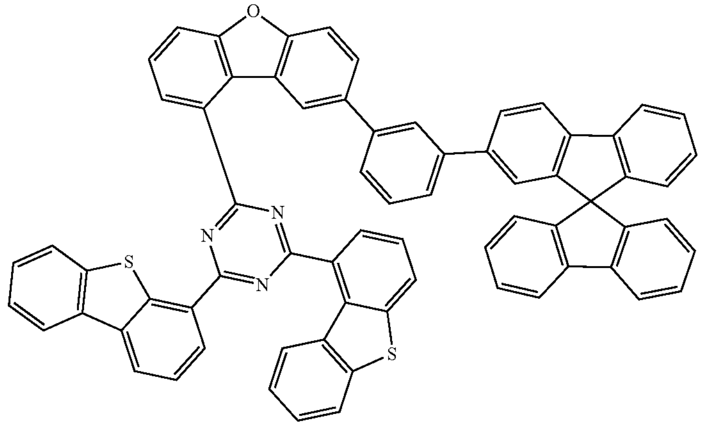

-continued
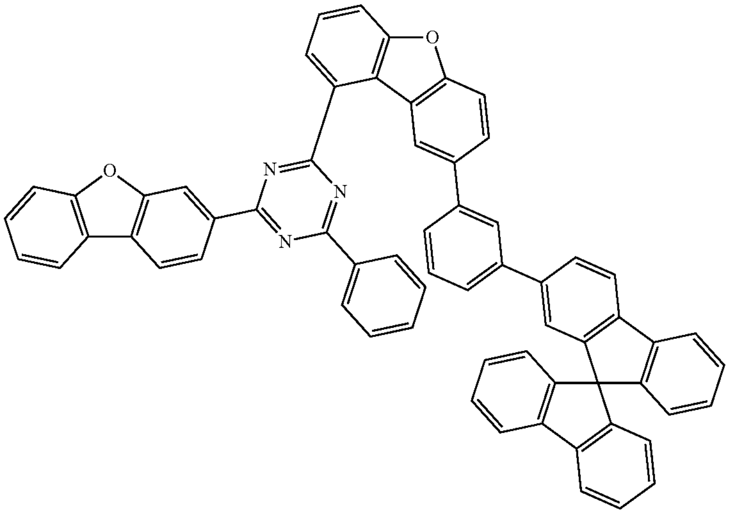
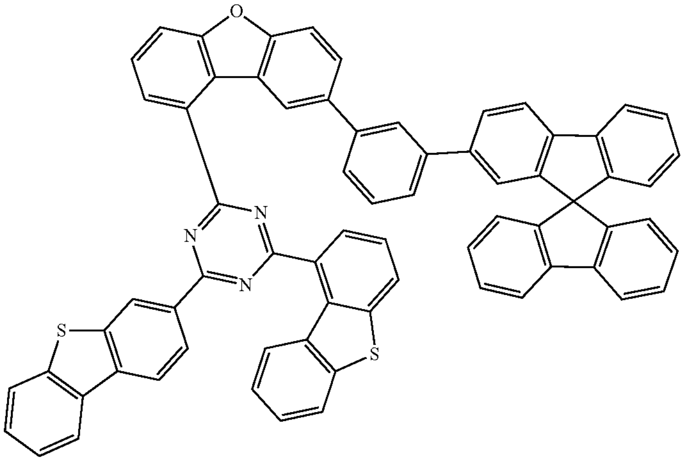
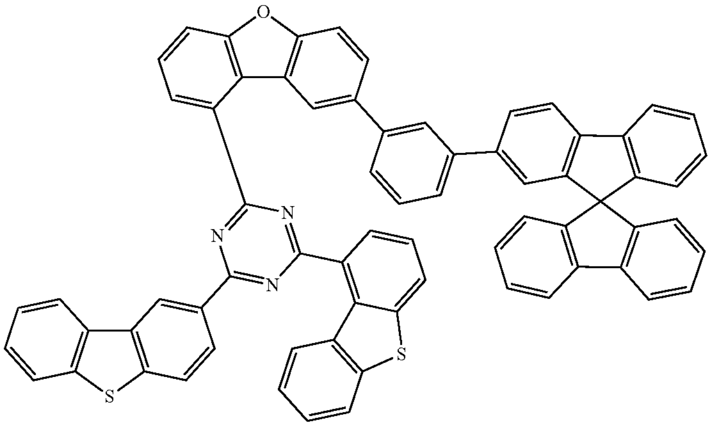

-continued
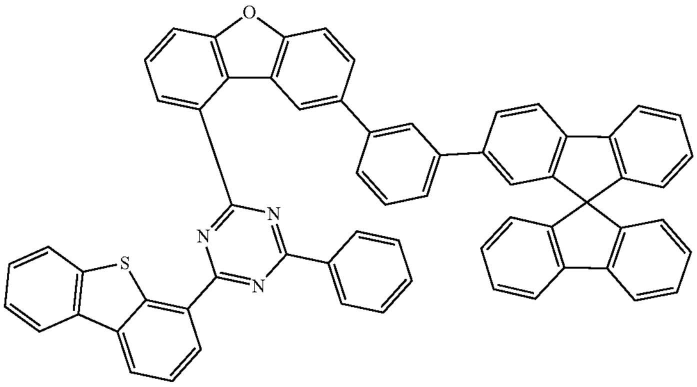
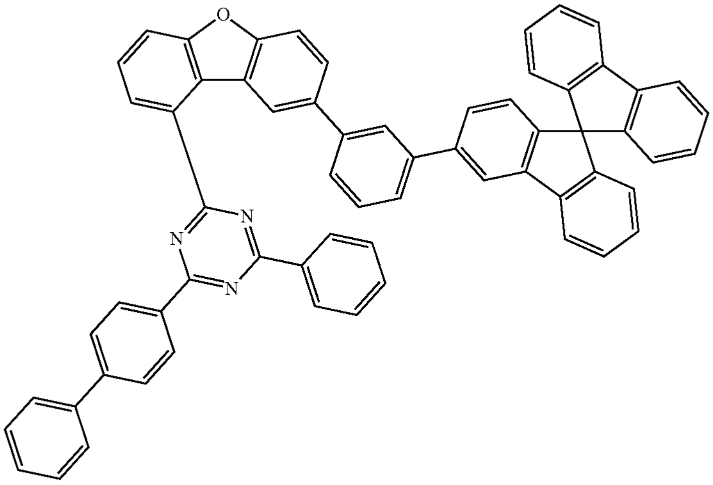
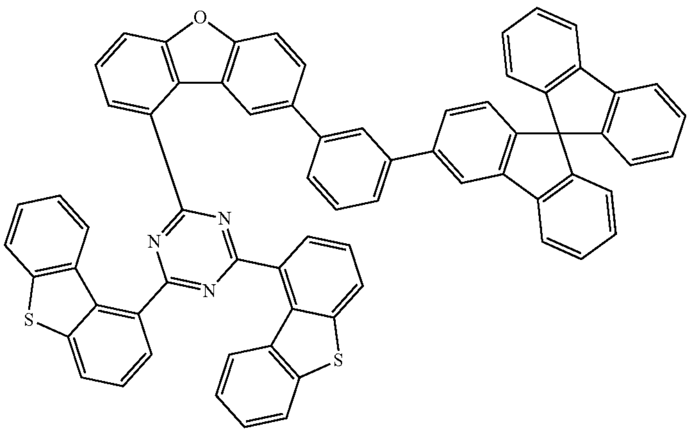

-continued
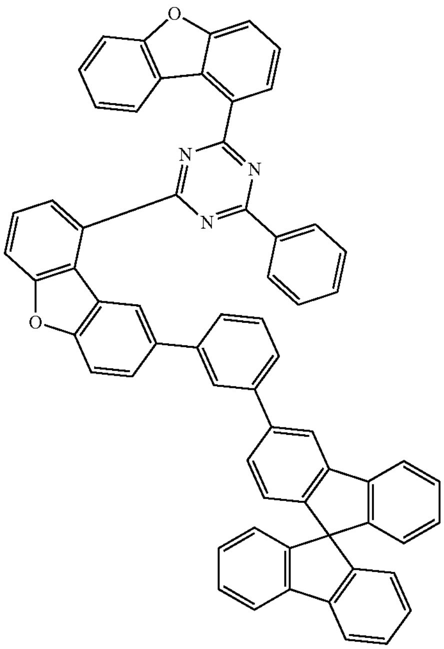
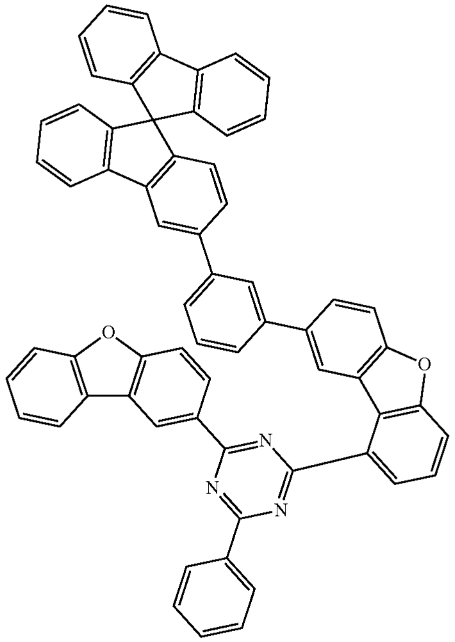
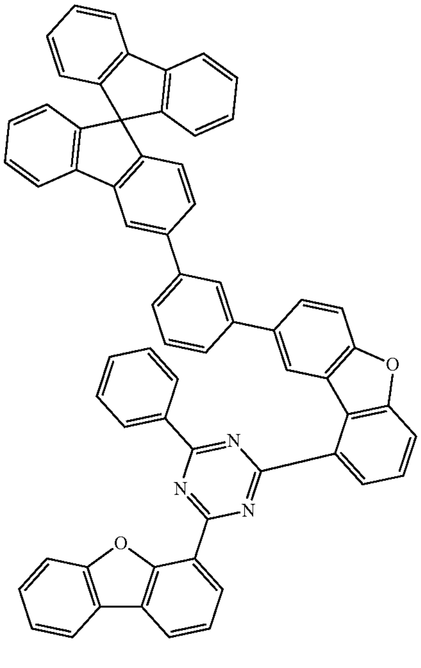
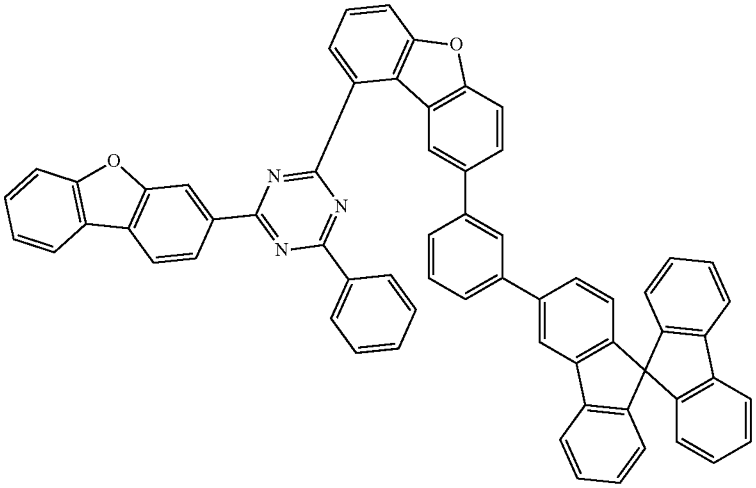

-continued
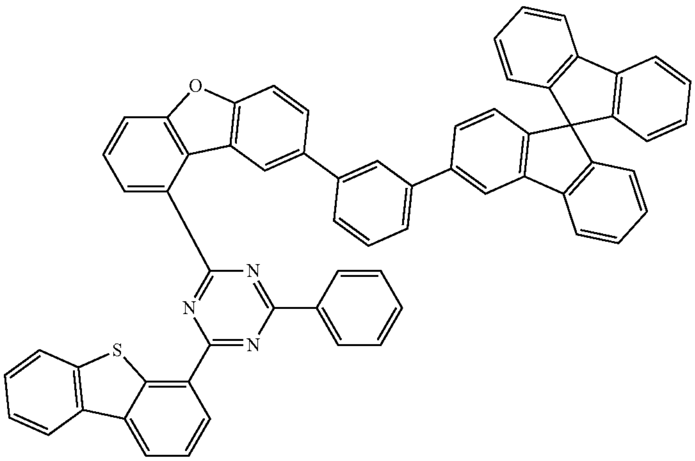
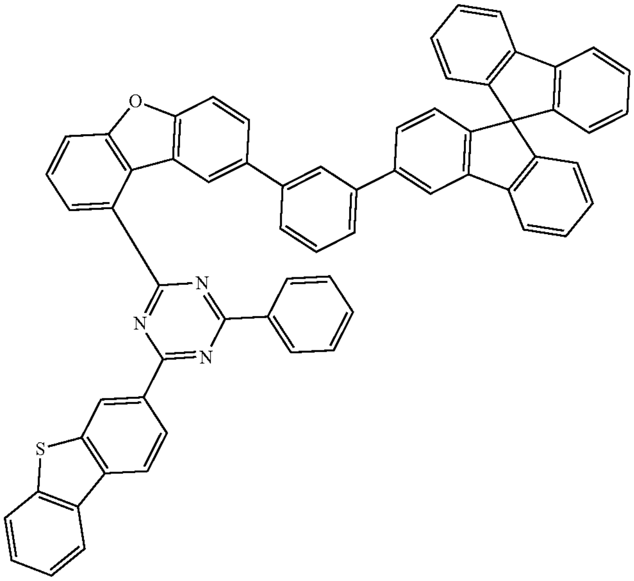
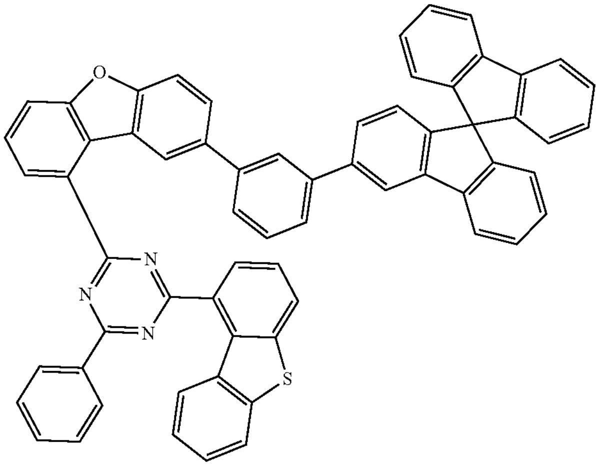

-continued
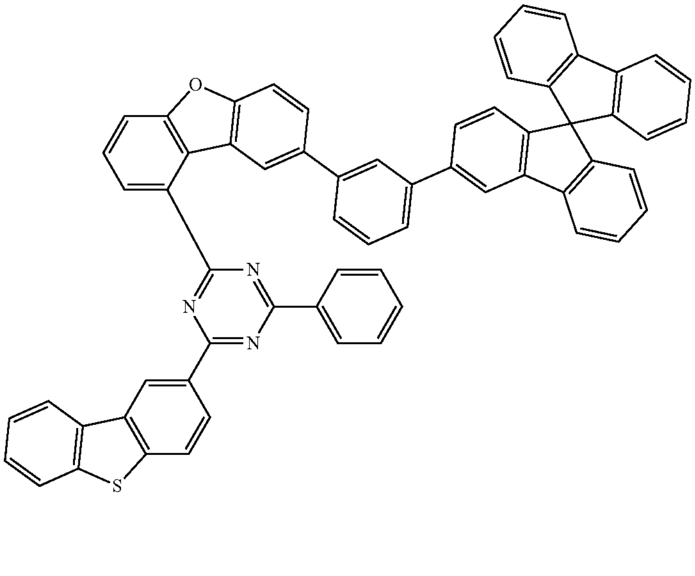
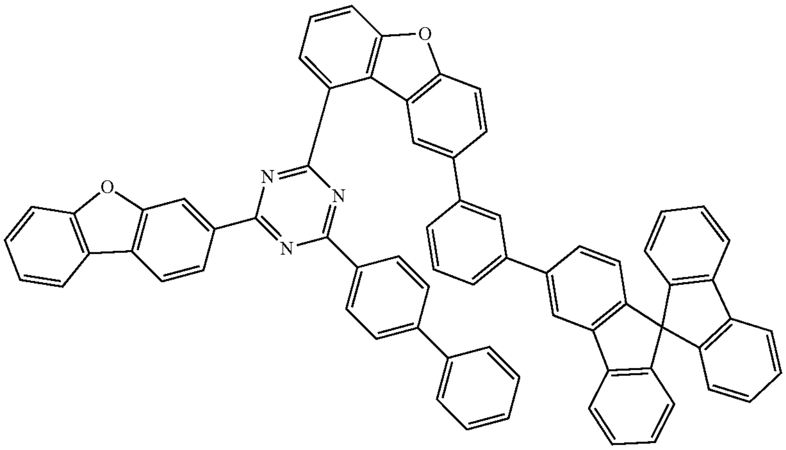
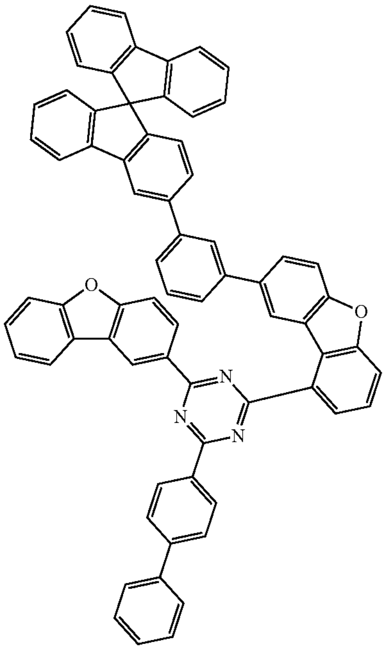
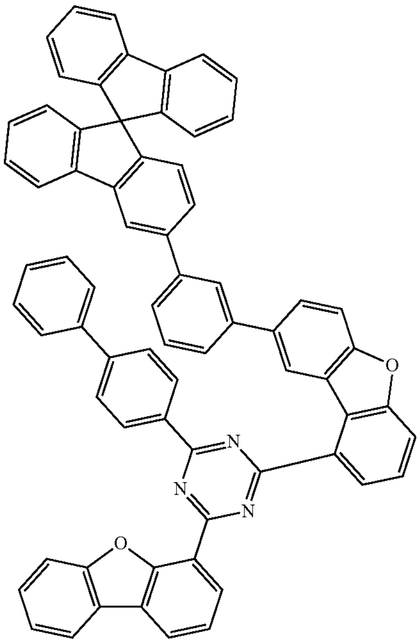

-continued
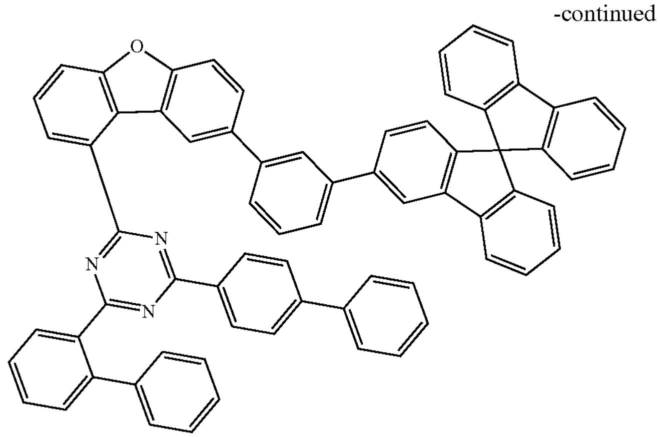
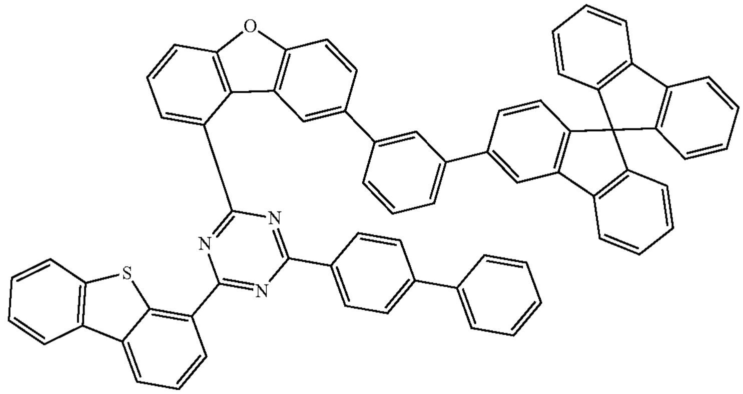 [SMILES: c1ccc(-c2ccc(-c3nc(-c4cccc5c4sc4ccccc45)nc(-c4cccc5oc6ccc(-c7cccc(-c8ccc9c(c8)-c8ccccc8C98c9ccccc9-c9ccccc98)c7)cc6c45)n3)cc2)cc1]
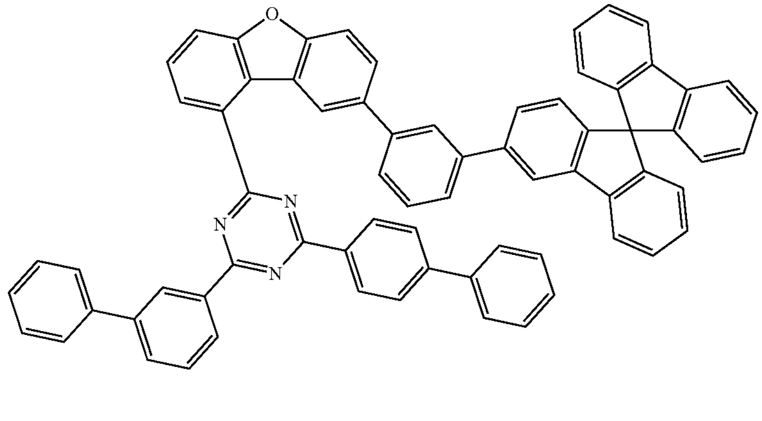

-continued
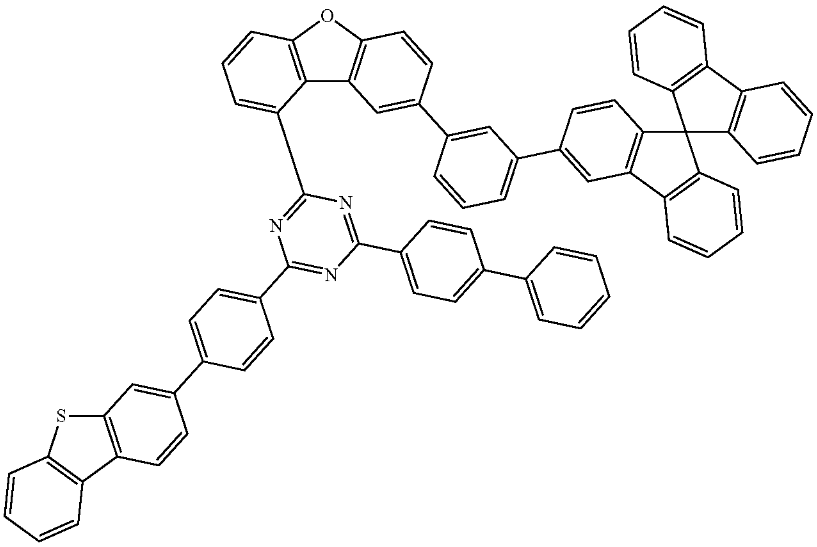
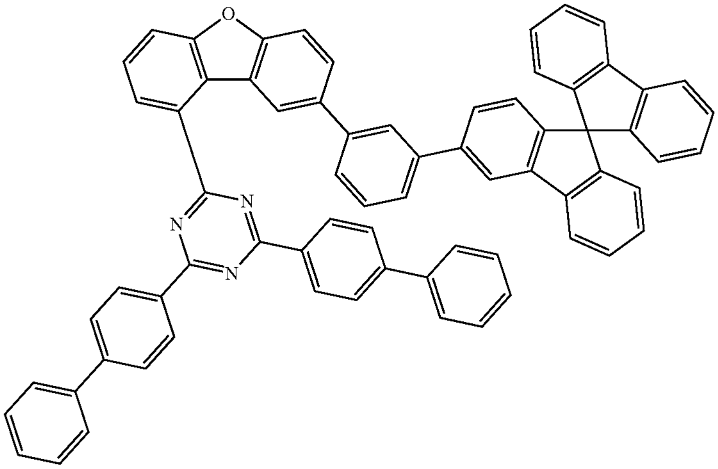
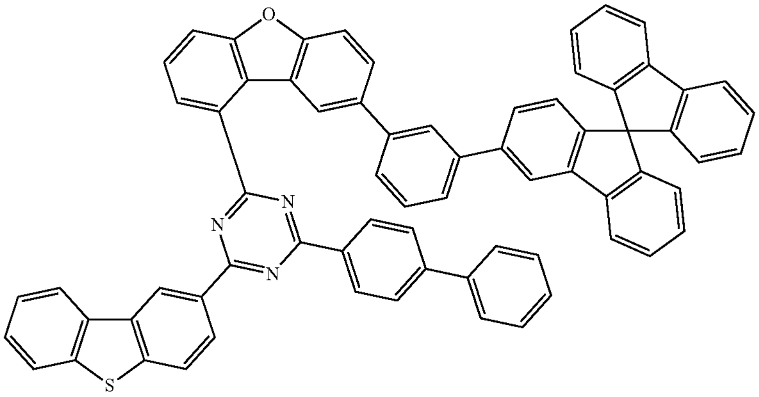

-continued
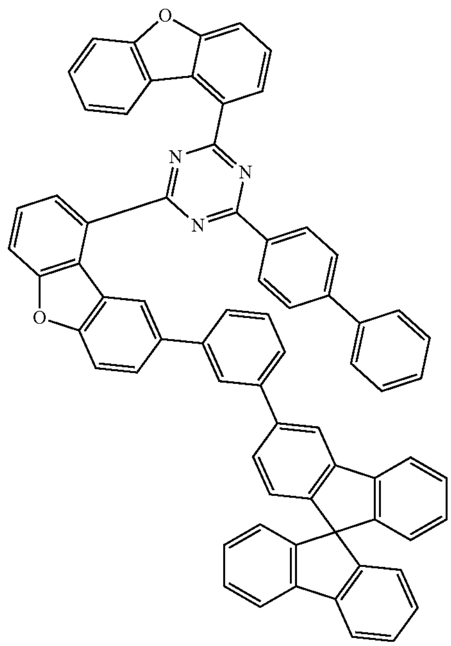
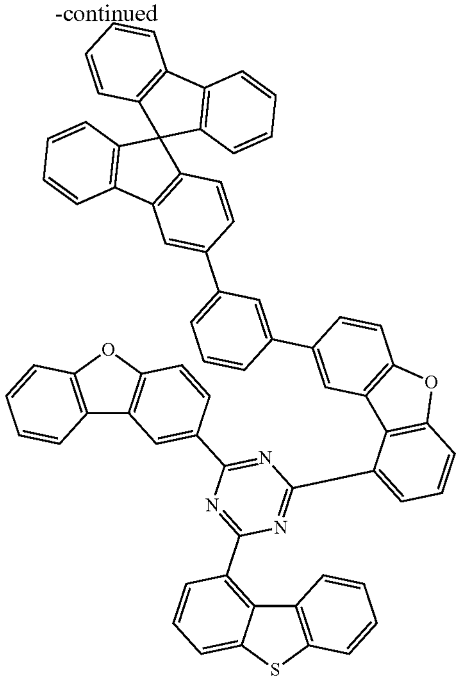
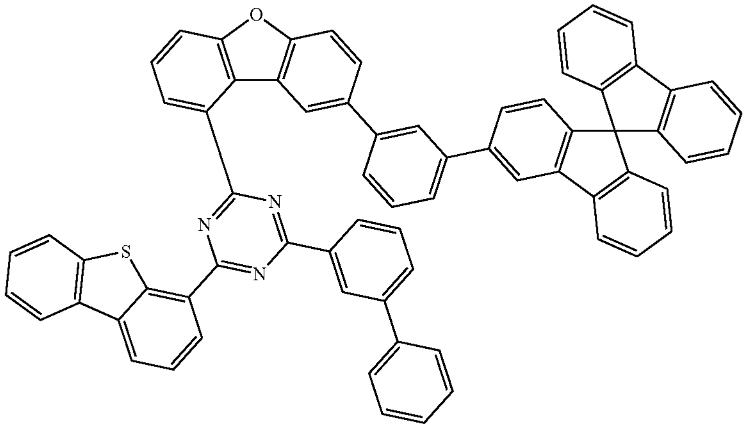
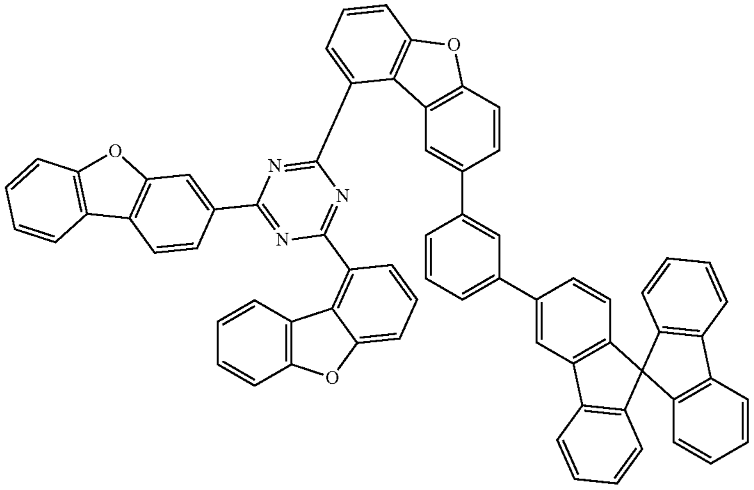

-continued
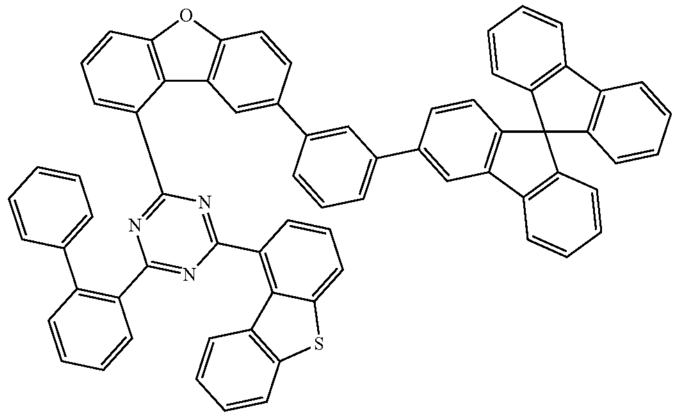
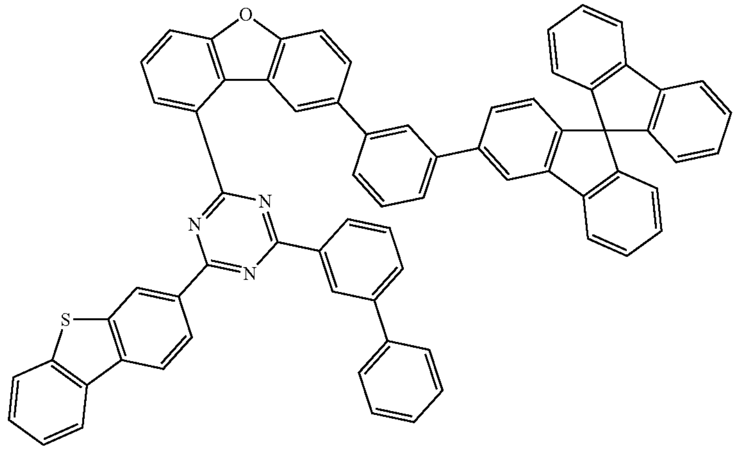
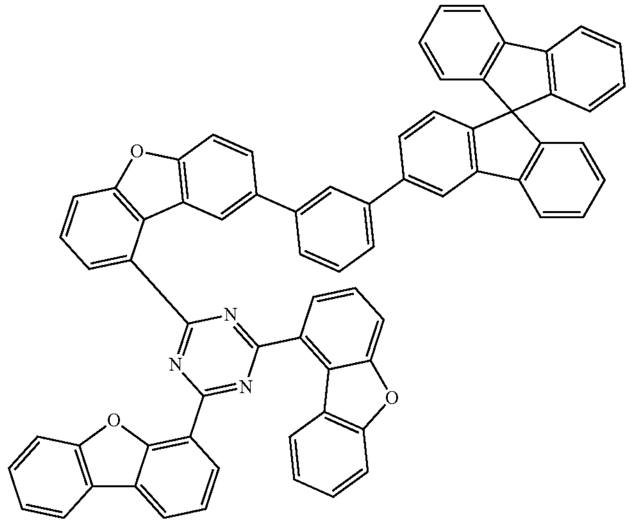

-continued
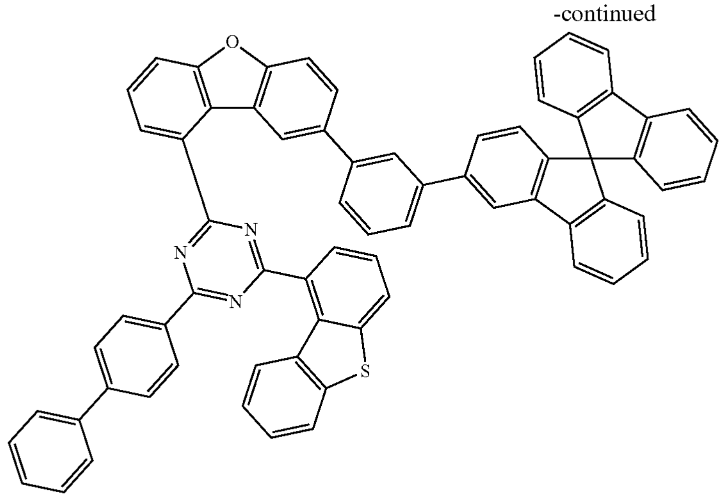
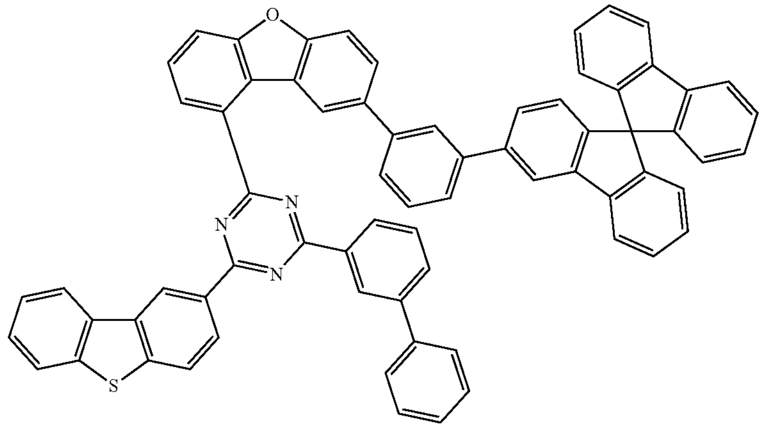
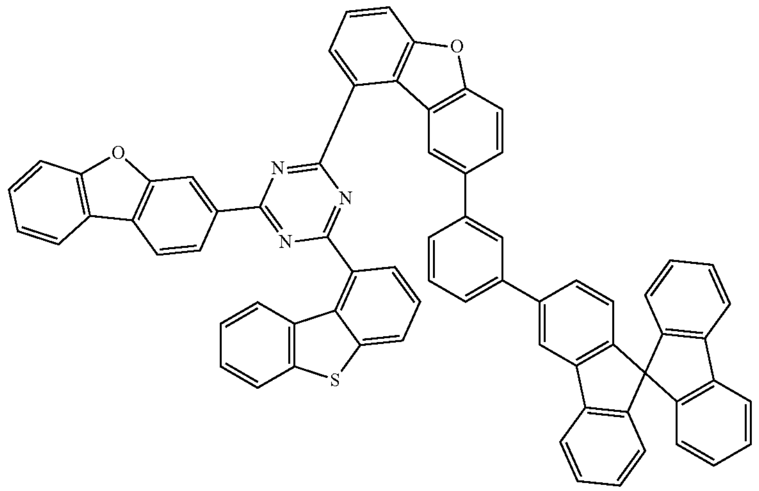

-continued
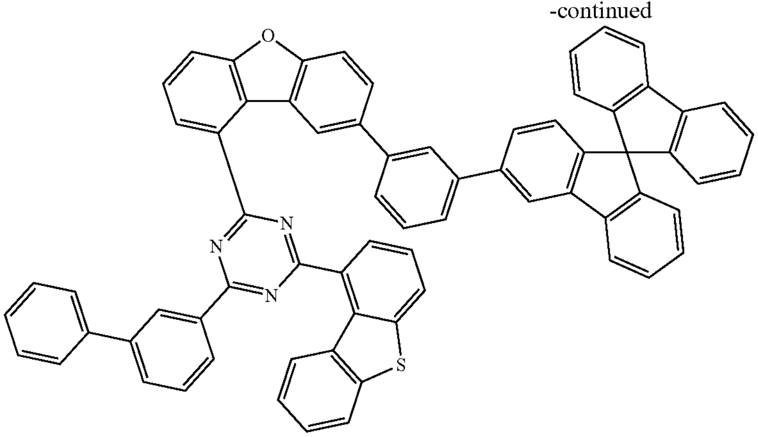
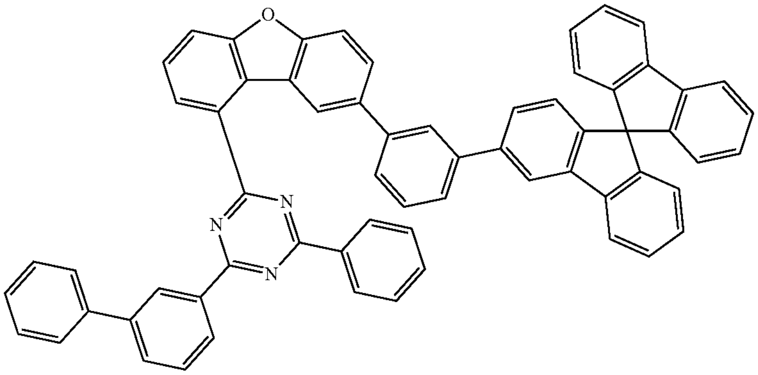
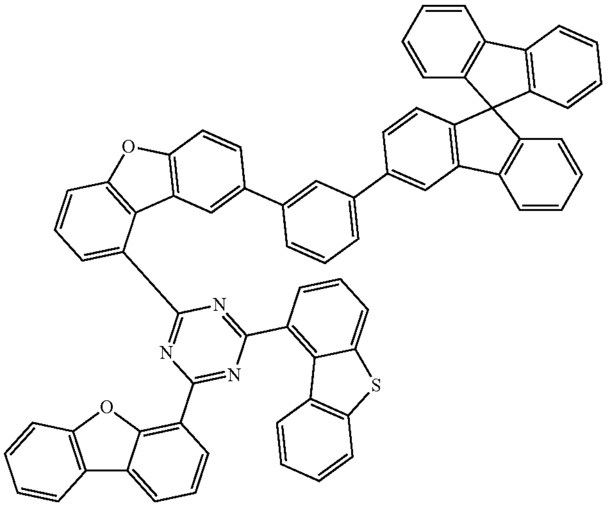
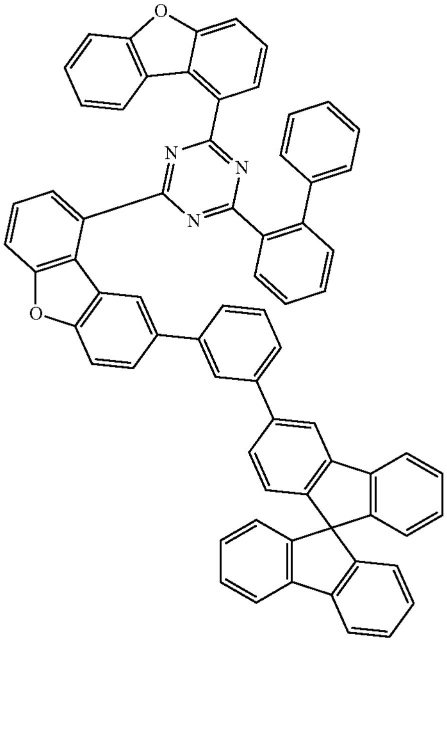

-continued
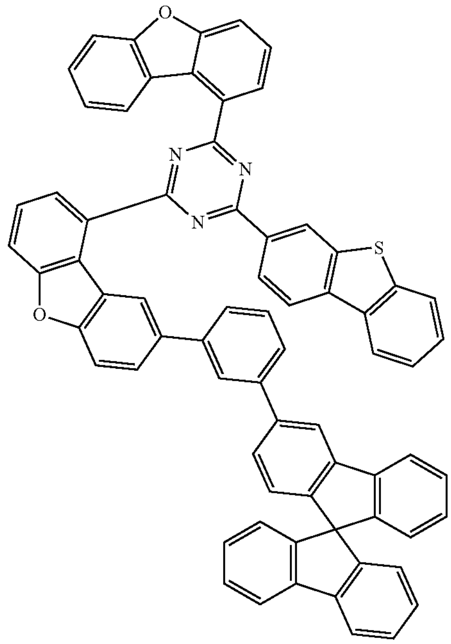
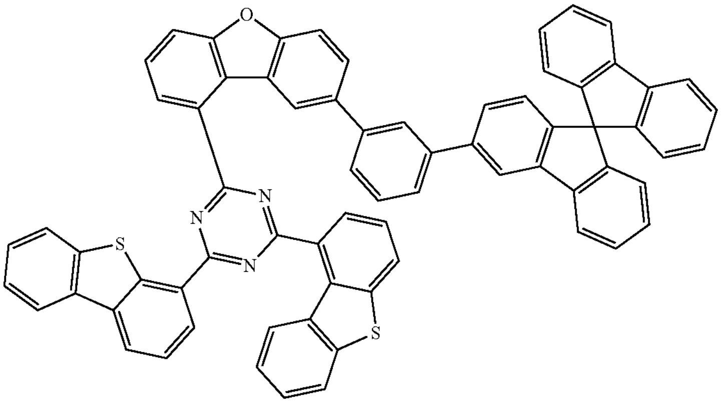
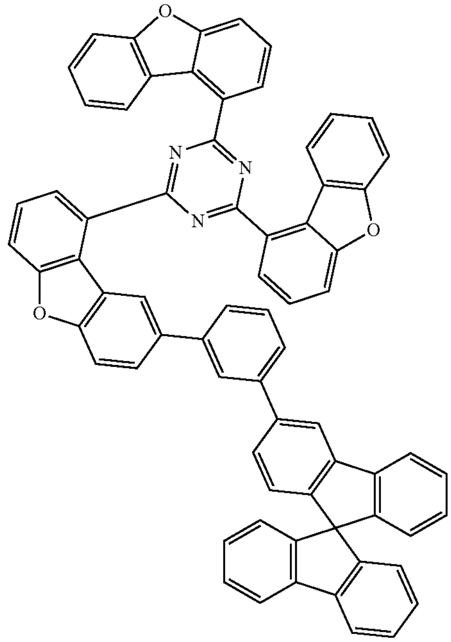
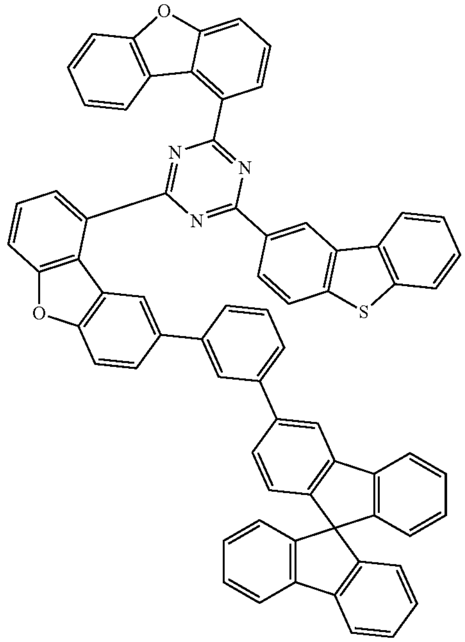

2051
2052
-continued
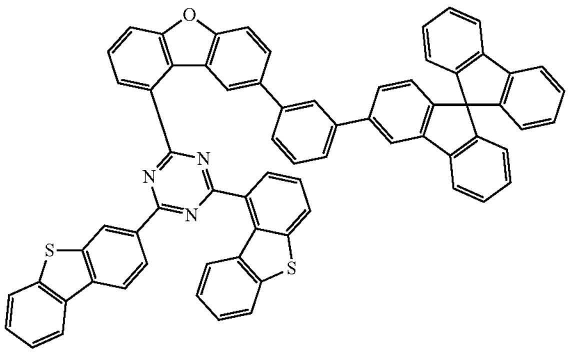
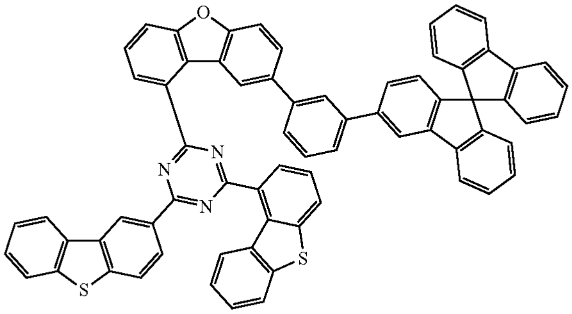
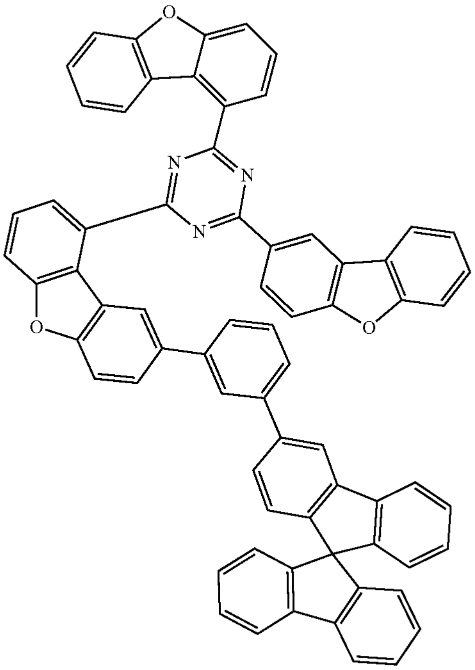
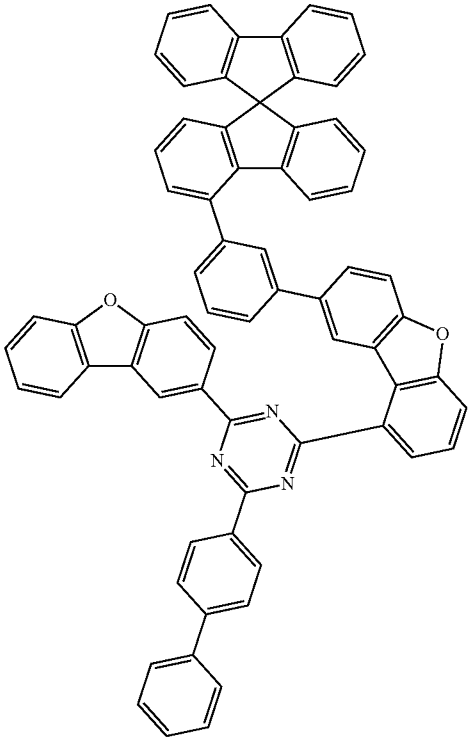
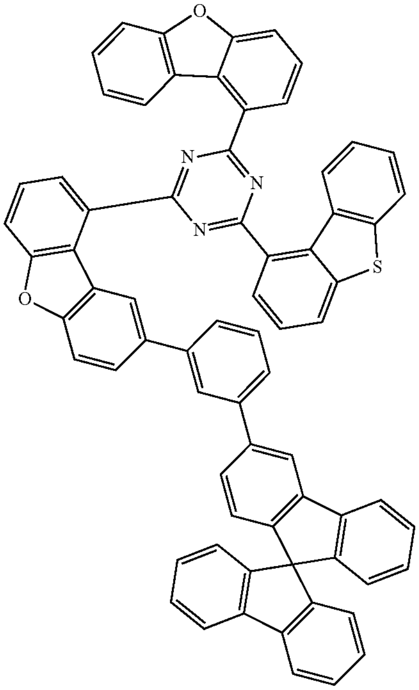
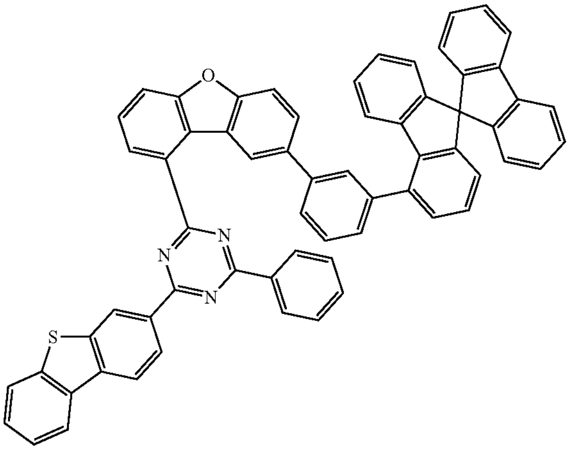

-continued
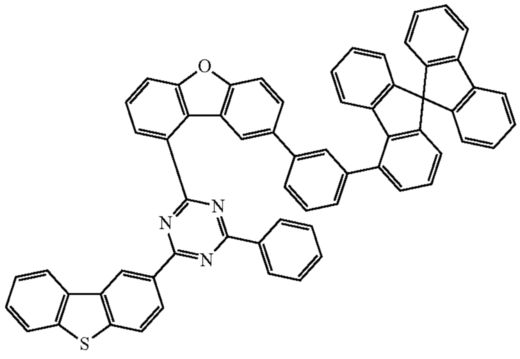
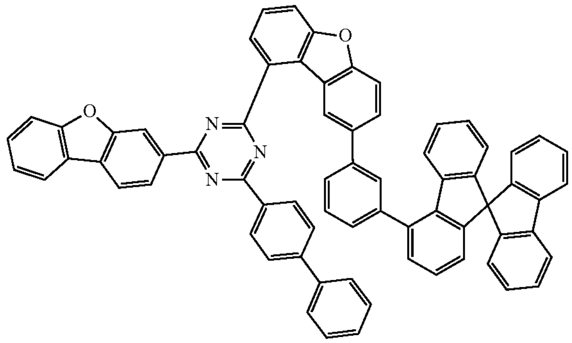
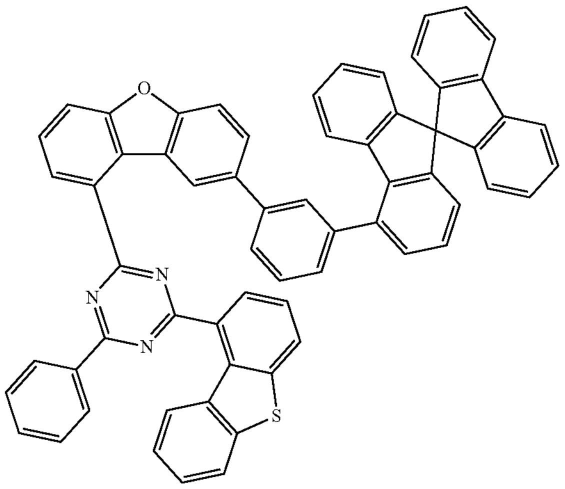
-continued
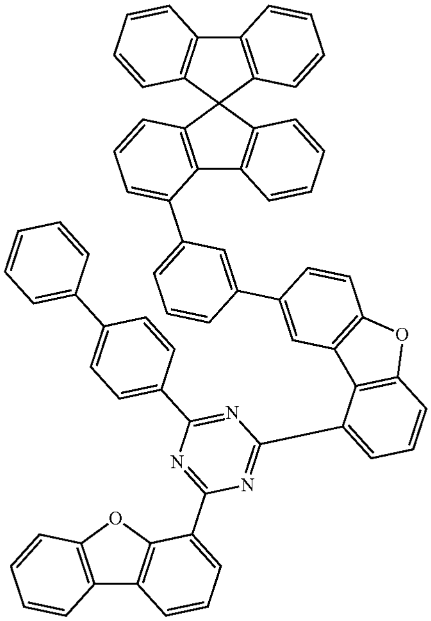
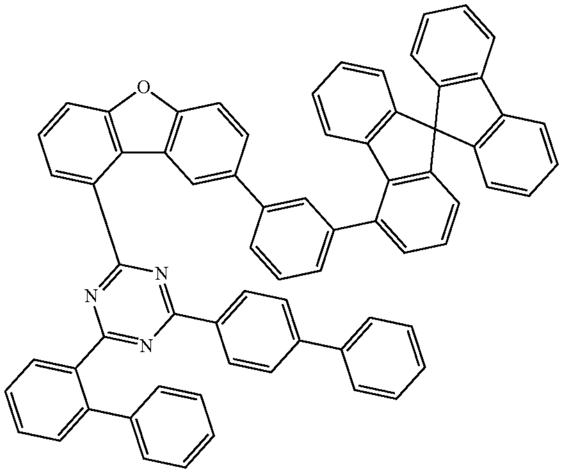
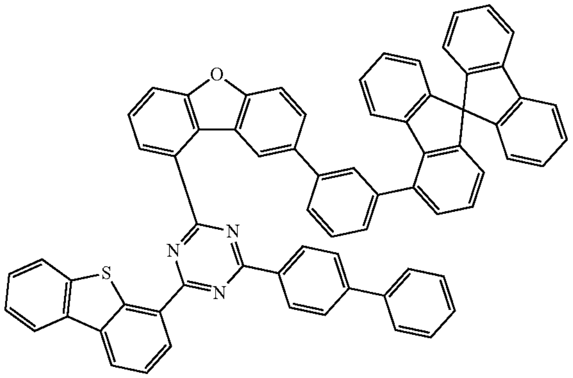

-continued
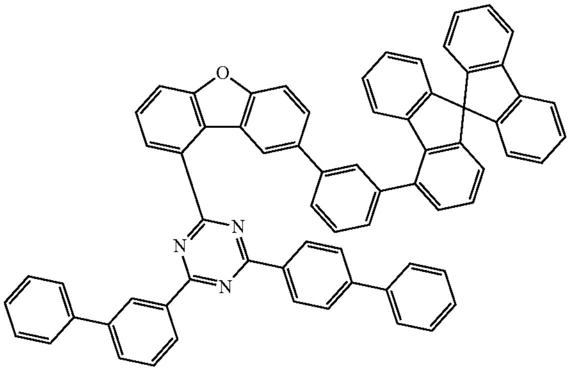
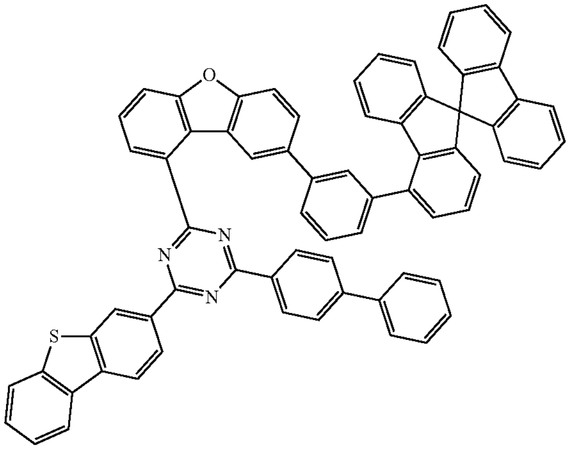
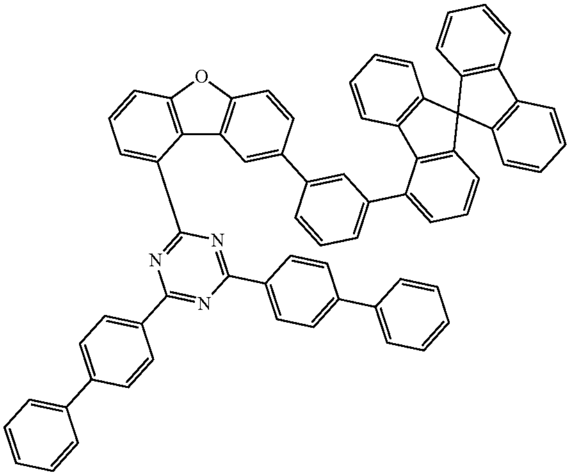
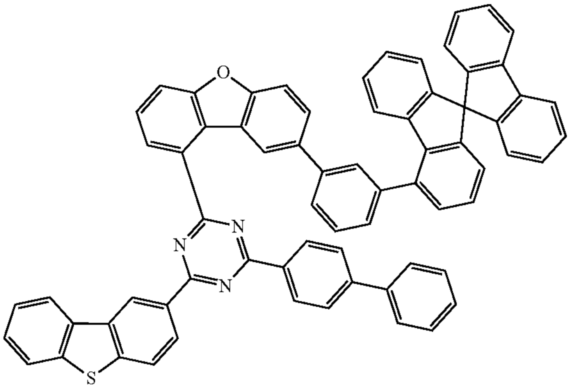
-continued
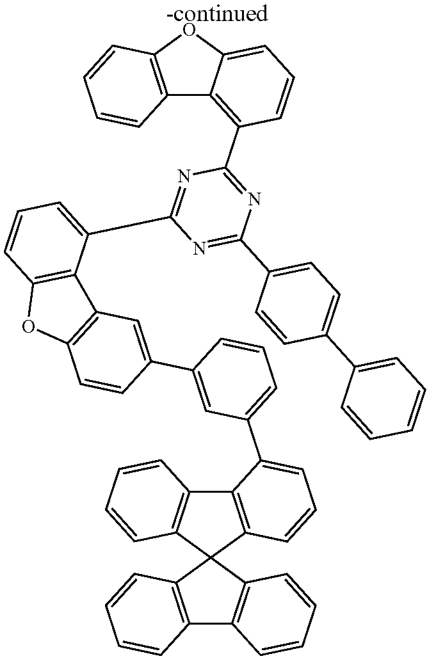
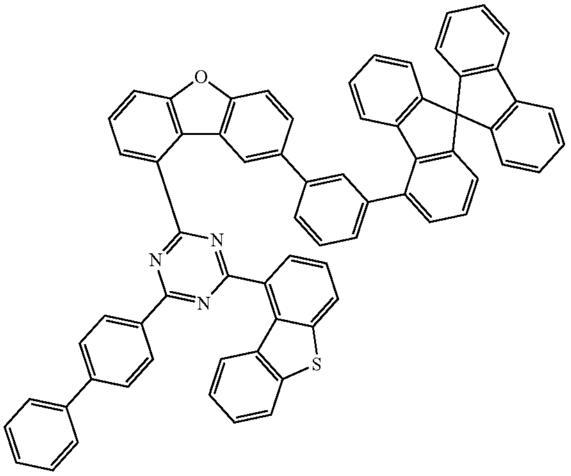
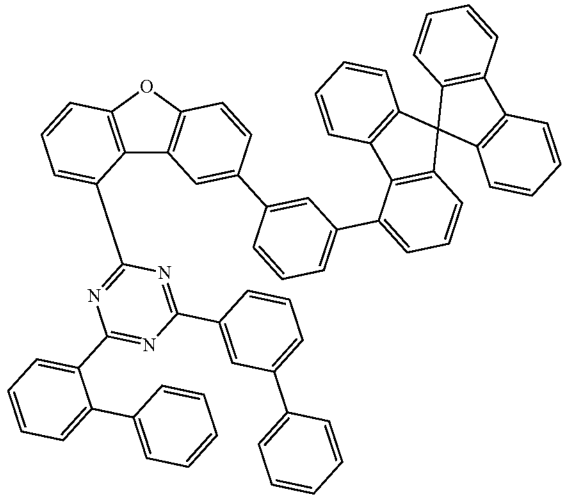

-continued
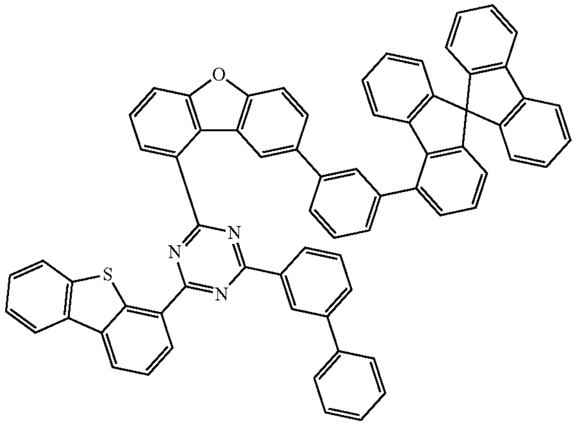
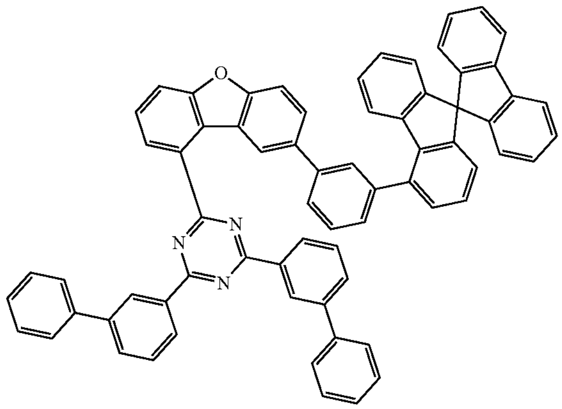
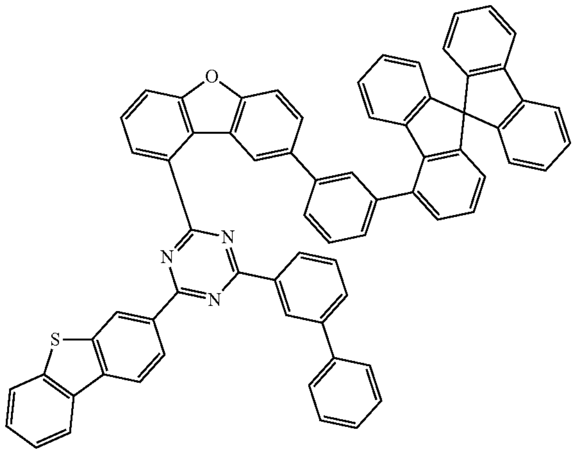
-continued
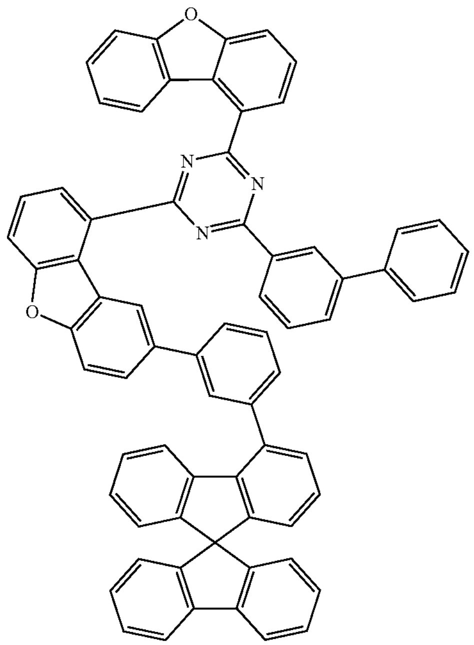
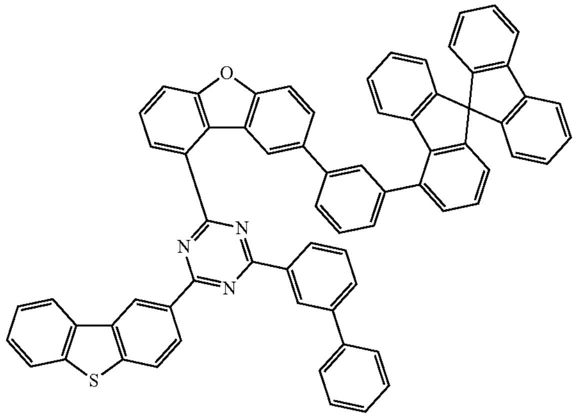
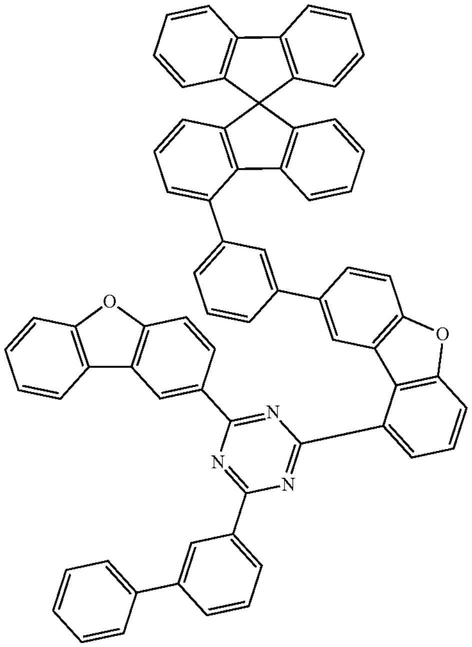

-continued
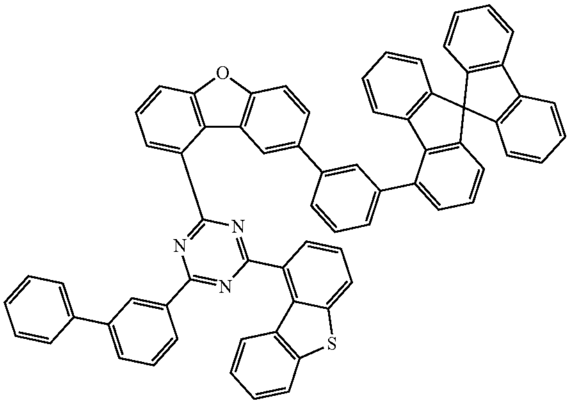
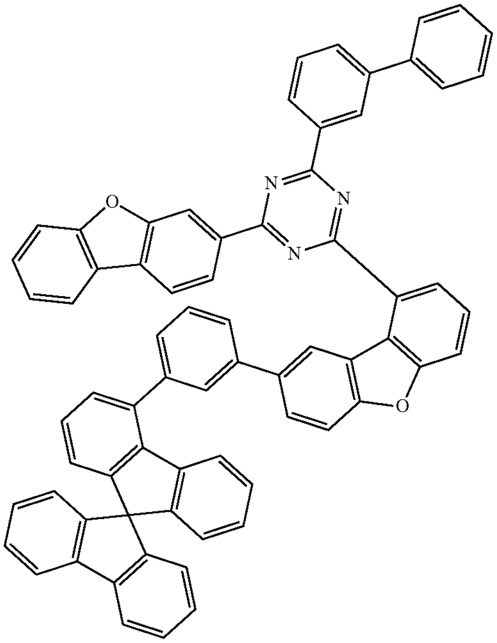
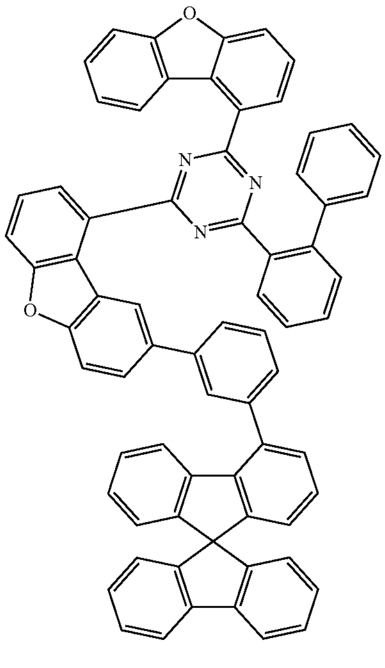
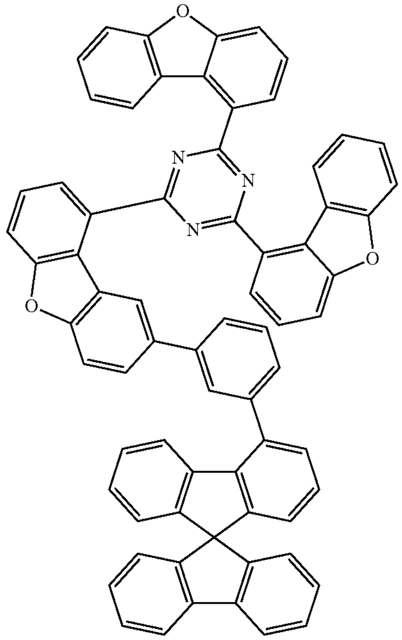
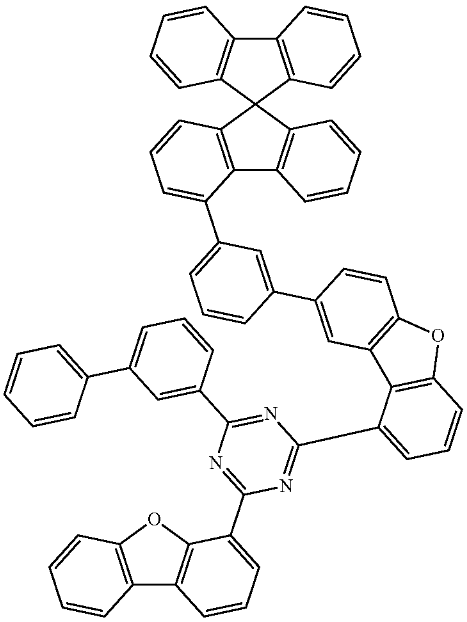

-continued
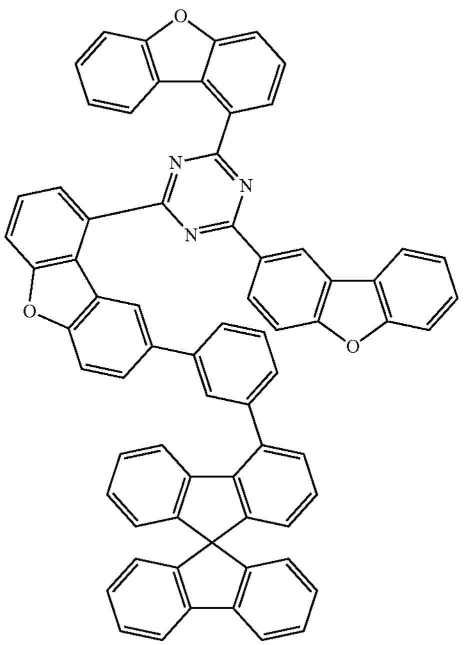
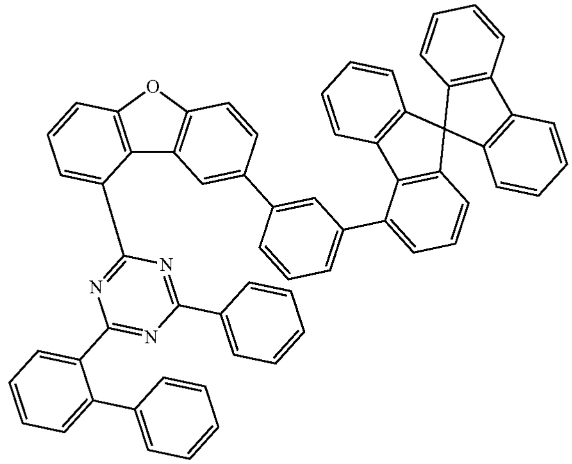
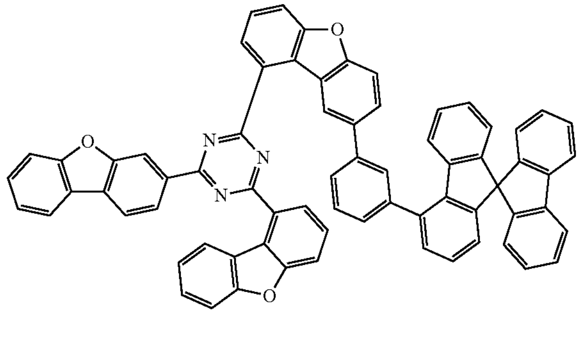
-continued
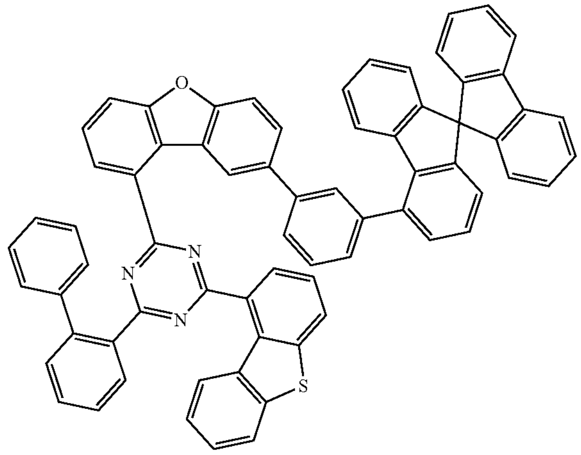
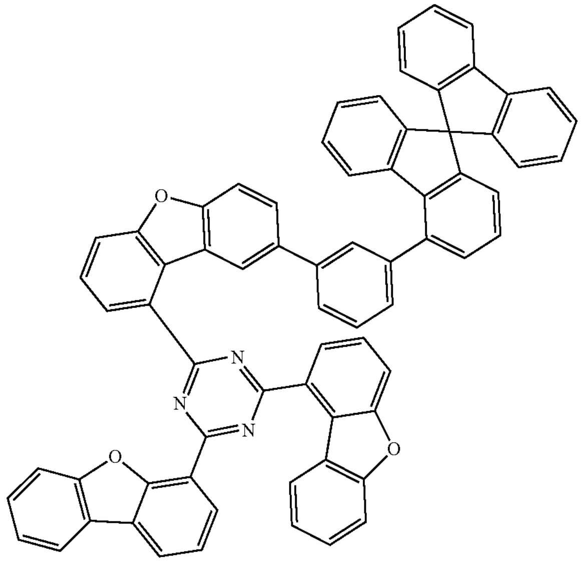
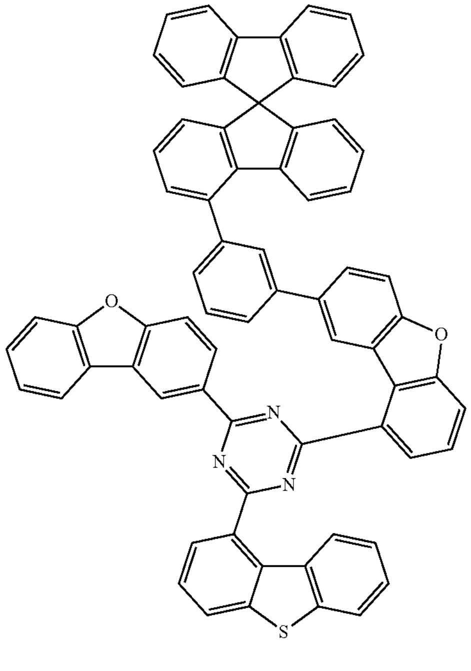

-continued
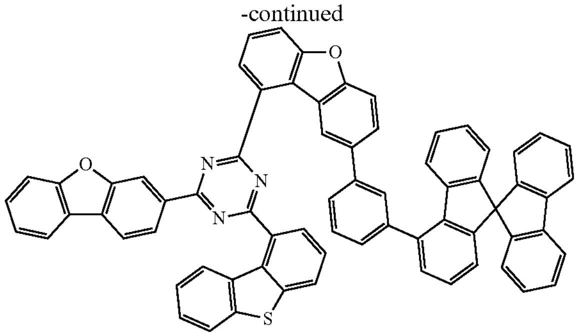
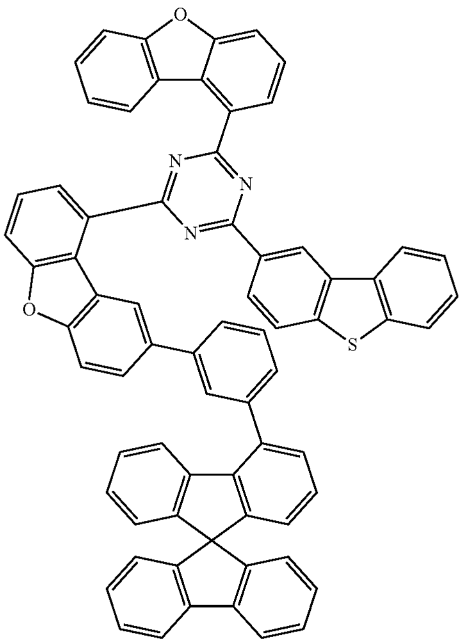
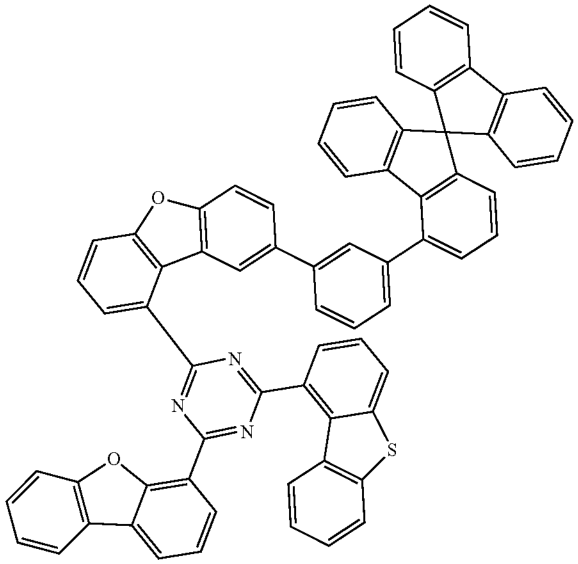
-continued
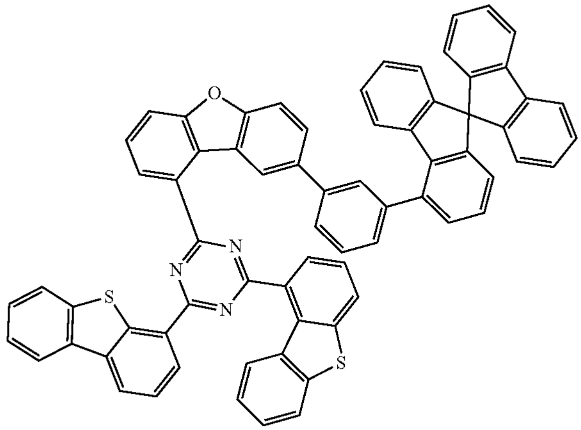
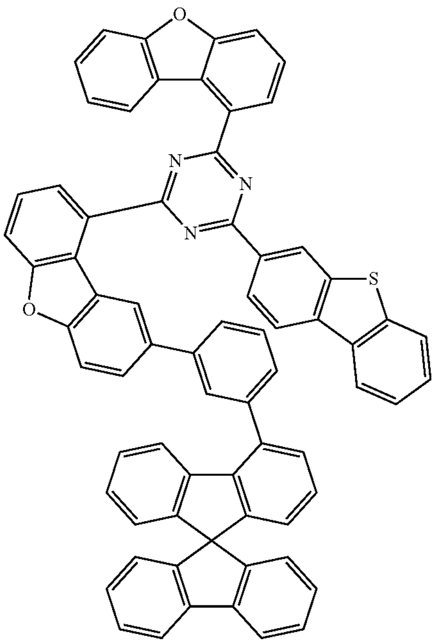
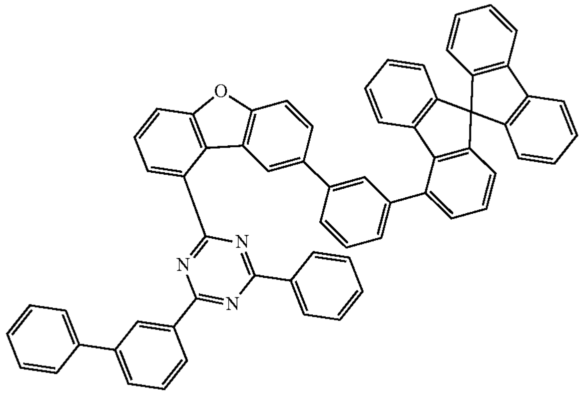

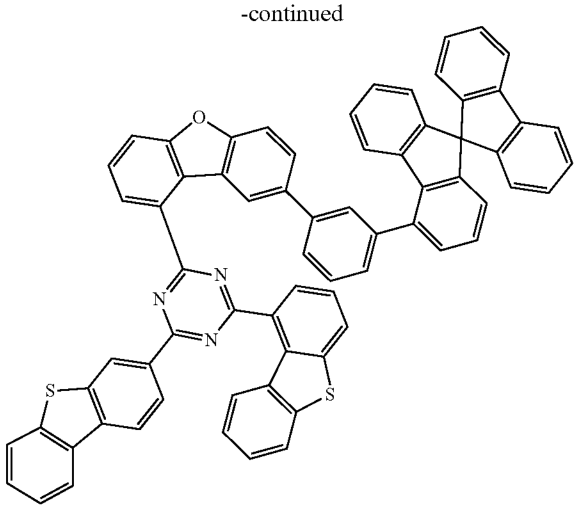
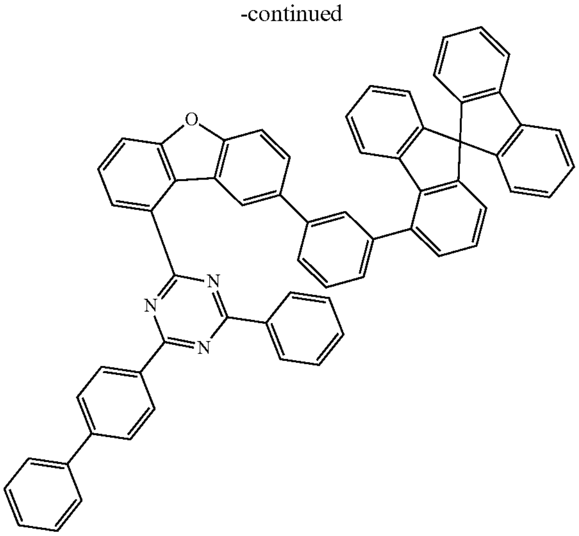
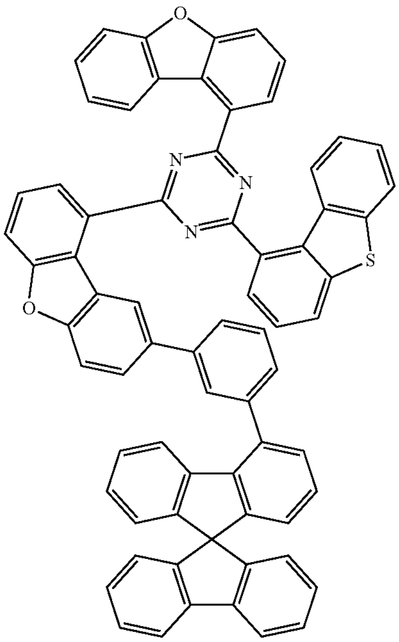
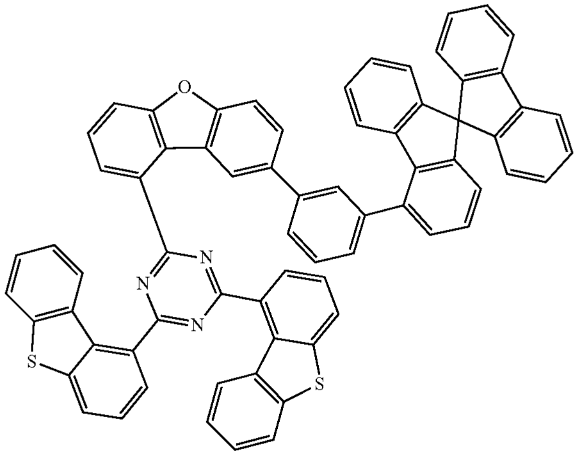
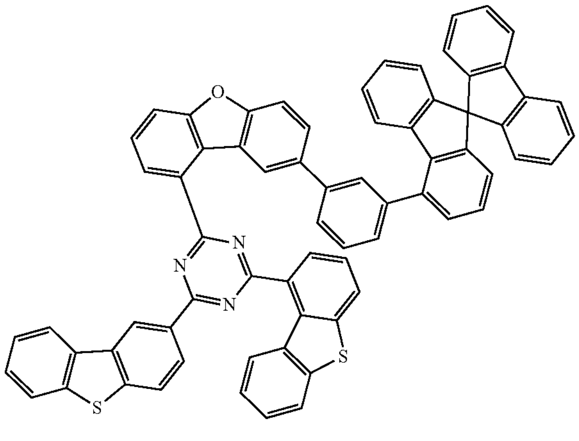
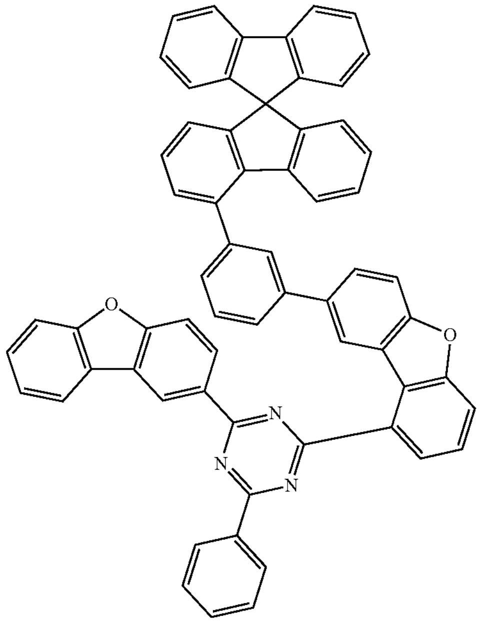

-continued
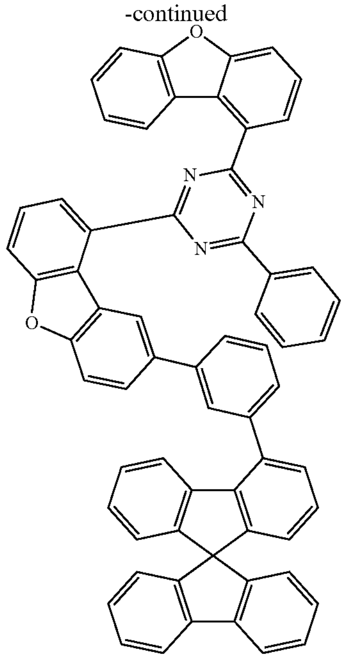
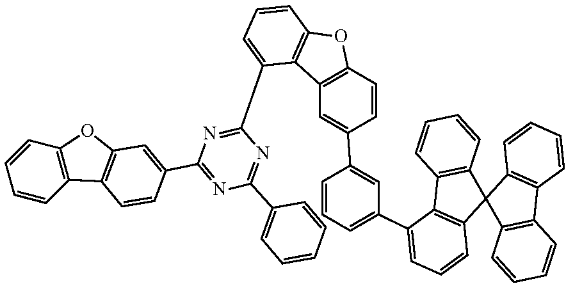
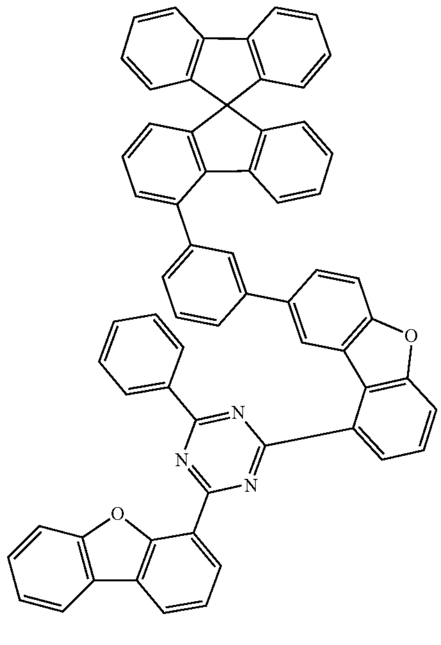
-continued
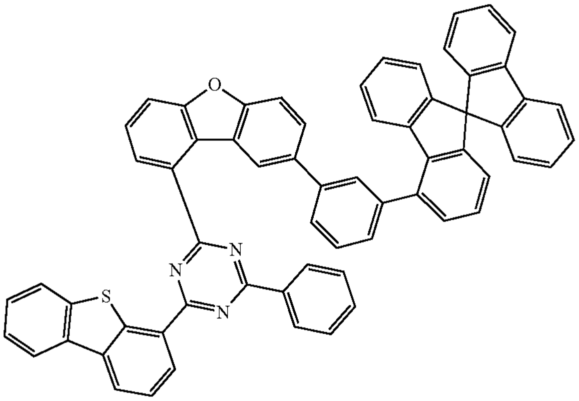
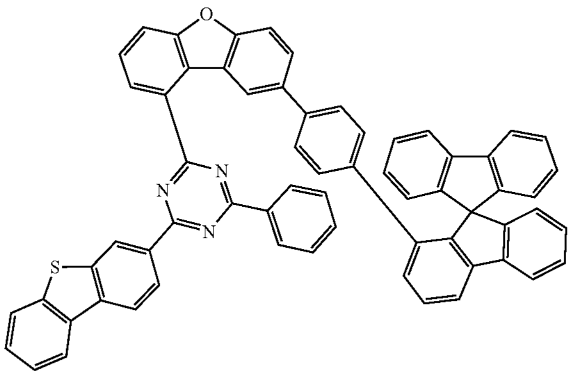
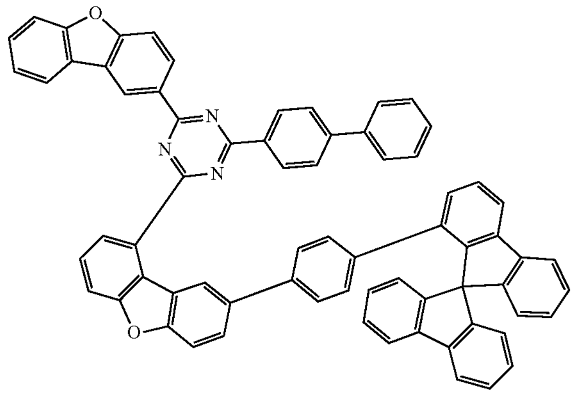
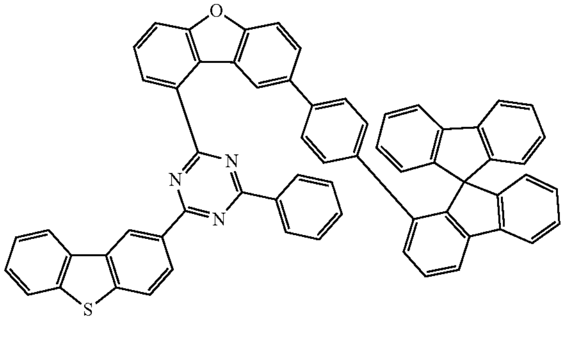

-continued
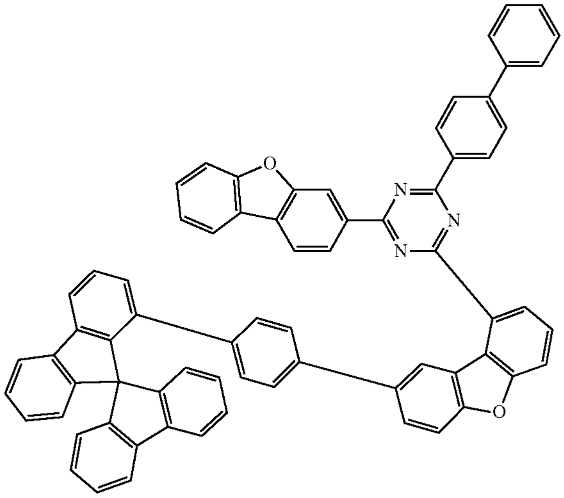
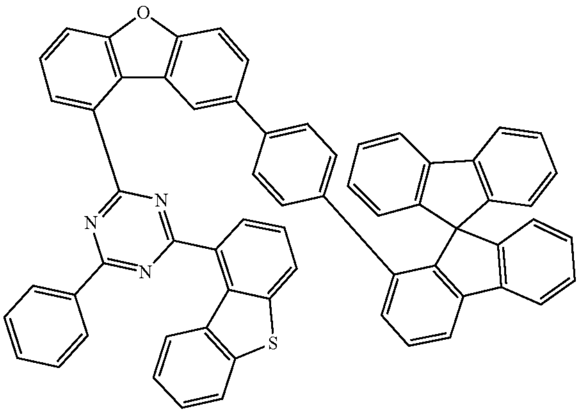
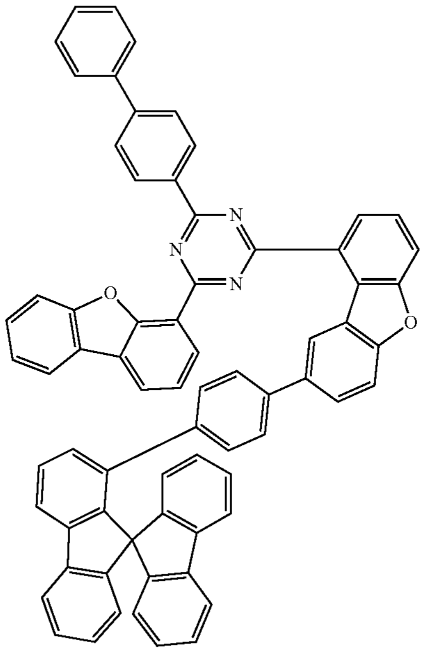
-continued
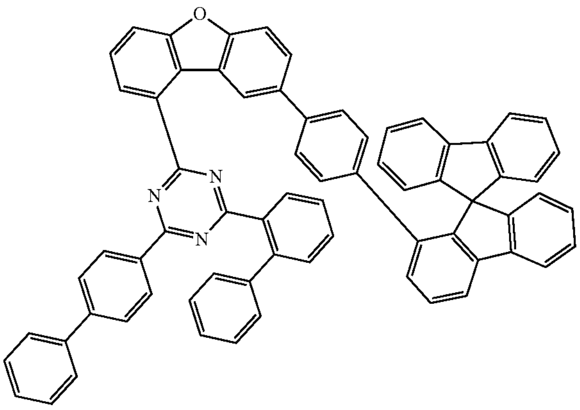
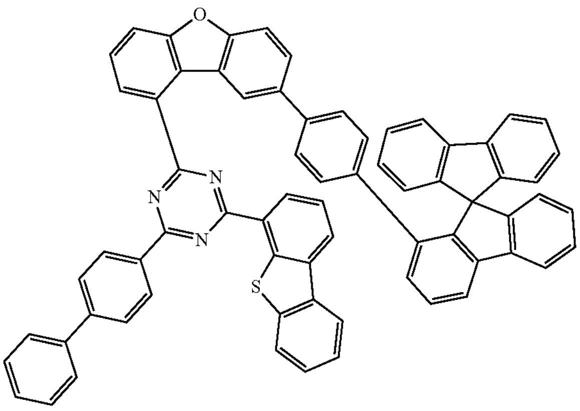
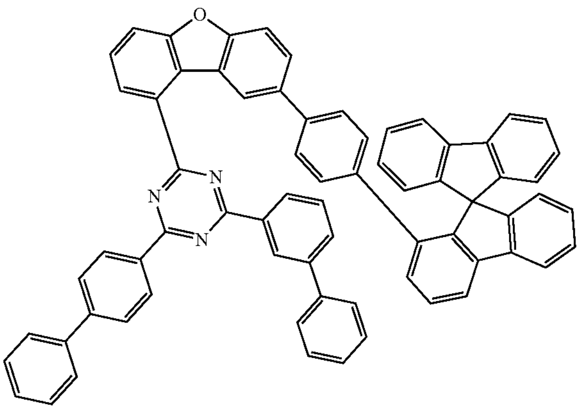
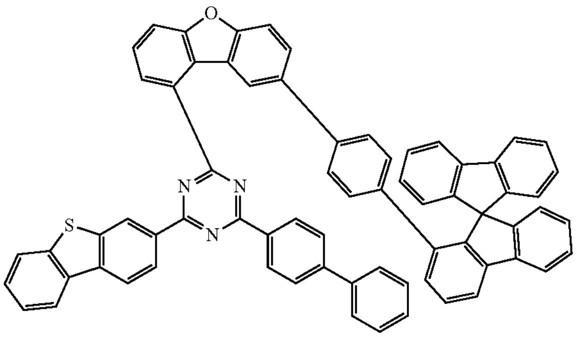

-continued
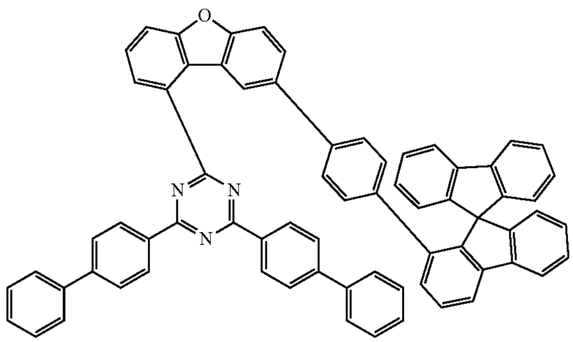
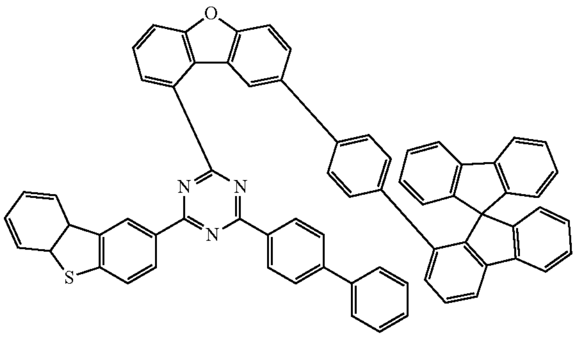
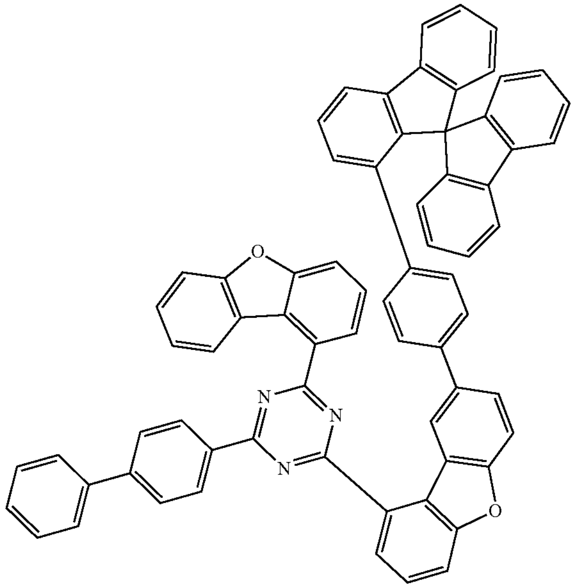
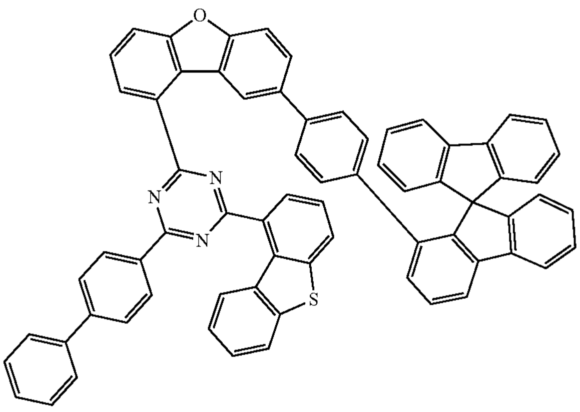
-continued
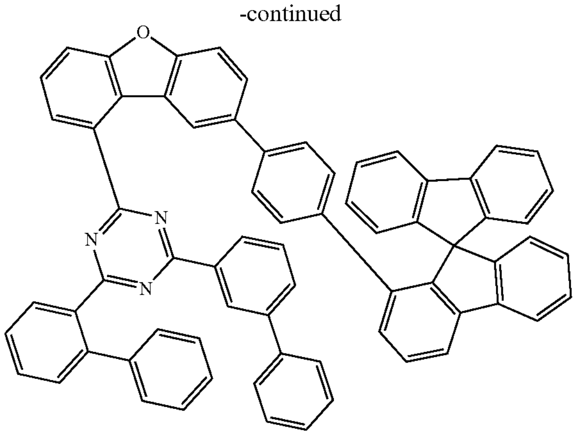
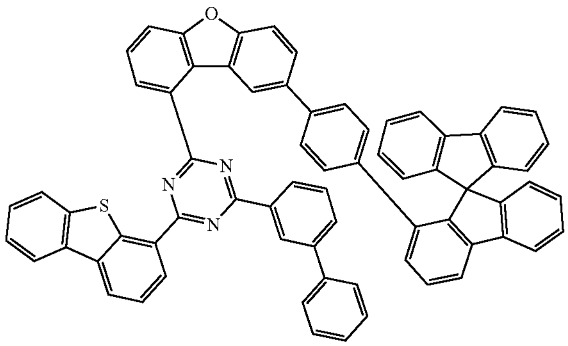
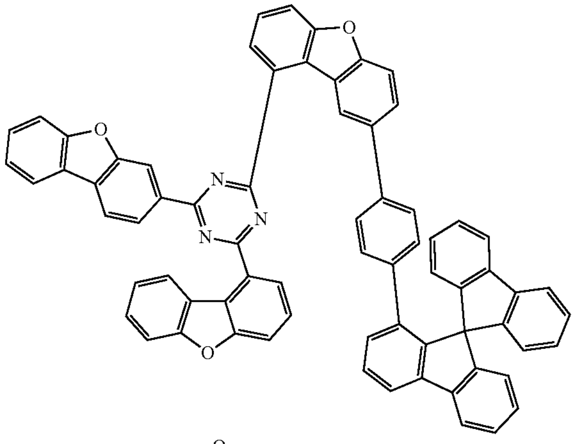
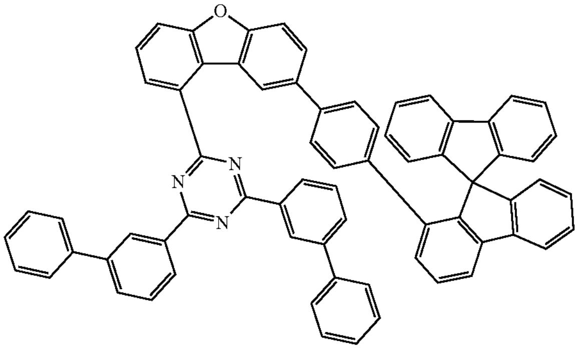

-continued
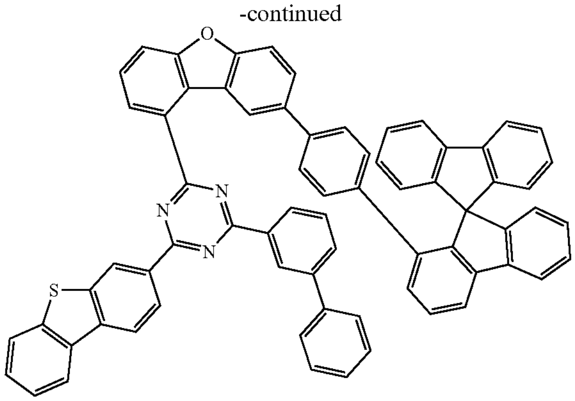
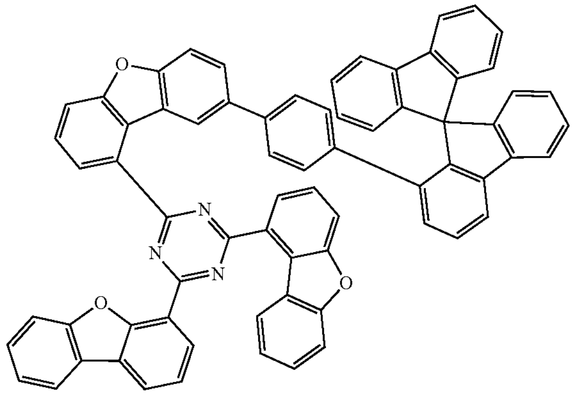
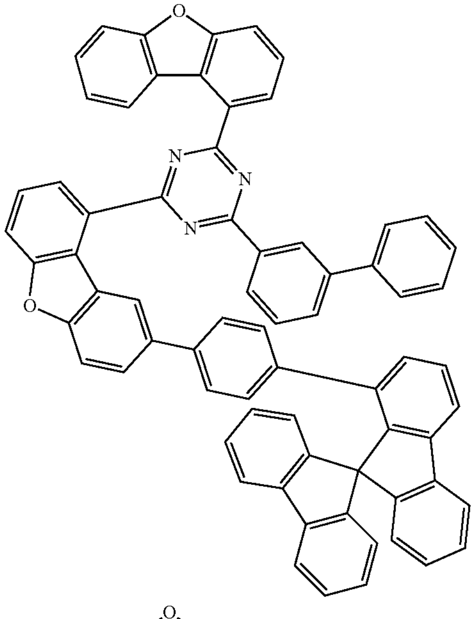
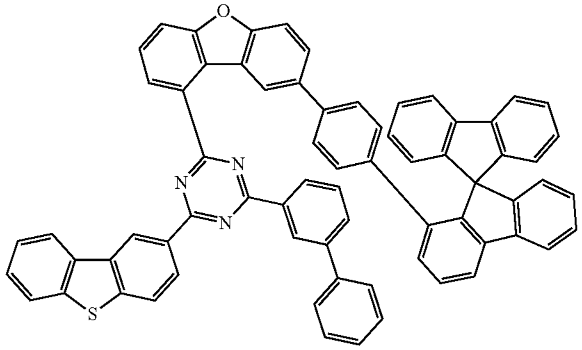
-continued
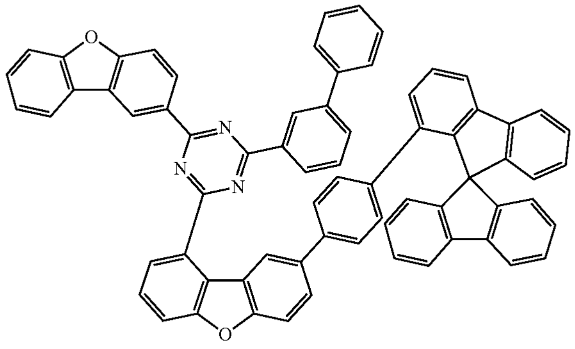
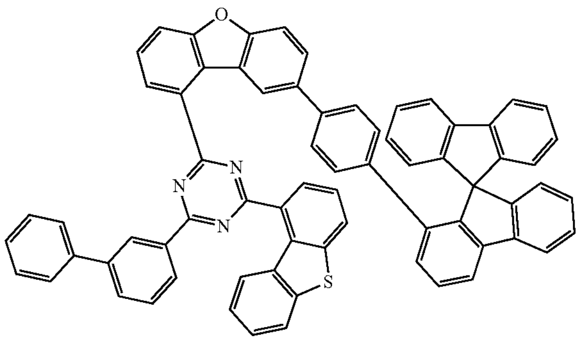
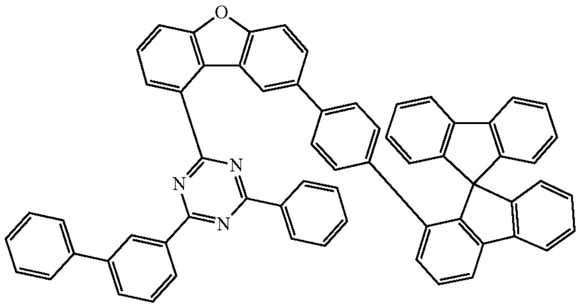
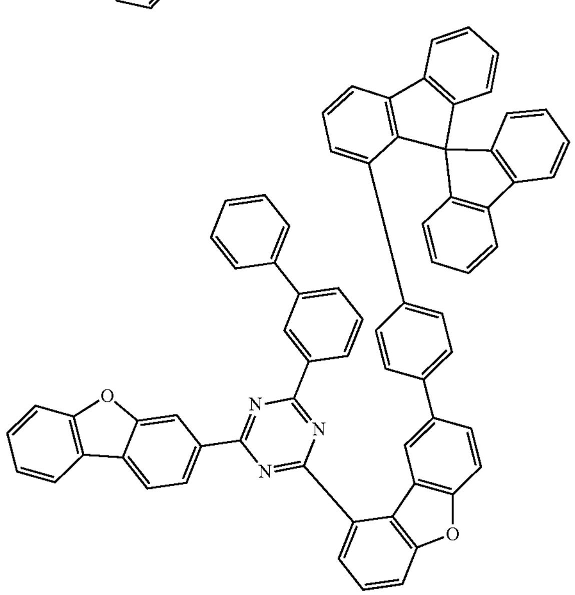

-continued
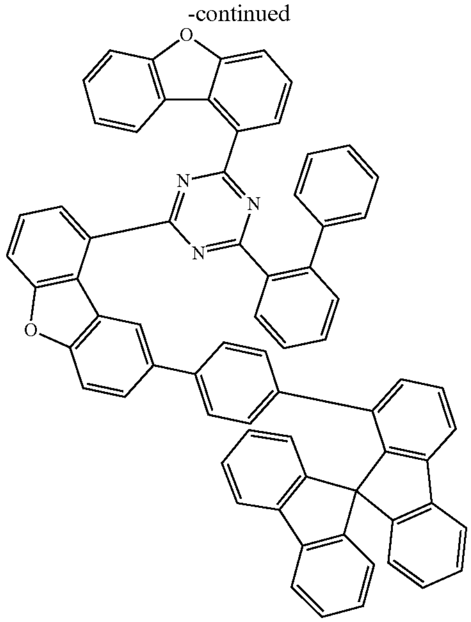
-continued
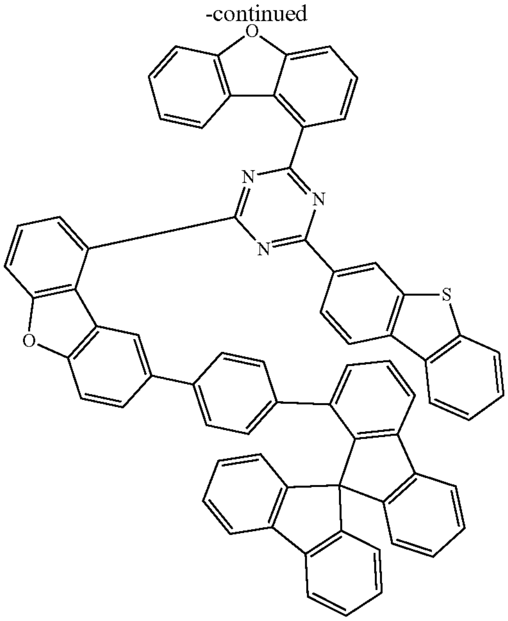
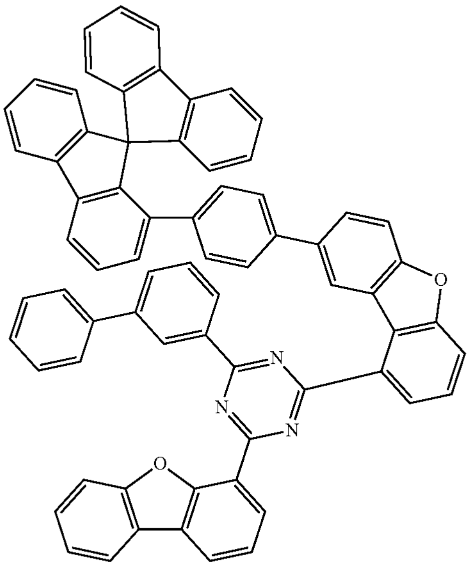
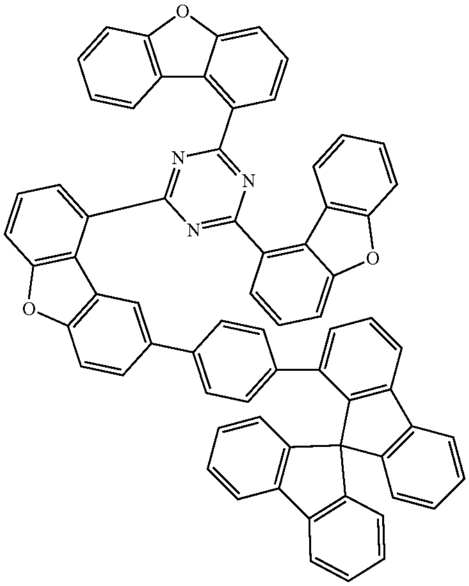

-continued
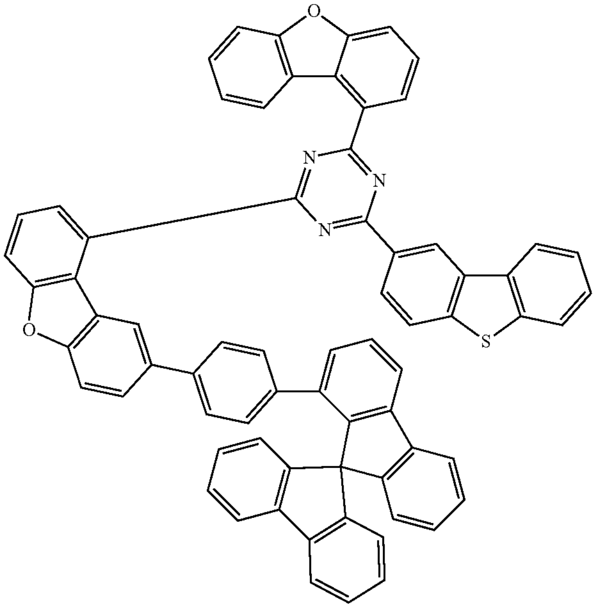
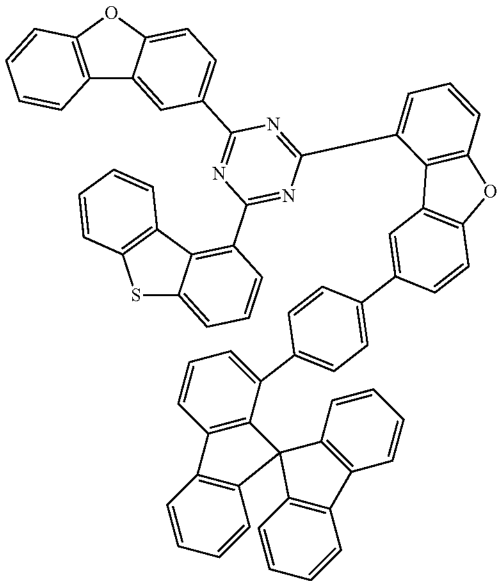
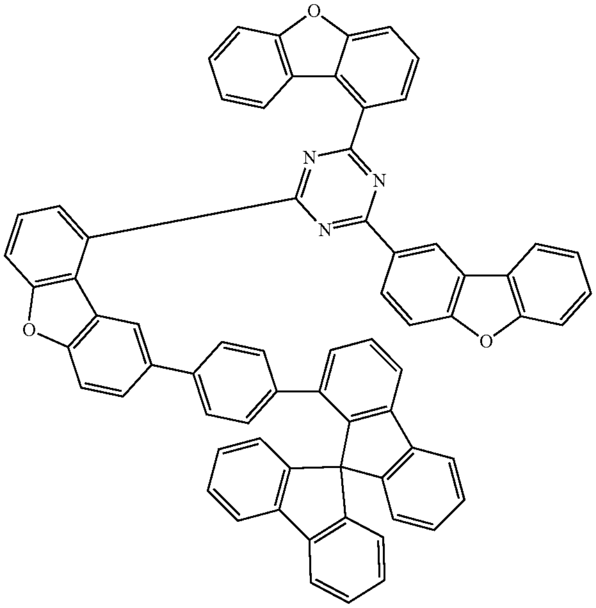
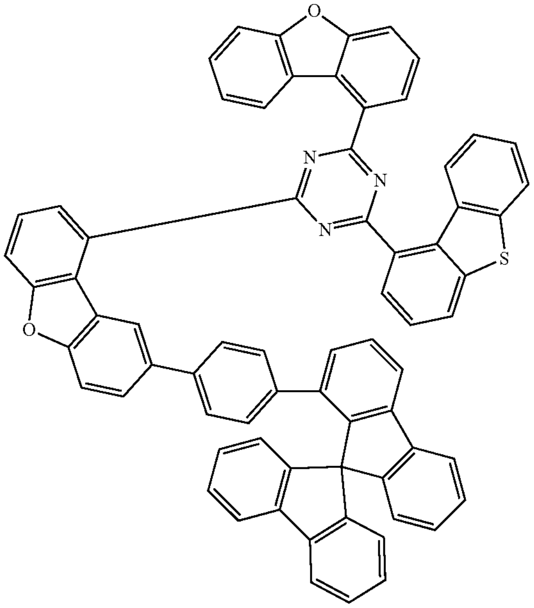
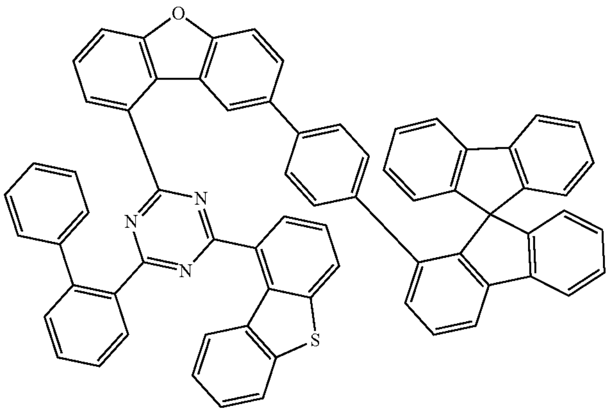

-continued
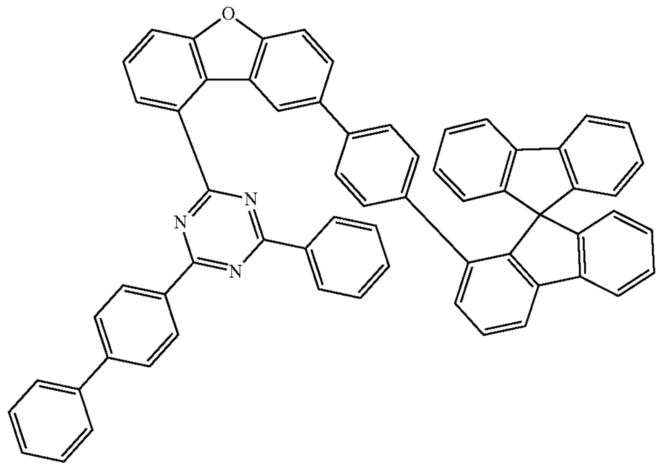
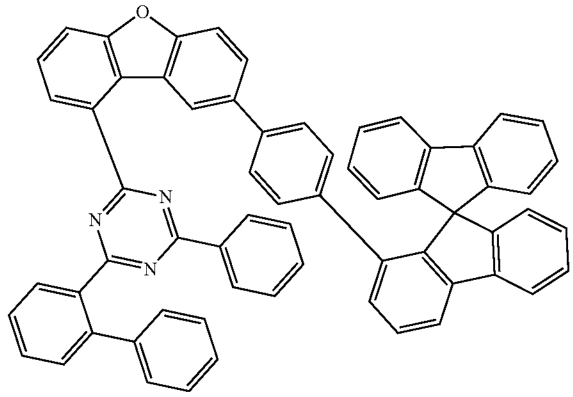
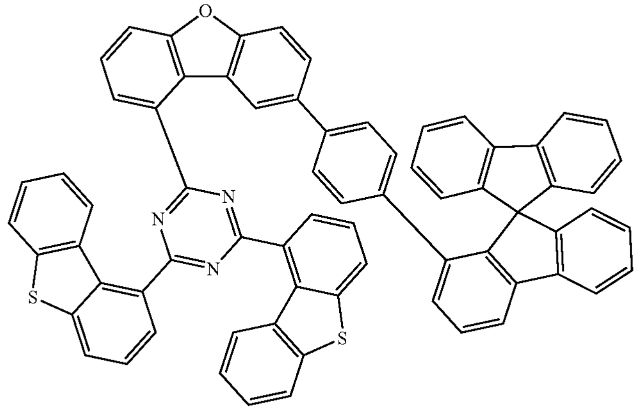

-continued
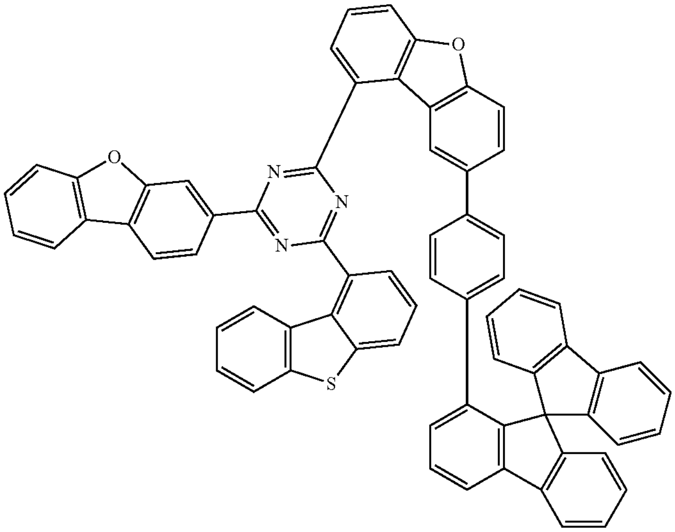
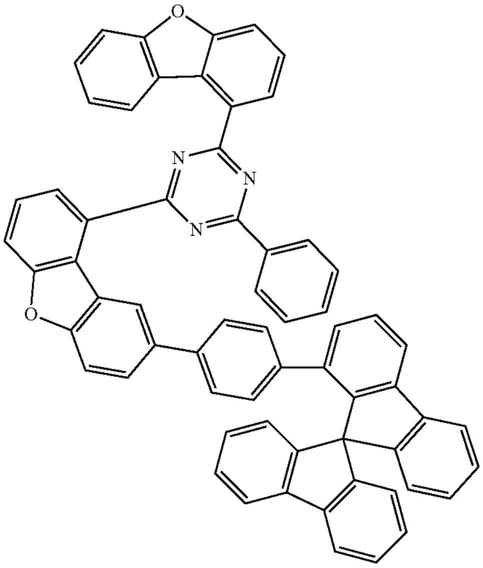
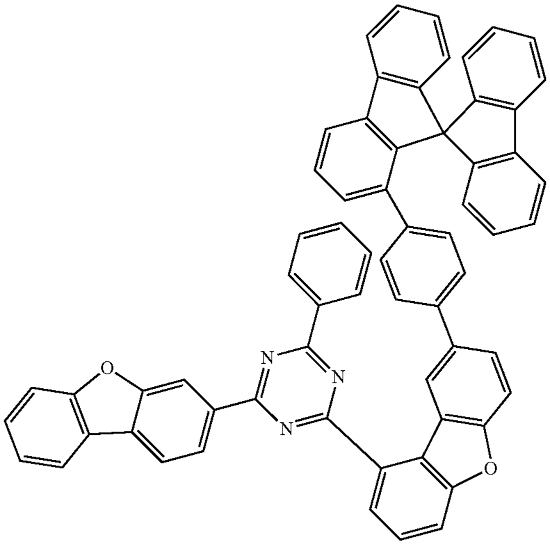
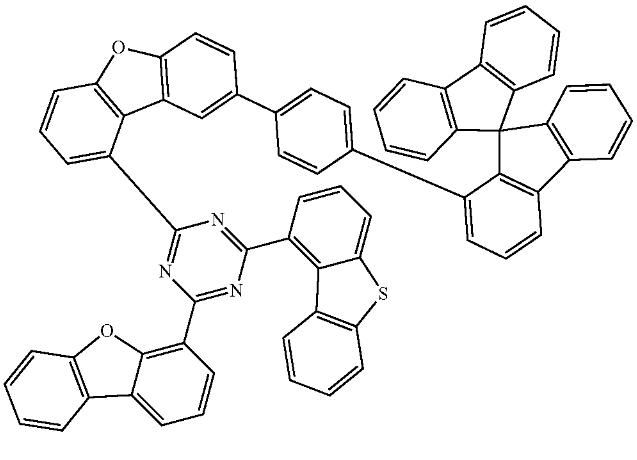

-continued
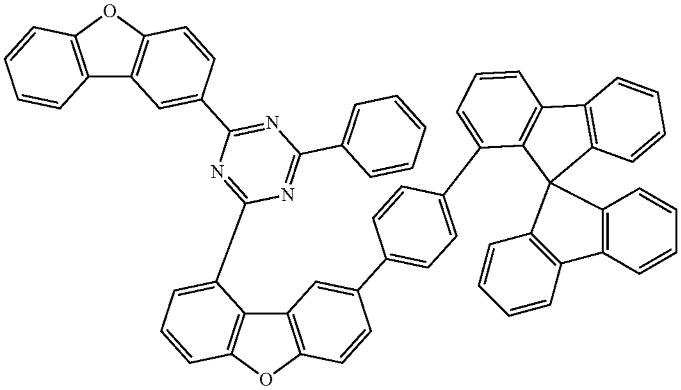
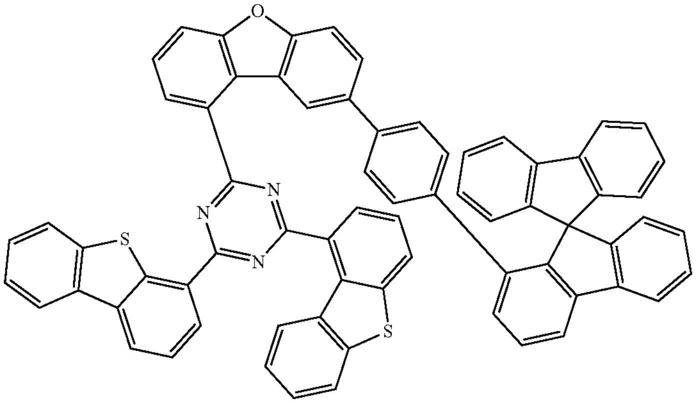
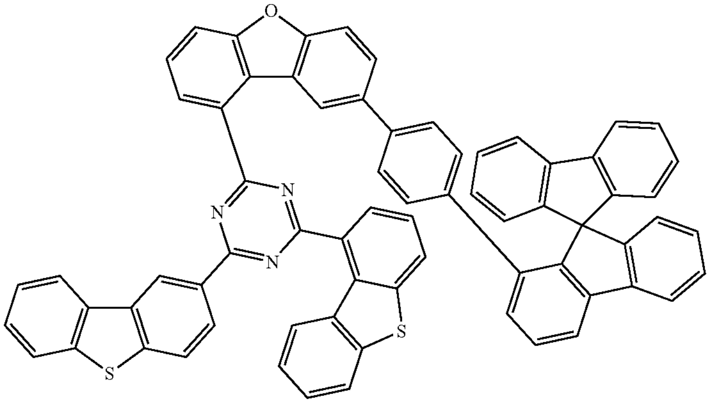
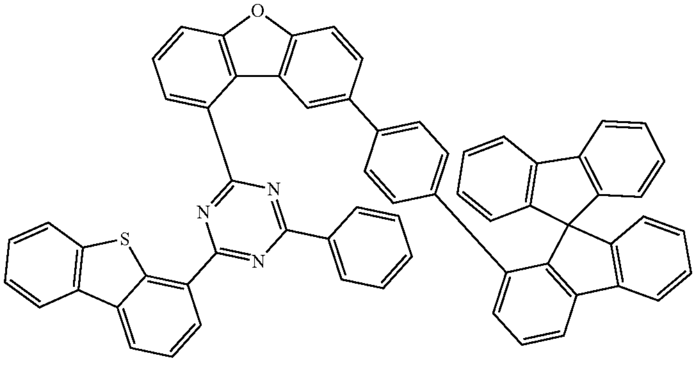

-continued
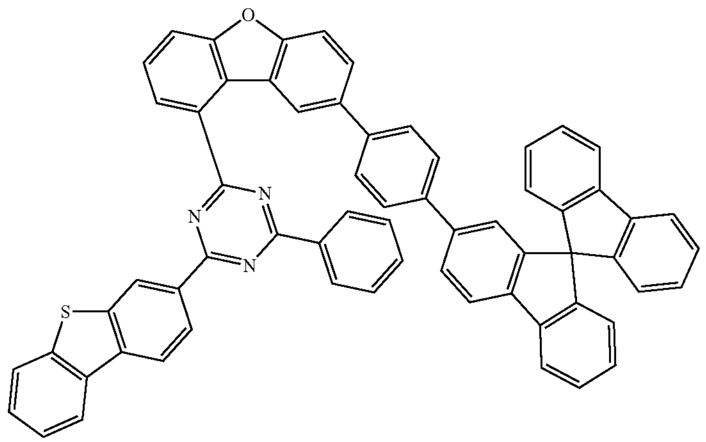
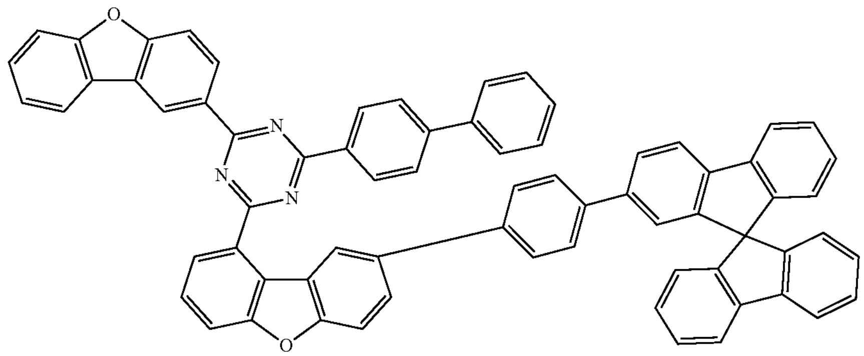
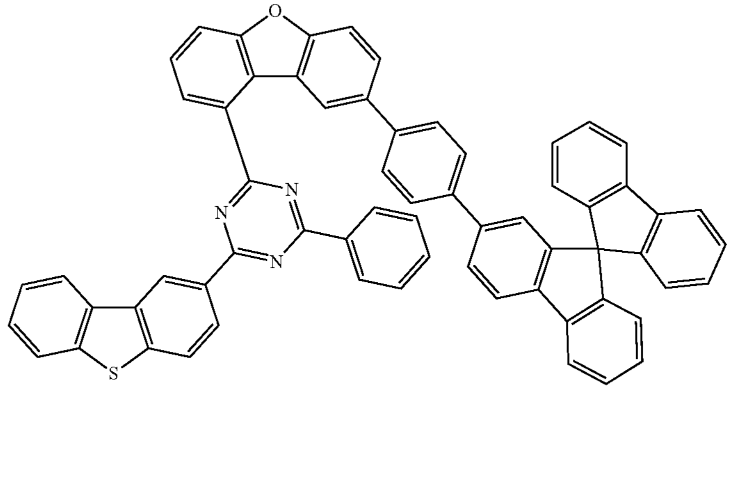

-continued
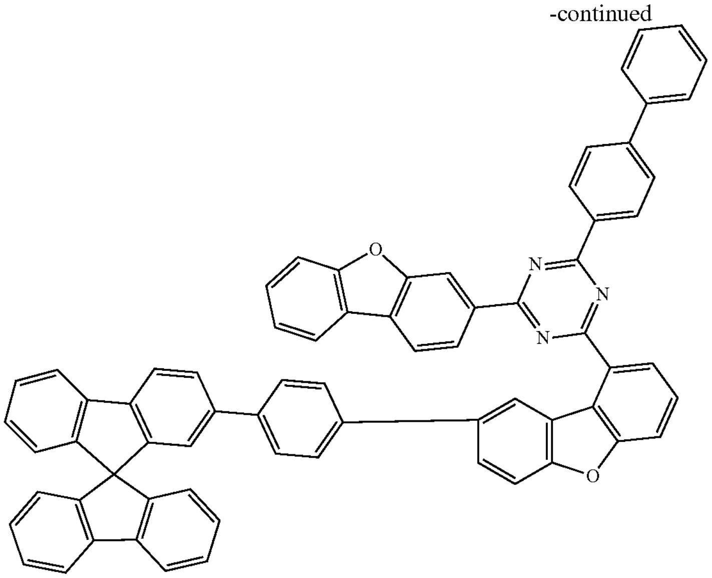
-continued
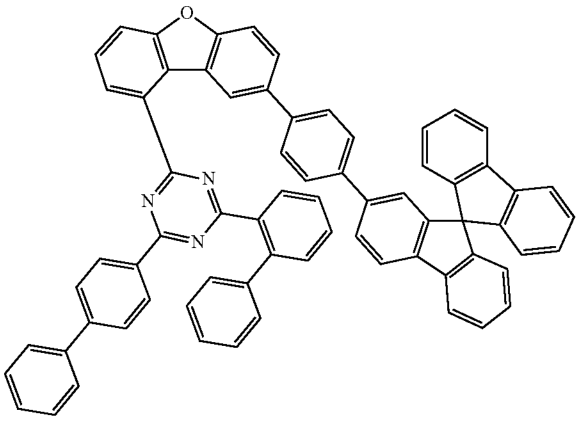
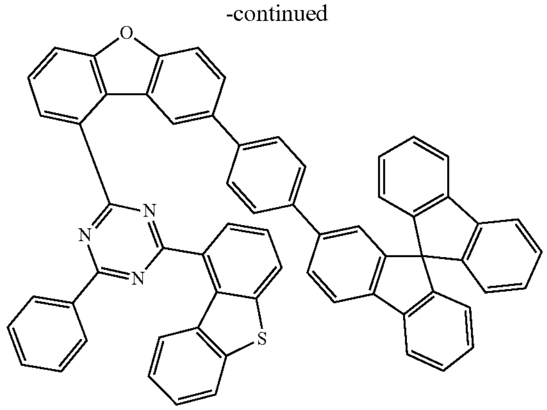
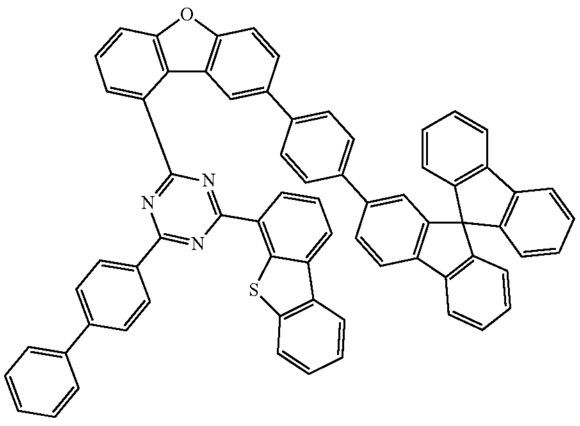
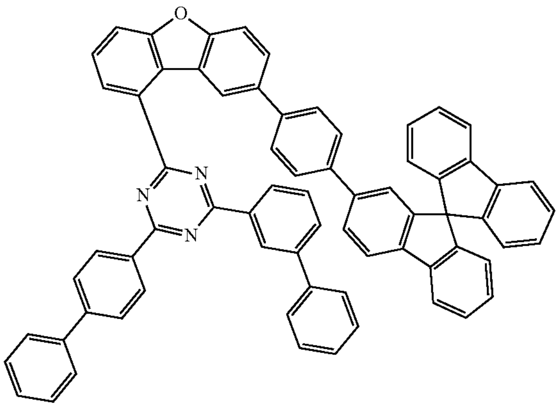

-continued
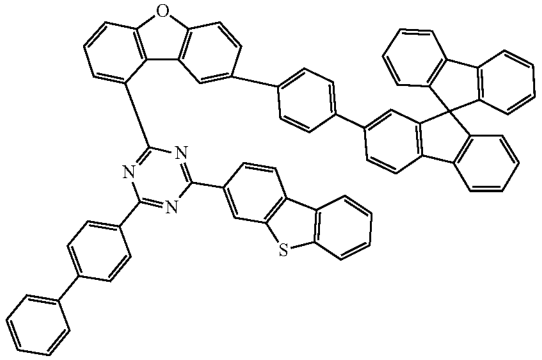
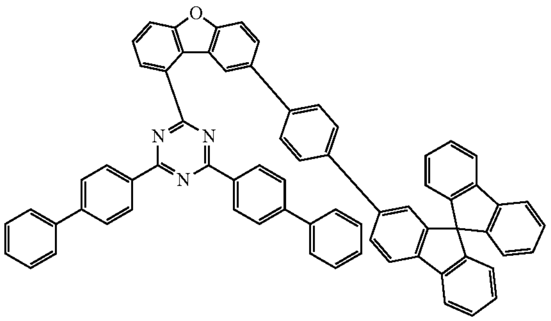
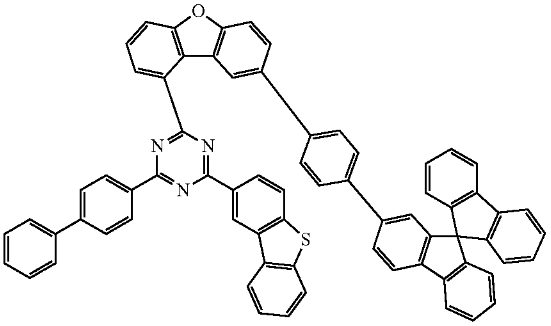
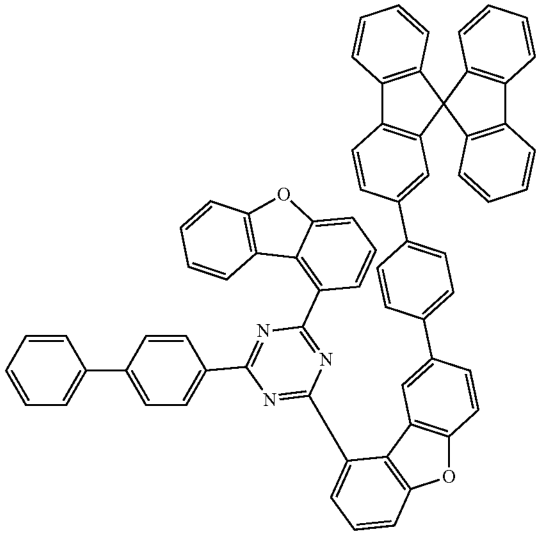
-continued
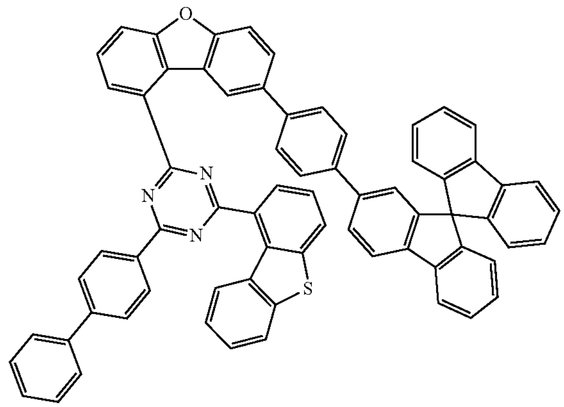
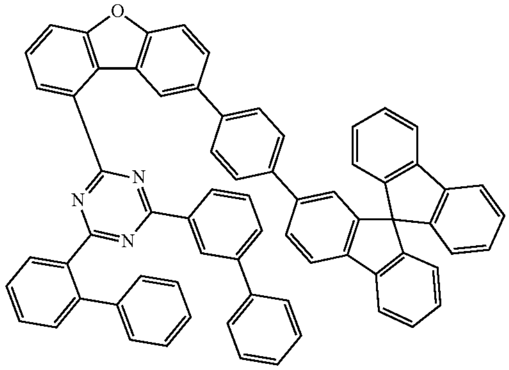
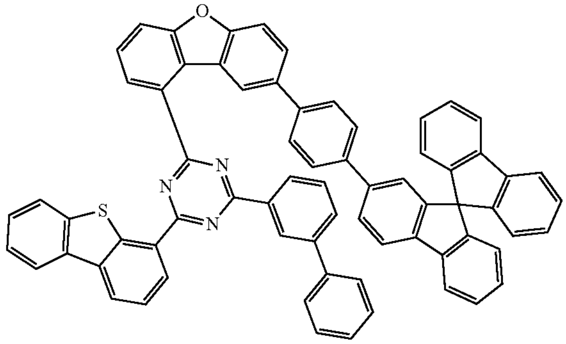
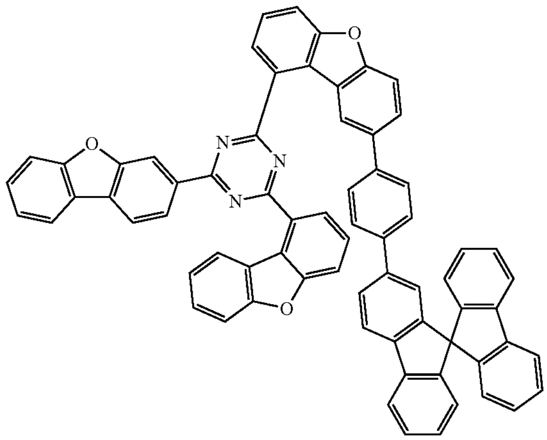

-continued
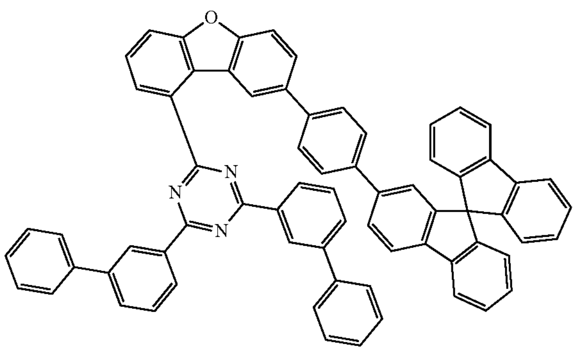
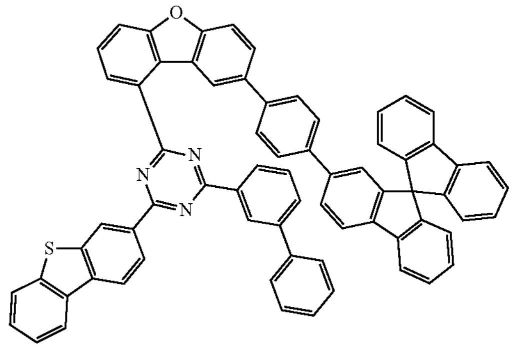
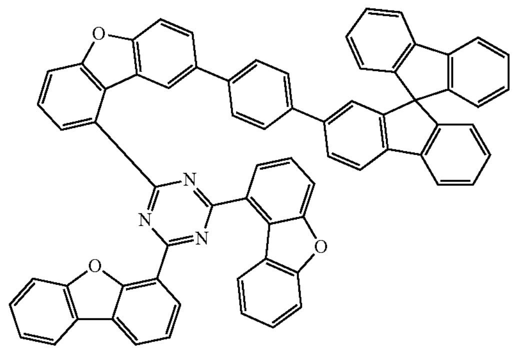
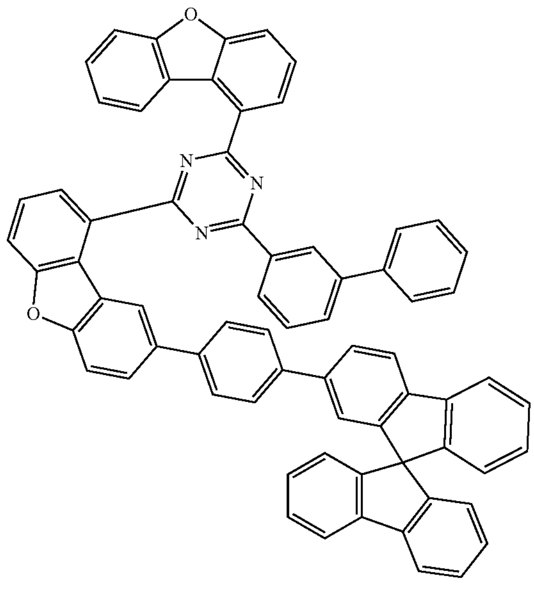
-continued
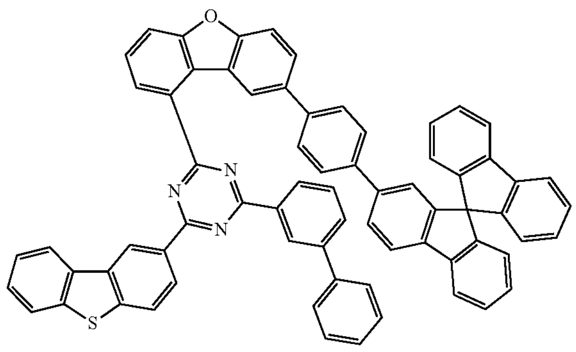
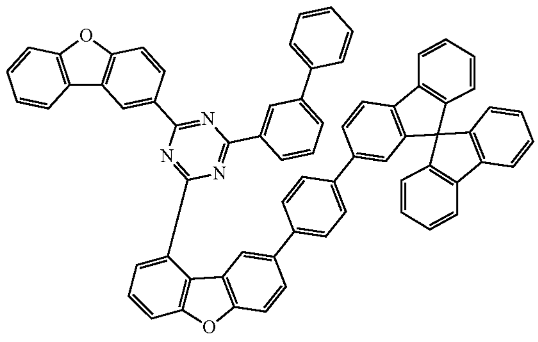
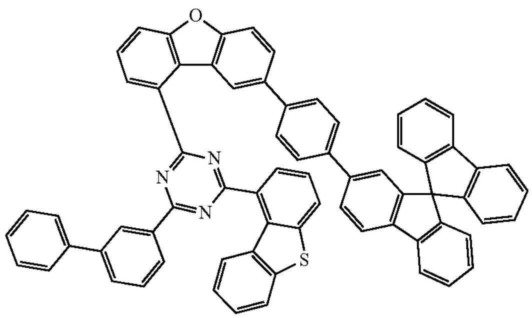
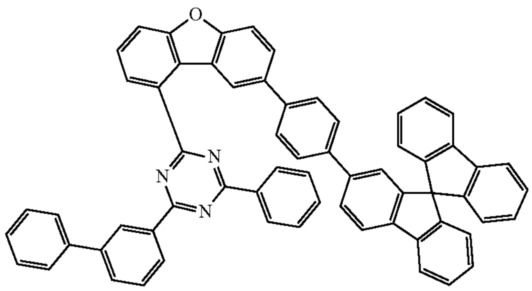

-continued
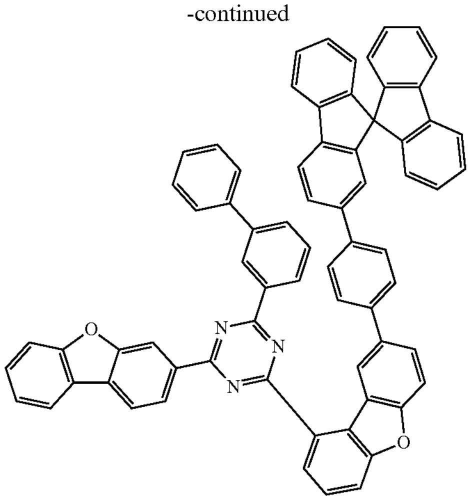
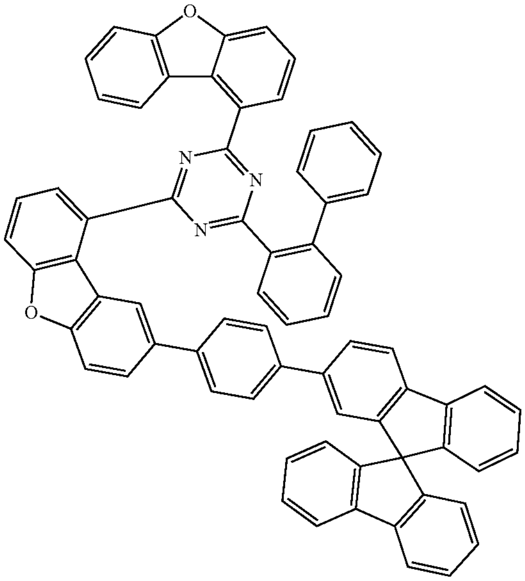
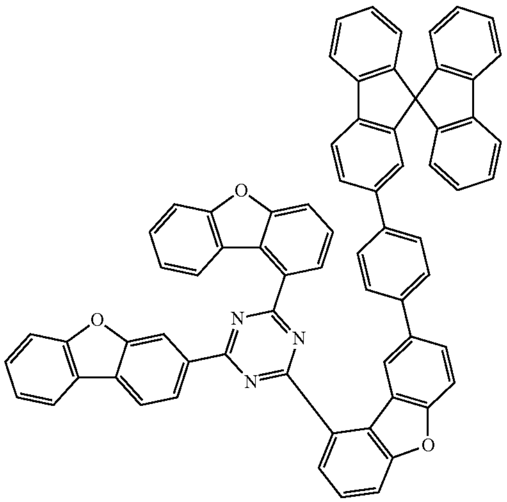
-continued
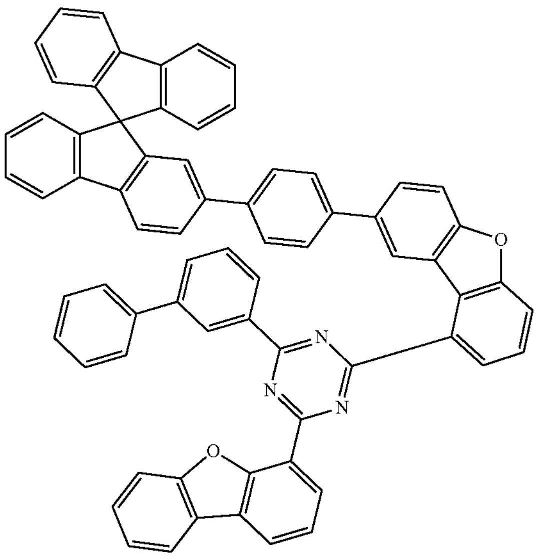
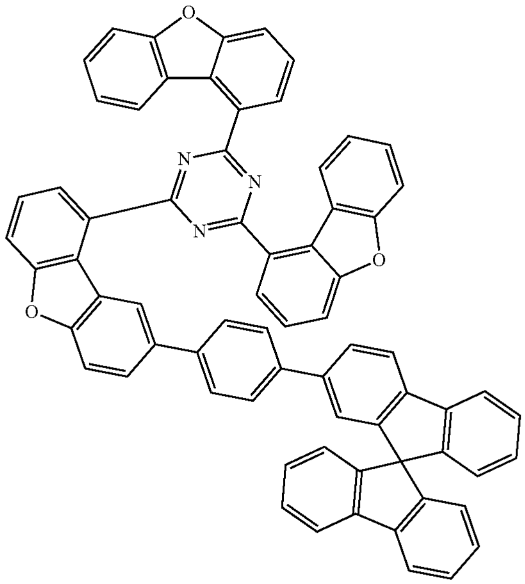
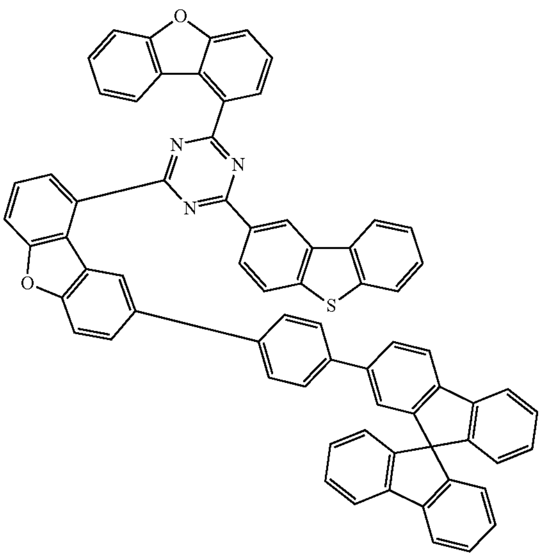

-continued
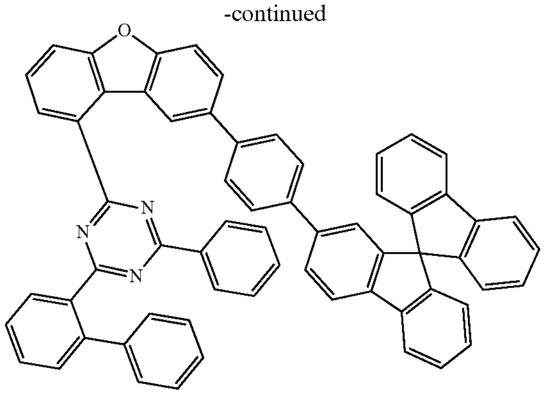
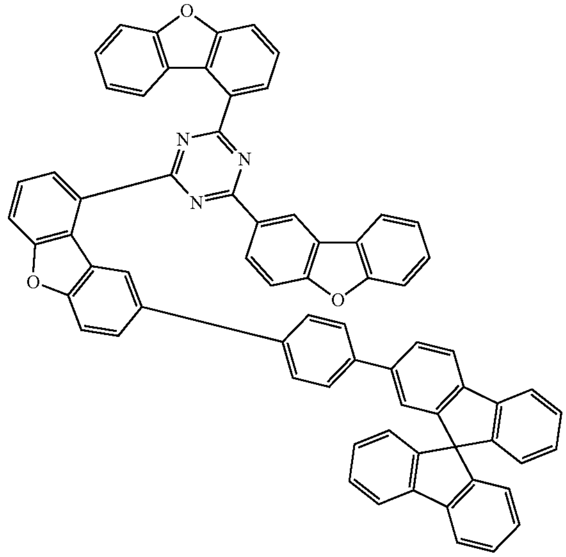
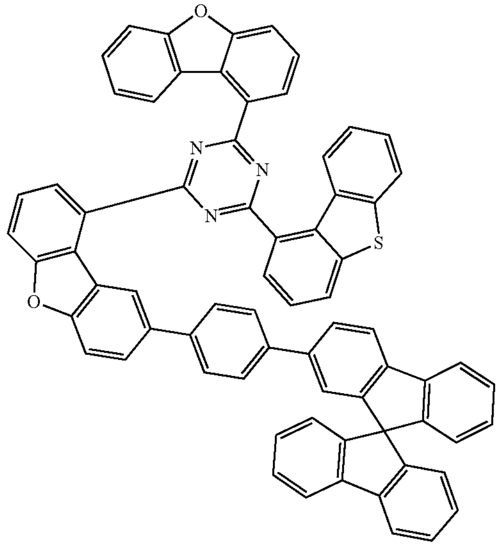
-continued
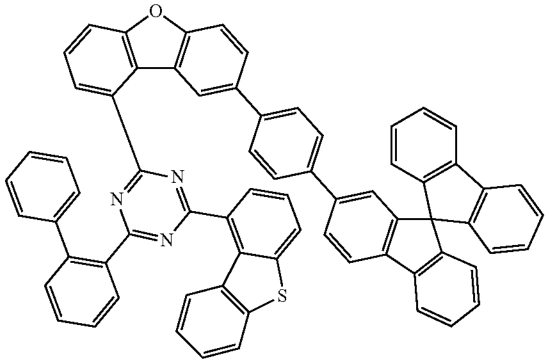
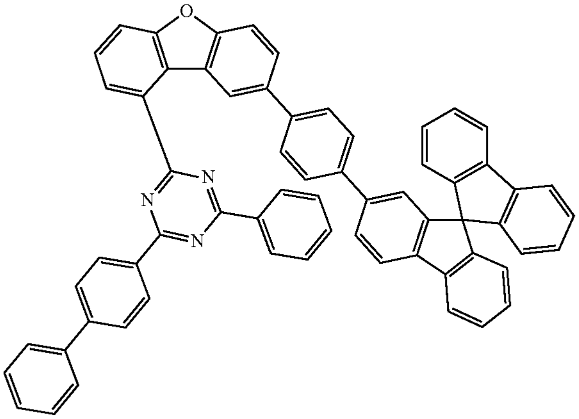
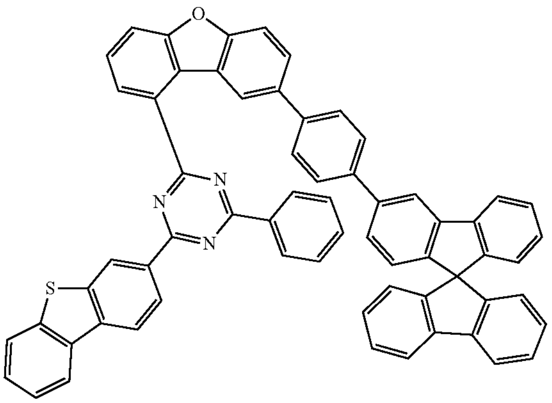

-continued
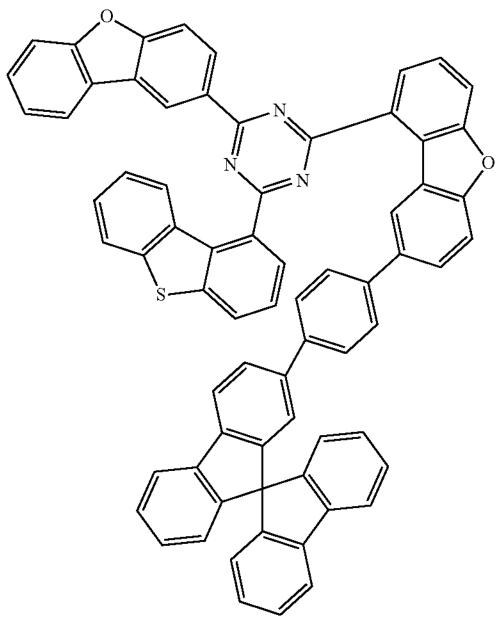
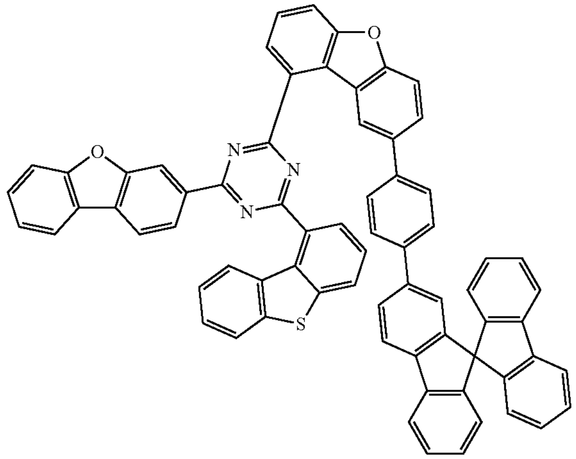
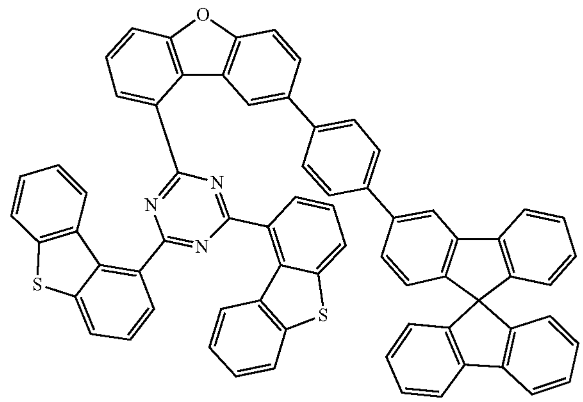
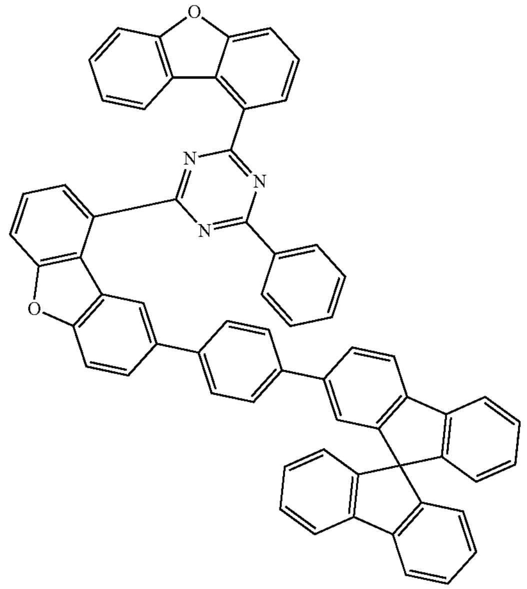
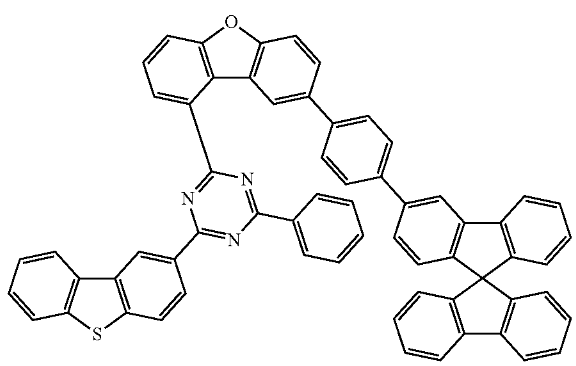
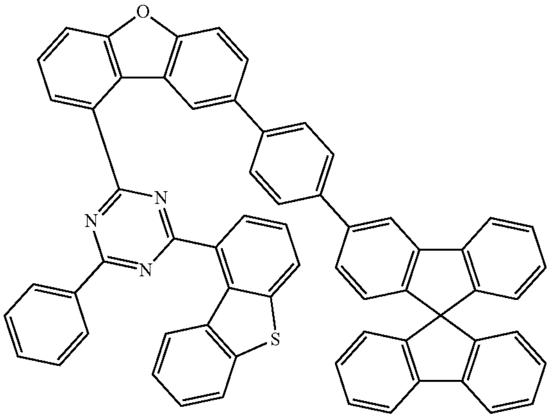

-continued
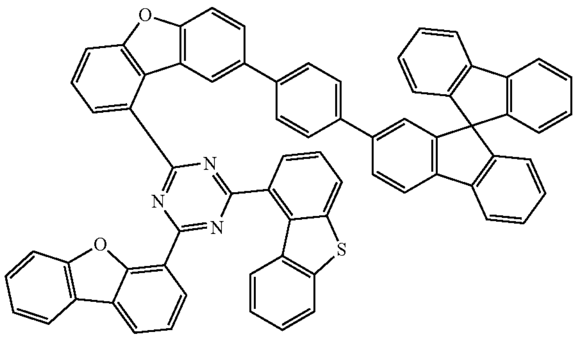
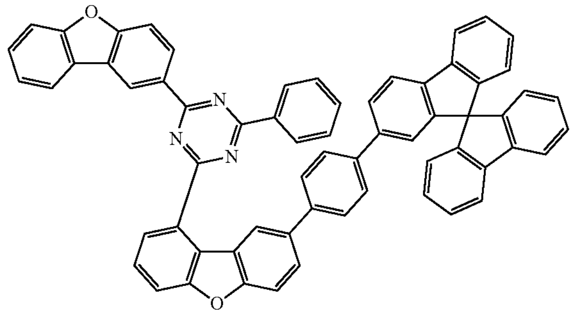
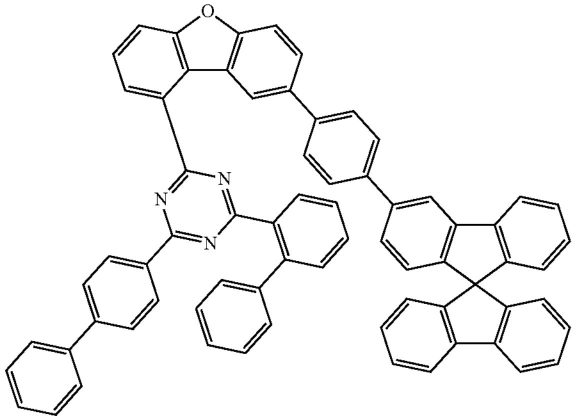
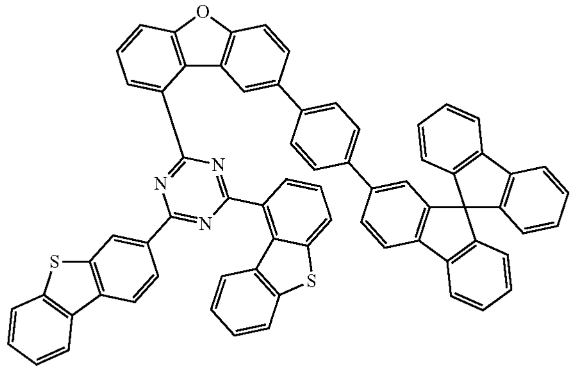
-continued
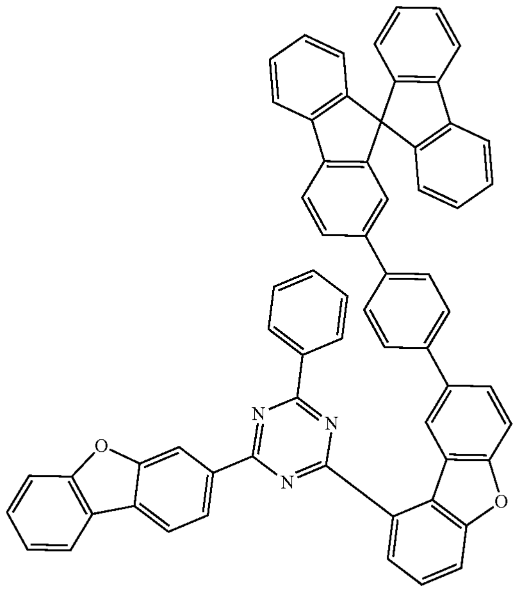
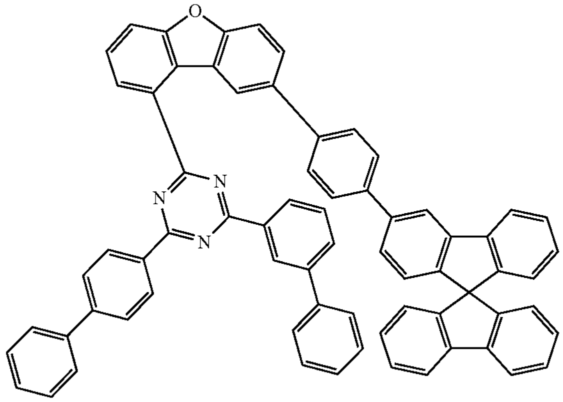
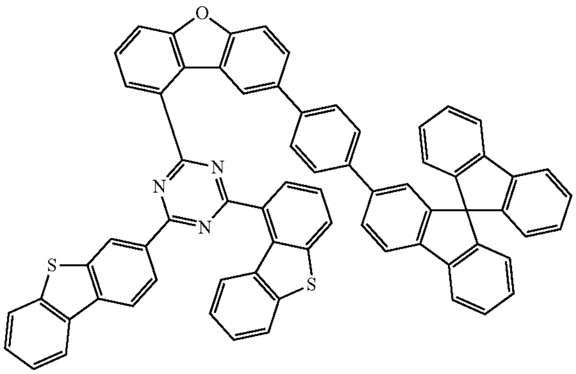

-continued
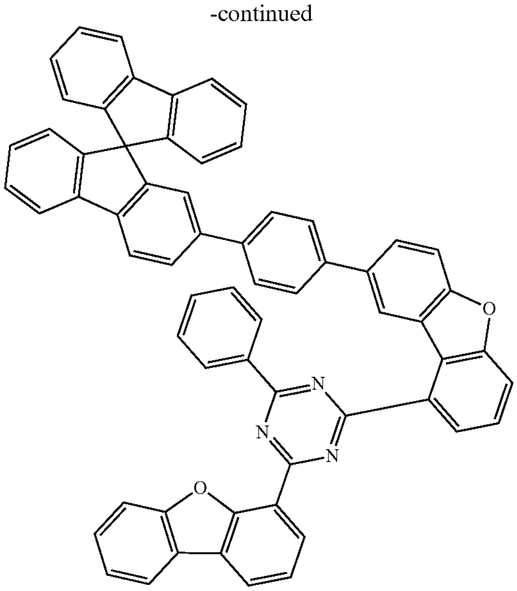
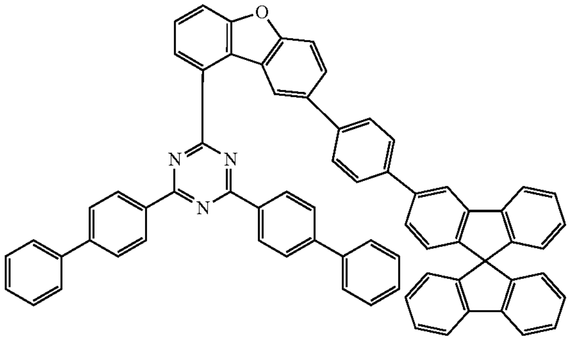
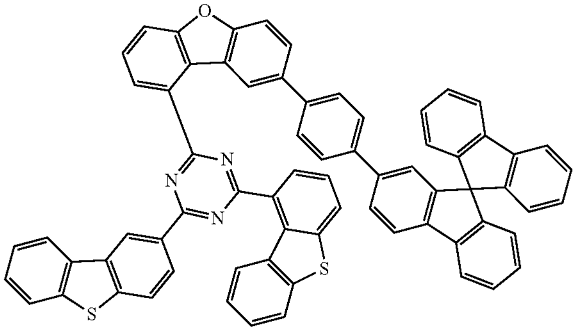
-continued
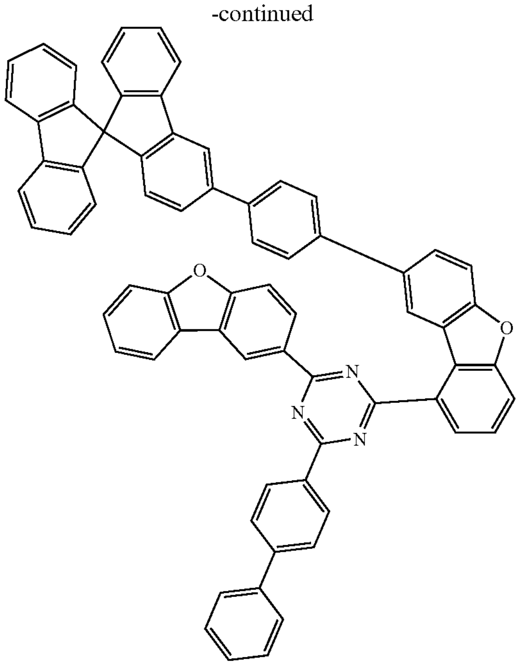
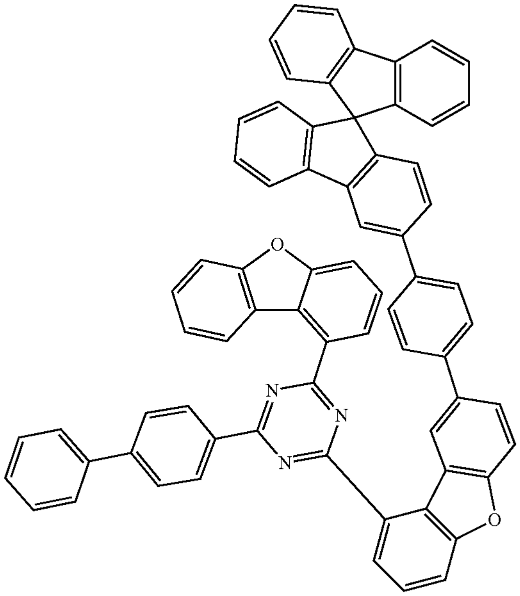
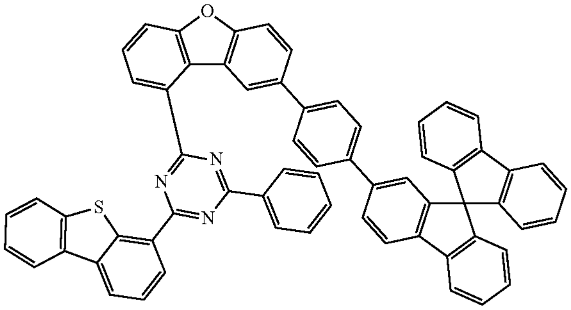

-continued
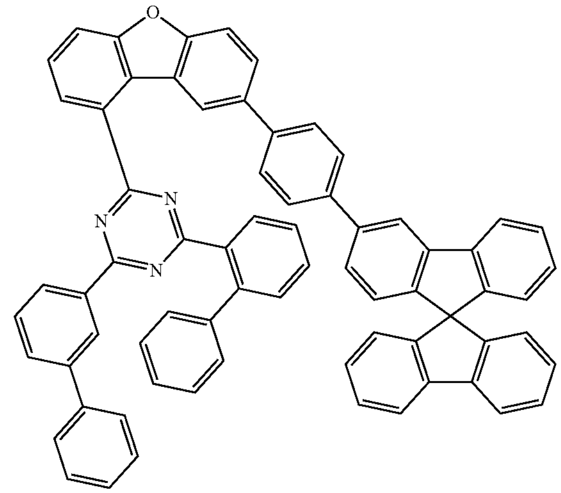
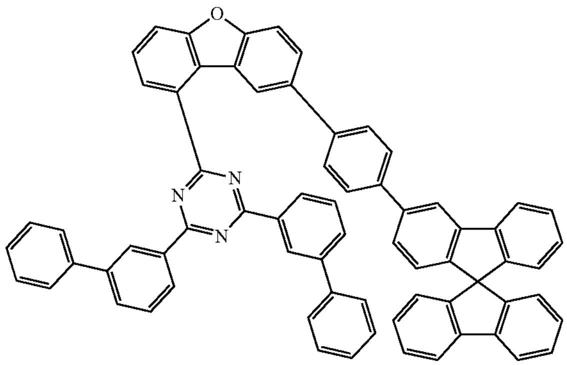
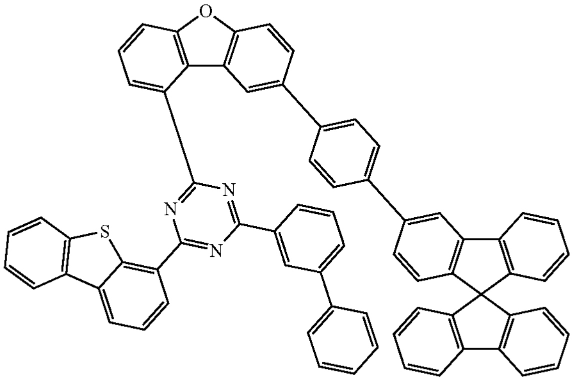
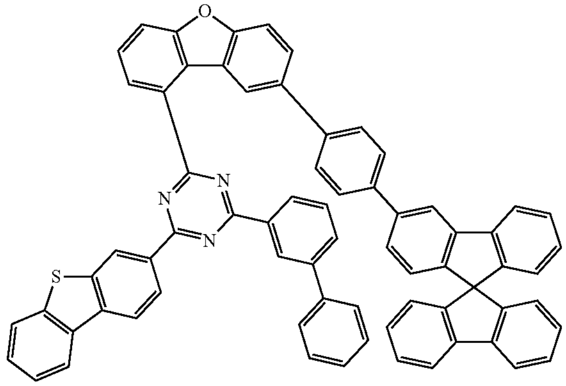
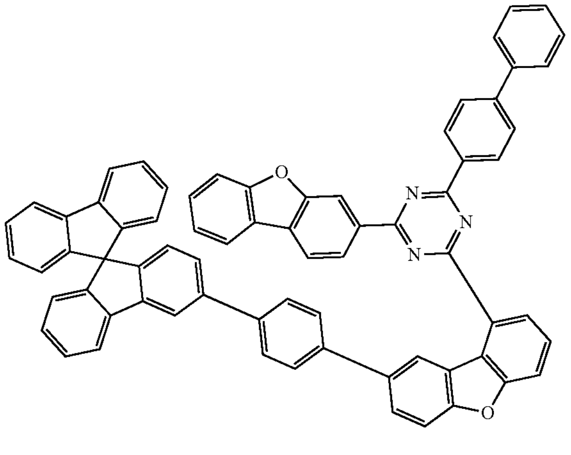
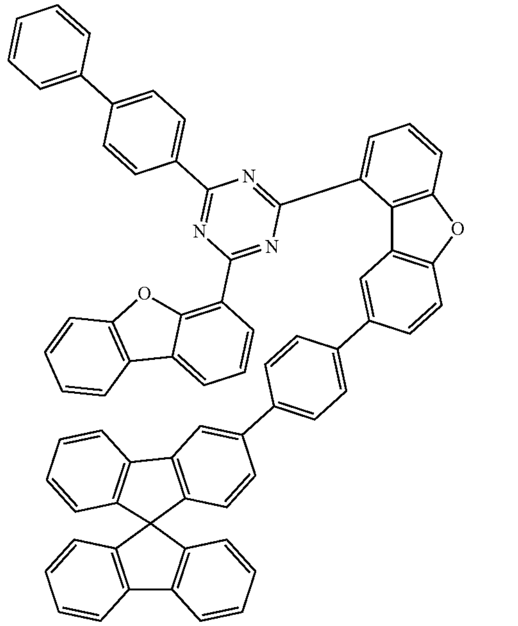

-continued
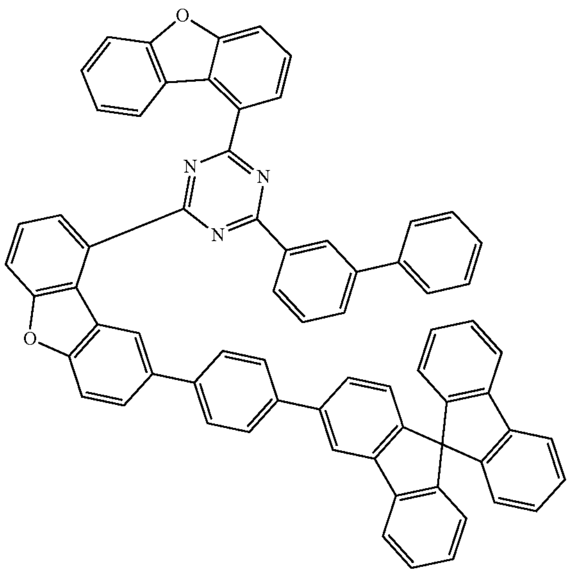
-continued
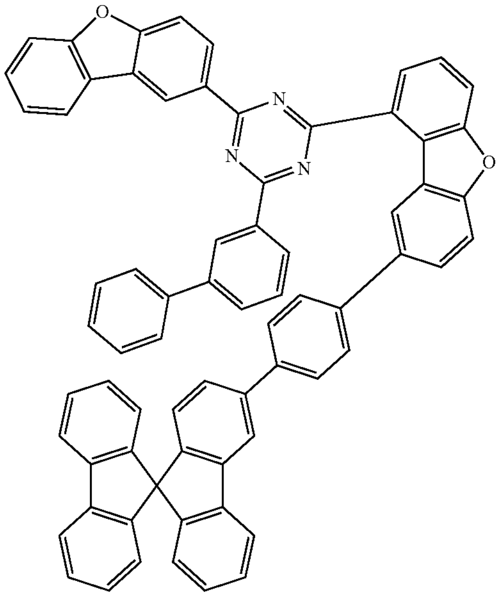
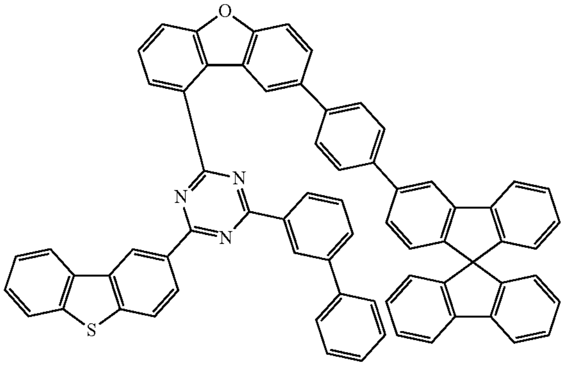
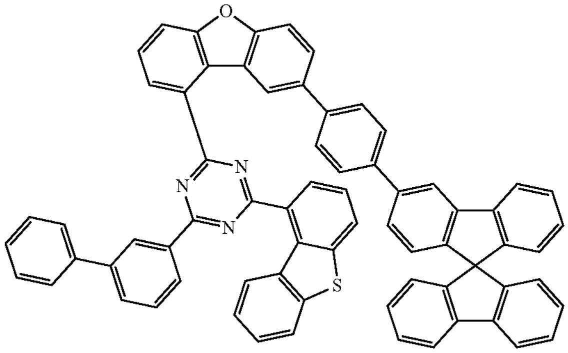
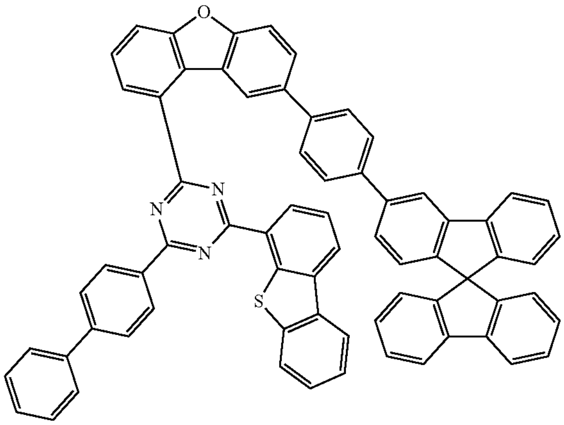
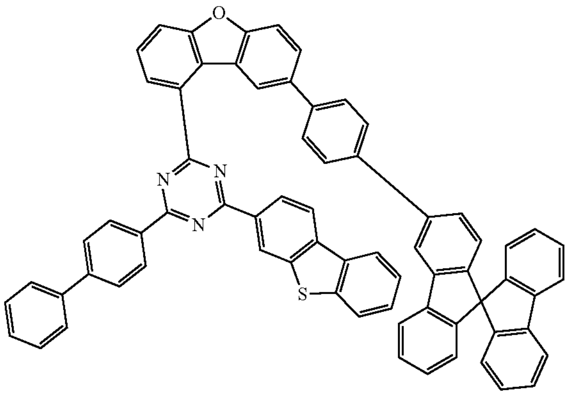

-continued
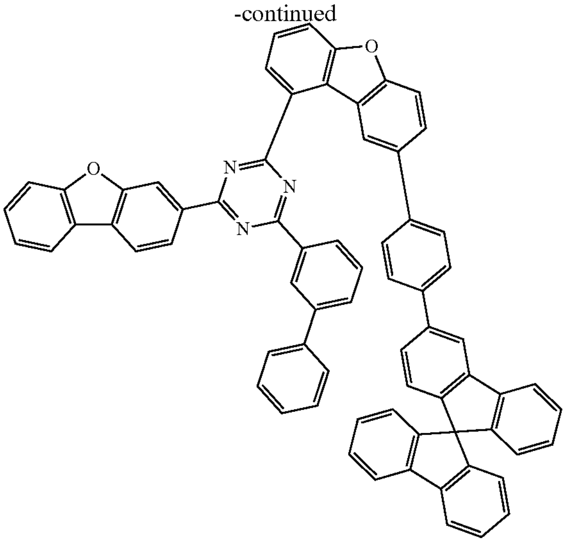
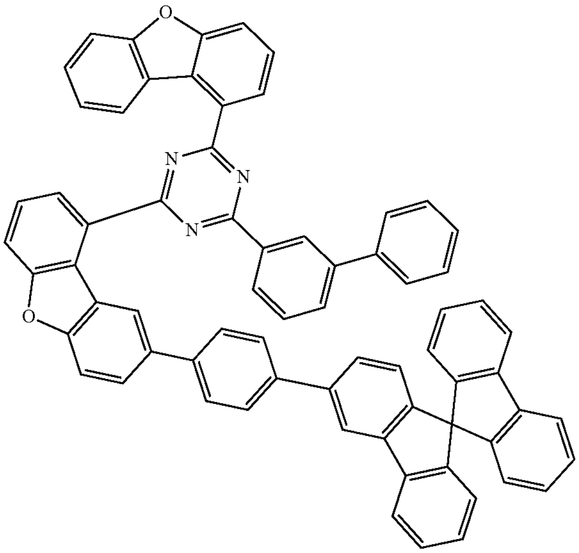
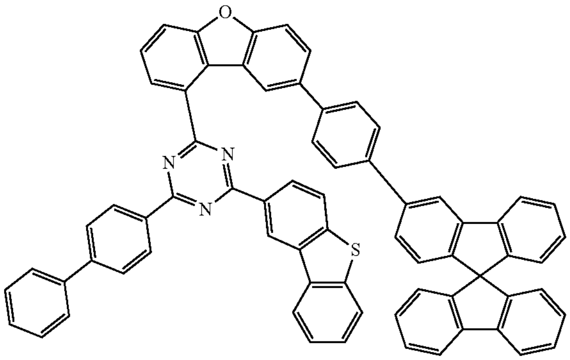
-continued
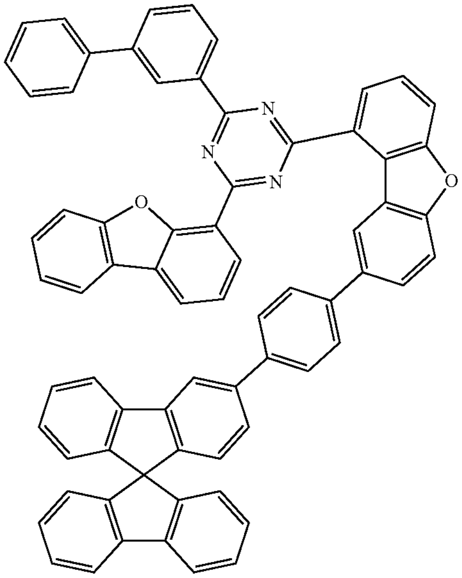
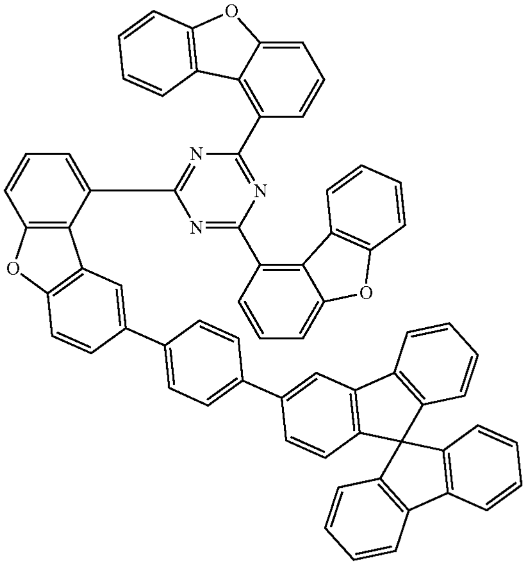
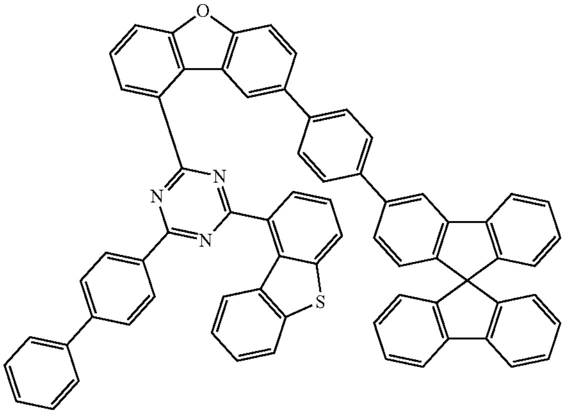

-continued
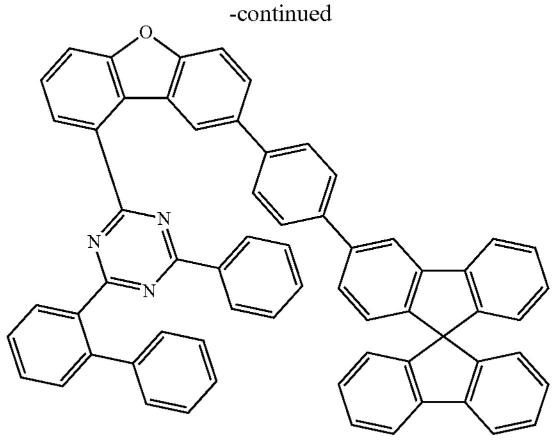
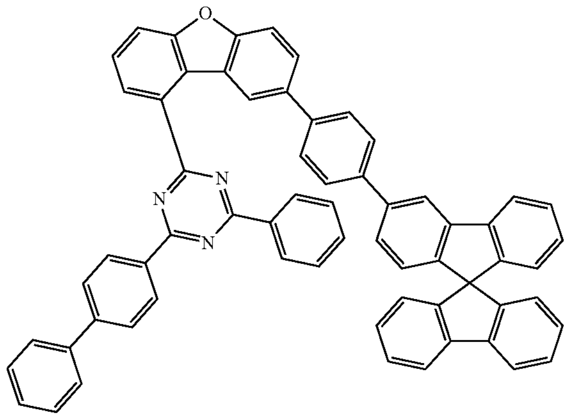
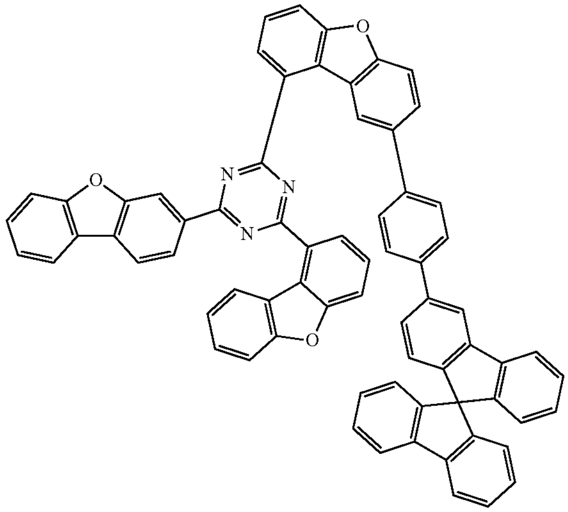
-continued
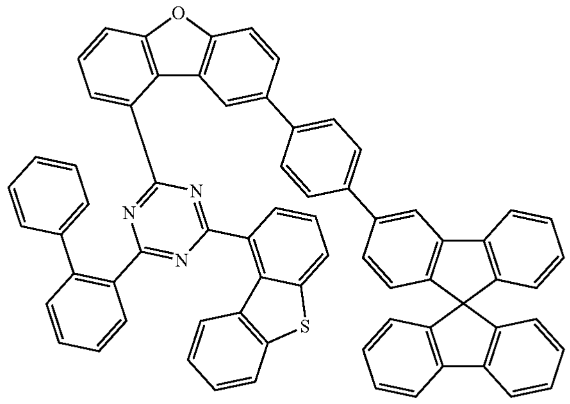
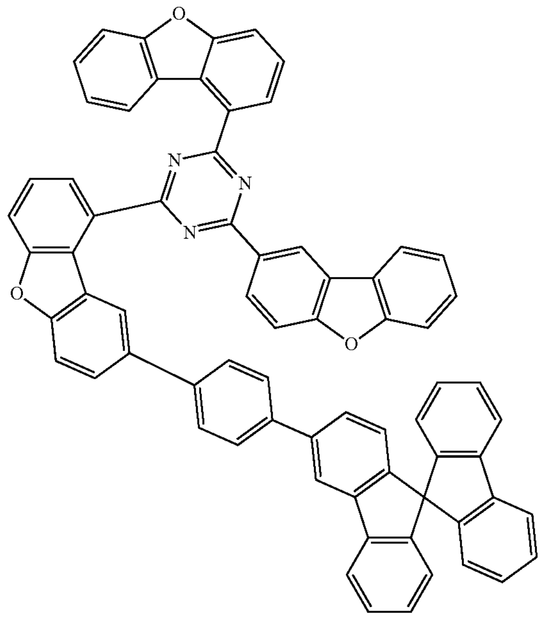 [SMILES: c1ccc2c(c1)-c1ccccc1C21c2ccccc2-c2cc(-c3ccc(-c4ccc5oc6cccc(-c7nc(-c8ccc9oc%10ccccc%10c9c8)nc(-c8cccc9oc%10ccccc%10c89)n7)c6c5c4)cc3)ccc21]
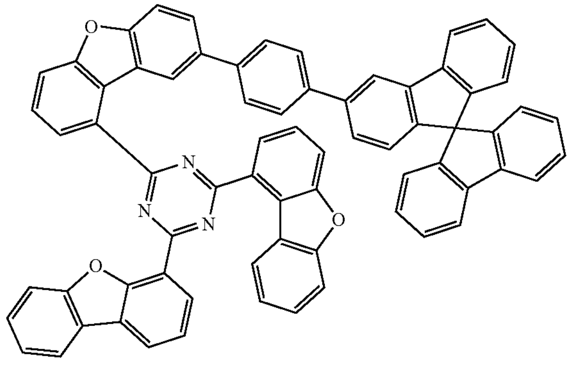

-continued
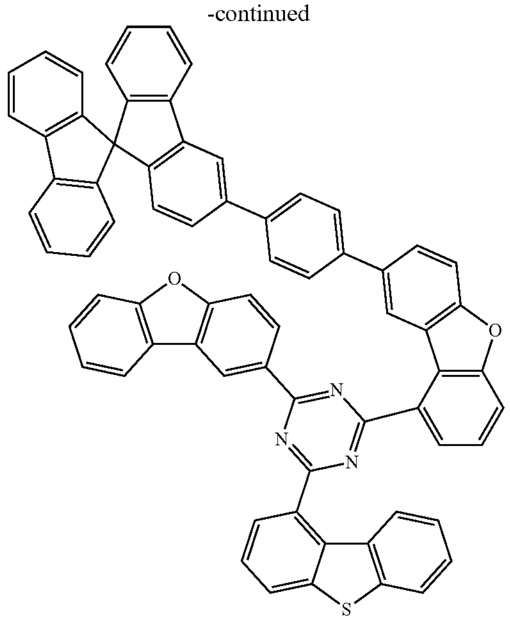
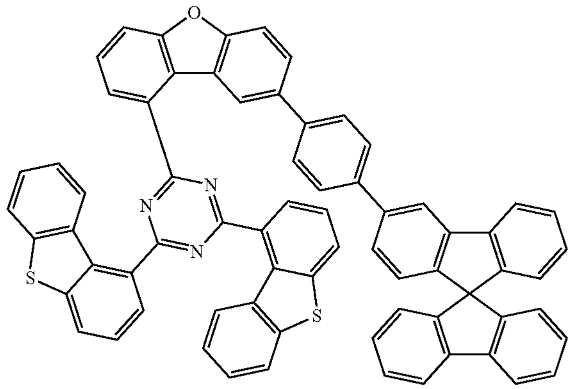
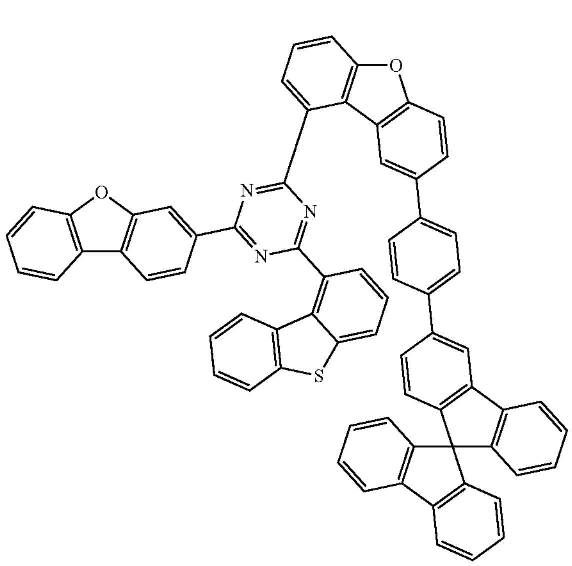
-continued
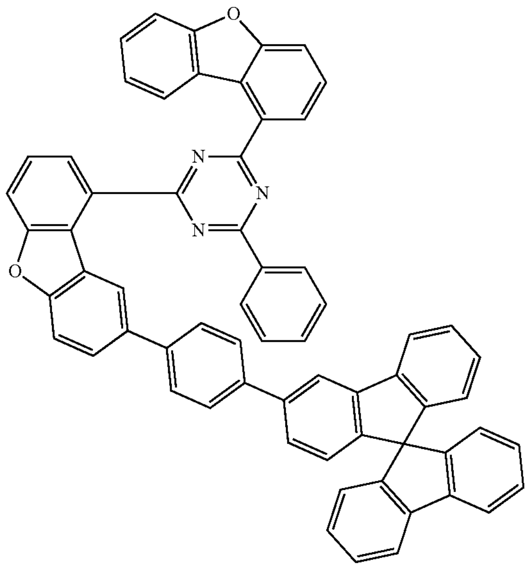
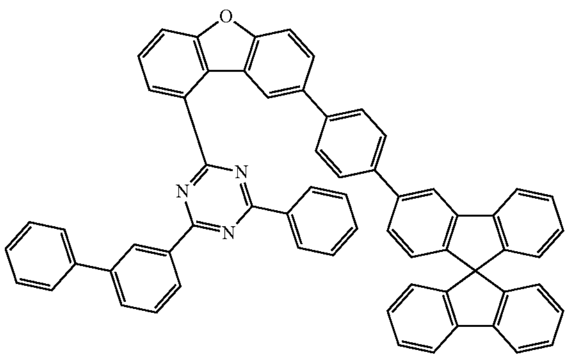
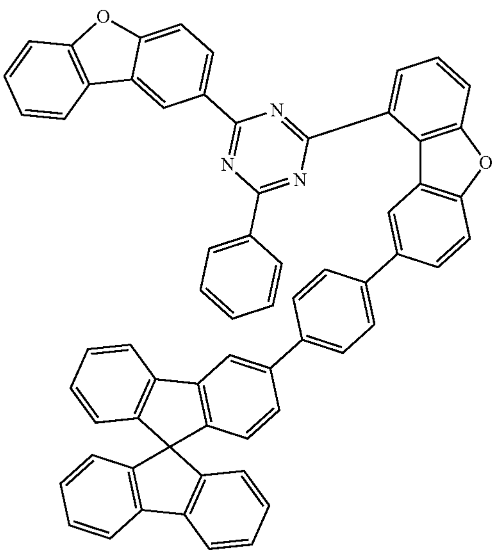

-continued
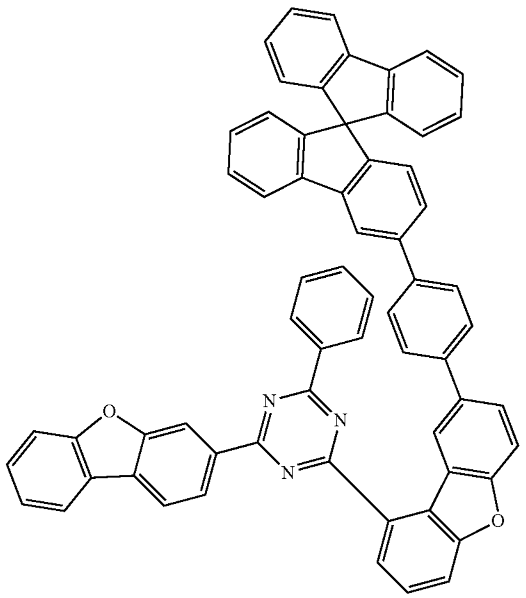
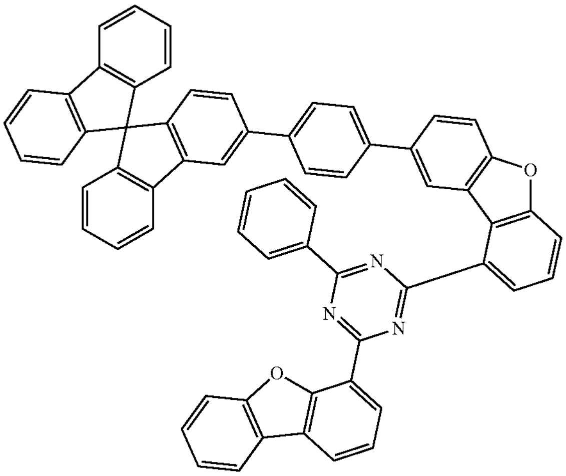
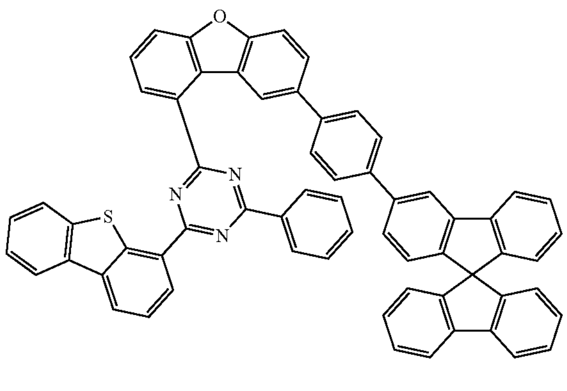
-continued
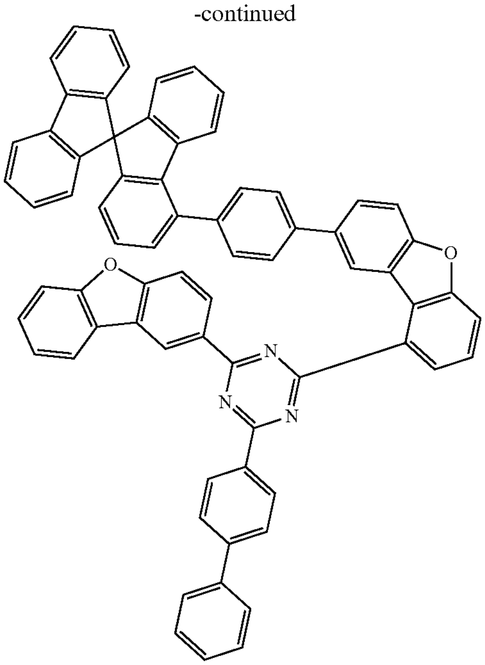
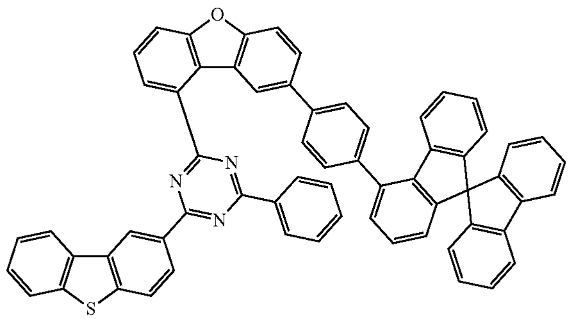
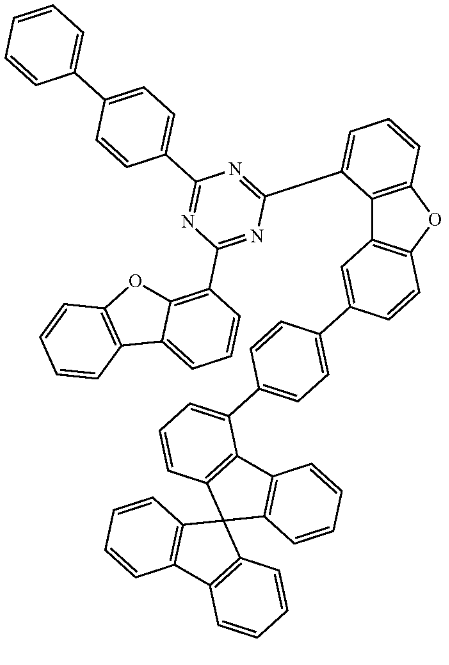

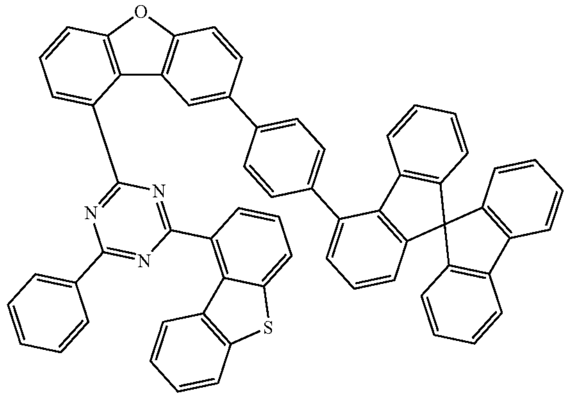
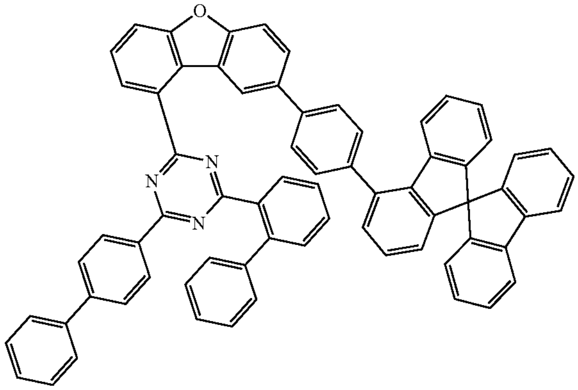
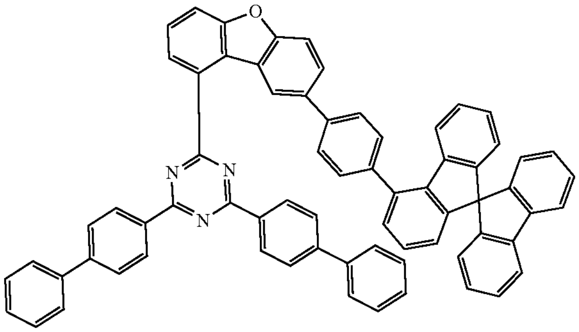
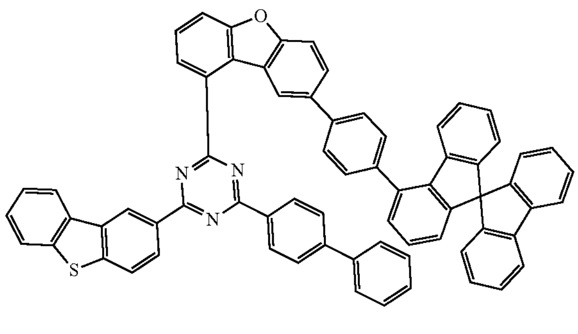
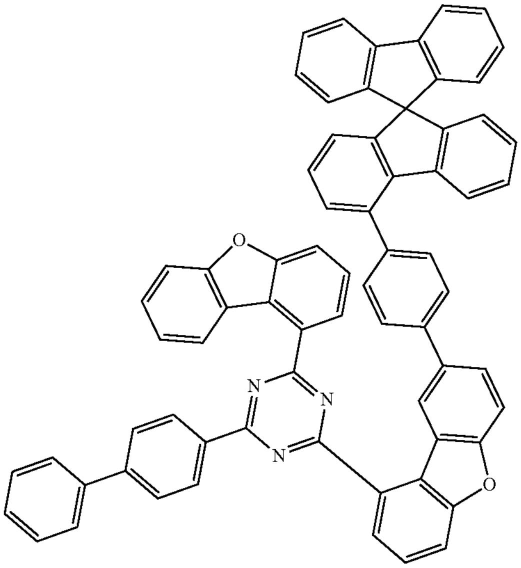
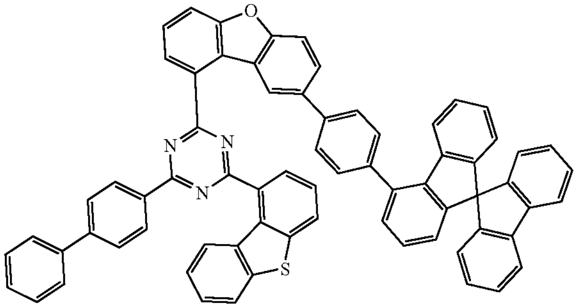
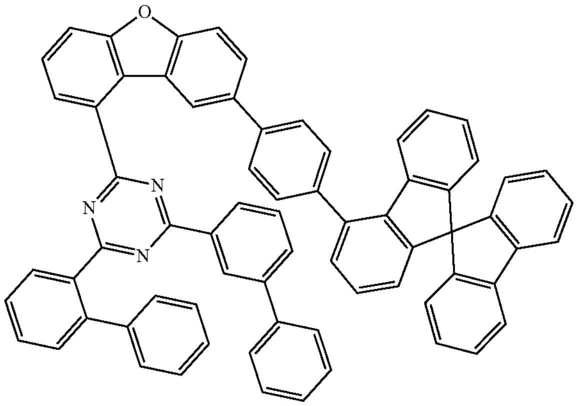
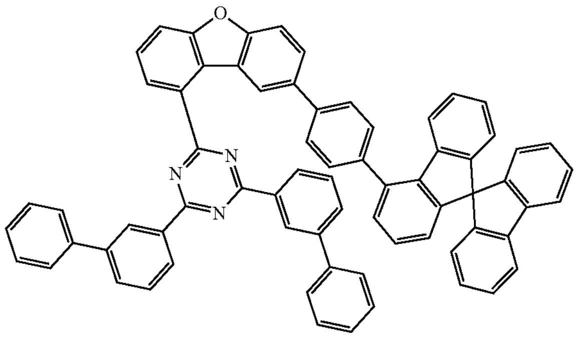

-continued
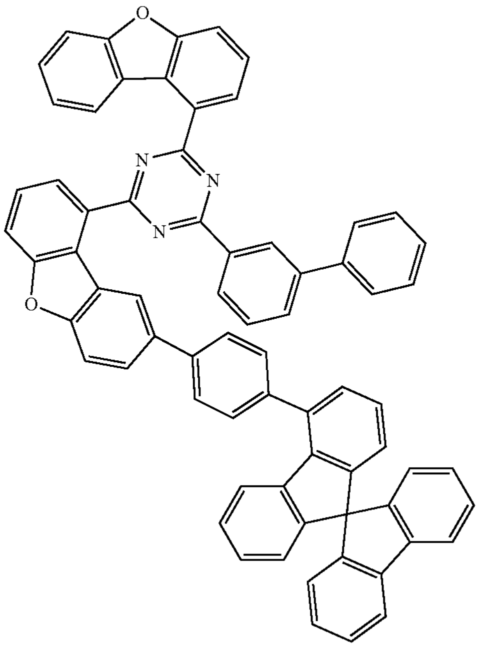
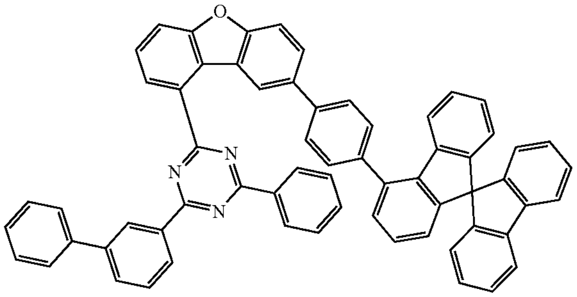
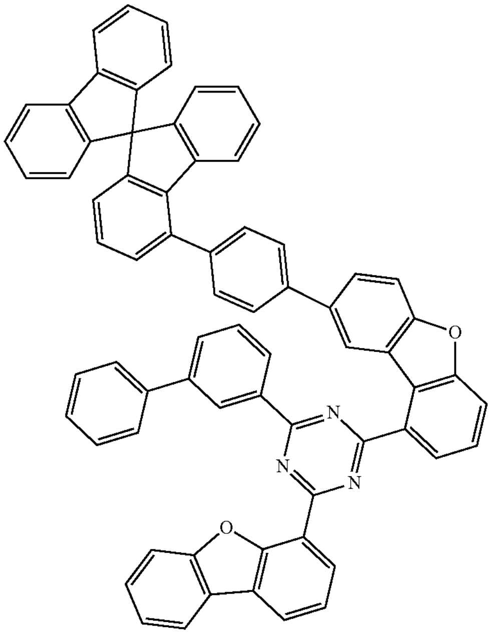
-continued
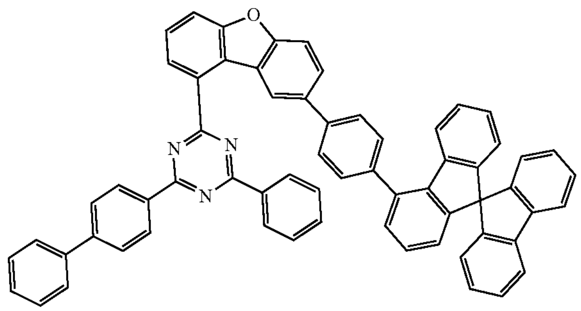
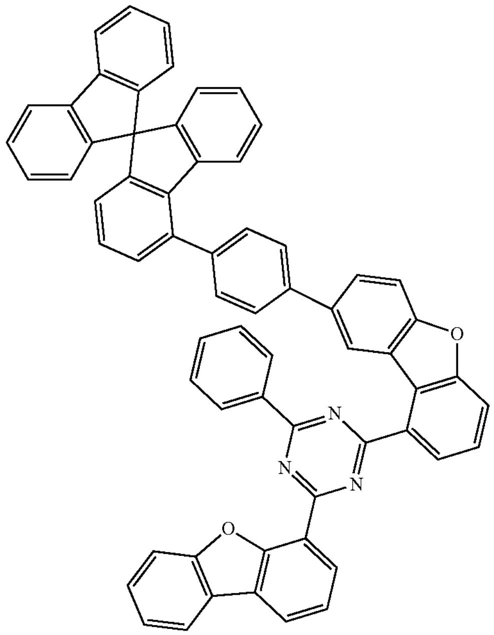
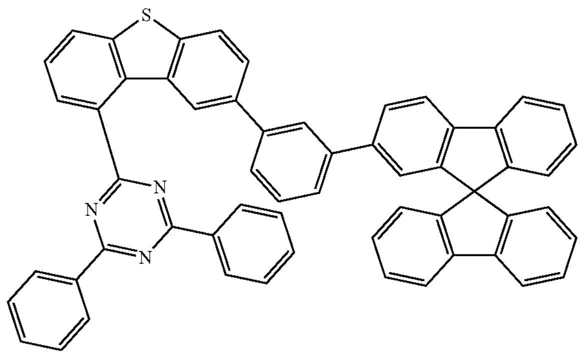

-continued
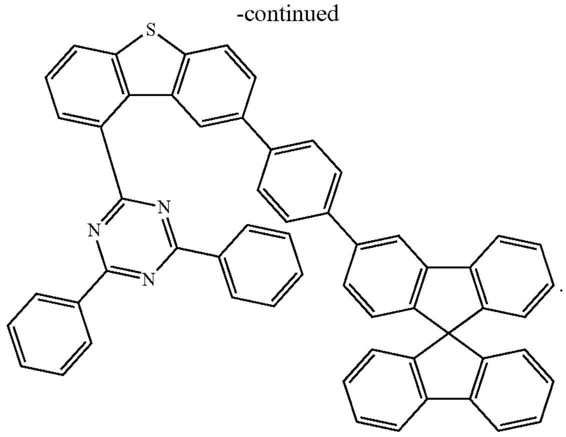
.
* * * * *